United States Patent
Masse et al.

(10) Patent No.: US 10,562,906 B2
(45) Date of Patent: *Feb. 18, 2020

(54) TYK2 INHIBITORS AND USES THEREOF

(71) Applicant: Nimbus Lakshmi, Inc., Cambridge, MA (US)

(72) Inventors: Craig E. Masse, Cambridge, MA (US); Jeremy Robert Greenwood, Brooklyn, NY (US); Sayan Mondal, New York, NY (US); Scott D. Cowen, Cambridge, MA (US); Thomas H. McLean, Cambridge, MA (US)

(73) Assignee: Nimbus Lakshimi, Inc., Cambridge, MA (US)

( * ) Notice: Subject to any disclaimer, the term of this patent is extended or adjusted under 35 U.S.C. 154(b) by 9 days.

This patent is subject to a terminal disclaimer.

(21) Appl. No.: 16/382,824

(22) Filed: Apr. 12, 2019

(65) Prior Publication Data
US 2019/0241576 A1    Aug. 8, 2019

Related U.S. Application Data

(63) Continuation of application No. 16/046,481, filed on Jul. 26, 2018.

(60) Provisional application No. 62/538,536, filed on Jul. 28, 2017, provisional application No. 62/560,615, filed on Sep. 19, 2017, provisional application No. 62/664,048, filed on Apr. 27, 2018.

(51) Int. Cl.
| | |
|---|---|
| *C07D 487/04* | (2006.01) |
| *C07D 519/00* | (2006.01) |
| *A61P 17/06* | (2006.01) |
| *A61P 37/02* | (2006.01) |
| *A61P 11/06* | (2006.01) |
| *A61P 19/02* | (2006.01) |
| *A61P 29/00* | (2006.01) |
| *A61P 35/00* | (2006.01) |

(52) U.S. Cl.
CPC ............ *C07D 487/04* (2013.01); *A61P 11/06* (2018.01); *A61P 17/06* (2018.01); *A61P 19/02* (2018.01); *A61P 29/00* (2018.01); *A61P 35/00* (2018.01); *A61P 37/02* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,891 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,552,065 B2 | 4/2003 | Remiszewski et al. | |
| 7,084,271 B2 | 8/2006 | Guzi et al. | |
| 7,119,200 B2 | 10/2006 | Guzi et al. | |
| 7,161,003 B1 | 1/2007 | Guzi et al. | |
| 7,196,078 B2 | 3/2007 | Guzi et al. | |
| 7,390,799 B2 | 6/2008 | Bruncko et al. | |
| 7,468,372 B2 | 12/2008 | Guzi et al. | |
| 7,557,100 B2 | 7/2009 | Kataoka et al. | |
| 7,691,851 B2 | 4/2010 | Gege et al. | |
| 7,776,865 B2 | 8/2010 | Paruch et al. | |
| 8,138,347 B2 | 3/2012 | Knight et al. | |
| 8,211,854 B2 | 7/2012 | Guzi et al. | |
| 8,518,931 B2 | 8/2013 | Jiang et al. | |
| 8,575,177 B2 | 11/2013 | Haddach et al. | |
| 8,580,782 B2 | 11/2013 | Guzi et al. | |
| 8,586,576 B2 | 11/2013 | Guzi et al. | |
| 8,637,526 B2 | 1/2014 | Blaney et al. | |
| 8,673,924 B2 | 3/2014 | Guzi et al. | |
| 8,946,415 B2 | 2/2015 | Bi et al. | |
| 8,969,360 B2 | 3/2015 | Charrier et al. | |
| 9,303,033 B2 | 4/2016 | Haddach et al. | |
| 9,340,546 B2 | 5/2016 | Ahmad et al. | |
| 9,346,810 B2 | 5/2016 | Su et al. | |
| 9,403,832 B2 | 8/2016 | Bi et al. | |
| 9,573,954 B2 | 2/2017 | Liu et al. | |
| 9,650,381 B2 | 5/2017 | Ahmad et al. | |
| 9,657,025 B2 | 5/2017 | Laufer et al. | |
| 9,718,827 B2 | 8/2017 | Ahmad et al. | |
| 9,879,028 B2 | 1/2018 | Gray et al. | |
| 9,932,344 B2 | 4/2018 | Bondke et al. | |
| 10,023,571 B2 | 7/2018 | Masse et al. | |
| 10,196,390 B2 | 2/2019 | Masse et al. | |
| 10,253,046 B2 | 4/2019 | Dahlgren et al. | |
| 2007/0027156 A1 | 2/2007 | Nakai et al. | |
| 2007/0082900 A1 | 4/2007 | Guzi et al. | |
| 2007/0179161 A1 | 8/2007 | Parratt et al. | |
| 2008/0176870 A1 | 7/2008 | Nolte et al. | |
| 2011/0071115 A1 | 3/2011 | Haddach et al. | |
| 2014/0107099 A1 | 4/2014 | Blaney et al. | |
| 2015/0299205 A1 | 10/2015 | Charrier et al. | |
| 2016/0228443 A1 | 8/2016 | Su et al. | |
| 2016/0244456 A1 | 8/2016 | Blaney et al. | |
| 2017/0129896 A1 | 5/2017 | Bi et al. | |
| 2017/0174692 A1 | 6/2017 | Marineau et al. | |
| 2017/0217966 A1 | 8/2017 | Liu et al. | |
| 2017/0320881 A1 | 11/2017 | Laufer et al. | |

(Continued)

FOREIGN PATENT DOCUMENTS

| | | |
|---|---|---|
| JP | 2006160628 | 6/2006 |
| WO | 2001042246 | 6/2001 |

(Continued)

OTHER PUBLICATIONS

Cancer Drug Design and Discovery; Neidle, Stephen, ed. (Elsevier/Academic Press, 2008), Chapter 18.*

(Continued)

*Primary Examiner* — Alicia L Otton
(74) *Attorney, Agent, or Firm* — Andrea L. C. Reid; Dechert LLP

(57) ABSTRACT

The present invention provides compounds, compositions thereof, and methods of using the same for the inhibition of TYK2, and the treatment of TYK2-mediated disorders.

28 Claims, No Drawings

(56) References Cited

U.S. PATENT DOCUMENTS

| | | |
|---|---|---|
| 2018/0051028 A1 | 2/2018 | Lim et al. |
| 2018/0057497 A1 | 3/2018 | Samajdar et al. |
| 2018/0134700 A1 | 5/2018 | Greenwood et al. |
| 2018/0155349 A1 | 6/2018 | Greenwood et al. |
| 2018/0258086 A1 | 9/2018 | Greenwood et al. |

FOREIGN PATENT DOCUMENTS

| | | |
|---|---|---|
| WO | 2002088112 | 11/2002 |
| WO | 2003063794 | 8/2003 |
| WO | 2004019973 | 3/2004 |
| WO | 2004022561 | 3/2004 |
| WO | 2004089925 | 10/2004 |
| WO | 2004106328 | 12/2004 |
| WO | 2005007623 | 1/2005 |
| WO | 2005113554 | 12/2005 |
| WO | 2006078846 | 7/2006 |
| WO | 2006122806 | 11/2006 |
| WO | 2007016176 | 2/2007 |
| WO | 2007044729 | 4/2007 |
| WO | 2007053452 | 5/2007 |
| WO | 2007070514 | 6/2007 |
| WO | 2007084786 | 7/2007 |
| WO | 2007129161 | 11/2007 |
| WO | 2008039218 | 4/2008 |
| WO | 2008109943 | 9/2008 |
| WO | 2008118802 | 10/2008 |
| WO | 2009114512 | 9/2009 |
| WO | 2010051549 | 5/2010 |
| WO | 2010086040 | 8/2010 |
| WO | 2011090760 | 7/2011 |
| WO | 2012170827 | 12/2012 |
| WO | 2013052263 | 4/2013 |
| WO | 2014074660 | 5/2014 |
| WO | 2017074661 | 5/2014 |
| WO | 2015089143 | 6/2015 |
| WO | 2015131080 | 9/2015 |
| WO | 2016144846 | 9/2016 |
| WO | 2017002120 | 1/2017 |
| WO | 2017009806 | 1/2017 |

OTHER PUBLICATIONS

Gura, Science Nov. 7, 1997: vol. 278. No. 5340, pp. 1041-1042.*
Roberts, Jr et al., JAMA 292(17): 2130-2140 (2004).*
Das, U.N. (Journal of Inflammation Research, 2010:3, pp. 143-170).*
Wang et al., J. Immunol. 2007, 179, pp. 5958-5965, See Introduction.*
Hartung, H., et al., "What do we know about the mechanism of action of disease-modifying treatments in MS?" J. Neurol., vol. 251(suppl. 5), pp. V/12-V/29 (2004).*
Bacon et al., "Interleukin 12 (IL-12) induces tyrosine phosphorylation of Jak2 and Tyk2: differential use of Janus family kinases by IL-2 and IL-12," The Journal of Experimental Medicine, vol. 181, No. 1, Jan. 1995 (pp. 399-404).
Ban et al., "Replication analysis identifies TYK2 as a multiple sclerosis susceptibility factor," European Journal of Human Genetics, vol. 17, No. 10, Oct. 2009 (pp. 1309-1313).
Berge et al., "Pharmaceutical salts," Journal Pharmaceutical Sciences, vol. 66, No. 1, Jan. 1977 (pp. 1-19).
Cho et al., "Genomics and the multifactorial nature of human auto-immune disease," The New England Journal Medicine, vol. 365, No. 17, Oct. 2011 (pp. 1612-1623).
Cortes et al., "Identification of multiple risk variants for ankylosing spondylitis through high-density genotyping of immune-related loci," Nature Genetics, vol. 45, No. 7, Jul. 2013 (pp. 730-738).
Duerr et al., "A Genome-Wide Association Study Identifies IL23R as an Inflammatory Bowel Disease Gene," Science, vol. 314, No. 5804, Dec. 2006 (pp. 1461-1463).
Finbloom et al., "IL-10 induces the tyrosine phosphorylation of Tyk2 and Jak1 and the differential assembly of Stat1 and Stat3 complexes in human T cells and monocytes," Journal immunology, vol. 155, No. 3, Aug. 1995 (pp. 1079-1090).
Fontan et al. "Discovering What Makes STAT Signaling TYK in T-ALL," Cancer Discovery, vol. 3, No. 5, May 2013 (pp. 494-496).
Graham et al., "Association of NCF2, IKZF1, IRF8, IFIH1, and TYK2 with Systemic Lupus Erythematosus," PLoS genetics, vol. 7, No. 10, Oct. 2011 (9 pages).
Harel et al., "Pharmacologic inhibition of JAK-STAT signaling promotes hair growth," Science Advances, vol. 1, No. 9, Oct. 2015 (12 pages).
Ishizaki et al., "Tyk2 deficiency protects joints against destruction in anti-type II collagen antibody-induced arthritis in mice," International Immunology, vol. 23, No. 9, Sep. 2011 (pp. 575-582).
Ishizaki et al., "Tyk2 is a therapeutic target for psoriasis-like skin inflammation," International Immunology, vol. 36, No. 5, Dec. 2013 (pp. 257-267).
Oyamada et al., "Tyrosine Kinase 2 Plays Critical Roles in the Pathogenic CD4 T Cell Responses for the Development of Experimental Autoimmune Encephalomyelitis," Journal of Immunology, vol. 83, No. 11, Dec. 2009 (pp. 1539-7546).
Parham et al., "A receptor for the heterodimeric cytokine IL-23 is composed of IL-12Rβ1 and a novel cytokine receptor subunit, IL-23R," Journal of Immunology, vol. 168, No. 11, Jun. 2002 (pp. 5699-5708).
Ramirez et al., "Defining causative factors contributing in the activation of hedgehog signaling in diffuse large B-cell lymphoma," Leukemia Research, vol. 36, No. 10, Oct. 2012 (pp. 1267-1273).
Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).
Rostovtsev et al., "A Stepwise Huisgen Cycloaddition Process: Copper(I)-Catalyzed Regioselectiv "Ligation" of Azides and Terminal Alkynes**," Angewandte Chemie, vol. 41, No. 14, Jul. 2002 (pp. 2596-2599).
Sanda et al. "TYK2-STAT1-BCL2 Pathway Dependence in T-Cell Acute Lymphoblastic Leukemia," Cancer Discovery, vol. 3, No. 5, May 2013 (pp. 564-577).
Sigurdsson et al., "Polymorphisms in the Tyrosine Kinase 2 and Interferon Regulatory Factor 5 Genes Are Associated with Systemic Lupis Erythematosus," American Journal of Human Genetics, vol. 76, No. 3, Mar. 2005 (pp. 528-537).
Simma et al., "Identification of an Indispensable Role for Tyrosine Kinase 2 in CTL-Mediated Tumor Surveillance," Cancer Research, vol. 69, No. 1, Jan. 2009 (pp. 203-211).
Stahl et al., "Association and activation of Jak-Tyk kinases by CNTF-LIF-OSM-IL-6β receptor components," Science, vol. 263, No. 5143, Jan. 1994 (pp. 92-95).
Strange et al., "A genome-wide association study identifies new psoriasis susceptibility loci and an interaction between HLA-C and ERAP1," Nature Genetics, vol. 42, No. 11, Nov. 2010 (pp. 985-990).
Sun et al., "Carbohydrate and protein immobilization onto solid surfaces by sequential Diels-Alder and azide-alkyne cycloadditions," Bioconjugate Chemistry, vol. 17, No. 1, Jan.-Feb. 2006 (52-57).
Velasquez et al., "A protein kinase in the interferon α/β signaling pathway," Cell, vol. 70, No. 2, Jul. 1992 (pp. 313-322).
Wan et al. "Tyk/STAT3 Signaling Mediates β-Amyloid-Induced Neuronal Cell Death: Implications in Alzheimer's Disease," Journal of Neuroscience, vol. 30, No. 20, May 2010 (pp. 6873-6881).
Welham et al., "Interleukin-13 signal transduction in lymphohemopoietic cells: similarities and differences in signal transduction with interleukin-4 and insulin," The Journal of Biological chemistry, vol. 270, No. 20, May 1995 (pp. 12286-12296).
Xing et al., "Alopecia areata is driven by cytotoxic T lymphocytes and is reversed by JAK inhibition," Nature Medicine, vol. 20, No. 9, Sep. 2014 (pp. 1043-1049).
Zhang et al., "Docking protein Gab2 regulates mucin expression and goblet cell hyperplasia through TYK2/STAT6 pathway," The FASEB Journal, vol. 26, No. 11, Nov. 2012 (pp. 4603-4613).

(56) References Cited

OTHER PUBLICATIONS

International Search Report and Written Opinion issued by the United States Patent and Trademark Office as International Searching Authority for International Application No. PCT/US2018/043917, dated Oct. 12, 2018 (8 pages).

* cited by examiner

TYK2 INHIBITORS AND USES THEREOF

CROSS-REFERENCE TO RELATED APPLICATIONS

The present application is a continuation of U.S. patent application Ser. No. 16/046,481, filed Jul. 26, 2018, which claims priority to U.S. provisional patent application Ser. No. 62/538,536, filed Jul. 28, 2017, U.S. provisional patent application Ser. No. 62/560,615, filed Sep. 19, 2017, and U.S. provisional patent application Ser. No. 62/664,048, filed Apr. 27, 2018, the entirety of each of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

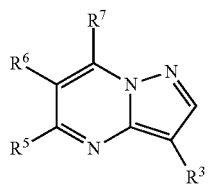

or a pharmaceutically acceptable salt thereof, wherein each of $R^3$, $R^5$, $R^6$, and $R^7$ is as defined below and described in embodiments herein, both singly and in combination.

In some embodiments, the present invention provides a pharmaceutical composition comprising a compound of formula I, and a pharmaceutically acceptable carrier, adjuvant, or diluent.

In some embodiments, the present invention provides a method of treating a TYK2-mediated disease, disorder, or condition comprising administering to a patient in need thereof, a a compound of formula I or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

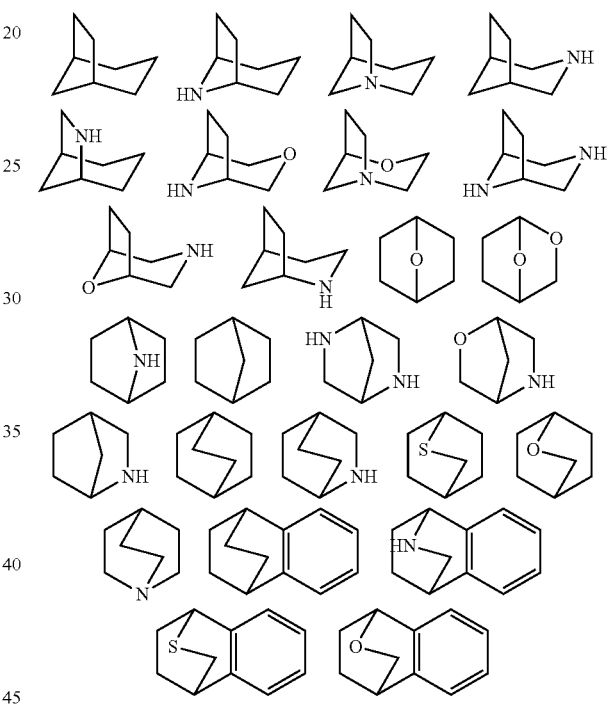

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R)C(O)R$^\circ$; —N(R$^\circ$)C(S)R$^\circ$; —(CH$_2$)$_{0-4}$N(R)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$;

—N(R$^\circ$)N(R$^\circ$)C(O)NR$^\circ{}_2$; —N(R$^\circ$)N(R$^\circ$)C(O)OR$^\circ$; —N(R$^\circ$)C(NR$^\circ$)N(R$^\circ$)$_2$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ{}_3$; —(CH$_2$)$_{0-4}$OC(O)R$^\circ$; —OC(O)(CH$_2$)$_{0-4}$SR$^\circ$; —SC(S)SR$^\circ$; —(CH$_2$)$_{0-4}$SC(O)R$^\circ$; —(CH$_2$)$_{0-4}$C(O)NR$^\circ{}_2$; —C(S)NR$^\circ{}_2$; —C(S)SR$^\circ$; —SC(S)SR$^\circ$, —(CH$_2$)$_{0-4}$OC(O)NR$^\circ{}_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ{}_2$; —(CH$_2$)$_{0-4}$S(O)R; —N(R$^\circ$)S(O)$_2$NR$^\circ{}_2$; —N(RO)S(O)$_2$R; —N(OR)R$^\circ$; —C(NH)NR$^\circ{}_2$; —P(O)$_2$R$^\circ$; —P(O)R$^\circ{}_2$; —OP(O)R$^\circ{}_2$; —OP(O)(OR$^\circ$)$_2$; —SiR$^\circ{}_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*2))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$ (C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

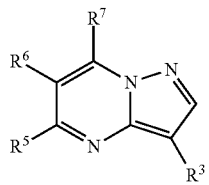

or a pharmaceutically acceptable salt thereof, wherein:

R³ is —C(O)NH₂; —C(O)NHR³·⁴; —C(O)N(R³·⁴)₂; or a 5-6 membered monocyclic heteroaryl ring having 1-4 heteroatoms independently selected from nitrogen, oxygen, and sulfur, wherein said ring is substituted with m instances of R³ᴮ;

R⁵ is hydrogen, or -L¹-R⁵·⁴;

R⁶ is hydrogen, Rᴬ, or Rᴮ;

or R⁵ and R⁶ are taken together with their intervening atoms to form a 4-7 membered partially unsaturated, or heteroaryl ring having 0-3 heteroatoms independently selected from nitrogen, oxygen, and sulfur, wherein said ring is substituted by R⁵·⁴ and n instances of Rᶜ;

R⁷ is hydrogen, halogen, —NH₂, —NHR⁷·⁴, or —NHC(O)R⁷·⁴;

or R⁶ and R⁷ are taken together with their intervening atoms to form a 4-7 membered partially unsaturated, or heteroaryl ring having 0-3 heteroatoms independently selected from nitrogen, oxygen, and sulfur; wherein said ring is substituted by p instances of Rᶜ;

L¹ is a covalent bond or a C₁₋₄ bivalent saturated or unsaturated, straight or branched hydrocarbon chain wherein one or two methylene units of the chain are optionally and independently replaced by —C(R⁵ᴮ)₂—, —CH(R⁵ᴮ)—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)—, or —S(O)₂—;

R³·⁴ and R⁷·⁴ are each independently Rᴮ, and are each substituted by q instances of Rᶜ;

R⁵·⁴ and each instance of R⁵ᴮ are each independently Rᴬ or Rᴮ, and are each substituted by r instances of Rᶜ;

each instance of Rᴬ is independently oxo, halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, or —N(R)S(O)₂R;

each instance of Rᴮ is independently C₁₋₆ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of Rᶜ is independently oxo, halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, or —N(R)S(O)₂R or an optionally substituted group selected from C₁₋₆ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from C₁₋₆ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4.

In certain embodiments, the present invention provides a compound of formula I:

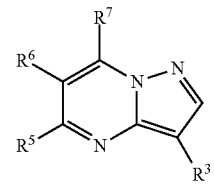

or a pharmaceutically acceptable salt thereof, wherein:

R³ is —C(O)NH₂; —C(O)NHR³·⁴; —C(O)N(R³·⁴)₂; —C(O)OR; —C(O)NOR; or a 5-6 membered monocyclic heteroaryl ring having 1-4 heteroatoms independently selected from nitrogen, oxygen, and sulfur, wherein said ring is substituted with m instances of R³ᴮ;

R⁵ is hydrogen, or -L¹-R⁵·⁴;

R⁶ is hydrogen, Rᴬ, or Rᴮ;

or R⁵ and R⁶ are taken together with their intervening atoms to form a 4-7 membered partially unsaturated, or heteroaryl ring having 0-3 heteroatoms independently selected from nitrogen, oxygen, and sulfur, wherein said ring is substituted by R⁵·⁴ and n instances of Rᶜ;

R⁷ is hydrogen, halogen, —NH₂, —NHR⁷·⁴, or —NHC(O)R⁷·⁴;

or R⁶ and R⁷ are taken together with their intervening atoms to form a 4-7 membered partially unsaturated, or heteroaryl ring having 0-3 heteroatoms independently selected from nitrogen, oxygen, and sulfur; wherein said ring is substituted by p instances of Rᶜ;

L¹ is a covalent bond or a C₁₋₄ bivalent saturated or unsaturated, straight or branched hydrocarbon chain wherein one or two methylene units of the chain are optionally and independently replaced by —C(R⁵ᴮ)₂—, —CH(R⁵ᴮ)—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)—, or —S(O)₂—;

R³·⁴ and R⁷·⁴ are each independently Rᴮ, and are each substituted by q instances of Rᶜ; R⁵·⁴ and each instance of R⁵ᴮ are each independently Rᴬ or Rᴮ, and are each substituted by r instances of Rᶜ;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4.

In certain embodiments, the present invention provides a compound of formula I':

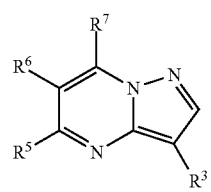

I' or a pharmaceutically acceptable salt thereof, wherein:
$R^3$ is —C(O)NH$_2$; —C(O)NHR$^{3A}$; —C(O)N(R$^{3A}$)$_2$; —C(O)OR; —C(O)NHOR; or a 5-6 membered monocyclic heteroaryl ring having 1-4 heteroatoms independently selected from nitrogen, oxygen, and sulfur, wherein said ring is substituted with m instances of R$^{3B}$;

$R^5$ is hydrogen, or -L$^1$-R$^{5A}$;

$R^6$ is hydrogen, R$^A$, or R$^B$;

or $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by R$^{5A}$ and n instances of R$^C$;

$R^7$ is hydrogen, halogen, —NH$_2$, —NHR$^{7A}$, or —NHC(O)R$^{7A}$;

or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of R$^C$;

L$^1$ is a covalent bond or a C$_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;

R$^{3A}$ and R$^{7A}$ are each independently R$^B$, and are each substituted by q instances of R$^C$, wherein two R$^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two R$^C$ substituents on adjacent carbons are optionally taken together to form a 3-6 membered saturated or partially unsaturated fused heterocyclic ring having 1-4 heteroatoms independently selected from nitrogen, oxygen, and sulfur;

R$^{5A}$ and each instance of R$^{5B}$ are each independently R$^A$ or R$^B$, and are each substituted by r instances of R$^C$;

each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;

each instance of $R^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4.

As defined generally above, $R^3$ is —C(O)NH$_2$; —C(O)NHR$^{3A}$; —C(O)N(R$^{3A}$)$_2$; —C(O)OR; —C(O)NOR; —C(O)NHOR; or a 5-6 membered monocyclic heteroaryl ring having 1-4 heteroatoms independently selected from nitrogen, oxygen, and sulfur, wherein said ring is substituted with m instances of $R^{3B}$. In some embodiments, $R^3$ is —C(O)NH$_2$; —C(O)NHR$^{3A}$; —C(O)N(R$^{3A}$)$_2$; or a 5-6 membered monocyclic heteroaryl ring having 1-4 heteroatoms independently selected from nitrogen, oxygen, and sulfur, wherein said ring is substituted with m instances of $R^{3B}$. In some embodiments, $R^3$ is —C(O)NH$_2$ or —C(O)NHR$^{3A}$. In some embodiments, $R^3$ is —C(O)NOR. In some embodiments, $R^3$ is —C(O)OR.

In some embodiments, $R^3$ is —C(O)N(R$^{3A}$)$_2$. In some embodiments, $R^3$ is —C(O)NHOR. In some embodiments, $R^3$ is a 5-6 membered monocyclic heteroaryl ring having 1-4 heteroatoms independently selected from nitrogen, oxygen, and sulfur, wherein said ring is substituted with m instances of $R^{3B}$.

In some embodiments, $R^3$ is —C(O)NH$_2$. In some embodiments, $R^3$ is —C(O)NHR$^{3A}$ In some embodiments, $R^3$ is —C(O)NHOR or —C(O)OR. In some embodiments, $R^3$ is —C(O)NH$_2$, —C(O)NHR$^{3A}$, —C(O)NHOR or —C(O)OR. In some embodiments, $R^3$ is —C(O)NH$_2$, —C(O)NHR$^{3A}$ or —C(O)NHOR.

In some embodiments, $R^3$ is selected from the following:

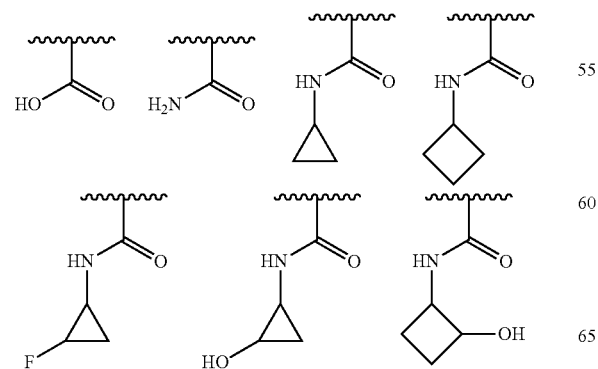

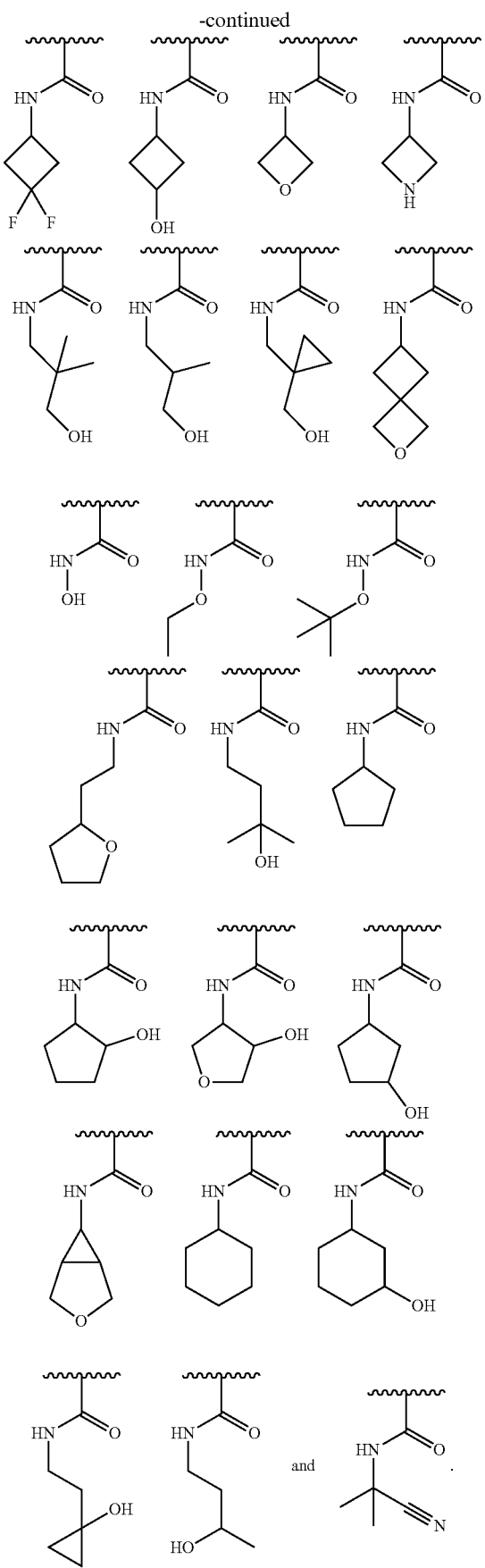

In some embodiments, R³ is selected from the following:
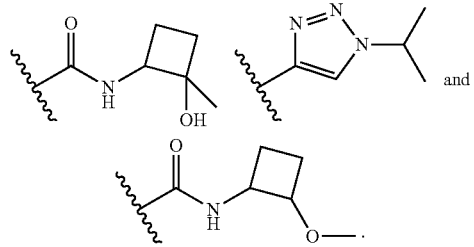
In some embodiments, R³ is selected from the following:
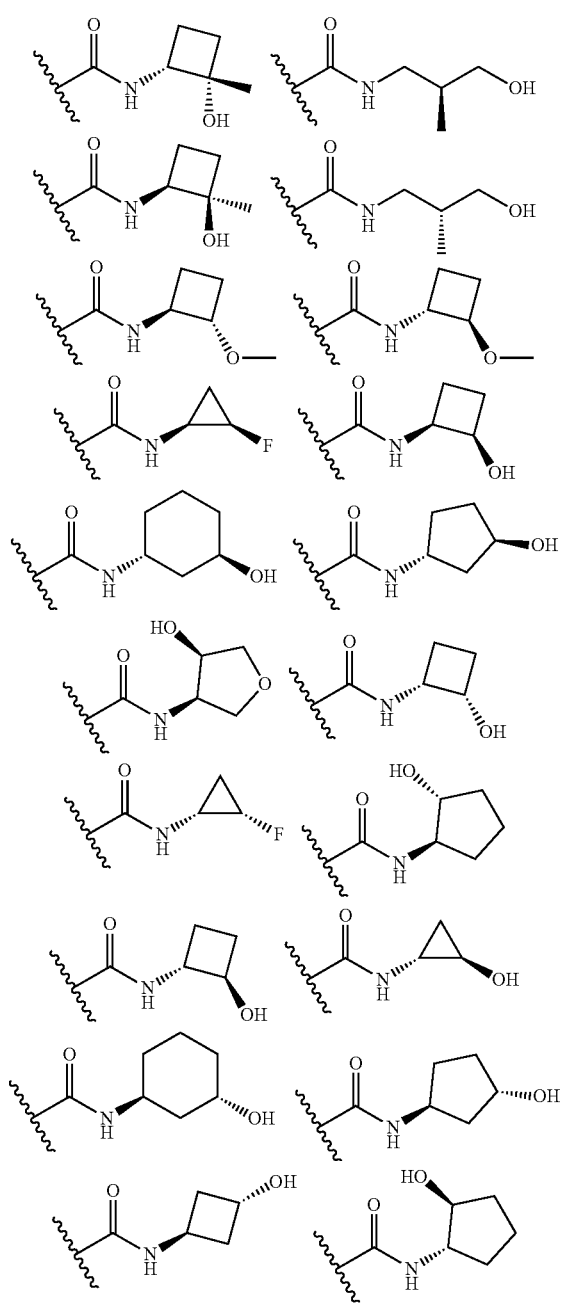
In some embodiments, R³ is selected from the following:
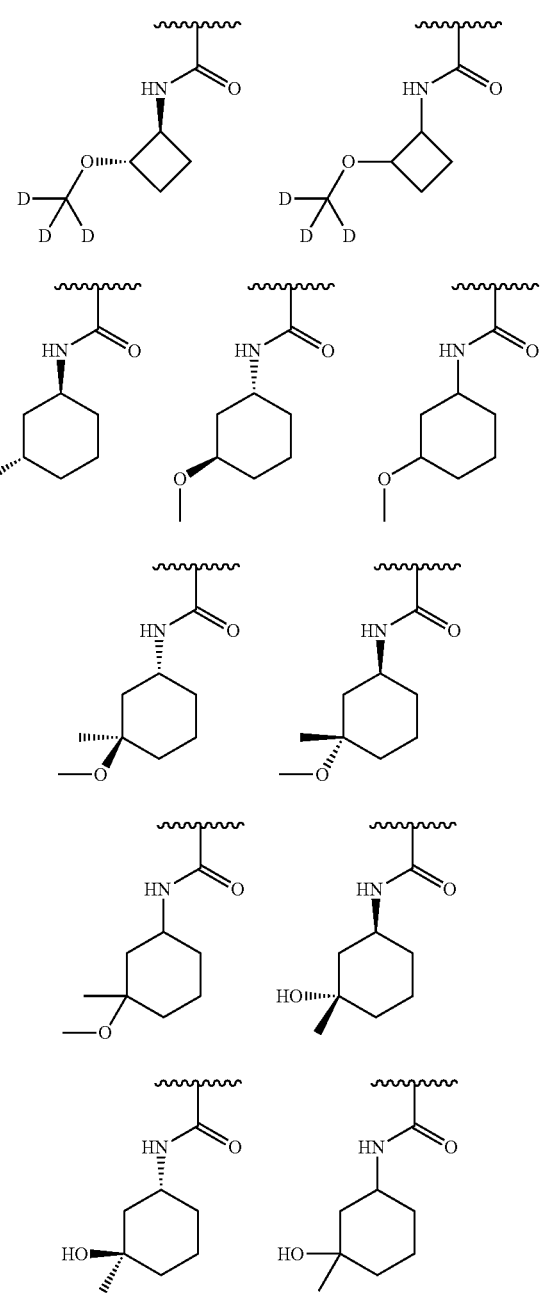

-continued

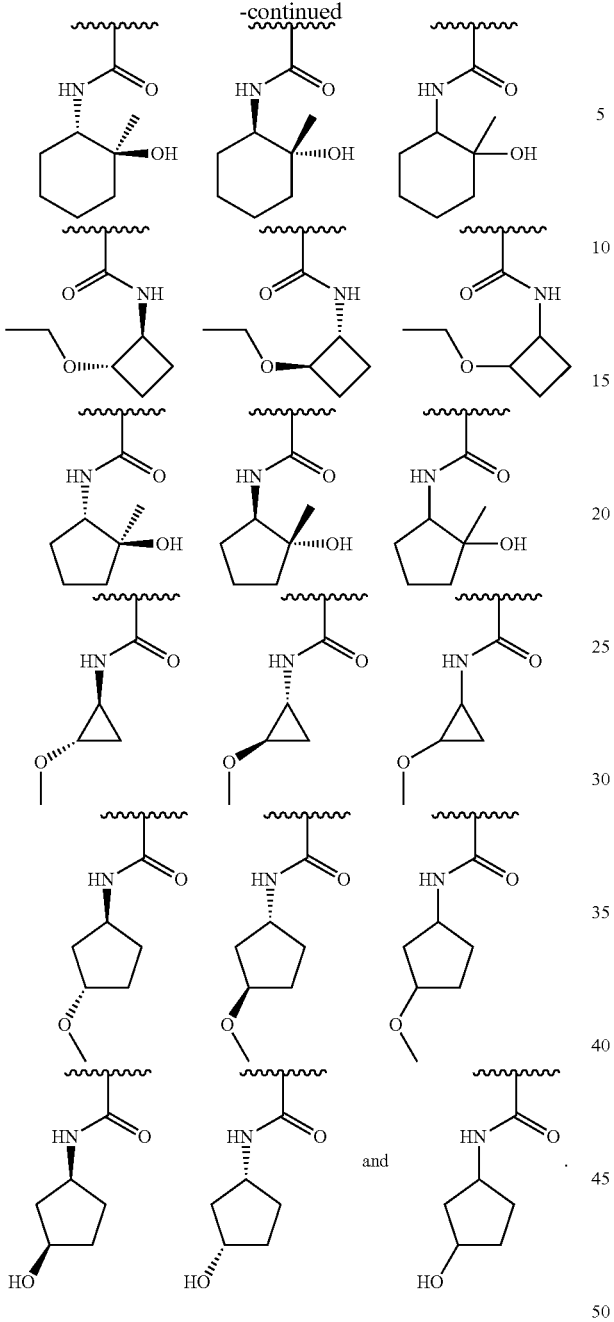

In some embodiments, R³ is selected from those depicted in Table 1, below.

As defined generally above, R⁵ is hydrogen, or -L¹-R⁵ᴬ; or R⁵ and R⁶ are taken together with their intervening atoms to form a 4-7 membered partially unsaturated, or heteroaryl ring having 0-3 heteroatoms independently selected from nitrogen, oxygen, and sulfur, wherein said ring is substituted by R⁵ᴬ and n instances of Rᶜ. In some embodiments, R⁵ is hydrogen. In some embodiments, R⁵ is -L¹-R⁵ᴬ.

In some embodiments, R⁵ and R⁶ are taken together with their intervening atoms to form a 4-7 membered partially unsaturated, or heteroaryl ring having 0-3 heteroatoms independently selected from nitrogen, oxygen, and sulfur, wherein said ring is substituted by R⁵ᴬ and n instances of Rᶜ. In some embodiments, R⁵ is hydrogen or -L¹-R⁵ᴬ.

In some embodiments, R⁵ is selected from the following:

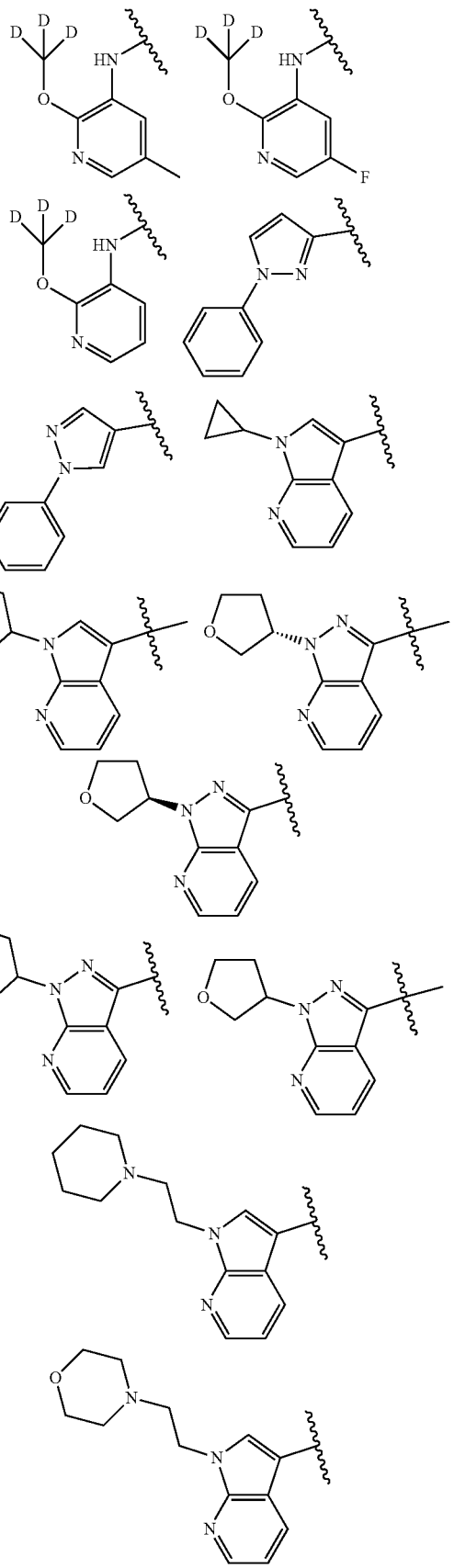

-continued
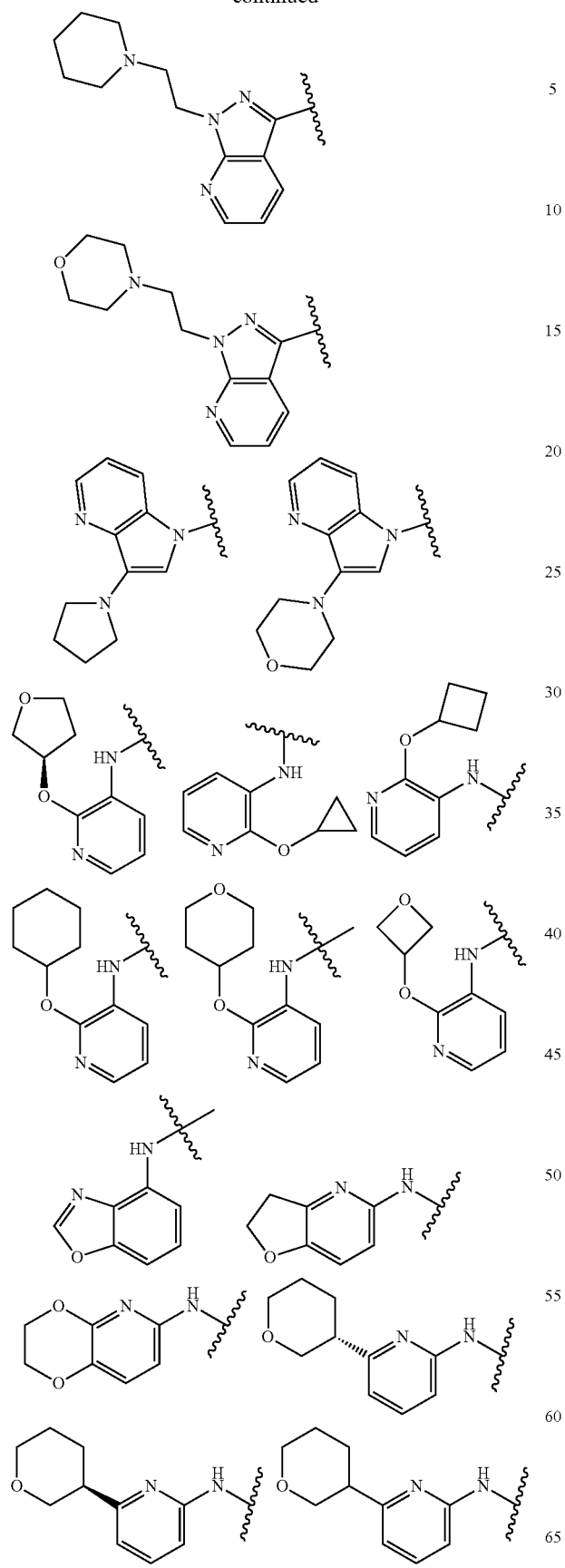
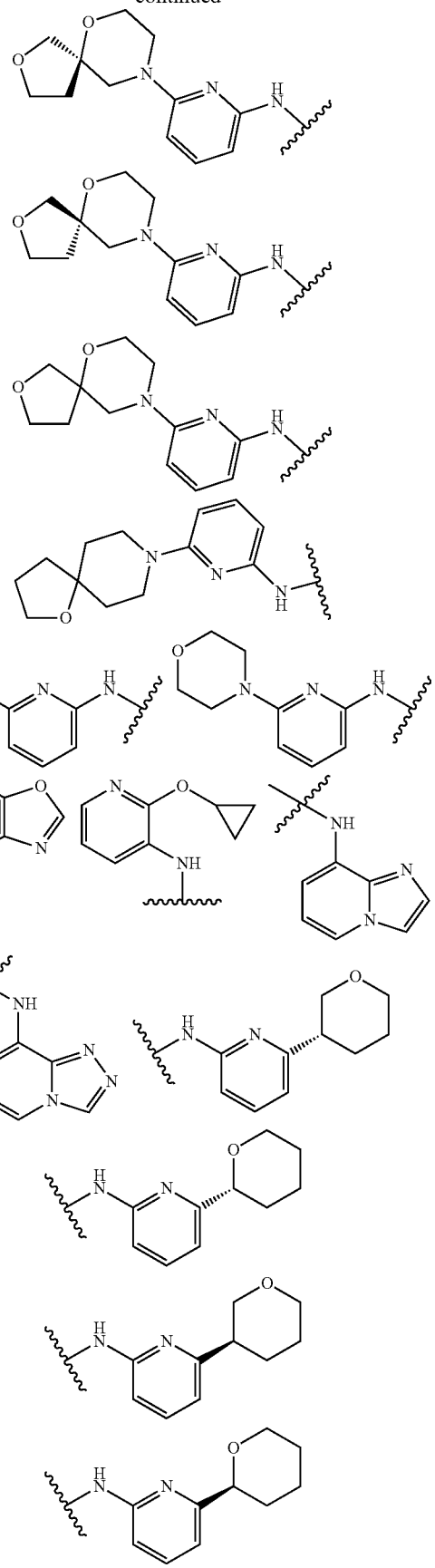

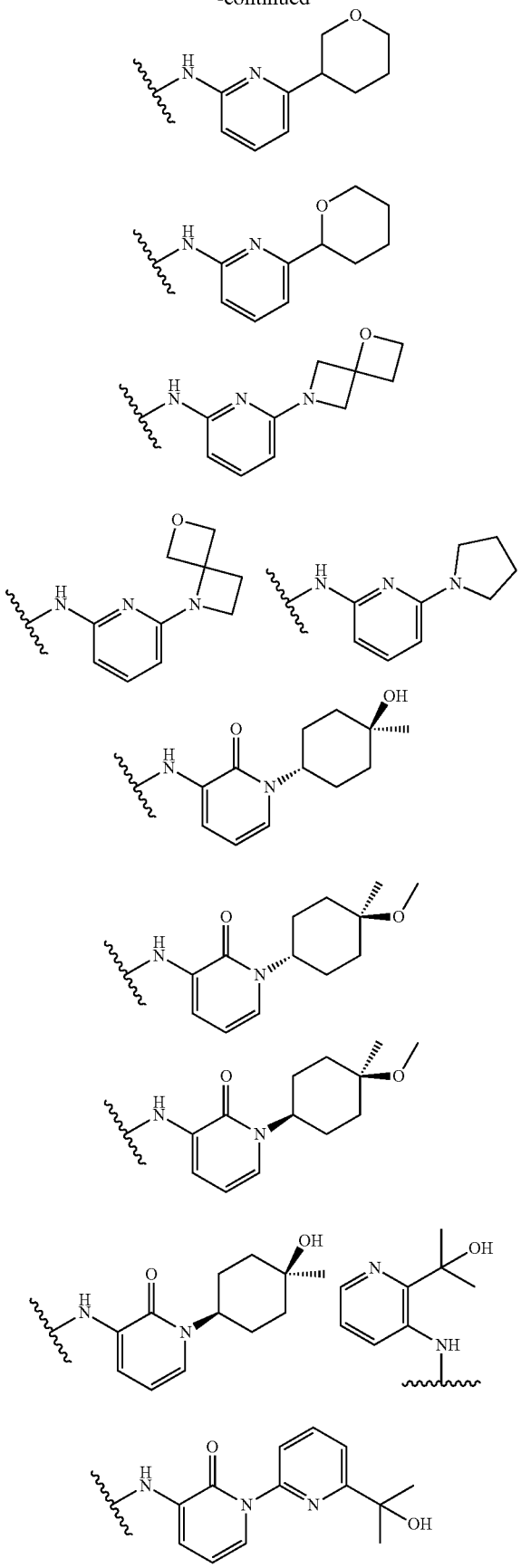
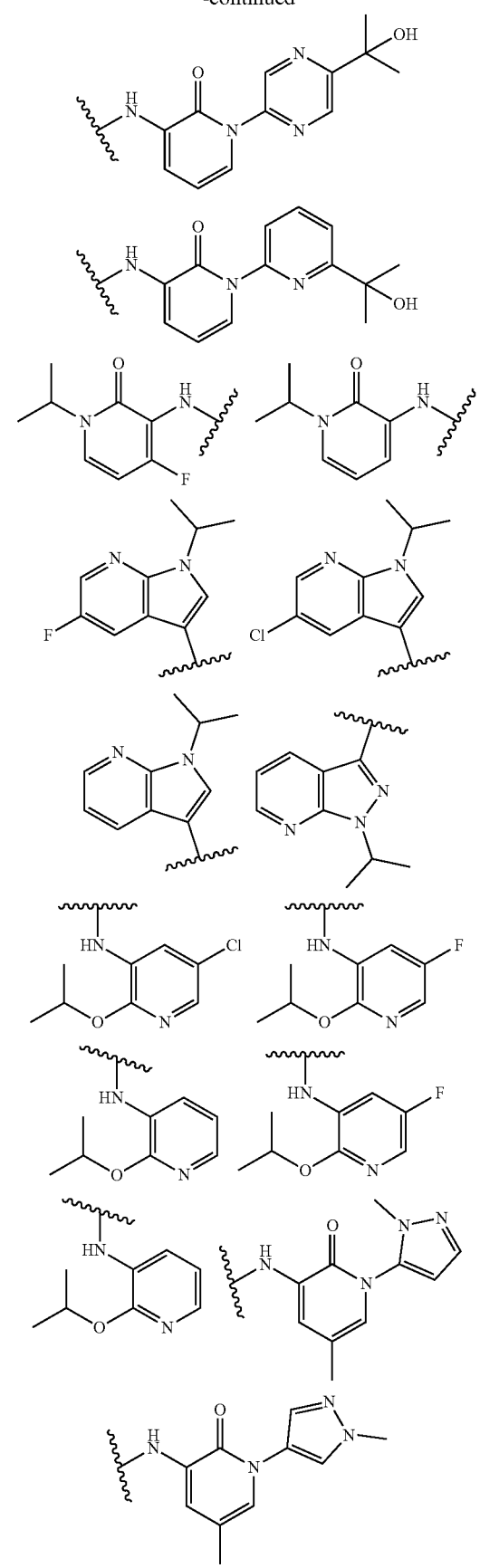

-continued
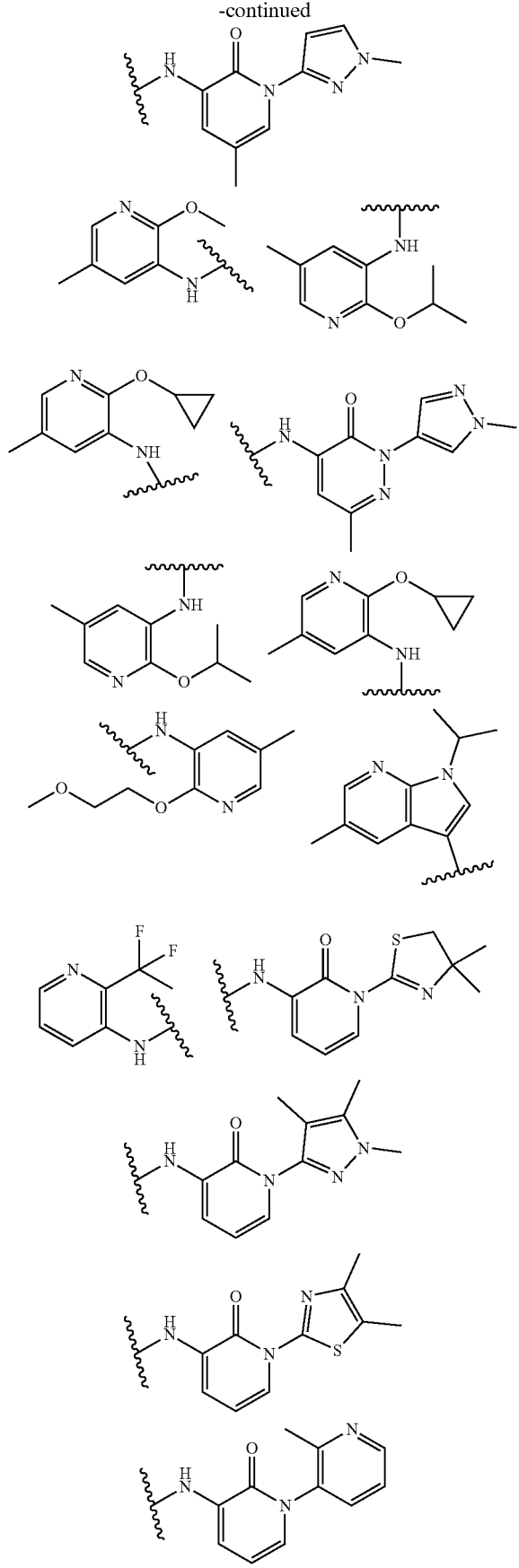
-continued
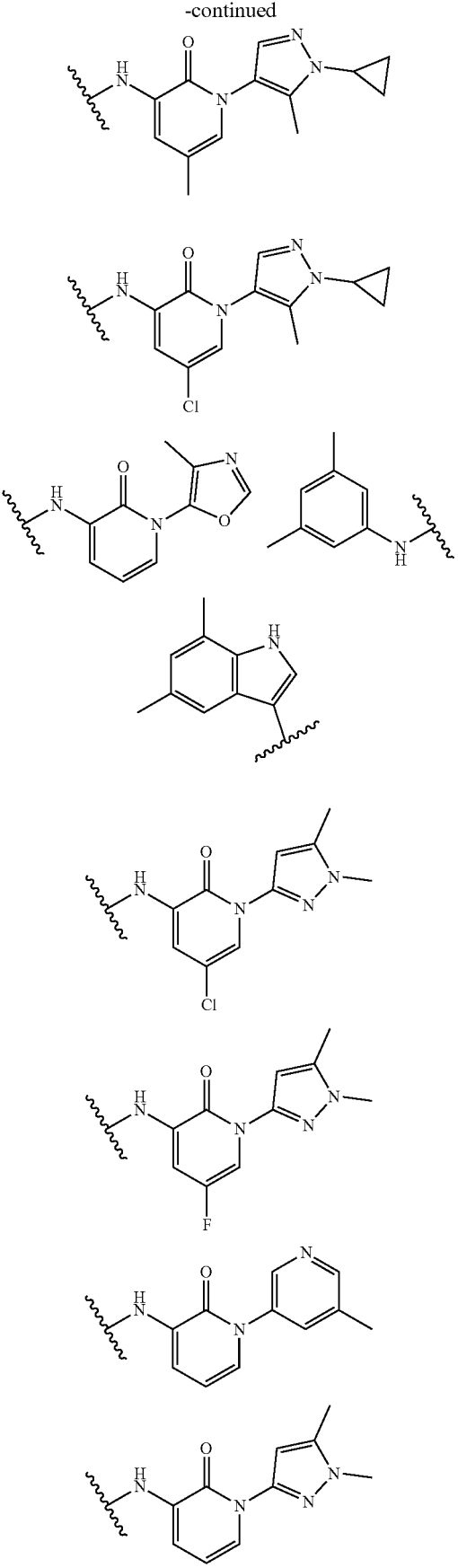

-continued
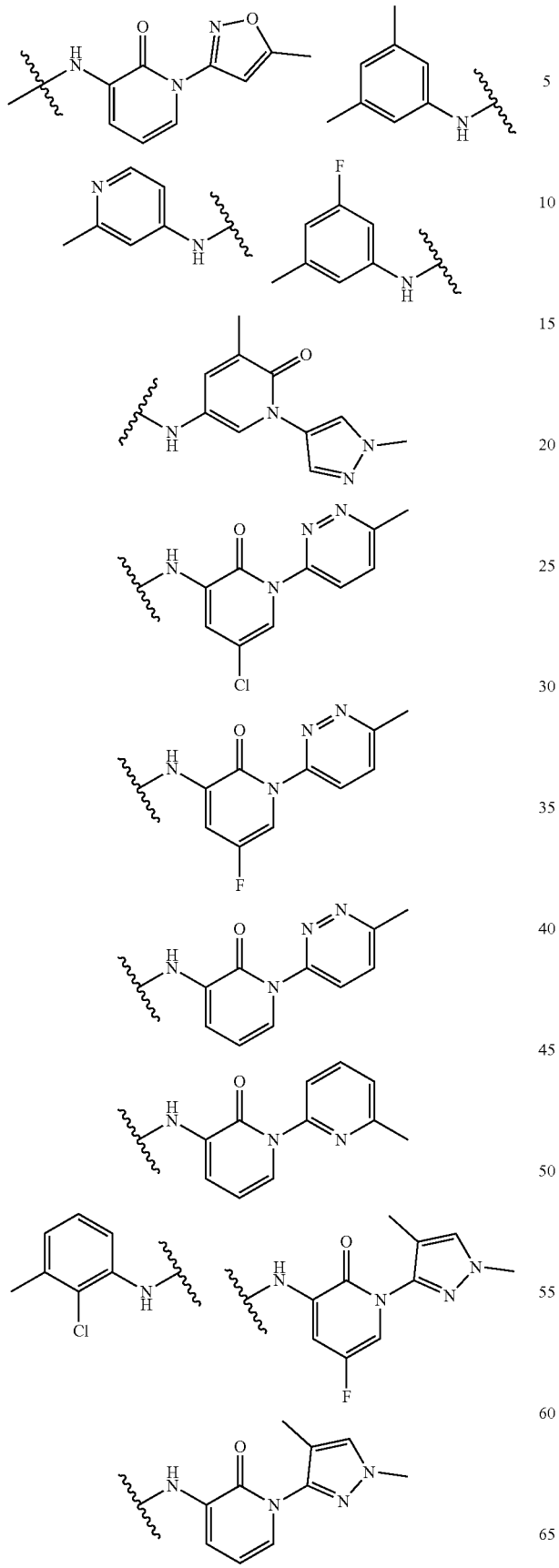
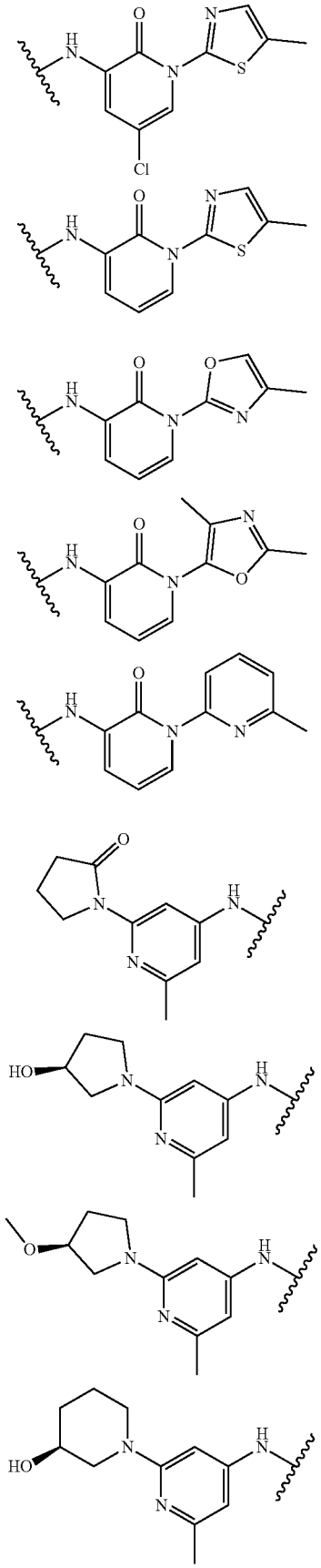

-continued
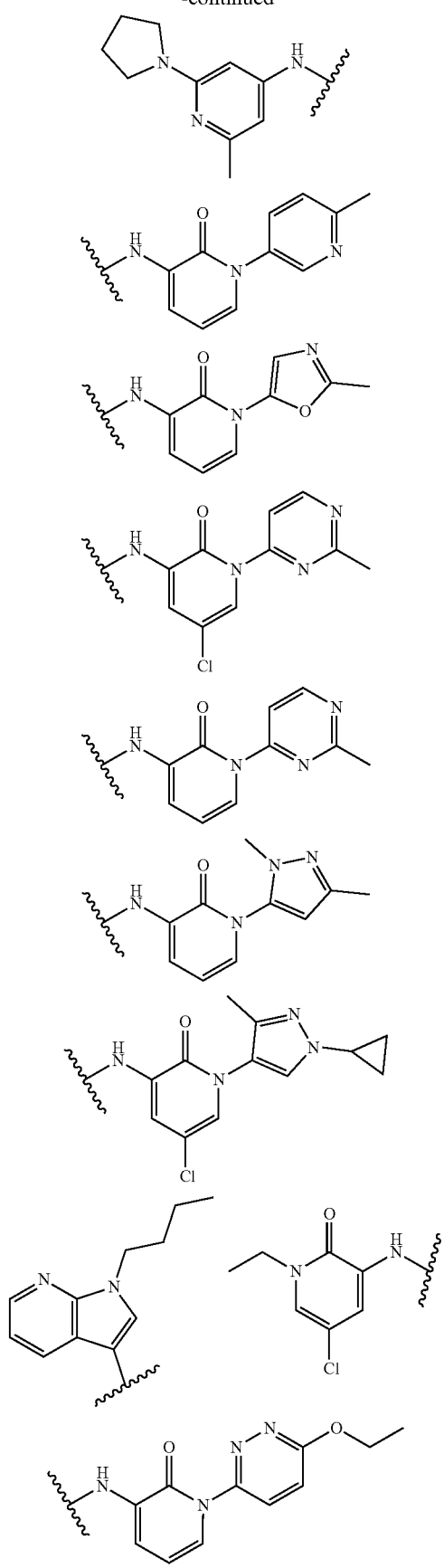
-continued
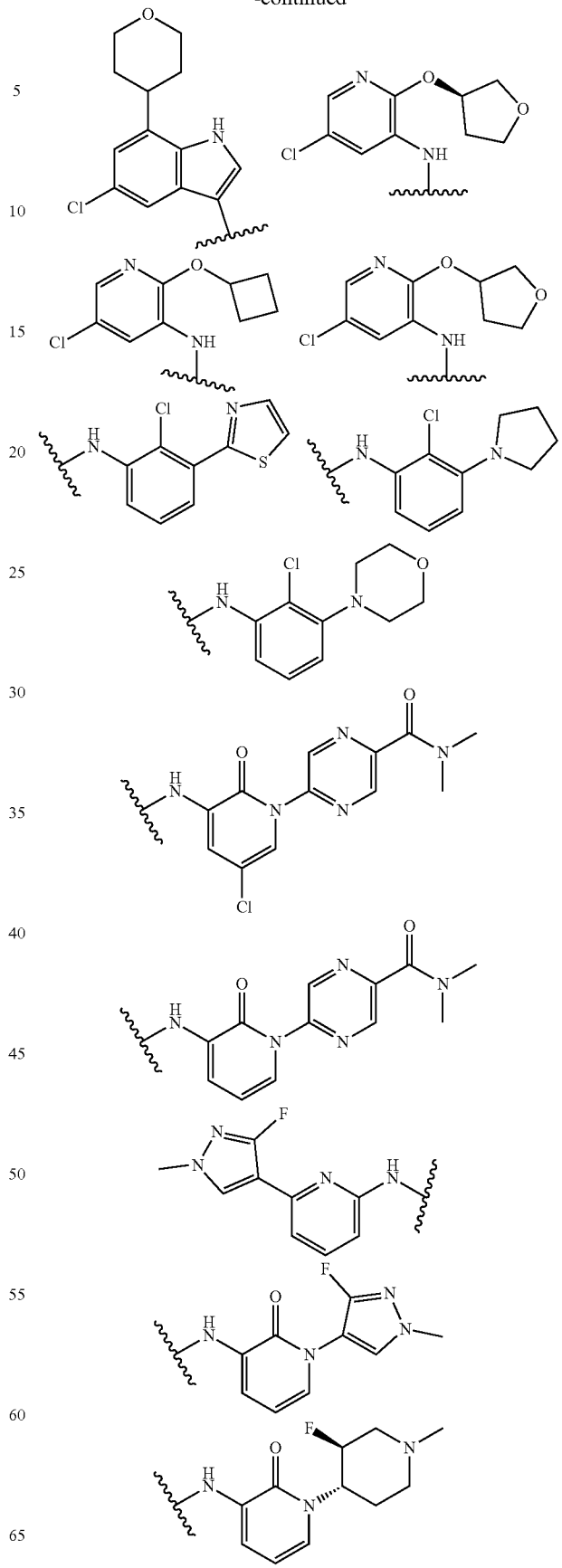

-continued
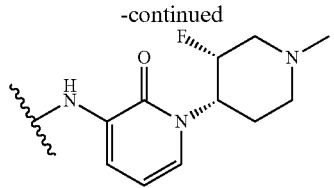

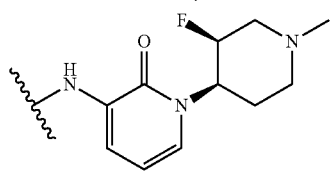
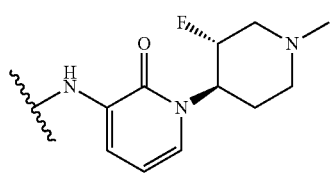
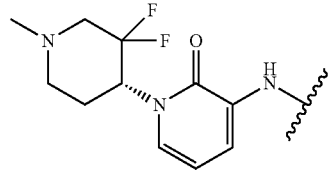
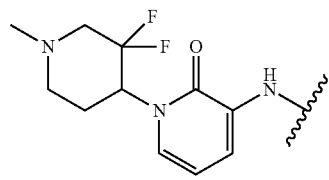
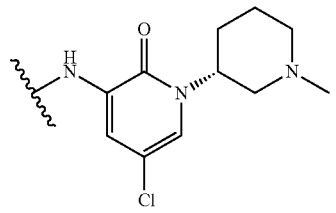
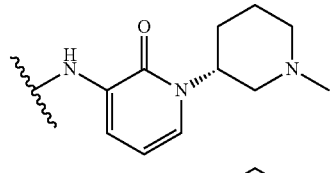
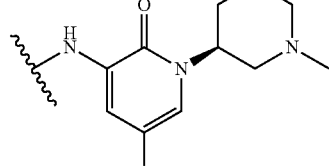
-continued
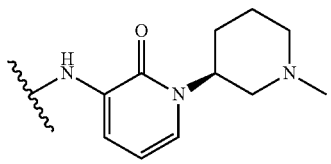
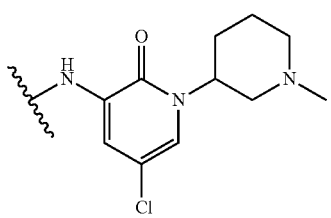
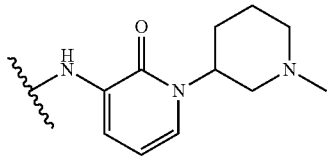
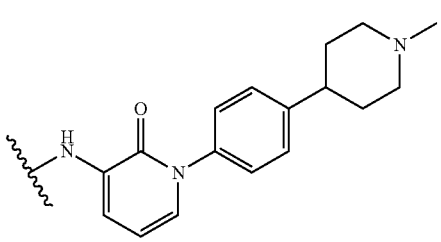
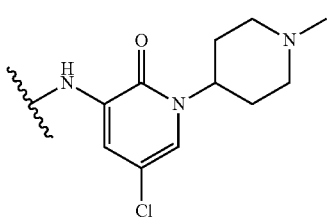
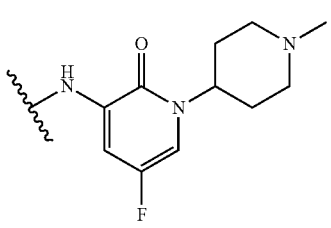
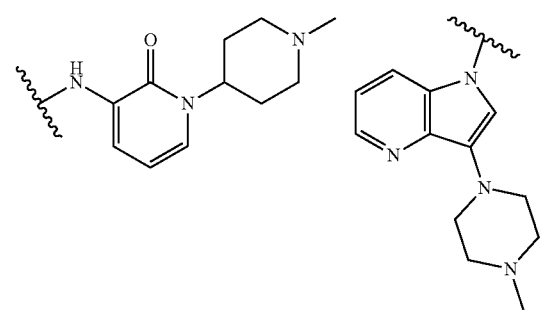

33 34
-continued -continued
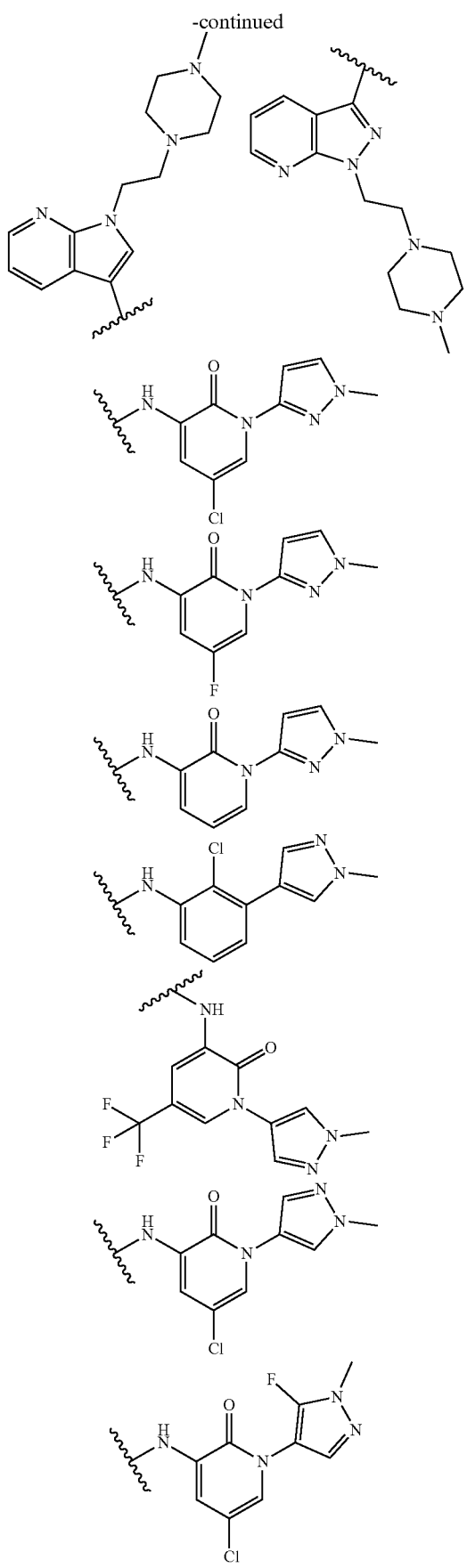
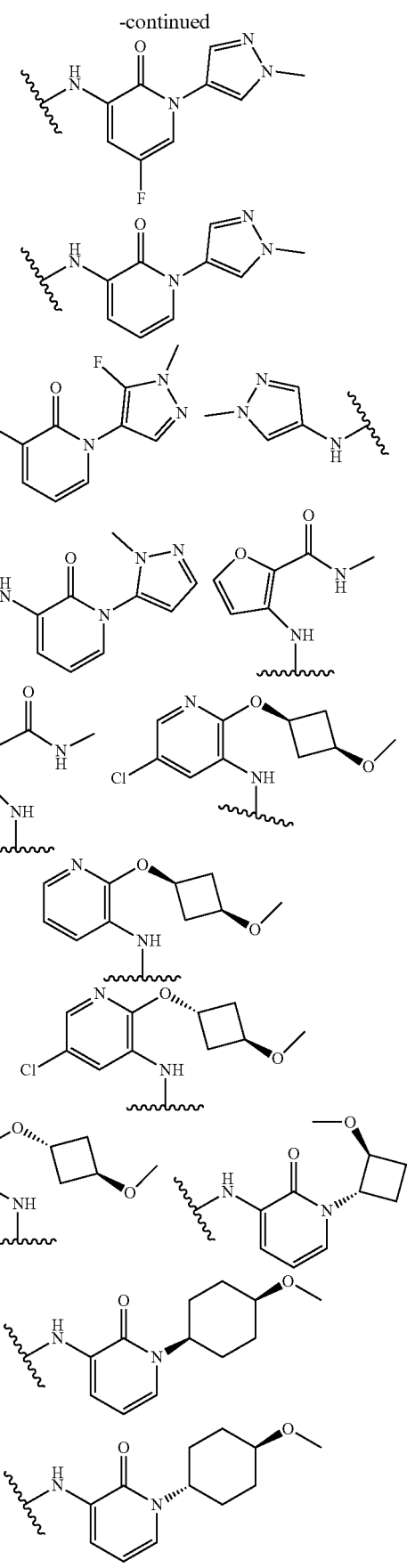

35
-continued
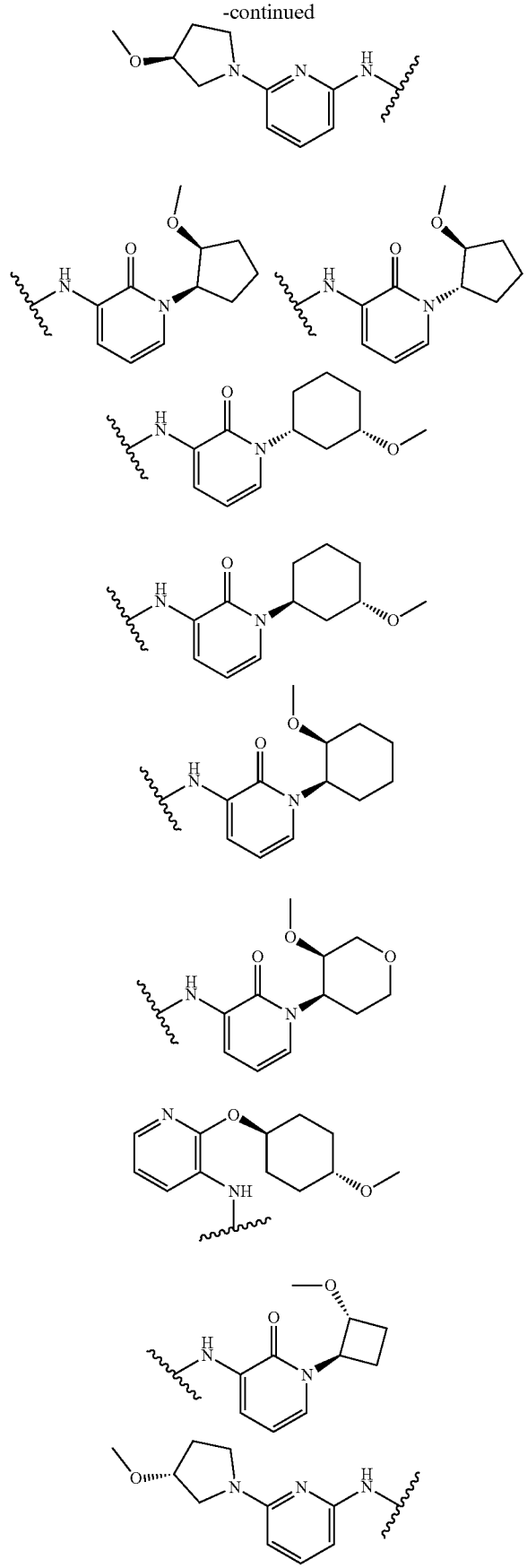
36
-continued
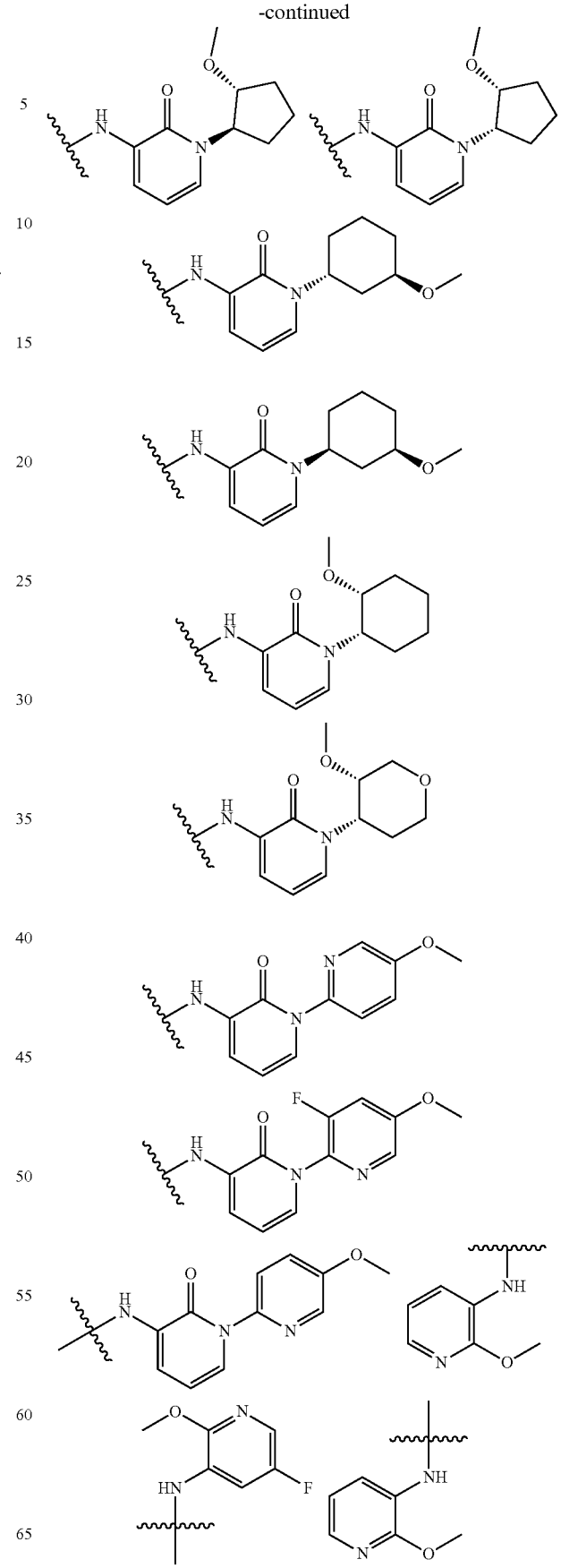

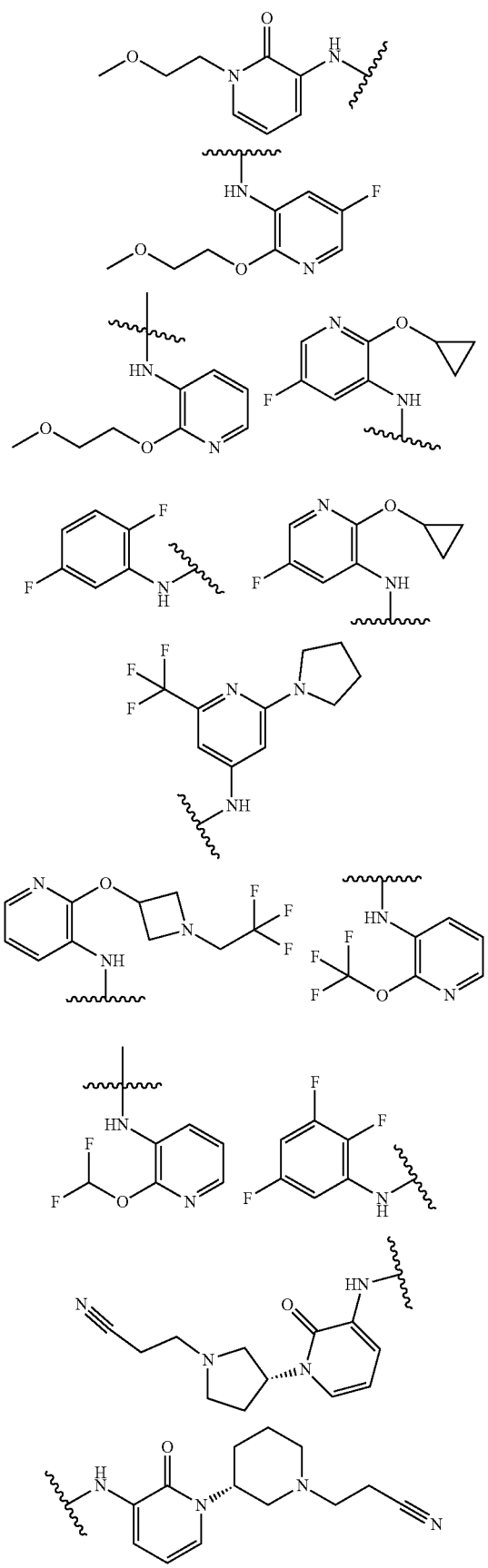
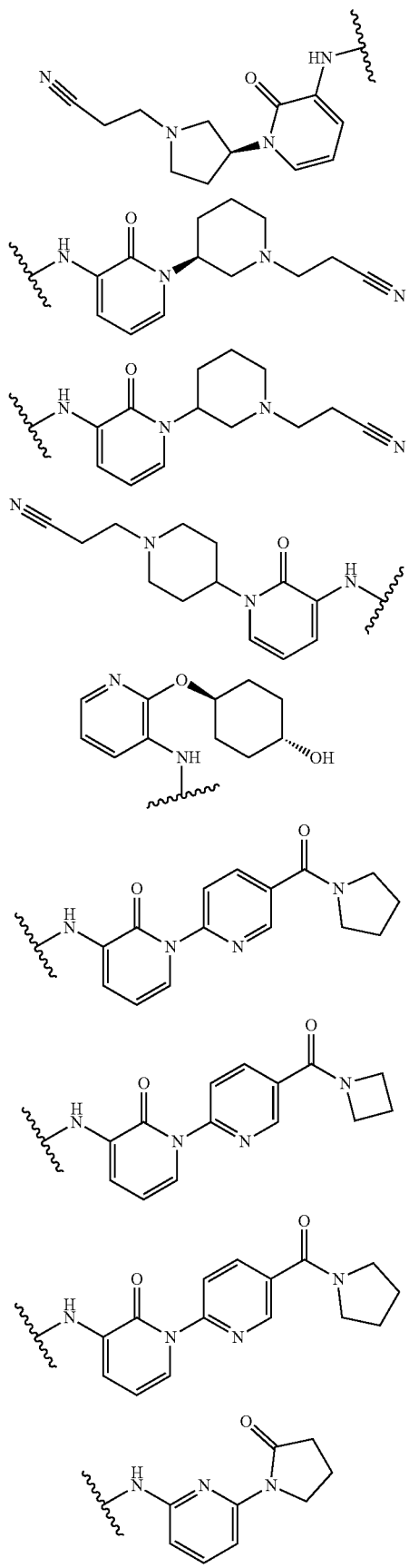

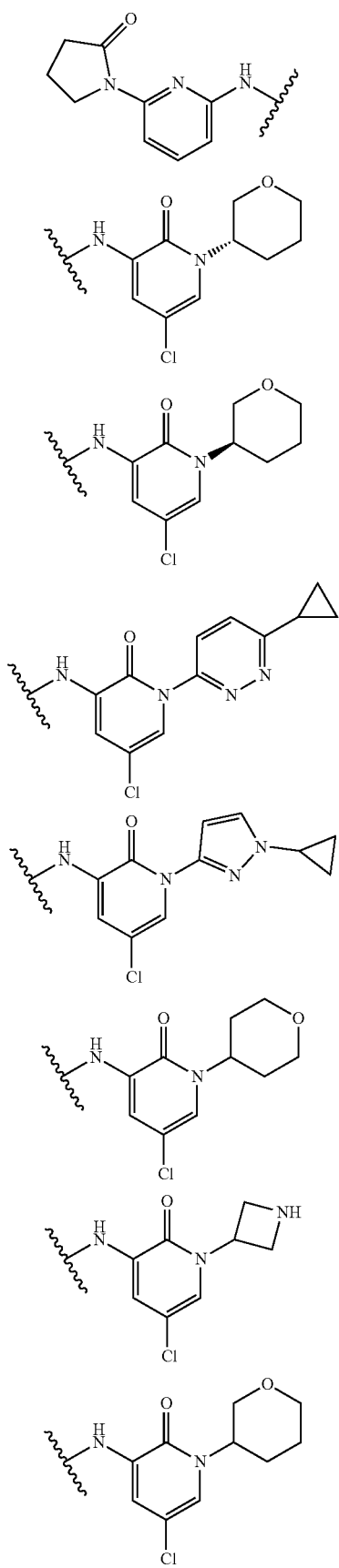
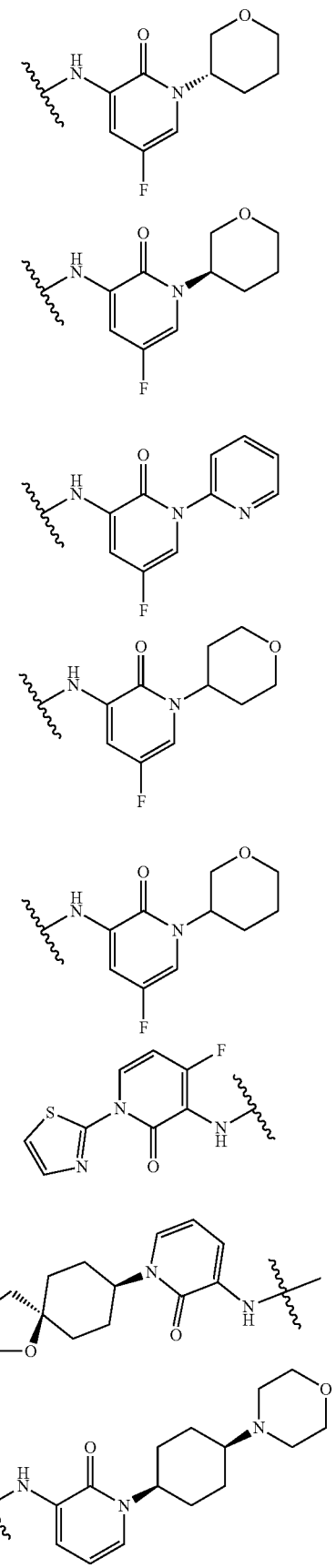

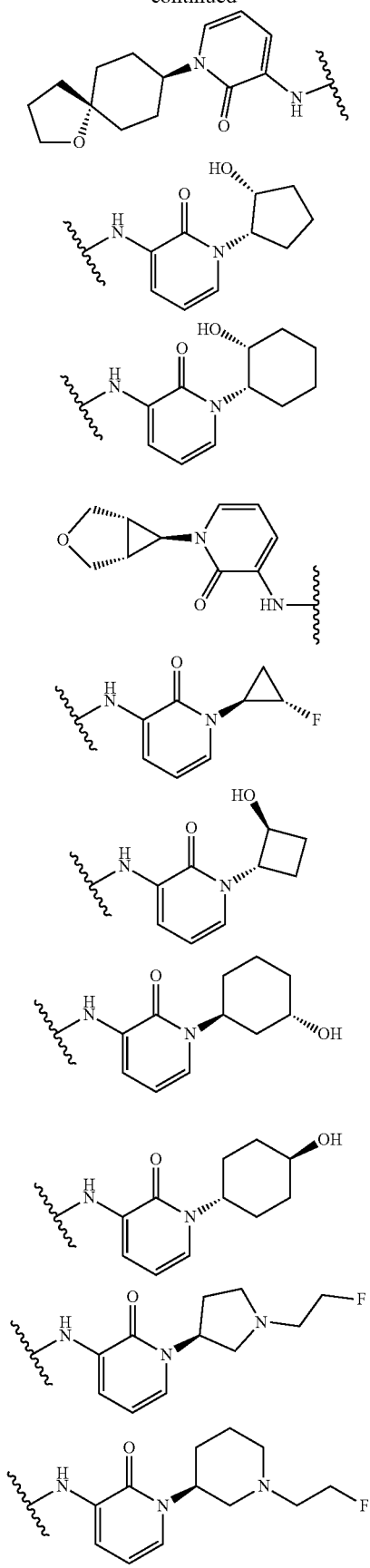
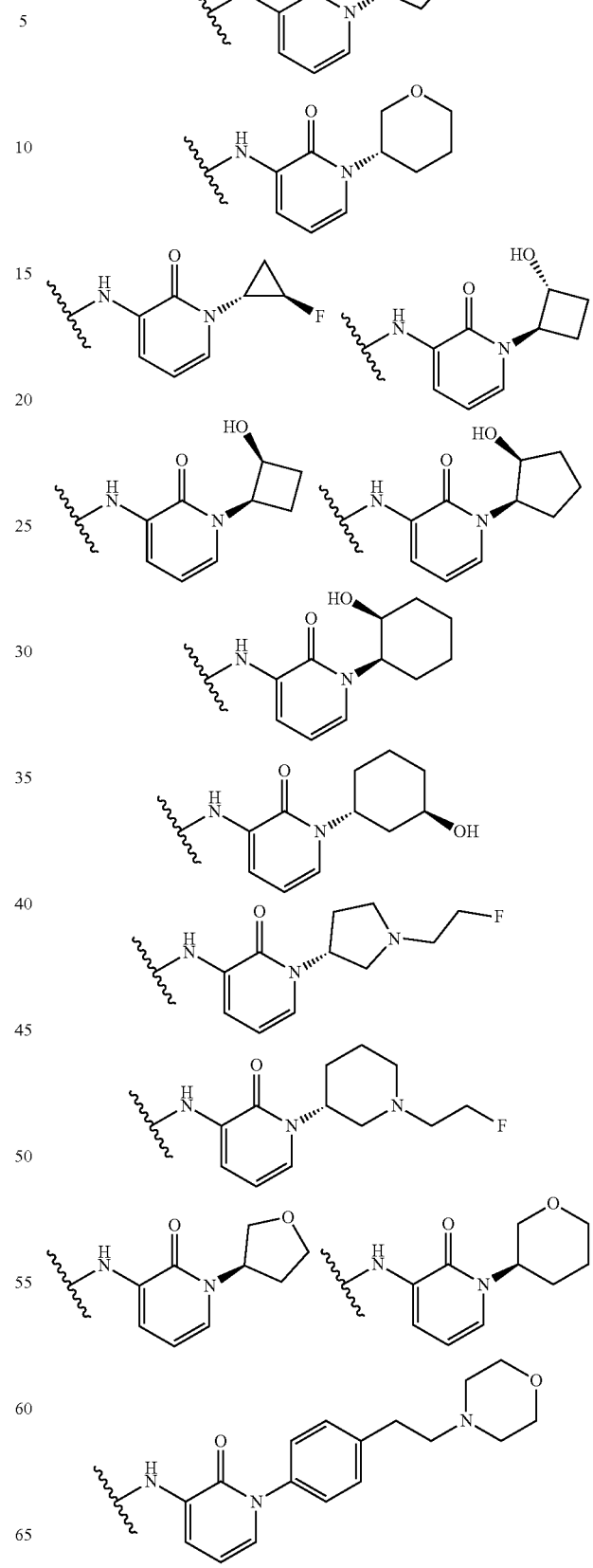

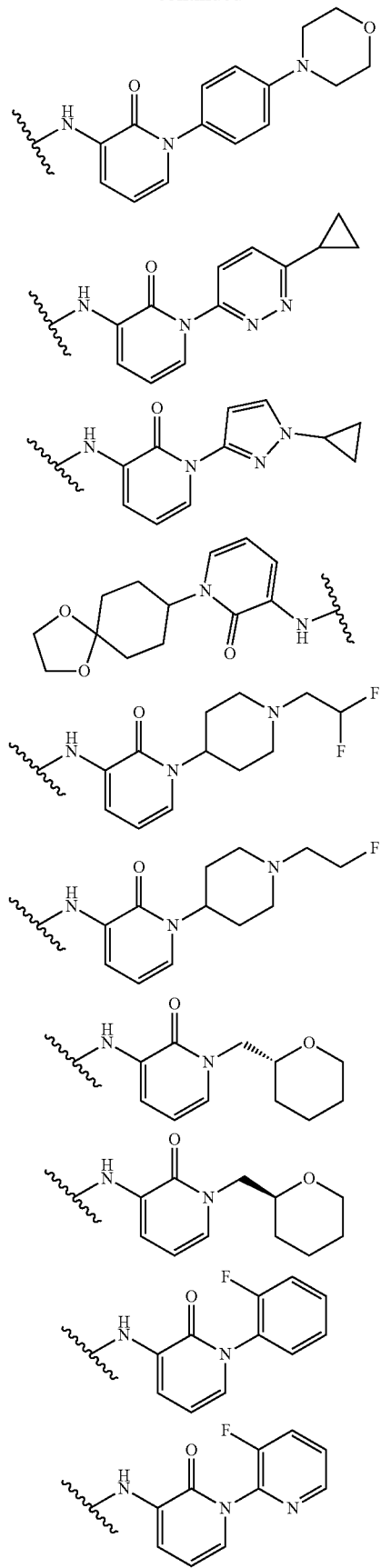
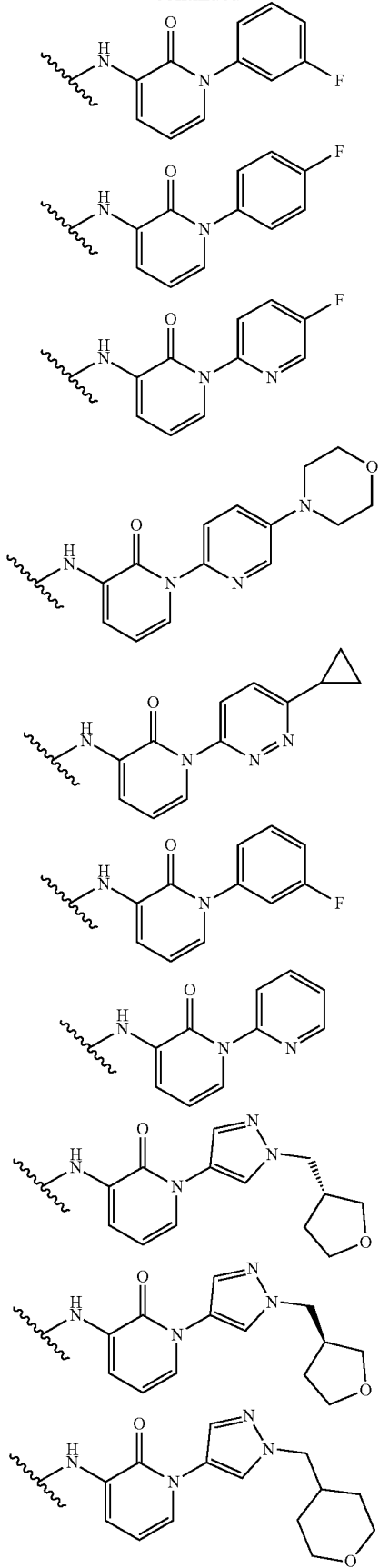

-continued
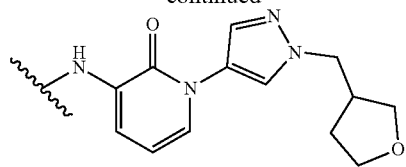
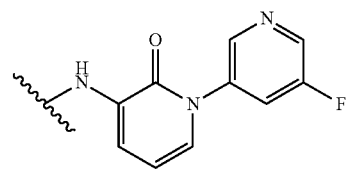
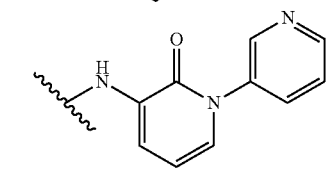
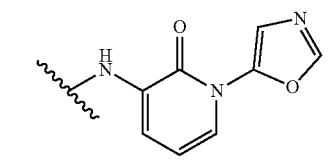
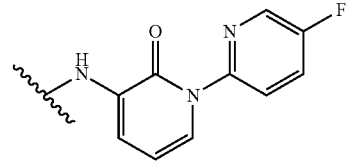
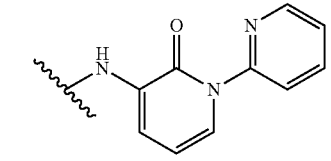
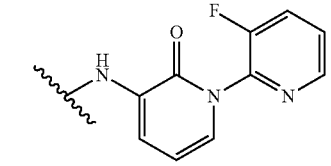
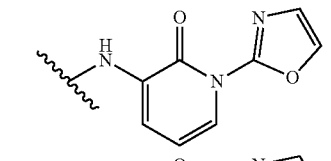
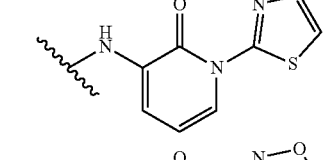
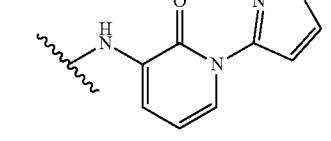
-continued
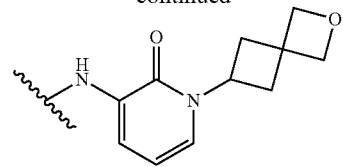
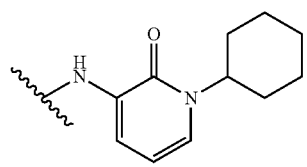
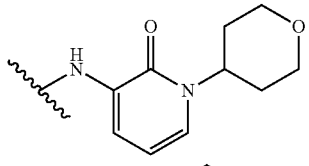
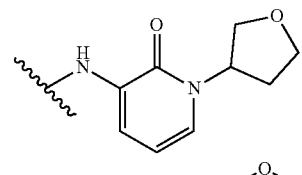
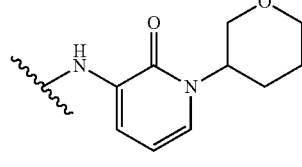
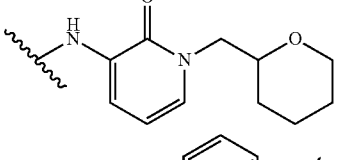
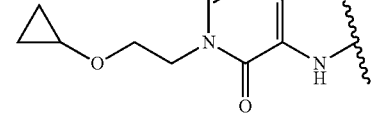
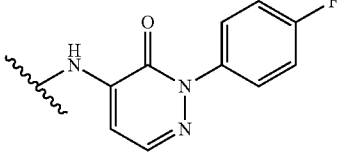
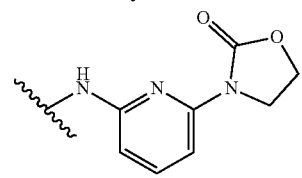

-continued
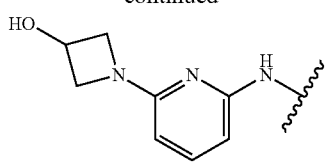
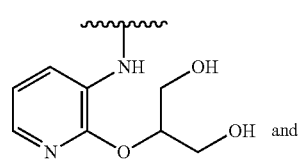
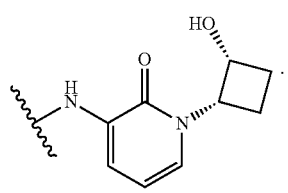
In some embodiments, R⁵ is selected from the following:
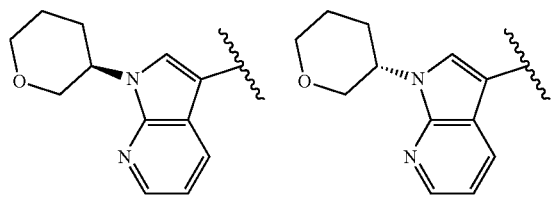
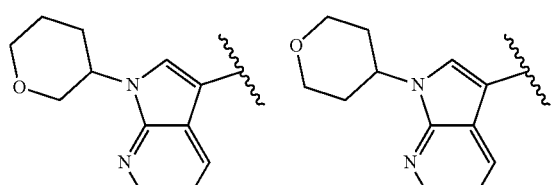
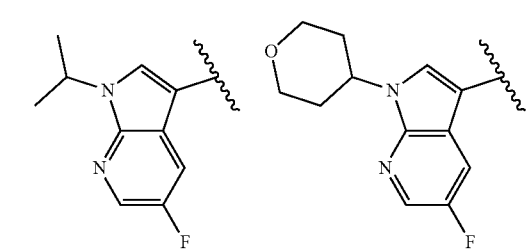
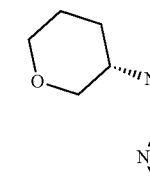
-continued
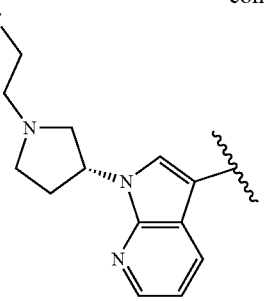
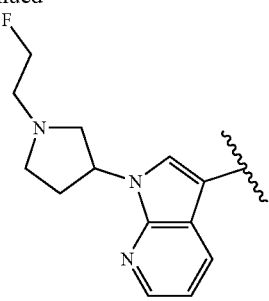
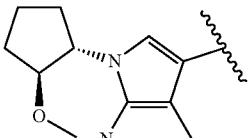
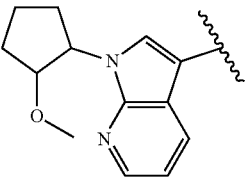
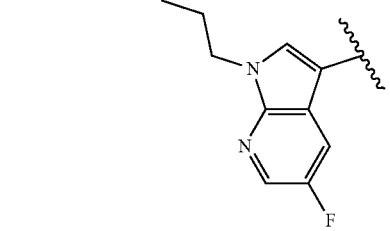
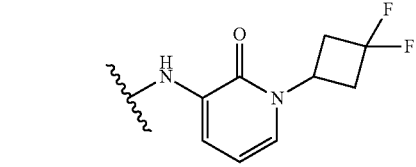
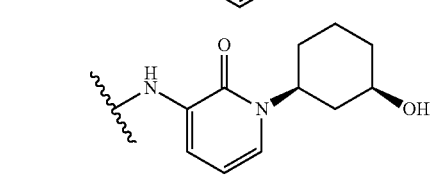
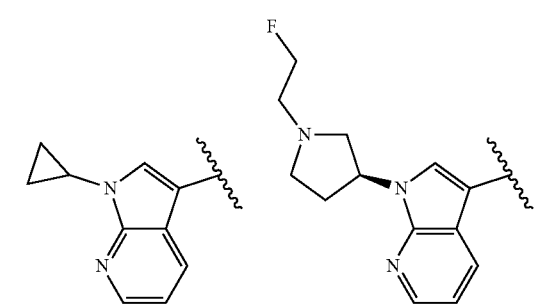
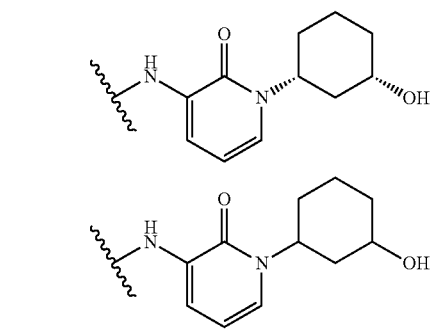
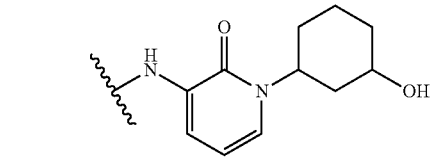

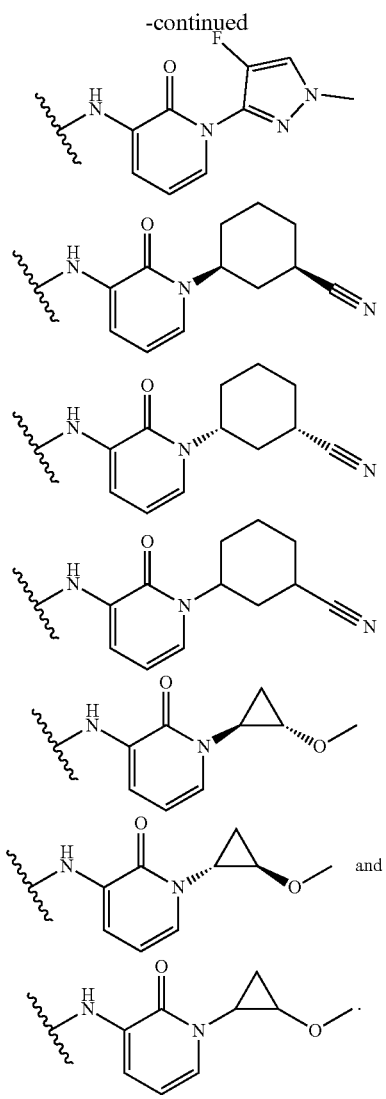

In some embodiments, $R^5$ is selected from those depicted in Table 1, below.

As defined generally above, $R^6$ is hydrogen, $R^A$, or $R^B$, or $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments, $R^6$ is hydrogen.

In some embodiments, $R^6$ is $R^A$. In some embodiments, $R^6$ is $R^B$. In some embodiments, $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{5A}$ and n instances of $R^C$. In some embodiments $R^6$ is hydrogen, $R^A$ or $R^B$.

In some embodiments, $R^6$ is methyl.

In some embodiments, $R^6$ is selected from those depicted in Table 1, below.

As defined generally above, $R^7$ is hydrogen, halogen, —NH$_2$, —NHR$^{7A}$, or —NHC(O)R$^{7A}$; or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$. In some embodiments, $R^7$ is —NH$_2$ or —NHR$^{7A}$. In some embodiments, $R^7$ is —NHMe. In some embodiments, $R^7$ is —NHCD$_3$.

In some embodiments, $R^7$ hydrogen. In some embodiments, $R^7$ halogen. In some embodiments, $R^7$—NH$_2$. In some embodiments, $R^7$—NHR$^{7A}$. In some embodiments, $R^7$—NHC(O)R$^{7A}$. In some embodiments, $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of $R^C$.

In some embodiments, $R^7$ is selected from the following:

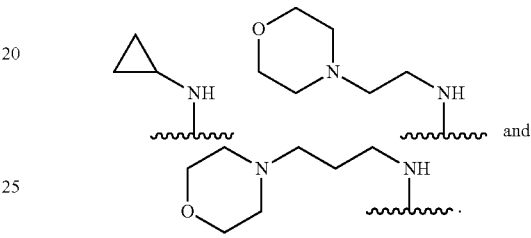

and

In some embodiments, $R^7$ is selected from those depicted in Table 1, below.

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^1$ is —N(R)—. In some embodiments, $L^1$ is —N(H)—.

In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—.

In some embodiments, $L^1$ is —N(R)— or a covalent bond. In some embodiments, $L^1$ is —N(H)— or a covalent bond.

In some embodiments, $L^1$ is selected from those depicted in Table 1, below.

As defined generally above, $R^{3A}$ is $R^B$, and is substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur. In some embodiments, $R^{3A}$ is $C_{1-6}$ aliphatic substituted by q instances of $R^C$. In some embodiments, $R^{3A}$ is a 3-7 membered saturated or partially unsaturated carbocyclic ring substituted by q instances of $R^C$. In some embodiments, $R^{3A}$ is cyclopropyl or cyclobutyl; each substituted by q instances of $R^C$. In some embodiments, $R^{3A}$ is cyclopropyl substituted by q instances of $R^C$. In some embodiments, $R^{3A}$ is cyclobutyl substituted by q instances of $R^C$. In some embodiments, $R^{3A}$ is $R^B$, and is substituted by q instances of $R^C$, provided that $R^{3A}$ is not phenyl.

In some embodiments, $R^{3A}$ is $R^B$, and is substituted by q instances of $R^C$, wherein two $R^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^C$ substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{3A}$ is $C_{1-6}$ aliphatic substituted by q instances of $R^C$ or a 3-7 membered saturated or partially unsaturated carbocyclic ring substituted by q instances of $R^C$.

In some embodiments, $R^{3A}$ is selected from the following:

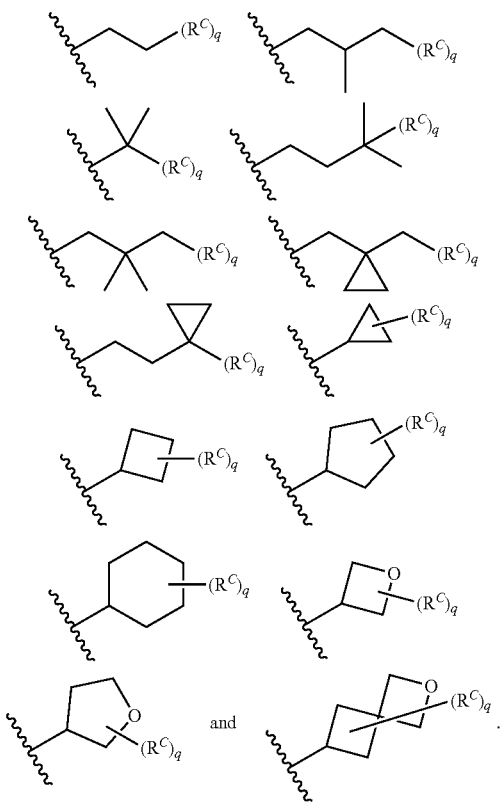

In some embodiments, $R^{3A}$ is selected from those depicted in Table 1, below.

As defined generally above, $R^{5A}$ is $R^A$ or $R^B$, and is substituted by r instances of $R^C$. In some embodiments, $R^{5A}$ is phenyl or a 5-6 membered monocyclic heteroaryl ring having 1-4 heteroatoms independently selected from nitrogen, oxygen, and sulfur; and is substituted by r instances of $R^C$.

In some embodiments, $R^{5A}$ is $R^A$ substituted by r instances of $R^C$. In some embodiments, $R^{5A}$ is $R^B$ substituted by r instances of $R^C$.

In some embodiments, $R^{5A}$ is selected from the following:

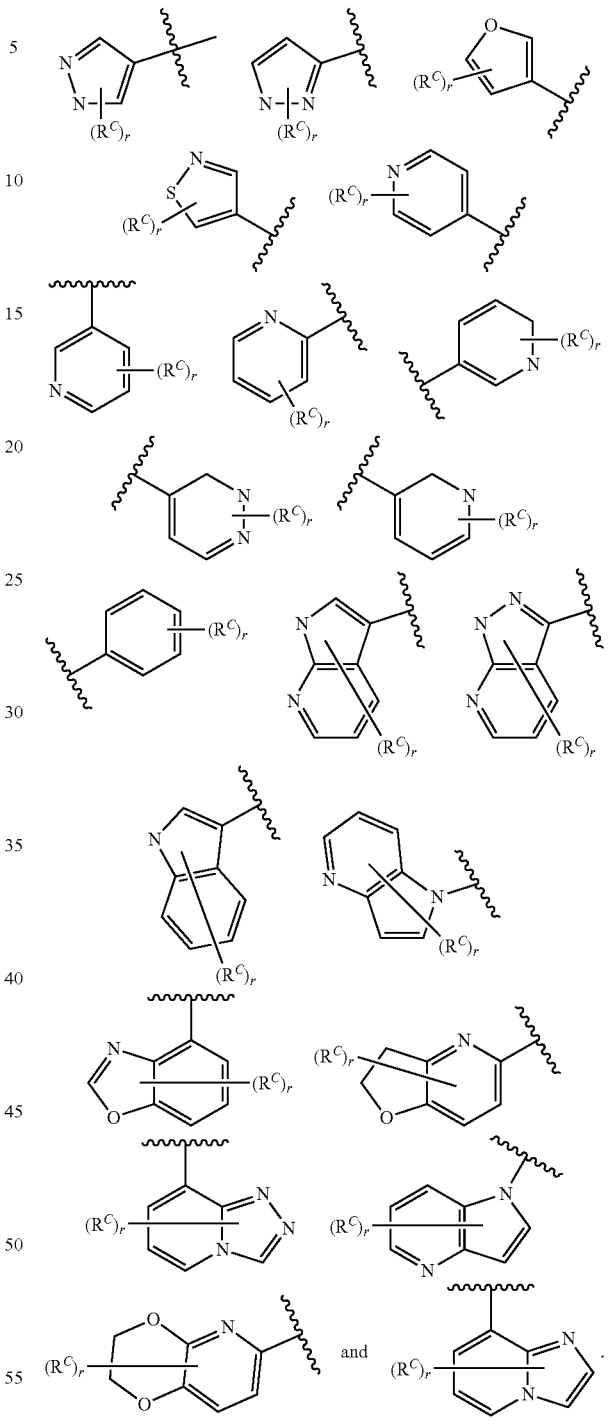

In some embodiments, $R^{5A}$ is selected from those depicted in Table 1, below.

As defined generally above, $R^{7A}$ is $R^B$, and is substituted by q instances of $R^C$. In some embodiments, $R^{7A}$ is $C_{1-6}$ aliphatic substituted by q instances of $R^C$. In some embodiments, $R^{7A}$ is methyl. In some embodiments, $R^{7A}$ is $R^B$, and is substituted by q instances of $R^C$, provided that $R^{7A}$ is not aromatic. In some embodiments, $R^{7A}$ is $R^B$, and is substituted by q instances of $R^C$, provided that $R^{7A}$ is not phenyl.

In some embodiments, $R^{7A}$ is $R^B$, and is substituted by q instances of $R^C$.

In some embodiments, $R^{7A}$ is hydrogen. In some embodiments, $R^{7A}$ is methyl.

In some embodiments, $R^{7A}$ is selected from the following:

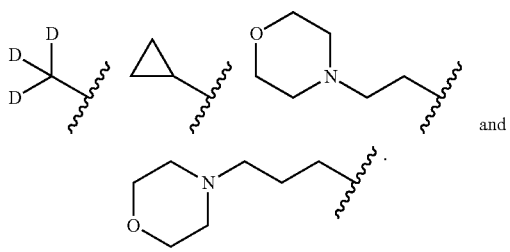

and

In some embodiments, $R^{7A}$ is selected from those depicted in Table 1, below.

As defined generally above, each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^A$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^A$ is selected from those depicted in Table 1, below.

As defined generally above, each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is methyl.

In some embodiments, $R^B$ is selected from those depicted in Table 1, below.

As defined generally above, each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^C$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^C$ is oxo. In some embodiments, $R^C$ is methyl, ethyl, isopropyl, or n-butyl. In some embodiments, $R^C$ is fluoro. In some embodiments, $R^C$ is chloro. In some embodiments, $R^C$ is phenyl.

In some embodiments, $R^C$ is selected from the following:

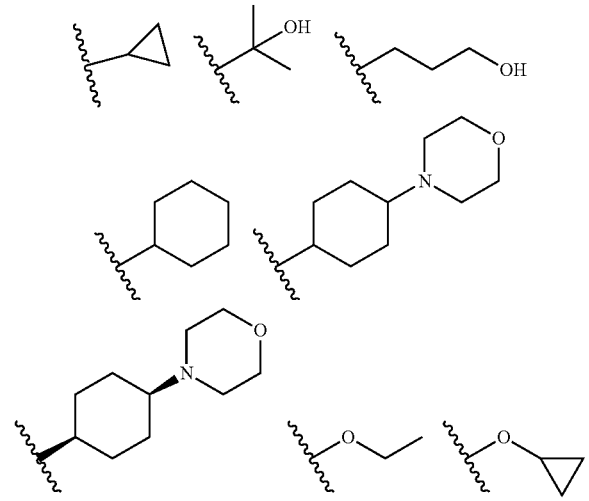

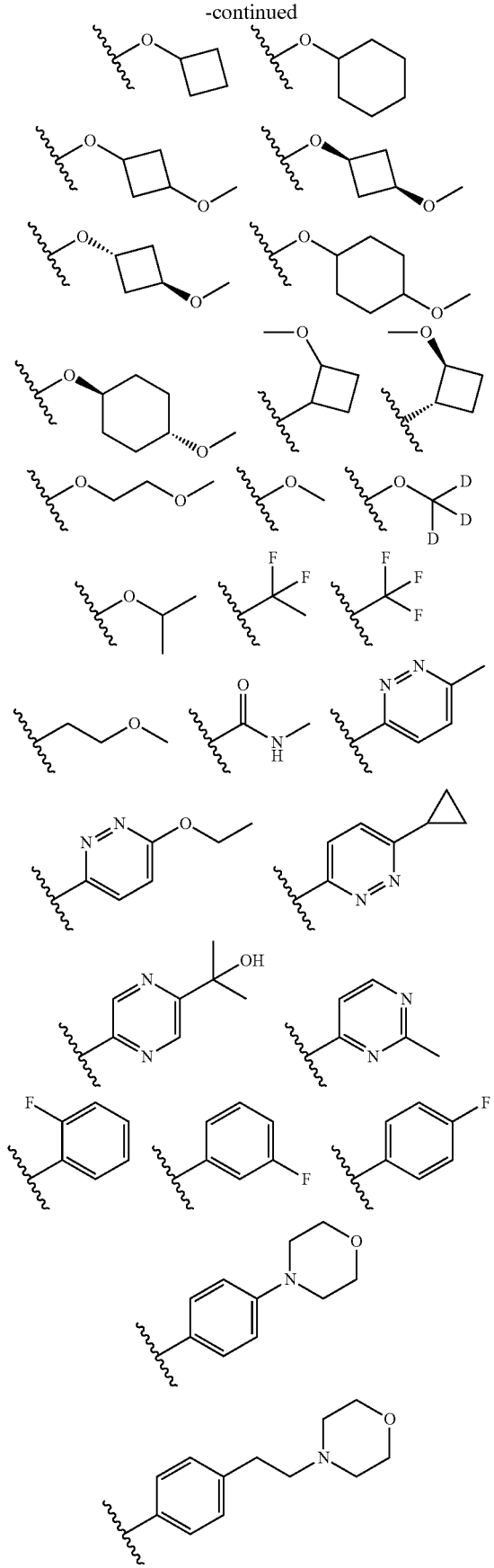
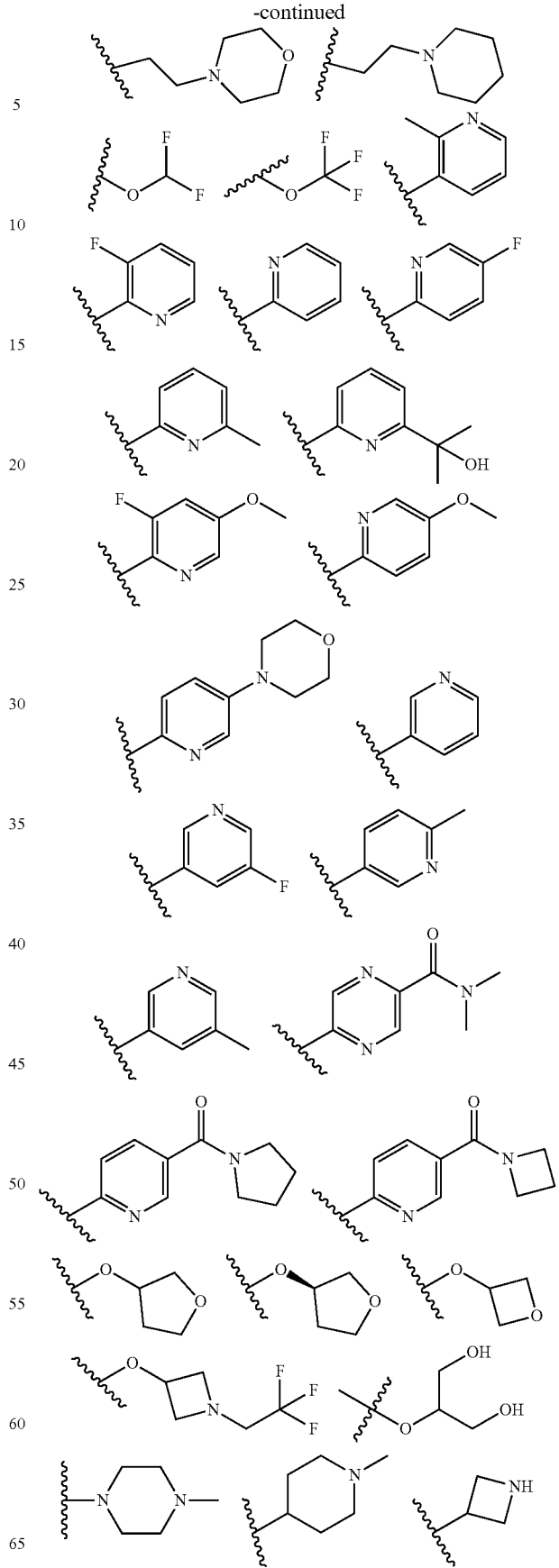

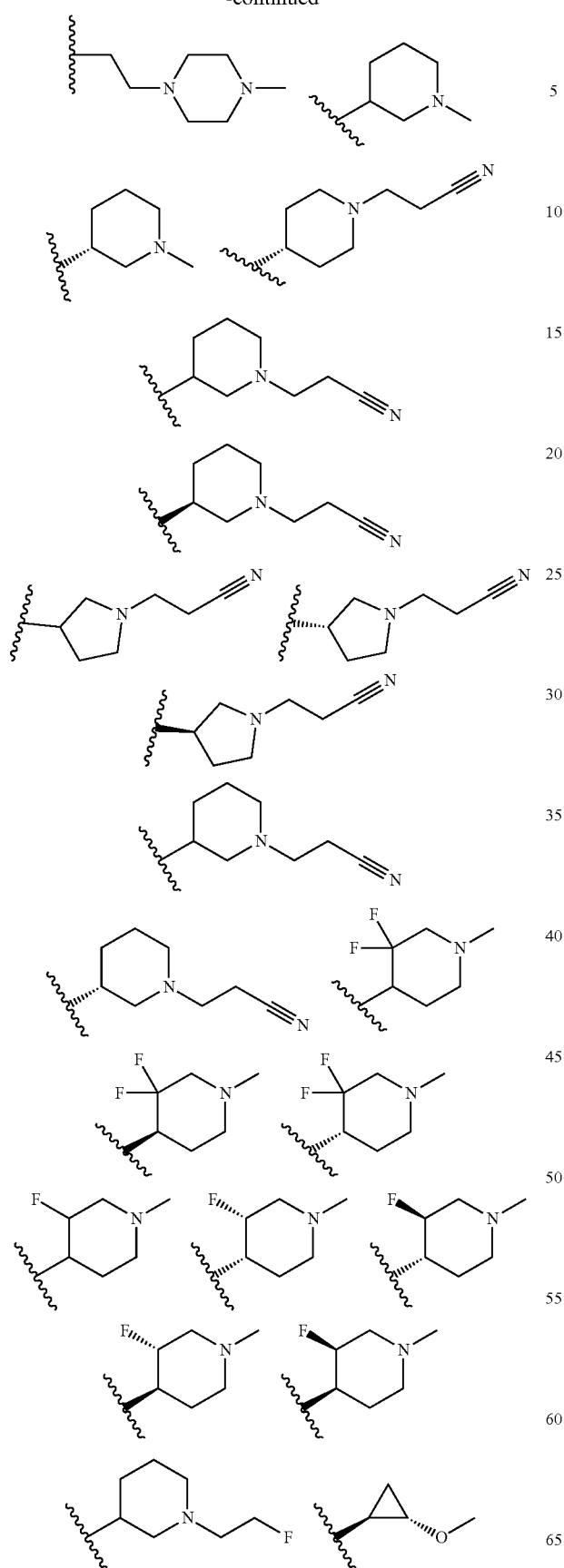
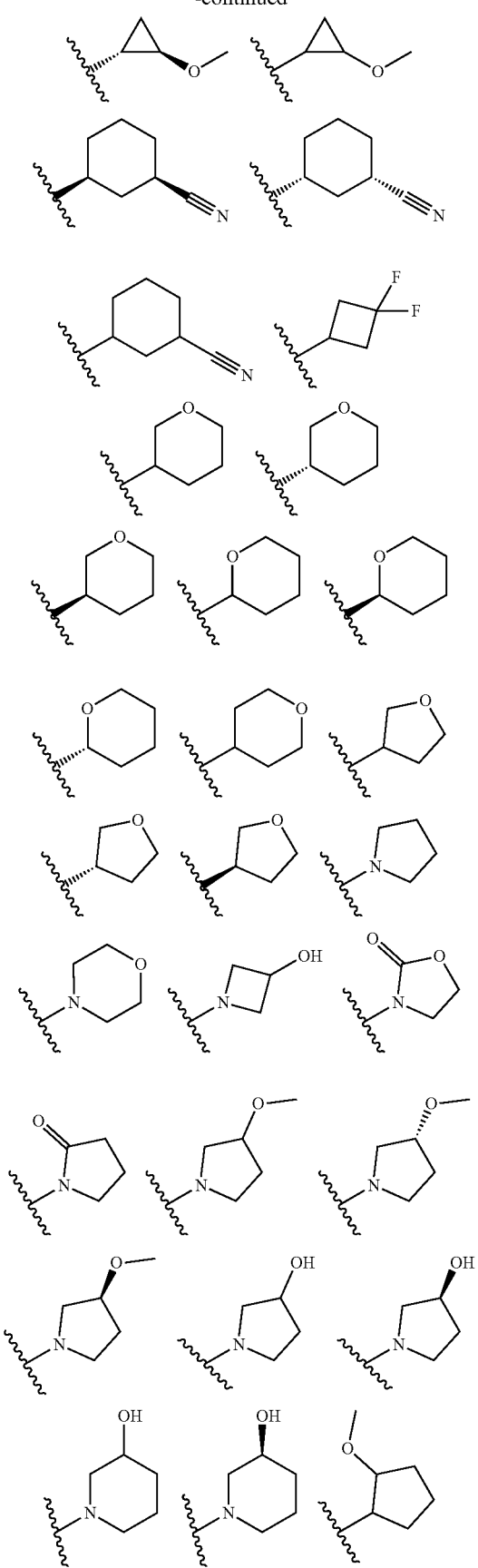

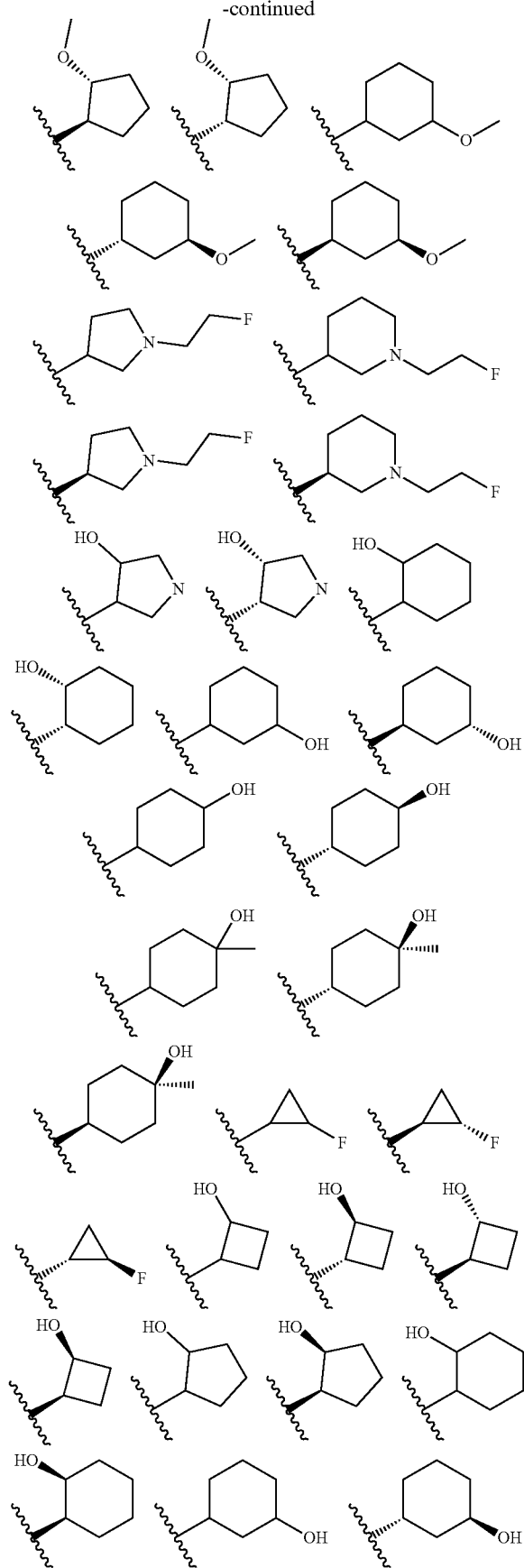
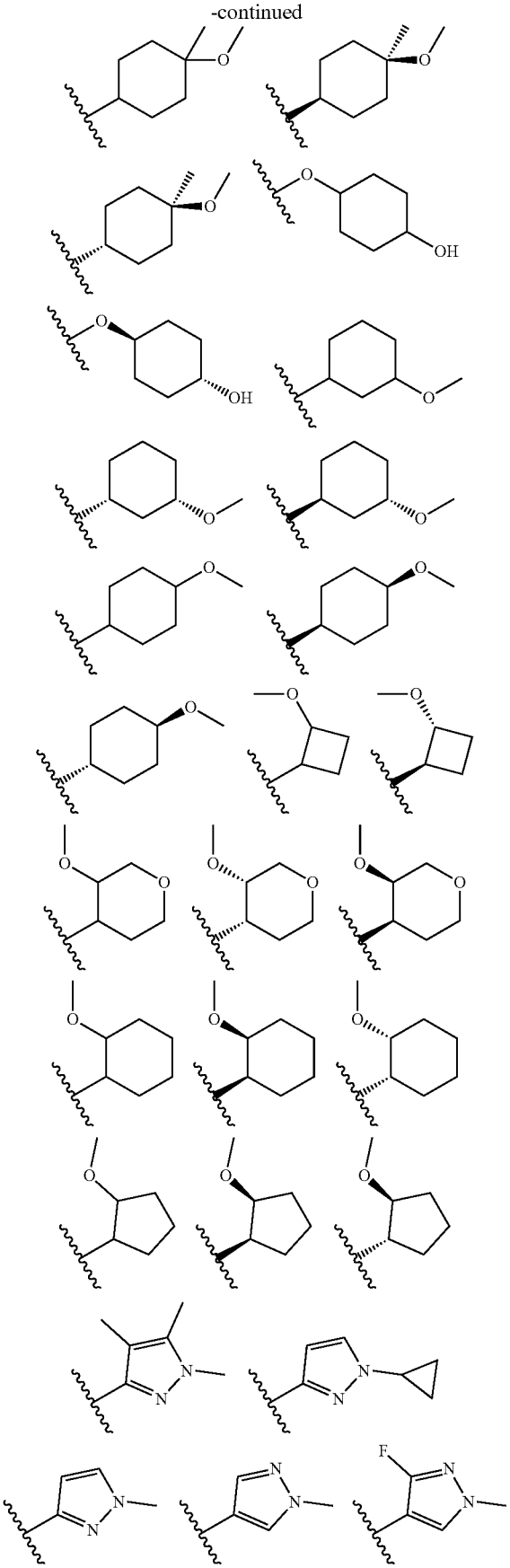

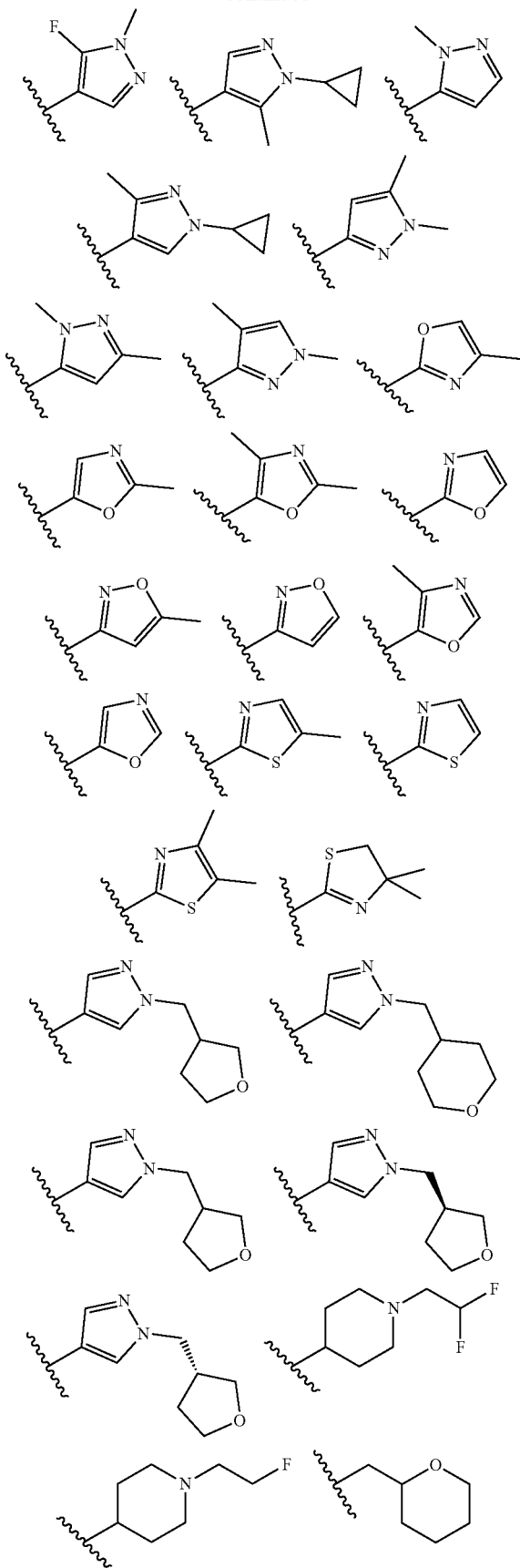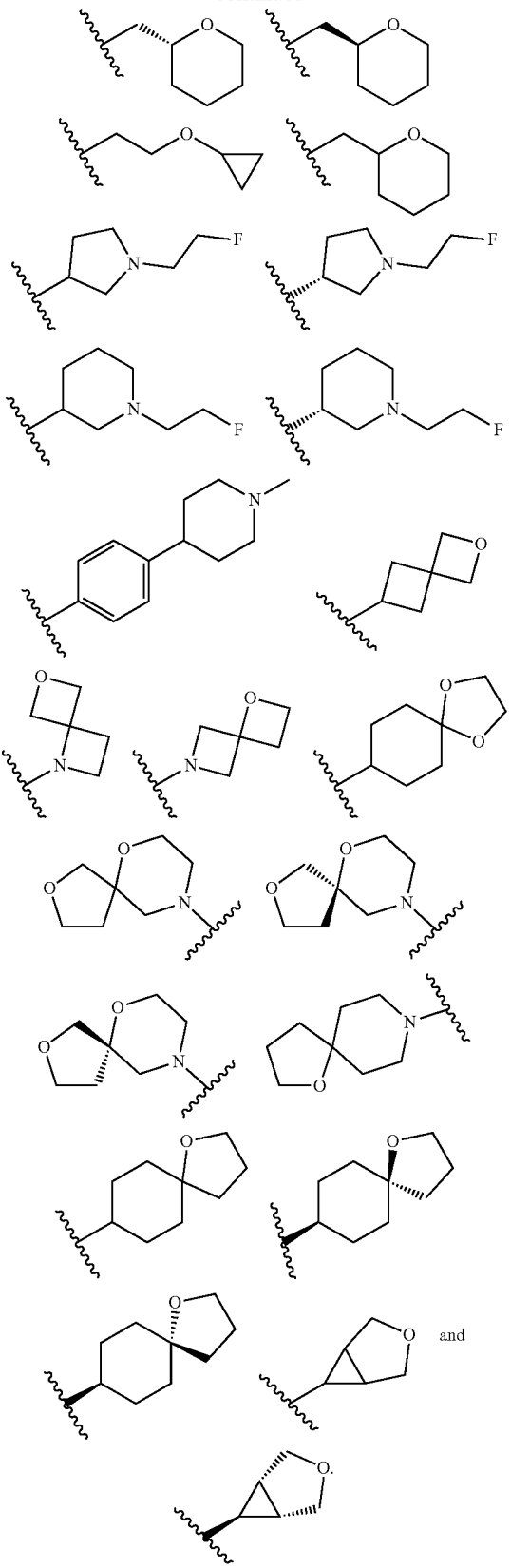
In some embodiments, $R^C$ is selected from those depicted in Table 1, below.

As defined generally above, each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined generally above, each hydrogen bound to carbon can be optionally and independently replaced by deuterium.

In some embodiments, a hydrogen bound to carbon is replaced by deuterium.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

In some embodiments, m is 1, 2, or 3. In some embodiments, m is 1 or 2. In some embodiments, m is 1 or 3. In some embodiments, m is 2 or 3. In some embodiments, m is 2 or 4. In some embodiments, m is 1, 2 or 4. In some embodiments, m is 1, 3 or 4. In some embodiments, m is 2, 3 or 4.

In some embodiments, m is selected from those depicted in Table 1, below.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

In some embodiments, n is 1, 2, or 3. In some embodiments, n is 1 or 2. In some embodiments, n is 1 or 3. In some embodiments, n is 2 or 3. In some embodiments, n is 2 or 4. In some embodiments, n is 1, 2 or 4. In some embodiments, n is 1, 3 or 4. In some embodiments, n is 2, 3 or 4.

In some embodiments, n is selected from those depicted in Table 1, below.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, p is 1, 2, or 3. In some embodiments, p is 1 or 2. In some embodiments, p is 1 or 3. In some embodiments, p is 2 or 3. In some embodiments, p is 2 or 4. In some embodiments, p is 1, 2 or 4. In some embodiments, p is 1, 3 or 4. In some embodiments, p is 2, 3 or 4.

In some embodiments, p is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is 1, 2, or 3. In some embodiments, q is 1 or 2. In some embodiments, q is 1 or 3. In some embodiments, q is 2 or 3. In some embodiments, q is 2 or 4. In some embodiments, q is 1, 2 or 4. In some embodiments, q is 1, 3 or 4. In some embodiments, q is 2, 3 or 4.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is 1, 2, or 3. In some embodiments, r is 1 or 2. In some embodiments, r is 1 or 3. In some embodiments, r is 2 or 3. In some embodiments, r is 2 or 4. In some embodiments, r is 1, 2 or 4. In some embodiments, r is 1, 3 or 4. In some embodiments, r is 2, 3 or 4.

In some embodiments, r is selected from those depicted in Table 1, below.

In some embodiments, the present invention provides a compound of formula I or I' wherein $R^3$ is —C(O)NH$_2$ or —C(O)NHR$^{3A}$, thereby forming a compound of formulas II or III:

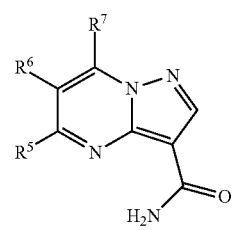

II

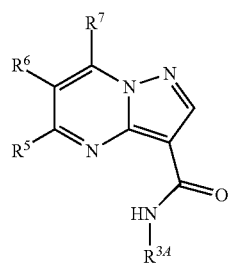

III or a pharmaceutically acceptable salt thereof, wherein each of $R^{3A}$, $R^5$, $R^6$, and $R^7$ is as defined above and described in embodiments herein, both singly and in combination.

In some embodiments, the present invention provides a compound of formula I or I', wherein $L^1$ is —N(R)—, thereby forming a compound of formula IV:

IV

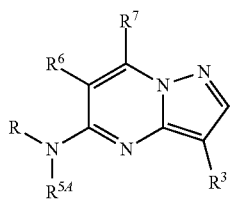

or a pharmaceutically acceptable salt thereof, wherein each of $R^3$, $R^{5A}$, $R^6$, and $R^7$ is as defined above and described in embodiments herein, both singly and in combination.

In some embodiments, the present invention provides a compound of formula II or III, wherein $L^1$ is —N(R)—, thereby forming a compound of formula V or VI respectively:

V

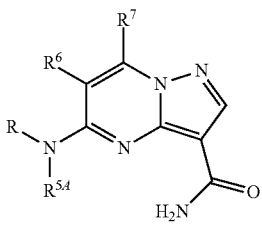

VI

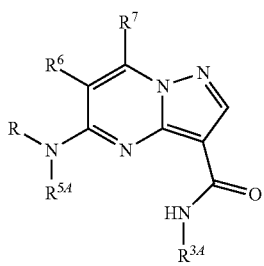

or a pharmaceutically acceptable salt thereof, wherein each of R, $R^{3A}$, $R^{5A}$, $R^6$, and $R^7$ is as defined above and described in embodiments herein, both singly and in combination.

In some embodiments, the present invention provides a compound of formula IV wherein $R^{5A}$ is phenyl or pyridin-3-yl, each substituted by r instances of $R^C$, thereby forming a compound of formula VII or VIII respectively:

VII

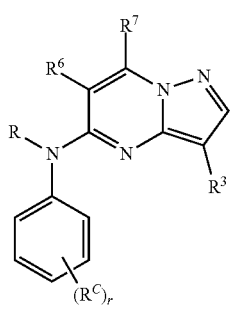

VIII

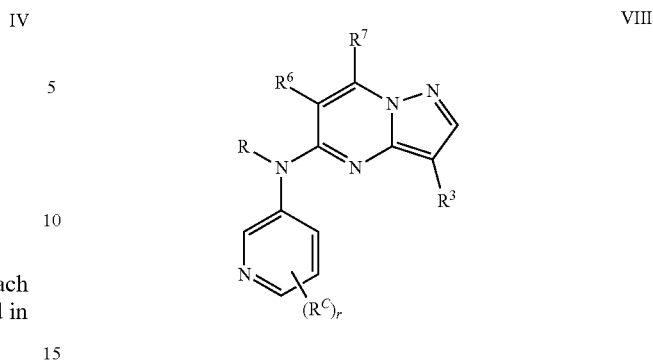

or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula VIII wherein one instance of $R^C$ on $R^{5A}$ is Oxo, thereby forming a compound of formula IX:

IX

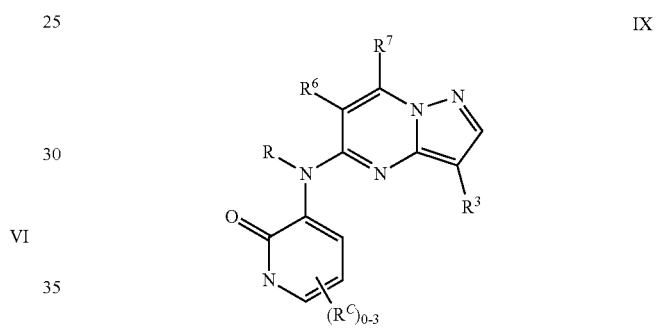

or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula IV, V, VI, VII, VIII, or IX, wherein R is hydrogen, thereby forming a compound of formula X, XI, XII, XIII, XIV, XV respectively:

X

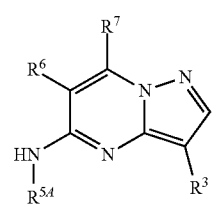

XI

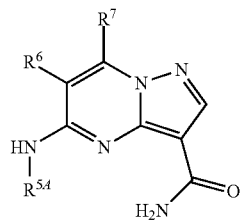

XII
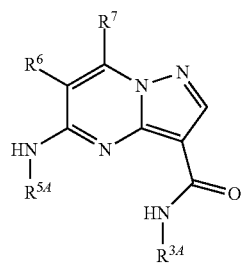

XIII
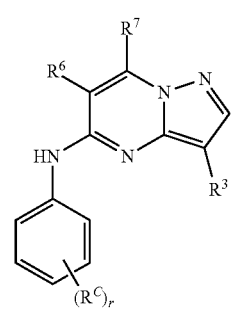

XIV
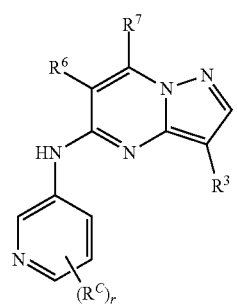

XV
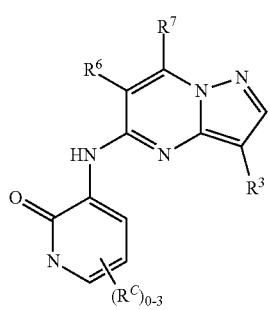

or a pharmaceutically acceptable salt thereof, wherein each of r, R, $R^C$, $R^3$, $R^{3A}$, $R^{5A}$, $R^6$, and $R^7$ is as defined above and described in embodiments herein, both singly and in combination.

In some embodiments, the present invention provides a compound of formula I, I', II, III, IV, V, VI, VII, VIII, IX, X, XI, XII, XIII, XIV, or XV, wherein $R^6$ is hydrogen, thereby forming a compound of formula I-a, II-a, III-a, IV-a, V-a, VI-a, VII-a, VIII-a, IX-a, X-a XI-a, XII-a, XIII-a, XIV-a, or XV-a respectively:

I-a
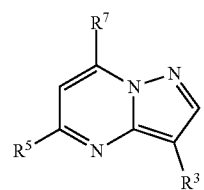

II-a
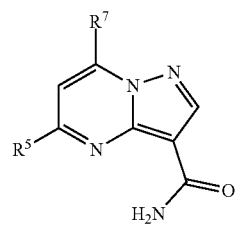

III-a
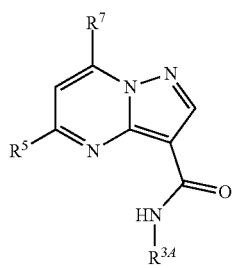

IV-a
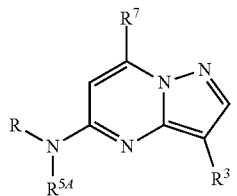

V-a
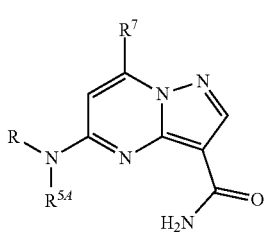

VI-a
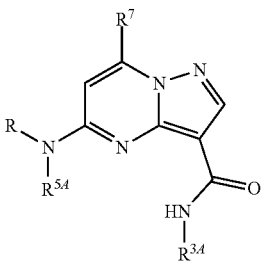

-continued

VII-a
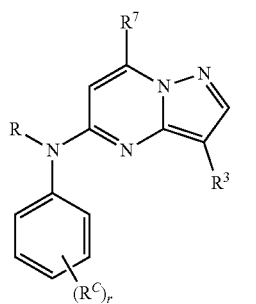

VIII-a
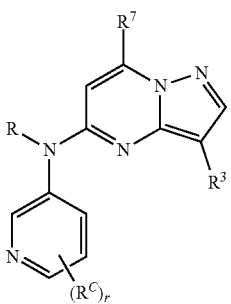

IX-a
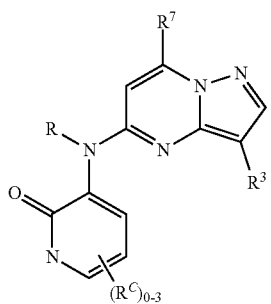

X-a
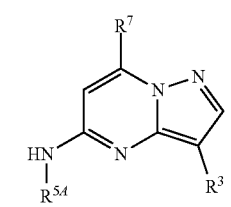

XI-a
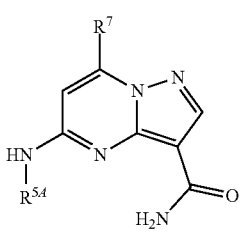

XII-a
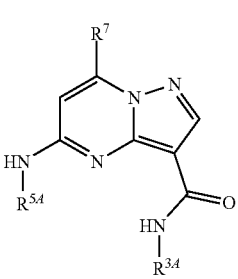

-continued

XIII-a
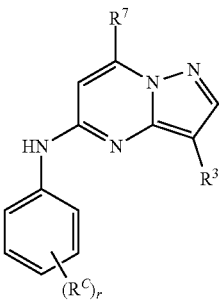

XIV-a
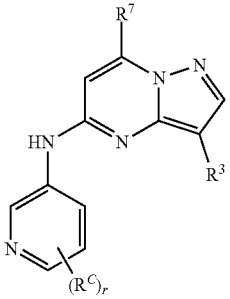

XV-a
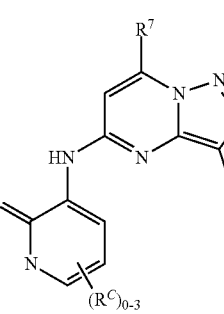

or a pharmaceutically acceptable salt thereof, wherein each of r, R, $R^C$, $R^3$, $R^{3A}$, $R^5$, $R^{5A}$, and $R^7$ is as defined above and described in embodiments herein, both singly and in combination.

In some embodiments, the present invention provides a compound of formula I, I', II, III, IV, V, VI, VII, VIII, IX, X, XI, XII, XIII, XIV, XV, I-a, II-a, III-a, IV-a, V-a, VI-a, VII-a, VIII-a, IX-a, X-a XI-a, XII-a, XIII-a, XIV-a, or XV-a wherein $R^7$ is —NH$_2$ or —NHR$^{7A}$.

In some embodiments, the present invention provides a compound of formula I, I', II, III, IV, V, VI, VII, VIII, IX, X, XI, XII, XIII, XIV, XV, I-a, II-a, III-a, IV-a, V-a, VI-a, VII-a, VIII-a, IX-a, X-a XI-a, XII-a, XIII-a, XIV-a, or XV-a wherein $R^7$ is —NHR$^{7A}$. thereby forming a compound of formula I-b, II-b, III-b, IV-b, V-b, VI-b, VII-b, VIII-b, IX-b, X-b, XI-b, XII-b, XIII-b, XIV-b, XV-b, I-c, II-c, III-c, IV-c, V-c, VI-c, VII-c, VIII-c, IX-c, X-c XI-c, XII-c, XIII-c, XIV-c, or XV-c respectively:

I-b
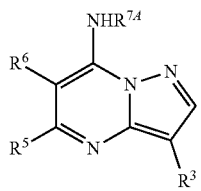

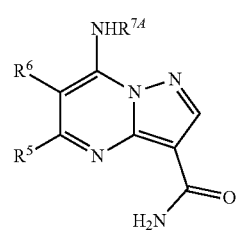
II-b
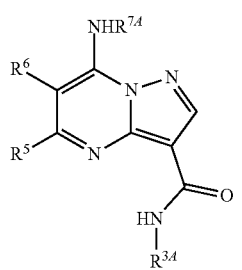
III-b
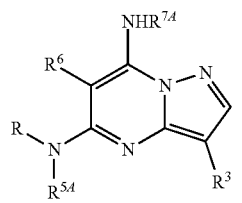
IV-b
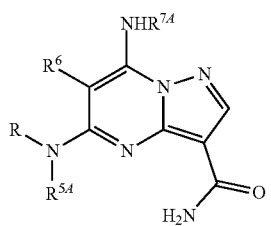
V-b
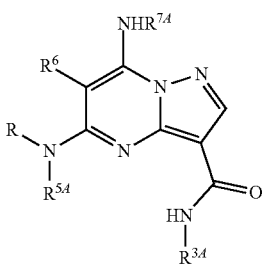
VI-b
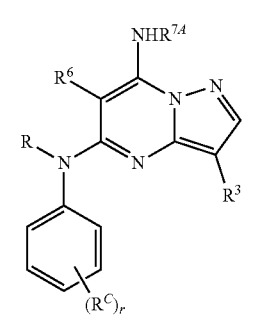
VII-b
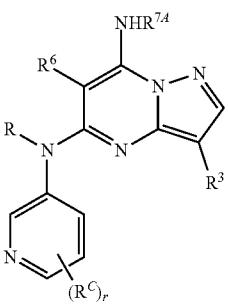
VIII-b
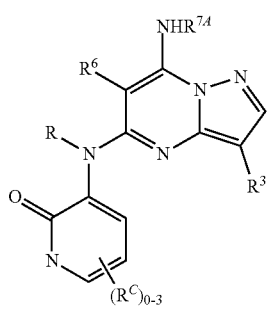
IX-b
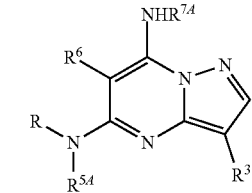
X-b
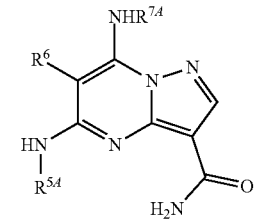
XI-b
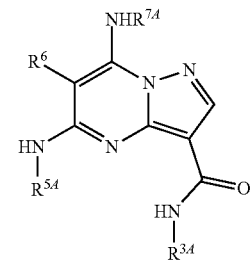
XII-b
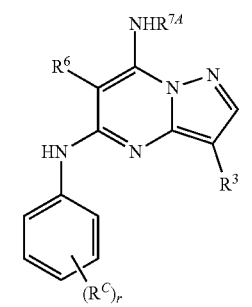
XIII-b

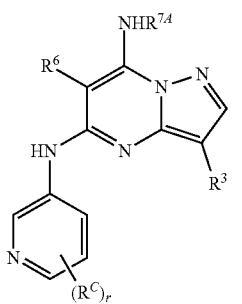 XIV-b
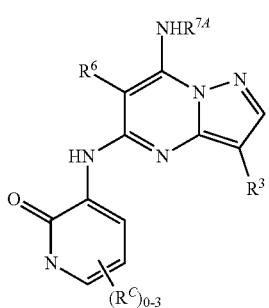 XV-b
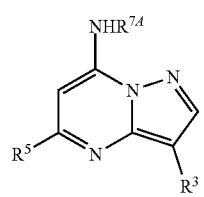 I-c
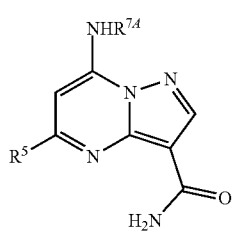 II-c
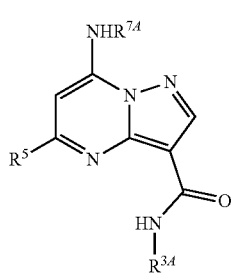 III-c
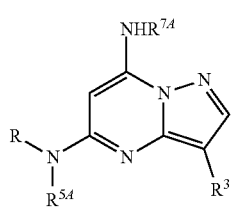 IV-c
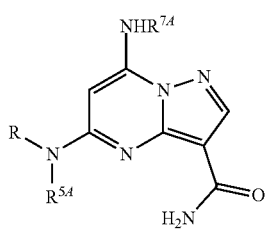 V-c
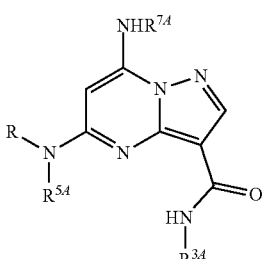 VI-c
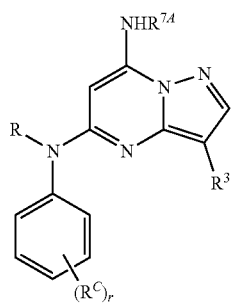 VII-c
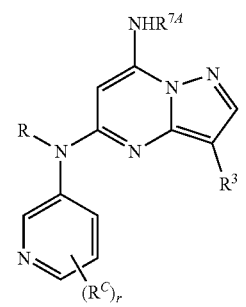 VIII-c
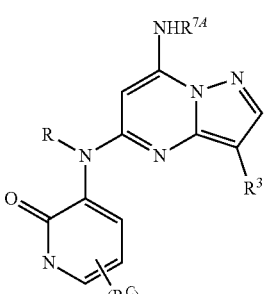 IX-c
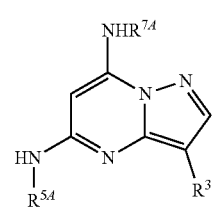 X-c XI-c

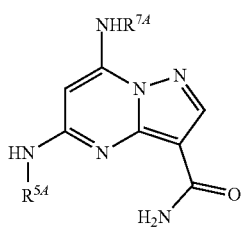

XII-c

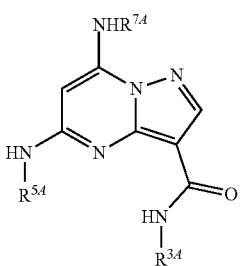

XIII-c

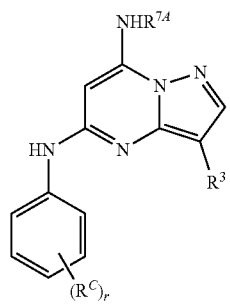

XIV-c

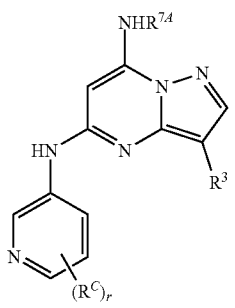

XV-c

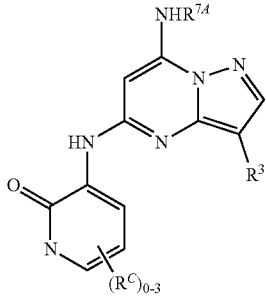

or a pharmaceutically acceptable salt thereof, wherein each of r, R, $R^C$, $R^3$, $R^{3A}$, $R^5$, $R^{5A}$, $R^6$, and $R^{7A}$ is as defined above and described in embodiments herein, both singly and in combination.

In some embodiments, the present invention provides a compound of formula I-b, II-b, III-b, IV-b, V-b, VI-b, VII-b, VIII-b, IX-b, X-b, XI-b, XII-b, XIII-b, XIV-b, XV-b, I-c, II-c, III-c, IV-c, V-c, VI-c, VII-c, VIII-c, IX-c, X-c XI-c, XII-c, XIII-c, XIV-c, or XV-c, wherein $R^{7A}$ is $R^B$, substituted by q instances of $R^C$, wherein $R^{7A}$ is not phenyl. In some embodiments, the present invention provides a compound of formula I-b, II-b, III-b, IV-b, V-b, VI-b, VII-b, VIII-b, IX-b, X-b, XI-b, XII-b, XIII-b, XIV-b, XV-b, I-c, II-c, III-c, IV-c, V-c, VI-c, VII-c, VIII-c, IX-c, X-c XI-c, XII-c, XIII-c, XIV-c, or XV-c, wherein $R^{7A}$ is methyl. In some embodiments, the present invention provides a compound of formula I-b, II-b, III-b, IV-b, V-b, VI-b, VII-b, VIII-b, IX-b, X-b, XI-b, XII-b, XIII-b, XIV-b, XV-b, I-c, II-c, III-c, IV-c, V-c, VI-c, VII-c, VIII-c, IX-c, X-c XI-c, XII-c, XIII-c, XIV-c, or XV-c, wherein $R^{7A}$ is —CD$_3$.

In some embodiments, the present invention provides a compound of formula I-b, III-b, IV-b, VI-b, VII-b, VIII-b, IX-b, X-b, XII-b, XIII-b, XIV-b, XV-b, I-c, III-c, IV-c, VI-c, VII-c, VIII-c, IX-c, X-c, XII-c, XIII-c, XIV-c, or XV-c, wherein $R^{3A}$ is $R^B$, and is substituted by q instances of $R^C$, provided that $R^{3A}$ is not phenyl.

In some embodiments, the present invention provides a compound of formula I-b, III-b, IV-b, VI-b, VII-b, VIII-b, IX-b, X-b, XII-b, XIII-b, XIV-b, XV-b, I-c, III-c, IV-c, VI-c, VII-c, VIII-c, IX-c, X-c, XII-c, XIII-c, XIV-c, or XV-c, wherein each of $R^{3A}$ and $R^{7A}$ is $R^B$, and is substituted by q instances of $R^C$, provided that neither $R^{3A}$ nor $R^{7A}$ is phenyl.

In some embodiments, the present invention provides a compound of formula IV wherein $R^{5A}$ is pyridin-2-yl substituted by r instances of $R^C$, thereby forming a compound of formula XVI:

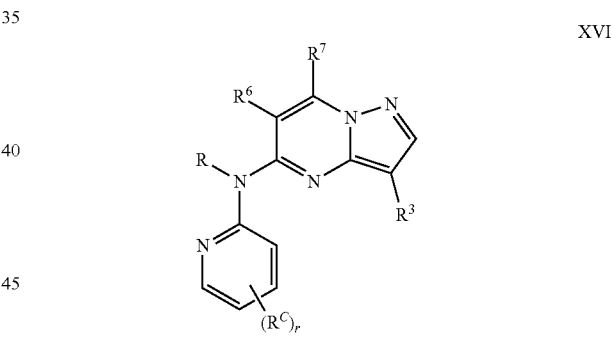

XVI or a pharmaceutically acceptable salt thereof, wherein each of r, R, $R^C$, $R^3$, $R^6$, and $R^7$ is as defined above and described in embodiments herein, both singly and in combination.

In some embodiments, the present invention provides a compound of formula I or I', wherein $R^5$ is -$L^1$-$R^{5A}$, $L^1$ is a covalent bond, and $R^{5A}$ is an 8-10 membered bicyclic heteroaryl ring having 1-4 heteroatoms independently selected from nitrogen, oxygen, and sulfur. In some embodiments, the present invention provides a compound of formula I or I', wherein $R^5$ is -$L^1$-$R^{5A}$, $L^1$ is a covalent bond, and $R^{5A}$ is an 8-10 membered bicyclic heteroaryl ring having 1-4 heteroatoms independently selected from nitrogen, oxygen, and sulfur.

In some embodiments, the present invention provides a compound of formula I or I', wherein $R^5$ is -$L^1$-$R^{5A}$, $L^1$ is a covalent bond, and $R^{5A}$ is indol-1-yl, indol-3-yl, 4-azaindol-1-yl, 7-azaindol-3-yl, or 7-azaindazol-3-yl, each $R^{5A}$ substituted by r instances of $R^C$, thereby providing a compound of formulas XVII, XVIII, XIX, XX, or XXI respectively:

XVII

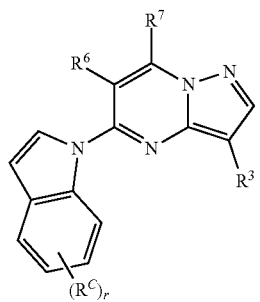

XVIII

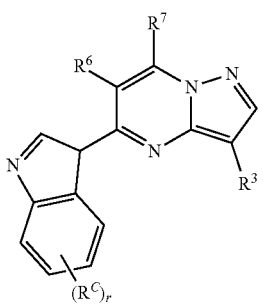

XIX

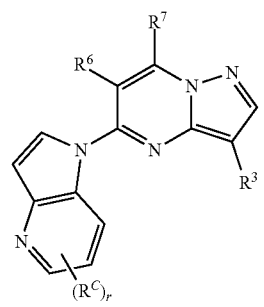

XX

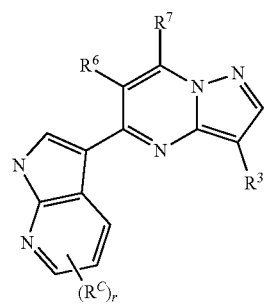

XXI

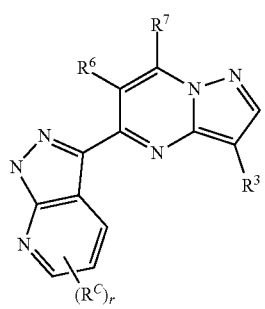

or a pharmaceutically acceptable salt thereof, wherein each of r, $R^C$, $R^3$, $R^6$, and $R^7$ is as defined above and described in embodiments herein, both singly and in combination.

In some embodiments, the present invention provides a compound of formula XVII, XVIII, XIX, XX, or XXI wherein $R^6$ is hydrogen, thereby providing a compound of formulas XVII-a, XVIII-a, XIX-a, XX-a, or XXI-a respectively:

XVII-a

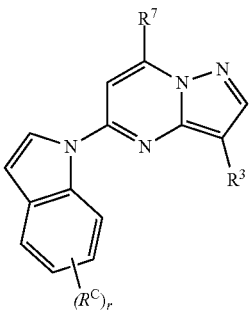

XVIII-a

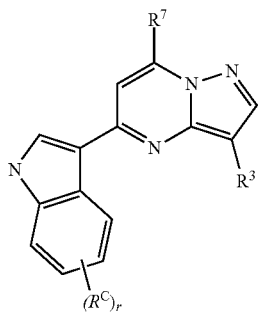

XIX-a

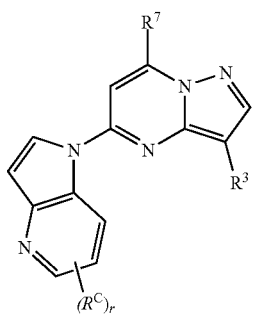

XX-a

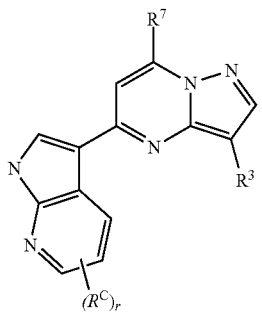

XXI-a

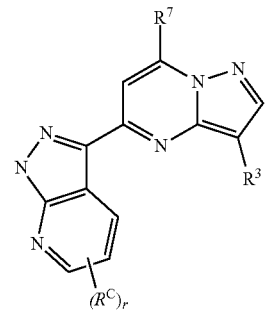

or a pharmaceutically acceptable salt thereof, wherein each of r, $R^C$, $R^3$, and $R^7$ is as defined above and described in embodiments herein, both singly and in combination.

In some embodiments, the present invention provides a compound of formula XVII-a, XVIII-a, XIX-a, XX-a, or XXI-a wherein $R^7$ is —$NHR^{7A}$, thereby providing a compound of formulas XVII-b, XVIII-b, XIX-b, XX-b, or XXI-b respectively:

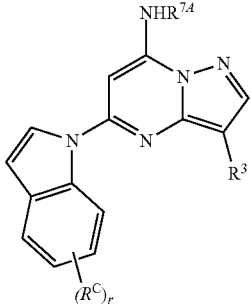

XVII-b

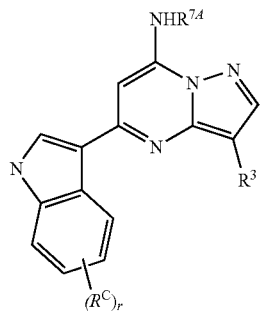

XVIII-b

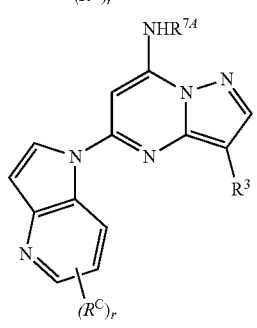

XIX-b

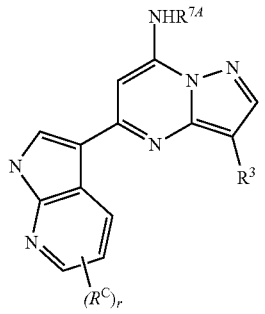

XX-b

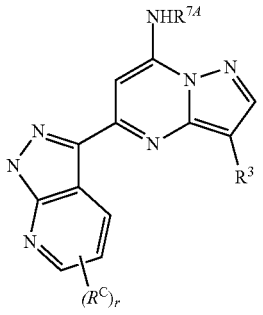

XXI-b or a pharmaceutically acceptable salt thereof, wherein each of r, $R^C$, $R^3$, and $R^{7A}$ is as defined above and described in embodiments herein, both singly and in combination.

In some embodiments, the present invention provides a compound of formula XVII-b, XVIII-b, XIX-b, XX-b, or XXI-b wherein $R^3$ is —C(O)$NHR^{3A}$, thereby providing a compound of formulas XVII-c, XVIII-c, XIX-c, XX-c, or XXI-c respectively:

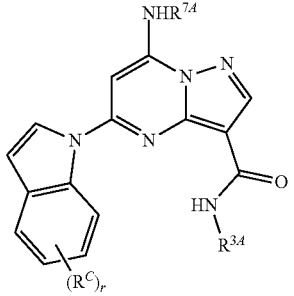

XVII-c

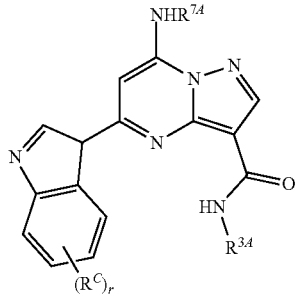

XVIII-c

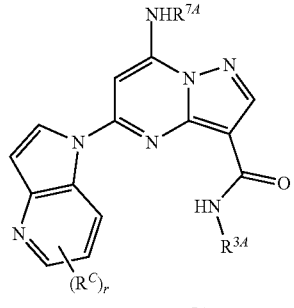

XIX-c

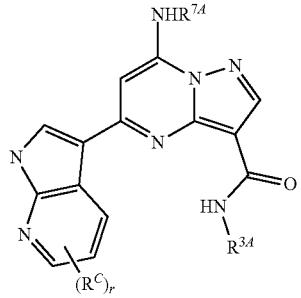

XX-c

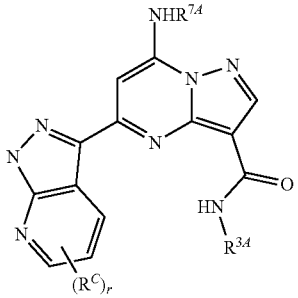

XXI-c or a pharmaceutically acceptable salt thereof, wherein each of r, $R^C$, $R^3$, and $R^{7A}$ is as defined above and described in embodiments herein, both singly and in combination.

Exemplary compounds of the invention are set forth in Table 1, below.

TABLE 1

Selected Compounds

| Compound | Structure |
|---|---|
| I-1 | 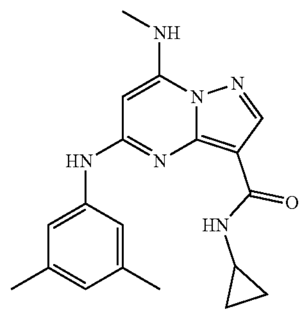 [SMILES: CNc1cc(Nc2cc(C)cc(C)c2)nc2c(C(=O)NC3CC3)cnn12] |
| I-2 | 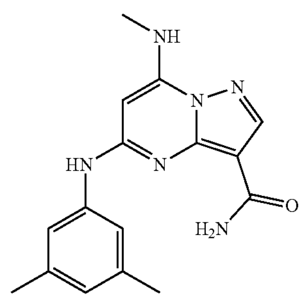 [SMILES: CNc1cc(Nc2cc(C)cc(C)c2)nc2c(C(N)=O)cnn12] |
| I-3 | 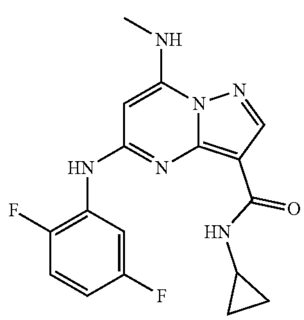 [SMILES: CNc1cc(Nc2cc(F)ccc2F)nc2c(C(=O)NC3CC3)cnn12] |
| I-4 | 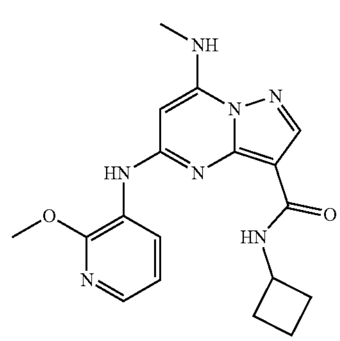 [SMILES: CNc1cc(Nc2cccnc2OC)nc2c(C(=O)NC3CCC3)cnn12] |

TABLE 1-continued
Selected Compounds
| Compound | Structure |
|---|---|
| I-5 | 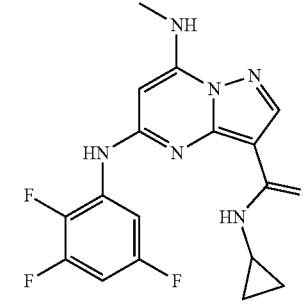 |
| I-6 | 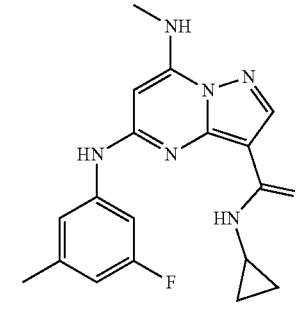 |
| I-7 | 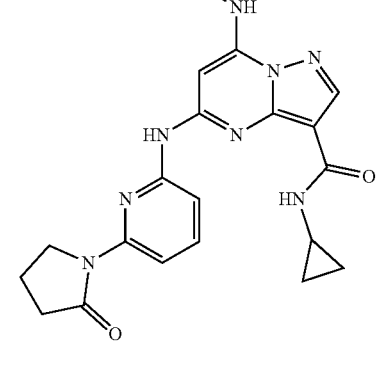 |
| I-8 | 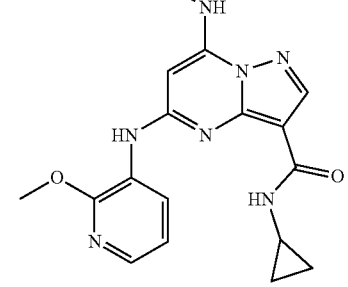 |

TABLE 1-continued

Selected Compounds

| Compound | Structure |
|---|---|
| I-9 | 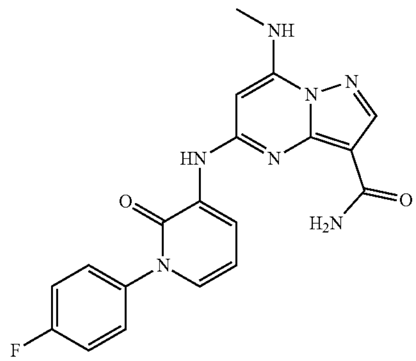 [SMILES: CNc1cc(Nc2cccn(-c3ccc(F)cc3)c2=O)nc2c(C(N)=O)cnn12] |
| I-10 | 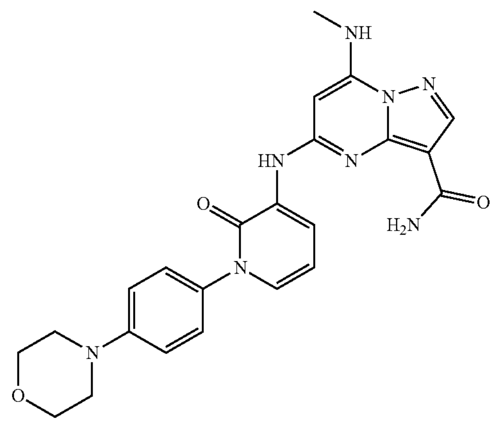 [SMILES: CNc1cc(Nc2cccn(-c3ccc(N4CCOCC4)cc3)c2=O)nc2c(C(N)=O)cnn12] |
| I-11 | 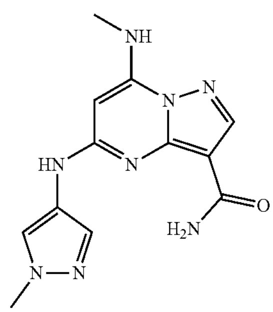 [SMILES: CNc1cc(Nc2cnn(C)c2)nc2c(C(N)=O)cnn12] |
| I-12 | 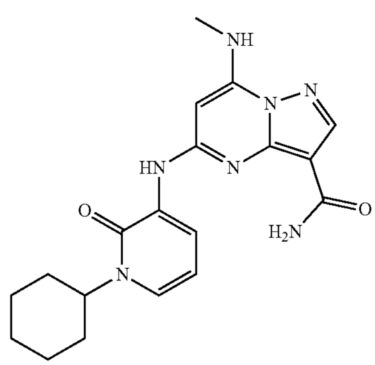 [SMILES: CNc1cc(Nc2cccn(C3CCCCC3)c2=O)nc2c(C(N)=O)cnn12] |

TABLE 1-continued
| Selected Compounds | |
|---|---|
| Compound | Structure |
| I-13 | 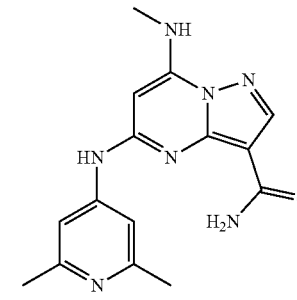 |
| I-14 | 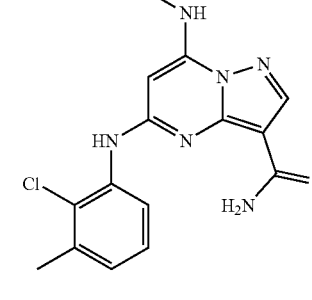 |
| I-15 | 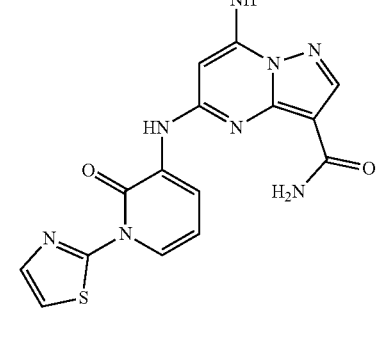 |
| I-16 | 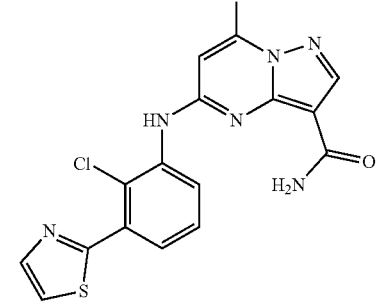 |

TABLE 1-continued
Selected Compounds
| Compound | Structure |
|---|---|
| I-17 | 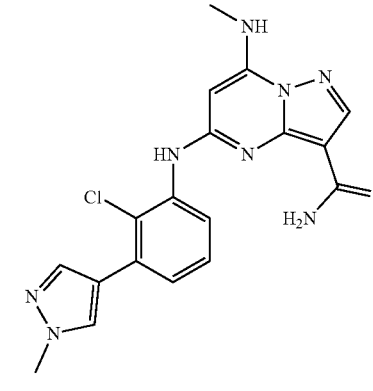 |
| I-18 | 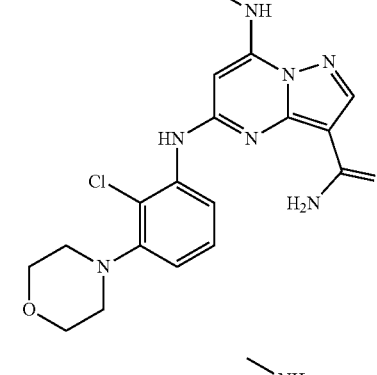 |
| I-19 | 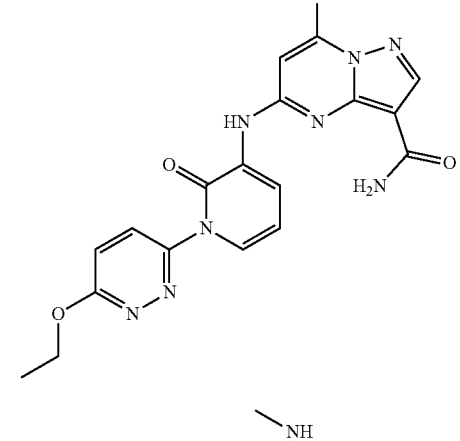 |
| I-20 | 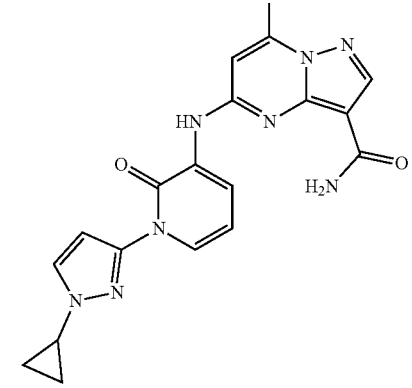 |

TABLE 1-continued

Selected Compounds

| Compound | Structure |
|---|---|
| I-21 | 7-amino-5-(3,5-dimethylphenylamino)pyrazolo[1,5-a]pyrimidine-3-carboxamide |
| I-22 | 7-amino-5-((2-chloro-3-morpholinophenyl)amino)pyrazolo[1,5-a]pyrimidine-3-carboxamide |
| I-23 | 7-amino-5-((2-chloro-3-(pyrrolidin-1-yl)phenyl)amino)pyrazolo[1,5-a]pyrimidine-3-carboxamide |
| I-24 | 5-((2-methoxypyridin-3-yl)amino)-7-(methylamino)pyrazolo[1,5-a]pyrimidine-3-carboxamide |

TABLE 1-continued

Selected Compounds

| Compound | Structure |
|---|---|
| I-25 | 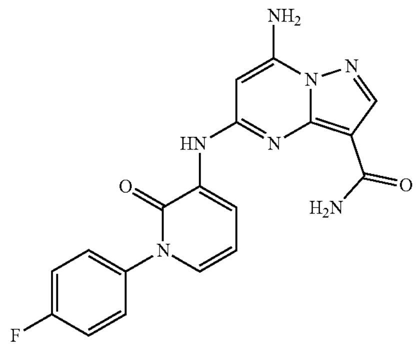 [SMILES: NC(=O)c1cnn2c(N)cc(Nc3cccn(-c4ccc(F)cc4)c3=O)nc12] |
| I-26 | 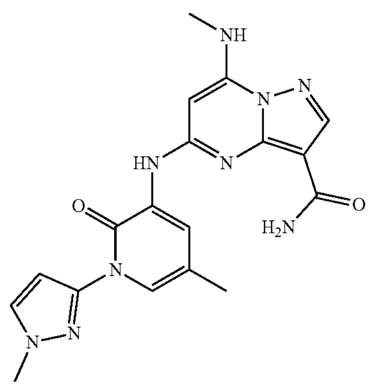 [SMILES: CNc1cc(Nc2cc(C)cn(-c3ccn(C)n3)c2=O)nc2c(C(N)=O)cnn12] |
| I-27 | 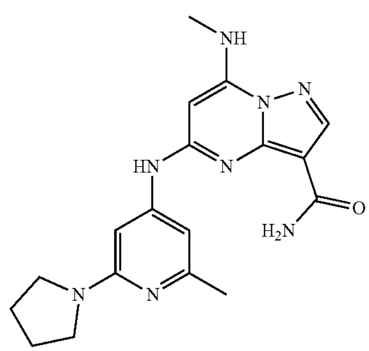 [SMILES: CNc1cc(Nc2cc(C)nc(N3CCCC3)c2)nc2c(C(N)=O)cnn12] |
| I-28 | 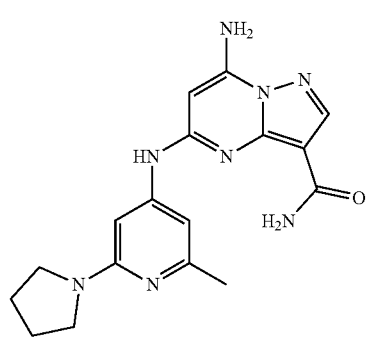 [SMILES: Cc1cc(Nc2cc(N)n3ncc(C(N)=O)c3n2)cc(N2CCCC2)n1] |

TABLE 1-continued

Selected Compounds

| Compound | Structure |
|---|---|
| I-29 | 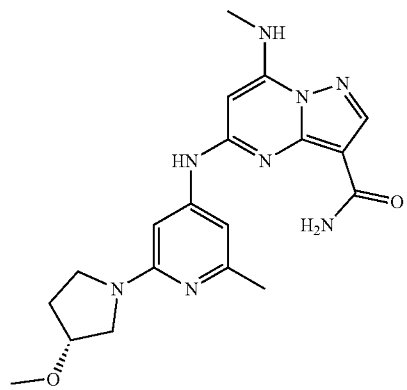 [SMILES: CNc1cc(Nc2cc(C)nc(N3CC[C@@H](OC)C3)c2)nc2c(C(N)=O)cnn12] |
| I-30 | 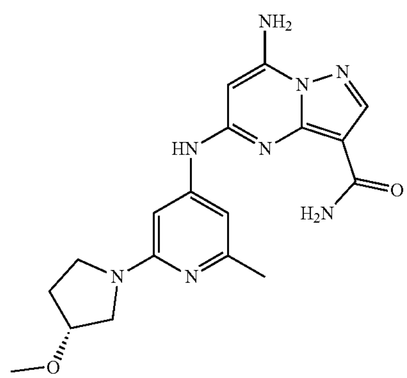 [SMILES: CO[C@@H]1CCN(c2cc(Nc3cc(N)n4ncc(C(N)=O)c4n3)cc(C)n2)C1] |
| I-31 | 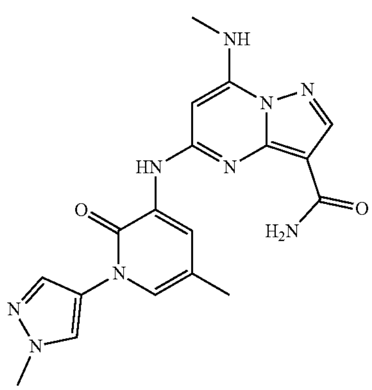 [SMILES: CNc1cc(Nc2cc(C)cn(-c3cnn(C)c3)c2=O)nc2c(C(N)=O)cnn12] |
| I-32 | 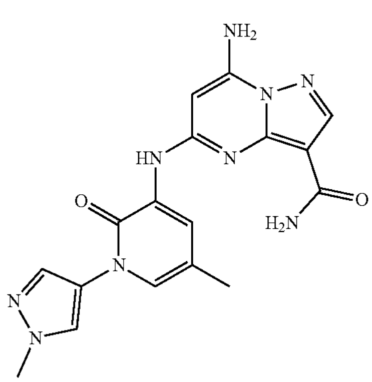 [SMILES: Cc1cc(Nc2cc(N)n3ncc(C(N)=O)c3n2)c(=O)n(-c2cnn(C)c2)c1] |

TABLE 1-continued
Selected Compounds
| Compound | Structure |
|---|---|
| I-33 | 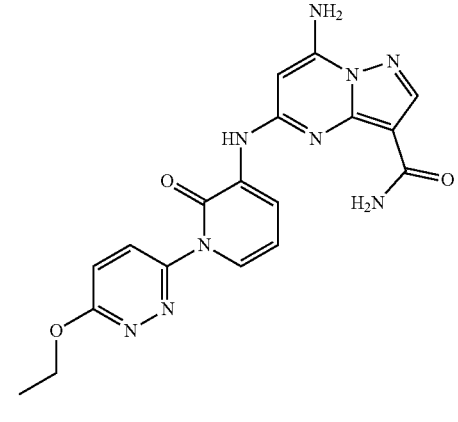 [SMILES: CCOc1ccc(-n2cccc(Nc3cc(N)n4ncc(C(N)=O)c4n3)c2=O)nn1] |
| I-34 | 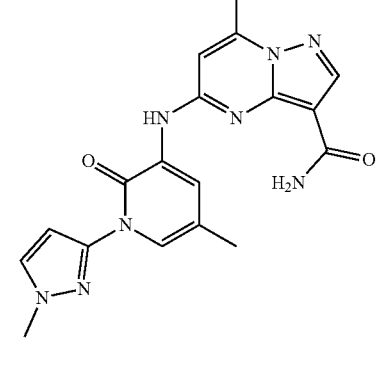 |
| I-35 | 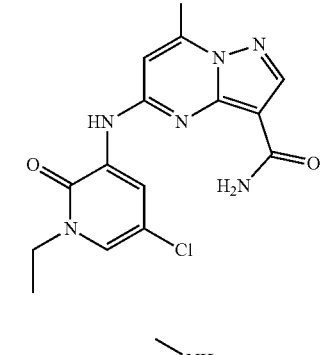 |
| I-36 | 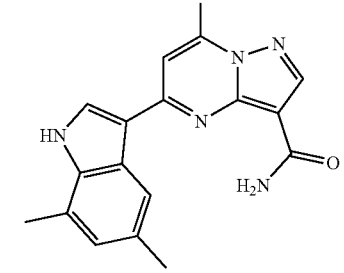 |

TABLE 1-continued

Selected Compounds

| Compound | Structure |
|---|---|
| I-37 | *(structure image)* |
| I-38 | *(structure image)* |
| I-39 | *(structure image)* |
| I-40 | *(structure image)* |

TABLE 1-continued

Selected Compounds

| Compound | Structure |
|---|---|
| I-41 | 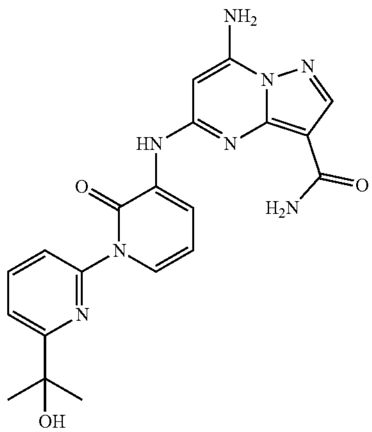 [SMILES: CC(C)(O)c1cccc(-n2cccc(Nc3cc(N)n4ncc(C(N)=O)c4n3)c2=O)n1] |
| I-42 | 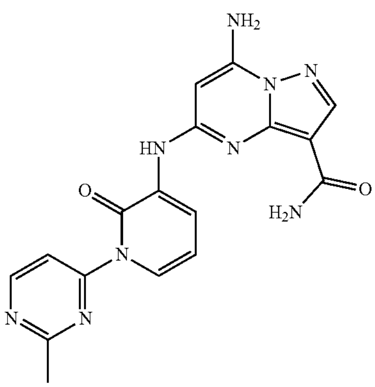 [SMILES: Cc1nccc(-n2cccc(Nc3cc(N)n4ncc(C(N)=O)c4n3)c2=O)n1] |
| I-43 | 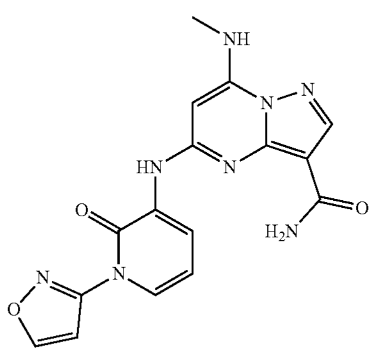 [SMILES: CNc1cc(Nc2cccn(-c3ccon3)c2=O)nc2c(C(N)=O)cnn12] |
| I-44 | 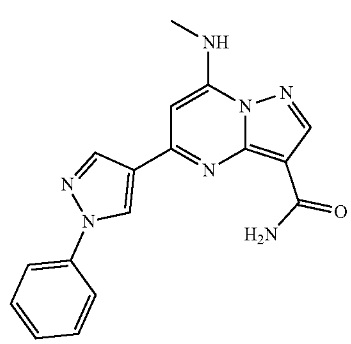 [SMILES: CNc1cc(-c2cnn(-c3ccccc3)c2)nc2c(C(N)=O)cnn12] |

TABLE 1-continued
Selected Compounds
| Compound | Structure |
|---|---|
| I-45 | 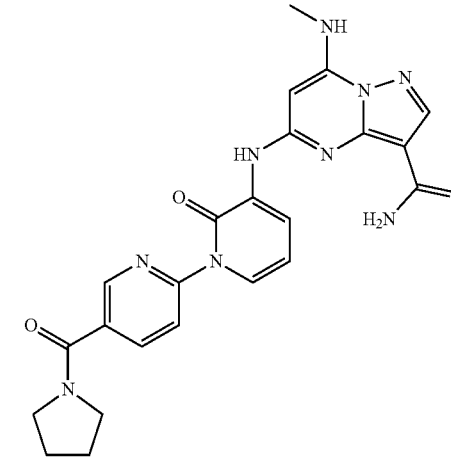 |
| I-46 | 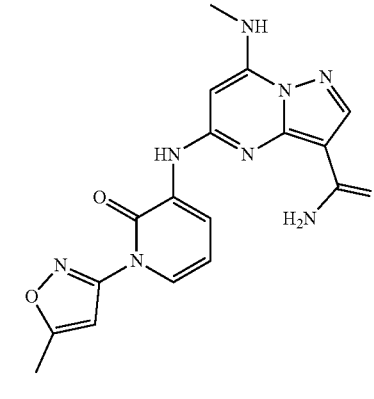 |
| I-47 | 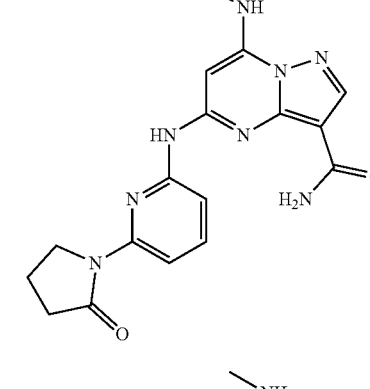 |
| I-48 | 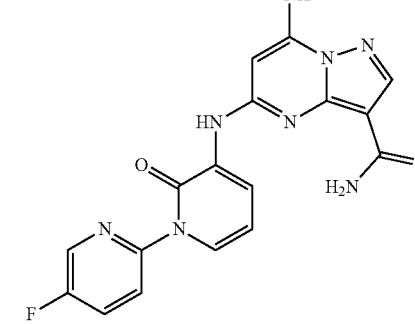 |

TABLE 1-continued

| Compound | Structure |
|---|---|
| I-49 | 7-amino-5-((1-ethyl-5-chloro-2-oxo-1,2-dihydropyridin-3-yl)amino)pyrazolo[1,5-a]pyrimidine-3-carboxamide |
| I-50 | 7-amino-5-((1-(trans-4-hydroxycyclohexyl)-2-oxo-1,2-dihydropyridin-3-yl)amino)pyrazolo[1,5-a]pyrimidine-3-carboxamide |
| I-51 | 7-(methylamino)-5-((1-(2-methylpyrimidin-4-yl)-2-oxo-1,2-dihydropyridin-3-yl)amino)pyrazolo[1,5-a]pyrimidine-3-carboxamide |
| I-52 | 7-amino-5-((1-(5-fluoropyridin-2-yl)-2-oxo-1,2-dihydropyridin-3-yl)amino)pyrazolo[1,5-a]pyrimidine-3-carboxamide |

TABLE 1-continued

Selected Compounds

| Compound | Structure |
|---|---|
| I-53 | 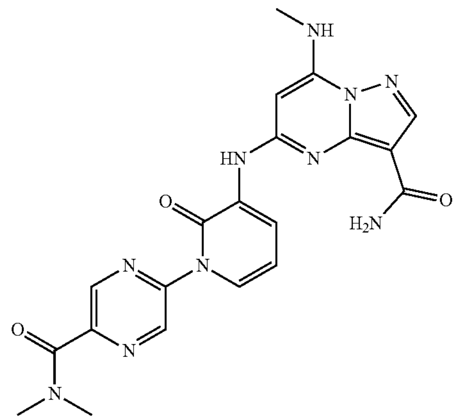 [SMILES: CNc1cc(Nc2cccn(-c3cnc(C(=O)N(C)C)cn3)c2=O)nc2c(C(N)=O)cnn12] |
| I-54 | 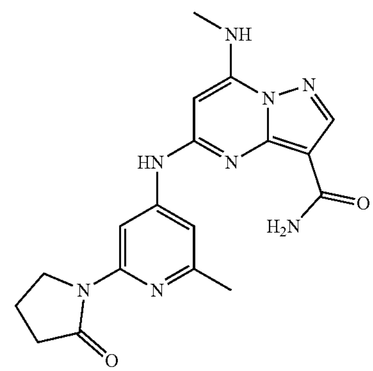 [SMILES: CNc1cc(Nc2cc(C)nc(N3CCCC3=O)c2)nc2c(C(N)=O)cnn12] |
| I-55 | 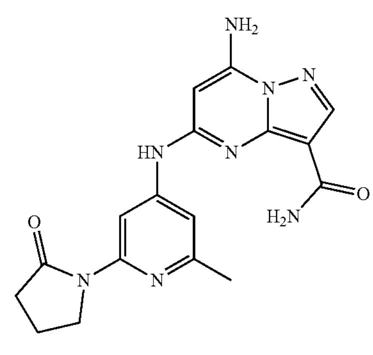 [SMILES: Cc1cc(Nc2cc(N)n3ncc(C(N)=O)c3n2)cc(N2CCCC2=O)n1] |
| I-56 | 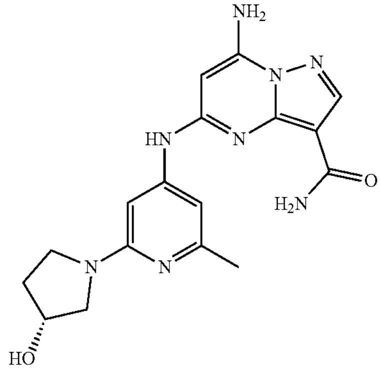 [SMILES: Cc1cc(Nc2cc(N)n3ncc(C(N)=O)c3n2)cc(N2CC[C@@H](O)C2)n1] |

TABLE 1-continued
Selected Compounds
| Compound | Structure |
|---|---|
| I-57 | 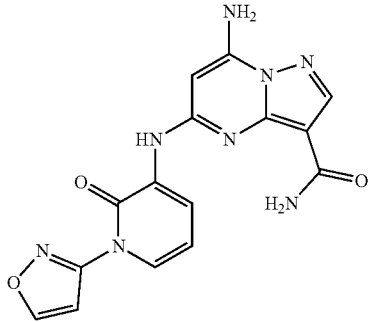 [SMILES: NC(=O)c1cnn2c(N)cc(Nc3cccn(-c4ccon4)c3=O)nc12] |
| I-58 | 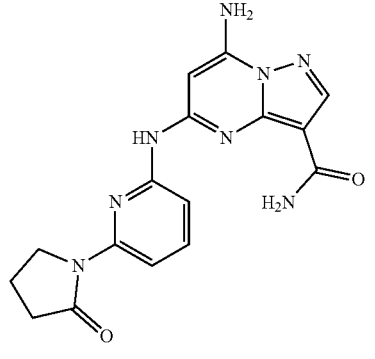 [SMILES: NC(=O)c1cnn2c(N)cc(Nc3cccc(N4CCCC4=O)n3)nc12] |
| I-59 | 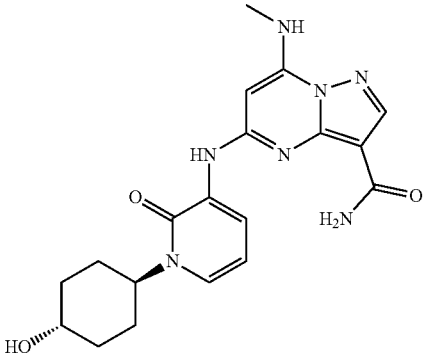 [SMILES: CNc1cc(Nc2cccn([C@H]3CC[C@H](O)CC3)c2=O)nc2c(C(N)=O)cnn12] |
| I-60 | 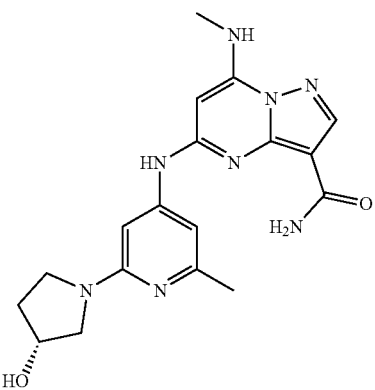 [SMILES: CNc1cc(Nc2cc(C)nc(N3CC[C@@H](O)C3)c2)nc2c(C(N)=O)cnn12] |

TABLE 1-continued

Selected Compounds

| Compound | Structure |
|---|---|
| I-61 | *(chemical structure)* |
| I-62 | *(chemical structure)* |
| I-63 | *(chemical structure)* |
| I-64 | *(chemical structure)* |

US 10,562,906 B2
113                                                                                           114
TABLE 1-continued
Selected Compounds
| Compound | Structure |
|---|---|
| I-65 | 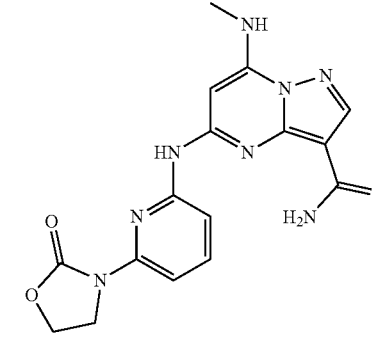 |
| I-66 | 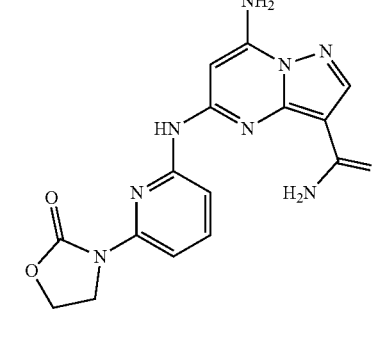 |
| I-67 | 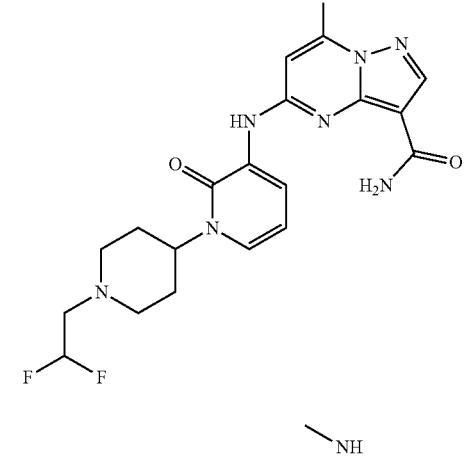 |
| I-68 | 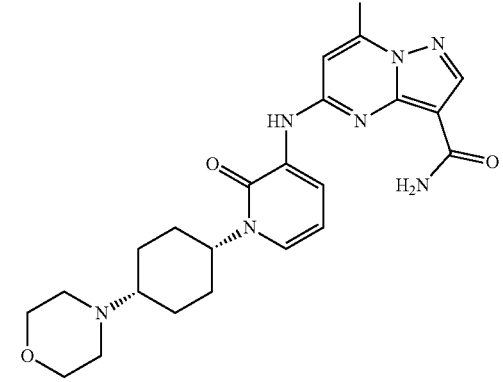 |

TABLE 1-continued

Selected Compounds

| Compound | Structure |
|---|---|
| I-69 | 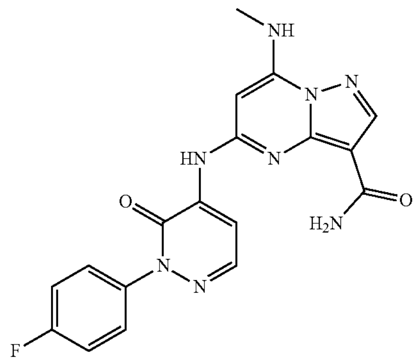 [SMILES: CNc1cc(Nc2ccnn(-c3ccc(F)cc3)c2=O)nc2c(C(N)=O)cnn12] |
| I-70 | 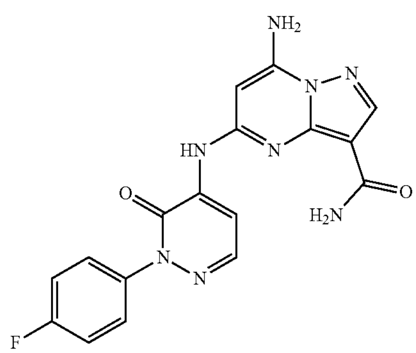 [SMILES: NC(=O)c1cnn2c(N)cc(Nc3ccnn(-c4ccc(F)cc4)c3=O)nc12] |
| I-71 | 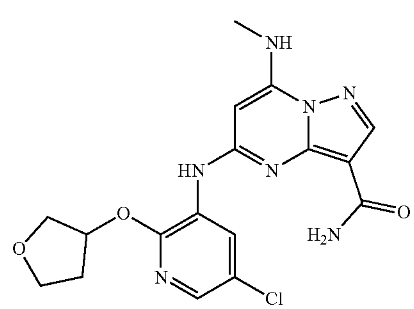 [SMILES: CNc1cc(Nc2cc(Cl)cnc2OC2CCOC2)nc2c(C(N)=O)cnn12] |
| I-72 | 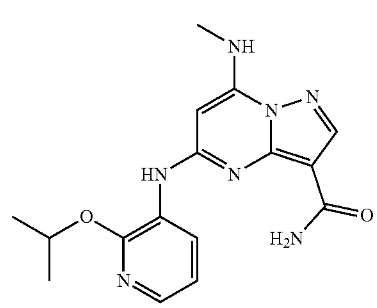 [SMILES: CNc1cc(Nc2cccnc2OC(C)C)nc2c(C(N)=O)cnn12] |

TABLE 1-continued

| Selected Compounds | |
|---|---|
| Compound | Structure |
| I-73 | (structure) |
| I-74 | (structure) |
| I-75 | (structure) |
| I-76 | (structure) |

TABLE 1-continued
Selected Compounds
| Compound | Structure |
|---|---|
| I-77 | 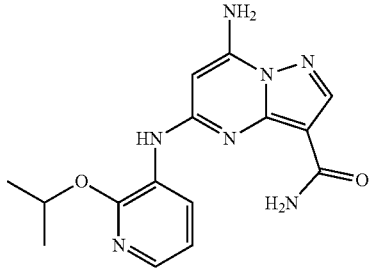 [SMILES: CC(C)Oc1ncccc1Nc1cc(N)n2ncc(C(N)=O)c2n1] |
| I-78 | 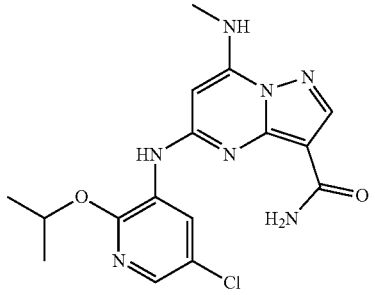 [SMILES: CNc1cc(Nc2cc(Cl)cnc2OC(C)C)nc2c(C(N)=O)cnn12] |
| I-79 | 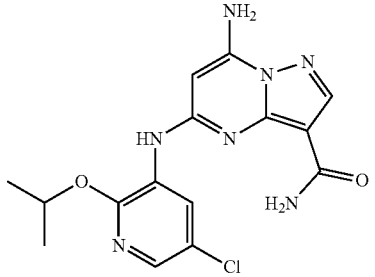 [SMILES: CC(C)Oc1ncc(Cl)cc1Nc1cc(N)n2ncc(C(N)=O)c2n1] |
| I-80 | 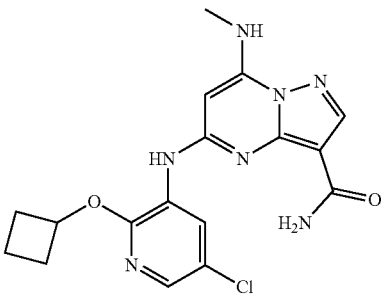 [SMILES: CNc1cc(Nc2cc(Cl)cnc2OC2CCC2)nc2c(C(N)=O)cnn12] |
| I-81 | 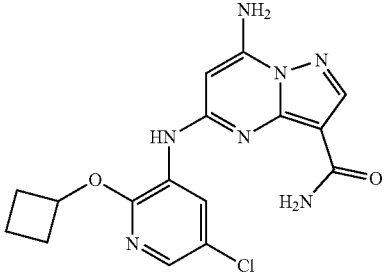 [SMILES: NC(=O)c1cnn2c(N)cc(Nc3cc(Cl)cnc3OC3CCC3)nc12] |

TABLE 1-continued

Selected Compounds

| Compound | Structure |
|---|---|
| I-82 | 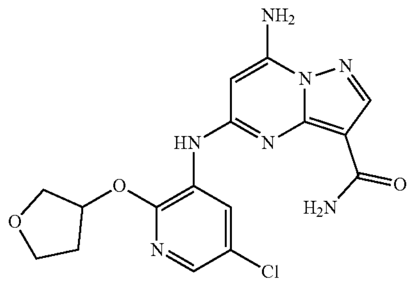 [SMILES: NC(=O)c1cnn2c(N)cc(Nc3cc(Cl)cnc3OC3CCOC3)nc12] |
| I-83 | 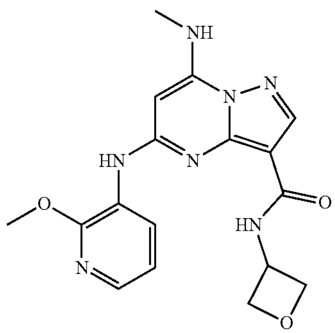 [SMILES: CNc1cc(Nc2cccnc2OC)nc2c(C(=O)NC3COC3)cnn12] |
| I-84 | 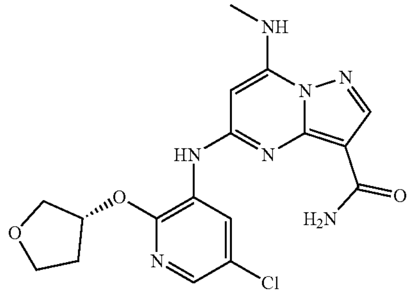 |
| I-85 | 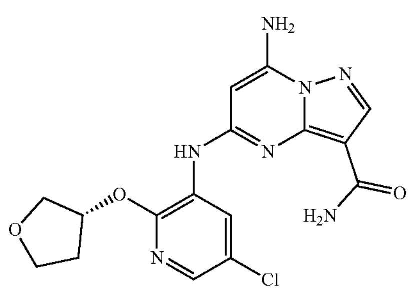 [SMILES: NC(=O)c1cnn2c(N)cc(Nc3cc(Cl)cnc3O[C@@H]3CCOC3)nc12] |
| I-86 | 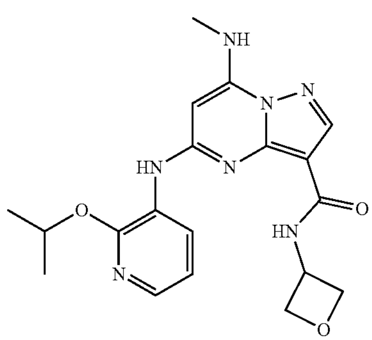 [SMILES: CNc1cc(Nc2cccnc2OC(C)C)nc2c(C(=O)NC3COC3)cnn12] |

TABLE 1-continued
| Selected Compounds | |
|---|---|
| Compound | Structure |
| I-87 | 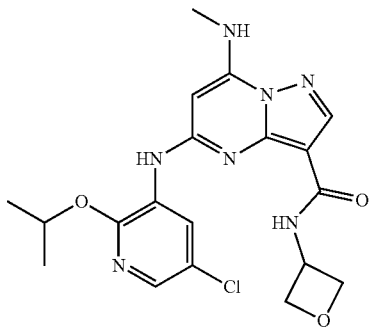 [SMILES: CNc1cc(Nc2cc(Cl)cnc2OC(C)C)nc2c(C(=O)NC3COC3)cnn12] |
| I-88 | 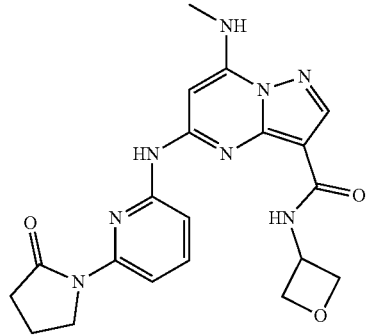 [SMILES: CNc1cc(Nc2cccc(N3CCCC3=O)n2)nc2c(C(=O)NC3COC3)cnn12] |
| I-89 | 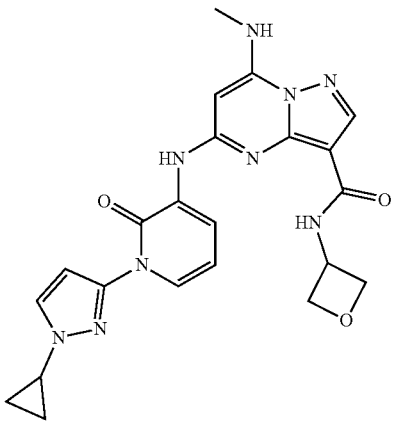 [SMILES: CNc1cc(Nc2cccn(-c3ccn(C4CC4)n3)c2=O)nc2c(C(=O)NC3COC3)cnn12] |
| I-90 | 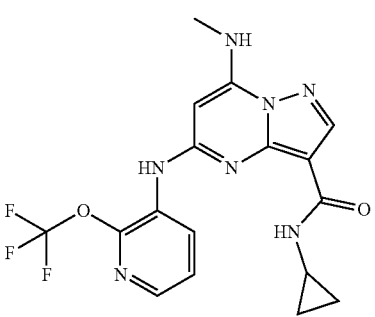 [SMILES: CNc1cc(Nc2cccnc2OC(F)(F)F)nc2c(C(=O)NC3CC3)cnn12] |

TABLE 1-continued
Selected Compounds
| Compound | Structure |
|---|---|
| I-91 | 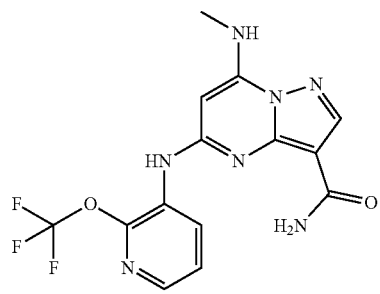 [SMILES: CNc1cc(Nc2cccnc2OC(F)(F)F)nc2c(C(N)=O)cnn12] |
| I-92 | 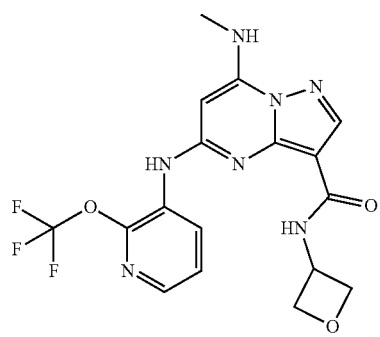 [SMILES: CNc1cc(Nc2cccnc2OC(F)(F)F)nc2c(C(=O)NC3COC3)cnn12] |
| I-93 | 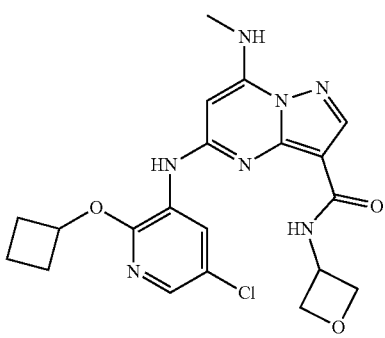 [SMILES: CNc1cc(Nc2cc(Cl)cnc2OC2CCC2)nc2c(C(=O)NC3COC3)cnn12] |
| I-94 | 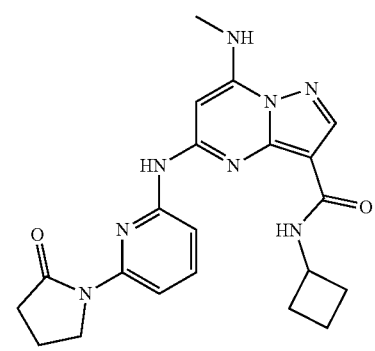 [SMILES: CNc1cc(Nc2cccc(N3CCCC3=O)n2)nc2c(C(=O)NC3CCC3)cnn12] |

TABLE 1-continued

| Compound | Structure |
|---|---|
| I-95 | 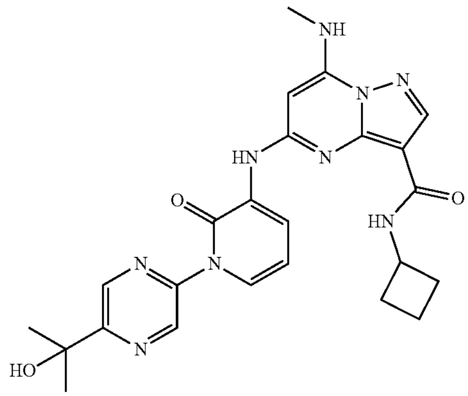 [SMILES: CNc1cc(Nc2cccn(-c3cnc(C(C)(C)O)cn3)c2=O)nc2c(C(=O)NC3CCC3)cnn12] |
| I-96 | 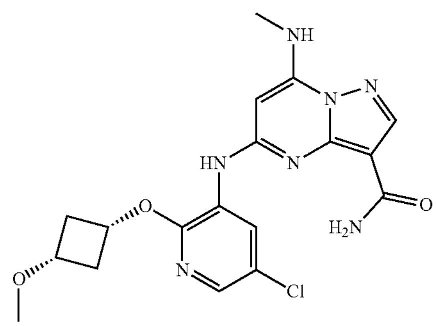 [SMILES: CNc1cc(Nc2cc(Cl)cnc2O[C@H]2C[C@@H](OC)C2)nc2c(C(N)=O)cnn12] |
| I-97 | 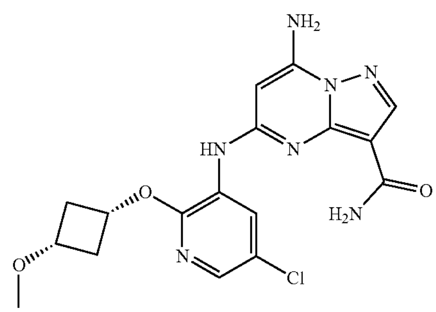 [SMILES: CO[C@H]1C[C@@H](Oc2ncc(Cl)cc2Nc2cc(N)n3ncc(C(N)=O)c3n2)C1] |
| I-98 | 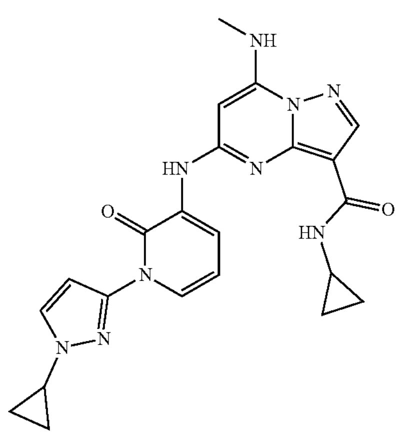 [SMILES: CNc1cc(Nc2cccn(-c3ccn(C4CC4)n3)c2=O)nc2c(C(=O)NC3CC3)cnn12] |

TABLE 1-continued

Selected Compounds

| Compound | Structure |
|---|---|
| I-99 | 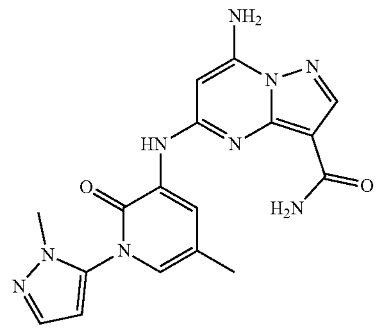 [SMILES: Cc1cc(Nc2cc(N)n3ncc(C(N)=O)c3n2)c(=O)n(-c2ccnn2C)c1] |
| I-100 | 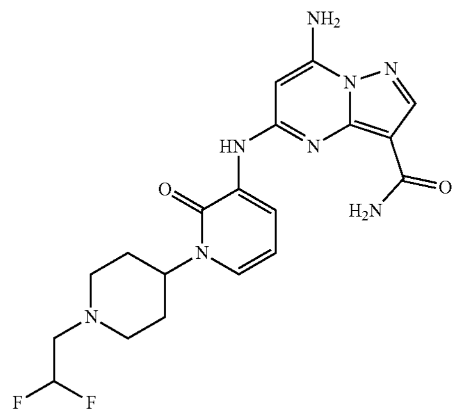 [SMILES: NC(=O)c1cnn2c(N)cc(Nc3cccn(C4CCN(CC(F)F)CC4)c3=O)nc12] |
| I-101 | 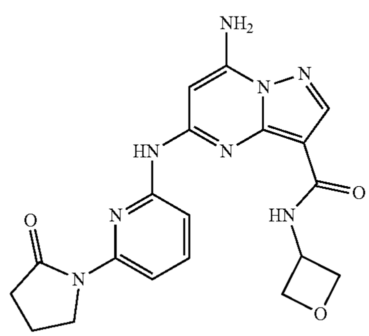 [SMILES: Nc1cc(Nc2cccc(N3CCCC3=O)n2)nc2c(C(=O)NC3COC3)cnn12] |
| I-102 | 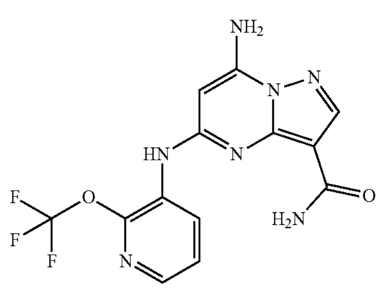 [SMILES: NC(=O)c1cnn2c(N)cc(Nc3cccnc3OC(F)(F)F)nc12] |

TABLE 1-continued

| Compound | Structure |
|---|---|
| I-103 | (structure) |
| I-104 | (structure) |
| I-105 | (structure) |
| I-106 | (structure) |

TABLE 1-continued
| Selected Compounds | |
|---|---|
| Compound | Structure |
| I-107 | 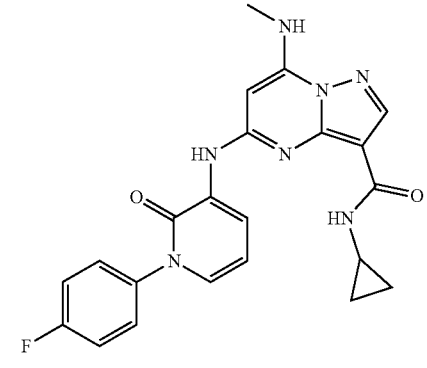 |
| I-108 | 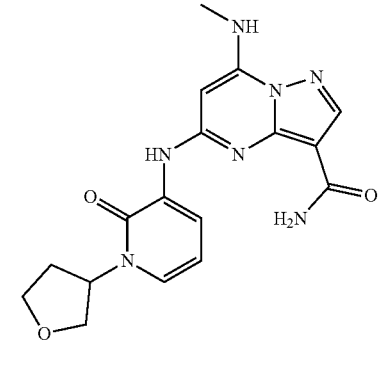 [SMILES: CNc1cc(Nc2cccn(C3CCOC3)c2=O)nc2c(C(N)=O)cnn12] |
| I-109 | 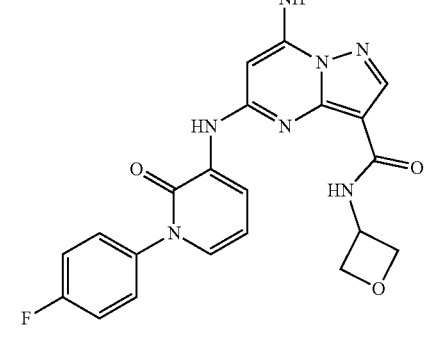 |
| I-110 | 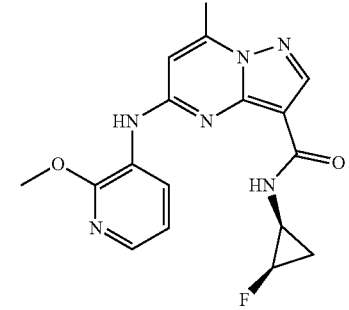 |

TABLE 1-continued
Selected Compounds
| Compound | Structure |
|---|---|
| I-111 | 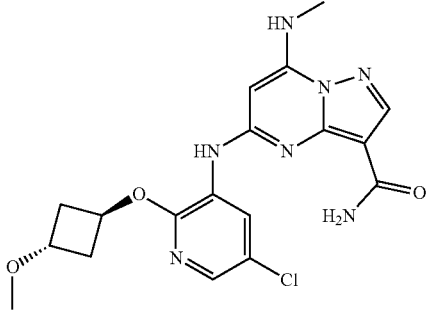 [SMILES: CNc1cc(Nc2cc(Cl)cnc2O[C@H]2C[C@H](OC)C2)nc2c(C(N)=O)cnn12] |
| I-112 | 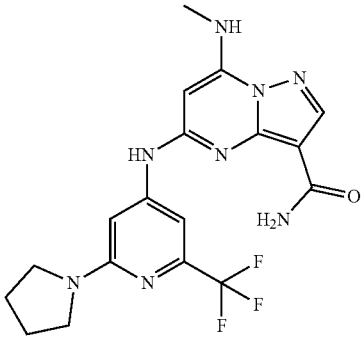 [SMILES: CNc1cc(Nc2cc(N3CCCC3)nc(C(F)(F)F)c2)nc2c(C(N)=O)cnn12] |
| I-113 | 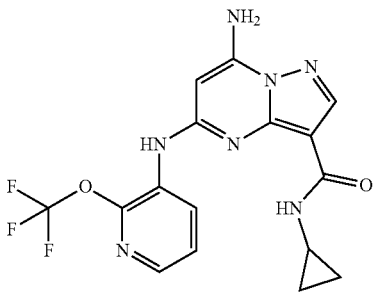 [SMILES: Nc1cc(Nc2cccnc2OC(F)(F)F)nc2c(C(=O)NC3CC3)cnn12] |
| I-114 | 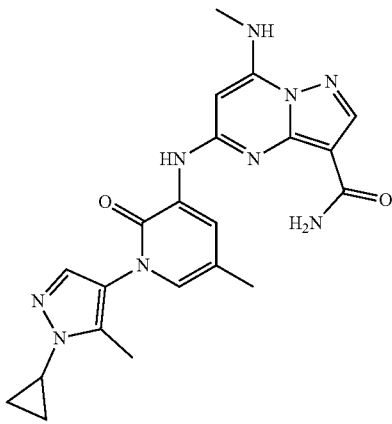 |

TABLE 1-continued
Selected Compounds
| Compound | Structure |
|---|---|
| I-115 | 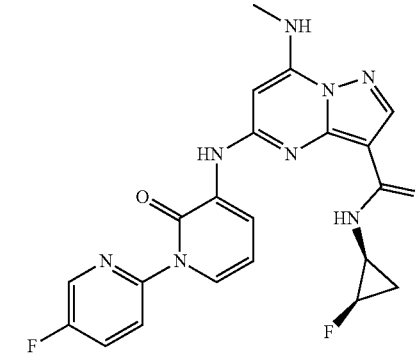 |
| I-116 | 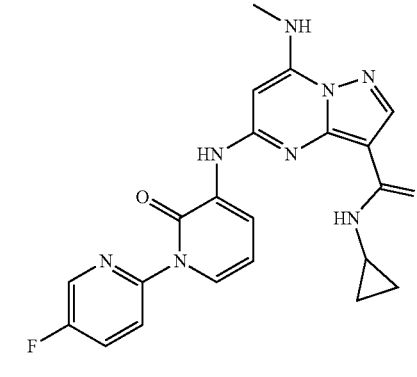 |
| I-117 | 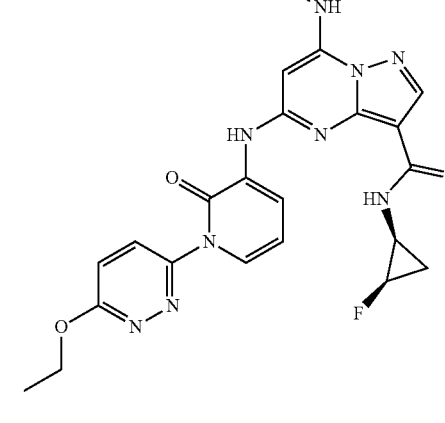 |
| I-118 | 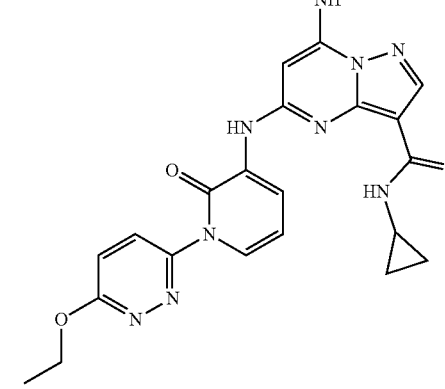 |

TABLE 1-continued

Selected Compounds

| Compound | Structure |
|---|---|
| I-119 | 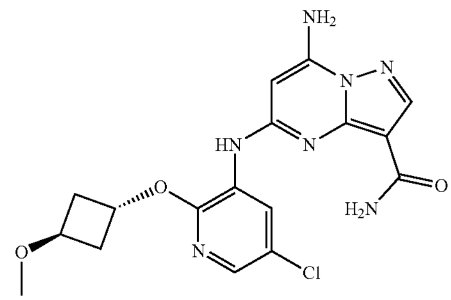 [SMILES: CO[C@H]1C[C@H](Oc2ncc(Cl)cc2Nc2cc(N)n3ncc(C(N)=O)c3n2)C1] |
| I-120 | 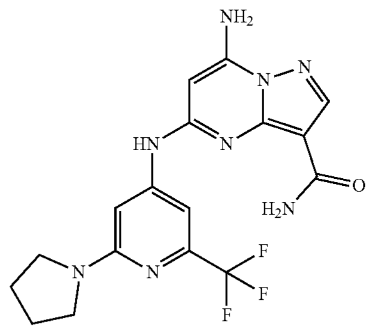 [SMILES: NC(=O)c1cnn2c(N)cc(Nc3cc(N4CCCC4)nc(C(F)(F)F)c3)nc12] |
| I-121 | 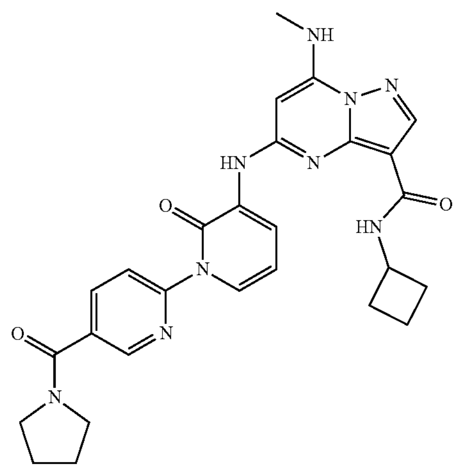 [SMILES: CNc1cc(Nc2cccn(-c3ccc(C(=O)N4CCCC4)cn3)c2=O)nc2c(C(=O)NC3CCC3)cnn12] |
| I-122 | 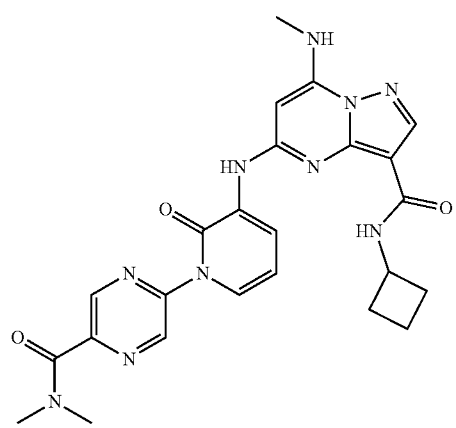 [SMILES: CNc1cc(Nc2cccn(-c3cnc(C(=O)N(C)C)cn3)c2=O)nc2c(C(=O)NC3CCC3)cnn12] |

TABLE 1-continued

Selected Compounds

| Compound | Structure |
|---|---|
| I-123 | 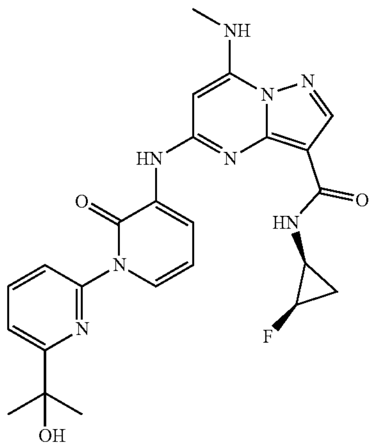 [SMILES: CNc1cc(Nc2cccn(-c3cccc(C(C)(C)O)n3)c2=O)nc2c(C(=O)N[C@H]3C[C@H]3F)cnn12] |
| I-124 | 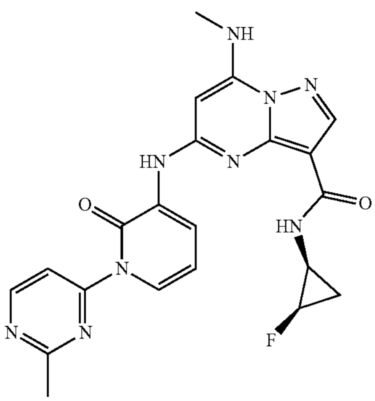 [SMILES: CNc1cc(Nc2cccn(-c3ccnc(C)n3)c2=O)nc2c(C(=O)N[C@H]3C[C@H]3F)cnn12] |
| I-125 | 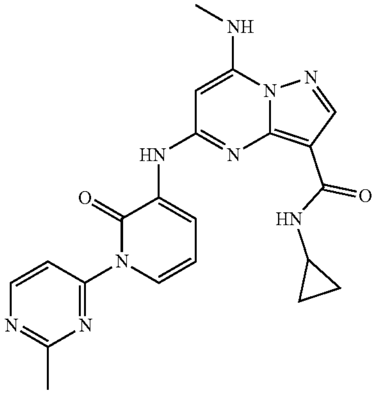 [SMILES: CNc1cc(Nc2cccn(-c3ccnc(C)n3)c2=O)nc2c(C(=O)NC3CC3)cnn12] |

TABLE 1-continued

Selected Compounds

| Compound | Structure |
|---|---|
| I-126 | 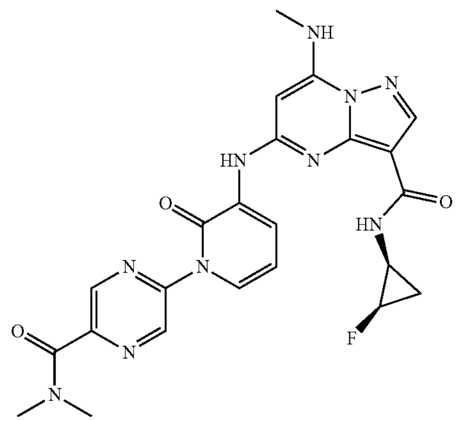 [SMILES: CNc1cc(Nc2cccn(-c3cnc(C(=O)N(C)C)cn3)c2=O)nc2c(C(=O)N[C@H]3C[C@H]3F)cnn12] |
| I-127 | 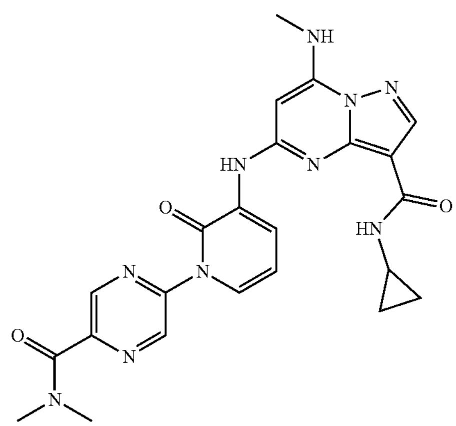 [SMILES: CNc1cc(Nc2cccn(-c3cnc(C(=O)N(C)C)cn3)c2=O)nc2c(C(=O)NC3CC3)cnn12] |
| I-128 | 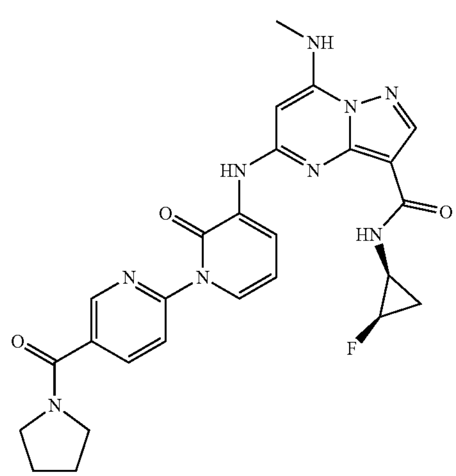 [SMILES: CNc1cc(Nc2cccn(-c3ccc(C(=O)N4CCCC4)cn3)c2=O)nc2c(C(=O)N[C@H]3C[C@H]3F)cnn12] |

TABLE 1-continued
Selected Compounds
| Compound | Structure |
|---|---|
| I-129 | 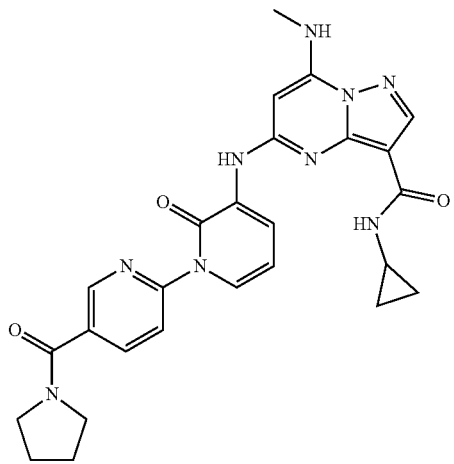 [SMILES: CNc1cc(Nc2cccn(-c3ccc(C(=O)N4CCCC4)cn3)c2=O)nc2c(C(=O)NC3CC3)cnn12] |
| I-130 | 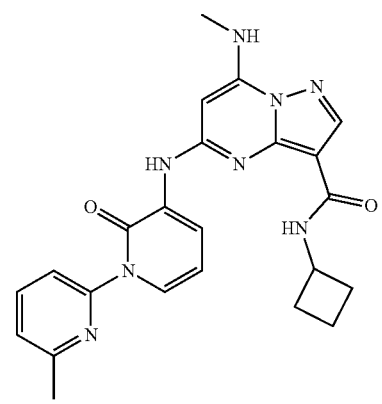 [SMILES: CNc1cc(Nc2cccn(-c3cccc(C)n3)c2=O)nc2c(C(=O)NC3CCC3)cnn12] |
| I-131 | 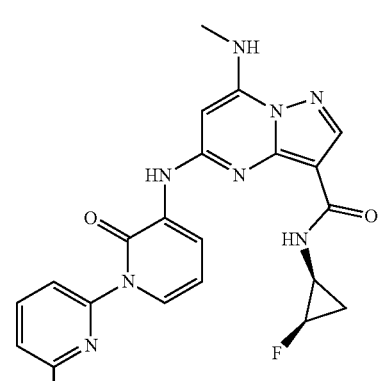 |

TABLE 1-continued

Selected Compounds

| Compound | Structure |
|---|---|
| I-132 | 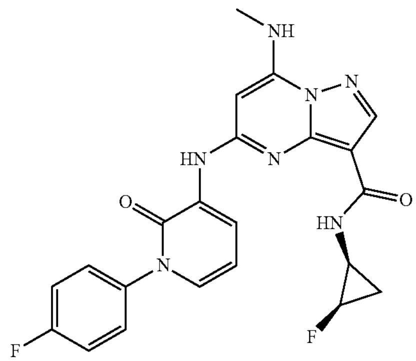 [SMILES: CNc1cc(Nc2cccn(-c3ccc(F)cc3)c2=O)nc2c(C(=O)N[C@H]3C[C@H]3F)cnn12] |
| I-133 | 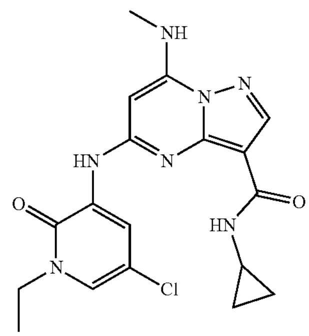 [SMILES: CCn1cc(Cl)cc(Nc2cc(NC)n3ncc(C(=O)NC4CC4)c3n2)c1=O] |
| I-134 | 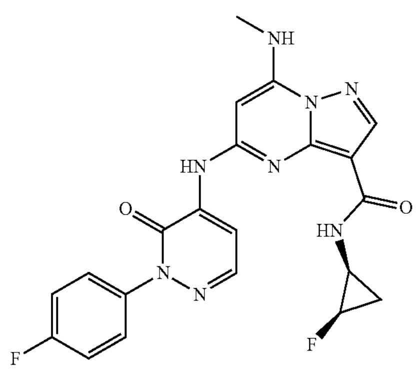 [SMILES: CNc1cc(Nc2ccnn(-c3ccc(F)cc3)c2=O)nc2c(C(=O)N[C@H]3C[C@H]3F)cnn12] |
| I-135 | 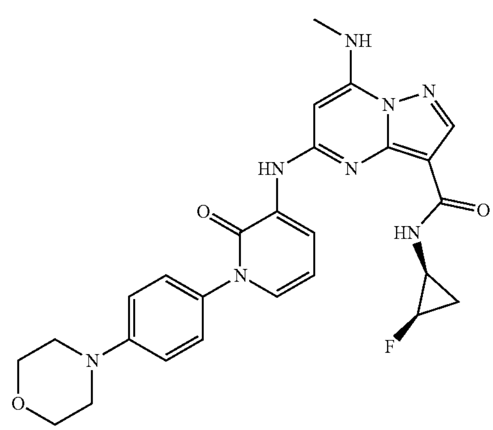 [SMILES: CNc1cc(Nc2cccn(-c3ccc(N4CCOCC4)cc3)c2=O)nc2c(C(=O)N[C@H]3C[C@H]3F)cnn12] |

TABLE 1-continued

Selected Compounds

| Compound | Structure |
|---|---|
| I-136 | 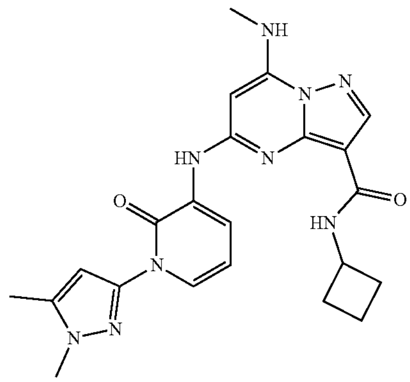 [SMILES: CNc1cc(Nc2cccn(-c3cc(C)n(C)n3)c2=O)nc2c(C(=O)NC3CCC3)cnn12] |
| I-137 | 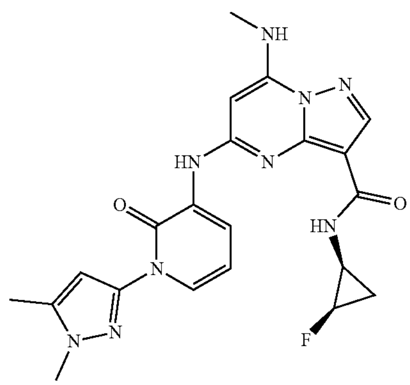 [SMILES: CNc1cc(Nc2cccn(-c3cc(C)n(C)n3)c2=O)nc2c(C(=O)N[C@H]3C[C@H]3F)cnn12] |
| I-138 | 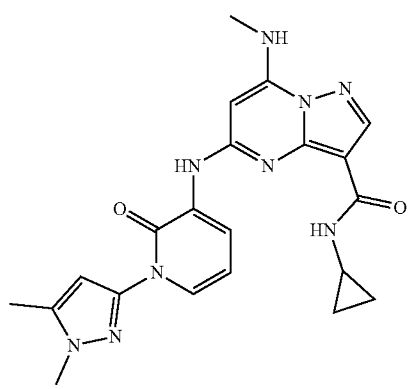 [SMILES: CNc1cc(Nc2cccn(-c3cc(C)n(C)n3)c2=O)nc2c(C(=O)NC3CC3)cnn12] |
| I-139 | 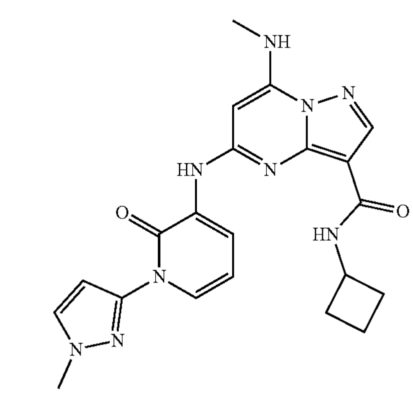 [SMILES: CNc1cc(Nc2cccn(-c3ccn(C)n3)c2=O)nc2c(C(=O)NC3CCC3)cnn12] |

TABLE 1-continued
Selected Compounds
| Compound | Structure |
|---|---|
| I-140 | 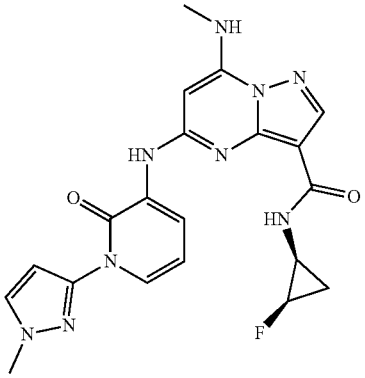 [SMILES: CNc1cc(Nc2cccn(-c3ccn(C)n3)c2=O)nc2c(C(=O)N[C@H]3C[C@H]3F)cnn12] |
| I-141 | 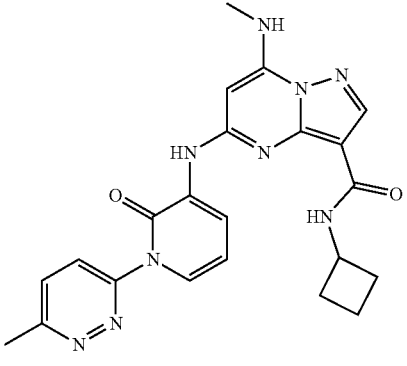 [SMILES: CNc1cc(Nc2cccn(-c3ccc(C)nn3)c2=O)nc2c(C(=O)NC3CCC3)cnn12] |
| I-142 | 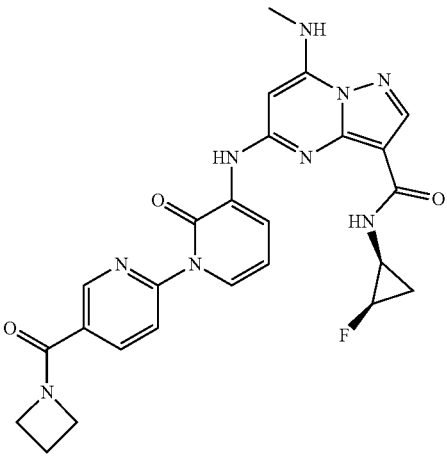 [SMILES: CNc1cc(Nc2cccn(-c3ccc(C(=O)N4CCC4)cn3)c2=O)nc2c(C(=O)N[C@H]3C[C@H]3F)cnn12] |
| I-143 | 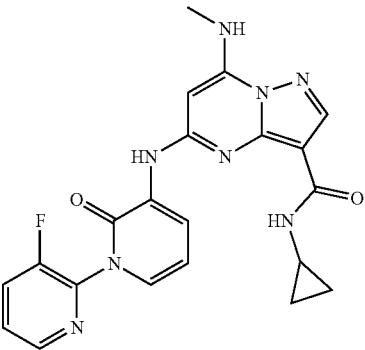 [SMILES: CNc1cc(Nc2cccn(-c3ncccc3F)c2=O)nc2c(C(=O)NC3CC3)cnn12] |

TABLE 1-continued

Selected Compounds

| Compound | Structure |
|---|---|
| I-144 | 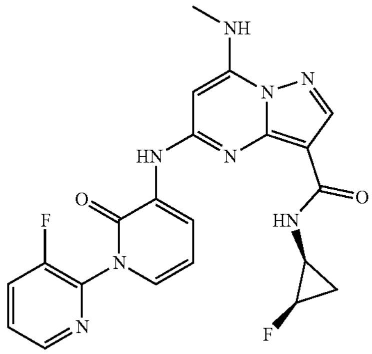 [SMILES: CNc1cc(Nc2cccn(-c3ncccc3F)c2=O)nc2c(C(=O)N[C@H]3C[C@H]3F)cnn12] |
| I-145 | 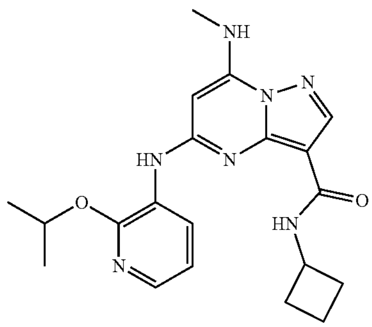 [SMILES: CNc1cc(Nc2cccnc2OC(C)C)nc2c(C(=O)NC3CCC3)cnn12] |
| I-146 | 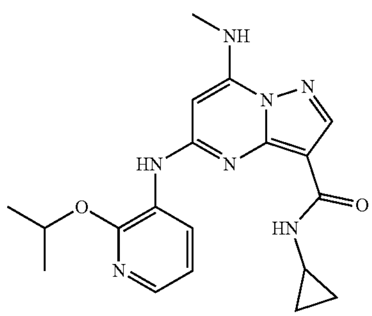 [SMILES: CNc1cc(Nc2cccnc2OC(C)C)nc2c(C(=O)NC3CC3)cnn12] |
| I-147 | 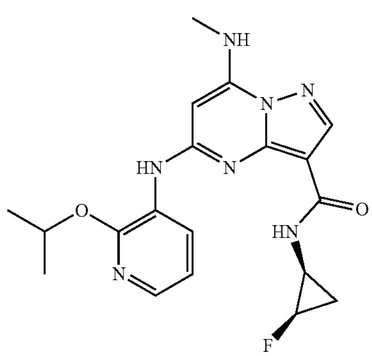 [SMILES: CNc1cc(Nc2cccnc2OC(C)C)nc2c(C(=O)N[C@H]3C[C@H]3F)cnn12] |

TABLE 1-continued
Selected Compounds
| Compound | Structure |
|---|---|
| I-148 | 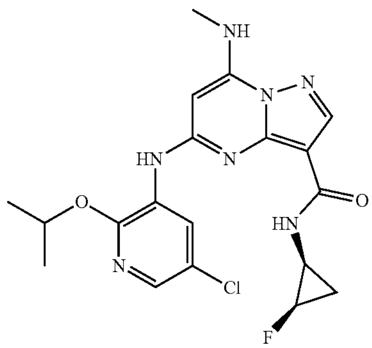 [SMILES: CNc1cc(Nc2cc(Cl)cnc2OC(C)C)nc2c(C(=O)N[C@H]3C[C@H]3F)cnn12] |
| I-149 | 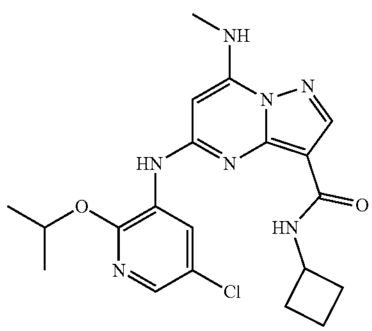 |
| I-150 | 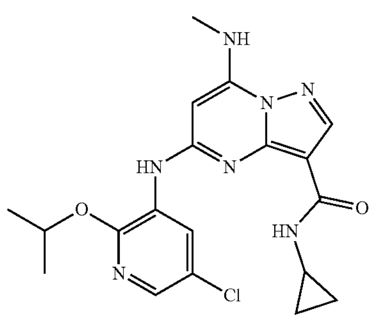 |
| I-151 | 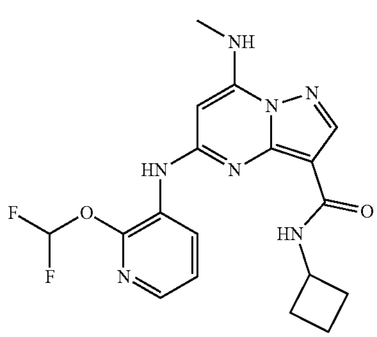 [SMILES: CNc1cc(Nc2cccnc2OC(F)F)nc2c(C(=O)NC3CCC3)cnn12] |

TABLE 1-continued

Selected Compounds

| Compound | Structure |
|---|---|
| I-152 | 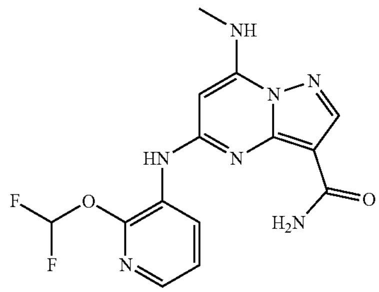 [SMILES: CNc1cc(Nc2cccnc2OC(F)F)nc2c(C(N)=O)cnn12] |
| I-153 | 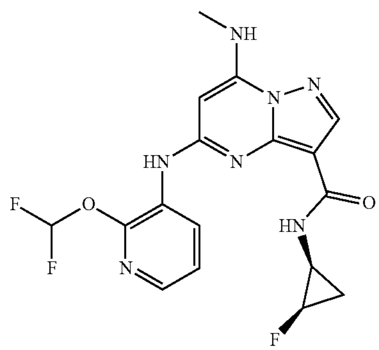 [SMILES: CNc1cc(Nc2cccnc2OC(F)F)nc2c(C(=O)N[C@H]3C[C@H]3F)cnn12] |
| I-154 | 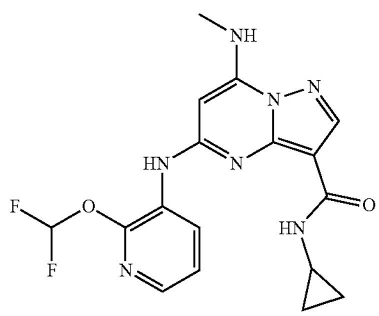 [SMILES: CNc1cc(Nc2cccnc2OC(F)F)nc2c(C(=O)NC3CC3)cnn12] |
| I-155 | 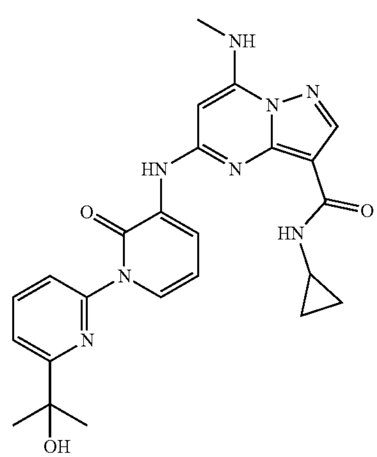 [SMILES: CNc1cc(Nc2cccn(-c3cccc(C(C)(C)O)n3)c2=O)nc2c(C(=O)NC3CC3)cnn12] |

TABLE 1-continued
Selected Compounds
| Compound | Structure |
|---|---|
| I-156 | 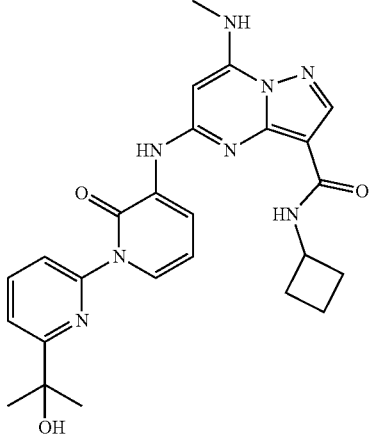 [SMILES: CNc1cc(Nc2cccn(-c3cccc(C(C)(C)O)n3)c2=O)nc2c(C(=O)NC3CCC3)cnn12] |
| I-157 | 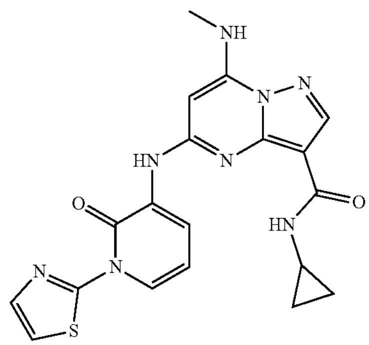 [SMILES: CNc1cc(Nc2cccn(-c3nccs3)c2=O)nc2c(C(=O)NC3CC3)cnn12] |
| I-158 | 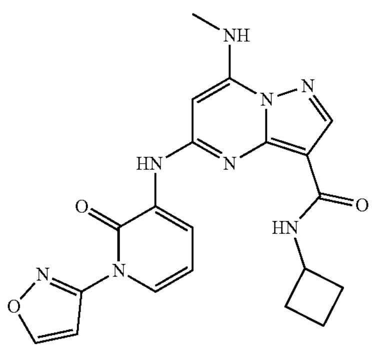 [SMILES: CNc1cc(Nc2cccn(-c3ccon3)c2=O)nc2c(C(=O)NC3CCC3)cnn12] |
| I-159 | 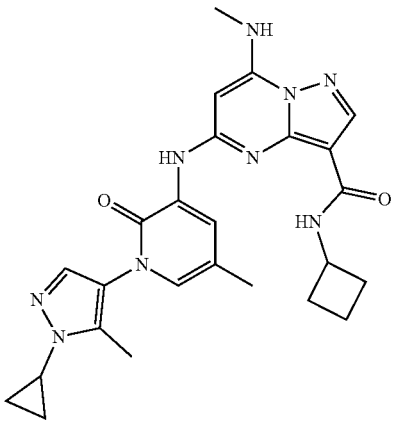 [SMILES: CNc1cc(Nc2cc(C)cn(-c3cnn(C4CC4)c3C)c2=O)nc2c(C(=O)NC3CCC3)cnn12] |

TABLE 1-continued
Selected Compounds
| Compound | Structure |
|---|---|
| I-160 | 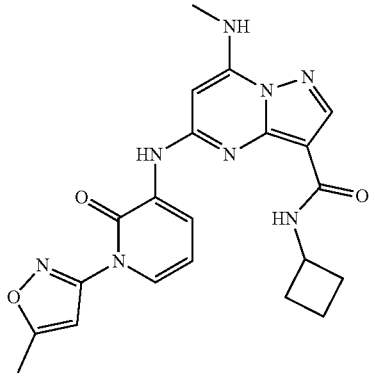 [SMILES: CNc1cc(Nc2cccn(-c3cc(C)on3)c2=O)nc2c(C(=O)NC3CCC3)cnn12] |
| I-161 | 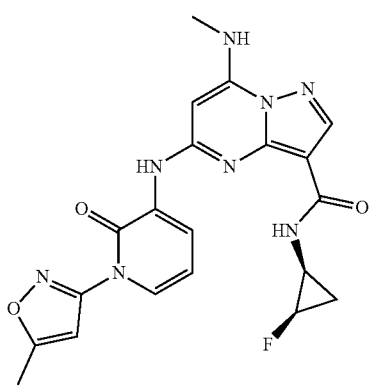 [SMILES: CNc1cc(Nc2cccn(-c3cc(C)on3)c2=O)nc2c(C(=O)N[C@H]3C[C@H]3F)cnn12] |
| I-162 | 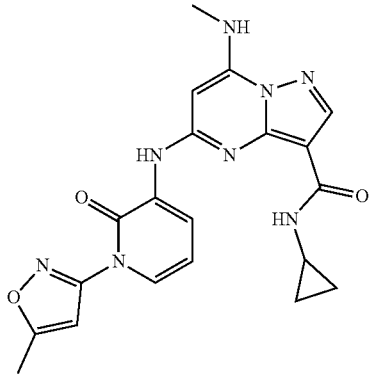 [SMILES: CNc1cc(Nc2cccn(-c3cc(C)on3)c2=O)nc2c(C(=O)NC3CC3)cnn12] |
| I-163 | 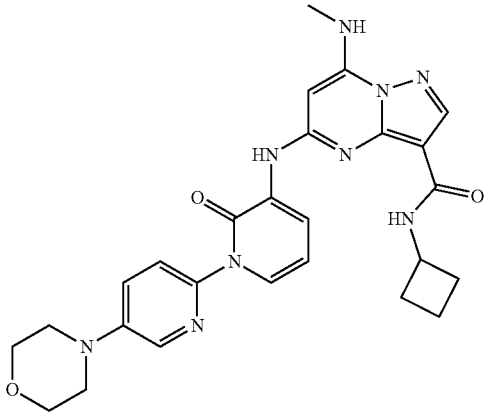 [SMILES: CNc1cc(Nc2cccn(-c3ccc(N4CCOCC4)cn3)c2=O)nc2c(C(=O)NC3CCC3)cnn12] |

TABLE 1-continued

Selected Compounds

| Compound | Structure |
|---|---|
| I-164 | (structure) |
| I-165 | (structure) |
| I-166 | (structure) |
| I-167 | (structure) |

TABLE 1-continued
Selected Compounds
| Compound | Structure |
|---|---|
| I-168 | 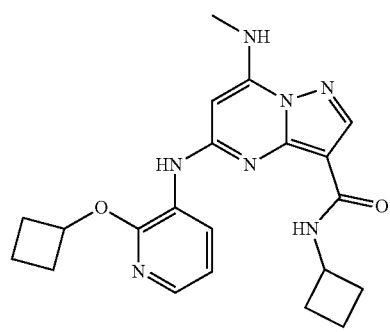 [SMILES: CNc1cc(Nc2cccnc2OC2CCC2)nc2c(C(=O)NC3CCC3)cnn12] |
| I-169 | 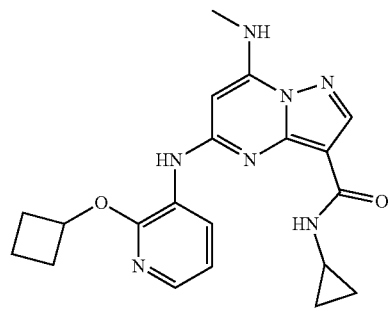 [SMILES: CNc1cc(Nc2cccnc2OC2CCC2)nc2c(C(=O)NC3CC3)cnn12] |
| I-170 | 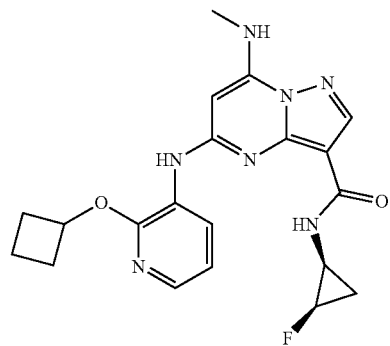 [SMILES: CNc1cc(Nc2cccnc2OC2CCC2)nc2c(C(=O)N[C@H]3C[C@H]3F)cnn12] |
| I-171 | 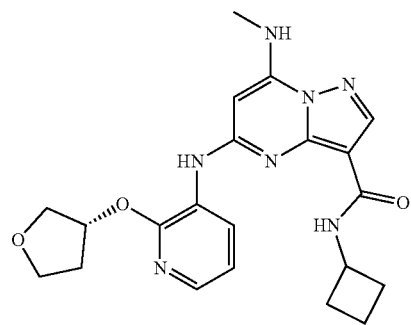 [SMILES: CNc1cc(Nc2cccnc2O[C@@H]2CCOC2)nc2c(C(=O)NC3CCC3)cnn12] |

TABLE 1-continued
Selected Compounds
| Compound | Structure |
|---|---|
| I-172 | 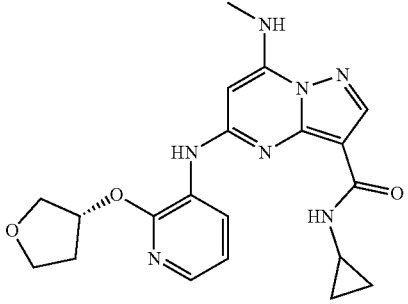 [SMILES: CNc1cc(Nc2cccnc2O[C@@H]2CCOC2)nc2c(C(=O)NC3CC3)cnn12] |
| I-173 | 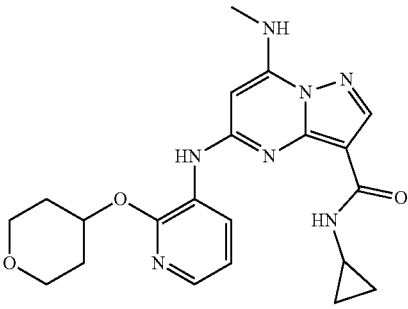 [SMILES: CNc1cc(Nc2cccnc2OC2CCOCC2)nc2c(C(=O)NC3CC3)cnn12] |
| I-174 | 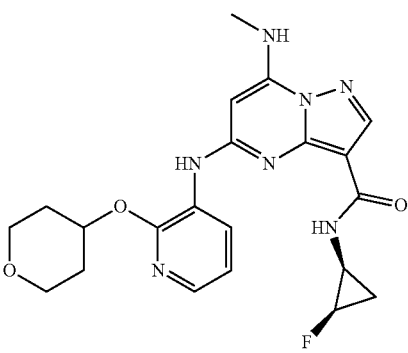 [SMILES: CNc1cc(Nc2cccnc2OC2CCOCC2)nc2c(C(=O)N[C@H]3C[C@H]3F)cnn12] |
| I-175 | 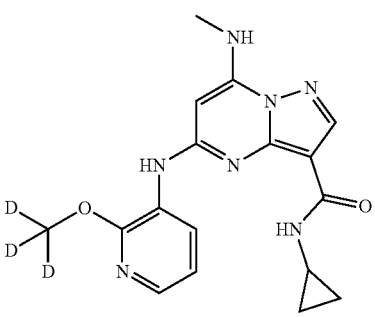 |

US 10,562,906 B2
169   170
TABLE 1-continued
Selected Compounds
| Compound | Structure |
|---|---|
| I-176 | 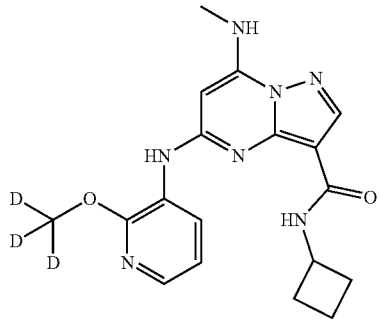 |
| I-177 | 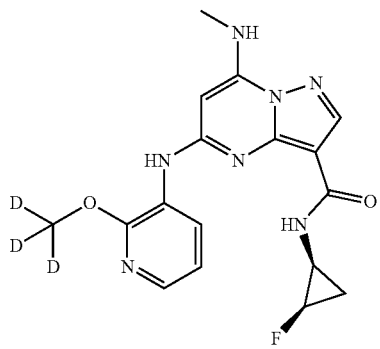 |
| I-178 | 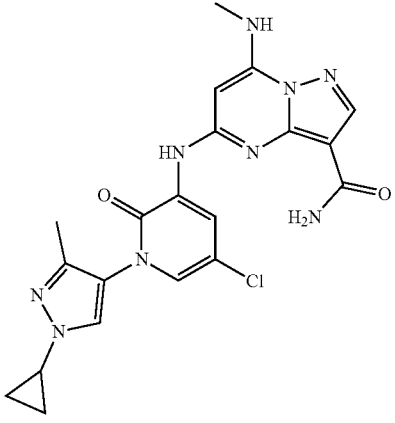 [SMILES: CNc1cc(Nc2cc(Cl)cn(-c3cn(C4CC4)nc3C)c2=O)nc2c(C(N)=O)cnn12] |
| I-179 | 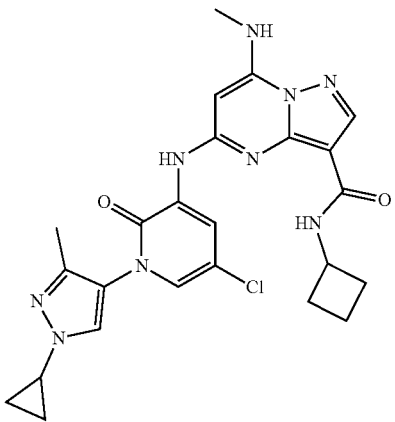 [SMILES: CNc1cc(Nc2cc(Cl)cn(-c3cn(C4CC4)nc3C)c2=O)nc2c(C(=O)NC3CCC3)cnn12] |

TABLE 1-continued

Selected Compounds

| Compound | Structure |
|---|---|
| I-180 | 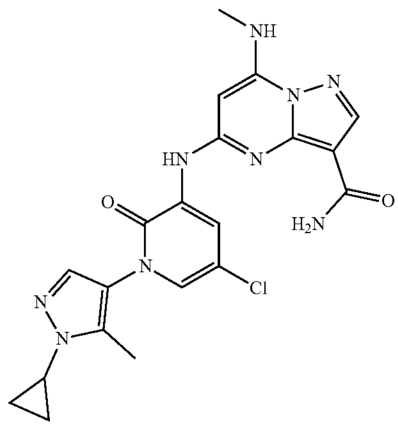 [SMILES: CNc1cc(Nc2cc(Cl)cn(-c3cnn(C4CC4)c3C)c2=O)nc2c(C(N)=O)cnn12] |
| I-181 | 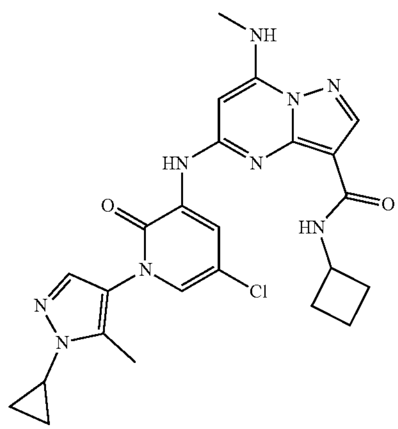 [SMILES: CNc1cc(Nc2cc(Cl)cn(-c3cnn(C4CC4)c3C)c2=O)nc2c(C(=O)NC3CCC3)cnn12] |
| I-182 | 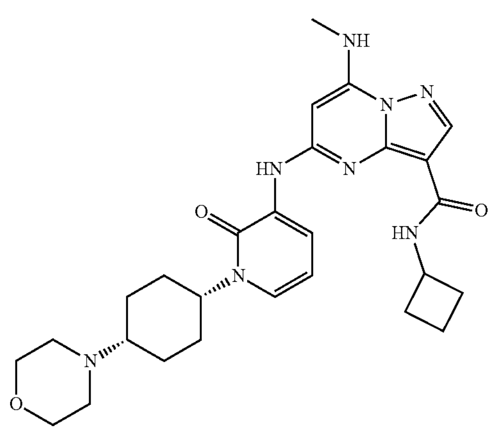 [SMILES: CNc1cc(Nc2cccn([C@H]3CC[C@@H](N4CCOCC4)CC3)c2=O)nc2c(C(=O)NC3CCC3)cnn12] |

TABLE 1-continued

| Selected Compounds | |
|---|---|
| Compound | Structure |
| I-183 | |
| I-184 | |
| I-185 | |
| I-186 | |

TABLE 1-continued

| Compound | Structure |
|---|---|
| I-187 | 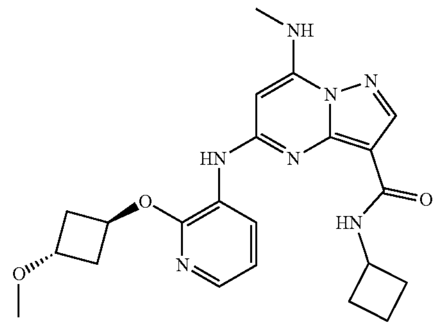 [SMILES: CNc1cc(Nc2cccnc2O[C@H]2C[C@H](OC)C2)nc2c(C(=O)NC3CCC3)cnn12] |
| I-188 | 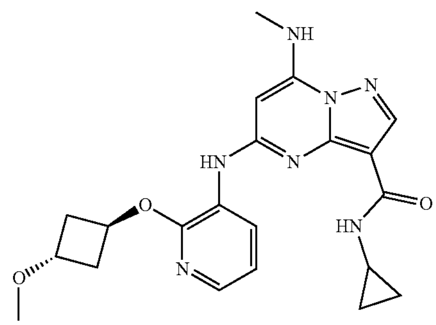 [SMILES: CNc1cc(Nc2cccnc2O[C@H]2C[C@H](OC)C2)nc2c(C(=O)NC3CC3)cnn12] |
| I-189 | 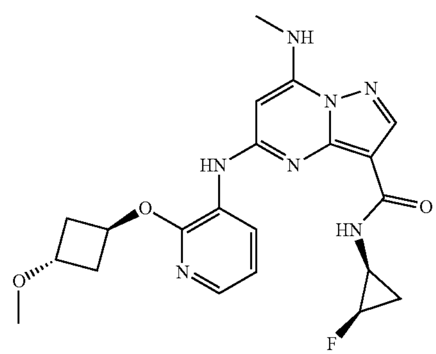 [SMILES: CNc1cc(Nc2cccnc2O[C@H]2C[C@H](OC)C2)nc2c(C(=O)N[C@H]3C[C@H]3F)cnn12] |
| I-190 | 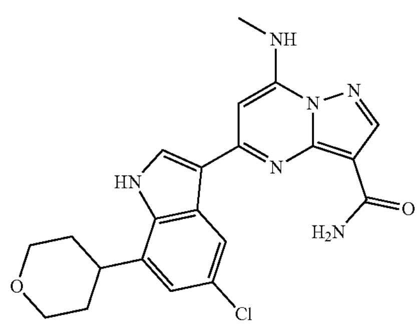 [SMILES: CNc1cc(-c2c[nH]c3c(C4CCOCC4)cc(Cl)cc23)nc2c(C(N)=O)cnn12] |

TABLE 1-continued
Selected Compounds
| Compound | Structure |
|---|---|
| I-191 | 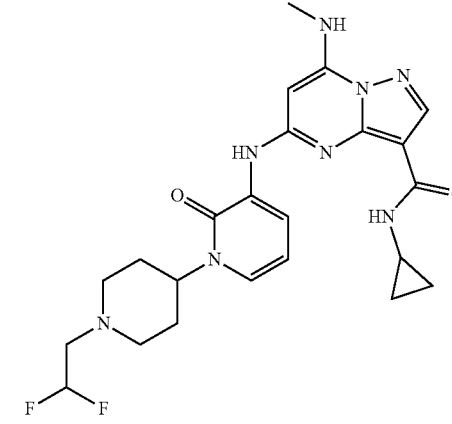 |
| I-192 | 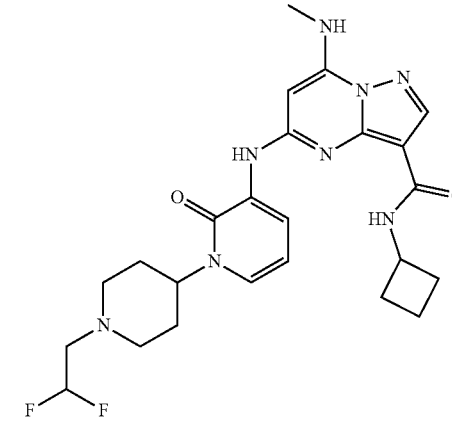 |
| I-193 | 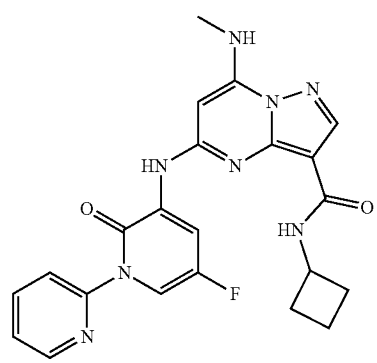 [SMILES: CNc1cc(Nc2cc(F)cn(-c3ccccn3)c2=O)nc2c(C(=O)NC3CCC3)cnn12] |
| I-194 | 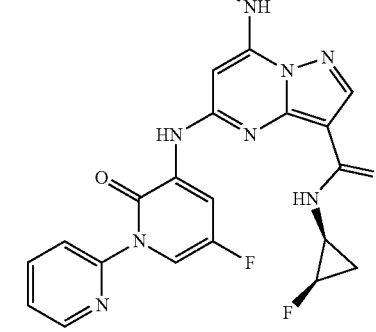 |

TABLE 1-continued
Selected Compounds
| Compound | Structure |
|---|---|
| I-195 | 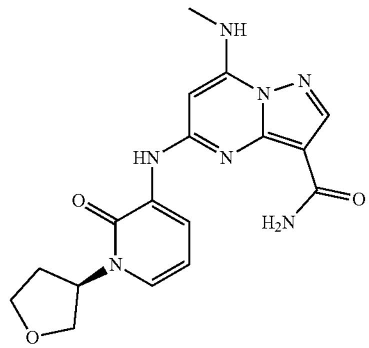 [SMILES: CNc1cc(Nc2cccn([C@@H]3CCOC3)c2=O)nc2c(C(N)=O)cnn12] |
| I-196 | 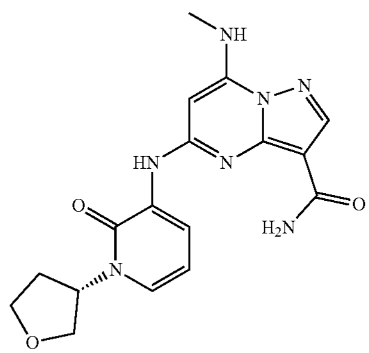 [SMILES: CNc1cc(Nc2cccn([C@H]3CCOC3)c2=O)nc2c(C(N)=O)cnn12] |
| I-197 | 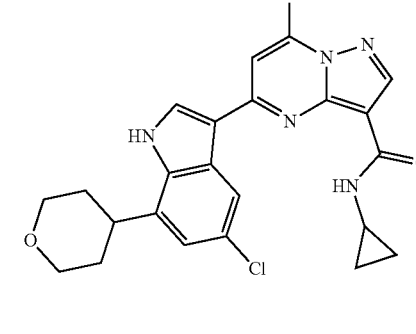 |
| I-198 | 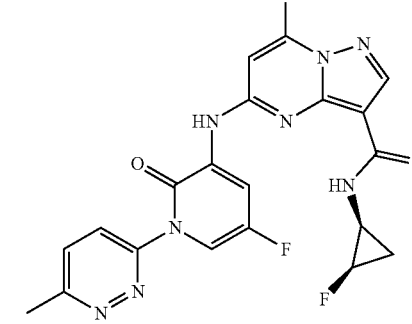 |

TABLE 1-continued

| Compound | Structure |
|---|---|
| I-199 | 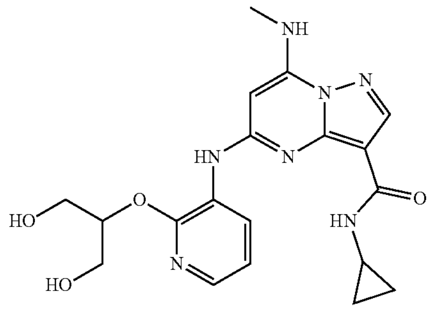 [SMILES: CNc1cc(Nc2cccnc2OC(CO)CO)nc2c(C(=O)NC3CC3)cnn12] |
| I-200 | 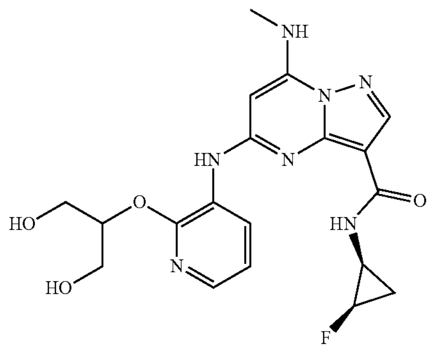 [SMILES: CNc1cc(Nc2cccnc2OC(CO)CO)nc2c(C(=O)N[C@H]3C[C@H]3F)cnn12] |
| I-201 | 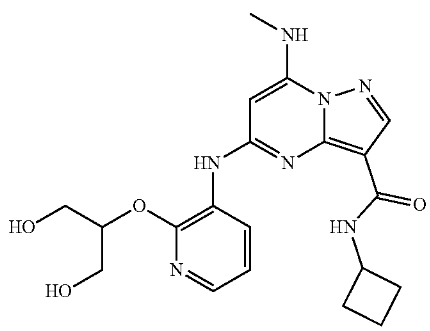 [SMILES: CNc1cc(Nc2cccnc2OC(CO)CO)nc2c(C(=O)NC3CCC3)cnn12] |
| I-202 | 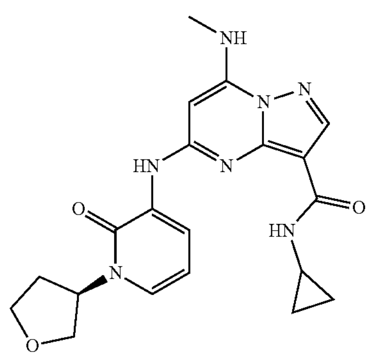 [SMILES: CNc1cc(Nc2cccn([C@@H]3CCOC3)c2=O)nc2c(C(=O)NC3CC3)cnn12] |

TABLE 1-continued

| Selected Compounds | |
|---|---|
| Compound | Structure |
| I-203 | |
| I-204 | |
| I-205 | |
| I-206 | |

TABLE 1-continued
Selected Compounds
| Compound | Structure |
|---|---|
| I-207 | 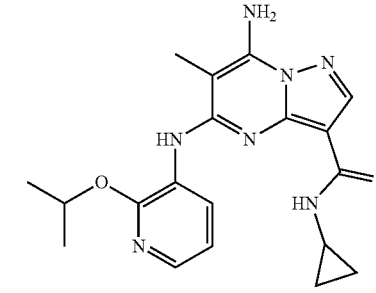 |
| I-208 | 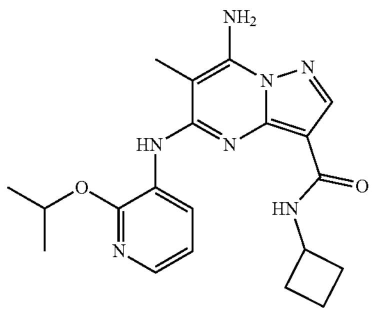 [SMILES: Cc1c(Nc2cccnc2OC(C)C)nc2c(C(=O)NC3CCC3)cnn2c1N] |
| I-209 | 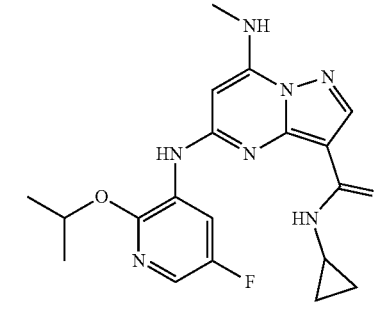 |
| I-210 | 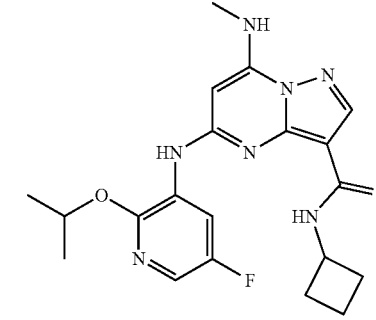 |

TABLE 1-continued

| Compound | Structure |
|---|---|
| I-211 | (pyrazolo[1,5-a]pyrimidine with 7-methylamino, 5-[(2-isopropoxy-5-fluoropyridin-3-yl)amino], 3-carboxamide N-[(1S,2R)-2-fluorocyclopropyl]) |
| I-212 | (pyrazolo[1,5-a]pyrimidine with 7-methylamino, 5-[(2-isopropoxy-5-methylpyridin-3-yl)amino], 3-carboxamide N-cyclopropyl) |
| I-213 | (pyrazolo[1,5-a]pyrimidine with 7-methylamino, 5-[(2-isopropoxy-5-methylpyridin-3-yl)amino], 3-carboxamide N-cyclobutyl) |
| I-214 | (pyrazolo[1,5-a]pyrimidine with 7-methylamino, 5-[(2-isopropoxy-5-methylpyridin-3-yl)amino], 3-carboxamide N-[(1S,2R)-2-fluorocyclopropyl]) |

TABLE 1-continued
Selected Compounds
| Compound | Structure |
|---|---|
| I-215 | 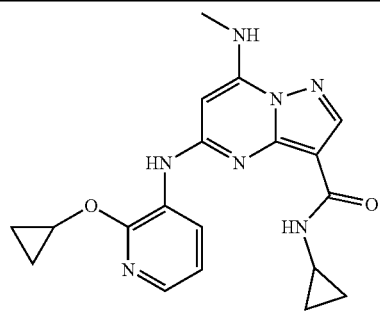 |
| I-216 | 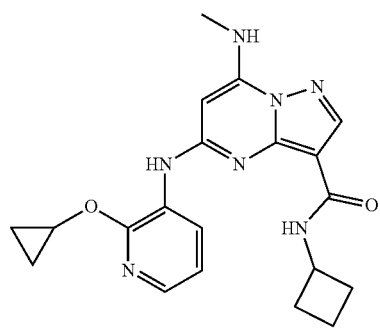 [SMILES: CNc1cc(Nc2cccnc2OC2CC2)nc2c(C(=O)NC3CCC3)cnn12] |
| I-217 | 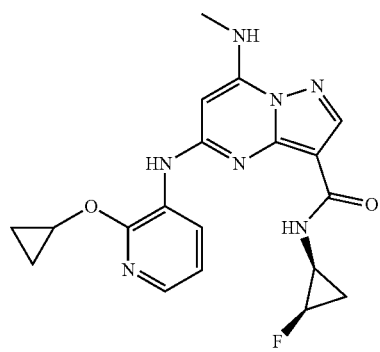 [SMILES: CNc1cc(Nc2cccnc2OC2CC2)nc2c(C(=O)N[C@H]3C[C@H]3F)cnn12] |
| I-218 | 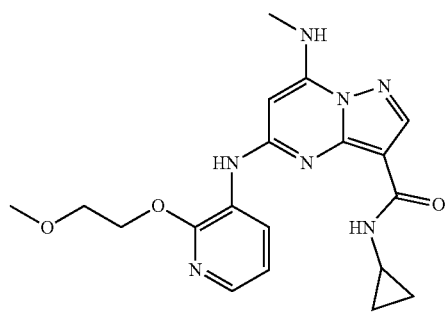 [SMILES: CNc1cc(Nc2cccnc2OCCOC)nc2c(C(=O)NC3CC3)cnn12] |

TABLE 1-continued
Selected Compounds
| Compound | Structure |
|---|---|
| I-219 | 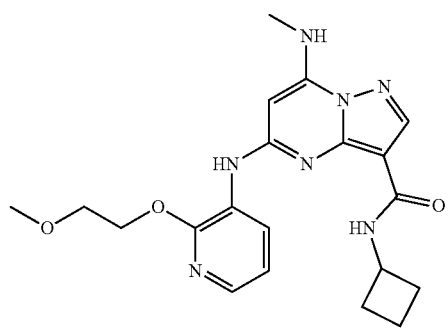 [SMILES: CNc1cc(Nc2cccnc2OCCOC)nc2c(C(=O)NC3CCC3)cnn12] |
| I-220 | 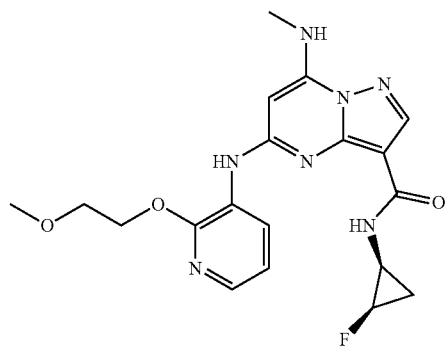 [SMILES: CNc1cc(Nc2cccnc2OCCOC)nc2c(C(=O)N[C@H]3C[C@H]3F)cnn12] |
| I-221 | 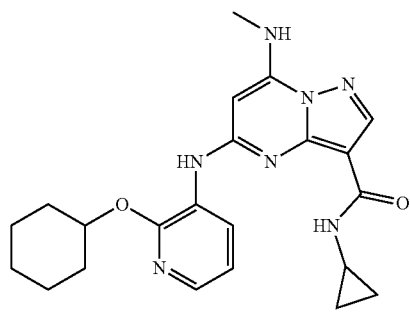 [SMILES: CNc1cc(Nc2cccnc2OC2CCCCC2)nc2c(C(=O)NC3CC3)cnn12] |
| I-222 | 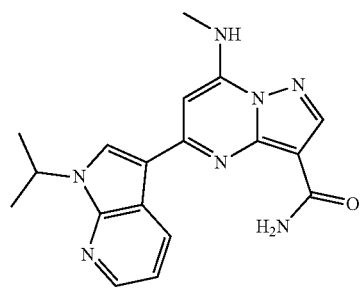 [SMILES: CNc1cc(-c2cn(C(C)C)c3ncccc23)nc2c(C(N)=O)cnn12] |

TABLE 1-continued

Selected Compounds

| Compound | Structure |
|---|---|
| I-223 | 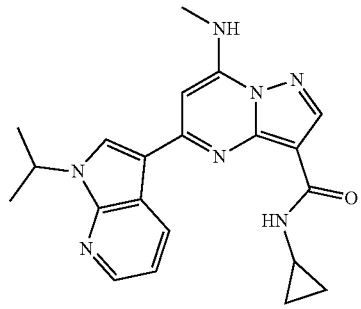 [SMILES: CNc1cc(-c2cn(C(C)C)c3ncccc23)nc2c(C(=O)NC3CC3)cnn12] |
| I-224 | 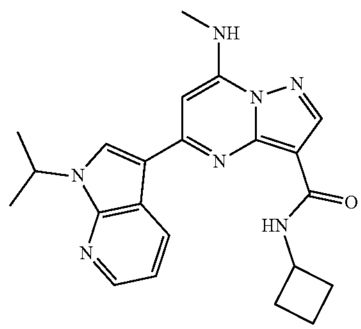 [SMILES: CNc1cc(-c2cn(C(C)C)c3ncccc23)nc2c(C(=O)NC3CCC3)cnn12] |
| I-225 | 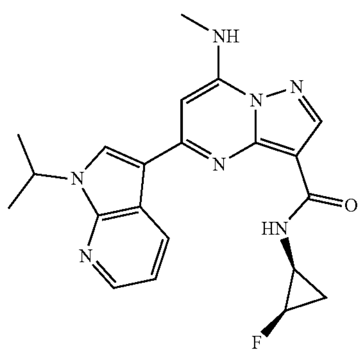 [SMILES: CNc1cc(-c2cn(C(C)C)c3ncccc23)nc2c(C(=O)N[C@H]3C[C@H]3F)cnn12] |
| I-226 | 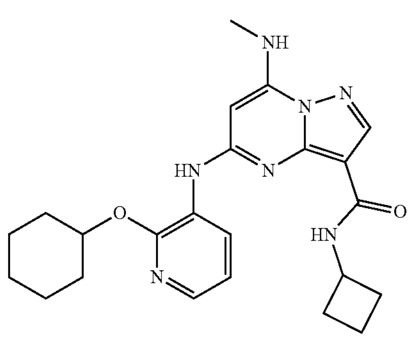 [SMILES: CNc1cc(Nc2cccnc2OC2CCCCC2)nc2c(C(=O)NC3CCC3)cnn12] |

TABLE 1-continued
Selected Compounds
| Compound | Structure |
|---|---|
| I-227 | 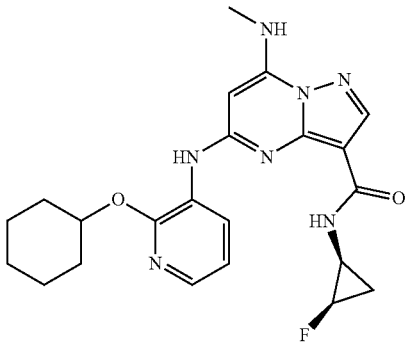 [SMILES: CNc1cc(Nc2cccnc2OC2CCCCC2)nc2c(C(=O)N[C@H]3C[C@H]3F)cnn12] |
| I-228 | 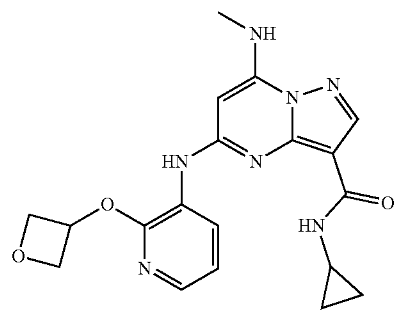 [SMILES: CNc1cc(Nc2cccnc2OC2COC2)nc2c(C(=O)NC3CC3)cnn12] |
| I-229 | 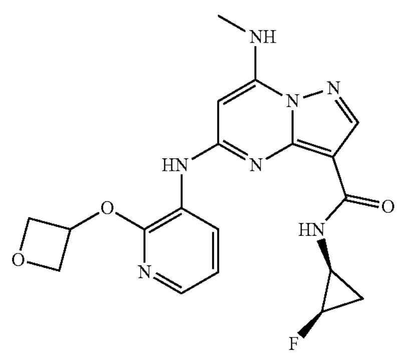 [SMILES: CNc1cc(Nc2cccnc2OC2COC2)nc2c(C(=O)N[C@H]3C[C@H]3F)cnn12] |
| I-230 | 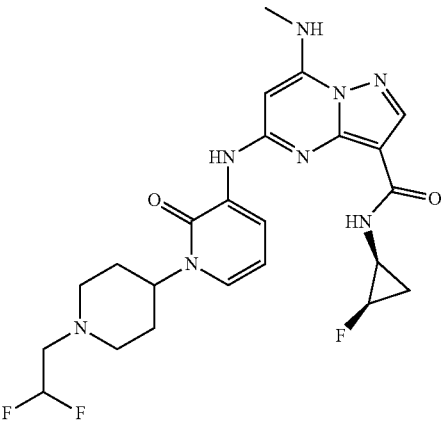 [SMILES: CNc1cc(Nc2cccn(C3CCN(CC(F)F)CC3)c2=O)nc2c(C(=O)N[C@H]3C[C@H]3F)cnn12] |

TABLE 1-continued
Selected Compounds
| Compound | Structure |
|---|---|
| I-231 | 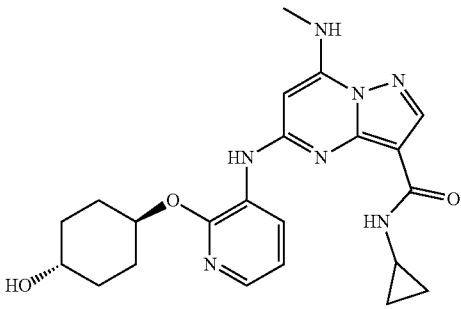 [SMILES: CNc1cc(Nc2cccnc2O[C@H]2CC[C@H](O)CC2)nc2c(C(=O)NC3CC3)cnn12] |
| I-232 | 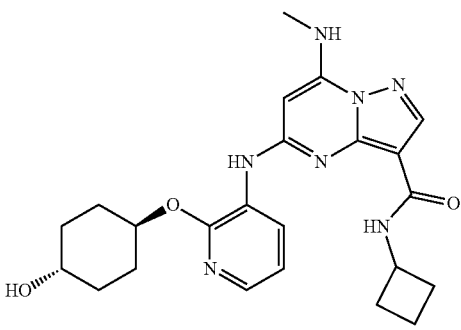 [SMILES: CNc1cc(Nc2cccnc2O[C@H]2CC[C@H](O)CC2)nc2c(C(=O)NC3CCC3)cnn12] |
| I-233 | 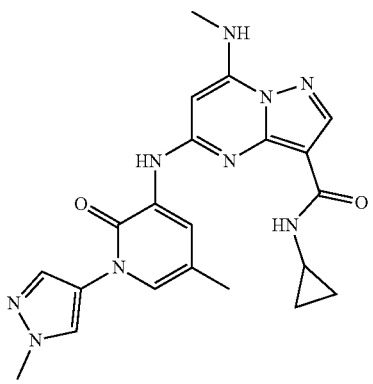 [SMILES: CNc1cc(Nc2cc(C)cn(-c3cnn(C)c3)c2=O)nc2c(C(=O)NC3CC3)cnn12] |
| I-234 | 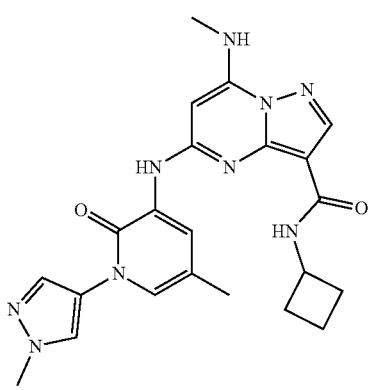 [SMILES: CNc1cc(Nc2cc(C)cn(-c3cnn(C)c3)c2=O)nc2c(C(=O)NC3CCC3)cnn12] |

TABLE 1-continued

Selected Compounds

| Compound | Structure |
|---|---|
| I-235 | 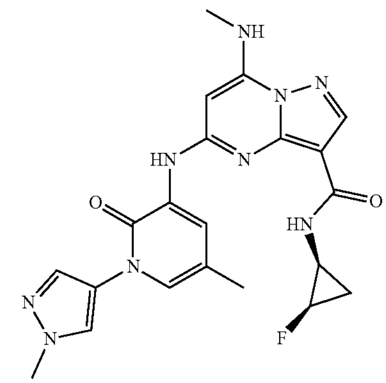 [SMILES: CNc1cc(Nc2cc(C)cn(-c3cnn(C)c3)c2=O)nc2c(C(=O)N[C@H]3C[C@H]3F)cnn12] |
| I-236 | 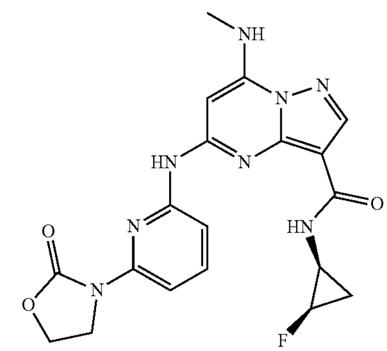 [SMILES: CNc1cc(Nc2cccc(N3CCOC3=O)n2)nc2c(C(=O)N[C@H]3C[C@H]3F)cnn12] |
| I-237 | 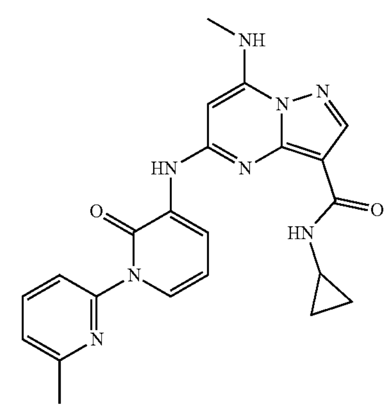 [SMILES: CNc1cc(Nc2cccn(-c3cccc(C)n3)c2=O)nc2c(C(=O)NC3CC3)cnn12] |
| I-238 | 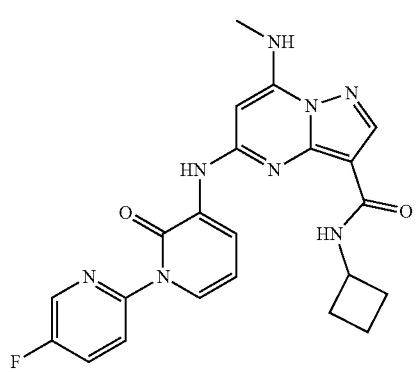 [SMILES: CNc1cc(Nc2cccn(-c3ccc(F)cn3)c2=O)nc2c(C(=O)NC3CCC3)cnn12] |

TABLE 1-continued
Selected Compounds
| Compound | Structure |
|---|---|
| I-239 | 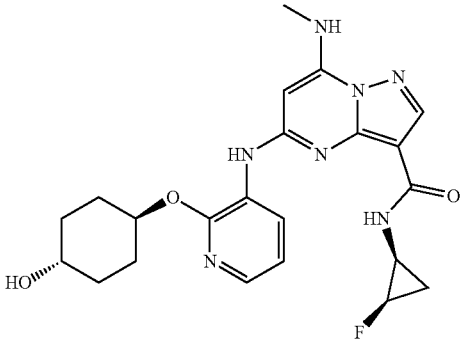 [SMILES: CNc1cc(Nc2cccnc2O[C@H]2CC[C@H](O)CC2)nc2c(C(=O)N[C@H]3C[C@H]3F)cnn12] |
| I-240 | 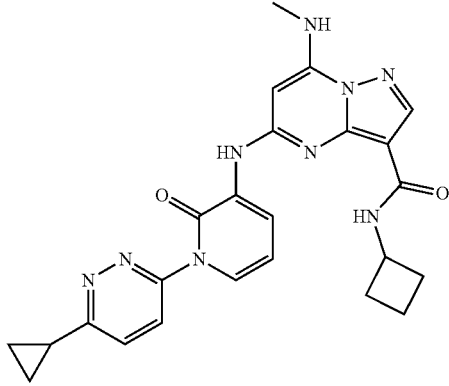 [SMILES: CNc1cc(Nc2cccn(-c3ccc(C4CC4)nn3)c2=O)nc2c(C(=O)NC3CCC3)cnn12] |
| I-241 | 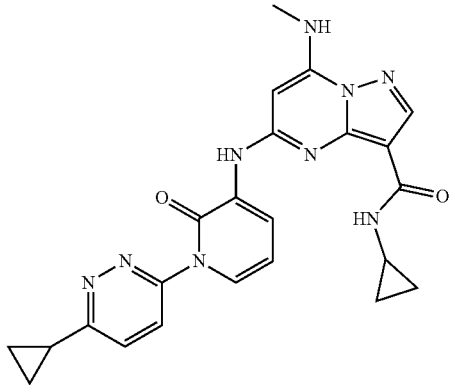 [SMILES: CNc1cc(Nc2cccn(-c3ccc(C4CC4)nn3)c2=O)nc2c(C(=O)NC3CC3)cnn12] |
| I-242 | 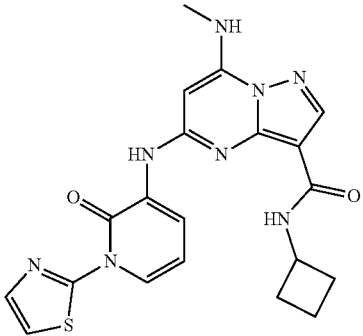 [SMILES: CNc1cc(Nc2cccn(-c3nccs3)c2=O)nc2c(C(=O)NC3CCC3)cnn12] |

TABLE 1-continued

Selected Compounds

| Compound | Structure |
|---|---|
| I-243 | 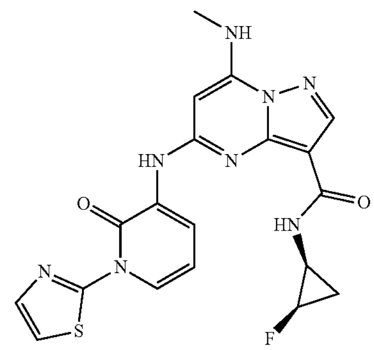 [SMILES: CNc1cc(Nc2cccn(-c3nccs3)c2=O)nc2c(C(=O)N[C@H]3C[C@H]3F)cnn12] |
| I-244 | 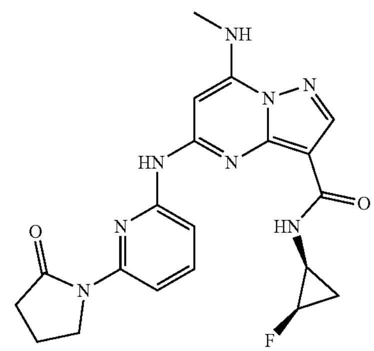 [SMILES: CNc1cc(Nc2cccc(N3CCCC3=O)n2)nc2c(C(=O)N[C@H]3C[C@H]3F)cnn12] |
| I-245 | 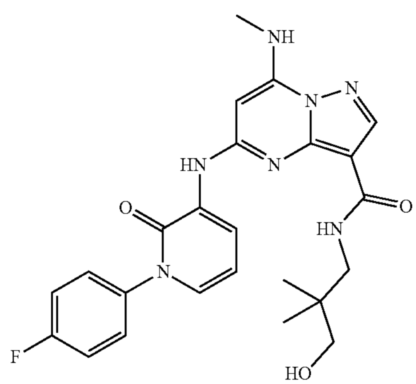 [SMILES: CNc1cc(Nc2cccn(-c3ccc(F)cc3)c2=O)nc2c(C(=O)NCC(C)(C)CO)cnn12] |
| I-246 | 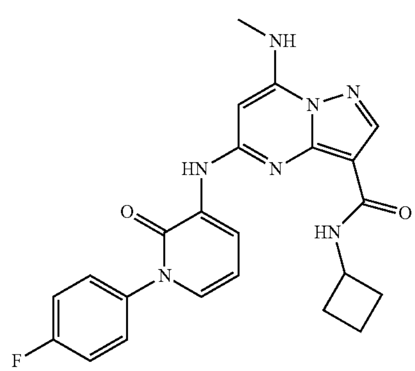 [SMILES: CNc1cc(Nc2cccn(-c3ccc(F)cc3)c2=O)nc2c(C(=O)NC3CCC3)cnn12] |

TABLE 1-continued

| Compound | Structure |
|---|---|
| I-247 | 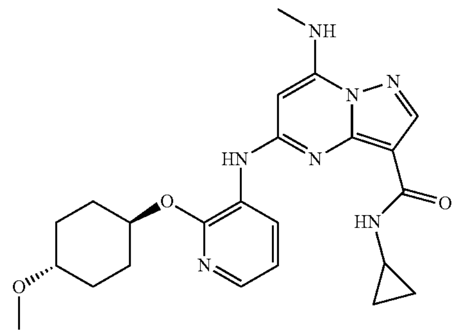 [SMILES: CNc1cc(Nc2cccnc2O[C@H]2CC[C@H](OC)CC2)nc2c(C(=O)NC3CC3)cnn12] |
| I-248 | 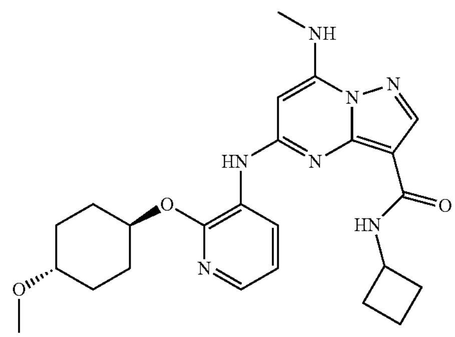 [SMILES: CNc1cc(Nc2cccnc2O[C@H]2CC[C@H](OC)CC2)nc2c(C(=O)NC3CCC3)cnn12] |
| I-249 | 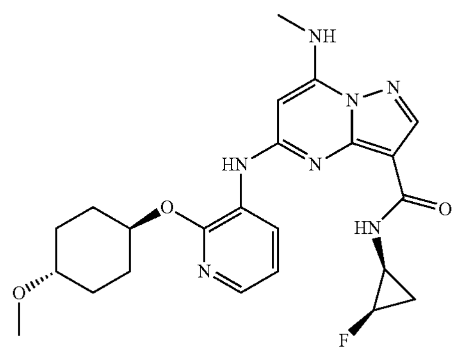 [SMILES: CNc1cc(Nc2cccnc2O[C@H]2CC[C@H](OC)CC2)nc2c(C(=O)N[C@H]3C[C@H]3F)cnn12] |
| I-250 | 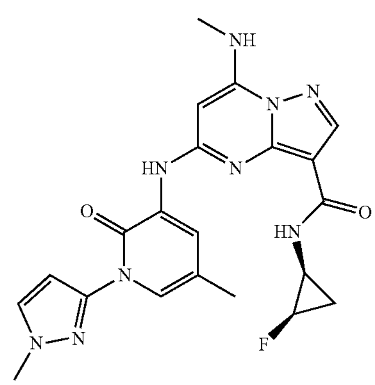 [SMILES: CNc1cc(Nc2cc(C)cn(-c3ccn(C)n3)c2=O)nc2c(C(=O)N[C@H]3C[C@H]3F)cnn12] |

TABLE 1-continued
Selected Compounds
| Compound | Structure |
|---|---|
| I-251 | 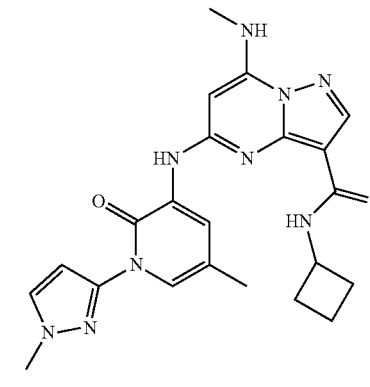 |
| I-252 | 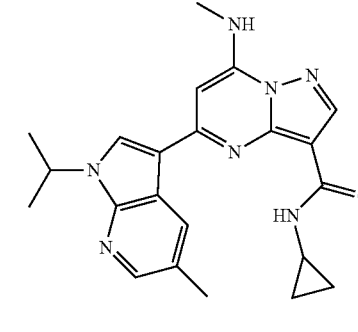 |
| I-253 | 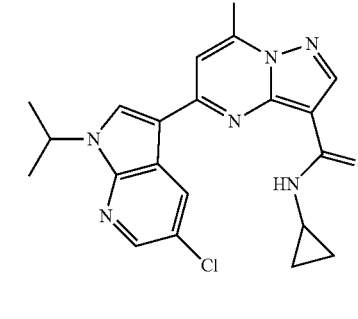 |
| I-254 | 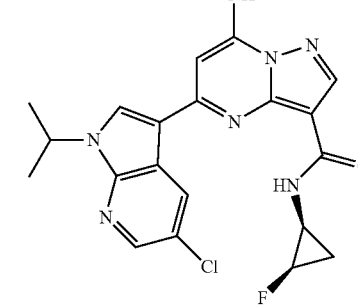 |

TABLE 1-continued

Selected Compounds

| Compound | Structure |
|---|---|
| I-255 | (structure) |
| I-256 | (structure) |
| I-257 | (structure) |
| I-258 | (structure) |

TABLE 1-continued
| Selected Compounds | |
|---|---|
| Compound | Structure |
| I-259 | 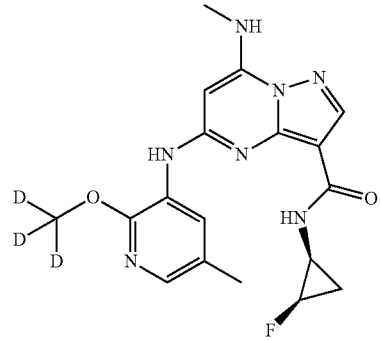 [SMILES: [2H]C([2H])([2H])Oc1ncc(C)cc1Nc1cc(NC)n2ncc(C(=O)N[C@H]3C[C@H]3F)c2n1] |
| I-260 | 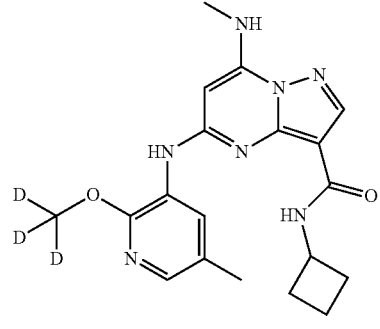 [SMILES: [2H]C([2H])([2H])Oc1ncc(C)cc1Nc1cc(NC)n2ncc(C(=O)NC3CCC3)c2n1] |
| I-261 | 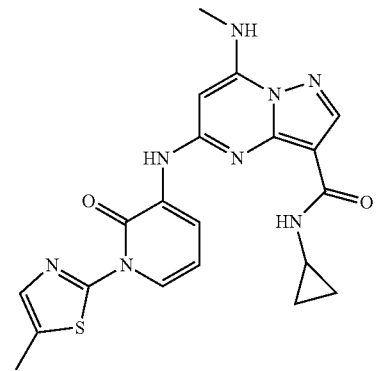 [SMILES: CNc1cc(Nc2cccn(-c3ncc(C)s3)c2=O)nc2c(C(=O)NC3CC3)cnn12] |
| I-262 | 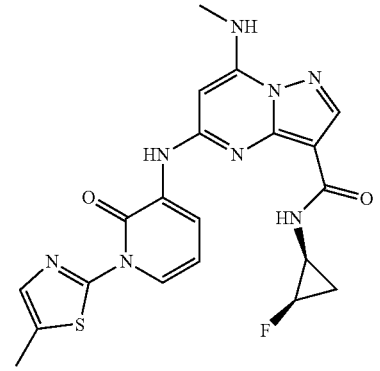 [SMILES: CNc1cc(Nc2cccn(-c3ncc(C)s3)c2=O)nc2c(C(=O)N[C@H]3C[C@H]3F)cnn12] |

TABLE 1-continued

Selected Compounds

| Compound | Structure |
|---|---|
| I-263 | 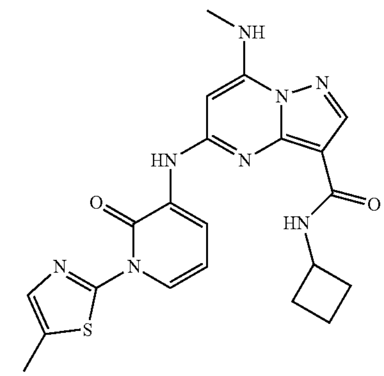 [SMILES: CNc1cc(Nc2cccn(-c3ncc(C)s3)c2=O)nc2c(C(=O)NC3CCC3)cnn12] |
| I-264 | 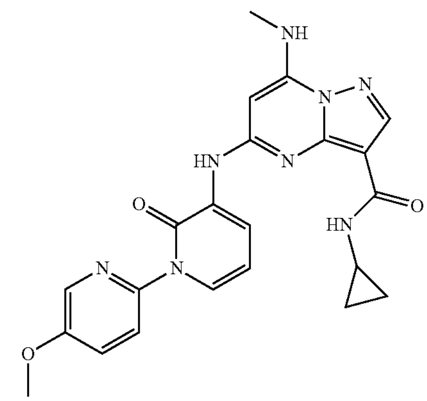 [SMILES: CNc1cc(Nc2cccn(-c3ccc(OC)cn3)c2=O)nc2c(C(=O)NC3CC3)cnn12] |
| I-265 | 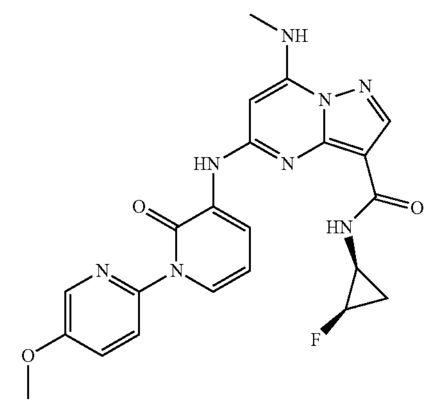 [SMILES: CNc1cc(Nc2cccn(-c3ccc(OC)cn3)c2=O)nc2c(C(=O)N[C@H]3C[C@H]3F)cnn12] |
| I-266 | 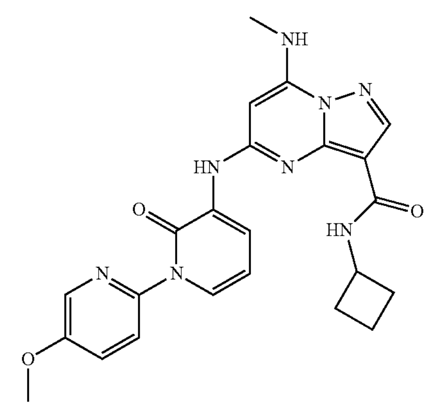 [SMILES: CNc1cc(Nc2cccn(-c3ccc(OC)cn3)c2=O)nc2c(C(=O)NC3CCC3)cnn12] |

TABLE 1-continued
Selected Compounds
| Compound | Structure |
|---|---|
| I-267 | 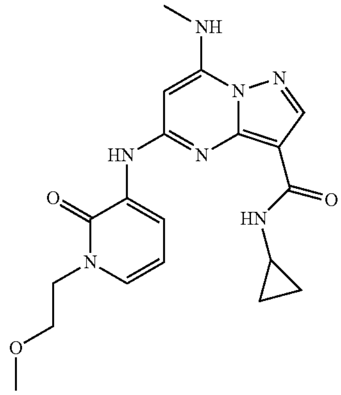 [SMILES: CNc1cc(Nc2cccn(CCOC)c2=O)nc2c(C(=O)NC3CC3)cnn12] |
| I-268 | 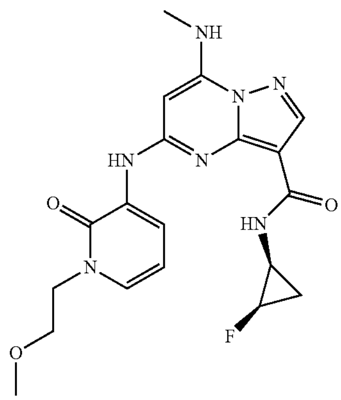 [SMILES: CNc1cc(Nc2cccn(CCOC)c2=O)nc2c(C(=O)N[C@H]3C[C@H]3F)cnn12] |
| I-269 | 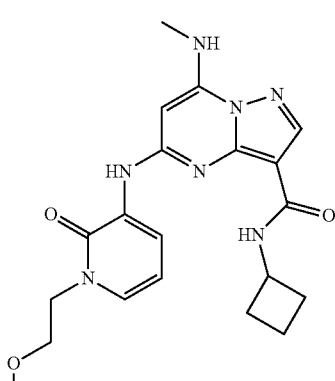 |
| I-270 | 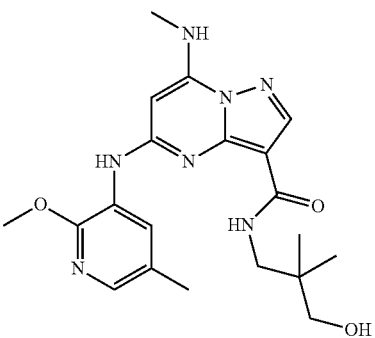 [SMILES: CNc1cc(Nc2cc(C)cnc2OC)nc2c(C(=O)NCC(C)(C)CO)cnn12] |

TABLE 1-continued

Selected Compounds

| Compound | Structure |
|---|---|
| I-271 | 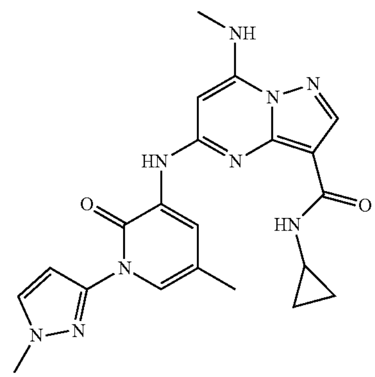 [SMILES: CNc1cc(Nc2cc(C)cn(-c3ccn(C)n3)c2=O)nc2c(C(=O)NC3CC3)cnn12] |
| I-272 | 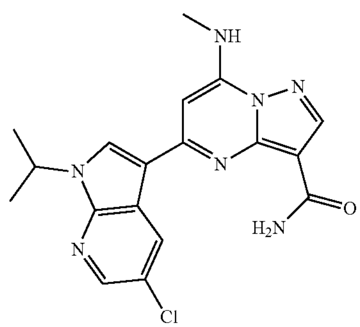 [SMILES: CNc1cc(-c2cn(C(C)C)c3ncc(Cl)cc23)nc2c(C(N)=O)cnn12] |
| I-273 | 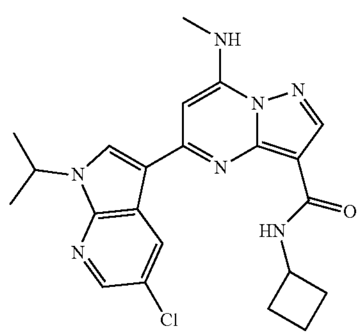 [SMILES: CNc1cc(-c2cn(C(C)C)c3ncc(Cl)cc23)nc2c(C(=O)NC3CCC3)cnn12] |
| I-274 | 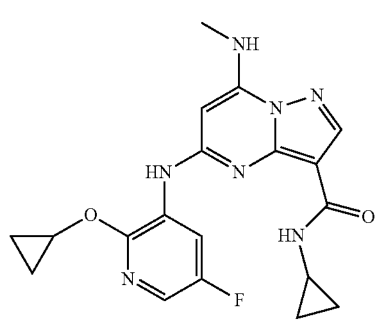 [SMILES: CNc1cc(Nc2cc(F)cnc2OC2CC2)nc2c(C(=O)NC3CC3)cnn12] |

TABLE 1-continued

Selected Compounds

| Compound | Structure |
|---|---|
| I-275 | 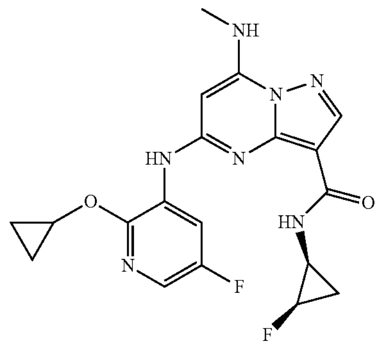 [SMILES: CNc1cc(Nc2cc(F)cnc2OC2CC2)nc2c(C(=O)N[C@H]3C[C@H]3F)cnn12] |
| I-276 | 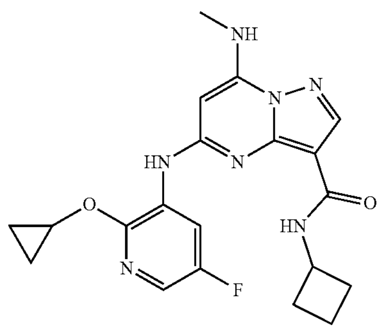 [SMILES: CNc1cc(Nc2cc(F)cnc2OC2CC2)nc2c(C(=O)NC3CCC3)cnn12] |
| I-277 | 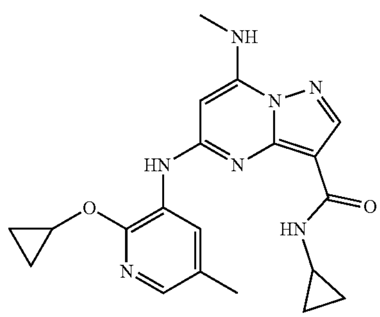 [SMILES: CNc1cc(Nc2cc(C)cnc2OC2CC2)nc2c(C(=O)NC3CC3)cnn12] |
| I-278 | 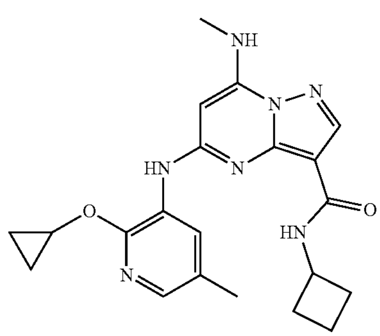 |

TABLE 1-continued
Selected Compounds
| Compound | Structure |
|---|---|
| I-279 | 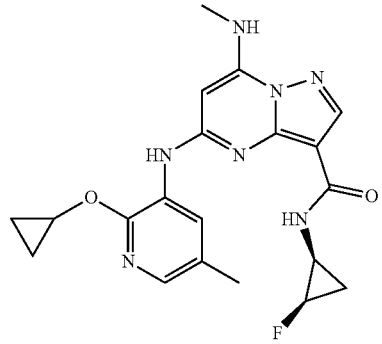 [SMILES: CNc1cc(Nc2cc(C)cnc2OC2CC2)nc2c(C(=O)N[C@H]3C[C@H]3F)cnn12] |
| I-280 | 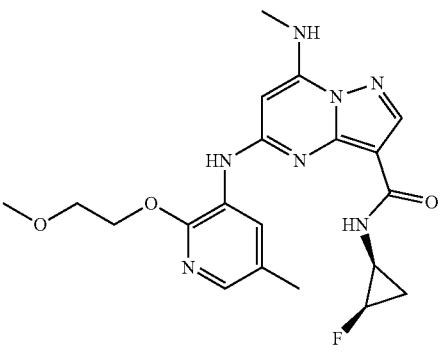 [SMILES: CNc1cc(Nc2cc(C)cnc2OCCOC)nc2c(C(=O)N[C@H]3C[C@H]3F)cnn12] |
| I-281 | 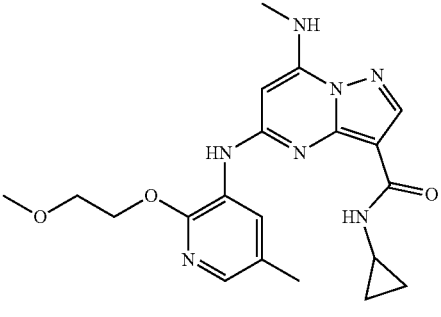 |
| I-282 | 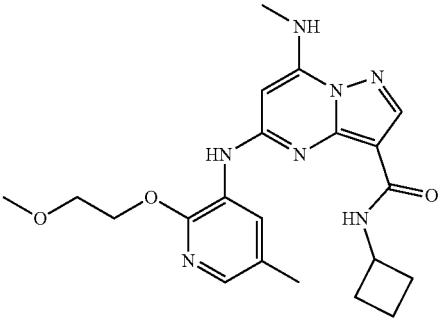 [SMILES: CNc1cc(Nc2cc(C)cnc2OCCOC)nc2c(C(=O)NC3CCC3)cnn12] |

TABLE 1-continued
Selected Compounds
| Compound | Structure |
|---|---|
| I-283 | 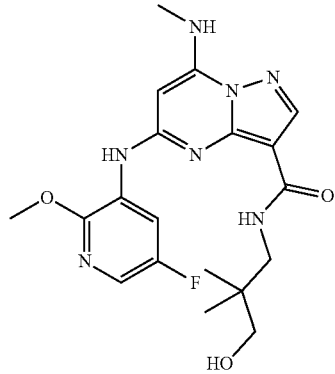 [SMILES: CNc1cc(Nc2cc(F)cnc2OC)nc2c(C(=O)NCC(C)(C)CO)cnn12] |
| I-284 | 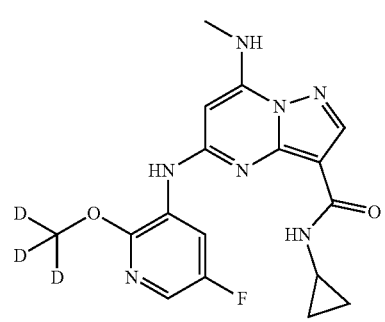 [SMILES: [2H]C([2H])([2H])Oc1ncc(F)cc1Nc1cc(NC)n2ncc(C(=O)NC3CC3)c2n1] |
| I-285 | 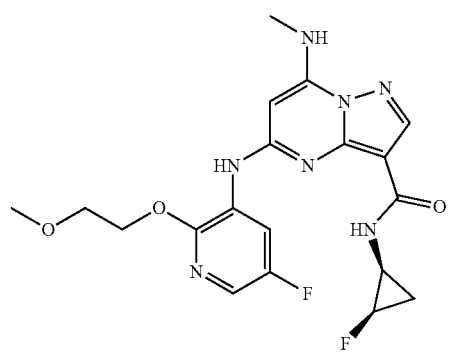 [SMILES: CNc1cc(Nc2cc(F)cnc2OCCOC)nc2c(C(=O)N[C@H]3C[C@H]3F)cnn12] |
| I-286 | 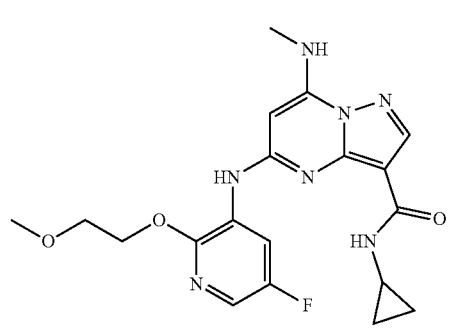 [SMILES: CNc1cc(Nc2cc(F)cnc2OCCOC)nc2c(C(=O)NC3CC3)cnn12] |

TABLE 1-continued

Selected Compounds

| Compound | Structure |
|---|---|
| I-287 | 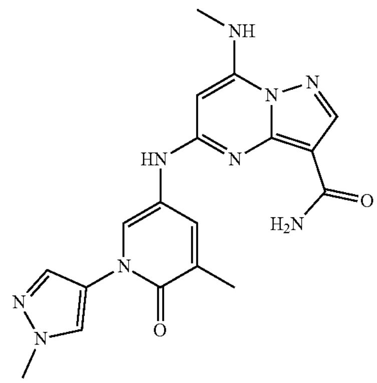 [SMILES: CNc1cc(Nc2cc(C)c(=O)n(-c3cnn(C)c3)c2)nc2c(C(N)=O)cnn12] |
| I-288 | 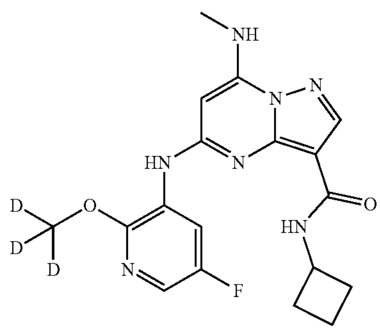 [SMILES: [2H]C([2H])([2H])Oc1ncc(F)cc1Nc1cc(NC)n2ncc(C(=O)NC3CCC3)c2n1] |
| I-289 | 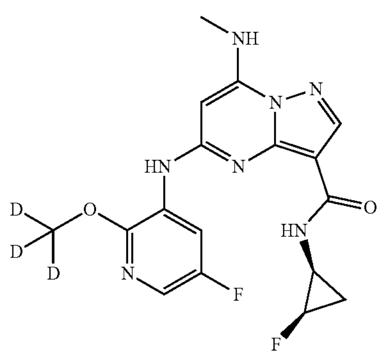 [SMILES: [2H]C([2H])([2H])Oc1ncc(F)cc1Nc1cc(NC)n2ncc(C(=O)N[C@H]3C[C@H]3F)c2n1] |
| I-290 | 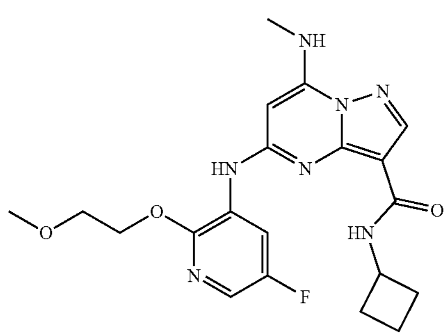 |

TABLE 1-continued
Selected Compounds
| Compound | Structure |
|---|---|
| I-291 | 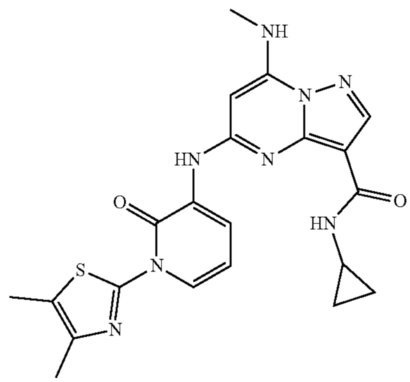 [SMILES: CNc1cc(Nc2cccn(-c3nc(C)c(C)s3)c2=O)nc2c(C(=O)NC3CC3)cnn12] |
| I-292 | 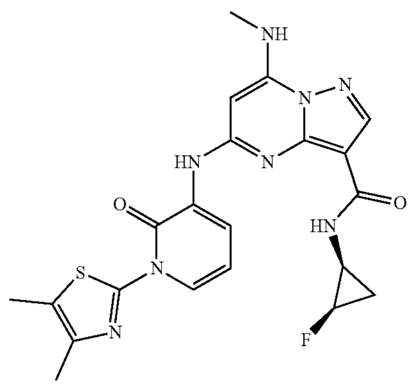 [SMILES: CNc1cc(Nc2cccn(-c3nc(C)c(C)s3)c2=O)nc2c(C(=O)N[C@H]3C[C@H]3F)cnn12] |
| I-293 | 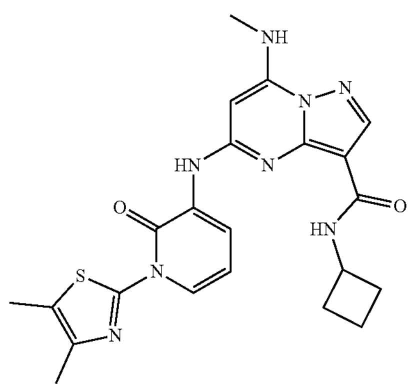 [SMILES: CNc1cc(Nc2cccn(-c3nc(C)c(C)s3)c2=O)nc2c(C(=O)NC3CCC3)cnn12] |
| I-294 | 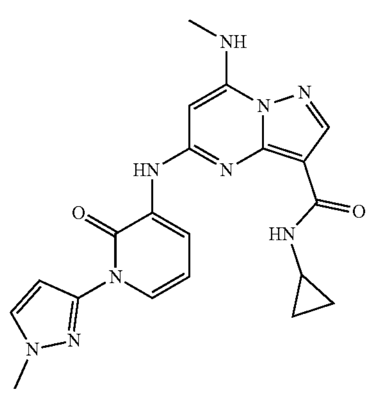 [SMILES: CNc1cc(Nc2cccn(-c3ccn(C)n3)c2=O)nc2c(C(=O)NC3CC3)cnn12] |

TABLE 1-continued
Selected Compounds
| Compound | Structure |
|---|---|
| I-295 | 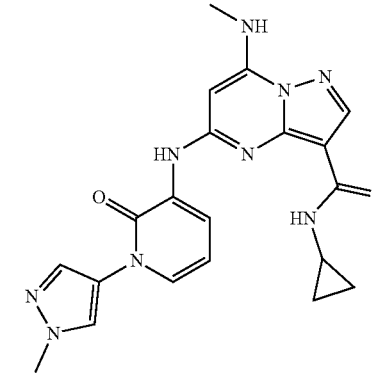 |
| I-296 | 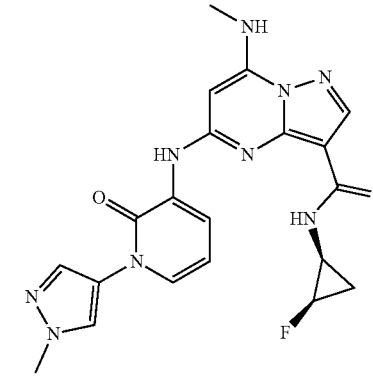 |
| I-297 | 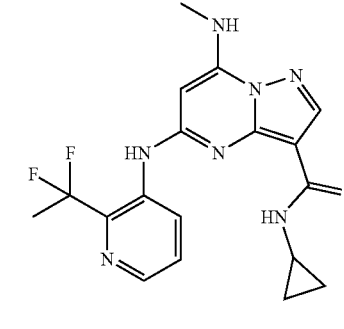 |
| I-298 | 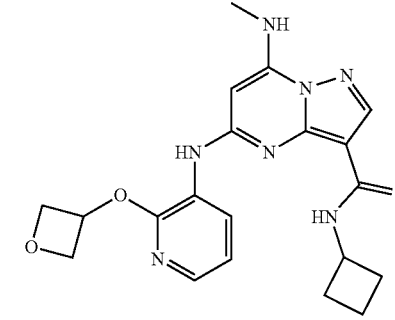 |

TABLE 1-continued

Selected Compounds

| Compound | Structure |
|---|---|
| I-299 | 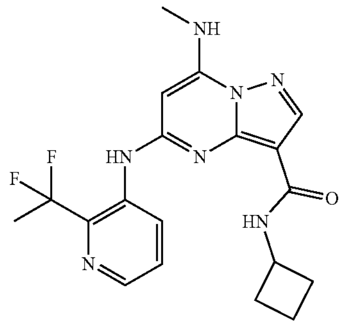 [SMILES: CNc1cc(Nc2cccnc2C(C)(F)F)nc2c(C(=O)NC3CCC3)cnn12] |
| I-300 | 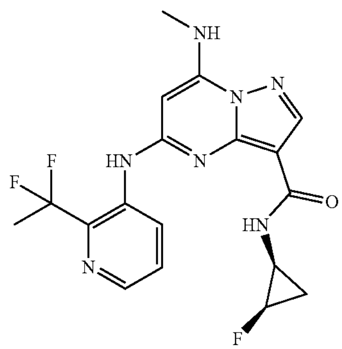 [SMILES: CNc1cc(Nc2cccnc2C(C)(F)F)nc2c(C(=O)N[C@H]3C[C@H]3F)cnn12] |
| I-301 | 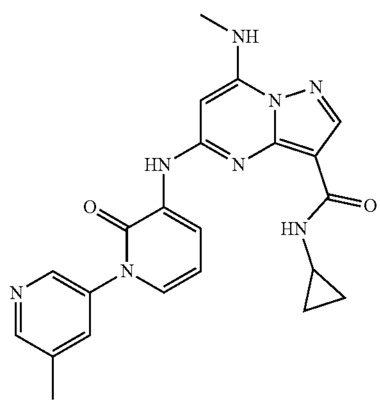 [SMILES: CNc1cc(Nc2cccn(-c3cncc(C)c3)c2=O)nc2c(C(=O)NC3CC3)cnn12] |
| I-302 | 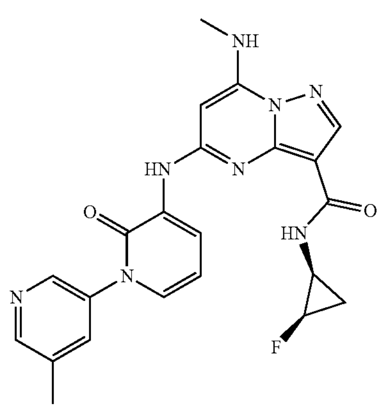 [SMILES: CNc1cc(Nc2cccn(-c3cncc(C)c3)c2=O)nc2c(C(=O)N[C@H]3C[C@H]3F)cnn12] |

TABLE 1-continued

Selected Compounds

| Compound | Structure |
|---|---|
| I-303 | 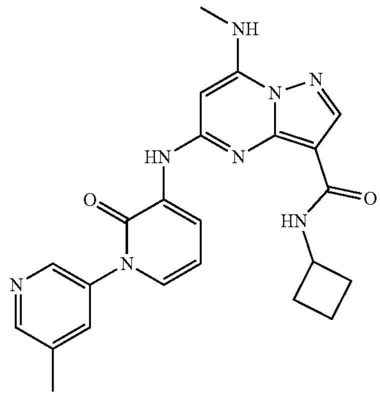 [SMILES: CNc1cc(Nc2cccn(-c3cncc(C)c3)c2=O)nc2c(C(=O)NC3CCC3)cnn12] |
| I-304 | 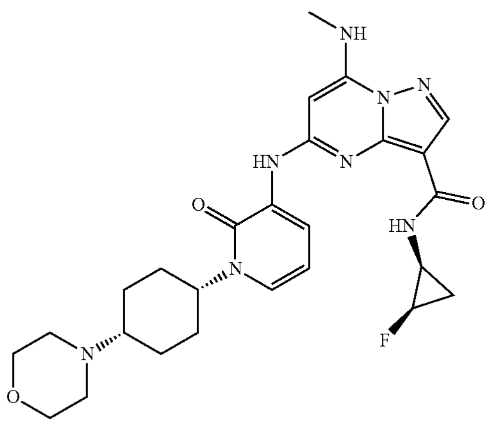 [SMILES: CNc1cc(Nc2cccn([C@H]3CC[C@@H](N4CCOCC4)CC3)c2=O)nc2c(C(=O)N[C@H]3C[C@H]3F)cnn12] |
| I-305 | 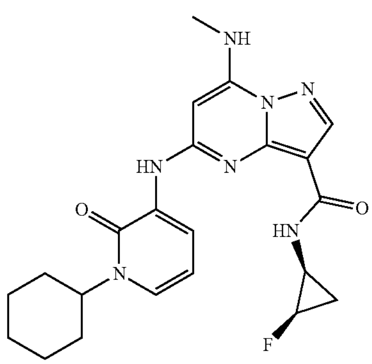 [SMILES: CNc1cc(Nc2cccn(C3CCCCC3)c2=O)nc2c(C(=O)N[C@H]3C[C@H]3F)cnn12] |
| I-306 | 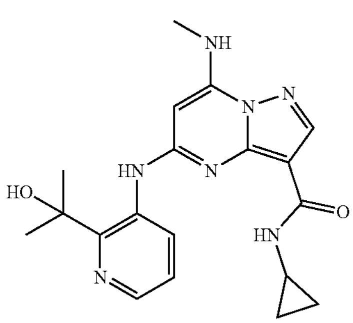 [SMILES: CNc1cc(Nc2cccnc2C(C)(C)O)nc2c(C(=O)NC3CC3)cnn12] |

TABLE 1-continued
Selected Compounds
| Compound | Structure |
|---|---|
| I-307 | 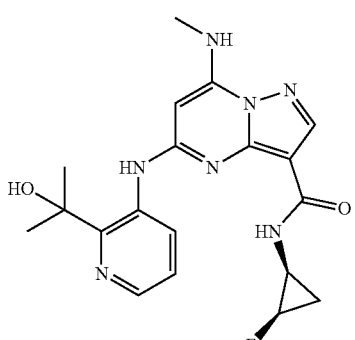 |
| I-308 | 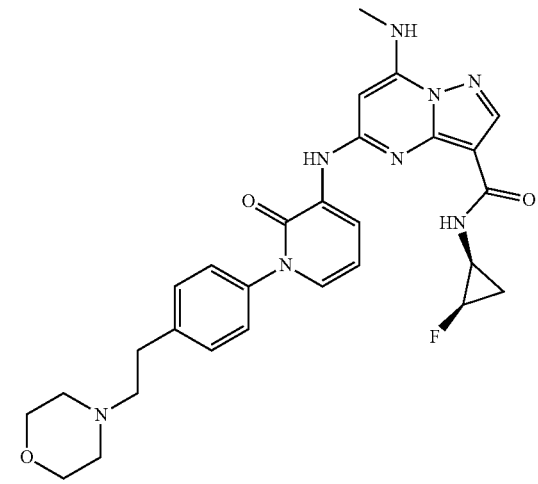 [SMILES: CNc1cc(Nc2cccn(-c3ccc(CCN4CCOCC4)cc3)c2=O)nc2c(C(=O)N[C@H]3C[C@H]3F)cnn12] |
| I-309 | 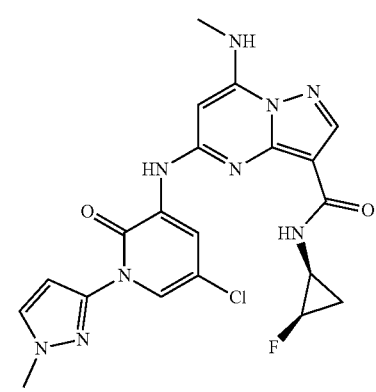 [SMILES: CNc1cc(Nc2cc(Cl)cn(-c3ccn(C)n3)c2=O)nc2c(C(=O)N[C@H]3C[C@H]3F)cnn12] |

TABLE 1-continued
| Selected Compounds | |
|---|---|
| Compound | Structure |
| I-310 | 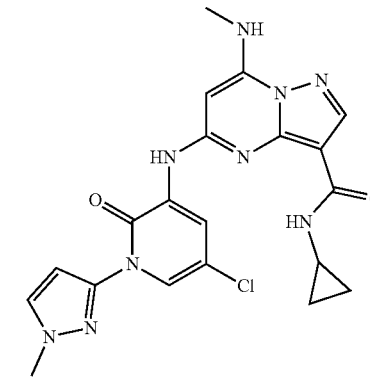 |
| I-311 | 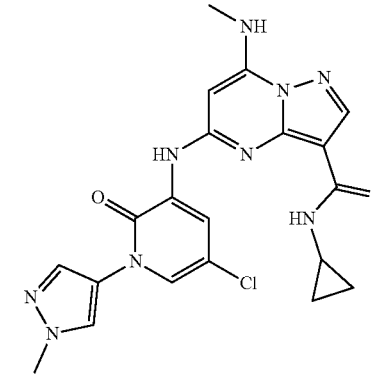 |
| I-312 | 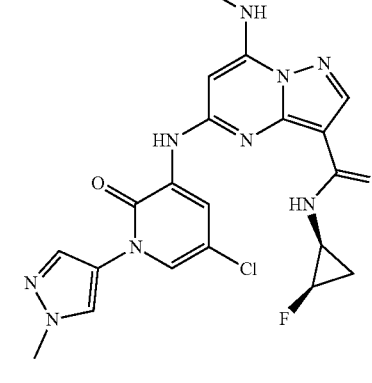 |
| I-313 | 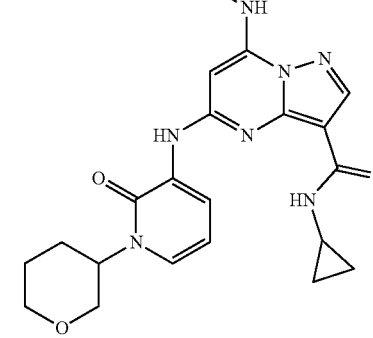 |

TABLE 1-continued
Selected Compounds
| Compound | Structure |
|---|---|
| I-314 | 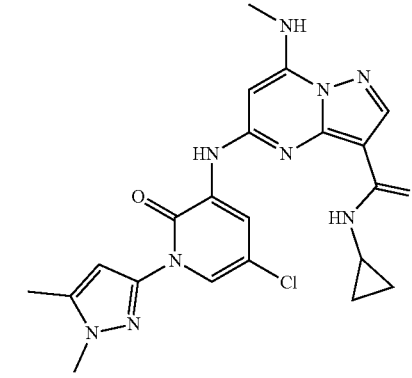 |
| I-315 | 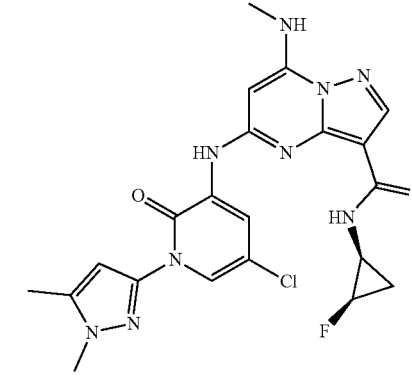 |
| I-316 | 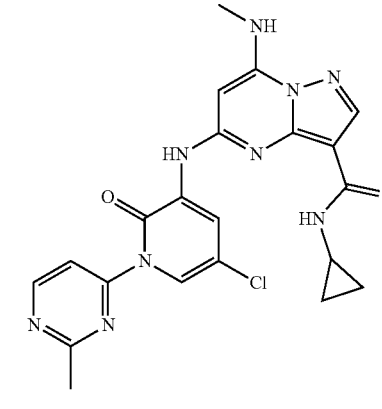 |
| I-317 | 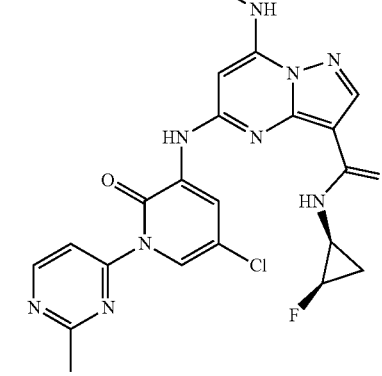 |

TABLE 1-continued
Selected Compounds
| Compound | Structure |
|---|---|
| I-318 | 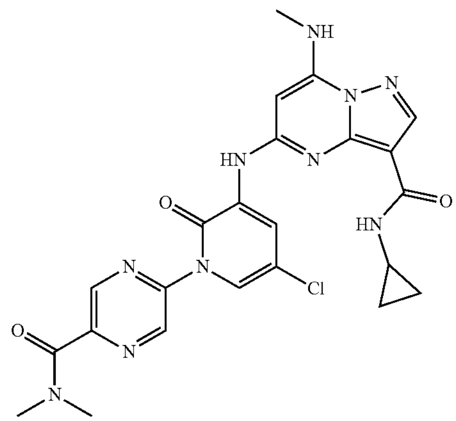 [SMILES: CNc1cc(Nc2cc(Cl)cn(-c3cnc(C(=O)N(C)C)cn3)c2=O)nc2c(C(=O)NC3CC3)cnn12] |
| I-319 | 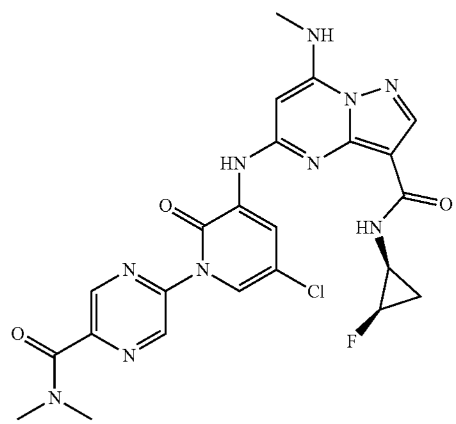 [SMILES: CNc1cc(Nc2cc(Cl)cn(-c3cnc(C(=O)N(C)C)cn3)c2=O)nc2c(C(=O)N[C@H]3C[C@H]3F)cnn12] |
| I-320 | 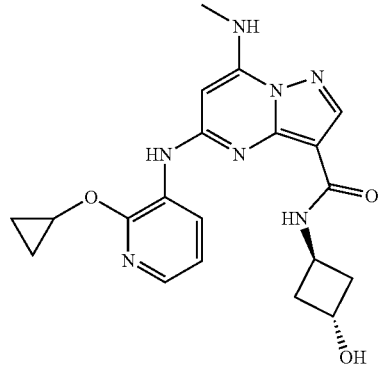 [SMILES: CNc1cc(Nc2cccnc2OC2CC2)nc2c(C(=O)N[C@H]3C[C@H](O)C3)cnn12] |

TABLE 1-continued
Selected Compounds
| Compound | Structure |
|---|---|
| I-321 | 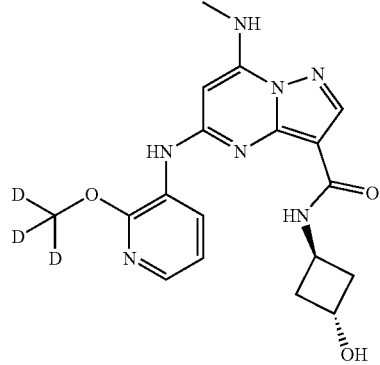 [SMILES: [2H]C([2H])([2H])Oc1ncccc1Nc1cc(NC)n2ncc(C(=O)N[C@H]3C[C@H](O)C3)c2n1] |
| I-322 | 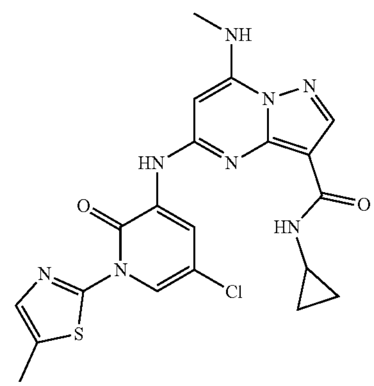 [SMILES: CNc1cc(Nc2cc(Cl)cn(-c3ncc(C)s3)c2=O)nc2c(C(=O)NC3CC3)cnn12] |
| I-323 | 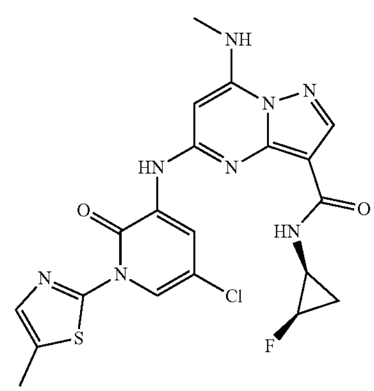 [SMILES: CNc1cc(Nc2cc(Cl)cn(-c3ncc(C)s3)c2=O)nc2c(C(=O)N[C@H]3C[C@H]3F)cnn12] |
| I-324 | 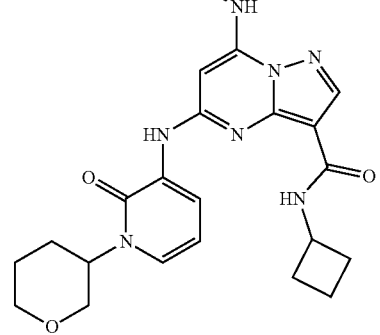 |

TABLE 1-continued
Selected Compounds
| Compound | Structure |
|---|---|
| I-325 | 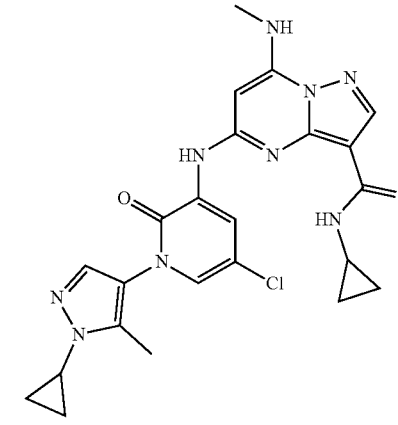 |
| I-326 | 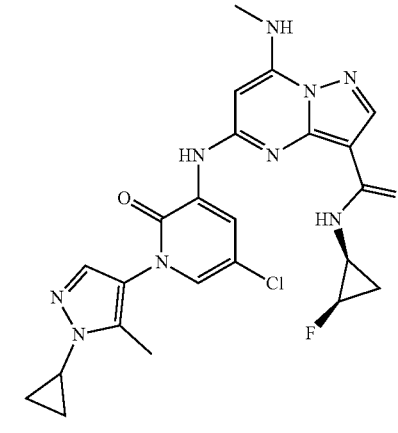 |
| I-327 | 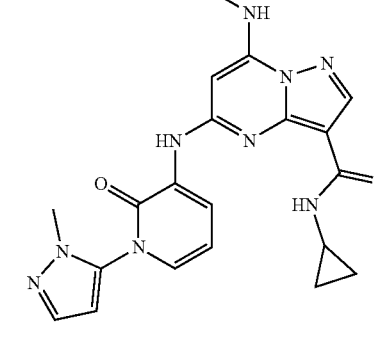 |
| I-328 | 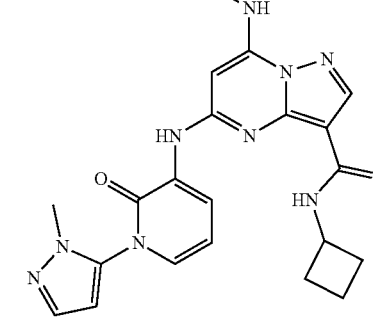 |

TABLE 1-continued

Selected Compounds

| Compound | Structure |
|---|---|
| I-329 | 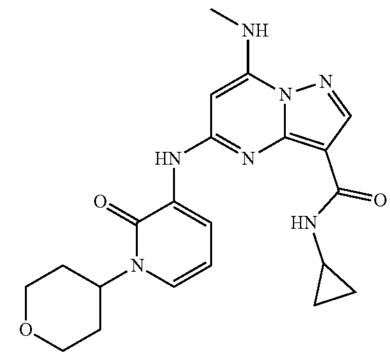 [SMILES: CNc1cc(Nc2cccn(C3CCOCC3)c2=O)nc2c(C(=O)NC3CC3)cnn12] |
| I-330 | 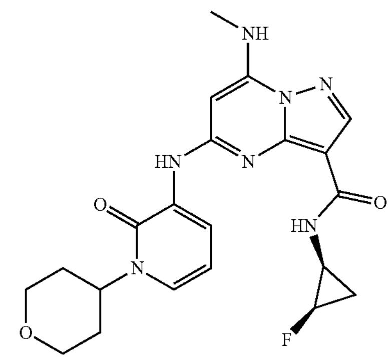 [SMILES: CNc1cc(Nc2cccn(C3CCOCC3)c2=O)nc2c(C(=O)N[C@H]3C[C@H]3F)cnn12] |
| I-331 | 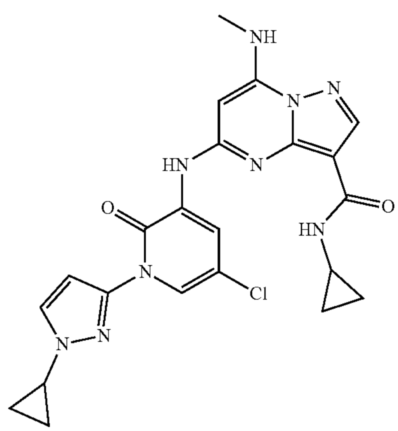 [SMILES: CNc1cc(Nc2cc(Cl)cn(-c3ccn(C4CC4)n3)c2=O)nc2c(C(=O)NC3CC3)cnn12] |
| I-332 | 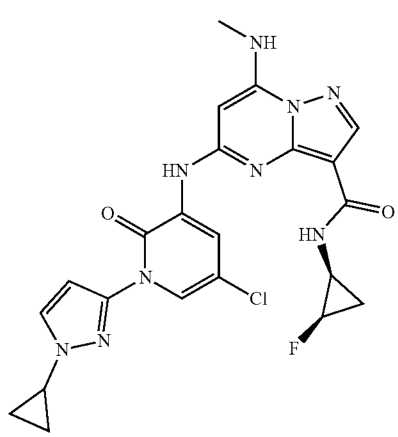 [SMILES: CNc1cc(Nc2cc(Cl)cn(-c3ccn(C4CC4)n3)c2=O)nc2c(C(=O)N[C@H]3C[C@H]3F)cnn12] |

TABLE 1-continued
Selected Compounds
| Compound | Structure |
|---|---|
| I-333 | 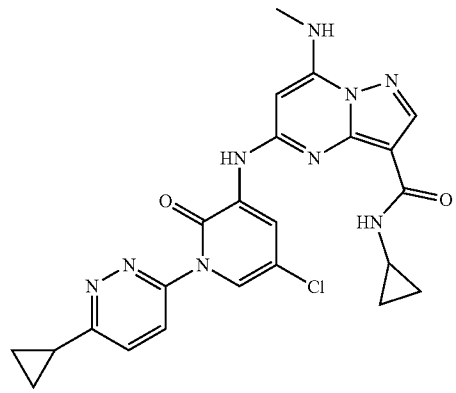 [SMILES: CNc1cc(Nc2cc(Cl)cn(-c3ccc(C4CC4)nn3)c2=O)nc2c(C(=O)NC3CC3)cnn12] |
| I-334 | 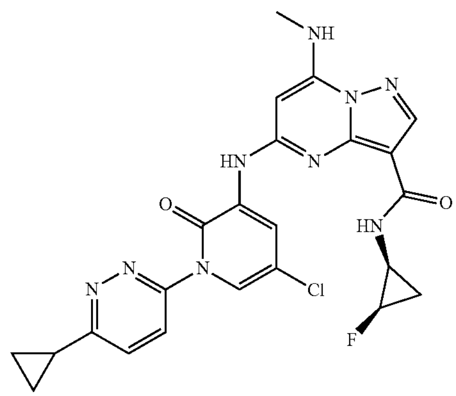 [SMILES: CNc1cc(Nc2cc(Cl)cn(-c3ccc(C4CC4)nn3)c2=O)nc2c(C(=O)N[C@H]3C[C@H]3F)cnn12] |
| I-335 | 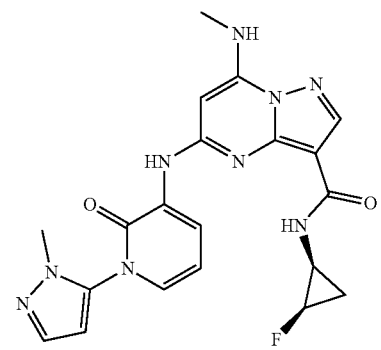 [SMILES: CNc1cc(Nc2cccn(-c3ccnn3C)c2=O)nc2c(C(=O)N[C@H]3C[C@H]3F)cnn12] |
| I-336 | 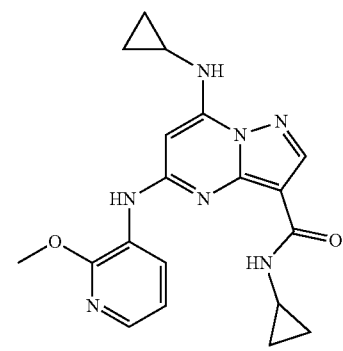 [SMILES: COc1ncccc1Nc1cc(NC2CC2)n2ncc(C(=O)NC3CC3)c2n1] |

TABLE 1-continued
Selected Compounds
| Compound | Structure |
|---|---|
| I-337 | 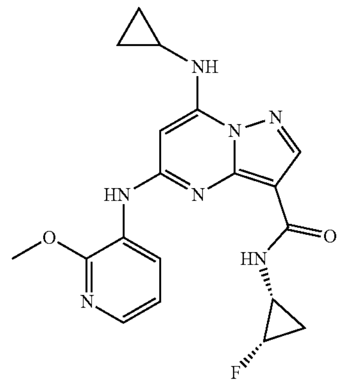 [SMILES: COc1ncccc1Nc1cc(NC2CC2)n2ncc(C(=O)N[C@@H]3C[C@@H]3F)c2n1] |
| I-338 | 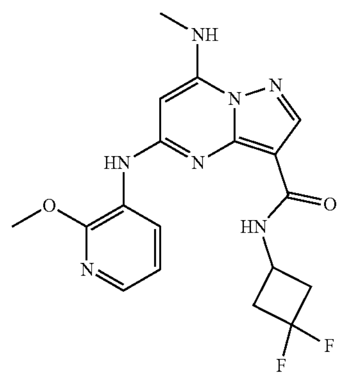 [SMILES: CNc1cc(Nc2cccnc2OC)nc2c(C(=O)NC3CC(F)(F)C3)cnn12] |
| I-339 | 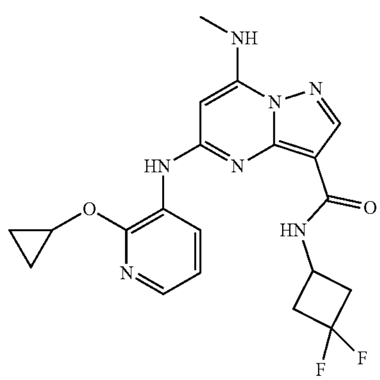 [SMILES: CNc1cc(Nc2cccnc2OC2CC2)nc2c(C(=O)NC3CC(F)(F)C3)cnn12] |
| I-340 | 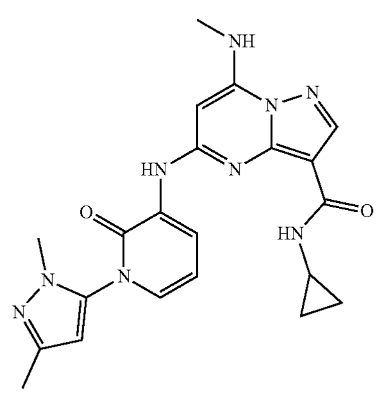 [SMILES: CNc1cc(Nc2cccn(-c3cc(C)nn3C)c2=O)nc2c(C(=O)NC3CC3)cnn12] |

TABLE 1-continued

Selected Compounds

| Compound | Structure |
|---|---|
| I-341 | 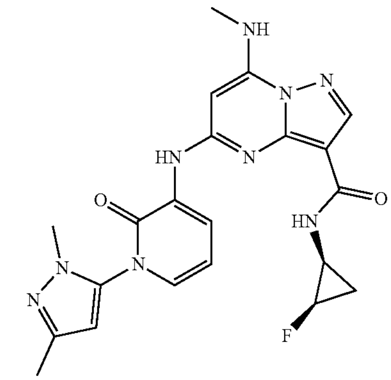 [SMILES: CNc1cc(Nc2cccn(-c3cc(C)nn3C)c2=O)nc2c(C(=O)N[C@H]3C[C@H]3F)cnn12] |
| I-342 | 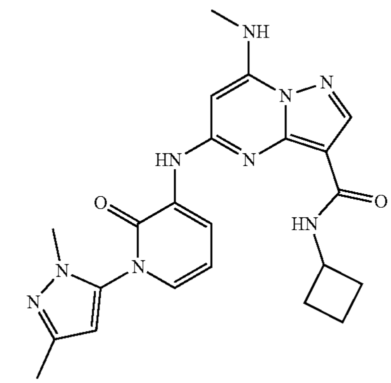 [SMILES: CNc1cc(Nc2cccn(-c3cc(C)nn3C)c2=O)nc2c(C(=O)NC3CCC3)cnn12] |
| I-343 | 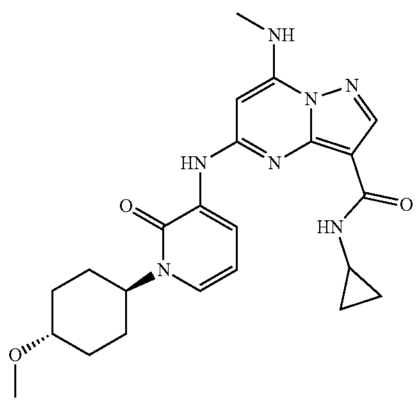 [SMILES: CNc1cc(Nc2cccn([C@H]3CC[C@H](OC)CC3)c2=O)nc2c(C(=O)NC3CC3)cnn12] |
| I-344 | 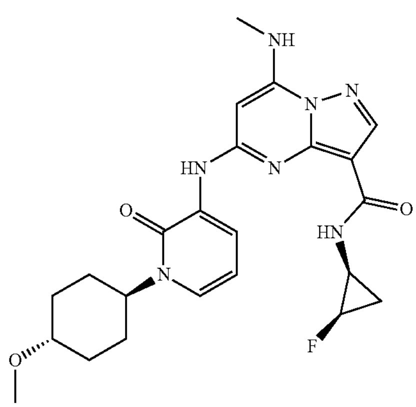 [SMILES: CNc1cc(Nc2cccn([C@H]3CC[C@H](OC)CC3)c2=O)nc2c(C(=O)N[C@H]3C[C@H]3F)cnn12] |

TABLE 1-continued

Selected Compounds

| Compound | Structure |
|---|---|
| I-345 | 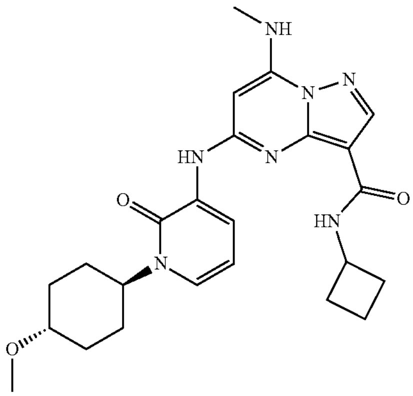 [SMILES: CNc1cc(Nc2cccn([C@H]3CC[C@H](OC)CC3)c2=O)nc2c(C(=O)NC3CCC3)cnn12] |
| I-346 | 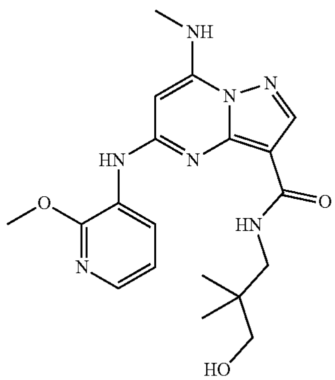 [SMILES: CNc1cc(Nc2cccnc2OC)nc2c(C(=O)NCC(C)(C)CO)cnn12] |
| I-347 | 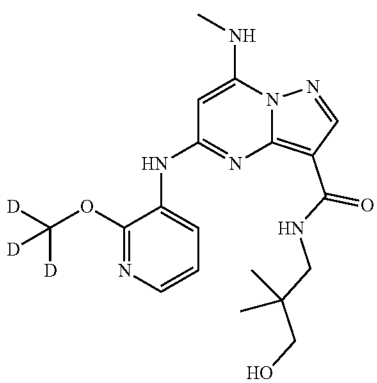 [SMILES: [2H]C([2H])([2H])Oc1ncccc1Nc1cc(NC)n2ncc(C(=O)NCC(C)(C)CO)c2n1] |
| I-348 | 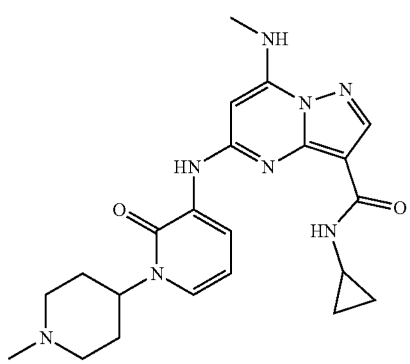 [SMILES: CNc1cc(Nc2cccn(C3CCN(C)CC3)c2=O)nc2c(C(=O)NC3CC3)cnn12] |

257 258
TABLE 1-continued
Selected Compounds
| Compound | Structure |
|---|---|
| I-349 | 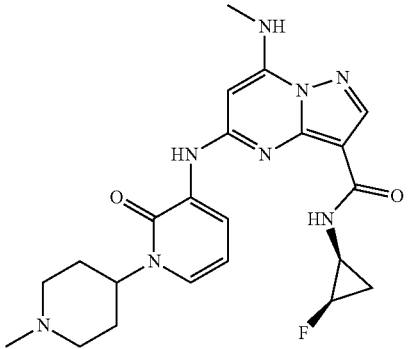 [SMILES: CNc1cc(Nc2cccn(C3CCN(C)CC3)c2=O)nc2c(C(=O)N[C@H]3C[C@H]3F)cnn12] |
| I-350 | 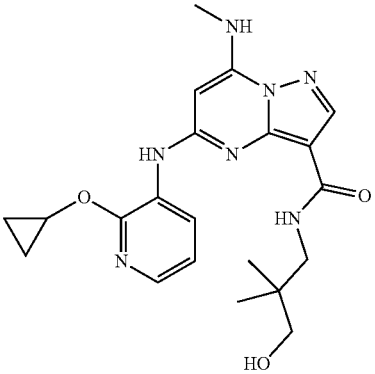 [SMILES: CNc1cc(Nc2cccnc2OC2CC2)nc2c(C(=O)NCC(C)(C)CO)cnn12] |
| I-351 | 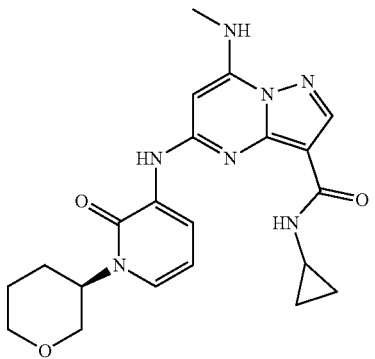 [SMILES: CNc1cc(Nc2cccn([C@@H]3CCCOC3)c2=O)nc2c(C(=O)NC3CC3)cnn12] |
| I-352 | 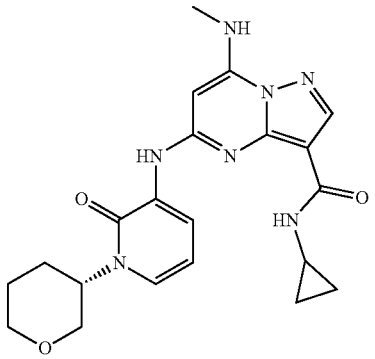 [SMILES: CNc1cc(Nc2cccn([C@H]3CCCOC3)c2=O)nc2c(C(=O)NC3CC3)cnn12] |

TABLE 1-continued
| Selected Compounds | |
|---|---|
| Compound | Structure |
| I-353 |  |
| I-354 | 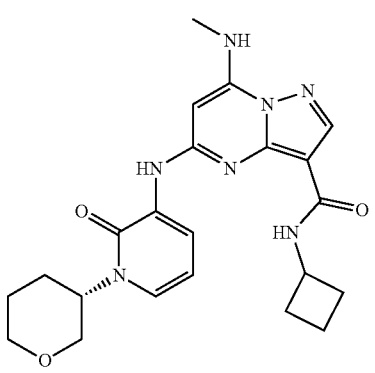 [SMILES: CNc1cc(Nc2cccn([C@H]3CCCOC3)c2=O)nc2c(C(=O)NC3CCC3)cnn12] |
| I-355 | 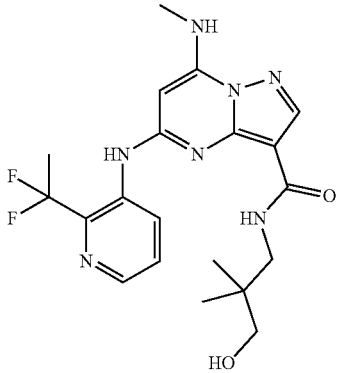 [SMILES: CNc1cc(Nc2cccnc2C(C)(F)F)nc2c(C(=O)NCC(C)(C)CO)cnn12] |
| I-356 | 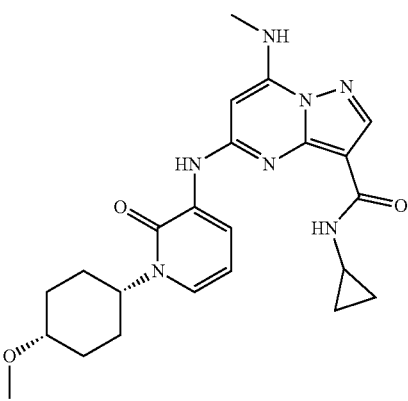 [SMILES: CNc1cc(Nc2cccn([C@H]3CC[C@@H](OC)CC3)c2=O)nc2c(C(=O)NC3CC3)cnn12] |

TABLE 1-continued
Selected Compounds
| Compound | Structure |
|---|---|
| I-357 | 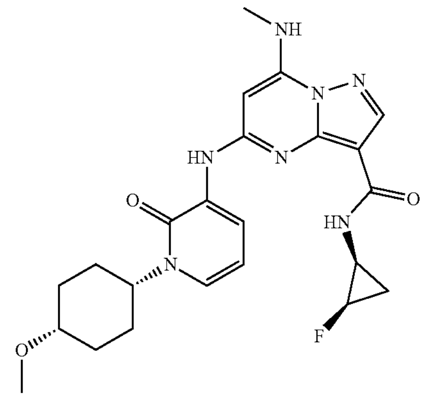 [SMILES: CNc1cc(Nc2cccn([C@H]3CC[C@@H](OC)CC3)c2=O)nc2c(C(=O)N[C@H]3C[C@H]3F)cnn12] |
| I-358 | 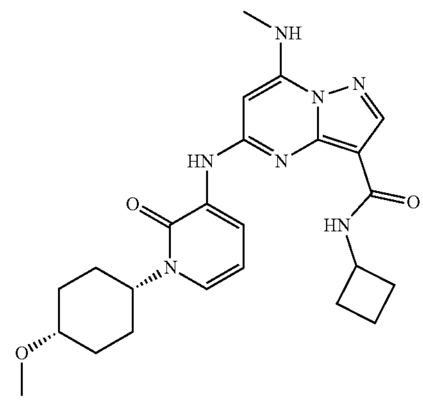 [SMILES: CNc1cc(Nc2cccn([C@H]3CC[C@@H](OC)CC3)c2=O)nc2c(C(=O)NC3CCC3)cnn12] |
| I-359 | 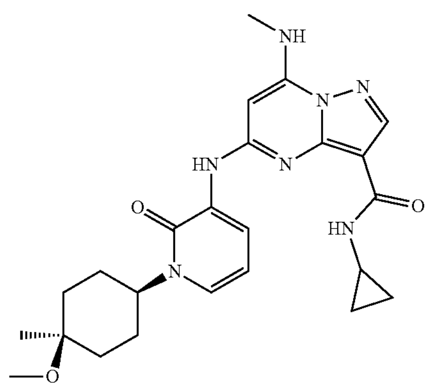 [SMILES: CNc1cc(Nc2cccn([C@H]3CC[C@@](C)(OC)CC3)c2=O)nc2c(C(=O)NC3CC3)cnn12] |
| I-360 | 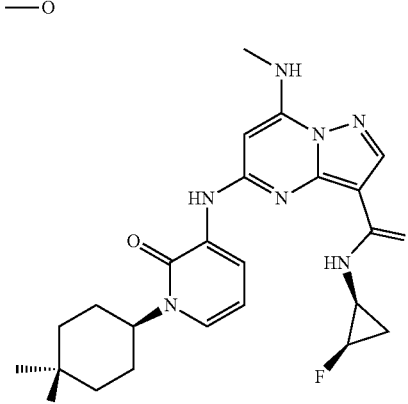 |

TABLE 1-continued

| Selected Compounds | |
|---|---|
| Compound | Structure |

I-361

I-362

I-363

I-364

TABLE 1-continued
| Selected Compounds | |
|---|---|
| Compound | Structure |
| I-365 | 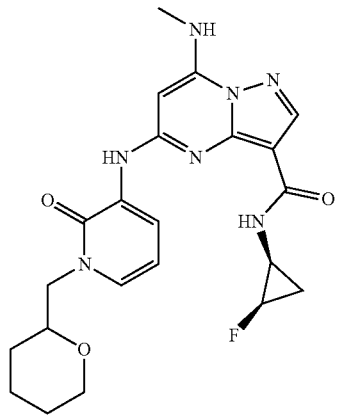 [SMILES: CNc1cc(Nc2cccn(CC3CCCCO3)c2=O)nc2c(C(=O)N[C@H]3C[C@H]3F)cnn12] |
| I-366 | 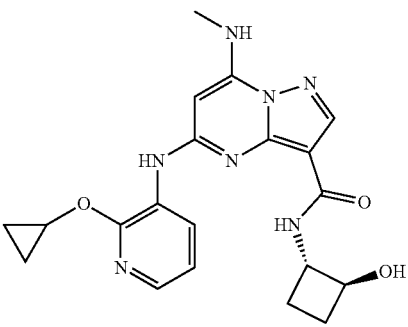 [SMILES: CNc1cc(Nc2cccnc2OC2CC2)nc2c(C(=O)N[C@H]3CC[C@@H]3O)cnn12] |
| I-367 | 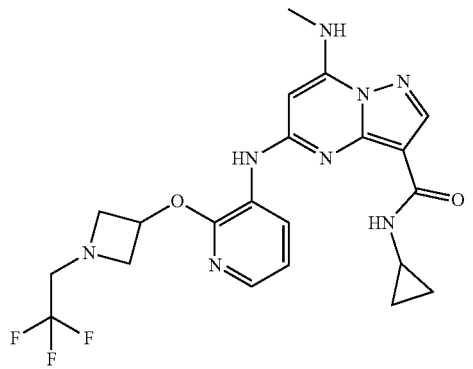 [SMILES: CNc1cc(Nc2cccnc2OC2CN(CC(F)(F)F)C2)nc2c(C(=O)NC3CC3)cnn12] |
| I-368 | 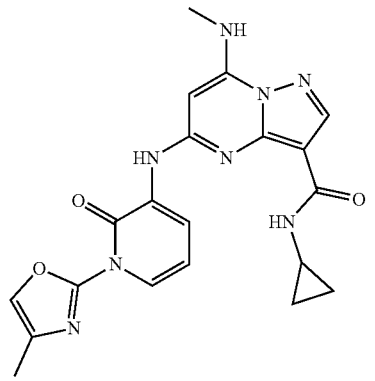 [SMILES: CNc1cc(Nc2cccn(-c3nc(C)co3)c2=O)nc2c(C(=O)NC3CC3)cnn12] |

TABLE 1-continued
Selected Compounds
| Compound | Structure |
|---|---|
| I-369 | 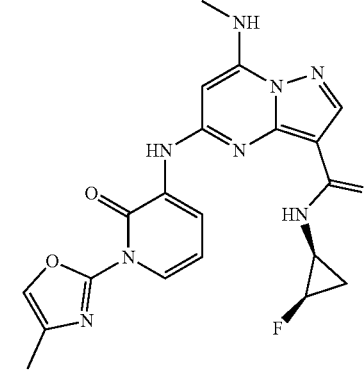 |
| I-370 | 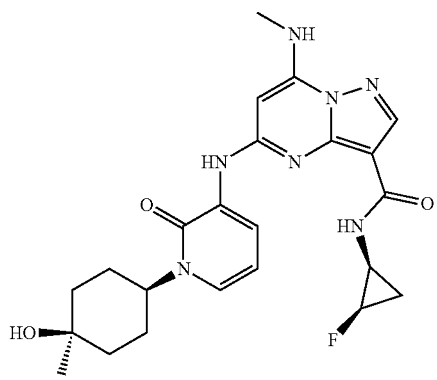 [SMILES: CNc1cc(Nc2cccn([C@H]3CC[C@@](C)(O)CC3)c2=O)nc2c(C(=O)N[C@H]3C[C@H]3F)cnn12] |
| I-371 | 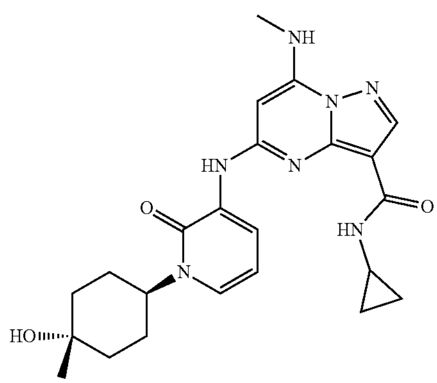 [SMILES: CNc1cc(Nc2cccn([C@H]3CC[C@](C)(O)CC3)c2=O)nc2c(C(=O)NC3CC3)cnn12] |
| I-372 | 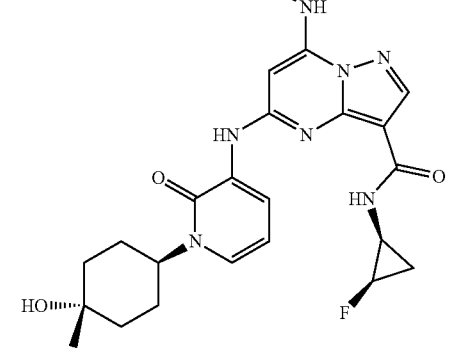 |

TABLE 1-continued

Selected Compounds

| Compound | Structure |
|---|---|
| I-373 | (chemical structure) |
| I-374 | (chemical structure) |
| I-375 | (chemical structure) |
| I-376 | (chemical structure) |

TABLE 1-continued
| Selected Compounds | |
|---|---|
| Compound | Structure |
| I-377 | 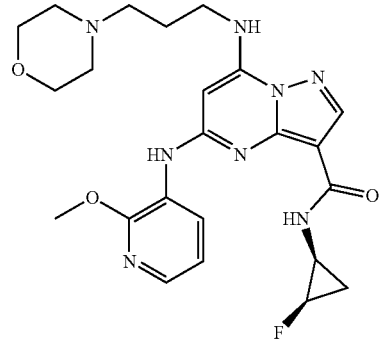 [SMILES: COc1ncccc1Nc1cc(NCCCN2CCOCC2)n2ncc(C(=O)N[C@H]3C[C@H]3F)c2n1] |
| I-378 | 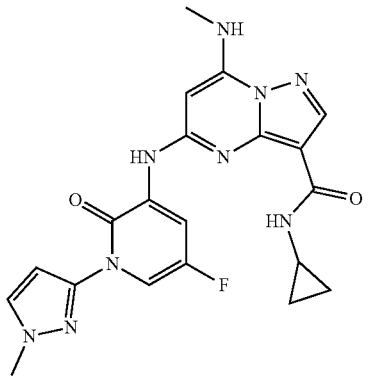 [SMILES: CNc1cc(Nc2cc(F)cn(-c3ccn(C)n3)c2=O)nc2c(C(=O)NC3CC3)cnn12] |
| I-379 | 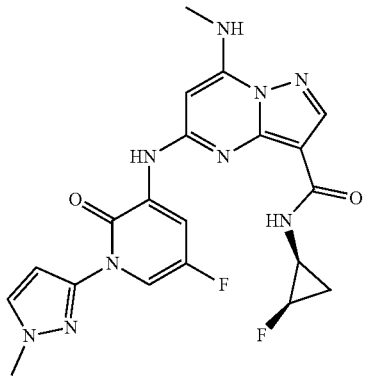 [SMILES: CNc1cc(Nc2cc(F)cn(-c3ccn(C)n3)c2=O)nc2c(C(=O)N[C@H]3C[C@H]3F)cnn12] |
| I-380 | 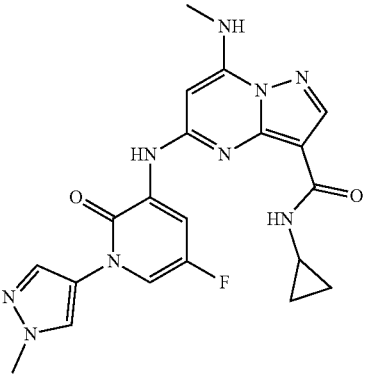 |

TABLE 1-continued

Selected Compounds

| Compound | Structure |
|---|---|
| I-381 | 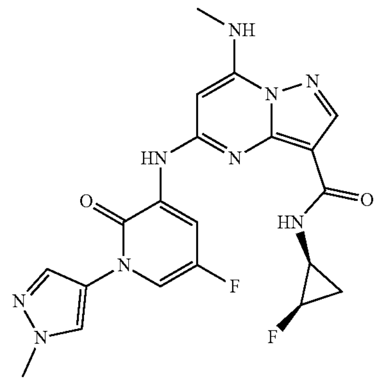 [SMILES: CNc1cc(Nc2cc(F)cn(-c3cnn(C)c3)c2=O)nc2c(C(=O)N[C@H]3C[C@H]3F)cnn12] |
| I-382 | 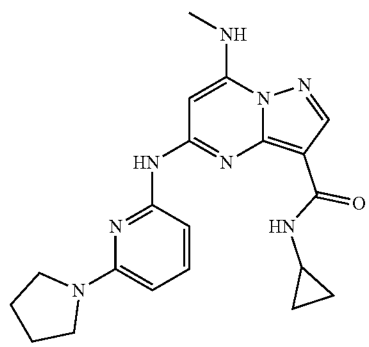 [SMILES: CNc1cc(Nc2cccc(N3CCCC3)n2)nc2c(C(=O)NC3CC3)cnn12] |
| I-383 | 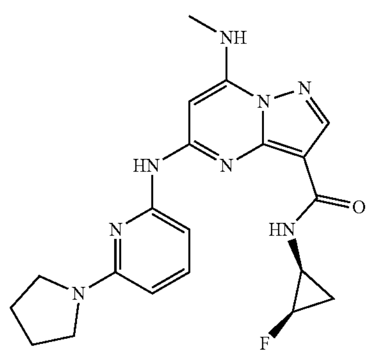 [SMILES: CNc1cc(Nc2cccc(N3CCCC3)n2)nc2c(C(=O)N[C@H]3C[C@H]3F)cnn12] |
| I-384 | 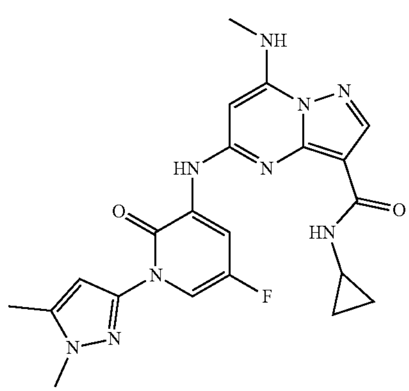 [SMILES: CNc1cc(Nc2cc(F)cn(-c3cc(C)n(C)n3)c2=O)nc2c(C(=O)NC3CC3)cnn12] |

TABLE 1-continued
Selected Compounds
| Compound | Structure |
|---|---|
| I-385 | 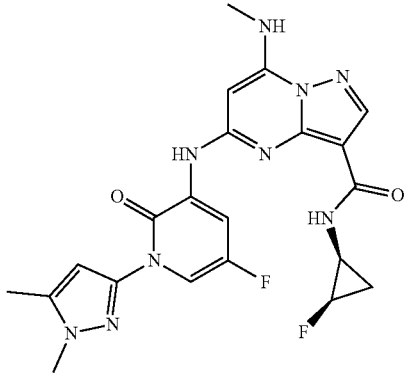 [SMILES: CNc1cc(Nc2cc(F)cn(-c3cc(C)n(C)n3)c2=O)nc2c(C(=O)N[C@H]3C[C@H]3F)cnn12] |
| I-386 | 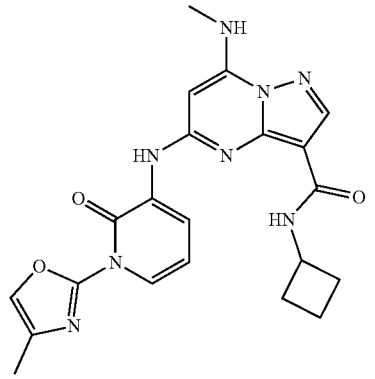 [SMILES: CNc1cc(Nc2cccn(-c3nc(C)co3)c2=O)nc2c(C(=O)NC3CCC3)cnn12] |
| I-387 | 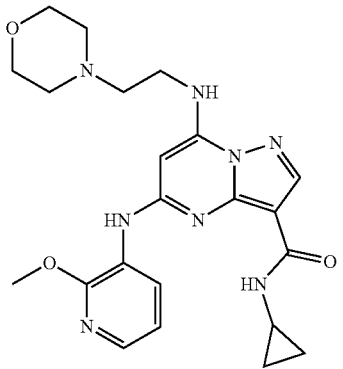 [SMILES: COc1ncccc1Nc1cc(NCCN2CCOCC2)n2ncc(C(=O)NC3CC3)c2n1] |
| I-388 | 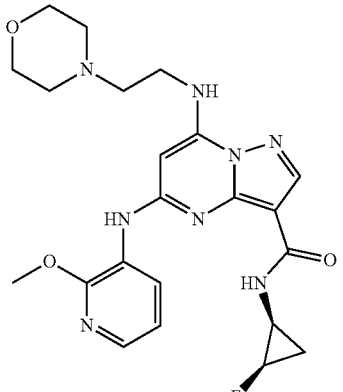 |

TABLE 1-continued

| Selected Compounds | |
|---|---|
| Compound | Structure |
| I-389 | |
| I-390 | |
| I-391 | |
| I-392 | |

TABLE 1-continued

| Selected Compounds | |
|---|---|
| Compound | Structure |//

I-393

I-394

I-395

I-396

TABLE 1-continued
Selected Compounds
| Compound | Structure |
|---|---|
| I-397 | 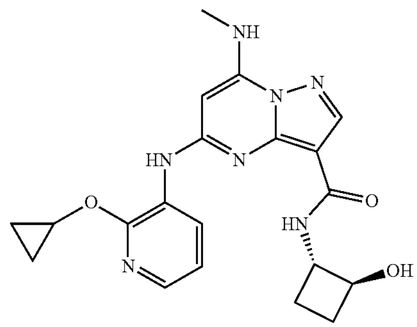 [SMILES: CNc1cc(Nc2cccnc2OC2CC2)nc2c(C(=O)N[C@H]3CC[C@@H]3O)cnn12] |
| I-398 | 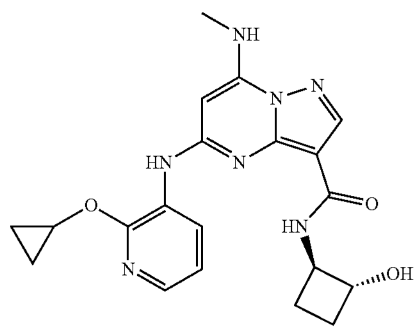 [SMILES: CNc1cc(Nc2cccnc2OC2CC2)nc2c(C(=O)N[C@@H]3CC[C@H]3O)cnn12] |
| I-399 | 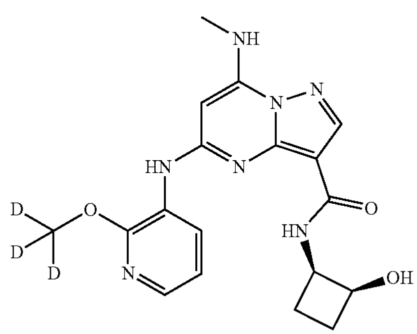 [SMILES: [2H]C([2H])([2H])Oc1ncccc1Nc1cc(NC)n2ncc(C(=O)N[C@@H]3CC[C@@H]3O)c2n1] |
| I-400 | 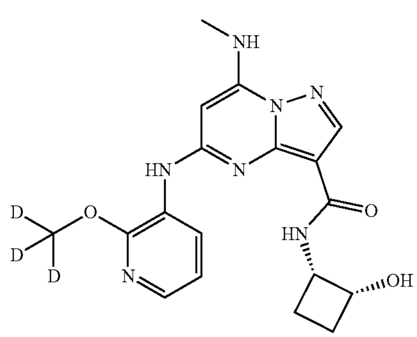 [SMILES: [2H]C([2H])([2H])Oc1ncccc1Nc1cc(NC)n2ncc(C(=O)N[C@H]3CC[C@H]3O)c2n1] |

TABLE 1-continued
Selected Compounds
| Compound | Structure |
|---|---|
| I-401 | 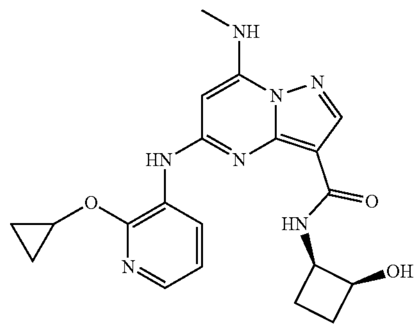 [SMILES: CNc1cc(Nc2cccnc2OC2CC2)nc2c(C(=O)N[C@@H]3CC[C@@H]3O)cnn12] |
| I-402 | 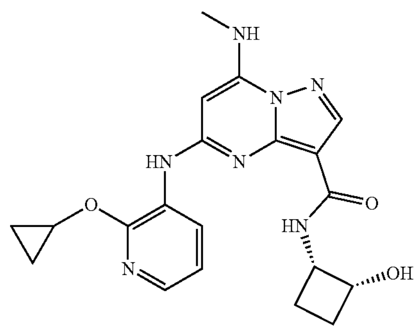 [SMILES: CNc1cc(Nc2cccnc2OC2CC2)nc2c(C(=O)N[C@H]3CC[C@H]3O)cnn12] |
| I-403 | 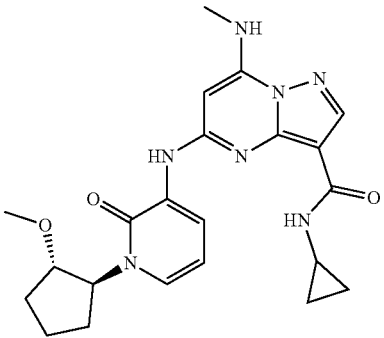 [SMILES: CNc1cc(Nc2cccn([C@H]3CCC[C@@H]3OC)c2=O)nc2c(C(=O)NC3CC3)cnn12] |
| I-404 | 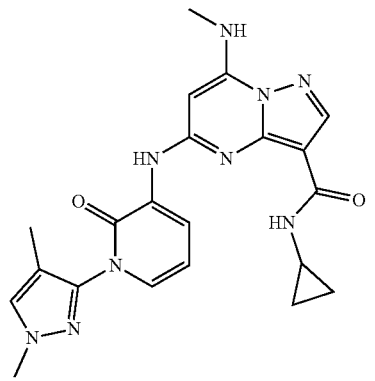 [SMILES: CNc1cc(Nc2cccn(-c3nn(C)cc3C)c2=O)nc2c(C(=O)NC3CC3)cnn12] |

TABLE 1-continued
Selected Compounds
| Compound | Structure |
|---|---|
| I-405 | 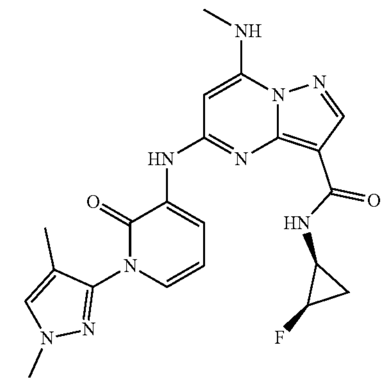 [SMILES: CNc1cc(Nc2cccn(-c3nn(C)cc3C)c2=O)nc2c(C(=O)N[C@H]3C[C@H]3F)cnn12] |
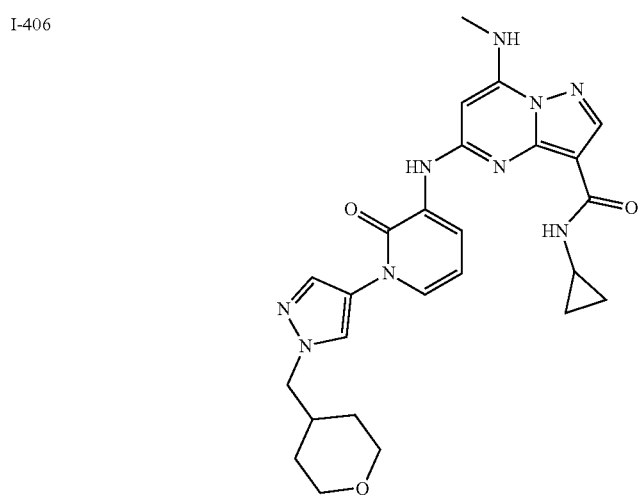
I-406
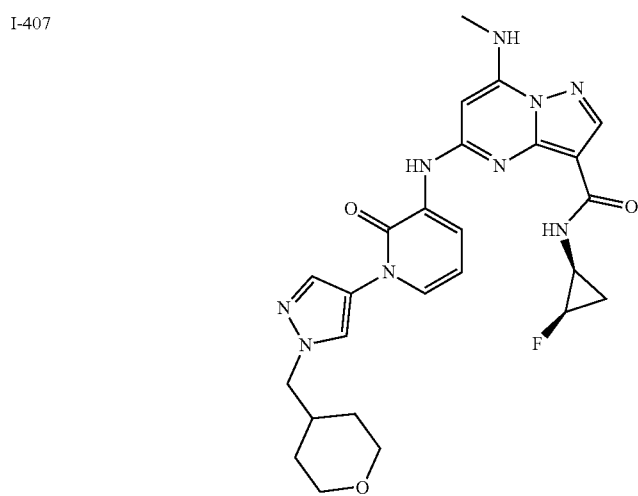
I-407

TABLE 1-continued
Selected Compounds
| Compound | Structure |
|---|---|
| I-408 | 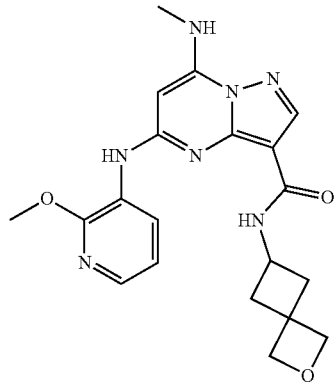 [SMILES: CNc1cc(Nc2cccnc2OC)nc2c(C(=O)NC3CC4(COC4)C3)cnn12] |
| I-409 | 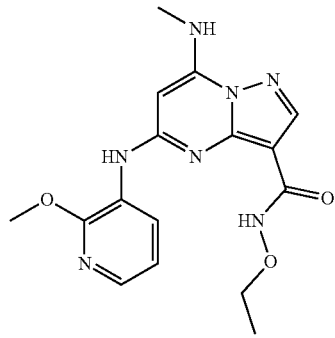 [SMILES: CCONC(=O)c1cnn2c(NC)cc(Nc3cccnc3OC)nc12] |
| I-410 | 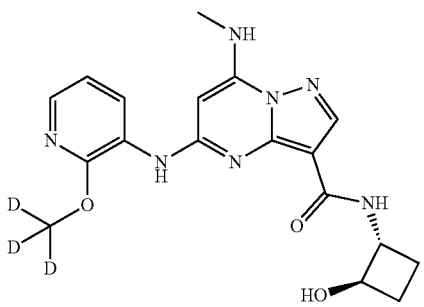 [SMILES: [2H]C([2H])([2H])Oc1ncccc1Nc1cc(NC)n2ncc(C(=O)N[C@@H]3CC[C@H]3O)c2n1] |
| I-411 | 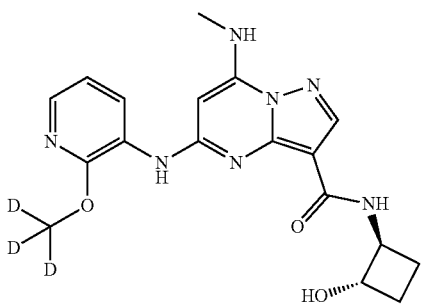 [SMILES: [2H]C([2H])([2H])Oc1ncccc1Nc1cc(NC)n2ncc(C(=O)N[C@H]3CC[C@@H]3O)c2n1] |

TABLE 1-continued

| Compound | Structure |
|---|---|
| I-412 | 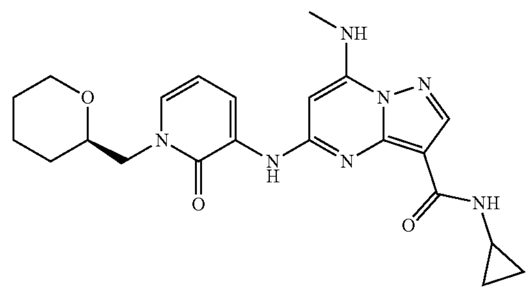 [SMILES: CNc1cc(Nc2cccn(C[C@H]3CCCCO3)c2=O)nc2c(C(=O)NC3CC3)cnn12] |
| I-413 | 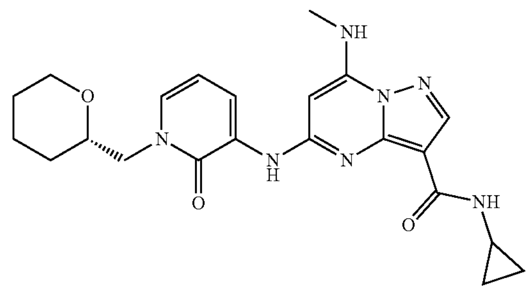 [SMILES: CNc1cc(Nc2cccn(C[C@@H]3CCCCO3)c2=O)nc2c(C(=O)NC3CC3)cnn12] |
| I-414 | 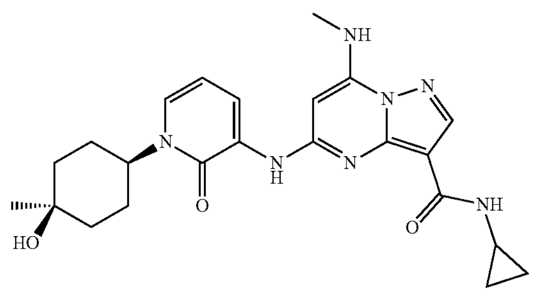 [SMILES: CNc1cc(Nc2cccn([C@H]3CC[C@@](C)(O)CC3)c2=O)nc2c(C(=O)NC3CC3)cnn12] |
| I-415 | 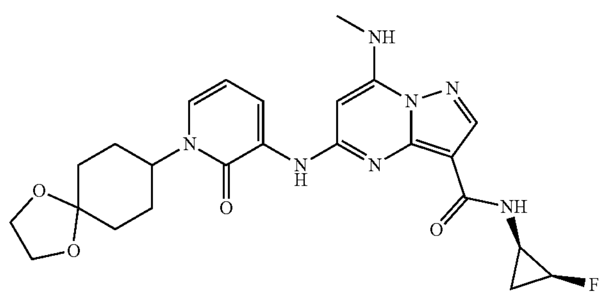 [SMILES: CNc1cc(Nc2cccn(C3CCC4(CC3)OCCO4)c2=O)nc2c(C(=O)N[C@@H]3C[C@@H]3F)cnn12] |
| I-416 | 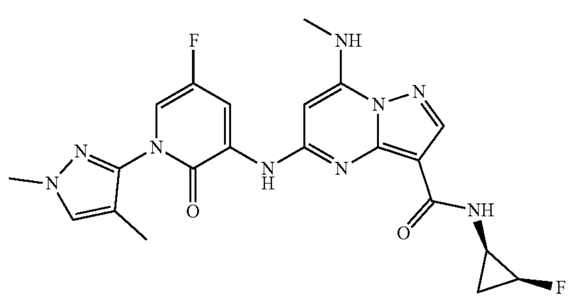 [SMILES: CNc1cc(Nc2cc(F)cn(-c3nn(C)cc3C)c2=O)nc2c(C(=O)N[C@@H]3C[C@@H]3F)cnn12] |

TABLE 1-continued
Selected Compounds
| Compound | Structure |
|---|---|
| I-417 | 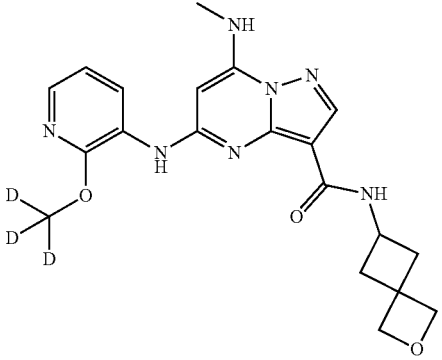 [SMILES: [2H]C([2H])([2H])Oc1ncccc1Nc1cc(NC)n2ncc(C(=O)NC3CC4(COC4)C3)c2n1] |
| I-418 | 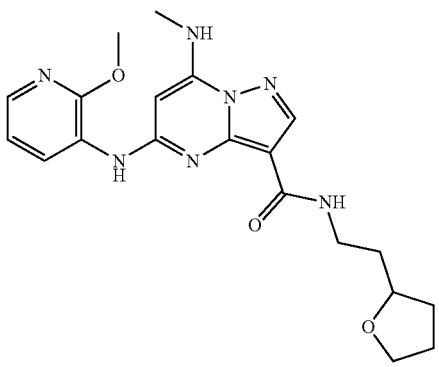 [SMILES: CNc1cc(Nc2cccnc2OC)nc2c(C(=O)NCCC3CCCO3)cnn12] |
| I-419 | 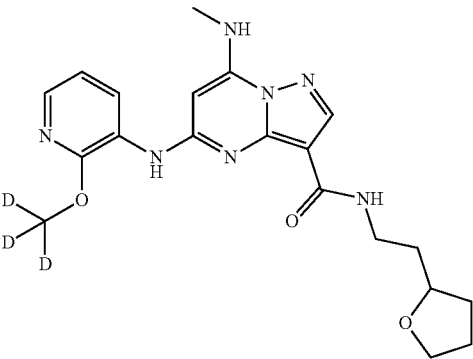 [SMILES: [2H]C([2H])([2H])Oc1ncccc1Nc1cc(NC)n2ncc(C(=O)NCCC3CCCO3)c2n1] |
| I-420 | 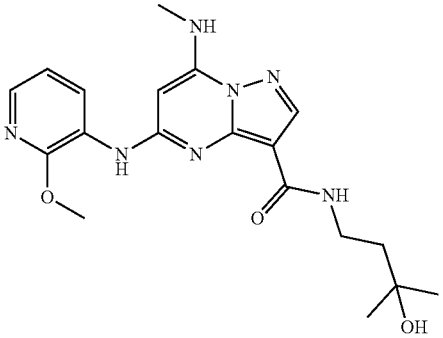 [SMILES: CNc1cc(Nc2cccnc2OC)nc2c(C(=O)NCCC(C)(C)O)cnn12] |

TABLE 1-continued

| Selected Compounds | |
|---|---|
| Compound | Structure |
| I-421 | |
| I-422 | |
| I-423 | |
| I-424 | |

TABLE 1-continued

Selected Compounds

| Compound | Structure |
|---|---|
| I-425 | 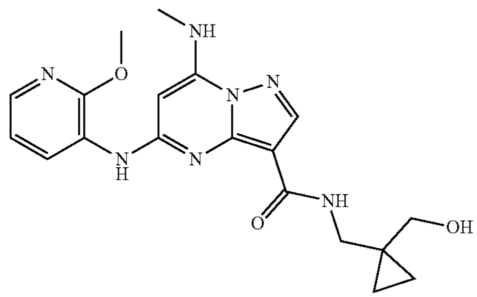 [SMILES: CNc1cc(Nc2cccnc2OC)nc2c(C(=O)NCC3(CO)CC3)cnn12] |
| I-426 | 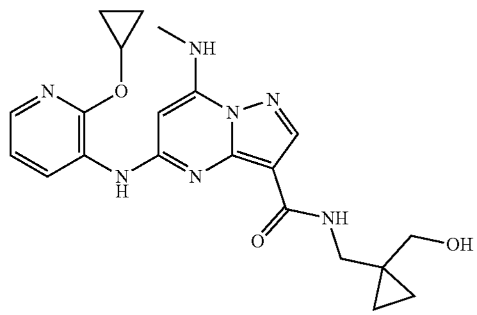 [SMILES: CNc1cc(Nc2cccnc2OC2CC2)nc2c(C(=O)NCC3(CO)CC3)cnn12] |
| I-427 | 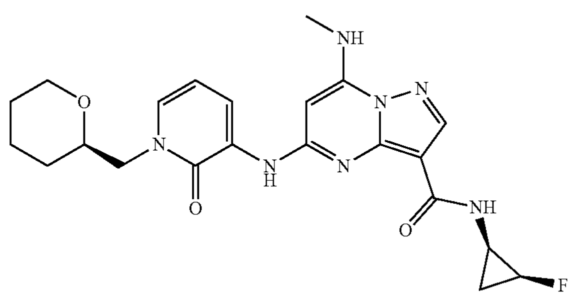 [SMILES: CNc1cc(Nc2cccn(C[C@H]3CCCCO3)c2=O)nc2c(C(=O)N[C@@H]3C[C@@H]3F)cnn12] |
| I-428 | 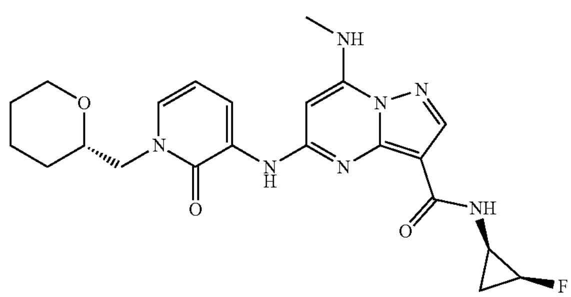 [SMILES: CNc1cc(Nc2cccn(C[C@@H]3CCCCO3)c2=O)nc2c(C(=O)N[C@@H]3C[C@@H]3F)cnn12] |
| I-429 | 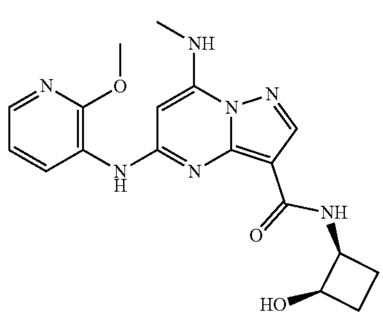 [SMILES: CNc1cc(Nc2cccnc2OC)nc2c(C(=O)N[C@H]3CC[C@H]3O)cnn12] |

TABLE 1-continued

Selected Compounds

| Compound | Structure |
|---|---|
| I-430 | 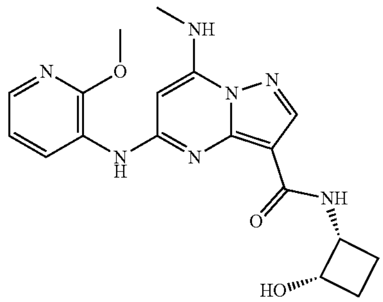 [SMILES: CNc1cc(Nc2cccnc2OC)nc2c(C(=O)N[C@@H]3CC[C@@H]3O)cnn12] |
| I-431 | 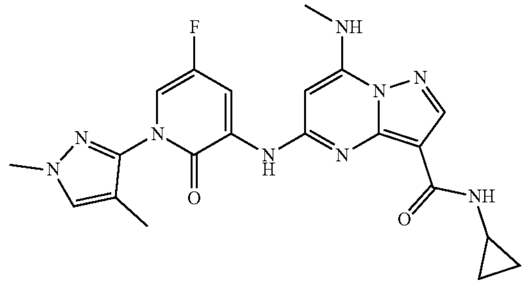 [SMILES: CNc1cc(Nc2cc(F)cn(-c3nn(C)cc3C)c2=O)nc2c(C(=O)NC3CC3)cnn12] |
| I-432 | 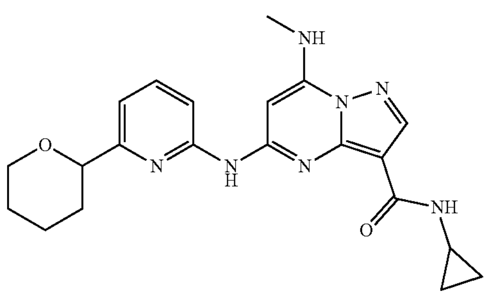 [SMILES: CNc1cc(Nc2cccc(C3CCCCO3)n2)nc2c(C(=O)NC3CC3)cnn12] |
| I-433 | 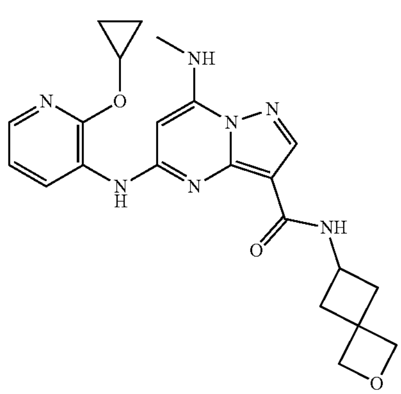 [SMILES: CNc1cc(Nc2cccnc2OC2CC2)nc2c(C(=O)NC3CC4(COC4)C3)cnn12] |

TABLE 1-continued
| Compound | Structure |
|---|---|
| I-434 | 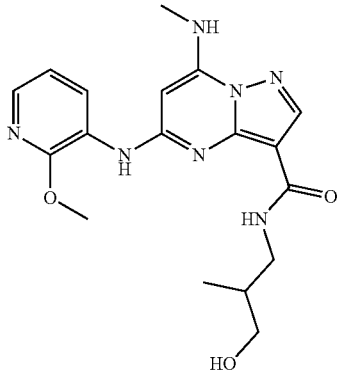 [SMILES: CNc1cc(Nc2cccnc2OC)nc2c(C(=O)NCC(C)CO)cnn12] |
| I-435 | 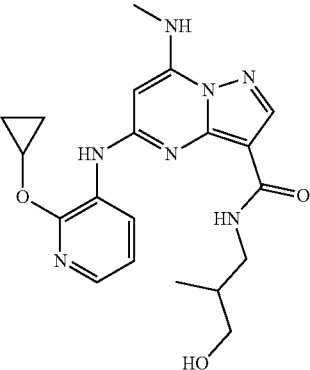 [SMILES: CNc1cc(Nc2cccnc2OC2CC2)nc2c(C(=O)NCC(C)CO)cnn12] |
| I-436 | 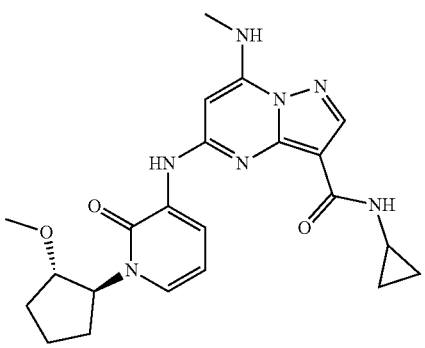 [SMILES: CNc1cc(Nc2cccn([C@H]3CCC[C@@H]3OC)c2=O)nc2c(C(=O)NC3CC3)cnn12] |
| I-437 | 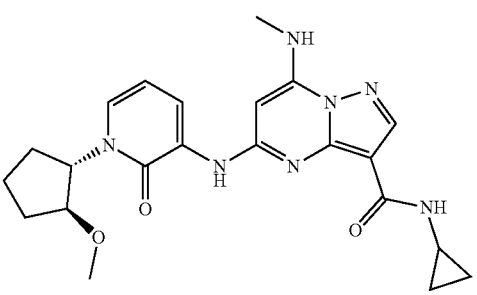 [SMILES: CNc1cc(Nc2cccn([C@H]3CCC[C@@H]3OC)c2=O)nc2c(C(=O)NC3CC3)cnn12] |

TABLE 1-continued

Selected Compounds

| Compound | Structure |
|---|---|
| I-438 | 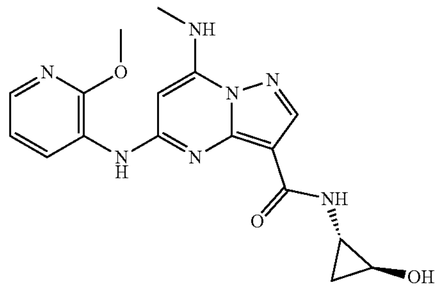 [SMILES: CNc1cc(Nc2cccnc2OC)nc2c(C(=O)N[C@H]3C[C@@H]3O)cnn12] |
| I-439 | 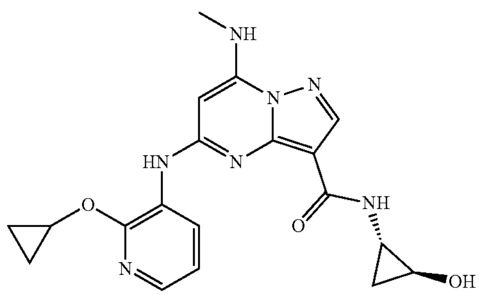 [SMILES: CNc1cc(Nc2cccnc2OC2CC2)nc2c(C(=O)N[C@H]3C[C@@H]3O)cnn12] |
| I-440 | 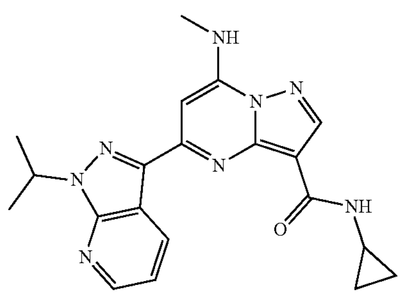 [SMILES: CNc1cc(-c2nn(C(C)C)c3ncccc23)nc2c(C(=O)NC3CC3)cnn12] |
| I-441 | 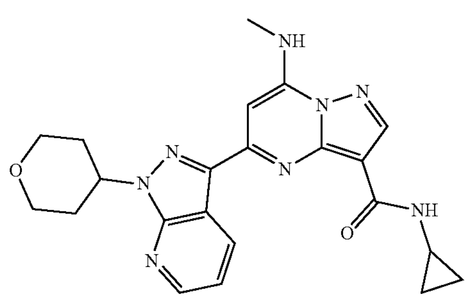 [SMILES: CNc1cc(-c2nn(C3CCOCC3)c3ncccc23)nc2c(C(=O)NC3CC3)cnn12] |
| I-442 | 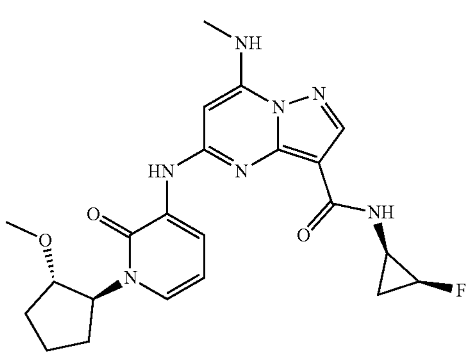 [SMILES: CNc1cc(Nc2cccn([C@H]3CCC[C@@H]3OC)c2=O)nc2c(C(=O)N[C@@H]3C[C@@H]3F)cnn12] |

TABLE 1-continued
Selected Compounds
| Compound | Structure |
|---|---|
| I-443 | 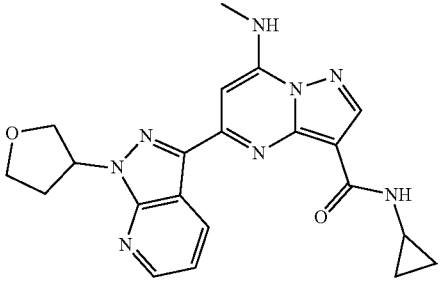 [SMILES: CNc1cc(-c2nn(C3CCOC3)c3ncccc23)nc2c(C(=O)NC3CC3)cnn12] |
| I-444 | 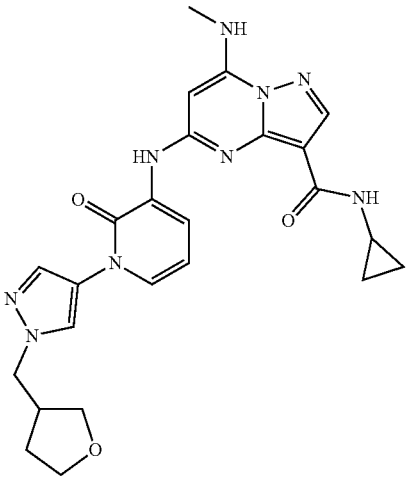 [SMILES: CNc1cc(Nc2cccn(-c3cnn(CC4CCOC4)c3)c2=O)nc2c(C(=O)NC3CC3)cnn12] |
| I-445 | 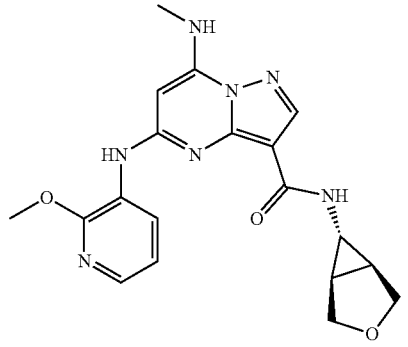 [SMILES: CNc1cc(Nc2cccnc2OC)nc2c(C(=O)N[C@H]3[C@@H]4COC[C@@H]43)cnn12] |
| I-446 | 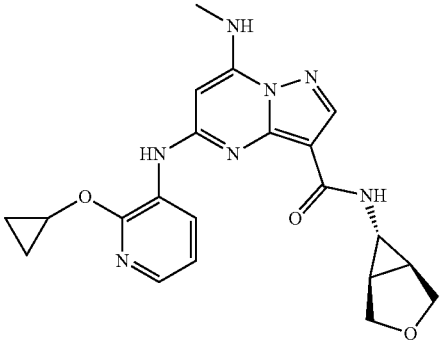 [SMILES: CNc1cc(Nc2cccnc2OC2CC2)nc2c(C(=O)N[C@H]3[C@@H]4COC[C@@H]43)cnn12] |

TABLE 1-continued

Selected Compounds

| Compound | Structure |
|---|---|
| I-447 | 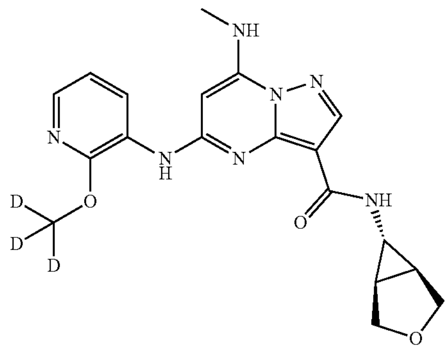 [SMILES: [2H]C([2H])([2H])Oc1ncccc1Nc1cc(NC)n2ncc(C(=O)N[C@H]3[C@@H]4COC[C@@H]43)c2n1] |
| I-448 | 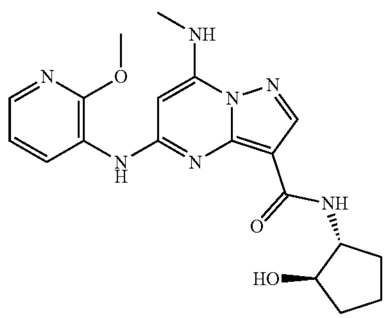 [SMILES: CNc1cc(Nc2cccnc2OC)nc2c(C(=O)N[C@@H]3CCC[C@H]3O)cnn12] |
| I-449 | 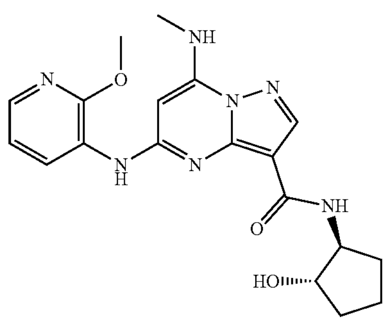 [SMILES: CNc1cc(Nc2cccnc2OC)nc2c(C(=O)N[C@H]3CCC[C@@H]3O)cnn12] |
| I-450 | 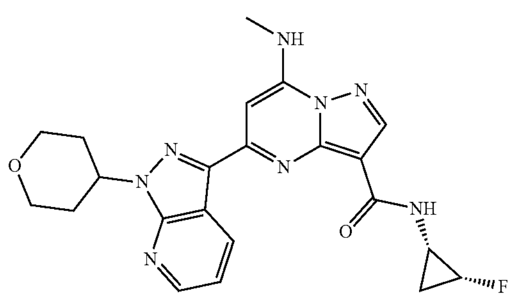 [SMILES: CNc1cc(-c2nn(C3CCOCC3)c3ncccc23)nc2c(C(=O)N[C@H]3C[C@H]3F)cnn12] |
| I-451 | 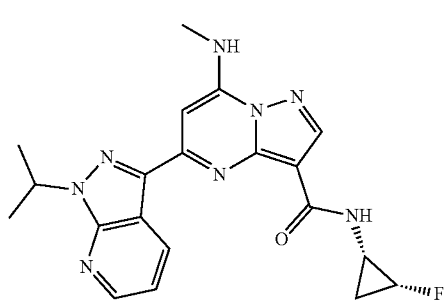 [SMILES: CNc1cc(-c2nn(C(C)C)c3ncccc23)nc2c(C(=O)N[C@H]3C[C@H]3F)cnn12] |

TABLE 1-continued

Selected Compounds

| Compound | Structure |
|---|---|
| I-452 | (structure) |
| I-453 | (structure) |
| I-454 | (structure) |
| I-455 | (structure) |

TABLE 1-continued
Selected Compounds
| Compound | Structure |
|---|---|
| I-456 | 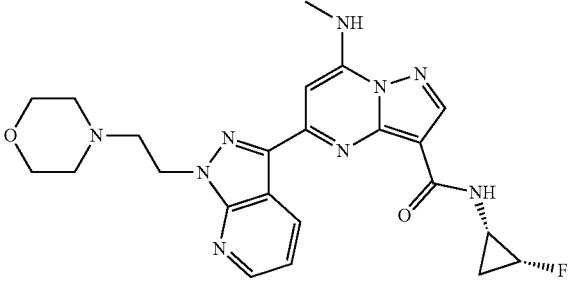 [SMILES: CNc1cc(-c2nn(CCN3CCOCC3)c3ncccc23)nc2c(C(=O)N[C@H]3C[C@H]3F)cnn12] |
| I-457 | 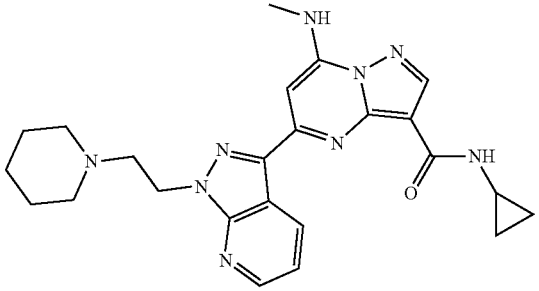 [SMILES: CNc1cc(-c2nn(CCN3CCCCC3)c3ncccc23)nc2c(C(=O)NC3CC3)cnn12] |
| I-458 | 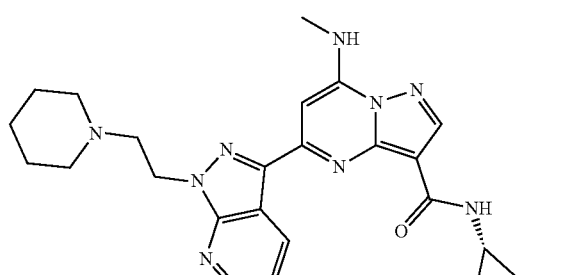 |
| I-459 | 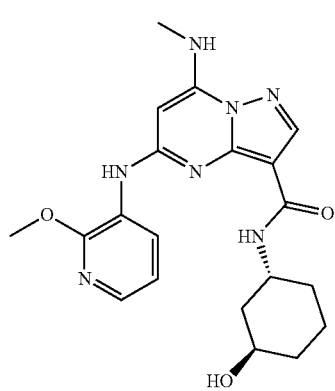 [SMILES: CNc1cc(Nc2cccnc2OC)nc2c(C(=O)N[C@@H]3CCC[C@@H](O)C3)cnn12] |

TABLE 1-continued
| Selected Compounds | |
|---|---|
| Compound | Structure |
| I-460 | 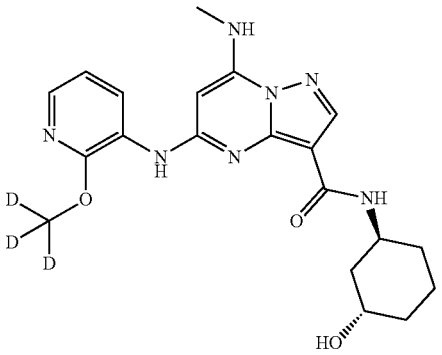 [SMILES: [2H]C([2H])([2H])Oc1ncccc1Nc1cc(NC)n2ncc(C(=O)N[C@H]3CCC[C@H](O)C3)c2n1] |
| I-461 | 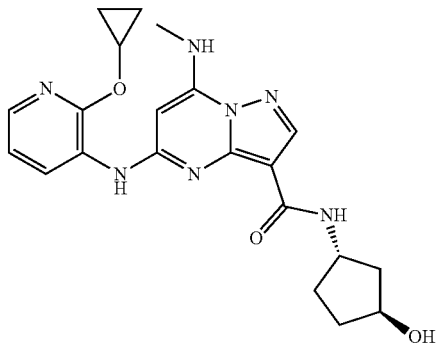 [SMILES: CNc1cc(Nc2cccnc2OC2CC2)nc2c(C(=O)N[C@H]3CC[C@H](O)C3)cnn12] |
| I-462 | 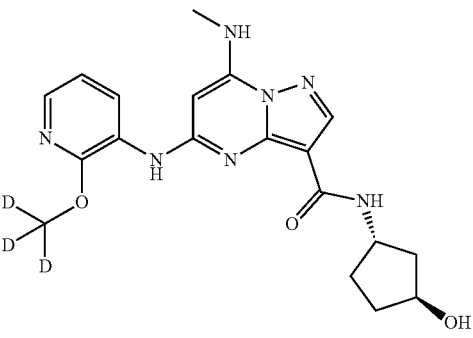 [SMILES: [2H]C([2H])([2H])Oc1ncccc1Nc1cc(NC)n2ncc(C(=O)N[C@H]3CC[C@H](O)C3)c2n1] |
| I-463 | 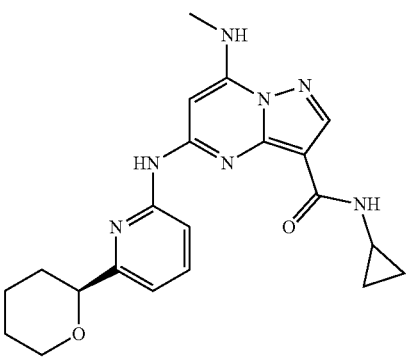 [SMILES: CNc1cc(Nc2cccc([C@@H]3CCCCO3)n2)nc2c(C(=O)NC3CC3)cnn12] |

TABLE 1-continued

Selected Compounds

| Compound | Structure |
|---|---|
| I-464 | 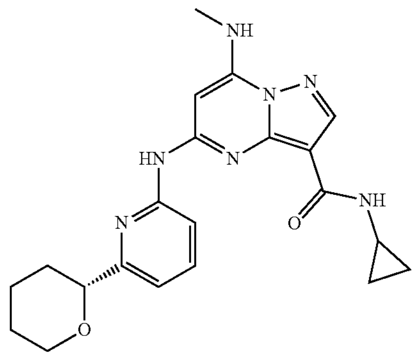 [SMILES: CNc1cc(Nc2cccc([C@H]3CCCCO3)n2)nc2c(C(=O)NC3CC3)cnn12] |
| I-465 | 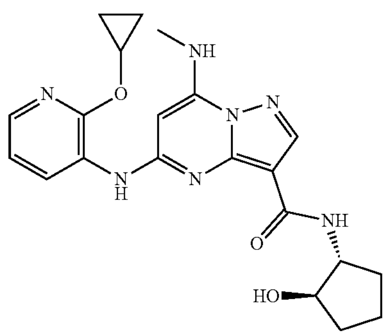 [SMILES: CNc1cc(Nc2cccnc2OC2CC2)nc2c(C(=O)N[C@@H]3CCC[C@H]3O)cnn12] |
| I-466 | 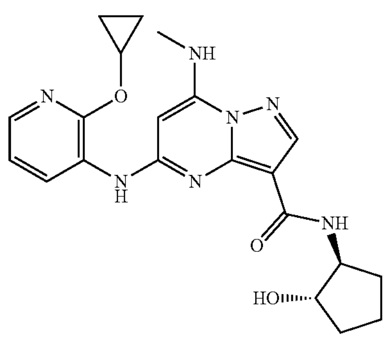 [SMILES: CNc1cc(Nc2cccnc2OC2CC2)nc2c(C(=O)N[C@H]3CCC[C@@H]3O)cnn12] |
| I-467 | 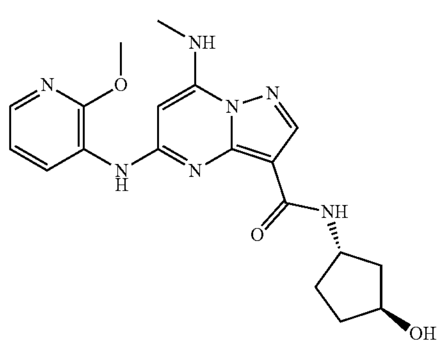 [SMILES: CNc1cc(Nc2cccnc2OC)nc2c(C(=O)N[C@H]3CC[C@H](O)C3)cnn12] |

TABLE 1-continued
| Selected Compounds | |
|---|---|
| Compound | Structure |
| I-468 | 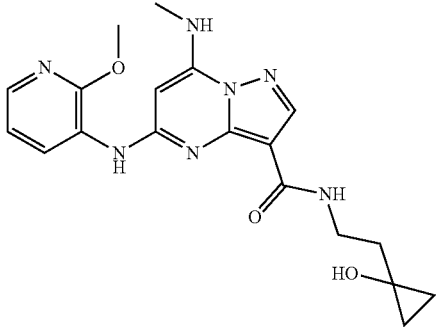 [SMILES: CNc1cc(Nc2cccnc2OC)nc2c(C(=O)NCCC3(O)CC3)cnn12] |
| I-469 | 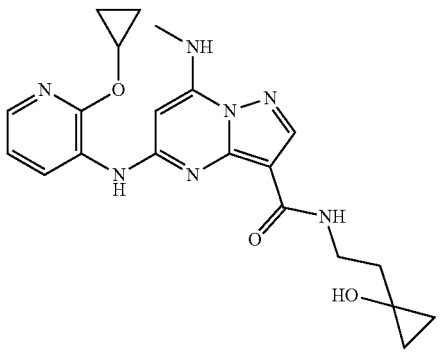 [SMILES: CNc1cc(Nc2cccnc2OC2CC2)nc2c(C(=O)NCCC3(O)CC3)cnn12] |
| I-470 | 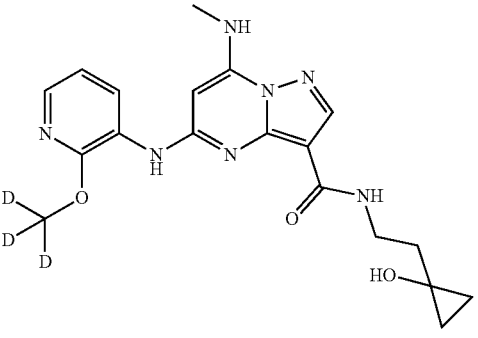 [SMILES: [2H]C([2H])([2H])Oc1ncccc1Nc1cc(NC)n2ncc(C(=O)NCCC3(O)CC3)c2n1] |
| I-471 | 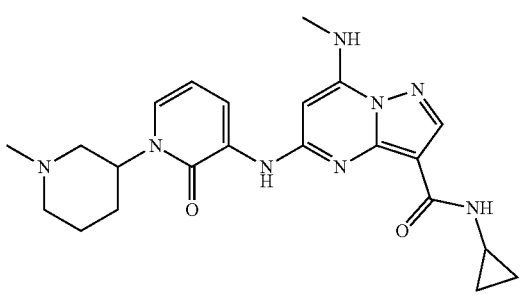 [SMILES: CNc1cc(Nc2cccn(C3CCCN(C)C3)c2=O)nc2c(C(=O)NC3CC3)cnn12] |

TABLE 1-continued
| Selected Compounds | |
|---|---|
| Compound | Structure |
| I-472 | 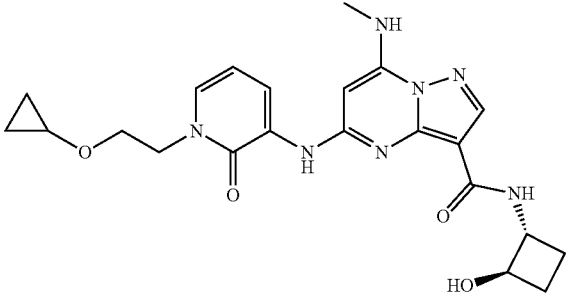 [SMILES: CNc1cc(Nc2cccn(CCOC3CC3)c2=O)nc2c(C(=O)N[C@@H]3CC[C@H]3O)cnn12] |
| I-473 | 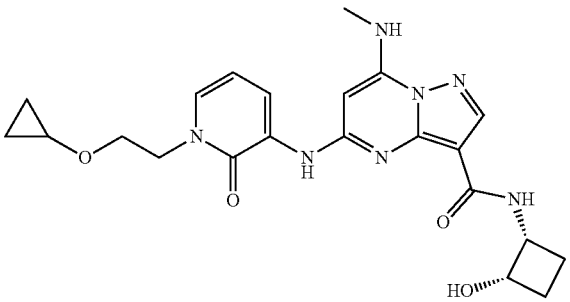 [SMILES: CNc1cc(Nc2cccn(CCOC3CC3)c2=O)nc2c(C(=O)N[C@@H]3CC[C@@H]3O)cnn12] |
| I-474 | 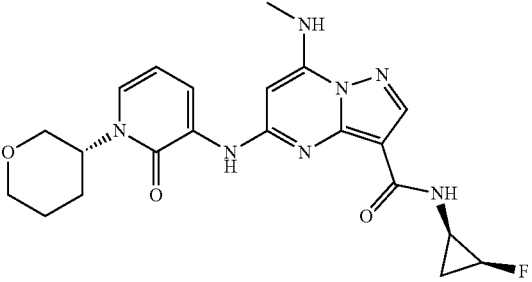 [SMILES: CNc1cc(Nc2cccn([C@@H]3CCCOC3)c2=O)nc2c(C(=O)N[C@@H]3C[C@@H]3F)cnn12] |
| I-475 | 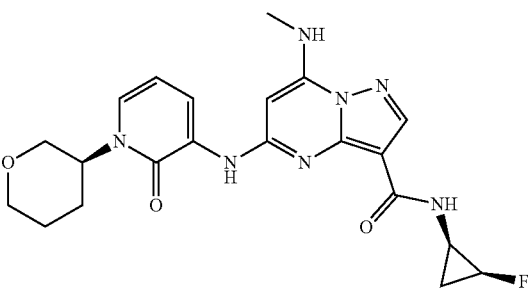 [SMILES: CNc1cc(Nc2cccn([C@H]3CCCOC3)c2=O)nc2c(C(=O)N[C@@H]3C[C@@H]3F)cnn12] |
| I-476 | 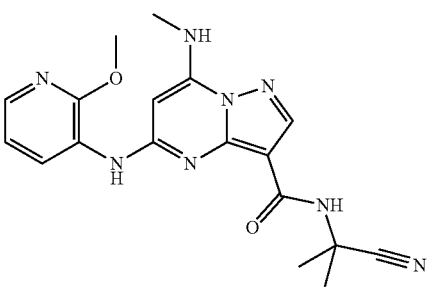 [SMILES: CNc1cc(Nc2cccnc2OC)nc2c(C(=O)NC(C)(C)C#N)cnn12] |

TABLE 1-continued
Selected Compounds
| Compound | Structure |
|---|---|
| I-477 | 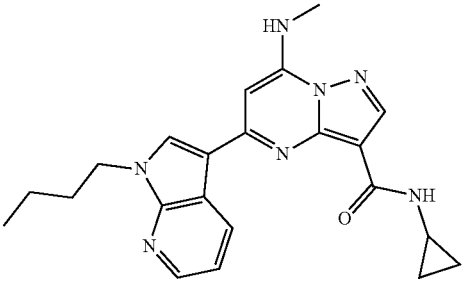 [SMILES: CCCCn1cc(-c2cc(NC)n3ncc(C(=O)NC4CC4)c3n2)c2cccnc21] |
| I-478 | 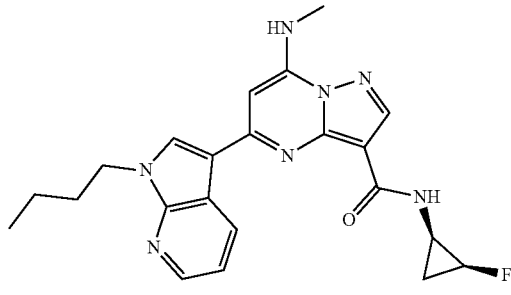 [SMILES: CCCCn1cc(-c2cc(NC)n3ncc(C(=O)N[C@@H]4C[C@@H]4F)c3n2)c2cccnc21] |
| I-479 | 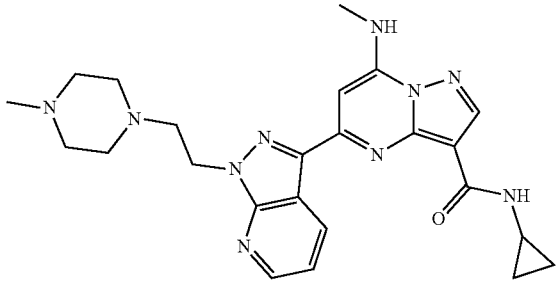 [SMILES: CNc1cc(-c2nn(CCN3CCN(C)CC3)c3ncccc23)nc2c(C(=O)NC3CC3)cnn12] |
| I-480 | 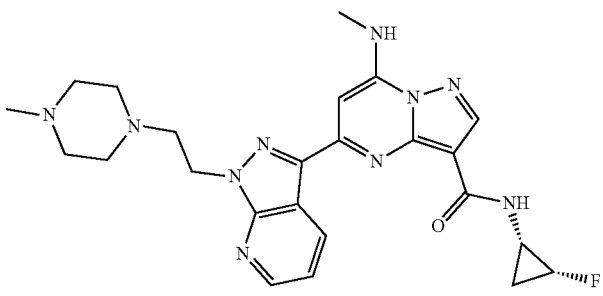 [SMILES: CNc1cc(-c2nn(CCN3CCN(C)CC3)c3ncccc23)nc2c(C(=O)N[C@H]3C[C@H]3F)cnn12] |
| I-481 | 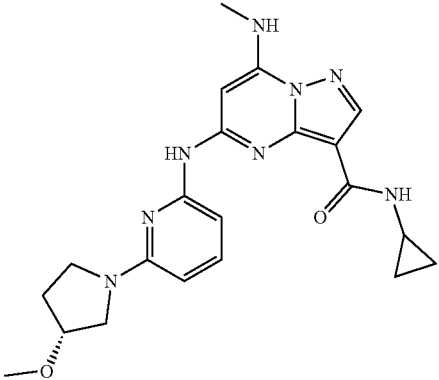 [SMILES: CNc1cc(Nc2cccc(N3CC[C@@H](OC)C3)n2)nc2c(C(=O)NC3CC3)cnn12] |

TABLE 1-continued

Selected Compounds

| Compound | Structure |
|---|---|
| I-482 | 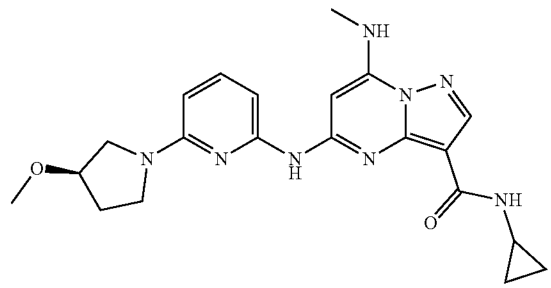 [SMILES: CNc1cc(Nc2cccc(N3CC[C@@H](OC)C3)n2)nc2c(C(=O)NC3CC3)cnn12] |
| I-483 | 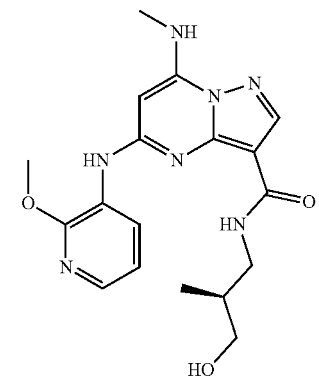 [SMILES: CNc1cc(Nc2cccnc2OC)nc2c(C(=O)NC[C@H](C)CO)cnn12] |
| I-484 | 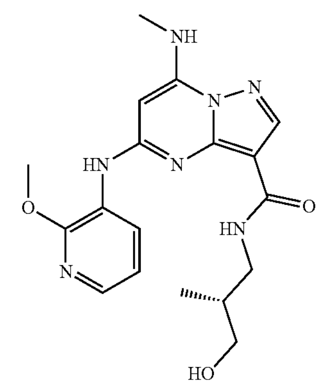 [SMILES: CNc1cc(Nc2cccnc2OC)nc2c(C(=O)NC[C@@H](C)CO)cnn12] |
| I-485 | 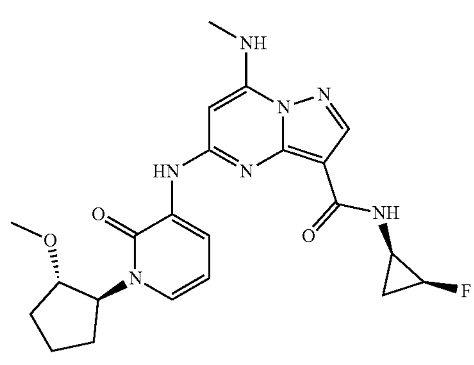 [SMILES: CNc1cc(Nc2cccn([C@H]3CCC[C@@H]3OC)c2=O)nc2c(C(=O)N[C@@H]3C[C@@H]3F)cnn12] |

TABLE 1-continued

Selected Compounds

| Compound | Structure |
|---|---|
| I-486 | 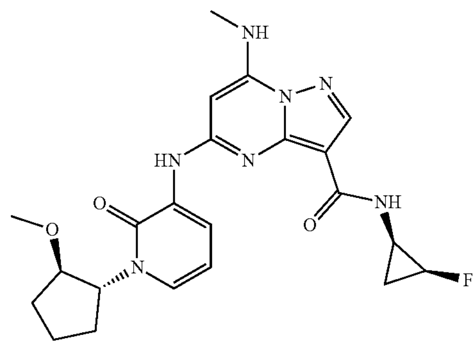 [SMILES: CNc1cc(Nc2cccn([C@@H]3CCC[C@H]3OC)c2=O)nc2c(C(=O)N[C@@H]3C[C@@H]3F)cnn12] |
| I-487 | 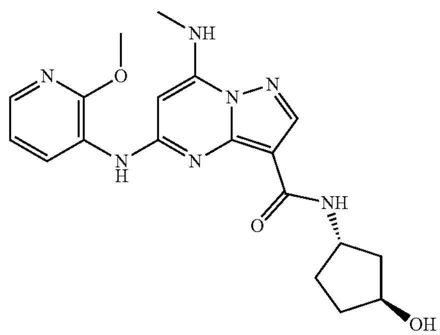 [SMILES: CNc1cc(Nc2cccnc2OC)nc2c(C(=O)N[C@H]3CC[C@H](O)C3)cnn12] |
| I-488 | 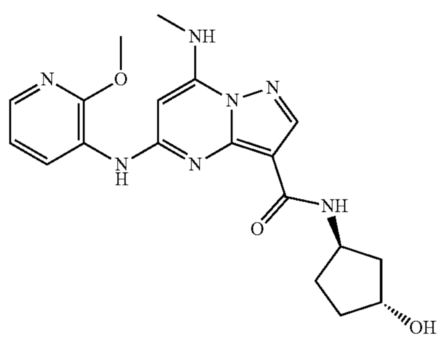 [SMILES: CNc1cc(Nc2cccnc2OC)nc2c(C(=O)N[C@@H]3CC[C@@H](O)C3)cnn12] |
| I-489 | 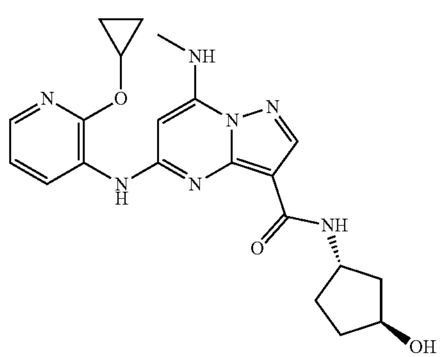 [SMILES: CNc1cc(Nc2cccnc2OC2CC2)nc2c(C(=O)N[C@H]3CC[C@H](O)C3)cnn12] |

TABLE 1-continued
Selected Compounds
| Compound | Structure |
|---|---|
| I-490 | 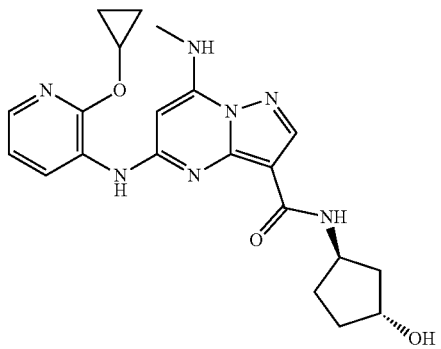 [SMILES: CNc1cc(Nc2cccnc2OC2CC2)nc2c(C(=O)N[C@@H]3CC[C@@H](O)C3)cnn12] |
| I-491 | 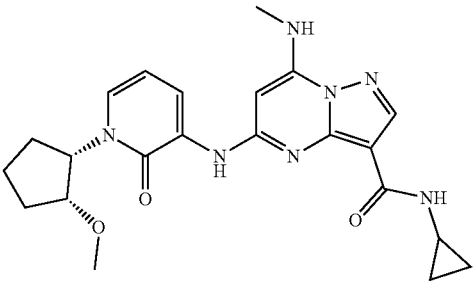 [SMILES: CNc1cc(Nc2cccn([C@H]3CCC[C@H]3OC)c2=O)nc2c(C(=O)NC3CC3)cnn12] |
| I-492 | 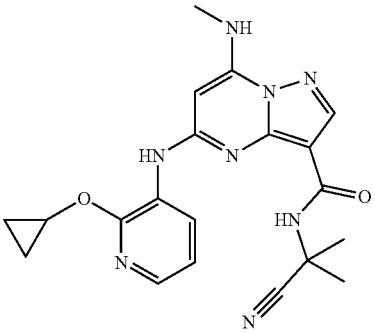 [SMILES: CNc1cc(Nc2cccnc2OC2CC2)nc2c(C(=O)NC(C)(C)C#N)cnn12] |
| I-493 | 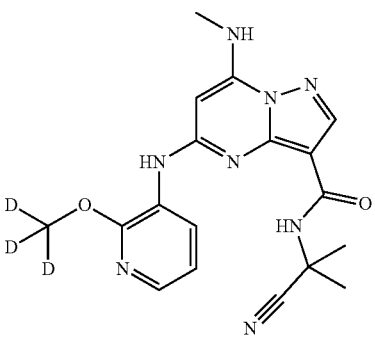 [SMILES: [2H]C([2H])([2H])Oc1ncccc1Nc1cc(NC)n2ncc(C(=O)NC(C)(C)C#N)c2n1] |

327
328
TABLE 1-continued
Selected Compounds
| Compound | Structure |
|---|---|
| I-494 | 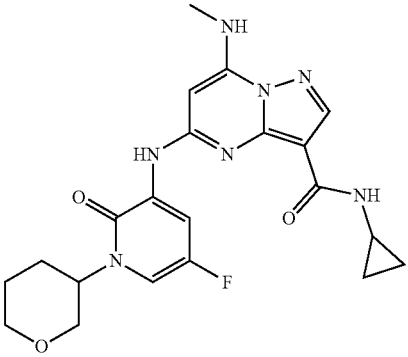 [SMILES: CNc1cc(Nc2cc(F)cn(C3CCCOC3)c2=O)nc2c(C(=O)NC3CC3)cnn12] |
| I-495 | 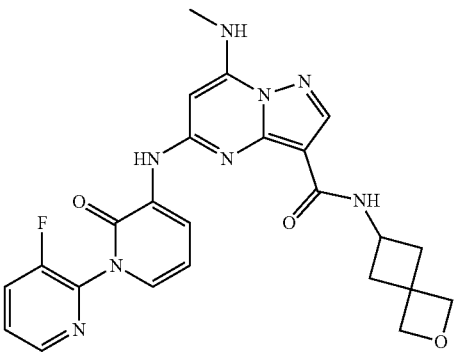 [SMILES: CNc1cc(Nc2cccn(-c3ncccc3F)c2=O)nc2c(C(=O)NC3CC4(COC4)C3)cnn12] |
| I-496 | 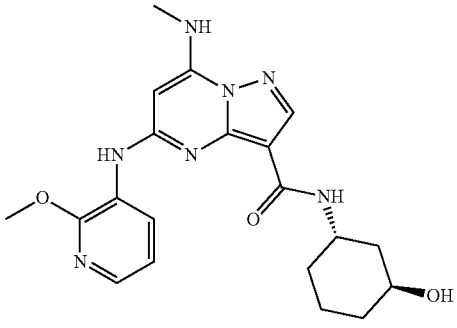 [SMILES: CNc1cc(Nc2cccnc2OC)nc2c(C(=O)N[C@H]3CCC[C@H](O)C3)cnn12] |
| I-497 | 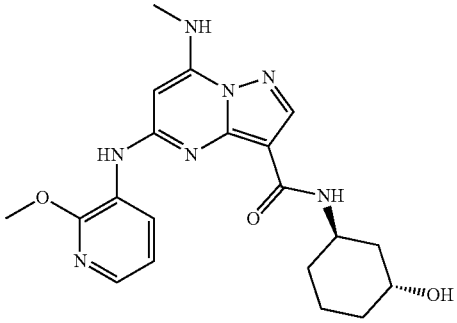 [SMILES: CNc1cc(Nc2cccnc2OC)nc2c(C(=O)N[C@@H]3CCC[C@@H](O)C3)cnn12] |

TABLE 1-continued
Selected Compounds
| Compound | Structure |
|---|---|
| I-498 | 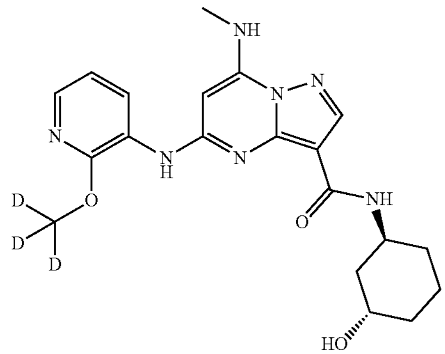 [SMILES: [2H]C([2H])([2H])Oc1ncccc1Nc1cc(NC)n2ncc(C(=O)N[C@H]3CCC[C@H](O)C3)c2n1] |
| I-499 | 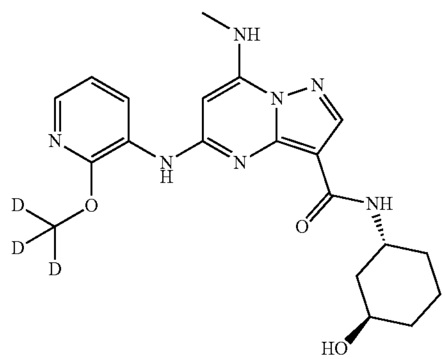 [SMILES: [2H]C([2H])([2H])Oc1ncccc1Nc1cc(NC)n2ncc(C(=O)N[C@@H]3CCC[C@@H](O)C3)c2n1] |
| I-500 | 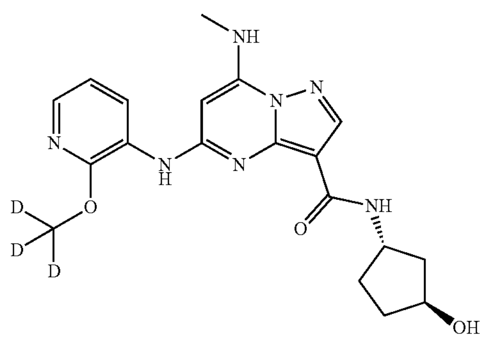 [SMILES: [2H]C([2H])([2H])Oc1ncccc1Nc1cc(NC)n2ncc(C(=O)N[C@H]3CC[C@H](O)C3)c2n1] |
| I-501 | 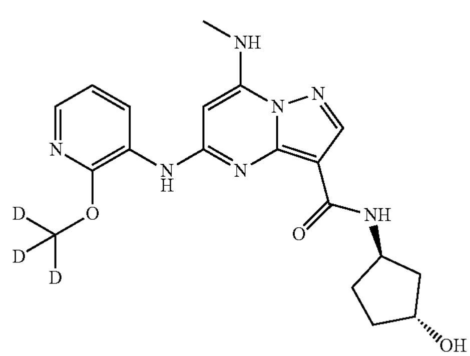 [SMILES: [2H]C([2H])([2H])Oc1ncccc1Nc1cc(NC)n2ncc(C(=O)N[C@@H]3CC[C@@H](O)C3)c2n1] |

TABLE 1-continued
Selected Compounds
| Compound | Structure |
|---|---|
| I-502 | 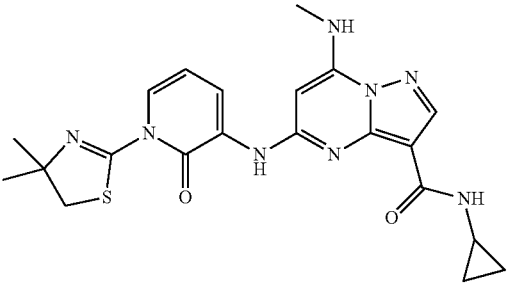 [SMILES: CNc1cc(Nc2cccn(C3=NC(C)(C)CS3)c2=O)nc2c(C(=O)NC3CC3)cnn12] |
| I-503 | 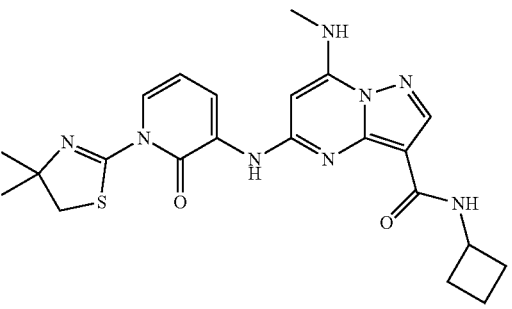 [SMILES: CNc1cc(Nc2cccn(C3=NC(C)(C)CS3)c2=O)nc2c(C(=O)NC3CCC3)cnn12] |
| I-504 | 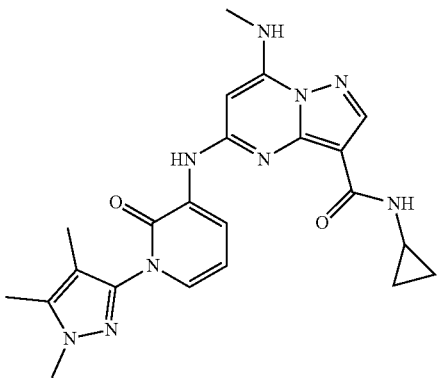 [SMILES: CNc1cc(Nc2cccn(-c3nn(C)c(C)c3C)c2=O)nc2c(C(=O)NC3CC3)cnn12] |
| I-505 | 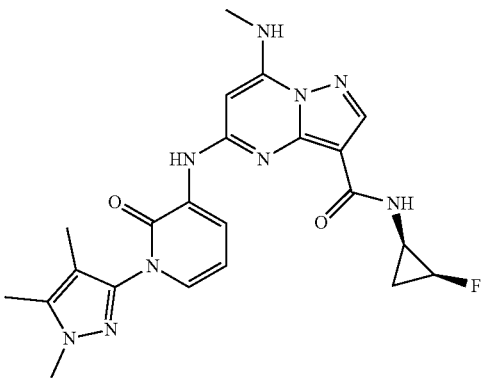 [SMILES: CNc1cc(Nc2cccn(-c3nn(C)c(C)c3C)c2=O)nc2c(C(=O)N[C@@H]3C[C@@H]3F)cnn12] |

TABLE 1-continued
Selected Compounds
| Compound | Structure |
|---|---|
| I-506 | 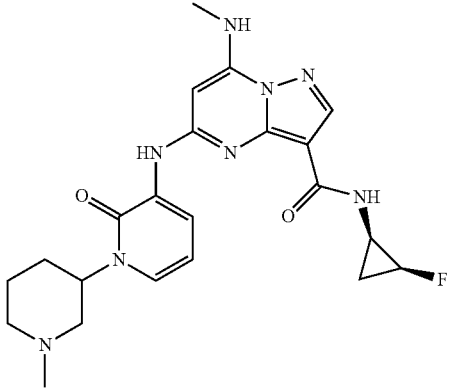 [SMILES: CNc1cc(Nc2cccn(C3CCCN(C)C3)c2=O)nc2c(C(=O)N[C@@H]3C[C@@H]3F)cnn12] |
| I-507 | 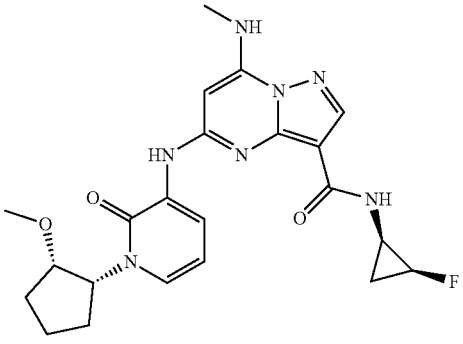 [SMILES: CNc1cc(Nc2cccn([C@@H]3CCC[C@@H]3OC)c2=O)nc2c(C(=O)N[C@@H]3C[C@@H]3F)cnn12] |
| I-508 | 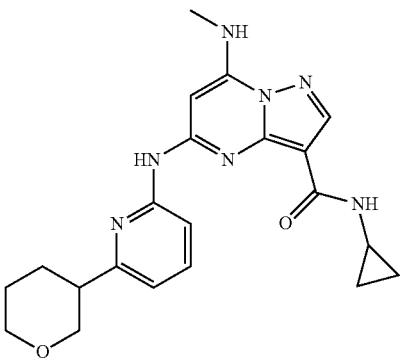 [SMILES: CNc1cc(Nc2cccc(C3CCCOC3)n2)nc2c(C(=O)NC3CC3)cnn12] |
| I-509 | 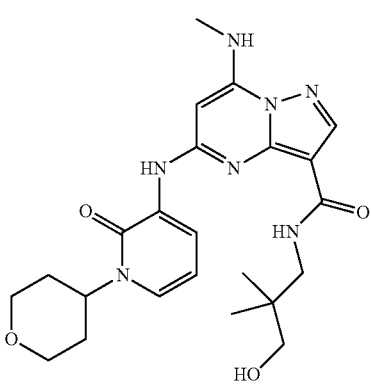 [SMILES: CNc1cc(Nc2cccn(C3CCOCC3)c2=O)nc2c(C(=O)NCC(C)(C)CO)cnn12] |

TABLE 1-continued
Selected Compounds
| Compound | Structure |
| --- | --- |
| I-510 | 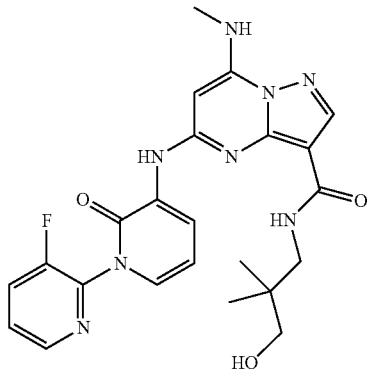 [SMILES: CNc1cc(Nc2cccn(-c3ncccc3F)c2=O)nc2c(C(=O)NCC(C)(C)CO)cnn12] |
| I-511 | 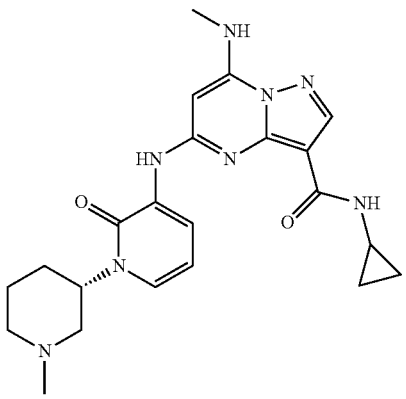 [SMILES: CNc1cc(Nc2cccn([C@H]3CCCN(C)C3)c2=O)nc2c(C(=O)NC3CC3)cnn12] |
| I-512 | 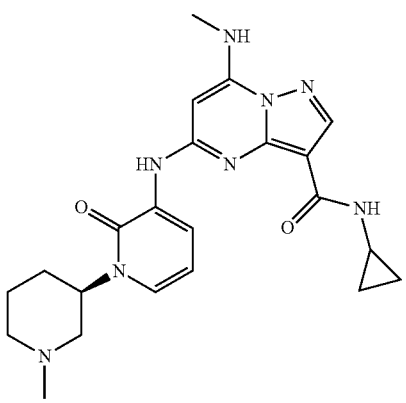 [SMILES: CNc1cc(Nc2cccn([C@@H]3CCCN(C)C3)c2=O)nc2c(C(=O)NC3CC3)cnn12] |

TABLE 1-continued
Selected Compounds
| Compound | Structure |
|---|---|
| I-513 | 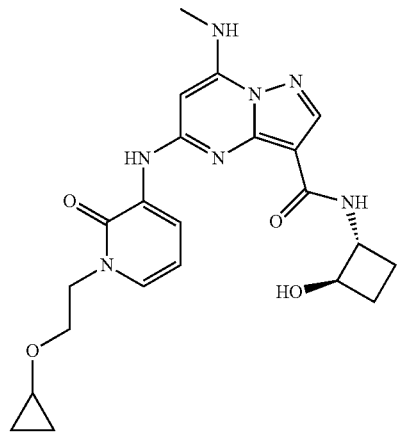 [SMILES: CNc1cc(Nc2cccn(CCOC3CC3)c2=O)nc2c(C(=O)N[C@@H]3CC[C@H]3O)cnn12] |
| I-514 | 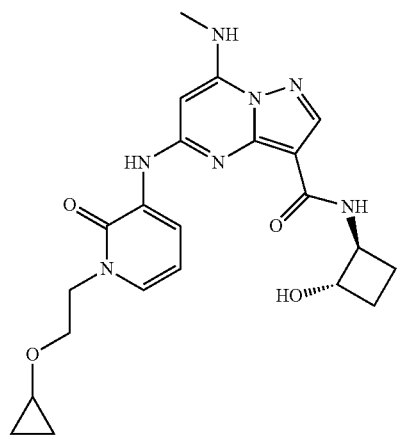 [SMILES: CNc1cc(Nc2cccn(CCOC3CC3)c2=O)nc2c(C(=O)N[C@H]3CC[C@@H]3O)cnn12] |
| I-515 | 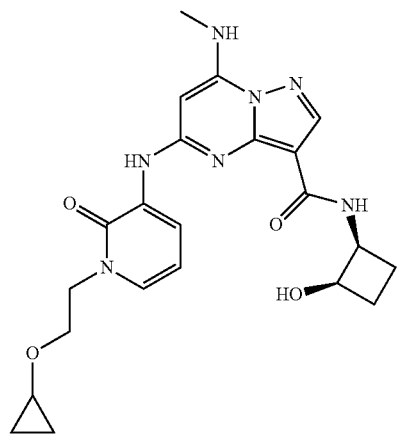 [SMILES: CNc1cc(Nc2cccn(CCOC3CC3)c2=O)nc2c(C(=O)N[C@H]3CC[C@H]3O)cnn12] |

TABLE 1-continued

| Selected Compounds | |
|---|---|
| Compound | Structure |
| I-516 | |
| I-517 | |
| I-518 | |
| I-519 | |

TABLE 1-continued

Selected Compounds

| Compound | Structure |
|---|---|
| I-520 | 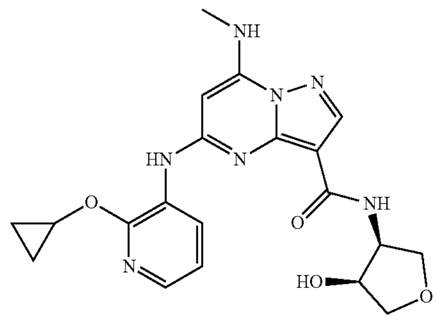 [SMILES: CNc1cc(Nc2cccnc2OC2CC2)nc2c(C(=O)N[C@H]3COC[C@H]3O)cnn12] |
| I-521 | 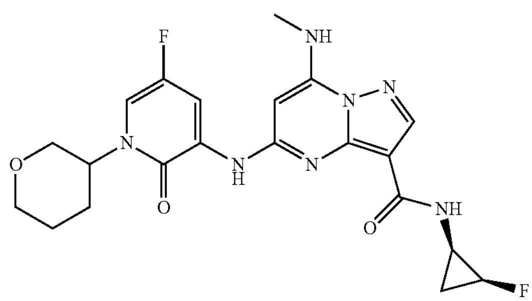 [SMILES: CNc1cc(Nc2cc(F)cn(C3CCCOC3)c2=O)nc2c(C(=O)N[C@@H]3C[C@@H]3F)cnn12] |
| I-522 | 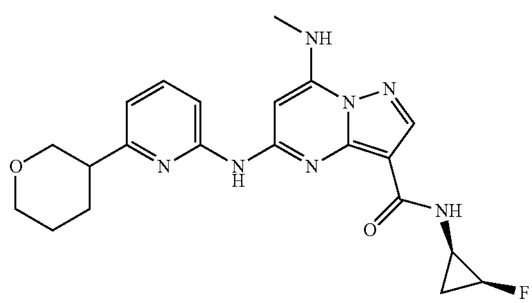 [SMILES: CNc1cc(Nc2cccc(C3CCCOC3)n2)nc2c(C(=O)N[C@@H]3C[C@@H]3F)cnn12] |
| I-523 | 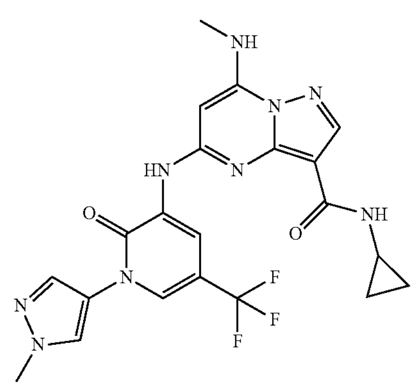 [SMILES: CNc1cc(Nc2cc(C(F)(F)F)cn(-c3cnn(C)c3)c2=O)nc2c(C(=O)NC3CC3)cnn12] |

TABLE 1-continued

Selected Compounds

| Compound | Structure |
|---|---|
| I-524 | 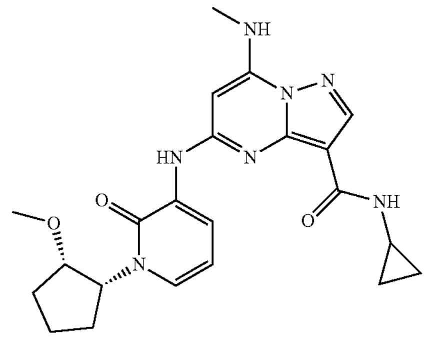 [SMILES: CNc1cc(Nc2cccn([C@@H]3CCC[C@@H]3OC)c2=O)nc2c(C(=O)NC3CC3)cnn12] |
| I-525 | 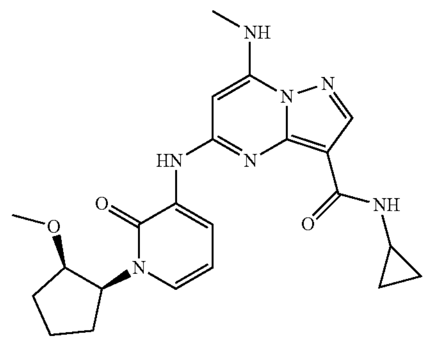 [SMILES: CNc1cc(Nc2cccn([C@H]3CCC[C@H]3OC)c2=O)nc2c(C(=O)NC3CC3)cnn12] |
| I-526 | 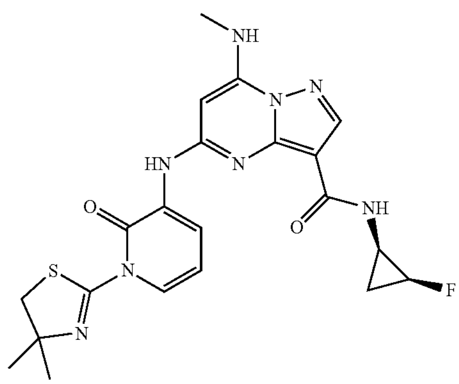 [SMILES: CNc1cc(Nc2cccn(C3=NC(C)(C)CS3)c2=O)nc2c(C(=O)N[C@@H]3C[C@@H]3F)cnn12] |
| I-527 | 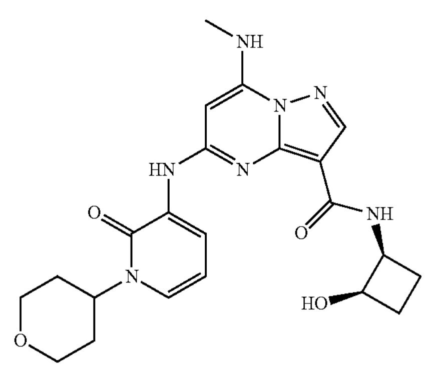 [SMILES: CNc1cc(Nc2cccn(C3CCOCC3)c2=O)nc2c(C(=O)N[C@H]3CC[C@H]3O)cnn12] |

TABLE 1-continued
| Selected Compounds | |
|---|---|
| Compound | Structure |
| I-528 | 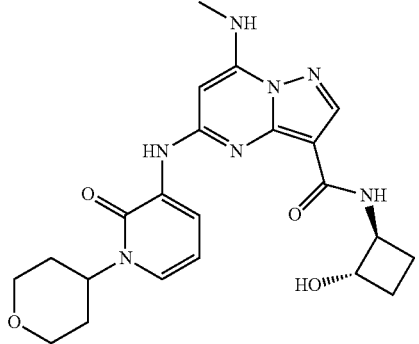 [SMILES: CNc1cc(Nc2cccn(C3CCOCC3)c2=O)nc2c(C(=O)N[C@H]3CC[C@@H]3O)cnn12] |
| I-529 | 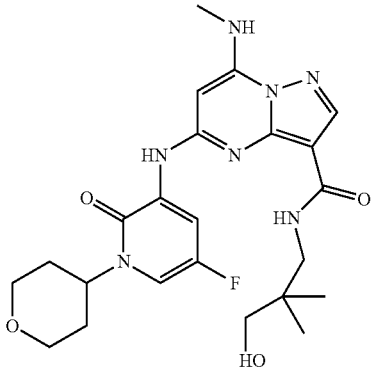 [SMILES: CNc1cc(Nc2cc(F)cn(C3CCOCC3)c2=O)nc2c(C(=O)NCC(C)(C)CO)cnn12] |
| I-530 | 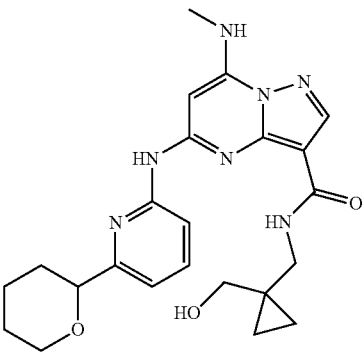 [SMILES: CNc1cc(Nc2cccc(C3CCCCO3)n2)nc2c(C(=O)NCC3(CO)CC3)cnn12] |
| I-531 | 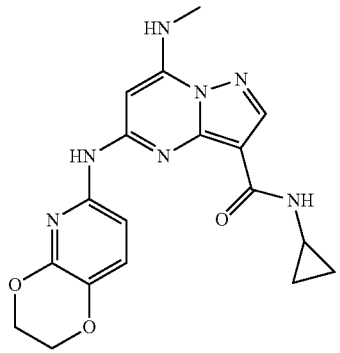 [SMILES: CNc1cc(Nc2ccc3c(n2)OCCO3)nc2c(C(=O)NC3CC3)cnn12] |

TABLE 1-continued

Selected Compounds

| Compound | Structure |
|---|---|
| I-532 | 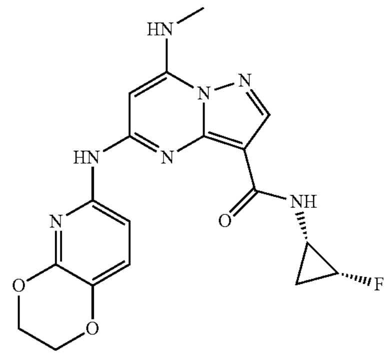 [SMILES: CNc1cc(Nc2ccc3c(n2)OCCO3)nc2c(C(=O)N[C@H]3C[C@H]3F)cnn12] |
| I-533 | 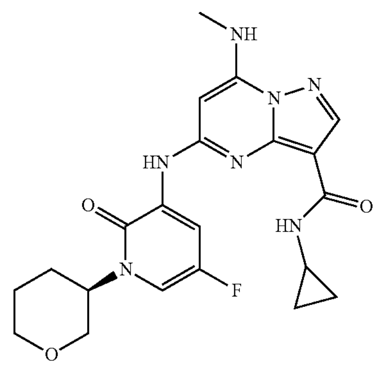 [SMILES: CNc1cc(Nc2cc(F)cn([C@@H]3CCCOC3)c2=O)nc2c(C(=O)NC3CC3)cnn12] |
| I-534 | 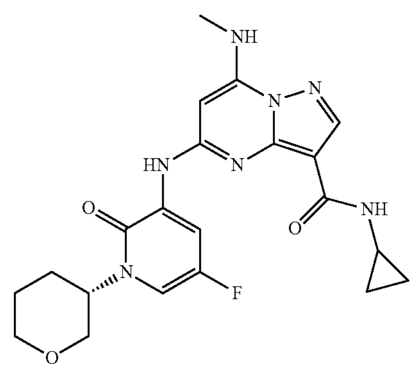 [SMILES: CNc1cc(Nc2cc(F)cn([C@H]3CCCOC3)c2=O)nc2c(C(=O)NC3CC3)cnn12] |
| I-535 | 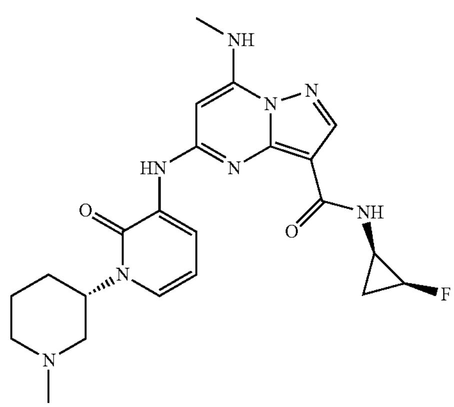 [SMILES: CNc1cc(Nc2cccn([C@H]3CCCN(C)C3)c2=O)nc2c(C(=O)N[C@@H]3C[C@@H]3F)cnn12] |

TABLE 1-continued
Selected Compounds
| Compound | Structure |
|---|---|
| I-536 | 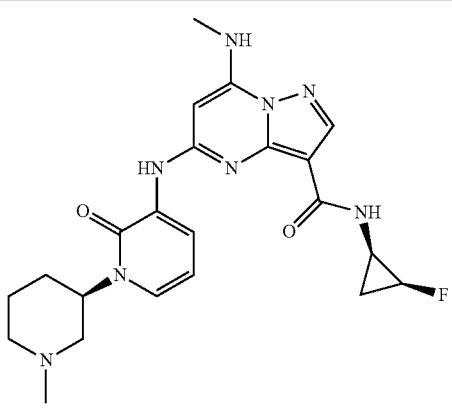 [SMILES: CNc1cc(Nc2cccn([C@@H]3CCCN(C)C3)c2=O)nc2c(C(=O)N[C@@H]3C[C@@H]3F)cnn12] |
| I-537 | 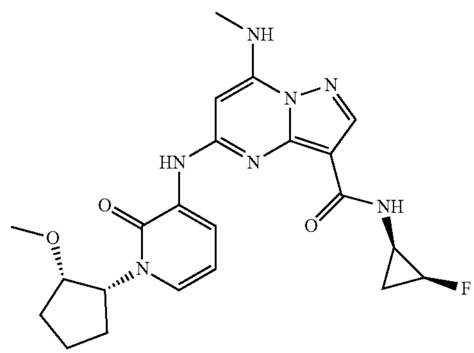 [SMILES: CNc1cc(Nc2cccn([C@@H]3CCC[C@@H]3OC)c2=O)nc2c(C(=O)N[C@@H]3C[C@@H]3F)cnn12] |
| I-538 | 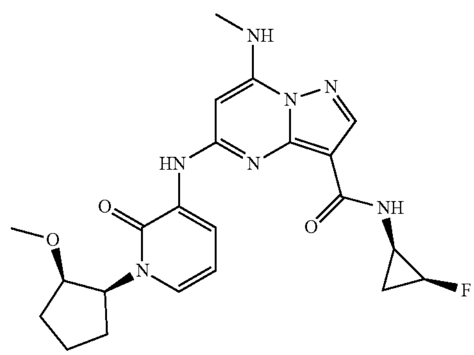 [SMILES: CNc1cc(Nc2cccn([C@H]3CCC[C@H]3OC)c2=O)nc2c(C(=O)N[C@@H]3C[C@@H]3F)cnn12] |
| I-539 | 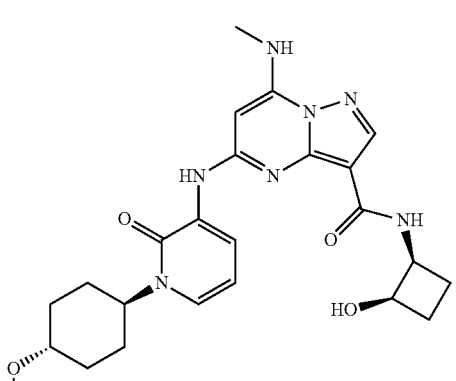 |

TABLE 1-continued

| Selected Compounds | |
|---|---|
| Compound | Structure |
| I-540 | |
| I-541 | |
| I-542 | |
| I-543 | |

TABLE 1-continued

Selected Compounds

| Compound | Structure |
|---|---|
| I-544 | 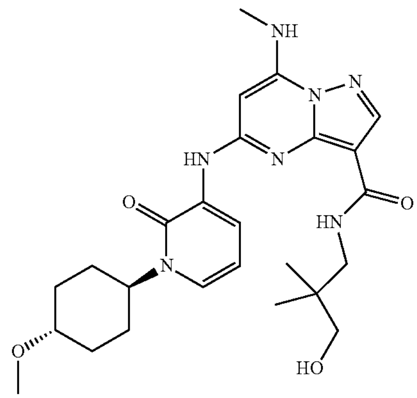 [SMILES: CNc1cc(Nc2cccn([C@H]3CC[C@H](OC)CC3)c2=O)nc2c(C(=O)NCC(C)(C)CO)cnn12] |
| I-545 | 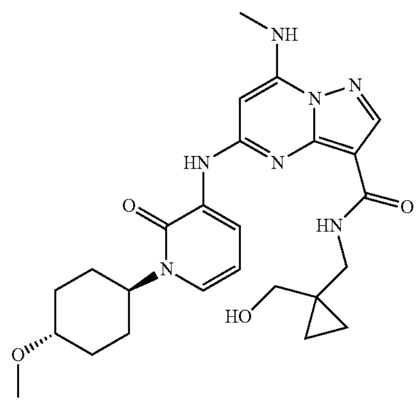 [SMILES: CNc1cc(Nc2cccn([C@H]3CC[C@H](OC)CC3)c2=O)nc2c(C(=O)NCC3(CO)CC3)cnn12] |
| I-546 | 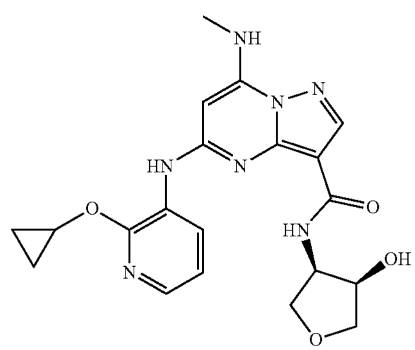 [SMILES: CNc1cc(Nc2cccnc2OC2CC2)nc2c(C(=O)N[C@@H]3COC[C@@H]3O)cnn12] |
| I-547 | 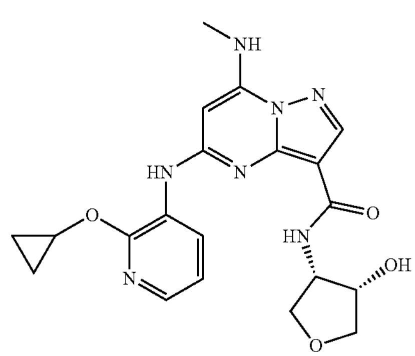 [SMILES: CNc1cc(Nc2cccnc2OC2CC2)nc2c(C(=O)N[C@H]3COC[C@H]3O)cnn12] |

TABLE 1-continued
Selected Compounds
| Compound | Structure |
|---|---|
| I-548 | 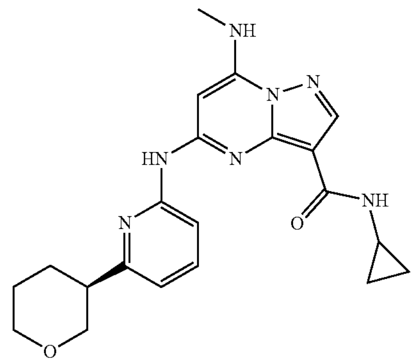 [SMILES: CNc1cc(Nc2cccc([C@@H]3CCCOC3)n2)nc2c(C(=O)NC3CC3)cnn12] |
| I-549 | 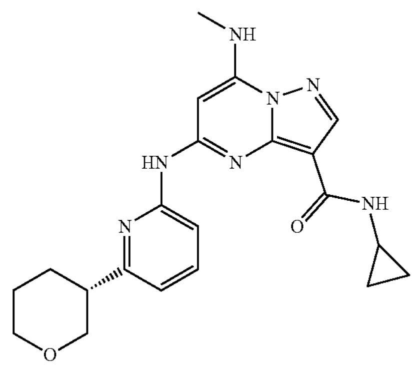 [SMILES: CNc1cc(Nc2cccc([C@H]3CCCOC3)n2)nc2c(C(=O)NC3CC3)cnn12] |
| I-550 | 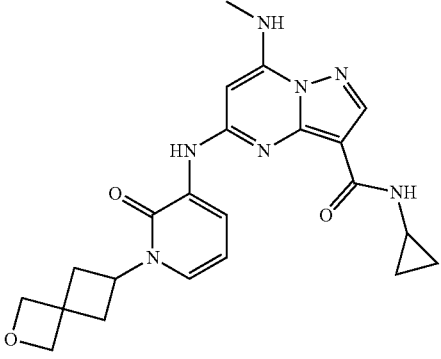 [SMILES: CNc1cc(Nc2cccn(C3CC4(COC4)C3)c2=O)nc2c(C(=O)NC3CC3)cnn12] |
| I-551 | 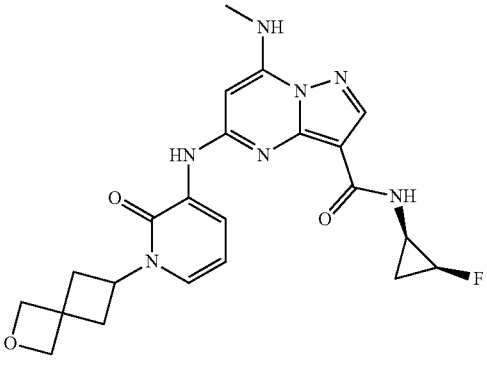 [SMILES: CNc1cc(Nc2cccn(C3CC4(COC4)C3)c2=O)nc2c(C(=O)N[C@@H]3C[C@@H]3F)cnn12] |

TABLE 1-continued
Selected Compounds
| Compound | Structure |
|---|---|
| I-552 | 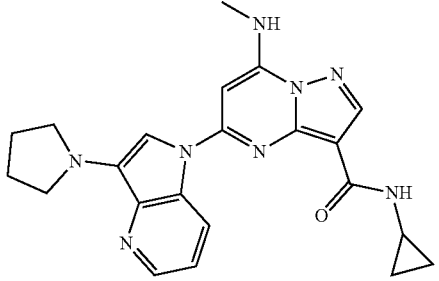 [SMILES: CNc1cc(-n2cc(N3CCCC3)c3ncccc32)nc2c(C(=O)NC3CC3)cnn12] |
| I-553 | 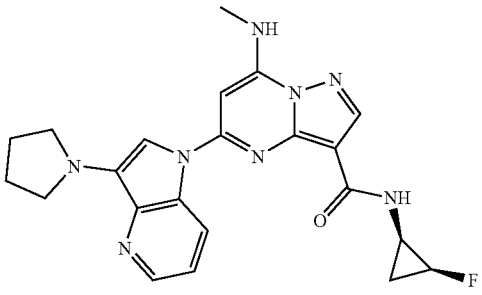 [SMILES: CNc1cc(-n2cc(N3CCCC3)c3ncccc32)nc2c(C(=O)N[C@@H]3C[C@@H]3F)cnn12] |
| I-554 | 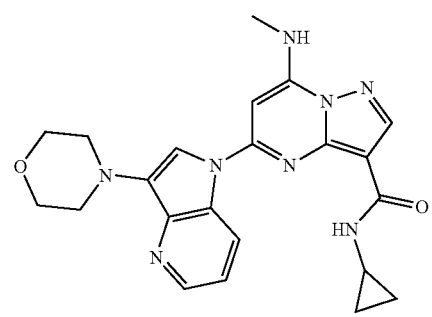 [SMILES: CNc1cc(-n2cc(N3CCOCC3)c3ncccc32)nc2c(C(=O)NC3CC3)cnn12] |
| I-555 | 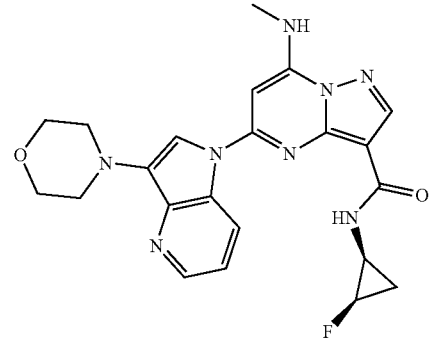 [SMILES: CNc1cc(-n2cc(N3CCOCC3)c3ncccc32)nc2c(C(=O)N[C@H]3C[C@H]3F)cnn12] |

TABLE 1-continued
Selected Compounds
| Compound | Structure |
|---|---|
| I-556 | 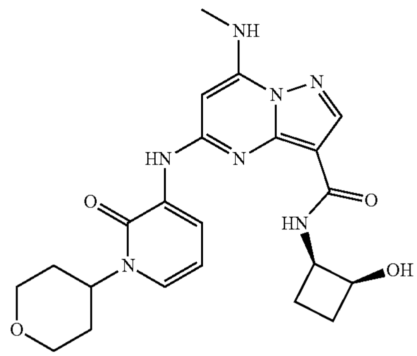 [SMILES: CNc1cc(Nc2cccn(C3CCOCC3)c2=O)nc2c(C(=O)N[C@@H]3CC[C@@H]3O)cnn12] |
| I-557 | 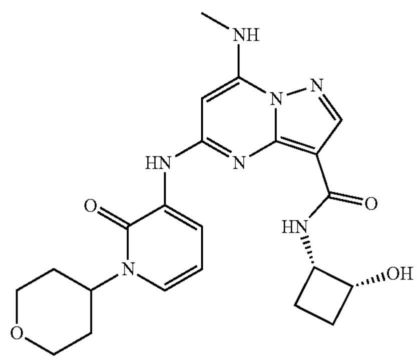 [SMILES: CNc1cc(Nc2cccn(C3CCOCC3)c2=O)nc2c(C(=O)N[C@H]3CC[C@H]3O)cnn12] |
| I-558 | 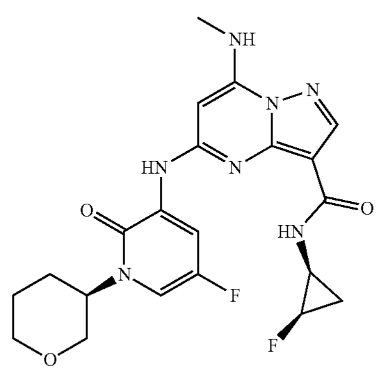 [SMILES: CNc1cc(Nc2cc(F)cn([C@@H]3CCCOC3)c2=O)nc2c(C(=O)N[C@H]3C[C@H]3F)cnn12] |
| I-559 | 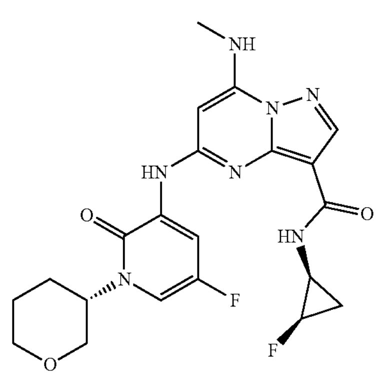 [SMILES: CNc1cc(Nc2cc(F)cn([C@H]3CCCOC3)c2=O)nc2c(C(=O)N[C@H]3C[C@H]3F)cnn12] |

TABLE 1-continued

| Compound | Structure |
|---|---|
| I-560 | 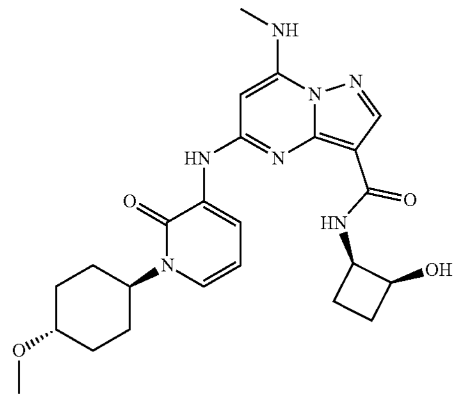 [SMILES: CNc1cc(Nc2cccn([C@H]3CC[C@H](OC)CC3)c2=O)nc2c(C(=O)N[C@@H]3CC[C@@H]3O)cnn12] |
| I-561 | 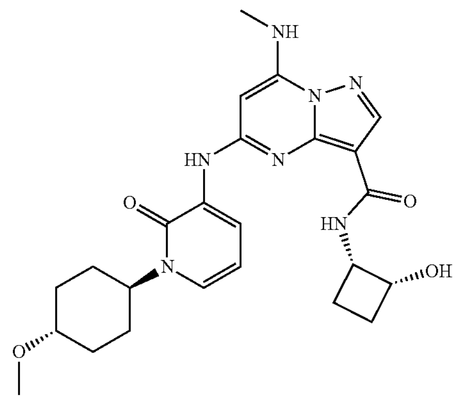 [SMILES: CNc1cc(Nc2cccn([C@H]3CC[C@H](OC)CC3)c2=O)nc2c(C(=O)N[C@H]3CC[C@H]3O)cnn12] |
| I-562 | 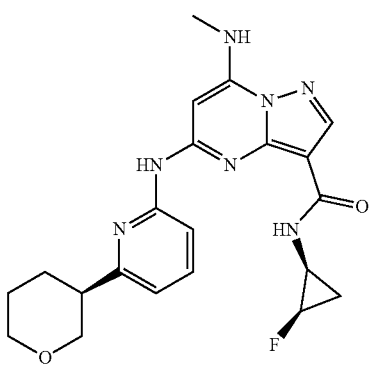 [SMILES: CNc1cc(Nc2cccc([C@@H]3CCCOC3)n2)nc2c(C(=O)N[C@H]3C[C@H]3F)cnn12] |
| I-563 | 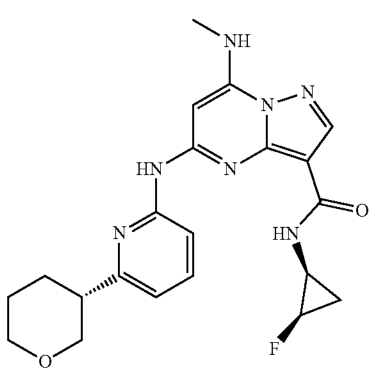 [SMILES: CNc1cc(Nc2cccc([C@H]3CCCOC3)n2)nc2c(C(=O)N[C@H]3C[C@H]3F)cnn12] |

TABLE 1-continued

Selected Compounds

| Compound | Structure |
|---|---|
| I-564 | 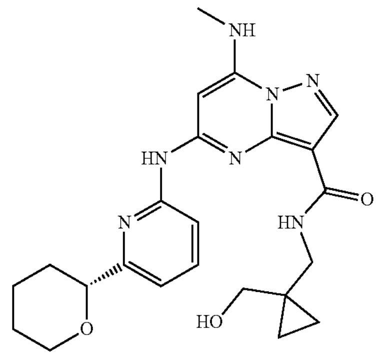 [SMILES: CNc1cc(Nc2cccc([C@H]3CCCCO3)n2)nc2c(C(=O)NCC3(CO)CC3)cnn12] |
| I-565 | 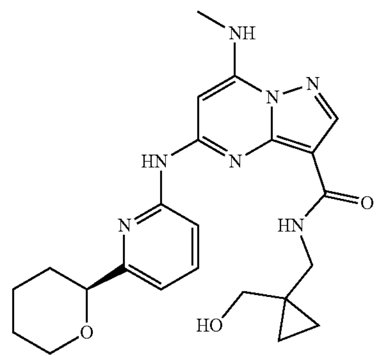 [SMILES: CNc1cc(Nc2cccc([C@@H]3CCCCO3)n2)nc2c(C(=O)NCC3(CO)CC3)cnn12] |
| I-566 | 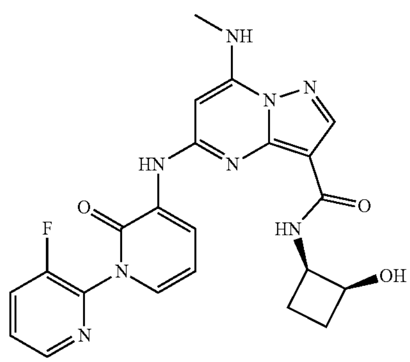 |
| I-567 | 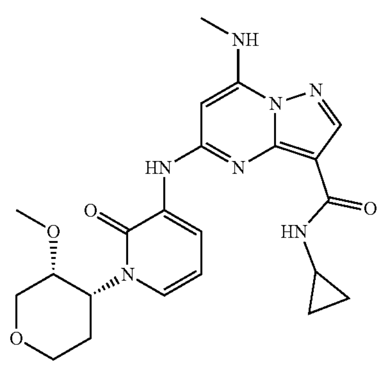 [SMILES: CNc1cc(Nc2cccn([C@@H]3CCOC[C@@H]3OC)c2=O)nc2c(C(=O)NC3CC3)cnn12] |

TABLE 1-continued

| Compound | Structure |
|---|---|
| I-568 | 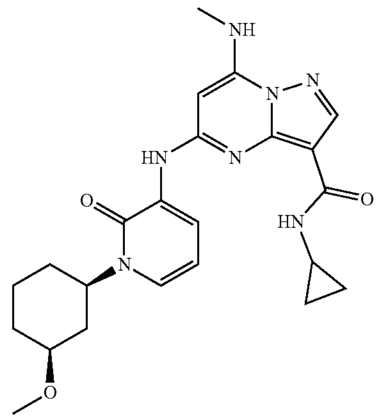 [SMILES: CNc1cc(Nc2cccn([C@@H]3CCC[C@H](OC)C3)c2=O)nc2c(C(=O)NC3CC3)cnn12] |
| I-569 | 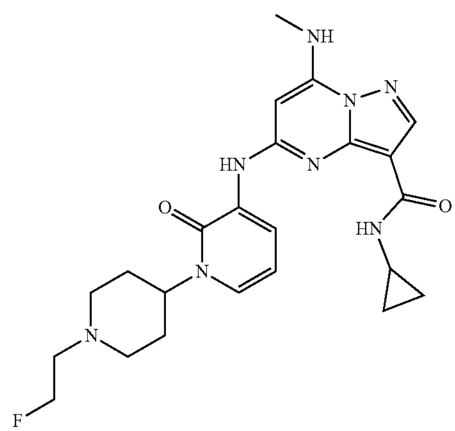 [SMILES: CNc1cc(Nc2cccn(C3CCN(CCF)CC3)c2=O)nc2c(C(=O)NC3CC3)cnn12] |
| I-570 | 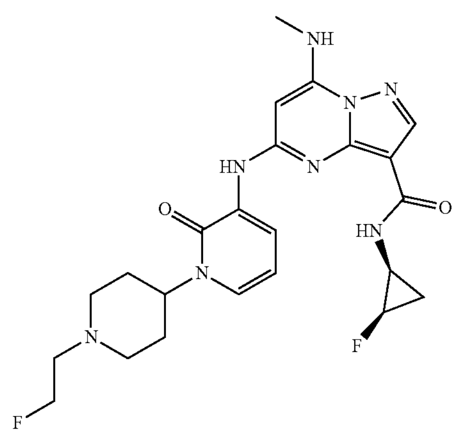 [SMILES: CNc1cc(Nc2cccn(C3CCN(CCF)CC3)c2=O)nc2c(C(=O)N[C@H]3C[C@H]3F)cnn12] |

TABLE 1-continued
Selected Compounds
| Compound | Structure |
|---|---|
| I-571 | 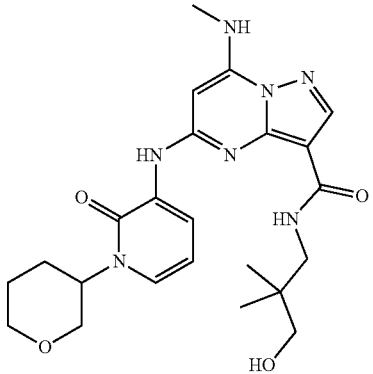 [SMILES: CNc1cc(Nc2cccn(C3CCCOC3)c2=O)nc2c(C(=O)NCC(C)(C)CO)cnn12] |
| I-572 | 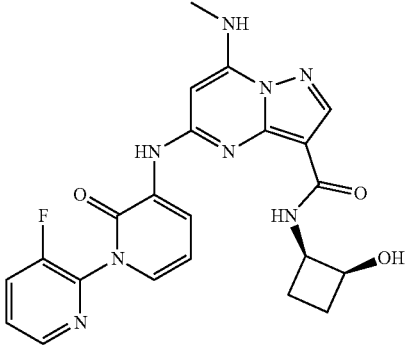 [SMILES: CNc1cc(Nc2cccn(-c3ncccc3F)c2=O)nc2c(C(=O)N[C@@H]3CC[C@@H]3O)cnn12] |
| I-573 | 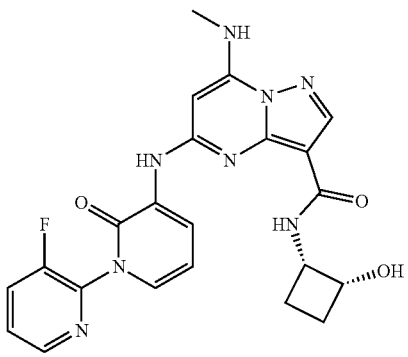 [SMILES: CNc1cc(Nc2cccn(-c3ncccc3F)c2=O)nc2c(C(=O)N[C@H]3CC[C@H]3O)cnn12] |
| I-574 | 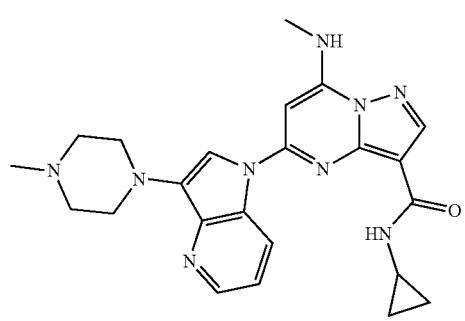 [SMILES: CNc1cc(-n2cc(N3CCN(C)CC3)c3ncccc32)nc2c(C(=O)NC3CC3)cnn12] |

TABLE 1-continued
Selected Compounds
| Compound | Structure |
|---|---|
| I-575 | 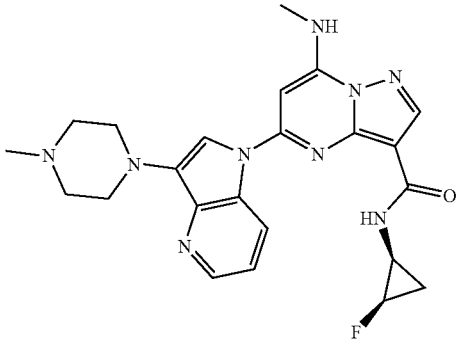 [SMILES: CNc1cc(-n2cc(N3CCN(C)CC3)c3ncccc32)nc2c(C(=O)N[C@H]3C[C@H]3F)cnn12] |
| I-576 | 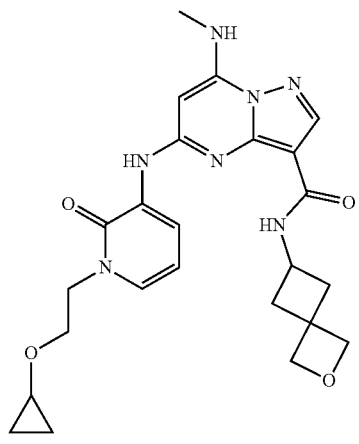 [SMILES: CNc1cc(Nc2cccn(CCOC3CC3)c2=O)nc2c(C(=O)NC3CC4(COC4)C3)cnn12] |
| I-577 | 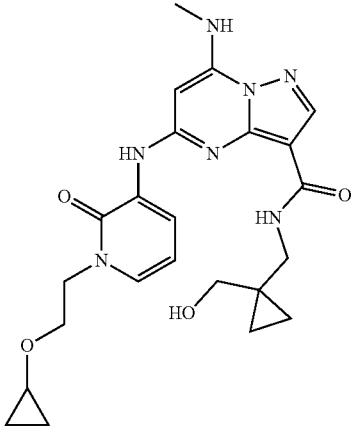 [SMILES: CNc1cc(Nc2cccn(CCOC3CC3)c2=O)nc2c(C(=O)NCC3(CO)CC3)cnn12] |
| I-578 | 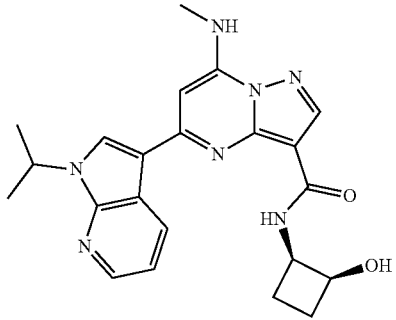 [SMILES: CNc1cc(-c2cn(C(C)C)c3ncccc23)nc2c(C(=O)N[C@@H]3CC[C@@H]3O)cnn12] |

TABLE 1-continued

| Compound | Structure |
|---|---|
| I-579 | 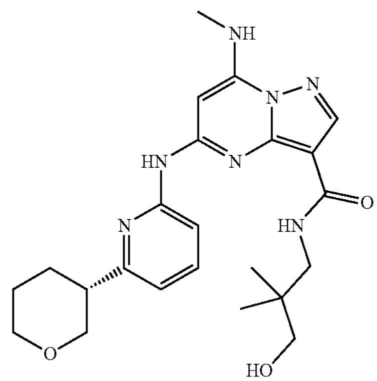 [SMILES: CNc1cc(Nc2cccc([C@H]3CCCOC3)n2)nc2c(C(=O)NCC(C)(C)CO)cnn12] |
| I-580 | 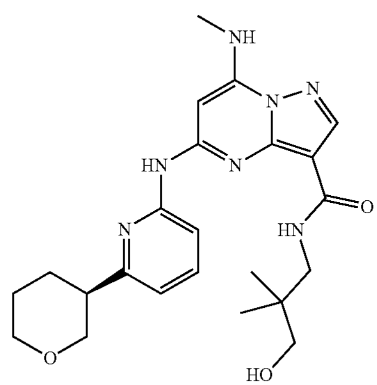 [SMILES: CNc1cc(Nc2cccc([C@@H]3CCCOC3)n2)nc2c(C(=O)NCC(C)(C)CO)cnn12] |
| I-581 | 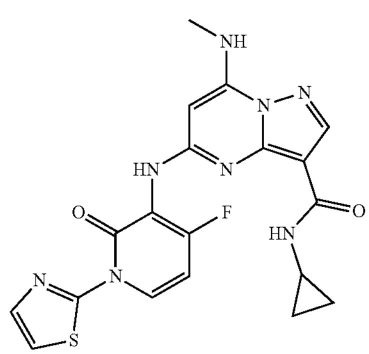 [SMILES: CNc1cc(Nc2c(F)ccn(-c3nccs3)c2=O)nc2c(C(=O)NC3CC3)cnn12] |
| I-582 | 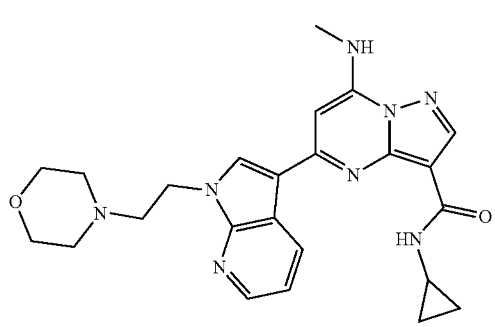 [SMILES: CNc1cc(-c2cn(CCN3CCOCC3)c3ncccc23)nc2c(C(=O)NC3CC3)cnn12] |

TABLE 1-continued
Selected Compounds
| Compound | Structure |
|---|---|
| I-583 | 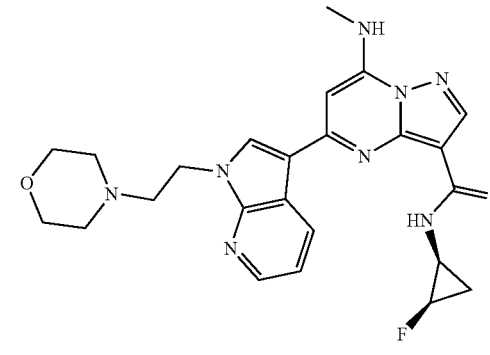 |
| I-584 | 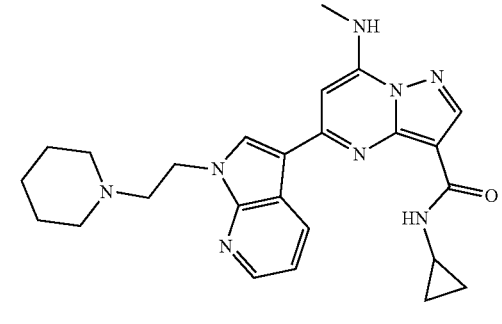 [SMILES: CNc1cc(-c2cn(CCN3CCCCC3)c3ncccc23)nc2c(C(=O)NC3CC3)cnn12] |
| I-585 | 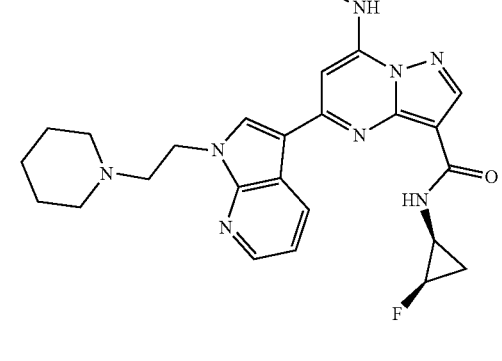 |
| I-586 | 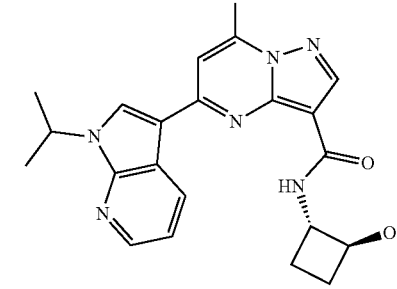 |

TABLE 1-continued

| Selected Compounds | |
|---|---|
| Compound | Structure |
| I-587 | |
| I-588 | |
| I-589 | |
| I-590 | |

TABLE 1-continued

Selected Compounds

| Compound | Structure |
|---|---|
| I-591 | 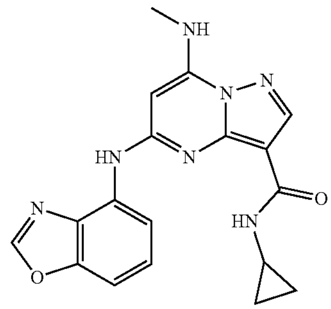 [SMILES: CNc1cc(Nc2cccc3ocnc23)nc2c(C(=O)NC3CC3)cnn12] |
| I-592 | 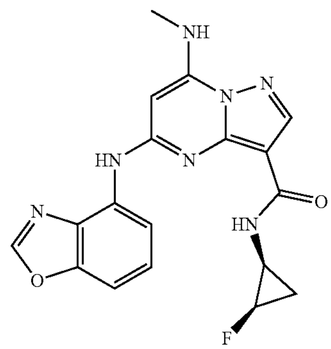 [SMILES: CNc1cc(Nc2cccc3ocnc23)nc2c(C(=O)N[C@H]3C[C@H]3F)cnn12] |
| I-593 | 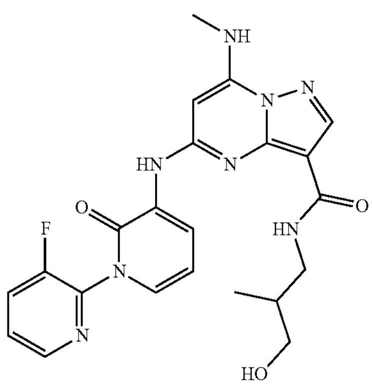 [SMILES: CNc1cc(Nc2cccn(-c3ncccc3F)c2=O)nc2c(C(=O)NCC(C)CO)cnn12] |
| I-594 | 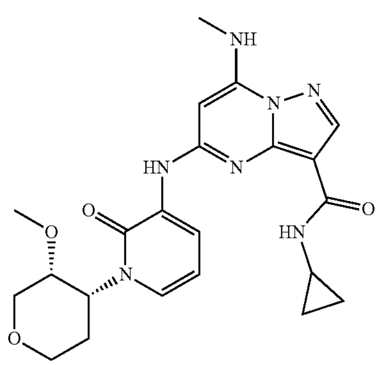 [SMILES: CNc1cc(Nc2cccn([C@@H]3CCOC[C@@H]3OC)c2=O)nc2c(C(=O)NC3CC3)cnn12] |

TABLE 1-continued
Selected Compounds
| Compound | Structure |
|---|---|
| I-595 | 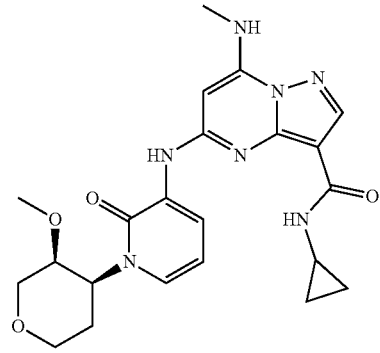 [SMILES: CNc1cc(Nc2cccn([C@H]3CCOC[C@H]3OC)c2=O)nc2c(C(=O)NC3CC3)cnn12] |
| I-596 | 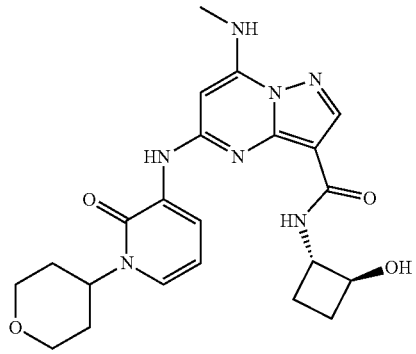 [SMILES: CNc1cc(Nc2cccn(C3CCOCC3)c2=O)nc2c(C(=O)N[C@H]3CC[C@@H]3O)cnn12] |
| I-597 | 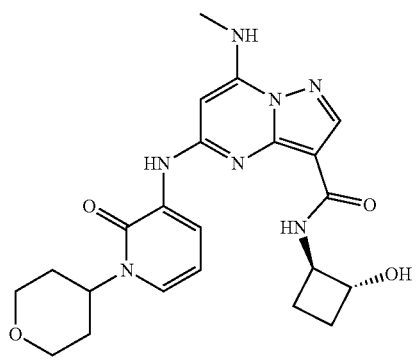 [SMILES: CNc1cc(Nc2cccn(C3CCOCC3)c2=O)nc2c(C(=O)N[C@@H]3CC[C@H]3O)cnn12] |
| I-598 | 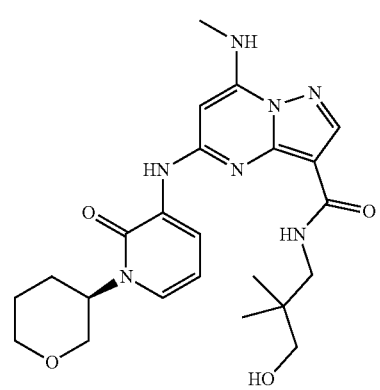 [SMILES: CNc1cc(Nc2cccn([C@@H]3CCCOC3)c2=O)nc2c(C(=O)NCC(C)(C)CO)cnn12] |

TABLE 1-continued

Selected Compounds

| Compound | Structure |
|---|---|
| I-599 | 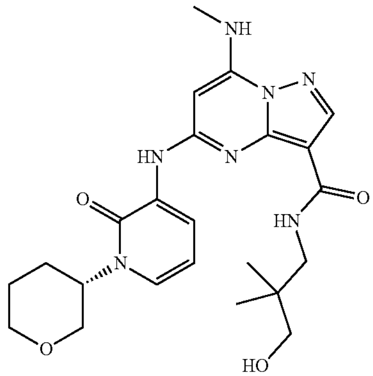 [SMILES: CNc1cc(Nc2cccn([C@H]3CCCOC3)c2=O)nc2c(C(=O)NCC(C)(C)CO)cnn12] |
| I-600 | 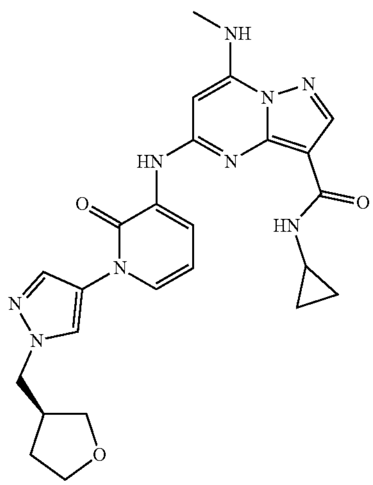 [SMILES: CNc1cc(Nc2cccn(-c3cnn(C[C@@H]4CCOC4)c3)c2=O)nc2c(C(=O)NC3CC3)cnn12] |
| I-601 | 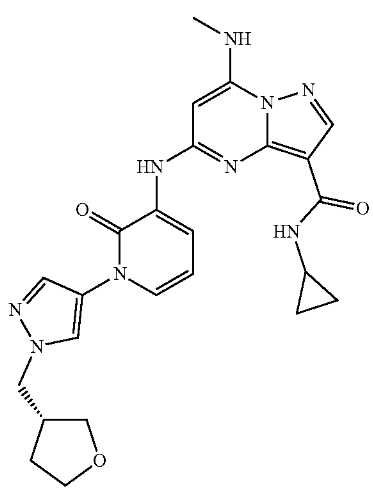 [SMILES: CNc1cc(Nc2cccn(-c3cnn(C[C@H]4CCOC4)c3)c2=O)nc2c(C(=O)NC3CC3)cnn12] |

TABLE 1-continued

Selected Compounds

| Compound | Structure |
|---|---|
| I-602 | 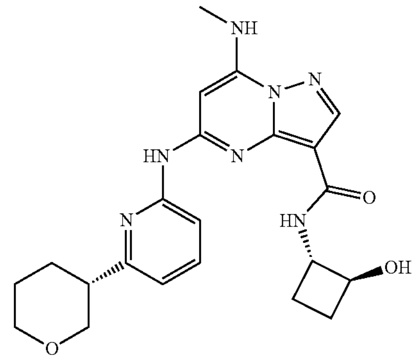 [SMILES: CNc1cc(Nc2cccc([C@H]3CCCOC3)n2)nc2c(C(=O)N[C@H]3CC[C@@H]3O)cnn12] |
| I-603 | 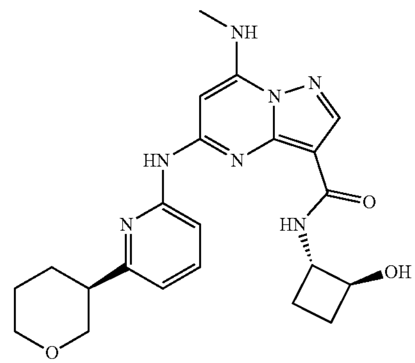 [SMILES: CNc1cc(Nc2cccc([C@@H]3CCCOC3)n2)nc2c(C(=O)N[C@H]3CC[C@@H]3O)cnn12] |
| I-604 | 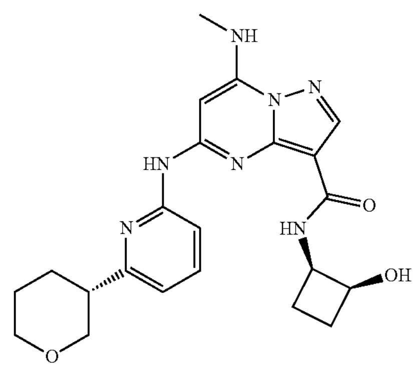 [SMILES: CNc1cc(Nc2cccc([C@H]3CCCOC3)n2)nc2c(C(=O)N[C@@H]3CC[C@@H]3O)cnn12] |
| I-605 | 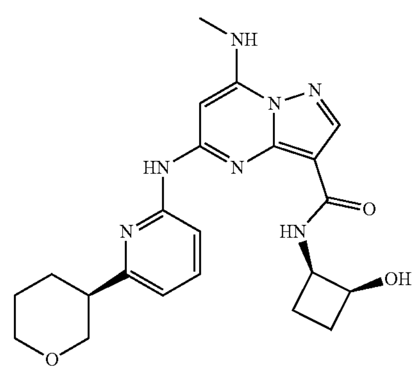 [SMILES: CNc1cc(Nc2cccc([C@@H]3CCCOC3)n2)nc2c(C(=O)N[C@@H]3CC[C@@H]3O)cnn12] |

TABLE 1-continued

Selected Compounds

| Compound | Structure |
|---|---|
| I-606 | 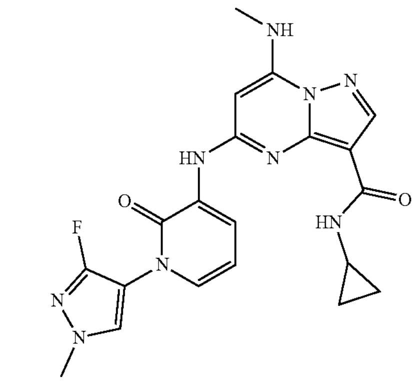 [SMILES: CNc1cc(Nc2cccn(-c3cn(C)nc3F)c2=O)nc2c(C(=O)NC3CC3)cnn12] |
| I-607 | 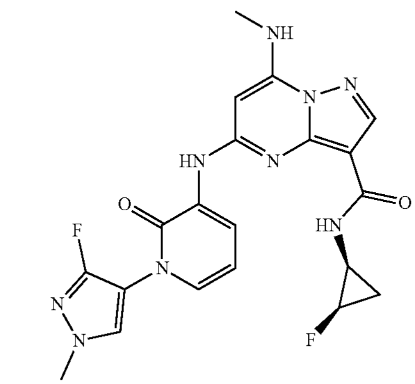 [SMILES: CNc1cc(Nc2cccn(-c3cn(C)nc3F)c2=O)nc2c(C(=O)N[C@H]3C[C@H]3F)cnn12] |
| I-608 | 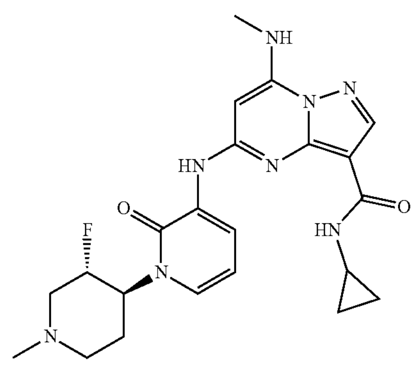 [SMILES: CNc1cc(Nc2cccn([C@H]3CCN(C)C[C@@H]3F)c2=O)nc2c(C(=O)NC3CC3)cnn12] |
| I-609 | 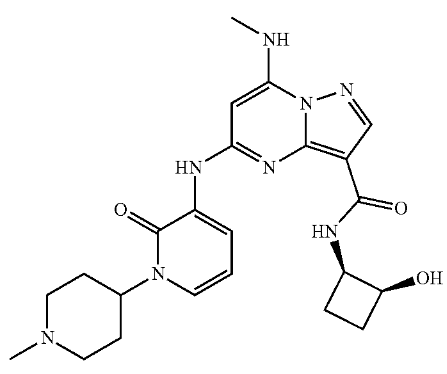 [SMILES: CNc1cc(Nc2cccn(C3CCN(C)CC3)c2=O)nc2c(C(=O)N[C@@H]3CC[C@@H]3O)cnn12] |

387
388
TABLE 1-continued
Selected Compounds
| Compound | Structure |
|---|---|
| I-610 | 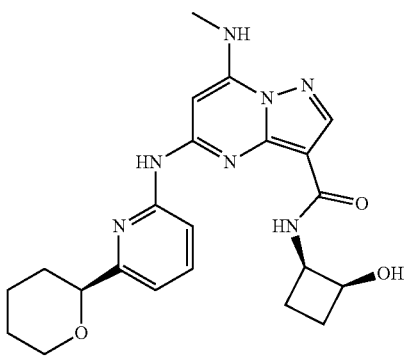 [SMILES: CNc1cc(Nc2cccc([C@@H]3CCCCO3)n2)nc2c(C(=O)N[C@@H]3CC[C@@H]3O)cnn12] |
| I-611 | 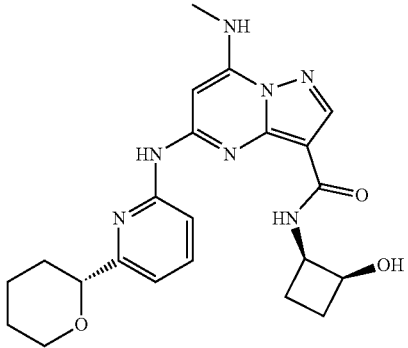 [SMILES: CNc1cc(Nc2cccc([C@H]3CCCCO3)n2)nc2c(C(=O)N[C@@H]3CC[C@@H]3O)cnn12] |
| I-612 | 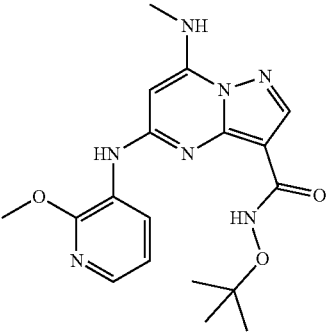 [SMILES: CNc1cc(Nc2cccnc2OC)nc2c(C(=O)NOC(C)(C)C)cnn12] |
| I-613 | 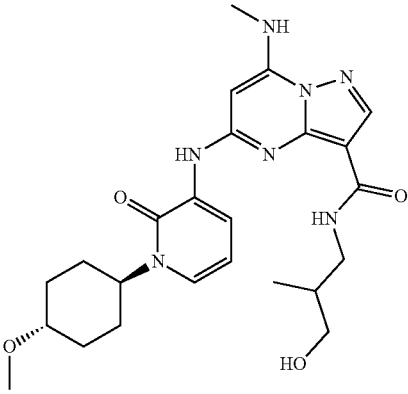 [SMILES: CNc1cc(Nc2cccn([C@H]3CC[C@H](OC)CC3)c2=O)nc2c(C(=O)NCC(C)CO)cnn12] |

TABLE 1-continued

Selected Compounds

| Compound | Structure |
|---|---|
| I-614 | 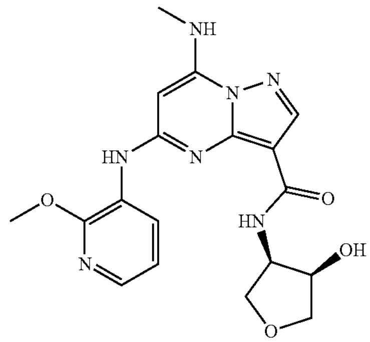 [SMILES: CNc1cc(Nc2cccnc2OC)nc2c(C(=O)N[C@@H]3COC[C@@H]3O)cnn12] |
| I-615 | 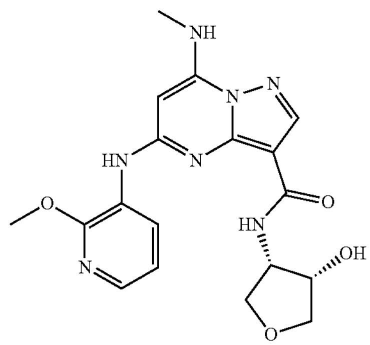 [SMILES: CNc1cc(Nc2cccnc2OC)nc2c(C(=O)N[C@H]3COC[C@H]3O)cnn12] |
| I-616 | 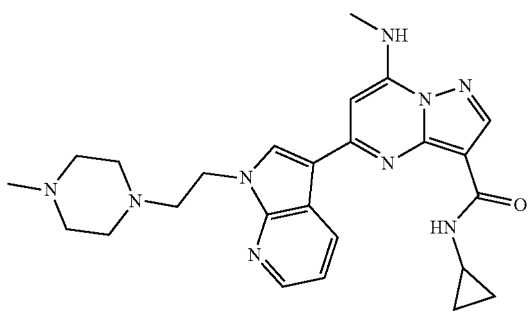 [SMILES: CNc1cc(-c2cn(CCN3CCN(C)CC3)c3ncccc23)nc2c(C(=O)NC3CC3)cnn12] |
| I-617 | 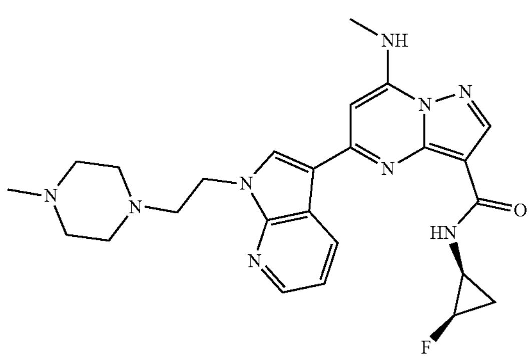 [SMILES: CNc1cc(-c2cn(CCN3CCN(C)CC3)c3ncccc23)nc2c(C(=O)N[C@H]3C[C@H]3F)cnn12] |

TABLE 1-continued

Selected Compounds

| Compound | Structure |
|---|---|
| I-618 | 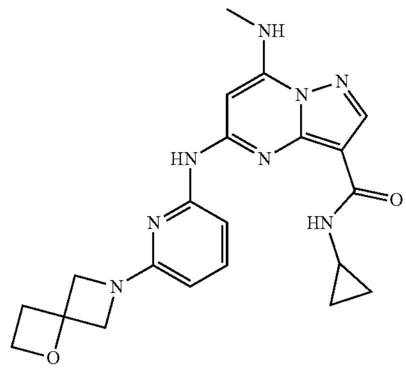 [SMILES: CNc1cc(Nc2cccc(N3CC4(CCO4)C3)n2)nc2c(C(=O)NC3CC3)cnn12] |
| I-619 | 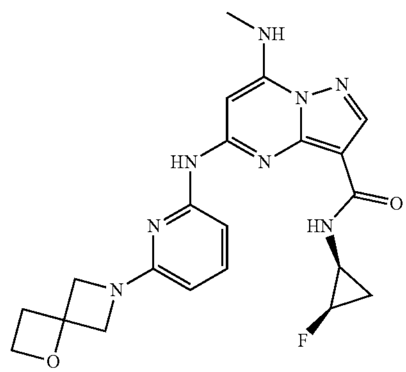 [SMILES: CNc1cc(Nc2cccc(N3CC4(CCO4)C3)n2)nc2c(C(=O)N[C@H]3C[C@H]3F)cnn12] |
| I-620 | 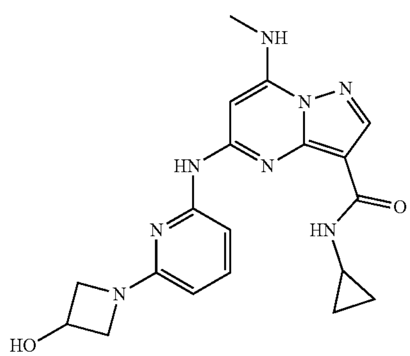 [SMILES: CNc1cc(Nc2cccc(N3CC(O)C3)n2)nc2c(C(=O)NC3CC3)cnn12] |
| I-621 | 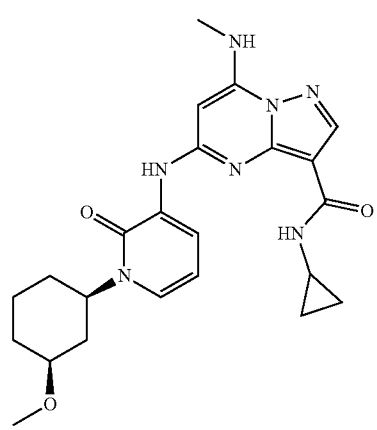 [SMILES: CNc1cc(Nc2cccn([C@@H]3CCC[C@H](OC)C3)c2=O)nc2c(C(=O)NC3CC3)cnn12] |

TABLE 1-continued
Selected Compounds
| Compound | Structure |
|---|---|
| I-622 | 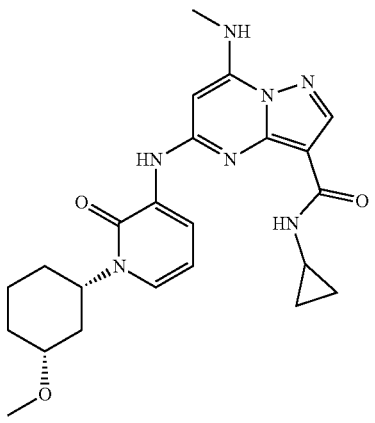 [SMILES: CNc1cc(Nc2cccn([C@H]3CCC[C@@H](OC)C3)c2=O)nc2c(C(=O)NC3CC3)cnn12] |
| I-623 | 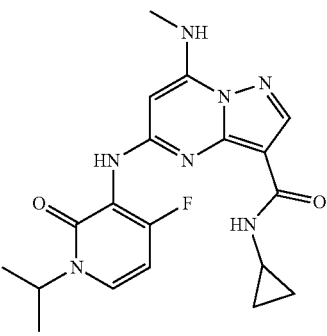 [SMILES: CNc1cc(Nc2c(F)ccn(C(C)C)c2=O)nc2c(C(=O)NC3CC3)cnn12] |
| I-624 | 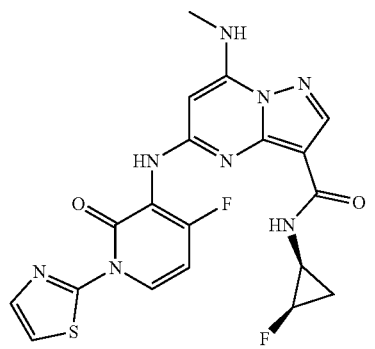 [SMILES: CNc1cc(Nc2c(F)ccn(-c3nccs3)c2=O)nc2c(C(=O)N[C@H]3C[C@H]3F)cnn12] |
| I-625 | 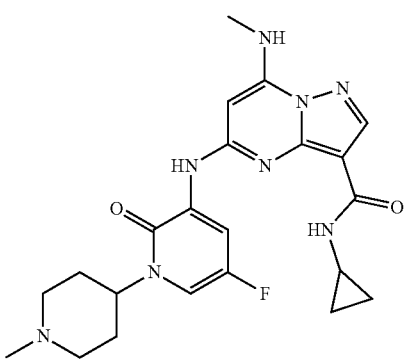 [SMILES: CNc1cc(Nc2cc(F)cn(C3CCN(C)CC3)c2=O)nc2c(C(=O)NC3CC3)cnn12] |

TABLE 1-continued
Selected Compounds
| Compound | Structure |
|---|---|
| I-626 | 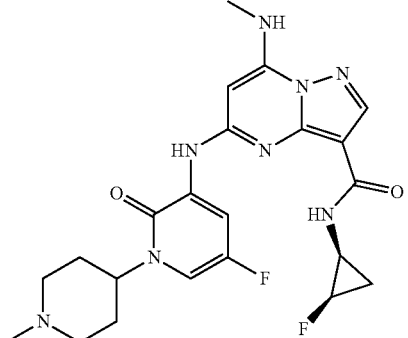 |
| I-627 | 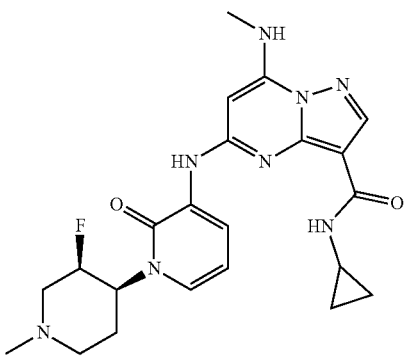 [SMILES: CNc1cc(Nc2cccn([C@H]3CCN(C)C[C@H]3F)c2=O)nc2c(C(=O)NC3CC3)cnn12] |
| I-628 | 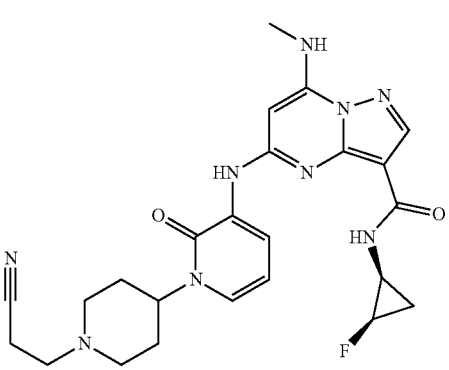 [SMILES: CNc1cc(Nc2cccn(C3CCN(CCC#N)CC3)c2=O)nc2c(C(=O)N[C@H]3C[C@H]3F)cnn12] |
| I-629 | 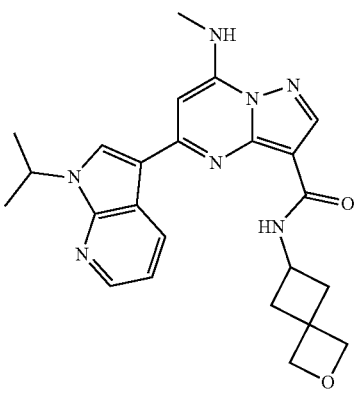 [SMILES: CNc1cc(-c2cn(C(C)C)c3ncccc23)nc2c(C(=O)NC3CC4(COC4)C3)cnn12] |

TABLE 1-continued

| Selected Compounds | |
|---|---|
| Compound | Structure |
| I-630 | |
| I-631 | |
| I-632 | |
| I-633 | |

TABLE 1-continued
Selected Compounds
| Compound | Structure |
|---|---|
| I-634 | 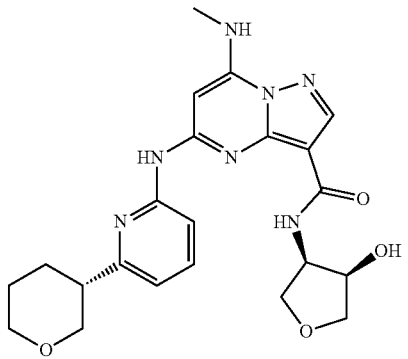 [SMILES: CNc1cc(Nc2cccc([C@H]3CCCOC3)n2)nc2c(C(=O)N[C@@H]3COC[C@@H]3O)cnn12] |
| I-635 | 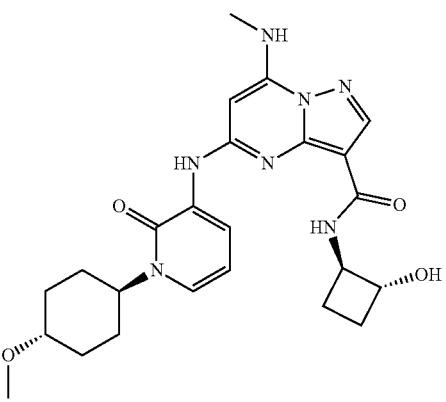 [SMILES: CNc1cc(Nc2cccn([C@H]3CC[C@H](OC)CC3)c2=O)nc2c(C(=O)N[C@@H]3CC[C@H]3O)cnn12] |
| I-636 | 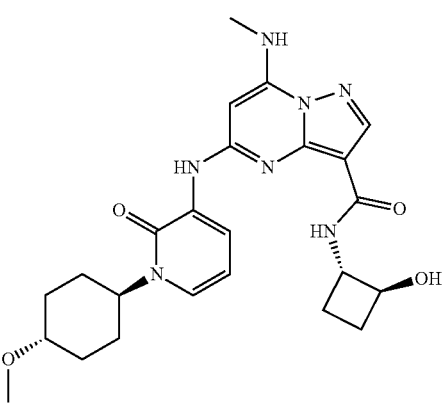 [SMILES: CNc1cc(Nc2cccn([C@H]3CC[C@H](OC)CC3)c2=O)nc2c(C(=O)N[C@H]3CC[C@@H]3O)cnn12] |
| I-637 | 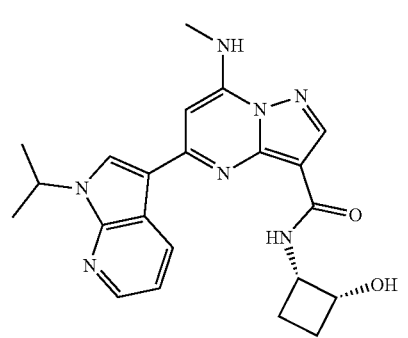 [SMILES: CNc1cc(-c2cn(C(C)C)c3ncccc23)nc2c(C(=O)N[C@H]3CC[C@H]3O)cnn12] |

TABLE 1-continued

Selected Compounds

| Compound | Structure |
|---|---|
| I-638 | 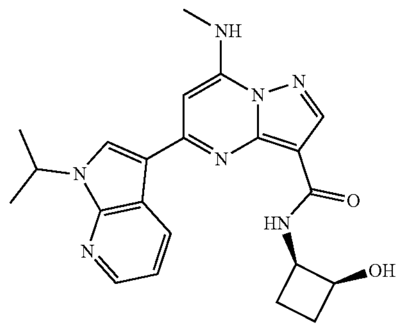 [SMILES: CNc1cc(-c2cn(C(C)C)c3ncccc23)nc2c(C(=O)N[C@@H]3CC[C@@H]3O)cnn12] |
| I-639 | 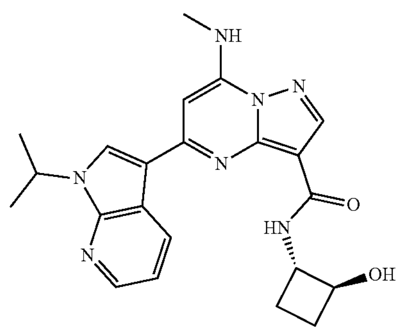 [SMILES: CNc1cc(-c2cn(C(C)C)c3ncccc23)nc2c(C(=O)N[C@H]3CC[C@@H]3O)cnn12] |
| I-640 | 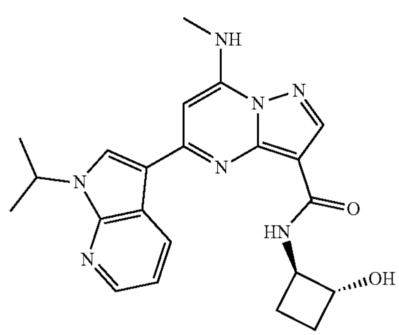 [SMILES: CNc1cc(-c2cn(C(C)C)c3ncccc23)nc2c(C(=O)N[C@@H]3CC[C@H]3O)cnn12] |
| I-641 | 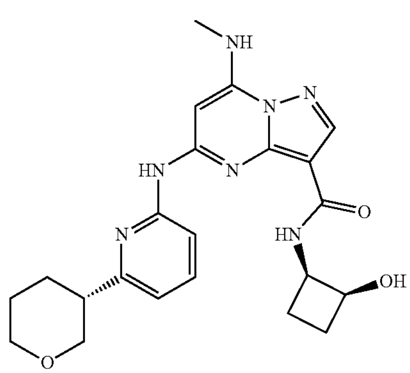 [SMILES: CNc1cc(Nc2cccc([C@H]3CCCOC3)n2)nc2c(C(=O)N[C@@H]3CC[C@@H]3O)cnn12] |

TABLE 1-continued
Selected Compounds
| Compound | Structure |
|---|---|
| I-642 | 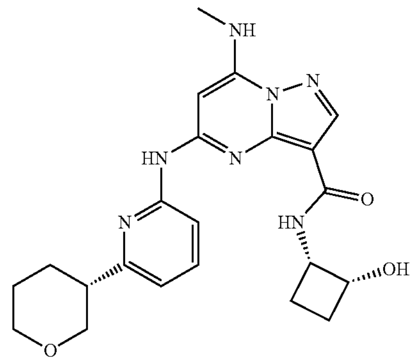 [SMILES: CNc1cc(Nc2cccc([C@H]3CCCOC3)n2)nc2c(C(=O)N[C@H]3CC[C@H]3O)cnn12] |
| I-643 | 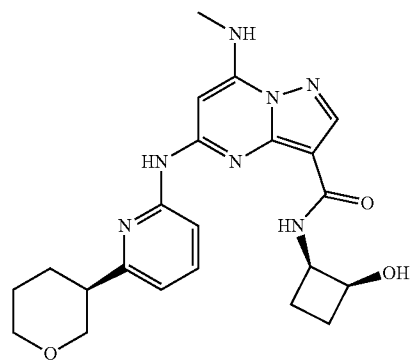 [SMILES: CNc1cc(Nc2cccc([C@@H]3CCCOC3)n2)nc2c(C(=O)N[C@@H]3CC[C@@H]3O)cnn12] |
| I-644 | 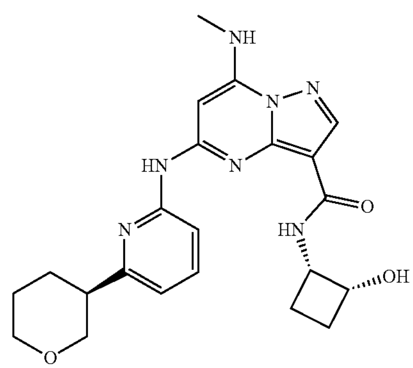 [SMILES: CNc1cc(Nc2cccc([C@@H]3CCCOC3)n2)nc2c(C(=O)N[C@H]3CC[C@H]3O)cnn12] |
| I-645 | 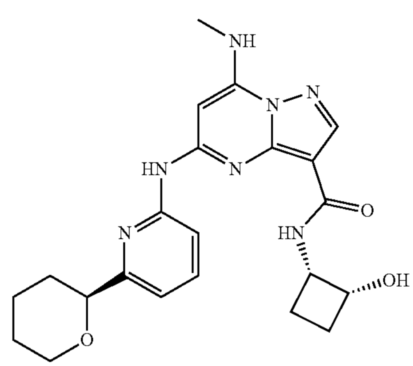 [SMILES: CNc1cc(Nc2cccc([C@@H]3CCCCO3)n2)nc2c(C(=O)N[C@H]3CC[C@H]3O)cnn12] |

TABLE 1-continued

| Selected Compounds | |
|---|---|
| Compound | Structure |
| I-646 | |
| I-647 | |
| I-648 | |
| I-649 | |

TABLE 1-continued

Selected Compounds

| Compound | Structure |
|---|---|
| I-650 | 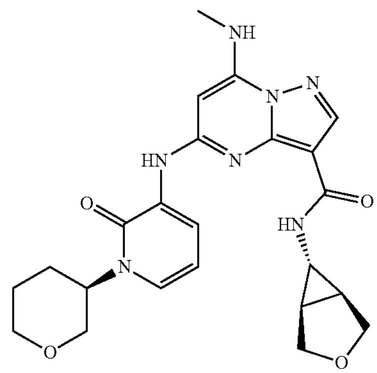 [SMILES: CNc1cc(Nc2cccn([C@@H]3CCCOC3)c2=O)nc2c(C(=O)N[C@H]3[C@@H]4COC[C@@H]43)cnn12] |
| I-651 | 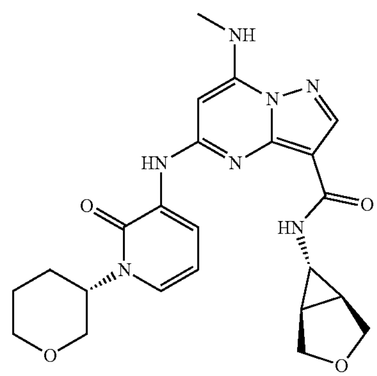 [SMILES: CNc1cc(Nc2cccn([C@H]3CCCOC3)c2=O)nc2c(C(=O)N[C@H]3[C@@H]4COC[C@@H]43)cnn12] |
| I-652 | 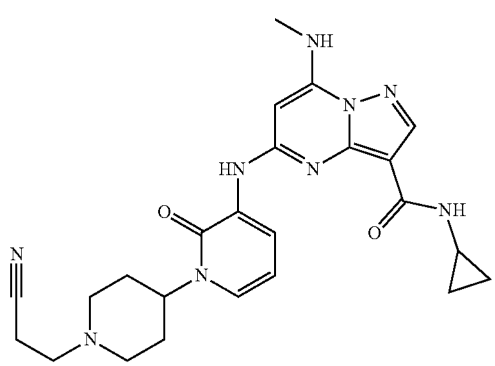 [SMILES: CNc1cc(Nc2cccn(C3CCN(CCC#N)CC3)c2=O)nc2c(C(=O)NC3CC3)cnn12] |
| I-653 | 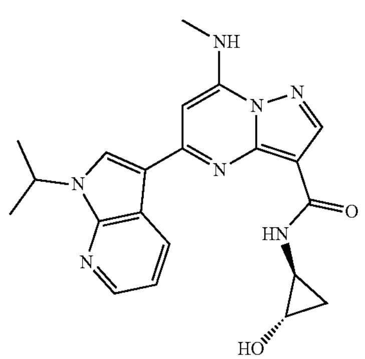 [SMILES: CNc1cc(-c2cn(C(C)C)c3ncccc23)nc2c(C(=O)N[C@H]3C[C@@H]3O)cnn12] |

TABLE 1-continued

Selected Compounds

| Compound | Structure |
|---|---|
| I-654 | 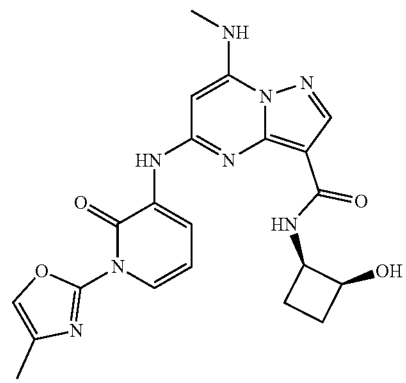 [SMILES: CNc1cc(Nc2cccn(-c3nc(C)co3)c2=O)nc2c(C(=O)N[C@@H]3CC[C@@H]3O)cnn12] |
| I-655 | 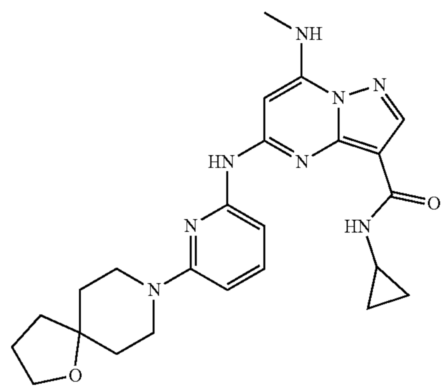 [SMILES: CNc1cc(Nc2cccc(N3CCC4(CCCO4)CC3)n2)nc2c(C(=O)NC3CC3)cnn12] |
| I-656 | 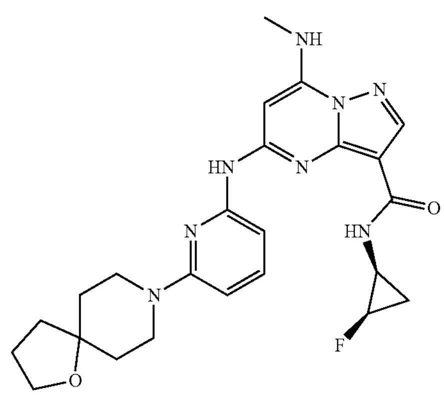 [SMILES: CNc1cc(Nc2cccc(N3CCC4(CCCO4)CC3)n2)nc2c(C(=O)N[C@H]3C[C@H]3F)cnn12] |
| I-657 | 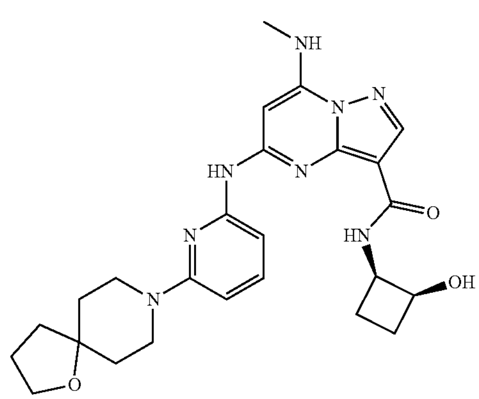 [SMILES: CNc1cc(Nc2cccc(N3CCC4(CCCO4)CC3)n2)nc2c(C(=O)N[C@@H]3CC[C@@H]3O)cnn12] |

TABLE 1-continued

Selected Compounds

| Compound | Structure |
|---|---|
| I-658 | 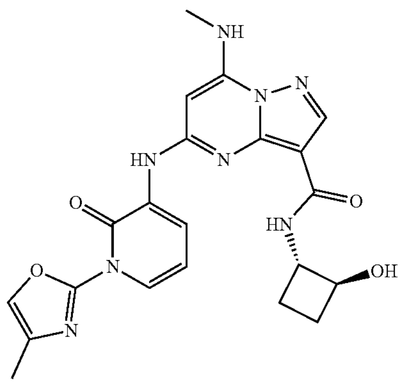 [SMILES: CNc1cc(Nc2cccn(-c3nc(C)co3)c2=O)nc2c(C(=O)N[C@H]3CC[C@@H]3O)cnn12] |
| I-659 | 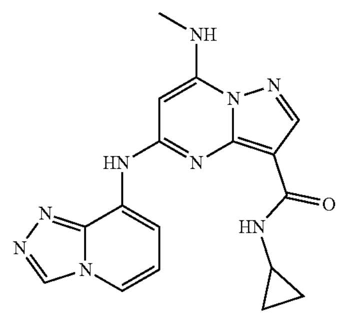 [SMILES: CNc1cc(Nc2cccn3cnnc23)nc2c(C(=O)NC3CC3)cnn12] |
| I-660 | 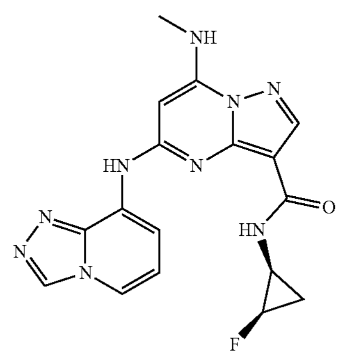 [SMILES: CNc1cc(Nc2cccn3cnnc23)nc2c(C(=O)N[C@H]3C[C@H]3F)cnn12] |
| I-661 | 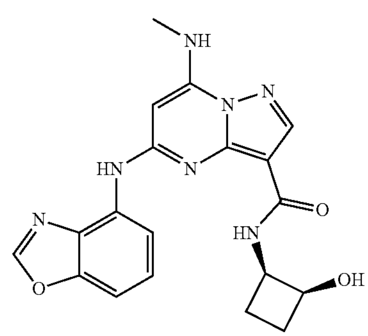 [SMILES: CNc1cc(Nc2cccc3ocnc23)nc2c(C(=O)N[C@@H]3CC[C@@H]3O)cnn12] |

TABLE 1-continued

Selected Compounds

| Compound | Structure |
| --- | --- |
| I-662 | 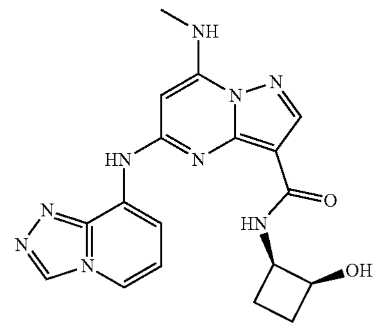 |
| I-663 | 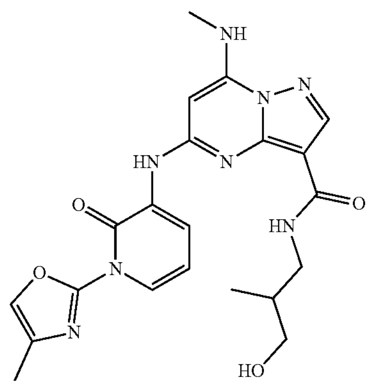 [SMILES: CNc1cc(Nc2cccn(-c3nc(C)co3)c2=O)nc2c(C(=O)NCC(C)CO)cnn12] |
| I-664 | 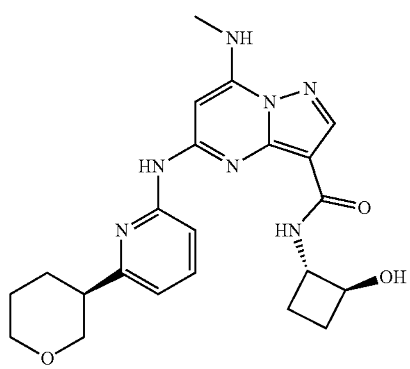 [SMILES: CNc1cc(Nc2cccc([C@@H]3CCCOC3)n2)nc2c(C(=O)N[C@H]3CC[C@@H]3O)cnn12] |
| I-665 | 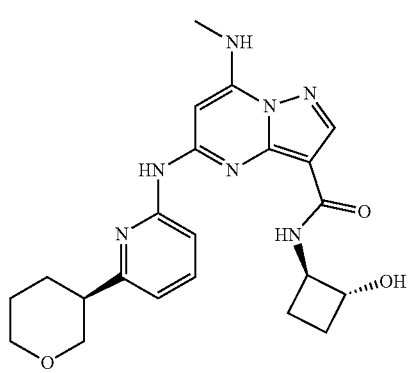 [SMILES: CNc1cc(Nc2cccc([C@@H]3CCCOC3)n2)nc2c(C(=O)N[C@@H]3CC[C@H]3O)cnn12] |

TABLE 1-continued

| Compound | Structure |
|---|---|
| I-666 | 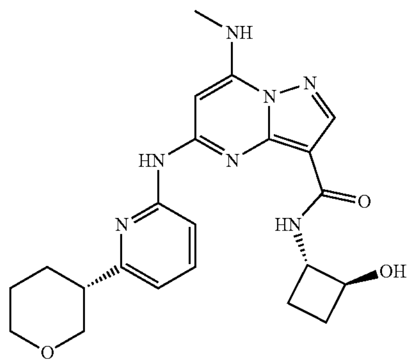 [SMILES: CNc1cc(Nc2cccc([C@H]3CCCOC3)n2)nc2c(C(=O)N[C@H]3CC[C@@H]3O)cnn12] |
| I-667 | 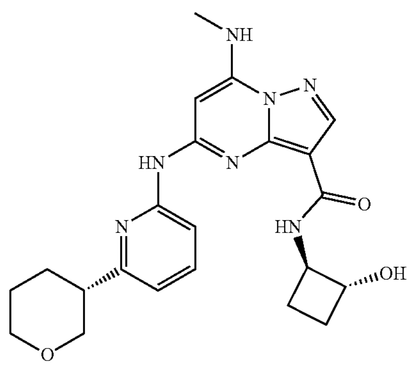 [SMILES: CNc1cc(Nc2cccc([C@H]3CCCOC3)n2)nc2c(C(=O)N[C@@H]3CC[C@H]3O)cnn12] |
| I-668 | 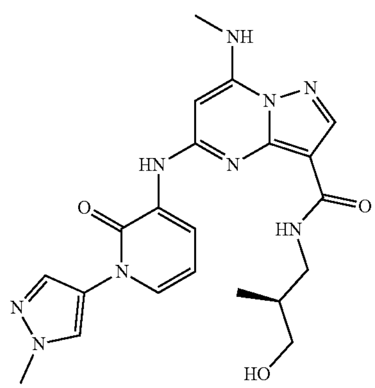 [SMILES: CNc1cc(Nc2cccn(-c3cnn(C)c3)c2=O)nc2c(C(=O)NC[C@H](C)CO)cnn12] |
| I-669 | 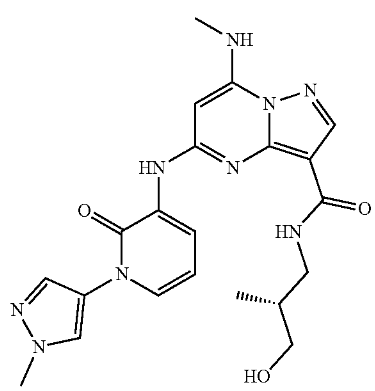 |

TABLE 1-continued

Selected Compounds

| Compound | Structure |
|---|---|
| I-670 | 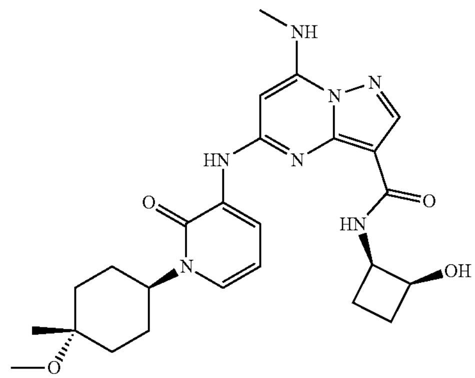 [SMILES: CNc1cc(Nc2cccn([C@H]3CC[C@](C)(OC)CC3)c2=O)nc2c(C(=O)N[C@@H]3CC[C@@H]3O)cnn12] |
| I-671 | 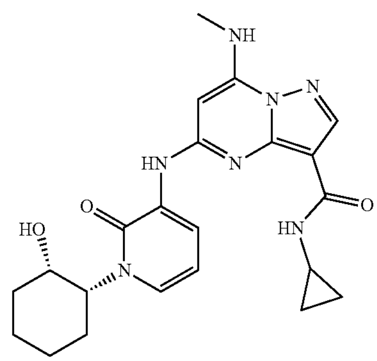 [SMILES: CNc1cc(Nc2cccn([C@@H]3CCCC[C@@H]3O)c2=O)nc2c(C(=O)NC3CC3)cnn12] |
| I-672 | 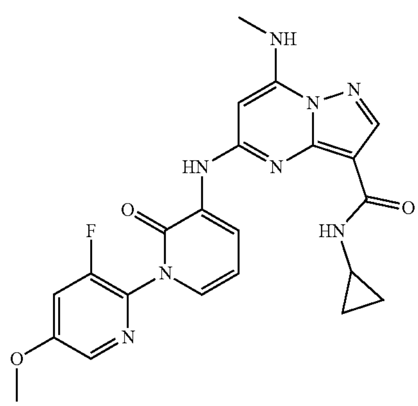 [SMILES: CNc1cc(Nc2cccn(-c3ncc(OC)cc3F)c2=O)nc2c(C(=O)NC3CC3)cnn12] |
| I-673 | 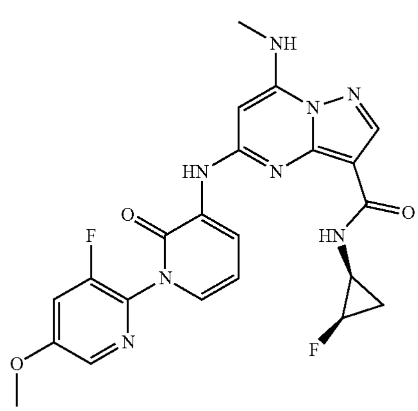 [SMILES: CNc1cc(Nc2cccn(-c3ncc(OC)cc3F)c2=O)nc2c(C(=O)N[C@H]3C[C@H]3F)cnn12] |

TABLE 1-continued
| Selected Compounds | |
|---|---|
| Compound | Structure |
| I-674 | 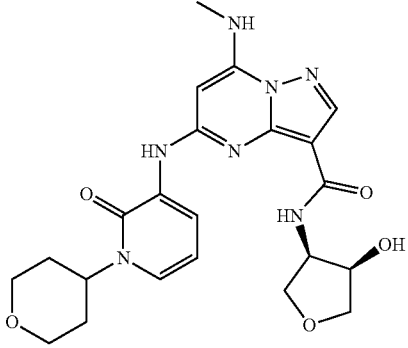 [SMILES: CNc1cc(Nc2cccn(C3CCOCC3)c2=O)nc2c(C(=O)N[C@@H]3COC[C@@H]3O)cnn12] |
| I-675 | 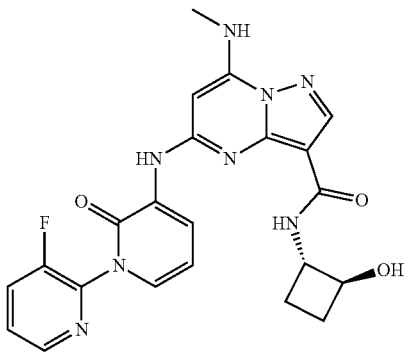 [SMILES: CNc1cc(Nc2cccn(-c3ncccc3F)c2=O)nc2c(C(=O)N[C@H]3CC[C@@H]3O)cnn12] |
| I-676 | 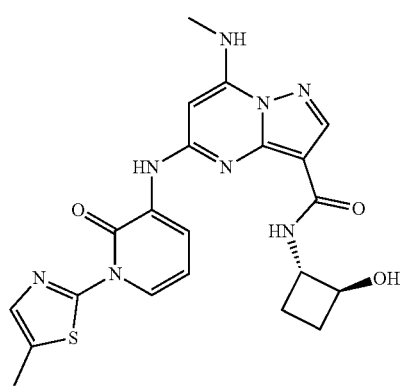 [SMILES: CNc1cc(Nc2cccn(-c3ncc(C)s3)c2=O)nc2c(C(=O)N[C@H]3CC[C@@H]3O)cnn12] |
| I-677 | 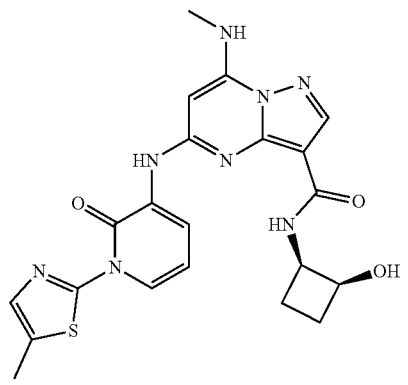 [SMILES: CNc1cc(Nc2cccn(-c3ncc(C)s3)c2=O)nc2c(C(=O)N[C@@H]3CC[C@@H]3O)cnn12] |

TABLE 1-continued
| Selected Compounds | |
|---|---|
| Compound | Structure |
| I-678 | 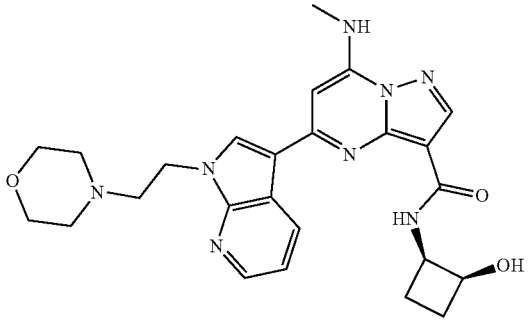 [SMILES: CNc1cc(-c2cn(CCN3CCOCC3)c3ncccc23)nc2c(C(=O)N[C@@H]3CC[C@@H]3O)cnn12] |
| I-679 | 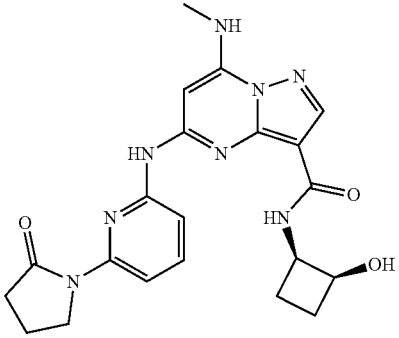 [SMILES: CNc1cc(Nc2cccc(N3CCCC3=O)n2)nc2c(C(=O)N[C@@H]3CC[C@@H]3O)cnn12] |
| I-680 | 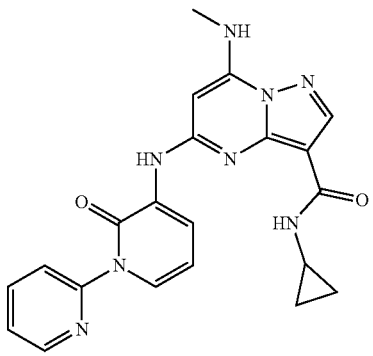 [SMILES: CNc1cc(Nc2cccn(-c3ccccn3)c2=O)nc2c(C(=O)NC3CC3)cnn12] |
| I-681 | 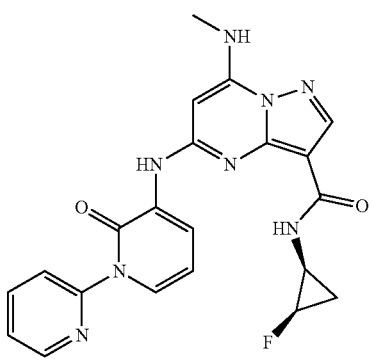 [SMILES: CNc1cc(Nc2cccn(-c3ccccn3)c2=O)nc2c(C(=O)N[C@H]3C[C@H]3F)cnn12] |

TABLE 1-continued
| Selected Compounds | |
|---|---|
| Compound | Structure |
| I-682 | 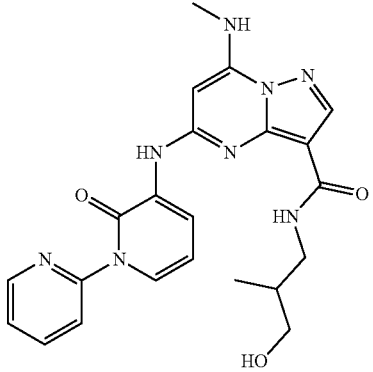 [SMILES: CNc1cc(Nc2cccn(-c3ccccn3)c2=O)nc2c(C(=O)NCC(C)CO)cnn12] |
| I-683 | 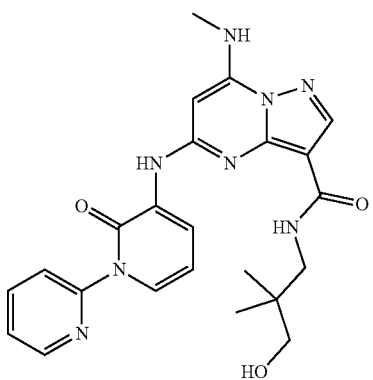 [SMILES: CNc1cc(Nc2cccn(-c3ccccn3)c2=O)nc2c(C(=O)NCC(C)(C)CO)cnn12] |
| I-684 | 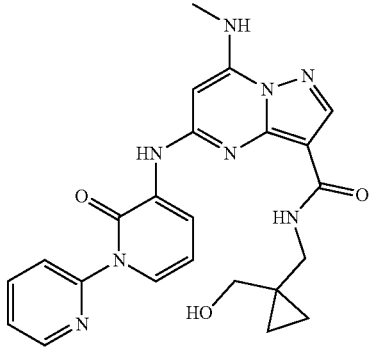 [SMILES: CNc1cc(Nc2cccn(-c3ccccn3)c2=O)nc2c(C(=O)NCC3(CO)CC3)cnn12] |
| I-685 | 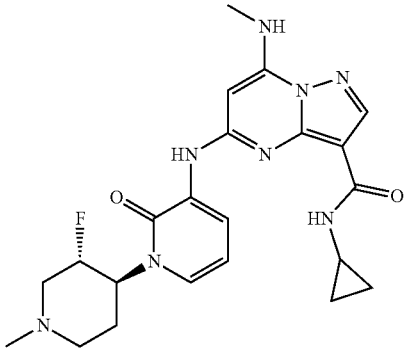 [SMILES: CNc1cc(Nc2cccn([C@H]3CCN(C)C[C@@H]3F)c2=O)nc2c(C(=O)NC3CC3)cnn12] |

TABLE 1-continued

| Compound | Structure |
|---|---|
| I-686 | 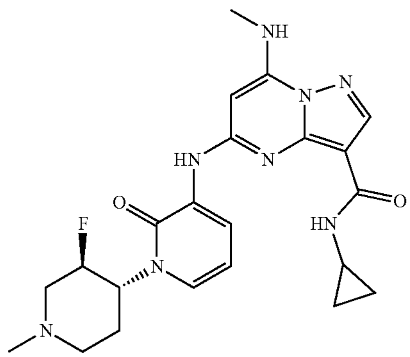 [SMILES: CNc1cc(Nc2cccn([C@@H]3CCN(C)C[C@H]3F)c2=O)nc2c(C(=O)NC3CC3)cnn12] |
| I-687 | 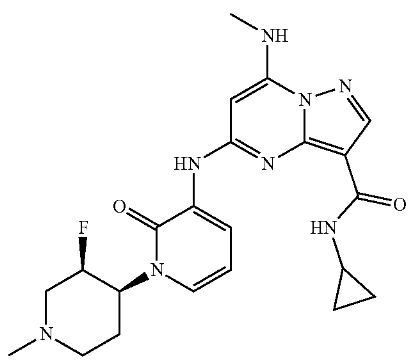 [SMILES: CNc1cc(Nc2cccn([C@H]3CCN(C)C[C@H]3F)c2=O)nc2c(C(=O)NC3CC3)cnn12] |
| I-688 | 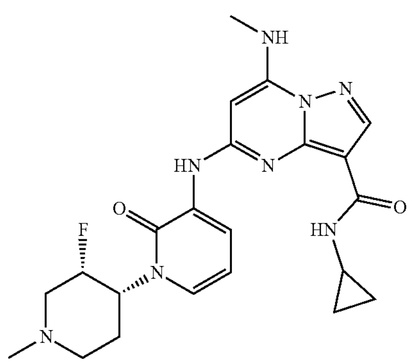 [SMILES: CNc1cc(Nc2cccn([C@@H]3CCN(C)C[C@@H]3F)c2=O)nc2c(C(=O)NC3CC3)cnn12] |
| I-689 | 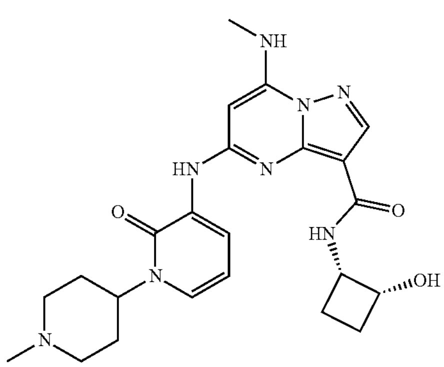 [SMILES: CNc1cc(Nc2cccn(C3CCN(C)CC3)c2=O)nc2c(C(=O)N[C@H]3CC[C@H]3O)cnn12] |

TABLE 1-continued
| Selected Compounds | |
|---|---|
| Compound | Structure |
| I-690 | 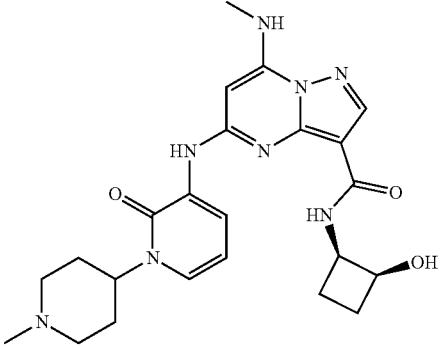 [SMILES: CNc1cc(Nc2cccn(C3CCN(C)CC3)c2=O)nc2c(C(=O)N[C@@H]3CC[C@@H]3O)cnn12] |
| I-691 | 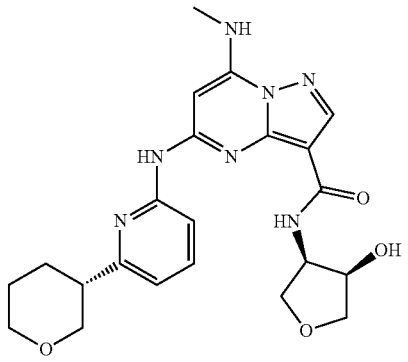 [SMILES: CNc1cc(Nc2cccc([C@H]3CCCOC3)n2)nc2c(C(=O)N[C@@H]3COC[C@@H]3O)cnn12] |
| I-692 | 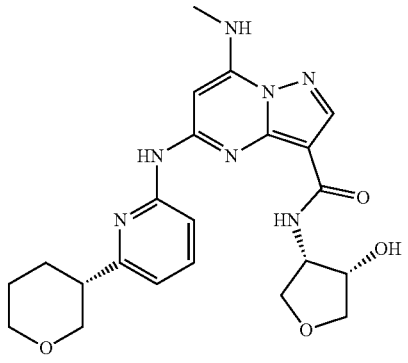 [SMILES: CNc1cc(Nc2cccc([C@H]3CCCOC3)n2)nc2c(C(=O)N[C@H]3COC[C@H]3O)cnn12] |
| I-693 | 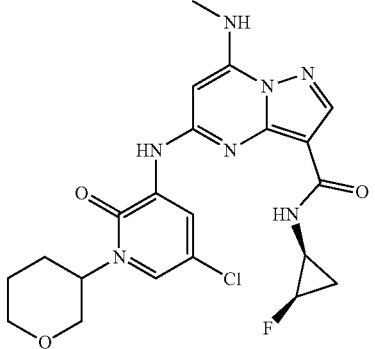 |

TABLE 1-continued

| Selected Compounds | |
|---|---|
| Compound | Structure |
| I-694 | |
| I-695 | |
| I-696 | |
| I-697 | |

TABLE 1-continued
Selected Compounds
| Compound | Structure |
|---|---|
| I-698 | 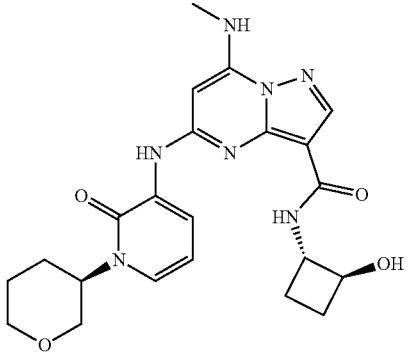 [SMILES: CNc1cc(Nc2cccn([C@@H]3CCCOC3)c2=O)nc2c(C(=O)N[C@H]3CC[C@@H]3O)cnn12] |
| I-699 | 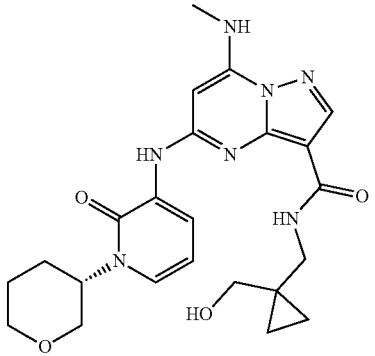 [SMILES: CNc1cc(Nc2cccn([C@H]3CCCOC3)c2=O)nc2c(C(=O)NCC3(CO)CC3)cnn12] |
| I-700 | 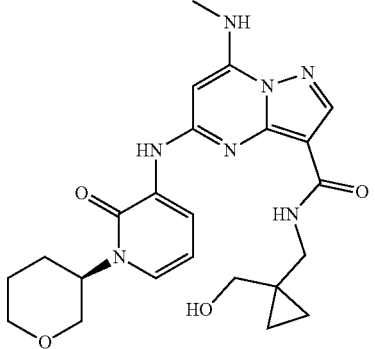 [SMILES: CNc1cc(Nc2cccn([C@@H]3CCCOC3)c2=O)nc2c(C(=O)NCC3(CO)CC3)cnn12] |
| I-701 | 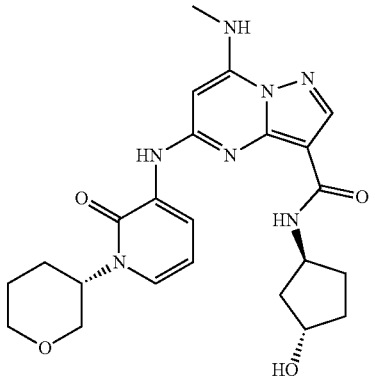 [SMILES: CNc1cc(Nc2cccn([C@H]3CCCOC3)c2=O)nc2c(C(=O)N[C@H]3CC[C@H](O)C3)cnn12] |

TABLE 1-continued
| Selected Compounds | |
|---|---|
| Compound | Structure |
| I-702 | 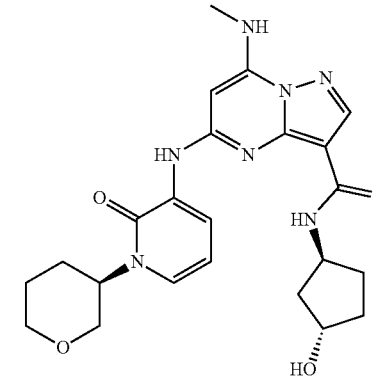 |
| I-703 | 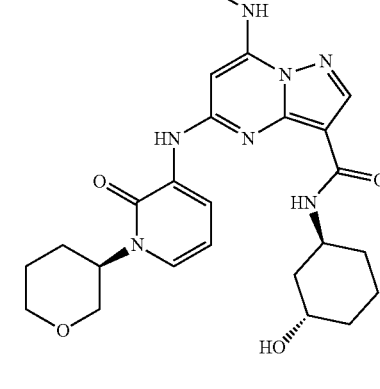 |
| I-704 | 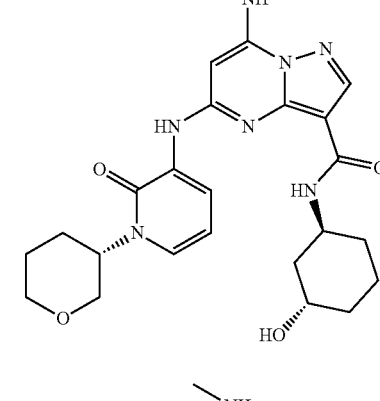 |
| I-705 | 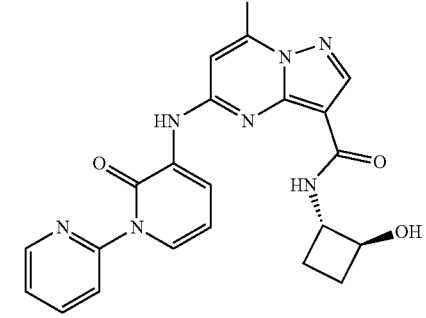 |

TABLE 1-continued

Selected Compounds

| Compound | Structure |
|---|---|
| I-706 | 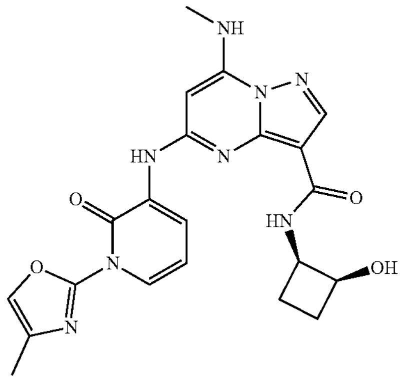 [SMILES: CNc1cc(Nc2cccn(-c3nc(C)co3)c2=O)nc2c(C(=O)N[C@@H]3CC[C@@H]3O)cnn12] |
| I-707 | 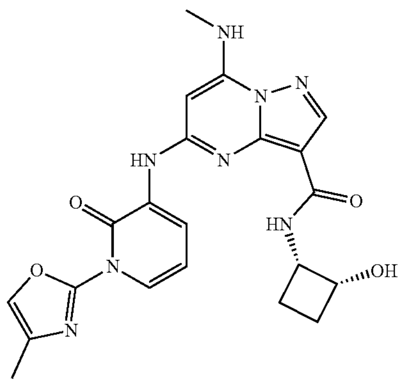 [SMILES: CNc1cc(Nc2cccn(-c3nc(C)co3)c2=O)nc2c(C(=O)N[C@H]3CC[C@H]3O)cnn12] |
| I-708 | 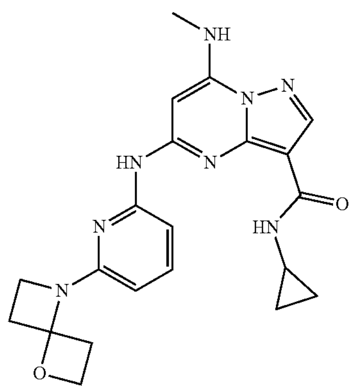 [SMILES: CNc1cc(Nc2cccc(N3CCC34CCO4)n2)nc2c(C(=O)NC3CC3)cnn12] |
| I-709 | 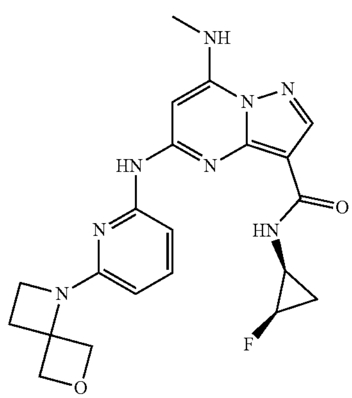 [SMILES: CNc1cc(Nc2cccc(N3CCC34COC4)n2)nc2c(C(=O)N[C@H]3C[C@H]3F)cnn12] |

TABLE 1-continued

| Compound | Structure |
|---|---|
| I-710 | 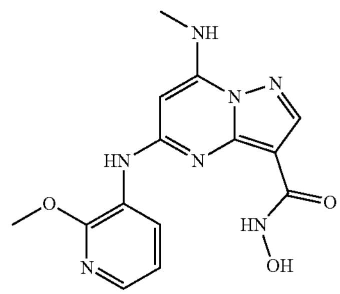 [SMILES: CNc1cc(Nc2cccnc2OC)nc2c(C(=O)NO)cnn12] |
| I-711 | 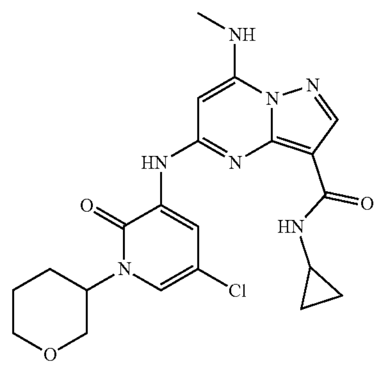 [SMILES: CNc1cc(Nc2cc(Cl)cn(C3CCCOC3)c2=O)nc2c(C(=O)NC3CC3)cnn12] |
| I-712 | 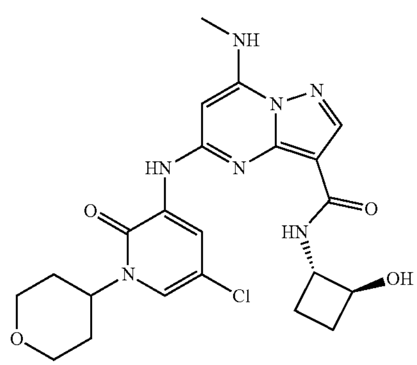 [SMILES: CNc1cc(Nc2cc(Cl)cn(C3CCOCC3)c2=O)nc2c(C(=O)N[C@H]3CC[C@@H]3O)cnn12] |
| I-713 | 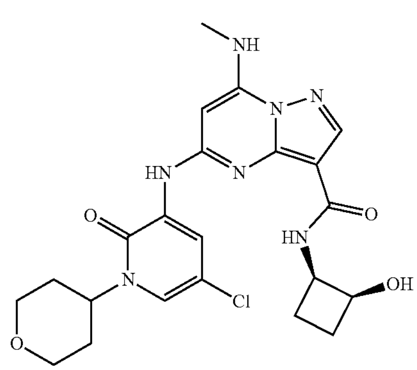 [SMILES: CNc1cc(Nc2cc(Cl)cn(C3CCOCC3)c2=O)nc2c(C(=O)N[C@@H]3CC[C@@H]3O)cnn12] |

TABLE 1-continued

| Selected Compounds | |
|---|---|
| Compound | Structure |
| I-714 | |
| I-715 | |
| I-716 | |
| I-717 | |

TABLE 1-continued

Selected Compounds

| Compound | Structure |
|---|---|
| I-718 | 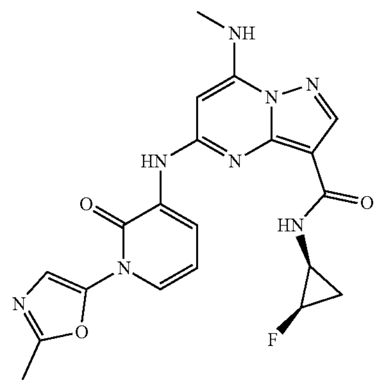 [SMILES: CNc1cc(Nc2cccn(-c3cnc(C)o3)c2=O)nc2c(C(=O)N[C@H]3C[C@H]3F)cnn12] |
| I-719 | 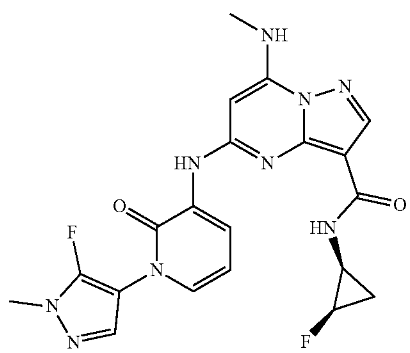 [SMILES: CNc1cc(Nc2cccn(-c3cnn(C)c3F)c2=O)nc2c(C(=O)N[C@H]3C[C@H]3F)cnn12] |
| I-720 | 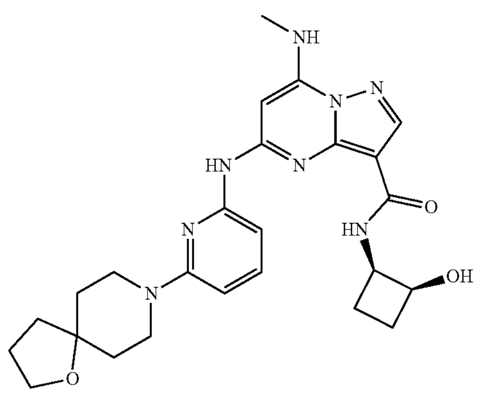 [SMILES: CNc1cc(Nc2cccc(N3CCC4(CCCO4)CC3)n2)nc2c(C(=O)N[C@@H]3CC[C@@H]3O)cnn12] |
| I-721 | 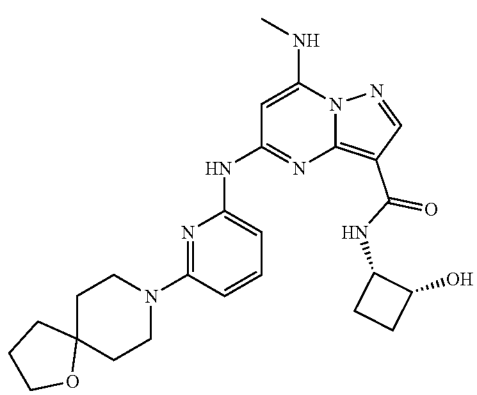 [SMILES: CNc1cc(Nc2cccc(N3CCC4(CCCO4)CC3)n2)nc2c(C(=O)N[C@H]3CC[C@H]3O)cnn12] |

TABLE 1-continued
Selected Compounds
| Compound | Structure |
|---|---|
| I-722 | 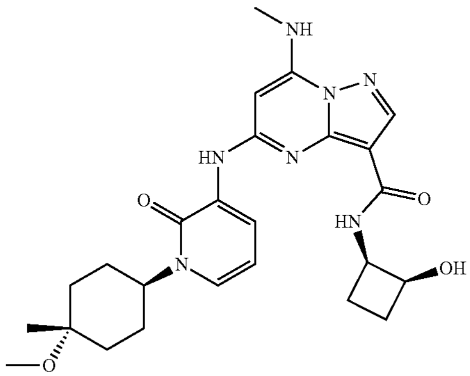 [SMILES: CNc1cc(Nc2cccn([C@H]3CC[C@](C)(OC)CC3)c2=O)nc2c(C(=O)N[C@@H]3CC[C@@H]3O)cnn12] |
| I-723 | 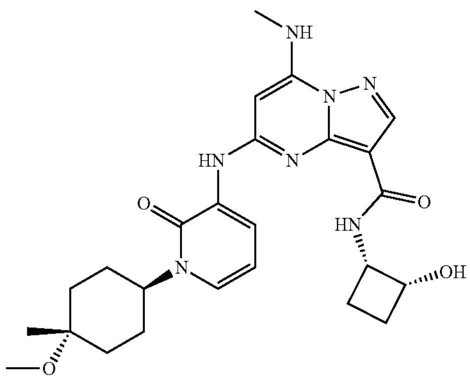 [SMILES: CNc1cc(Nc2cccn([C@H]3CC[C@](C)(OC)CC3)c2=O)nc2c(C(=O)N[C@H]3CC[C@H]3O)cnn12] |
| I-724 | 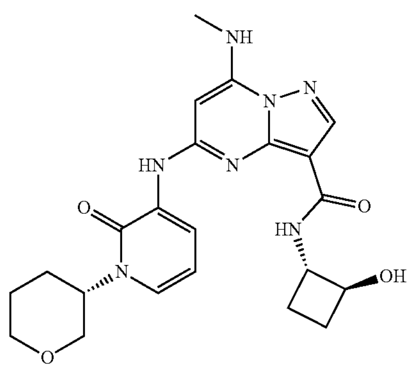 [SMILES: CNc1cc(Nc2cccn([C@H]3CCCOC3)c2=O)nc2c(C(=O)N[C@H]3CC[C@@H]3O)cnn12] |
| I-725 | 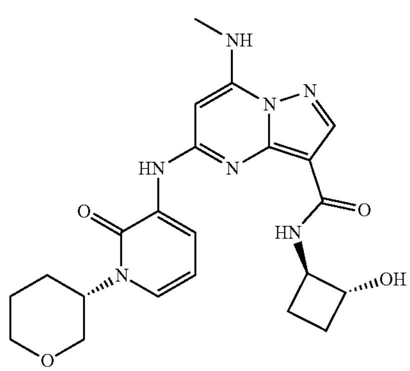 [SMILES: CNc1cc(Nc2cccn([C@H]3CCCOC3)c2=O)nc2c(C(=O)N[C@@H]3CC[C@H]3O)cnn12] |

445
446
TABLE 1-continued
| Selected Compounds | |
|---|---|
| Compound | Structure |
| I-726 | 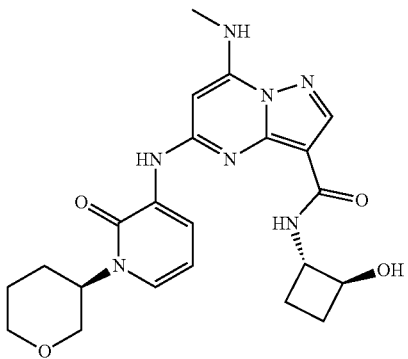 |
| I-727 | 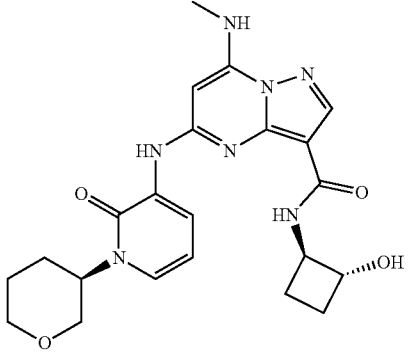 [SMILES: CNc1cc(Nc2cccn([C@@H]3CCCOC3)c2=O)nc2c(C(=O)N[C@@H]3CC[C@H]3O)cnn12] |
| I-728 | 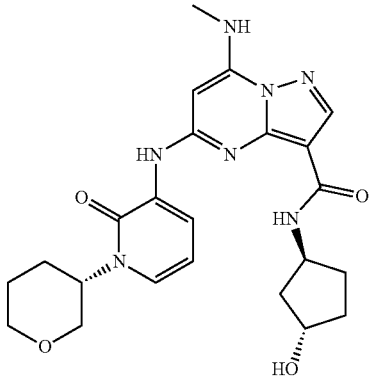 [SMILES: CNc1cc(Nc2cccn([C@H]3CCCOC3)c2=O)nc2c(C(=O)N[C@H]3CC[C@H](O)C3)cnn12] |
| I-729 | 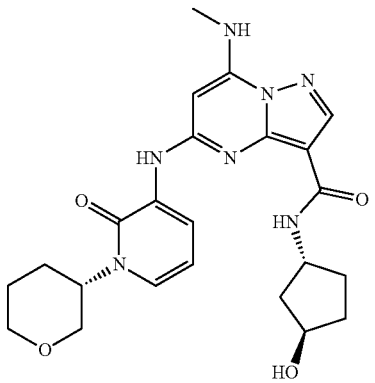 [SMILES: CNc1cc(Nc2cccn([C@H]3CCCOC3)c2=O)nc2c(C(=O)N[C@@H]3CC[C@@H](O)C3)cnn12] |

TABLE 1-continued
Selected Compounds
| Compound | Structure |
|---|---|
| I-730 | 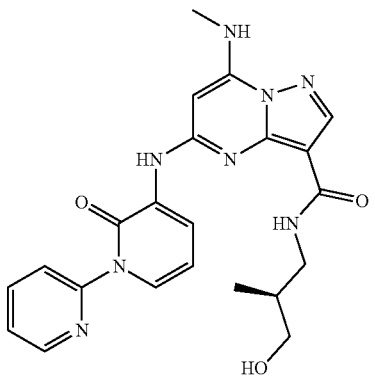 [SMILES: CNc1cc(Nc2cccn(-c3ccccn3)c2=O)nc2c(C(=O)NC[C@H](C)CO)cnn12] |
| I-731 | 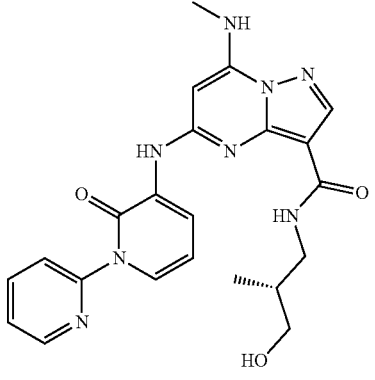 [SMILES: CNc1cc(Nc2cccn(-c3ccccn3)c2=O)nc2c(C(=O)NC[C@@H](C)CO)cnn12] |
| I-732 | 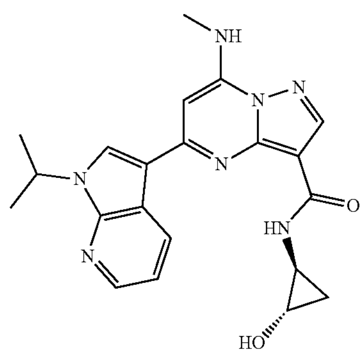 [SMILES: CNc1cc(-c2cn(C(C)C)c3ncccc23)nc2c(C(=O)N[C@H]3C[C@@H]3O)cnn12] |
| I-733 | 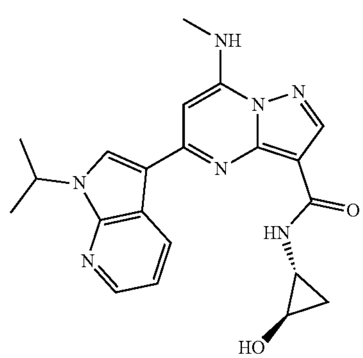 [SMILES: CNc1cc(-c2cn(C(C)C)c3ncccc23)nc2c(C(=O)N[C@@H]3C[C@H]3O)cnn12] |

TABLE 1-continued

Selected Compounds

| Compound | Structure |
|---|---|
| I-734 | 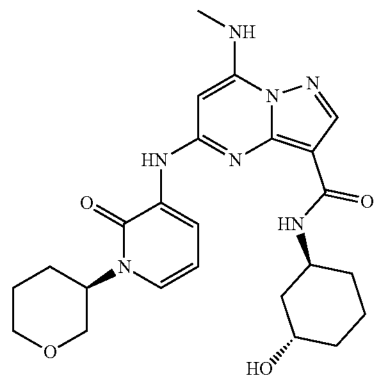 [SMILES: CNc1cc(Nc2cccn([C@@H]3CCCOC3)c2=O)nc2c(C(=O)N[C@H]3CCC[C@H](O)C3)cnn12] |
| I-735 | 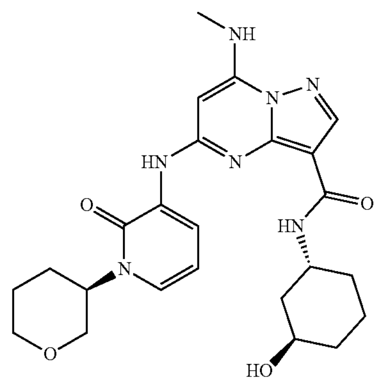 [SMILES: CNc1cc(Nc2cccn([C@@H]3CCCOC3)c2=O)nc2c(C(=O)N[C@@H]3CCC[C@@H](O)C3)cnn12] |
| I-736 | 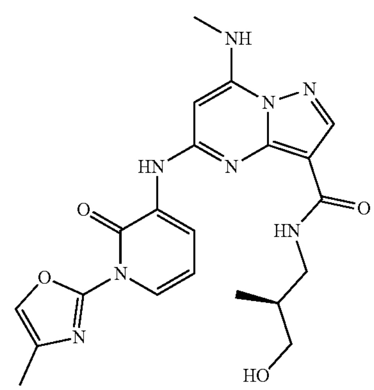 [SMILES: CNc1cc(Nc2cccn(-c3nc(C)co3)c2=O)nc2c(C(=O)NC[C@H](C)CO)cnn12] |
| I-737 | 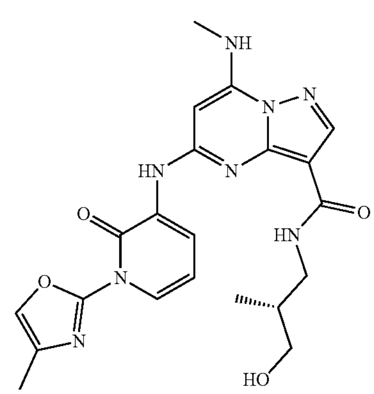 [SMILES: CNc1cc(Nc2cccn(-c3nc(C)co3)c2=O)nc2c(C(=O)NC[C@@H](C)CO)cnn12] |

TABLE 1-continued

Selected Compounds

| Compound | Structure |
|---|---|
| I-738 | 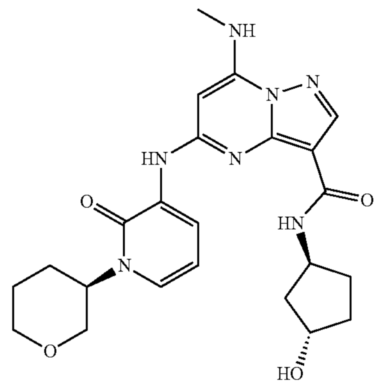 [SMILES: CNc1cc(Nc2cccn([C@@H]3CCCOC3)c2=O)nc2c(C(=O)N[C@H]3CC[C@H](O)C3)cnn12] |
| I-739 | 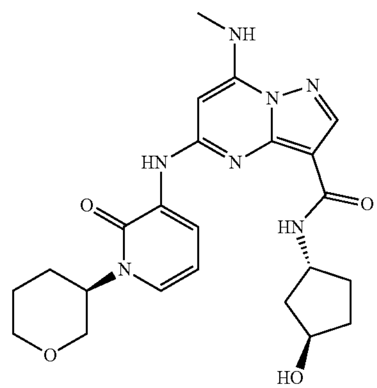 [SMILES: CNc1cc(Nc2cccn([C@@H]3CCCOC3)c2=O)nc2c(C(=O)N[C@@H]3CC[C@@H](O)C3)cnn12] |
| I-740 | 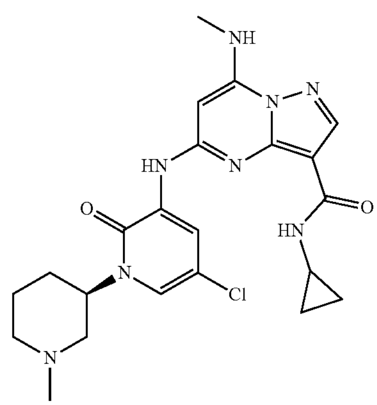 [SMILES: CNc1cc(Nc2cc(Cl)cn([C@@H]3CCCN(C)C3)c2=O)nc2c(C(=O)NC3CC3)cnn12] |
| I-741 | 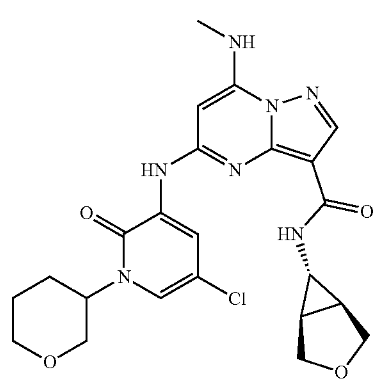 [SMILES: CNc1cc(Nc2cc(Cl)cn(C3CCCOC3)c2=O)nc2c(C(=O)N[C@H]3[C@@H]4COC[C@@H]43)cnn12] |

TABLE 1-continued

| Selected Compounds | |
|---|---|
| Compound | Structure |
| I-742 | |
| I-743 | |
| I-744 | |
| I-745 | |

TABLE 1-continued
Selected Compounds
| Compound | Structure |
|---|---|
| I-746 | 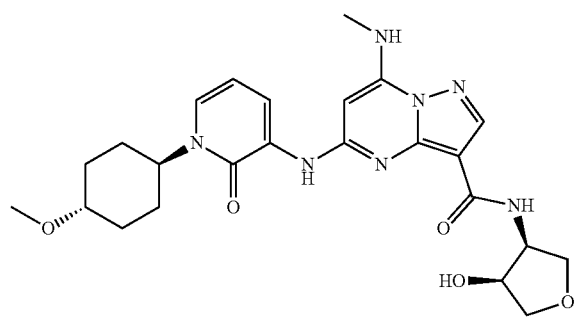 [SMILES: CNc1cc(Nc2cccn([C@H]3CC[C@H](OC)CC3)c2=O)nc2c(C(=O)N[C@H]3COC[C@H]3O)cnn12] |
| I-747 | 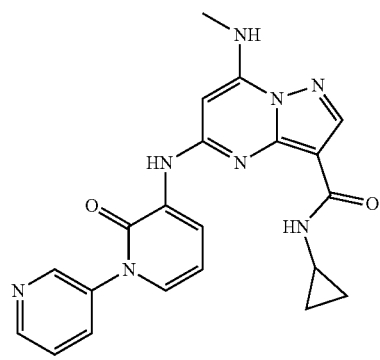 [SMILES: CNc1cc(Nc2cccn(-c3cccnc3)c2=O)nc2c(C(=O)NC3CC3)cnn12] |
| I-748 | 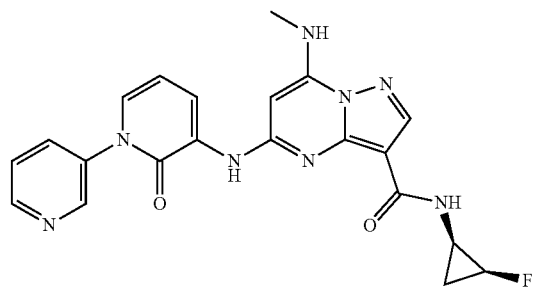 [SMILES: CNc1cc(Nc2cccn(-c3cccnc3)c2=O)nc2c(C(=O)N[C@@H]3C[C@@H]3F)cnn12] |
| I-749 | 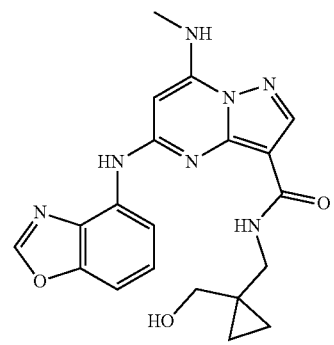 [SMILES: CNc1cc(Nc2cccc3ocnc23)nc2c(C(=O)NCC3(CO)CC3)cnn12] |

TABLE 1-continued

Selected Compounds

| Compound | Structure |
|---|---|
| I-750 | 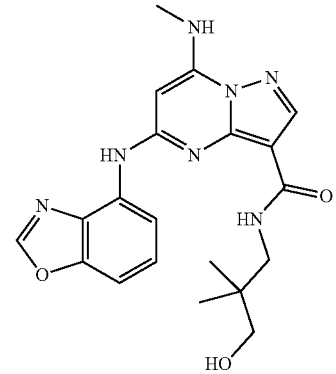 [SMILES: CNc1cc(Nc2cccc3ocnc23)nc2c(C(=O)NCC(C)(C)CO)cnn12] |
| I-751 | 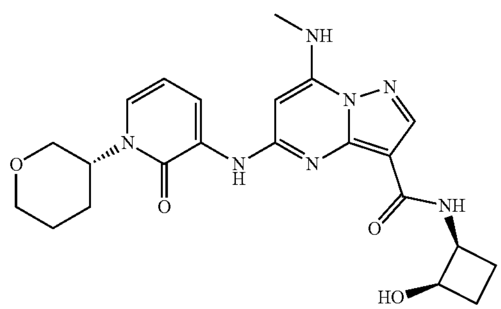 [SMILES: CNc1cc(Nc2cccn([C@@H]3CCCOC3)c2=O)nc2c(C(=O)N[C@H]3CC[C@H]3O)cnn12] |
| I-752 | 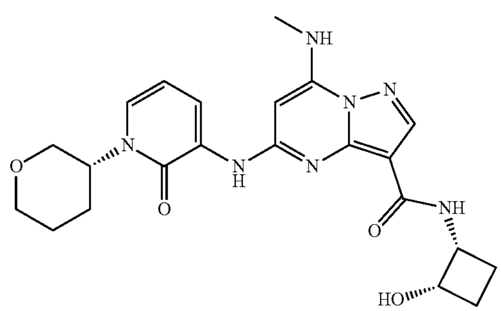 [SMILES: CNc1cc(Nc2cccn([C@@H]3CCCOC3)c2=O)nc2c(C(=O)N[C@@H]3CC[C@@H]3O)cnn12] |
| I-753 | 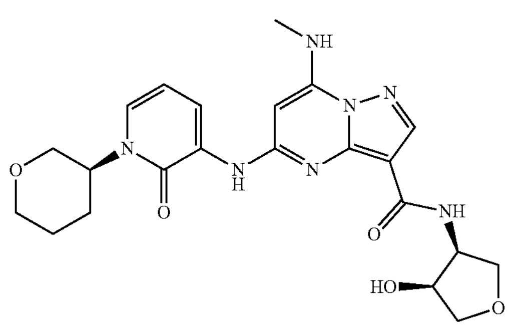 [SMILES: CNc1cc(Nc2cccn([C@H]3CCCOC3)c2=O)nc2c(C(=O)N[C@H]3COC[C@H]3O)cnn12] |

TABLE 1-continued

Selected Compounds

| Compound | Structure |
| --- | --- |
| I-754 | 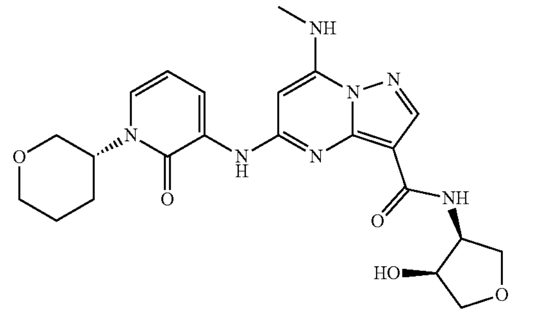 [SMILES: CNc1cc(Nc2cccn([C@@H]3CCCOC3)c2=O)nc2c(C(=O)N[C@H]3COC[C@H]3O)cnn12] |
| I-755 | 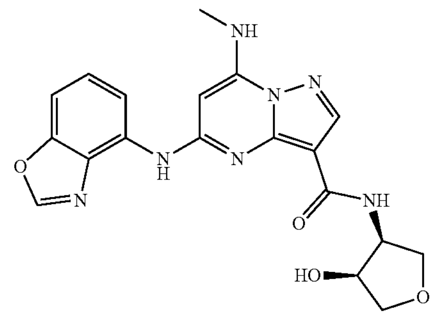 [SMILES: CNc1cc(Nc2cccc3ocnc23)nc2c(C(=O)N[C@H]3COC[C@H]3O)cnn12] |
| I-756 | 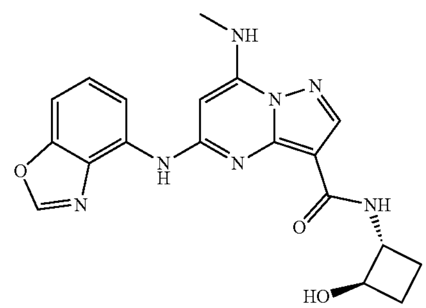 [SMILES: CNc1cc(Nc2cccc3ocnc23)nc2c(C(=O)N[C@@H]3CC[C@H]3O)cnn12] |
| I-757 | 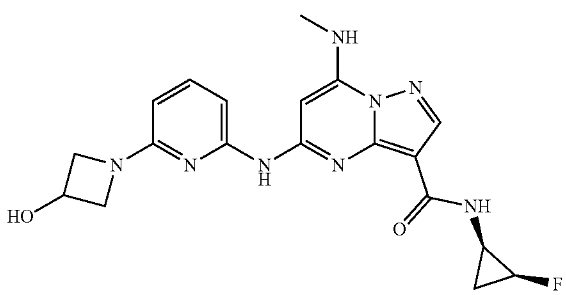 [SMILES: CNc1cc(Nc2cccc(N3CC(O)C3)n2)nc2c(C(=O)N[C@@H]3C[C@@H]3F)cnn12] |
| I-758 | 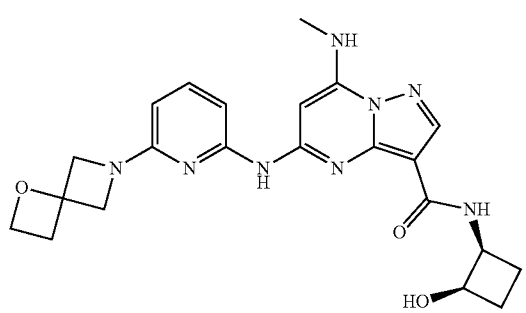 [SMILES: CNc1cc(Nc2cccc(N3CC4(CCO4)C3)n2)nc2c(C(=O)N[C@H]3CC[C@H]3O)cnn12] |

TABLE 1-continued

| Selected Compounds | |
|---|---|
| Compound | Structure |
| I-759 | |
| I-760 | |
| I-761 | |
| I-762 | |
| I-763 | |

TABLE 1-continued
| Selected Compounds | |
|---|---|
| Compound | Structure |
| I-764 | 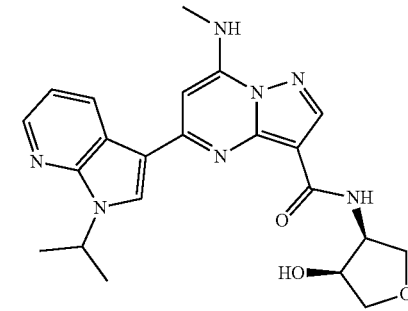 |
| I-765 | 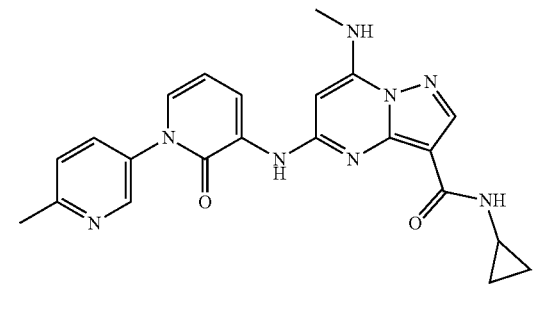 [SMILES: CNc1cc(Nc2cccn(-c3ccc(C)nc3)c2=O)nc2c(C(=O)NC3CC3)cnn12] |
| I-766 | 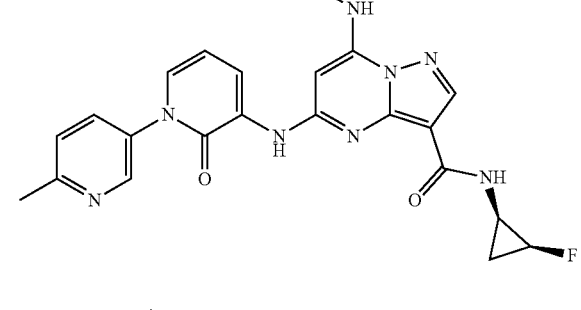 |
| I-767 | 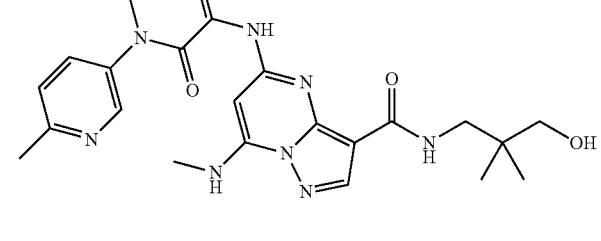 |
| I-768 | 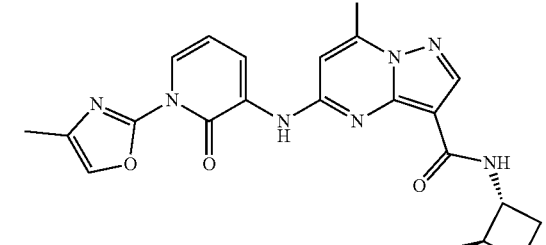 |

TABLE 1-continued
| Selected Compounds | |
|---|---|
| Compound | Structure |
| I-769 | 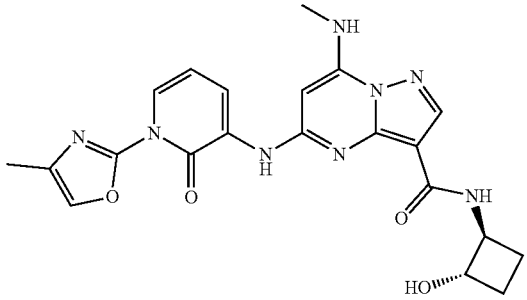 [SMILES: CNc1cc(Nc2cccn(-c3nc(C)co3)c2=O)nc2c(C(=O)N[C@H]3CC[C@@H]3O)cnn12] |
| I-770 | 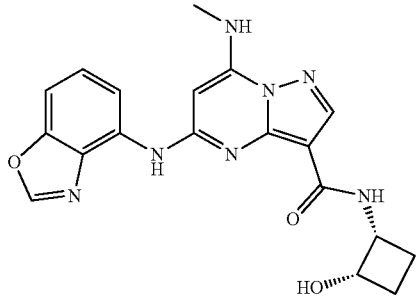 [SMILES: CNc1cc(Nc2cccc3ocnc23)nc2c(C(=O)N[C@@H]3CC[C@@H]3O)cnn12] |
| I-771 | 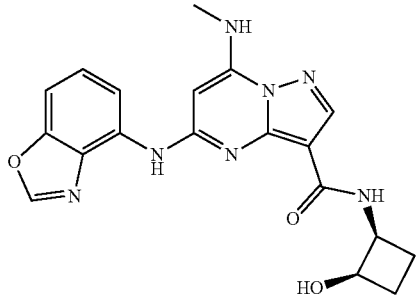 [SMILES: CNc1cc(Nc2cccc3ocnc23)nc2c(C(=O)N[C@H]3CC[C@H]3O)cnn12] |
| I-772 | 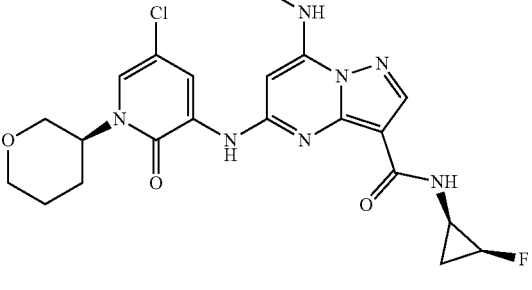 |
| I-773 | 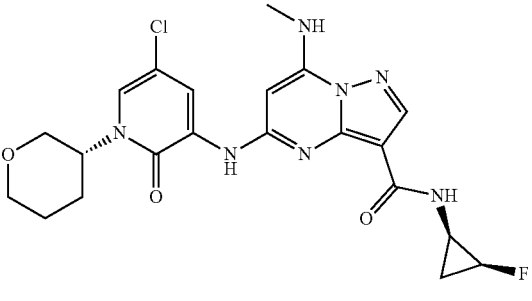 [SMILES: CNc1cc(Nc2cc(Cl)cn([C@@H]3CCCOC3)c2=O)nc2c(C(=O)N[C@@H]3C[C@@H]3F)cnn12] |

TABLE 1-continued
Selected Compounds
| Compound | Structure |
|---|---|
| I-774 | 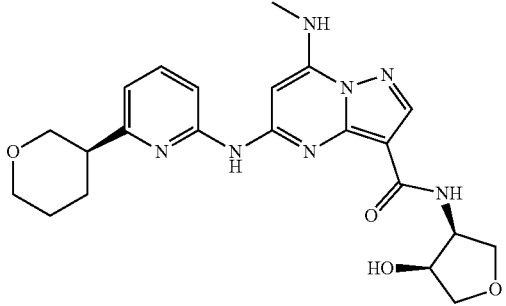 [SMILES: CNc1cc(Nc2cccc([C@H]3CCCOC3)n2)nc2c(C(=O)N[C@H]3COC[C@H]3O)cnn12] |
| I-775 | 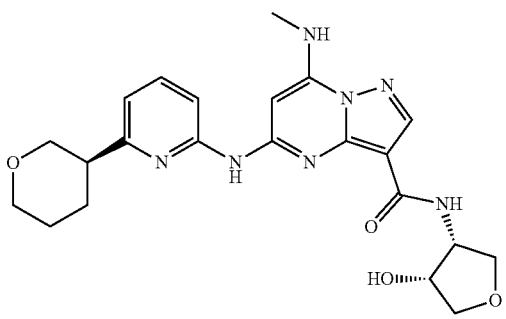 [SMILES: CNc1cc(Nc2cccc([C@H]3CCCOC3)n2)nc2c(C(=O)N[C@@H]3COC[C@@H]3O)cnn12] |
| I-776 | 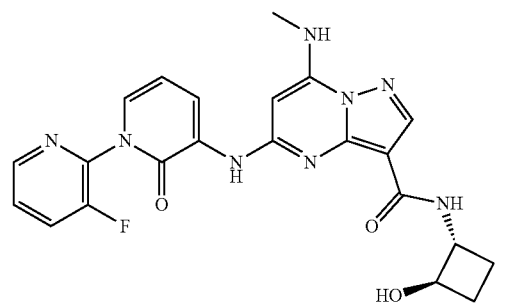 [SMILES: CNc1cc(Nc2cccn(-c3ncccc3F)c2=O)nc2c(C(=O)N[C@@H]3CC[C@H]3O)cnn12] |
| I-777 | 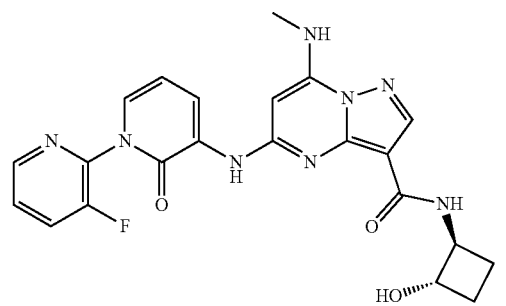 [SMILES: CNc1cc(Nc2cccn(-c3ncccc3F)c2=O)nc2c(C(=O)N[C@H]3CC[C@@H]3O)cnn12] |

TABLE 1-continued
Selected Compounds
| Compound | Structure |
|---|---|
| I-778 | 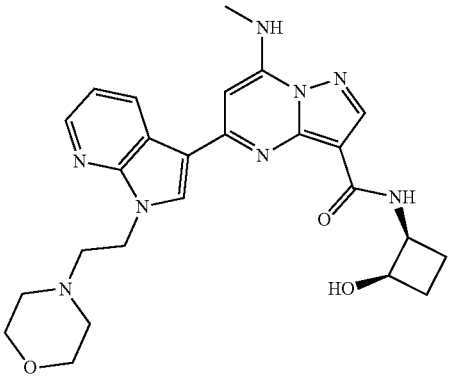 [SMILES: CNc1cc(-c2cn(CCN3CCOCC3)c3ncccc23)nc2c(C(=O)N[C@H]3CC[C@H]3O)cnn12] |
| I-779 | 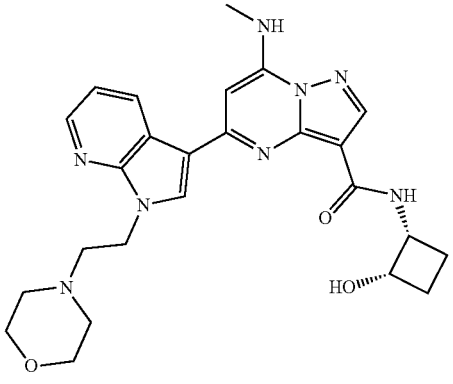 [SMILES: CNc1cc(-c2cn(CCN3CCOCC3)c3ncccc23)nc2c(C(=O)N[C@@H]3CC[C@@H]3O)cnn12] |
| I-780 | 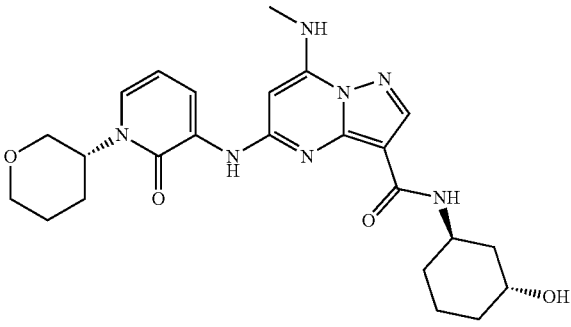 [SMILES: CNc1cc(Nc2cccn([C@@H]3CCCOC3)c2=O)nc2c(C(=O)N[C@@H]3CCC[C@@H](O)C3)cnn12] |
| I-781 | 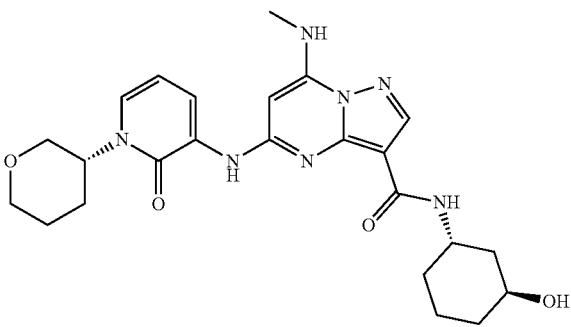 [SMILES: CNc1cc(Nc2cccn([C@@H]3CCCOC3)c2=O)nc2c(C(=O)N[C@H]3CCC[C@H](O)C3)cnn12] |

TABLE 1-continued
Selected Compounds
| Compound | Structure |
|---|---|
| I-782 | 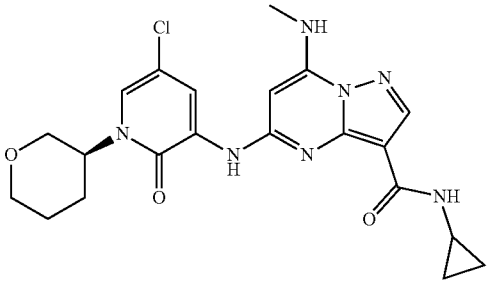 [SMILES: CNc1cc(Nc2cc(Cl)cn([C@H]3CCCOC3)c2=O)nc2c(C(=O)NC3CC3)cnn12] |
| I-783 | 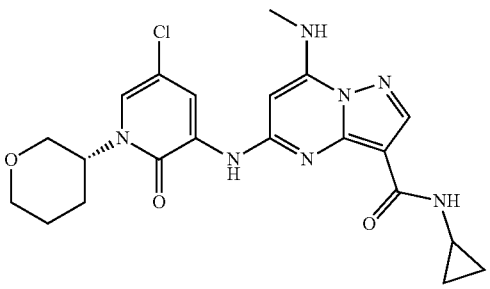 [SMILES: CNc1cc(Nc2cc(Cl)cn([C@@H]3CCCOC3)c2=O)nc2c(C(=O)NC3CC3)cnn12] |
| I-784 | 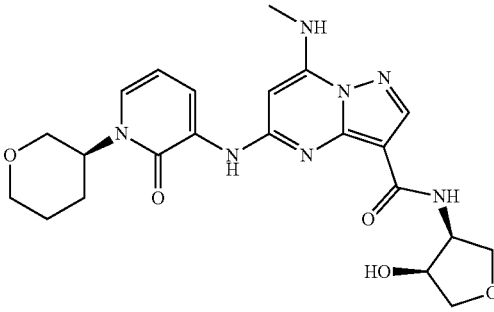 |
| I-785 | 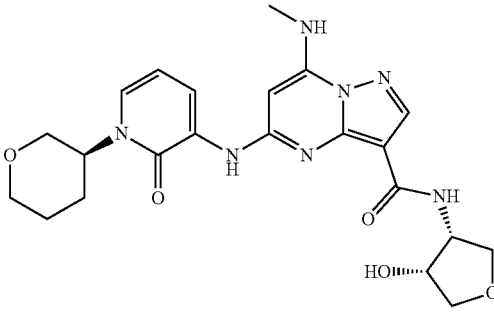 |
| I-786 | 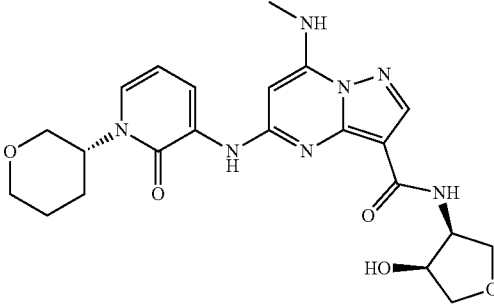 |

TABLE 1-continued

Selected Compounds

| Compound | Structure |
|---|---|
| I-787 | 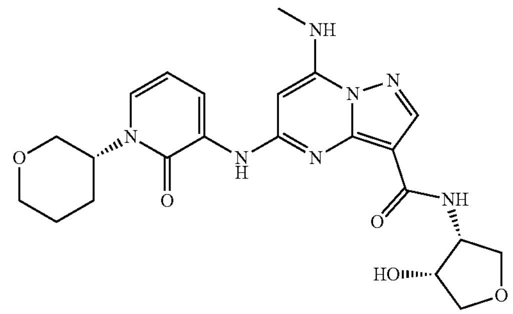 [SMILES: CNc1cc(Nc2cccn([C@@H]3CCCOC3)c2=O)nc2c(C(=O)N[C@@H]3COC[C@@H]3O)cnn12] |
| I-788 | 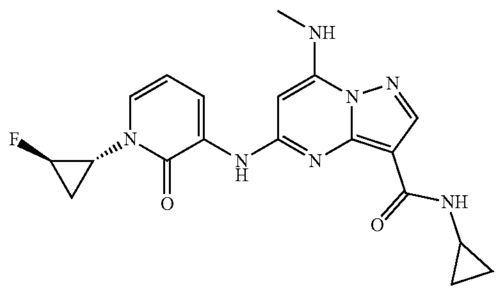 [SMILES: CNc1cc(Nc2cccn([C@@H]3C[C@H]3F)c2=O)nc2c(C(=O)NC3CC3)cnn12] |
| I-789 | 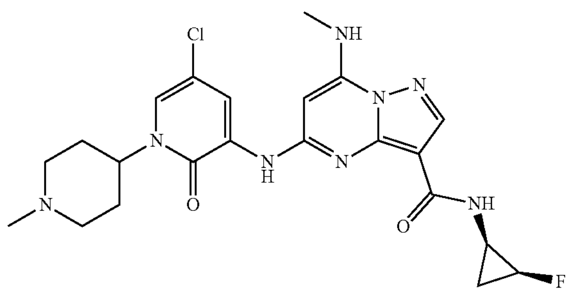 [SMILES: CNc1cc(Nc2cc(Cl)cn(C3CCN(C)CC3)c2=O)nc2c(C(=O)N[C@@H]3C[C@@H]3F)cnn12] |
| I-790 | 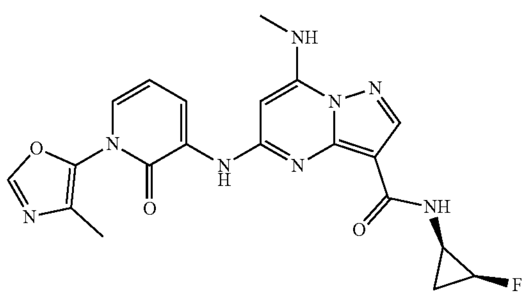 [SMILES: CNc1cc(Nc2cccn(-c3ocnc3C)c2=O)nc2c(C(=O)N[C@@H]3C[C@@H]3F)cnn12] |
| I-791 | 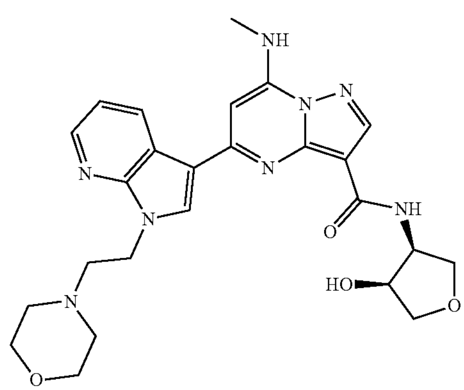 [SMILES: CNc1cc(-c2cn(CCN3CCOCC3)c3ncccc23)nc2c(C(=O)N[C@H]3COC[C@H]3O)cnn12] |

475
TABLE 1-continued
Selected Compounds
| Compound | Structure |
|---|---|
| I-792 | 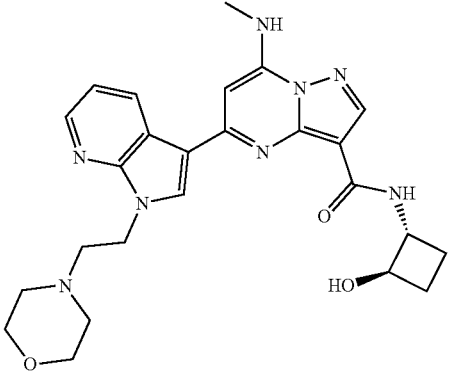 [SMILES: CNc1cc(-c2cn(CCN3CCOCC3)c3ncccc23)nc2c(C(=O)N[C@@H]3CC[C@H]3O)cnn12] |
| I-793 | 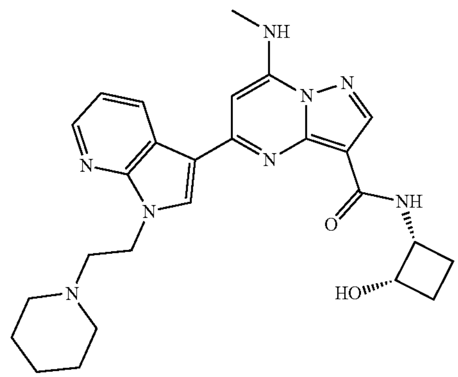 [SMILES: CNc1cc(-c2cn(CCN3CCCCC3)c3ncccc23)nc2c(C(=O)N[C@@H]3CC[C@@H]3O)cnn12] |
| I-794 | 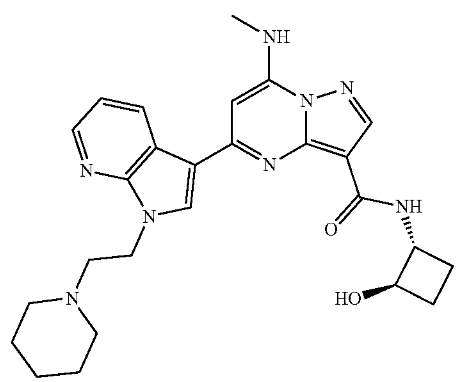 [SMILES: CNc1cc(-c2cn(CCN3CCCCC3)c3ncccc23)nc2c(C(=O)N[C@@H]3CC[C@H]3O)cnn12] |
| I-795 | 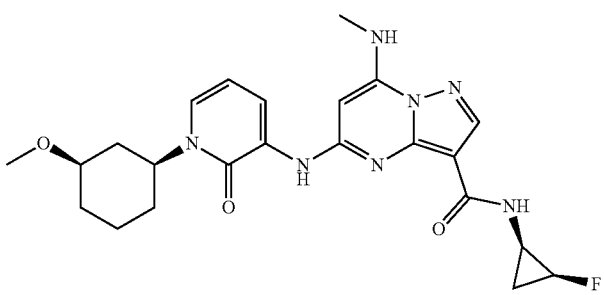 [SMILES: CNc1cc(Nc2cccn([C@H]3CCC[C@@H](OC)C3)c2=O)nc2c(C(=O)N[C@@H]3C[C@@H]3F)cnn12] |

TABLE 1-continued
| Selected Compounds | |
|---|---|
| Compound | Structure |
| I-796 | 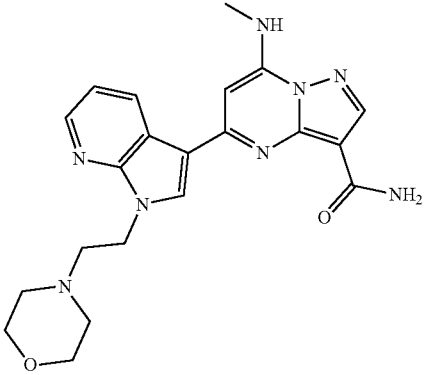 [SMILES: CNc1cc(-c2cn(CCN3CCOCC3)c3ncccc23)nc2c(C(N)=O)cnn12] |
| I-797 | 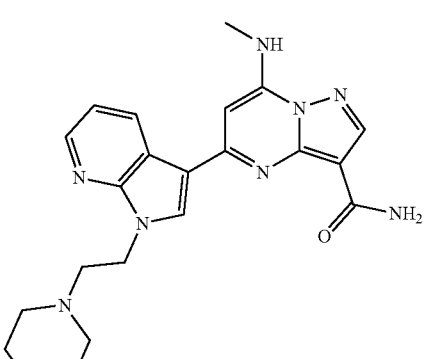 |
| I-798 | 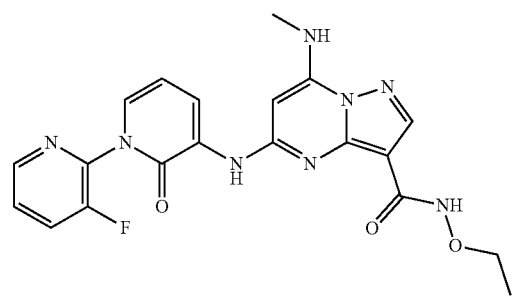 [SMILES: CCONC(=O)c1cnn2c(NC)cc(Nc3cccn(-c4ncccc4F)c3=O)nc12] |
| I-799 | 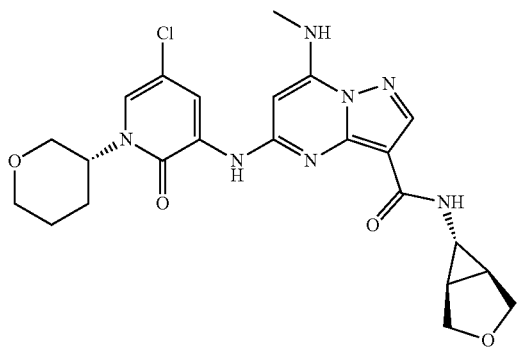 [SMILES: CNc1cc(Nc2cc(Cl)cn([C@@H]3CCCOC3)c2=O)nc2c(C(=O)N[C@H]3[C@@H]4COC[C@@H]43)cnn12] |

TABLE 1-continued
Selected Compounds
| Compound | Structure |
|---|---|
| I-800 | 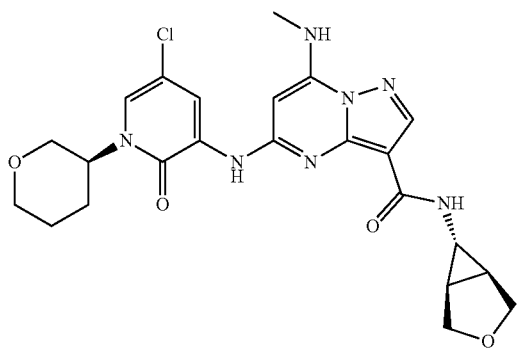 [SMILES: CNc1cc(Nc2cc(Cl)cn([C@H]3CCCOC3)c2=O)nc2c(C(=O)N[C@H]3[C@@H]4COC[C@@H]43)cnn12] |
| I-801 | 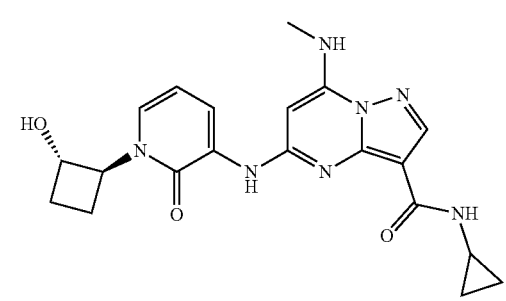 [SMILES: CNc1cc(Nc2cccn([C@H]3CC[C@@H]3O)c2=O)nc2c(C(=O)NC3CC3)cnn12] |
| I-802 | 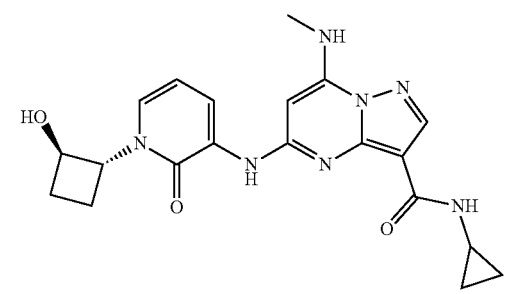 [SMILES: CNc1cc(Nc2cccn([C@@H]3CC[C@H]3O)c2=O)nc2c(C(=O)NC3CC3)cnn12] |
| I-803 | 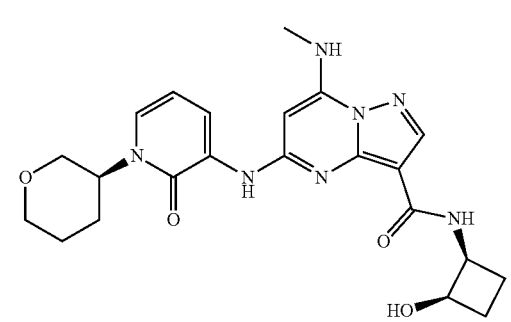 [SMILES: CNc1cc(Nc2cccn([C@H]3CCCOC3)c2=O)nc2c(C(=O)N[C@H]3CC[C@H]3O)cnn12] |
| I-804 | 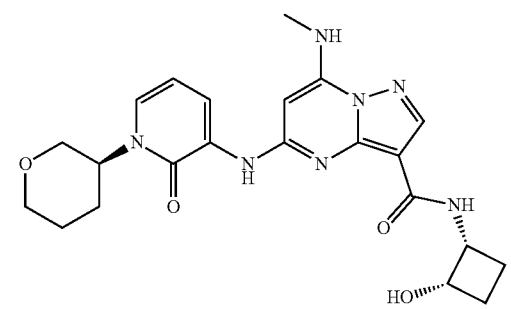 [SMILES: CNc1cc(Nc2cccn([C@H]3CCCOC3)c2=O)nc2c(C(=O)N[C@@H]3CC[C@@H]3O)cnn12] |

TABLE 1-continued
Selected Compounds
| Compound | Structure |
|---|---|
| I-805 | 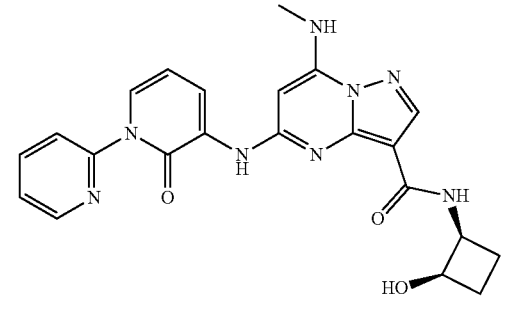 [SMILES: CNc1cc(Nc2cccn(-c3ccccn3)c2=O)nc2c(C(=O)N[C@H]3CC[C@H]3O)cnn12] |
| I-806 | 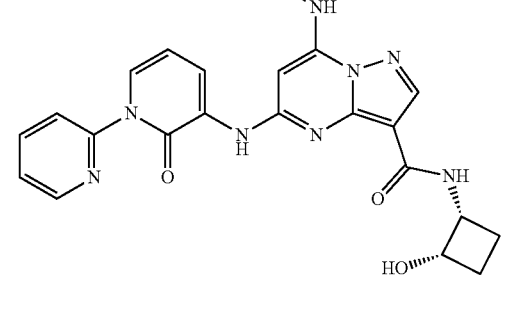 |
| I-807 | 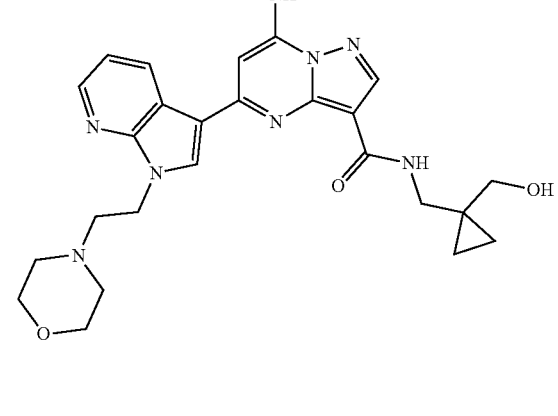 |
| I-808 | 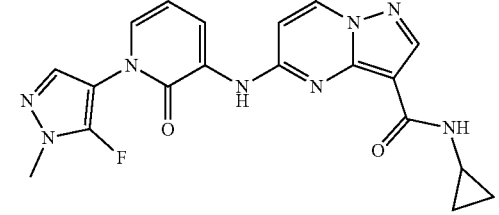 |

TABLE 1-continued
| Selected Compounds | |
|---|---|
| Compound | Structure |
| I-809 | 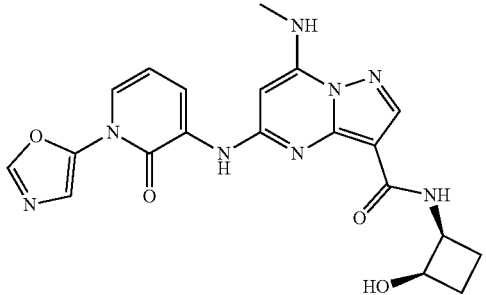 [SMILES: CNc1cc(Nc2cccn(-c3cnco3)c2=O)nc2c(C(=O)N[C@H]3CC[C@H]3O)cnn12] |
| I-810 | 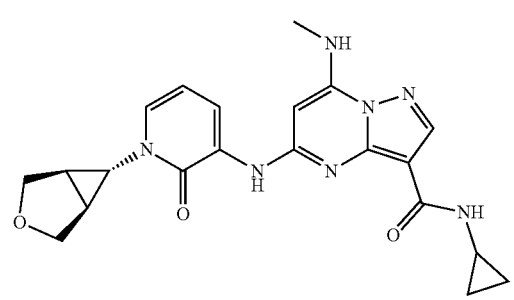 [SMILES: CNc1cc(Nc2cccn([C@H]3[C@@H]4COC[C@@H]43)c2=O)nc2c(C(=O)NC3CC3)cnn12] |
| I-811 | 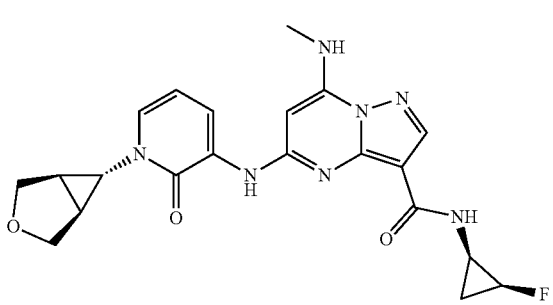 [SMILES: CNc1cc(Nc2cccn([C@H]3[C@@H]4COC[C@@H]43)c2=O)nc2c(C(=O)N[C@@H]3C[C@@H]3F)cnn12] |
| I-812 | 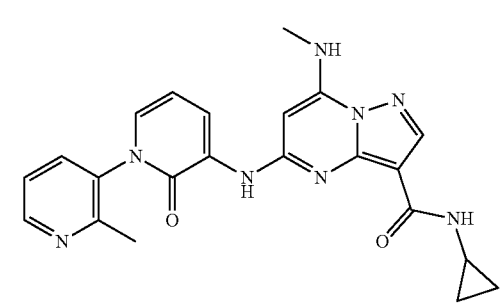 [SMILES: CNc1cc(Nc2cccn(-c3cccnc3C)c2=O)nc2c(C(=O)NC3CC3)cnn12] |
| I-813 | 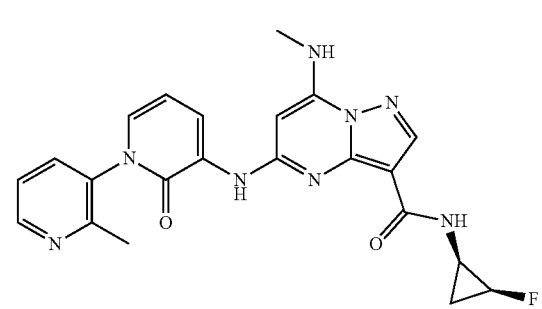 [SMILES: CNc1cc(Nc2cccn(-c3cccnc3C)c2=O)nc2c(C(=O)N[C@@H]3C[C@@H]3F)cnn12] |

TABLE 1-continued
Selected Compounds
| Compound | Structure |
|---|---|
| I-814 | 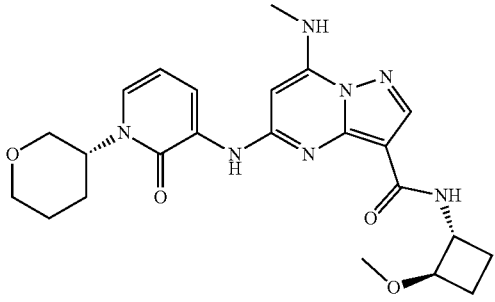 [SMILES: CNc1cc(Nc2cccn([C@@H]3CCCOC3)c2=O)nc2c(C(=O)N[C@@H]3CC[C@H]3OC)cnn12] |
| I-815 | 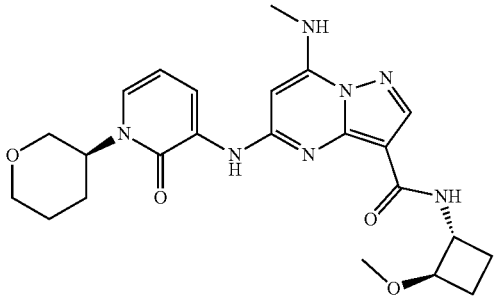 [SMILES: CNc1cc(Nc2cccn([C@H]3CCCOC3)c2=O)nc2c(C(=O)N[C@@H]3CC[C@H]3OC)cnn12] |
| I-816 | 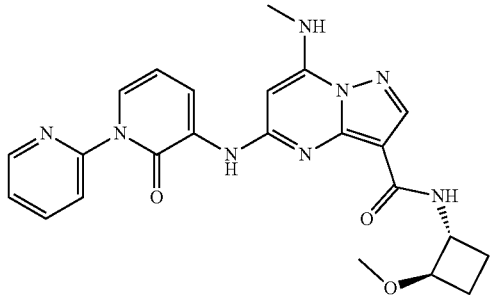 [SMILES: CNc1cc(Nc2cccn(-c3ccccn3)c2=O)nc2c(C(=O)N[C@@H]3CC[C@H]3OC)cnn12] |
| I-817 | 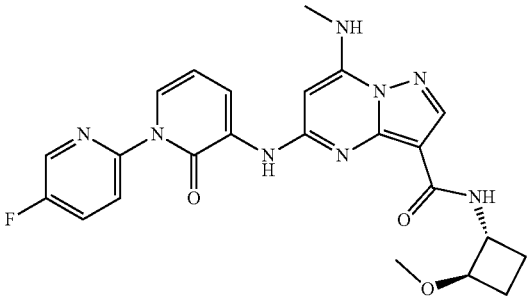 [SMILES: CNc1cc(Nc2cccn(-c3ccc(F)cn3)c2=O)nc2c(C(=O)N[C@@H]3CC[C@H]3OC)cnn12] |

TABLE 1-continued
Selected Compounds
| Compound | Structure |
|---|---|
| I-818 | 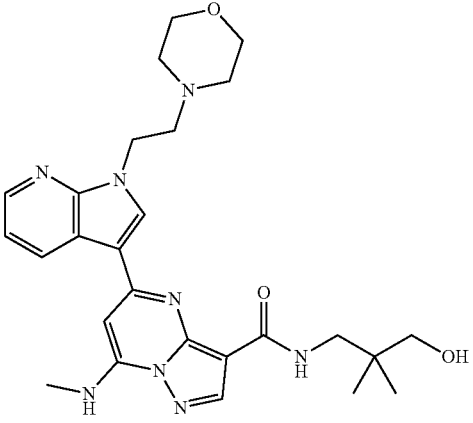 [SMILES: CNc1cc(-c2cn(CCN3CCOCC3)c3ncccc23)nc2c(C(=O)NCC(C)(C)CO)cnn12] |
| I-819 | 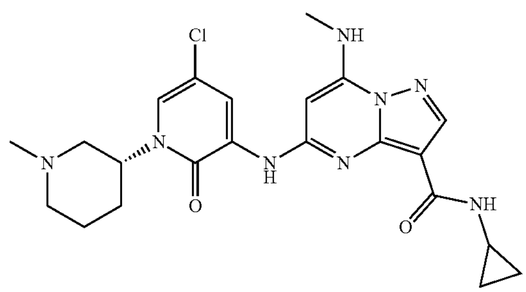 [SMILES: CNc1cc(Nc2cc(Cl)cn([C@@H]3CCCN(C)C3)c2=O)nc2c(C(=O)NC3CC3)cnn12] |
| I-820 | 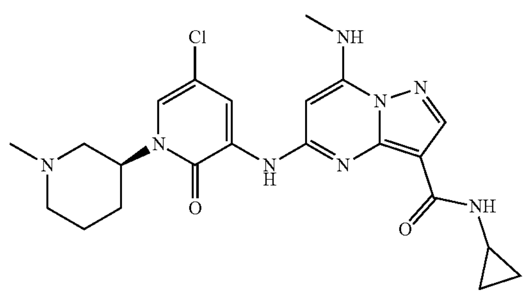 [SMILES: CNc1cc(Nc2cc(Cl)cn([C@H]3CCCN(C)C3)c2=O)nc2c(C(=O)NC3CC3)cnn12] |
| I-821 | 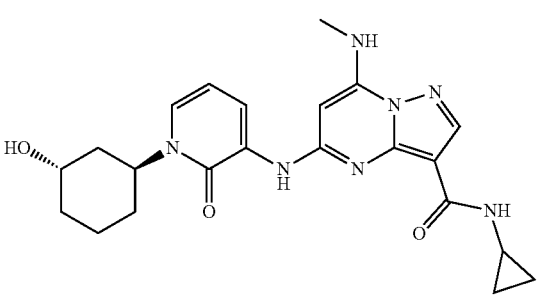 [SMILES: CNc1cc(Nc2cccn([C@H]3CCC[C@H](O)C3)c2=O)nc2c(C(=O)NC3CC3)cnn12] |

TABLE 1-continued

Selected Compounds

| Compound | Structure |
|---|---|
| I-822 | 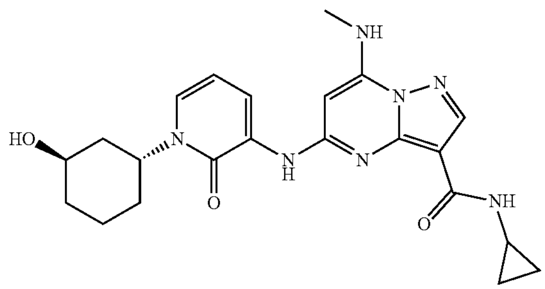 [SMILES: CNc1cc(Nc2cccn([C@@H]3CCC[C@@H](O)C3)c2=O)nc2c(C(=O)NC3CC3)cnn12] |
| I-823 | 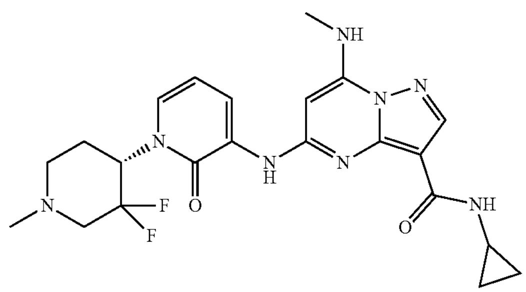 [SMILES: CNc1cc(Nc2cccn([C@H]3CCN(C)CC3(F)F)c2=O)nc2c(C(=O)NC3CC3)cnn12] |
| I-824 | 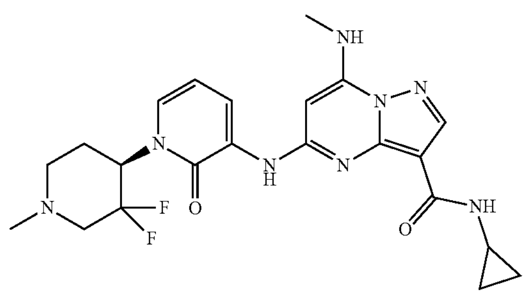 [SMILES: CNc1cc(Nc2cccn([C@@H]3CCN(C)CC3(F)F)c2=O)nc2c(C(=O)NC3CC3)cnn12] |
| I-825 | 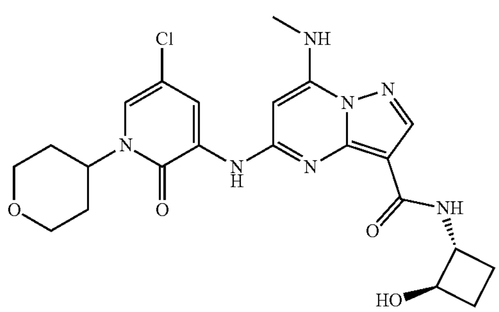 [SMILES: CNc1cc(Nc2cc(Cl)cn(C3CCOCC3)c2=O)nc2c(C(=O)N[C@@H]3CC[C@H]3O)cnn12] |
| I-826 | 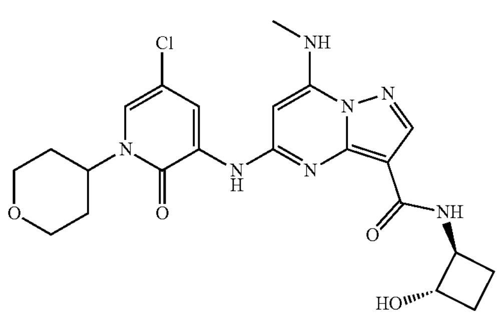 [SMILES: CNc1cc(Nc2cc(Cl)cn(C3CCOCC3)c2=O)nc2c(C(=O)N[C@H]3CC[C@@H]3O)cnn12] |

TABLE 1-continued

Selected Compounds

| Compound | Structure |
|---|---|
| I-827 | 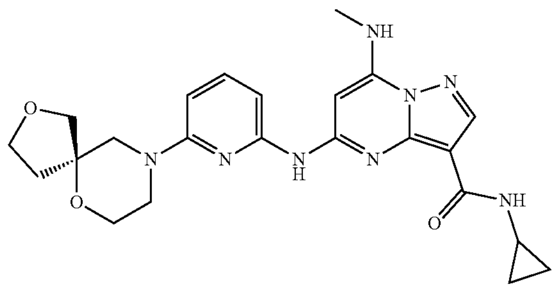 [SMILES: CNc1cc(Nc2cccc(N3CCO[C@]4(CCOC4)C3)n2)nc2c(C(=O)NC3CC3)cnn12] |
| I-828 | 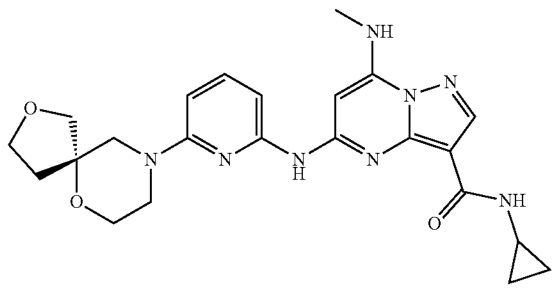 [SMILES: CNc1cc(Nc2cccc(N3CCO[C@@]4(CCOC4)C3)n2)nc2c(C(=O)NC3CC3)cnn12] |
| I-829 | 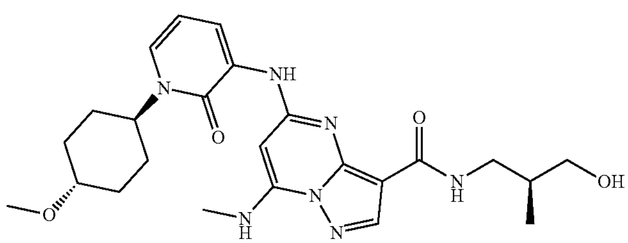 [SMILES: CNc1cc(Nc2cccn([C@H]3CC[C@H](OC)CC3)c2=O)nc2c(C(=O)NC[C@H](C)CO)cnn12] |
| I-830 | 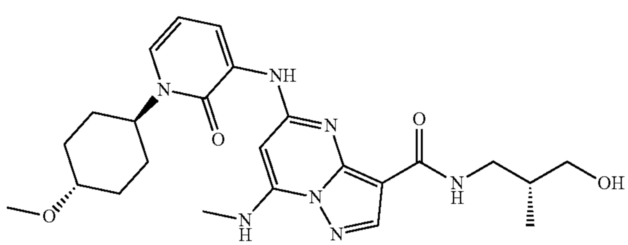 [SMILES: CNc1cc(Nc2cccn([C@H]3CC[C@H](OC)CC3)c2=O)nc2c(C(=O)NC[C@@H](C)CO)cnn12] |
| I-831 | 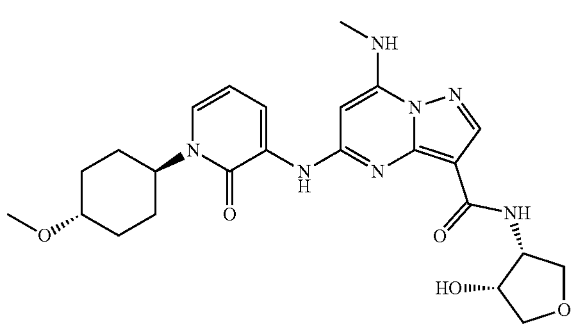 [SMILES: CNc1cc(Nc2cccn([C@H]3CC[C@H](OC)CC3)c2=O)nc2c(C(=O)N[C@@H]3COC[C@@H]3O)cnn12] |

TABLE 1-continued

Selected Compounds

| Compound | Structure |
|---|---|
| I-832 | 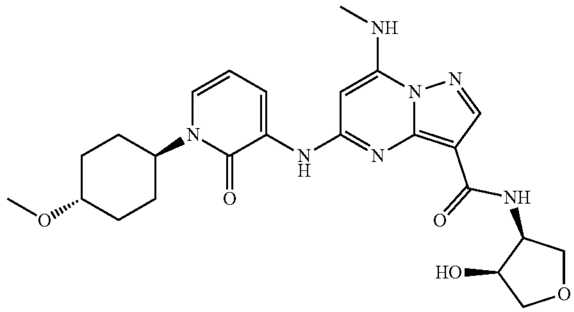 [SMILES: CNc1cc(Nc2cccn([C@H]3CC[C@H](OC)CC3)c2=O)nc2c(C(=O)N[C@H]3COC[C@H]3O)cnn12] |
| I-833 | 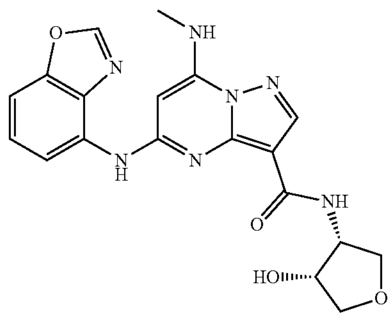 [SMILES: CNc1cc(Nc2cccc3ocnc23)nc2c(C(=O)N[C@@H]3COC[C@@H]3O)cnn12] |
| I-834 | 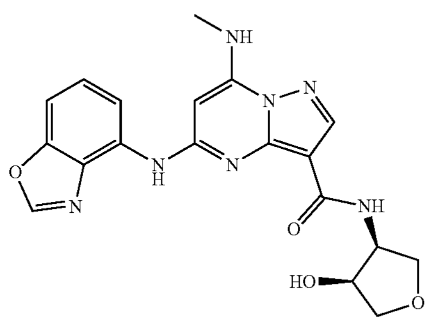 [SMILES: CNc1cc(Nc2cccc3ocnc23)nc2c(C(=O)N[C@H]3COC[C@H]3O)cnn12] |
| I-835 | 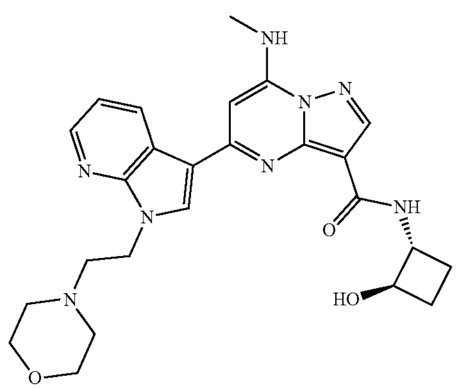 [SMILES: CNc1cc(-c2cn(CCN3CCOCC3)c3ncccc23)nc2c(C(=O)N[C@@H]3CC[C@H]3O)cnn12] |

TABLE 1-continued

Selected Compounds

| Compound | Structure |
|---|---|
| I-836 | 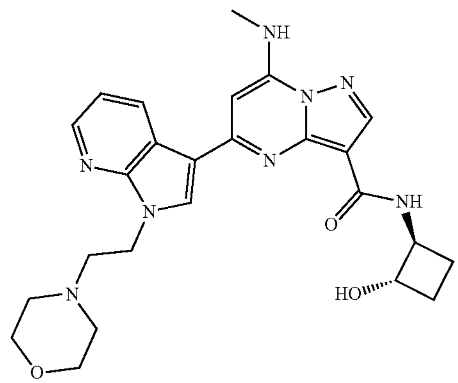 [SMILES: CNc1cc(-c2cn(CCN3CCOCC3)c3ncccc23)nc2c(C(=O)N[C@H]3CC[C@@H]3O)cnn12] |
| I-837 | 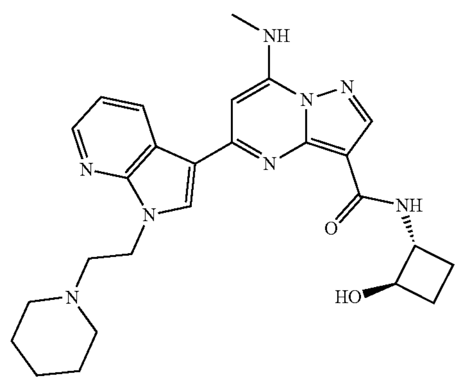 [SMILES: CNc1cc(-c2cn(CCN3CCCCC3)c3ncccc23)nc2c(C(=O)N[C@@H]3CC[C@H]3O)cnn12] |
| I-838 | 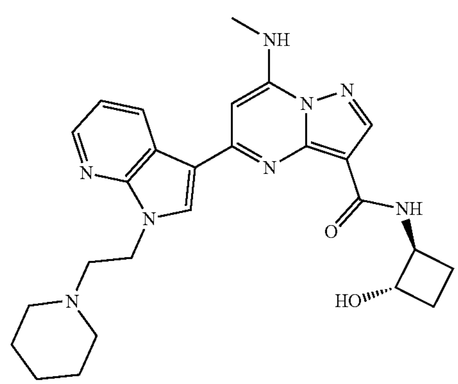 [SMILES: CNc1cc(-c2cn(CCN3CCCCC3)c3ncccc23)nc2c(C(=O)N[C@H]3CC[C@@H]3O)cnn12] |
| I-839 | 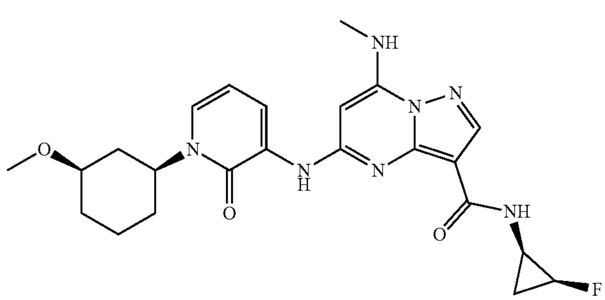 [SMILES: CNc1cc(Nc2cccn([C@H]3CCC[C@@H](OC)C3)c2=O)nc2c(C(=O)N[C@@H]3C[C@@H]3F)cnn12] |

TABLE 1-continued
Selected Compounds
| Compound | Structure |
|---|---|
| I-840 | 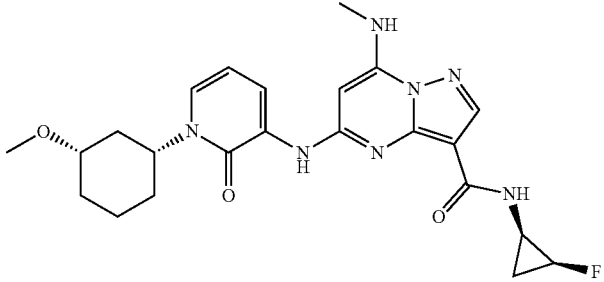 [SMILES: CNc1cc(Nc2cccn([C@@H]3CCC[C@H](OC)C3)c2=O)nc2c(C(=O)N[C@@H]3C[C@@H]3F)cnn12] |
| I-841 | 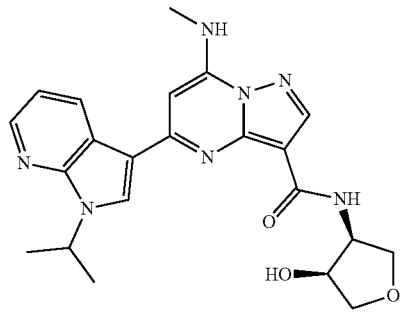 [SMILES: CNc1cc(-c2cn(C(C)C)c3ncccc23)nc2c(C(=O)N[C@H]3COC[C@H]3O)cnn12] |
| I-842 | 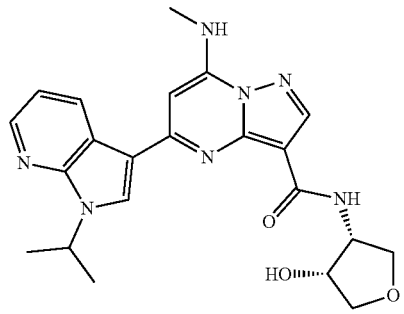 [SMILES: CNc1cc(-c2cn(C(C)C)c3ncccc23)nc2c(C(=O)N[C@@H]3COC[C@@H]3O)cnn12] |
| I-843 | 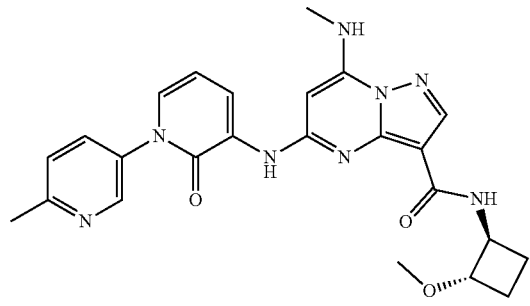 [SMILES: CNc1cc(Nc2cccn(-c3ccc(C)nc3)c2=O)nc2c(C(=O)N[C@H]3CC[C@@H]3OC)cnn12] |
| I-844 | 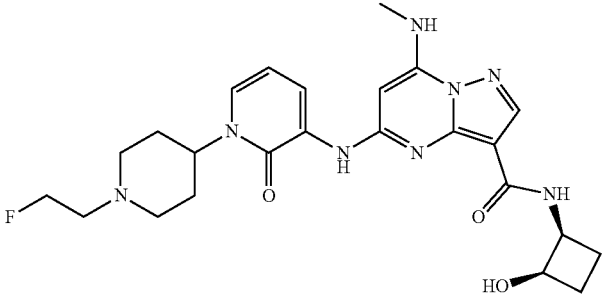 |

TABLE 1-continued

Selected Compounds

| Compound | Structure |
|---|---|
| I-845 | 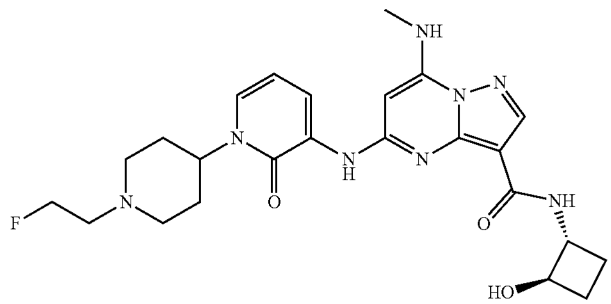 [SMILES: CNc1cc(Nc2cccn(C3CCN(CCF)CC3)c2=O)nc2c(C(=O)N[C@@H]3CC[C@H]3O)cnn12] |
| I-846 | 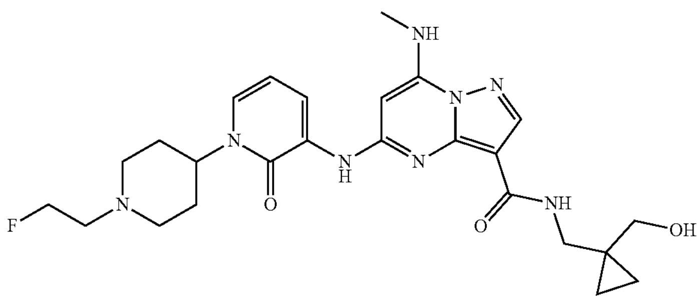 [SMILES: CNc1cc(Nc2cccn(C3CCN(CCF)CC3)c2=O)nc2c(C(=O)NCC3(CO)CC3)cnn12] |
| I-847 | 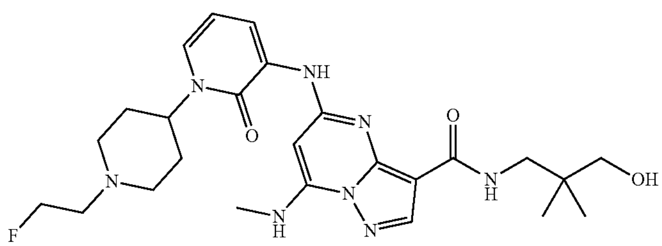 [SMILES: CNc1cc(Nc2cccn(C3CCN(CCF)CC3)c2=O)nc2c(C(=O)NCC(C)(C)CO)cnn12] |
| I-848 | 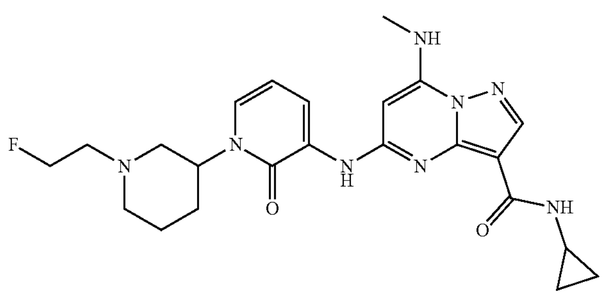 [SMILES: CNc1cc(Nc2cccn(C3CCCN(CCF)C3)c2=O)nc2c(C(=O)NC3CC3)cnn12] |
| I-849 | 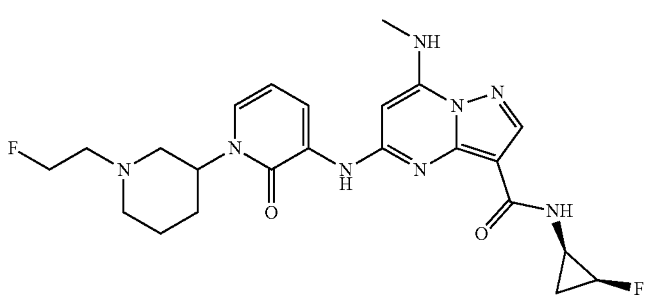 [SMILES: CNc1cc(Nc2cccn(C3CCCN(CCF)C3)c2=O)nc2c(C(=O)N[C@@H]3C[C@@H]3F)cnn12] |

TABLE 1-continued
Selected Compounds
| Compound | Structure |
|---|---|
| I-850 | 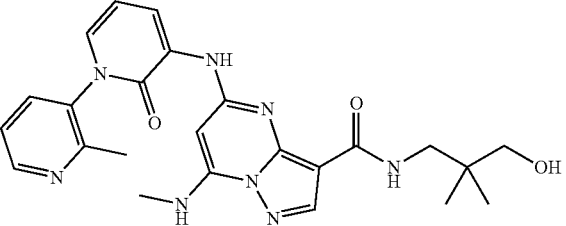 [SMILES: CNc1cc(Nc2cccn(-c3cccnc3C)c2=O)nc2c(C(=O)NCC(C)(C)CO)cnn12] |
| I-851 | 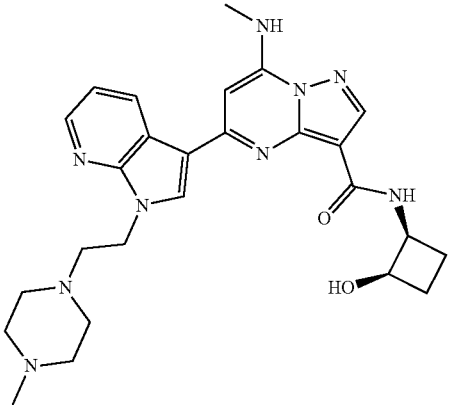 [SMILES: CNc1cc(-c2cn(CCN3CCN(C)CC3)c3ncccc23)nc2c(C(=O)N[C@H]3CC[C@H]3O)cnn12] |
| I-852 | 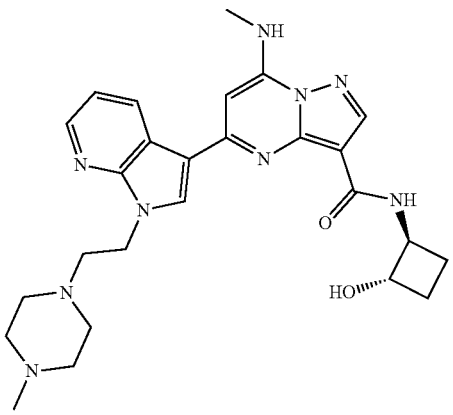 [SMILES: CNc1cc(-c2cn(CCN3CCN(C)CC3)c3ncccc23)nc2c(C(=O)N[C@H]3CC[C@@H]3O)cnn12] |
| I-853 | 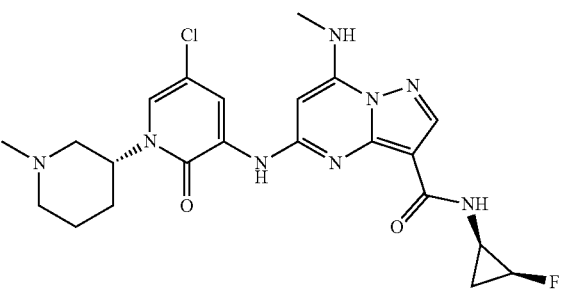 [SMILES: CNc1cc(Nc2cc(Cl)cn([C@@H]3CCCN(C)C3)c2=O)nc2c(C(=O)N[C@@H]3C[C@@H]3F)cnn12] |

TABLE 1-continued

Selected Compounds

| Compound | Structure |
|---|---|
| I-854 | 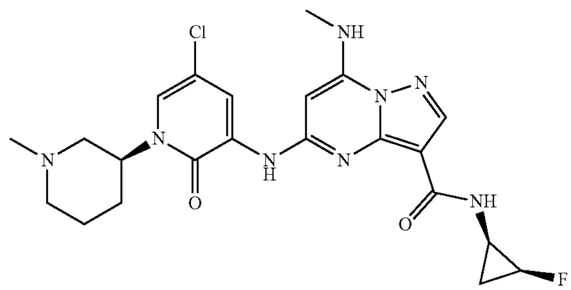 [SMILES: CNc1cc(Nc2cc(Cl)cn([C@H]3CCCN(C)C3)c2=O)nc2c(C(=O)N[C@@H]3C[C@@H]3F)cnn12] |
| I-855 | 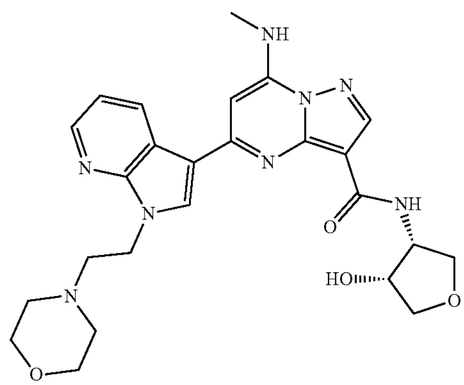 [SMILES: CNc1cc(-c2cn(CCN3CCOCC3)c3ncccc23)nc2c(C(=O)N[C@@H]3COC[C@@H]3O)cnn12] |
| I-856 | 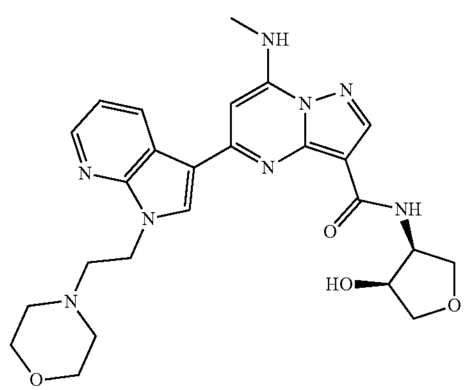 [SMILES: CNc1cc(-c2cn(CCN3CCOCC3)c3ncccc23)nc2c(C(=O)N[C@H]3COC[C@H]3O)cnn12] |
| I-857 | 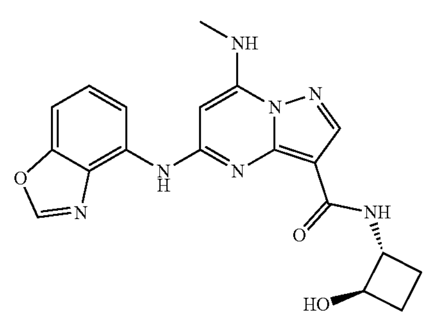 [SMILES: CNc1cc(Nc2cccc3ocnc23)nc2c(C(=O)N[C@@H]3CC[C@H]3O)cnn12] |

TABLE 1-continued

| Selected Compounds | |
|---|---|
| Compound | Structure |
| I-858 | |
| I-859 | |
| I-860 | |
| I-861 | |
| I-862 | |

TABLE 1-continued

Selected Compounds

| Compound | Structure |
|---|---|
| I-863 | 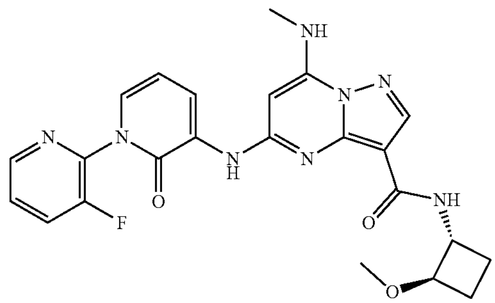 [SMILES: CNc1cc(Nc2cccn(-c3ncccc3F)c2=O)nc2c(C(=O)N[C@@H]3CC[C@H]3OC)cnn12] |
| I-864 | 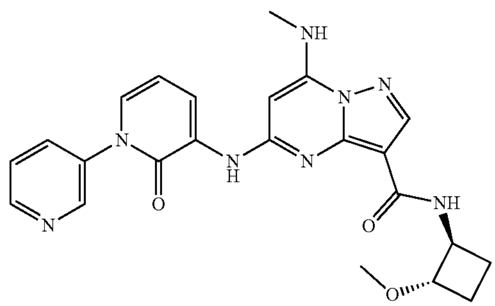 [SMILES: CNc1cc(Nc2cccn(-c3cccnc3)c2=O)nc2c(C(=O)N[C@H]3CC[C@@H]3OC)cnn12] |
| I-865 | 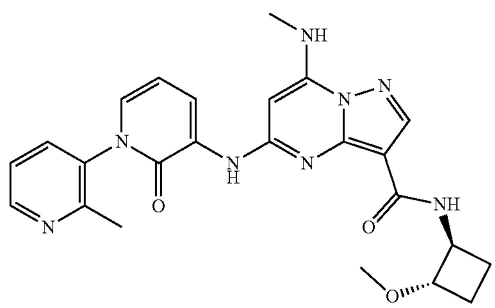 [SMILES: CNc1cc(Nc2cccn(-c3cccnc3C)c2=O)nc2c(C(=O)N[C@H]3CC[C@@H]3OC)cnn12] |
| I-866 | 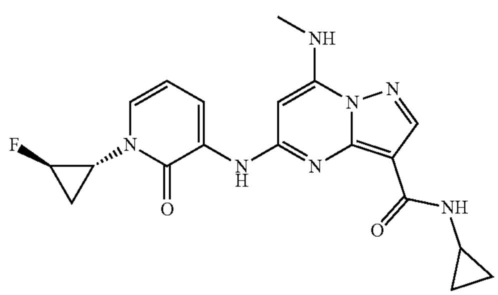 [SMILES: CNc1cc(Nc2cccn([C@@H]3C[C@H]3F)c2=O)nc2c(C(=O)NC3CC3)cnn12] |
| I-867 | 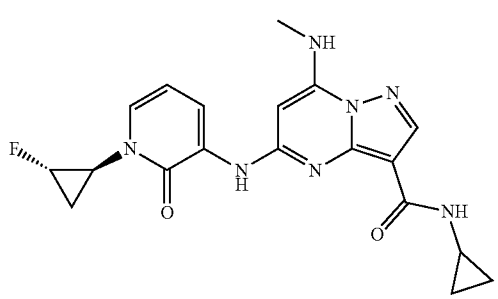 [SMILES: CNc1cc(Nc2cccn([C@H]3C[C@@H]3F)c2=O)nc2c(C(=O)NC3CC3)cnn12] |

TABLE 1-continued

Selected Compounds

| Compound | Structure |
|---|---|
| I-868 | 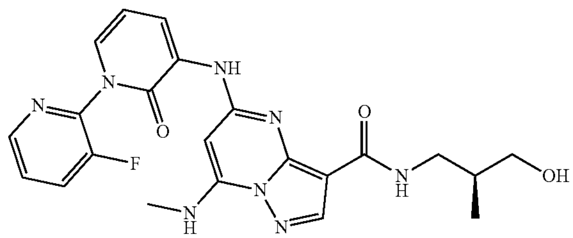 [SMILES: CNc1cc(Nc2cccn(-c3ncccc3F)c2=O)nc2c(C(=O)NC[C@H](C)CO)cnn12] |
| I-869 | 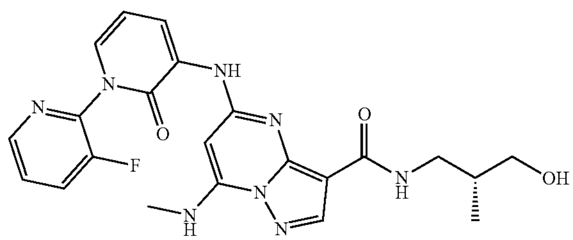 [SMILES: CNc1cc(Nc2cccn(-c3ncccc3F)c2=O)nc2c(C(=O)NC[C@@H](C)CO)cnn12] |
| I-870 | 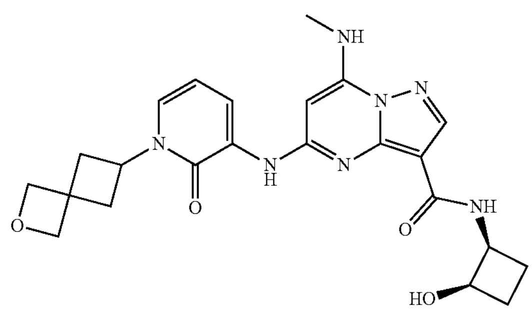 [SMILES: CNc1cc(Nc2cccn(C3CC4(COC4)C3)c2=O)nc2c(C(=O)N[C@H]3CC[C@H]3O)cnn12] |
| I-871 | 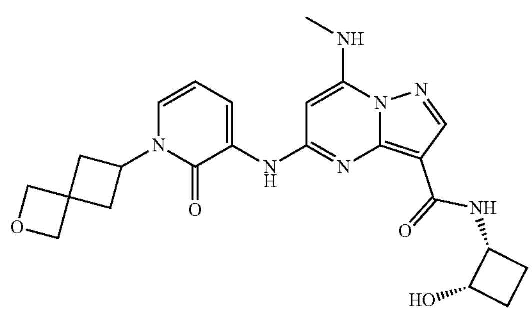 [SMILES: CNc1cc(Nc2cccn(C3CC4(COC4)C3)c2=O)nc2c(C(=O)N[C@@H]3CC[C@@H]3O)cnn12] |
| I-872 | 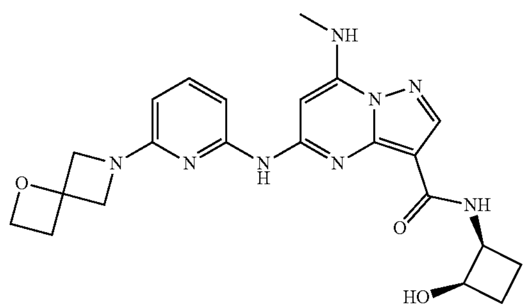 [SMILES: CNc1cc(Nc2cccc(N3CC4(CCO4)C3)n2)nc2c(C(=O)N[C@H]3CC[C@H]3O)cnn12] |

TABLE 1-continued
Selected Compounds
| Compound | Structure |
|---|---|
| I-873 | 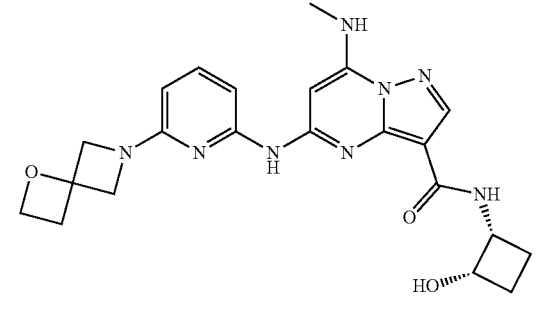 [SMILES: CNc1cc(Nc2cccc(N3CC4(CCO4)C3)n2)nc2c(C(=O)N[C@@H]3CC[C@@H]3O)cnn12] |
| I-874 | 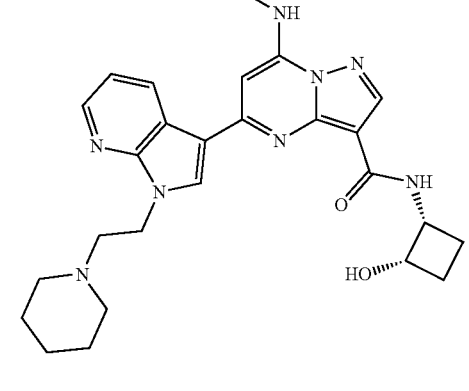 |
| I-875 | 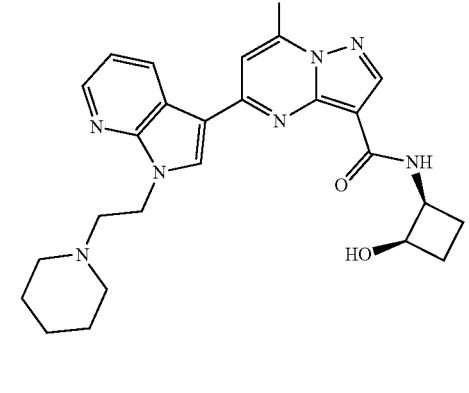 |
| I-876 | 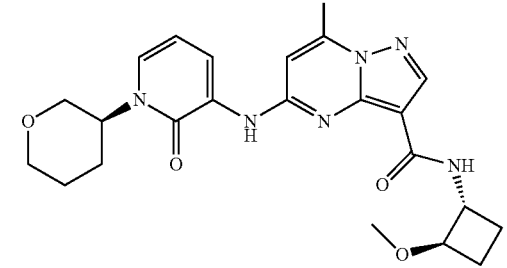 |

TABLE 1-continued
Selected Compounds
| Compound | Structure |
|---|---|
| I-877 | 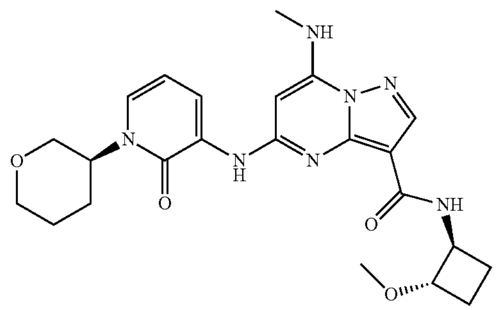 [SMILES: CNc1cc(Nc2cccn([C@H]3CCCOC3)c2=O)nc2c(C(=O)N[C@H]3CC[C@@H]3OC)cnn12] |
| I-878 | 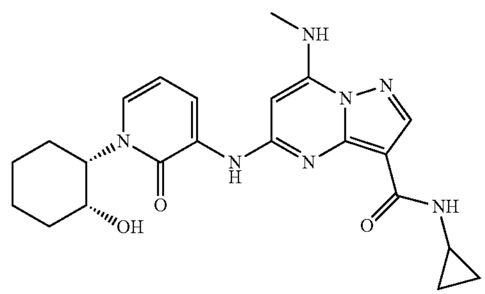 [SMILES: CNc1cc(Nc2cccn([C@H]3CCCC[C@H]3O)c2=O)nc2c(C(=O)NC3CC3)cnn12] |
| I-879 | 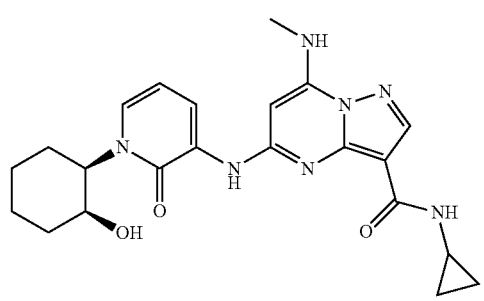 [SMILES: CNc1cc(Nc2cccn([C@@H]3CCCC[C@@H]3O)c2=O)nc2c(C(=O)NC3CC3)cnn12] |
| I-880 | 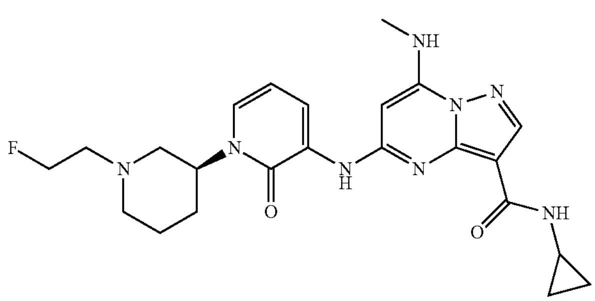 [SMILES: CNc1cc(Nc2cccn([C@H]3CCCN(CCF)C3)c2=O)nc2c(C(=O)NC3CC3)cnn12] |
| I-881 | 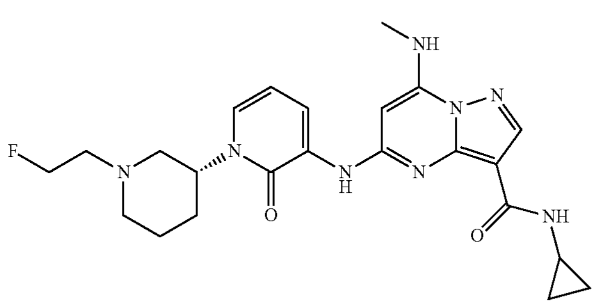 [SMILES: CNc1cc(Nc2cccn([C@@H]3CCCN(CCF)C3)c2=O)nc2c(C(=O)NC3CC3)cnn12] |

TABLE 1-continued

Selected Compounds

| Compound | Structure |
|---|---|
| I-882 | 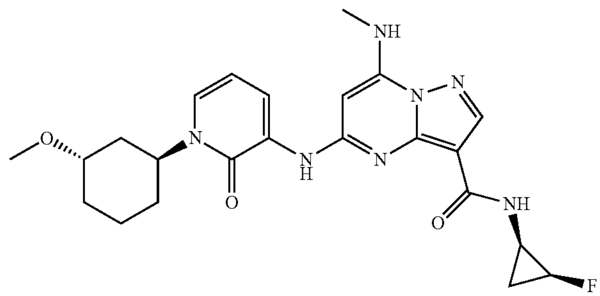 [SMILES: CNc1cc(Nc2cccn([C@H]3CCC[C@H](OC)C3)c2=O)nc2c(C(=O)N[C@@H]3C[C@@H]3F)cnn12] |
| I-883 | 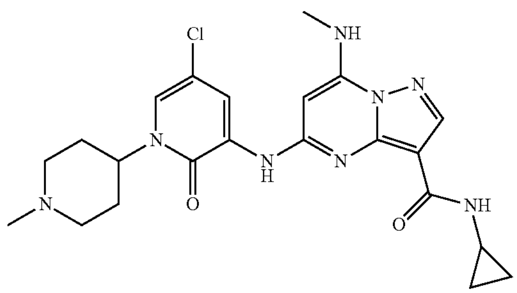 [SMILES: CNc1cc(Nc2cc(Cl)cn(C3CCN(C)CC3)c2=O)nc2c(C(=O)NC3CC3)cnn12] |
| I-884 | 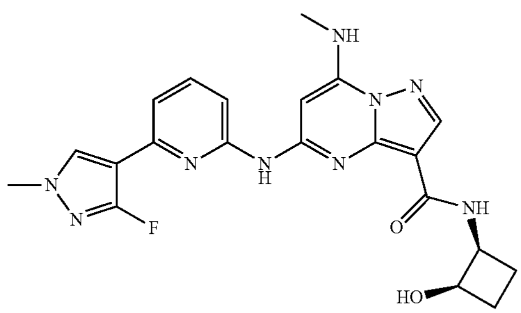 [SMILES: CNc1cc(Nc2cccc(-c3cn(C)nc3F)n2)nc2c(C(=O)N[C@H]3CC[C@H]3O)cnn12] |
| I-885 | 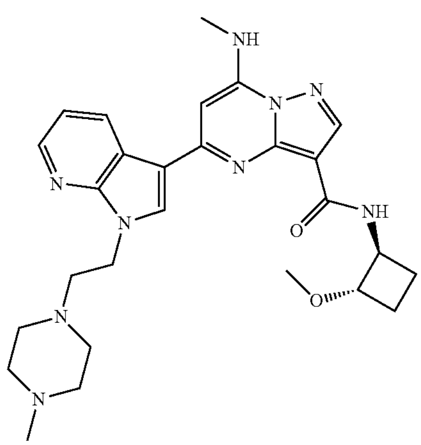 [SMILES: CNc1cc(-c2cn(CCN3CCN(C)CC3)c3ncccc23)nc2c(C(=O)N[C@H]3CC[C@@H]3OC)cnn12] |

TABLE 1-continued

Selected Compounds

| Compound | Structure |
|---|---|
| I-886 | 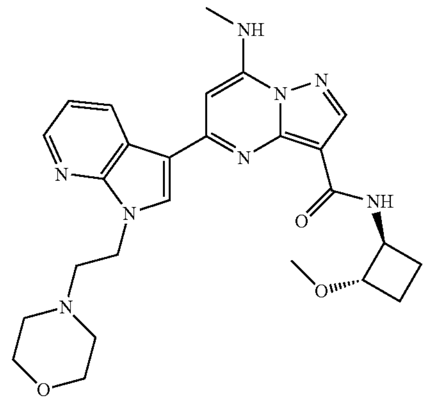 [SMILES: CNc1cc(-c2cn(CCN3CCOCC3)c3ncccc23)nc2c(C(=O)N[C@H]3CC[C@@H]3OC)cnn12] |
| I-887 | 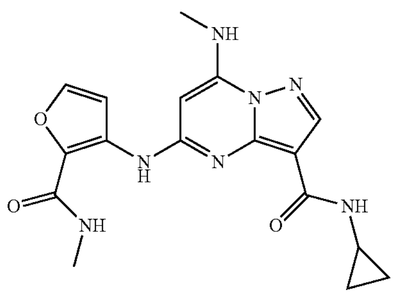 [SMILES: CNC(=O)c1occc1Nc1cc(NC)n2ncc(C(=O)NC3CC3)c2n1] |
| I-888 | 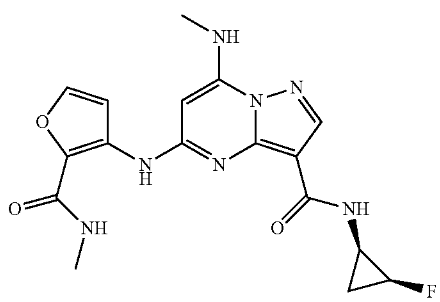 [SMILES: CNC(=O)c1occc1Nc1cc(NC)n2ncc(C(=O)N[C@@H]3C[C@@H]3F)c2n1] |
| I-889 | 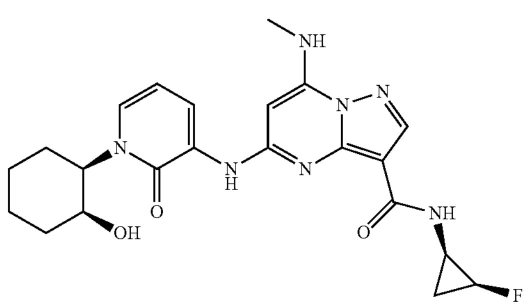 [SMILES: CNc1cc(Nc2cccn([C@@H]3CCCC[C@@H]3O)c2=O)nc2c(C(=O)N[C@@H]3C[C@@H]3F)cnn12] |

TABLE 1-continued
Selected Compounds
| Compound | Structure |
|---|---|
| I-890 | 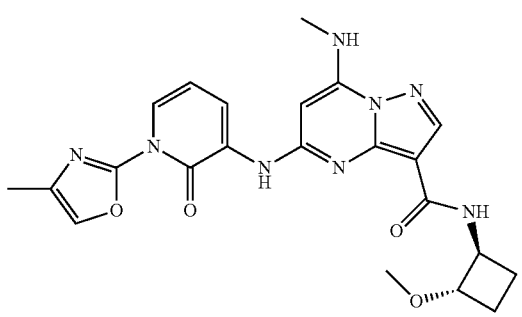 [SMILES: CNc1cc(Nc2cccn(-c3nc(C)co3)c2=O)nc2c(C(=O)N[C@H]3CC[C@@H]3OC)cnn12] |
| I-891 | 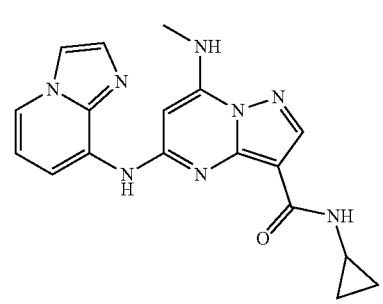 [SMILES: CNc1cc(Nc2cccn3ccnc23)nc2c(C(=O)NC3CC3)cnn12] |
| I-892 | 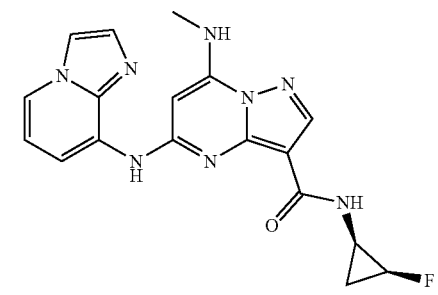 [SMILES: CNc1cc(Nc2cccn3ccnc23)nc2c(C(=O)N[C@@H]3C[C@@H]3F)cnn12] |
| I-893 | 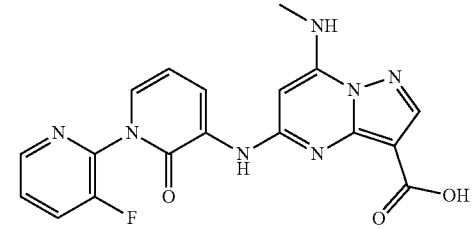 [SMILES: CNc1cc(Nc2cccn(-c3ncccc3F)c2=O)nc2c(C(=O)O)cnn12] |
| I-894 | 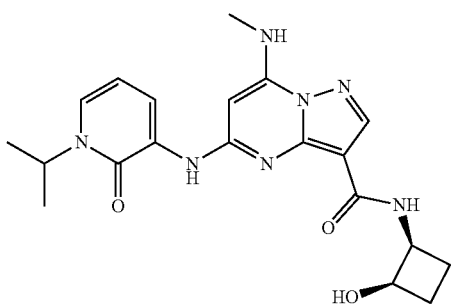 [SMILES: CNc1cc(Nc2cccn(C(C)C)c2=O)nc2c(C(=O)N[C@H]3CC[C@H]3O)cnn12] |

TABLE 1-continued

Selected Compounds

| Compound | Structure |
|---|---|
| I-895 | 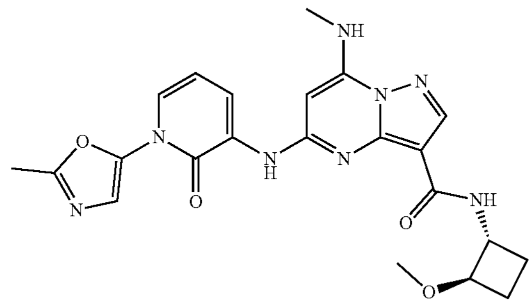 [SMILES: CNc1cc(Nc2cccn(-c3cnc(C)o3)c2=O)nc2c(C(=O)N[C@@H]3CC[C@H]3OC)cnn12] |
| I-896 | 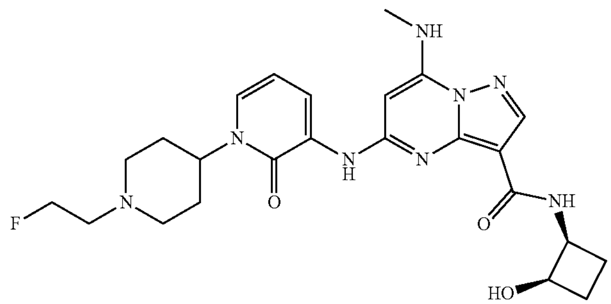 [SMILES: CNc1cc(Nc2cccn(C3CCN(CCF)CC3)c2=O)nc2c(C(=O)N[C@H]3CC[C@H]3O)cnn12] |
| I-897 | 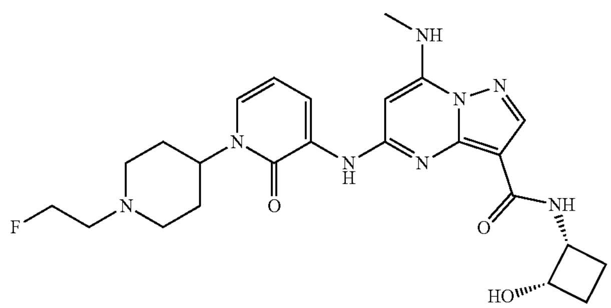 [SMILES: CNc1cc(Nc2cccn(C3CCN(CCF)CC3)c2=O)nc2c(C(=O)N[C@@H]3CC[C@@H]3O)cnn12] |
| I-898 | 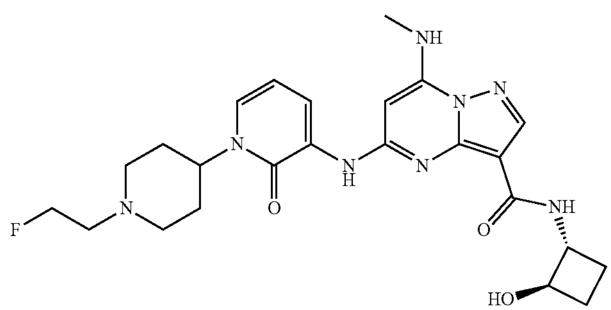 [SMILES: CNc1cc(Nc2cccn(C3CCN(CCF)CC3)c2=O)nc2c(C(=O)N[C@@H]3CC[C@H]3O)cnn12] |
| I-899 | 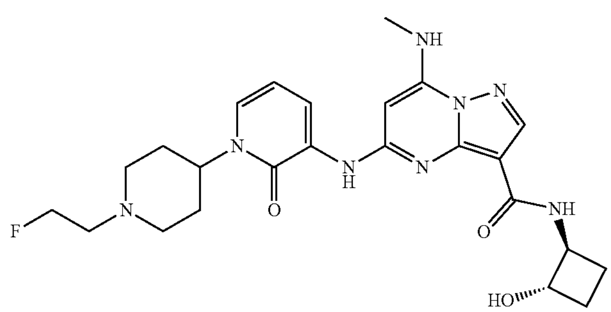 [SMILES: CNc1cc(Nc2cccn(C3CCN(CCF)CC3)c2=O)nc2c(C(=O)N[C@H]3CC[C@@H]3O)cnn12] |

TABLE 1-continued

| Selected Compounds | |
|---|---|
| Compound | Structure |
| I-900 | |
| I-901 | |
| I-902 | |
| I-903 | |
| I-904 | |

TABLE 1-continued

| Selected Compounds | |
|---|---|
| Compound | Structure |
| I-905 | |
| I-906 | |
| I-907 | |
| I-908 | |

TABLE 1-continued

Selected Compounds

| Compound | Structure |
|---|---|
| I-909 | 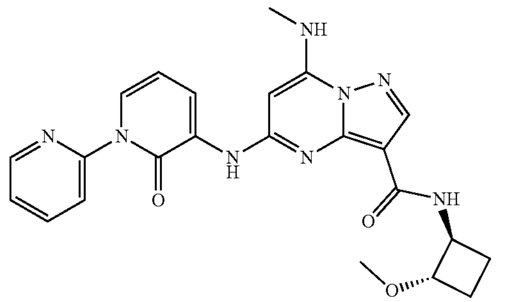 [SMILES: CNc1cc(Nc2cccn(-c3ccccn3)c2=O)nc2c(C(=O)N[C@H]3CC[C@@H]3OC)cnn12] |
| I-910 | 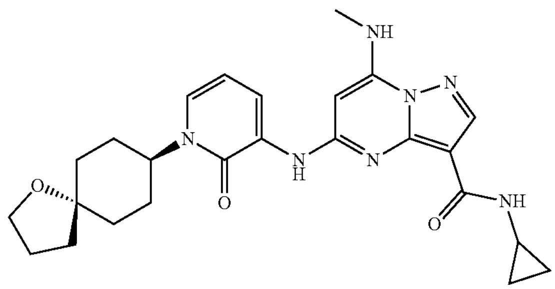 [SMILES: CNc1cc(Nc2cccn([C@H]3CC[C@@]4(CCCO4)CC3)c2=O)nc2c(C(=O)NC3CC3)cnn12] |
| I-911 | 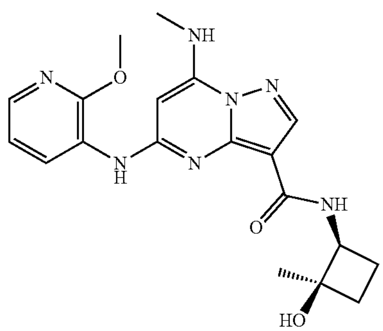 [SMILES: CNc1cc(Nc2cccnc2OC)nc2c(C(=O)N[C@H]3CC[C@@]3(C)O)cnn12] |
| I-912 | 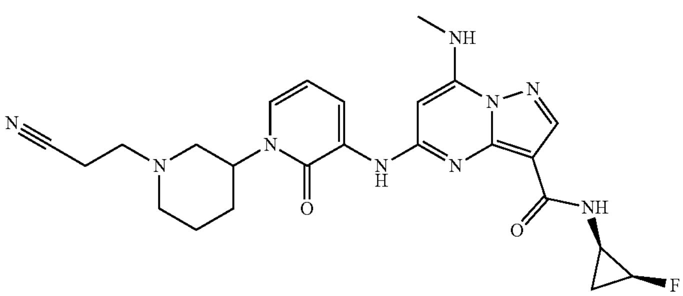 [SMILES: CNc1cc(Nc2cccn(C3CCCN(CCC#N)C3)c2=O)nc2c(C(=O)N[C@@H]3C[C@@H]3F)cnn12] |
| I-913 | 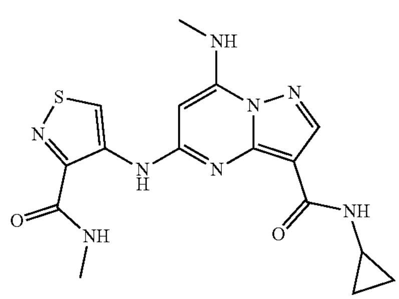 [SMILES: CNC(=O)c1nscc1Nc1cc(NC)n2ncc(C(=O)NC3CC3)c2n1] |

TABLE 1-continued

| Selected Compounds | |
|---|---|
| Compound | Structure |
| I-914 | |
| I-915 | |
| I-916 | |
| I-917 | |
| I-918 | |

TABLE 1-continued

Selected Compounds

| Compound | Structure |
|---|---|
| I-919 | 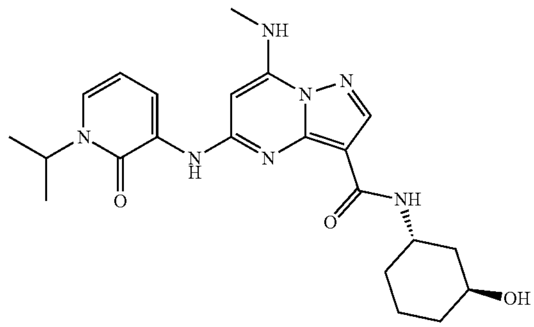 [SMILES: CNc1cc(Nc2cccn(C(C)C)c2=O)nc2c(C(=O)N[C@H]3CCC[C@H](O)C3)cnn12] |
| I-920 | 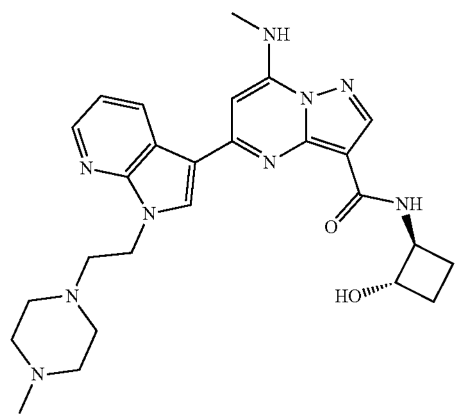 [SMILES: CNc1cc(-c2cn(CCN3CCN(C)CC3)c3ncccc23)nc2c(C(=O)N[C@H]3CC[C@@H]3O)cnn12] |
| I-921 | 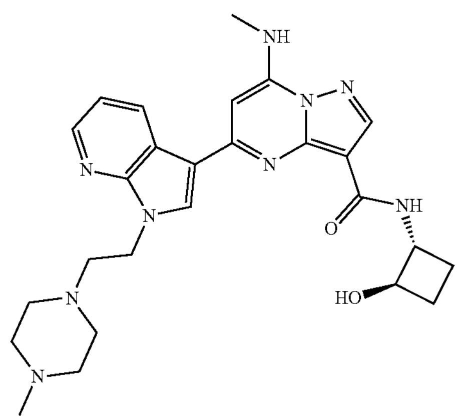 [SMILES: CNc1cc(-c2cn(CCN3CCN(C)CC3)c3ncccc23)nc2c(C(=O)N[C@@H]3CC[C@H]3O)cnn12] |
| I-922 | 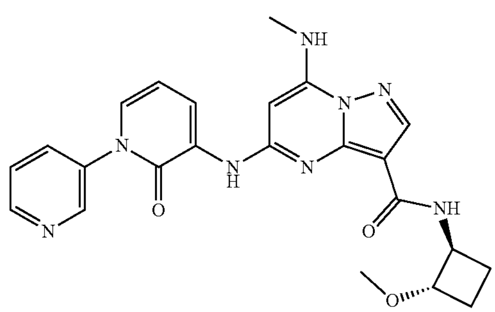 [SMILES: CNc1cc(Nc2cccn(-c3cccnc3)c2=O)nc2c(C(=O)N[C@H]3CC[C@@H]3OC)cnn12] |

TABLE 1-continued

Selected Compounds

| Compound | Structure |
|---|---|
| I-923 | 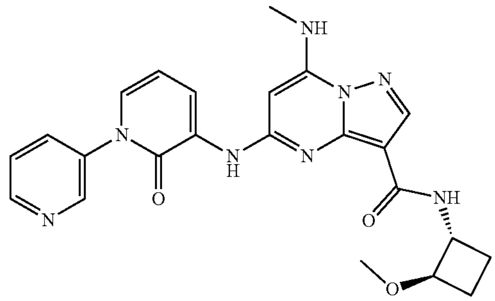 [SMILES: CNc1cc(Nc2cccn(-c3cccnc3)c2=O)nc2c(C(=O)N[C@@H]3CC[C@H]3OC)cnn12] |
| I-924 | 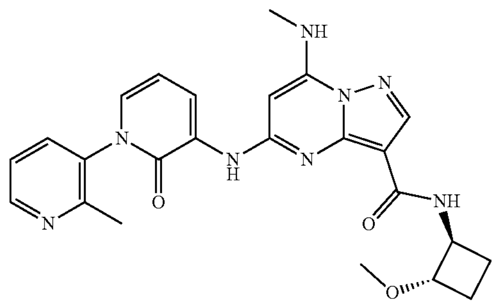 [SMILES: CNc1cc(Nc2cccn(-c3cccnc3C)c2=O)nc2c(C(=O)N[C@H]3CC[C@@H]3OC)cnn12] |
| I-925 | 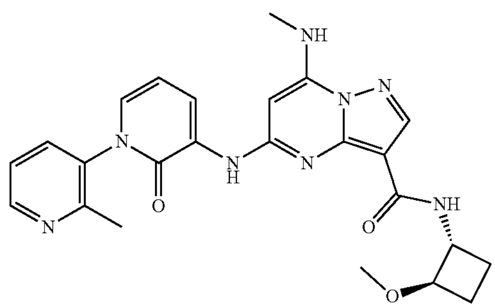 [SMILES: CNc1cc(Nc2cccn(-c3cccnc3C)c2=O)nc2c(C(=O)N[C@@H]3CC[C@H]3OC)cnn12] |
| I-926 | 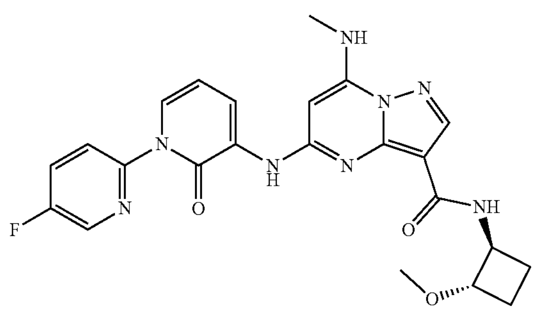 [SMILES: CNc1cc(Nc2cccn(-c3ccc(F)cn3)c2=O)nc2c(C(=O)N[C@H]3CC[C@@H]3OC)cnn12] |
| I-927 | 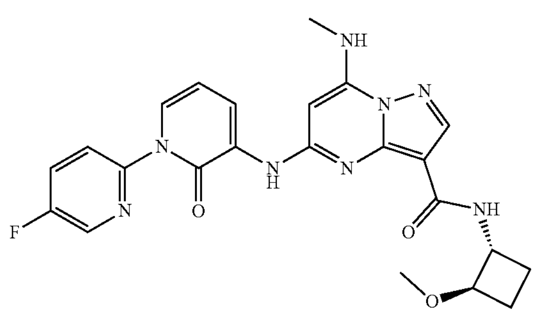 [SMILES: CNc1cc(Nc2cccn(-c3ccc(F)cn3)c2=O)nc2c(C(=O)N[C@@H]3CC[C@H]3OC)cnn12] |

TABLE 1-continued

Selected Compounds

| Compound | Structure |
|---|---|
| I-928 | 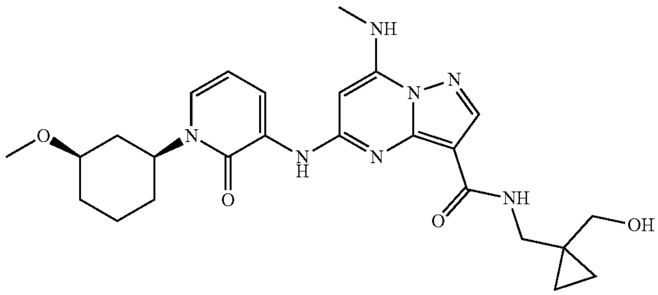 [SMILES: CNc1cc(Nc2cccn([C@H]3CCC[C@@H](OC)C3)c2=O)nc2c(C(=O)NCC3(CO)CC3)cnn12] |
| I-929 | 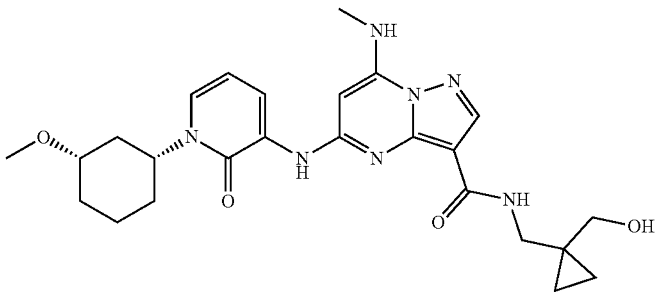 [SMILES: CNc1cc(Nc2cccn([C@@H]3CCC[C@H](OC)C3)c2=O)nc2c(C(=O)NCC3(CO)CC3)cnn12] |
| I-930 | 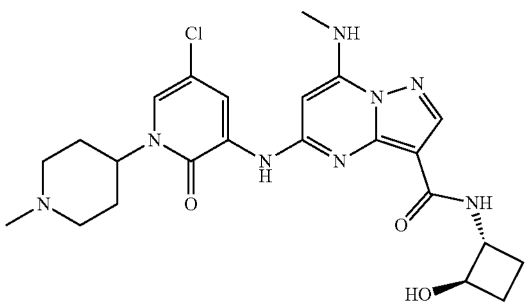 [SMILES: CNc1cc(Nc2cc(Cl)cn(C3CCN(C)CC3)c2=O)nc2c(C(=O)N[C@@H]3CC[C@H]3O)cnn12] |
| I-931 | 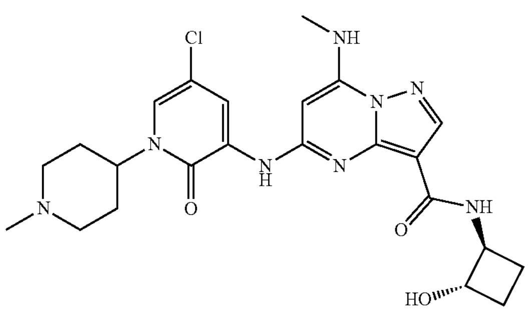 [SMILES: CNc1cc(Nc2cc(Cl)cn(C3CCN(C)CC3)c2=O)nc2c(C(=O)N[C@H]3CC[C@@H]3O)cnn12] |
| I-932 | 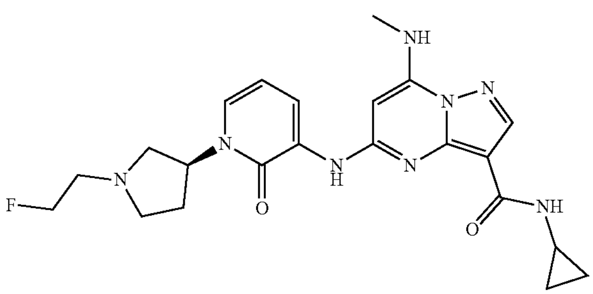 [SMILES: CNc1cc(Nc2cccn([C@H]3CCN(CCF)C3)c2=O)nc2c(C(=O)NC3CC3)cnn12] |

TABLE 1-continued

| Selected Compounds | |
|---|---|
| Compound | Structure |
| I-933 | |
| I-934 | |
| I-935 | |
| I-936 | |
| I-937 | |

TABLE 1-continued

| Selected Compounds | |
|---|---|
| Compound | Structure |
| I-938 | |
| I-939 | |
| I-940 | |
| I-941 | |
| I-942 | |

TABLE 1-continued

| Selected Compounds | |
|---|---|
| Compound | Structure |
| I-943 | |
| I-944 | |
| I-945 | |
| I-946 | |
| I-947 | |

TABLE 1-continued

Selected Compounds

| Compound | Structure |
| --- | --- |
| I-948 | 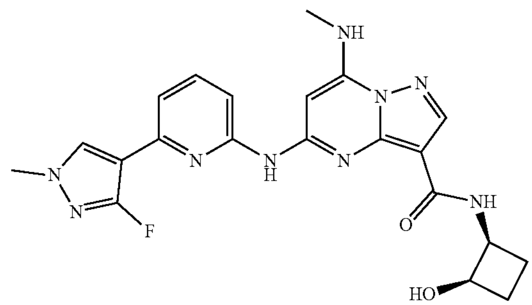 [SMILES: CNc1cc(Nc2cccc(-c3cn(C)nc3F)n2)nc2c(C(=O)N[C@H]3CC[C@H]3O)cnn12] |
| I-949 | 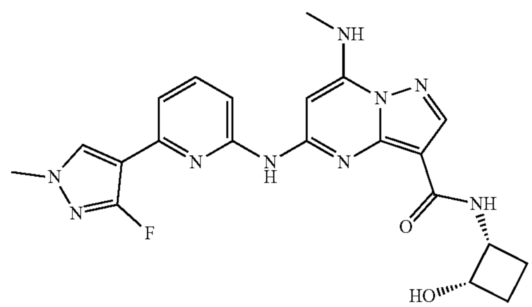 [SMILES: CNc1cc(Nc2cccc(-c3cn(C)nc3F)n2)nc2c(C(=O)N[C@@H]3CC[C@@H]3O)cnn12] |
| I-950 | 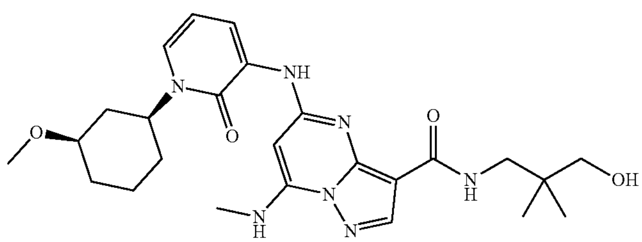 [SMILES: CNc1cc(Nc2cccn([C@H]3CCC[C@@H](OC)C3)c2=O)nc2c(C(=O)NCC(C)(C)CO)cnn12] |
| I-951 | 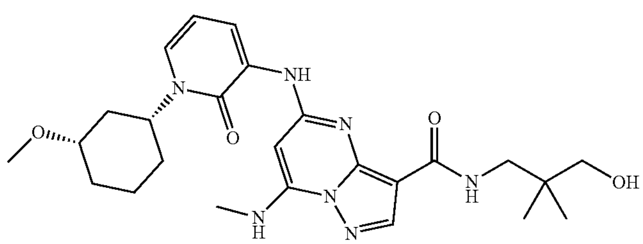 [SMILES: CNc1cc(Nc2cccn([C@@H]3CCC[C@H](OC)C3)c2=O)nc2c(C(=O)NCC(C)(C)CO)cnn12] |
| I-952 | 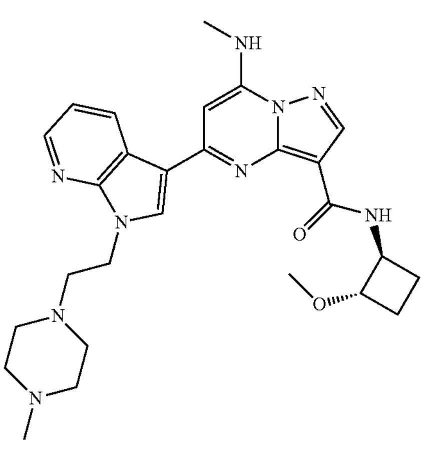 [SMILES: CNc1cc(-c2cn(CCN3CCN(C)CC3)c3ncccc23)nc2c(C(=O)N[C@H]3CC[C@@H]3OC)cnn12] |

TABLE 1-continued
| Selected Compounds | |
|---|---|
| Compound | Structure |
| I-953 | 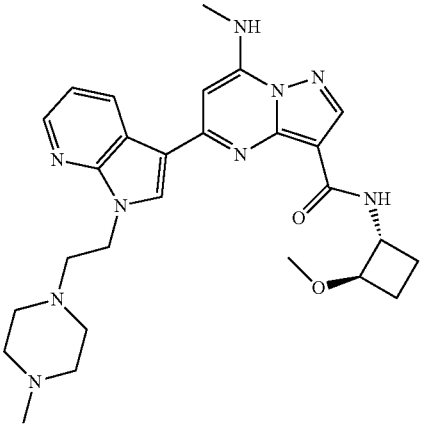 [SMILES: CNc1cc(-c2cn(CCN3CCN(C)CC3)c3ncccc23)nc2c(C(=O)N[C@@H]3CC[C@H]3OC)cnn12] |
| I-954 | 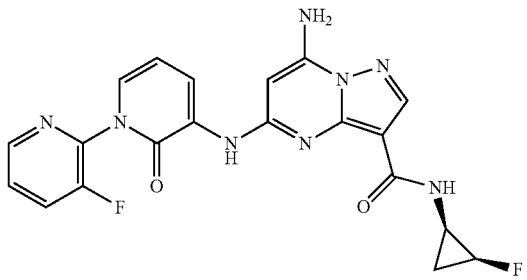 [SMILES: Nc1cc(Nc2cccn(-c3ncccc3F)c2=O)nc2c(C(=O)N[C@@H]3C[C@@H]3F)cnn12] |
| I-955 | 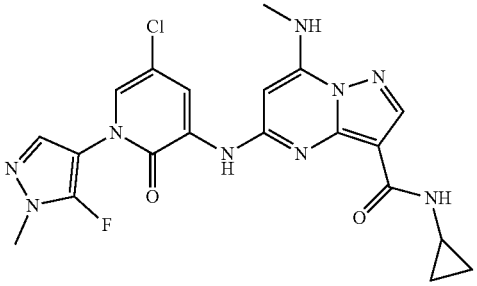 [SMILES: CNc1cc(Nc2cc(Cl)cn(-c3cnn(C)c3F)c2=O)nc2c(C(=O)NC3CC3)cnn12] |
| I-956 | 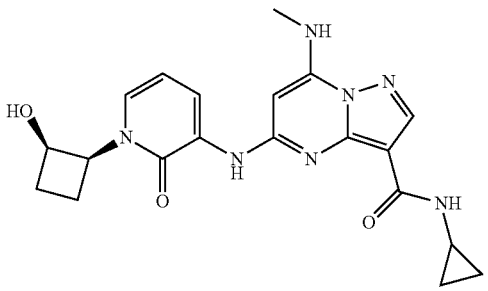 [SMILES: CNc1cc(Nc2cccn([C@H]3CC[C@H]3O)c2=O)nc2c(C(=O)NC3CC3)cnn12] |

TABLE 1-continued

Selected Compounds

| Compound | Structure |
|---|---|
| I-957 | 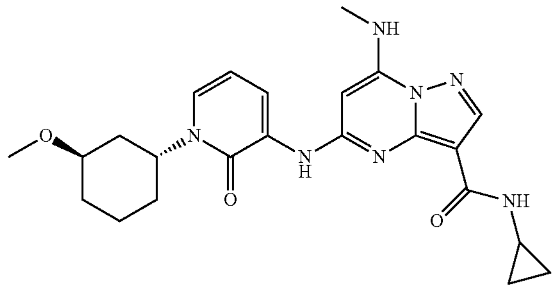 [SMILES: CNc1cc(Nc2cccn([C@@H]3CCC[C@@H](OC)C3)c2=O)nc2c(C(=O)NC3CC3)cnn12] |
| I-958 | 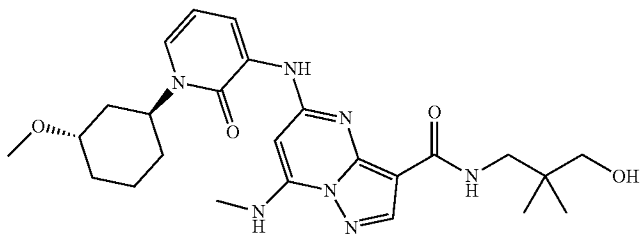 [SMILES: CNc1cc(Nc2cccn([C@H]3CCC[C@H](OC)C3)c2=O)nc2c(C(=O)NCC(C)(C)CO)cnn12] |
| I-959 | 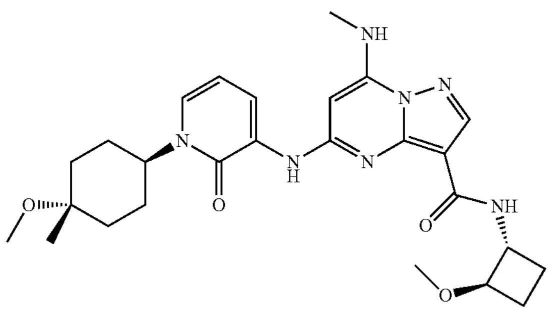 [SMILES: CNc1cc(Nc2cccn([C@H]3CC[C@](C)(OC)CC3)c2=O)nc2c(C(=O)N[C@@H]3CC[C@H]3OC)cnn12] |
| I-960 | 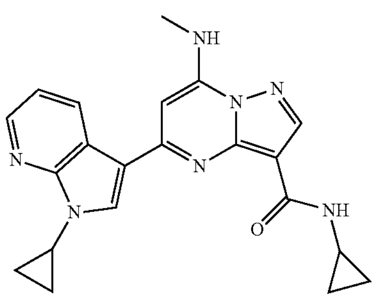 [SMILES: CNc1cc(-c2cn(C3CC3)c3ncccc23)nc2c(C(=O)NC3CC3)cnn12] |
| I-961 | 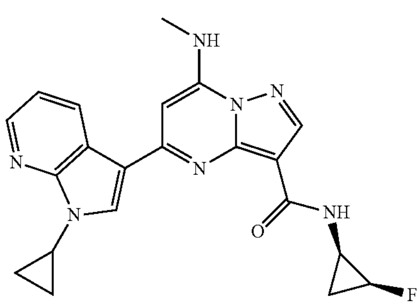 [SMILES: CNc1cc(-c2cn(C3CC3)c3ncccc23)nc2c(C(=O)N[C@@H]3C[C@@H]3F)cnn12] |

TABLE 1-continued
| Selected Compounds | |
|---|---|
| Compound | Structure |
| I-962 | 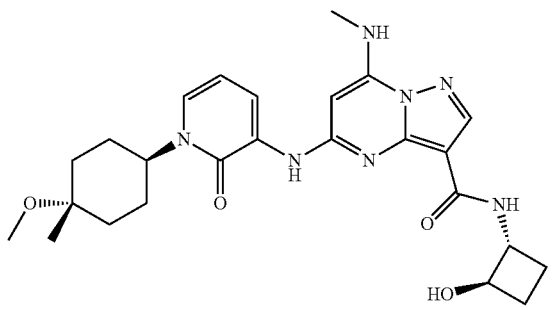 [SMILES: CNc1cc(Nc2cccn([C@H]3CC[C@](C)(OC)CC3)c2=O)nc2c(C(=O)N[C@@H]3CC[C@H]3O)cnn12] |
| I-963 | 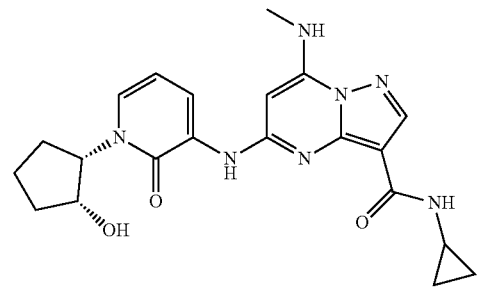 [SMILES: CNc1cc(Nc2cccn([C@H]3CCC[C@H]3O)c2=O)nc2c(C(=O)NC3CC3)cnn12] |
| I-964 | 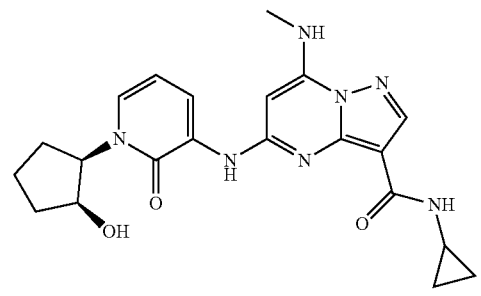 [SMILES: CNc1cc(Nc2cccn([C@@H]3CCC[C@@H]3O)c2=O)nc2c(C(=O)NC3CC3)cnn12] |
| I-965 | 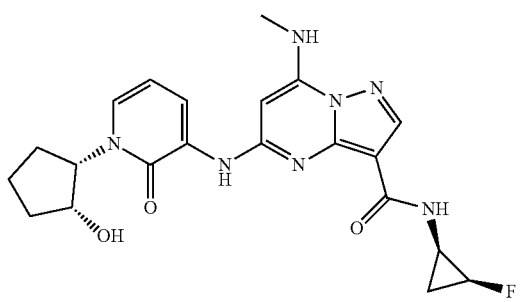 [SMILES: CNc1cc(Nc2cccn([C@H]3CCC[C@H]3O)c2=O)nc2c(C(=O)N[C@@H]3C[C@@H]3F)cnn12] |
| I-966 | 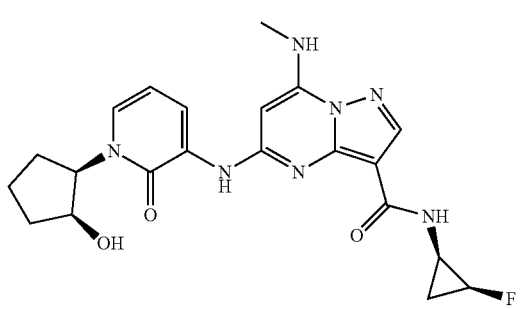 [SMILES: CNc1cc(Nc2cccn([C@@H]3CCC[C@@H]3O)c2=O)nc2c(C(=O)N[C@@H]3C[C@@H]3F)cnn12] |

TABLE 1-continued
Selected Compounds
| Compound | Structure |
|---|---|
| I-967 | 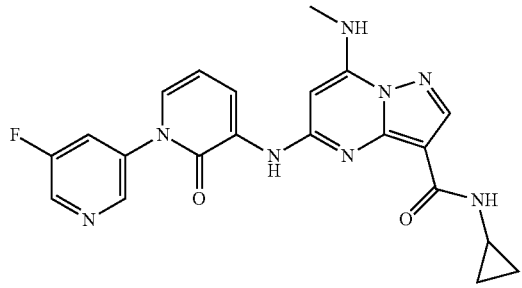 [SMILES: CNc1cc(Nc2cccn(-c3cncc(F)c3)c2=O)nc2c(C(=O)NC3CC3)cnn12] |
| I-968 | 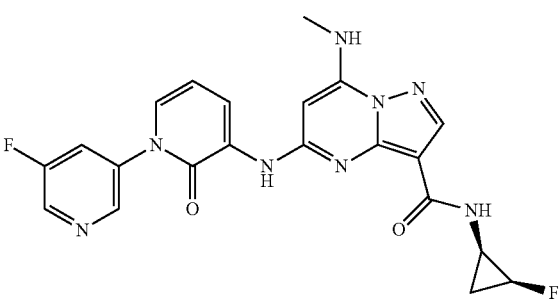 [SMILES: CNc1cc(Nc2cccn(-c3cncc(F)c3)c2=O)nc2c(C(=O)N[C@@H]3C[C@@H]3F)cnn12] |
| I-969 | 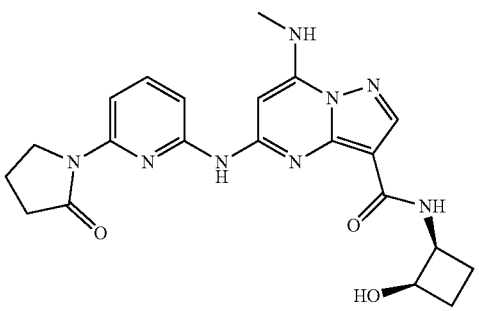 [SMILES: CNc1cc(Nc2cccc(N3CCCC3=O)n2)nc2c(C(=O)N[C@H]3CC[C@H]3O)cnn12] |
| I-970 | 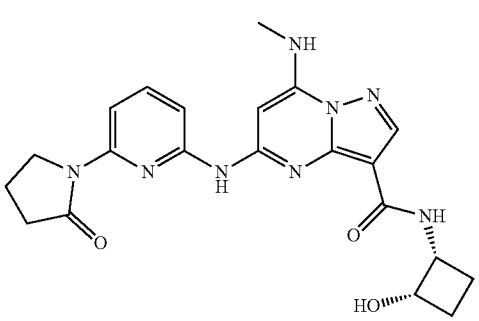 [SMILES: CNc1cc(Nc2cccc(N3CCCC3=O)n2)nc2c(C(=O)N[C@@H]3CC[C@@H]3O)cnn12] |
| I-971 | 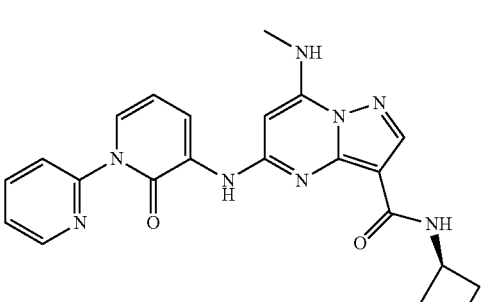 |

TABLE 1-continued

Selected Compounds

| Compound | Structure |
|---|---|
| I-972 | 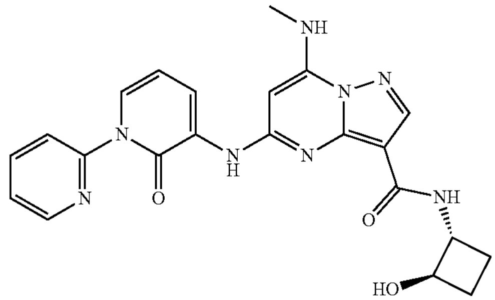 [SMILES: CNc1cc(Nc2cccn(-c3ccccn3)c2=O)nc2c(C(=O)N[C@@H]3CC[C@H]3O)cnn12] |
| I-973 | 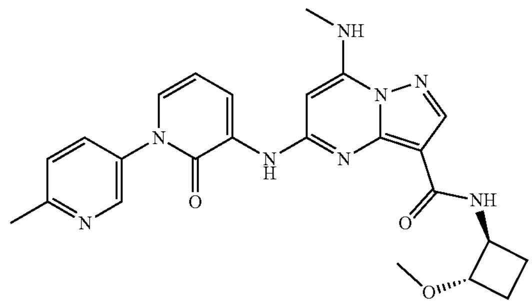 [SMILES: CNc1cc(Nc2cccn(-c3ccc(C)nc3)c2=O)nc2c(C(=O)N[C@H]3CC[C@@H]3OC)cnn12] |
| I-974 | 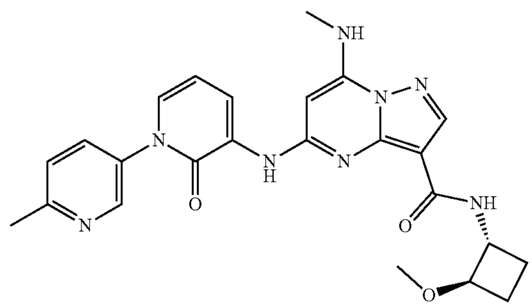 [SMILES: CNc1cc(Nc2cccn(-c3ccc(C)nc3)c2=O)nc2c(C(=O)N[C@@H]3CC[C@H]3OC)cnn12] |
| I-975 | 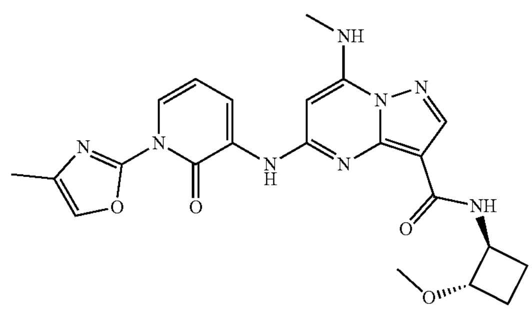 [SMILES: CNc1cc(Nc2cccn(-c3nc(C)co3)c2=O)nc2c(C(=O)N[C@H]3CC[C@@H]3OC)cnn12] |
| I-976 | 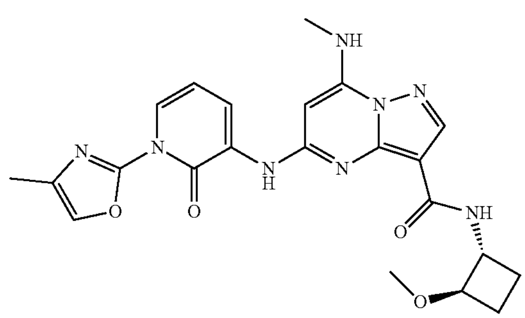 [SMILES: CNc1cc(Nc2cccn(-c3nc(C)co3)c2=O)nc2c(C(=O)N[C@@H]3CC[C@H]3OC)cnn12] |

TABLE 1-continued
| Compound | Structure |
|---|---|
| I-977 | 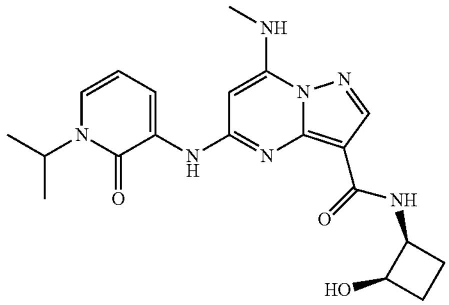 [SMILES: CNc1cc(Nc2cccn(C(C)C)c2=O)nc2c(C(=O)N[C@H]3CC[C@H]3O)cnn12] |
| I-978 | 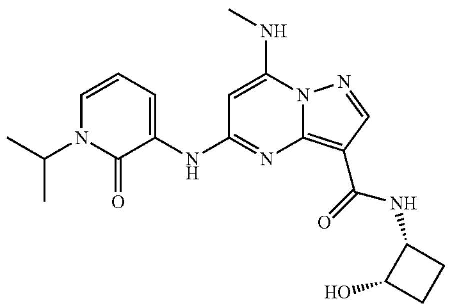 [SMILES: CNc1cc(Nc2cccn(C(C)C)c2=O)nc2c(C(=O)N[C@@H]3CC[C@@H]3O)cnn12] |
| I-979 | 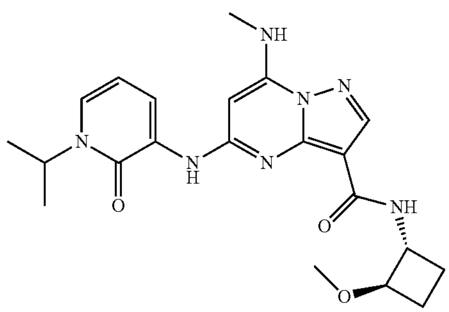 [SMILES: CNc1cc(Nc2cccn(C(C)C)c2=O)nc2c(C(=O)N[C@@H]3CC[C@H]3OC)cnn12] |
| I-980 | 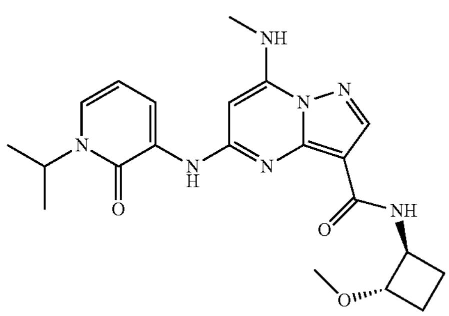 [SMILES: CNc1cc(Nc2cccn(C(C)C)c2=O)nc2c(C(=O)N[C@H]3CC[C@@H]3OC)cnn12] |
| I-981 | 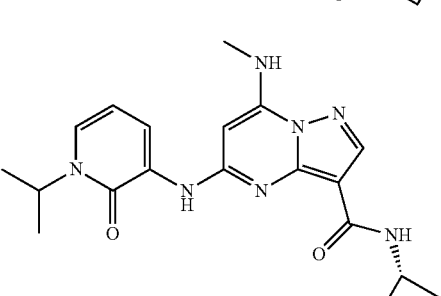 |

TABLE 1-continued

Selected Compounds

| Compound | Structure |
|---|---|
| I-982 | 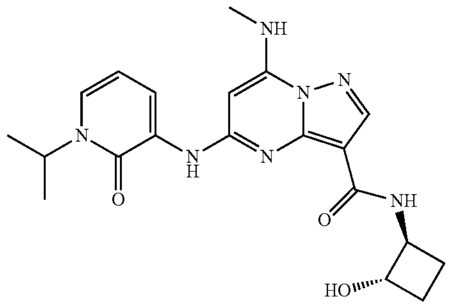 [SMILES: CNc1cc(Nc2cccn(C(C)C)c2=O)nc2c(C(=O)N[C@H]3CC[C@@H]3O)cnn12] |
| I-983 | 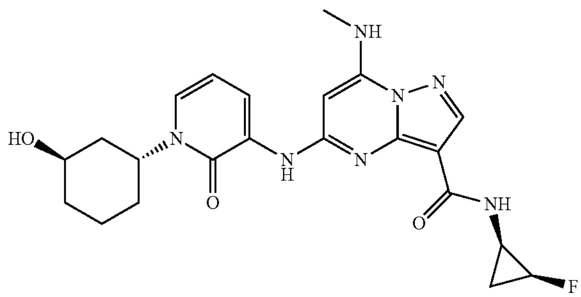 [SMILES: CNc1cc(Nc2cccn([C@@H]3CCC[C@@H](O)C3)c2=O)nc2c(C(=O)N[C@@H]3C[C@@H]3F)cnn12] |
| I-984 | 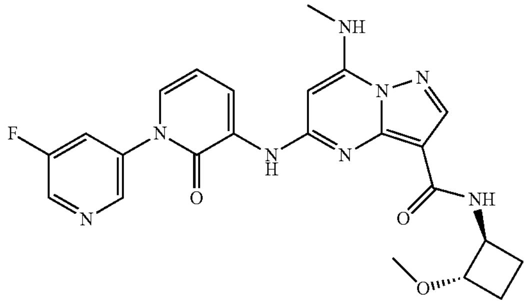 [SMILES: CNc1cc(Nc2cccn(-c3cncc(F)c3)c2=O)nc2c(C(=O)N[C@H]3CC[C@@H]3OC)cnn12] |
| I-985 | 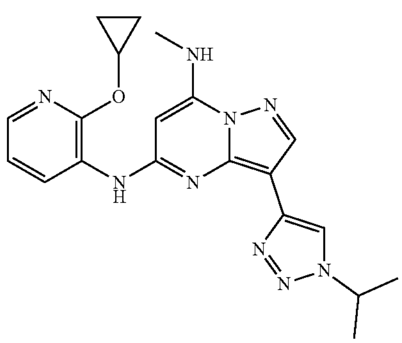 [SMILES: CNc1cc(Nc2cccnc2OC2CC2)nc2c(-c3cn(C(C)C)nn3)cnn12] |
| I-986 | 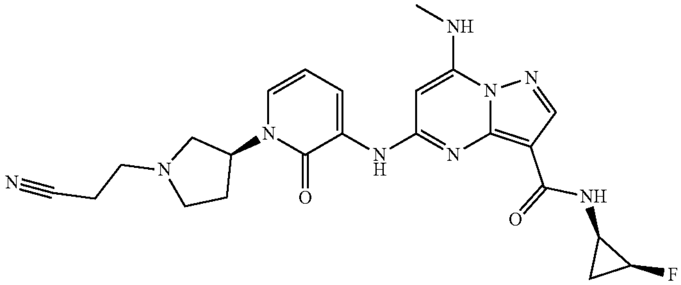 [SMILES: CNc1cc(Nc2cccn([C@H]3CCN(CCC#N)C3)c2=O)nc2c(C(=O)N[C@@H]3C[C@@H]3F)cnn12] |

TABLE 1-continued
Selected Compounds
| Compound | Structure |
|---|---|
| I-987 | 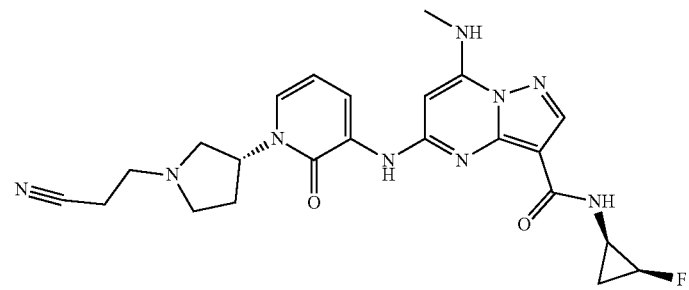 [SMILES: CNc1cc(Nc2cccn([C@@H]3CCN(CCC#N)C3)c2=O)nc2c(C(=O)N[C@@H]3C[C@@H]3F)cnn12] |
| I-988 | 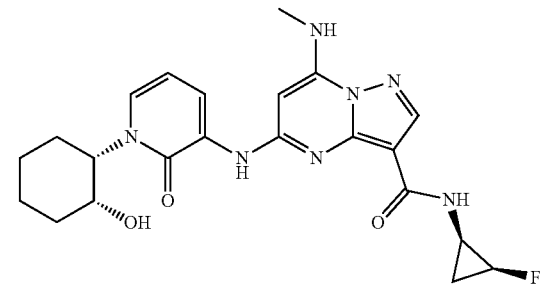 [SMILES: CNc1cc(Nc2cccn([C@H]3CCCC[C@H]3O)c2=O)nc2c(C(=O)N[C@@H]3C[C@@H]3F)cnn12] |
| I-989 | 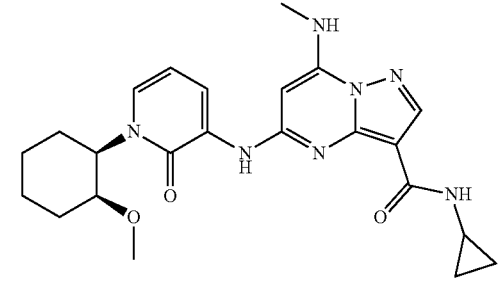 [SMILES: CNc1cc(Nc2cccn([C@@H]3CCCC[C@@H]3OC)c2=O)nc2c(C(=O)NC3CC3)cnn12] |
| I-990 | 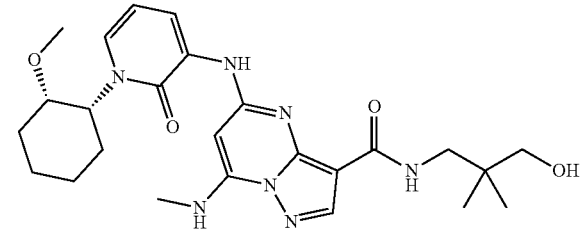 [SMILES: CNc1cc(Nc2cccn([C@@H]3CCCC[C@@H]3OC)c2=O)nc2c(C(=O)NCC(C)(C)CO)cnn12] |
| I-991 | 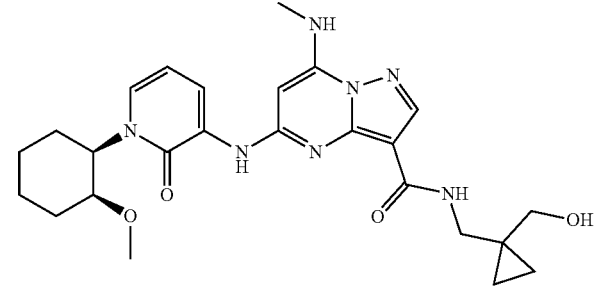 [SMILES: CNc1cc(Nc2cccn([C@@H]3CCCC[C@@H]3OC)c2=O)nc2c(C(=O)NCC3(CO)CC3)cnn12] |

TABLE 1-continued

Selected Compounds

| Compound | Structure |
|---|---|
| I-992 | 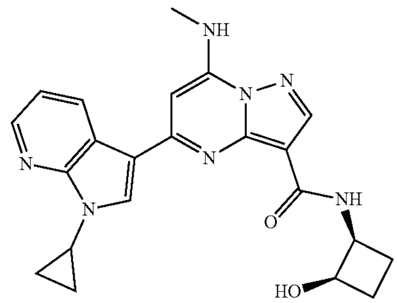 [SMILES: CNc1cc(-c2cn(C3CC3)c3ncccc23)nc2c(C(=O)N[C@H]3CC[C@H]3O)cnn12] |
| I-993 | 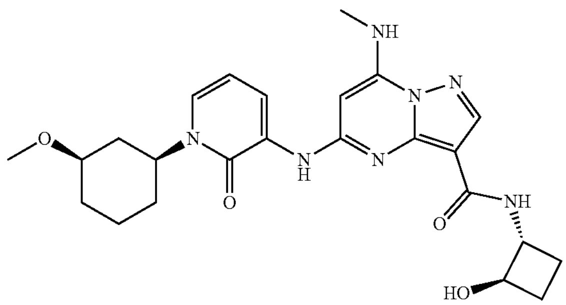 |
| I-994 | 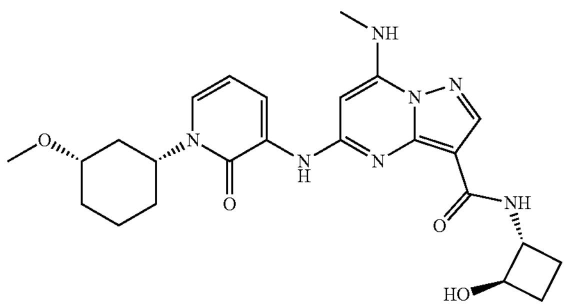 [SMILES: CNc1cc(Nc2cccn([C@@H]3CCC[C@H](OC)C3)c2=O)nc2c(C(=O)N[C@@H]3CC[C@H]3O)cnn12] |
| I-995 | 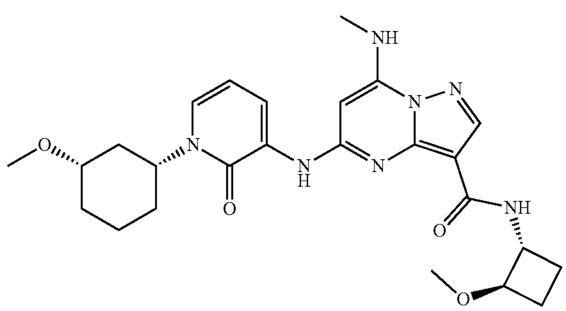 [SMILES: CNc1cc(Nc2cccn([C@@H]3CCC[C@H](OC)C3)c2=O)nc2c(C(=O)N[C@@H]3CC[C@H]3OC)cnn12] |
| I-996 | 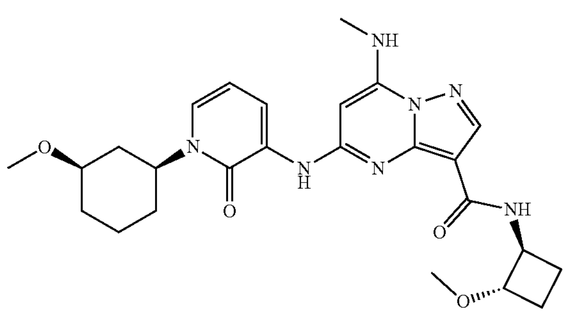 [SMILES: CNc1cc(Nc2cccn([C@H]3CCC[C@@H](OC)C3)c2=O)nc2c(C(=O)N[C@H]3CC[C@@H]3OC)cnn12] |

TABLE 1-continued
| Selected Compounds | |
|---|---|
| Compound | Structure |
| I-997 | 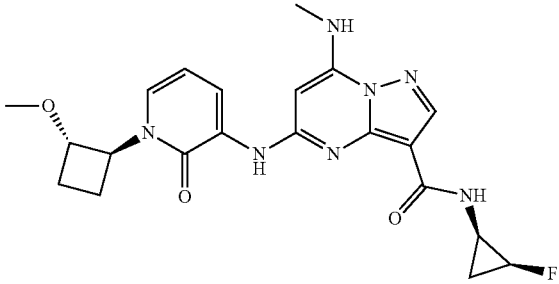 [SMILES: CNc1cc(Nc2cccn([C@H]3CC[C@@H]3OC)c2=O)nc2c(C(=O)N[C@@H]3C[C@@H]3F)cnn12] |
| I-998 | 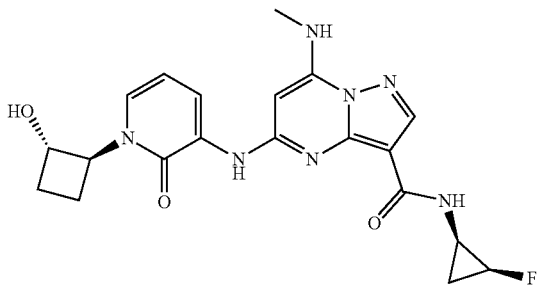 [SMILES: CNc1cc(Nc2cccn([C@H]3CC[C@@H]3O)c2=O)nc2c(C(=O)N[C@@H]3C[C@@H]3F)cnn12] |
| I-999 | 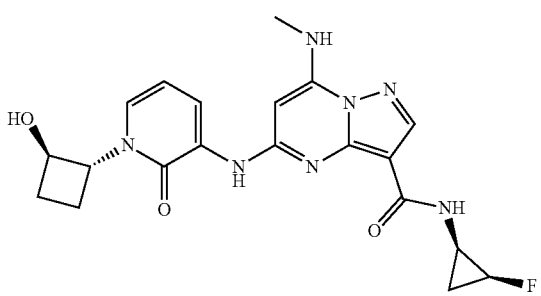 [SMILES: CNc1cc(Nc2cccn([C@@H]3CC[C@H]3O)c2=O)nc2c(C(=O)N[C@@H]3C[C@@H]3F)cnn12] |
| I-1000 | 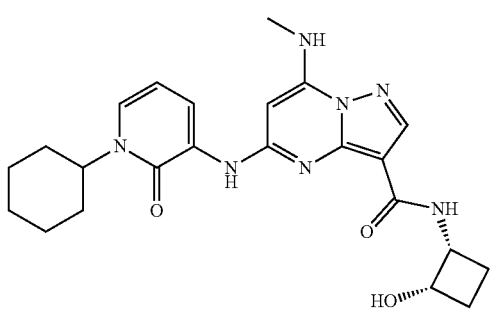 [SMILES: CNc1cc(Nc2cccn(C3CCCCC3)c2=O)nc2c(C(=O)N[C@@H]3CC[C@@H]3O)cnn12] |
| I-1001 | 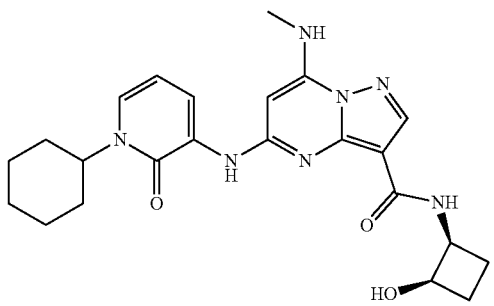 [SMILES: CNc1cc(Nc2cccn(C3CCCCC3)c2=O)nc2c(C(=O)N[C@H]3CC[C@H]3O)cnn12] |

TABLE 1-continued

Selected Compounds

| Compound | Structure |
|---|---|
| I-1002 | 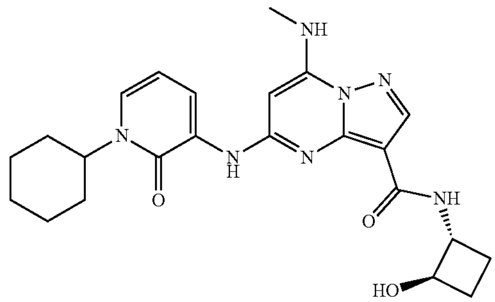 [SMILES: CNc1cc(Nc2cccn(C3CCCCC3)c2=O)nc2c(C(=O)N[C@@H]3CC[C@H]3O)cnn12] |
| I-1003 | 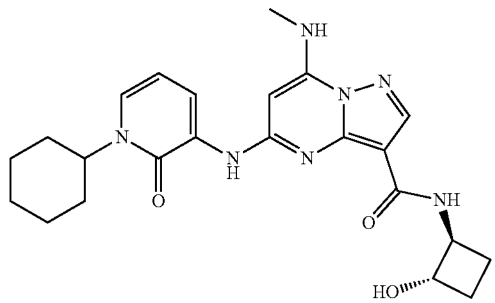 [SMILES: CNc1cc(Nc2cccn(C3CCCCC3)c2=O)nc2c(C(=O)N[C@H]3CC[C@@H]3O)cnn12] |
| I-1004 | 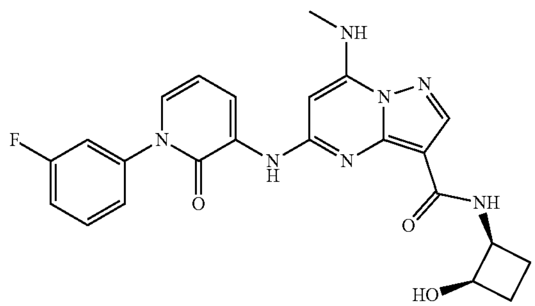 [SMILES: CNc1cc(Nc2cccn(-c3cccc(F)c3)c2=O)nc2c(C(=O)N[C@H]3CC[C@H]3O)cnn12] |
| I-1005 | 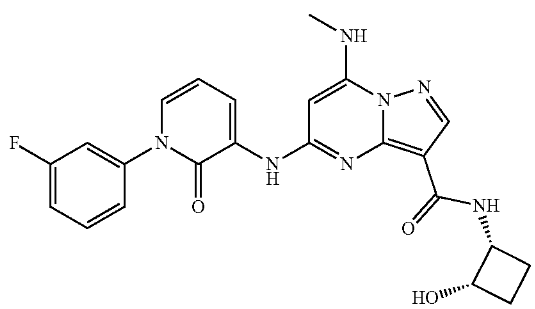 [SMILES: CNc1cc(Nc2cccn(-c3cccc(F)c3)c2=O)nc2c(C(=O)N[C@@H]3CC[C@@H]3O)cnn12] |
| I-1006 | 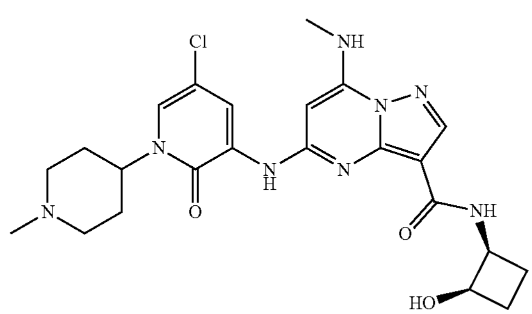 [SMILES: CNc1cc(Nc2cc(Cl)cn(C3CCN(C)CC3)c2=O)nc2c(C(=O)N[C@H]3CC[C@H]3O)cnn12] |

TABLE 1-continued
Selected Compounds
| Compound | Structure |
|---|---|
| I-1007 | 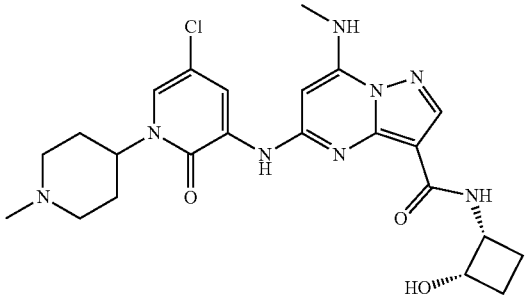 [SMILES: CNc1cc(Nc2cc(Cl)cn(C3CCN(C)CC3)c2=O)nc2c(C(=O)N[C@@H]3CC[C@@H]3O)cnn12] |
| I-1008 | 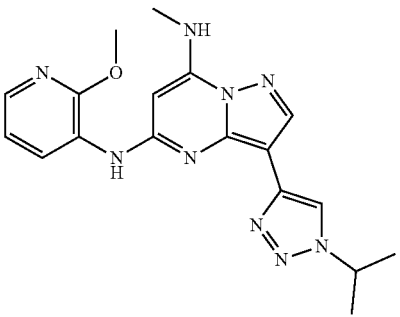 [SMILES: CNc1cc(Nc2cccnc2OC)nc2c(-c3cn(C(C)C)nn3)cnn12] |
| I-1009 | 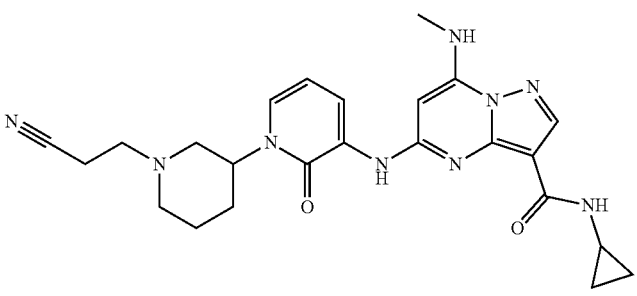 [SMILES: CNc1cc(Nc2cccn(C3CCCN(CCC#N)C3)c2=O)nc2c(C(=O)NC3CC3)cnn12] |
| I-1010 | 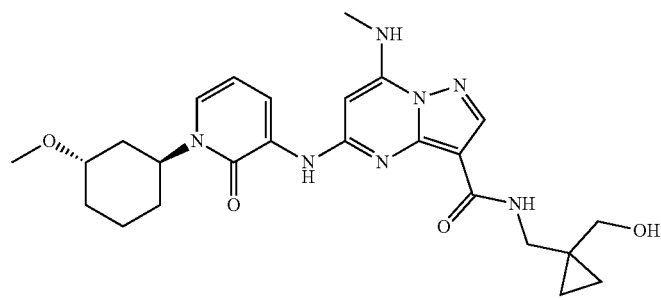 [SMILES: CNc1cc(Nc2cccn([C@H]3CCC[C@H](OC)C3)c2=O)nc2c(C(=O)NCC3(CO)CC3)cnn12] |
| I-1011 | 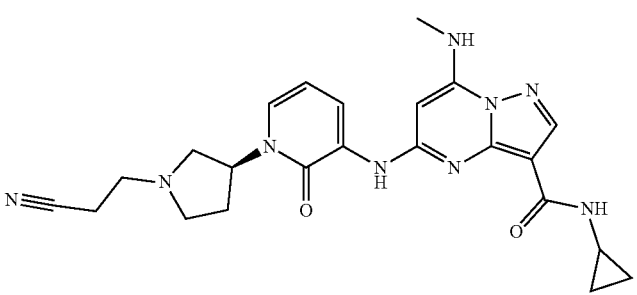 [SMILES: CNc1cc(Nc2cccn([C@H]3CCN(CCC#N)C3)c2=O)nc2c(C(=O)NC3CC3)cnn12] |

TABLE 1-continued
Selected Compounds
| Compound | Structure |
|---|---|
| I-1012 | 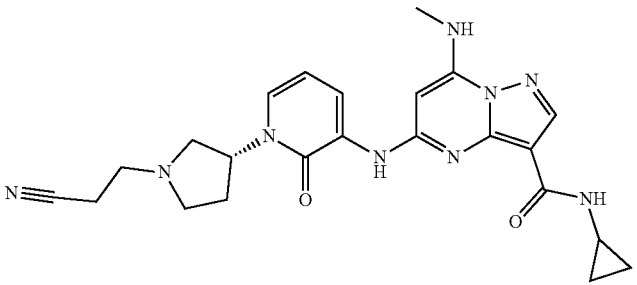 [SMILES: CNc1cc(Nc2cccn([C@@H]3CCN(CCC#N)C3)c2=O)nc2c(C(=O)NC3CC3)cnn12] |
| I-1013 | 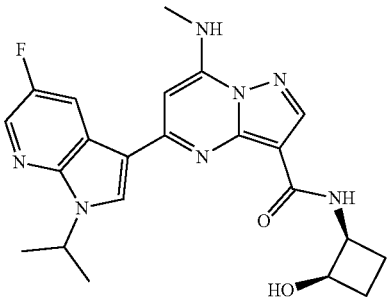 [SMILES: CNc1cc(-c2cn(C(C)C)c3ncc(F)cc23)nc2c(C(=O)N[C@H]3CC[C@H]3O)cnn12] |
| I-1014 | 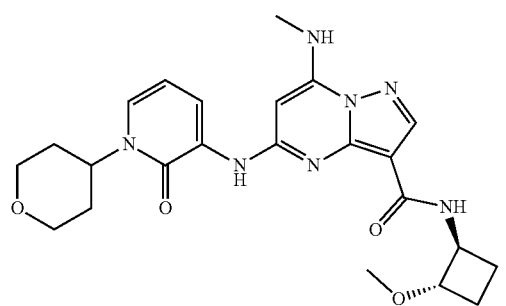 [SMILES: CNc1cc(Nc2cccn(C3CCOCC3)c2=O)nc2c(C(=O)N[C@H]3CC[C@@H]3OC)cnn12] |
| I-1015 | 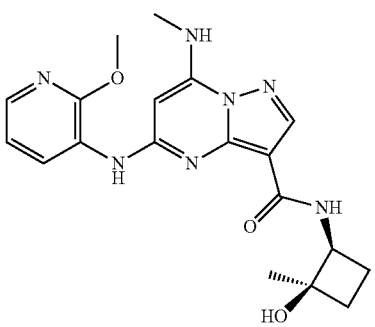 [SMILES: CNc1cc(Nc2cccnc2OC)nc2c(C(=O)N[C@H]3CC[C@@]3(C)O)cnn12] |
| I-1016 | 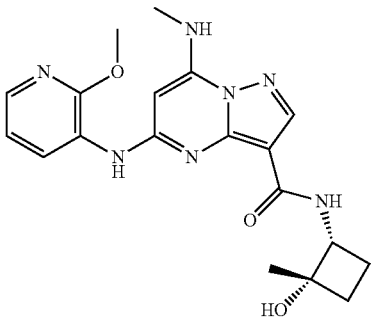 [SMILES: CNc1cc(Nc2cccnc2OC)nc2c(C(=O)N[C@@H]3CC[C@]3(C)O)cnn12] |

TABLE 1-continued

Selected Compounds

| Compound | Structure |
|---|---|
| I-1017 | 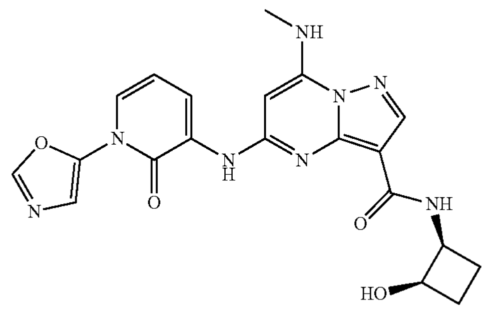 [SMILES: CNc1cc(Nc2cccn(-c3cnco3)c2=O)nc2c(C(=O)N[C@H]3CC[C@H]3O)cnn12] |
| I-1018 | 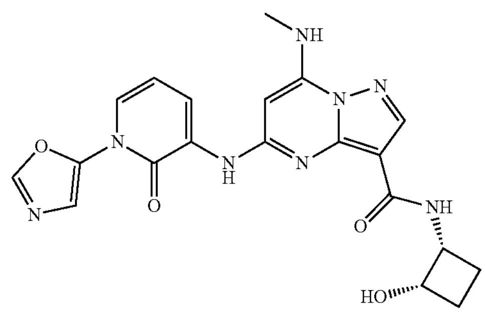 [SMILES: CNc1cc(Nc2cccn(-c3cnco3)c2=O)nc2c(C(=O)N[C@@H]3CC[C@@H]3O)cnn12] |
| I-1019 | 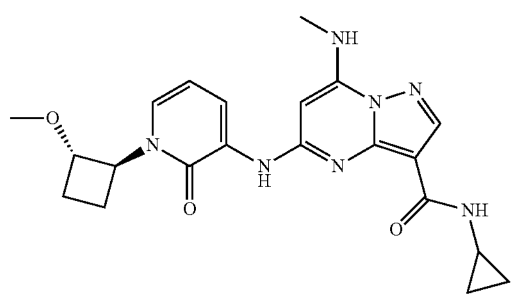 [SMILES: CNc1cc(Nc2cccn([C@H]3CC[C@@H]3OC)c2=O)nc2c(C(=O)NC3CC3)cnn12] |
| I-1020 | 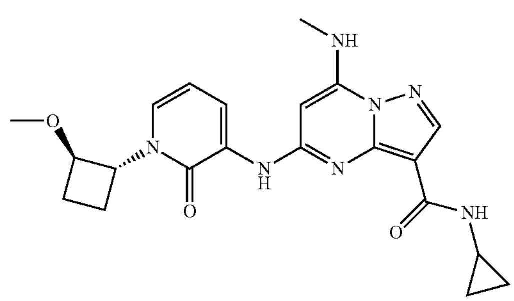 [SMILES: CNc1cc(Nc2cccn([C@@H]3CC[C@H]3OC)c2=O)nc2c(C(=O)NC3CC3)cnn12] |
| I-1021 | 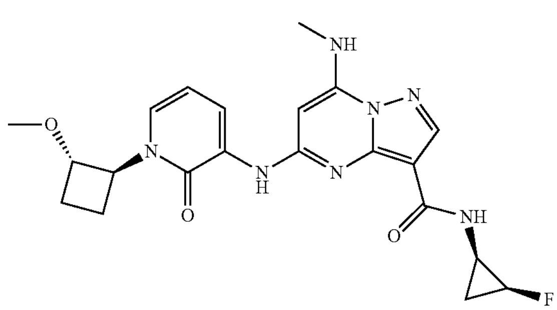 [SMILES: CNc1cc(Nc2cccn([C@H]3CC[C@@H]3OC)c2=O)nc2c(C(=O)N[C@@H]3C[C@@H]3F)cnn12] |

TABLE 1-continued
| Compound | Structure |
|---|---|
| I-1022 | 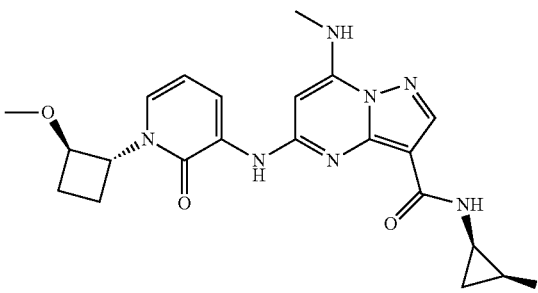 |
| I-1023 | 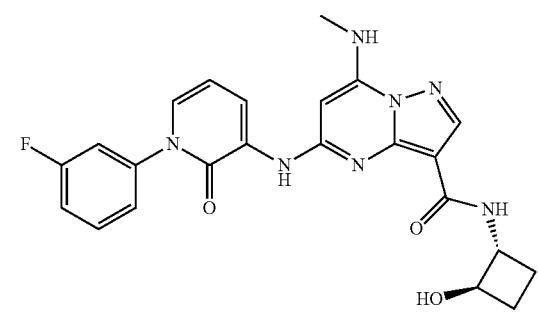 [SMILES: CNc1cc(Nc2cccn(-c3cccc(F)c3)c2=O)nc2c(C(=O)N[C@@H]3CC[C@H]3O)cnn12] |
| I-1024 | 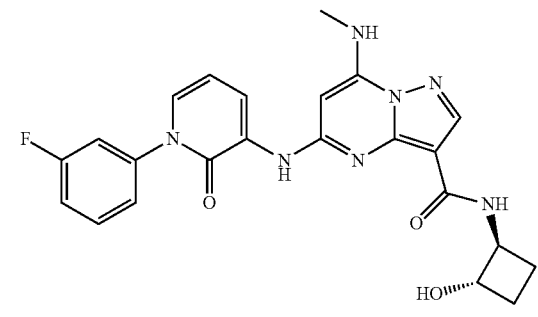 [SMILES: CNc1cc(Nc2cccn(-c3cccc(F)c3)c2=O)nc2c(C(=O)N[C@H]3CC[C@@H]3O)cnn12] |
| I-1025 | 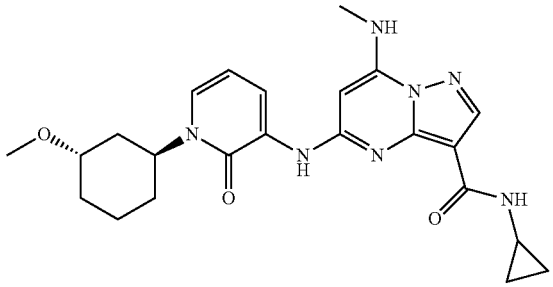 [SMILES: CNc1cc(Nc2cccn([C@H]3CCC[C@H](OC)C3)c2=O)nc2c(C(=O)NC3CC3)cnn12] |
| I-1026 | 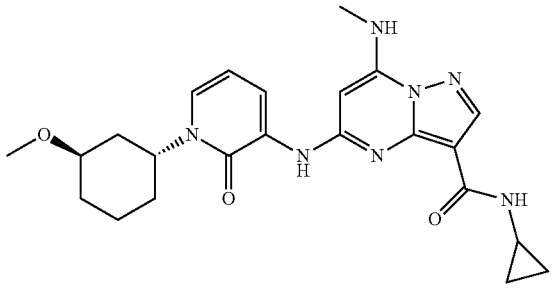 [SMILES: CNc1cc(Nc2cccn([C@@H]3CCC[C@@H](OC)C3)c2=O)nc2c(C(=O)NC3CC3)cnn12] |

TABLE 1-continued

Selected Compounds

| Compound | Structure |
|---|---|
| I-1027 | 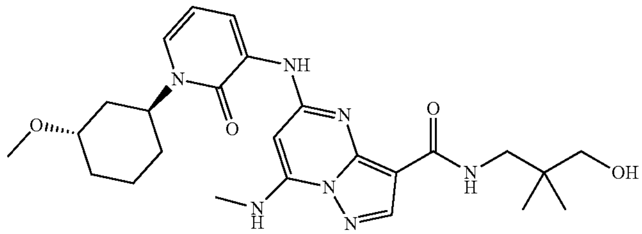 [SMILES: CNc1cc(Nc2cccn([C@H]3CCC[C@H](OC)C3)c2=O)nc2c(C(=O)NCC(C)(C)CO)cnn12] |
| I-1028 | 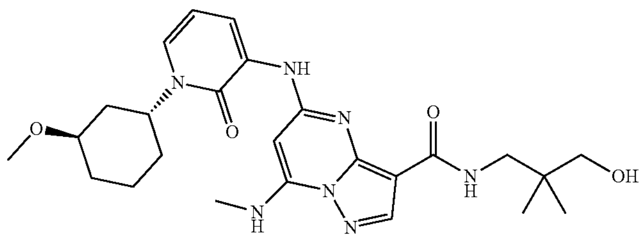 [SMILES: CNc1cc(Nc2cccn([C@@H]3CCC[C@@H](OC)C3)c2=O)nc2c(C(=O)NCC(C)(C)CO)cnn12] |
| I-1029 | 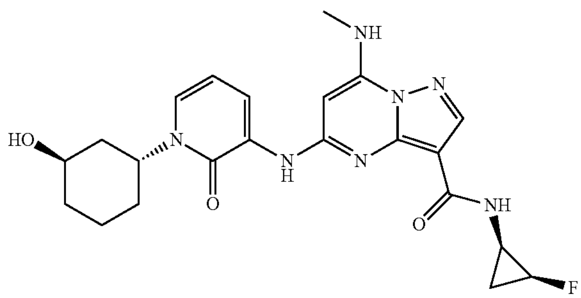 [SMILES: CNc1cc(Nc2cccn([C@@H]3CCC[C@@H](O)C3)c2=O)nc2c(C(=O)N[C@@H]3C[C@@H]3F)cnn12] |
| I-1030 | 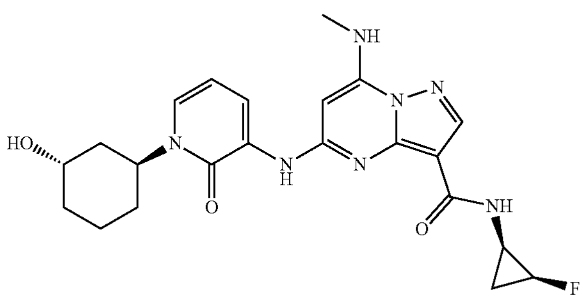 [SMILES: CNc1cc(Nc2cccn([C@H]3CCC[C@H](O)C3)c2=O)nc2c(C(=O)N[C@@H]3C[C@@H]3F)cnn12] |
| I-1031 | 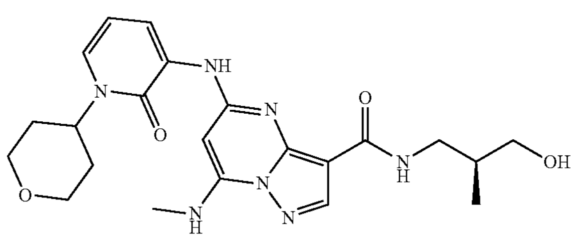 [SMILES: CNc1cc(Nc2cccn(C3CCOCC3)c2=O)nc2c(C(=O)NC[C@H](C)CO)cnn12] |
| I-1032 | 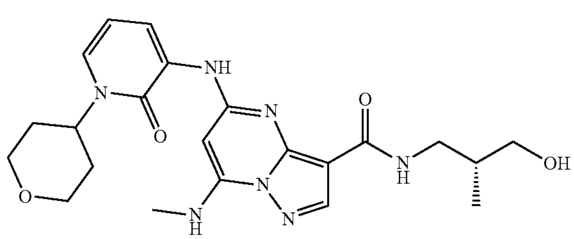 [SMILES: CNc1cc(Nc2cccn(C3CCOCC3)c2=O)nc2c(C(=O)NC[C@@H](C)CO)cnn12] |

TABLE 1-continued
Selected Compounds
| Compound | Structure |
|---|---|
| I-1033 | 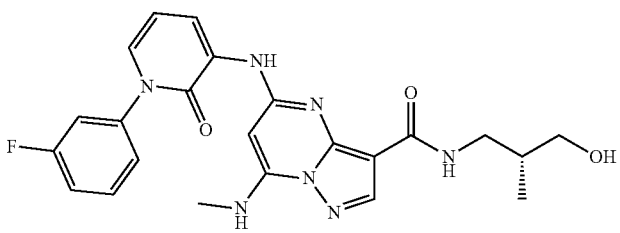 [SMILES: CNc1cc(Nc2cccn(-c3cccc(F)c3)c2=O)nc2c(C(=O)NC[C@@H](C)CO)cnn12] |
| I-1034 | 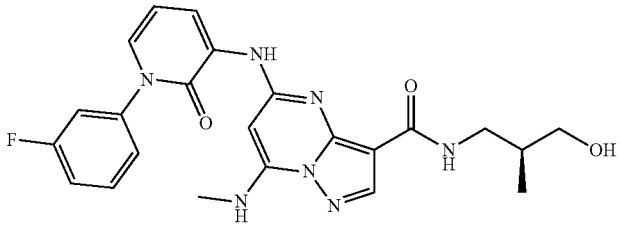 [SMILES: CNc1cc(Nc2cccn(-c3cccc(F)c3)c2=O)nc2c(C(=O)NC[C@H](C)CO)cnn12] |
| I-1035 | 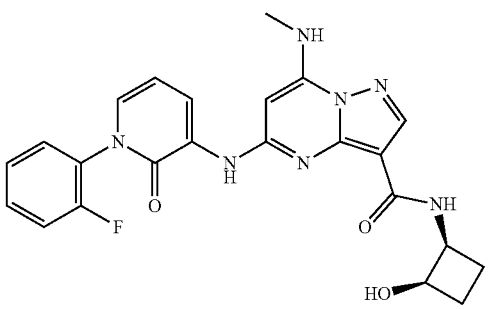 [SMILES: CNc1cc(Nc2cccn(-c3ccccc3F)c2=O)nc2c(C(=O)N[C@H]3CC[C@H]3O)cnn12] |
| I-1036 | 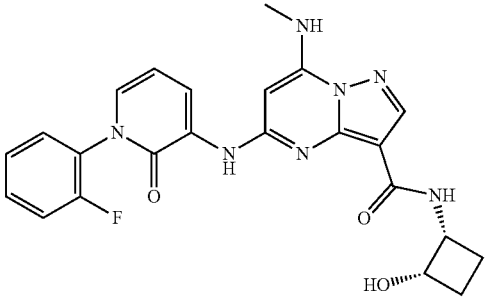 [SMILES: CNc1cc(Nc2cccn(-c3ccccc3F)c2=O)nc2c(C(=O)N[C@@H]3CC[C@@H]3O)cnn12] |
| I-1037 | 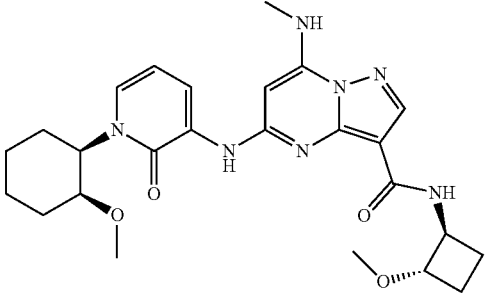 [SMILES: CNc1cc(Nc2cccn([C@@H]3CCCC[C@@H]3OC)c2=O)nc2c(C(=O)N[C@H]3CC[C@@H]3OC)cnn12] |

TABLE 1-continued

| Compound | Structure |
|---|---|
| I-1038 | 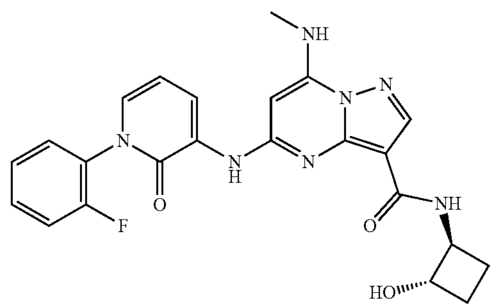 [SMILES: CNc1cc(Nc2cccn(-c3ccccc3F)c2=O)nc2c(C(=O)N[C@H]3CC[C@@H]3O)cnn12] |
| I-1039 | 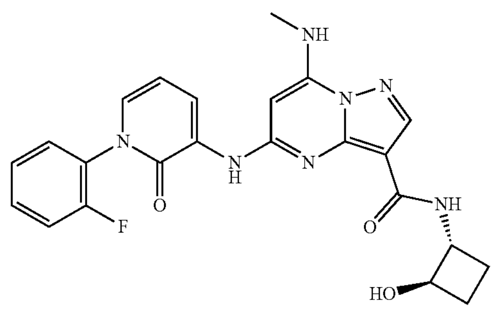 [SMILES: CNc1cc(Nc2cccn(-c3ccccc3F)c2=O)nc2c(C(=O)N[C@@H]3CC[C@H]3O)cnn12] |
| I-1040 | 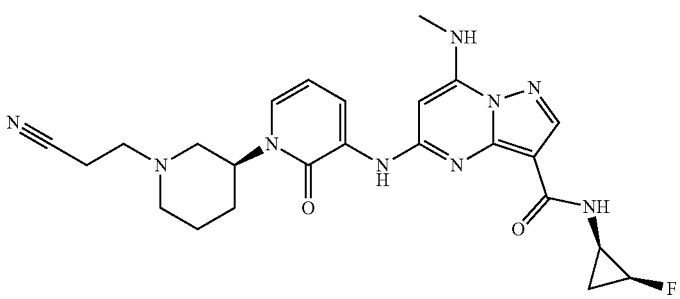 [SMILES: CNc1cc(Nc2cccn([C@H]3CCCN(CCC#N)C3)c2=O)nc2c(C(=O)N[C@@H]3C[C@@H]3F)cnn12] |
| I-1041 | 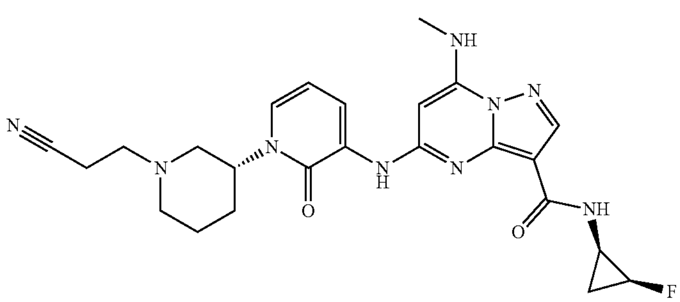 [SMILES: CNc1cc(Nc2cccn([C@@H]3CCCN(CCC#N)C3)c2=O)nc2c(C(=O)N[C@@H]3C[C@@H]3F)cnn12] |
| I-1042 | 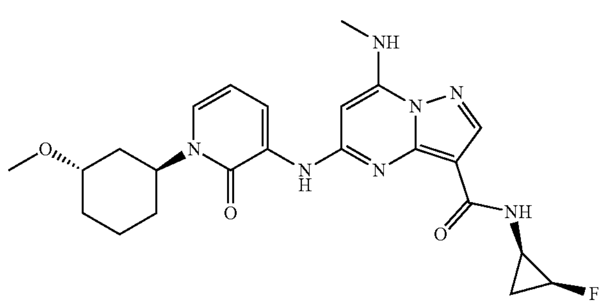 [SMILES: CNc1cc(Nc2cccn([C@H]3CCC[C@H](OC)C3)c2=O)nc2c(C(=O)N[C@@H]3C[C@@H]3F)cnn12] |

TABLE 1-continued

| Selected Compounds | |
|---|---|
| Compound | Structure |

I-1043

I-1044

I-1045

I-1046

I-1047

TABLE 1-continued

Selected Compounds

| Compound | Structure |
|---|---|
| I-1048 | 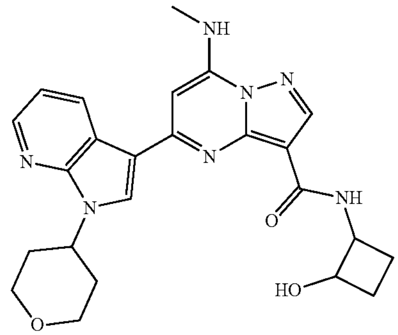 [SMILES: CNc1cc(-c2cn(C3CCOCC3)c3ncccc23)nc2c(C(=O)NC3CCC3O)cnn12] |
| I-1049 | 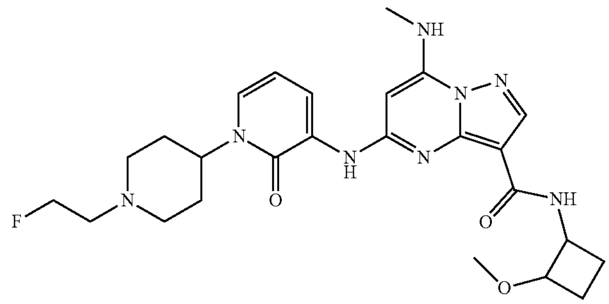 [SMILES: CNc1cc(Nc2cccn(C3CCN(CCF)CC3)c2=O)nc2c(C(=O)NC3CCC3OC)cnn12] |
| I-1050 | 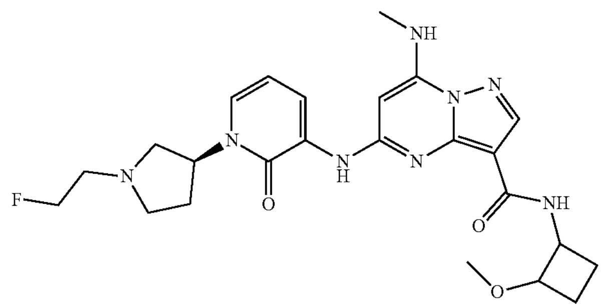 [SMILES: CNc1cc(Nc2cccn([C@H]3CCN(CCF)C3)c2=O)nc2c(C(=O)NC3CCC3OC)cnn12] |
| I-1051 | 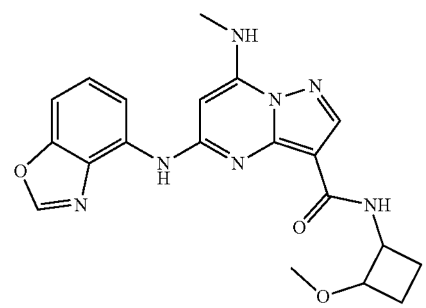 [SMILES: CNc1cc(Nc2cccc3ocnc23)nc2c(C(=O)NC3CCC3OC)cnn12] |
| I-1052 | 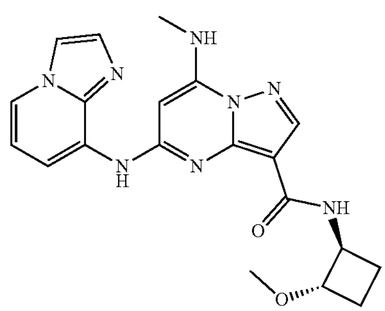 [SMILES: CNc1cc(Nc2cccn3ccnc23)nc2c(C(=O)N[C@H]3CC[C@@H]3OC)cnn12] |

TABLE 1-continued

Selected Compounds

| Compound | Structure |
|---|---|
| I-1053 | 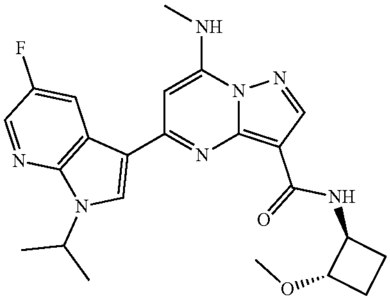 [SMILES: CNc1cc(-c2cn(C(C)C)c3ncc(F)cc23)nc2c(C(=O)N[C@H]3CC[C@@H]3OC)cnn12] |
| I-1054 | 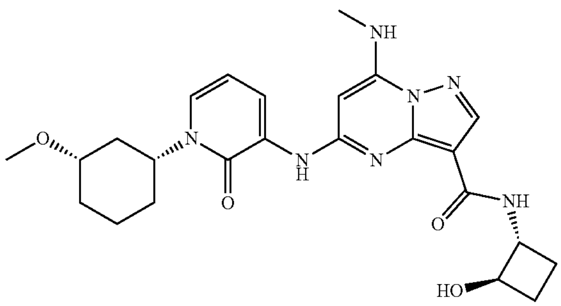 [SMILES: CNc1cc(Nc2cccn([C@@H]3CCC[C@H](OC)C3)c2=O)nc2c(C(=O)N[C@@H]3CC[C@H]3O)cnn12] |
| I-1055 | 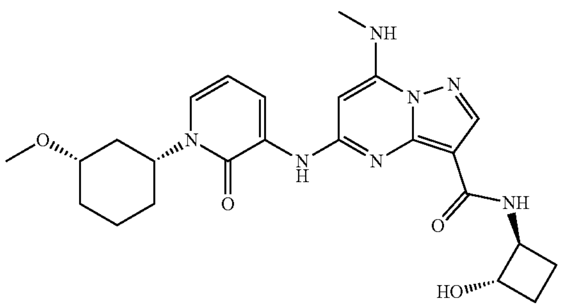 [SMILES: CNc1cc(Nc2cccn([C@@H]3CCC[C@H](OC)C3)c2=O)nc2c(C(=O)N[C@H]3CC[C@@H]3O)cnn12] |
| I-1056 | 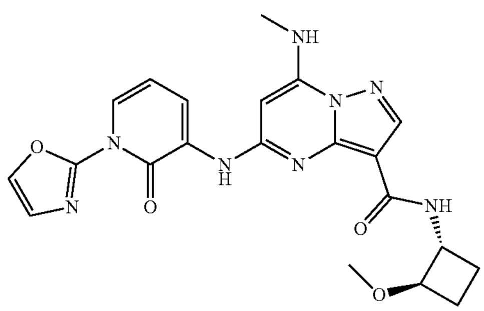 [SMILES: CNc1cc(Nc2cccn(-c3ncco3)c2=O)nc2c(C(=O)N[C@@H]3CC[C@H]3OC)cnn12] |
| I-1057 | 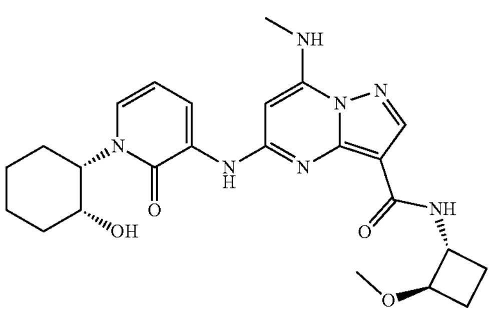 [SMILES: CNc1cc(Nc2cccn([C@H]3CCCC[C@H]3O)c2=O)nc2c(C(=O)N[C@@H]3CC[C@H]3OC)cnn12] |

TABLE 1-continued
| Selected Compounds | |
|---|---|
| Compound | Structure |
| I-1058 | 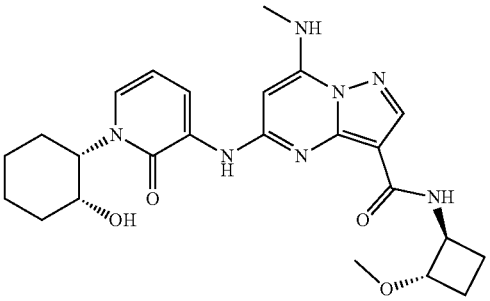 [SMILES: CNc1cc(Nc2cccn([C@H]3CCCC[C@H]3O)c2=O)nc2c(C(=O)N[C@H]3CC[C@@H]3OC)cnn12] |
| I-1059 | 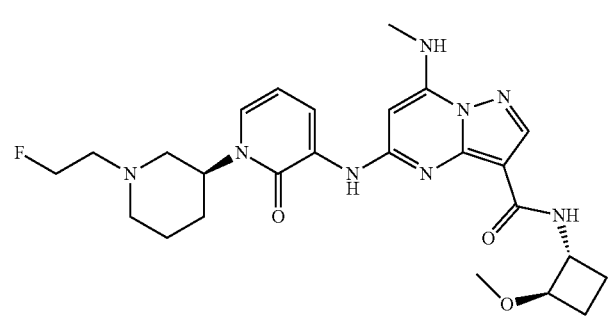 [SMILES: CNc1cc(Nc2cccn([C@H]3CCCN(CCF)C3)c2=O)nc2c(C(=O)N[C@@H]3CC[C@H]3OC)cnn12] |
| I-1060 | 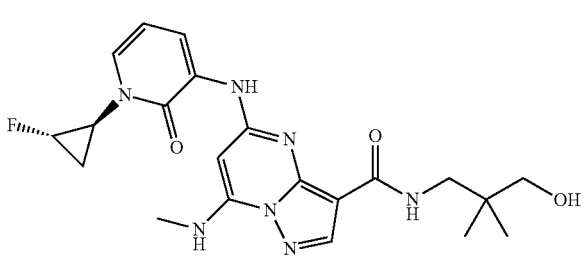 [SMILES: CNc1cc(Nc2cccn([C@H]3C[C@@H]3F)c2=O)nc2c(C(=O)NCC(C)(C)CO)cnn12] |
| I-1061 | 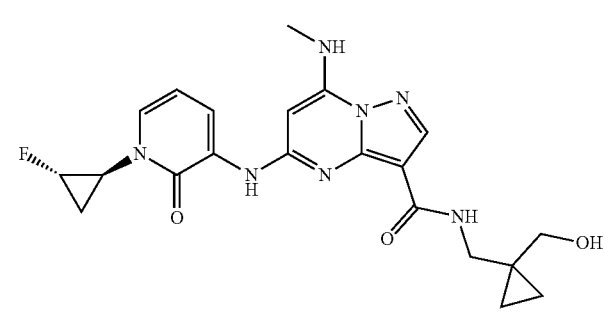 [SMILES: CNc1cc(Nc2cccn([C@H]3C[C@@H]3F)c2=O)nc2c(C(=O)NCC3(CO)CC3)cnn12] |
| I-1062 | 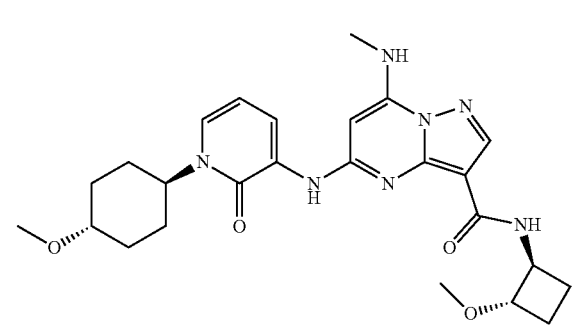 [SMILES: CNc1cc(Nc2cccn([C@H]3CC[C@H](OC)CC3)c2=O)nc2c(C(=O)N[C@H]3CC[C@@H]3OC)cnn12] |

TABLE 1-continued
Selected Compounds
| Compound | Structure |
|---|---|
| I-1063 | 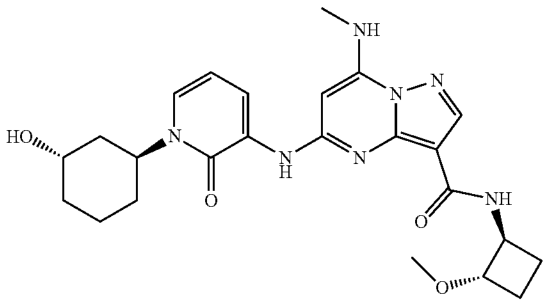 [SMILES: CNc1cc(Nc2cccn([C@H]3CCC[C@H](O)C3)c2=O)nc2c(C(=O)N[C@H]3CC[C@@H]3OC)cnn12] |
| I-1064 | 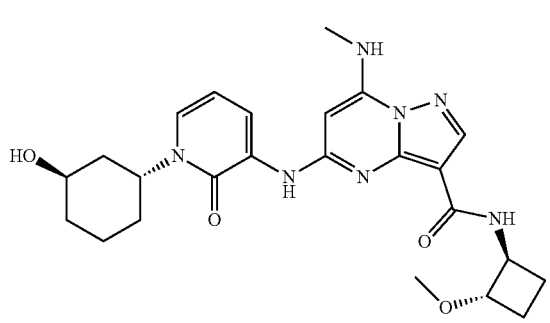 [SMILES: CNc1cc(Nc2cccn([C@@H]3CCC[C@@H](O)C3)c2=O)nc2c(C(=O)N[C@H]3CC[C@@H]3OC)cnn12] |
| I-1065 | 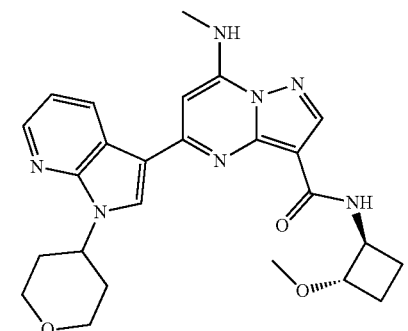 |
| I-1066 | 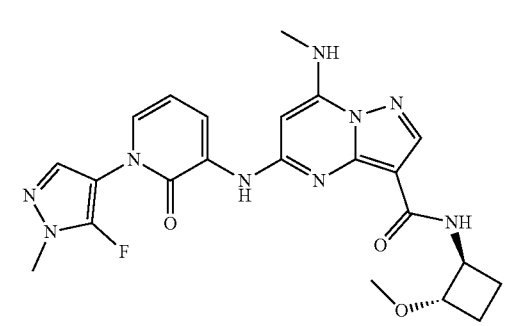 [SMILES: CNc1cc(Nc2cccn(-c3cnn(C)c3F)c2=O)nc2c(C(=O)N[C@H]3CC[C@@H]3OC)cnn12] |
| I-1067 | 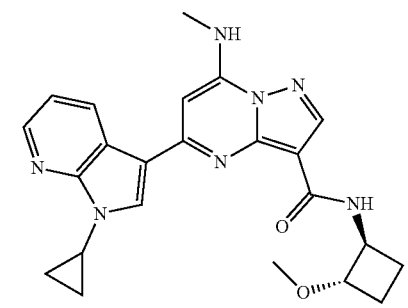 [SMILES: CNc1cc(-c2cn(C3CC3)c3ncccc23)nc2c(C(=O)N[C@H]3CC[C@@H]3OC)cnn12] |

TABLE 1-continued
Selected Compounds
| Compound | Structure |
|---|---|
| I-1068 | 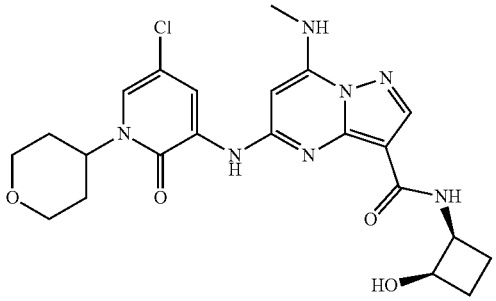 [SMILES: CNc1cc(Nc2cc(Cl)cn(C3CCOCC3)c2=O)nc2c(C(=O)N[C@H]3CC[C@H]3O)cnn12] |
| I-1069 | 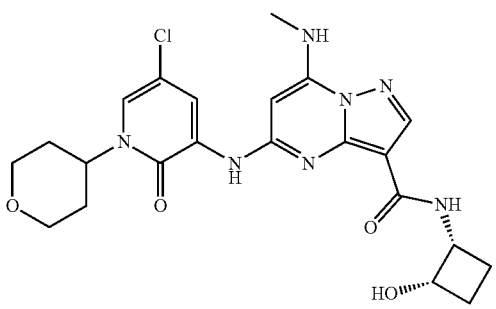 [SMILES: CNc1cc(Nc2cc(Cl)cn(C3CCOCC3)c2=O)nc2c(C(=O)N[C@@H]3CC[C@@H]3O)cnn12] |
| I-1070 | 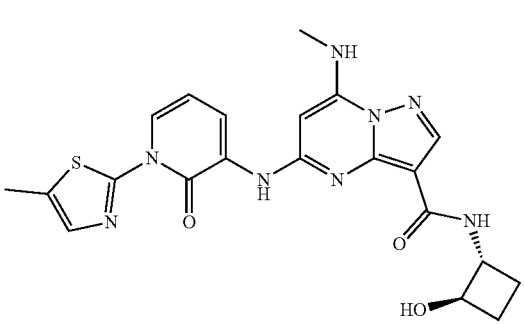 [SMILES: CNc1cc(Nc2cccn(-c3ncc(C)s3)c2=O)nc2c(C(=O)N[C@@H]3CC[C@H]3O)cnn12] |
| I-1071 | 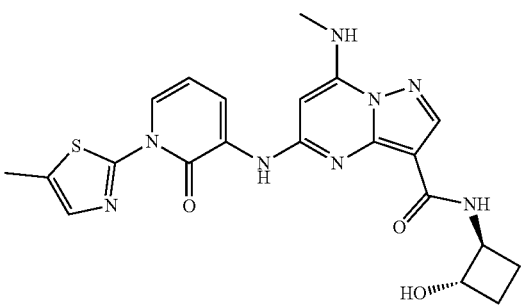 [SMILES: CNc1cc(Nc2cccn(-c3ncc(C)s3)c2=O)nc2c(C(=O)N[C@H]3CC[C@@H]3O)cnn12] |
| I-1072 | 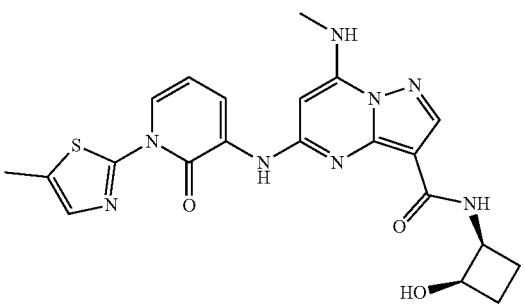 [SMILES: CNc1cc(Nc2cccn(-c3ncc(C)s3)c2=O)nc2c(C(=O)N[C@H]3CC[C@H]3O)cnn12] |

TABLE 1-continued

Selected Compounds

| Compound | Structure |
|---|---|
| I-1073 | 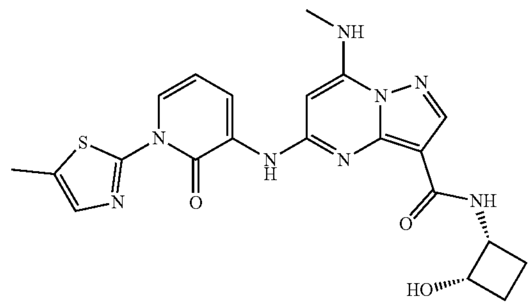 [SMILES: CNc1cc(Nc2cccn(-c3ncc(C)s3)c2=O)nc2c(C(=O)N[C@@H]3CC[C@@H]3O)cnn12] |
| I-1074 | 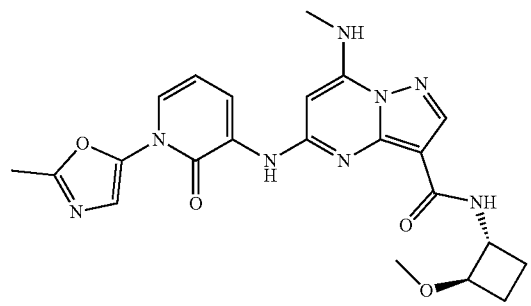 [SMILES: CNc1cc(Nc2cccn(-c3cnc(C)o3)c2=O)nc2c(C(=O)N[C@@H]3CC[C@H]3OC)cnn12] |
| I-1075 | 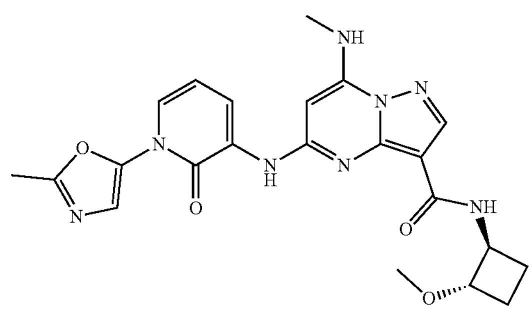 [SMILES: CNc1cc(Nc2cccn(-c3cnc(C)o3)c2=O)nc2c(C(=O)N[C@H]3CC[C@@H]3OC)cnn12] |
| I-1076 | 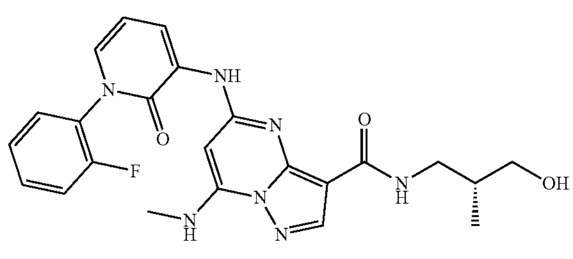 [SMILES: CNc1cc(Nc2cccn(-c3ccccc3F)c2=O)nc2c(C(=O)NC[C@@H](C)CO)cnn12] |
| I-1077 | 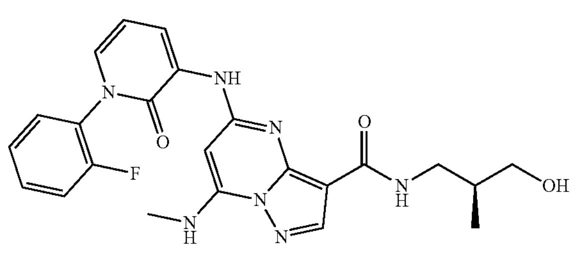 [SMILES: CNc1cc(Nc2cccn(-c3ccccc3F)c2=O)nc2c(C(=O)NC[C@H](C)CO)cnn12] |

TABLE 1-continued

Selected Compounds

| Compound | Structure |
|---|---|
| I-1078 | 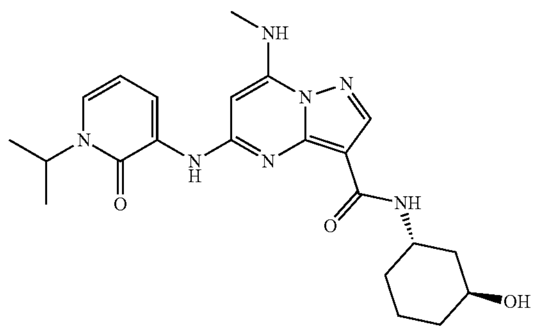 [SMILES: CNc1cc(Nc2cccn(C(C)C)c2=O)nc2c(C(=O)N[C@H]3CCC[C@H](O)C3)cnn12] |
| I-1079 | 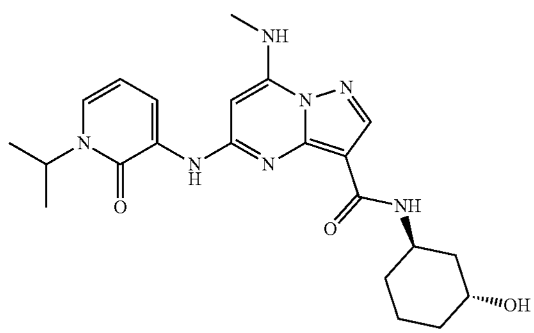 [SMILES: CNc1cc(Nc2cccn(C(C)C)c2=O)nc2c(C(=O)N[C@@H]3CCC[C@@H](O)C3)cnn12] |
| I-1080 | 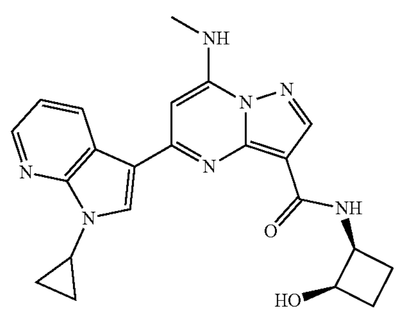 [SMILES: CNc1cc(-c2cn(C3CC3)c3ncccc23)nc2c(C(=O)N[C@H]3CC[C@H]3O)cnn12] |
| I-1081 | 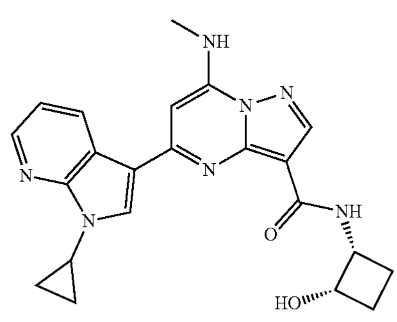 [SMILES: CNc1cc(-c2cn(C3CC3)c3ncccc23)nc2c(C(=O)N[C@@H]3CC[C@@H]3O)cnn12] |

TABLE 1-continued

Selected Compounds

| Compound | Structure |
|---|---|
| I-1082 | 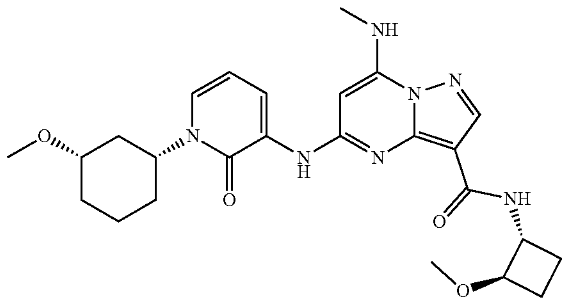 [SMILES: CNc1cc(Nc2cccn([C@@H]3CCC[C@H](OC)C3)c2=O)nc2c(C(=O)N[C@@H]3CC[C@H]3OC)cnn12] |
| I-1083 | 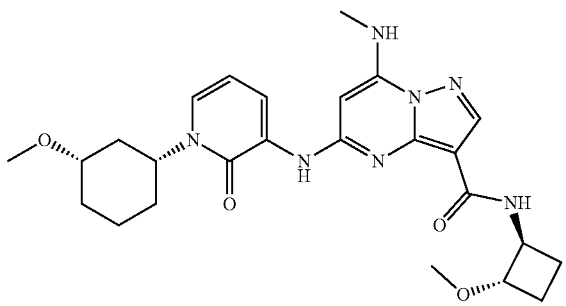 [SMILES: CNc1cc(Nc2cccn([C@@H]3CCC[C@H](OC)C3)c2=O)nc2c(C(=O)N[C@H]3CC[C@@H]3OC)cnn12] |
| I-1084 | 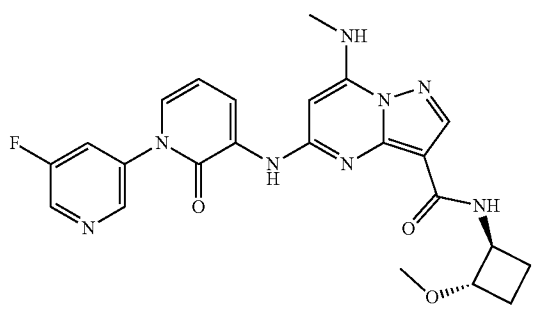 [SMILES: CNc1cc(Nc2cccn(-c3cncc(F)c3)c2=O)nc2c(C(=O)N[C@H]3CC[C@@H]3OC)cnn12] |
| I-1085 | 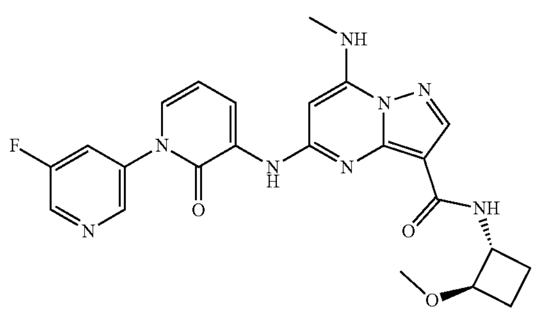 [SMILES: CNc1cc(Nc2cccn(-c3cncc(F)c3)c2=O)nc2c(C(=O)N[C@@H]3CC[C@H]3OC)cnn12] |
| I-1086 | 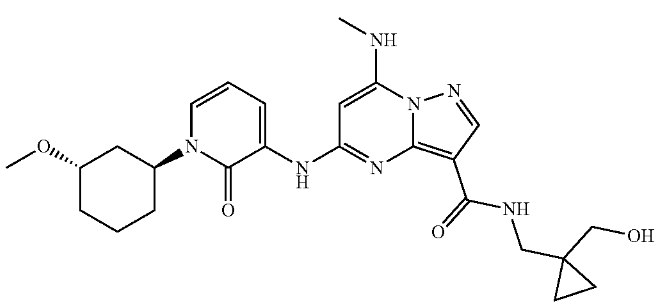 [SMILES: CNc1cc(Nc2cccn([C@H]3CCC[C@H](OC)C3)c2=O)nc2c(C(=O)NCC3(CO)CC3)cnn12] |

TABLE 1-continued
Selected Compounds
| Compound | Structure |
|---|---|
| I-1087 | 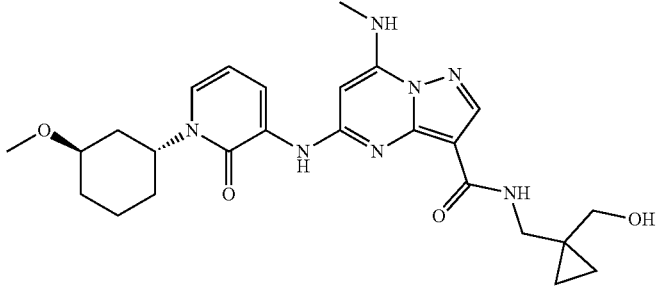 [SMILES: CNc1cc(Nc2cccn([C@@H]3CCC[C@@H](OC)C3)c2=O)nc2c(C(=O)NCC3(CO)CC3)cnn12] |
| I-1088 | 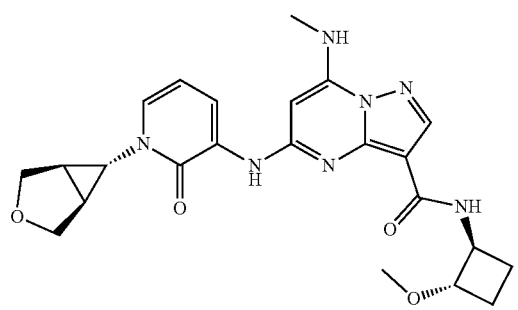 [SMILES: CNc1cc(Nc2cccn([C@H]3[C@@H]4COC[C@@H]43)c2=O)nc2c(C(=O)N[C@H]3CC[C@@H]3OC)cnn12] |
| I-1089 | 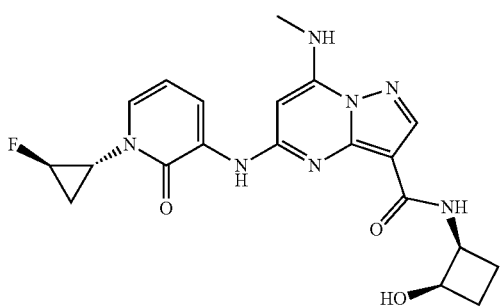 [SMILES: CNc1cc(Nc2cccn([C@@H]3C[C@H]3F)c2=O)nc2c(C(=O)N[C@H]3CC[C@H]3O)cnn12] |
| I-1090 | 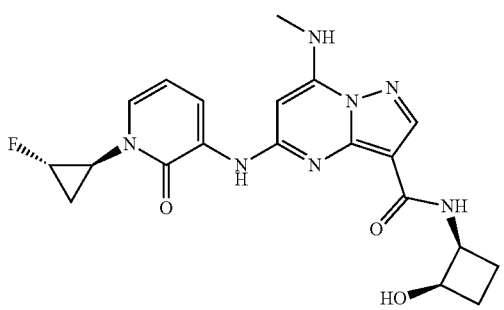 [SMILES: CNc1cc(Nc2cccn([C@H]3C[C@@H]3F)c2=O)nc2c(C(=O)N[C@H]3CC[C@H]3O)cnn12] |
| I-1091 | 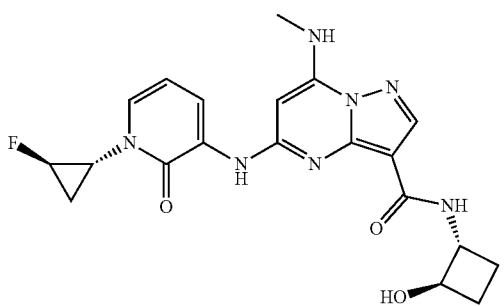 [SMILES: CNc1cc(Nc2cccn([C@@H]3C[C@H]3F)c2=O)nc2c(C(=O)N[C@@H]3CC[C@H]3O)cnn12] |

TABLE 1-continued

Selected Compounds

| Compound | Structure |
|---|---|
| I-1092 | 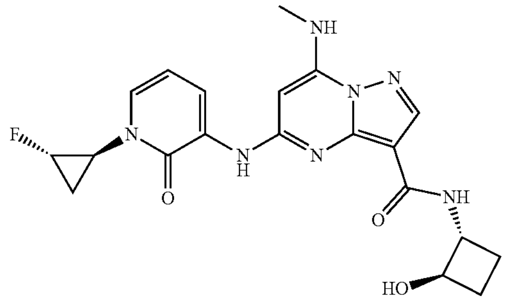 [SMILES: CNc1cc(Nc2cccn([C@H]3C[C@@H]3F)c2=O)nc2c(C(=O)N[C@@H]3CC[C@H]3O)cnn12] |
| I-1093 | 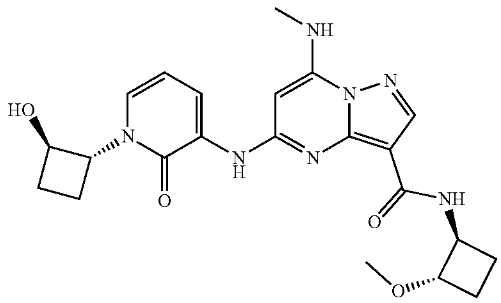 [SMILES: CNc1cc(Nc2cccn([C@@H]3CC[C@H]3O)c2=O)nc2c(C(=O)N[C@H]3CC[C@@H]3OC)cnn12] |
| I-1094 | 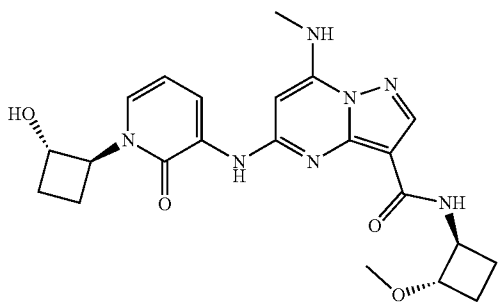 [SMILES: CNc1cc(Nc2cccn([C@H]3CC[C@@H]3O)c2=O)nc2c(C(=O)N[C@H]3CC[C@@H]3OC)cnn12] |
| I-1095 | 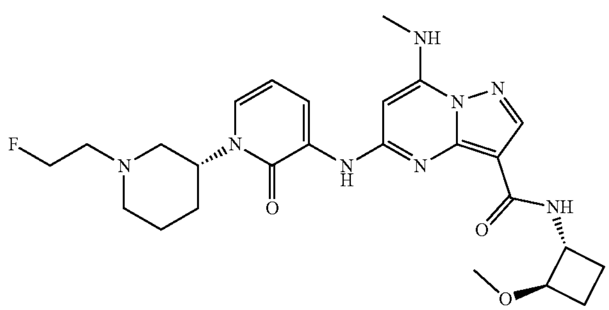 [SMILES: CNc1cc(Nc2cccn([C@@H]3CCCN(CCF)C3)c2=O)nc2c(C(=O)N[C@@H]3CC[C@H]3OC)cnn12] |
| I-1096 | 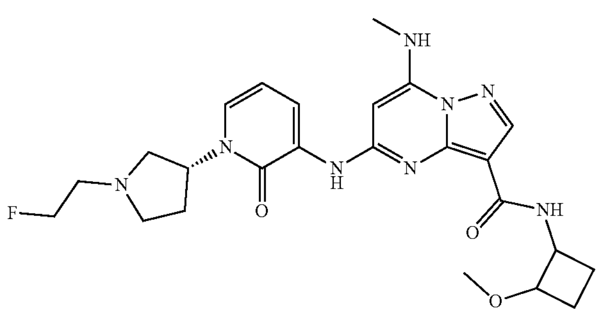 [SMILES: CNc1cc(Nc2cccn([C@@H]3CCN(CCF)C3)c2=O)nc2c(C(=O)NC3CCC3OC)cnn12] |

TABLE 1-continued

Selected Compounds

| Compound | Structure |
| --- | --- |
| I-1097 | 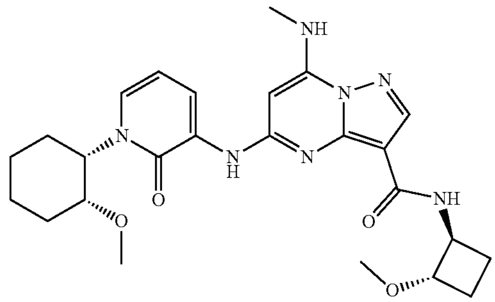 [SMILES: CNc1cc(Nc2cccn([C@H]3CCCC[C@H]3OC)c2=O)nc2c(C(=O)N[C@H]3CC[C@@H]3OC)cnn12] |
| I-1098 | 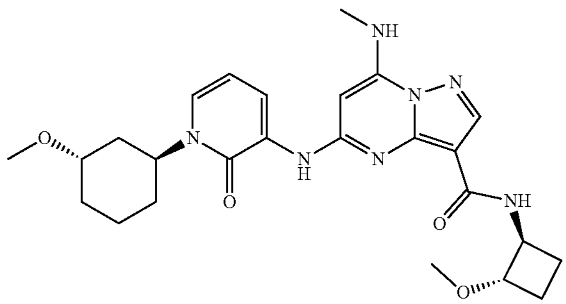 [SMILES: CNc1cc(Nc2cccn([C@H]3CCC[C@H](OC)C3)c2=O)nc2c(C(=O)N[C@H]3CC[C@@H]3OC)cnn12] |
| I-1099 | 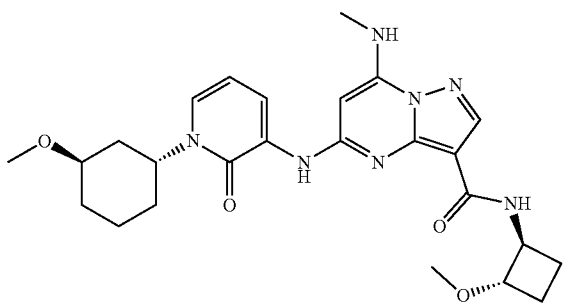 [SMILES: CNc1cc(Nc2cccn([C@@H]3CCC[C@@H](OC)C3)c2=O)nc2c(C(=O)N[C@H]3CC[C@@H]3OC)cnn12] |
| I-1100 | 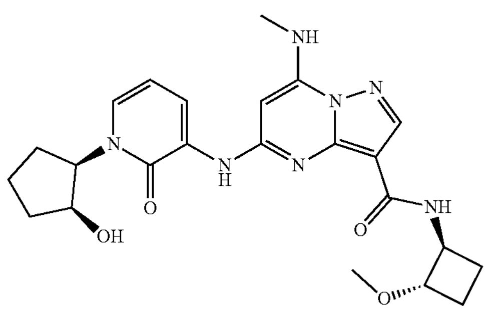 [SMILES: CNc1cc(Nc2cccn([C@@H]3CCC[C@@H]3O)c2=O)nc2c(C(=O)N[C@H]3CC[C@@H]3OC)cnn12] |
| I-1101 | 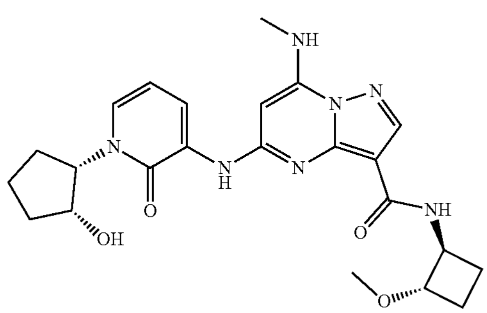 [SMILES: CNc1cc(Nc2cccn([C@H]3CCC[C@H]3O)c2=O)nc2c(C(=O)N[C@H]3CC[C@@H]3OC)cnn12] |

TABLE 1-continued
Selected Compounds
| Compound | Structure |
|---|---|
| I-1102 | 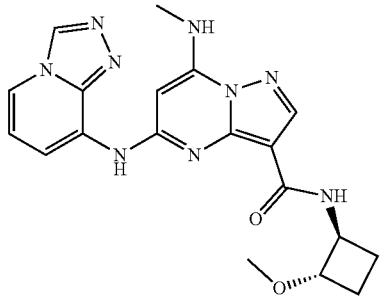 [SMILES: CNc1cc(Nc2cccn3cnnc23)nc2c(C(=O)N[C@H]3CC[C@@H]3OC)cnn12] |
| I-1103 | 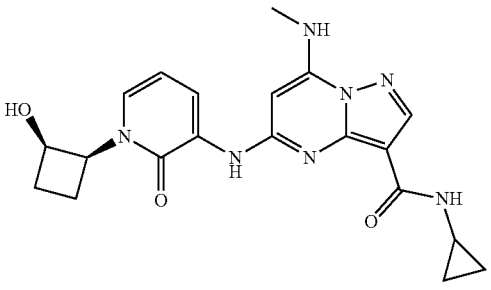 [SMILES: CNc1cc(Nc2cccn([C@H]3CC[C@H]3O)c2=O)nc2c(C(=O)NC3CC3)cnn12] |
| I-1104 | 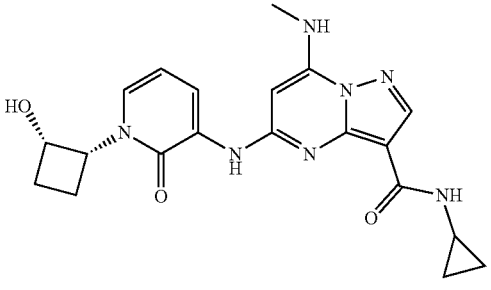 [SMILES: CNc1cc(Nc2cccn([C@@H]3CC[C@@H]3O)c2=O)nc2c(C(=O)NC3CC3)cnn12] |
| I-1105 | 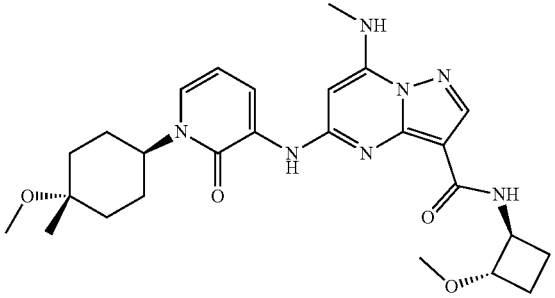 [SMILES: CNc1cc(Nc2cccn([C@H]3CC[C@](C)(OC)CC3)c2=O)nc2c(C(=O)N[C@H]3CC[C@@H]3OC)cnn12] |
| I-1106 | 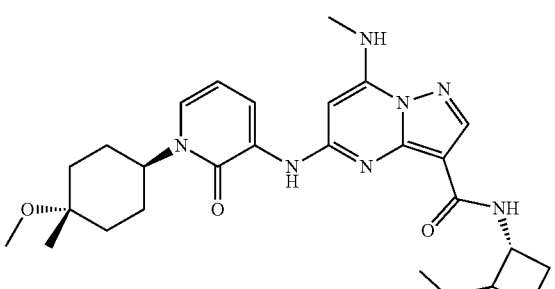 |

TABLE 1-continued

Selected Compounds

| Compound | Structure |
|---|---|
| I-1107 | 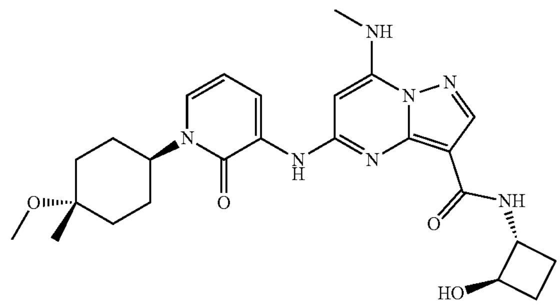 [SMILES: CNc1cc(Nc2cccn([C@H]3CC[C@](C)(OC)CC3)c2=O)nc2c(C(=O)N[C@@H]3CC[C@H]3O)cnn12] |
| I-1108 | 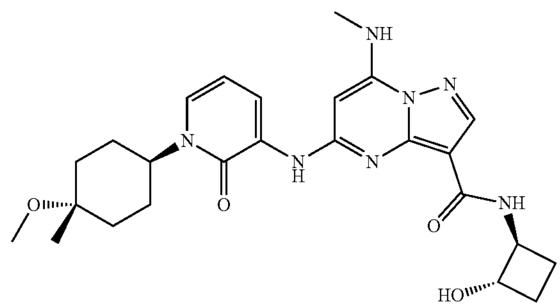 [SMILES: CNc1cc(Nc2cccn([C@H]3CC[C@](C)(OC)CC3)c2=O)nc2c(C(=O)N[C@H]3CC[C@@H]3O)cnn12] |
| I-1109 | 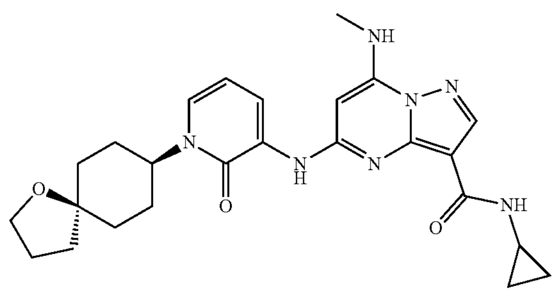 [SMILES: CNc1cc(Nc2cccn([C@H]3CC[C@]4(CCCO4)CC3)c2=O)nc2c(C(=O)NC3CC3)cnn12] |
| I-1110 | 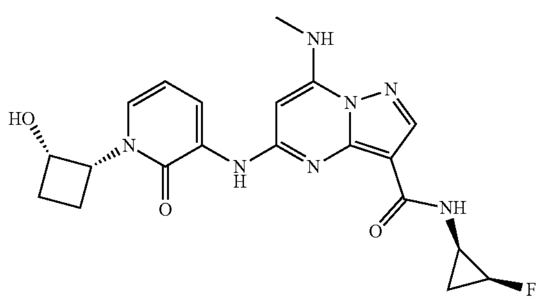 [SMILES: CNc1cc(Nc2cccn([C@@H]3CC[C@@H]3O)c2=O)nc2c(C(=O)N[C@@H]3C[C@@H]3F)cnn12] |
| I-1111 | |

US 10,562,906 B2

TABLE 1-continued

Selected Compounds

| Compound | Structure |
|---|---|
| I-1112 | 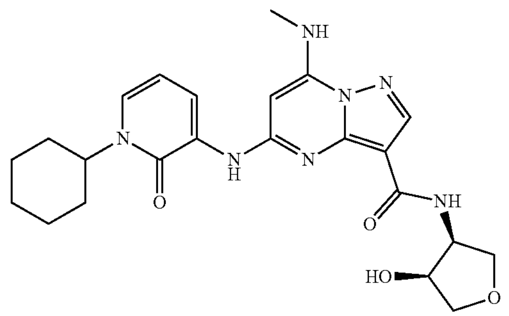 [SMILES: CNc1cc(Nc2cccn(C3CCCCC3)c2=O)nc2c(C(=O)N[C@H]3COC[C@H]3O)cnn12] |
| I-1113 | 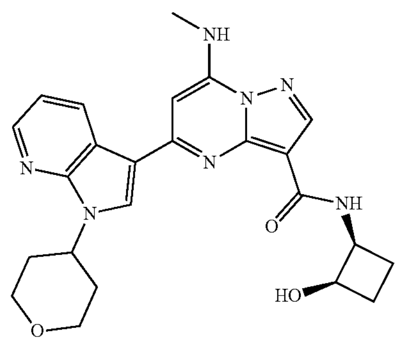 [SMILES: CNc1cc(-c2cn(C3CCOCC3)c3ncccc23)nc2c(C(=O)N[C@H]3CC[C@H]3O)cnn12] |
| I-1114 | 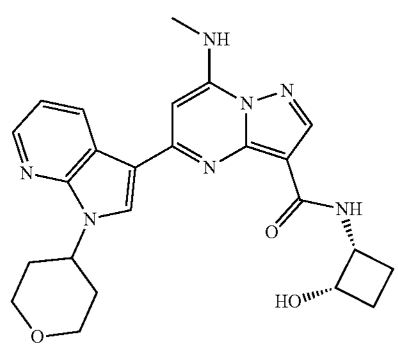 [SMILES: CNc1cc(-c2cn(C3CCOCC3)c3ncccc23)nc2c(C(=O)N[C@@H]3CC[C@@H]3O)cnn12] |
| I-1115 | 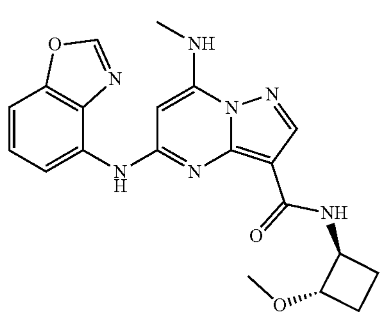 [SMILES: CNc1cc(Nc2cccc3ocnc23)nc2c(C(=O)N[C@H]3CC[C@@H]3OC)cnn12] |

TABLE 1-continued
Selected Compounds
| Compound | Structure |
|---|---|
| I-1116 | 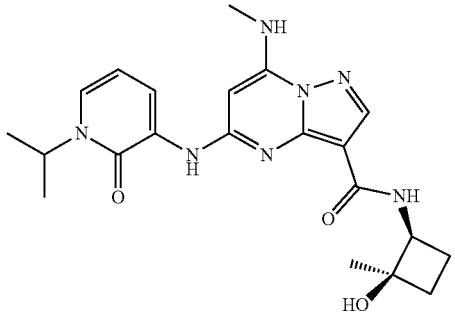 [SMILES: CNc1cc(Nc2cccn(C(C)C)c2=O)nc2c(C(=O)N[C@H]3CC[C@@]3(C)O)cnn12] |
| I-1117 | 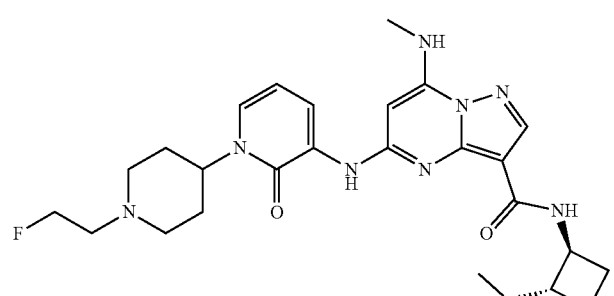 |
| I-1118 | 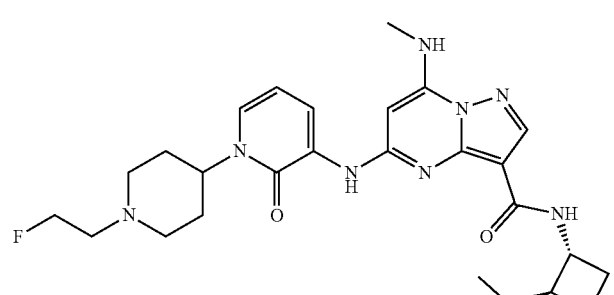 |
| I-1119 | 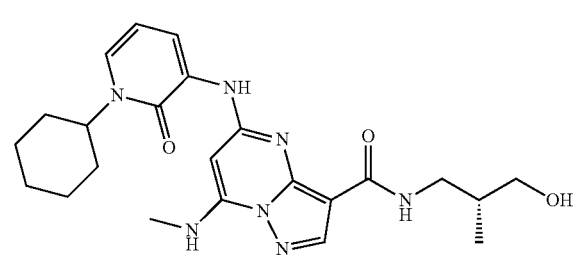 [SMILES: CNc1cc(Nc2cccn(C3CCCCC3)c2=O)nc2c(C(=O)NC[C@@H](C)CO)cnn12] |
| I-1120 | 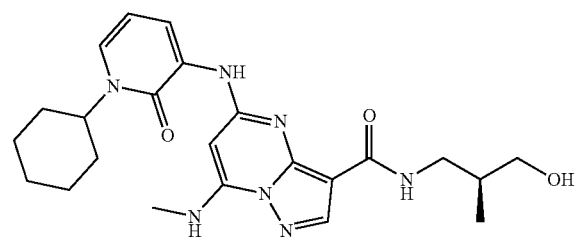 [SMILES: CNc1cc(Nc2cccn(C3CCCCC3)c2=O)nc2c(C(=O)NC[C@H](C)CO)cnn12] |

TABLE 1-continued

Selected Compounds

| Compound | Structure |
|---|---|
| I-1121 | 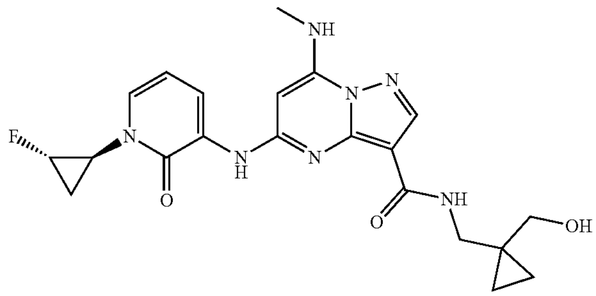 [SMILES: CNc1cc(Nc2cccn([C@H]3C[C@@H]3F)c2=O)nc2c(C(=O)NCC3(CO)CC3)cnn12] |
| I-1122 | 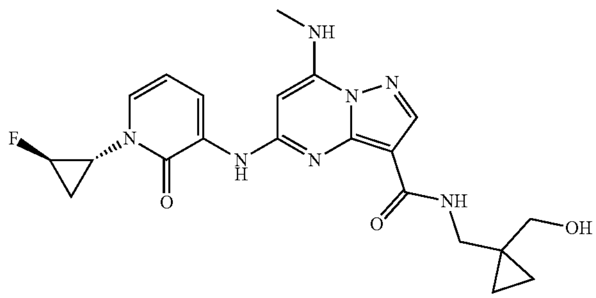 [SMILES: CNc1cc(Nc2cccn([C@@H]3C[C@H]3F)c2=O)nc2c(C(=O)NCC3(CO)CC3)cnn12] |
| I-1123 | 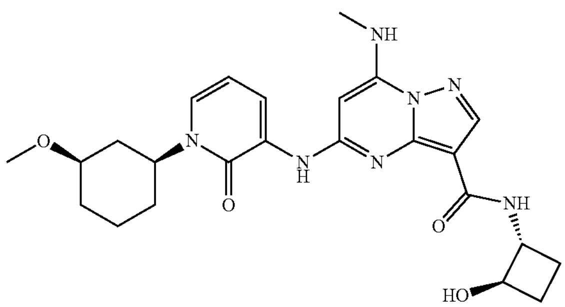 [SMILES: CNc1cc(Nc2cccn([C@H]3CCC[C@@H](OC)C3)c2=O)nc2c(C(=O)N[C@@H]3CC[C@H]3O)cnn12] |
| I-1124 | 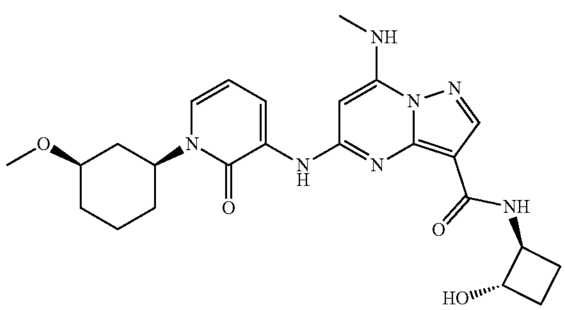 [SMILES: CNc1cc(Nc2cccn([C@H]3CCC[C@@H](OC)C3)c2=O)nc2c(C(=O)N[C@H]3CC[C@@H]3O)cnn12] |
| I-1125 | 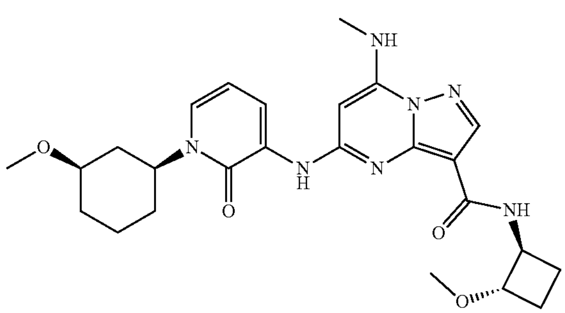 [SMILES: CNc1cc(Nc2cccn([C@H]3CCC[C@@H](OC)C3)c2=O)nc2c(C(=O)N[C@H]3CC[C@@H]3OC)cnn12] |

TABLE 1-continued
Selected Compounds
| Compound | Structure |
|---|---|
| I-1126 | 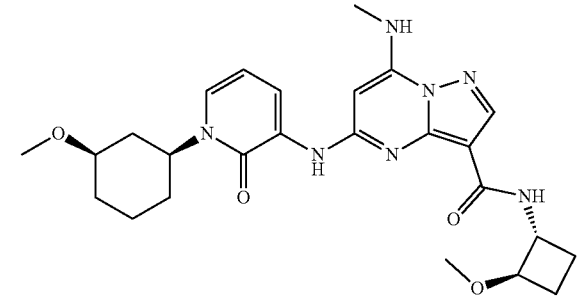 [SMILES: CNc1cc(Nc2cccn([C@H]3CCC[C@@H](OC)C3)c2=O)nc2c(C(=O)N[C@@H]3CC[C@H]3OC)cnn12] |
| I-1127 | 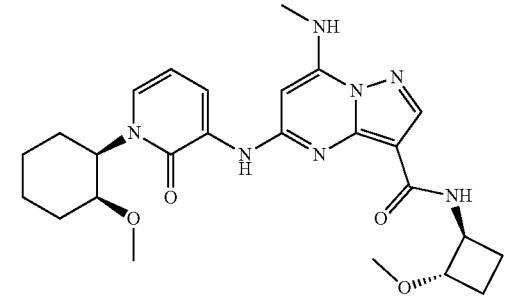 [SMILES: CNc1cc(Nc2cccn([C@@H]3CCCC[C@@H]3OC)c2=O)nc2c(C(=O)N[C@H]3CC[C@@H]3OC)cnn12] |
| I-1128 | 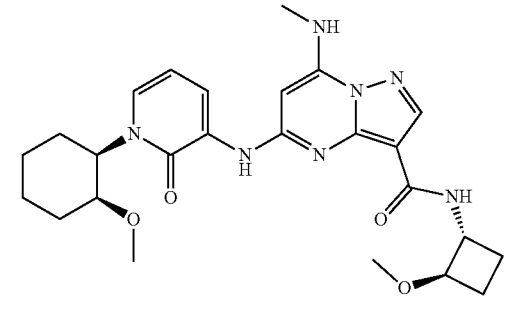 [SMILES: CNc1cc(Nc2cccn([C@@H]3CCCC[C@@H]3OC)c2=O)nc2c(C(=O)N[C@@H]3CC[C@H]3OC)cnn12] |
| I-1129 | 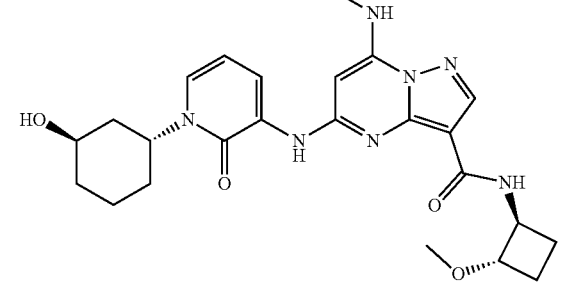 |
| I-1130 | 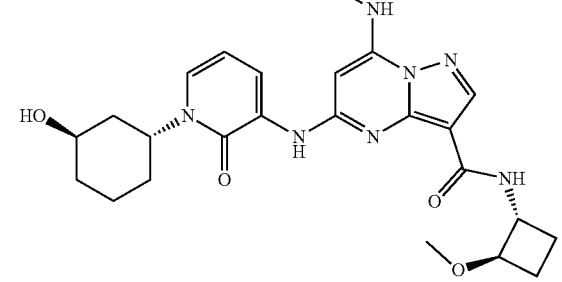 |

TABLE 1-continued

Selected Compounds

| Compound | Structure |
|---|---|
| I-1131 | 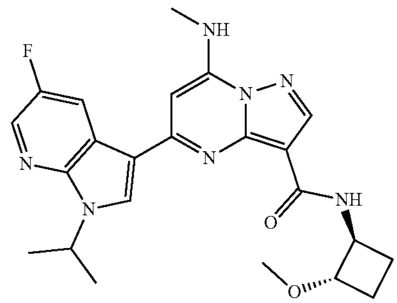 [SMILES: CNc1cc(-c2cn(C(C)C)c3ncc(F)cc23)nc2c(C(=O)N[C@H]3CC[C@@H]3OC)cnn12] |
| I-1132 | 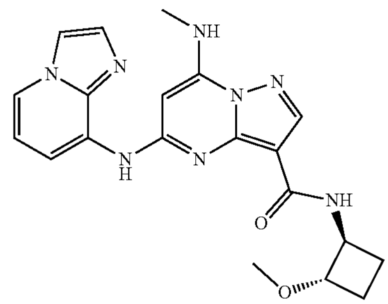 [SMILES: CNc1cc(Nc2cccn3ccnc23)nc2c(C(=O)N[C@H]3CC[C@@H]3OC)cnn12] |
| I-1133 | 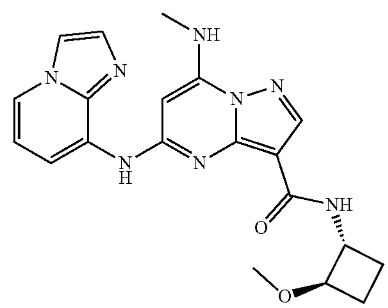 [SMILES: CNc1cc(Nc2cccn3ccnc23)nc2c(C(=O)N[C@@H]3CC[C@H]3OC)cnn12] |
| I-1134 | 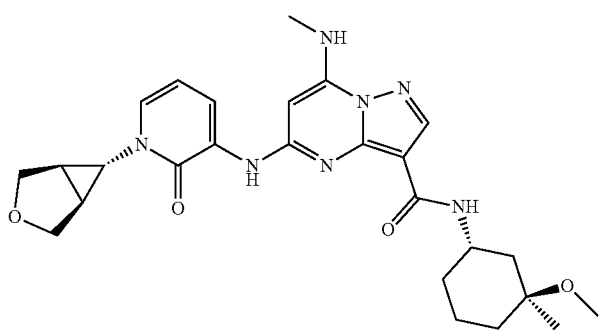 [SMILES: CNc1cc(Nc2cccn([C@H]3[C@@H]4COC[C@@H]43)c2=O)nc2c(C(=O)N[C@H]3CCC[C@](C)(OC)C3)cnn12] |
| I-1135 | 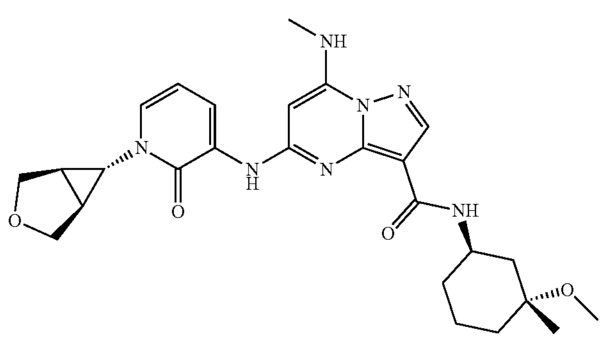 [SMILES: CNc1cc(Nc2cccn([C@H]3[C@@H]4COC[C@@H]43)c2=O)nc2c(C(=O)N[C@@H]3CCC[C@@](C)(OC)C3)cnn12] |

TABLE 1-continued

| Selected Compounds | |
|---|---|
| Compound | Structure |
| I-1136 | |
| I-1137 | |
| I-1138 | |
| I-1139 | |

TABLE 1-continued
| Compound | Structure |
|---|---|
| I-1140 | 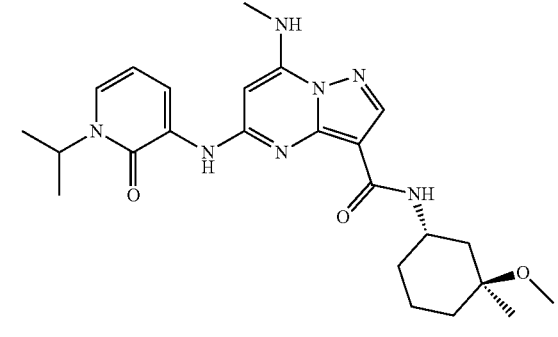 [SMILES: CNc1cc(Nc2cccn(C(C)C)c2=O)nc2c(C(=O)N[C@H]3CCC[C@](C)(OC)C3)cnn12] |
| I-1141 | 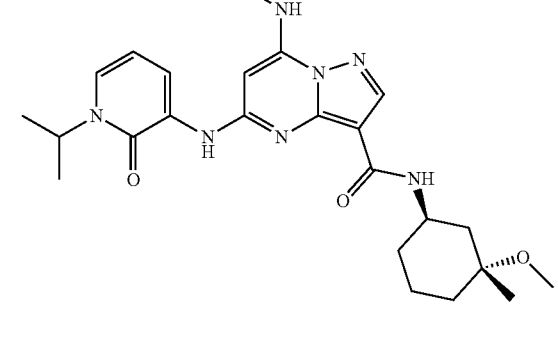 |
| I-1142 | 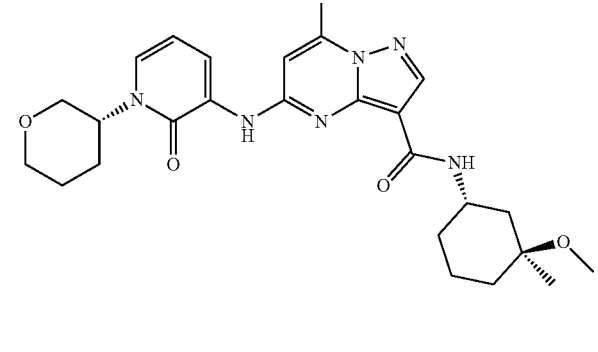 |
| I-1143 | 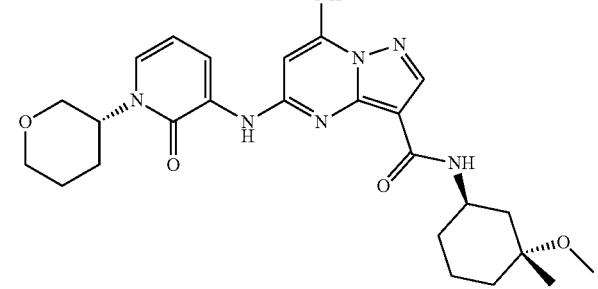 |

TABLE 1-continued
| Compound | Structure |
|---|---|
| I-1144 | 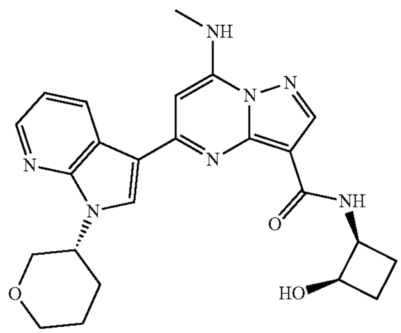 [SMILES: CNc1cc(-c2cn([C@@H]3CCCOC3)c3ncccc23)nc2c(C(=O)N[C@H]3CC[C@H]3O)cnn12] |
| I-1145 | 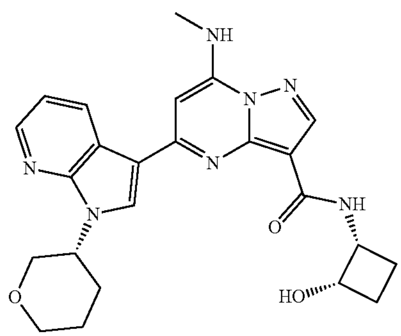 [SMILES: CNc1cc(-c2cn([C@@H]3CCCOC3)c3ncccc23)nc2c(C(=O)N[C@@H]3CC[C@@H]3O)cnn12] |
| I-1146 | 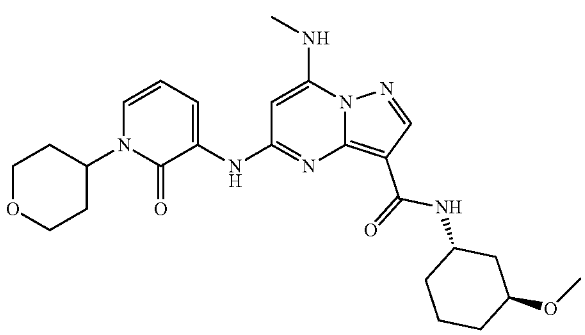 [SMILES: CNc1cc(Nc2cccn(C3CCOCC3)c2=O)nc2c(C(=O)N[C@H]3CCC[C@H](OC)C3)cnn12] |
| I-1147 | 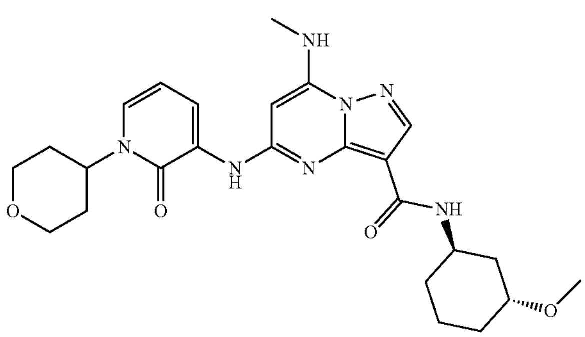 [SMILES: CNc1cc(Nc2cccn(C3CCOCC3)c2=O)nc2c(C(=O)N[C@@H]3CCC[C@@H](OC)C3)cnn12] |

TABLE 1-continued

Selected Compounds

| Compound | Structure |
|---|---|
| I-1148 | 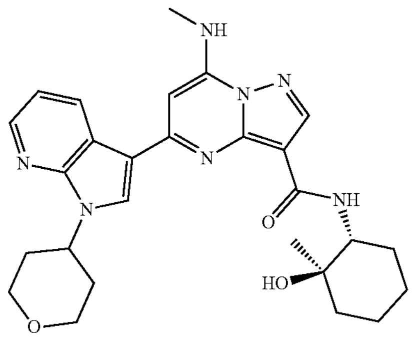 [SMILES: CNc1cc(-c2cn(C3CCOCC3)c3ncccc23)nc2c(C(=O)N[C@@H]3CCCC[C@@]3(C)O)cnn12] |
| I-1149 | 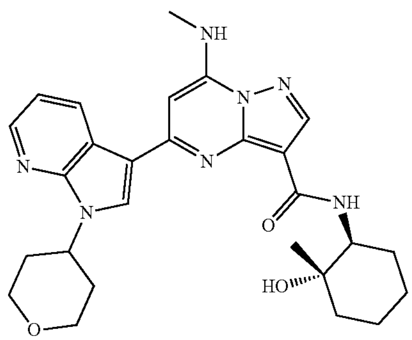 [SMILES: CNc1cc(-c2cn(C3CCOCC3)c3ncccc23)nc2c(C(=O)N[C@H]3CCCC[C@]3(C)O)cnn12] |
| I-1150 | 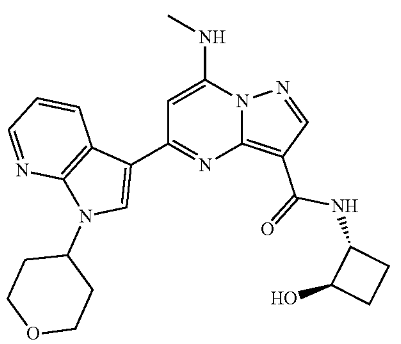 [SMILES: CNc1cc(-c2cn(C3CCOCC3)c3ncccc23)nc2c(C(=O)N[C@@H]3CC[C@H]3O)cnn12] |
| I-1151 | 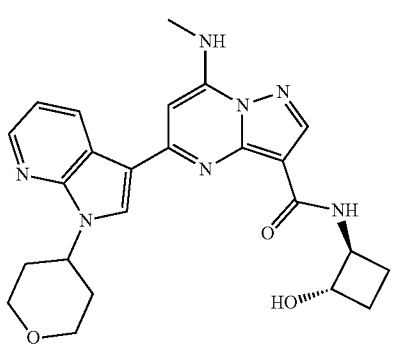 [SMILES: CNc1cc(-c2cn(C3CCOCC3)c3ncccc23)nc2c(C(=O)N[C@H]3CC[C@@H]3O)cnn12] |

TABLE 1-continued
| Selected Compounds | |
|---|---|
| Compound | Structure |
| I-1152 | 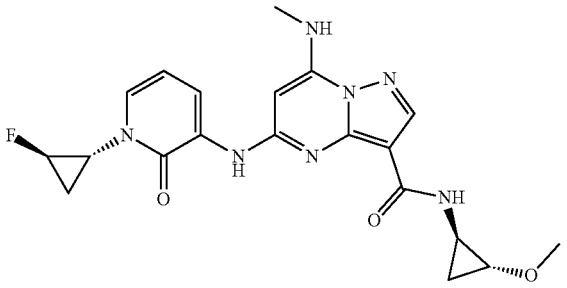 [SMILES: CNc1cc(Nc2cccn([C@@H]3C[C@H]3F)c2=O)nc2c(C(=O)N[C@@H]3C[C@H]3OC)cnn12] |
| I-1153 | 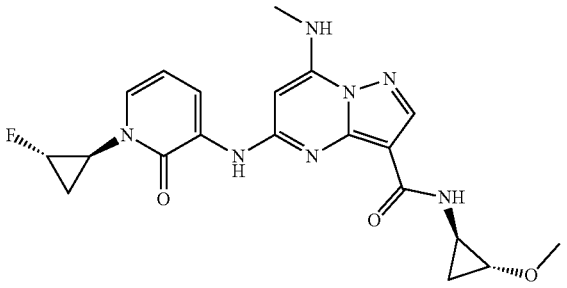 [SMILES: CNc1cc(Nc2cccn([C@H]3C[C@@H]3F)c2=O)nc2c(C(=O)N[C@@H]3C[C@H]3OC)cnn12] |
| I-1154 | 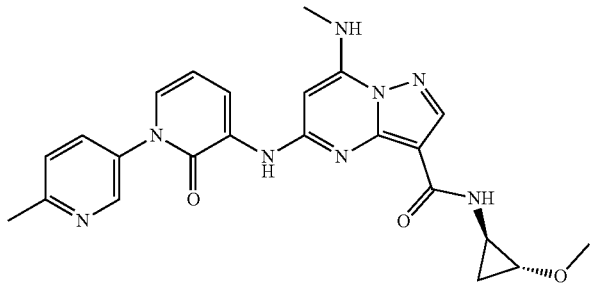 |
| I-1155 | 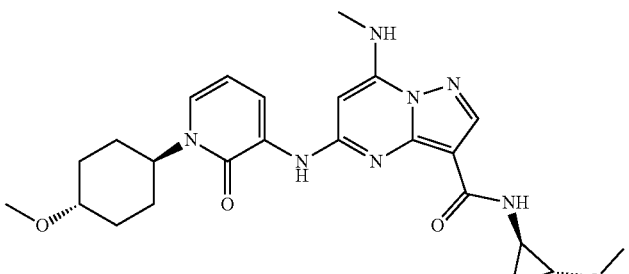 |
| I-1156 | 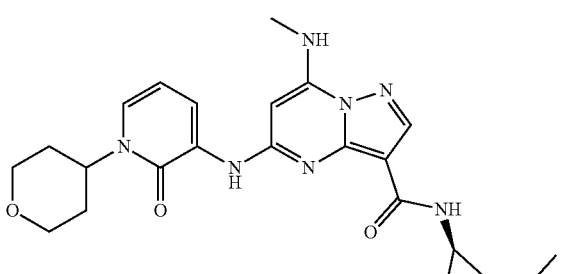 |

TABLE 1-continued

| Selected Compounds | |
|---|---|
| Compound | Structure |
| I-1157 | |
| I-1158 | |
| I-1159 | |
| I-1160 | |

TABLE 1-continued

Selected Compounds

| Compound | Structure |
|---|---|
| I-1161 | 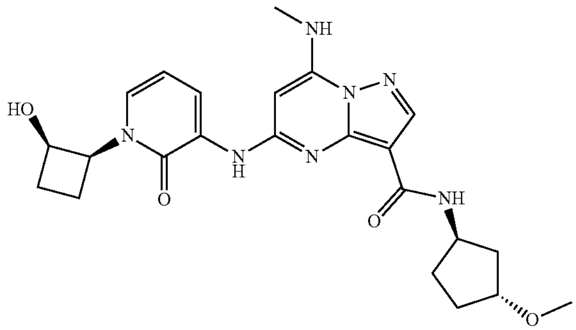 [SMILES: CNc1cc(Nc2cccn([C@H]3CC[C@H]3O)c2=O)nc2c(C(=O)N[C@@H]3CC[C@@H](OC)C3)cnn12] |
| I-1162 | 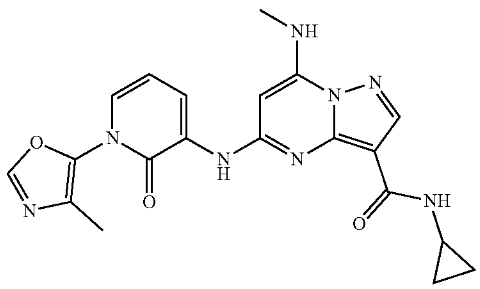 [SMILES: CNc1cc(Nc2cccn(-c3ocnc3C)c2=O)nc2c(C(=O)NC3CC3)cnn12] |
| I-1163 | 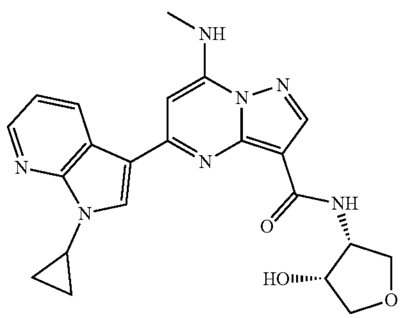 [SMILES: CNc1cc(-c2cn(C3CC3)c3ncccc23)nc2c(C(=O)N[C@@H]3COC[C@@H]3O)cnn12] |
| I-1164 | 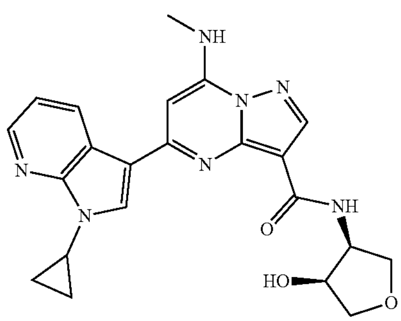 [SMILES: CNc1cc(-c2cn(C3CC3)c3ncccc23)nc2c(C(=O)N[C@H]3COC[C@H]3O)cnn12] |
| I-1165 | 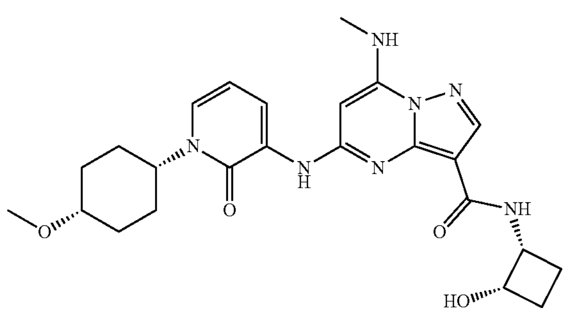 [SMILES: CNc1cc(Nc2cccn([C@H]3CC[C@@H](OC)CC3)c2=O)nc2c(C(=O)N[C@@H]3CC[C@@H]3O)cnn12] |

TABLE 1-continued
Selected Compounds
| Compound | Structure |
|---|---|
| I-1166 | 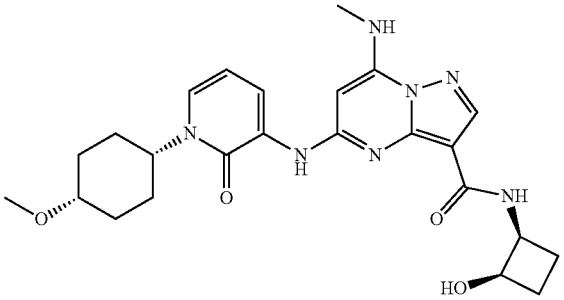 [SMILES: CNc1cc(Nc2cccn([C@H]3CC[C@@H](OC)CC3)c2=O)nc2c(C(=O)N[C@H]3CC[C@H]3O)cnn12] |
| I-1167 | 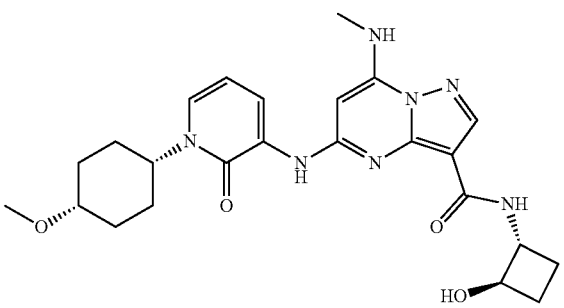 [SMILES: CNc1cc(Nc2cccn([C@H]3CC[C@@H](OC)CC3)c2=O)nc2c(C(=O)N[C@@H]3CC[C@H]3O)cnn12] |
| I-1168 | 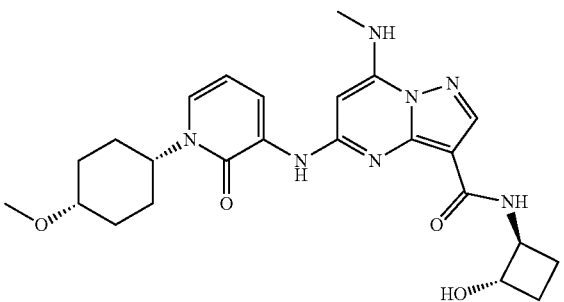 [SMILES: CNc1cc(Nc2cccn([C@H]3CC[C@@H](OC)CC3)c2=O)nc2c(C(=O)N[C@H]3CC[C@@H]3O)cnn12] |
| I-1169 | 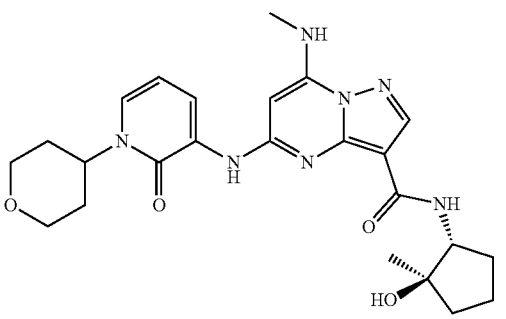 [SMILES: CNc1cc(Nc2cccn(C3CCOCC3)c2=O)nc2c(C(=O)N[C@@H]3CCC[C@@]3(C)O)cnn12] |
| I-1170 | 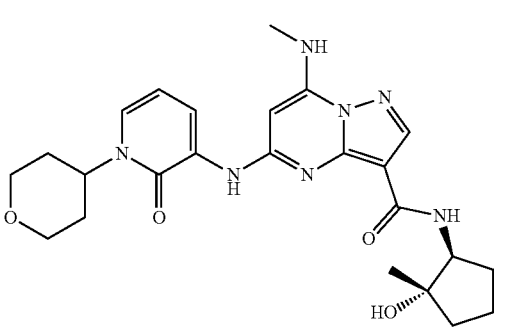 [SMILES: CNc1cc(Nc2cccn(C3CCOCC3)c2=O)nc2c(C(=O)N[C@H]3CCC[C@]3(C)O)cnn12] |

US 10,562,906 B2
635
636
TABLE 1-continued
Selected Compounds
| Compound | Structure |
|---|---|
| I-1171 | 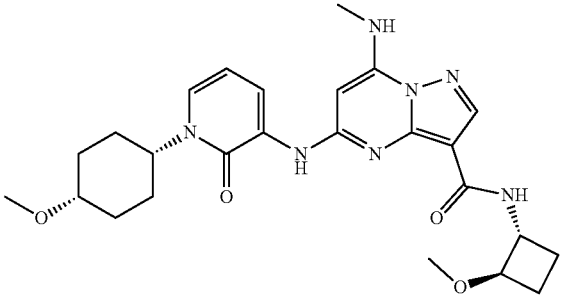 [SMILES: CNc1cc(Nc2cccn([C@H]3CC[C@@H](OC)CC3)c2=O)nc2c(C(=O)N[C@@H]3CC[C@H]3OC)cnn12] |
| I-1172 | 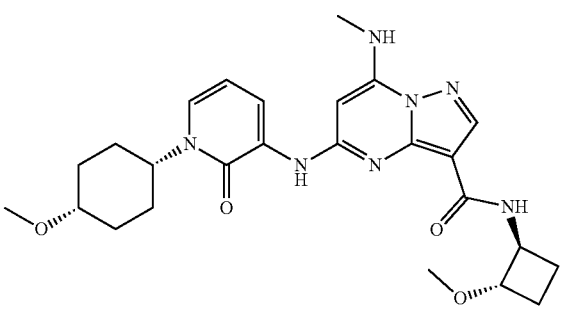 [SMILES: CNc1cc(Nc2cccn([C@H]3CC[C@@H](OC)CC3)c2=O)nc2c(C(=O)N[C@H]3CC[C@@H]3OC)cnn12] |
| I-1173 | 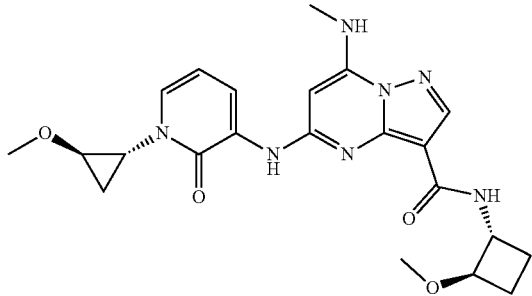 [SMILES: CNc1cc(Nc2cccn([C@@H]3C[C@H]3OC)c2=O)nc2c(C(=O)N[C@@H]3CC[C@H]3OC)cnn12] |
| I-1174 | 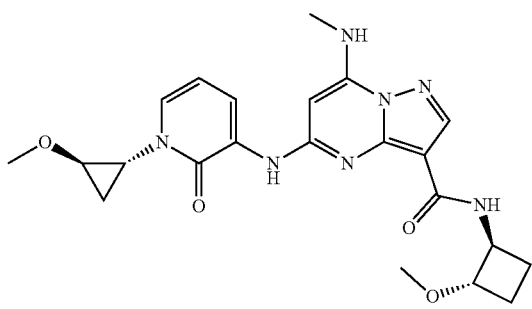 [SMILES: CNc1cc(Nc2cccn([C@@H]3C[C@H]3OC)c2=O)nc2c(C(=O)N[C@H]3CC[C@@H]3OC)cnn12] |
| I-1175 | 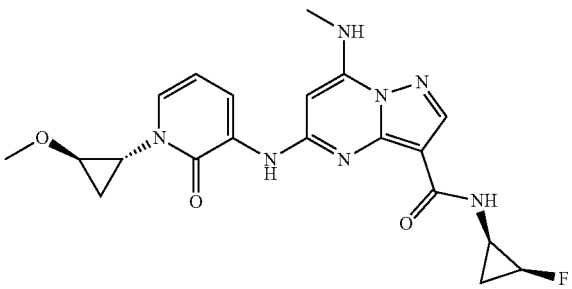 [SMILES: CNc1cc(Nc2cccn([C@@H]3C[C@H]3OC)c2=O)nc2c(C(=O)N[C@@H]3C[C@@H]3F)cnn12] |

TABLE 1-continued
Selected Compounds
| Compound | Structure |
|---|---|
| I-1176 | 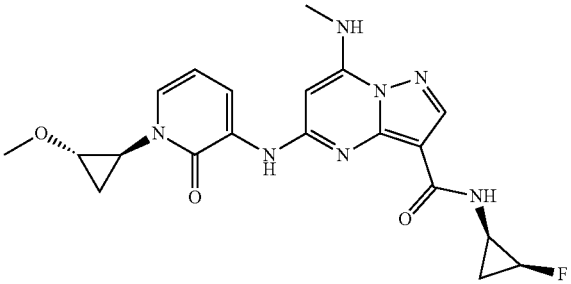 [SMILES: CNc1cc(Nc2cccn([C@H]3C[C@@H]3OC)c2=O)nc2c(C(=O)N[C@@H]3C[C@@H]3F)cnn12] |
| I-1177 | 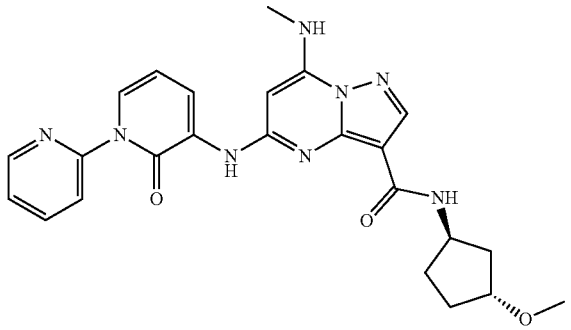 [SMILES: CNc1cc(Nc2cccn(-c3ccccn3)c2=O)nc2c(C(=O)N[C@@H]3CC[C@@H](OC)C3)cnn12] |
| I-1178 | 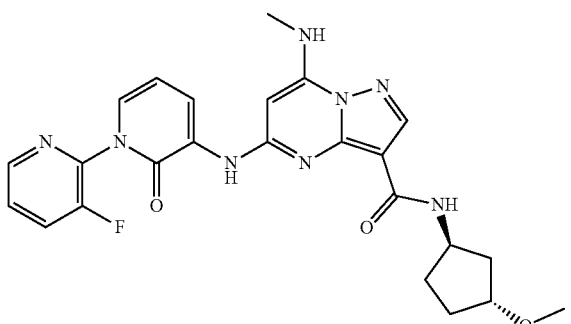 |
| I-1179 | 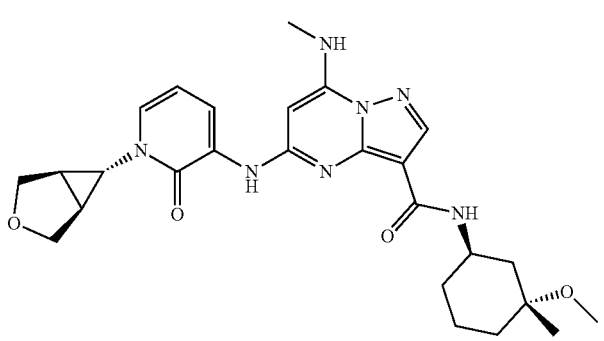 [SMILES: CNc1cc(Nc2cccn([C@H]3[C@@H]4COC[C@@H]43)c2=O)nc2c(C(=O)N[C@@H]3CCC[C@@](C)(OC)C3)cnn12] |

TABLE 1-continued

| Selected Compounds | |
|---|---|
| Compound | Structure |
| I-1180 | |
| I-1181 | |
| I-1182 | |
| I-1183 | |

TABLE 1-continued

Selected Compounds

| Compound | Structure |
|---|---|
| I-1184 | 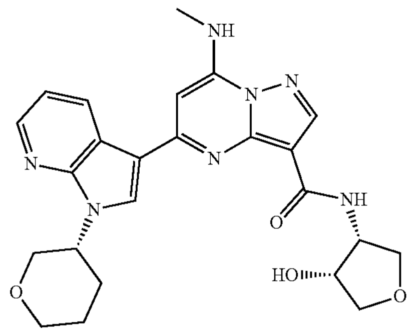 [SMILES: CNc1cc(-c2cn([C@@H]3CCCOC3)c3ncccc23)nc2c(C(=O)N[C@@H]3COC[C@@H]3O)cnn12] |
| I-1185 | 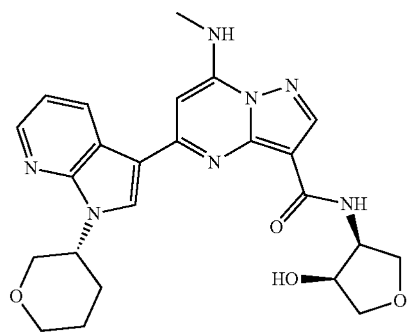 [SMILES: CNc1cc(-c2cn([C@@H]3CCCOC3)c3ncccc23)nc2c(C(=O)N[C@H]3COC[C@H]3O)cnn12] |
| I-1186 | 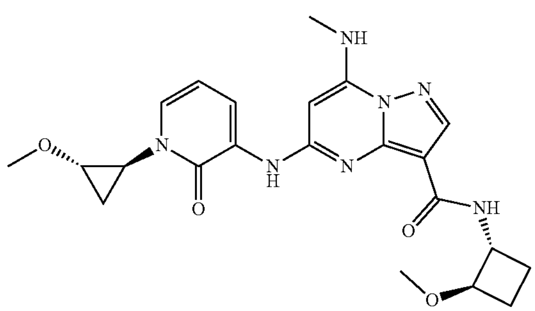 [SMILES: CNc1cc(Nc2cccn([C@H]3C[C@@H]3OC)c2=O)nc2c(C(=O)N[C@@H]3CC[C@H]3OC)cnn12] |
| I-1187 | 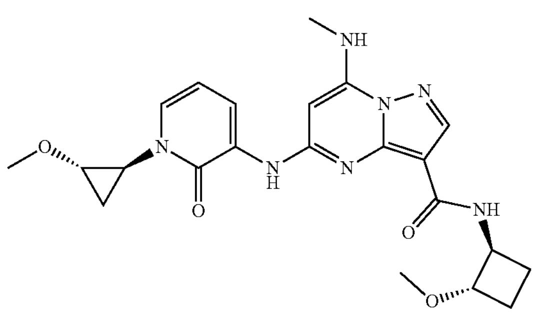 [SMILES: CNc1cc(Nc2cccn([C@H]3C[C@@H]3OC)c2=O)nc2c(C(=O)N[C@H]3CC[C@@H]3OC)cnn12] |

TABLE 1-continued
Selected Compounds
| Compound | Structure |
|---|---|
| I-1188 | 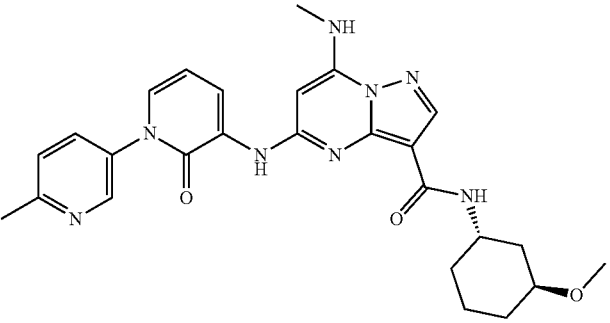 |
| I-1189 | 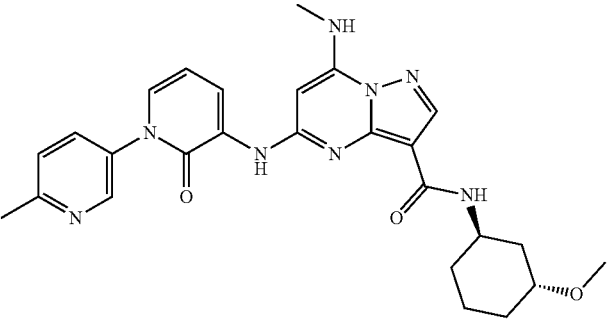 |
| I-1190 | 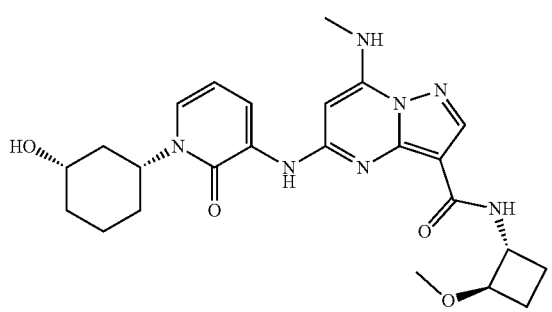 [SMILES: CNc1cc(Nc2cccn([C@@H]3CCC[C@H](O)C3)c2=O)nc2c(C(=O)N[C@@H]3CC[C@H]3OC)cnn12] |
| I-1191 | 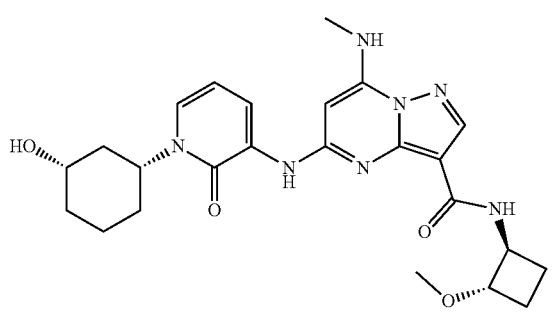 [SMILES: CNc1cc(Nc2cccn([C@@H]3CCC[C@H](O)C3)c2=O)nc2c(C(=O)N[C@H]3CC[C@@H]3OC)cnn12] |

TABLE 1-continued

Selected Compounds

| Compound | Structure |
|---|---|
| I-1192 | 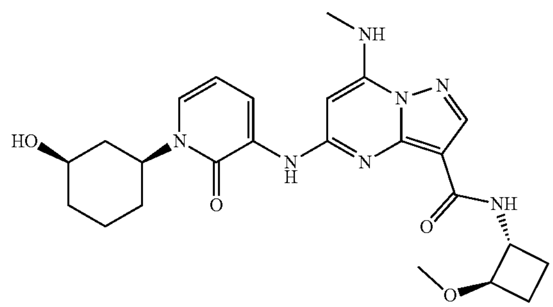 [SMILES: CNc1cc(Nc2cccn([C@H]3CCC[C@@H](O)C3)c2=O)nc2c(C(=O)N[C@@H]3CC[C@H]3OC)cnn12] |
| I-1193 | 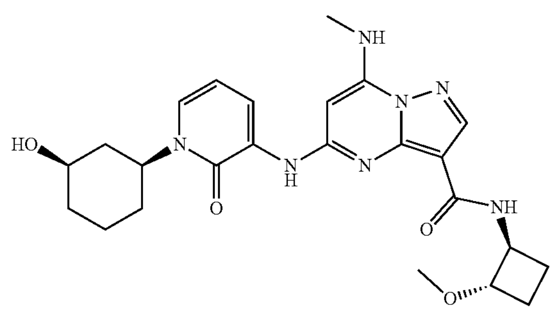 [SMILES: CNc1cc(Nc2cccn([C@H]3CCC[C@@H](O)C3)c2=O)nc2c(C(=O)N[C@H]3CC[C@@H]3OC)cnn12] |
| I-1194 | 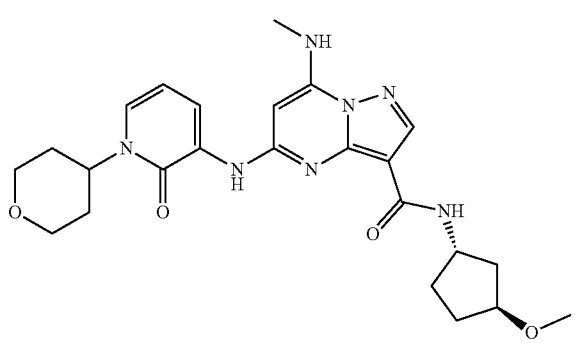 [SMILES: CNc1cc(Nc2cccn(C3CCOCC3)c2=O)nc2c(C(=O)N[C@H]3CC[C@H](OC)C3)cnn12] |
| I-1195 | 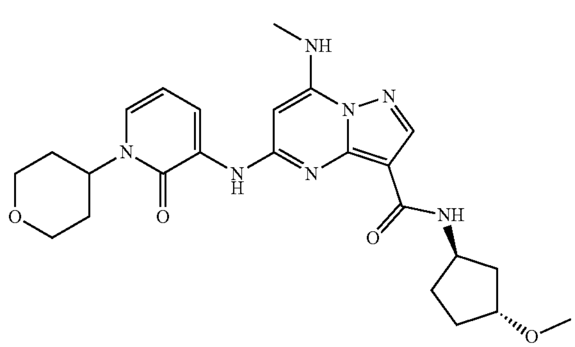 [SMILES: CNc1cc(Nc2cccn(C3CCOCC3)c2=O)nc2c(C(=O)N[C@@H]3CC[C@@H](OC)C3)cnn12] |

TABLE 1-continued

| Compound | Structure |
|---|---|
| I-1196 | 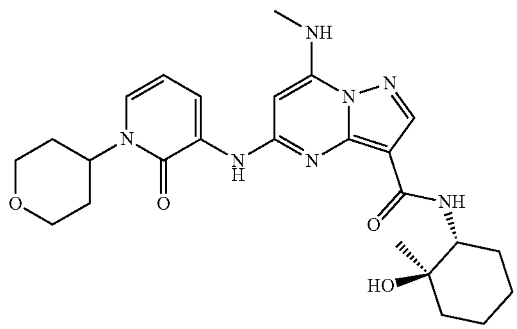 [SMILES: CNc1cc(Nc2cccn(C3CCOCC3)c2=O)nc2c(C(=O)N[C@@H]3CCCC[C@@]3(C)O)cnn12] |
| I-1197 | 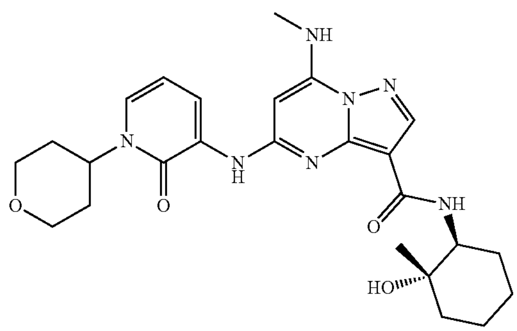 [SMILES: CNc1cc(Nc2cccn(C3CCOCC3)c2=O)nc2c(C(=O)N[C@H]3CCCC[C@]3(C)O)cnn12] |
| I-1198 | 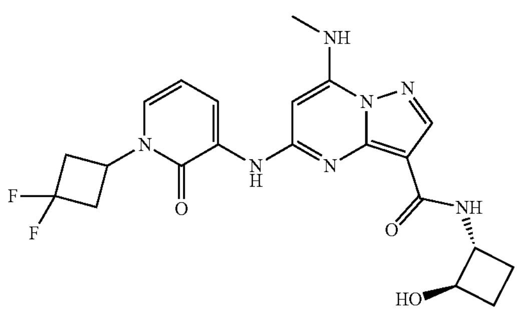 [SMILES: CNc1cc(Nc2cccn(C3CC(F)(F)C3)c2=O)nc2c(C(=O)N[C@@H]3CC[C@H]3O)cnn12] |
| I-1199 | 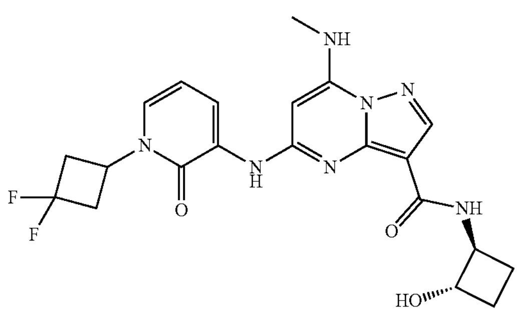 [SMILES: CNc1cc(Nc2cccn(C3CC(F)(F)C3)c2=O)nc2c(C(=O)N[C@H]3CC[C@@H]3O)cnn12] |

TABLE 1-continued

Selected Compounds

| Compound | Structure |
|---|---|
| I-1200 | 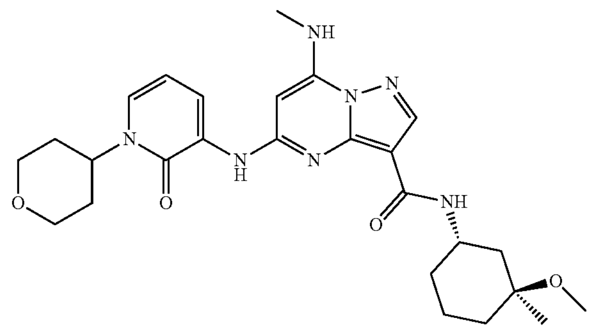 [SMILES: CNc1cc(Nc2cccn(C3CCOCC3)c2=O)nc2c(C(=O)N[C@H]3CCC[C@](C)(OC)C3)cnn12] |
| I-1201 | 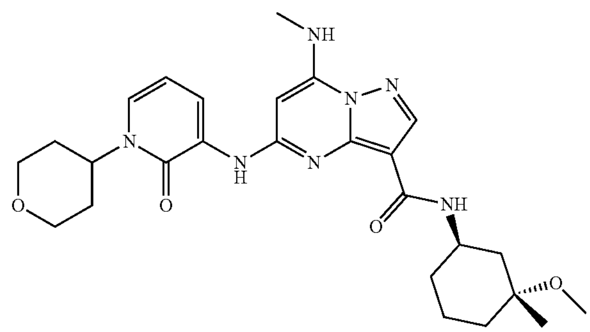 [SMILES: CNc1cc(Nc2cccn(C3CCOCC3)c2=O)nc2c(C(=O)N[C@@H]3CCC[C@@](C)(OC)C3)cnn12] |
| I-1202 | 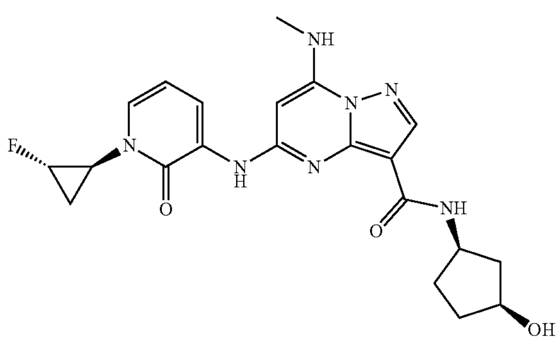 [SMILES: CNc1cc(Nc2cccn([C@H]3C[C@@H]3F)c2=O)nc2c(C(=O)N[C@@H]3CC[C@H](O)C3)cnn12] |
| I-1203 | 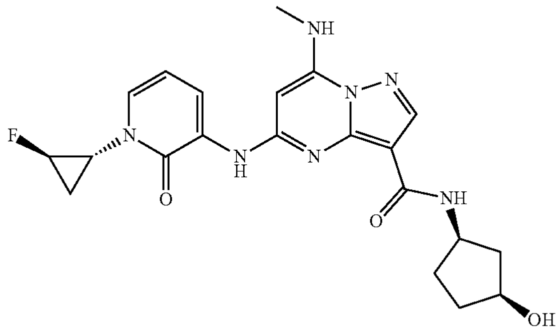 [SMILES: CNc1cc(Nc2cccn([C@@H]3C[C@H]3F)c2=O)nc2c(C(=O)N[C@@H]3CC[C@H](O)C3)cnn12] |

TABLE 1-continued

Selected Compounds

| Compound | Structure |
|---|---|
| I-1204 | 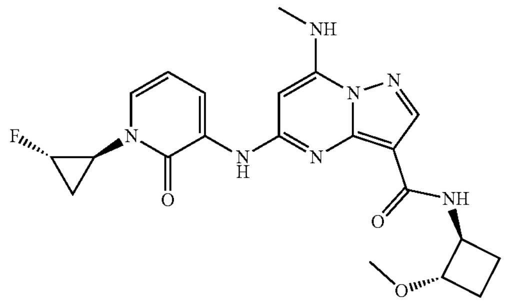 [SMILES: CNc1cc(Nc2cccn([C@H]3C[C@@H]3F)c2=O)nc2c(C(=O)N[C@H]3CC[C@@H]3OC)cnn12] |
| I-1205 | 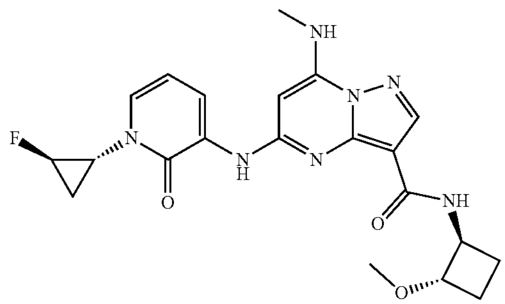 [SMILES: CNc1cc(Nc2cccn([C@@H]3C[C@H]3F)c2=O)nc2c(C(=O)N[C@H]3CC[C@@H]3OC)cnn12] |
| I-1206 | 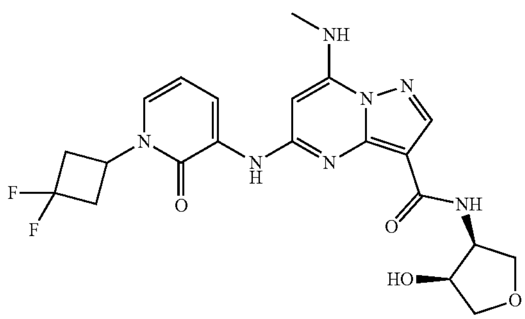 [SMILES: CNc1cc(Nc2cccn(C3CC(F)(F)C3)c2=O)nc2c(C(=O)N[C@H]3COC[C@H]3O)cnn12] |
| I-1207 | 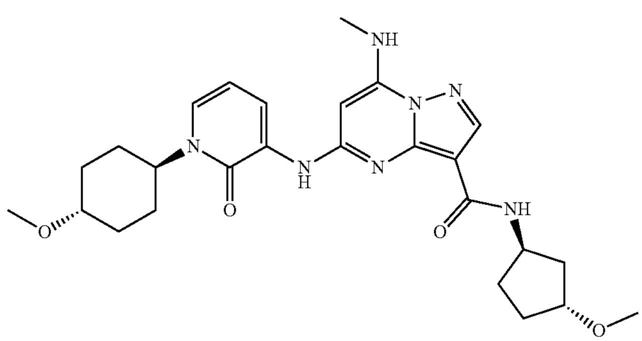 |

TABLE 1-continued
| Compound | Structure |
|---|---|
| I-1208 | 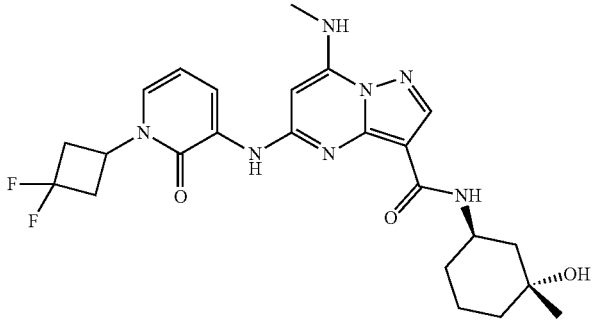 [SMILES: CNc1cc(Nc2cccn(C3CC(F)(F)C3)c2=O)nc2c(C(=O)N[C@@H]3CCC[C@@](C)(O)C3)cnn12] |
| I-1209 | 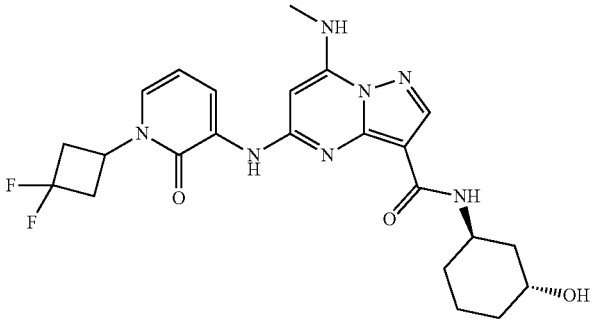 [SMILES: CNc1cc(Nc2cccn(C3CC(F)(F)C3)c2=O)nc2c(C(=O)N[C@@H]3CCC[C@@H](O)C3)cnn12] |
| I-1210 | 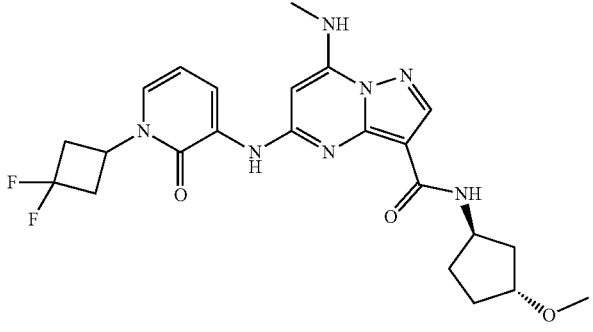 [SMILES: CNc1cc(Nc2cccn(C3CC(F)(F)C3)c2=O)nc2c(C(=O)N[C@@H]3CC[C@@H](OC)C3)cnn12] |
| I-1211 | 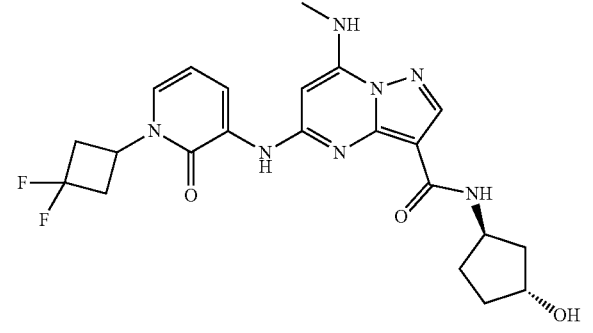 [SMILES: CNc1cc(Nc2cccn(C3CC(F)(F)C3)c2=O)nc2c(C(=O)N[C@@H]3CC[C@@H](O)C3)cnn12] |

TABLE 1-continued

Selected Compounds

| Compound | Structure |
|---|---|
| I-1212 | 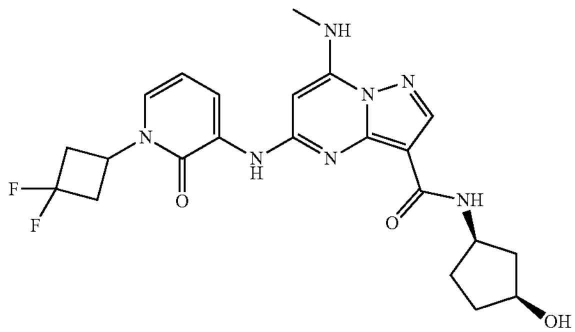 [SMILES: CNc1cc(Nc2cccn(C3CC(F)(F)C3)c2=O)nc2c(C(=O)N[C@@H]3CC[C@H](O)C3)cnn12] |
| I-1213 | 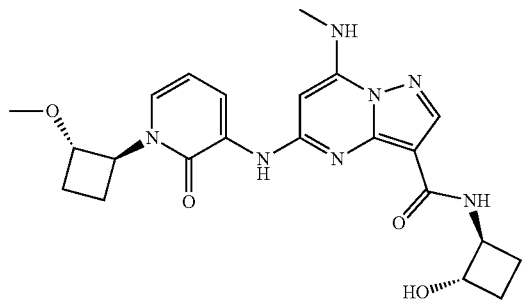 [SMILES: CNc1cc(Nc2cccn([C@H]3CC[C@@H]3OC)c2=O)nc2c(C(=O)N[C@H]3CC[C@@H]3O)cnn12] |
| I-1214 | 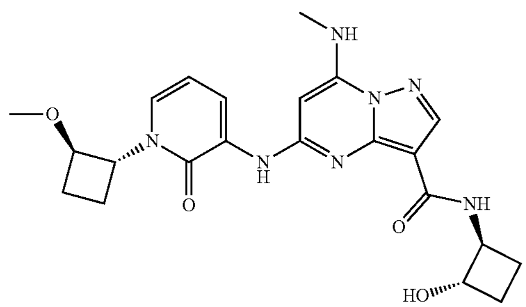 [SMILES: CNc1cc(Nc2cccn([C@@H]3CC[C@H]3OC)c2=O)nc2c(C(=O)N[C@H]3CC[C@@H]3O)cnn12] |
| I-1215 | 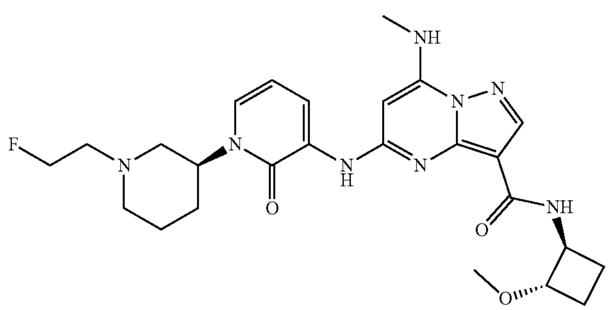 [SMILES: CNc1cc(Nc2cccn([C@H]3CCCN(CCF)C3)c2=O)nc2c(C(=O)N[C@H]3CC[C@@H]3OC)cnn12] |
| I-1216 | 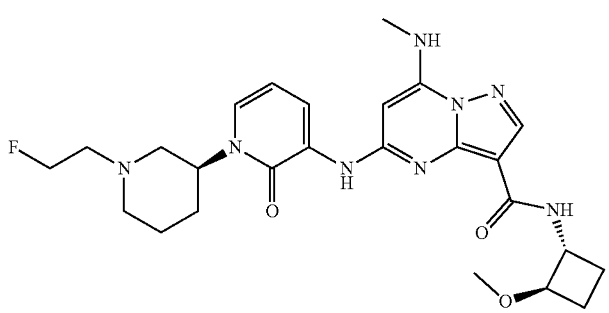 [SMILES: CNc1cc(Nc2cccn([C@H]3CCCN(CCF)C3)c2=O)nc2c(C(=O)N[C@@H]3CC[C@H]3OC)cnn12] |

TABLE 1-continued

Selected Compounds

| Compound | Structure |
|---|---|
| I-1217 | 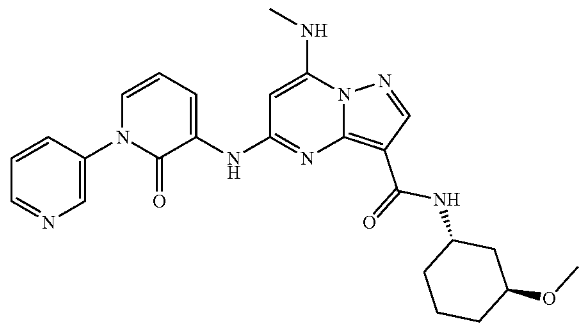 [SMILES: CNc1cc(Nc2cccn(-c3cccnc3)c2=O)nc2c(C(=O)N[C@H]3CCC[C@H](OC)C3)cnn12] |
| I-1218 | 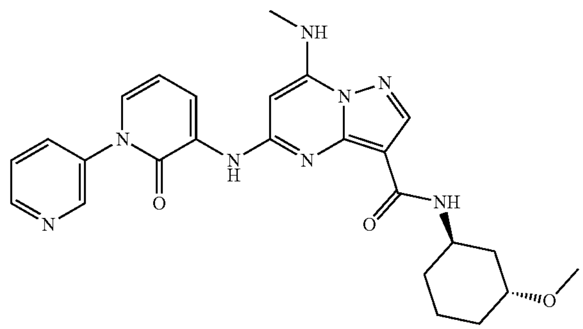 [SMILES: CNc1cc(Nc2cccn(-c3cccnc3)c2=O)nc2c(C(=O)N[C@@H]3CCC[C@@H](OC)C3)cnn12] |
| I-1219 | 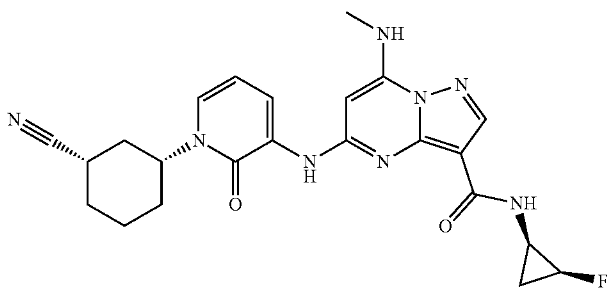 [SMILES: CNc1cc(Nc2cccn([C@@H]3CCC[C@H](C#N)C3)c2=O)nc2c(C(=O)N[C@@H]3C[C@@H]3F)cnn12] |
| I-1220 | 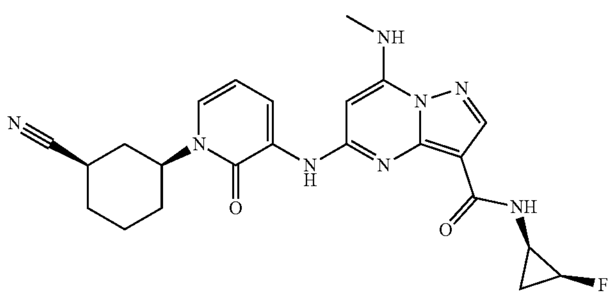 [SMILES: CNc1cc(Nc2cccn([C@H]3CCC[C@@H](C#N)C3)c2=O)nc2c(C(=O)N[C@@H]3C[C@@H]3F)cnn12] |
| I-1221 | 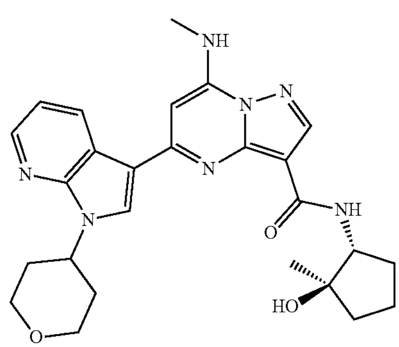 [SMILES: CNc1cc(-c2cn(C3CCOCC3)c3ncccc23)nc2c(C(=O)N[C@@H]3CCC[C@@]3(C)O)cnn12] |

TABLE 1-continued
| Compound | Structure |
|---|---|
| I-1222 | 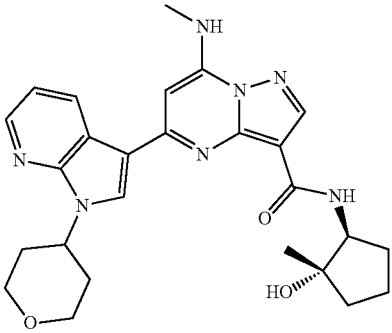 [SMILES: CNc1cc(-c2cn(C3CCOCC3)c3ncccc23)nc2c(C(=O)N[C@H]3CCC[C@]3(C)O)cnn12] |
| I-1223 | 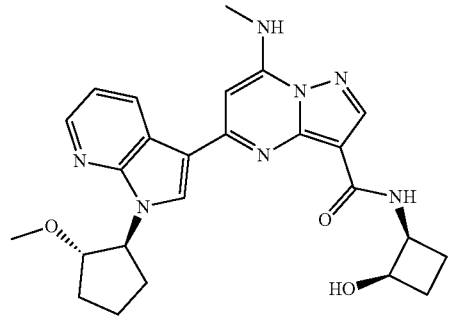 [SMILES: CNc1cc(-c2cn([C@H]3CCC[C@@H]3OC)c3ncccc23)nc2c(C(=O)N[C@H]3CC[C@H]3O)cnn12] |
| I-1224 | 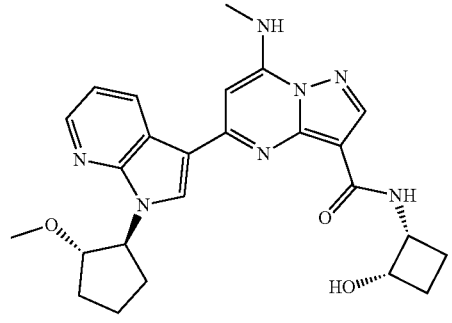 [SMILES: CNc1cc(-c2cn([C@H]3CCC[C@@H]3OC)c3ncccc23)nc2c(C(=O)N[C@@H]3CC[C@@H]3O)cnn12] |
| I-1225 | 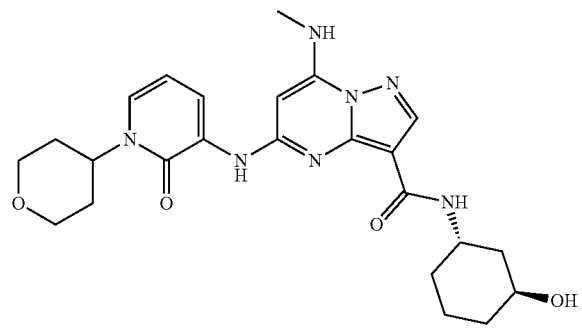 [SMILES: CNc1cc(Nc2cccn(C3CCOCC3)c2=O)nc2c(C(=O)N[C@H]3CCC[C@H](O)C3)cnn12] |

TABLE 1-continued

Selected Compounds

| Compound | Structure |
|---|---|
| I-1226 | 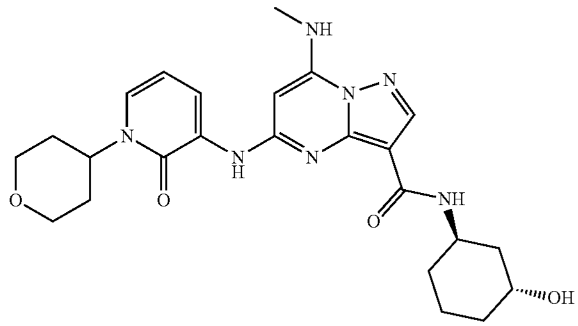 [SMILES: CNc1cc(Nc2cccn(C3CCOCC3)c2=O)nc2c(C(=O)N[C@@H]3CCC[C@@H](O)C3)cnn12] |
| I-1227 | 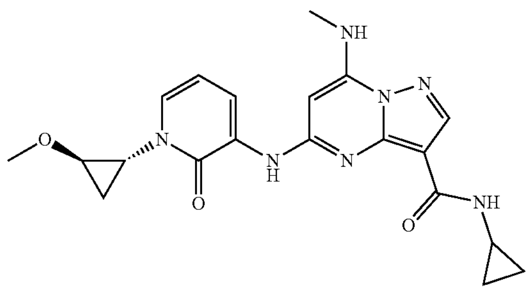 [SMILES: CNc1cc(Nc2cccn([C@@H]3C[C@H]3OC)c2=O)nc2c(C(=O)NC3CC3)cnn12] |
| I-1228 | 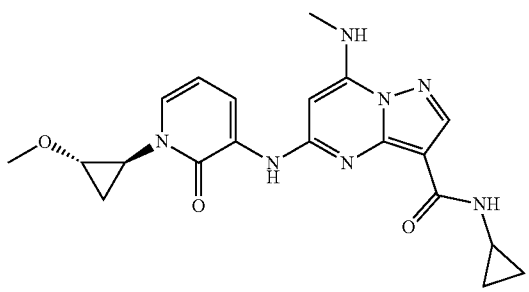 [SMILES: CNc1cc(Nc2cccn([C@H]3C[C@@H]3OC)c2=O)nc2c(C(=O)NC3CC3)cnn12] |
| I-1229 | 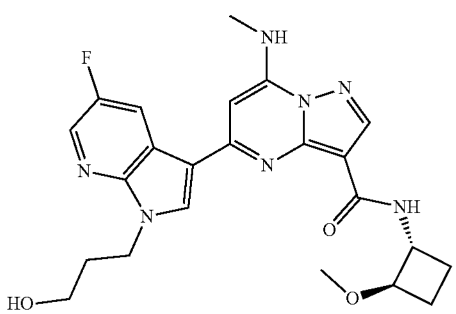 [SMILES: CNc1cc(-c2cn(CCCO)c3ncc(F)cc23)nc2c(C(=O)N[C@@H]3CC[C@H]3OC)cnn12] |
| I-1230 | 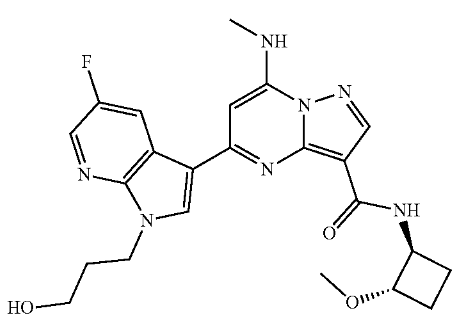 [SMILES: CNc1cc(-c2cn(CCCO)c3ncc(F)cc23)nc2c(C(=O)N[C@H]3CC[C@@H]3OC)cnn12] |

TABLE 1-continued

Selected Compounds

| Compound | Structure |
|---|---|
| I-1231 | 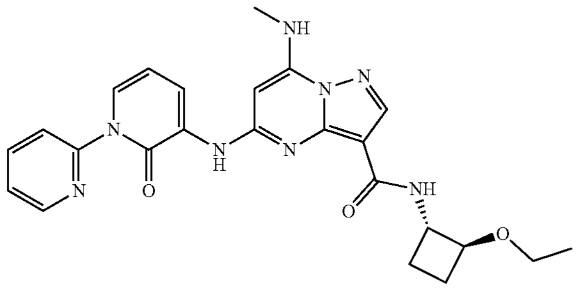 [SMILES: CCO[C@H]1CC[C@@H]1NC(=O)c1cnn2c(NC)cc(Nc3cccn(-c4ccccn4)c3=O)nc12] |
| I-1232 | 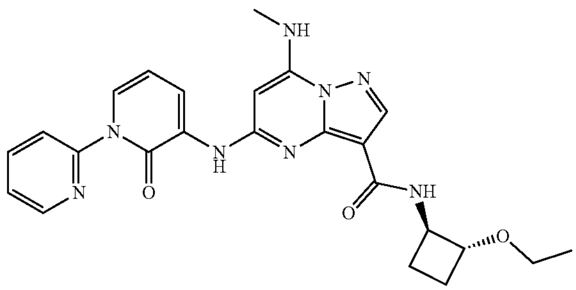 [SMILES: CCO[C@@H]1CC[C@H]1NC(=O)c1cnn2c(NC)cc(Nc3cccn(-c4ccccn4)c3=O)nc12] |
| I-1233 | 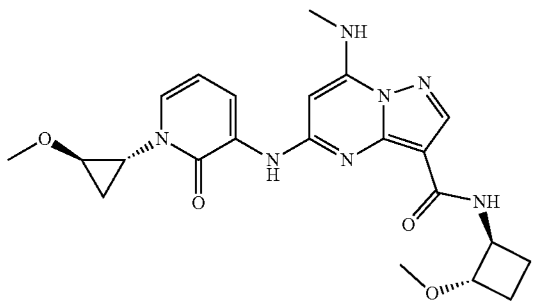 [SMILES: CNc1cc(Nc2cccn([C@@H]3C[C@H]3OC)c2=O)nc2c(C(=O)N[C@H]3CC[C@@H]3OC)cnn12] |
| I-1234 | 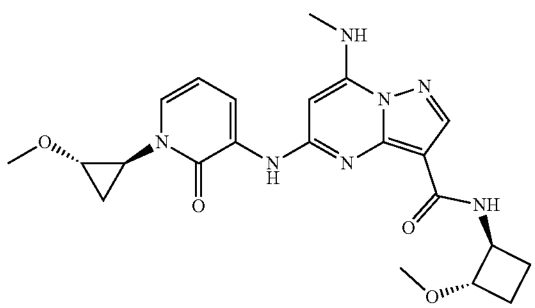 [SMILES: CNc1cc(Nc2cccn([C@H]3C[C@@H]3OC)c2=O)nc2c(C(=O)N[C@H]3CC[C@@H]3OC)cnn12] |
| I-1235 | 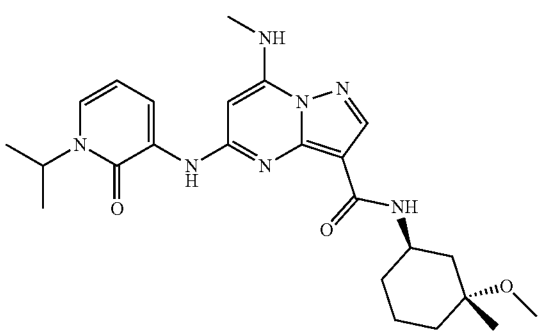 [SMILES: CNc1cc(Nc2cccn(C(C)C)c2=O)nc2c(C(=O)N[C@@H]3CCC[C@@](C)(OC)C3)cnn12] |

TABLE 1-continued

Selected Compounds

| Compound | Structure |
|---|---|
| I-1236 | 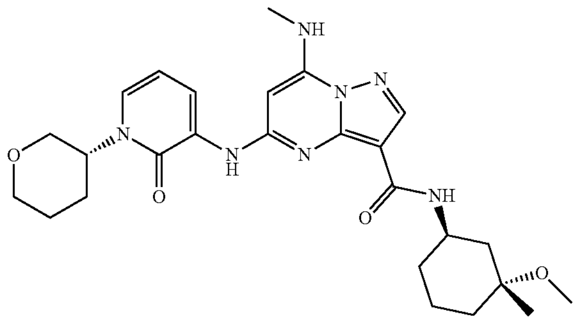 [SMILES: CNc1cc(Nc2cccn([C@@H]3CCCOC3)c2=O)nc2c(C(=O)N[C@@H]3CCC[C@@](C)(OC)C3)cnn12] |
| I-1237 | 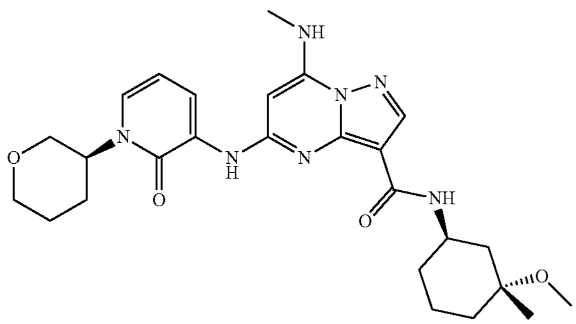 [SMILES: CNc1cc(Nc2cccn([C@H]3CCCOC3)c2=O)nc2c(C(=O)N[C@@H]3CCC[C@@](C)(OC)C3)cnn12] |
| I-1238 | 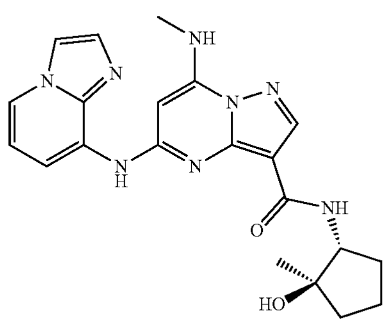 [SMILES: CNc1cc(Nc2cccn3ccnc23)nc2c(C(=O)N[C@@H]3CCC[C@@]3(C)O)cnn12] |
| I-1239 | 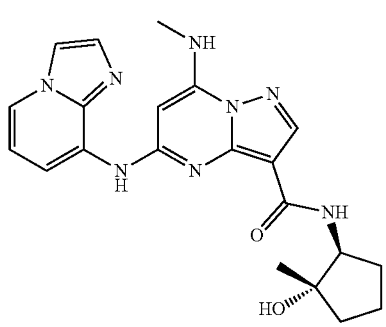 [SMILES: CNc1cc(Nc2cccn3ccnc23)nc2c(C(=O)N[C@H]3CCC[C@]3(C)O)cnn12] |

TABLE 1-continued

| Selected Compounds | |
|---|---|
| Compound | Structure |
| I-1240 | |
| I-1241 | |
| I-1242 | |
| I-1243 | |

TABLE 1-continued

Selected Compounds

| Compound | Structure |
|---|---|
| I-1244 | 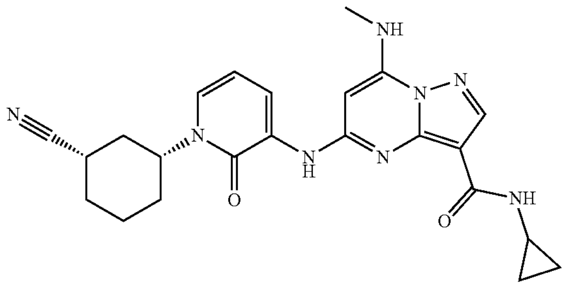 [SMILES: CNc1cc(Nc2cccn([C@@H]3CCC[C@H](C#N)C3)c2=O)nc2c(C(=O)NC3CC3)cnn12] |
| I-1245 | 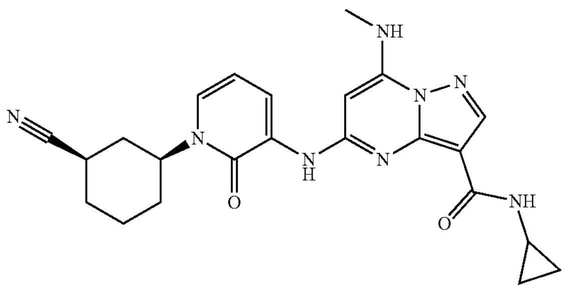 [SMILES: CNc1cc(Nc2cccn([C@H]3CCC[C@@H](C#N)C3)c2=O)nc2c(C(=O)NC3CC3)cnn12] |
| I-1246 | 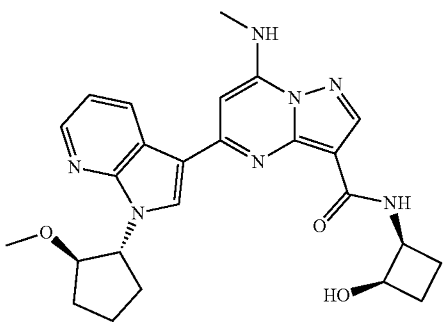 [SMILES: CNc1cc(-c2cn([C@@H]3CCC[C@H]3OC)c3ncccc23)nc2c(C(=O)N[C@H]3CC[C@H]3O)cnn12] |
| I-1247 | 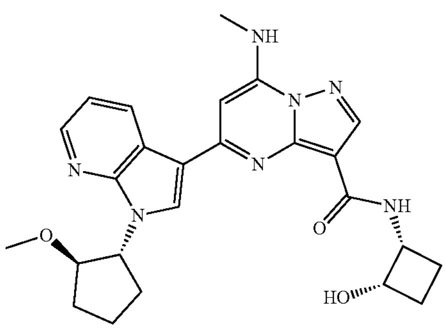 [SMILES: CNc1cc(-c2cn([C@@H]3CCC[C@H]3OC)c3ncccc23)nc2c(C(=O)N[C@@H]3CC[C@@H]3O)cnn12] |
| I-1248 | 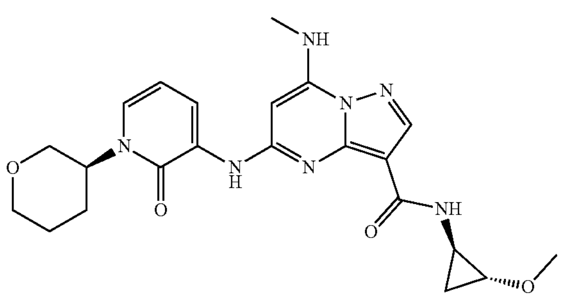 [SMILES: CNc1cc(Nc2cccn([C@H]3CCCOC3)c2=O)nc2c(C(=O)N[C@@H]3C[C@H]3OC)cnn12] |

TABLE 1-continued

Selected Compounds

| Compound | Structure |
|---|---|
| I-1249 | 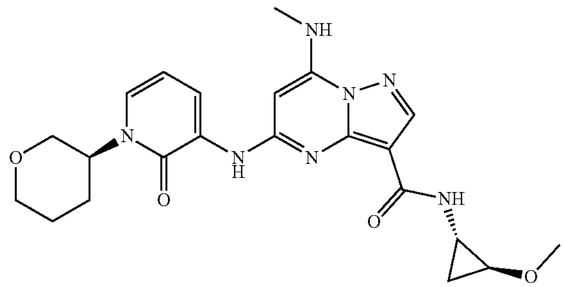 [SMILES: CNc1cc(Nc2cccn([C@H]3CCCOC3)c2=O)nc2c(C(=O)N[C@H]3C[C@@H]3OC)cnn12] |
| I-1250 | 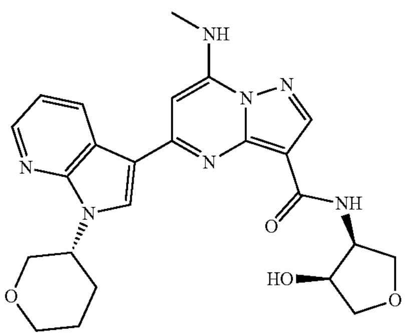 [SMILES: CNc1cc(-c2cn([C@@H]3CCCOC3)c3ncccc23)nc2c(C(=O)N[C@H]3COC[C@H]3O)cnn12] |
| I-1251 | 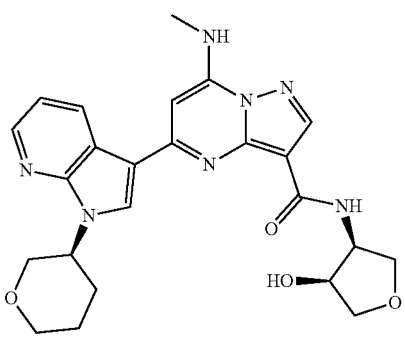 [SMILES: CNc1cc(-c2cn([C@H]3CCCOC3)c3ncccc23)nc2c(C(=O)N[C@H]3COC[C@H]3O)cnn12] |
| I-1252 | 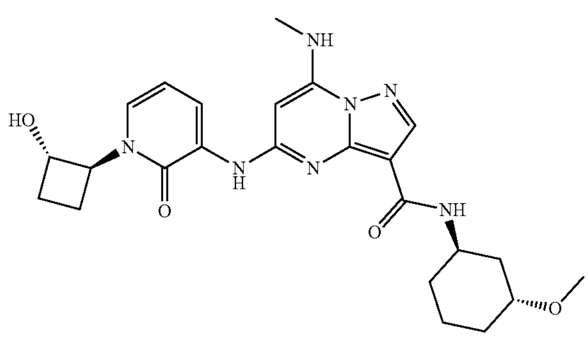 [SMILES: CNc1cc(Nc2cccn([C@H]3CC[C@@H]3O)c2=O)nc2c(C(=O)N[C@@H]3CCC[C@@H](OC)C3)cnn12] |

TABLE 1-continued
Selected Compounds
| Compound | Structure |
|---|---|
| I-1253 | 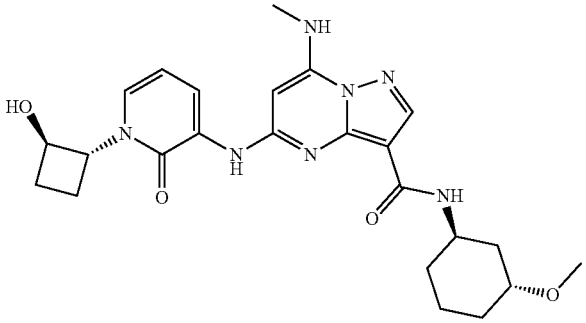 [SMILES: CNc1cc(Nc2cccn([C@@H]3CC[C@H]3O)c2=O)nc2c(C(=O)N[C@@H]3CCC[C@@H](OC)C3)cnn12] |
| I-1254 | 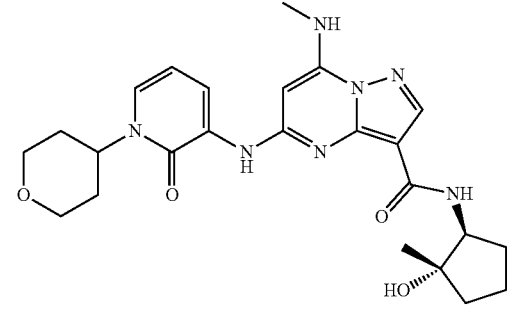 [SMILES: CNc1cc(Nc2cccn(C3CCOCC3)c2=O)nc2c(C(=O)N[C@H]3CCC[C@]3(C)O)cnn12] |
| I-1255 | 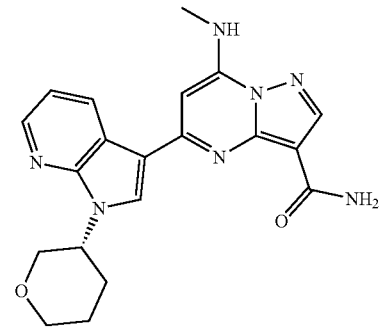 [SMILES: CNc1cc(-c2cn([C@@H]3CCCOC3)c3ncccc23)nc2c(C(N)=O)cnn12] |
| I-1256 | 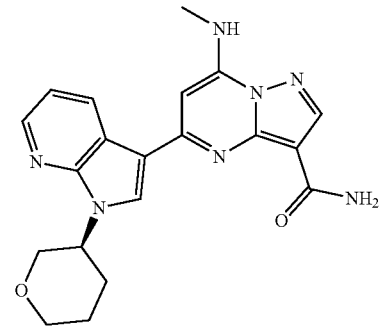 [SMILES: CNc1cc(-c2cn([C@H]3CCCOC3)c3ncccc23)nc2c(C(N)=O)cnn12] |

TABLE 1-continued
Selected Compounds
| Compound | Structure |
|---|---|
| I-1257 | 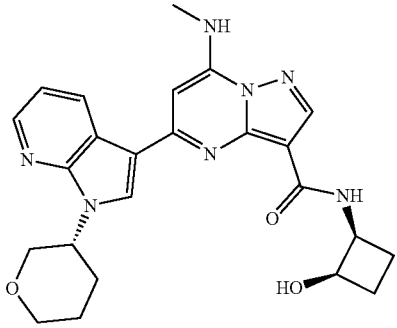 [SMILES: CNc1cc(-c2cn([C@@H]3CCCOC3)c3ncccc23)nc2c(C(=O)N[C@H]3CC[C@H]3O)cnn12] |
| I-1258 | 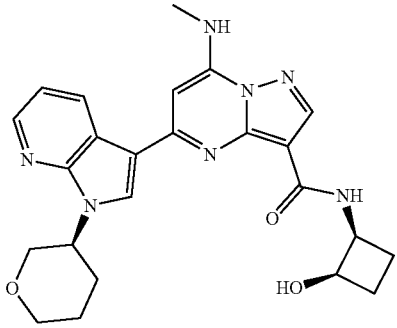 [SMILES: CNc1cc(-c2cn([C@H]3CCCOC3)c3ncccc23)nc2c(C(=O)N[C@H]3CC[C@H]3O)cnn12] |
| I-1259 | 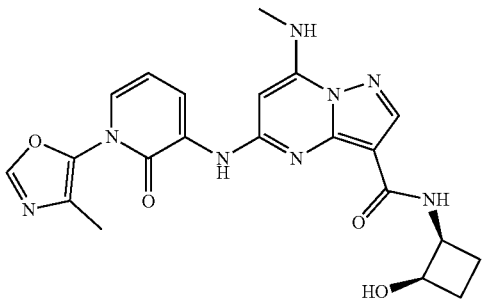 [SMILES: CNc1cc(Nc2cccn(-c3ocnc3C)c2=O)nc2c(C(=O)N[C@H]3CC[C@H]3O)cnn12] |
| I-1260 | 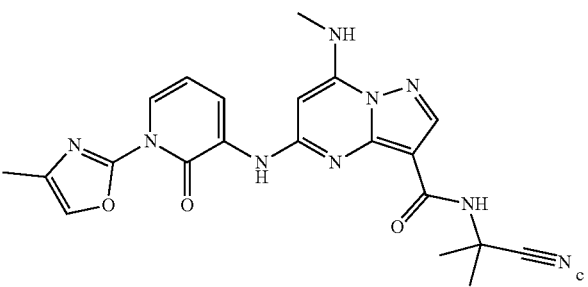 [SMILES: CNc1cc(Nc2cccn(-c3nc(C)co3)c2=O)nc2c(C(=O)NC(C)(C)C#N)cnn12] |

TABLE 1-continued

Selected Compounds

| Compound | Structure |
|---|---|
| I-1261 | 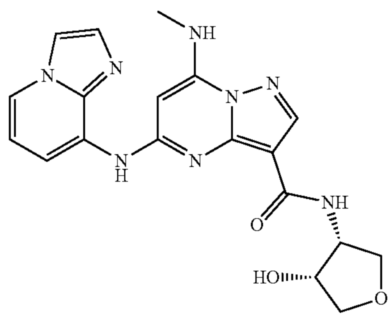 [SMILES: CNc1cc(Nc2cccn3ccnc23)nc2c(C(=O)N[C@@H]3COC[C@@H]3O)cnn12] |
| I-1262 | 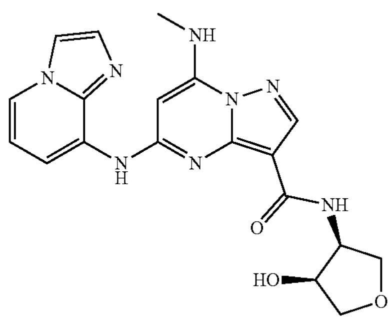 [SMILES: CNc1cc(Nc2cccn3ccnc23)nc2c(C(=O)N[C@H]3COC[C@H]3O)cnn12] |
| I-1263 | 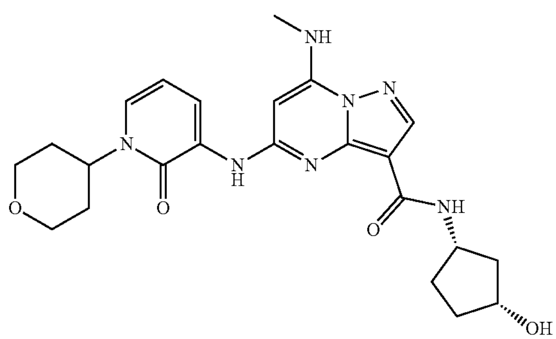 [SMILES: CNc1cc(Nc2cccn(C3CCOCC3)c2=O)nc2c(C(=O)N[C@H]3CC[C@@H](O)C3)cnn12] |
| I-1264 | 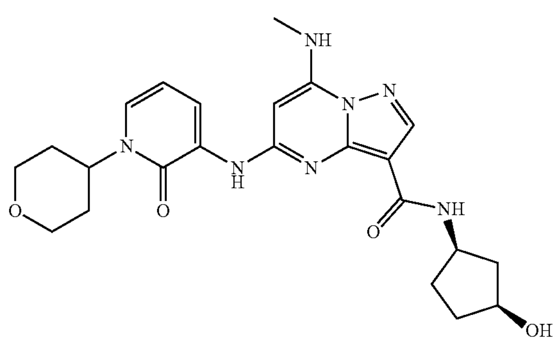 [SMILES: CNc1cc(Nc2cccn(C3CCOCC3)c2=O)nc2c(C(=O)N[C@@H]3CC[C@H](O)C3)cnn12] |

TABLE 1-continued

Selected Compounds

| Compound | Structure |
|---|---|
| I-1265 | 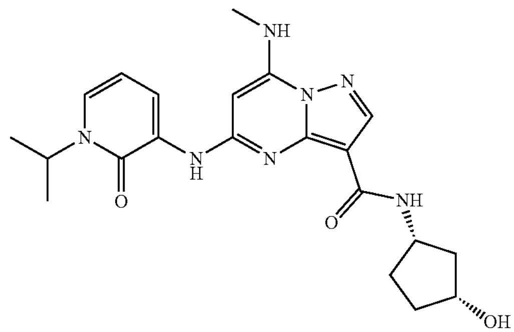 [SMILES: CNc1cc(Nc2cccn(C(C)C)c2=O)nc2c(C(=O)N[C@H]3CC[C@@H](O)C3)cnn12] |
| I-1266 | 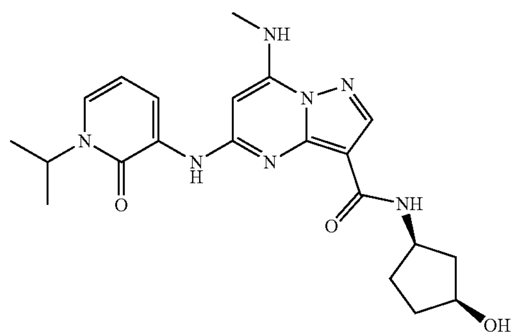 [SMILES: CNc1cc(Nc2cccn(C(C)C)c2=O)nc2c(C(=O)N[C@@H]3CC[C@H](O)C3)cnn12] |
| I-1267 | 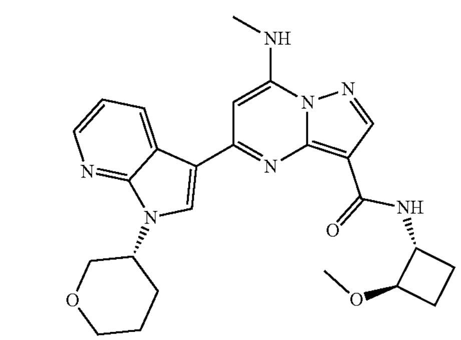 [SMILES: CNc1cc(-c2cn([C@@H]3CCCOC3)c3ncccc23)nc2c(C(=O)N[C@@H]3CC[C@H]3OC)cnn12] |
| I-1268 | 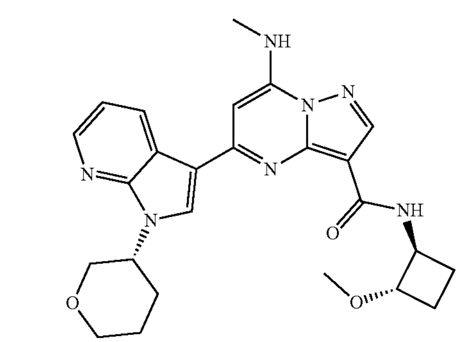 [SMILES: CNc1cc(-c2cn([C@@H]3CCCOC3)c3ncccc23)nc2c(C(=O)N[C@H]3CC[C@@H]3OC)cnn12] |

TABLE 1-continued

Selected Compounds

| Compound | Structure |
|---|---|
| I-1269 | 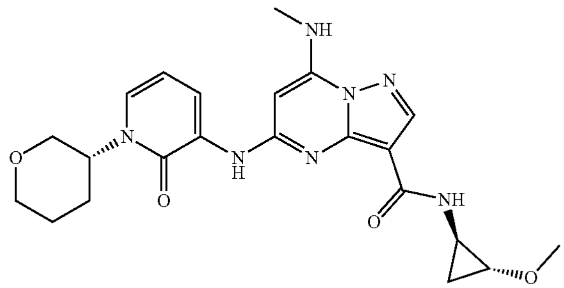 [SMILES: CNc1cc(Nc2cccn([C@@H]3CCCOC3)c2=O)nc2c(C(=O)N[C@@H]3C[C@H]3OC)cnn12] |
| I-1270 | 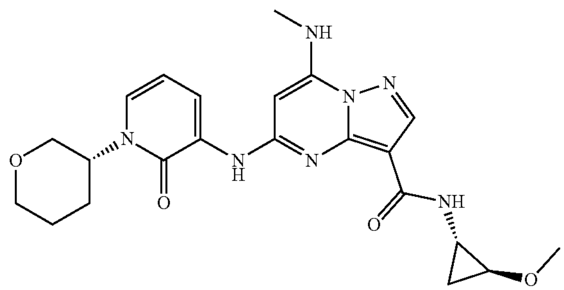 [SMILES: CNc1cc(Nc2cccn([C@@H]3CCCOC3)c2=O)nc2c(C(=O)N[C@H]3C[C@@H]3OC)cnn12] |
| I-1271 | 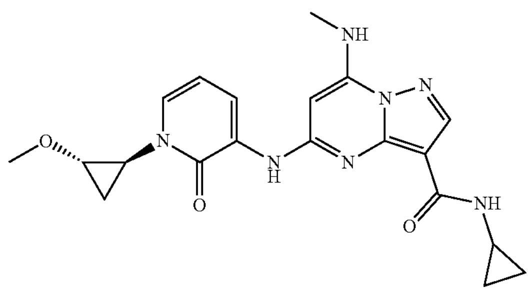 [SMILES: CNc1cc(Nc2cccn([C@H]3C[C@@H]3OC)c2=O)nc2c(C(=O)NC3CC3)cnn12] |
| I-1272 | 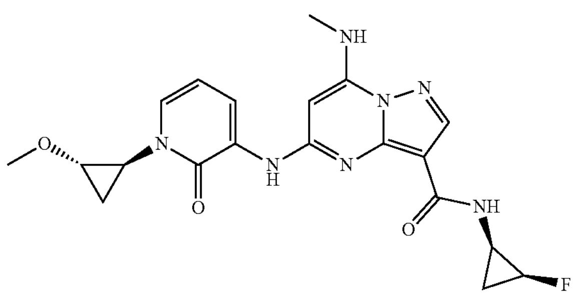 [SMILES: CNc1cc(Nc2cccn([C@H]3C[C@@H]3OC)c2=O)nc2c(C(=O)N[C@@H]3C[C@@H]3F)cnn12] |
| I-1273 | 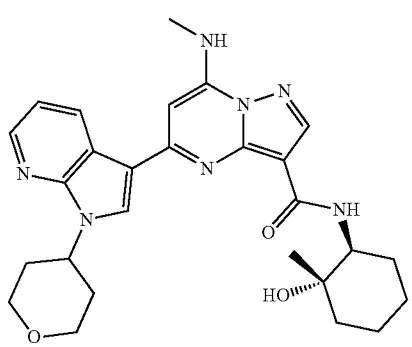 [SMILES: CNc1cc(-c2cn(C3CCOCC3)c3ncccc23)nc2c(C(=O)N[C@H]3CCCC[C@]3(C)O)cnn12] |

TABLE 1-continued

Selected Compounds

| Compound | Structure |
|---|---|
| I-1274 | 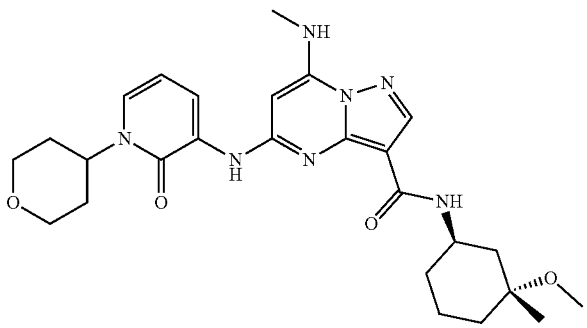 [SMILES: CNc1cc(Nc2cccn(C3CCOCC3)c2=O)nc2c(C(=O)N[C@@H]3CCC[C@@](C)(OC)C3)cnn12] |
| I-1275 | 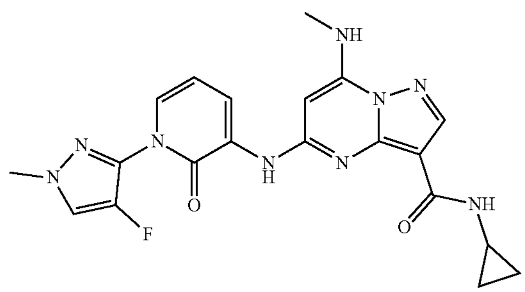 [SMILES: CNc1cc(Nc2cccn(-c3nn(C)cc3F)c2=O)nc2c(C(=O)NC3CC3)cnn12] |
| I-1276 | 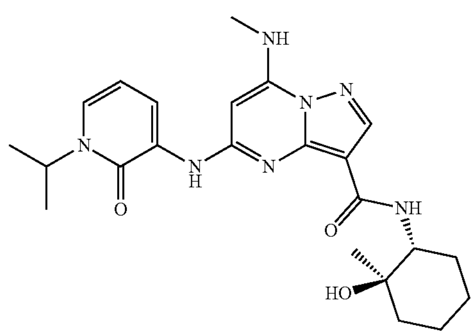 [SMILES: CNc1cc(Nc2cccn(C(C)C)c2=O)nc2c(C(=O)N[C@@H]3CCCC[C@@]3(C)O)cnn12] |
| I-1277 | 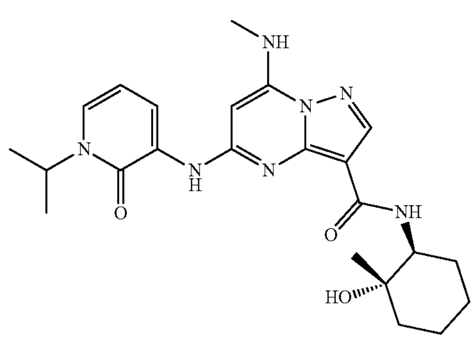 [SMILES: CNc1cc(Nc2cccn(C(C)C)c2=O)nc2c(C(=O)N[C@H]3CCCC[C@]3(C)O)cnn12] |

TABLE 1-continued

Selected Compounds

| Compound | Structure |
|---|---|
| I-1278 | 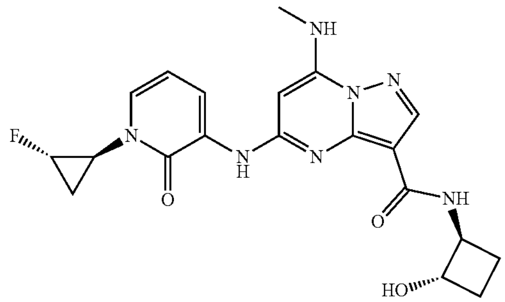 [SMILES: CNc1cc(Nc2cccn([C@H]3C[C@@H]3F)c2=O)nc2c(C(=O)N[C@H]3CC[C@@H]3O)cnn12] |
| I-1279 | 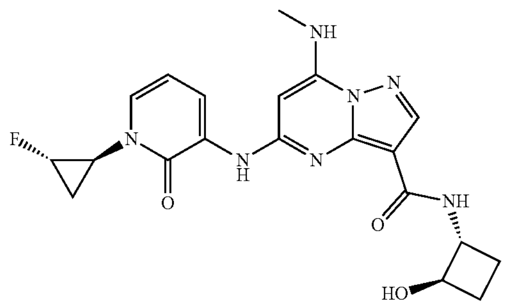 [SMILES: CNc1cc(Nc2cccn([C@H]3C[C@@H]3F)c2=O)nc2c(C(=O)N[C@@H]3CC[C@H]3O)cnn12] |
| I-1280 | 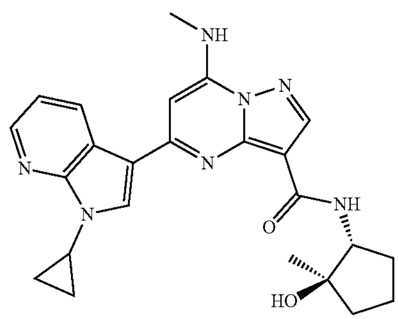 [SMILES: CNc1cc(-c2cn(C3CC3)c3ncccc23)nc2c(C(=O)N[C@@H]3CCC[C@@]3(C)O)cnn12] |
| I-1281 | 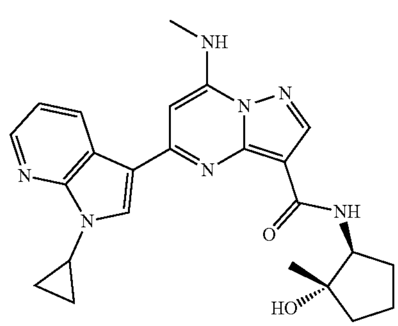 [SMILES: CNc1cc(-c2cn(C3CC3)c3ncccc23)nc2c(C(=O)N[C@H]3CCC[C@]3(C)O)cnn12] |

TABLE 1-continued

Selected Compounds

| Compound | Structure |
|---|---|
| I-1282 | 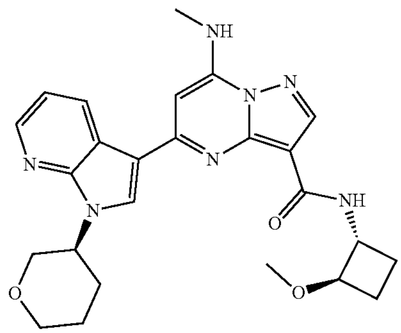 [SMILES: CNc1cc(-c2cn([C@H]3CCCOC3)c3ncccc23)nc2c(C(=O)N[C@@H]3CC[C@H]3OC)cnn12] |
| I-1283 | 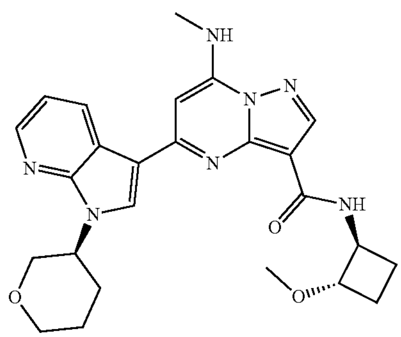 [SMILES: CNc1cc(-c2cn([C@H]3CCCOC3)c3ncccc23)nc2c(C(=O)N[C@H]3CC[C@@H]3OC)cnn12] |
| I-1284 | 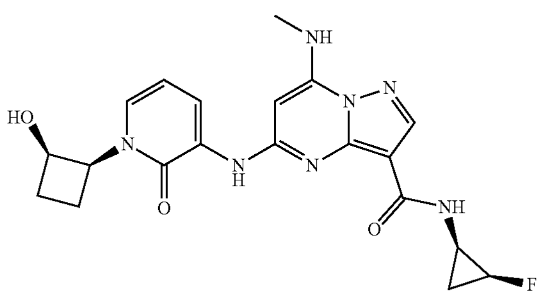 [SMILES: CNc1cc(Nc2cccn([C@H]3CC[C@H]3O)c2=O)nc2c(C(=O)N[C@@H]3C[C@@H]3F)cnn12] |
| I-1285 | 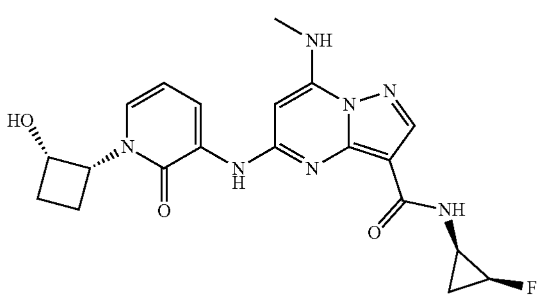 [SMILES: CNc1cc(Nc2cccn([C@@H]3CC[C@@H]3O)c2=O)nc2c(C(=O)N[C@@H]3C[C@@H]3F)cnn12] |
| I-1286 | 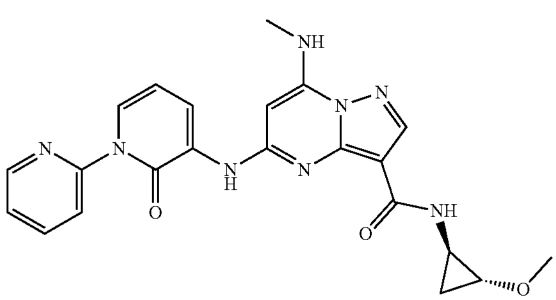 [SMILES: CNc1cc(Nc2cccn(-c3ccccn3)c2=O)nc2c(C(=O)N[C@@H]3C[C@H]3OC)cnn12] |

TABLE 1-continued

Selected Compounds

| Compound | Structure |
|---|---|
| I-1287 | 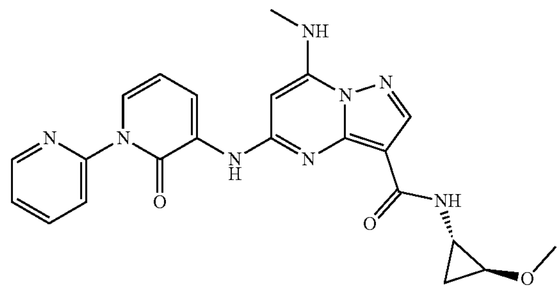 [SMILES: CNc1cc(Nc2cccn(-c3ccccn3)c2=O)nc2c(C(=O)N[C@H]3C[C@@H]3OC)cnn12] |
| I-1288 | 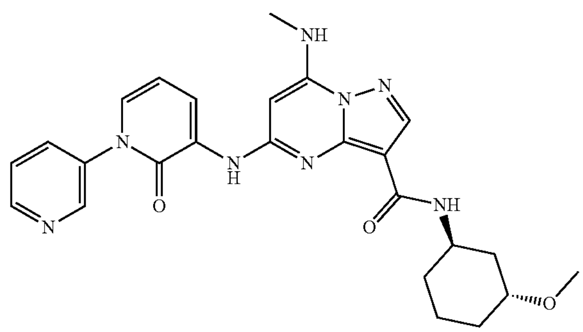 [SMILES: CNc1cc(Nc2cccn(-c3cccnc3)c2=O)nc2c(C(=O)N[C@@H]3CCC[C@@H](OC)C3)cnn12] |
| I-1289 | 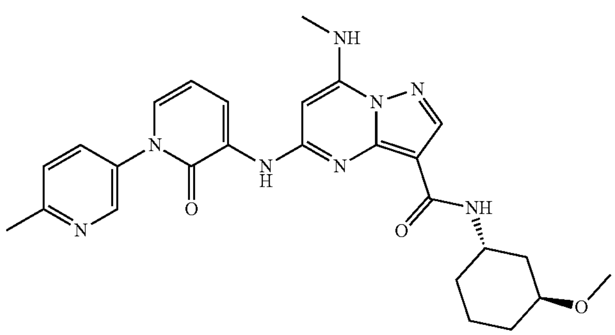 |
| I-1290 | 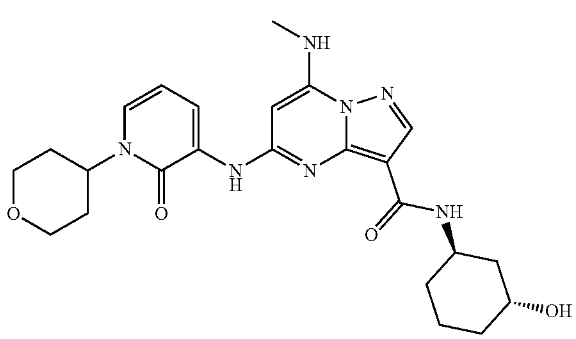 [SMILES: CNc1cc(Nc2cccn(C3CCOCC3)c2=O)nc2c(C(=O)N[C@@H]3CCC[C@@H](O)C3)cnn12] |

TABLE 1-continued

Selected Compounds

| Compound | Structure |
|---|---|
| I-1291 | 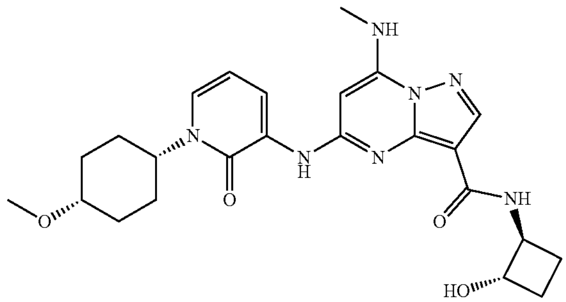 [SMILES: CNc1cc(Nc2cccn([C@H]3CC[C@@H](OC)CC3)c2=O)nc2c(C(=O)N[C@H]3CC[C@@H]3O)cnn12] |
| I-1292 | 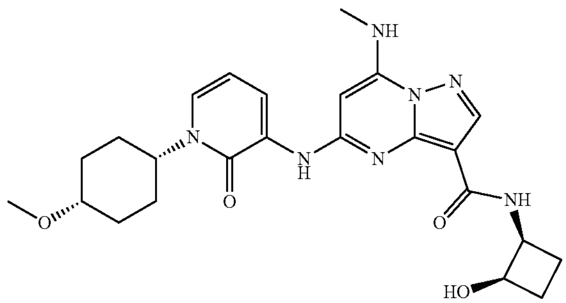 [SMILES: CNc1cc(Nc2cccn([C@H]3CC[C@@H](OC)CC3)c2=O)nc2c(C(=O)N[C@H]3CC[C@H]3O)cnn12] |
| I-1293 | 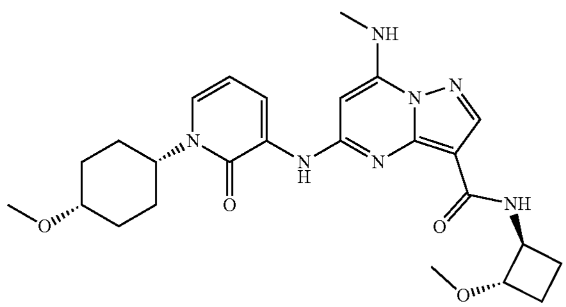 [SMILES: CNc1cc(Nc2cccn([C@H]3CC[C@@H](OC)CC3)c2=O)nc2c(C(=O)N[C@H]3CC[C@@H]3OC)cnn12] |
| I-1294 | 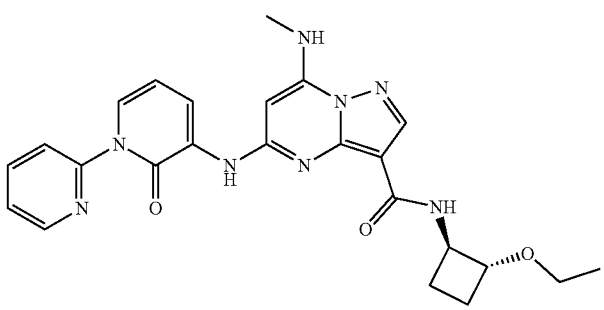 [SMILES: CCO[C@@H]1CC[C@H]1NC(=O)c1cnn2c(NC)cc(Nc3cccn(-c4ccccn4)c3=O)nc12] |
| I-1295 | 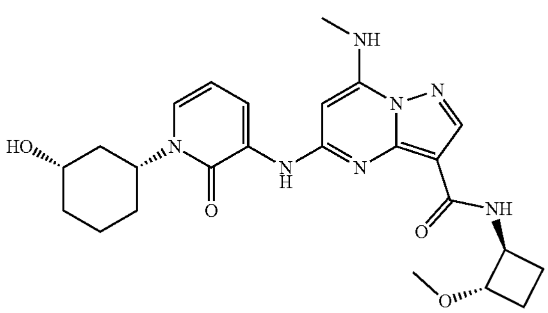 [SMILES: CNc1cc(Nc2cccn([C@@H]3CCC[C@H](O)C3)c2=O)nc2c(C(=O)N[C@H]3CC[C@@H]3OC)cnn12] |

TABLE 1-continued

| Selected Compounds | |
|---|---|
| Compound | Structure |
| I-1296 | |
| I-1297 | |
| I-1298 | |
| I-1299 | |

TABLE 1-continued
Selected Compounds
| Compound | Structure |
|---|---|
| I-1300 | 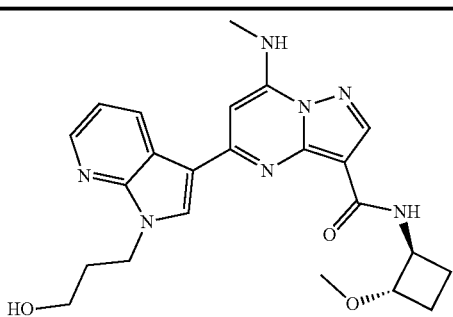 |
| I-1301 | 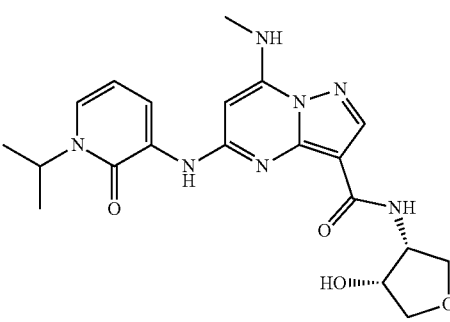 |
| I-1302 | 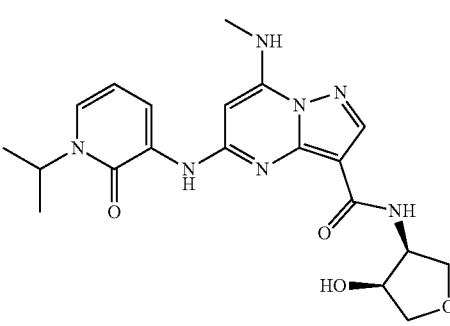 |
| I-1303 | 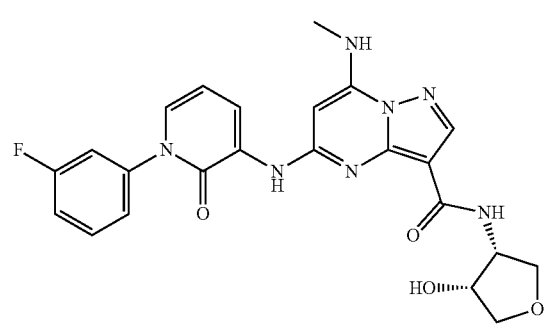 [SMILES: CNc1cc(Nc2cccn(-c3cccc(F)c3)c2=O)nc2c(C(=O)N[C@@H]3COC[C@@H]3O)cnn12] |
| I-1304 | 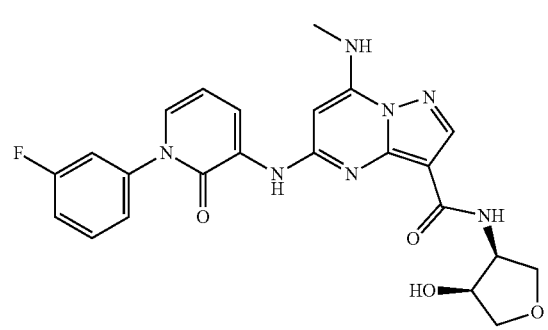 [SMILES: CNc1cc(Nc2cccn(-c3cccc(F)c3)c2=O)nc2c(C(=O)N[C@H]3COC[C@H]3O)cnn12] |

TABLE 1-continued

Selected Compounds

| Compound | Structure |
|---|---|
| I-1305 | 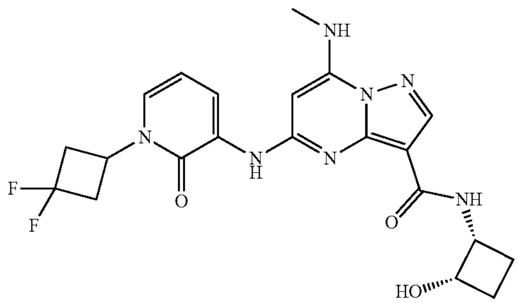 [SMILES: CNc1cc(Nc2cccn(C3CC(F)(F)C3)c2=O)nc2c(C(=O)N[C@@H]3CC[C@@H]3O)cnn12] |
| I-1306 | 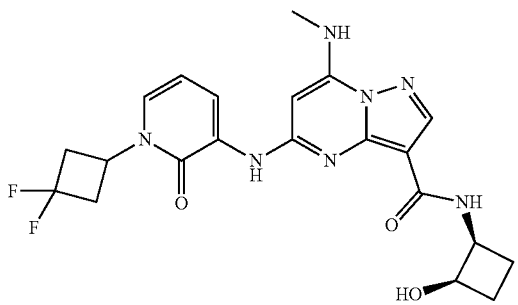 [SMILES: CNc1cc(Nc2cccn(C3CC(F)(F)C3)c2=O)nc2c(C(=O)N[C@H]3CC[C@H]3O)cnn12] |
| I-1307 | 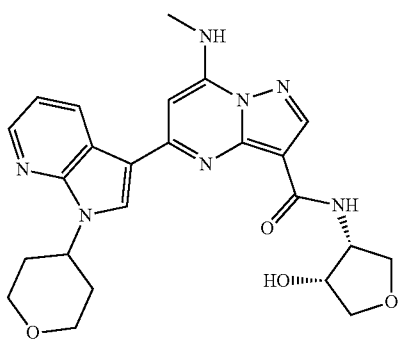 [SMILES: CNc1cc(-c2cn(C3CCOCC3)c3ncccc23)nc2c(C(=O)N[C@@H]3COC[C@@H]3O)cnn12] |
| I-1308 | 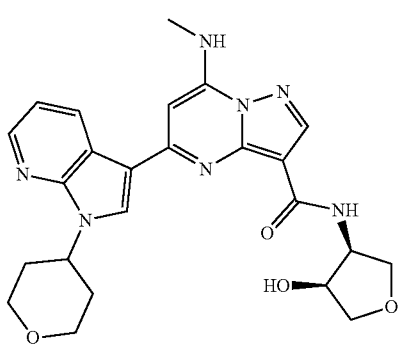 [SMILES: CNc1cc(-c2cn(C3CCOCC3)c3ncccc23)nc2c(C(=O)N[C@H]3COC[C@H]3O)cnn12] |

TABLE 1-continued

Selected Compounds

| Compound | Structure |
|---|---|
| I-1309 | 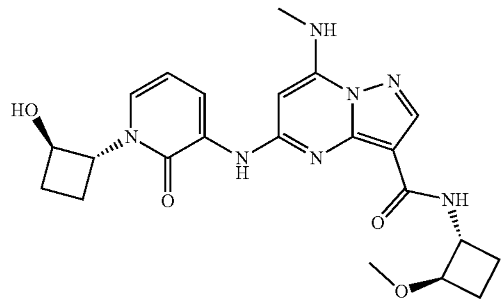 [SMILES: CNc1cc(Nc2cccn([C@@H]3CC[C@H]3O)c2=O)nc2c(C(=O)N[C@@H]3CC[C@H]3OC)cnn12] |
| I-1310 | 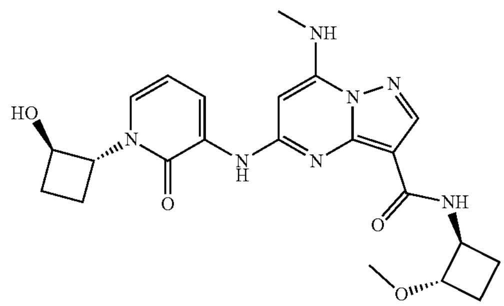 [SMILES: CNc1cc(Nc2cccn([C@@H]3CC[C@H]3O)c2=O)nc2c(C(=O)N[C@H]3CC[C@@H]3OC)cnn12] |
| I-1311 | 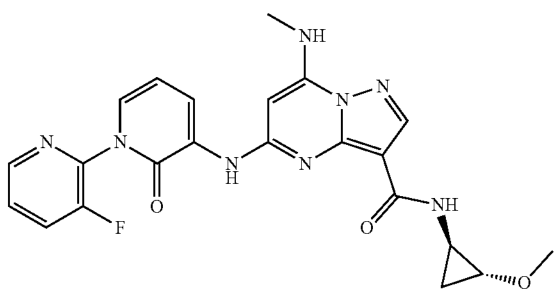 [SMILES: CNc1cc(Nc2cccn(-c3ncccc3F)c2=O)nc2c(C(=O)N[C@@H]3C[C@H]3OC)cnn12] |
| I-1312 | 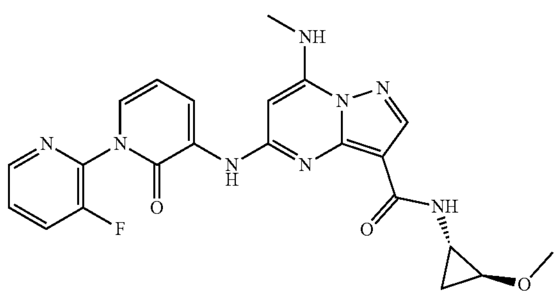 [SMILES: CNc1cc(Nc2cccn(-c3ncccc3F)c2=O)nc2c(C(=O)N[C@H]3C[C@@H]3OC)cnn12] |
| I-1313 | 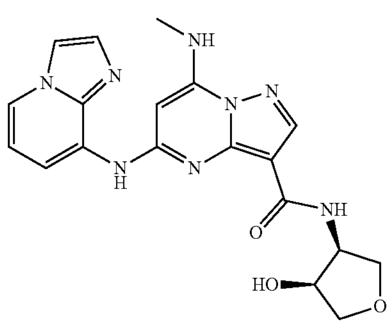 [SMILES: CNc1cc(Nc2cccn3ccnc23)nc2c(C(=O)N[C@H]3COC[C@H]3O)cnn12] |

TABLE 1-continued

Selected Compounds

| Compound | Structure |
|---|---|
| I-1314 | 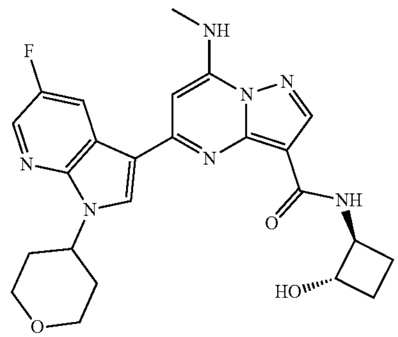 [SMILES: CNc1cc(-c2cn(C3CCOCC3)c3ncc(F)cc23)nc2c(C(=O)N[C@H]3CC[C@@H]3O)cnn12] |
| I-1315 | 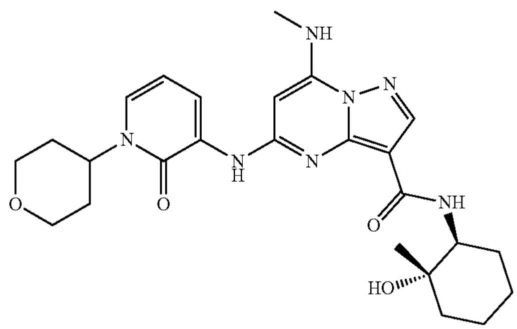 [SMILES: CNc1cc(Nc2cccn(C3CCOCC3)c2=O)nc2c(C(=O)N[C@H]3CCCC[C@]3(C)O)cnn12] |
| I-1316 | 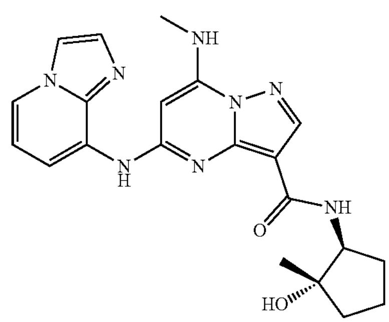 [SMILES: CNc1cc(Nc2cccn3ccnc23)nc2c(C(=O)N[C@H]3CCC[C@]3(C)O)cnn12] |
| I-1317 | 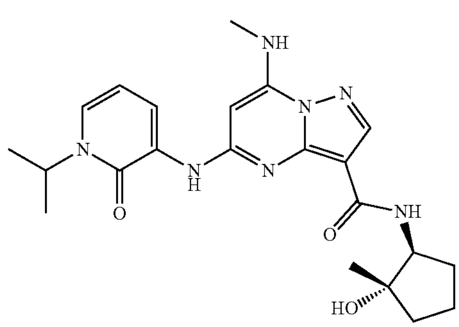 [SMILES: CNc1cc(Nc2cccn(C(C)C)c2=O)nc2c(C(=O)N[C@H]3CCC[C@]3(C)O)cnn12] |

TABLE 1-continued

Selected Compounds

| Compound | Structure |
|---|---|
| I-1318 | 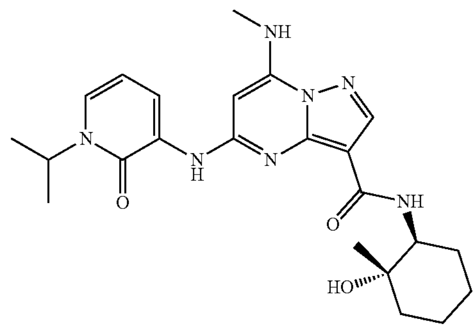 [SMILES: CNc1cc(Nc2cccn(C(C)C)c2=O)nc2c(C(=O)N[C@H]3CCCC[C@]3(C)O)cnn12] |
| I-1319 | 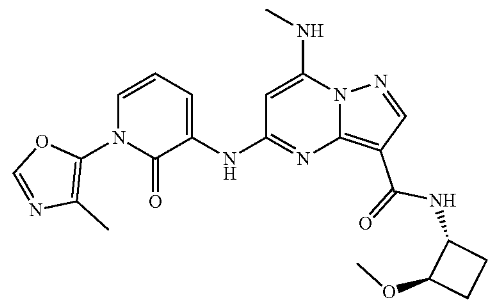 [SMILES: CNc1cc(Nc2cccn(-c3ocnc3C)c2=O)nc2c(C(=O)N[C@@H]3CC[C@H]3OC)cnn12] |
| I-1320 | 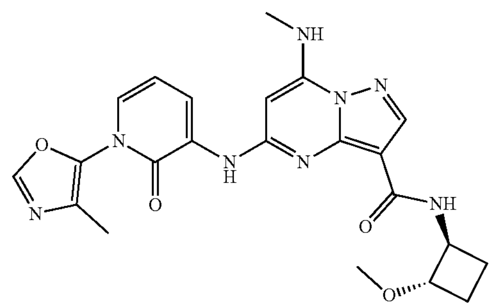 [SMILES: CNc1cc(Nc2cccn(-c3ocnc3C)c2=O)nc2c(C(=O)N[C@H]3CC[C@@H]3OC)cnn12] |
| I-1321 | 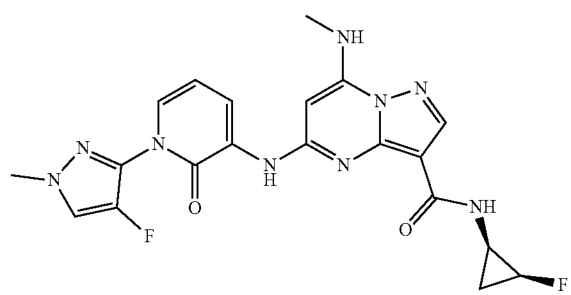 [SMILES: CNc1cc(Nc2cccn(-c3nn(C)cc3F)c2=O)nc2c(C(=O)N[C@@H]3C[C@@H]3F)cnn12] |
| I-1322 | 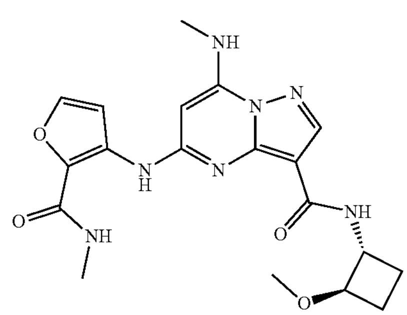 [SMILES: CNC(=O)c1occc1Nc1cc(NC)n2ncc(C(=O)N[C@@H]3CC[C@H]3OC)c2n1] |

TABLE 1-continued

Selected Compounds

| Compound | Structure |
|---|---|
| I-1323 | 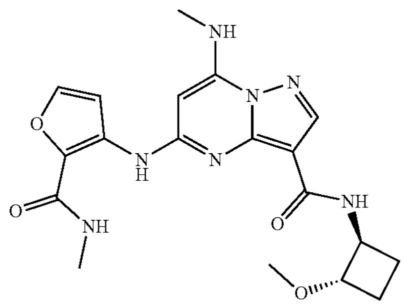 [SMILES: CNC(=O)c1occc1Nc1cc(NC)n2ncc(C(=O)N[C@H]3CC[C@@H]3OC)c2n1] |
| I-1324 | 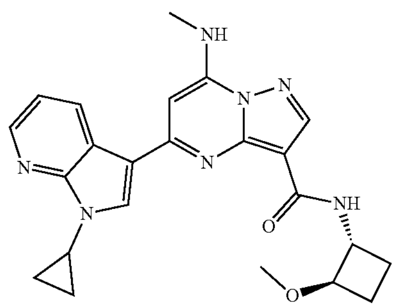 [SMILES: CNc1cc(-c2cn(C3CC3)c3ncccc23)nc2c(C(=O)N[C@@H]3CC[C@H]3OC)cnn12] |
| I-1325 | 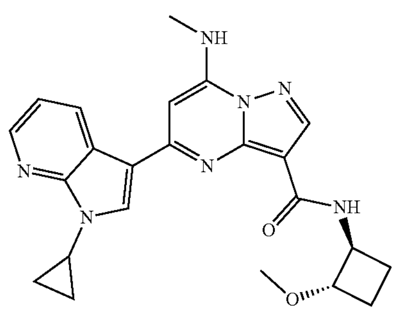 [SMILES: CNc1cc(-c2cn(C3CC3)c3ncccc23)nc2c(C(=O)N[C@H]3CC[C@@H]3OC)cnn12] |
| I-1326 | 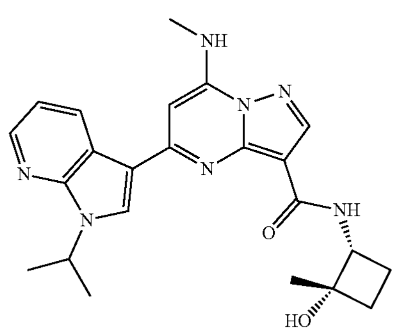 [SMILES: CNc1cc(-c2cn(C(C)C)c3ncccc23)nc2c(C(=O)N[C@@H]3CC[C@]3(C)O)cnn12] |
| I-1327 | 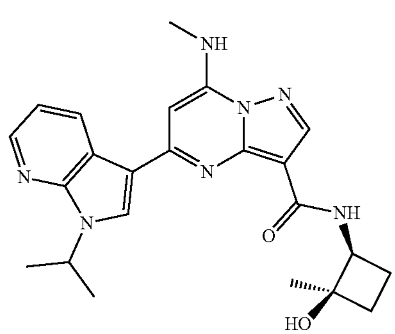 [SMILES: CNc1cc(-c2cn(C(C)C)c3ncccc23)nc2c(C(=O)N[C@H]3CC[C@@]3(C)O)cnn12] |

TABLE 1-continued
| Selected Compounds | |
|---|---|
| Compound | Structure |
| I-1328 | 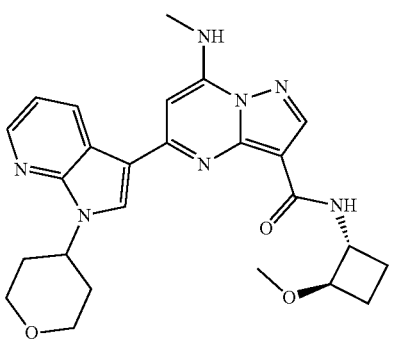 [SMILES: CNc1cc(-c2cn(C3CCOCC3)c3ncccc23)nc2c(C(=O)N[C@@H]3CC[C@H]3OC)cnn12] |
| I-1329 | 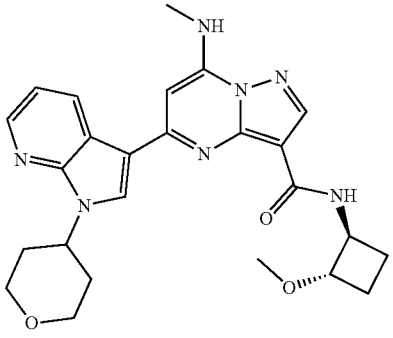 [SMILES: CNc1cc(-c2cn(C3CCOCC3)c3ncccc23)nc2c(C(=O)N[C@H]3CC[C@@H]3OC)cnn12] |
| I-1330 | 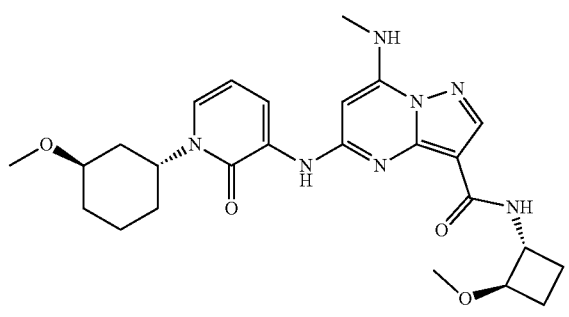 [SMILES: CNc1cc(Nc2cccn([C@@H]3CCC[C@@H](OC)C3)c2=O)nc2c(C(=O)N[C@@H]3CC[C@H]3OC)cnn12] |
| I-1331 | 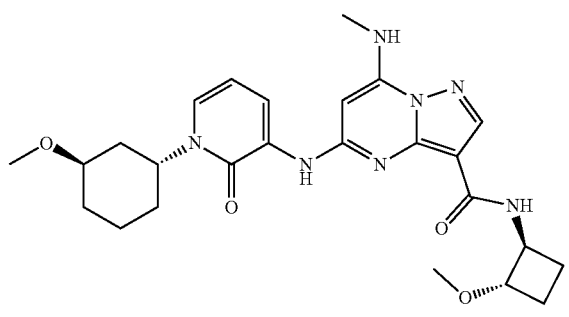 [SMILES: CNc1cc(Nc2cccn([C@@H]3CCC[C@@H](OC)C3)c2=O)nc2c(C(=O)N[C@H]3CC[C@@H]3OC)cnn12] |

TABLE 1-continued
Selected Compounds
| Compound | Structure |
|---|---|
| I-1332 | 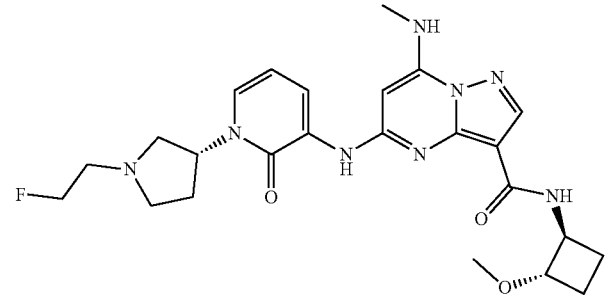 [SMILES: CNc1cc(Nc2cccn([C@@H]3CCN(CCF)C3)c2=O)nc2c(C(=O)N[C@H]3CC[C@@H]3OC)cnn12] |
| I-1333 | 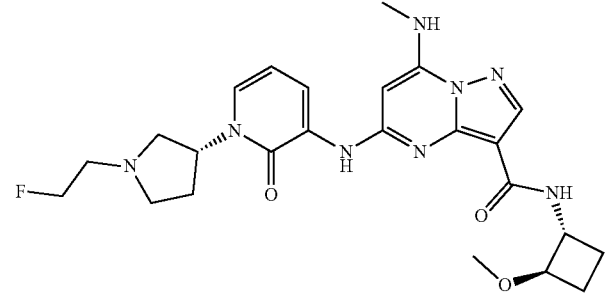 [SMILES: CNc1cc(Nc2cccn([C@@H]3CCN(CCF)C3)c2=O)nc2c(C(=O)N[C@@H]3CC[C@H]3OC)cnn12] |
| I-1334 | 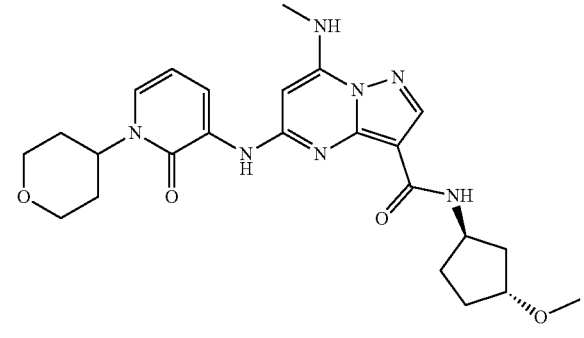 [SMILES: CNc1cc(Nc2cccn(C3CCOCC3)c2=O)nc2c(C(=O)N[C@@H]3CC[C@@H](OC)C3)cnn12] |
| I-1335 | 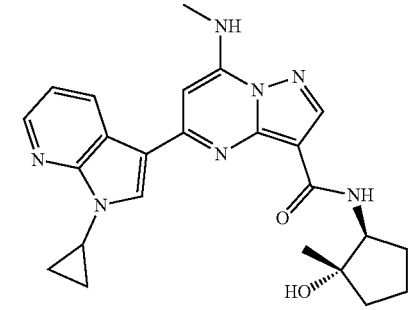 [SMILES: CNc1cc(-c2cn(C3CC3)c3ncccc23)nc2c(C(=O)N[C@H]3CCC[C@]3(C)O)cnn12] |

TABLE 1-continued

Selected Compounds

| Compound | Structure |
|---|---|
| I-1336 | 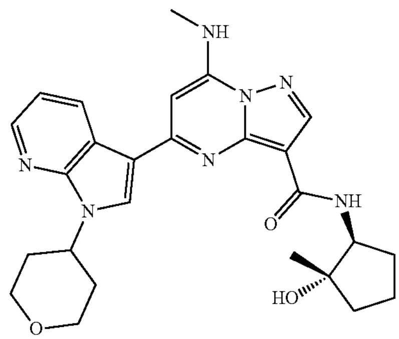 [SMILES: CNc1cc(-c2cn(C3CCOCC3)c3ncccc23)nc2c(C(=O)N[C@H]3CCC[C@]3(C)O)cnn12] |
| I-1337 | 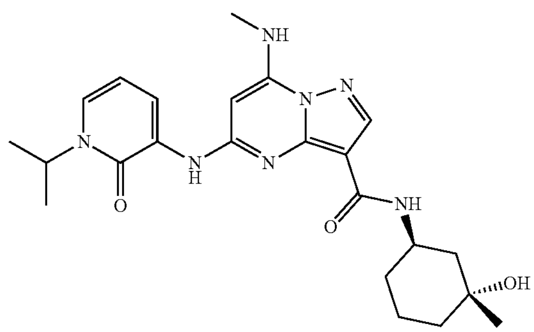 [SMILES: CNc1cc(Nc2cccn(C(C)C)c2=O)nc2c(C(=O)N[C@@H]3CCC[C@@](C)(O)C3)cnn12] |
| I-1338 | 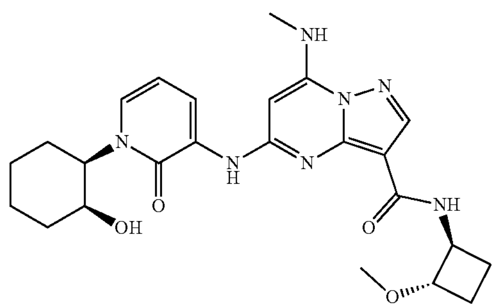 [SMILES: CNc1cc(Nc2cccn([C@@H]3CCCC[C@@H]3O)c2=O)nc2c(C(=O)N[C@H]3CC[C@@H]3OC)cnn12] |
| I-1339 | 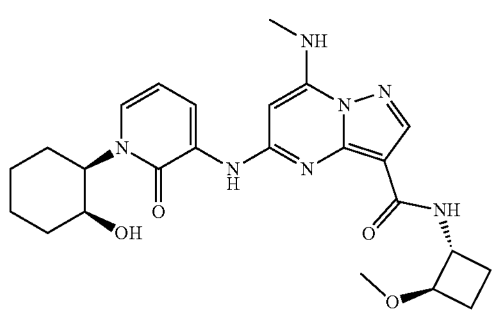 [SMILES: CNc1cc(Nc2cccn([C@@H]3CCCC[C@@H]3O)c2=O)nc2c(C(=O)N[C@@H]3CC[C@H]3OC)cnn12] |

TABLE 1-continued
Selected Compounds
| Compound | Structure |
|---|---|
| I-1340 | 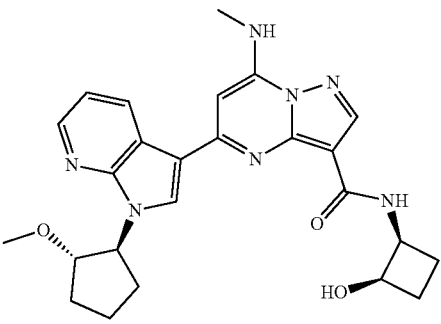 [SMILES: CNc1cc(-c2cn([C@H]3CCC[C@@H]3OC)c3ncccc23)nc2c(C(=O)N[C@H]3CC[C@H]3O)cnn12] |
| I-1341 | 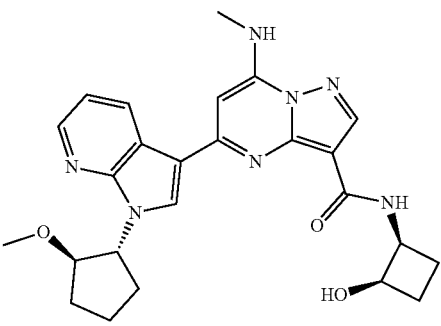 [SMILES: CNc1cc(-c2cn([C@@H]3CCC[C@H]3OC)c3ncccc23)nc2c(C(=O)N[C@H]3CC[C@H]3O)cnn12] |
| I-1342 | 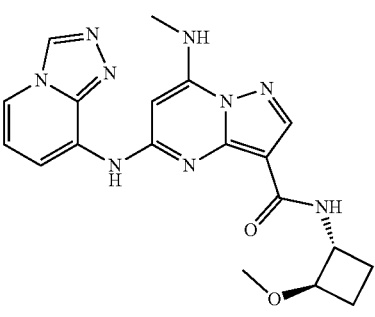 |
| I-1343 | 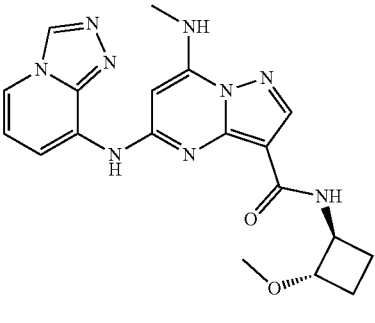 [SMILES: CNc1cc(Nc2cccn3cnnc23)nc2c(C(=O)N[C@H]3CC[C@@H]3OC)cnn12] |
| I-1344 | 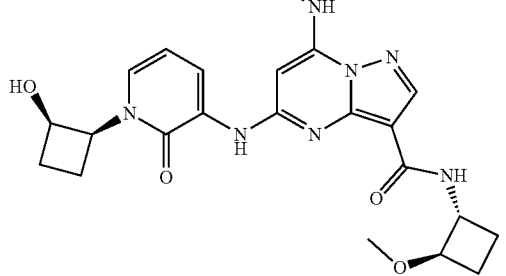 |

TABLE 1-continued
Selected Compounds
| Compound | Structure |
|---|---|
| I-1345 | 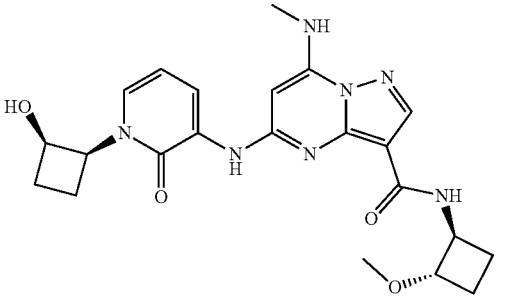 [SMILES: CNc1cc(Nc2cccn([C@H]3CC[C@H]3O)c2=O)nc2c(C(=O)N[C@H]3CC[C@@H]3OC)cnn12] |
| I-1346 | 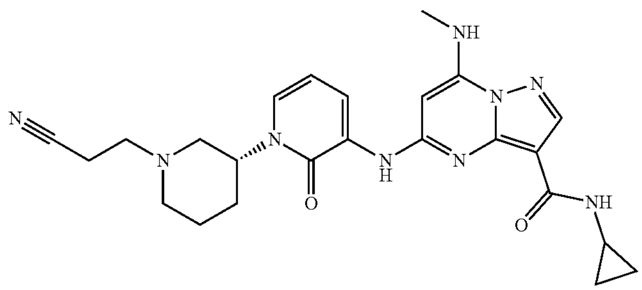 |
| I-1347 | 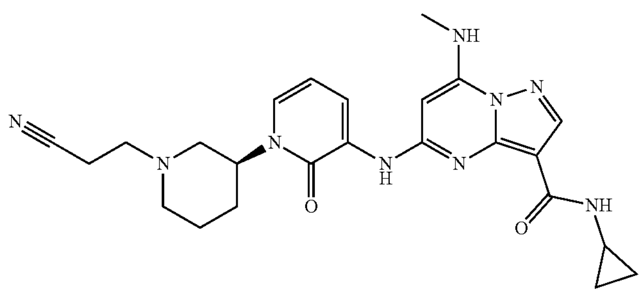 [SMILES: CNc1cc(Nc2cccn([C@H]3CCCN(CCC#N)C3)c2=O)nc2c(C(=O)NC3CC3)cnn12] |
| I-1348 | 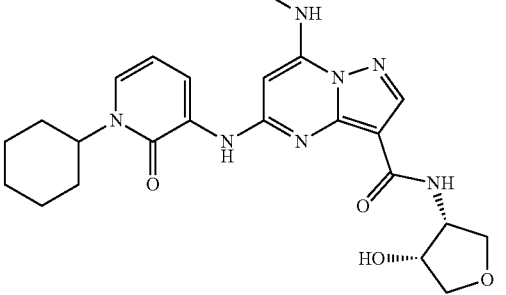 |
| I-1349 | 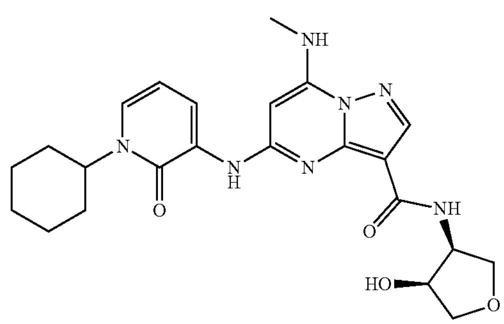 [SMILES: CNc1cc(Nc2cccn(C3CCCCC3)c2=O)nc2c(C(=O)N[C@H]3COC[C@H]3O)cnn12] |

TABLE 1-continued

| Compound | Structure |
|---|---|
| I-1350 | 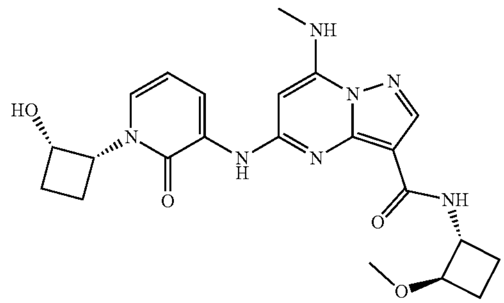 [SMILES: CNc1cc(Nc2cccn([C@@H]3CC[C@@H]3O)c2=O)nc2c(C(=O)N[C@@H]3CC[C@H]3OC)cnn12] |
| I-1351 | 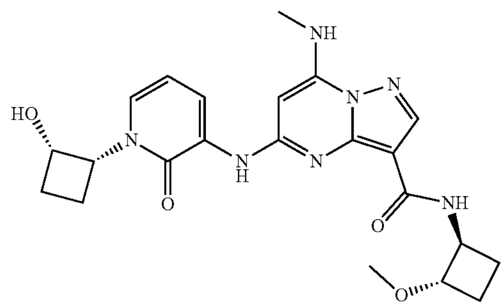 [SMILES: CNc1cc(Nc2cccn([C@@H]3CC[C@@H]3O)c2=O)nc2c(C(=O)N[C@H]3CC[C@@H]3OC)cnn12] |
| I-1352 | 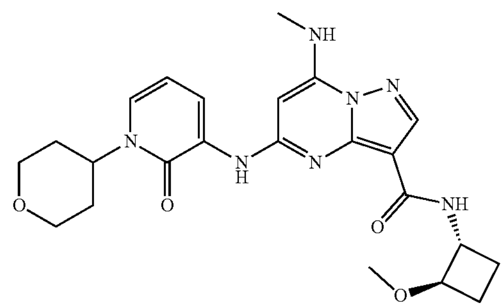 [SMILES: CNc1cc(Nc2cccn(C3CCOCC3)c2=O)nc2c(C(=O)N[C@@H]3CC[C@H]3OC)cnn12] |
| I-1353 | 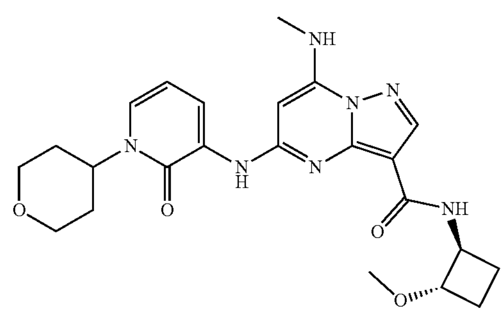 [SMILES: CNc1cc(Nc2cccn(C3CCOCC3)c2=O)nc2c(C(=O)N[C@H]3CC[C@@H]3OC)cnn12] |
| I-1354 | 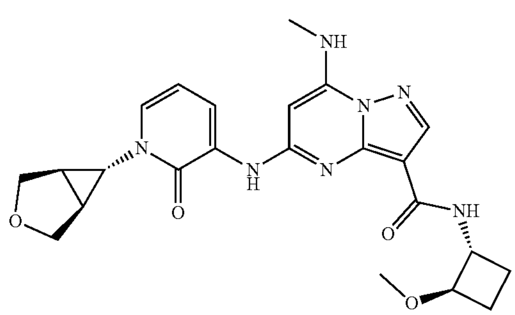 [SMILES: CNc1cc(Nc2cccn([C@H]3[C@@H]4COC[C@@H]43)c2=O)nc2c(C(=O)N[C@@H]3CC[C@H]3OC)cnn12] |

TABLE 1-continued
Selected Compounds
| Compound | Structure |
|---|---|
| I-1355 | 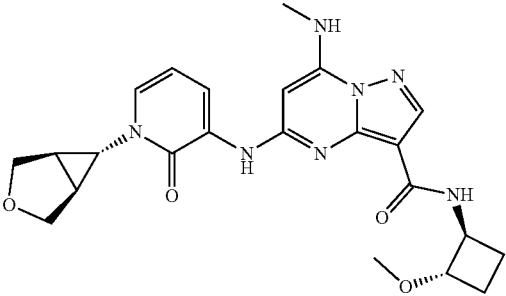 [SMILES: CNc1cc(Nc2cccn([C@H]3[C@@H]4COC[C@@H]43)c2=O)nc2c(C(=O)N[C@H]3CC[C@@H]3OC)cnn12] |
| I-1356 | 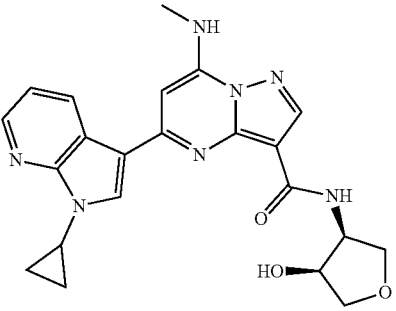 [SMILES: CNc1cc(-c2cn(C3CC3)c3ncccc23)nc2c(C(=O)N[C@H]3COC[C@H]3O)cnn12] |
| I-1357 | 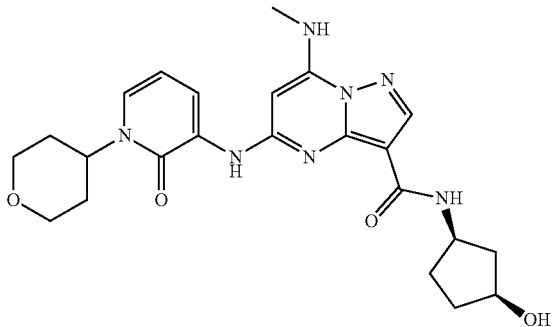 [SMILES: CNc1cc(Nc2cccn(C3CCOCC3)c2=O)nc2c(C(=O)N[C@@H]3CC[C@H](O)C3)cnn12] |
| I-1358 | 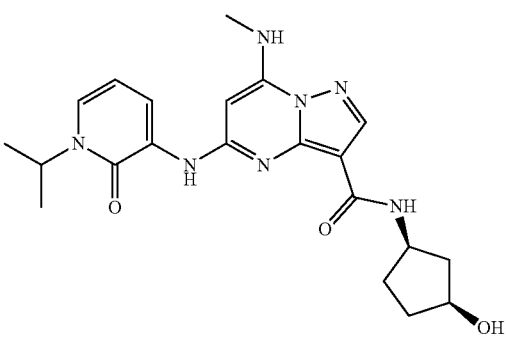 [SMILES: CNc1cc(Nc2cccn(C(C)C)c2=O)nc2c(C(=O)N[C@@H]3CC[C@H](O)C3)cnn12] |

TABLE 1-continued

| Selected Compounds | |
|---|---|
| Compound | Structure |
| I-1359 | |
| I-1360 | |
| I-1361 | |
| I-1362 | |

TABLE 1-continued

Selected Compounds

| Compound | Structure |
|---|---|
| I-1363 | 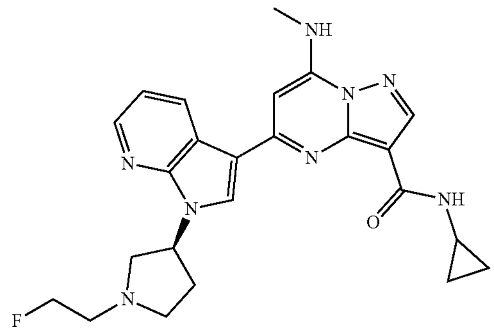 [SMILES: CNc1cc(-c2cn([C@H]3CCN(CCF)C3)c3ncccc23)nc2c(C(=O)NC3CC3)cnn12] |
| I-1364 | 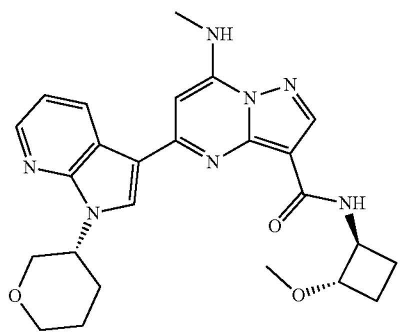 [SMILES: CNc1cc(-c2cn([C@@H]3CCCOC3)c3ncccc23)nc2c(C(=O)N[C@H]3CC[C@@H]3OC)cnn12] |
| I-1365 | 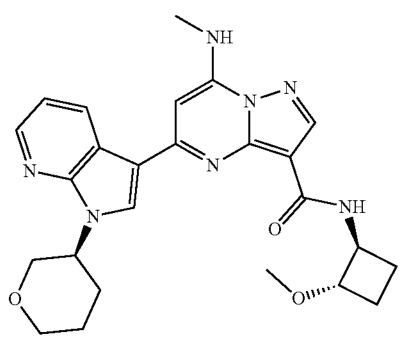 [SMILES: CNc1cc(-c2cn([C@H]3CCCOC3)c3ncccc23)nc2c(C(=O)N[C@H]3CC[C@@H]3OC)cnn12] |
| I-1366 | 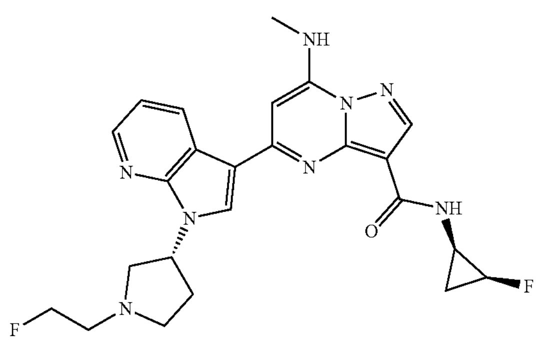 [SMILES: CNc1cc(-c2cn([C@@H]3CCN(CCF)C3)c3ncccc23)nc2c(C(=O)N[C@@H]3C[C@@H]3F)cnn12] |

TABLE 1-continued
Selected Compounds
| Compound | Structure |
|---|---|
| I-1367 | 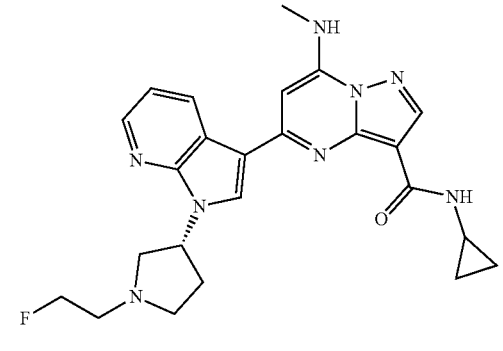 [SMILES: CNc1cc(-c2cn([C@@H]3CCN(CCF)C3)c3ncccc23)nc2c(C(=O)NC3CC3)cnn12] |
| I-1368 | 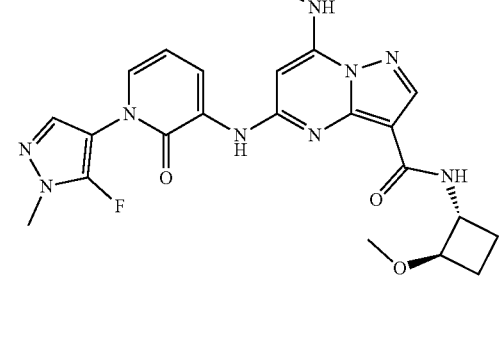 |
| I-1369 | 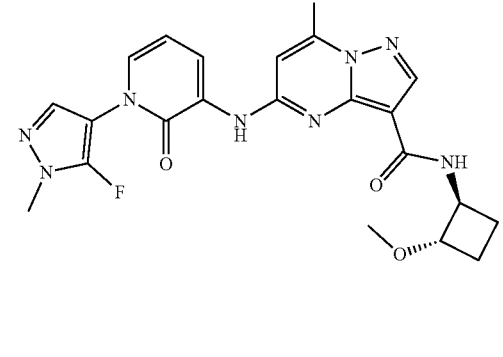 |
| I-1370 | 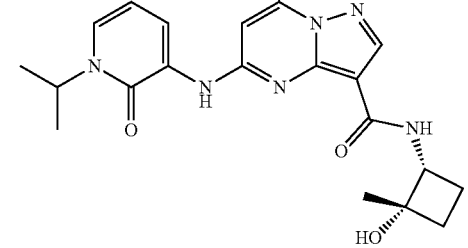 |

TABLE 1-continued

Selected Compounds

| Compound | Structure |
|---|---|
| I-1371 | 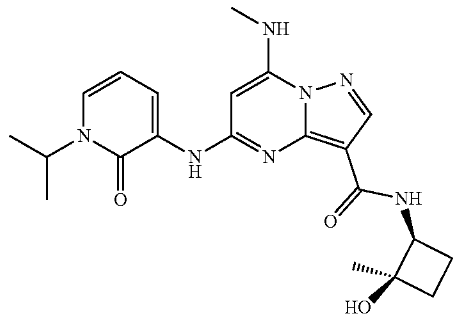 [SMILES: CNc1cc(Nc2cccn(C(C)C)c2=O)nc2c(C(=O)N[C@H]3CC[C@@]3(C)O)cnn12] |
| I-1372 | 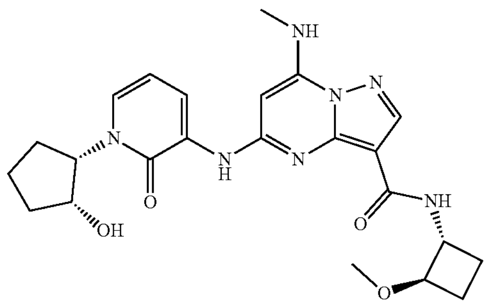 [SMILES: CNc1cc(Nc2cccn([C@H]3CCC[C@H]3O)c2=O)nc2c(C(=O)N[C@@H]3CC[C@H]3OC)cnn12] |
| I-1373 | 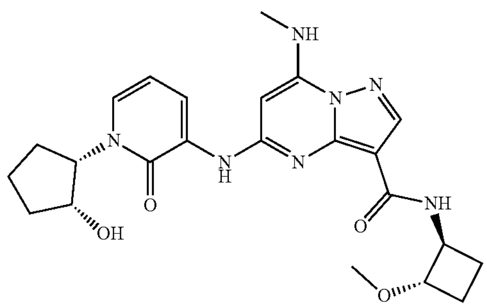 [SMILES: CNc1cc(Nc2cccn([C@H]3CCC[C@H]3O)c2=O)nc2c(C(=O)N[C@H]3CC[C@@H]3OC)cnn12] |
| I-1374 | 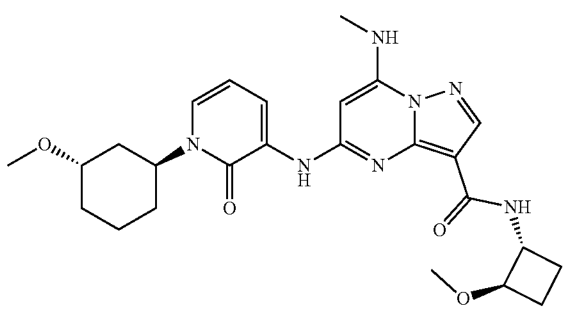 [SMILES: CNc1cc(Nc2cccn([C@H]3CCC[C@H](OC)C3)c2=O)nc2c(C(=O)N[C@@H]3CC[C@H]3OC)cnn12] |
| I-1375 | 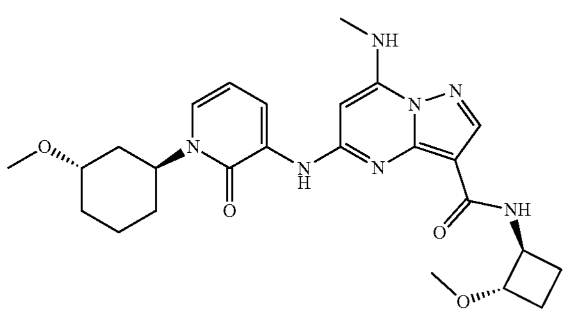 [SMILES: CNc1cc(Nc2cccn([C@H]3CCC[C@H](OC)C3)c2=O)nc2c(C(=O)N[C@H]3CC[C@@H]3OC)cnn12] |

TABLE 1-continued
Selected Compounds
| Compound | Structure |
|---|---|
| I-1376 | 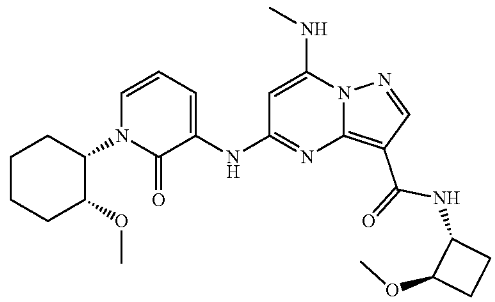 [SMILES: CNc1cc(Nc2cccn([C@H]3CCCC[C@H]3OC)c2=O)nc2c(C(=O)N[C@@H]3CC[C@H]3OC)cnn12] |
| I-1377 | 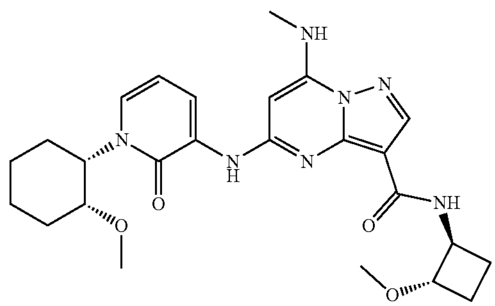 [SMILES: CNc1cc(Nc2cccn([C@H]3CCCC[C@H]3OC)c2=O)nc2c(C(=O)N[C@H]3CC[C@@H]3OC)cnn12] |
| I-1378 | 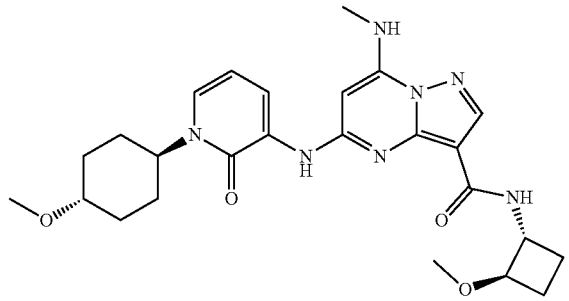 [SMILES: CNc1cc(Nc2cccn([C@H]3CC[C@H](OC)CC3)c2=O)nc2c(C(=O)N[C@@H]3CC[C@H]3OC)cnn12] |
| I-1379 | 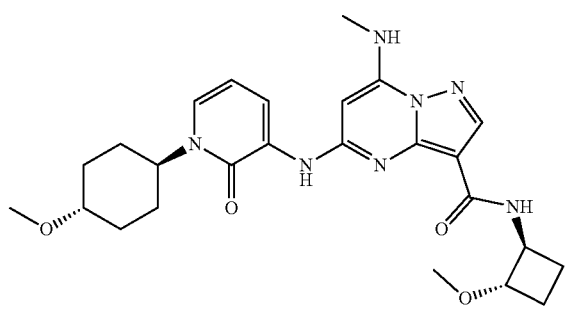 [SMILES: CNc1cc(Nc2cccn([C@H]3CC[C@H](OC)CC3)c2=O)nc2c(C(=O)N[C@H]3CC[C@@H]3OC)cnn12] |
| I-1380 | 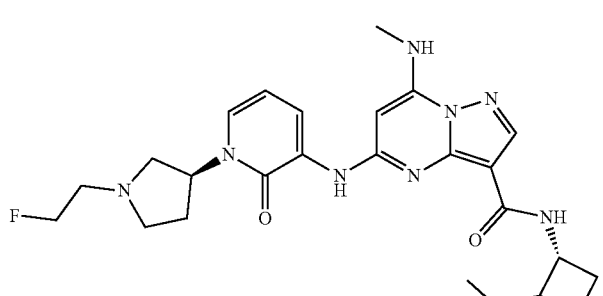 |

TABLE 1-continued

Selected Compounds

| Compound | Structure |
|---|---|
| I-1381 | 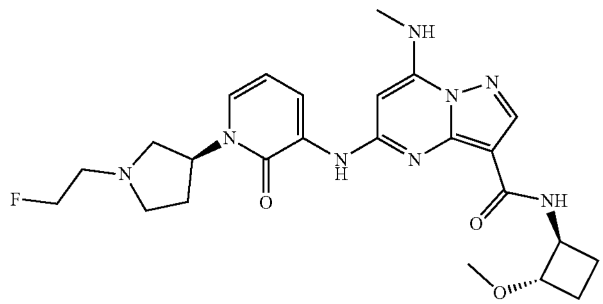 [SMILES: CNc1cc(Nc2cccn([C@H]3CCN(CCF)C3)c2=O)nc2c(C(=O)N[C@H]3CC[C@@H]3OC)cnn12] |
| I-1382 | 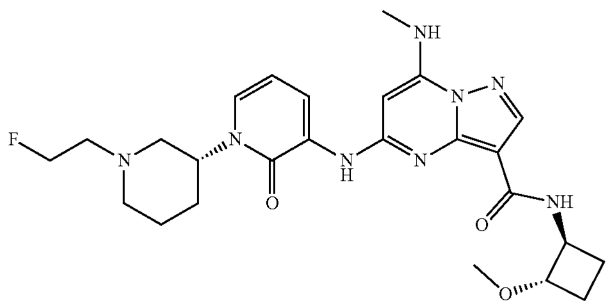 [SMILES: CNc1cc(Nc2cccn([C@@H]3CCCN(CCF)C3)c2=O)nc2c(C(=O)N[C@H]3CC[C@@H]3OC)cnn12] |
| I-1383 | 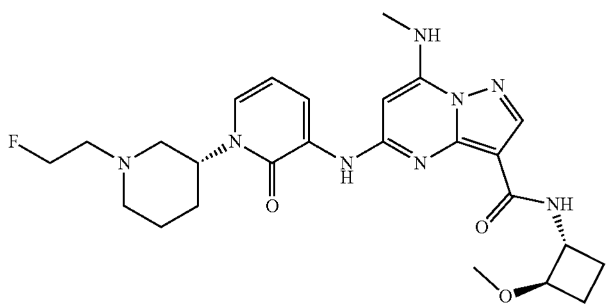 [SMILES: CNc1cc(Nc2cccn([C@@H]3CCCN(CCF)C3)c2=O)nc2c(C(=O)N[C@@H]3CC[C@H]3OC)cnn12] |
| I-1384 | 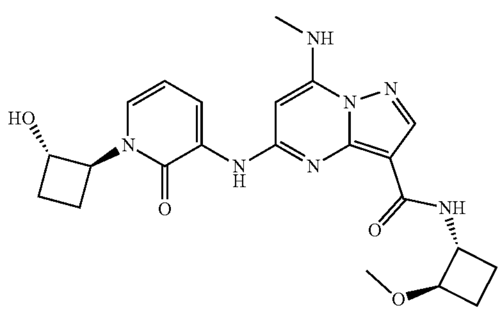 [SMILES: CNc1cc(Nc2cccn([C@H]3CC[C@@H]3O)c2=O)nc2c(C(=O)N[C@@H]3CC[C@H]3OC)cnn12] |
| I-1385 | 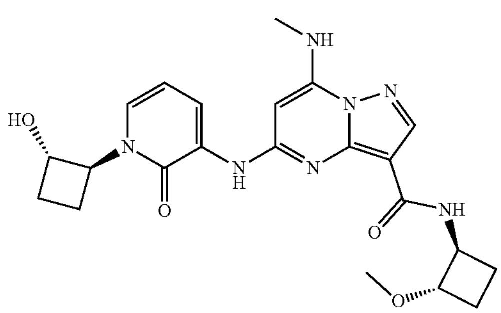 [SMILES: CNc1cc(Nc2cccn([C@H]3CC[C@@H]3O)c2=O)nc2c(C(=O)N[C@H]3CC[C@@H]3OC)cnn12] |

TABLE 1-continued

Selected Compounds

| Compound | Structure |
|---|---|
| I-1386 | 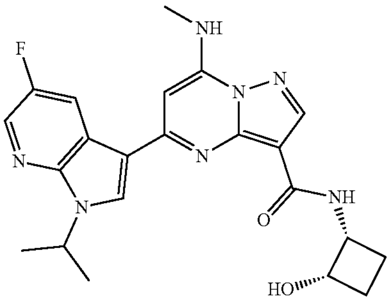 [SMILES: CNc1cc(-c2cn(C(C)C)c3ncc(F)cc23)nc2c(C(=O)N[C@@H]3CC[C@@H]3O)cnn12] |
| I-1387 | 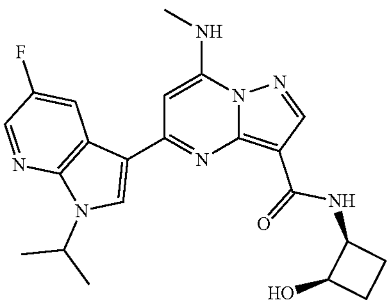 [SMILES: CNc1cc(-c2cn(C(C)C)c3ncc(F)cc23)nc2c(C(=O)N[C@H]3CC[C@H]3O)cnn12] |
| I-1388 | 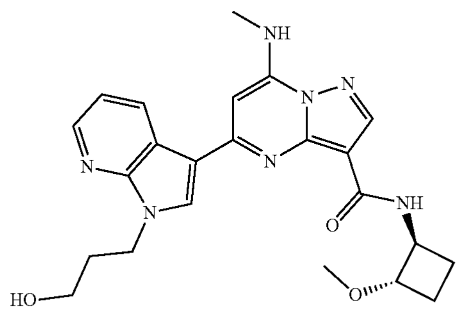 [SMILES: CNc1cc(-c2cn(CCCO)c3ncccc23)nc2c(C(=O)N[C@H]3CC[C@@H]3OC)cnn12] |
| I-1389 | 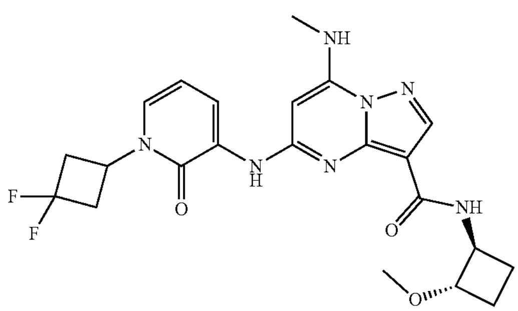 [SMILES: CNc1cc(Nc2cccn(C3CC(F)(F)C3)c2=O)nc2c(C(=O)N[C@H]3CC[C@@H]3OC)cnn12] |
| I-1390 | 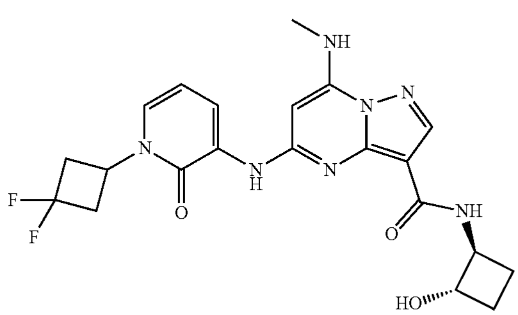 [SMILES: CNc1cc(Nc2cccn(C3CC(F)(F)C3)c2=O)nc2c(C(=O)N[C@H]3CC[C@@H]3O)cnn12] |

TABLE 1-continued

Selected Compounds

| Compound | Structure |
|---|---|
| I-1391 | 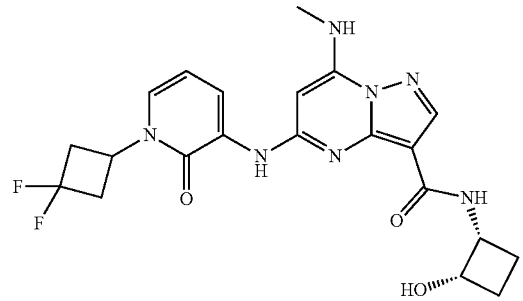 [SMILES: CNc1cc(Nc2cccn(C3CC(F)(F)C3)c2=O)nc2c(C(=O)N[C@@H]3CC[C@@H]3O)cnn12] |
| I-1392 | 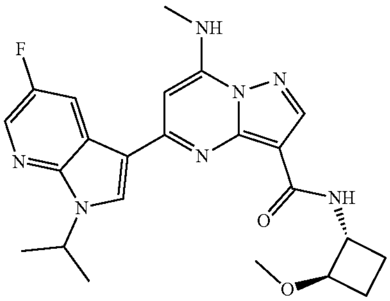 [SMILES: CNc1cc(-c2cn(C(C)C)c3ncc(F)cc23)nc2c(C(=O)N[C@@H]3CC[C@H]3OC)cnn12] |
| I-1393 | 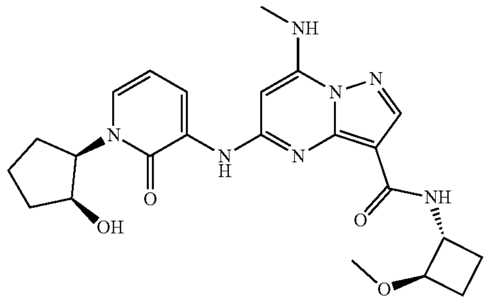 [SMILES: CNc1cc(Nc2cccn([C@@H]3CCC[C@@H]3O)c2=O)nc2c(C(=O)N[C@@H]3CC[C@H]3OC)cnn12] |
| I-1394 | 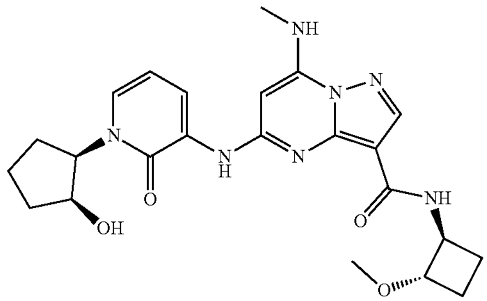 [SMILES: CNc1cc(Nc2cccn([C@@H]3CCC[C@@H]3O)c2=O)nc2c(C(=O)N[C@H]3CC[C@@H]3OC)cnn12] |
| I-1395 | 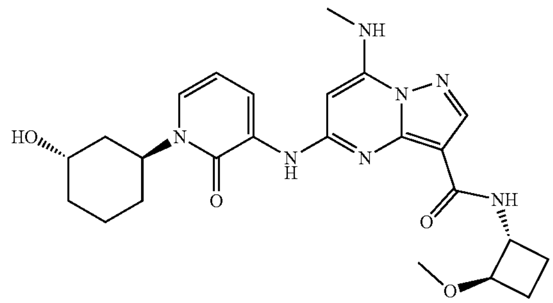 [SMILES: CNc1cc(Nc2cccn([C@H]3CCC[C@H](O)C3)c2=O)nc2c(C(=O)N[C@@H]3CC[C@H]3OC)cnn12] |

TABLE 1-continued

Selected Compounds

| Compound | Structure |
|---|---|
| I-1396 | 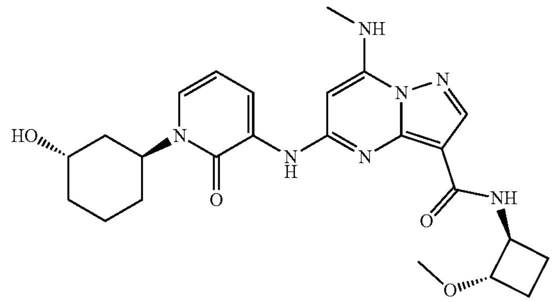 [SMILES: CNc1cc(Nc2cccn([C@H]3CCC[C@H](O)C3)c2=O)nc2c(C(=O)N[C@H]3CC[C@@H]3OC)cnn12] |
| I-1397 | 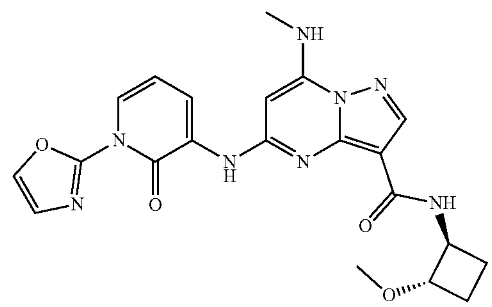 [SMILES: CNc1cc(Nc2cccn(-c3ncco3)c2=O)nc2c(C(=O)N[C@H]3CC[C@@H]3OC)cnn12] |
| I-1398 | 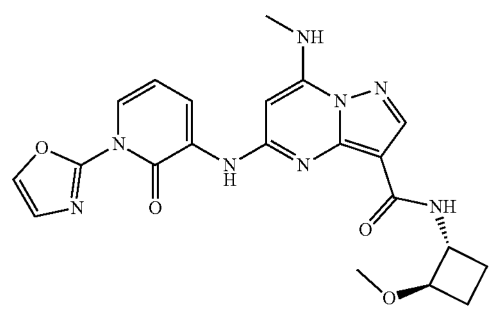 [SMILES: CNc1cc(Nc2cccn(-c3ncco3)c2=O)nc2c(C(=O)N[C@@H]3CC[C@H]3OC)cnn12] |
| I-1399 | 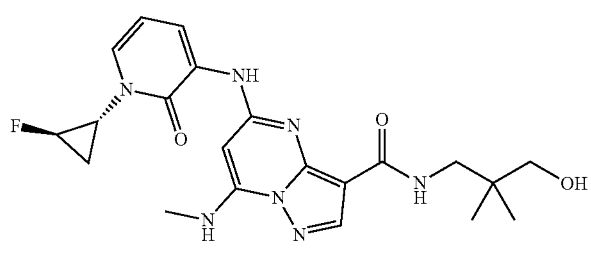 [SMILES: CNc1cc(Nc2cccn([C@@H]3C[C@H]3F)c2=O)nc2c(C(=O)NCC(C)(C)CO)cnn12] |
| I-1400 | 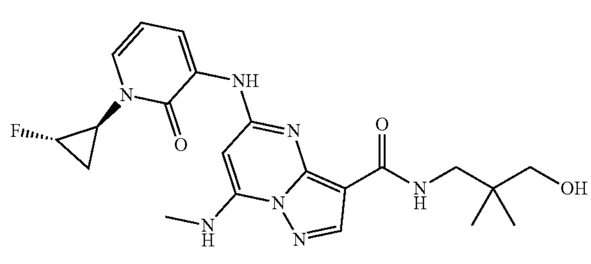 [SMILES: CNc1cc(Nc2cccn([C@H]3C[C@@H]3F)c2=O)nc2c(C(=O)NCC(C)(C)CO)cnn12] |

TABLE 1-continued

Selected Compounds

| Compound | Structure |
|---|---|
| I-1401 | 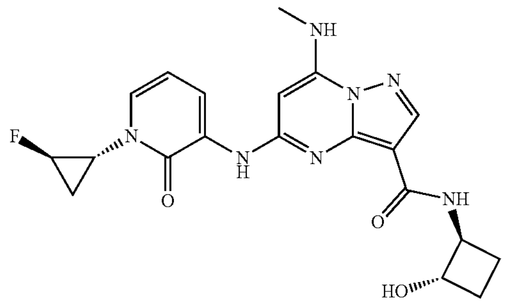 [SMILES: CNc1cc(Nc2cccn([C@@H]3C[C@H]3F)c2=O)nc2c(C(=O)N[C@H]3CC[C@@H]3O)cnn12] |
| I-1402 | 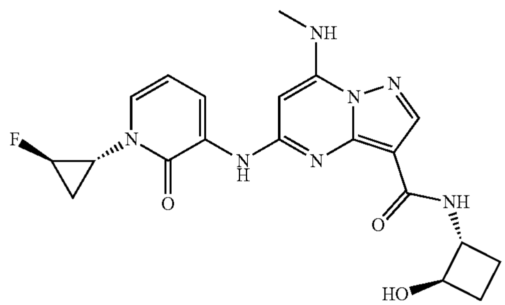 [SMILES: CNc1cc(Nc2cccn([C@@H]3C[C@H]3F)c2=O)nc2c(C(=O)N[C@@H]3CC[C@H]3O)cnn12] |
| I-1403 | 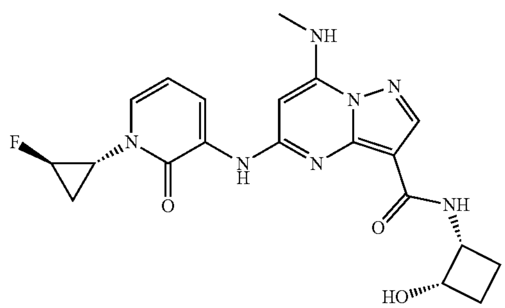 [SMILES: CNc1cc(Nc2cccn([C@@H]3C[C@H]3F)c2=O)nc2c(C(=O)N[C@@H]3CC[C@@H]3O)cnn12] |
| I-1404 | 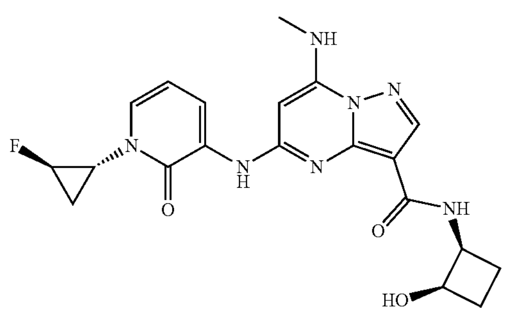 [SMILES: CNc1cc(Nc2cccn([C@@H]3C[C@H]3F)c2=O)nc2c(C(=O)N[C@H]3CC[C@H]3O)cnn12] |
| I-1405 | 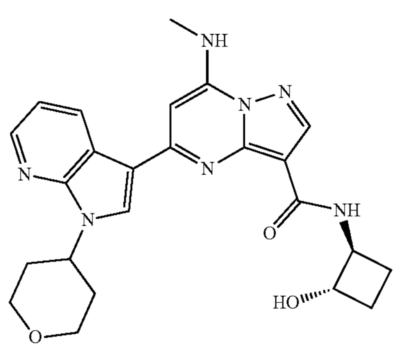 [SMILES: CNc1cc(-c2cn(C3CCOCC3)c3ncccc23)nc2c(C(=O)N[C@H]3CC[C@@H]3O)cnn12] |

TABLE 1-continued
Selected Compounds
| Compound | Structure |
|---|---|
| I-1406 | 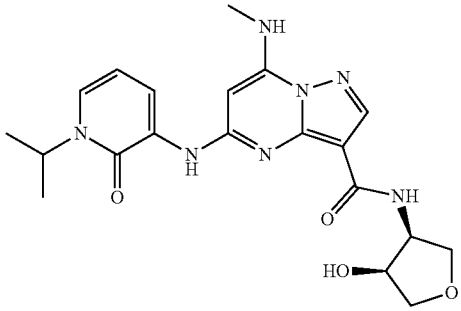 [SMILES: CNc1cc(Nc2cccn(C(C)C)c2=O)nc2c(C(=O)N[C@H]3COC[C@H]3O)cnn12] |
| I-1407 | 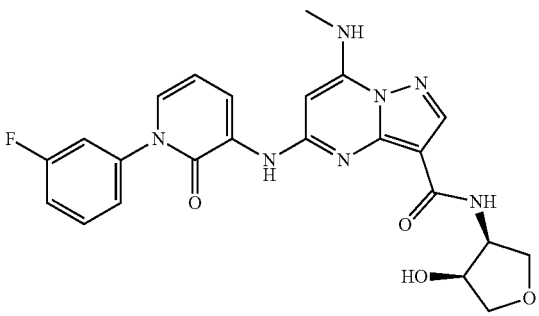 [SMILES: CNc1cc(Nc2cccn(-c3cccc(F)c3)c2=O)nc2c(C(=O)N[C@H]3COC[C@H]3O)cnn12] |
| I-1408 | 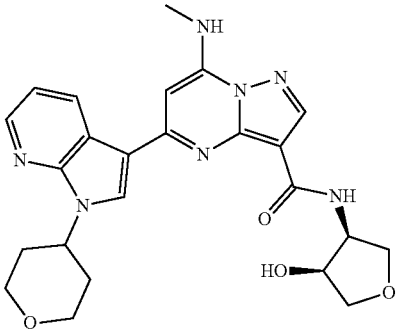 [SMILES: CNc1cc(-c2cn(C3CCOCC3)c3ncccc23)nc2c(C(=O)N[C@H]3COC[C@H]3O)cnn12] |
| I-1409 | 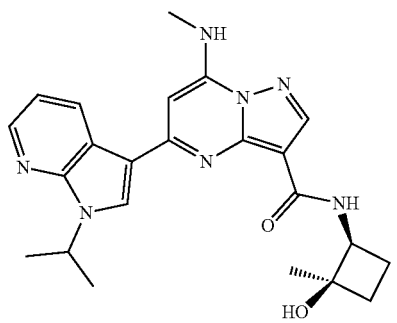 [SMILES: CNc1cc(-c2cn(C(C)C)c3ncccc23)nc2c(C(=O)N[C@H]3CC[C@@]3(C)O)cnn12] |

TABLE 1-continued
| Selected Compounds | |
|---|---|
| Compound | Structure |
| I-1410 | 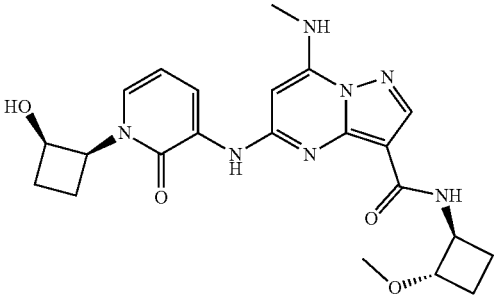 [SMILES: CNc1cc(Nc2cccn([C@H]3CC[C@H]3O)c2=O)nc2c(C(=O)N[C@H]3CC[C@@H]3OC)cnn12] |
| I-1411 | 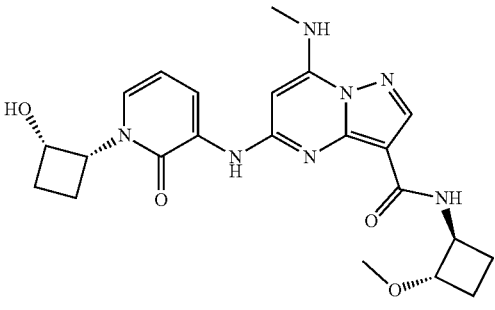 [SMILES: CNc1cc(Nc2cccn([C@@H]3CC[C@@H]3O)c2=O)nc2c(C(=O)N[C@H]3CC[C@@H]3OC)cnn12] |
| I-1412 | 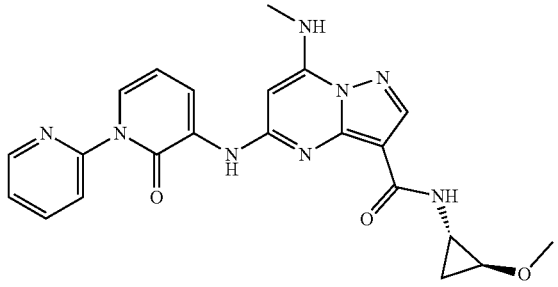 [SMILES: CNc1cc(Nc2cccn(-c3ccccn3)c2=O)nc2c(C(=O)N[C@H]3C[C@@H]3OC)cnn12] |
| I-1413 | 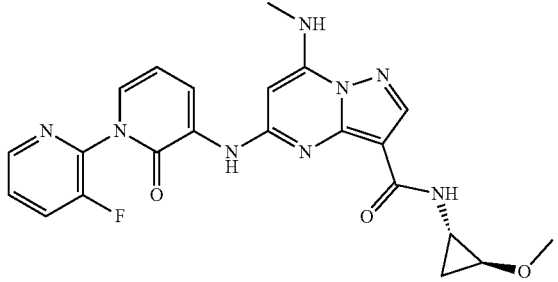 [SMILES: CNc1cc(Nc2cccn(-c3ncccc3F)c2=O)nc2c(C(=O)N[C@H]3C[C@@H]3OC)cnn12] |
| I-1414 | 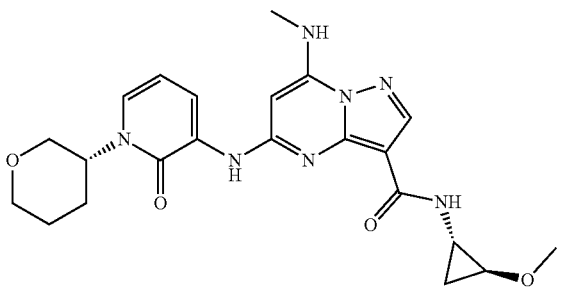 [SMILES: CNc1cc(Nc2cccn([C@@H]3CCCOC3)c2=O)nc2c(C(=O)N[C@H]3C[C@@H]3OC)cnn12] |

TABLE 1-continued

Selected Compounds

| Compound | Structure |
|---|---|
| I-1415 | 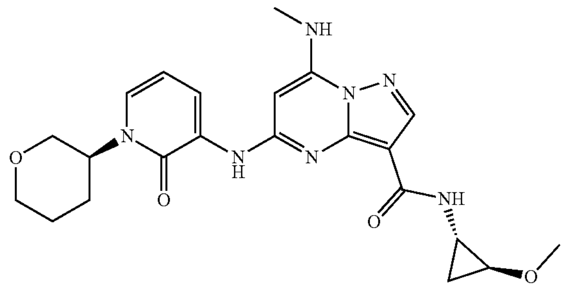 [SMILES: CNc1cc(Nc2cccn([C@H]3CCCOC3)c2=O)nc2c(C(=O)N[C@H]3C[C@@H]3OC)cnn12] |

In some embodiments, the method employs a compound set forth in Table 1, above, or a pharmaceutically acceptable salt thereof. In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I or I' as described above, wherein the compound is denoted as "A" as set forth in Table 2. In some embodiments, the present invention provides a compound of formula I or I' as described above, wherein the compound is denoted as "B" as set forth in Table 2. In some embodiments, the present invention provides a compound of formula I or I' as described above, wherein the compound is denoted as "C" as set forth in Table 2. In some embodiments, the present invention provides a compound of formula I or I' as described above, wherein the compound is denoted as "D" as set forth in Table 2. In some embodiments, the present invention provides a compound of formula I or I' as described above, wherein the compound is denoted as "A" or "B" as set forth in Table 2. In some embodiments, the present invention provides a compound of formula I or I' as described above, wherein the compound is denoted as "A" or "B" or "C" as set forth in Table 2. In some embodiments, the present invention provides a compound of formula I or I' as described above, wherein the compound is denoted as "A" or "B" or "C" or "D" as set forth in Table 2.

In some embodiments, the present invention provides a compound of formula I or I' as defined above, or a pharmaceutically acceptable salt thereof, or a pharmaceutical composition comprising a compound of formula I or I' as defined above, or a pharmaceutically acceptable salt thereof, and a pharmaceutically acceptable carrier, adjuvant, or vehicle for use as a medicament.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ξ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12R31 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behcet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmorterm brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radio-ligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, cutaneous lupus erythematosus, systemic lupus erythematosus, multiple sclerosis, psoriasis, Behcet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, cutaneous lupus erythematosus, systemic lupus erythematosus, pemphigus vulgaris, pemphigus *foliaceus*, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from cutaneous lupus erythematosus, Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I or I' and one or more additional therapeutic agents. The therapeutic agent may be administered together with a compound of formula I or I', or may be administered prior to or following administration of a compound of formula I or I'. Suitable therapeutic agents are described in further detail below. In certain embodiments, a compound of formula I or I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I or I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I or I' and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I or I' and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I or I' and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I or I' and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I or I' and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I or I' and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I or I' and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I or I' and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I or I' and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I or I' and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I or I' and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I or I' and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I or I' and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I or I'. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of the present invention are another embodiment of the present invention.

The present invention is now further described by means of non-limiting embodiments 1-32:

Embodiment 1

A compound of formula I':

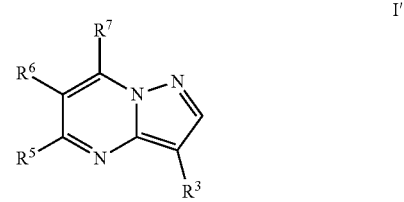

or a pharmaceutically acceptable salt thereof, wherein:
$R^3$ is —C(O)NH$_2$; —C(O)NHR$^{3A}$; —C(O)N(R$^{3A}$)$_2$; —C(O)OR; —C(O)NHOR; or a 5-6 membered monocyclic heteroaryl ring having 1-4 heteroatoms independently selected from nitrogen, oxygen, and sulfur, wherein said ring is substituted with m instances of R$^{3B}$;
$R^5$ is hydrogen, or -L$^1$-R$^{5A}$;
$R^6$ is hydrogen, R$^A$, or R$^B$;
or $R^5$ and $R^6$ are taken together with their intervening atoms to form a 4-7 membered partially unsaturated, or heteroaryl ring having 0-3 heteroatoms independently selected from nitrogen, oxygen, and sulfur, wherein said ring is substituted by R$^{5A}$ and n instances of R$^C$;
$R^7$ is hydrogen, halogen, —NH$_2$, —NHR$^{7A}$, or —NHC(O)R$^{7A}$;
or $R^6$ and $R^7$ are taken together with their intervening atoms to form a 4-7 membered partially unsaturated, or heteroaryl ring having 0-3 heteroatoms independently selected from nitrogen, oxygen, and sulfur; wherein said ring is substituted by p instances of R$^C$;
$L^1$ is a covalent bond or a C$_{1-4}$ bivalent saturated or unsaturated, straight or branched hydrocarbon chain wherein one or two methylene units of the chain are optionally and independently replaced by —C(R$^{5B}$)$_2$—, —CH(R$^{5B}$)—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;
$R^{3A}$ and $R^{7A}$ are each independently R$^B$, and are each substituted by q instances of R$^C$, wherein two R$^C$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two R$^C$ substituents on adjacent carbons are optionally taken together to form a 3-6 membered saturated or partially unsaturated fused heterocyclic ring having 1-4 heteroatoms independently selected from nitrogen, oxygen, and sulfur;
$R^{5A}$ and each instance of R$^{5B}$ are each independently R$^A$ or R$^B$, and are each substituted by r instances of R$^C$;
each instance of R$^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R;
each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium; and each instance of m, n, p, q, and r is independently 0, 1, 2, 3, or 4.

Embodiment 2

The compound of embodiment 1 of one of formulas II or III:

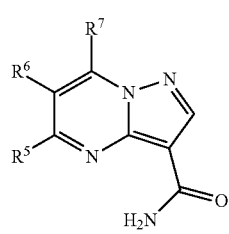

II

III or a pharmaceutically acceptable salt thereof.

Embodiment 3

The compound of any one of embodiments 1 or 2 of formula V or VI:

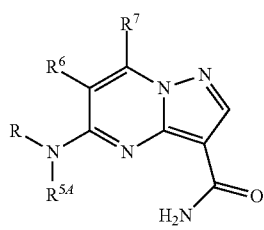

V

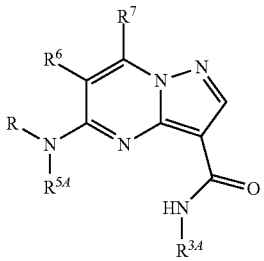

VI or a pharmaceutically acceptable salt thereof.

Embodiment 4

The compound of any one of embodiments 1-3 of formula V-a or VI-a:

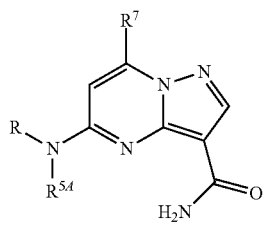

V-a

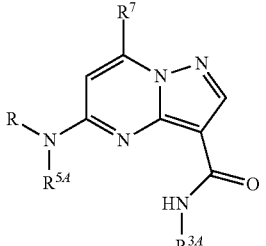

VI-a or a pharmaceutically acceptable salt thereof.

Embodiment 5

The compound of any one of embodiments 1-4 wherein $R^7$ is —$NH_2$ or —$NHR^{7A}$, or a pharmaceutically acceptable salt thereof.

Embodiment 6

The compound of any one of embodiments 1-5 of one of formulas V-c or VI-c:

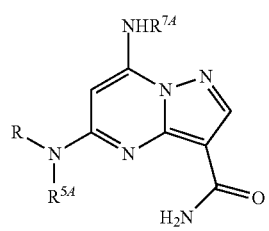

V-c

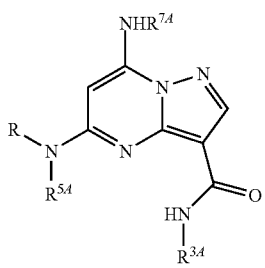

VI-c or a pharmaceutically acceptable salt thereof.

Embodiment 7

The compound of any one of embodiments 1-6 wherein each of $R^{3A}$ and $R^{7A}$ is independently $R^B$, and is substituted by q instances of $R^C$, provided that neither of $R^{3A}$ or $R^{7A}$ is phenyl.

Embodiment 8

The compound of any one of embodiments 1-7 wherein $R^{7A}$ is $C_{1-6}$ aliphatic.

Embodiment 9

The compound of any one of embodiments 1-8 wherein $R^{7A}$ is methyl.

Embodiment 10

The compound of any one of embodiments 1-9, selected from those depicted in Table 1 of the specification, or a pharmaceutically acceptable salt thereof.

Embodiment 11

A pharmaceutical composition comprising a compound according to any one of embodiments 1-10, or a pharmaceutically acceptable salt thereof, and a pharmaceutically acceptable carrier, adjuvant, or vehicle.

Embodiment 12

The compound of claims 1 to 10, or the pharmaceutical composition of claim 11 for use as a medicament.

Embodiment 13

A method, optionally an in-vitro method, of inhibiting TYK2 in a biological sample comprising contacting the sample with the compound of any one of embodiments 1-10, or a pharmaceutically acceptable salt thereof, or a pharmaceutical composition of claim 11.

Embodiment 14

The compound of any one of embodiments 1-10 or the pharmaceutical composition of embodiment 11 for use in the treatment of an TYK2-mediated disorder, disease, or condition in a patient comprising administering to said patient the compound of any one of embodiments 1-10 or the pharmaceutical composition of embodiment 11.

Embodiment 15

The compound of any one of embodiments 1-10 or the pharmaceutical composition of embodiment 11 for use according to embodiment 14, wherein the disorder is selected from an autoimmune disorder, an inflammatory disorder, a proliferative disorder, an endocrine disorder, a neurological disorder, or a disorder associated with transplantation.

Embodiment 16

The compound of any one of embodiments 1-10 or the pharmaceutical composition of embodiment 11 for use according to embodiment 15, wherein the disorder is an autoimmune disorder.

Embodiment 17

The compound of any one of embodiments 1-10 or the pharmaceutical composition of embodiment 11 for use according to embodiment 16, wherein the autoimmune disorder is selected from type 1 diabetes, ankylosing spondylitis, cutaneous lupus erythematosus, systemic lupus erythematosus, multiple sclerosis, systemic sclerosis, psoriasis, Crohn's disease, ulcerative colitis, and inflammatory bowel disease.

Embodiment 18

The compound of any one of embodiments 1-10 or the pharmaceutical composition of embodiment 11 for use according to embodiment 15, wherein the disorder is an inflammatory disorder.

Embodiment 19

The compound of any one of embodiments 1-10 or the pharmaceutical composition of embodiment 11 for use according to embodiment 18, wherein the inflammatory disorder is selected from rheumatoid arthritis, asthma, chronic obstructive pulmonary disease, psoriasis, Crohn's disease, ulcerative colitis, and inflammatory bowel disease.

Embodiment 20

The compound of any one of embodiments 1-10 or the pharmaceutical composition of embodiment 11 for use according to embodiment 15, wherein the disorder is a proliferative disorder.

Embodiment 21

The compound of any one of embodiments 1-10 or the pharmaceutical composition of embodiment 11 for use according to embodiment 20, wherein the proliferative disorder is a hematological cancer.

Embodiment 22

The compound of any one of embodiments 1-10 or the pharmaceutical composition of embodiment 11 for use according to embodiment 20, wherein the proliferative disorder is a leukemia.

Embodiment 23

The compound of any one of embodiments 1-10 or the pharmaceutical composition of embodiment 11 for use according to embodiment 22, wherein the leukemia is a T-cell leukemia.

Embodiment 24

The compound of any one of embodiments 1-10 or the pharmaceutical composition of embodiment 11 for use according to embodiment 23, wherein the T-cell leukemia is T-cell acute lymphoblastic leukemia (T-ALL).

Embodiment 25

The compound of any one of embodiments 1-10 or the pharmaceutical composition of embodiment 11 for use according to embodiment 20, wherein the proliferative disorder is associated with one or more activating mutations in TYK2.

Embodiment 26

The compound of any one of embodiments 1-10 or the pharmaceutical composition of embodiment 11 for use according to embodiment 15, wherein the disorder is associated with transplantation.

Embodiment 27

The compound of any one of embodiments 1-10 or the pharmaceutical composition of embodiment 11 for use according to embodiment 26, wherein the disorder is transplant rejection or graft versus host disease.

Embodiment 28

The compound of any one of embodiments 1-10 or the pharmaceutical composition of embodiment 11 for use according to embodiment 15, wherein the disorder is an endocrine disorder.

Embodiment 29

The compound of any one of embodiments 1-10 or the pharmaceutical composition of embodiment 11 for use according to embodiment 28, wherein the endocrine disorder is polycystic ovary syndrome, Crouzon's syndrome, or type 1 diabetes.

Embodiment 30

The compound of any one of embodiments 1-10 or the pharmaceutical composition of embodiment 11 for use according to embodiment 15, wherein the disorder is a neurological disorder.

Embodiment 31

The compound of any one of embodiments 1-10 or the pharmaceutical composition of embodiment 11 for use according to embodiment 30, wherein the neurological disorder is Alzheimer's disease.

Embodiment 32

The compound of any one of embodiments 1-10 or the pharmaceutical composition of embodiment 11 for use according to embodiment 14, wherein the disorder is associated with type I interferon, IL-10, IL-12, or IL-23 signaling.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

General Procedure A (Acid-Amine Coupling):

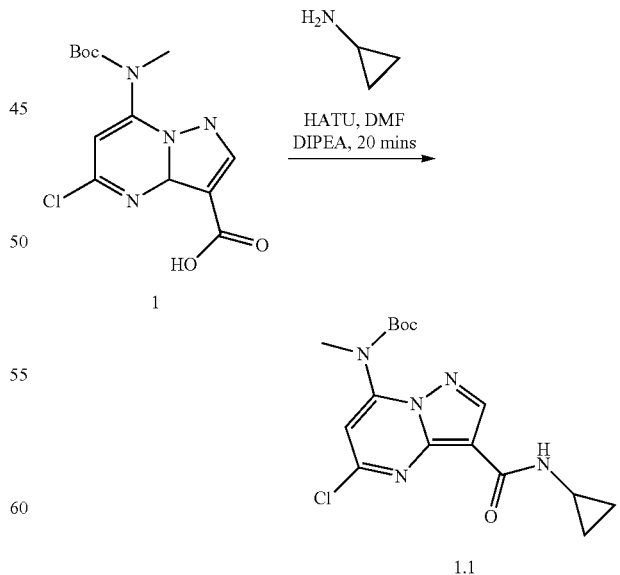

Synthesis of Compound 1.1.

To a solution of 1 (4 g, 12.26 mmol, 1.0 eq), in N,N-dimethylformamide (40 mL) was added 1-[Bis(dimethyl-amino)methylene]-1H-1,2,3-triazolo[4,5-b]pyridinium 3-oxid hexafluorophosphate (9.32 g, 24.53 mmol, 2.0 eq) and stirred at room temperature for 15 min. To this added diisopropylethylamine (6.40 mL, 36.78 mmol, 3.0 eq) followed by addition of cyclopropanamine (0.699 g, 12.26 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.1 (2.4 g, 53.69%). MS(ES): m/z 366.13 [M+H]⁺.

General Procedure B (Buchwald Amination):

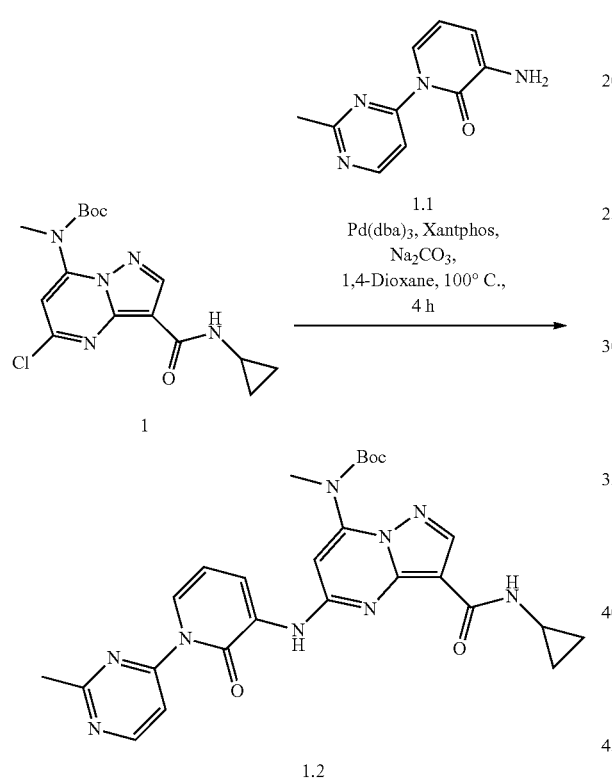

Synthesis of Compound 1.2.

To a solution of 1 (0.125 g, 0.342 mmol, 1.0 eq) in 1,4-dioxane (5 mL) was added 1.1 (0.082 g, 0.410 mmol, 1.2 eq), sodium carbonate (0.072 g, 0.684 mmol, 2.0 eq). The reaction mixture was degassed for 10 min. under argon atmosphere, then tris(dibenzylideneacetone)dipalladium(0) (0.015 g, 0.017 mmol, 0.05 eq) and 4,5-Bis(diphenylphosphino)-9,9-dimethylxanthene (0.019 g, 0.034 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 1.2 (0.070 g, 38.6%). MS(ES): m/z 532.23 [M+H]⁺.

General Procedure C (BOC-Deprotection):

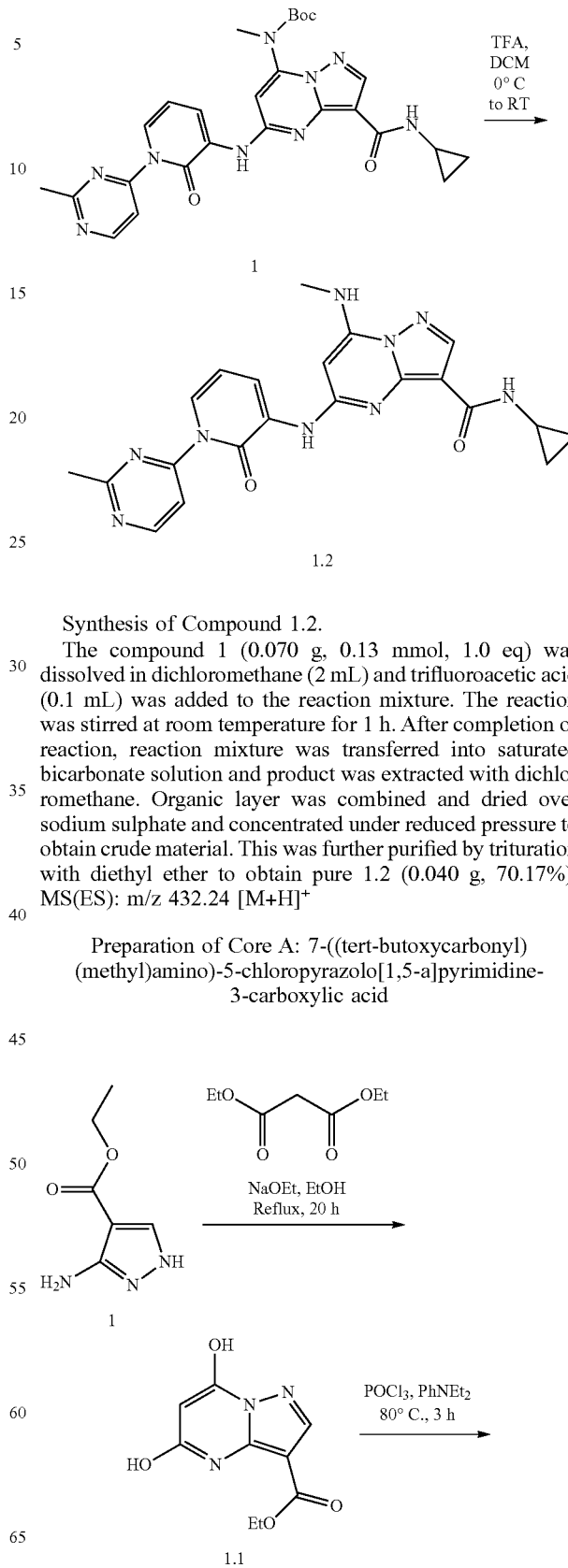

Synthesis of Compound 1.2.

The compound 1 (0.070 g, 0.13 mmol, 1.0 eq) was dissolved in dichloromethane (2 mL) and trifluoroacetic acid (0.1 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 1.2 (0.040 g, 70.17%). MS(ES): m/z 432.24 [M+H]⁺

Preparation of Core A: 7-((tert-butoxycarbonyl)(methyl)amino)-5-chloropyrazolo[1,5-a]pyrimidine-3-carboxylic acid

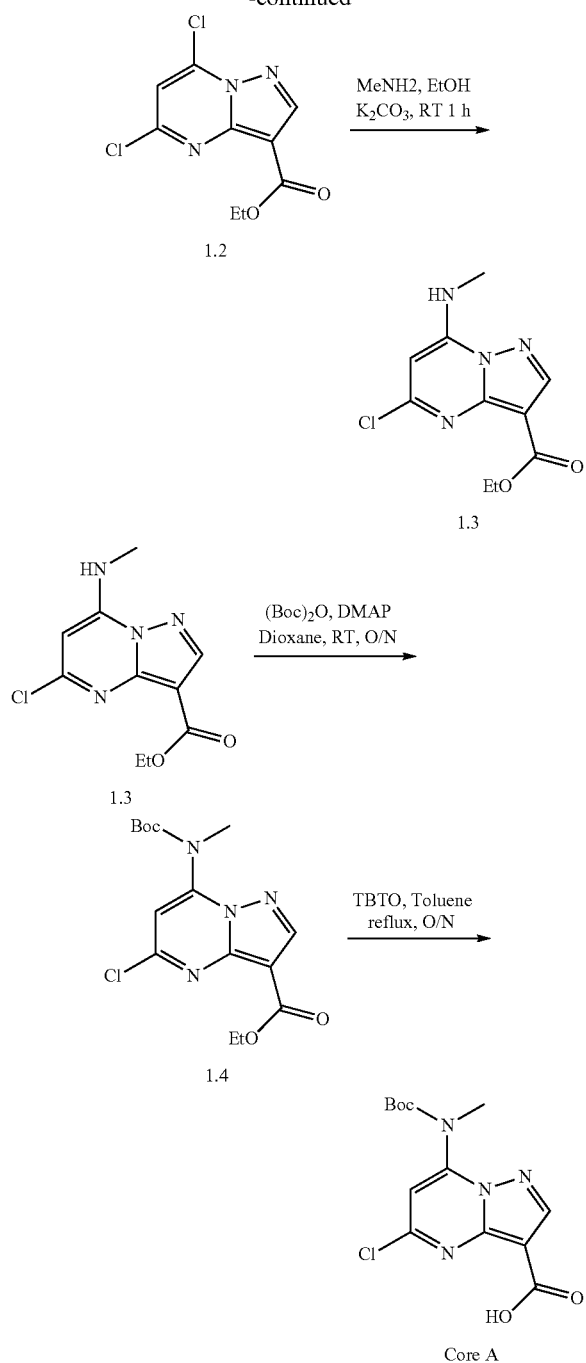

Synthesis of Compound 1.1.

To a solution of 1 (50 g, 322.25 mmol, 1.0 eq) in ethanol (250 mL) was added diethyl malonate (103.2 g, 644.51 mmol, 2.0 eq) followed by dropwise addition of sodium ethoxide (75 mL, 21% ethanol solution, 3.0 eq). Reaction mixture was stirred with heating under reflux for 20 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure 1.1 (43 g, 59.79%). MS(ES): m/z 224.2 [M+H]$^+$.

Synthesis of Compound 1.2.

To a mixture of 1.1 (43 g, 192.6 mmol, 1.0 eq) in phosphorous oxychloride (191 g, 1251 mmol, 6.5 eq) was added diethyl aniline (43 g, 288.9 mmol, 1.5 eq). Reaction mixture stirred at 80° C. for 3 h. After completion of reaction; reaction mixture was concentrated under reduced pressure to obtained residue which was transferred into ice cold water and extracted with dichloromethane. Organic layer was combined, washed with saturated sodium bicarbonate solution followed by brine solution, dried over sodium sulphate and concentrated under reduced pressure to pressure to obtain crude material. This was further purified by column chromatography and the compound was eluted in 20% ethyl acetate in hexane to obtain pure 1.2 (35 g, 69.85%). MS(ES): m/z 261 [M+H]$^+$.

Synthesis of Compound 1.3.

To a solution of 1.2 (35 g, 134.58 mmol, 1.0 eq) in ethanol (350 mL) was added potassium carbonate (18.57 g, 134.58 mmol, 1.0 eq) at 0° C. followed by methylamine (40% in water)(10.95 mL, 141.3 mmol, 1.05 eq) and reaction mixture stirred at room temperature for 1 h. After completion of reaction; reaction mixture was concentrated under reduced pressure to obtained residue which was transferred into ice cold water. Precipitated solid was filtered, washed with water and dried well under vacuum to obtain 1.3. (30 g, 87.53%). MS(ES): m/z 255.6 [M+H]$^+$.

Synthesis of Compound 1.4.

To a solution of 1.3 (30 g, 117.8 mmol, 1.0 eq) in 1,4-dioxane (300 mL) was added N,N-dimethylaminopyridine (1.43, 11.78 mmol, 0.1 eq) followed by Di-tert-butyl dicarbonate (51.36 g, 235.6 mmol, 2.0 eq) and reaction mixture was stirred at room temperature for 12 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 12% ethyl acetate in hexane to obtain 1.4. (26 g, 62.21%). MS(ES): m/z 355 [M+H]$^+$.

Synthesis of Core A.

To a suspension of 1.4 (20 g, 56.37 mmol, 1.0 eq) in toluene (200 mL) was added Tributyltin oxide (67.19 g, 112.73 mmol, 2.0) and reaction mixture was heated at 120° C. for 12 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulphate and concentrated under reduced pressure to obtain solid which was triturated with hexane to obtain pure Core A. (13.2 g, 71.67%). $^1$H NMR (DMSO-d6, 400 MHZ): 12.63 (s, 1H), 8.63 (s, 1H), 7.55 (s, 1H), 3.31 (s, 3H), 1.29 (s, 9H).

Preparation of Core B: 5-chloro-7-(dibenzylamino) pyrazolo[1,5-a]pyrimidine-3-carboxamide

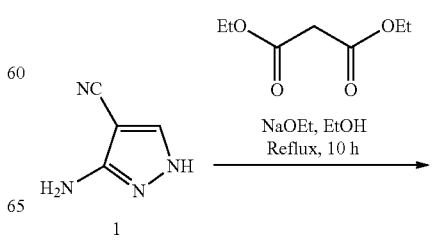

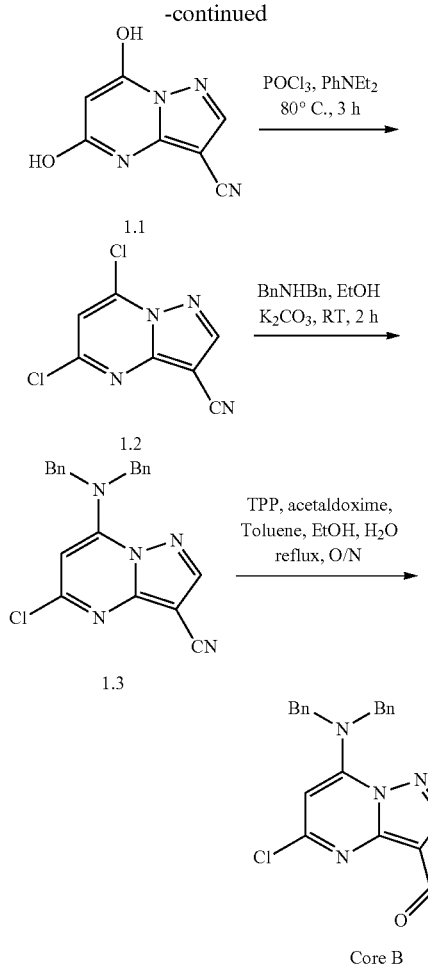

Synthesis of Compound 1.1.

To a solution of 1 (50 g, 462.5 mmol, 1.0 eq) in ethanol (400 mL) was added diethyl malonate (141 mL, 925.06 mmol, 2.0 eq) followed by dropwise addition of sodium ethoxide (21% in ethanol) (108 mL, 1387.5 mmol, 3.0 eq). Reaction mixture was stirred with heating under reflux for 10 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure 1.1 (50 g, 61.38%). MS(ES): m/z 177.14 [M+H]+.

Synthesis of Compound 1.2.

To a mixture of 1.1 (50 g, 283.87 mmol, 1.0 eq) in phosphorous oxychloride (163 mL, 1704.54 mmol, 6.0 eq) was added diethyl aniline (68.26 mL, 426.13 mmol, 1.5 eq). Reaction mixture stirred at 90° C. for 3 h. After completion of reaction; reaction mixture was concentrated under reduced pressure to obtained residue which was transferred into ice cold water and extracted with dichloromethane. Organic layer was combined, washed with saturated sodium bicarbonate solution followed by brine solution, dried over sodium sulphate and concentrated under reduced pressure to obtain crude material. This was further purified by column chromatography and the compound was eluted in 20% ethyl acetate in hexane to obtain pure 1.2 (45 g, 74.42%). MS(ES): m/z 214.02 [M+H]+.

Synthesis of Compound 1.3.

To a solution of 1.2 (10 g, 46.94 mmol, 1.0 eq) in ethanol (315 mL) was added potassium carbonate (7.12 g, 51.63 mmol, 1.1 eq) at 0° C. followed by dibenzyl amine (9.97 mL, 51.63 mmol, 1.1 eq) and reaction mixture stirred at room temperature for 2 h. After completion of reaction; reaction mixture was concentrated under reduced pressure to obtained residue which was transferred into ice cold water. Precipitated solid was filtered, washed with water and dried well under vacuum to obtain 1.3. (1 g, 62.68%). MS(ES): m/z 374.84 [M+H]+.

Synthesis of Core B.

To a solution of 1.3 (1 g, 29.42 mmol, 1.0 eq) in mixture of toluene:ethanol:water (160 mL, 1.0:0.5:0.25) was added triphenylphosohine (1.54, 5.88 mmol, 0.2 eq) at 0° C. followed by acetaldoxime (3.47 g, 58.84 mmol, 2.0 eq) and reaction mixture was stirred at 110° C. for 5 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 25% ethyl acetate in hexane to obtain Core B. (4.3 g, 37.29%). MS(ES): m/z 392.86 [M+H]+, $^1$H NMR (DMSO-$d_6$, 400 MHZ): 8.48 (s, 1H), 7.44-7.28 (m, 10H), 6.46 (s, 1H), 5.19 (s, 4H).

Preparation of Core C: Ethyl 5-chloro-7-(dibenzylamino)pyrazolo[1,5-a]pyrimidine-3-carboxylate

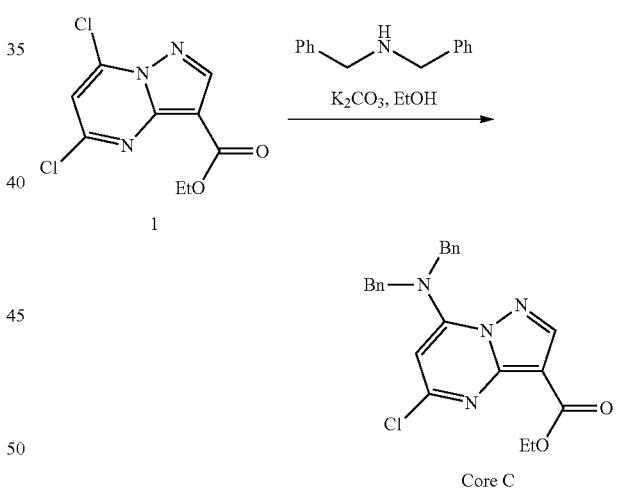

Synthesis of Compound 1.

Compound was synthesized as per experimental procedure [0002] of core synthesis.

Synthesis of Core C

To a solution of 1 (1.0 g, 3.85 mmol, 1.0 eq) in ethanol (8 mL) was added potassium carbonate (1.06 g, 7.7 mmol, 2.0 eq) followed by dropwise addition of dibenzyl amine (0.834 g, 4.23 mmol, 1.1 eq). Reaction mixture was stirred at room temperature for 4 h. After completion of reaction, reaction mixture was transferred into ice cold water, precipitated solid was filtered, washed with water followed by diethyl ether and dried well to obtain pure Core C (1.0 g, 62%). MS(ES): m/z 421.9 [M+H]+. $^1$H NMR (DMSO-d6, 400

MHZ): 8.47 (s, 1H), 7.39-7.35 (m, 6H), 7.30-7.26 (m, 4H), 6.18 (s, 1H), 5.37 (s, 4H), 4.47-4.42 (q, 2H), 1.46-1.43 (t, 3H).

Intermediate A: 3-amino-1-(tetrahydro-2H-pyran-3-yl)pyridin-2(1H)-one

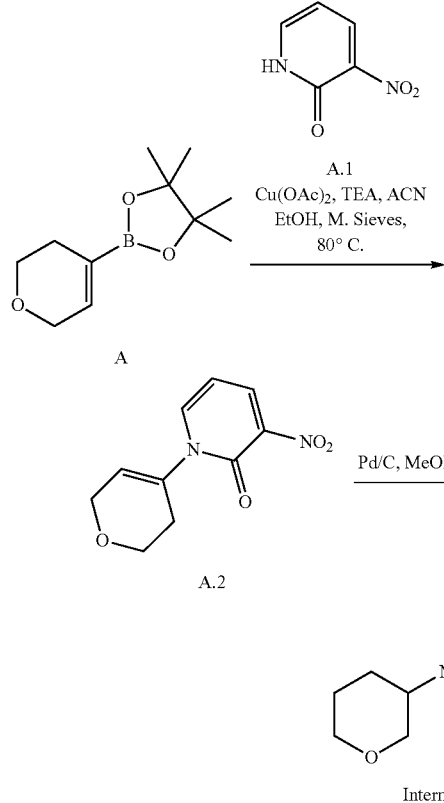

Synthesis of Compound A.2.

To a solution of A (0.60 g, 2.86 mmol, 1.0 eq), in ethanol:acetonitrile (1:1) (1 mL), A.1 (0.40 g, 2.86 mmol, 1.0 eq) copper acetate (0.51 g, 2.86 mmol, 1.0 eq), molecular sieve (0.40 g, 2.86 mmol, 1.0 eq) and triethylamine (0.5 g, 5.72 mmol, 2.0 eq) was added. The reaction mixture was stirred at 80° C. for 3 h. After completion of reaction, reaction mixture was, filtered through celite and product was washed with methanol. Organic layer was combined, dried over sodium sulphate and concentrated under reduced pressure to obtain crude material. This was further purified by column chromatography to obtain pure A.2 (0.19 g, 29.94%). MS(ES): m/z 222.20 [M+H]+

Synthesis of Intermediate A.

To a solution of A.2 (0.19 g, 0.85 mmol, 1.0 eq) in methanol (3 mL), palladium on charcoal (0.04 g) was added. Hydrogen was purged through reaction mixture for 24 h at room temperature. After completion of reaction, reaction mixture was filtered through celite-bed and washed with methanol. Filtrate was concentrated under reduced pressure to obtain Intermediate A (0.06 g, 36.13%). MS(ES): m/z 195.23 [M+H]+.

Intermediates B-i and B-ii: (S)-3-amino-1-(tetrahydro-2H-pyran-3-yl)pyridin-2(1H)-one (B-i) and (R)-3-amino-1-(tetrahydro-2H-pyran-3-yl)pyridin-2(1H)-one (B-ii)

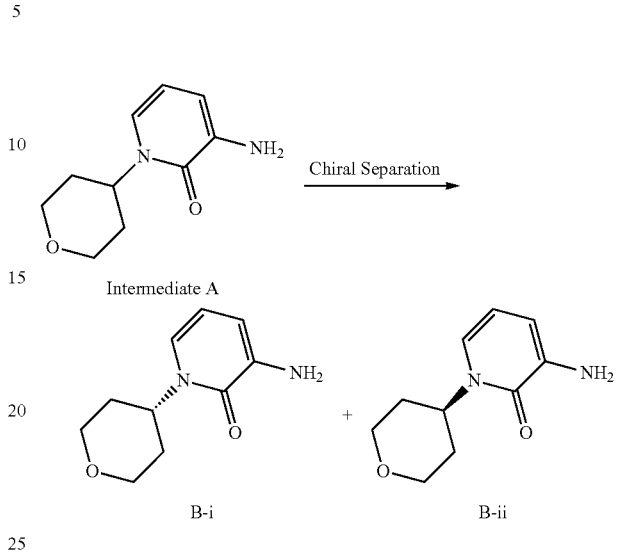

Synthesis of Intermediate A.

Compound was synthesized as per experimental protocol of Intermediate A to obtain Intermediate A. (Yield: 36.13%). MS (ES): m/z 195.23 [M+H]+

Synthesis of Compounds B-i and B-ii.

Isomers of Intermediate A (0.8 g) were separated using column (CHIRAL PAK AD-H 250×4.6 mm, 5 μM) and 0.3% Diethylamine in methanol as co-solvent with flow rate of 4 mL/min. to get pure 1a. fraction-1 and 1b. fraction-2 (FR-b). FR-a was evaporated under reduced pressure at 30° C. to afford pure fraction-1. (0.3 g). MS(ES): m/z 195.11 [M+H]+. FR-b was evaporated under reduced pressure at 30° C. to afford pure fraction-2. (0.3 g). MS(ES): m/z 195.11 [M+H]+.

Example 1: N-cyclopropyl-5-((3,5-dimethylphenyl)amino)-7-(methylamino)pyrazolo[1,5-a]pyrimidine-3-carboxamide (I-1)

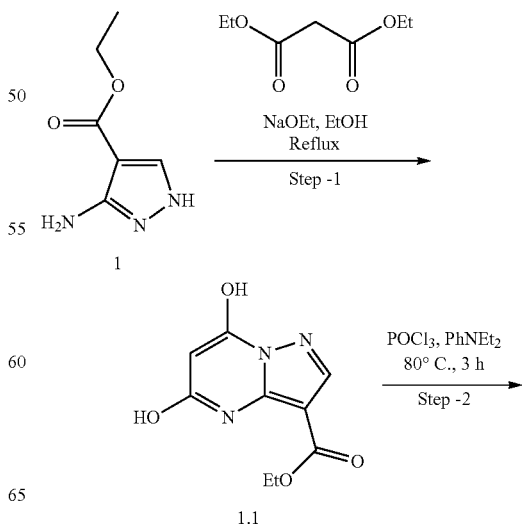

791
-continued

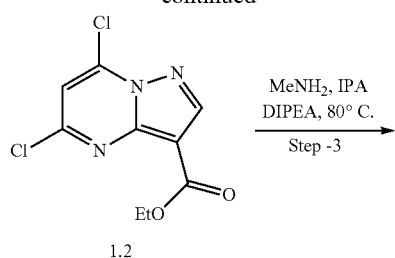

1.2

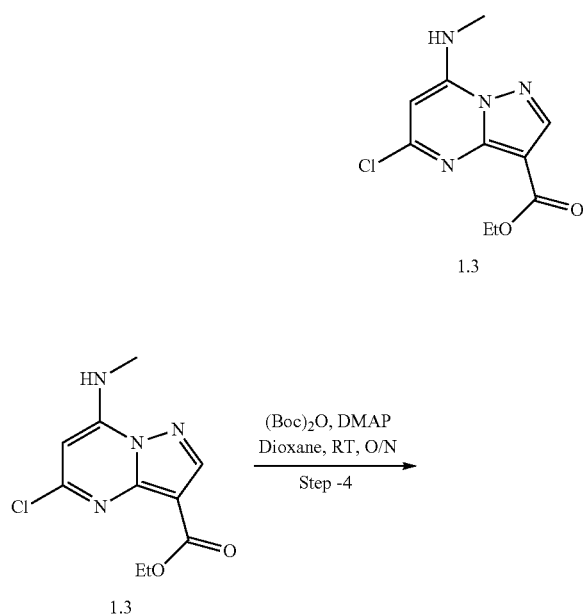

1.3

1.4

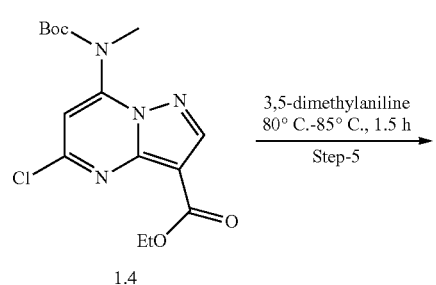

1.5

792
-continued

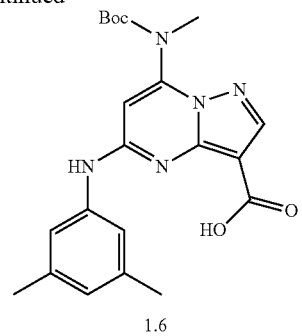

1.6

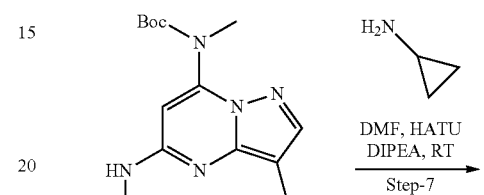

1.6

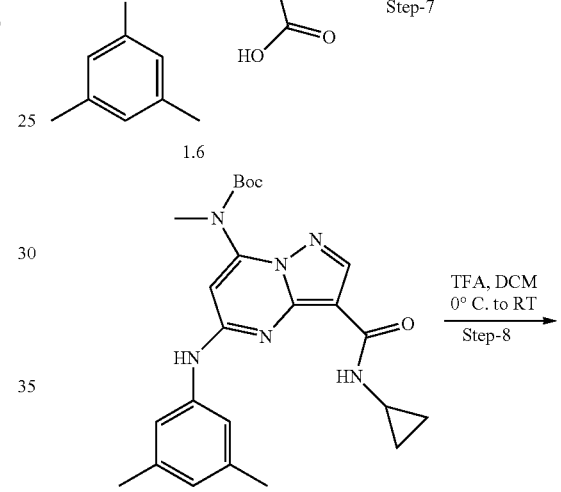

1.7

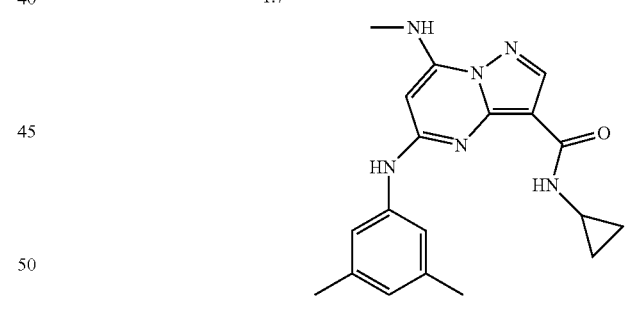

I-1

Synthesis of Compound 1.1.

To a solution of 1 (10 g, 64.45 mmol, 1.0 eq) in ethanol (300 mL) was added diethyl malonate (20.65 g, 128.9 mmol, 2.0 eq) followed by dropwise addition of sodium ethoxide (74.97 g, 21% ethanol solution, 3.59 eq). The reaction mixture was stirred with heating under reflux for 18 h. After completion of reaction, the mixture was concentrated under reduced pressure to obtain a residue which was dissolved in water, acidified with concentrated hydrochloric acid to pH~3-4. The precipitated solid was filtered, washed with water, diethyl ether and dried to obtain pure 1.1 (10 g, 69.52%). MS(ES): m/z 224.2 [M+H]$^+$.

Synthesis of Compound 1.2.

To a mixture of 1.1 (3 g, 13.44 mmol, 1.0 eq) in phosphorous oxychloride (8.7 mL) was added diethyl aniline (3.37 g, 22.56 mmol, 1.68 eq). The reaction mixture stirred at 80° C. for 3 h. After completion of reaction, the mixture was diluted with ice cold water, neutralized with saturated sodium bicarbonate solution and extracted with dichloromethane. The organic layers were combined, washed with a brine solution, dried over sodium sulphate and concentrated under reduced pressure to pressure to obtain the crude material. This was further purified by column chromatography and the compound was eluted in 15% ethyl acetate in hexane to obtain pure 1.2 (3.0 g, 85.82%). MS(ES): m/z 261 [M+H]$^+$.

Synthesis of Compound 1.3.

To a solution of 1.2 (3.0 g, 11.54 mmol, 1.0 eq) in isopropylalcohol (30 mL) was added diisopropylethylamine (4.2 mL, 23 mmol, 2.0 eq) at 0° C. followed by methylamine (6.9 mL, 13 mmol, 1.2 eq) and the reaction mixture stirred at 80° C. for 16 h. After completion of reaction, the mixture was concentrated under reduced pressure to obtain a crude residue. To this residue, was added water and the mixture extracted with dichloromethane. The organic layers were combined, washed with a brine solution, dried over sodium sulphate and concentrated under reduced pressure to pressure to obtain the crude material. This was further purified by column chromatography and the compound was eluted in 40% ethyl acetate in hexane to obtain 1.3. (2.9 g, 95.12%). MS(ES): m/z 310[M+H]$^+$.

Synthesis of Compound 1.4.

To a solution of 1.3 (2.9 g, 11.39 mmol, 1.0 eq) in 1,4-dioxane (15 mL) was added N,N-dimethylaminopyridine (0.138 g, 1.139 mmol, 0.1 eq) followed by di-tert-butyl dicarbonate (4.79 g, 22.78, 2.0 eq) and the reaction mixture was stirred at room temperature for 16 h. After completion of reaction, the mixture was diluted with water and the product was extracted with dichloromethane. The organic layers were combined, dried over sodium sulphate and concentrated under reduced pressure to obtain the crude material. This was further purified by column chromatography and the compound was eluted in 10% ethyl acetate in hexane to obtain 1.4. (2.9 g, 71.78%). MS(ES): m/z 355 [M+H]$^+$.

Synthesis of Compound 1.5.

A mixture of 1.4 (1.0 g, 2.82 mmol, 1.0 eq) and 3,5-dimethylaniline (2 mL) was stirred at 80° C.-85° C. for 1.5 h. After completion of reaction, the mixture was diluted with water and the product was extracted with dichloromethane. The organic layers were combined, dried over sodium sulphate and concentrated under reduced pressure to obtain the crude material. This was further purified by column chromatography and the compound was eluted in 20% ethyl acetate in hexane to obtain 1.5. (1.0 g, 80.72%). MS(ES): m/z 440.5 [M+H]$^+$.

Synthesis of Compound 1.6.

To a solution of 1.5 (1.0 g, 2.28 mmol, 1.0 eq), in tetrahydrofuran:methanol:water (15 mL, 1:1:1) was added lithium hydroxide (0.957 g, 22.8 mmol, 10 eq). The reaction was stirred at room temperature for 16 h. After completion of reaction, the mixture was concentrated under reduced pressure to obtain residue. To this residue, was added aqueous 1N hydrochloric acid to adjust pH~6-6.5 at 10° C. The product was extracted with dichloromethane. The organic layers were combined, washed with a brine solution, dried over sodium sulphate and concentrated under reduced pressure to obtain 1.6 (0.8 g, 85.45%). MS(ES): m/z 412 [M+H]$^+$.

Synthesis of Compound 1.7.

To a solution of 1.6 (0.110 g, 0.267 mmol, 1.0 eq), in N,N-dimethylformamide (2 mL) was added 1-[bis(dimethylamino)methylene]-1H-1,2,3-triazolo[4,5-b]pyridinium 3-oxid hexafluorophosphate (0.203 g, 0.535 mmol, 2.0 eq) and the mixture was stirred at room temperature for 20 min. To this mixture, was added diisopropylethylamine (0.14 mL, 0.801 mmol, 3.0 eq) followed by the addition of cyclopropanamine (0.030 g, 0.535 mmol, 2.0 eq). The reaction mixture was stirred at room temperature for 1 h. After completion of reaction, the mixture was diluted with water and the product was extracted with ethyl acetate. The organic layers were combined, washed with a brine solution, dried over sodium sulphate and concentrated under reduced pressure to obtain the crude material. This was further purified by column chromatography and the compound was eluted in 25% ethyl acetate in hexane to obtain 1.7. (0.070 g, 58.12%). MS(ES): m/z 451.5 [M+H]$^+$.

Synthesis of Compound I-1.

Compound 1.7 (0.070 g, 0.155 mmol, 1.0 eq) was dissolved in dichloromethane (2 mL) and trifluoroacetic acid (0.1 mL) was added to the reaction mixture. The reaction was stirred at room temperature for 2 h. After completion of reaction, the mixture was poured in water, basified with a saturated bicarbonate solution and the product was extracted with ethyl acetate. The organic layers were combined, dried over sodium sulphate and concentrated under reduced pressure to obtain the crude material. This was further purified by trituration with diethyl ether to obtain pure I-1 (0.025 g, 45.92%). MS(ES): m/z 351.56 [M+H]$^+$, LCMS purity: 96.68%, HPLC purity: 96.09%, $^1$H NMR (DMSO-d$_6$, 400 MHZ): 9.32 (s, 1H), 8.14 (s, 1H), 7.97-7.96 (d, J=3.2 Hz, 1H), 7.86-7.85 (d, J=5.2 Hz, 1H), 7.14 (s, 2H), 6.73 (s, 1H), 5.50 (s, 1H), 2.91 (s, 3H), 2.77-2.74 (m, 1H), 2.30 (s, 6H), 0.72-0.67 (m, 2H), 0.35 (m, 2H).

Example 2: 5-((3,5-dimethylphenyl)amino)-7-(methylamino)pyrazolo[1,5-a]pyrimidine-3-carboxamide (I-2)

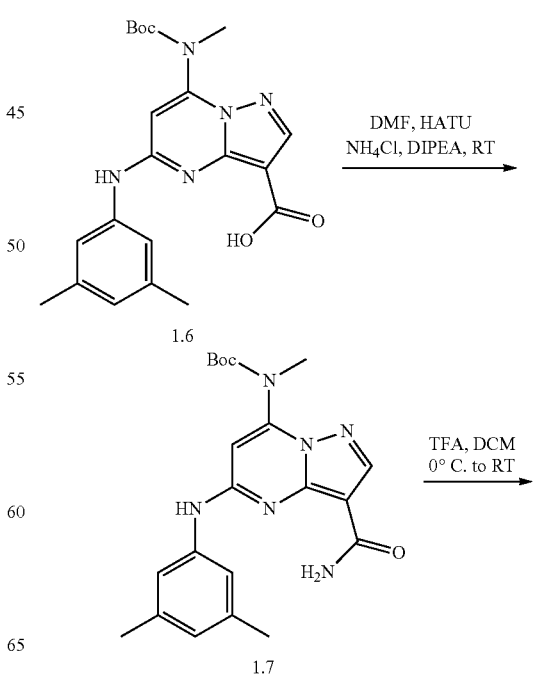

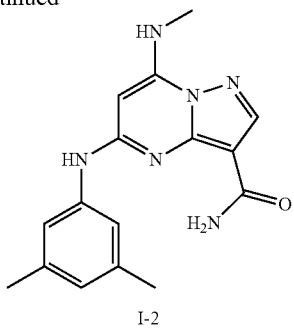

I-2

Synthesis of Compound 1.7.

To a solution of 1.6 (0.150 g, 0.364 mmol, 1.0 eq), in N,N-dimethylformamide (3 mL) was added 1-[bis(dimethylamino)methylene]-1H-1,2,3-triazolo[4,5-b]pyridinium 3-oxid hexafluorophosphate (0.276 g, 0.728 mmol, 2.0 eq) and the mixture was stirred at room temperature for 20 min. To this mixture, was added diisopropylethylamine (0.195 mL, 1.092 mmol, 3.0 eq) followed by the addition of ammonium chloride (0.058 g, 1.092 mmol, 3.0 eq). The reaction mixture was stirred at room temperature for 1 h. After completion of reaction, the mixture was diluted with water and the product was extracted with ethyl acetate. The organic layers were combined, washed with a brine solution, dried over sodium sulphate and concentrated under reduced pressure to obtain the crude material. This was further purified by column chromatography and the compound was eluted in 40% ethyl acetate in hexane to obtain 1.7. (0.070 g, 46.78%). MS(ES): m/z 411.5 [M+H]$^+$.

Synthesis of Compound I-2.

Compound 1.7 (0.070 g, 0.170 mmol, 1.0 eq) was dissolved in dichloromethane (2 mL) and trifluoroacetic acid (0.1 mL) was added to the reaction mixture. The reaction was stirred at room temperature for 2 h. After completion of reaction, the mixture was diluted with water, basified with saturated bicarbonate solution and the product was extracted with ethyl acetate. The organic layers were combined, dried over sodium sulphate and concentrated under reduced pressure to obtain the crude material. This was further purified by trituration with diethyl ether to obtain pure I-2 (0.025 g, 94.47%). MS(ES): m/z 311.54 [M+H]$^+$, LCMS purity: 98.61%, HPLC purity: 97.72%, $^1$H NMR (DMSO-d$_6$, 400 MHZ): 9.37 (s, 1H), 8.13 (s, 1H), 7.85-7.84 (d, J=4.8 Hz, 1H), 7.53 (s, 1H), 7.34 (s, 1H), 6.66 (s, 1H), 5.51 (s, 1H), 2.91 (s, 3H), 2.25 (s, 6H).

Example 3. TYK2 JH2 Domain Binding Assay

Binding constants for compounds of the present invention against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP_003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2 (JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a ≥10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{Hill\,Slope}}{Dose^{Hill\,Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)).

Results of the Tyk2 JH2 Domain Binding Assay are presented in Table 2. Compounds denoted as "A" had a Kd lower than 200 pM; compounds denoted as "B" had a Kd between 200 pM and 1 nM; compounds denoted as "C" had a Kd between 1 nM and 10 nM; and compounds denoted as "D" had a Kd greater than 10 nM.

TABLE 2

Results of Tyk2 JH2 Domain Binding Assay

| Compound | Tyk2 JH2 Kd |
|---|---|
| I-1 | A |
| I-2 | A |
| I-3 | A |
| I-4 | A |
| I-5 | A |
| I-6 | A |
| I-7 | A |
| I-8 | A |
| I-9 | A |
| I-10 | A |
| I-11 | C |
| I-12 | C |
| I-13 | C |
| I-14 | A |
| I-15 | B |
| I-16 | B |
| I-17 | A |
| I-18 | A |
| I-19 | C |
| I-20 | A |
| I-21 | B |
| I-22 | B |
| I-23 | C |
| I-24 | A |
| I-25 | B |
| I-26 | A |
| I-27 | C |
| I-28 | D |
| I-29 | C |
| I-30 | C |
| I-31 | A |
| I-32 | B |
| I-33 | B |
| I-34 | B |
| I-35 | A |
| I-36 | A |
| I-37 | A |
| I-38 | B |
| I-39 | C |
| I-40 | B |
| I-41 | C |
| I-42 | C |
| I-43 | A |
| I-44 | B |
| I-45 | A |
| I-46 | A |
| I-47 | A |
| I-48 | B |
| I-49 | B |
| I-50 | B |
| I-51 | B |
| I-52 | B |
| I-53 | A |
| I-54 | C |
| I-55 | D |
| I-56 | D |
| I-57 | B |
| I-58 | A |
| I-59 | A |
| I-60 | C |
| I-61 | B |
| I-62 | D |
| I-63 | A |
| I-64 | B |

TABLE 2-continued

Results of Tyk2 JH2 Domain Binding Assay

| Compound | Tyk2 JH2 Kd |
|---|---|
| I-65 | A |
| I-66 | B |
| I-67 | A |
| I-68 | B |
| I-69 | B |
| I-70 | C |
| I-71 | A |
| I-72 | A |
| I-73 | C |
| I-74 | B |
| I-75 | B |
| I-76 | C |
| I-77 | B |
| I-78 | A |
| I-79 | B |
| I-80 | B |
| I-81 | C |
| I-82 | C |
| I-83 | D |
| I-84 | B |
| I-85 | C |
| I-86 | D |
| I-87 | D |
| I-88 | D |
| I-89 | D |
| I-90 | B |
| I-91 | A |
| I-92 | D |
| I-93 | D |
| I-94 | A |
| I-95 | A |
| I-96 | B |
| I-97 | C |
| I-98 | A |
| I-99 | C |
| I-100 | C |
| I-101 | D |
| I-102 | B |
| I-103 | D |
| I-104 | C |
| I-105 | A |
| I-106 | A |
| I-107 | A |
| I-108 | B |
| I-109 | D |
| I-110 | A |
| I-111 | B |
| I-112 | C |
| I-113 | C |
| I-114 | C |
| I-115 | A |
| I-116 | A |
| I-117 | A |
| I-118 | B |
| I-119 | C |
| I-120 | C |
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | C |
| I-132 | A |
| I-133 | A |
| I-134 | B |
| I-135 | A |
| I-136 | A |
| I-137 | A |
| I-138 | A |
| I-139 | A |
| I-140 | A |

TABLE 2-continued

Results of Tyk2 JH2 Domain Binding Assay

| Compound | Tyk2 JH2 Kd |
|---|---|
| I-141 | A |
| I-142 | A |
| I-143 | D |
| I-144 | A |
| I-145 | A |
| I-146 | B |
| I-147 | A |
| I-148 | B |
| I-149 | C |
| I-150 | B |
| I-151 | A |
| I-152 | B |
| I-153 | A |
| I-154 | B |
| I-155 | A |
| I-156 | A |
| I-157 | A |
| I-158 | A |
| I-159 | B |
| I-160 | A |
| I-161 | A |
| I-162 | A |
| I-163 | B |
| I-164 | A |
| I-165 | A |
| I-166 | A |
| I-167 | A |
| I-168 | B |
| I-169 | B |
| I-170 | A |
| I-171 | B |
| I-172 | B |
| I-173 | B |
| I-174 | A |
| I-175 | A |
| I-176 | A |
| I-177 | A |
| I-178 | B |
| I-179 | B |
| I-180 | A |
| I-181 | B |
| I-182 | A |
| I-183 | A |
| I-184 | B |
| I-185 | B |
| I-186 | A |
| I-187 | A |
| I-188 | A |
| I-189 | A |
| I-190 | A |
| I-191 | A |
| I-192 | A |
| I-193 | B |
| I-194 | A |
| I-195 | B |
| I-196 | B |
| I-197 | B |
| I-198 | A |
| I-199 | B |
| I-200 | B |
| I-201 | A |
| I-202 | B |
| I-203 | A |
| I-204 | B |
| I-205 | A |
| I-206 | C |
| I-207 | C |
| I-208 | C |
| I-209 | B |
| I-210 | B |
| I-211 | B |
| I-212 | B |
| I-213 | C |
| I-214 | A |
| I-215 | A |
| I-216 | A |
| I-217 | A |
| I-218 | A |
| I-219 | A |
| I-220 | A |
| I-221 | C |
| I-222 | B |
| I-223 | A |
| I-224 | A |
| I-225 | A |
| I-226 | C |
| I-227 | B |
| I-228 | C |
| I-229 | B |
| I-230 | B |
| I-231 | B |
| I-232 | A |
| I-233 | A |
| I-234 | A |
| I-235 | A |
| I-236 | A |
| I-237 | A |
| I-238 | A |
| I-239 | A |
| I-240 | A |
| I-241 | A |
| I-242 | A |
| I-243 | B |
| I-244 | A |
| I-245 | A |
| I-246 | A |
| I-247 | B |
| I-248 | B |
| I-249 | A |
| I-250 | A |
| I-251 | A |
| I-252 | C |
| I-253 | B |
| I-254 | B |
| I-255 | A |
| I-256 | B |
| I-257 | B |
| I-258 | A |
| I-259 | A |
| I-260 | B |
| I-261 | B |
| I-262 | A |
| I-263 | A |
| I-264 | B |
| I-265 | A |
| I-266 | A |
| I-267 | A |
| I-268 | A |
| I-269 | A |
| I-270 | B |
| I-271 | B |
| I-272 | A |
| I-273 | C |
| I-274 | A |
| I-275 | A |
| I-276 | A |
| I-277 | B |
| I-278 | B |
| I-279 | A |
| I-280 | A |
| I-281 | B |
| I-282 | B |
| I-283 | A |
| I-284 | A |
| I-285 | A |
| I-286 | B |
| I-287 | C |
| I-288 | A |
| I-289 | A |
| I-290 | B |
| I-291 | B |
| I-292 | B |

TABLE 2-continued

Results of Tyk2 JH2 Domain Binding Assay

| Compound | Tyk2 JH2 Kd |
| --- | --- |
| I-293 | B |
| I-294 | B |
| I-295 | A |
| I-296 | A |
| I-297 | B |
| I-298 | C |
| I-299 | B |
| I-300 | B |
| I-301 | B |
| I-302 | A |
| I-303 | A |
| I-304 | A |
| I-305 | A |
| I-306 | C |
| I-307 | B |
| I-308 | A |
| I-309 | A |
| I-310 | A |
| I-311 | A |
| I-312 | A |
| I-313 | A |
| I-314 | A |
| I-315 | A |
| I-316 | A |
| I-317 | A |
| I-318 | A |
| I-319 | A |
| I-320 | A |
| I-321 | A |
| I-322 | B |
| I-323 | A |
| I-324 | A |
| I-325 | B |
| I-326 | A |
| I-327 | B |
| I-328 | A |
| I-329 | A |
| I-330 | A |
| I-331 | A |
| I-332 | A |
| I-333 | A |
| I-334 | A |
| I-335 | A |
| I-336 | B |
| I-337 | B |
| I-338 | A |
| I-339 | B |
| I-340 | B |
| I-341 | B |
| I-342 | B |
| I-343 | A |
| I-344 | A |
| I-345 | A |
| I-346 | A |
| I-347 | A |
| I-348 | B |
| I-349 | A |
| I-350 | A |
| I-351 | A |
| I-352 | A |
| I-353 | A |
| I-354 | A |
| I-355 | B |
| I-356 | A |
| I-357 | A |
| I-358 | A |
| I-359 | A |
| I-360 | A |
| I-361 | A |
| I-362 | A |
| I-363 | A |
| I-364 | A |
| I-365 | A |
| I-366 | A |
| I-367 | B |
| I-368 | A |
| I-369 | A |
| I-370 | A |
| I-371 | A |
| I-372 | A |
| I-373 | A |
| I-374 | A |
| I-375 | A |
| I-376 | B |
| I-377 | B |
| I-378 | A |
| I-379 | A |
| I-380 | A |
| I-381 | A |
| I-382 | B |
| I-383 | B |
| I-384 | A |
| I-385 | A |
| I-386 | A |
| I-387 | C |
| I-388 | B |
| I-389 | A |
| I-390 | A |
| I-391 | A |
| I-392 | A |
| I-393 | A |
| I-394 | B |
| I-395 | A |
| I-396 | A |
| I-397 | A |
| I-398 | B |
| I-399 | A |
| I-400 | B |
| I-401 | A |
| I-402 | B |
| I-403 | B |
| I-404 | B |
| I-405 | B |
| I-406 | A |
| I-407 | A |
| I-408 | A |
| I-409 | A |
| I-410 | A |
| I-411 | A |
| I-412 | B |
| I-413 | A |
| I-414 | B |
| I-415 | A |
| I-416 | D |
| I-417 | A |
| I-418 | C |
| I-419 | C |
| I-420 | B |
| I-421 | B |
| I-422 | C |
| I-423 | A |
| I-424 | A |
| I-425 | A |
| I-426 | A |
| I-427 | B |
| I-428 | A |
| I-429 | A |
| I-430 | B |
| I-431 | D |
| I-432 | A |
| I-433 | A |
| I-434 | A |
| I-435 | A |
| I-436 | B |
| I-437 | B |
| I-438 | A |
| I-439 | B |
| I-440 | B |
| I-441 | B |
| I-442 | B |
| I-443 | B |
| I-444 | A |

TABLE 2-continued

Results of Tyk2 JH2 Domain Binding Assay

| Compound | Tyk2 JH2 Kd |
|---|---|
| I-445 | B |
| I-446 | B |
| I-447 | A |
| I-448 | A |
| I-449 | B |
| I-450 | B |
| I-451 | A |
| I-452 | A |
| I-453 | B |
| I-454 | A |
| I-455 | C |
| I-456 | C |
| I-457 | C |
| I-458 | B |
| I-459 | A |
| I-460 | A |
| I-461 | A |
| I-462 | A |
| I-463 | B |
| I-464 | B |
| I-465 | B |
| I-466 | B |
| I-467 | B |
| I-468 | B |
| I-469 | C |
| I-470 | A |
| I-471 | B |
| I-472 | B |
| I-473 | B |
| I-474 | A |
| I-475 | A |
| I-476 | A |
| I-477 | B |
| I-478 | B |
| I-479 | C |
| I-480 | B |
| I-481 | B |
| I-482 | B |
| I-483 | A |
| I-484 | A |
| I-485 | B |
| I-486 | B |
| I-487 | A |
| I-488 | A |
| I-489 | A |
| I-490 | A |
| I-491 | C |
| I-492 | A |
| I-493 | B |
| I-494 | B |
| I-495 | B |
| I-496 | A |
| I-497 | A |
| I-498 | A |
| I-499 | A |
| I-500 | A |
| I-501 | A |
| I-502 | B |
| I-503 | B |
| I-504 | B |
| I-505 | B |
| I-506 | A |
| I-507 | B |
| I-508 | B |
| I-509 | A |
| I-510 | A |
| I-511 | B |
| I-512 | A |
| I-513 | A |
| I-514 | C |
| I-515 | B |
| I-516 | C |
| I-517 | B |
| I-518 | B |
| I-519 | A |
| I-520 | B |

TABLE 2-continued

Results of Tyk2 JH2 Domain Binding Assay

| Compound | Tyk2 JH2 Kd |
|---|---|
| I-521 | A |
| I-522 | A |
| I-523 | B |
| I-524 | C |
| I-525 | D |
| I-526 | B |
| I-527 | B |
| I-528 | A |
| I-529 | A |
| I-530 | B |
| I-531 | B |
| I-532 | B |
| I-533 | A |
| I-534 | B |
| I-535 | A |
| I-536 | B |
| I-537 | C |
| I-538 | C |
| I-539 | A |
| I-540 | A |
| I-541 | A |
| I-542 | B |
| I-543 | B |
| I-544 | A |
| I-545 | A |
| I-546 | C |
| I-547 | A |
| I-548 | A |
| I-549 | A |
| I-550 | A |
| I-551 | A |
| I-552 | C |
| I-553 | B |
| I-554 | C |
| I-555 | C |
| I-556 | A |
| I-557 | B |
| I-558 | A |
| I-559 | A |
| I-560 | A |
| I-561 | B |
| I-562 | A |
| I-563 | A |
| I-564 | A |
| I-565 | A |
| I-566 | A |
| I-567 | C |
| I-568 | A |
| I-569 | A |
| I-570 | A |
| I-571 | A |
| I-572 | A |
| I-573 | B |
| I-574 | C |
| I-575 | C |
| I-576 | C |
| I-577 | B |
| I-578 | A |
| I-579 | A |
| I-580 | A |
| I-581 | C |
| I-582 | A |
| I-583 | A |
| I-584 | A |
| I-585 | A |
| I-586 | A |
| I-587 | B |
| I-588 | B |
| I-589 | A |
| I-590 | A |
| I-591 | A |
| I-592 | A |
| I-593 | A |
| I-594 | B |
| I-595 | C |
| I-596 | A |

TABLE 2-continued

Results of Tyk2 JH2 Domain Binding Assay

| Compound | Tyk2 JH2 Kd |
|---|---|
| I-597 | B |
| I-598 | A |
| I-599 | A |
| I-600 | A |
| I-601 | A |
| I-602 | A |
| I-603 | A |
| I-604 | A |
| I-605 | A |
| I-606 | A |
| I-607 | A |
| I-608 | A |
| I-609 | A |
| I-610 | A |
| I-611 | A |
| I-612 | A |
| I-613 | A |
| I-614 | C |
| I-615 | A |
| I-616 | A |
| I-617 | A |
| I-618 | A |
| I-619 | A |
| I-620 | A |
| I-621 | A |
| I-622 | B |
| I-623 | C |
| I-624 | B |
| I-625 | A |
| I-626 | A |
| I-627 | A |
| I-628 | A |
| I-629 | B |
| I-630 | A |
| I-631 | B |
| I-632 | A |
| I-633 | A |
| I-634 | A |
| I-635 | A |
| I-636 | A |
| I-637 | A |
| I-638 | B |
| I-639 | A |
| I-640 | A |
| I-641 | B |
| I-642 | A |
| I-643 | B |
| I-644 | A |
| I-645 | C |
| I-646 | A |
| I-647 | A |
| I-648 | B |
| I-649 | A |
| I-650 | C |
| I-651 | D |
| I-652 | A |
| I-653 | A |
| I-654 | A |
| I-655 | B |
| I-656 | A |
| I-657 | A |
| I-658 | A |
| I-659 | A |
| I-660 | A |
| I-661 | A |
| I-662 | A |
| I-663 | A |
| I-664 | A |
| I-665 | A |
| I-666 | A |
| I-667 | A |
| I-668 | A |
| I-669 | A |
| I-670 | A |
| I-671 | A |
| I-672 | A |
| I-673 | A |
| I-674 | B |
| I-675 | A |
| I-676 | A |
| I-677 | A |
| I-678 | B |
| I-679 | A |
| I-680 | A |
| I-681 | A |
| I-682 | B |
| I-683 | A |
| I-684 | B |
| I-685 | A |
| I-686 | B |
| I-687 | B |
| I-688 | A |
| I-689 | B |
| I-690 | C |
| I-691 | C |
| I-692 | A |
| I-693 | A |
| I-694 | A |
| I-695 | A |
| I-696 | A |
| I-697 | A |
| I-698 | A |
| I-699 | A |
| I-700 | B |
| I-701 | B |
| I-702 | B |
| I-703 | A |
| I-704 | B |
| I-705 | A |
| I-706 | A |
| I-707 | A |
| I-708 | A |
| I-709 | A |
| I-710 | A |
| I-711 | A |
| I-712 | A |
| I-713 | A |
| I-714 | A |
| I-715 | A |
| I-716 | A |
| I-717 | A |
| I-718 | A |
| I-719 | A |
| I-720 | C |
| I-721 | A |
| I-722 | A |
| I-723 | B |
| I-724 | A |
| I-725 | A |
| I-726 | A |
| I-727 | A |
| I-728 | A |
| I-729 | A |
| I-730 | A |
| I-731 | B |
| I-732 | A |
| I-733 | A |
| I-734 | B |
| I-735 | A |
| I-736 | A |
| I-737 | A |
| I-738 | B |
| I-739 | B |
| I-740 | A |
| I-741 | A |
| I-742 | A |
| I-743 | A |
| I-744 | A |
| I-745 | A |
| I-746 | B |
| I-747 | A |
| I-748 | A |

TABLE 2-continued

Results of Tyk2 JH2 Domain Binding Assay

| Compound | Tyk2 JH2 Kd |
|---|---|
| I-749 | A |
| I-750 | A |
| I-751 | A |
| I-752 | B |
| I-753 | B |
| I-754 | A |
| I-755 | A |
| I-756 | A |
| I-757 | A |
| I-758 | B |
| I-759 | A |
| I-760 | A |
| I-761 | B |
| I-762 | A |
| I-763 | A |
| I-764 | A |
| I-765 | A |
| I-766 | A |
| I-767 | A |
| I-768 | A |
| I-769 | A |
| I-770 | A |
| I-771 | B |
| I-772 | A |
| I-773 | A |
| I-774 | C |
| I-775 | A |
| I-776 | A |
| I-777 | A |
| I-778 | A |
| I-779 | B |
| I-780 | A |
| I-781 | A |
| I-782 | A |
| I-783 | A |
| I-784 | D |
| I-785 | A |
| I-786 | A |
| I-787 | D |
| I-788 | A |
| I-789 | A |
| I-790 | A |
| I-791 | B |
| I-792 | A |
| I-793 | A |
| I-794 | A |
| I-795 | A |
| I-796 | A |
| I-797 | A |
| I-798 | A |
| I-799 | B |
| I-800 | B |
| I-801 | B |
| I-802 | A |
| I-803 | A |
| I-804 | B |
| I-805 | A |
| I-806 | B |
| I-807 | B |
| I-808 | A |
| I-809 | B |
| I-810 | A |
| I-811 | A |
| I-812 | C |
| I-813 | B |
| I-814 | A |
| I-815 | A |
| I-816 | A |
| I-817 | A |
| I-818 | B |
| I-819 | A |
| I-820 | A |
| I-821 | A |
| I-822 | A |
| I-823 | B |
| I-824 | B |
| I-825 | A |
| I-826 | A |
| I-827 | A |
| I-828 | A |
| I-829 | A |
| I-830 | A |
| I-831 | A |
| I-832 | C |
| I-833 | D |
| I-834 | A |
| I-835 | A |
| I-836 | B |
| I-837 | A |
| I-838 | A |
| I-839 | A |
| I-840 | A |
| I-841 | C |
| I-842 | A |
| I-843 | A |
| I-844 | A |
| I-845 | A |
| I-846 | A |
| I-847 | A |
| I-848 | A |
| I-849 | A |
| I-850 | C |
| I-851 | A |
| I-852 | A |
| I-853 | A |
| I-854 | A |
| I-855 | C |
| I-856 | B |
| I-857 | A |
| I-858 | A |
| I-859 | A |
| I-860 | A |
| I-861 | A |
| I-862 | B |
| I-863 | A |
| I-864 | A |
| I-865 | A |
| I-866 | A |
| I-867 | A |
| I-868 | A |
| I-869 | A |
| I-870 | A |
| I-871 | B |
| I-872 | A |
| I-873 | C |
| I-874 | C |
| I-875 | A |
| I-876 | C |
| I-877 | A |
| I-878 | A |
| I-879 | C |
| I-880 | A |
| I-881 | B |
| I-882 | A |
| I-883 | A |
| I-884 | A |
| I-885 | A |
| I-886 | A |
| I-887 | A |
| I-888 | A |
| I-889 | C |
| I-890 | A |
| I-891 | A |
| I-892 | A |
| I-893 | C |
| I-894 | A |
| I-895 | A |
| I-896 | A |
| I-897 | B |
| I-898 | A |
| I-899 | A |
| I-900 | A |

TABLE 2-continued

Results of Tyk2 JH2 Domain Binding Assay

| Compound | Tyk2 JH2 Kd |
|---|---|
| I-901 | B |
| I-902 | A |
| I-903 | B |
| I-904 | A |
| I-905 | A |
| I-906 | A |
| I-907 | B |
| I-908 | A |
| I-909 | A |
| I-910 | A |
| I-911 | C |
| I-912 | B |
| I-913 | B |
| I-914 | A |
| I-915 | C |
| I-916 | A |
| I-917 | A |
| I-918 | A |
| I-919 | A |
| I-920 | A |
| I-921 | B |
| I-922 | A |
| I-923 | B |
| I-924 | A |
| I-925 | C |
| I-926 | A |
| I-927 | B |
| I-928 | B |
| I-929 | A |
| I-930 | A |
| I-931 | A |
| I-932 | B |
| I-933 | A |
| I-934 | A |
| I-935 | A |
| I-936 | B |
| I-937 | C |
| I-938 | B |
| I-939 | A |
| I-940 | A |
| I-941 | A |
| I-942 | A |
| I-943 | A |
| I-944 | A |
| I-945 | A |
| I-946 | A |
| I-947 | A |
| I-948 | A |
| I-949 | C |
| I-950 | B |
| I-951 | A |
| I-952 | A |
| I-953 | B |
| I-954 | A |
| I-955 | A |
| I-956 | A |
| I-957 | A |
| I-958 | A |
| I-959 | A |
| I-960 | A |
| I-961 | A |
| I-962 | A |
| I-963 | A |
| I-964 | C |
| I-965 | A |
| I-966 | B |
| I-967 | A |
| I-968 | A |
| I-969 | A |
| I-970 | A |
| I-971 | A |
| I-972 | B |
| I-973 | A |
| I-974 | B |
| I-975 | A |
| I-976 | B |
| I-977 | A |
| I-978 | B |
| I-979 | B |
| I-980 | A |
| I-981 | A |
| I-982 | B |
| I-983 | A |
| I-984 | A |
| I-985 | B |
| I-986 | A |
| I-987 | A |
| I-988 | A |
| I-989 | D |
| I-990 | C |
| I-991 | C |
| I-992 | A |
| I-993 | A |
| I-994 | A |
| I-995 | A |
| I-996 | A |
| I-997 | A |
| I-998 | A |
| I-999 | A |
| I-1000 | A |
| I-1001 | C |
| I-1002 | A |
| I-1003 | B |
| I-1004 | A |
| I-1005 | B |
| I-1006 | A |
| I-1007 | B |
| I-1008 | A |
| I-1009 | B |
| I-1010 | A |
| I-1011 | B |
| I-1012 | B |
| I-1013 | A |
| I-1014 | A |
| I-1015 | C |
| I-1016 | C |
| I-1017 | A |
| I-1018 | C |
| I-1019 | B |
| I-1020 | B |
| I-1021 | A |
| I-1022 | A |
| I-1023 | A |
| I-1024 | A |
| I-1025 | A |
| I-1026 | A |
| I-1027 | A |
| I-1028 | B |
| I-1029 | A |
| I-1030 | A |
| I-1031 | A |
| I-1032 | B |
| I-1033 | A |
| I-1034 | A |
| I-1035 | A |
| I-1036 | B |
| I-1037 | B |
| I-1038 | A |
| I-1039 | A |
| I-1040 | B |
| I-1041 | B |
| I-1042 | A |
| I-1043 | B |
| I-1044 | B |
| I-1045 | B |
| I-1046 | A |
| I-1047 | B |
| I-1048 | A |
| I-1049 | A |
| I-1050 | A |
| I-1051 | A |
| I-1052 | A |

TABLE 2-continued

Results of Tyk2 JH2 Domain Binding Assay

| Compound | Tyk2 JH2 Kd |
|---|---|
| I-1053 | A |
| I-1054 | A |
| I-1055 | B |
| I-1056 | B |
| I-1057 | A |
| I-1058 | B |
| I-1059 | A |
| I-1060 | A |
| I-1061 | A |
| I-1062 | A |
| I-1063 | A |
| I-1064 | A |
| I-1065 | A |
| I-1066 | A |
| I-1067 | A |
| I-1068 | A |
| I-1069 | B |
| I-1070 | A |
| I-1071 | C |
| I-1072 | A |
| I-1073 | A |
| I-1074 | A |
| I-1075 | A |
| I-1076 | A |
| I-1077 | B |
| I-1078 | A |
| I-1079 | B |
| I-1080 | A |
| I-1081 | B |
| I-1082 | A |
| I-1083 | C |
| I-1084 | A |
| I-1085 | A |
| I-1086 | A |
| I-1087 | A |
| I-1088 | A |
| I-1089 | A |
| I-1090 | A |
| I-1091 | A |
| I-1092 | B |
| I-1093 | A |
| I-1094 | A |
| I-1095 | A |
| I-1096 | A |
| I-1097 | A |
| I-1098 | A |
| I-1099 | A |
| I-1100 | B |
| I-1101 | A |
| I-1102 | A |
| I-1103 | C |
| I-1104 | A |
| I-1105 | A |
| I-1106 | C |
| I-1107 | A |
| I-1108 | A |
| I-1109 | A |
| I-1110 | A |
| I-1111 | A |
| I-1112 | B |
| I-1113 | A |
| I-1114 | B |
| I-1115 | C |
| I-1116 | D |
| I-1117 | A |
| I-1118 | B |
| I-1119 | A |
| I-1120 | B |
| I-1121 | A |
| I-1122 | B |
| I-1123 | A |
| I-1124 | A |
| I-1125 | D |
| I-1126 | A |
| I-1127 | D |
| I-1128 | C |
| I-1129 | C |
| I-1130 | A |
| I-1131 | A |
| I-1132 | A |
| I-1133 | C |
| I-1183 | B |
| I-1184 | A |
| I-1185 | C |
| I-1186 | A |
| I-1187 | A |
| I-1188 | C |
| I-1189 | A |
| I-1190 | A |
| I-1191 | A |
| I-1192 | A |
| I-1193 | A |
| I-1194 | A |
| I-1195 | C |
| I-1196 | B |
| I-1197 | A |
| I-1198 | A |
| I-1199 | B |
| I-1200 | B |
| I-1201 | B |
| I-1202 | C |
| I-1203 | A |
| I-1204 | A |
| I-1205 | A |
| I-1206 | C |
| I-1207 | A |
| I-1208 | C |
| I-1209 | A |
| I-1210 | B |
| I-1211 | A |
| I-1212 | D |
| I-1213 | A |
| I-1214 | A |
| I-1215 | A |
| I-1216 | B |
| I-1217 | A |
| I-1218 | C |
| I-1219 | A |
| I-1220 | B |
| I-1221 | B |
| I-1222 | A |
| I-1223 | B |
| I-1224 | C |
| I-1225 | A |
| I-1226 | C |
| I-1227 | A |
| I-1228 | C |
| I-1229 | A |
| I-1230 | B |
| I-1231 | A |
| I-1232 | B |
| I-1233 | C |
| I-1234 | B |
| I-1235 | A |
| I-1236 | A |
| I-1237 | D |
| I-1238 | A |
| I-1239 | A |
| I-1240 | A |
| I-1241 | A |
| I-1242 | A |
| I-1243 | C |
| I-1244 | A |
| I-1245 | B |
| I-1246 | B |
| I-1247 | A |
| I-1248 | A |
| I-1249 | A |
| I-1250 | B |
| I-1251 | C |
| I-1252 | A |
| I-1253 | D |

TABLE 2-continued

Results of Tyk2 JH2 Domain Binding Assay

| Compound | Tyk2 JH2 Kd |
|---|---|
| I-1254 | B |
| I-1255 | B |
| I-1256 | A |
| I-1257 | A |
| I-1258 | D |
| I-1259 | D |
| I-1260 | B |
| I-1261 | B |
| I-1262 | C |
| I-1263 | A |
| I-1264 | C |
| I-1265 | C |
| I-1266 | A |
| I-1267 | A |
| I-1268 | D |
| I-1269 | B |
| I-1270 | C |
| I-1271 | A |
| I-1272 | C |
| I-1273 | D |
| I-1274 | A |
| I-1275 | A |
| I-1276 | B |
| I-1277 | A |
| I-1278 | B |
| I-1279 | A |
| I-1280 | A |
| I-1281 | B |
| I-1282 | C |
| I-1283 | C |
| I-1284 | B |
| I-1285 | A |
| I-1286 | A |
| I-1287 | A |
| I-1288 | A |
| I-1289 | C |
| I-1290 | D |
| I-1291 | C |
| I-1292 | A |
| I-1293 | A |
| I-1294 | A |
| I-1295 | A |
| I-1296 | A |
| I-1297 | B |
| I-1298 | D |
| I-1299 | A |
| I-1300 | C |
| I-1301 | B |
| I-1302 | A |
| I-1303 | C |
| I-1304 | B |
| I-1305 | B |
| I-1306 | C |
| I-1307 | A |
| I-1308 | D |
| I-1309 | A |
| I-1310 | A |
| I-1311 | A |
| I-1312 | D |
| I-1313 | D |
| I-1314 | A |
| I-1315 | A |
| I-1316 | C |
| I-1317 | A |
| I-1318 | A |
| I-1319 | C |
| I-1320 | C |
| I-1321 | A |
| I-1322 | A |
| I-1323 | C |
| I-1324 | A |
| I-1325 | A |
| I-1326 | A |
| I-1327 | A |
| I-1328 | B |
| I-1329 | D |
| I-1330 | A |
| I-1331 | C |
| I-1332 | C |
| I-1333 | C |
| I-1334 | A |
| I-1335 | A |
| I-1336 | C |
| I-1337 | A |
| I-1338 | B |
| I-1339 | B |
| I-1340 | C |
| I-1341 | D |
| I-1342 | A |
| I-1343 | A |
| I-1344 | B |
| I-1345 | A |
| I-1346 | A |
| I-1347 | C |
| I-1348 | A |
| I-1349 | C |
| I-1350 | A |
| I-1351 | A |
| I-1352 | A |
| I-1353 | C |
| I-1354 | B |
| I-1355 | C |
| I-1356 | A |
| I-1357 | D |
| I-1358 | A |
| I-1359 | A |
| I-1360 | A |
| I-1361 | B |
| I-1362 | B |
| I-1363 | B |
| I-1364 | B |
| I-1365 | A |
| I-1366 | C |
| I-1367 | A |
| I-1368 | A |
| I-1369 | A |
| I-1370 | C |
| I-1371 | A |
| I-1372 | B |
| I-1373 | A |
| I-1374 | B |
| I-1375 | C |
| I-1376 | D |
| I-1377 | A |
| I-1378 | C |
| I-1379 | C |
| I-1380 | A |
| I-1381 | B |
| I-1382 | A |
| I-1383 | C |
| I-1384 | B |
| I-1385 | B |
| I-1386 | C |
| I-1387 | C |
| I-1388 | B |
| I-1389 | B |
| I-1390 | C |
| I-1391 | A |
| I-1392 | B |
| I-1393 | A |
| I-1394 | A |
| I-1395 | B |
| I-1396 | B |
| I-1397 | B |
| I-1398 | C |
| I-1399 | C |
| I-1400 | A |
| I-1401 | A |
| I-1402 | C |
| I-1403 | B |
| I-1404 | A |
| I-1405 | C |

TABLE 2-continued

Results of Tyk2 JH2 Domain Binding Assay

| Compound | Tyk2 JH2 Kd |
|---|---|
| I-1406 | D |
| I-1407 | A |
| I-1408 | B |
| I-1409 | B |
| I-1410 | A |
| I-1411 | C |
| I-1412 | B |
| I-1413 | C |
| I-1414 | D |
| I-1415 | B |

Example 4. Tyk2 & JAK2 Radioactive Kinase Assay

Peptide substrate, [KKSRGDYMTMQIG], (20 μM) is prepared in reaction buffer (20 mM Hepes pH 7.5, 10 mM $MgCl_2$, 1 mM EGTA, 0.02% Brij35, 0.02 mg/mL BSA, 0.1 mM $Na_3PO_4$, 2 mM DTT, 1% DMSO. TYK2 (Invitrogen) kinase is added, followed by compounds in DMSO. 33PATP is added to initiate the reaction in ATP at 10 μM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu: Tyr](4:1), 0.2 mg/ml is used, in the reaction carried out the same as for TYK2.

The Tyk2 and JAK2 radioactive kinase assay measures the percent inhibition at the Tyk2 kinase domain (JH1) and the percent inhibition at the JAK2 kinase domain (JH1). Results of the assay are expressed as percent inhibition at 10 μM.

Results of the Tyk2 and JAK2 Radioactive Kinase Assay are presented in Table 3. Compounds denoted as "A" had a percent inhibition at 10 μM lower than 50; compounds denoted as "B" had a percent inhibition at 10 μM between 50 and 70; compounds denoted as "C" had a percent inhibition at 10 μM between 70 and 90; and compounds denoted as "D" had a percent inhibition at 10 μM greater than 90.

TABLE 3

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-1 | A | A |
| I-2 | A | A |
| I-3 | A | A |
| I-4 | A | A |
| I-5 | A | A |
| I-6 | A | A |
| I-7 | A | A |
| I-8 | A | A |
| I-9 | A | A |
| I-10 | A | A |
| I-11 | A | A |
| I-12 | A | A |
| I-15 | A | A |
| I-16 | D | C |
| I-17 | C | A |
| I-18 | A | A |
| I-19 | A | A |
| I-20 | A | A |
| I-21 | A | C |
| I-22 | A | C |
| I-23 | A | C |
| I-24 | A | A |
| I-25 | A | A |
| I-26 | A | A |
| I-27 | A | A |
| I-28 | A | A |
| I-29 | A | A |
| I-30 | A | A |
| I-31 | A | A |
| I-32 | A | A |
| I-33 | A | A |
| I-34 | A | A |
| I-35 | A | A |
| I-36 | A | A |
| I-37 | A | A |
| I-38 | A | A |
| I-39 | A | A |
| I-40 | A | A |
| I-41 | A | A |
| I-42 | A | A |
| I-43 | A | A |
| I-44 | A | A |
| I-45 | A | A |
| I-46 | A | A |
| I-47 | A | A |
| I-48 | A | A |
| I-49 | A | A |
| I-50 | A | A |
| I-51 | A | A |
| I-52 | A | A |
| I-53 | A | A |
| I-54 | A | A |
| I-55 | A | A |
| I-56 | A | A |
| I-57 | A | A |
| I-58 | A | B |
| I-59 | A | A |
| I-60 | A | A |
| I-61 | A | A |
| I-62 | A | A |
| I-63 | A | A |
| I-64 | A | A |
| I-65 | A | A |
| I-66 | A | B |
| I-67 | A | A |
| I-68 | A | A |
| I-69 | A | A |
| I-70 | A | A |
| I-71 | A | A |
| I-72 | A | A |
| I-73 | A | A |
| I-74 | A | A |
| I-75 | A | A |
| I-76 | A | A |
| I-77 | A | A |
| I-78 | A | A |
| I-79 | A | A |
| I-80 | A | A |
| I-81 | A | A |
| I-82 | A | A |
| I-83 | A | A |
| I-89 | A | A |
| I-90 | A | A |
| I-91 | A | A |
| I-92 | A | A |
| I-93 | A | A |
| I-94 | A | A |
| I-95 | A | A |
| I-96 | A | A |
| I-97 | A | A |
| I-98 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-99 | A | A |
| I-100 | A | A |
| I-101 | A | A |
| I-102 | C | D |
| I-103 | A | A |
| I-104 | A | A |
| I-105 | A | B |
| I-106 | A | A |
| I-107 | A | A |
| I-108 | A | A |
| I-109 | A | A |
| I-110 | A | A |
| I-111 | A | A |
| I-112 | A | A |
| I-113 | D | D |
| I-114 | A | A |
| I-115 | A | A |
| I-116 | A | A |
| I-117 | A | A |
| I-118 | A | A |
| I-119 | A | A |
| I-120 | A | A |
| I-121 | A | A |
| I-122 | A | A |
| I-123 | A | A |
| I-124 | A | A |
| I-125 | A | A |
| I-126 | A | A |
| I-127 | A | A |
| I-128 | A | A |
| I-129 | A | A |
| I-130 | A | A |
| I-131 | A | A |
| I-132 | A | A |
| I-133 | A | A |
| I-134 | A | A |
| I-135 | A | A |
| I-136 | A | A |
| I-137 | A | A |
| I-138 | A | A |
| I-139 | A | A |
| I-140 | A | A |
| I-141 | A | A |
| I-142 | A | A |
| I-143 | A | A |
| I-144 | A | A |
| I-145 | A | A |
| I-146 | A | A |
| I-147 | A | A |
| I-148 | A | A |
| I-149 | A | A |
| I-150 | A | A |
| I-151 | A | A |
| I-152 | A | A |
| I-153 | A | B |
| I-154 | A | B |
| I-155 | A | A |
| I-156 | A | A |
| I-157 | A | A |
| I-158 | A | A |
| I-159 | A | A |
| I-160 | A | A |
| I-161 | A | A |
| I-162 | A | A |
| I-163 | A | A |
| I-164 | A | A |
| I-165 | A | A |
| I-166 | A | A |
| I-167 | A | A |
| I-168 | A | A |
| I-169 | A | A |
| I-170 | A | A |
| I-171 | A | A |
| I-172 | A | A |
| I-173 | A | A |
| I-174 | A | A |
| I-175 | A | A |
| I-176 | A | A |
| I-177 | A | A |
| I-178 | A | A |
| I-179 | A | A |
| I-180 | A | A |
| I-181 | A | A |
| I-182 | A | A |
| I-183 | A | A |
| I-184 | A | A |
| I-185 | A | A |
| I-186 | A | A |
| I-187 | A | A |
| I-188 | A | A |
| I-189 | A | A |
| I-190 | A | A |
| I-191 | A | A |
| I-192 | A | A |
| I-193 | A | A |
| I-194 | A | A |
| I-195 | A | A |
| I-196 | A | A |
| I-197 | A | A |
| I-198 | A | A |
| I-199 | A | A |
| I-200 | A | A |
| I-201 | A | A |
| I-202 | A | A |
| I-203 | A | A |
| I-204 | A | A |
| I-205 | A | A |
| I-206 | A | A |
| I-207 | A | A |
| I-208 | A | A |
| I-209 | A | A |
| I-210 | A | A |
| I-211 | A | A |
| I-212 | A | A |
| I-213 | A | A |
| I-214 | A | A |
| I-215 | A | A |
| I-216 | A | A |
| I-217 | A | A |
| I-218 | A | A |
| I-219 | A | A |
| I-220 | A | A |
| I-221 | A | A |
| I-222 | A | A |
| I-223 | A | A |
| I-224 | A | A |
| I-225 | A | A |
| I-226 | A | A |
| I-227 | A | A |
| I-228 | A | A |
| I-229 | A | A |
| I-230 | A | A |
| I-231 | A | A |
| I-232 | A | A |
| I-233 | A | A |
| I-234 | A | A |
| I-235 | A | A |
| I-236 | A | A |
| I-237 | A | A |
| I-238 | A | A |
| I-239 | A | A |
| I-240 | A | A |
| I-241 | A | A |
| I-242 | A | A |
| I-243 | A | A |
| I-244 | A | A |
| I-245 | A | A |
| I-246 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-247 | A | A |
| I-248 | A | A |
| I-249 | A | A |
| I-250 | A | A |
| I-251 | A | A |
| I-252 | A | A |
| I-253 | A | A |
| I-254 | A | A |
| I-255 | A | A |
| I-256 | A | A |
| I-257 | A | A |
| I-258 | A | A |
| I-259 | A | A |
| I-260 | A | A |
| I-261 | A | A |
| I-262 | A | A |
| I-263 | A | A |
| I-264 | A | A |
| I-265 | A | A |
| I-266 | A | A |
| I-267 | A | A |
| I-268 | A | A |
| I-269 | A | A |
| I-270 | A | A |
| I-271 | A | A |
| I-272 | A | A |
| I-273 | A | A |
| I-274 | A | A |
| I-275 | A | A |
| I-276 | A | A |
| I-277 | A | A |
| I-278 | A | A |
| I-279 | A | A |
| I-280 | A | A |
| I-281 | A | A |
| I-282 | A | A |
| I-283 | A | A |
| I-284 | A | A |
| I-285 | A | A |
| I-286 | A | A |
| I-287 | A | A |
| I-288 | A | A |
| I-289 | A | A |
| I-290 | A | A |
| I-291 | A | A |
| I-292 | A | A |
| I-293 | A | A |
| I-294 | A | A |
| I-295 | A | A |
| I-296 | A | A |
| I-297 | A | A |
| I-298 | A | A |
| I-299 | A | A |
| I-300 | A | A |
| I-301 | A | A |
| I-302 | A | A |
| I-303 | A | A |
| I-304 | A | A |
| I-305 | A | A |
| I-306 | A | A |
| I-307 | A | A |
| I-308 | A | A |
| I-309 | A | A |
| I-310 | A | A |
| I-311 | A | A |
| I-312 | A | A |
| I-313 | A | A |
| I-314 | A | A |
| I-315 | A | A |
| I-316 | A | A |
| I-317 | A | A |
| I-318 | A | A |
| I-319 | A | A |
| I-320 | A | B |
| I-321 | A | A |
| I-322 | A | A |
| I-323 | A | A |
| I-324 | A | A |
| I-325 | A | A |
| I-326 | A | A |
| I-327 | A | A |
| I-328 | A | A |
| I-329 | A | A |
| I-330 | A | A |
| I-331 | A | A |
| I-332 | A | A |
| I-333 | A | A |
| I-334 | A | A |
| I-335 | A | A |
| I-336 | A | A |
| I-337 | A | A |
| I-338 | A | A |
| I-339 | A | A |
| I-340 | A | A |
| I-341 | A | A |
| I-342 | A | A |
| I-343 | A | A |
| I-344 | A | A |
| I-345 | A | A |
| I-346 | A | A |
| I-347 | A | A |
| I-348 | A | A |
| I-349 | A | A |
| I-350 | A | A |
| I-351 | A | A |
| I-352 | A | A |
| I-353 | A | A |
| I-354 | A | A |
| I-355 | A | A |
| I-356 | A | A |
| I-357 | A | A |
| I-358 | A | A |
| I-359 | A | A |
| I-360 | A | A |
| I-361 | A | A |
| I-362 | A | A |
| I-363 | A | B |
| I-364 | A | A |
| I-365 | A | A |
| I-366 | A | A |
| I-367 | A | A |
| I-368 | A | A |
| I-369 | A | A |
| I-370 | A | A |
| I-371 | A | A |
| I-372 | A | A |
| I-373 | A | A |
| I-374 | A | A |
| I-375 | A | B |
| I-376 | A | A |
| I-377 | A | A |
| I-378 | A | A |
| I-379 | A | A |
| I-380 | A | A |
| I-381 | A | A |
| I-382 | A | A |
| I-383 | A | A |
| I-384 | A | A |
| I-385 | A | A |
| I-386 | A | A |
| I-387 | A | A |
| I-388 | A | A |
| I-389 | A | A |
| I-390 | A | A |
| I-391 | A | A |
| I-392 | A | A |
| I-393 | A | A |
| I-394 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-395 | A | A |
| I-396 | A | A |
| I-397 | A | A |
| I-398 | A | A |
| I-399 | A | A |
| I-400 | A | A |
| I-401 | A | A |
| I-402 | A | A |
| I-403 | A | A |
| I-404 | A | A |
| I-405 | A | A |
| I-406 | A | A |
| I-407 | A | A |
| I-408 | A | A |
| I-409 | A | A |
| I-410 | A | B |
| I-411 | A | A |
| I-412 | A | A |
| I-413 | A | A |
| I-414 | A | A |
| I-415 | A | A |
| I-416 | A | A |
| I-417 | A | A |
| I-418 | A | A |
| I-419 | A | A |
| I-420 | A | A |
| I-421 | A | A |
| I-422 | A | A |
| I-423 | A | A |
| I-424 | A | A |
| I-425 | A | A |
| I-426 | A | A |
| I-427 | A | A |
| I-428 | A | A |
| I-429 | A | A |
| I-430 | A | A |
| I-431 | A | A |
| I-432 | A | A |
| I-433 | A | B |
| I-434 | A | A |
| I-435 | A | A |
| I-436 | A | A |
| I-437 | A | A |
| I-438 | A | A |
| I-439 | A | A |
| I-440 | A | A |
| I-441 | A | A |
| I-442 | A | A |
| I-443 | A | A |
| I-444 | A | A |
| I-445 | A | A |
| I-446 | A | A |
| I-447 | A | A |
| I-448 | A | A |
| I-449 | A | A |
| I-450 | A | A |
| I-451 | A | A |
| I-452 | A | A |
| I-453 | A | A |
| I-454 | A | A |
| I-455 | A | A |
| I-456 | A | A |
| I-457 | A | A |
| I-458 | A | A |
| I-459 | A | A |
| I-460 | A | A |
| I-461 | A | A |
| I-462 | A | A |
| I-463 | A | B |
| I-464 | A | A |
| I-465 | A | A |
| I-466 | A | A |
| I-467 | A | A |
| I-468 | A | A |
| I-469 | A | A |
| I-470 | A | A |
| I-471 | A | A |
| I-472 | A | A |
| I-473 | A | A |
| I-474 | A | A |
| I-475 | A | A |
| I-476 | A | A |
| I-477 | A | A |
| I-478 | A | A |
| I-479 | A | A |
| I-480 | A | A |
| I-481 | A | A |
| I-482 | A | A |
| I-483 | A | A |
| I-484 | A | A |
| I-485 | A | A |
| I-486 | A | A |
| I-487 | A | A |
| I-488 | A | A |
| I-489 | A | A |
| I-490 | A | A |
| I-491 | A | A |
| I-492 | A | A |
| I-493 | A | A |
| I-494 | A | A |
| I-495 | A | A |
| I-496 | A | A |
| I-497 | A | A |
| I-498 | A | A |
| I-499 | A | A |
| I-500 | A | A |
| I-501 | A | A |
| I-502 | A | A |
| I-503 | A | A |
| I-504 | A | A |
| I-505 | A | A |
| I-506 | A | A |
| I-507 | A | A |
| I-508 | A | A |
| I-509 | A | A |
| I-510 | A | A |
| I-511 | A | A |
| I-512 | A | A |
| I-513 | A | A |
| I-514 | A | A |
| I-515 | A | A |
| I-516 | A | A |
| I-517 | A | A |
| I-518 | A | A |
| I-526 | A | A |
| I-527 | A | A |
| I-528 | A | A |
| I-529 | A | A |
| I-530 | A | A |
| I-531 | A | A |
| I-532 | A | A |
| I-533 | A | A |
| I-534 | A | A |
| I-535 | A | A |
| I-536 | A | A |
| I-537 | A | A |
| I-538 | A | A |
| I-539 | A | A |
| I-540 | A | A |
| I-541 | A | A |
| I-542 | A | A |
| I-543 | A | A |
| I-544 | A | A |
| I-545 | A | A |
| I-546 | A | A |
| I-547 | A | A |
| I-548 | A | B |
| I-549 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-550 | A | A |
| I-551 | A | A |
| I-552 | A | A |
| I-553 | A | A |
| I-554 | A | A |
| I-555 | A | A |
| I-556 | A | A |
| I-557 | A | A |
| I-558 | A | A |
| I-559 | A | A |
| I-560 | A | A |
| I-561 | A | A |
| I-562 | A | B |
| I-563 | A | A |
| I-564 | A | A |
| I-565 | A | A |
| I-566 | A | A |
| I-567 | A | A |
| I-568 | A | A |
| I-569 | A | A |
| I-570 | A | A |
| I-571 | A | A |
| I-572 | A | A |
| I-573 | A | A |
| I-574 | A | A |
| I-575 | A | A |
| I-576 | A | A |
| I-577 | A | A |
| I-578 | A | A |
| I-579 | A | A |
| I-580 | A | A |
| I-581 | A | A |
| I-582 | A | A |
| I-583 | A | A |
| I-584 | A | A |
| I-585 | A | A |
| I-586 | A | A |
| I-587 | A | A |
| I-588 | A | A |
| I-589 | A | A |
| I-590 | A | B |
| I-591 | A | A |
| I-592 | A | A |
| I-593 | A | A |
| I-594 | A | A |
| I-595 | A | A |
| I-596 | A | A |
| I-597 | A | A |
| I-598 | B | A |
| I-599 | A | A |
| I-600 | A | A |
| I-601 | A | A |
| I-602 | A | A |
| I-603 | B | B |
| I-604 | A | A |
| I-605 | A | A |
| I-606 | A | A |
| I-607 | A | A |
| I-608 | A | A |
| I-609 | A | A |
| I-610 | A | A |
| I-611 | A | A |
| I-612 | A | A |
| I-613 | A | A |
| I-614 | A | A |
| I-615 | A | A |
| I-616 | A | A |
| I-617 | A | A |
| I-618 | A | A |
| I-619 | A | A |
| I-620 | A | A |
| I-621 | A | A |
| I-622 | A | A |
| I-623 | A | A |
| I-624 | C | A |
| I-625 | A | A |
| I-626 | A | A |
| I-627 | A | A |
| I-628 | A | A |
| I-629 | A | A |
| I-630 | A | A |
| I-631 | A | A |
| I-632 | A | A |
| I-633 | A | A |
| I-634 | A | A |
| I-635 | A | A |
| I-636 | A | A |
| I-637 | A | A |
| I-638 | A | A |
| I-639 | A | A |
| I-640 | A | A |
| I-641 | A | A |
| I-642 | A | A |
| I-643 | A | A |
| I-644 | A | A |
| I-645 | A | A |
| I-646 | A | A |
| I-647 | A | A |
| I-648 | A | A |
| I-649 | A | A |
| I-650 | A | A |
| I-651 | A | A |
| I-652 | A | A |
| I-653 | A | A |
| I-654 | A | A |
| I-655 | A | A |
| I-656 | A | A |
| I-657 | A | A |
| I-658 | A | A |
| I-659 | A | A |
| I-660 | A | A |
| I-661 | A | A |
| I-662 | A | A |
| I-663 | A | A |
| I-664 | A | A |
| I-665 | A | B |
| I-666 | A | A |
| I-667 | A | A |
| I-668 | A | A |
| I-669 | A | A |
| I-670 | A | A |
| I-671 | A | A |
| I-672 | A | A |
| I-673 | A | A |
| I-674 | A | A |
| I-675 | A | A |
| I-676 | A | A |
| I-677 | A | A |
| I-678 | A | A |
| I-679 | A | A |
| I-680 | A | A |
| I-681 | A | A |
| I-682 | A | A |
| I-683 | A | A |
| I-684 | A | A |
| I-685 | A | A |
| I-686 | A | A |
| I-687 | A | A |
| I-688 | A | A |
| I-689 | A | A |
| I-690 | A | A |
| I-691 | A | A |
| I-692 | A | A |
| I-693 | A | A |
| I-694 | A | A |
| I-695 | A | A |
| I-696 | A | A |
| I-697 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-698 | A | A |
| I-699 | A | A |
| I-700 | A | A |
| I-701 | A | A |
| I-702 | A | A |
| I-703 | A | A |
| I-704 | A | A |
| I-705 | A | A |
| I-706 | A | A |
| I-707 | A | A |
| I-708 | A | A |
| I-709 | A | A |
| I-710 | A | A |
| I-711 | A | A |
| I-712 | A | A |
| I-713 | A | A |
| I-714 | A | A |
| I-715 | A | A |
| I-716 | A | A |
| I-717 | A | A |
| I-718 | A | A |
| I-719 | A | A |
| I-720 | A | A |
| I-721 | A | A |
| I-722 | A | A |
| I-723 | A | A |
| I-724 | A | A |
| I-725 | A | A |
| I-726 | A | A |
| I-727 | A | A |
| I-728 | A | A |
| I-729 | A | A |
| I-730 | A | A |
| I-731 | A | A |
| I-732 | A | A |
| I-733 | A | A |
| I-734 | A | A |
| I-735 | A | A |
| I-736 | A | A |
| I-737 | A | A |
| I-738 | A | A |
| I-739 | A | A |
| I-740 | A | A |
| I-741 | A | A |
| I-742 | A | A |
| I-743 | A | A |
| I-744 | A | A |
| I-745 | A | A |
| I-746 | A | A |
| I-747 | A | A |
| I-748 | A | A |
| I-749 | A | A |
| I-750 | A | A |
| I-751 | A | A |
| I-752 | A | A |
| I-753 | A | A |
| I-754 | A | A |
| I-755 | A | A |
| I-756 | A | A |
| I-757 | A | A |
| I-758 | A | A |
| I-759 | A | A |
| I-760 | A | A |
| I-761 | A | A |
| I-762 | A | A |
| I-763 | A | A |
| I-764 | A | A |
| I-765 | A | A |
| I-766 | A | A |
| I-767 | A | A |
| I-768 | A | A |
| I-769 | A | A |
| I-770 | A | A |
| I-771 | A | A |
| I-772 | A | A |
| I-773 | A | A |
| I-774 | A | A |
| I-775 | A | A |
| I-776 | A | A |
| I-777 | A | A |
| I-778 | A | A |
| I-779 | A | A |
| I-780 | A | A |
| I-781 | A | A |
| I-782 | A | A |
| I-783 | A | A |
| I-784 | A | A |
| I-785 | A | A |
| I-786 | A | A |
| I-787 | A | A |
| I-788 | A | A |
| I-789 | A | A |
| I-790 | A | A |
| I-791 | A | A |
| I-792 | A | A |
| I-793 | A | A |
| I-794 | A | A |
| I-795 | A | A |
| I-796 | A | A |
| I-797 | A | A |
| I-798 | A | A |
| I-799 | A | A |
| I-800 | A | A |
| I-801 | A | A |
| I-802 | A | A |
| I-803 | A | A |
| I-804 | A | A |
| I-805 | A | A |
| I-806 | A | A |
| I-807 | A | A |
| I-808 | A | A |
| I-809 | A | A |
| I-810 | A | A |
| I-811 | A | A |
| I-812 | A | A |
| I-813 | A | A |
| I-814 | A | A |
| I-815 | A | A |
| I-816 | A | A |
| I-817 | A | A |
| I-818 | A | A |
| I-819 | A | A |
| I-820 | A | A |
| I-821 | A | A |
| I-822 | A | A |
| I-823 | A | A |
| I-824 | A | A |
| I-825 | A | A |
| I-826 | A | A |
| I-827 | A | A |
| I-828 | A | A |
| I-829 | A | A |
| I-830 | A | A |
| I-831 | A | A |
| I-832 | A | A |
| I-833 | A | A |
| I-834 | A | A |
| I-835 | A | A |
| I-836 | A | A |
| I-837 | A | A |
| I-838 | A | A |
| I-839 | A | A |
| I-840 | A | A |
| I-841 | A | A |
| I-842 | A | A |
| I-843 | A | A |
| I-844 | A | A |
| I-845 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-846 | A | A |
| I-847 | A | A |
| I-848 | A | A |
| I-849 | A | A |
| I-850 | A | A |
| I-851 | A | A |
| I-852 | A | A |
| I-853 | A | A |
| I-854 | A | A |
| I-855 | A | A |
| I-856 | A | A |
| I-857 | A | A |
| I-858 | A | A |
| I-859 | A | A |
| I-860 | A | A |
| I-861 | A | A |
| I-862 | A | A |
| I-863 | A | A |
| I-864 | A | A |
| I-865 | A | A |
| I-866 | A | A |
| I-867 | A | A |
| I-868 | A | A |
| I-869 | A | A |
| I-870 | A | A |
| I-871 | A | A |
| I-872 | A | A |
| I-873 | A | A |
| I-874 | A | A |
| I-875 | A | A |
| I-876 | A | A |
| I-877 | A | A |
| I-878 | A | A |
| I-879 | A | A |
| I-880 | A | A |
| I-881 | A | A |
| I-882 | A | A |
| I-883 | A | A |
| I-884 | A | A |
| I-885 | A | A |
| I-886 | A | A |
| I-887 | A | A |
| I-888 | A | A |
| I-889 | A | A |
| I-890 | A | A |
| I-891 | A | A |
| I-892 | A | A |
| I-893 | A | A |
| I-894 | A | A |
| I-895 | A | A |
| I-896 | A | A |
| I-897 | A | A |
| I-898 | A | A |
| I-899 | A | A |
| I-900 | A | A |
| I-901 | A | A |
| I-902 | A | A |
| I-903 | A | A |
| I-904 | A | A |
| I-905 | A | A |
| I-906 | A | A |
| I-907 | A | A |
| I-908 | A | A |
| I-909 | A | A |
| I-910 | A | A |
| I-911 | A | A |
| I-912 | A | A |
| I-913 | A | A |
| I-914 | A | A |
| I-915 | A | A |
| I-916 | A | A |
| I-917 | A | A |
| I-918 | A | A |
| I-919 | A | A |
| I-920 | A | A |
| I-921 | A | A |
| I-922 | A | A |
| I-923 | A | A |
| I-924 | A | A |
| I-925 | A | A |
| I-926 | A | A |
| I-927 | A | A |
| I-928 | A | A |
| I-929 | A | A |
| I-930 | A | A |
| I-931 | A | A |
| I-932 | A | A |
| I-933 | A | A |
| I-934 | A | A |
| I-935 | A | A |
| I-936 | A | A |
| I-937 | A | A |
| I-938 | A | A |
| I-939 | A | A |
| I-940 | A | A |
| I-941 | A | A |
| I-942 | A | A |
| I-943 | A | A |
| I-944 | A | A |
| I-945 | A | A |
| I-946 | A | A |
| I-947 | A | A |
| I-948 | A | A |
| I-949 | A | A |
| I-950 | A | A |
| I-951 | A | A |
| I-952 | A | A |
| I-953 | A | A |
| I-954 | A | A |
| I-955 | A | A |
| I-956 | A | A |
| I-957 | A | A |
| I-958 | A | A |
| I-959 | A | A |
| I-960 | A | A |
| I-961 | A | A |
| I-962 | A | A |
| I-963 | A | A |
| I-964 | A | A |
| I-965 | A | A |
| I-966 | A | A |
| I-967 | A | A |
| I-968 | A | A |
| I-969 | A | A |
| I-970 | A | A |
| I-971 | A | A |
| I-972 | A | A |
| I-973 | A | A |
| I-974 | A | A |
| I-975 | A | A |
| I-976 | A | A |
| I-977 | A | A |
| I-978 | A | A |
| I-979 | A | A |
| I-980 | A | A |
| I-981 | A | A |
| I-982 | A | A |
| I-983 | A | A |
| I-984 | A | A |
| I-985 | A | A |
| I-986 | A | A |
| I-987 | A | A |
| I-988 | A | A |
| I-989 | A | A |
| I-990 | A | A |
| I-991 | A | A |
| I-992 | A | A |
| I-993 | A | A |

TABLE 3-continued

Tyk2 & JAK2 Radioactive Kinase Assay

| Compound | Tyk2 JH1 % Inhibition @ 10 μM | JAK2 JH1 % Inhibition @ 10 μM |
|---|---|---|
| I-994 | A | A |
| I-995 | A | A |
| I-996 | A | A |
| I-997 | A | A |
| I-998 | A | A |
| I-999 | A | A |
| I-1000 | A | A |
| I-1001 | A | A |
| I-1002 | A | A |
| I-1003 | A | A |
| I-1004 | A | A |
| I-1005 | A | A |
| I-1006 | A | A |
| I-1007 | A | A |
| I-1008 | A | B |
| I-1009 | A | A |
| I-1010 | A | A |
| I-1011 | A | A |
| I-1012 | A | A |
| I-1013 | A | A |
| I-1014 | A | A |
| I-1015 | A | A |
| I-1016 | A | A |
| I-1017 | A | A |
| I-1018 | A | A |
| I-1019 | A | A |
| I-1020 | A | A |
| I-1021 | A | A |
| I-1022 | A | A |
| I-1023 | A | A |
| I-1024 | A | A |
| I-1025 | A | A |
| I-1026 | A | A |
| I-1027 | A | A |
| I-1028 | A | A |
| I-1029 | A | A |
| I-1030 | A | A |
| I-1031 | A | A |
| I-1032 | A | A |
| I-1033 | A | A |
| I-1034 | A | A |
| I-1035 | A | A |
| I-1036 | A | A |
| I-1037 | A | A |
| I-1038 | A | A |
| I-1039 | A | A |
| I-1040 | A | A |
| I-1041 | A | A |
| I-1042 | A | A |
| I-1043 | A | A |
| I-1044 | A | A |
| I-1045 | A | A |
| I-1046 | A | A |
| I-1047 | A | A |
| I-1048 | A | A |
| I-1049 | A | A |
| I-1050 | A | A |
| I-1051 | A | A |
| I-1052 | A | A |
| I-1053 | A | A |
| I-1054 | A | A |
| I-1055 | A | A |
| I-1056 | A | A |
| I-1057 | A | A |
| I-1058 | A | A |
| I-1059 | A | A |
| I-1060 | A | A |
| I-1061 | A | A |
| I-1062 | A | A |
| I-1063 | A | A |
| I-1064 | A | A |
| I-1065 | A | A |
| I-1066 | A | A |
| I-1067 | A | A |
| I-1068 | A | A |
| I-1069 | A | A |
| I-1070 | A | A |
| I-1071 | A | A |
| I-1072 | A | A |
| I-1073 | A | A |
| I-1074 | A | A |
| I-1075 | A | A |
| I-1076 | A | A |
| I-1077 | A | A |
| I-1078 | A | A |
| I-1079 | A | A |
| I-1080 | A | A |
| I-1081 | A | A |
| I-1082 | A | A |
| I-1083 | A | A |
| I-1084 | A | A |
| I-1085 | A | A |
| I-1086 | A | A |
| I-1087 | A | A |
| I-1088 | A | A |
| I-1089 | A | A |
| I-1090 | A | A |
| I-1091 | A | A |
| I-1092 | A | A |
| I-1093 | A | A |
| I-1094 | A | A |
| I-1095 | A | A |
| I-1096 | A | A |
| I-1097 | A | A |
| I-1098 | A | A |
| I-1099 | A | A |
| I-1100 | A | A |
| I-1101 | A | A |
| I-1102 | A | A |
| I-1103 | A | A |
| I-1104 | A | A |
| I-1105 | A | A |
| I-1106 | A | A |
| I-1107 | A | A |
| I-1108 | A | A |
| I-1109 | A | A |
| I-1110 | A | A |
| I-1111 | A | A |
| I-1112 | A | A |
| I-1113 | A | A |
| I-1114 | A | A |
| I-1115 | A | A |
| I-1116 | A | A |
| I-1117 | A | A |
| I-1118 | A | A |
| I-1119 | A | A |
| I-1120 | A | A |
| I-1121 | A | A |
| I-1122 | A | A |
| I-1123 | A | A |
| I-1124 | A | A |
| I-1125 | A | A |
| I-1126 | A | A |
| I-1127 | A | A |
| I-1128 | A | A |
| I-1129 | A | A |
| I-1130 | A | A |

Example 5. Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM MgCl$_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Example 6. IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 μl per well is 200,000 cells. 15 μl of compound or DMSO is added to the well at the desired concentrations and incubated at 1 hr at 37 C. 15 μl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

The IL-12 Induced pSTAT4 assay evaluates the inhibition of IL-12 induced STAT4 phophorylation mediated by Tyk2/JAK2 (heterodimeric complex).

Results of the IL-12 Induced pSTAT4 in human PBMC are presented in Table 4. Compounds denoted as "A" had an IC$_{50}$ lower than 0.1 μM; compounds denoted as "B" had an IC$_{50}$ between 0.1 and 0.5 μM; compounds denoted as "C" had an IC$_{50}$ between 0.5 and 1.0 μM; and compounds denoted as "D" had an IC$_{50}$ greater than 1.0 μM.

TABLE 4

IL-12 Induced pSTAT4 in human PBMC assay results.

| Compound | IL-12-pSTAT4 IC$_{50}$ (μM) |
|---|---|
| I-1 | A |
| I-2 | A |
| I-3 | A |
| I-4 | A |
| I-5 | A |
| I-6 | A |
| I-7 | A |
| I-8 | A |
| I-9 | B |
| I-14 | A |
| I-16 | A |
| I-17 | A |
| I-31 | B |
| I-35 | A |
| I-36 | A |
| I-47 | A |
| I-72 | B |
| I-94 | A |
| I-95 | A |
| I-105 | A |
| I-106 | A |
| I-107 | A |
| I-110 | A |
| I-115 | A |
| I-117 | A |
| I-121 | B |
| I-122 | A |
| I-123 | A |
| I-124 | A |
| I-126 | A |
| I-127 | A |
| I-131 | A |
| I-132 | A |
| I-133 | A |
| I-135 | A |
| I-136 | A |
| I-137 | A |
| I-138 | A |
| I-139 | A |
| I-141 | A |
| I-143 | A |
| I-144 | A |
| I-145 | B |
| I-147 | A |
| I-151 | A |
| I-153 | A |
| I-154 | A |
| I-156 | A |
| I-158 | A |
| I-160 | A |
| I-161 | A |
| I-162 | A |
| I-163 | A |
| I-164 | A |
| I-165 | A |
| I-170 | A |
| I-175 | A |
| I-176 | A |
| I-177 | A |
| I-182 | A |
| I-190 | A |
| I-192 | A |
| I-193 | A |
| I-194 | A |
| I-198 | A |
| I-211 | B |
| I-215 | A |
| I-216 | A |
| I-217 | A |
| I-219 | A |
| I-220 | A |
| I-222 | A |
| I-223 | A |
| I-224 | A |
| I-225 | A |
| I-233 | A |
| I-234 | A |
| I-235 | A |
| I-236 | A |
| I-238 | A |
| I-240 | A |
| I-243 | A |
| I-244 | A |
| I-246 | A |
| I-250 | A |
| I-255 | A |
| I-258 | A |
| I-259 | A |
| I-261 | A |
| I-262 | A |
| I-263 | A |
| I-265 | A |
| I-266 | A |
| I-269 | A |
| I-272 | A |
| I-274 | A |
| I-275 | A |
| I-276 | A |
| I-277 | B |
| I-281 | B |
| I-282 | B |
| I-283 | A |
| I-284 | A |
| I-285 | A |
| I-288 | A |

TABLE 4-continued

IL-12 Induced pSTAT4 in human PBMC assay results.

| Compound | IL-12-pSTAT4 IC$_{50}$ (μM) |
|---|---|
| I-290 | A |
| I-292 | A |
| I-294 | A |
| I-295 | A |
| I-296 | A |
| I-303 | A |
| I-305 | A |
| I-309 | A |
| I-310 | A |
| I-311 | A |
| I-312 | A |
| I-314 | A |
| I-315 | A |
| I-317 | A |
| I-318 | A |
| I-319 | A |
| I-321 | A |
| I-323 | A |
| I-324 | A |
| I-326 | A |
| I-329 | A |
| I-330 | A |
| I-331 | A |
| I-332 | A |
| I-333 | A |
| I-334 | A |
| I-342 | A |
| I-343 | A |
| I-344 | A |
| I-345 | A |
| I-346 | A |
| I-347 | A |
| I-350 | A |
| I-351 | A |
| I-352 | A |
| I-354 | A |
| I-357 | A |
| I-359 | B |
| I-360 | A |
| I-362 | A |
| I-363 | A |
| I-365 | A |
| I-366 | A |
| I-368 | A |
| I-369 | A |
| I-370 | A |
| I-371 | B |
| I-372 | A |
| I-373 | A |
| I-374 | A |
| I-375 | A |
| I-377 | B |
| I-378 | A |
| I-379 | A |
| I-380 | A |
| I-381 | A |
| I-384 | A |
| I-385 | A |
| I-386 | A |
| I-390 | A |
| I-391 | A |
| I-392 | A |
| I-393 | A |
| I-395 | A |
| I-396 | A |
| I-397 | A |
| I-399 | A |
| I-401 | A |
| I-404 | D |
| I-405 | B |
| I-406 | B |
| I-407 | A |
| I-408 | B |
| I-409 | A |
| I-410 | A |
| I-411 | A |
| I-413 | A |
| I-415 | A |
| I-417 | B |
| I-423 | A |
| I-425 | A |
| I-426 | A |
| I-428 | A |
| I-429 | A |
| I-435 | B |
| I-438 | A |
| I-448 | A |
| I-474 | A |
| I-483 | A |
| I-499 | A |
| I-500 | A |
| I-510 | A |
| I-522 | A |
| I-539 | A |
| I-540 | A |
| I-541 | B |
| I-544 | A |
| I-545 | B |
| I-547 | B |
| I-551 | A |
| I-559 | A |
| I-560 | A |
| I-562 | A |
| I-563 | A |
| I-570 | A |
| I-578 | A |
| I-585 | A |
| I-586 | A |
| I-590 | A |
| I-591 | A |
| I-592 | A |
| I-603 | A |
| I-606 | B |
| I-607 | A |
| I-612 | A |
| I-621 | A |
| I-630 | A |
| I-635 | A |
| I-637 | A |
| I-639 | A |
| I-640 | A |
| I-658 | A |
| I-661 | A |
| I-665 | A |
| I-667 | A |
| I-670 | A |
| I-673 | A |
| I-676 | A |
| I-677 | A |
| I-680 | A |
| I-681 | A |
| I-693 | A |
| I-694 | A |
| I-706 | A |
| I-709 | A |
| I-710 | B |
| I-711 | A |
| I-712 | A |
| I-715 | A |
| I-716 | A |
| I-718 | A |
| I-722 | A |
| I-725 | A |
| I-740 | A |
| I-747 | B |
| I-748 | A |
| I-750 | A |
| I-751 | A |
| I-756 | B |
| I-759 | A |

TABLE 4-continued

IL-12 Induced pSTAT4 in human PBMC assay results.

| Compound | IL-12-pSTAT4 IC$_{50}$ (µM) |
|---|---|
| I-762 | A |
| I-770 | A |
| I-772 | A |
| I-773 | A |
| I-776 | B |
| I-782 | A |
| I-783 | A |
| I-789 | A |
| I-790 | A |
| I-798 | A |
| I-805 | A |
| I-811 | A |
| I-814 | A |
| I-815 | A |
| I-816 | A |
| I-817 | A |
| I-819 | A |
| I-820 | A |
| I-825 | A |
| I-827 | B |
| I-829 | A |
| I-834 | B |
| I-837 | A |
| I-840 | A |
| I-842 | A |
| I-843 | A |
| I-847 | B |
| I-849 | B |
| I-854 | A |
| I-857 | B |
| I-860 | A |
| I-861 | A |
| I-863 | A |
| I-864 | B |
| I-877 | A |
| I-883 | A |
| I-886 | A |
| I-887 | A |
| I-888 | A |
| I-890 | A |
| I-891 | A |
| I-892 | A |
| I-893 | D |
| I-895 | A |
| I-900 | A |
| I-902 | A |
| I-904 | A |
| I-908 | A |
| I-914 | A |
| I-916 | A |
| I-917 | A |
| I-918 | A |
| I-922 | A |
| I-926 | A |
| I-930 | A |
| I-943 | A |
| I-946 | A |
| I-951 | A |
| I-952 | B |
| I-959 | A |
| I-960 | A |
| I-961 | A |
| I-973 | A |
| I-975 | A |
| I-980 | A |
| I-984 | A |
| I-988 | A |
| I-992 | A |
| I-995 | A |
| I-1000 | A |
| I-1002 | A |
| I-1133 | A |
| I-1283 | A |
| I-1286 | A |
| I-1293 | A |
| I-1296 | A |
| I-1299 | A |
| I-1309 | A |
| I-1312 | A |
| I-1314 | A |
| I-1319 | A |
| I-1321 | A |
| I-1323 | A |
| I-1325 | A |
| I-1328 | A |
| I-1331 | A |
| I-1333 | A |
| I-1343 | A |
| I-1350 | A |
| I-1353 | A |
| I-1354 | A |
| I-1362 | A |
| I-1364 | A |
| I-1365 | A |
| I-1366 | A |
| I-1369 | A |
| I-1373 | A |
| I-1374 | A |
| I-1377 | A |
| I-1378 | A |
| I-1381 | A |
| I-1382 | A |
| I-1385 | A |
| I-1387 | A |
| I-1388 | A |
| I-1389 | A |
| I-1395 | A |
| I-1398 | A |
| I-1411 | A |

Example 7. GM-CSF Induced pSTAT5 in Human PBMC

Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

The GM-CSF Induced pSTAT5 assay is a JAK2 cellular selectivity assay which evaluates inhibition of GM-CSF induced STAT5 phosphorylation mediated by the JAK2/JAK2 homodimeric complex.

Results of the GM-CSF Induced pSTAT5 assay are presented in Table 5. Compounds denoted as "A" had an IC$_{50}$>50 VIM; compounds denoted as "B" had an IC$_{50}$ result of >12.5, >20, >25, or >30 µM; compounds denoted as "C" had an IC$_{50}$ result of >2.5 or >10 µM; and compounds denoted as "D" had an IC$_{50}$ result of >0.3, >0.5, or >1.0 µM.

TABLE 5

GM-CSF Induced pSTAT5 assay results.

| Compound | PBMC_GMCSF_pSTAT5 IC$_{50}$ (µM) |
|---|---|
| I-1 | A |
| I-2 | A |
| I-3 | B |
| I-4 | B |
| I-5 | A |
| I-6 | A |

TABLE 5-continued

GM-CSF Induced pSTAT5 assay results.

| Compound | PBMC_GMCSF_pSTAT5 IC$_{50}$ (μM) |
|---|---|
| I-7 | B |
| I-8 | A |
| I-14 | A |
| I-16 | C |
| I-17 | C |
| I-31 | D |
| I-35 | D |
| I-36 | B |
| I-47 | D |
| I-72 | B |
| I-94 | A |
| I-95 | A |
| I-105 | B |
| I-106 | B |
| I-107 | C |
| I-110 | A |
| I-115 | B |
| I-117 | C |
| I-121 | B |
| I-122 | C |
| I-123 | A |
| I-124 | B |
| I-126 | A |
| I-127 | B |
| I-131 | B |
| I-132 | C |
| I-133 | B |
| I-135 | C |
| I-136 | C |
| I-137 | A |
| I-138 | A |
| I-139 | A |
| I-141 | A |
| I-143 | A |
| I-144 | A |
| I-145 | A |
| I-147 | A |
| I-151 | A |
| I-153 | B |
| I-154 | B |
| I-156 | B |
| I-158 | A |
| I-160 | B |
| I-161 | B |
| I-162 | C |
| I-163 | C |
| I-164 | A |
| I-165 | C |
| I-170 | A |
| I-175 | B |
| I-176 | A |
| I-177 | B |
| I-182 | C |
| I-190 | B |
| I-192 | B |
| I-193 | B |
| I-194 | B |
| I-198 | C |
| I-211 | A |
| I-215 | A |
| I-216 | B |
| I-217 | A |
| I-219 | B |
| I-220 | B |
| I-222 | C |
| I-223 | B |
| I-224 | A |
| I-225 | A |
| I-233 | A |
| I-234 | C |
| I-235 | C |
| I-236 | C |
| I-238 | A |
| I-240 | C |
| I-243 | C |
| I-244 | B |
| I-246 | C |
| I-250 | B |
| I-255 | A |
| I-258 | A |
| I-259 | B |
| I-261 | C |
| I-263 | C |
| I-269 | A |
| I-272 | B |
| I-274 | B |
| I-275 | A |
| I-276 | A |
| I-277 | A |
| I-281 | C |
| I-262 | C |
| I-283 | A |
| I-284 | B |
| I-285 | A |
| I-288 | C |
| I-290 | C |
| I-292 | C |
| I-294 | B |
| I-296 | A |
| I-303 | A |
| I-265 | B |
| I-266 | B |
| I-282 | C |
| I-309 | B |
| I-310 | C |
| I-295 | A |
| I-305 | B |
| I-317 | C |
| I-318 | C |
| I-319 | C |
| I-321 | C |
| I-311 | B |
| I-323 | C |
| I-312 | B |
| I-326 | A |
| I-314 | C |
| I-315 | B |
| I-324 | A |
| I-329 | C |
| I-330 | C |
| I-331 | B |
| I-332 | C |
| I-333 | B |
| I-334 | A |
| I-342 | B |
| I-343 | B |
| I-344 | B |
| I-345 | A |
| I-346 | C |
| I-347 | A |
| I-350 | A |
| I-352 | A |
| I-354 | C |
| I-357 | C |
| I-359 | B |
| I-360 | A |
| I-362 | A |
| I-363 | A |
| I-365 | A |
| I-366 | A |
| I-368 | B |
| I-369 | A |
| I-373 | A |
| I-374 | A |
| I-375 | A |
| I-377 | A |
| I-378 | B |
| I-379 | C |
| I-380 | B |
| I-381 | B |

TABLE 5-continued

GM-CSF Induced pSTAT5 assay results.

| Compound | PBMC_GMCSF_pSTAT5 IC$_{50}$ (μM) |
|---|---|
| I-384 | D |
| I-385 | C |
| I-386 | A |
| I-390 | A |
| I-391 | A |
| I-392 | A |
| I-393 | B |
| I-395 | B |
| I-396 | A |
| I-397 | A |
| I-399 | B |
| I-401 | B |
| I-406 | B |
| I-407 | B |
| I-409 | B |
| I-410 | B |
| I-411 | A |
| I-413 | A |
| I-415 | A |
| I-417 | A |
| I-423 | A |
| I-425 | A |
| I-426 | A |
| I-428 | A |
| I-429 | A |
| I-435 | A |
| I-438 | A |
| I-448 | A |
| I-474 | B |
| I-483 | A |
| I-499 | A |
| I-500 | A |
| I-510 | A |
| I-522 | A |
| I-539 | A |
| I-540 | B |
| I-541 | A |
| I-544 | C |
| I-545 | C |
| I-547 | A |
| I-551 | C |
| I-559 | A |
| I-560 | C |
| I-562 | A |
| I-563 | A |
| I-570 | A |
| I-578 | A |
| I-585 | B |
| I-586 | A |
| I-590 | B |
| I-591 | B |
| I-592 | B |
| I-603 | C |
| I-606 | B |
| I-607 | A |
| I-612 | A |
| I-621 | A |
| I-630 | C |
| I-635 | A |
| I-637 | B |
| I-639 | B |
| I-640 | B |
| I-658 | A |
| I-661 | B |
| I-665 | C |
| I-667 | B |
| I-670 | A |
| I-673 | A |
| I-676 | C |
| I-677 | C |
| I-680 | B |
| I-681 | B |
| I-693 | A |
| I-694 | A |
| I-706 | A |
| I-709 | A |
| I-710 | A |
| I-711 | A |
| I-712 | B |
| I-715 | C |
| I-716 | C |
| I-718 | B |
| I-722 | B |
| I-725 | C |
| I-740 | C |
| I-747 | B |
| I-748 | C |
| I-750 | C |
| I-751 | B |
| I-756 | A |
| I-759 | A |
| I-762 | C |
| I-770 | C |
| I-772 | D |
| I-773 | B |
| I-776 | B |
| I-782 | A |
| I-783 | A |
| I-789 | B |
| I-790 | B |
| I-798 | A |
| I-805 | B |
| I-811 | A |
| I-814 | A |
| I-815 | B |
| I-816 | C |
| I-817 | C |
| I-819 | A |
| I-820 | B |
| I-825 | A |
| I-827 | A |
| I-829 | A |
| I-834 | A |
| I-837 | B |
| I-840 | A |
| I-842 | A |
| I-843 | C |
| I-847 | A |
| I-849 | A |
| I-854 | A |
| I-857 | A |
| I-860 | A |
| I-863 | A |
| I-864 | A |
| I-877 | A |
| I-878 | A |
| I-883 | B |
| I-886 | D |
| I-887 | A |
| I-888 | A |
| I-890 | B |
| I-891 | A |
| I-892 | B |
| I-895 | A |
| I-902 | A |
| I-904 | A |
| I-908 | A |
| I-914 | A |
| I-916 | A |
| I-917 | A |
| I-918 | A |
| I-922 | A |
| I-926 | C |
| I-930 | A |
| I-943 | A |
| I-946 | A |
| I-951 | A |
| I-952 | C |
| I-955 | B |
| I-957 | A |

TABLE 5-continued

GM-CSF Induced pSTAT5 assay results.

| Compound | PBMC_GMCSF_pSTAT5 IC$_{50}$ (µM) |
|---|---|
| I-958 | A |
| I-959 | A |
| I-960 | A |
| I-961 | A |
| I-962 | A |
| I-963 | A |
| I-965 | A |
| I-969 | A |
| I-971 | A |
| I-973 | A |
| I-975 | A |
| I-980 | A |
| I-984 | A |
| I-988 | A |
| I-992 | A |
| I-993 | A |
| I-995 | A |
| I-996 | A |
| I-999 | A |
| I-1000 | A |
| I-1002 | A |
| I-1004 | B |
| I-1010 | A |
| I-1013 | B |
| I-1014 | A |
| I-1017 | B |
| I-1022 | B |
| I-1023 | A |
| I-1025 | A |
| I-1027 | A |
| I-1029 | C |
| I-1035 | C |
| I-1038 | A |
| I-1042 | C |
| I-1048 | C |
| I-1049 | A |
| I-1050 | A |
| I-1051 | A |
| I-1052 | A |
| I-1053 | B |
| I-1057 | A |
| I-1059 | A |
| I-1062 | A |
| I-1063 | A |
| I-1066 | A |
| I-1067 | B |
| I-1070 | B |
| I-1073 | A |
| I-1074 | A |
| I-1080 | A |
| I-1082 | A |
| I-1086 | A |
| I-1088 | A |
| I-1093 | A |
| I-1094 | A |
| I-1095 | A |
| I-1096 | A |
| I-1097 | A |
| I-1098 | A |
| I-1099 | A |
| I-1101 | A |
| I-1102 | C |
| I-1105 | A |
| I-1107 | C |
| I-1117 | A |
| I-1378 | A |
| I-1398 | A |

Example 8. Ex Vivo Mouse IL-12 Induced IFNγ Studies

C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 9. T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1\times10^4$ cells per well in 96-well plates. T-ALL cell lines DU.528, LOUCY, and SUP-T13 are cultured in the same medium and plated at a density of $1.5\times10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. IC$_{50}$ value is calculated by nonlinear regression using GraphPad Prism software.

Example 10: N-((1R,2S)-2-fluorocyclopropyl)-5-((2-methoxypyridin-3-yl)amino)-7-((2-morpholino-ethyl)amino)pyrazolo[1,5-a]pyrimidine-3-carboxamide I-388

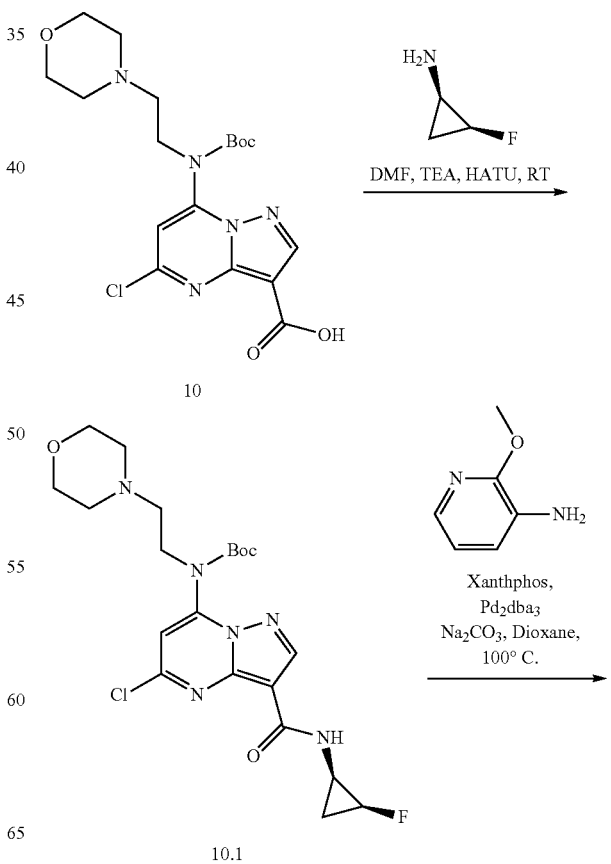

843 -continued

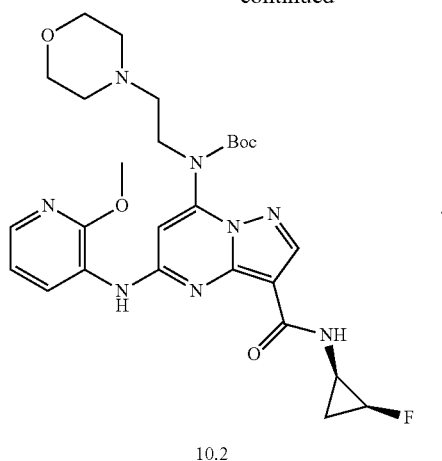

10.2

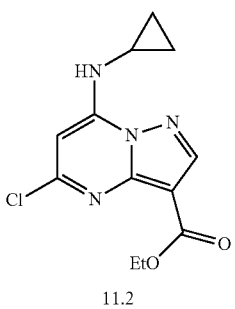

I-388

Synthesis of Compound 1.

Compound was synthesized as per experimental protocol of I-387. to obtain 1. (Yield: 64.66%). MS (ES): m/z 426.15 [M+H]+

Synthesis of Compound 1.1.

Compound was synthesized using general procedure A to obtain 1.1. (0.200 g, 39.19%), MS (ES): 483.19 [M+H]+

Synthesis of Compound 1.2.

Compound was synthesized using general procedure B to obtain 1.2. (0.058 g, 24.54%), MS (ES): 571.27 [M+H]+

Synthesis of Compound I-388:

Compound was synthesized using general procedure C to obtain I-388 (0.036 g, 75.28%), MS (ES): m/z 471.56 [M+H]+, LCMS purity: 98.38%, HPLC purity: 98.69%, $^1$H NMR (DMSO-$d_6$, 400 MHZ): 8.90 (s, 1H), 8.21 (s, 2H), 7.89-7.88 (d, J=3.6 Hz 1H), 7.82-7.81 (d, J=4.4 Hz, 1H), 7.67 (s, 1H), 6.99-6.96 (m, 1H), 6.05 (s, 1H), 4.87-4.71 (m, 1H), 3.96 (s, 3H), 3.59 (s, 4H) 3.34 (s, 2H), 2.90-2.89 (d, J=4 Hz, 1H), 2.63-2.59 (t, J=13.2 Hz, 2H), 2.47 (s, 4H), 1.20-1.10 (m, 1H), 0.76 (bs, 1H).

844

Example 11: N-cyclopropyl-7-(cyclopropylamino)-5-((2-methoxypyridin-3-yl)amino)pyrazolo[1,5-a]pyrimidine-3-carboxamide I-336

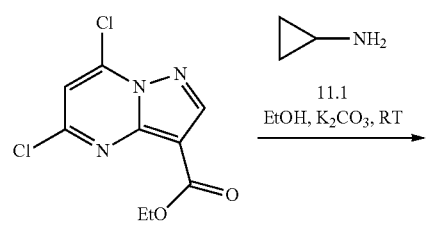

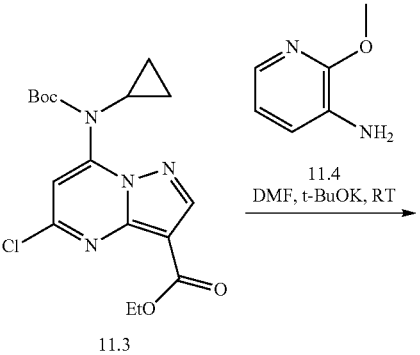

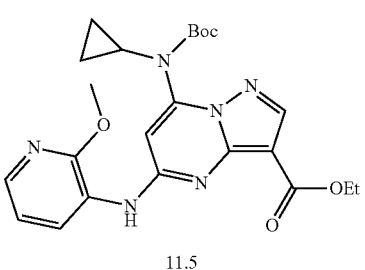

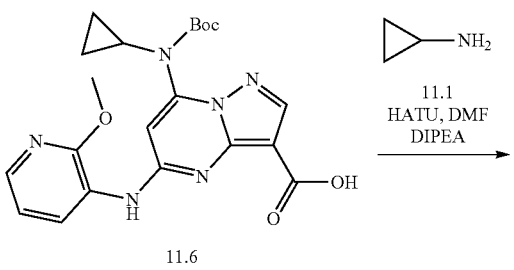

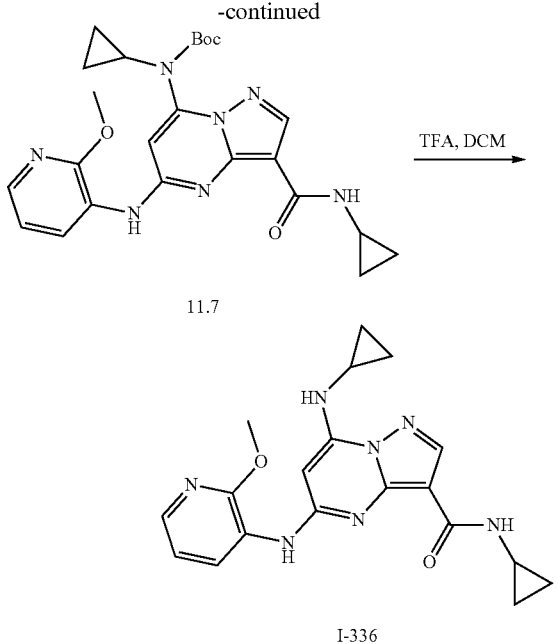

11.7

I-336

Synthesis of Compound 11.

Compound was synthesized using general procedure of core A synthesis to obtain 11.

Synthesis of Compound 11.2.

To a solution of 1 (5 g, 19.23 mmol, 1.0 eq), and 11.1 (1.21 g, 21.15 mmol, 1.1 eq) in ethanol (50 mL) was added potassium carbonate (2.92 g, 21.15 mmol, 1.1 eq). The reaction was stirred at room temperature for 2 h. After completion of reaction, reaction mixture was transferred into cold ice water and product was extracted with ethyl acetate. Organic layer was combined and dried over sodium sulphate and concentrated under reduced pressure to obtain crude material. This was further purified by column chromatography and compound was eluted in 13% ethyl acetate in hexane to obtain pure 1.2 (4 g, 74.12%). MS (ES): m/z 281.71 [M+H]$^+$.

Synthesis of Compound 11.3.

To a cooled solution of 11.2 (4 g, 14.25 mmol, 1.0 eq), in dioxane (30 mL) was added di-tert-butyl dicarbonate (4.66 g, 21.37 mmol, 1.5 eq) and 4-Dimethylaminopyridine (0.173 g, 1.42 mmol, 0.1 eq). The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 11% ethyl acetate in hexane to obtain 1.3 (4.2 g, 77.44%). MS(ES): m/z 381.83 [M+H]$^+$.

Synthesis of Compound 11.5.

To a cooled solution of 11.3 (0.800 g, 2.10 mmol, 1.0 eq), and 11.4 (0.290 g, 2.31 mmol, 1.1 eq) in dimethylformamide (8 mL) at 0° C. was added potassium ter-butoxide (5.2 mL, 5.26 mmol, 2.5 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 18% ethyl acetate in hexane to obtain pure 1.5. (0.500 g, 50.80%). MS (ES): m/z 469.51 [M+H]$^+$.

Synthesis of Compound 11.6.

To a solution of 11.5 (0.500 g, 1.07 mmol, 1.0 eq), in tetrahydrofuran:methanol:water (20 mL, 2:1:1) was added lithium hydroxide (0.449 g, 10.7 mmol, 10 eq). The reaction was stirred at 80° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.2% methanol in dichloromethane to obtain pure 11.6 (0.400 g, 85.10%). MS(ES): m/z 441.46 [M+H]$^+$.

Synthesis of Compound 11.7.

Compound was synthesized using general procedure A to obtain 11.7. (0.060 g, 55.11%). MS (ES): m/z 480.44 [M+H]$^+$ Synthesis of Compound I-336.

Compound was synthesized using general procedure C to obtain I-336 (0.025 g, 52.66%). MS (ES): m/z 380.39 [M+H]$^+$, LCMS purity: 100%, HPLC purity: 99.13%, $^1$H NMR (DMSO-d$_6$, 400 MHZ): 9.09 (s, 1H), 8.19 (s, 1H), 8.14 (s, 1H), 7.949-7.941 (d, J=3.2 Hz, 1H), 7.80 (s, 1H), 7.07-7.04 (m, 1H), 6.84 (m, 1H), 6.23 (s, 1H), 3.96 (s, 3H), 1.56 (bs, 1H), 1.24 (m, 1H), 0.84-00.82 (m, 2H), 0.72-0.69 (m, 4H), 0.34-0.36 (m, 2H).

Example 12: 7-(cyclopropylamino)-N-((1R,2S)-2-fluorocyclopropyl)-5-((2-methoxypyridin-3-yl)amino)pyrazolo[1,5-a]pyrimidine-3-carboxamide I-337

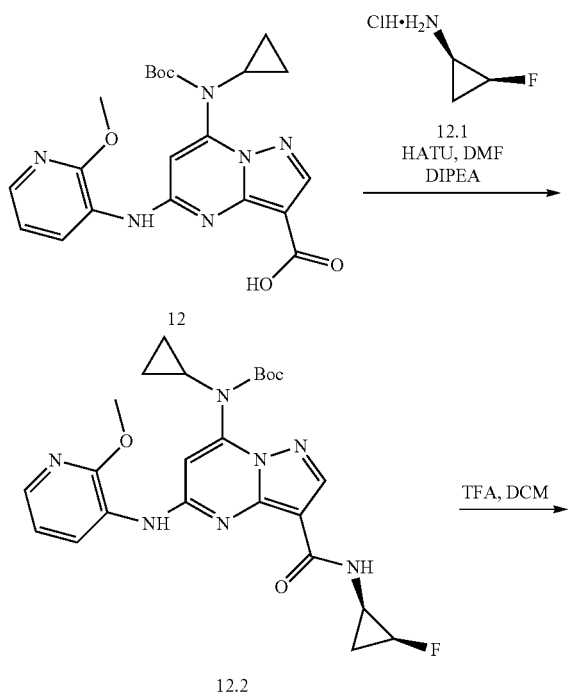

-continued

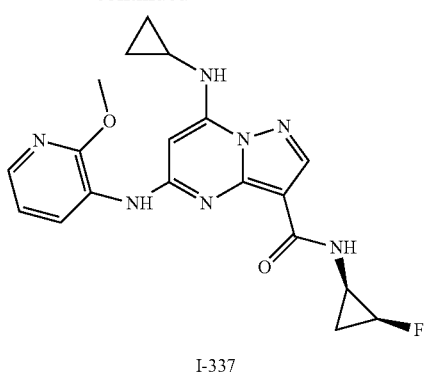

I-337

Synthesis of Compound 12.

Compound was synthesized as per experimental protocol of I-336.

Synthesis of Compound 12.2.

Compound was synthesized using general procedure B to obtain 1.2 (0.070 g, 61.97%), MS (ES): m/z 498.53 [M+H]$^+$ Synthesis of Compound I-337:

Compound was synthesized using general procedure C to obtain I-337 (0.050 g, 89.42%), MS (ES): m/z 398.17 [M+H]—, LCMS purity: 100%, HPLC purity: 99.62%, CHIRAL HPLC purity: 100%, $^1$H NMR (DMSO-d$_6$, 400 MHZ): 9.07 (s, 1H), 8.22 (s, 1H), 8.20 (s, 1H), 8.18 (s, 1H), 7.91-7.90 (d, J=4 Hz, 1H), 7.83-7.82 (d, J=4 Hz, 1H), 7.01-6.99 (t, J=8 Hz, 1H), 6.28 (s, 1H), 4.87-4.69 (m, 1H), 3.96 (s, 3H), 2.91-2.88 (m, 1H), 2.60 (bs, 1H), 1.26-1.10 (m, 2H), 0.86-0.82 (m, 2H), 0.79-0.68 (m, 2H).

Example 13: N-((1R,2S)-2-fluorocyclopropyl)-5-((2-methoxypyridin-3-yl)amino)-7-((methyl-d3)amino)pyrazolo[1,5-a]pyrimidine-3-carboxamide I-374

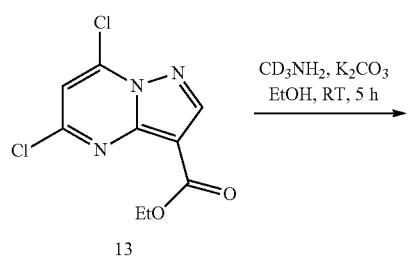

13

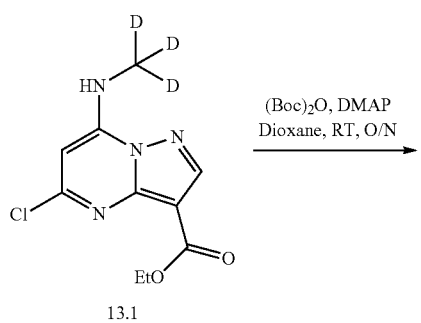

13.1

-continued

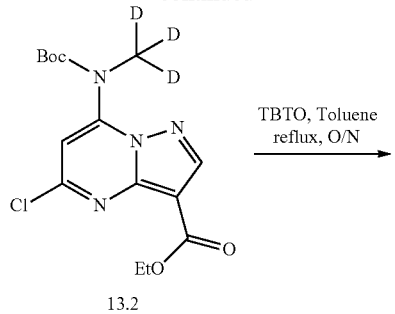

13.2

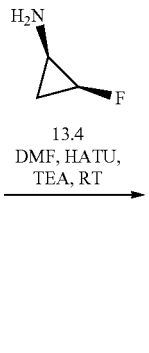

13.3

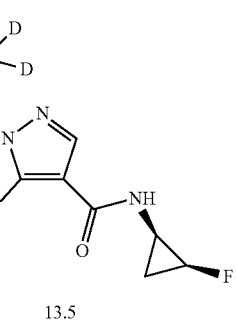

13.5

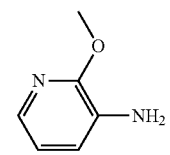

13.6
Xanthphos, Pd$_2$dba$_3$
Na$_2$CO$_3$, Dioxane,
100° C.

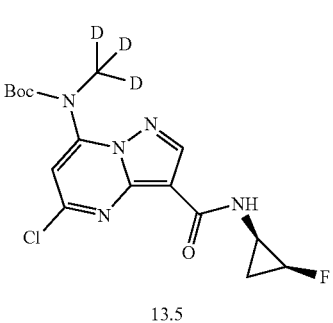

13.5

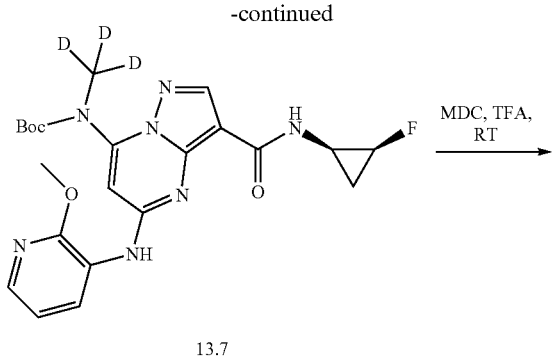

13.7

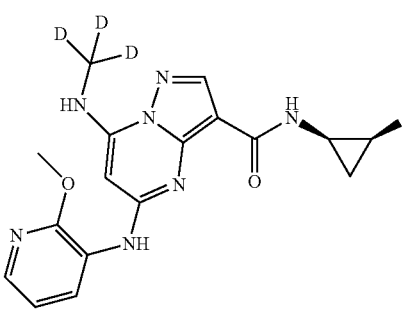

I-374

Synthesis of Compound 13.

Compound was synthesized as per experimental procedure [0002] of core synthesis (Yield: 69.85%). MS(ES): m/z 261 [M+H]$^+$.

Synthesis of Compound 13.1.

To a solution of 13 (1.5 g, 5.76 mmol, 1.0 eq) in ethanol (20 mL), methyl-D3-amine (0.215 g, 6.33 mmol, 1.1 eq) was added. The reaction mixture was degassed for 10 min under argon atmosphere followed by addition of potassium carbonate (0.873 g, 6.33 mmol, 1.1 eq). The reaction mixture was stirred at room temperature for 5 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 20% ethyl acetate in hexane to obtain 13.1. (1.5 g, Yield: 100%). MS (ES): m/z 258.08 [M+H]$^+$.

Synthesis of Compound 13.2.

To a solution of 13.1 (1.5 g, 5.82 mmol, 1.0 eq) in 1,4-dioxane (15 mL) was added N,N-dimethylaminopyridine (0.071 g, 0.58 mmol, 0.1 eq) followed by Di-tert-butyl dicarbonate (2.53 g, 11.64 mmol, 2.0 eq) and reaction mixture was stirred at room temperature for 12 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 12% ethyl acetate in hexane to obtain 13.2. (1.2 g, 57.62%). MS(ES): m/z 358.13 [M+H]$^+$.

Synthesis of Compound 13.3.

To a suspension of 13.2. (1.2 g, 3.35 mmol, 1.0 eq) in toluene (20 mL) was added Tributyltin oxide (3.99 g, 6.7 mmol, 2.0 eq) and reaction mixture was heated at 120° C. for 12 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulphate and concentrated under reduced pressure to obtain solid which was triturated with hexane to obtain pure 13.3. (1 g, 90.42%). MS(ES): m/z 330.10 [M+H]$^+$.

Synthesis of Compound 13.5.

Compound was synthesized using general procedure A to obtain 13.5. (0.480 g, 40.92%), MS (ES): 387.14 [M+H]$^+$ Synthesis of Compound 13.7.

Compound was synthesized using general procedure B to obtain 13.7. (0.065 g, 52.99%), MS (ES): 475.23 [M+H]$^+$ Synthesis of Compound I-374:

Compound was synthesized using general procedure C to obtain I-374 (0.028 g, 54.60%), MS (ES): m/z 375.30 [M+H]$^+$, LCMS purity: 99.13%, HPLC purity: 98.12%, CHIRAL HPLC: 98.42%, $^1$H NMR (DMSO-d$_6$, 400 MHZ): 8.92 (s, 1H), 8.24-8.20 (t, J=7.6 Hz, 2H), 7.91-7.89 (m, 2H), 7.83-7.82 (d, J=4.4 Hz, 1H), 7.00-6.97 (m, 1H), 5.94 (s, 1H), 4.87-4.72 (m, 1H), 2.90 (bs, 1H), 1.24-1.13 (m, 2H), 1.05-1.04 (m, 2H), 0.76-0.70 (m, 1H).

Example 14: 5-((2-cyclopropoxypyridin-3-yl)amino)-N-((1R,2S)-2-fluorocyclopropyl)-7-((methyl-d3)amino)pyrazolo[1,5-a]pyrimidine-3-carboxamide I-375

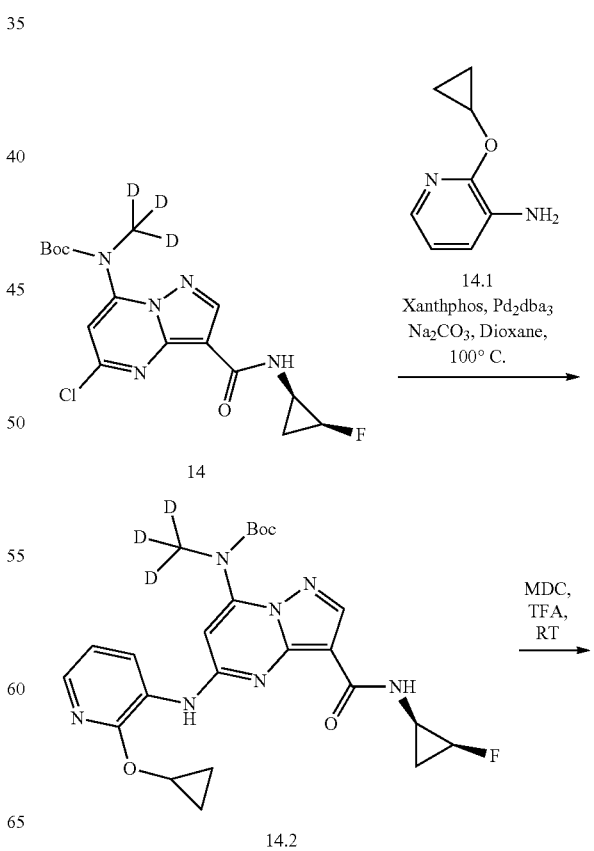

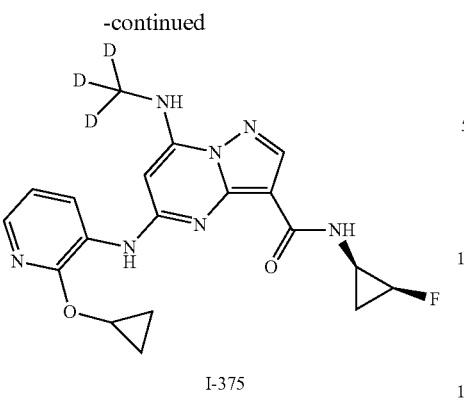

I-375

Synthesis of Compound 14.

Compound was synthesized as per experimental protocol of I-374 to obtain 14. (Yield: 40.92%), MS (ES): m/z 387.14 [M+H]$^+$ Synthesis of Compound 14.1.

Compound was synthesized as per experimental protocol of I-366 to obtain 14.1. (Yield: 79.98%), MS (ES): m/z 151.18 [M+H]$^+$ Synthesis of Compound 14.2.

Compound was synthesized using general procedure B to obtain 14.2. (0.070 g, 54.10%), MS (ES): 501.24 [M+H]$^+$ Synthesis of Compound I-375:

Compound was synthesized using general procedure C to obtain I-375 (0.035 g, 62.50%), MS (ES): m/z 401.50 [M+H]$^+$, LCMS purity: 96.08%, HPLC purity: 97.25%, CHIRAL HPLC: 99.31%, $^1$H NMR (DMSO-d$_6$, 400 MHZ): 8.69 (s, 1H), 8.19 (s, 2H), 7.92 (bs, 2H), 7.81-7.80 (d, J=4.4 Hz, 1H), 7.01-6.98 (m, 1H), 5.89 (s, 1H), 2.90 (bs, 1H), 1.19-1.12 (m, 1H), 1.24 (bs, 2H), 0.76-0.75 (m, 5H).

Example 15: N-((1R,2S)-2-fluorocyclopropyl)-5-((2-methoxypyridin-3-yl)amino)-7-((3-morpholinopropyl)amino)pyrazolo[1,5-a]pyrimidine-3-carboxamide I-377

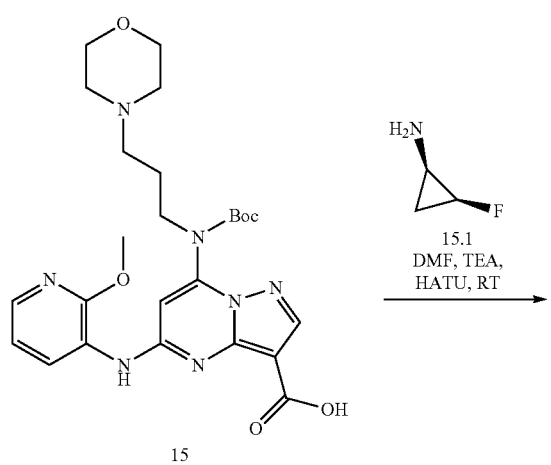

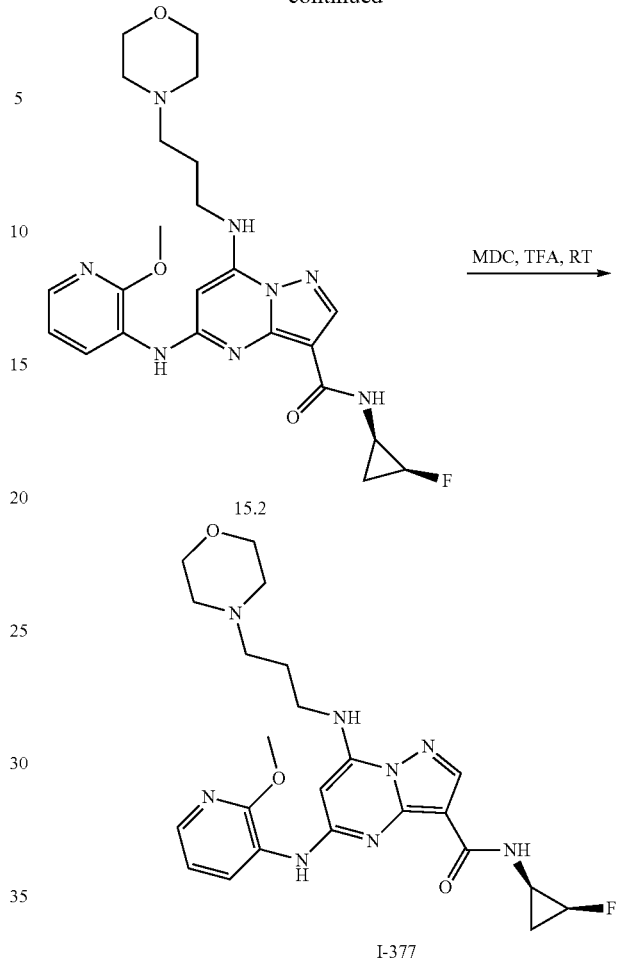

Synthesis of Compound 15.

Compound was synthesized as per experimental protocol of I-376 to obtain 1. (Yield: 78.4%), MS (ES): m/z 588.44 [M+H]$^+$ Synthesis of Compound 15.2.

To a solution of 1 (0.150 g, 0.284 mmol, 1.0 eq), in N,N-dimethylformamide (2 mL) was added 1-[Bis(dimethylamino)methylene]-1H-1,2,3-triazolo[4,5-b]pyridinium 3-oxid hexafluorophosphate (0.216 g, 0.569 mmol, 2.0 eq) and stirred at room temperature for 15 min. To this added diisopropylethylamine (0.3 mL, 1.42 mmol, 5.0 eq) followed by addition of 1 (0.140 g, 0.569 mmol, 2.0 eq). The reaction mixture was stirred at room temperature for 30 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% dichloromethane in methanol to obtain 1.2. (0.130 g, 93.2%). MS(ES): m/z 485.1 [M+H]$^+$.

Synthesis of Compound I-377:

Compound was synthesized using general procedure C to obtain I-377 (0.050 g, 55.56%), MS (ES): m/z 485.26 [M+H]$^+$, LCMS purity: 95.78%, HPLC purity: 96.31%, $^1$H NMR (DMSO-d$_6$, 400 MHZ): 8.87 (s, 1H), 8.24-8.23 (m, 3H), 7.90-7.89 (d, J=3.6 Hz, 1H), 7.83-7.82 (d, J=4.8 Hz, 1H), 7.00-6.97 (m, 1H), 6.02 (s, 1H), 4.87 (s, 2H), 3.96 (s, 3H), 3.63 (s, 3H), 2.92-2.90 (t, J=9.6 Hz, 1H) 2.42-2.39 (d, J=12.8 Hz, 6H), 1.86-1.83 (t, J=13.2 Hz, 2H), 1.21-1.08 (m, 2H), 0.87 (s, 1H), 0.78 (s, 1H).

Example 16: N-cyclopropyl-5-((2-methoxypyridin-3-yl)amino)-7-((3-morpholinopropyl)amino)pyrazolo[1,5-a]pyrimidine-3-carboxamide I-376

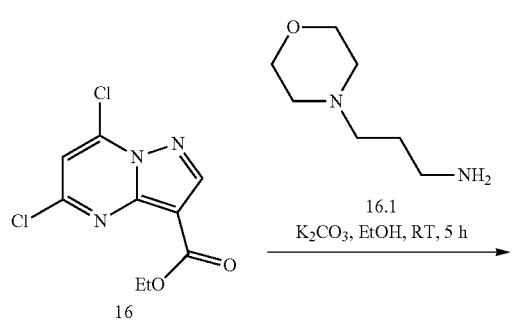

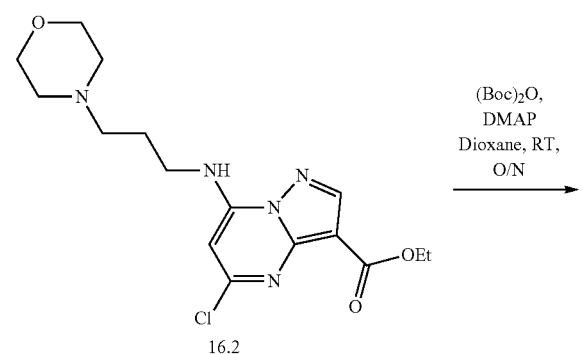

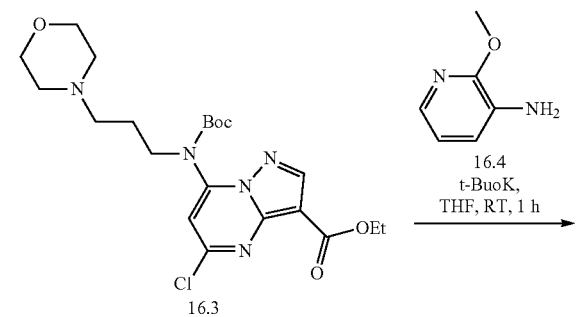

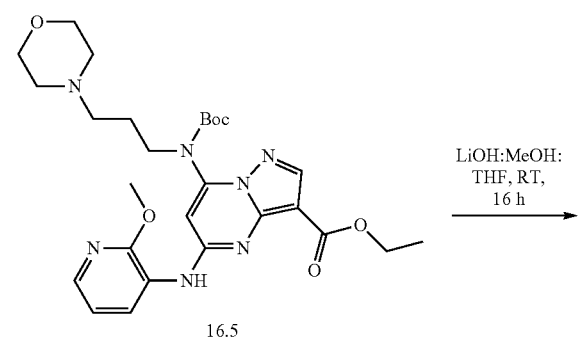

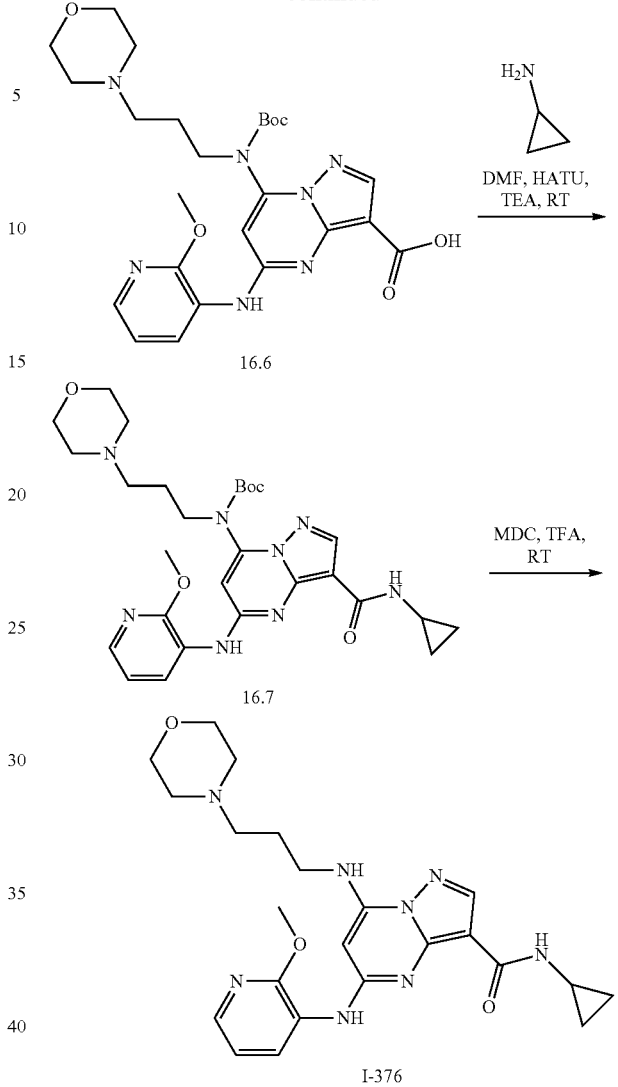

Synthesis of Compound 16.

Compound was synthesized using general procedure [0002] of core synthesis to obtain 16. (35 g, 69.85%). MS(ES): m/z 261 [M+H]⁺.

Synthesis of Compound 16.2.

To a solution of 16 (2.2 g, 8.46 mmol, 1.0 eq), in ethanol (25 mL) was added 16.2 (1.3 g, 9.30 mmol, 1.1 eq) and stirred at room temperature for 5 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 16.2 (1.5 g, 48.21%). MS(ES): m/z 368.83 [M+H]⁺.

Synthesis of Compound 16.3.

To a solution of 16.2 (1.5 g, 4.08 mmol, 1.0 eq) in 1,4-dioxane (15 mL) was added N,N-dimethylaminopyridine (49 mg, 40.8 mmol, 0.1 eq) followed by Di-tert-butyl dicarbonate (1.7 g, 8.15 mmol, 2.0 eq) and reaction mixture was stirred at room temperature for 12 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 12% ethyl acetate in hexane to obtain 16.3 (1.5 g, 78.61%). MS(ES): m/z 468.9 [M+H]$^+$.

Synthesis of Compound 16.5.

To a suspension of 16.3 (2 g, 4.21 mmol, 1.0 eq) and 1.4 (0.7 g, 5.55 mmol, 1.3 eq) in tetrahydrofuran (40 mL) was added potassium tert-butoxide (8.5 mL, 8.52 mmol, 2.0) and reaction mixture was stirred at room temperature for 1 h. After completion of reaction, reaction mixture was diluted with water extracted with ethyl acetate. Organic layer was combined, dried over sodium sulphate and concentrated under reduced pressure to obtain solid which was. This was further purified by column chromatography and the compound was eluted in 50% ethyl acetate in hexane to obtain pure 16.5 (2 g, 84.42%), MS(ES): m/z 556.28 [M+H]$^+$.

Synthesis of Compound 16.6.

To a suspension of 16.5 (2 g, 3.60 mmol, 1.0 eq) in tetrahydrofuran:water (20 mL, 2:1) was added lithium hydroxide (1.5 g, 36.01 mmol, 10 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 16.6 (1.5 g, 78.4%). MS(ES): m/z 528.44 [M+H]$^+$.

Synthesis of Compound 16.7.

Compound was synthesized using general procedure A to obtain 16.7. (0.480 g, 40.92%), MS (ES): 567.1 [M+H]$^+$ Synthesis of Compound I-376:

Compound was synthesized using general procedure C to obtain I-376 (0.050 g, 60.73%), MS (ES): m/z 467.3 [M+H]$^+$ LCMS purity: 100%, HPLC purity: 95.21%, $^1$H NMR (DMSO-d$_6$, 400 MHZ): 8.89 (s, 1H), 8.23-8.19 (m, 2H), 8.15 (s, 1H), 7.93-7.92 (m, 1H), 7.80-7.79 (d, J=4.0 Hz, 1H), 7.04-7.01 (m, 1H), 5.97 (s, 1H), 3.96 (s, 3H), 3.64-3.62 (m, 4H), 3.35-3.33 (m, 2H), 2.81-2.77 (m, 1H), 2.44-2.39 (m, 6H), 1.86-1.82 (m, 2H), 0.73-0.69 (m, 2H), 0.38-0.34 (m, 2H).

Example 17: N-cyclopropyl-5-((2-methoxypyridin-3-yl)amino)-7-((2-morpholinoethyl)amino)pyrazolo[1,5-a]pyrimidine-3-carboxamide I-387

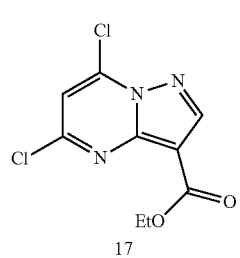

17

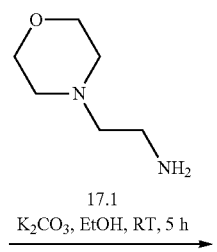

17.1
K$_2$CO$_3$, EtOH, RT, 5 h

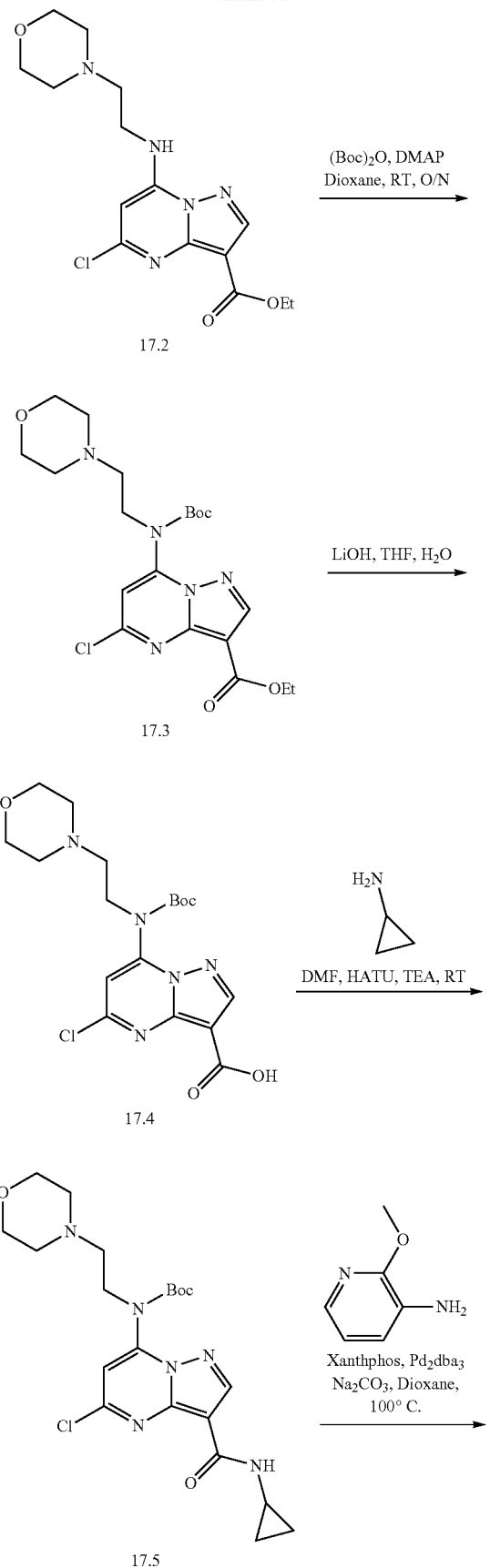

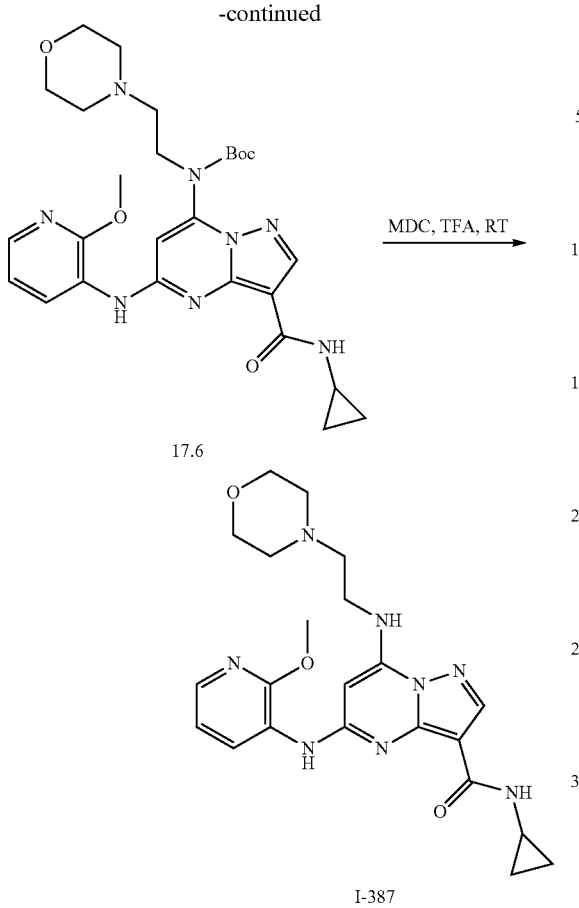

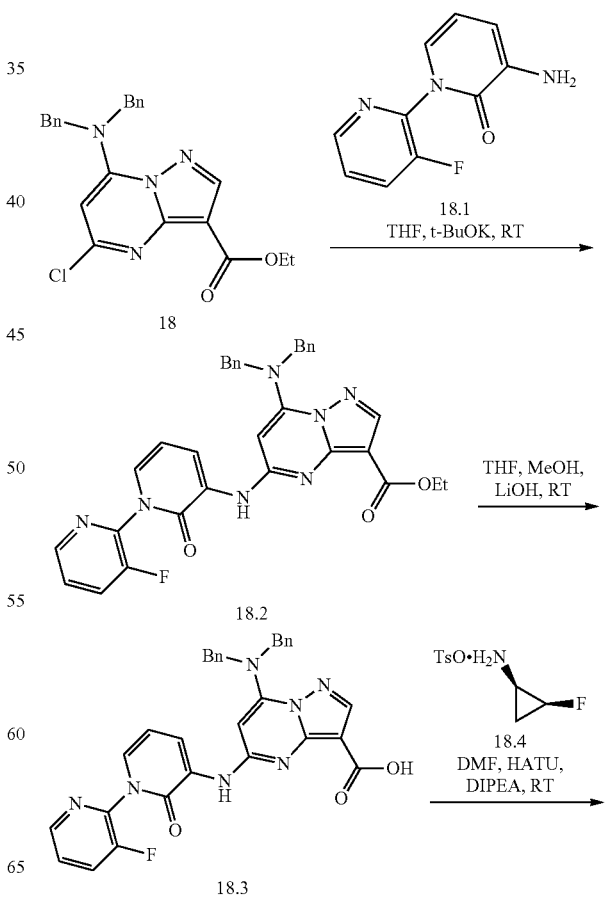

reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 17.4 (0.910 g, 64.66%). MS(ES): m/z 426.15 [M+H]$^+$.

Synthesis of Compound 17.5.

Compound was synthesized using general procedure A to obtain 17.5 (0.170 g, 34.60%), MS (ES): 465.20 [M+H]$^+$ Synthesis of Compound 17.6.

Compound was synthesized using general procedure B to obtain 17.6 (0.070 g, 45.30%), MS (ES): 553.28 [M+H]$^+$ Synthesis of Compound I-387:

Compound was synthesized using general procedure C to obtain I-387 (0.034 g, 59.32%), MS (ES): m/z 453.51 [M+H]$^+$, LCMS purity: 99.67%, HPLC purity: 99.85%, $^1$H NMR (DMSO-$d_6$, 400 MHZ): 8.92 (s, 1H), 8.22-8.20 (d, J=6.4 Hz, 2H), 7.93-7.92 (d, J=3.6 Hz 1H), 7.79-7.78 (d, J=3.6 Hz, 1H), 7.64 (s, 1H), 7.04-7.00 (m, 1H), 6.00 (s, 1H), 3.95 (s, 3H), 3.59 (s, 4H), 3.34 (s, 2H), 2.80-2.76 (s, 1H), 2.62-2.60 (d, J=6.8 Hz, 2H), 2.59-2.46 (m, 4H), 0.73-0.68 (m, 2H), 0.36 (bs, 2H).

Example 18: 7-amino-5-((3'-fluoro-2-oxo-2H-[1,2'-bipyridin]-3-yl)amino)-N-((1R,2S)-2-fluorocyclopropyl)pyrazolo[1,5-a]pyrimidine-3-carboxamide I-954

Synthesis of Compound 17.2.

To a solution of 17 (2.2 g, 8.46 mmol, 1.0 eq) in ethanol (22 mL), 17.1 (1.20 g, 9.30 mmol, 1.1 eq) was added. The reaction mixture was degassed for 10 min under argon atmosphere followed by addition of potassium carbonate (1.28 g, 9.3 mmol, 1.1 eq). The reaction mixture was heated at RT for 5 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 20% ethyl acetate in hexane to obtain 17.2 (1.8 g, Yield: 60.14%). MS (ES): m/z 354.13 M+H]$^+$.

Synthesis of Compound 17.3.

To a solution of 17.2 (1.8 g, 5.09 mmol, 1.0 eq) in 1,4-dioxane (20 mL) was added N,N-dimethylaminopyridine (0.062 g, 0.50 mmol, 0.1 eq) followed by Di-tert-butyl dicarbonate (1.66 g, 7.63, 1.5 eq) and reaction mixture was stirred at room temperature for 16 h. After completion of reaction, reaction mixture was transferred in water product was extracted with dichloromethane. Organic layer was combined and dried over sodium sulphate and concentrated under reduced pressure to obtain crude material. This was further purified by column chromatography and the compound was eluted in 15% ethyl acetate in hexane to obtain 17.3. (1.5 g, 64.95%). MS(ES): m/z 454.18[M+H]$^+$.

Synthesis of Compound 17.4.

To a solution of 17.3 (1.5 g, 3.3 mmol, 1.0 eq), in tetrahydrofuran:methanol:water (10 mL, 2:2:1) was added lithium hydroxide (1.39 g, 33.1 mmol, 10 eq). The reaction was stirred at 60° C. for 16 h. After completion of reaction,

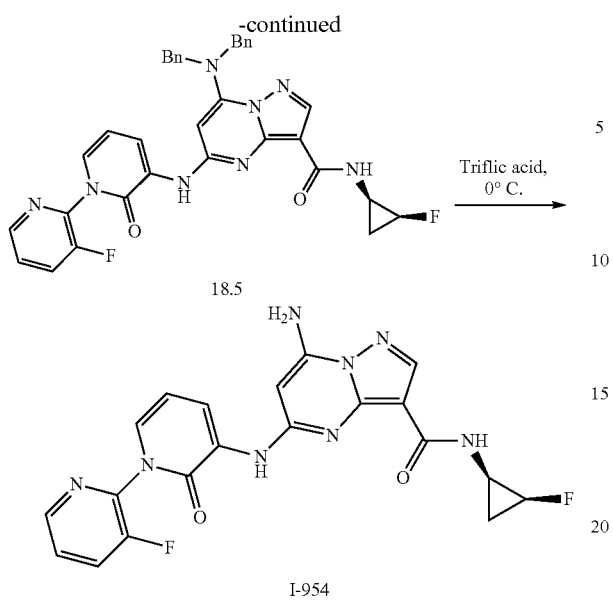

I-954

Synthesis of Compound 18.

Compound was synthesized using general procedure of core synthesis to obtain 18. MS (ES): m/z 421.14 [M+H]+

Synthesis of Compound 18.1.

Compound was synthesized as per experimental protocol of Example 19 (I-144) to obtain 18.1. (Yield: 80.70%), MS (ES): m/z 206.29 [M+H]+

Synthesis of Compound 18.2:

To a cooled solution of 18 (0.1 g, 0.23 mmol, 1.0 eq), and 18.1. (0.047 g, 0.23 mmol, 1.0 eq) in tetrahydrofuran (2 mL) at 0° C. was added potassium ter-butoxide (1M in tetrahydrofuran) (0.5 mL, 0.46 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 18.2. (0.089 g, 63.53%). MS (ES): m/z 590.23 [M+H]+

Synthesis of Compound 18.3.

To a solution of 18.2 (0.089 g, 0.15 mmol, 1.0 eq), in tetrahydrofuran:methanol (2 mL, 1:1) was added lithium hydroxide (0.036 g, 1.5 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 18.3. (0.079 g, 93.20%). MS(ES): m/z 562.20 [M+H]+

Synthesis of Compound 18.5.

Compound was synthesized using general procedure A to obtain 18.5. (0.059 g, 67.79%), MS (ES): m/z 619.23 [M+H]+

Synthesis of Compound I-954:

Mixture of 18.5 (0.059 g, 0.95 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with dichloromethane. Organic layer was combined, dried over sodium sulphate and concentrated under reduced pressure to obtain crude material. This was further purified by trituration with diethyl ether to a obtain I-954 (0.033 g, 78.93%), MS (ES): m/z 439.61 [M+H]+, LCMS purity: 98.70%, HPLC purity: 98.19%, CHIRAL HPLC: 100%, ¹H NMR (DMSO-d₆, 400 MHZ): 9.05 (bs, 1H), 8.51-8.50 (d, J=4.4 Hz, 1H), 8.24 (s, 1H), 8.22-8.20 (d, J=7.2 Hz, 1H), 8.08-8.03 (t, J=8.4 Hz, 1H), 7.85-7.84 (d, J=4.4 Hz, 1H), 7.74-7.70 (m, 3H), 4.44-7.43 (d, J=1.2 Hz, 1H), 6.43-6.39 (t, J=7.2 Hz, 1H), 6.13 (bs, 1H), 4.97-4.95 (m, 1H), 4.80 (bs, 1H), 3.00-2.97 (m, 1H), 1.26-1.18 (m, 1H).

Example 19: 5-((3'-fluoro-2-oxo-2H-[1,2'-bipyridin]-3-yl)amino)-N-((1R,2S)-2-fluorocyclopropyl)-7-(methylamino)pyrazolo[1,5-a]pyrimidine-3-carboxamide I-144

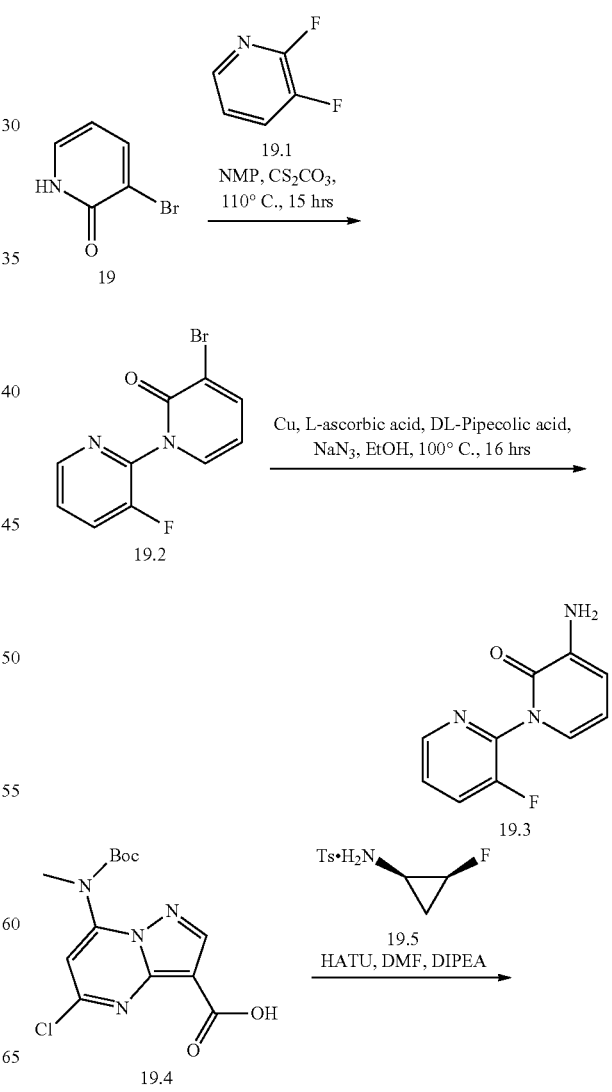

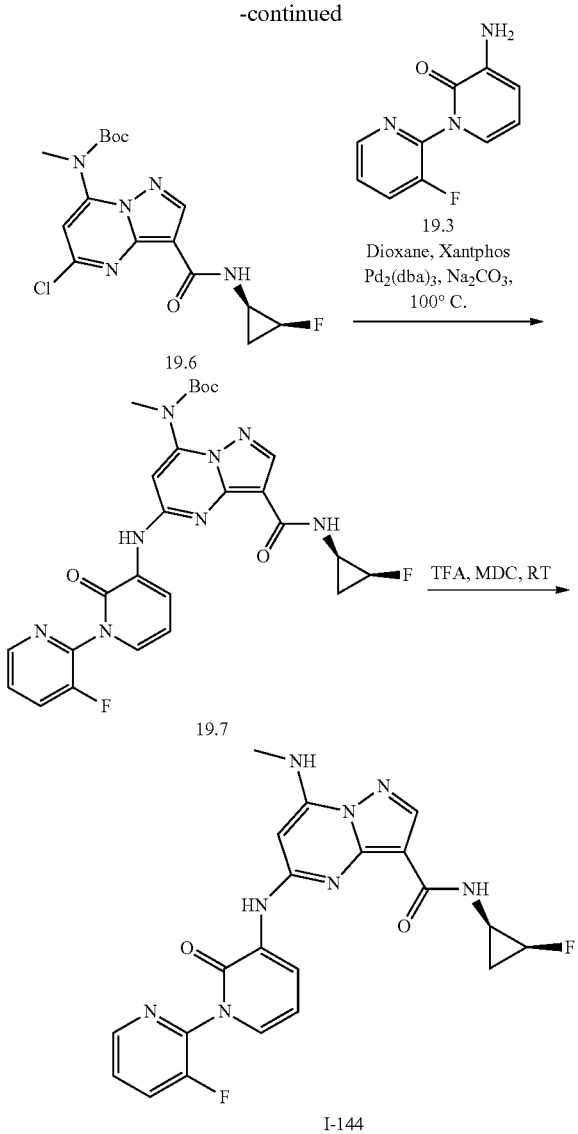

Synthesis of Compound 19.2.

To a solution of 19 (10 g, 57.47 mmol, 1.0 eq) in 1-methylpyrrolidin-2-one (240 mL), 19.1 (7.34 g, 63.79 mmol, 1.1 eq) was added followed by addition of cesium carbonate (46.81 g, 143.67 mmol, 2.5 eq). The reaction mixture was heated at 110° C. for 15 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified column chromatography using 50% ethyl acetate in hexane as eluant to obtain 19.2 (2.6 g, 16.81%). MS (ES): m/z 269.04 [M].

Synthesis of Compound 19.3.

To a solution of 19.2 (2.6 g, 9.66 mmol, 1.0 eq) in ethanol (26 mL) was added copper powder (0.073 g, 1.15 mmol, 0.12 eq), L-ascorbic acid (0.34 g, 1.93 mmol, 0.2 eq), DL-Pipecolic acid (0.37 g, 2.89 mmol, 0.3 eq) and sodium azide (2.26 g, 34.77 mmol, 3.6 eq). The reaction mixture was heated at 100° C. for 16 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified column chromatography using 55-60% ethyl acetate in hexane as eluant to obtain 19.3 (1.6 g, 80.70%). MS (ES): m/z 206.29 [M+H]$^+$ Synthesis of Compound 19.4.

Compound was synthesized using general procedure of core synthesis to obtain 19.4. (Yield: 71.67%).

Synthesis of Compound 19.6.

To a solution of 19.4 (10 g, 30.61 mmol, 1.0 eq), in N,N-dimethylformamide (300 mL) was added 1-[Bis(dimethylamino)methylene]-1H-1,2,3-triazolo[4,5-b]pyridinium 3-oxid hexafluorophosphate (15.12 g, 39.79 mmol, 1.3 eq) and stirred at room temperature for 15 min. To this added 19.5 (7.5 g, 30.61 mmol, 1.0 eq) followed by addition of diisopropylethylamine (16 mL, 91.83 mmol, 3.0 eq). Reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 35% ethyl acetate in hexane to obtain 19.6 (6 g, 51.08%). MS (ES): m/z 384.8 [M+H]$^+$ Synthesis of Compound 19.7.

Compound was synthesized using general procedure B to obtain 1.7. (Yield: 42.78%). MS (ES): m/z 553.47 [M+H]$^+$ Synthesis of Compound I-144.

Compound was synthesized using general procedure C to obtain I-144 (Yield: 91.05%). MS (ES): m/z 453.40 [M+H]$^+$, LCMS purity: 100%, HPLC purity: 99.68%, Chiral HPLC: 99.34%, $^1$H NMR (DMSO-$d_6$, 400 MHZ): 9.02 (s, 1H), 8.52-8.51 (d, J=4.4 Hz, 1H), 8.30-8.27 (m, 2H), 8.09-8.05 (t, J=8.8 Hz, 1H), 7.99-7.98 (d, J=4.8 Hz, 1H), 7.84-7.83 (d, J=4.4 Hz, 1H), 7.75-7.71 (m, 1H), 7.44-7.43 (d, J=5.6 Hz, 1H), 6.45-6.41 (t, J=7.2 Hz, 1H), 6.25 (s, 1H), 5.01-4.83 (m, 1H), 3.03-3.00 (m, 1H), 2.91-2.90 (d, J=4.8 Hz, 3H), 1.28-1.22 (m, 1H), 0.96-0.87 (m, 1H).

Additionally, a revised synthesis of I-144 was developed as described below.

Revised synthetic route.

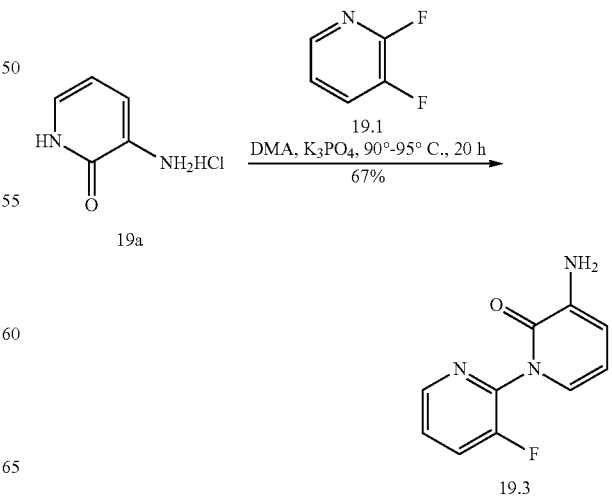

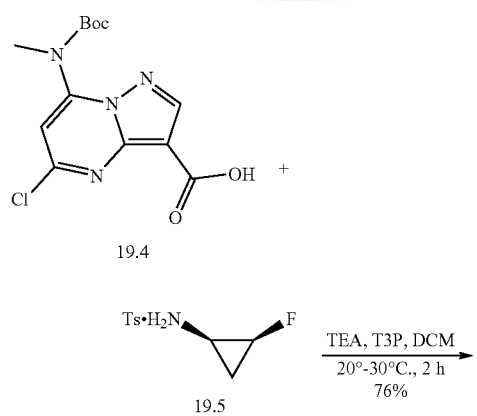
19.4
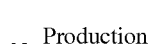
19.5
TEA, T3P, DCM
20°-30°C., 2 h
76%
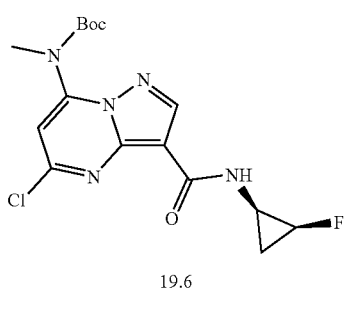
19.6
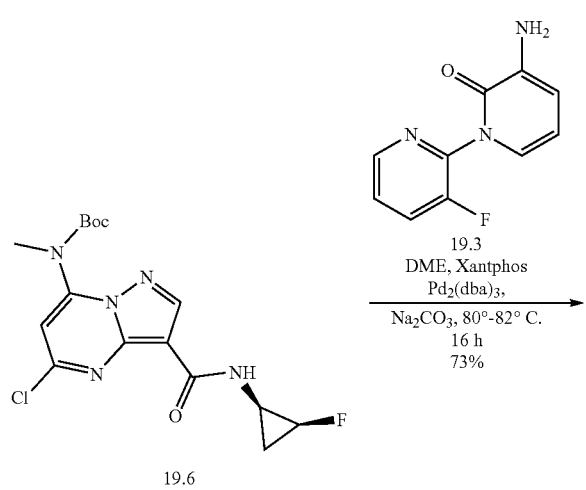
19.7
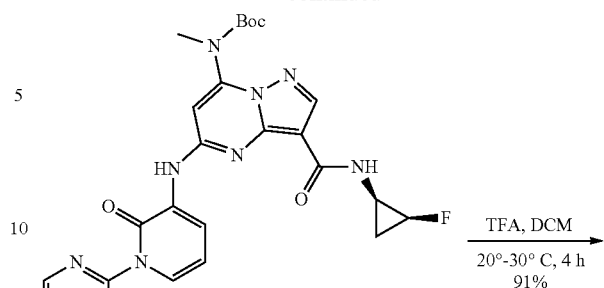
19.7
TFA, DCM
20°-30° C, 4 h
91%
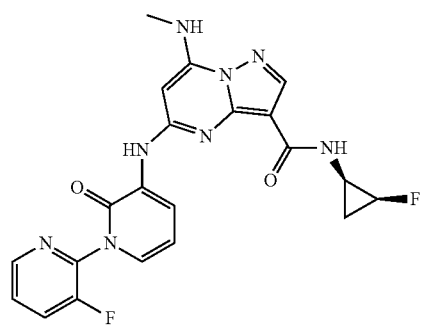
I-144
Production
All reactions and processes were performed under inert atmosphere of N₂ gas unless indicated otherwise.
Synthesis of Compound 19.6
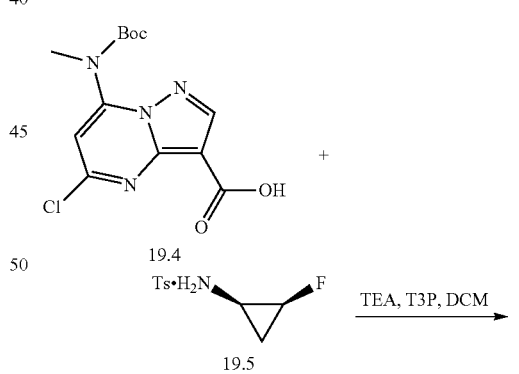
19.4
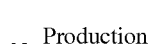
19.5
TEA, T3P, DCM
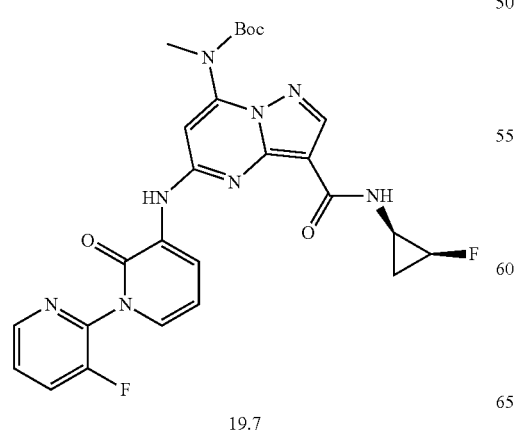
19.6

Table of Raw Materials, Solvents and Reagents

TABLE 6

Reagents and conditions for the preparation of 19.6.

| | Starting Materials | | | | | Reaction Conditions | | IPC Reference analytical method 1 | Result |
|---|---|---|---|---|---|---|---|---|---|
| Entry | 19.4 | 19.5 | TEA | T3P | DCM | Temp. (° C.) | Time (h) | (HPLC/ 220 nm) | (HPLC/ 220 nm) |
| 1 | 1.5 g (1.0 eq.) | 1.3 eq. | 4.0 eq. | 1.4 eq. | 10 V | 20~30 | 2 h | Compound 19.4: 1.1% product: 85.6% | No work up |
| 2 | 550 g (1.0 eq.) | 1.3 eq. | 4.0 eq. | 1.4 eq. | 10 V | 20~30 | 2 h | Compound 19.4: 1.2% product: 84.2%. | 494 g as off-white solid. Purity: 99.27% |

Process Description
1. Charged DCM (5.5 L, 10 V), 19.4 (550 g, 1.0 eq.) and TEA (681 g, 4.0 eq.) into a reactor under Nitrogen protection.
2. Charged drop wise T3P (750 g, 1.4 eq.) to the reactor at 20-30° C.
3. Stirred for 20 mins at 20-30° C.
4. Charged compound 19.5 (539 g, 1.3 eq.) to reactor batches at 20-30° C.
5. Stirred for 2 h at 20-30° C. under Nitrogen.
6. Sampled for IPC (84% purity).
7. Charged 1.0 N K$_2$CO$_3$ aqueous solution (11 L, 20 V) to reactor and justed the pH of aqueous to 9-10 with K$_2$CO$_3$ powder.
8. Stirred for 30 mins.
9. Separated, charged 1.0 N K$_2$CO$_3$ aqueous solution (4 L, 10 V) to organic phase.
10. Stirred for 30 mins.
11. Separated. Repeated step 10-12 for 4 times.
12. Washed the organic layer with brine (1.4 L, 2.5 V). Concentrated the organic phase under 40° C. under vacuum to 1V, charged EA (1.65 L, 3V) to residual, Concentrated the organic phase under 50° C. under vacuum to 1V.
13. Charged heptane (2.75 L, 5 V) to the residual, stirred for 30 mins, filtered.
14. Collected the cake, dried under vacuum under 60° C. until a constant weight to get 494 g compound 19.6 with 99.27% purity and 76.5% isolated yield.

Synthesis of Compound 19.3

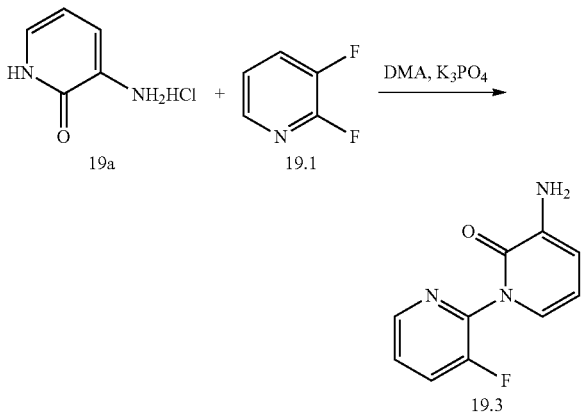

TABLE 7

Reagents and conditions for the preparation of 19.3.

| | Starting Materials | | | | Reaction Conditions | | IPC Reference analytical method 1 | Result |
|---|---|---|---|---|---|---|---|---|
| Entry | 19a (HCl salt) | 19.1 | K$_3$PO$_4$ | DMA | Temp (° C.) | Time (h) | (HPLC/ 220 nm) | (HPLC/ 220 nm) |
| 1 | 1.0 g (1.0 eq.) | 1.3 eq. | 3.6 eq. | 20 V | 90~95 | 20 h | Compound 19a: 0.7% Product: 87.0% | 141 g as light brown solid Purity: 97.41% |
| 2 | 150 g (1.0 eq.) | 1.3 eq. | 3.6 eq. | 20 V | 90~95 | 20 h | Compound 19a: 4.1% Product: 86.5% | |

Process Description

1. Charged DMA (3.0 L, 20 V), compound 19a HCl salt (150 g, 1.0 eq.), compound 19.1 (152.6 g, 1.3 eq.) and $K_3PO_4$ (780 g, 3.6 eq.) into a reactor under Nitrogen protection.
2. Heated to 90-95° C.
3. Stirred for overnight at 90-95° C.
4. Sampled for IPC (HPLC showed that compound 19a was 4.1%).
5. Cooled to 15~25° C.
6. Charged DCM (3.0 L, 20 V) and water (3.0 L, 20 V) to reactor, stirred for 0.5 h.
7. Filtered through Celite pad (300 g, 2 w/w, 15 cm wide and packed to a 3-4 cm height), washed the Celite pad with DCM (1.5 L, 10 V). If no Celite pad, the emulsification would occur during extraction.
8. Separated, extracted the aqueous phase with DCM (3.0 L, 20 V) for three times. (Note: About 5% compound 19.3 lost in aqueous phase)
9. Combined the organic phase, washed with brine (1.5 L, 10 V) for thrice times. (Note: About 5% compound 19.3 lost in brine)
10. Concentrated the organic phase under vacuum under 60° C. until no fractions to get crude oil (Assay yield 75%).
11. Charged drop wise the residual to heptane (7.5 L, 50 V) and stirred for 2 h at 20~30° C.
12. Filtered, washed the cake with heptane (1.5 L, 10 V).
13. Charge EA (0.3 L, 2 V) and crude solid (HPLC: 92%) to a reactor, stirred for 2 h, then charged drop wise heptane (1.2 L, 8 V) to mixture, stirred for 2 h.
14. Filtered, collected the cake and dried under vacuum under 60° C. until a constant weight to get 141.2 g compound 19.3 with 97.41% purity and 67.2% isolated yield.

Synthesis of Compound 19.7

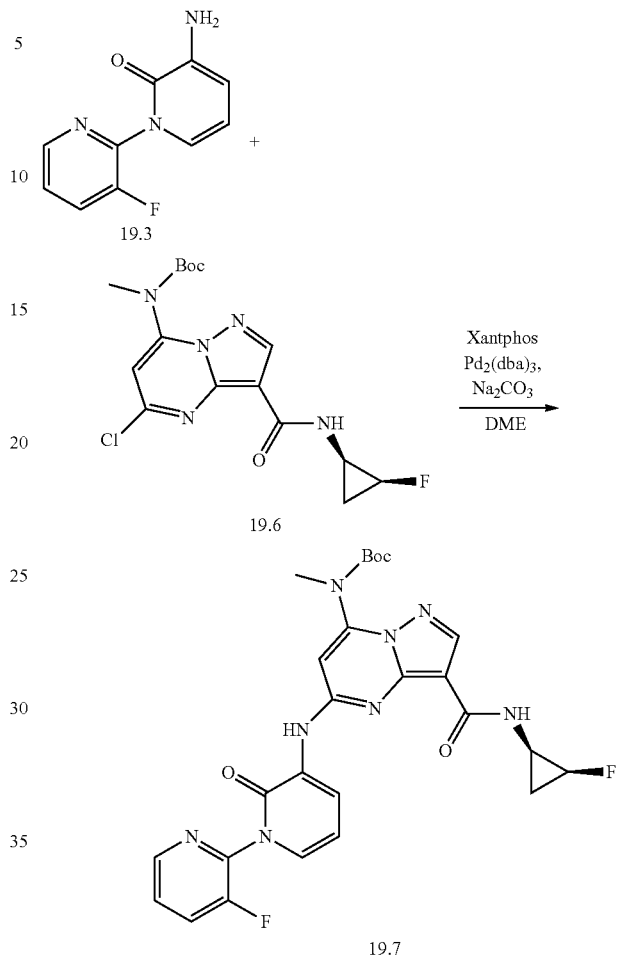

TABLE 8

| | Reagents and conditions for the preparation of 19.7. | | | | | | | | | |
|---|---|---|---|---|---|---|---|---|---|---|
| | | Starting Materials | | | | | Reaction Conditions | | IPC Reference analytical method 2 | Result |
| Entry | 19.3 | 19.6 | $Pd_2(dba)_3$ | Xantphos | $Na_2CO_3$ | DME | Temp (° C.) | Time (h) | (HPLC/ 220 nm) | (HPLC/ 220 nm) |
| 1 | 1.15 g (1.0 eq.) | 1.15 eq. | 0.065 eq. | 0.13 eq. | 2.2 eq. | 10 V | 80~82 | 16 h | Compound 19.3: 2.5% product: 89.3% | No work up |
| 2 | 240 g (1.0 eq.) | 1.15 eq. | 0.065 eq. | 0.13 eq. | 2.2 eq. | 10 V | 80~82 | 16 h | Compound 19.3: 1.5% product: 90.5% | 470 g as off-white solid Purity: 99.56% |

Process Description
1. Charged DME (2.4 L, 10 V), compound 19.3 (240 g, 1.0 eq.), compound 19.6 (514 g, 1.15 eq.) and Na$_2$CO$_3$ (272 g, 2.2 eq.) into a reactor under Nitrogen protection.
2. Stirred for 15 mins at room temperature with bubbled Nitrogen below the liquid level.
3. Charged Pd$_2$(dba)$_3$ (78.4 g, 0.065 eq.) and Xantphos (88.8 g, 0.13 eq.) to the reactor under Nitrogen.
4. Stirred for 30 mins with bubbled Nitrogen below the liquid level.
5. Heated to 80-82° C. and stirred for 16 h under Nitrogen.
6. Sampled for IPC (90.0% purity).
7. Cooled to 15~25° C.
8. Charged EA (7.2 L, 30 V) and water (12 L, 50V) to a reactor, charged reaction mixture to the reactor, stirred for 2 h.
9. Filtered, washed the cake with EA (1.2 L, 5 V), and separated the filtrate.
10. Separated.
11. Extracted the aqueous phase with EA (2.4 L, 10 V) for twice. Combined organic phase, washed with water (1.2 L, 5 V) for once.
12. Concentrated the organic layer under 50° C. under vacuum to 6 V.
13. Charged the residual to a reactor, charged drop wise n-Heptane (1.4 L, 6 V) to the reactor.
14. Filtered, washed the cake with EA:n-Heptane=1:1 (0.5 L, 2 V), charged the cake back to the reactor.
15. Charged EA (1.9 L, 8 V) to the reactor, heated to 77° C. and stirred for 1 h at 77° C.
16. Cooled to 15-25° C., charged drop wise n-Heptane (3.8 L, 12 V) to the reactor, stirred for 2 h.
17. Filtered, washed the cake with EA:n-Heptane=1:1 (0.5 L, 2 V).
18. Collected the cake, dried under vacuum under 60° C. until a constant weight to get 609 g compound 19.7 with 96.23% purity and 94.7% isolated yield. (Residual Pd: 10800 ppm)
19. Charged crude compound 19.7 to a reactor, charged Acetone (14.4 L, 60 V) to reactor. Heated to 55° C. and stirred until to get a clear solution.
20. Concentrated the solution to 9 V, stirred for 2 h at 15-25° C.
21. Filtered, washed the cake with Acetone (0.48 L, 2 V).
22. Collected the cake, dried under vacuum under 60° C. until a constant weight to get 550 g compound 19.7 with 99.51% purity and 78% isolated yield. (Residual Pd: 2120 ppm)
23. Charged pure compound 19.7 to a reactor, charged THF (14.4 L, 60 V) to reactor. Heated to 65° C. until to get a clear solution.
24. Charged Activated Carbon (100 g, 0.42 w/w) to reactor, stirred for overnight at 65° C. (Residual Pd: 512 ppm)
25. Cooled to 20-30° C., filtered.
26. Charged the filtration back to reactor, charged Thiol silica gel (50 g, 0.21 w/w) to reactor. Heated to 65° C. and stirred for overnight. (Residual Pd: 62 ppm)
27. Cooled to 20-30° C., filtered.
28. Concentrated the filtration to 4V, stirred for 2 hours at 20-30° C.
29. Filtered, collected the cake and dried under vacuum under 50° C. until a constant weight to get 470 g compound 19.7 with 99.56% purity and 73% isolated yield. (Residual Pd: 13 ppm)

Synthesis of I-144

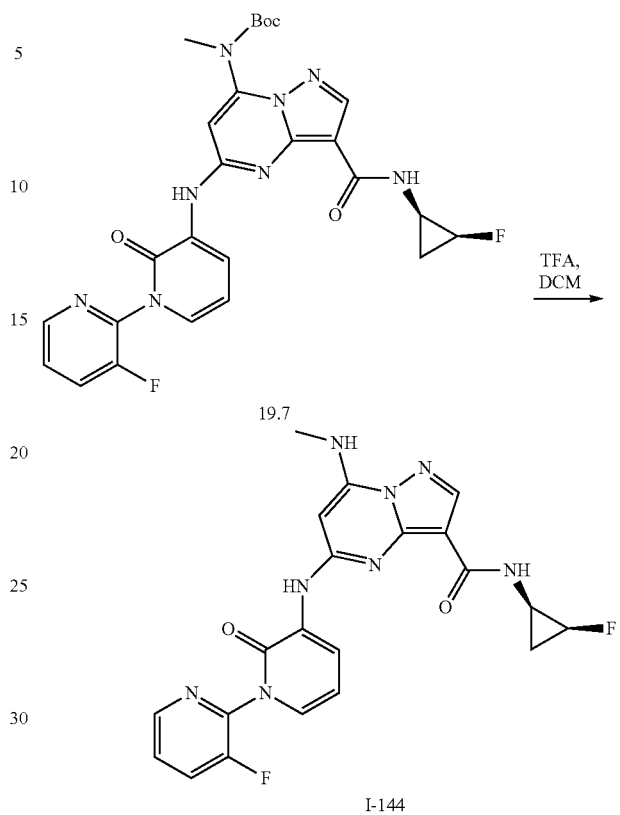

TABLE 9

Reagents and conditions for the preparation of I-144.

| Entry | Starting Materials | | | Reaction Conditions | | IPC Reference analytical method 1 (HPLC/ 220 nm) | Result (HPLC/ 220 nm) |
|---|---|---|---|---|---|---|---|
| | 19.7 | TFA | DCM | Temp (° C.) | Time (h) | | |
| 1 | 1.0 g | 2 V | 10V | 20~30 | 4 h | Compound 19.7: 0.4% Product: 98.7% | No work up |
| 2 | 468 g | 2 V | 10 V | 20~30 | 4 h | Compound 19.7: 0.5% Product: 98.7% | 350 g as off-white solid Purity: 99.5% |

Process Description
1. Charged DCM (4.7 L, 10 V), compound 19.7 (468 g, 1.0 eq.), TFA (940 mL, 2V) into a reactor under Nitrogen protection.
2. Stirred for 4 h at room temperature.
3. Sampled for IPC (HPLC showed that compound 19.7 was 0.5%).
4. Filtered to remove mechanical admixture.
5. Charged drop wise reaction mixture to 0.5 N K$_2$CO$_3$ (23.5 L, 50 v/w).
6. Stirred for 2 h.

7. Filtered, washed with soft water (2.4 L, 5 V) and DCM (940 mL, 2V).
8. Dried the cake to give an incompact solid. (KF≈15%)
9. Slurry the crude material with soft water (4.7 L, 10 V) for 3 h.
10. Filtered, wash with soft water (940 mL, 2 V).
11. Collected the cake, dried under vacuum under 60° C. until the KF was less than 0.5% to get 350 g I-144 with 99.1% purity and 91% isolated yield. The residual Pd was 15 ppm.

Analytical Section

TABLE 10

ANALYTICAL METHOD 1 ON IPC

| Instrument | Agilent LC 1260 System |
|---|---|
| Column | XDB C18 4.6*50 mm 1.8 um |
| Eluent A | 0.05% TFA in water |
| Eluent B | 0.05% TFA in ACN |
| Column temperature | 40° C. |
| Detector wavelength | 220 nm |
| Flow rate | 1.2 ml/min |
| Injection volume | 1 ul |

TABLE 11

Gradient for Analytical method 1 on IPC.

| Time (min) | 0.0 | 5.0 | 6.0 | 6.1 |
|---|---|---|---|---|
| % Mobile Phase A | 100 | 0 | 0 | 100 |
| % Mobile Phase B | 0 | 100 | 100 | 0 |

Post time: 1.5 min

TABLE 12

Analytical method 2 on IPC.

| Instrument | Agilent LC 1260 System |
|---|---|
| Column | XDB C18 4.6*50 mm 1.8 um |
| Eluent A | 0.05% TFA in water |
| Eluent B | 0.05% TFA in ACN |
| Column temperature | 40° C. |
| Detector wavelength | 220 nm |
| Flow rate | 1.2 ml/min |
| Injection volume | 1 ul |

TABLE 13

Gradient for Analytical method 2 on IPC.

| Time (min) | 0.0 | 4.5 | 6.5 | 6.6 |
|---|---|---|---|---|
| % Mobile Phase A | 90 | 0 | 0 | 90 |
| % Mobile Phase B | 10 | 100 | 100 | 10 |

Post time: 1.5 min

Example 20: 7-amino-N-cyclopropyl-5-((2-(trifluoromethoxy)pyridin-3-yl)amino)pyrazolo[1,5-a]pyrimidine-3-carboxamide (I-113)

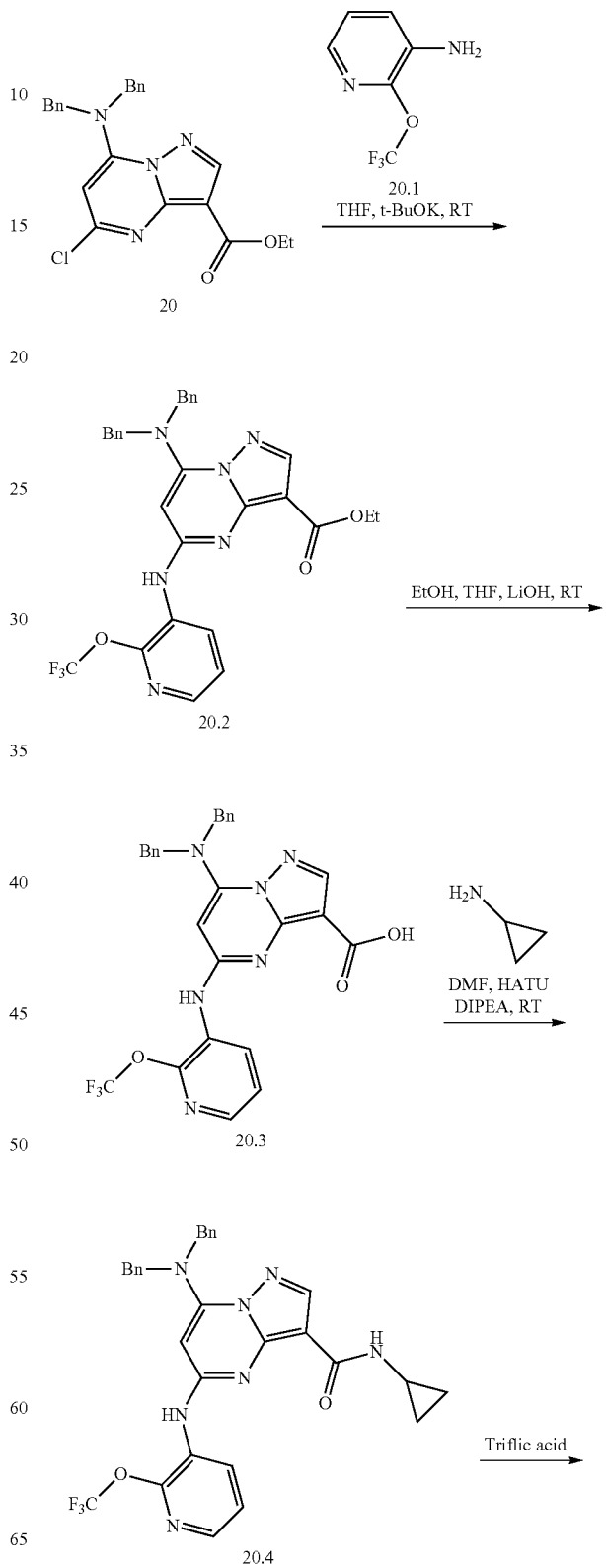

-continued

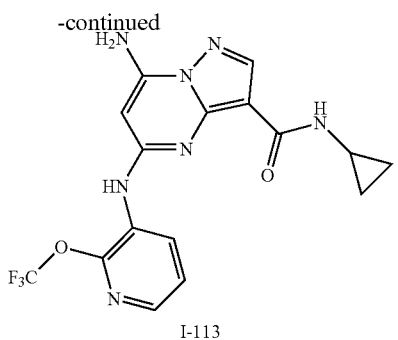

I-113

Synthesis of Compound 20.

Compound was synthesized using general procedure of core synthesis to obtain 20 (Yield: 62.0%). MS (ES): m/z 422.0 [M+H]$^+$ Synthesis of Compound 20.2.

To a cooled solution of 20 (0.380 g, 0.902 mmol, 1 eq), and 20.1 (0.144 g, 0.812 mmol, 0.9 eq) in tetrahydrofuran (5 mL) at 0° C. was added potassium ter-butoxide (1.80 mL, 1.80 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 17% ethyl acetate in hexane to obtain pure 20.2. (0.270 g, 53.16%). MS (ES): m/z 563.55 [M+H]$^+$.

Synthesis of Compound 20.3.

To a solution of 20.2 (0.270 g, 0.497 mmol, 1.0 eq), in tetrahydrofuran:methanol:water (8 mL, 2:2:1) was added lithium hydroxide (0.208 g, 4.97 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.4% methanol in dichloromethane to obtain pure 20.3 (0.210 g, 78.94%). MS(ES): m/z 535.50 [M+H]$^+$.

Synthesis of Compound 20.4.

Compound was synthesized using general procedure A to obtain 1.4. (0.060 g, 78.87%). MS (ES): m/z 574.58 [M+H]$^+$ Synthesis of Compound I-113.

Mixture of 20.4 (0.060 g, 0.104 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-113 (0.025 g, 60.76%). MS (ES): m/z 394.47 [M+H]$^+$, LCMS purity: 96.64%, HPLC purity: 95.18%, $^1$H NMR (DMSO-d$_6$, 400 MHZ): 9.25 (s, 1H), 8.33-8.31 (d, J=8 Hz, 1H), 8.16 (s, 1H), 8.13-8.12 (d, J=4 Hz, 1H), 7.74 (s, 2H), 7.65-7.64 (d, J=4 Hz, 1H), 7.47-7.44 (m, 1H), 5.84 (s, 1H), 2.74-2.70 (m, 1H), 0.67-0.62 (m, 2H), 0.24-0.20 (m, 2H).

Example 21: 7-amino-N-(oxetan-3-yl)-5-((6-(2-oxopyrrolidin-1-yl)pyridin-2-yl)amino)pyrazolo[1,5-a]pyrimidine-3-carboxamide (I-101)

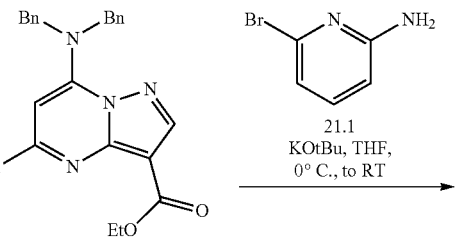

21
21.1
KOtBu, THF,
0° C., to RT

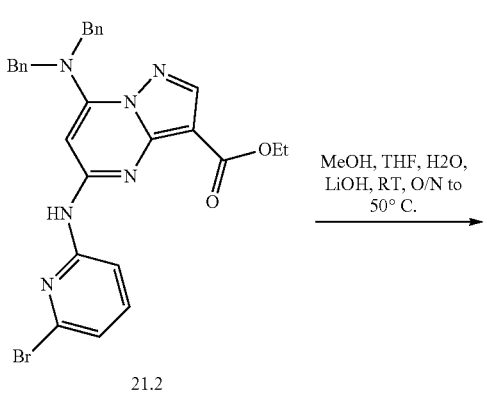

21.2
MeOH, THF, H2O,
LiOH, RT, O/N to
50° C.

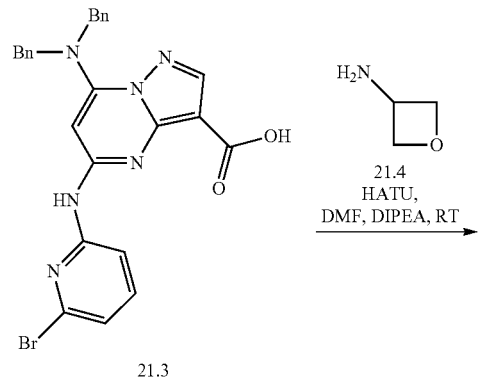

21.3
21.4
HATU,
DMF, DIPEA, RT

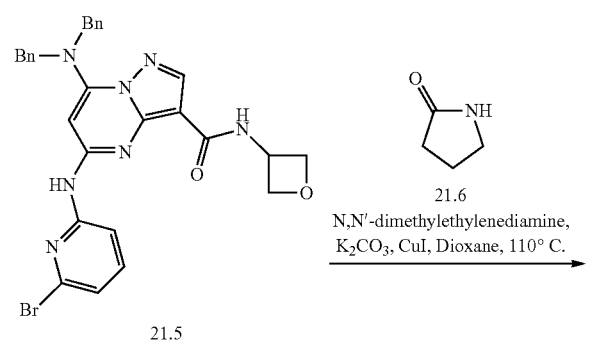

21.5
21.6
N,N'-dimethylethylenediamine,
K$_2$CO$_3$, CuI, Dioxane, 110° C.

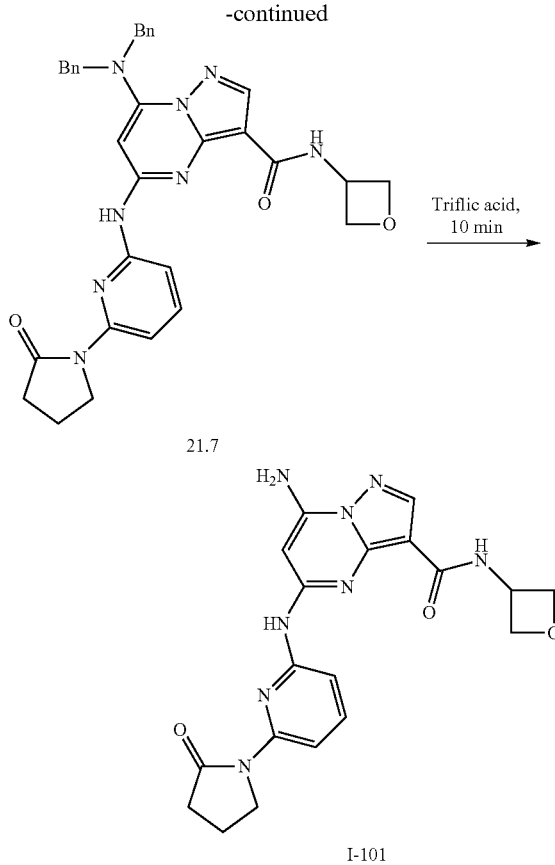

21.7

I-101

Synthesis of Compound 21.

Compound was synthesized using general procedure of core synthesis to obtain 21 (Yield: 62.0%). MS (ES): m/z 422.0 [M+H]+

Synthesis of Compound 21.2.

To a cooled solution of 21 (0.300 g, 0.712 mmol, 1 eq), and 21.1 (0.123 g, 0.712 mmol, 1 eq) in tetrahydrofuran (6 mL) at 0° C. was added potassium ter-butoxide (1.43 mL, 1.42 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 21.2. (0.180 g, 45.30%). MS (ES): m/z 558.45 [M+H]+

Synthesis of Compound 21.3.

To a solution of 21.2 (0.180 g, 0.322 mmol, 1.0 eq), in tetrahydrofuran:methanol:water (6 mL, 2:1:1) was added lithium hydroxide (0.135 g, 3.22 mmol, 10 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.2% methanol in dichloromethane to obtain pure 21.3 (0.165 g, 96.52%). MS(ES): m/z 530.40 [M+H]+.

Synthesis of Compound 21.5.

Compound was synthesized using general procedure A to obtain 21.5 (0.150 g, 82.34%). MS (ES): m/z 585.48 [M+H]+

Synthesis of Compound 21.7.

To a solution of 21.5 (0.150 g, 0.256 mmol, 1 eq) and 21.6 (0.043 g, 0.513 mmol, 2.0 eq) in 1,4-dioxane (2 mL) was added potassium carbonate (0.071 g, 0.513 mmol, 2.0 eq) and degassed with argon for 15 min. Copper iodide (0.0073 g, 0.038 mmol, 0.15 eq) and 1,2-dimethylethylenediamine (0.0067 g, 0.076 mmol, 0.3 eq) was added and reaction mixture again degassed with argon for 5 min followed by heating at 110° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.8% methanol in dichloromethane to obtain pure 21.7 (0.062 g, 41.04%). MS(ES): m/z 589.67 [M+H]+.

Synthesis of Compound I-101.

Mixture of 1.7 (0.062 g, 0.105 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-101 (0.027 g, 62.77%). MS (ES): m/z 409.39 [M+H]+, LCMS purity: 98.18%, HPLC purity: 95.11%, $^1$H NMR (DMSO-$d_6$, 400 MHZ): 9.50 (s, 1H), 8.18 (s, 1H), 7.84-7.82 (d, J=8 Hz, 1H), 7.67-7.65 (d, J=8 Hz, 1H), 7.42 (s, 2H), 7.16 (m, 2H), 6.77 (s, 1H), 4.50 (s, 1H), 4.38 (s, 1H), 4.24 (m, 2H), 4.09 (s, 2H), 3.64 (m, 1H), 3.47 (s, 1H), 2.12-2.08 (m, 3H).

Example 22: 7-amino-N-(oxetan-3-yl)-5-((2-(trifluoromethoxy)pyridin-3-yl)amino)pyrazolo[1,5-a]pyrimidine-3-carboxamide (I-103)

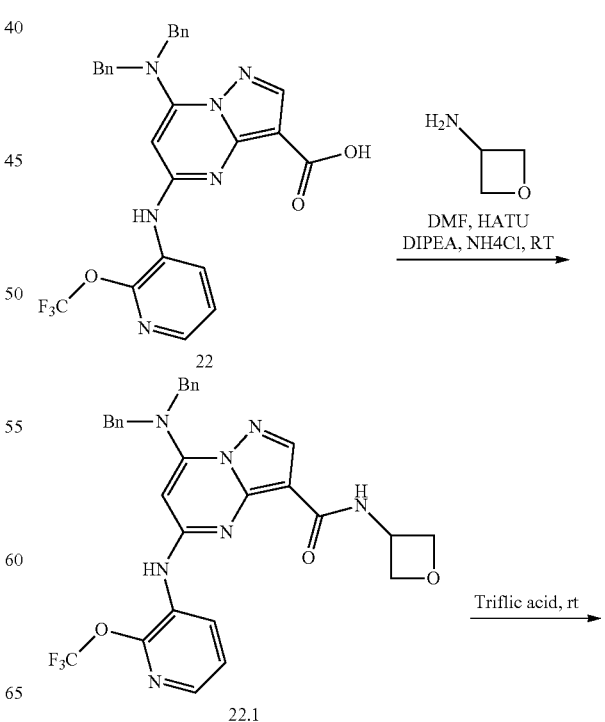

-continued

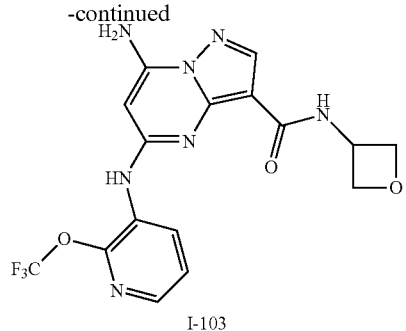

I-103

Synthesis of Compound 22.

Compound was synthesized as per experimental protocol of Example 20 (I-113) to obtain 22.

Synthesis of Compound 22.1.

Compound was synthesized using general procedure A to obtain 22.1. (0.055 g, 71.23%). MS (ES): m/z 590.58 [M+H]$^+$ Synthesis of Compound I-103:

Mixture of 22.1 (0.055 g, 0.093 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-103 (0.030 g, 78.76%), MS (ES): m/z 410.39 [M+H]$^+$, LCMS purity: 95.74%, HPLC purity: 96.31%, $^1$H NMR (DMSO-d$_6$, 400 MHZ): 9.49-9.46 (d, J=8.8 Hz, 1H), 9.03 (s, 1H), 8.20 (s, 1H), 7.92 (s, 1H), 7.61 (s, 2H), 7.38-7.36 (t, J=4 Hz, 1H), 7.02 (s, 1H), 6.06 (s, 1H), 4.78 (s, 1H), 4.37-4.35 (t, J=8 Hz, 1H), 4.17-4.16 (d, J=4 Hz, 2H), 3.64-3.63 (d, J=4 Hz, 1H).

Example 23: 7-amino-N-((1R,2S)-2-fluorocyclopropyl)-5-((2-isopropoxypyridin-3-yl)amino)-6-methylpyrazolo[1,5-a]pyrimidine-3-carboxamide (I-206)

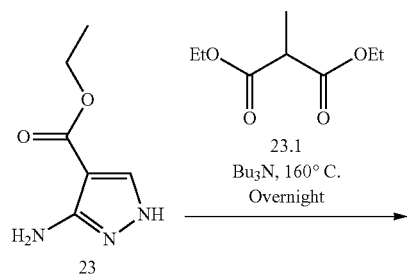

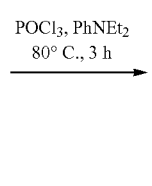

-continued

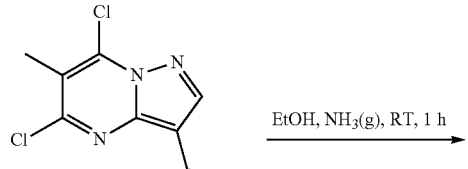

23.3

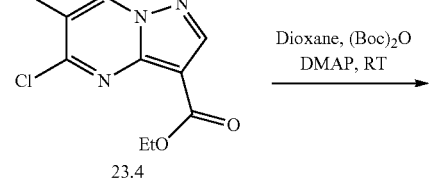

23.4

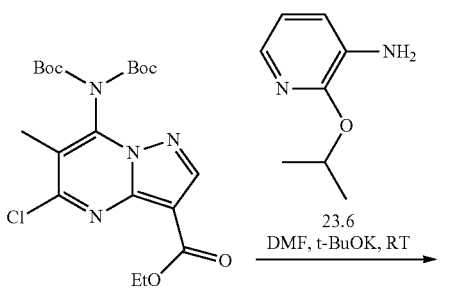

23.5    23.6

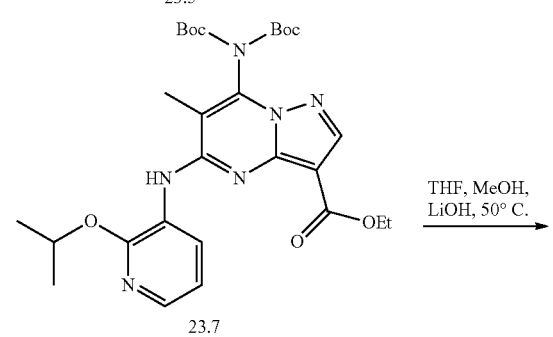

23.7

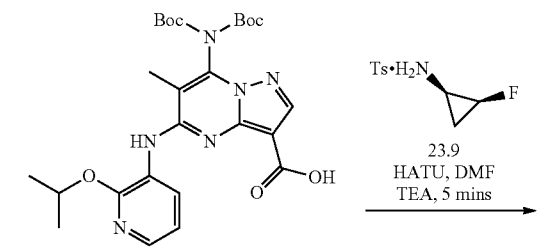

23.8    23.9

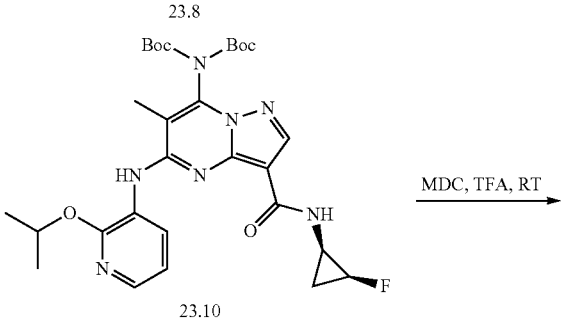

23.10

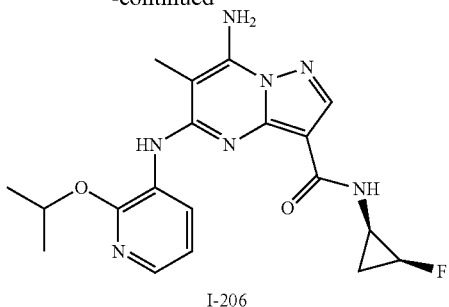

I-206

Synthesis of Compound 23.2.

A mixture of 23 (20 g, 128.90 mmol, 1.0 eq) and 23.1 (22.45 g, 128.90 mmol, 1.0 eq) in tributyl amine (48 mL) was stirred at 160° C. for 16 h. After completion of reaction, reaction mixture was cooled to room temperature and transferred in 1N sodium hydroxide solution and product was extracted with ethyl acetate. Aqueous layer was acidified using 1M hydrochloric acid. Precipitated solid was filtered, dried well to obtain pure 23.2 (13.5 g, 44.15%). MS(ES): m/z 238.22 [M+H]$^+$.

Synthesis of Compound 23.3.

To a cooled mixture of 23.2 (13.5 g, 56.91 mmol, 1.0 eq) and N,N-diethyl aniline (13.67 mL, 85.36 mmol, 1.5 eq) was added phosphoroxychloride (135 mL) at 0° C. The reaction mixture was stirred at 85° C. for 3 h. After completion of reaction, reaction mixture was transferred into ice cold water and product was extracted with dichloromethane. Organic layer was combined, dried over sodium sulphate and concentrated under reduced pressure to obtain crude material. This was further purified by column chromatography and compound was eluted in 24% ethyl acetate in hexane to obtain pure 23.3 (8 g, 51.28%). MS (ES): m/z 275.10 [M+H]$^+$ Synthesis of Compound 23.4.

To a solution of 23.3 (2 g, 7.30 mmol, 1.0 eq), in ethanol (40 mL) was added potassium carbonate (1.10 g, 8.03 mmol, 1.1 eq). Ammonia was purged through reaction mixture for 30 min. at room temperature. After completion of reaction, reaction mixture was transferred into ice cold water. Precipitated solid was filtered, dried well to obtain to obtain pure 23.4 (1.62 g, 87.18%). MS(ES): m/z 255.67 [M+H]$^+$.

Synthesis of Compound 23.5.

To a solution of 23.4 (1.62 g, 6.36 mmol, 1.0 eq) in N,N-dimethylformamide (16 mL) was added 4-Dimethylaminopyridine (0.076 g, 0.63 mmol, 0.1 eq) followed by Di-tert-butyl dicarbonate (2.77 g, 12.72 mmol, 2 eq). The reaction was stirred at room temperature for 1 h. After completion of reaction, reaction mixture transferred into ice cold water and precipitated solid was filtered, dried well to obtain crude material. This was further purified by column chromatography and compound was eluted in 15% ethyl acetate in hexane to obtain pure 23.5 (1 g, 34.56%). MS(ES): m/z 455.91 [M+H]$^+$.

Synthesis of Compound 23.6.

Compound was synthesized as per experimental protocol of I-72. to obtain 23.6.

Synthesis of Compound 23.7.

To a cooled solution of 23.5 (0.700 g, 1.54 mmol, 1.0 eq), and 23.6 (0.281 g, 1.85 mmol, 1.2 eq) in N,N-dimethylformamide (7 mL) at 0° C. was added potassium ter-butoxide (3.1 mL, 3.08 mmol, 2.0 eq). The reaction was stirred at 0° C. for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 18% ethyl acetate in hexane to obtain pure 23.7 (0.690 g, 78.58%). MS (ES): m/z 571.65 [M+H].

Synthesis of Compound 23.8.

To a solution of 23.7 (0.690 g, 1.21 mmol, 1.0 eq), in tetrahydrofuran:methanol:water (12 mL, 1:1:1) was added lithium hydroxide (0.508 g, 12.1 mmol, 10 eq). The reaction was stirred at 50° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.9% methanol in dichloromethane to obtain pure 23.8 (0.480 g, 73.16%). MS(ES): m/z 543.59 [M+H]$^+$.

Synthesis of Compound 23.10.

Compound was synthesized using general procedure A to obtain 23.10. (0.104 g, 58.81%). MS (ES): m/z 600.66 [M+H]$^+$ Synthesis of Compound I-206:

Compound was synthesized using general procedure C to obtain I-206 (0.065 g, 93.83%), MS (ES): m/z 400.50 [M+H]$^+$, LCMS purity: 100%, HPLC purity: 99.61%, CHIRAL HPLC purity: 100%, $^1$H NMR (DMSO-d$_6$, 400 MHZ): 8.17 (s, 1H), 8.02-8.00 (d, J=8 Hz, 1H), 7.95-7.94 (d, J=4 Hz, 1H), 7.79 (s, 1H), 7.69-7.68 (d, J=4 Hz, 1H), 7.49 (s, 2H), 6.99-6.98 (t, J=4 Hz, 1H), 5.30-5.24 (m, 1H), 4.80-4.68 (m, 1H), 2.85-2.82 (m, 1H), 2.16 (s, 3H), 1.27-1.25 (t, J=8 Hz, 6H), 1.10-1.05 (m, 1H), 0.57-0.51 (m, 1H).

Example 24: 7-amino-N-cyclopropyl-5-((2-isopropoxypyridin-3-yl)amino)-6-methylpyrazolo[1,5-a]pyrimidine-3-carboxamide (I-207)

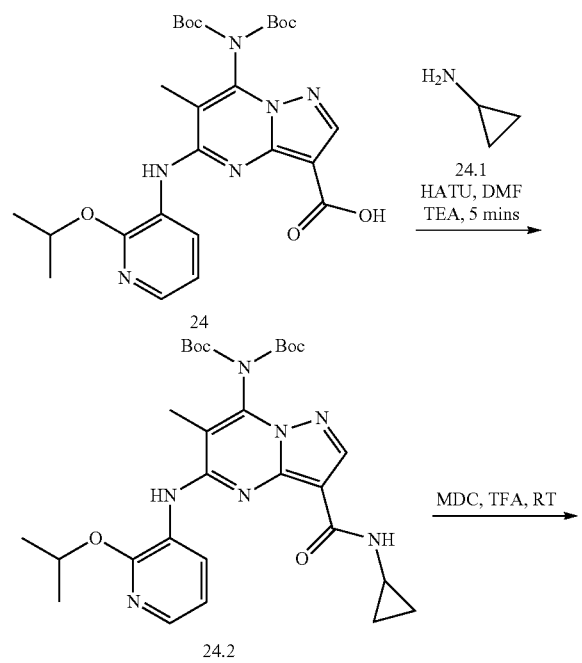

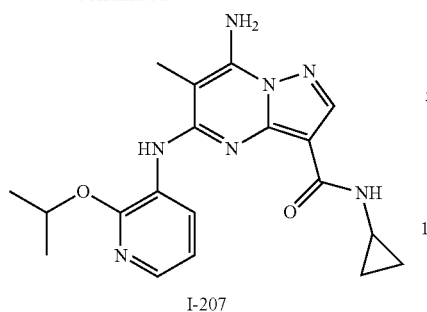

I-207

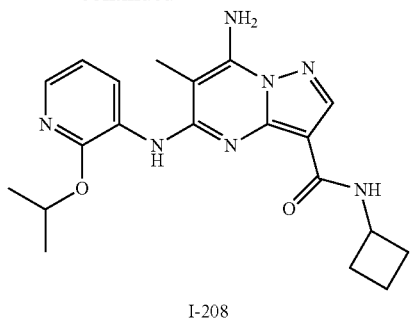

I-208

Synthesis of Compound 24.

Compound was synthesized as per experimental protocol of Example 23 to obtain 24.

Synthesis of Compound 24.2.

Compound was synthesized using general procedure A to obtain 24.2. (0.089 g, 51.89%). MS (ES): m/z 582.67 [M+H]$^+$ Synthesis of Compound I-207:

Compound was synthesized using general procedure C to obtain I-207 (0.055 g, 94.24%), MS (ES): m/z 382.33 [M+H]$^+$, LCMS purity: 98.84%, HPLC purity: 98.21%, $^1$H NMR (DMSO-d$_6$, 400 MHZ): 8.12 (s, 1H), 7.99-7.98 (d, J=4 Hz, 1H), 7.95-7.93 (d, J=8 Hz, 1H), 7.84 (s, 1H), 7.63-7.62 (d, J=4 Hz, 1H), 7.44 (s, 2H), 7.03-7.00 (m, 1H), 5.28-5.24 (m, 1H), 2.74-2.69 (m, 1H), 2.15 (s, 3H), 1.23-1.22 (d, J=4 Hz, 6H), 0.65-0.61 (m, 2H), 0.19-0.15 (m, 2H).

Example 25: 7-amino-N-cyclobutyl-5-((2-isopropoxypyridin-3-yl)amino)-6-methyl pyrazolo[1,5-a]pyrimidine-3-carboxamide (I-208)

Synthesis of Compound 25.

Compound was synthesized as per experimental protocol of Example 23 to obtain 25.

Synthesis of Compound 25.2.

Compound was synthesized using general procedure A to obtain 25.2. (0.095 g, 54.08%). MS (ES): m/z 596.70 [M+H]$^+$ Synthesis of Compound I-208:

Compound was synthesized using general procedure C to obtain I-208 (0.058 g, 91.96%), MS (ES): m/z 396.53 [M+H]$^+$, LCMS purity: 100%, HPLC purity: 99.73%, $^1$H NMR (DMSO-d$_6$, 400 MHZ): 8.09 (s, 1H), 8.02-8.00 (d, J=8 Hz, 2H), 7.90 (s, 1H), 7.84-7.82 (d, J=8 Hz, 1H), 7.43 (s, 2H), 7.05-7.03 (t, J=8 Hz, 1H), 5.35-5.28 (m, 1H), 4.38-4.32 (m, 1H), 2.16 (s, 5H), 1.62-1.55 (m, 4H), 1.24-1.22 (d, J 8 Hz, 6H).

Example 26: 5-((1-(5-(dimethylcarbamoyl)pyrazin-2-yl)-2-oxo-1,2-dihydropyridin-3-yl)amino)-7-(methylamino)pyrazolo[1,5-a]pyrimidine-3-carboxamide (I-53)

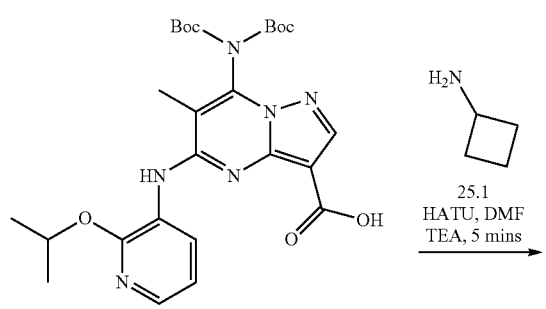

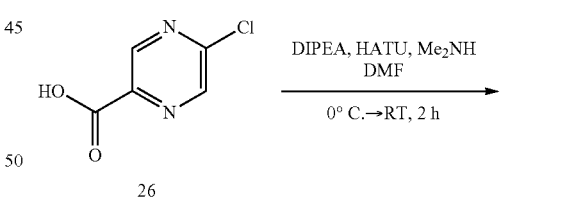

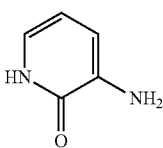

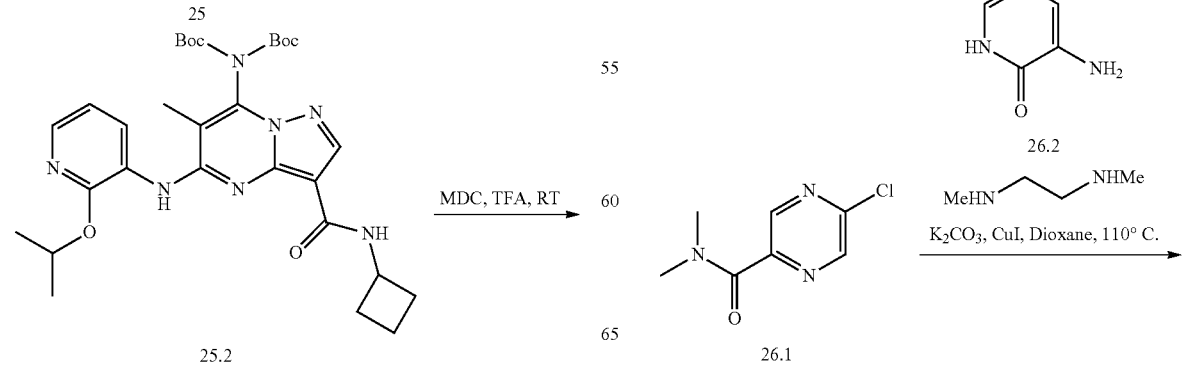

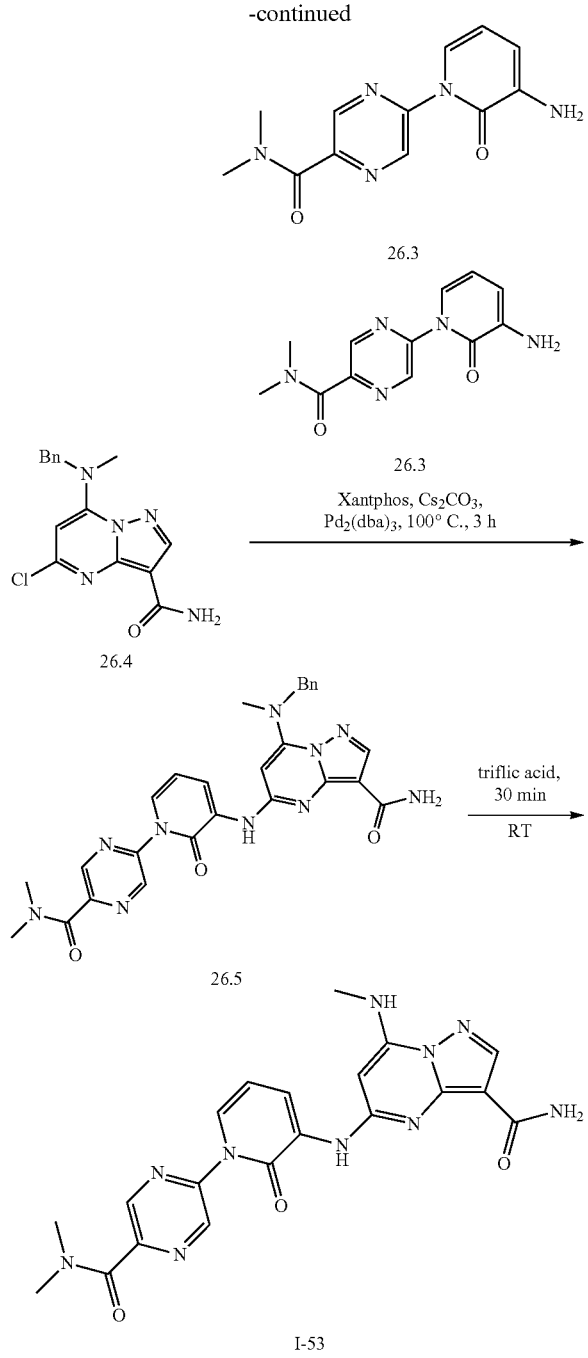

Synthesis of Compound 26.1.

To a cooled solution of 26 (3 g, 18.92 mmol, 1.0 eq), in N,N-dimethylformamide (30 mL) was added 1-[Bis(dimethylamino)methylene]-1H-1,2,3-triazolo[4,5-b]pyridinium 3-oxid hexafluorophosphate (8.65 g, 22.70 mmol, 1.2 eq) and stirred at room temperature for 20 min. Reaction mixture again cooled diisopropylethylamine (7.32 mL, 56.76 mmol, 3.0 eq) was added followed by addition of dimethylamine (0.851 g, 18.92 mmol, 1.0 eq). The reaction mixture was stirred at room temperature for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 0.9% methanol in dichloromethane to obtain 26.1 (2.5 g, 71.18%). MS(ES): m/z 186.61 [M+H]$^+$.

Synthesis of Compound 26.3.

To a solution of 26.1 (3 g, 13.47 mmol, 1.2 eq) and 26.2 (0.989 g, 11.22 mmol, 1.0 eq) in 1,4-dioxane (30 mL) was added potassium carbonate (3.71 g, 26.94 mmol, 2.0 eq) and degassed with argon for 15 min. Copper iodide (0.371 g, 2.69 mmol, 0.2 eq) and 1,2-dimethylethylenediamine (0.474 g, 5.38 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 26.3 (1.2 g, 41.24%). MS(ES): m/z 260.27 [M+H]$^+$.

Synthesis of Compound 26.4.

Compound was synthesized using general procedure of core synthesis to obtain 26.4 (Yield: 62.0%). MS (ES): m/z 316.76 [M+H]$^+$ Synthesis of Compound 26.5.

To a solution of 26 (0.150 g, 0.478 mmol, 1.0 eq) in 1,4-dioxane (5 mL) was added 26.1 (0.147 g, 0.570 mmol, 1.2 eq), cesium carbonate (0.359 g, 1.53 mmol, 2.0 eq). The reaction mixture was degassed for 10 min. under argon atmosphere, then tris(dibenzylideneacetone)dipalladium(0) (0.023 g, 0.023 mmol, 0.05 eq) and 4,5-Bis(diphenylphosphino)-9,9-dimethylxanthene (0.027 g, 0.047 mmol, 0.1 eq) were added, again degassed for 5 min. The reaction was stirred at 100° C. for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 2% methanol in dichloromethane as eluant to obtain pure 26.5 (0.090 g, 35.18%). MS(ES): m/z 539.57 [M+H]$^+$.

Synthesis of Compound I-53.

Mixture of 26.5 (0.090 g, 0.167 mmol, 1.0 eq) and triflic acid (2 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-53 (0.025 g, 33.36%). MS (ES): m/z 449.51 [M+H]$^+$, LCMS purity: 98.97%, HPLC purity: 97.25%, $^1$H NMR (DMSO-d$_6$, 400 MHZ): 9.21 (s, 1H), 9.06 (s, 1H), 8.91 (s, 1H), 8.33-8.31 (t, J=8 Hz, 1H), 8.21 (s, 1H), 7.93 (s, 1H), 7.65-7.63 (d, J=8 Hz, 1H), 7.33 (s, 1H), 7.24 (bs, 1H), 6.51-6.50 (t, J=4 Hz, 1H), 6.24 (s, 1H), 3.08-3.05 (d, J=12 Hz, 6H), 2.92-2.91 (d, J=4 Hz, 3H).

Example 27: N-cyclopropyl-5-((1-(5-(dimethylcar-bamoyl)pyrazin-2-yl)-2-oxo-1,2-dihydropyridin-3-yl)amino)-7-(methylamino)pyrazolo[1,5-a]pyrimidine-3-carboxamide (I-127)

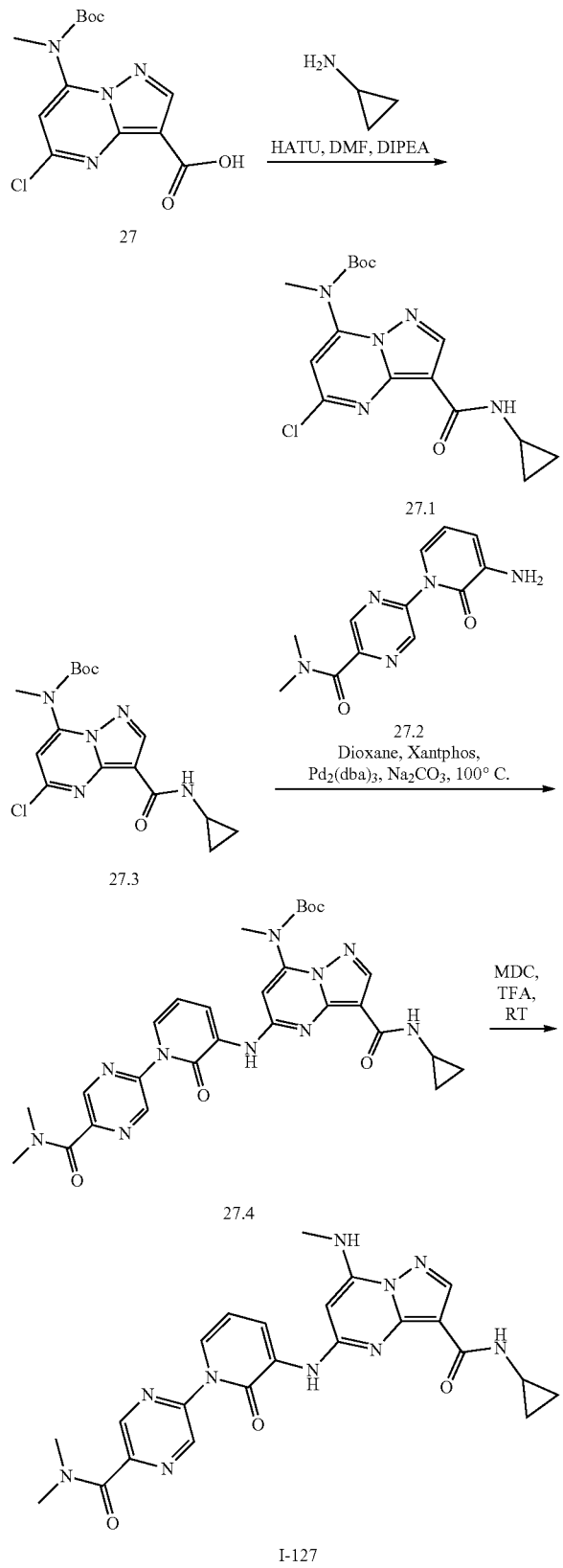

Synthesis of Compound 27.

Compound was synthesized using general procedure of core synthesis to obtain 27. (Yield: 71.67%). MS (ES): m/z 326.74 [M+H]+

Synthesis of Compound 27.1.

Compound was synthesized using general procedure of A synthesis to obtain 27.1 (Yield: 57.16%). MS (ES): m/z 366.82 [M+H]+.

Synthesis of Compound 27.2.

Compound was synthesized as per experimental protocol of Example 26.

Synthesis of Compound 27.3.

Compound was synthesized using general procedure B to obtain 27.3. (Yield: 22.37%). MS (ES): m/z 589.63 [M+H]+

Synthesis of Compound I-127.

Compound was synthesized using general procedure C to obtain I-127 (Yield: 66.94%). MS (ES): m/z 489.51 [M+H]+, LCMS purity: 100%, HPLC purity: 98.60%, $^1$H NMR (DMSO-$d_6$, 400 MHZ): 9.23 (s, 1H), 9.09 (s, 1H), 8.93 (s, 1H), 8.29-8.28 (d, J=7.2 Hz, 1H), 8.22 (s, 1H), 7.97-7.96 (d, J=4.8 Hz, 1H), 7.85-7.84 (d, J=4 Hz, 1H), 7.70-7.68 (d, J=6.8 Hz, 1H), 6.56-6.52 (t, J=7.2 Hz, 1H), 6.24 (s, 1H), 3.09-3.06 (m, 6H), 2.92-2.86 (m, 4H), 1.35-1.33 (d, J=8 Hz, 1H), 1.24 (s, 1H), 0.834-0.788 (m, 2H).

Example 28: N-cyclopropyl-7-(methylamino)-5-((1-(5-methylthiazol-2-yl)-2-oxo-1,2-dihydropyridin-3-yl)amino)pyrazolo[1,5-a]pyrimidine-3-carboxamide (I-261)

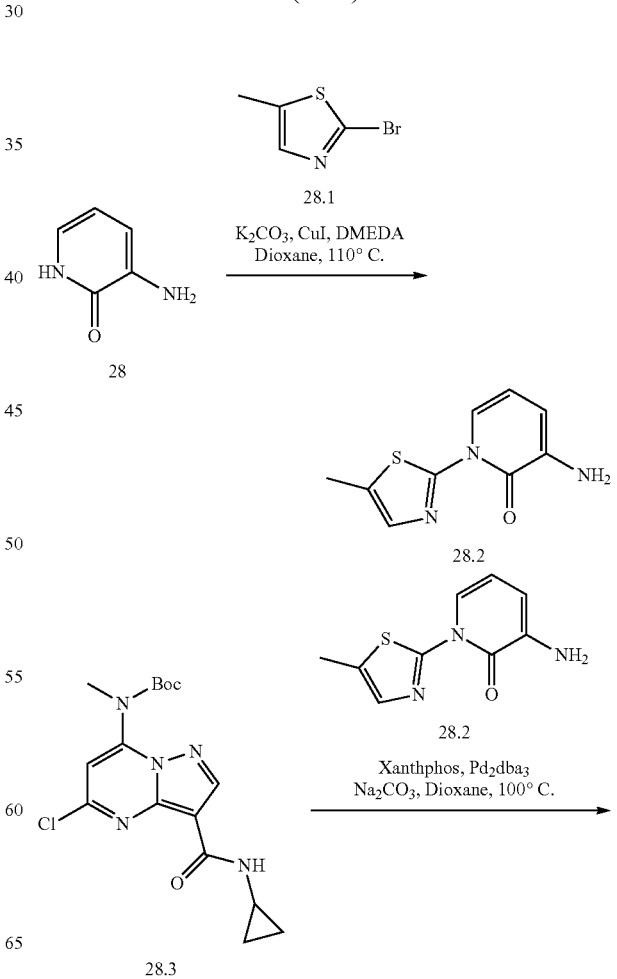

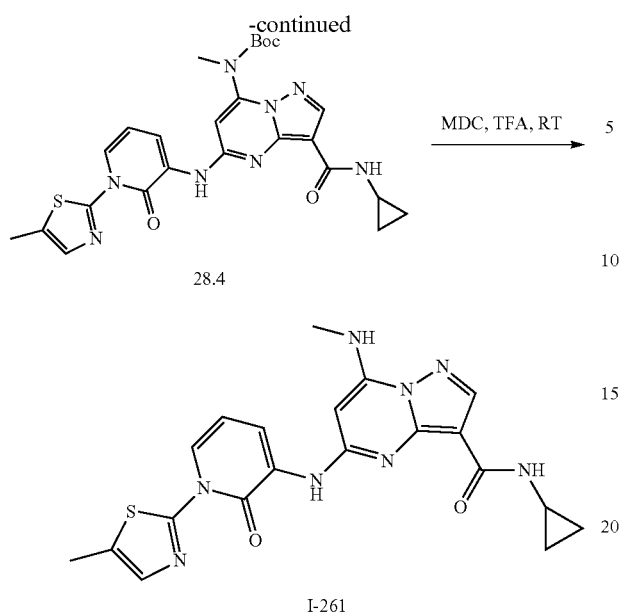

Synthesis of Compound 28.2.

To a solution of 28 (1 g, 9.08 mmol, 1 eq) and 28.1 (1.94 g, 10.90 mmol, 1.2 eq) in 1,4-dioxane (10 mL) was added potassium carbonate (2.50 g, 18.16 mmol, 2.0 eq) and degassed with argon for 15 min. Copper iodide (0.345 g, 1.81 mmol, 0.2 eq) and 1,2-dimethylethylenediamine (0.320 g, 3.63 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 28.2 (0.400 g, 21.25%). MS(ES): m/z 208.25 [M+H]$^+$.

Synthesis of Compound 28.3.

Compound was synthesized as per experimental protocol of Example 27 to obtain 28.3 (Yield: 57.16%), MS (ES): m/z 366.82 [M+H]$^+$

Synthesis of Compound 28.4.

Compound was synthesized using general procedure B to obtain 28.4 (0.060 g, 40.90%), MS (ES): m/z 537.61 [M+H]$^+$

Synthesis of Compound I-261:

Compound was synthesized using general procedure C to obtain I-261 (0.030 g, 61.47%), MS (ES): m/z 437.17 [M+H]$^+$, LCMS purity: 98.07%, HPLC purity: 99.38%, $^1$H NMR (DMSO-d$_6$, 400 MHZ): 9.29 (s, 1H), 8.46-8.44 (d, J=8 Hz, 1H), 8.28-8.27 (d, J=4 Hz, 1H), 8.22 (s, 1H), 8.00-7.99 (d, J=4 Hz, 1H), 7.81-7.80 (d, J=4 Hz, 1H), 7.53 (s, 1H), 6.65-6.64 (t, J=4 Hz, 1H), 6.26 (s, 1H), 2.92-2.91 (d, J=4 Hz, 3H), 2.86-2.85 (m, 1H), 2.48 (s, 3H), 0.80-0.78 (m, 2H), 0.51 (bs, 2H).

Example 29: N-(2-hydroxycyclobutyl)-7-(methylamino)-5-((1-(5-methylthiazol-2-yl)-2-oxo-1,2-dihydropyridin-3-yl)amino)pyrazolo[1,5-a]pyrimidine-3-carboxamide (I-676)

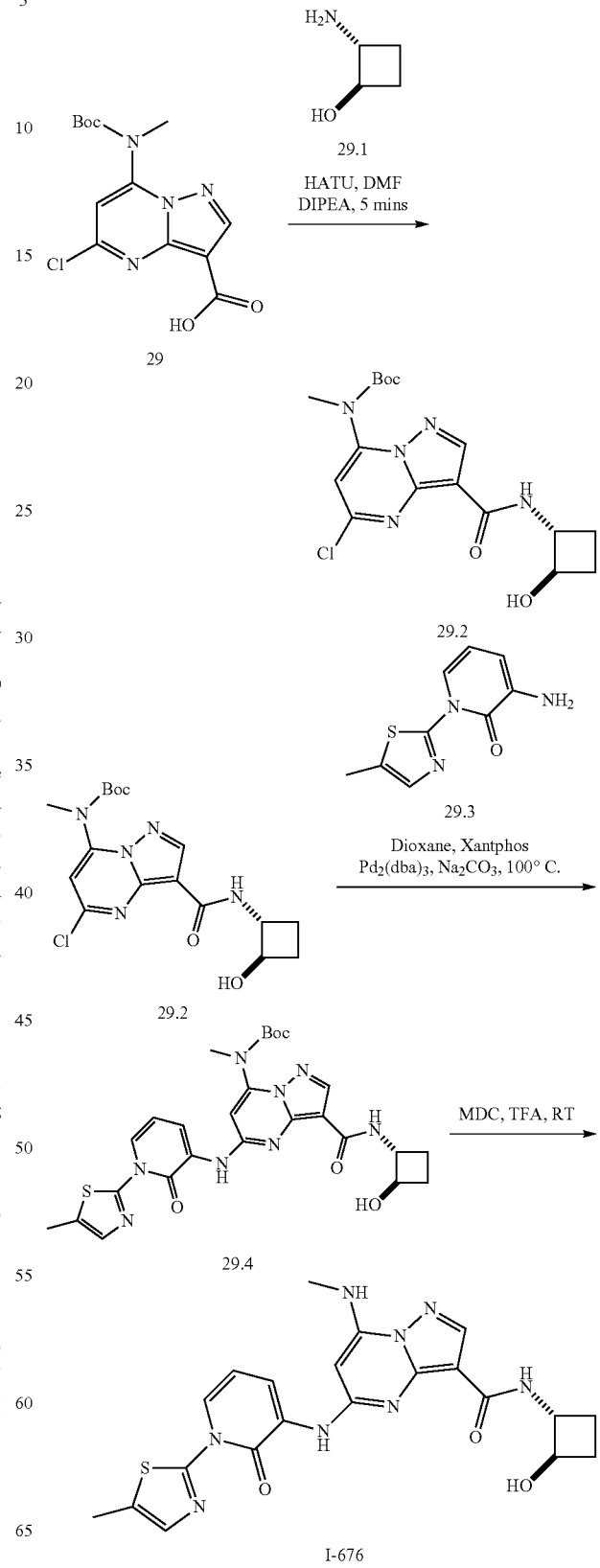

889

Synthesis of Compound 29.

Compound was synthesized using general procedure of core synthesis to obtain 29 (Yield: 71.67%), MS (ES): m/z 327.08 [M+H]+.

Synthesis of Compound 29.2.

Compound was synthesized using general procedure A to obtain 29.2. (0.640 g, 52.83%), MS (ES): m/z 396.14 [M+H]+

Synthesis of Compound 29.3.

Compound was synthesized as per experimental protocol of Example 28 to obtain 29.3. (Yield: 21.25%), MS (ES): m/z 208.25 [M+H]+

Synthesis of Compound 29.4.

Compound was synthesized using general procedure B to obtain 29.4. (0.130 g, 72.65%), MS (ES): m/z 567.2 [M+H]+

Synthesis of Compound I-676:

Compound was synthesized using general procedure C to obtain I-676 (0.100 g, 93.43%), MS (ES): m/z 467.22 [M+H]+, LCMS purity: 100%, HPLC purity: 95.88%, CHIRAL HPLC: 47.58%, 46.55%, $^1$H NMR (DMSO-$d_6$, 400 MHZ): 9.34 (s, 1H), 8.47-8.46 (d, J=6.4 Hz, 1H), 8.39-8.37 (d, J=7.2 Hz, 1H), 8.23 (s, 1H), 8.02-8.00 (d, J=8.8 Hz, 2H), 7.54 (s, 1H), 6.68-6.64 (t, J=7.2 Hz, 1H), 6.29 (s, 1H), 5.78 (bs, 1H), 4.25-4.20 (t, J=8.4 Hz, 2H), 3.87-3.85 (d, J=8 Hz, 1H), 2.93 (bs, 3H), 2.07-2.01 (m, 2H), 1.52-1.47 (d, J=9.2 Hz, 2H), 1.25-1.20 (m, 2H).

Example 30: N-(-2-methoxycyclobutyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-814)

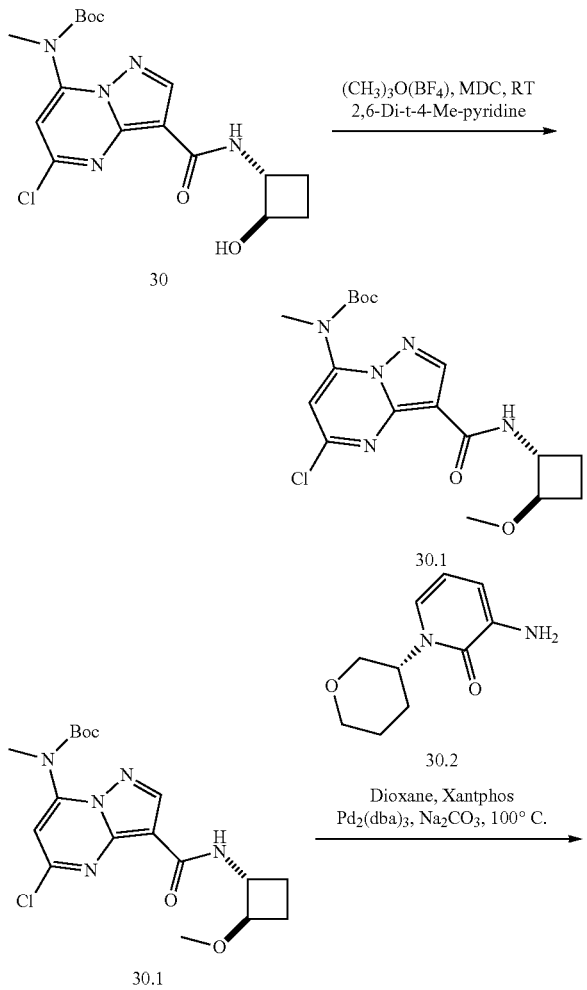

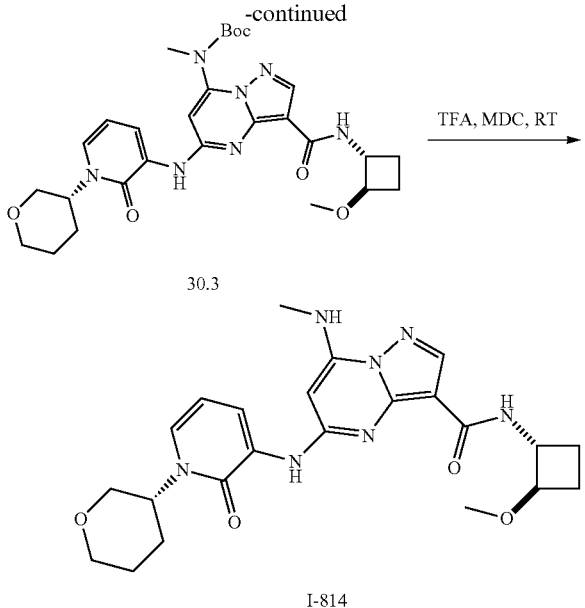

Synthesis of Compound 30.

Compound was synthesized as per experimental protocol of Example 29 to obtain 30. (Yield: 52.83%), MS (ES): m/z 396.14 [M+H]+

Synthesis of Compound 30.1.

To a solution of 30 (1.0 g, 2.52 mmol, 1 eq) in dichloromethane (20 mL), Triethyloxonium tetrafluoroborate (0.957 g, 5.04 mmol, 2.0 eq) and 2,6-Di-tert-butyl-4-methylpyridine (1.54 g, 7.56 mmol, 3.0 eq) was added. The reaction mixture was stirred at room temperature for 4 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 30.1. (0.600 g, Yield: 57.95%). MS (ES): m/z 410.16 [M+H]+

Synthesis of Compound 30.2.

Compound was synthesized as per experimental protocol of Intermediate B-i to obtain 30.2. MS (ES): m/z 195.11 [M+H]+

Synthesis of Compound 30.3.

Compound was synthesized using general procedure B to obtain 30.3. (0.150 g, 86.65%), MS (ES): 568.28 [M+H]+

Synthesis of Compound I-814:

Compound was synthesized using general procedure C to obtain I-814 (0.120 g, 97.13%), MS (ES): m/z 468.51 [M+H]+, LCMS purity: 100%, HPLC purity: 96.92%, Chiral HPLC: 49.46%, 49.90%, $^1$H NMR (DMSO-$d_6$, 400 MHZ): 8.96 (s, 1H), 8.26-8.24 (d, J=7.2 Hz, 1H), 8.21 (s, 1H), 8.08-8.06 (d, J=8.8 Hz, 1H), 7.95-7.94 (d, J=4.4 Hz, 1H), 7.58-7.56 (t, J=7.2 Hz, 1H), 6.36-6.33 (t, J=6.8 Hz, 1H), 6.24 (s, 1H), 4.90 (bs, 1H), 4.35-4.30 (m, 1H), 3.86 (bs, 2H), 3.73-3.68 (m, 1H), 3.62-3.57 (t, J=10 Hz, 1H), 3.50-3.45 (t, J=10.4 Hz, 1H), 3.36 (s, 1H), 3.21 (bs, 2H), 2.92-2.91 (d, J=4.8 Hz, 3H), 1.78 (bs, 2H), 1.56-1.51 (m, 1H), 1.43-1.35 (m, 2H), 1.25 (bs, 2H), 1.12-1.09 (m, 1H).

Example 31: N-((1R,2R)-2-methoxycyclobutyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-902), N-((1S,2S)-2-methoxycyclobutyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-903)

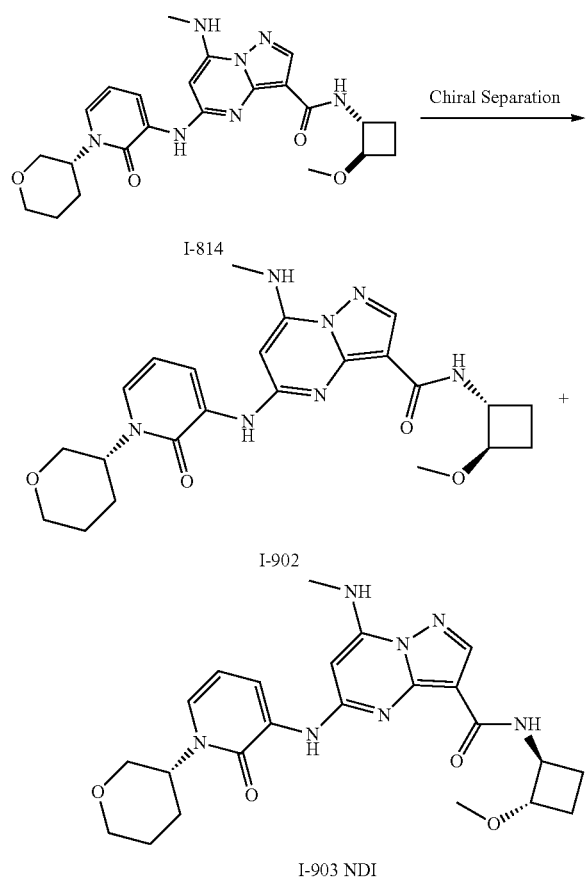

Synthesis of Compound I-902 & I-903.

Isomers of I-814 (0.12 g) were separated using column (CHIRAL PAK AD-H 250×4.6 mm, 5 u) 0.1% DEA in MEOH (70-30) to get pure fraction-1 (FR-a) and fraction-2 (FR-b). FR-a was concentrated under reduced pressure at 30° C. to afford pure FR-a (0.025 g). MS(ES): m/z 468.52 [M+H]⁺, LCMS purity: 99.58%, HPLC purity: 99.24%, CHIRAL HPLC purity: 100%, ¹H NMR (DMSO-d₆, 400 MHZ): 8.96 (s, 1H), 8.28-8.26 (d, J=5.6 Hz, 1H), 8.21 (s, 1H), 8.08-8.06 (d, J=9.2 Hz, 1H), 7.96-7.94 (d, J=4.8 Hz, 1H), 7.58-7.56 (d, J=6.8 Hz, 1H), 6.36-6.33 (t, J=7.2 Hz, 1H), 6.24 (s, 1H), 4.92-4.87 (m, 1H), 4.34-4.30 (m, 1H), 3.88-3.83 (m, 2H), 3.73-3.68 (m, 1H), 3.62-3.57 (m, 1H), 3.50-3.45 (t, J=8.8 Hz, 1H), 3.21 (s, 3H), 2.92-2.91 (d, J=4.8 Hz, 3H), 2.17-1.97 (m, 4H), 1.78-1.72 (m, 2H), 1.56-1.49 (m, 1H), 1.43-1.35 (m, 1H).

FR-b was concentrated under reduced pressure at 30° C. to afford pure FR-b (0.026 g). MS(ES): m/z 468.23 [M+H]⁺, LCMS purity: 100%, HPLC purity: 99.27%, CHIRAL HPLC purity: 100%, ¹H NMR (DMSO-d₆, 400 MHZ): 8.96 (s, 1H), 8.26-8.24 (d, J 6.8 Hz, 1H), 8.21 (s, 1H), 8.08-8.06 (d, J=7.6 Hz, 1H), 7.95-7.94 (d, J=5.2 Hz, 1H), 7.57-7.56 (d, J=6.4 Hz, 1H), 6.36-6.33 (t, J=7.2 Hz, 1H), 6.24 (s, 1H), 4.92-4.87 (m, 1H), 4.34-4.28 (m, 1H), 3.88-3.83 (m, 2H), 3.73-3.68 (m, 1H), 3.62-3.57 (m, 1H), 3.50-3.45 (t, J=8.8 Hz, 1H), 3.21 (s, 3H), 2.92-2.91 (d, J=4.8 Hz, 3H), 2.16-1.97 (m, 4H), 1.81-1.72 (m, 2H), 1.58-1.48 (m, 1H), 1.43-1.32 (m, 1H).

Example 32: N-((1R,2R)-2-hydroxycyclobutyl)-5-((2-methoxypyridin-3-yl)amino)-7-(methylamino)pyrazolo[1,5-a]pyrimidine-3-carboxamide (I-363)

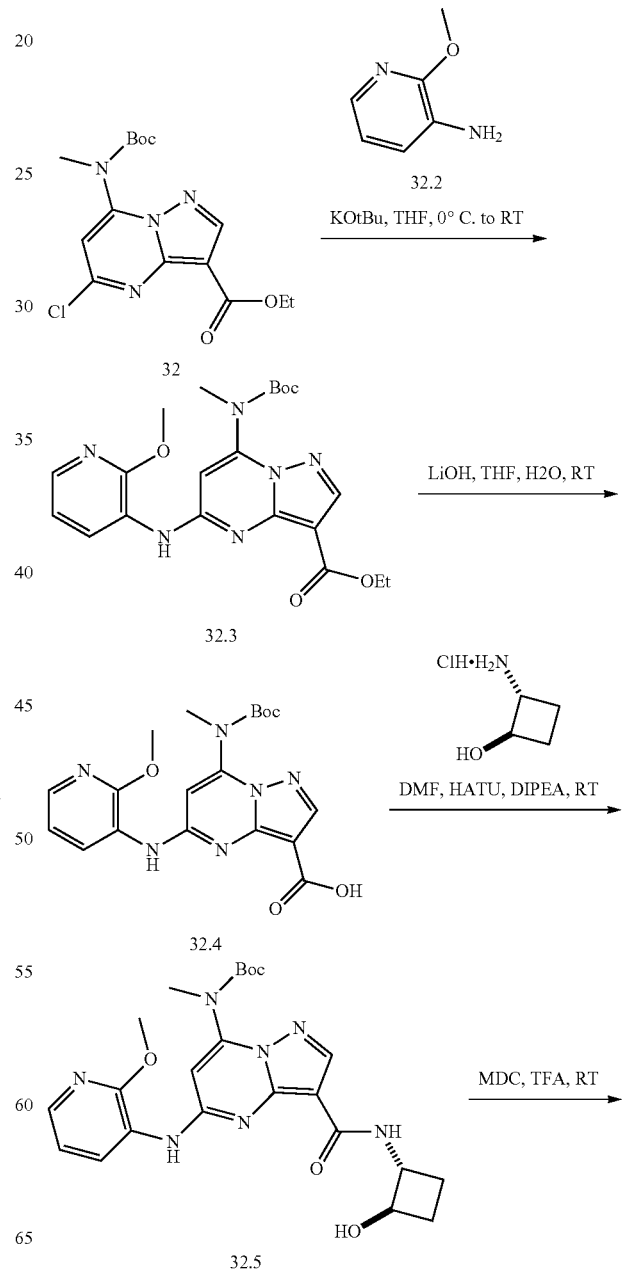

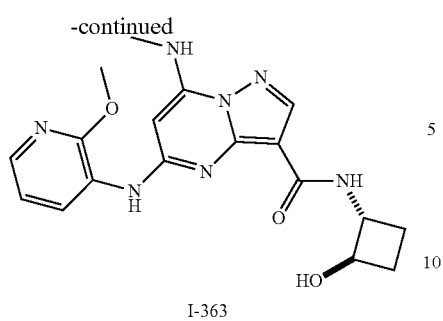

I-363

Synthesis of Compound 32.

Compound was synthesized using general procedure of core synthesis to obtain 32. (Yield: 62.21%). MS (ES): m/z 355.5 [M+H].

Synthesis of Compound 32.3.

To a cooled solution of 32. (0.500 g, 1.41 mmol, 1.0 eq), and 32.2 (0.174 g, 1.41 mmol, 1.0 eq) in tetrahydrofuran (10 mL) at 0° C. was added potassium ter-butoxide (2.8 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 32.3 (0.630 g, 96.22%). MS (ES): m/z 442.48 [M+H]$^+$.

Synthesis of Compound 32.4.

To a solution of 32.3 (0.600 g, 1.36 mmol, 1.0 eq), in tetrahydrofuran:water (20 mL, 2:1) was added lithium hydroxide (0.312 g, 13.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 32.4 (0.400 g, 71.18%). MS(ES): m/z 415.42 [M+H]$^+$.

Synthesis of Compound 32.5.

Compound was synthesized using general procedure A to obtain 32.5. (0.160 g, 768.57%). MS (ES): m/z 484.53 [M+H]$^+$ Synthesis of Compound I-363.

Compound was synthesized using general procedure C to obtain I-363 (0.105 g, 82.76%). MS (ES): m/z 384.41 [M+H]$^+$, LCMS purity: 99.67%, HPLC purity: 98.98%, Chiral HPLC purity: 49.64%+49.66%, $^1$H NMR (DMSO-d$_6$, 400 MHZ): 8.97 (s, 1H), 8.30-8.28 (d, J=7.2 Hz, 1H), 8.15 (s, 1H), 8.05-8.02 (d, J=9.2 Hz, 1H), 7.94 (s, 2H), 7.05-7.02 (m, 1H), 5.92 (s, 1H), 5.36-5.34 (d, 1 J=7.2 Hz, 1H), 4.20-4.15 (t, J=8 Hz, 1H), 3.90 (s, 3H), 3.68-3.62 (m, 1H), 2.92-2.91 (d, J=4.4 Hz, 1H), 2.02-1.90 (m, 2H), 1.48-1.33 (m, 1H), 1.24 (bs, 1H), 1.13-1.03 (m, 2H).

Example 33: N-(2-hydroxy-2-methylcyclobutyl)-5-((2-methoxypyridin-3-yl)amino)-7-(methylamino)pyrazolo[1,5-a]pyrimidine-3-carboxamide (I-911)

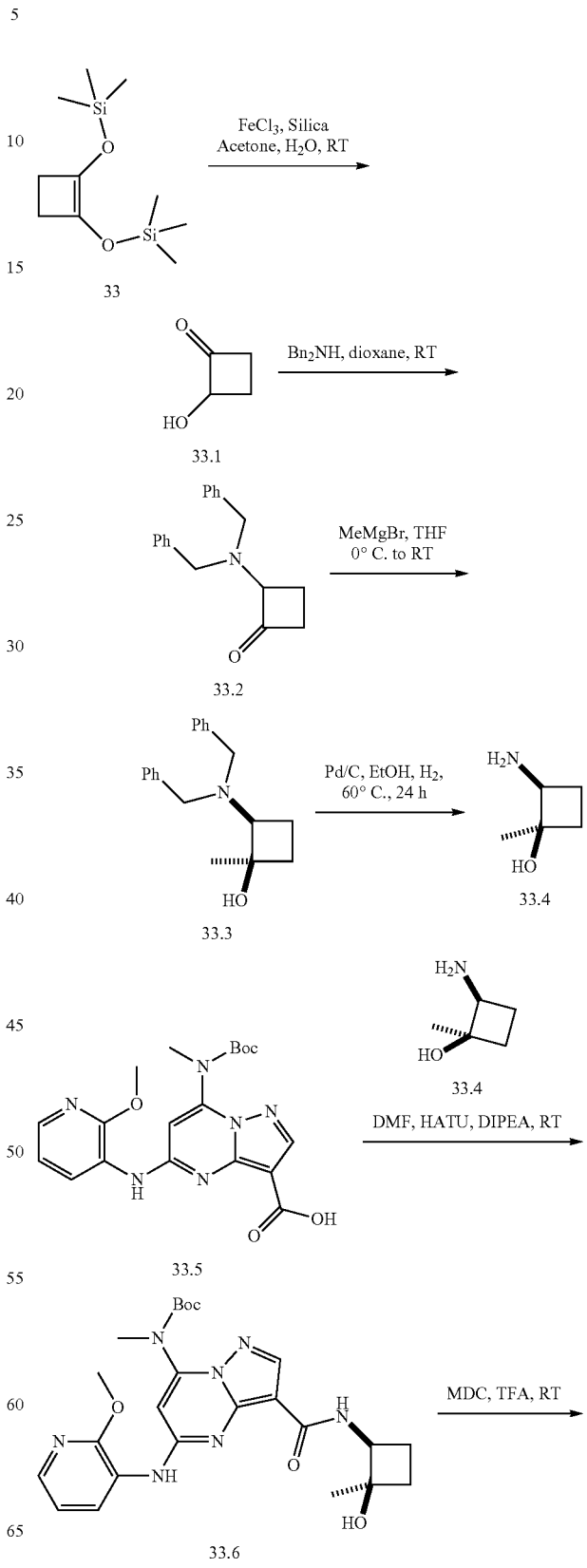

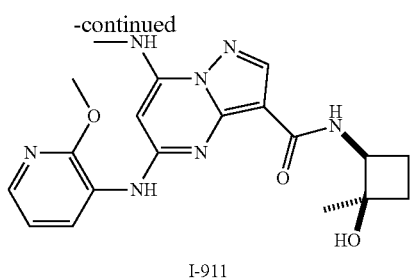

I-911

Synthesis of Compound 33.1.

To a cooled solution of 33 (5 g, 21.70 mmol, 1.0 eq), in mixture of acetone (10 mL) and water (5 mL) was added iron chloride (III) (3.519 g, 21.70 mmol, 1.0 eq). The reaction mixture was stirred at room temperature for 20 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 10% ethyl acetate in hexane to obtain 33.1. (1.0 g, 53.54%). MS(ES): m/z 87.09 [M+H]$^+$.

Synthesis of Compound 33.2.

To a solution of 33.1 (1.0 g, 11.62 mmol, 1.0 eq), in 1,4-dioxane (10 mL) was added diphenyl amine (3.93 g, 23.24 mmol, 2.0 eq). The reaction was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 10% ethyl acetate in hexane to obtain 33.2 (1.2 g, 38.93%). MS(ES): m/z 266.36 [M+H]$^+$.

Synthesis of Compound 33.3.

To a solution of 33.2 (1.2 g, 4.52 mmol, 1.0 eq) in tetrahydrofuran (6 mL) was added methyl magnesium bromide (0.81 g, 6.78 mmol, 1.5 eq) under nitrogen condition at 0° C. for 1 h. The reaction was stirred at room temperature for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 33.3. (0.8 g, 62.87%). MS(ES): m/z 282.40 [M+H]$^+$.

Synthesis of Compound 33.4.

To a solution of 33.3 (0.5 g, 1.78 mmol, 1.0 eq) in ethanol (4 ml), palladium on charcoal (0.070 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 92% ethyl acetate in hexane to obtain pure 33.4. (0.11 g, 61.76%). MS (ES): m/z 102.15 [M+H]$^+$ Synthesis of Compound 33.5.

Compound was synthesized as per experimental protocol of Example 32 to obtain 33.5 (Yield: 71.18%). MS(ES): m/z 415.42 [M+H]$^+$.

Synthesis of Compound 33.6.

Compound was synthesized using general procedure A to obtain 33.6. (0.15 g, 62.47%), MS (ES): m/z 498.56 [M+H]$^+$ Synthesis of Compound I-911:

Compound was synthesized using general procedure C to obtain I-911 (0.11 g, 91.81%), MS (ES): m/z 398.52 [M+H]$^+$, LCMS purity: 100%, HPLC purity: 97.66%, CHIRAL HPLC: 50%, 50%, $^1$H NMR (DMSO-d$_6$, 400 MHZ): 8.82 (s, 1H), 8.71-8.69 (d, J=7.6 Hz, 1H), 8.18 (s, 1H), 7.99-7.98 (d, J=5.2 Hz, 1H), 7.91-7.89 (d, J=4.8 Hz, 1H), 7.85-7.84 (d, J=4.4 Hz, 1H), 7.11-7.08 (t, J=5.2 Hz, 1H), 6.09 (s, 1H), 4.99 (s, 1H), 4.32-4.27 (m, 1H), 3.99 (s, 3H), 2.93-2.92 (d, J=4.4 Hz, 3H), 2.10-2.09 (m, 1H), 1.86-1.76 (m, 2H), 1.28-1.23 (m, 4H).

Example 34: N-((1S,2R)-2-hydroxy-2-methylcyclobutyl)-5-((2-methoxypyridin-3-yl)amino)-7-(methylamino)pyrazolo[1,5-a]pyrimidine-3-carboxamide (I-1015), N-((1R,2S)-2-hydroxy-2-methylcyclobutyl)-5-((2-methoxypyridin-3-yl)amino)-7-(methylamino)pyrazolo[1,5-a]pyrimidine-3-carboxamide (I-1016)

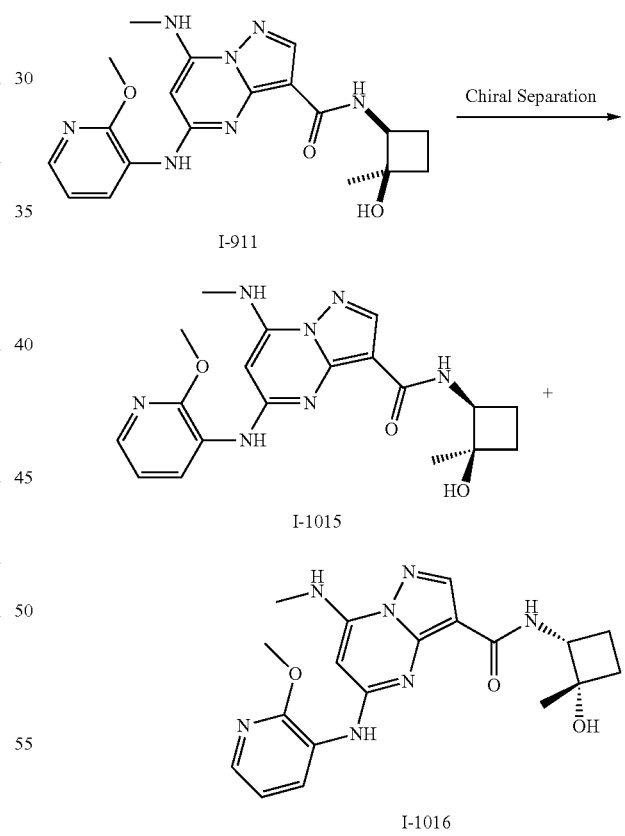

Synthesis of Compound I-1015 & I-1016.

Isomers of I-911 (0.09 g) were separated using column CHIRALCEL OJ-H (250 mm*4.6 mm, 5 u) 0.1% _DEA_ HEX_IPA-MEOH (50-50) to get pure fraction-1 (FR-a) and fraction-2 (FR-b). FR-a was concentrated under reduced pressure at 30° C. to afford pure FR-a (0.021 g). MS(ES): m/z 398.52 [M+H]$^+$, LCMS purity: 97.34%, HPLC purity:

98.14%, CHIRAL HPLC purity: 98.16%, ¹H NMR (DMSO-d₆, 400 MHZ): 8.83 (s, 1H), 8.68-8.70 (d, J=8 Hz, 1H), 8.18 (s, 1H), 7.97-7.99 (d, J=8 Hz, 1H), 7.90-7.92 (d, J=8 Hz, 1H), 7.84-7.85 (d, J=4 Hz, 1H), 6.09 (s, 1H), 5.00 (s, 1H), 4.29-4.31 (d, J=8 Hz, 1H), 4.00 (s, 3H), 2.92-2.93 (d, J=4 Hz, 3H), 2.09 (s, 1H), 1.76-1.86 (m, 3H), 1.25 (s, 3H), 1.14-1.16 (t, J=8 Hz, 1H).

FR-b was concentrated under reduced pressure at 30° C. to afford pure FR-b (0.023 g). MS(ES): m/z 398.25 [M+H]⁺, LCMS purity: 96.44%, HPLC purity: 97.70%, CHIRAL HPLC purity: 97.97%, ¹H NMR (DMSO-d₆, 400 MHZ): 8.63-8.65 (d, J=8 Hz, 1H), 8.18 (s, 1H), 8.02-8.04 (d, J=8 Hz, 1H), 7.82-7.83 (d, J=4 Hz, 1H), 7.06-7.09 (m, 1H), 6.01 (s, 1H), 4.24-4.30 (m, 1H), 4.00 (s, 3H), 2.88-2.92 (m, 4H), 2.08-2.09 (t, J=4 Hz, 1H), 1.73-1.84 (m, 3H), 1.23 (s, 3H), 1.14-1.16 (t, J=8 Hz, 1H).

Example 35: 5-((3'-fluoro-2-oxo-2H-[1,2'-bipyridin]-3-yl)amino)-N-(2-methoxycyclobutyl)-7-(methylamino)pyrazolo[1,5-a]pyrimidine-3-carboxamide (I-863)

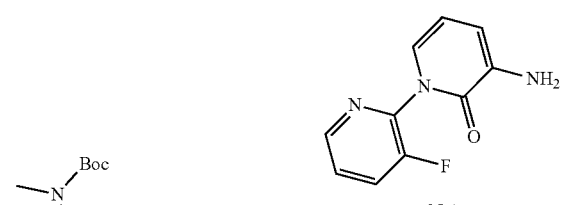

35.1

Dixoane, Xantphos
Pd₂(dba)₃, Na₂CO₃, 100° C.

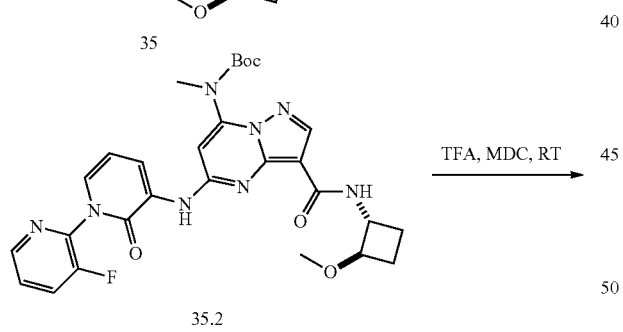

35

TFA, MDC, RT

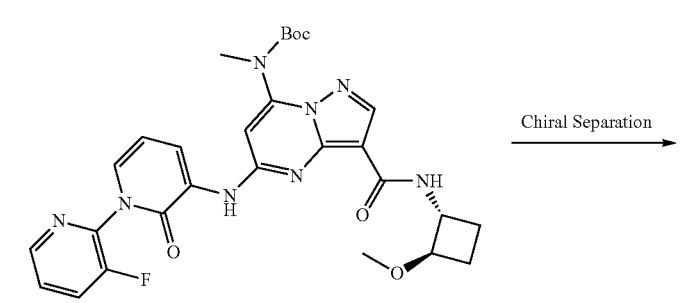

35.2

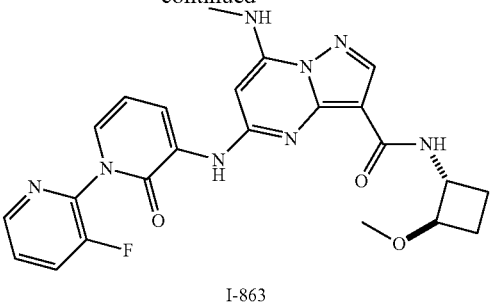

I-863

Synthesis of Compound 35.

Compound was synthesized as per experimental protocol of Example 30 to obtain 35. (Yield: 57.95%), MS (ES): m/z 410.16 [M+H]⁺

Synthesis of Compound 35.1.

Compound was synthesized as per experimental protocol of Example 19 to obtain 35.1. (Yield: 80.70%), MS (ES): m/z 206.29 [M+H]⁺

Synthesis of Compound 35.2.

Compound was synthesized using general procedure B to obtain 35.2. (0.150 g, 70.84%), MS (ES): 579.24 [M+H]⁺

Synthesis of Compound I-863:

Compound was synthesized using general procedure C to obtain I-863 (0.020 g, 60.46%), MS (ES): m/z 479.42 [M+H]⁺, LCMS purity: 100%, HPLC purity: 98.97%, Chiral HPLC: 49.85%, 49.96%, ¹H NMR (DMSO-d₆, 400 MHZ): 9.08 (s, 1H), 8.53-8.52 (d, J=4.4 Hz, 1H), 8.39-8.37 (d, J=7.2 Hz, 1H), 8.23 (s, 1H), 8.11 (s, 1H), 8.09 (s, 1H), 7.98 (bs, 1H), 7.76-7.72 (m, 1H), 7.50-7.49 (d, J=7.2 Hz, 1H), 6.50-6.47 (t, J=6.8 Hz, 1H), 6.22 (s, 1H), 4.36-4.32 (t, J=8 Hz, 1H), 3.78-3.72 (m, 1H), 3.23 (s, 3H), 2.92 (s, 2H), 2.18-2.06 (m, 2H), 1.59-1.49 (m, 1H), 1.42-1.37 (m, 1H), 1.25 (bs, 1H).

Example 36: 5-((3'-fluoro-2-oxo-2H-[1,2'-bipyridin]-3-yl)amino)-N-((1R,2R)-2-methoxycyclobutyl)-7-(methylamino)pyrazolo[1,5-a]pyrimidine-3-carboxamide (I-904), 5-((3'-fluoro-2-oxo-2H-[1,2'-bipyridin]-3-yl)amino)-N-((1S,2S)-2-methoxycyclobutyl)-7-(methylamino)pyrazolo[1,5-a]pyrimidine-3-carboxamide (I-905)

Chiral Separation

36

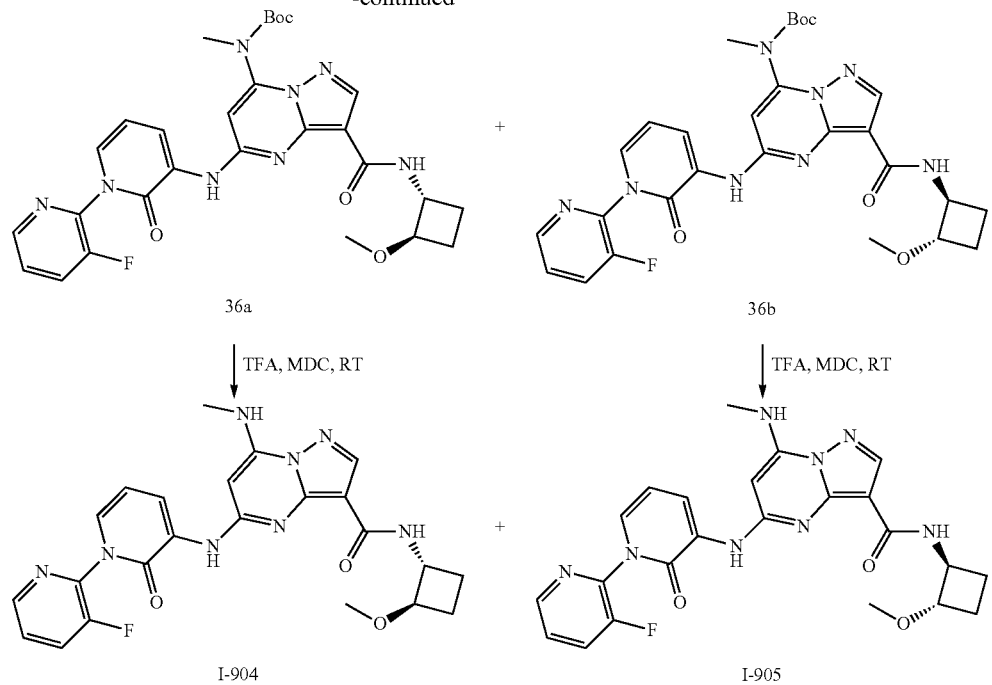

36a, 36b → I-904, I-905 (TFA, MDC, RT)

Synthesis of Compound 36.

Compound was synthesized as per experimental protocol of Example 35 to obtain 36. (Yield: 70.84%). MS (ES): m/z 579.24 [M+H]

Synthesis of Compound 36a and 36b.

Isomers of 36 (0.100 g) were separated using column (CHIRALPAK IB 250 mm*4.6 mm, u) and 0.1%_DEA_HEX_IPA-MEOH (50-50) as co-solvent with flow rate of 4 mL/min. to get pure fraction-1 (FR-a) and fraction-2 (FR-b). FR-a was concentrated under reduced pressure at 30° C. to afford pure FR-a (0.041 g). MS(ES): m/z 579.50 [M+H]$^+$. FR-b was concentrated under reduced pressure at 30° C. to afford pure FR-b (0.043 g). MS(ES): m/z 579.50 [M+H]$^+$.

Synthesis of Compound I-904 and I-905:

Compound was synthesized using general procedure C to obtain deprotected FR-a (0.030 g) MS (ES): m/z 479.31 [M+H]$^+$, LCMS purity: 100%, HPLC purity: 98.30%, Chiral HPLC: 98.50 $^1$H NMR (DMSO-d$_6$, 400 MHZ): 9.08 (s, 1H), 8.53-8.52 (d, J=4.6 Hz, 1H), 8.39-8.37 (d, J=6.8 Hz, 1H), 8.23 (s, 1H), 8.11 (s, 1H), 8.09-8.06 (d, J=12 Hz, 1H), 7.99-7.98 (d, J=4 Hz, 1H), 7.76-7.72 (m, 1H), 7.50-7.49 (d, J=4.2 Hz, 1H), 6.50-6.48 (t, J=8 Hz, 1H), 6.22 (s, 1H), 4.36-4.34 (t, J=8 Hz, 1H), 3.77-3.72 (m, 1H), 3.22 (s, 3H), 2.91-2.90 (d, J=4 Hz, 3H), 2.18-2.06 (m, 1H), 1.56-1.46 (m, 1H), 1.44-1.37 (m, 1H), 1.25 (s, 1H).

and deprotected FR-b (0.030 g) MS (ES): m/z 479.31 [M+H]$^+$, LCMS purity: 97.33%, HPLC purity: 98.61% Chiral HPLC: 100%, $^1$H NMR (DMSO-d$_6$, 400 MHZ): 9.08 (s, 1H), 8.53-8.52 (d, J=4.6 Hz, 1H), 8.39-8.37 (d, J=6.8 Hz, 1H), 8.23 (s, 1H), 8.11 (s, 1H), 8.09-8.06 (d, J=12 Hz, 1H), 7.99-7.98 (d, J=4 Hz, 1H), 7.76-7.72 (m, 1H), 7.50-7.49 (d, J=4.2 Hz, 1H), 6.50-6.48 (t, J=8 Hz, 1H), 6.22 (s, 1H), 4.36-4.34 (t, J=8 Hz, 1H), 3.77-3.72 (m, 1H), 3.22 (s, 3H), 2.92-2.91 (d, J=4 Hz, 3H), 2.18-2.06 (m, 1H), 1.56-1.46 (m, 1H), 1.44-1.37 (m, 1H), 1.25 (s, 1H).

Example 37: N-(2-hydroxy-2-methylcyclobutyl)-5-((1-isopropyl-2-oxo-1,2-dihydropyridin-3-yl)amino)-7-(methylamino)pyrazolo[1,5-a]pyrimidine-3-carboxamide (I-1116)

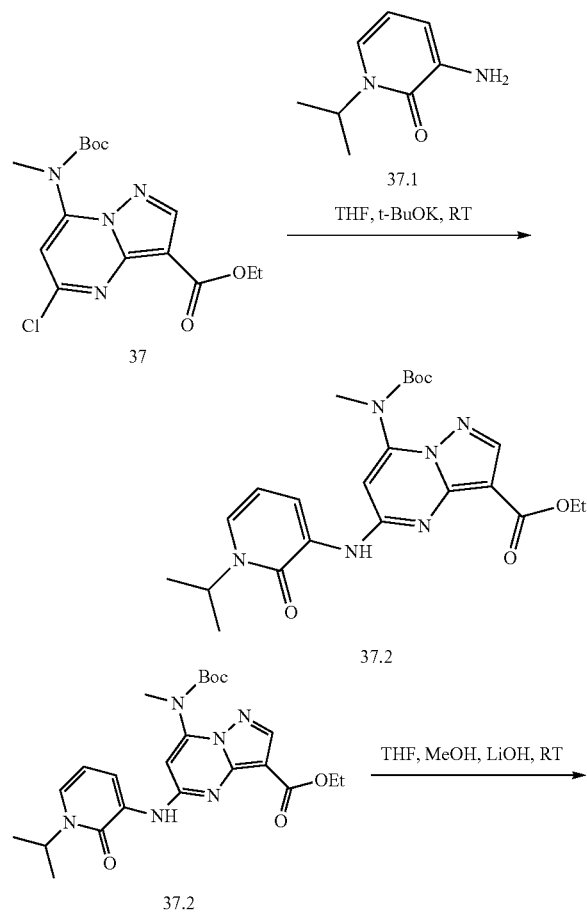

37 + 37.1 → 37.2 (THF, t-BuOK, RT)

37.2 → 37.2 (THF, MeOH, LiOH, RT)

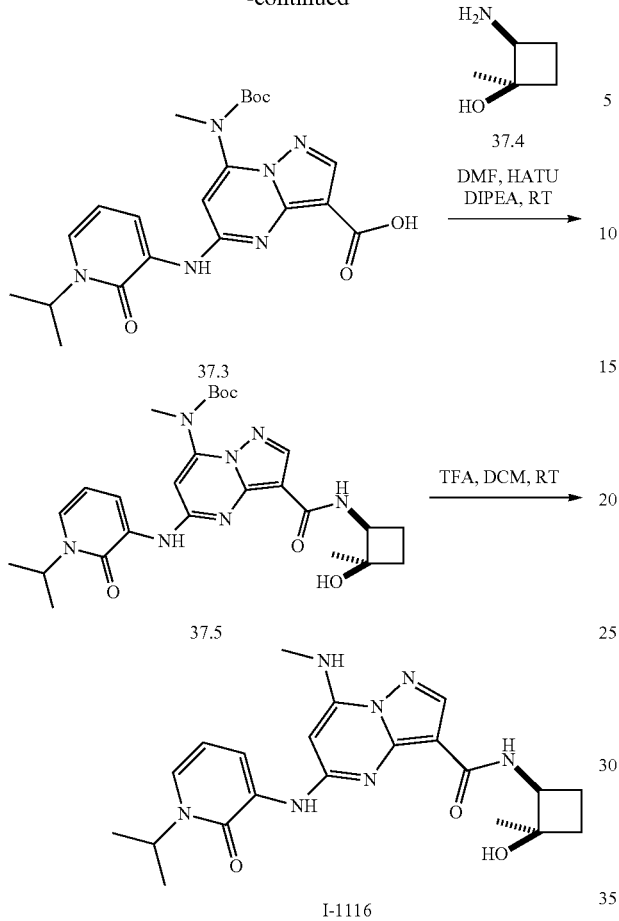

Synthesis of Compound 37.5.

Compound was synthesized using general procedure A to obtain 37.5. (0.188 g, 79.13%), MS (ES): m/z 526.27 [M+H]⁺

Synthesis of Compound I-1116:

Compound was synthesized using general procedure C to obtain I-1116 (0.133 g, 87.39%), MS (ES): m/z 426.47 [M+H]⁺, LCMS purity: 96.88%, HPLC purity: 98.90%, CHIRAL HPLC: 49.74%, 50.25%, $^1$H NMR (DMSO-d$_6$, 400 MHZ): 8.84 (s, 1H), 8.53-8.51 (d, J=6 Hz, 1H), 8.19 (s, 1H), 7.98 (bs, 1H), 7.88-7.87 (d, J=4.8 Hz, 1H), 7.43-7.41 (d, J=6 Hz, 1H), 6.44-6.41 (t, J=7.2 Hz, 1H), 6.27 (s, 1H), 5.23-5.16 (m, 1H), 5.09 (s, 1H), 4.37-4.31 (s, 1H), 2.92-2.91 (d, J=4.8 Hz, 3H), 2.10 (bs, 1H), 1.81-1.77 (t, J=6.4 Hz, 1H), 1.78 (bs, 2H), 1.53 (bs, 2H), 1.37-1.35 (d, J=6.8 Hz, 6H), 1.24 (bs, 1H).

Example 38: N-(3-hydroxy-2,2-dimethylpropyl)-7-(methylamino)-5-((2-oxo-2H-[1,2'-bipyridin]-3-yl)amino)pyrazolo[1,5-a]pyrimidine-3-carboxamide (I-683)

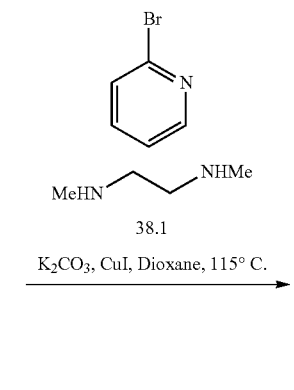

Synthesis of Compound 37.

Compound was synthesized using general procedure of core synthesis to obtain 37. MS(ES): m/z 355.11 [M+H]⁺.

Synthesis of Compound 37.2.

To a cooled solution of 37 (1.0 g, 2.81 mmol, 1.0 eq), and 37.1 (0.512 g, 2.37 mmol, 1.2 eq) in tetrahydrofuran (20 mL) at 0° C. was added potassium ter-butoxide (1M in tetrahydrofuran) (5.6 mL, 5.62 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 37.2. (0.820 g, 61.83%). MS (ES): m/z 471.23 [M+H]⁺

Synthesis of Compound 37.3.

To a solution of 37.2 (0.820 g, 1.74 mmol, 1.0 eq), in methanol:tetrahydrofuran:water (15 mL, 2:1:1) was added lithium hydroxide (0.417 g, 17.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 37.3. (0.690 g, 89.48%). MS(ES): m/z 443.20 [M+H]⁺

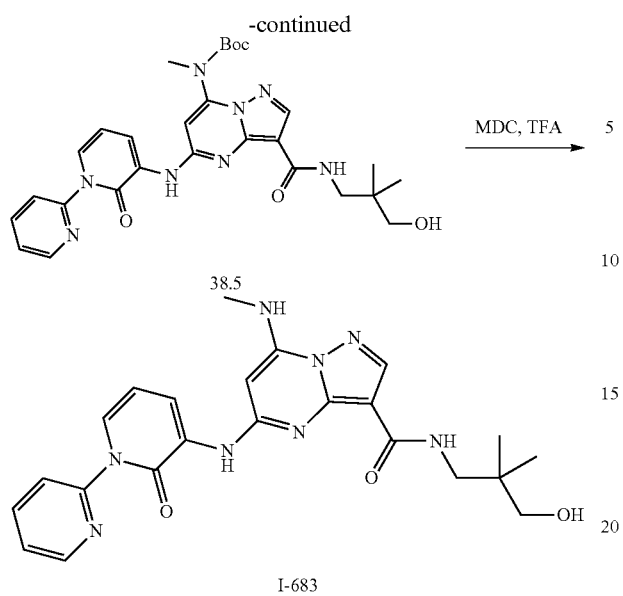

I-683

Synthesis of Compound 38.2.

To a solution of 38 (2 g, 18.18 mmol, 1.0 eq) in 1,4-dioxane (40 mL), 38.1 (7.2 g, 45.45 mmol, 2.5 eq) was added. The reaction mixture was degassed for 10 min under argon atmosphere followed by addition of potassium carbonate (7.5 g, 54.54 mmol, 3.0 eq), N,N-dimethylethylenediamine (0.640 g, 7.27 mmol, 0.4 eq), and copper iodide (0.692 g, 3.636 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 38.2 (2 g, Yield: 58.82%). MS (ES): m/z 188.20 [M+H]$^+$ Synthesis of Compound 38.3.

Compound was synthesized using general procedure of core synthesis obtain 38.3. 13.2 g, 71.67%). $^1$H NMR (DMSO-d6, 400 MHZ): 12.63 (s, 1H), 8.63 (s, 1H), 7.55 (s, 1H), 3.31 (s, 3H), 1.29 (s, 9H).

Synthesis of Compound 38.4.

Compound was synthesized using general procedure A to obtain 38.4. (0.15 g, Yield: 59.80%). MS (ES): m/z 412.88 [M+H]$^+$.

Synthesis of Compound 38.5.

Compound was synthesized using general procedure B to obtain 38.5. (0.07 g, Yield: 51.25%). MS (ES): m/z 563.63 [M+H]$^+$ Synthesis of Compound I-683.

Compound was synthesized using general procedure C to obtain I-683 (0.041 g, 88.65%). MS(ES): m/z 463.50 [M+H]$^+$ LCMS purity: 98.74%, HPLC purity: 98.50%, $^1$H NMR (DMSO-d$_6$, 400 MHZ): 8.97 (s, 1H), 8.65-8.64 (d, J=3.6 Hz, 1H), 8.29-8.28 (d, J=6.4 Hz, 1H), 8.23 (s, 1H), 8.06-8.03 (t, J=7.2 Hz, 1H), 7.96 (bs, 1H), 7.87-7.83 (t, J=9.2 Hz, 2H), 7.57-7.53 (m, 2H), 6.50-6.46 (t, J=7.2 Hz, 1H), 6.25 (s, 1H), 4.71 (bs, 1H), 3.28-3.27 (d, J=6 Hz, 2H), 3.12 (s, 2H), 2.91 (s, 3H), 0.84 (bs, 6H).

Example 39: N-(2-methoxycyclobutyl)-7-(methylamino)-5-((2-oxo-2H-[1,2'-bipyridin]-3-yl)amino)pyrazolo[1,5-a]pyrimidine-3-carboxamide (I-816)

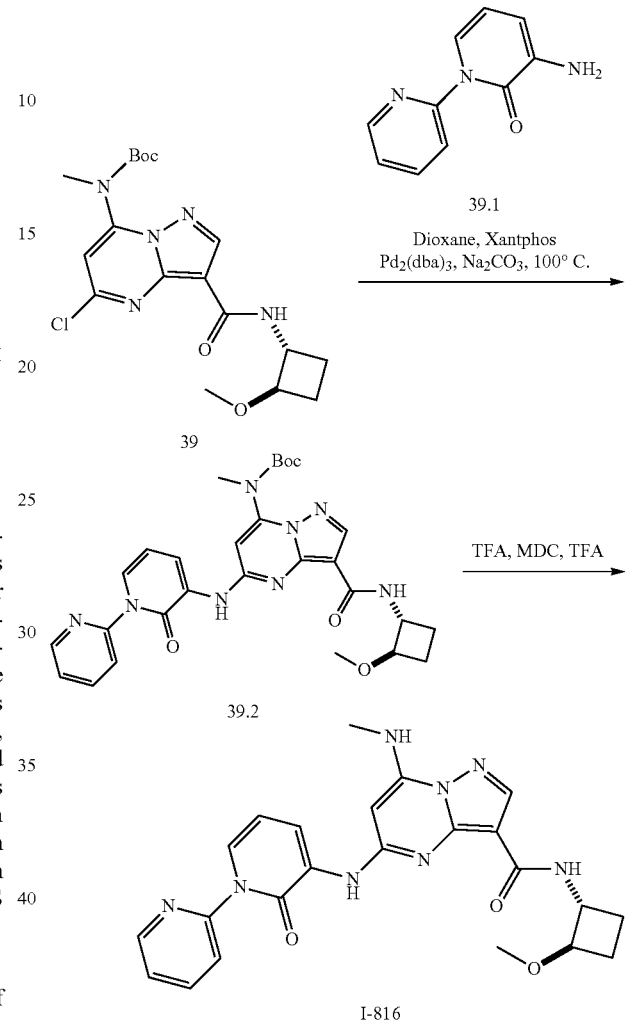

I-816

Synthesis of Compound 39.

Compound was synthesized as per experimental protocol of Example 30 to obtain 39. (Yield: 57.95%), MS (ES): m/z 410.16 [M+H]$^+$ Synthesis of Compound 39.1.

Compound was synthesized as per experimental protocol of Example 38 to obtain 39.1. (Yield: 58.82%), MS (ES): m/z 188.20 [M+H]$^+$ Synthesis of Compound 39.2.

Compound was synthesized using general procedure B to obtain 39.2. (0.125 g, 60.93%), MS (ES): 561.25 [M+H]$^+$ Synthesis of Compound I-816:

Compound was synthesized using general procedure C to obtain I-816 (0.105 g, 97.39%), MS (ES): m/z 461.40 [M+H]$^+$, LCMS purity: 98.84%, HPLC purity: 93.86%, Chiral HPLC: 47.78%, 51.75%, $^1$H NMR (DMSO-d$_6$, 400 MHZ): 9.06 (s, 1H), 8.66 (bs, 1H), 8.36-8.34 (d, J=7.2 Hz, 1H), 8.22 (s, 1H), 8.12-8.07 (m, 1H), 8.05-8.04 (d, J=1.6 Hz, 1H), 7.99-7.97 (d, J=5.2 Hz, 1H), 7.88-7.86 (d, J=8 Hz, 1H), 7.64-7.62 (d, J=7.2 Hz, 1H), 7.57-7.54 (m, 1H), 6.47-6.44 (t, J=7.2 Hz, 1H), 6.24 (s, 1H), 4.36-4.29 (m, 1H), 3.77-3.71 (m, 1H), 3.22 (s, 3H), 2.92-2.91 (d, J=4.8 Hz, 3H), 2.18-2.06 (m, 2H), 1.56-1.49 (m, 1H), 1.46-1.39 (m, 1H).

Example 40: N-((1R,2R)-2-methoxycyclobutyl)-7-(methylamino)-5-((2-oxo-2H-[1,2'-bipyridin]-3-yl)amino)pyrazolo[1,5-a]pyrimidine-3-carboxamide (I-908), N-((1S,2S)-2-methoxycyclobutyl)-7-(methylamino)-5-((2-oxo-2H-[1,2'-bipyridin]-3-yl)amino)pyrazolo[1,5-a]pyrimidine-3-carboxamide (I-909)

Example 41: N-cyclopropyl-5-((6'-methyl-2-oxo-2H-[1,3'-bipyridin]-3-yl)amino)-7-(methylamino)pyrazolo[1,5-a]pyrimidine-3-carboxamide (I-765)

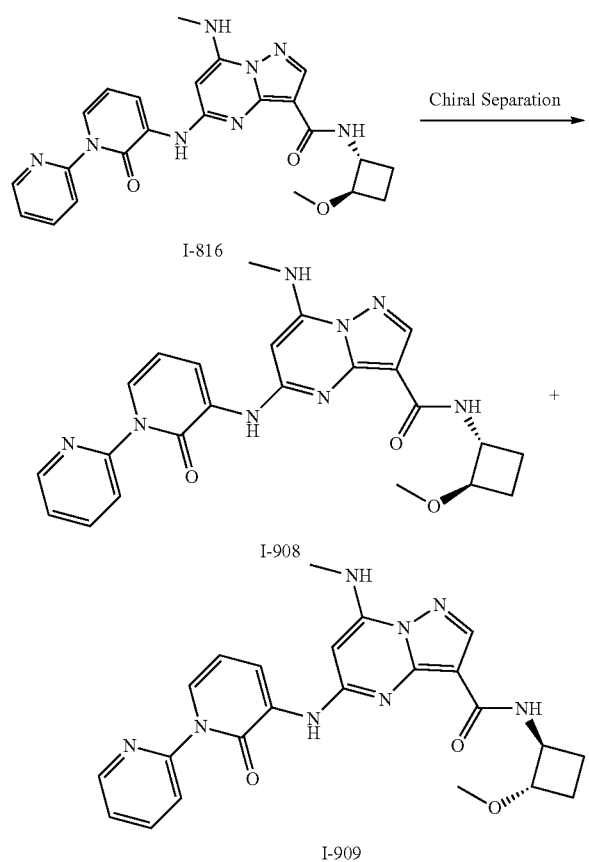

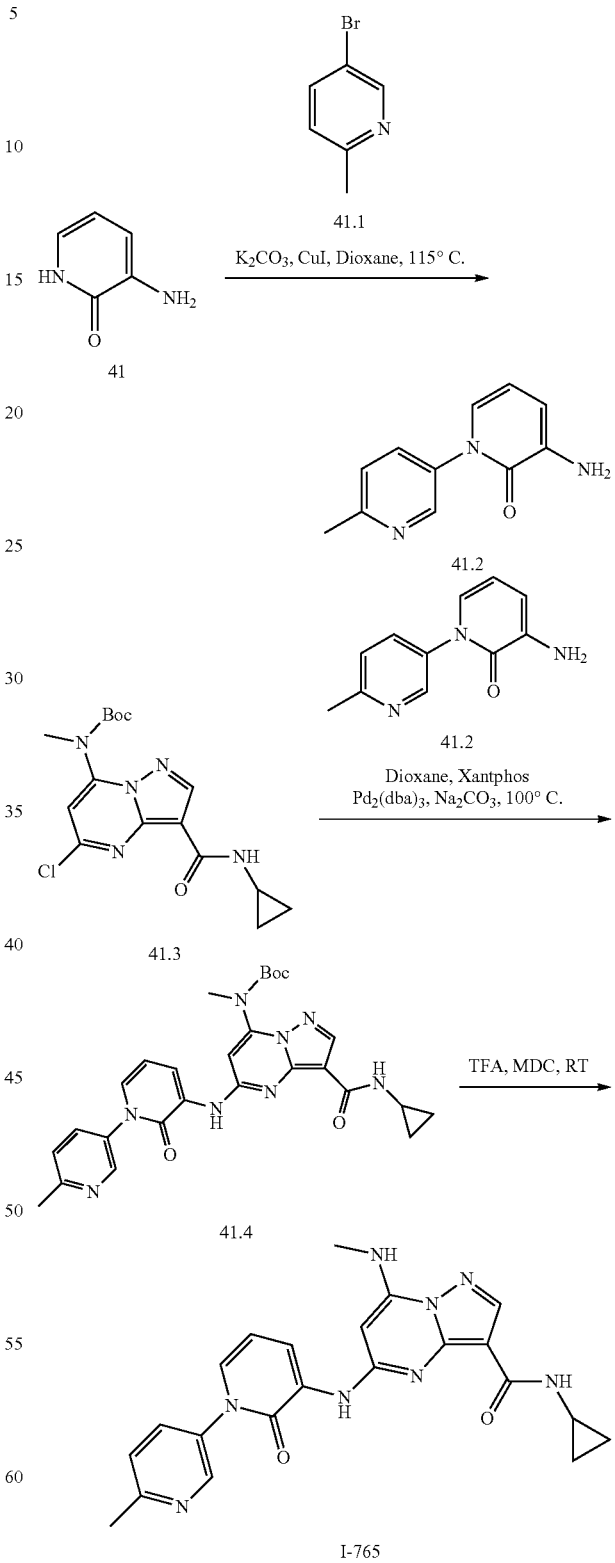

Synthesis of Compound I-908 & I-909.

Isomers of I-816 (0.105 g) were separated using column (CHIRAL PAK AD-H 250×4.6 mm, 5 u) 0.1% DEA_MEOH (70-30) to get pure fraction-1 (FR-a) and fraction-2 (FR-b). FR-a was concentrated under reduced pressure at 30° C. to afford pure FR-a (0.025 g). MS(ES): m/z 461.42 [M+H]+, LCMS purity: 99.70%, HPLC purity: 99.53%, CHIRAL HPLC purity: 100%, $^1$H NMR (DMSO-$d_6$, 400 MHZ): 9.05 (s, 1H), 8.27 (s, 1H), 8.37-8.35 (m, 2H), 8.23 (s, 1H), 8.12-8.05 (m, 1H), 7.97 (s, 1H), 7.88-7.87 (d, J=8.0 Hz, 1H), 7.65-7.63 (d, J=6.0 Hz, 1H), 7.58-7.56 (m, 1H), 6.48-6.45 (t, J=6.8 Hz, 1H), 6.25 (s, 1H), 4.37-4.33 (m, 1H), 3.76-3.74 (d, J=7.6 Hz, 1H), 3.23 (s, 3H), 2.93 (s, 3H), 2.82-2.79 (m, 2H), 2.16-2.08 (m, 2H).

FR-b was concentrated under reduced pressure at 30° C. to afford pure FR-b (0.026 g). MS(ES): m/z 461.57 [M+H]+, LCMS purity: 95.64%, HPLC purity: 95.06%, CHIRAL HPLC purity: 98.21%, $^1$H NMR (DMSO-$d_6$, 400 MHZ): 8.66-8.65 (d, J=3.6 Hz, 1H), 8.38 (s, 1H), 8.34-8.32 (d, J=5.6 Hz, 1H), 8.22 (s, 1H), 8.15-8.12 (d, J=9.2 Hz, 1H), 8.08-8.04 (t, J=8.0 Hz, 1H), 7.85-7.83 (d, J=8.0 Hz, 1H), 7.63-7.61 (d, J=7.2 Hz, 1H), 7.57-7.54 (m, 1H), 6.48-6.45 (t, J=7.2 Hz, 1H), 6.19 (s, 1H), 4.35-4.31 (m, 1H), 3.76-3.71 (m, 2H), 3.21 (s, 3H), 2.92 (s, 3H), 2.82-2.79 (m, 2H), 2.17-2.06 (m, 2H).

Synthesis of Compound 41.2.

To a solution of 41 (3.0 g, 17.44 mmol, 1 eq) in 1,4-dioxane (150 mL), 41.1 (2.30 g, 20.92 mmol, 1.2 eq) was added. The reaction mixture was degassed for 10 min under argon atmosphere followed by addition of potassium carbonate (6.0 g, 43.6 mmol, 2.5 eq), N,N-dimethylethylenediamine (0.384 g, 4.36 mmol, 0.25 eq), and copper iodide (0.497 g, 2.61 mmol, 0.15 eq). The reaction mixture was heated at 115° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 41.2. (1.56 g, Yield: 44.45%). MS (ES): m/z 202.09 [M+H]+

Synthesis of Compound 41.3.

Compound was synthesized as per experimental protocol of Example 27 to obtain 41.3. (Yield: 57.16%), MS (ES): m/z 366.82[M+H]+

Synthesis of Compound 41.4.

Compound was synthesized using general procedure B to obtain 41.4. (0.070 g, 48.26%), MS (ES): 531.24 [M+H]+

Synthesis of Compound I-765:

Mixture of 41.4 (0.070 g, 0.13 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-765 (0.040 g, 70.43%), MS (ES): m/z 431.43 [M+H]+, LCMS purity: 95.00%, HPLC purity: 95.38%, $^1$H NMR (DMSO-$d_6$, 400 MHZ): 9.01 (s, 1H), 8.59-8.59 (d, J=2 Hz, 1H), 8.26-8.25 (d, J=7.2 Hz, 1H), 8.22 (s, 1H), 7.96-7.95 (d, J=4.8 Hz, 1H), 7.90-7.89 (d, J=2.4 Hz, 1H), 7.88-7.86 (m, 1H), 7.48-7.46 (d, J=8.4 Hz, 1H), 7.43-7.41 (d, J=6.8 Hz, 1H), 6.44-6.41 (t, J=7.2 Hz, 1H), 6.23 (s, 1H), 2.91-2.89 (d, J=4.8 Hz, 3H), 2.87 (s, 1H), 2.57 (s, 3H), 0.84-0.79 (m, 2H), 0.54 (bs, 2H).

Example 42: N-(2-methoxycyclobutyl)-5-((6'-methyl-2-oxo-2H-[1,3'-bipyridin]-3-yl)amino)-7-(methylamino)pyrazolo[1,5-a]pyrimidine-3-carboxamide (I-843)

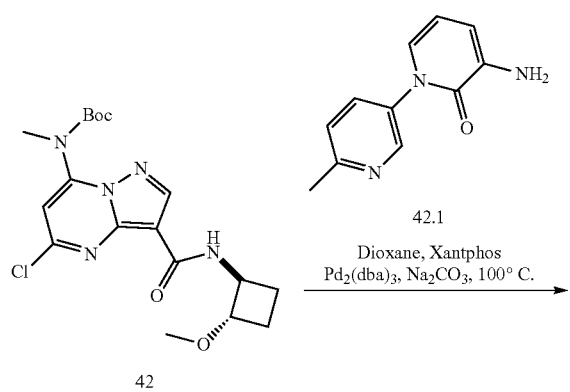

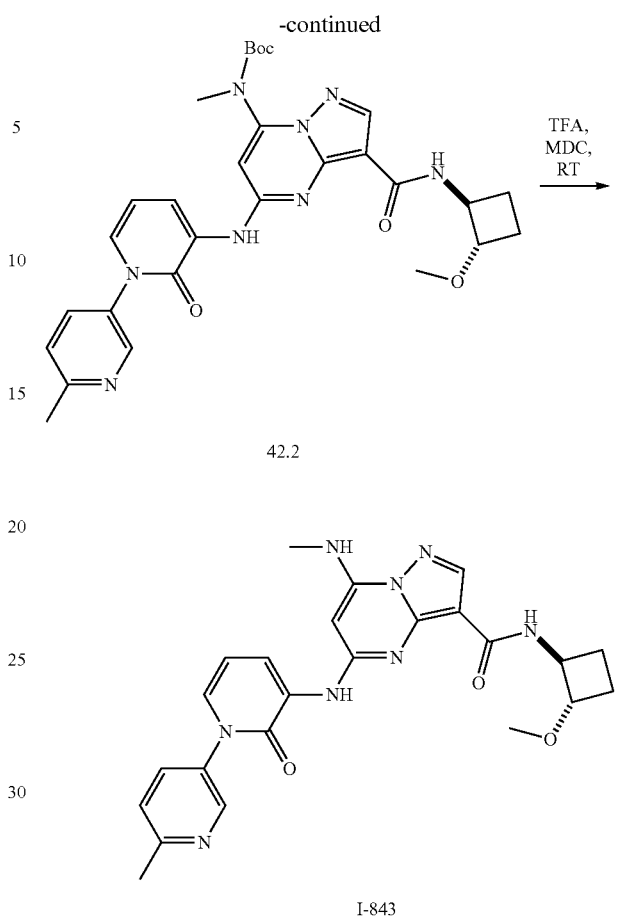

Synthesis of Compound 42.

Compound was synthesized as per experimental protocol of Example 30 to obtain 42. (Yield: 57.95%), MS (ES): m/z 410.16 [M+H]+

Synthesis of Compound 42.1.

Compound was synthesized as per experimental protocol of Example 41 to obtain 42.1. (Yield: 44.45%), MS (ES): m/z 202.09 [M+H]+

Synthesis of Compound 42.2.

Compound was synthesized using general procedure B to obtain 42.2. (0.150 g, 71.33%), MS (ES): 575.27 [M+H]+

Synthesis of Compound I-843:

Compound was synthesized using general procedure C to obtain I-843 (0.020 g, 69.20%), MS (ES): m/z 475.36 [M+H]+, LCMS purity: 97.78%, HPLC purity: 97.44%, CHIRAL HPLC: 46.90%, 46.26%, $^1$H NMR (DMSO-$d_6$, 400 MHZ): 9.04 (bs, 1H), 8.60 (bs, 1H), 8.38-8.36 (d, J=7.6 Hz, 1H), 8.23 (s, 1H), 8.10-8.08 (d, J=8.8 Hz, 1H), 7.97 (bs, 1H), 7.90-7.88 (d, J=8 Hz, 1H), 7.48-7.43 (m, 2H), 6.44-6.41 (t, J=6.8 Hz, 1H), 6.26 (s, 1H), 4.37-4.33 (t, J=7.6 Hz, 1H), 3.76-3.74 (d, J=7.6 Hz, 1H), 3.23 (s, 3H), 2.91 (bs, 3H), 2.58 (bs, 3H), 1.57-1.52 (t, J=9.6 Hz, 2H), 1.45-1.40 (t, J=9.2 Hz, 1H), 1.25 (bs, 1H).

Example 43: N-((1S,2S)-2-methoxycyclobutyl)-5-((6'-methyl-2-oxo-2H-[1,3'-bipyridin]-3-yl)amino)-7-(methylamino)pyrazolo[1,5-a]pyrimidine-3-carboxamide (I-973), N-((1R,2R)-2-methoxycyclobutyl)-5-((6'-methyl-2-oxo-2H-[1,3'-bipyridin]-3-yl)amino)-7-(methylamino)pyrazolo[1,5-a]pyrimidine-3-carboxamide (I-974)

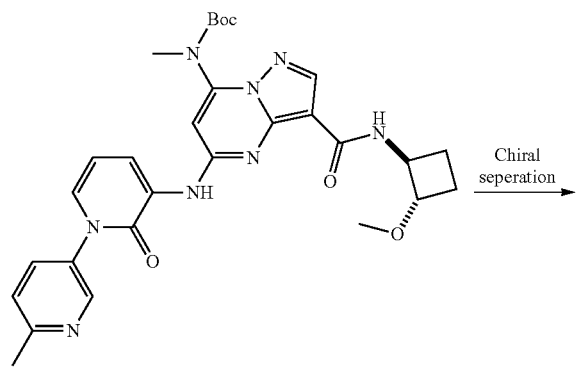

Chiral seperation

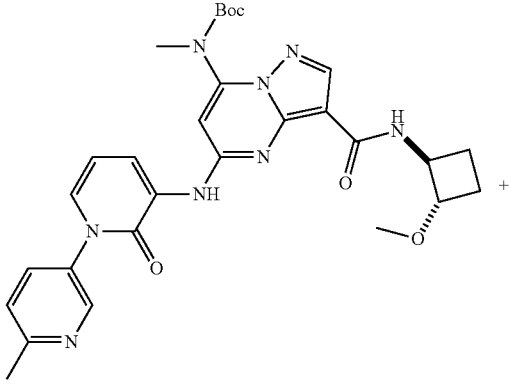

43.1

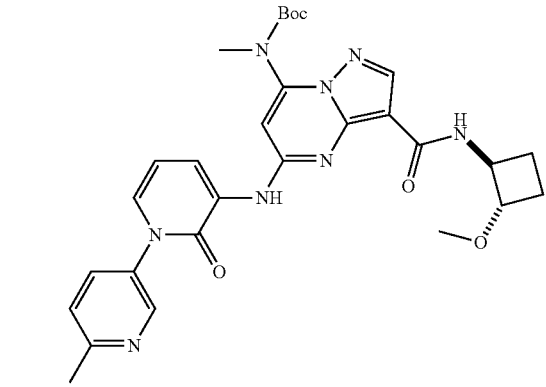

43.1

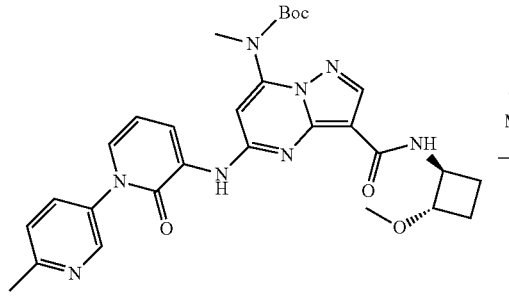

TFA, MDC, RT

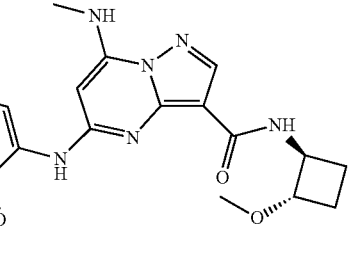

I-973

43.2

I-974

Synthesis of Compound 43.

Compound was synthesized as per experimental protocol of Example 42 to obtain 43. (Yield: 67.75%), MS (ES): m/z 565.25 [M+H]$^+$.

Isomers of I-890 (0.09 g) were separated using column CHIRALCEL OJ-H (250 mm*4.6 mm, 5 u) 0.1%_DEA_HEX_IPA-MEOH (50-50) to get pure fraction-1 (43.1) and fraction-2 (43.2). FR-1 was evaporated under reduced pressure at 30° C. to afford pure 43.1. (0.040 g). MS(ES): m/z 575.64 [M+H]$^+$. FR-2 was evaporated under reduced pressure at 30° C. to afford pure 43.2. (0.038 g). MS(ES): m/z 575.64 [M+H]$^+$.

Synthesis of I-973 and I-974.

Compound was synthesized using general procedure C to obtain deprotected 43.1 (0.025 g). MS(ES): m/z 475.66 [M+H]$^+$, LCMS purity: 100%, HPLC purity: 98.05%, CHIRAL HPLC purity: 99.89%, $^1$H NMR (DMSO-d$_6$, 400 MHZ): 8.35-8.32 (d, J=8 Hz, 1H), 8.23 (s, 1H), 8.06-8.00 (m, 3H), 7.51-7.49 (m, 3H), 6.45-6.43 (t, J=8 Hz, 1H), 6.21 (s, 1H), 4.32-4.30 (t, J=8 Hz, 1H), 3.73-3.71 (d, J=8 Hz, 3H), 3.21 (s, 3H), 2.93-2.91 (d, 3H), 2.20 (s, 2H), 2.14-2.05 (m, 1H), 1.52-1.50 (t, J=8 Hz, 1H), 1.38-1.35 (t, J=12 Hz, 1H), 1.27-1.25 (d, J=8 Hz, 1H); and deprotected 43.2 (0.025 g). MS(ES): m/z 475.66 [M+H]$^+$, LCMS purity: 100%, HPLC purity: 99.17%, CHIRAL HPLC purity: 96.45%, $^1$H NMR (DMSO-d$_6$, 400 MHZ): 9.10 (s, 1H), 8.35-8.33 (d, J=8 Hz, 1H), 8.23 (s, 1H), 8.06-8.00 (m, 3H), 7.51-7.49 (m, 3H), 6.45-6.43 (t, J=8 Hz, 1H), 6.21 (s, 1H), 4.31-4.29 (t, J=8 Hz, 1H), 3.72-3.70 (d, J=8 Hz, 3H), 3.21 (s, 3H), 2.93-2.91 (d, J=8 Hz, 3H), 2.20 (s, 2H), 2.14-2.05 (m, 1H), 1.52-1.50 (t, J=8 Hz, 1H), 1.38-1.35 (t, J=12 Hz, 1H), 1.27-1.25 (d, J=8 Hz, 1H).

Example 44: N-((1R,2S)-2-fluorocyclopropyl)-5-((1-((1S,2R)-2-hydroxycyclohexyl)-2-oxo-1,2-dihydropyridin-3-yl)amino)-7-(methylamino)pyrazolo[1,5-a]pyrimidine-3-carboxamide (I-988)

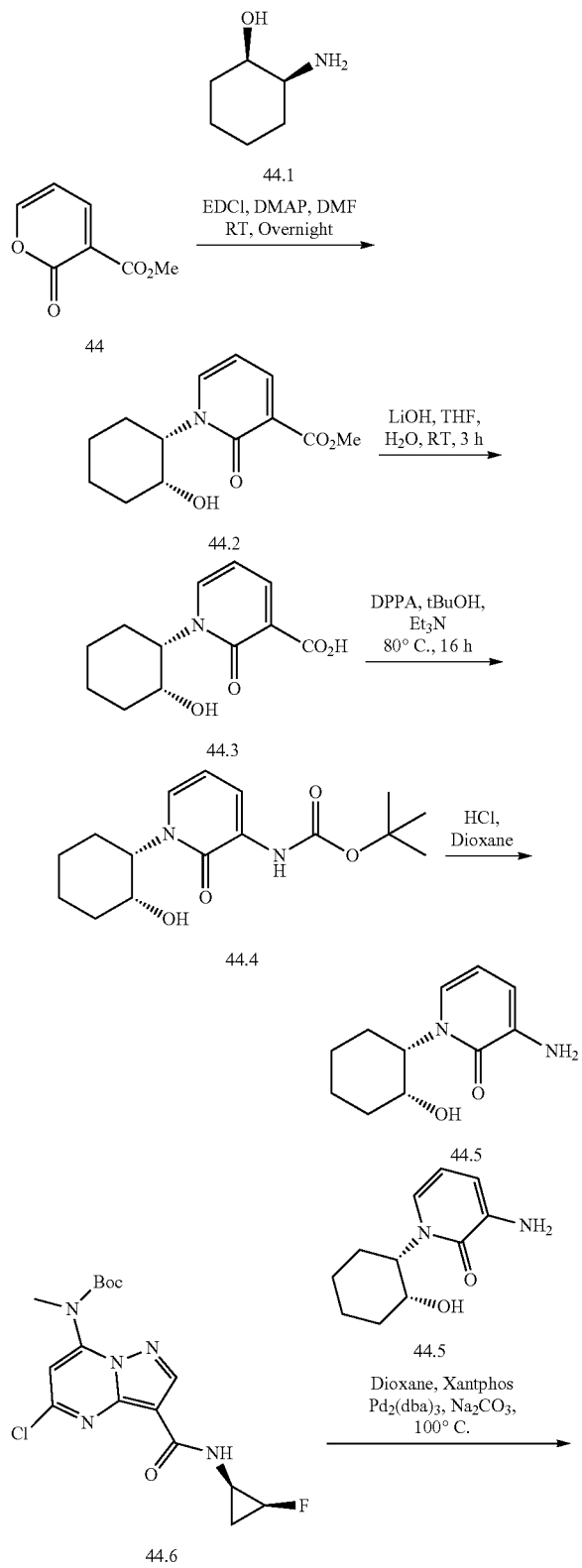

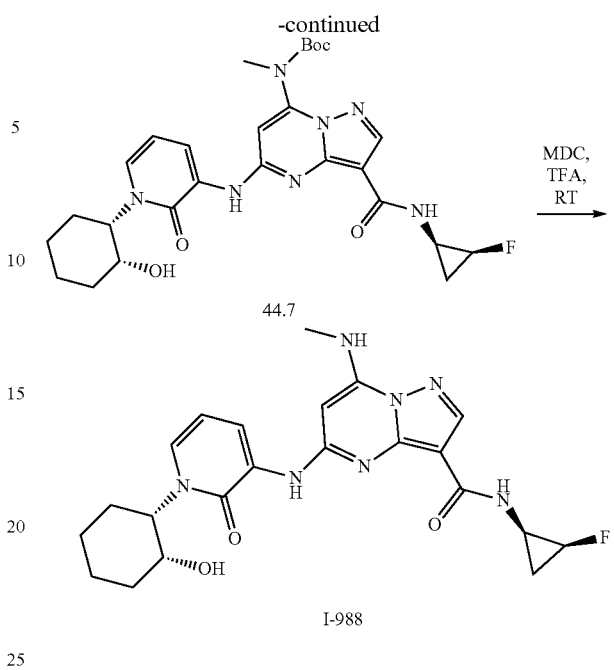

Synthesis of Compound 44.2.

To a stirred solution of 44.1 (5.0 g, 32.47 mmol, 1.0 eq) in N,N-dimethyl formamide (50 mL) was added 44 (5.0 g, 32.47 mmol, 1.0 eq) in one portion at 0° C. under Ar followed by diisopropyl ethyl amine (6.3 g, 48.71 mmol, 1.5 eq) and the reaction mixture was stirred at 0° C. for 3 h. 1-Ethyl-3-(3-dimethylaminopropyl)carbodiimide hydrochloride (8.1 g, 42.21 mmol, 1.3 eq) and then 4-Dimethylaminopyridine (1.0 g, 8.11 mmol, 0.25 eq) were added under argon and the reaction mixture was stirred at room temperature overnight. The reaction mixture was concentrated under reduced pressure to obtain residue which was purified by column chromatography and compound was eluted in 1.9% methanol in dichloromethane to obtain pure 44.2 (4.3 g, 52.76%). MS(ES): m/z 252.42 [M+H]⁺.

Synthesis of Compound 44.3.

To a stirred solution of 44.2 (1.5 g, 5.98 mmol, 1.0 eq) in tetrahydrofuran (45 mL) was added methanol (16.5 mL) and a solution of lithium hydroxide monohydrate (1.1 g, 25.71 mmol, 4.5 eq) in water (22 mL) and the reaction mixture was stirred at room temperature for 3 h. The reaction mixture was concentrated under vacuum and the residue was adjusted to pH 3 by slow addition of 1N hydrochloric acid at 0° C. The precipitate was collected by filtration and dried to obtain pure compound 44.3 (0.90 g, 48.06%). MS(ES): m/z 238.45 [M+H]⁺.

Synthesis of Compound 44.4.

A stirred mixture of 44.3 (0.90 g, 3.80 mmol, 1.0 eq), tert butanol (11 mL), diphenyl phosphoryl azide (1.5 g, 5.32 mmol, 1.4 eq) and triethyl amine (540 mg, 5.32 mmol, 1.4 eq) was heated at 80° C. under N₂ for 18 h. The reaction mixture was evaporated under reduced pressure. The residue was dissolved in ethyl acetate and the organic solution was washed with water. The organic phase was dried over sodium sulfate and concentrated under reduced pressure to obtain the crude. This was further purified by column chromatography and compound was eluted in 1% methanol in dichloromethane to obtain pure 44.4 (0.70 g, 59.82%). MS(ES): m/z 309.45 [M+H]⁺.

913

Synthesis of Compound 44.5.

To a stirred solution of 44.4 (0.70 g, 2.27 mmol) in dichloromethane (10 mL) was added 4 M HCl in dioxane (5 mL) dropwise at 0° C. under N$_2$ and the reaction mixture was stirred at room temperature for 3 h. Reaction mixture concentrated under reduced pressure to obtain residue which was triturated with diethyl ether to obtain 44.5 (0.40 g, 72.11%). MS(ES): m/z 209.32 [M+H]$^+$.

Synthesis of Compound 44.6.

Compound was synthesized as per experimental protocol of Example 19 to obtain 44.6 (Yield: 51.08%). MS (ES): m/z 384.81 [M+H]$^+$ Synthesis of Compound 44.7.

To a degassed mixture of 44.5 (0.077 g, 0.313 mmol, 1.2 eq) and 44.6 (0.100 g, 0.261 mmol, 1.0 eq) in 1,4-dioxane (7 mL) was added sodium carbonate (0.083 g, 0.783 mmol, 3.0 eq), 4,5-Bis(diphenylphosphino)-9,9-dimethylxanthene (0.015 g, 0.026 mmol, 0.1 eq) and tris(dibenzylideneacetone)dipalladium(0) (0.012 g, 0.013 mmol, 0.05 eq) and the reaction mixture was stirred at 100° C. for 5 h. After completion of reaction, reaction mixture was cooled to room temperature and filtered. The filtrate was concentrated under reduced pressure to obtain crude material. This was further purified by combi flash using 2% methanol in dichloromethane as eluant to obtain pure 44.7 (0.100 g, 69.90%). MS(ES): m/z 556.41 [M+H]$^+$.

Synthesis of Compound I-988.

To a stirred solution of 44.7 (0.100 g, 0.180 mmol) in dichloromethane (2 mL) was added 4 M HCl in dioxane (2 mL) dropwise at 0° C. under N$_2$ and the reaction mixture was stirred at room temperature for 2 h. Solvent was removed under vacuum and the solid residue was triturated with saturated sodium carbonate aqueous solution. The off white precipitate was collected by filtration and dried to obtain I-988 (0.040 g, 48.10%). MS(ES): m/z 456.52 [M+H]$^+$, LCMS purity: 100%, HPLC purity: 99.70%, Chiral HPLC purity: 100%, $^1$H NMR (DMSO-d$_6$, 400 MHZ): 8.84 (s, 1H), 8.24 (s, 1H), 8.15-8.12 (d, J=7.6 Hz, 1H), 7.93 (bs, 1H), 7.85-7.83 (m, 1H), 7.39-7.37 (d, J=6.8 Hz, 1H), 6.27-6.22 (m, 2H), 5.00-4.97 (m, 1H), 4.84-4.81 (m, 1H), 3.95 (bs, 1H), 2.99 (bs, 1H), 2.91 (s, 3H), 2.21-2.13 (m, 1H), 1.92-1.85 (m, 1H), 1.84-1.75 (m, 1H), 1.70-1.55 (m, 2H), 1.55-1.39 (m, 3H), 1.31-1.16 (m, 1H), 0.95-0.85 (m, 2H).

Example 45: 5-((2-methoxypyridin-3-yl)amino)-7-(methylamino)-N-(spiro[3.3]heptan-2-yl)pyrazolo[1,5-a]pyrimidine-3-carboxamide (I-408)

914

Synthesis of Compound 45.

Compound was synthesized as per experimental protocol of Example 32 to obtain 45. (Yield: 71.18%), MS (ES): m/z 415.42 [M+H]$^+$ Synthesis of Compound 45.1.

To 45 (0.150 g, 0.36 mmol, 1.0 eq) was added 4M hydrochloric acid in 1,4 Dioxane (3 mL) and stirred at room temperature for 4 h. After completion of reaction, reaction mixture was concentrated under reduced pressure, residue was triturated with diethyl ether to obtain 45.1 (0.110 g, 100%). MS (ES): m/z 315.38 [M+H]$^+$ Synthesis of Compound I-408.

Compound was synthesized using general procedure A to obtain I-408 (0.04 g, 27.8%). MS (ES): m/z 410.22 [M+H]$^+$, LCMS purity: 99.15%, HPLC purity: 96.75%, $^1$H NMR (DMSO-d$_6$, 400 MHZ): 8.97 (s, 1H), 8.23-8.21 (d, J=7.6 Hz, 1H), 8.13 (s, 1H), 7.95-7.89 (m, 3H), 7.00-6.97 (m, 1H), 5.86 (s, 1H), 4.63 (s, 2H), 4.59 (s, 2H), 4.24-4.13 (m, 1H), 3.95 (s, 3H), 2.91-2.90 (d, J=4.8 Hz, 3H), 2.58-2.55 (m, 2H), 1.89-1.84 (m, 2H), Example 46: N-(2-cyanopropan-2-yl)-5-((2-methoxypyridin-3-yl)amino)-7-(methylamino)-pyrazolo[1,5-a]pyrimidine-3-carboxamide (I-476)

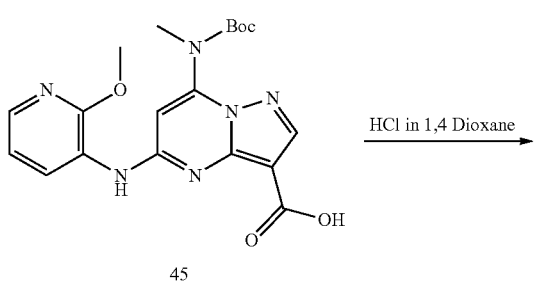

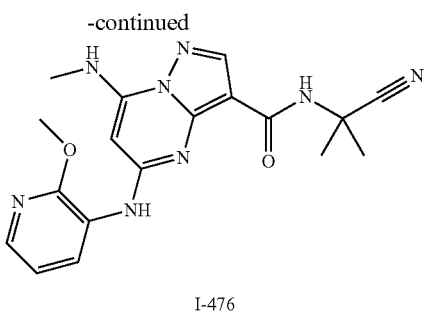

I-476

Synthesis of Compound 46.

Compound was synthesized as per experimental protocol of Example 45 to obtain 46. (Yield: 100%). MS (ES): m/z 315.38 [M+H]+

Synthesis of Compound I-476.

To a solution of 46 (0.35 g, 1.0 eq) in dichloromethane (4 mL) was added oxalyl chloride (0.279 g, 2.22 mmol, 2.0 eq) at 0° C. followed by N,N-dimethylformamide (catalytic). Reaction mixture was stirred at room temperature for 1 h. After completion of reaction, reaction mixture was concentrated under reduced pressure and 46.1 (0.280 g, 3.33 mmol, 3.0 eq) in tetrahydrofuran (5 mL), Triethylamine (0.699 g, 5.55 mmol, 5.0 eq) was added at 0° C. and reaction mixture was stirred for 16 h. After completion of reaction, reaction mixture was transferred into water and product was extracted with ethyl acetate. Organic layer was combined, washed with brine solution, dried over sodium sulfate and concentrated under reduced pressure to obtain crude which was triturated with diethyl ether to obtain I-476. (0.28 g, 7.0%), MS(ES): m/z 381.31 [M+H]+ LCMS purity: 96.33%, HPLC purity: 97.85%, $^1$H NMR (DMSO-$d_6$, 400 MHZ): 8.96 (s, 1H), 8.20 (s, 2H), 7.97-7.95 (d, J=4.8 Hz, 1H), 7.89-7.88 (d, J=3.6 Hz, 2H), 7.01-6.97 (m, 1H), 5.88 (m, 1H), 3.93 (s, 3H), 2.91-2.89 (d, J=4.8 Hz, 3H), 1.58 (s, 6H).

Example 47: N-cyclopropyl-7-(methylamino)-5-((6-(tetrahydro-2H-pyran-2-yl)pyridin-2-yl)amino)pyrazolo[1,5-a]pyrimidine-3-carboxamide (I-432), (R)—N-cyclopropyl-7-(methylamino)-5-((6-(tetrahydro-2H-pyran-2-yl)pyridin-2-yl)amino)pyrazolo[1,5-a]pyrimidine-3-carboxamide (I-463), and (S)—N-cyclopropyl-7-(methylamino)-5-((6-(tetrahydro-2H-pyran-2-yl)pyridin-2-yl)amino)pyrazolo[1,5-a]pyrimidine-3-carboxamide (I-464)

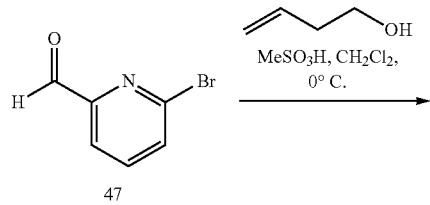

47

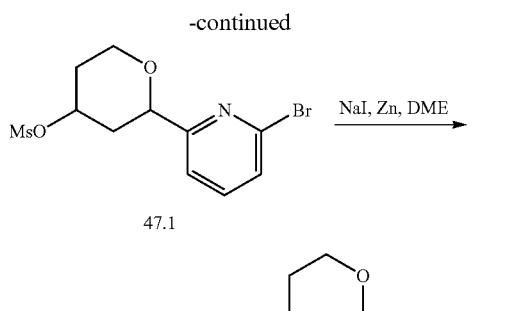

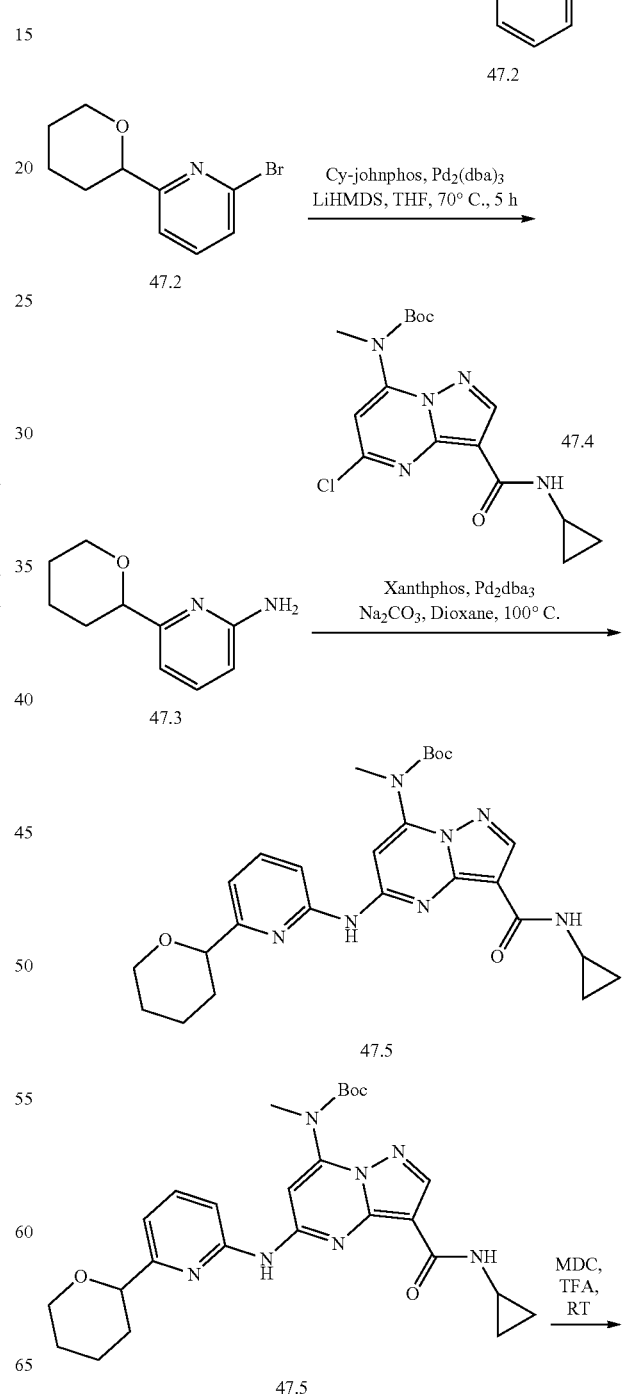

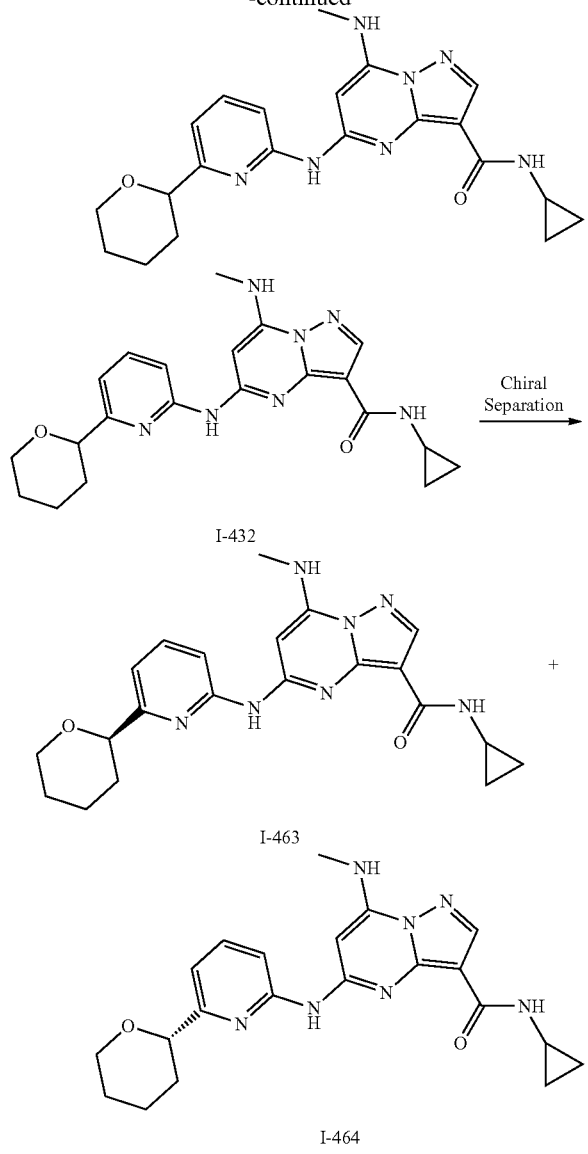

Synthesis of Compound 47.1

To a solution of 47 (0.2 g, 1.075 mmol, 1.0 eq), in dry dichloromethane (5 mL) was added but-3-en-1-ol (0.077 g, 1.075 mmol, 2.0 eq) followed by methane sulphonic acid (0.7 mL) and stirred at 0° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 47.1 (0.25. g, 69.16%). MS(ES): m/z 337.20 [M+H]$^+$.

Synthesis of Compound 47.2.

To a solution of 47.1 (0.240 g, 0.711 mmol, 1.0 eq), in dimethoxy ethane (10 mL) were added zinc (0.231 g, 3.5 mmol, 5.0 eq) and sodium iodide (1.58 g, 10.66 mmol, 15 eq) at room temperature. The reaction mixture was stirred at 80° C. for 3 hrs. After completion of reaction, reaction mixture was transferred into water and product was extracted with diethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 47.2 (0.12 g, 57.86%). MS(ES): m/z 243.12 [M+H]$^+$.

Synthesis of Compound 47.3.

A solution of 1 (0.125 g, 0.52 mmol, 1.0 eq) in tetrahydrofuran (5 mL) was degassed for 10 min. under argon atmosphere, then (2-Biphenyl)dicyclohexylphosphino(0) (0.009 g, 0.025 mmol, 0.05 eq) and Tris(dibenzylideneacetone)dipalladium(0) (0.047 g, 0.052 mmol, 0.1 eq) were added, again degassed for 5 min. Then Lithium bis(trimethylsilyl)amide (0.10 mL, 0.104 mmol, 2.00 eq) was added to reaction mixture at 0° c. The reaction was stirred at 60° C. for 45 min. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluent to obtain pure 47.3 (0.09 g, 97.81%). MS(ES): m/z 179.2 [M+H]$^+$ Synthesis of Compound 47.4.

Compound was synthesized as per experimental protocol of Example 27 to obtain 47.4 (Yield: 57.16%), MS (ES): m/z 366.82 [M+H]$^+$ Synthesis of Compound 47.5.

Compound was synthesized using general procedure B to obtain 47.5. (0.150 g, 26.34%) MS(ES): m/z 508.60 [M+H]$^+$ Synthesis of Compound I-432.

Compound was synthesized using general procedure C to obtain I-432. (0.120 g, 99.06%). MS(ES): m/z 408.48 [M+H]$^+$ LCMS purity: 98.06%, HPLC purity: 96.46%, $^1$H NMR (DMSO-d$_6$, 400 MHZ): 9.97 (s, 1H), 8.21 (s, 1H), 8.05-8.04 (d, J=4.8 Hz, 1H), 7.96-7.95 (d, J=3.2 Hz, 1H), 7.76-7.72 (t, J=8 Hz, 1H), 7.51-7.49 (d, J=7.6 Hz, 1H), 7.06-7.04 (d, J=7.6 Hz, 1H), 6.69 (s, 1H), 4.34-4.32 (d, J=10 Hz, 1H), 4.07-4.04 (d, J=11.6 Hz, 1H), 3.60-3.54 (m, 1H), 2.94-2.93 (d, J=4.4 Hz, 3H), 2.88-2.82 (m, 1H), 2.04-2.02 (d, J=11.26 Hz, 1H), 1.91-1.88 (d, J=12.8 Hz, 1H), 1.65-1.49 (m, 4H), 0.80-0.75 (m, 2H). 0.56-0.55 (m, 2H), Synthesis of Compound I-463 & I-464.

Isomers of I-432 (0.8 g) were separated using a column (CHIRAL PAK AD-H 250×4.6 mm, 5 u) and 0.1% DEA in methanol and isopropyl alcohol as co-solvent with flow rate of 4 mL/min. to get pure fraction-1 (FR-a) and fraction-2 (FR-b). FR-a was concentrated under reduced pressure at 30° C. to afford pure FR-a (0.026 g). MS(ES): m/z 408.48 [M+H]$^+$, LCMS purity: 100%, HPLC purity: 99.89%, CHIRAL HPLC purity: 100%, $^1$H NMR (DMSO-d$_6$, 400 MHZ): 9.97 (s, 1H), 8.21 (s, 1H), 8.05-8.04 (d, J=4.8 Hz, 1H), 7.96-7.95 (d, J=3.2 Hz, 1H), 7.76-7.72 (t, J=8 Hz, 1H), 7.51-7.49 (d, J=7.6 Hz, 1H), 7.06-7.04 (d, J=7.6 Hz, 1H), 6.69 (s, 1H), 4.34-4.32 (d, J=10 Hz, 1H), 4.07-4.04 (d, J=11.6 Hz, 1H), 3.60-3.54 (m, 1H), 2.94-2.93 (d, J=4.4 Hz, 3H), 2.88-2.82 (m, 1H), 2.04-2.02 (d, J=11.26 Hz, 1H), 1.91-1.88 (d, J=12.8 Hz, 1H), 1.65-1.49 (m, 4H), 0.80-0.75 (m, 2H). 0.56-0.55 (m, 2H). FR-b was concentrated under reduced pressure at 30° C. to afford pure FR-b (0.028 g).

MS(ES): m/z 406.46 [M+H]+, LCMS purity: 100%, HPLC purity: 99.48%, CHIRAL HPLC purity: 100%, ¹H NMR (DMSO-d₆, 400 MHZ): 9.97 (s, 1H), 8.21 (s, 1H), 8.05-8.04 (d, J=4.8 Hz, 1H), 7.96-7.95 (d, J=3.2 Hz, 1H), 7.76-7.72 (t, J=8 Hz, 1H), 7.51-7.49 (d, J=7.6 Hz, 1H), 7.06-7.04 (d, J=7.6 Hz, 1H), 6.69 (s, 1H), 4.34-4.32 (d, J=10 Hz, 1H), 4.07-4.04 (d, J=11.6 Hz, 1H), 3.60-3.54 (m, 1H), 2.94-2.93 (d, J=4.4 Hz, 3H), 2.88-2.82 (m, 1H), 2.04-2.02 (d, J=11.26 Hz, 1H), 1.91-1.88 (d, J=12.8 Hz, 1H), 1.65-1.49 (m, 4H), 0.80-0.75 (m, 2H) 0.56-0.55 (m, 2H).

Example 48: N-(2-cyanopropan-2-yl)-5-((2-cyclopropoxypyridin-3-yl)amino)-7-(methylamino)pyrazolo[1,5-a]pyrimidine-3-carboxamide (I-492)

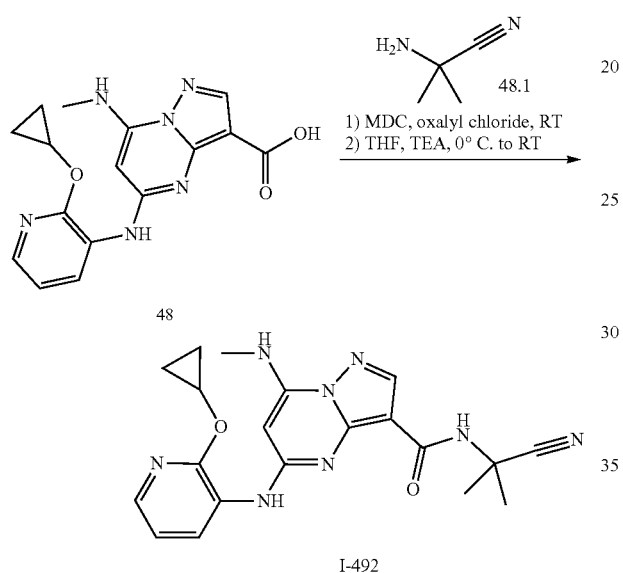

Synthesis of Compound 48.

Compound was synthesized as per experimental protocol of Example 47 to obtain 48. (Yield: 90.59%). MS (ES): m/z 341.1 [M+H]+

Synthesis of Compound I-492.

To a solution of 48. (0.2 g, 0.58 mmol, 1.0 eq) in dichloromethane (3 mL) was added oxalyl chloride (0.149 g, 1.16 mmol, 2.0 eq) at 0° C. followed by N,N-dimethylformamide (catalytic). Reaction mixture was stirred at room temperature for 1 h. After completion of reaction, reaction mixture was concentrated under reduced pressure and 48.1 (0.097 g, 1.16 mmol, 2.0 eq) in tetrahydrofuran (4 ml), Triethylamine (0.292 g, 2.9 mmol, 5.0 eq) was added at 0° C. and reaction mixture was stirred for 16 h. After completion of reaction, reaction mixture was transferred into water and product was extracted with ethyl acetate. Organic layer was combined, washed with brine solution, dried over sodium sulfate and concentrated under reduced pressure to obtain crude which was triturated with diethyl ether to obtain I-492. (0.28 g, 11.72%), MS(ES): m/z 407.67 [M+H]+ LCMS purity: 95.01%, HPLC purity: 97.29%, ¹H NMR (DMSO-d₆, 400 MHZ): 8.79 (s, 1H), 8.20 (s, 1H), 8.17-8.15 (d, J=7.6 Hz, 1H), 7.97-7.93 (m, 2H), 7.85 (s, 1H), 7.04-4.01 (m, 1H), 5.83 (s, 1H), 4.35-7.32 (bs, 1H), 2.92-2.91 (d, J=4.8 Hz, 3H), 1.59 (s, 6H), 0.79-0.74 (m, 2H), 0.68 (bs, 2H).

Example 49: N-(2-hydroxycyclobutyl)-5-((2-(methoxy-d3)pyridin-3-yl)amino)-7-(methylamino)pyrazolo[1,5-a]pyrimidine-3-carboxamide (I-391), N-((1S,2R)-2-hydroxycyclobutyl)-5-((2-(methoxy-d3)pyridin-3-yl)amino)-7-(methylamino)pyrazolo[1,5-a]pyrimidine-3-carboxamide (I-399), and N-((1R,2S)-2-hydroxycyclobutyl)-5-((2-(methoxy-d3)pyridin-3-yl)amino)-7-(methylamino)pyrazolo[1,5-a]pyrimidine-3-carboxamide (I-400)

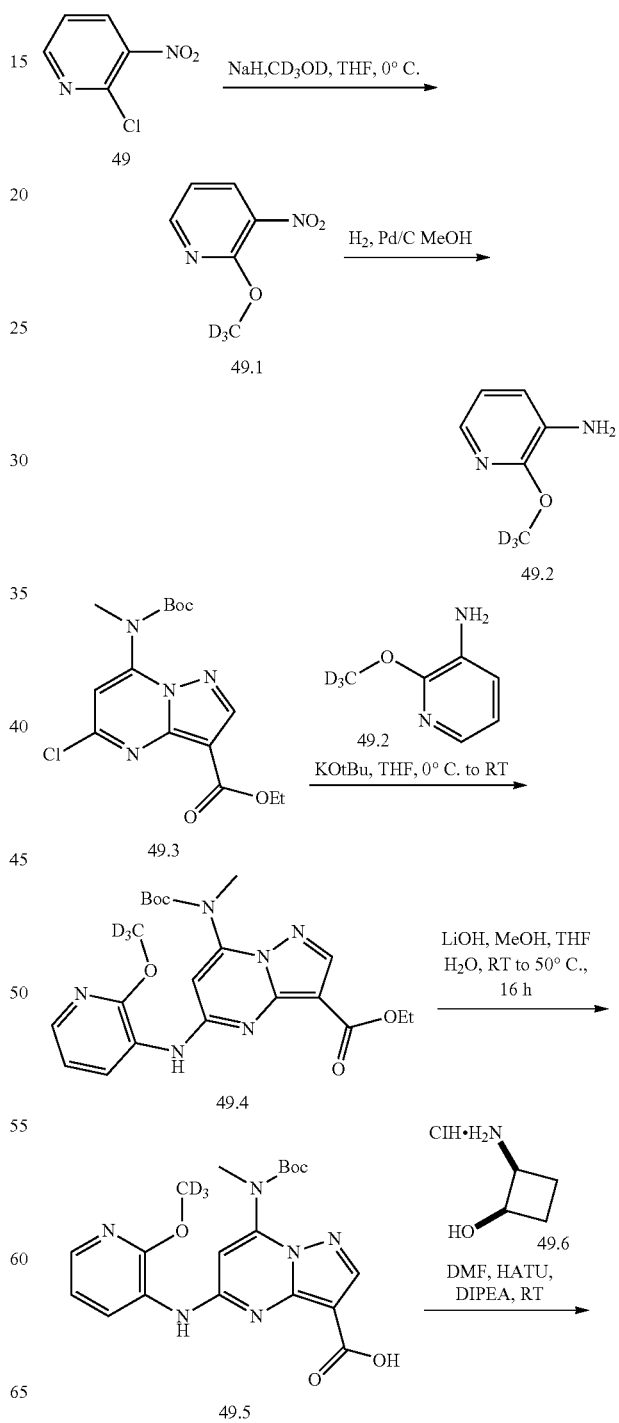

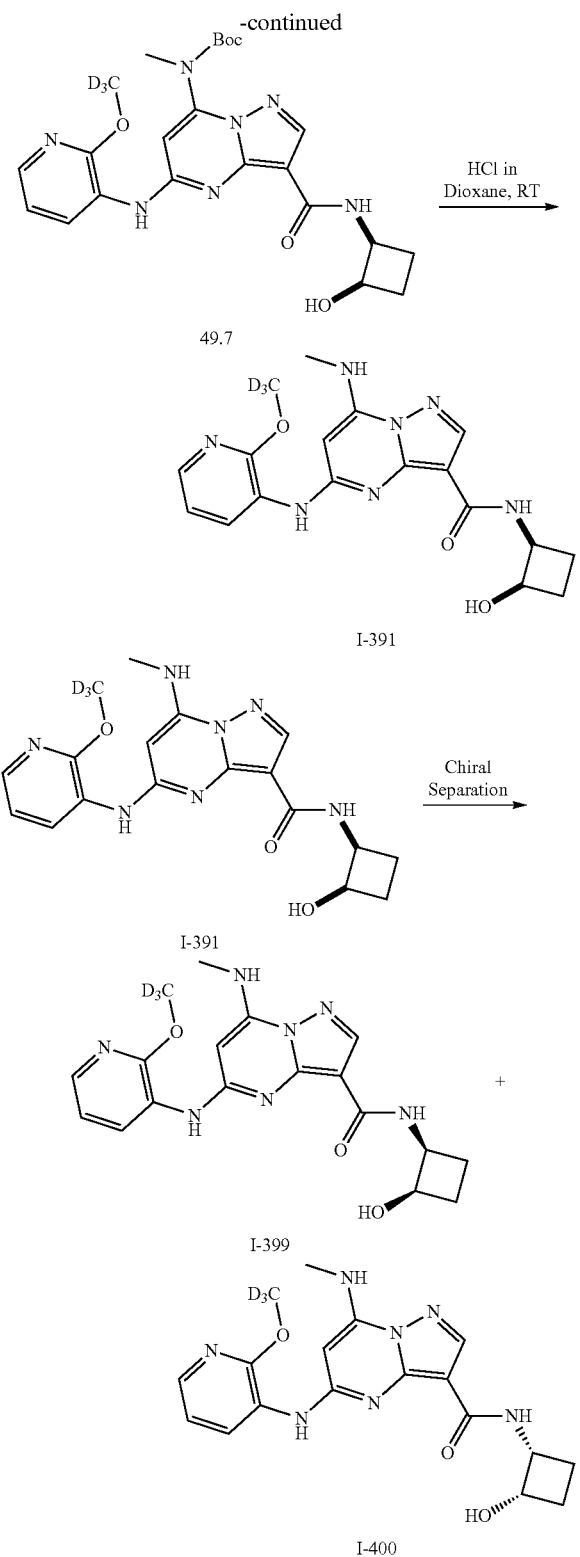

Synthesis of Compound 49.1.

To a cooled solution of 49 (1 g, 6.31 mmol, 1.0 eq) in tetrahydrofuran (10 mL) was added sodium hydride (0.505 g, 12.62 mmol, 2.0 eq) and stirred for 20 min. followed by addition of tetradeuteromethanol (0.250 g, 6.94 mmol, 1.1 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 13% ethyl acetate in hexane to obtain pure 49.1 (0.900 g, 90.80%), MS(ES): m/z 158.14 [M+H]$^+$.

Synthesis of Compound 49.2.

To a solution of 49.1 (0.900 g, 5.73 mmol, 1.0 eq) in methanol (10 mL), palladium on charcoal (0.400 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 49.2 (0.650 g, 89.25%). MS (ES): m/z 128.16 [M+H]$^+$ Synthesis of Compound 49.3.

Compound was synthesized using general procedure of core synthesis to obtain 49.3 (Yield: 62.21%). MS (ES): m/z 355.5 [M+H]$^+$ Synthesis of Compound 49.4.

To a cooled solution of 49.3 (0.600 g, 1.69 mmol, 1.0 eq), and 49.2 (0.215 g, 1.69 mmol, 1.0 eq) in tetrahydrofuran (10 mL) at 0° C. was added potassium ter-butoxide (1M in tetrahydrofuran) (3.3 mL, 3.38 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 49.4. (0.59 g, 78.31%). MS (ES): m/z 446.40 [M+H]$^+$.

Synthesis of Compound 49.5.

To a solution of 49.4 (0.590 g, 1.32 mmol, 1.0 eq), in tetrahydrofuran: methanol: water (8 mL, 2:2:1) was added lithium hydroxide (0.554 g, 13.2 mmol, 10 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 49.5 (0.380 g, 68.74%). MS(ES): m/z 418.44 [M+H]$^+$.

Synthesis of Compound 49.7.

To a solution of 49.5 (0.190 g, 0.455 mmol, 1.0 eq), in N,N-dimethylformamide (3 mL) was added 1-[Bis(dimethylamino)methylene]-1H-1,2,3-triazolo[4,5-b]pyridinium 3-oxid hexafluorophosphate (0.345 g, 0.91 mmol, 2.0 eq) and stirred at room temperature for 15 min. To this added diisopropylethylamine (0.4 mL, 2.275 mmol, 5.0 eq) followed by addition of 49.6 (0.113 g, 0.910 mmol, 2.0 eq). The reaction mixture was stirred at room temperature for 30 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% dichlormethane in methanol to obtain 49.7 (0.145 g, 65.48%). MS(ES): m/z 487.5 [M+H]$^+$.

Synthesis of Compound I-391.

To the cooled solution of 49.7 (0.145 g, 0.298 mmol, 1.0 eq) in dichloromethane (5 mL) at 0° C. was added hydrochloric acid in dioxane (4 mL) drop wise. The reaction was stirred at room temperature for 30-50 min. After completion of reaction, reaction mixture concentrated under reduced pressure. To the residue added saturated bicarbonate solution and product was extracted with dichloromethane. Organic layer was combined and dried over sodium sulphate and concentrated under reduced pressure to obtain crude material. This was further purified by trituration with diethyl ether to obtain pure I-391 (0.100 g, 86.83%). MS (ES): m/z 387.23 [M+H]⁺, LCMS purity: 100%, HPLC purity: 95%, Chiral HPLC: 47.49% and 48.37% ¹H NMR (DMSO-d₆, 400 MHZ): 8.81 (s, 1H), 8.66-8.64 (d, J=8 Hz, 1H), 8.17 (s, 1H), 8.04-8.01 (d, J=8.8 Hz, 1H), 7.89-7.88 (d, J=4.8 Hz, 1H), 7.83-7.82 (d, J=3.6 Hz, 1H), 7.08-705 (m, 1H), 6.05 (s, 1H), 5.27-5.26 (d, J=4 Hz, 1H), 4.56-4.52 (m, 1H), 4.29 (bs, 1H), 2.92-2.91 (d, J=5.2 Hz, 3H), 2.13-2.01 (m, 2H), 1.95-1.86 (m, 1H), 1.71-1.69 (m, 1H).

Isomers of I-391 (0.085 g) were separated out using column (CHIRALPAK IC (250 mm*4.6 mm, 5 u)) in 0.1% DEA in IPA:ACN (50:50) as co-solvent with flow rate of 4 mL/min. to get pure fraction-1 (FR-a) and fraction-2 (FR-b).

FR-a was concentrated under reduced pressure at 30° C. to afford pure FR-a (0.025 g). MS(ES): m/z 387.2 [M+H]⁺, LCMS purity: 95.12%, HPLC purity: 96.61%, CHIRAL HPLC purity: 100%, ¹H NMR (DMSO-d₆, 400 MHZ): 8.81 (s, 1H), 8.67-8.65 (d, J=6.8 Hz, 1H), 8.17 (s, 1H), 8.04-8.01 (d, J=9.2 Hz, 1H), 7.89-7.88 (d, J=4.8 Hz, 1H), 7.83-7.82 (d, J=3.6 Hz, 1H), 7.08-705 (m, 1H), 6.07 (s, 1H), 5.26-5.25 (d, J=3.6 Hz, 1H), 4.56-4.49 (m, 1H), 4.30 (bs, 1H), 2.92-2.91 (d, J=5.2 Hz, 3H), 2.13-2.01 (m, 2H), 1.95-1.86 (m, 1H), 1.71-1.69 (m, 1H).

FR-b was concentrated under reduced pressure at 30° C. to afford pure FR-b (0.025 g). MS(ES): m/z 387.2 [M+H]⁺, LCMS purity: 96.16%, HPLC purity: 96.61%, CHIRAL HPLC purity: 100%, ¹H NMR (DMSO-d₆, 400 MHZ): 8.81 (s, 1H), 8.68-8.66 (d, J=7.6 Hz, 1H), 8.18 (s, 1H), 8.04-8.01 (d, J=8.8 Hz, 1H), 7.90-7.89 (d, J=5.2 Hz, 1H), 7.84-7.83 (d, J=4 Hz, 1H), 7.09-7.06 (m, 1H), 6.07 (s, 1H), 5.27-5.26 (d, J=3.6 Hz, 1H), 4.55-4.52 (m, 1H), 4.30 (bs, 1H), 2.93-2.92 (d, J=4.4 Hz, 3H), 2.14-2.07 (m, 2H), 1.93-1.87 (m, 1H), 1.71-1.69 (m, 1H).

Example 50: 5-((2-(methoxy-d3)pyridin-3-yl)amino)-7-(methylamino)-N-(2-oxaspiro[3.3]heptan-6-yl)pyrazolo[1,5-a]pyrimidine-3-carboxamide (I-417)

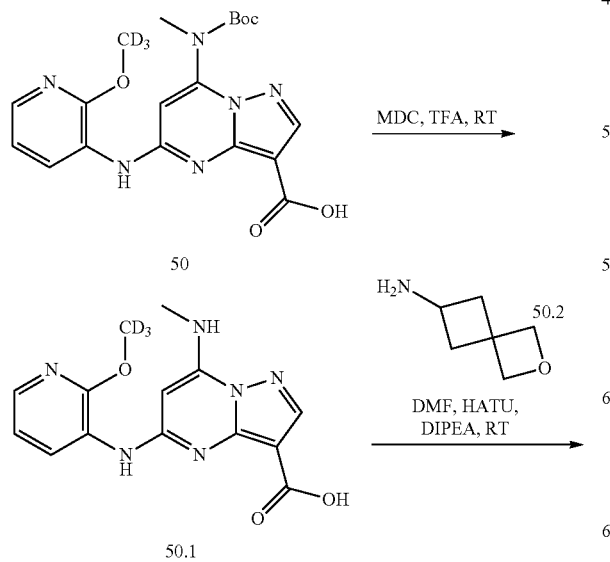

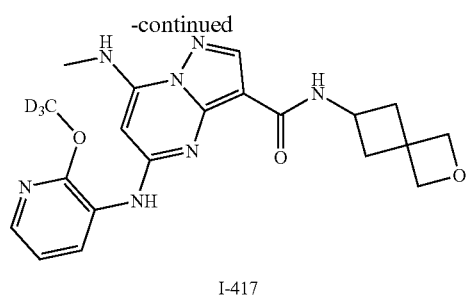

I-417

Synthesis of Compound 50.
Compound was synthesized as per experimental protocol of Example 49 to obtain 50. (Yield: 68.74%). MS (ES): m/z 418.44 [M+H]⁺

Synthesis of Compound 50.1.
Compound was synthesized using general procedure C to obtain 50.1. (0.148 g, 77.88%), MS (ES): 318.13 [M+H]⁺

Synthesis of Compound I-417:
Compound was synthesized using general procedure A to obtain I-417 (0.030 g, 32.97%), MS (ES): m/z 413.23 [M+H]⁺, LCMS purity: 99.07%, HPLC purity: 98.17%, ¹H NMR (DMSO-d₆, 400 MHZ): 8.97 (s, 1H), 8.23-8.21 (d, J=4 Hz, 1H), 8.13 (s, 1H), 7.95-7.89 (m, 3H), 7.00-6.97 (m, 1H), 5.87 (s, 1H), 4.64 (s, 2H), 4.51 (s, 2H) 4.24-4.18 (m, 1H), 2.92-2.90 (d, J=4.8 Hz, 3H), 2.51 (bs, 2H), 1.89-1.84 (m, 1H), 1.28-1.25 (m, 1H).

Example 51: N-(2-cyanopropan-2-yl)-5-((2-(methoxy-d3)pyridin-3-yl)amino)-7-(methylamino)pyrazolo[1,5-a]pyrimidine-3-carboxamide (I-493)

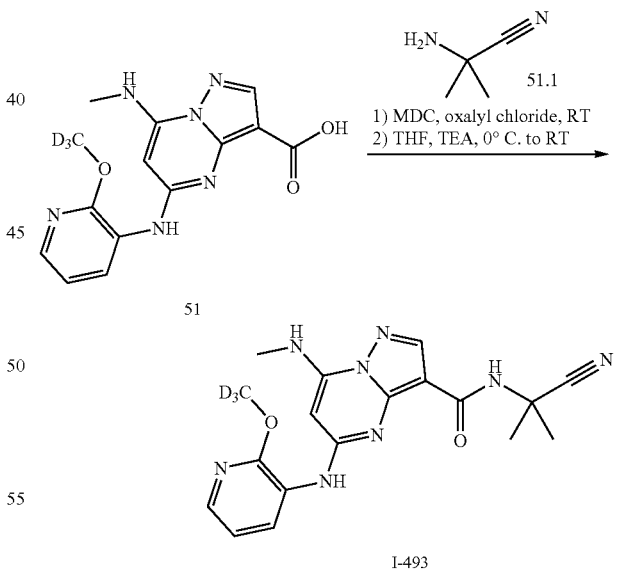

Synthesis of Compound 51.
Compound was synthesized as per experimental protocol of Example 50 to obtain 51. (Yield: 77.88%). MS (ES): m/z 318.13 [M+H]⁺

Synthesis of Compound I-493.
To a solution of 51. (0.2 g, 0.63 mmol, 1.0 eq) in dichloromethane (4 mL) was added oxalyl chloride (0.162 g, 1.26 mmol, 2.0 eq) at 0° C. followed by N,N-dimethylformamide (catalytic). Reaction mixture was stirred at room temperature for 1 h. After completion of reaction, reaction mixture was concentrated under reduced pressure and 51.1 (0.158 g, 1.89 mmol, 3.0 eq) in tetrahydrofuran (5 ml), Triethylamine (0.406 g, 3.15 mmol, 5.0 eq) was added at 0° C. and reaction mixture was stirred for 16 h. After completion of reaction, reaction mixture was transferred into water and product was extracted with ethyl acetate. Organic layer was combined, washed with brine solution, dried over sodium sulfate and concentrated under reduced pressure to obtain crude which was triturated with diethyl ether to obtain I-493. (0.26 g, 10.76%), MS(ES): m/z 384.45 [M+H]+ LCMS purity: 98.60%, HPLC purity: 98.08%, $^1$H NMR (DMSO-$d_6$, 400 MHZ): 8.97 (s, 1H), 8.22 (s, 2H), 7.98-7.97 (d, J=4.8 Hz, 1H), 7.91-7.90 (d, J=3.6 Hz, 1H), 7.87 (s, 1H), 7.02-6.99 (m, 1H), 5.90 (s, 1H), 2.92-2.91 (d, J=4.4 Hz, 3H), 1.60 (s, 6H).

Example 52: N-(tert-butoxy)-5-((2-methoxypyridin-3-yl)amino)-7-(methylamino)pyrazolo[1,5-a]pyrimidine-3-carboxamide (I-612)

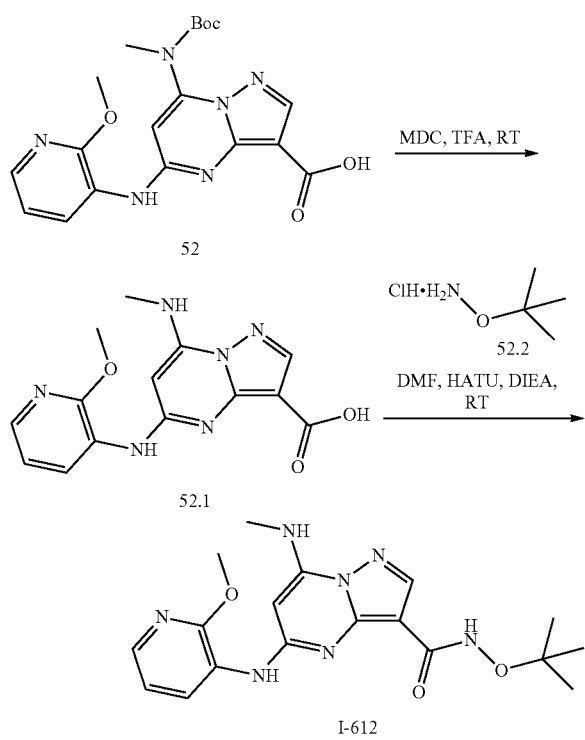

Synthesis of Compound 52.

Compound was synthesized as per experimental protocol of Example 32 to obtain 52. (Yield: 71.18%), MS (ES): m/z 415.42 [M+H]+

Synthesis of Compound 52.1.

The compound 1 (0.200 g, 0.483 mmol, 1.0 eq) was dissolved in dichloromethane (6 mL) and trifluoroacetic acid (1.5 mL) was added to the reaction mixture. The reaction mixture was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 52.1 (0.140 g, 92.30%). MS(ES): m/z 315.12 [M+H]+

Synthesis of Compound I-612.

Compound was synthesized using general procedure A to obtain I-612 (0.04 g, 37.67%). MS (ES): m/z 386.4 [M+H]+, LCMS purity: 100%, HPLC purity: 99.82%, $^1$H NMR (DMSO-$d_6$, 400 MHZ): 9.79 (s, 1H), 8.94 (s, 1H), 8.262-8.244 (d, J=7.2 Hz, 2H), 8.18 (s, 1H), 7.94-7.89 (d, J=18 Hz, 2H), 6.97 (s, 1H), 3.94 (s, 3H), 2.90 (s, 3H), 1.18 (s, 9H).

Example 53: N-(3-hydroxy-3-methylbutyl)-5-((2-methoxypyridin-3-yl)amino)-7-(methylamino)pyrazolo[1,5-a]pyrimidine-3-carboxamide (I-420)

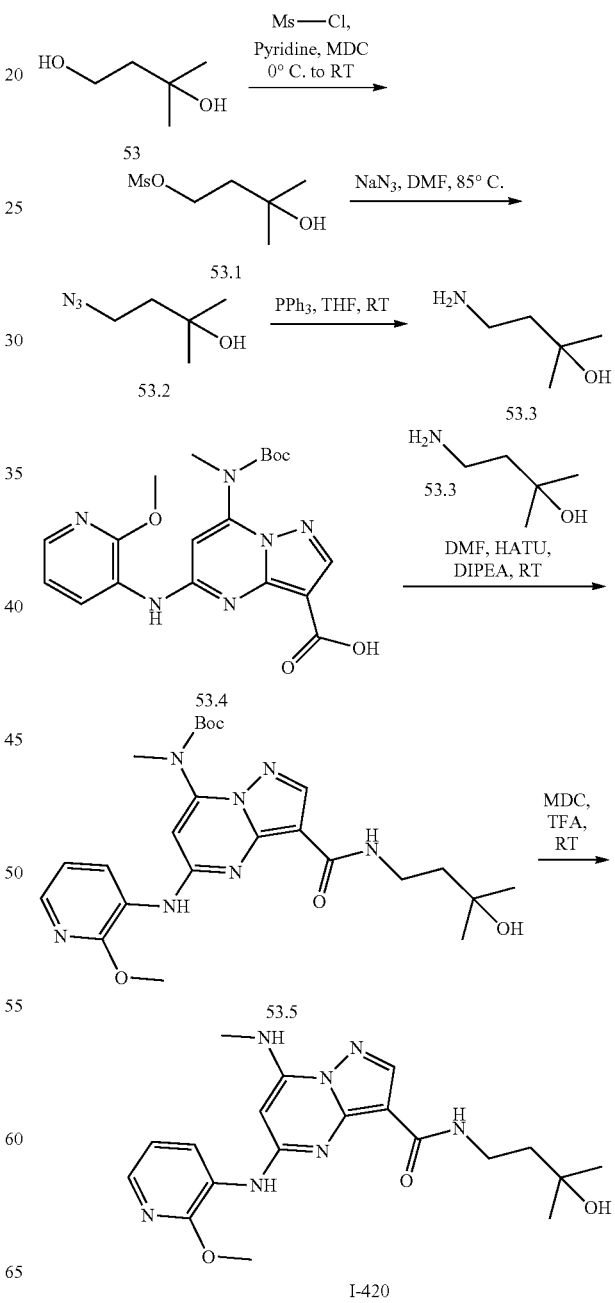

Synthesis of Compound 53.1.

To a cooled solution of 53 (2.0 g, 19.20 mmol, 1.0 eq) in dichloromethane (40 mL) was added pyridine (3.03 g, 38.4 mmol, 2.0 eq) followed by mesyl chloride (2.29 g, 20.16 mmol, 1.05 eq) dropwise at 0° C. The reaction mixture was stirred at room temperature for 1 h. After completion of reaction, reaction mixture was transferred into ice cold water and product was extracted with dichloro methane. Organic layer was combined, dried over sodium sulphate and concentrated under reduced pressure to obtain 53.1. (1.5 g, 42.86%), MS(ES): m/z 183.06 [M+H]+.

Synthesis of Compound 53.2.

To a solution of 53.1 (1.5 g, 8.23 mmol, 1.0 eq) in dimethyl formamide (15 mL) was added sodium azide (1.60 g, 24.69 mmol, 3.0 eq) at room temperature. The reaction was stirred at 80° C. for 20 h. After completion of reaction, reaction mixture was transferred into water and product was extracted with dichloro methane. Organic layer was combined and dried over sodium sulphate and concentrated under reduced pressure to obtain 53.2. (0.330 g, 31.04%), MS(ES): m/z 130.09 [M+H]+.

Synthesis of Compound 53.3.

To a solution of 53.2 (0.330 g, 2.55 mmol, 1.0 eq) in tetrahydrofuran (15 mL) was added Triphenylphosphine (1.0 g, 3.82 mmol, 1.5 eq) at room temperature. The reaction was stirred at 80° C. for 20 h. After completion of reaction, reaction mixture was transferred into water and product was extracted with dichloro methane. Organic layer was combined and dried over sodium sulphate and concentrated under reduced pressure to obtain 53.3. (0.2 g, 75.88%), MS(ES): m/z 104.10 [M+H]+.

Synthesis of Compound 53.4.

Compound was synthesized as per experimental protocol of Example 32 to obtain 53.4. (Yield: 71.18%), MS (ES): m/z 415.42 [M+H]+

Synthesis of Compound 53.5.

Compound was synthesized using general procedure A to obtain 53.5. (0.065 g, 71.89%), MS (ES): 500.2 [M+H]+

Synthesis of Compound I-420:

Compound was synthesized using general procedure C to obtain I-420 (0.027 g, 51.95%), MS (ES): m/z 400.22 [M+H]+, LCMS purity: 95.47%, HPLC purity: 95.82%, 1H NMR (DMSO-d6, 400 MHZ): 8.92 (s, 1H), 8.32-8.30 (d, J=7.6 Hz, 1H), 8.15 (s, 1H), 7.93-7.89 (m, 2H), 7.69 (bs, 1H), 7.06-7.03 (m, 1H), 5.92 (s, 1H), 3.97 (s, 3H), 3.35-3.30 (m, 3H), 2.92-2.91 (d, J=4.4 Hz, 3H), 1.59-1.53 (m, 2H), 1.16 (s, 6H).

Example 54: N-(3-hydroxy-3-methylbutyl)-5-((2-(methoxy-d3)pyridin-3-yl)amino)-7-(methylamino)pyrazolo[1,5-a]pyrimidine-3-carboxamide (I-421)

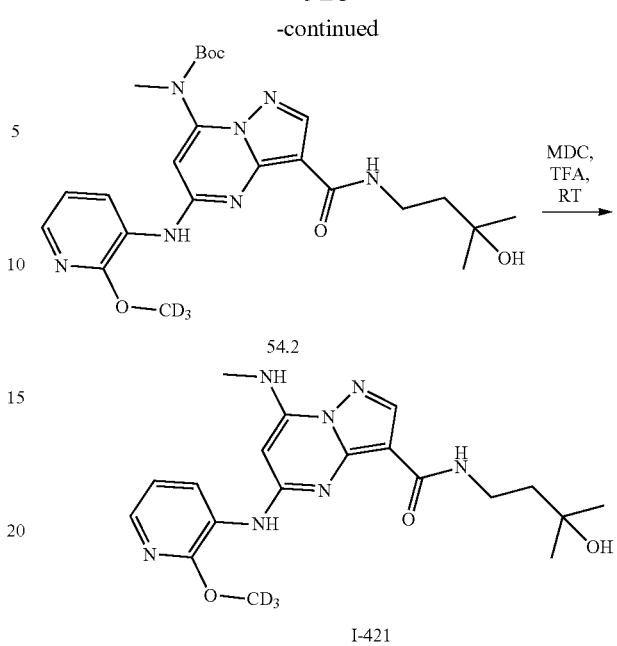

Synthesis of Compound 54.

Compound was synthesized as per experimental protocol of Example 49 to obtain 54. (Yield: 68.74%). MS (ES): m/z 418.44 [M+H]+

Synthesis of Compound 54.1.

Compound was synthesized as per experimental protocol of Example 53 to obtain 54.1. (Yield: 75.78%). MS (ES): m/z 104.10 [M+H]+

Synthesis of Compound 54.2.

Compound was synthesized using general procedure A to obtain 54.2. (0.058 g, 48.17%), MS (ES): 503.28 [M+H]+

Synthesis of Compound I-421:

Compound was synthesized using general procedure C to obtain I-421 (0.029 g, 62.44%), MS (ES): m/z 403.42 [M+H]+, LCMS purity: 100%, HPLC purity: 97.56%, 1H NMR (DMSO-d6, 400 MHZ): 8.91 (s, 1H), 8.32-8.30 (d, J=7.2 Hz, 1H), 8.15 (s, 1H), 7.92-7.89 (m, 2H), 7.70-7.67 (t, J=5.2 Hz, 1H), 7.05-7.02 (m, 1H), 5.93 (s, 1H), 4.34 (s, 1H) 3.35 (bs, 2H), 2.92-2.91 (d, J=4.4 Hz, 3H), 1.57-1.53 (t, J=8 Hz, 2H), 1.13 (s, 6H).

Example 55: 5-((2-cyclopropoxypyridin-3-yl)amino)-N-cyclopropyl-7-(methylamino)pyrazolo[1,5-a]pyrimidine-3-carboxamide (I-215)

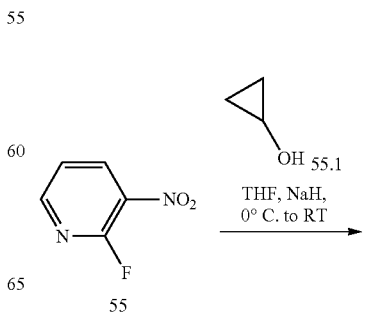

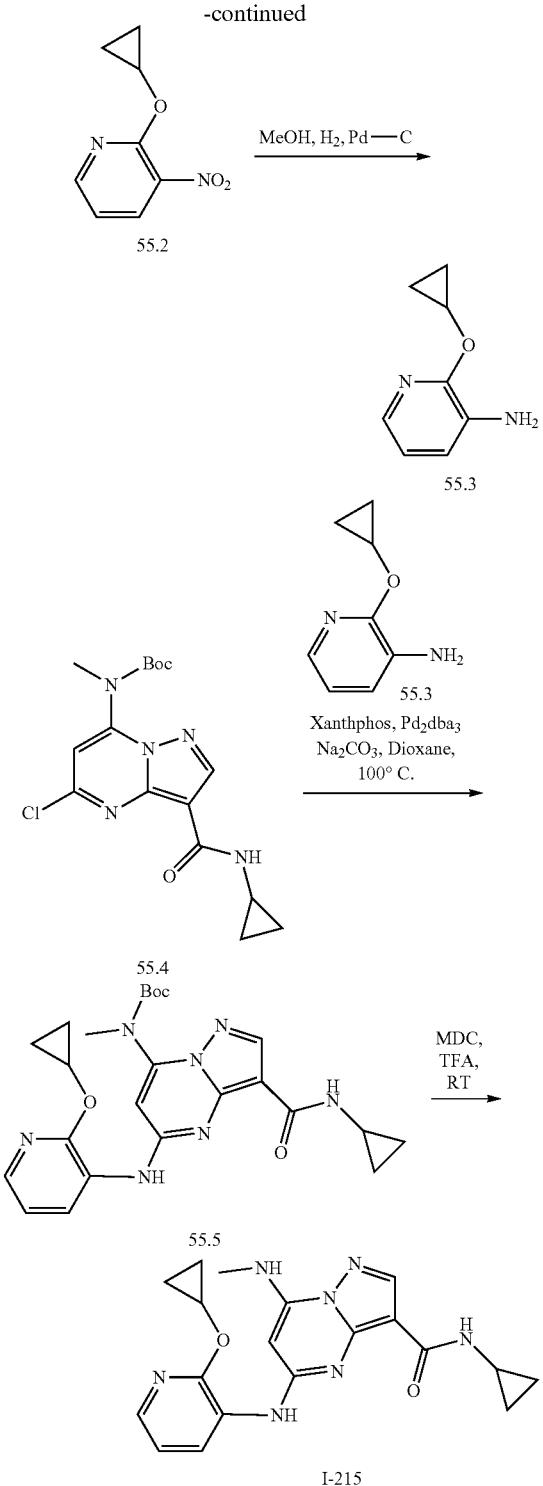

Synthesis of Compound 55.2.

To a cooled solution of 55.1 (0.224 g, 3.87 mmol, 1.1 eq) in tetrahydrofuran (5 mL) was added sodium hydride (0.155 g, 3.87 mmol, 1.1 eq) followed by addition of 1 (0.500 g, 3.52 mmol, 1 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 11% ethyl acetate in hexane to obtain pure 55.2 (0.400 g, 63.09%), MS(ES): m/z 181.16 [M+H]$^+$.

Synthesis of Compound 55.3.

To a solution of 55.2 (0.400 g, 2.22 mmol, 1.0 eq) in methanol (6 ml), palladium on charcoal (0.100 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 1.2% methanol in dichloromethane to obtain pure 55.3 (0.300 g, 89.97%). MS (ES): m/z 151.18 [M+H]$^+$ Synthesis of Compound 55.4.

Compound was synthesized as per experimental protocol of Example 27 to obtain 55.4 (Yield: 57.16%), MS (ES): m/z 366.82 [M+H]$^+$ Synthesis of Compound 55.5.

Compound was synthesized using general procedure B to obtain 55.5 (0.68 g, 51.87%), MS (ES): m/z 480.54 [M+H]$^+$ Synthesis of Compound I-215:

Compound was synthesized using general procedure C to obtain I-215 (0.035 g, 70.63%), MS (ES): m/z 380.24 [M+H]$^+$, LCMS purity: 95.07%, HPLC purity: 96.22%, $^1$H NMR (MEOD-d$_6$, 400 MHZ): 8.73 (s, 1H), 8.20-8.18 (d, J=8 Hz, 1H), 8.15 (s, 1H), 7.96-7.95 (d, J=4 Hz, 1H), 7.92-7.91 (d, J=4 Hz, 1H), 7.78-7.77 (d, J=4 Hz, 1H), 7.06-7.03 (m, 1H), 5.84 (s, 1H), 4.348-4.340 (m, 1H), 2.91-2.90 (d, J=4 Hz, 3H), 2.78-2.77 (d, J=4 Hz, 1H), 0.78-0.69 (m, 6H), 0.34 (bs, 2H).

Example 56: 5-((2-cyclopropoxypyridin-3-yl)amino)-N-(3-hydroxycyclopentyl)-7-(methylamino)pyrazolo[1,5-a]pyrimidine-3-carboxamide (I-461), 5-((2-cyclopropoxypyridin-3-yl)amino)-N-((1S,3S)-3-hydroxycyclopentyl)-7-(methylamino)pyrazolo[1,5-a]pyrimidine-3-carboxamide (I-489), and 5-((2-cyclopropoxypyridin-3-yl)amino)-N-((1R,3R)-3-hydroxycyclopentyl)-7-(methylamino)pyrazolo[1,5-a]pyrimidine-3-carboxamide (I-490)

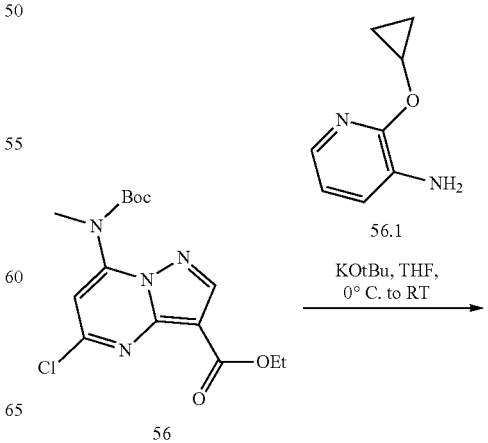

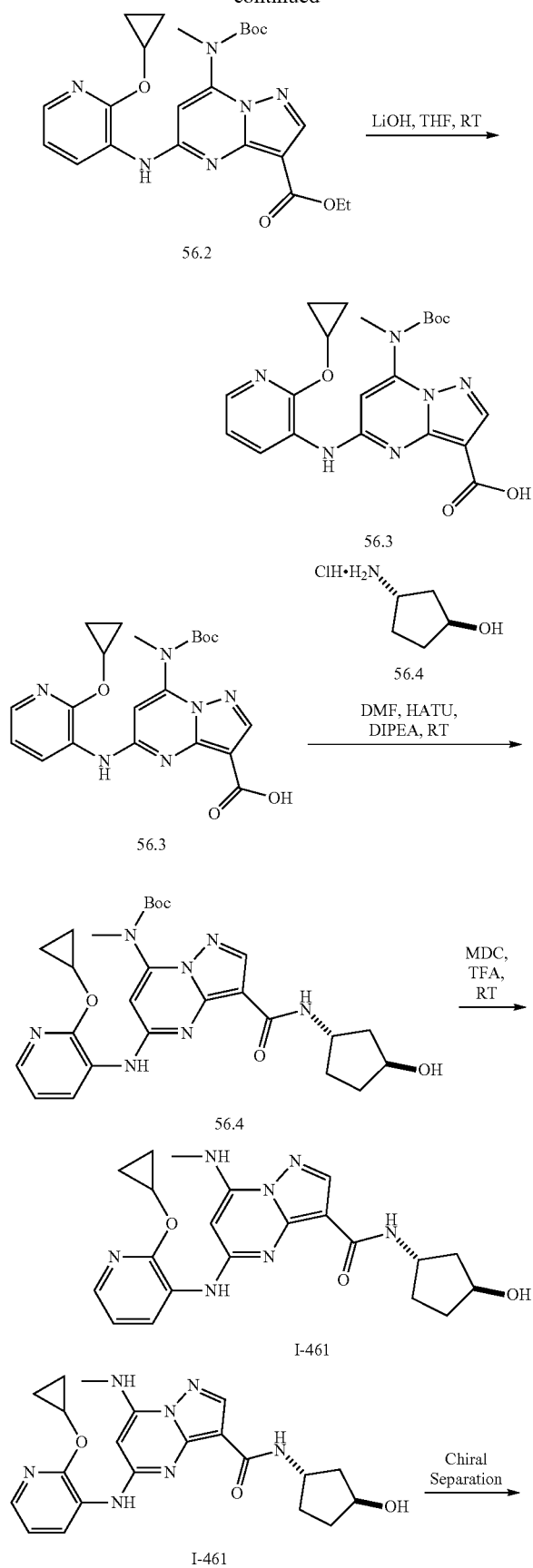
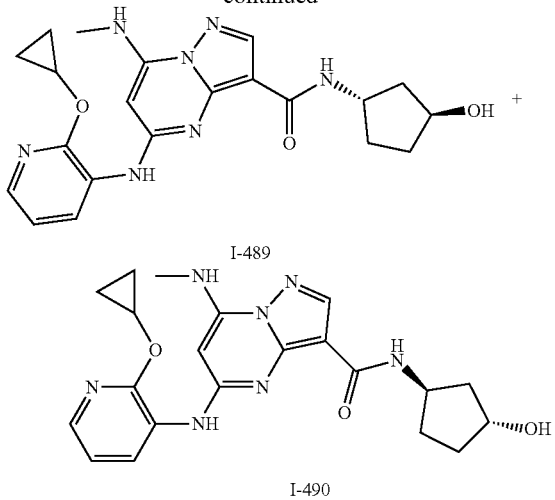

Synthesis of Compound 56.

Compound was synthesized using general procedure of core synthesis to obtain 56. (Yield: 62.21%). MS (ES): m/z 355.5 [M+H].

Synthesis of Compound 56.1.

Compound was synthesized as per experimental protocol of Example 55 to obtain 56.1

Synthesis of Compound 56.2.

To a cooled solution of 56. (3.0 g, 8.46 mmol, 1.0 eq), and 56.1 (1.27 g, 8.46 mmol, 1.0 eq) in tetrahydrofuran (30 mL) at 0° C. was added potassium ter-butoxide (16.9 mL, 16.92 mmol, 2.0 eq). The reaction was stirred at room temperature for 1 h. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 56.2 (2.45 g, 61.84%). MS (ES): m/z 469.5 [M+H]$^+$.

Synthesis of Compound 56.3.

To a solution of 56.2 (2.4 g, 5.12 mmol, 1.0 eq), in tetrahydrofuran: water (80 mL, 2:1) was added lithium hydroxide (2.150 g, 51.2 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 56.3 (1.8 g, 79.78%). MS(ES): m/z 441.5 [M+H]$^+$.

Synthesis of Compound I-461.

Compound was synthesized using general procedure C to obtain I-461 (0.150 g, 97.60%), MS (ES): m/z 424.22 [M+H]$^+$, LCMS purity: 100%, HPLC purity: 99.01%, Chiral HPLC purity: 50.06%+49.93%, $^1$H NMR (DMSO-d$_6$, 400 MHZ): 8.72 (s, 1H), 8.21-8.19 (d, J 8 Hz, 1H), 8.13 (s, 1H), 7.95-7.90 (m, 2H), 7.64-7.62 (d, J=8 Hz, 1H), 7.00-6.97 (m, 1H), 5.83 (s, 1H), 4.56-4.55 (s, 1H), 4.40-4.32 (m, 2H), 4.14 (bs, 1H), 2.91 (s, 3H), 2.06-2.03 (m, 1H), 1.89-1.88 (m, 2H), 1.46-1.44 (bs, 1H), 1.38-1.31 (m, 1H), 1.23-1.14 (m, 1H), 0.79-0.76 (m, 4H).

Isomers of I-461 (0.120 g) were separated out using column (CHIRALPAK AD-H (250 mm*4.6 mm, 5 u)) in 0.1% DEA in MEOH as co-solvent (25%) with flow rate of 3 mL/min. to get pure fraction-1 (FR-a) and fraction-2 (FR-b). FR-a was concentrated under reduced pressure at 30° C. to afford pure FR-a (0.040 g). MS(ES): m/z 424.38 [M+H]+, LCMS purity: 99.33%, HPLC purity: 98.88%, CHIRAL HPLC purity: 100%, ¹H NMR (DMSO-d₆, 400 MHZ): 8.73 (s, 1H), 8.21-8.20 (d, J=6.4 Hz, 1H), 8.14 (s, 1H), 7.96-7.95 (d, J=3.6 Hz, 1H), 7.92-7.90 (d, J=4.8 Hz, 2H), 7.64-7.63 (d, J=7.6 Hz, 1H), 7.01-6.98 (m, 1H), 5.85 (s, 1H), 4.57-4.56 (d, J=3.6 Hz, 1H), 4.41-4.35 (m, 1H), 4.16 (bs, 1H), 2.92-2.91 (d, J=4.8 Hz, 3H), 2.08-2.01 (m, 1H), 1.89-1.80 (m, 2H), 1.47-1.45 (bs, 1H), 1.39-1.32 (m, 1H), 1.24-1.13 (m, 1H), 0.80-0.69 (m, 4H).

FR-b was concentrated under reduced pressure at 30° C. to afford pure FR-b (0.045 g). MS(ES): m/z 424.33 [M+H]+, LCMS purity: 98.33%, HPLC purity: 99.03%, CHIRAL HPLC purity: 97.83%, ¹H NMR (DMSO-d₆, 400 MHZ): 8.73 (s, 1H), 8.21-8.20 (d, J=6.4 Hz, 1H), 8.14 (s, 1H), 7.96-7.95 (d, J=3.6 Hz, 2H), 7.92-7.90 (d, J=4.8 Hz, 1H), 7.64-7.63 (d, J=7.6 Hz, 1H), 7.01-6.98 (m, 1H), 5.85 (s, 1H), 4.57-4.56 (d, J=3.6 Hz, 1H), 4.42-4.33 (m, 1H), 4.16 (bs, 1H), 2.92-2.91 (d, J=4.8 Hz, 3H), 2.07-2.03 (m, 1H), 1.89-1.81 (m, 2H), 1.47-1.45 (bs, 1H), 1.39-1.32 (m, 1H), 1.21-1.13 (m, 1H), 0.80-0.69 (m, 4H).

Example 57: 5-((2-cyclopropoxypyridin-3-yl)amino)-N-(3-hydroxy-3-methylbutyl)-7-(methylamino)pyrazolo[1,5-a]pyrimidine-3-carboxamide (I-422)

Synthesis of Compound 57:

Compound was synthesized as per experimental protocol of Example 56 to obtain 57.

Synthesis of Compound 57.1:

Compound was synthesized using general procedure A to obtain 57.1 (0.058 g, 48.60%). MS (ES): m/z 526.61 [M+H]+.

Synthesis of Compound I-422:

Compound was synthesized using general procedure C to obtain I-422 (0.029 g, 61.76%). MS (ES): m/z 426.60 [M+H]+, LCMS purity: 95.34%, HPLC purity: 94.48%, ¹H NMR (DMSO-d₆, 400 MHZ): 8.71 (s, 1H), 8.31-8.30 (d, J=4.0 Hz, 1H), 8.15 (s, 1H), 7.93-7.91 (m, 2H), 7.68-7.66 (t, 1H), 7.07-7.04 (m, 1H), 5.89 (s, 1H), 4.35 (s, 2H), 3.37-3.29 (m, 2H), 2.92-2.91 (d, J=4.0 Hz, 3H), 1.56-1.52 (m, 2H), 1.13 (s, 6H), 0.79-0.76 (m, 4H).

Example 58: 3-(1-isopropyl-1H-1,2,3-triazol-4-yl)-N5-(2-methoxypyridin-3-yl)-N7-methylpyrazolo[1,5-a]pyrimidine-5,7-diamine (I-1008)

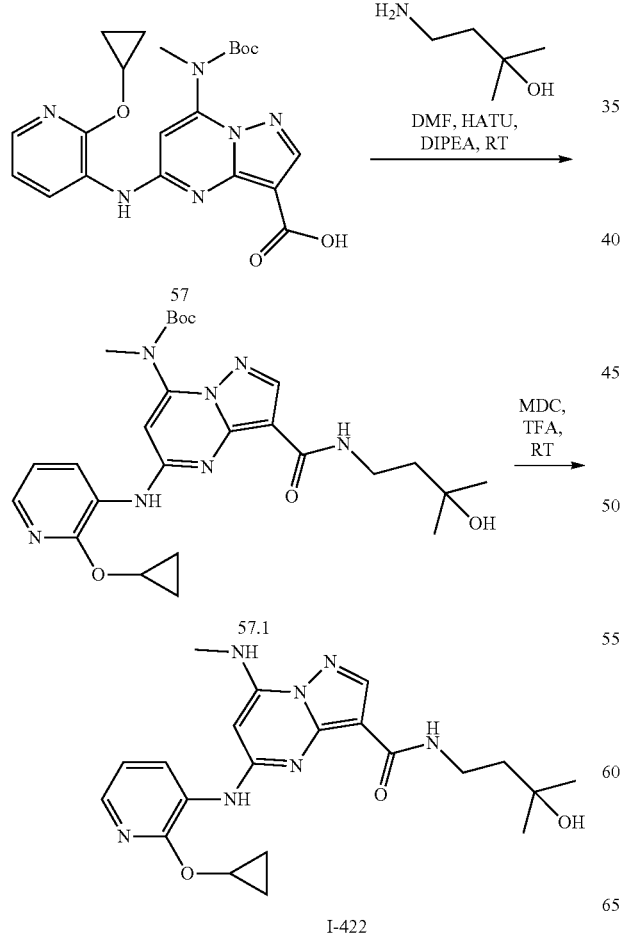

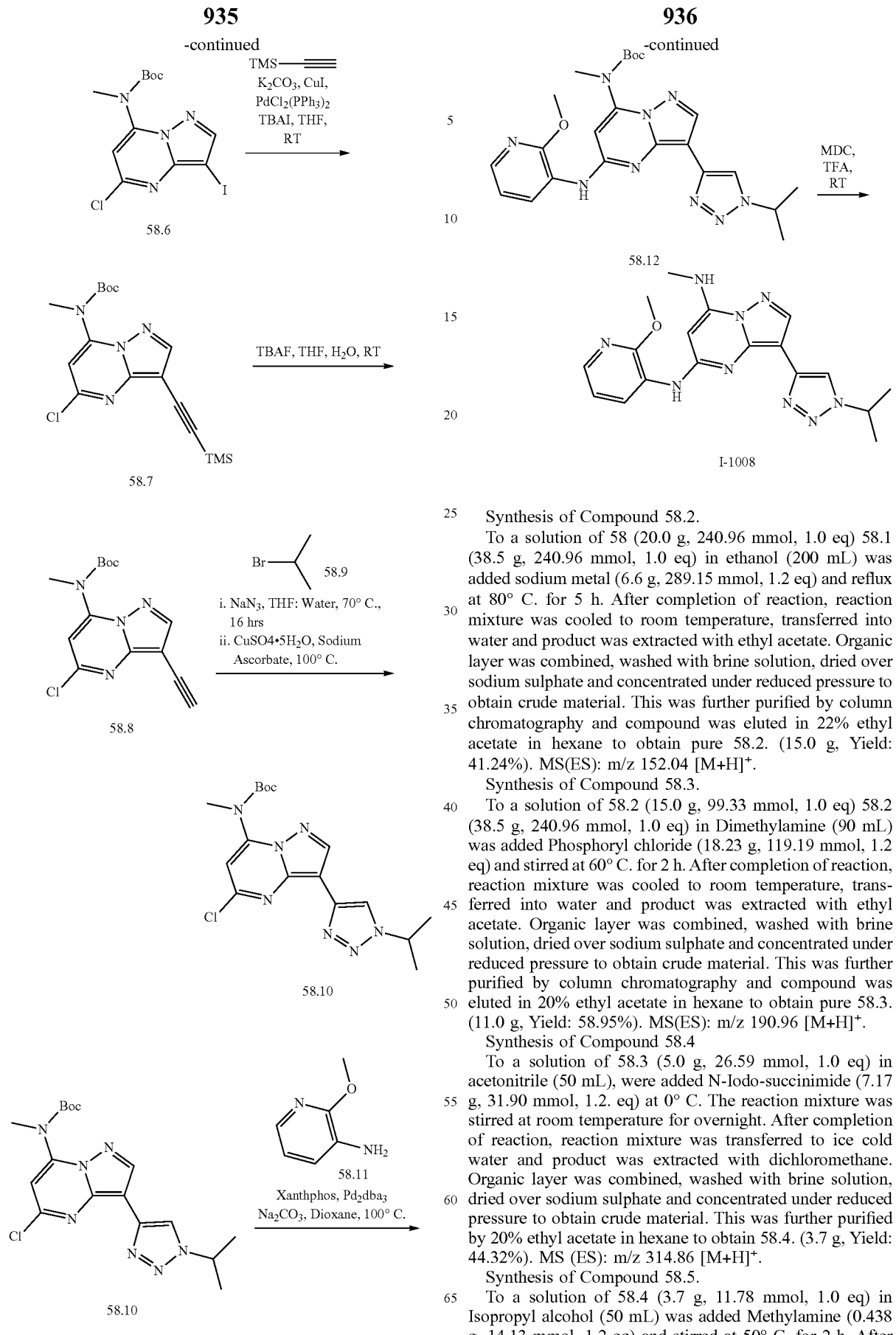

Synthesis of Compound 58.2.

To a solution of 58 (20.0 g, 240.96 mmol, 1.0 eq) 58.1 (38.5 g, 240.96 mmol, 1.0 eq) in ethanol (200 mL) was added sodium metal (6.6 g, 289.15 mmol, 1.2 eq) and reflux at 80° C. for 5 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 58.2. (15.0 g, Yield: 41.24%). MS(ES): m/z 152.04 [M+H]$^+$.

Synthesis of Compound 58.3.

To a solution of 58.2 (15.0 g, 99.33 mmol, 1.0 eq) 58.2 (38.5 g, 240.96 mmol, 1.0 eq) in Dimethylamine (90 mL) was added Phosphoryl chloride (18.23 g, 119.19 mmol, 1.2 eq) and stirred at 60° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 58.3. (11.0 g, Yield: 58.95%). MS(ES): m/z 190.96 [M+H]$^+$.

Synthesis of Compound 58.4

To a solution of 58.3 (5.0 g, 26.59 mmol, 1.0 eq) in acetonitrile (50 mL), were added N-Iodo-succinimide (7.17 g, 31.90 mmol, 1.2 eq) at 0° C. The reaction mixture was stirred at room temperature for overnight. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 20% ethyl acetate in hexane to obtain 58.4. (3.7 g, Yield: 44.32%). MS (ES): m/z 314.86 [M+H]$^+$.

Synthesis of Compound 58.5.

To a solution of 58.4 (3.7 g, 11.78 mmol, 1.0 eq) in Isopropyl alcohol (50 mL) was added Methylamine (0.438 g, 14.13 mmol, 1.2 eq) and stirred at 50° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 58.5. (2.8 g, Yield: 77.00%). MS(ES): m/z 309.93 [M+H]$^+$.

Synthesis of Compound 58.6.

To a solution of 58.5 (2.8 g, 9.07 mmol, 1.0 eq) in 1,4-dioxane (30 mL) were added Di-tert-butyl dicarbonate (3.5 g, 16.32 mmol, 1.8 eq) and 4-Dimethylaminopyridine (0.197 g, 0.90 mmol, 0.1 eq) stirred at room temperature for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 58.6. (2.3 g, Yield: 62.02%). MS(ES): m/z 409.98 [M+H]$^+$.

Synthesis of Compound 58.7.

To a solution of 58.6. (2.3 g, 5.62 mmol, 1.0 eq) in tetrahydrofuran (25 mL) were added bis(triphenylphosphine)palladium(II)dichloride (0.394 g, 0.56 mmol, 0.1 eq), Potassium carbonate (1.5 g, 11.24 mmol, 2.0 eq), followed by addition of Tetrabutylammonium iodide (0.207 g, 0.56 mmol, 0.1 eq) and Copper(I) iodide (0.213 g, 1.12 mmol, 0.2 eq) at room temperature. The reaction was stirred at room temperature for 3 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 58.7. (1.7 g, Yield: 79.70%), MS(ES): m/z 379.13 [M+H]$^+$ Synthesis of Compound 58.8.

To a solution of 58.7. (1.7 g, 4.48 mmol, 1.0 eq) in tetrahydrofuran (20 mL) was added Tetra-n-butylammonium fluoride (2.3 g, 8.96 mmol, 2.0 eq) at room temperature. The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 50% ethyl acetate in hexane to obtain pure 58.8. (0.9 g, Yield: 65.40%), MS(ES): m/z 307.09 [M+H]$^+$ Synthesis of Compound 58.10.

To a solution of 58.8 (1.0 g, 3.25 mmol, 1.0 eq) in tetrahydrofuran: water (20 mL, 1:1) was added Sodium azide (0.274 g, 4.22 mmol, 1.3 eq) and 58.9 (0.399 g, 3.25 mmol, 1.0 eq) followed by addition of Copper(II) sulfate (0.039 g, 0.16 mmol, 0.05 eq) and Sodium Ascorbate, (0.320 g, 1.62 mmol, 0.5 eq) at room temperature. The reaction was stirred at 75° C. for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 3% methanol in dichloromethane to obtain pure 58.10. (0.390 g, Yield: 30.53%), MS(ES): m/z 392.16 [M+H]$^+$ Synthesis of Compound 58.12.

Compound was synthesized using general procedure B to obtain 58.12. (0.070 g, 28.60%), MS (ES): 480.24 [M+H]$^+$ Synthesis of Compound I-1008:

Compound was synthesized using general procedure C to obtain I-1008 (0.040 g, 72.22%), MS (ES): 380.44 [M+H]$^+$ LCMS purity: 100%, HPLC purity: 99.04%, $^1$H NMR (DMSO-d$_6$, 400 MHZ): 8.90-8.88 (d, J=8 Hz, 1H), 8.68 (s, 1H), 8.29 (s, 1H), 8.16 (s, 1H), 7.84-7.83 (d, J=4.8 Hz, 1H), 7.76-7.75 (d, J=4.8 Hz, 1H), 7.05-7.01 (m, 1H), 6.02 (s, 1H), 3.99 (s, 3H), 2.94-2.93 (d, J=4.4 Hz, 3H), 1.58-1.56 (d, J=6.8 Hz, 5H), 1.22 (bs, 2H).

Example 59: N5-(2-cyclopropoxypyridin-3-yl)-3-(1-isopropyl-1H-1,2,3-triazol-4-yl)-N7-methylpyrazolo[1,5-a]pyrimidine-5,7-diamine (I-985)

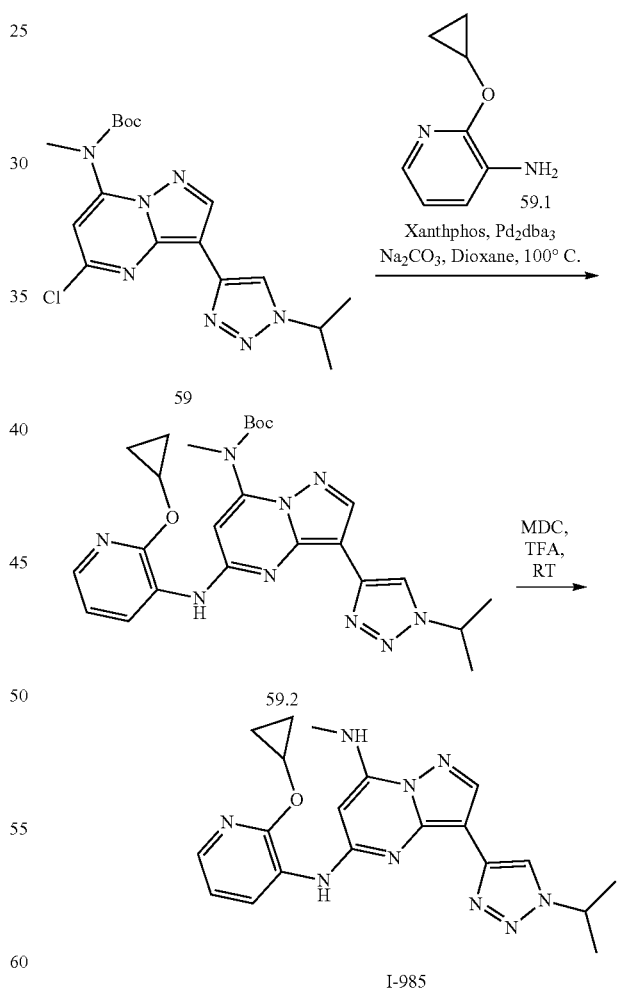

Synthesis of Compound 59.

Compound was synthesized as per experimental protocol of Example 58 to obtain 59. (Yield: 30.53%). MS (ES): m/z 392.16 [M+H]$^+$ Synthesis of Compound 59.2.

Compound was synthesized using general procedure B to obtain 59.2. (0.085 g, Yield: 34.67%). MS (ES): m/z 506.26 [M+H]+

Synthesis of Compound I-985:

Compound was synthesized using general procedure C to obtain I-985 (0.040 g, 58.68%), MS (ES): m/z 406.30 [M+H]+, LCMS purity: 98.69%, HPLC purity: 98.37%, 1H NMR (DMSO-d6, 400 MHZ): 8.90-8.88 (d, J 8 Hz, 1H), 8.42 (s, 1H), 8.29 (s, 1H), 8.14 (s, 1H), 7.86-7.85 (d, J=4.8 Hz, 1H), 7.76-7.75 (d, J=4.8 Hz, 1H), 7.06-7.03 (m, 2H), 5.96 (s, 1H), 4.92-4.85 (s, 1H), 2.94-2.93 (d, J=4.8 Hz, 3H), 2.74 (bs, 1H), 1.57-1.56 (d, J=6.8 Hz, 6H), 1.24 (bs, 3H).

Example 60: N-ethoxy-5-((2-methoxypyridin-3-yl)amino)-7-(methylamino)pyrazolo[1,5-a]pyrimidine-3-carboxamide (I-409)

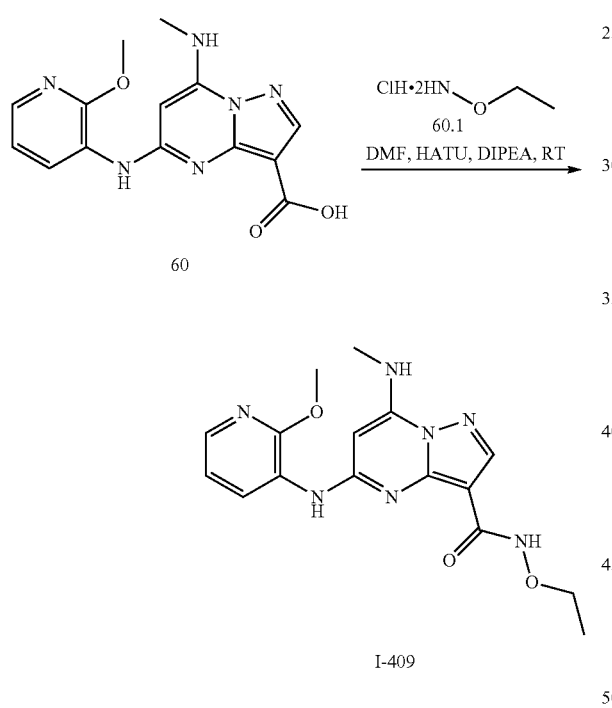

Synthesis of Compound 60.

Compound was synthesized as per experimental protocol of Example 32 to obtain 60. (Yield: 71.18%), MS (ES): m/z 415.42 [M+H]+

Synthesis of Compound I-409.

Compound was synthesized using general procedure A to obtain I-409 (0.04 g, 27.8%). MS (ES): m/z 358.49 [M+H]+, LCMS purity: 98.72%, HPLC purity: 99.24%, 1H NMR (DMSO-d6, 400 MHZ): 10.30 (s, 1H), 8.97 (s, 1H), 8.38-8.36 (d, J=7.6 Hz, 1H), 8.20 (s, 1H), 7.95-7.91 (m, 2H), 7.03-6.99 (m, 1H), 5.90 (s, 1H), 3.96 (s, 3H), 3.91-3.86 (dd, J=6.8 Hz, 7.2 Hz, 2H), 2.91-2.90 (d, J=4.8 Hz, 3H), 1.19-1.16 (t, 3H).

Example 61: N-ethoxy-5-((3'-fluoro-2-oxo-2H-[1,2'-bipyridin]-3-yl)amino)-7-(methylamino)pyrazolo[1,5-a]pyrimidine-3-carboxamide (I-798)

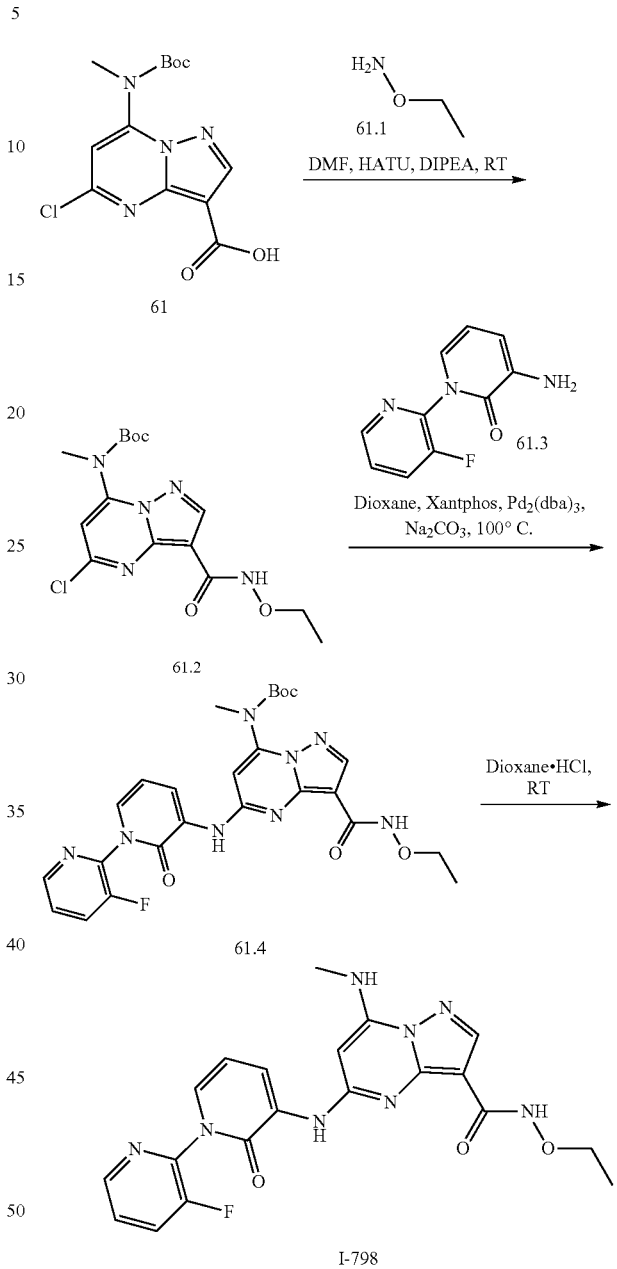

Synthesis of Compound 61.

Compound was synthesized using general procedure of core synthesis to obtain 61 (Yield, 71.67%). 1H NMR (DMSO-d6, 400 MHZ): 12.63 (s, 1H), 8.63 (s, 1H), 7.55 (s, 1H), 3.31 (s, 3H), 1.29 (s, 9H).

Synthesis of Compound 61.2.

Compound was synthesized using general procedure A to obtain 61.2 (0.1 g, 29.45%), MS (ES): m/z 370.4 [M+H]+

Synthesis of Compound 61.3.

Compound was synthesized as per experimental protocol of Example 19 to obtain 61.3 (Yield: 80.70%). MS (ES): m/z 206.29 [M+H]+

Synthesis of Compound 61.4.

Compound was synthesized using general procedure B to obtain 61.4 (0.080 g, 54.93%), MS (ES): m/z 539.6 [M+H]+

Synthesis of Compound I-798:

Compound was synthesized using general procedure C to obtain I-798 (0.040 g, 61.42%), MS (ES): m/z 439.2 [M+H]+, LCMS purity: 97.23%, HPLC purity: 97.23%, $^1$H NMR (DMSO-$d_6$, 400 MHZ): 10.42 (s, 1H), 9.05 (s, 1H), 8.55-8.51 (m, 2H), 8.25 (s, 1H), 8.07 (s, 1H), 7.96-7.95 (d, J=4.8 Hz, 1H), 7.78-7.71 (m, 1H), 7.44-7.42 (d, J=6.4 Hz, 1H), 6.46 (t, 1H), 6.21 (s, 1H), 3.98-3.96 (q, 2H), 3.90-3.89 (d, 3H), 1.27-1.24 (t, 3H).

Example 62: N-cyclopropyl-5-((1-(1-(2-fluoroethyl)piperidin-4-yl)-2-oxo-1,2-dihydropyridin-3-yl)amino)-7-(methylamino)pyrazolo[1,5-a]pyrimidine-3-carboxamide (I-569)

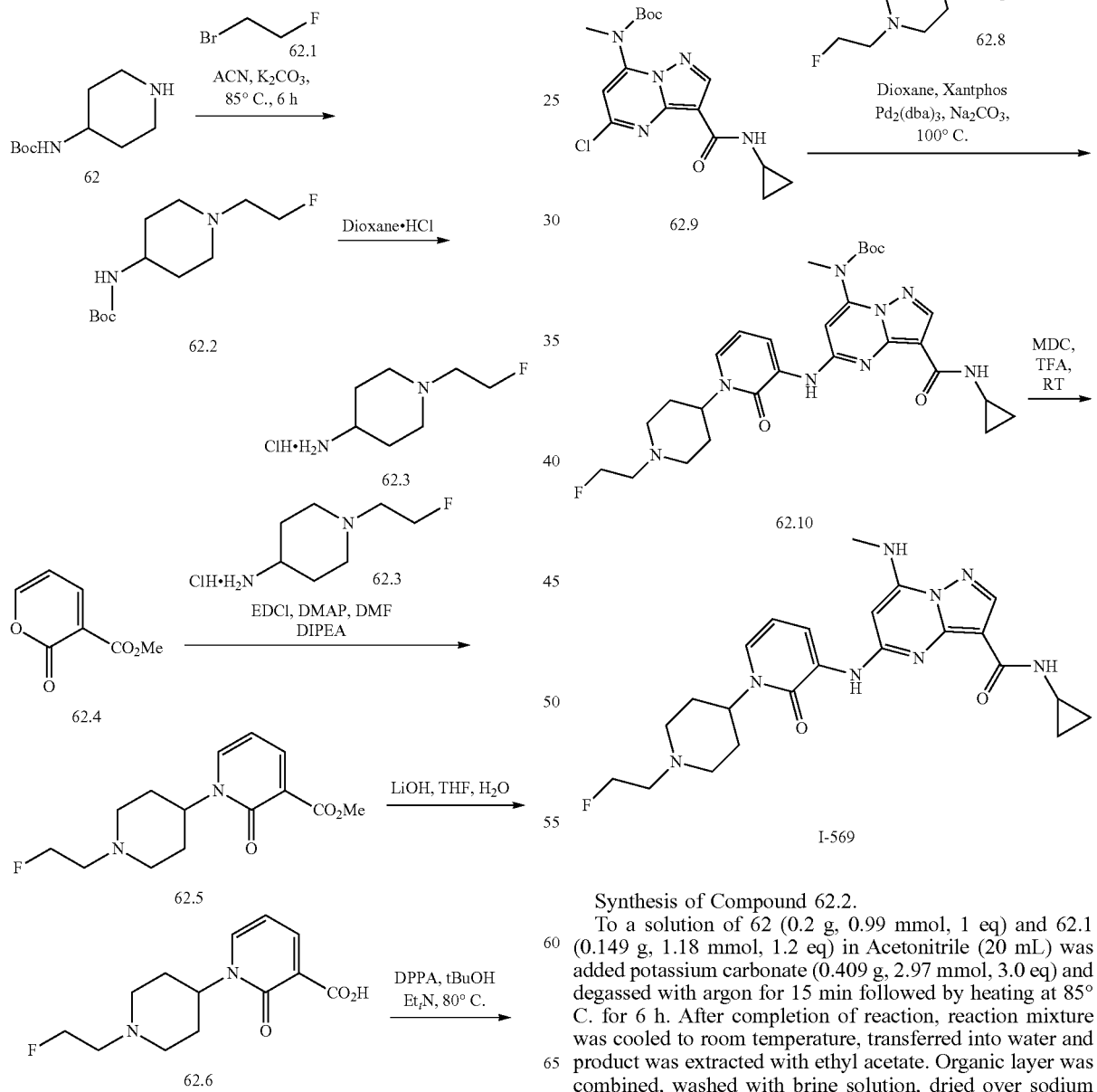

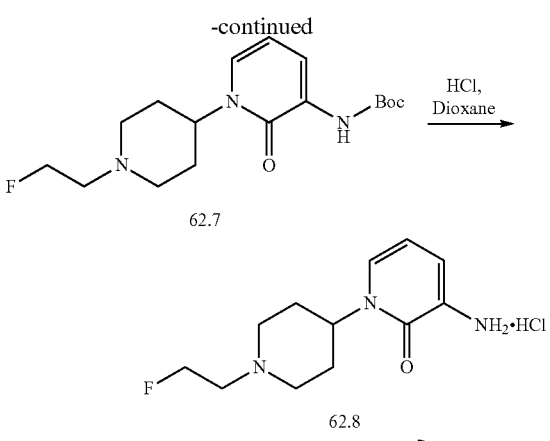

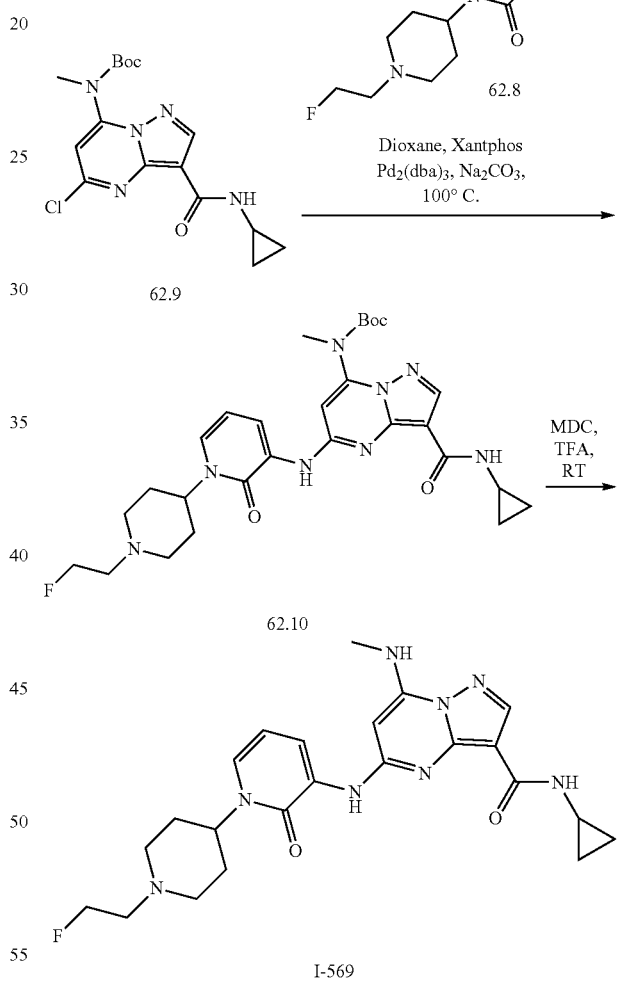

Synthesis of Compound 62.2.

To a solution of 62 (0.2 g, 0.99 mmol, 1 eq) and 62.1 (0.149 g, 1.18 mmol, 1.2 eq) in Acetonitrile (20 mL) was added potassium carbonate (0.409 g, 2.97 mmol, 3.0 eq) and degassed with argon for 15 min followed by heating at 85° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 62.2 (1.3 g, 52.85%). MS(ES): m/z 247.1 [M+H]+.

Synthesis of Compound 62.3.

To 62.2 (1.3 g, 5.27 mmol, 1.0 eq) was added 4M hydrochloric acid in 1,4 Dioxane (25 mL) and stirred at room temperature for 4 h. After completion of reaction, reaction mixture was concentrated under reduced pressure, residue was triturated with diethyl ether to obtain 62.3. (0.9 g, 93.36%). MS (ES): m/z 183.1 [M+H]+

Synthesis of Compound 62.5.

To a cooled solution of 62.4 (0.9 g, 5.83 mmol, 1.0 eq), in N,N-dimethylformamide (20 mL) was added 62.3 (1.06 g, 5.83 mmol, 1.0 eq). The reaction mixture was stirred at 0° C. for 6 h and further stirred at room temperature for 15 min. N-Ethyl-N'-(3-dimethylaminopropyl)carbodiimide hydrochloride (1.44 g, 7.57 mmol, 1.3 eq) and 4-Dimethylaminopyridine (0.141 g, 1.16 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 62.5. (0.440 g, 26.69%). MS(ES): m/z 283.1 [M+H]+.

Synthesis of Compound 62.6.

To a solution of 62.5 (0.340 g, 1.20 mmol, 1.0 eq), in tetrahydrofuran: water (6 mL, 2:1) was added lithium hydroxide (0.288 g, 12.0 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 62.6. (0.220 g, 68.09%). MS(ES): m/z 269.1 [M+H]+.

Synthesis of Compound 62.7.

To a solution of 62.6 (0.220 g, 0.82 mmol, 1.0 eq) in tert.butanol (6 mL) was added triethylamine (0.140 g, 1.39 mmol, 1.7 eq) and diphenyl phosphoryl azide (0.291 g, 1.06 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 62.7. (0.220 g, 79.05%). MS(ES): m/z 340.2 [M+H]+.

Synthesis of Compound 62.8.

To 62.7 (0.220 g, 0.64 mmol, 1.0 eq) was added 4M hydrochloric acid in 1,4 Dioxane (5 mL) and stirred at room temperature for 4 h. After completion of reaction, reaction mixture was concentrated under reduced pressure, residue was triturated with diethyl ether to obtain 62.8. (0.180 g, 97.91%). MS (ES): m/z 240.1 [M+H]+

Synthesis of Compound 62.9.

Compound was synthesized as per experimental protocol of Example 27 to obtain 62.9. (Yield: 57.16%), MS (ES): m/z 366.82 [M+H]+

Synthesis of Compound 62.10.

Compound was synthesized using general procedure B to obtain 62.10. (0.070 g, Yield: 45.03%). MS (ES): m/z 569.3 [M+H]+

Synthesis of Compound I-569.

Compound was synthesized using general procedure C to obtain I-569. (Yield: 0.038 g, 65.89%). MS (ES): m/z 469.35 [M+H]+, LCMS purity: 100%, HPLC purity: 100%, ¹H NMR (DMSO-d6, 400 MHZ): 8.88 (bs, 1H), 8.20 (s, 1H), 8.13-8.11 (d, J=6 Hz, 1H), 7.92 (bs, 1H), 7.82 (bs, 1H), 7.50 (bs, 1H), 6.32 (bs, 1H), 6.20 (s, 1H), 4.80 (bs, 1H), 4.63 (bs, 1H), 4.51 (bs, 1H), 3.18 (bs, 1H), 3.08-3.06 (d, J=10 Hz, 2H), 2.90 (s, 3H), 2.73 (bs, 1H), 1.96-1.94 (d, J=8 Hz, 2H), 1.79 (bs, 2H), 1.56 (bs, 1H), 1.24 (bs, 2H), 0.79 (bs, 2H), 0.50 (bs, 2H).

Example 63: 5-((1-(1-(2-fluoroethyl)piperidin-4-yl)-2-oxo-1,2-dihydropyridin-3-yl)amino)-N-(2-methoxycyclobutyl)-7-(methylamino)pyrazolo[1,5-a]pyrimidine-3-carboxamide (I-1049)

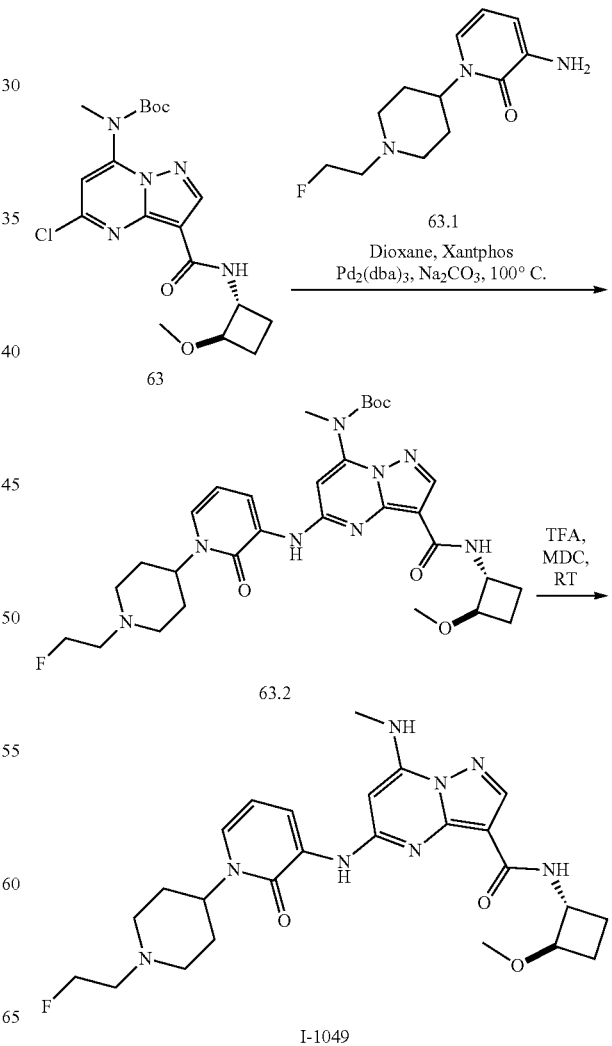

Synthesis of Compound 63.

Compound was synthesized as per experimental protocol of Example 30 to obtain 63. (Yield: 57.95%), MS (ES): m/z 410.16 [M+H]$^+$ Synthesis of Compound 63.1.

Compound was synthesized as per experimental protocol of Example 62 to obtain 63.1. (Yield: 97.91%), MS (ES): m/z 240.1 [M+H]$^+$ Synthesis of Compound 63.2.

Compound was synthesized using general procedure B to obtain 63.2. (0.130 g, 57.98%), MS (ES): 613.32 [M+H]$^+$ Synthesis of Compound I-1049:

Compound was synthesized using general procedure C to obtain I-1049 (0.100, 91.95%), MS (ES): 513.72 [M+H]$^+$ LCMS purity: 100%, HPLC purity: 97.03%, CHIRAL HPLC: 49.13% 50.65%, $^1$H NMR (DMSO-$d_6$, 400 MHZ): 8.92 (s, 1H), 8.24-8.22 (d, J=6.4 Hz, 1H), 8.20 (s, 1H), 8.07-8.05 (d, J=9.2 Hz, 1H), 7.95-7.93 (d, J=4.8 Hz, 1H), 7.53-7.51 (d, J=6.8 Hz, 1H), 6.34-6.30 (t, J=7.2 Hz, 1H), 6.22 (s, 1H), 4.83-4.77 (m, 1H), 4.64-4.62 (t, J=4.8 Hz, 1H), 4.52-4.50 (t, J=4.8 Hz, 1H), 4.36-4.28 (m, 1H), 3.73-3.67 (m, 1H), 3.42-3.36 (m, 2H), 3.20 (s, 3H), 3.08-3.05 (d, J=11.2 Hz, 2H), 2.92-2.91 (d, J=4.4 Hz, 3H), 2.74-2.71 (t, J=4.8 Hz, 1H), 2.67-2.65 (t, J=4.8 Hz, 1H), 1.98-1.90 (m, 2H), 1.77 (bs, 2H), 1.58-1.48 (m, 1H), 1.42-1.32 (m, 1H), 1.24 (bs, 1H), 1.12 (bs, 1H).

Example 64: 5-((1-((S)-1-(2-fluoroethyl)pyrrolidin-3-yl)-2-oxo-1,2-dihydropyridin-3-yl)amino)-N-((1S,2S)-2-methoxycyclobutyl)-7-(methylamino)pyrazolo[1,5-a]pyrimidine-3-carboxamide (I-1050)

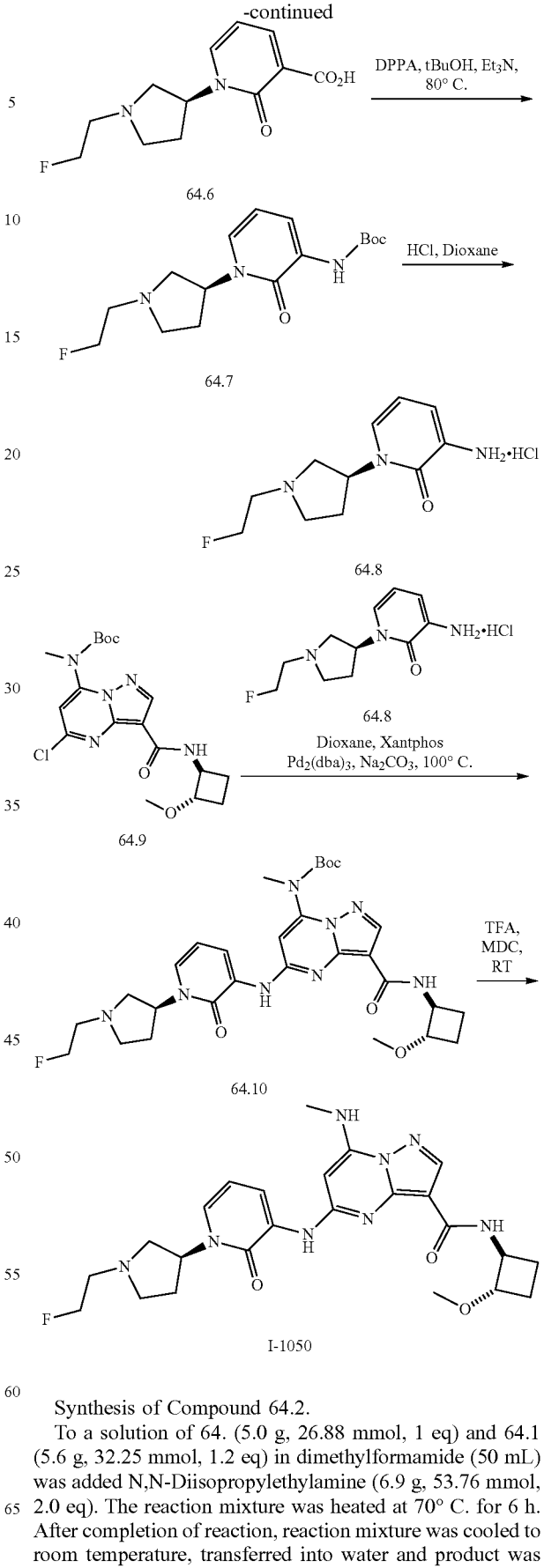

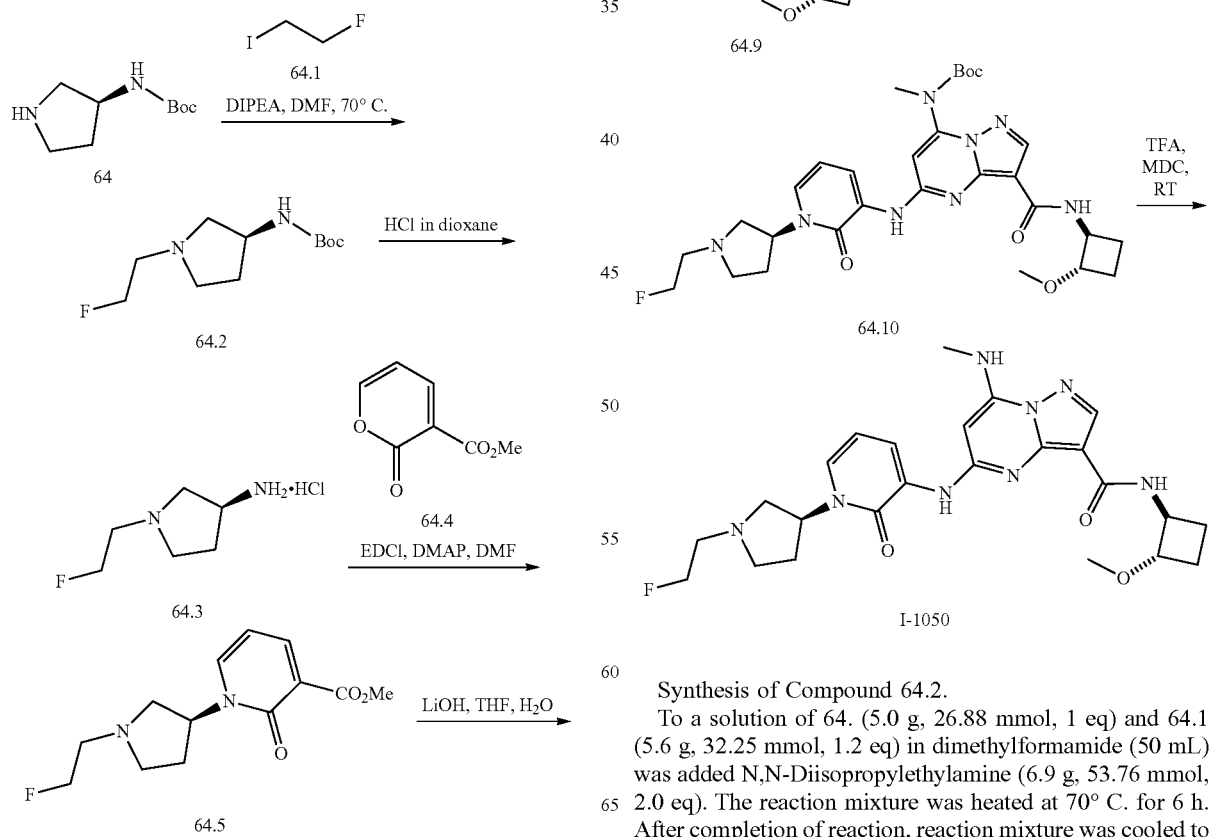

Synthesis of Compound 64.2.

To a solution of 64. (5.0 g, 26.88 mmol, 1 eq) and 64.1 (5.6 g, 32.25 mmol, 1.2 eq) in dimethylformamide (50 mL) was added N,N-Diisopropylethylamine (6.9 g, 53.76 mmol, 2.0 eq). The reaction mixture was heated at 70° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 64.2 (4.0 g, 64.14%). MS(ES): m/z 233.16 [M+H]$^+$.

Synthesis of Compound 64.3.

To 64.2 (4.0 g, 17.24 mmol, 1.0 eq) was added 4M hydrochloric acid in 1,4 Dioxane (90 mL) and stirred at room temperature for 4 h. After completion of reaction, reaction mixture was concentrated under reduced pressure, residue was triturated with diethyl ether to obtain 64.3. (2.4 g, 82.65%). MS (ES): m/z 169.09 [M+H]$^+$ Synthesis of Compound 64.5.

To a cooled solution of 64.3 (2.4 g, 14.26 mmol, 1.0 eq), in N,N-dimethylformamide (45 mL) was added 64.4 (2.1 g, 14.26 mmol, 1.0 eq). The reaction mixture was stirred at 0° C. for 6 h and further stirred at room temperature for 15 min. N-Ethyl-N'-(3-dimethylaminopropyl)carbodiimide hydrochloride (2.8 g, 18.53 mmol, 1.3 eq) and 4-Dimethylaminopyridine (0.347 g, 2.85 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 64.5. (0.7 g, 18.33%). MS(ES): m/z 269.13 [M+H]$^+$.

Synthesis of Compound 64.6.

To a solution of 64.5 (0.7 g, 2.60 mmol, 1.0 eq), in tetrahydrofuran: water (15 mL, 2:1) was added lithium hydroxide (0.624 g, 26.0 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 64.6. (0.5 g, 75.37%). MS(ES): m/z 255.11 [M+H]$^+$.

Synthesis of Compound 64.7.

To a solution of 64.6 (0.5 g, 1.96 mmol, 1.0 eq) in tert.butanol (10 mL) was added triethylamine (0.336 g, 3.33 mmol, 1.7 eq) and diphenyl phosphoryl azide (0.698 g, 2.54 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 64.7. (0.4 g, 62.51%). MS(ES): m/z 326.18 [M+H]$^+$.

Synthesis of Compound 64.8.

To 64.7 (0.4 g, 1.22 mmol, 1.0 eq) was added 4M hydrochloric acid in 1,4 Dioxane (6 mL) and stirred at room temperature for 4 h. After completion of reaction, reaction mixture was concentrated under reduced pressure, residue was triturated with diethyl ether to obtain 64.8. (0.250 g, 77.70%). MS (ES): m/z 240.1 [M+H]$^+$ Synthesis of Compound 64.9.

Compound was synthesized as per experimental protocol of Example 30 to obtain 64.9. (Yield: 57.95%), MS (ES): m/z 410.16 [M+H]$^+$ Synthesis of Compound 64.10.

Compound was synthesized using general procedure B to obtain 64.10. (0.126 g, 57.51%), MS (ES): 599.31 [M+H]$^+$ Synthesis of Compound I-1050:

Compound was synthesized using general procedure C to obtain I-1050 (0.095, 90.54%), MS (ES): 499.5 [M+H]$^+$ LCMS purity: 100%, HPLC purity: 99.47%, CHIRAL HPLC: 48.30% 51.69%, $^1$H NMR (DMSO-d$_6$, 400 MHZ): 8.94 (bs, 1H), 8.24-8.22 (d, J=6.8 Hz, 1H), 8.20 (s, 1H), 8.15 (bs, 1H), 8.08-8.06 (d, J=9.2 Hz, 1H), 7.95-7.93 (d, J=4.8 Hz, 1H), 7.64-7.63 (d, J=6 Hz, 1H), 4.67-4.64 (t, J=4.8 Hz, 1H), 4.55-4.52 (t, J=4.8 Hz, 1H), 4.34-4.30 (m, 1H), 3.73-3.67 (m, 1H), 3.20 (s, 3H), 3.15-3.12 (m, 1H), 3.12 (bs, 1H), 2.92-2.90 (d, J=4.8 Hz, 3H), 2.85-2.82 (m, 1H), 2.75-2.68 (m, 2H), 2.41-2.34 (m, 3H), 2.16-2.06 (m, 2H), 1.81-1.76 (m, 1H), 1.55-1.50 (m, 1H), 1.50-1.37 (m, 1H), 1.24 (bs, 1H).

Example 65: 5-(benzo[d]oxazol-4-ylamino)-N-(2-methoxycyclobutyl)-7-(methylamino)pyrazolo[1,5-a]pyrimidine-3-carboxamide (I-1051)

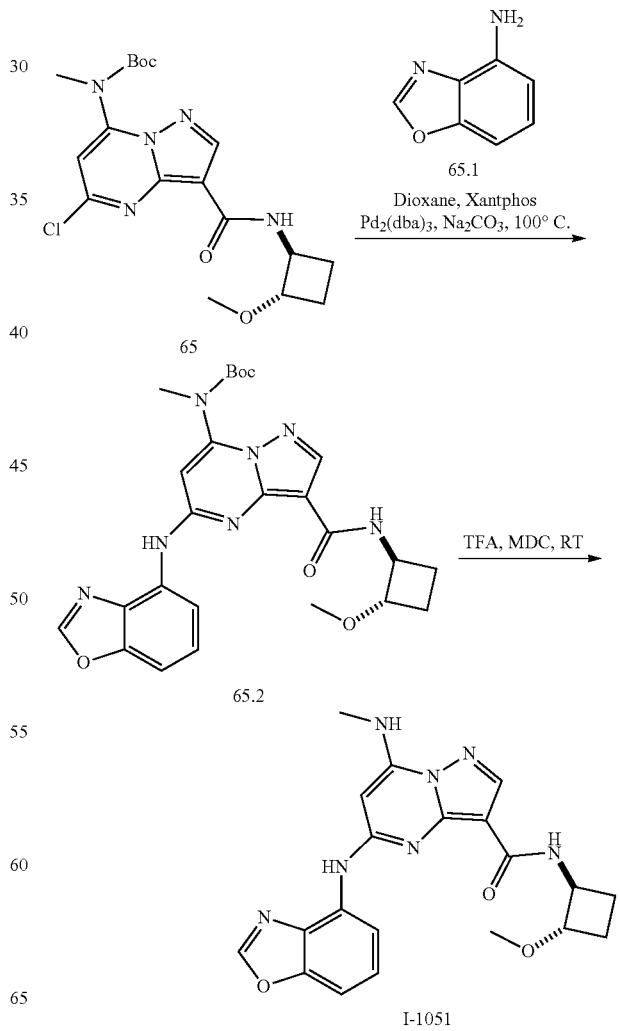

Synthesis of Compound 65.

Compound was synthesized as per experimental protocol of Example 30 to obtain 65. (Yield: 57.95%), MS (ES): m/z 410.16 [M+H]$^+$ Synthesis of Compound 65.2.

Compound was synthesized using general procedure B to obtain 65.2. (Yield: 0.130 g, 69.99%). MS (ES): m/z 508.23 [M+H]$^+$ Synthesis of Compound I-1051:

Compound was synthesized using general procedure C to obtain I-1051 (0.025 g, Yield: 77.86%), MS (ES): m/z 408.57 [M+H]$^+$, LCMS purity: 96%, HPLC purity: 98.16%, CHIRAL HPLC: 50%, 49%, $^1$H NMR (DMSO-d$_6$, 400 MHZ): 9.79 (s, 1H), 8.82 (s, 1H), 8.18 (s, 1H), 8.15-8.13 (d, J=9.2 Hz, 1H), 8.00-7.95 (m, 2H), 7.56-7.54 (d, J=8 Hz, 1H), 7.47-7.43 (t, 1H), 6.00 (s, 1H), 4.24-4.20 (m, 1H), 3.45-3.39 (m, 1H), 3.13 (s, 3H), 2.95-2.94 (d, J=4.4 Hz, 3H), 2.04-1.97 (m, 2H), 1.48-1.44 (m, 1H), 1.11-1.06 (m, 1H).

Example 66: 5-((1-((R)-1-(2-fluoroethyl)pyrrolidin-3-yl)-2-oxo-1,2-dihydropyridin-3-yl)amino)-N-(2-methoxycyclobutyl)-7-(methylamino)pyrazolo[1,5-a]pyrimidine-3-carboxamide (I-1096)

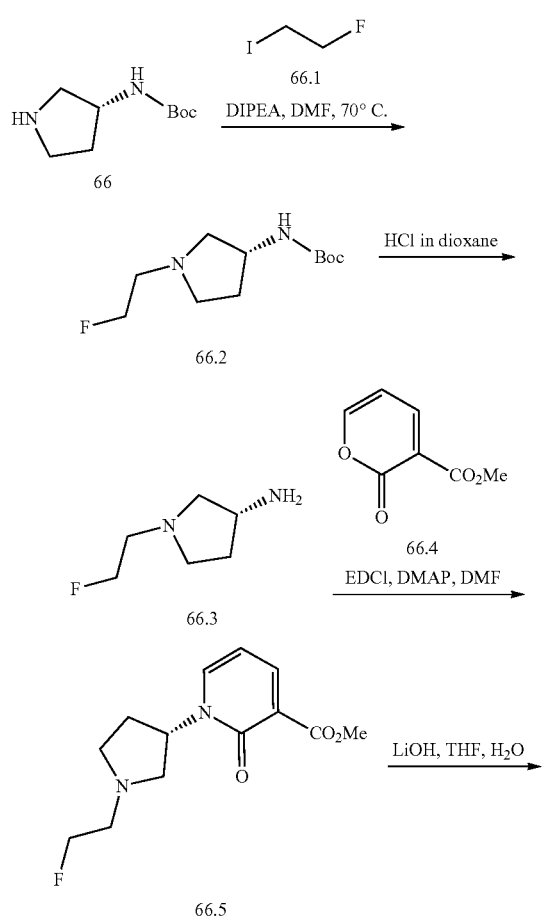

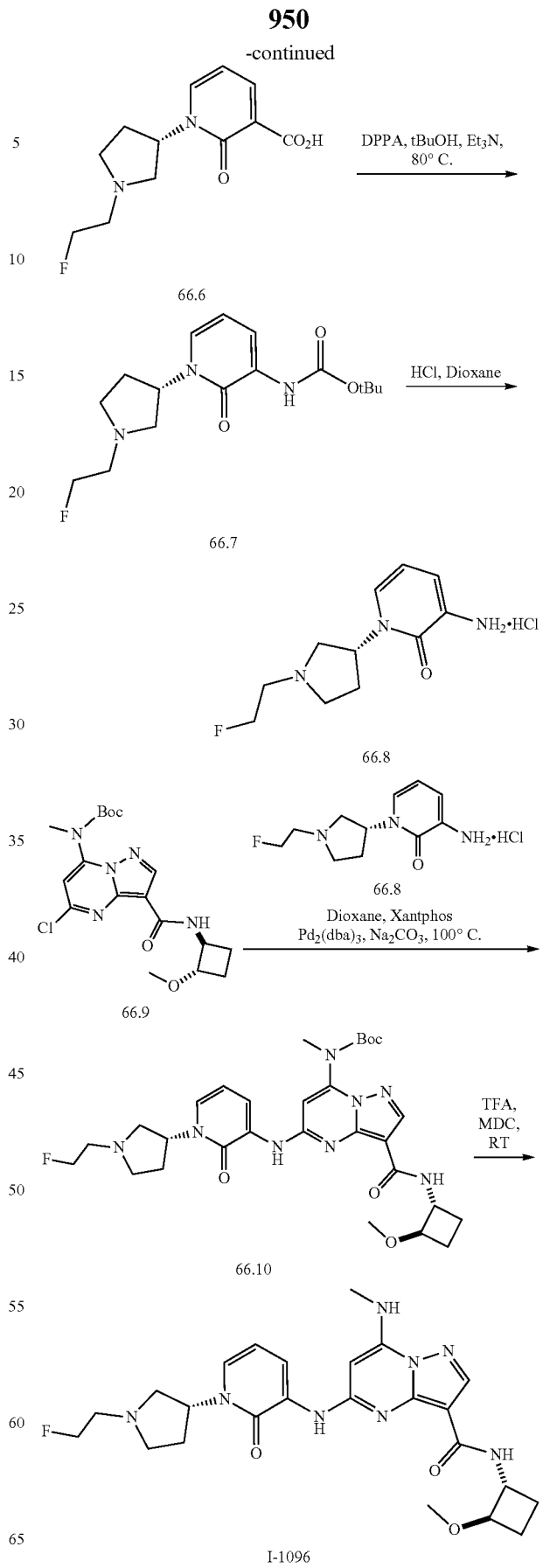

Synthesis of Compound 66.2.

To a solution of 66 (5.0 g, 26.88 mmol, 1 eq) and 66.1 (5.6 g, 32.25 mmol, 1.2 eq) in dimethylformamide (50 mL) was added N,N-Diisopropylethylamine (6.9 g, 53.76 mmol, 2.0 eq). The reaction mixture was heated at 70° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 66.2 (3.8 g, 60.94%). MS(ES): m/z 233.16 [M+H]$^+$.

Synthesis of Compound 66.3.

To 66.2 (3.8 g, 16.35 mmol, 1.0 eq) was added 4M hydrochloric acid in 1,4 Dioxane (80 mL) and stirred at room temperature for 4 h. After completion of reaction, reaction mixture was concentrated under reduced pressure, residue was triturated with diethyl ether to obtain 66.3. (2.4 g, 97.12%). MS (ES): m/z 133.11 [M+H]$^+$ Synthesis of Compound 66.5.

To a cooled solution of 66.3 (1.7 g, 12.87 mmol, 1.0 eq), in N,N-dimethylformamide (32 mL) was added 66.4 (1.98 g, 12.87 mmol, 1.0 eq). The reaction mixture was stirred at 0° C. for 6 h and further stirred at room temperature for 15 min. N-Ethyl-N'-(3-dimethylaminopropyl)carbodiimide hydrochloride (2.5 g, 16.73 mmol, 1.3 eq) and 4-Dimethylaminopyridine (0.314 g, 2.57 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 66.5. (0.610 g, 17.68%). MS(ES): m/z 269.13 [M+H]$^+$.

Synthesis of Compound 66.6.

To a solution of 66.5 (0.610 g, 2.27 mmol, 1.0 eq), in tetrahydrofuran: water (10 mL, 2:1) was added lithium hydroxide (0.544 g, 22.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 66.6. (0.5 g, 86.49%). MS(ES): m/z 255.11 [M+H]$^+$.

Synthesis of Compound 66.7.

To a solution of 66.6 (0.5 g, 1.96 mmol, 1.0 eq) in tert.butanol (10 mL) was added triethylamine (0.336 g, 3.33 mmol, 1.7 eq) and diphenyl phosphoryl azide (0.698 g, 2.54 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 66.7. (0.390 g, 60.95%). MS(ES): m/z 326.18 [M+H]$^+$.

Synthesis of Compound 66.8.

To 66.7 (0.390 g, 1.22 mmol, 1.0 eq) was added 4M hydrochloric acid in 1,4 Dioxane (6 mL) and stirred at room temperature for 4 h. After completion of reaction, reaction mixture was concentrated under reduced pressure, residue was triturated with diethyl ether to obtain 66.8. (0.320 g, 98.82%). MS (ES): m/z 226.61M+H]$^+$ Synthesis of Compound 66.9.

Compound was synthesized as per experimental protocol of Example 30 to obtain 66.9. (Yield: 57.95%), MS (ES): m/z 410.16 [M+H]$^+$ Synthesis of Compound 66.10.

Compound was synthesized using general procedure B to obtain 66.10. (0.130 g, 59.33%), MS (ES): 599.31 [M+H]$^+$ Synthesis of Compound I-1096:

Compound was synthesized using general procedure C to obtain I-1096 (0.108 g, 99.76%), MS (ES): 499.47 [M+H]$^+$ LCMS purity: 99.50%, HPLC purity: 98.07%, CHIRAL HPLC: 49.40%, 50.60%, $^1$H NMR (DMSO-d$_6$, 400 MHZ): 8.93 (s, 1H), 8.24-8.22 (d, J=6.8 Hz, 1H), 8.20 (s, 1H), 8.08-8.06 (d, J=9.2 Hz, 1H), 7.93-7.92 (d, J=4.8 Hz, 1H), 7.65-7.63 (d, J=6 Hz, 1H), 6.39-6.36 (t, J=7.2 Hz, 1H), 6.23 (s, 1H), 5.49 (bs, 1H), 4.66-4.64 (t, J=4.8 Hz, 1H), 4.55-4.52 (t, J=5.2 Hz, 1H), 4.35-4.28 (m, 1H), 3.73-3.67 (m, 1H), 3.21 (s, 3H), 3.15-3.11 (m, 1H), 2.99-2.97 (m, 1H), 2.92-2.91 (d, J=4.8 Hz, 3H), 2.85 (bs, 1H), 2.76-2.70 (m, 2H), 2.40-2.34 (m, 2H), 1.83-1.76 (m, 2H), 1.55-1.42 (m, 2H), 1.24 (bs, 1H).

Example 67: N-((1R,2R)-2-hydroxycyclopropyl)-5-(1-isopropyl-1H-pyrrolo[2,3-b]pyridin-3-yl)-7-(methylamino)pyrazolo[1,5-a]pyrimidine-3-carboxamide (I-653)

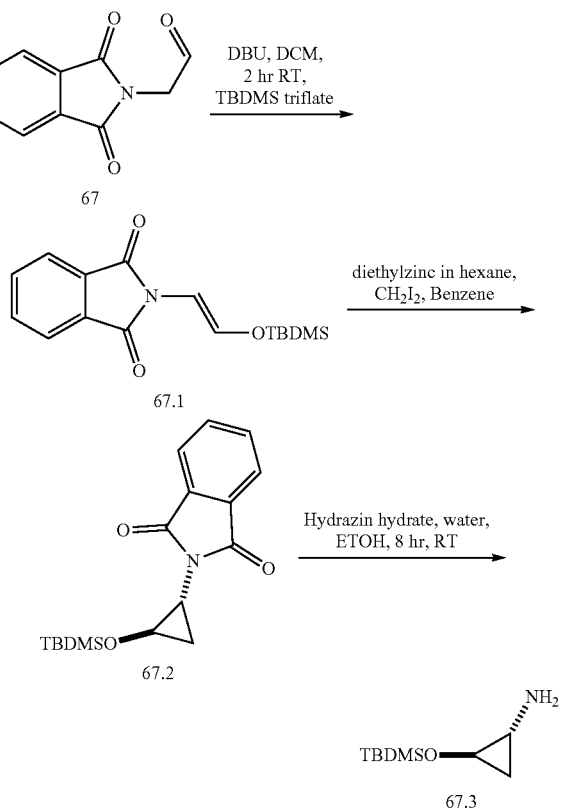

953
-continued

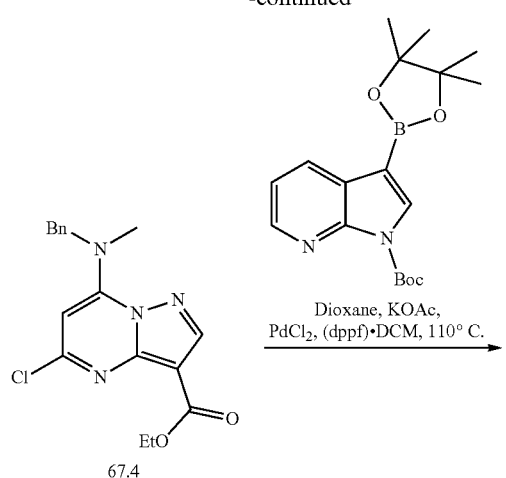

67.4

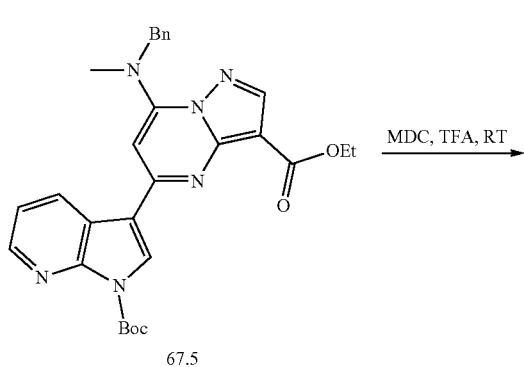

67.5

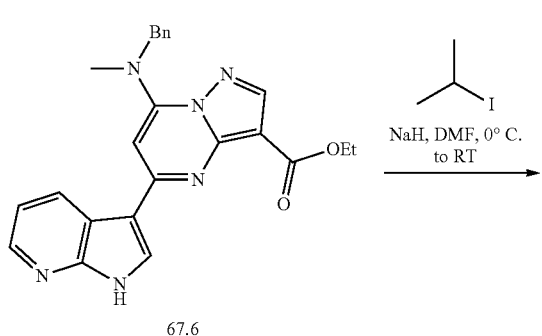

67.6

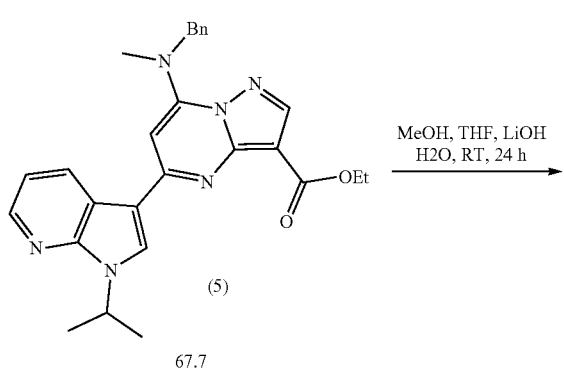

67.7

954
-continued

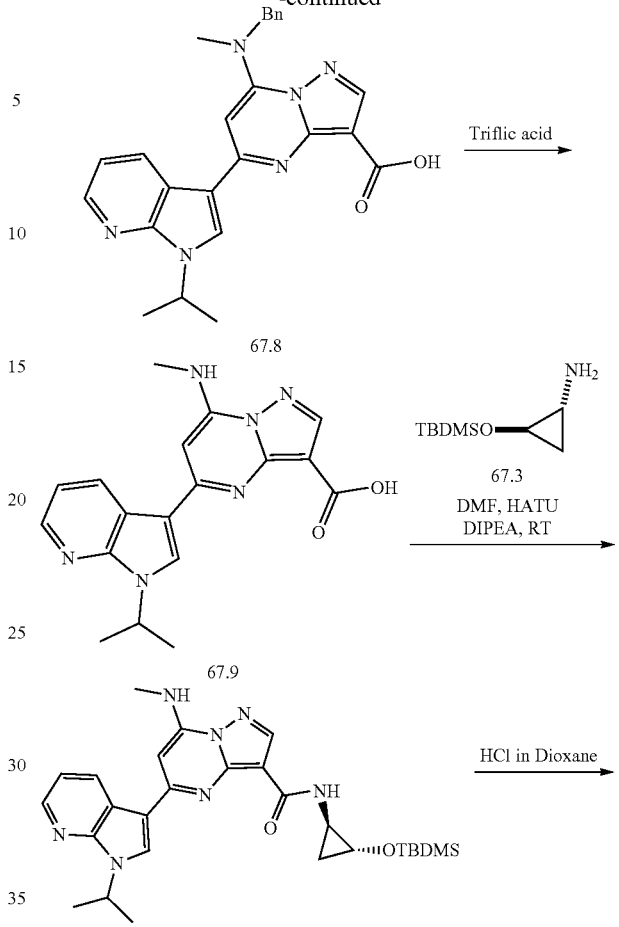

67.8

67.9

67.10

I-653

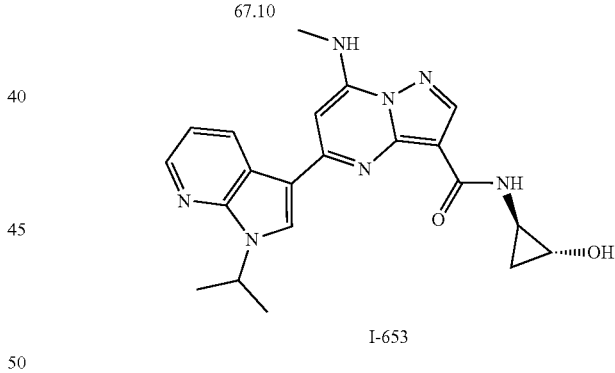

Synthesis of Compound 67.1.

To a solution of 1 (5 g, 26.455 mmol, 1.0 eq), in dichloromethane (85 mL) were added tert-Butyldimethylsilyl trifluoromethanesulfonate (13.2, 50.26 mmol, 1.9 eq) and 1,8-Diazabicyclo[5.4.0]undec-7-ene (12.9 g, 85.97 mmol, 1.9 eq) at 0° C. over 15 min. The reaction mixture was stirred at room temperature for 2 h. After completion of reaction, reaction mixture was transferred into 2N sulphuric acid solution and product was extracted with dichloromethane. Organic layer was combined, washed with brine solution, dried over sodium sulphate and concentrated under reduced pressure to obtain crude material. This was further purified by column chromatography and the compound was eluted in 5% ethyl acetate in hexane to obtain 67.1 (2 g, 24.94%). MS(ES): m/z 304.43 [M+H]$^+$.

Synthesis of Compound 67.2.

To a solution of 67.1 (2 g, 6.5 mmol, 1.0 eq), in benzene (40 mL) were added diethyl zinc (112.3 mL, 98.73, 15 eq) and di-iodomethane (26.36 g, 98.73 mmol, 15 eq) drop-wise at 0° C. over 15 min. The reaction mixture was stirred at 65° C. for 2 h. After completion of reaction, reaction mixture was transferred into 2N sulphuric acid solution and product was extracted with dichloromethane. Organic layer was combined, washed with brine solution and saturated sodium bicarbonate solution, dried over sodium sulphate and concentrated under reduced pressure to obtain crude material. This was further purified by column chromatography and the compound was eluted in 5% ethyl acetate in hexane to obtain 67.2 (1. g, 47.79%). MS(ES): m/z 318.36 [M+H]$^+$.

Synthesis of Compound 67.3.

To a solution of 67.2 (0.55 gg, 1.757 mmol, 1.0 eq) was added drop-wise hydrazine hydrate (0.52 g, 10.50 mmol, 6 eq) over 5 min in mixture of dichloromethane (2.5 mL) and ethanol (2.5 mL). The reaction mixture was stirred at room temperature for 8 h. After completion of reaction, reaction mixture was transferred into water and product was extracted with dichloromethane. Organic layer was combined, washed with brine solution, dried over sodium sulphate and concentrated under reduced pressure to obtain crude material to obtain 67.3 (0.3. g, 92.42%). MS(ES): m/z 188.36 [M+H]$^+$.

Synthesis of Compound 67.4.

Compound was synthesized using general procedure of core synthesis to obtain 67.4 (26 g, 62.21%). MS(ES): m/z 355 [M+H]$^+$.

Synthesis of Compound 67.5.

To a solution of 67.4 (0.1 g, 0.290 mmol, 1.0 eq), in dioxane (5 mL) were added tert-butyl 3-(4,4,5,5-tetramethyl-1,3,2-dioxaborolan-2-yl)-1H-pyrrolo[2,3-b]pyridine-1-carboxylate (0.129 g, 0.377, 1.3 eq) and sodium carbonate (0.076 g, 0.725 mmol 2.5 eq). The reaction mixture was degassed for 10 min. under argon atmosphere, then [1,1'-Bis(diphenylphosphino) ferrocene]dichloropalladium (II), complex with dichloromethane (0) (0.028 g, 0.029 mmol 0.1 eq) was added, again degassed for 5 min. The reaction was stirred at 100° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using eluted in 25% ethyl acetate in hexane to obtain pure 67.5 (0.083 g, 54.35%). MS(ES): m/z 527 [M+H]$^+$.

Synthesis of Compound 67.6.

Compound was synthesized using general procedure C to obtain 67.6 (0.220 g, 9055%). MS(ES): m/z 427 [M+H]$^+$.

Synthesis of Compound 67.7.

To a cooled solution of 67.6 (1 g, 2.34 mmol, 1.0 eq) in tetrahydrofuran (10 mL) was added sodium hydride (0.200 g, 4.68 mmol, 2 eq) and stirred for 20 min. followed by addition of 2-Iodopropane (1.3 g, 3.52 mmol, 1.5 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 52% ethyl acetate in hexane to obtain pure 67.7 (0.85 g, 77.37%), MS(ES): m/z 469.60 [M+H]$^+$.

Synthesis of Compound 67.8.

To a solution of 67.7 (0.3 g, 0.95 mmol, 1.0 eq), in tetrahydrofuran: methanol: water (10 mL, 2:2:1) was added lithium hydroxide (0.396 g, 9.58 mmol, 5 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 67.8 (0.25 g, 83.64%). MS(ES): m/z 441.51 [M+H]$^+$.

Synthesis of Compound 67.9.

The compound 67.8 (0.2 g, 0.45 mmol, 1.0 eq) was dissolved in dichloromethane (2 mL). Triflic acid was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 67.9 (0.12 g, 75.40%). MS(ES): m/z 351.38 [M+H]$^+$ Synthesis of Compound 67.10.

Compound was synthesized using general procedure A to obtain 67.10. (0.070 g, 39.33%), MS(ES): m/z 520.7 [M+H]$^+$.

Synthesis of Compound I-653.

The compound 2.0 (0.070 g, 0.134 mmol, 1.0 eq) was dissolved in dichloromethane (2 mL) and 4M HCl in dioxane (0.2 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-653. (0.040 g, 73.25%). MS(ES): m/z 406.44 [M+H]$^+$ LCMS purity: 98.80%, HPLC purity: 95.27%, $^1$H NMR (DMSO-d$_6$, 400 MHZ): 8.79 (s, 1H), 8.65-8.63 (d, J=7.6 Hz, 1H), 8.42-8.41 (d, J=2.4 Hz, 1H), 8.37 (s, 1H), 8.25-8.20 (m, 2H), 7.35-7.32 (m, 1H), 6.78 (s, 1H), 5.69 (s, 1H), 5.23-5.20 (m, 1H), 3.13-3.11 (d, J=4.8 Hz, 3H), 2.92-2.90 (m, 1H), 1.60-1.58 (d, J=6.8 Hz, 6H), 1.06-1.01 (m, 1H), 0.85-0.80 (m, 2H).

Example 68: 5-((2-cyclopropoxypyridin-3-yl)amino)-N-((1S,2S)-2-hydroxycyclopropyl)-7-(methylamino)pyrazolo[1,5-a]pyrimidine-3-carboxamide (I-439)

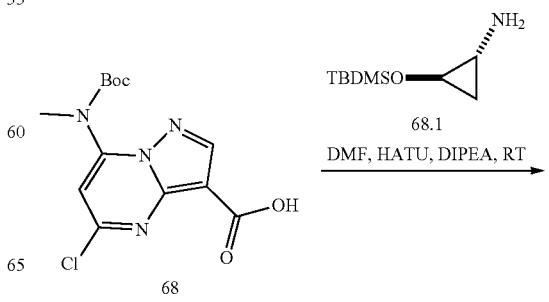

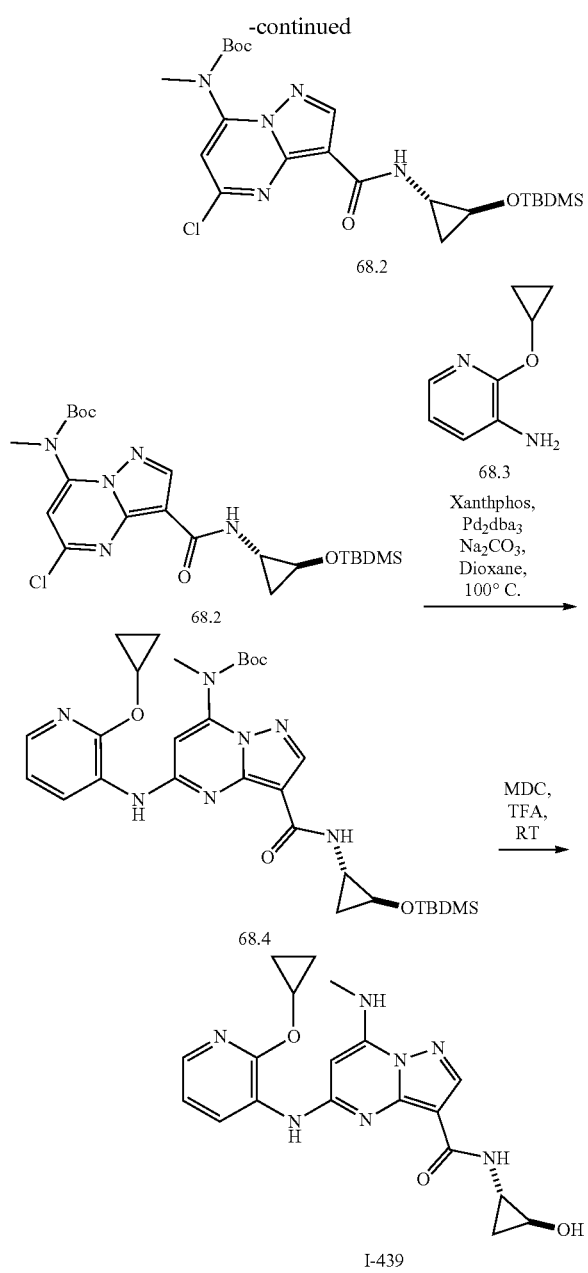

Synthesis of Compound 68.

Compound was synthesized using general procedure of core synthesis to obtain 68. (Yield: 71.67%). MS (ES): m/z 327.08 [M+H]+

Synthesis of Compound 68.1.

Compound was synthesized as per experimental process of Example 67 to obtain 68. (Yield: 92.42%). MS (ES): m/z 188.36 [M+H]+

Synthesis of Compound 68.2.

Compound was synthesized using general procedure A to obtain 68.2. (0.340 g, 63.98%), MS (ES): 497.20 [M+H]+

Synthesis of Compound 68.4.

Compound was synthesized using general procedure B to obtain 68.4. (0.159 g, 76.09%), MS (ES): 610.31 [M+H]+

Synthesis of Compound I-439:

Compound was synthesized using general procedure C to obtain I-439 (0.126 g, 96.99%), MS (ES): m/z 396.17 [M+H]+, LCMS purity: 95.90%, HPLC purity: 98.08%, CHIRAL HPLC purity: 46.20%, 40.94% $^1$H NMR (DMSO-$d_6$, 400 MHZ): 8.76 (s, 1H), 8.20-8.16 (t, J=7.2 Hz, 1H), 7.96-7.95 (d, J=3.6 Hz, 1H), 7.66-7.65 (d, J=3.6 Hz, 1H), 7.08-7.05 (m, 1H), 5.84 (s, 1H), 4.35-4.34 (d, J=6 Hz 1H), 3.41-3.35 (m, 1H), 2.91-2.89 (d, J=4.8 Hz, 3H), 2.75 (s, 1H), 2.69 (s, 1H), 1.33 (s, 1H), 1.19-1.11 (m, 1H), 0.87-0.85 (m, 1H), 0.74-0.73 (d, J=5.2 Hz, 4H), 0.55 (bs, 1H).

Example 69: N-((1R,2R)-2-hydroxycyclopropyl)-5-(1-isopropyl-1H-pyrrolo[2,3-b]pyridin-3-yl)-7-(methylamino)pyrazolo[1,5-a]pyrimidine-3-carboxamide (I-732) and N-((1S,2S)-2-hydroxycyclopropyl)-5-(1-isopropyl-1H-pyrrolo[2,3-b]pyridin-3-yl)-7-(methylamino)pyrazolo[1,5-a]pyrimidine-3-carboxamide (I-733)

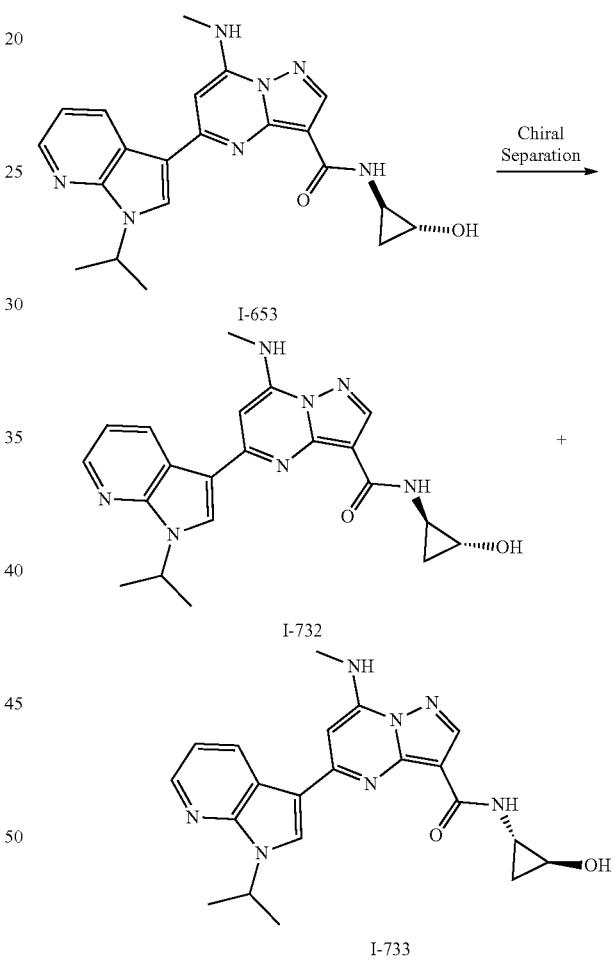

Synthesis of Compound I-732 & I-733.

Isomers of I-653 (Example 67) (0.8 g) were separated using a column (CHIRAL PAK AD-H 250×4.6 mm, 5 u) and 0.1% DEA in methanol and isopropyl alcohol as co-solvent with flow rate of 4 mL/min. to get pure fraction-1 (FR-a) and fraction-2 (FR-b). FR-a was concentrated under reduced pressure at 30° C. to afford pure FR-a. (0.026 g). MS(ES): m/z 406.48 [M+H]+, LCMS purity: 95.16%, HPLC purity: 97.46%, CHIRAL HPLC purity: 96.12%, $^1$H NMR (DMSO-$d_6$, 400 MHZ): 8.79 (s, 1H), 8.65-8.63 (d, J=7.6 Hz, 1H), 8.42-8.41 (d, J=2.4 Hz, 1H), 8.37 (s, 1H), 8.25-8.20 (m, 2H), 7.35-7.32 (m, 1H), 6.78 (s, 1H), 5.71-5.70 (d, J=2 Hz, 1H), 5.23-5.20 (m, 2H), 3.13-3.11 (d, J=4.8 Hz, 3H), 2.92-2.90 (d, J=3.6 Hz, 1H), 1.60-1.58 (d, J=6.8 Hz, 6H), 1.06-1.01 (m, 1H), 0.85-0.80 (m, 1H).

FR-b was concentrated under reduced pressure at 30° C. to afford pure FR-b (0.025 g). MS(ES): m/z 406.46 [M+H]+, LCMS purity: 96.16%, HPLC purity: 98.21%, CHIRAL HPLC purity: 93.76%, $^1$H NMR (DMSO-d$_6$, 400 MHZ): 8.79 (s, 1H), 8.64-8.63 (d, J=6.8 Hz, 1H), 8.42-8.41 (d, J=3.6 Hz, 1H), 8.37 (s, 1H), 8.25-8.20 (m, 2H), 7.35-7.32 (m, 1H), 6.78 (s, 1H), 5.71-5.70 (d, J=2 Hz, 1H), 5.23-5.20 (m, 1H 3.12-3.11 (d, J=4.8 Hz, 3H), 2.90 (bs, 1H), 1.59-1.58 (d, J=6.8 Hz, 6H), 1.05-1.01 (m, 1H), 0.84-0.80 (m, 1H).

Example 70: N-((1S,2S)-2-hydroxycyclopropyl)-5-((2-methoxypyridin-3-yl)amino)-7-(methylamino) pyrazolo[1,5-a]pyrimidine-3-carboxamide (I-438)

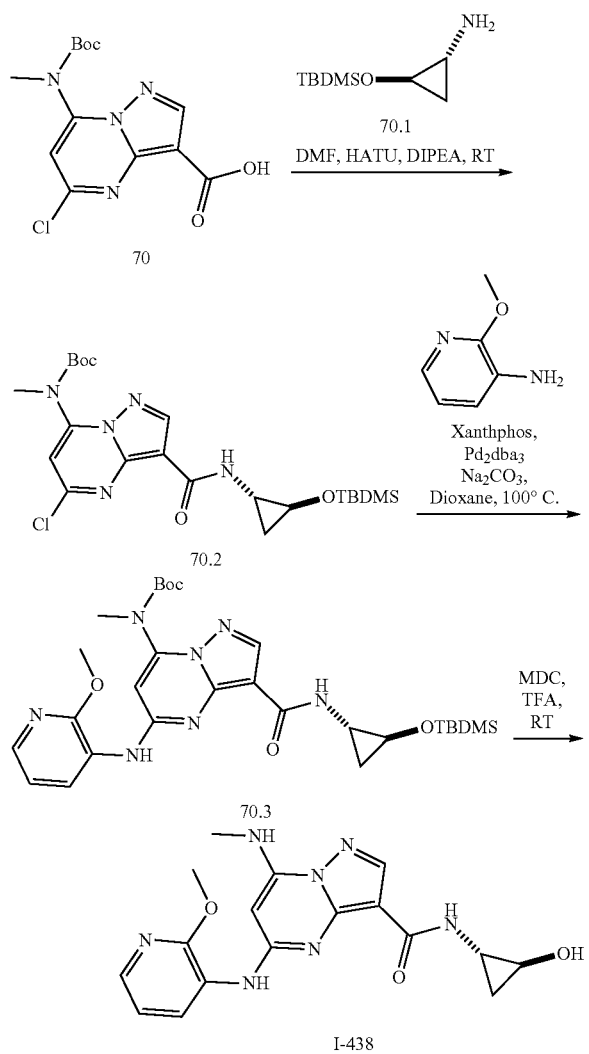

Synthesis of Compound 70.

Compound was synthesized using general procedure of core synthesis to obtain 70. (Yield: 71.67%). MS (ES): m/z 327.08 [M+H]+

Synthesis of Compound 70.1.

Compound was synthesized as per experimental process of Example 67 to obtain 70. (Yield: 92.42%). MS (ES): m/z 188.36 [M+H]+

Synthesis of Compound 70.2.

Compound was synthesized using general procedure A to obtain 70.2. (0.340 g, 63.98%), MS (ES): 497.20 [M+H]+

Synthesis of Compound 70.3.

Compound was synthesized using general procedure B to obtain 70.4. (0.162 g, 80.98%), MS (ES): 584.30 [M+H]+

Synthesis of Compound I-438:

Compound was synthesized using general procedure C to obtain I-438 (0.110 g, 97.55%), MS (ES): m/z 370.44 [M+H]+, LCMS purity: 96.21%, HPLC purity: 90.76%, CHIRAL HPLC purity: 47.52%, 42.26% $^1$H NMR (DMSO-d$_6$, 400 MHZ): 8.93 (s, 1H), 8.21-8.19 (d, J=8.8 Hz, 1H), 8.15 (s, 1H), 7.93-7.91 (m, 2H), 7.66-7.65 (d, J=4 Hz 1H), 7.08-7.03 (m, 2H), 6.83-6.81 (d, J=7.6 Hz, 1H), 5.88 (s, 1H), 5.54-5.52 (m, 1H), 3.97 (s, 3H), 2.90-2.89 (d, J=4.8 Hz, 3H), 2.76-2.73 (m, 1H), 1.55 (bs, 1H).

Example 71: N-((1R,2R)-2-hydroxycyclopentyl)-5-((2-methoxypyridin-3-yl)amino)-7-(methylamino) pyrazolo[1,5-a]pyrimidine-3-carboxamide (I-423)

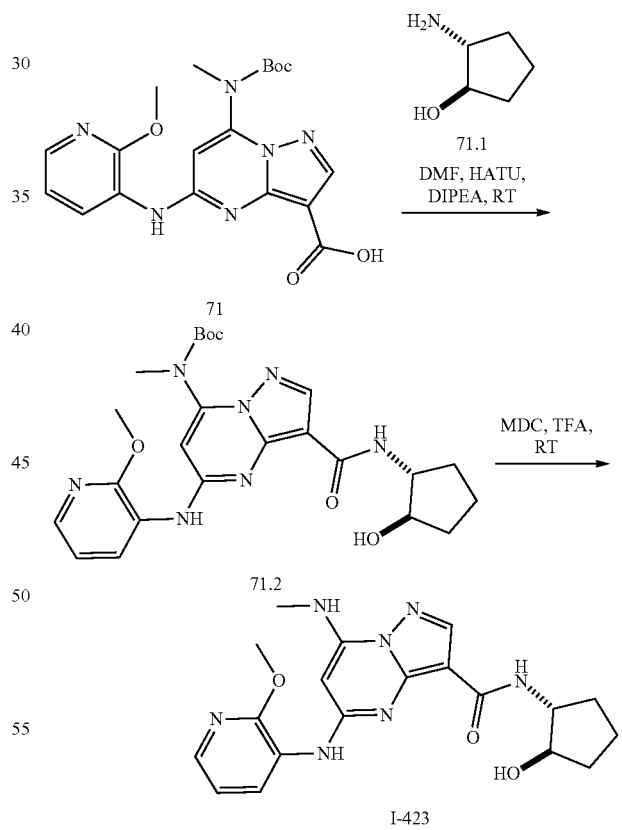

Synthesis of Compound 71.

Compound was synthesized as per experimental protocol of Example 32 to obtain 71. (Yield: 71.18%), MS (ES): m/z 415.42 [M+H]+

Synthesis of Compound 71.2.

Compound was synthesized using general procedure A to obtain 71.2. (0.150 g, 62.47%), MS (ES): 498.24 [M+H]+

Synthesis of Compound I-423:

Compound was synthesized using general procedure C to obtain I-423 (0.104 g, 86.80%), MS (ES): m/z 398.22 [M+H]+, LCMS purity: 98.12%, HPLC purity: 97.55%, CHIRAL HPLC: (48.18%, 48.70%) 1H NMR (DMSO-d6, 400 MHZ): 8.91 (s, 1H), 8.25-8.24 (d, J=6.8 Hz, 1H), 8.16 (s, 1H), 7.92-7.91 (d, J=4.8 Hz, 1H), 7.65-7.64 (d, J=7.2 Hz, 1H), 7.01-6.98 (m, 1H), 5.91 (s, 1H), 4.91-4.90 (d, J=4 Hz, 1H), 3.93 (s, 4H), 3.76-3.73 (t, J=5.2 Hz, 1H), 2.92-2.91 (d, J=4.4 Hz, 3H), 2.03-2.00 (m, 2H), 1.34 (bs, 4H), 0.73 (bs, 1H).

Example 72: (R)-N-((1R,2R)-2-hydroxycyclopentyl)-5-((2-methoxypyridin-3-yl)amino)-7-(methylamino)pyrazolo[1,5-a]pyrimidine-3-carboxamide (I-448) and (S)-N-((1S,2S)-2-hydroxycyclopentyl)-5-((2-methoxypyridin-3-yl)amino)-7-(methylamino)pyrazolo[1,5-a]pyrimidine-3-carboxamide (I-449)

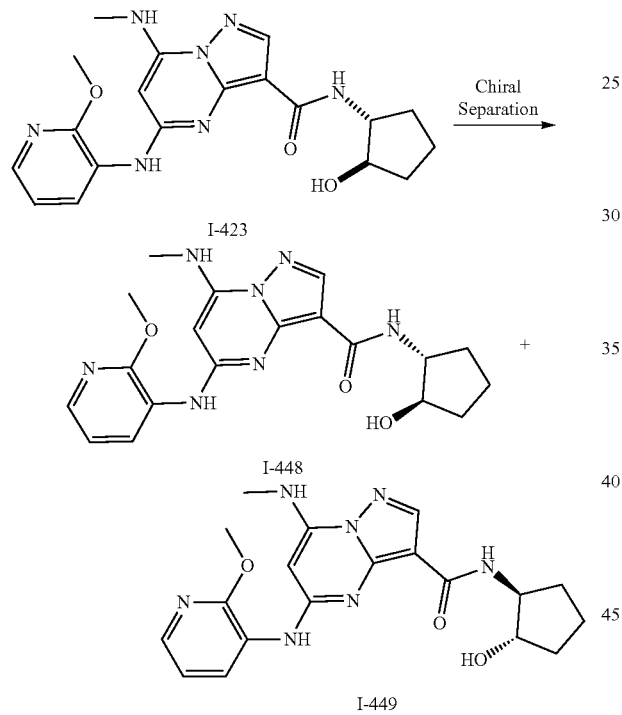

Synthesis of Compound I-449 & I-449.

Isomers of I-423 (Example 71) (0.090 g) were separated using a column (CHIRAL PAK AD-H 250×4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure FR-a (0.025 g). MS(ES): m/z 398.55 [M+H]+, LCMS purity: 100%, HPLC purity: 100%, CHIRAL HPLC purity: 100%, 1H NMR (DMSO-d6, 400 MHZ): 8.90 (s, 1H), 8.25-8.23 (d, J=7.6 Hz, 1H), 8.15 (s, 1H), 7.91-7.90 (t, J=3.2 Hz, 2H), 7.64-7.63 (d, J=7.2 Hz, 1H), 7.00-6.97 (m, 1H), 5.90 (s, J=7.6 Hz, 1H), 4.90-4.89 (d, J=4.4 Hz, 1H), 3.92 (s, 4H), 3.75-3.73 (t, J=4.8 Hz, 1H), 2.91-2.90 (d, J=4.8 Hz, 3H), 2.01-1.96 (m, 1H), 1.74-1.70 (m, 2H), 1.52-1.48 (m, 1H), 1.47-1.43 (m, 2H).

FR-b was concentrated under reduced pressure at 30° C. to afford pure FR-b (0.025 g). MS(ES): m/z 396.6 [M−H]+, LCMS purity: 98.76%, HPLC purity: 98.66%, CHIRAL HPLC purity: 96.99%, 1H NMR (DMSO-d6, 400 MHZ): 8.90 (s, 1H), 8.24-8.23 (d, J=6.8 Hz, 1H), 8.15 (s, 1H), 7.91-7.90 (d, J=3.6 Hz, 2H), 7.64-7.63 (d, J=7.2 Hz, 1H), 7.00-6.97 (m, 1H), 5.90 (s, 1H), 4.90 (s, 1H), 3.92 (s, 4H), 3.75 (bs, 1H), 2.91-2.90 (d, J=2.8 Hz, 3H), 2.01-1.98 (m, 1H), 1.74-1.70 (m, 2H), 1.52-1.48 (m, 1H), 1.48-1.44 (m, 2H).

Example 73: 5-((2-cyclopropoxypyridin-3-yl)amino)-N-(2-hydroxycyclopentyl)-7-(methylamino)pyrazolo[1,5-a]pyrimidine-3-carboxamide (I-424), 5-((2-cyclopropoxypyridin-3-yl)amino)-N-((1R,2R)-2-hydroxycyclopentyl)-7-(methylamino)pyrazolo[1,5-a]pyrimidine-3-carboxamide (I-465), and 5-((2-cyclopropoxypyridin-3-yl)amino)-N-((1S,2S)-2-hydroxycyclopentyl)-7-(methylamino)pyrazolo[1,5-a]pyrimidine-3-carboxamide (I-466)

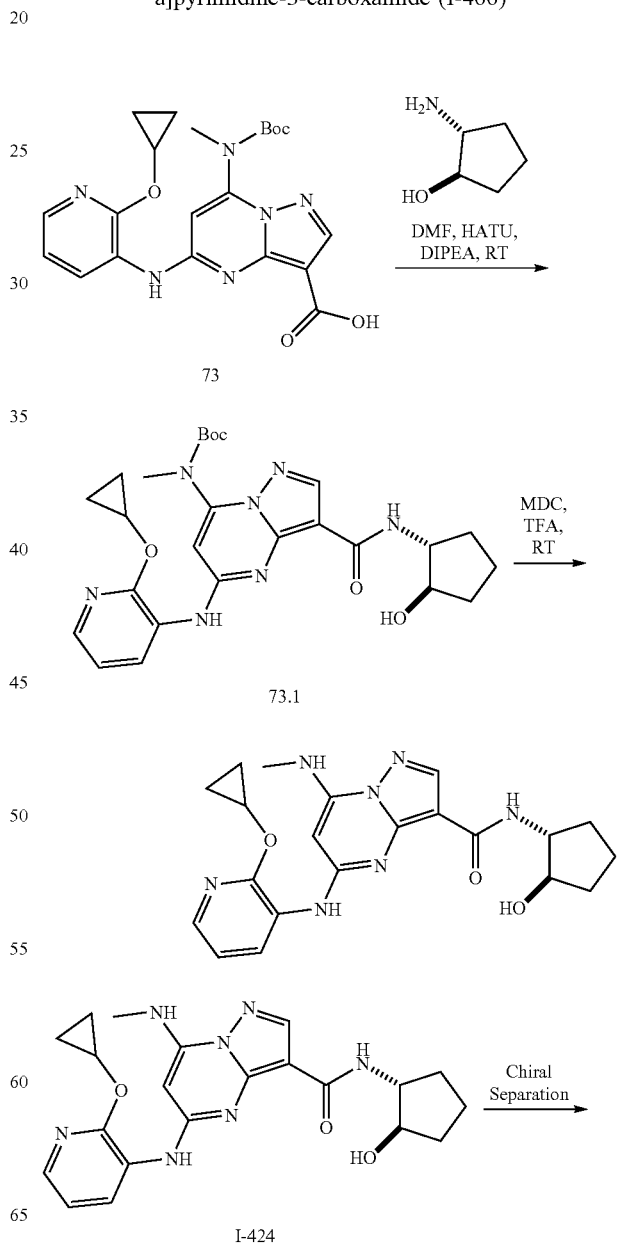

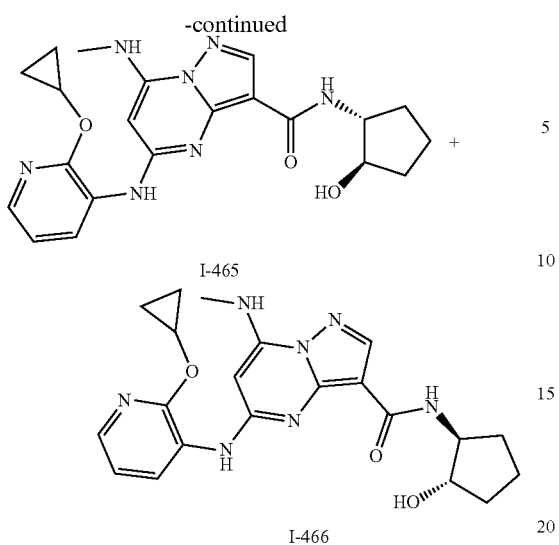

Synthesis of Compound 73:

Compound was synthesized as per experimental protocol of Example 56 to obtain 73. (Yield: 79.78%). MS (ES): m/z 441.18 [M+H]$^+$.

Synthesis of Compound 73.1:

Compound was synthesized using general procedure A to obtain 73.1 (0.147 g, 61.83%). MS (ES): m/z 524.59 [M+H]$^+$.

Synthesis of Compound I-424:

Compound was synthesized using general procedure C to obtain I-424 (0.118 g, 99.25%). MS (ES): m/z 424.22 [M+H]$^+$, LCMS purity: 100%, HPLC purity: 97.91%, Chiral HPLC: 49.99% and 50.00% $^1$H NMR (DMSO-d$_6$, 400 MHZ): 8.71 (s, 1H), 8.24-8.22 (d, J=8.0 Hz, 1H), 8.16 (s, 1H), 7.95-7.92 (m, 1H), 7.64-7.62 (d, J=8.0 Hz, 1H), 7.03-7.00 (m, 1H), 5.87 (s, 1H), 4.91-4.90 (d, J=4.0, 1H), 4.35-4.34 (d, J=4.0 Hz, 1H), 3.97-3.92 (m, 1H), 3.75-3.74 (m, 1H), 2.92-2.91 (d, J=4.0 Hz, 3H), 2.01-1.98 (m, 1H), 1.72-1.62 (m, 2H), 1.51-1.43 (m, 2H), 1.26-1.21 (m, 2H), 0.80-0.73 (m, 4H).

Isomers of I-424 (0.118 g) were separated out using column (CHIRALPAK AD-H (250 mm*4.6 mm, 5 u) in 0.1% DEA in IPA:MeOH (50:50) as co-solvent with flow rate of 4 mL/min. to get pure fraction-1 (FR-a) and fraction-2 (FR-b). FR-a was concentrated under reduced pressure at 30° C. to afford pure FR-a (0.015 g). MS(ES): m/z 424.28 [M+H]$^+$, LCMS purity: 100%, HPLC purity: 99.17%, CHIRAL HPLC purity: 100%, $^1$H NMR (DMSO-d$_6$, 400 MHZ): 8.71 (s, 1H), 8.23-8.21 (d, J=8.0 Hz, 1H), 8.15 (s, 1H), 7.94-7.90 (m, 1H), 7.63-7.61 (d, J=8.0 Hz, 1H), 7.02-6.99 (m, 1H), 5.86 (s, 1H), 4.90-4.89 (d, J=4.0, 1H), 4.35-4.32 (m, 1H), 3.95-3.90 (m, 1H), 3.75-3.74 (m, 1H), 2.92-2.90 (d, J=8.0 Hz, 3H), 2.01-1.98 (m, 1H), 1.73-1.59 (m, 2H), 1.51-1.45 (m, 2H), 1.27-1.18 (m, 2H), 0.80-0.72 (m, 4H).

FR-b was concentrated under reduced pressure at 30° C. to afford pure FR-b (0.016 g). MS(ES): m/z 424.33 [M+H]$^+$, LCMS purity: 100%, HPLC purity: 97.91%, CHIRAL HPLC purity: 97.19%, $^1$H NMR (DMSO-d$_6$, 400 MHZ): 8.70 (s, 1H), 8.23-8.21 (d, J=8.0 Hz, 1H), 8.15 (s, 1H), 7.94-7.90 (m, 1H), 7.63-7.61 (d, J=8.0 Hz, 1H), 7.02-6.99 (m, 1H), 5.86 (s, 1H), 4.90-4.89 (d, J=4.0, 1H), 4.35-4.32 (m, 1H), 3.95-3.91 (m, 1H), 3.75-3.73 (m, 1H), 2.92-2.90 (d, J=8.0 Hz, 3H), 2.02-1.97 (m, 1H), 1.73-1.59 (m, 2H), 1.51-1.45 (m, 2H), 1.27-1.20 (m, 2H), 0.80-0.72 (m, 4H).

Example 74: 5-((2-cyclopropoxypyridin-3-yl)amino)-N-((1r,3r)-3-hydroxycyclobutyl)-7-(methylamino)pyrazolo[1,5-a]pyrimidine-3-carboxamide (I-320)

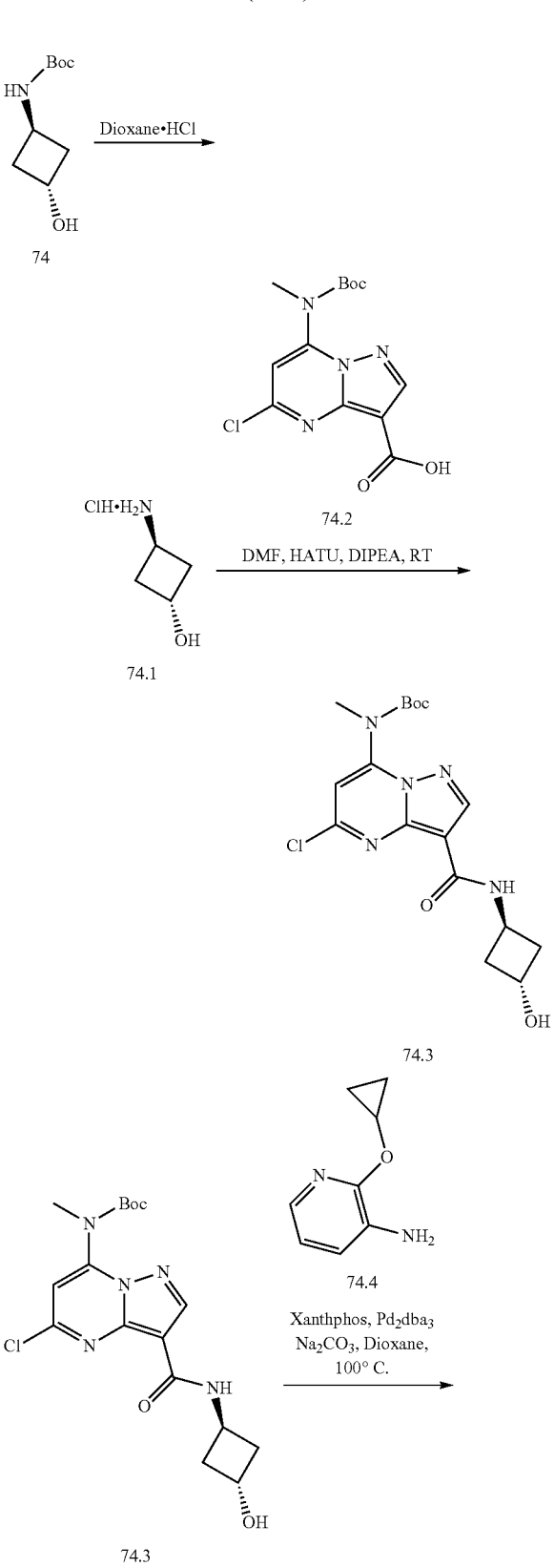

965

-continued

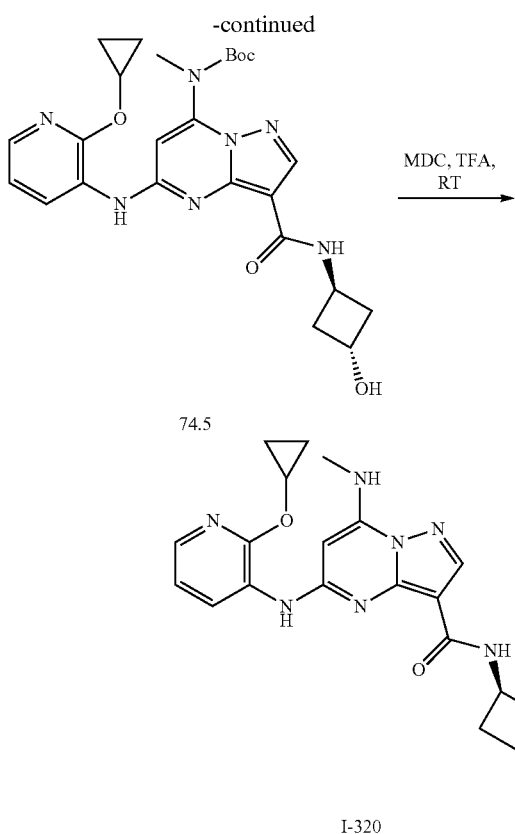

Synthesis of Compound 74.1.

To 74 (0.50 g, 2.67 mmol, 1.0 eq) added hydrochloric acid in dioxane (5 mL) at 0° C. The reaction mixture was stirred at room temperature for 1 h. After completion of reaction, reaction mixture was concentrated under reduced pressure to obtain crude material. This was further purified by trituration with diethylether to obtain 74.1 (0.30 g, 90.91%). MS(ES): m/z 124.58 [M+H]$^+$.

Synthesis of Compound 74.2.

Compound was synthesized as per general synthesis of core to obtain 74.2.

Synthesis of Compound 74.3.

Compound was synthesized using general procedure A to obtain 74.3 (Yield: 26.02%). MS (ES): m/z 396.84 [M+H]$^+$.

Synthesis of Compound 74.4.

Compound was synthesized as per experimental protocol of Example 55.

Synthesis of Compound 74.5.

Compound was synthesized using general procedure B to obtain 74.5 (0.05 g, 38.84%). MS (ES): m/z 510.57 [M+H]$^+$ Synthesis of Compound I-320.

Compound was synthesized using general procedure C to a obtain I-320 (0.02 g, 62.23%). MS(ES): m/z 410.45 [M+H]$^+$, LCMS purity: 95.11%, HPLC purity: 95.18%, CHIRAL HPLC: 98%, $^1$H NMR (DMSO-d$_6$, 400 MHZ): 8.75 (s, 1H), 8.30-8.28 (d, J=6.4 Hz, 1H), 8.14 (s, 1H), 7.96-7.86 (m, 3H), 7.06-7.03 (m, 1H), 5.87 (s, 1H), 5.10-5.09 (d, J=5.6 Hz, 1H), 4.41-4.34 (m, 2H), 4.24-4.23 (d, J=5.2 Hz, 1H), 3.18-3.17 (d, J=5.2 Hz, 1H), 2.93-2.91 (d, J=4.8 Hz, 3H), 2.19-2.13 (m, 2H), 2.07-1.95 (m, 2H), 0.81-0.75 (m, 3H).

966

Example 75: N-cyclopropyl-5-((2-(methoxy-d3)pyridin-3-yl)amino)-7-(methylamino)pyrazolo[1,5-a]pyrimidine-3-carboxamide (I-175)

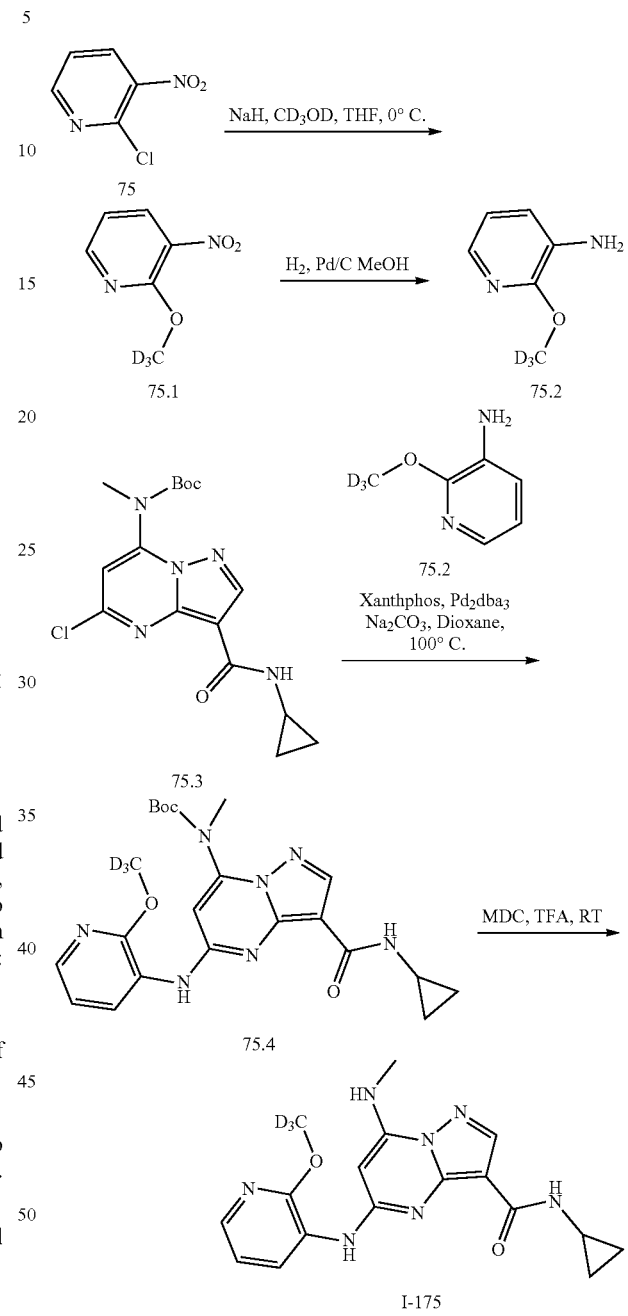

Synthesis of Compound 75.2.

To a cooled solution of 75 (1 g, 6.31 mmol, 1 eq) in tetrahydrofuran (10 mL) was added sodium hydride (0.505 g, 12.62 mmol, 2 eq) followed by addition of tetradeuteromethanol (0.250 g, 6.94 mmol, 1.1 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 13% ethyl acetate in hexane to obtain pure 75.2 (0.900 g, 90.80%), MS(ES): m/z 158.14 [M+H]$^+$.

Synthesis of Compound 75.3.

To a solution of 75.2 (0.900 g, 5.73 mmol, 1.0 eq) in methanol (10 ml), palladium on charcoal (0.220 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 75.3 (0.650 g, 89.25%). MS (ES): m/z 128.16 $[M+H]^+$.

Synthesis of Compound 75.4.

Compound was synthesized as per experimental protocol of Example 27 to obtain 75.4 (Yield: 57.16%), MS (ES): m/z 366.82 $[M+H]^+$ Synthesis of Compound 75.5.

Compound was synthesized using general procedure B to obtain 75.5 (0.075 g, 60.10%), MS (ES): m/z 457.52 $[M+H]^+$ Synthesis of Compound I-175:

Compound was synthesized using general procedure C to obtain I-175 (0.035 g, 59.78%), MS (ES): m/z 357.4 $[M+H]^+$, LCMS purity: 100%, HPLC purity: 99.53%, $^1$H NMR (DMSO-$d_6$, 400 MHZ): 8.93 (s, 1H), 8.21-8.19 (d, J=8 Hz, 1H), 8.15 (s, 1H), 7.93-7.90 (m, 2H), 7.80-7.79 (d, J=4 Hz, 1H), 7.03-7.00 (m, 1H), 5.88 (s, 1H), 2.91-2.89 (d, J=8 Hz, 3H), 2.80-2.76 (m, 1H), 0.72-0.68 (m, 2H), 0.37-0.35 (m, 2H).

Example 76: N-((1r,3r)-3-hydroxycyclobutyl)-5-((2-(methoxy-d3)pyridin-3-yl)amino)-7-(methylamino)pyrazolo[1,5-a]pyrimidine-3-carboxamide (I-321)

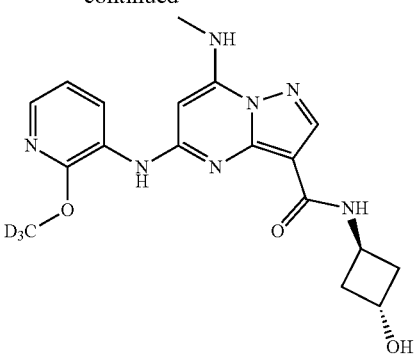

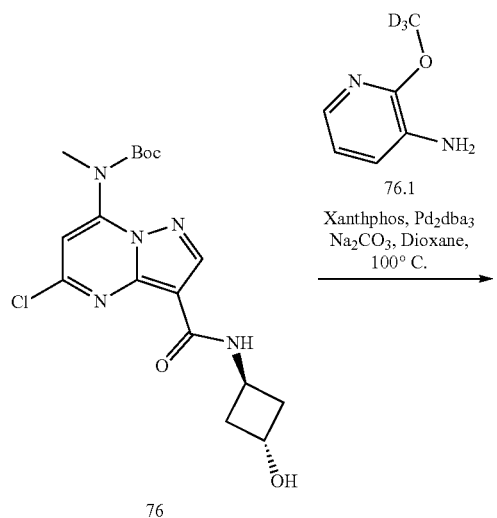

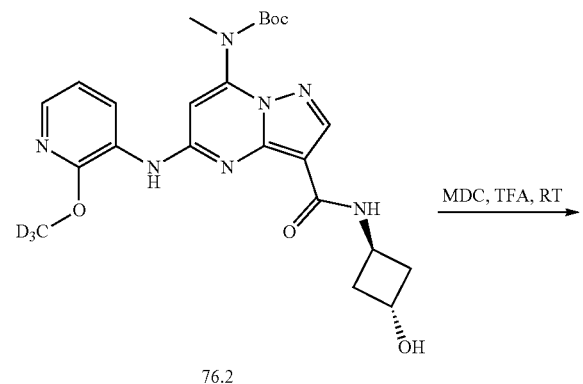

Synthesis of Compound 76.

Compound was synthesized as per experimental protocol of Example 74.

Synthesis of Compound 76.1.

Compound was synthesized as per experimental protocol of Example 75.

Synthesis of Compound 76.2.

Compound was synthesized using general procedure B to obtain 76.2. (0.06 g, 48.81%). MS (ES): m/z 487.55 $[M+H]^+$.

Synthesis of Compound I-321.

Compound was synthesized using general procedure C to obtain I-321 (0.02 g, 56.66%). MS(ES): m/z 387.43 $[M+H]$—, LCMS purity: 95.02%, HPLC purity: 97.27%, CHIRAL HPLC: 98.24%, $^1$H NMR (DMSO-$d_6$, 400 MHZ): 8.94 (s, 1H), 8.32-8.30 (d, J=7.6 Hz, 1H), 8.14 (s, 1H), 7.93-7.88 (m, 2H), 7.03-7.00 (m, 1H), 5.92 (s, 1H), 5.77 (s, 1H), 5.10 (s, 1H), 4.42-4.38 (m, 1H), 4.24 (s, 1H), 2.92 (s, 3H), 2.19-2.13 (m, 2H), 2.02-1.96 (m, 2H).

Example 77: N-((1r,3r)-3-hydroxycyclobutyl)-5-(1-isopropyl-1H-pyrrolo[2,3-b]pyridin-3-yl)-7-(methylamino)pyrazolo[1,5-a]pyrimidine-3-carboxamide (I-630)

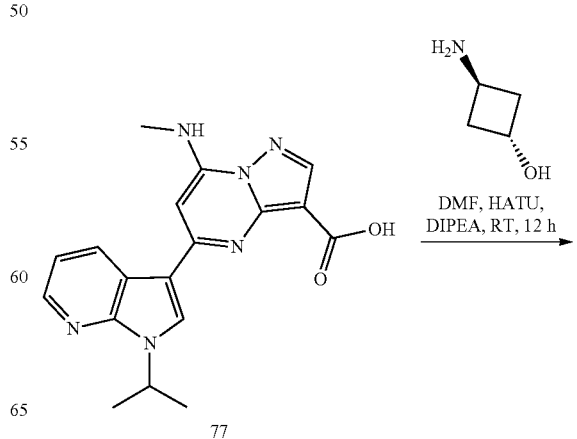

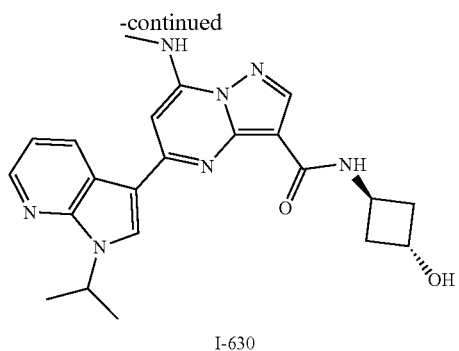

I-630

Synthesis of Compound 77

Compound was synthesized as per experimental protocol of Example 67. (0.12 g, 75.40%). MS(ES): m/z 351.38 [M+H]+

Synthesis of Compound I-630:

Compound was synthesized using general procedure A to obtain I-630 (0.035 g, 34.39%). MS(ES): m/z 420.49 [M+H]+ LCMS purity: 100%, HPLC purity: 99.67%, Chiral HPLC purity: 98.60%, NMR (DMSO-$d_6$, 400 MHZ): 8.80-8.79 (d, J=5.2 Hz, 2H), 8.42-8.41 (d, J=3.6 Hz, 1H), 8.37-8.35 (d, J=6.4 Hz, 1H), 8.25-8.23 (d, J=4.8 Hz, 2H), 7.30-7.27 (m, 1H), 6.79 (s, 1H), 5.24-5.20 (m, 2H), 4.57-4.56 (d, J=7.2 Hz, 1H), 4.46-4.45 (d, J=7.2 Hz, 1H), 3.13-3.12 (d, J=4.4 Hz, 3H), 2.34-2.28 (m, 4H), 1.60-1.59 (d, J=6.8 Hz, 6H).

Example 78: N-cyclopropyl-5-(1-cyclopropyl-1H-pyrrolo[2,3-b]pyridin-3-yl)-7-(methylamino)pyrazolo[1,5-a]pyrimidine-3-carboxamide (I-960)

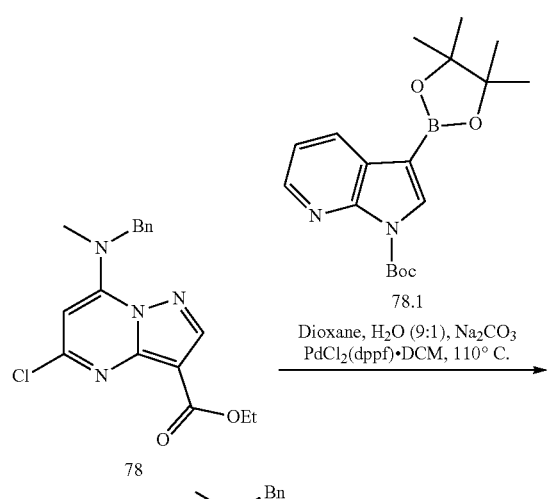

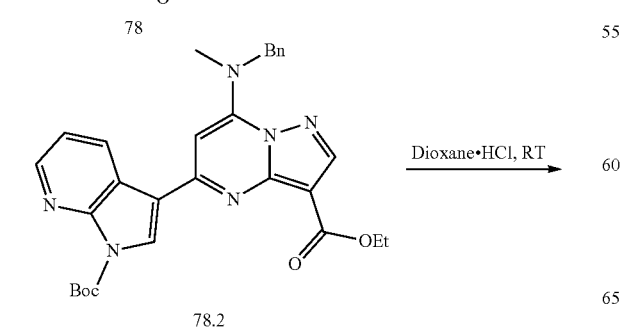

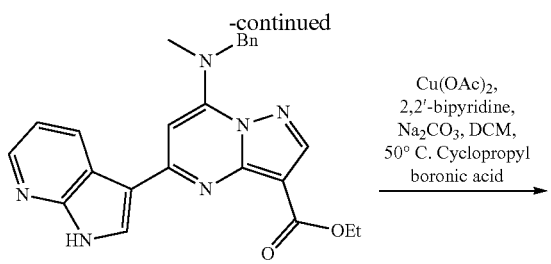

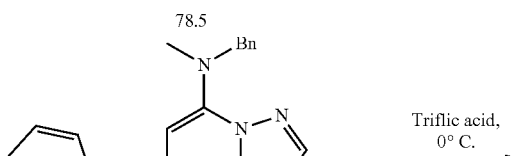

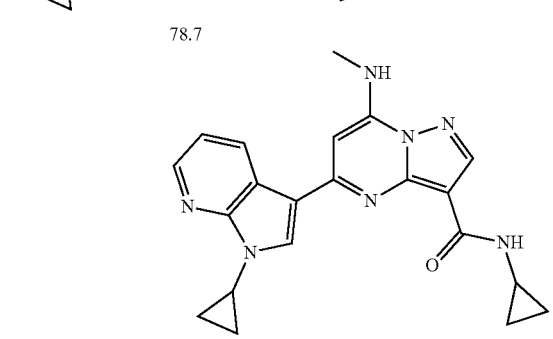

I-960

Synthesis of Compound 78.

Compound was synthesized using general procedure of core synthesis to obtain 78. (Yield: 45%), MS(ES): m/z 345.10 [M+H]+.

Synthesis of Compound 78.2.

Argon was purged for 15 min through a stirring solution of 78 (3.5 g, 10.15 mmol, 1.0 eq), 78.1 (4.5 g, 13.19 mmol, 1.3 eq) and Sodium carbonate (2.6 g, 25.37 mmol, 2.5 eq) in 1,4 dioxane:water (140 mL, 9:1) [1,1'-Bis(diphenylphosphino)ferrocene]palladium(II) dichloride (0.738 mg, 1.01 mmol, 0.1 eq) was added to it and further purging done for 10 min. Reaction was allowed to stirred at 110° C. for 6 h. After completion of reaction, reaction mixture was poured over water and product was extracted with ethyl acetate. Organic layer was combined, washed with brine solution, dried over sodium sulphate and concentrated under reduced pressure to obtain 78.2. (3.1 g, 57.99%). MS (ES): m/z 527.24[M+H]$^+$ Synthesis of Compound 78.3.

To 78.2 (3.1 g, 5.88 mmol, 1.0 eq) was added 4M hydrochloric acid in 1,4 Dioxane (60 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 78.3. (2.1 g, 83.64%). MS (ES): m/z 427.18 [M+H]$^+$ Synthesis of Compound 78.4.

Argon was purged for 15 min through a stirring solution of 78.3 (1.0 g, 2.34 mmol, 1.0 eq), cyclopropyl boronic acid (0.261 g, 3.04 mmol, 1.3 eq) and Cupric acetate (1.0 g, 5.85 mmol, 2.5 eq) in dichloromethane (80 mL) 2,2'-Bipyridine (0.182 mg, 1.17 mmol, 0.5 eq) was added to it and further purging done for 10 min. Reaction was allowed to stirred at 50° C. for 6 h. After completion of reaction, reaction mixture was poured over water and product was extracted with ethyl acetate. Organic layer was combined, washed with brine solution, dried over sodium sulphate and concentrated under reduced pressure to obtain 78.4. (0.539 g, 49.27%). MS (ES): m/z 467.22 [M+H]$^+$ Synthesis of Compound 78.5.

To a solution of 78.4 (0.539 g, 1.15 mmol, 1.0 eq), in tetrahydrofuran:methanol (12 mL, 2:1) was added lithium hydroxide (0.276 g, 11.5 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 78.5. (0.4 g, 78.96%). MS(ES): m/z 439.18 [M+H]$^+$.

Synthesis of Compound 78.7.

Compound was synthesized using general procedure A to obtain 78.7. (0.065 g, 59.68%), MS (ES): 478.23 [M+H]$^+$ Synthesis of Compound I-960.

Mixture of 78.2 (0.065 g, 0.13 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to obtain I-960 (0.040 g, 75.85%), MS (ES): m/z 388.34 [M+H]$^+$, LCMS purity: 100%, HPLC purity: 99.01%, $^1$H NMR (DMSO-d$_6$, 400 MHZ): 8.65-8.63 (d, J=8 Hz, 1H), 8.61 (s, 1H), 8.44-8.43 (d, J=3.6 Hz, 1H), 8.37 (s, 1H), 8.32-8.31 (d, J=3.2 Hz, 1H), 8.25-8.23 (d, J=4.8 Hz, 1H), 7.35-7.32 (m, 1H), 6.84-6.82 (d, J=6.8 Hz, 1H), 6.78 (s, 1H), 3.81-3.78 (t, J=5.6 Hz, 1H), 3.11-3.09 (d, J=4.8 Hz, 3H), 2.94-2.93 (m, 1H), 1.56 (bs, 1H), 1.24 (bs, 2H), 0.88-0.86 (d, J=5.6 Hz, 2H), 0.62 (bs, 2H).

Example 79: N-(2-hydroxycyclobutyl)-7-(methylamino)-5-(1-(tetrahydro-2H-pyran-4-yl)-1H-pyrrolo[2,3-b]pyridin-3-yl)pyrazolo[1,5-a]pyrimidine-3-carboxamide (I-1048)

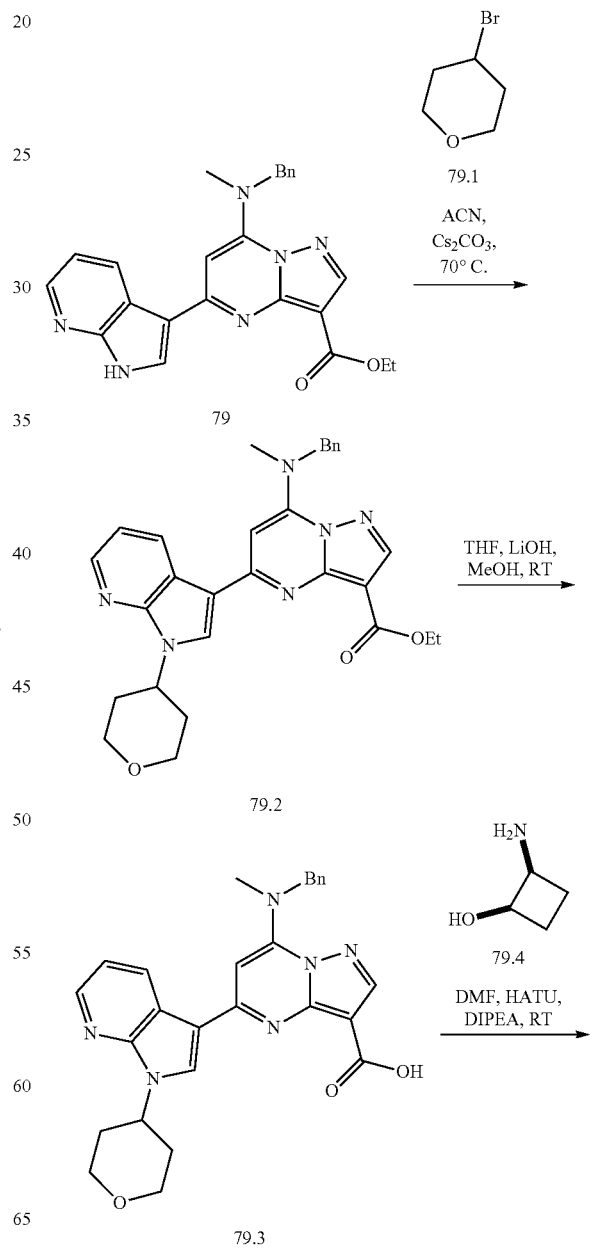

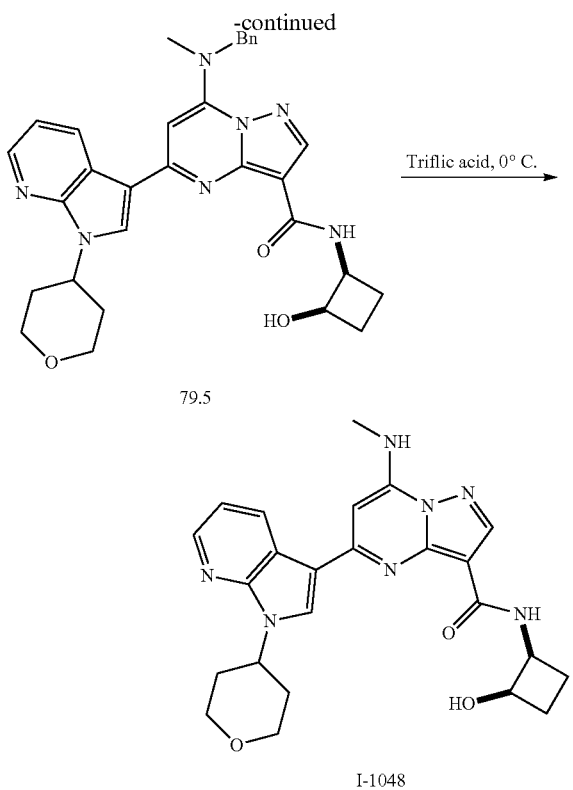

Synthesis of Compound I-1048:

Solution of 79.5 (0.035 g, 0.063 mmol, 1.0 eq) in dichloromethane (0.5 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1048 (0.025 g, 85.38%), MS (ES): m/z 462.36 [M+H]$^+$, LCMS purity: 98.10%, HPLC purity: 96.75%, CHIRAL HPLC: 52.72%, 47.27%, $^1$H NMR (DMSO-d$_6$, 400 MHZ): 8.99-8.97 (d, J=6.8 Hz, 1H), 8.72 (s, 1H), 8.56-8.54 (d, J=8 Hz, 1H), 8.38-8.37 (d, J=1.6 Hz, 1H), 8.32 (s, 1H), 8.85-8.84 (d, J=4.8 Hz, 1H), 7.31-7.28 (m, 1H), 6.72 (s, 1H), 5.15-5.14 (d, J=4.4 Hz, 1H), 5.09-5.05 (m, 1H), 4.63-4.60 (t, J=6.8 Hz, 1H), 4.46 (bs, 1H), 4.11-4.07 (m, 2H), 3.66-3.61 (t, J=10.4 Hz, 2H), 3.17-3.16 (t, J=4.8 Hz, 3H), 2.33-2.25 (m, 4H), 2.09 (bs, 3H), 1.94-1.88 (m, 1H).

Example 80: 5-((2-cyclopropoxypyridin-3-yl)amino)-N-((1R,2R)-2-hydroxycyclobutyl)-7-(methylamino)pyrazolo[1,5-a]pyrimidine-3-carboxamide (I-366)

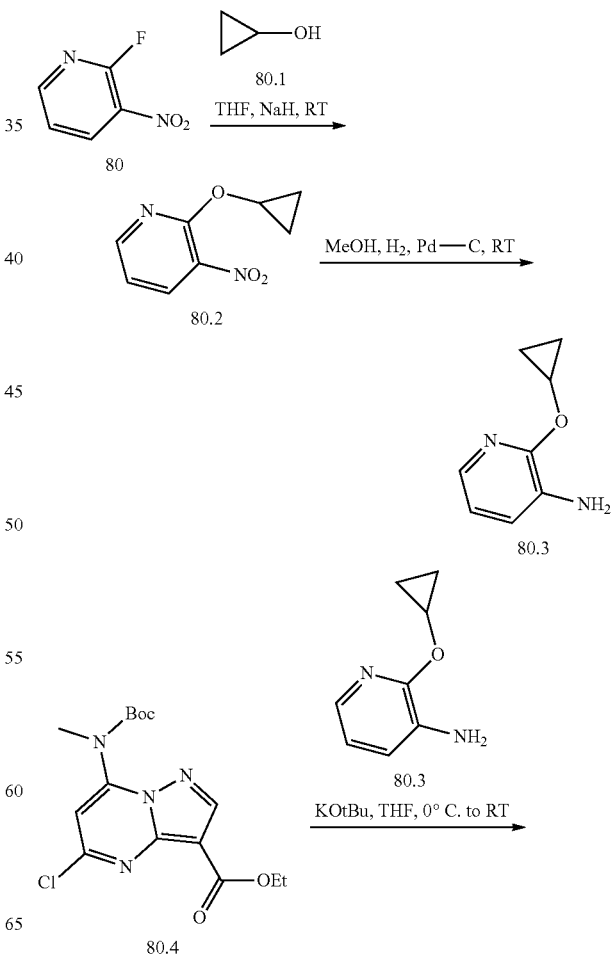

Synthesis of Compound 79.

Compound was synthesized as per experimental protocol of Example 78 to obtain 79. (Yield: 83.64%), MS (ES): m/z 427.18 [M+H]$^+$ Synthesis of Compound 79.2.

To a cooled solution of 79 (0.5 g, 1.17 mmol, 1.0 eq), and 79.1 (0.386 g, 2.34 mmol, 1.2 eq) in Acetonitrile (15 mL) at 0° C. was added Cesium carbonate (0.9 g, 2.92 mmol, 2.5 eq). The reaction was stirred at 70° C. for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 79.2. (0.150 g, 25.06%). MS (ES): m/z 511.24 [M+H]$^+$.

Synthesis of Compound 79.3.

To a solution of 79.2 (0.150 g, 0.29 mmol, 1.0 eq), in methanol:tetrahydrofuran (4 mL, 2:1) was added lithium hydroxide (0.069 g, 2.9 mmol, 10 eq). The reaction was stirred at 60° C. for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 79.3. (0.140 g, 98.76%). MS(ES): m/z 483.21 [M+H]$^+$ Synthesis of Compound 79.5.

Compound was synthesized using general procedure A to obtain 79.5. (0.135 g, 84.35%), MS (ES): 552.27 [M+H]$^+$

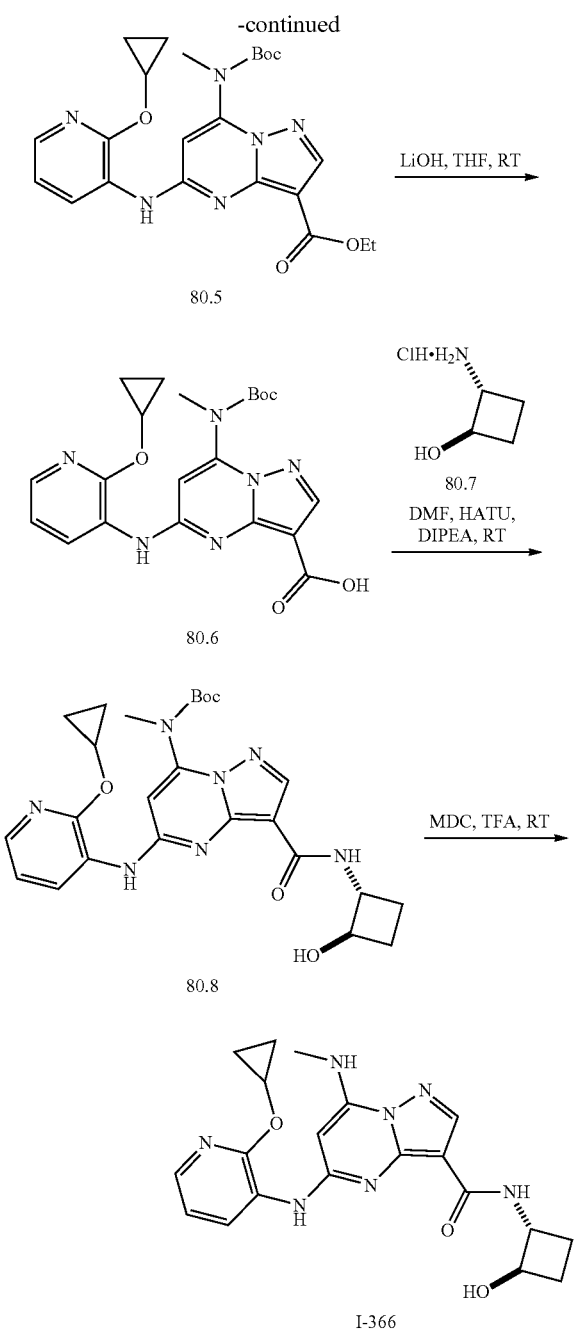

Synthesis of Compound 80.2.

To a cooled solution of 80 (1 g, 7.04 mmol, 1.0 eq) in tetrahydrofuran (10 mL) was added sodium hydride (0.323 g, 14.08 mmol, 2.0 eq) followed by addition of cyclo propanol (0.530 g, 9.15 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 3-4% ethyl acetate in hexane to obtain pure 80.2 (0.900 g, 70.98%), MS(ES): m/z 181.16 [M+H]$^+$.

Synthesis of Compound 80.3.

To a solution of 80.2 (0.900 g, 5.00 mmol, 1.0 eq) in methanol (10 mL), palladium on charcoal (0.4 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 80.3 (0.600 g, 79.98%). MS (ES): m/z 151.18 [M+H]$^+$.

Synthesis of Compound 80.4

Compound was synthesized using general procedure of core synthesis to obtain 80.4. (Yield: 62.21%). MS (ES): m/z 355.5 [M+H]$^+$.

Synthesis of Compound 80.5.

To a cooled solution of 80.4 (0.600 g, 1.69 mmol, 1.0 eq), and 80.3 (0.253 g, 1.69 mmol, 1.0 eq) in tetrahydrofuran (10 mL) at 0° C. was added potassium ter-butoxide (3.4 mL, 3.38 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 80.5 (0.480 g, 60.58%). MS (ES): m/z 469.51 [M+H]$^+$.

Synthesis of Compound 80.6.

To a solution of 80.5 (0.480 g, 1.02 mmol, 1.0 eq), in tetrahydrofuran (10 mL) was added lithium hydroxide (0.428 g, 10.2 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 80.6 (0.300 g, 66.48%). MS(ES): m/z 441.46 [M+H]$^+$.

Synthesis of Compound 80.8.

Compound was synthesized using general procedure A to obtain 80.8. (0.127 g, 73.18%). MS (ES): m/z 510.17 [M+H]$^+$ Synthesis of Compound I-366.

Compound was synthesized using general procedure C to obtain I-366 (0.095 g, 87.43%). MS (ES): m/z 410.45 [M+H]$^+$, LCMS purity: 100%, HPLC purity: 99.41%, Chiral HPLC purity: 49.33%+49.52%, $^1$H NMR (DMSO-d$_6$, 400 MHZ): 8.76 (s, 1H), 8.29-8.27 (d, J=6.4 Hz, 1H), 8.19 (s, 1H), 8.01-7.92 (m, 3H), 7.07-7.04 (m, 1H), 5.87 (s, 1H), 5.34-5.32 (d, J=7.2 Hz, 1H), 4.37-4.34 (m, 1H), 4.21-4.41 (m, 1H), 3.72-3.57 (m, 1H), 2.92-2.91 (d, J=4.8 Hz, 2H), 2.01-1.90 (m, 2H), 1.56-1.34 (m, 1H), 1.33 (s, 1H), 1.10-1.05 (m, 1H), 1.03-0.74 (m, 4H).

Example 81: 5-((2-cyclopropoxypyridin-3-yl)amino)-N-(2-hydroxycyclobutyl)-7-(methylamino)pyrazolo[1,5-a]pyrimidine-3-carboxamide (I-392)

Example 82: N-(2-hydroxycyclobutyl)-5-((2-methoxypyridin-3-yl)amino)-7-(methylamino)pyrazolo[1,5-a]pyrimidine-3-carboxamide (I-390)

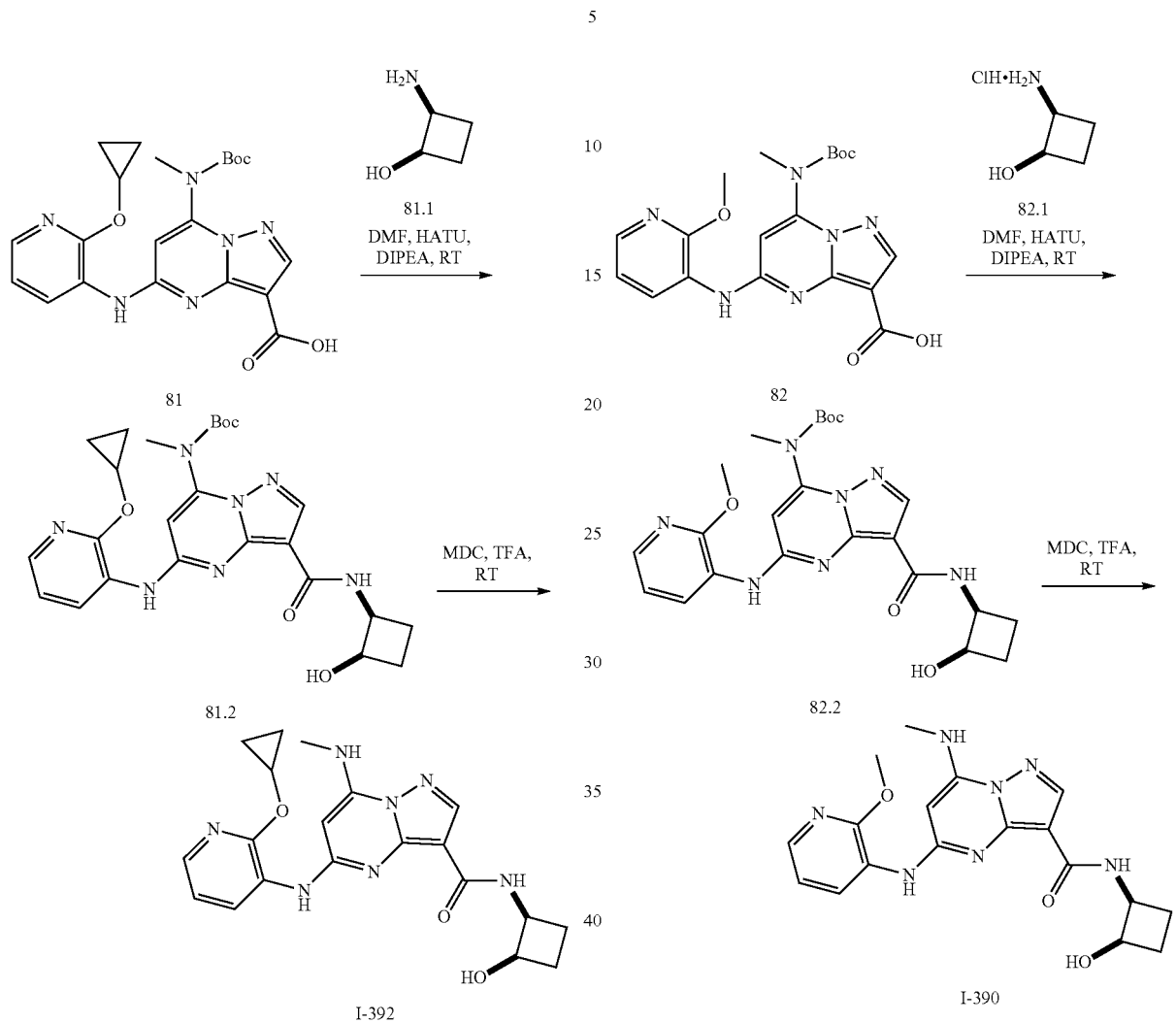

Synthesis of Compound 81.

Compound was synthesized as per experimental protocol of Example 80 to obtain 81. (Yield: 66.48%), MS (ES): m/z 441.46 [M+H]+

Synthesis of Compound 81.2.

Compound was synthesized using general procedure A to obtain 81.2. (0.120 g, 69.15%), MS (ES): 510.24 [M+H]+

Synthesis of Compound I-392:

Compound was synthesized using general procedure C to obtain I-392 (0.090 g, 93.34%), MS (ES): m/z 410.22 [M+H]+, LCMS purity: 100%, HPLC purity: 99.85%, CHIRAL HPLC: 59.62%, 50.37%, 1H NMR (DMSO-d6, 400 MHZ): 8.68-8.66 (d, J=8 Hz, 1H), 8.57 (bs, 1H), 8.18 (s, 1H), 8.02-8.00 (d, J=8.8 Hz, 1H), 7.91 (bs, 1H), 7.87-7.86 (d, J=4.4 Hz, 1H), 7.12-7.08 (m, 1H), 6.03 (s, 1H), 5.87 (s, 1H), 4.55-4.51 (m, 1H), 4.36 (bs, 1H), 4.31 (bs, 1H), 2.93 (s, 3H), 2.14 (bs, 1H), 2.08-2.03 (m, 1H), 2.02-1.93 (m, 1H), 1.72 (bs, 1H), 0.81 (bs, 4H).

Synthesis of Compound 82.

Compound was synthesized as per experimental protocol of Example 32 to obtain 82. (Yield: 71.18%). MS(ES): m/z 415.42 [M+H]+.

Synthesis of Compound 82.2.

Compound was synthesized using general procedure A to obtain 82.2. (0.150 g, 64.28%), MS (ES): 554.27 [M+H]+

Synthesis of Compound I-390:

Compound was synthesized using general procedure C to obtain I-390 (0.110 g, 92.48%), MS (ES): m/z 384.40 [M+H]+, LCMS purity: 100%, HPLC purity: 99.00%, CHIRAL HPLC: 48.85%, 50.78%, 1H NMR (DMSO-d6, 400 MHZ): 8.81 (s, 1H), 8.67-8.65 (d, J=8 Hz, 1H), 8.17 (s, 1H), 8.03-8.01 (d, J=9.2 Hz, 1H), 7.90-7.89 (d, J=4.8 Hz, 1H), 7.84-7.82 (m, 1H), 7.09-7.05 (m, 1H), 6.06 (s, 1H), 5.26-5.26 (d, J=3.6 Hz, 1H), 4.54-4.49 (m, 1H), 4.36 (bs, 1H), 3.98 (s, 3H), 2.92-2.91 (d, J=4.8 Hz, 3H), 1.95-1.86 (m, 1H), 1.68 (bs, 1H), 1.04-1.03 (d, J=6.4 Hz, 2H).

Example 83: N-(3,3-difluorocyclobutyl)-5-((2-methoxypyridin-3-yl)amino)-7-(methylamino)pyrazolo[1,5-a]pyrimidine-3-carboxamide (I-338)

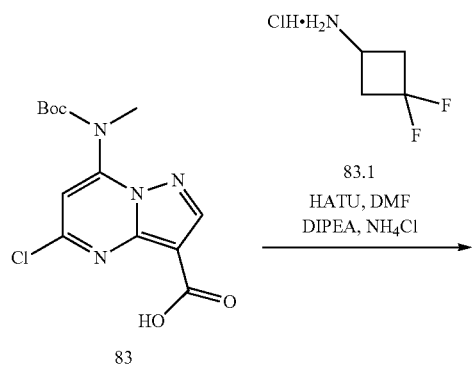

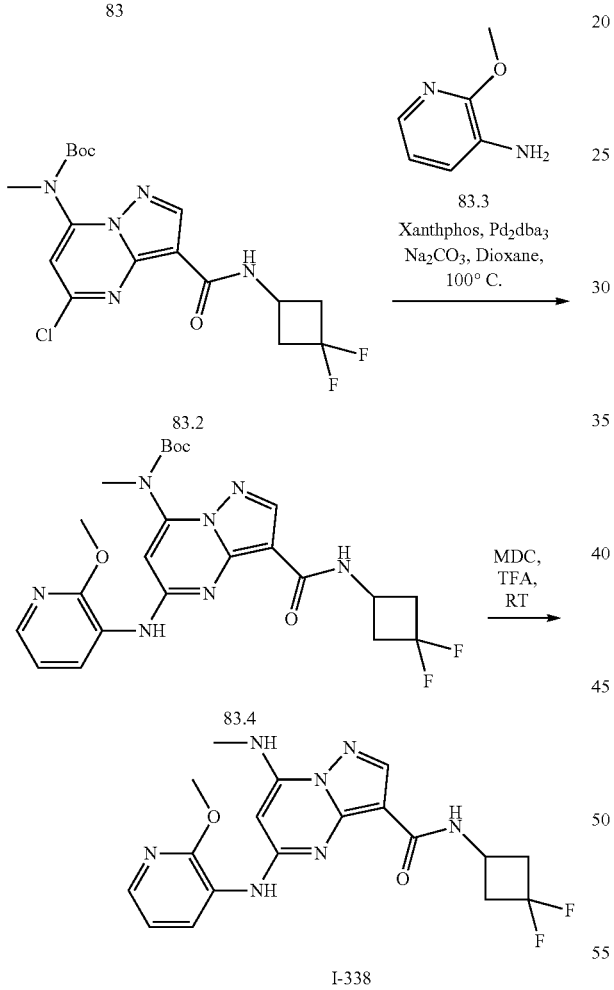

I-338

Synthesis of Compound 83.

Compound was synthesized using general procedure of core synthesis to obtain 83. (Yield: 71.67%). MS (ES): m/z 327.08 [M+H]$^+$

Synthesis of Compound 83.2.

Compound was synthesized using general procedure A to obtain 83.2 (0.300 g, 47.15%), MS (ES): m/z 416.83 [M+H]$^+$

Synthesis of Compound 83.4.

Compound was synthesized using general procedure B to obtain 83.4 (0.050 g, 41.29%), MS (ES): m/z 504.51 [M+H]$^+$

Synthesis of Compound I-338:

Compound was synthesized using general procedure C to obtain I-338 (0.025 g, 62.41%), MS (ES): m/z 404.17 [M+H]$^+$, LCMS purity: 99.60%, HPLC purity: 99.57%, $^1$H NMR (DMSO-d$_6$, 400 MHZ): 8.96 (s, 1H), 8.31-8.30 (d, J=4 Hz, 1H), 8.16 (s, 1H), 8.01-8.00 (d, J=4 Hz, 1H), 7.93 (m, 2H), 7.02-7.00 (t, J=8 Hz, 1H), 5.96 (s, 1H), 4.25 (bs, 1H), 3.95 (s, 3H), 2.97-2.90 (m, 4H), 2.46 (m, 3H).

Example 84: 5-((2-cyclopropoxypyridin-3-yl)amino)-N-(3,3-difluorocyclobutyl)-7-(methylamino)pyrazolo[1,5-a]pyrimidine-3-carboxamide (I-339)

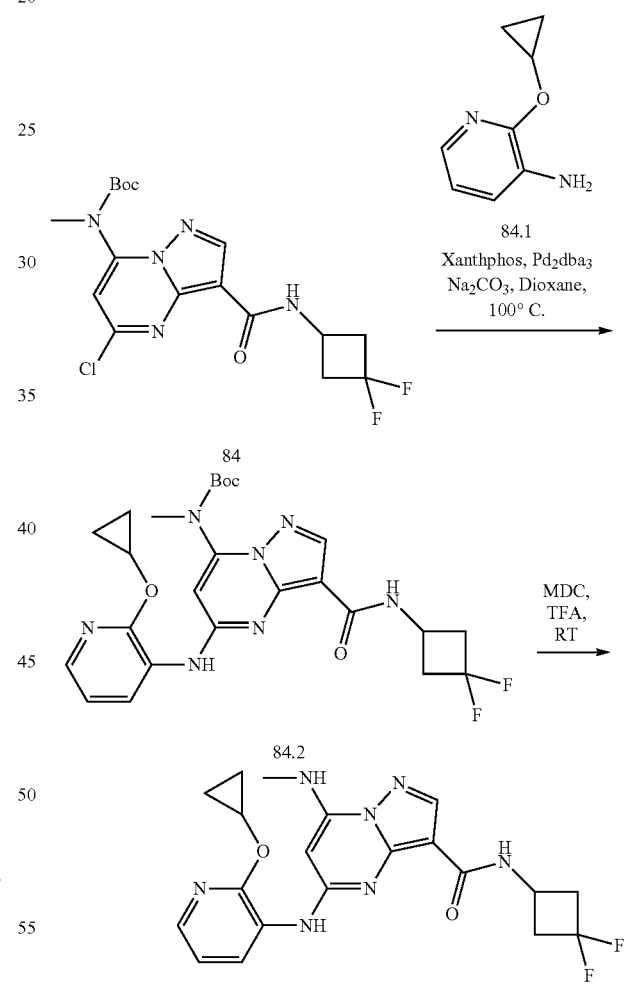

I-339

Synthesis of Compound 84.

Compound was synthesized as per experimental protocol of Example 83.

Synthesis of Compound 84.1.

Compound was synthesized as per experimental protocol of Example 55.

Synthesis of Compound 84.2.

Compound was synthesized using general procedure B to obtain 84.2 (0.052 g, 40.83%), MS (ES): m/z 530.55 [M+H]$^+$ Synthesis of Compound I-339:

Compound was synthesized using general procedure C to obtain I-339 (0.025 g, 59.29%), MS (ES): m/z 430.21 [M+H]$^+$, LCMS purity: 97.66%, HPLC purity: 97.54%, $^1$H NMR (DMSO-d$_6$, 400 MHZ): 8.77 (s, 1H), 8.30-8.28 (d, J=8 Hz, 1H), 8.16 (s, 1H), 7.99-7.98 (d, J=4 Hz, 2H), 7.95-7.94 (t, J=4 Hz, 1H), 7.04-7.03 (t, J=4 Hz, 1H), 5.85 (s, 1H), 4.359-4.351 (m, 1H), 4.24 (m, 1H), 2.98-2.90 (m, 4H), 2.46 (m, 3H), 0.78-0.73 (m, 4H).

Example 85: N-(2-(1-hydroxycyclopropyl)ethyl)-5-((2-methoxypyridin-3-yl)amino)-7-(methylamino)pyrazolo[1,5-a]pyrimidine-3-carboxamide (I-468)

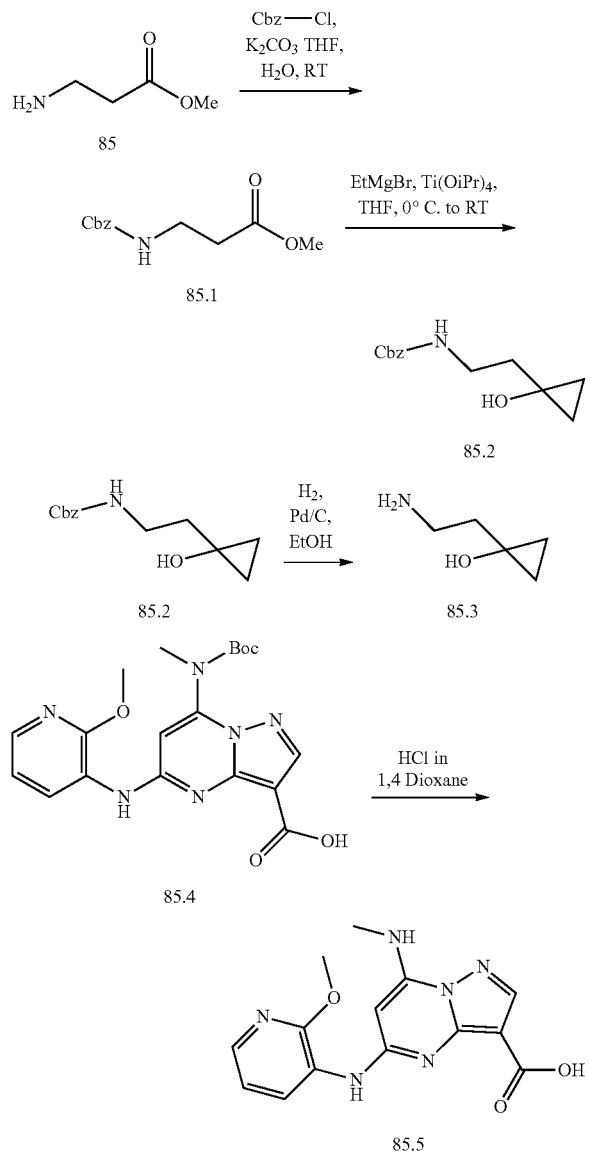

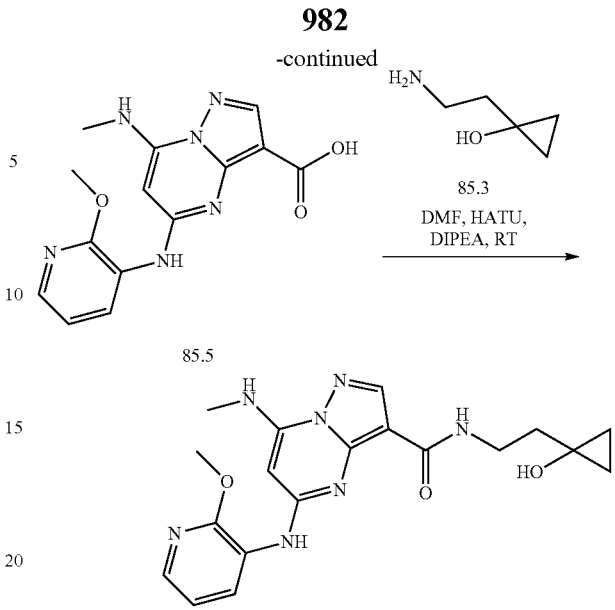

I-468

Synthesis of Compound 85.1.

To a solution of 85 (2 g, 1.43 mmol, 1.0 eq) in tetrahydrofuran (25 mL) and water (15 mL) was added potassium carbonate (5.93 g, 4.29 mmol, 3.0 eq). The reaction mixture was stirred for 30 min and added benzyl chloroformate (2.93 g, 1.72 mmol, 1.2 eq) at 0° C. The reaction mixture was stirred at room temperature for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 30% ethyl acetate in hexane to obtain 85.1 (2.5 g, Yield: 54.33%). MS (ES): m/z 238.26 [M+H]$^+$.

Synthesis of Compound 85.2.

To a cooled solution of 85.1 (1 g, 4.22 mmol, 1.0 eq) and titanium (IV) isopropoxide (0.36 g, 1.26 mmol, 0.3 eq) in tetrahydrofuran (25 mL) was added dropwise ethyl magnesium bromide (1M) in tetrahydrofuran (12.63 mL, 12.63 mmol, 3.0 eq) over 45 min. The reaction mixture was stirred at room temperature for 8 h. The reaction mixture was transferred in 1N hydrochloric acid. The product was extracted with ethyl acetate. Organic layer was combined, washed with saturated sodium bicarbonate and brine solution, dried over sodium sulphate and concentrated under reduced pressure to obtain crude material. This was further purified by 20% ethyl acetate in hexane to obtain 85.2 (0.4 g, Yield: 40.34%). MS (ES): m/z 236.28 [M+H]$^+$ Synthesis of Compound 85.3.

To a solution of 85.2 (1 g, 4.25 mmol, 1.0 eq) in ethanol (10 mL), palladium on charcoal (0.33 g) was added. Hydrogen was purged through reaction mixture for 4 h at room temperature. After completion of reaction, reaction mixture was filtered through celite-bed and washed with ethanol. Filtrate was concentrated under reduced pressure to obtain 85.3 (0.3 g, 69.78%). MS(ES): m/z 102.15 [M+H]$^+$.

Synthesis of Compound 85.4.

Compound was synthesized as per experimental protocol of Example 32 to obtain 85.4 (Yield: 71.18%), MS (ES): m/z 415.42 [M+H]$^+$ Synthesis of Compound 85.5.

To 85.4 (0.150 g, 0.36 mmol, 1.0 eq) was added 4M hydrochloric acid in 1,4 Dioxane (3 mL) and stirred at room temperature for 4 h. After completion of reaction, reaction mixture was concentrated under reduced pressure, residue was triturated with diethyl ether to obtain 85.5 (0.110 g, 100%). MS (ES): m/z 315.38 [M+H]$^+$ Synthesis of Compound I-468.

Compound was synthesized using general procedure A to obtain I-468. (Yield: 0.04 g, 33.03%). MS (ES): m/z 398.22 [M+H]$^+$, LCMS purity: 95.00%, HPLC purity: 95.25%, $^1$H NMR (DMSO-d$_6$, 400 MHZ): 8.92 (s, 1H), 8.31-8.29 (d, J=7.2 Hz, 1H), 8.16 (s, 1H), 7.93-7.84 (m, 2H), 7.84-7.81 (t, J=5.6 Hz, 1H), 7.03-6.99 (m, 1H), 5.92 (s, 1H), 5.22 (s, 1H), 3.96 (s, 3H), 3.47-3.42 (m, 2H), 2.92-2.91 (d, J=4.4 Hz, 3H), 1.63-1.56 (m, 2H), 0.54-0.53 (d, J=5.6 Hz, 2H), 0.34-0.31 (m, 2H).

Example 86: 5-((2-cyclopropoxypyridin-3-yl)amino)-N-(2-(1-hydroxycyclopropyl)ethyl)-7-(methylamino)pyrazolo[1,5-a]pyrimidine-3-carboxamide (I-469)

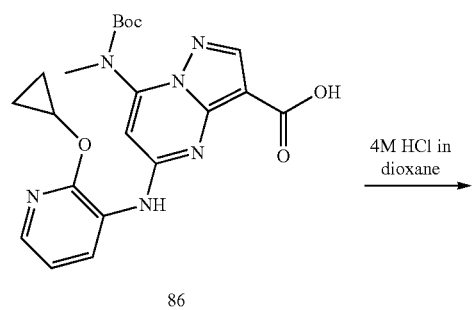

86

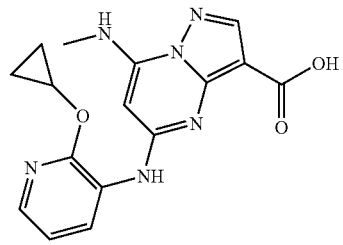

86.1

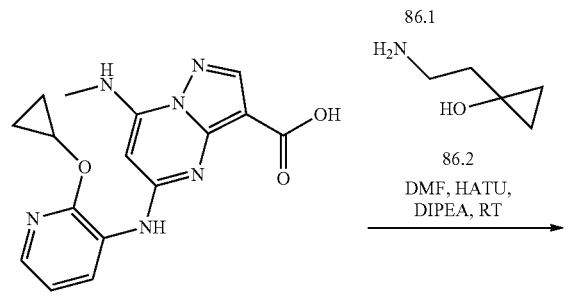

86.1

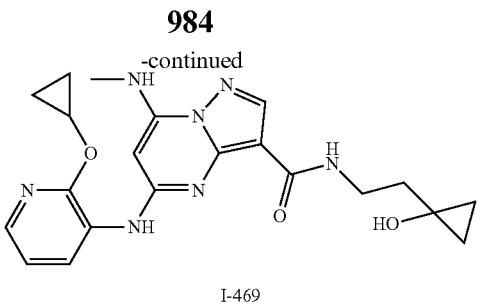

I-469

Synthesis of Compound 86.

Compound was synthesized as per experimental protocol of Example 56 to obtain 86.

Synthesis of Compound 86.1.

To 86 (0.2 g, 0.45 mmol, 1.0 eq) was added 4M hydrochloric acid in 1,4 Dioxane (3 mL) and stirred at room temperature for 4 h. After completion of reaction, reaction mixture was concentrated under reduced pressure, residue was triturated with diethyl ether to obtain 86.1 (0.120 g, 77.65%). MS (ES): m/z 341.34 [M+H]$^+$.

Synthesis of Compound 86.2

Compound was synthesized as per experimental protocol of Example 85 to obtain 86.2.

Synthesis of Compound I-469.

Compound was synthesized using general procedure A to obtain I-469. (Yield: 0.04 g, 33.03%). MS (ES): m/z 424.27 [M+H]$^+$, LCMS purity: 95.51%, HPLC purity: 95.00%, $^1$H NMR (DMSO-d$_6$, 400 MHZ): 8.70 (s, 1H), 8.31-8.29 (d, J=7.2 Hz, 1H), 8.16 (s, 1H), 7.92-7.91 (d, J=4.4 Hz, 2H), 7.80 (s, 1H), 7.05-7.02 (t, J=5.2 Hz, 1H), 5.88 (s, 1H), 5.21 (s, 1H), 4.34 (s, 1H), 3.45-3.43 (d, J=6.8 Hz, 2H), 2.92-2.91 (d, J=4.4 Hz, 3H), 1.62-1.52 (m, 2H), 0.86-0.76 (m, 4H), 0.53 (s, 2H), 0.342 (s, 2H).

Example 87: N-(2-(1-hydroxycyclopropyl)ethyl)-5-((2-(methoxy-d3)pyridin-3-yl)amino)-7-(methylamino)pyrazolo[1,5-a]pyrimidine-3-carboxamide (I-470)

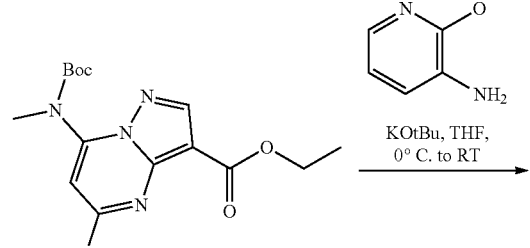

87

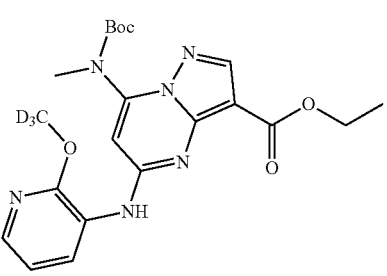

87.1

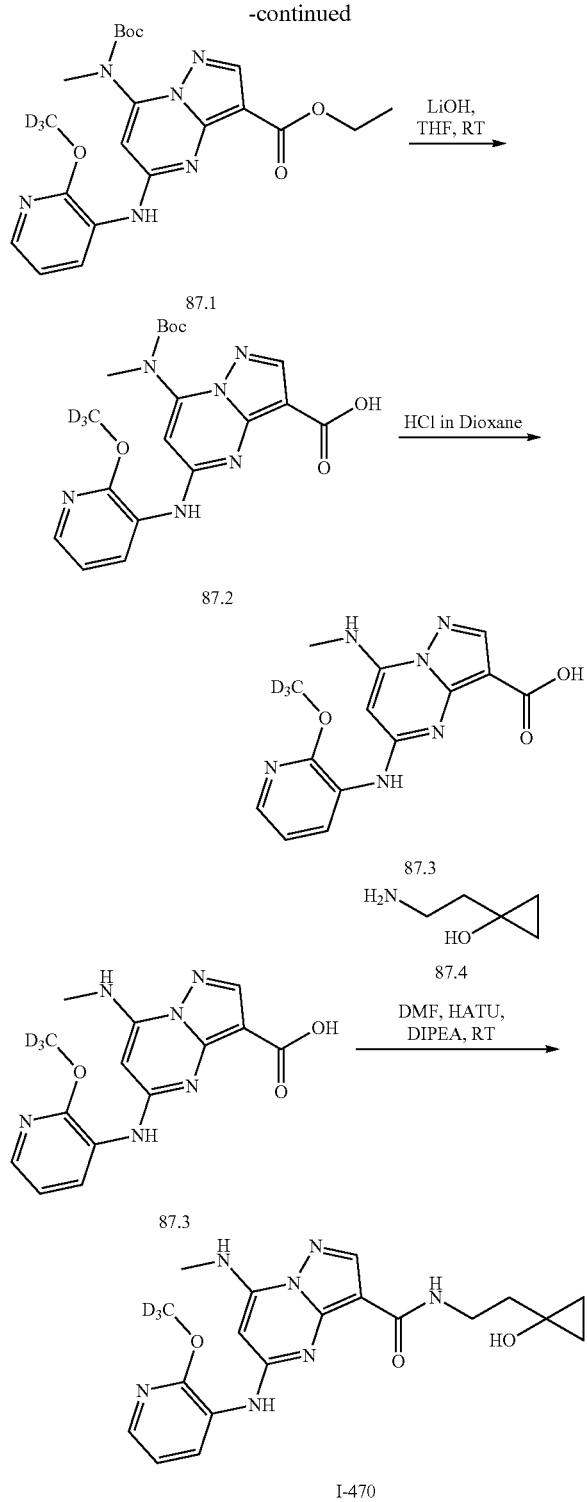

stirred at room temperature for 1 h. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 87.1 (0.9 g, 71.68%). MS (ES): m/z 446.49 [M+H]$^+$.

Synthesis of Compound 87.2.

To a solution of 87.1 (0.9 g, 2.02 mmol, 1.0 eq), in tetrahydrofuran: water (8 mL, 2:1) was added lithium hydroxide (0.848 g, 20.2 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with n-pentane to obtain pure 87.2 (0.6 g, 71.15%). MS(ES): m/z 418.44 [M+H]$^+$.

Synthesis of Compound 87.3.

Compound was synthesized as per general procedure C to obtain 87.3. (0.4 g, 87.70%). MS(ES): m/z 318.44 [M+H]$^+$.

Synthesis of Compound 87.4.

Compound was synthesized as per experimental protocol of Example 85 to obtain 87.4.

Synthesis of Compound I-470.

Compound was synthesized using general procedure A to obtain I-470. (Yield: 0.04 g, 33.03%). MS (ES): m/z 401.22 [M+H]$^+$, LCMS purity: 97.37%, HPLC purity: 96.38%, $^1$H NMR (DMSO-d$_6$, 400 MHZ): 8.91 (s, 1H), 8.32-8.30 (d, J=7.2 Hz, 1H), 8.16 (s, 1H), 7.91-7.89 (d, J=8.8 Hz, 2H), 7.83 (s, 1H), 7.02 (s, 1H), 5.93 (s, 1H), 5.21 (s, 1H), 4.44 (s, 1H), 3.36 (s, 1H), 2.92 (s, 3H), 1.61 (s, 2H), 0.53 (bs, 2H), 0.33 (bs, 2H).

Example 88: 5-((2-methoxypyridin-3-yl)amino)-7-(methylamino)-N-(2-(tetrahydrofuran-2-yl)ethyl) pyrazolo[1,5-a]pyrimidine-3-carboxamide (I-418)

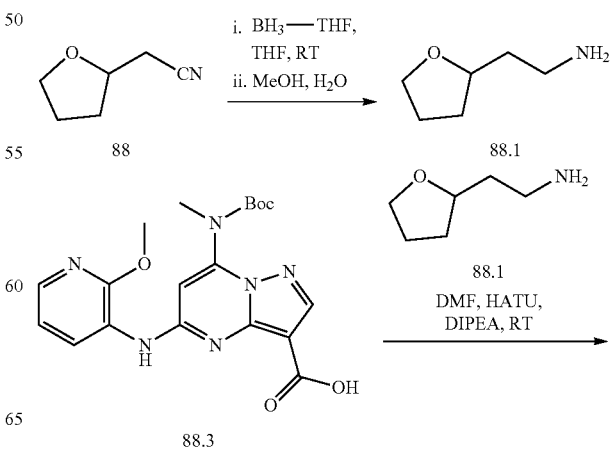

Synthesis of Compound 87.

Compound was synthesized using general procedure of core synthesis to obtain 87. (Yield: 62.21%). MS (ES): m/z 355.5 [M+H]$^+$ Synthesis of Compound 87.1.

To a cooled solution of 87 (1.0 g, 2.82 mmol, 1.0 eq), and 2-(methoxy-d3)pyridin-3-amine (0.36 g, 2.82 mmol, 1.0 eq) in tetrahydrofuran (30 mL) at 0° C. was added potassium tert-butoxide (5.6 mL, 5.64 mmol, 2.0 eq). The reaction was

987

-continued

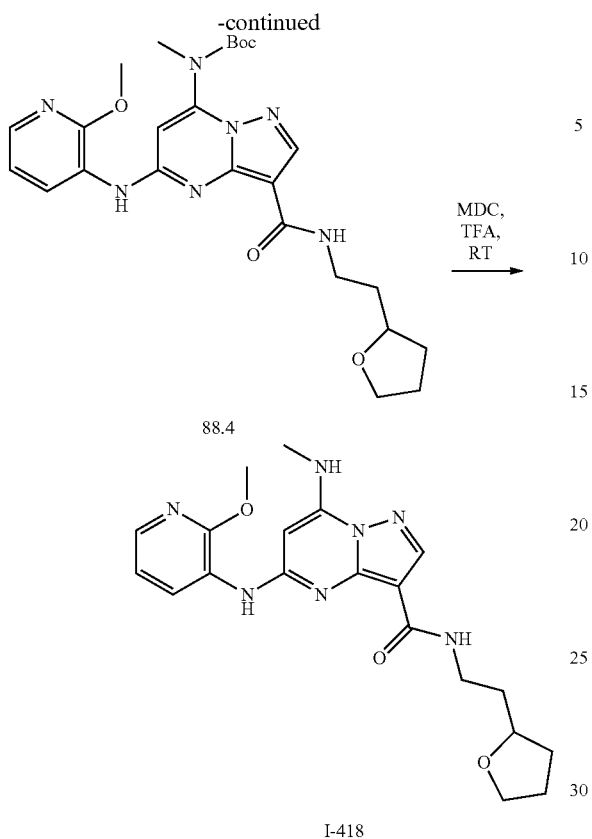

88.4

I-418

Synthesis of Compound 88.1.

To a cooled solution of 88 (1 g, 9.09 mmol, 1.0 eq), in tetrahydrofuran (20 mL) was added Borane-tetrahydrofuran (63 mL, 63.06 mmol, 7.0 eq). The reaction mixture was stirred at room temperature for 16 h. After completion of reaction, methanol was slowly added at 0° C. and reaction mixture stirred at room temperature for 15 min. Reaction mixture was concentrated under reduced pressure to obtain crude. This was further purified by column chromatography and the compound was eluted in 10% methanol in dichloromethane to obtain 88.1 (0.350 g, 33.77%). 1H NMR (DMSO-$d_6$, 400 MHz): 3.80-3.70 (m, 2H), 3.59-3.54 (m, 1H), 3.02 (bs, 2H), 2.68-2.56 (m, 2H), 1.97-1.78 (m, 6H).

Synthesis of Compound 88.3.

Compound was synthesized as per experimental protocol of Example 32 to obtain 88.3 (Yield: 71.18%), MS (ES): m/z 415.42 [M+H]$^+$ Synthesis of Compound 88.4.

Compound was synthesized using general procedure A to obtain 88.4 (0.150 g, 60.76%), MS (ES): m/z 512.25 [M+H]$^+$ Synthesis of Compound I-418:

Compound was synthesized using general procedure C to obtain I-418 (0.100 g, 82.89%), MS (ES): m/z 412.25 [M+H]$^+$, LCMS purity: 98.88%, HPLC purity: 99.50%, Chiral HPLC purity: 48.73% and 51.27%, $^1$H NMR (DMSO-$d_6$, 400 MHZ): 8.91 (s, 1H), 8.31-8.21 (d, J=8 Hz 1H), 8.15 (s, 1H), 7.92-7.89 (t, J=4 Hz, 2H), 7.82-7.80 (t, J=8 Hz, 1H), 7.03-7.00 (m, 1H), 5.92 (s, 1H), 3.96 (s, 3H), 3.76-3.17 (m, 5H), 2.92 (s, 3H), 1.93-1.24 (m, 6H).

988

Example 89: 5-((2-(methoxy-d3)pyridin-3-yl) amino)-7-(methylamino)-N-(2-(tetrahydrofuran-2-yl) ethyl)pyrazolo[1,5-a]pyrimidine-3-carboxamide (I-419)

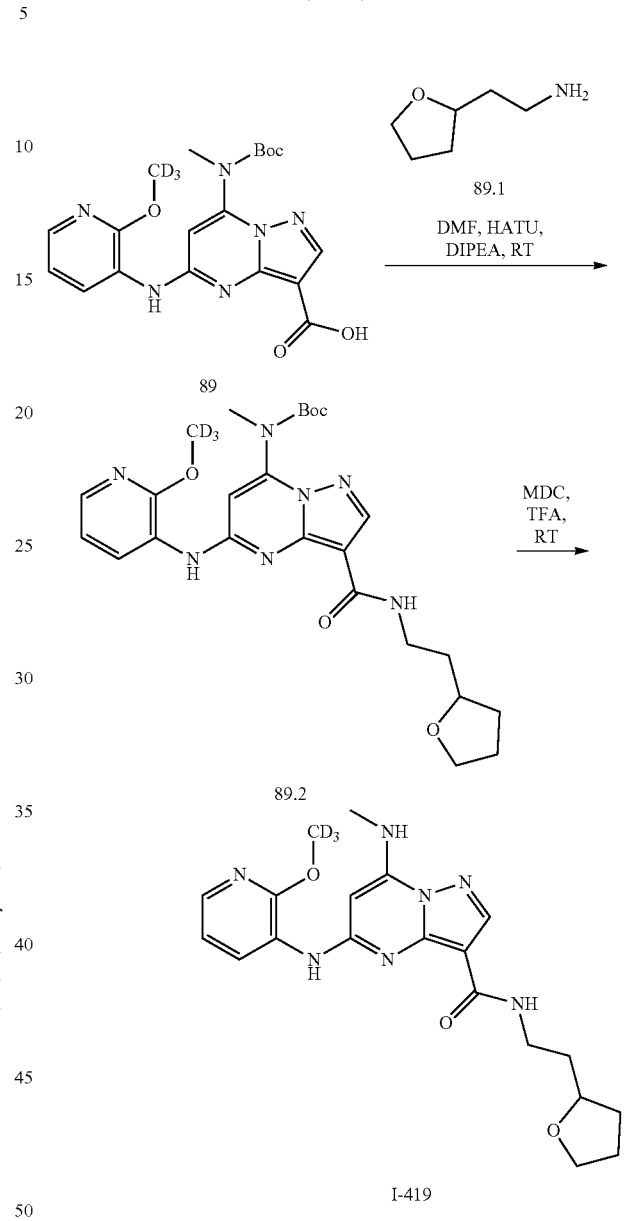

Synthesis of Compound 89.

Compound was synthesized as per experimental protocol of Example 87 to obtain 89. (Yield: 71.15%), MS(ES): m/z 418.44 [M+H]$^+$.

Synthesis of Compound 89.1.

Compound was synthesized as per experimental protocol of Example 88 to obtain 89.1 (Yield: 33.77%).

Synthesis of Compound 89.2.

Compound was synthesized using general procedure A to obtain 89.2 (0.150 g, 60.84%), MS (ES): m/z 515.27 [M+H]$^+$ Synthesis of Compound I-419:

Compound was synthesized using general procedure C to obtain I-419 (0.100 g, 82.77%), MS (ES): m/z 415.60 [M+H]$^+$, LCMS purity: 99.27%, HPLC purity: 99.58%, Chiral HPLC purity: 48.72% and 51.28%, $^1$H NMR (DMSO-d$_6$, 400 MHZ): 8.91 (s, 1H), 8.31-8.29 (d, J=8 Hz 1H), 8.15 (s, 1H), 7.92-7.89 (t, J=4 Hz, 2H), 7.82-7.79 (t, J=8 Hz, 1H), 7.02-7.00 (m, 1H), 5.92 (s, 1H), 3.76-3.17 (m, 5H), 2.92 (s, 3H), 1.93-1.24 (m, 6H).

Example 90: Synthesis of Compounds where R$^3$ is Carboxamide, R$^6$ is Hydrogen, and R$^7$ is Amine Synthesis of 7-amino-5-((5-chloro-2-((tetrahydro-furan-3-yl)oxy)pyridin-3-yl)amino)pyrazolo[1,5-a]pyrimidine-3-carboxamide (I-82)

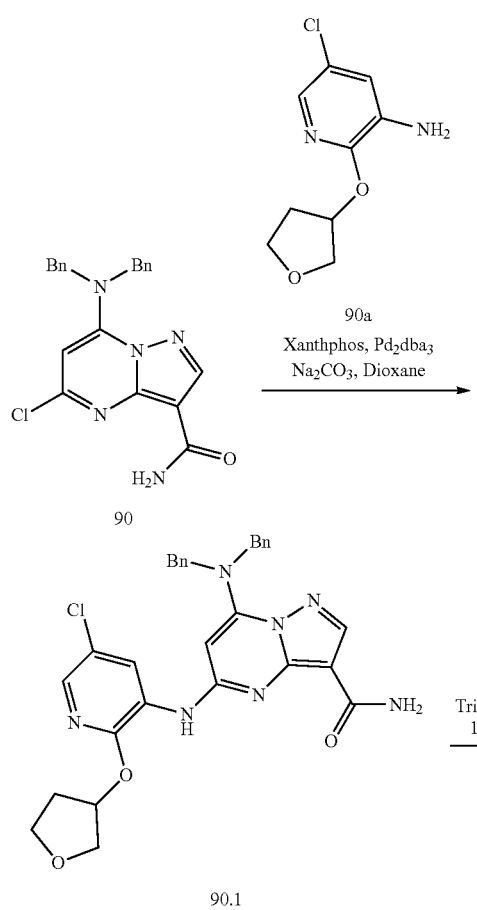

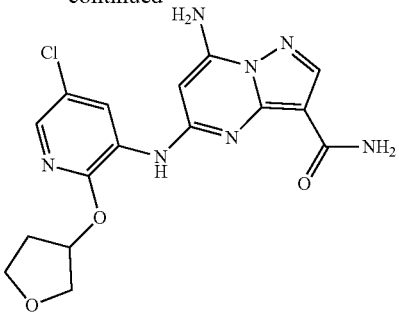

I-82

Synthesis of Compound 90.

Compound was synthesized using general procedure of core synthesis to obtain 90. (Yield: 38.00%). MS (ES): m/z 391.86 [M+H]$^+$.

Synthesis of 90a.

Compound was synthesized as per Example 103 (I-84) to obtain 90a.

Synthesis of 90.1.

Compound was synthesized using general procedure B to obtain 90.2. (Yield: 33.00%). MS (ES): m/z 571.05 [M+H]$^+$ Synthesis of I-82.

Mixture of 90.1 (0.12 g, 0.21 mmol, 1.0 eq) and triflic acid (1 mL) was allowed to stir at 60° C. for 10 min. After completion of reaction, reaction mixture was transferred into saturated sodium bicarbonate solution and product was extracted with dichloromethane. Organic layer was combined, washed with brine solution, dried over sodium sulphate and concentrated under reduced pressure to obtain crude material. This was further purified by trituration with diethyl ether to a obtain I-82. (0.03 g, 36.56%). MS(ES): m/z 390.43 [M+H]$^+$, LCMS purity: 100%, HPLC purity: 98.40%, Chiral HPLC: 49.31%, 49.31%, $^1$H NMR (DMSO-d$_6$, 400 MHZ): 8.85 (s, 1H), 8.42-8.41 (d, J=2.4 Hz, 1H), 8.18 (s, 1H), 7.86 (d, J=2.4 Hz, 1H), 7.73 (bs, 2H), 7.26-7.22 (d, 2H), 5.99 (s, 1H), 5.51-5.48 (m, 1H), 3.95-3.84 (m, 3H), 3.76-3.71 (m, 1H), 2.26-2.19 (m, 1H), 2.15-2.12 (m, 1H).

Characterization data for further compounds prepared by the above methods are presented in Table 14 below. Compounds in Table 14 were prepared by methods substantially similar to those described to prepare I-82, where 90.1 was replaced with the reagent as indicated in Table 14.

TABLE 14

| Compound # | Reagent | Characterization Data |
|---|---|---|
| I-85 | ![structure] | MS (ES): m/z 390.80 [M + H]$^+$, LCMS purity: 98.30%, HPLC purity: 96.47%, CHIRAL HPLC: 100%, $^1$H NMR (DMSO-d$_6$, 400 MHZ): 8.85 (s, 1H), 8.43 (s, 1H), 8.19 (s, 1H), 7.88 (s, 1H), 7.74 (s, 2H), 7.26-7.23 (d, J = 13.2 Hz, 2H), 6.00 (s, 1H), 5.15 (s, 1H), 3.96-3.93 (m, 1H), 3.91-3.85 (m, 2H), 3.77-3.72 (m, 1H), 2.34-2.24 (m, 1H), 2.22-2.21 (m, 1H). |

TABLE 14-continued

| Compound # | Reagent | Characterization Data |
| --- | --- | --- |
| I-97 | (5-chloro-3-amino-pyridin-2-yl oxy cyclobutyl methyl ether, trans) | MS (ES): m/z 404.42 [M + H]⁺, LCMS purity: 98.84%, HPLC purity: 95.58%, ¹H NMR (DMSO-d₆, 400 MHZ): 8.91 (s, 1H), 8.44 (s, 1H), 8.19 (s, 1H), 7.83 (s, 1H), 7.73 (s, 2H), 7.26 (s, 1H), 7.22 (s, 1H), 6.01 (s, 1H), 4.89-4.87 (t, J = 8 Hz, 1H), 3.66-3.64 (m, 1H), 3.17 (s, 3H), 2.83 (m, 2H), 2.12 (m, 2H). |
| I-119 | (5-chloro-3-amino-pyridin-2-yl oxy cyclobutyl methyl ether, cis) | MS (ES): m/z 404.83 [M + H]⁺, LCMS purity: 98.95%, HPLC purity: 97.56%, CHIRAL HPLC: 93.13%, ¹H NMR (DMSO-d₆, 400 MHZ): 8.95 (s, 1H), 8.39 (s, 1H), 8.21 (s, 1H), 7.87 (d, J = 1.6 Hz, 1H), 7.80 (s, 2H), 7.27 (s, 2H), 5.98 (s, 1H), 5.30-5.27 (t, J = 5.6 Hz, 1H), 4.08-4.05 (t, J = 5.6 Hz, 1H), 3.16 (s, 3H), 2.41-2.34 (m, 4H). |
| I-81 | (5-chloro-3-amino-pyridin-2-yl oxy cyclobutane) | MS (ES): m/z 374.43 [M + H]⁺, LCMS purity: 97.62%, HPLC purity: 96.69%, ¹H NMR (DMSO-d₆, 400 MHZ): 8.90 (s, 1H), 8.41-8.41 (d, J = 2.4 Hz, 1H), 8.19 (s, 1H), 7.83-7.83 (d, J = 2.4 Hz, 1H), 7.72 (s, 2H), 7.26-7.23 (d, J = 10 Hz, 2H), 6.01 (s, 1H), 5.19 (m, 1H), 2.43-2.41 (m, 2H), 2.20-2.10 (m, 2H), 1.81-1.79 (d, J = 10 Hz, 1H), 1.70-1.63 (m, 1H). |
| I-79 | (5-chloro-3-amino-pyridin-2-yl oxy isopropyl) | MS (ES): m/z 362.48 [M + H]⁺, LCMS purity: 99.84%, HPLC purity: 99.63%, ¹H NMR (DMSO-d₆, 400 MHZ): 8.87 (s, 1H), 8.37 (d, J = 2 Hz, 1H), 8.18 (s, 1H), 7.86-7.87 (d, J = 2.4 Hz, 1H), 7.70 (s, 2H), 7.24 (s, 2H), 5.99 (s, 1H), 5.32-5.26 (m, 1H), 1.35-1.24 (m, 6H). |
| I-77 | (3-amino-pyridin-2-yl oxy isopropyl) | MS (ES): m/z 328.35 [M + H]⁺, LCMS purity: 95.25%, HPLC purity: 100%, ¹H NMR (DMSO-d₆, 400 MHZ): 8.64 (s, 1H), 8.18 (s, 1H), 8.06-8.04 (d, J = 7.2 Hz, 1H), 7.88-7.87 (d, J = 4 Hz, 1H), 7.59 (s, 2H), 7.35 (bs, 1H), 7.08 (s, 1H), 6.94-6.90 (t, J = 4.8 Hz, 1H), 5.82 (s, 1H), 5.33-5.30 (t, J = 6.4 Hz, 1H), 1.32-1.30 (d, J = 6 Hz, 6H). |

TABLE 14-continued

| Compound # | Reagent | Characterization Data |
|---|---|---|
| I-64 | 3-amino-1-(5-methylisoxazol-3-yl)pyridin-2(1H)-one | MS (ES): m/z 367.28 [M + H]+, LCMS purity: 100%, HPLC purity: 100%, 1H NMR (DMSO-d6, 400 MHZ): 8.76 (s, 1H), 8.19-8.17 (d, J = 7.6 Hz, 2H), 7.56-7.54 (d, J = 7.2 Hz, 2H), 7.43 (s, 1H), 7.06 (bs, 2H), 6.85 (s, 1H), 6.45-6.41 (t, J = 7.2 Hz, 1H), 6.10 (s, 1H), 2.50 (s, 3H). |
| I-74 | 4-amino-6-methyl-2-(1-methyl-1H-pyrazol-4-yl)pyridazin-3(2H)-one | MS (ES): m/z 381.69 [M + H]+, LCMS purity: 100%, HPLC purity: 98.33%, 1H NMR (DMSO-d6, 400 MHZ): 9.00 (s, 1H), 8.32-8.30 (d, J = 7.2 Hz, 1H), 8.20 (s, 1H), 8.04-8.01 (d, J = 9.6 Hz, 1H), 7.94-7.93 (d, J = 4.8 Hz, 1H), 7.56-7.55 (d, J = 5.6 Hz, 1H), 7.46-7.43 (d, J = 12 Hz, 1H), 7.35 (s, 1H), 7.24 (s, 1H), 6.46-6.42 (t, J = 14.4 Hz, 1H), 6.21 (s, 1H), 4.58-4.52 (m, 2H), 2.91-2.90 (d, J = 4.8 Hz, 3H). |
| I-57 | 3-amino-1-(isoxazol-4-yl)pyridin-2(1H)-one | MS (ES): m/z 353.43 [M + H]+, LCMS purity: 96.68%, HPLC purity: 95.53%, 1H NMR (DMSO-d6, 400 MHZ): 9.13-9.10 (d, J = 12 Hz, 2H), 8.23-8.21 (d, J = 8 Hz, 1H), 8.19 (s, 1H), 7.68 (s, 2H), 7.60-7.59 (d, J = 4 Hz, 1H), 7.32 (s, 1H), 7.18 (s, 2H), 6.46-6.44 (t, J = 8 Hz, 1H), 6.13 (s, 1H). |
| I-42 | 3-amino-1-(2-methylpyrimidin-4-yl)pyridin-2(1H)-one (90b) | MS (ES): m/z 378.28 [M + H]+, LCMS purity: 98.29%, HPLC purity: 97.47%, 1H NMR (DMSO-d6, 400 MHZ): 9.05 (s, 1H), 8.90-8.89 (d, J = 4 Hz, 1H), 8.21-8.19 (d, J = 8 Hz, 2H), 7.94-7.92 (d, J = 8 Hz, 1H), 7.76-7.74 (d, J = 8 Hz, 1H), 7.67 (bs, 2H), 7.35 (s, 1H), 7.19 (s, 1H), 6.47-6.43 (t, 1H), 6.12 (s, 1H), 2.71 (s, 3H). |
| I-120 | 6-(pyrrolidin-1-yl)-2-(trifluoromethyl)pyridin-4-amine | MS (ES): m/z 407.37 [M + H]+, LCMS purity: 97.54%, HPLC purity: 95.38%, 1H NMR (DMSO-d6, 400 MHZ): 9.82 (s, 1H), 8.23 (s, 1H), 7.81 (s, 2H), 7.48 (s, 1H), 7.26 (s, 1H), 7.11 (s, 1H), 7.03 (s, 1H), 5.78 (s, 1H), 4.04-4.02 (d, J = 6.8 Hz, 1H), 2.09-1.95 (m, 6H), 1.23-1.16 (m, 1H). |
| I-58 | 1-(6-aminopyridin-2-yl)pyrrolidin-2-one | MS (ES): m/z 353.48 [M + H]+, LCMS purity: 95.94%, HPLC purity: 98.94%, 1H NMR (DMSO-d6, 400 MHZ): 9.17 (s, 2H), 8.57 (s, 1H), 8.06 (s, 1H), 7.96-7.87 (m, 2H), 7.58 (s, 1H), 7.20 (s, 1H), 6.88-6.86 (d, J = 8 Hz, 1H), 6.39 (s, 1H), 4.22-4.20 (t, J = 8 Hz, 2H), 2.60-2.58 (t, J = 8 Hz, 2H), 2.14-2.07 (m, 2H). |

TABLE 14-continued

| Compound # | Reagent | Characterization Data |
|---|---|---|
| I-76 | (structure) | MS (ES): m/z 453.52 [M + H]+, LCMS purity: 95.83%, HPLC purity: 98.33%, CHIRAL HPLC purity: 99.0% $^1$H NMR (DMSO-d$_6$, 400 MHZ): 8.83 (s, 1H), 8.17 (s, 1H), 8.08-8.06 (d, J = 6.8 Hz, 1H), 7.62 (s, 2H), 7.34-7.28 (m, 2H), 7.18 (s, 1H), 6.33 (m, 1H), 6.07 (s, 1H), 4.88-4.85 (m, 1H), 3.66 (s, 4H), 2.41 (s, 4H), 2.16-2.10 (m, 3H), 1.96-1.92 (m, 2H), 1.53 (s, 4H). |
| I-66 | (structure) | MS (ES): m/z 355.27 [M + H]+, LCMS purity: 98.75%, HPLC purity: 99.19%, $^1$H NMR (DMSO-d$_6$, 400 MHZ): 9.70 (s, 1H), 8.20 (s, 1H), 7.74-7.70 (t, J = 8 Hz, 1H), 7.65-7.63 (m, 2H), 7.11-7.09 (d, J = 8.4 Hz, 2H), 6.94 (s, 1H), 4.52-4.48 (t, J = 7.6 Hz, 2H), 4.33-4.29 (t, J = 7.6 Hz, 2H), 3.8 (bs, 2H). |
| I-55 | (structure) | MS (ES): m/z 367.42 [M + H]+, LCMS purity: 95.51%, HPLC purity: 95.00%, $^1$H NMR (DMSO-d$_6$, 400 MHZ): 9.85 (s, 1H), 8.21 (s, 2H), 7.75 (s, 2H), 7.47 (s, 1H), 7.39 (s, 1H), 7.23 (s, 1H), 5.82 (s, 1H), 3.99-3.97 (t, J = 8 Hz, 2H), 2.60-2.56 (m, 2H), 2.38 (s, 3H), 2.04-2.02 (t, J = 8 Hz, 2H). |
| I-100 | (structure) | MS (ES): m/z 433.30 [M + H]+, LCMS purity: 100%, HPLC purity: 96.14%, $^1$H NMR (DMSO-d$_6$, 400 MHZ): 8.83 (s, 1H), 8.16 (s, 1H), 8.05-8.04 (d, J = 4 Hz, 1H), 7.61 (s, 2H), 7.46-7.44 (d, J = 8 Hz, 1H), 7.34 (s, 1H), 7.16 (s, 1H), 6.28-6.25 (t, J = 12 Hz, 2H), 6.17-6.16 (d, J = 4 Hz, 1H), 6.05 (s, 1H), 4.47 (s, 1H), 3.07-3.05 (d, J = 8 Hz, 2H), 2.81-2.80 (d, J = 4 Hz, 2H), 1.94-1.91 (m, 2H), 1.76-1.73 (d, J = 12 Hz, 2H), 1.24 (s, 1H). |
| I-38 | (structure) | MS (ES): m/z 435.62 [M + H]+, LCMS purity: 95.41%, HPLC purity: 95.08%, $^1$H NMR (DMSO-d$_6$, 400 MHZ): 9.25-9.23 (t, J = 8 Hz, 1H), 9.09 (s, 1H), 8.91 (s, 1H), 8.28-8.19 (m, 2H), 7.68-7.65 (m, 2H), 7.37-7.35 (d, J = 8 Hz, 1H), 7.20-7.14 (m, 1H), 6.50-6.48 (t, J = 8 Hz, 1H), 6.29-6.26 (m, 1H), 6.13 (s, 1H), 3.07-3.04 (d, J = 12 Hz, 6H). |

TABLE 14-continued

| Compound # | Reagent | Characterization Data |
|---|---|---|
| I-50 | (structure shown) | MS (ES): m/z 384.53 [M + H]+, LCMS purity: 97.72%, HPLC purity: 96.73%, 1H NMR (DMSO-d6, 400 MHZ): 8.83 (s, 1H), 8.17 (s, 1H), 8.06-8.04 (d, J = 8 Hz, 1H), 7.62 (s, 2H), 7.41-7.40 (d, J = 4 Hz, 1H), 7.34 (s, 1H), 7.17 (s, 1H), 6.29-6.27 (t, J = 8 Hz, 1H), 6.06 (s, 1H), 4.71-4.70 (d, J = 4 Hz, 1H), 3.51 (s, 1H), 1.97-1.95 (d, J = 8 Hz, 2H), 1.80-1.75 (m, 4H), 1.36-1.35 (d, J = 4 Hz, 2H). |

Synthesis of (S)-7-amino-5-((2-(3-hydroxypiperidin-1-yl)-6-methylpyridin-4-yl)amino)pyrazolo[1,5-a]pyrimidine-3-carboxamide (I-62)

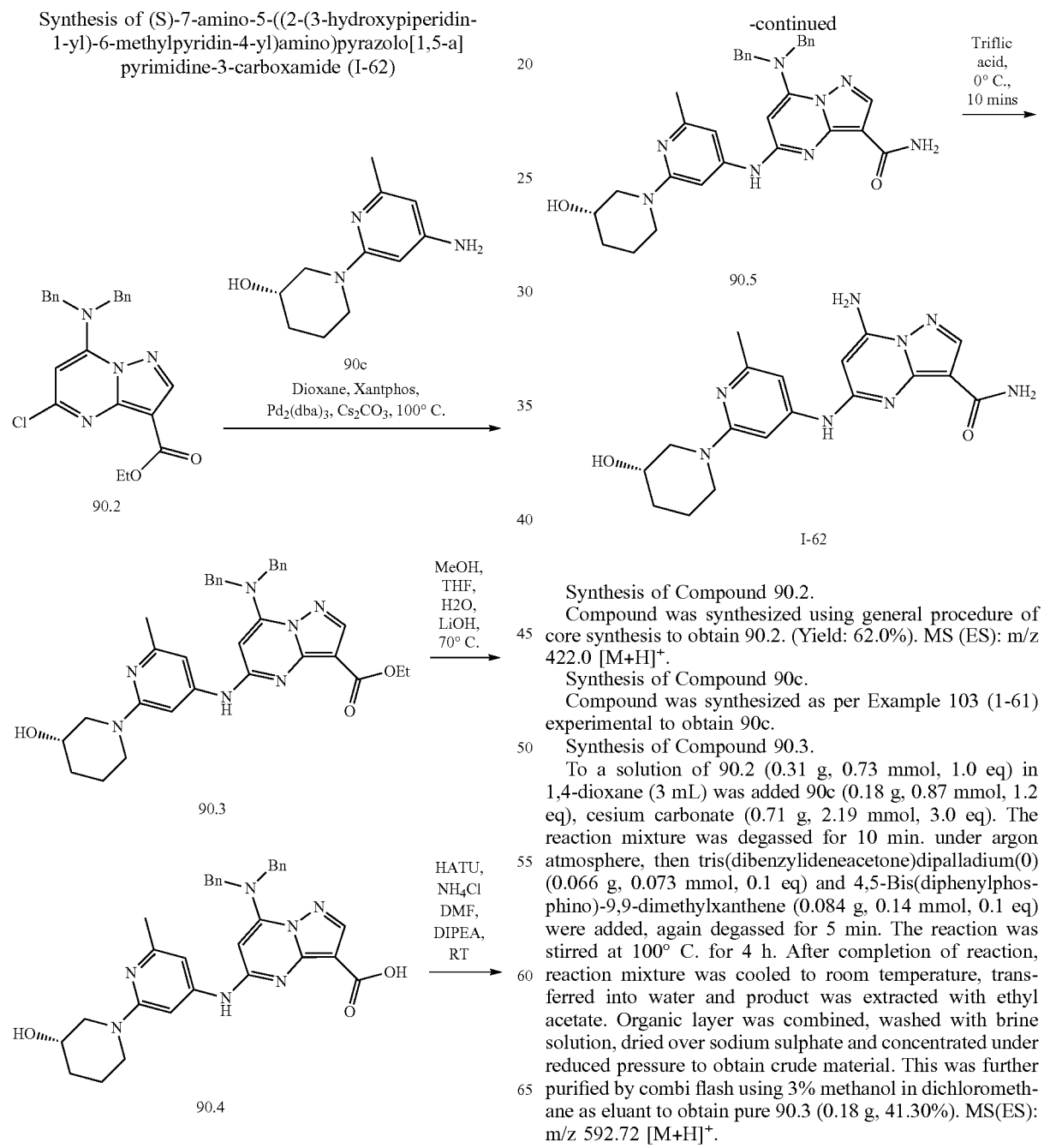

Synthesis of Compound 90.2.

Compound was synthesized using general procedure of core synthesis to obtain 90.2. (Yield: 62.0%). MS (ES): m/z 422.0 [M+H]+.

Synthesis of Compound 90c.

Compound was synthesized as per Example 103 (1-61) experimental to obtain 90c.

Synthesis of Compound 90.3.

To a solution of 90.2 (0.31 g, 0.73 mmol, 1.0 eq) in 1,4-dioxane (3 mL) was added 90c (0.18 g, 0.87 mmol, 1.2 eq), cesium carbonate (0.71 g, 2.19 mmol, 3.0 eq). The reaction mixture was degassed for 10 min. under argon atmosphere, then tris(dibenzylideneacetone)dipalladium(0) (0.066 g, 0.073 mmol, 0.1 eq) and 4,5-Bis(diphenylphosphino)-9,9-dimethylxanthene (0.084 g, 0.14 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 90.3 (0.18 g, 41.30%). MS(ES): m/z 592.72 [M+H]+.

Synthesis of Compound 90.4.

To a solution of 90.3 (0.18 g, 0.30 mmol, 1.0 eq), in tetrahydrofuran: methanol: water (5 mL, 1:1:1) was added lithium hydroxide (0.12 g, 3.0 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 90.4 (0.12 g, 69.98%). MS(ES): m/z 564.66 [M+H]$^+$.

Synthesis of Compound 90.5.

Compound was synthesized using general procedure A to obtain 90.5 (Yield: 75.13%). MS (ES): m/z 563.68 [M+H]$^+$ Synthesis of Compound I-62.

Compound was synthesized using general procedure C to obtain I-62 (Yield: 106.26%). MS (ES): m/z 383.53 [M+H]$^+$, LCMS purity: 98.76%, HPLC purity: 98.31%, CHIRAL HPLC purity: 100%, $^1$H NMR (DMSO-d$_6$, 400 MHZ): 9.47 (s, 1H), 8.19 (s, 1H), 7.70 (s, 2H), 7.43 (s, 1H), 7.30 (s, 1H), 6.86 (s, 1H), 6.67 (s, 1H), 5.76 (s, 1H), 4.89 (s, 1H), 4.16-4.13 (d, J=9.6 Hz, 1H), 3.95-3.92 (d, J=12.8 Hz, 1H), 3.47 (s, 1H), 2.82-2.72 (m, 1H), 2.24 (s, 3H), 1.89 (bs, 1H), 1.70 (bs, 1H), 1.44-1.28 (m, 2H), 1.10-1.08 (m, 1H).

Characterization data for further compounds prepared by the above methods are presented in Table 15 below. Compounds in Table 15 were prepared by methods substantially similar to those described to prepare I-62, where 90c was replaced with the reagent as indicated in Table 15.

TABLE 15

| Compound # | Reagent | Characterization Data |
|---|---|---|
| I-62 | (structure) | MS (ES): m/z 383.53 [M + H]$^+$, LCMS purity: 98.76%, HPLC purity: 98.31%, CHIRAL HPLC purity: 100%, $^1$H NMR (DMSO-d$_6$, 400 MHZ): 9.47 (s, 1H), 8.19 (s, 1H), 7.70 (s, 2H), 7.43 (s, 1H), 7.30 (s, 1H), 6.86 (s, 1H), 6.67 (s, 1H), 5.76 (s, 1H), 4.89 (s, 1H), 4.16-4.13 (d, J = 9.6 Hz, 1H), 3.95-3.92 (d, J = 12.8 Hz, 1H), 3.47 (s, 1H), 2.82-2.72 (m, 1H), 2.24 (s, 3H), 1.89 (bs, 1H), 1.70 (bs, 1H), 1.44-1.28 (m, 2H), 1.10-1.08 (m, 1H). |
| I-56 | (structure) | MS (ES): m/z 369.52 [M + H]$^+$, LCMS purity: 98.14%, HPLC purity: 97.13%, $^1$H NMR (DMSO-d$_6$, 400 MHZ): 9.46 (s, 1H), 8.20 (s, 1H), 7.71 (s, 2H), 7.43 (s, 2H), 6.52 (s, 1H), 5.78 (s, 1H), 4.90 (s, 1H), 4.38 (s, 1H), 3.44-3.40 (m, 4H), 3.30-3.24 (m, 1H), 2.25 (s, 3H), 2.01-1.91 (m, 2H). |
| I-41 | (structure) | MS (ES): m/z 421.23 [M + H]$^+$, LCMS purity: 95.01%, HPLC purity: 95.00%, $^1$H NMR (DMSO-d$_6$, 400 MHZ): 9.00 (s, 1H), 8.19 (s, 1H), 8.02-8.00 (t, J = 8 Hz, 1H), 7.76-7.74 (d, J = 8 Hz, 1H), 7.68-7.66 (d, J = 8 Hz, 2H), 7.59-7.57 (d, J = 8 Hz, 1H), 7.39 (s, 2H), 7.22 (s, 2H), 6.43-6.42 (t, J = 4 Hz, 1H), 6.11 (s, 1H), 5.39 (s, 1H), 1.48 (s, 6H). |
| I-21 | (structure) | MS (ES): m/z 297.48 [M + H]$^+$, LCMS purity: 95.04%, HPLC purity: 95.37%, $^1$H NMR (DMSO-d$_6$, 400 MHZ): 9.27 (s, 1H), 8.13-8.12 (d, J = 4.4 Hz, 1H), 7.548 (s, 3H), 7.305 (s, 1H), 7.184 (s, 2H), 6.66 (s, 1H), 5.67 (s, 1 H), 2.25 (s, 6H). |

1001

Synthesis of 7-amino-5-((2-(4-fluorophenyl)-3-oxo-2,3-dihydropyridazin-4-yl)amino)pyrazolo[1,5-a]pyrimidine-3-carboxamide (I-70)

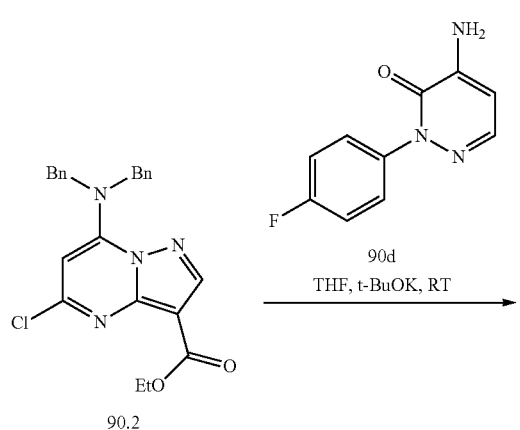

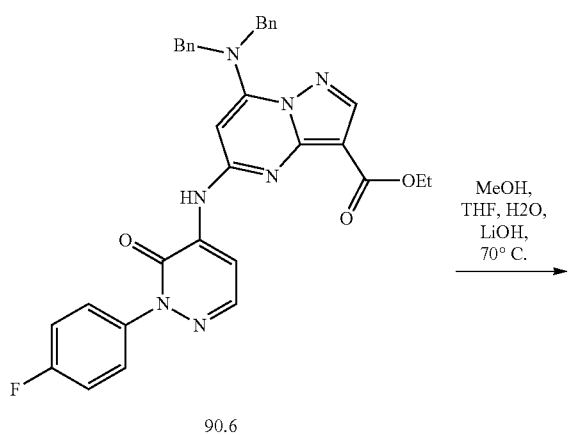

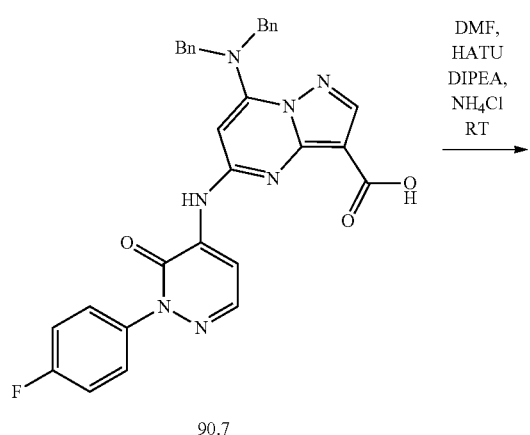

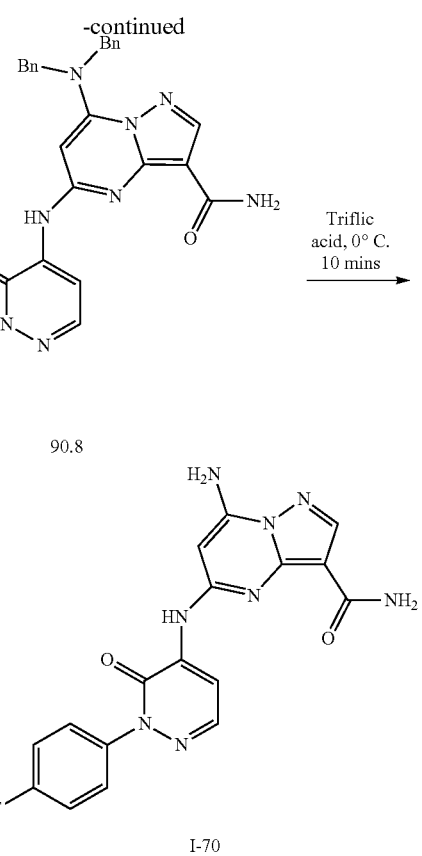

Synthesis of Compound 90.2.
Compound was synthesized using general procedure of core synthesis to obtain 90.2 (Yield: 62.00%). MS (ES): m/z 422.05 [M+H]$^+$.

Synthesis of Compound 90d.
Compound was synthesized as per Example 103 (1-69) to obtain 90d.

Synthesis of Compound 90.6.
To a solution of 90.2 (0.20 g, 0.47 mmol, 1.0 eq) and 90d (0.09 g, 0.47 mmol, 1.0 eq) in tetrahydrofuran (3 mL) was added potassium tert.butoxide (0.9 mL, 0.94 mmol, 2.0 eq) at 0° C. The reaction mixture was stirred at room temperature. After completion of reaction, reaction mixture was transferred to ice cold water and product was extracted with ethylacetate. Organic layer was combined, dried over sodium sulphate and concentrated under reduced pressure to obtain crude material. This was further purified by column chromatography to obtain pure 90.6 (0.17 g, 62.46%). MS(ES): m/z 590.63 [M+H]$^+$.

Synthesis of Compound 90.7.
To a solution of 90.6 (0.17 g, 0.29 mmol, 1.0 eq), in tetrahydrofuran: methanol: water (5 mL, 1:1:1) was added lithium hydroxide (0.12 g, 2.9 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 70° C. Product was extracted with dichloromethane. Organic layer was combined, washed with brine solution, dried over sodium sulphate and concentrated under reduced pressure to obtain 90.7 (0.12 g, 72.60%). MS(ES): m/z 562.58 [M+H]$^+$.

Synthesis of Compound 90.8.
Compound was synthesized using general procedure A to obtain 90.8. (Yield: 74.51%). MS (ES): m/z 561.59 [M+H]$^+$.

Synthesis of Compound I-70.

Mixture of 90.8 (0.05 g, 0.13 mmol, 1.0 eq) and triflic acid (1.5 mL) was allowed to stir at 0° C. for 10 min. After completion of reaction, reaction mixture was transferred into saturated sodium bicarbonate solution and product was extracted with dichloromethane. Organic layer was combined, washed with brine solution, dried over sodium sulphate and concentrated under reduced pressure to obtain crude material. This was further purified by trituration with diethyl ether to a obtain I-70 (Yield: 81.88%). MS (ES): m/z 381.88 [M+H]$^+$, LCMS purity: 98.34%, HPLC purity: 98.40%, $^1$H NMR (DMSO-d$_6$, 400 MHZ): 9.71 (s, 1H), 8.30 (s, 1H), 8.12-8.11 (d, J=4.8 Hz, 1H), 7.96-7.92 (t, J=15.2 Hz, 3H), 7.70-7.66 (m, 2H), 7.40-7.35 (m, 2H), 7.25-7.23 (d, J=8 Hz, 2H), 6.38 (s, 1H).

Characterization data for further compounds prepared by the above methods are presented in Table 16 below. Compounds in Table 16 were prepared by methods substantially similar to those described to prepare I-70, where 90d was replaced with the reagent as indicated in Table 16.

TABLE 16

| Compound # | Reagent | Characterization Data |
|---|---|---|
| I-33 | (3-amino-1-(6-ethoxypyridazin-3-yl)pyridin-2(1H)-one reagent) | MS (ES): m/z 408.54 [M + H]$^+$, LCMS purity: 94.51%, HPLC purity: 97.32%, $^1$H NMR (DMSO-d$_6$, 400 MHZ): 9.03 (s, 1H), 8.25-8.23 (d, J = 8 Hz, 1H), 8.20 (s, 1H), 8.03-8.01 (d, J = 8 Hz, 1H), 7.67 (s, 2H), 7.58-7.56 (d, J = 8 Hz, 1H), 7.46-7.43 (d, 8 Hz, 1H), 7.38 (s, 1H), 7.20 (s, 1H), 6.45-6.44 (t, J = 7.2 Hz, 1H), 6.12 (s, 1H), 4.58-4.32 (m, 2H), 1.45-1.41 (t, J = 8 Hz, 3H). |
| I-34 | (3-amino-5-methyl-1-(1-methyl-1H-pyrazol-4-yl)pyridin-2(1H)-one reagent) | MS (ES): m/z 380.43 [M + H]$^+$, LCMS purity: 98.36%, HPLC purity: 98.64%, $^1$H NMR (DMSO-d$_6$, 400 MHZ): 9.03 (s, 1H), 8.18-8.15 (d, J = 12 Hz, 2H), 7.81 (s, 1H), 7.66 (s, 2H), 7.46-7.31 (m, 3H), 6.73 (s, 1H), 6.13 (s, 1H), 3.89 (s, 3H), 2.12 (s, 3H). |
| I-22 | 90e (2-chloro-3-morpholinoaniline reagent) | MS (ES): m/z 388.83 [M + H]$^+$, LCMS purity: 98.23%, HPLC purity: 96.95%, $^1$H NMR (DMSO-d$_6$, 400 MHZ): 9.00 (s, 1H), 8.10 (s, 1H), 7.57 (s, 2H), 7.36-7.34 (d, J = 6.8 Hz, 2H), 7.310-7.27 (t, J = 8 Hz, 1H), 7.04-6.99 (m, 2H), 5.68 (s, 1H), 3.76 (bs, 4H), 2.98 (bs, 4H). |
| I-52 | (3-amino-1-(5-fluoropyridin-2-yl)pyridin-2(1H)-one reagent) | MS (ES): m/z 381.34 [M + H]$^+$, LCMS purity: 95.13%, HPLC purity: 99.62%, $^1$H NMR (DMSO-d$_6$, 400 MHZ): 9.79 (s, 1H), 8.70 (s, 1H), 8.64 (s, 2H), 8.47 (s, 1H), 7.99-7.98 (d, J = 4 Hz, 1H), 7.94-7.93 (d, J = 4 Hz, 1H), 7.86-7.84 (d, J = 8 Hz, 2H), 7.76-7.74 (d, J = 8 Hz, 2H), 6.53-6.52 (t, J = 4 Hz, 1H), 6.01 (s, 1H). |
| I-28 | (2-methyl-6-(pyrrolidin-1-yl)pyridin-4-amine reagent) | MS (ES): m/z 353.22 [M + H]$^+$, LCMS purity: 100%, HPLC purity: 98.79%, $^1$H NMR (DMSO-d$_6$, 400 MHZ): 9.43 (s, 1H), 8.19 (s, 1H), 7.68 (s, 2H), 7.44 (s, 2H), 6.64 (s, 1H), 6.51 (s, 1H), 5.77 (s, 1 H), 3.33 (s, 4H), 2.28 (s, 3H), 1.93 (s, 4H). |

TABLE 16-continued

| Compound # | Reagent | Characterization Data |
|---|---|---|
| I-99 | (structure) | MS (ES): m/z 380.38 [M + H]+, LCMS purity: 95.68%, HPLC purity: 96.50%, 1H NMR (DMSO-d6, 400 MHZ): 9.06 (s, 1H), 8.24-8.23 (d, J = 4 Hz, 1H), 8.19 (s, 1H), 7.67 (s, 2H), 7.55-7.55 (d, J = 2 Hz, 1H), 7.41 (s, 1H), 7.38 (s, 1H), 7.04 (s, 1H), 6.44-6.43 (d, J = 4 Hz, 1H), 6.14 (s, 1H), 3.62 (s, 3H), 2.10 (s, 3H). |
| I-25 | (structure) | MS (ES): m/z 380.53 [M + H]+, LCMS purity: 96.47%, HPLC purity: 95.95%, 1H NMR (DMSO-d6, 400 MHZ): 8.93 (s, 1H), 8.19 (s, 1H), 7.63-7.54 (m, 3H), 7.41-7.32 (m, 3H), 7.19 (s, 1H), 6.37-6.33 (t, 1H), 6.10 (s, 1H). |
| I-30 | (structure) | MS (ES): m/z 383.53 [M + H]+, LCMS purity: 100%, HPLC purity: 100%, Chiral HPLC purity: 100%, 1H NMR (DMSO-d6, 400 MHZ): 9.44 (s, 1H), 8.19 (s, 1H), 7.71 (s, 1H), 7.42 (s, 2H), 6.62 (s, 1H), 6.54 (s, 2H), 5.77 (s, 1H), 4.04 (s, 1H), 3.42-3.38 (m, 3H), 3.27-3.24 (m, 4H), 2.22 (s, 3H), 2.03 (s, 2H). |
| I-32 | (structure) | MS (ES): m/z 380.48 [M + H]+, LCMS purity: 96.53%, HPLC purity: 97.58%, 1H NMR (DMSO-d6, 400 MHZ): 9.00 (s, 1H), 8.29 (s, 1H), 8.18 (s, 1H), 8.11 (s, 1H), 7.89 (s, 1H), 7.65 (s, 2H), 7.40 (bs, 2H), 7.35 (s, 1H), 6.12 (s, 1H), 3.90 (s, 3H), 2.11 (s, 3H). |
| I-49 | (structure) | MS (ES): m/z 348.43 [M + H]+, LCMS purity: 97.59%, HPLC purity: 97.25%, 1H NMR (DMSO-d6, 400 MHZ): 9.10 (s, 1H), 8.29-8.28 (d, J = 4 Hz, 1H), 8.21 (s, 1H), 7.70 (s, 2H), 7.63-7.62 (d, J = 4 Hz, 1H), 7.40 (s, 1H), 7.17 (s, 1H), 6.18 (s, 1H), 4.03-3.97 (m, 2H), 1.28-1.26 (t, J = 8 Hz, 3H). |
| I-23 | (structure) | MS (ES): m/z 372.47 [M + H]+, LCMS purity: 100%, HPLC purity: 96.36%, 1H NMR (DMSO-d6, 400 MHZ): 8.93 (s, 1H), 8.09 (s, 1H), 7.54 (s, 2H), 7.43 (m, 1H), 7.17-7.15 (t, J = 8 Hz 1H), 7.10-7.09 (d, J = 4 Hz 1H), 7.03 (s, 1H), 6.85-6.83 (d, J = 8 Hz, 1H), 5.64 (s, 1H), 3.30 (s, 4H), 1.89 (s, 4H). |

Synthesis of 7-amino-5-((2-(trifluoromethoxy)pyridin-3-yl)amino)pyrazolo[1,5-a]-pyrimidine-3-carboxamide (I-102)

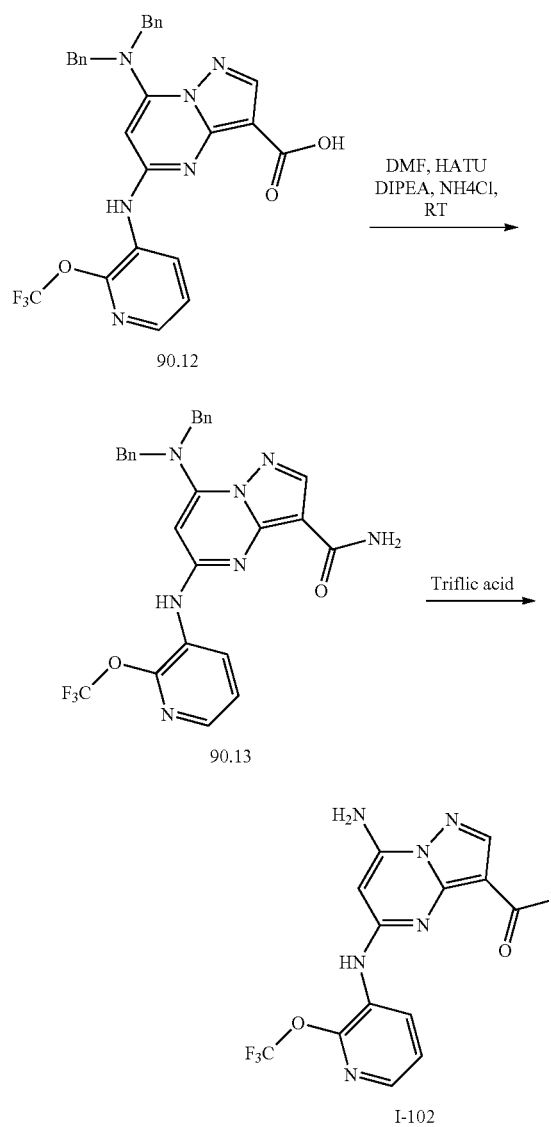

Synthesis of Compound 90.12.
Compound was synthesized as per Example 20 (1-113) to obtain 90.12.

Synthesis of Compound 90.13.
Compound was synthesized using general procedure A to obtain 91.13. (0.059 g, 84.44%). MS (ES): m/z 534.32 [M+H]$^+$ Synthesis of Compound I-102.
Mixture of 90.13 (0.059 g, 0.110 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-102 (0.030 g, 76.79%), MS (ES): m/z 354.36 [M+H]$^+$, LCMS purity: 95.21%, HPLC purity: 96.82%, $^1$H NMR (DMSO-d$_6$, 400 MHZ): 9.22 (s, 1H), 8.36-8.34 (d, J=8 Hz, 1H), 8.15 (S, 1H), 8.07-8.06 (d, J=4 Hz, 1H), 7.72 (s, 2H), 7.41-7.38 (m, 1H), 7.19 (s, 1H), 7.05 (s, 1H), 5.82 (s, 1H).

Synthesis of Intermediate 90a.

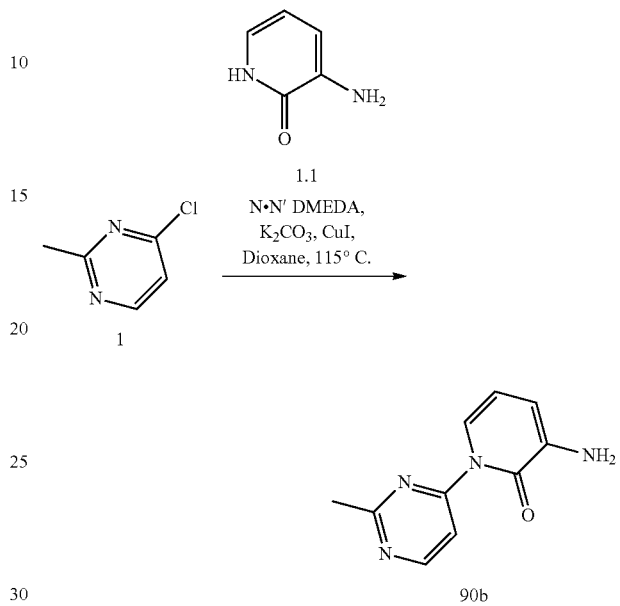

Synthesis of Compound 90b.
To a solution of 1 (0.800 g, 6.22 mmol, 1.3 eq) and 1.1 (0.527 g, 4.79 mmol, 1.0 eq) in 1,4-dioxane (8 mL) was added potassium carbonate (1.71 g, 12.44 mmol, 2.0 eq) and degassed with argon for 15 min. Copper iodide (0.177 g, 0.933 mmol, 0.15 eq) and 1,2-dimethylethylenediamine (0.164 g, 1.866 mmol, 0.3 eq) was added and reaction mixture again degassed with argon for 5 min followed by heating at 115° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 90b (0.460 g, 47.52%). MS(ES): m/z 203.22 [M+H]$^+$.

Synthesis of Intermediate 90e

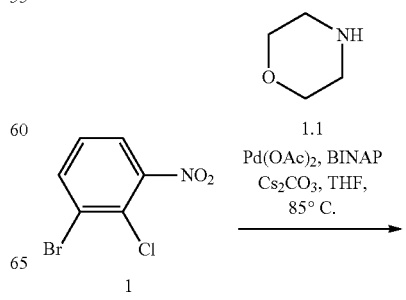

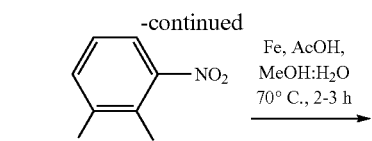

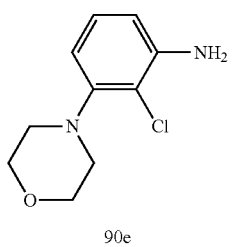

90e

Synthesis of Compound 1.2.

To a solution of 1 (2.0 g, 8.46 mmol, 1.0 eq) in tetrahydrofuran (3 mL) was added palladium acetate (0.189 g, 0.846 mmol, 0.1 eq) and cesium carbonate (4.1 g, 12.69 mmol, 1.5 eq). The reaction mixture was degassed for 10 min under argon atmosphere followed by addition of 1.1 (2.20 g, 25.38 mmol, 3 eq) and again degassed for 5 min. The reaction was stirred at 85° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 1.2 (1.1 g, 49.50%). MS(ES): m/z 243.60 [M+H]$^+$.

Synthesis of Compound 90e.

To 1.2 (1.1 g, 4.43 mmol, 1.0 eq) added mixture of methanol:water (10 mL, 2:1) and acetic acid (2.7 g, 44.3 mmol, 10 eq). The reaction mixture was heated 70° C. then iron powder (2.48 g, 44.3 mmol, 10 eq) was added portionwise. The reaction was stirred at 70° C. for 3 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 30% ethyl acetate in hexane to obtain pure 90e (0.60 g, 62.23%). MS(ES): m/z 213.68 [M+H]$^+$.

Synthesis of Intermediate 90f.

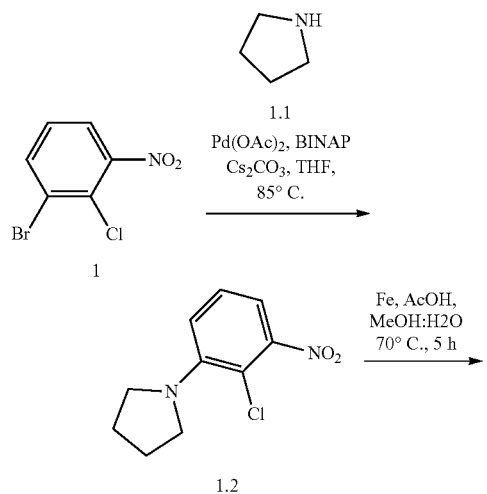

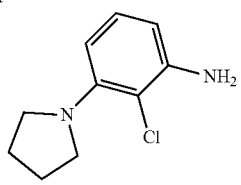

90f

Synthesis of Compound 1.2.

To a solution of 1 (1 g, 4.23 mmol, 1.0 eq) in tetrahydrofuran (15 mL) was added palladium acetate (0.095 g, 0.423 mmol, 0.1 eq), cesium carbonate (2.06 g, 6.33 mmol, 1.5 eq) and (2,2'-bis(diphenylphosphino)-1,1'-binaphthyl) (0.394 g, 0.63 mmol, 0.15 eq). The reaction mixture was degassed for 10 min under argon atmosphere and 1.1 (1.2 g, 16.91 mmol, 4.0 eq) was added, again degassed for 5 min. The reaction mixture was stirred at 85° C. for 18 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 2% ethyl acetate in hexane to obtain pure 1.2 (0.380 g, 39.64%). MS(ES): m/z 227.66[M+H]$^+$.

Synthesis of Compound 90f.

To 1.2 (0.380 g, 1.68 mmol, 1.0 eq) added mixture of methanol:water (1 mL, 2:1) and acetic acid (1.008 g, 16.8 mmol, 10 eq). The reaction mixture was heated 60° C. then iron powder (0.564 g, 10.08 mmol, 6 eq) was added portionwise. The reaction was stirred at 70° C. for 5 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 90f (0.250 g, 75.82%). MS(ES): m/z 197.68 [M+H]$^+$.

Example 91: Synthesis of Compounds where $R^3$ is N-(cis)-(2-hydroxycyclobutyl)carboxamide, $R^6$ is Hydrogen, and $R^7$ is Methylamine

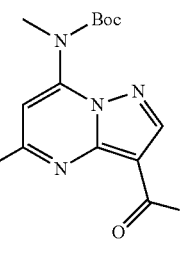 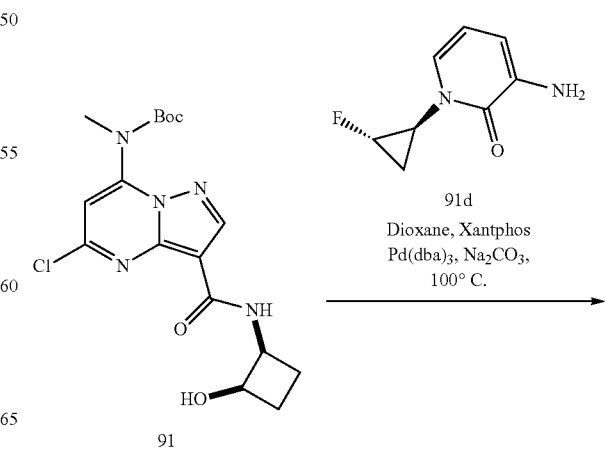

91

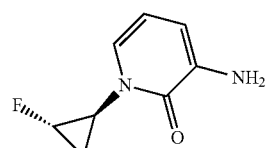

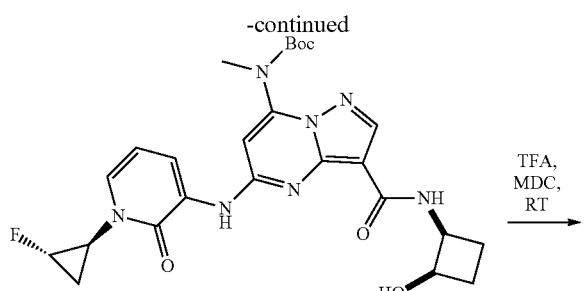

91.1

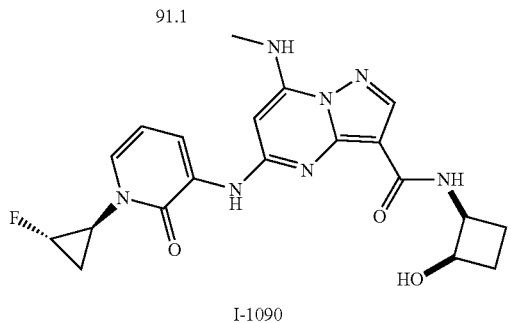

I-1090

Synthesis of 5-((1-((1S,2S)-2-fluorocyclopropyl)-2-oxo-1,2-dihydropyridin-3-yl)amino)-N-(2-hydroxycyclobutyl)-7-(methylamino)pyrazolo[1,5-a]pyrimidine-3-carboxamide (I-1090)

Synthesis of Compound 91.

Compound was synthesized as per I-654 to obtain 91. (Yield: 50.51%), MS (ES): m/z 396.84 [M+H]⁺.

Synthesis of Compound 91d.

Compound was synthesized as per Example 101 (I-1060) to obtain 91d MS (ES): m/z 169.07 [M+H]⁺.

Synthesis of Compound 91.1.

Compound was synthesized using general procedure B to obtain 91.1 (0.135 g, 67.53%). MS(ES): m/z 527.5 [M+H]⁺.

Synthesis of Compound I-1090:

Compound was synthesized using general procedure C to obtain I-1090 (0.022 g, 77.58%), MS (ES): m/z 428.51 [M+H]⁺, LCMS purity: 100%, HPLC purity: 99.80%, CHIRAL HPLC Purity: 47.59%, 51.10%, ¹H NMR (DMSO-d₆, 400 MHZ): 8.89 (s, 1H), 8.51-8.50 (d, J=6 Hz, 1H), 8.20 (s, 2H), 8.04-8.00 (m, 1H), 7.90-7.89 (d, J=4.8 Hz, 1H), 7.15-7.13 (m, 1H), 7.08-7.06 (d, J=7.6 Hz, 1H), 6.83-6.81 (d, J=8 Hz, 1H), 6.35-6.34 (t, J=2 Hz, 1H), 6.28 (bs, 1H), 5.41-5.35 (m, 1H), 4.58-4.54 (m, 1H), 4.34 (bs, 1H), 3.90-3.82 (m, 1H), 2.92-2.91 (d, J=4.8 Hz, 3H), 2.33 (bs, 1H), 1.98-1.91 (m, 1H), 1.55 (bs, 2H).

Characterization data for further compounds prepared by the above methods are presented in Table 17 below. Compounds in Table 17 were prepared by methods substantially similar to those described to prepare I-1090, where 91d was replaced with the reagent as indicated in Table 17.

TABLE 17

| Compound # | Reagent | Characterization Data |
|---|---|---|
| I-1089 | 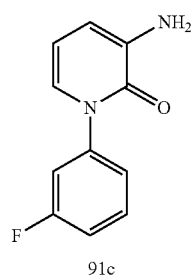 [SMILES: Nc1cccn(-c2cccc(F)c2)c1=O] | MS (ES): m/z 428.44 [M + H]⁺, LCMS purity: 100%, HPLC purity: 97.31%, CHIRAL HPLC, 49:49%, ¹H NMR (DMSO-d₆, 400 MHZ): 8.89 (s, 1H), 8.51-8.50 (d, J = 6 Hz, 1H), 8.20 (s, 1H), 8.04-8.00 (m, 1H), 7.90-7.89 (d, J = 4.8 Hz, 1H), 7.15-7.13 (m, 1H), 6.35-6.34 (m, 1H), 6.28 (s, 1H), 5.41-5.38 (m, 1H), 5.08-4.92 (m, 1H), 4.58-4.54 (m, 1H), 4.34-4.13 (m, 1H), 3.90-3.82 (m, 1H), 2.91-2.50 (bs, 3H), 2.18-2.17 (m, 1H), 2.17-2.04 (m, 2H), 1.98-1.88 (m, 2H) 1.74-1.66 (m, 1H). |
| I-945 | 91c | MS (ES): m/z 464.52 [M + H]⁺, LCMS purity: 96.44%, HPLC purity: 95.27%, CHIRAL HPLC: 48.11%, 48.70%, ¹H NMR (DMSO-d₆, 400 MHZ): 8.92 (s, 1H), 8.64-8.62 (d, J = 7.2 Hz, 1H), 8.22 (s, 1H), 8.07-8.05 (d, J = 8.8 Hz, 1H), 7.92-7.91 (d, J = 4.8 Hz, 1H), 7.63-7.51 (m, 1H), 7.50-7.48 (d, J = 9.6 Hz, 1H), 7.38-7.34 (t, J = 8 Hz, 3H), 6.50-6.46 (t, J = 7.2 Hz, 1H), 6.30 (s, 1H), 5.46-5.45 (d, J = 3.6 Hz, 1H), 4.60-4.57 (m, 1H), 4.37 (bs, 1H), 2.91-2.90 (d, J = 4.8 Hz, 3H), 2.21 (bs, 1H), 1.76 (bs, 1H), 1.34-1.32 (d, J = 6 Hz, 1H), 1.22 (bs, 1H). |

TABLE 17-continued

| Compound # | Reagent | Characterization Data |
|---|---|---|
| I-1004<br>I-1005 | 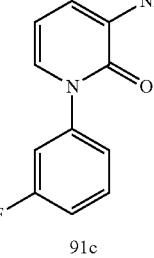<br>91c | Intermediate corresponding to 91.1 en route to I-945 was separated into isomers before BOC removal: (CHIRAL PAK AD-H 250 × 4.6 mm, 5 μM) using 0.1% DEA_HEX_IPA-MEOH (50-50).<br>Product prepared from FR-a: MS (ES): m/z 464.47 [M + H]$^+$, LCMS purity: 100%, HPLC purity: 99.40%, Chiral HPLC: 100%, $^1$H NMR (DMSO-d$_6$, 400 MHZ): 8.91 (s, 1H), 8.66-8.64 (d, J = 8 Hz, 1H), 8.23 (s, 1H), 8.08-8.06 (d, J = 8.8 Hz, 1H), 7.93-7.92 (d, J = 4.8 Hz, 1H), 7.65-7.59 (m, 1H), 7.52-7.49 (d, J = 9.6 Hz, 1H), 7.39-7.37 (t, J = 8 Hz, 3H), 6.49-6.47 (t, J = 8 Hz, 1H), 6.31 (s, 1H), 5.48-5.47 (d, J = 4 Hz, 1H), 4.62-4.60 (t, J = 8 Hz, 1H), 4.39 (s, 1H), 2.92-2.91 (d, J = 4 Hz, 3H), 2.22-2.21 (d, J = 3.8 Hz, 1H), 2.14-2.00 (bs, 1H), 2.17-2.15 (d, J = 8 Hz, 2H).<br>Product prepared from FR-b: MS (ES): m/z 464.47 [M + H]$^+$, LCMS purity: 100%, HPLC purity: 97.37%, Chiral HPLC: 99.38%, $^1$H NMR (DMSO-d$_6$, 400 MHZ): 8.93 (s, 1H), 8.66-8.64 (d, J = 8 Hz, 1H), 8.23 (s, 1H), 8.08-8.06 (d, J = 8.8 Hz, 1H), 7.93-7.92 (d, J = 4.8 Hz, 1H), 7.65-7.59 (m, 1H), 7.52-7.49 (d, J = 9.6 Hz, 1H), 7.39-7.37 (t, J = 8 Hz, 3H), 6.49-6.47 (t, J = 8 Hz, 1H), 6.31 (s, 1H), 5.48-5.47 (d, J = 4 Hz, 1H), 4.62-4.60 (t, J = 8 Hz, 1H), 4.39 (s, 1H), 4.35(s, 1H), 2.92-2.91 (d, J = 4 Hz, 3H), 2.22-2.21 (d, J = 3.8 Hz, 1H), 2.14-2.00 (bs, 1H), 2.17-2.15 (d, J = 8 Hz, 1H). |
| I-942 | 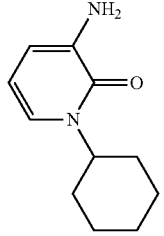 [SMILES: Nc1cccn(C2CCCCC2)c1=O] | MS (ES): m/z 452.76 [M + H]$^+$, LCMS purity: 96.31%, HPLC purity: 96.96%, CHIRAL HPLC 49.81%, 48.10%, $^1$H NMR (DMSO-d$_6$, 400 MHZ): 8.80 (s, 1H), 8.51-8.49 (d, J = 6.4 Hz, 1H), 8.19 (s, 1H), 8.04-8.02 (d, J = 8.8 Hz, 1H), 7.88-7.86 (d, J = 4.8 Hz, 1H), 7.41-7.40 (d, J = 6 Hz, 1H), 6.41-6.37 (t, J = 7.2 Hz, 1H), 6.25 (s, 1H), 5.40-5.39 (d, J = 4 Hz, 1H), 4.83-4.77 (t, J = 11.6 Hz, 1H), 4.58-4.55 (t, J = 6.8 Hz, 1H), 4.35 (bs, 1H), 3.17-3.16 (d, J = 5.2 Hz, 1H), 2.91-2.90 (d, J = 4.8 Hz, 3H), 2.18 (bs, 1H), 1.93-1.84 (m, 1H), 1.77 (bs, 2H), 1.72-1.63 (m, 4H), 1.45-1.34 (m, 2H), 1.27-1.22 (m, 3H). |
| I-1000<br>I-1001 | 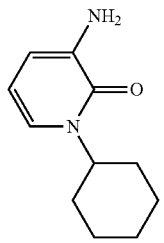 [SMILES: Nc1cccn(C2CCCCC2)c1=O] | I-942 was separated into isomers: (CHIRAL PAK AD-H 250 × 4.6 mm, 5 μM, DEA in HEX_IPA-MEOH (50-50) at 4 mL/min).<br>FR-a: MS (ES): m/z 452.51 [M + H]$^+$, LCMS purity: 97.38%, HPLC purity: 95%, Chiral HPLC: 100%, $^1$H NMR (DMSO-d$_6$, 400 MHZ): 8.81 (s, 1H), 8.53-8.51 (d, J = 6.4 Hz, 1H), 8.21 (s, 1H), 8.05-8.03 (d, J = 8.8 Hz, 1H), 7.89-7.88 (d, J = 4.8 Hz, 1H), 7.43-7.41 (d, J = 6.0 Hz, 1H), 6.42-6.38 (t, J = 7.2 Hz, 1H), 6.26 (s, 1H), 5.40-5.39 (d, J = 4 Hz, 1H), 4.85-4.79 (t, J = 12.0 Hz, 1H), 4.59-4.56 (m, 1H), 4.36 (bs, 1H), 2.93-2.92 (d, J = 4.8 Hz, 3H), 2.18 (bs, 1H), 1.93-1.84 (m, 1H), 1.77 (m, 1H), 1.72-1.63 (m, 4H), 1.45-1.34 (m, 3H), 1.27-1.22 (m, 2H), 1.95 (s, 2H).<br>FR-b: MS (ES): m/z 452.51 [M + H]$^+$, LCMS purity: 96.23%, HPLC purity: 96.37%, Chiral HPLC: 96.24%, $^1$H NMR (DMSO-d$_6$, 400 MHZ): 8.81 (s, 1H), 8.53-8.51 (d, J = 7.2 Hz, 1H), 8.21 |

TABLE 17-continued

| Compound # | Reagent | Characterization Data |
|---|---|---|
| | | (s, 1H), 8.05-8.03 (d, J = 8.8 Hz, 1H), 7.89-7.88 (d, J = 4.8 Hz, 1H), 7.43-7.41 (d, J = 6.8 Hz, 1H), 6.42-6.38 (t, J = 7.2 Hz, 1H), 6.26 (s, 1H), 5.43 (bs, 1H), 4.84-4.79 (t, J = 12.0 Hz, 1H), 4.59-4.56 (m, 1H), 4.36 (bs, 1H), 2.93-2.92 (d, J = 4.8 Hz, 3H), 2.18 (bs, 1H), 1.93-1.84 (m, 1H), 1.77 (m, 1H), 1.72-1.63 (m, 4H), 1.45-1.34 (m, 3H), 1.27-1.22 (m, 2H), 1.95 (s, 2H). |
| I-939 | 91b | MS (ES): 464.47 [M + H]+ LCMS purity: 98.52%, HPLC purity: 97.48%, CHIRAL HPLC purity: 49.30%, 49.93%, $^1$H NMR (DMSO-d$_6$, 400 MHZ): 8.93 (s, 1H), 8.67-8.65 (d, J = 7.6 Hz, 1H), 8.23 (s, 1H), 8.08-8.06 (d, J = 8.8 Hz, 1H), 7.93-7.92 (d, J = 4.8 Hz, 1H), 7.62-7.57 (m, 2H), 7.51-7.47 (t, J = 9.6 Hz, 1H), 7.43-7.39 (t, J = 8 Hz, 1H), 7.33-7.31 (d, J = 6.8 Hz, 1H), 6.52-6.48 (t, J = 7.2 Hz, 1H), 6.30 (s, 1H), 5.48-5.47 (d, J = 3.6 Hz, 1H), 4.62-4.58 (m, 1H), 4.38 (bs, 1H), 2.92-2.91(d, J = 4.8 Hz, 3H), 2.25-2.19 (m, 1H), 1.24 (s, 3H). |
| I-1035 I-1036 | 91b | Intermediate corresponding to 91.1 en route to I-939 was separated into isomers before BOC removal: (CHIRAL PAK AD-H 250 × 4.6 mm, 5 μM) and 0.1% DEA_HEX_IPA-MEOH (50-50) at 4 mL/min). Product prepared from FR-a: MS (ES): m/z 464.51 [M + H]+, LCMS purity: 98.42%, HPLC purity: 98.93%, Chiral HPLC: 98.26%, $^1$H NMR (DMSO-d$_6$, 400 MHZ): 8.93 (s, 1H), 8.66-8.64 (d, J = 6.4 Hz, 1H), 8.22 (s, 1H), 8.07-8.05 (d, J = 8.8 Hz, 1H), 7.93-7.92 (d, J = 4.8 Hz, 1H), 7.61-7.56 (m, 1H), 7.51-7.46 (m, 1H), 7.42-7.39 (m, 1H), 7.32-7.31 (d, J = 5.2 Hz, 1H), 7.08-7.06 (d, J = 7.6 Hz, 1H), 6.83-6.81 (d, J = 6.8 Hz, 1H), 6.51-6.47 (t, J = 6.8 Hz, 1H), 5.46 (s, 1H), 4.61-4.57 (m, 1H), 4.37 (s, 1H), 2.91-2.90 (d, J = 4.8 Hz, 3H), 0.95-0.82 (m, 4H). Product prepared from FR-b: MS (ES): m/z 464.46 [M + H]+, LCMS purity: 97.04%, HPLC purity: 98.48%, Chiral HPLC: 97.57%, $^1$H NMR (DMSO-d$_6$, 400 MHZ): 8.93 (s, 1H), 8.66-8.64 (d, J = 6.4 Hz, 1H), 8.22 (s, 1H), 8.07-8.05 (d, J = 8.8 Hz, 1H), 7.93-7.92 (d, J = 4.8 Hz, 1H), 7.61-7.56 (m, 1H), 7.51-7.46 (m, 1H), 7.42-7.39 (m, 1H), 7.32-7.31 (d, J = 5.2 Hz, 1H), 7.08-7.06 (d, J = 7.6 Hz, 1H), 6.83-6.81 (d, J = 6.8 Hz, 1H), 6.51-6.47 (t, J = 6.8 Hz, 1H), 5.46 (s, 1H), 4.61-4.57 (m, 1H), 4.37 (s, 1H), 2.91-2.90 (d, J = 4.8 Hz, 3H), 0.95-0.82 (m, 4H). |
| I-894 | | MS (ES): m/z 412.62 [M + H]+, LCMS purity: 98.28%, HPLC purity: 99.16%, CHIRAL HPLC purity: 98.82%, $^1$H NMR (DMSO-d$_6$, 400 MHZ): 8.85 (s, 1H), 8.53-8.51 (d, J = 6.4 Hz, 1H), 8.21 (s, 1H), 8.06-8.04 (d, J = 8.8 Hz, 1H), 7.89-7.88 (d, J = 4.8 Hz, 1H), 7.43-7.41 (d, J = 6 Hz, 1H), 6.44-6.40 (t, J = 7.2 Hz, 1H), 6.28 (s, 1H), 5.41-5.40 (d, J = 4 Hz, 1H), 5.23-5.16 (m, 1H), 4.62-4.55 (m, 1H), 4.36 (bs, 1H), 2.92-2.91 (d, J = 4.8 Hz, 3H), 2.21-2.18 (m, 1H), 2.13-2.06 (m, 2H), 1.77 (bs, 1H), 1.37-1.35 (d, J = 6.8 Hz, 6H). |

TABLE 17-continued

| Compound # | Reagent | Characterization Data |
|---|---|---|
| I-977<br>I-978 | 3-amino-1-isopropylpyridin-2(1H)-one | I-894 was separated into isomers: (CHIRALCEL OJ-H 250 mm*4.6 mm, 5 μM) in 0.1% DEA_HEX_IPA:ACN (70:30).<br>FR-a: MS(ES): m/z 412.52 [M + H]⁺, LCMS purity: 100%, HPLC purity: 100%, CHIRAL HPLC purity: 99.88%, ¹H NMR (DMSO-d₆, 400 MHZ): 8.84 (s, 1H), 8.53-8.51 (d, J = 8 Hz, 1H), 8.20 (s, 1H), 8.06-8.04 (d, J = 8 Hz, 1H), 7.89-7.87 (d, J = 8 Hz, 1H), 7.43-7.41 (d, J = 8 Hz, 1H), 6.42-6.40 (t, J = 8 Hz, 1H), 5.41-5.40 (d, J = 4 Hz, 1H), 5.22-5.16 (m, 1H), 4.58-4.56 (t, J = 8 HZ, 1H), 4.37-4.36 (d, J = 4 Hz, 1H), 2.92-2.91 (d, J = 4 Hz, 3H), 2.34-2.19 (m, 1H), 2.12-1.97 (m, 2H), 1.74-1.72 (t, J = 8 Hz, 2H), 1.37-1.35 (d, J = 8 Hz, 6H).<br>FR-b: MS(ES): m/z 412.52 [M + H]⁺, LCMS purity: 100%, HPLC purity: 99.41%, CHIRAL HPLC purity: 100%, ¹H NMR (DMSO-d₆, 400 MHZ): 8.84 (s, 1H), 8.53-8.51 (d, J = 8 Hz, 1H), 8.20 (s, 1H), 8.06-8.04 (d, J = 8 Hz, 1H), 7.89-7.87 (d, J = 8 Hz, 1H), 7.43-7.41 (d, J = 8 Hz, 1H), 6.42-6.40 (t, J = 8 Hz, 1H), 5.41-5.40 (d, J = 4 Hz, 1H), 5.22-5.16 (m, 1H), 4.58-4.56 (t, J = 8 HZ, 1H), 4.37-4.36 (d, J = 4 Hz, 1H), 2.92-2.91 (d, J = 4 Hz, 3H), 2.34-2.19 (m, 1H), 2.12-1.97 (m, 2H), 1.74-1.72 (t, J = 8 Hz, 2H), 1.37-1.35 (d, J = 8 Hz, 6H). |
| I-884 | 91d | MS (ES): m/z 552.57 [M + H]⁺, LCMS purity: 99.58%, HPLC purity: 98.93%, Chiral HPLC: 49.58%, 49.54%, ¹H NMR (DMSO-d₆, 400 MHZ): 8.23 (s, 1H), 8.14 (s, 1H), 8.12 (s, 1H), 8.04-8.02 (d, J = 4.8 Hz, 1H), 7.98 (bs, 1H), 7.84-7.80 (t, J = 8 Hz, 1H), 7.20-7.18 (d, J = 7.6 Hz, 1H), 6.42 (bs, 1H), 5.33-5.32 (d, J = 4 Hz, 1H), 4.56-4.53 (t, J = 6.4 Hz, 1H), 4.36 (bs, 1H), 3.82 (s, 3H), 2.97-2.95 (d, J = 4.8 Hz, 3H), 2.20-2.16 (m, 1H), 2.13-2.01 (m, 2H), 1.77 (bs, 1H), 1.24 (bs, 1H). |
| I-948<br>I-949 | 91d | Intermediate corresponding to 91.1 en route to I-884 was separated into isomers before BOC removal: (CHIRAL PAK AD-H 250 × 4.6 mm, 5 μM, 0.3% DEA in MeOH at 4 mL/min).<br>Product prepared from FR-a: MS (ES): m/z 452.47 [M + H]⁺, LCMS purity: 98.09%, HPLC purity: 98.29%, Chiral HPLC: 100%, ¹H NMR (DMSO-d₆, 400 MHZ): 8.23 (s, 1H), 8.18 (bs, 1H), 8.15 (bs, 1H), 8.04-8.02 (d, J = 4.8 Hz, 1H), 7.98 (bs, 1H), 7.83-7.80 (t, J = 8 Hz, 1H), 7.19-7.17 (d, J = 7.6 Hz, 1H), 6.49 (bs, 1H), 4.55-4.52 (t, J = 6.8 Hz, 1H), 4.34 (bs, 1H), 3.82 (s, 3H), 2.97-2.96 (d, J = 4.8 Hz, 3H), 1.65 (s, 1H), 1.24 (bs, 5H).<br>Product prepared from FR-b: MS (ES): m/z 452.47 [M + H]⁺, LCMS purity: 97.73%, HPLC purity: 96.98%, Chiral HPLC: 100%, ¹H NMR (DMSO-d₆, 400 MHZ): 9.91 (s, 1H), 8.22 (s, 1H), 8.19 (s, 1H), 8.15 (s, 1H), 8.04-8.03 (d, J = 5.2 Hz, 1H), 7.97 (bs, 1H), 7.83-7.79 (t, J = 8 Hz, 1H), 7.19-7.17 (d, J = 7.2 Hz, 1H), 6.50 (bs, 1H), 4.52 (bs, 1H), 4.34 (bs, 1H), 3.82 (s, 3H), 2.97-2.96 (d, J = 4.8 Hz, 3H), 1.63 (s, 1H), 1.24 (bs, 4H). |

TABLE 17-continued

| Compound # | Reagent | Characterization Data |
|---|---|---|
| I-844 | 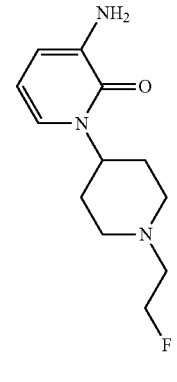 [SMILES: Nc1cccn(C2CCN(CCF)CC2)c1=O] | MS (ES): m/z 499.32 [M + H]$^+$, LCMS purity: 98.26%, HPLC purity: 95.24%, CHIRAL HPLC: 40.36%, 59.06%, $^1$H NMR (DMSO-d$_6$, 400 MHZ): 8.85 (s, 1H), 8.56-8.55 (d, J = 6.8 Hz, 1H), 8.21 (s, 1H), 8.04-8.02 (d, J = 8.8 Hz, 1H), 8.92-7.90 (d, J = 4.4 Hz, 1H), 7.24 (bs, 1H), 6.50 (bs, 1H), 6.30 (s, 1H), 5.42 (bs, 1H), 5.11 (bs, 1H), 4.98 (bs, 1H), 4.86 (bs, 1H), 4.58 (bs, 1H), 4.36 (bs, 1H), 3.73-3.68 (m, 3H), 3.50-3.47 (m, 2H), 2.93-2.92 (d, J = 4.4 Hz, 3H), 2.20 (bs, 2H), 2.08 (bs, 3H), 2.03-1.94 (m, 2H), 1.76 (bs, 2H). |
| I-896 I-897 | 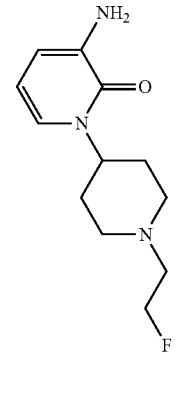 [SMILES: Nc1cccn(C2CCN(CCF)CC2)c1=O] | Intermediate corresponding to 91.1 en route to I-844 was separated into isomers before BOC removal: (CHIRAL PAK AD-H 250 × 4.6 mm, 5 μM, 0.1% DEA_HEX_ IPA-MeOH (50:50) at 4 mL/min). Product prepared from FR-a: MS (ES): m/z 499.40 [M + H]$^+$, LCMS purity: 98.67%, HPLC purity: 95.99%, Chiral HPLC: 96.05 $^1$H NMR (DMSO-d$_6$, 400 MHZ): 8.84 (s, 1H), 8.55-8.53 (d, J = 8 Hz, 1H), 8.21 (s, 1H), 8.05-8.03 (d, J = 6.8 Hz, 1H), 7.90-7.89 (d, J = 4 Hz, 1H), 7.46 (s, 1H), 6.41 (s, 1H), 6.28 (s, 1H), 5.42-5.41 (d, J = 4.4 Hz, 1H), 4.62-4.54 (m, 2H), 4.58 (s, 1H), 4.36 (s, 1H), 3.42-3.40 (d, J = 8 Hz, 1H), 3.08-3.02 (m, 2H), 2.93-2.92 (d, J = 4 Hz, 3H), 2.75 (s, 1H), 2.21-2.20 (d, J = 4 Hz, 3H), 2.21-2.06 (m, 2H), 2.05-1.94 (m, 2H), 1.78-1.75 (d, J = 12.6 Hz, 3H), 1.35-1.33 (d, J = 8 Hz, 1H). Product prepared from FR-b: MS (ES): m/z 499.40 [M + H]$^+$, LCMS purity: 96.81%, HPLC purity: 98.19% Chiral HPLC: 100%, $^1$H NMR (DMSO-d$_6$, 400 MHZ): 8.83 (s, 1H), 8.54-8.52 (d, J = 8 Hz, 1H), 8.21 (s, 1H), 8.05-8.03 (d, J = 6.8 Hz, 1H), 7.90-7.89 (d, J = 4 Hz, 1H), 7.46-7.45 (d, J = 4.6 Hz, 1H), 6.42-6.40 (t, J = 8 Hz, 1H), 6.28 (s, 1H), 5.42-5.41 (d, J = 4.4 Hz, 1H), 4.64-4.50 (m, 3H), 4.58 (s, 1H), 4.36 (s, 1H), 3.09-3.06 (d, J = 12 Hz, 2H), 2.93-2.91 (d, J = 8 Hz, 3H), 2.73-2.66 (m, 2H), 2.26-2.12 (m, 3H), 2.11-2.04 (m, 1H), 2.03-1.96 (m, 2H), 1.79-1.76 (d, J = 12.6 Hz, 3H), 1.35-1.33 (d, J = 8 Hz, 1H). |
| I-809 | 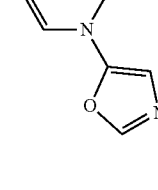 | MS (ES): m/z 437.34 [M + H]$^+$, LCMS purity: 95.32%, HPLC purity: 94.07%, Chiral HPLC: 97.91%, $^1$H NMR (DMSO-d$_6$, 400 MHZ): 9.06 (s, 1H), 8.63-8.62 (s, J = 6.4 Hz, 1H), 8.52 (s, 1H), 8.23 (s, 1H), 8.05-8.03 (d, J = 8.8 Hz, 1H), 7.97-7.96 (d, J = 4.8 Hz, 1H), 7.59 (s, 1H), 7.57-7.55 (d, J = 6 Hz, 1H), 6.60-6.56 (t, J = 7.2 Hz, 1H), 6.34 (s, 1H), 5.48-5.47 (d, J = 4 Hz, 1H), 4.60-4.56 (t, J = 7.2 Hz, 1H), 4.38 (bs, 1H), 2.93-2.91 (d, J = 4.8 Hz, 3H), 2.03-1.94 (m, 2H), 1.77 (bs, 2H). |

TABLE 17-continued

| Compound # | Reagent | Characterization Data |
|---|---|---|
| I-1017<br>I-1018 | 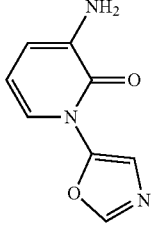 [SMILES: Nc1cccn(-c2cnco2)c1=O] | I-809 was separated into isomers: (CHIRAL PAK AD-H 250 × 4.6 mm, 5 μM) using DEA in HEX_IPA-MEOH (50-50) at 4 mL/min.<br>FR-a: MS (ES): m/z 437.57 [M + H]$^+$, LCMS purity: 99.26%, HPLC purity: 96.49%, Chiral HPLC: 98.09%, $^1$H NMR (DMSO-d$_6$, 400 MHZ): 8.54-8.53 (d, J = 6.0 Hz, 1H), 8.32 (s, 1H), 8.20 (s, 1H), 7.50 (s, 1H), 7.46-7.44 (d, J = 7.2 Hz, 1H), 7.07 (s, 1H), 6.81 (s, 1H), 6.57-6.53 (t, J = 7.2 Hz, 1H), 6.14 (s, 1H), 4.58-4.53 (m, 1H), 4.38 (s, 1H), 4.09-4.02 (m, 2H), 3.01 (s, 3H), 2.24-2.20 (m, 1H), 2.14-2.08 (m, 1H), 2.02-1.95 (m, 1H), 1.83-1.78 (m, 1H).<br>FR-b: MS (ES): m/z 437.57 [M + H]$^+$, LCMS purity: 100%, HPLC purity: 98.06%, Chiral HPLC: 99.55%, $^1$H NMR (DMSO-d$_6$, 400 MHZ): 8.59-8.58 (d, J = 7.6 Hz, 1H), 8.37 (s, 1H), 8.20 (s, 1H), 7.53 (s, 1H), 7.48-7.47 (d, J = 7.2 Hz, 1H), 7.02 (s, 1H), 6.85 (s 1H), 6.59-6.55 (t, J = 7.6 Hz, 1H), 6.23 (s, 1H), 4.61-4.53 (m, 1H), 4.41 (s, 1H), 4.07-4.00 (m, 2H), 2.97 (s, 3H), 2.24-2.20 (m, 1H), 2.14-2.08 (m, 1H), 2.02-1.95 (m, 1H), 1.83-1.78 (m, 1H). |
| I-654 | 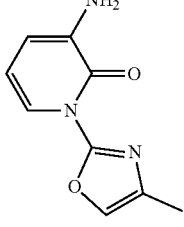 | MS(ES): m/z 451.83 [M + H]$^+$ LCMS purity: 99.63%, HPLC purity: 97.24%, Chiral HPLC purity: 49.49%, 49.41%, NMR (DMSO-d$_6$, 400 MHZ): 9.98 (s, 1H), 8.63-8.61 (t, J = 6 Hz, 1H), 8.23 (s, 1H), 8.03-7.96 (m, 3H), 7.41-7.39 (m, 1H), 6.53-6.49 (t, J = 7.6 Hz, 1H), 6.30 (s, 1H), 5.47 (s, 1H), 4.60-4.55 (m, 1H), 4.36 (s, 1H), 3.57 (s, 3H), 2.91 (s, 3H), 2.19-2.17 (d, J = 0.8 Hz, 2H), 2.02-1.93 (m, 2H). |
| I-706<br>I-707 | 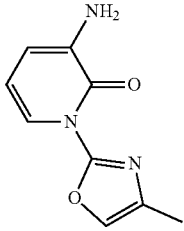 | I-654 was separated into isomers: (CHIRAL PAK AD-H 250 × 4.6 mm, 5 u) using 0.1% DEA in HEX_IPA-MEOH (50-50) at 4 mL/min.<br>FR-a: MS(ES): m/z 451.22 [M + H]$^+$, LCMS purity: 98.60%, HPLC purity: 100%, CHIRAL HPLC purity: 100%, $^1$H NMR (DMSO-d$_6$, 400 MHZ): 8.98 (s, 1H), 8.65-8.63 (d, J = 7.2 Hz, 1H), 8.24 (s, 1H), 8.04-7.95 (m, 3H), 7.42-7.41 (d, J = 6.4 Hz, 1H), 6.54-6.50 (t, J = 7.2 Hz, 1H), 6.31 (s, 1H), 5.47-46 (d, J = 3.2 Hz, 1H), 4.60-4.55 (m, 1H), 4.37 (s, 1H), 3.19-17 (d, J = 5.2 Hz, 1H), 2.93-2.92 (d, J = 4.8 Hz, 3H), 2.20 (bs, 2H), 2.13-1.94 (m, 2H), 1.76 (bs, 2H).<br>FR-b: MS(ES): m/z 451.22 [M + H]$^+$, LCMS purity: 98.32%, HPLC purity: 98.53%, CHIRAL HPLC purity: 98.38%, $^1$H NMR (DMSO-d$_6$, 400 MHZ): 8.98 (s, 1H), 8.65-8.63 (d, J = 7.2 Hz, 1H), 8.23 (s, 1H), 8.04 (s, 1H), 8.02 (s, 1H), 7.95 (s, 1H), 7.42-7.49 (d, J = 6.8 Hz, 1H), 6.54-6.50 (t, J = 7.2 Hz, 1H), 6.31 (s, 1H), 5.47-46 (d, J = 3.2 Hz, 1H), 4.60-4.56 (t, J = 7.2 Hz, 1H), 4.37 (s, 1H), 2.93-2.92 (d, J = 4.8 Hz, 3H), 2.20 (bs, 2H), 2.13-1.94 (m, 2H), 1.76 (bs, 2H). |

TABLE 17-continued

| Compound # | Reagent | Characterization Data |
|---|---|---|
| I-677 | 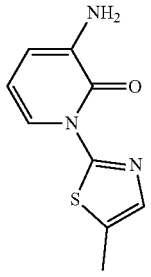 | MS (ES): m/z 467.17 [M + H]+, LCMS purity: 95.78%, HPLC purity: 96.69%, CHIRAL HPLC: 47.77%, 50.09%, $^1$H NMR (DMSO-d$_6$, 400 MHZ): 9.23 (s, 1H), 8.68-8.66 (d, J = 6.8 Hz, 1H), 8.42-8.41 (d, J = 7.2 Hz, 1H), 8.24 (s, 1H), 8.06-8.04 (d, J = 8.8 Hz, 1H), 7.98-7.97 (d, J = 4.8 Hz, 1H), 7.54 (s, 1H), 6.73-6.69 (d, J = 7.2 Hz, 1H), 6.38 (s, 1H), 5.49-5.48 (t, J = 4 Hz, 1H), 4.39 (bs, 1H), 2.94-2.93 (d, J = 4.4 Hz, 3H), 2.52 (s, 3H), 1.57 (bs, 2H), 1.24 (s, 3H). |
| I-1072 I-1073 | 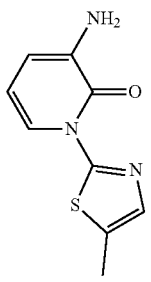 | I-677 was separated into isomers: (CHIRAL PAK AD-H 250 × 4.6 mm, 5 μM) using DEA in HEX_IPA-MEOH (50-50) at 4 mL/min. FR-a: MS (ES): m/z 467.29 [M + H]+, LCMS purity: 100%, HPLC purity: 95.00%, Chiral HPLC: 99.69%, $^1$H NMR (DMSO-d$_6$, 400 MHZ): 9.34 (s, 1H), 8.48-8.46 (d, J = 7.2 Hz, 1H), 8.40-8.38 (d, J = 7.2 Hz, 1H), 8.23 (s, 1H), 8.02-8.99 (d, J = 8.4 Hz, 2H), 7.55 (s, 1H), 6.68-6.64 (t, J = 7.6 Hz, 1H), 6.29 (s, 1H), 5.46-5.44 (d, J = 7.2 Hz, 1H), 4.25-4.20 (t, J = 8.8 Hz, 1H), 3.88-3.84 (t, J = 7.6 Hz, 1H), 2.93-2.92 (d, J = 4.8 Hz, 3H), 2.30 (s, 3H), 2.10-2.02 (m, 2H), 1.54-1.47 (m, 1H), 1.24-1.20 (m, 1H). FR-b: MS (ES): m/z 467.36 [M + H]+, LCMS purity: 95.21%, HPLC purity: 99.73%, Chiral HPLC: 100%, $^1$H NMR (DMSO-d$_6$, 400 MHZ): 9.33 (s, 1H), 8.47-8.46 (d, J = 6.4 Hz, 1H), 8.39-8.37 (d, J = 6.4 Hz, 1H), 8.22 (s, 1H), 8.01-7.99 (m, 2H), 7.54 (s, 1H), 6.68-6.64 (t, J = 7.2 Hz, 1H), 6.29 (s, 1H), 5.46-5.44 (d, J = 7.2 Hz, 1H), 4.25-4.20 (t, J = 8.8 Hz, 1H), 3.88-3.84 (t, J = 7.6 Hz, 1H), 2.94-2.93 (d, J = 4.8 Hz, 3H), 2.68 (s, 3H), 2.10-2.02 (m, 2H), 1.52-1.47 (m, 1H), 1.24-1.20 (m, 1H). |
| I-758 | 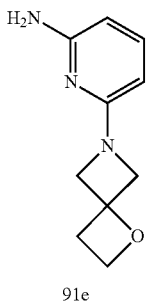 [SMILES: Nc1cccc(N2CC3(CCO3)C2)n1]91e | MS (ES): m/z 451.46 [M + H]+, LCMS purity: 95.08%, HPLC purity: 98.30%, CHIRAL HPLC: 100%, $^1$H NMR (DMSO-d$_6$, 400 MHZ): 9.51 (s, 1H), 8.19 (s, 1H), 8.14-8.12 (d, J = 8.8 Hz, 1H), 7.95-7.94 (d, J = 4.8 Hz, 1H), 7.55-7.51 (t, J = 7.6 Hz, 1H), 7.38 (bs, 1H), 6.24 (bs, 1H), 6.05-6.03 (d, J = 8 Hz, 1H), 4.47-4.44 (t, J = 7.6 Hz, 3H), 4.32 (bs, 1H), 4.22-4.20 (d, J = 9.6 Hz, 2H), 4.05-4.02 (d, J = 9.6 Hz, 2H), 2.94-2.93 (d, J = 4.8 Hz, 3H), 2.90-2.86 (t, J = 7.2 Hz, 2H), 2.17-2.15 (m, 1H), 2.06-2.00 (m, 3H), 1.27-1.74 (bs, 1H). |
| I-892 I-893 | 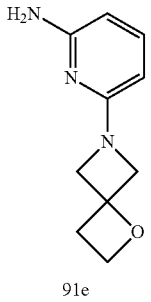 [SMILES: Nc1cccc(N2CC3(CCO3)C2)n1]91e | I-758 was separated into isomers: (CHIRAL PAK AD-H 250 × 4.6 mm, 5 μM) using DEA_HEX_IPA_MEOH (50-50) ISO (50-50). FR-a: MS(ES): m/z 451.21 [M + H]+, LCMS purity: 95.40%, HPLC purity: 95.23%, CHIRAL HPLC purity: 98.78%, $^1$H NMR (DMSO-d$_6$, 400 MHZ): 9.52 (s, 1H), 8.20 (s, 1H), 8.15-8.13 (d, J = 8.8 Hz, 1H), 7.54-7.52 (m, 1H), 6.06-6.04 (d, J = 8 Hz, 1H), 5.26-5.25 (d, J = 4 Hz, 1H), 4.48-4.45 (m, 3H), 4.33 (bs, 1H), 4.23-4.21 (d, J = 9.6 Hz, 2H), 4.06-4.03 (d, J = 9.6 Hz, 3H), 2.95-2.94 (d, J = 4 Hz, 3H), 2.91-2.87 (t, J = 7.2 Hz, 2H), 2.07-2.03 (m, 4H), 1.24 (bs, 2H). FR-b: MS(ES): m/z 451.21 |

TABLE 17-continued

| Compound # | Reagent | Characterization Data |
|---|---|---|
| | | [M + H]+, LCMS purity: 94.40%, HPLC purity: 95.26%, CHIRAL HPLC purity: 97.95%, 1H NMR (DMSO-d6, 400 MHZ): 9.52 (s, 1H), 8.20 (s, 1H), 8.15-8.13 (d, J = 8.8 Hz, 1H), 7.95-7.94 (d, J = 4.8 Hz, 1H), 7.56-7.52 (t, J = 8 Hz, 1H), 7.41-7.39 (d, J = 6.8 Hz, 1H), 6.43 (bs, 1H), 6.06-6.04 (d, J = 7.6 Hz, 1H), 5.26-5.25 (d, J = 3.6 Hz, 1H), 4.54-4.47 (m, 3H), 4.33 (bs, 1H), 4.23-4.21 (d, J = 9.6 Hz, 2H), 4.06-4.03 (d, J = 9.6 Hz, 2H), 2.95-2.94 (d, J = 4.8 Hz, 3H), 2.91-2.87 (t, J = 7.2 Hz, 2H), 2.07-2.03 (m, 3H), 1.78 (bs, 1H). |
| I-763 | 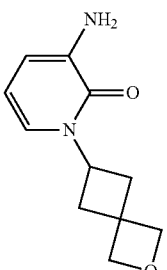<br>91f | MS (ES): m/z 466.37 [M + H]+ LCMS purity: 98.37%, HPLC purity: 98.48%, CHIRAL HPLC: 100%, 1H NMR (DMSO-d6, 400 MHZ): 8.81 (s, 1H), 8.51-8.49 (d, J = 4.8 Hz, 1H), 8.19 (s, 1H), 8.04-8.02 (d, J = 8.8 Hz, 1H), 7.88-7.87 (d, J = 4.8 Hz, 1H), 7.40-7.39 (d, J = 5.6 Hz, 1H), 6.41-6.37 (d, J = 7.2 Hz, 1H), 6.26 (s, 1H), 5.39-5.38 (d, J = 4 Hz, 1H), 4.96-4.92 (t, J = 8.4 Hz, 1H), 4.71 (s, 2H), 4.55 (s, 2H), 4.34 (bs, 1H), 2.90-2.89 (d, J = 4.8 Hz, 3H), 2.77-2.67 (m, 3H), 2.09 (bs, 1H), 2.03-1.94 (m, 3H), 1.72 (bs, 2H). |
| I-870<br>I-871 | 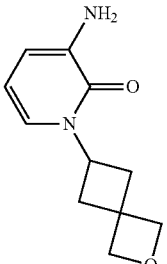<br>91f | I-763 was separated into isomers: (CHIRAL PAK AD-H 250 × 4.6 mm, 5 μM) using DEA_HEX_IPA-MEOH (50-50) ISO (50-50).<br>FR-a: MS(ES): m/z 466.40 [M + H]+, LCMS purity: 96.32%, HPLC purity: 95.08%, CHIRAL HPLC purity: 97.94%, 1H NMR (DMSO-d6, 400 MHZ): 8.81 (s, 1H), 8.51-8.49 (d, J = 7.2 Hz, 1H), 8.19 (s, 1H), 8.04-8.02 (d, J = 8.8 Hz, 1H), 7.88 (bs, 1H), 7.41-7.39 (d, J = 6.8 Hz, 1H), 6.41-6.38 (t, J = 6.8 Hz, 1H), 6.26 (s, 1H), 5.39 (bs, 1H), 4.96-4.92 (t, J = 8.4 Hz, 1H), 4.71 (s, 2H), 4.55 (s, 3H), 4.34 (bs, 1H), 2.90-2.89 (d, J = 4 Hz, 3H), 2.67 (bs, 2H), 2.50 (s, 2H), 2.18 (bs, 1H), 2.06 (bs, 1H), 2.01-1.95 (m, 1H), 1.73 (bs, 1H).<br>FR-b: MS(ES): m/z 466.46 [M + H]+, LCMS purity: 100%, HPLC purity: 99.48%, CHIRAL HPLC purity: 100%, 1H NMR (DMSO-d6, 400 MHZ): 8.83 (s, 1H), 8.52-8.50 (d, J = 7.2 Hz, 1H), 8.20 (s, 1H), 8.05-8.03 (d, J = 9.2 Hz, 1H), 7.89-7.88 (d, J = 4.4 Hz, 1H), 7.42-7.40 (d, J = 6.8 Hz, 1H), 6.42-6.39 (t, J = 7.2 Hz, 1H), 6.27 (s, 1H), 5.42 (bs, 1H), 4.97-4.93 (t, J = 8.4 Hz, 1H), 4.72 (s, 2H), 4.56 (s, 3H), 4.35 (bs, 1H), 3.35 (s, 1H), 2.91-2.90 (d, J = 4 Hz, 3H), 2.78-2.68 (m, 2H), 2.57 (s, 2H), 2.02-1.96 (m, 2H), 1.74 (bs, 1H). |
| I-745 | 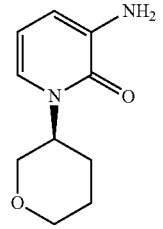<br>B-ii | MS (ES): m/z 454.45 [M + H]+, LCMS purity: 98.06%, HPLC purity: 98.07%, Chiral HPLC: 99.99%, 1H NMR (DMSO-d6, 400 MHZ): 8.84 (s, 1H), 8.53-8.52 (d, J = 6.8 Hz, 1H), 8.19 (s, 1H), 8.04-8.01 (d, J = 9.2 Hz, 1H), 7.89-7.88 (d, J = 4.4 Hz, 1H), 7.48-7.46 (d, J = 6.8 Hz, 1H), 6.42-6.38 (t, J = 7.2 Hz, 1H), 6.28 (s, 1H), 5.40-5.39 (d, J = 3.6 Hz, 1H), 4.88 (bs, 1H), 4.55 (bs, 1H), 4.34 (bs, 1H), 3.85-3.83 (d, J = 9.6 Hz, 2H), 3.58-3.53 (t, J = 10 Hz, 1H), 2.91-2.90 (d, J = 4.4 Hz, 3H), 2.33 (bs, 1H), 2.06-1.97 (m, 5H), 1.76 (bs, 3H). |

TABLE 17-continued

| Compound # | Reagent | Characterization Data |
|---|---|---|
| I-803<br>I-804 | 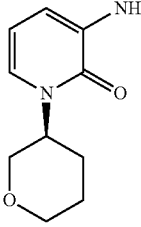<br>B-ii | I-745 was separated into isomers: (CHIRAL PAK AD-H 250 × 4.6 mm, 5 μM) using 0.1% DEA_MEOH (76:24). FR-a: MS(ES): m/z 454.27 [M + H]+, LCMS purity: 97.18%, HPLC purity: 96.03%, CHIRAL HPLC purity: 100%, $^1$H NMR (DMSO-$d_6$, 400 MHZ): 8.85 (s, 1H), 8.53-8.52 (d, J = 7.2 Hz, 1H), 8.20 (s, 1H), 8.04-8.02 (d, J = 8.4 Hz, 1H), 7.89 (s, 1H), 7.49-7.47 (d, J = 6.8 Hz, 1H), 6.42-6.38 (t, J = 7.2 Hz, 1H), 6.28 (s, 1H), 5.41 (s, 1H), 4.89 (s, 1H), 4.57 (s, 1H), 4.35 (s, 1H), 3.83 (s, 2H), 3.59-3.53 (t, J = 9.6 Hz, 2H), 2.91-2.90 (d, J = 4.0 Hz, 3H), 2.19 (bs, 1H), 2.07-1.97 (m, 4H), 1.77 (bs, 3H). FR-b: MS(ES): m/z 454.32 [M + H]+, LCMS purity: 100%, HPLC purity: 98.05%, CHIRAL HPLC purity: 100%, $^1$H NMR (DMSO-$d_6$, 400 MHZ): 8.85 (s, 1H), 8.54-8.52 (d, J = 6.8 Hz, 1H), 8.20 (s, 1H), 8.04-8.02 (d, J = 8.8 Hz, 1H), 7.89-7.88 (d, J = 4.8 Hz, 1H), 7.49-7.47 (d, J = 6.8 Hz, 1H), 6.42-6.38 (t, J = 7.2 Hz, 1H), 6.28 (s, 1H), 5.41 (s, 1H), 4.91-4.89 (m, 1H), 4.58-4.55 (m, 1H), 4.35 (s, 1H), 3.85-3.82 (d, J = 10.4 Hz, 2H), 3.59-3.42 (m, 2H), 2.91-2.90 (d, J = 4.4 Hz, 3H), 2.19 (bs, 1H), 2.07-1.96 (m, 4H), 1.77-1.73 (bs, 3H). |
| I-696 | 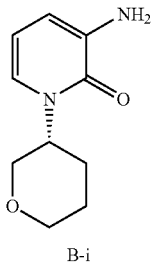 [SMILES: Nc1cccn([C@@H]2CCCOC2)c1=O]<br>B-i | MS (ES): m/z 454.30 [M + H]+, LCMS purity: 100%, HPLC purity: 97.41%, $^1$H NMR (DMSO-$d_6$, 400 MHZ): 8.85 (s, 1H), 8.53-8.52 (d, J = 6.4 Hz, 1H), 8.19 (s, 1H), 8.04-8.01 (d, J = 8.8 Hz, 1H), 7.89-7.88 (d, J = 4.8 Hz, 1H), 7.48-7.46 (d, J = 6.8 Hz, 1H), 6.42-6.38 (t, J = 7.2 Hz, 1H), 6.28 (s, 1H), 5.40-5.39 (d, J = 3.6 Hz, 1H), 4.88 (bs, 1H), 4.58-4.54 (t, J = 7.2 Hz, 1H), 4.35 (bs, 1H), 3.85-3.82 (m, 2H), 3.58-3.56 (t, J = 6 Hz, 1H), 3.17-3.16 (m, J = 5.6 Hz, 1H), 2.91-2.90 (d, J = 4.8 Hz, 3H), 2.21-2.18 (m, 1H), 2.07-2.05 (m, 2H), 2.02-1.97 (m, 2H), 1.73 (bs, 3H). |
| I-751<br>I-752 | 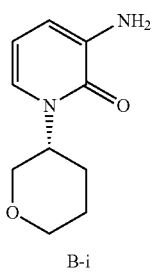 [SMILES: Nc1cccn([C@@H]2CCCOC2)c1=O]<br>B-i | I-696 was separated into isomers: (CHIRAL PAK AD-H 250 × 4.6 mm, 5 μM) using 0.1% DEA in MeOH. FR-a: MS(ES): m/z 454.32 [M + H]+, LCMS purity: 100%, HPLC purity: 99.21%, CHIRAL HPLC purity: 100%, $^1$H NMR (DMSO-$d_6$, 400 MHZ): 8.85 (s, 1H), 8.53-8.52 (d, J = 6.4 Hz, 1H), 8.20 (s, 1H), 8.04-8.01 (d, J = 8.8 Hz, 1H), 7.89-7.88 (d, J = 4.8 Hz, 1H), 7.48-7.47 (d, J = 7.2 Hz, 1H), 6.42-6.38 (t, J = 7.2 Hz, 1H), 6.28 (s, 1H), 5.41 (bs, 1H), 4.88 (m, 1H), 4.56 (m, 1H), 4.35 (bs, 2H), 3.85-3.82 (d, J = 11.2 Hz, 2H), 3.58-3.53 (t, J = 10 Hz, 2H), 2.91-2.90 (d, J = 4.8 Hz, 3H), 2.19 (bs, 1H), 1.73(bs, 4H), 1.04-1.03 (d, J = 6 Hz, 2H). FR-b: MS(ES): m/z 454.32 [M + H]+, LCMS purity: 100%, HPLC purity: 99.39%, CHIRAL HPLC purity: 97.64%, $^1$H NMR (DMSO-$d_6$, 400 MHZ): 8.85 (s, 1H), 8.53-8.51 (d, J = 7.6 Hz, 1H), 8.19 (s, 1H), 8.04-8.01 (d, J = 8.8 Hz, 1H), 7.89-7.88 (d, J = 4.8 Hz, 1H), 7.48-7.46 (d, J = 6 Hz, 1H), 6.42-6.38 (t, J = 7.2 Hz, 1H), 6.28 (s, 1H), 5.41 (bs, 1H), 4.89 (m, 1H), 4.56 (m, 1H), 4.34 (bs, 2H), 3.85-3.82 (d, J = 10.8 Hz, 2H), 3.58-3.53 (t, |

TABLE 17-continued

| Compound # | Reagent | Characterization Data |
|---|---|---|
| | | J = 10.4 Hz, 2H), 2.91-2.90 (d, J = 4.8 Hz, 3H), 2.19 (bs, 1H), 1.73 (bs, 4H), 1.04-1.03 (d, J = 6 Hz, 2H). |
| I-743 | 3-amino-1-(pyridin-2-yl)pyridin-2(1H)-one | MS (ES): m/z 447.56 [M + H]+, LCMS purity: 100%, HPLC purity: 100%, Chiral HPLC: 100%, 1H NMR (DMSO-d6, 400 MHZ): 8.95 (s, 1H), 8.65 (s, 1H), 8.63 (s, 1H), 8.23 (s, 1H), 8.09-8.04 (m, 2H), 7.93-7.92 (d, J = 4.8 Hz, 1H), 7.87-7.85 (d, J = 8 Hz, 1H), 7.57-7.54 (m, 2H), 6.55-6.51 (t, J = 7.2 Hz, 1H), 6.31 (s, 1H), 5.47-5.46 (d, J = 3.6 Hz, 1H), 4.61-4.59 (m, 1H), 4.38 (bs, 1H), 2.93-2.92 (d, J = 4.4 Hz, 3H), 2.12-2.00 (m, 3H), 1.78 (bs, 1H). |
| I-805 I-806 | 3-amino-1-(pyridin-2-yl)pyridin-2(1H)-one | Intermediate corresponding to 91.1 en route to I-743 was separated into isomers before BOC removal: (CHIRAL PAK AD-H 250 × 4.6 mm, 5 μM) using DEA_HEX_IPA-MeOH (50:50) at 4 mL/min. Product prepared from FR-a: MS (ES): m/z 447.44 [M + H]+, LCMS purity: 98.18%, HPLC purity: 99.52%, Chiral HPLC: 99.09%, 1H NMR (DMSO-d6, 400 MHZ): 8.96 (s, 1H), 8.66-8.65 (d, J = 4 Hz, 1H), 8.64 (s, 1H), 8.23 (s, 1H), 8.09-8.05 (m, 2H), 7.94-7.93 (d, J = 4.8 Hz, 1H), 7.88-7.85 (d, J = 8.4 Hz, 1H), 7.57-7.54 (m, 2H), 6.55-6.52 (t, J = 7.2 Hz, 1H), 6.32 (s, 1H), 5.47-5.46 (d, J = 3.6 Hz, 1H), 4.61-4.58 (t, J = 7.6 Hz, 1H), 4.39 (bs, 1H), 2.93-2.92 (d, J = 4.4 Hz, 3H), 2.22 (bs, 1H), 2.12-1.98 (m, 2H), 1.78 (bs, 1H). Product prepared from FR-b: MS (ES): m/z 447.39 [M + H]+, LCMS purity: 98.76%, HPLC purity: 98.17%, Chiral HPLC: 97.87%, 1H NMR (DMSO-d6, 400 MHZ): 8.96 (s, 1H), 8.66-8.65 (d, J = 3.6 Hz, 1H), 8.64 (s, 1H), 8.23 (s, 1H), 8.10-8.05 (m, 2H), 7.94-7.93 (d, J = 5.2 Hz, 1H), 7.88-7.85 (d, J = 8.4 Hz, 1H), 7.57-7.54 (m, 2H), 6.55-6.52 (t, J = 7.2 Hz, 1H), 6.32 (s, 1H), 5.47-5.47 (d, J = 3.6 Hz, 1H), 4.63-4.58 (m, 1H), 4.38 (bs, 1H), 2.93-2.92 (d, J = 4.8 Hz, 3H), 2.22 (bs, 1H), 2.12-1.98 (m, 2H), 1.78 (bs, 1H). |
| I-713 | 3-amino-5-chloro-1-(tetrahydro-2H-pyran-4-yl)pyridin-2(1H)-one | MS (ES): m/z 488.26 [M + H]+, LCMS purity: 100%, HPLC purity: 97.33%, CHIRAL HPLC: 70%, 28%, 1H NMR (DMSO-d6, 400 MHZ): 8.92 (s, 1H), 8.31-8.30 (d, J = 2.4 Hz, 1H), 8.25 (s, 1H), 7.99 (bs, 1H), 7.90-7.88 (d, J = 8.4 Hz, 1H), 7.62-7.61 (d, J = 2.4 Hz, 1H), ), 6.33 (s, 1H), 5.12-5.11 (d, J = 3.2 Hz, 1H), 5.01 (bs, 1H), 4.53-4.50 (t, J = 6.4 Hz, 1H), 4.29 (bs, 1H), 4.02-4.00 (d, J = 7.6 Hz, 2H), 3.53-3.48 (t, J = 11.2 Hz, 2H), 2.93-2.92 (d, J = 4.8 Hz, 3H), 2.24-2.20 (m, 2H), 2.07-2.00 (m, 3H), 1.77-1.74 (d, J = 10.4 Hz, 3H). |
| I-1068 I-1069 | 3-amino-5-chloro-1-(tetrahydro-2H-pyran-4-yl)pyridin-2(1H)-one | Intermediate corresponding to 91.1 en route to I-713 was resolved before BOC removal: (CHIRAL PAK AD-H 250 × 4.6 mm, 5 μM, DEA in HEX_IPA-MEOH (50-50) 4 mL/min). Product prepared from FR-a: MS (ES): m/z 488.41 [M + H]+, LCMS purity: 96.55%, HPLC purity: 95.02%, Chiral HPLC: 97.58%, 1H NMR (DMSO-d6, 400 MHZ): 8.92 (s, 1H), 8.31-8.30 (d, J = 2.4 Hz, 1H), 8.25 (s, |

TABLE 17-continued

| Compound # | Reagent | Characterization Data |
|---|---|---|
| | | 1H), 7.99 (bs, 1H), 7.90-7.88 (d, J = 8.4 Hz, 1H), 7.62-7.61 (d, J = 2.4 Hz, 1H), ), 6.33 (s, 1H), 5.12-5.11 (d, J = 3.2 Hz, 1H), 5.01 (bs, 1H), 4.53-4.50 (t, J = 6.4 Hz, 1H), 4.29 (bs, 1H), 4.02-4.00 (d, J = 7.6 Hz, 2H), 3.53-3.48 (t, J = 11.2 Hz, 2H), 2.93-2.92 (d, J = 4.8 Hz, 3H), 2.24-2.20 (m, 2H), 2.07-2.00 (m, 3H), 1.77-1.74 (d, J = 10.4 Hz, 3H). Product prepared from FR-b: MS (ES): m/z 488.47 [M + H]$^+$, LCMS purity: 97.07%, HPLC purity: 99.09%, Chiral HPLC: 99.15%, $^1$H NMR (DMSO-d$_6$, 400 MHZ): 8.92 (s, 1H), 8.31-8.30 (d, J = 2.4 Hz, 1H), 8.25 (s, 1H), 7.99 (bs, 1H), 7.90-7.88 (d, J = 8.4 Hz, 1H), 7.62-7.61 (d, J = 2.4 Hz, 1H), ), 6.33 (s, 1H), 5.12-5.11 (d, J = 3.2 Hz, 1H), 5.01 (bs, 1H), 4.53-4.50 (t, J = 6.4 Hz, 1H), 4.29 (bs, 1H), 4.02-4.00 (d, J = 7.6 Hz, 2H), 3.53-3.48 (t, J = 11.2 Hz, 2H), 2.93-2.92 (d, J = 4.8 Hz, 3H), 2.24-2.20 (m, 2H), 2.07-2.00 (m, 3H), 1.77-1.74 (d, J = 10.4 Hz, 3H). |
| I-679 | [structure: 2-amino-6-(2-oxopyrrolidin-1-yl)pyridine] | MS (ES): m/z 437.34 [M + H]$^+$, LCMS purity: 100%, HPLC purity: 97.90%, $^1$H NMR (DMSO-d$_6$, 400 MHZ): 9.74 (s, 1H), 8.21 (s, 1H), 8.13-8.10 (d, J = 8.4 Hz, 1H), 8.03-8.02 (d, J = 4.8 Hz, 1H), 7.92-7.89 (d, J = 8.8 Hz, 1H), 7.80-7.79 (m, 2H), 6.36 (s, 1H), 5.31-5.30 (d, J = 4.0 Hz, 1H), 4.52 (bs, 1H), 4.34(bs, 1H), 4.09-4.06 (t, 7.2 Hz, 2H), 2.95-2.94 (d, J = 4.0 Hz, 3H), 2.67 (bs, 2H), 2.08-2.02 (m, 4H), 1.78-1.76 (m, 1H), 1.55 (bs, 1H). |
| I-969 I-970 | [structure: 2-amino-6-(2-oxopyrrolidin-1-yl)pyridine] | Intermediate corresponding to 91.1 en route to I-679 was separated into isomers before BOC removal: CHIRALPAK IB 250 mm*4.6 mm, 5 u) and 0.1% DEA IPA:MEOH (50:50) at 4 mL/min. Product prepared from FR-a: MS (ES): m/z 437.36 [M + H]$^+$, LCMS purity: 94%, HPLC purity: 97.02%, Chiral HPLC: 98.20%, $^1$H NMR (DMSO-d$_6$, 400 MHZ): 9.79 (s, 1H), 8.24 (s, 1H), 8.15-8.13 (d, J = 8 Hz, 1H), 8.06 (s, 1H), 7.92-7.91 (t, J = 4 Hz, 1H), 7.81 (s, 1H), 7.09 (s, 1H), 6.84 (s, 1H), 6.38 (s, 1H), 4.53 (s, 1H), 4.35 (s, 1H), 4.10-4.09 (d, J = 6 Hz, 2H), 2.96-2.95 (d, J = 4.8 Hz, 1H), 2.62-2.60 (d, J = 4.9 Hz, 3H), 2.17 (s, J = 4.5 Hz, 2H), 2.09-2.08 (t, J = 4.5 Hz, 3H), 1.78 (s, 1H), 1.56 (s, 1H). Product prepared from FR-b: MS (ES): m/z 437.30 [M + H]$^+$, LCMS purity: 100%, HPLC purity: 100%, Chiral HPLC: 100%, $^1$H NMR (DMSO-d$_6$, 400 MHZ): 9.79 (s, 1H), 8.24 (s, 1H), 8.15-8.13 (d, J = 8 Hz, 1H), 8.06 (s, 1H), 7.93-7.92 (d, J = 4 Hz, 1H), 7.81 (s, 1H), 7.09 (s, 1H), 6.84 (s, 1H), 6.38 (s, 1H), 4.38 (s, 1H), 4.35 (s, 1H), 4.10-4.09 (t, J = 6 Hz, 2H), 2.96-2.95 (d, J = 4.8 Hz, 1H), 2.62-2.60 (d, J = 4.9 Hz, 3H), 2.17 (s, J = 4.5 Hz, 2H), 2.09-2.08 (t, J = 4.5 Hz, 3H), 1.78 (s, 1H), 1.56 (s, 1H). |
| I-662 | [structure: 8-amino-[1,2,4]triazolo[4,3-a]pyridine] | MS (ES): m/z 394.17 [M + H]$^+$, LCMS purity: 100%, HPLC purity: 98.67%, CHIRAL HPLC: 49.18%, 49.14%, $^1$H NMR (DMSO-d$_6$, 400 MHZ): 9.78 (bs, 1H), 8.67-8.62 (m, 2H), 8.56 (bs, 1H), 8.26 (bs, 1H), 8.11-8.09 (d, J = 8.4 Hz, 1H), 8.04 (bs, 1H), |

TABLE 17-continued

| Compound # | Reagent | Characterization Data |
|---|---|---|
| | | 7.26-7.23 (t, J = 6.8 Hz, 1H), 6.37 (bs, 1H), 5.46 (bs, 1H), 4.59 (bs, 1H), 4.38 (bs, 1H), 2.96 (bs, 3H), 2.19 (bs, 1H), 2.09 (bs, 1H), 1.76 (bs, 1H), 1.24 (s, 1H). |
| I-657 | | MS(ES): m/z 493.42 [M + H]⁺· LCMS purity: 98.58%, HPLC purity: 98.23%, CHIRAL HPLC: 50.17%, 48.96%, NMR (DMSO-d₆, 400 MHZ): 9.44 (s, 1H), 8.20 (s, 1H), 8.17-8.14 (d, J = 8.8 Hz, 1H), 7.95-7.94 (d, J = 4.8 Hz, 1H), 7.55-7.51 (t, J = 8 Hz, 1H), 7.35 (bs, 1H), 6.48-6.46 (d, J = 8.4 Hz, 1H), 6.33 (bs, 1H), 5.27-5.26 (d, J = 4 Hz, 1H), 4.55-4.52 (t, J = 6.8 Hz, 1H), 4.34 (bs, 1H), 3.79-3.74 (m, 2H), 3.71 (s, 2H), 3.53-3.47 (m, 2H), 2.93-2.92 (d, J = 4.8 Hz, 3H), 2.17 (bs, 1H), 2.15-2.07 (m, 2H), 1.94-1.91(t, J = 7.2 Hz, 2H), 1.79-1.70 (m, 3H), 1.61-1.59 (m, 4H). |
| I-720 I-721 | | I-657 was separated into isomers: (CHIRAL PAK AD-H 250 × 4.6 mm, 5 μM) using 0.1% DEA in IPA:ACN (50:50). FR-a: MS(ES): m/z 493.52 [M + H]⁺, LCMS purity: 96.24%, HPLC purity: 95.18%, CHIRAL HPLC purity: 99.51%, ¹H NMR (DMSO-d₆, 400 MHZ): 9.45 (s, 1H), 8.20 (s, 1H), 8.16-8.14 (d, J = 8.8 Hz, 1H), 7.96-7.95 (d, J = 4.8 Hz, 1H), 7.54-7.50 (t, J = 7.6 Hz, 1H), 7.35 (bs, 1H), 6.48-6.46 (d, J = 8 Hz, 1H), 6.32 (bs, 1H), 5.27-5.26 (d, J = 4 Hz, 1H), 4.54-4.51 (m, 1H), 4.34 (bs, 1H), 3.78-3.70 (m, 4H), 3.51-3.48 (m, 2H), 2.93-2.91 (d, J = 4.4 Hz, 3H), 2.17 (bs, 1H), 2.06-2.02 (t, J = 6.8 Hz, 2H), 1.92-1.88 (t, J = 6.8 Hz, 2H), 1.73-1.69 (m, 3H), 1.59 (bs, 4H). FR-b: MS(ES): m/z 493.52 [M + H]⁺, LCMS purity: 100%, HPLC purity: 98.75%, CHIRAL HPLC purity: 100%, ¹H NMR (DMSO-d₆, 400 MHZ): 9.45 (s, 1H), 8.20 (s, 1H), 8.16-8.14 (d, J = 8.8 Hz, 1H), 7.96-7.95 (d, J = 4.8 Hz, 1H), 7.54-7.50 (t, J = 8 Hz, 1H), 7.35 (bs, 1H), 6.48-6.46 (d, J = 8.4 Hz, 1H), 6.32 (bs, 1H), 5.27-5.26 (d, J = 4.4 Hz, 1H), 4.54-4.51 (m, 1H), 4.33 (bs, 1H), 3.78-3.74 (m, 4H), 3.51-3.47 (m, 2H), 2.93-2.91 (d, J = 4.8 Hz, 3H), 2.06-2.02 (m, 3H), 1.92-1.87 (t, J = 6.8 Hz, 2H), 1.73-1.69 (m, 3H), 1.59 (bs, 4H). |
| I-654 | | MS(ES): m/z 451.83 [M + H]⁺· LCMS purity: 99.63%, HPLC purity: 97.24%, Chiral HPLC purity: 49.49%, 49.41%, NMR (DMSO-d₆, 400 MHZ): 9.98 (s, 1H), 8.63-8.61 (t, J = 6 Hz, 1H), 8.23 (s, 1H), 8.03-7.96 (m, 3H), 7.41-7.39 (m, 1H), 6.53-6.49 (t, J = 7.6 Hz, 1H), 6.30 (s, 1H), 5.47 (s, 1H), 4.60-4.55 (m, 1H), 4.36 (s, 1H), 3.57 (s, 3H), 2.91 (s, 3H), 2.19-2.17 (d, J = 0.8 Hz, 2H), 2.02-1.93 (m, 2H). |
| I-661 | | MS (ES): m/z 394.22 [M + H]⁺, LCMS purity: 99.46%, HPLC purity: 95.08%, CHIRAL HPLC: 48.61%, 49.32%, ¹H NMR (DMSO-d₆, 400 MHZ): 9.65 (bs, 1H), 8.78 (s, 1H), 8.43-8.41 (d, J = 8 Hz, 1H), 8.20 (s, 1H), 8.12-8.10 (d, J = 8.8 Hz, 1H), 7.93-7.92 (d, J = 4.8 Hz, 1H), 7.53-7.49 (t, |

TABLE 17-continued

| Compound # | Reagent | Characterization Data |
|---|---|---|
| | | J = 8.4 Hz, 1H), 7.44-7.42 (d, J = 8 Hz, 1H), 6.19 (s, 1H), 5.25-5.24 (d, J = 3.6 Hz, 1H), 4.57-4.52 (m, 1H), 4.32 (bs, 1H), 2.95-2.94 (d, J = 4.8 Hz, 3H), 2.15-2.13 (m, 1H), 2.09-2.04 (m, 1H), 2.03-1.99 (m, 1H), 1.97-1.90 (m, 1H). |
| I-770 I-771 | 4-amino-benzoxazole (NH$_2$ substituted benzoxazole) | I-661 was separated into isomers: (CHIRAL PAK AD-H 250 × 4.6 mm, 5 μM) 0.1% DEA in methanol. FR-a: MS(ES): m/z 394.50 [M + H]$^+$, LCMS purity: 100%, HPLC purity: 98.72%, CHIRAL HPLC purity: 97.41%, $^1$H NMR (DMSO-d$_6$, 400 MHZ): 9.66 (s, 1H), 8.79 (s, 1H), 8.43-8.41 (d, J = 8 Hz, 1H), 8.21 (s, 1H), 8.12-8.10 (d, J = 9.2 Hz, 1H), 7.95-7.93 (d, J = 4.8 Hz, 1H), 7.54-7.50 (t, J = 8 Hz, 1H), 7.44-7.42 (s, J = 8 Hz, 1H), 6.20 (s, 1H), 5.26 (s, 1H), 4.57-4.54 (t J = 6.4 Hz, 1H), 4.32 (bs, 1H), 2.95-2.94 (d, J = 4.4 Hz, 3H), 2.09-1.91 (m, 3H), 1.25 (bs, 1H). FR-b: MS(ES): m/z 394.27 [M + H]$^+$, LCMS purity: 100%, HPLC purity: 99.58%, CHIRAL HPLC purity: 99.48%, $^1$H NMR (DMSO-d$_6$, 400 MHZ): 9.67 (s, 1H), 8.78 (s, 1H), 8.43-8.41 (d, J = 7.6 Hz, 1H), 8.20 (s, 1H), 8.12-8.10 (d, J = 9.2 Hz, 1H), 7.95-7.93 (d, J = 4.8 Hz, 1H), 7.53-7.49 (t, J = 8 Hz, 1H), 7.44-7.42 (s, J = 8 Hz, 1H), 6.19 (s, 1H), 5.27-5.26 (d, J = 4 Hz, 1H), 4.57-4.53 (t J = 7.2 Hz, 1H), 4.32 (bs, 1H), 2.95-2.94 (d, J = 4.8 Hz, 3H), 2.09-1.99 (m, 3H), 1.24 (bs, 1H). |
| I-1006 I-1007 | 3-amino-5-chloro-1-(1-methylpiperidin-4-yl)pyridin-2(1H)-one | Intermediate corresponding to 91.1 en route was separated into isomers before BOC removal: (CHIRAL PAK AD-H 250 × 4.6 mm, 5 μM) using DEA in HEX_IPA-MEOH (50-50) at 4 mL/min. Product prepared from FR-a: MS (ES): m/z 501.47 [M + H]$^+$, LCMS purity: 99.02%, HPLC purity: 97.36%, Chiral HPLC: 100%, $^1$H NMR (DMSO-d$_6$, 400 MHZ): 8.92 (s, 1H), 8.31-8.30 (d, J = 2.4 Hz, 1H), 8.25 (s, 1H), 8.00-7.99 (d, J = 4.8 Hz, 1H), 7.91-7.88 (d, J = 8.4 Hz, 1H), 7.56 (s, 1H), 6.32 (s, 1H), 5.13-5.12 (d, J = 4.0 Hz, 1H), 4.75 (s, 1H), 4.54-4.48 (m, 1H), 4.29 (bs, 1H), 2.97 (s, 2H), 2.93-2.92 (d, J = 4.8 Hz, 3H), 2.34 (s, 3H), 2.28-2.19 (m, 2H), 2.10-2.00 (m, 3H), 1.79-1.68 (m, 3H), 1.56 (bs, 1H), 1.24 (s, 1H). Product prepared from FR-b: MS (ES): m/z 501.52 [M + H]$^+$, LCMS purity: 100%, HPLC purity: 98.24%, Chiral HPLC: 99.45%, $^1$H NMR (DMSO-d$_6$, 400 MHZ): 8.93 (s, 1H), 8.31-8.30 (d, J = 2.4 Hz, 1H), 8.25 (s, 1H), 8.00-7.99 (d, J = 4.8 Hz, 1H), 7.90-7.88 (d, J = 8.4 Hz, 1H), 7.56 (s, 1H), 6.32 (s, 1H), 5.13-5.12 (d, J = 4.4 Hz, 1H), 4.75 (s, 1H), 4.54-4.50 (m, 1H), 4.29 (bs, 1H), 2.97 (s, 2H), 2.93-2.92 (d, J = 4.8 Hz, 3H), 2.34 (s, 3H), 2.28-2.19 (m, 2H), 2.10-2.00 (m, 3H), 1.79-1.68 (m, 3H), 1.56 (bs, 1H), 1.24 (s, 1H). |

TABLE 17-continued

| Compound # | Reagent | Characterization Data |
|---|---|---|
| I-1391 | 911 (3,3-difluorocyclobutyl pyridinone with NH₂) | MS (ES): 460.47 [M + H]⁺ LCMS purity: 94.61%, HPLC purity: 95.66%, CHIRAL HPLC: 52.11%, 47.88%, $^1$H NMR (DMSO-d$_6$, 400 MHZ): 8.89 (s, 1H), 8.56-8.54 (d, J = 6.4 Hz, 1H), 8.20 (s, 1H), 8.04-8.02 (d, J = 9.2 Hz, 1H), 7.89-7.88 (d, J = 4.8 Hz, 1H), 7.41-7.39 (d, J = 6.8 Hz, 1H), 7.08 (bs, 1H), 6.83 (bs, 1H), 6.44-6.41 (t, J = 7.2 Hz, 1H), 6.28 (s, 1H), 4.90 (bs, 1H), 4.59-4.55 (m, 1H), 4.35 (bs, 1H), 3.32 (s, 1H), 2.90-2.89 (d, J = 4.8 Hz, 3H), 2.18 (m, 1H), 2.09-2.05 (m, 1H), 2.01-1.95 (m, 1H), 1.73 (bs, 1H), 1.47 (bs, 1H), 1.23 (bs, 1H). |
| I-1306 I-1307 | 911 (3,3-difluorocyclobutyl pyridinone with NH₂) | Intermediate corresponding to 91.1 en route to I-1391 was separated into isomers before BOC removal: CHIRALPAK IC (250 mm*4.6 mm, 5 u) and 0.1% DEA MEOH (70-30) at 4 mL/min.<br>Product prepared from FR-a: MS (ES): m/z 460.35 [M + H]⁺, LCMS purity: 100%, HPLC purity: 99.50%, Chiral HPLC: 100%, $^1$H NMR (DMSO-d$_6$, 400 MHZ): 8.90 (s, 1H), 8.56-8.54 (d, J = 7.6 Hz, 1H), 8.20 (s, 1H), 8.05-8.03 (d, J = 8.2 Hz, 1H), 7.90-7.89 (d, J = 4.8 Hz, 1H), 7.41-7.39 (d, J = 8.4 Hz, 1H), 6.45-6.43 (t, J = 7.8 Hz, 1H), 6.28 (s, 1H), 5.42-5.41 (d, J = 4 Hz, 1H), 4.94-4.89 (m, 1H), 4.59-4.53 (m, 1H), 4.36-4.35 (d, J = 4 Hz, 1H), 3.28-3.10 (m, 4H), 2.90-2.89 (d, J = 4 Hz, 3H), 2.19-2.18 (d, J = 3.6 Hz, 1H), 2.11-1.95 (m, 2H), 1.76-1.73 (d, J = 11.4 Hz, 1H).<br>Product prepared from FR-b: MS (ES): m/z 460.35 [M + H]⁺, LCMS purity: 99.44%, HPLC purity: 99.04% Chiral HPLC: 99.90%, $^1$H NMR (DMSO-d$_6$, 400 MHZ): 8.90 (s, 1H), 8.56-8.54 (d, J = 7.6 Hz, 1H), 8.20 (s, 1H), 8.05-8.03 (d, J = 8.2 Hz, 1H), 7.90-7.89 (d, J = 4.8 Hz, 1H), 7.41-7.39 (d, J = 8.4 Hz, 1H), 6.45-6.43 (t, J = 7.8 Hz, 1H), 6.28 (s, 1H), 5.42 (s, 1H), 4.91-4.90 (t, J = 4 Hz, 1H), 4.60-4.55 (m, 1H), 4.35 (s, 1H), 3.30-3.12 (m, 4H), 2.90-2.89 (d, J = 4 Hz, 3H), 2.19-2.18 (d, J = 3.6 Hz, 1H), 2.11-1.95 (m, 2H), 1.76-1.73 (d, J = 11.4 Hz, 1H). |
| I-1292 | (4-methoxycyclohexyl pyridinone with NH₂·HCl) | MS (ES): 482.87 [M + H]⁺ LCMS purity: 96.99%, HPLC purity: 95.47%, CHIRAL HPLC: 47.57%, 49.02%, $^1$H NMR (DMSO-d$_6$, 400 MHZ): 8.81 (s, 1H), 8.51-8.49 (d, J = 7.2 Hz, 1H), 8.19 (s, 1H), 8.04-8.02 (d, J = 9.2 Hz, 1H), 7.89-7.88 (d, J = 4.4 Hz, 1H), 7.32-7.30 (d, J = 6.4 Hz, 1H), 6.41-6.38 (t, J = 7.6 Hz, 1H), 6.25 (s, 1H), 5.37-5.36 (d, J = 4.4 Hz, 1H), 4.85-4.79 (m, 1H), 4.60-4.52 (m, 1H), 4.35 (bs, 1H), 3.57 (bs, 1H), 3.26 (s, 3H), 2.91-2.90 (d, J = 4.8 Hz, 3H), 2.03-1.95 (m, 3H), 1.76 (bs, 2H), 1.61-1.55 (m, 5H), 1.23 (bs, 2H). |

TABLE 17-continued
| Compound # | Reagent | Characterization Data |
|---|---|---|
| I-1259 | (structure shown) | MS (ES): m/z 451.51 [M + H]$^+$, LCMS purity: 100%, HPLC purity: 97.57%, $^1$H NMR (DMSO-$d_6$, 400 MHZ): 8.98 (s, 1H), 8.66-8.64 (d, J = 7.6 Hz, 1H), 8.44 (s, 1H), 8.23 (s, 1H), 8.05-8.02 (d, J = 8.4 Hz, 1H), 7.96-7.95 (d, J = 4.8 Hz, 1H), 7.34-7.32 (d, J = 5.6 Hz, 1H), 6.53-6.49 (d, J = 7.2 Hz, 1H), 6.32 (s, 1H), 5.48-5.47 (d, J = 3.6 Hz, 1H), 4.60 (bs, 1H), 4.38 (bs, 1H), 2.92-2.91 (d, J = 4.8 Hz, 3H), 2.20 (bs, 1H), 2.07 (s, 4H), 1.24 (bs, 1H), 1.12-1.08 (t, J = 7.2 Hz, 1H). |
Synthesis of 5-(5-fluoro-1-isopropyl-1-pyrrolo[2,3-b]pyridin-3-yl)-N-(2-hydroxycyclobutyl)-7-(methylamino)pyrazolo[1,5-a]pyrimidine-3-carboxamide (I-1013)
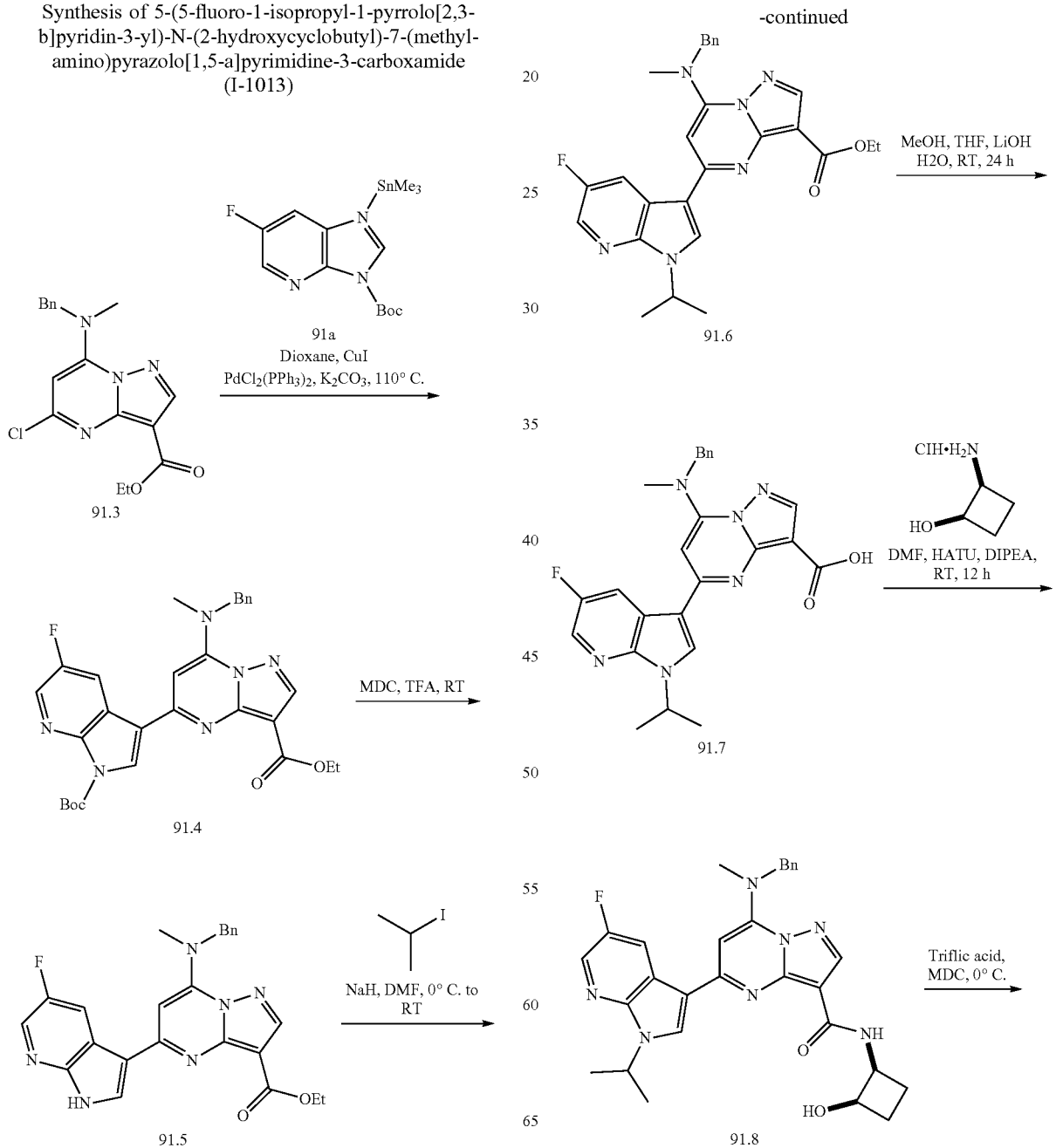

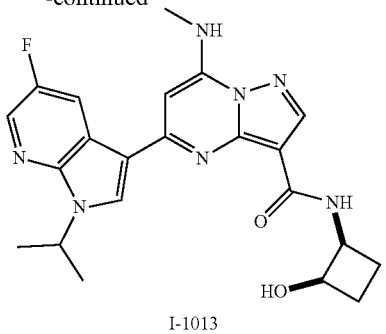

I-1013

Synthesis of Compound 91.3.

Compound was synthesized using general procedure of core synthesis to obtain 91.3. (Yield: 45%) MS(ES): m/z 345.10 [M+H]⁺.

Synthesis of Compound 91.4.

Argon was purged for 15 min through a stirring solution of 91.3 (3.5 g, 1.16 mmol, 1.0 eq), 91a (0.696 g, 1.74 mmol, 1.5 eq) and potassium carbonate (0.4 g, 2.9 mmol, 2.5 eq) in 1,4-dioxane (8 ml). Copper(I) iodide (0.043 g, 0.23 mmol, 0.2 eq) and Bis(triphenylphosphine)palladium(II) dichloride (0.077 mg, 0.11 mmol, 0.1 eq) was added to it and further purging done for 10 min. Reaction was allowed to stirred at 110° C. for 6 h. After completion of reaction, reaction mixture was poured over water and product was extracted with ethyl acetate. Organic layer was combined, washed with brine solution, dried over sodium sulphate and concentrated under reduced pressure to obtain 91.4. (0.4 g, 63.31%). MS (ES): m/z 545.23 [M+H]⁺.

Synthesis of Compound 91.5.

Compound was synthesized using general procedure C to obtain 91.5. (0.310 g, 94.96%), MS (ES): 445.17 [M+H]⁺.

Synthesis of Compound 91.6.

To a solution of 91.5 (0.310 g, 0.69 mmol, 1 eq) in dimethylformamide (3 mL), Sodium hydride (0.033 g, 1.38 mmol, 2 eq) was added at 0° C. Isopropyl iodide (0.053 mg, 0.89 mmol, 1.3 eq) was added to it and stirred at room temperature for 1 h. The reaction mixture was stirred at room temperature for 1 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 10% ethyl acetate in hexane to obtain 91.6. (0.262 g, Yield: 77.21%). MS (ES): m/z 487.22 [M+H]⁺

Synthesis of Compound 91.7.

To a solution of 91.6 (0.262 g, 0.53 mmol, 1.0 eq), in methanol:tetrahydrofuran: water (5 mL, 2:2:1) was added lithium hydroxide (0.127 g, 5.3 mmol, 10 eq). The reaction was stirred at 60° C. for 24 h. After completion of reaction, reaction mixture was concentrated under reduced pressure to obtain residue. To this added water and acidified with IN hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.7. (0.2 g, 81.01%). MS(ES): m/z 459.19 [M+H]⁺

Synthesis of Compound 91.8.

Compound was synthesized using general procedure A to obtain 91.8. (0.130 g, 56.49%), MS (ES): 528.25 [M+H]⁺

Synthesis of Compound I-1013:

Solution of 91.8 (0.030 g, 0.056 mmol, 1.0 eq) in dichloromethane (0.5 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1013 (0.020 g, 80.40%), MS (ES): m/z 438.51 [M+H]⁺, LCMS purity: 95.94%, HPLC purity: 94.13%, CHIRAL HPLC: 47.78%, 47.89%, ¹H NMR (DMSO-d₆, 400 MHZ): 8.92 (s, 1H), 8.73-8.72 (d, J=2.4 Hz, 1H), 8.66-8.64 (d, J=8.4 Hz, 1H), 8.44 (s, 1H), 8.37 (s, 1H), 8.28-8.27 (d, J=4 Hz, 1H), 6.73 (s, 1H), 5.42 (bs, 1H), 5.21-5.14 (m, 1H), 4.59-4.56 (m, 1H), 4.40 (bs, 1H), 3.15-3.14 (d, J=4 Hz, 3H), 2.23-2.19 (m, 1H), 2.12-2.09 (m, 2H), 1.91-1.86 (m, 1H), 1.60 (m, 6H).

Synthesis of 5-(1-cyclopropyl-1H-pyrrolo[2,3-b]pyridin-3-yl)-N-((1 S,2R)-2-hydroxycyclobutyl)-7-(methylamino)pyrazolo[1,5-a]pyrimidine-3-carboxamide (I-992)

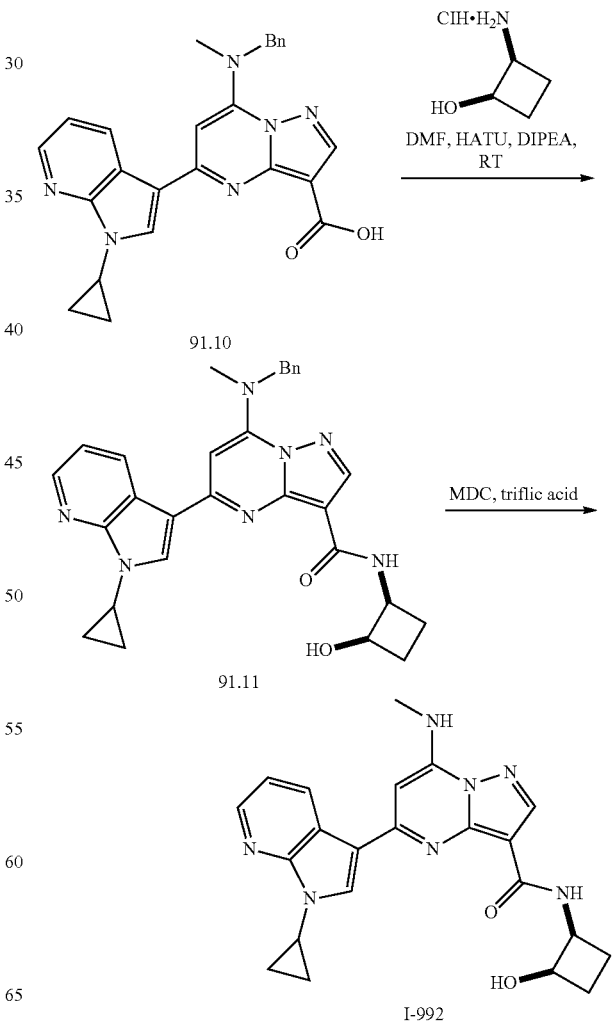

Synthesis of Compound 91.10.

Compound was synthesized as per Example 78 to obtain 91.10. (Yield: 78.96%). MS (ES): m/z 439.18 [M+H]$^+$.

Synthesis of Compound 91.11.

Compound was synthesized using general procedure A to obtain 91.11. (0.170 g, 73.43%), MS (ES): 508.24 [M+H]$^+$.

Synthesis of Compound I-992.

Mixture of 91.11 (0.170 g, 0.33 mmol, 1.0 eq) in dichloromethane (2 mL) was cooled to 0° C. and triflic acid (2 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-992 (0.110 g, 78.67%), MS (ES): m/z 418.57 [M+H]$^+$, LCMS purity: 100%, HPLC purity: 99.01%, $^1$H NMR (DMSO-d$_6$, 400 MHZ): 9.02-9.00 (d, J=6.8 Hz, 1H), 8.62 (bs, 1H), 8.59 (bs, 1H), 8.40-8.39 (d, J=3.2 Hz, 1H), 8.35 (s, 1H), 8.23-8.22 (d, J=4.8 Hz, 1H), 7.32-7.29 (m, 1H), 6.75 (s, 1H), 5.51-5.50 (d, J=4 Hz, 1H), 4.59-4.57 (m, 1H), 4.42 (bs, 1H), 3.78 (bs, 1H), 3.12-3.10 (d, J=4.8 Hz, 3H), 2.21-2.13 (m, 3H), 1.84 (bs, 1H), 1.33 (bs, 2H), 1.19-1.14 (m, 2H).

Synthesis of 5-(1-cyclopropyl-1H-pyrrolo[2,3-b]pyridin-3-yl)-N-((1S,2R)-2-hydroxy cyclobutyl)-7-(methylamino)pyrazolo[1,5-a]pyrimidine-3-carboxamide (I-1080) and 5-(1-cyclopropyl-1H-pyrrolo[2,3-b]pyridin-3-yl)-N-((1R,2S)-2-hydroxycyclobutyl)-7-(methylamino)pyrazolo[1,5-a]pyrimidine-3-carboxamide (I-1081)

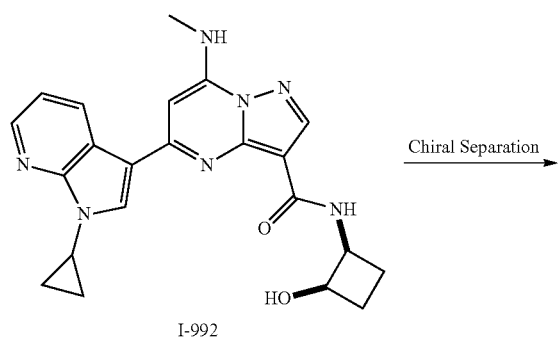

I-992

Chiral Separation →

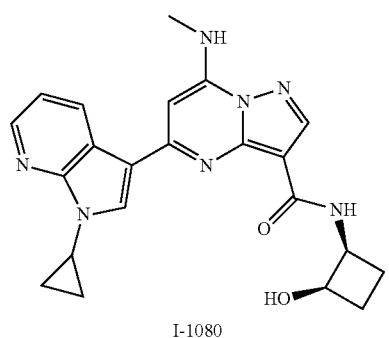

I-1080

+

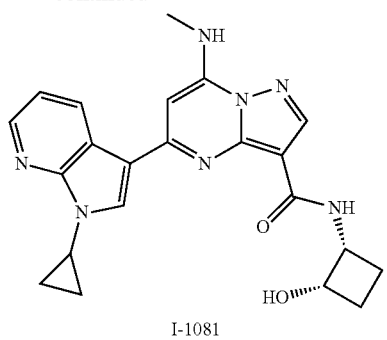

I-1081

Synthesis of Compound I-1080 & I-1081.

Isomers of I-992 (0.090 g) were separated out using column (CHIRAL PAK AD-H 250×4.6 mm, 5 u) 0.1% DEA_MEOH (70-30) to get pure fraction-1 (FR-a) and fraction-2 (FR-b). FR-a was concentrated under reduced pressure at 30° C. to afford 0.030 g. MS(ES): m/z 418.57 [M+H]$^+$, LCMS purity: 100%, HPLC purity: 97.96%, CHIRAL HPLC purity: 99.81%, $^1$H NMR (DMSO-d$_6$, 400 MHZ): 9.02-9.00 (d, J=6.8 Hz, 1H), 8.63-8.60 (m, 2H), 8.41-8.40 (d, J=3.6 Hz, 1H), 8.35 (s, 1H), 8.24-8.23 (d, J=4.8 Hz, 1H), 7.32-7.29 (m, 1H), 6.75 (s, 1H), 5.51-5.50 (d, J=4.0 Hz, 1H), 4.59-4.57 (m, 1H), 4.42 (s, 1H), 3.79-3.78 (m, 1H), 3.12-3.11 (d, J=4.8 Hz, 3H), 2.33-2.04 (m, 4H), 1.23-1.14 (m, 4H).

FR-b was concentrated under reduced pressure at 30° C. to afford 0.030 g. MS(ES): m/z 418.20 [M+H]$^+$, LCMS purity: 99.03%, HPLC purity: 99.50%, CHIRAL HPLC purity: 98.50%, $^1$H NMR (DMSO-d$_6$, 400 MHZ): 9.02-9.00 (d, J=7.6 Hz, 1H), 8.63-8.59 (m, 2H), 8.41-8.40 (d, J=3.6 Hz, 1H), 8.35 (s, 1H), 8.24-8.23 (d, J=5.2 Hz, 1H), 7.32-7.29 (m, 1H), 6.75 (s, 1H), 5.51-5.50 (d, J=4.0 Hz, 1H), 4.59 (s, 1H), 4.42 (s, 1H), 3.79-3.78 (m, 1H), 3.12-3.11 (d, J=4.8 Hz, 3H), 2.33-2.04 (m, 4H), 1.23-1.14 (m, 4H).

Synthesis of N-(2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-851)

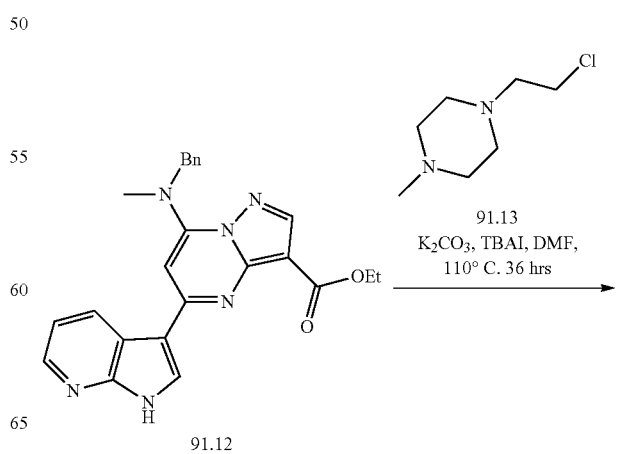

91.12

91.13
K$_2$CO$_3$, TBAI, DMF,
110° C. 36 hrs →

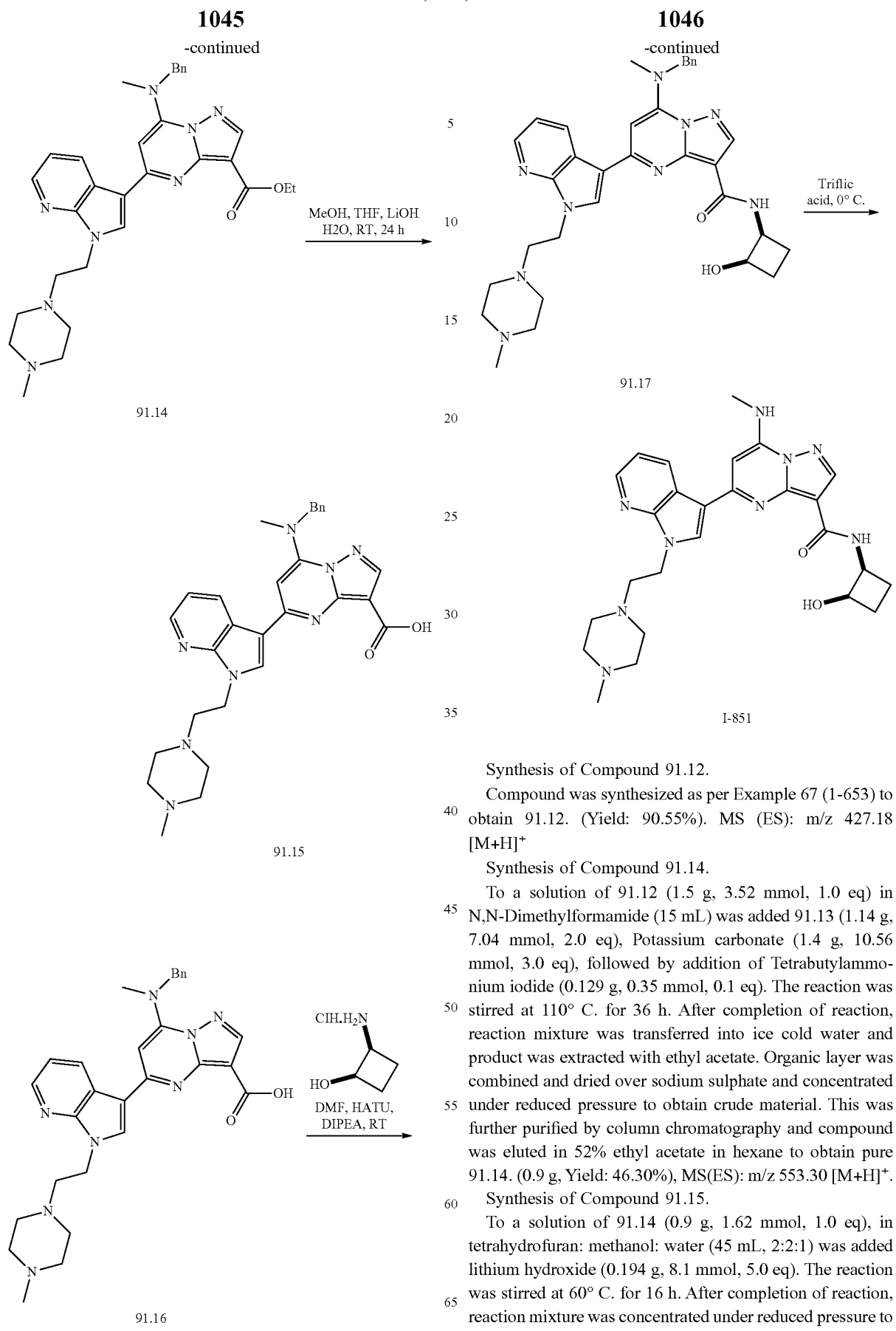

Synthesis of Compound 91.12.

Compound was synthesized as per Example 67 (1-653) to obtain 91.12. (Yield: 90.55%). MS (ES): m/z 427.18 [M+H]+

Synthesis of Compound 91.14.

To a solution of 91.12 (1.5 g, 3.52 mmol, 1.0 eq) in N,N-Dimethylformamide (15 mL) was added 91.13 (1.14 g, 7.04 mmol, 2.0 eq), Potassium carbonate (1.4 g, 10.56 mmol, 3.0 eq), followed by addition of Tetrabutylammonium iodide (0.129 g, 0.35 mmol, 0.1 eq). The reaction was stirred at 110° C. for 36 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 52% ethyl acetate in hexane to obtain pure 91.14. (0.9 g, Yield: 46.30%), MS(ES): m/z 553.30 [M+H]+.

Synthesis of Compound 91.15.

To a solution of 91.14 (0.9 g, 1.62 mmol, 1.0 eq), in tetrahydrofuran: methanol: water (45 mL, 2:2:1) was added lithium hydroxide (0.194 g, 8.1 mmol, 5.0 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 91.15. (0.7 g, Yield: 81.94%). MS(ES): m/z 525.27 [M+H]$^+$.

Synthesis of Compound 91.16.

Compound was synthesized using general procedure A to obtain 91.16. (0.150 g, Yield: 66.27%). MS(ES): m/z 594.33 [M+H]$^+$.

Synthesis of Compound I-851.

The compound 91.17 (0.030 g, 0.050 mmol, 1.0 eq) was dissolved in dichloromethane (1 mL). Triflic acid (0.5 mL) was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-851 (0.019 g, Yield: 74.67%). MS(ES): m/z 504.47 [M+H]$^+$, LCMS purity: 96.98%, HPLC purity: 96.07%, CHIRAL HPLC: 97.12%, $^1$H NMR (DMSO-d$_6$, 400 MHZ): 8.99 (bs, 1H), 8.74 (s, 1H), 8.68-8.66 (d, J=8.4 Hz, 1H), 8.38 (s, 1H), 8.36 (s, 1H), 8.26-8.25 (d, J=5.2 Hz, 1H), 7.30-7.27 (m, 1H), 6.67 (s, 1H), 5.57-5.56 (d, J=3.6 Hz, 1H), 4.61-4.57 (t, J=6 Hz, 1H), 4.50-4.44 (m, 3H), 3.33 (s, 1H), 3.13-3.11 (d, J=4.4 Hz, 3H), 2.84-2.80 (t, J=6.4 Hz, 2H), 2.22 (bs, 3H), 2.14 (s, 4H), 2.06-2.02 (m, 1H), 1.85 (bs, 1H), 1.40 (s, 1H), 1.24 (bs, 1H), 1.12-1.08 (t, J=7.2 Hz, 2H), 0.86 (bs, 1H).

Synthesis of N-((1S,2R)-2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-906) and N-((1R,2S)-2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-907)

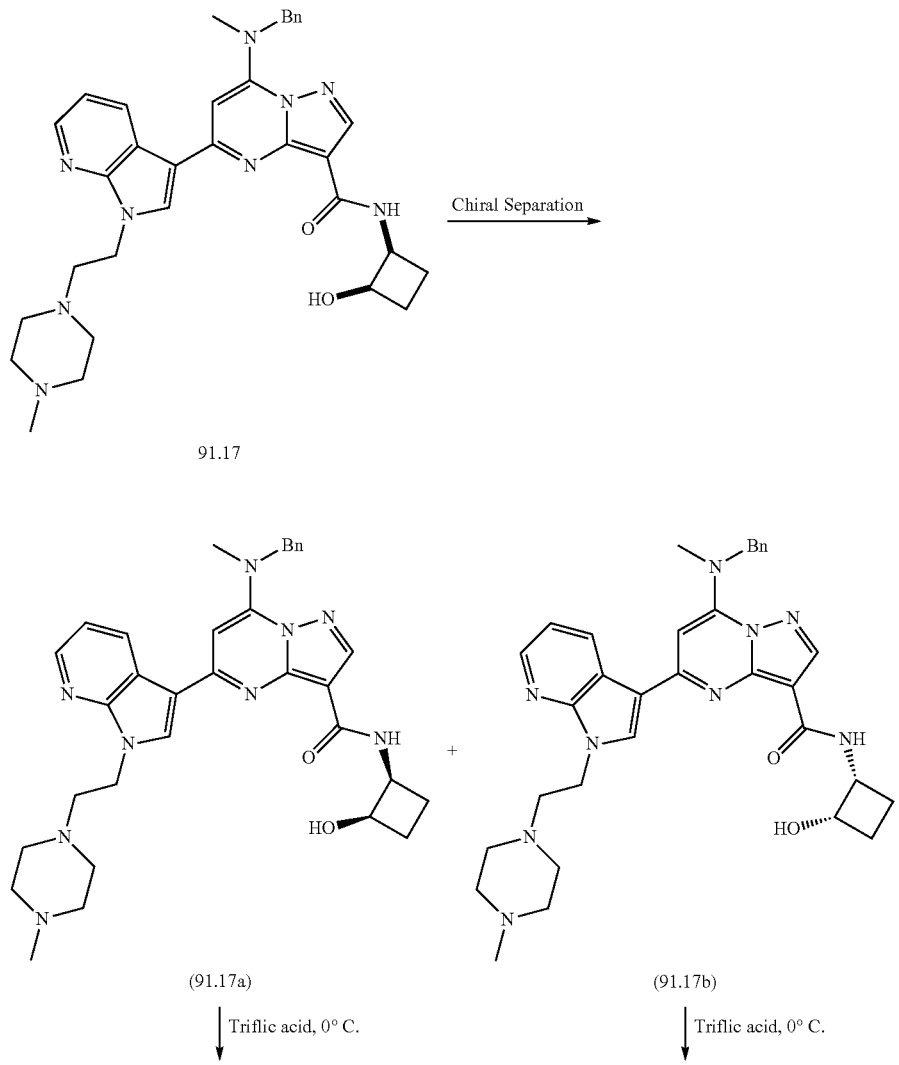

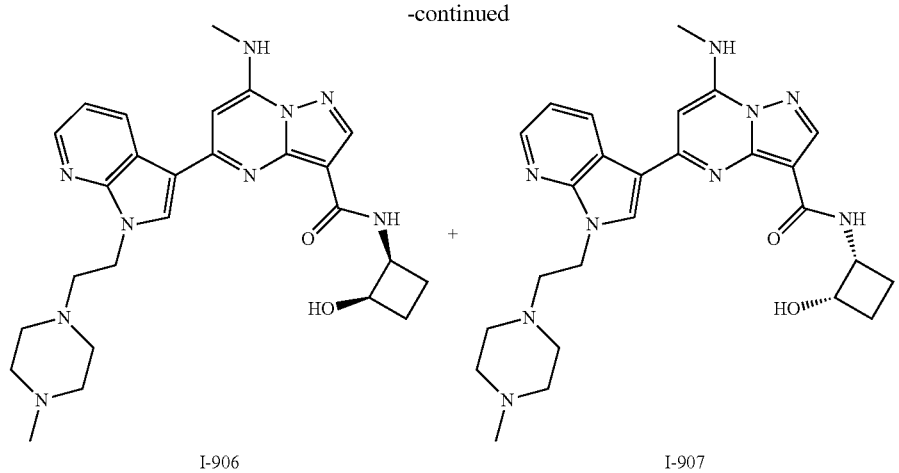

I-906     I-907

Synthesis of Compound 91.16a and 91.16b.

Isomers of 91.16 (0.120 g) were separated out using column (CHIRAL PAK AD-H 250×4.6 mm, 5 µM) and DEA in HEX_IPA-MEOH (50-50) as co-solvent with flow rate of 4 mL/min. to get pure fraction-1 (FR-a) and fraction-2 (FR-b). FR-a was concentrated under reduced pressure at 30° C. to afford pure 91.16a. (0.036 g). MS(ES): m/z 594.33 [M+H]$^+$. FR-b was concentrated under reduced pressure at 30° C. to afford pure 91.16b. (0.056 g). MS(ES): m/z 594.33 [M+H]$^+$.

Synthesis of Compound I-906 and I-907.

Compound was synthesized using general procedure C to obtain FR-a: (0.024 g) MS (ES): m/z 504.47 [M+H]$^+$, LCMS purity: 98.55%, HPLC purity: 95.11%, Chiral HPLC: 97.57%, $^1$H NMR (DMSO-d$_6$, 400 MHZ): 8.90-8.65 (m, 3H), 8.43-8.42 (t, J=7.2 Hz, 2H), 8.08 (s, 1H), 7.39-7.28 (m, 5H), 6.80-6.76 (d, 1H), 5.39 (s, 2H), 5.35 (s, 1H), 4.99-4.97 (d, J=6.8 Hz, 1H), 4.51-4.48 (t, J=12.4 Hz, 3H), 3.25 (s, 3H), 3.13-3.11 (t, J=8.4 Hz, 2H), 2.39-2.05 (m, 6H), 1.25-1.10 (m, 2H), 0.89 (t, J=13.6 Hz, 1H) and FR-b: (0.038 g) MS (ES): m/z 504.47 [M+H]$^+$, LCMS purity: 100%, HPLC purity: 96.51%, Chiral HPLC: 97.57%, $^1$H NMR (DMSO-d$_6$, 400 MHZ): 8.90-8.65 (m, 3H), 8.43-8.42 (t, J=7.2 Hz, 2H), 8.08 (s, 1H), 7.39-7.28 (m, 5H), 6.80-6.76 (d, 1H), 5.39 (s, 2H), 5.35 (s, 1H), 4.99-4.97 (d, J=6.8 Hz, 1H), 4.51-4.48 (t, J=12.4 Hz, 3H), 3.25 (s, 3H), 3.13-3.11 (t, J=8.4 Hz, 2H), 2.39-2.05 (m, 6H), 1.25-1.10 (m, 2H), 0.89 (t, J=13.6 Hz, 1H).

Characterization data for further compounds prepared by the above methods are presented in Table 18 below. Compounds in Table 18 were prepared by methods substantially similar to those described to prepare I-851, where 91.13 was replaced with the reagent as indicated in Table 18.

TABLE 18

| Compound # | Reagent | Characterization Data |
|---|---|---|
| I-578 | 2-Iodopropane | MS(ES): m/z 420.49 [M + H]$^+$, LCMS purity: 95.90%, HPLC purity: 95.25%, Chiral HPLC: 49.78: 50.22%, $^1$H NMR (DMSO-d$_6$, 400 MHZ): 8.99-8.98 (d, J = 6.4 Hz, 1H), 8.83 (s, 1H), 8.69-8.67 (d, J = 7.6 Hz, 1H), 8.37-8.35 (d, J = 9.2 Hz, 2H), 8.22 (s, 1H), 7.29 (s, 1H), 6.74 (s, 1H), 5.52 (s, 1H), 5.21 (s, 1H), 4.58 (s, 1H), 4.43 (s, 1H), 3.13 (s, 3H), 2.18-2.05 (m, 2H), 2.03-1.97 (m, 1H), 1.86 (s, 1H), 1.58 (bs, 6H). |

TABLE 18-continued

| Compound # | Reagent | Characterization Data |
|---|---|---|
| I-637<br>I-638 | 2-Iodopropane | I-578 was separated into isomers: (CHIRAL PAR IB 250 mm * 4.6 mm, 5 µM) using 0.1% diethylamine in methanol at 4 mL/min.<br>FR-a: MS(ES): m/z 420.33 [M + H]$^+$ LCMS purity: 95.88%, HPLC purity: 95.71%, Chiral HPLC purity: 95.68%, NMR (DMSO-d$_6$, 400 MHZ): 9.00-8.98 (d, J = 7.6 Hz, 1H), 8.83 (s, 1H), 8.68-8.66 (d, J = 8 Hz, 1H), 8.37-8.35 (m, 2H), 8.24 (s, 1H), 7.30-7.27 (m, 2H), 6.74 (s, 1H), 5.53-5.52 (m, J = 12.4 Hz, 1H), 5.22-5.19 (m, 1H), 4.58 (s, 1H), 4.43 (s, 1H), 3.13-3.12 (d, J = 4.4 Hz, 3H), 2.21-2.20 (m, 2H), 1.87 (s, 1H), 1.57 (bs, 6H).<br>FR-b: MS(ES): m/z 420.33 [M + H]$^+$ LCMS purity: 97.73%, HPLC purity: 98.73%, Chiral HPLC purity: 98.03%, NMR (DMSO-d$_6$, 400 MHZ): 8.97-8.96 (d, J = 7.6 Hz, 1H), 8.80 (s, 1H), 8.74-8.75 (d, J = 8.4 Hz, 1H), 8.40-8.36 (m, 2H), 8.24 (s, 1H), 7.33-7.28 (m, 1H), 6.73 (s, 1H), 5.54-5.53 (d, J = 3.6 Hz, 1H), 5.26-5.19 (m, 1H), 4.61-4.57 (s, 1H), 4.43 (s, 1H), 3.19-3.17 (d, J = 5.2 Hz, 3H), 2.21-2.20 (m, 2H), 1.87 (s, 1H), 1.57 (bs, 6H). |
| I-1048 | ![Br-tetrahydropyran] | MS(ES): m/z 462.36 [M + H]$^+$, LCMS purity: 98.10%, HPLC purity: 96.75%, CHIRAL HPLC: 52.72%, 47.27%, $^1$H NMR (DMSO-d$_6$, 400 MHZ): 8.99-8.97 (d, J = 6.8 Hz, 1H), 8.72 (s, 1H), 8.56-8.54 (d, J = 8 Hz, 1H), 8.38-8.37 (d, J = 1.6 Hz, 1H), 8.32 (s, 1H), 8.85-8.84 (d, J = 4.8 Hz, 1H), 7.31-7.28 (m, 1H), 6.72 (s, 1H), 5.15-5.14 (d, J = 4.4 Hz, 1H), 5.09-5.05 (m, 1H), 4.63-4.60 (t, J = 6.8 Hz, 1H), 4.46 (bs, 1H), 4.11-4.07 (m, 2H), 3.66-3.61 (t, J = 10.4 Hz, 2H), 3.17-3.16 (t, J = 4.8 Hz, 3H), 2.33-2.25 (m, 4H), 2.09 (bs, 3H), 1.94-1.88 (m, 1H). |
| I-1113<br>I-1114 | ![Br-tetrahydropyran] | Intermediate corresponding to 91.17 en route to I-1048 was separated into isomers before debenzylation: (CHIRAL PAK AD-H 250 × 4.6 mm, 5 µM) using DEA in HEX_IPA-MeOH (50-50) at 4 mL/min.<br>Product prepared from FR-a: MS (ES): m/z 462.57 [M + H]$^+$, LCMS purity: |

TABLE 18-continued

| Compound # | Reagent | Characterization Data |
|---|---|---|
| | | 95.29%, HPLC purity: 95.97%, Chiral HPLC: 100%, ¹H NMR (DMSO-d₆, 400 MHZ): 9.07-9.06 (d, J = 6.8 Hz, 1H), 8.89 (s, 1H), 8.62-8.60 (d, J = 8.4 Hz, 1H), 8.39-8.38 (d, J = 3.2 Hz, 1H), 8.37 (s, 1H), 8.24-8.22 (d, J = 4.8 Hz, 1H), 7.36-7.29 (m, 1H), 6.80 (s, 1H), 5.50-5.49 (d, J = 4.0 Hz, 1H), 5.13-5.07 (m, 1H), 4.63-4.60 (t, J = 6.8 Hz, 1H), 4.43 (bs, 1H), 4.09-4.07 (m, 2H), 3.66-3.61 (t, J = 11.8 Hz, 2H), 3.17-3.16 (t, J = 4.8 Hz, 3H), 2.33-2.25 (m, 4H), 2.09 (bs, 3H), 1.94-1.88 (m, 1H). Product prepared from FR-b: MS (ES): m/z 462.31 [M + H]⁺, LCMS purity: 99.35%, HPLC purity: 98.38%, Chiral HPLC: 100%, ¹H NMR (DMSO-d₆, 400 MHZ): 9.07-9.06 (d, J = 6.8 Hz, 1H), 8.90 (s, 1H), 8.62-8.60 (d, J = 8.4 Hz, 1H), 8.39-8.38 (d, J = 3.2 Hz, 1H), 8.37 (s, 1H), 8.24-8.22 (d, J = 4.8 Hz, 1H), 7.33-7.29 (m, 1H), 6.80 (s, 1H), 5.50-5.49 (d, J = 4.0 Hz, 1H), 5.13-5.07 (m, 1H), 4.63-4.60 (t, J = 6.8 Hz, 1H), 4.43 (bs, 1H), 4.09-4.07 (m, 2H), 3.66-3.61 (t, J = 11.8 Hz, 2H), 3.17-3.16 (t, J = 4.8 Hz, 3H), 2.33-2.25 (m, 4H), 2.09 (bs, 3H), 1.94-1.88 (m, 1H). |
| I-678 | 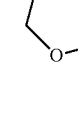 | MS(ES): m/z 491.33 [M + H]⁺, LCMS purity: 98.87%, HPLC purity: 98.20%, CHIRAL HPLC: 49.57% + 48.61%, ¹H NMR (DMSO-d₆, 400 MHZ): 8.98-8.96 (d, J = 7.6 Hz, 1H), 8.76-8.72 (m, 2H), 8.38-8.37 (d, J = 4 Hz, 1H), 8.30-8.26 (m, 2H), 7.30-7.27 (m, 1H), 6.59 (s, 1H), 5.57 (s, 1H), 4.58-4.54 (m, 4H), 3.54 (bs, 4H), 3.11 (s, 3H), 2.85-2.81 (m, 2H), 2.21-2.05 (m, 4H), 1.85 (bs, 2H). |
| I-778 I-779 | 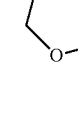 | I-678 was separated into isomers: (CHIRAL PAK AD-H 250 × 4.6 mm, 5 u) using 0.1% DEA in IPA:ACN (50:50). FR-a: MS(ES): m/z 491.6 [M + H]⁺, LCMS purity: 100%, HPLC purity: 96.95%, CHIRAL HPLC purity: 100%, ¹H NMR (DMSO-d₆, 400 MHZ): 9.02-9.00 (d, J = 8 Hz, 1H), 8.75 (s, 1H), 8.68-8.66 (d, J = 8 Hz, 1H), 8.38-8.37 (d, J = 4.8 Hz, 1H), 8.36 (s, 1H), 8.27-8.25 (d, J = 5.2 Hz, 1H), 7.31-7.28 (m, 1H), 6.68 (s, 1H), 5.57-5.56 (d, J = 4 Hz, 1H), 4.61-4.57 (t, J = 6.4 Hz, 1H), 4.51-4.48 (t, J = 6.4 Hz, 2H), 4.44 (bs, 1H), 3.54 (s, 4H), 3.13-3.12 (d, J = 4.8 Hz, 3H), 2.85-2.81 (t, J = 6.8 Hz, 2H), 2.16-2.06 (m, 3H), 1.85 (bs, 1H), 1.24 (s, 3H), 0.86 (bs, 1H). FR-b: MS(ES): m/z 491.4 [M + H]⁺, LCMS purity: 97.77%, HPLC purity: 95.53%, CHIRAL HPLC purity: 98.01%, ¹H NMR (DMSO-d₆, 400 MHZ): 9.02-9.00 (d, J = 7.6 Hz, 1H), 8.75 (s, 1H), 8.68-8.66 (d, J = 8.4 Hz, 1H), 8.39-8.37 (t, J = 4 Hz, 1H), 8.37 (s, 1H), 8.26-8.25 (d, J = 4.8 Hz, 1H), 7.31-7.28 (m, 1H), 6.68 (s, 1H), 5.56-5.55 (d, J = 3.6 Hz, 1H), 4.61-4.57 (t, J = 6.8 Hz, 1H), 4.52-4.49 (t, J = 6.4 Hz, 2H), 4.45 (bs, 1H), 3.54 (s, 4H), 3.13-3.12 (d, J = 4.8 Hz, 3H), 2.85-2.82 (t, J = 6.4 Hz, 2H), 2.14-2.06 (m, 3H), 1.86 (bs, 1H), 1.25 (s, 3H), 0.87 (bs, 1H). |
| I-793 | 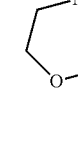 | MS(ES): m/z 489.52 [M + H]⁺, LCMS purity: 100%, HPLC purity: 99.14%, Chiral HPLC: 98.00%, ¹H NMR (DMSO-d₆, 400 MHZ): 9.27-9.25 (d, J = 6.4 Hz, 1H), 8.70 (s, 1H), 8.62-8.60 (d, J = 7.6 Hz, 1H), 8.29 (bs, 1H), 8.26 (bs, 1H), 8.03 (bs, 1H), 7.19 (bs, 1H), 6.66 (bs, 1H), 5.54 (bs, 1H), 4.84 (bs, 2H), 4.33-4.62 (bs, 1H), 4.42 (bs, 1H), 3.09 (bs, 3H), 2.86 (bs, 2H), 2.42 (s, 4H), 2.33 (bs, 1H), 2.10 (bs, 2H), 1.84 (bs, 1H), 1.43 (s, 6H). |
| I-874 I-875 | 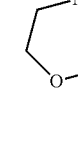 | I-793 was separated into isomers: (CHIRAL PAK AD-H 250 × 4.6 mm, 5 μM) using 0.1% DEA_HEX_IPA-ACN (70-30). FR-a: MS(ES): m/z 489.62 [M + H]⁺, LCMS purity: 100%, HPLC purity: 98.85%, CHIRAL HPLC purity: 98.87%, ¹H NMR (DMSO-d₆, 400 MHZ): 9.29-9.28 (d, J = 7.2 Hz, 1H), 8.73 (s, 1H), 8.63-8.61 (d, J = 8.8 Hz, 1H), 8.31 (s, 1H), 8.28-8.27 (d, J = 5.6 Hz, 1H), 8.06-8.05 (d, J = 4.8 Hz, 1H), 7.23-7.20 (t, J = 6.4 Hz, 1H), 6.68 (s, 1H), 5.56 (s, 1H), 4.87 (s, 2H), 4.65-4.62 (t, J = 7.2 Hz, 1H), 4.44 (s, 1H), 3.11-3.10 (d, J = 4.8 Hz, 3H), 2.91 (s, 2H), 2.34-2.03 (m, 5H), 1.88-1.85 (m, 1H), 1.46-1.35 (m, 6H), 1.25 (bs, 2H). FR-b: MS(ES): m/z 489.67 [M + H]⁺, LCMS purity: 100%, HPLC purity: 98.24%, CHIRAL HPLC purity: 98.53%, ¹H NMR (DMSO-d₆, 400 MHZ): 9.29-9.27 (d, J = 7.6 Hz, 1H), 8.72 (s, 1H), 8.63-8.60 (d, J = 8.4 Hz, 1H), 8.31 (s, 1H), 8.28-8.27 (d, J = 6.0 Hz, 1H), 8.05-8.04 (d, J = 4.8 Hz, 1H), 7.23-7.20 (m, 1H), 6.67 (s, 1H), 5.55 (s, 1H), 4.87 (s, 2H), 4.65-4.61 (m, 1H), 4.45 (s, 1H), 3.11-3.10 (d, J = 4.8 Hz, 3H), 2.91 (s, 2H), 2.34-2.05 (m, 5H), 1.88-1.83 (m, 1H), 1.46-1.35 (m, 6H), 1.24 (bs, 2H). |

1053

Synthesis of N-(2-hydroxycyclobutyl)-5-((1-((1R,4S)-4-methoxy-4-methylcyclohexyl)-2-oxo-1,2-dihydropyridin-3-yl)amino)-7-(methylamino)pyrazolo[1,5-a]pyrimidine-3-carboxamide (I-670), N-((1S,2R)-2-hydroxycyclobutyl)-5-((1-((1R,4S)-4-methoxy-4-methylcyclohexyl)-2-oxo-1,2-dihydropyridin-3-yl)amino)-7-(methylamino)pyrazolo[1,5-a]pyrimidine-3-carboxamide (I-722), N-((1R,2S)-2-hydroxycyclobutyl)-5-((1-((1R,4R)-4-methoxy-4-methylcyclohexyl)-2-oxo-1,2-dihydropyridin-3-yl)amino)-7-(methylamino)pyrazolo[1,5-a]pyrimidine-3-carboxamide (I-723)

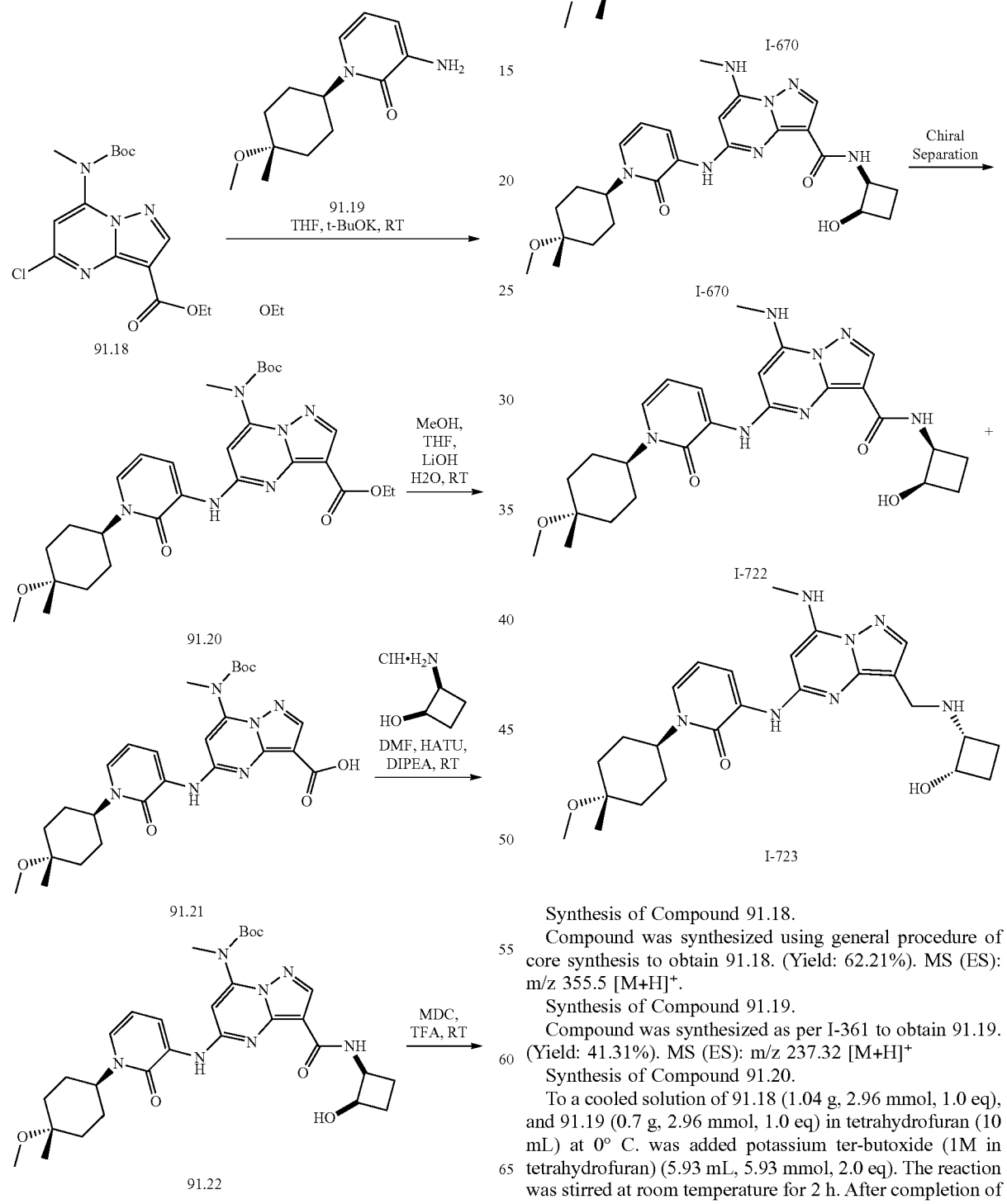

Synthesis of Compound 91.18.

Compound was synthesized using general procedure of core synthesis to obtain 91.18. (Yield: 62.21%). MS (ES): m/z 355.5 [M+H]+.

Synthesis of Compound 91.19.

Compound was synthesized as per I-361 to obtain 91.19. (Yield: 41.31%). MS (ES): m/z 237.32 [M+H]+

Synthesis of Compound 91.20.

To a cooled solution of 91.18 (1.04 g, 2.96 mmol, 1.0 eq), and 91.19 (0.7 g, 2.96 mmol, 1.0 eq) in tetrahydrofuran (10 mL) at 0° C. was added potassium ter-butoxide (1M in tetrahydrofuran) (5.93 mL, 5.93 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 0-5% Methanol in DCM to obtain pure 91.20 (0.400 g, 24.60%). MS (ES): m/z 555.49 [M+H]$^+$.

Synthesis of Compound 91.21.

To a solution of 91.20 (0.300 g, 0.54 mmol, 1.0 eq), in tetrahydrofuran: methanol: water (8 mL, 3:3:2) was added lithium hydroxide (0.228 g, 5.41 mmol, 10 eq). The reaction was stirred at 50° C. for 16 h. After completion of reaction, reaction mixture was concentrated under reduced pressure to obtain residue. To this added water and acidified with IN hydrochloric acid to adjust pH~6-6.5 at 10° C. Product was extracted with dichloromethane. Organic layer was combined, washed with brine solution, dried over sodium sulphate and concentrated under reduced pressure to obtain 91.21 (0.150 g, 52.66%). MS(ES): m/z 527.25 [M+H]$^+$.

Synthesis of Compound 91.22.

Compound was synthesized using general procedure A to obtain 91.22 (0.120 g, 70.72%). MS(ES): m/z 596.31 [M+H]$^+$ Synthesis of Compound I-670.

Compound was synthesized using general procedure C to obtain I-670 (0.100 g, 95.12%). MS (ES): m/z 496.37 [M+H]$^+$, LCMS purity: 100%, HPLC purity: 96.69%, Chiral HPLC: 50.03% and 49.96% $^1$H NMR (DMSO-d$_6$, 400 MHZ): 8.83 (s, 1H), 8.53-8.51 (d, J=8 Hz, 1H), 8.21 (s, 1H), 8.06-8.04 (d, J=8 Hz, 1H), 7.89-7.88 (d, J=4 Hz, 1H), 7.51-7.49 (d, J=8 Hz, 1H), 6.42-6.38 (t, J=8 Hz, 1H), 6.27 (s, 1H), 5.41-5.40 (d, J=4 Hz, 1H), 4.79-4.73 (m, 1H), 4.60-4.56 (m, 1H), 4.36 (s, 1H), 3.19 (s, 3H), 2.93-2.92 (d, J=4 Hz, 3H), 2.34 (bs, 1H), 2.20 (bs, 1H), 2.13-1.75 (m, 7H), 1.60-1.55 (m, 3H), 1.38 (s, 3H).

Isomers of I-670 (0.085 g) were separated out using column CHIRALCEL OJ-H (250 mm*4.6 mm, 5 u) in 0.1% DEA in methanol as co-solvent with flow rate of 4 mL/min. to get pure fraction-1 (FR-a) and pure fraction-2 (FR-b).

FR-a was concentrated under reduced pressure at 30° C. to afford 0.032 g. MS(ES): m/z 496.26 [M+H]$^+$, LCMS purity: 100%, HPLC purity: 98.74%, CHIRAL HPLC purity: 100%, $^1$H NMR (DMSO-d$_6$, 400 MHZ): 8.83 (s, 1H), 8.53-8.51 (d, J=8 Hz, 1H), 8.21 (s, 1H), 8.06-8.04 (d, J=8 Hz, 1H), 7.89-7.88 (d, J=4 Hz, 1H), 7.51-7.49 (d, J=8 Hz, 1H), 6.42-6.38 (t, J=8 Hz, 1H), 6.27 (s, 1H), 5.41-5.40 (d, J=4 Hz, 1H), 4.79-4.73 (m, 1H), 4.60-4.56 (m, 1H), 4.36 (s, 1H), 3.19 (s, 3H), 2.93-2.92 (d, J=4 Hz, 3H), 2.34 (bs, 1H), 2.20 (bs, 1H), 2.13-1.75 (m, 7H), 1.60-1.55 (m, 3H) 1.38 (s, 3H).

FR-b was concentrated under reduced pressure at 30° C. to afford 0.032 g. MS(ES): m/z 496.31 [M+H]$^+$, LCMS purity: 100%, HPLC purity: 97.34%, CHIRAL HPLC purity: 98.89%, $^1$H NMR (DMSO-d$_6$, 400 MHZ): 8.83 (s, 1H), 8.53-8.51 (d, J=8 Hz, 1H), 8.21 (s, 1H), 8.06-8.04 (d, J=8 Hz, 1H), 7.89-7.88 (d, J=4 Hz, 1H), 7.51-7.49 (d, J=8 Hz, 1H), 6.42-6.38 (t, J=8 Hz, 1H), 6.27 (s, 1H), 5.41-5.40 (d, J=4 Hz, 1H), 4.79-4.73 (m, 1H), 4.60-4.56 (m, 1H), 4.36 (s, 1H), 3.19 (s, 3H), 2.93-2.92 (d, J=4 Hz, 3H), 2.34 (bs, 1H), 2.20 (bs, 1H), 2.13-1.75 (m, 7H), 1.60-1.55 (m, 3H)$_{1.38}$ (s, 3H).

Characterization data for further compounds prepared by the above methods are presented in Table 19 below. Compounds in Table 19 were prepared by methods substantially similar to those described to prepare I-670, where 91.19 was replaced with the reagent as indicated in Table 19.

TABLE 19

| Compound # | Reagent | Chiral Purification Conditions and Characterization Data |
|---|---|---|
| I-611 | 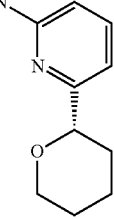 91g | MS(ES): m/z 438.39 [M + H]$^+$ LCMS purity: 99.54%, HPLC purity: 97.63%, $^1$H NMR (DMSO-d$_6$, 400 MHZ): 9.91 (s, 1H), 8.21 (s, 1H), 8.10-8.09 (d, J = 6 Hz, 2H), 7.98-7.97 (d, J = 4.8 Hz, 1H), 7.80-7.77 (t, J = 6 Hz, 1H), 7.06-7.04 (d, J = 7.2 Hz, 1H), 6.25 (s, 1H), 5.33-5.31 (t, J = 4 Hz, 1H), 4.5 (s, 1H), 4.32-4.39 (d, J = 11.2 Hz, 2H), 4.07-4.04 (d, J = 10.8 Hz, 1H), 3.60-3.57 (d, J = 4.4 Hz, 1H), 2.92-2.91 (d, J = 4.4 Hz, 3H), 2.18-2.16 (d, J = 6 Hz 1H), 2.07-1.98 (m, 3H), 1.91-1.88 (d, J = 11.6 Hz, 1H), 1.75 (bs, 1H), 1.63-1.49 (m, 4H). |
| I-647 I-648 | 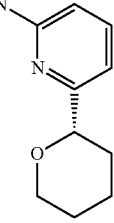 91g | I-611 was separated into isomers: (CHIRAL PAK AD-H 250 × 4.6 mm, 5 u) using 0.1% DEA in MeOH/iPrOH. FR-a: MS(ES): m/z 438.50 [M + H]$^+$, LCMS purity: 98.87%, HPLC purity: 96.23%, CHIRAL HPLC purity: 99.5%, $^1$H NMR (DMSO-d$_6$, 400 MHZ): 9.92 (s, 1H), 8.22 (s, 1H), 8.13-8.09 (t, J = 5.2 Hz, 2H), 7.99-7.97 (d, J = 7.2 Hz, 1H), 7.81-7.77 (t, J = 7.6 Hz, 1H), 7.07-7.05 (d, J = 7.6 Hz, 1H), 6.28 (s, 1H), 4.56-5.53 (t, J = 7.2 Hz, 1H), 4.34-4.31 (d, J = 11.2 Hz, 2H), 4.08-4.05 (d, J = 11.6 Hz, 1H), 3.61-3.55 (m, 1H), 2.93-2.92 (d, J = 4.8 Hz, 3H), 2.19-2.17 (d, J = 10 Hz 1H), 2.13-1.99 (m, 3H), 1.92-1.89 (d, J = 12.4 Hz, 1H), 1.77-1.74 (d, J = 10 Hz, 2H), 1.65-1.50 (m, 4H). FR-b: MS(ES): m/z 438.50 [M + H]$^+$, LCMS purity: 99.07%, HPLC purity: 95.54%, CHIRAL HPLC purity: 98.58%, $^1$H NMR (DMSO-d$_6$, 400 MHZ): 9.93 (s, 1H), 8.22 (s, 1H), 8.12-8.09 (d, J = 8.4 Hz, 2H), 7.99-7.97 (d, J = 4.8 Hz, 1H), 7.82-7.78 (t, J = 8 Hz, 1H), 7.07-7.05 (d, J = 7.2 Hz, 1H), 6.27 (s, 1H), 4.57-5.53 (t, J = 6.8 Hz, 1H), 4.35-4.30 (d, J = 9.2 Hz, 2H), 4.08-4.05 (d, J = 11.6 Hz, 1H), 3.61-3.55 (m, 1H), 2.93-2.92 (d, J = 4.4 Hz, 3H), 2.19-2.17 (d, J = 9.6 Hz 1H), 2.12-2.00 (m, 3H), 1.92-1.89 (d, J = 11.2 Hz, 1H), 1.79-1.71 (d, J = 10.8 Hz, 2H), 1.64-1.50 (m, 4H). |
| I-602 | 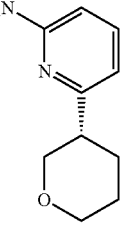 91j | MS(ES): m/z 438.6 [M + H]$^+$ LCMS purity: 100%, HPLC purity: 97.69%, NMR (DMSO-d$_6$, 400 MHZ): 9.90 (s, 1H), 8.21-8.076 (m, 3H), 7.72-7.68 (d, J = 7.6 Hz, 1H), 7.56 (s, 1H), 6.97-6.96 (d, J = 7.6 Hz, 1H), 6.69 (s, 1H), 5.41 (d, J = 7.2 Hz, 1H), 4.24-4.20 (t, J = 8.4 Hz, 1H), 4.02-3.88 (m, 4H), 4.55-4.50 (d, J = 10.8 Hz, 1H), 2.97-42.89 (m, J = 10.8 Hz, 4H), 2.01-1.89 (m, 4H), 1.67 (s, 2H), 1.50-1.45 (d, J = 9.2 Hz 1H), 1.31-1.24 (m, 1H). |

TABLE 19-continued

| Compound # | Reagent | Chiral Purification Conditions and Characterization Data |
|---|---|---|
| I-604 | 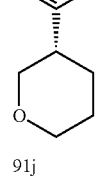 91j | MS(ES): m/z 438.34 [M + H]+, LCMS purity: 97.63%, HPLC purity: 99.55%, CHIRAL HPLC: 47.57%, 49.29%, 1H NMR (DMSO-d6, 400 MHZ): 9.82 (s, 1H), 8.22 (s, 1H), 8.12-8.10 (d, J = 8.4 Hz, 1H), 8.04-8.00 (m, 2H), 7.76-7.72 (t, J = 7.6 Hz, 1H), 6.97-6.95 (d, J = 7.2 Hz, 1H), 6.36 (bs, 1H), 5.33-5.32 (d, J = 4 Hz, 1H), 4.56-4.53 (t, J = 6.8 Hz, 1H), 4.35 (bs, 1H), 4.05-3.99 (m, 1H), 3.92-3.89 (d, J = 11.2 Hz, 1H), 3.55-3.50 (d, J = 10.4 Hz, 1H), 2.95-2.94 (d, J = 4.8 Hz, 3H), 2.87 (bs, 1H), 2.17-2.15 (d, J = 5.6 Hz, 1H), 2.11-2.02 (m, 3H), 2.00 (s, 1H), 1.78-1.74 (m, 1H), 1.70 (bs, 2H), 1.28 (bs, 1H). |
| I-641 I-642 | 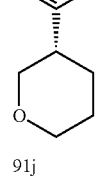 91j | I-604 was separated into isomers: (CHIRAL PAK IB 250 mm * 4.6 mm, 5 u) using 0.1% diethylamine in methanol at 4 mL/min. FR-a: MS(ES): m/z 438.50 [M + H]+· LCMS purity: 100%, HPLC purity: 98.10%, Chiral HPLC purity: 93.50%, NMR (DMSO-d6, 400 MHZ): 9.80 (s, 1H), 8.21 (s, 1H), 8.11-8.09 (d, J = 8.4 Hz, 1H), 8.02-7.98 (m, 2H), 7.75-7.71 (t, J = 8 Hz, 1H), 6.96-6.94 (d, J = 7.2 Hz, 1H), 6.34 (s, 1H), 5.31-5.30 (d, J = 4 Hz, 1H), 4.57-4.51 (m, 1H), 4.34 (s, 1H), 4.01-3.99 (d, J = 8.4 Hz, 2H), 3.91-3.88 (d, J = 4 Hz, 1H), 3.54-3.49 (t, J = 10.8 Hz, 1H), 2.94-2.93 (d, J = 4.8 Hz, 3H), 2.89-2.86 (m, 1H), 2.18-2.01 (m, J = 7.2 Hz, 3H), 1.91-1.67 (m, 4H). FR-b: MS(ES): m/z 438.50 [M + H]+· LCMS purity: 100%, HPLC purity: 96.51%, Chiral HPLC purity: 100%, NMR (DMSO-d6, 400 MHZ): 9.80 (s, 1H), 8.21 (s, 1H), 8.11-8.09 (d, J = 8.4 Hz, 1H), 8.02-7.98 (m, 2H), 7.75-7.71 (t, J = 8 Hz, 1H), 6.96-6.94 (d, J = 7.2 Hz, 1H), 6.35 (s, 1H), 5.31-5.30 (d, J = 4 Hz, 1H), 4.55-4.51 (m, 1H), 4.34 (s, 1H), 4.01-3.98 (d, J = 10.4 Hz, 2H), 3.91-3.88 (d, J = 11.2 Hz, 1H), 3.54-3.48 (t, J = 10.8 Hz, 1H), 2.94-2.93 (d, J = 4.8 Hz, 3H), 2.90-2.89 (m, 1H), 2.18-2.01 (m, 3H), 1.94-1.67 (m, 4H). |
| I-610 | 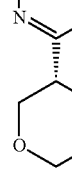 91h | MS(ES): m/z 438.39 [M + H]+ LCMS purity: 99.59%, HPLC purity: 97.02%, chiral HPLC purity: 50%, 49.9%. 1H NMR (DMSO-d6, 400 MHZ): 9.91 (s, 1H), 8.21 (s, 1H), 8.10-8.09 (d, J = 6 Hz, 2H), 7.98-7.97 (d, J = 4.8 Hz, 1H), 7.80-7.77 (t, J = 6 Hz, 1H), 7.06-7.04 (d, J = 7.2 Hz, 1H), 6.25 (s, 1H), 5.33-5.31 (t, J = 4 Hz, 1H), 4.54 (s, 1H), 4.32-4.29 (d, J = 11.2 Hz, 2H), 4.07-4.04 (d, J = 10.8 Hz, 1H), 3.57-3.53 (m, 1H), 2.92-2.91 (d, J = 4.4 Hz, 3H), 2.18-2.16 (d, J = 8.4 Hz, 1H), 2.06-1.98 (m, 4H), 1.91-1.88 (d, J = 11.6 Hz, 1H), 1.75 (bs, 1H), 1.63-1.49 (m, 3H). |
| I-645 I-646 | 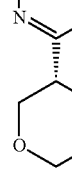 91h | I-610 was separated into isomers: (CHIRAL PAK AD-H 250 × 4.6 mm, 5 μM) using 0.1% DEA in methanol/IPA. FR-a: MS(ES): m/z 438.50 [M + H]+, LCMS purity: 100%, HPLC purity: 99.24%, CHIRAL HPLC purity: 100%, 1H NMR (DMSO-d6, 400 MHZ): 9.92 (s, 1H), 8.22 (s, 1H), 8.13-8.09 (t, J = 6.4 Hz, 2H), 7.99-7.98 (d, J = 4.8 Hz, 1H), 7.81-7.77 (t, J = 7.6 Hz, 1H), 7.07-7.05 (d, J = 7.6 Hz, 1H), 6.27 (s, 1H), 5.33-5.32 (d, J = 4 Hz, 1H), 4.56-4.53 (t, J = 6.8 Hz, 1H), 4.34-4.31 (d, J = 11.2 Hz, 2H), 4.08-4.035 (t, J = 11.6 Hz, 1H), 3.61-3.54 (m, 1H), 2.93-2.92 (d, J = 4.4 Hz, 3H), 2.19-2.17 (d, J = 10 Hz, 1H), 2.12-2.00 (d, J = 12.4 Hz, 3H), 1.92-1.90 (d, J = 8.8 Hz, 1H), 1.79-1.47 (m, 3H), 1.35-1.72 (m, 2H). FR-b: MS(ES): m/z 438.50 [M + H]+, LCMS purity: 98.56%, HPLC purity: 97.75%, CHIRAL HPLC purity: 100%, 1H NMR (DMSO-d6, 400 MHZ): 9.96 (s, 1H), 8.22 (s, 1H), 8.14-8.10 (t, J = 8.8 Hz, 2H), 7.99-7.98 (d, J = 4.8 Hz, 1H), 7.82-7.78 (t, J = 7.6 Hz, 1H), 7.07-7.05 (d, J = 7.6 Hz, 1H), 6.31 (s, 1H), 5.33-5.32 (d, J = 4 Hz, 1H), 4.57-5.53 (t, J = 2.8 Hz, 1H), 4.33-4.30 (d, J = 11.6 Hz, 2H), 4.08-4.05 (d, J = 0 Hz, 1H), 3.61-3.55 (t, J = 11.2 Hz 1H), 2.93-2.92 (d, J = 4.4 Hz, 3H), 2.19-2.16(d, J = 10 Hz 1H), 2.09-2.00 (m, 3H), 1.92-1.89 (d, J = 11.6 Hz, 1H), 11.79-1.47 (m, 3H), 1.35-1.72 (m, 2H). |
| I-603 | 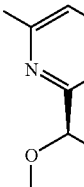 91k | MS(ES): m/z 438.6 [M + H]+ LCMS purity: 98.99%, HPLC purity: 97.46%, NMR (DMSO-d6, 400 MHZ): 9.90 (s, 1H), 8.21 (s, 1H), 8.162-140 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.41-5.39 (d, J = 7.2 Hz, 1H), 4.24-4.20 (m, 1H), 4.02-3.88 (m, 3H), 3.55-3.50 (t, J = 10.8 Hz, 1H), 2.97-2.96 (m, 1H), 2.89 (s, 3H), 2.03-1.89 (m, 4H), 1.67 (bs, 2H), 1.50-1.45 (m, 1H), 1.31-1.24 (m, 2H). |
| I-605 | 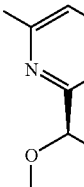 91k | MS(ES): m/z 438.34 [M + H]+ LCMS purity: 100%, HPLC purity: 96.23% Chiral HPLC purity: 49.92%, 49.44%, 1H NMR (DMSO-d6, 400 MHZ): 9.80 (s, 1H), 8.27 (s, 1H), 8.11-8.09 (d, J = 8.0 Hz, 1H), 8.06 (s, 2H), 7.74-7.71 (m, 1H), 6.96-6.94 (d, J = 8.0 Hz, 1H), 6.34 (s, 1H), 5.32-5.31 (d, J = 4.0 Hz, 1H), 4.55-4.52 (m, 1H), 4.34 (s, 1H), 4.01-3.88 (m, 2H), 3.54-3.48 (t, J = 12 Hz, 1H), 2.94-2.89 (m, 4H), 2.18-2.16 (d, J = 8.0 Hz, 1H), 2.03-2.01 (m, 3H), 1.90-1.86 (m, 2H) 1.77-1.67 (m, 3H). |

TABLE 19-continued

| Compound # | Reagent | Chiral Purification Conditions and Characterization Data |
|---|---|---|
| I-643<br>I-644 | 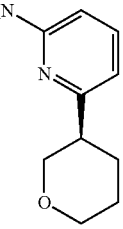91k | I-605 was separated into isomers: (CHIRALPAK AD-H 250 mm * 4.6 mm, 5 µM) using 0.1% diethylamine in MeOH at 4 mL/min.<br>FR-a: MS(ES): m/z 438.27 [M + H]$^+$, LCMS purity: 100%, HPLC purity: 97.67%, CHIRAL HPLC purity: 100%, $^1$H NMR (DMSO-d$_6$, 400 MHZ): ): 9.80 (s, 1H), 8.21 (s, 1H), 8.11-8.09 (d, J = 8.0 Hz, 1H), 8.02-7.98 (m, 2H), 7.75-7.71 (t, J = 8.0 Hz, 2H), 6.96-6.94 (d, 8.0 Hz, 1H), 6.35 (s, 1H), 5.76 (s, 1H), 5.32-5.31 (d, J = 4.0 Hz, 1H), 4.55-4.51(m, 1H), 4.34 (s, 1H), 4.01-3.88 (m, 2H), 3.54-3.48 (t, J = 12.0 Hz, 1H), 2.94-2.84 (m, 3H), 2.18-2.10 (m, 4H), 1.97-1.88 (m, 1H) 1.86-1.72 (m, 3H).<br>FR-b: MS(ES): m/z 438.40 [M + H]$^+$, LCMS purity: 99.28%, HPLC purity: 97.62%, CHIRAL HPLC purity: 99.32%,<br>$^1$HNMR (DMSO-d$_6$, 400 MHZ): 9.81 (s, 1H), 8.22 (s, 1H), 8.12-8.10 (d, J = 8.0 Hz, 1H), 8.03-7.99 (m, 2H), 7.76-7.72 (t, J = 8.0 Hz, 1H), 6.97-6.95 (d, J = 8.0 Hz, 1H), 6.36 (s, 1H), 5.32-5.31 (d, J = 4.0 Hz, 1H), 4.56-4.53 (m, 1H), 4.35 (s, 1H), 4.01-3.89 (m, 2H), 3.55-3.49 (t, J = 12.0 Hz, 1H), 2.95-2.87 (m, 3H), 2.19-2.10 (m, 4H), 1.97-1.88 (m, 1H) 1.86-1.72 (m, 3H). |
| I-609 | 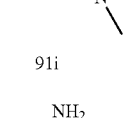91i | MS(ES): m/z 467.4 [M + H]$^+$, LCMS purity: 100%, HPLC purity: 98.16%, Chiral HPLC: 49.93% and 48.93% $^1$H NMR (DMSO-d$_6$, 400 MHZ): 8.83 (s, 1H), 8.54-8.52 (d, J = 6.8 Hz, 1H), 8.21 (s, 1H), 8.05-8.03 (d, J = 8.8 Hz, 1H), 7.90-7.89 (d, J = 4.8 Hz, 1H), 7.44-7.42 (d, J = 8 Hz, 1H), 6.43-6.39 (t, 1H), 6.27 (s, 1H), 5.41-5.40 (d, J = 4 Hz, 1H), 4.81-4.75 (m, 1H), 4.60-4.56 (m, 1H), 4.36 (bs, 1H), 2.93-2.92 (d, J = 4.4 Hz, 4H), 2.24 (s, 4H), 2.11-2.06 (m, 3H), 2.03-1.91 (m, 3H), 1.77-1.74 (d, J = 10.4 Hz, 3H). |
| I-689<br>I-690 | 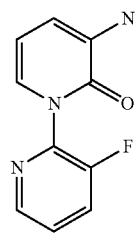91i | I-609 was separated into isomers: (CHIRALCEL OX-H 250 mm * 4.6 mm, 5 µM) using 0.1% DEA in IPA:ACN (50:50) at 5 mL/min.<br>FR-a: MS(ES): m/z 467.4 [M + H]$^+$, LCMS purity: 100%, HPLC purity: 98.16%, Chiral HPLC: 49.93% and 48.93% $^1$H NMR (DMSO-d$_6$, 400 MHZ): 8.83 (s, 1H), 8.54-8.52 (d, J = 6.8 Hz, 1H), 8.21 (s, 1H), 8.05-8.03 (d, J = 8.8 Hz, 1H), 7.90-7.89 (d, J = 4.8 Hz, 1H), 7.44-7.42 (d, J = 8 Hz, 1H), 6.43-6.39 (t, 1H), 6.27 (s, 1H), 5.41-5.40 (d, J = 4 Hz, 1H), 4.81-4.75 (m, 1H), 4.60-4.56 (m, 1H), 4.36 (bs, 1H), 2.93-2.92 (d, J = 4.4 Hz, 4H), 2.24 (s, 4H), 2.11-2.06 (m, 3H), 2.03-1.91 (m, 3H), 1.77-1.74 (d, J = 10.4 Hz, 3H).<br>FR-b: MS(ES): m/z 467.3 [M + H]$^+$, LCMS purity: 100%, HPLC purity: 98.92%, CHIRAL HPLC purity: 95.13%,<br>$^1$H NMR (DMSO-d$_6$, 400 MHZ): 8.83 (s, 1H), 8.54-8.52 (d, J = 7.2 Hz, 1H), 8.21 (s, 1H), 8.05-8.03 (d, J = 8.8 Hz, 1H), 7.90-7.88 (d, J = 4.4 Hz, 1H), 7.44-7.42 (d, J = 6.4 Hz, 1H), 6.43- 4.39 (t, 1H), 6.27 (s, 1H), 5.41-5.40 (d, J = 3.6 Hz, 1H), 4.81-4.78 (m, 1H), 4.59-4.56 (m, 1H), 4.36 (bs, 1H), 2.93-2.92 (d, J = 4.4 Hz, 4H), 2.24 (s, 3H), 2.09-2.06 (m, 3H), 2.01-1.94(m, 3H), 1.77-1.75 (d, J = 9.6 Hz, 3H). |
| I-566 | 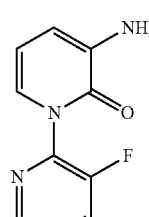 | MS(ES): m/z 465.3 [M + H]$^+$, LCMS purity: 98.29%, HPLC purity: 96.61%, CHIRAL HPLC: 49.10%, 49.64%, $^1$H NMR (DMSO-d$_6$, 400 MHZ): 8.92 (bs, 1H), 8.69-8.67 (d, J = 7.2 Hz, 1H), 8.53-8.52 (d, J = 4.4 Hz, 1H), 8.24 (s, 1H), 8.10-8.06 (m, 2H), 7.95-7.94 (d, J = 4.8 Hz, 1H), 7.75-7.73 (m, 1H), 7.43-7.41 (d, J = 6.4 Hz, 1H), 6.57-6.54 (t, J = 7.2 Hz, 1H), 6.31 (s, 1H), 5.49-5.48 (d, J = 3.6 Hz, 1H), 4.60 (bs 1H), 4.39 (bs, 1H), 2.92-2.91(d, J = 4.4 Hz, 3H), 2.22 (bs, 1H), 2.12-2.00 (m, 2H), 1.78 (bs, 1H). |
| I-572<br>I-573 | 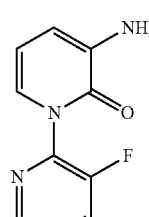 | I-566 was separated into isomers: CHIRAL PAK AD-H (250 × 4.6 mm, 5 u) and 0.1% DEA in methanol at 4 mL/min.<br>FR-a: MS(ES): m/z 465.51 [M + H]$^+$, LCMS purity: 97.30%, HPLC purity: 98.58%, CHIRAL HPLC purity: 100%, $^1$H NMR (DMSO-d$_6$, 400 MHZ): 8.97 (s, 1H), 8.68-8.67 (d, J = 6 Hz, 1H), 8.53-8.52 (d, J = 4.8 Hz, 1H), 8.24 (s, 1H), 8.10-8.06 (m, 2H), 7.94-7.93 (d, J = 4.8 Hz, 1H), 7.76-7.72 (m, 1H), 7.42-7.41 (s, J = 5.6 Hz, 1H), 6.57-6.54 (t, J = 7.2 Hz, 1H), 6.30 (s, 1H), 5.48-5.47 (d, J = 4 Hz, 1H), 4.61-4.58 (t, J = 7.2 Hz, 1H), 4.39 (bs, 1H), 2.92-2.91 (d, J = 4.8 Hz, 3H), 2.26-2.21 (m, 2H), 2.04-2.00 (m, 1H), 1.81 (bs, 1H).<br>FR-b: MS(ES): m/z 465.51 [M + H]$^+$, LCMS purity: 100%, HPLC purity: 97.86%, CHIRAL HPLC purity: 99.72%,<br>$^1$H NMR (DMSO-d$_6$, 400 MHZ): 8.97 (s, 1H), 8.68-8.67 (d, J = 7.2 Hz, 1H), 8.53-8.52 (d, J = 4.4 Hz, 1H), 8.23 (s, 1H), 8.10-8.06 (m, 2H), 7.94-7.93 (d, J = 4.4 Hz, 1H), 7.76-7.72 (m, 1H), 7.42-7.41 (s, J = 6.8 Hz, 1H), 6.57-6.54 (t, J = 7.2 Hz, 1H), 6.31 (s, 1H), 5.48-5.47 (d, J = 3.6 Hz, 1H), 4.61-4.58 (t, J = 6.8 Hz, 1H), 4.38 (bs, 1H), 2.92-2.91 (d, J = 4.4 Hz, 3H), 2.22 (bs, 1H), 2.10-2.00 (m, 2H), 1.78 (bs, 1H). |
| I-527 | 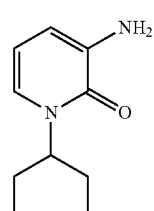 | MS(ES): m/z 454.5 [M + H]$^+$ LCMS purity: 100%, HPLC purity: 100%, Chiral HPLC purity: 49.70%, 46.01%, NMR (DMSO-d$_6$, 400 MHZ): 8.81 (s, 1H), 8.53-8.52 (d, J = 6.4 Hz, 1H), 8.19 (s, 1H), 8.04-7.01 (d, J = 8.8 Hz, 1H), 7.87 (s, 1H), 7.45-7.43 (d, J = 6.8 Hz, 1H), 7.07 (s, 1H), 6.83-6.81 (d, J = 7.2 Hz, 1H), 6.42-6.39 (t, J = 7.2 Hz, 1H), 5.40 (s, 1H), 4.56-4.55 (d, J = 6.4 Hz, 1H) 4.35 (s, 1H), 4.02-4.00 (d, J = 8.8 Hz, 1H), 3.54-3.48 (t, J = 4.8 Hz, 3H), 2.92-2.91 (d, J = 4 Hz, 3H), 2.19-2.02 (m, 4H), 1.98-1.95 (d, J = 8.8 Hz, 4H). |

TABLE 19-continued

| Compound # | Reagent | Chiral Purification Conditions and Characterization Data |
|---|---|---|
| I-556 I-557 |  | I-527 was separated into isomers: (CHIRAL PAK AD-H 250 × 4.6 mm, 5 µM) using 0.1% DEA in MEOH at 4 mL/min. FR-a: MS(ES): m/z 454.62 [M + H]+· LCMS purity: 97.71%, HPLC purity: 97.45%, Chiral HPLC purity: 100%, NMR (DMSO-$d_6$, 400 MHZ): 8.82 (s, 1H), 8.53-8.52 (d, J = 7.2 Hz, 1H), 8.20 (s, 1H), 8.14 (s, 1H), 8.04-8.02 (d, J = 8.8 Hz, 1H), 7.89-7.88 (d, J = 4.8 Hz, 1H), 7.46-7.44 (d, J = 7.2 Hz, 1H), 6.42-6.39 (d, J = 7.2 Hz, 1H), 6.27 (s, 1H), 5.41 (s, 1H), 5.09-5.02 (t, J = 12.4 Hz, 1H), 4.60-4.56 (t, J = 7.2 Hz, 1H), 4.36 (s, 1H), 4.03-4.01 (d, J = 8.4 Hz, 1H), 3.55-3.50 (t, J = 11.6 Hz, 2H), 2.93-2.92 (d, J = 4.4 Hz, 3H), 2.21-2.20 (m, 2H), 2.08-2.06 (m, 1H), 1.99-1.97 (d, J = 8 Hz, 1H), 1.78-1.75 (d, J = 10.8 Hz, 2H), 1.25 (s, 2H). FR-b: MS(ES): m/z 454.62 [M + H]+· LCMS purity: 95.26%, HPLC purity: 95.30%, Chiral HPLC purity: 97.06%, NMR (DMSO-$d_6$, 400 MHZ): 8.82 (s, 1H), 8.53-8.52 (d, J = 7.2 Hz, 1H), 8.20 (s, 1H), 8.14 (s, 1H), 8.04-8.02 (d, J = 8.8 Hz, 1H), 7.89-7.88 (d, J = 4.8 Hz, 1H), 7.46-7.44 (d, J = 7.2 Hz, 1H), 6.42-6.39 (d, J = 7.2 Hz, 1H), 6.27 (s, 1H), 5.04-5.01 (d, J = 12 Hz, 1H), 4.58-4.55 (t, J = 7.6 Hz, 1H), 4.35 (s, 1H), 4.02-4.00 (d, J = 7.6 Hz, 1H), 3.54-3.48 (t, J = 13.6 Hz, 2H), 2.91-2.90 (d, J = 4.8 Hz, 3H), 2.19 (bs, 2H), 2.11-1.91 (m, 3H), 1.76-1.73 (d, J = 12 Hz, 2H), 1.23 (s, 2H). |
| I-539 |  | MS(ES): m/z 482.31 [M + H]+, LCMS purity: 100%, HPLC purity: 99.59%, CHIRAL HPLC purity: 49.75%, 49.76% $^1$H NMR (DMSO-$d_6$, 400 MHZ): 8.79 (s, 1H), 8.51-8.50 (d, J = 6 Hz, 1H), 8.19 (s, 1H), 8.03-8.01 (d, J = 8.8 Hz, 1H), 7.86-7.85 (d, J = 5.2 Hz, 1H), 7.38-7.37 (d, J = 6 Hz, 1H), 6.40-6.37 (t, J = 7.2 Hz, 1H), 6.25 (s, 1H), 5.38-5.37 (d, J = 4 Hz, 1H), 4.82-4.78 (m, 1H), 4.58-4.55 (t, J = 6 Hz, 1H), 4.35 (bs, 1H), 4.15-4.13 (m, 1H), 3.27 (s, 3H), 2.92-2.91 (d, J = 4.8 Hz, 3H), 2.19-2.13 (m, 3H), 2.09-2.03 (m, 3H), 1.80 (bs, 2H), 1.37-1.31 (m, 2H), 1.28 (bs, 2H). |
| I-560 I-561 | 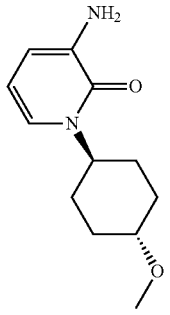 | I-539 was separated into isomers: (CHIRAL PAK IB 250 mm * 4.6 mm, 5 µM) using 0.1% diethylamine in methanol at 4 mL/min. FR-a: MS(ES): m/z 482.62 [M + H]+· LCMS purity: 100%, HPLC purity: 99.07%, Chiral HPLC purity: 100%, NMR (DMSO-$d_6$, 400 MHZ): 8.80 (s, 1H), 8.51-8.49 (d, J = 6.8 Hz, 1H), 8.19 (s, 1H), 8.03-8.01 (d, J = 8.8 Hz, 1H), 7.39-7.37 (d, J = 6.4 Hz, 1H), 6.40-6.37 (d, J = 7.2 Hz, 1H), 6.25 (s, 1H), 4.80 (s, 1H), 4.58-4.54 (t, J = 6.8 Hz, 1H), 4.34 (s, 1H), 3.27 (s, 3H), 3.22 (s, 1H), 2.91 (s, 3H), 2.16-1.95 (m, 6H), 1.80-1.73 (m, 5H), 1.33-1.31 (d, J = 10.8 Hz, 3H). FR-b: MS(ES): m/z 438.50 [M + H]+· LCMS purity: 100%, HPLC purity: 99.89%, Chiral HPLC purity: 99.43%, NMR (DMSO-$d_6$, 400 MHZ): 8.80 (s, 1H), 8.51-8.49 (d, J = 7.2 Hz, 1H), 8.19 (s, 1H), 8.03-8.01 (d, J = 8.4 Hz, 1H), 7.88-7.87 (d, J = 4.8 Hz, 1H), 7.39-7.38 (d, J = 6.4 Hz, 1H), 6.40-6.37 (t, J = 7.2 Hz, 1H), 6.25 (s, 1H), 4.80 (s, 1H), 4.56-4.54 (d, J = 7.2 Hz, 1H), 4.34 (s, 1H), 3.27 (s, 3H) 3.22 (s, 1H), 2.91-90 (d, J = 3.6 Hz, 3H), 2.16-1.19 (m, 5H), 1.80-1.73 (m, 5H), 1.33-1.1.23 (d, J = 10.8 Hz, 3H). |
| I-473 | 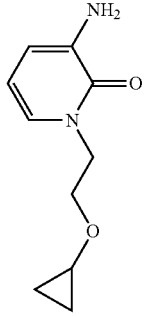 [SMILES: Nc1cccn(CCOC2CC2)c1=O] | MS(ES): m/z 454.35 [M + H]+, LCMS purity: 96.22%, HPLC purity: 95.49%, CHIRAL HPLC: 47.53%, 47.67%, $^1$H NMR (DMSO-$d_6$, 400 MHZ): 8.84 (s, 1H), 8.54-8.52 (d, J = 7.2 Hz, 1H), 8.20 (s, 1H), 8.04-8.02 (d, J = 8.8 Hz, 1H), 7.89-7.87 (d, J = 5.2 Hz, 1H), 7.28-7.26 (d, J = 6.8 Hz, 1H), 6.35-6.32 (t, J = 7.2 Hz, 1H), 6.26 (s, 1H), 5.38 (bs, 1H), 4.58-4.55 (t, J = 7.2 Hz, 1H), 4.35 (bs, 1H), 4.17-4.14 (t, J = 4.8 Hz, 2H), 3.76-3.74 (t, J = 10.4 Hz, 2H), 2.91-2.90 (d, J = 4.8 Hz, 3H), 2.19-2.17 (m, 1H), 2.06-1.96 (m, 2H), 1.77-1.72 (m, 2H), 0.39 (bs, 4H). |
| I-515 I-516 | 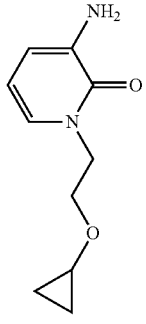 [SMILES: Nc1cccn(CCOC2CC2)c1=O] | I-473 was separated into isomers: CHIRAL PAK AD-H (250 × 4.6 mm, 5 u) and 0.1% DEA in IPA:ACN (50:50) at 4 mL/min. FR-a: MS(ES): m/z 454.3 [M + H]+, LCMS purity: 94.73%, HPLC purity: 88.16%, CHIRAL HPLC purity: 95.12%, $^1$H NMR (DMSO-$d_6$, 400 MHZ): 8.83 (s, 1H), 8.55-8.53 (d, J = 7.2 Hz, 1H), 8.20 (s, 1H), 8.05-8.03 (d, J = 8.8 Hz, 1H), 7.88-7.86 (d, J = 4.8 Hz, 1H), 7.28-7.27 (d, J = 6 Hz, 1H), 6.36-6.33 (t, J = 7.2 Hz, 1H), 6.27 (s, 1H), 5.40-5.38 (m, 1H), 4.59-4.56 (t, J = 7.2 Hz, 1H), 4.36 (bs, 1H), 4.17-4.15 (t, J = 4.8 Hz, 2H), 3.77-3.75 (d, J = 5.2 Hz, 2H), 3.18 (s, 1H), 2.20 (bs, 1H), 2.12-1.96 (m, 3H), 1.83-1.73 (m, 1H), 1.24 (s, 1H), 1.05-1.04 (d, J = 6 Hz, 1H), 0.84-0.80 (m, 1H), 0.41 (bs, 3H). FR-b: MS(ES): m/z 454.2 [M + H]+, LCMS purity: 100%, HPLC purity: 98.95%, CHIRAL HPLC purity: 99.72%, $^1$H NMR (DMSO-$d_6$, 400 MHZ): 8.83 (s, 1H), 8.55-8.53 (d, J = 7.6 Hz, 1H), 8.20 (s, 1H), 8.05-8.03 (d, J = 8.8 Hz, 1H), 7.88-7.86 (d, J = 5.2 Hz, 1H), 7.28-7.27 (d, J = 6.8 Hz, 1H), 6.36-6.33 (t, J = 6.8 Hz, 1H), 6.27 (s, 1H), 5.39-5.38 (d, J = 4 Hz, 1H), 4.59-4.56 (t, J = 7.2 Hz, 1H), 4.35 (bs, 2H), 4.17-4.15 (t, J = 4.8 Hz, 2H), 3.77-3.75 (t, J = 5.2 Hz, 2H), 2.19 (bs, 2H), 2.12-1.96 (m, 3H), 1.78-1.73 (m, 2H), 1.05-1.04 (d, J = 6 Hz, 1H), 0.41 (bs, 3H). |

1063
Synthesis of N-(2-hydroxycyclobutyl)-5-(1-((1R, 2R)-2-methoxycyclopentyl)-1H-pyrrolo[2,3-b]pyridin-3-yl)-7-(methylamino)pyrazolo[1,5-a]pyrimidine-3-carboxamide (I-1341)
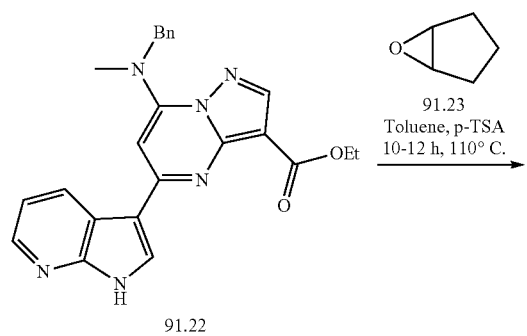
91.22
→ 91.23 Toluene, p-TSA 10-12 h, 110° C.
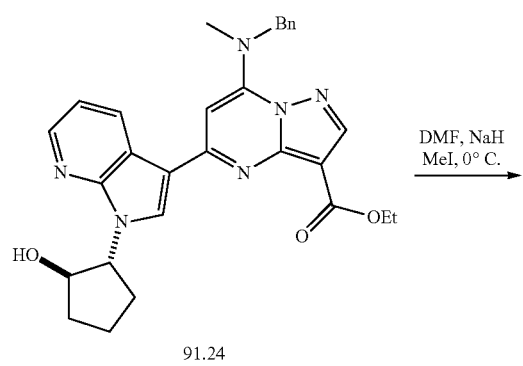
91.24
→ DMF, NaH MeI, 0° C.
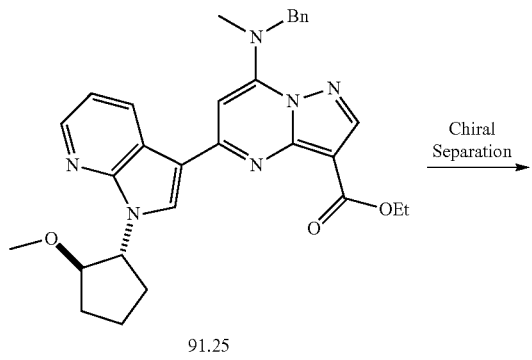
91.25
→ Chiral Separation
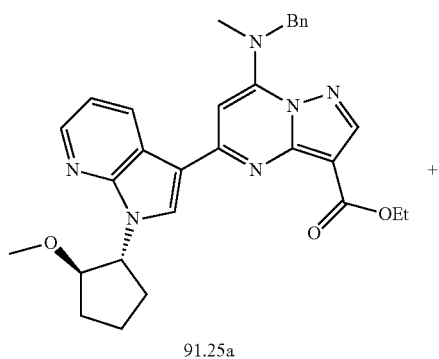
91.25a
1064
-continued
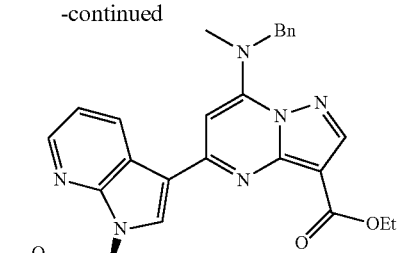
91.25b
+
91.25a
→ MeOH, THF, LiOH H2O, RT, 24 h
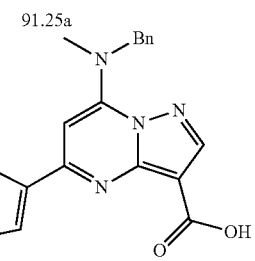
91.26a
→ ClH·H2N / HO DMF, HATU, DIPEA, RT
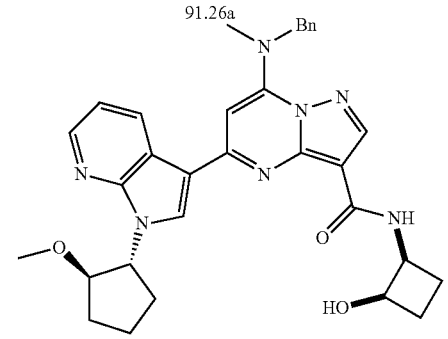
91.27a
→ Triflic acid, 0° C.
I-1341

Synthesis of Compound 91.22.

Compound was synthesized as per I-960 to obtain 91.22. (Yield: 83.64%), MS (ES): m/z 427.18 [M+H]+

Synthesis of Compound 91.24.

To a cooled solution of 91.22 (1.0 g, 2.34 mmol, 1.0 eq), in Toluene (10 mL) was added 91.23 (0.393 g, 4.68 mmol, 2.0 eq) and p-Toluenesulfonic acid (0.040 g, 0.23 mmol, 0.1 eq). The reaction mixture was stirred at 100° C. for 10-12 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.5% methanol in dichloromethane to obtain 91.24. (0.6 g, 50.12%). MS(ES): m/z 511.24 [M+H]

Synthesis of Compound 91.25.

To a solution of 91.24 (0.6 g, 1.75 mmol, 1.0 eq) in Dimethylformamide (6 mL), was added Methyl iodide (0.273 g, 1.92 mmol, 1.1 eq). Sodium hydride (0.084 g, 3.5 mmol, 2 eq) was added at 0° C. Reaction mixture was stirred at room temperature for 2 h. After completion of reaction, reaction mixture was diluted with water extracted with diethyl ether. Organic layer was combined, dried over sodium sulphate and concentrated under reduced pressure to obtain solid which was. This was further purified by distillation to obtain pure 91.25. (0.560 g, Yield: 90.84%). MS (ES): m/z 425.26 [M+H]+.

Synthesis of Compound 91.25a and 91.25b.

Isomers of 91.25 (0.75 g) were separated out using column (CHIRALPAK IB 250 mm*4.6 mm, 5 u) and 0.1% DEA in IPA:MEOH (50:50) as co-solvent with flow rate of 4 mL/min. to get pure fraction-1 (FR-a) and fraction-2 (FR-b). FR-a was concentrated under reduced pressure at 30° C. to afford pure 91.25a. (0.280 g). MS(ES): m/z 525.26 [M+H]+. FR-b was concentrated under reduced pressure at 30° C. to afford pure 91.25b. (0.290 g). MS(ES): m/z 525.26 [M+H]+.

Synthesis of Compound 91.26a.

To a solution of 91.25a (0.280 g, 0.53 mmol, 1.0 eq), in methano: tetrahydrofuran: water (6 mL, 2:2:1) was added lithium hydroxide (0.127 g, 5.3 mmol, 10 eq). The reaction was stirred at 60° C. for 16 h. After completion of reaction, reaction mixture was concentrated under reduced pressure to obtain residue. To this added water and acidified with IN hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 91.26a. (0.220 g, 83.01%). MS(ES): m/z 497.23 [M+H]+.

Synthesis of Compound 91.27a.

Compound was synthesized using general procedure A to obtain 91.27a. (0.160 g, 63.84%), MS (ES): 566.28 [M+H]+.

Synthesis of Compound I-1341:

To a solution of 91.27a (0.040 g, 0.070 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1341 (0.030 g, 89.21%), MS (ES): m/z 476.82 [M+H]+, LCMS purity: 100%, HPLC purity: 98.94%, CHIRAL HPLC: 49.62%, 50.37%, $^1$H NMR (DMSO-$d_6$, 400 MHZ): 9.30-9.28 (d, J=7.2 Hz, 1H), 8.71 (s, 1H), 8.61-8.59 (d, J=8.4 Hz, 1H), 8.44-8.42 (d, J=5.6 Hz, 1H), 8.30 (s, 1H), 8.07-8.06 (d, J=4.8 Hz, 1H), 7.25-7.23 (t, J=6.8 Hz, 1H), 6.67 (s, 1H), 5.70-5.69 (d, J=6.4 Hz, 1H), 5.56-5.55 (d, J=3.2 Hz, 1H), 4.63-4.60 (t, J=6.8 Hz, 1H), 4.47-4.44 (m, 2H), 3.15 (s, 1H), 3.09-3.08 (d, J=4.8 Hz, 3H), 2.28-2.21 (m, 3H), 2.05-2.01 (m, 3H), 1.82-1.76 (m, 3H), 1.11-1.07 (t, J=6.8 Hz, 3H).

Synthesis of N-((1R,2S)-2-hydroxycyclobutyl)-5-(1-((1R,2R)-2-methoxycyclopentyl)-1H-pyrrolo[2,3-b]pyridin-3-yl)-7-(methylamino)pyrazolo[1,5-a]pyrimidine-3-carboxamide (I-1247) and N-((1S,2R)-2-hydroxycyclobutyl)-5-(1-((1R,2R)-2-methoxycyclopentyl)-1H-pyrrolo[2,3-b]pyridin-3-yl)-7-(methylamino)pyrazolo[1,5-a]pyrimidine-3-carboxamide (I-1246)

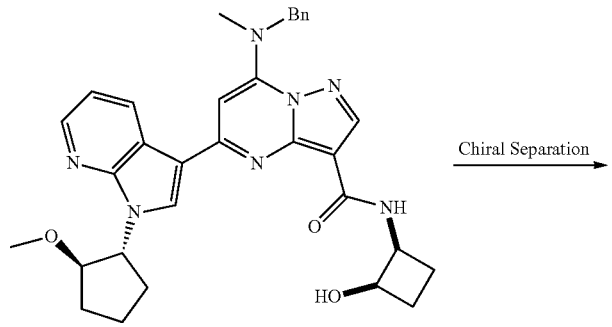

91.27a

Chiral Separation →

-continued

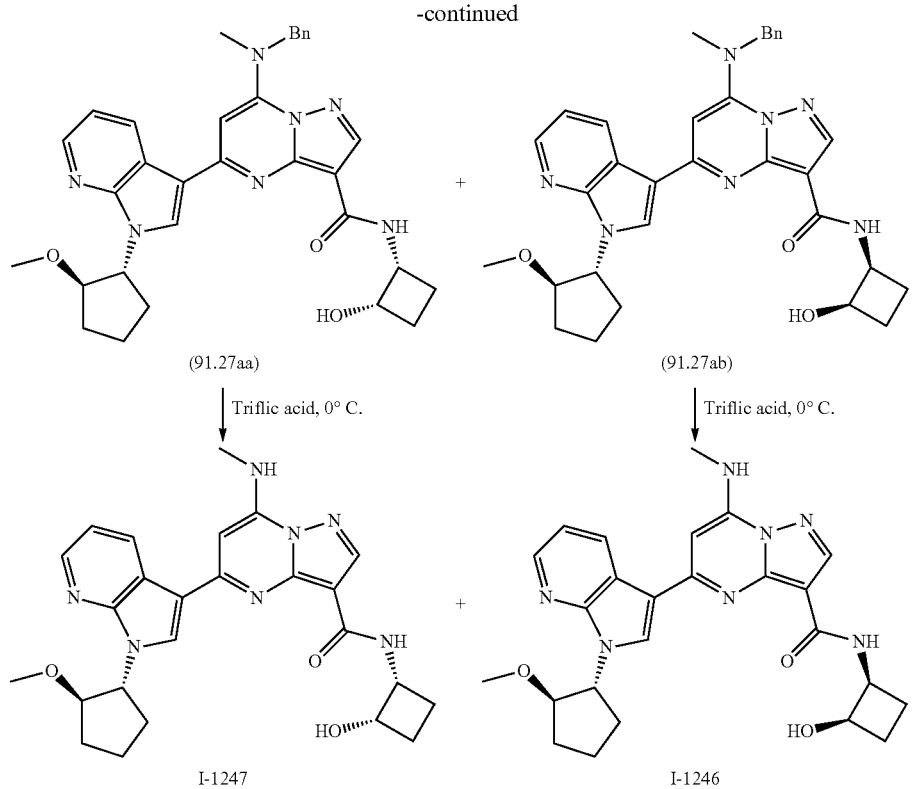

Synthesis of Compound 91.27aa and 91.27ab.

Isomers of 91.27a (0.120 g) were separated out using column CHIRALPAK AD-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford 0.045 g. MS(ES): m/z 566.28 [M+H]$^+$. FR-b was concentrated under reduced pressure at 30° C. to afford 0.045 g. MS(ES): m/z 566.28 [M+H]$^+$.

Synthesis of Compound I-1247 and I-1246.

To a solution of FR-a (0.045 g, 0.079 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 0.035 g, 92.52%, MS (ES): m/z 476.36 [M+H]$^+$, LCMS purity: 99.18%, HPLC purity: 98.19%, CHIRAL HPLC: 99.27%, $^1$H NMR (DMSO-d$_6$, 400 MHZ): 9.30-9.28 (d, J=7.2 Hz, 1H), 8.71 (s, 1H), 8.61-8.59 (d, J=8.4 Hz, 1H), 8.43-8.42 (d, J=5.6 Hz, 1H), 8.30 (s, 1H), 8.04 (bs, 1H), 7.24 (bs, 1H), 6.67 (s, 1H), 5.70-5.69 (d, J=6.4 Hz, 1H), 5.55-5.54 (d, J=3.2 Hz, 1H), 4.63-4.61 (d, J=6.8 Hz, 1H), 4.47-4.44 (m, 2H), 3.17 (s, 3H), 3.09-3.08 (d, J=4.8 Hz, 3H), 2.29-2.23 (m, 3H), 1.92-1.85 (m, 4H), 1.23 (bs, 2H), 0.86 (s, 1H).

To a solution of FR-b (0.045 g, 0.079 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane.

Organic layer was combined, dried over sodium sulphate and concentrated under reduced pressure to obtain crude material. This was further purified by trituration with diethyl ether to a obtain 0.032 g, 92.52%, MS (ES): m/z 476.4 [M+H]$^+$, LCMS purity: 98.66%, HPLC purity: 97.89%, CHIRAL HPLC: 98.01%, $^1$H NMR (DMSO-d$_6$, 400 MHZ): 9.30-9.28 (d, J=7.2 Hz, 1H), 8.71 (s, 1H), 8.61-8.59 (d, J=8.4 Hz, 1H), 8.43-8.42 (d, J=5.6 Hz, 1H), 8.30 (s, 1H), 8.06-8.04 (d, J=4.8 Hz, 1H), 7.26-7.23 (t, J=6.8 Hz, 1H), 6.67 (s, 1H), 5.76-5.67 (m, 1H), 5.55-5.54 (d, J=3.2 Hz, 1H), 4.63-4.60 (m, 1H), 4.49-4.43 (m, 2H), 3.15 (s, 3H), 3.09-3.08 (d, J=4.8 Hz, 3H), 2.29-2.23 (m, 3H), 1.92-1.85 (m, 4H), 1.23 (bs, 2H), 0.85 (s, 1H).

Synthesis of N-(2-hydroxycyclobutyl)-5-(1-((1S, 2S)-2-methoxycyclopentyl)-1H-pyrrolo[2,3-b]pyridin-3-yl)-7-(methylamino)pyrazolo[1,5-a]pyrimidine-3-carboxamide (I-1340)

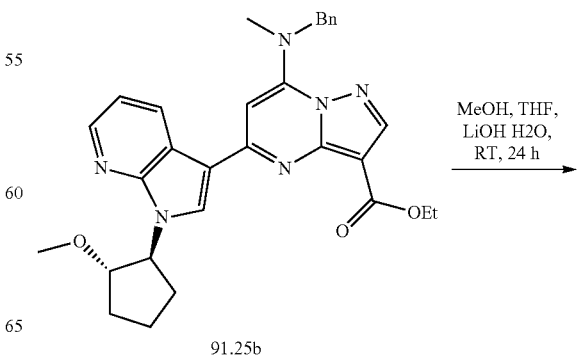

91.25b

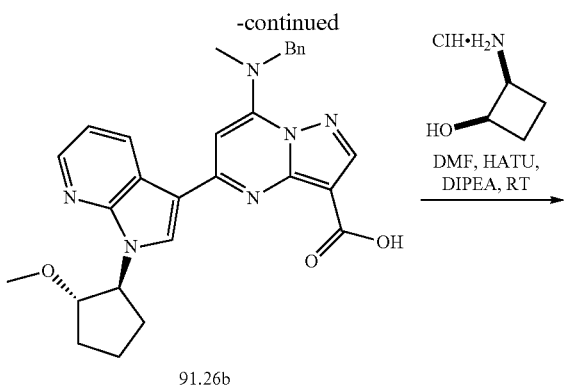

91.26b

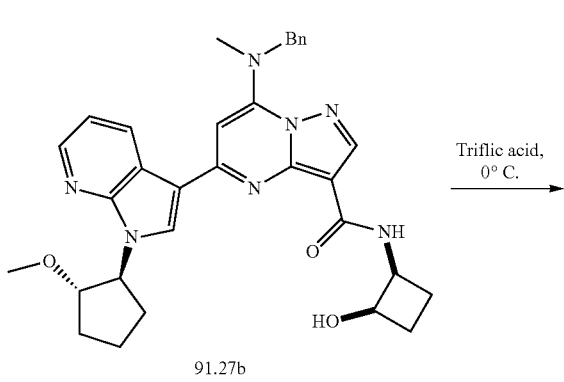

91.27b

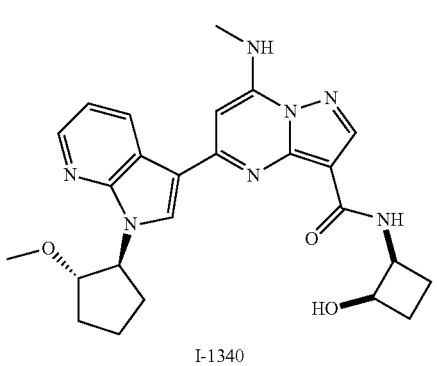

I-1340

Synthesis of Compound 91.26b.

To a solution of 91.25b (0.290 g, 0.55 mmol, 1.0 eq), in methano: tetrahydrofuran: water (6 mL, 2:2:1) was added lithium hydroxide (0.132 g, 5.5 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 91.26b. (0.220 g, 80.15%). MS(ES): m/z 497.23 [M+H]$^+$ Synthesis of Compound 91.27b.

Compound was synthesized using general procedure A to obtain 91.27b. (0.155, 61.85%), MS (ES): 566.28 [M+H]$^+$ Synthesis of Compound I-1340.

To a solution of 91.27b (0.040 g, 0.070 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1340 (0.030 g, 89.21%), MS (ES): m/z 476.77 [M+H]$^+$, LCMS purity: 100%, HPLC purity: 100%, CHIRAL HPLC: 48.69%, 48.24%, $^1$H NMR (DMSO-d$_6$, 400 MHZ): 9.31-9.29 (d, J=7.6 Hz, 1H), 8.72 (s, 1H), 8.62-8.60 (d, J=8.4 Hz, 1H), 8.44-8.43 (d, J=6 Hz, 1H), 8.31 (s, 1H), 8.07-8.06 (d, J=4.8 Hz, 1H), 7.27-7.24 (t, J=6.8 Hz, 1H), 6.68 (s, 1H), 5.74-5.68 (m, 1H), 5.56-5.55 (d, J=3.6 Hz, 1H), 4.64-4.61 (m, 1H), 4.50-4.44 (m, 2H), 3.35 (s, 2H), 3.16 (s, 3H), 3.10-3.09 (d, J=4.8 Hz, 3H), 2.27-2.19 (m, 1H), 1.86-1.81 (m, 4H), 1.24 (bs, 3H).

Synthesis of N-((1R,2S)-2-hydroxycyclobutyl)-5-(1-((1S,2S)-2-methoxycyclopentyl)-1H-pyrrolo[2,3-b]pyridin-3-yl)-7-(methylamino)pyrazolo[1,5-a]pyrimidine-3-carboxamide (I-1224) and N-((1S,2R)-2-hydroxycyclobutyl)-5-(1-((1S,2S)-2-methoxycyclopentyl)-1H-pyrrolo[2,3-b]pyridin-3-yl)-7-(methylamino)pyrazolo[1,5-a]pyrimidine-3-carboxamide (I-1223)

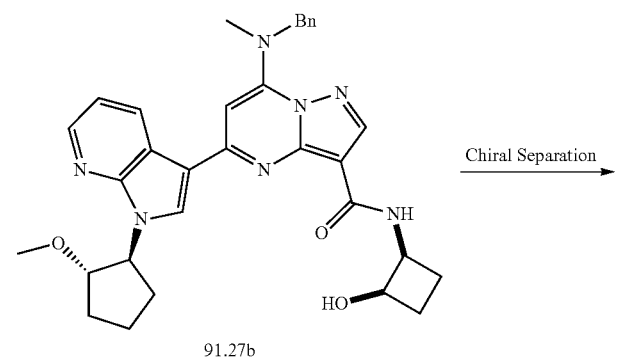

91.27b

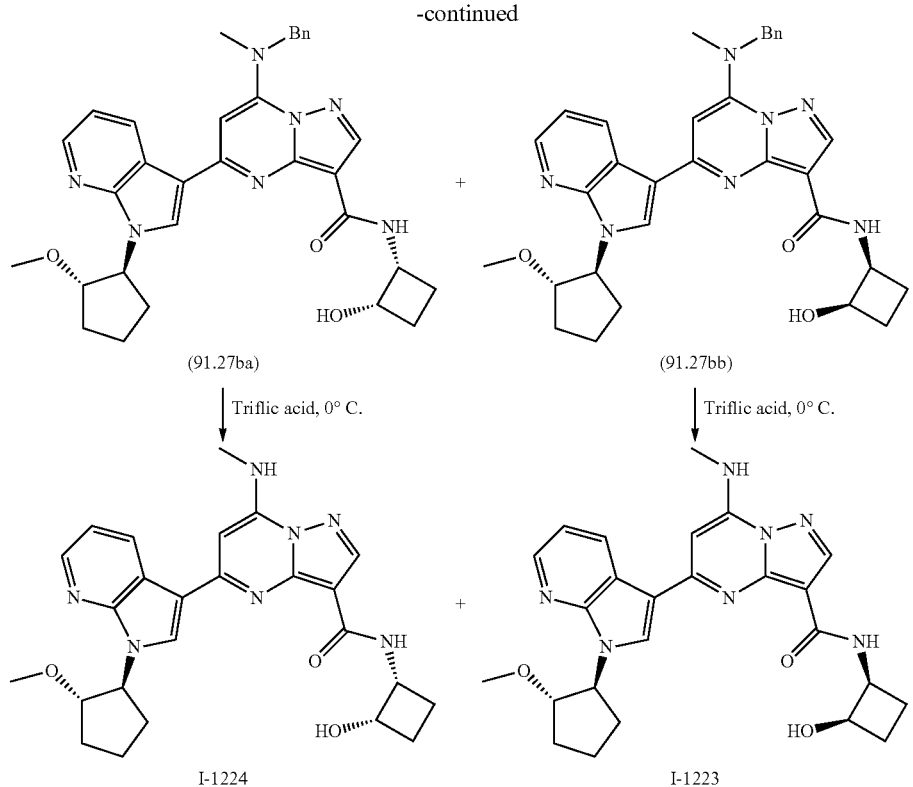

(91.27ba)     (91.27bb)

I-1224     I-1223

Synthesis of Compound 91.27ba and 91.27bb.

Isomers of 91.27b (0.115 g) were separated out using column CHIRALPAK OX-H_0.1% DEA in HEX_IPA-ACN (70-30)_and 0.1% DEA in HEX_IPA-ACN (70-30)_as co-solvent with flow rate of 4 mL/min. to get pure fraction-1 (FR-a) and fraction-2 (FR-b). FR-a was concentrated under reduced pressure at 30° C. to afford 0.043 g. MS(ES): m/z 566.28 [M+H]$^+$. FR-b was concentrated under reduced pressure at 30° C. to afford 0.043 g. MS(ES): m/z 566.28 [M+H]$^+$.

Synthesis of I-1224 and I-1223.

To a solution of FR-a (0.043 g, 0.076 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 0.031 g, 85.76%, MS (ES): m/z 476.77 [M+H]$^+$, LCMS purity: 100%, HPLC purity: 100%, CHIRAL HPLC: 99.55%, $^1$H NMR (DMSO-d$_6$, 400 MHZ): 9.31-9.29 (d, J=7.6 Hz, 1H), 8.72 (s, 1H), 8.63-8.60 (d, J=8.4 Hz, 1H), 8.44-8.42 (d, J=6.4 Hz, 1H), 8.31 (s, 1H), 8.07-8.05 (d, J=4.8 Hz, 1H), 7.27-7.23 (t, J=6.8 Hz, 1H), 6.68 (s, 1H), 5.74-5.68 (m, 1H), 5.56-5.55 (d, J=4 Hz, 1H), 4.65-4.61 (m, 1H), 4.50-4.47 (m, 2H), 3.19 (s, 3H), 3.11-3.09 (d, J=4.8 Hz, 3H), 2.20-2.16 (m, 3H), 2.02-1.93 (m, 4H), 1.60-1.24 (bs, 3H).

To a solution of FR-b (0.043 g, 0.076 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 0.031 g, 85.76%, MS (ES): m/z 476.77 [M+H]$^+$, LCMS purity: 100%, HPLC purity: 100%, CHIRAL HPLC: 100%, $^1$H NMR (DMSO-d$_6$, 400 MHZ): 9.31-9.29 (d, J=7.6 Hz, 1H), 8.72 (s, 1H), 8.62-8.60 (d, J=8.4 Hz, 1H), 8.44-8.42 (d, J=6.4 Hz, 1H), 8.31 (s, 1H), 8.07-8.05 (d, J=4.8 Hz, 1H), 7.27-7.23 (t, J=6.8 Hz, 1H), 6.68 (s, 1H), 5.72-5.71 (d, J=6.8 Hz, 1H), 5.56-5.55 (d, J=4 Hz, 1H), 4.63 (bs, 1H), 4.50-4.44 (m, 2H), 3.16 (s, 3H), 3.11-3.09 (d, J=4.8 Hz, 3H), 2.20-2.16 (m, 3H), 2.02-1.93 (m, 4H), 1.60-1.24 (bs, 3H).

Synthesis of N-(2-hydroxycyclobutyl)-7-(methylamino)-5-(1-((R)-tetrahydro-2H-pyran-3-yl)-1H-pyrrolo[2,3-b]pyridin-3-yl)pyrazolo[1,5-a]pyrimidine-3-carboxamide (-I-1257)

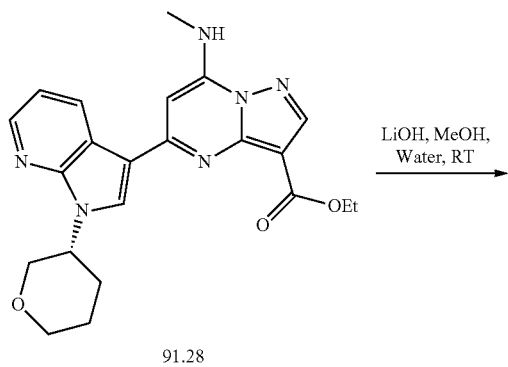

91.28

Synthesis of Intermediate 91a.

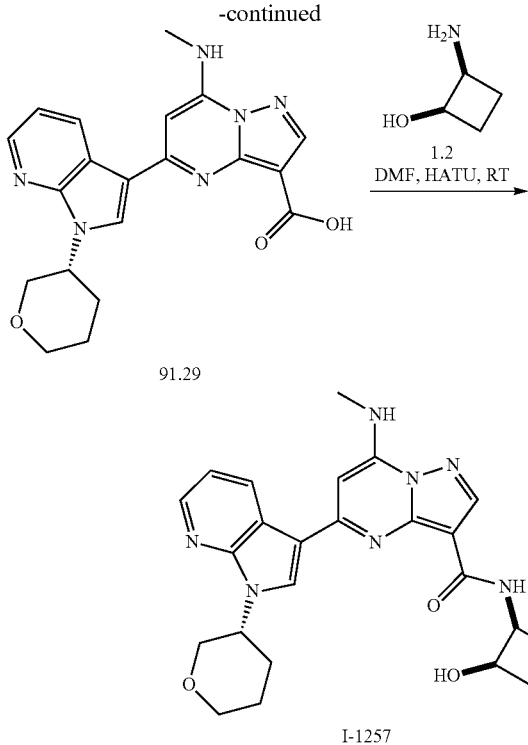

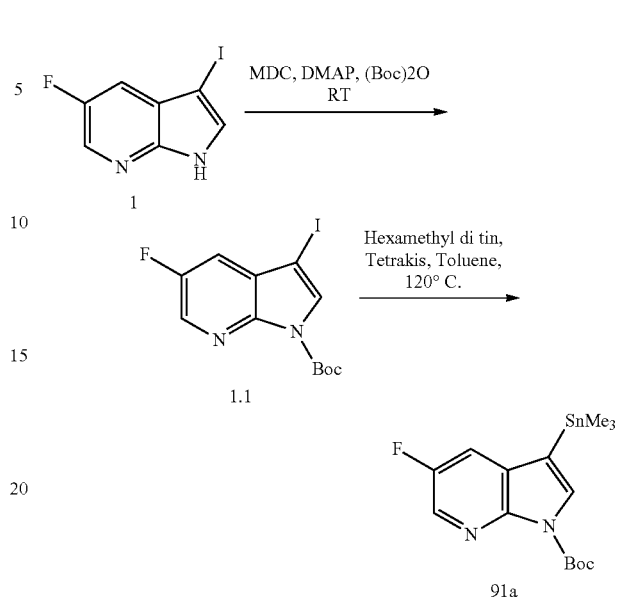

Synthesis of Compound 91.28.

Compound was synthesized as per I-1258 to obtain 91.28. MS (ES): m/z 421.19 [M+H]$^+$

Synthesis of Compound 91.29.

To a solution of 91.28 (0.4 g, 0.956 mmol, 1.0 eq), in methanol:water (8 mL, 2:1) was added lithium hydroxide (0.219 g, 9.56 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 91.29. (0.340 g, 91.08%). MS(ES): m/z 393.16 [M+H]$^+$

Synthesis of Compound I-1257.

Compound was synthesized using general procedure A to obtain I-1257 (0.120 g, 88.72%), MS (ES): m/z 462.77 [M+H]$^+$, LCMS purity: 98.94%, HPLC purity: 98.02%, CHIRAL HPLC: 47.81%, 49.84%, $^1$H NMR (DMSO-d$_6$, 400 MHZ): 9.04-9.02 (d, J=8.4 Hz, 1H), 8.82-8.81 (d, J=3.6 Hz, 1H), 8.68-8.64 (t, J=7.6 Hz, 1H), 8.41-8.40 (d, J=4 Hz, 1H), 8.37 (s, 1H), 8.27-8.26 (d, J=4.4 Hz, 1H), 7.34-7.31 (m, 1H), 6.75 (s, 1H), 4.97 (bs, 1H), 4.60 (bs, 1H), 4.44 (bs, 1H), 4.04 (bs, 1H), 3.98-3.95 (d, J=10.8 Hz, 1H), 3.75-3.72 (d, J=10.4 Hz, 1H), 3.46 (s, 1H), 3.15-3.014 (d, J=4.4 Hz, 4H), 2.22 (bs, 4H), 1.86 (bs, 3H), 1.28-1.25 (m, 1H).

Synthesis of Compound 1.1.

To a solution of 1. (0.7 g, 2.67 mmol, 1 eq) in dichloromethane (7 mL), 4-Dimethylaminopyridine (0.015 g, 0.13 mmol, 0.05 eq) and Triethylamine (0.809 g, 8.01 mmol, 3 eq) was added. Di-tert-butyl dicarbonate (0.638 g, 2.93 mmol, 1.1 eq) was added at 0° C. The reaction mixture was stirred at room temperature for 1 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by column chromatography using 10% ethylacetate in hexane as eluant to obtain 1.1. (0.650 g, Yield: 67.19%). MS (ES): m/z 361.99 [M−H]$^+$

Synthesis of Compound 91a.

To a degassed solution of 1.1 (0.650 g, 1.79 mmol, 1.0 eq) and hexamethylditin (2.3 g, 7.16 mmol, 4.0 eq) in toluene (39 mL) was added tetrakis(triphenylphosphine)palladium (0) (0.196 g, 0.17 mmol, 0.1 eq) and the reaction mixture was heated at 120° C. for 2 h under N$_2$. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by column chromatography using 10% ethylacetate in hexane as eluant to obtain 91a. (0.5 g, Yield: 69.81%). MS (ES): m/z 400.06 [M+H]$^+$

Synthesis of Intermediate 91b.

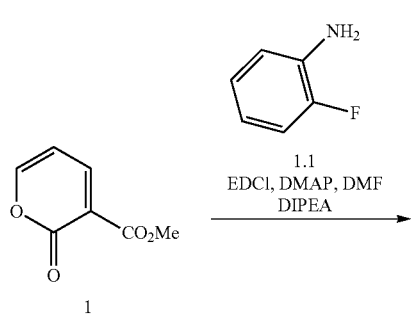

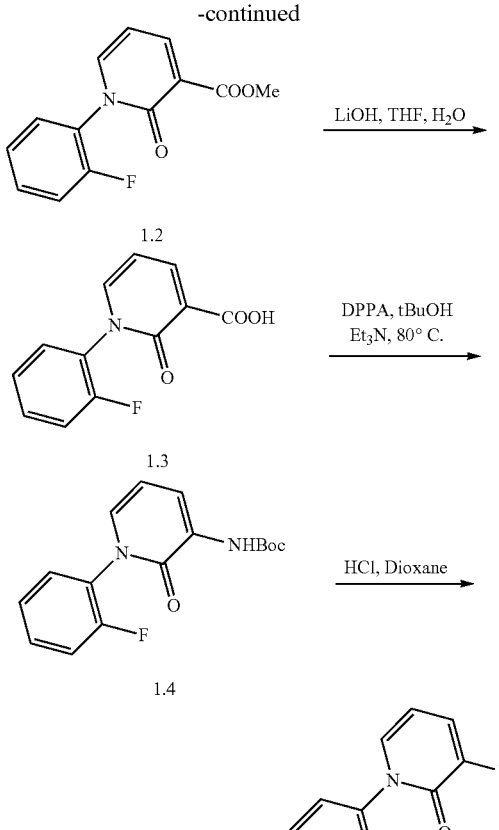

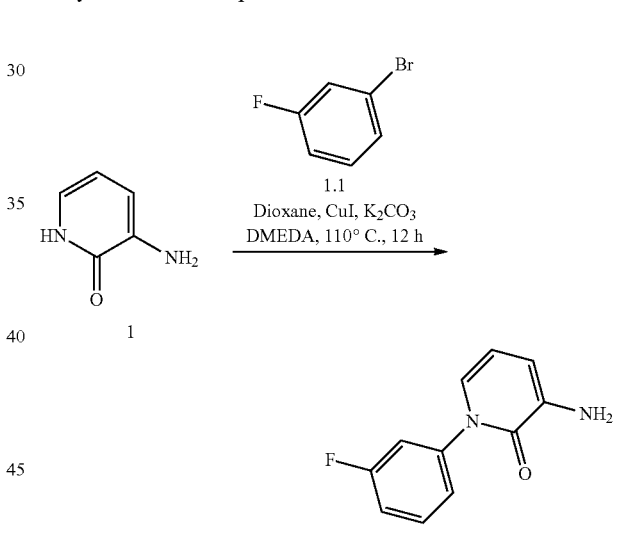

Synthesis of Compound 1.2.

To a cooled solution of 1. (2.0 g, 12.97 mmol, 1.0 eq), in N,N-dimethylformamide (25 mL) was added 1.1 (1.43 g, 12.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.6 g, 16.86 mmol, 1.3 eq), 4-Dimethylaminopyridine (0.315 g, 2.59 mmol, 0.2 eq) and N,N-Diisopropylethylamine (1.17 g, 9.07 mmol, 0.7 eq), was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (1.5 g, 46.76%). MS(ES): m/z 248.07 [M+H]$^+$.

Synthesis of Compound 1.3.

To a solution of 1.2 (1.5 g, 6.06 mmol, 1.0 eq), in tetrahydrofuran: water (20 mL, 2:1) was added lithium hydroxide (1.45 g, 60.6 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (1.0 g, 70.68%). MS(ES): m/z 234.05 [M+H]$^+$.

Synthesis of Compound 1.4.

To a solution of 1.3 (1.0 g, 4.28 mmol, 1.0 eq) in tert.butanol (10 mL) was added triethylamine (0.735 g, 7.27 mmol, 1.7 eq) and diphenyl phosphoryl azide (1.52 g, 5.56 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.640 g, 49.04%). MS(ES): m/z 305.13 [M+H]$^+$.

Synthesis of Compound 91b.

A cooled solution of 1.4 (0.640 g, 2.10 mmol, 1 eq) in dioxane (8 mL) was added 4N hydrochloric acid in dioxane (12 mL) as a dropwise. The reaction mixture was stirred at room temperature for 2 h. After completion of reaction, reaction mixture was concentrated under reduced pressure to obtain pure 91b. (0.480 g, 97.80%). MS(ES): m/z 205.07 [M+HCl]$^+$.

Synthesis of Compound 91c.

Synthesis of Compound 91c.

To a solution of 1. (1.0 g, 9.08 mmol, 1 eq) and 1.1 (1.90 g, 10.89 mmol, 1.2 eq) in 1,4-dioxane (100 mL) was added potassium carbonate (2.5 g, 18.16 mmol, 2.0 eq) and degassed with argon for 15 min. Copper iodide (0.344 g, 1.81 mmol, 0.2 eq) and 1,2-dimethylethylenediamine (0.319 g, 3.63 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 91c. (0.6 g, 32.35%). MS(ES): m/z 205.07 [M+H]$^+$.

Synthesis of Intermediate 91d.

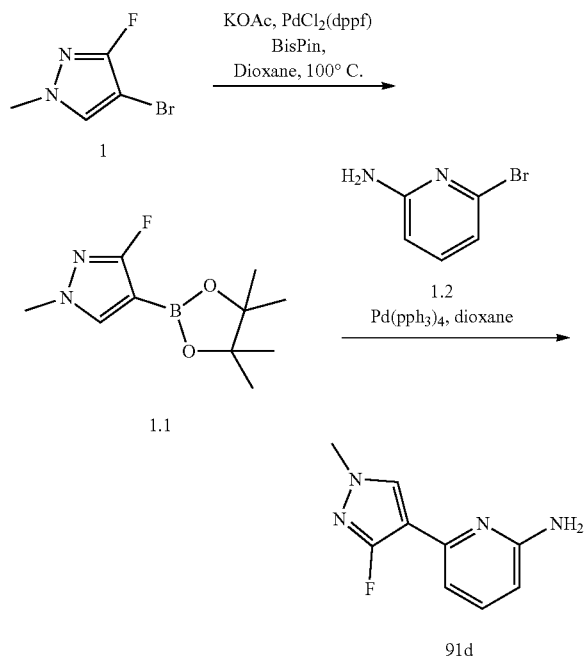

Synthesis of Compound 1.1.

Argon was purged for 15 min through a stirring solution of 1 (0.250 g, 1.39 mmol, 1.0 eq), Bis(pinacolato)diboron (0.457 g, 1.80 mmol, 1.3 eq) and Potassium acetate (0.340 g, 3.47 mmol, 2.5 eq) in 1,4 dioxane (10 mL) [1,1'-Bis(diphenylphosphino)ferrocene]palladium(II) dichloride (0.095 mg, 0.13 mmol, 0.1 eq) was added to it and further purging done for 10 min. Reaction was allowed to stirred at 100° C. for 6 h. After completion of reaction, reaction mixture was poured over water and product was extracted with ethyl acetate. Organic layer was combined, washed with brine solution, dried over sodium sulphate and concentrated under reduced pressure to obtain 1.1. (0.163 g, 51.63%). MS (ES): m/z 227.13 [M+H]$^+$.

Synthesis of Compound 91d.

Argon was purged for 15 min through a stirring solution of 1.1 (0.163 g, 0.72 mmol, 1.0 eq), 1.2 (0.136 g, 0.79 mmol, 1.1 eq) and Sodium carbonate (0.228 g, 2.16 mmol, 3.00 eq) in 1,4dioxane:water (4 mL, 3:1) Tetrakis(triphenylphosphine)palladium(0) (0.041 mg, 0.036 mmol, 0.05 eq) was added to it and further purging done for 10 min. Reaction was allowed to stirred at 100° C. for 6 h. After completion of reaction, reaction mixture was poured over water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 91d (0.072 g, 51.95%). MS (ES): m/z 193.08 [M+H]$^+$.

Synthesis of Intermediate 91e

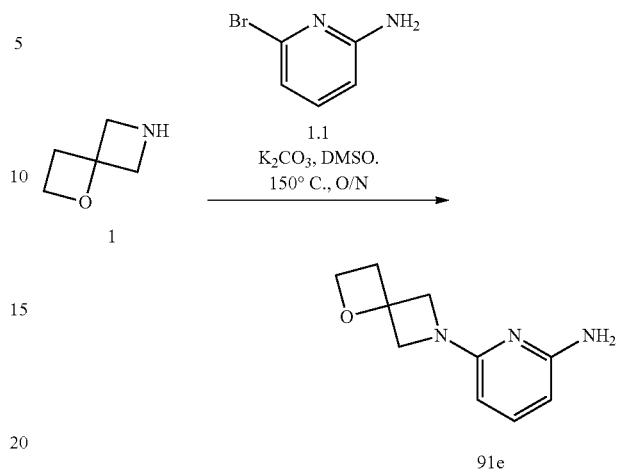

Synthesis of Compound 91e.

To a solution of 1 (1.8 g, 18.18 mmol, 1.0 eq) and 1.1 (3.7 g, 21.81 mmol, 1.2 eq) in dimethyl sulphoxide (30 mL) was added potassium carbonate (5.0 g, 36.36 mmol, 2.0 eq) and reaction mixture heated at 150° C. for 16 h. After completion of reaction, reaction mixture was transferred into ice cold water and the product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 91e (0.8 g, 23.04%). MS(ES): m/z 192.11 [M+H]$^+$.

Synthesis of Intermediate 91f.

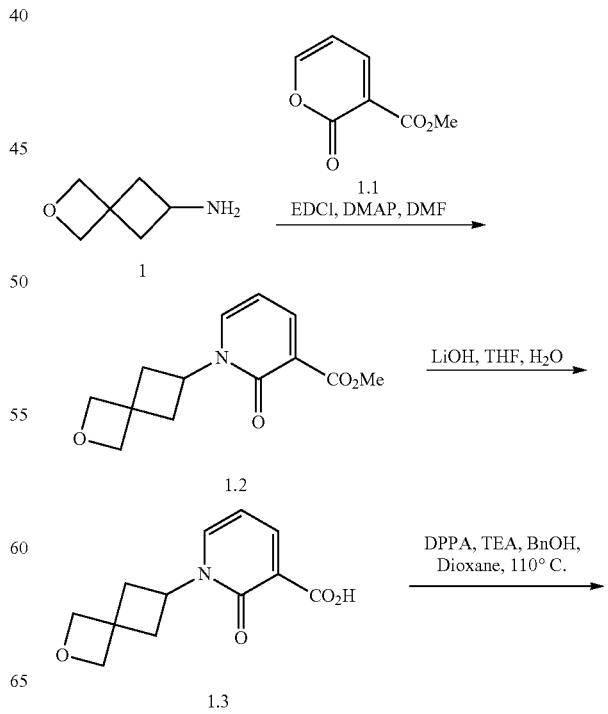

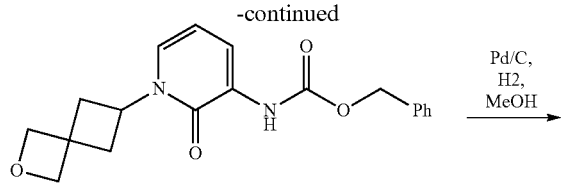

1.4

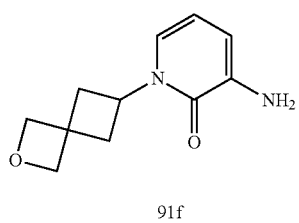

91f

Synthesis of Compound 1.2.

To a cooled solution of 1 (4.0 g, 35.34 mmol, 1.0 eq), in N,N-dimethylformamide (48 mL) was added 1.1 (6.5 g, 42.40 mmol, 1.1 eq). The reaction mixture was stirred at 0° C. for 30 min and further stirred at room temperature for 15 min. N-Ethyl-N'-(3-dimethylaminopropyl)carbodiimide hydrochloride (7.1 g, 45.94 mmol, 1.3 eq), 4-Dimethylaminopyridine (0.86 g, 7.06 mmol, 0.2 eq) and was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (2.2 g, 24.97%). MS(ES): m/z 250.10 [M+H]$^+$.

Synthesis of Compound 1.3.

To a solution of 1.2 (2.2 g, 8.83 mmol, 1.0 eq), in tetrahydrofuran: water (36 mL, 2:1) was added lithium hydroxide (0.883 g, 88.3 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (1.7 g, 81.88%). MS(ES): m/z 236.09 [M+H]$^+$.

Synthesis of Compound 1.4.

To a solution of 1.3 (1.7 g, 7.22 mmol, 1.0 eq) in 1,4-dioxane (40 mL) was added triethylamine (1.2 g, 12.27 mmol, 1.7 eq) and diphenyl phosphoryl azide (3.4 g, 9.38 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (1.0 g, 40.65%). MS(ES): m/z 341.15 [M+H]$^+$.

Synthesis of Compound 91f.

To a solution of 1.4 (1.0 g, 2.93 mmol, 1.0 eq) in methanol (40 ml), palladium on charcoal (0.2 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 91f. (0.350 g, 57.76%). MS (ES): m/z 207.11 [M+H]$^+$.

Synthesis of Intermediate 91h and 91g

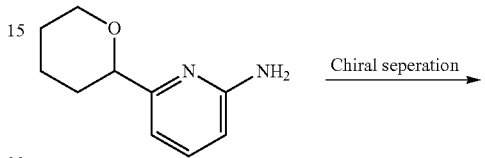

1

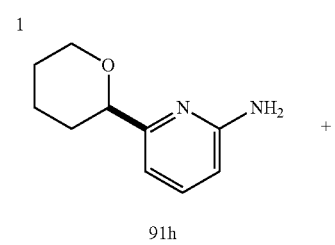

91h

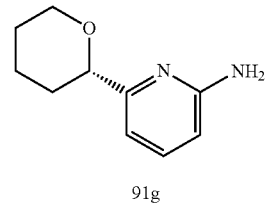

91g

Synthesis of Compound 91h and 91g.

Isomers of 1 (1 g) were separated out using column (CHIRAL PAK AD-H 250×4.6 mm, 5 μM) and 0.3% Diethylamine in methanol as co-solvent with flow rate of 4 mL/min. to get pure 91 h fraction-1 and 91 g fraction-2 (FR-b). FR-a was evaporated under reduced pressure at 30° C. to afford pure 91 h. (0.3 g). MS(ES): m/z 179.2 [M+H]$^+$, LCMS purity: 100%, CHIRAL HPLC purity: 100%. FR-b was evaporated under reduced pressure at 30° C. to afford pure 91 g. (0.35 g). MS(ES): m/z 179.2 [M+H]$^+$, LCMS purity: 98%, CHIRAL HPLC purity: 100%.

Synthesis of Intermediate 91i.

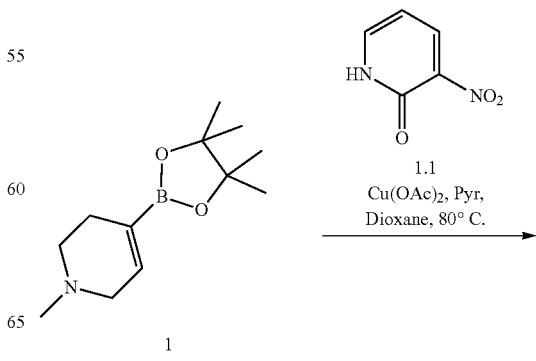

1.1
Cu(OAc)$_2$, Pyr,
Dioxane, 80° C.

1

-continued

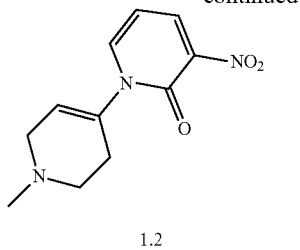

1.2

Pd/C, MeOH, H2 →

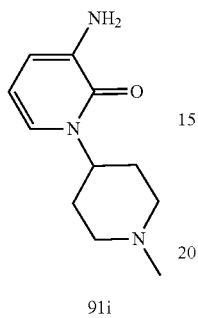

91i

Synthesis of Compound 1.2.

To a solution of 1 (1 g, 4.48 mmol, 1.0 eq) in acetonitrile (6.3 mL) and ethanol (1.3 mL), 1.1 (0.63 g, 4.48 mmol, 1.0 eq), copper acetate (0.81 g, 4.48 mmol, 1.0 eq), molecular sieve (0.20 g) and triethylamine (0.90 g, 8.96 mmol, 2.0 eq) was added and degassed under oxygen. The reaction mixture was heated at 80° C. for 2 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 5% ethyl methanol dichloromethane as eluant to obtain pure 1.2 (0.400 g, 37.94%). MS(ES): m/z 236.24 [M+H]$^+$.

Synthesis of Compound 91i.

To a solution of 1.2 (0.40 g, 1.70 mmol, 1.0 eq) in palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 91i (0.142 g, 39.72%). MS(ES): m/z 208.28 [M+H]$^+$.

Synthesis of Intermediate 91j and 91k

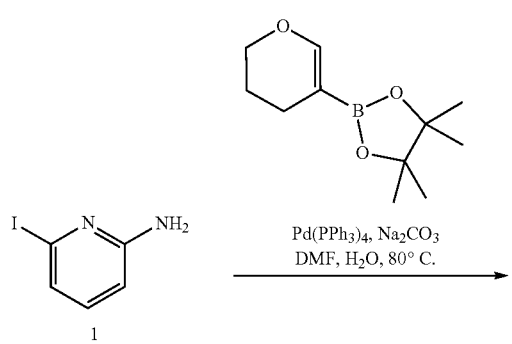

Pd(PPh3)4, Na2CO3
DMF, H2O, 80° C.
→

-continued

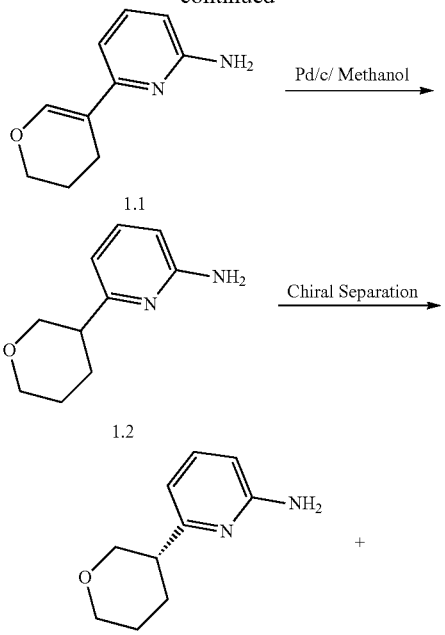

Synthesis of Compound 1.1:

To a solution of 1 (2 g, 9.09 mmol, 1.0 eq), in N,N-dimethylformamide (18 mL) and water (1.6 mL) were added sodium carbonate (4.2 g, 40.297 mmol, 4.5 eq) and 2-(3,4-dihydro-2H-pyran-5-yl)-4,4,5,5-tetramethyl-1,3,2-dioxaborolane (2.49 g, 11.81 mmol, 1.3 eq) at room temperature. The reaction mixture was degassed with argon for 15 min. Then Tetrakis(triphenylphosphine)palladium(0) (1.06 g, 0.909 mmol, 0.1 eq) was added to reaction mixture and stirred at 80° C. for 7 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.1 (1.32 g, 82.40%). MS(ES): m/z 177.23 [M+H]$^+$ Synthesis of Compound 1.2:

To a solution of 1.1 (1.3 g, 7.45 mmol, 1.0 eq) in methanol (15 mL), palladium on charcoal (0.511 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 1.2 (0.8 g, 52.13%). MS (ES): m/z 179.2 [M+H]$^+$ Synthesis of Compound 91j and 91k.

Isomers of 1.2 (0.8 g) were separated out using column (CHIRAL PAK AD-H 250×4.6 mm, 5 pM) and 0.360% Diethylamine in methanol as co-solvent with flow rate of 4 mL/min. to get pure 91j fraction-1 and 91k fraction-2 (FR-b). FR-a was evaporated under reduced pressure at 30° C. to afford pure 91j. (0.36 g). MS(ES): m/z 179.2 [M+H]$^+$, LCMS purity: 100%, CHIRAL HPLC purity: 100%. FR-b was evaporated under reduced pressure at 30° C. to afford pure 91k. (0.36 g). MS(ES): m/z 179.2 [M+H]$^+$, LCMS purity: 98%, CHIRAL HPLC purity: 100%.

Synthesis of Intermediate 911

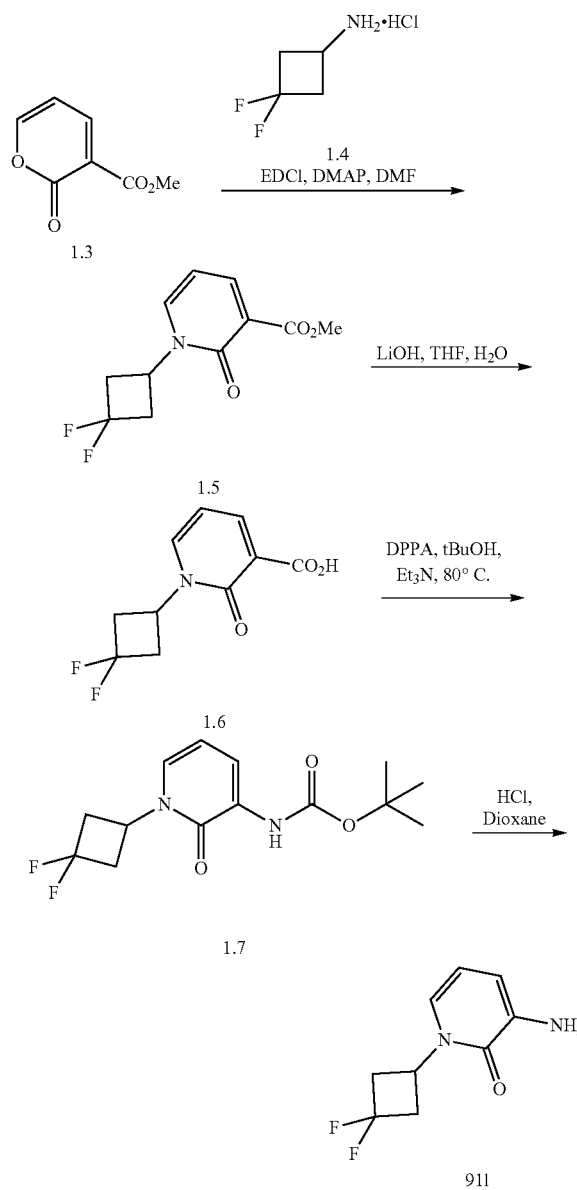

Synthesis of Compound 1.5.

To a cooled solution of 1.3 (2.0 g, 12.97 mmol, 1.0 eq), in N,N-dimethylformamide (22 mL) was added 1.4 (1.3 g, 12.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.6 g, 16.86 mmol, 1.3 eq) and 4-Dimethyl-aminopyridine (0.316 g, 2.59 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.5. (1.8 g, 57.03%). MS(ES): m/z 244.07 [M+H]$^+$.

Synthesis of Compound 1.6.

To a solution of 1.5 (1.8 g, 7.40 mmol, 1.0 eq), in tetrahydrofuran: water (20 mL, 2:1) was added lithium hydroxide (1.7 g, 74.5 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6. (1.4 g, 82.54%). MS(ES): m/z 230.06 [M+H]$^+$.

Synthesis of Compound 1.7.

To a solution of 1.6 (1.4 g, 6.10 mmol, 1.0 eq) in tert.butanol (14 mL) was added triethylamine (1.0 g, 10.37 mmol, 1.7 eq) and diphenyl phosphoryl azide (2.1 g, 7.93 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7. (1.1 g, 59.96%). MS(ES): m/z 301.13 [M+H]$^+$.

Synthesis of Compound 911.

A cooled solution of 1.7 (1.1 g, 3.66 mmol, 1 eq) in dioxane (10 mL) was added 4N hydrochloric acid in dioxane (15 mL) as a dropwise. The reaction mixture was stirred at room temperature for 2 h. After completion of reaction, reaction mixture was concentrated under reduced pressure to obtain pure 911. (0.750 g, 99.55%). MS(ES): m/z 201.08 [M+HCl]$^+$.

Example 92: Synthesis of Compounds where $R^3$ is N-(4-hydroxytetrahydrofuran-3-yl)carboxamide, $R^6$ is Hydrogen, and $R^7$ is Methylamine Synthesis of 5-((1-cyclohexyl-2-oxo-1,2-dihydro-pyridin-3-yl)amino)-N-(4-hydroxytetrahydrofuran-3-yl)-7-(methylamino)pyrazolo[1,5-a]pyrimidine-3-carboxamide (I-1112)

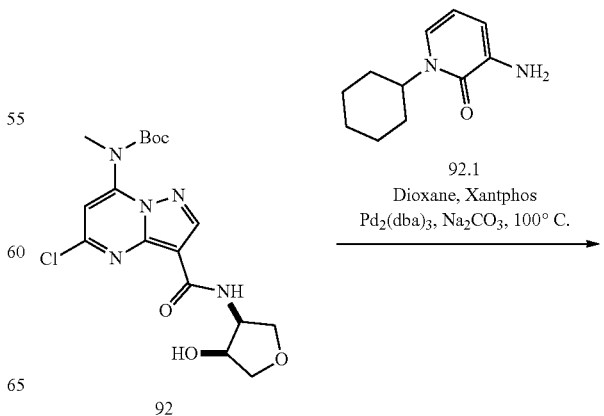

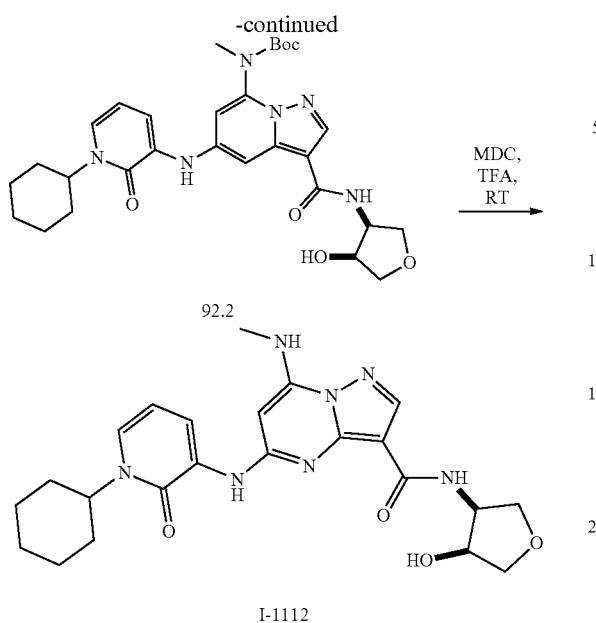

Synthesis of Compound 92.

Compound was synthesized as per I-753 to obtain 92. (Yield: 83.30%), MS (ES): m/z 412.13 [M+H]$^+$ Synthesis of Compound 92.1.

Compound was synthesized as per Example 108 (I-305) to obtain 92.1. (Yield: 96.92%), MS (ES): m/z 193.26 [M+H]$^+$ Synthesis of Compound 92.2.

Compound was synthesized using general procedure B to obtain 92.2. (0.140 g, Yield: 67.72%), MS (ES): 568.28 [M+H]$^+$ Synthesis of Compound I-1112.

Compound was synthesized using general procedure C to obtain I-1112 (0.025 g, 75.88%), MS (ES): m/z 468.52 [M+H]$^+$, LCMS purity: 99.61%, HPLC purity: 99.38%, CHIRAL HPLC: 49.50%, 50.49%, $^1$H NMR (DMSO-d$_6$, 400 MHZ): 8.79 (bs, 1H), 8.43-8.41 (d, J=6.8 Hz, 1H), 8.22 (s, 1H), 7.89 (bs, 1H), 7.85-7.82 (d, J=8.8 Hz, 1H), 7.41-7.40 (d, J=6.8 Hz, 1H), 6.35-6.32 (t, J=7.2 Hz, 1H), 6.25 (s, 1H), 5.58 (bs, 1H), 4.79 (bs, 1H), 4.57 (bs, 1H), 4.08 (bs, 1H), 4.00-3.93 (m, 2H), 3.73-3.70 (d, J=9.6 Hz, 2H), 3.47-3.43 (t, J=8.4 Hz, 2H), 2.91-2.90 (d, J=4.4 Hz, 3H), 1.76 (bs, 1H), 1.55 (bs, 1H), 1.34 (bs, 3H), 1.12 (bs, 3H).

Characterization data for further compounds prepared by the above methods are presented in Table 20 below. Compounds in Table 20 were prepared by methods substantially similar to those described to prepare I-1112, where I-305 was replaced with the reagent as indicated in Table 20.

TABLE 20

| Compound # | Reagent | Chiral Separation Conditions and Characterization Data |
|---|---|---|
| I-755 | 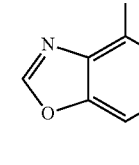 | MS (ES): m/z 410.22 [M + H]$^+$, LCMS purity: 98.65%, HPLC purity: 98.05%, Chiral HPLC: 49.93%, 49.49%, $^1$H NMR (DMSO-d$_6$, 400 MHZ): 9.65 (bs, 1H), 8.77 (s, 1H), 8.36-8.34 (d, J = 7.2 Hz, 1H), 8.23 (s, 1H), 7.96-7.91 (m, 2H), 7.48-7.41 (m, 2H), 6.19 (s, 1H), 5.46-5.45 (d, J = 3.6 Hz, 1H), 4.57-4.54 (m, 1H), 4.19 (bs, 1H), 4.01-3.98 (m, 1H), 3.92-3.89 (t, J = 7.6 Hz, 1H), 3.73-3.70 (d, J = 9.6 Hz, 1H), 2.94-2.93 (d, J = 4.4 Hz, 3H), 1.95 (bs, 1H). |
| I-833 I-834 | 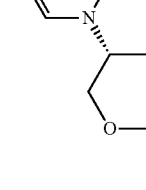 | I-755 was separated into isomers: CHIRALPAK IB (250 mm * 4.6 mm, 5 μM) and 0.1% DEA_HEX_IPA-CAN (70-30) at 4 mL/min. FR-a: MS (ES): m/z 410.22 [M + H]$^+$, LCMS purity: 98.54%, HPLC purity: 99.27%, Chiral HPLC: 99.90 $^1$H NMR (DMSO-d$_6$, 400 MHZ): 8.65 (s, 1H), 8.77 (s, 1H), 8.36-8.34 (d, J = 8 Hz, 1H), 8.24 (s, 1H), 7.96-7.92 (m, 2H), 7.48-7.42 (m, 2H), 6.19 (s, 1H), 5.45 (s, 1H), 4.59-4.52 (m, 1H), 4.19 (s, 1H), 4.01-3.98 (m, 1H), 3.93-3.91 (t, J = 8 Hz, 1H), 3.73-3.71 (d, J = 8.2 Hz, 1H), 3.45-3.42 (t, J = 8 Hz, 1H), 2.94-2.93 (d, J = 4 Hz, 3H). FR-b: MS (ES): m/z 410.22 [M + H]$^+$, LCMS purity: 98.68%, HPLC purity: 99.25% Chiral HPLC: 98.28%, $^1$H NMR-(DMSO-d$_6$, 400 MHZ): 8.65 (s, 1H), 8.77 (s, 1H), 8.37-8.35 (d, J = 8 Hz, 1H), 8.24 (s, 1H), 7.96-7.92 (m, 2H), 7.46-7.44 (m, 2H), 6.19 (s, 1H), 5.45 (s, 1H), 4.59-4.52 (m, 1H), 4.19 (s, 1H), 4.01-3.98 (m, 1H), 3.93-3.91 (t, J = 8 Hz, 1H), 3.73-3.71 (d, J = 8.2 Hz, 1H), 3.45-3.42 (t, J = 8 Hz, 1H), 2.94-2.93 (d, J = 4 Hz, 3H). |
| I-754 |  | MS (ES): m/z 470.51 [M + H]$^+$, LCMS purity: 100%, HPLC purity: 96.93%, Chiral HPLC: 50.22%, 49.32%, $^1$H NMR (DMSO-d$_6$, 400 MHZ): 8.85 (s, 1H), 8.46-8.44 (d, J = 6.8 Hz, 1H), 8.23 (s, 1H), 7.91-7.90 (d, J = 4.8 Hz, 1H), 7.85-7.83 (d, J = 8.8 Hz, 1H), 7.48-7.47 (d, J = 6.4 Hz, 1H), 6.37-6.34 (t, J = 6.8 Hz, 1H), 6.29 (s, 1H), 5.59-5.58 (d, J = 4 Hz, 1H), 4.89 (bs, 1H), 5.58-4.56 (m, 1H), 4.22-4.21 (d, J = 4 Hz, 1H), 4.02-3.98 (m, 1H), 3.96 (bs, 1H), 3.84 (bs, 2H), 3.74-3.71 (d, J = 9.6 Hz, 1H), 3.59-3.54 (t, J = 10 Hz, 1H), 3.48-3.44 (t, J = 8.8 Hz, 2H), 2.92-2.91 (d, J = 4.8 Hz, 3H), 2.08-2.05 (m, 1H), 1.97 (bs, 1H), 1.25 (bs, 1H), 0.87 (bs, 1H). |

TABLE 20-continued

| Compound # | Reagent | Chiral Separation Conditions and Characterization Data |
|---|---|---|
| I-786<br>I-787 | 3-amino-1-(tetrahydro-2H-pyran-3-yl)pyridin-2(1H)-one | I-754 was separated into isomers: CHIRALPAK IB (250 mm * 4.6 mm, 5 μM) and 0.1% DEA_HEX_IPA-ACN (70-30) at 4 mL/min. FR-a: MS (ES): m/z 470.36 [M + H]⁺, LCMS purity: 99.28%, HPLC purity: 99.23%, Chiral HPLC: 99.08%, $^1$H NMR (DMSO-$d_6$, 400 MHZ): 8.84 (s, 1H), 8.45-8.43 (d, J = 7.2 Hz, 1H), 8.22 (s, 1H), 7.90-7.89 (d, J = 4 Hz, 1H), 7.84-7.82 (d, J = 8 Hz, 1H), 7.48-7.46 (d, J = 8 Hz, 1H), 6.36-6.34 (t, J = 7.8 Hz, 1H), 6.28 (s, 1H), 5.77 (s, 1H), 5.58-5.57 (d, J = 8 Hz, 1H), 4.90-4.88 (t, J = 6.4 Hz, 1H), 4.60-4.55 (m, 1H), 4.20-4.19 (d, J = 4 Hz, 1H), 4.01-3.93 (m, 2H), 3.73-3.71 (d, J = 8 Hz, 1H), 3.57-3.55 (d, J = 8 Hz, 1H), 3.52-3.35 (m, 3H), 2.91-2.90 (d, J = 4 Hz, 3H), 2.09-1.96 (m, 2H), 1.77-1.73 (t, J = 15.4 Hz, 2H). FR-b: MS (ES): m/z 470.36 [M + H]⁺, LCMS purity: 100%, HPLC purity: 99.56% Chiral HPLC: 99.00%, $^1$H NMR (DMSO-$d_6$, 400 MHZ): 8.84 (s, 1H), 8.45-8.43 (d, J = 7.2 Hz, 1H), 8.22 (s, 1H), 7.90-7.89 (d, J = 4 Hz, 1H), 7.84-7.82 (d, J = 8 Hz, 1H), 7.48-7.46 (d, J = 8 Hz, 1H), 6.36-6.34 (t, J = 7.8 Hz, 1H), 6.27 (s, 1H), 5.81 (s, 1H), 4.90-4.88 (t, J = 6.4 Hz, 1H), 4.58-4.55 (t, J = 13.6 Hz, 1H), 4.20-4.19 (d, J = 4 Hz, 1H), 4.01-3.93 (m, 2H), 3.85-3.82 (d, J = 8 Hz, 2H), 3.73-3.71 (d, J = 8 Hz, 1H), 3.57-3.55 (d, J = 8 Hz, 1H), 3.52-3.35 (m, 3H), 2.91-2.90 (d, J = 4 Hz, 3H), 2.09-1.96 (m, 1H), 1.77-1.73 (t, J = 15.4 Hz, 2H). |
| I-753 | 3-amino-1-(tetrahydro-2H-pyran-3-yl)pyridin-2(1H)-one | MS (ES): m/z 470.37 [M + H]⁺, LCMS purity: 100%, HPLC purity: 99.19%, Chiral HPLC: 46.01%, 46.24%, $^1$H NMR (DMSO-$d_6$, 400 MHZ): 8.85 (s, 1H), 8.46-8.44 (d, J = 6.8 Hz, 1H), 8.23 (s, 1H), 7.91-7.90 (d, J = 4.8 Hz, 1H), 7.85-7.83 (d, J = 8.8 Hz, 1H), 7.48-7.47 (d, J = 6.4 Hz, 1H), 6.37-6.34 (t, J = 7.2 Hz, 1H), 6.29 (s, 1H), 5.58 (bs, 1H), 4.92-4.87 (m, 1H), 4.60-4.56 (m, 1H), 4.21 (bs, 1H), 4.02-3.98 (m, 2H), 3.86-3.84 (d, J = 10.8 Hz, 2H), 3.74-3.72 (d, J = 8.4 Hz, 1H), 2.92-2.91 (d, J = 4.8 Hz, 3H), 2.08-2.03 (m, 1H), 1.97 (bs, 1H), 1.81 (bs, 2H), 1.27 (bs, 3H). |
| I-784<br>I-785 | 3-amino-1-(tetrahydro-2H-pyran-3-yl)pyridin-2(1H)-one | Intermediate corresponding to 92.2 en route to I-753 was separated into isomers before BOC removal: CHIRAL PAK AD-H (250 x 4.6 mm, 5 μM) and 0.3% diethylamine at 4 mL/min. Product prepared from FR-a: MS (ES): m/z 470.56 [M + H]⁺, LCMS purity: 100%, HPLC purity: 99.19%, Chiral HPLC: 97.53%, $^1$H NMR (DMSO-$d_6$, 400 MHZ): 8.85 (s, 1H), 8.46-8.44 (s, J = 6.4 Hz, 1H), 8.23 (s, 1H), 7.91-7.90 (d, J = 5.2 Hz, 1H), 7.85-7.83 (d, J = 8.8 Hz, 1H), 7.49-7.47 (d, J = 6 Hz, 1H), 6.37-6.34 (t, J = 7.2 Hz, 1H), 6.29 (s, 1H), 5.78 (s, 1H), 5.58 (bs, 1H), 4.89 (bs, 1H), 4.60-4.56 (m, 1H), 4.21 (s, 1H), 4.02-3.96 (m, 1H), 3.94 (s, 1H), 3.86-3.84 (d, J = 10.8 Hz, 2H), 3.74-3.72 (d, J = 8.4 Hz, 1H), 3.59-3.53 (t, J = 10 Hz, 1H), 3.48-3.44 (m, 1H), 2.92-2.91 (d, J = 4.8 Hz, 3H), 1.97 (bs, 1H), 1.78 (bs, 2H), 1.24 (bs, 1H). Product prepared from FR-b: MS (ES): m/z 470.51 [M + H]⁺, LCMS purity: 100%, HPLC purity: 98.96%, Chiral HPLC: 98.32%, $^1$H NMR (DMSO-$d_6$, 400 MHZ): 8.84 (s, 1H), 845-8.43 (s, J = 6.4 Hz, 1H), 8.22 (s, 1H), 7.90-7.89 (d, J = 5.2 Hz, 1H), 7.84-7.82 (d, J = 8.8 Hz, 1H), 7.47-7.46 (d, J = 6.4 Hz, 1H), 6.36-6.32 (t, J = 7.2 Hz, 1H), 6.27 (s, 1H), 5.58 (s, 1H), 4.90-4.85 (m, 1H), 4.58-4.55 (m, 1H), 4.20 (s, 1H), 4.01-3.96 (m, 2H), 3.93 (s, 1H), 3.85-3.82 (d, J = 10.4 Hz, 2H), 3.72-3.70 (d, J = 8.4 Hz, 1H), 3.57-3.52 (t, J = 10.4 Hz, 2H), 3.50-3.45 (m, 2H), 2.91-2.89 (d, J = 4.8 Hz, 3H), 0.89-0.85 (m, 2H). |
| I-746 | 3-amino-1-(4-methoxycyclohexyl)pyridin-2(1H)-one · HCl<br>92a | MS(ES): m/z 498.67 [M + H]⁺, LCMS purity: 100%, HPLC purity: 97.99%, Chiral HPLC purity: 49.25%, 50.72%, NMR (DMSO-$d_6$, 400 MHZ): 8.80 (s, 1H), 8.44-8.42 (d, J = 7.6 Hz, 1H), 8.23 (s, 1H), 7.90-7.89 (d, J = 4.8 Hz, 1H), 7.85-7.83 (d, J = 8.8 Hz, 1H), 7.40-7.38 (d, J = 6 Hz, 1H), 6.36-6.32 (t, J = 7.2 Hz, 1H) 6.26 (s, 1H), 5.77 (s, 1H), 5.58-5.57 (d, J = 4 Hz, 1H), 4.48-5.79 (d, J = 4.8 Hz, 1H), 4.59-4.54 (m, 1H), 4.21-4.20 (d, J = 4 Hz, 1H), 4.02-3.94 (m, 2H), 3.74-3.71 (d, J = 9.2 Hz, 1H), 3.48-3.44 (t, J = 8.4 Hz, 1H), 3.28 (s, 3H), 2.92-2.91 (d, J = 4.8 Hz, 3H), 2.17-2.14 (d, J = 10 Hz, 2H), 1.81-1.75 (m, 4H), 1.34-1.30 (m, 2H). |

TABLE 20-continued

| Compound # | Reagent | Chiral Separation Conditions and Characterization Data |
|---|---|---|
| I-831<br>I-832 | structure 92a (pyridinone with NH₂·HCl, N-linked to 4-methoxycyclohexyl) | I-746 was separated into isomers: (CHIRAL PAK AD-H 250 x 4.6 mm, 5 μM) 0.1% DEA in IPA:MEOH (50:50). FR-a: MS(ES): m/z 498.52 [M + H]⁺, LCMS purity: 100%, HPLC purity: 96.55%, CHIRAL HPLC purity: 99.87%, ¹H NMR (DMSO-d₆, 400 MHZ): 8.80 (s, 1H), 8.44-8.42 (d, J = 7.2 Hz, 1H), 8.23 (s, 1H), 7.91-7.90 (d, J = 4 Hz, 1H), 7.85-7.83 (d, J = 8.8 Hz, 1H), 7.40-7.38 (d, J = 6.8 Hz, 1H), 6.36-6.32 (t, J = 7.2 Hz, 1H), 6.26 (s, 1H), 5.59 (bs, 1H), 4.80 (bs, 1H), 4.61-4.54 (m, 1H), 4.21 (bs, 1H), 4.02-3.96 (m, 1H), 3.94 (s, 1H), 3.78-3.76 (d, J = 6 Hz, 1H), 3.48-3.44 (t, J = 8.8 Hz, 1H), 3.28 (s, 3H), 2.92-2.91 (d, J = 4 Hz, 3H), 2.17-2.14 (d, J = 10.4 Hz, 2H), 1.34-1.30 (m, 3H), 1.24 (s, 1H), 1.05-1.04 (d, J = 6 Hz, 3H). FR-b: MS(ES): m/z 498.47 [M + H]⁺, LCMS purity: 100%, HPLC purity: 97.12%, CHIRAL HPLC purity: 99.31%, ¹H NMR (DMSO-d₆, 400 MHZ): 8.80 (s, 1H), 8.44-8.42 (d, J = 7.2 Hz, 1H), 8.23 (s, 1H), 7.91-7.90 (d, J = 4 Hz, 1H), 7.85-7.83 (d, J = 8.8 Hz, 1H), 7.40-7.38 (d, J = 6.4 Hz, 1H), 6.36-6.32 (t, J = 7.2 Hz, 1H), 6.26 (s, 1H), 4.80 (bs, 1H), 4.59-4.56 (m, 1H), 4.21 (bs, 1H), 4.02-3.96 (m, 1H), 3.94 (s, 1H), 3.73-3.71 (d, J = 8.8 Hz, 1H), 3.48-3.44 (t, J = 8.4 Hz, 1H), 3.28 (s, 3H), 2.92-2.91 (d, J = 4 Hz, 3H), 2.17-2.14 (d, J = 11.2 Hz, 3H), 1.34-1.30 (m, 3H), 1.24 (s, 1H), 1.05-1.04 (d, J = 6 Hz, 3H). |
| I-1407 | 3-amino-1-(3-fluorophenyl)pyridin-2(1H)-one | MS (ES): 480.47 [M + H]⁺, LCMS purity: 100%, HPLC purity: 99.67%, CHIRAL HPLC: 49.03%, 50.96%, ¹H NMR (DMSO-d₆, 400 MHZ): 9.00 (s, 1H), 8.56-8.55 (d, J = 7.6 Hz, 1H), 8.25 (s, 1H), 7.94-7.93 (d, J = 4.8 Hz, 1H), 7.88-7.86 (d, J = 8.8 Hz, 1H), 7.64-7.59 (m, 1H), 7.50-7.48 (d, J = 10 Hz, 1H), 7.35 (bs, 3H), 6.45-6.41 (t, J = 8.8 Hz, 1H), 6.30 (s, 1H), 5.65-5.64 (d, J = 3.6 Hz, 1H), 4.62-4.59 (m, 1H), 4.23 (bs, 1H), 3.76-3.74 (d, J = 9.6 Hz, 1H), 3.52-3.48 (t, J = 8.4 Hz, 2H), 2.92-2.91 (d, J = 4.8 Hz, 3H), 2.51 (s, 1H). |
| I-1304<br>I-1303 | 3-amino-1-(3-fluorophenyl)pyridin-2(1H)-one | Intermediate corresponding to 92.2 en route to I-1407 was separated into isomers before BOC removal: CHIRALCEL OJ-H (250 mm * 4.6 mm, 5u) and 0.1% DEA MEOH (50:50) at 4 mL/min. Product prepared from FR-a: MS (ES): m/z 480.67 [M + H]⁺, LCMS purity: 100%, HPLC purity: 99.43%, Chiral HPLC: 100%, ¹H NMR (DMSO-d₆, 400 MHZ): 8.91 (s, 1H), 8.55-8.54 (d, J = 6 Hz, 1H), 8.24 (s, 1H), 7.94-7.85 (m, 2H), 7.61-7.58 (t, J = 6.8 Hz, 1H), 7.49-7.75 (d, J = 9.6 Hz, 1H), 7.36-7.34 (d, J = 6.8 Hz, 2H), 644-6.40 (t, J = 7.2 Hz, 1H), 6.30 (s, 1H), 5.64-5.63 (d, J = 4 Hz, 1H), 4.59-4.58 (d, J = 5.6, 1H), 4.23 (s, 1H), 4.02-3.95 (m, 3H), 3.75-3.73 (d, J = 9.2 Hz, 1H), 3.51-3.47 (t, J = 8.4 Hz, 1H), 2.91-2.89 (d, J = 4.4 Hz, 3H). Product prepared from FR-b: MS (ES): m/z 480.67 [M + H]⁺, LCMS purity: 100%, HPLC purity: 99.67% Chiral HPLC: 97.82%, ¹H NMR (DMSO-d₆, 400 MHZ): 8.91 (s, 1H), 8.55-8.54 (m, J = 6 Hz, 1H), 8.24 (s, 1H), 7.94-7.85 (m, 2H), 7.61-7.58 (t, J = 6.8 Hz, 1H), 7.49-7.75 (d, J = 9.6 Hz, 1H), 7.36-7.34 (d, J = 6.8 Hz, 2H), 644-6.40 (t, J = 7.2 Hz, 1H), 6.30 (s, 1H), 5.64-5.63 (d, J = 4 Hz, 1H), 4.59-4.58 (d, J = 5.6, 1H), 4.23 (s, 1H), 4.02-3.95 (m, 3H), 3.75-3.73 (d, J = 9.2 Hz, 1H), 3.51-3.47 (t, J = 8.4 Hz, 1H), 2.91-2.89 (d, J = 4.4 Hz, 3H). |
| I-1406 | 3-amino-1-isopropylpyridin-2(1H)-one | MS (ES): 428.57 [M + H]⁺, LCMS purity: 98.49%, HPLC purity: 99.02%, CHIRAL HPLC purity : 48.92%, 49.96%, ¹H NMR (DMSO-d₆, 400 MHZ): 8.84 (s, 1H), 8.45-8.43 (d, J = 7.2 Hz, 1H), 8.23 (s, 1H), 7.90-7.84 (m, 2H), 7.43-7.41 (d, J = 7.2 Hz, 1H), 6.39-6.35 (t, J = 7.2 Hz, 1H), 6.28 (s, 1H), 5.58 (bs, 1H), 5.22-5.17 (m, 1H), 4.60-4.56 (m, 1H), 4.21 (bs, 1H), 4.03-3.94 (m, 2H), 3.74-3.72 (d, J = 9.6 Hz, 1H), 3.49-3.45 (t, J = 8.4 Hz, 1H), 2.92-2.91 (d, J = 4.8 Hz, 3H), 1.36-1.35 (d, J = 6.8 Hz, 6H). |
| I-1301<br>I-1302 | 3-amino-1-isopropylpyridin-2(1H)-one | Intermediate corresponding to 92.2 en route to I-1406 was separated into isomers before BOC removal: CHIRALCEL OJ-H (250 mm * 4.6 mm, 5u) and 0.1% DEA MEOH (70:30) at 4 mL/min. Product prepared from FR-a: MS (ES): m/z 428.52 [M + H]⁺, LCMS purity: 100%, HPLC purity: 95.27%, Chiral HPLC: 100%, ¹H NMR (DMSO-d₆, 400 |

TABLE 20-continued

| Compound # | Reagent | Chiral Separation Conditions and Characterization Data |
|---|---|---|
| | | MHZ): 8.84 (s, 1H), 8.45-8.43 (s, J = 7.2 Hz, 1H), 8.23 (s, 1H), 7.90-7.89 (d, J = 4 Hz, 1H), 7.86-7.84 (d, J = 8 Hz, 1H), 7.42-7.41 (d, J = 6.4 Hz, 1H), 6.39-6.37 (t, J = 7.8 Hz, 1H), 6.28 (s, 1H), 5.59-5.58 (d, J = 8 Hz, 1H), 5.20-5.18 (t, J = 8 Hz, 1H), 4.60-4.59 (t, J = 6.4 Hz, 1H), 4.22-4.21 (d, J = 4 Hz, 1H), 4.02-3.94 (m, 2H), 3.74-3.72 (d, J = 8 Hz, 1H), 3.49-3.47 (t, J = 8 Hz, 1H), 2.92-2.91 (d, J = 4 Hz, 3H), 1.36-1.17 (m, 6H). Product prepared from FR-b: MS (ES): m/z 428.52 [M + H]+, LCMS purity: 100%, HPLC purity: 95.27% Chiral HPLC: 95.21%, 1H NMR (DMSO-d6, 400 MHZ): 8.84 (s, 1H), 8.44-8.42 (s, J = 7.2 Hz, 1H), 8.23 (s, 1H), 7.90-7.89 (d, J = 4 Hz, 1H), 7.86-7.84 (d, J = 8 Hz, 1H), 7.42-7.41 (d, J = 6.4 Hz, 1H), 6.39-6.37 (t, J = 7.8 Hz, 1H), 6.28 (s, 1H), 5.59-5.58 (d, J = 8 Hz, 1H), 5.20-5.18 (t, J = 8 Hz, 1H), 4.60-4.59 (t, J = 6.4 Hz, 1H), 4.22-4.21 (d, J = 4 Hz, 1H), 4.05-3.94 (m, 2H), 3.74-3.72 (d, J = 8 Hz, 1H), 3.49-3.47 (t, J = 8 Hz, 1H), 2.92-2.91 (d, J = 4 Hz, 3H), 1.36-1.17 (m, 6H). |
| I-1313 | 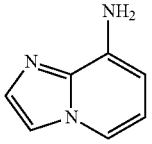 | MS (ES): 409.52 [M + H]+ LCMS purity: 100%, HPLC purity: 98.34%, CHIRAL HPLC: 50.36%, 49.64%, 1H NMR (DMSO-d6, 400 MHZ): 9.45 (s, 1H), 8.26 (s, 1H), 8.23-8.22 (d, J = 6 Hz, 1H), 8.20 (s, 1H), 7.97 (s, 1H), 7.96-7.93 (m, 2H), 7.59 (s, 1H), 6.92-6.88 (t, J = 7.2 Hz, 1H), 6.38 (s, 1H), 5.58-5.57 (d, J = 3.6 Hz, 1H), 4.60-4.55 (m, 1H), 4.23 (bs, 1H), 4.03-4.00 (m, 1H), 3.98-3.94 (m, 1H), 3.76-3.74 (d, J = 7.4 Hz, 1H), 3.51-3.46 (t, J = 8.4 Hz, 1H), 2.95-2.94 (d, J = 4.4 Hz, 3H). |
| I-1261 I-1262 | | Intermediate corresponding to 92.2 en route to I-1313 was separated into isomers before BOC removal: CHIRALPAK OX-H 250 mm * 4.6 mm, 5u) and 0.1% DEA_HEX_IPA_ MEOH (50-50) at 4 mL/min. Product prepared from FR-a: MS (ES): m/z 409.72 [M + H]+, LCMS purity: 100%, HPLC purity: 98.45%, Chiral HPLC: 100%, 1H NMR (DMSO-d6, 400 MHZ): 9.44 (s, 1H), 8.25-8.22 (d, J = 10.4 Hz, 1H), 8.21-8.20 (t, J = 3.2 Hz, 1H), 7.99-7.92 (m, 3H), 7.58 (s, 1H), 6.90-6.88 (t, J = 4.8 Hz, 1H), 6.38 (s, 1H), 5.58-5.57 (d, J = 4 Hz, 1H), 4.60-4.59 (t, J = 4.8 Hz, 1H), 4.22 (s, 1H), 4 08-3.99 (m, 1H), 3.97-3.95 (t, J = 8.2 Hz, 1H), 3.76- |
| | | 3.74 (d, J = 8.4 Hz, 1H), 3.50-3.48 (t, J = 8.8 Hz, 1H), 3.18-3.16 (d, J = 8.2 Hz, 1H), 2.94-2.93 (d, J = 4.6 Hz, 3H). Product prepared from FR-b: MS (ES): m/z 409.72 [M + H]+, LCMS purity: 100%, HPLC purity: 100% Chiral HPLC: 95.39%, 1H NMR (DMSO-d6, 400 MHZ): 9.46 (s, 1H), 8.25-8.22 (d, J = 10.4 Hz, 1H), 8.21-8.20 (t, J = 3.2 Hz, 1H), 7.99-7.92 (m, 3H), 7.58 (s, 1H), 6.90-6.88 (t, J = 4.8 Hz, 1H), 6.38 (s, 1H), 5.58-5.57 (d, J = 4 Hz, 1H), 4.60-4.59 (t, J = 4.8 Hz, 1H), 4.22 (s, 1H), 4.08-3.99 (m, 1H), 3.97-3.95 (t, J = 8.2 Hz, 1H), 3.76-3.74 (d, J = 8.4 Hz, 1H), 3.50-3.48 (t, J = 8.8 Hz, 1H), 3.18-3.16 (d, J = 8.2 Hz, 1H), 2.94-2.93 (d, J = 4.6 Hz, 3H). |

Synthesis of N-(4-hydroxytetrahydrofuran-3-yl)-7-(methylamino)-5-(1-(2-morpholinoethyl)-1H-pyrrolo[2,3-b]pyridin-3-yl)pyrazolo[1,5-a]pyrimidine-3-carboxamide (I-791)

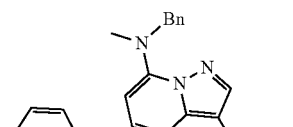

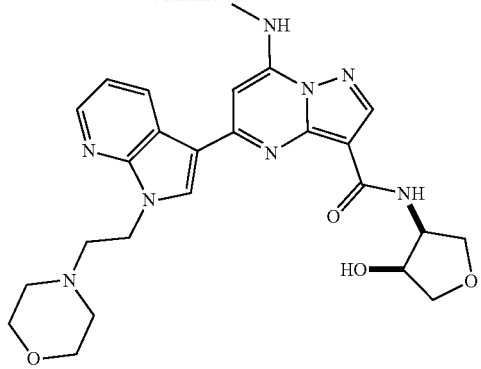

I-791

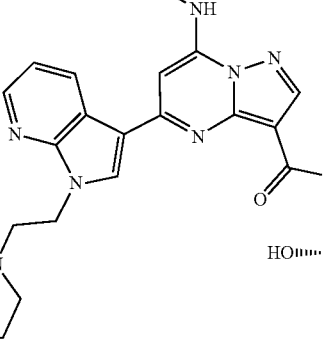

I-855

Synthesis of Compound 92.3.
Compound was synthesized as per I-582 to obtain 92.3 (Yield: 94.47%). MS (ES): m/z 512.44 [M+H]$^+$.

Synthesis of Compound 92.4.
Compound was synthesized using general procedure of A using 92b to obtain 92.4 (0.150 g, 64.30%). MS (ES): m/z 597.29 [M+H]$^+$.

Synthesis of Compound I-791.
Mixture of 92.4 (0.150 g, 0.251 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-791 (0.100 g, 78.53%), MS (ES): m/z 507.47 [M+H]$^+$, LCMS purity: 100%, HPLC purity: 98.61%, Chiral HPLC: 49.87% and 50.13%, $^1$H NMR (DMSO-d$_6$, 400 MHZ): 8.92-8.90 (d, J=8 Hz, 1H), 8.70 (s, 1H), 8.51-8.49 (d, J=8 Hz, 1H), 8.39-8.37 (t, J=4 Hz, 2H), 8.28-8.27 (d, J=4 Hz, 1H), 7.28-7.25 (m, 1H), 6.67 (s, 1H), 5.72-5.71 (d, J=4 Hz, 1H), 4.61-4.53 (m, 3H), 4.32-4.31 (d, J=4 Hz, 1H), 4.06-4.00 (m, 2H), 3.77-3.74 (m, 1H), 3.58-3.54 (m, 5H), 3.13-3.11 (d, J=8 Hz, 3H), 2.84-2.80 (t, J=8 Hz, 2H), 2.51 (m, 4H).

Synthesis of N-((3R,4R)-4-hydroxytetrahydrofuran-3-yl)-7-(methylamino)-5-(1-(2-morpholinoethyl)-1H-pyrrolo[2,3-b]pyridin-3-yl)pyrazolo[1,5-a]pyrimidine-3-carboxamide (I-855) and N-((3S,4S)-4-hydroxytetrahydrofuran-3-yl)-7-(methylamino)-5-(1-(2-morpholinoethyl)-1H-pyrrolo[2,3-b]pyridin-3-yl)pyrazolo[1,5-a]pyrimidine-3-carboxamide

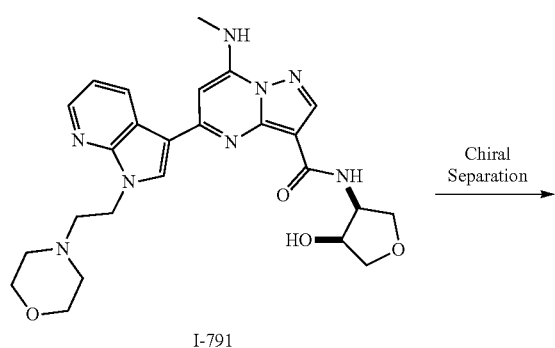

I-791

→ Chiral Separation

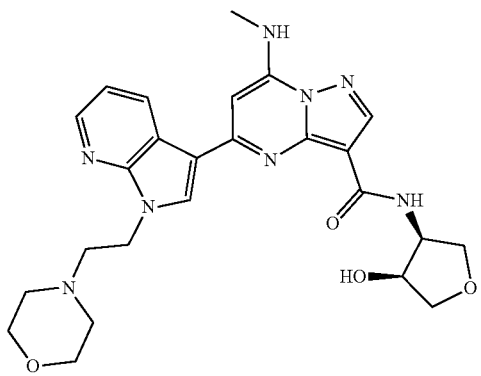

I-856

Synthesis of Compound I-855 & I-856.
Isomers of I-791 (0.125 g) were separated out using column (CHIRAL PAK AD-H 250×4.6 mm, 5 u) 0.1% DEA_HEX_IPA-ACN (70-30) to get pure fraction-1 (FR-a) and pure fraction-2 (FR-b). FR-a was concentrated under reduced pressure at 30° C. to afford 0.025 g. MS(ES): m/z 507.47 [M+H]$^+$, LCMS purity: 100%, HPLC purity: 98.45%, CHIRAL HPLC purity: 99.11%, $^1$H NMR (DMSO-d$_6$, 400 MHZ): 8.92-8.90 (d, J=7.6 Hz, 1H), 8.71 (s, 1H), 8.52-8.49 (d, J=8.4 Hz, 1H), 8.41-8.35 (m, 2H), 8.29-8.28 (d, J=4.8 Hz, 1H), 7.28-7.25 (m, 1H), 6.67 (s, 1H), 5.73-5.72 (d, J=4.4 Hz, 1H), 4.57-4.43 (m, 3H), 4.33 (s, 1H), 4.08-4.00 (m, 2H), 3.83-3.75 (m, 2H), 3.58-3.54 (m, 4H), 3.42-3.38 (m, 2H), 3.13-3.11 (d, J=4.8 Hz, 3H), 2.84-2.81 (t, J=6.4 Hz, 2H), 1.24 (bs, 1H), 1.12-1.08 (m, 1H).

FR-b was concentrated under reduced pressure at 30° C. to afford 0.025 g. MS(ES): m/z 507.42 [M+H]$^+$, LCMS purity: 100%, HPLC purity: 98.83%, CHIRAL HPLC purity: 99.72%, $^1$H NMR (DMSO-d$_6$, 400 MHZ): 8.92-8.90 (d, J=7.6 Hz, 1H), 8.71 (s, 1H), 8.52-8.50 (d, J=8.4 Hz, 1H), 8.39-8.35 (m, 2H), 8.29-8.27 (d, J=4.8 Hz, 1H), 7.29-7.26 (m, 1H), 6.67 (s, 1H), 5.73-5.72 (d, J=4.4 Hz, 1H), 4.59-4.49 (m, 3H), 4.32 (s, 1H), 4.06-4.00 (m, 2H), 3.80-3.75 (m, 2H), 3.58-3.54 (m, 4H), 3.42-3.38 (m, 2H), 3.13-3.11 (d, J=4.8 Hz, 3H), 2.84-2.81 (t, J=6.4 Hz, 2H), 1.25 (bs, 1H), 1.12-1.08 (m, 1H).

1095

Synthesis of N-(4-hydroxytetrahydrofuran-3-yl)-5-(1-isopropyl-1H-pyrrolo[2,3-b]pyridin-3-yl)-7-(methylamino)pyrazolo[1,5-a]pyrimidine-3-carboxamide (I-764)

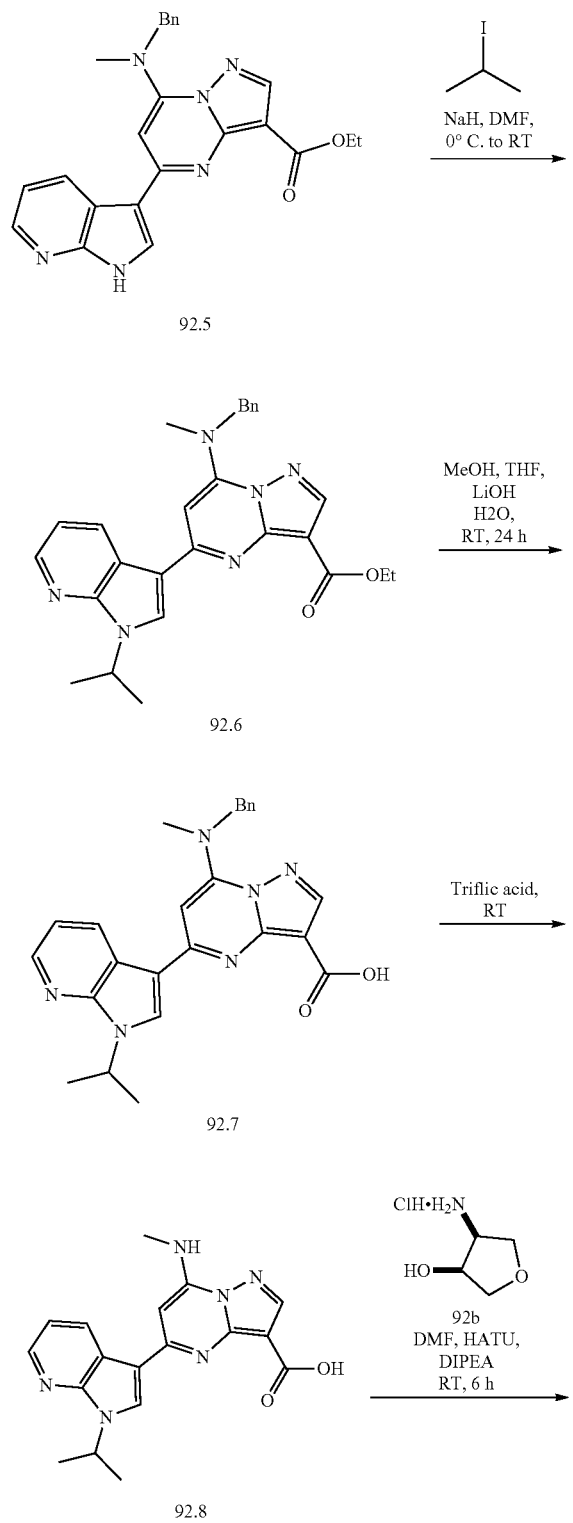

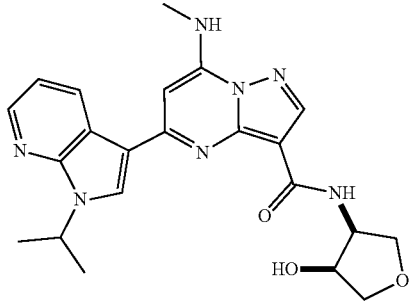

I-764

Synthesis of Compound 92.5.

Compound was synthesized as per experimental protocol Example 78 (I-960) to obtain 92.5. (Yield: 83.64%), MS (ES): m/z 427.18 [M+H]$^+$.

Synthesis of Compound 92.6.

To a solution of 92.5 (0.2 g, 0.93 mmol, 1.0 eq) in dimethylformamide (2 mL), was added 2-iodopropane (0.173 g, 1.02 mmol, 1.1 eq). Sodium hydride (0.044 g, 1.86 mmol, 2 eq) was added at 0° C. Reaction mixture was stirred at room temperature for 2 h. After completion of reaction, reaction mixture was diluted with water extracted with diethyl ether. Organic layer was combined, dried over sodium sulphate and concentrated under reduced pressure to obtain solid which was. This was further purified by distillation to obtain pure 92.6. (0.182 g, Yield: 82.83%). MS (ES): m/z 469.23 [M+H]$^+$.

Synthesis of Compound 92.7.

To a solution of 92.6 (0.182 g, 0.38 mmol, 1.0 eq), in methanol:tetrahydrofuran:water (6 mL, 2:2:1) was added lithium hydroxide (0.091 g, 3.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 92.7 (0.150 g, 87.67%). MS(ES): m/z 441.20 [M+H]$^+$.

Synthesis of Compound 92.8.

Solution of 92.7 (0.150 g, 0.34 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 92.8. (0.120 g, 96.39%). MS(ES): m/z 351.15 [M+H]$^+$.

Synthesis of Compound I-764.

Compound was synthesized using general procedure A using 92b to obtain I-764 (0.110 g, 73.75%), MS (ES): m/z 436.32 [M+H]$^+$, LCMS purity: 100%, HPLC purity: 100%, CHIRAL HPLC: 49.22%, 49.75%, $^1$H NMR (DMSO-d$_6$, 400 MHZ): 8.91-8.89 (d, J=8.8 Hz, 1H), 8.78 (s, 1H), 8.49-8.47 (d, J=8 Hz, 1H), 8.37 (s, 1H), 8.36 (s, 1H), 8.25-8.24 (d, J=5.2 Hz, 1H), 7.27-7.24 (m, 1H), 6.74 (s, 1H), 5.76 (s, 1H), 5.69-5.68 (d, J=4.4 Hz, 1H), 5.22-5.18 (m, 1H), 4.32 (bs, 1H), 4.05-3.98 (m, 2H), 3.59-3.55 (t, J=8 Hz, 1H), 3.13-3.12 (d, J=4.8 Hz, 3H), 1.58-1.56 (m, 6H), 1.27-1.24 (m, 1H).

Synthesis of N-((3S,4S)-4-hydroxytetrahydrofuran-3-yl)-5-(1-isopropyl-1H-pyrrolo[2,3-b]pyridin-3-yl)-7-(methylamino)pyrazolo[1,5-a]pyrimidine-3-carboxamide (I-841) and N-((3R,4R)-4-hydroxytetrahydrofuran-3-yl)-5-(1-isopropyl-1H-pyrrolo[2,3-b]pyridin-3-yl)-7-(methylamino) pyrazolo[1,5-a]pyrimidine-3-carboxamide (I-842)

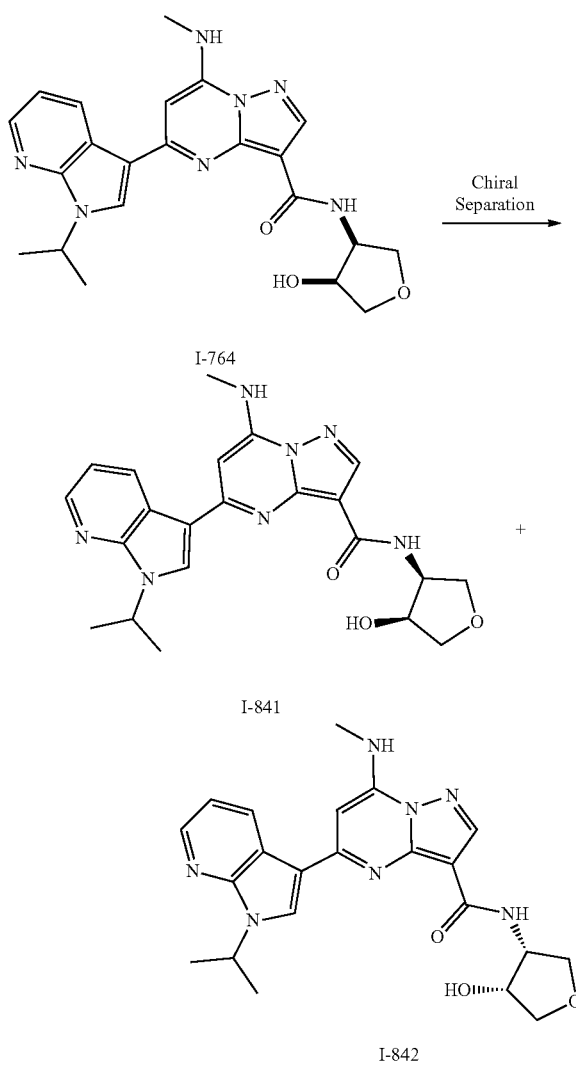

Synthesis of Compound I-841 & I-842.

Isomers of I-764 (0.125 g) were separated out using column CHIRAL PAK AD-H (250×4.6 mm, 5 μM) and 0.1% DEA_HEX_IPA-ACN (70-30) to get pure fraction-1 (FR-a) and fraction-2 (FR-b). FR-a was concentrated under reduced pressure at 30° C. to afford 0.025 g. MS(ES): m/z 436.46 [M+H]+, LCMS purity: 100%, HPLC purity: 100%, CHIRAL HPLC purity: 99.29%, ¹H NMR (DMSO-d₆, 400 MHZ): 8.93-8.91 (d, J=8.0 Hz, 1H), 8.80 (s, 1H), 8.51-8.49 (d, J=8.0 Hz, 1H), 8.39-8.37 (m, 2H), 8.26-8.25 (d, J=4.8 Hz, 1H), 7.28-7.25 (m, 1H), 6.75 (s, 1H), 5.71-5.69 (d, J=4.4 Hz, 1H), 5.25-5.19 (m, 1H), 4.60-4.53 (m, 1H), 4.33 (s, 1H), 4.06-3.99 (m, 2H), 3.77-3.74 (dd, J=2.0 & 7.6 Hz, 1H), 3.60-3.56 (t, J=8.0 Hz, 1H), 3.15-3.13 (d, J=4.8 Hz, 3H), 1.59-1.57 (m, 6H).

FR-b was concentrated under reduced pressure at 30° C. to afford 0.026 g. MS(ES): m/z 436.46 [M+H]+, LCMS purity: 100%, HPLC purity: 99.52%, CHIRAL HPLC purity: 100%, ¹H NMR (DMSO-d₆, 400 MHZ): 8.93-8.91 (d, J=8.0 Hz, 1H), 8.80 (s, 1H), 8.50-8.48 (d, J=8.0 Hz, 1H), 8.39-8.37 (m, 2H), 8.27-8.26 (d, J=4.8 Hz, 1H), 7.29-7.25 (m, 1H), 6.75 (s, 1H), 5.71-5.70 (d, J=4.4 Hz, 1H), 5.25-5.18 (m, 1H), 4.658-4.53 (m, 1H), 4.33 (s, 1H), 4.06-3.99 (m, 2H), 3.77-3.74 (dd, J=2.0 & 7.6 Hz, 1H), 3.60-3.56 (t, J=8.0 Hz, 1H), 3.15-3.13 (d, J=4.8 Hz, 3H), 1.60-1.57 (m, 6H).

Characterization data for further compounds prepared by the above methods are presented in Table 20.1 below. Compounds in Table 20.1 were prepared by methods substantially similar to those described to prepare I-764, where 2-iodopropane was replaced with the reagent as indicated in Table 20.1.

TABLE 20.1

| Cpnd # | Reagent | Chiral Separation Conditions and Characterization Data |
|---|---|---|
| I-1408 | Br-(tetrahydropyran) | MS(ES): mz 478.32 [M + H]+ LCMS purity: 95.11%, HPLC purity: 95.17%, ¹H NMR (DMSO-d₆, 400 MHZ): 8.98 (s, 1H), 8.86 (s, 1H), 8.43-8.41 (d, J = 8.4 Hz, 1H), 8.37 (s, 1H), 8.25-8.23 (d, J = 4.8 Hz, 1H), 7.29-7.26 (m, 1H), 6.84 (s, 1H), 5.09 (bs, 1H), 4.62-4.55 (m, 1H), 4.31 (bs, 1H), 4.09-3.99 (m, 4H), 3.77-3.75 (d, J = 8 Hz, 1H), 3.65-3.56 (m, 3H), 3.13-3.12 (d, J = 4.8 Hz, 3H), 2.24-2.18 (m, 2H), 1.98 (bs, 2H), 1.24 (bs, 2H). |
| I-1356 | cyclopropyl-B(OH)₂ | Reagent coupling conditions: Cu(OAc)₂, 2,2'-bipyridine, Na₂CO₃, DCE, 80 °C. MS (ES): m/z 434.47 [M + H]+, LCMS purity: 99.27%, HPLC purity: 98.72%, CHIRAL HPLC: 47.02%, 51.79%, ¹H NMR (DMSO-d₆, 400 MHz): 8.89-8.85 (d, J = 8 Hz, 1H), 8.59 (s, 1H), 8.43-8.37 (m, 3H), 8.25-8.24 (d, J = 4.8 Hz, 1H), 7.29-7.26 (m, 1H), 6.74 (s, 1H), 5.67-5.66 (d, J = 4 Hz, 1H), 4.58-4.52 (m, 1H), 4.30 (s, 1H), 4.05-4.39 (m, 2H), 3.78-3.74 (m, 2H), 3.58-3.54 (t, J = 8 Hz, 1H), 3.11 (s, 1H), 1.33-1.14 (m, 6H). |

1099

Synthesis of N-(4-hydroxytetrahydrofuran-3-yl)-7-(methylamino)-5-((6-((R)-tetrahydro-2H-pyran-3-yl)pyridin-2-yl)amino)pyrazolo[1,5-a]pyrimidine-3-carboxamide (I-695)

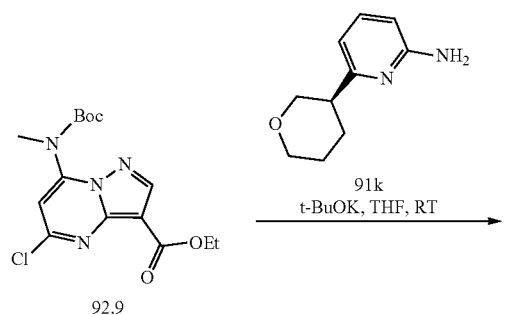

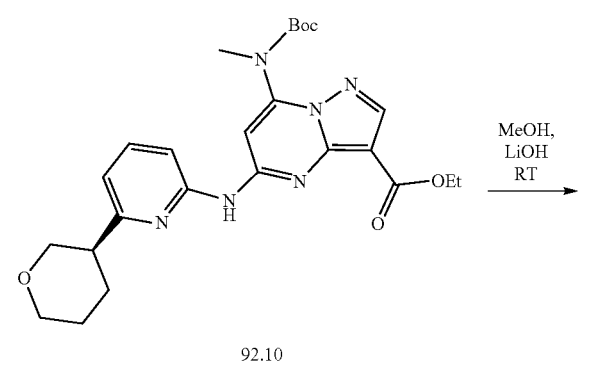

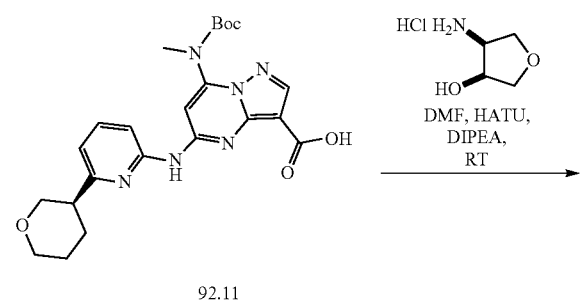

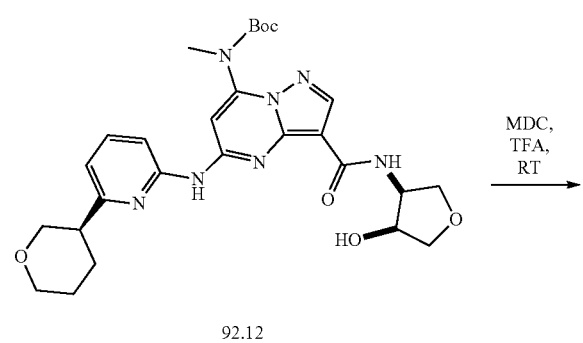

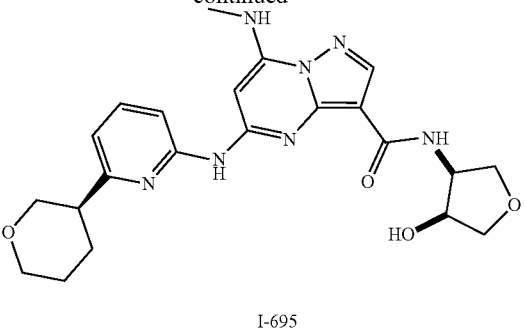

I-695

Synthesis of Compound 92.9.

Compound was synthesized using general procedure of core synthesis to obtain 92.9. (Yield: 62.21%). MS (ES): m/z 355.5 [M+H]+.

Synthesis of Compound 91k.

Compound was synthesized as depicted for the synthesis of intermediate 91k. MS (ES): m/z 179.1 [M+H]+.

Synthesis of Compound 92.10.

To a cooled solution of 92.9 (0.250 g, 0.70 mmol, 1.0 eq), and 91k (0.124 g, 0.70 mmol, 1.0 eq) in tetrahydrofuran (5 mL) at 0° C. was added potassium tert-butoxide (1M in tetrahydrofuran) (1.4 mL, 1.4 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 92.10 (0.206 g, 58.87%). MS (ES): m/z 497.25 [M+H]+.

Synthesis of Compound 92.11.

To a solution of 92.10 (0.206 g, 0.41 mmol, 1.0 eq), in methanol: water (5 mL, 2:1) was added lithium hydroxide (0.098 g, 4.1 mmol, 10 eq). The reaction was stirred at RT for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 92.11 (0.162 g, 83.35%). MS(ES): m/z 469.22 [M+H]+.

Synthesis of Compound 92.12.

Compound was synthesized using general procedure A to obtain 92.12 (0.110 g, 57.46%), MS (ES): 554.27 [M+H]+.

Synthesis of Compound I-695.

Compound was synthesized using general procedure C to obtain I-695 (0.085 g, 94.33%), MS (ES): m/z 454.51 [M+H]+, LCMS purity: 97.33%, HPLC purity: 97.44%, CHIRAL HPLC: 49.04%, 49.43%, $^1$H NMR (DMSO-d$_6$, 400 MHZ): 9.79 (s, 1H), 8.24 (s, 1H), 8.04-8.03 (d, J=4.4 Hz, 2H), 7.96-7.90 (m, 1H), 7.71-7.67 (t, J=7.6 Hz, 1H), 6.96-6.95 (d, J=7.2 Hz, 1H), 6.40 (bs, 1H), 5.53-5.52 (d, J=4 Hz, 1H), 4.55-4.49 (m, 1H), 4.23-4.22 (d, J=3.6 Hz, 1H), 4.01-3.98 (m, 2H), 3.96-3.89 (m, 2H), 3.73-3.71 (d, J=9.2 Hz, 1H), 3.54-3.47 (m, 2H), 2.95-2.94 (d, J=4.4 Hz, 4H), 2.01 (bs, 1H), 1.94-1.84 (m, 1H), 1.68 (bs, 3H).

Characterization data for further compounds prepared by the above methods are presented in Table 21 below. Compounds in Table 21 were prepared by methods substantially similar to those described to prepare I-695, where 91k was replaced with the reagent as indicated in Table 21.

TABLE 21

| Compound # | Reagent | Chiral Separation Conditions and Characterization Data |
|---|---|---|
| I-674 | (structure with NH₂, pyridinone, tetrahydropyran) | MS (ES): m/z 470.51 [M + H]⁺, LCMS purity: 100%, HPLC purity: 98.65%, CHIRAL HPLC: (48.09%, 48.19%) ¹H NMR (DMSO-d₆, 400 MHZ): 8.82 (s, 1H), 8.46-8.44 (d, J = 6.8 Hz, 1H), 8.23 (s, 1H), 7.91-7.90 (d, J = 4.8 Hz, 1H), 7.85-7.83 (d, J = 8.8 Hz, 1H), 7.47-6.45 (d, J = 6.8 Hz, 1H), 6.38-6.35 (t, J = 7.2 Hz, 1H), 6.28 (s, 1H), 5.59-5.58 (d, J = 4.4 Hz, 1H), 5.08-5.02 (m, 1H), 4.60-4.57 (m, 1H), 4.21 (bs, 1H), 4.02-3.94 (m, 4H), 3.74-3.72 (d, J = 9.2 Hz, 1H), 3.55-3.44 (m, 3H), 2.92-2.91 (d, J = 4.8 Hz, 3H), 2.01-1.93 (m, 2H), 1.76-1.74 (m, 2H). |
| I-634 | 91j (structure with NH₂, pyridine, tetrahydropyran) | MS (ES): m/z 454.22 [M + H]⁺ LCMS purity: 97.90%, HPLC purity: 98.13%, Chiral HPLC purity: 48.0%, 47.9%, NMR (DMSO-d₆, 400 MHZ): 9.78 (s, 1H), 8.23 (s, 1H), 8.03-7.99 (d, J = 4.8 Hz, 1H), 7.95-7.89 (m, 3H), 7.70-7.66 (t, J = 8 Hz, 1H), 6.95-6.94 (d, J = 7.2 Hz, 1H), 6.39 (s, 1H), 5.55-5.51 (d, J = 16 Hz, 1H), 4.54-4.51 (m, 1H), 4.22-4.21 (d, J = 3.6 Hz, 2H), 4.00-3.88 (m, 3H), 3.72-3.70 (d, J = 8.4 Hz, 1H), 3.53-3.46 (m, 2H), 2.94-2.86 (m, 4H), 2.03-1.86 (m, 2H), 1.66 (bs, 2H). |
| I-691 I-692 | 91j (structure with NH₂, pyridine, tetrahydropyran) | I-634 was separated into isomers: CHIRAL PAK AD-H (250 × 4.6 mm, 5u) and 0.1% DEA in methanol and isopropyl alcohol-acetonitrile (50-50) at 4 mL/min. FR-a: MS (ES): m/z 454.22 [M + H]⁺, LCMS purity: 98.15%, HPLC purity: 99.04%, CHIRAL HPLC purity: 93.04%, ¹H NMR (DMSO-d₆, 400 MHZ): 9.80 (s, 1H), 8.23 (s, 1H), 8.02-7.89 (m, 3H), 7.70-7.66 (t, J = 7.6 Hz, 1H), 6.95-6.93 (d, J = 7.2 Hz, 1H), 6.43 (s, 1H), 5.52 (s, 1H), 4.52-4.49 (t, J = 5.2 Hz, 1H), 4.22 (s, 1H), 4.00-3.88 (m, 4H), 3.72-3.70 (d, J = 8 Hz, 1H), 3.53-3.46 (m, 2H), 2.94-2.78 (m, 5H), 2.00 (bs, 1H), 1.89-1.86 (m, 1H), 1.66 (bs, 2H). FR-b: MS (ES): m/z 454.22 [M + H]⁺, LCMS purity 100%, HPLC purity: 99.72% Chiral HPLC purity: 98.47%, ¹H NMR (DMSO-d₆, 400 MHZ): 9.77 (s, 1H), 8.23 (s, 1H), 8.02-7.89 (m, J = 4.8 Hz, 3H), 7.70-7.66 (t, J = 8 Hz, 1H), 6.95-6.93 (d, J = 7.2 Hz, 1H), 6.40 (s, 1H), 5.52 (s, 1H), 4.56-4.50 (m, J = 5.2 Hz, 1H), 4.22 (s, 1H), 4.00-3.88 (m, 4H), 3.72-3.70 (d, J = 9.6 Hz, 1H), 3.53-3.47 (m, 2H), 2.94-2.83 (m, 5H), 2.00 (bs, 1H), 1.89-1.86 (m, 1H), 1.66 (bs, 2H). |
| I-695 | 91k (structure with NH₂, pyridine, tetrahydropyran) | MS (ES): m/z 454.51 [M + H]⁺, LCMS purity: 97.33%, HPLC purity: 97.44%, CHIRAL HPLC: 49.04%, 49.43%, ¹H NMR (DMSO-d₆, 400 MHZ): 9.79 (s, 1H), 8.24 (s, 1H), 8.04-8.03 (d, J = 4.4 Hz, 2H), 7.96-7.90 (m, 1H), 7.71-7.67 (t, J = 7.6 Hz, 1H), 6.96-6.95 (d, J = 7.2 Hz, 1H), 6.40 (bs, 1H), 5.53-5.52 (d, J = 4 Hz, 1H), 4.55-4.49 (m, 1H), 4.23-4.22 (d, J = 3.6 Hz, 1H), 4.01-3.98 (m, 2H), 3.96-3.89 (m, 2H), 3.73-3.71 (d, J = 9.2 Hz, 1H), 3.54-3.47 (m, 2H), 2.95-2.94 (d, J = 4.4 Hz, 4H), 2.01 (bs, 1H), 1.94-1.84 (m, 1H), 1.68 (bs, 3H). |
| I-774 I-775 | 91k (structure with NH₂, pyridine, tetrahydropyran) | I-695 was separated into isomers: CHIRAL PAK AD-H (250 × 4.6 mm, 5 μM) and 0.1% DEA_MEOH (50-50). FR-a: MS (ES): m/z 454.50 [M + H]⁺, LCMS purity: 98.4%, HPLC purity: 95%, CHIRAL HPLC purity: 100%, ¹H NMR (DMSO-d₆, 400 MHZ): 9.93 (s, 1H), 8.24 (s, 1H), 8.03 (s, 1H), 7.88 (s, 1H), 7.71-7.67 (t, J = 7.6 Hz, 1H), 6.95-6.94 (d, J = 7.2 Hz, 1H), 6.60 (s, 1H), 5.74 (s, 1H), 4.47 (s, 1H), 4.25 (s, 1H), 4.00-3.89 (m, 4H), 3.74-3.71 (d, J = 9.6 Hz, 1H), 3.55-3.47 (m, 3H), 2.97-2.96 (m, 3H), 2.90 (bs, 1H), 2.02 (bs, 1H), 1.92 (bs, 2H), 1.68 (bs, 2H). FR-b: MS (ES): m/z 454.55 [M + H]⁺, LCMS purity: 100%, HPLC purity: 99.12%, CHIRAL HPLC purity: 100%, ¹H NMR (DMSO-d₆, 400 MHZ): 9.93 (s, 1H), 8.24 (s, 1H), 8.03 (s, 1H), 7.86 (s, 1H), 7.71-7.67 (t, J = 7.6 Hz, 1H), 6.95-6.94 (d, J = 7.2 Hz, 1H), 6.60 (s, 1H), 5.74 (s, 1H), 4.47 (s, 1H), 4.25 (s, 1H), 4.00-3.89 (m, 4H), 3.74-3.71 (d, J = 9.6 Hz, 1H), 3.55-3.47 (m, 3H), 2.97-2.96 (d, J = 4.8 Hz, 3H), 2.90 (bs, 1H), 2.02 (bs, 1H), 1.92 (bs, 2H), 1.68 (bs, 2H). |
| I-520 | (structure with H₂N, pyridine, cyclopropylmethoxy) | MS (ES): m/z 426.38 [M + H]⁺, LCMS purity: 95.62%, HPLC purity: 95.43%, Chiral HPLC purity: 50.31%, 48.40%, ¹H NMR (DMSO-d₆, 400 MHZ): 8.62-8.60 (d, J = 8.0 Hz, 1H), 8.56 (s, 1H), 8.21 (s, 1H), 7.93-7.92 (d, J = 4.0 Hz, 1H), 7.86-7.81 (m, 2H), 7.06-7.03 (m, 1H), 6.04 (s, 1H), 5.67 (s, 1H), 4.55-4.52 (t, J = 4.0 Hz, 1H), 4.37-4.35 (t, J = 4.0 Hz, 1H), 4.17-4.14 (m, 2H), 4.01-3.97 (m, 1H), 3.93-3.89 (m, 1H), 3.72-3.70 (d, J = 8.0 Hz, 1H), 2.94-2.93 (d, J = 4.0 Hz, 3H), 0.91-0.88 (m, 2H), 0.82-0.80 (m, 2H). |
| I-546 I-547 | (structure with H₂N, pyridine, cyclopropylmethoxy) | I-520 was separated into isomers: CHIRALPAK AD-H (250 mm*4.6 mm, 5 μM) and 0.1% diethylamine in methanol at 4 mL/min. FR-a: MS (ES): m/z 426.50 [M + H]⁺, LCMS purity: 96.73%, HPLC purity: 95.18%, CHIRAL HPLC purity: 100%, ¹H NMR (DMSO-d₆, 400 MHZ): ): 8.60-8.59 (d, J = 4.0 Hz, 1H), 8.55 (s, 1H), 8.20 (s, 1H), 7.92-7.91 (d, J = 4.0 Hz, 1H), 7.85-7.80 (m, 2H), 7.05-7.02 (m, 1H), 6.02 (s, 1H), 5.44-5.43 (d, J = 4.0 Hz, 1H), 4.54-4.50 (t, J = 8.0 Hz, 1H), 4.36-4.34 (t, J = 8.0 Hz, 1H), 4.17-4.16 (m, 1H), 3.99-3.96 (m, 1H), 3.91-3.87 (m, 1H), 3.70-3.68 (m, 1H), 2.92-2.91 (d, J = 4.0 Hz, 3H), 1.23 (bs, 2H) 0.85-0.79 (m, 3H). FR-b: MS (ES): m/z 426.40 [M + H]⁺, LCMS purity: 98.94%, HPLC purity: 98.39%, CHIRAL HPLC purity: 98.37%, ¹H NMR (DMSO-d₆, 400 MHZ): 8.60-8.58 (d, J = 8.0 Hz, 1H), 8.55 (s, 1H), 8.20 (s, 1H), 7.92-7.91 (d, J = 4.0 Hz, 1H), 7.85-7.80 (m, 2H), 7.05-7.02 (m, 1H), 6.02 (s, 1H), 5.44 (s, 1H), 4.54-4.50 (t, J = 8.0 Hz, 1H), 4.35 (s, 1H), 4.17 (s, 1H), 3.99-3.96 (m, 1H), 3.91-3.87 (m, 1H), 3.70-3.68 (m, 1H), 2.92-2.91 (d, J = 4.0 Hz, 3H), 1.34-1.23 (m, 2H), 0.85-0.79 (m, 3H). |

TABLE 21-continued

| Compound # | Reagent | Chiral Separation Conditions and Characterization Data |
|---|---|---|
| I-519 | H₂N-pyridine-OMe | MS (ES): m/z 400.24 [M + H]⁺, LCMS purity: 100%, HPLC purity: 99.74%, Chiral HPLC purity: 49.59%, 49.29%, ¹H NMR (DMSO-d₆, 400 MHZ): 8.79 (s, 1H), 8.61-8.59 (d, J = 8.0 Hz, 1H), 8.21 (s, 1H), 7.91-7.90 (d, J = 4.0 Hz, 1H), 7.85-7.82 (m, 2H), 7.04-7.01 (m, 1H), 6.08 (s, 1H), 5.45-5.44 (d, J = 4.0 Hz, 1H), 4.55-4.52 (m, 1H), 4.18-4.17 (d, J = 4.0 Hz, 1H), 4.00-3.98 (d, J = 8.0 Hz, 3H), 3.92-3.88 (t, J = 4.0 Hz, 1H) 3.72-3.69 (d, J = 12 Hz, 1H), 3.40-3.38 (d, J = 8.0 Hz, 1H), 2.96 (s, 1H), 2.93-2.92 (d, J = 4.0 Hz, 3H). |
| I-614 I-615 | H₂N-pyridine-OMe | I-519 was separated into isomers: CHIRALPAK IC (250 mm*4.6 mm, 5 μM) and 0.1% diethylamine in IPA:acetonitrile (50:50) at 4 mL/min FR-a: MS (ES): mz 400.17 [M + H]⁺, LCMS purity: 100%, HPLC purity: 100%, CHIRAL HPLC purity: 100%, ¹H NMR (DMSO-d₆, 400 MHZ): 8.80 (s, 1H), 8.60-8.58 (d, J = 8.0 Hz, 1H), 8.20 (s, 1H), 7.91-7.90 (d, J = 4.0 Hz, 1H), 7.84-7.81 (m, 2H), 7.03-7.00 (m, 1H), 6.07 (s, 1H), 5.45-5.44 (d, J = 4.0 Hz, 1H), 4.54-4.51 (m, 1H), 4.17-4.16 (d, J = 4.0 Hz, 1H), 3.99 (s, 3H), 3.97 (s, 1H), 3.91-3.87 (t, J = 8.0 Hz, 1H) 3.71-3.68 (d, J = 12 Hz, 1H), 3.39-3.37 (d, J = 8.0 Hz, 1H), 2.91-2.90 (d, J = 4.0 Hz, 3H). FR-b: MS (ES): m/z 400.17 [M + H]⁺, LCMS purity: 100%, HPLC purity: 100%, CHIRAL HPLC purity: 100%, ¹H NMR (DMSO-d₆, 400 MHZ): 8.80 (s, 1H), 8.60-8.58 (d, J = 8 0 Hz, 1H), 8.20 (s, 1H), 7.91-7.90 (d, J = 4.0 Hz, 1H), 7.84-7.81 (m, 2H), 7.03-7.00 (m, 1H), 6.07 (s, 1H), 5.45-5.44 (d, J = 4.0 Hz, 1H), 4.54-4.51 (m, 1H), 4.17-4.16 (d, J = 4.0 Hz, 1H), 3.99 (s, 3H), 3.97 (s, 1H), 3.91-3.87 (t, J = 8.0 Hz, 1H) 3.71-3.68 (d, J = 12 Hz, 1H), 3.39-3.37 (d, J = 8.0 Hz, 1H), 2.91-2.90 (d, J = 4.0 Hz, 3H). |

Synthesis of N-(4-hydroxytetrahydrofuran-3-yl)-7-(methylamino)-5-(1-((S)-tetrahydro-2H-pyran-3-yl)-1H-pyrrolo[2,3-b]pyridin-3-yl)pyrazolo[1,5-a]pyrimidine-3-carboxamide (I-1251)

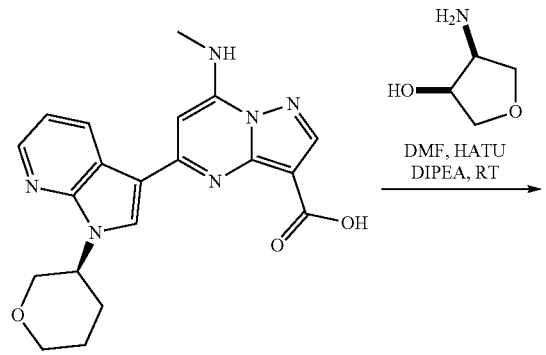

92.13

Synthesis of Compound 92.13.

Compound was synthesized as per I-1258 to obtain 92.13. (Yield: 93.76%), MS (ES): 393.16 [M+H]⁺

Synthesis of Compound I-1251.

Compound was synthesized using general procedure A to obtain I-1251 (0.110 g, 60.26%), MS (ES): m/z 478.76 [M+H]⁺, LCMS purity: 100%, HPLC purity: 98.75%, CHIRAL HPLC: 50.02%, 47.59%, ¹H NMR (DMSO-d₆, 400 MHZ): 8.94-8.92 (d, J=7.6 Hz, 1H), 8.77 (s, 1H), 8.49-8.45 (t, J=7.6 Hz, 1H), 8.39 (s, 1H), 8.28-8.27 (d, J=4 Hz, 1H), 7.30-7.27 (m, 1H), 6.73 (s, 1H), 5.77 (s, 1H), 5.71-5.68 (m, 1H), 4.96 (bs, 1H), 4.57 (bs, 1H), 4.32 (bs, 1H), 4.05-3.97 (m, 3H), 3.76-3.70 (m, 2H), 3.59-3.51 (m, 2H), 3.14-3.13 (d, J=4.4 Hz, 3H), 3.02 (s, 1H), 2.21 (bs, 2H), 1.86 (bs, 2H).

Synthesis of N-(4-hydroxytetrahydrofuran-3-yl)-7-(methylamino)-5-(1-((R)-tetrahydro-2H-pyran-3-yl)-1H-pyrrolo[2,3-b]pyridin-3-yl)pyrazolo[1,5-a]pyrimidine-3-carboxamide (I-1250)

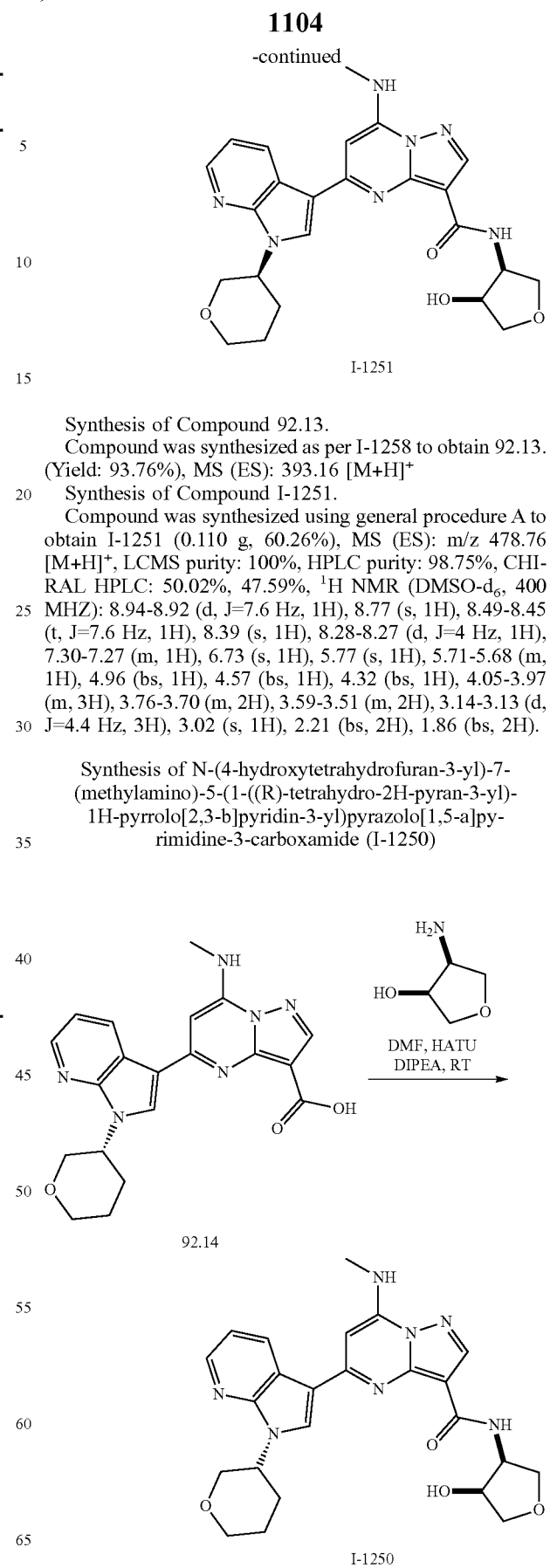

1105

Synthesis of Compound 92.14.

Compound was synthesized as per I-1258 to obtain 92.14. (Yield: 91.76%), MS (ES): 393.16 [M+H]+

Synthesis of Compound I-1250.

Compound was synthesized using general procedure A to obtain I-1250 (0.120 g, 65.74%), MS (ES): m/z 478.62 [M+H]+, LCMS purity: 100%, HPLC purity: 99.24%, CHIRAL HPLC: 49.29%, 49.83%, $^1$H NMR (DMSO-$d_6$, 400 MHZ): 8.93-8.91 (d, J=7.6 Hz, 1H), 8.76 (s, 1H), 8.46-8.44 (t, J=7.6 Hz, 1H), 8.38 (bs, 2H), 8.27 (bs, 1H), 7.27-7.26 (m, 1H), 6.73 (s, 1H), 5.70-5.67 (m, 1H), 4.95 (bs, 1H), 4.56 (bs, 1H), 4.31 (bs, 1H), 4.04-3.98 (m, 4H), 3.75-3.73 (m, 2H), 3.58-3.54 (m, 2H), 3.13-3.12 (d, J=4.4 Hz, 3H), 2.38 (bs, 1H), 1.85 (bs, 2H), 1.24 (bs, 1H).

Synthesis of Intermediate 92a.

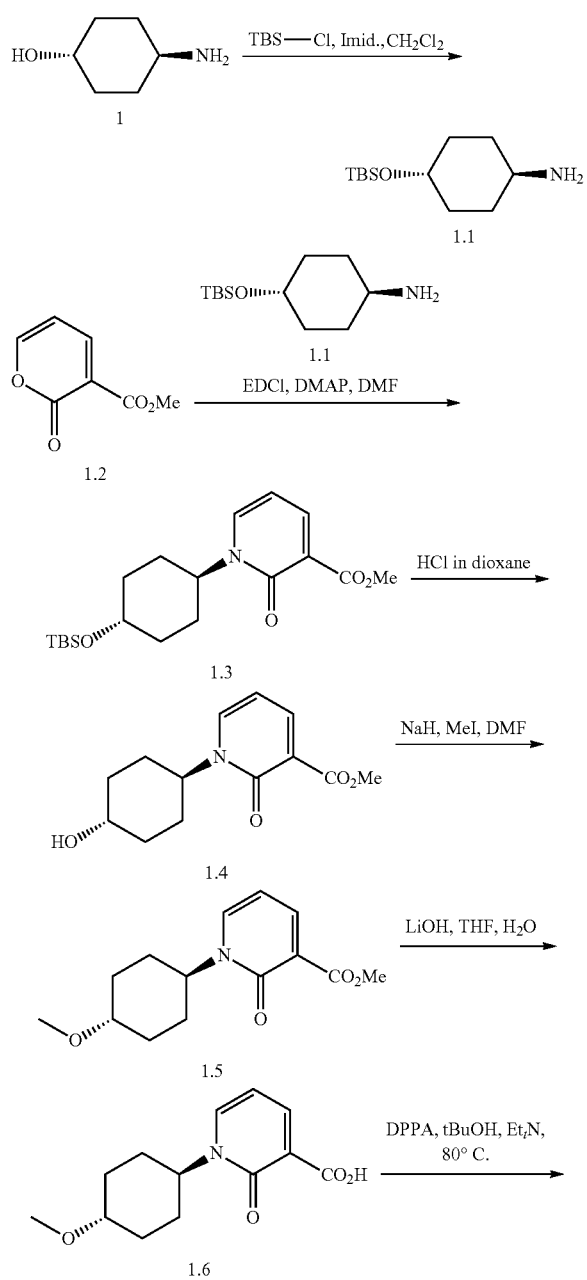

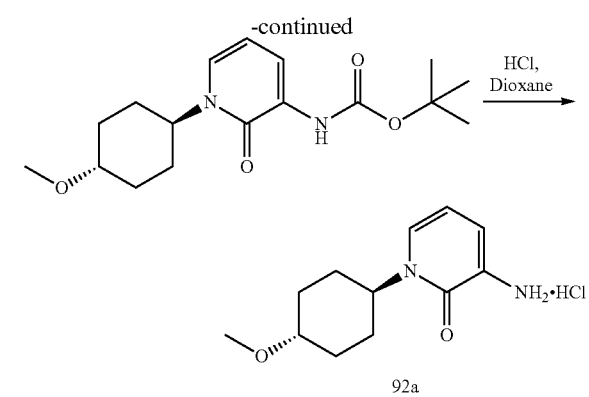

Synthesis of Compound 1.1:

To a solution of 1 (2.0 g, 1.31 mmol, 1.0 eq) in dichloromethane (20 mL) was added imidazole (1.5 g, 6.55 mmol, 5.0 eq). The reaction mixture was stirred at room temperature for 30 min. Further tert-Butyldimethylsilyl chloride (0.985 g, 1396 mmol, 1.5 eq) was added and stirred reaction mixture at room temperature for 15 h. After completion of reaction, reaction mixture was transferred into water and product was extracted by dichloromethane. Organic layer was combined, washed with brine solution, dried over sodium sulphate and concentrated under reduced pressure to obtain product 1.1 (1.2 g, 39.65%). MS(ES): m/z 230.44 [M+H]+.

Synthesis of Compound 1.3.

To a cooled solution of 1.2 (1.3 g, 8.4 mmol, 1.0 eq), in N,N-dimethylformamide (20 mL) was added 1.1 (1.93 g, 8.4 mmol, 1.0 eq). The reaction mixture was stirred at 0° C. for 6 h and further stirred at room temperature for 15 min. N-Ethyl-N'-(3-dimethylaminopropyl) carbodiimide hydrochloride (2 g, 10.92 mmol, 1.3 eq) and 4-Dimethylaminopyridine (0.25 g, 2.1 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.3 (0.9 g, 29.18%). MS(ES): m/z 366.55 [M+H]+.

Synthesis of Compound 1.4:

A cooled solution of 1.3 (0.9 g, 2.46 mmol, 1 eq) in 1,4-dioxane (10 mL) was added 4N hydrochloric acid in dioxane (10 mL) dropwise. The reaction mixture was stirred at room temperature for 2 h. After completion of reaction, reaction mixture was concentrated under reduced pressure to obtain pure 1.4 (0.6 g, 96.98%). MS(ES): m/z 252.28 [M+H]+

Synthesis of Compound 1.5:

To a cooled solution of 1.4 (0.6 g, 2.3 mmol, 1.0 eq), in N, N-dimethylformamide (10 mL) was added sodium hydride (0.19 g, 4.6 mmol, 2.0 eq). The reaction mixture was stirred at 0° C. for 30 min and methyl iodide (0.480 g, 3.45 mmol, 1.50 eq) was added. The reaction mixture was stirred at room temperature for 6 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.5 (0.4 g, 63.14%). MS(ES): m/z 266.31 [M+H]⁺.

Synthesis of Compound 1.6:

To a solution of 1.5 (0.85 g, 3.2 mmol, 1.0 eq), in tetrahydrofuran: methanol: water (10 mL, 2:2:1) was added lithium hydroxide (1.3 g, 32.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6 (0.67 g, 83.22%). MS(ES): m/z 253.3 [M+H]⁺.

Synthesis of Compound 1.7:

To a solution of 1.7 (0.670 g, 2.66 mmol, 1.0 eq) in tert. Butanol (6 mL) was added triethylamine (0.45 g, 4.53 mmol, 1.7 eq) and diphenyl phosphoryl azide (0.95 g, 3.45 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7 (0.5 g, 58.16%). MS(ES): m/z 322.41 [M+H]⁺.

Synthesis of Compound 92a:

A cooled solution of 1.7 (0.5 g, 1.5 mmol, 1 eq) in 1,4-dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 92a (0.34 g, 92.21%). MS(ES): m/z 259.75 [M+H]⁺

Synthesis of Intermediate 92b.

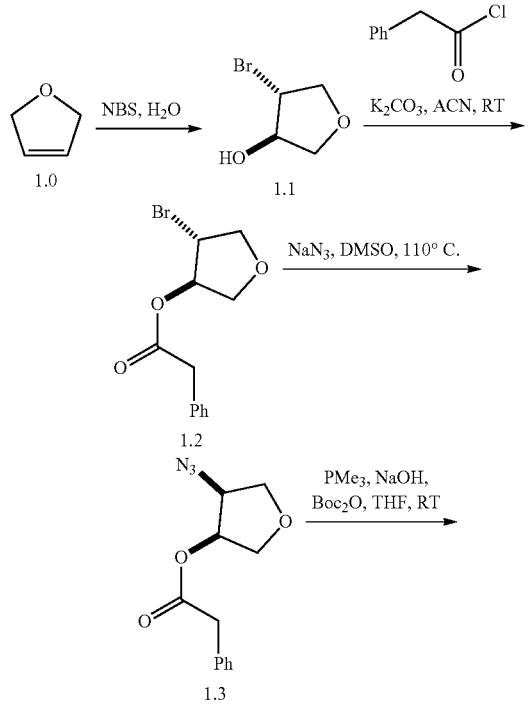

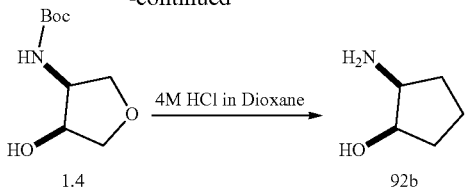

Synthesis of Compound 1.1.

To a stirred solution of N-bromo succinimide (12.69 g, 71.34 mmol, 1.0 eq) in water at 0° C. was added 2,5-dihydrofuran (5.0 g, 71.34 mmol, 1.0 eq) drop wise at 0° C. Reaction mixture was stirred for 5 h at room temperature. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 4.0% ethyl acetate in hexane to obtain 1.1 (2.50 g, 20.99%). MS(ES): m/z 168.00 [M+H]⁺.

Synthesis of Compound 1.2.

To a solution of 1.1 (2.50 g, 14.97 mmol, 1.0 eq) in Acetonitrile (33.00 mL), was added potassium carbonate (3.10 g, 22.45 mmol, 1.5 eq) and stirred for 20 min. followed by addition of 2-phenylacetyl chloride (2.31 g, 14.97 mmol, 1.0 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 1.2 (2.20 g, 51.54%), MS(ES): m/z 286.14 [M+H]⁺.

Synthesis of Compound 1.3.

To a solution of 1.2 (2.20 g, 7.72 mmol, 1.0 eq) in Dimethyl sulfoxide (31.0 mL), was added Sodium azide (2.50 g, 38.60 mmol, 5.0 eq). The reaction was stirred at 110° C. for 12 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 14% ethyl acetate in hexane to obtain pure 1.3 (1.1 g, 57.66%), MS(ES): m/z 248.25 [M+H]⁺.

Synthesis of Compound 1.4.

To a solution of 1.3 (0.500 g, 2.02 mmol, 1.0 eq) in tetrahydrofuron (19.0 mL), was added 1M Sodium Hydroxide solution (26 mL), trimethylphosphine (0.461 g, 6.06 mmol, 3.0 eq) followed by Di-tert-butyl dicarbonate (1.32 g, 6.06 mmol, 3.0 eq) and reaction mixture was stirred at room temperature for 3 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 30% ethyl acetate in hexane to obtain pure 1.4 (0.285 g, 69.34%), MS(ES): m/z 204.24 [M+H]⁺.

Synthesis of Compound 92b.

To 1.4 (0.285 g, 1.40 mmol, 1.0 eq) was added 4M hydrochloric acid (2.8 mL) in 1,4-dioxane (3.0 mL) and stirred at room temperature for 1 h. After completion of reaction, reaction mixture was concentrated under reduced pressure, residue was triturated with diethyl ether to obtain 92b (0.140 g, 96.81%). MS (ES): m/z 104.12 [M+H]⁺.

Example 93: Synthesis of Compounds where R³ is N-(trans)-(4-hydroxytetrahydrofuran-3-yl)carboxamide, R⁶ is Hydrogen, and R⁷ is Methylamine Synthesis of N-(2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-852)

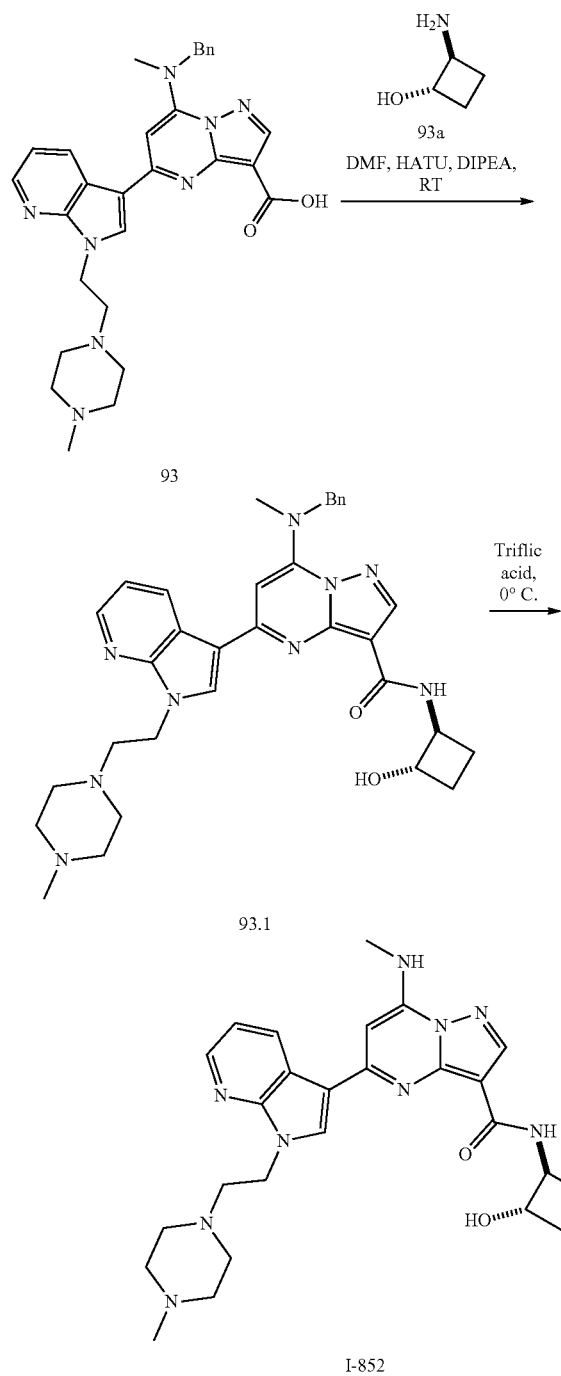

Synthesis of Compound 93.
Compound was synthesized as per I-851 to obtain 93. (Yield: 81.94%). MS (ES): m/z 525.27 [M+H]⁺.

Synthesis of Compound 93.1.
Compound was synthesized using general procedure A to obtain 93.1. (320 g, Yield: 70.69%). MS (ES): m/z 594.33 [M+H]⁺.

Synthesis of Compound I-852.
The compound 93.1 (0.160 g, 0.269 mmol, 1.0 eq) was dissolved in dichloromethane (2 mL). Triflic acid (1 mL) was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-852 (0.123 g, Yield: 90.63%). MS(ES): m/z 504.47 [M+H]⁺, LCMS purity: 100%, HPLC purity: 99.16%, CHIRAL HPLC: 50.78%, 49.22%, ¹H NMR (DMSO-d₆, 400 MHZ): 8.77-8.75 (d, J=7.6 Hz, 1H), 8.70 (s, 1H), 8.51-8.49 (d, J=8.8 Hz, 1H), 8.41-8.40 (d, J=3.2 Hz, 1H), 8.37 (s, 1H), 8.29-8.28 (d, J=4.8 Hz, 1H), 7.33-7.30 (m, 1H), 6.69 (s, 1H), 5.78 (s, 1H), 5.51-5.49 (d, J=7.2 Hz, 1H), 4.51-4.47 (t, J=6.4 Hz, 2H), 4.35-4.27 (m, 2H), 4.06-3.98 (m, 2H), 3.33 (s, 1H), 3.11-3.10 (d, J=4.8 Hz, 3H), 2.83-2.80 (t, J=6.8 Hz, 2H), 2.14 (s, 3H), 2.10 (s, 3H), 1.59-1.49 (m, 2H), 1.40-1.30 (m, 2H), 0.87 (bs, 1H).

Synthesis of N-((1S,2S)-2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-920) and N-((1R,2R)-2-hydroxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-921)

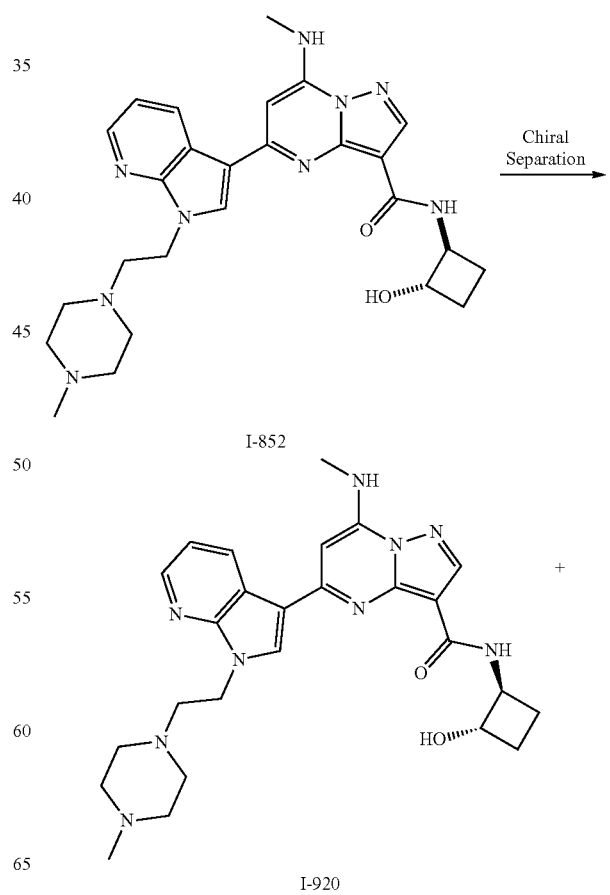

-continued

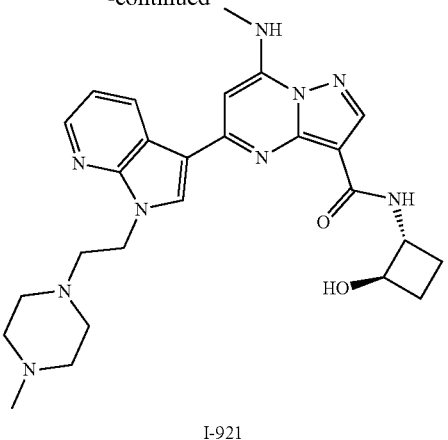

I-921

Synthesis of Compound I-920 & I-921.

Isomers of I-852 (0.123 g) were separated out using column (CHIRAL PAK AD-H 250×4.6 mm, 5 μM) 0.1% DEA_MEOH (70-30) to get pure fraction-1 (FR-a) and fraction-2 (FR-b). FR-a was concentrated under reduced pressure at 30° C. to afford 0.030 g. MS(ES): m/z 504.82 [M+H]+, LCMS purity: 100%, HPLC purity: 99.19%, CHIRAL HPLC purity: 97.72%, $^1$H NMR (DMSO-$d_6$, 400 MHZ): 8.77-8.75 (d, J=6.8 Hz, 1H), 8.71 (s, 1H), 8.51-8.49 (d, J=8.8 Hz, 1H), 8.42-8.41 (d, J=3.6 Hz, 1H), 8.38 (s, 1H), 8.29-8.28 (d, J=4.8 Hz, 1H), 7.34-7.31 (m, 1H), 6.69 (s, 1H), 5.51-5.49 (d, J=7.2 Hz, 1H), 4.51-4.48 (t, J=6.8 Hz, 2H), 4.33-4.29 (m, 1H), 4.04-4.00 (m, 1H), 3.12-3.10 (d, J=4.8 Hz, 3H), 2.84-2.81 (t, J=6.8 Hz, 2H), 2.34-2.29 (m, 4H), 2.13-2.10 (m, 6H), 1.57-1.52 (m, 2H), 1.38-1.28 (m, 3H).

FR-b was concentrated under reduced pressure at 30° C. to afford 0.028 g. MS(ES): m/z 504.67 [M+H]+, LCMS purity: 98.13%, HPLC purity: 97.28%, CHIRAL HPLC purity: 97.21%, $^1$H NMR (DMSO-$d_6$, 400 MHZ): 8.77-8.76 (d, J=6.8 Hz, 1H), 8.71 (s, 1H), 8.51-8.49 (d, J=8.8 Hz, 1H), 8.42-8.41 (d, J=3.6 Hz, 1H), 8.38 (s, 1H), 8.29-8.28 (d, J=4.8 Hz, 1H), 7.34-7.31 (m, 1H), 6.70 (s, 1H), 5.51-5.49 (d, J=7.2 Hz, 1H), 4.51-4.48 (t, J=6.8 Hz, 2H), 4.34-4.29 (m, 1H), 4.04-4.01 (m, 1H), 3.12-3.10 (d, J=4.8 Hz, 3H), 2.84-2.81 (t, J=6.8 Hz, 2H), 2.35-2.31 (m, 4H), 2.14-2.10 (m, 6H), 1.59-1.50 (m, 2H), 1.44-1.31 (m, 3H).

Characterization data for further compounds prepared by the above methods are presented in Table 22 below. Compounds in Table 22 were prepared by methods substantially similar to those described to prepare I-1112, where 93 was replaced with the reagent as indicated in Table 22.

TABLE 22

| Compound # | Reagent | Chiral Separation Conditions and Characterization Data |
|---|---|---|
| I-792 | (structure with Bn, morpholine) | MS (ES): mz 491.57 [M + H]+, LCMS purity: 100%, HPLC purity: 97.71%, Chiral HPLC: 47.82%, 46.59%, $^1$H NMR (DMSO-$d_6$, 400 MHZ): 8.77-8.76 (d, J = 6.8 Hz, 1H), 8.71 (s, 1H), 8 51-8.49 (d, J = 8.4 Hz, 1H), 8.41-8.41 (d, J = 3.6 Hz, 1H), 8.37 (s, 1H), 8.28 (bs, 1H), 7.34-7.30 (m, 1H), 6.70 (m, 1H), 5.51 (bs, 1H), 4.53-4.49 (t, J = 6.8 Hz, 2H), 4.33-4.27 (m, 1H), 4.03-4.01 (d, J = 8 Hz, 1H), 3.55 (bs, 4H), 3.13-3.11 (s, 3H), 2.85-2.81 (t, J = 6.4 Hz, 3H), 2.11-2.09 (d, J = 6.8 Hz, 3H), 1.59-1.49 (m, 2H), 1.40-1.30 (m, 1H), 1.12-1.08 (t, J = 7.2 Hz, 1H). |
| I-834 I-835 | (structure with Bn, morpholine) | I-792 was separated into isomers: CHIRAL PAK AD-H (250 × 4.6 mm, 5u) 0.1% DEA_HEX_IPA-ACN (70-30). FR-a: MS (ES): m/z 491.57 [M + H]+, LCMS purity: 100%, HPLC purity: 99.58%, CHIRAL HPLC purity: 99.38%, $^1$H NMR (DMSO-$d_6$, 400 MHZ): 8.77-8.75 (d, J = 7.6 Hz, 1H), 8.71 (s, 1H), 8.51-8.49 (d, J = 8.4 Hz, 1H), 8.41-8.40 (d, J = 3.6 Hz, 1H), 8.37 (s, 1H), 8.30-8.28 (d, J = 4.4 Hz, 1H), 7.33-7.30 (m, 1H), 6.70 (s, 1H), 5.52-5.50 (d, J = 6.4 Hz, 1H), 4.52-4.49 (t, J = 6.4 Hz, 2H), 4.33-4.29 (m, 1H), 4.03-4.00 (m, 1H), 3.55 (bs, 4H), 3.11-3.10 (d, J = 3.6 Hz, 3H), |

TABLE 22-continued

| Compound # | Reagent | Chiral Separation Conditions and Characterization Data |
|---|---|---|
| | | 2.84-2.81 (t, J = 6.4 Hz, 2H), 2.52 (bs, 4H), 2.11-2.09 (d, J = 6 Hz, 2H), 1.56-1.52 (m, 1H), 1.37-1.32 (m, 1H). FR-b: MS (ES): m/z 491.41 [M + H]+, LCMS purity: 100%, HPLC purity: 99.22%, CHIRAL HPLC purity: 100%, $^1$H NMR (DMSO-d$_6$, 400 MHZ): ): 8.77-8.75 (d, J = 8 Hz, 1H), 8.72 (s, 1H), 8.51-8.49 (d, J = 8.4 Hz, 1H), 8.42-8.41 (d, J = 4.4 Hz, 1H), 8.37 (s, 1H), 8.30-8.29 (d, J = 4.4 Hz, 1H), 7.34-7.30 (m, 1H), 6.70 (s, 1H), 5.52-5.50 (d, J = 6.8 Hz, 1H), 4.53-4.49 (t, J = 6.4 Hz, 2H), 4.33-4.29 (m, 1H), 4.03-4.00 (m, 1H), 3.55 (bs, 4H), 3.11-3.10 (d, J = 4.4 Hz, 3H), 2.84-2.81 (t, J = 6.8 Hz, 2H), 2.52 (bs, 4H), 2.11-2.09 (d, J = 6 Hz, 2H), 1.56-1.52 (m, 1H), 1.37-1.32 (m, 1H). |
| I-794 | [chemical structure] | MS (ES): m/z 489.57 [M + H]+, LCMS purity: 100%, HPLC purity: 99.76%, Chiral HPLC: 49.65%, 50.20%, $^1$H NMR (DMSO-d$_6$, 400 MHZ): 8.76-8.74 (d, J = 7.6 Hz, 1H), 8.69 (s, 1H), 8.50-8.48 (d, J = 8.8 Hz, 1H), 8.41-8.40 (d, J = 4 Hz, 1H), 8.36 (s, 1H), 8.28-8.27 (d, J = 4.4 Hz, 1H), 7.32-7.29 (m, 1H), 6.69 (s, 1H), 4.30-4.26 (t, J = 8.4 Hz, 1H), 4.03-3.97 (m, 1H), 3.75 (bs, 2H), 3.10-3.09 (d, J = 4.4 Hz, 3H), 2.77 (bs, 2H), 2.45 (bs, 4H), 2.10-2.08 (d, J = 6.8 Hz, 2H), 1.47 (bs, 4H), 1.36-1.27 (m, 3H), 0.87-0.84 (t, J = 6 Hz, 2H). |
| I-837 I-838 | [chemical structure] | I-794 was separated into isomers: (CHIRAL PAK AD-H 250 × 4.6 mm, 5u) 0.1% DEA_HEX_IPA-ACN (70-30). FR-a: MS (ES): m/z 489.26 [M + H]+, LCMS purity: 100%, HPLC purity: 99.49%, CHIRAL HPLC purity: 99.92%, $^1$H NMR (DMSO-d$_6$, 400 MHZ): 8.77-8.76 (d, J = 6.8 Hz, 1H), 8.71 (s, 1H), 8.51-8.49 (d, J = 8.4 Hz, 1H), 8.42-8.41 (d, J = 4.0 Hz, 1H), 8.38 (s, 1H), 8.29-8.28 (d, J = 4.8 Hz, 1H), 7.34-7.31 (m, 1H), 6.70 (s, 1H), 5.51-5.49 (d, J = 7.2 Hz, 1H), 4.49 (s, 1H), 4.35-4.27 (m, 1H), 4.06-3.98 (m, 1H), 3.11-3.10 (d, J = 4.8 Hz, 3H), 2.78 (s, 1H), 2.11-2.09 (d, J = 7.2 Hz, 2H), 1.59-1.48 (m, 5H), 1.38-1.24 (m, 6H), 1.08-1.04 (m, 1H), 0.89-0.85 (m, 2H). FR-b: MS (ES): m/z 489.47 [M + H]+, LCMS purity: 100%, HPLC purity: 99.52%, CHIRAL HPLC |

TABLE 22-continued

| Compound # | Reagent | Chiral Separation Conditions and Characterization Data |
|---|---|---|
| | | purity: 98.93%, $^1$H NMR (DMSO-d$_6$, 400 MHZ): 8.77-8.75 (d, J = 7.2 Hz, 1H), 8.71 (s, 1H), 8.51-8.49 (d, J = 8.4 Hz, 1H), 8.42-8.41 (d, J = 4.0 Hz, 1H), 8.38 (s, 1H), 8.29-8.28 (d, J = 4.8 Hz, 1H), 7.34-7.31 (m, 1H), 6.70 (s, 1H), 5.52-5.50 (d, J = 7.2 Hz, 1H), 4.51 (s, 1H), 4.35-4.27 (m, 1H), 4.06-3.98 (m, 1H), 3.11-3.10 (d, J = 4.8 Hz, 3H), 2.74 (s, 1H), 2.11-2.09 (d, J = 7.2 Hz, 2H), 1.59-1.48 (m, 5H), 1.38-1.24 (m, 6H), 1.08-1.04 (m, 1H), 0.89-0.85 (m, 2H). |
| I-586 | 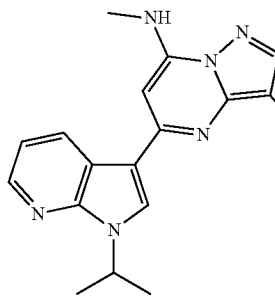 | MS (ES): m/z 420.49 [M + H]$^+$, LCMS purity: 96.49%, HPLC purity: 96.15%, Chiral HPLC: 50.03%, 49.97%, $^1$H NMR (DMSO-d$_6$, 400 MHZ): 8.81 (s, 1H), 8.79-8.77 (d, J = 8.0 Hz, 1H), 8.52-8.50 (d, J = 8.4 Hz, 1H), 8.42-8.41 (d, J = 4.4 Hz, 1H), 8.37 (s, 1H), 8.26-8.24 (d, J = 5.2 Hz, 1H), 7.34-7.31 (m, 1H), 6.81 (s, 1H), 5.50-5.48 (d, J = 7.2 Hz, 1H), 5.24-5.21 (m, 1H), 4.33-4.29 (t, J = 8.8 Hz, 1H), 4.03-3.99 (d, J = 8.0 Hz, 1H), 3.13-3.12 (d, J = 4.8 Hz, 3H), 2.11-2.09 (d, J = 5.2 Hz, 2H), 1.60-1.59 (d, J = 6.4 Hz, 6H), 1.37-1.32 (t, J = 9.2 Hz, 1H), 1.25 (bs, 1H). |
| I-639 I-640 | 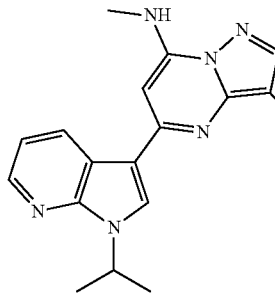 | I-586 was separated into isomers: CHIRAL PAK IB (250 mm*4.6 mm, 5u) in 0.1% diethylamine in methanol at 4 mL/min. FR-a: MS (ES): m/z 420.33 [M+H]$^+$ LCMS purity: 96.79%, HPLC purity: 95.24%, Chiral HPLC purity: 95.68%, NMR (DMSO-d$_6$, 400 MHZ): 9.00-8.82 (s, 1H), 8.79-8.77 (d, J = 6.8 Hz, 1H), 8.52-8.50 (d, J = 8.8 Hz, 1H), 8.42-8.41 (d, J = 4.4 Hz, 1H), 8.37 (s, 1H), 8.27 (s, 1H), 7.30-7.27 (m, 1H), 6.81 (s, 1H), 5.53-5.52 (bs, J = 12.4 Hz, 1H), 5.22-5.21 (m, 1H), 4.33-4.27 (m, 1H), 4.02-00 (m, 1H), 3.13-3.12 (d, J = 4 Hz, 3H), 2.82-2.80 (m, 2H), 2.11-2.09 (m, 2H), 1.60-1.59 (d, 6H). FR-b: MS (ES): m/z 420.33 [M + H]$^+$ LCMS purity: 99.51%, HPLC purity: 97.19%, Chiral HPLC purity: 98.03%, NMR (DMSO-d$_6$, 400 MHZ): 8.82 (s, 1H), 8.79-8.77 (d, J = 7.6 Hz, 1H), 8.52-8.50 (d, |

TABLE 22-continued

| Compound # | Reagent | Chiral Separation Conditions and Characterization Data |
|---|---|---|
| | | J = 8.8 Hz, 1H), 8.42-8.41 (d, J = 3.6 Hz, 1H), 8.37 (s, 1H), 8.27-8.25 (d, J = 4.8 Hz, 1H), 7.34-7.231 (m, 1H), 6.81 (s, 1H), 5.51-5.49 (d, J = 7.2 Hz, 1H), 5.24-5.19 (m, 1H), 4.33-4.29 (m, 1H), 4.03-3.99 (m, 1H), 3.13-3.12 (d, J = 4.4 Hz, 3H), 2.82-2.80 (m, 2H), 2.11-2.09 (m, 2H), 1.60-1.59 (d, 6H). |
| I-1405 | 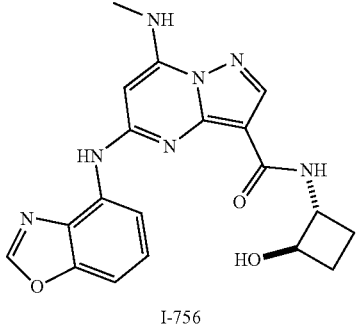 | MS (ES): m/z 462.37 [M + H]+ LCMS purity: 94.77%, HPLC purity: 95.35%, CHIRAL HPLC: 49.15%, 47.09%, $^1$H NMR (DMSO-d$_6$, 400 MHZ): 8.80-8.78 (d, J = 7.6 Hz, 1H), 8.70 (s, 1H), 8.40 (bs, 1H), 8.32 (s, 1H), 7.87 (bs, 1H), 7.33-7.29 (m, 1H), 6.76 (s, 1H), 5.10 (bs, 2H), 4.31-4.27 (t, J = 7.6 Hz, 1H), 4.08 (bs, 3H), 3.67-3.61 (t, J = 11.6 Hz, 2H), 3.17-3.16 (d, J = 4.8 Hz, 3H), 2.32-2.23 (m, 2H), 2.14-2.04 (m, 4H), 1.59-1.53 (m, 2H), 1.45-1.38 (m, 1H). |

Synthesis of 5-(benzo[d]oxazol-4-ylamino)-N-(2-hydroxycyclobutyl)-7-(methylamino)pyrazolo[1,5-a]pyrimidine-3-carboxamide (I-756)

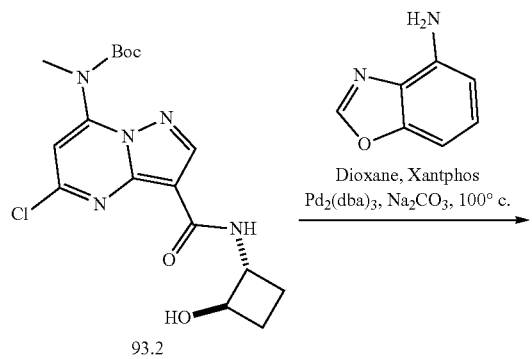

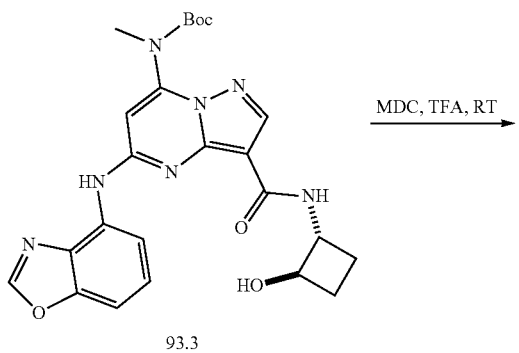

Synthesis of Compound 93.2.

Compound was synthesized as per Example 29 (1-676) to obtain 93.2. (Yield: 52.83%), MS (ES): m/z 396.14 [M+H]+.

Synthesis of Compound 93.3.

Compound was synthesized using general procedure B to obtain 93.3. (0.120 g, 64.17%), MS (ES): 494.21 [M+H]+.

Synthesis of Compound I-756.

Compound was synthesized using general procedure C to obtain I-756 (0.020 g, 83.63%), MS (ES): m/z 394.4 [M+H]+, LCMS purity: 98.95%, HPLC purity: 98.42%, Chiral HPLC: 44.46%, 51.41%, $^1$H NMR (DMSO-d$_6$, 400 MHZ): 9.78 (s, 1H), 8.80 (s, 1H), 8.18 (s, 1H), 8.12-8.10 (d, J=9.2 Hz, 1H), 8.05-8.03 (d, J=8 Hz, 1H), 7.99-7.98 (d, J=4.8 Hz, 1H), 7.53-7.51 (d, J=8 Hz, 1H), 7.47-7.42 (m, 1H), 6.05 (s, 1H), 5.36-5.35 (d, J=7.6 Hz, 1H), 4.20-4.16 (t, J=4.8 Hz, 1H), 3.67-3.63 (t, J=8 Hz, 1H), 2.95-2.94 (d, J=4.4 Hz, 3H), 2.02-1.91 (m, 2H), 1.46-1.41 (t, J=8.8 Hz, 1H), 1.24 (bs, 1H).

Synthesis of 5-(benzo[d]oxazol-4-ylamino)-N-((1S, 2S)-2-hydroxycyclobutyl)-7-(methylamino)pyrazolo [1,5-a]pyrimidine-3-carboxamide (I-858)

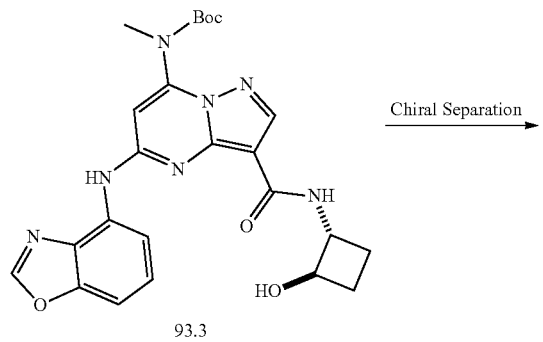

93.3

Chiral Separation →

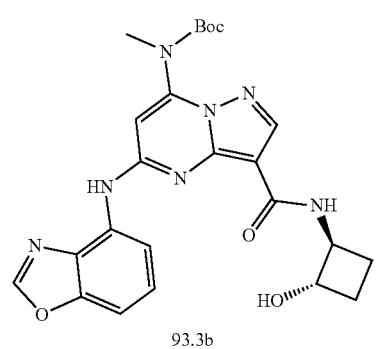

93.3a

+

93.3b

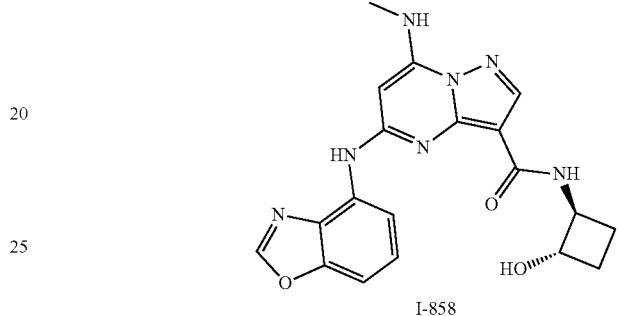

93.3a

MDC, TFA, RT →

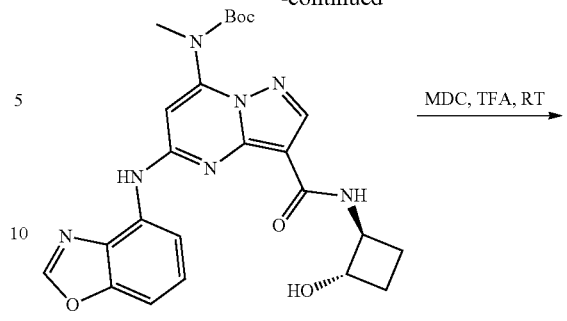

I-858

Synthesis of Compound 93.3.

Compound was synthesized as above to obtain 93.3. (Yield: 64.17%), MS (ES): m/z 494.21 [M+H]$^+$ Synthesis of Compound 93.3a and 93.3b.

Isomers of 93.3 (0.090 g) were separated out using column (CHIRAL PAK AD-H 250×4.6 mm, 5 μM) and DEA in IPA-ACN (70-30) as co-solvent with flow rate of 4 mL/min. to get pure fraction-1 (FR-a) and pure fraction-2 (FR-b). FR-a was evaporated under reduced pressure at 30° C. to afford 0.037 g. MS(ES): m/z 494.21 [M+H]$^+$. FR-b was evaporated under reduced pressure at 30° C. to afford 0.040 g. MS(ES): m/z 494.21 [M+H]$^+$.

Synthesis of Compound I-858.

Compound was synthesized using general procedure C to obtain I-858 (0.025 g, 78.41%), MS (ES): m/z 394.17 [M+H]$^+$, LCMS purity: 96.18%, HPLC purity: 97.26%, Chiral HPLC: 98.43%, $^1$H NMR (DMSO-d$_6$, 400 MHZ): 9.79 (s, 1H), 8.80 (s, 1H), 8.18 (s, 1H), 8.12-8.10 (d, J=9.2 Hz, 1H), 8.05-8.03 (d, J=7.6 Hz, 1H), 7.99-7.98 (d, J=4 Hz, 1H), 7.53-7.51 (d, J=8 Hz, 1H), 7.46-7.42 (m, 1H), 6.05 (s, 1H), 5.37 (bs, 1H), 4.22-4.14 (m, 1H), 3.65 (bs, 1H), 2.94-2.94 (d, J=3.2 Hz, 3H), 2.02-1.91 (m, 2H), 1.62 (bs, 1H), 1.24 (s, 1H).

Characterization data for further compounds prepared by the above methods are presented in Table 23 below. Compounds in Table 23 were prepared by methods substantially similar to those described to prepare I-756, where benzo[d]oxazol-4-amine was replaced with the reagent as indicated in Table 23.

TABLE 23

| Compound # | Reagent | Chiral Separation Conditions and Characterization Data |
|---|---|---|
| I-994 | (structure) | MS (ES): 482.57 [M + H]+ LCMS purity: 98.07%, HPLC purity: 97.72%, CHIRAL HPLC: 50.73%, 48.17%, $^1$H NMR (DMSO-$d_6$, 400 MHZ): 8.91 (s, 1H), 8.24-8.22 (d, J = 6.8 Hz, 1H), 8.20 (s, 1H), 8.03-8.01 (d, J = 8.4 Hz, 1H), 7.94-7.93 (d, J = 4.8 Hz, 1H), 7.51-7.50 (d, J = 6.4 Hz, 1H), 6.36-6.33 (t, J = 7.2 Hz, 1H), 6.23 (s, 1H), 5.45 (bs, 1H), 4.87-4.81 (t, J = 12.4 Hz, 1H), 4.26-4.18 (m, 1H), 3.86-3.84 (d, J = 7.2 Hz, 1H), 3.28 (s, 3H), 2.92-2.91 (d, J = 4.8 Hz, 3H), 2.17 (bs, 1H), 2.06-2.00 (m, 3H), 1.88-1.85 (d, J = 13.2 Hz, 1H), 1.75 (bs, 1H), 1.61-1.56 (m, 2H), 1.49-1.39 (m, 2H), 1.30-1.20 (m, 3H). |
| I-1054<br>I-1055 | (structure) | Intermediate corresponding to 93.3 en route to I-994 was separated into isomers before BOC removal: CHIRAL PAK AD-H (250 × 4.6 mm, 5 μM) and DEA in HEX_IPA-MEOH (50-50) at 4 mL/min.<br>Product prepared from FR-a: MS (ES): m/z 482.56 [M + H]+, LCMS purity: 100%, HPLC purity: 99.24%, Chiral HPLC: 99.48%, $^1$H NMR (DMSO-$d_6$, 400 MHZ): 8.91 (s, 1H), 8.25-8.23 (d, J = 6.8 Hz, 1H), 8.20 (s, 1H), 8.04-8.01 (d, J = 8.8 Hz, 1H), 7.95-7.93 (d, J = 4.8 Hz, 1H), 7.52-7.50 (d, J = 6.4 Hz, 1H), 6.37-6.33 (t, J = 7.2 Hz, 1H), 6.24 (s, 1H), 5.46-5.45 (d, J = 5.6 Hz, 1H), 4.88-4.82 (t, J = 12.4 Hz, 1H), 4.28-4.21 (m, 1H), 3.85 (s, 1H), 3.28 (s, 3H), 2.92-2.91 (d, J = 4.8 Hz, 3H), 2.20-2.17 (m, 2H), 2.07-1.92 (m, 3H), 1.68-1.43 (m, 4H), 1.40-1.20 (m, 3H).<br>Product prepared from FR-b: MS (ES): m/z 582.51 [M + H]+, LCMS purity: 100%, HPLC purity: 96.40%, Chiral HPLC: 95.67%, $^1$H NMR (DMSO-$d_6$, 400 MHZ): 8.91 (s, 1H), 8.25-8.23 (d, J = 6.8 Hz, 1H), 8.20 (s, 1H), 8.04-8.01 (d, J = 8.8 Hz, 1H), 7.95-7.93 (d, J = 4.8 Hz, 1H), 7.52-7.50 (d, J = 6.4 Hz, 1H), 6.37-6.33 (t, J = 7.2 Hz, 1H), 6.24 (s, 1H), 5.46-5.45 (d, J = 5.6 Hz, 1H), 4.88-4.82 (t, J = 12.4 Hz, 1H), 4.28-4.21 (m, 1H), 3.85 (s, 1H), 3.28 (s, 3H), 2.92-2.91 (d, J = 4.8 Hz, 3H), 2.20-2.17 (m, 2H), 2.07-1.92 (m, 3H), 1.68-1.43 (m, 4H), 1.40-1.20 (m, 3H). |
| I-993 | (structure)<br>93a | MS (ES): m/z 482.52 [M + H]+, LCMS purity: 100%, HPLC purity: 99.00%, CHIRAL HPLC purity: 49.7%, 50.3%, $^1$H NMR (DMSO-$d_6$, 400 MHZ): 8.91 (s, 1H), 8.24-8.22 (d, J = 7.2 Hz, 1H), 8.20 (s, 1H), 8.03-8.01 (d, J = 8.8 Hz, 1H), 7.95-7.93 (d, J = 5.2 Hz, 1H), 7.51-7.50 (d, J = 6.4 Hz, 1H), 6.36-6.33 (t, J = 6.8 Hz, 1H), 6.23 (s, 1H), 5.46 (bs, 1H), 4.81 (bs, 1H), 4.24-4.20 (m, 1H), 3.85 (bs, 1H), 3.28 (s, 3H), 2.92-2.91 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). |

TABLE 23-continued

| Compound # | Reagent | Chiral Separation Conditions and Characterization Data |
|---|---|---|
| I-1123<br>I-1124 | 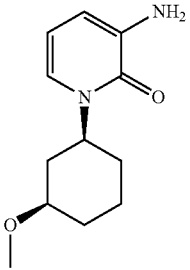<br>93a | Intermediate corresponding to 93.3 en route to I-993 was separated into isomers before BOC removal: CHIRAL PAK AD-H (250 × 4.6 mm, 5 μM) and DEA in methanol at 4 mL/min.<br>Product prepared from FR-a: MS (ES): m/z 482.67 [M + H]$^+$, LCMS purity: 100%, HPLC purity: 98.85%, Chiral HPLC: 100%, $^1$H NMR (DMSO-d$_6$, 400 MHZ): 8.91 (s, 1H), 8.25-8.23 (d, J = 7.2 Hz, 1H), 8.20 (s, 1H), 8.03-8.01 (d, J = 8.8 Hz, 1H), 7.94-7.93 (d, J = 4.8 Hz, 1H), 7.52-7.51 (d, J = 6.4 Hz, 1H), 6.37-6.33 (t, J = 7.2 Hz, 1H), 6.23 (s, 1H), 5.46-5.44 (d, J = 7.2 Hz, 1H), 4.88-4.82 (m, 1H), 4.25-4.21 (m, 1H), 3.87-3.84 (m, 1H), 3.28 (s, 3H), 2.93-2.91 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H).<br>Product prepared from FR-b: MS (ES): m/z 482.41 [M + H]$^+$, LCMS purity: 100%, HPLC purity: 98.87%, Chiral HPLC: 97.65%, $^1$H NMR (DMSO-d$_6$, 400 MHZ): 8.91 (s, 1H), 8.23-8.22 (d, J = 6.4 Hz, 1H), 8.20 (s, 1H), 8.03-8.01 (d, J = 8.8 Hz, 1H), 7.94-7.93 (d, J = 5.2 Hz, 1H), 7.51-7.50 (d, J = 6.4 Hz, 1H), 6.36-6.33 (t, J = 6.8 Hz, 1H), 6.22 (s, 1H), 5.46 (bs, 1H), 4.87-4.81 (m, 1H), 4.24-4.20 (m, 1H), 3.85-3.83 (m, 1H), 3.27 (s, 3H), 2.92-2.90 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). |
| I-930<br>I-931 | 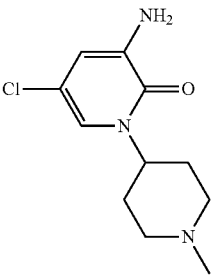<br>91i | Intermediate corresponding the 93.3 en route was separated into isomers before BOC removal: CHIRAL PAK AD-H (250 × 4.6 mm, 5 μM) and DEA in HEX_IPA-MEOH (50-50) at 4 mL/min.<br>Product prepared from FR-a: MS (ES): m/z 501.52 [M + H]$^+$, LCMS purity: 95.11%, HPLC purity: 95.45%, Chiral HPLC: 97.89%, $^1$H NMR (DMSO-d$_6$, 400 MHz): 9.02 (s, 1H), 8.26 (s, 1H), 8.21-8.20 (d, J = 2.4 Hz, 1H), 8.03-8.02 (d, J = 4.8 Hz, 1H), 7.72-7.70 (d, J = 8.8 Hz, 1H), 7.64 (s, 1H), 6.33 (s, 1H), 5.37-5.36 (d, J = 7.2 Hz, 1H), 4.73 (s, 1H), 4.31-4.27 (m, 1H), 4.02-3.98 (m, 1H), 3.58 (s, 2H), 2.93-2.92 (d, J = 4.8 Hz, 3H), 2.34 (s, 3H), 2.09-1.96 (m, 6H), 1.77-1.74 (m, 2H), 1.49-1.35 (s, 2H).<br>Product prepared from FR-b: MS (ES): m/z 501.52 [M + H]$^+$, LCMS purity: 96.49%, HPLC purity: 95.94%, Chiral HPLC: 98.76%, $^1$H NMR (DMSO-d$_6$, 400 MHz): 97.89%, $^1$H NMR (DMSO-d$_6$, 400 MHz): 9.02 (s, 1H), 8.26 (s, 1H), 8.21-8.20 (d, J = 2.4 Hz, 1H), 8.03-8.02 (d, J = 4.8 Hz, 1H), 7.73-7.71 (d, J = 8.8 Hz, 1H), 7.65 (s, 1H), 6.34 (s, 1H), 5.38-5.36 (d, J = 7.2 Hz, 1H), 4.73 (s, 1H), 4.34-4.27 (m, 1H), 4.02-3.96 (m, 1H), 3.58 (s, 2H), 2.93-2.92 (d, J = 4.8 Hz, 3H), 2.23 (s, 3H), 2.09-1.96 (m, 6H), 1.77-1.74 (m, 2H), 1.49-1.35 (s, 2H). |

TABLE 23-continued

| Compound # | Reagent | Chiral Separation Conditions and Characterization Data |
|---|---|---|
| I-825 I-826 | 3-amino-5-chloro-1-(tetrahydropyran-4-yl)pyridin-2(1H)-one | Intermediate corresponding the 93.3 en route was separated into isomers before BOC removal: CHIRALCEL OJ-H (250 mm*4.6 mm, 5u) 0.1% _DEA_HEX_IPA-MEOH (50-50). Product prepared from FR-a: MS (ES): m/z 488.37 [M + H]⁺, LCMS purity: 98.62%, HPLC purity: 97.36%, CHIRAL HPLC purity: 96.69%, $^1$H NMR (DMSO-d$_6$, 400 MHZ): 9.03 (s, 1H), 8.26 (s, 1H), 8.22-8.21 (d, J = 4 Hz, 1H) 8.03-8.02 (d, J = 8 Hz, 1H), 7.73-7.68 (m, 2H), 6.34 (s, 1H), 5.37-5.35 (d, J = 8 Hz, 1H), 5.04-5.01 (t, J = 12 Hz, 1H), 4.31-4.29 (t, J = 8 Hz, 1H), 4.02-3.98 (m, 3H), 2.93-2.92 (d, J = 4.2 Hz, 3H), 2.06-1.96 (m, 5H), 1.78-1.75 (d, J = 11.8 Hz, 2H), 1.49-1.35 (m, 3H). Product prepared from FR-b: MS (ES): m/z 488.42 [M + H]⁺, LCMS purity: 100%, HPLC purity: 96.94%, CHIRAL HPLC purity: 99.43%, $^1$H NMR (DMSO-d$_6$, 400 MHZ): 9.03 (s, 1H), 8.26 (s, 1H), 8.22-8.21 (d, J = 4 Hz, 1H), 8.03 (s, 1H), 7.73-7.68 (m, 2H), 6.34 (s, 1H), 5.37 (s, 1H), 5.04-5.01 (t, J = 12 Hz, 1H), 4.31-4.29 (t, J = 8 Hz, 1H), 4.03-4.01 (d, J = 8 Hz, 3H), 2.92 (s, 3H), 2.06-1.96 (m, 5H), 1.78-1.75 (d, J = 11.8 Hz, 2H), 1.49-1.35 (m, 3H). |
| I-898 I-899 | 3-amino-1-(2-fluoroethyl)pyridin-2(1H)-one | Intermediate corresponding the 93.3 en route was separated into isomers before BOC removal: CHIRALPAK IB (250 mm*4.6 mm, 5u) and 0.1% DEA_HEX_IPA-ACN (70-30) at 4 mL/min. Product prepared from FR-a: MS (ES): m/z 499.42 [M + H]⁺, LCMS purity: 100%, HPLC purity: 99.45%, Chiral HPLC: 100%, $^1$H NMR (DMSO-d$_6$, 400 MHZ): 8.28 (s, 1H), 8.54-8.52 (d, J = 8 Hz, 1H), 8.21 (s, 1H), 8.05-8.03 (d, J = 8 Hz, 1H), 7.90-7.89 (d, J = 4.6 Hz, 1H), 7.46-7.44 (d, J = 8 Hz, 1H), 6.42-6.40 (t, J = 8.2 Hz, 1H), 6.27 (s, 1H), 5.78 (s, 1H), 5.42-5.40 (d, J = 8 Hz, 1H), 4.84-4.81 (t, J = 12.8 Hz, 1H), 4.63-4.50 (m, 3H), 4.36 (s, 1H), 3.09-3.06 (d, J = 12.6 Hz, 2H), 2.92-2.91 (d, J = 4.6 Hz, 3H), 2.73-2.61 (m, 2H), 2.26-2.24 (t, J = 8.2 Hz, 3H), 2.16-1.93 (m, 4H), 1.79-1.77 (m, 2H). Product prepared from FR-b: MS (ES): m/z 499.42 [M + H]⁺, LCMS purity: 100%, HPLC purity: 98.88% Chiral HPLC: 100%, $^1$H NMR (DMSO-d$_6$, 400 MHZ): 8.28 (s, 1H), 8.54-8.52 (d, J = 8 Hz, 1H), 8.21 (s, 1H), 8.05-8.03 (d, J = 8 Hz, 1H), 7.90-7.89 (d, J = 4.6 Hz, 1H), 7.46-7.44 (d, J = 8 Hz, 1H), 6.42-6.40 (t, J = 8.2 Hz, 1H), 6.27 (s, 1H), 5.78 (s, 1H), 5.42-5.40 (d, J = 8 Hz, 1H), 4.84-4.81 (t, J = 12.8 Hz, 1H), 4.63-4.50 (m, 3H), 4.36 (s, 1H), 3.09-3.06 (d, J = 12.6 Hz, 2H), 2.92-2.91 (d, J = 4.6 Hz, 3H), 2.73-2.61 (m, 2H), 2.26-2.24 (t, J = 8.2 Hz, 3H), 2.16-1.93 (m, 4H), 1.79-1.77 (m, 2H). |

TABLE 23-continued

| Compound # | Reagent | Chiral Separation Conditions and Characterization Data |
|---|---|---|
| I-962 | (3-amino-1-(4-methoxy-4-methylcyclohexyl)pyridin-2(1H)-one derivative) | MS (ES): m/z 496.57 [M + H]$^+$, LCMS purity: 100%, HPLC purity: 95.47%, Chiral HPLC: 50.49%, 49.51%, $^1$H NMR (DMSO-d$_6$, 400 MHZ): 8.92 (s, 1H), 8.24-8.22 (d, J = 6.8 Hz, 1H), 8.20 (s, 1H), 8.04-8.02 (d, J = 8.8 Hz, 1H), 7.94-7.93 (d, J = 4.8 Hz, 1H), 7.57-7.55 (d, J = 6.8 Hz, 1H), 6.35-6.31 (t, J = 6.8 Hz, 1H), 6.23 (s, 1H), 5.46-45.44 (d, J = 7.2 Hz, 1H), 4.76 (bs, 1H), 4.27-4.18 (m, 1H), 3.89-31 (m, 1H), 3.17 (s, 3H), 2.92-2.91 (d, J = 4.8 Hz, 3H), 2.06-2.00 (m, 2H), 1.80 (bs, 6H), 1.60-1.50 (m, 3H), 1.24 (bs, 4H). |
| I-1107 I-1108 | (3-amino-1-(4-methoxy-4-methylcyclohexyl)pyridin-2(1H)-one derivative) | Intermediate corresponding the 93.3 en route to I-962 was separated into isomers before BOC removal: CHIRAL PAK AD-H (250 × 4.6 mm, 5 μM) and DEA in HEX_IPA-MEOH (50-50) at 4 mL/min. Product prepared from FR-a: MS (ES): m/z 496.57 [M + H]$^+$, LCMS purity: 95.08%, HPLC purity: 95.02%, Chiral HPLC: 95.53%, $^1$H NMR (DMSO-d$_6$, 400 MHZ): 8.92 (s, 1H), 8.23-8.22 (d, J = 6.4 Hz, 1H), 8.19 (s, 1H), 8.04-8.02 (d, J = 8.8 Hz, 1H), 7.95-7.93 (d, J = 4.8 Hz, 1H), 7.57-7.55 (d, J = 6.4 Hz, 1H), 6.34-6.31 (t, J = 7.2 Hz, 1H), 6.22 (s, 1H), 5.49 (s, 1H), 4.76 (bs, 1H), 4.24-4.19 (m, 1H), 3.85-3.83 (m, 1H), 3.16 (s, 3H), 2.91-2.90 (d, J = 4.4 Hz, 3H), 2.06-2.00 (m, 2H), 1.80 (bs, 6H), 1.60-1.50 (m, 3H), 1.24 (bs, 4H). Product prepared from FR-b: MS (ES): m/z 496.57 [M + H]$^+$, LCMS purity: 95.71%, HPLC purity: 95.11%, Chiral HPLC: 98.80%, $^1$H NMR (DMSO-d$_6$, 400 MHZ): 8.92 (s, 1H), 8.23-8.22 (d, J = 7.2 Hz, 1H), 8.19 (s, 1H), 8.04-8.02 (d, J = 8.8 Hz, 1H), 7.94-7.93 (d, J = 4.4 Hz, 1H), 7.57-7.55 (d, J = 6.4 Hz, 1H), 6.35-6.31 (t, J = 7.2 Hz, 1H), 6.23 (s, 1H), 5.48 (bs, 1H), 4.76 (bs, 1H), 4.24-4.19 (m, 1H), 3.85-3.83 (m, 1H), 3.16 (s, 3H), 2.91-2.90 (d, J = 4.0 Hz, 3H), 2.06-2.00 (m, 2H), 1.80 (bs, 6H), 1.60-1.50 (m, 3H), 1.24 (bs, 4H). |
| I-946 | 91c (3-amino-1-(3-fluorophenyl)pyridin-2(1H)-one derivative) | MS (ES): m/z 464.71 [M + H]$^+$, LCMS purity: 97.18%, HPLC purity: 95.98%, CHIRAL HPLC: 49.08%, 50.92%, $^1$H NMR (DMSO-d$_6$, 400 MHZ): 9.02 (bs, 1H), 8.37-8.35 (d, J = 6.4 Hz, 1H), 8.22 (s, 1H), 8.06-8.03 (d, J = 8.8 Hz, 1H), 7.65-7.59 (m, 1H), 7.52-7.50 (d, J = 10 Hz, 1H), 7.42-7.36 (m, 3H), 6.45-6.41 (t, J = 7.2 Hz, 1H), 6.26 (s, 1H), 4.28-4.20 (m, 1H), 3.93-3.87 (m, 1H), 2.91 (s, 3H), 2.08-2.00 (m, 2H), 1.51-1.46 (t, J = 10 Hz, 1H), 1.26 (bs, 3H). |

TABLE 23-continued

| Compound # | Reagent | Chiral Separation Conditions and Characterization Data |
|---|---|---|
| I-1023<br>I-1024 | 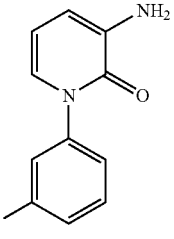<br>91c | I-946 was separated into isomers: CHIRAL PAK AD-H (250 × 4.6 mm, 5u) and 0.1% DEA_HEX_IPA-ACN (70-30).<br>FR-a: MS (ES): m/z 464.31 [M + H]$^+$, LCMS purity: 99.57%, HPLC purity: 99.14%, CHIRAL HPLC purity: 95.01%, $^1$H NMR (DMSO-d$_6$, 400 MHZ): 9.04 (s, 1H), 8.36-8.38 (d, J = 8 Hz, 1H), 8.22 (s, 1H), 8.04-8.06 (d, J = 8 Hz, 1H), 7.99-7.98 (m, 1H), 7.60-7.65 (m, 1H), 7.50-7.52 (d, J = 8 Hz, 1H), 7.36-7.42 (m, 3H), 6.43-6.45 (t, J = 8 Hz, 1H), 6.27 (s, 1H), 5.48-5.50 (d, J = 8 Hz, 1H), 4.20-4.27 (m, 1H), 3.88-3.92 (m, 1H), 2.91-2.92 (d, J = 4 Hz, 3H), 2.02-2.08 (m, 2H), 1.48-1.54 (m, 2H).<br>FR-b: MS (ES): m/z 464.31 [M + H]$^+$, LCMS purity: 99.41%, HPLC purity: 99.57%, CHIRAL HPLC purity: 95.01%, $^1$H NMR (DMSO-d$_6$, 400 MHZ): 9.04 (s, 1H), 8.36-8.38 (d, J = 7.2 Hz, 1H), 8.22 (s, 1H), 8.04-8.06 (d, J = 8 Hz, 1H), 7.99-7.98 (m, 1H), 7.60-7.65 (m, 1H), 7.50-7.52 (d, J = 8 Hz, 1H), 7.36-7.42 (m, 3H), 6.43-6.45 (t, J = 8 Hz, 1H), 6.27 (s, 1H), 5.48-5.50 (d, J = 8 Hz, 1H), 4.20-4.28 (m, 1H), 3.86-3.92 (m, 1H), 2.90-2.92 (d, J = 8 Hz, 3H), 2.02-2.08 (m, 2H), 1.48-1.54 (m, 2H). |
| I-940 | 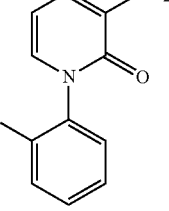 | MS (ES): m/z 464.71 [M + H]$^+$, LCMS purity: 96.38%, HPLC purity: 96.25%, CHIRAL HPLC purity: 50.25%, 49.74%, $^1$H NMR (DMSO-d$_6$, 400 MHZ): 9.07 (bs, 1H), 8.40-8.38 (d, J = 7.2 Hz, 1H), 8.23 (s, 1H), 8.06-8.03 (d, J = 8.8 Hz, 1H), 7.98-7.97 (d, J = 4.8 Hz, 1H), 7.61-7.59 (d, J = 7.6 Hz, 2H), 7.52-7.48 (t, J = 9.2 Hz, 1H), 7.44-7.38 (m, 2H), 6.47-6.43 (t, J = 7.2 Hz, 1H), 6.26 (s, 1H), 5.49-5.47 (d, J = 7.2 Hz, 1H), 4.27-4.23 (m, 1H), 3.58 (s, 3H), 2.92-2.91 (d, J = 4.4 Hz, 3H), 2.09-2.02 (m, 2H). |
| I-1038<br>I-1039 | 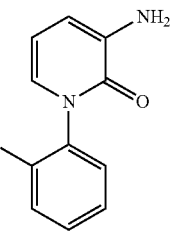 | Intermediate corresponding to 93.3 en route to I-940 was separated into isomers before BOC removal: CHIRAL PAK AD-H (250 × 4.6 mm, 5 μM) and DEA in HEX_IPA-MEOH (50-50) at 4 mL/min.<br>Product prepared from FR-a: MS (ES): m/z 464.67 [M + H]$^+$, LCMS purity: 99.07%, HPLC purity: 96.25%, Chiral HPLC: 100%, $^1$H NMR (DMSO-d$_6$, 400 MHZ): 9.04-9.02 (d, J = 6.4 Hz, 1H), 8.38-8.35 (t, J = 6.8 Hz, 1H), 8.21 (s, 1H), 8.04-8.02 (d, J = 8.8 Hz, 1H), 7.98-7.97 (d, J = 4.8 Hz, 1H), 7.64-7.35 (m, 4H), 6.45-6.40 (m, 1H), 6.26-6.25 (d, J = 6.0 Hz, 1H), 5.49-5.47 (d, J = 7.2 Hz, 1H), 4.28-4.21 (m, 1H), 3.91-3.87 (t, J = 8.0 Hz, 1H), 3.57 (s, 2H), 2.91-2.90 (d, J = 4.4 Hz, 3H), 2.07-2.01 (m, 2H), 1.33-1.23 (m, 2H).<br>Product prepared from FR-b: MS (ES): m/z 464.47 [M + H]$^+$, LCMS purity: 97.025%, HPLC purity: 98.08%, Chiral HPLC: 100%, $^1$H NMR (DMSO-d$_6$, 400 MHZ): 9.04 (s, 1H), 8.36 (s, 1H), 8.21 (s, 1H), 8.04-8.02 (m, 2H), 7.60-7.39 (m, 4H), 6.43 (s, 1H), 6.26 (s, 1H), 5.47 (bs, 1H), 4.23 (bs, 1H), 3.89 (bs, 1H), 3.57 (bs, 2H), 2.90 (bs, 3H), 2.05 (bs, 2H), 1.33-1.23 (m, 2H). |

TABLE 23-continued

| Compound # | Reagent | Chiral Separation Conditions and Characterization Data |
|---|---|---|
| I-675 | (structure: 3-amino-1-(3-fluoropyridin-2-yl)pyridin-2(1H)-one derivative with NH₂) | MS (ES): m/z 465.35 [M + H]⁺, LCMS purity: 98.06%, HPLC purity: 94.39%, Chiral HPLC purity: 49.33% + 47.90%, ¹H NMR (DMSO-d₆, 400 MHZ): 9.08 (s, 1H), 8.52-8.51 (d, J = 4.4 Hz, 1H), 8.39-8.38 (d, J = 5.6, 1H), 8.21 (s, 1H), 8.10-8.02 (m, 2H), 7.98-7.97 (d, J = 5.2 Hz, 1H), 7.75-7.71 (m, 1H), 7.47-7.46 (d, J = 5.6, 1H), 6.51-6.47 (m, 1H), 6.23 (s, 1H), 5.47-5.45 (d, J = 7.6 Hz, 1H), 4.25-4.21 (m, 1H), 3.91-3.87 (m, 1H), 2.91-2.89 (d, J = 4.8 Hz, 3H), 2.04-2.02 (m, 2H), 1.51-1.41 (m, 1H), 1.28-1.25 (m, 1H). |
| I-776 I-777 | (structure: same as I-675) | Intermediate corresponding to 93.3 en route to I-675 was separated into isomers before BOC removal: CHIRALCEL OJ-H (250 mm*4.6 mm, 5u) and 0.1% diethyl amine in methanol at 4 mL/min.<br>Product prepared from FR-a: MS (ES): m/z 465.32 [M + H]⁺, LCMS purity: 100%, HPLC purity: 99.0% CHIRAL HPLC: 97%, ¹H NMR (DMSO-d₆, 400 MHZ): 9.08 (s, 1H), 8.52-8.51 (d, J = 4.0 Hz, 1H), 8.39-8.38 (d, J = 4.0 Hz, 1H), 8.21 (s, 1H), 8.10-8.02 (m, 2H), 7.98-7.97 (d, J = 4.0 Hz, 1H), 7.75-7.71 (m, 1H), 7.48-7.46 (m, 1H), 6.51-6.47 (t, J = 7.2 Hz 1H), 6.23 (s, 1H), 5.48-5.46 (d, J = 8.0 Hz, 1H), 4.27-4.19 (m, 1H), 3.93-3.85, (m, 1H), 2.91-2.89, (d, J = 8.0 Hz, 3H), 2.08-2.00 (m, 2H), 1.54-1.44 (m, 1H), 1.31-1.21 (m, 1H).<br>Product prepared from FR-b: MS (ES): m/z 465.32 [M + H]⁺, LCMS purity: 100%, HPLC purity: 99.05% CHIRAL HPLC: 98.04%, ¹H NMR (DMSO-d₆, 400 MHZ): 9.08 (s, 1H), 8.52-8.51 (d, J = 4.0 Hz, 1H), 8.39-8.38 (d, J = 4.0 Hz, 1H), 8.21 (s, 1H), 8.10-8.02 (m, 2H), 7.98-7.97 (d, J = 4.0 Hz, 1H), 7.75-7.71 (m, 1H), 7.48-7.46 (m, 1H), 6.51-6.47 (t, J = 7.2 Hz 1H), 6.23 (s, 1H), 5.48-5.46 (d, J = 8.0 Hz, 1H), 4.27-4.21 (m, 1H), 3.91-3.87, (m, 1H), 2.91-2.89, (d, J = 8.0 Hz, 3H), 2.06-2.02 (m, 2H), 1.54-1.47 (m, 1H), 1.31-1.21 (m, 1H). |
| I-705 | (structure: 3-amino-1-(pyridin-2-yl)pyridin-2(1H)-one derivative) | MS (ES): m/z 447.46 [M + H]⁺, LCMS purity: 97.43%, HPLC purity: 97.25%, ¹H NMR (DMSO-d₆, 400 MHZ): 9.06 (s, 1H), 8.67-8.66 (d, J = 4.0 Hz, 1H), 8.37-8.35 (d, J = 8.0 Hz, 1H), 8.22 (s, 1H), 8.07-8.05 (d, J = 8.0 Hz, 2H), 7.98 (s, 1H), 7.87-7.85 (d, J = 8.0 Hz, 1H), 7.62-7.54 (m, 2H), 6.49-6.45 (t, J = 8.0 Hz 1H), 6.26 (s, 1H), 4.26-4.22 (m, 1H), 3.89 (s, 1H), 2.92 (s, 3H), 2.07-2.00 (m, 2H), 1.55-1.48 (m, 1H), 1.28-1.24 (m, 1H), 1.20-1.17 (m, 1H). |
| I-971 I-972 | (structure: same as I-705) | Intermediate corresponding to 93.3 en route to I-705 was separated into isomers before BOC removal: CHIRAL PAK AD-H 250 × 4.6 mm, 5 μM) and 0.1% DEA_HEX_IPA-ACN (70-30) at 4 mL/min.<br>Product prepared from FR-a: MS (ES): m/z 447.46 [M + H]⁺, LCMS purity: 100%, HPLC purity: 95.36%, Chiral HPLC: 97.98%, ¹H NMR (DMSO-d₆, 400 MHZ): 9.06 (s, 1H), 8.67-8.66 (d, J = 4.2 Hz, 1H), 8.37-8.35 (d, J = 6 Hz, 1H), 8.22 (s, 1H), 8.09-8.06 (m, 2H), 7.98-7.97 (d, J = 4.2 Hz, 1H), 7.87-7.85 (d, |

TABLE 23-continued

| Compound # | Reagent | Chiral Separation Conditions and Characterization Data |
|---|---|---|
| | | J = 8 Hz, 1H), 7.62-7.60 (m, 1H), 7.57-7.54 (m, 1H), 6.49-6.47 (t, J = 8 Hz, 1H) 6.26 (s, 1H), 5.48-5.46 (d, J = 6 Hz, 1H), 4.26-4.24 (t, J = 8 Hz, 1H), 3.91-3.89 (t, J = 7.9 Hz, 1H), 2.92-2.91 (d, J = 4.5 Hz, 3H), 2.10-2.01 (m, 2H), 1.52-1.50 (t, J = 7.8 Hz, 1H), 1.31-1.24 (m, 1H). Product prepared from FR-b: MS (ES): m/z 447.21 [M + H]+, LCMS purity: 100%, HPLC purity: 95%, Chiral HPLC: 95.14%, 1H NMR (DMSO-d6, 400 MHZ): 9.06 (s, 1H), 8.67-8.66 (d, J = 4.2 Hz, 1H), 8.37-8.35 (d, J = 6 Hz, 1H), 8.22 (s, 1H), 8.09-8.06 (m, 2H), 7.98-7.97 (d, J = 4.2 Hz, 1H), 7.87-7.85 (d, J = 8 Hz, 1H), 7.62-7.60 (m, 1H), 7.57-7.54 (m, 1H), 6.49-6.47 (t, J = 8 Hz, 1H) 6.26 (s, 1H), 5.48-5.46 (d, J = 6 Hz, 1H), 4.26-4.24 (t, J = 8 Hz, 1H), 3.91-3.89 (t, J = 7.9 Hz, 1H), 2.92-2.91 (d, J = 4.5 Hz, 3H), 2.10-2.01 (m, 2H), 1.52-1.50 (t, J = 7.8 Hz, 1H), 1.31-1.24 (m, 1H). |
| I-698 | 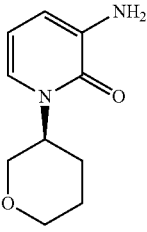 [SMILES: Nc1cccn([C@H]2CCCOC2)c1=O] | MS (ES): m/z 454.45 [M + H]+, LCMS purity: 100%, HPLC purity: 95.44%, CHIRAL HPLC: 50.39%, 48.75%, 1H NMR (DMSO-d6, 400 MHZ): 8.94 (s, 1H), 8.25-8.23 (d, J = 6 Hz, 1H), 8.19 (s, 1H), 7.99 (bs, 1H), 7.93-7.92 (d, J = 4.8 Hz, 1H), 7.54-7.53 (d, J = 6 Hz, 1H), 6.36-6.32 (t, J = 7.2 Hz, 1H), 6.24 (s, 1H), 5.45-5.43 (d, J = 7.2 Hz, 1H), 4.91-4.86 (m, 1H), 4.13-4.09 (m, 1H), 3.86-3.82 (t, J = 7.6 Hz, 3H), 3.60-3.55 (t, J = 10.4 Hz, 1H), 3.48-3.44 (t, J = 9.2 Hz, 1H), 2.91-2.89 (d, J = 4.8 Hz, 3H), 1.77 (bs, 3H), 1.51-1.43 (m, 2H), 1.23-1.16 (m, 3H). |
| I-726 I-727 | | I-698 was separated into isomers: CHIRAL PAK (AD-H 250 × 4.6 mm, 5u) and 0.1% DEA in methanol. FR-a: MS (ES): m/z 454.5 [M + H]+, LCMS purity: 95.02%, HPLC purity: 95.43%, CHIRAL HPLC purity: 100%, 1H NMR (DMSO-d6, 400 MHZ): 8.94 (s, 1H), 8.25-8.23 (d, J = 6.4 Hz, 1H), 8.19 (s, 1H), 7.99 (bs, 1H), 7.93-7.92 (d, J = 4.8 Hz, 1H), 7.54-7.53 (d, J = 6 Hz, 1H), 6.36-6.33 (t, J = 7.2 Hz, 1H), 6.24 (s, 1H), 5.45-5.43 (d, J = 7.2 Hz, 1H), 4.91-4.86 (m, 1H), 4.23-4.19 (m, 1H), 3.84-3.82 (m, 3H), 3.60-3.55 (t, J = 10.4 Hz, 1H), 3.48-3.43 (t, J = 11.2 Hz, 1H), 2.91-2.89 (d, J = 4.4 Hz, 3H), 2.04-2.02 (d, J = 6 Hz, 5H), 1.51-1.46 (m, 1H), 1.23-1.18 (m, 2H). FR-b: MS (ES): m/z 454.4 [M + H]+, LCMS purity: 98.96%, HPLC purity: 100%, CHIRAL HPLC purity: 100%, 1H NMR (DMSO-d6, 400 MHZ): 8.94 (s, 1H), 8.25-8.23 (d, J = 7.2 Hz, 1H), 8.19 (s, 1H), 7.99 (bs, 1H), 7.93-7.92 (d, J = 4.4 Hz, 1H), 7.54-7.53 (d, J = 6 Hz, 1H), 6.36-6.32 (t, J = 7.2 Hz, 1H), 6.24 (s, 1H), 5.45-5.43 (d, J = 7.2 Hz, 1H), 4.91-4.86 (m, 1H), 4.23-4.19 (m, 1H), 3.86-3.82 (m, 3H), 3.60-3.54 (t, J = 10 Hz, 1H), 3.48-3.43 (t, J = 8.4 Hz, 1H), 2.91-2.89 (d, J = 4.4 Hz, 3H), 2.04-2.03 (d, J = 6 Hz, 5H), 1.51-1.46 (m, 1H), 1.23-1.19 (m, 2H). |

TABLE 23-continued

| Compound # | Reagent | Chiral Separation Conditions and Characterization Data |
|---|---|---|
| I-1070 I-1071 | [structure: 3-amino-1-(4-methylthiazol-2-yl)pyridin-2(1H)-one] | Intermediate corresponding the 93.3 en route was separated into isomers before BOC removal: CHIRAL PAK AD-H (250 × 4.6 mm, 5 μM) and DEA in HEX_IPA-MEOH (50-50) at 4 mL/min. Product prepared from FR-a: MS (ES): m/z 467.42 [M + H]$^+$, LCMS purity: 100%, HPLC purity: 99.83%, Chiral HPLC: 98.86%, $^1$H NMR (DMSO-d$_6$, 400 MHZ): 9.23 (s, 1H), 8.68-8.66 (d, J = 6.8 Hz, 1H), 8.43-8.41 (d, J = 7.2 Hz, 1H), 8.24 (s, 1H), 8.06-8.04 (d, J = 8.8 Hz, 1H), 7.98-7.97 (d, J = 4.8 Hz, 1H), 7.54 (s, 1H), 6.73-6.69 (t, J = 7.2 Hz, 1H), 6.38 (s, 1H), 5.78 (bs, 1H), 4.60-4.57 (t, J = 6.0 Hz, 1H), 4.38 (s, 1H), 3.35-3.33 (m, 1H), 2.94-2.93 (d, J = 4.8 Hz, 3H), 2.20-1.95 (m, 3H), 1.79 (s, 1H), 1.56 (s, 1H), 1.35-1.24 (m, 1H). Product prepared from FR-b: MS (ES): m/z 467.47 [M + H]$^+$, LCMS purity: 98.83%, HPLC purity: 97.74%, Chiral HPLC: 100%, $^1$H NMR (DMSO-d$_6$, 400 MHZ): 9.22 (s, 1H), 8.68-8.66 (d, J = 7.2 Hz, 1H), 8.43-8.41 (d, J = 6.4 Hz, 1H), 8.24 (s, 1H), 8.06-8.04 (d, J = 8.8 Hz, 1H), 7.98-7.97 (d, J = 5.2 Hz, 1H), 7.54 (s, 1H), 6.73-6.69 (t, J = 7.2 Hz, 1H), 6.38 (s, 1H), 5.48-5.47 (d, J = 3.6 Hz, 1H), 4.60-4.57 (t, J = 6.0 Hz, 1H), 4.39 (s, 1H), 3.35-3.33 (m, 1H), 2.94-2.93 (d, J = 4.8 Hz, 3H), 2.20-1.95 (m, 3H), 1.79 (s, 1H), 1.56 (s, 1H), 1.35-1.24 (m, 1H). |
| I-658 | [structure: 3-amino-1-(4-methyloxazol-2-yl)pyridin-2(1H)-one] | MS (ES): m/z 451.83 [M + H]$^+$ LCMS purity: 100%, HPLC purity: 95.78%, Chiral HPLC purity: 49.79%, 49.91%, NMR (DMSO-d$_6$, 400 MHZ): 9.98 (s, 1H), 8.63-8.61 (t, J = 6 Hz, 1H), 8.23 (s, 1H), 8.03-7.96 (m, 3H), 7.41-7.39 (m, 1H), 6.53-6.49 (t, J = 7.6 Hz, 1H), 6.30 (s, 1H), 5.47 (s, 1H), 4.60-4.55 (m, 1H), 4.36 (s, 1H), 3.57 (s, 3H), 2.91 (s, 3H), 2.19-2.17 (d, J = 0.8 Hz, 2H), 2.02-1.93 (m, 2H). |
| I-768 I-769 | [structure: 3-amino-1-(4-methyloxazol-2-yl)pyridin-2(1H)-one] | I-658 was separated into isomers: CHIRAL PAK (AD-H 250 × 4.6 mm, 5u) and 0.1% DEA in methanol at 4 mL/min. FR-a: MS (ES): m/z 451.22 [M + H]$^+$, LCMS purity: 98.60%, HPLC purity: 100%, CHIRAL HPLC purity: 100%, $^1$H NMR (DMSO-d$_6$, 400 MHZ): 8.98 (s, 1H), 8.65-8.63 (d, J = 7.2 Hz, 1H), 8.24 (s, 1H), 8.04-7.95 (m, 3H), 7.42-7.41 (d, J = 6.4 Hz, 1H), 6.54-6.50 (t, J = 7.2 Hz, 1H), 6.31 (s, 1H), 5.47-46 (d, J = 3.2 Hz, 1H), 4.60-4.55 (m, 1H), 4.37 (s, 1H), 3.19-17 (d, J = 5.2 Hz, 1H), 2.93-2.92 (d, J = 4.8 Hz, 3H), 2.20 (s, 2H), 2.13-1.94 (m, 2H), 1.76 (s, 2H). FR-b: MS (ES): m/z 451.22 [M + H]$^+$, LCMS purity: 98.32%, HPLC purity: 98.53%, CHIRAL HPLC purity: 98.38%, $^1$H NMR (DMSO-d$_6$, 400 MHZ): 8.98 (s, 1H), 8.65-8.63 (d, J = 7.2 Hz, 1H), 8.23 (s, 1H), 8.04 (s, 1H), 8.02 (s, 1H), 7.95 (s, 1H), 7.42-7.49 (d, J = 6.8 Hz, 1H), 6.54-6.50 (t, J = 7.2 Hz, 1H), 6.31 (s, 1H), 4.60-4.56 (t, J = 7.2 Hz, 1H), 4.37 (s, 1H), 2.93-2.92 (s, 3H), 2.20 (s, 4H), 2.13-1.94 (m, 2H), 1.79-1.76 (d, J = 9.6 Hz, 2H). |

TABLE 23-continued

| Compound # | Reagent | Chiral Separation Conditions and Characterization Data |
|---|---|---|
| I-943 | 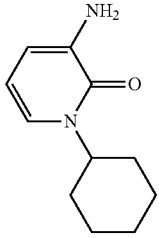 [SMILES: Nc1cccn(C2CCCCC2)c1=O] | MS (ES): m/z 452.76 [M + H]$^+$, LCMS purity: 95.56%, HPLC purity: 94.86%, CHIRAL HPLC: 49.03%, 50.86%, $^1$H NMR (DMSO-d$_6$, 400 MHZ): 8.89 (s, 1H), 8.22-8.21 (d, J = 6.8 Hz, 1H), 8.18 (s, 1H), 8.02-8.00 (d, J = 8.4 Hz, 1H), 7.92-7.91 (d, J = 4.8 Hz, 1H), 7.47-7.46 (d, J = 6.8 Hz, 1H), 6.35-6.31 (t, J = 7.2 Hz, 1H), 6.22 (s, 1H), 4.80 (bs, 1H), 4.23-4.19 (m, 1H), 3.57 (s, 1H), 2.91-2.90 (d, J = 4.4 Hz, 3H), 2.03-2.01 (d, J = 8 Hz, 2H), 1.87-1.78 (m, 4H), 1.70-1.67 (m, 3H), 1.57-1.42 (m, 3H), 1.23 (bs, 3H). |
| I-1002 I-1003 | 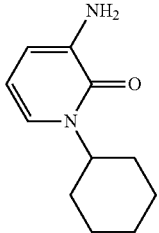 [SMILES: Nc1cccn(C2CCCCC2)c1=O] | Intermediate corresponding the 93.3 en route to I-943 was separated into isomers before BOC removal: CHIRAL PAK AD-H (250 × 4.6 mm, 5 μM) and DEA in HEX_IPA-MEOH (50-50) at 4 mL/min. Product prepared from FR-a: MS (ES): m/z 452.51 [M + H]$^+$, LCMS purity: 97.43%, HPLC purity: 96.74%, Chiral HPLC: 98.30%, $^1$H NMR (DMSO-d$_6$, 400 MHZ): 8.95 (s, 1H), 8.22 (s, 1H), 8.21 (s, 1H), 8.06-8.04 (d, J = 8.4 Hz, 1H), 7.98 (s, 1H), 7.49-7.48 (d, J = 6.8 Hz, 1H), 6.37-6.33 (t, J = 7.2 Hz, 1H), 6.22 (s, 1H), 4.84-4.78 (m, 1H), 4.25-4.21 (m, 1H), 3.75-3.68 (m, 1H), 3.52-3.47 (m, 1H), 2.93-2.92 (d, J = 4.4 Hz, 3H), 2.03-2.01 (d, J = 8 Hz, 2H), 1.87-1.78 (m, 3H), 1.70-1.67 (m, 2H), 1.52-1.42 (m, 3H), 1.25-1.21 (m, 4H). Product prepared from FR-b: MS (ES): m/z 452.51 [M + H]$^+$, LCMS purity: 96.44%, HPLC purity: 95%, Chiral HPLC: 99.05%, $^1$H NMR (DMSO-d$_6$, 400 MHZ): 8.94 (s, 1H), 8.22 (s, 1H), 8.21 (s, 1H), 8.06-8.04 (d, J = 8.4 Hz, 1H), 7.98 (s, 1H), 7.49-7.48 (d, J = 6.8 Hz, 1H), 6.37-6.33 (t, J = 6.8 Hz, 1H), 6.22 (s, 1H), 4.84-4.78 (m, 1H), 4.25-4.18 (m, 1H), 3.75-3.68 (m, 1H), 3.52-3.47 (m, 1H), 2.93-2.92 (d, J = 4.4 Hz, 3H), 2.04-2.02 (d, J = 8 Hz, 2H), 1.87-1.78 (m, 3H), 1.70-1.67 (m, 2H), 1.52-1.42 (m, 3H), 1.25-1.21 (m, 4H). |
| I-918 | 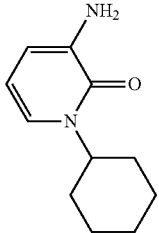 | MS (ES): m/z 412.20 [M + H]$^+$, LCMS purity: 96.64%, HPLC purity: 96.03%, CHIRAL HPLC purity: 48.49%, 50.57%, 1H NMR (DMSO-d6, 400 MHZ): 8.94 (s, 1H), 8.23-8.19 (m, 2H), 8.04-8.80 (d, J = 8.8 Hz, 2H), 7.48-7.46 (d, J = 6.8 Hz, 1H), 6.37-6.33 (m, 1H), 5.19-5.16 (m, 1H), 4.24-4.20 (m, 1H), 3.85-3.81 (m, 1H), 3.64 (s, 3H), 2.90 (s, 3H), 2.03-2.01 (d, J = 7.2 Hz, 2H), 1.36-1.34 (d, J = 6.8 Hz, 6H), 1.29-1.19 (m, 1H). |
| I-981 I-982 | 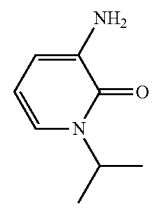 | I-918 was separated into isomers: CHIRAL PAK AD-H (250 × 4.6 mm, 5 μM) and 0.1% DEA_HEX_IPA-ACN (70-30) at 4 mL/min. FR-a: MS (ES): m/z 412.42 [M + H]$^+$, LCMS purity: 98.47%, HPLC purity: 98.30%, Chiral HPLC: 97.30%, $^1$H NMR (DMSO-d$_6$, 400 MHZ): 8.93 (s, 1H), 8.25-8.23 (d, J = 8 Hz, 1H), 8.20 (s, 1H), 8.04-8.02 (d, J = 8.8 Hz, 1H), 7.93-7.92 (d, J = 4.8 Hz, 1H), 7.48-7.46 (d, J = 8.3 Hz, 1H), 6.36-6.34 (t, J = 8.6 Hz, 1H), 6.24 (s, 1H), 5.21-5.16 (m, 1H), |

| Compound # | Reagent | Chiral Separation Conditions and Characterization Data |
|---|---|---|
| | | 4.25-4.19 (m, 1H), 3.85-3.83 (t, J = 7.8 Hz, 1H), 3.58 (s, 1H), 2.92-2.91 (d, J = 4 Hz, 3H), 2.07-2.05 (d, J = 8 Hz, 1H), 1.56-1.52 (m, 1H), 1.50-1.45 (m, 2H), 1.38-1.36 (d, J = 8 Hz, 6H).<br>FR-b: MS (ES): m/z 412.57 [M + H]+, LCMS purity: 9, 6.57%, HPLC purity: 99.53%, Chiral HPLC: 98.80%, $^1$H NMR (DMSO-$d_6$, 400 MHZ): 8.94 (s, 1H), 8.25-8.24 (d, J = 4.8 Hz, 1H), 8.20 (s, 1H), 8.04-8.02 (d, J = 8.8 Hz, 1H), 7.93-7.92 (d, J = 4.8 Hz, 1H), 7.48-7.46 (t, J = 8.3 Hz, 1H), 6.38-6.37 (t, J = 4 Hz, 1H), 6.24 (s, 1H), 5.21-5.16 (m, 1H), 4.27-4.19 (m, 1H), 3.85-3.83 (t, J = 7.8 Hz, 1H), 3.58 (s, 1H), 2.92-2.91 (d, J = 4 Hz, 3H), 2.07-2.05 (d, J = 8 Hz, H), 1.50-1.45 (m, 2H), 1.38-1.36 (d, J = 8 Hz, 6H). |
| I-697 | 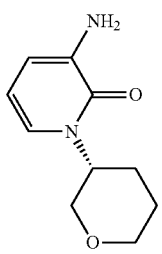 [SMILES: Nc1cccn([C@@H]2CCCOC2)c1=O] | MS (ES): m/z 454.40 [M + H]+, LCMS purity: 100%, HPLC purity: 97.56%, CHIRAL HPLC: 50.29%, 49.70%, $^1$H NMR (DMSO-$d_6$, 400 MHZ): 8.94 (s, 1H), 8.25-8.23 (d, J = 6 Hz, 1H), 8.19 (s, 1H), 7.99 (s, 1H), 7.93-7.92 (d, J = 5.2 Hz, 1H), 7.54-7.52 (d, J = 6.8 Hz, 1H), 6.36-6.33 (t, J = 6.8 Hz, 1H), 6.24 (s, 1H), 5.45-5.43 (d, J = 7.2 Hz, 1H), 4.91-4.86 (m, 1H), 4.23-4.19 (t, J = 8.8 Hz, 1H), 3.82 (bs, 3H), 3.55 (s, 2H), 2.91-2.90 (d, J = 4.8 Hz, 3H), 1.99 (s, 6H), 1.55 (bs, 1H), 1.51-1.44 (m, 1H). |
| I-724<br>I-725 | 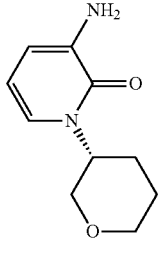 [SMILES: Nc1cccn([C@@H]2CCCOC2)c1=O] | I-697 was separated into isomers: CHIRAL PAK IB (250 mm*4.6 mm, 5u) in 0.1% diethylamine in methanol at 4 mL/min.<br>FR-a: MS (ES): m/z 454.66 [M + H]+ LCMS purity: 100%, HPLC purity: 97.82%, Chiral HPLC purity: 97.82%, NMR (DMSO-$d_6$, 400 MHZ): 8.95 (s, 1H), 8.25-8.23 (d, J = 6.4 Hz, 1H), 8.19 (s, 1H), 8.02-7.99 (d, J = 8.8 Hz, 1H), 7.94-7.92 (d, J = 4.8 Hz, 1H), 7.54-7.53 (d, J = 6.4 Hz, 1H), 6.36-6.32 (t, J = 7.2 Hz, 1H), 6.24 (s, 1H), 5.45 (s, 1H), 4.91-4.86 (m, 1H), 4.23-4.19 (t, J = 8.4 Hz, 1H), 3.84 (s, 3H), 3.59-3.54 (t, J = 10 Hz, 1H), 3.48-3.43 (t, J = 11.2 Hz, 1H), 3.17-3.16 (J = 4 Hz, 1H), 2.91-2.89 (d, J = 4.4 Hz, 3H), 2.05-2.03 (m, 5H), 1.77-1.71 (m, 2H).<br>FR-b: MS (ES): m/z 454.66 [M + H]+ LCMS purity: 100%, HPLC purity: 98.63%, Chiral HPLC purity: 97.82%, NMR (DMSO-$d_6$, 400 MHZ): 8.95 (s, 1H), 8.25-8.23 (d, J = 6.4 Hz, 1H), 8.19 (s, 1H), 8.02-7.99 (d, J = 8.8 Hz, 1H), 7.94-7.92 (d, J = 4.8 Hz, 1H), 7.54-7.53 (d, J = 6 Hz, 1H), 6.36-6.33 (t, J = 7.2 Hz, 1H), 6.24 (s, 1H), 5.45-43 (d, J = 7.6 Hz, 1H), 4.91-4.86 (m, 1H), 4.23-4.19 (t, J = 8 Hz, 1H), 3.86-3.82 (t, J = 8 Hz, 3H), 3.60-3.55 (t, J = 10.4 Hz, 1H), 3.48-3.43 (t, J = 11.2 Hz, 1H), 3.17-3.16 (d, J = 5.2 Hz, 1H), 2.91-2.89 (d, J = 4.8 Hz, 3H), 2.04-2.03 (m, 5H), 1.77-1.71 (m, 2H). |
| I-1390 | 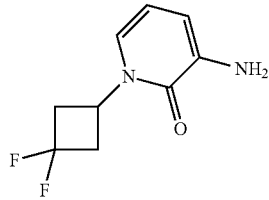 [SMILES: Nc1cccn(C2CC(F)(F)C2)c1=O] | MS (ES): 460.42 [M + H]+ LCMS purity: 98.78%, HPLC purity: 95.66%, CHIRAL HPLC: 48.80%, 50.33%, $^1$H NMR (DMSO-$d_6$, 400 MHZ): 9.00 (s, 1H), 8.28-8.26 (d, J = 6.8 Hz, 1H), 8.19 (s, 1H), 8.02-8.00 (d, J = 8.4 Hz, 1H), 7.94-7.93 (d, J = 4.8 Hz, 1H), 7.46-7.45 (d, J = 6 Hz, 1H), 6.39-6.35 (t, J = 7.2 Hz, 1H), 6.24 (s, 1H), 5.45-5.43 (d, J = 7.2 Hz, 1H), |

TABLE 23-continued

| Compound # | Reagent | Chiral Separation Conditions and Characterization Data |
|---|---|---|
| | | 4.91 (bs, 1H), 4.24-4.19 (m, 1H), 3.86-3.82 (m, 1H), 3.71-3.67 (m, 1H), 3.57 (bs, 1H), 3.32 (s, 1H), 2.90-2.89 (d, J = 4.4 Hz, 3H), 2.05-1.99 (m, 2H), 1.51-1.46 (m, 1H), 1.23 (bs, 2H). |

Synthesis of 5-((1-(2-cyclopropoxyethyl)-2-oxo-1,2-dihydropyridin-3-yl)amino)-N-(2-hydroxycyclobutyl)-7-(methylamino)pyrazolo[1,5-a]pyrimidine-3-carboxamide (I-472)

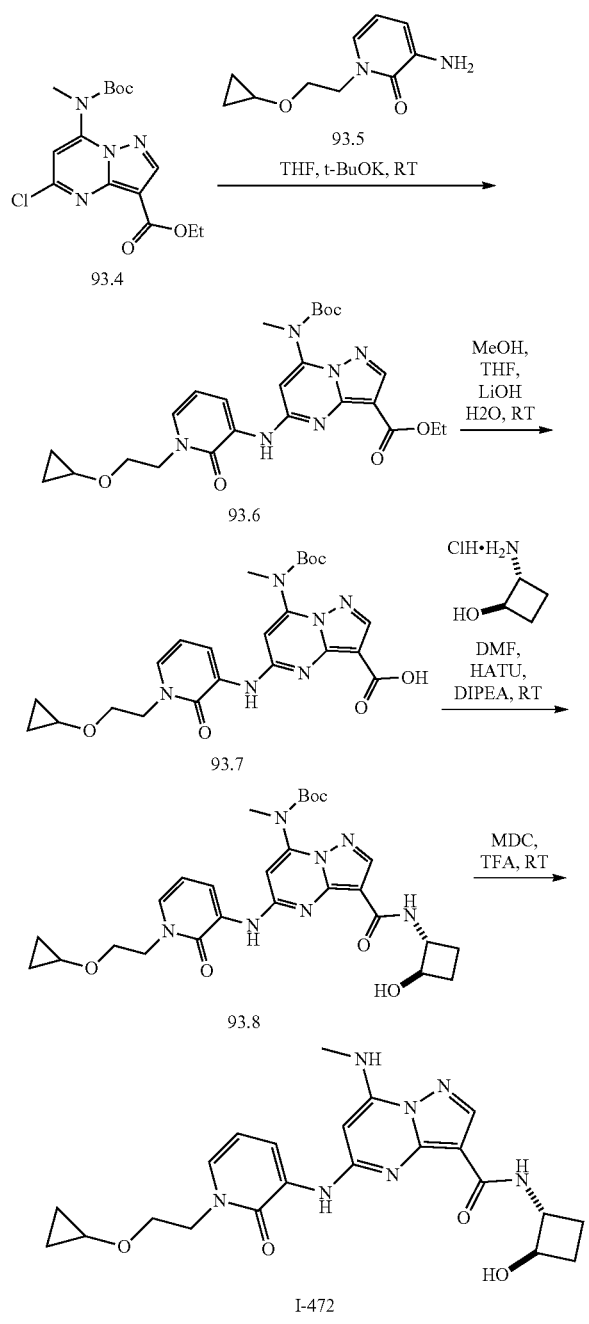

Synthesis of Compound 93.4.

Compound was synthesized using general procedure of core synthesis to obtain 93.4. (Yield: 62.21%). MS (ES): m/z 355.5 [M+H]$^+$.

Synthesis of Compound 93.5.

Compound was synthesized as per I-453 to obtain 93.5. (Yield: 82.45%). MS (ES): m/z 195.1 [M+H]$^+$.

Synthesis of Compound 93.6.

To a cooled solution of 93.4 (0.5 g, 1.41 mmol, 1.0 eq), and 93.5 (0.273 g, 1.41 mmol, 1.0 eq) in tetrahydrofuran (10 mL) at 0° C. was added potassium ter-butoxide (1M in tetrahydrofuran) (2.8 mL, 2.82 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 93.6. (0.450 g, 62.30%). MS (ES): m/z 513.24 [M+H]$^+$.

Synthesis of Compound 93.7.

To a solution of 93.6 (0.450 g, 0.87 mmol, 1.0 eq), in tetrahydrofuran: methanol: water (10 mL, 2:2:1) was added lithium hydroxide (0.365 g, 8.7 mmol, 10 eq). The reaction was stirred at RT for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 93.7 (0.380 g, 89.33%). MS(ES): m/z 485.21 [M+H]$^+$.

Synthesis of Compound 93.8.

Compound was synthesized using general procedure A to obtain 93.8. (0.152 g, 70.01%), MS (ES): 554.27 [M+H]$^+$.

Synthesis of Compound I-472.

Compound was synthesized using general procedure C to obtain I-472 (0.132 g, 96.38%), MS (ES): m/z 454.47 [M+H]$^+$, LCMS purity: 96.20%, HPLC purity: 95.86%, CHIRAL HPLC purity: 48.09%, 47.56% $^1$H NMR (DMSO-d$_6$, 400 MHZ): 8.95 (s, 1H), 8.26-8.24 (d, J=7.2 Hz, 1H), 8.19 (s, 1H), 8.04-8.02 (d, J=8.8 Hz, 1H), 7.94-7.93 (s, J=4.8 Hz, 1H), 7.35-7.33 (d, J=6.8 Hz, 1H), 6.31-6.28 (t, J=7.2 Hz, 1H), 6.23 (s, 1H), 5.45-5.43 (d, J=7.2 Hz, 1H), 4.25-4.16 (m, 3H), 3.87-3.83 (t, J=8 Hz, 1H), 3.77-3.75 (t, J=5.2 Hz, 2H), 2.91-2.90 (d, J=4.4 Hz, 3H), 2.06-1.99 (m, 2H), 1.51-1.46 (t, J=9.6 Hz, 2H), 1.26-1.19 (m, 2H), 0.40 (bs, 3H).

Synthesis of 5-((1-(2-cyclopropoxyethyl)-2-oxo-1,2-dihydropyridin-3-yl)amino)-N-((1R,2R)-2-hydroxycyclobutyl)-7-(methylamino)pyrazolo[1,5-a]pyrimidine-3-carboxamide (I-515) and 5-((1-(2-cyclopropoxyethyl)-2-oxo-1,2-dihydropyridin-3-yl)amino)-N-((1S,2S)-2-hydroxycyclobutyl)-7-(methylamino)pyrazolo[1,5-a]pyrimidine-3-carboxamide (I-514)

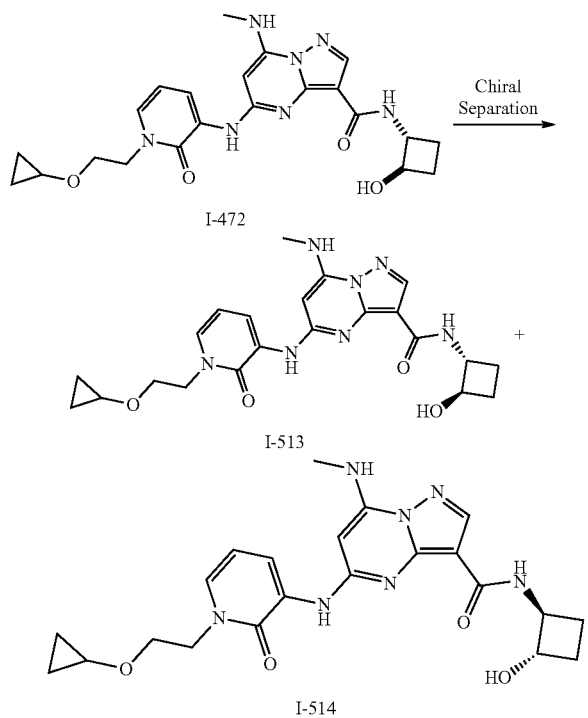

Synthesis of Compound I-513 and I-514.

Isomers of I-472 (0.100 g) were separated out using column (CHIRAL PAK IB 250 mm*4.6 mm, 5 u) in 0.1% diethylamine in methanol as co-solvent with flow rate of 4 mL/min. to get pure fraction-1 (FR-a) and fraction-2 (FR-b).

Fraction-1 was concentrated under reduced pressure at 30° C. to afford 0.040 g. MS(ES): m/z 454.50 [M+H]+ LCMS purity: 95.95%, HPLC purity: 96.49%, Chiral HPLC purity: 100%, NMR (DMSO-$d_6$, 400 MHZ): 8.93 (s, 1H), 8.25-8.23 (d, J=6 Hz, 1H), 8.19 (s, 1H), 8.03-8.01 (d, J=8.8 Hz, 1H), 7.92 (s, 1H), 7.34-7.32 (d, J=6.8 Hz, 1H), 6.30-6.27 (t, J=7.2 Hz, 1H), 6.22 (s, 1H), 5.43 (s, 1H), 4.24-4.15 (m, 4H), 3.85-3.83 (d, J=6 Hz, 1H), 3.77-3.74 (t, J=5.2 Hz, 2H), 2.90-2.90 (d, J=2.8 Hz, 3H), 2.12-1.98 (m, 2H), 1.53-1.43 (m, 1H), 1.29-1.14 (m, 3H), 0.41-0.40 (m, 2H).

Fraction-2 was concentrated under reduced pressure at 30° C. to afford 0.025 g. MS(ES): m/z 454.50 [M+H]+ LCMS purity: 100%, HPLC purity: 99.72%, Chiral HPLC purity: 98.37%, NMR (DMSO-$d_6$, 400 MHZ): 8.93 (s, 1H), 8.25-8.23 (d, J=7.2 Hz, 1H), 8.19 (s, 1H), 8.03-8.01 (d, J=8.8 Hz, 1H), 7.92-7.91 (d, J=4.8 Hz, 1H), 7.34-7.32 (d, J=6.8 Hz, 1H), 6.30-6.27 (t, J=7.2 Hz, 1H), 6.22 (s, 1H), 5.43-5.42 (d, J=7.2 Hz, 1H), 4.24-4.15 (m, 4H), 3.86-3.80 (m, 1H), 3.77-3.74 (t, J=5.2 Hz, 2H), 2.91-2.89 (d, J=4.8 Hz, 3H), 2.12-1.98 (m, 2H), 1.53-1.43 (m, 1H), 1.23-1.15 (m, 3H), 0.41-0.40 (m, 2H).

Characterization data for further compounds prepared by the above methods are presented in Table 24 below. Compounds in Table 24 were prepared by methods substantially similar to those described to prepare I-472, where 93.5 was replaced with the reagent as indicated in Table 24.

TABLE 24

| Compound # | Reagent | Chiral Separation Conditions and Characterization Data |
|---|---|---|
| I-528 | 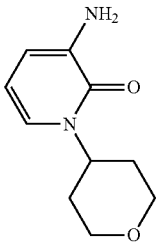 [SMILES: Nc1cccn(C2CCOCC2)c1=O] | MS(ES): m/z 454.50 [M + H]+. LCMS purity: 100%, HPLC purity: 100%, Chiral HPLC purity: 47.90%, 48.93%, NMR (DMSO-$d_6$, 400 MHZ): 8.91 (s, 1H), 8.25-8.23 (d, J = 6.4 Hz, 1H), 8.19 (s, 1H), 8.02-7.99 (d, J = 8.8 Hz, 1H), 7.92-7.91 (d, J = 4.8 Hz, 1H), 7.51-7.49 (d, J = 5.6 Hz, 1H), 6.37-6.33 (t, J = 7.2 Hz, 1H), 6.23 (s, 1H), 5.44-5.42 (d, J = 7.6 Hz, 1H), 5.07-5.01 (t, J = 12 Hz, 1H), 4.25-4.19 (m, 1H) 4.02-4.00 (d, 2H), 3.86-3.80 (m, 2H), 3.54-3.49 (t, 2H), 2.91-2.90 (d, J = 4.8 Hz, 3H), 2.03-1.93 (m, 5H), 1.77-1.74 (d, J = 11.2 Hz, 2H). |
| I-596 I-597 | 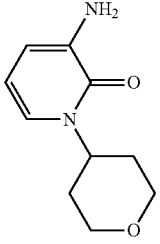 [SMILES: Nc1cccn(C2CCOCC2)c1=O] | I-528 was separated into isomers: CHIRAL PAK IB (250 mm * 4.6 mm, 5u) in 0.1% diethylamine in methanol at 4 mL/min. FR-a: MS (ES): m/z 454.50 [M + H]+, LCMS purity: 100%, HPLC purity: 100% CHIRAL HPLC: 100%, 1H NMR (DMSO-$d_6$, 400 MHZ): 8.92 (s, 1H), 8.26-8.24 (d, J = 6.8 Hz, 1H), 8.20 (s, 1H), 8.03-8.01 (d, J = 8.4 Hz, 1H), 7.94-7.92 (d, J = 4.8 Hz, 1H), 7.52-7.50 (d, J = 6 Hz, 1H), 6.38-6.34 (t, J = 7.2 Hz, 1H), 6.24 (s, 1H), 5.45-5.44 (d, J = 7.2 Hz, 1H), |

TABLE 24-continued

| Compound # | Reagent | Chiral Separation Conditions and Characterization Data |
|---|---|---|
| | | 5.08-5.02 (m, 1H), 4.24-4.20 (t, J = 7.6 Hz, 1H), 4.03-4.00 (m, 2H), 3.87-3.83 (t, J = 7.6 Hz, 1H), 3.55-3.50 (t, J = 12 Hz, 2H), 2.92-2.91 (d, J = 4.4 Hz, 3H), 2.04-2.1.94 (m, 2H), 1.78-1.76 (d, J = 10.4 Hz, 2H), 1.56-1.47 (m, 2H), 1.25-1.16 (m, 2H). FR-b: MS (ES): m/z 454.50 [M + H]⁺, LCMS purity: 100%, HPLC purity: 100% CHIRAL HPLC: 99.58%, ¹H NMR (DMSO-d₆, 400 MHZ): 8.92 (s, 1H), 8.26-8.24 (d, J = 6.4 Hz, 1H), 8.20 (s, 1H), 8.03-8.01 (d, J = 9.2 Hz, 1H), 7.94-7.93 (d, J = 4.8 Hz, 1H), 7.52-7.51 (d, J = 5.6 Hz, 1H), 6.38-6.34 (t, J = 7.2 Hz, 1H), 6.25 (s, 1H), 4.24-4.20 (t, J = 8.8 Hz, 1H), 4.03-4.01 (m, 2H), 3.87-3.83 (t, J = 7.2 Hz, 1H), 3.55-3.50 (t, J = 11 Hz, 2H), 2.92-2.91 (d, J = 4.8 Hz, 3H), 2.04-2.1.97 (m, 4H), 1.78-1.75 (d, J = 12.4.4 Hz, 2H), 1.54-1.47 (m, 2H), 1.30-1.11 (m, 2H). |
| I-540 | 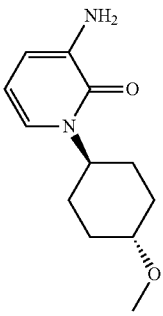<br>92a | MS (ES): m/z 482.41 [M + H]⁺, LCMS purity: 100%, HPLC purity: 95.18%, ¹H NMR (DMSO-d₆, 400 MHZ): 8.89 (s, 1H), 8.24-8.22 (d, J = 7.2 Hz, 1H), 8.19 (s, 1H), 8.02-8.00 (d, J = 8.8 Hz, 1H), 7.93-7.91 (d, J = 4.8 Hz, 1H), 7.45-7.44 (d, J = 6.8 Hz, 1H), 6.35-6.32 (t, J = 7.2 Hz, 1H), 6.22 (s, 1H), 5.44-5.42 (d, J = 7.2 Hz, 1H), 4.79 (bs, 1H), 4.24-4.20 (t, J = 8.4 Hz, 1H), 3.87-3.83 (t, J = 7.6 Hz, 1H), 3.23 (s, 3H), 2.92-2.91 (d, J = 4.8 Hz, 3H), 2.14 (bs, 2H), 2.04-2.02 (d, J = 7.6 Hz, 2H), 1.78 (bs, 4H), 1.54-1.49 (m, 1H), 1.24-1.19 (m, 4H). |
| I-635<br>I-636 | 92a | I-540 was separated into isomers: CHIRAL PAK IB (250 mm * 4.6 mm, 5u) in 0.1% diethyl amine in methanol at 4 mL/min. FR-a: MS(ES): m/z 482.82 [M + H]⁺. LCMS purity: 100%, HPLC purity: 99.77%, Chiral HPLC purity: 100%, NMR (DMSO-d₆, 400 MHZ): 8.89 (s, 1H), 8.23-8.21 (d, J = 7.2 Hz, 1H), 8.18 (s, 1H), 8.02-8.01 (d, J = 8.8 Hz, 1H), 7.93-7.92 (d, J = 4.8 Hz, 1H), 7.45-7.43 (d, J = 8.8 Hz, 1H), 6.35-6.31 (t, J = 7.2 Hz, 1H), 6.22 (s, 1H), 5.45-5.44 (d, J = 6.8 Hz, 1H), 4.23-4.19 (t, J = 8.4 Hz, 1H), 3.85-3.82 (t, J = 7.2 Hz, 1H), 3.27 (s, 3H), 3.23-3.22 (m, 1H), 2.91-2.90 (d, J = 4.8 Hz, 3H), 2.16-2.13 (d, J = 10.8 Hz, 2H), 2.03-2.01 (d, J = 7.2 Hz, 2H), 1.81-1.77 (m, 4H), 1.50-1.46 (t, J = 8.8 Hz, 2H), 1.34-1.18 (m, 4H). FR-b: MS(ES): m/z 482.82 [M + H]⁺. LCMS purity: 100%, HPLC purity: 100%, Chiral HPLC purity: 97.89%, NMR (DMSO-d₆, 400 MHZ): 8.90 (s, 1H), 8.24-8.22 (d, J = 7.2 Hz, 1H), 8.20 (s, 1H), 8.03-8.01 (d, J = 8.8 Hz, 1H), 7.94-7.93 (d, J = 4.8 Hz, 1H), 7.46-7.44 (d, J = 6.8 Hz, 1H), 6.36-6.32 (t, J = 7.2 Hz, 1H), 6.23 (s, 1H), 5.46-5.44 (d, J = 7.2 Hz, 1H), 4.24-4.20 (t, J = 8.4 Hz, 1H), 3.87-3.83 (t, J = 7.2 Hz, 1H), 3.28 (s, 3H), 3.25-3.21 (m, 1H), 2.92-2.91 (d, J = 4.4 Hz, 3H), 2.17-2.14 (d, J = 11.2 Hz, 2H), 2.06-2.02 (d, J = 8 Hz, 2H), 1.81-1.76 (m, 4H), 1.52-1.47 (t, J = 9.6 Hz, 2H), 1.35-1.19 (m, 4H). |

TABLE 24-continued

| Compound # | Reagent | Chiral Separation Conditions and Characterization Data |
|---|---|---|
| I-373 | H₂N-pyridine-O-CD₃ 49.2 | MS (ES): m/z 387.45 [M + H]⁺, LCMS purity: 100%, HPLC purity: 100%, CHIRAL HPLC purity: 49.35%, 50.64%, $^1$H NMR (DMSO-$d_6$, 400 MHZ): 8.97 (s, 1H), 8.30-8.28 (d, J = 6.4 Hz, 1H), 8.15 (s, 1H), 8.05-8.02 (d, J = 9.2 Hz, 1H), 7.93 (bs, 2H), 7.05-7.02 (m, 1H), 5.92 (s, 1H), 5.36-5.34 (d, J = 7.2 Hz, 1H) 4.20-4.15 (t, J = 8.4 Hz, 1H), 3.68-3.64 (t, J = 7.6 Hz, 1H), 2.92-2.91 (d, J = 4.8 Hz, 3H), 2.02-1.90 (m, 3H), 1.13-1.06(m, 1H). |
| I-410 I-411 | H₂N-pyridine-O-CD₃ 49.2 | I-373 was separated into isomers: CHIRAL PAK AD-H (250 × 4.6 mm, 5u) and 0.1% DEA in methanol at 4 mL/min. FR-a: MS(ES): m/z 385.51 [M − H]⁺, LCMS purity: 100%, HPLC purity: 100%, CHIRAL HPLC purity: 100%, $^1$H NMR (DMSO-$d_6$, 400 MHZ): 8.97 (s, 1H), 8.30-8.28 (d, J = 7.6 Hz, 1H), 8.15 (s, 1H), 8.04-8.02 (d, J = 9.2 Hz, 1H), 7.94-7.92 (m, 2H), 7.05-7.02 (m, 1H), 5.92 (s, 1H), 5.35-5.33 (d, J = 7.2 Hz, 1H), 3.68-3.64 (t, J = 7.6 Hz, 1H), 2.92-2.91 (d, J = 4.8 Hz, 3H), 2.02-1.91 (m, 3H), 1.45-1.41 (t, J = 9.6 Hz, 1H), 1.11-1.06 (m, 1H). FR-b: MS(ES): m/z 385.34 [M − H]⁺, LCMS purity: 100%, HPLC purity: 100%, CHIRAL HPLC purity: 99.27%, $^1$H NMR (DMSO-$d_6$, 400 MHZ): 8.97 (s, 1H), 8.30-8.28 (d, J = 7.6 Hz, 1H), 8.15 (s, 1H), 8.04-8.02 (d, J = 8.8 Hz, 1H), 7.94-7.92 (t, J = 4.4 Hz, 2H), 7.05-7.02 (m, 1H), 5.92 (s, 1H), 5.35-5.33 (d, J = 7.2 Hz, 1H), 3.68-3.64 (m, 1H), 2.92-2.91 (d, J = 4.4 Hz, 3H), 2.00-1.91 (m, 3H), 1.45-1.40 (t, J = 9.6 Hz, 1H) 1.11-1.06 (m, 1H). |
| I-602 | pyridine-NH₂ / tetrahydropyran 91j | MS(ES): m/z 438.6 [M + H]⁺ LCMS purity: 100%, HPLC purity: 97.69%, NMR (DMSO-$d_6$, 400 MHZ): 9.90 (s, 1H), 8.21-8.076 (m, 3H), 7.72-7.68 (d, J = 7.6 Hz, 1H), 7.56 (s, 1H), 6.97-6.96 (d, J = 7.6 Hz, 1H), 6.69 (s, 1H), 5.41 (d, J = 7.2 Hz, 1H), 4.24-4.20 (t, J = 8.4 Hz, 1H), 4.02-3.88 (m, 4H), 4.55-4.50 (d, J = 10.8 Hz, 1H), 2.97-42.89 (m, J = 10 .8 Hz , 4H), 2.01-1.89 (m, 4H), 1.67 (s, 2H), 1.50-1.45 (d, J = 9.2 Hz 1H), 1.31-1.24 (m, 1H). |
| I-666 I-667 | pyridine-NH₂ / tetrahydropyran 91j | I-602 was separated into isomers: CHIRAL PAK AD-H (250 × 4.6 mm, 5u) and 0.1% DEA in methanol and isopropyl alcohol at 4 mL/min. FR-a: MS(ES): m/z 438.50 [M + H]⁺, LCMS purity: 100%, HPLC purity: 100%, CHIRAL HPLC purity: 100%, $^1$H NMR (DMSO-$d_6$, 400 MHZ): 9.91 (s, 1H), 8.21 (s, 1H), 8.16-14 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.42-5.40 (d, J = 7.2 Hz, 1H), 4.26-4.18 (m, 1H), 4.02-3.88 (m, 3H), 3.55-3.50 (t, J = 10.8 Hz, 1H), 2.97-2.89 (m, 4H), 2.06-1.86 (m, 4H), 1.69-1.67 (m, 2H), 1.52-1.34 (m, 3H). FR-b: MS(ES): m/z 438.50 [M + H]⁺, LCMS purity: 100%, HPLC purity: 100%, CHIRAL HPLC purity: 99%, $^1$H NMR (DMSO-$d_6$, 400 MHZ): 9.91 (s, 1H), 8.21 (s, 1H), 8.16-14 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, |

TABLE 24-continued

| Compound # | Reagent | Chiral Separation Conditions and Characterization Data |
|---|---|---|
| | | 1H), 6.97-6.96 (d, J = 7.6 Hz, 1H), 6.69 (s, 1H), 5.42-5.40 (d, J = 7.2 Hz, 1H), 4.26-4.18 (m, 1H), 4.02-3.88 (m, 3H), 3.55-3.50 (t, J = 10.8 Hz, 1H), 2.97-2.89 (m, 4H), 2.06-1.86 (m, 4H), 1.69-1.67 (m, 2H), 1.52-1.34 (m, 3H). |
| I-603 | 91k | MS(ES): m/z 438.6 [M + H]⁺ LCMS purity: 98.99%, HPLC purity: 97.46%, NMR (DMSO-d₆, 400 MHZ): 9.90 (s, 1H), 8.21 (s, 1H), 8.162-140 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.41-5.39 (d, J = 7.2 Hz, 1H), 4.24-4.20 (m, 1H), 4.02-3.88 (m, 3H), 3.55-3.50 (t, J = 10.8 Hz, 1H), 2.97-2.96 (m, 1H), 2.89 (s, 3H), 2.03-1.89 (m, 4H), 1.67 (bs, 2H), 1.50-1.45 (m, 1H), 1.31-1.24 (m, 2H). |
| I-664 I-665 | 91k | I-603 was separated into isomers: CHIRAL PAK AD-H (250 × 4.6 mm, 5u) and 0.1% DEA in methanol and isopropyl alcohol at 4 mL/min. FR-a: MS(ES): m/z 438.50 [M + H]⁺, LCMS purity: 100%, HPLC purity: 100%, CHIRAL HPLC purity: 100%, ¹H NMR (DMSO-d₆, 400 MHZ): 9.90 (s, 1H), 8.21-8.08 (m, 3H), 7.70 (m, 1H), 7.56 (m, 1H), 6.97-6.96 (d, J = 6.8 Hz, 1H), 6.69 (s, 1H), 5.41-5.39 (d, J = 6.8 Hz, 1H), 4.22 (s, 1H), 4.00-3.88 (m, 3H), 3.55-3.50 (t, J = 10.4 Hz, 1H), 2.97 (s, 4H), 2.01-1.91 (m, 4H), 1.67 (s, 2H), 1.50-1.214 (t, J = 9.2 Hz, 1H). 1.31-1.23 (m, 2H). FR-b: MS(ES): m/z 438.50 [M + H]⁺, LCMS purity: 100%, HPLC purity: 98.84%, CHIRAL HPLC purity: 96.69%, ¹H NMR (DMSO-d₆, 400 MHZ): 9.90 (s, 1H), 8.21 (s, 1H), 8.16-8.13 (d, J = 8.8 Hz, 1H), 8.08-8.07 (d, J = 4.4 Hz, 1H), 7.72-7.68 (t, J = 7.6 Hz, 1H), 7.57 (s, 1H), 6.98-6.96 (d, J = 7.6 Hz, 1H), 6.69 (s, 1H), 5.41-5.39 (d, J = 7.6 Hz, 1H), 4.24-4.20 (m, 1H), 4.02-3.88 (m, 3H), 3.55-3.50 (t, J = 10.8 Hz, 1H), 2.97-2.89 (m, 4H), 2.01-1.89 (m, 4H), 1.67 (s, 2H), 1.50-1.45 (t, J = 9.2 Hz, 1H), 1.34-1.11 (m, 2H). |

Synthesis of Intermediate of 93a and 93b.

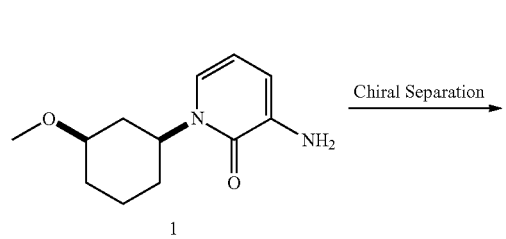

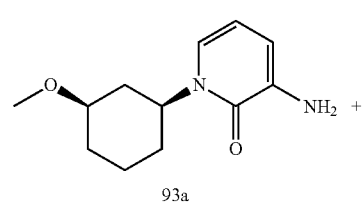

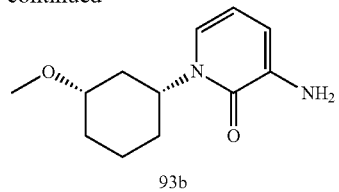

Synthesis of Compound 1.

Compound was synthesized as per I-568 to obtain 1. (Yield: 94.28%), MS (ES): m/z 223.1 [M+H]⁺

Synthesis of Compound 93a and 93b.

Isomers of 1 (0.855 g) were separated out using column (CHIRAL PAK AD-H 250×4.6 mm, 5 pM) and DEA in methanol as co-solvent with flow rate of 4 mL/min. to get pure fraction-1 (FR-a) and pure fraction-2 (FR-b). FR-a was evaporated under reduced pressure at 30° C. to afford 0.233 g. MS(ES): m/z 223.14 [M+H]+. FR-b was evaporated under reduced pressure at 30° C. to afford 0.246 g. MS(ES): m/z 223.14 [M+H]+.

Example 94: Synthesis of Compounds where R³ is N-(trans)-(3-hydroxycyclopentyl)carboxamide, R⁶ is Hydrogen, and R⁷ is Methylamine Synthesis of N-(3-hydroxycyclopentyl)-7-(methylamino)-5-((2-oxo-1-((S)-tetrahydro-2H-pyran-3-yl)-1,2-dihydropyridin-3-yl)amino)pyrazolo[1,5-a]pyrimidine-3-carboxamide (I-702)

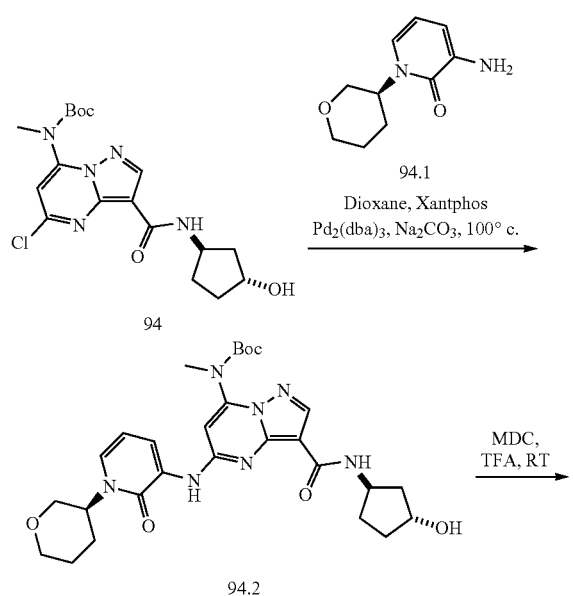

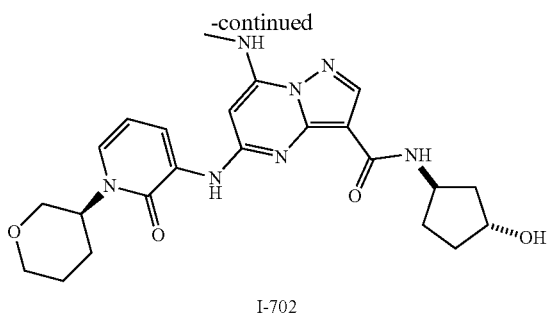

I-702

Synthesis of Compound 94.
Compound was synthesized as per Example 105 (I-701) to obtain 94. (Yield: 59.79%), MS (ES): m/z 410.1 [M+H]+.
Synthesis of Compound 94.1.
Compound was synthesized as per I-696 to obtain 94.1. MS (ES): m/z 195.11 [M+H]+.
Synthesis of Compound 94.2.
Compound was synthesized using general procedure B to obtain 94.2. (0.140 g, 67.39%), MS (ES): 568.28 [M+H]+.
Synthesis of Compound I-702.
Compound was synthesized using general procedure C to obtain I-702 (0.105 g, 91.06%), MS (ES): m/z 468.32 [M+H]+, LCMS purity: 99.39%, HPLC purity: 99.24%, CHIRAL HPLC: 50.85%, 49.14%, ¹H NMR (DMSO-d₆, 400 MHZ): 8.87 (s, 1H), 8.30-8.28 (d, J=6.8 Hz, 1H), 8.18 (s, 1H), 7.90-7.89 (d, J=4.8 Hz, 1H), 7.68-7.66 (d, J=8 Hz, 1H), 7.50-7.48 (d, J=6.8 Hz, 1H), 6.49-6.46 (t, J=7.2 Hz, 1H), 6.26 (s, 1H), 4.88 (bs, 1H), 4.30-4.24 (m, 1H), 4.16 (bs, 1H), 3.60 (s, 3H), 3.41-3.36 (m, 4H), 2.90-2.89 (d, J=4.8 Hz, 3H), 1.72-1.64 (m, 6H), 1.11-1.07 (t, J=6.8 Hz, 2H).

Characterization data for further compounds prepared by the above methods are presented in Table 25 below. Compounds in Table 25 were prepared by methods substantially similar to those described to prepare I-702, where 94.1 was replaced with the reagent as indicated in Table 25.

TABLE 25

| Compound # | Reagent | Chiral Separation Conditions and Characterization Data |
|---|---|---|
| I-701 | ![NH2 pyridone THP] | MS (ES): m/z 468.32 [M + H]+, LCMS purity: 97.78%, HPLC purity: 97.41%, CHIRAL HPLC purity: 49.80%, 50.19%, ¹H NMR (DMSO-d₆, 400 MHZ): 8.87 (s, 1H), 8.30-8.28 (d, J = 6.8 Hz, 1H), 8.18 (s, 1H), 7.90-7.89 (d, J = 4.8 Hz, 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.90-4.85 (m, 1H), 4.74-4.74 (d, J = 3.2 Hz, 1H), 4.30-4.24 (m, 1H), 4.16 (bs, 1H), 3.85-3.82 (m, 2H), 3.60-3.55 (t, J = 10.4 Hz, 1H), 2.90-2.89 (d, J = 4.4 Hz, 3H), 2.28-2.21 (m, 1H), 1.96 (s, 4H), 1.76-1.62 (m, 5H), 1.19-1.16 (d, J = 7.2 Hz, 1H). |
| I-728 I-729 | ![NH2 pyridone THP chiral] | I-701 was separated into isomers: CHIRAL PAK AD-H (250 × 4.6 mm, 5u) and 0.1% DEA in methanol. FR-a: MS(ES): m/z 468.46 [M + H]+, LCMS purity: 100%, HPLC purity: 99.38%, CHIRAL HPLC purity: 100%, ¹H NMR (DMSO-d₆, 400 MHZ): 8.87 (s, 1H), 8.30-8.28 (d, J = 7.2 Hz, 1H), 8.18 (s, 1H), 7.90-7.89 (d, J = 4.8 Hz 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.90-4.85 (m, 1H), 4.75-4.74 (d, J = 3.2 Hz,1H), 4.30-4.24 |

TABLE 25-continued

| Compound # | Reagent | Chiral Separation Conditions and Characterization Data |
|---|---|---|
| | | (m, 1H), 4.16 (bs, 1H), 3.85-3.82 (m, 2H), 3.60-3.55 (t, J = 10 Hz, 1H), 2.90-2.89 (d, J = 4.4 Hz, 3H), 2.28-2.21 (m, 1H), 1.66-1.60 (m, 5H), 1.44-1.38 (m, 1H), 1.23 (bs, 2H), 1.04-1.03 (d, J = 6 Hz, 1H), 0.87-0.83 (m, 1H). FR-b: MS(ES): m/z 468.48 [M + H]$^+$, LCMS purity: 100%, HPLC purity: 99.44%, CHIRAL HPLC purity: 98.38%, $^1$H NMR (DMSO-d$_6$, 400 MHZ): 8.87 (s, 1H), 8.30-8.28 (d, J = 7.2 Hz, 1H), 8.18 (s, 1H), 7.90-7.89 (d, J = 4.4 Hz 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.90-4.85 (m, 1H), 4.75-4.74 (d, J = 3.2 Hz, 1H), 4.30-4.24 (m, 1H), 4.16 (bs, 1H), 3.85-3.82 (m, 2H), 3.60-3.55 (t, J = 10 Hz, 1H), 2.90-2.89 (d, J = 4.4 Hz, 3H), 2.28-2.21 (m, 1H), 1.66-1.62 (m, 5H), 1.44-1.38 (m, 1H), 1.23 (bs, 2H), 1.04-1.03 (d, J = 6 Hz, 1H), 0.87-0.83 (m, 1H). |
| I-702 | [structure] | MS (ES): m/z 468.32 [M + H]$^+$, LCMS purity: 99.39%, HPLC purity: 99.24%, CHIRAL HPLC: 50.85%, 49.14%, $^1$H NMR (DMSO-d$_6$, 400 MHZ): 8.87 (s, 1H), 8.30-8.28 (d, J = 6.8 Hz, 1H), 8.18 (s, 1H), 7.90-7.89 (d, J = 4.8 Hz, 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.88 (bs, 1H), 4.30-4.24 (m, 1H), 4.16 (bs, 1H), 3.60 (s, 3H), 3.41-3.36 (m, 4H), 2.90-2.89 (d, J = 4.8 Hz, 3H), 1.72-1.64 (m, 6H), 1.11-1.07 (t, J = 6.8 Hz, 2H). |
| I-738 I-739 | [structure] | I-702 was separated into isomers: CHIRAL PAK AD-H 250 × 4.6 mm, 5u) 0.1% DEA in methanol. FR-a: MS(ES): m/z 468.66 [M + H]$^+$, LCMS purity: 95.03%, HPLC purity: 99.90%, CHIRAL HPLC purity: 99.00%, $^1$H NMR (DMSO-d$_6$, 400 MHZ): 8.87 (s, 1H), 8.30-8.28 (d, J = 7.2 Hz, 1H), 8.18 (s, 1H), 7.89 (bs, 1H), 7.68-7.66 (d, J = 8 Hz, 1H), 7.50-7.48 (d, J = 6.8 Hz, 1H), 6.49-6.46 (t, J = 6.8 Hz, 1H), 6.26 (s, 1H), 4.88 (bs, 1H), 4.74 (bs, 1H), 4.28-4.26 (d, J = 6.8 Hz, 1H), 4.16 (bs, 1H), 3.82 (bs, 2H), 3.60-3.55 (t, J = 10.4 Hz, 1H), 2.90-2.89 (d, J = 3.6 Hz, 3H), 2.26-2.23 (m, 2H), 1.64 (bs, 6H), 1.24 (bs, 1H), 1.18-1.14 (t, J = 7.2 Hz, 1H), 0.85 (bs, 1H). FR-b: MS(ES): m/z 468.66 [M + H]$^+$, LCMS purity: 100%, HPLC purity: 98.75%, CHIRAL HPLC purity: 98%, $^1$H NMR (DMSO-d$_6$, 400 MHZ): 8.87 (s, 1H), 8.30-8.29 (d, J = 6.4 Hz, 1H), 8.18 (s, 1H), 7.90-7.89 (d, J = 4.8 Hz, 1H), 7.68-7.66 (d, J = 7.6 Hz, 1H), 7.50-7.48 (d, J = 6.4 Hz, 1H), 6.49-6.46 (t, J = 7.2 Hz, 1H), 6.26 (s, 1H), 4.88 (bs, 1H), 4.75-4.74 (d, J = 2.8 Hz, 1H), 4.28-4.26 (d, J = 7.6 Hz, 1H), 4.16 (bs, 1H), 3.82 (bs, 2H), 3.60-3.55 (t, J = 10.4 Hz, 1H), 2.90-2.89 (d, J = 4.8 Hz, 3H), 2.26-2.23 (m, 2H), 1.60 (bs, 6H), 1.24 (bs, 1H), 1.18-1.14 (t, J = 7.2 Hz, 1H), 0.85 (bs, 1H). |

TABLE 25-continued

| Compound # | Reagent | Chiral Separation Conditions and Characterization Data |
|---|---|---|
| I-467 | 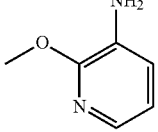 32.2 | MS (ES): m/z 398.22 [M + H]$^+$, LCMS purity: 100%, HPLC purity: 100%, CHIRAL HPLC: 49.73%, 0.26%, $^1$H NMR (DMSO-d$_6$, 400 MHZ): 8.92 (s, 1H), 8.23-8.21 (d, J = 6.8 Hz, 1H), 8.14 (s, 1H), 7.92-7.90 (m, 2H), 7.66-7.64 (d, J = 8 Hz, 1H), 6.98-6.95 (m, 1H), 5.89 (s, 1H), 4.57-4.56 (d, J = 3.6 Hz, 1H), 4.42-4.36 (m, 1H), 4.15 (bs, 1H), 3.95 (s, 3H), 2.92-2.90 (d, J = 4.8 Hz, 3H), 2.08-2.03 (m, 1H), 1.89-1.82 (m, 2H), 1.56 (bs,1H), 1.45 (bs, 1H), 1.36-1.33 (m, 1H). |
| I-487 I-488 | 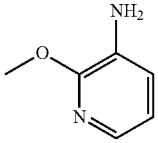 32.2 | I-467 was separated into isomers: CHIRAL PAK AD-H (250 × 4.6 mm, 5u) and 0.1% DEA in methanol at 4 mL/min. FR-a: MS(ES): m/z 398.22 [M + H]$^+$, LCMS purity: 100%, HPLC purity: 99.51%, CHIRAL HPLC purity: 100%, $^1$H NMR (DMSO-d$_6$, 400 MHZ): 8.91 (s, 1H), 8.22-8.20 (d, J = 7.6 Hz, 1H), 8.13 (s, 1H), 7.92-7.90 (m, 2H), 7.65-7.63 (d, J = 7.6 Hz, 1H), 6.98-6.94 (m, 1H), 5.88 (s, 1H), 4.56 (bs, 1H), 4.41-4.36 (m, 1H), 4.15 (bs, 1H), 3.94 (s, 3H), 2.90 (bs, 3H), 2.07-2.02 (m, 2H), 1.88-1.81 (m, 2H), 1.39-1.32 (m, 1H), 1.21-1.15 (m, 1H). FR-b: MS(ES): m/z 398.17 [M + H]$^+$, LCMS purity: 100%, HPLC purity: 99.36%, CHIRAL HPLC purity: 96.63%, $^1$H NMR (DMSO-d$_6$, 400 MHZ): 8.92 (s, 1H), 8.23-8.21 (d, J = 7.2 Hz, 1H), 8.14 (s, 1H), 7.92-7.91(d, J = 4 Hz, 2H), 7.66-7.64 (d, J = 8 Hz, 1H), 6.98-6.95 (m, 1H), 5.89 (s, 1H), 4.57-4.56 (d, J = 3.2 Hz ,1H), 4.42-4.36 (m, 1H), 4.15 (bs, 1H), 3.95 (s, 3H), 3.18-3.17 (d, J = 4.4 Hz, 1H), 2.92-2.90 (bs, 3H), 2.69-2.67 (d, J = 6.8 Hz, 1H), 2.09-2.01 (m, 2H), 1.40-1.33 (m, 1H), 1.21-1.15 (m, 1H). |
| I-462 | 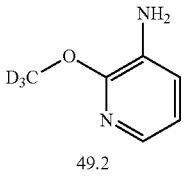 [SMILES: [2H]C([2H])([2H])Oc1ncccc1N] 49.2 | MS (ES): m/z 401.22 [M + H]$^+$, LCMS purity: 100%, HPLC purity: 99.66%, CHIRAL HPLC: (50.04%, 49.95%) $^1$H NMR (DMSO-d$_6$, 400 MHZ): 9.92 (s, 1H), 8.23-8.21 (d, J = 6.4 Hz, 1H), 8.14 (s, 1H), 7.92-7.91 (d, J = 3.2 Hz, 2H), 7.66-7.64 (d, J = 8 Hz, 1H), 6.98-6.95 (m, 1H), 5.89 (d, 1H), 4.57-4.56 (d, J = 4 Hz, 1H), 4.42-4.36 (m, 1H), 4.05 (s, 1H), 2.92-2.90 (m, 3H), 2.74 (s, 1H), 2.10-2.03 (m, 1H), 1.89-1.81 (m, 2H), 1.40-1.34 (m, 2H). |
| I-500 I-501 | 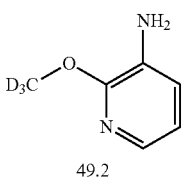 [SMILES: [2H]C([2H])([2H])Oc1ncccc1N] 49.2 | I-462 was separated into isomers: CHIRAL PAK AD-H (250 × 4.6 mm, 5u) and 0.1% DEA in methanol at 4 mL/min. FR-a: MS(ES): m/z 401.22 [M + H]$^+$, LCMS purity: 100%, HPLC purity: 100%, CHIRAL HPLC purity: 100%, $^1$H NMR (DMSO-d$_6$, 400 MHZ): 8.89 (s, 1H), 8.22-8.20 (m, 1H), 8.13 (s, 1H), 7.92-7.87 (m, 2H), 7.65-7.63 (d, J = 9.6 Hz, 1H), 6.97-6.94 (m, 1H), 5.88 (s, 1H), 4.55-4.54 (d, J = 3.6 Hz, 1H), 4.42-4.36 (m, 1H), 4.15 (bs, 1H), 2.91-2.90 (d, J = 4.4 Hz, 3H), 2.07-2.02 (m, 1H), 1.88-1.84 (m, 2H), 1.46-1.44 (m, 1H), 1.39-1.32 (m, 1H), 1.23-1.14 (m, 1H). FR-b: MS(ES): m/z 401.27 [M + H]$^+$, LCMS purity: 100%, HPLC purity: 99.64%, CHIRAL HPLC purity: 96.13%, $^1$H NMR (DMSO-d$_6$, |

TABLE 25-continued

| Compound # | Reagent | Chiral Separation Conditions and Characterization Data |
|---|---|---|
| | | 400 MHZ): 8.90 (s, 1H), 8.23-8.21 (d, J = 6.8 Hz, 1H), 8.14 (s, 1H), 7.93-7.88(m, 2H), 7.66-7.64 (d, J = 7.6 Hz, 1H), 6.98-6.95 (m, 1H), 5.89 (s, 1H), 4.55 (bs, 1H), 4.42-4.37 (m, 1H), 4.16 (bs, 1H), 2.92-2.91 (d, J = 4.8 Hz, 3H), 2.10-2.07 (m, 1H), 1.89-1.81 (m, 2H), 1.40-1.33 (m, 1H), 1.19-1.16 (m, 2H). |

Example 95: Synthesis of Compounds where $R^3$ is N-(trans)-(3-hydroxycyclohexyl)carboxamide, $R^6$ is Hydrogen, and $R^7$ is Methylamine Synthesis of N-(3-hydroxycyclohexyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-704)

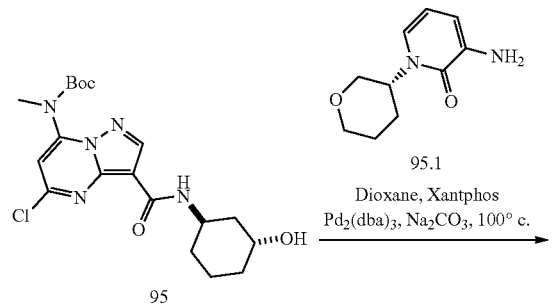

Synthesis of Compound 95.
Compound was synthesized using general procedure A to obtain 95. (Yield: 46.25%). MS (ES): m/z 424.17 [M+H]⁺.

Synthesis of Compound 95.1.
Compound was synthesized as per I-696 to obtain 95.1. MS (ES): m/z 195.11 [M+H]⁺.

Synthesis of Compound 95.2.
Compound was synthesized using general procedure B to obtain 95.2. (0.130, 63.16%), MS (ES): 582.3 [M+H]⁺.

Synthesis of Compound I-704.
Compound was synthesized using general procedure C to obtain I-704 (0.110 g, 97.56%), MS (ES): m/z 482.31 [M+H]⁺, LCMS purity: 100%, HPLC purity: 96.83%, CHIRAL HPLC: 52.32%, 47.67%, ¹H NMR (DMSO-d₆, 400 MHZ): 8.90 (s, 1H), 8.21 (s, 1H), 8.19 (s, 1H), 7.92-7.91 (d, J=4.8 Hz, 1H), 7.54-7.52 (d, J=8 Hz, 2H), 6.31-6.27 (t, J=7.2 Hz, 1H), 6.24 (s, 1H), 4.88 (bs, 1H), 4.55-4.54 (d, J=2.8 Hz, 1H), 4.24-4.21 (m, 1H), 3.99 (bs, 1H), 3.85 (bs, 2H), 3.60-3.55 (t, J=9.6 Hz, 1H), 3.49-6.44 (t, J=8 Hz, 1H), 2.91-2.90 (d, J=4.4 Hz, 3H), 1.88 (bs, 2H), 1.77-1.71 (m, 4H), 1.40-1.37 (d, J=12.4 Hz, 4H), 1.24-1.19 (m, 2H).

Characterization data for further compounds prepared by the above methods are presented in Table 26 below. Compounds in Table 26 were prepared by methods substantially similar to those described to prepare I-702, where I-696 was replaced with the reagent as indicated in Table 26.

TABLE 26

| Compound # | Reagent | Chiral Separation Conditions and Characterization Data |
|---|---|---|
| I-704 | ![structure] | MS (ES): m/z 482.31 [M + H]⁺, LCMS purity: 100%, HPLC purity: 96.83%, CHIRAL HPLC: 52.32%, 47.67%, ¹H NMR (DMSO-d₆, 400 MHZ): 8.90 (s, 1H), 8.21 (s, 1H), 8.19 (s, 1H), 7.92-7.91 (d, J = 4.8 Hz, 1H), 7.54-7.52 (d, J = 8 Hz, 2H), 6.31-6.27 (t, J = 7.2 Hz, 1H), 6.24 (s, 1H), 4.88 (bs, 1H), 4.55-4.54 (d, J = 2.8 Hz, 1H), 4.24-4.21 (m, 1H), 3.99 (bs, 1H), 3.85 (bs, 2H), 3.60-3.55 (t, J = 9.6 Hz, 1H), 3.49-6.44 (t, J = 8 Hz, 1H), 2.91-2.90 (d, |

TABLE 26-continued

| Compound # | Reagent | Chiral Separation Conditions and Characterization Data |
|---|---|---|
| | | J = 4.4 Hz, 3H), 1.88 (bs, 2H), 1.77-1.71 (m, 4H), 1.40-1.37 (d, J = 2.4 Hz, 4H), 1.24-1.19 (m, 2H). |
| I-780 I-781 | 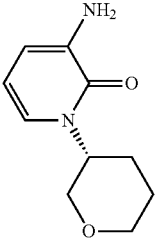 [SMILES: Nc1cccn([C@@H]2CCCOC2)c1=O] | I-704 was separated into isomers: CHIRAL PAK AD-H (250 × 4.6 mm, 5u) and 0.1% DEA in methanol. FR-a: MS(ES): m/z 482.62 [M + H]+, LCMS purity: 97.97%, HPLC purity: 98.34%, CHIRAL HPLC purity: 100%, $^1$H NMR (DMSO-$d_6$, 400 MHZ): 8.90 (s, 1H), 8.21 (s, 1H), 8.19 (s, 1H), 7.92-7.91 (d, J = 4.8 Hz, 1H), 7.54-7.52 (d, J = 8 Hz, 2H), 6.31-6.27 (t, J = 7.2 Hz, 1H), 6.24 (s, 1H), 4.91-4.86 (m, 1H), 4.55 (bs, 1H), 4.23-4.21 (m, 1H), 3.99 (bs, 1H), 3.86-3.82 (t, J = 7.6 Hz, 2H), 3.60-3.55 (t, J = 10.4 Hz, 1H), 3.49-3.44 (t, J = 8.4 Hz, 1H), 2.91-2.90 (d, J = 4.8 Hz, 3H), 1.88 (bs, 3H), 1.77-1.72 (m, 4H), 1.48-1.40 (m, 3H), 1.24-1.19 (m, 2H). FR-b: MS(ES): m/z 482.62 [M + H]+, LCMS purity: 99.37%, HPLC purity: 96.94%, CHIRAL HPLC purity: 100%, $^1$H NMR (DMSO-$d_6$, 400 MHZ): 8.90 (s, 1H), 8.21 (s, 1H), 8.19 (s, 1H), 7.92-7.91 (d, J = 4.4 Hz, 1H), 7.54-7.53 (d, J = 7.6 Hz, 2H), 6.31-6.27 (t, J = 7.2 Hz, 1H), 6.24 (s, 1H), 4.88 (bs, 1H), 4.55 (bs, 1H), 4.23 (bs, 1H), 3.99 (bs, 1H), 3.85 (bs, 2H), 3.60-3.55 (t, J = 10 Hz, 1H), 3.49-3.44 (t, J = 10.4 Hz, 1H), 2.91-2.90 (d, J = 4 Hz, 3H), 1.88 (bs, 3H), 1.77-1.72 (m, 4H), 1.49-1.40 (m, 3H), 1.12-1.08 (t, J = 6.8 Hz, 2H). |
| I-703 | 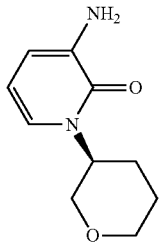 [SMILES: Nc1cccn([C@H]2CCCOC2)c1=O] | MS (ES): m/z 482.52 [M + H]+, LCMS purity: 100%, HPLC purity: 98.44%, CHIRAL HPLC: 48.94%, 49.35%, $^1$H NMR (DMSO-$d_6$, 400 MHZ): 8.91 (s, 1H), 8.21 (s, 1H), 8.19 (s, 1H), 7.93-7.92 (d, J = 4.8 Hz, 1H), 7.55-7.53 (d, J = 8 Hz, 2H), 6.31-6.27 (t, J = 6.8 Hz, 1H), 6.24 (s, 1H), 5.78 (s, 1H), 4.91-4.86 (m, 1H), 4.56 (bs, 1H), 4.23-4.21 (m, 1H), 3.98 (bs, 1H), 3.86-3.82 (t, J = 5.2 Hz, 2H), 3.60-3.55 (t, J = 9.6 Hz, 1H), 3.18 (s, 1H), 2.91-2.90 (d, J = 6.8 Hz, 3H), 2.69 (bs, 1H), 2.10-2.03 (m, 1H), 1.77-1.72 (m, 3H), 1.49-1.48 (d, J = 4.4 Hz, 3H), 1.24-1.19 (m, 2H), 1.09 (s, 1H). |
| I-734 I-735 | 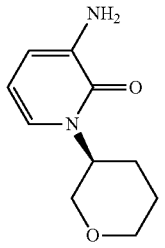 [SMILES: Nc1cccn([C@H]2CCCOC2)c1=O] | I-703 was separated into isomers: CHIRAL PAK AD-H 250 × 4.6 mm, 5u) 0.1% DEA in methanol. FR-a: MS(ES): m/z 482.31 [M + H]+, LCMS purity: 100%, HPLC purity: 99.66%, CHIRAL HPLC purity: 100%, $^1$H NMR (DMSO-$d_6$, 400 MHZ): 8.89 (s, 1H), 8.21 (s, 1H), 8.19 (s, 1H), 7.92-7.91 (d, J = 4.8 Hz, 1H), 7.54-7.52 (d, J = 7.6 Hz, 2H), 6.31-6.27 (t, J = 7.2 Hz,1H), 6.24 (s, 1H), 5.77 (s, 1H), 4.91-4.86 (m, 1H), 4.55 (bs, 1H), 4.24-4.21 (m, 1H), 3.98 (bs, 1H), 3.86-3.82 (m, 2H), 3.61-3.56 (t, J = 10.4 Hz, 1H), 3.49-3.44 (t, J = 8.8 Hz, 1H), 2.91-2.90 (d, J = 4.4 Hz, 3H), 2.08 (bs, 1H), 1.77-1.72 (m, 4H), 1.49-1.40 (m, 4H), 1.24-1.19 (m, 2H). FR-b: MS(ES): m/z 482.56 [M + H]+, LCMS purity: 97.79%, HPLC purity: 96.00%, CHIRAL HPLC purity: 100%, $^1$H NMR (DMSO-$d_6$, 400 MHZ): 8.89 (s, 1H), 8.20 (s, 1H), 8.18 (s, 1H), 7.91- |

TABLE 26-continued

| Compound # | Reagent | Chiral Separation Conditions and Characterization Data |
|---|---|---|
| | | 7.90 (d, J = 4.8 Hz, 1H), 7.53-7.51 (d, J = 7.6 Hz, 2H), 6.30-6.26 (t, J = 7.2 Hz, 1H), 6.23 (s, 1H), 5.76 (s, 1H), 4.87 (bs, 1H), 4.54 (bs, 1H), 4.20 (bs, 1H), 3.97 (bs, 1H), 3.84 (bs, 2H), 3.59-3.54 (t, J = 9.2 Hz, 1H), 3.48-3.43 (t, J = 8.4 Hz, 1H), 2.90-2.89 (d, J = 4.4 Hz, 3H), 2.06 (bs, 1H), 1.76-1.71 (m, 4H), 1.48-1.38 (m, 4H), 1.23-1.18 (m, 2H). |
| I-459 | 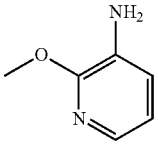 32.2 | MS (ES): m/z 412.17 [M + H]$^+$, LCMS purity: 97.51%, HPLC purity: 95.08%, Chiral HPLC: 50.01% and 48.68%. $^1$H NMR (DMSO-d$_6$, 400 MHZ): 8.91 (s, 1H), 8.24-8.23 (d, J = 4.0 Hz, 1H), 8.14 (s, 1H), 7.92-7.91 (m, 2H), 7.59-7.57 (d, J = 8.0 Hz, 1H), 7.01-6.98 (m, 1H), 5.90 (s, 1H), 4.15-4.11 (m, 1H), 3.90 (bs, 4H), 2.92-2.90 (d, J = 8.0 Hz, 3H), 1.76-1.52 (m, 4H), 1.55-1.52 (m, 1H), 1.39-1.36 (m, 2H), 1.08-1.00 (m, 2H). |
| I-496<br>I-497 | 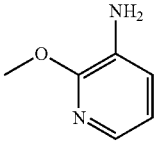 32.2 | I-459 was separated into isomers: CHIRAL PAK AD-H (250 × 4.6 mm, 5u) and 0.1% DEA in methanol at 4 mL/min.<br>FR-a: MS(ES): m/z 412.30 [M + H]$^+$, LCMS purity: 99.45%, HPLC purity: 99.04%, CHIRAL HPLC purity: 99.83%, $^1$H NMR (DMSO-d$_6$, 400 MHZ: 8.89 (s, 1H), 8.24-8.22 (d, J = 8.0 Hz, 1H), 8.14 (s, 1H), 7.92-7.90 (m, 2H), 7.58-7.55 (d, J = 12 Hz, 1H), 7.00-6.91 (m, 1H), 5.90 (s, 1H), 4.15-4.13 (m, 1H), 3.95(s, 1H), 3.90-3.88 (m, 4H), 2.91-2.90 (d, J = 4.0 Hz, 3H), 1.76-1.52 (m, 4H), 1.38-1.00 (m, 4H).<br>FR-b: MS(ES): m/z 412.22 [M + H]$^+$, LCMS purity: 98.58%, HPLC purity: 97.29%, CHIRAL HPLC purity: 99.37%, $^1$H NMR (DMSO-d$_6$, 400 MHZ): 8.89 (s, 1H), 8.23-8.22 (d, J = 4.0 Hz, 1H), 8.14 (s, 1H), 7.92-7.91 (m, 2H), 7.58-7.55 (d, J = 12 Hz, 1H), 7.00-6.97 (m, 1H), 5.90 (s, 1H) 4.47 (s, 1H), 4.15-4.13 (m, 1H), 4.00-3.90 (m, 4H), 2.91-2.90 (d, J = 8.0 Hz, 3H), 1.75-1.51 (m, 4H), 1.38-1.23 (m, 4H). |
| I-460 | 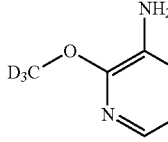 49.2 | MS (ES): m/z 415.33 [M + H]$^+$, LCMS purity: 98.87%, HPLC purity: 98.20%, CHIRAL HPLC: 49.57% + 48.61%, $^1$H NMR (DMSO-d$_6$, 400 MHZ): 8.89 (s, 1H), 8.23-8.21 (d, J = 7.6 Hz, 1H), 8.14-8.13 (m, 1H), 7.91-7.90 (m, 2H), 7.58-7.56 (m, 1H), 7.00-6.97 (m, 1H), 5.90 (s, 1H), 4.48 (s ,1H), 4.15 (s, 1H), 3.90 (s, 1H), 2.90 (s, 3H), 1.75 (s, 2H), 1.66-1.63 (m, 2H), 1.38-1.36 (m, 2H), 1.28-1.22 (m, 1H), 1.05-1.02(m, 1H). |
| I-500<br>I-501 | 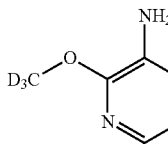 49.2 | I-460 was separated into isomers: CHIRALPAK AD-H (250 mm * 4.6 mm, 5u) in 0.1% DEA in 25% MEOH at 3 mL/min.<br>FR-a: MS (ES): m/z 414.48 [M + H]$^+$, LCMS purity: 99.52%, HPLC purity: 98.48%, CHIRAL HPLC: 100% $^1$H NMR (DMSO-d$_6$, 400 MHZ): 8.88 (s, 1H), 8.23-8.21 (dd, J = 6.4 Hz, 7.6 Hz, 1H), 8.13 (s, 1H), 7.97-7.87 (m, 2H), 7.57-7.55 (m, 1H), 7.00-6.97 (m, 1H), 5.90 (s, 1H), 4.47-4.46 (m, 1H), 4.15-4.13 (m, 1H), 3.90 (s, 1H), 2.91-2.90 (d, J = 4.8, 3H), 1.75-1.66 (m, 2H), 1.63-1.60 |

TABLE 26-continued

| Compound # | Reagent | Chiral Separation Conditions and Characterization Data |
|---|---|---|
| | | (m, 1H), 1.54-1.52 (m, 1H), 1.38-1.36 (m, 2H), 1.28-1.23 (m, 1H), 1.09-1.00 (m, 1H).<br>FR-b: MS (ES): m/z 414.48 [M + H]⁺, LCMS purity: 100%, HPLC purity: 99.01%, CHIRAL HPLC : 99.52% ¹H NMR (DMSO-d₆, 400 MHZ): 8.88 (s, 1H), 8.23-8.21 (dd, J = 6.0 Hz ,7.6 Hz, 1H), 8.13 (s, 1H), 7.92-7.88 (m, 2H), 7.57-7.55 (d, J = 8.4, 1H), 7.00-6.97 (m, 1H), 5.90 (s, 1H), 4.47-4.46(m ,1H), 4.14-4.10 (m, 1H), 3.90 (s, 1H), 2.91-2.90 (d, J = 4.8, 3H), 1.75-1.66 (m, 2H), 1.67-1.63 (m, 1H), 1.54-1.52 (m, 1H), 1.38-1.36 (m, 2H), 1.28-1.23 (m, 1H), 1.08-1.00 (m, 1H). |
| I-919 | 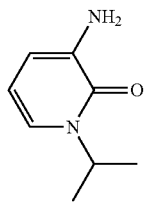 | MS (ES): m/z 440.23 [M + H]⁺, LCMS purity: 95.01%, HPLC purity: 98.24%, CHIRAL HPLC purity: 46.35%, 50.58%,¹H NMR (DMSO-d₆, 400 MHZ): 8.96 (bs, 1H), 8.21 (s, 1H), 8.15-8.14 (d, J = 6.8 Hz, 1H), 7.99 (bs, 1H), 7.59-7.57 (d, J = 7.6 Hz 1H), 7.47-7.46 (d, J = 6.8 1H), 6.31-6.27 (t, J = 14.4 Hz, 1H), 6.19 (s, 1H), 5.20-5.13 (m, 1H), 4.22 (s, 1H), 3.98 (s, 1H), 2.91-2.90 (d, J = 3.2 Hz, 3H), 1.89-1.86 (d, J = 11.2 Hz, 2H) ,1.59-1.56 (m, 2H), 1.45 (m, 3H), 1.40-1.35 (d, J = 18 Hz, 6H), 1.22-1.15 (m, 2H). |
| I-1078<br>I-1079 | 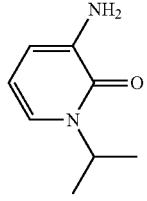 | I-919 was separated into isomers:<br>CHIRAL PAK AD-H (250 × 4.6 mm, 5u) 0.1% DEA_MEOH (70-30).<br>FR-a: MS(ES): m/z 440.37 [M + H]⁺, LCMS purity: 96.64%, HPLC purity: 97.41%, CHIRAL HPLC purity: 100%, ¹H NMR (DMSO-d₆, 400 MHZ): 8.88 (s, 1H), 8.19-8.18 (m, 2H), 7.91-7.90 (d, J = 4.8 Hz, 1H), 7.56-7.54 (d, J = 8.4 Hz, 1H), 7.47-7.45 (d, J = 6.8 Hz, 1H), 6.31-6.28 (t, J = 7.2 Hz, 1H), 6.24 (s, 1H), 5.21-5.15 (m, 1H), 4.57-4.56 (d, J = 3.2 Hz, 1H), 4.24-4.22 (m, 1H), 3.99 (s, 1H), 2.92-2.91 (d, J = 4.8 Hz, 3H), 1.92-1.88 (m, 2H), 1.75-1.69 (m, 1H), 1.60-1.57 (m, 1H), 1.50-1.46 (m, 2H), 1.37-1.35 (d, J = 4.2 Hz, 6H), 1.25-1.17 (m, 2H).<br>FR-b: MS(ES): m/z 440.37 [M + H]⁺, LCMS purity: 96.81%, HPLC purity: 98.24%, CHIRAL HPLC purity: 95.57%, ¹H NMR (DMSO-d₆, 400 MHZ): 8.88 (s, 1H), 8.19-8.18 (m, 2H), 7.91-7.90 (d, J = 4.8 Hz, 1H), 7.56-7.54 (d, J = 8.4 Hz, 1H), 7.47-7.45 (d, J = 6.8 Hz, 1H), 6.31-6.28 (t, J = 7.2 Hz, 1H), 6.24 (s, 1H), 5.21-5.15 (m, 1H), 4.57-4.56 (d, J = 3.2 Hz, 1H), 4.24-4.22 (m, 1H), 3.99 (s, 1H), 2.92-2.91 (d, J = 4.8 Hz, 3H), 1.92-1.88 (m, 2H), 1.75-1.69 (m, 1H), 1.60-1.57 (m, 1H), 1.50-1.46 (m, 2H), 1.37-1.35 (d, J = 4.2 Hz, 6H), 1.25-1.17 (m, 2H). |

1165

Synthesis of N-(3-hydroxycyclohexyl)-7-(methylamino)-5-(1-(tetrahydro-2H-pyran-4-yl)-1H-pyrrolo[2,3-b]pyridin-3-yl)pyrazolo[1,5-a]pyrimidine-3-carboxamide (I-1359)

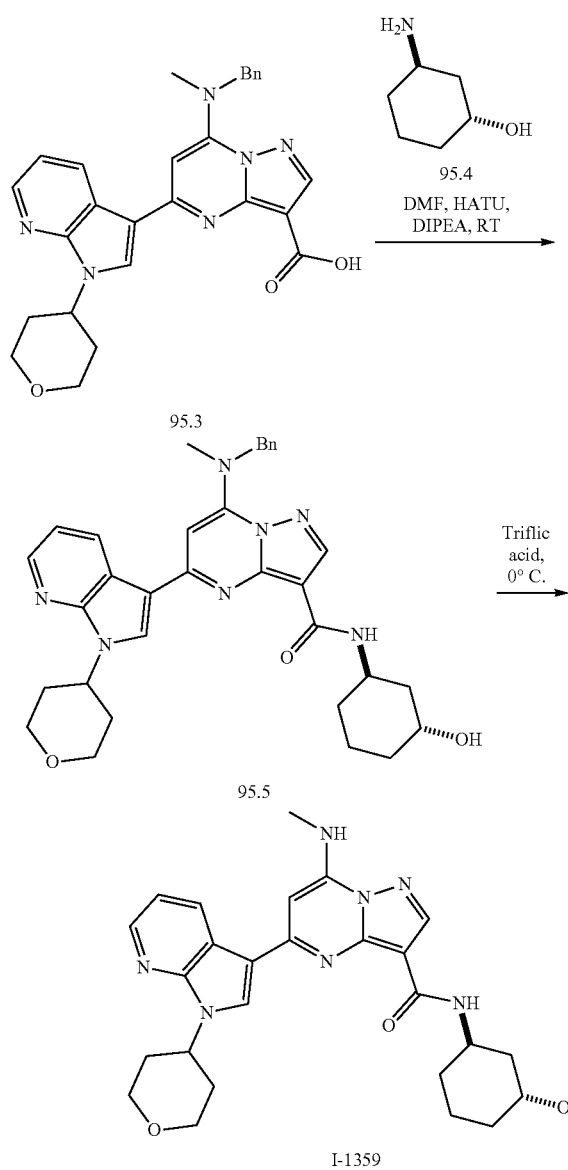

Synthesis of Compound 95.3.

Compound was synthesized as per I-1048 using 95.4 to obtain 95.3. (Yield: 98.76%). MS(ES): m/z 493.54 [M+H]$^+$.

Synthesis of Compound 95.5.

Compound was synthesized using general procedure A to obtain 95.5. (0.15 g, 62.64%), MS (ES): 590.70 [M+H]$^+$.

Synthesis of Compound I-1359.

Solution of 95.5 (0.040 g, 0.067 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane.

1166

Organic layer was combined, dried over sodium sulphate and concentrated under reduced pressure to obtain crude material. This was further purified by trituration with diethyl ether to a obtain 95.5 (0.025 g, 75.28%), MS (ES): m/z 490.18 [M+H]$^+$, LCMS purity: 100%, HPLC purity: 98.65%, CHIRAL HPLC: 50.40%, 47.94%, 1H NMR (DMSO-d$_6$, 400 MHz): 8.84 (s, 1H), 8.74-8.72 (d, J=6.8 Hz, 1H), 8.41-8.40 (d, J=3.2 Hz, 1H), 8.35 (s, 1H), 8.25-8.24 (d, J=4.8 Hz, 1H), 8.04-8.01 (d, J=8.4 Hz, 1H), 7.29-7.26 (m, 1H) 6.79 (s, 1H), 5.12-5.06 (t, J=11.6 Hz, 1H), 4.58 (s, 1H), 4.31 (s, 1H), 4.08-4.01 (m, 3H), 3.65-3.59 (t, J=11.6 Hz, 2H), 3.11-3.10 (d, J=4.4 Hz, 3H), 2.21-2.18 (m, 3H), 2.01-1.92 (m, 4H), 1.77-1.74 (m, 2H), 1.39-1.22 (m, 3H).

Example 96: Synthesis of Compounds where R$^3$ is N-(cyclopropyl)carboxamide, R$^6$ is Hydrogen, and R$^7$ is Methylamine Synthesis of 5-((1-(1-(2-cyanoethyl)piperidin-3-yl)-2-oxo-1,2-dihydropyridin-3-yl)amino)-N-cyclopropyl-7-(methylamino)pyrazolo[1,5-a]pyrimidine-3-carboxamide (I-1009)

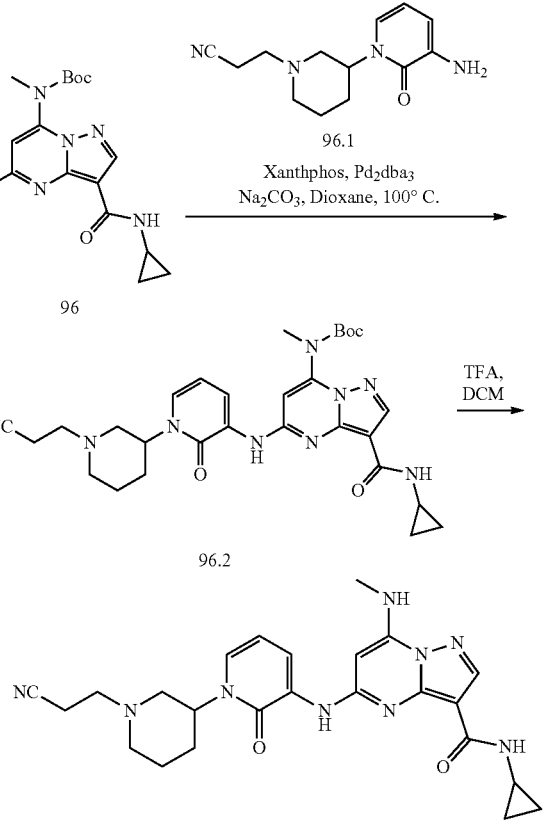

Synthesis of Compound 96.

Compound was synthesized as per Example 27 (I-127) to obtain 96. (Yield: 57.16%), MS (ES): m/z 366.82 [M+H]$^+$.

Synthesis of Compound 96.1.

Compound was synthesized as per Example 108 (1-912) to obtain 96.1. (Yield: 42.59%), MS (ES): m/z 247.15 [M+H]+.

Synthesis of Compound 96.2.

Compound was synthesized using general procedure B to obtain 96.2. (0.092 g, 48.72%), MS (ES): 576.30 [M+H]+.

Synthesis of Compound I-1009.

Compound was synthesized using general procedure C to obtain I-1009 (0.078 g, 98.68%), MS (ES): 476.32 [M+H]+ LCMS purity: 100%, HPLC purity: 95.34%, CHIRAL HPLC: 46.67%, 51.35%, $^1$H NMR (DMSO-$d_6$, 400 MHZ): 8.37-8.36 (d, J=7.6 Hz, 1H), 8.28 (bs, 1H), 8.20 (s, 1H), 8.86-7.85 (d, J=3.6 Hz, 1H), 7.02-6.99 (m, 1H), 7.81 (s, 1H), 5.41 (bs, 1H), 3.06 (s, 3H), 2.88-2.86 (m, 3H), 2.76-2.72 (m, 1H), 2.57 (bs, 1H), 1.97-1.85 (m, 4H), 1.69 (bs, 1H), 1.42 (s, 1H), 1.31 (s, 2H), 1.29 (s, 1H), 0.94-0.91 (m, 1H), 0.87-0.82 (m, 2H), 0.52 (bs, 2H).

Synthesis of (S)-5-((1-(1-(2-cyanoethyl)piperidin-3-yl)-2-oxo-1,2-dihydropyridin-3-yl)amino)-N-cyclopropyl-7-(methylamino)pyrazolo[1,5-a]pyrimidine-3-carboxamide (I-1347) and (R)-5-((1-(1-(2-cyanoethyl)piperidin-3-yl)-2-oxo-1,2-dihydropyridin-3-yl)amino)-N-cyclopropyl-7-(methylamino)pyrazolo[1,5-a]pyrimidine-3-carboxamide (I-1346)

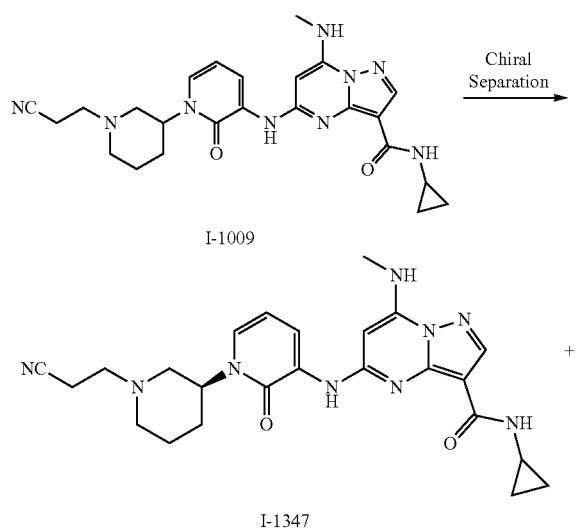

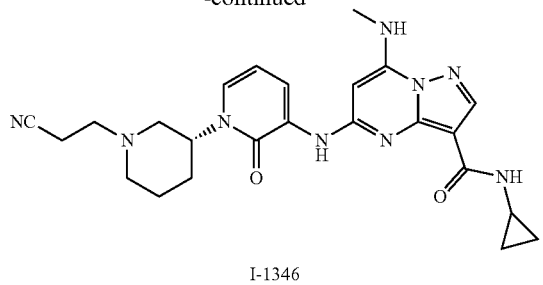

Synthesis of Compound I-1347 & 11346.

Isomers of I-1009 (0.078 g) were separated out using column (CHIRAL PAK OX-H_250×4.6 mm, 5 u) and DEA_HEX_IPA-MEOH (50-50) as co-solvent with flow rate of 4 mL/min. to get pure fraction-1 (FR-a) and fraction-2 (FR-b). FR-a was concentrated under reduced pressure at 30° C. to afford 0.028 g. MS(ES): m/z 476.41 [M+H]+, LCMS purity: 98.91%, HPLC purity: 95.11%, CHIRAL HPLC purity: 96.31%, $^1$H NMR (DMSO-$d_6$, 400 MHZ): 8.91 (s, 1H), 8.19 (s, 1H), 8.13-8.11 (d, J=7.2 Hz, 1H), 7.93-7.92 (d, J=4.8 Hz, 1H), 7.83-7.82 (d, J=4 Hz, 1H), 7.60 (bs, 1H), 6.32 (bs, 1H), 6.20 (s, 1H), 4.95 (bs, 1H), 2.90-2.89 (d, J=4.8 Hz, 4H), 2.86-2.82 (m, 2H), 2.73-2.67 (m, 3H), 2.18 (bs, 1H), 1.82 (bs, 3H), 1.65 (bs, 1H), 1.24 (s, 2H), 0.80-0.76 (m, 2H), 0.49 (bs, 2H).

FR-b was concentrated under reduced pressure at 30° C. to afford 0.030 g. MS(ES): m/z 476.46 [M+H]+, LCMS purity: 94.44%, HPLC purity: 95.07%, CHIRAL HPLC purity: 95.74%, $^1$H NMR (DMSO-$d_6$, 400 MHZ): 8.92 (s, 1H), 8.19 (s, 1H), 8.14-8.12 (d, J=7.2 Hz, 1H), 7.93-7.92 (d, J=4.8 Hz, 1H), 7.82-7.81 (d, J=4 Hz, 1H), 7.56 (bs, 1H), 7.39 (bs, 1H), 6.33 (s, 1H), 6.21 (bs, 1H), 2.90-2.89 (d, J=4.8 Hz, 4H), 2.86-2.84 (m, 3H), 1.85 (bs, 4H), 1.33-1.32 (m, 1H), 1.23 (bs, 3H), 0.85 (bs, 1H), 0.79-0.77 (d, J=5.6 Hz, 2H), 0.49 (bs, 2H).

Characterization data for further compounds prepared by the above methods are presented in Table 27 below. Compounds in Table 27 were prepared by methods substantially similar to those described to prepare I-1009, where compound 96.1 was replaced with the reagent as indicated in Table 27.

TABLE 27

| Compound # | Reagent | Chiral Separation Conditions and Characterization Data |
|---|---|---|
| I-957 | 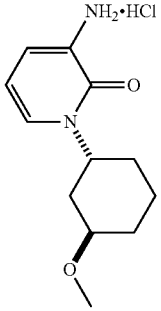 | MS (ES): 452.52 [M + H]+ LCMS purity: 100%, HPLC purity: 99.36%, CHIRAL HPLC: 50.02%, 49.97%, $^1$H (DMSO-$d_6$, 400 MHZ): 8.88 (s, 1H), 8.18 (s, 1H), 8.10-8.08 (d, J = 6.4 Hz, 1H), 7.91-7.90 (d, J = 4.8 Hz, 1H), 7.83-7.82 (d, J = 3.6 Hz, 1H), 8.47-8.45 (d, J = 6 Hz, 1H), 6.33-6.30 (t, J = 7.2 Hz, 1H), 6.19 (s, 1H), 5.11 (bs, 1H), 3.70 (bs, 1H), 3.28 (s, 3H), 2.90-2.89 (d, J = 4.8 Hz, 3H), 2.86-2.82 (m, 1H), 1.37 (bs, 3H), 1.23 (bs, 4H), 0.87-0.84 (t, J = 6.8 Hz, 1H), 0.80-0.76 (m, 2H), 0.47 (bs, 2H). |

TABLE 27-continued

| Compound # | Reagent | Chiral Separation Conditions and Characterization Data |
|---|---|---|
| I-1025<br>I-1026 | 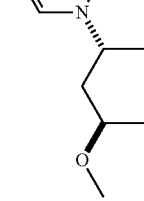 | Intermediate corresponding to 96.2 en route to I-957 was separated into isomers before BOC removal: CHIRAL PAK AD-H (250 × 4.6 mm, 5u) and DEA_HEX_IPA-MEOH (50-50) at 4 mL/min.<br>FR-a: MS (ES): m/z 452.37 [M + H]$^+$, LCMS purity: 100%, HPLC purity: 99.71%, Chiral HPLC: 100%, $^1$H NMR (DMSO-$d_6$, 400 MHZ): 8.89 (s, 1H), 8.20 (s, 1H), 8.12-8.10 (d, J = 6.8 Hz, 1H), 7.92-7.91 (d, J = 4.8 Hz, 1H), 7.84-7.83 (d, J = 3.6 Hz, 1H), 8.48-8.46 (d, J = 6.0 Hz, 1H), 6.35-6.31 (t, J = 7.2 Hz, 1H), 6.20 (s, 1H), 5.12 (bs, 1H), 3.72 (bs, 1H), 3.29 (s, 3H), 2.92-2.84 (m, 4H), 1.37 (bs, 3H), 1.23 (bs, 4H), 0.87-0.84 (t, J = 6.8 Hz, 1H), 0.82-0.77 (m, 2H), 0.52-0.49 (m, 2H).<br>FR-b: MS (ES): m/z 452.37 [M + H]$^+$, LCMS purity: 100%, HPLC purity: 100%, Chiral HPLC: 100%, $^1$H NMR (DMSO-$d_6$, 400 MHZ): 8.89 (s, 1H), 8.20 (s, 1H), 8.12-8.10 (d, J = 6.8 Hz, 1H), 7.92-7.91 (d, J = 4.8 Hz, 1H), 7.84-7.83 (d, J = 3.6 Hz, 1H), 8.48-8.46 (d, J = 6.0 Hz, 1H), 6.35-6.31 (t, J = 7.2 Hz, 1H), 6.20 (s, 1H), 5.12 (bs, 1H), 3.72 (bs, 1H), 3.29 (s, 3H), 2.92-2.84 (m, 4H), 1.37 (bs, 3H), 1.23 (bs, 4H), 0.87-0.84 (t, J = 6.8 Hz, 1H), 0.82-0.77 (m, 2H), 0.52-0.49 (m, 2H). |
| I-956 | 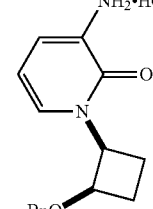<br>96a | Benzyl group was removed using Pd/C, ammonium formate, MeOH, reflux to afford I-956: MS(ES): m/z 410.25 [M + H]$^+$ LCMS purity: 94.87%, HPLC purity: 95.01%, CHIRAL HPLC: 48.63%, 49.13%, $^1$H NMR (DMSO-$d_6$, 400 MHZ): 8.86 (s, 1H), 8.19 (s, 1H), 8.13-8.11 (d, J = 6 Hz, 1H), 7.90-7.86 (m, 2H), 7.49-7.47 (d, J = 6.8 Hz, 1H), 6.33-6.29 (t, J = 7.2 Hz, 1H), 6.19 (s, 1H), 5.21-5.17 (m, 2H), 4.53 (bs, 1H), 2.91-2.89 (d, J = 4.8 Hz, 3H), 2.87-2.85 (m, 1H), 2.30-2.27 (m, 1H), 1.75 (bs, 1H), 1.24 (bs, 2H), 0.82-0.78 (m, 2H), 0.53-0.51 (m, 2H). |
| I-1103<br>I-1104 | 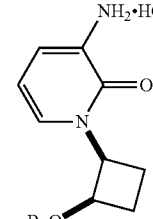<br>96a | I-956 was separated into isomers: CHIRAL PAK AD-H (250 × 4.6 mm, 5u) 0.1% DEA_MEOH (70-30).<br>FR-a: MS(ES): m/z 410.40 [M + H]$^+$, LCMS purity: 97.91%, HPLC purity: 95.67%, CHIRAL HPLC purity: 99.03%, $^1$H NMR (DMSO-$d_6$, 400 MHZ): 8.87 (s, 1H), 8.19 (s, 1H), 8.14-8.12 (d, J = 7.2 Hz, 1H), 7.91-7.86 (m, 2H), 7.49-7.47 (d, J = 7.2 Hz, 1H), 6.33-6.29 (t, J = 6.8 Hz, 1H), 6.20 (s, 1H), 5.20-5.16 (m, 2H), 4.53 (s, 1H), 2.91-2.85 (m, 4H), 2.75-2.70 (m, 1H), 2.30-2.17 (m, 2H), 1.75-1.71 (m, 1H), 0.83-0.74 (m, 2H), 0.54-0.50 (m, 2H).<br>FR-b: MS(ES): m/z 410.42 [M + H]$^+$, LCMS purity: 100%, HPLC purity: 97.18%, CHIRAL HPLC purity: 99.15%, $^1$H NMR (DMSO-$d_6$, 400 MHZ): 8.86 (s, 1H), 8.19 (s, 1H), 8.13-8.12 (d, J = 6.0 Hz, 1H), 7.90-7.86 (m, 2H), 7.49-7.47 (d, J = 6.0 Hz, 1H), 6.33-6.29 (t, J = 7.2 Hz, 1H), 6.20 (s, 1H), 5.20-5.16 (m, 2H), 4.53 (s, 1H), 2.91-2.85 (m, 4H), 2.75-2.70 (m, 1H), 2.30-2.17 (m, 2H), 1.76-1.70 (m, 1H), 0.87-0.78 (m, 2H), 0.54-0.50 (m, 2H). |

TABLE 27-continued

| Compound # | Reagent | Chiral Separation Conditions and Characterization Data |
|---|---|---|
| I-936 | 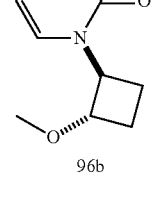 96b | MS (ES): m/z 424.47 [M + H]+, LCMS purity: 100%, HPLC purity: 98.83%, CHIRAL HPLC purity: 49.65%, 49.69%, $^1$H NMR (DMSO-$d_6$, 400 MHZ): 8.92 (s, 1H), 8.19 (s, 1H), 8.13-8.12 (d, J = 6 Hz, 1H), 7.92-7.90 (d, J = 4.8 Hz, 1H), 7.82-7.81 (d, J = 3.6 Hz, 1H), 7.58-7.57 (d, J = 6 Hz, 1H), 6.37-6.34 (t, J = 7.2 Hz, 1H), 6.20 (s, 1H), 5.19-5.13 (m, 1H), 4.26-4.20 (m, 1H), 3.16 (s, 3H), 2.89-2.88 (d, J = 4.8 Hz, 3H), 2.86-2.83 (m, 1H), 2.20-2.13 (m, 2H), 1.99 (s, 1H), 1.34 (bs, 1H), 0.85-0.76 (m, 2H), 0.51-0.48 (m, 2H). |
| I-1019 I-1020 | 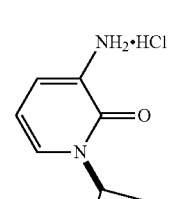 96b | I-936 was separated into isomers: CHIRAL PAK AD-H (250 × 4.6 mm, 5u) 0.1% DEA_HEX_IPA-MEOH (50-50). FR-a: MS(ES): m/z 424.52 [M + H]+, LCMS purity: 100%, HPLC purity: 98.31%, CHIRAL HPLC purity: 100%, $^1$H NMR (DMSO-$d_6$, 400 MHZ): 8.94 (s, 1H), 8.20 (s, 1H), 8.13-8.15 (d, J = 8 Hz, 1H), 7.93-7.94 (d, J = 4 Hz, 1H), 7.83-7.84 (d, J = 4 Hz, 1H), 7.58-7.60 (d, J = 8 Hz, 1H), 6.35-6.37 (t, J = 8 Hz, 1H), 6.21 (s, 1H), 5.14-5.21 (m, 1H), 4.21-4.23 (d, J = 8 Hz, 1H), 3.17-3.18 (d, J = 4 Hz, 3H), 2.88-2.90(d, J = 8 Hz, 3H), 2.84-2.87 (m, 2H), 2.14-2.22 (m, 2H), 1.82-1.84 (t, J = 8 Hz, 1H), 1.64-1.66 (t, J = 8 Hz, 1H), 0.80-0.82 (m, 1H), 0.50-0.52 (m, 2H). FR-b: MS(ES): m/z 424.52 [M + H]+, LCMS purity: 100%, HPLC purity: 98.33%, CHIRAL HPLC purity: 99.71%, $^1$H NMR (DMSO-$d_6$, 400 MHZ): 8.94 (s, 1H), 8.20 (s, 1H), 8.13-8.15 (d, J = 8 Hz, 1H), 7.93-7.94 (d, J = 4 Hz, 1H), 7.83-7.84 (d, J = 4 Hz, 1H), 7.58-7.60 (d, J = 8 Hz, 1H), 6.35-6.37 (t, J = 8 Hz, 1H), 6.21 (s, 1H), 5.14-5.21 (m, 1H), 4.21-4.23 (d, J = 8 Hz, 1H), 3.17-3.18 (d, J = 4 Hz, 3H), 2.88-2.90(d, J = 8 Hz, 3H), 2.84-2.87 (m, 2H), 2.14-2.22 (m, 2H), 1.82-1.84 (t, J = 8 Hz, 1H), 1.64-1.66 (t, J = 8 Hz, 1H), 0.80-0.82 (m, 1H), 0.50-0.52 (m, 2H). |
| I-848 | 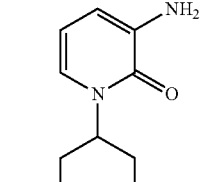 96c | MS (ES): 469.46 [M + H]+ LCMS purity: 100%, HPLC purity: 99.34%, CHIRAL HPLC: 56.31% 43.58%, $^1$H NMR (DMSO-$d_6$, 400 MHZ): 8.91 (s, 1H), 8.20(s, 1H), 8.14-8.12 (d, J = 7.2 Hz, 1H), 7.92-7.91 (d, J = 4.8 Hz, 1H), 7.84-7.83 (d, J = 4 Hz, 1H), 7.60-7.58 (d, J = 6.8 Hz, 1H), 6.34-6.30 (t, J = 7.2 Hz, 1H), 6.21 (s, 1H), 4.95 (bs, 1H), 4.63-4.61 (t, J = 4.8 Hz, 1H), 4.51-4.49 (t, J = 4.8 Hz, 1H), 2.91-2.90 (d, J = 4.8 Hz, 3H), 2.88-2.84 (m, 3H), 2.75-2.72 (t, J = 4.4 Hz, 1H), 2.68-2.65 (m, 1H), 2.38-2.34 (m, 1H), 2.22-2.16 (t, J = 10.4 Hz, 1H), 1.81 (bs, 1H), 1.77 (bs, 1H), 1.66 (bs, 1H), 1.24 (s, 1H), 0.82-0.77 (m, 2H), 0.52-0.50 (m, 2H). |

TABLE 27-continued

| Compound # | Reagent | Chiral Separation Conditions and Characterization Data |
|---|---|---|
| I-880<br>I-881 | 96c | I-848 was separated into isomers:<br>CHIRAL PAK AD-H (250 × 4.6 mm, 5u)<br>0.1% DEA_HEX_IPA-ACN (70-30).<br>FR-a: MS(ES): m/z 469.37 [M + H]$^+$,<br>LCMS purity: 100%, HPLC purity:<br>99.32%, CHIRAL HPLC purity: 100%,<br>$^1$H NMR (DMSO-d$_6$, 400 MHZ): 8.91<br>(s, 1H), 8.20 (s, 1H), 8.14-8.12 (d,<br>J = 6.0 Hz, 1H), 7.93-7.92 (d, J = 4.8 Hz,<br>1H), 7.84-7.83 (d, J = 3.6 Hz, 1H), 7.60-<br>7.58 (d, J = 6.8 Hz, 1H), 6.34-6.31 (t, J =<br>7.2 Hz, 1H), 6.21 (s, 1H), 4.95-4.93 (m,<br>1H), 4.64-4.61 (t, J = 4.8 Hz, 1H), 4.52-<br>4.49 (t, J = 4.8 Hz, 1H), 2.97-2.84 (m,<br>6H), 2.75-2.73 (t, J = 4.8 Hz, 1H), 2.68-<br>2.65 (t, J = 4.8 Hz, 1H), 2.38-2.34 (m,<br>1H), 2.22-2.17 (t, J = 6.4 Hz, 1H), 1.81-<br>1.78 (m, 3H), 1.66 (s, 1H), 0.82-1.77 (m,<br>2H), 0.52-0.48 (m, 2H).<br>FR-b: MS(ES): m/z 469.66 [M + H]$^+$,<br>LCMS purity: 100%, HPLC purity:<br>99.09%, CHIRAL HPLC purity:<br>99.80%, $^1$H NMR (DMSO-d$_6$,<br>400 MHZ): 8.91 (s, 1H), 8.20 (s, 1H),<br>8.14-8.12 (d, J = 6.4 Hz, 1H), 7.93-7.92<br>(d, J = 5.2 Hz, 1H), 7.84-7.83 (d,<br>J = 4.0 Hz, 1H), 7.60-7.59 (d, J = 6.8 Hz,<br>1H), 6.34-6.31 (t, J = 7.2 Hz, 1H), 6.21 (s,<br>1H), 4.95 (s, 1H), 4.64-4.61 (t, J = 4.8 Hz,<br>1H), 4.52-4.49 (t, J = 6.4 Hz, 1H), 2.96-<br>2.84 (m, 6H), 2.75-2.73 (t, J = 4.8 Hz,<br>1H), 2.68-2.65 (t, J = 4.8 Hz, 1H), 2.39-<br>2.34 (m, 1H), 2.22-2.17 (t, J = 6.8 Hz,<br>1H), 1.81-1.78 (m, 3H), 1.66 (s, 1H),<br>0.82-0.77 (m, 2H), 0.52-0.89 (m, 2H). |
| I-384 | 96d | MS (ES): m/z 452.37 [M + H]$^+$,<br>LCMS purity: 100%, HPLC purity:<br>98.40%, $^1$H NMR (DMSO-d$_6$,<br>400 MHZ): 9.21 (s, 1H), 8.36-8.33 (m,<br>1H), 8.26 (s, 1H), 8.04-8.02 (d, J = 5.2 Hz,<br>1H), 7.77-7.75 (m, 2H), 6.64 (s, 1H),<br>6.36 (s, 1H), 3.78 (s, 3H), 2.92-2.91 (d,<br>J = 4.8 Hz, 3H), 2.33 (s, 3H), 2.00 (s, 1H),<br>0.75-0.74 (d, J = 6.8 Hz, 2H), 0.57 (bs,<br>2H). |
| I-788 | 96e | MS (ES): m/z 398.37 [M + H]$^+$,<br>LCMS purity: 100%, HPLC purity:<br>100%, CHIRAL HPLC: 49.13%,<br>50.87%, $^1$H NMR (DMSO-d$_6$,<br>400 MHZ): 8.96 (s, 1H), 8.20 (s, 1H),<br>8.12-8.10 (d, J = 6.4 Hz, 1H), 7.94-7.942<br>(d, J = 4.4 Hz, 1H), 7.83-7.82 (d, J = 3.6 Hz,<br>1H), 7.21-7.19 (d, J = 6 Hz, 1H), 6.28-6.24<br>(t, J = 7.2 Hz, 1H), 6.20 (s, 1H), 5.09 (bs,<br>1H), 4.94 (bs, 1H), 3.90-3.82 (m, 1H),<br>2.91-2.90 (d, J = 4 Hz, 3H), 2.87-2.83 (m,<br>1H), 2.10 (s, 1H), 0.80-0.77 (m, 2H),<br>0.49 (bs, 2H). |
| I-866<br>I-867 | 96e | I-788 was separated into isomers:<br>CHIRAL PAK AD-H (250 × 4.6 mm, 5u)<br>0.1% DEA_HEX_IPA-ACN (70-30).<br>FR-a: MS(ES): m/z 398.32 [M + H]$^+$,<br>LCMS purity: 100%, HPLC purity:<br>99.74%, CHIRAL HPLC purity: 100%,<br>$^1$H NMR (DMSO-d$_6$, 400 MHZ): 8.96<br>(s, 1H), 8.20 (s, 1H), 8.12-8.10 (d,<br>J = 8.2 Hz, 1H), 7.94-7.93 (d, J = 4.8 Hz,<br>1H), 7.83-7.82 (d, J = 3.6 Hz, 1H), 7.21-<br>7.19 (d, J = 6.8 Hz, 1H), 6.28-6.25 (t,<br>J = 7.2 Hz, 1H), 6.21 (s, 1H), 5.09 (bs, |

TABLE 27-continued

| Compound # | Reagent | Chiral Separation Conditions and Characterization Data |
|---|---|---|
| | | 1H), 4.94 (bs, 1H), 3.89-3.85 (m, 1H), 2.91-2.90 (d, J = 4.8 Hz, 3H), 2.87-2.83 (m, 1H), 2.10 (s, 1H), 0.80-0.76 (m, 2H), 0.50-0.47 (m, 2H).<br>FR-b: MS(ES): m/z 398.52 [M + H]$^+$, LCMS purity: 100%, HPLC purity: 99.80%, CHIRAL HPLC purity: 98.45%, $^1$H NMR (DMSO-d$_6$, 400 MHZ): ): 8.96 (s, 1H), 8.20 (s, 1H), 8.12-8.11 (d, J = 7.2 Hz, 1H), 7.93-7.92 (d, J = 4.8 Hz, 1H), 7.83-7.82 (d, J = 4 Hz, 1H), 7.21-7.19 (d, J = 6 Hz, 1H), 6.28-6.25 (t, J = 7.2 Hz, 1H), 6.21 (s, 1H), 5.09 (bs, 1H), 4.94 (bs, 1H), 3.90-3.82 (m, 1H), 2.91-2.90 (d, J = 4.8 Hz, 3H), 2.87-2.83 (m, 1H), 2.10 (s, 1H), 0.80-0.76 (m, 2H), 0.50-0.47 (m, 2H). |
| I-760 | 96f | MS (ES): 438.37 [M + H]$^+$ LCMS purity: 98.20%, HPLC purity: 97.60%, CHIRAL HPLC: 47.98% 49.91%, $^1$H NMR (DMSO-d$_6$, 400 MHZ): 8.87 (s, 1H), 8.20 (s, 1H), 8.11-8.09 (d, J = 6.8 Hz, 1H), 7.92 (bs, 1H), 7.84-7.83(d, J = 3.6 Hz, 1H), 7.46-7.44 (d, J = 6.4 Hz, 1H), 6.33-6.29 (t, J = 6.8 Hz, 1H), 6.20 (s, 1H), 5.28 (bs, 1H), 4.70 (bs, 1H), 4.15 (bs, 1H), 2.91 (s, 3H), 2.87-2.86 (m, 1H), 2.09 (s, 1H), 1.94-1.87 (m, 3H), 1.62 (bs, 3H), 1.47-1.41(t, J = 12.8 Hz, 1H), 0.80-0.79 (d, J = 5.6 Hz, 2H), 0.50 (bs, 2H). |
| I-821<br>I-822 | 96f | I-760 was separated into isomers: CHIRAL PAK AD-H (250 × 4.6 mm, 5u) 0.1% DEA_HEX_IPA-ACN (70-30).<br>FR-a: MS(ES): m/z 438.44 [M + H]$^+$, LCMS purity: 100%, HPLC purity: 99.39%, CHIRAL HPLC purity: 99.87%, $^1$H NMR (DMSO-d$_6$, 400 MHZ): 8.87 (s, 1H), 8.20 (s, 1H), 8.10-8.09 (d, J = 6.8 Hz, 1H), 7.92-7.91 (d, J = 4.4 Hz, 1H), 7.84-7.83 (d, J = 3.6 Hz, 1H), 7.46-7.44 (d, J = 6.4 Hz, 1H), 6.33-6.29 (t, J = 7.2 Hz, 1H), 6.20 (s, 1H), 5.31-5.25 (t, J = 12 Hz, 1H), 4.70 (bs, 1H), 4.15 (bs, 1H), 2.91-2.90 (d, J = 4 Hz, 3H), 2.88-2.83 (m, 1H), 2.09 (s, 1H), 1.93-1.83 (m, 4H), 1.76-1.62 (m, 3H), 0.81-0.77 (m, 2H), 0.52 (bs, 2H).<br>FR-b: MS(ES): m/z 438.32 [M + H]$^+$, LCMS purity: 97.60%, HPLC purity: 98.69%, CHIRAL HPLC purity: 95.31%, $^1$H NMR (DMSO-d$_6$, 400 MHZ): 8.86 (s, 1H), 8.20 (s, 1H), 8.10-8.09 (d, J = 6.8 Hz, 1H), 7.92-7.91 (d, J = 4.4 Hz, 1H), 7.84-7.83 (d, J = 3.6 Hz, 1H), 7.46-7.44 (d, J = 6 Hz, 1H), 6.33-6.29 (t, J = 6.8 Hz, 1H), 6.20 (s, 1H), 5.31-5.25 (t, J = 12 Hz, 1H), 4.70 (bs, 1H), 4.15 (bs, 1H), 2.91-2.90 (d, J -3.6 Hz, 3H), 2.88-2.84 (m, 1H), 1.93-1.87 (m, 2H), 1.76 (bs, 2H), 1.66-1.47 (m, 3H), 1.47-1.41 (m, 1H), 0.81-0.77 (m, 2H), 0.52 (bs, 2H). |

TABLE 27-continued

| Compound # | Reagent | Chiral Separation Conditions and Characterization Data |
|---|---|---|
| I-744 | 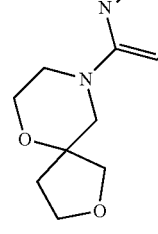

96g | MS (ES): m/z 465.32 [M + H]⁺, LCMS purity: 95.94%, HPLC purity: 96.91%, Chiral HPLC: 49.07%, 49.20%, ¹H NMR (DMSO-d₆, 400 MHZ): 9.64 (s, 1H), 8.20 (s, 1H), 8.05-8.03 (d, J = 4.4 Hz, 1H), 7.96 (s, 1H), 7.57-7.53 (t, J = 8 Hz, 1H), 6.93-6.91 (d, J = 7.6 Hz, 1H), 6.54-6.52 (d, J = 8.4 Hz, 2H), 3.84-3.75 (m, 4H), 3.65 (s, 1H), 3.55 (bs, 3H), 3.02-3.01 (d, J = 4.8 Hz, 1H), 2.94-2.93 (d, J = 4.4 Hz, 3H), 2.74 (s, 1H), 2.68 (bs, 1H), 2.05-2.00 (m, 1H), 1.94-1.89 (m, 1H), 0.77-0.76 (d, J = 6.8 Hz, 2H), 0.56 (bs, 2H). |
| I-827 I-828 | 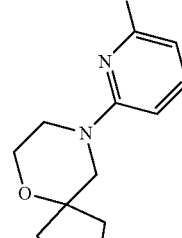

96g | Intermediate corresponding to 96.1 en route to I-744 was separated into isomers before BOC removal: CHIRALPAK IB (250 mm * 4.6 mm, 5u) and 0.1% DEA_HEX_IPA-MEOH (50-50) at 4 mL/min.
Product prepared from FR-a: MS (ES): m/z 465.32 [M + H]⁺, LCMS purity: 99.20%, HPLC purity: 99.19%, Chiral HPLC: 99.22 ¹H NMR (DMSO-d₆, 400 MHZ): 9.64 (s, 1H), 8.20 (s, 1H), 8.04-8.03 (t, J = 4 Hz, 1H), 7.96 (s, 1H), 7.57-7.55 (t, J = 8 Hz, 1H), 6.93-6.91 (d, J = 8 Hz, 2H), 6.54-6.52 (d, J = 8 Hz, 2H), 3.82-3.64 (m, 6H), 3.55 (s, 2H), 3.49 (s, 2H), 2.94-2.93 (d, J = 4 Hz, 3H), 2.85 (s, 1H), 2.75 (s, 1H), 2.68 (s, 1H), 2.05-2.03 (t, J = 8 Hz, 1H), 1.93-1.87 (m, 1H), 1.24 (bs, 1H).
Product prepared from FR-b: MS (ES): m/z 465.32 [M + H]⁺, LCMS purity: 98.68%, HPLC purity: 99.25% Chiral HPLC: 98.28%, ¹H NMR (DMSO-d₆, 400 MHZ): 9.64 (s, 1H), 8.20 (s, 1H), 8.04-8.03 (t, J = 4 Hz, 2H), 7.57-7.55 (t, J = 8 Hz, 1H), 6.93-6.91 (d, J = 8 Hz, 1H), 6.54-6.52 (d, J = 8 Hz, 2H), 3.82-3.64 (m, 6H), 3.55 (s, 2H), 3.49 (s, 2H), 2.94-2.93 (d, J = 4 Hz, 3H), 2.85 (s, 1H), 2.75 (s, 1H), 2.68 (s, 1H), 2.05-2.03 (t, J = 8 Hz, 1H), 1.93-1.87 (m, 1H), 1.24 (bs, 1H). |
| I-742 | 

96h | MS(ES): m/z 410.5 [M + H]⁺. LCMS purity: 97.55%, HPLC purity: 95.40%, Chiral HPLC purity: 49.57%, 49.78%, NMR (DMSO-d₆, 400 MHZ): 8.92 (s, 1H), 8.20 (s, 1H), 8.13-8.12(d, J = 6.4 Hz, 1H), 7.93-7.92 (d, J = 4.8 Hz, 1H), 7.85-7.84 (d, J = 3.6 Hz, 1H), 7.53-7.51 (d, J = 5.6 Hz, 1H), 6.38-6.34 (t, J = 7.2 Hz, 1H), 6.21 (s, 1H), 5.66 (s, 1H), 4.95-93 (d, J = 8.4 Hz, 1H), 4.38 (s, 1H), 2.91-2.90 (d, J = 4.4 Hz, 3H), 2.88-2.85 (m, 1H), 2.14-2.13 (d, J = 7.2 Hz, 2H), 1.66-1.63 (d, J = 12.8 Hz, 2H), 0.82-0.77 (m, 2H), 0.51(bs, 2H). |

TABLE 27-continued

| Compound # | Reagent | Chiral Separation Conditions and Characterization Data |
|---|---|---|
| I-801<br>I-802 | NH₂·HCl, 96h (pyridinone-N-cyclobutyl-OH structure) | I-742 was separated into isomers:<br>CHIRAL PAK D3 (250 mm * 4.6 mm, 5u) in 0.1% diethylamine in methanol at 4 mL/min<br>FR-a: MS(ES): m/z 410.5 [M + H]⁺.<br>LCMS purity: 100%, HPLC purity: 99.23%, Chiral HPLC purity: 100%, NMR (DMSO-d₆, 400 MHZ): 8.92 (s, 1H), 8.20 (s, 1H), 8.14-8.12 (d, J = 6.8 Hz, 1H), 7.93-7.92 (d, J = 4.8 Hz, 1H), 7.85-7.84 (d, J = 3.6 Hz, 1H), 7.53-7.51 (d, J = 6.4 Hz, 1H), 6.38-6.34 (t, J = 7.2 Hz, 1H), 6.21 (s, 1H), 5.66 (s, 1H), 4.95-4.93 (d, J = 8.4 Hz, 1H), 4.38 (s, 1H), 2.91-2.90 (d, J = 4.4 Hz, 3H), 2.88-2.86 (m, 1H), 2.14-2.13 (d, J = 6.8 Hz, 2H), 1.63-1.61 (d, J = 8 Hz, 2H), 0.82-0.79 (m, 2H), 0.51 (bs, 2H).<br>FR-b: MS(ES): m/z 410.5 [M + H]⁺·<br>LCMS purity: 95.95%, HPLC purity: 95.10%, Chiral HPLC purity: 99%, NMR (DMSO-d₆, 400 MHZ): 8.91 (s, 1H), 8.19 (s, 1H), 8.13-8.11 (d, J = 7.6 Hz, 1H), 7.92-7.91 (d, J = 4.8 Hz, 1H), 7.84-7.83 (d, J = 4 Hz, 1H), 7.52-7.50 (d, J = 6.8 Hz, 1H), 6.36-6.33 (t, J = 6.8 Hz, 1H), 6.20 (s, 1H), 5.65-5.63 (d, J = 6.4 Hz, 1H), 4.96-4.92 (t, J = 8.8 Hz, 1H), 4.36 (s, 1H), 2.90-2.88 (d, J = 4.8 Hz, 3H), 2.86-2.85 (m, 1H), 2.13-2.11 (d, J = 6.4 Hz, 2H) 1.65-1.62 (d, J = 13.2 Hz, 2H), 0.79-0.78 (m, 2H), 0.50 (bs, 2H). |
| I-913 | isothiazole-NH₂-OEt ester structure | Ethyl ester was converted to N-methyl carboxamide (THF, TMA, MeNH₂, 70° C., DIPEA) before final removal of BOC: MS (ES): m/z 387.60 [M + H]⁺, LCMS purity: 98.96%, HPLC purity: 98.60%, CHIRAL HPLC: 98.55%, ¹H NMR (DMSO-d₆, 400 MHZ): 10.29 (s, 1H), 9.32 (s, 1H), 8.99 (s, 1H), 8.25 (s, 1H), 8.00 (s, 1H), 7.82 (s, 1H), 5.89 (s, 1H), 2.96 (s, 3H), 2.85 (s, 3H), 1.24 (s, 1H), 0.76-0.53 (m, 4H). |
| I-887 | furan-NH₂-OEt ester structure | Ethyl ester was converted to N-methyl carboxamide (THF, TMA, MeNH₂, 70° C., DIPEA) before final removal of BOC: MS (ES): m/z 370.33 [M + H]⁺, LCMS purity: 99.36%, HPLC purity: 98.89%, ¹H NMR (DMSO-d₆, 400 MHZ): 9.35 (s, 1H), 8.28-8.26 (d, J = 4.8 Hz, 1H), 8.21 (s, 1H), 7.99 (s, 1H), 7.88 (s, 1H), 7.86-7.85 (d, J = 3.6 Hz, 1H), 7.32-7.30 (m, 1H), 5.97 (s, 1H), 2.93-2.92 (d, J = 4.8 Hz, 3H), 2.79-2.78 (d, J = 4.4 Hz, 3H), 1.24 (s, 1H), 0.79-0.72 (m, 2H), 0.54-0.52 (m, 2H). |
| I-671 | NH₂·HCl, 96i (pyridinone-N-cyclohexyl-OH structure) | MS (ES): m/z 438.50 [M + H]⁺, LCMS purity: 98.11%, HPLC purity: 95.03%, Chiral HPLC: 48.07: 48.72%, ¹H NMR (DMSO-d₆, 400 MHZ): 8.86 (s, 1H), 8.19 (s, 1H), 8.13-8.11 (d, J = 6.8 Hz, 1H), 7.92-7.91 (d, J = 4.8 Hz, 1H), 7.86-7.85 (d, J = 3.6 Hz, 1H), 7.42-7.41 (d, J = 6.4 Hz, 1H), 6.31-6.27 (t, J = 6.8 Hz, 1H), 6.19 (s, 1H), 4.92 (s, 1H), 4.84-4.81 (d, J = 12.8 Hz, 1H), 3.96 (s, 1H), 2.91-2.90 (d, J = 4.4 Hz, 3H), 2.55 (s, 1H), 2.17-2.12 (m, 1H), 1.89-1.78 (m, 2H), 1.62-1.45 (m, 5H), 0.80-0.79 (m, 2H), 0.51 (bs, 2H). |

TABLE 27-continued

| Compound # | Reagent | Chiral Separation Conditions and Characterization Data |
|---|---|---|
| I-878<br>I-879 | 96i (NH₂·HCl pyridinone with cyclohexyl-OH) | I-671 was separated into isomers: CHIRAL PAK AD-H (250 × 4.6 mm, 5u) and 0.1% DEA in methanol at 4 mL/min. FR-a: MS(ES): m/z 438.49 [M + H]⁺, LCMS purity: 98.70%, HPLC purity: 95.00%, CHIRAL HPLC purity: 98.76%, ¹H NMR (DMSO-d₆, 400 MHZ): 8.86 (s, 1H), 8.19 (s, 1H), 8.13-8.11 (d, J = 6.8 Hz, 1H), 7.92-7.91 (d, J = 4.8 Hz, 1H), 7.86-7.85 (d, J = 3.6 Hz, 1H), 7.42-7.41 (d, J = 6.4 Hz, 1H), 6.31-6.27 (t, J = 6.8 Hz, 1H), 6.19 (s, 1H), 4.92 (s, 1H), 4.84-4.81 (d, J = 12.8 Hz, 1H), 3.96 (s, 1H), 2.91-2.85 (m, 3H), 2.17-2.12 (m, 1H), 1.89-1.78 (m, 3H), 1.62-1.45 (m, 4H), 0.81-0.79 (m, 2H), 0.51 (s, 2H). FR-b: MS(ES): m/z 438.31 [M + H]⁺, LCMS purity: 95.11%, HPLC purity: 95.00%, CHIRAL HPLC purity: 95.00%, ¹H NMR (DMSO-d₆, 400 MHZ): 8.86 (s, 1H), 8.19 (s, 1H), 8.13-8.11 (d, J = 7.2 Hz, 1H), 7.92-7.90 (d, J = 4.8 Hz, 1H), 7.86-7.85 (d, J = 3.6 Hz, 1H), 7.43-7.41 (d, J = 7.2 Hz, 1H), 6.31-6.27 (t, J = 7.2 Hz, 1H), 6.19 (s, 1H), 4.92-4.91 (d, J = 4.8 Hz, 1H), 4.84-4.81 (d, J = 13.2 Hz, 1H), 3.96 (s, 1H), 2.92-2.84 (m, 4H), 2.17-2.10 (m, 1H), 1.88-1.78 (m, 3H), 1.66-1.46 (m, 4H), 0.82-0.77 (m, 2H), 0.53 (bs, 2H). |
| I-989 | 96bb (NH₂·HCl pyridinone with cyclohexyl-OH) | MS (ES): m/z 452.31 [M + H]⁺, LCMS purity: 100%, HPLC purity: 99.43%, CHIRAL HPLC: 100%, ¹H NMR (DMSO-d₆, 400 MHZ): 8.86 (s, 1H), 8.19 (s, 1H), 8.14-8.12 (d, J = 7.2 Hz, 1H), 7.92-7.91 (d, J = 4.4 Hz, 1H), 7.85-7.84 (d, J = 4 Hz, 1H), 7.40-7.38 (d, J = 6.8 Hz, 1H), 6.32-6.28 (t, J = 7.2 Hz, 1H), 6.17 (s, 1H), 4.90-4.87 (d, J = 12.8 Hz, 1H), 3.13 (s, 3H), 2.91-2.90 (d, J = 4.4 Hz, 3H), 2.88-2.84 (m, 1H), 2.10 (bs, 3H), 1.85 (bs, 1H), 1.59 (bs, 1H), 1.47 (bs, 4H), 0.81-0.80 (d, J = 6.8 Hz, 2H), 0.48 (bs, 2H). |
| I-627 | 96j (NH₂ pyridinone with N-methyl fluoropiperidine) | MS(ES): m/z 455.50 [M + H]⁺. LCMS purity: 100%, HPLC purity: 99.54%, Chiral HPLC purity: 49.64%, 49.66%, NMR (DMSO-d₆, 400 MHZ): 8.92 (s, 1H), 8.20-8.17 (t, J = 6 Hz, 2H), 7.94-7.93 (d, J = 4.8 Hz, 1H), 7.83-7.83 (d, J = 3.2 Hz, 1H), 7.39-7.37 (d, J = 6.8 Hz, 1H), 6.38-6.34 (t, J = 7.2 Hz, 1H), 6.21 (s, 1H), 5.06 (m, 2H), 4.94 (s, 1H), 3.58 (s, 1H), 3.18-3.17 (d, J = 4.4 Hz, 2H), 2.91-2.90 (d, J = 4.4 Hz, 2H), 2.86-2.74 (d, J = 3.6 Hz, 2H), 1.88 (bs, 1H), 1.27-1.18 (m, 3H), 0.80-0.78 (d, J = 5.6 Hz, 3H), 0.50 (bs, 2H). |

TABLE 27-continued

| Compound # | Reagent | Chiral Separation Conditions and Characterization Data |
|---|---|---|
| I-687<br>I-688 | 96j | I-627 was separated into isomers:<br>CHIRAL PAK AD-H (250 × 4.6 mm, 5u) and 0.1% DEA at 4 mL/min.<br>FR-a: MS(ES): m/z 455.3 [M + H]⁺,<br>LCMS purity: 100%, HPLC purity: 99.37%, CHIRAL HPLC purity: 100%,<br>$^1$H NMR (DMSO-$d_6$, 400 MHZ): 8.91 (s, 1H), 8.20-8.17 (t, J = 7.2 Hz, 2H), 7.94-93 (d, J = 4.8 Hz, 1H), 7.84-7.83 (d, J = 3.6 Hz, 1H), 7.39-7.37 (d, J = 7.2 Hz, 1H), 6.38-6.35 (t, J = 7.2 Hz, 1H), 6.20 (s, 1H), 5.06 (s, 2H), 4.94 (s, 1H), 3.58 (s, 2H), 3.18-3.17 (d, J = 4.4 Hz, 2H), 2.91-2.90 (d, J = 4.8 Hz, 3H), 2.88-2.28 (d, J = 3.6 Hz, 1H), 2.51 (s, 3H), 1.88 (bs, 1H), 1.24 (bs, 1H), 0.81-0.77 (m, 1H), 0.52 (bs, 2H).<br>FR-b: MS(ES): m/z 455.50 [M + H]⁺. LCMS purity: 100%, HPLC purity: 99.21%, Chiral HPLC purity: 100%, NMR (DMSO-$d_6$, 400 MHZ): 8.91 (s, 1H), 8.20-8.17 (t, J = 6 Hz, 2H), 7.93-92 (d, J = 4.8 Hz, 1H), 7.84-7.83 (d, J = 3.2 Hz, 1H), 7.39-7.37 (d, J = 6.8 Hz, 1H), 6.38-6.34 (t, J = 7.2 Hz, 1H), 6.21 (s, 1H), 5.06 (s, 1H), 4.94 (s, 1H), 3.58 (s, 2H), 3.18-3.17 (d, J = 4.4 Hz, 2H), 2.91-2.90 (d, J = 4.8 Hz, 3H), 2.88-2.28 (d, J = 3.6 Hz, 1H), 2.51 (s, 3H), 1.88 (bs, 1H), 1.24 (bs, 1H), 0.81-0.77 (m, 1H), 0.52 (bs, 2H). |
| I-608 | 96k | MS(ES): m/z 455.50 [M + H]⁺.<br>LCMS purity: 99.35%, HPLC purity: 99.27%, Chiral HPLC purity: 49.00%, 49.74%, NMR (DMSO-$d_6$, 400 MHZ): 8.91 (s, 1H), 8.20 (s, 1H), 8.15-8.13 (d, J = 6.4 Hz, 2H), 7.94-7.93 (d, J = 4.8 Hz, 1H), 7.83-7.82 (d, J = 4 Hz, 1H), 7.60-7.58 (d, J = 6.8 Hz, 1H), 6.37-6.34 (t, J = 7.2 Hz, 1H), 6.21 (s, 1H), 5.06 (m, 2H), 4.94 (s, 1H), 3.58 (s, 1H), 3.30-3.27 (t, J = 5.2 Hz, 1H), 2.91-2.90 (d, J = 4.8 Hz, 3H), 2.88-2.85 (m, 2H), 2.34-2.28 (m, 2H), 2.16-2.07 (m, 2H), 1.87 (bs, 1H), 0.82-0.77 (m, J = 5.6 Hz, 1H), 0.52-0.49 (s, 2H). |
| I-685<br>I-686 | 96k | I-608 was separated into isomers:<br>CHIRAL PAK AD-H (250 × 4.6 mm, 5u) and 0.1% DEA at 4 mL/min.<br>FR-a: MS(ES): m/z 455.3 [M + H]⁺,<br>LCMS purity: 99.13%, HPLC purity: 99.82%, CHIRAL HPLC purity: 98.90%, $^1$H NMR (DMSO-$d_6$, 400 MHZ): 8.91 (s, 1H), 8.20 (s, 1H), 8.15-8.13 (d, J = 7.2 Hz, 1H), 7.94-7.93 (d, J = 4.8 Hz, 1H), 7.84-7.82 (d, J = 3.6 Hz, 1H), 7.60-7.58 (d, J = 6.8 Hz, 1H), 6.37-6.34 (t, J = 7.2 Hz, 1H), 6.21 (s, 1H), 5.18 (bs, 1H), 4.92 (s, 1H), 3.80-3.76 (m, J = 4.4 Hz, 1H), 3.30 (s, 1H), 2.91-2.90 (d, J = 4.4 Hz, 2H), 2.86-2.85 (t, J = 4 Hz, 1H), 2.30 (s, 2H), 2.16-2.13 (t, J = 5.2 Hz, 2H), 1.86 (bs, 1H), 1.05-1.04 (d, J = 5.2 Hz, 3H), 0.80-0.77 (t, J = 5.2 Hz, 2H), 0.51 (bs, 2H).<br>FR-b: MS(ES): m/z 455.50 [M + H]⁺. LCMS purity: 100%, HPLC purity: 99.66%, Chiral HPLC purity: 100%, NMR (DMSO-$d_6$, 400 MHZ): 8.90 (s, 1H), 8.19 (s, 1H), 8.14-8.12 (d, J = 6.8 Hz, 1H), 7.93-7.92 (d, J = 4 Hz, 1H), 7.82-7.81 (d, J = 3.6 Hz, 1H), 7.59-7.57 (d, J = 6.4 Hz, 1H), 6.36-6.33 (t, J = 6.8 Hz, 1H), 6.20 (s, 1H), 5.18 (bs, 1H), 4.92 (s, 1H), 3.29-3.26 (m, 1H), 3.17 (s, 1H), 2.90-2.89 (d, J = 4.4 Hz, 3H), 2.85-2.84 (t, |

TABLE 27-continued

| Compound # | Reagent | Chiral Separation Conditions and Characterization Data |
|---|---|---|
| | | J = 6.8 Hz, 2H), 2.29 (s, 2H), 2.15-2.12 (m, 2H), 1.85 (bs, 1H), 1.23-1.04 (s, 1H), 0.81-076(m, 2H), 0.51-0.50 (d, J = 6.8 Hz, 2H). |
| I-761 | 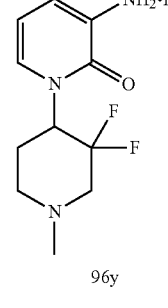 96y | MS(ES): m/z 473.50 [M + H]⁺. LCMS purity: 100%, HPLC purity: 99.40%, Chiral HPLC purity: 49.74%, 50.02%, NMR (DMSO-$d_6$, 400 MHZ): 8.93 (s, 1H), 8.21 (s, 1H), 8.17-8.15(d, J = 7.2 Hz, 1H), 7.95-7.93 (d, J = 4.4 Hz, 1H), 7.83-7.82 (d, J = 3.6 Hz, 1H), 7.45-7.43 (d, J = 6.4 Hz, 1H), 6.37-6.33 (t, J = 7.2 Hz, 1H), 6.20(s, 1H), 5.49-5.43 (m, 1H), 3.24-19(t, J = 10 Hz, 1H) 2.96 (bs, 1H), 2.91-2.90 (d, J = 4.8 Hz, 3H), 2.86-2.86 (m, 2H), 2.35-2.33 (d, J = 8 Hz, 6H), 1.93 (s, 1H), 1.24 (s, 1H), 0.80-0.78 (d, J = 6.4 Hz, 1H), 0.51 (bs, 1H). |
| I-823 I-824 | 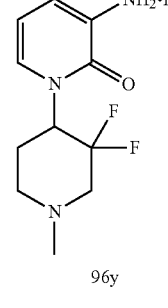 96y | I-761 was separated into isomers: CHIRAL PAK IB (250 mm * 4.6 mm, 5u) in 0.1% Diethyl amine in methanol at 4 mL/min. FR-a: MS(ES): m/z 473.50 [M + H]⁺. LCMS purity: 100%, HPLC purity: 99.08%, Chiral HPLC purity: 99.36%, NMR (DMSO-$d_6$, 400 MHZ): 8.92 (s, 1H), 8.19 (s, 1H), 8.16-8.14 (d, J = 7.2 Hz, 1H), 7.93-7.92 (d, J = 4.8 Hz, 1H), 7.82-7.81 (d, J = 3.6 Hz, 1H), 7.43-7.42 (d, J = 6.8 Hz, 1H), 6.35-6.32 (t, J = 7.2 Hz ,1H), 6.19 (s, 1H), 5.47-5.42 (m, 1H), 3.22-3.17 (t, J = 11.2 Hz, 1H) 2.95 (bs, 1H), 2.90-2.89 (d, J = 4.8 Hz, 3H), 2.86-2.84 (m, 2H), 2.33-2.31 (m, 5H), 1.91 (s, 1H), 0.79-0.77 (d, J = 6 Hz, 2H), 0.49 (bs, 2H). FR-b: MS(ES): MS(ES): m/z 473.50 [M + H]⁺. LCMS purity: 100%, HPLC purity: 99.65%, Chiral HPLC purity: 98.82%, NMR (DMSO-$d_6$, 400 MHZ): 8.94 (s, 1H), 8.20 (s, 1H), 8.17-8.15 (d, J = 6.4 Hz, 1H), 7.95-7.94 (d, J = 4.8 Hz, 1H), 7.83-7.82 (d, J = 4 Hz, 1H), 7.45-7.43 (d, J = 7.2 Hz, 1H), 6.36-6.33 (t, J = 7.2 Hz, 1H), 6.20 (s, 1H), 5.47-5.42 (m, 1H), 3.23-3.18 (t, J = 11.6 Hz, 1H) 2.96 (bs, 1H), 2.91-2.90 (d, J = 6 Hz, 3H), 2.88-2.83 (m, 2H), 2.35-2.32 (m, 5H), 1.92(s, 1H), 0.80-0.78 (d, J = 5.6 Hz, 2H), 0.51(bs, 2H). |
| I-568 |  96l | MS (ES): m/z 452.51 [M + H]⁺, LCMS purity: 100%, HPLC purity: 99.57%, CHIRAL HPLC: 49.81%, 49.83%, ¹H NMR (DMSO-$d_6$, 400 MHZ): 8.87 (s, 1H), 8.20 (s, 1H), 8.12-8.10 (d, J = 6.4 Hz, 1H), 7.92-7.90 (d, J = 4.8 Hz, 1H), 7.83-7.82 (d, J = 3.6 Hz, 1H), 7.50-7.49 (d, J = 5.6 Hz, 1H), 6.35-6.31 (t, J = 7.2 Hz, 1H), 6.20 (s, 1H), 4.87-4.80 (t, J = 12.4 Hz, 1H), 3.32 (s, 4H), 2.92-2.90 (d, J = 4.4 Hz, 4H), 2.20-2.17 (d, J = 10.4 Hz, 1H), 2.07-2.04 (d, J = 10.4 Hz, 1H), 2.00 (s, 1H), 1.88-1.85 (d, J = 13.2 Hz, 1H), 1.74 (bs, 1H), 1.46-1.36 (m, 1H), 1.20-1.11(m, 2H), 0.79-0.77 (d, J = 6.8 Hz, 2H), 0.52 (bs, 2H). |

TABLE 27-continued

| Compound # | Reagent | Chiral Separation Conditions and Characterization Data |
|---|---|---|
| I-621<br>I-622 | 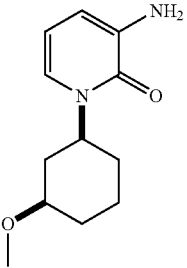<br>96l | I-568 was separated into isomers:<br>CHIRAL PAK IB (250 mm * 4.6 mm, 5u) in 0.1% Diethyl amine in methanol at 4 mL/min.<br>FR-a: MS(ES): m/z 452.51 [M + H]$^+$.<br>LCMS purity: 100%, HPLC purity: 99.07%, Chiral HPLC purity: 95.68%, NMR (DMSO-$d_6$, 400 MHZ): 8.87 (s, 1H), 8.20 (s, 1H), 8.12-8.10 (d, J = 6 Hz, 1H), 7.92-7.91 (d, J = 4.8 Hz, 1H), 7.84-7.83 (d, J = 4 Hz, 1H), 7.51-7.49 (d, J = 6 Hz, 1H), 6.35-6.31 (d, J = 7.2 Hz, 1H), 6.19 (s, 1H), 4.83 (bs, 1H), 3.28 (s, 3H), 2.91-2.90 (d, J = 4.4 Hz, 3H), 2.88-2.85 (m, 1H), 2.19-2.17(d, J = 10.8 Hz, 1H), 2.06-2.04 (d, J = 10 Hz, 2H), 1.88-1.85 (d, J = 13. Hz, 2H), 1.77-1.74 (m, 2H), 1.60-1.14 (m, 4H), 0.82-0.77 (m, 2H).<br>FR-b: MS(ES): m/z 452.51 [M + H]$^+$.<br>LCMS purity: 100%, HPLC purity: 990.7%, Chiral HPLC purity: 95.68%, NMR (DMSO-$d_6$, 400 MHZ): 8.87 (s, 1H), 8.18 (s, 1H), 8.11-8.09 (d, J = 7.2 Hz, 1H), 7.91-7.90 (d, J = 4.8 Hz, 1H), 7.82-7.81 (d, J = 4 Hz, 1H), 7.50-7.48 (d, J = 6.8 Hz, 1H), 6.33-6.30 (t, J = 7.2 Hz, 1H), 6.18 (s, 1H), 4.85-4.79 (t, J = 12 Hz, 1H), 3.26 (s, 3H), 2.90-2.89 (d, J = 4.8 Hz, 3H), 2.86-2.82 (m, 1H), 2.18-2.15 (d, J = 10.8 Hz, 1H), 2.05-2.02 (d, J = 11.6 Hz, 2H), 1.87-1.83 (d, J = 16 Hz, 2H), 1.77-1.74 (m, 2H), 1.60-1.14 (m, 4H), 0.82-0.77 (m, 2H). |
| I-567 | 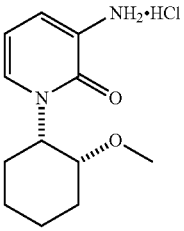<br>96m | MS (ES): m/z 454.71 [M + H]$^+$, LCMS purity: 100%, HPLC purity: 99.80%, CHIRAL HPLC: 49.82%, 50.17%, $^1$H (DMSO-$d_6$, 400 MHZ): 8.91 (bs, 1H), 8.21 (s, 1H), 8.16 (bs, 1H), 7.92 (bs, 1H), 7.84 (bs, 1H), 7.44 (bs, 1H), 6.29 (bs, 1H), 6.21 (s, 1H), 5.14 (bs, 1H), 4.15 (bs, 2H), 3.25 (bs, 3H), 2.91(bs, 4H), 2.01 (bs, 2H), 1.83 (bs, 1H), 1.11(bs, 1H), 0.80 (bs, 3H), 0.51 (bs, 2H). |
| I-594<br>I-595 | 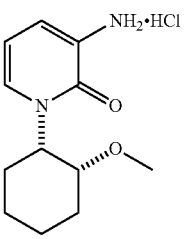<br>96m | I-567 was separated into isomers:<br>CHIRAL PAK IB (250 mm * 4.6 mm, 5u) in 0.1% Diethyl amine in methanol at 4 mL/min.<br>FR-a: MS (ES): m/z 454.50 [M + H]$^+$, LCMS purity: 100%, HPLC purity: 99.32% CHIRAL HPLC: 100%, $^1$H NMR (DMSO-$d_6$, 400 MHZ): 8.90 (s, 1H), 8.20 (s, 1H), 8.15-8.13 (d, J = 6 Hz, 1H), 7.92-7.91(d, J = 4.8 Hz, 1H), 7.84-7.83 (d, J = 3.6 Hz, 1H), 7.44-7.43 (d, J = 6 Hz, 1H), 6.30-6.27 (t, J = 7.2 Hz, 1H), 6.20 (s, 1H), 5.18 (bs, 1H), 4.07-4.02 (s, (d, J = 10.4 Hz,1H), 3.80-3.76 (m, 1H), 3.73-3.71 (d, J = 8.4 Hz, 2H), 3.25 (s, 3H), 2.91-2.90 (t, J = 4.8 Hz, 3H), 2.88-2.83 (m, 1H), 2.01-2.1.99 (m, 1H), 1.83-10.82 (d, J = 6 Hz, 1H), 1.41 (bs, 1H), 0.87-0.84 (m, 2H), 0.52-0.48 (m, 2H).<br>FR-b: MS (ES): m/z 454.45 [M + H]$^+$, LCMS purity: 100%, HPLC purity: 99.40% CHIRAL HPLC: 97.35%, $^1$H NMR (DMSO-$d_6$, 400 MHZ): 8.90 (s, 1H), 8.20 (s, 1H), 8.15-8.13 (d, J = 6.4 Hz, 1H), 7.92-7.91(d, J = 4.8 Hz, 1H), 7.84-7.83 (d, J = 3.6 Hz, 1H), 7.44-7.43 (d, J = 6.4 Hz, 1H), 6.30-6.27 (t, J = 7.2 Hz, 1H), 6.20 (s, 1H), 5.14-5.12 (t, J = 5.2 Hz, 1H), 4.07-4.02 (t, |

TABLE 27-continued

| Compound # | Reagent | Chiral Separation Conditions and Characterization Data |
|---|---|---|
| | | J = 10.4 Hz,1H), 3.80-3.76 (m, 2H), 3.71 (bs, 2H), 3.25 (s, 3H), 2.91-2.90 (d, J = 4.8 Hz, 3H), 2.88-2.83 (m, 1H), 2.01-2.1.99 (m, 1H), 1.83-10.82 (m, 1H), 1.24 (bs, 1H), 1.06-1.04 (d, J = 6 Hz, 1H), 0.87-0.84 (m, 2H), 0.52-0.48 (m, 2H). |
| I-672 | <br>96n | MS (ES): m/z 465.4 [M + H]$^+$, LCMS purity: 98.02%, HPLC purity: 98.12%, $^1$H NMR (DMSO-d$_6$, 400 MHZ): 9.02 (s, 1H), 8.26-8.21 (m, 3H), 7.96-7.95 (d, J = 4.8 Hz, 1H), 7.85-7.81 (m, 2H), 7.41-7.39 (d, J = 5.6 Hz, 1H), 6.46-6.42 (t, J = 7.2 Hz, 1H), 6.20 (s, 1H), 3.95 (s, 3H), 2.90-2.88 (d, J = 4.8 Hz, 4H), 0.80-0.79 (d, J = 5.2 Hz, 2H), 0.53 (bs, 2H). |
| I-659 | 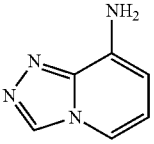 | MS (ES): m/z 364.39 [M + H]$^+$, LCMS purity: 100%, HPLC purity: 99.41%, $^1$H NMR (DMSO-d$_6$, 400 MHZ): 9.85 (bs, 1H), 8.69-8.67 (d, J = 6.4 Hz, 1H), 8.55 (s, 1H), 8.22 (bs, 2H), 8.05-8.03 (d, J = 4.4 Hz, 1H), 7.83-7.82 (d, J = 3.2 Hz, 1H), 7.19-7.15 (t, J = 7.2 Hz, 1H), 6.19 (s, 1H), 2.93-2.92 (d, J = 4.8 Hz, 3H), 2.82 (bs, 1H), 0.75-0.74 (d, J = 5.6 Hz, 2H), 0.42 (bs, 2H). |
| I-740 | 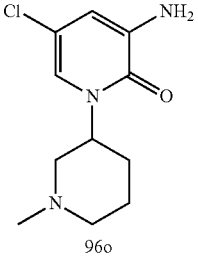<br>96o | MS(ES): m/z 471.99 [M + H]$^+$ LCMS purity: 100%, HPLC purity: 99.56%, Chiral HPLC purity: 50.45%, 49.55%, NMR (DMSO-d$_6$, 400 MHZ): 9.02 (s, 1H), 8.24-8.22 (t, J = 3.6 Hz, 2H), 8.00-7.99 (d, J = 4 Hz, 1H), 7.80 (s, 1H), 6.66-6.65 (d, J = 2.8 Hz, 1H), 6.31 (s, 1H), 4.93-92 (d, J = 4.4 Hz, 1H), 2.91-2.90 (d, J = 4.4 Hz, 3H), 2.81-2.63 (m, 3H), 2.34-2.31 (d, J = 11.6 Hz, 1H), 2.23 (s, 3H), 2.09 (s,1H), 1.83-1.74 (m, 3H), 1.63 (bs, 1H), 0.78-0.73 (m, 2H), 0.57 (s, 2H). |
| I-819<br>I-820 | 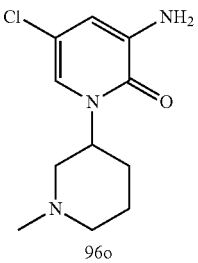<br>96o | I-740 was separated into isomers: CHIRAL PAK IB (250 mm * 4.6 mm, 5u) in 0.1% diethylamine in methanol at 4 mL/min.<br>FR-a: MS(ES): m/z 471.99 [M + H]$^+$ LCMS purity: 100%, HPLC purity: 99.13%, Chiral HPLC purity: 99.50%, NMR (DMSO-d$_6$, 400 MHZ): 9.02 (s, 1H), 8.23-8.22 (t, J = 5.2 Hz, 2H), 7.99 (s, 1H), 7.80 (s, 1H), 7.65-7.64 (d, J = 3.2 Hz, 1H), 6.30 (s, 1H), 4.92-90 (t, J = 4.8 Hz, 1H), 2.91-2.90 (d, J = 4.4 Hz, 3H), 2.82-2.76 (m, 2H), 2.65-2.62 (d, J = 10.8 Hz, 2H), 2.33-2.8 (t, J = 9.6 Hz, 1H), 2.23 (s, 3H), 1.83-1.78 (m, 3H), 1.63(bs, 1H), 0.86-0.73 (m, 2H), 0.58-0.55 (m, 2H).<br>FR-b: MS (ES): m/z 471.99 [M + H]$^+$, LCMS purity: 100%, HPLC purity: 96.19% CHIRAL HPLC: 99.19%, $^1$H NMR (DMSO-d$_6$, 400 MHZ): 9.03 (s, 1H), 8.24-8.22 (t, J = 4 Hz, 2H), 8.00-7.99 (d, J = 4 Hz, 1H), 7.80 (s, 1H), 7.66-7.65 (d, J = 2.8 Hz, 1H), 6.31(s, 1H), 4.95-4.90 (m, 1H), 2.91-2.90 (d, J = 4.4 Hz, 3H), 2.82-2.78 (m, 2H), 2.65-2.63 (d, J = 10 Hz, 2H), 2.33-2.28 (t, J = 10.4 Hz, 1H), 2.23 (s, 3H), |

TABLE 27-continued

| Compound # | Reagent | Chiral Separation Conditions and Characterization Data |
|---|---|---|
| | | 1.86-1.73 (m, 3H), 1.63-1.60 (d, J = 12.4 Hz, 1H), 0.78-0.73 (m, 2H), 0.59-0.55 (m, 2H). |
| I-508 | *[structure: 6-amino-2-(tetrahydropyran-3-yl)pyridine]* | MS(ES): m/z 408.40 [M + H]$^+$ LCMS purity: 98.99%, HPLC purity: 99.76%, Chiral HPLC purity: 49.78%, 50.2%, NMR (DMSO-d$_6$, 400 MHZ): 9.88 (s, 1H), 8.21 (s, 1H), 8.07-8.06 (d, J = 4.8 Hz, 1H), 7.97-7.96 (t, J = 3.6 Hz, 1H), 7.70-7.66 (t, J = 8 Hz, 1H), 7.41-7.39 (d, J = 7.6 Hz, 1H), 6.96-6.94 (d, J = 7.2 Hz, 1H), 6.81 (s, 1H), 4.05-4.00 (m, 2H), 3.91-3.88 (d, J = 10.8 Hz, 1H), 3.55-3.50 (t, J = 10.4 Hz, 1H), 2.92-2.91 (d, J = 3.6 Hz, 3H), 2.88-2.80 (m, 2H), 1.92-1.86 (m, 1H), 1.68 (m, 2H), 1.19-1.16 (t, J = 6.8 Hz, 1H), 0.79-0.75 (m, 2H), 0.56-0.56 (m, 2H). |
| I-548<br>I-549 | *[structure: 6-amino-2-(tetrahydropyran-3-yl)pyridine]* | I-508 was separated into isomers: CHIRAL PAK IB (250 mm * 4.6 mm, 5u) in 0.1% diethylamine in methanol at 4 mL/min.<br>FR-a: MS(ES): m/z 408.60 [M + H]$^+$, LCMS purity: 100%, HPLC purity: 99.88%, CHIRAL HPLC purity: 100%, $^1$H NMR (DMSO-d$_6$, 400 MHZ): 9.89 (s, 1H), 8.21-08 (s, 1H), 8.085 (s, 1H), 7.690 (m, 1H), 7.39 (s, 1H), 6.96-6.94 (d, J = 7.2 Hz, 1H), 6.81 (bs, 1H), 4.02-4.00 (d, J = 9.2 Hz, 1H), 3.91-3.88 (d, J = 11.6 Hz, 1H), 3.55-3.50 (t, J = 10.8 Hz, 1H), 2.98-2.91 (m, 2H), 2.82 (s, 2H), 2.05-1.91 (m, 3H), 1.67 (bs, 2H), 1.33 b(s, 2H), 0.78-0.76 (d, J = 4.8 Hz, 2H), 0.56 (bs, 2H).<br>FR-b: MS(ES): mZ 408.60 [M + H]$^+$, LCMS purity: 100%, HPLC purity: 100, CHIRAL HPLC purity: 99.5%, $^1$H NMR (DMSO-d$_6$, 400 MHZ): 9.89 (s, 1H), 8.21-08 (s, 1H), 8.08 (s, 1H), 7.96 (s, 1H), 7.70-7.67 (t, J = 7.6 Hz, 1H), 7.41-4.39 (d, J = 6.8 Hz, 1H), 6.96-6.946 (d, J = 7.6 Hz, 1H), 6.80 (s, 1H), 4.02-4.00 (d, J = 9.2 Hz, 1H), 3.91-3.88 (d, J = 10.8 Hz, 1H), 3.55-3.50 (t, J = 10.4 Hz, 1H), 2.98-2.96 (m, 2H), 2.82 (s, 1H), 2.08-1.89 (m, 3H), 1.67 (bs, 2H), 1.23(bs, 2H), 0.78-0.76 (d, J = 6 Hz, 2H), 0.55 (bs, 2H). |
| I-655 | *[structure: 96p, spirocyclic amine pyridine]* | MS(ES): m/z 463.61 [M + H]$^+$. LCMS purity: 98.10%, HPLC purity: 97.28%, NMR (DMSO-d$_6$, 400 MHZ): 9.58 (s, 1H), 8.21 (s, 1H), 8.02-8.00 (d, J = 3.2 Hz, 1H), 7.51-7.47 (d, J = 8 Hz, 1H), 6.79-6.77 (d, J = 7.6 Hz, 1H), 6.66(s, 1H), 6.47-6.45 (d, J = 8.4 Hz, 1H), 3.78-3.71(m, 4H), 3.53-3.47 (m, 2H), 3.42-3.35 (m, 1H), 2.93-2.92 (d, J = 4.8 Hz, 3H), 2.86-2.83 (m, 1H), 1.94-1.87 (m, 2H), 1.73-1.69 (t, J = 7.6 Hz, 2H), 1.61-1.59 (d, J = 5.2 Hz, 4H), 0.88-0.87 (d, J = 7.2 Hz, 2H), 0.57 (m, 2H). |
| I-631 | *[structure: 2,3-dihydrofuro[3,2-b]pyridin-5-amine]* | MS (ES): m/z 366.30 [M + H]$^+$, LCMS purity: 100%, HPLC purity: 97.55%, $^1$H NMR (DMSO-d$_6$, 400 MHZ): 9.81 (s, 1H), 8.18 (s, 1H), 7.95 (bs, 2H), 7.52-7.50 (d, J = 8.8 Hz, 1H), 7.20-7.18 (d, J = 8.8 Hz, 1H), 6.06 (bs, 1H), 4.67-4.63 (t, J = 8.8 Hz, 2H), 3.29-3.24 (t, J = 8.8 Hz, 2H), 3.19-3.17 (d, J = 5.2 Hz, 1H), 2.91-2.90 (d, J = 4.4 Hz, |

TABLE 27-continued

| Compound # | Reagent | Chiral Separation Conditions and Characterization Data |
|---|---|---|
| | | 3H), 0.89-0.87 (d, J = 8 Hz, 2H), 0.48 (bs, 2H). |
| I-494 | 96q | MS (ES): m/z 442.34 [M + H]$^+$, LCMS purity: 96.95%, HPLC purity: 96.51%, $^1$H NMR (DMSO-d$_6$, 400 MHZ): 9.10 (s, 1H), 8.28-8.27 (d, J = 2.8 Hz, 1H), 8.23 (s, 1H), 7.99-7.98 (d, J = 4.8 Hz, 1H), 7.68-7.64 (m, 2H), 6.33 (s, 1H), 4.87 (bs, 1H), 3.84 (bs, 2H), 3.62-3.57 (t, J-10 Hz ,1H), 3.48-3.41 (m, 4H), 2.90-2.89 (d, J = 4.4 Hz, 2H), 2.08-2.07 (d, J = 4 Hz, 1H), 1.11-1.07 (t, J = 6.8 Hz, 2H), 0.74-0.72 (d, J = 5.6 Hz 2H), 0.54 (bs, 2H). |
| I-533 I-534 | 96q | I-494 was separated into isomers: CHIRAL PAK IB (250 mm * 4.6 mm, 5u) in 0.1% diethylamine in methanol at 4 mL/min. FR-a: MS(ES): m/z 442.29 [M + H]$^+$, LCMS purity: 97.19%, HPLC purity: 97.47%, CHIRAL HPLC purity: 98.99%, $^1$H NMR (DMSO-d$_6$, 400 MHZ): 9.12 (s, 1H), 8.27-8.26 (d, J = 3.2 Hz, 1H), 8.25 (s, 1H), 8.01 (bs, 1H), 7.70-7.66 (m, 2H), 6.34 (s, 1H), 4.91-4.86 (m, 1H), 3.85-3.82 (m, 2H), 3.62-3.57 (t, J = 10 Hz, 1H), 3.49-3.44 (t, J = 11.2 Hz, 1H), 2.91 (s, 3H), 2.86-2.82 (m, 1H), 1.77-1.70 (m, 3H), 1.24 (bs, 1H), 0.73-0.72 (d, J = 6.4 Hz, 2H), 0.53 (bs, 2H). FR-b: MS(ES): m/z 442.22 [M − H]$^+$, LCMS purity: 95.16%, HPLC purity: 92.86%, CHIRAL HPLC purity: 98.46%, $^1$H NMR (DMSO-d$_6$, 400 MHZ): 9.10 (s, 1H), 8.28-8.27 (d, J = 2.8 Hz, 1H), 8.23 (s, 1H), 7.99 (bs, 1H), 7.68-7.64 (m, 2H), 6.33 (s, 1H), 4.90-4.85 (m, 1H), 3.84-3.81 (m, 2H), 3.62-3.57 (t, J = 10.4 Hz, 1H), 3.48-3.43 (t, J = 10.8 Hz, 1H), 2.90 (s, 3H), 2.85-2.81 (m, 1H), 2.12-2.04 (m, 1H), 1.95 (bs, 1H), 1.76-1.70 (m, 2H), 0.74-0.72 (d, J = 5.2 Hz, 2H), 0.54 (bs, 2H). |
| I-491 | 96r | MS(ES): m/z 438.50 [M + H]$^+$. LCMS purity: 100%, HPLC purity: 100%, Chiral HPLC purity: 49.78%, 50.2%, NMR (DMSO-d$_6$, 400 MHZ): 8.89 (s, 1H), 8.19 (s, 1H), 8.14-8.12 (d, J = 6.8 Hz, 1H), 7.92-7.91 (d, J = 4.8 Hz, 1H), 7.85-7.84 (d, J = 3.6 Hz, 1H), 7.41-7.40 (d, J = 6.4 Hz, 1H), 6.30-6.27 (t, J = 7.2 Hz, 1H), 6.19 (s, 1H), 5.10-5.04 (m, 1H), 3.91 (s, 1H) 3.04 (s, 3H), 2.90-2.89 (d, J = 4.8 Hz, 3H), 2.87-2.85 (m, 1H), 2.16-2.06 (m, 1H), 1.96-1.83 (m, 4H), 1.66-1.64 (d, J = 9.2 Hz, 1H), 0.81-0.78 (d, J = 5.2 Hz, 2H) 0.52-0.48 (s, 2H). |
| I-524 I-525 | 96r | I-491 was separated into isomers: CHIRAL PAK IB (250 mm * 4.6 mm, 5u) in 0.1% diethylamine in methanol at 4 mL/min. FR-a: MS(ES): m/z 438.50 [M + H]$^+$. LCMS purity: 100%, HPLC purity: 99.83%, Chiral HPLC purity: 100%, NMR (DMSO-d$_6$, 400 MHZ): 8.88 (s, 1H), 8.18 (s, 1H), 8.13-8.12 (d, J = 6.4 Hz, 1H), 7.90-7.89 (d, J = 4.8 Hz, 1H), 7.84-7.83 (d, J = 3.6 Hz, 1H), 7.40-7.39 (d, J = 6 Hz, 1H), 6.29-6.26 (t, J = 6.8 Hz,1H), 6.18 (s, 1H), 5.09-5.03 (m, 1H), 3.91 (s, |

TABLE 27-continued

| Compound # | Reagent | Chiral Separation Conditions and Characterization Data |
|---|---|---|
| | | 1H) 3.03 (s, 3H), 2.90-2.89 (d, J = 4.8 Hz, 3H), 2.87-2.83 (m, 1H), 2.12-2.05 (m, 1H), 1.99-1.82 (m, 4H), 1.65-1.63 (d, J = 8.4 Hz,1H), 0.80-0.77 (m, 2H), 0.51-0.47 (m, 2H).<br>FR-b: MS(ES): m/z 438.50 [M + H]⁺.<br>LCMS purity: 100%, HPLC purity: 99.89%, Chiral HPLC purity: 99.43%, NMR (DMSO-d₆, 400 MHZ): 8.88 (s, 1H), 8.18 (s, 1H), 8.13-8.12 (d, J = 6.4 Hz, 1H), 7.90-7.89 (d, J = 4.8 Hz,1H), 7.84-7.83 (d, J = 3.6 Hz, 1H), 7.40-7.39 (d, J = 6.4 Hz, 1H), 6.29-6.26 (t, J = 7.2 Hz, 1H), 6.18 (s, 1H), 5.09-5.03 (m, 1H), 3.90 (s, 1H) 3.03 (s, 3H), 2.90-2.89 (d, J = 4.8 Hz, 3H), 2.87-2.85 (m, 1H), 2.12-2.05 (m, 1H), 1.95-1.82 (m, 4H), 1.63 (bs, 1H), 0.79-0.78 (m, 2H) 0.50-0.46 (m, 2H). |
| I-403 | 96ff | MS(ES): m/z 438.50 [M + H]⁺.<br>LCMS purity: 95.37%, HPLC purity: 98.81%, Chiral HPLC purity: 46.95%, 47.54%, NMR (DMSO-d₆, 400 MHZ): 8.93 (s, 1H), 8.19 (s, 1H), 8.13-8.11 (d, J = 6 Hz, 1H), 7.92-7.91 (d, J4.8 Hz, 1H), 7.83-7.82 (d, J = 3.6 Hz, 1H), 7.44-7.42 (d, J = 6.8 Hz, 1H), 6.35-6.31 (t, J = 7.2 Hz, 1H), 6.20 (s, 1H), 5.01-4.98 (m, 1H), 4.09-4.04 (m, 1H) 3.19 (s, 3H), 2.89-2.88 (d, J = 4.8 Hz, 3H), 2.86-2.83 (m, 1H), 2.13-2.08 (m, 2H), 1.85-1.66 (m, 4H), 0.81-0.76 (m, 2H), 0.52-0.48 (bs, 2H). |
| I-436<br>I-437 | 96ff | I-403 was separated into isomers:<br>CHIRAL PAK IB (250 mm * 4.6 mm, 5u) in 0.1% diethylamine in methanol at 4 mL/min.<br>FR-a: MS(ES): m/z 438.32 [M + H]⁺, LCMS purity: 99.30%, HPLC purity: 99.02%, CHIRAL HPLC purity: 100%, ¹H NMR (DMSO-d₆, 400 MHZ): 8.93 (s, 1H), 8.39 (s, 1H), 8.19 (s, 1H), 8.13-8.11 (d, J = 6.4 Hz, 1H), 7.92-7.91 (d, J = 4.8 Hz, 1H), 7.83-7.82 (d, J = 4 Hz, 1H), 7.44-7.42 (d, J = 6 Hz, 1H), 6.35-6.31 (t, J = 7.2 Hz 1H), 6.20 (s, 1H), 5.03-4.98 (m, 1H), 4.07-4.06 (d, J = 6.4 Hz, 1H), 3.19 (s, 3H), 2.88-2.84 (m, 4H), 2.11-2.10 (d, J = 6.8 Hz, 3H), 1.73-1.66 (m, 2H), 0.81-0.78 (s, 2H), 0.50 (bs, 2H).<br>FR-b: MS(ES): m/z 438.27 [M + H]⁺, LCMS purity: 100%, HPLC purity: 99.29%, CHIRAL HPLC purity: 95.21%, ¹H NMR (DMSO-d₆, 400 MHZ): 8.93 (s, 1H), 8.39 (s, 1H), 8.19 (s, 1H), 8.13-8.11 (d, J = 6.4 Hz, 1H), 7.92-7.91(s, 1H), 7.83-7.82 (d, J = 3.6 Hz, 1H), 7.42 (s, 1H), 7.16 (s, 1H), 6.35(s, 1H), 6.33(s, 1H) 6.20 (s, 1H), 5.03-5.00 (t, J = 6 Hz,1H), 3.23 (s, 3H), 2.88-2.85 (m, 4H), 2.13-2.08 (m, 2H)? 1.73-1.67 (m, 2H), 0.81-0.76 (m, 2H), 0.52 (bs, 2H). |
| I-162 | | MS(ES) : m/z 421.43 [M + H]⁺, LCMS purity: 100%, HPLC purity: 100%, ¹H NMR (DMSO- d₆, 400 MHZ) 9.09 (s, 1H), 8.25-8.22 (m, 2H) ,7.98-7.97 (d, J = 4.8 Hz, 1H), 7.82-7.81(d, J = 4 Hz, 1H), 7.62-7.60 (d, J = 6.8 Hz 1H), 6.89 (s, 1H), 6.49-6.46 (t, J = 7.2 Hz, 1H), 6.24 (s, 1H), 2.92-2.90 (d, J = 4.8 Hz, 3H), 2.87-2.86 (m, 3H), 1.24 (s, 1H), 0.80-0.78 (d, J = 5.2 Hz, 2H), 0.51 (bs, 2H). |

TABLE 27-continued

| Compound # | Reagent | Chiral Separation Conditions and Characterization Data |
|---|---|---|
| I-531 | 96s | MS (ES): m/z 382.40 [M + H]$^+$, LCMS purity: 100%, HPLC purity: 99.46%, $^1$H NMR (DMSO-d$_6$, 400 MHZ): 9.797 (s, 1H), 8.180 (s, 1H), 7.971-7.929 (m, 2H), 7.298 (s, 2H), 6.162 (s, 1H), 4.426-4.421 (bs, 2H), 4.254-4.245 (bs, 2H), 2.904-2.892 (d, J = 4.8 Hz, 3H), 2.848-2.803 (m, 1H), 0.796-0.749 (m, 2H), 0.528-0.490 (m, 2H). |
| I-471 | 96t | MS (ES): m/z 437.07[M + H]$^+$, LCMS purity: 100%, HPLC purity: 99.45%, CHIRAL HPLC: 48.39%, 51.60% $^1$H NMR (DMSO-d$_6$, 400 MHZ): 8.90 (s, 1H), 8.20 (s, 1H), 8.13-8.11 (d, J = 6.8 Hz, 1H), 7.93-7.92 (d, J = 4.8 Hz, 1H), 7.83-7.83 (d, J = 3.6 Hz, 1H), 7.59-7.58 (d, J = 6.8 Hz, 1H), 6.34-6.30 (t, J = 6.8 Hz, 1H), 6.21 (s, 1H), 4.95 (s, 1H), 2.91-2.89 (d, J = 4.8 Hz 2H), 2.09 (s, 4H), 1.79-1.73 (m, 5H), 1.24 (s, 3H), 0.86 (s, 1H), 0.81-0.77 (m, 2H), 0.50 (bs, 2H). |
| I-511 I-512 | 96t | I-471 was separated into isomers: CHIRAL PAK IB (250 mm * 4.6 mm, 5u) in 0.1% diethylamine in methanol at 4 mL/min. FR-a: MS(ES): m/z 437.44 [M + H]$^+$, LCMS purity: 98.26%, HPLC purity: 99.21%, CHIRAL HPLC purity: 95.60%, $^1$H NMR (DMSO-d$_6$, 400 MHZ): 8.89 (s, 1H), 8.19 (s, 1H), 8.13-8.11 (d, J = 7.2 Hz, 1H), 7.91-7.90 (d, J = 4.8 Hz, 1H), 7.83-7.82 (d, J = 4 Hz, 1H), 7.59-7.58 (d, J = 6.4 Hz, 1H), 6.33-6.30 (t, J = 7.2 Hz, 1H), 6.21 (s, 1H), 3.42-3.36 (m, 2H), 2.90-2.87 (d, J = 11.2 Hz, 3H), 2.86-2.84 (m, 1H), 2.81-2.79 (d, J = 7.2 Hz, 1H), 2.68 (s, 1H), 2.22 (s, 3H), 2.00 (s, 1H), 1.75-1.73 (d, J = 9.6 Hz, 3H), 1.66-1.62 (m, 1H), 1.20-1.17 (t, J = 7.2 Hz, 1H) 1.12-1.08 (t, J = 7.2 Hz, 1H), 0.81-0.80 (d, J = 6.8 Hz, 2H). FR-b: MS(ES): m/z 437.51 [M + H]$^+$, LCMS purity: 100%, HPLC purity: 99.40%, CHIRAL HPLC purity: 98.98%, $^1$H NMR (DMSO-d$_6$, 400 MHZ): 8.89 (s, 1H), 8.19 (s, 1H), 8.13-8.11 (d, J = 6.8 Hz, 1H), 7.91-7.90 (d, J = 4.8 Hz, 1H), 7.83-7.82 (d, J = 3.6 Hz, 1H), 7.59-7.57 (d, J = 6.8 Hz, 1H), 6.34-6.30 (t, J = 7.2 Hz, 1H), 6.21 (s, 1H), 3.44 (bs, 2H), 2.90-2.87 (d, J = 11.2 Hz, 3H), 2.86-2.84 (m, 1H), 2.81-2.79 (d, J = 7.2 Hz, 1H), 2.68 (s, 1H), 2.22 (s, 3H), 2.00 (s, 1H), 1.75-1.73 (d, J = 9.6 Hz, 3H), 1.66-1.62 (m, 1H), 1.20-1.17 (t, J = 7.2 Hz, 1H) 1.12-1.08 (t, J = 7.2 Hz, 1H), 0.81-0.80 (d, J = 6.8 Hz, 2H). |

TABLE 27-continued

| Compound # | Reagent | Chiral Separation Conditions and Characterization Data |
|---|---|---|
| I-574 | 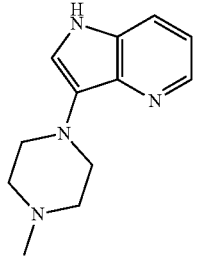<br>96u | MS (ES): m/z 446.53 [M + H]$^+$,<br>LCMS purity: 100%, HPLC purity: 99.81%, $^1$H NMR (DMSO-d$_6$, 400 MHZ): 8.86- 8.84 (d, J = 8 Hz, 1H), 8.49-8.48 (d, J = 4.4 Hz, 2H), 8.40 (s, 1H), 7.85-7.83 (t, J = 4 Hz, 2H), 7.35-7.32 (m, 1H), 6.51 (s, 1H), 3.44 (bs, 4H), 3.13-3.12 (d, J = 4.8 Hz, 3H), 2.93-2.89 (m, 1H), 2.29 (s, 3H), 2.59 (bs, 3H), 1.56(s, 1H), 0.83-0.79 (m, 2H), 0.59-0.55 (m, 2H). |
| I-444 | 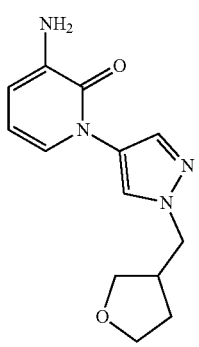<br>96v | MS (ES): m/z 490.32[M + H]$^+$.<br>LCMS purity: 96.96%, HPLC purity: 96.48%, $^1$H NMR (DMSO-d$_6$, 400 MHZ): 9.03 (s, 1H), 8.40 (s, 1H), 8.20 (s, 1H), 8.17-8.15 (d, J = 7.6 Hz, 1H), 7.94 (s, 2H), 7.84-7.83 (d, J = 3.6 Hz, 1H), 7.59-7.57 (d, J = 7.2 Hz, 1H), 6.42-6.38 (t, J = 7.2 Hz, 1H), 6.21 (s, 1H), 5.76 (s, 1H), 4.18-4.16 (d, J = 7.6 Hz, 2H), 3.80-3.75 (m, 1H), 3.71-3.64 (m, 2H), 3.52-3.49 (m, 1H), 2.90-2.84 (m, 4H), 1.96-1.92 (m, 1H), 1.23 (s, 1H), 0.79-0.78 (d, J = 5.2 Hz, 2H), 0.51 (bs, 2H). |
| I-600<br>I-601 | 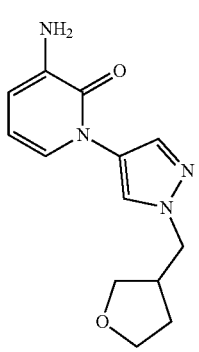<br>96v | I-444 was separated into isomers:<br>CHIRAL PAK IB (250 mm * 4.6 mm, 5u) in 0.1% Diethyl amine in methanol at 4 mL/min.<br>FR-a: MS(ES): m/z 490.54 [M + H]$^+$.<br>LCMS purity: 98.76%, HPLC purity: 98.04%, Chiral HPLC purity: 100%, NMR (DMSO-d$_6$, 400 MHZ): 9.04 (s, 1H), 8.41 (s, 1H), 8.22 (s, 1H), 8.19-8.17 (d, J = 7.2 Hz, 1H), 7.96-7.94 (d, J = 6.4 Hz, 2H), 7.86-7.85 (d, J = 3.2 Hz, 1H), 7.61-7.59 (d, J = 6.8 Hz, 1H), 6.43-6.40 (t, J = 7.2 Hz, 1H), 6.22 (s, 1H), 4.20-4.18 (d, J = 7.2 Hz, 2H), 3.82-3.76 (m, 1H), 3.70-3.63 (m, 2H), 3.54-3.50 (m, 1H), 2.92-2.91 (d, J = 4.4 Hz, 3H), 2.89-2.87 (m, 1H), 2.78-2.74 (m, 1H), 2.00-1.92 (m, 1H), 1.69-1.58 (m, 1H), 0.87-0.80 (m, 2H), 0.53 (bs, 2H).<br>FR-b: MS(ES): m/z 490.54 [M + H]$^+$.<br>LCMS purity: 95.69%, HPLC purity: 95.40%, Chiral HPLC purity: 100%, NMR (DMSO-d$_6$, 400 MHZ): 9.04 (s, 1H), 8.41 (s, 1H), 8.21 (s, 1H), 8.18-8.17 (d, J = 7.2 Hz, 1H), 7.96 (s, 2H), 7.86-7.85 (d, J = 4 Hz, 1H), 7.60-7.59 (d, J = 5.6 Hz, 1H), 6.43-6.39 (t, J = 6.8 Hz, 1H), 6.22 (s, 1H), 4.18-4.17 (J = 7.6 Hz, 2H), 3.78-3.75 (m, 2H), 3.70-3.62 (m, 2H), 2.90-2.89 (d, J = 4.8 Hz, 3H), 2.89-2.87 (m, 1H), 2.76-2.73 (m, 1H), 1.97-1.93 (m, 1H), 1.65-1.61 (m, 1H), 0.85-0.83 (m, 2H), 0.51(bs, 2H). |

TABLE 27-continued

| Compound # | Reagent | Chiral Separation Conditions and Characterization Data |
|---|---|---|
| I-443 | 96w | MS (ES): m/z 419.46 [M + H]+, LCMS purity: 100%, HPLC purity: 98.57%, Chiral HPLC: 50.15: 49.85%, $^1$H NMR (DMSO-d$_6$, 400 MHZ): 8.69 (s, 2H), 8.54 (s, 1H), 8.45 (s, 1H), 8.16 (s, 1H), 7.45 (s, 1H), 6.81 (s, 1H), 5.78 (s, 1H), 4.21 (s, 2H), 4.07 (s, 1H), 3.99-3.97 (d, J = 6.4 Hz, 1H), 3.11 (s, 3H), 2.91 (s, 1H), 1.22 (bs, 2H), 0.85 (bs, 2H), 0.601 (bs, 2H). |
| I-318 | 96x | MS (ES): m/z 523.28 [M + H]+, LCMS purity: 100%, HPLC purity: 97.18%, CHIRAL HPLC purity: 97.18%, $^1$H NMR (DMSO-d$_6$, 400 MHZ): 9.24-9.23 (d, J = 5.6 Hz, 2H), 8.93 (s, 1H), 8.40-8.39 (d, J = 2 Hz, 1H), 8.27 (s, 1H), 8.06-8.05 (d, J = 4.8 Hz, 1H), 7.84-7.84 (d, J = 2.4 Hz, 1H), 7.70-7.70 (d, J = 2.8 Hz, 1H), 6.34 (s, 1H), 3.09-3.05 (m, 6H), 2.92-2.91 (d, J = 4.8 Hz, 3H), 2.83-2.81 (m, 1H), 0.78-0.76 (m, 2H), 0.59 (bs, 2H). |
| I-329 | 96z | MS (ES): m/z 424.20 [M + H]+, LCMS purity: 100%, HPLC purity: 97.46%, $^1$H NMR (DMSO-d$_6$, 400 MHZ): 8.88 (s, 1H), 8.19 (s, 1H), 8.12-8.11 (d, J = 4 Hz, 1H), 7.92-7.91 (d, J = 4 Hz, 1H), 7.82-7.81 (d, J = 4 Hz, 1H), 7.50-7.49 (d, J = 4 Hz, 1H), 6.35-6.33 (t, J = 8 Hz, 1H), 6.20 (s, 1H), 5.03-5.00 (m, 1H), 4.02-4.00 (d, J = 8 Hz, 2H), 3.54-3.51 (t, J = 12 Hz, 2H), 2.90-2.89 (d, J = 4 Hz, 3H), 2.86-2.84 (m, 1H), 2.01-1.93 (m, 2H), 1.77-1.74 (m, 2H), 0.81-0.76 (m, 2H), 0.51-0.47 (m, 2H). |
| I-1044 | 96aa | MS(ES): m/z 452.57 [M + H]+, LCMS purity: 100%, HPLC purity: 99.67%, Chiral HPLC purity: 100%, $^1$H NMR (DMSO-d$_6$, 400 MHZ): 8.87 (s, 1H), 8.20 (s, 1H), 8.15-8.12 (d, J = 7.6 Hz, 1H), 7.93-7.91 (d, J = 4.8 Hz, 1H), 7.86-7.85 (d, J = 3.6 Hz, 1H), 7.41-7.39 (d, J = 6.4 Hz, 1H), 6.32-6.28 (t, J = 7.2 Hz, 1H), 6.18 (s, 1H), 4.91-4.87 (d, J = 13.2 Hz, 1H), 3.58 (bs, 1H), 3.13 (s, 3H), 2.91-2.84 (m, 4H), 2.18-2.06 (m, 2H), 1.93-1.84 (m, 1H), 1.93-1.84 (m, 1H), 1.62-1.41 (m, 4H), 0.84-0.76 (m, 2H), 0.54-0.47 (m, 2H). |
| I-311 | | MS (ES): m/z 454.3 [M + H]+, LCMS purity: 100%, HPLC purity: 98.35%, $^1$H NMR (DMSO-d$_6$, 400 MHZ): 8.30-8.30 (d, J = 2 Hz, 2H), 8.03-8.02 (d, J = 4.4 Hz, 2H), 7.80-7.79 (d, J = 2.4 Hz, 2H), 7.68 (s, 1H), 6.78 (s, 1H), 6.33 (s, 1H), 3.91 (s, 3H), 2.91-2.90 (d, J = 4.8 Hz, 3H), 2.82-2.80 (m, 1H), 0.77-0.75 (m, 4H). |

TABLE 27-continued

| Compound # | Reagent | Chiral Separation Conditions and Characterization Data |
|---|---|---|
| I-955 | 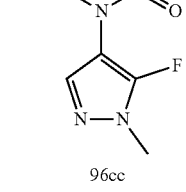<br>96cc | MS (ES): m/z 472.37 [M + H] $^+$<br>LCMS purity: 100%, HPLC purity: 99.20%, $^1$H NMR (DMSO-$d_6$, 400 MHZ): 9.15 (bs, 1H), 8.51-8.32 (bs, 1H), 8.25 (s, 1H), 8.04-8.03 (d, J = 4.4 Hz, 1H), 7.78 (bs, 1H), 7.68 (bs, 1H), 7.63 (bs, 1H), 6.31(bs, 1H), 3.81 (s, 3H), 2.91-2.90 (d, J = 4.4 Hz, 3H), 1.56 (bs, 1H), 0.77-0.75 (d, J = 6 Hz, 2H), 0.58 (bs, 2H). |
| I-281 | 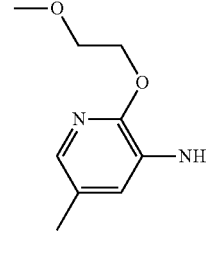 | MS (ES): m/z 412.22 [M + H]$^+$,<br>LCMS purity: 100%, HPLC purity: 99.66%, $^1$H NMR (DMSO-$d_6$, 400 MHZ): 8.77 (s, 1H), 8.15 (s, 1H), 7.99-7.98 (d, J = 2 Hz, 1H), 7.91-7.89 (d, J = 8 Hz, 1H), 7.82-7.81 (d, J = 4 Hz, 1H), 7.75 (s, 1H), 7.82 (s, 1H), 4.46-4.44 (t, J = 8 Hz, 2H), 3.68-3.67 (t, J = 4 Hz, 2H), 3.24 (s, 3H), 2.92-2.90 (d, J = 8 Hz, 3H), 2.74-2.71 (m, 1H), 2.29 (s, 3H), 0.68-0.64 (m, 2H), 0.26-0.22 (m, 2H). |
| I-808 | 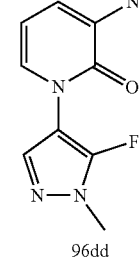<br>96dd | MS (ES): m/z 438.27 [M + H]$^+$,<br>LCMS purity: 100%, HPLC purity: 100%, $^1$H NMR (DMSO-$d_6$, 400 MHZ): 9.03 (s, 1H), 8.22 (s, 1H), 8.20 (s, 1H), 7.96-7.95 (d, J = 4.8 Hz, 1H), 7.84-7.83 (d, J = 3.6 Hz, 1H), 7.76 (bs, 1H), 7.39-7.37 (d, J = 6.8 Hz, 1H), 6.42-6.39 (t, J = 7.2 Hz, 1H), 6.22 (s, 1H), 3.81 (s, 3H), 3.33 (s, 1H), 2.91-2.90 (d, J = 4.8 Hz, 3H), 0.82-0.79 (m, 2H), 0.52 (bs, 2H). |
| I-1012 | 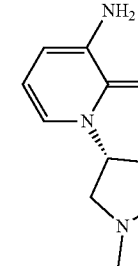 | MS (ES): m/z 462.57 [M + H] $^+$,<br>LCMS purity: 100%, HPLC purity: 99%, CHIRAL HPLC, 100%, $^1$H NMR (DMSO-$d_6$, 400 MHZ): 8.90 (s, 1H), 8.20 (s, 1H), 8.12-8.11(d, J = 6.4 Hz, 1H), 7.92-7.91 (d, J = 5.2 Hz, 1H), 7.83-7.82 (d, J = 4 Hz, 1H), 7.68-7.66 (d, J = 6.8 Hz, 1H), 6.35-6.32 (m, 1H), 6.21 (s, 1H), 5.50 (s, 1H), 3.19-3.02 (m, 1H), 3.00-2.88 (m, 1H), 2.87-2.83 (m, 4H), 2.79-2.70 (m, 3H), 2.68-2.46 (m, 2H), 2.44-2.34 (m, 2H), 1.82-1.77 (m, 1H), 1.24 (bs, 2H), 0.88-0.85 (m, 1H), 0.80-0.79 (m, 1H) |
| I-1011 | 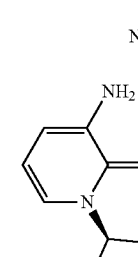 | MS (ES): m/z 462.62 [M + H] $^+$,<br>LCMS purity: 97.26%, HPLC purity: 96.64%, CHIRAL HPLC purity: 95.76%, $^1$H NMR (DMSO-$d_6$, 400 MHZ): 8.90 (s, 1H), 8.20 (s, 1H), 8.13-8.11 (d, J = 7.6 Hz, 1H), 7.93-7.91 (d, J = 4.4 Hz, 1H), 7.68-7.66 (d, J = 7.6 Hz, 1H), 6.35-6.32 (t, J = 7.2 Hz, 1H), 6.21 (s, 1H), 5.51 (m, 1H), 3.97 (m, 1H), 3.14 (m, 1H), 3.02-3.00 (m, 1H), 2.91-2.90 (d, J = 4.4 Hz 2H), 2.87-2.85 (m, 1H), 2.77 (m, 2H), 2.68 (m, 2H), 2.38-2.36 (d, J = 7.6 Hz, 2H), 1.78-1.76 (m, 2H), 1.56 (bs, 1H), 1.25 (bs, 2H), 0.86 (bs, 2H). |

TABLE 27-continued

| Compound # | Reagent | Chiral Separation Conditions and Characterization Data |
| --- | --- | --- |
| I-314 | 96gg | MS (ES): m/z 468.92 [M + H]+, LCMS purity: 98.69%, HPLC purity: 98.19%, ¹H NMR (DMSO-d₆, 400 MHZ): 9.08 (s, 1H), 8.23 (s, 2H), 7.97 (s, 1H), 7.73-7.74 (d, J = 2 Hz, 2H), 6.55 (s, 1H), 6.23 (s, 1H), 3.75 (s, 3H), 2.89 (s, 4H), 2.30 (s, 3H), 0.76 (bs, 2H), 0.55 (bs, 2H). |
| I-933 | | MS (ES): m/z 455.64 [M + H]+, LCMS purity: 98.44%, HPLC purity: 95.52%, ¹H NMR (DMSO-d₆, 400 MHZ): 8.91 (s, 1H), 8.20 (s, 1H), 8.12-8.11 (d, J = 6 Hz 1H), 7.93-7.92 (d, J = 4.8 Hz, 1H), 7.84-7.84 (d, J = 3.6 Hz, 1H), 7.64-7.62 (d, J = 6.8 Hz, 1H), 6.40-6.36 (t, J = 7.2 Hz, 1H), 6.21 (s, 1H), 5.48 (bs, 1H), 4.67-4.65 (t, J = 4.8 Hz, 1H), 4.55-4.53 (t, J = 4.8 Hz, 1H), 3.19-3.12 (m, 1H), 3.17-3.12 (m, 1H), 3.00-2.98 (d, J = 8.8 Hz, 3H), 2.86-2.84 (m, 2H), 2.75-2.71 (m, 2H), 2.47-2.31 (m, 2H), 1.81-1.76 (m, 1H), 1.25-1.24 (d, J = 3.2 Hz, 2H), 0.87-0.87 (d, J = 2 Hz, 2H). |
| I-932 | | MS (ES): m/z 455.64 [M + H]+, LCMS purity: 98.23%, HPLC purity: 95.65%, ¹H NMR (DMSO-d₆, 400 MHZ): 8.91 (s, 1H), 8.20 (s, 1H), 8.12-8.11 (d, J = 6 Hz 1H), 7.93-7.92 (d, J = 4.8 Hz, 1H), 7.84-7.84 (d, J = 3.6 Hz, 1H), 7.64-7.62 (d, J = 6.8 Hz, 1H), 6.40-6.36 (t, J = 7.2 Hz, 1H), 6.21 (s, 1H), 5.48 (bs, 1H), 4.67-4.65 (t, J = 4.8 Hz, 1H), 4.55-4.53 (t, J = 4.8 Hz, 1H), 3.19-3.12 (m, 1H), 3.17-3.12 (m, 1H), 3.00-2.98 (d, J = 8.8 Hz, 3H), 2.86-2.84 (m, 2H), 2.75-2.71 (m, 2H), 2.47-2.31 (m, 2H), 1.81-1.76 (m, 1H), 1.25-1.24 (d, J = 3.2 Hz, 2H), 0.87-0.87 (d, J = 2 Hz, 2H). |
| I-859 | | MS (ES): m/z 422.48 [M + H]+, LCMS purity: 95.51%, HPLC purity: 95.98%, ¹H NMR (DMSO-d₆, 400 MHZ): 9.92 (bs, 1H), 8.23 (s, 1H), 8.19 (s, 1H), 8.11 (bs, 1H), 7.99 (s, 1H), 7.80-7.76 (t, J = 8 Hz, 1H), 7.39-7.36 (d, J = 8.4 Hz, 1H), 7.20-7.18 (d, J = 7.2 Hz, 1H), 6.86 (bs, 1H), 3.81 (s, 3H), 2.99 (s, 3H), 2.85-2.82 (m, 1H), 1.24 (s, 2H), 0.80-0.76 (m, 2H). |

TABLE 27-continued

| Compound # | Reagent | Chiral Separation Conditions and Characterization Data |
|---|---|---|
| I-479 | 96hh | MS (ES): m/z 475.56 [M + H]$^+$, LCMS purity: 100%, HPLC purity: 100 %, $^1$H NMR (DMSO-d$_6$, 400 MHZ): 8.72 (bs, 2H), 8.56-8.54 (d, J = 4.4 Hz, 2H), 8.46 (s, 1H), 8.20-8.19 (d, J = 3.2 Hz, 2H), 7.45-7.42 (m, 1H), 6.85 (s, 1H), 4.73-4.70 (t, J = 6.4 Hz, 2H), 3.10-3.09 (d, J = 4.4 Hz, 3H), 2.94-2.88 (m, 3H), 2.26 (bs, 4H), 2.12 (s, 4H), 0.85-0.83 (d, J = 6.4 Hz, 3H), 0.62 (bs, 2H). |
| I-457 | 96jj | MS (ES): m/z 460.22 [M + H]$^+$, LCMS purity: 100%, HPLC purity: 99.75 %, $^1$H NMR (DMSO-d$_6$, 400 MHZ): 8.68 (s, 2H), 8.54 (s, 1H), 8.45 (s, 1H), 8.18 (s, 1H), 7.43 (bs, 1H), 6.83 (s, 1H), 4.71 (bs, 2H), 3.10 (s, 3H), 2.92-2.86 (bs, 3H), 2.36 (bs, 4H), 1.41-1.35 (m, 6H), 0.87-0.85 (m, 2H) 0.64-0.60 (m, 2H). |
| I-455 | 96ll | MS (ES): m/z 462.22 [M + H]$^+$, LCMS purity: 100 %, HPLC purity: 100%, $^1$H NMR (DMSO-d$_6$, 400 MHZ): 8.69-8.67 (d, J = 5.6 Hz 2H), 8.55-8.54 (d, J = 4.4 Hz, 1H), 8.45 (s, 1H), 8.17 (s, 1H), 7.44-7.41 (t, J = 12 Hz, 1H), 6.82 (s, 1H), 4.75-4.71 (t, J = 12.8 Hz, 2H), 3.57 (s, 1H), 3.49 (s, 3H), 3.41-3.46 (m, 3H), 3.09 (s, 3H), 2.91-2.80 (t, J = 12.4 Hz, 3H), 1.11.1.08 (m, 1H), 0.91-0.90 (m, 2H) 0.76-0.74 (m, 2H). |
| I-680 | | MS (ES): m/z 417.33 [M + H]$^+$, LCMS purity: 99.37%, HPLC purity: 99.25%, $^1$H NMR (DMSO-d$_6$, 400 MHZ): 9.01 (s, 1H), 8.65-8.64 (d, J = 4.0 Hz, 1H), 8.24-8.23 (d, J = 4.0 Hz, 1H) 8.21 (s, 2H), 8.07-8.03 (m, 1H), 7.95-7.94 (d, J = 4.0 Hz, 2H), 7.86-7.84 (d, J = 8.0 Hz, 1H), 7.61-7.53 (m, 2H), 6.46-6.42 (t, J = 8.0 Hz, 1H), 6.22 (s, 1H), 2.90-2.89 (d, J = 4.0 Hz, 3H), 0.80-0.79 (d, J = 4.0 Hz, 2H), 0.54-0.52 (m, 2H). |

TABLE 27-continued

| Compound # | Reagent | Chiral Separation Conditions and Characterization Data |
|---|---|---|
| I-364 | 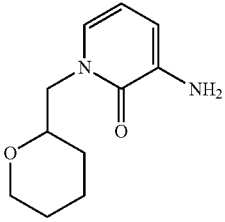<br>96mm | MS (ES): m/z 438.50 [M + H]⁺, LCMS purity: 100%, HPLC purity: 99.67%, Chiral HPLC purity: 49.58% + 3050.41%, $^1$H NMR (DMSO-$d_6$, 400 MHZ): 8.86 (s, 1H), 8.18 (s, 1H), 8.12-8.11 (d, J = 7.2 Hz, 1H), 7.90-7.88 (d, J = 4.8 Hz, 1H), 7.83-7.82 (dJ = 3.6 Hz, 1H), 7.31-7.29 (d, J = 6.8 Hz, 1H), 6.27-6.23 (t, J = 6.8 Hz, 1H), 6.17 (s, 1H), 4.15-4.11 (m, 1H), 3.92-3.85 (m, 2H), 3.67-3.65 (d, J = 8 Hz, 1H), 3.27-3.25 (bs, 1H), 2.90-2.83 (m, 4H), 1.79 (bs, 1H), 1.62-1.59 (d, J = 11.6 Hz, 1H), 1.46 (bs, 2H), 1.28-1.23 (t, J-12 Hz, 2H), 0.81-0.78 (t, J = 6.4 Hz, 2H), 0.31-0.47 (m, 2H). |
| I-412<br>I-413 | 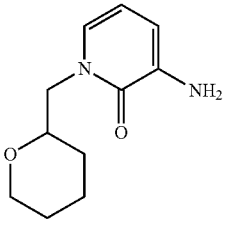<br>96mm | I-364 was separated into isomers: CHIRAL PAK IB (250 mm * 4.6 mm, 5u) in 0.1% diethylamine in methanol at 4 mL/min.<br>FR-a: MS(ES): m/z 438.2 [M + H]⁺, LCMS purity: 100%, HPLC purity: 100%, CHIRAL HPLC purity: 100%, $^1$H NMR (DMSO-$d_6$, 400 MHZ): 8.87 (s, 1H), 8.19(s, 1H), 8.12-8.10 (d, J = 7.2 Hz, 1H), 7.90-7.88 (d, J = 4.8 Hz, 1H), 7.83-7.82 (d, J = 3.6 Hz, 1H), 7.30-7.29 (d, J = 6.8 Hz, 1H), 6.27-6.23 (t, J = 6.8 Hz, 1H), 6.17 (s, 1H), 4.15-4.11 (m, 1H), 3.92-3.84 (m, 2H), 3.67-3.65 (d, J = 8 Hz, 1H), 3.30-3.27 (m, 1H), 2.89-2.82 (m, 4H), 1.79 (bs, 1H), 1.62-1.59 (d, J = 11.6 Hz, 1H), 1.45 (bs, 3H), 1.28-1.23 (m, 1H), 0.81-0.78 (t, J = 6.4 Hz, 2H), 0.51-0.47 (m, 2H).<br>FR-b: MS(ES): m/z 438.3 [M + H]⁺, LCMS purity: 100%, HPLC purity: 100%, CHIRAL HPLC purity: 97.8%, $^1$H NMR (DMSO-$d_6$, 400 MHZ): 8.87 (s, 1H), 8.19 (s, 1H), 8.12-8.10 (d, J = 7.2 Hz, 1H), 7.92-7.88 (m, 1H), 7.83-7.82 (d, J = 3.6 Hz, 1H), 7.30-7.29 (d, J = 6.8 Hz, 1H), 6.27-6.23 (t, J = 6.8 Hz, 1H), 6.17 (s, 1H), 4.15-4.11 (m, 1H), 3.92-3.84 (m, 2H), 3.67-3.61 (m, 1H), 3.33-3.27 (m, 1H), 2.89-2.82 (m, 4H), 1.79 (bs, 1H), 1.62-1.59 (d, J = 11.6 Hz, 1H), 1.46 (bs, 3H), 1.28-1.23 (m, 1H), 0.80-0.76 (t, J = 6.4 Hz, 2H), 0.51-0.47 (m, 2H). |
| I-708 | 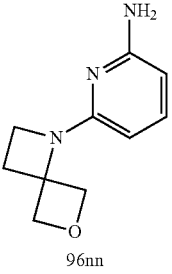 [SMILES: Nc1cccc(N2CCC23COC3)n1]<br>96nn | MS (ES): m/z 421.27[M + H]⁺, LCMS purity: 99.66%, HPLC purity: 99.48%, $^1$H NMR (DMSO-$d_6$, 400 MHZ): 9.61 (s, 1H), 8.20 (s, 1H), 8.02-8.01 (d, J = 3.2 Hz, 2H), 7.58-7.54 (t, J = 8 Hz, 1H), 6.88-6.86 (d,J = 7.2 Hz, 1H), 6.75 (bs, 1H), 6.35-6.33(d, J = 8 Hz, 1H), 5.26-5.25 (d, J = 6.8 Hz, 2H), 4.67-4.65 (d, J = 7.2 Hz, 2H), 3.88-3.84 (t, J = 6.8 Hz, 2H), 3.19-3.17 (d, J = 5.2 Hz, 1H), 2.95-2.93 (d, J = 4.8 Hz, 3H), 2.87-2.83 (m, 1H), 2.69 (bs, 1H), 0.80-0.76 (m, 2H), 0.57 (bs, 2H). |

TABLE 27-continued

| Compound # | Reagent | Chiral Separation Conditions and Characterization Data |
|---|---|---|
| I-618 | 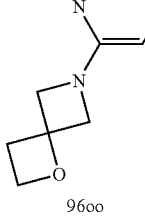<br>96oo | MS(ES): m/z 421.48 [M + H]+<br>LCMS purity: 100%, HPLC purity: 99.77%, NMR (DMSO-$d_6$, 400 MHZ): 9.64 (s, 1H), 8.19 (s, 1H), 8.02-8.00 (m, 2H), 7.50-7.46 (t, J = 8 Hz, 1H), 6.83 (s, 2H), 6.03-6.01 (d, J = 8 Hz, 1H), 4.47-4.44 (t, J = 7.2 Hz, 2H), 4.24-4.22 (d, J = 9.2 Hz, 2H), 2.97-2.82 (m, 4H), 2.09 (s, 3H), 1.34 (m, 1H), 0.77-0.75 (d, J = 14 Hz, 2H), 0.56 (bs, 2H). |
| I-378 | 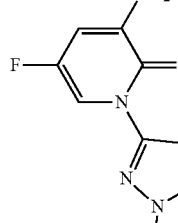<br>96pp | MS (ES): m/z 438.44 [M + H]+,<br>LCMS purity: 100%, HPLC purity: 99.61%, $^1$H NMR (DMSO-$d_6$, 400 MHZ): 9.22 (s, 1H), 8.36-8.33 (dd, J = 2.8 Hz, 9.6 Hz, 1H), 8.25 (s, 1H), 8.02-8.01 (d, J = 4.4 Hz, 1H), 7.85-7.77 (m, 2H), 7.66-7.65 (d, J = 3.2 Hz, 1H), 6.82-6.81 (d, J = 1.6 Hz, 1H), 6.35 (s, 1H), 3.90 (s, 3H), 2.91-2.90 (d, J = 4.4 Hz, 3H), 2.86-2.84 (m, 1H), 0.75-0.73 (m, 2H), 0.56 (s, 2H). |
| I-380 | 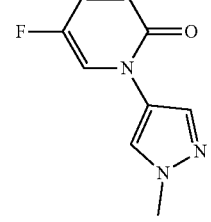<br>96qq | MS (ES): m/z 438.22 [M + H]+,<br>LCMS purity: 100%, HPLC purity: 99.24%, $^1$H NMR (DMSO-$d_6$, 400 MHZ): 9.21 (s, 1H), 8.36-8.33 (m, 2H), 8.26 (s, 1H), 8.03-8.02 (s, 1H), 7.97 (s, 1H), 7.80 (s, 1H), 7.68-7.68 (d, J = 3.2 Hz 1H), 6.36 (s, 1H), 3.92 (s, 3H), 2.92-2.85 (m, 3H), 2.51 (s, 1H), 0.75-0.74 (d, J = 5.6 Hz ,2H), 0.57 (bs, 2H). |
| I-310 | 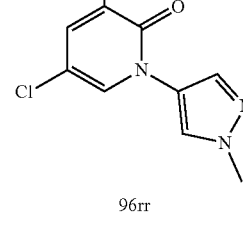<br>96rr | MS (ES): m/z 454.89 [M + H]+,<br>LCMS purity: 100%, HPLC purity: 99.64%, $^1$H NMR (DMSO-$d_6$, 400 MHZ): 9.15(s, 1H), 8.35 (s, 1H), 8.29-8.28 (m, 2H), 8.06-8.05 (d, J = 4.8 Hz, 1H), 7.96 (s, 1H), 7.80-7.76 (m, 2H), 6.34 (s, 1H), 3.92 (s, 3H), 2.92-2.91 (m, 3H), 2.89-2.87 (m, 1H), 1.25-1.15 (m, 2H), 1.04-0.96 (m, 1H), 1.06-1.05 (m, 1H). |
| I-431 | 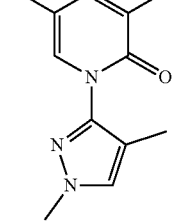<br>96ss | MS (ES): m/z 452.17 [M + H]+,<br>LCMS purity: 97.83%, HPLC purity: 96.58%, $^1$H NMR (DMSO-$d_6$, 400 MHZ): 8.81-8.79 (d, J = 5.2 Hz, 1H), 8.52 (s, 1H), 7.81 (s, 2H), 7.74-7.72 (m, 1H), 7.66 (s, 1H), 7.46 (s, 1H), 6.87 (s, 1H), 3.78 (s, 3H), 3.04-3.03 (d, J = 4.8 Hz, 3H), 2.82-2.79 (m, 1H), 1.98 (s, 3H), 0.76-0.75 (d, J = 5.2 Hz, 2H), 0.53 (bs, 2H). |

TABLE 27-continued

| Compound # | Reagent | Chiral Separation Conditions and Characterization Data |
|---|---|---|
| I-333 | 96tt | MS (ES): m/z 492.27 [M + H]+, LCMS purity: 97.69%, HPLC purity: 97.92%, 1H NMR (DMSO-d6, 400 MHZ): 9.17 (s, 1H), 8.39 (s, 1H), 8.26 (s, 1H), 8.03-8.00 (m, 2H), 7.82-7.781 (m, 2H), 7.70 (s, 1H), 6.32 (s, 1H), 2.91 (bs, 3H), 2.81 (bs, 1H), 2.38 (m, 1H), 1.19-1.15 (m, 4H), 0.77-0.76 (m, 2H), 0.59 (bs, 2H). |
| I-581 | 96uu | MS (ES): m/z 441.41 [M + H]+, LCMS purity: 99.09%, HPLC purity: 97.46%, 1H NMR (DMSO-d6, 400 MHZ): 9.09 (s, 1H), 8.91-8.86 (t, J = 8.0 Hz, 1H), 8.14 (s, 1H), 7.97-7.95 (m, 1H), 7.86-7.84 (d, J = 3.6 Hz, 1H), 7.78-7.72 (m, 1H), 7.71-7.70 (d, J = 3.2 Hz, 1H), 6.93-6.89 (t, J = 8.0 Hz, 1H), 5.71(s, 1H), 2.93 (s, 3H), 2.65-2.60 (m, 1H), 0.58-0.53 (m, 2H), 0.12 (bs, 2H). |
| I-883 | 96vv | MS (ES): m/z 471.60 [M + H]+, LCMS purity: 99.30%, HPLC purity: 98.75%, 1H NMR (DMSO-d6, 400 MHZ) : 9.01 (s, 1H), 8.24 (s, 1H), 8.22 (s, 1H), 8.01-8.00 (d, J = 4.8 Hz, 1H), 7.66-7.65 (d, J = 3.2 Hz, 1H), 7.62-7.61 (d, J = 2.4 Hz, 1H), 6.30 (s, 1H), 3.19-3.17 (d, J = 5.2 Hz, 1H), 2.95 (bs, 2H), 2.91-2.90 (d, J = 4.8 Hz, 3H), 2.82-2.77 (m, 1H), 2.24 (s, 3H), 2.09-1.97 (m, 4H), 1.77 (bs, 2H), 0.78-0.77 (m, 2H), 0.58-0.54 (m, 2H). |
| I-623 | 96ww | MS (ES): m/z 400.41 [M + H]+, LCMS purity: 98.27%, HPLC purity: 97.95%, 1H NMR (DMSO-d6, 400 MHZ): 8.69 (s, 1H), 8.12 (s, 1H), 7.91-7.83 (m, 3H), 6.55-6.50 (t, J = 7.6 Hz, 1H), 5.66 (s, 1H), 5.10-5.07 (t, J = 6.4 Hz, 1H), 2.91-2.90 (d, J = 4.4 Hz, 3H), 2.73 (bs, 1H), 1.37-1.35 (d, J = 6.4 Hz, 6H), 0.66 (bs, 2H), 0.22 (bs, 2H). |
| I-453 | 96xx | MS (ES): m/z 424.17 [M + H]+, LCMS purity: 97.92%, HPLC purity: 95.02%, 1H NMR (DMSO-d6, 400 MHZ): 8.91 (s, 1H), 8.19 (s, 1H), 8.14-8.13 (d, J = 1.6 Hz, 1H), 7.92-7.91 (d, J = 5.2 Hz, 1H), 7.84-7.83 (d, J = 4 Hz, 1H), 7.33-7.32 (m, 1H), 6.29-6.25 (t, J = 7.2 Hz, 1H), 6.19 (s, 1H), 4.17-4.14 (t, J = 5.2 Hz, 2H), 3.76-3.73 (t, J = 10.4 Hz, 2H), 3.35 (s, 1H), 2.89-2.84 (m, 4H), 0.81-0.76 (m, 2H), 0.49 (bs, 2H), 0.41 (bs, 4H). |

TABLE 27-continued

| Compound # | Reagent | Chiral Separation Conditions and Characterization Data |
|---|---|---|
| I-313 | Intermediate A | MS (ES): m/z 424.48 [M + H]$^+$, LCMS purity: 97.21%, HPLC purity: 97.58%, CHIRAL HPLC: (50%), (40%), $^1$H NMR (DMSO-d$_6$, 400 MHZ): 8.92 (s, 1H), 8.19 (s, 1H), 8.14-8.12 (d, J = 7.2 Hz, 1H), 7.93-7.92 (d, J = 4.4 Hz, 1H), 7.83-7.82 (d, J = 2.8 Hz, 1H), 7.55-7.53 (d, J = 6.8 Hz, 1H), 6.35-6.32 (t, J = 14.4 Hz, 1H), 6.21 (s, 1H), 4.88 (s, 1H), 3.60-3.55(m, 1H), 3.49-3.44(m, 1H), 3.18-3.17 (d, J = 5.2 Hz, 1H), 2.90-2.89 (d, J = 4.4 Hz, 3H), 2.68 (s, 1H), 2.07-1.98 (m, 2H), 1.77-1.73 (m, 2H), 1.56 (s, 1H), 0.80-0.078 (d, J = 6 Hz, 2H), 0.50 (bs, 2H). |
| I-351 I-352 | Intermediate A | I-313 was separated into isomers: CHIRAL PAK IB (250 mm * 4.6 mm, 5u) in 0.1% diethylamine in methanol at 4 mL/min. FR-a: MS (ES): m/z 424.48 [M + H]$^+$, LCMS purity: 100%, HPLC purity: 99.84% CHIRAL HPLC: 100%, $^1$H NMR (DMSO-d$_6$, 400 MHZ): 8.91 (s, 1H), 8.19 (s, 1H), 7.92-7.90 (d, J = 4.8 Hz, 1H), 7.82-7.81 (d, J = 4 Hz, 1H), 7.54-7.52 (d, J = 8 Hz, 1H), 6.34-6.31 (t, J = 7.2 Hz, 1H), 6.20 (s, 1H), 4.90-4.85 (m, 1H), 3.85-3.81 (m, 2H), 3.60-3.48 (m, 3H), 2.90-2.84 (m, 4H), 2.09-2.01 (m, 2H), 1.76-1.70 (m, 2H), 1.10-1.07 (t, 1H), 0.85-0.80 (m, 2H), 0.76 (bs, 1H). FR-b: MS (ES): m/z 424.48 [M + H]$^+$, LCMS purity: 100%, HPLC purity: 99.90%, CHIRAL HPLC: 100%, $^1$H NMR (DMSO-d$_6$, 400 MHZ): 8.91 (s, 1H), 8.19 (s, 1H), 7.92-7.90 (d, J = 4.8 Hz, 1H), 7.82-7.81 (d, J = 4 Hz, 1H), 7.54-7.52 (d, J = 8 Hz, 1H), 6.34-6.31 (t, J = 7.2 Hz, 1H), 6.20 (s, 1H), 4.90-4.85 (m, 1H), 3.85-3.81 (m, 2H), 3.60-3.48 (m, 3H), 2.90-2.84 (m, 4H), 2.09-2.01 (m, 2H), 1.76-1.70 (m, 2H), 1.10-1.07 (t, J = 12 Hz, 1H), 0.85-0.80 (m, 2H), 0.76 (bs, 1H). |
| I-322 | 96yy | MS (ES): m/z 471.94 [M + H]$^+$, LCMS purity: 100%, HPLC purity: 100%, $^1$H NMR (CDC13, 400 MHZ): 8.51 (s, 1H), 8.36 (s, 1H), 7.82 (s, 1H), 7.65 (s, 1H), 7.30 (s, 1H) 5.81(s, 3H), 3.26 (s, 3H), 2.83(s, 1H), 2.64(s, 3H), 0.97-0.95 (d, J = 6.4 Hz, 2H), 0.74 (bs, 2H). |
| I-368 | 96zz | MS (ES): m/z 421.45 [M + H]$^+$, LCMS purity: 100%, HPLC purity: 99.87%, $^1$H NMR (DMSO-d$_6$, 400 MHZ): 9.06 (s, 1H), 8.25-8.21 (m, 2H), 8.03 (s, 1H), 7.99-7.97 (d, J = 4.4 Hz, 1H), 7.80-7.79 (d, J = 3.6 Hz, 1H), 7.48-7.46 (dd, J = 1.6 Hz, J = 5.2 Hz, 1H), 6.45-6.41 (t, J = 8 Hz, 1H), 6.19 (s, 1H), 2.90-2.87 (m, 3H), 2.86-2.84 (m, 1H), 2.19 (s, 3H), 0.80-0.76 (m, 2H), 0.52-0.48 (m, 2H). |

TABLE 27-continued

| Compound # | Reagent | Chiral Separation Conditions and Characterization Data |
|---|---|---|
| I-331 | 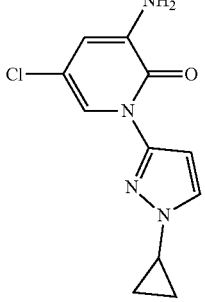<br>36aaa | MS (ES): m/z 480.21 [M + H]+, LCMS purity: 100%, HPLC purity: 99.89%, $^1$H NMR (DMSO-d$_6$, 400 MHZ): 9.17 (s, 1H), 8.30-8.29 (d, J = 8 Hz, 1H), 8.24 (s, 1H), 8.02-8.01 (d, J = 4 Hz, 1H), 7.956-7.951 (d, J = 2 Hz, 1H), 7.80-7.79 (d, J = 4 Hz, 1H), 7.67-7.66 (d, J = 4 Hz, 1H), 6.77-6.76 (d, J = 4 Hz, 1H), 6.32 (s, 1H), 3.81-3.78 (m, 1H), 2.90-2.89 (d, J = 4 Hz, 3H), 2.82-2.78 (m, 1H), 1.14-1.07 (m, 2H), 1.03-0.98 (m, 2H), 0.78-0.73 (m, 2H), 0.59-0.55 (m, 2H). |
| I-406 | 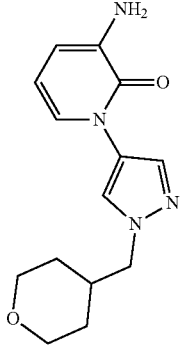<br>96bbb | MS (ES): m/z 504.57 [M + H]+. LCMS purity: 100%, HPLC purity: 93.37%, $^1$H NMR (DMSO-d$_6$, 400 MHZ): 9.03 (s, 1H), 8.34 (s, 1H), 8.20(s, 1H), 8.17-8.15 (d, J = 8.0 Hz, 1H), 7.94-7.93 (d, J = 4.0 Hz, 2H), 7.84-7.83 (d, J = 4.0 Hz, 1H), 7.59-7.57 (d, J = 8.0 Hz, 1H), 6.41-6.38 (t 1H), 6.21(s, 1H), 4.08-4.07 (d, J = 4.0 Hz, 2H), 3.85-3.83 (d, J = 8.0 Hz, 2H), 3.29-3.24 (m, 2H), 2.90-2.84 (m, 4H), 2.09-2.08 (d, J = 4.0 Hz, 1H), 1.45-1.42 (d, J = 12.0 Hz, 2H), 1.31-1.22(m, 2H), 0.81-.077 (m, 2H), 0.51(bs, 2H). |
| I-964 | 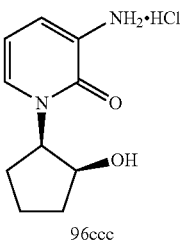<br>96ccc | MS (ES): m/z 424.57 [M + H]+, LCMS purity: 97.94%, HPLC purity: 97.99%, CHIRAL HPLC: 98.63%, $^1$H NMR (DMSO-d$_6$, 400 MHZ): 8.88 (s, 1H), 8.20 (s, 1H), 8.13-8.12 (d, J = 6.4 Hz, 1H), 7.92-7.90 (d, J = 4.8 Hz, 1H), 7.87-7.86 (d, J = 3.6 Hz, 1H), 7.45-7.43 (d, J = 6.0 Hz, 1H), 6.30-6.26 (t, J = 7.2 Hz, 1H), 6.21 (s, 1H), 4.99-4.94 (m, 1H), 4.88 (bs, 1H), 4.20 (s, 1H), 2.91-2.85 (m, 4H), 2.15-1.88 (m, 4H), 1.71-1.61 (m, 2H), 0.82-0.77 (m, 2H), 0.53-0.52 (m, 2H). |
| I-294 | 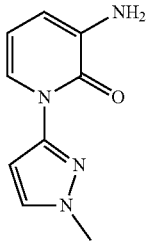 | MS (ES): m/z 420.38 [M + H]+, LCMS purity: 100%, HPLC purity: 98.47%, $^1$H NMR (DMSO-d$_6$, 400 MHZ): 9.03 (s, 1H), 8.21 (s, 1H), 8.20-8.18 (d, J = 8 Hz, 1H), 7.95-7.94 (d, J = 4 Hz, 1H), 7.84 (s, 2H), 7.69-7.67 (d, J = 8 Hz, 1H), 6.756-6.751 (d, J = 2 Hz, 1H), 6.42-6.41 (d, J = 4 Hz, 1H), 6.22 (s, 1H), 3.91 (s, 3H), 2.91-2.90 (d, J = 4 Hz, 3H), 2.88-2.87 (m, 1H), 0.80-0.79 (m, 2H), 0.52 (bs, 2H). |
| I-963 | 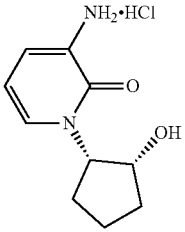<br>96ddd | MS (ES): m/z 424.35 [M + H]+, LCMS purity: 98.35%, HPLC purity: 97.78%, CHIRAL HPLC: 97.73%, $^1$H NMR (DMSO-d$_6$, 400 MHZ): 8.88 (s, 1H), 8.20 (s, 1H), 8.13-8.12 (d, J = 6.4 Hz, 1H), 7.92-7.90 (d, J = 4.8 Hz, 1H), 7.87-7.86 (d, J = 3.6 Hz, 1H), 7.44-7.43 (d, J = 6.0 Hz, 1H), 6.29-6.26 (t, J = 7.2 Hz, 1H), 6.21 (s, 1H), 5.00-4.93 (m, 1H), 4.89 (bs, 1H), 4.20 (s, 1H), 2.91-2.85 (m, 4H), 2.15-1.88 (m, 4H), 1.71-1.61 (m, 2H), 0.82-0.77 (m, 2H), 0.53-0.52 (m, 2H). |

TABLE 27-continued

| Compound # | Reagent | Chiral Separation Conditions and Characterization Data |
|---|---|---|
| I-625 | 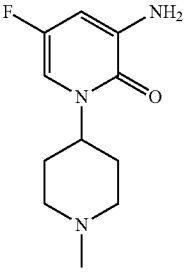<br>96eee | MS (ES): m/z 455.35 [M + H]$^+$, LCMS purity: 98.77%, HPLC purity: 98.24%, $^1$H NMR (DMSO-d$_6$, 400 MHZ): 9.08 (s, 1H), 8.28-8.27 (d, J = 2.8 Hz, 1H), 8.25 (s, 1H), 8.01 (bs, 1H), 7.67-7.63 (m, 2H), 6.33 (s, 1H), 4.73 (bs, 1H), 2.91 (s, 3H), 2.86-2.83 (m, 1H), 2.23 (s, 3H), 2.09-2.07 (d, J = 11.6 Hz, 3H), 2.04-1.94 (m, 2H), 1.76-1.67 (m, 2H), 1.12-1.09 (t, J = 6.85 Hz, 1H), 0.75-0.74 (d, J = 5.2 Hz, 2H), 0.55 (bs, 2H). |
| I-348 | 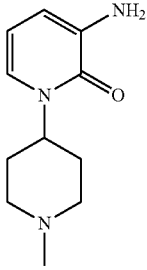<br>96fff | MS(ES): m/z 437.52 [M + H]$^+$, LCMS purity: 100%, HPLC purity: 99.68%, $^1$H NMR (DMSO-d$_6$, 400 MHZ): 8.87 (s, 1H), 8.19 (s, 1H), 8.12-8.10 (d, J = 6.8 Hz, 1H), 7.90-7.89 (d, J = 4 Hz, 1H), 7.82-7.81 (d, J = 3.2 Hz, 1H), 7.47-7.45 (d, J = 6.4 Hz, 1H), 6.33-6.30 (t, J = 7.2 Hz, 1H), 6.19 (s, 1H), 4.78-4.75 (d, J = 7.6 Hz, 1H), 2.93-2.84 (m, 6H), 2.22 (s, 3H), 2.09-2.03 (m, 4H), 1.76-1.73 (d, J = 10.4 Hz, 2H), 0.79-0.77 (d, J = 5.6 Hz, 2H), 0.49 (bs, 1H). |
| I-154 | 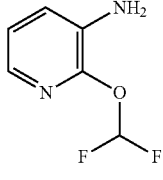 [SMILES: Nc1cccnc1OC(F)F] | MS(ES): m/z 390.47 [M + H]$^+$, LCMS purity: 100%, HPLC purity: 98.89%, $^1$H NMR (DMSO-d$_6$, 400 MHZ): 9.15 (s, 1H), 8.36-8.34 (d, J = 8 Hz, 1H), 8.16 (s, 1H), 8.02-8.01 (m, 2H), 7.78 (s, 1H), 7.72-7.71 (d, J = 3.6 Hz 1H), 7.32-7.29 (m, 1H) 5.87 (s, 1H), 2.92 (s, 3H), 2.76-2.76 (d, J = 3.2 Hz, 1H), 0.69-0.682 (d, J = 6.8 Hz, 2H), 0.30 (bs, 2H). |
| I-910 | 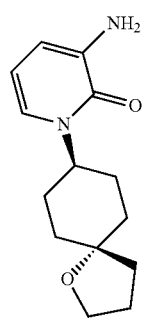<br>96ggg | MS (ES): m/z 478.87 [M + H]$^+$, LCMS purity: 100%, HPLC purity: 98.27%, Chiral HPLC: 99.53%, $^1$H NMR (DMSO-d$_6$, 400 MHZ): 8.88 (s, 1H), 8.20 (s, 1H), 8.12-8.10 (d, J = 6.4 Hz, 1H), 7.92-7.91 (d, J = 4.8 Hz, 1H), 7.83-7.82 (d, J = 4 Hz, 1H), 7.39-7.38 (d, J = 6 Hz, 1H), 6.34-6.30 (t, J = 6.8 Hz, 1H), 6.20 (bs, 1H), 4.86-4.80 (t, J = 12 Hz, 1H), 3.79-3.75 (t, J = 6.8 Hz, 2H), 2.91-2.84 (m, 4H), 2.19-1.23 (m, 10H), 0.88-0.85 (t, J = 13.6 Hz, 2H), 0.81-0.77 (m, 2H), 0.52-0.48 (m, 2H). |
| I-1109 | 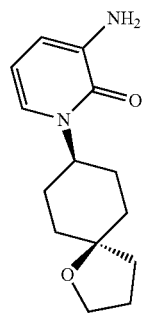 [SMILES: Nc1cccn([C@H]2CC[C@]3(CCCO3)CC2)c1=O] | MS (ES): 478.52 [M + H]$^+$ LCMS purity: 100%, HPLC purity: 97.86%, %, $^1$H NMR (DMSO-d$_6$, 400 MHZ): 8.87 (s, 1H), 8.19 (s, 1H), 8.11-8.09 (d, J = 6.4 Hz, 1H), 7.92-7.91 (d, J = 4.8 Hz, 1H), 7.82-7.81 (d, J = 4 Hz, 1H), 7.38-7.37 (d, J = 6 Hz, 1H), 6.33-6.29 (t, J = 7.2 Hz, 1H), 6.19 (s, 1H), 3.77-3.74 (t, J = 6.4 Hz, 2H), 2.90-2.89 (d, J = 4.8 Hz, 3H), 2.86-2.83 (m, 1H), 1.96-1.84 (m, 4H), 1.75 (bs, 2H), 1.58 (bs, 1H), 1.23 (bs, 4H), 0.87-0.84 (t, J = 6.8 Hz, 2H), 0.79-0.76 (m, 2H), 0.51 (bs, 2H). |

TABLE 27-continued

| Compound # | Reagent | Chiral Separation Conditions and Characterization Data |
|---|---|---|
| I-361 | 96hhh | MS (ES): m/z 466.26 [M + H]+, LCMS purity: 98.98%, HPLC purity: 95.08%, Chiral HPLC purity: 97.85%, $^1$H NMR (DMSO-d$_6$, 400 MHZ): 8.88 (s, 1H), 8.19 (s, 1H), 8.12-8.10 (d, J = 6.4 Hz, 1H), 7.92-7.91 (d, J = 5.2 Hz, 1H), 7.84-7.83 (d, J = 4 Hz, 1H), 7.56-7.54 (d, J = 6.4 Hz, 1H), 6.33-6.31 (t, J = 7.2 Hz, 1H), 6.19 (s, 1H), 3.17 (s, 3H), 2.91-2.83 (m, 4H), 2.09 (s, 1H), 1.94-1.75 (m, 6H), 1.60-1.54 (m, 3H), 1.26 (s, 4H), 0.52 (bs, 2H). |
| I-371 | 96iii | MS (ES): m/z 452.27 [M + H]+, LCMS purity: 97.89%, HPLC purity: 95.45%, Chiral HPLC purity: 96.89%, $^1$H NMR (DMSO-d$_6$, 400 MHZ): 8.88 (s, 1H), 8.19 (s, 1H), 8.11-8.10 (d, J = 7.2 Hz, 1H), 7.91-7.90 (d, J = 4.4 Hz, 1H), 7.83 (bs, 1H), 7.54-7.52 (d, J = 6.4 Hz, 1H), 6.32-6.29 (t, J = 6.8 Hz, 1H), 6.19 (s, 1H), 4.74-4.71 (m, 1H), 2.91-2.85 (m, 4H), 1.90-1.81 (m, 2H), 1.71-1.68 (m, 4H), 1.62-1.59 (m, 2H), 1.27 (bs, 4H), 0.79-0.78 (d, 2H), 0.50 (bs, 2H). |
| I-414 | | MS (ES): m/z 452.22 [M + H]+, LCMS purity: 100 %, HPLC purity: 100 %, $^1$H NMR (DMSO-d$_6$, 400 MHZ): 8.87 (s, 1H), 8.18 (s, 1H), 8.10-8.09 (d, J = 6.8 Hz, 1H), 7.90-7.89 (d, J = 4.8 Hz, 1H), 7.83-7.82 (d, J = 3.6 Hz, 1H), 7.53-7.51 (d, J = 6.4 Hz, 1H), 6.32-6.28 (t, J = 14 Hz, 1H), 6.18 (s, 1H), 4.73 (bs, 1H), 4.48 (s, 1H), 2.90-2.84 (m, 4H), 1.86-1.80 (m, 2H), 1.70-1.68 (m, 4H), 1.61-1.55 (m, 2H), 1.26 (s, 3H), 0.78-0.77 (m, 2H), 0.55-0.45 (m, 2H). |
| I-223 | | MS (ES): m/z 390.53 [M + H]+, LCMS purity: 100%, HPLC purity: 99.31%, $^1$H NMR (DMSO-d$_6$, 400 MHZ): 8.79 (s, 1H), 8.67-8.65 (d, J = 8 Hz, 1H), 8.42-8.41 (d, J = 3.6 Hz, 1H), 8.37 (s, 1H), 8.33 (d, J = 3.6 Hz, 1H), 8.24-8.22 (d, J = 8 Hz, 1H), 7.33-7.29 (m, 1H), 6.78 (s, 1H), 6.23-6.22 (t, J = 4 Hz, 1H), 3.13-3.11 (d, J = 8 Hz, 3H), 2.96-2.93 (m, 1H), 1.60-1.58 (d, J = 8 Hz, 6H), 0.89-0.85 (m, 2H), 0.65-0.61 (m, 2H). |
| I-228 | 96jjj | MS (ES): m/z 396.46 [M + H]+, LCMS purity: 99.50%, HPLC purity: 95.0%, $^1$H NMR (MEOD-d$_6$, 400 MHZ): 8.92-8.90 (d, J = 4 Hz, 1H), 8.36-8.34 (d, J = 8 Hz, 1H), 8.30 (s, 1H), 7.57 (s, 1H), 5.71 (s, 1H), 5.19-5.16 (m, 1H), 5.06 (s, 1H), 4.18-4.15 (d, J = 12 Hz, 1H), 3.96-3.93 (d, J = 12 Hz, 1H), 3.70-3.60 (m, 1H), 3.10 (s, 3H), 2.84 (s, 1H), 1.62 (s, 1H), 0.88-0.80 (m, 2H), 0.60-0.52 (m, 2H). |

TABLE 27-continued

| Compound # | Reagent | Chiral Separation Conditions and Characterization Data |
|---|---|---|
| I-274 | 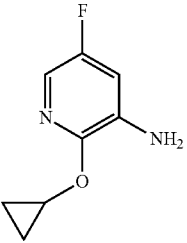 96kkk | MS (ES): m/z 398.22 [M + H]$^+$, LCMS purity: 97.75%, HPLC purity: 97.55%, $^1$H NMR (CDCL$_3$-d$_6$, 400 MHZ): 8.42 (s, 1H), 8.40-8.38 (d, J = 8 Hz, 1H), 7.80-7.79 (d, J = 4 Hz, 1H), 7.40 (s, 1H), 6.99 (s, 1H), 6.36-6.35 (d, J = 4 Hz, 1H), 5.42 (s, 1H), 4.39-4.36 (m, 1H), 3.14-3.13 (d, J = 4 Hz, 3H), 3.00-2.96 (m, 1H), 0.96-0.65 (m, 6H), 0.71-0.67 (m, 2H). |
| I-325 | 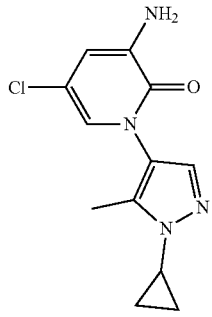 | MS (ES): m/z 494.37 [M + H]$^+$, LCMS purity: 100%, HPLC purity: 99.73%, $^1$H NMR (DMSO-d$_6$, 400 MHZ): 9.06 (s, 1H), 8.31 (s, 1H), 8.24 (s, 1H), 8.01-8.00 (d, J = 4 Hz, 1H), 7.68 (bs, 1H), 7.57 (s, 1H), 7.49-7.48 (d, J = 4 Hz, 1H), 6.31 (s, 1H), 2.90-2.89 (d, J = 4 Hz, 3H), 2.81-2.80 (m, 1H), 2.25 (s, 4H), 1.08-1.04 (m, 4H), 0.76-0.75 (m, 2H), 0.58 (bs, 2H). |
| I-199 | 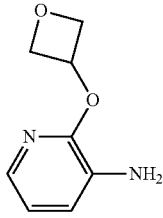 [SMILES: Nc1cccnc1OC1COC1] | MS (ES): m/z 414.23 [M + H]$^+$, LCMS purity: 95.07%, HPLC purity: 95.00%, $^1$H NMR (DMSO-d$_6$, 400 MHZ): 8.88 (s, 1H), 8.15-8.13 (d, J = 8 Hz, 1H), 7.91-7.89 (d, J = 8 Hz, 1H), 7.85-7.84 (d, J = 4 Hz, 1H), 7.07 (s, 1H), 6.84 (s, 1H), 6.30-3.28 (t, J = 8 Hz, 1H), 6.19 (s, 1H), 5.02-5.01 (d, J = 4 Hz, 1H), 4.80-4.78 (t, J = 8 Hz, 1H), 3.84-3.83 (d, J = 4 Hz, 1H), 3.77-3.75 (m, 1H), 3.74-3.72 (m, 1H), 3.42-3.39 (m, 2H), 2.91-2.90 (d, J = 4 Hz, 3H), 1.56 (s, 1H), 0.82-0.79 (m, 2H), 0.51 (bs, 2H). |
| I-197 | 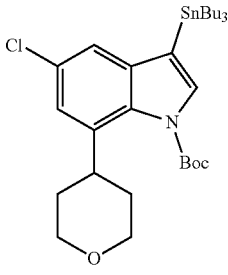 96lll | MS (ES): m/z 465.47 [M + H]$^+$, LCMS purity: 97.36%, HPLC purity: 95.18%, $^1$H (DMSO-d$_6$, 400 MHZ): 12.07 (s, 1H), 8.48 (s, 1H), 8.35 (s, 1H), 8.23-8.22 (d, J = 4 Hz, 1H), 8.17 (s, 2H), 7.13 (s, 1H), 6.96 (s, 1H), 4.03-4.01 (d, J = 8 Hz, 2H), 3.57-3.53 (m, 2H), 3.09-3.08 (d, J = 4 Hz, 3H), 2.91-2.90 (m, 2H), 1.81 (bs, 4H), 0.83-0.81 (d, J = 4 Hz, 2H), 0.64 (bs, 2H). |
| I-286 | 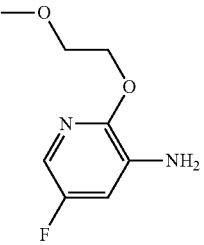 | MS (ES): m/z 416.40 [M + H]$^+$, LCMS purity: 100%, HPLC purity: 100%, $^1$H NMR (DMSO-d$_6$, 400 MHZ): 8.93 (bs, 1H), 8.33-8.31 (d, J = 8 Hz, 1H), 8.20 (s, 1H), 7.83 (s, 1H), 7.72 (s, 1H), 6.03 (s, 1H), 4.50 (s, 2H), 3.72 (s, 2H), 3.28 (s, 3H), 2.92 (s, 3H), 2.79-2.78 (d, J = 4 Hz, 1H), 0.69-0.68 (m, 2H), 0.40 (bs, 2H). |

US 10,562,906 B2

TABLE 27-continued

| Compound # | Reagent | Chiral Separation Conditions and Characterization Data |
|---|---|---|
| I-747 | 96mmm | MS(ES): m/z 417.55 [M + H]+<br>LCMS purity: 100%, HPLC purity: 100%, 1H NMR (DMSO-d6, 400 MHZ): 9.01 (s, 1H), 8.75-8.74 (d, J = 4.0 Hz, 1H), 8.68-8.67 (d, J = 4.0 Hz, 1H), 8.26-8.25 (d, J = 4.0 Hz, 1H) 8.21 (s, 1H), 8.02-8.01 (d, J = 4.0 Hz, 1H), 7.95-7.94 (d, J = 4.0 Hz, 1H), 7.86-7.85 (d, J = 4.0 Hz, 1H), 7.64-7.61 (m, 1H), 7.46-7.44 (d, J = 8.0 Hz, 1H), 6.45-6.41 (t, J = 8.0 Hz, 1H), 6.22 (s, 1H), 2.90-2.89 (d, J = 4.0, 3H), 2.86 (s, 1H), 0.83-0.80 (m, 2H), 0.54 (bs, 2H). |
| I-343 | 96nnn | MS (ES): m/z 452.53 [M + H]+,<br>LCMS purity: 100%, HPLC purity: 99.84%, CHIRAL HPLC:99.01%, 1H (DMSO-d6, 400 MHZ): 8.86 (s, 1H), 8.19 (s, 1H), 8.11-8.09 (d, J = 7.2 Hz, 1H), 7.91-7.90 (d, J = 4.8 Hz, 1H), 7.91-7.90 (d, J = 4.8 Hz, 1H), 7.82-7.81 (d, J = 3.6 Hz, 1H), 7.44-7.43 (d, J = 6.4 Hz, 1H), 6.33-6.29 (t, J = 7.2 Hz, 1H), 6.19 (s, 1H), 4.79-4.78 (m, 1H), 3.22 (s, 4H), 2.90-2.84 (m, 4H), 2.16-2.13 (d, J = 10 Hz, 2H), 1.80-1.77 (m, 4H), 1.33-1.23 (m, 5H), 0.79-0.77 (d, J = 5.6 Hz, 1H). |
| I-284 | 96ooo | MS (ES): m/z 375.51 [M + H]+,<br>LCMS purity: 100%, HPLC purity: 99.55%, 1H NMR (DMSO-d6, 400 MHZ): 9.06 (s, 1H), 8.37-8.35 (d, J = 8 Hz, 1H), 8.21 (s, 1H), 8.01-8.00 (d, J = 4 Hz, 1H), 7.86 (s, 1H), 7.72 (s, 1H), 6.06 (s, 1H), 2.92-2.91 (d, J = 4 Hz, 3H), 2.81-2.80 (m, 1H), 0.71-0.70 (m, 2H), 0.44 (bs, 2H). |
| I-306 | 96ppp | MS (ES): m/z 382.44 [M + H]+,<br>LCMS purity: 99.15%, HPLC purity: 98.78%, 1H NMR (DMSO-d6, 400 MHZ): 8.34-8.33 (d, J = 7.2 Hz, 1H), 8.25-8.24 (d, J = 4.4 Hz, 1H), 8.18(s, 1H), 7.99-7.97 (d, J = 4.8 Hz, 2H), 7.80-7.79 (d, J = 4 Hz, 1H), 7.34-7.31 (m, 1H), 6.29 (s, 1H), 5.67 (s, 1H), 2.95-2.94 (d, J = 4 Hz, 3H), 2.79-2.75 (m, 1H), 1.56 (s, 6H), 0.75-0.70 (m, 2H), 0.39-0.36 (m, 2H). |
| I-552 | 96qqq | MS (ES): m/z 417.2 [M + H]+,<br>LCMS purity: 97.03%, HPLC purity: 98.20%, 1H NMR (DMSO-d6, 400 MHZ): 8.82-8.81 (d, J = 7.2 Hz, 1H), 8.46-8.42 (m, 2H), 8.37 (s, 1H), 7.84-7.83 (d, J = 3.6 Hz, 1H), 7.60 (s, 1H), 7.32-7.28 (m, 1H), 6.44 (s, 1H), 3.50 (bs, 4H), 3.12-3.10 (d, J = 4.8 Hz, 3H), 1.96 (bs, 4H), 1.23 (s, 1H), 0.83-0.78 (m, 2H), 0.59-0.55 (m, 2H). |

TABLE 27-continued

| Compound # | Reagent | Chiral Separation Conditions and Characterization Data |
|---|---|---|
| I-393 | 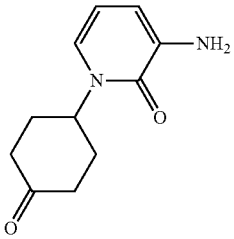<br>96rrr | Product was reacted with ethylene glycol, PTSA, and mol. seives in refluxing toluene after BOC removal: MS (ES) m/z 480.91 [M + H]$^+$, LCMS purity: 98.61%, HPLC purity: 98.50%, $^1$H NMR (DMSO-d$_6$, 400 MHZ): 8.87 (s, 1H), 8.19 (s, 1H), 8.11-8.10 (d, J = 4.0 Hz, 1H), 7.92-7.91(d, J = 4.0 Hz, 1H), 7.81-7.80 (d, J = 4.0 Hz, 1H), 7.40-7.38 (d, J = 8.0 Hz, 1H), 6.33-6.29 (t, J = 8.0 Hz, 1H), 6.19 (s, 1H), 4.89-4.83 (t, J = 12.0 Hz, 1H), 3.92-3.89 (m, 4H), 2.90-2.89 (d, J = 4.0 Hz, 3H), 2.87-2.83 (m, 1H), 1.92-1.69 (m, 8H), 0.80-0.76 (m, 2H), 0.51-0.47 (m, 2H). |
| I-359 | 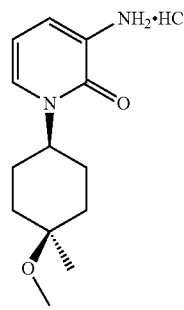<br>96sss | MS (ES): m/z 466.32 [M + H]$^+$, LCMS purity: 98.29%, HPLC purity: 97.82%, Chiral HPLC purity: 98.13%, $^1$H NMR (DMSO-d$_6$, 400 MHZ): 8.88 (s, 1H), 8.20 (s, 1H), 8.12-8.10 (d, J = 6.8 Hz, 1H), 7.92 (s, 1H), 7.84 (s, 1H), 7.38-7.36 (d, J = 6.4 Hz, 1H), 6.35-6.33 (t, J = 6.8 Hz, 1H), 6.20 (s, 1H), 4.79 (bs, 1H), 3.15 (s, 3H), 2.90-2.89 (m, 4H), 1.94-1.83 (m, 4H), 1.60-1.47 (m, 4H), 1.24(s, 3H), 0.80-0.78 (d, J = 6.0 Hz, 2H), 0.50 (bs, 2H). |
| I-554 | 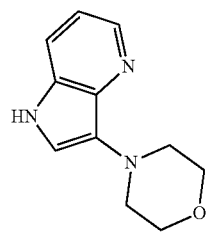<br>96ttt | MS (ES): m/z 433.39 [M + H]$^+$, LCMS purity: 99.47%, HPLC purity: 98.84%, $^1$H NMR (DMSO-d$_6$, 400 MHZ): 8.85-8.83 (d, J = 8 Hz, 1H), 8.49-8.46 (m, 2H), 8.39 (s, 1H), 7.84-7.82 (m, 2H), 7.34-7.31 (m, 1H), 6.49 (s, 1H), 3.85 (bs, 4H), 3.41 (bs, 4H), 3.12-3.11 (d, J = 4.8 Hz, 3H), 2.92-2.87 (m, 1H), 0.79-0.77 (d, J = 6.4 Hz, 2H), 0.58-0.54 (m, 2H). |
| I-481 | 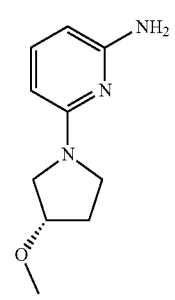<br>96uuu | MS(ES): m/z 423.49 [M + H]$^+$ LCMS purity: 98.92%, HPLC purity: 100%, chiral HPLC purity: 100%, $^1$H (DMSO-d$_6$, 400 MHZ): 9.55 (s, 1H), 8.19 (s, 1H), 8.04-8.01 (d, J = 11.2 Hz, 2H), 7.47-7.43 (t, J = 8 Hz, 1H), 7.04 (s, 1H), 6.64 (s, 1H), 6.08-6.06 (d, J = 7.6 Hz, 1H), 4.09 (s, 1H), 3.54 (s, 2H), 3.43-3.41 (d, J = 8.4 Hz, 1H), 3.28 (s, 3H), 2.96-2.95 (d, J = 3.2 Hz, 3H), 2.83(s, 2H), 2.08 (s, 2H). 0.77-0.76 (d, J = 3.2 Hz, 2H), 0.58 (bs, 2H). |
| I-482 | 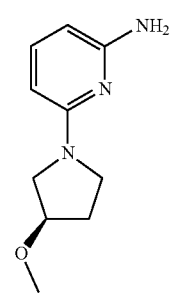<br>96vvv | MS(ES): m/z 423.49 [M + H]$^+$ LCMS purity: 99.73%, HPLC purity: 100%, chiral HPLC purity: 100%, $^1$H NMR (DMSO-d$_6$, 400 MHZ): 9.55 (s, 1H), 8.18 (s, 1H), 8.04-8.01 (d, J = 11.2 Hz, 2H), 7.47-7.43 (t, J = 8 Hz, 1H), 7.03 (s, 1H), 6.64-6.62 (d, J = 6.8 Hz, 1H), 6.07-6.05 (d, J = 8.4 Hz, 1H), 4.09 (s, 1H), 3.59 (m, 3H), 3.45-3.43 (d, J = 8. Hz, 1H), 3.27 (s, 3H), 2.95-2.94 (d, J = 4.8 Hz, 3H), 2.84-2.80 (m, 1H), 2.07 (s, 2H). 0.78-0.77 (m, 2H), 0.58 (d, J = 2 Hz, 2H). |

TABLE 27-continued

| Compound # | Reagent | Chiral Separation Conditions and Characterization Data |
|---|---|---|
| I-620 | 96www | MS (ES): m/z 395.37 [M + H]+, LCMS purity: 100%, HPLC purity: 99.40%, $^1$H NMR (DMSO-d$_6$, 400 MHZ): 9.48 (bs, 1H), 8.33 (bs, 1H), 7.53 (bs, 1H), 6.66 (bs, 1H), 6.18 (bs, 1H), 4.61-4.59 (t, J = 4.8 Hz, 1H), 4.31 (bs, 2H), 3.78 (bs, 2H), 3.18 (s, 1H), 2.98-2.97 (d, J = 4.4 Hz, 3H), 2.89-2.87 (d, J = 4.8 Hz, 1H), 2.86-2.84 (m, 1H), 1.24 (bs, 1H), 0.80-0.76 (m, 2H), 0.58 (bs, 2H), 0.49 (bs, 1H). |
| I-356 | 96xxx | MS (ES): m/z 452.40 +M-41 [M + H]+, LCMS purity: 100%, HPLC purity: 99.28%, $^1$H NMR (DMSO-d$_6$, 400 MHZ): 8.87 (s, 1H), 8.19 (s, 1H), 8.11-8.10 (d, J = 4 Hz, 1H), 7.92-7.91 (d, J = 4 Hz, 1H), 7.83-7.82 (d, J = 4 Hz, 1H), 7.38-7.36 (d, J = 8 Hz, 1H), 6.34-6.32 (t, J = 2 Hz, 1H), 6.19 (s, 1H), 4.85-4.82 (t, J = 12 Hz, 1H), 3.48 (bs, 1H), 3.25 (s, 3H), 2.91-2.90 (d, J = 4 Hz, 3H), 2.87-2.84 (m, 1H), 2.07-2.03 (m, 2H), 1.93-1.83 (m, 2H), 1.62-1.56 (m, 4H) 0.81-0.56 (m, 2H) 0.50 (bs, 2H). |
| I-316 | 96yyy | MS (ES): m/z 466.90 [M + H]+, LCMS purity: 99.67%, HPLC purity: 98.45%, $^1$H NMR (DMSO-d$_6$, 400 MHZ): 9.21 (s, 1H), 8.94-8.92 (d, J = 5.6 Hz, 1H), 8.35-8.35 (d, J = 2.4 Hz, 1H), 8.26 (s, 1H), 8.05-8.35 (m, 1H), 7.98-7.96 (d, J = 5.6 Hz, 1H), 7.94-7.94 (d, J = 2.4 Hz, 1H), 7.69-7.68 (d, J = 3.2 Hz, 1H), 6.34 (s, 1H), 2.92-2.90 (d, J = 4.8 Hz, 3H), 2.83-2.80 (m, 1H), 2.73 (s, 3H), 0.76-0.74 (d, J = 6.4 Hz, 2H), 0.59-0.56 (m, 2H). |
| I-264 | 96zzz | MS (ES): m/z 447.17 [M + H]+, LCMS purity: 100%, HPLC purity: 99.43%, $^1$H NMR (DMSO-d$_6$, 400 MHZ): 8.99 (s, 1H), 8.32-8.31 (d, J = 4 Hz, 1H), 8.23 (s, 1H), 8.21 (s, 1H), 7.95-7.94 (d, J = 4 Hz, 1H), 7.86-7.85 (d, J = 4 Hz, 1H), 7.77-7.75 (d, J = 8 Hz, 1H), 7.65-7.63 (d, J = 8 Hz, 1H), 7.53-7.52 (d, J = 4 Hz, 1H), 6.43-6.42 (t, J = 4 Hz, 1H), 6.21 (s, 1H), 3.92 (s, 3H), 3.90-3.86 (m, 4H), 0.82-0.77 (m, 2H), 0.54-0.53 (m, 2H). |
| I-241 | | MS (ES): m/z 458.56 [M + H]+, LCMS purity: 100%, HPLC purity: 98.66%, $^1$H NMR (DMSO-d$_6$, 400 MHZ): 9.04 (s, 1H), 8.29-8.27 (d, J = 8 Hz, 1H), 8.22 (s, 1H), 8.03-8.00 (d, J = 12 Hz, 1H), 7.97-7.96 (d, J = 4 Hz, 1H), 7.87-7.86 (d, J = 4 Hz, 1H), 7.79-7.76 (d, J = 12 Hz, 1H), 7.65-7.63 (d, J = 4 Hz, 1H), 6.51-6.49 (t, J = 8 Hz, 1H), 6.23 (s, 1H), 2.91-2.90 (d, J = 4 Hz, 3H), 2.88-2.87 (m, 1H), 2.40-2.35 (m, 1H), 1.20-1.15 (m, 4H), 0.81-0.80 (m, 2H), 0.54 (bs, 2H). |

TABLE 27-continued

| Compound # | Reagent | Chiral Separation Conditions and Characterization Data |
|---|---|---|
| I-606 | 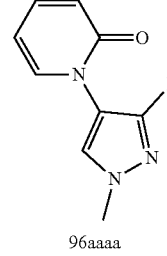<br>96aaaa | MS (ES): m/z 438.45 [M + H]$^+$, LCMS purity: 98.74%, HPLC purity: 97.64%, $^1$H NMR (DMSO-d$_6$, 400 MHZ): 9.02 (s, 1H), 8.20-8.19 (m, 2H), 8.13 (s, 1H), 7.97-7.93 (m, 1H), 7.83-7.82 (d, J = 3.6 Hz, 1H), 7.37-7.35 (d, J = 5.6 Hz, 1H), 6.40-6.36 (t, J = 14.4 Hz, 1H), 6.21 (s, 1H), 3.81 (s, 3H), 2.89-2.84 (m, 4H), 0.79-0.78 (m, 2H), 0.51-0.50 (m, 2H). |
| I-591 | 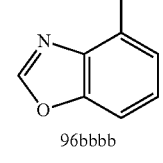<br>96bbbb | MS (ES): m/z 364.38 [M + H]$^+$, LCMS purity: 98.66%, HPLC purity: 98.25%, $^1$H NMR (DMSO-d$_6$, 400 MHZ): 9.74 (s, 1H), 8.79 (s, 1H), 8.18 (s, 1H), 7.96 (s, 1H), 7.92-7.90 (d, J = 8 Hz, 1H), 7.88-7.87 (d, J = 4 Hz, 1H), 7.52-7.50 (d, J = 8.4 Hz, 1H), 7.45-7.41 (t, J = 8 Hz, 1H), 6.00 (s, 1H), 2.93 (s, 3H), 2.80-2.76 (m, 1H), 0.72-0.68 (m, 2H), 0.33-0.29 (m, 2H). |
| I-301 | 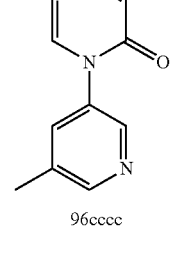<br>96cccc | MS (ES): m/z 431.47 [M + H]$^+$, LCMS purity: 97.85%, HPLC purity: 97.47%, $^1$H NMR (DMSO-d$_6$, 400 MHZ): 9.00(s, 1H), 8.56-8.56 (d, J = 2 Hz, 2H), 8.26-8.21 (m, 2H), 7.96-7.95 (d, J = 4.8 Hz, 1H), 7.86 (s, 2H), 7.43-7.41 (d, J = 8.4 Hz, 1H), 6.44-6.41 (t, J = 7.2 Hz, 1H), 6.21 (s, 1H), 3.73-3.72 (s, 1H), 2.90-2.87 (m, 4H), 2.38 (s, 3H), 1.23 (s, 1H), 0.81-0.79 (m, 2H). |
| I-812 | 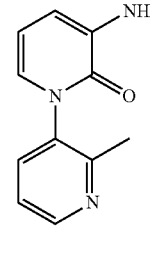 | MS (ES): m/z 431.80 [M + H]$^+$, LCMS purity: 99.80%, HPLC purity: 99.32%, $^1$H NMR (DMSO-d$_6$, 400 MHZ): 8.99 (s, 1H), 8.48-8.47 (d, J = 3.6 Hz, 1H), 8.30-8.29 (d, J = 7.2 Hz, 1H), 8.22 (s, 1H), 7.95 (bs, 1H), 7.88-7.87 (d, J = 3.2 Hz, 2H), 7.55-7.52 (m, 1H), 7.35-7.33 (d, J = 6.4 Hz, 1H), 6.46-6.42 (t, J = 7.2 Hz, 1H), 6.22 (s, 1H), 4.06-4.01 (m, 1H), 2.91-2.90 (d, J = 4.4 Hz, 3H), 2.16 (s, 3H), 0.82-0.81 (d, J = 6 Hz, 2H), 0.55 (bs, 2H). |
| I-237 | 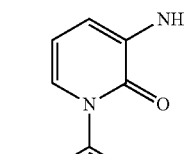 | MS (ES): m/z 431.34 [M + H]$^+$, LCMS purity: 100%, HPLC purity: 99.83%, $^1$H NMR (DMSO-d$_6$, 400 MHZ): 9.01 (s, 1H), 8.24-8.22 (d, J = 8 Hz, 2H), 7.93-7.92 (d, J = 4 Hz, 1H), 7.91 (s, 1H), 7.87 (bs, 1H), 7.63-7.61 (d, J = 8 Hz, 1H), 7.58-7.56 (d, J = 8 Hz, 1H), 7.41-7.39 (d, J = 8 Hz, 1H), 6.45-6.43 (t, J = 8 Hz, 1H), 6.22 (s, 1H), 2.91-2.90 (d, J = 4 Hz, 4H), 2.55 (s, 3H), 0.81-0.80 (m, 2H), 0.53 (bs, 2H). |

TABLE 27-continued

| Compound # | Reagent | Chiral Separation Conditions and Characterization Data |
|---|---|---|
| I-967 | 96dddd | MS (ES): m/z 435.26 [M + H]$^+$, LCMS purity: 100%, HPLC purity: 96.83%, $^1$H NMR (DMSO-d$_6$, 400 MHZ): 9.05 (s, 1H), 8.76-8.75 (d, J = 2.4 Hz, 1H), 8.69 (s, 1H), 8.28-8.26 (d, J = 7.6 Hz, 1H), 8.22 (s, 1H), 8.19-8.16 (d, J = 9.6 Hz, 1H), 7.98-7.96 (d, J = 4.8 Hz, 1H), 7.87-7.86 (d, J = 3.6 Hz, 1H), 7.50-7.49 (d, J = 6.8 Hz, 1H), 6.48-6.44 (t, J = 7.2 Hz, 1H), 6.24 (s, 1H), 2.91-2.90 (d, J = 4.4 Hz, 3H), 1.56 (bs, 1H), 0.82-0.81 (d, J = 5.2 Hz, 2H), 0.54 (bs, 2H). |
| I-297 | 96eeee | MS (ES): m/z 388.40 [M + H]$^+$, LCMS purity: 100%, HPLC purity: 98.30%, $^1$H NMR (DMSO-d$_6$, 400 MHZ): 8.83 (s, 1H), 8.52-8.51 (d, J = 4 Hz, 1H), 8.19-8.17 (d, J = 8 Hz, 1H), 8.13 (s, 1H), 7.96-7.95 (d, J = 4 Hz, 1H), 7.65-7.60 (m, 2H), 5.86 (s, 1H), 2.93-2.92 (d, J = 4 Hz, 3H), 2.68-2.66 (m, 1H), 2.09-1.99 (m, 3H), 0.62-0.58 (m, 2H), 0.09 (bs, 2H). |
| I-441 | 96ffff | MS (ES): m/z 433.34 [M + H]$^+$, LCMS purity: 100%, HPLC purity: 98.98%, $^1$H NMR (DMSO-d$_6$, 400 MHZ): 8.81-8.78 (d, J = 7.6 Hz, 1H), 8.67-8.66 (m, 1H), 8.59 (s, 1H), 8.35 (bs, 1H), 7.39-7.35 (m, 1H), 7.03 (s, 1H), 6.59-6.57 (m, 1H), 5.32-5.28 (m, 1H), 4.28- 4.24 (m, 2H), 3.78-3.72 (t, J = 11.2 Hz, 2H), 3.34-3.32 (d, J = 4.8 Hz, 3H), 3.11-3.08 (m, 1H), 2.66-2.55 (m, 2H), 2.12-2.08 (m, 2H), 1.01-.96 (m, 2H), 0.76 (bs, 2H). |
| I-143 | 96gggg | MS (ES): m/z 435.44 [M + H]$^+$, LCMS purity: 96.87%, HPLC purity: 95.11%, $^1$H NMR (DMSO-d$_6$, 400 MHZ): 8.80-8.79 (d, J = 4.8 Hz, 1H), 8.61-8.59 (d, J = 7.6 Hz, 1H), 8.52 (s, 1H), 8.13 (s, 2H), 7.78-7.77 (d, J = 2.8 Hz, 1H), 7.73-7.03 (m, 2H), 7.01-6.91 (m, 1H), 6.76 (s, 1H), 6.57-6.52 (t, J = 14.4 Hz, 1H) 3.04 (d, J = 4.8 Hz, 3H), 2.80-2.77 (m, 1H), 1.29-1.23 (bs, 3H), 0.88-0.84 (m, 1H). |
| I-440 | 96hhhh | MS (ES): m/z 391.31 [M + H]$^+$, LCMS purity: 100%, HPLC purity: 99.88%, $^1$H NMR (DMSO-d$_6$, 400 MHZ): 8.73-8.70 (m, 2H), 8.57-8.55 (m, 1H), 8.47 (s, 1H), 8.22 (s, 1H), 7.47-7.43 (m, 1H), 6.86 (s, 1H), 5.39-5.38 (d, J = 6.6 Hz, 1H), 3.12 (s, 3H), 2.95-2.93 (m, 1H), 1.71-1.58 (d, J = 6.4 Hz, 6H), 0.87-0.85 (m, 2H), 0.63-0.61 (m, 2H). |
| I-523 | 96iiii | MS (ES): m/z 488.26 [M + H]$^+$, LCMS purity: 97.82%, HPLC purity: 100%, $^1$H NMR (DMSO-d$_6$, 400 MHZ): 9.17 (s, 1H), 8.44 (bs, 1H), 8.24 (s, 2H), 8.02 (bs, 2H), 7.94 (s, 1H), 7.61 (bs, 1H), 6.30 (s, 1H), 3.92 (s, 3H), 2.91-2.90 (d, J = 4 Hz, 3H), 2.68 (bs, 1H), 0.69-0.68 (d, J = 6 Hz, 2H), 0.45 (bs, 2H). |

TABLE 27-continued

| Compound # | Reagent | Chiral Separation Conditions and Characterization Data |
|---|---|---|
| I-502 | 96jjjj | MS (ES): m/z 453.40 [M + H]$^+$, LCMS purity: 100%, HPLC purity: 98.72%, $^1$H NMR (DMSO-d$_6$, 400 MHZ): 9.23 (s, 1H), 8.23 (bs, 2H), 8.06 (bs, 2H), 7.87 (bs, 1H), 6.57-6.55 (m, 1H), 6.30 (s, 1H), 3.32 (bs, 3H), 2.99 (bs, 4H), 1.47 (s, 4H), 0.88 (bs, 3H), 0.58 (bs, 2H). |
| I-550 | 91f | MS(ES): m/z 436.39 [M + H]$^+$. LCMS purity: 97.90%, HPLC purity: 100%, $^1$H NMR (DMSO-d$_6$, 400 MHZ): 8.90 (s, 1H), 8.19 (s, 1H), 8.12-8.10 (d, J = 8.0 Hz, 1H), 7.93-7.91 (d, J = 8.0 Hz, 1H), 7.84-7.83 (d, J = 8.0 Hz, 1H) 7.47-7.45 (d, J = 8.0 Hz, 1H), 6.35-6.31 (t, J = 8.0 Hz, 1H), 6.20 (s, 1H), 4.97-4.92 (m, 1H), 4.72 (s, 2H), 4.56 (s, 2H), 2.90-2.89 (d, J = 4.0 Hz, 2H), 2.86-2.85 (d, J = 4.0 Hz, 1H), 2.78-2.73 (m, 2H), 2.68-2.56 (m, 3H), 0.81-0.78 (m, 2H), 0.50 (bs, 2H). |
| I-233 | | MS (ES): m/z 434.55 [M + H]$^+$, LCMS purity: 99.55%, HPLC purity: 99.48%, $^1$H NMR (DMSO-d$_6$, 400 MHZ): 8.92 (s, 1H), 8.23 (s, 1H), 8.21 (s, 1H), 8.11-8.10 (d, J = 4 Hz, 1H), 7.92 (s, 2H), 7.82-7.81 (d, J = 4 Hz, 1H), 7.40 (s, 1H), 6.22 (s, 1H), 3.92 (s, 3H), 2.92-2.90 (d, J = 8 Hz, 3H), 2.81-2.78 (m, 1H), 2.21 (s, 3H), 0.78-0.74 (m, 2H), 0.53-0.50 (m, 2H). |
| I-810 | 96kkkk | MS (ES): m/z 422.38 [M + H]$^+$, LCMS purity: 99.42%, HPLC purity: 97.92%, CHIRAL HPLC purity: 99.10, $^1$H NMR (DMSO-d$_6$, 400 MHZ): 8.94 (s, 1H), 8.19 (s, 1H), 8.10-8.09 (d, J = 4.0 Hz, 1H), 7.92-7.91 (d, J = 4.0 Hz, 1H), 7.82-7.81 (d, J = 4.0 Hz, 1H), 7.31-7.30 (d, J = 4.0 Hz, 1H), 6.27-6.23 (t, J = 8.0 Hz, 1H), 6.17 (s, 1H), 4.00-3.98 (d, J = 8.0 Hz, 2H), 3.74-3.72 (m, 2H), 3.14 (s, 1H), 2.89-2.88 (d, J = 4.0 Hz, 3H), 2.86-2.82 (m, 1H), 2.27 (s, 2H), 0.80-0.75 (m, 2H), 0.49 (bs, 2H). |
| I-252 | | MS (ES): m/z 404.50 [M + H]$^+$, LCMS purity: 100%, HPLC purity: 99.44%, $^1$H NMR (DMSO-d$_6$, 400 MHZ): 8.71 (s, 1H), 8.45 (s, 1H), 8.36 (s, 1H), 8.32-8.31 (d, J = 4 Hz, 1H), 8.25 (s, 1H), 8.19-8.18 (d, J = 4 Hz, 1H), 6.74 (s, 1H), 5.18-5.15 (m, 1H), 3.12-3.11 (d, J = 4 Hz, 3H), 2.95-2.92 (m, 1H), 2.68 (s, 3H), 1.58-1.57 (d, J = 4 Hz, 6H), 0.87-0.83 (m, 2H), 0.62 (bs, 2H). |

TABLE 27-continued

| Compound # | Reagent | Chiral Separation Conditions and Characterization Data |
|---|---|---|
| I-129 | 96llll | MS (ES): m/z 514.56 [M + H]$^+$, LCMS purity: 98.69%, HPLC purity: 99.10%, $^1$H NMR (DMSO-d$_6$, 400 MHZ): 9.03 (s, 1H), 8.80 (s, 1H), 8.26-8.19 (m, 3H), 7.97-7.95 (d, J = 8.4 Hz, 2H), 7.86-7.85 (d, J = 3.6 Hz 1H), 7.67-7.65 (d, J = 6.4 Hz, 1H), 6.49-6.46 (t, J = 7.2 Hz, 1H), 6.23 (s, 1H), 3.53-3.51 (m, 4H), 2.92-2.87 (m, 4H), 1.89 (s, 4H), 0.81-0.80 (d, J = 5.6 Hz, 2H), 0.53 (bs, 2H). |
| I-125 | 96llll | MS(ES): m/z 432.24 [M + H]$^+$, LCMS purity: 97.43%, HPLC purity: 95.01%, $^1$H NMR (DMSO-d$_6$, 400 MHz): 9.07(s, 1H), 8.92-8.91 (d, J = 5.6 Hz, 1H), 8.25-8.22 (m, 2H), 7.96-7.95 (d, J = 5.6 Hz, 2H) 7.84 (d, J = 3.6 Hz, 1H), 7.80-7.78 (d, J = 6 Hz, 1H), 6.52-6.49 (t, J = 7.2 Hz, 1H), 6.23 (s, 1H), 2.92-2.91 (d, J = 4.8 Hz, 3H), 2.72 (s, 3H), 0.86-0.85 (m, 1H), 0.82-0.78 (m, 2H), 0.54-0.52 (m, 2H). |
| I-212 | 96mmmm | MS (ES): m/z 396.33 [M + H]$^+$, LCMS purity: 98.76%, HPLC purity: 98.82%, $^1$H NMR (MEOD-d$_6$, 400 MHZ): 8.60 (s, 1H), 8.13 (s, 1H), 7.96 (s, 1H), 7.88-7.87 (d, J = 4 Hz, 1H), 7.82 (s, 1H), 7.74 (s, 1H), 5.82 (s, 1H), 5.31-5.26 (m, 1H), 2.92-2.91 (d, J = 4 Hz, 3H), 2.72 (m, 1H), 2.27 (s, 3H), 1.29-1.28 (d, J = 4 Hz, 6H), 0.66-0.65 (m, 2H), 0.24 (bs, 2H). |
| I-209 | 96nnnn | MS (ES): m/z 400.53 [M + H]$^+$, LCMS purity: 99.50%, HPLC purity: 95.0%, $^1$H NMR (MEOD-d$_6$, 400 MHZ): 8.72 (s, 1H), 8.33-8.31 (d, J = 8 Hz, 1H), 8.21 (s, 1H), 8.00 (m, 1H), 7.84-7.83 (d, J = 4 Hz, 1H), 7.72-7.71 (d, J = 4 Hz, 1H), 6.05 (s, 1H), 5.34-5.29 (m, 1H), 2.95 (s, 3H), 2.80-2.79 (d, J = 4 Hz, 1H), 1.37-1.36 (d, J = 4 Hz, 6H), 0.71-0.69 (m, 2H), 0.42 (bs, 2H). |
| I-277 | 96oooo | MS (ES): m/z 394.36 [M + H]$^+$, LCMS purity: 100%, HPLC purity: 99.53%, $^1$H NMR (DMSO-d$_6$, 400 MHZ): 8.67 (s, 1H), 8.15 (s, 1H), 8.00 (s, 1H), 7.91-7.90 (d, J = 4 Hz, 1H), 7.80-7.79 (d, J = 4 Hz, 2H), 5.79 (s, 1H), 4.31-4.27 (m, 1H), 2.91-2.90 (d, J = 4 Hz, 3H), 2.75-2.71 (m, 1H), 2.30 (s, 3H), 0.78-0.64 (m, 6H), 0.28-0.24 (m, 2H). |

TABLE 27-continued

| Compound # | Reagent | Chiral Separation Conditions and Characterization Data |
|---|---|---|
| I-247 | 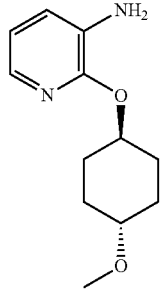<br>96pppp | MS (ES): m/z 452.32 [M + H]$^+$, LCMS purity: 96.03%, HPLC purity: 97.73%, CHIRAL HPLC purity: 100%, $^1$H NMR (DMSO-d$_6$, 400 MHZ): 8.69 (s, 1H), 8.15 (s, 1H), 8.14-8.012 (d, J = 8 Hz, 1H), 7.93-7.92 (t, J = 4 Hz, 2H), 7.79-7.78 (d, J = 4 Hz, 1H), 7.00-6.97 (m, 1H), 5.85 (s, 1H), 5.11-5.06 (m, 1H), 3.24 (s, 3H), 3.21-3.18 (m, 1H), 2.93-2.92 (d, J = 4 Hz, 3H), 2.78-2.74 (m, 1H), 2.04-1.96 (m, 4H), 1.56-1.49 (m, 2H), 1.37-1.28 (m, 2H), 0.70-0.66 (m, 2H), 0.32-0.29 (m, 2H). |
| I-231 | 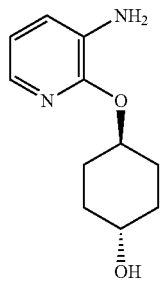<br>96qqqq | MS (ES): m/z 438.55 [M + H]$^+$, LCMS purity: 97.70%, HPLC purity: 97.38%, CHIRAL HPLC purity: 100%, $^1$H NMR (DMSO-d$_6$, 400 MHZ): 8.67 (s, 1H), 8.15-8.13 (d, J = 8 Hz, 2H), 7.92-7.91 (t, J = 4 Hz, 2H), 7.79-7.78 (d, J = 4 Hz, 1H), 7.00-6.96 (m, 1H), 5.86 (s, 1H), 5.06-5.01 (m, 1H), 4.60-4.59 (d, J = 4 Hz, 1H), 3.51-3.49 (m, 1H), 2.93 - 2.92 (d, J = 4 Hz, 3H), 2.78-2.75 (m, 1H), 2.04-2.02 (m, 2H), 1.86-1.83 (m, 2H), 1.54-1.46 (m, 2H), 1.34-1.24 (m, 2H), 0.71-0.67 (m, 2H), 0.31 (bs, 2H). |
| I-221 | 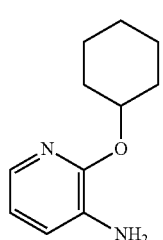<br>96rrrr | MS (ES): m/z 422.46 [M + H]$^+$, LCMS purity: 99.76%, HPLC purity: 99.59%, $^1$H NMR (DMSO-d$_6$, 400 MHZ): 8.67 (s, 1H), 8.15 (s, 1H), 8.12 (s, 1H), 7.92 (m, 2H), 7.79 (s, 1H), 6.98 (s, 1H), 5.87 (s, 1H), 5.09 (s, 1H), 2.93 (s, 3H), 1.95 (m, 2H), 1.72 (m, 2H), 1.52-1.49 (m, 3H), 1.37-1.24 (m, 4H), 0.70-0.68 (m, 2H), 0.31 (bs, 2H). |
| I-173 | 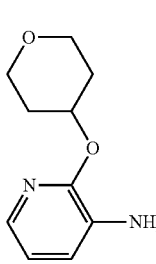 | MS (ES): m/z 424.24 [M + H]$^+$, LCMS purity: 95.00%, HPLC purity: 95.00%, $^1$H NMR (DMSO-d$_6$, 400 MHZ): 8.72 (s, 1H), 8.16-8.15 (d, J = 4 Hz, 1H), 7.93-7.92 (t, J = 4 Hz, 2H), 7.78-7.77 (d, J = 4 Hz, 1H), 7.03-7.00 (m, 1H), 5.87 (s, 1H), 5.31.5.17 (m, 1H), 3.87-3.83 (m, 1H), 3.50-3.48 (t, J = 8 Hz, 2H), 2.94-2.93 (d, J = 4 Hz, 3H), 2.78-2.74 (m, 2H), 2.01-1.98 (m, 2H), 1.74-1.65 (m, 2H), 1.24 (bs, 1H), 0.71-0.66 (m, 2H), 0.32-0.28 (m, 2H). |
| I-172 | 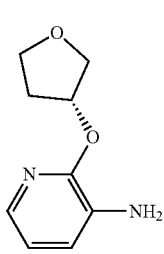 [SMILES: Nc1cccnc1O[C@@H]1CCOC1] | MS (ES): m/z 410.52 [M + H]$^+$, LCMS purity: 99.51%, HPLC purity: 99.38%, CHIRAL HPLC purity: 100%, $^1$H NMR (DMSO-d$_6$, 400 MHZ): 8.74 (s, 1H), 8.21-8.20 (d, J = 4 Hz, 1H), 8.16 (s, 1H), 7.93-7.92 (d, J = 4 Hz, 2H), 7.80-7.79 (d, J = 4 Hz, 1H), 7.05-7.02 (m, 1H), 5.87 (s, 1H), 5.56 (s, 1H), 3.98-3.94 (m, 1H), 3.88-3.82 (m, 2H), 3.77-3.71 (m, 1H), 2.93 (s, 3H), 2.79-2.77 (m, 1H), 2.25-2.20 (m, 2H), 0.71-0.69 (m, 2H), 0.34 (bs, 2H). |

TABLE 27-continued

| Compound # | Reagent | Chiral Separation Conditions and Characterization Data |
|---|---|---|
| I-184 | 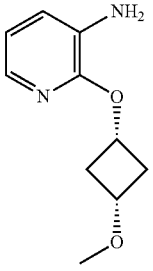 | MS (ES): m/z 424.52 [M + H]$^+$, LCMS purity: 95.98%, HPLC purity: 95.08%, $^1$H NMR (DMSO-d$_6$, 400 MHZ): 8.79 (s, 1H), 8.23-8.21 (d, J = 8 Hz, 1H), 8.16 (s, 1H), 7.92-7.91 (d, J = 4 Hz, 1H), 7.89-7.87 (d, J = 8 Hz, 1H), 7.80-7.79 (d, J = 4 Hz, 1H), 7.02-7.01 (t, J = 4 Hz, 1H), 5.91 (s, 1H), 4.96-4.89 (m, 1H), 3.68-3.66 (t, J = 8 Hz, 1H), 3.16 (s, 3H), 2.94-2.93 (d, J = 4 Hz, 3H), 2.84-2.78 (m, 3H), 2.06-2.02 (m, 2H), 0.71-0.70 (m, 2H), 0.35 (bs, 2H). |
| I-711 | 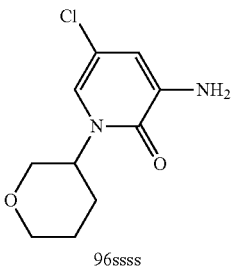 [SMILES: Nc1cc(Cl)cn(C2CCCOC2)c1=O]<br>96ssss | MS (ES): m/z 458.32 [M + H]$^+$, LCMS purity: 100%, HPLC purity: 99.50%, Chiral HPLC: 49.77% and 49.80% $^1$H NMR (DMSO-d$_6$, 400 MHZ): 9.05 (s, 1H), 8.24-8.23 (d, J = 4 Hz, 2H), 8.01-8.00 (d, 4 Hz, 1H), 7.71-7.65 (dd, J = 2.4 and 2.8 Hz, 2H), 6.31 (s, 1H), 4.88-4.83 (t, J = 9.6 Hz, 1H), 3.85-3.80 (t, J = 6.4 Hz, 2H), 3.68-3.63 (m, 1H), 3.51-3.48 (t, J = 12 Hz, 1H), 2.91-2.90 (d, 3H), 2.82-2.77 (m, 1H), 2.13-2.09 (m, 1H), 1.96 (s, 1H), 1.76-1.69 (m, 2H), 0.78-0.73 (m, 2H), 0.58-0.57 (t, J = 4.8 Hz 2H). |
| I-782<br>I-783 | 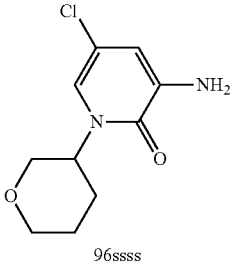 [SMILES: Nc1cc(Cl)cn(C2CCCOC2)c1=O]<br>96ssss | I-711 was separated into isomers: CHIRAL PAK IB (250 mm * 4.6 mm, 5u) and 0.1% DEA in IPA:Methanol (50:50) at 4 mL/min.<br>FR-a: MS(ES): m/z 458.61 [M + H]$^+$, LCMS purity: 98.71%, HPLC purity: 98.98%, CHIRAL HPLC purity: 100%, $^1$H NMR (DMSO-d$_6$, 400 MHZ): 9.05 (s, 1H), 8.24-8.23 (d, J = 4 Hz, 2H), 8.01-8.00 (d, 4 Hz, 1H), 7.71-7.65 (dd, J = 2.4 and 2.8 Hz, 2H), 6.31 (s, 1H), 4.88-4.83 (t, J = 9.6 Hz, 1H), 3.85-3.80 (t, J = 6.4 Hz, 2H), 3.68-3.63 (m, 1H), 3.51-3.48 (t, J = 12 Hz, 1H), 2.91-2.90 (d, 3H), 2.82-2.77 (m, 1H), 2.13-2.09 (m, 1H), 1.96(s, 2H), 0.58-0.57 (t, J = 4.8 Hz 2H).<br>FR-b: MS(ES): m/z 458.61 [M + H]$^+$, LCMS purity: 100%, HPLC purity: 100%, CHIRAL HPLC purity: 100%, $^1$H NMR (DMSO-d$_6$, 400 MHZ): 9.05 (s, 1H), 8.24-8.23 (d, J = 4 Hz, 2H), 8.01-8.00 (d, 4 Hz, 1H), 7.71-7.65 (dd, J = 2.4 and 2.8 Hz, 2H), 6.31 (s, 1H), 4.88-4.83 (t, J = 9.6 Hz, 1H), 3.85-3.80 (t, J = 6.4 Hz, 2H), 3.68-3.63 (m, 1H), 3.51-3.48 (t, J = 12 Hz, 1H), 2.91-2.90 (d, 3H), 2.82-2.77 (m, 1H), 2.13-2.09 (m, 1H), 1.96(s, 1H), 1.76-1.69 (m, 2H), 0.78-0.73 (m, 2H), 0.58-0.57 (t, J = 4.8 Hz 2H). |
| I-188 | 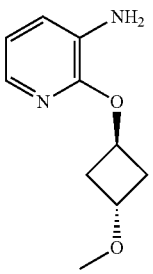 | MS (ES): m/z 424.19 [M + H]$^+$, LCMS purity: 99.20%, HPLC purity: 95.00%, CHIRAL HPLC purity: 100%, $^1$H NMR (DMSO-d$_6$, 400 MHZ): 8.78 (s, 1H), 8.19-8.15 (m, 2H), 7.92-7.89 (m, 2H), 7.789-7.780 (d, J = 3.6 Hz, 1H), 7.02-7.00 (t, J = 8 Hz, 1H), 8.87 (s, 1H), 5.35-5.30 (m, 1H), 4.04-3.99 (m, 1H), 3.14 (s, 3H), 2.93-2.92 (d, J = 4 Hz, 3H), 2.78-2.76 (m, 1H), 2.40-2.33 (m, 4H), 0.71-0.66 (m, 2H), 0.33-0.29 (m, 2H). |

TABLE 27-continued

| Compound # | Reagent | Chiral Separation Conditions and Characterization Data |
| --- | --- | --- |
| I-367 | 96tttt | MS(ES): m/z 477.46 [M + H]$^+$.<br>LCMS purity: 97.59%, HPLC purity: 100%, NMR (DMSO-d$_6$, 400 MHZ): 8.83 (s, 1H), 8.28-8.27 (m, 1H), 8.20 (s, 1H), 7.87-7.86 (d, J = 3.6 Hz, 1H), 7.07-7.04 (m, 1H), 5.77 (s, 1H), 5.43-5.38 (m, 1H), 4.00-3.98 (t, J = 8 Hz, 1H), 3.53-5.50 (m, 2H), 3.29-3.22 (m, 3H) 3.07 (s, 3H), 2.85-2.83 (m, 1H), 1.31-1.28 (m, 2H), 0.85-0.80 (d, 2H), 0.50 (bs, 2H). |
| I-169 |  | MS (ES): m/z 394.48 [M + H]$^+$,<br>LCMS purity: 100%, HPLC purity: 99.08%, $^1$H NMR (DMSO-d$_6$, 400 MHZ): 8.78 (s, 1H), 8.21-8.19 (d, J = 8 Hz, 1H), 8.16 (s, 1H), 7.93-7.91 (d, J = 8 Hz, 1H), 7.89-7.88 (d, J = 4 Hz, 1H), 7.80-7.79 (d, J = 4 Hz, 1H), 7.01-6.98 (m, 1H), 5.91 (s, 1H), 5.26-5.24 (t, J = 8 Hz, 1H), 2.93-2.92 (d, J = 4 Hz, 3H), 2.79-2.76 (m, 1H), 2.43-2.39 (m, 2H), 2.14-2.12 (t, J = 8 Hz, 2H), 1.80-1.77 (m, 1H), 1.67-1.65 (m, 1H), 0.71-0.68 (m, 2H), 0.36-0.32 (m, 2H). |
| I-218 | 96uuuu | MS (ES): m/z 398.40 [M + H]$^+$,<br>LCMS purity: 99.51%, HPLC purity: 98.41%, $^1$H NMR (DMSO-d$_6$, 400 MHZ): 8.82 (s, 1H), 8.19-8.17 (d, J = 8 Hz, 1H), 8.15 (s, 1H), 7.919-7.911 (m, 2H), 7.79-7.78 (d, J = 4 Hz, 1H), 7.03-7.00 (m, 1H), 5.88 (s, 1H), 4.49-4.48 (t, J = 4 Hz, 2H), 3.69-3.68 (t, J = 4 Hz, 2H), 3.25 (s, 3H), 2.92-2.90 (d, J = 8 Hz, 3H), 2.78-2.76 (m, 1H), 0.71-0.66 (m, 2H), 0.33 (bs, 2H). |
| I-258 | 96wwww | MS (ES): m/z 371.52 [M + H]$^+$,<br>LCMS purity: 98.87%, HPLC purity: 99.45%, $^1$H NMR (DMSO-d$_6$, 400 MHZ): 8.86 (s, 1H), 8.15 (s, 1H), 8.01 (s, 1H), 7.91-7.90 (d, J = 4 Hz, 1H), 7.83-7.82 (d, J = 4 Hz, 1H), 7.76 (s, 1H), 5.83 (s, 1H), 2.91-2.89 (d, J = 8 Hz, 3H), 2.75-2.72 (m, 1H), 2.29 (s, 3H), 0.69-0.65 (m, 2H), 0.29-0.26 (m, 2H). |
| I-327 | 96vvvv | MS (ES): m/z 420.38 [M + H]$^+$,<br>LCMS purity: 97.34%, HPLC purity: 96.66%, $^1$H NMR (DMSO-d$_6$, 400 MHZ): 9.04 (s, 1H), 8.30-8.28 (d, J = 8 Hz, 1H), 8.22 (s, 1H), 7.97-7.96 (d, J = 4 Hz, 1H), 7.83-7.82 (d, J = 4 Hz, 1H), 7.58-7.57 (d, J = 4 Hz, 1H), 7.30-7.29 (d, J = 4 Hz, 1H), 6.49-6.49 (d, J = 2 Hz, 1H), 6.45-6.43 (t, J = 8 Hz, 1H), 6.23 (s, 1H), 5.76 (s, 1H), 3.64 (s, 3H), 2.90-2.89 (d, J = 4 Hz, 3H), 0.81-0.79 (m, 2H), 0.53-0.52 (m, 2H). |

TABLE 27-continued

| Compound # | Reagent | Chiral Separation Conditions and Characterization Data |
|---|---|---|
| I-340 | 96xxxx | MS (ES): m/z 434.46 [M + H]+, LCMS purity: 99.48%, HPLC purity: 99.71%, $^1$H NMR (DMSO-$d_6$, 400 MHZ): 9.04 (s, 1H), 8.29-8.27 (d, J = 7.6 Hz, 1H), 8.22 (s, 1H), 7.98-7.97 (d, J = 4.8 Hz, 1H), 7.83 (d, J = 3.6 Hz, 1H), 7.29-7.27 (d, J = 5.6 Hz, 1H), 6.44-6.40 (t, J = 7.2 Hz, 1H), 6.27-6.24 (d, J = 12.4 Hz, 1H), 3.55 (s, 3H), 2.90-2.84 (m, 4H), 2.21 (s, 3H), 1.24 (bs, 1H), 0.86-0.74 (m, 2H), 0.54-0.51 (m, 2H). |
| I-715 | 96yyyy | MS (ES): m/z 407.31 [M + H]+, LCMS purity: 100%, HPLC purity: 93.75%, $^1$H NMR (DMSO-$d_6$, 400 MHZ): 9.09 (s, 1H), 8.35 (s, 1H), 8.26-8.25 (d, J = 6.4 Hz, 1H), 8.22 (s, 1H), 7.99-7.98 (d, J = 4.8 Hz, 1H), 7.81-7.80 (d, J = 3.2 Hz, 1H), 7.49 (bs, 2H), 6.47-6.45 (m, 1H), 6.19 (s, 1H), 2.90-2.89 (d, J = 4.8 Hz, 4H), 0.79-0.77 (d, J = 5.6 Hz, 2H), 0.51 (bs, 2H). |
| I-291 | 96zzzz | MS (ES): m/z 451.46 [M + H]+, LCMS purity: 97.85%, HPLC purity: 99.78%, $^1$H NMR (DMSO-$d_6$, 400 MHZ): 9.28 (s, 1H), 8.44-8.43 (d, J = 4 Hz, 1H), 8.37-8.36 (d, J = 4 Hz, 1H), 8.19 (s, 1H), 7.99-7.98 (d, J = 4 Hz, 1H), 7.95-7.93 (d, J = 4 Hz, 1H), 6.63-6.61 (t, J = 8 Hz, 1H), 6.25 (s, 1H), 4.47-4.45 (m, 1H), 2.92-2.91 (d, J = 4 Hz, 3H), 2.36 (s, 3H), 2.30 (s, 3H), 1.92-1.87 (m, 2H), 1.72 (m, 2H). |
| I-174 | 96aaaaa | MS (ES): m/z 407.37 [M + H]+, LCMS purity: 98.06%, HPLC purity: 95.58%, $^1$H NMR (DMSO-$d_6$, 400 MHZ): 9.12 (s, 1H), 8.51 (s, 1H), 8.24-8.21 (d, J = 8.8 Hz, 2H), 7.98 (bs, 1H), 7.80 (bs, 1H), 7.57 (bs, 2H), 6.83 (bs, 1H), 6.51-6.48 (t, J = 7.2 Hz, 1H), 6.22 (s, 1H), 2.90-2.89 (d, J = 4 Hz, 3H), 1.55 (bs, 2H), 0.51 (bs, 2H). |
| I-937 | 96bbbbb | MS (ES): m/z 435.62 [M + H]+, LCMS purity: 100%, HPLC purity: 99.58%, $^1$H NMR (DMSO-$d_6$, 400 MHZ): 9.04 (s, 1H), 8.25 (s, 1H), 8.23-8.22 (d, J = 3.6 Hz, 1H), 7.99-7.98 (d, J = 4.8 Hz, 1H), 7.83-7.82 (d, J = 3.6 Hz, 1H), 7.37-7.35 (d, J = 6.8 Hz, 1H), 6.44-6.40 (t, J = 7.2 Hz, 1H), 6.20 (s, 1H), 2.91-2.90 (d, J = 4.4 Hz, 3H), 2.87-2.85 (m, 1H), 2.44 (s, 3H), 2.00 (s, 3H), 0.82-0.77 (m, 2H), 0.52 (bs, 2H). |

TABLE 27-continued

| Compound # | Reagent | Chiral Separation Conditions and Characterization Data |
|---|---|---|
| I-267 | 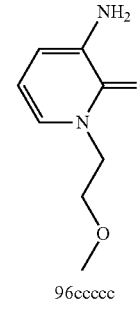<br>96ccccc | MS(ES): m/z 398.44 [M + H]+, LCMS purity: 100%, HPLC purity: 99.09%, $^1$H NMR (DMSO-$d_6$, 400 MHZ): 8.90 (s, 1H), 8.19 (s, 1H), 8.13-8.13 (d, J = 1.2 Hz, 1H), 7.91-7.90 (d, J = 4.8 Hz, 1H), 7.83-7.82 (d, J = 3.6 Hz, 1H), 7.35-7.35 (d, J = 1.6 Hz, 1H), 7.01 (s, 1H), 6.29-6.25 (t, J = 7.2 Hz, 1H), 4.19-4.16 (t, 2H), 3.66-3.63 (t, 2H), 3.26 (s, 3H), 2.90-2.84 (m, 4H), 0.79-0.77 (m, 2H), 0.50-0.48 (m, 2H). |
| I-404 | 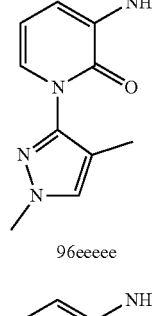<br>96eeeee | MS (ES): m/z 434.34 [M + H]+, LCMS purity: 100%, HPLC purity: 99.57%, $^1$H NMR (DMSO-$d_6$, 400 MHZ): 8.96 (s, 1H), 8.23-8.20 (t, J = 12 Hz, 2H), 7.93-7.92 (d, J = 4.4 Hz, 1H), 7.85-7.84 (d, J = 8.2 Hz, 1H), 7.62 (s, 1H), 7.26-7.24 (d, J = 6.8 Hz, 1H), 6.37-6.33 (t, J = 7.2 Hz, 1H), 6.21 (s, 1H), 3.83 (s, 3H), 2.90-2.89 (d, J = 4.4 Hz, 4H), 1.91 (s, 3H), 0.80-0.79 (d, J = 5.2 Hz, 2H), 0.52 (bs, 2H). |
| I-717 | 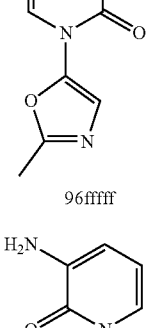<br>96fffff | MS (ES): m/z 421.38 [M + H]+, LCMS purity: 99.36%, HPLC purity: 98.19%, $^1$H NMR (DMSO-$d_6$, 400 MHZ): 9.11 (s, 1H), 8.22 (s, 2H), 7.98 (bs, 1H), 7.83-7.82 (d, J = 4 Hz, 1H), 7.57-7.55 (d, J = 5.6 Hz, 1H), 7.40 (s, 1H), 6.51-6.47 (t, J = 7.6 Hz, 1H), 6.22 (s, 1H), 2.92-2.90 (d, J = 4.8 Hz, 3H), 2.52 (s, 3H), 1.24 (bs, 1H), 0.82-0.77 (m, 2H), 0.52 (bs, 2H). |
| I-504 | 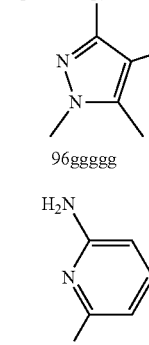<br>96ggggg | MS (ES): m/z 448.50 [M + H]+, LCMS purity: 100%, HPLC purity: 99.81%, $^1$H NMR (DMSO-$d_6$, 400 MHZ): 8.94 (s, 1H), 8.23 (s, 1H), 8.21 (s, 1H), 7.94-7.92 (d, J = 4.8 Hz, 1H), 7.85-7.84 (d, J = 3.6 Hz, 1H), 7.23-7.22 (d, J = 6.0 Hz, 1H), 6.36-6.32 (t, J = 7.2 Hz, 1H), 6.22 (s, 1H), 3.75 (s, 3H), 2.90-2.89 (d, J = 4.8 Hz, 4H), 2.24 (s, 3H), 1.80 (s, 3H), 0.87-0.79 (m, 2H), 0.52 (bs, 2H). |
| I-382 | 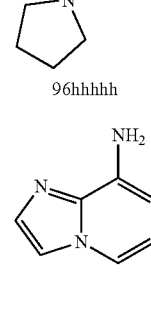<br>96hhhhh | MS (ES): m/z 393.36 [M + H]+, LCMS purity: 100%, HPLC purity: 98.71%, $^1$H NMR (DMSO-$d_6$, 400 MHZ): 9.53 (s, 1H), 8.19 (s, 1H), 8.05-8.04 (d, J = 3.6 Hz, 1H), 8.00-7.98 (m, 1H), 7.46-7.42 (m, 1H), 7.08 (s, 1H), 6.61-6.59 (d, J = 6.8 Hz, 1H), 6.06-6.04 (d, J = 8.4 Hz 1H), 3.45 (s, 4H), 3.18-3.17 (d, J = 4.8 Hz, 3H), 2.95-2.94 (d, J = 4.8 Hz, 1H), 1.96 (s, 4H), 0.79-0.75 (m, 2H), 0.59 (bs, 2H). |
| I-891 |  | MS (ES): m/z 363.47 [M + H]+, LCMS purity: 99.10%, HPLC purity: 99.14%, $^1$H NMR (DMSO-$d_6$, 400 MHZ) : 9.57 (s, 1H), 8.30-8.28 (d, J = 6.4 Hz, 1H), 8.22 (s, 1H), 8.03 (s, 1H), 7.99 (bs, 1H), 7.94-7.93 (d, J = 3.6 Hz, |

TABLE 27-continued

| Compound # | Reagent | Chiral Separation Conditions and Characterization Data |
|---|---|---|
| | | 1H), 7.87-7.86 (d, J = 7.2 Hz, 1H), 7.61 (s, 1H), 6.91-6.87 (t, J = 6.8 Hz, 1H), 6.28 (s, 1H), 2.94-2.93 (d, J = 4.4 Hz, 3H), 1.24 (bs, 1H), 0.82-0.77 (m, 2H), 0.49 (bs, 2H). |
| I-589 | 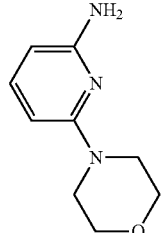<br>96iiiiii | MS (ES): m/z 409.50 [M + H]$^+$, LCMS purity: 100%, HPLC purity: 96.09%, $^1$H NMR (DMSO-d$_6$, 400 MHZ): 9.63 (s, 1H), 8.19 (s, 1H), 8.01 (s, 2H), 7.55-7.51 (t, J = 7.6 Hz, 1H), 6.84-6.82 (d, J = 6.8 Hz, 1H), 6.68 (s, 1H), 6.46-6.44 (d, J = 8.4 Hz, 1H), 3.72 (s ,4H), 3.84 (s, 4H), 2.92-2.91 (d, J = 4.4 Hz, 3H), 2.83-2.82 (m, 1H), 0.77-0.76 (m, 2H), 0.56 (bs, 2H). |
| I-203 | 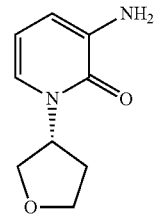 [SMILES: Nc1cccn([C@@H]2CCOC2)c1=O] | MS (ES): m/z 410.49 [M + H]$^+$, LCMS purity: 100%, HPLC purity: 100%, CHIRAL HPLC purity: 100%, $^1$H NMR (DMSO-d$_6$, 400 MHZ): 8.91 (s, 1H), 8.19 (s, 1H), 8.13-8.11 (d, J = 8 Hz, 1H), 7.91-7.90 (d, J = 4 Hz, 1H), 7.83-7.82 (d, J = 4 Hz, 1H), 7.32-7.31 (d, J = 4 Hz, 1H), 6.37-6.35 (t, J = 8 Hz, 1H), 6.20 (s, 1H), 5.52-5.49 (m, 1H), 4.11-4.05 (m, 1H), 3.91-3.90 (d, J = 4 Hz, 2H), 3.80-3.75 (m, 1H), 2.90-2.89 (d, J = 4 Hz, 3H), 2.87-2.82 (m, 1H), 2.09-2.02 (m, 1H), 1.23 (s, 1H), 0.80-0.76 (m, 2H), 0.51-0.47 (m, 2H). |
| I-295 | 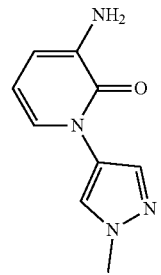<br>96jjjjjj | MS (ES): m/z 420.38 [M + H]$^+$, LCMS purity: 96.78%, HPLC purity: 97.19%, $^1$H NMR (DMSO-d$_6$, 400 MHZ): 9.00 (s, 1H), 8.30 (s, 1H), 8.20 (s, 1H), 8.17-8.15 (d, J = 8 Hz, 1H), 7.94-7.93 (d, J = 4 Hz, 1H), 7.89 (s, 1H), 7.84-7.83 (d, J = 4 Hz, 1H), 7.56-7.55 (d, J = 4 Hz, 1H), 6.40-6.39 (t, J = 4 Hz, 1H), 6.22 (s, 1H), 3.91 (s, 3H), 2.90-2.89 (d, J = 4 Hz, 3H), 2.87-2.84 (m, 1H), 0.81-0.76 (m, 2H), 0.53-0.49 (m, 2H). |
| I-394 | 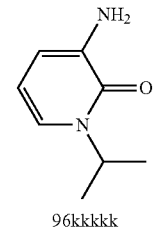<br>96kkkkk | MS (ES): m/z 382.4 [M + H]$^+$, LCMS purity: 100%, HPLC purity: 99.75%, $^1$H NMR (DMSO-d$_6$, 400 MHZ): 8.89 (s, 1H), 8.19 (s, 1H), 8.11-8.09 (d, J = 6.4 Hz, 1H), 7.83-7.82 (d, J = 3.6 Hz, 1H), 7.46-7.45 (d, J = 6 Hz, 1H), 6.35-6.31 (m, 1H), 6.20 (s, 1H), 5.21-5.14 (m, 1H), 3.18-3.16 (d, J = 5.2 Hz, 1H), 2.90-2.84 (m, 4H), 1.36-1.34 (d, J = 6.8 Hz, 6H), 0.81 (bs, 2H), 0.79-0.76 (m, 2H). |
| I-167 | 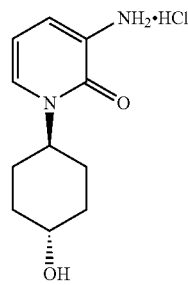 | MS (ES): m/z 438.39 [M + H]$^+$, LCMS purity: 100%, HPLC purity: 97.67%, $^1$H NMR (DMSO-d$_6$, 400 MHz): 8.87 (s, 1H), 8.19 (s, 1H), 8.11-8.09 (d, J = 8 Hz, 1H), 7.92-7.90 (d, J = 8 Hz, 1H), 7.83-7.82 (d, J = 4 Hz, 1H), 7.46-7.44 (d, J = 8 Hz, 1H), 6.33-6.31 (t, J = 8 Hz, 1H), 6.19 (s, 1H), 4.77 (m, 1H), 4.71-4.70 (d, J = 4 Hz, 1H), 3.54-3.53 (m, 1H), 2.91-2.90 (d, J = 4 Hz, 3H), 2.86-2.83 (m, 1H), 1.99-1.95 (m, 2H), 1.82-1.78 (m, 2H), 1.36-1.34 (m, 1H), 1.24 (bs, 4H), 0.86-0.84 (m, 1H), 0.81-0.78 (m, 1H), 0.49 (bs, 1H). |

TABLE 27-continued

| Compound # | Reagent | Chiral Separation Conditions and Characterization Data |
|---|---|---|
| I-271 | (structure shown) | MS (ES): m/z 434.22 [M + H]$^+$, LCMS purity: 99.25%, HPLC purity: 96.98%, $^1$H NMR (DMSO-d$_6$, 400 MHZ): 8.95 (s, 1H), 8.21 (s, 1H), 8.13-8.012 (d, J = 4 Hz, 1H), 7.95-7.93 (d, J = 8 Hz, 1H), 7.83-7.82 (d, J = 4 Hz, 2H), 7.50 (s, 1H), 6.76-6.75 (d, J = 4 Hz, 1H), 6.22 (s, 1H), 3.90 (s, 3H), 2.91-2.90 (d, J = 4 Hz, 3H), 2.79 (m, 1H), 2.21 (s, 3H), 0.76-0.75 (m, 2H), 0.52-0.51 (m, 2H). |
| I-191 | (structure shown) | MS (ES): m/z 487.53 [M + H]$^+$, LCMS purity: 100%, HPLC purity: 100%, $^1$H NMR (DMSO-d$_6$, 400 MHZ): 8.87 (s, 1H), 8.19 (s, 1H), 8.12-8.10 (d, J = 8 Hz, 1H), 7.91-7.90 (d, J = 4 Hz, 1H), 7.81 (s, 1H), 7.50-7.48 (d, J = 8 Hz, 1H), 6.32-6.30 (t, J = 8 Hz, 1H), 6.19 (s, 1H), 6.03 (s, 1H), 4.79 (m, 1H), 3.08-3.05 (d, J = 12 Hz, 2H), 2.90-2.89 (d, J = 4 Hz, 3H), 2.85-2.77 (m, 3H), 2.39-2.33 (m, 2H), 1.95-1.92 (d, J = 12 Hz, 2H), 1.77-1.74 (m, 2H), 0.79-0.77 (m, 2H), 0.49 (bs, 2H). |
| I-202 | (structure shown) | MS (ES): m/z 410.49 [M + H]$^+$, LCMS purity : 100%, HPLC purity: 99.57%, CHIRAL HPLC purity: 100%, $^1$H NMR (DMSO-d$_6$, 400 MHZ): 8.91 (s, 1H), 8.19 (s, 1H), 8.13-8.11 (d, J = 8 Hz, 1H), 7.92-7.91 (d, J = 4 Hz, 1H), 7.83-7.82 (d, J = 4 Hz, 1H), 7.32-7.31 (d, J = 4 Hz, 1H), 6.37-6.35 J = 8 Hz, 1H), 6.20 (s, 1H), 5.52-5.49 (m, 1H), 4.11-4.05 4.05 (m, 1H), 3.91-3.90 (d, J = 4 Hz, 2H), 3.80-3.75 (m, 1H), 2.90-2.89 (d, J = 4 Hz, 3H), 2.87-2.82 (m, 1H), 2.09-2.02 (m, 1H), 1.23 (s, 1H), 0.80-0.76 (m, 2H), 0.51-0.47 (m, 2H). |
| I-550 | (structure shown) 96lllll | MS(ES): m/z 436.39 [M + H]$^+$. LCMS purity: 97.90%, HPLC purity: 100%, $^1$H NMR (DMSO-d$_6$, 400 MHZ): 8.90 (s, 1H), 8.19 (s, 1H), 8.12-8.10 (d, J = 8.0 Hz, 1H), 7.93-7.91 (d, J = 8.0 Hz, 1H), 7.84-7.83 (d, J = 8.0 Hz, 1H) 7.47-7.45 (d, J = 8. 0 Hz, 1H), 6.35-6.31 (t, J = 8.0 Hz, 1H), 6.20 (s, 1H), 4.97-4.92 (m, 1H), 4.72 (s, 2H), 4.56 (s, 2H), 2.90-2.89 (d, J = 4.0 Hz, 2H), 2.86-2.85 (d, J = 4.0 Hz, 1H), 2.78-2.73 (m, 2H), 2.68-2.56 (m, 3H), 0.81-0.78 (m, 2H), 0.50 (bs, 2H). |
| I-1361 | (structure shown) 96mmmmm | MS (ES): m/z 447.52 [M + H]$^+$, LCMS purity: 100%, HPLC purity: 100%, CHIRAL HPLC: 50.35%, 48.55%, $^1$H NMR (DMSO-d$_6$, 400 MHz): 8.88 (s, 1H), 8.20-8.11 (m, 2H), 7.93-7.83 (m, 2H), 7.50-7.48 (d, J = 6 Hz, 1H), 6.36-6.20 (m, 2H), 4.86 (bs, 1H), 3.17 (bs, 1H), 2.90 (s, 3H), 2.12-2.03 (m, 3H), 1.89 (bs, 2H), 1.76-1.71 (d, J = 21.2 Hz, 2H), 1.54 (bs, 2H), 0.80-0.79 (d, J = 5.6 Hz, 2H), 0.50 (bs, 2H). |

TABLE 27-continued

| Compound # | Reagent | Chiral Separation Conditions and Characterization Data |
|---|---|---|
| I-1244<br>I-1245 | 96mmmmm | Intermediate corresponding to 96.1 en route to I-1361 was separated into isomers before BOC removal: CHIRALCEL OJ-H (250 mm * 4.6 mm, 5u) and 0.1% DEA in methanol at 4 mL/min.<br>Product prepared from FR-a: MS (ES): 447.61 [M + H]$^+$ LCMS purity: 99.25%, HPLC purity: 99.22%, CHIRAL HPLC: 98.70%, $^1$H NMR (DMSO-d$_6$, 400 MHZ): 8.87 (s, 1H), 8.19 (s, 1H), 8.11-8.10 (d, J = 6.4 Hz, 1H), 7.92-7.91 (d, J = 4.8 Hz, 1H), 7.82-7.81 (d, J = 3.6 Hz, 1H), 7.49-7.47 (d, J = 7.2 Hz, 1H), 6.35-6.32 (t, J = 7.2 Hz, 1H), 6.19 (s, 1H), 3.06 (bs, 1H), 2.90-2.89 (d, J = 4.4 Hz, 3H), 2.87-2.83 (m, 1H), 1.76 (bs, 3H), 1.56 (bs, 3H), 1.23 (bs, 2H), 0.87-0.84 (m, 1H), 0.81-0.76 (m, 2H), 0.50 (bs, 2H).<br>Product prepared from FR-b: MS (ES): 447.66 [M + H]$^+$ LCMS purity :100%, HPLC purity: 98.65%, CHIRAL HPLC: 97.34%, $^1$H NMR (DMSO-d$_6$, 400 MHZ): 8.87 (s, 1H), 8.19 (s, 1H), 8.11-8.10 (d, J = 6.4 Hz, 1H), 7.92-7.91 (d, J = 4.8 Hz, 1H), 7.82 (bs, 1H), 7.49-7.47 (d, J = 7.2 Hz, 1H), 6.35-6.32 (t, J = 7.2 Hz, 1H), 6.19 (s, 1H), 4.85 (bs, 1H), 3.07 (bs, 1H), 2.90-2.89 (d, J = 4.4 Hz, 3H), 1.76 (bs, 3H), 1.56 (bs, 3H), 1.24 (bs, 2H), 0.86 (bs, 1H), 0.79-0.78 (d, J = 5.6 Hz, 2H), 0.49 (bs, 2H). |
| I-1275 | | MS (ES): m/z 438.71 [M + H]$^+$, LCMS purity: 97.34%, HPLC purity: 95.44% $^1$H NMR (DMSO-d$_6$, 400 MHZ): 9.06 (s, 1H), 8.24 (s, 1H), 8.21 (s, 1H), 8.06 (s, 1H), 7.96 (bs, 1H), 7.83 (bs, 1H), 7.36-7.35 (d, J = 5.2 Hz, 1H), 6.40 (bs, 1H), 6.21(bs, 1H), 3.86 (s, 3H), 2.89 (s, 3H), 1.23 (bs, 1H), 0.80-0.78 (d, J = 5.2 Hz, 2H), 0.52 (bs, 2H). |
| I-1271 | 96nnnnn | MS (ES): 410.32 [M + H]$^+$ LCMS purity: 100%, HPLC purity: 99.33%, CHIRAL HPLC purity: 49.64%, 50.35%, $^1$H NMR (DMSO-d$_6$, 400 MHZ): 8.92 (s, 1H), 8.20 (s, 1H), 8.15-8.13 (d, J = 6.8 Hz, 1H), 7.92-7.91 (d, J = 4.4 Hz, 1H), 7.85-7.84 (d, J = 3.2 Hz, 1H), 7.34-7.32 (d, J = 6.8 Hz, 1H), 6.27-6.23 (t, J = 6.8 Hz, 1H), 6.21 (s, 1H), 3.54-3.53 (d, J = 3.2 Hz, 2H), 3.22 (s, 3H), 2.91-2.90 (d, J = 4.8 Hz, 3H), 2.88-2.85 (m, 1H), 1.33 (bs, 1H), 1.27-1.23 (m, 1H), 0.80-0.78 (d, J = 5.6 Hz, 2H), 0.50 (bs, 2H). |

TABLE 27-continued

| Compound # | Reagent | Chiral Separation Conditions and Characterization Data |
|---|---|---|
| I-1228<br>I-1227 | 96nnnnn | Intermediate corresponding to 96.1 en route to I-1271 was separated into isomers before BOC removal: CHIRALCEL OJ-H (250 mm * 4.6 mm, 5u) and 0.1% DEA in methanol at 4 mL/min.<br>Product prepared from FR-a: MS (ES): 410.70 [M + H]+ LCMS purity: 100%, HPLC purity: 97.75%, CHIRAL HPLC: 95.92%, $^1$H NMR (DMSO-$d_6$, 400 MHZ): 8.92 (s, 1H), 8.20 (s, 1H), 8.15-8.13 (d, J = 7.2 Hz, 1H), 7.92-7.91 (d, J = 4.8 Hz, 1H), 7.85 (bs, 1H), 7.34-7.32 (d, J = 6.8 Hz, 1H), 6.27-6.23 (t, J = 7.2 Hz, 1H), 6.21 (s, 1H), 3.54-3.52 (m, 2H), 3.50-3.45 (m, 1H), 3.22 (s, 3H), 2.91-2.90 (d, J = 4.8 Hz, 3H), 1.33 (bs, 1H), 1.27-1.21 (m, 1H), 0.80-0.78 (d, J = 5.6 Hz, 2H), 0.50 (bs, 2H).<br>Product prepared from FR-b: MS (ES): 410.75 [M + H]+ LCMS purity: 100%, HPLC purity: 99.60%, CHIRAL HPLC: 96.30%, $^1$H NMR (DMSO-$d_6$, 400 MHZ): 8.92 (s, 1H), 8.20 (s, 1H), 8.15-8.13 (d, J = 7.2 Hz, 1H), 7.92-7.91 (d, J = 4.8 Hz, 1H), 7.85 (bs, 1H), 7.34-7.32 (d, J = 6.8 Hz, 1H), 6.27-6.23 (t, J = 7.2 Hz, 1H), 6.21 (s, 1H), 3.54-3.50 (m, 2H), 3.50-3.45 (m, 1H), 3.22 (s, 3H), 2.91-2.90 (d, J = 4.8 Hz, 3H), 1.34 (bs, 1H), 1.26-1.21 (m, 1H), 0.80-0.78 (d, J = 5.6 Hz, 2H), 0.50 (bs, 2H). |

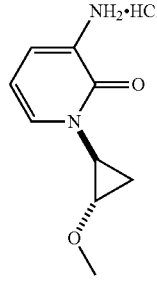

Synthesis of N-cyclopropyl-5-((1-(4-fluorophenyl)-2-oxo-1,2-dihydropyridin-3-yl)amino)-7-(methylamino)pyrazolo[1,5-a]pyrimidine-3-carboxamide (I-107)

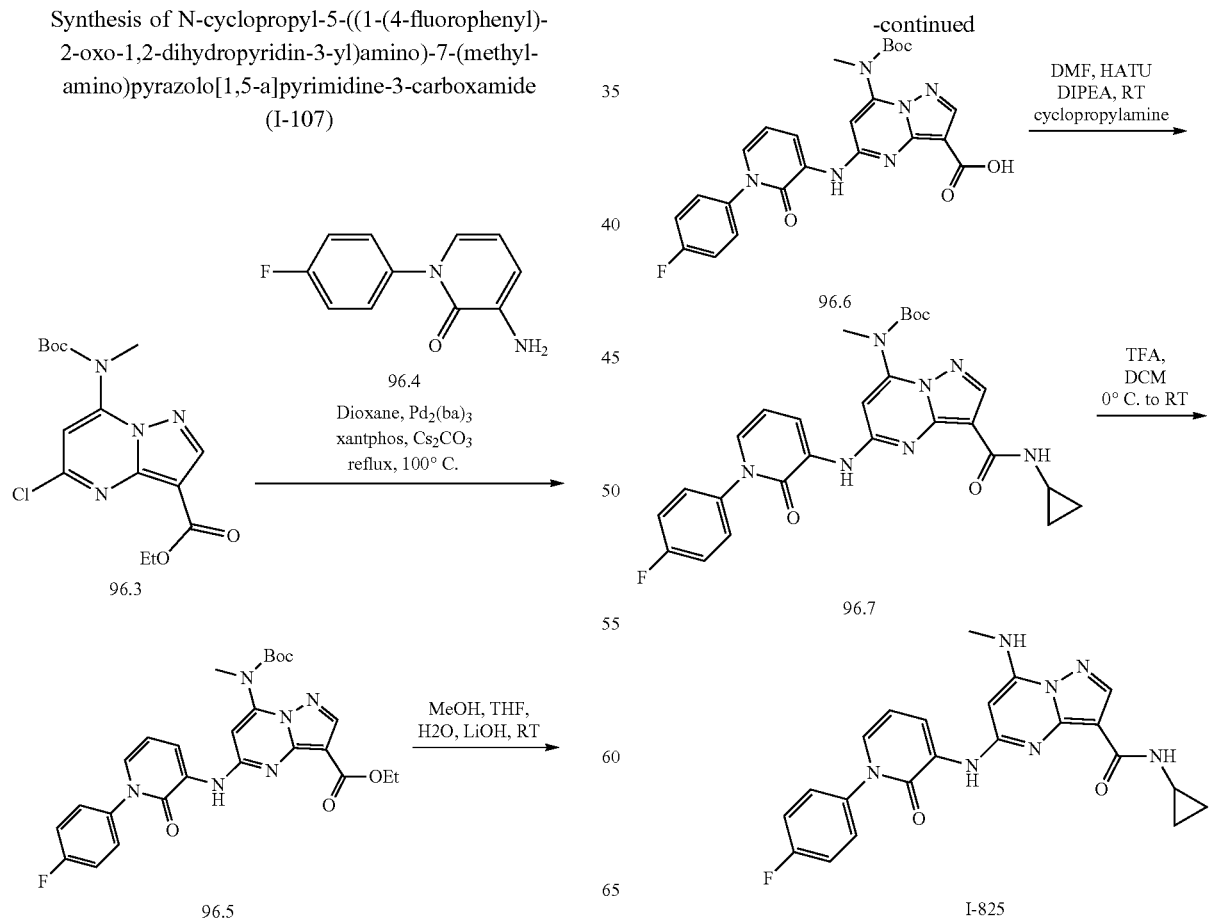

Synthesis of Compound 96.3.

Compound was synthesized using general procedure of core synthesis to obtain 96.3 (Yield: 62.21%). MS (ES): m/z 355.5 [M+H]+.

Synthesis of Compound 96.4.

Compound was synthesized as per I-25 to obtain 96.4.

Synthesis of Compound 96.5.

Compound was synthesized using general procedure B to obtain 96.5 (0.370 g, 50.24%). MS (ES): m/z 523.54 [M+H]+.

Synthesis of Compound 96.6.

To a solution of 96.5 (0.370 g, 0.708 mmol, 1.0 eq), in tetrahydrofuran: methanol: water (12 mL, 1:1:1) was added lithium hydroxide (0.297 g, 7.08 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.9% methanol in dichloromethane to obtain pure 96.6 (0.260 g, 74.26%). MS(ES): m/z 495.48 [M+H]+.

Synthesis of Compound 96.7.

Compound was synthesized using general procedure A to obtain 96.7 (0.100 g, 71.29%). MS (ES): m/z 534.56 [M+H]+.

Synthesis of Compound I-107:

Compound was synthesized using general procedure C to obtain I-107 (0.060 g, 73.86%), MS (ES): m/z 434.34 [M+H]+, LCMS purity: 100%, HPLC purity: 98.32%, $^1$H NMR (DMSO-d$_6$, 400 MHZ): 8.96 (s, 1H), 8.24 (s, 1H), 8.21 (s, 1H), 7.94-7.93 (d, J=4 Hz, 1H), 7.86-7.85 (d, J=4 Hz, 1H), 7.59-7.56 (m, 2H), 7.42-7.36 (m, 3H), 6.41-6.39 (t, J=8 Hz, 1H), 6.22 (s, 1H), 2.91-2.88 (m, 4H), 0.82-0.80 (d, J=8 Hz, 2H), 0.54 (bs, 2H).

Characterization data for further compounds prepared by the above methods are presented in Table 28 below. Compounds in Table 28 were prepared by methods substantially similar to those described to prepare I-825, where compound 96.4 was replaced with the reagent

TABLE 28

| Compound # | Reagent | Chiral Separation Conditions and Characterization Data |
|---|---|---|
| I-3 | 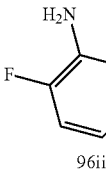 96ii | MS (ES): m/z 359.48 [M + H]+, LCMS purity: 98.12%, HPLC purity: 96.01%, $^1$H NMR (DMSO-d$_6$, 400 MHZ): 9.37 (s, 1H), 8.26 (s, 1H), 8.00-7.99 (d, J = 4.8 Hz, 1H), 7.83-7.80 (m, 1H), 7.75-7.74 (d, J = 3.6 Hz, 1H), 7.39-7.33 (m, 1H), 7.01-6.96 (m, 1H), 5.80 (s, 1H), 2.91-2.89 (d , J = 5.6 Hz, 3H), 2.79-2.67 (m, 1H), 0.69-0.65 (m, 2H), 0.36-0.33 (m, 2H). |
| I-7 | 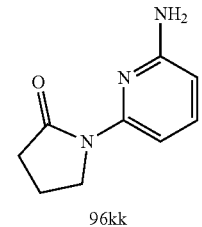 [SMILES: Nc1cccc(N2CCCC2=O)n1] 96kk | MS (ES): m/z 407.54 [M + H]+, LCMS purity: 97.35%, HPLC purity: 97.51%, $^1$HNMR (DMSO-d$_6$, 400 MHZ): 8.22 (s, 1H), 8.08-8.07 (d, J = 5.2 Hz, 1H), 7.99-7.99 (d, J = 3.6 Hz, 1H), 7.93-7.91 (d, J = 8 Hz, 1H), 7.79-7.75 (t, J = 8 Hz, 1H), 7.24-7.22 (d, J = 8 Hz, 1H), 6.77 (bs, 1H), 4.14-4.10 (t, J = 6.8 Hz, 2H), 3.19-3.18 (d, J = 4 Hz, 1H), 2.98-2.97 (d, J = 4.8 Hz, 3H), 2.85-2.82 (m, 1H), 2.62-2.58 (t, J = 8 Hz, 2H), 2.10-2.06 (t, J = 7.6 Hz, 2H), 0.79-0.76 (m, 2H), 0.56 (bs, 2H). |
| I-6 | 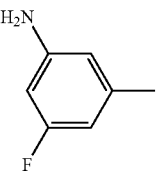 | MS (ES) m/z 355.3 [M + H]+, LCMS purity: 96.35%, HPLC purity: 95.23%, 1H NMR (DMSO-d$_6$, 400 MHZ): 9.61(s, 1H), 8.19(s, 1H), 7.96-7.95 (d, J = 4.80 Hz, 1H), 7.84-7.83 (d, J = 3.6 Hz, 1H), 7.42-7.39 (d, J = 11.2 Hz 1H), 7.02 (s, 1H), 6.73-6.71 (d, J = 9.2, 1H), 5.54 (S, 1H), 2.93-2.92 (d, J = 4.8 Hz, 3H), 2.83-2.80 (m, 1H), 2.34 (s, 3H), 0.74-0.70 (m, 2H), 0.48-0.45 (m, 2H). |
| I-5 | 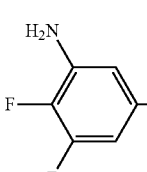 | MS (ES): m/z 377.53 [M + H]+, LCMS purity: 100%, HPLC purity: 98.61%, $^1$H NMR (DMSO-d$_6$, 400 MHZ): 9.59 (s, 1H), 8.21 (s, 1H), 8.07-8.06 (d, J = 4.8 Hz, 1H), 7.72-7.70 (t, J = 5.6 Hz, 2H), 7.29-7.25 (m, 1H), 5.83 (s, 1H), 2.94-2.92 (d, J = 4.8 Hz, 3H), 2.80-2.76 (m, 1H), 0.71-0.66 (m, 2H), 0.38-0.34 (m, 2H). |
| I-8 | 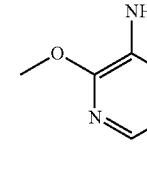 | MS (ES): m/z 354.52 [M + H]+, LCMS purity: 98.92%, HPLC purity: 97.7%, $^1$H NMR (DMSO-d$_6$, 400 MHZ): 8.92 (s, 1H), 8.22 (d, J = 8.8 Hz, 1H), 8.16 (s, 1H), 7.94-7.89 (m, 2H), 7.80-7.79 (d, J = 4 Hz, 1H), 7.05-7.01 (m, 1H), 5.89 (s, 1H), 3.96 (s, 3H), 2.92-2.91 (d, J = 4.8 Hz, 3H), 2.81-2.77 (m, 1H), 0.73-0.69 (m, 2H), 0.38-0.34 (m, 2H). |
| I-98 | 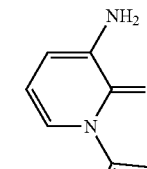 | MS (ES): m/z 446.60 [M + H]+, LCMS purity: 100%, HPLC purity: 100%, $^1$H NMR (DMSO-d$_6$, 400 MHZ): 9.02 (s, 1H), 8.20-8.17 (m, 2H), 7.93 (s, 2H), 7.84-7.83 (d, J = 4 Hz, 1H), 7.70-7.68 (d, J = 8 Hz, 1H), 6.75-6.74 (d, J = 4 Hz, 1H), 6.42-6.40 (t, J = 8 Hz, 1H), 6.21 (s, 1H), 3.81-3.77 (m, 1H), 2.90-2.89 (d, J = 4 Hz, 3H), 2.87-2.86 (d, J = 4 Hz, 1H), 1.11-1.05 (m, 2H), 1.01-0.98 (m, 2H), 0.80-0.78 (d, J = 8 Hz, 2H), 0.51 (s, 2H). |
| I-155 | 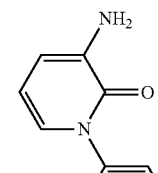 | MS(ES): m/z 475.53 [M + H]+, LCMS purity: 99.17%, HPLC purity: 98.66%, $^1$H NMR (DMSO-d$_6$, 400 MHZ): 9.01 (s, 1H), 8.24-8.21 (m, 2H), 8.02-7.98 (m, 1H), 7.94-7.93 (d, J = 4.8 Hz, 1H), 7.86-7.85 (m, 1H), 7.76-7.74 (d, J = 8 Hz, 1H), 7.70-7.68 (d, J = 8 Hz, 1H), 7.63-7.61 (d, J = 5.6 Hz, 1H), 6.47-6.44 (t, J = 14.4 Hz, 1H), 6.22 (s, 1H), 5.37 (s, 1H), 2.91-2.89 (m, 3H), 1.48 (s, 6H), 0.80-0.78 (m, 2H), 0.53 (bs, 2H). |

Synthesis of 5-((1-(1-(2-cyanoethyl)piperidin-4-yl)-2-oxo-1,2-dihydropyridin-3-yl)amino)-N-cyclopropyl-7-(methylamino)pyrazolo[1,5-a]pyrimidine-3-carboxamide (I-652)

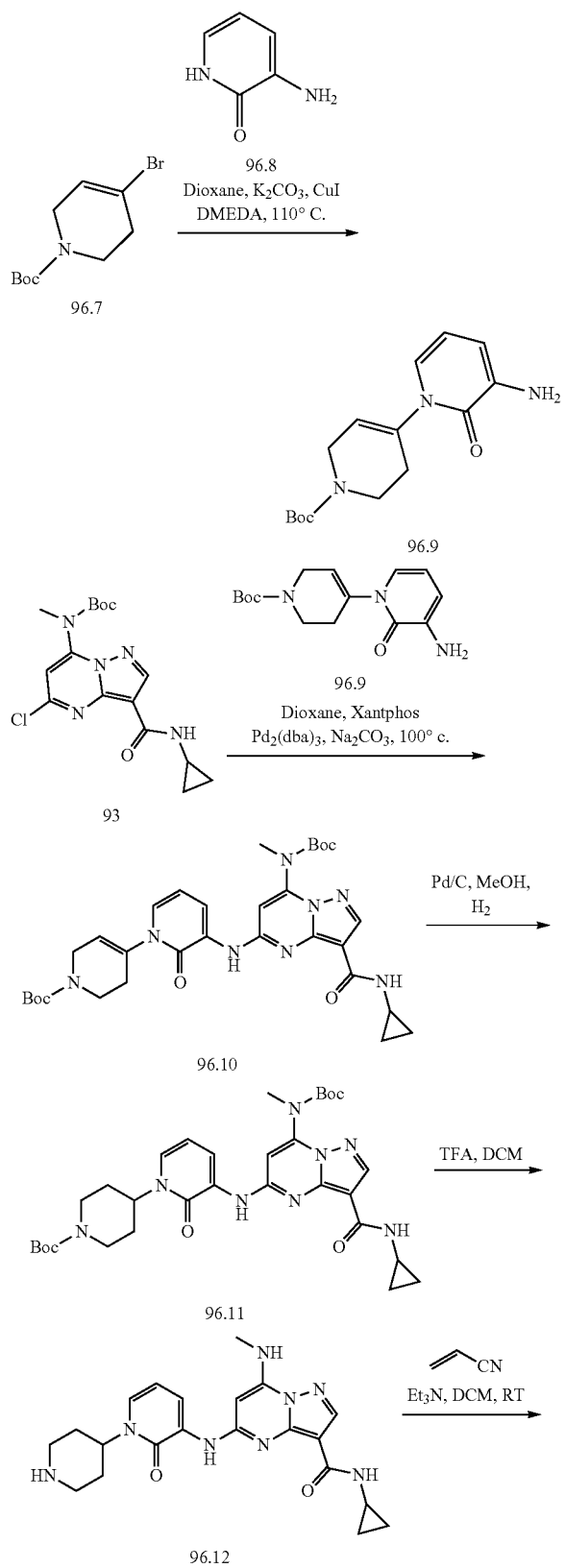

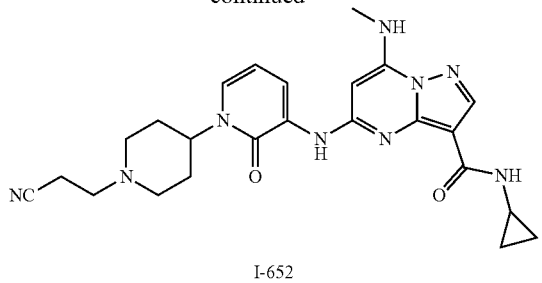

I-652

Synthesis of Compound 96.9.

To a solution of 96.7 (1.0 g, 3.81 mmol, 1 eq) in 1,4-dioxane (50 mL), 96.8 (0.545 g, 4.95 mmol, 1.3 eq) was added. The reaction mixture was degassed for 10 min under argon atmosphere followed by addition of potassium carbonate (1.31 g, 9.52 mmol, 2.5 eq), N,N-dimethylethylenediamine (0.083 g, 0.95 mmol, 0.25 eq), and copper iodide (0.108 g, 0.57 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96.9. (0.450 g, Yield: 40.49%). MS (ES): m/z 292.1 [M+H]$^+$.

Synthesis of Compound 93.

Compound was synthesized as per Example 27 (I-127) using compound 96.9 to obtain 93. (Yield: 57.16%), MS (ES): m/z 366.82 [M+H]$^+$.

Synthesis of Compound 96.10.

Compound was synthesized using general procedure B to obtain 96.10. (0.240 g, Yield: 70.72%). MS (ES): m/z 621.3 [M+H]$^+$ Synthesis of Compound 96.11.

To a solution of 96.10 (0.240 g, 0.38 mmol, 1.0 eq) in methanol (4 ml), palladium on charcoal (0.070 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 92% ethyl acetate in hexane to obtain pure 96.11. (0.190 g, 78.91%). MS (ES): m/z 623.3 [M+H]$^+$ Synthesis of Compound 96.12.

Compound was synthesized using general procedure C to obtain 96.12. (0.160 g, Yield: 93.09%). MS (ES): m/z 423.2 [M+H]$^+$ Synthesis of Compound I-652.

To a solution of 96.12 (0.160 g, 0.37 mmol, 1 eq) and acrylonitrile (0.022 g, 0.43 mmol, 1.1 eq) in dichloromethane (10 mL) was added triethylamine (0.074 g, 0.74 mmol, 2.0 eq). The reaction mixture was stirred at room temperature for 4 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure I-652 (0.035 g, 19.43%). MS (ES): m/z 476.26 [M+H]+, LCMS purity: 100%, HPLC purity: 99.72%, 1H NMR (DMSO-d6, 400 MHZ): 8.88 (s, 1H), 8.20 (s, 1H), 8.13-8.11 (d, J=7.2 Hz, 1H), 7.92-7.91 (d, J=4.4 Hz, 1H), 7.83-7.82 (d, J=3.6 Hz, 1H), 7.51-7.49 (d, J=7.2 Hz, 1H), 6.34.6.30 (t, J=6.8 Hz, 1H), 6.20 (s, 1H), 3.08-3.05 (d, J=10.5 Hz, 2H), 2.91-2.90 (d, J=4.8 Hz, 4H), 4.72-2.66 (m, 4H), 2.25-2.19 (t, J=11.2 Hz, 3H), 1.97-1.91 (m, 2H), 1.81-1.79 (m, 2H), 0.80-0.79 (d, J=5.6 Hz, 2H), 0.50 (bs, 2H).

Synthesis of N-cyclopropyl-7-(methylamino)-5-(1-(2-(piperidin-1-yl)ethyl)-1H-pyrrolo[2,3-b]pyridin-3-yl)pyrazolo[1,5-a]pyrimidine-3-carboxamide (I-584)

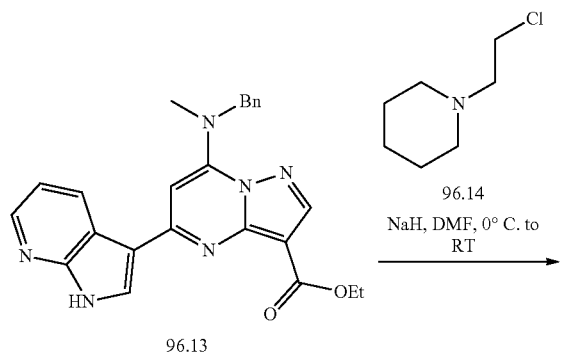

96.13

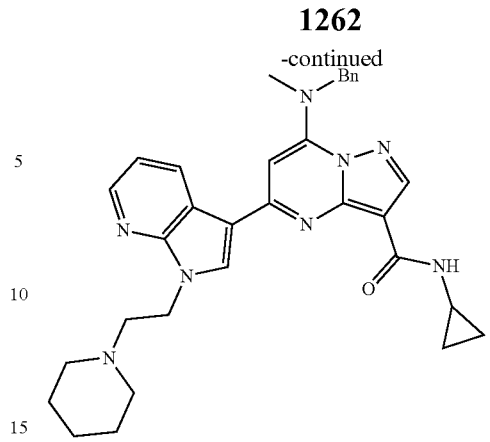

96.17

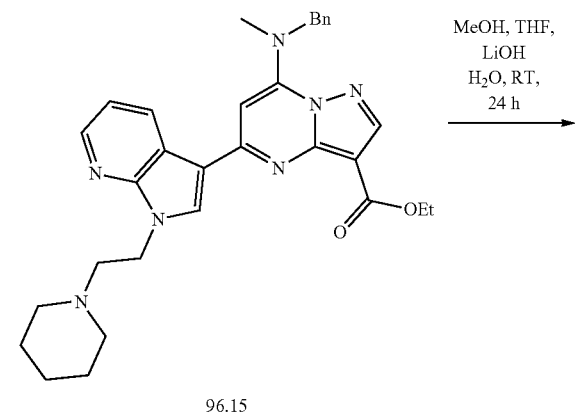

96.15

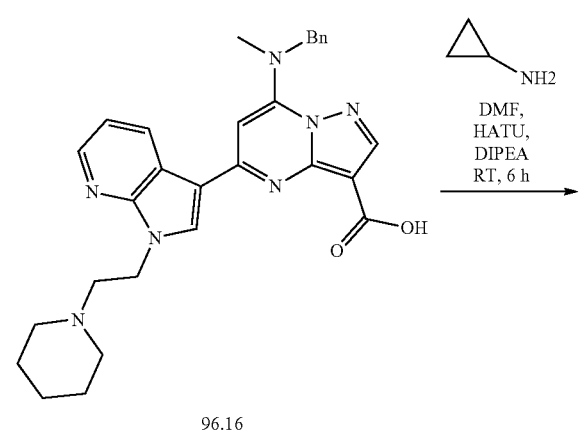

96.16

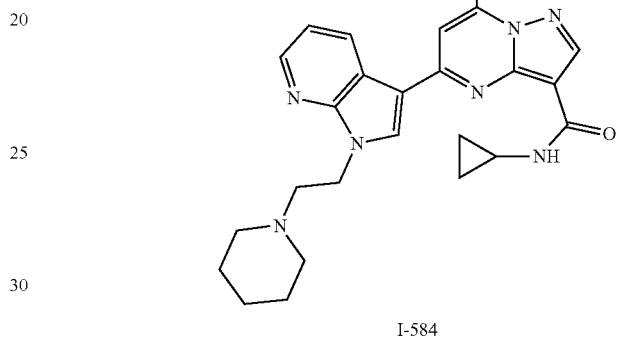

I-584

Synthesis of Compound 96.13.

Compound was synthesized as per I-582 using compound 96.14 to obtain 96.13 (Yield: 99.41%). MS (ES): m/z 427.51 [M+H]+.

Synthesis of Compound 96.15.

Sodium hydride (0.225 g, 5.6 mmol, 4.0 eq) was added to a solution of 96.13 (0.600 g, 1.4 mmol, 1.0 eq) in N—N-Dimethylformamide (12 mL) at 0° C. portion wise. Reaction mixture was stirred at same temperature for 20 min, 96.14 (0.780 g, 4.22 mmol, 3.0 eq) was added and mixture was allowed to stirred at room temperature for 16 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography eluting pure compound in 2-3% methanol in dichloromethane to obtain pure 96.15 (0.420 g, 54.23%). MS (ES): m/z 538.51 [M+H]+.

Synthesis of Compound 96.16.

To a solution of 96.15 (0.400 g, 0.744 mmol, 1.0 eq), in tetrahydrofuran: methanol: water (20 mL, 1:1:1) was added lithium hydroxide (0.315 g, 7.44 mmol, 10 eq). The reaction was stirred 60° C. for 6 h. After completion of reaction, reaction mixture was concentrated under reduced pressure to obtain residue. To this added water and acidified with 1N hydrochloric acid to adjust pH~6-6.5 at 10° C. Product was filtered and dried under vacuum to obtain pure 96.16 (370 mg, 97.37%). MS(ES): m/z 510.2 [M+H]+.

Synthesis of Compound 96.17.

Compound was synthesized using general procedure A to obtain 96.17 (0.130 g, 67.01%). MS (ES): m/z 549 [M+H]+.

Synthesis of Compound I-584.

Mixture of 96.17 (0.130 g, 0.236 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-584 (0.045 g, 41.67%), MS (ES): m/z 459.39 [M+H]$^+$, LCMS purity: 100%, HPLC purity: 100%, $^1$H NMR (DMSO-d$_6$, 400 MHZ): 8.67-8.63 (m, 2H), 8.41-8.40 (d, J=3.2 Hz, 1H), 8.37 (s, 1H), 8.33-8.32 (d, J=3.6 Hz, 1H), 8.26 (bs, 1H), 7.32-7.29 (m, 1H), 6.67 (s, 1H), 4.49-4.46 (t, J=13.6 Hz, 2H), 3.10 (s, 3H), 2.96-2.92 (m, 1H), 2.79-2.76 (t, J=13.2 Hz, 2H), 2.52-2.46 (m, 4H), 1.48-1.46 (m, 4H), 1.40-1.37 (m, 2H), 0.89-0.85 (m, 2H), 0.65-0.61 (m, 2H).

Characterization data for further compounds prepared by the above methods are presented in Table 29 below. Compounds in Table 29 were prepared by methods substantially similar to those described to prepare I-584, where compound 96.14 was replaced with the reagent as indicated in Table 29.

TABLE 29

| Compound # | Reagent | Chiral Separation Conditions and Characterization Data |
|---|---|---|
| I-616 | Cl-CH₂CH₂-N(piperazine-N-methyl) | MS(ES): m/z 474.36 [M + H]$^+$, LCMS purity: 100%, HPLC purity: 99.03%, $^1$H NMR (DMSO-d$_6$, 400 MHZ): 8.68-8.63 (m, 2H), 8.41-8.27 (m, 3H), 7.32-7.29 (m, 1H), 6.66 (s, 1H), 4.48 (s, 2H), 3.10-3.09 (d, J = 4.0 Hz, 3H), 2.93-2.90 (m, 2H), 2.81 (s, 2H), 2.34-2.30 (m, 6H), 2.13 (s, 3H), 1.24 (s, 1H), 0.88-0.86 (d, J = 8.0 Hz, 2H), 0.63 (bs, 2H). |
| I-582 | Cl-CH₂CH₂-N(morpholine) | MS (ES): m/z 461.39 [M + H]$^+$, LCMS purity: 97.08%, HPLC purity: 96.19%, $^1$H NMR (DMSO-d$_6$, 400 MHZ): 8.67 (s, 1H), 8.63-8.61 (d, J = 6.8 Hz, 1H), 8.40-8.39 (d, J = 3.6 Hz, 1H), 8.36 (s, 1H), 8.31-8.30 (d, J = 3.6 Hz, 1H), 8.26-8.25 (d, J = 4.8 Hz, 1H), 7.31-7.28 (m, 1H), 6.65 (s, 1H), 4.50-4.47 (t, J = 13.2 Hz, 2H), 3.56-3.51 (m, 4H), 3.10-3.07 (m, 3H), 2.95-2.89 (m, 1H), 2.83-2.78 (m, 2H), 2.50-2.45 (m, 4H) 0.85-0.83 (m, 2H), 0.56-0.54 (m, 2H). |
| I-477 | 4-iodobutane | MS (ES): m/z 404.37 [M + H]$^+$, LCMS purity: 97.66%, HPLC purity: 97.27%, $^1$H NMR (DMSO-d$_6$, 400 MHZ): 8.67 (s, 1H), 8.65-8.63 (d, J = 7.6 Hz, 1H), 8.41-8.40 (d, J = 3.6 Hz, 1H), 8.37-8.24 (m, 3H), 7.30 (bs, 1H), 6.71 (s, 1H), 4.37 (bs, 2H), 3.10-3.09 (d, J = 4 Hz, 3H), 2.94 (bs, 1H), 1.92-1.88 (d, J = 7.2 Hz, 2H), 1.35-1.30 (m, 2H) 0.96-0.86 (m, 5H), 0.63 (bs, 2H). |

Synthesis of 5-((5-chloro-1-ethyl-2-oxo-1,2-dihydropyridin-3-yl)amino)-N-cyclopropyl-7-(methylamino)pyrazolo[1,5-a]pyrimidine-3-carboxamide (I-133)

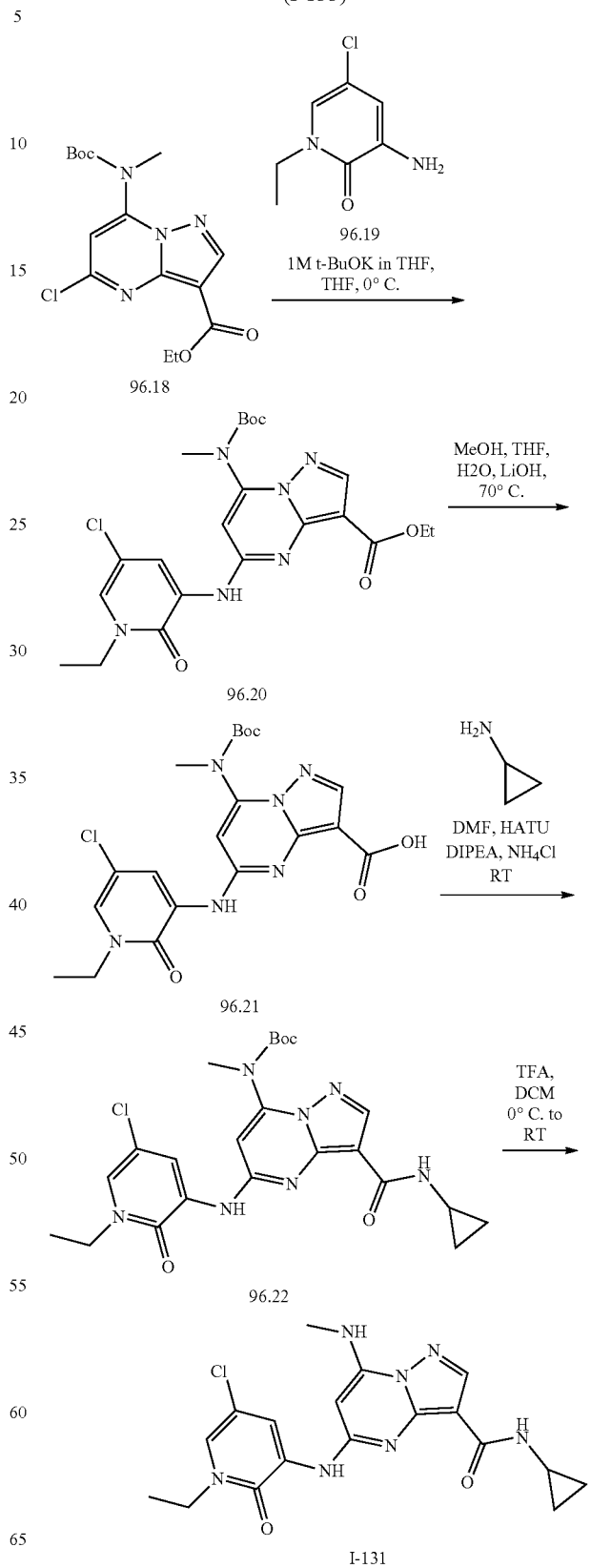

Synthesis of Compound 96.18.

Compound was synthesized using general procedure of core synthesis to obtain 96.18. (Yield: 62.21%). MS (ES): m/z 355.5 [M+H]$^+$ Synthesis of Compound 96.19.

Compound was synthesized as per Example 103 (I-35).

Synthesis of Compound 96.20.

To a solution of 96.18 (0.20 g, 0.56 mmol, 1.0 eq) and 96.19 (0.11 g, 0.67 mmol, 1.2 eq) in tetrahydrofuran (3 mL) was added, potassium tert.butoxide (1.1 mL, 1.12 mmol, 2.0 eq) at 0° C. The reaction mixture was stirred at 0° C. for 30 min. After completion of reaction, reaction mixture was transferred to ice cold water and product was extracted with ethylacetate. Organic layer was combined, dried over sodium sulphate and concentrated under reduced pressure to obtain crude material. This was further purified by column chromatography to obtain pure 96.20 (0.11 g, 39.75%). MS (ES): m/z 491.95 [M+H]$^+$ Synthesis of Compound 96.21.

To a solution of 96.20 (0.1 g, 0.22 mmol, 1.0 eq), in tetrahydrofuran: methanol: water (5 mL, 1:1:1) was added lithium hydroxide (0.09 g, 2.2 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 70° C. Product was extracted with dichloromethane. Organic layer was combined, washed with brine solution, dried over sodium sulphate and concentrated under reduced pressure to obtain 96.21 (0.06 g, 62.67%). MS(ES): m/z 463.89 [M+H]$^+$.

Synthesis of Compound 96.22.

Compound was synthesized using general procedure A to obtain 96.22 (Yield: 70.97%). MS (ES): m/z 402.86 [M+H]$^+$.

Synthesis of Compound I-133.

Compound was synthesized using general procedure C to obtain I-133. (Yield: 52.36%). MS (ES): m/z 401.86 [M+H]$^+$, LCMS purity: 95.85%, HPLC purity: 96.35%, $^1$H NMR (DMSO-d$_6$, 400 MHZ): 9.00 (s, 1H), 8.22-8.21 (d, J=6.8 Hz, 2H), 7.97-7.96 (d, J=4.8 Hz, 1H), 7.66-7.65 (m, 2H), 6.28 (s, 1H), 4.04-3.99 (m, 2H), 2.90-2.89 (d, J=4.8 Hz, 3H), 2.79-2.78 (m, 1H), 1.30-1.23 (m, 3H), 0.75-0.74 (d, J=5.2 Hz, 2H), 0.56 (bs, 2H).

Characterization data for further compounds prepared by the above methods are presented in Table 30 below. Compounds in Table 30 were prepared by methods substantially similar to those described to prepare I-133, where compound 96.19 was replaced with the reagent as indicated in Table 30.

TABLE 30

| Compound # | Reagent | Chiral Separation Conditions and Characterization Data |
|---|---|---|
| I-1 | 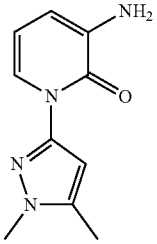 | MS(ES): m/z 351.56 [M + H]$^+$, LCMS purity: 96.68%, HPLC purity: 96.09%, $^1$H NMR (DMSO-d$_6$, 400 MHZ): 9.32 (s, 1H), 8.14 (s, 1H), 7.97-7.96 (d, J = 3.2 Hz, 1H), 7.86-7.85 (d, J = 5.2 Hz, 1H), 7.14 (s, 2H), 6.73(s, 1H), 5.50 (s, 1H), 2.91(s, 3H), 2.77-2.74 (m, 1H), 2.30 (s, 6H), 0.72-0.67 (m, 2H), 0.35 (m, 2H). |
| I-138 | 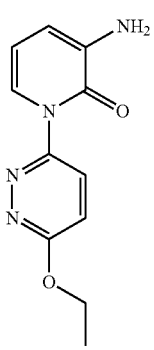 | MS (ES): m/z 434.48 [M + H]$^+$, LCMS purity: 98.67%, HPLC purity: 97.12%, $^1$H NMR (DMSO-d$_6$, 400 MHZ): 8.99 (s, 1H), 8.20-8.15 (m, 2H), 7.94-7.93 (d, J = 4.8 Hz, 1H), 7.83-7.82 (d, J = 4 Hz, 1H), 7.65-7.63 (m, 1H), 6.55 (s, 1H), 6.40-6.36 (t, J = 7.2 Hz, 1H), 6.21 (s, 1H), 3.77 (s, 3H), 2.90-2.84 (m, 4H), 2.32 (s, 3H), 1.23 (s, 2H), 0.78-0.76 (d, J = 4.8 Hz, 2H). |
| I-118 | 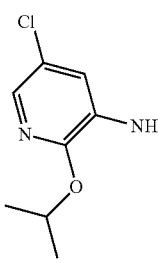 | MS (ES): m/z 462.35 [M + H]$^+$, LCMS purity: 100%, HPLC purity: 96.33%, $^1$H NMR (DMSO-d$_6$, 400 MHZ): 9.02 (s, 1H), 8.28-8.26 (d, J = 8 Hz, 1H), 8.21 (s, 1H), 8.06-8.02 (m, 1H), 7.94 (s, 1H), 7.85-7.84 (d, J = 4 Hz, 1H), 7.61-7.59 (d, J = 8 Hz, 1H), 7.49-7.43 (m, 1H), 6.49-6.48 (t, J = 4 Hz, 1H), 6.22 (s, 1H), 4.58-4.53 (m, 1H), 4.11 (s, 1H), 2.90-2.86 (m, 4H), 1.45-1.43 (t, J = 8 Hz, 3H), 0.82-0.78 (m, 2H), 0.53 (m, 2H). |
| I-150 | 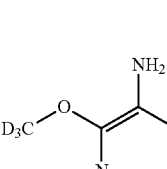 | MS (ES): m/z 416.88 [M + H]$^+$, LCMS purity: 98.22%, HPLC purity: 98.41%, $^1$H NMR (DMSO-d$_6$, 400 MHZ): 8.75 (s, 1H), 8.33-8.33 (d, J = 2 Hz, 1H), 8.19 (s, 1H), 7 99-7.98 (d, J = 4.8 Hz, 1H), 7.91-7.90 (d, J = 2 Hz, 1H), 7.76-7.69 (d, J = 3.6 Hz, 1H), 5.97 (s, 1H), 5.34-5.27 (m, 1H), 4.13-4.00 (m, 1H), 2.93-2.92 (d, J = 4.8 Hz, 3H), 2.76-2.72 (m, 1H), 1.99 (s, 1H), 1.35-1.23 (m, 6H), 1.23-1.97 (m, 1H), 0.714-0.69 (m, 1H). |
| I-90 | 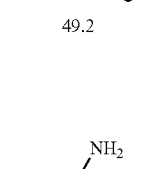 49.2 | MS (ES): m/z 408.09 [M + H]$^+$, LCMS purity: 98.41%, HPLC purity: 98.52%, $^1$H NMR (DMSO-d$_6$, 400 MHZ): 9.29 (s, 1H), 8.41-8.39 (d, J = 8 Hz, 1H), 8.17 (s, 1H), 8.13-8.12 (d, J = 4 Hz, 1H), 8.04-8.03 (d, J = 4 Hz, 1H), 7.66-7.65 (d, J = 4 Hz, 1H), 7.47-7.45 (t, J = 8 Hz, 1H), 5.79 (s, 1H), 2.93-2.92 (d, J = 4 Hz, 3H), 2.67 (s, 1H), 0.66-0.65 (d, J = 4 Hz, 2H), 0.25 (s, 2H). |
| I-157 | 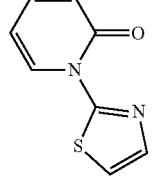 | MS (ES): m/z 423.47 [M + H]$^+$, LCMS purity: 95.45%, HPLC purity: 96.95%, $^1$H NMR (DMSO-d$_6$, 400 MHZ): 9.29 (s, 1H), 8.51 (s, 1H), 8.02-8.00 (m, 2H), 7.97 (s, 1H), 7.83-7.71 (m, 3H), 6.64 (s, 1H), 6.24 (s, 1H), 2.90 (s, 3H), 1.94 (s, 1H), 1.74 (s, 1H), 1.21-1.09 (m, 1H), 0.78 (bs, 2H). |
| I-146 | 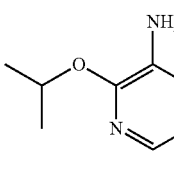 | MS (ES): m/z 382.44 [M + H]$^+$, LCMS purity: 95 12%, HPLC purity: 96.13%, $^1$H NMR (DMSO-d$_6$, 400 MHZ): 8.66 (s, 1H), 8.17-8.17(d, J = 1.2 Hz, 2H), 7.91-7.91 (m, 2H), 7.79-7.78 (d, J = 4 Hz, 1H), 6.98-6.95 (m, 1H), 5.88 (s, 1H), 5.37-5.33 (m, 1H), 2.93-2.91 |

TABLE 30-continued

| Compound # | Reagent | Chiral Separation Conditions and Characterization Data |
|---|---|---|
|  |  | (d, J = 4.8 Hz, 3H), 2.78-2.76 (m, 1H), 1.33-1.31 (m, 6H), 0.71-0.67 (m, 2H), 0.35-0.312 (m, 2H). |
| I-116 |  | MS (ES): m/z 435.72 [M + H]$^+$, LCMS purity: 95.20%, HPLC purity: 95.44%, $^1$H NMR (DMSO-d$_6$, 400 MHZ): 9.15 (s, 1H), 8.678-8.672 (d, J = 2.4 Hz, 1H), 8.25-8.22 (m, 2H), 8.05-8.00 (m, 1H), 7.95-7.92 (m, 2H), 7.86-7.85 (d, J = 4 Hz, 1H), 7.58-7.56 (d, J = 8 Hz, 1H), 6.47-6.45 (t, J = 8 Hz, 1H), 6.22 (s, 1H), 2.91-2.87 (m, 4H), 0.81-0.80 (d, J = 4 Hz, 2H), 0.53 (m, 2H). |

Synthesis of 5-(5-chloro-1-isopropyl-1H-pyrrolo[2,3-b]pyridin-3-yl)-N-cyclopropyl-7-(methylamino)pyrazolo[1,5-a]pyrimidine-3-carboxamide (I-253)

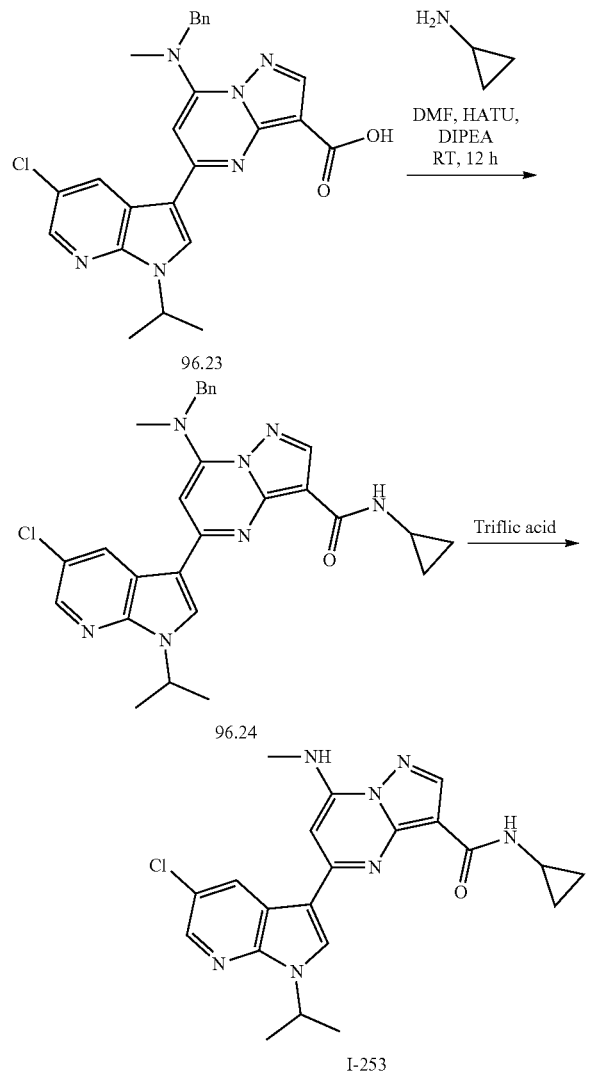

Synthesis of Compound 96.23.

Compound was synthesized as per Example 103 (I-272) to obtain 96.23.

Synthesis of Compound 96.24.

Compound was synthesized using general procedure of A to obtain 96.24 (0.063 g, 58.21%). MS (ES): m/z 515.03 [M+H]$^+$.

Synthesis of Compound I-253.

Mixture of 96.24 (0.063 g, 0.122 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-253 (0.025 g, 50.04%), MS (ES): m/z 424.50 [M+H]$^+$, LCMS purity: 96.47%, HPLC purity: 95.00%, $^1$H NMR (DMSO-d$_6$, 400 MHZ): 8.86 (s, 1H), 8.62 (s, 1H), 8.40-8.37 (d, J=12 Hz, 2H), 8.26 (s, 1H), 8.13 (s, 1H), 6.77 (s, 1H), 5.15 (bs, 1H), 3.11 (s, 3H), 2.90 (bs, 1H), 1.57 (s, 6H), 0.83 (bs, 2H), 0.64 (bs, 2H).

Synthesis of (R)—N-cyclopropyl-5-(1-(1-(2-fluoroethyl)pyrrolidin-3-yl)-1H-pyrrolo[2,3-b]pyridin-3-yl)-7-(methylamino)pyrazolo[1,5-a]pyrimidine-3-carboxamide (I-1367)

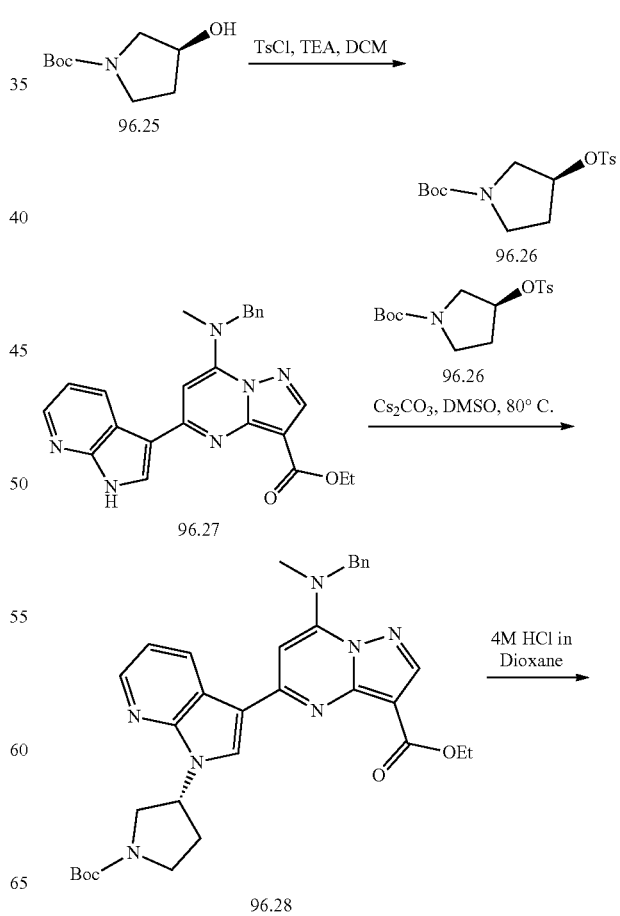

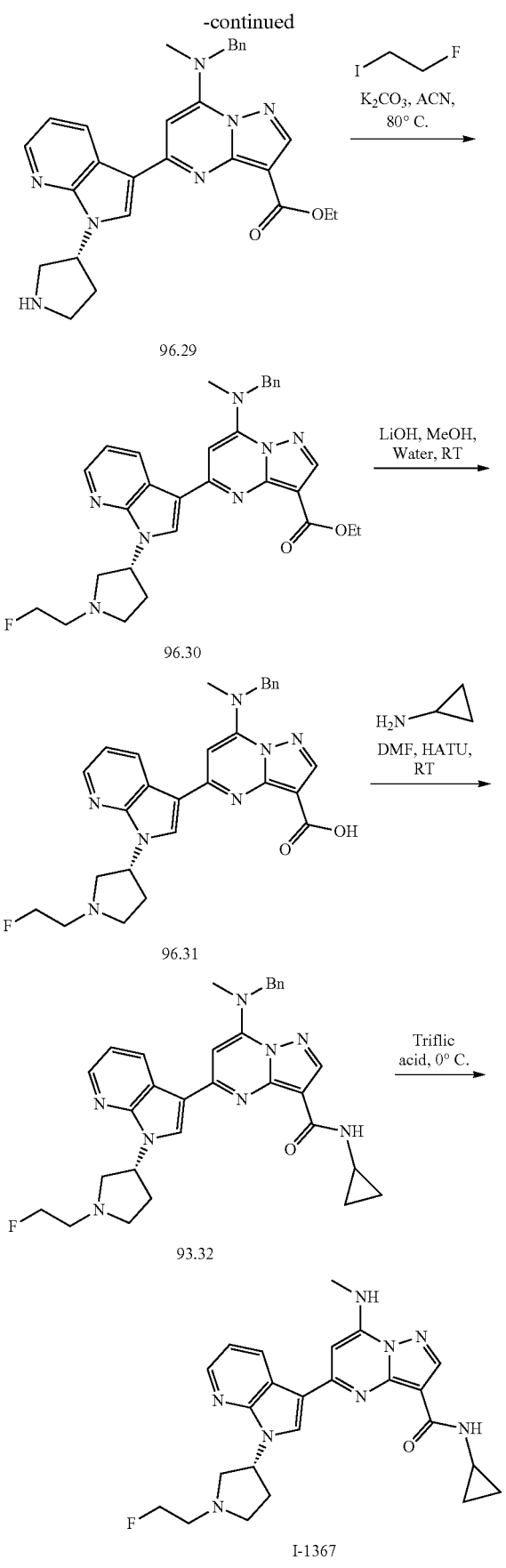

Synthesis of Compound 96.26.

To a solution of 96.25 (1.0 g, 5.34 mmol, 1.0 eq) in dichloromethane (10 mL) were added 4-Toluenesulfonyl chloride (1.0 g, 5.34 mmol, 1.0 eq) and triethylamine (0.646 g, 6.40 mmol, 1.2 eq). The reaction mixture stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 96.26 (0.8 g, 43.87%). MS(ES): m/z 342.13 [M+H]$^+$.

Synthesis of Compound 96.27.

Compound was synthesized as per I-960 to obtain 96.27. (Yield: 83.64%), MS (ES): m/z 427.18 [M+H]$^+$ Synthesis of Compound 96.28.

To a solution of 96.27 (1.0 g, 2.34 mmol, 1.0 eq) and 96.26 (1.5 g, 4.68 mmol, 2.0 eq) in dimethyl sulphoxide (10 mL) was added Caesium carbonate (1.52 g, 4.68 mmol, 2.0 eq) and reaction mixture heated at 80° C. for 10 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 96.28. (0.6 g, 42.96%). MS(ES): m/z 596.29 [M+H]$^+$.

Synthesis of Compound 96.29.

To 96.28 (0.6 g, 1.00 mmol, 1.0 eq) was added 4M hydrochloric acid in 1,4 Dioxane (8 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 96.29 (0.450 g, Yield: 90.15%), MS (ES): m/z 596.24 [M+H]$^+$.

Synthesis of Compound 96.30.

To a solution of 96.29. (0.4 g, 0.80 mmol, 1 eq) and 2-fluoroiodoethane (0.167 g, 0.96 mmol, 1.2 eq) in Acetonitrile (5 mL) was added potassium carbonate (0.220 g, 1.6 mmol, 2.0 eq). The reaction mixture was heated at 80° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96.30. (0.310 g, 70.91%). MS(ES): m/z 542.26 [M+H]$^+$ Synthesis of Compound 96.31.

To a solution of 96.30 (0.310 g, 0.57 mmol, 1.0 eq), in methanol: water (6 mL, 2:1) was added lithium hydroxide (0.136 g, 5.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 96.31. (0.262 g, 89.63%). MS(ES): m/z 514.23 [M+H]$^+$.

Synthesis of Compound 96.32.

Compound was synthesized using general procedure A to obtain 96.32. (0.090 g, 64.34%), MS (ES): 553.28 [M+H]$^+$ Synthesis I-1367.

To a solution of 96.32 (0.090 g, 0.16 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1367 (0.058 g, 77.00%), MS (ES): m/z 463.61 [M+H]$^+$, LCMS purity: 96.14%, HPLC purity: 98.39%, CHIRAL HPLC: 96.89%, $^1$H NMR (DMSO-d$_6$, 400 MHZ): 8.70 (s, 1H), 8.65-8.63 (d, J=8 Hz, 1H), 8.41-8.40 (d, J=4.4 Hz, 1H), 8.36 (s, 1H), 8.32-8.31 (d, J=3.6 Hz, 1H), 8.28-8.27 (d, J=4.8 Hz, 1H), 7.33-7.30 (m, 1H), 6.71 (s, 1H), 5.55 (bs, 1H), 4.68-4.65 (t, J=4.8 Hz, 1H), 4.56-4.53 (t, J=4.8 Hz, 1H), 3.11-3.10 (d, J=4.8 Hz, 4H), 3.04-3.00 (m, 1H), 2.94-2.91 (m, 4H), 2.73-2.68 (m, 2H), 2.21-2.18 (m, 1H), 0.87-0.83 (m, 2H), 0.59 (bs, 2H).

Synthesis of Intermediate of 96a

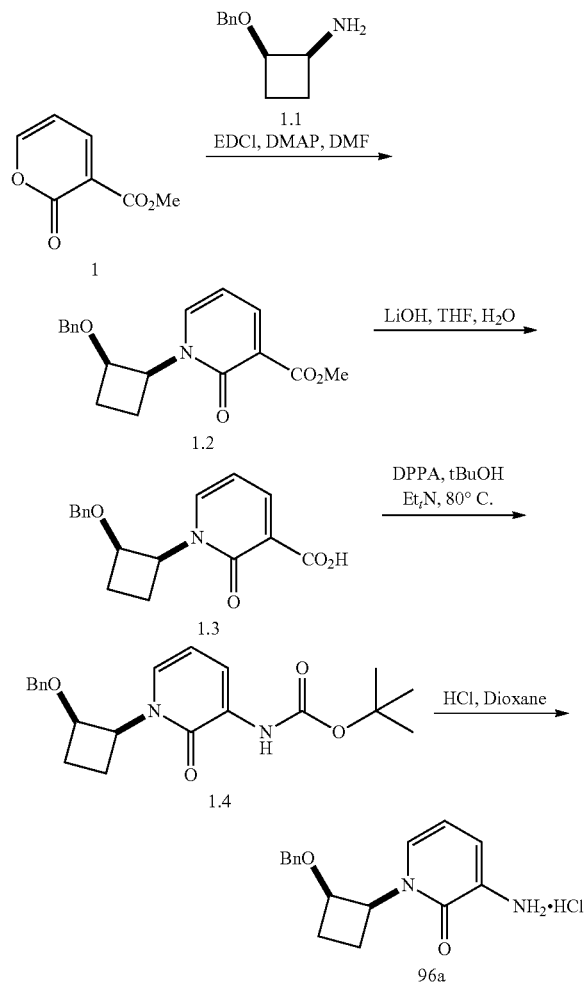

Synthesis of Compound 1.2.

To a cooled solution of 1. (1.0 g, 6.48 mmol, 1.0 eq), in N,N-dimethylformamide (12 mL) was added 1.1 (1.14 g, 6.48 mmol, 1.0 eq). The reaction mixture was stirred at 0° C. for 30 min and further stirred at room temperature for 15 min.  N-Ethyl-N'-(3-dimethylaminopropyl)carbodiimide hydrochloride (1.3 g, 8.42 mmol, 1.3 eq) and 4-Dimethylaminopyridine (0.157 g, 1.29 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.680 g, 33.45%). MS(ES): m/z 314.13 [M+H]$^+$.

Synthesis of Compound 1.3.

To a solution of 1.2 (0.680 g, 2.17 mmol, 1.0 eq), in tetrahydrofuran: water (10 mL, 2:1) was added lithium hydroxide (0.520 g, 21.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.490 g, 75.44%). MS(ES): m/z 300.12 [M+H]$^+$.

Synthesis of Compound 1.4.

To a solution of 1.3. (0.490 g, 1.63 mmol, 1.0 eq) in tert.butanol (5 mL) was added triethylamine (0.279 g, 2.77 mmol, 1.7 eq) and diphenyl phosphoryl azide (0.582 g, 2.11 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.4 g, 65.96%). MS(ES): m/z 371.19 [M+H]$^+$.

Synthesis of Intermediate 96a.

To a cooled solution of 1.4 (0.4 g, 1.07 mmol, 1 eq) in dioxane (8 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96a. (0.3 g, 90.56%). MS(ES): m/z 307.12 [M+HCl]$^+$.

Synthesis of Intermediate 96b

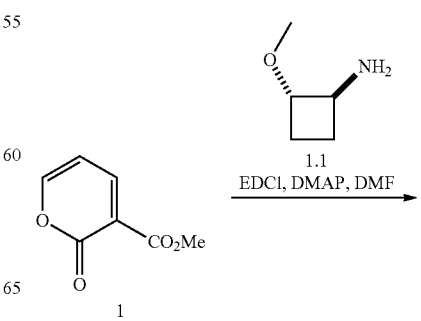

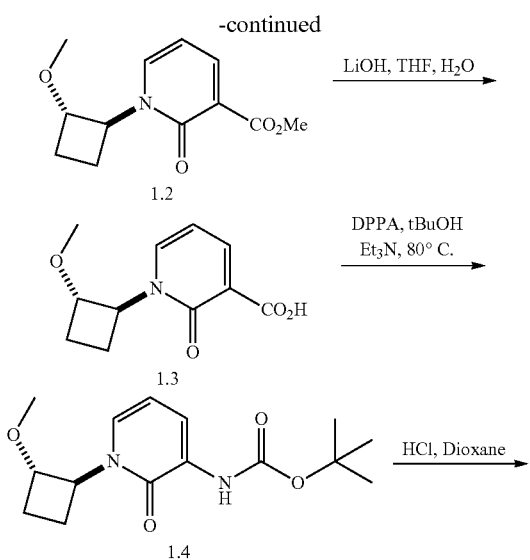

for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.275 g, 69.52%). MS(ES): m/z 295.16 [M+H]$^+$.

Synthesis of Intermediate 96b.

To a cooled solution of 1.4 (0.275 g, 0.93 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96b. (0.2 g, 92.80%). MS(ES): m/z 231.09 [M+HCl]$^+$.

Synthesis of Intermediate 96c

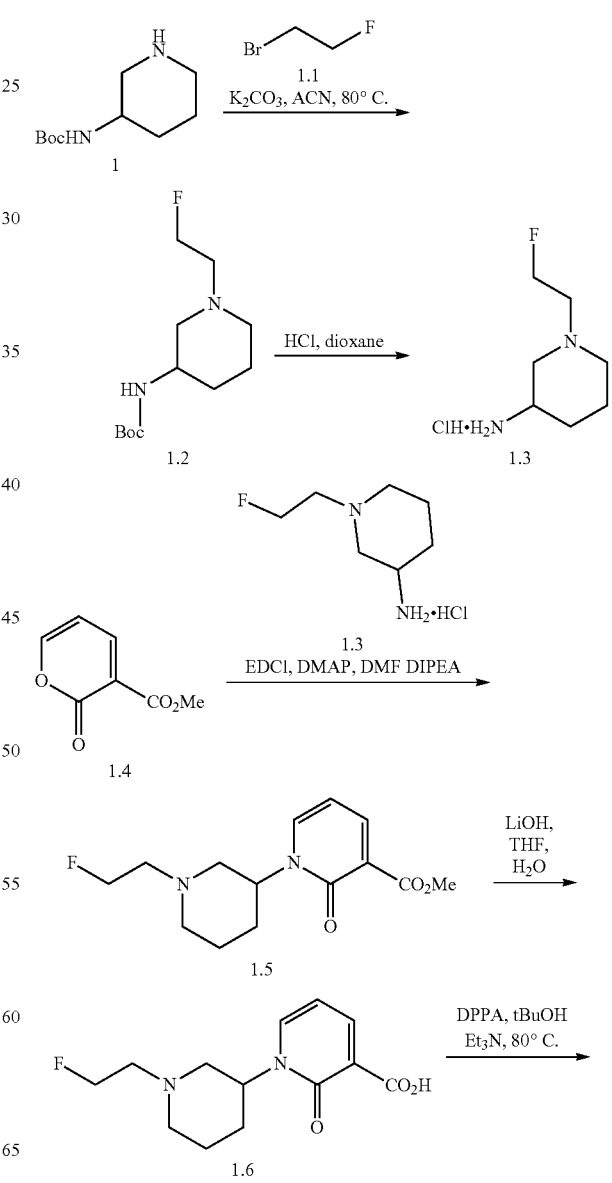

Synthesis of Compound 1.2.

To a cooled solution of 1. (0.5 g, 3.24 mmol, 1.0 eq), in N,N-dimethylformamide (8 mL) was added 1.1 (0.327 g, 3.24 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.653 g, 4.21 mmol, 1.3 eq) and 4-Dimethylaminopyridine (0.078 g, 0.64 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.390 g, 50.67%). MS(ES): m/z 238.10 [M+H]$^+$.

Synthesis of Compound 1.3.

To a solution of 1.2 (0.390 g, 1.64 mmol, 1.0 eq), in tetrahydrofuran: water (5 mL, 2:1) was added lithium hydroxide (0.393 g, 16.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.3 g, 81.76%). MS(ES): m/z 224.09 [M+H]$^+$.

Synthesis of Compound 1.4.

To a solution of 1.3 (0.3 g, 1.34 mmol, 1.0 eq) in tert.butanol (5 mL) was added triethylamine (0.229 g, 2.27 mmol, 1.7 eq) and diphenyl phosphoryl azide (0.478 g, 1.74 mmol, 1.3 eq) under nitrogen followed by heating at 80° C.

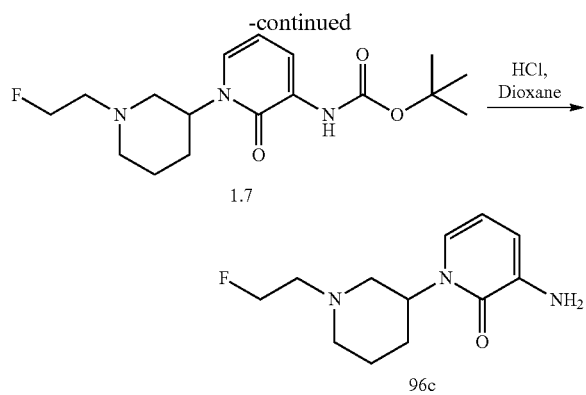

Synthesis of Compound 1.2.

To a cooled solution of 1 (2.0 g, 10.0 mmol, 1.0 eq), and 1.1 (1.5 g, 12.0 mmol, 1.2 eq) in Acetonitrile (60 mL) at 0° C. was added potassium carbonate (3.4 g, 25 mmol, 2.5 eq). The reaction was stirred at 80° C. for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 1.2. (2.0 g, 81.31%). MS (ES): m/z 247.18 [M+H]$^+$.

Synthesis of Compound 1.3.

A cooled solution of 1.2 (2.0 g, 8.11 mmol, 1 eq) in dioxane (40 mL) was added 4N hydrochloric acid in dioxane (80 mL) as a dropwise. The reaction mixture was stirred at room temperature for 2 h. After completion of reaction, reaction mixture was concentrated under reduced pressure to obtain pure 1.3. (1.5 g, 97.77%). MS(ES): m/z 183.10 [M+HCl]$^+$.

Synthesis of Compound 1.5.

To a cooled solution of 1.4 (1.5 g, 9.73 mmol, 1.0 eq), in N,N-dimethylformamide (18 mL) was added 1.3 (1.7 g, 9.73 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.9 g, 12.64 mmol, 1.3 eq), 4-Dimethylaminopyridine (0.236 g, 1.94 mmol, 0.2 eq) and N,N-Diisopropylethylamine (0.878 g, 6.81 mmol, 0.7 eq), was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.5. (0.6 g, 21.84%). MS(ES): m/z 283.14 [M+H]$^+$.

Synthesis of Compound 1.6.

To a solution of 1.5 (0.670 g, 2.37 mmol, 1.0 eq), in tetrahydrofuran: water (8 mL, 2:1) was added lithium hydroxide (0.568 g, 23.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6. (0.580 g, 91.09%). MS(ES): m/z 269.13 [M+H]$^+$.

Synthesis of Compound 1.7.

To a solution of 1.6 (0.580 g, 2.16 mmol, 1.0 eq) in tert.butanol (10 mL) was added triethylamine (0.370 g, 3.67 mmol, 1.7 eq) and diphenyl phosphoryl azide (0.77 g, 2.80 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7. (0.470 g, 64.05%). MS(ES): m/z 340.20[M+H]$^+$.

Synthesis of Intermediate 96c.

To 1.7 (0.470 g, 1.38 mmol, 1.0 eq) was added 4M hydrochloric acid in 1,4 Dioxane (10 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 96c. (Yield: 90.54%), MS (ES): m/z 240.15 [M+H]$^+$.

Synthesis of Intermediate 96d.

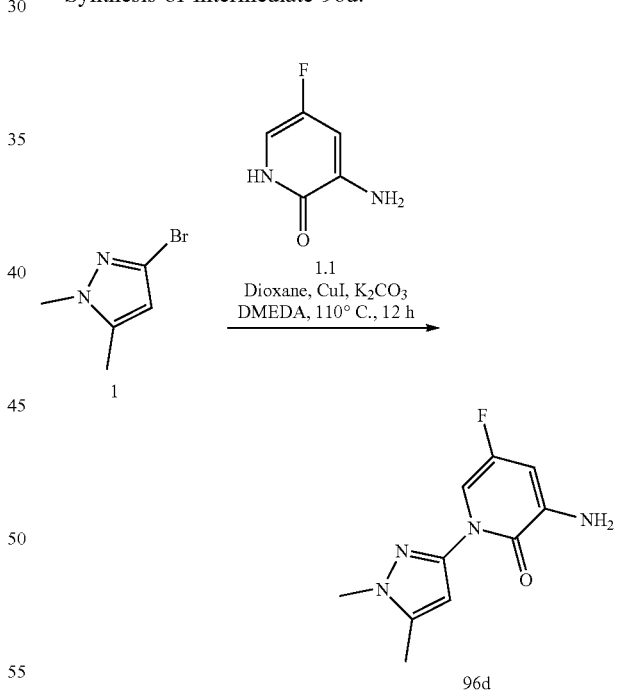

Synthesis of Intermediate 96d.

To a solution of 1 (1 g, 5.71 mmol, 1.0 eq) in 1,4-dioxane (100 mL), 1.1 (1.8 g, 8.57 mmol, 1.5 eq) was added. The reaction mixture was degassed for 10 min under argon atmosphere followed by addition of potassium carbonate (1.57 g, 11.42 mmol, 2.0 eq), N,N-dimethylethylenediamine (0.20 g, 2.28 mmol, 0.4 eq), and copper iodide (0.216 g, 1.14 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96d (0.550 g, Yield: 43.32%). MS (ES): m/z 223.10 [M+H]+.

Synthesis of Intermediate 96e

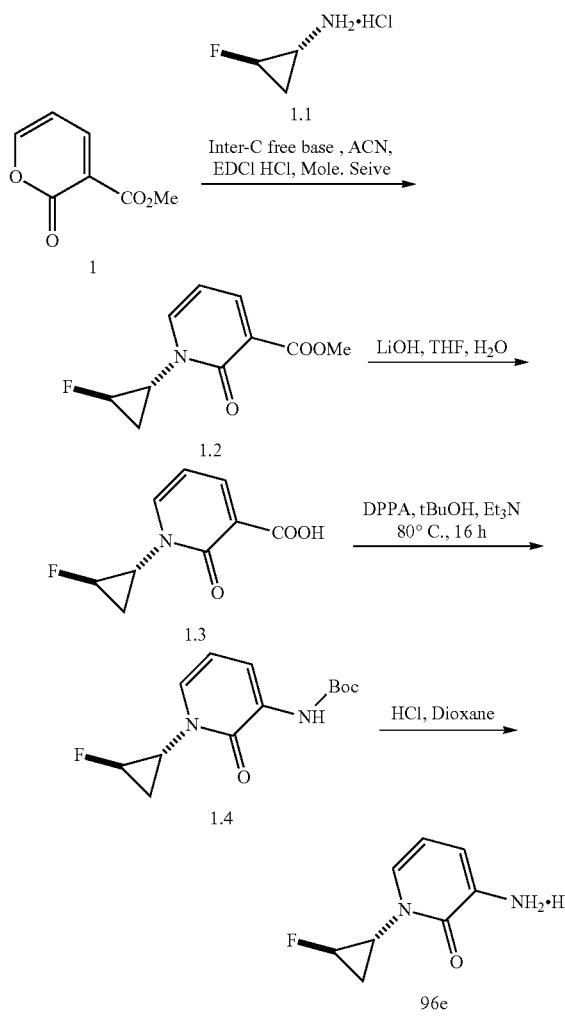

Synthesis of Compound 1.2.

To a cooled solution of 1 (0.5 g, 3.24 mmol, 1.0 eq), in Acetonitrile (10 mL) was added 1.1 (0.395 g, 3.56 mmol, 1.1 eq). The reaction mixture was stirred at 0° C. for 30 min and further stirred at room temperature for 15 min. N-Ethyl-N'-(3-dimethylaminopropyl)carbodiimide hydrochloride (0.652 g, 4.21 mmol, 1.3 eq) and Mole. Sieve were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.320 g, 46.71%). MS(ES): m/z 212.07 [M+H]+.

Synthesis of Compound 1.3.

To a solution of 1.2 (0.320 g, 1.51 mmol, 1.0 eq), in tetrahydrofuran: water (8 mL, 2:1) was added lithium hydroxide (0.362 g, 15.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.265 g, 88.70%). MS(ES): m/z 198.05 [M+H]+.

Synthesis of Compound 1.4.

To a solution of 1.3 (0.265 g, 1.34 mmol, 1.0 eq) in tert.butanol (6 mL) was added triethylamine (0.230 g, 2.27 mmol, 1.7 eq) and diphenyl phosphoryl azide (0.478 g, 1.74 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.160 g, 44.37%). MS(ES): m/z 269.13 [M+H]+.

Synthesis of Intermediate 96e.

A cooled solution of 1.4 (0.160 g, 0.59 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96e. (0.125 g, 98.3³%). MS(ES): m/z 205.05 [M+HCl]+.

Synthesis of Intermediate 96f

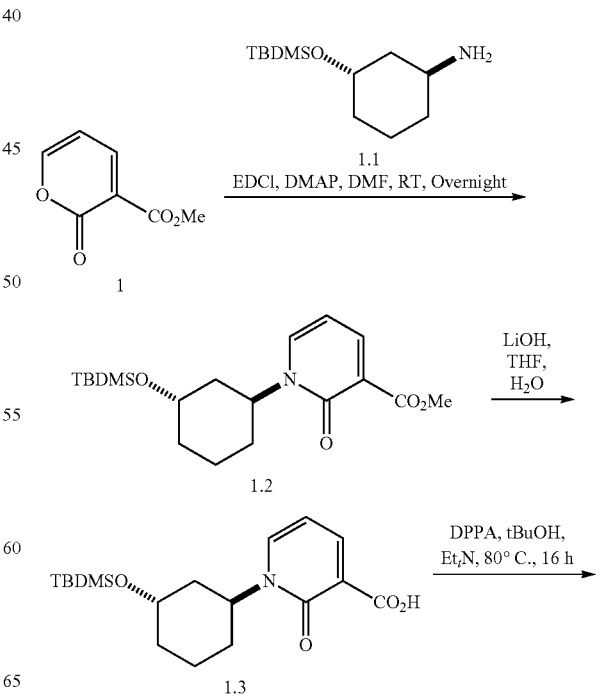

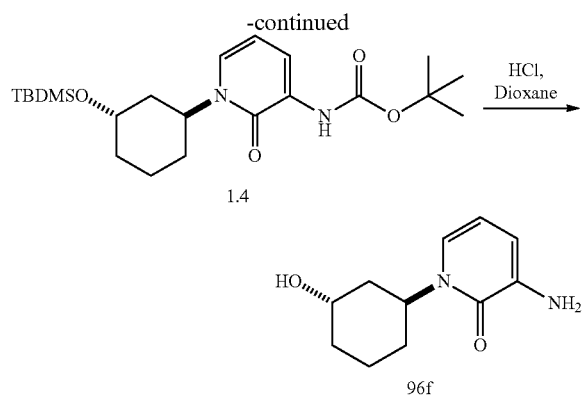

Synthesis of Compound 1.2.

To a cooled solution of 1 (0.5 g, 3.24 mmol, 1.0 eq), in N,N-dimethylformamide (6 mL) was added 1.1 (0.816 g, 3.56 mmol, 1.1 eq). The reaction mixture was stirred at 0° C. for 30 min and further stirred at room temperature for 15 min. N-Ethyl-N'-(3-dimethylaminopropyl)carbodiimide hydrochloride (0.652 g, 4.21 mmol, 1.3 eq), 4-Dimethylaminopyridine (0.078 g, 0.64 mmol, 0.2 eq) and was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.360 g, 30.36%). MS(ES): m/z 366.21 [M+H]$^+$.

Synthesis of Compound 1.3.

To a solution of 1.2 (0.360 g, 0.98 mmol, 1.0 eq), in tetrahydrofuran: water (6 mL, 2:1) was added lithium hydroxide (0.235 g, 9.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.262 g, 75.68%). MS(ES): m/z 352.19 [M+H]$^+$.

Synthesis of Compound 1.4.

To a solution of 1.3 (0.262 g, 0.74 mmol, 1.0 eq) in tert.butanol (6 mL) was added triethylamine (0.126 g, 1.25 mmol, 1.7 eq) and diphenyl phosphoryl azide (0.264 g, 0.96 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.160 g, 50.79%). MS(ES): m/z 423.26[M+H]$^+$.

Synthesis of Intermediate 96f.

To 1.4 (0.160 g, 0.37 mmol, 1.0 eq) was added 4M hydrochloric acid in 1,4 Dioxane (4 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 96f. (0.100 g, Yield: 95.13%), MS (ES): m/z 209.12 [M+H]$^+$.

Synthesis of Intermediate 96g

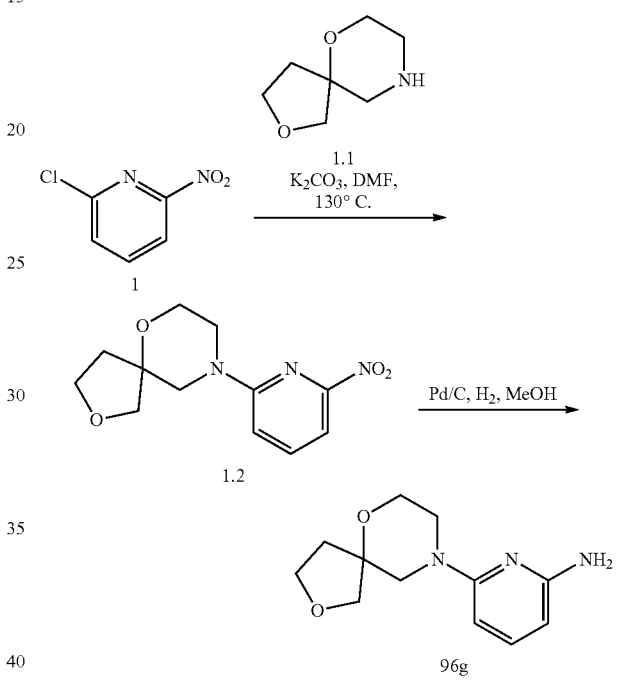

Synthesis of Compound 1.2.

A solution of compound 1 (0.300 g, 1.89 mmol, 1.0 eq) and compound 1.1 (0.270 g, 1.89 mmol, 1.0 eq) in Dimethylformamide (3 mL) was added potassium carbonate (0.782 g, 5.67 mmol, 3.0 eq) at room temperature. The reaction mixture was degassed for 10 min and heated at 130° C. for 8 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 20% ethylacetate in hexane to obtain 1.2. (0.230 g, Yield: 45.82%). MS (ES): m/z 266.11 [M+H]$^+$.

Synthesis of Intermediate 96g.

To a solution of 1.2 (0.230 g, 0.86 mmol, 1.0 eq) in methanol (5 ml), palladium on charcoal (0.104 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 196 g. (0.200 g, 98.04%). MS (ES): m/z 236.14 [M+H]$^+$.

Synthesis of Intermediate 96h

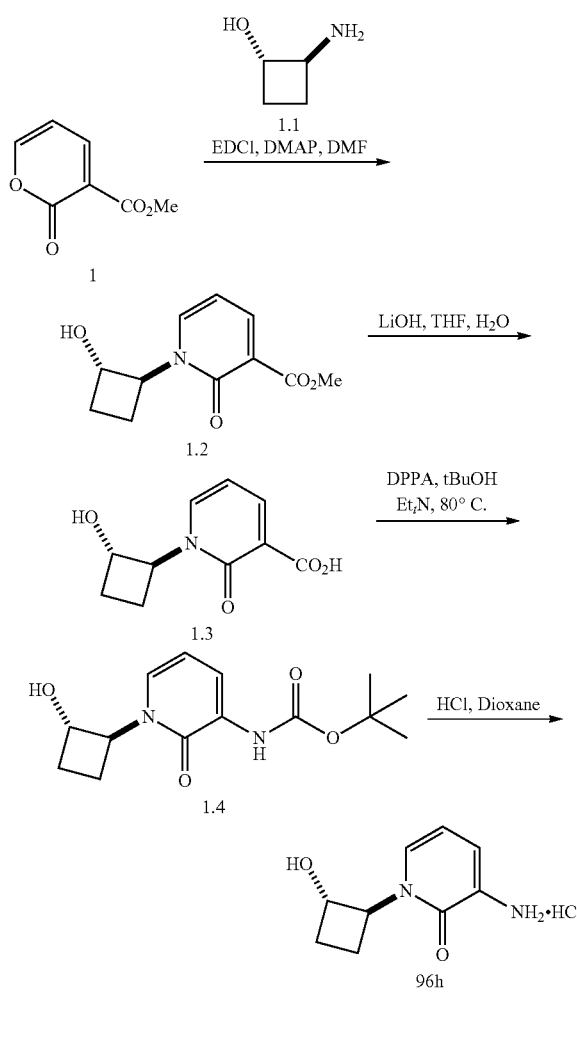

Synthesis of Compound 1.2.

To a cooled solution of 1 (0.8 g, 5.19 mmol, 1.0 eq), in N,N-dimethylformamide (50 mL) was added 1.1 (0.451 g, 5.19 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.28 g, 6.747 mmol, 1.3 eq) and 4-Dimethylaminopyridine (0.158 g, 1.29 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (0.520 g, 44.88%). MS(ES): m/z 224.45 [M+H]$^+$.

Synthesis of Compound 1.3:

To a solution of 1.2 (0.520 g, 2.33 mmol, 1.0 eq), in tetrahydrofuran: methanol: water (10 mL, 2:2:1) was added lithium hydroxide (0.979 g, 23.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.5 (0.410 g, 84.5%). MS(ES): m/z 210 [M+H]$^+$.

Synthesis of Compound 1.4:

To a solution of 1.3 (0.41 g, 1.96 mmol, 1.0 eq) in tert. Butanol (6 mL) was added triethylamine (0.333 g, 3.33 mmol, 1.7 eq) and diphenyl phosphoryl azide (0.700 g, 2.54 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.230 g, 41.86%). MS(ES): m/z 281.3 [M+H]$^+$.

Synthesis of Intermediate 96h:

A cooled solution of 1.4 (0.230 g, 0.820 mmol, 1 eq) in 1,4-dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 96 h (0.150 g, 84.3%). MS(ES): m/z 217.35 [M+H]$^+$ Synthesis of Intermediate 96i

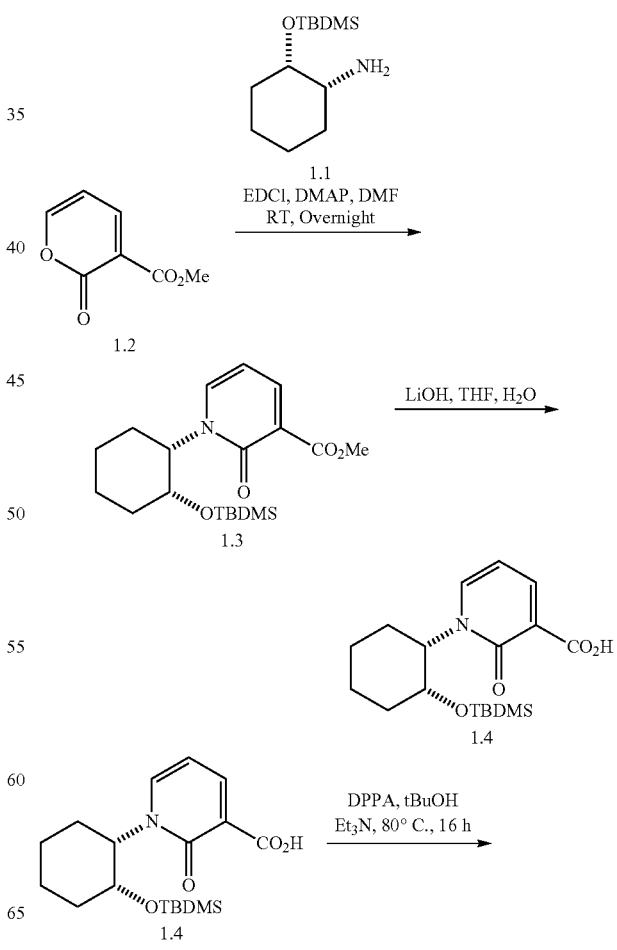

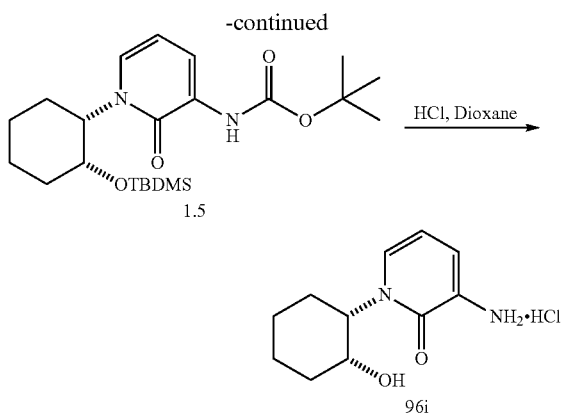

Synthesis of Compound 1.1.

To a solution of 1 (2.0 g, 1.31 mmol, 1.0 eq) in dichloromethane (10 mL) was added imidazole (1.5 g, 6.55 mmol, 5.0 eq). The reaction mixture was stirred at room temperature for 30 min. Further tert-Butyldimethylsilyl chloride (0.98 g, 1.96 mmol, 1.5 eq) was added and stirred the reaction mixture at room temperature for 15 h. After completion of reaction, reaction mixture was transferred into water and product was extracted by dichloromethane. Organic layer was combined, washed with brine solution, dried over sodium sulphate and concentrated under reduced pressure to obtain product 1.1 (1.2 g, 39.65%). MS(ES): m/z 230.44 [M+H]$^+$.

Synthesis of Compound 1.3.

To a cooled solution of 1.2 (0.65 g, 6.49 mmol, 1.0 eq), in N,N-dimethylformamide (10 mL) was added 1.1 (1.0 g, 6.49 mmol, 1.0 eq). The reaction mixture was stirred at 0° C. for 6 h and further stirred at room temperature for 15 min. N-Ethyl-N'-(3-dimethylaminopropyl)carbodiimide hydrochloride (1.65 g, 8.43 mmol, 1.3 eq) and 4-Dimethylaminopyridine (0.2 g, 1.62 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.3 (0.6 g, 38.92%). MS(ES): m/z 366.55 [M+H]$^+$.

Synthesis of Compound 1.4.

To a solution of 1.3 (0.6 g, 1.64 mmol, 1.0 eq), in tetrahydrofuran: methanol: water (10 mL, 2:2:1) was added lithium hydroxide (0.69 g, 1.64 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.4 (0.5 g, 86.66%). MS(ES): m/z 352.52 [M+H]$^+$.

Synthesis of Compound 1.5.

To a solution of 1.4 (0.50 g, 1.42 mmol, 1.0 eq) in tert. butanol (8 mL) was added triethylamine (0.25 g, 2.41 mmol, 1.7 eq) and diphenyl phosphoryl azide (0.51 g, 1.85 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 10% ethyl acetate in hexane to obtain pure 1.5 (0.3 g, 49.90%). MS(ES): m/z 423.64 [M+H]$^+$.

Synthesis of Intermediate 96i.

A cooled solution of 1.5 (0.3 g, 0.709 mmol, 1 eq) in 1,4-Dioxane (2 mL) was added 4M hydrochloric acid in dioxane (3 mL) as a dropwise. The reaction mixture was stirred at room temperature for 2 h. After completion of reaction, reaction mixture was concentrated under reduced pressure to obtain pure 96i (0.12 g, 94.70%). MS(ES): m/z 209.26 [M+H]$^+$.

Synthesis of Intermediate 96j

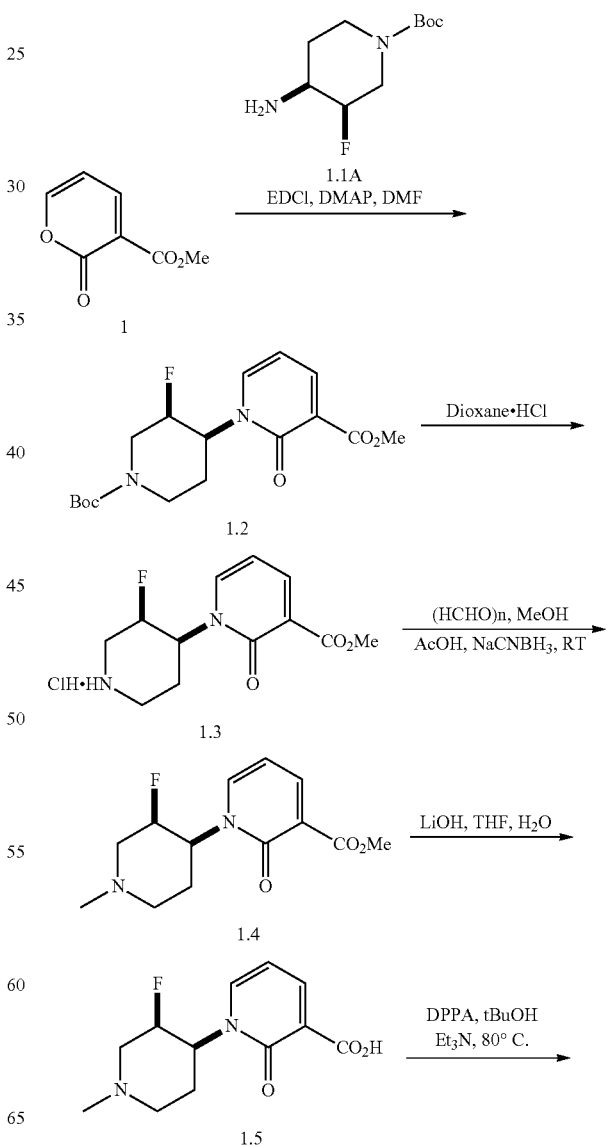

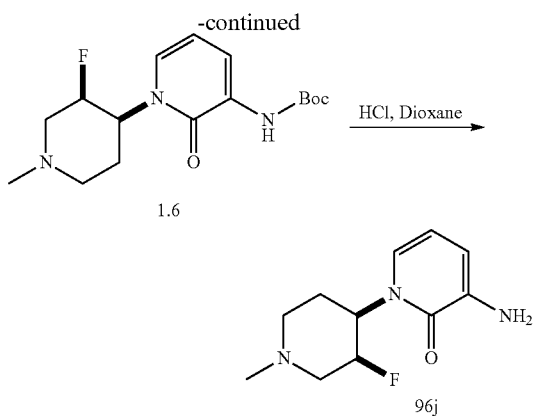

Synthesis of Compound 1.1A:
Compound was synthesized as per I-608 to obtain 1.1A.

Synthesis of Compound 1.2:
To a cooled solution of 1 (2 g, 12.98 mmol, 1.0 eq), in N,N-dimethylformamide (50 mL) was added 1.1 (2.83 g, 12.98 mmol, 1.0 eq). The reaction mixture was stirred at 0° C. for 30 min and further stirred at room temperature for 15 min. N-Ethyl-N'-(3-dimethylaminopropyl)carbodiimide hydrochloride (3.22 g, 16.88 mmol, 1.3 eq) and 4-Dimethylaminopyridine (0.39 g, 3.5 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (1.6 g, 34.94%). MS(ES): m/z 355.34 [M+H]⁺.

Synthesis of Compound 1.3:
The compound 1.2 (1.6 g, 4.5 mmol, 1.0 eq) was dissolved in dichloromethane (4 mL) and 4M HCl in dioxane (0.2 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain 1.3 (1.6 g, 76.19%). MS(ES): m/z 290 [M+H]⁺.

Synthesis of Compound 1.4:
To a cooled solution of 1.3 (1.6 g, 5.55 mmol, 1.0 eq), in methanol (20 mL) were added formaldehyde (0.827 g, 27.58 mmol, 5.0 eq) and acetic acid (1.9 g, 33 mmol, 6 eq) at 0° C. The reaction mixture was stirred at 0° C. for 60 min and sodium cyanoborohydride (1.02 g, 16.88 mmol, 3 eq) was added. The reaction mixture was stirred at room temperature for 48 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.4 (0.8 g, 54.18%). MS(ES): m/z 269.34 [M+H]⁺.

Synthesis of Compound 1.5:
To a solution of 1.4 (0.5 g, 1.86 mmol, 1.0 eq), in tetrahydrofuran: methanol: water (10 mL, 2:2:1) was added lithium hydroxide (0.78 g, 18.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.5 (0.350 g, 73.86%). MS(ES): m/z 255.35 [M+H]⁺.

Synthesis of Compound 1.6:
To a solution of 1.5 (0.350 g, 1.33 mmol, 1.0 eq) in tert. Butanol (6 mL) was added triethylamine (0.236 g, 2.33 mmol, 1.7 eq) and diphenyl phosphoryl azide (0.475 g, 1.72 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.6 (0.220 g, 49.12%). MS(ES): m/z 326.5 [M+H]⁺.

Synthesis of Intermediate 96j:
A cooled solution of 1.6 (0.220 g, 0.670 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 96j (0.150 g, 98.48%). MS(ES): m/z 226.35 [M+H]⁺

Synthesis of Intermediate 96k

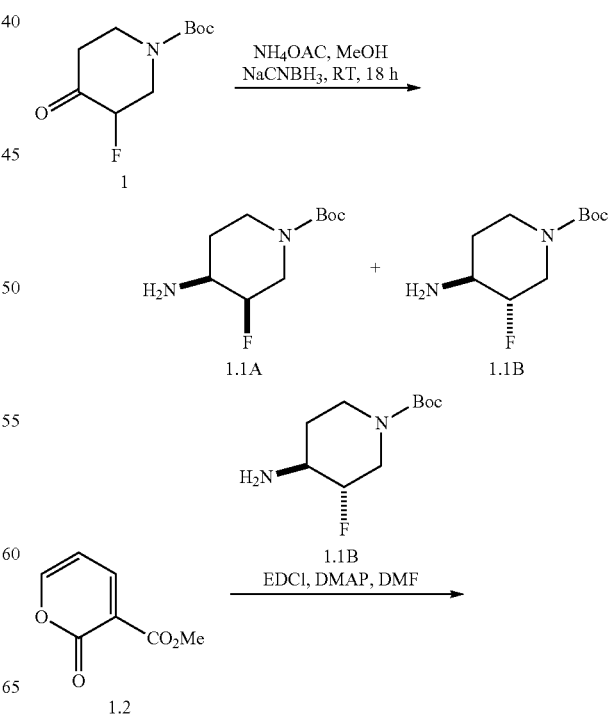

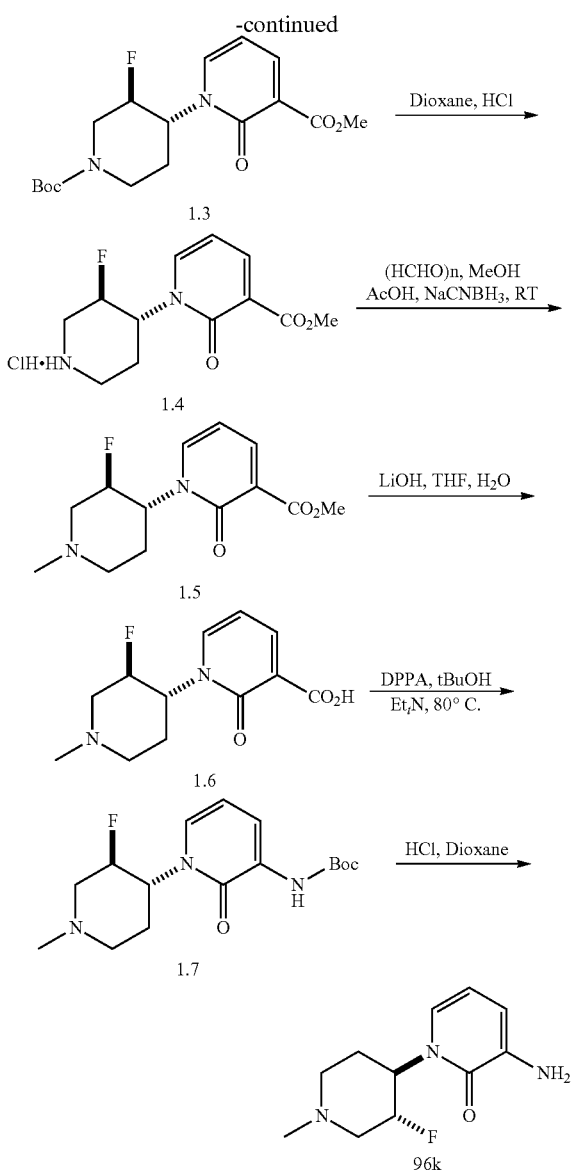

Synthesis of Compound 1.1A and 1.1B:

To a cooled solution of 1 (0.2 g, 0.92 mmol, 1.0 eq), in methanol (20 mL) was added ammonium acetate (0.499 g, 6.48 mmol, 7.0 eq) at 0° C. The reaction mixture was stirred at 0° C. for 1 h and sodium cyanoborohydride (0.085 g, 1.3 mmol, 1.5 eq) was added. The reaction mixture was stirred at room temperature for 18 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.1A (0.02 g, 19.91%) MS(ES): m/z 219.35 [M+H]+ and 1.1B (0.02 g, 19.91%) MS(ES): m/z 219.35 [M+H]+.

Synthesis of Compound 1.3:

To a cooled solution of 1.2 (2 g, 12.98 mmol, 1.0 eq), in N,N-dimethylformamide (50 mL) was added 1.1B (2.83 g, 12.98 mmol, 1.0 eq). The reaction mixture was stirred at 0° C. for 30 min and further stirred at room temperature for 15 min. N-Ethyl-N'-(3-dimethylaminopropyl) carbodiimide hydrochloride (3.22 g, 16.88 mmol, 1.3 eq) and 4-Dimethylaminopyridine (0.39 g, 3.5 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.3 (1.6 g, 34.94%). MS(ES): m/z 355.34 [M+H]+.

Synthesis of Compound 1.4:

The compound 1.3 (1.6 g, 4.5 mmol, 1.0 eq) was dissolved in dichloromethane (4 mL) and 4M HCl in dioxane (0.2 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain 1.4 (1.6 g, 76.19%). MS(ES): m/z 290 [M+H]+.

Synthesis of Compound 1.5:

To a cooled solution of 1.4 (1.6 g, 5.55 mmol, 1.0 eq), in methanol (20 mL) were added formaldehyde (0.827 g, 27.58 mmol, 5.0 eq) and acetic acid (1.9 g, 33 mmol, 6 eq) at 0° C. The reaction mixture was stirred at 0° C. for 1 h and sodium cyanoborohydride (1.02 g, 16.88 mmol, 3 eq) was added. The reaction mixture was stirred at room temperature for 48 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.5 (0.8 g, 54.18%). MS(ES): m/z 269.34 [M+H]+.

Synthesis of Compound 1.6:

To a solution of 1.5 (0.5 g, 1.86 mmol, 1.0 eq), in tetrahydrofuran: methanol: water (10 mL, 2:2:1) was added lithium hydroxide (0.78 g, 18.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6 (0.350 g, 73.86%). MS(ES): m/z 255.35 [M+H]+.

Synthesis of Compound 1.7:

To a solution of 1.6 (0.350 g, 1.33 mmol, 1.0 eq) in tert. Butanol (6 mL) was added triethylamine (0.236 g, 2.33 mmol, 1.7 eq) and diphenyl phosphoryl azide (0.475 g, 1.72 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7 (0.220 g, 49.12%). MS(ES): m/z 326.5 [M+H]⁺.

Synthesis of Intermediate 96k:

A cooled solution of 1.7 (0.220 g, 0.670 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 96k (0.150 g, 98.48%). MS(ES): m/z 226.35 [M+H]⁺

Synthesis of Intermediate 96l

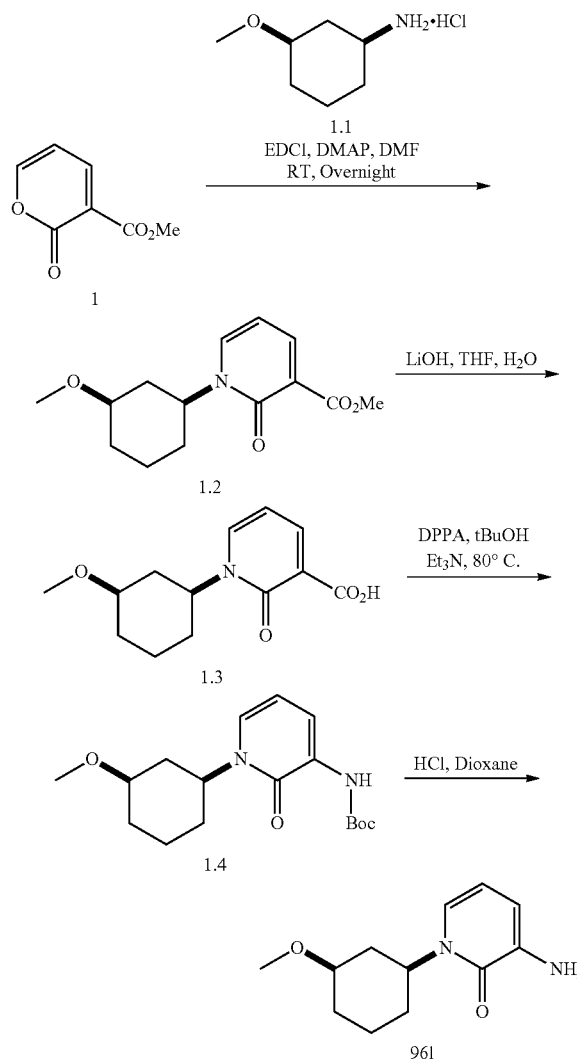

Synthesis of Compound 1.2.

To a cooled solution of 1 (0.5 g, 3.24 mmol, 1.0 eq), in N,N-dimethylformamide (12 mL) was added 1.1 (0.536 g, 3.24 mmol, 1.0 eq). The reaction mixture was stirred at 0° C. for 6 h and further stirred at room temperature for 15 min. N-Ethyl-N'-(3-dimethylaminopropyl)carbodiimide hydrochloride (0.807 g, 4.21 mmol, 1.3 eq) and 4-Dimethylaminopyridine (0.078 g, 0.64 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 1.2. (0.420 g, 48.80%). MS(ES): m/z 266.1 [M+H]⁺.

Synthesis of Compound 1.3.

To a solution of 1.2 (0.420 g, 1.58 mmol, 1.0 eq), in tetrahydrofuran: water (8 mL, 2:1) was added lithium hydroxide (0.379 g, 15.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.240 g, 60.33%). MS(ES): m/z 252.1 [M+H]⁺.

Synthesis of Compound 1.4.

To a solution of 1.3 (0.240 g, 0.95 mmol, 1.0 eq) in tert.butanol (6 mL) was added triethylamine (0.162 g, 1.61 mmol, 1.7 eq) and diphenyl phosphoryl azide (0.338 g, 1.23 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 1.4. (0.2 g, 64.95%). MS(ES): m/z 323.1 [M+H]⁺.

Synthesis of Intermediate 96l.

To 1.4 (0.2 g, 0.62 mmol, 1.0 eq) was added 4M hydrochloric acid in 1,4 Dioxane (4 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 96l. (0.140 g, 94.28%). MS (ES): m/z 223.1 [M+H]⁺

Synthesis of Intermediate 96m

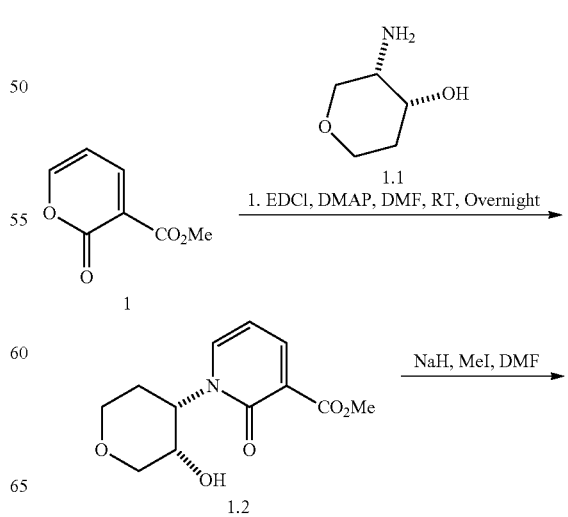

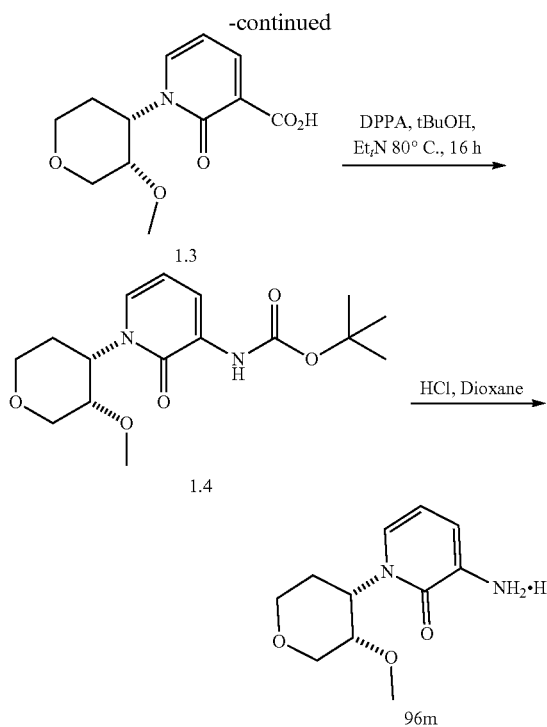

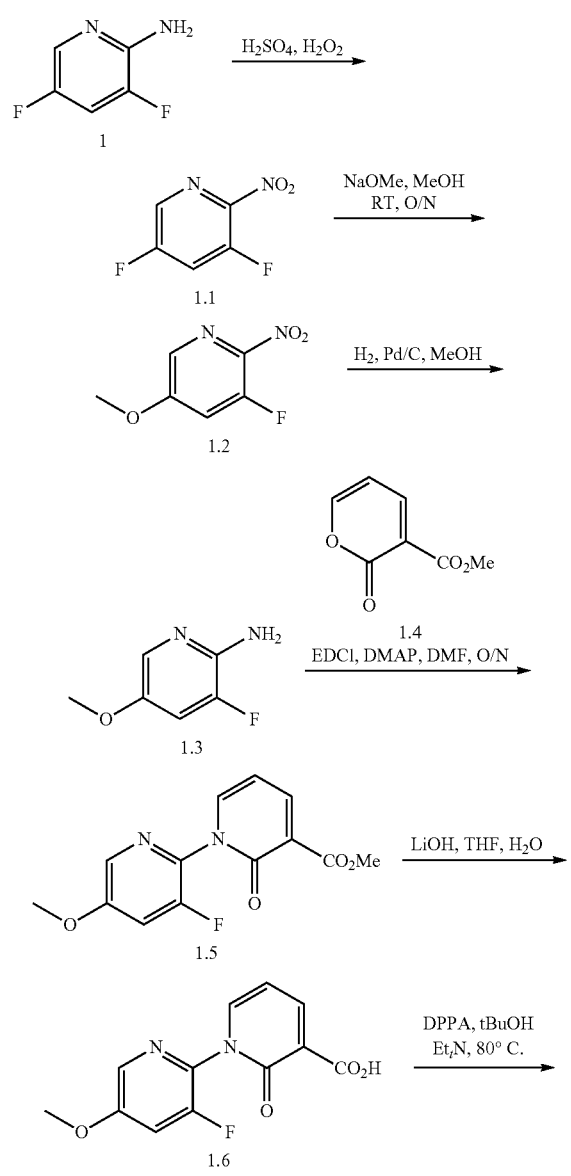

Synthesis of Compound 1.2.

To a cooled solution of 1 (0.6 g, 3.89 mmol, 1.0 eq), in N,N-dimethylformamide (15 mL) was added 1.1 (0.455 g, 3.89 mmol, 1.0 eq). The reaction mixture was stirred at 0° C. for 6 h and further stirred at room temperature for 15 min. N-Ethyl-N'-(3-dimethylaminopropyl)carbodiimide hydrochloride (0.968 g, 5.05 mmol, 1.3 eq) and 4-Dimethylaminopyridine (0.093 g, 0.77 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 1.2. (0.450 g, 45.64%). MS(ES): m/z 254.1 [M+H]$^+$.

Synthesis of Compound 1.3.

To a stirred suspension of sodium hydride (0.055 g, 2.30 mmol, 1.3 eq, 60% dispersion) in N,N-dimethyl formamide (5 mL) was added a solution of 1.2 (0.450 g, 1.77 mmol, 1.0 eq) in N,N-dimethyl formamide (10 mL) dropwise at 0° C. under $N_2$. The mixture was stirred for 20 mins under the same conditions and a solution of methyl iodide (0.301 g, 2.12 mmol, 1.2 eq) in N,N-dimethyl formamide (5 mL) was added dropwise. The reaction mixture was stirred at room temperature for 14 h. After completion of reaction, reaction mixture was transferred into ice cold water and the product was extracted with ethyl acetate. Organic layer was combined, washed with brine, dried over sodium sulfate and concentrated under reduced pressure to obtain crude material. This was further purified by column chromaography using 30% ethyl acetate in hexane as eluant to obtain pure 1.3. (0.340 g, 75.56%). MS(ES): m/z 254.1 [M+H]$^+$.

Synthesis of Compound 1.4.

To a solution of 1.3 (0.340 g, 1.34 mmol, 1.0 eq) in tert.butanol (8 mL) was added triethylamine (0.229 g, 2.27 mmol, 1.7 eq) and diphenyl phosphoryl azide (0.478 g, 1.74 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 1.4. (0.280 g, 64.30%). MS(ES): m/z 325.1 [M+H]$^+$.

Synthesis of Intermediate 96m.

To 1.4 (0.280 g, 0.86 mmol, 1.0 eq) was added 4M hydrochloric acid in 1,4 Dioxane (5 mL) and stirred at room temperature for 4 h. After completion of reaction, reaction mixture was concentrated under reduced pressure, residue was triturated with diethyl ether to obtain 96m. (0.190 g, 84.43%). MS (ES): m/z 261.1 [M+H]$^+$.

Synthesis of Intermediate 96n

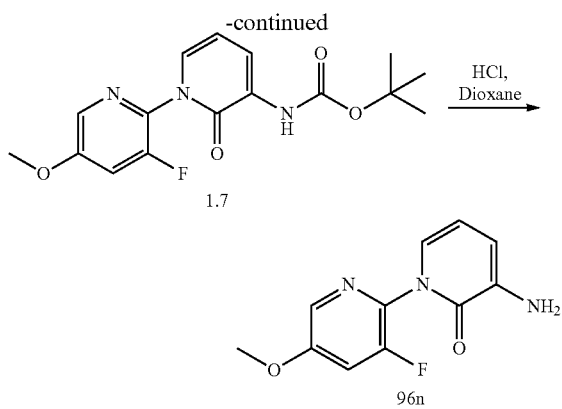

Synthesis of Compound 1.1.

Hydrogen peroxide (30%) (60 ml) was added dropwise into concentrated $H_2SO_4$ (120 mL). A solution of 1 (10 g, 76.92 mmol, 1.0 eq) in concentrated $H_2SO_4$ (180 mL) was added dropwise at 0° C. into the first solution. The reaction mixture was stirred at room temperature for 48 h. After completion of reaction, reaction mixture was transferred into ice cold water and basified with sodium bicarbonate. The resulting insoluble salts were filtered and the aqueous phase was extracted with ethyl acetate. Organic layer was combined, dried over sodium sulphate and concentrated under reduced pressure to obtain crude material. This was further purified by column chromatography and the compound was eluted in 20% ethyl acetate in hexane to obtain 1.1. (4.4 g, 35.76%), MS(ES): m/z 161.01 [M+H]$^+$.

Synthesis of Compound 1.2.

To a solution of 1.1 (4.4 g, 27.5 mmol, 1.0 eq) in methanol (95 mL) was added dropwise sodium methoxide (1.63 g, 30.25 mmol, 1.1 eq) at room temperature. The reaction was stirred at RT for 16 h. After completion of reaction, reaction mixture was concentrated under reduced pressure to obtain crude material. This was further purified by column chromatography and the compound was eluted in 24% ethyl acetate in hexane to obtain 1.2. (0.670 g, 14.16%), MS(ES): m/z 173.03 [M+H]$^+$.

Synthesis of Compound 1.3.

To a solution of 1.2 (0.670 g, 3.89 mmol, 1.0 eq) in methanol (10 ml), palladium on charcoal (0.200 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 92% ethyl acetate in hexane to obtain pure 1.3. (0.520 g, 93.98%). MS (ES): m/z 143.06 [M+H]$^+$ Synthesis of Compound 1.5.

To a cooled solution of 1.4 (0.180 g, 1.16 mmol, 1.0 eq), in N,N-dimethylformamide (5 mL) was added 1.3 (0.164 g, 1.16 mmol, 1.0 eq). The reaction mixture was stirred at 0° C. for 6 h and further stirred at room temperature for 15 min. N-Ethyl-N'-(3-dimethylaminopropyl)carbodiimide hydrochloride (0.288 g, 1.50 mmol, 1.3 eq) and 4-Dimethylaminopyridine (0.028 g, 0.23 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 1.5. (0.210 g, 64.62%). MS(ES): m/z 279.07 [M+H]$^+$.

Synthesis of Compound 1.6.

To a solution of 1.5 (0.210 g, 0.75 mmol, 1.0 eq), in tetrahydrofuran: methanol: water (10 mL, 2:2:1) was added lithium hydroxide (0.125 g, 3.0 mmol, 4.0 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 1.6. (0.180 g, 90.26%). MS(ES): m/z 265.06 [M+H]$^+$.

Synthesis of Compound 1.7.

To a solution of 1.6. (0.180 g, 0.68 mmol, 1.0 eq) in tert.butanol (4 mL) was added triethylamine (0.116 g, 1.15 mmol, 1.7 eq) and diphenyl phosphoryl azide (0.242 g, 0.88 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 1.7. (0.125 g, 54.72%). MS(ES): m/z 336.13 [M+H]$^+$.

Synthesis of Intermediate 96n.

A cooled solution of 1.7 (0.125 g, 0.37 mmol, 1 eq) in dioxane (1 mL) was added 4N hydrochloric acid in dioxane (1 mL) as a dropwise. The reaction mixture was stirred at room temperature for 2 h. After completion of reaction, reaction mixture was concentrated under reduced pressure to obtain pure 96n. (0.070 g, 79.84%). MS(ES): m/z 236.08 [M+H]$^+$.

Synthesis of Intermediate 96o

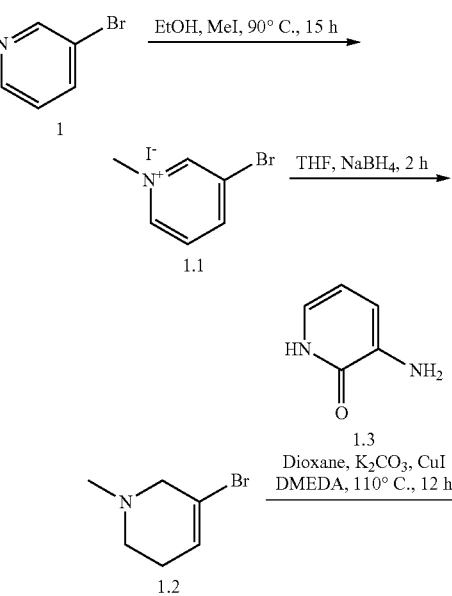

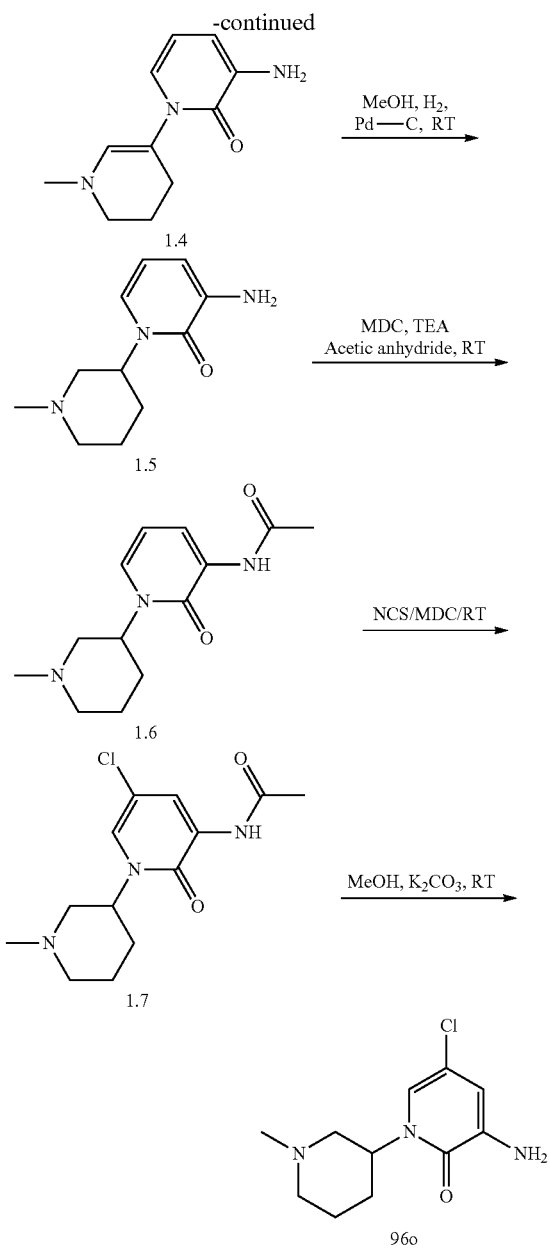

Synthesis of Compound 1.1:

To a solution of 1 (12 g, 75.94 mmol, 1.0 eq) in ethanol (120 mL) was added methyl iodide (54 g, 379 mmol, 5 eq) at room temperature in a sealed tube. Reaction mixture was stirred at 90° C. for 16 h. After completion of reaction, reaction mixture was cooled to room temperature and precipitate solid was filtered out to obtain crude material. This was further purified by trituration with diethyl ether to obtain pure 1.1 (12 g, 91.31%). MS(ES): m/z 174.23 [M+H]$^+$ Synthesis of Compound 1.2:

To a solution of 1.1 (12 g, 69.36 mmol, 1.0 eq) in tetrahydrofuran (120 mL), was added sodium borohydride (5.12 g, 138.64 mmol, 2 eq) at −0° C. Reaction mixture was stirred at room temperature for 2 h. After completion of reaction, reaction mixture was diluted with water extracted with diethyl ether. Organic layer was combined, dried over sodium sulphate and concentrated under reduced pressure to obtain solid which was. This was further purified by distillation to obtain pure 1.2 (8.0 g, Yield: 65.52%). MS (ES): m/z 177.23 [M+H]$^+$ Synthesis of Compound 1.4:

To a solution of 1.2 (8.0 g, 45.45 mmol, 1.0 eq) in 1,4-dioxane (80 mL), 1.3 (12.0 g, 113.62 mmol, 2.5 eq) was added. The reaction mixture was degassed for 10 min under argon atmosphere followed by addition of potassium carbonate (18.8 g, 136.35 mmol, 3.0 eq), N,N-dimethylethylenediamine (1.5 g, 18.18 mmol, 0.4 eq), and copper iodide (1.7 g, 9.09 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 1.4 (4.45 g, Yield: 47.71%). MS (ES): m/z 206.20 [M+H]$^+$.

Synthesis of Compound 1.5:

To a solution of 1.4 (2 g, 9.75 mmol, 1.0 eq) in methanol (15 mL), palladium on charcoal (0.511 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 1.5 (1.4 g, 69.32%). MS (ES): m/z 208 [M+H]$^+$ Synthesis of Compound 1.6:

To a solution of 1.5 (1.5 g, 7.23 mmol, 1.0 eq) in dichloromethane (20 mL), were added triethylamine (1.4 g, 14.46 mmol, 2. eq) and acetic anhydride (3.6 g, 36.15 mmol, 5.0 eq) at 0° C. The reaction mixture was stirred at room temperature for 3 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.6. (0.8 g, Yield: 51.16%). MS (ES): m/z 250.15 [M+H]$^+$ Synthesis of Compound 1.7:

To a solution of 1.6 (0.1 g, 403 mmol, 1.0 eq) in dichloromethane (10 mL), were added N-Iodo-succinimide (0.064 g, 0.48 mmol, 1.2. eq) at 0° C. The reaction mixture was stirred at room temperature for overnight. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.7. (0.02 g, Yield: 17.18%). MS (ES): m/z 284.5 [M+H]$^+$ Synthesis of Intermediate 96o:

To a solution of 1.7 (031 g, 1.095 mmol, 1.0 eq) in methanol (15 mL), potassium carbonate (0.301 g, 2.18 mmol, 2 eq.) was added. Reaction mixture was stirred for overnight at room temperature. After completion of reaction, reaction mixture was filtered through celite-bed and washed with methanol. Filtrate was concentrated under reduced pressure to obtain crude material. This was further purified by trituration with n-pentane to obtain pure 96o. (0.120 g, 45.44%). MS (ES): m/z 242.5 [M+H]$^+$

Synthesis of Intermediate 96p

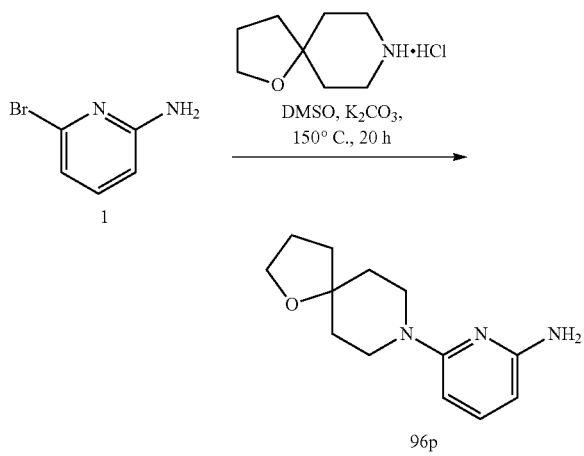

Synthesis of Intermediate 96p.

To a solution of 1. (0.5 g, 2.8 mmol, 1 eq) in dimethyl sulfoxide (10 mL) were added potassium carbonate (0.797 g, 5.78 mmol, 2.0 eq) and 1-oxa-8-azaspiro[4.5]decane hydrochloride (0.772 g, 4.2 mmol, 1.5 eq) followed by heating at 150° C. for 20 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96p (0.280 g, 41.53%). MS(ES): m/z 234.32 [M+H]$^+$.

Synthesis of Intermediate 96q

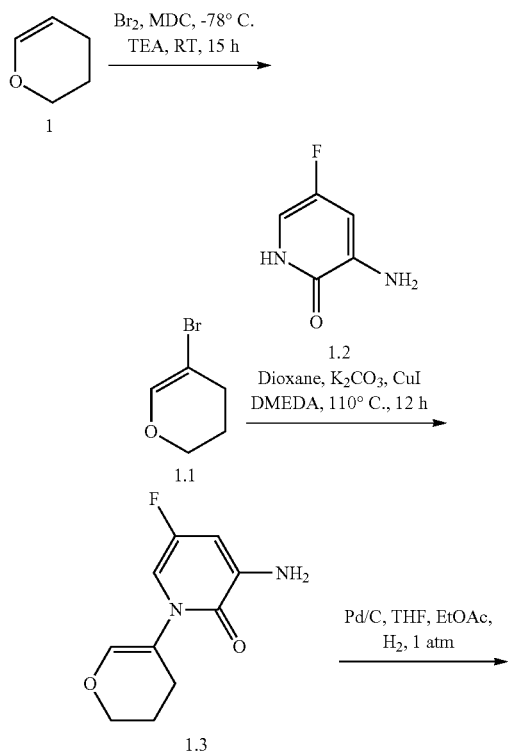

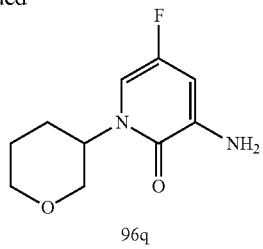

Synthesis of Compound 1.1.

To a solution of 1 (10.0 g, 119.04 mmol, 1.0 eq), in dichloromethane (50 mL) added bromine (19.04 g, 119.04 mmol, 1.0 eq) dropwise at −78° C. and triethylamine (24.0 g, 238.08 mmol, 2.0 eq) was added. The reaction mixture was stirred at room temperature for 15 h. After completion of reaction, reaction mixture was, filtered through celite and product was washed with methanol. Organic layer was combined, dried over sodium sulphate and concentrated under reduced pressure to obtain crude material. This was further purified by column chromatography to obtain pure 1.1. (4.5 g, 23.22%). MS(ES): m/z 162 [M−H]$^+$

Synthesis of Compound 1.3.

To a solution of 1.1 (2.0 g, 12.26 mmol, 1 eq) in 1,4-dioxane (20 mL), 1.2 (1.88 g, 14.71 mmol, 1.2 eq) was added. The reaction mixture was degassed for 10 min under argon atmosphere followed by addition of potassium carbonate (3.38 g, 24.52 mmol, 2.0 eq), N,N-dimethylethylenediamine (0.107 g, 1.22 mmol, 0.1 eq), and copper iodide (0.465 g, 2.45 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.3. (1.3 g, Yield: 22.40%). MS (ES): m/z 211.08 [M+H]$^+$

Synthesis of Intermediate 96q.

To a solution of 1.3. (0.5 g, 2.38 mmol, 1.0 eq) in methanol (10 ml), palladium on charcoal (0.2 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96q (0.300 g, 59.43%). MS (ES): m/z 213.10 [M+H]$^+$

Synthesis of Intermediate 96r

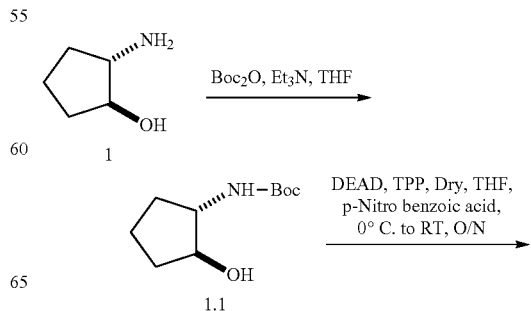

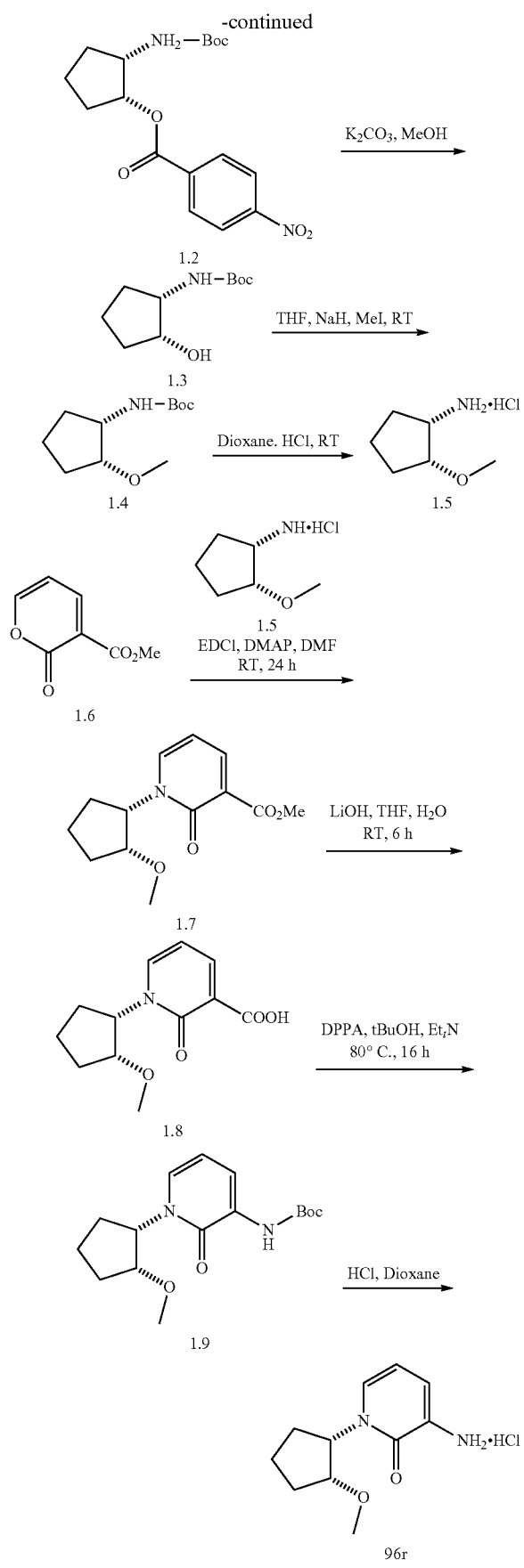

Synthesis of Compound 1.1:
To a cooled solution of 1. (20 g, 198.01 mmol, 1.0 eq), in tetrahydrofuran (30 mL) were added Triethylamine (60 g, 594.01 mmol, 3 eq) and Di-Tert-butyl dicarbonate (64.74 g, 297.05 mmol, 1.5 eq)) at 0° C. The reaction mixture was stirred at room temperature for 3 h. After completion of reaction, reaction mixture was transferred into water and precipitated product was filtered and dried well to obtain 1.1 (14.7 g, 36.94%). MS(ES): m/z 202.5 [M+H]$^+$ Synthesis of Compound 1.2:
To a cooled solution of 1.1 (14.7 g, 73.13 mmol, 1.0 eq), in tetrahydrofuran (10 mL) were added diethyl azocarboxylate (19.4 g, 109.5 mmol, 1.5 eq) triphenyl phosphine (28.7 g, 109 mmol, 1.50 eq) and finally nitro benzoic acid (18.31 g, 109 mmol, 1.50 eq) at 0° C. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (12 g, 46.89%). MS(ES): m/z 351.5 [M+H]$^+$.

Synthesis of Compound 1.3:
To a solution of 1.2 (12 g, 34.18 mmol, 1.0 eq) in methanol (15 mL), potassium carbonate (14.15 g, 102 mmol, 3 eq.) was added. Reaction mixture was stirred for overnight at room temperature. After completion of reaction, reaction mixture was filtered through celite-bed and washed with methanol. Filtrate was concentrated under reduced pressure to obtain crude material. This was further purified by trituration with n-pentane to obtain pure 1.3 (6.2 g, 89.94%). MS (ES): m/z 202.27 [M+H]$^+$ Synthesis of Compound 1.4:
To a cooled solution of 1.3 (6 g, 29.85 mmol, 1.0 eq), in tetrahydrofuran (10 mL) was added sodium hydride (2.3 gg, 59.70 mmol, 2.0 eq). The reaction mixture was stirred at 0° C. for 30 min and methyl iodide (6.35 g, 44.77 mmol, 1.50 eq) was added. The reaction mixture was stirred at room temperature for 6 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.4 (3.4 g, 51.27%). MS(ES): m/z 216.5 [M+H]$^+$.

Synthesis of Compound 1.5:
A cooled solution of 1.4 (3.4 g, 15.84 mmol, 1 eq) in 1,4-dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 1.5 (1.6 g, 66.82%). MS(ES): m/z 152.63 [M+H]$^+$ Synthesis of Compound 1.7:
To a cooled solution of 1.6 (1 g, 6.4 mmol, 1.0 eq), in N,N-dimethylformamide (10 mL) was added 1.5 (0.98 g, 6.4 mmol, 1.0 eq). The reaction mixture was stirred at 0° C. for 6 h and further stirred at room temperature for 15 min. N-Ethyl-N'-(3-dimethylaminopropyl) carbodiimide hydrochloride (1.59 g, 8.32 mmol, 1.3 eq) and 4-Dimethylaminopyridine (0.192 g, 1.6 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.7 (0.650 g, 39.87%). MS(ES): m/z 252.5 [M+H]⁺.

Synthesis of Compound 1.8:

To a solution of 1.7 (0.650 g, 2.58 mmol, 1.0 eq), in tetrahydrofuran: methanol: water (10 mL, 2:2:1) was added lithium hydroxide (1 g, 25.79 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.8 (0.4 g, 65.18%). MS(ES): m/z 238.23 [M+H]⁺.

Synthesis of Compound 1.9:

To a solution of 1.8 (0.40 g, 1.68 mmol, 1.0 eq) in tert.butanol (6 mL) was added triethylamine (0.29 g, 2.86 mmol, 1.7 eq) and diphenyl phosphoryl azide (0.6 g, 2.18 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.9 (0.190 g, 36.54%). MS(ES): m/z 309.38 [M+H]⁺.

Synthesis of Intermediate 96r:

A cooled solution of 1.9 (0.190 g, 0.61 mmol, 1 eq) in 1,4-dioxane (4 mL) was added 4N hydrochloric acid in dioxane (5 mL) dropwise. The reaction mixture was stirred at room temperature for 2 h. After completion of reaction, reaction mixture was concentrated under reduced pressure to obtain pure 96r (0.1 g, 77.93%). MS(ES): m/z 210 [M+H]⁺.

Synthesis of Intermediate 96s

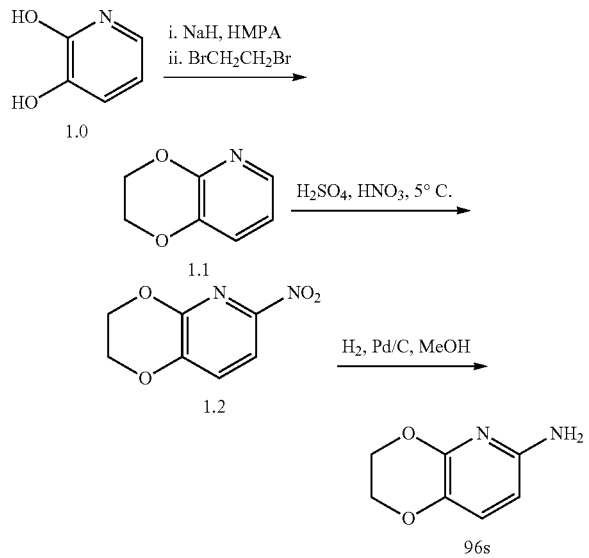

Synthesis of Compound 1.1

To a solution of compound 1 (10.0 g, 90.01 mmol, 1.0 eq) in Hexamethylphosphoramide (16.12 g, 90.01 mmol, 1.0 eq) at 0° C. was added sodium hydride (7.2 g, 180.0 mmol, 2.0 eq) portion wise. Reaction mixture was allowed to stir at 0° C. for 20 min followed by addition of 1,2-dibromoethane (25.36 g, 135.01 mmol, 1.5 eq). Reaction mixture was heated at 100° C. for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography by eluting in hexane to obtain 1.1 (1.5 g, 12.15%) MS(ES): m/z 138.14.[M+H]⁺.

Synthesis of Compound 1.2

A solution of compound 1.2 (1.50 g, 13.50 mmol, 1.0 eq) in sulfuric acid (1.5 ml) was added to a mixture of sulfuric acid (9.0 ml) and nitric acid (1.50 ml) drop wise at 0° C. Reaction mixture was allowed to stir at room temperature for 60 min. After completion of the reaction, the reaction mixture was transferred into ice and stirred. The precipitated product was filtered and dried well to obtain 1.2 (1.10 g, 59.41%) MS(ES): m/z 183.14.[M+H]⁺.

Synthesis of Intermediate 96s.

To a solution of 1.2 (1.10 g, 6.03 mmol, 1.0 eq) in methanol (15 mL), palladium on charcoal (0.511 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 96 (0.479 g, 52.13%). MS (ES): m/z 153.15 [M+H]⁺.

Synthesis of Intermediate 96t

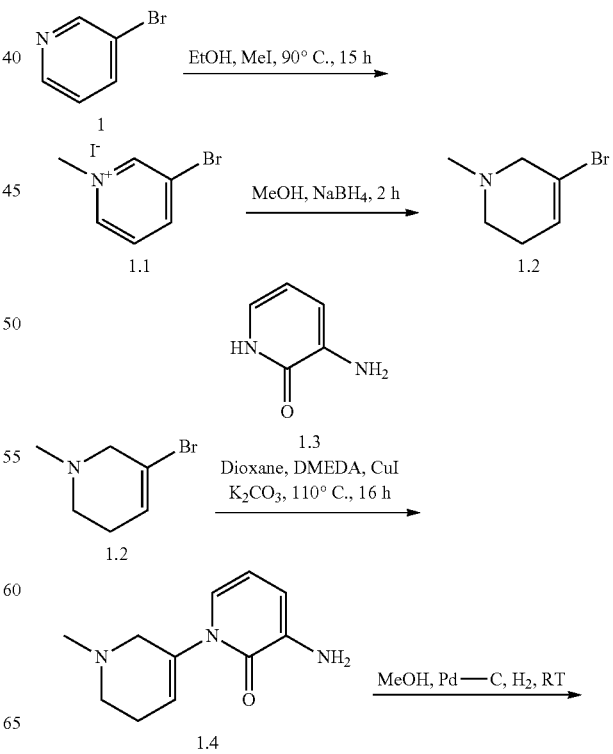

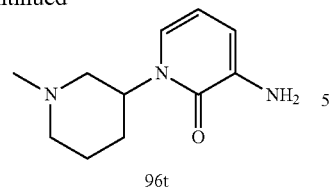

96t

Synthesis of Compound 1.1.

To a solution of 1. (10 g, 63.29 mmol, 1.0 eq) in ethanol (400 ml), methyl iodide (44.9 g, 316.45 mmol, 5.0 eq) was added. The reaction mixture was heated at 90° C. for 15 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 15% ethyl acetate in hexane to obtain 1.1. (13 g, Yield: 99.60%). MS (ES): m/z 172.98 [M+H]+

Synthesis of Compound 1.2.

To a solution of 1.1 (13 g, 43.33 mmol, 1.0 eq) in methanol (200 ml), sodium borohydride (2.404 g, 64.99 mmol, 1.5 eq) was added. The reaction mixture was stirred at RT for 2 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 15% ethyl acetate in hexane to obtain 1.2. (3.2 g, Yield: 91.31%). MS (ES): m/z 177.00 [M+H]+

Synthesis of Compound 1.4.

To a solution of 1.2 (1.5 g, 8.52 mmol, 1.0 eq) in 1,4-dioxane (25 mL), 1.3 (0.721 g, 6.56 mmol, 0.8 eq) was added. The reaction mixture was degassed for 10 min under argon atmosphere followed by addition of potassium carbonate (2.35 g, 17.04 mmol, 2.0 eq), N,N-dimethylethylenediamine (0.149 g, 1.70 mmol, 0.2 eq), and copper iodide (0.323 g, 1.70 mmol, 0.2 eq). The reaction mixture was heated at 110° C. for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.4. (0.9 g, Yield: 51.46%). MS (ES): m/z 206.12 [M+H]+

Synthesis of Intermediate 96t.

To a solution of 1.4. (0.9 g, 4.39 mmol, 1.0 eq) in methanol (20 ml), palladium on charcoal (0.4 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96t (0.540 g, 51.46%). MS (ES): m/z 208.14 [M+H]+.

Synthesis of Intermediate 96u

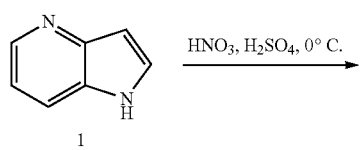

1

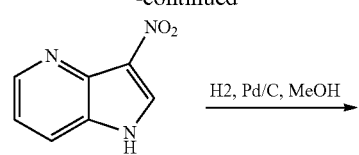

1.1

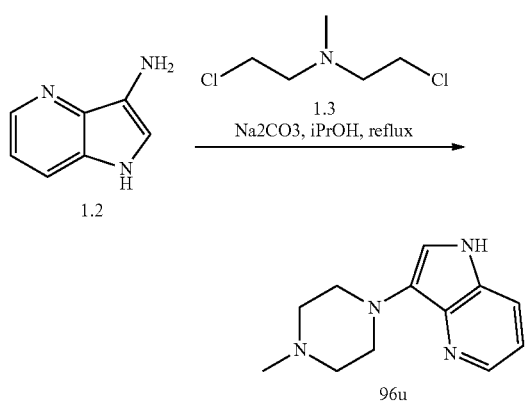

96u

Synthesis of Compound 1.1.

To a solution of 1 (3 g, 16.93 mmol, 1.0 eq), in sulfuric acid (3 mL) was added nitric acid (2 mL) at 0° C. and stirred at 0° C. for 1.5 h. After completion of reaction, reaction mixture was transferred into ice water and precipitated product was filtered, dried well to obtain 1.1 (1.2 g, 43.45%). MS(ES): m/z 164.50 [M+H]+

Synthesis of Compound 1.2.

To a solution of 1.1 (1.2 g, 7.36 mmol, 1.0 eq) in methanol (5 mL), palladium on charcoal (0.12 g) was added. Hydrogen was purged through reaction mixture for 24 h at room temperature. After completion of reaction, reaction mixture was filtered through celite-bed and washed with methanol. Filtrate was concentrated under reduced pressure to obtain 1.2 (0.75 g, 76.57.00%). MS(ES): m/z 135.14 [M+H]+

Synthesis of Intermediate 96u.

To a solution of 1.3 (0.4 g, 1.025 mmol, 1.0 eq) in isopropyl alcohol (100 mL), were added sodium carbonate (0.217 g, 2.05 mmol, 2.0 eq) and 1.2 (0.136 g, 1.025 mmol, 1.0 eq) and stirred for 16 h at room temperature. After completion of reaction, reaction mixture transferred into water and product was extracted with ethyl acetate. Organic layer was combined and dried over sodium sulphate and concentrated under reduced pressure to obtain concentrated under reduced pressure to obtain 96 u (0.170 g, 30.66%). MS(ES): m/z 217.35 [M+H]+.

Synthesis of Intermediate 96v

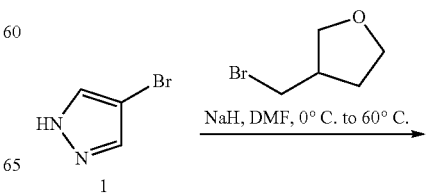

1

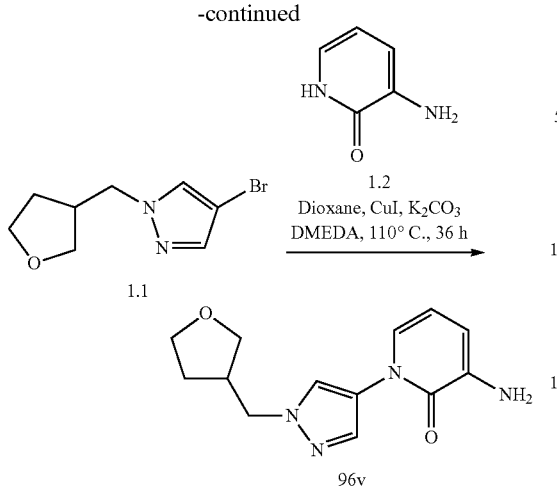

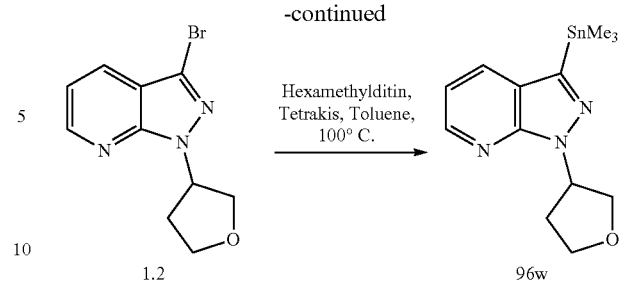

Synthesis of Compound 1.2

To a solution of 1 (0.6 g, 3.03 mmol, 1.0 eq) and 1.1 (0.27 g, 3.03 mmol, 1.0 eq) in tetrahydrofuran (10 mL) was added triphenyl phosphine (1.19 g, 4.54 mmol, 1.5 eq) and Diisopropyl azodicarboxylate (0.918 g, 4.54 mmol, 1.5 eq). The reaction was stirred at room temperature for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 10% ethyl acetate in hexane as eluant to obtain pure 1.2 (0.7 g, 86.17%). MS(ES): m/z 269.11 [M+H]⁺.

Synthesis of Compound 1.1

To a solution of compound 1 (1.4 g, 9.52 mmol, 1.0 eq) in N,N-Dimethylformamide (15 mL), at 0° C. was added sodium hydride (0.274 g, 11.42 mmol, 1.2 eq) portionwise and allowed to stir at 0° C. for 60 min followed by addition of 3-(bromomethyl)tetrahydrofuran (1.70 g, 10.47 mmol, 1.1 eq) dropwise. Reaction mixture was heated at 60° C. for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and product was eluted in hexane to obtain pure 1.1 (0.800 g, 36.34%) MS(ES): m/z 232 [M+H]⁺.

Synthesis of Intermediate 96v.

To a solution of 1.1 (0.800 g, 3.47 mmol, 1.0 eq) and 1.2 (0.496 g, 4.51 mmol, 1.3 eq) in 1,4-dioxane (10 mL) was added potassium carbonate (1.19 g, 8.67 mmol, 2.5 eq) and degassed with argon for 15 min. Copper iodide (0.098 g, 0.520 mmol, 0.15 eq) and 1,2-dimethylethylenediamine (0.076 g, 0.867 mmol, 0.25 eq) was added and reaction mixture again degassed with argon for 5 min followed by heating at 110° C. for 36 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 4.0% methanol in dichloromethane to obtain pure 96v (0.150 g, 16.65%). MS (ES): m/z 261.13 [M+H]⁺.

Synthesis of Intermediate 96w

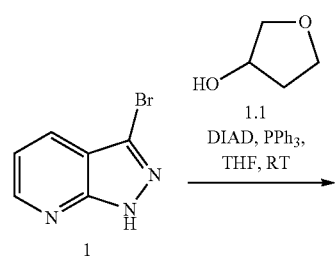

Synthesis of Intermediate 96w.

To a solution of 1.2 (0.52 g, 1.94 mmol, 1.0 eq) in toluene (26 mL) was added hexamethylditin (1.91 g, 5.82 mmol, 3.0 eq) and Tetrakis(triphenylphosphine)palladium(0) (0.224 g, 0.194 mmol, 2.0 eq). The reaction mixture was degassed for 10 min under argon atmosphere. The reaction was stirred at 100° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 10% ethyl acetate in hexane as eluant to obtain pure 96 w (0.35 g, 51.26%). MS(ES): m/z 353.03 [M+H]⁺.

Synthesis of Intermediate 96x

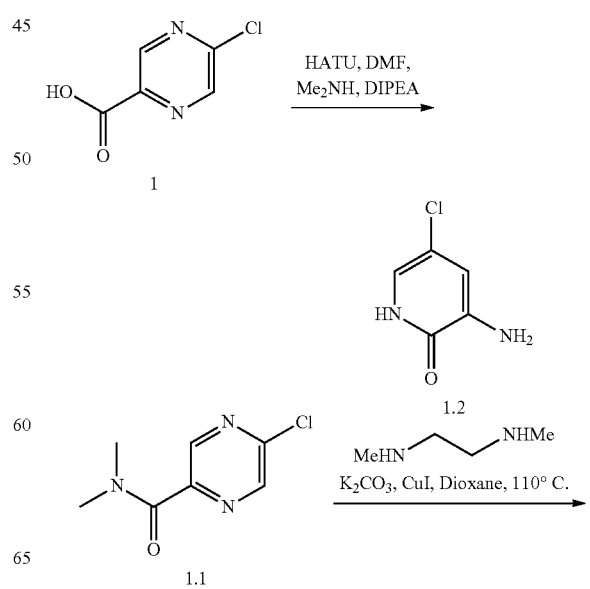

-continued

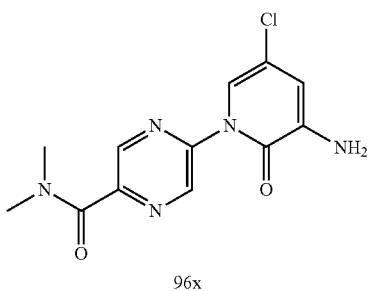

96x

Synthesis of Compound 1.1.

Compound was synthesized using general procedure A to obtain 1.1. (Yield: 59.79%). MS (ES): m/z 186.61 [M+H].

Synthesis of Intermediate 96x.

To a solution of 1.1. (1.4 g, 7.54 mmol, 1.0 eq) in 1,4-dioxane (100 mL), 1.2 (1.6 g, 11.3 mmol, 1.5 eq) was added. The reaction mixture was degassed for 10 min under argon atmosphere followed by addition of potassium carbonate (2.0 g, 15.08 mmol, 2.0 eq), N,N-dimethylethylenediamine (0.26 g, 3.01 mmol, 0.4 eq), and copper iodide (0.28 g, 1.50 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96x (0.36 g, Yield: 16.25%). MS (ES): m/z 294.71 [M+H]$^+$.

Synthesis of Intermediate 96y

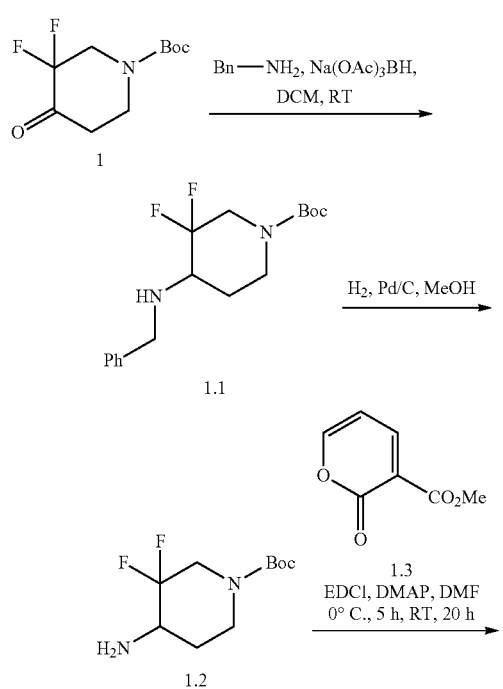

-continued

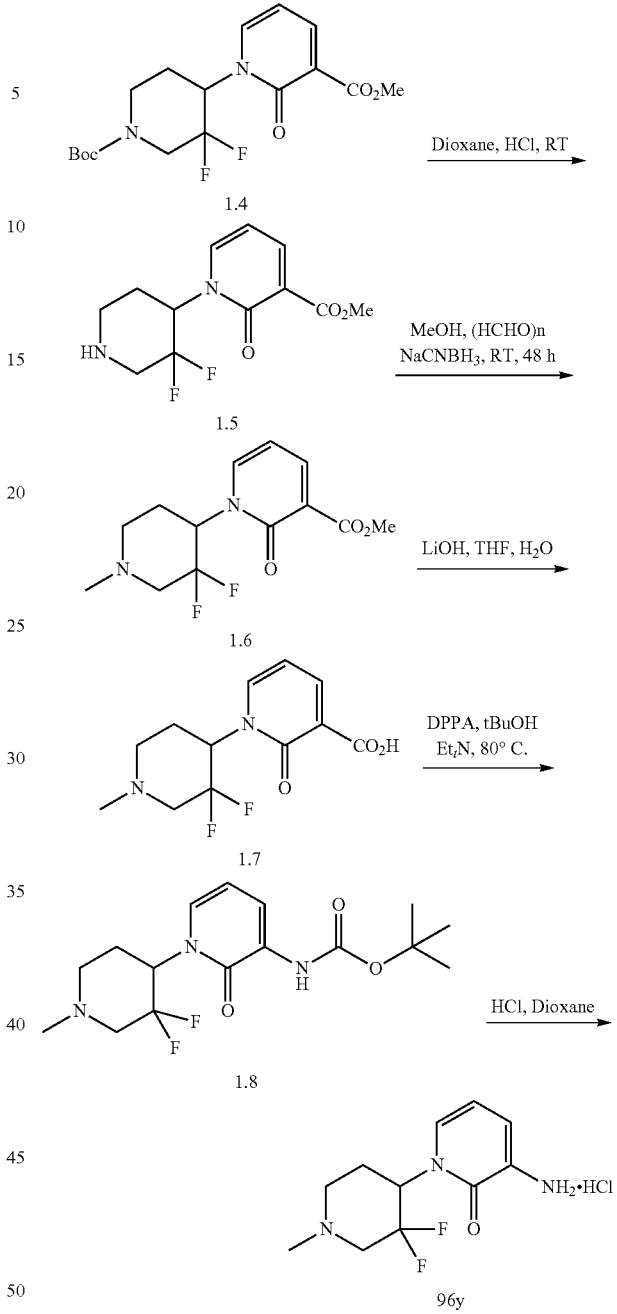

Synthesis of Compound 1.1:

To a cooled solution of 1 (2 g, 8.51 mmol, 1.0 eq), in dichloromethane (50 mL) was added benzyl amine (1.3 g, 12.7 mmol, 1.5 eq) at 0° C. The reaction mixture was stirred at 0° C. for 30 min and sodium triacetoxyborohydride (5.4 g, 25.53 mmol, and 3.0 eq) was added portion wise. The reaction mixture was stirred at room temperature for 16 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.1 (1.2 g, 43.24%). MS(ES): m/z 327.39 [M+H]$^+$.

Synthesis of Compound 1.2:

To a solution of 1.1 (1.2 g, 3.6 mmol, 1.0 eq) in methanol (15 mL), palladium on charcoal (0.511 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 1.1 (0.8 g, 92.10%). MS (ES): m/z 237 [M+H]$^+$.

Synthesis of Compound 1.4:

To a cooled solution of 1.3 (0.66 g, 4.2 mmol, 1.0 eq), in N,N-dimethylformamide (50 mL) was added 1.2 (1.0 g, 4.2 mmol, 1.0 eq). The reaction mixture was stirred at 0° C. for 30 min and further stirred at room temperature for 15 min. N-Ethyl-N'-(3-dimethylaminopropyl) carbodiimide hydrochloride (0.104 g, 6.747 mmol, 1.3 eq) and 4-Dimethylaminopyridine (0.120 g, 1.05 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.4 (0.35 g, 22.21%). MS(ES): m/z 373.45 [M+H]$^+$.

Synthesis of Compound 1.5:

A cooled solution of 1.4 (0.520 g, 1.39 mmol, 1.0 eq) in 1,4-dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain 1.5 (0.420 g, 99.95%). MS(ES): m/z 273.35 [M+H]$^+$ Synthesis of Compound 1.6:

To a cooled solution of 1.5 (0.41 g, 1.5 mmol, 1.0 eq), in methanol (50 mL) was added paraformaldehyde (0.27 g, 9.1 mmol, 6.0 eq) at 0° C. The reaction mixture was stirred at 0° C. for 30 min and sodium cyanoborohydride (0.5 g, 9.1 mmol, 6.0 eq) and acetic acid (0.54 g, 9.1 mmol, 6.0 eq) was added portion wise. The reaction mixture was stirred at room temperature for 16 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.6 (0.3 g, 69.59%). MS(ES): m/z 287.5 [M+H]$^+$.

Synthesis of Compound 1.7:

To a solution of 1.6 (0.3 g, 1.01 mmol, 1.0 eq), in tetrahydrofuran: methanol: water (10 mL, 2:2:1) was added lithium hydroxide (0.432 g, 10.10 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.7 (0.220 g, 77.1%). MS(ES): m/z 274.5 [M+H]$^+$.

Synthesis of Compound 1.8.

To a solution of 1.7 (0.220 g, 0.80 mmol, 1.0 eq) in tert. Butanol (6 mL) was added triethylamine (0.138 g, 1.36 mmol, 1.7 eq) and diphenyl phosphoryl azide (0.286 g, 1.04 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.8 (0.160 g, 57.66%). MS(ES): m/z 344.34 [M+H]$^+$.

Synthesis of Intermediate 96y:

A cooled solution of 1.8 (0.160 g, 0.46 mmol, 1 eq) in 1,4-dioxane (4 mL) was added 4N hydrochloric acid in dioxane (10 mL) drop wise. The reaction mixture was stirred at room temperature for 2 h. After completion of reaction, reaction mixture was concentrated under reduced pressure to obtain 96y (0.125 g, 95.21%). MS(ES): m/z 280 [M+H]$^+$.

Synthesis of Intermediate 96z

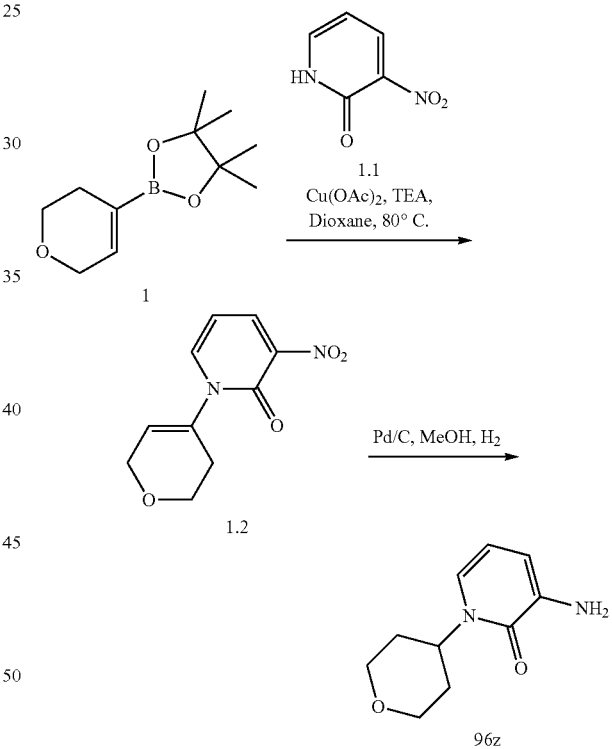

Synthesis of Compound 1.2.

To a solution of 1 (3 g, 14.28 mmol, 1.0 eq) and 1.1 (2.4 g, 17.14 mmol, 1.2 eq) in dioxane (30 mL) was added copper acetate (2.60 g, 14.28 mmol, 1.0 eq) and triethylamine (5.00 mL, 35.7 mmol, 2.5 eq) under nitrogen. The reaction was stirred at 80° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 10% ethyl acetate in hexane to obtain pure 1.2 (0.380 g, 11.98%), MS(ES): m/z 222.20 [M+H]$^+$.

1311

Synthesis of Intermediate 96z.

To a solution of 1.1 (0.380 g, 1.71 mmol, 1.0 eq) in methanol (4 ml), palladium on charcoal (0.100 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 1.4% methanol in dichloromethane to obtain pure 96z (0.120 g, 36.13%). MS (ES): m/z 195.23 [M+H]$^+$.

Synthesis of Intermediate 96aa

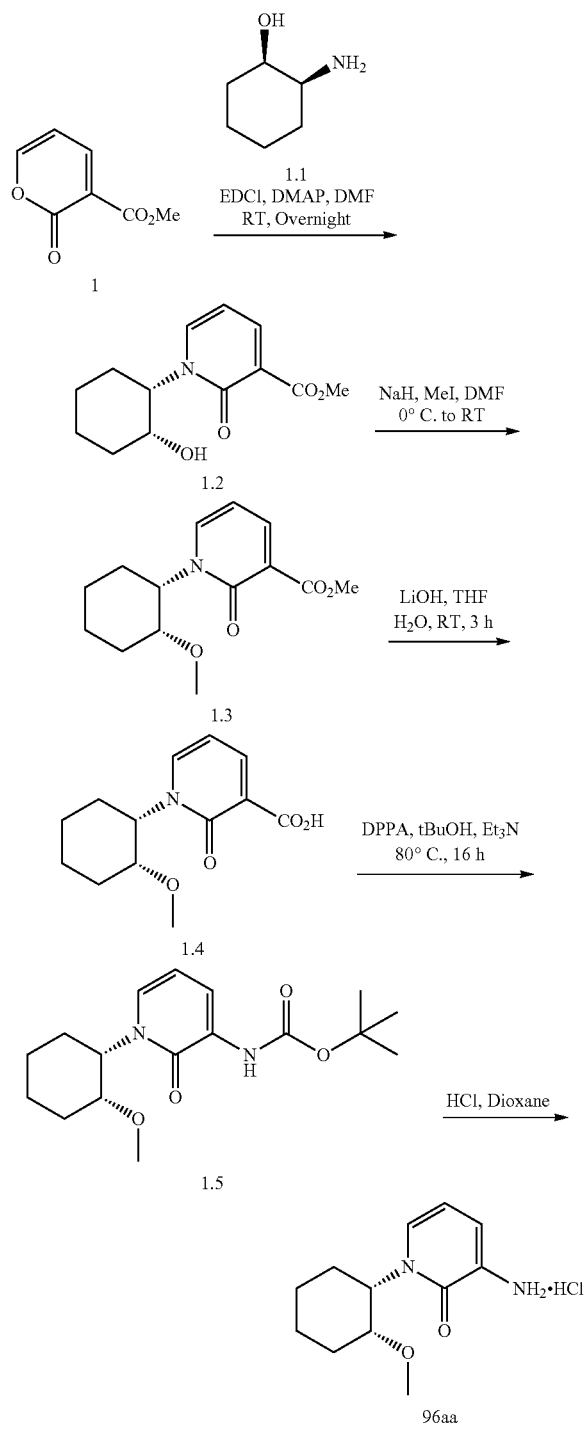

1312

Synthesis of Compound 1.2.

To a stirred solution of 1.1 (5.0 g, 32.47 mmol, 1.0 eq) in N,N-dimethyl formamide (50 mL) was added 1 (5.0 g, 32.47 mmol, 1.0 eq) in one portion at 0° C. under Ar followed by diisopropyl ethyl amine (6.3 g, 48.71 mmol, 1.5 eq) and the reaction mixture was stirred at 0° C. for 3 h. 1-Ethyl-3-(3-dimethylaminopropyl)carbodiimide hydrochloride (8.1 g, 42.21 mmol, 1.3 eq) and 4-Dimethylaminopyridine (1.0 g, 8.11 mmol, 0.25 eq) were added under Ar and the reaction mixture was stirred at room temperature overnight. The reaction mixture was concentrated under reduced pressure and the residue was purified by column chromatography using 1.9% methanol in dichloromethane to obtain pure 1.2 (4.3 g, 52.76%). MS(ES): m/z 252.42 [M+H]$^+$.

Synthesis of Compound 1.3.

To a stirred solution of 1.2 (4.0 g, 15.94 mmol, 1.0 eq) in dimethylformamide (40 mL) was added sodium hydride (1.3 g, 31.88 mmol, 2.0 eq, 60% dispersion) in small portions over 10 minutes under N$_2$ at 0° C. After stirring at room temperature for 15 minutes the reaction mixture was cooled to 0° C. and methyl iodide (2.9 g, 20.72 mmol, 1.3 eq) was added dropwise slowly over 10 minutes. The reaction mixture was stirred at room temperature for 2 h and then quenched with ice-water and extracted with ethyl acetate. The combined organic extract was washed with brine dried over sodium sulphate and concentrated under reduced pressure to obtain crude product. This was purified by column chromatography and compound was eluted in 30% ethyl acetate in hexane to obtain pure 1.3 (2.30 g, 54.50%). MS(ES): m/z 266.34 [M+H]$^+$.

Synthesis of Compound 1.4.

To a stirred solution of 1.3 (2.30 g, 8.68 mmol, 1.0 eq) in tetrahydrofuran (70 mL) was added methanol (24.5 mL) and a solution of lithium hydroxide monohydrate (1.5 g, 34.72 mmol, 4.0 eq) in water (35 mL) and the reaction mixture was stirred at room temperature for 3 h. The reaction mixture was concentrated under vacuum and the residue was adjusted to pH 3 by slow addition of 1N HCl at 0° C. The precipitate was collected by filtration and dried to obtain pure compound 1.4 (1.9 g, 87.55%). MS(ES): m/z 252.45 [M+H]$^+$.

Synthesis of Compound 1.5.

A stirred mixture of 1.4 (1.90 g, 7.57 mmol, 1.0 eq), tert butanol (20 mL), diphenyl phosphoryl azide (2.9 g, 10.60 mmol, 1.4 eq) and triethyl amine (1.07 g, 10.60 mmol, 1.4 eq) was heated at 80° C. under N$_2$ for 18 h. The reaction mixture was evaporated under reduced pressure. The residue was dissolved in ethyl acetate and the organic solution was washed with water. The organic phase was dried over sodium sulfate and concentrated under reduced pressure to get the crude product. This was purified by column chromatography and compound was eluted in 1% methanol in dichloromethane to obtain pure 1.5 (1.8 g, 74.07%). MS(ES): m/z 323.34 [M+H]$^+$.

Synthesis of Intermediate 96aa.

To a stirred solution of 1.5 (1.8 g, 5.59 mmol) in dichloromethane (18 mL) was added 4 M HCl in dioxane (15 mL) dropwise at 0° C. under N$_2$ and the reaction mixture was stirred at room temperature for 3 h. Reaction mixture concentrated under reduced pressure and the solid residue was triturated with diethyl ether to obtain the hydrochloride salt of 96aa (1.20 g, 82.75%). MS(ES): m/z 223.64 [M+H]$^+$.

Synthesis of Intermediate 96bb

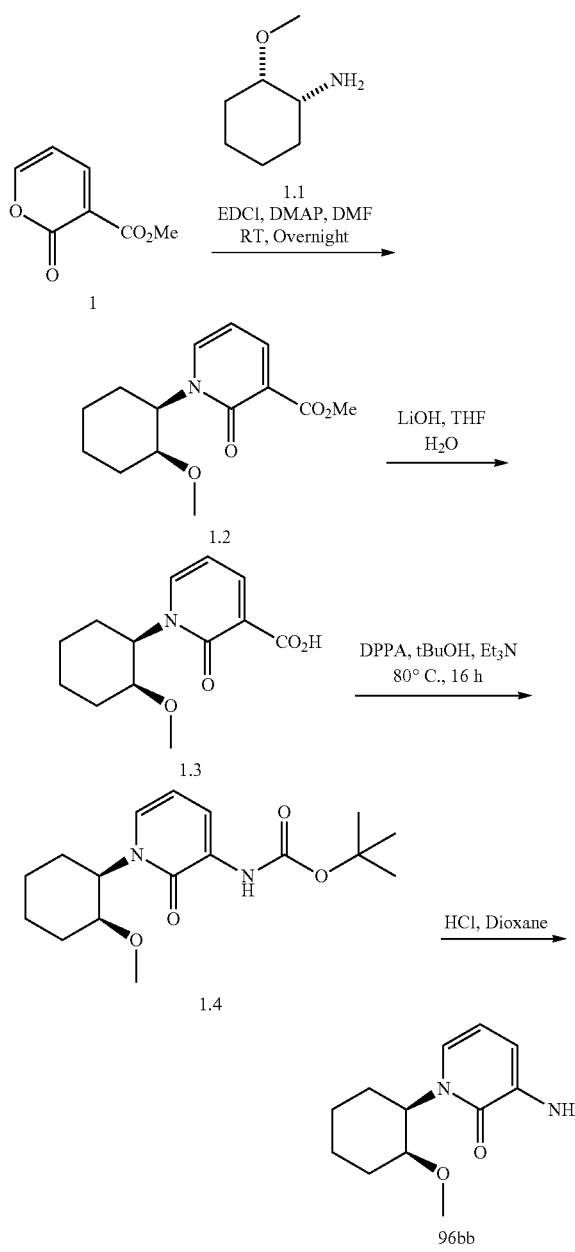

Synthesis of Compound 1.2.

To a cooled solution of 1 (3.0 g, 19.46 mmol, 1.0 eq), in N,N-dimethylformamide (30 mL) was added 1.1 (2.5 g, 19.46 mmol, 1.0 eq). The reaction mixture was stirred at 0° C. for 30 min and further stirred at room temperature for 15 min. N-Ethyl-N'-(3-dimethylaminopropyl)carbodiimide hydrochloride (3.9 g, 25.29 mmol, 1.3 eq) and 4-Dimethylaminopyridine (0.475 g, 3.89 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (1.1 g, 21.30%). MS(ES): m/z 266.13 [M+H]$^+$.

Synthesis of Compound 1.3.

To a solution of 1.2 (1.1 g, 4.14 mmol, 1.0 eq), in tetrahydrofuran: water (22 mL, 2:1) was added lithium hydroxide (0.993 g, 41.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.8 g, 76.79%). MS(ES): m/z 252.12 [M+H]$^+$.

Synthesis of Compound 1.4.

To a solution of 1.3 (0.8 g, 3.18 mmol, 1.0 eq) in tert.butanol (20 mL) was added triethylamine (0.545 g, 5.40 mmol, 1.7 eq) and diphenyl phosphoryl azide (1.1 g, 4.13 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.550 g, 53.58%). MS(ES): m/z 323.19 [M+H]$^+$.

Synthesis of Intermediate 96bb.

A cooled solution of 1.4 (0.550 g, 1.70 mmol, 1 eq) in dioxane (12 mL) was added 4N hydrochloric acid in dioxane (24 mL) as a dropwise. The reaction mixture was stirred at room temperature for 2 h. After completion of reaction, reaction mixture was concentrated under reduced pressure to obtain pure 96bb. (0.4 g, 98.89%). MS(ES): m/z 223.14 [M−HCl]$^+$.

Synthesis of Intermediate 96cc

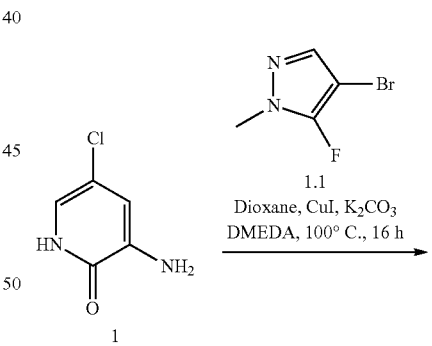

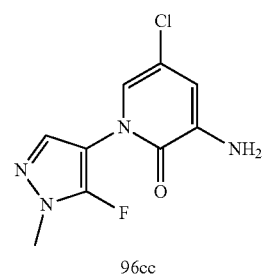

Synthesis of Intermediate 96cc.

To a solution of 1. (0.180 g, 1.24 mmol, 1 eq) and 1.1 (0.264 g, 1.48 mmol, 1.2 eq) in 1,4-dioxane (6 mL) was added potassium carbonate (0.342 g, 2.48 mmol, 2.0 eq) and degassed with argon for 15 min. Copper iodide (0.045 g, 0.24 mmol, 0.2 eq) and 1,2-dimethylethylenediamine (0.043 g, 0.49 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96cc (0.050 g, 23.17%). MS(ES): m/z 243.04 [M+H]$^+$.

Synthesis of Intermediate 96dd

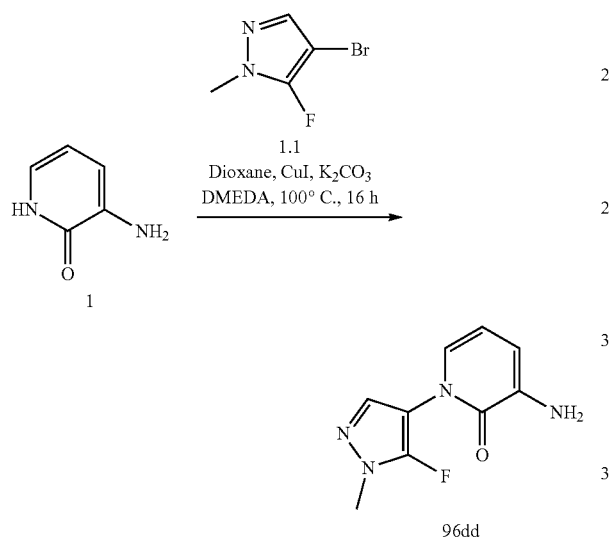

Synthesis of Intermediate 96dd.

To a solution of 1. (0.070 g, 0.63 mmol, 1.0 eq) and 1.1 (0.123 g, 0.69 mmol, 1.1 eq) in 1,4-dioxane (3 mL) was added potassium carbonate (0.173 g, 1.26 mmol, 2.0 eq) and degassed with argon for 15 min. Copper iodide (0.022 g, 0.12 mmol, 0.2 eq) and 1,2-dimethylethylenediamine (0.022 g, 0.25 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96dd. (0.035 g, 26.45%). MS(ES): m/z 209.08 [M+H]$^+$.

Synthesis of Intermediate 96ee and 96ff

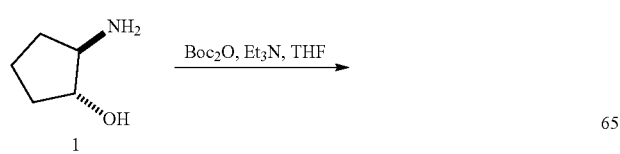

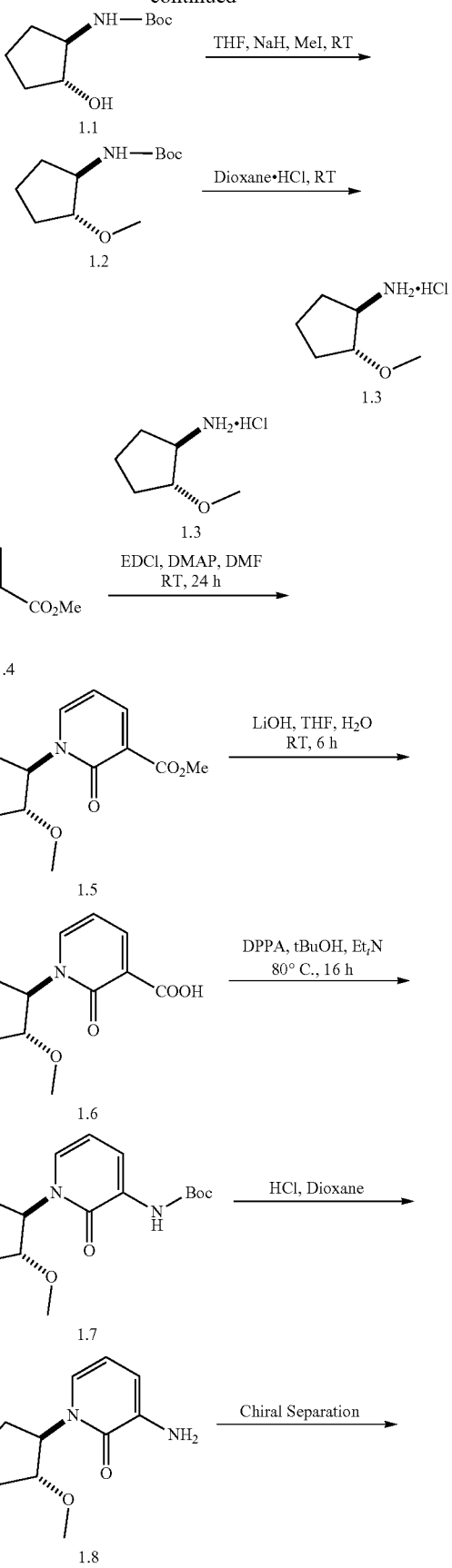

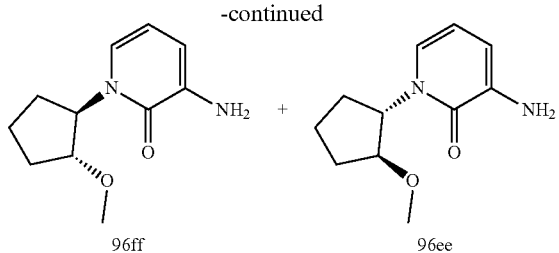

Synthesis of Compound 1.1:

To a cooled solution of 1. (3 g, 29.7 mmol, 1.0 eq), in methanol (30 mL) was added Triethylamine (8.9 g, 89 mmol, 3 eq) and Di-Tert-butyl dicarbonate (9.7 g, 44.5 mmol, 1.5 eq) at 0° C. The reaction mixture was stirred at room temperature for 3 h. After completion of reaction, reaction mixture was transferred into water and product was precipitate out. Solid compound was filtered under reduced pressure to obtain crude material as 1.1 (0.650 g, 39.87%). MS(ES): m/z 252.5 [M+H]$^+$ Synthesis of Compound 1.2:

To a cooled solution of 1.1 (4 g, 19.9 mmol, 1.0 eq) in tetrahydrofuran (40 mL) was added sodium hydride (1.5 g, 39.8 mmol, 2.0 eq). The reaction mixture was stirred at 0° C. for 30 min and methyl iodide (4 g, 28.5 mmol, 1.5 eq) was added. The reaction mixture was stirred at room temperature for 6 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (2.8 g, 65.44%). MS(ES): m/z 216.5 [M+H]$^+$.

Synthesis of Compound 1.3:

To a cooled solution of 1.2 (1.8 g, 8.33 mmol, 1.0 eq) in 1,4-dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 1.3 (1.2 g, 94.98%). MS(ES): m/z 152.63 [M+H]$^+$.

Synthesis of Compound 1.5:

To a cooled solution of 1.4 (1 g, 6.4 mmol, 1.0 eq), in N,N-dimethylformamide (10 mL) was added 1.3 (0.98 g, 6.4 mmol, 1.0 eq). The reaction mixture was stirred at 0° C. for 6 h and further stirred at room temperature for 15 min. N-Ethyl-N'-(3-dimethylaminopropyl) carbodiimide hydrochloride (1.59 g, 8.32 mmol, 1.3 eq) and 4-Dimethylaminopyridine (0.192 g, 1.6 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.5 (0.650 g, 39.87%). MS(ES): m/z 252.5 [M+H]$^+$.

Synthesis of Compound 1.6:

To a solution of 1.5 (0.650 g, 2.58 mmol, 1.0 eq), in tetrahydrofuran: methanol: water (10 mL, 2:2:1) was added lithium hydroxide (1 g, 25.79 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6 (0.4 g, 65.18%). MS(ES): m/z 238.23 [M+H]$^+$.

Synthesis of Compound 1.7:

To a solution of 1.6 (0.40 g, 1.68 mmol, 1.0 eq) in tertiary butanol (6 mL) was added triethylamine (0.29 g, 2.86 mmol, 1.7 eq) and diphenyl phosphoryl azide (0.6 g, 2.18 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7 (0.190 g, 36.54%). MS(ES): m/z 309.38 [M+H]$^+$.

Synthesis of Compound 1.8:

A cooled solution of 1.7 (0.190 g, 0.61 mmol, 1 eq) in 1,4-dioxane (4 mL) was added 4N hydrochloric acid in dioxane (5 mL) dropwise. The reaction mixture was stirred at room temperature for 2 h. After completion of reaction, reaction mixture was concentrated under reduced pressure to obtain pure 1.8 (0.1 g, 77.93%). MS(ES): m/z 210 [M+H]$^+$.

Synthesis of Intermediate 96ff and 96ee:

Isomers of 1.8 (0.1 g) were separated out using column (CHIRAL PAK AD-H 250×4.6 mm, 5 μM) and 0.360% Diethylamine in methanol as co-solvent with flow rate of 4 mL/min. to get pure fraction-1 and fraction-2. Fraction-1 was concentrated under reduced pressure at 30° C. to afford 0.04 g. MS(ES): m/z 210 [M+H]$^+$, LCMS purity: 100%, CHIRAL HPLC purity: 100%. Fraction-2 was concentrated under reduced pressure at 30° C. to afford 0.045 g. MS (ES): m/z 210 [M+H]$^+$, LCMS purity: 98%, CHIRAL HPLC purity: 100%.

Synthesis of Intermediate 96gg

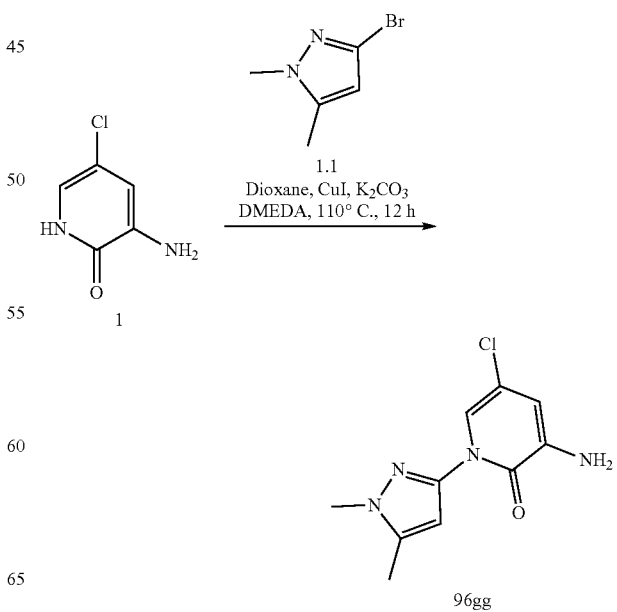

Synthesis of Intermediate 96gg.

To a solution of 1 (1 g, 6.92 mmol, 1.0 eq) in 1,4-dioxane (100 mL), 1.1 (1.8 g, 10.38 mmol, 1.5 eq) was added. The reaction mixture was degassed for 10 min under argon atmosphere followed by addition of potassium carbonate (1.9 g, 13.84 mmol, 2.0 eq), N,N-dimethylethylenediamine (0.24 g, 2.76 mmol, 0.4 eq), and copper iodide (0.26 g, 1.38 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96 gg (0.27 g, Yield: 16.35%). MS (ES): m/z 239.68 [M+H]$^+$.

Synthesis of Intermediate 96hh

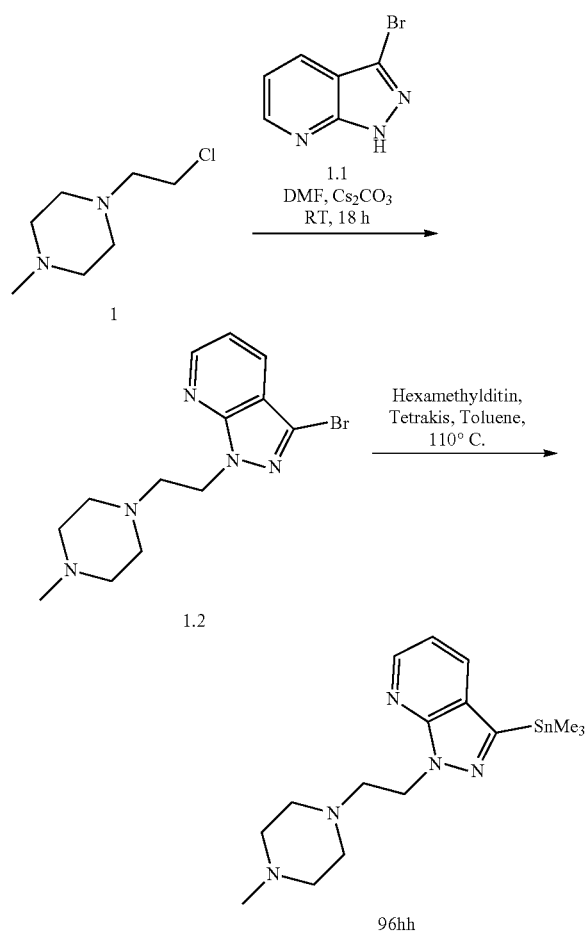

Synthesis of Compound 1.2.

A solution of 1.0 (1 gm, 6.14 mmol, 1.0 eq) and 1.1 (1.45 g, 7.36 mmol, 1.2 eq) in N—N-Dimethylformamide (20 mL) was added Cesium carbonate (3.99 gm, 12.28 mmol, 2.0 eq) and allowed to stir at room temperature for 18 h. After completion of reaction, reaction mixture transferred into water and product was extracted with ethyl acetate. Organic layer was combined, washed with brine solution, dried over sodium sulphate and concentrated under reduced pressure to obtain crude product which was purified by column chromatography using silica gel (100-200 mesh) eluting pure compound in 40-80% ethyl acetate in hexane to obtain pure 1.2. (0.580 g, 29.10%). MS (ES): m/z 325.07 [M+H]$^+$.

Synthesis of Intermediate 96hh.

Argon was purged for 10 min through a stirred solution of 1.2 (0.580 g, 1.78 mmol, 1.0 eq) in toluene (15 mL) followed by addition of hexamethylditin (0.583 g, 1.78 mmol, 1.0 eq) and Tetrakis(triphenylphosphine)palladium(0) (0.205 g, 0.17 mmol, 0.1 eq) and further purging done for 5 min. Reaction was allowed to stir at 100° C. for 2 h. After completion of reaction, reaction mixture was transferred into water and product was extracted with ethyl acetate. Organic layer was combined, washed with brine solution, dried over sodium sulphate and concentrated under reduced pressure to obtain to obtain 96hh. (0.300 g, 41.09%), MS (ES): m/z 409.13 [M+H]$^+$.

Synthesis of Intermediate 96ii

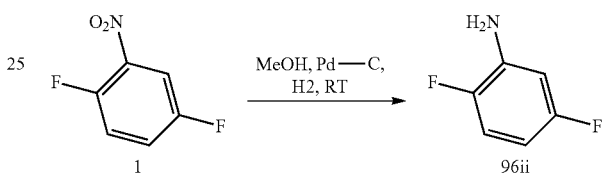

Synthesis of Intermediate 96ii.

To a solution of 1 (1.0 g, 6.29 mmol, 1.0 eq) in methanol (25 mL), 10% palladium on charcoal (0.200 g) was added. Hydrogen was purged through reaction mixture for 2-3 h at room temperature. After completion of reaction, reaction mixture was filtered through celite-bed and washed with methanol. Filtrate was concentrated under reduced pressure to obtain 96ii (0.8 g, 98%). MS(ES): m/z 130.11 [M+H]$^+$.

Synthesis of Intermediate 96jj

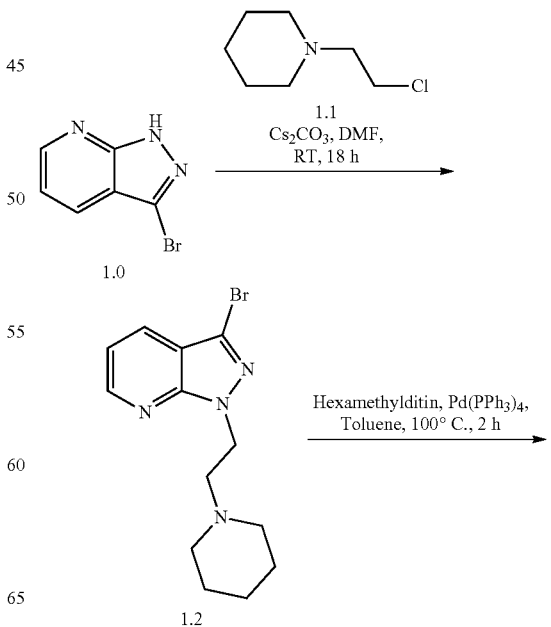

-continued

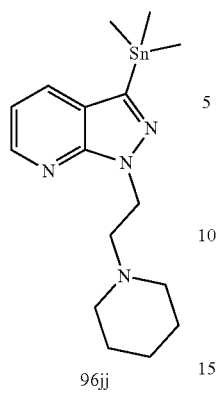

96jj

Synthesis of Compound 1.2.

A mixture of 1.0 (1.0 g, 5.05 mmol, 1.0 eq), 1.1 (0.910 g, 6.06 mmol, 1.2 eq) and cesium carbonate (3.3 g, 10.10 mmol, 2.0 eq) in N—N-Dimethylformamide (20 mL), was allowed to stir at room temperature for 18 h. After completion of reaction, reaction mixture transferred into water and product was extracted with ethyl acetate. Organic layer was combined, washed with brine solution, dried over sodium sulphate and concentrated under reduced pressure to obtain crude product which was purified by column chromatography eluting pure compound in 40-80% ethyl acetate in hexane to obtain pure 1.2 (1.3 g, 83.34%). MS (ES): m/z 310.51 [M+H]$^+$ Synthesis of Compound 1.3.

Argon was purged for 10 min through a stirred solution of 1.2 (0.5 g, 1.6 mmol, 1.0 eq), hexabutylditin (0.530 g, 1.60 mmol, 1.0 eq) in toluene (15 mL). Tetrakis(triphenylphosphine)palladium(0) (0.185 g, 0.16 mmol, 0.1 eq) was added to it and further purging done for 5 min. Reaction was allowed to stir at 100° C. for 2 h. After completion of reaction, reaction mixture was transferred into water and product was extracted with ethyl acetate. Organic layer was combined, washed with brine solution, dried over sodium sulphate and concentrated under reduced pressure to obtain 1.3 (0.710 g), MS (ES): m/z 395.63 [M+H]$^+$ Synthesis of Intermediate 96kk

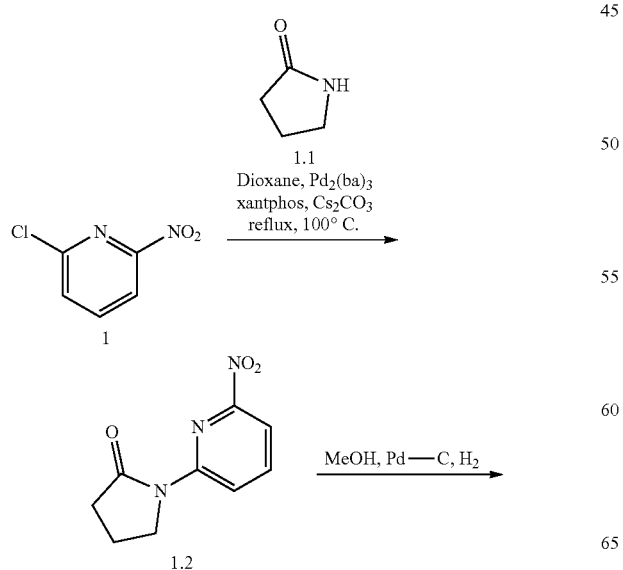

-continued

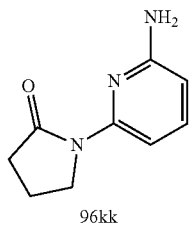

96kk

Synthesis of Compound 1.2.

Compound was synthesized using general procedure B to obtain 1.2. (1.1 g, Yield: 56.11%), MS (ES): m/z 208.07 [M+H]$^+$.

Synthesis of Intermediate 96kk.

To a solution of 1.2 (1.1 g, 5.30 mmol, 1.0 eq) in methanol (12 mL), palladium on charcoal (0.48 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 96kk. (0.620 g, 65.90%). MS (ES): m/z 178.09 [M+H]$^+$ Synthesis of Intermediate 96ll

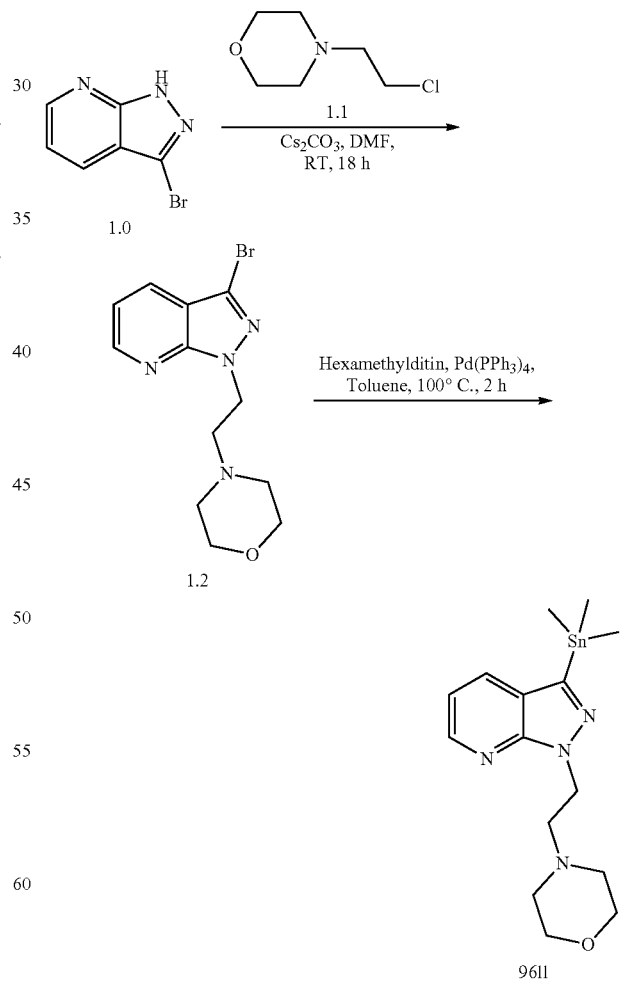

Synthesis of Compound 1.2.

A solution of 1.0 (1.0 gm, 5.05 mmol, 1.0 eq), 1.1 (0.910 g, 6.06 mmol, 1.2 eq) and Cesium carbonate (3.3 g, 10.10 mmol, 2.0 eq) in N—N-Dimethylformamide (20 mL), was allowed to stir at room temperature for 18 h. After completion of reaction, reaction mixture transferred into water and product was extracted with ethyl acetate. Organic layer was combined, washed with brine solution, dried over sodium sulphate and concentrated under reduced pressure to obtain crude product which was purified by column chromatography using silica gel (100-200 mesh) eluting pure compound in 40-80% ethyl acetate in hexane to obtain pure 1.2 (0.600 g, 38.21%). MS (ES): m/z 312.51 [M+H]$^+$.

Synthesis of Intermediate 96ll.

Argon was purged for 10 min through a stirred solution of 1.2 (0.5 g, 1.6 mmol, 1.0 eq), hexabutylditin (0.530 g, 1.60 mmol, 1.0 eq) in toluene (15 mL). Tetrakis(triphenylphosphine)palladium(0) (0.185 g, 0.16 mmol, 0.1 eq) was added to it and further purging done for 5 min. Reaction was allowed to stirred at 100° C. for 2 h. After completion of reaction, reaction mixture was transferred into water and product was extracted with ethyl acetate. Organic layer was combined, washed with brine solution, dried over sodium sulphate and concentrated under reduced pressure to obtain 96ll (0.710 g), MS (ES): m/z 397.63 [M+H]$^+$ Synthesis of Intermediate 96mm

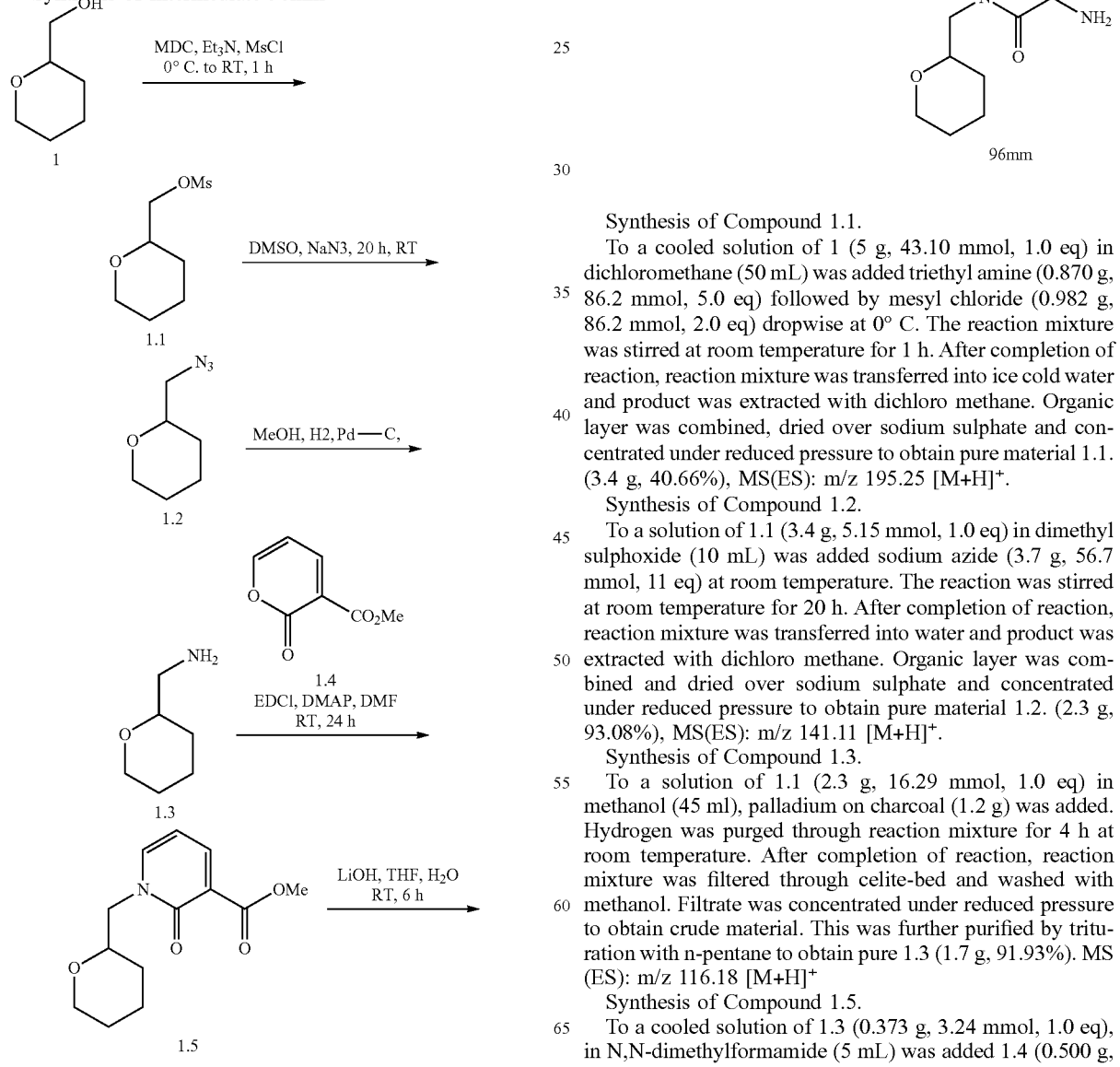

Synthesis of Compound 1.1.

To a cooled solution of 1 (5 g, 43.10 mmol, 1.0 eq) in dichloromethane (50 mL) was added triethyl amine (0.870 g, 86.2 mmol, 5.0 eq) followed by mesyl chloride (0.982 g, 86.2 mmol, 2.0 eq) dropwise at 0° C. The reaction mixture was stirred at room temperature for 1 h. After completion of reaction, reaction mixture was transferred into ice cold water and product was extracted with dichloro methane. Organic layer was combined, dried over sodium sulphate and concentrated under reduced pressure to obtain pure material 1.1. (3.4 g, 40.66%), MS(ES): m/z 195.25 [M+H]$^+$.

Synthesis of Compound 1.2.

To a solution of 1.1 (3.4 g, 5.15 mmol, 1.0 eq) in dimethyl sulphoxide (10 mL) was added sodium azide (3.7 g, 56.7 mmol, 11 eq) at room temperature. The reaction was stirred at room temperature for 20 h. After completion of reaction, reaction mixture was transferred into water and product was extracted with dichloro methane. Organic layer was combined and dried over sodium sulphate and concentrated under reduced pressure to obtain pure material 1.2. (2.3 g, 93.08%), MS(ES): m/z 141.11 [M+H]$^+$.

Synthesis of Compound 1.3.

To a solution of 1.1 (2.3 g, 16.29 mmol, 1.0 eq) in methanol (45 ml), palladium on charcoal (1.2 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 1.3 (1.7 g, 91.93%). MS (ES): m/z 116.18 [M+H]$^+$ Synthesis of Compound 1.5.

To a cooled solution of 1.3 (0.373 g, 3.24 mmol, 1.0 eq), in N,N-dimethylformamide (5 mL) was added 1.4 (0.500 g, 3.24 mmol, 1.0 eq). The reaction mixture was stirred at 0°

C. for 30 min and further stirred at room temperature for 15 min. N-Ethyl-N'-(3-dimethylaminopropyl)carbodiimide hydrochloride (0.810 g, 4.22 mmol, 1.3 eq) and 4-Dimethylaminopyridine (0.079 g, 0.649 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.5 (0.240 g, 29.49%). MS(ES): m/z 252.28 [M+H]$^+$.

Synthesis of Compound 1.6.

To a solution of 1.5 (0.240 g, 0.956 mmol, 1.0 eq), in tetrahydrofuran: water (5 mL, 2:1) was added lithium hydroxide (0.219 g, 9.56 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6 (0.210 g, 92.67%). MS(ES): m/z 238.26 [M+H]$^+$.

Synthesis of Compound 1.7.

To a solution of 1.6 (0.210 g, 0.885 mmol, 1.0 eq) in tert.butanol (5 mL) was added triethylamine (0.151 g, 1.50 mmol, 1.7 eq) and diphenyl phosphoryl azide (0.316 g, 1.15 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7 (0.172 g, 63%). MS(ES): m/z 309.38 [M+H]$^+$.

Synthesis of Intermediate 96mm.

A cooled solution of 1.7 (0.172 g, 0.55 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96mm (0.110 g, 80.59%). MS(ES): m/z 208.72 [M–HCl]$^+$.

Synthesis of Intermediate 96nn

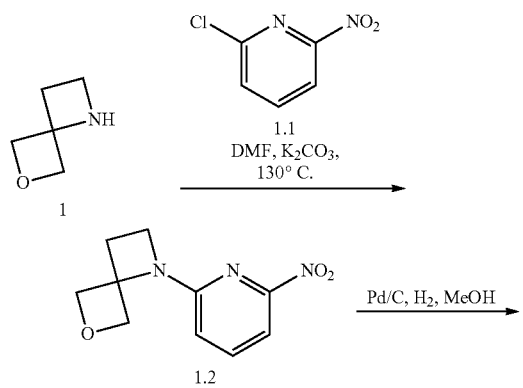

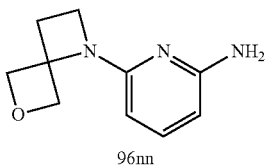

96nn

Synthesis of Compound 1.2.

A solution of compound 1 (0.500 g, 5.04 mmol, 1.0 eq) and compound 1.1 (0.878 g, 5.54 mmol, 1.1 eq) in Dimethylformamide (5 mL) was added potassium carbonate (3.47 g, 25.2 mmol, 5.0 eq) at room temperature. The reaction mixture was degassed for 10 min and heated at 130° C. for 8 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 20% ethylacetate in hexane to obtain 1.2. (0.2 g, Yield: 18.82%). MS (ES): m/z 221.22 [M+H]$^+$.

Synthesis of Intermediate 96nn.

To a solution of 1.2 (0.2 g, 0.90 mmol, 1.0 eq) in methanol (5 ml), palladium on charcoal (0.104 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96nn. (0.170 g, 98.33%). MS (ES): m/z 192.11 [M+H]$^+$ Synthesis of Intermediate 96oo

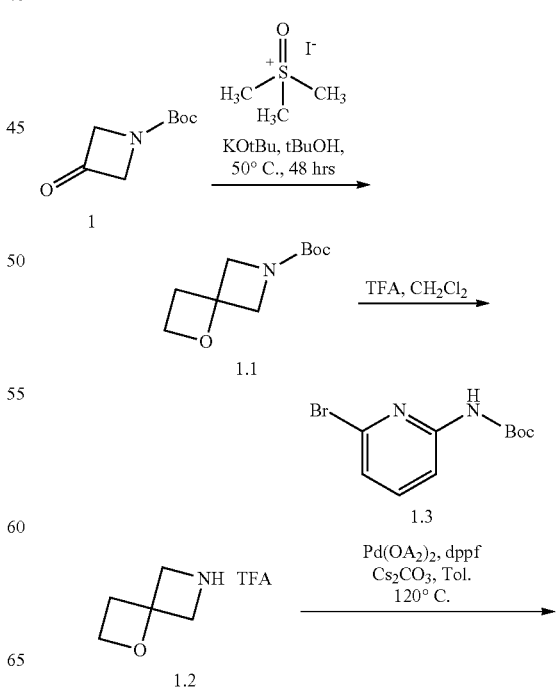

-continued

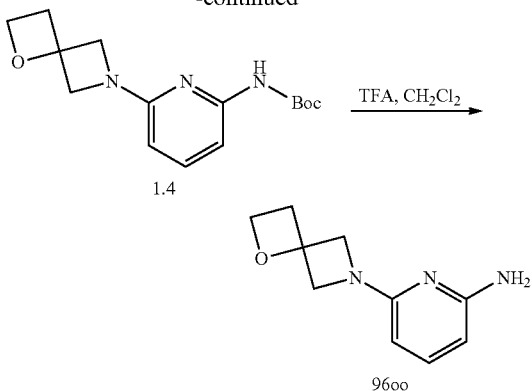

Synthesis of Intermediate 96pp

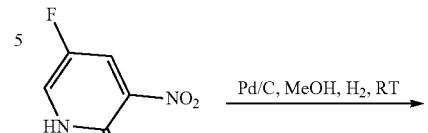

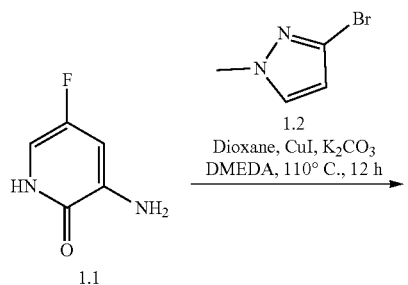

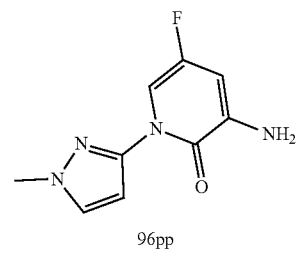

Synthesis of Compound 1.1:

To a solution of 1 (3 g, 17.55 mmol, 1.0 eq), in t-butanol was added potassium tert-butoxide (4.9 g, 43.87 mmol, 2.5 eq), trimethyl sulfoxonium iodide (9.6 g, 43.87 mmol, 2.5 eq) and stirred at 50° C. for 48 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.1 (1.5 g, 42.96%). MS(ES): m/z 200.20 [M+H]$^+$.

Synthesis of Compound 1.2:

The compound 1.1 (1.5 g, 7.53 mmol, 1.0 eq) was dissolved in dichloromethane (2 mL) and 4M HCl in dioxane (0.2 mL) was added to the reaction mixture. The reaction was stirred at room temperature for 1 h. After completion of reaction, reaction mixture was concentrated under reduced pressure to obtain crude material. This was further purified by trituration with diethyl ether to obtain pure 1.2 (0.6 g, 80.40%). MS (ES): m/z 100.1 [M+H]$^+$ Synthesis of Compound 1.4:

To a solution of 1.2 (1 g, 4.69 mmol, 1.0 eq) in toluene (20 mL) was added 1.3 (1.5 g, 5.6 mmol, 1.2 eq), Cesium carbonate (3 g, 9.38 mmol, 2.0 eq). The reaction mixture was degassed for 10 min. under argon atmosphere, then Palladium acetate(0) (0.052 g, 0.234 mmol, 0.05 eq) and 1,1'-Ferrocenediyl-bis(diphenylphosphine) (0.259.9 g, 0.469 mmol, 0.1 eq) were added, again degassed for 5 min. The reaction was stirred at 120° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluent to obtain pure 1.4 (0.450, 15.31%). MS(ES): m/z 292.3 [M+H]$^+$.

Synthesis of Compound 1.5.

The compound 1.4 (0.45 g, 1.5 mmol, 1.0 eq) was dissolved in dichloromethane (2 mL) and 4M HCl in dioxane (0.2 mL) was added to the reaction mixture. The reaction was stirred at room temperature for 1 h. After completion of reaction, reaction mixture was concentrated under reduced pressure to obtain crude material. This was further purified by trituration with diethyl ether to obtain pure 1.5 (0.24 g, 81.26%). MS (ES): m/z 192.23 [M+H]$^+$ Synthesis of Compound 1.1.

To a solution of 1 (1 g, 6.33 mmol, 1.0 eq) in methanol (10 mL), palladium on charcoal (0.1 g) was added. Hydrogen was purged through reaction mixture for 24 h at room temperature. After completion of reaction, reaction mixture was filtered through celite-bed and washed with methanol. Filtrate was concentrated under reduced pressure to obtain 1.1 (0.75 g, 93.00%). MS(ES): m/z 129.11 [M+H]$^+$.

Synthesis of Intermediate 96pp.

To a solution of 1.1 (1 g, 7.81 mmol, 1.0 eq) in 1,4-dioxane (100 mL), 1.2 (1.88 g, 11.72 mmol, 1.5 eq) was added. The reaction mixture was degassed for 10 min under argon atmosphere followed by addition of potassium carbonate (1.9 g, 15.62 mmol, 2.0 eq), N,N-dimethylethylenediamine (0.38 g, 3.125 mmol, 0.4 eq), and copper iodide (0.19 g, 1.56 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 3% methanol in dichloromethane to obtain 96pp (0.40 g, Yield: 24.24%). MS (ES): m/z 208.20 [M+H]$^+$.

Synthesis of Intermediate 96qq

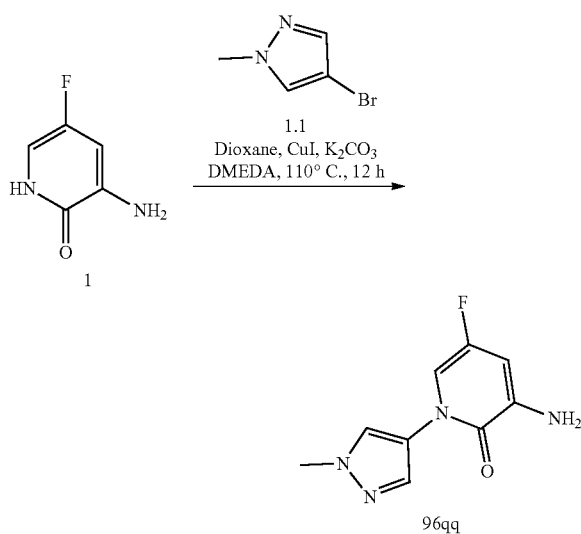

Synthesis of Intermediate 96qq.

To a solution of 1 (1 g, 7.81 mmol, 1.0 eq) in 1,4-dioxane (100 mL), 1.1 (1.8 g, 11.57 mmol, 1.5 eq) was added. The reaction mixture was degassed for 10 min under argon atmosphere followed by addition of potassium carbonate (2.1 g, 15.62 mmol, 2.0 eq), N,N-dimethylethylenediamine (0.274 g, 3.21 mmol, 0.4 eq), and copper iodide (0.296 g, 1.56 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96qq (0.610 g, Yield: 37.53%). MS (ES): m/z 209.08 M+H]$^+$.

Synthesis of Intermediate 96rr.

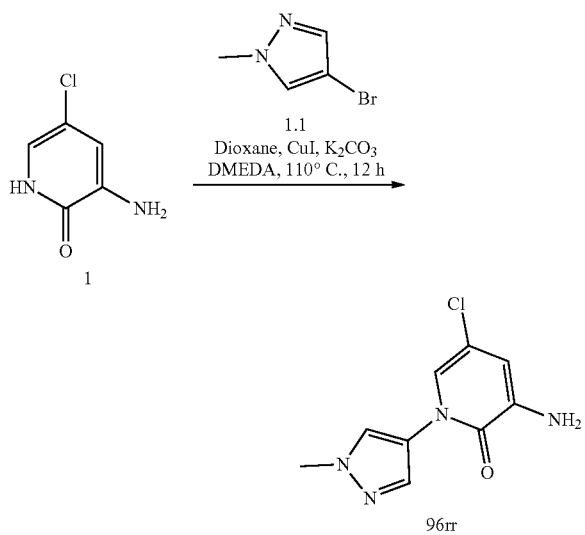

Synthesis of Intermediate 96rr.

To a solution of 1 (1 g, 6.92 mmol, 1.0 eq) in 1,4-dioxane (100 mL), 1.1 (1.6 g, 10.38 mmol, 1.5 eq) was added. The reaction mixture was degassed for 10 min under argon atmosphere followed by addition of potassium carbonate (1.9 g, 13.84 mmol, 2.0 eq), N,N-dimethylethylenediamine (0.24 g, 2.76 mmol, 0.4 eq), and copper iodide (0.26 g, 1.38 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96rr (0.70 g, Yield: 45.04%). MS (ES): m/z 225.65 [M+H]$^+$.

Synthesis of Intermediate 96ss.

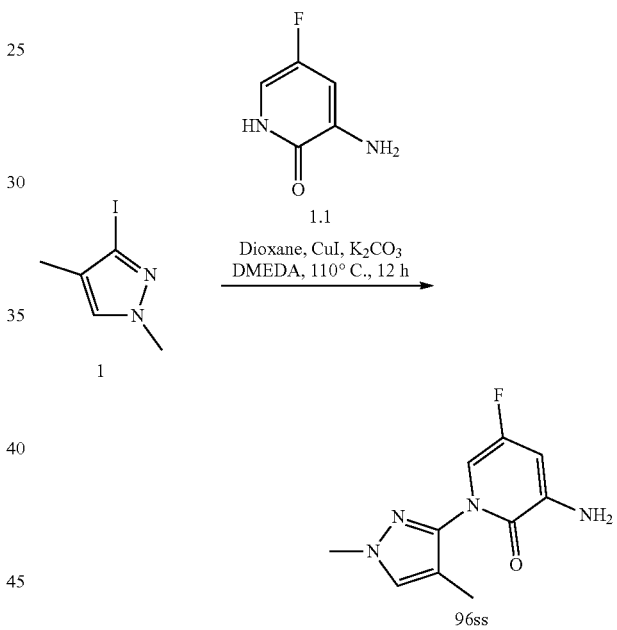

Synthesis of Intermediate 96ss.

To a solution of 1 (0.8 g, 3.60 mmol, 1 eq) in 1,4-dioxane (40 mL), 1.1 (0.599 g, 4.68 mmol, 1.3 eq) was added. The reaction mixture was degassed for 10 min under argon atmosphere followed by addition of potassium carbonate (1.24 g, 9.0 mmol, 2.5 eq), N,N-dimethylethylenediamine (0.079 g, 0.9 mmol, 0.25 eq), and copper iodide (0.102 g, 0.54 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96ss (0.045 g, Yield: 5.62%). MS (ES): m/z 223.10 [M+H]$^+$

Synthesis of Intermediate 96tt.

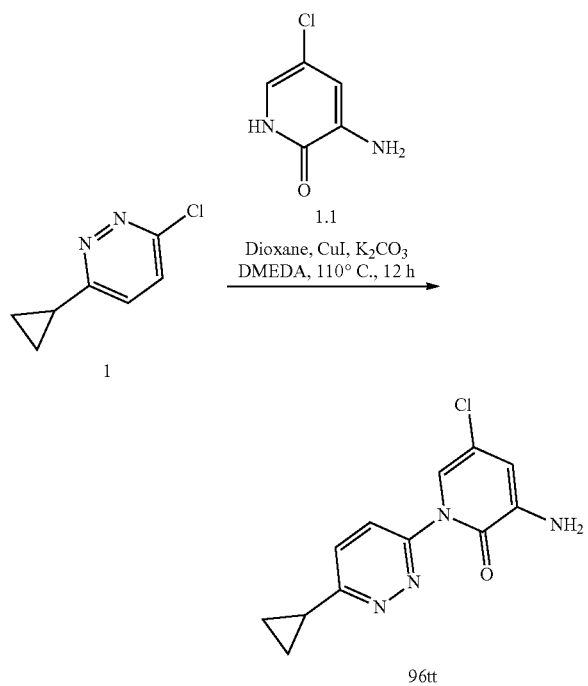

Synthesis of Intermediate 96tt.

To a solution of 1 (0.850 g, 5.50 mmol, 1 eq) and 1.1 (1.03 g, 7.15 mmol, 1.3 eq) in 1,4-dioxane (10 mL) was added potassium carbonate (1.51 g, 11.0 mmol, 2.0 eq) and degassed with argon for 15 min. Copper iodide (0.209 g, 1.1 mmol, 0.2 eq) and 1,2-dimethylethylenediamine (0.193 g, 2.2 mmol, 0.4 eq) was added and reaction mixture again degassed with argon for 5 min followed by heating at 110° C. for 12 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.7% methanol in dichloromethane to obtain pure 96tt (0.121 g, 8.38%). MS(ES): m/z 263.70 [M+H]$^+$.

Synthesis of Intermediate 96uu.

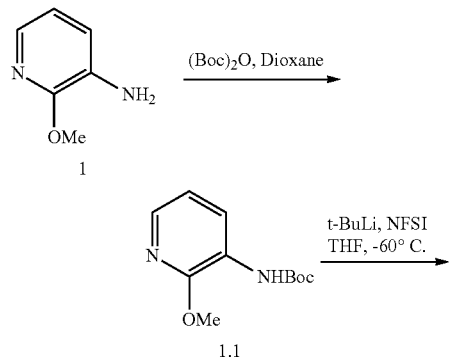

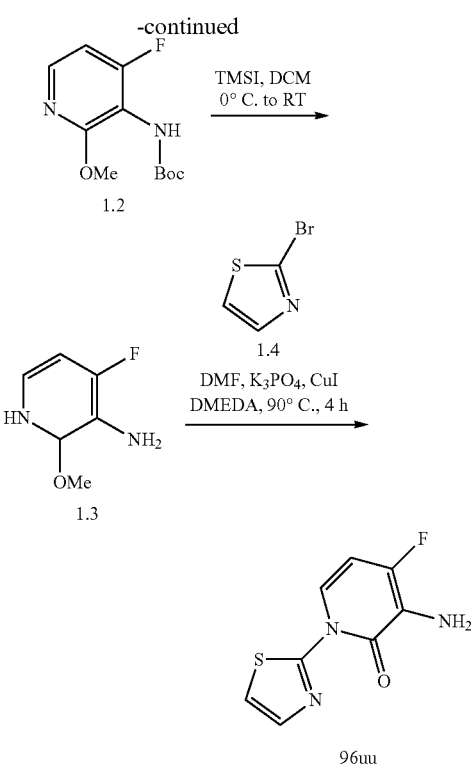

Synthesis of Compound 1.1.

To a stirred solution of 1 (10.0 g, 80.64 mmol, 1.0 eq) in 1,4-dioxane (100 mL) was added di-tert-butyl carbonate (1.595 g, 11.56 mmol, 1.2 eq) at room temperature under N$_2$ and the reaction mixture was heated at 100° C. for 14 h. After completion of reaction, reaction mixture was transferred into cold water and product was extracted with ethyl acetate. The combined organic phase was dried over sodium sulphate and concentrated under reduced pressure to obtain crude material. This was further purified by column chromatography and compound was eluted in 1% ethyl acetate in hexane to obtain pure 1.1 (12.0 g, 66.66%). MS(ES): m/z 225.44 [M+H]$^+$.

Synthesis of Compound 1.2.

To a stirred solution of 1.1 (10.0 g, 44.64 mmol, 1.0 eq) in dry tetrahydrofuran (200 mL) was added ter-butyl lithium (105 mL, 1.7 M in pentane, 178.57 mmol, 4.0 eq) at −70° C. under Ar dropwise over 20 mins. The reaction mixture was allowed to warm to −25° C. over 40 mins, stirred for 10 mins and recooled to −70° C. A solution of N-fluorobenzenesulfonamide (15.0 g, 47.61 mmol, 1.06 eq) in dry tetrahydrofuran (50 mL) was added dropwise over 5 mins and the mixture was allowed to warm to −20° C. over 40 mins. The reaction was quenched by slow addition of cold water and the product was extracted with ethyl acetate. The combined organic layer dried over sodium sulphate and concentrated under reduced pressure to obtain crude material. This was further purified by column chromatography and compound was eluted in 4% ethyl acetate in hexane to obtain pure 1.2 (5.2 g, 48.06%). MS(ES): m/z 243.425 [M+H]$^+$.

Synthesis of Compound 1.3.

To a stirred solution of 1.2 (5.0 g, 20.66 mmol, 1.0 eq) in dichloromethane (50 mL) was added a solution of trimethyl silyl iodide (4.6 g, 22.72 mmol, 1.1 eq) in dichloromethane (20 mL) dropwise at 0° C. under N$_2$ and the reaction mixture was stirred at room temperature for 4 h. The reaction mixture was concentrated under reduced pressure. The residue was mixed with dichloromethane (10 mL) and some wet crystals of sodium thiosulfate were added. The mixture was stirred until the brown colour disappeared. The mixture was filtered and the solid residue obtained was stirred with 20% methanol in dichloromethane, filtered and the filtrate was concentrated under reduced pressure to obtain 1.3 (1.0 g, 34.42%).
$^1$H NMR (DMSO-$d_6$, 400 MHZ): 11.56 (brs, 1H), 6.76-6.72 (t, J=7.2 Hz, 1H), 6.24-6.20 (t, J=7.6 Hz, 1H), 4.76 (s, 2H).

Synthesis of Intermediate 96uu.

To a degassed solution of 1.3 (0.650 g, 5.08 mmol, 1.0 eq) and 1.4 (1.33 g, 7.62 mmol, 1.5 eq) in dimethylformamide (16 mL) was added potassium orthophosphate (2.15 g, 10.15 mmol, 2.0 eq), cuprous iodide (0.193 g, 1.02 mmol, 0.2 eq) and N, N'-dimethylethylene diamine (0.180 g, 2.03 mmol, 0.4 eq) and the reaction mixture was heated at 90° C. for 4 h under N$_2$. Reaction mixture was cooled to room temperature filtered and the filtrate was concentrated under reduced pressure to obtain the residue which was further purified by column chromatography and compound was eluted in 8.5% ethyl acetate in hexane to obtain pure 96uu (0.100 g, 9.35%).
$^1$H NMR (DMSO-$d_6$, 400 MHZ): 8.20-8.15 (t, J=7.2 Hz, 1H), 7.80-7.78 (d, J=3.6 Hz, 1H), 7.67-7.60 (d, J=3.6 Hz, 1H), 6.72-6.67 (t, J=8.4 Hz, 1H), 5.41 (s, 2H).

Synthesis of Intermediate 96vv.

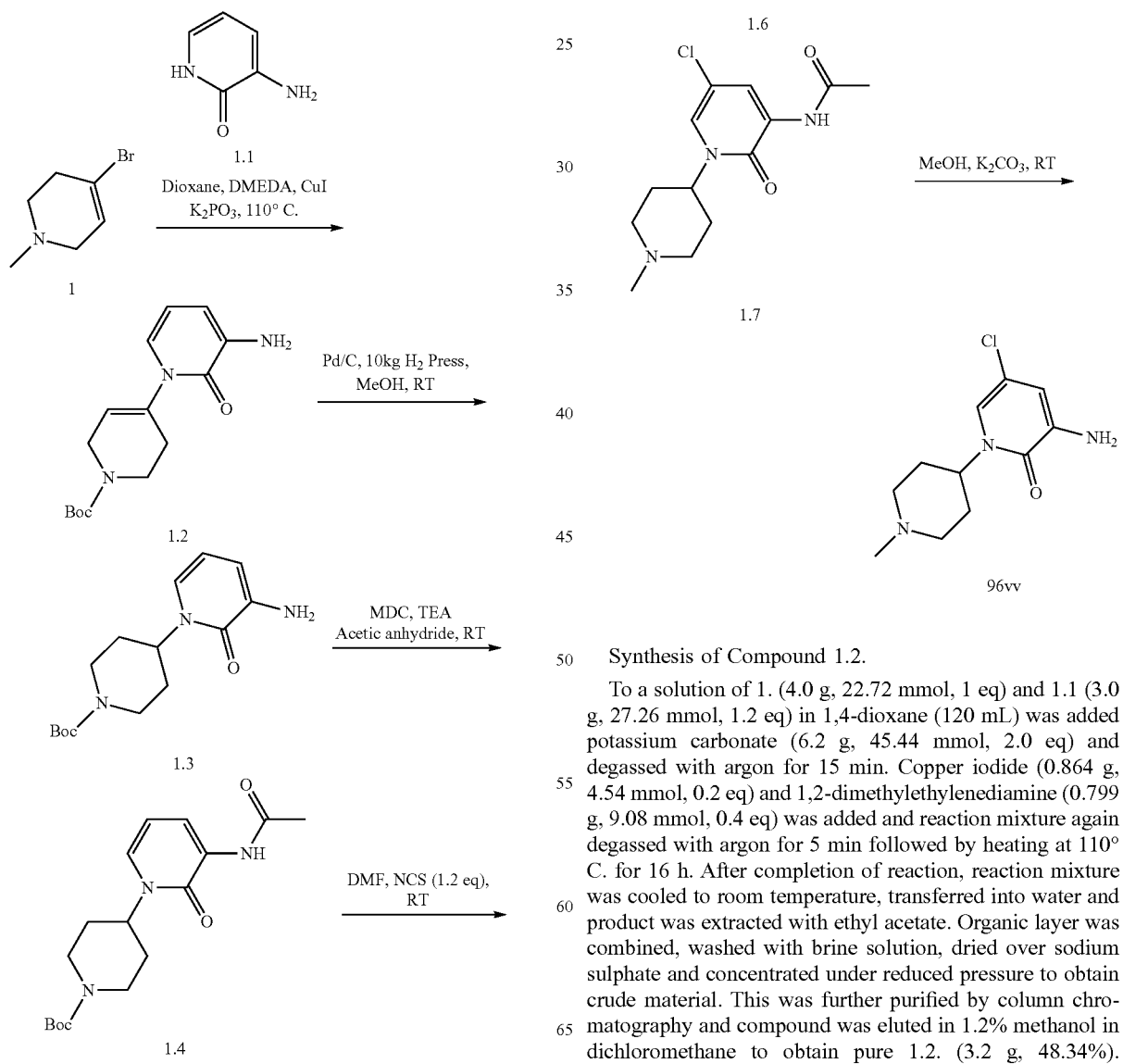

Synthesis of Compound 1.2.

To a solution of 1. (4.0 g, 22.72 mmol, 1 eq) and 1.1 (3.0 g, 27.26 mmol, 1.2 eq) in 1,4-dioxane (120 mL) was added potassium carbonate (6.2 g, 45.44 mmol, 2.0 eq) and degassed with argon for 15 min. Copper iodide (0.864 g, 4.54 mmol, 0.2 eq) and 1,2-dimethylethylenediamine (0.799 g, 9.08 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 1.2. (3.2 g, 48.34%). MS(ES): m/z 292.16 [M+H]$^+$.

Synthesis of Compound 1.3.

To a solution of 1.2 (3.2 g, 10.99 mmol, 1.0 eq) in methanol (60 ml), palladium on charcoal (1.5 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 1.3. (2.0 g, 62.07%). MS (ES): m/z 294.18 [M+H]$^+$ Synthesis of Compound 1.4

To a solution of 1.3 (2.0 g, 6.82 mmol, 1.0 eq) in dichloromethane (20 mL), were added triethylamine (1.3 g, 13.64 mmol, 2. eq) and acetic anhydride (3.4 g, 34.1 mmol, 5.0 eq) at 0° C. The reaction mixture was stirred at room temperature for 3 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.4. (1.7 g, Yield: 74.35%). MS (ES): m/z 336.19 [M+H]$^+$.

Synthesis of Compound 1.5.

To a solution of 1.4 (1.5 g, 4.47 mmol, 1.0 eq) in dichloromethane (20 mL), were added N-Iodo-succinimide (1.2 g, 5.36 mmol, 1.2. eq) at 0° C. The reaction mixture was stirred at room temperature for overnight. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.5. (0.810 g, Yield: 48.97%). MS (ES): m/z 370.15 [M+H]$^+$ Synthesis of Compound 1.6.

A cooled solution of 1.5 (0.810 g, 2.19 mmol, 1 eq) in dioxane (12 mL) was added 4N hydrochloric acid in dioxane (6 mL) as a dropwise. The reaction mixture was stirred at room temperature for 2 h. After completion of reaction, reaction mixture was concentrated under reduced pressure to obtain pure 1.6. (0.726 g, 98.42%). MS(ES): m/z 307.07 [M+HCl]$^+$ Synthesis of Compound 1.7.

To a solution of 1.6 (0.726 g, 2.37 mmol, 1.0 eq) in methanol (20 mL), were added Formaldehyde (0.142 g, 4.74 mmol, 2.0 eq) and Formic acid (2 ml). The reaction mixture was stirred at 80° C. for 1 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 4% methanol in dichloromethane to obtain 1.7. (0.510 g, Yield: 75.80%). MS (ES): m/z 284.11 [M+H]$^+$ Synthesis of Intermediate 96vv.

To a solution of 1.7 (0.510 g, 1.79 mmol, 1.0 eq) in methanol (10 mL), were added potassium carbonate (0.494 g, 3.58 mmol, 2.0 eq) The reaction mixture was stirred at room temperature for 4 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 96vv. (0.260 g, Yield: 59.85%). MS (ES): m/z 242.10 [M+H]$^+$ Synthesis of Intermediate 96ww.

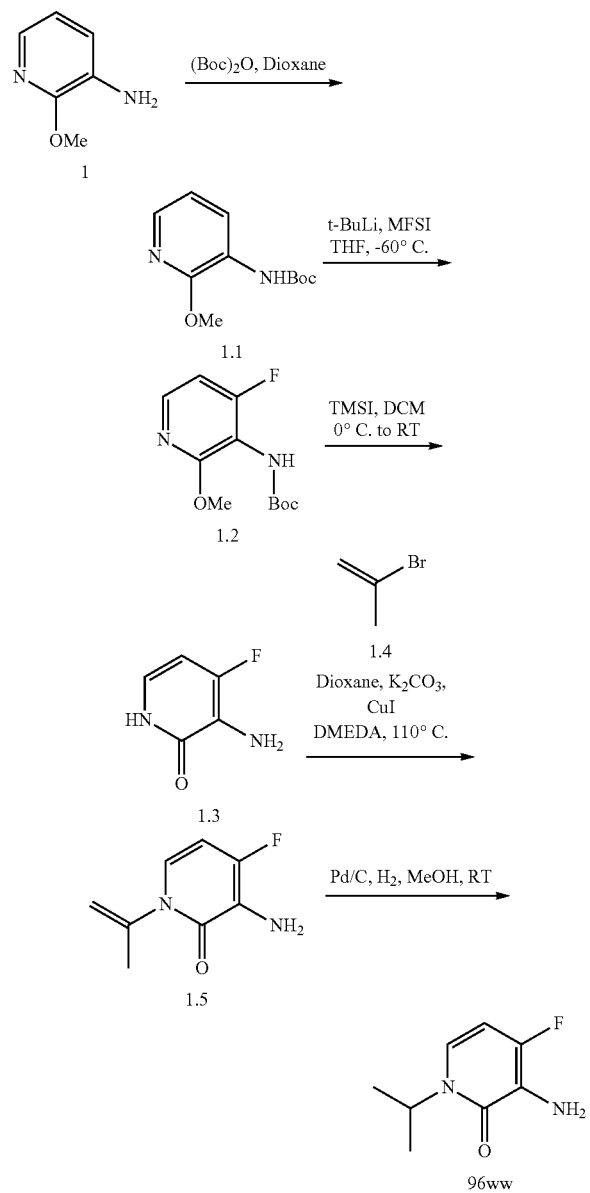

Synthesis of Compound 1.1.

To a stirred solution of 1 (10.0 g, 80.64 mmol, 1.0 eq) in 1,4-dioxane (100 mL) was added di-tert-butyl carbonate (1.595 g, 11.56 mmol, 1.2 eq) at room temperature under N$_2$ and the reaction mixture heated at 100° C. for 14 h. The reaction mixture was transferred into cold water and product was extracted with ethyl acetate. The combined organic phase was dried over sodium sulphate and concentrated under reduced pressure to obtain crude material. This was further purified by column chromatography and compound was eluted in 1% ethyl acetate in hexane to obtain pure 1.1 (12.0 g, 66.66%). MS(ES): m/z 225.44 [M+H]$^+$.

Synthesis of Compound 1.2.

To a stirred solution of 1.1 (10.0 g, 44.64 mmol, 1.0 eq) in dry tetrahydrofuran (200 mL) was added ter-butyl lithium (105 mL, 1.7 M in pentane, 178.57 mmol, 4.0 eq) at −70° C. under argon dropwise over 20 mins. The reaction mixture was allowed to warm to −25° C. over 40 mins, stirred for 10 mins and recooled to −70° C. A solution of N-fluorobenzenesulfonamide (15.0 g, 47.61 mmol, 1.06 eq) in dry tetrahydrofuran (50 mL) was added dropwise over 5 mins and the mixture was allowed to warm to −20° C. over 40 mins. The reaction was quenched by slow addition of cold water and the product was extracted with ethyl acetate. The combined organic phase was dried over sodium sulphate and concentrated under reduced pressure to obtain crude material. This was further purified by column chromatography and compound was eluted in 4% ethyl acetate in hexane to obtain pure 1.2 (5.2 g, 48.06%). MS(ES): m/z 243.425 [M+H]$^+$.

Synthesis of Compound 1.3.

To a stirred solution of 1.2 (5.0 g, 20.66 mmol, 1.0 eq) in dichloromethane (50 mL) was added a solution of trimethyl silyl iodide (4.6 g, 22.72 mmol, 1.1 eq) in dichloromethane (20 mL) dropwise at 0° C. under $N_2$ and the reaction mixture was stirred at room temperature for 4 h. The reaction mixture was evaporated under reduced pressure. The residue was dissolved in dichloromethane and some wet crystals of sodium thiosulfate were added. The mixture was stirred until the brown colour disappeared. The mixture was filtered and the solid residue was washed with 30% ethyl acetate in hexane, dried well to obtain 1.3 (1.0 g, 34.42%). $^1$H NMR (DMSO-$d_6$, 400 MHZ): 11.56 (brs, 1H), 6.76-6.72 (t, J=7.2 Hz, 1H), 6.24-6.20 (t, J=7.6 Hz, 1H), 4.76 (s, 2H).

Synthesis of Compound 1.5.

To a degassed solution of 1.4 (0.600 g, 4.68 mmol, 1.0 eq) in 1,4-dioxane (12 mL) were added 1.4 (0.680 g, 5.63 mmol, 1.2 eq), potassium carbonate (1.6 g, 11.72 mmol, 2.5 eq), cuprous iodide (0.178 g, 0.94 mmol, 0.2 eq) and N, N'-dimethylethylene diamine (0.163 g, 1.84 mmol, 0.4 eq) and the reaction mixture was heated at 100° C. for 14 h under $N_2$. Reaction mixture was cooled to room temperature filtered and the filtrate was concentrated under reduced pressure to obtain the residue which was further purified by column chromatography and compound was eluted in 2.0% methanol in dichloromethane to obtain pure 1.5. (0.250 g, 31.76%). MS(ES): m/z 169.14 [M+H]$^+$.

Synthesis of Intermediate 96ww.

A mixture of 1.5 (0.250 g, 1.49 mmol, 1.0 eq) and palladium on charcoal (0.150 g, 5% on C) in methanol (5 mL) was stirred under hydrogen at room temperature for 4 h. The reaction mixture was filtered through celite and the filtrate was concentrated under vacuum to obtain pure 96ww. (0.220 g, 86.91%). MS(ES): m/z 171.14 [M+H]$^+$.

Synthesis of Intermediate 96xx.

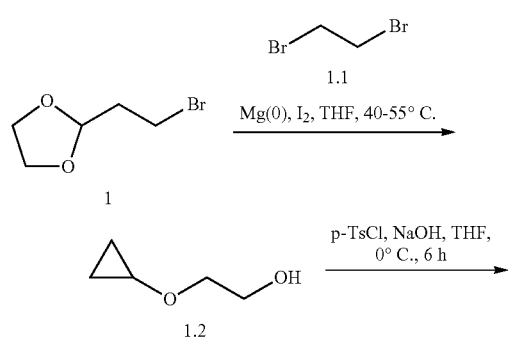

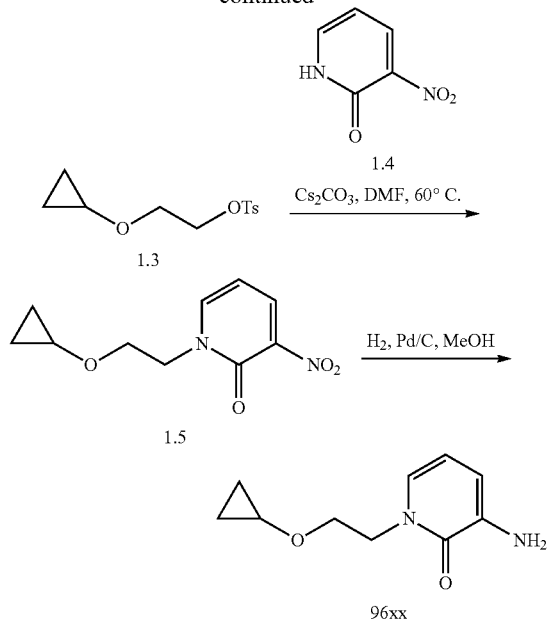

Synthesis of Compound 1.2.

To a solution of 1. (10 g, 55.24 mmol, 1.0 eq) in tetrahydrofuran (25 mL) was added magnesium powder (8.48 g, 353.53 mmol, 6.4 eq) and iodine (catalytic). 1.1 (44.2 g, 236.42 mmol, 4.28 eq) was added dropwise to the solution. The reaction mixture was stirred at 40-50° C. for 16 h. After completion of reaction, reaction mixture transferred into water and product was extracted with ethyl acetate. Organic layer was combined, dried over sodium sulphate and concentrated under reduced pressure to obtain crude material. This was further purified by 40% ethyl acetate in hexane to obtain 1.2 (2.5 g, Yield: 44.31%). MS (ES): m/z 103.07 [M+H]

Synthesis of Compound 1.3.

To a solution of 1.2 (2.5 g, 24.50 mmol, 1.0 eq) in tetrahydrofuran (50 mL) was added sodium hydroxide (2.94 g, 73.5 mmol, 3.0 eq) followed by p-Toluenesulfonyl chloride (5.12 g, 26.95 mmol, 1.1 eq) at 0° C. The reaction mixture was stirred for 6 h at 0° C. After completion of reaction, reaction mixture transferred into water and product was extracted with ethyl acetate. Organic layer was combined, dried over sodium sulphate and concentrated under reduced pressure to obtain crude material. This was further purified by 10% ethyl acetate in hexane to obtain 1.3. (1.0 g, Yield: 16%). MS (ES): m/z 257.08 [M+H]$^+$.

Synthesis of Compound 1.5.

To a solution of 1.3 (1 g, 3.90 mmol, 1.0 eq) in dimethylformamide (10 mL), 1.4 (0.546 g, 3.90 mmol, 1.0 eq) and cesium carbonate (1.26 g, 3.90 mmol, 1 eq) were added. The reaction mixture was heated at 60° C. for 4 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 20% ethyl acetate in hexane as eluent to obtain pure 1.5. (0.7 g, 80.02%). MS(ES): m/z 199.18 [M+H]$^+$.

Synthesis of Intermediate 96xx.

To a solution of 1.5 (0.700 g, 3.12 mmol, 1.0 eq) in palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 96xx. (0.5 g, 82.45%). MS(ES): m/z 195.1 [M+H]$^+$.

Synthesis of Intermediate 96yy.

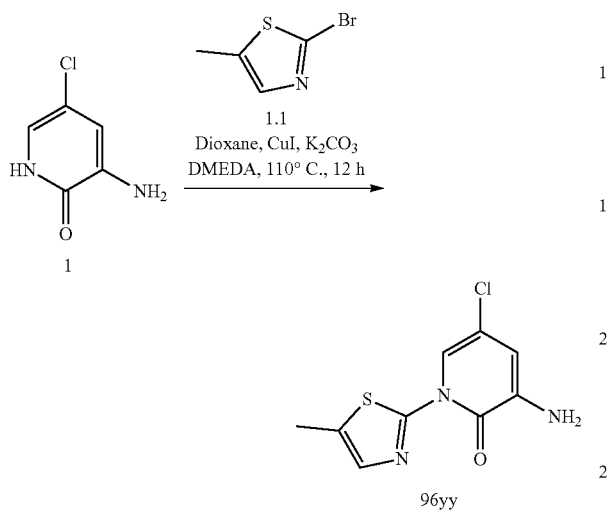

Synthesis of Intermediate 96yy.

To a solution of 1 (1 g, 6.92 mmol, 1.0 eq) in 1,4-dioxane (10 mL), 1.1. (1.3 g, 7.61 mmol, 1.1 eq) was added. The reaction mixture was degassed for 10 min under argon atmosphere followed by addition of potassium carbonate (1.9 g, 13.84 mmol, 2.0 eq), N,N-dimethylethylenediamine (0.24 g, 2.76 mmol, 0.4 eq), and copper iodide (0.26 g, 1.38 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96yy (0.61 g, Yield: 36.48%). MS (ES): m/z 242.69 [M+H]$^+$.

Synthesis of Intermediate 96zz.

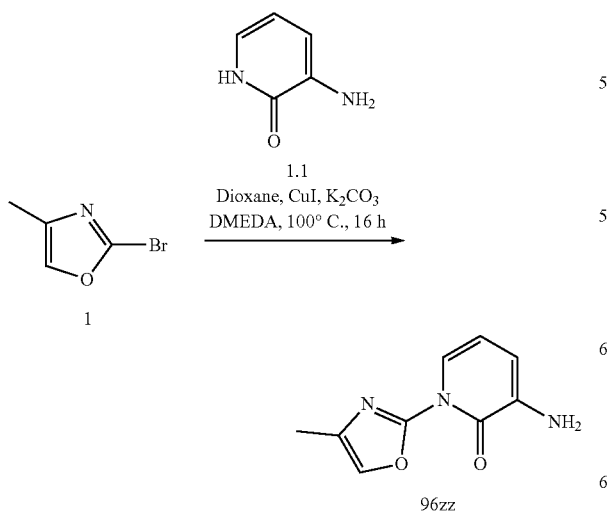

Synthesis of Compound 1.2.

To a solution of 1. (0.300 g, 1.85 mmol, 1 eq) and 1.1 (0.244 g, 2.22 mmol, 1.2 eq) in 1,4-dioxane (10 mL) was added potassium carbonate (0.510 g, 3.77 mmol, 2.0 eq) and degassed with argon for 15 min. Copper iodide (0.703 g, 3.77 mmol, 0.2 eq) and 1,2-dimethylethylenediamine (0.065 g, 0.74 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 1.2 (0.090 g, 25.42%). MS(ES): m/z 192.19 [M+H]$^+$.

Synthesis of Intermediate 96aaa.

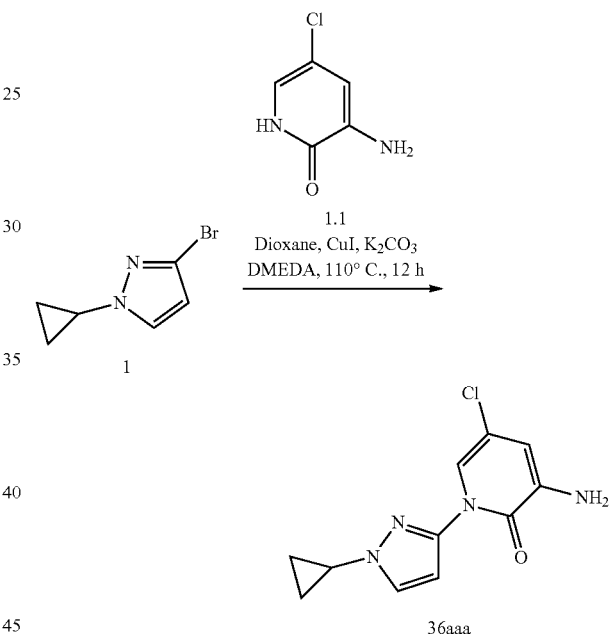

Synthesis of Compound 1.

Compound was synthesized as per I-89 to obtain 1.

Synthesis of Compound 36aaa.

To a solution of 1 (0.600 g, 3.21 mmol, 1.0 eq) and 1.1 (0.417 g, 2.89 mmol, 0.9 eq) in 1,4-dioxane (6 mL) was added potassium carbonate (0.886 g, 6.42 mmol, 2.0 eq) and degassed with argon for 15 min. Copper iodide (0.091 g, 0.481 mmol, 0.15 eq) and 1,2-dimethylethylenediamine (0.084 g, 0.962 mmol, 0.3 eq) was added and reaction mixture again degassed with argon for 5 min followed by heating at 110° C. for 12 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.0% methanol in dichloromethane to obtain pure 36aaa (0.200 g, 24.87%). MS(ES): m/z 251.69 [M+H]$^+$.

Synthesis of Intermediate 96bbb.

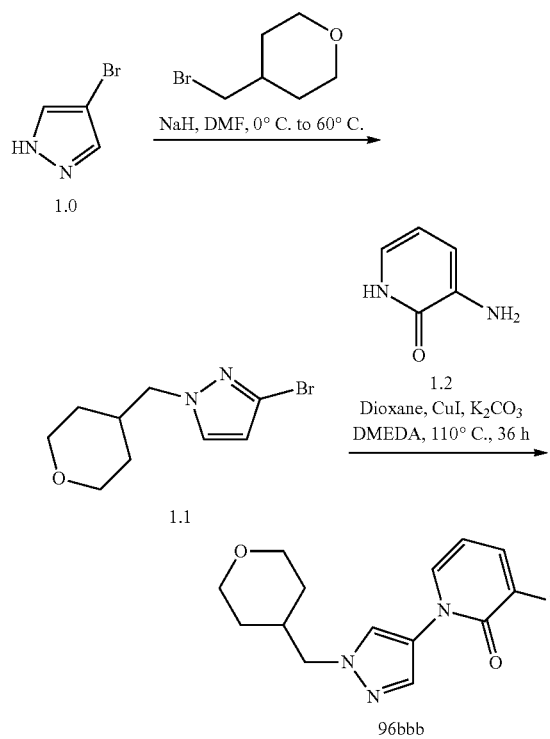

Synthesis of Compound 1.1.

To a solution of compound 1 (1.0 g, 6.80 mmol, 1.0 eq) in N,N Dimethylformamide (10 mL), at 0° C. was added sodium hydride (0.323 g, 8.092 mmol, 1.19 eq) portionwise and allowed to stir at 0° C. for 60 min followed by addition of 4-(bromomethyl)tetrahydro-2H-pyran (1.32 g, 7.41 mmol, 1.09 eq) dropwise. Reaction mixture was heated at 60° C. for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and product was eluted in hexane to obtain pure 1.1 (0.630 g, 37.78%) MS(ES): m/z 246.12.[M+H]$^+$.

Synthesis of Intermediate 96bbb.

To a solution of 1.1 (0.630 g, 2.57 mmol, 1.0 eq) and 1.2 (0.367 g, 3.34 mmol, 1.3 eq) in 1,4-dioxane (10 mL) was added potassium carbonate (0.710 g, 5.14 mmol, 2.0 eq) and degassed with argon for 15 min. Copper iodide (0.097 g, 0.514 mmol, 0.2 eq) and 1,2-dimethylethylenediamine (0.090 g, 1.02 mmol, 0.4 eq) was added and reaction mixture again degassed with argon for 5 min followed by heating at 110° C. for 36 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 4.0% methanol in dichloromethane to obtain pure 96bbb (0.260 g, 36.88.00%). MS (ES): m/z 275.32 [M+H]$^+$.

Synthesis of Intermediate 96ccc.

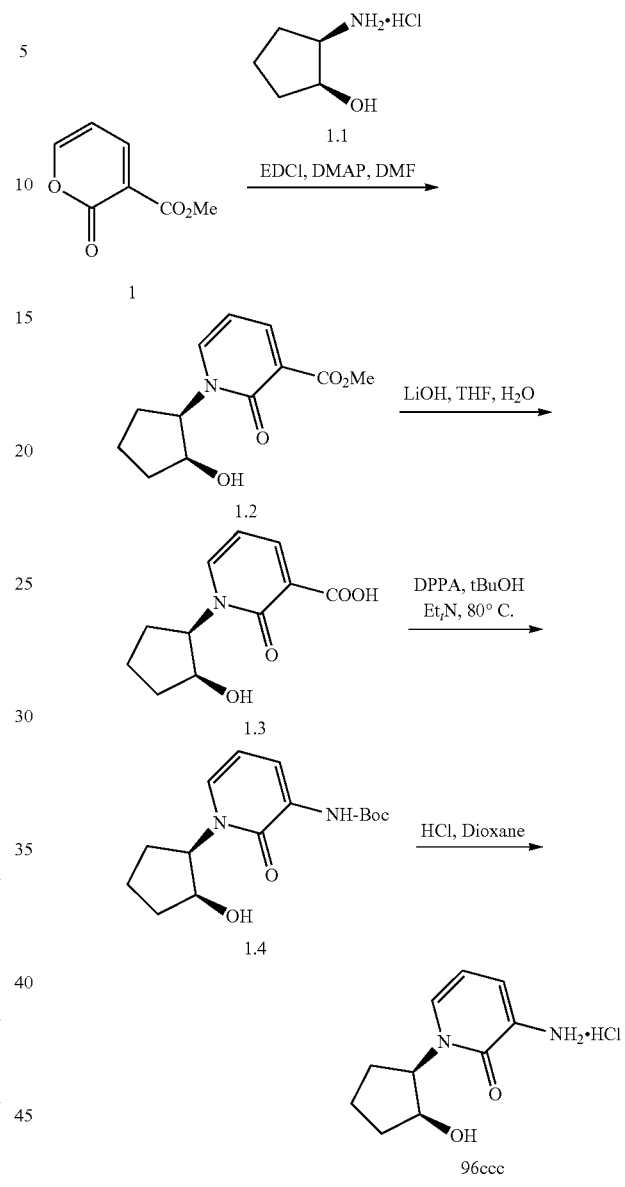

Synthesis of Compound 1.2.

To a cooled solution of 1 (0.7 g, 4.54 mmol, 1.0 eq), in N,N-dimethylformamide (10 mL) was added 1.1 (0.625 g, 4.54 mmol, 1.0 eq). The reaction mixture was stirred at 0° C. for 6 min and further stirred at room temperature for 15 min. N-Ethyl-N'-(3-dimethylaminopropyl)carbodiimide hydrochloride (1.131 g, 5.90 mmol, 1.3 eq) and 4-Dimethylaminopyridine (0.139 g, 1.135 mmol, 0.25 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.450 g, 41.76%). MS(ES): m/z 238.26 [M+H]$^+$.

Synthesis of Compound 1.3.

To a solution of 1.2 (0.45 g, 1.90 mmol, 1.0 eq), in tetrahydrofuran: water (8 mL, 2:1) was added lithium hydroxide (0.362 g, 15.1 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.36 g, 85.03%). MS(ES): m/z 224.23 [M+H]$^+$.

Synthesis of Compound 1.4.

To a solution of 1.3 (0.36 g, 1.61 mmol, 1.0 eq) in tert.butanol (6 mL) was added triethylamine (0.277 g, 2.74 mmol, 1.7 eq) and diphenyl phosphoryl azide (0.576 g, 2.093 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.320 g, 67.41%). MS(ES): m/z 295.35 [M+H]$^+$.

Synthesis of Intermediate 96ccc.

A cooled solution of 1.4 (0.320 g, 1.09 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96ccc. (0.24 g, 95.70%). MS(ES): m/z 231.69 [M+HCl]$^+$.

Synthesis of Intermediate 96ddd.

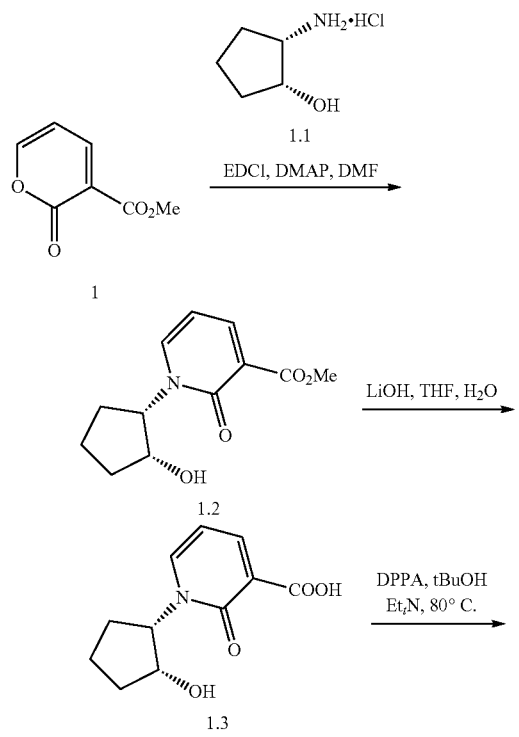

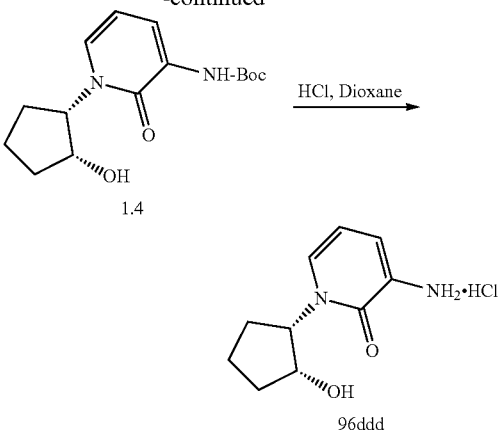

Synthesis of Compound 1.2.

To a cooled solution of 1 (0.7 g, 4.54 mmol, 1.0 eq), in N,N-dimethylformamide (10 mL) was added 1.1 (0.625 g, 4.54 mmol, 1.0 eq). The reaction mixture was stirred at 0° C. for 6 min and further stirred at room temperature for 15 min. N-Ethyl-N'-(3-dimethylaminopropyl)carbodiimide hydrochloride (1.131 g, 5.90 mmol, 1.3 eq) and 4-Dimethylaminopyridine (0.1$^{39}$ g, 1.135 mmol, 0.25 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.450 g, 41.76%). MS(ES): m/z 238.26 [M+H]$^+$.

Synthesis of Compound 1.3.

To a solution of 1.2 (0.45 g, 1.90 mmol, 1.0 eq), in tetrahydrofuran: water (8 mL, 2:1) was added lithium hydroxide (0.362 g, 15.1 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.36 g, 85.03%). MS(ES): m/z 224.23 [M+H]$^+$.

Synthesis of Compound 1.4.

To a solution of 1.3 (0.36 g, 1.61 mmol, 1.0 eq) in tert.butanol (6 mL) was added triethylamine (0.277 g, 2.74 mmol, 1.7 eq) and diphenyl phosphoryl azide (0.576 g, 2.093 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.320 g, 67.41%). MS(ES): m/z 295.35 [M+H]$^+$.

Synthesis of Intermediate 96ddd.

To a cooled solution of 1.4 (0.320 g, 1.09 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96ddd. (0.24 g, 95.70%). MS(ES): m/z 231.69 [M+HCl]+.

Synthesis of Intermediate 96eee.

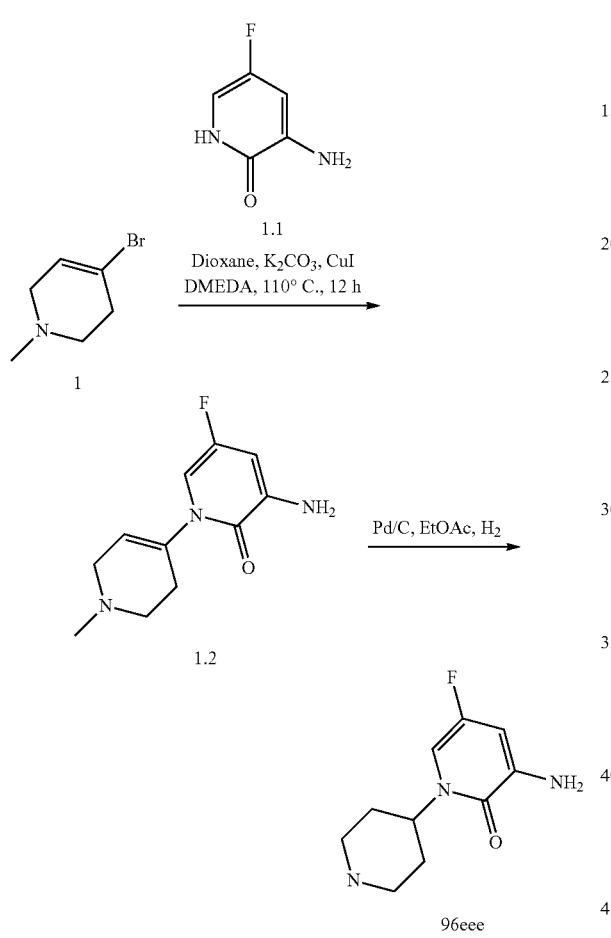

96eee

Synthesis of Compound 1.2.

To a solution of 1. (2.0 g, 11.35 mmol, 1 eq) in 1,4-dioxane (20 mL), 1.1. (1.74 g, 13.62 mmol, 1.2 eq) was added. The reaction mixture was degassed for 10 min under argon atmosphere followed by addition of potassium carbonate (7.83 g, 56.75 mmol, 5.0 eq), N,N-dimethylethylenediamine (0.249 g, 2.83 mmol, 0.25 eq), and copper iodide (0.323 g, 1.70 mmol, 0.15 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.2. (1.5 g, Yield: 59.15%). MS (ES): m/z 224.12 [M+H]+.

Synthesis of Intermediate 96eee.

To a solution of 1.2. (1.5 g, 6.71 mmol, 1.0 eq) in methanol (30 ml), palladium on charcoal (0.6 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96eee. (1.2 g, 79.28%). MS (ES): m/z 226.12 [M+H]+

Synthesis of Intermediate 96fff.

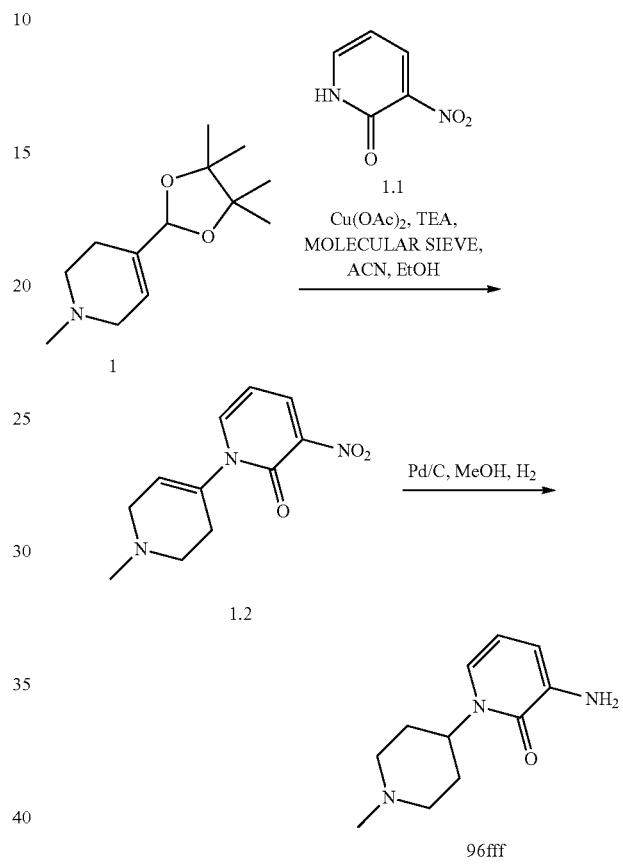

96fff

Synthesis of Compound 1.2.

To a solution of 1 (1 g, 4.48 mmol, 1.0 eq) in acetonitrile (6.3 mL) and ethanol (1.3 mL), 1.1 (0.63 g, 4.48 mmol, 1.0 eq), copper acetate (0.81 g, 4.48 mmol, 1.0 eq), molecular sieve (0.20 g) and triethylamine (0.90 g, 8.96 mmol, 2.0 eq) was added and degassed under oxygen. The reaction mixture was heated at 80° C. for 2 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 5% ethyl methanol dichloromethane as eluant to obtain pure 1.2 (0.46 g, 43.63%). MS(ES): m/z 236.24 [M+H]+.

Synthesis of Intermediate 96fff.

To a solution of 1.2 (0.46 g, 1.96 mmol, 1.0 eq) in palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 96fff (0.17 g, 41.94%). MS(ES): m/z 208.28 [M+H]+.

Synthesis of Intermediate 96ggg.

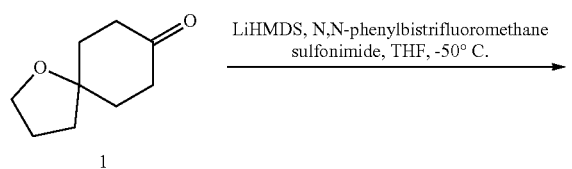

1

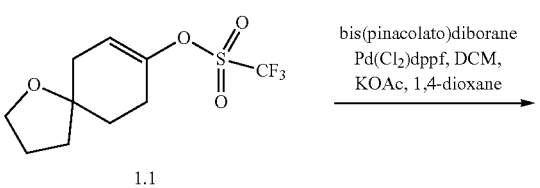

1.1

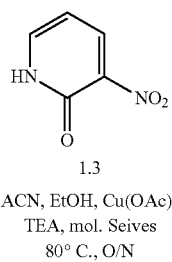

1.2

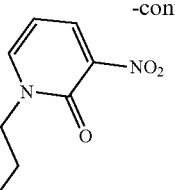

1.3

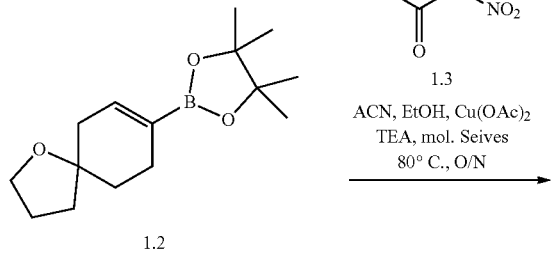

1.4

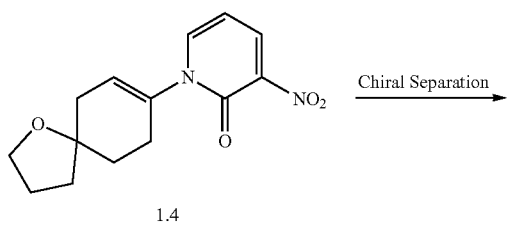

1.4a

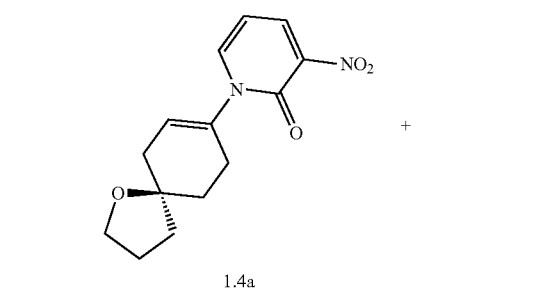

1.4b

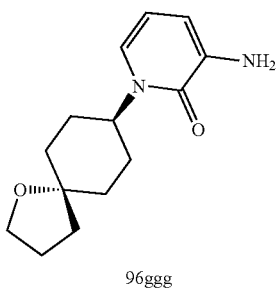 [SMILES: Nc1cccn([C@H]2CC[C@@]3(CCCO3)CC2)c1=O]

1.4b

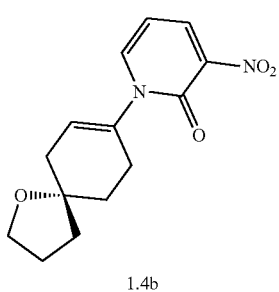

96ggg

Synthesis of Compound 1.1.

To Lithium bis(trimethylsilyl)amide solution (21 mL, 1M in THF) (2.5 g, 21 mmol, 1.3 eq) was added 1 (2.5 g, 26.21 mmol, 1.0 eq) in tetrahydrofuran (18 mL) at −50° C. The reaction mixture was stirred at −50° C. for 15 min. N,N-phenylbistrifluoromethane sulfonamide (5.79 g, 16.21 mmol, 1.0 eq) in tetrahydrofuran (60 mL) was added at −50° C. reaction mixture was stirred 1 h at −50° C. and 1 h at room temperature. After completion of reaction, reaction mixture was transferred into ice cold water and the product was extracted with ethyl acetate. Organic layer was combined, washed with brine, dried over sodium sulfate and concentrated under reduced pressure to obtain crude material. This was further purified by column chromaography using 3% ethyl acetate in hexane as eluant to obtain pure 1.1 (1.3 g, 28%). $^1$H NMR (CDCl$_3$, 400 MHZ): 5.71-5.00 (d, J=4.0 Hz, 1H), 3.95-3.86 (m, 2H), 2.63-2.58 (t, 1H), 2.41-2.32 (m, 1H), 2.28-1.90 (m, 3H), 1.85-1.74 (m, 1-3H), 0.92 (s, 1H).

Synthesis of Compound 1.2.

To a solution of 1.1 (1.3 g, 0.453 mmol, 1.0 eq) in 1,4-dioxane (5 mL) was added bis(pinacolato)diborane (1.17 g, 0.462 mmol, 1.02 eq), potassium acetate (1.25 g, 1.27 mmol, 2.8 eq). The reaction mixture was degassed for 10 min. under argon atmosphere, then [1,1′-Bis(diphenylphosphino)ferrocene]dichloropalladium(II), complex with dichloromethane (0.231 g, 0.028 mmol, 0.05 eq) was added, again degassed for 5 min. The reaction was stirred at 100° C. for 16 h. After completion of reaction, reaction mixture was concentrated under reduced pressure to obtain residue which was dissolved in acetonitrile and product was extracted with Heptane. Organic layer was combined and concentrated under reduced pressure to obtain 1.2. (1.1 g, 91.69%). $^1$H NMR (CDCl$_3$, 400 MHZ): 6.51 (s, 1H), 3.92-3.86 (m, 3H), 2.44-2.43 (d, J=4 Hz, 1H), 2.40-2.38 (m, 3H), 2.19-2.18 (m, 1H), 2.00-1.93 (m, 3H), 1.78-1.70 (m, 4H), 1.63-1.57 (m, 3H), 1.31-1.26 (m, 12H).

Synthesis of Compound 1.4.

To a solution of 1.3 (0.600 gm, 0.42 mmol, 1.0 eq) and 1.2 (1.1 g, 0.42 mmol, 1.0 eq) in acetonitrile (9 mL) and ethanol (1 mL) (9:1) was added triethyl amine (1.8 mL, 1.28 mmol, 3.0 eq) and copper acetate (0.777 g, 0.42 mmol, 1.0 eq). Reaction mixture was refluxed for 12 h. After completion of reaction, reaction mixture filtered and product was washed with methanol. Organic layer was combined, dried over sodium sulphate and concentrated under reduced pressure to obtain crude material. This was further purified by column chromatography to obtain 1.4. (0.300 g, 47.87%). MS (ES): m/z 278.5 [M+H]⁺

Synthesis of Compound 1.4b.

Isomers of 1.4 (0.300 g) were separated out using column (CHIRALCEL OJ-H (250 mm*4.6 mm, 5 u) in 0.1% Diethyl amine in methanol as co-solvent with flow rate of 4 mL/min. to get pure fraction-1 and fraction-2. Fraction-2 was concentrated under reduced pressure at 30° C. to afford 0.120 g. MS (ES): m/z 277.5 [M+H]⁺

Synthesis of Intermediate 96ggg.

To a solution of 1.4b (0.120 g, 0.043 mmol, 1.0 eq) in methanol (5 mL), palladium on charcoal (0.120 g) was added and the reaction mixture was stirred under hydrogen pressure for 12 h at room temperature. After completion of reaction, reaction mixture was filtered through celite-bed and washed with methanol. Filtrate was concentrated under reduced pressure to obtain crude material. This was further purified by trituration with n-pentane to obtain pure 96ggg (0.035 g, 52.13%). MS (ES): m/z 249.5 [M+H]⁺

Synthesis of Intermediate 96hhh.

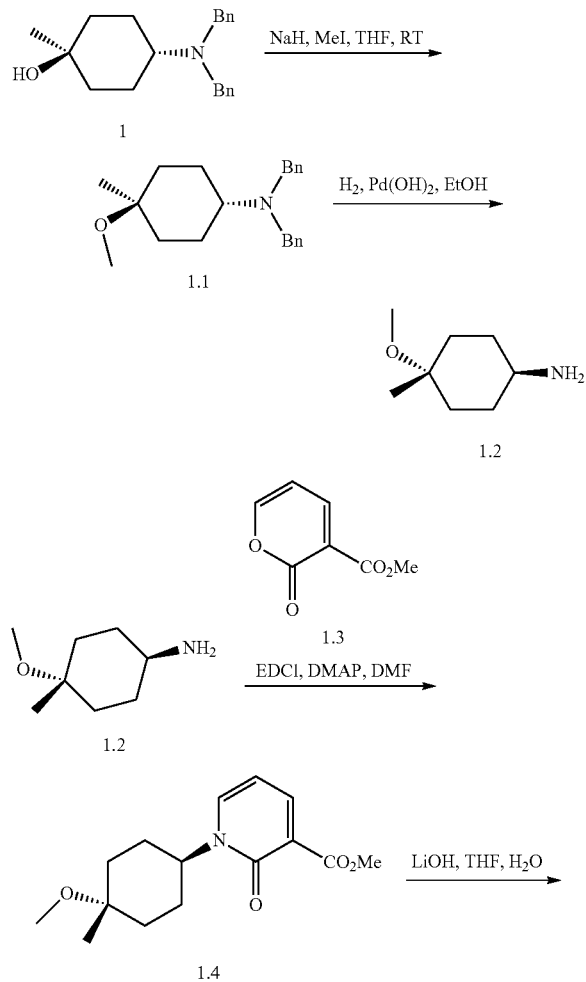

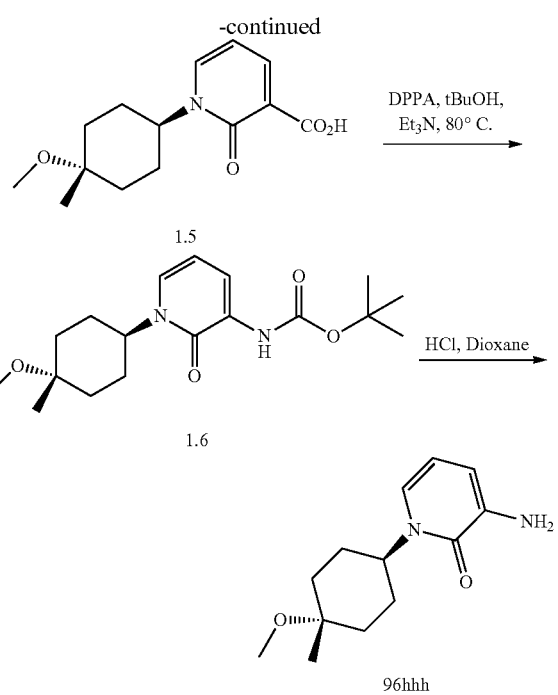

Synthesis of Compound 1.1.

To a cooled solution of 1 (4 g, 12.94 mmol, 1.0 eq) in tetrahydrofuran (40 mL) was added sodium hydride (1.04 g, 25.88 mmol, 2.0 eq) followed by addition of methyl iodide (2.39 g, 16.82 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 3-4% ethyl acetate in hexane to obtain pure 1.1 (2.7 g, 64.57%), MS(ES): m/z 324.22 [M+H]⁺.

Synthesis of Compound 1.2.

To a solution of 1.1 (1.7 g, 2.32 mmol, 1.0 eq) in ethanol (20 mL), palladium on charcoal (0.8 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 1.2 (0.6 g, 78.78%). MS (ES): m/z 144.23 [M+H]⁺

Synthesis of Compound 1.4.

To a cooled solution of 1.2 (0.600 g, 4.19 mmol, 1.0 eq), in N,N-dimethylformamide (5 mL) was added 1.3 (0.645 g, 4.19 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.838 g, 5.40 mmol, 1.3 eq) and 4-Dimethylaminopyridine (0.286 g, 1.04 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.4 (0.156 g, 13.33%). MS(ES): m/z 280.34 [M+H]$^+$.

Synthesis of Compound 1.5.

To a solution of 1.4 (0.156 g, 0.55 mmol, 1.0 eq), in tetrahydrofuran: water (10 mL, 2:1) was added lithium hydroxide (0.128 g, 5.58 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.5 (0.138 g, 92.44%). MS(ES): m/z 268.33 [M+H]$^+$.

Synthesis of Compound 1.6.

To a solution of 1.5 (0.136 g, 0.51 mmol, 1.0 eq) in tert.butanol (5 mL) was added triethylamine (0.885 g, 0.87 mmol, 1.7 eq) and diphenyl phosphoryl azide (0.184 g, 0.67 mmol, 1.3 eq) under nitrogen followed by heating at 75° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.6 (0.130 g, 74.45%). MS(ES): m/z 337.43 [M+H]$^+$.

Synthesis of Intermediate 96hhh.

A cooled solution of 1.6 (0.130 g, 0.102 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 96hhh (0.100 g, 41.31%). MS(ES): m/z 237.32 [M+H]$^+$.

Synthesis of Intermediate 96iii.

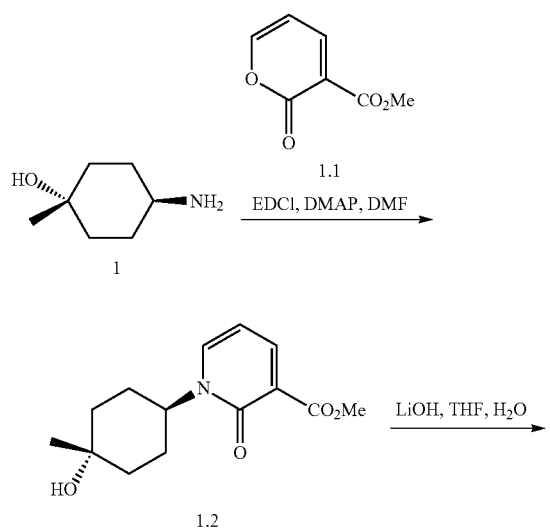

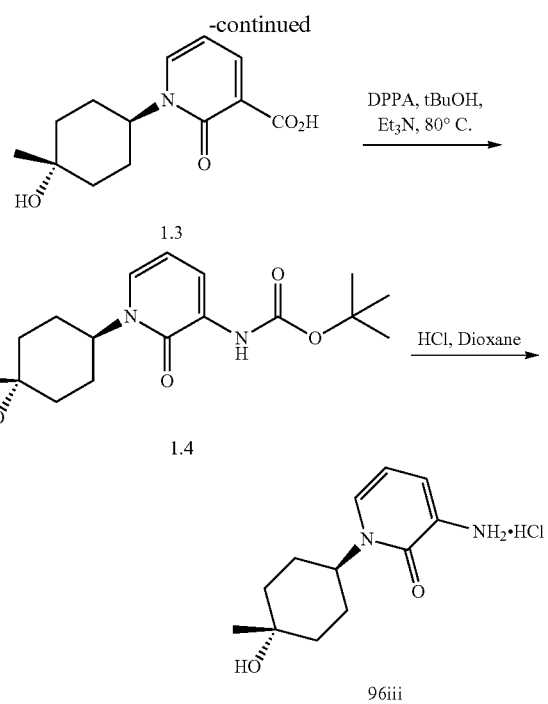

Synthesis of Compound 1.2.

To a cooled solution of 1 (0.900 g, 6.97 mmol, 1.0 eq), in N,N-dimethylformamide (8 mL) was added 1.1 (1.07 g, 6.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.140 g, 9.06 mmol, 1.3 eq) and 4-Dimethylaminopyridine (0.479 g, 1.74 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (0.172 g, 9.31%). MS(ES): m/z 266.31 [M+H]$^+$.

Synthesis of Compound 1.3.

To a solution of 1.2 (0.172 g, 0.648 mmol, 1.0 eq), in tetrahydrofuran: water (10 mL, 2:1) was added lithium hydroxide (0.272 g, 6.48 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.150 g, 92.08%). MS(ES): m/z 252.12 [M+H]$^+$.

Synthesis of Compound 1.4.

To a solution of 1.3 (0.150 g, 0.596 mmol, 1.0 eq) in tert.butanol (5 mL) was added triethylamine (0.102 g, 1.01 mmol, 1.7 eq) and diphenyl phosphoryl azide (0.212 g, 0.778 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.100 g, 51.96%). MS(ES): m/z 323.41 [M+H]⁺.

Synthesis of Compound 96iii.

A cooled solution of 1.4 (0.100 g, 0.310 mmol, 1 eq) in dioxane (5 mL) was added 4N hydrochloric acid in dioxane (4 mL) as a dropwise. The reaction mixture was stirred at room temperature for 2 h. After completion of reaction, reaction mixture was concentrated under reduced pressure to obtain pure 96iii (0.070 g, 87.22%). MS(ES): m/z 223.41 [M−HCl]⁺.

Synthesis of Intermediate 96jjj.

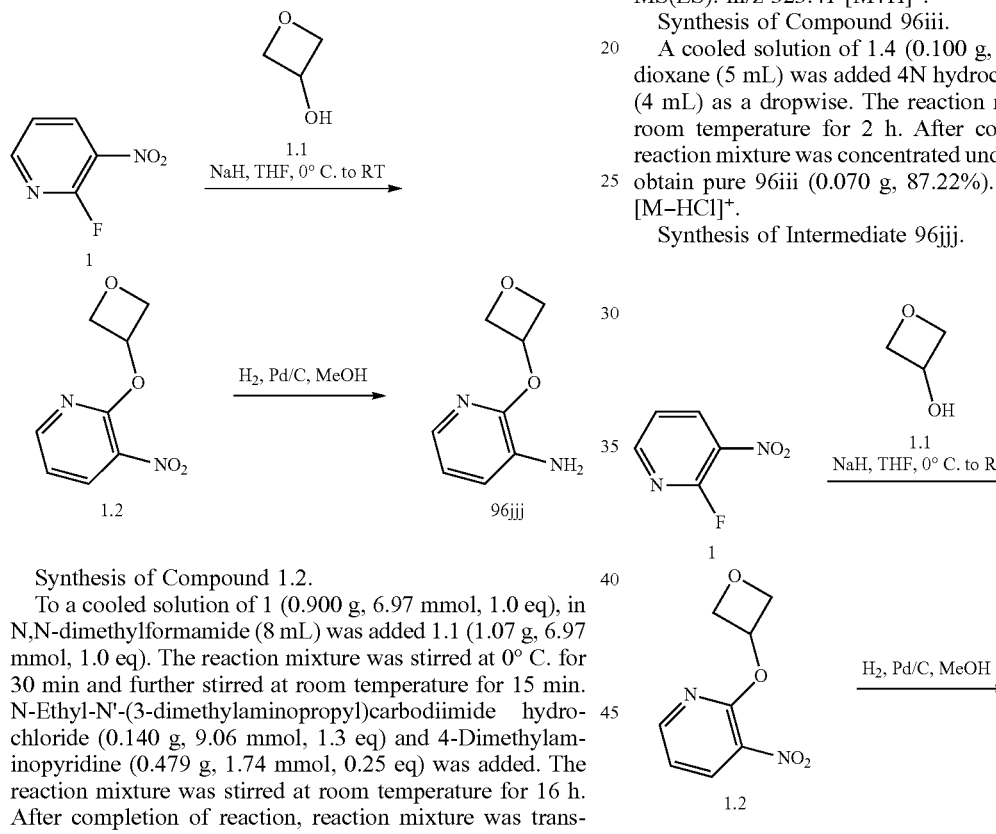

Synthesis of Compound 1.2.

To a cooled solution of 1 (0.900 g, 6.97 mmol, 1.0 eq), in N,N-dimethylformamide (8 mL) was added 1.1 (1.07 g, 6.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.140 g, 9.06 mmol, 1.3 eq) and 4-Dimethylaminopyridine (0.479 g, 1.74 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (0.172 g, 9.31%). MS(ES): m/z 266.31 [M+H]⁺.

Synthesis of Compound 1.3.

To a solution of 1.2 (0.172 g, 0.648 mmol, 1.0 eq), in tetrahydrofuran: water (10 mL, 2:1) was added lithium hydroxide (0.272 g, 6.48 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.150 g, 92.08%). MS(ES): m/z 252.12 [M+H]⁺.

Synthesis of Compound 1.4.

To a solution of 1.3 (0.150 g, 0.596 mmol, 1.0 eq) in tert.butanol (5 mL) was added triethylamine (0.102 g, 1.01 mmol, 1.7 eq) and diphenyl phosphoryl azide (0.212 g, 0.778 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.100 g, 51.96%). MS(ES): m/z 323.41 [M+H]⁺.

Synthesis of Compound 96iii.

A cooled solution of 1.4 (0.100 g, 0.310 mmol, 1 eq) in dioxane (5 mL) was added 4N hydrochloric acid in dioxane (4 mL) as a dropwise. The reaction mixture was stirred at room temperature for 2 h. After completion of reaction, reaction mixture was concentrated under reduced pressure to obtain pure 96iii (0.070 g, 87.22%). MS(ES): m/z 223.41 [M−HCl]⁺.

Synthesis of Intermediate 96jjj.

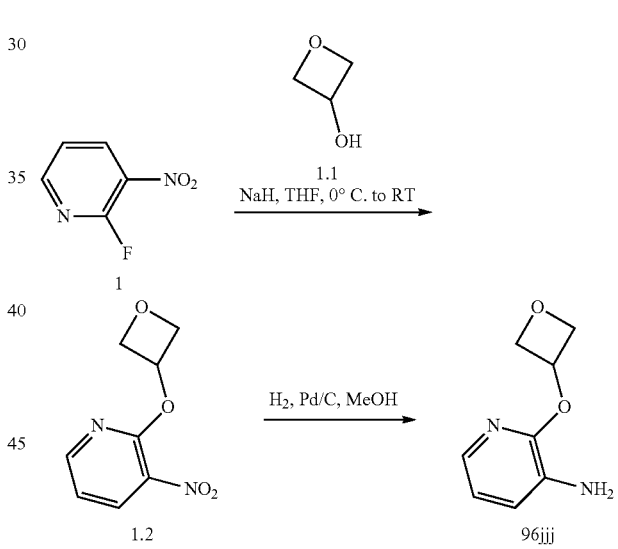

Synthesis of Compound 1.2.

To a cooled solution of 1.1 (0.860 g, 11.61 mmol, 1.1 eq) in tetrahydrofuran (15 mL) was added sodium hydride (0.464 g, 11.61 mmol, 1.1 eq) followed by addition of 1 (1.5 g, 10.56 mmol, 1 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 8% ethyl acetate in hexane to obtain pure 1.2 (1 g, 48.29%), MS(ES): m/z 197.16 [M+H]⁺.

Synthesis of Compound 96jjj.

To a solution of 1.2 (1 g, 5.10 mmol, 1.0 eq) in methanol (6 ml), palladium on charcoal (0.200 g) was added. Hydrogen was purged through reaction mixture for 4 h at room temperature. After completion of reaction, reaction mixture was filtered through celite-bed and washed with methanol. Filtrate was concentrated under reduced pressure to obtain 96jjj (0.700 g, 82.63%). MS (ES): m/z 167.18 [M+H]$^+$ Synthesis of Intermediate 96kkk.

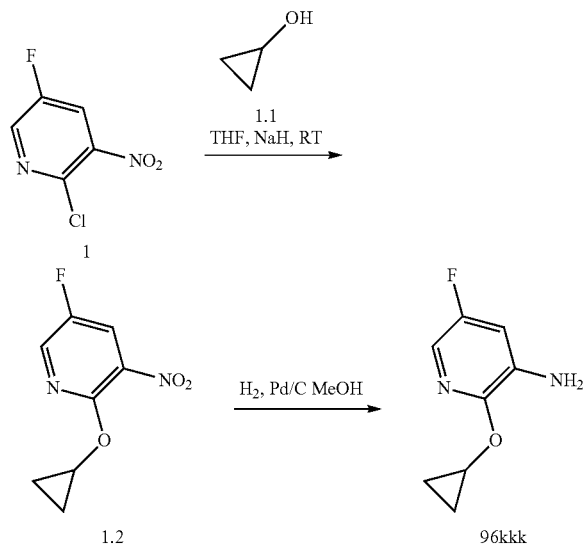

Synthesis of Compound 1.2.

To a cooled solution of 1 (1 g, 5.66 mmol, 1 eq) in tetrahydrofuran (10 mL) was added sodium hydride (0.163 g, 11.32 mmol, 2 eq) followed by addition of 1.1 (0.427 g, 7.36 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 15% ethyl acetate in hexane to obtain pure 1.2 (0.720 g, 64.14%), MS(ES): m/z 199.15 [M+H]$^+$.

Synthesis of Compound 96kkk.

To a solution of 1.2 (0.720 g, 3.63 mmol, 1.0 eq) in methanol (8 ml), palladium on charcoal (0.180 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 1.8% methanol in dichloromethane to obtain pure 96kkk (0.580 g, 94.92%). MS (ES): m/z 169.17 [M+H]$^+$ Synthesis of Intermediate 96lll.

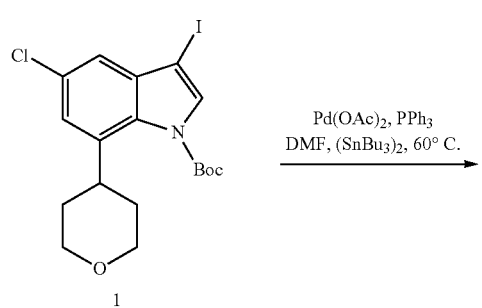

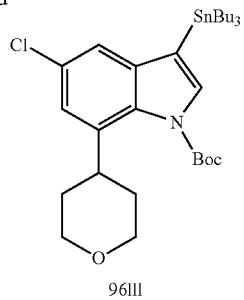

Synthesis of Compound 1.

Compound was synthesized as per Example 103 (I-190).

Synthesis of Compound 96lll.

To a solution of 1 (0.400 g, 0.867 mmol, 1.0 eq) in dimethylformamide (8 mL), was added Hexabutylditin (0.528 g, 0.911 mmol, 1.05 eq), palladium acetate (0.010 g, 0.043 mmol, 0.05 eq) and triphenylphosphine (0.002 g, 0.0069 mmol, 0.008 eq). The reaction mixture was degassed for 10 min. under argon atmosphere, then reaction was stirred at 60° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude 96lll (0.610 g). MS(ES): m/z 626.23 [M+H]$^+$. [crude was directly use for next step].

Synthesis of Intermediate 96mmm.

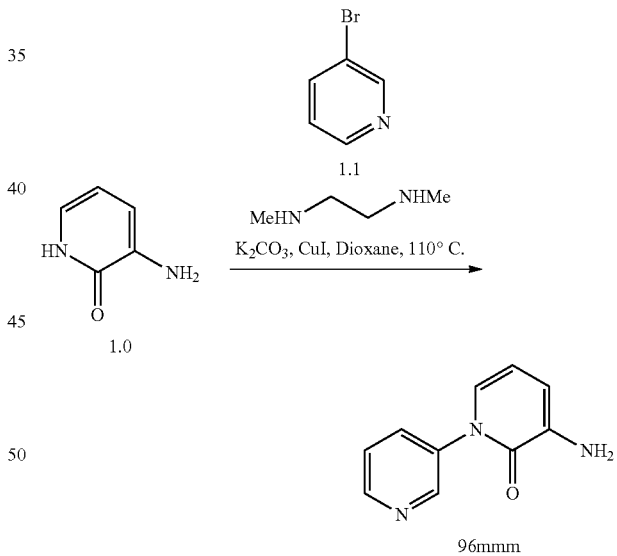

Synthesis of Compound 96mmm.

To a solution of 1.0 (0.5 g, 4.54 mmol, 1.0 eq) in 1,4-dioxane (40 mL), 1.1 (1.79 g, 11.35 mmol, 2.5 eq) was added. The reaction mixture was degassed for 10 min under argon atmosphere followed by addition of potassium carbonate (1.87 g, 13.62 mmol, 3.0 eq), N,N-dimethylethylenediamine (0.160 g, 1.81 mmol, 0.4 eq), and copper iodide (0.172 g, 0.90 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 96mmm (0.180 g, Yield: 21.18%). MS (ES): m/z 188.20 [M+H]$^+$.

Synthesis of Intermediate 96nnn.

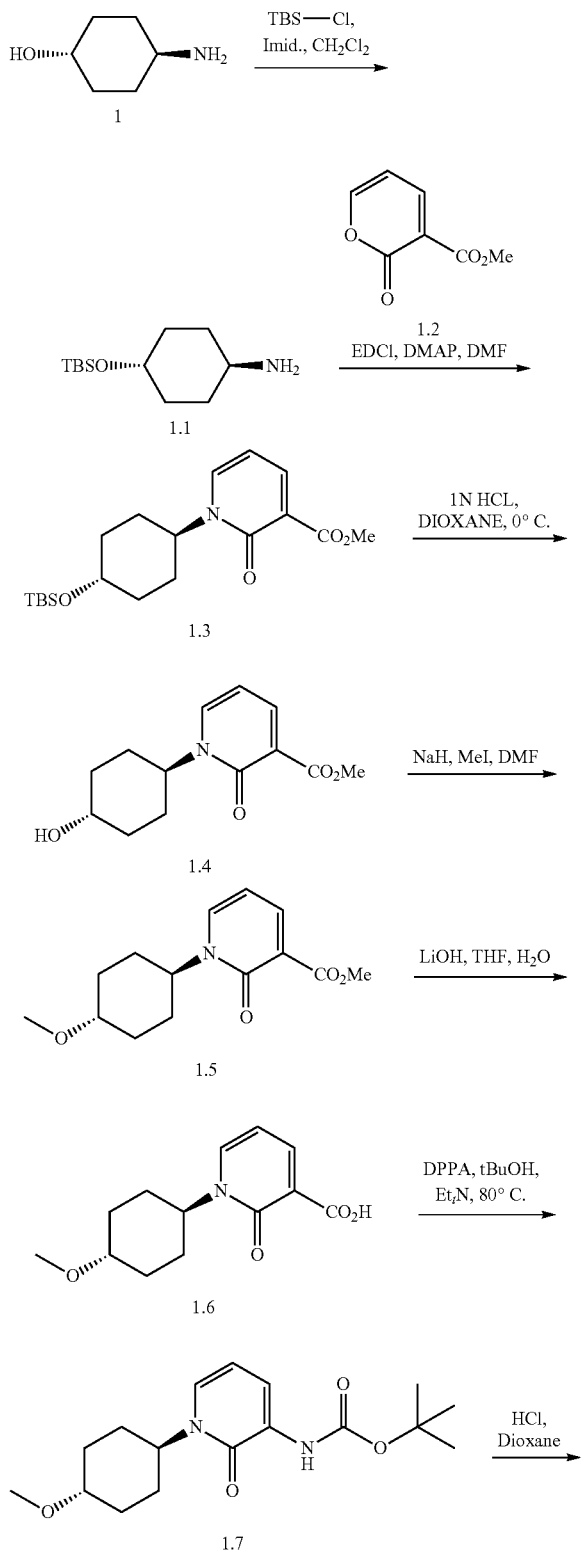

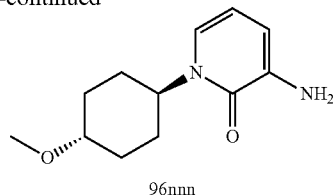

Synthesis of Compound 1.1.

To a solution of 1 (4 g, 34.73 mmol, 1.0 eq) in dichloromethane (40 mL), imidazole (7 g, 104.19 mmol, 3.00 eq), tert-butyldimethylsilyl chloride (7.8 g, 52.09 mmol, 1.5 eq) was added at 0° C. The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% methanol in dichloromethane as eluant to 1.1. (5.2 g, 65.26%). MS(ES): m/z 230.44 [M+H]$^+$ Synthesis of Compound 1.3.

To a solution of 1.1 (5.2 g, 22.66 mmol, 1.0 eq) in dimethylformamide (50 mL) was added 1.2 (3.4 g, 22.66 mmol, 1.0 eq). The reaction mixture was stirred at room temperature for 1 h followed by addition of N-Ethyl-N'-(3-dimethylaminopropyl) carbodiimidehydrochloride (6.5 g, 33.99 mol, 1.5 eq) and 4-dimethylaminopryidine (0.69 g, 5.66 mmol, 0.25 eq). The reaction was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 30% ethylacetate in hexane as eluant to 1.3 (1.8 g, 21.73%). MS(ES): m/z 366.55 [M+H]$^+$.

Synthesis of Compound 1.4.

To 1.3. (1.8 g, 4.92 mmol, 1.0 eq) added hydrochloric acid in 1,4-dioxane (10 mL). The reaction mixture was stirred at room temperature for 1 h. After completion of reaction, reaction mixture was concentrated under reduced pressure to obtain residue which was stirred with diethyl ether and filtered to obtain pure 1.4 (1.2 g, 96.98%). MS (ES): m/z 252.28 [M+H]$^+$.

Synthesis of Compound 1.5.

To a solution of 1.4. (1.2 g, 4.78 mmol, 1.0 eq) in tetrahydrofuran (10 mL), sodium hydride (0.10 g, 7.17 mmol, 1.5 eq), was added 0° C. followed by addition of methyl iodide (0.67 g, 4.78 mmol, 1.0 eq). The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 1.4% methanol in dichloromethane as eluant to 1.5. (0.78 g, 61.56%). MS(ES): m/z 266.31 [M+H]$^+$ Synthesis of Compound 1.6.

To a solution of 1.5 (0.78 g, 2.94 mmol, 1.0 eq), in tetrahydrofuran: methanol: water (5 mL, 1:1:1) was added lithium hydroxide (1.2 g, 29.4 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.6 (0.65 g, 87.99%). MS(ES): m/z: 252.28 [M+H]$^+$.

Synthesis of Compound 1.7.

To a solution of 1.6 (0.65 g, 2.59 mmol, 1.0 eq) in tert-butanol (6 mL) was added diphenylphosphorylazide (1.1 g, 4.14 mmol, 1.6 eq), trimethylamine (10 mL, 7.7 mmol, 3.0 eq). The reaction mixture was heated at 80° C. for 18 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% ethyl acetate in hexane as eluant to 1.7 (0.38 g, 45.56%). MS(ES): m/z 323.41 [M+H]$^+$.

Synthesis of Compound 96nnn.

To 1.7 (0.38 g, 1.18 mmol, 1.0 eq) added hydrochloric acid in 1,4-dioxane (1 mL). The reaction mixture was stirred at room temperature for 1 h. After completion of reaction, reaction mixture was concentrated under reduced pressure to obtain residue which was stirred with diethyl ether and filtered to obtain pure 96nnn (0.20 g, 76.34%). MS (ES): m/z 223.29 [M+H]$^+$.

Synthesis of Intermediate 96ooo.

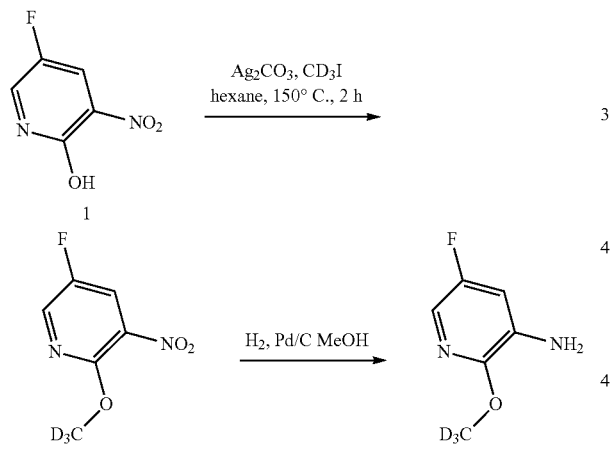

Synthesis of Compound 1.1.

To a cooled solution of 1 (1 g, 6.32 mmol, 1 eq) in hexane (10 mL) was added silver carbonate (3.50 g, 12.65 mmol, 2 eq) followed by addition of iodomethane-d$_3$ (1.10 g, 7.59 mmol, 1.1 eq) under nitrogen. The reaction was stirred at 150° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 7% ethyl acetate in hexane to obtain pure 1.1 (0.470 g, 42.33%), MS(ES): m/z 176.13 [M+H]$^+$.

Synthesis of Compound 96ooo.

To a solution of 1.1 (0.470 g, 2.68 mmol, 1.0 eq) in methanol (7 ml), palladium on charcoal (0.230 g) was added. Hydrogen was purged through reaction mixture for 1 h at room temperature. After completion of reaction, reaction mixture was filtered through celite-bed and washed with methanol. Filtrate was concentrated under reduced pressure to obtain crude material. This was further purified by trituration with pantane to obtain pure 96ooo (0.280 g, 71.88%). MS (ES): m/z 146.15 [M+H]$^+$ Synthesis of Intermediate 96ppp.

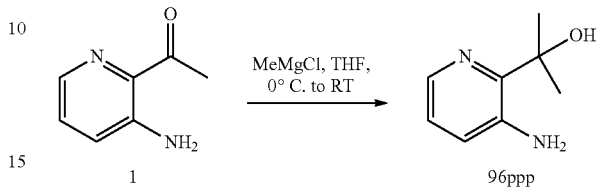

Synthesis of compound 96ppp.

To a solution of 1. (0.40 g, 2.94 mmol, 1.0 eq) in Tetrahydrofuran (4 mL), methyl magnesium chloride (0.43 g, 5.88 mmol, 2.0 eq) was added at 0° C. The reaction mixture was stirred at room temperature for 2 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 20% ethylacetate in hexane to obtain 96ppp. (0.12 g, Yield: 26.84%). MS (ES): m/z 153.20 [M+H]$^+$ Synthesis of Intermediate 96qqq.

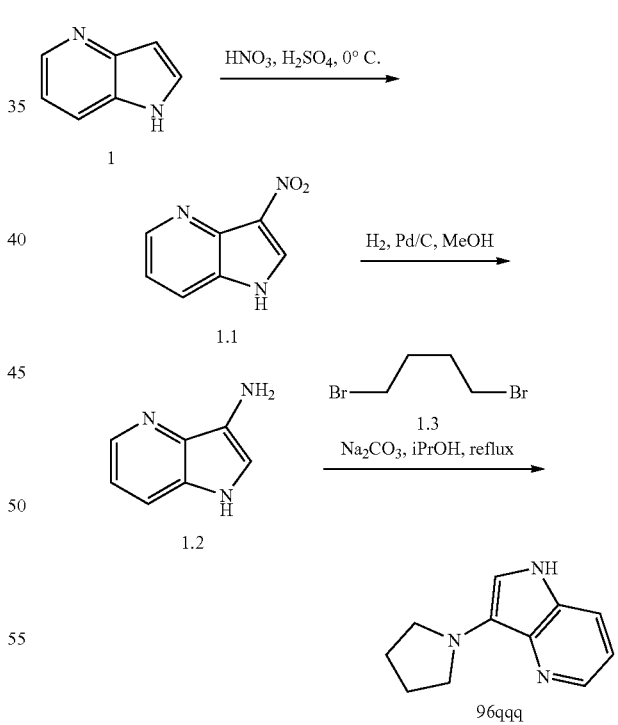

Synthesis of Compound 1.1.

To 1 (2.0 g, 17.54 mmol, 1.0 eq) was added mixture of Sulfuric acid (10 mL) added Nitric acid (1.35 ml, 21.04 mmol, 1.2 eq) at 0° C. The reaction mixture was stirred at 0° C. for 2 h. After completion of reaction, reaction mixture was transferred into ice. Precipitated compound was filtered and dried well to obtain 1.1. (1.2 g, 43.45%). MS(ES): m/z 164.04 [M+H]$^+$.

Synthesis of Compound 1.2.

To a solution of 1.1 (1.2 g, 7.35 mmol, 1.0 eq) in methanol (45 ml), palladium on charcoal (0.6 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 1.2. (0.750 g, 76.57%). MS (ES): m/z 134.07 [M+H]$^+$

Synthesis of Compound 96qqq.

To a solution of 1.2 (0.750 gm, 5.63 mmol, 1.0 eq) and 1.3 (1.09 g, 5.06 mmol, 0.9 eq) in Isopropyl alcohol (30 mL) was added Sodium carbonate (1.8 g, 16.89 mmol, 3.0 eq) and heated to reflux for 18 h. After completion of reaction, reaction mixture was, filtered and product was washed with methanol. Organic layer was combined, dried over sodium sulphate and concentrated under reduced pressure to obtain crude material. This was further purified by column chromatography to obtain 96qqq. (0.100 g, 11.38%). MS (ES): m/z 188.1 [M+H]$^+$

Synthesis of Intermediate 96rrr.

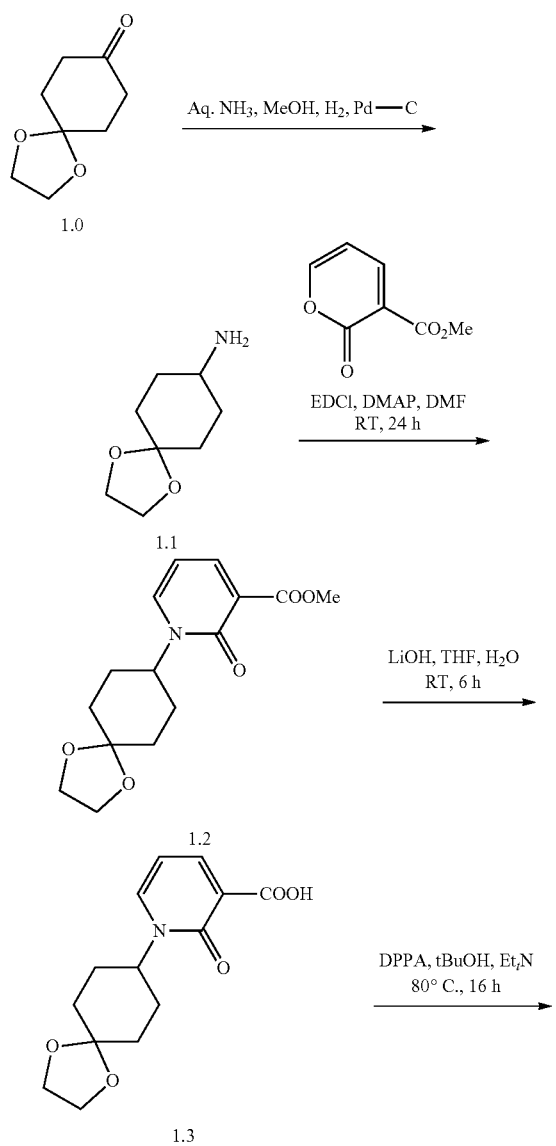

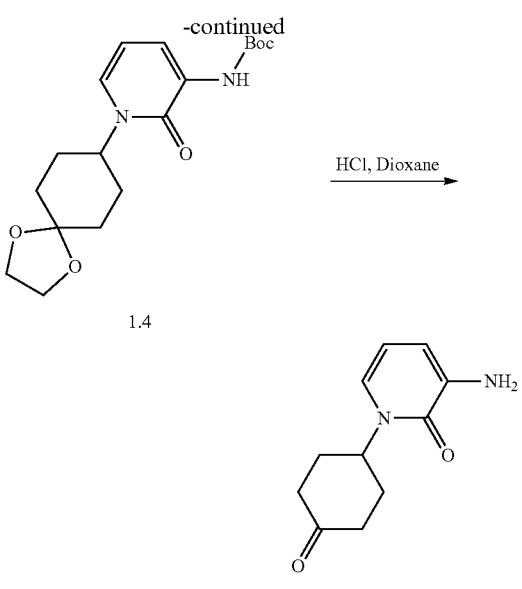

Synthesis of Compound 1.1.

To a solution of 1.0 (5.0 g, 32.01 mmol, 1.0 eq) in methanolic ammonia (65 mL) was added palladium on charcoal (2.3 g). Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 1.1 (2.5 g, 49.67%). MS (ES): m/z 158.21 [M+H]$^+$

Synthesis of Compound 1.2.

To a solution of 1.1 (1.2 g, 7.63 mmol, 1.0 eq) in N,N-dimethylformamide (12 mL) was added methyl 2-oxo-2H-pyran-3-carboxylate (1.17 g, 7.63 mmol, 1.0 eq). The reaction mixture was stirred at room temperature for 1 h followed by addition of N-Ethyl-N'-(3-dimethylaminopropyl) carbodiimide hydrochloride (1.90 g, 9.91 mmol, 1.3 eq) and 4-dimethylaminopryidine (0.233 g, 1.90 mmol, 0.25 eq). The reaction was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 30% ethyl acetate in hexane as eluant to 1.2 (0.630 g, Yield: 28.14%). MS(ES): m/z 294.32 [M+H]$^+$

Synthesis of Compound 1.3.

To a solution of 1.2 (0.630 g, 2.15 mmol, 1.0 eq), in tetrahydrofuran: methanol: water (5 mL, 1:1:1) was added lithium hydroxide (0.451 g, 10.75 mmol, 5.0 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.3 (0.500 g, Yield: 83.35%). MS(ES): m/z: 280.29 [M+H]$^+$.

Synthesis of Compound 1.4.

To a solution of 1.3 (0.500 g, 1.79 mmol, 1.0 eq) in Tert-Butyl alcohol was added diphenylphosphorylazide (0.640 g, 2.32 mmol, 1.3 eq), triethylamine (0.307 g, 2.148 mmol, 1.7 eq). The reaction was stirred at 90° C. for 16 h. After completion of reaction, reaction mixture was concentrated under reduced pressure to obtain crude material. This was further purified by combi flash using 1.0% MeOH in Dichloromethane as eluent to 1.4 (0.330 g, Yield: 52.60%). MS(ES): m/z 351.42 [M+H]⁺.

Synthesis of Compound 96rrr.

To 1.4 (0.330 g, 0.941 mmol, 1.0 eq) was added 4M hydrochloric acid in 1,4-Dioxane (7 mL) and stirred at room temperature for 4 h. After completion of reaction, reaction mixture was concentrated under reduced pressure, residue was triturated with diethyl ether to obtain 96rrr (0.038 g, 19.56%). MS (ES): m/z 207.25 [M+H]⁺.

Synthesis of Intermediate 96sss.

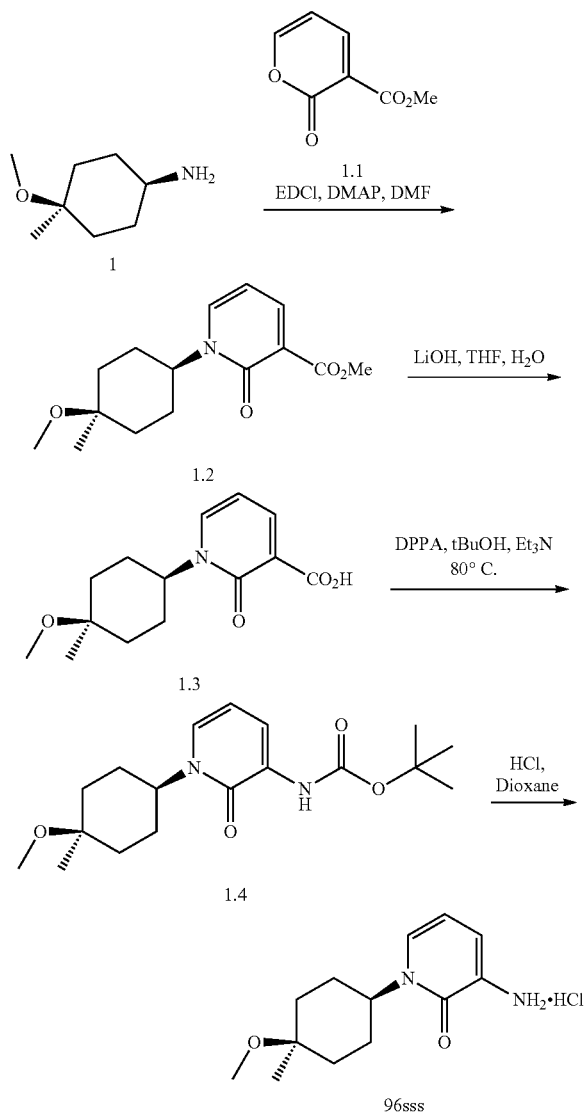

Synthesis of Compound 1.2.

To a cooled solution of 1 (0.750 g, 5.24 mmol, 1.0 eq), in N,N-dimethylformamide (50 mL) was added 1.1 (0.807 g, 5.24 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.105 g, 6.81 mmol, 1.3 eq) and 4-Dimethylaminopyridine (0.159 g, 1.31 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (0.267 g, 18.25%). MS(ES): m/z 280.34 [M+H]⁺.

Synthesis of Compound 1.3.

To a solution of 1.2 (0.267 g, 0.95 mmol, 1.0 eq), in tetrahydrofuran: methanol: water (10 mL, 2:2:1) was added lithium hydroxide (0.396 g, 9.58 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.237 g, 93.47%). MS(ES): m/z 266.31 [M+H]⁺.

Synthesis of Compound 1.4.

To a solution of 1.3 (0.232 g, 0.87 mmol, 1.0 eq) in tert.butanol (6 mL) was added triethylamine (0.150 g, 1.48 mmol, 1.7 eq) and diphenyl phosphoryl azide (0.320 g, 1.13 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.180 g, 61.18%). MS(ES): m/z 337.43 [M+H]⁺.

Synthesis of Compound 96sss.

A cooled solution of 1.4 (0.180 g, 0.535 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 96sss (0.140 g, 95.93%). MS(ES): m/z 273.77 [M+H]⁺.

Synthesis of Intermediate 96ttt.

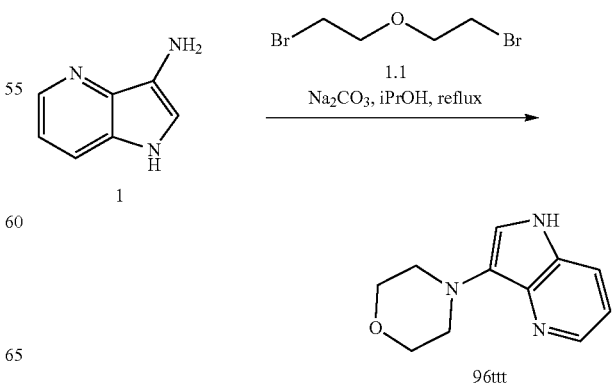

Synthesis of Compound 1.

Compound was synthesized as per I-552 to obtain 1. (Yield: 76.57%), MS (ES): m/z 134.07 [M+H]+

Synthesis of Compound 96ttt.

A solution of 1 (0.250 gm, 1.87 mmol, 1.0 eq) and 1.1. (0.389 g, 1.68 mmol, 0.9 eq) in Isopropyl alcohol (10 mL) was added Sodium carbonate (0.594 g, 5.61 mmol, 3.0 eq) and heated to reflux for 18 h. After completion of reaction, reaction mixture was filtered and washed with methanol. Filtrate was concentrated under reduced pressure to obtain crude material. This was further purified by silica column chromatography to obtain 96ttt. (0.120 g, 31.45%). MS (ES): m/z 204.1 [M+H]+.

Synthesis of Intermediate 96uuu.

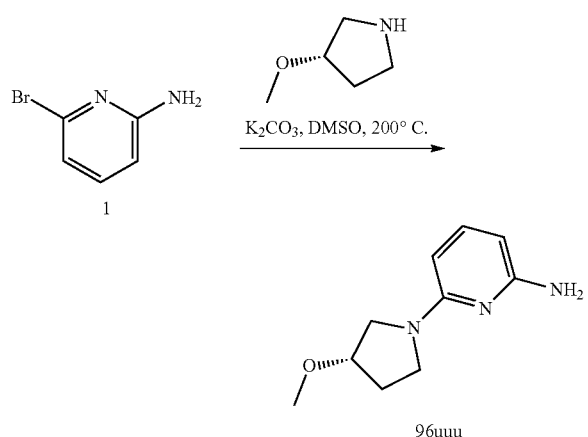

Synthesis of Compound 96uuu.

To a solution of 1 (0.2 g, 1.156 mmol, 1.0 eq), in dimethyl sulphoxide (1.6 mL) was added potassium carbonate (0.638 g, 4.624 mmol, 4 eq) and (s)-3-methoxypyrrolidine hydrochloride (0.316 g, 2.31 mmol, 2.0 eq) at room temperature. The reaction mixture was stirred at 200° C. for 10 h. After completion of reaction, reaction mixture was transferred into water and product was extracted with dichloromethane. Organic layer was combined and dried over sodium sulphate and concentrated under reduced pressure to obtain crude material. This was further purified by trituration with diethyl ether to obtain pure 96uuu (0.12 g, 5.72.40%). MS(ES): m/z 194.35 [M+H]+

Synthesis of Intermediate 96vvv.

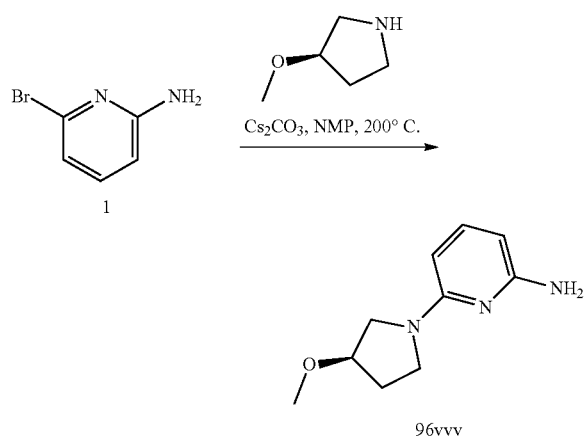

Synthesis of Compound 96vvv.

Compound was synthesized as per experimental of 96uuu to obtain 96vvv (0.12 g, 53.72. %). MS(ES): m/z 194.35 [M+H]+

Synthesis of Intermediate 96www.

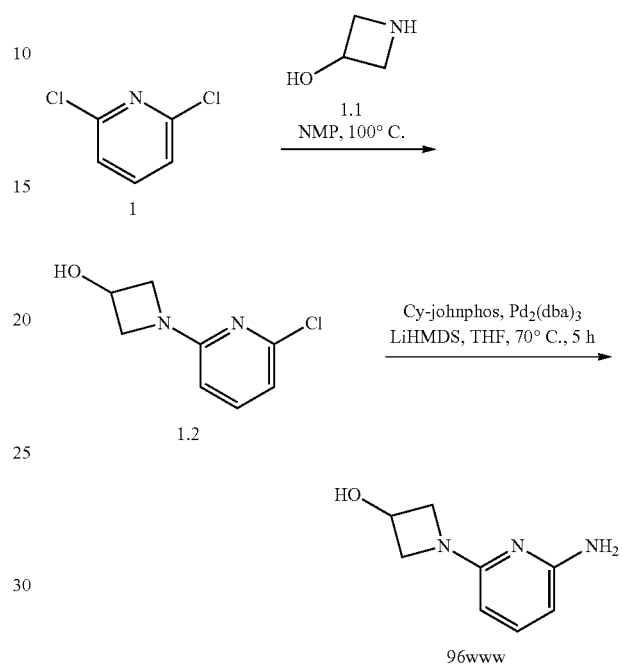

Synthesis of Compound 1.2.

To a solution of 1 (2.5 g, 16.89 mmol, 1.0 eq) in N-Methyl-2-pyrrolidone (30 mL) 1.1 (1.8 g, 25.33 mmol, 1.5 eq) was added. The reaction was stirred at 100° C. for 4 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 2% methanol in dichloromethane to obtain pure 1.2. (0.7 g, 22.44%). MS (ES): m/z 185.04 [M+H]+

Synthesis of Compound 96www.

To a solution of 1.2 (0.7 g, 3.80 mmol, 1.0 eq) in tetrahydrofuran (7 mL) was added (2-Biphenyl)dicyclohexylphosphine, 2-(Dicyclohexylphosphino)biphenyl (0.133 g, 0.38 mmol, 0.1 eq), tris(dibenzylideneacetone)dipalladium (0) (0.173 g, 0.19 mmol, 0.05 eq). The reaction mixture was degassed for 10 min under argon atmosphere, then Lithium bis(trimethylsilyl)amide (1M in tetrahydrofuran) (11.4 ml, 11.4 mmol, 3.0 eq) was added, again degassed for 5 min. The reaction was stirred at 70° C. for 5 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 96www. (0.310 g, 49.49%). MS(ES): m/z 166.09 [M+H]+.

Synthesis of Intermediate 96xxx.

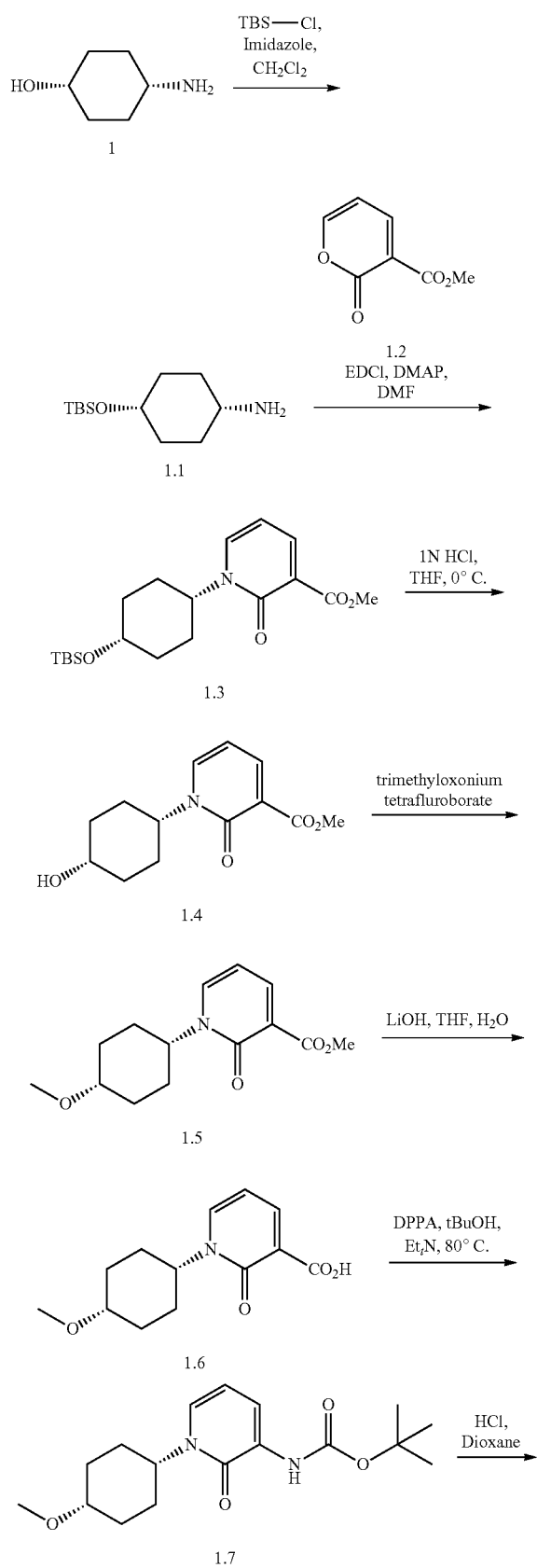

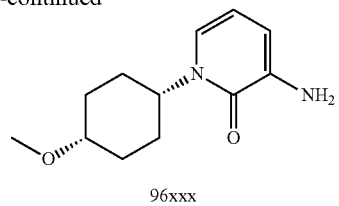

Synthesis of Compound 1.1.

To a solution of 1 (5 g, 43.41 mmol, 1.0 eq) in dichloromethane (75 mL) was added imidazole (14.76 g, 217.05 mmol, 5.0 eq) and stirred at for 30 min followed by addition of tert-Butyl(chloro)dimethylsilyl chloride (9.76 g, 65.11 mmol, 1.5 eq). The reaction was stirred at room temperature for 16 h. After completion of reaction, reaction mixture was transferred into ice cold water and product was extracted with ethyl acetate. Organic layer was combined, dried over sodium sulphate and concentrated under reduced pressure to obtain 1.1 (5 g, 50.20%), MS(ES): m/z 230.44 [M+H]$^+$.

Synthesis of Compound 1.3.

To a cooled solution of 1.1 (5 g, 21.79 mmol, 1.0 eq), in N,N-dimethylformamide (50 mL) was added 1.2 (3.36 g, 21.79 mmol, 1.0 eq). The reaction mixture was stirred at 0° C. for 30 min and further stirred at room temperature for 15 min. N-Ethyl-N'-(3-dimethylaminopropyl)carbodiimide hydrochloride (5.44 g, 28.32 mmol, 1.3 eq) and 4-Dimethylaminopyridine (0.655 g, 5.44 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.3 (3.0 g, 37.66%). MS(ES): m/z 366.55 [M+H]$^+$.

Synthesis of Compound 1.4.

A cooled solution of 1.3 (3.0 g, 8.21 mmol, 1.0 eq) in tetrahydrofuran (30 mL) was added 1N hydrochloric acid (10 mL) dropwise. The reaction mixture was stirred at room temperature for 16 h. After completion of reaction, reaction mixture was concentrated under reduced pressure to obtain pure 1.4 (1.90 g, 92.13%). MS(ES): m/z 178.16 [M+H]$^+$.

Synthesis of Compound 1.5.

To a solution of 1.4 (1.90 g, 7.56 mmol, 1.0 eq) in dichloromethane (38 ml), trimethyloxoniumtetrfluoroborate (3.33 g, 22.68 mmol, 3.0 eq) was added. Hydrogen gas was purged through reaction mixture for 4 h at room temperature. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.2% methanol in dichloromethane to obtain 1.5 (1.0 g, 49.85%). MS (ES): m/z 266.31 [M+H]$^+$.

Synthesis of Compound 1.6.

To a solution of 1.5 (1.0 g, 3.77 mmol, 1.0 eq), in tetrahydrofuran: methanol: water (10 mL, 2:2:1) was added lithium hydroxide (1.58 g, 37.7 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6 (0.650 g, 68.63%). MS(ES): m/z 252.32 [M+H]⁺.

Synthesis of Compound 1.7.

To a solution of 1.6 (0.650 g, 2.59 mmol, 1.0 eq) in tert.butanol (8 mL) was added triethylamine (0.444 g, 4.40 mmol, 1.7 eq) and diphenyl phosphoryl azide (0.925 g, 3.36 mmol, 1.3 eq) under nitrogen followed by heating at 75° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7 (0.410 g, 49.16%). MS(ES): m/z 323.41 [M+H]⁺.

Synthesis of Compound 96xxx.

A cooled solution of 1.7 (0.410 g, 8.21 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96xxx (0.270 g, 95.51%). MS(ES): m/z 223.29 [M+H]⁺.

Synthesis of Intermediate 96yyy.

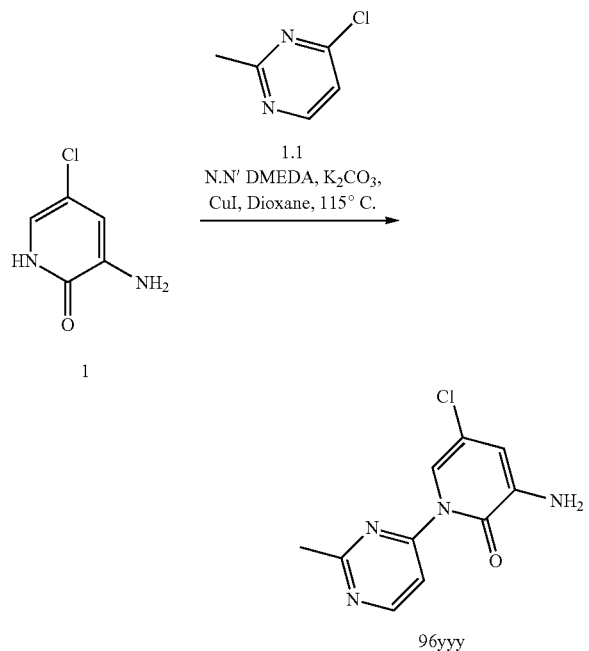

Synthesis of Compound 96yyy.

To a solution of 1 (1 g, 6.92 mmol, 1.0 eq) in 1,4-dioxane (100 mL), 1.1 (1.3 g, 10.38 mmol, 1.5 eq) was added. The reaction mixture was degassed for 10 min under argon atmosphere followed by addition of potassium carbonate (1.9 g, 13.84 mmol, 2.0 eq), N,N-dimethylethylenediamine (0.24 g, 2.76 mmol, 0.4 eq), and copper iodide (0.26 g, 1.38 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96yyy (0.16 g, Yield: 10.08%). MS (ES): m/z 237.66 [M+H]⁺.

Synthesis on Intermediate 96zzz

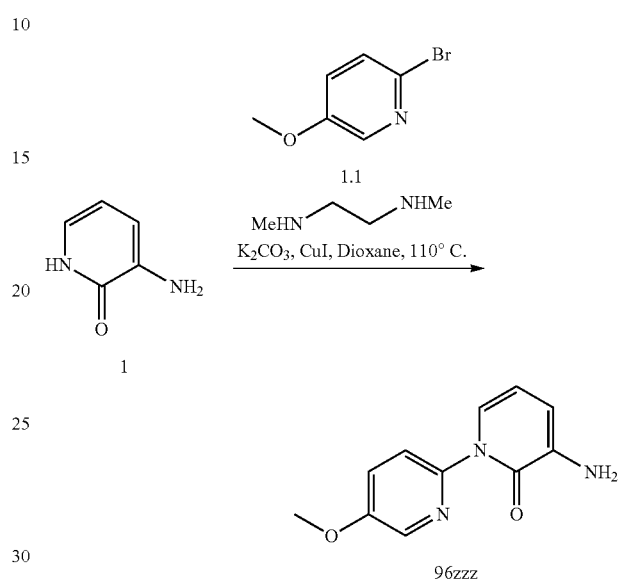

Synthesis of Compound 96zzz.

To a solution of 1. (1 g, 9.08 mmol, 1 eq) and 1.1 (2.05 g, 10.90 mmol, 1.2 eq) in 1,4-dioxane (10 mL) was added potassium carbonate (2.50 g, 18.16 mmol, 2.0 eq) and degassed with argon for 15 min. Copper iodide (0.345 g, 1.81 mmol, 0.2 eq) and 1,2-dimethylethylenediamine (0.320 g, 3.63 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 96zzz (0.500 g, 25.35%). MS(ES): m/z 218.23 [M+H]⁺.

Synthesis on Intermediate 96aaaa.

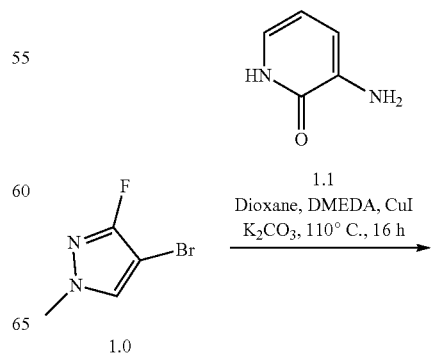

1372
Synthesis of Intermediate 96cccc

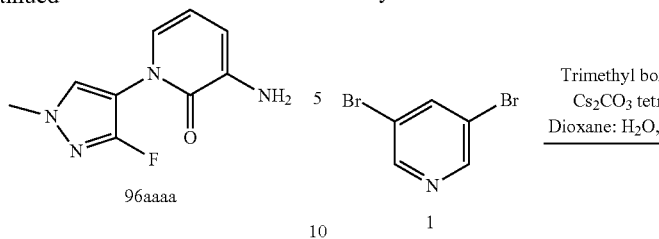

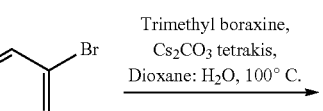

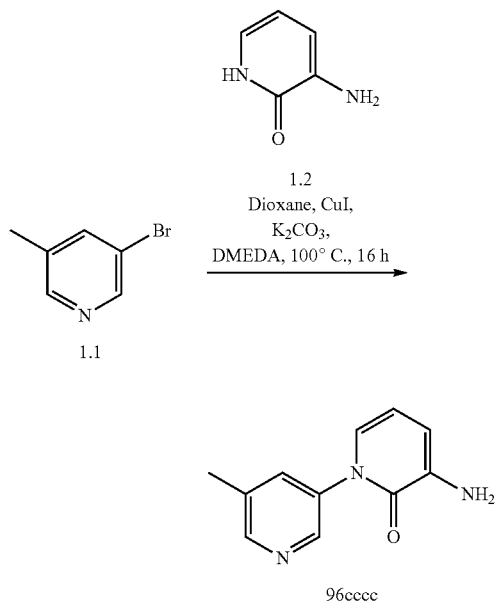

1371
-continued

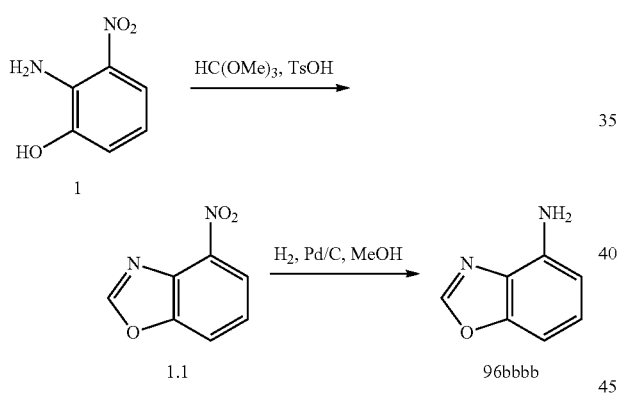

Synthesis of Compound 96aaaa.

To a solution of 1. (0.160 g, 0.893 mmol, 1.1 eq) and 1.1 (0.09 g, 0.812 mmol, 1.2 eq) in 1,4-dioxane (6 mL) was added potassium carbonate (0.220 g, 1.62 mmol, 2.0 eq) and degassed with argon for 15 min. Copper iodide (0.023 g, 0.121 mmol, 0.15 eq) and 1,2-dimethylethylenediamine (0.015 g, 0.162 mmol, 0.2 eq) was added and reaction mixture again degassed with argon for 5 min followed by heating at 100° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 96aaaa (0.026 g, 15.30%). MS(ES): m/z 209.19 [M+H]$^+$.

Synthesis of Intermediate 96bbbb.

Synthesis of Compound 1.1.

To a solution of 1 (1 g, 1.33 mmol, 1.0 eq) in trimethyl orthoformate (3.6 mL) was added p-toluene sulphonic acid (0.06 g) under nitrogen followed by heating at 80° C. in microwave for 15 min. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.1 (0.5 g, 46.95%). MS(ES): m/z 165.12 [M+H]$^+$.

Synthesis of Compound 96bbbb.

To a solution of 1.1 (0.5 g, 3.05 mmol, 1.0 eq) in methanol (5 mL), palladium on charcoal (0.05 g) was added. Hydrogen was purged through reaction mixture for 24 h at room temperature. After completion of reaction, reaction mixture was filtered through celite-bed and washed with methanol. Filtrate was concentrated under reduced pressure to obtain 96bbbb (0.3 g, 73.41.00%). MS(ES): m/z 135.14 [M+H]$^+$ Synthesis of Compound 1.1.

To a solution of 1. (10 g, 42.21 mmol, 1.0 eq) in 1,4-dioxane:water (9:1, 100 mL), Trimethyl boraxine (1.8 g, 14.35 mmol, 0.34 eq), cesium carbonate (13.7 g, 42.21 mmol, 1.0 eq) and tetrakis (4.8 g, 4.22 mmol, 0.1 eq) was added. The reaction mixture was heated at 110° C. for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by 15% ethylacetate in hexane to obtain 1.1. (2.6 g, Yield: 35.80%). MS (ES): m/z 173.03 [M+H]$^+$.

Synthesis of Compound 96cccc.

To a solution of 1.1 (2 g, 14.53 mmol, 1.0 eq) in 1,4-dioxane (20 mL), 1.2 (1.2 g, 11.62 mmol, 0.8 eq) was added. The reaction mixture was degassed for 10 min under argon atmosphere followed by addition of potassium carbonate (4.0 g, 29.06 mmol, 2.0 eq), N,N-dimethylethylenediamine (5.1 g, 58.12 mmol, 0.4 eq), and copper iodide (0.55 g, 2.90 mmol, 0.2 eq). The reaction mixture was heated at 100° C. for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96cccc (1 g, Yield: 34.19%). MS (ES): m/z 202.23 [M+H]$^+$.

Synthesis of Intermediate 96dddd.

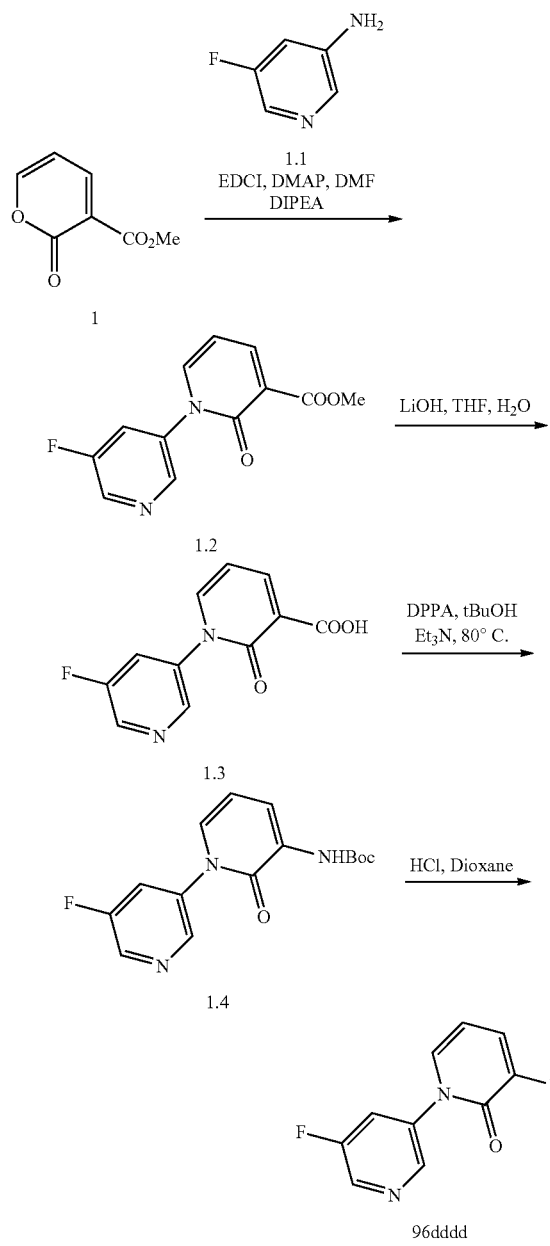

Synthesis of Compound 1.2.

To a cooled solution of 1. (1.0 g, 6.48 mmol, 1.0 eq), in N,N-dimethylformamide (12 mL) was added 1.1 (0.726 g, 6.48 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.3 g, 8.42 mmol, 1.3 eq), 4-Dimethylaminopyridine (0.157 g, 1.29 mmol, 0.2 eq) and N,N-Diisopropylethylamine (0.584 g, 4.53 mmol, 0.7 eq), was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (0.8 g, 49.67%). MS(ES): m/z 249.06 [M+H]$^+$.

Synthesis of Compound 1.3.

To a solution of 1.2 (0.8 g, 3.22 mmol, 1.0 eq), in tetrahydrofuran: water (10 mL, 2:1) was added lithium hydroxide (0.772 g, 32.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.6 g, 79.49%). MS(ES): m/z 235.05 [M+H]$^+$

Synthesis of Compound 1.4.

To a solution of 1.3 (0.6 g, 2.56 mmol, 1.0 eq) in tert.butanol (10 mL) was added triethylamine (0.439 g, 4.35 mmol, 1.7 eq) and diphenyl phosphoryl azide (0.913 g, 3.32 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.430 g, 54.97%). MS(ES): m/z 306.12 [M+H]$^+$.

Synthesis of Compound 96dddd.

A cooled solution of 1.4 (0.430 g, 1.40 mmol, 1 eq) in dioxane (6 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 96dddd. (0.3 g, 96.89%). MS(ES): m/z 206.07 [M+HCl]$^+$.

Synthesis of Intermediate 96eeee.

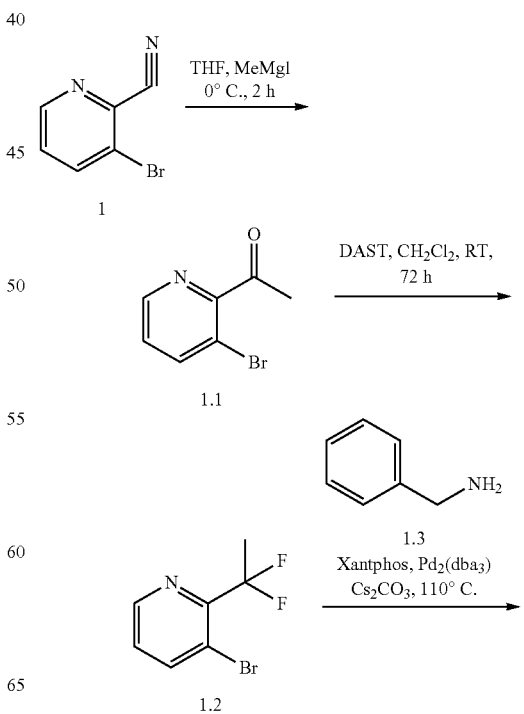

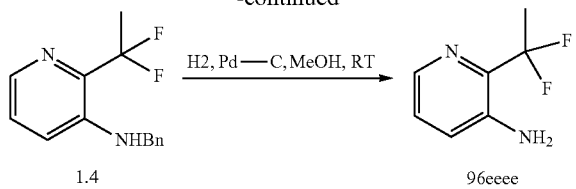

Synthesis of Compound 1.1.

To a cooled solution of 1 (5 g, 27.32 mmol, 1.0 eq) in tetrahydrofuran (100 mL) was added 3M methyl magnesium iodide (18 mL, 54.64 mmol, 2.0 eq). The reaction was stirred at 0° C. for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 14% ethyl acetate in hexane to obtain pure 1.1 (2.5 g, 45.74%), MS(ES): m/z 201.04[M+H]$^+$.

Synthesis of Compound 1.2.

To a cooled solution of 1.1 (2.5 g, 12.50 mmol, 1.0 eq) in dichloromethane (25 mL) was added diethylaminosulfur trifluoride (16.5 mL, 125 mmol, 10 eq) drop wise. The reaction was stirred at room temperature for 72 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 12% ethyl acetate in hexane to obtain pure 1.2 (2.5 g, 45.74%), MS(ES): m/z 201.04[M+H]$^+$.

Synthesis of Compound 1.4.

Compound was synthesized using general procedure B to obtain 1.4 (0.410 g, 45.83%), MS (ES): m/z 249.28 [M+H]$^+$.

Synthesis of Compound 96eeee.

To a solution of 1.4 (0.410 g, 1.65 mmol, 1.0 eq) in methanol (5 ml), palladium on charcoal (0.140 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 6% ethyl acetate in hexane to obtain pure 96eeee (0.170 g, 65.09%). MS (ES): m/z 159.15 [M+H]$^+$ Synthesis of Intermediate 96ffff.

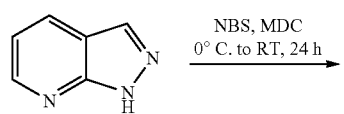

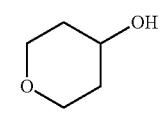

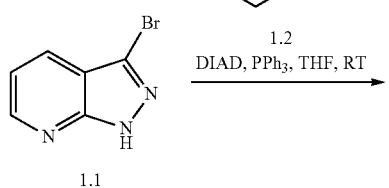

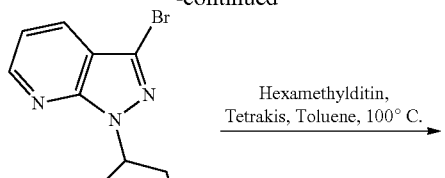

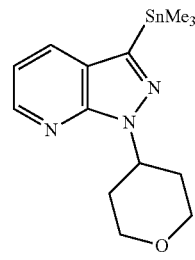

Synthesis of Compound 1.1.

To a stirred solution of 1 (3.0 g, 25.21 mmol, 1.0 eq) in dimethyl formamide (30 mL) was added N-bromosuccinimide (4.7 g, 26.47 mmol, 1.05 eq) at 10° C. under N$_2$ portionwise. Reaction mixture was stirred for 30 min. After completion of reaction, reaction mixture was transferred into ice cold water and the precipitated solid was collected by filtration, dried well to obtain 1.1 (3.23 g, 66.00%). MS(ES): m/z 198.96 [M+2H]$^+$.

Synthesis of Compound 1.3.

To a stirred solution of 1.1 (3.0 g, 15.15 mmol, 1.0 eq), 1.2 (3.1 g, 30.30 mmol, 2.0 eq) and triphenyl phosphine (7.9 g, 30.30 mmol, 2.0 eq) in dry tetrahydrofuran (75 mL) was added diisipropyl azodicarboxylate (6.1 g, 30.30 mmol, 2.0 eq) at 0° C. under Ar dropwise over 20 min. The reaction mixture was stirred at room temperature for 16 h. The reaction mixture was concentrated under reduced pressure to obtain the crude material. The residue was further purified by column chromatography and compound was eluted in 24% ethyl acetate in hexane to obtain pure 1.3 (3.0 g, 70.25%). MS(ES): m/z 283.21 [M+H]$^+$.

Synthesis of Compound 96ffff.

To a degassed solution of 1.3 (1.0 g, 3.54 mmol, 1.0 eq) and hexamethyl ditin (4.6 g, 14.18 mmol, 4.0 eq) in toluene (60 mL) was added tetrakis(triphenylphosphine)palladium (0) (0.410 g, 0.35 mmol, 0.1 eq) and the reaction mixture was heated at 100° C. for 2 h under N$_2$. Reaction mixture was cooled to room temperature purified by column chromaography using 6.0% ethyl acetate in hexane to obtain pure 96ffff (0.840 g, 64.61%). MS(ES): m/z 368.25 [M+H]$^+$.

Synthesis of Intermediate 96gggg.

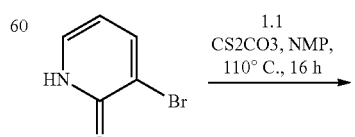

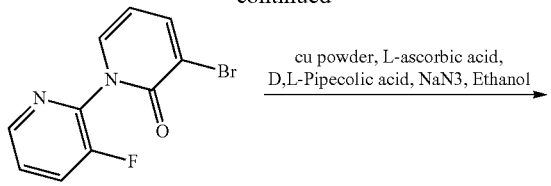

1.2

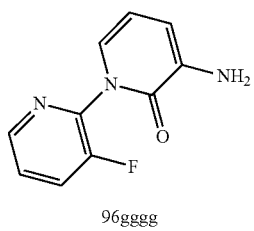

96gggg

Synthesis of Compound 1.2.

To a solution of 1. (3 g, 17.24 mmol, 1.0 eq) in N-methyl-2-pyrrolidone (60 mL), 1.1 (2.4 g, 21.55 mmol, 1.25 eq) and cesium carbonate (1.6 g, 51.72 mmol, 3.0 eq.) were added. The reaction mixture was heated at 110° C. for 16 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 40% ethylacetate in hexane to obtain 1.2. (0.71 g, Yield: 15.30%). MS (ES): m/z 270.07 [M+H]$^+$ Synthesis of Compound 96gggg.

To a solution of 1.2. (0.70 g, 2.60 mmol, 1.0 eq) in ethanol (9 mL), copper powder (0.01 g, 0.31 mmol, 0.12 eq), L-ascorbic acid (0.09 g, 0.52 mmol, 0.2 eq) and Sodium azide (0.33 g, 5.2 mmol, 2.0 eq.) was added. The reaction mixture was heated at 100° C. for 20 h. After completion of reaction, reaction mixture was filtered through celite and product was extracted with ethylacetate. Organic layer was combined, washed with brine solution, dried over sodium sulphate and concentrated under reduced pressure to obtain crude material. This was further purified by 70% ethylacetate in hexane to obtain 96ggg (0.23 g, Yield: 43.09%). MS (ES): m/z 207.19 [M+H]$^+$ Synthesis of Intermediate 96hhhh.

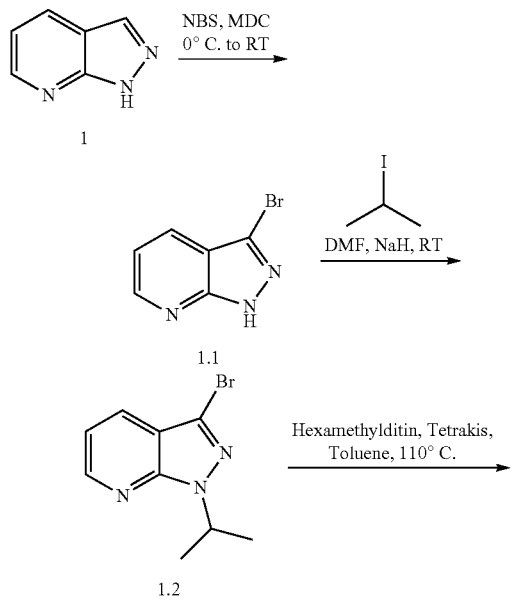

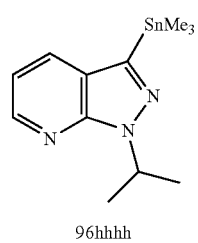

96hhhh

Synthesis of Compound 1.1.

To a stirred solution of 1 (3.0 g, 25.21 mmol, 1.0 eq) in dimethyl formamide (30 mL) was added N-bromo succinimide (4.7 g, 26.47 mmol, 1.05 eq) at 10° C. under N$_2$ portionwise. Reaction mixture was stirred for 30 min. After completion of reaction, reaction mixture was transferred into ice cold water and the precipitated solid was collected by filtration, dried well to obtain 1.1 (3.23 g, 66.00%). MS(ES): m/z 198.96 [M+2H]$^+$.

Synthesis of Compound 1.2.

To a stirred suspension of sodium hydride (0.796 g, 19.89 mmol, 1.3 eq, 60% dispersion) in N,N-dimethyl formamide (10 mL) was added a solution of 1.1 (3.0 g, 15.30 mmol, 1.0 eq) in N,N-dimethyl formamide (15 mL) dropwise at 0° C. under N$_2$. The mixture was stirred for 20 mins under the same conditions and a solution of isopropyl iodide (3.1 g, 18.36 mmol, 1.2 eq) in N,N-dimethyl formamide (5 mL) was added dropwise. The reaction mixture was stirred at room temperature for 14 h. After completion of reaction, reaction mixture was transferred into ice cold water and the product was extracted with ethyl acetate. Organic layer was combined, washed with brine, dried over sodium sulfate and concentrated under reduced pressure to obtain crude material. This was further purified by column chromaography using 30% ethyl acetate in hexane as eluant to obtain pure 1.2 (2.46 g, 67.5%). MS(ES): m/z 240.41 [M+H]$^+$.

Synthesis of Compound 96hhhh.

To a degassed solution of 1.2 (0.200 g, 0.83 mmol, 1.0 eq) and hexamethyl ditin (1.05 g, 3.33 mmol, 4.0 eq) in toluene (10 mL) was added Tetrakis(triphenylphosphine)palladium (0) (0.097 g, 0.08 mmol, 0.1 eq) and the reaction mixture was heated at 100° C. for 1 h under N$_2$. The RM was cooled to room temperature purified by column chromaography using 5.0% ethyl acetate in hexane as eluant to obtain pure 96hhhh (0.260 g, 99.05%). MS(ES): m/z 325.44 [M+H]$^+$.

Synthesis of Intermediate 96iiii.

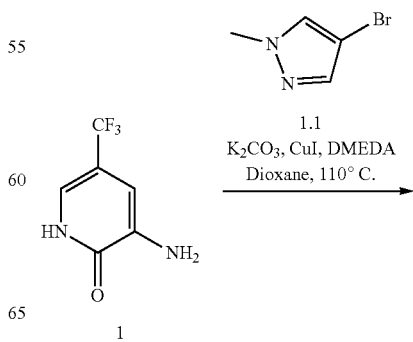

1

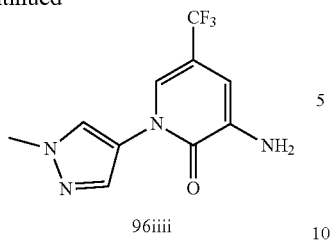

96iiii

Synthesis of Compound 96iiii.

To a solution of 1. (0.5 g, 2.80 mmol, 1 eq) and 1.1 (0.54 g, 3.36 mmol, 1.2 eq) in 1,4-dioxane (15 mL) was added potassium carbonate (0.772 g, 5.6 mmol, 2.0 eq) and degassed with argon for 15 min. Copper iodide (0.106 g, 0.56 mmol, 0.2 eq) and 1,2-dimethylethylenediamine (0.098 g, 1.12 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96iiii. (0.3 g, 41.39%). MS(ES): m/z 259.08 [M+H]$^+$.

Synthesis of Intermediate 96jjjj.

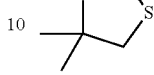

1.1
THF, RT

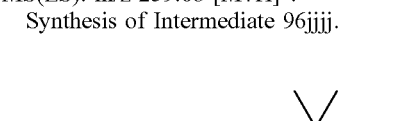

1

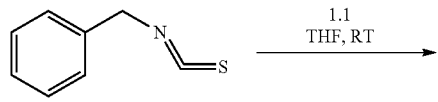

CDI (1.5 eq), THF RT 1.2

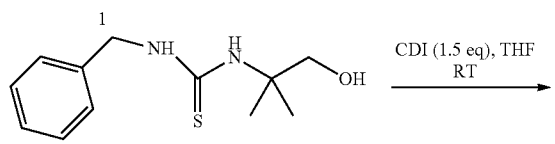

1) Triflic acid, DCM, Aq w/up
2) (Boc)$_2$O, DMAP NaHCO$_3$, Water, THF, RT 1.3

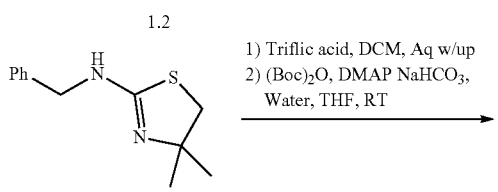

4M HCl in Dioxane, RT 1.4

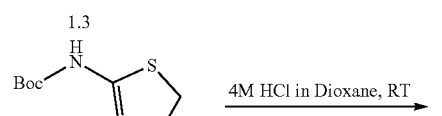

1.5

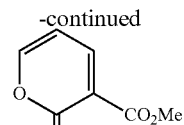

1.6
EDCl, DMAP, DMF

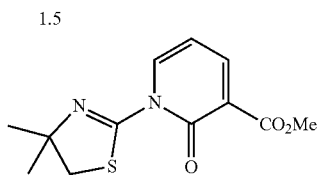

1.7
LiOH, THF, H$_2$O

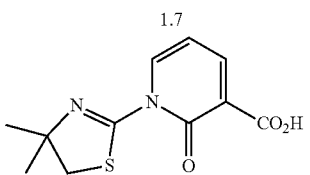

1.8
DPPA, tBuOH, Et$_3$N, 80° C.

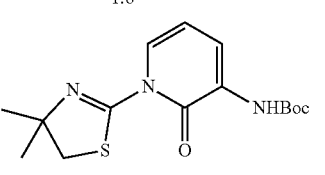

1.9
HCl, Dioxane

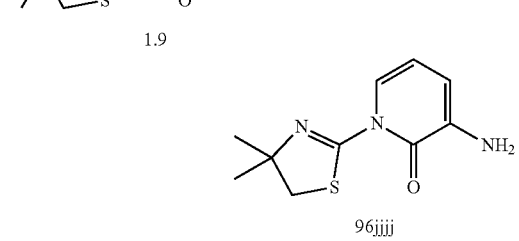

96jjjj

Synthesis of Compound 1.2.

To a solution of 1 (10 g, 67.11 mmol, 1.0 eq) in tetrahydrofuran (100 ml), 2-amino-2-methylpropan-1-ol (7.17 g, 80.53 mmol, 1.2 eq) was added. The reaction mixture was stirred at room temperature for 4 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.2. (14 g, Yield: 87.64%). MS (ES): m/z 239.1 [M+H]$^+$ Synthesis of Compound 1.3.

To a solution of 1 (14 g, 58.73 mmol, 1.0 eq) in tetrahydrofuran (140 mL), Carbonyldiimidazole (14.28 g, 88.09 mmol, 1.5 eq) was added. The reaction mixture was stirred at room temperature for 2 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.3. (11.2 g, Yield: 86.54%). MS (ES): m/z 221.1 [M+H]$^+$.

Synthesis of Compound 1.4.

To a solution of 1.3 (11.2 g, 50.83 mmol, 1.0 eq) in dichloromethane (110 mL) was added triflic acid (56 ml) at 0° C. Reaction mixture was stirred at room temperature for 24 h. After completion of reaction, reaction mixture was transferred into ice cold water and used for next step. In the reaction mixture Di-tert-butyl dicarbonate (16.62 g, 76.24 mmol, 1.5 eq) and 4-Dimethylaminopyridine (1.23 g, 10.16 mmol, 0.2 eq) in tetrahydrofuran (100 ml) was added. The reaction mixture was stirred at room temperature for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 20% ethyl acetate in hexane to obtain 1.4. (4.6 g, 39.29%), MS(ES): m/z 231.1 [M+H]$^+$ Synthesis of Compound 1.5.

To 1.4 (1.4 g, 6.07 mmol, 1.0 eq) was added 4M hydrochloric acid in 1,4 Dioxane (14 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 1.5. (0.860 g, 84.89%). MS (ES): m/z 167.04 [M+H]$^+$.

Synthesis of Compound 1.7.

To a cooled solution of 1.5 (0.860 g, 5.15 mmol, 1.0 eq), in N,N-dimethylformamide (50 mL) was added 1.6. (0.793 g, 5.15 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.27 g, 6.69 mmol, 1.3 eq) and 4-Dimethylaminopyridine (0.156 g, 1.28 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.7. (0.650 g, 47.30%). MS(ES): m/z 267.08 [M+H]$^+$.

Synthesis of Compound 1.8.

To a solution of 1.7 (0.650 g, 2.44 mmol, 1.0 eq), in tetrahydrofuran: methanol: water (6.5 mL, 2:2:1) was added lithium hydroxide (1.0 g, 24.4 mmol, 10 eq). The reaction was stirred at 60° C. for 16 h. After completion of reaction, reaction mixture was concentrated under reduced pressure to obtain residue. To this added water and acidified with IN hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.8. (0.532 g, 86.40%). MS(ES): m/z 253.06 [M+H]$^+$.

Synthesis of Compound 1.9.

To a solution of 1.8 (0.532 g, 2.10 mmol, 1.0 eq) in tert-butanol (10 mL) was added triethylamine (0.360 g, 3.57 mmol, 1.7 eq) and diphenyl phosphoryl azide (0.751 g, 2.73 mmol, 1.3 eq) under nitrogen followed by heating at 80° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.9. (0.355 g, 52.05%). MS(ES): m/z 324.1 [M+H]$^+$.

Synthesis of Compound 96jjjj. To 1.9 (0.355 g, 1.09 mmol, 1.0 eq) was added 4M hydrochloric acid in 1,4-dioxane (4 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 96jjjj. (0.205 g, 83.64%). MS (ES): m/z 224.08 [M+H]$^+$.

Synthesis of Intermediate 96kkkk.

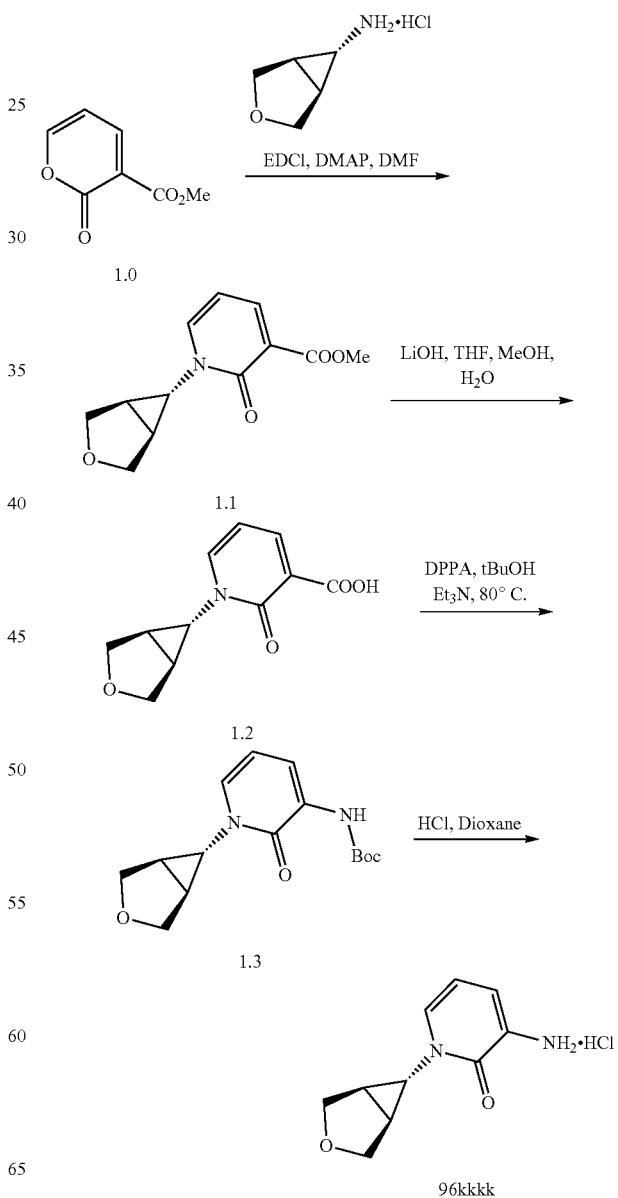

Synthesis of Compound 1.1.

To a solution of 1.0 (0.250 g, 1.62 mmol, 1.0 eq) in N,N-dimethylformamide (12 mL) was added (1R,5S,6r)-3-oxabicyclo[3.1.0]hexan-6-amine hydrochloride (0.218 g, 1.62 mmol, 1.0 eq). The reaction mixture was stirred at room temperature for 1 h followed by addition of N-Ethyl-N'-(3-dimethylaminopropyl) carbodiimide hydrochloride (0.402 g, 2.10 mmol, 1.3 eq) and 4-dimethylaminopryidine (0.049 g, 0.405 mmol, 0.25 eq). The reaction was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 30% ethyl acetate in hexane as eluant to 1.1 (0.180 g, Yield: 47.17%). MS(ES): m/z 236.24 [M+H]$^+$ Synthesis of Compound 1.2.

To a solution of 1.1 (0.180 g, 0.765 mmol, 1.0 eq), in tetrahydrofuran: methanol: water (5 mL, 1:1:1) was added lithium hydroxide (0.160 g, 3.82 mmol, 5.0 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.2 (0.140 g, Yield: 82.71%). MS(ES): m/z: 222.07 [M+H]$^+$.

Synthesis of Compound 1.3.

To a solution of 1.2 (0.140 g, 0.632 mmol, 1.0 eq) in Tert-Butyl alcohol was added diphenylphosphorylazide (0.226 g, 0.821 mmol, 1.3 eq), triethylamine (0.108 g, 1.074 mmol, 1.7 eq). The reaction was stirred at 90° C. for 16 h. After completion of reaction, reaction mixture was concentrated under reduced pressure to obtain crude material. This was further purified by combi flash using 1.0% MeOH in Dichloromethane as eluent to 1.3 (0.150 g, Yield: 81.08%). MS(ES): m/z 293.34 [M+H]$^+$.

Synthesis of Compound 96kkkk

To 1.3 (0.150 g, 0.513 mmol, 1.0 eq) was added 4M hydrochloric acid in 1,4-Dioxane (7 mL) and stirred at room temperature for 4 h. After completion of reaction, reaction mixture was concentrated under reduced pressure, residue was triturated with diethyl ether to obtain 96kkkk (0.090 g, 76.70%). MS (ES): m/z 229.68 [M+H]$^+$ Synthesis of Intermediate 96llll.

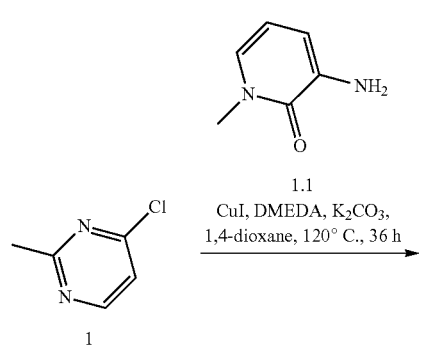

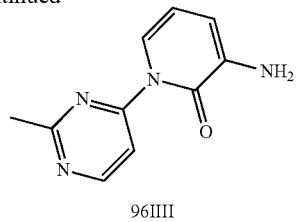

96IIII

Synthesis of Compound 96llll.

To a solution of 1 (0.5 g, 3.90 mmol, 1.0 eq) and 1.1 0.58 g, 4.68 mmol, 1.2 eq) in 1,4-dioxane was added potassium carbonate (1.34 g, 9.75 mmol, 2.5 eq) and reaction mixture was degassed with Argon for 10 min. To this N,N'-Dimethylethylenediamine (0.14 g, 1.56 mmol, 0.4 eq) was added followed by addition of copper(I) iodide (015 g, 0.79 mmol, 0.2 q). The reaction mixture was heated to 120° C. for 36 h. After completion of reaction, reaction mixture was transferred into water and extracted with ethyl acetate. Organic layer combined, washed with brine, dried over sodium sulphate and concentrated under reduced pressure to obtain crude material. Several batches were combined and further purified by column chromatography and compound was eluted in 50% ethyl acetate in hexane to obtain 96llll (0.3 g, 4.76%). MS(ES): m/z 203.09 [M+H]$^+$.

Synthesis of Intermediate 96mmmm.

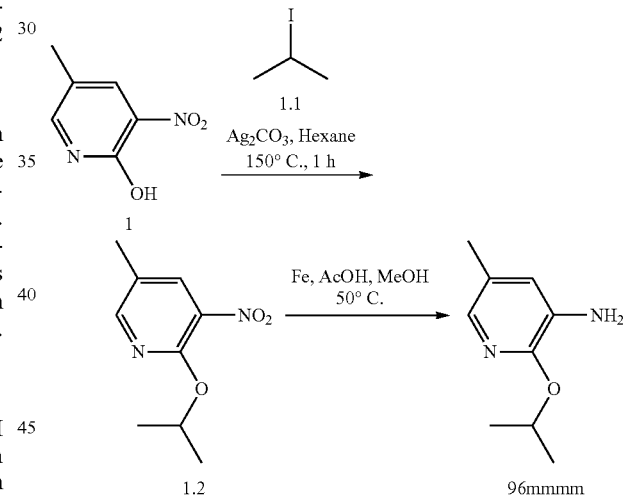

Synthesis of Compound 1.2.

To a solution of 1 (3 g, 19.4 mmol, 1 eq) in hexane (30 mL) was added 1.1 (3.89 mL, 38.96 mmol, 2 eq) followed by addition of silver carbonate (6.40 g, 23.3 mmol, 1.2 eq). The reaction was stirred at 150° C. for 1 h. After completion of reaction, reaction mixture was filtered through celite-bed and washed with ethyl acetate. Filtrate was concentrated under reduced pressure to obtain crude material. This was further purified by column chromatography and compound was eluted in 12% ethyl acetate in hexane to obtain pure 1.2 (1.5 g, 39.28%), MS(ES): m/z 197.21 [M+H]$^+$.

Synthesis of Compound 96mmmm.

To 1.2 (1.5 g, 7.65 mmol, 1.0 eq) added mixture of methanol:water (30 mL, 4:1) and acetic acid (4.41 mL, 76.5 mmol, 10 eq). The reaction mixture was heated 50° C. for 30 min. then iron powder (3.38 g, 60.48 mmol, 8 eq) was added portionwise. The reaction was stirred at 50° C. for 30 min. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 16% ethyl acetate in hexane to obtain pure 96mmmm (1 g, 78.69%). MS(ES): m/z 167.22 [M+H]⁺.

Synthesis of Intermediate 96nnnn.

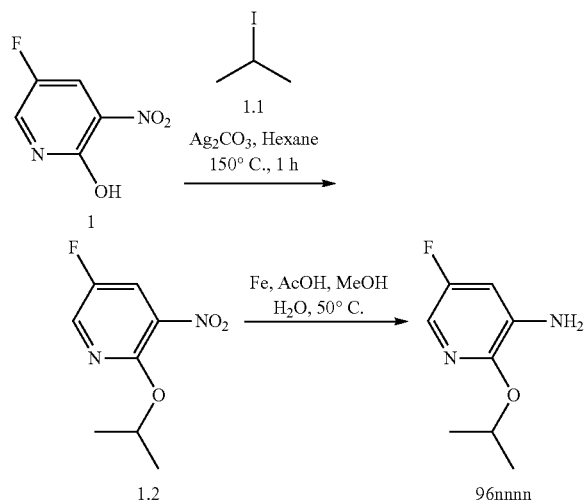

Synthesis of Compound 1.2.

To a solution of 1 (3 g, 18.98 mmol, 1 eq) in hexane (50 mL) was added 1.1 (3.79 mL, 37.97 mmol, 2 eq) followed by addition of silver carbonate (6.28 g, 22.27 mmol, 1.2 eq). The reaction was stirred at 150° C. for 1 h. After completion of reaction, reaction mixture was filtered through celite-bed and washed with ethyl acetate. Filtrate was concentrated under reduced pressure to obtain crude material. This was further purified by column chromatography and compound was eluted in 6% ethyl acetate in hexane to obtain pure 1.2 (2.2 g, 48.29%), MS(ES): m/z 197.16 [M+H]⁺.

Synthesis of Compound 96nnnn.

To 1.2 (2.2 g, 10.99 mmol, 1.0 eq) added mixture of methanol:water (44 mL, 4:1), acetic acid (6.34 mL, 109.9 mmol, 10 eq) and iron powder (4.92 g, 87.92 mmol, 8 eq) was added. The reaction was stirred at 50° C. for 30 min. After completion of reaction, reaction mixture was filtered through celite-bed and washed with ethyl acetate. Filtrate was concentrated under reduced pressure to obtain crude material. This was further purified by column chromatography and compound was eluted in 14% ethyl acetate in hexane to obtain pure 96nnnn (1.3 g, 68.47%). MS(ES): m/z 173.61 [M+H]⁺.

Synthesis of Intermediate 96oooo.

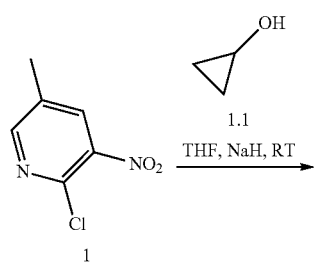

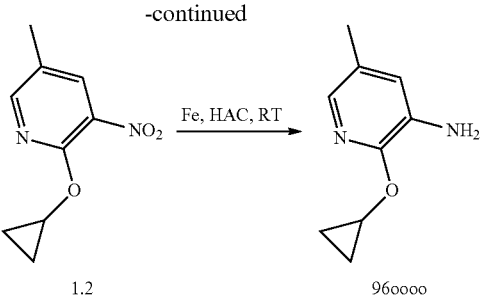

Synthesis of Compound 1.2.

To a cooled solution of 1 (1 g, 5.79 mmol, 1.0 eq) in tetrahydrofuran (10 mL) was added sodium hydride (0.166 g, 11.58 mmol, 2.0 eq) followed by addition of 1.1 (0.437 g, 7.53 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 14% ethyl acetate in hexane to obtain pure 1.2 (0.750 g, 66.65%), MS(ES): m/z 195.19 [M+H]⁺.

Synthesis of Compound 96oooo.

To a solution of 1.2 (0.750 g, 3.86 mmol, 1.0 eq) in acetic acid (11 ml), iron powder (1.08 g, 19.3 mmol, 5.0 eq) was added. The reaction was stirred at room temperature for 1 h. After completion of reaction, reaction mixture was filtered through celite-bed and washed with methanol. Filtrate was concentrated under reduced pressure to obtain crude material. This was further purified by column chromatography and compound was eluted in 1.6% methanol in dichloromethane to obtain pure 96oooo (0.600 g, 94.61%). MS (ES): m/z 165.21 [M+H]⁺.

Synthesis of Intermediate 96pppp.

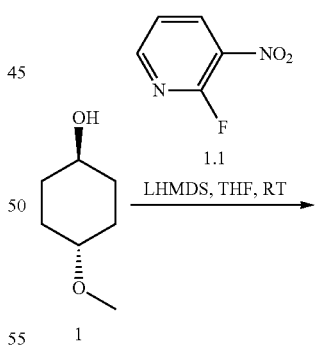

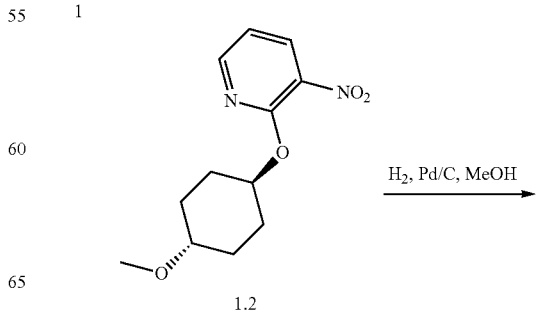

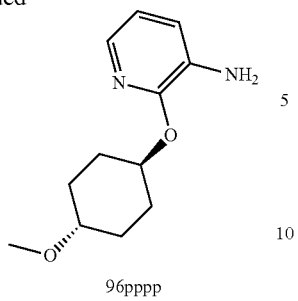

96pppp

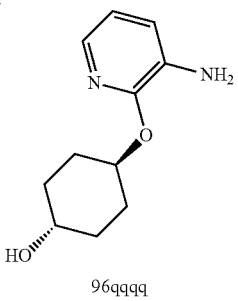

96qqqq

Synthesis of Compound 1.2.

To a cooled solution of 1 (0.500 g, 3.84 mmol, 1.0 eq) in tetrahydrofuran (6 mL) was added lithium bis(trimethylsilyl)amide (9.6 mL, 9.6 mmol, 2.5 eq) followed by addition of 1.1 (0.546 g, 3.84 mmol, 1.0 eq) under nitrogen atmosphere. The reaction was stirred at room temperature for 12 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 8% ethyl acetate in hexane to obtain pure 1.2 (0.370 g, 38.19%), MS(ES): m/z 253.27 [M+H]$^+$.

Synthesis of Compound 1.3.

To a solution of 1.2 (0.370 g, 1.47 mmol, 1.0 eq) in methanol (10 ml), palladium on charcoal (0.100 g) was added. Hydrogen was purged through reaction mixture for 16 h at room temperature. After completion of reaction, reaction mixture was filtered through celite-bed and washed with methanol. Filtrate was concentrated under reduced pressure to obtain crude material. This was further purified by column chromatography and compound was eluted in 22% ethyl acetate in hexane to obtain pure 1.3 (0.370 g, 92.02%). MS (ES): m/z 223.29 [M+H]$^+$ Synthesis of Intermediate 96qqqq.

Synthesis of Compound 1.2.

To a cooled solution of 1 (2 g, 17.24 mmol, 1 eq) in tetrahydrofuran (20 mL) was added lithium bis(trimethylsilyl)amide (12.5 mL, 12.58 mmol, 0.73 eq) followed by addition of 1.1 (2.4 g, 17.24 mmol, 1 eq) under nitrogen atmosphere. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 26% ethyl acetate in hexane to obtain pure 1.2 (0.740 g, 18.04%), MS(ES): m/z 239.24 [M+H]$^+$.

Synthesis of Compound 96qqqq.

To a solution of 1.2 (0.740 g, 3.11 mmol, 1.0 eq) in methanol (8 ml), palladium on charcoal (0.200 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by trituration with pantane to obtain pure 96qqqq (0.490 g, 75.75%). MS (ES): m/z 209.26 [M+H]$^+$.

Synthesis of Intermediate 96rrrr.

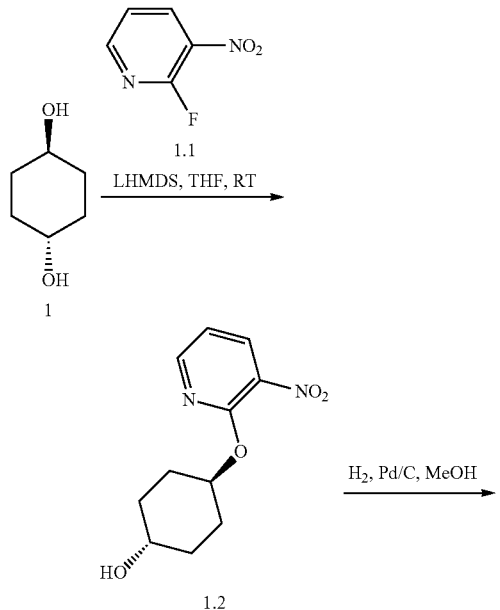

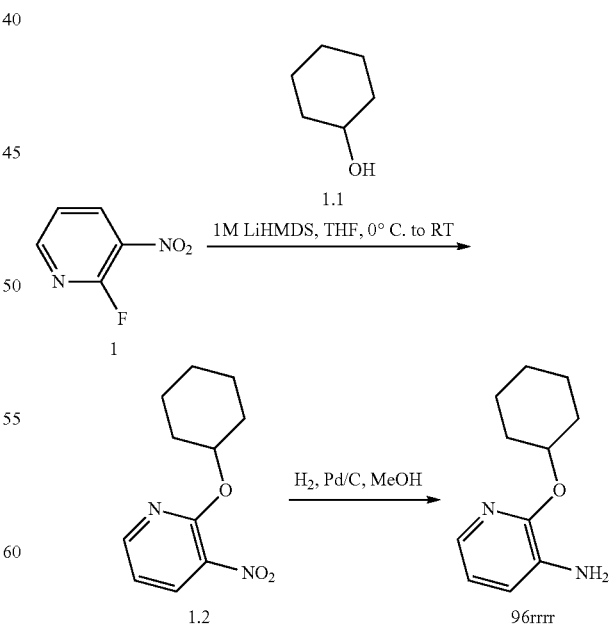

Synthesis of Compound 1.2.

To a cooled solution of 1 (0.500 g, 3.52 mmol, 1 eq) in tetrahydrofuran (6 mL) was added lithium bis(trimethylsilyl)amide (7 mL, 7.04 mmol, 2 eq) followed by addition of 1.1 (0.458 g, 4.57 mmol, 1.3 eq) under nitrogen. The reaction was stirred at 0° C. for 1 h. After completion of reaction, reaction mixture was transferred into ice cold water and product was extracted with ethyl acetate. Organic layer was combined, dried over sodium sulphate and concentrated under reduced pressure to obtain crude material. This was further purified by column chromatography and compound was eluted in 10% ethyl acetate in hexane to obtain pure 1.2 (0.200 g, 25.57%), MS(ES): m/z 223.24 [M+H]$^+$.

Synthesis of Compound 96rrrr.

To a solution of 1.2 (0.200 g, 0.899 mmol, 1.0 eq) in methanol (3 ml), palladium on charcoal (0.050 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 0.9% methanol in dichloromethane to obtain pure 96rrrr (0.120 g, 69.36%). MS (ES): m/z 193.26 [M+H]$^+$ Synthesis of Intermediate 96ssss.

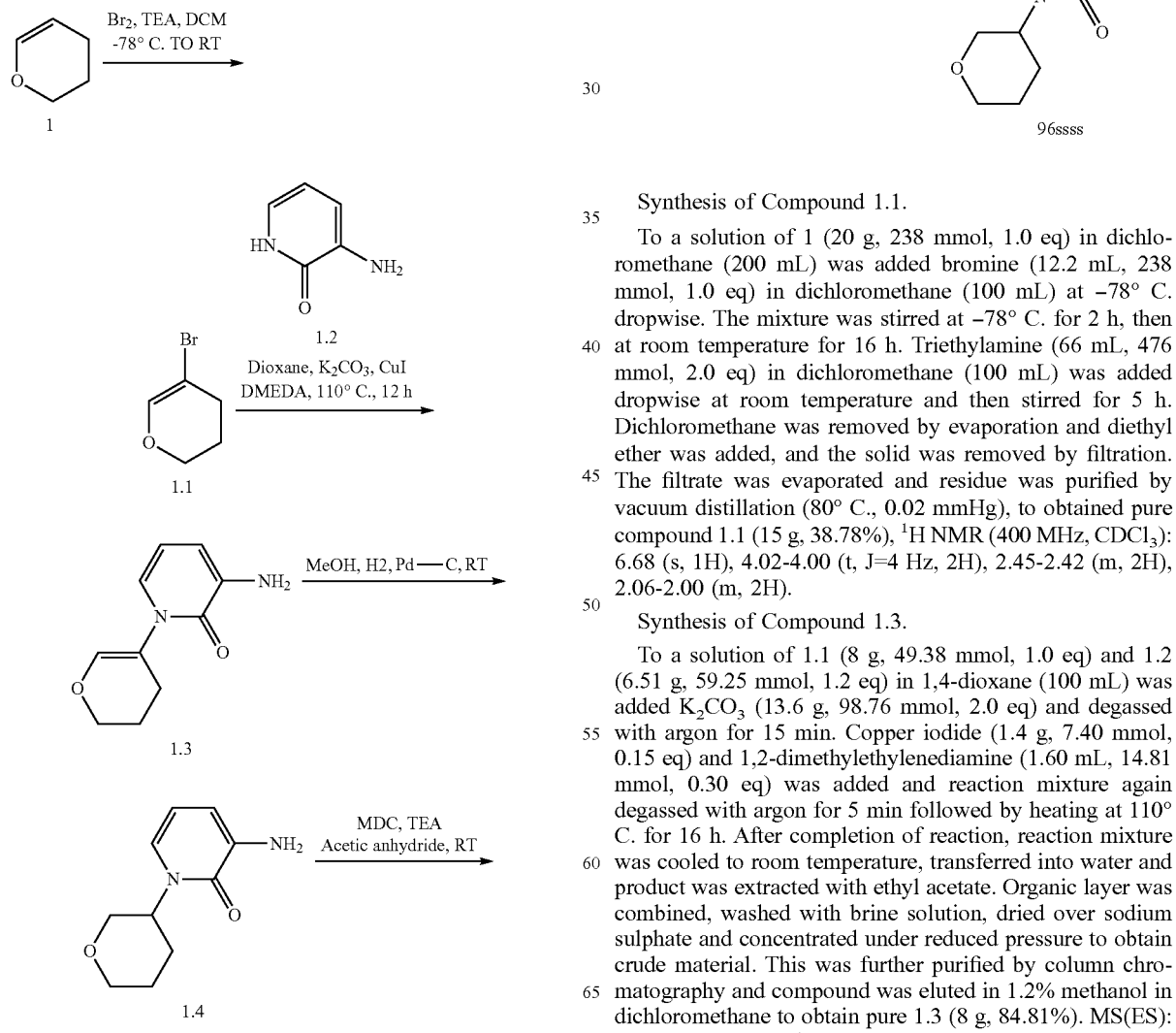

Synthesis of Compound 1.1.

To a solution of 1 (20 g, 238 mmol, 1.0 eq) in dichloromethane (200 mL) was added bromine (12.2 mL, 238 mmol, 1.0 eq) in dichloromethane (100 mL) at −78° C. dropwise. The mixture was stirred at −78° C. for 2 h, then at room temperature for 16 h. Triethylamine (66 mL, 476 mmol, 2.0 eq) in dichloromethane (100 mL) was added dropwise at room temperature and then stirred for 5 h. Dichloromethane was removed by evaporation and diethyl ether was added, and the solid was removed by filtration. The filtrate was evaporated and residue was purified by vacuum distillation (80° C., 0.02 mmHg), to obtained pure compound 1.1 (15 g, 38.78%), $^1$H NMR (400 MHz, CDCl$_3$): 6.68 (s, 1H), 4.02-4.00 (t, J=4 Hz, 2H), 2.45-2.42 (m, 2H), 2.06-2.00 (m, 2H).

Synthesis of Compound 1.3.

To a solution of 1.1 (8 g, 49.38 mmol, 1.0 eq) and 1.2 (6.51 g, 59.25 mmol, 1.2 eq) in 1,4-dioxane (100 mL) was added K$_2$CO$_3$ (13.6 g, 98.76 mmol, 2.0 eq) and degassed with argon for 15 min. Copper iodide (1.4 g, 7.40 mmol, 0.15 eq) and 1,2-dimethylethylenediamine (1.60 mL, 14.81 mmol, 0.30 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 1.3 (8 g, 84.81%). MS(ES): m/z 193.09 [M+H]$^+$.

Synthesis of Compound 1.4.

To a solution of 1.3 (8 g, 20.83 mmol, 1.0 eq) in methanol (100 mL), palladium on charcoal (4 g) was added. Hydrogen was purged through reaction mixture for 16 h at room temperature. After completion of reaction, reaction mixture was filtered through celite-bed and washed with methanol. Filtrate was concentrated under reduced pressure to obtain crude material. This was further purified by trituration with n-pentane to obtain pure 1.4 (4 g, 49.48%). MS (ES): m/z 195.11 [M+H]+

Synthesis of Compound 1.5.

To a cooled solution of 1.4 (2 g, 10.30 mmol, 1.0 eq) in dichloromethane (20 mL) at 0° C. was added triethylamine (4.33 mL, 30.9 mmol, 3.0 eq) and acetic anhydride (1.55 mL, 16.49 mmol, 1.6 eq). The reaction was stirred at room temperature for 2 h. After completion of reaction, reaction mixture was transferred into water and product was extracted with dichloromethane. Organic layer was combined and dried over sodium sulphate and concentrated under reduced pressure to obtain crude material. This was further purified by column chromatography and compound was eluted in 0-5% Methanol in DCM to obtain pure 1.5 (2.3 g, 94.54%). MS (ES): m/z 237.12 [M+H]+

Synthesis of Compound 1.6.

To a cooled solution of 1.5 (2.3 g, 9.70 mmol, 1.0 eq), in dichloromethane (20 mL) at 0° C. was added N-chlorosuccinimide (1.95 g, 14.55 mmol, 1.5 eq). The reaction was stirred at room temperature for 16 h. After completion of reaction, reaction mixture was transferred into water and product was extracted with dichloromethane. Organic layer was combined and dried over sodium sulphate and concentrated under reduced pressure to obtain crude material. This was further purified by column chromatography and compound was eluted in 0-5% Methanol in DCM to obtain pure 1.6 (0.7 g, 26.56%). MS (ES): m/z 271.08 [M+H]+

Synthesis of Compound 96ssss.

To a solution of compound 1.6 (0.7 g, 2.59 mmol, 1.0 eq) in methanol (20 mL) was added K$_2$CO$_3$ (3.57 g, 25.92 mmol, 10 eq.). The reaction was heated at 60° C. for 16 h. After completion of reaction, methanol was evaporated and solid was diluted with water and extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 96ssss (0.4 g, 67.65%). MS(ES): m/z: 229.07 [M+H]+.

Synthesis of Intermediate 96tttt.

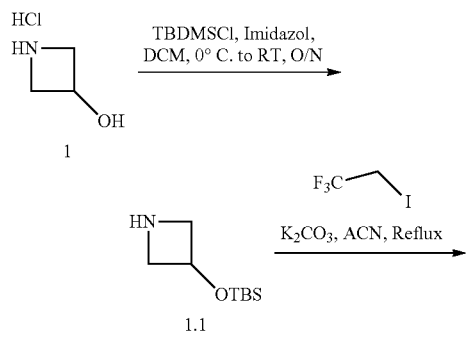

Synthesis of Compound 1.1:

To a solution of 1 (2.0 g, 55.86 mmol, 1.0 eq) in dichloromethane (10 mL) was added imidazole (18 g, 277 mmol, 5.0 eq). The reaction mixture was stirred at room temperature for 30 min. Further tert-Butyldimethylsilyl chloride (12.5 g, 83.79 mmol, 1.5 eq) was added and the reaction mixture was stirred at room temperature for 15 h. After completion of reaction, reaction mixture was transferred into water and product was extracted with dichloromethane. Organic layer was combined, washed with brine solution, dried over sodium sulphate and concentrated under reduced pressure to obtain product 1.1 (1.2 g, 19.46%). MS(ES): m/z 188.36 [M+H]+.

Synthesis of Compound 1.2:

To a solution of 1.1 (2.0 g, 10 mmol, 1.0 eq), in acetonitrile (30 mL) were added potassium carbonate (2.9 g, 21.39 mmol, 2 eq) and 1,1,1-trifluoro-2-iodoethane (3.3 g, 15 mmol, 1.5 eq)) at room temperature. The reaction mixture was refluxed for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (1.2 g, 41.73%). MS(ES): m/z 270.38 [M+H]+.

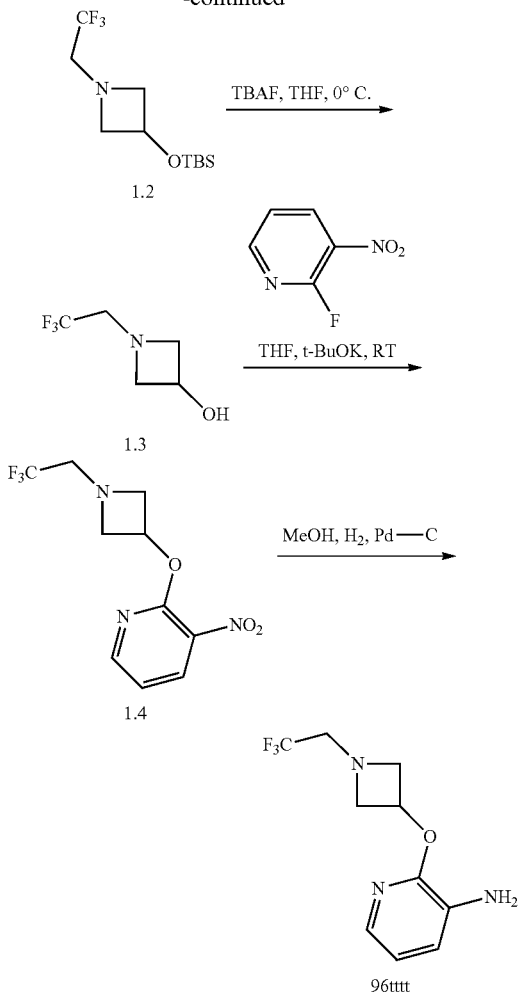

Synthesis of Compound 1.3:

To a cooled solution of 1.2 (1.2 g, 4.45 mmol, 1.0 eq), in tetrahydrofuran (30 mL) were added tetra-n-butylammonium fluoride (5.82 g, 22.3 mmol, 5.0 eq) at 0° C. The reaction mixture was stirred at room temperature for 3 h. After completion of reaction, reaction mixture was transferred into water and precipitated solid was filtered and dried well to obtain 1.3 (0.650 g, 156.12%). MS(ES): m/z 92.62 [M+H]$^+$ Synthesis of Compound 1.4:

To a cooled solution of 1.3 (0.670 g, 4.13 mmol, 1.0 eq), and 2-fluoro-3-nitropyridine (0.584 g, 4.13 mmol, 1.0 eq) in tetrahydrofuran (10 mL) at 0° C. was added potassium ter-butoxide (4.13 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 1.4 (0.500 g, 43.72%). MS (ES): m/z 278.2 [M+H]$^+$.

Synthesis of Compound 96tttt.

To a solution of 1.4 (0.500 g, 1.8 mmol, 1.0 eq) in methanol (10 mL), palladium on charcoal (0.2 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96tttt (0.4 g, 89.70%). MS (ES): m/z 248.22 [M+H]$^+$.

Synthesis of Intermediate 96uuuu.

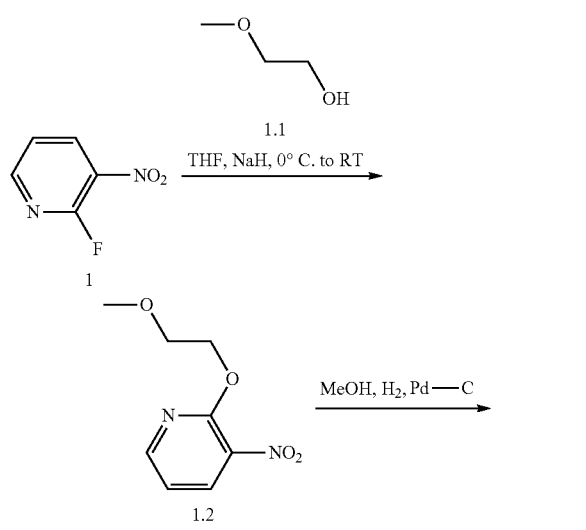

Synthesis of Compound 1.2.

To a cooled solution of 1 (2 g, 14.08 mmol, 1 eq) in tetrahydrofuran (20 mL) was added sodium hydride (1.12 g, 28.16 mmol, 2 eq) followed by addition of 1.1 (1.61 g, 21.1 mmol, 1.5 eq) under nitrogen. The reaction was stirred at 0° C. for 30 min. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 11% ethyl acetate in hexane to obtain pure 1.2 (1.7 g, 60.94%), MS(ES): m/z 199.18 [M+H]$^+$.

Synthesis of Compound 96uuuu.

To a solution of 1.2 (1.7 g, 8.58 mmol, 1.0 eq) in methanol (15 ml), palladium on charcoal (0.500 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 1% methanol in dichloromethane to obtain pure 96uuuu (1.3 g, 90.10%). MS (ES): m/z 169.20 [M+H]$^+$.

Synthesis of Intermediate 96wwww.

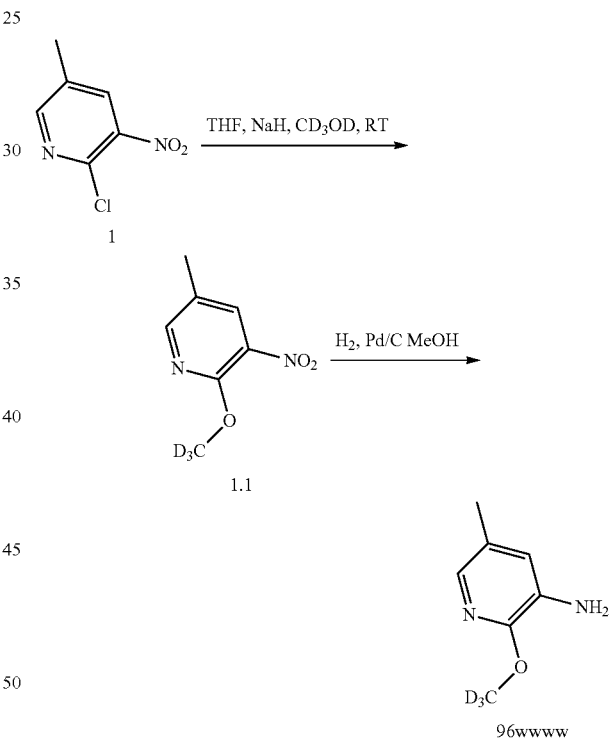

Synthesis of Compound 1.1.

To a cooled solution of 1 (0.500 g, 2.90 mmol, 1 eq) in tetrahydrofuran (5 mL) was added sodium hydride (0.084 g, 5.80 mmol, 2 eq) followed by addition of tetradeuteromethanol (0.114 g, 3.19 mmol, 1.1 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 13% ethyl acetate in hexane to obtain pure 1.1 (0.400 g, 80.65%), MS(ES): m/z 171.17 [M+H]$^+$.

Synthesis of Compound 96wwww.

To a solution of 1.1 (0.400 g, 5.73 mmol, 1.0 eq) in methanol (5 ml), palladium on charcoal (0.100 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 96wwww (0.300 g, 90.93%). MS (ES): m/z 142.19 [M+H]$^+$.

Synthesis of Intermediate 96vvvv.

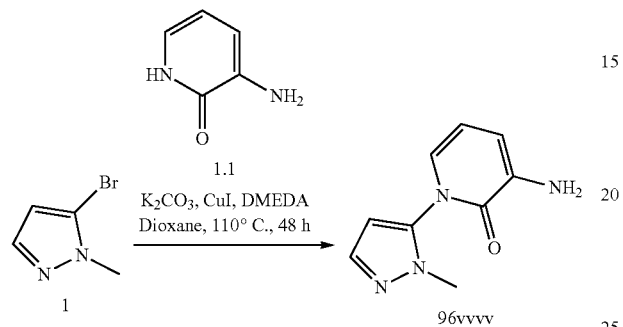

Synthesis of Compound 96vvvv.

To a solution of 1. (2 g, 12.42 mmol, 1 eq) and 1.1 (1.64 g, 14.91 mmol, 1.2 eq) in 1,4-dioxane (20 mL) was added potassium carbonate (3.42 g, 24.84 mmol, 2.0 eq) and degassed with argon for 15 min. Copper iodide (0.354 g, 1.86 mmol, 0.15 eq) and 1,2-dimethylethylenediamine (0.328 g, 3.72 mmol, 0.3 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 2.1% methanol in dichloromethane to obtain pure 96vvvv (0.145 g, 6.14%). MS(ES): m/z 191.21 [M+H]$^+$.

Synthesis of Intermediate 96xxxx.

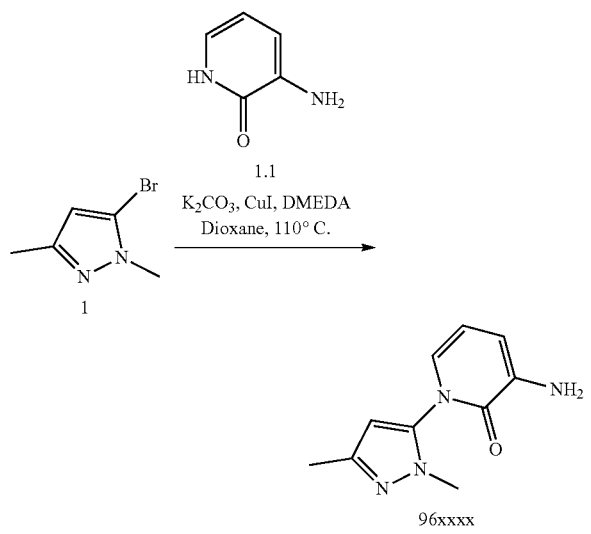

Synthesis of Compound 96xxxx.

To a solution of 1. (1.6 g, 9.14 mmol, 1.2 eq) and 1.1 (0.838 g, 7.62 mmol, 1 eq) in 1,4-dioxane (16 mL) was added potassium carbonate (2.62 g, 19.09 mmol, 2.5 eq) and degassed with argon for 15 min. Copper iodide (0.217 g, 1.14 mmol, 0.15 eq) and 1,2-dimethylethylenediamine (0.200 g, 2.28 mmol, 0.3 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.9% methanol in dichloromethane to obtain pure 96xxxx (0.200 g, 12.86%). MS(ES): m/z 205.23 [M+H]$^+$.

Synthesis of Intermediate 96yyyy.

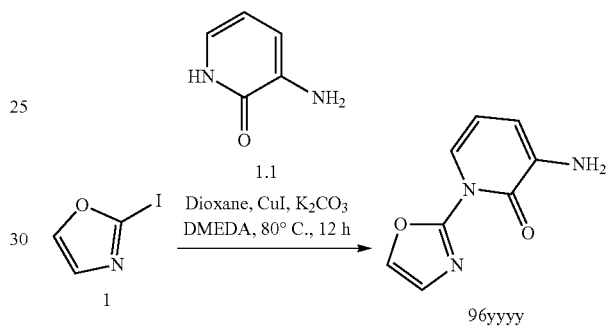

Synthesis of Compound 96yyyy.

To a solution of 1. (0.250 g, 1.28 mmol, 1 eq) in 1,4-dioxane (15 mL), 1.1. (0.169 g, 1.53 mmol, 1.2 eq) was added. The reaction mixture was degassed for 10 min under argon atmosphere followed by addition of potassium carbonate (0.441 g, 3.2 mmol, 2.5 eq), N,N-dimethylethylenediamine (0.028 g, 0.32 mmol, 0.25 eq), and copper iodide (0.036 g, 0.19 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96yyyy (0.060 g, Yield: 26.41%). MS (ES): m/z 178.06 [M+H]$^+$ Synthesis of Intermediate 96zzzz

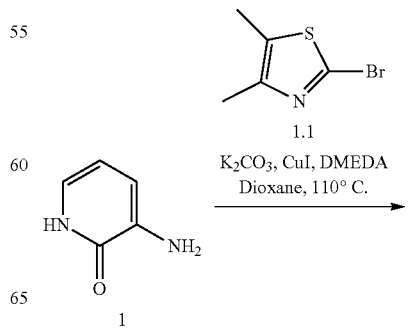

1397

-continued

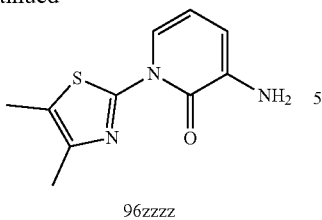

96zzzz

Synthesis of Compound 96zzzz.

To a solution of 1. (2 g, 18.16 mmol, 1.0 eq) and 1.1 (4.19 g, 21.80 mmol, 1.2 eq) in 1,4-dioxane (20 mL) was added potassium carbonate (5.01 g, 36.32 mmol, 2.0 eq) and degassed with argon for 15 min. Copper iodide (0.689 g, 3.63 mmol, 0.2 eq) and 1,2-dimethylethylenediamine (0.639 g, 7.26 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.3% methanol in dichloromethane to obtain pure 96zzzz (0.700 g, 17.42%). MS(ES): m/z 222.28 [M+H]$^+$.

Synthesis of Intermediate 96aaaaa.

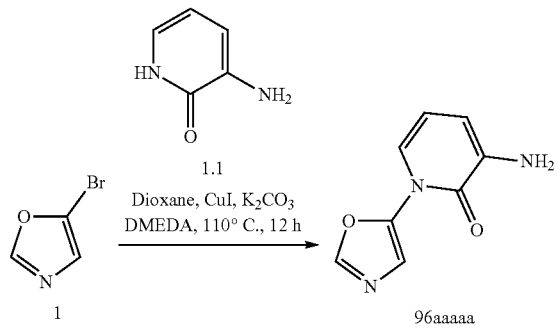 [SMILES: Brc1cnco1 ; Nc1ccc[nH]c1=O ; Nc1cccn(-c2cnco2)c1=O]

Synthesis of Compound 96aaaaa.

To a solution of 1 (1.0 g, 6.75 mmol, 1 eq) in 1,4-dioxane (50 mL), 1.1 (0.891 g, 8.1 mmol, 1.2 eq) was added. The reaction mixture was degassed for 10 min under argon atmosphere followed by addition of potassium carbonate (2.3 g, 16.87 mmol, 2.5 eq), N,N-dimethylethylenediamine (0.148 g, 1.68 mmol, 0.25 eq), and copper iodide (0.192 g, 1.01 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96aaaaa. (0.230 g, Yield: 19.21%). MS (ES): m/z 178.06 [M+H]$^+$

1398

Synthesis of Intermediate 96bbbbb.

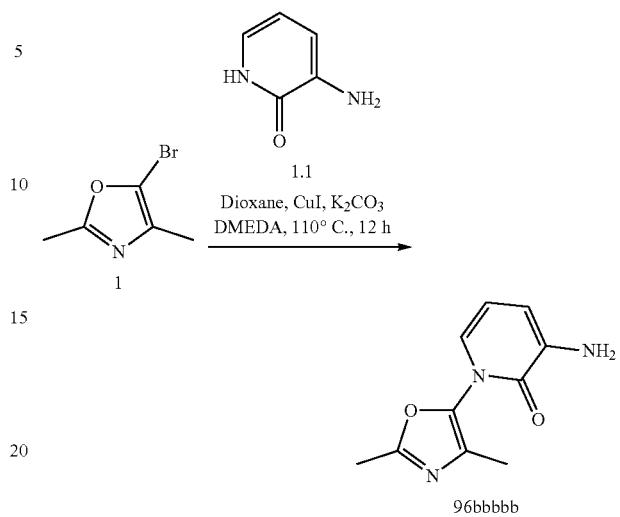

Synthesis of Compound 96bbbbb.

To a solution of 1 (0.5 g, 2.84 mmol, 1 eq) in 1,4-dioxane (28 mL), 1.1 (0.381 g, 3.40 mmol, 1.2 eq) was added. The reaction mixture was degassed for 10 min under argon atmosphere followed by addition of potassium carbonate (0.979 g, 7.1 mmol, 2.5 eq), N,N-dimethylethylenediamine (0.062 g, 0.71 mmol, 0.25 eq), and copper iodide (0.079 g, 0.42 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96bbbbb (0.2 g, Yield: 34.31%). MS (ES): m/z 206.09 [M+H]$^+$ Synthesis of Intermediate 96ccccc.

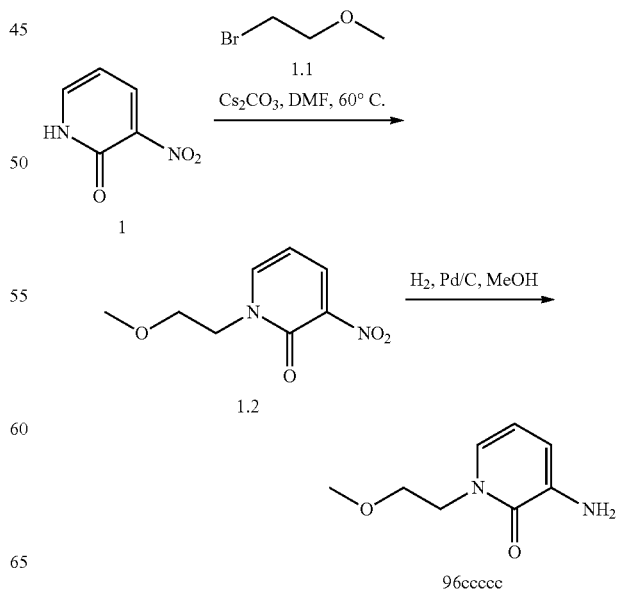

Synthesis of Compound 1.2.

To a solution of 1 (1 g, 7.14 mmol, 1.0 eq) in dimethylformamide (10 mL), 1.1 (0.98 g, 7.14 mmol, 1.0 eq) and cesium carbonate (0.5 g, 17.85 mmol, 2.5 eq) were added. The reaction mixture was heated at 60° C. for 4 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 20% ethyl acetate in hexane as eluant to obtain pure 1.2 (0.40 g, 28.28%). MS(ES): m/z 199.18 [M+H]$^+$ Synthesis of Compound 96ccccc.

To a solution of 1.2 (0.40 g, 2.02 mmol, 1.0 eq) in palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 96ccccc (0.25 g, 73.64%). MS(ES): m/z 169.20 [M+H]$^+$ Synthesis of Intermediate 96eeeee.

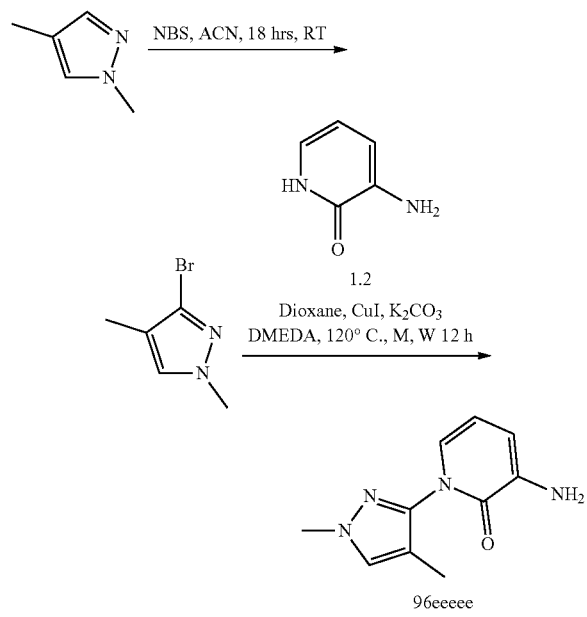

Synthesis of Compound 1.1

To a cooled solution of 1 (10 g, 104.02 mmol, 1.0 eq), in acetonitrile (92 mL) was added N-Bromosuccinimide (20.36 g, 114.22 mmol, 1.1 eq). The reaction was stirred at 0° C. for 30 min. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 10% ethyl acetate in hexane to obtain 1.1 (3.5 g, 19.22%). MS(ES): m/z 173.98 [M+H]$^+$.

Synthesis of Compound 96eeeee.

To a solution of 1.1 (1 g, 5.71 mmol, 1.0 eq) and 1.2 (1.25 g, 11.42 mmol, 2 eq) in 1,4-dioxane (20 mL) was added potassium carbonate (1.57 g, 11.42 mmol, 2.0 eq) and degassed with argon for 15 min. Copper iodide (0.325 g, 1.71 mmol, 0.3 eq) and 1,2-dimethylethylenediamine (0.150 g, 1.71 mmol, 0.3 eq) was added and reaction mixture again degassed with argon for 5 min followed by heating at 120° C. for 12 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1% methanol in dichloromethane to obtain pure 96eeeee (0.120 g, 10.28%). MS(ES): m/z 205.10 [M+H]$^+$.

Synthesis of Intermediate 96fffff.

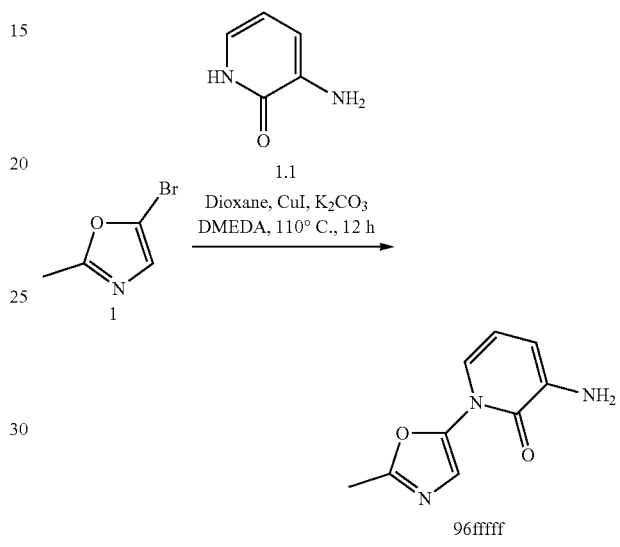

Synthesis of Compound 96fffff.

To a solution of 1 (0.340 g, 2.09 mmol, 1 eq) in 1,4-dioxane (20 mL), 1.1 (0.275 g, 2.50 mmol, 1.2 eq) was added. The reaction mixture was degassed for 10 min under argon atmosphere followed by addition of potassium carbonate (0.720 g, 5.22 mmol, 2.5 eq), N,N-dimethylethylenediamine (0.045 g, 0.52 mmol, 0.25 eq), and copper iodide (0.059 g, 0.31 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96fffff (0.092 g, Yield: 22.93%). MS (ES): m/z 192.07 [M+H]$^+$ Synthesis of Intermediate 96ggggg.

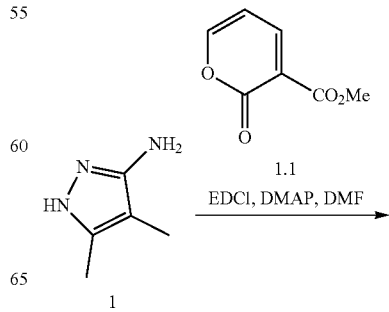

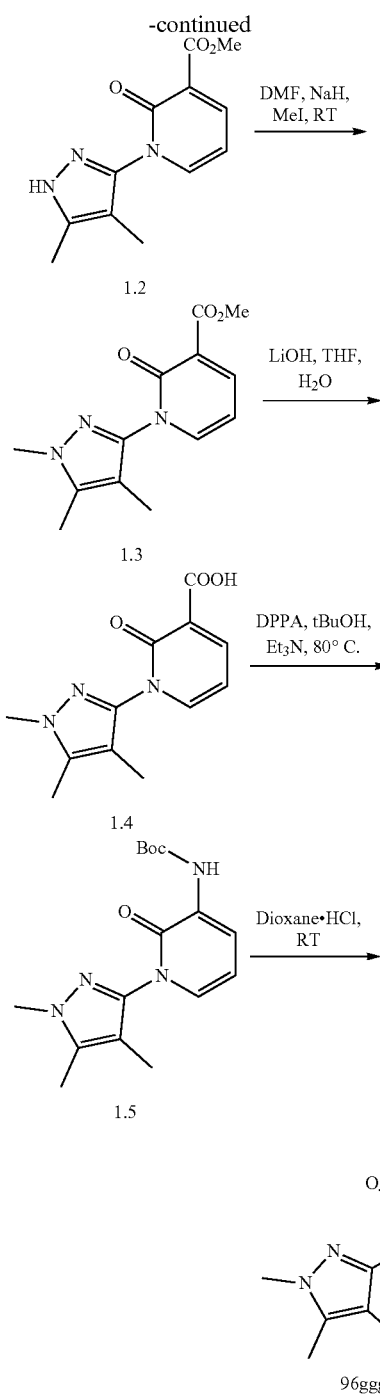

Synthesis of Compound 1.2.

To a cooled solution of 1 (1.0 g, 9.00 mmol, 1.0 eq), in N,N-dimethylformamide (10 mL) was added 1.1 (1.39 g, 9.00 mmol, 1.0 eq). The reaction mixture was stirred at 0° C. for 6 h and further stirred at room temperature for 15 min. N-Ethyl-N'-(3-dimethylaminopropyl)carbodiimide hydrochloride (2.23 g, 11.7 mmol, 1.3 eq) and 4-Dimethylaminopyridine (0.275 g, 0.225 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (0.61 g, 27.42%). MS(ES): m/z 248.25 [M+H]$^+$.

Synthesis of Compound 1.3.

To a cooled solution of 1.2 (0.610 g, 2.47 mmol, 1.0 eq), in N,N-dimethylformamide (10 mL) was added sodium hydride (0.19 g, 4.94 mmol, 2.0 eq) and methyl iodide (0.42 g, 2.96 mmol, 1.2 eq). The reaction mixture was stirred at room temperature for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.0% methanol in dichloromethane to obtain 1.3 (0.450 g, 69.81%). MS(ES): m/z 262.28 [M+H]$^+$.

Synthesis of Compound 1.4.

To a solution of 1.3 (0.45 g, 1.72 mmol, 1.0 eq), in tetrahydrofuran: methanol: water (10 mL, 2:2:1) was added lithium hydroxide (1.06 g, 17.2 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.4 (0.362 g, 85.01%). MS(ES): m/z 248.25 [M+H]$^+$.

Synthesis of Compound 1.5.

To a solution of 1.4 (0.362 g, 1.46 mmol, 1.0 eq) in tertiary butanol (8 mL) was added triethylamine (0.251 g, 2.48 mmol, 1.7 eq) and diphenyl phosphoryl azide (0.521 g, 1.9 mmol, 1.3 eq) under nitrogen followed by heating at 80° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.5 (0.17 g, 36.47%). MS(ES): m/z 319.38 [M+H]$^+$.

Synthesis of Compound 96ggggg.

To a cooled solution of 1.5 (0.17 g, 0.533 mmol, 1 eq) in dioxane (2 mL) was added 4N hydrochloric acid in dioxane (1 mL) as a dropwise. The reaction mixture was stirred at room temperature for 2 h. After completion of reaction, reaction mixture was concentrated under reduced pressure to obtain pure 96ggggg (0.082 g, 70.36%). MS(ES): m/z 219.26 [M+H]$^+$.

Synthesis of 96hhhhh.

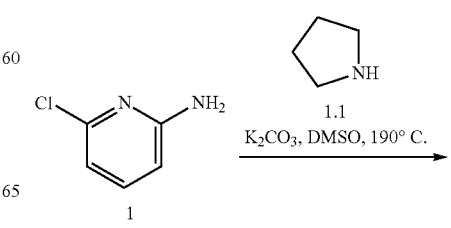

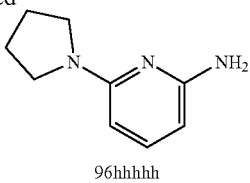

96hhhhh

Synthesis of Compound 96hhhhh.

To a solution of 1 (1 g, 7.77 mmol, 1.0 eq) in dimethyl sulphoxide (10 mL), 1.1 (1.65 g, 23.31 mmol, 3.0 eq) was added. The reaction mixture was degassed for 10 min under argon atmosphere followed by addition of potassium carbonate (3.21 g, 23.31 mmol, 3.0 eq). The reaction mixture was heated at 190° C. for 10 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 96hhhhh (0.400 g, Yield: 31.50%). MS (ES): m/z 164.11 [M+H]$^+$ Synthesis of Intermediate 96iiiii.

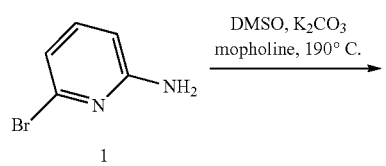

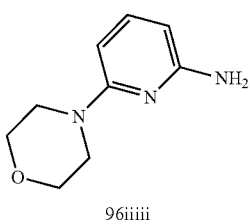

96iiiii

Synthesis of Compound 96iiiii.

To a solution of 1 (1.0 g, 5.78 mmol, 1.0 eq) and morpholine (1.5 g, 17.34 mmol, 3.0 eq) in dimethyl sulphoxide (10 mL) was added potassium carbonate (1.595 g, 11.56 mmol, 2.0 eq) and reaction mixture heated at 190° C. for 10 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 96iiiii (0.6 g, 57.92%). MS(ES): m/z 180.22 [M+H]$^+$.

Synthesis of Intermediate 96jjjjj.

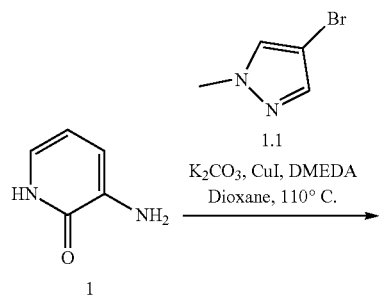

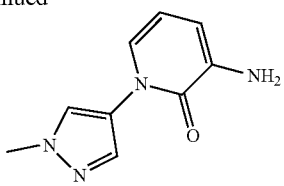

96jjjjj

Synthesis of Compound 96jjjjj.

To a solution of 1. (1 g, 9.08 mmol, 1.0 eq) and 1.1 (1.94 g, 11.80 mmol, 1.3 eq) in 1,4-dioxane (10 mL) was added potassium carbonate (3.75 g, 27.24 mmol, 3.0 eq) and degassed with argon for 15 min. Copper iodide (0.345 g, 1.8 mmol, 0.2 eq) and 1,2-dimethylethylenediamine (0.320 g, 3.63 mmol, 0.4 eq) was added and reaction mixture again degassed with argon for 5 min followed by heating at 110° C. for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 2.6% methanol in dichloromethane to obtain pure 96jjjjj (0.820 g, 47.47%). MS(ES): m/z 191.21 [M+H]$^+$.

Synthesis of Intermediate 96kkkkk.

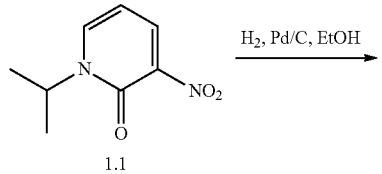

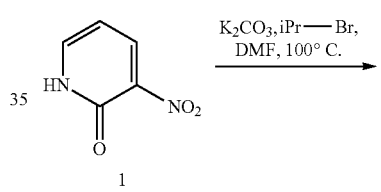

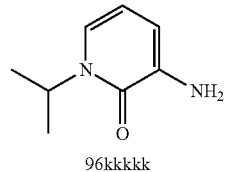

96kkkkk

Synthesis of Compound 1.1.

To a solution of 1 (1 g, 7.14 mmol, 1.0 eq) in dimethylformamide (10 mL), 2-propyl bromide (1.3 g, 10.71 mmol, 1.5 eq) was added. The reaction mixture was degassed for 10 min under argon atmosphere followed by addition of potassium carbonate (2.9 g, 21.42 mmol, 3.0 eq). The reaction mixture was heated at 100° C. for 10 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 1.1 (0.320 g, Yield: 24.61%). MS (ES): m/z 183.07 [M+H]$^+$.

Synthesis of Compound 96kkkkk.

To a solution of 1.1 (0.32 g, 1.75 mmol, 1.0 eq) in ethanol (7 ml), palladium on charcoal (0.16 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 96kkkkk (0.220 g, 82.29%). MS (ES): m/z 153.10 [M+H]$^+$.

Synthesis of Intermediate 96mmmmm

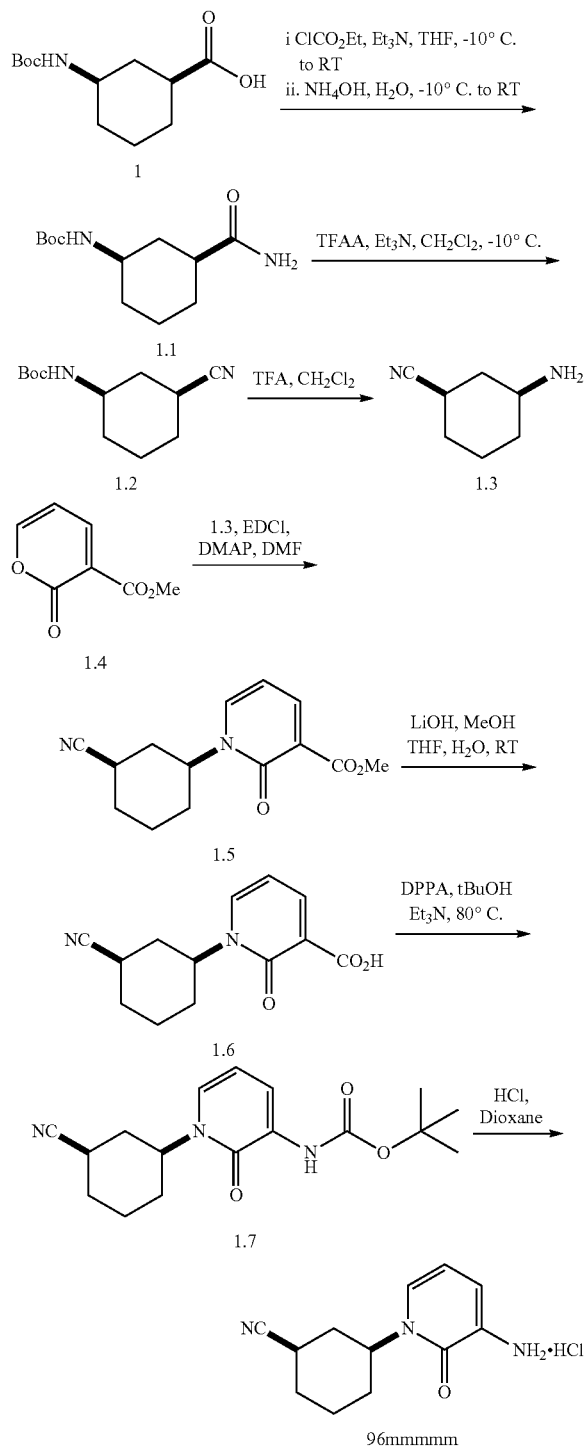

Synthesis of Compound 1.1.

To a stirred solution of 1 (5.0 g, 20.55 mmol, 1.0 eq) in Tetrahydrofuran (30 mL) was added triethylamine (5.7 mL, 41.1 mmol, 2.0 eq) drop wise at 0° C. under nitrogen followed by the addition of ethyl chloroformate (2.56 g, 23.63 mmol, 1.15 eq). Reaction mixture stirred at room temperature for 3 h, cooled to −10° C. and added NH$_4$OH (12.33 mL, 123.3 mmol, 6 eq) drop wise, resulting reaction mixture stirred at room temperature for 18 h. After completion of reaction, reaction mixture transferred into cold water and filtered, washed with water and dried to obtain 1.1. (Yield: 3.50 g, 70.28%). MS (ES): m/z 243.3 [M+H]$^+$ Synthesis of Compound 1.2.

To a stirred solution of 1.1 (3.5 g, 14.4 mmol, 1.0 eq) in dichloromethane (25 mL) was added triethylamine (4.0 mL, 28.8 mmol, 2.0 eq) drop wise at −10° C. under nitrogen followed by the drop wise addition of trifluoroacetic anhydride (2.2 mL, 15.84 mmol, 1.1 eq) and stirred for 3 h at same temperature. After completion of reaction, reaction mixture transferred into cold water and product was extracted with ethyl acetate. Organic layer was combined, washed with brine solution, dried over sodium sulphate and concentrated under reduced pressure to obtain crude material. This was further purified column chromatography using 10% ethyl acetate in hexane as eluent to obtain 1.2 (2.8 g, 86.43%). MS(ES): m/z 225.34 [M+H]$^+$.

Synthesis of Compound 1.3.

To a stirred solution of 1.2 (2.8 g, 12.48 mmol, 1.0 eq) in dichloromethane (40 mL) was added trifluoroacetic acid (8.0 mL) drop wise at 0° C. The reaction was stirred at room temperature for 1 h. After completion of reaction, reaction mixture was concentrated under reduced pressure to obtain crude material. This was further purified by trituration with n-pentane to obtain pure 1.3 (2.50 g, 84.15%). MS (ES): m/z 126.19 [M+H]$^+$ Synthesis of Compound 1.5.

To a solution of 1.4 (2.3 g, 14.92 mmol, 1.0 eq) in N,N-dimethylformamide (65 mL) was added 1.3 (1.85 g, 14.92 mmol, 1.0 eq). The reaction mixture was stirred at room temperature for 1 h followed by addition of N-Ethyl-N'-(3-dimethylaminopropyl) carbodiimide hydrochloride (3.7 g, 19.39 mmol, 1.3 eq) and 4-dimethylaminopryidine (0.455 g, 3.73 mmol, 0.25 eq). The reaction was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 30% ethyl acetate in hexane as eluant to obtain pure 1.5 (Yield: 1.8 g, 42.63%). MS (ES): m/z 261.29 [M+H]$^+$.

Synthesis of Compound 1.6.

To a solution of 1.5 (1.8 g, 6.91 mmol, 1.0 eq), in tetrahydrofuran: methanol: water (30 mL, 1:1:1) was added lithium hydroxide (0.829 g, 34.55 mmol, 5.0 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.6. (Yield: 1.1 g, 72.67%). MS (ES): m/z 247.29 [M+H]$^+$ Synthesis of Compound 1.7.

To a solution of 1.6 (1.1 g, 4.47 mmol, 1.0 eq) in Tert-Butyl alcohol (12 ml) was added di-phenylphosphorylazide (1.59 g, 5.81 mmol, 1.3 eq), triethylamine (0.766 g, 7.59 mmol, 1.7 eq). The reaction was stirred at 90° C. for 16 h. After completion of reaction, reaction mixture was concentrated under reduced pressure to obtain crude material. This was further purified by combi flash using 1.0% MeOH in Dichloromethane as eluent to 1.7 (Yield: 0.7 g, 49.38%). MS (ES): m/z 318.39 [M+H]$^+$ Synthesis of Compound 96mmmmm.

To 1.7 (0.7 g, 2.20 mmol, 1.0 eq) was added 4M hydrochloric acid in 1,4-Dioxane (10 mL) and stirred at room temperature for 4 h. After completion of reaction, reaction mixture was concentrated under reduced pressure, residue was triturated with diethyl ether to obtain 96mmmmm (Yield: 0.39 g, 69.69%). MS (ES): m/z 254.73 [M+H]$^+$.

Synthesis of Intermediate 96nnnnn.

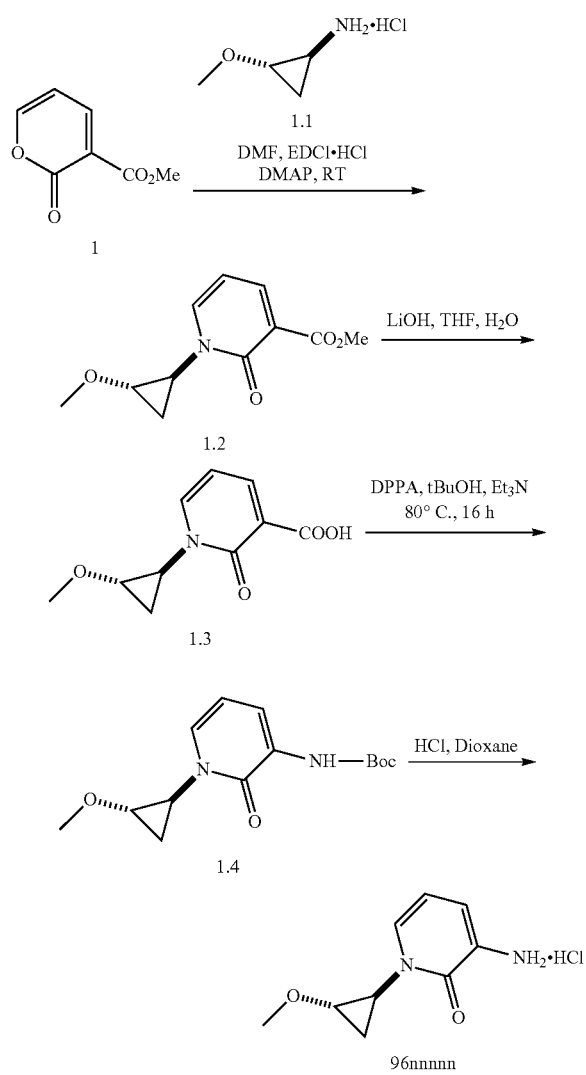

Synthesis of Compound 1.2.

To a cooled solution of 1. (2.0 g, 12.97 mmol, 1.0 eq), in N,N-dimethylformamide (20 mL) was added 1.1 (1.6 g, 12.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.6 g, 16.86 mmol, 1.3 eq) and 4-Dimethylaminopyridine (0.316 g, 2.59 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (1.3 g, 44.88%). MS(ES): m/z 224.09 [M+H]$^+$.

Synthesis of Compound 1.3.

To a solution of 1.2 (1.3 g, 5.82 mmol, 1.0 eq), in tetrahydrofuran: water (15 mL, 2:1) was added lithium hydroxide (1.39 g, 58.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (1.1 g, 90.29%). MS(ES): m/z 210.07 [M+H]$^+$.

Synthesis of Compound 1.4.

To a solution of 1.3 (1.1 g, 5.25 mmol, 1.0 eq) in tert.butanol (14 mL) was added triethylamine (0.9 g, 8.92 mmol, 1.7 eq) and diphenyl phosphoryl azide (1.87 g, 6.82 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (1.1 g, 74.63%). MS(ES): m/z 281.15 [M+H]$^+$.

Synthesis of Compound 96nnnnn. To a cooled solution of 1.4 (0.300 g, 1.07 mmol, 1 eq) in dioxane (4 mL) was added 4N hydrochloric acid in dioxane (8 mL) as a dropwise. The reaction mixture was stirred at room temperature for 2 h. After completion of reaction, reaction mixture was concentrated under reduced pressure to obtain pure 96nnnnn. (0.220 g, 94.88%). MS(ES): m/z 181.09 [M+HCl]$^+$.

Example 97: Synthesis of Compounds where R³ is N-(cyclobutyl)carboxamide, R⁶ is Hydrogen, and R⁷ is Methylamine Synthesis of N-cyclobutyl-5-((2-(methoxy-d3)-5-methylpyridin-3-yl)amino)-7-(methylamino)pyrazolo[1,5-a]pyrimidine-3-carboxamide (I-260)

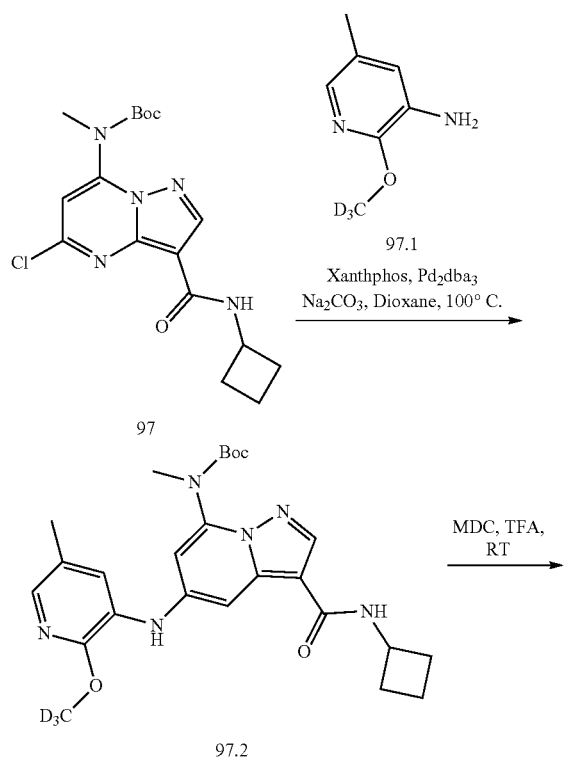

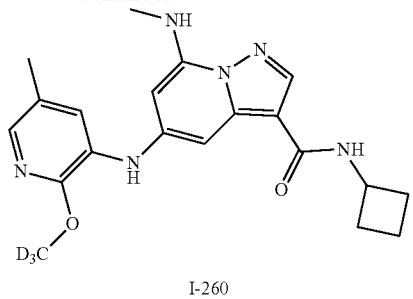

I-260

Synthesis of Compound 97.

Compound was synthesized as per I-122 to obtain 97. (Yield: 60.21%), MS (ES): m/z 380.85 [M+H]⁺

Synthesis of Compound 97.1.

Compound was synthesized as per I-258 to obtain 97.1.

Synthesis of Compound 97.2.

Compound was synthesized using general procedure B to obtain 97.2 (0.065 g, 50.95%), MS (ES): m/z 485.58 [M+H]⁺.

Synthesis of Compound I-260. Compound was synthesized using general procedure C to obtain I-260 (0.030 g, 58.17%), MS (ES): m/z 385.53 [M+H]⁺, LCMS purity: 98.30%, HPLC purity: 99.78%, ¹H NMR (DMSO-d₆, 400 MHZ): 8.88 (s, 1H), 8.12 (s, 1H), 7.96 (s, 1H), 7.93-7.91 (t, J 8 Hz, 2H), 7.81 (s, 1H), 5.78 (s, 1H), 4.37-4.33 (m, 1H), 2.19-2.17 (d, J=8 Hz, 3H), 2.29 (s, 3H), 2.19-2.17 (m, 2H), 1.63 (bs, 4H).

Characterization data for further compounds prepared by the above methods are presented in Table 31 below. Compounds in Table 31 were prepared by methods substantially similar to those described to prepare I-260, where 97.1 was replaced with the reagent as indicated in Table 31.

TABLE 31

| Compound # | Reagent | Chiral Separation Conditions and Characterization Data |
|---|---|---|
| I-201 | | Hydrolysis of oxetane ring was achieved using PTSA in methanol: MS (ES): m/z 428.29 [M + H]⁺, LCMS purity: 98.34%, HPLC purity: 96.36%, ¹H NMR (DMSO-d₆, 400 MHZ): 8.91 (s, 1H), 8.31-8.29 (d, J = 8 Hz, 1H), 8.18 (s, 1H), 7.99-7.97 (d, J = 8 Hz, 1H), 7.91-7.89 (d, J = 8 Hz, 1H), 7.33-7.32 (d, J = 4 Hz, 1H), 6.30-6.28 (t, J = 8 Hz, 1H), 6.22 (s, 1H), 5.02-5.01 (d, J = 4 Hz, 1H), 4.80-4.79 (t, J = 4 Hz, 1H), 4.51-4.45 (m, 1H), 4.32-4.30 (d, J = 8 Hz, 1H), 3.85 (s, 1H), 3.78-3.73 (m, 1H), 3.41-3.38 (m, 2H), 2.92-2.91 (d, J = 4 Hz, 3H), 2.34-2.33 (m, 2H), 1.94-1.90 (m, 2H), 1.77-1.70 (m, 2H). |
| I-299 | | MS (ES): m/z 402.22 [M + H]⁺, LCMS purity: 97.19%, HPLC purity: 95.43%, ¹H NMR (DMSO-d₆, 400 MHZ): 8.90 (s, 1H), 8.55-8.54 (d, J = 4 Hz, 1H), 8.24-8.22 (d, J = 8 Hz, 1H), 8.10 (s, 1H), 7.95-7.94 (d, J = 4 Hz, 1H), 7.84-7.81 (d, J = 12 Hz, 1H), 7.69-7.68 (t, J = 4 Hz, 1H), 5.85 (s, 1H), 4.32-4.24 (m, 1H), 2.94-2.93 (d, J = 4 Hz, 3H), 2.12-2.11 (m, 1H), 2.09-1.99 (m, 3H), 1.57-1.54 (m, 2H), 1.45-1.36 (m, 2H), 1.24-1.12 (m, 1H). |

TABLE 31-continued

| Compound # | Reagent | Chiral Separation Conditions and Characterization Data |
|---|---|---|
| I-358 | (3-amino-2-oxopyridin-1-yl cyclohexyl methyl ether structure) | MS (ES): m/z 466.68 [M + H]⁺, LCMS purity: 99.72%, HPLC purity: 98.12%, ¹H NMR (DMSO-d₆, 400 MHZ): 8.90 (s, 1H), 8.27-8.25 (d, J = 7.2 Hz, 1H), 8.17 (s, 1H), 7.98-7.92 (d, J = 8 Hz, 1H), 7.92 (bs, 1H), 7.39-7.37 (d, J = 6.4 Hz, 1H), 6.34-6.30 (t, J = 7.2 Hz, 1H), 6.22 (s, 1H), 4.86-4.80 (t, J = 12 Hz, 1H), 4.51-4.44 (m, 1H), 3.27-3.25 (d, J = 8.4 Hz, 3H), 2.91 (s, 3H), 2.33 (bs, 2H), 2.07-2.03 (d, J = 12.8 Hz, 2H), 1.93-1.87 (m, 4H), 1.75-1.68 (m, 2H), 1.62-1.56 (m, 4H). |
| I-266 | (3-amino-1-(5-methoxypyridin-2-yl)pyridin-2-one structure) | MS (ES): m/z 461.50 [M + H]⁺, LCMS purity: 100%, HPLC purity: 99.70%, ¹H NMR (DMSO-d₆, 400 MHZ): 9.02 (s, 1H), 8.38-8.32 (m, 2H), 8.20 (s, 1H), 8.01-7.95 (m, 2H), 7.79-7.77 (m, 1H), 7.66-7.63 (m, 1H), 7.55-7.53 (d, 1H), 6.44-6.42 (m, 1H), 6.25 (s, 1H), 4.48 (s, 1H), 3.94 (d, 3H), 2.92-2.91 (d, J = 4.4 Hz, 3H), 2.34 (s, 3H), 1.95-1.93 (t, 2H), 1.75 (bs, 1H). |
| I-503 | (3-amino-1-(4,4-dimethyl-4,5-dihydrothiazol-2-yl)pyridin-2-one structure) | MS (ES): m/z 467.40 [M + H]⁺, LCMS purity: 98.93%, HPLC purity: 97.46%, ¹H NMR (DMSO-d₆, 400 MHZ): 9.26 (s, 1H), 8.41 (bs, 1H), 8.28 (s, 1H), 8.06 (bs, 2H), 6.55 (bs, 1H), 6.31 (bs, 1H), 3.33 (s, 3H), 3.00 (s, 3H), 2.42 (bs, 3H), 1.98 (bs, 2H), 1.82 (bs, 2H), 1.47 (s, 6H). |
| I-278 | (3-amino-2-(cyclopropyloxy)-5-methylpyridine structure) | MS (ES): m/z 408.37 [M + H]⁺, LCMS purity: 98.15%, HPLC purity: 95.36%, ¹H NMR (DMSO-d₆, 400 MHZ): 8.71 (s, 1H), 8.11 (s, 1H), 7.94 (s, 1H), 7.91-7.89 (d, J = 8 Hz, 1H), 7.84 (s, 2H), 5.77-5.74 (m, 1H), 4.36-4.28 (m, 2H), 2.91-2.90 (d, J = 4 Hz, 3H), 2.29 (s, 3H), 2.18-2.16 (m, 2H), 1.64-1.56 (m, 4H), 0.76-0.71 (m, 2H), 0.69-0.65 (m, 2H). |
| I-256 | (1-isopropyl-5-methyl-3-(pinacol boronate)-7-azaindole structure) | MS (ES): m/z 418.22 [M+H]⁺, LCMS purity: 100%, HPLC purity: 99.04%, ¹H NMR (DMSO-d₆, 400 MHZ): 8.71 (s, 1H), 8.56 (s, 1H), 8.35-8.33 (d, J = 8 Hz, 2H), 8.25 (s, 1H), 8.22-8.21 (d, J = 4 Hz, 1H), 6.74 (s, 1H), 5.18-5.13 (m, 1H), 4.61-4.55 (m, 1H), 3.12-3.11 (d, J = 4 Hz, 3H), 2.50 (s, 3H), 2.36 (bs, 2H), 2.06-2.01 (m, 2H), 1.79-1.74 (m, 2H), 1.58-1.57 (d, J = 4 Hz, 6H) |

TABLE 31-continued

| Compound # | Reagent | Chiral Separation Conditions and Characterization Data |
|---|---|---|
| I-234 | (structure) | MS (ES): m/z 448.35 [M + H]⁺, LCMS purity: 100%, HPLC purity: 99.48%, ¹H NMR (DMSO-d₆, 400 MHZ): 8.88 (s, 1H), 8.32 (s, 1H), 8.19 (s, 1H), 8.10-8.09 (d, J = 4 Hz, 1H), 7.91 (s, 1H), 7.89 (s, 1H), 7.83-7.82 (d, J = 4 Hz, 1H), 7.42 (s, 1H), 6.19 (s, 1H), 4.51-4.44 (m, 1H), 3.91 (s, 3H), 2.92-2.90 (d, J = 8 Hz, 3H), 2.33-2.25 (m, 2H), 2.20 (s, 3H), 1.99-1.88 (m, 2H), 1.73-1.63 (m, 2H). |
| I-263 | (structure) | MS (ES): m/z 451.46 [M + H]⁺, LCMS purity: 100%, HPLC purity: 100%, ¹H NMR (DMSO-d₆, 400 MHZ): 9.30 (bs, 1H), 8.46-8.44 (d, J = 8 Hz, 1H), 8.39-8.37 (d, J = 8 Hz, 1H), 8.19 (s, 1H), 7.94-7.92 (d, J = 8 Hz, 2H), 7.52 (s, 1H), 6.64-6.6 (t, J = 8 Hz, 1H), 6.26 (s, 1H), 4 49-4.43 (m, 1H), 2.92 (s, 3H), 2.48 (s, 3H), 2.32-2.30 (m, 2H), 1.92-1.87 (m, 2H), 1.75-1.68 (m, 2H). |
| I-179 | (structure) | MS (ES): m/z 508.16 [M + H]⁺, LCMS purity: 100%, HPLC purity: 99.05%, ¹H NMR (DMSO-d₆, 400 MHZ): 9.08 (s, 1H), 8.36-8.36 (d, J = 2.4 Hz, 1H), 8.25 (s, 1H), 8.11 (s, 1H), 8.03-8.01 (d, J = 8 Hz, 1H), 7.74-7.72 (d, J = 8 Hz, 1H), 7.54-7.53 (d, J = 4 Hz, 1H), 6.54 (s, 1H), 4.55-4.49 (m, 1H), 3.73-3.68 (m, 1H), 2.92-2.91 (d, J = 4 Hz, 3H), 2.30-2.29 (m, 2H), 2.06 (s, 4H), 1.70-1.67 (m, 2H), 1.24 (s, 1H), 1.09-1.05 (m, 2H), 1.00-0.97 (m, 2H). |
| I-159 | (structure) | MS (ES): m/z 488.57 [M + H]⁺, LCMS purity: 99.67%, HPLC purity: 98.82%, ¹H NMR (DMSO-d₆, 400 MHZ): 8.84 (s, 1H), 8.20 (s, 1H), 8.14 (d, J = 2 Hz, 1H), 7.95-7.94 (d, J = 4.4 Hz, 1H), 7.85-7.83 (d, J = 8 Hz, 1H), 7.52 (s, 1H), 7.09 (s, 1H), 6.18 (s, 1H), 4.52-4.38 (m, 1H), 3.62-3.57 (m, 1H), 2.90-2.89 (d, J = 4.8 Hz, 3H), 2.33-2.26 (m, 1H), 2.23 (s, 3H), 2.16 (s, 3H), 1.98-1.93 (m, 2H), 1.76-1.64 (m, 2H), 1.19-1.17 (m, 1H), 1.08-1.04 (m, 4H). |
| I-181 | (structure) | MS (ES): m/z 508.51 [M + H]⁺, LCMS purity: 98.47%, HPLC purity: 97.96%, ¹H NMR (DMSO-d₆, 400 MHZ): 9.06 (s, 1H), 8.35-8.35 (d, J = 2.8 Hz, 1H), 8 24 (s, 1H), 8.02-8.01 (d, J = 4.8 Hz, 1H), 7.73-7.71 (d, J = 8 Hz, 1H), 7.57 (s, 1H), 7.51-7.50 (d, J = 2.4 Hz, 1H), 6.32 (s, 1H), 4.54-4.48 (m, 1H), 3.64-3.58 (m, 1H), 2.91-2.90 (d, J = 4.8 Hz, 3H), 2.21 (s, 3H), 2.08-1.96 (m, 3H), 1.72-1.66 (m, 2H), 1.23 (bs, 2H), 1.08-1.05 (m, 3H). |

TABLE 31-continued

| Compound # | Reagent | Chiral Separation Conditions and Characterization Data |
|---|---|---|
| I-213 | 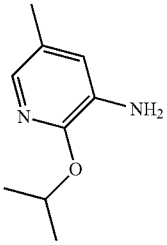 | MS (ES): m/z 410.45 [M + H]+, LCMS purity: 97.33%, HPLC purity: 97.13%, 1H NMR (DMSO-d6, 400 MHZ): 8.65 (s, 1H), 8.10 (s, 1H), 7.92-7.90 (m, 1H), 7.86-7.85 (d, J = 4 Hz, 1H), 7.77 (s, 1H), 5.77 (s, 1H), 5.31-5.28 (t, J = 12 Hz, 1H), 4.35-4.33 (m, 1H), 3.57 (s, 1H), 2.92-2.91 (d, J = 4 Hz, 3H), 2.26 (s, 3H), 2.17-2.15 (m, 2H), 1.61 (bs, 4H), 1.28-1.26 (d, J = 8 Hz, 6H). |
| I-324 | 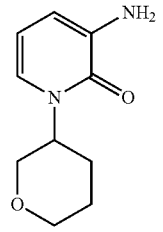 [SMILES: Nc1cccn(C2CCCOC2)c1=O] | MS (ES): m/z 438.4 [M+H]+, LCMS purity: 99.68%, HPLC purity: 99.43%, CHIRAL HPLC purity: (50.24%, 49.75%), 1H NMR (DMSO-d6, 400 MHZ): 8.94 (s, 1H), 8.29-8.27 (d, J = 8 Hz, 1H), 8.17 (s, 1H), 7.96-7.91 (m, 2H), 7.55-7.53 (d, J = 8 Hz, 1H), 6.34-6.33 (t, J = 4Hz, 1H), 6.23 (s, 1H), 4.91-4 86 (m, 1H), 4.50-4.44 (m, 1H), 3 87-3.82 (m, 2H), 3.60-3.55 (m, 1H), 3.46 (m, 1H), 2.91-2.89 (d, J = 8 Hz, 3H), 2.33-2.31 (m, 2H), 2.10-2.01 (m, 2H), 1.95-1.80 (m, 2H), 1.76-1.71 (m, 4H). |
| I-353 I-354 | 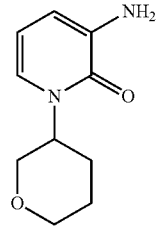 | I-324 was separated into isomers: CHIRAL PAK IB (250 mm * 4.6 mm, 5u) in 0.1% DEA IPA: MEOH (50:50) at 4 mL/min.<br>FR-a: MS(ES): m/z 438.34 [M + H]+, LCMS purity: 100%, HPLC purity: 100%, CHIRAL HPLC purity: 100%, 1H NMR (DMSO-d6, 400 MHZ): 8.94 (s, 1H), 8.29-8.27 (d, J = 8 Hz, 1H), 8.17 (s, 1H), 7.96-7.91 (m, 2H), 7.54-7.53 (d, J = 4 Hz, 1H), 6.34-6.32 (d, t = 8 Hz, 1H), 6.23 (s, 1H), 4.90-4.86 (m, 1H), 4.50-4.43 (m, 1H), 3.86-3.81 (m, 1H), 3.60-3.55 (m, 1H), 3.48-3.43 (m, 1H), 2.90-2.89 (d, J = 4 Hz, 3H), 2.33-2.31 (d, J = 8 Hz, 2H), 2.09-2.05 (m, 2H), 1.97-1.88 (m, 2H), 1.85-1.65 (m, 4H), 1.15-1.13 (t, J = 8 Hz, 1H).<br>FR-b: MS(ES): m/z 438.34 [M + H]+, LCMS purity: 100%, HPLC purity: 100%, CHIRAL HPLC purity: 99.45%, 1H NMR (DMSO-d6, 400 MHZ): 8.94 (s, 1H), 8.29-8.27 (d, J = 8 Hz, 1H), 8.17 (s, 1H), 7.96-7.91 (m, 2H), 7.54-7.53 (d, J = 4 Hz, 1H), 6.34-6.32 (d, t = 8 Hz, 1H), 6.23 (s, 1H), 4.90-4.86 (m, 1H), 4.50-4.43 (m, 1H), 3.86-3.81 (m, 1H), 3.60-3.55 (m, 1H), 3.48-3.43 (m, 1H), 2.90-2.89 (d, J = 4 Hz, 3H), 2.33-2.31 (d, J = 8 Hz, 2H), 2.09-2.05 (m, 2H), 1.97-1.88 (m, 2H), 1.85-1.65 (m, 4H), 1.15-1.13 (t, J = 8 Hz, 1H). |
| I-210 | 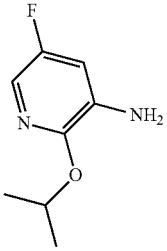 | MS (ES): m/z 414.29 [M + H]+, LCMS purity: 99.25%, HPLC purity: 99.46%, CHIRAL HPLC purity: 99.05%, 1H NMR (DMSO-d6, 400 MHZ): 8.76 (s, 1H), 8.43-8.41 (d, J = 8 Hz, 1H), 8.19 (s, 1H), 8.01-8.00 (d, J = 4 Hz, 1H), 7.87-7.85 (m, 2H), 6.08 (s, 1H), 5.34-5.32 (t, J = 8 Hz, 1H), 4.46-4.44 (d, J = 8 Hz, 1H), 2.96-2.95 (d, J = 8 Hz, 3H), 2.23 (m, 2H), 1 85-1.83 (t, J = 8 Hz, 2H), 1.66-1.64 (m, 2H), 1.38-1.36 (d, J = 8 Hz, 6H). |
| I-248 | 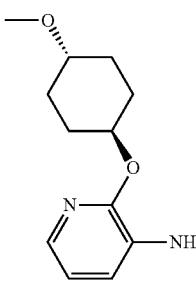 | MS (ES): m/z 466.56 [M + H]+, LCMS purity: 96.93%, HPLC purity: 96.91%, CHIRAL HPLC purity: 98.87%, 1H NMR (DMSO-d6, 400 MHZ): 8.70 (s, 1H), 8.23-8.21 (d, J = 8 Hz, 1H), 8.11 (s, 1H), 7.97 (s, 1H), 7.94-7.92 (t, J = 8 Hz, 1H), 7.90-7.89 (d, J = 4 Hz, 1H), 7.01-6.98 (m, 1H), 5.88 (s, 1H), 5.10 (s, 1H), 4.38-4.34 (m, 1H), 3.23 (s, 3H), 3.20-3.16 (m, 1H), 2.93-2.92 (d, J = 4 Hz, 3H), 2.20-2.19 (m, 2H), 2.02-1.95 (m, 4H), 1.65 (bs, 4H), 1.56-1.49 (m, 2H), 1.36-1.29 (m, 2H). |

TABLE 31-continued

| Compound # | Reagent | Chiral Separation Conditions and Characterization Data |
|---|---|---|
| I-226 | (cyclohexyl-O-pyridine-NH₂ structure) | MS (ES): m/z 436.46 [M + H]⁺, LCMS purity: 98.26%, HPLC purity: 96.16%, ¹H NMR (DMSO-d₆, 400 MHZ): 8.69 (s, 1H), 8.24-8.22 (d, J = 8 Hz, 1H), 8.12 (s, 1H), 7.98-7.96 (d, J = 8 Hz, 1H), 7.94-7.92 (d, J = 8 Hz, 1H), 7.89-7.88 (d, J = 4 Hz, 1H), 7.01-6.98 (m, 1H), 5.89 (s, 1H), 5.14-5.09 (m, 1H), 4.42-4.36 (m, 1H), 2.95-2.93 (d, J = 8 Hz, 3H), 2.21-2.20 (m, 2H), 1.96 (m, 2H), 1.72-1.67 (m, 6H), 1.55-1.48 (m, 3H), 1.37-1.34 (m, 2H), 0.89 (bs, 1H). |
| I-171 | 97b (tetrahydrofuranyl-O-pyridine-NH₂ structure) | MS (ES): m/z 424.52 [M + H]⁺, LCMS purity: 100%, HPLC purity: 100%, CHIRAL HPLC purity: 100%, ¹H NMR (DMSO-d₆, 400 MHZ): 8.76 (s, 1H), 8.32-8.30 (d, J = 8 Hz, 1H), 8.13 (s, 1H), 7.97 (s, 1H), 7.95 (s, 1H), 7.93-7.91 (m, 1H), 5.89 (s, 1H), 5.59-5.56 (m, 1H), 4.42-4.36 (m, 1H), 3.97-3.93 (m, 1H), 3.87-3.82 (m, 2H), 3.76-3.70 (m, 1H), 2.94-2.92 (d, J = 8 Hz, 3H), 2.29-2.22 (m, 3H), 2.12-2.08 (m, 1H), 1.71-1.60 (m, 4H), 1.23 (bs, 1H). |
| I-183 | 97c (pyridine-NH₂ with cis-methoxycyclobutyl-O structure) | MS (ES): m/z 438.50 [M + H]⁺, LCMS purity: 97.87%, HPLC purity: 96.92%, CHIRAL HPLC purity: 96.92%, ¹H NMR (DMSO-d₆, 400 MHZ): 8.82 (s, 1H), 8.32 (s, 1H), 8.14 (s, 1H), 7.95-7.90 (m, 3H), 7.02 (s, 1H), 5.93 (s, 1H), 4.94 (bs, 1H), 4.40 (bs, 1H), 3.67 (bs, 1H), 3.16 (s, 3H), 2.94 (s, 3H), 2.84 (bs, 2H), 2.22 (bs, 2H), 2.20 (bs, 2H), 1.68 (m, 4H). |
| I-187 | 97d (pyridine-NH₂ with trans-methoxycyclobutyl-O structure) | MS (ES): m/z 438.19 [M + H]⁺, LCMS purity: 96.01%, HPLC purity: 95.36%, ¹H NMR (DMSO-d₆, 400 MHZ): 8.80 (s, 1H), 8.32-8.30 (d, J = 4 Hz, 1H), 8.14 (s, 1H), 7.97-7.91 (m, 3H), 7.04-7.01 (m, 1H), 5.91 (s, 1H), 5.37-5.36 (t, J = 4 Hz, 1H), 4.43-4.37 (m, 1H), 4.04-4.03 (m, 1H), 3.16 (s, 3H), 2.95-2.94 (d, J = 4 Hz, 3H), 2.22-2.21 (m, 2H), 1.72-1.66 (m, 4H). |
| I-182 | (NH₂·HCl pyridinone-cyclohexyl-morpholine structure) | MS (ES): m/z 521.31 [M + H]⁺, LCMS purity: 100%, HPLC purity: 95.00%, CHIRAL HPLC purity: 100%, ¹H NMR (DMSO-d₆, 400 MHZ): 8.89 (s, 1H), 8.28-8.26 (d, J = 8 Hz, 1H), 8.17 (s, 1H), 7.97-7.95 (d, J = 8 Hz, 1H), 7.91-7.89 (d, J = 8 Hz, 1H), 7.34-7.32 (d, J = 8 Hz, 1H), 6.39-6.37 (t, J = 8 Hz, 1H), 6.22 (s, 1H), 4.93-4.88 (m, 1H), 4.51-4.44 (m, 1H), 3.66 (s, 4H), 2.91-2.90 (d, J = 4 Hz, 3H), 2.40-2.29 (m, 6H), 2.16-2.09 (m, 3H), 1.99-1.86 (m, 4H), 1.76-1.67 (m, 2H), 1.56-1.53 (m, 4H). |

TABLE 31-continued

| Compound # | Reagent | Chiral Separation Conditions and Characterization Data |
|---|---|---|
| I-298 | 96jjj | MS (ES): m/z 410.45 [M + H]+, LCMS purity: 100%, HPLC purity: 98.18%, $^1$H NMR (DMSO-d$_6$, 400 MHZ): 9.89 (s, 1H), 9.07-9.05 (d, J = 8 Hz, 1H), 8.38-8.36 (d, J = 6 Hz, 1H), 8.24 (s, 1H), 8.21-8.20 (d, J = 4.8 Hz, 1H), 7.80-7.78 (d, J = 8 Hz, 1H), 7.54-7.51 (t, J = 6.4 Hz, 1H), 6.02 (s, 1H), 5.60-5.51 (m, 2H), 5.10-5.04 (m, 1H), 4.89-4.84 (m, 1H), 4.43-4.39 (m, 1H), 3.97-3.91 (m, 2H), 2.94-2.93 (d, J = 4 Hz, 3H), 2.34-2.27 (m, 2H), 1.87-1.77 (m, 2H), 1.24-1.18 (m, 1H). |
| I-168 | 97e | MS (ES): m/z 408.44 [M + H]+, LCMS purity: 95.10%, HPLC purity: 95.01%, $^1$H NMR (DMSO-d$_6$, 400 MHZ): 8.80 (s, 1H), 8.32-8.30 (d, J = 8 Hz, 1H), 8.14 (s, 1H), 7.98-7.96 (d, J = 4 Hz, 1H), 7.92-7.89 (m, 2H), 7.02-6.99 (m, 1H), 5.93 (s, 1H), 5.28-5.26 (t, J = 8 Hz, 1H), 4.39 (m, 1H), 4.12 (m, 1H), 3 18-317 (d, J = 4 Hz, 1H), 2.94-2.93 (d, J = 4 Hz, 3H), 2.23-2.13 (m, 4H), 1.80-1.63 (m, 6H). |
| I-232 | | MS (ES): m/z 452.47 [M + H]+, LCMS purity: 96.84%, HPLC purity: 96.50%, CHIRAL HPLC purity: 98.74%, $^1$H NMR (DMSO-d$_6$, 400 MHZ): 8.69 (s, 1H), 8.24-8.23 (d, J = 4 Hz, 1H), 8.12 (s, 1H), 7.97-7.91 (m, 3H), 6.99 (s, 1H), 5.88 (s, 1H), 5.06 (bs, 1H), 4.60-4.59 (d, J = 4 Hz, 1H), 4.39-4.38 (d, J = 4 Hz, 1H), 3.35 (s, 1H), 2.94-2.93 (d, J = 4 Hz, 3H), 2.20 (m, 2H), 2.02 (m, 2H), 1.83 (m, 2H), 1.67 (bs, 4H), 1.53-1.50 (m, 2H), 1.32-1.29 (m, 2H). |
| I-185 | 97f | MS (ES): m/z 438.52 [M + H]+, LCMS purity: 97.44%, HPLC purity: 95.04%, $^1$H NMR (DMSO-d$_6$, 400 MHZ): 8.74 (s, 1H), 8.26-8.25 (d, J = 6.4 Hz, 1H), 8.12 (s, 1H), 7.96-7.90 (m, 3H), 7.03-7.01 (m, 1H), 5.89 (s, 1H), 5.31-5.28 (m, 1H), 4.38-4.34 (m, 1H), 3.86-3.83 (m, 2H), 3.49-3.45 (m, 3H), 2.94-2.92 (d, J = 8 Hz, 3H), 2.21-2.19 (m, 2H), 2.00-1.98 (m, 2H), 1.73-1.65 (m, 5H). |
| I-240 | 97g | MS (ES): m/z 472.57 [M + H]+, LCMS purity: 98.57%, HPLC purity: 96.29%, $^1$H NMR (DMSO-d$_6$, 400 MHZ): 9.07 (s, 1H), 8.44-8.42 (d, J = 8 Hz, 1H), 8.21 (s, 1H), 8.04-7.98 (m, 3H), 7.79-7.77 (d, J = 8 Hz, 1H), 7.65-7.64 (d, J = 4 Hz, 1H), 6.51-6.49 (t, J = 8 Hz, 1H), 6.26 (s, 1H), 4.50 (m, 2H), 2.92-2.91 (d, J = 4 Hz, 3H), 1.97-1.92 (m, 3H), 1.75-1.73 (m, 3H), 1.21-1.15 (m, 4H). |

TABLE 31-continued

| Compound # | Reagent | Chiral Separation Conditions and Characterization Data |
|---|---|---|
| I-293 | (4,5-dimethylthiazol-2-yl-substituted 3-amino-pyridin-2(1H)-one) | MS (ES): m/z 465.46 [M + H]⁺ LCMS purity: 100%, HPLC purity: 100%, ¹H NMR (DMSO-$d_6$, 400 MHZ): 9.27 (s, 1H), 8.44-8.42 (d, J = 8 Hz, 1H), 8.26-8.25 (d, J = 4 Hz, 1H), 8.21 (s, 1H), 7.99-7.98 (d, J = 4 Hz, 1H), 7.81 (s, 1H), 6.63-6.62 (t, J = 4 Hz, 1H), 6.24 (s, 1H), 2.91-2.90 (d, J = 4 Hz, 3H), 2.86 (m, 1H), 2.37 (s, 3H), 2.32 (s, 3H), 1.23 (bs, 2H), 0.79-0.78 (m, 2H), 0.50 (bs, 2H). |
| I-282 | (3-amino-5-methyl-2-(3-methoxypropyl)pyridine) | MS (ES): m/z 426.22 [M + H]⁺, LCMS purity: 98.64%, HPLC purity: 98.33%, ¹H NMR (DMSO-$d_6$, 400 MHZ): 8.79 (s, 1H), 8.10 (s, 1H), 7.92 (s, 1H), 7.90 (s, 1H), 7.88-7.87 (d, J = 4 Hz, 1H), 7.79 (s, 1H), 5.77 (s, 1H), 4.45-4.44 (t, J = 4 Hz, 2H), 4.33 (m, 1H), 3.65-3.64 (t, J = 4 Hz, 2H), 3.20 (s, 3H), 2.92-2.90 (d, J = 8 Hz, 3H), 2.28 (s, 3H), 2.16-2.15 (m, 2H), 1.60-1.56 (m, 4H). |
| I-328 | (3-amino-1-(1-methyl-1H-pyrazol-5-yl)pyridin-2(1H)-one) | MS (ES): mz 434.22 [M + H]⁺, LCMS purity: 100%, HPLC purity: 99.13%, ¹H NMR (DMSO-$d_6$, 400 MHZ): 9.07 (s, 1H), 8.45-8.44 (d, J = 4 Hz, 1H), 8.20 (s, 1H), 7.98-7.94 (m, 2H), 7.585-7.580 (d, J = 2 Hz, 1H), 6.499-6.494 (d, J = 2 Hz, 1H), 6.44-6.43 (t, J = 4 Hz, 1H), 6.26 (s, 1H), 5.76 (s, 1H), 4.51-4.45 (m, 1H), 3.64 (s, 3H), 2.90-2.89 (d, J = 4 Hz, 3H), 2.35-2.33 (m, 2H), 1.99-1.89 (m, 2H), 1.76-1.68 (m, 2H). |
| I-251 | (3-amino-5-methyl-1-(1-methyl-1H-pyrazol-3-yl)pyridin-2(1H)-one) | MS (ES): mz 448.56 [M + H]⁺, LCMS purity: 100%, HPLC purity: 100%, ¹H NMR (DMSO-$d_6$, 400 MHZ): 8.92 (s, 1H), 8.20 (s, 1H), 8.129-8.124 (d, J = 2 Hz, 1H), 7.94-7.92 (d, J = 8 Hz, 1H), 7.85-7.83 (d, J = 8 Hz, 1H), 7.832 (s, 1H), 7.53 (s, 1H), 6.768-6.763 (d, J = 2 Hz, 1H), 6.20 (s, 1H), 4.52-4.45 (m, 1H), 3.90 (s, 3H), 2.92-2.91 (d, J = 4 Hz, 3H), 2.30-2.26 (m, 2H), 2.21 (s, 3H), 1.97-1.91 (m, 2H), 1.73-1.64 (m, 2H). |
| I-242 | (3-amino-1-(thiazol-2-yl)pyridin-2(1H)-one) 97h | MS (ES): m/z 437.49 [M + H]⁺, LCMS purity: 100%, HPLC purity: 99.13%, ¹H NMR (DMSO-$d_6$, 400 MHZ): 9.36 (s, 1H), 8.56-8.54 (d, J = 8 Hz, 1H), 8.43-8.42 (d, J = 4 Hz, 1H), 8.21 (s, 1H), 8.02 (s, 1H), 7.97-7.95 (d, J = 8 Hz, 1H), 7.86-7.85 (d, J = 4 Hz, 1H), 7.74-7.73 (d, J = 8 Hz, 1H), 6.69-6.67 (t, J = 8 Hz, 1H), 6.28 (s, 1H), 4.48-4.46 (m, 1H), 2.93-2.92 (d, J = 4 Hz, 3H), 191-1.88 (m, 3H), 1.73-1.72 (m, 3H). |
| I-204 | (3-amino-1-((S)-tetrahydrofuran-3-yl)pyridin-2(1H)-one) | MS (ES): m/z 424.51 [M + H]⁺, LCMS purity: 98.63%, HPLC purity: 98.19%, CHIRAL HPLC purity: 100%, ¹H NMR (DMSO-$d_6$, 400 MHZ): 8.94 (s, 1H), 8.29-8.27 (d, J = 8 Hz, 1H), 8.17 (s, 1H), 7.96-7.91 (m, 2H), 7.33-7.31 (d, J = 8 Hz, 1H), 6.37-6.35 (t, J = 8 Hz, 1H), 6.23 (s, 1H), 5.53-5.49 (m, 1H), 4.50-4.44 (m, 1H), 4.11-4.05 (m, 1H), 3.91-3.90 (d, J = 4 Hz, 2H), 3.79-3.75 (m, 1H), 2.91-2.90 (d, J = 4 Hz, 3H), 2.33-2.29 (m, 2H), 1.93-1.85 (m, 2H), 1.76-1.69 (m, 2H), 1.23-1.21 (m, 2H). |

TABLE 31-continued

| Compound # | Reagent | Chiral Separation Conditions and Characterization Data |
|---|---|---|
| I-205 | (structure) | MS (ES): m/z 424.51 [M + H]⁺, LCMS purity: 98.77%, HPLC purity: 95.05%, CHIRAL HPLC purity: 99.53%, $^1$H NMR (DMSO-$d_6$, 400 MHZ): 8.94 (s, 1H), 8.29-8.27 (d, J = 8 Hz, 1H), 8.17 (s, 1H), 7.96-7.91 (m, 2H), 7.33-7.31 (d, J = 8 Hz, 1H), 6.37-6.35 (t, J = 8 Hz, 1H), 6.23 (s, 1H), 5.53-5.49 (m, 1H), 4.50-4.44 (m, 1H), 4.11-4.05 (m, 1H), 3.91-3.90 (d, J = 4 Hz, 2H), 3.79-3.75 (m, 1H), 2.91-2.90 (d, J = 4 Hz, 3H), 2.33-2.29 (m, 2H), 1.93-1.85 (m, 2H), 1.76-1.69 (m, 2H), 1.23-1.21 (m, 2H). |
| I-345 | (structure) 96nnn | MS (ES): mz 466.56 [M + H]⁺, LCMS purity: 99.62%, HPLC purity: 99.44%, CHIRAL HPLC: 100%, $^1$H NMR (DMSO-$d_6$, 400 MHZ): 8.89 (s, 1H), 8.26-8.25 (d, J = 6.8 Hz, 1H), 8.17 (s, 1H), 7.96-7.90 (m, 2H), 7.45-7.43 (d, J = 6.4 Hz, 1H), 6.33-6.29 (t, J = 7.2 Hz, 1H), 6.21 (s, 1H), 4.82-4.78 (m, 1H), 4.49-4.43 (m, 1H), 3.22 (s, 3H), 2.91-2.90 (d, J = 4.8 Hz, 3H), 2.33-2.31 (m, 2H), 2.16-1.92 (m, 2H), 1.92-167 (m, 6H), 1.56 (bs, 1H), 1.34-1.23 (m, 4H). |
| I-303 | (structure) | MS (ES): m/z 445.50 [M + H]⁺, LCMS purity: 96.41%, HPLC purity: 96.77%, $^1$H NMR (DMSO-$d_6$, 400 MHZ): 9.02 (s, 1H), 8.56-8.53 (d, J = 10 Hz, 2H), 8.41-8.39 (d, J = 6 Hz, 1H), 8.19 (s, 1H), 7.99-7.94 (m, 2H), 7.85 (s, 1H), 7.43-7.43 (d, J = 1.6 Hz, 1H), 6.43-6.40 (t, J = 7.2 Hz, 1H), 6.25 (s, 1H), 4.52-4.46 (m, 1H), 2.91-2.89 (d, J = 4.8 Hz, 3H), 2.40-2.34 (m, 6H), 1.97-1.90 (m, 2H), 1.74-1.68 (m, 1H). |
| I-176 | (structure) | MS (ES): m/z 371.48 [M + H]⁺, LCMS purity: 99.40%, HPLC purity: 99.18%, $^1$H NMR (DMSO-$d_6$, 400 MHZ): 8.96 (s, 1H), 8.31-8.30 (d, J = 4 Hz, 1H), 8.12 (s, 1H), 7.99-7.96 (d, J = 12 Hz, 1H), 7.94-7.90 (m, 2H), 7.05-7.02 (m, 1H), 5.90 (s, 1H), 4.43-4.37 (m, 1H), 2.91-2.90 (d, J = 4 Hz, 3H), 2.23-2.21 (m, 2H), 1.76-1.60 (m, 4H). |
| I-278 | (structure) | MS (ES): m/z 412.22 [M + H]⁺, LCMS purity: 97.74%, HPLC purity: 96.88%, $^1$H NMR (DMSO-$d_6$, 400 MHZ): 8.56-8.53 (m, 1H), 8.41 (s, 1H), 7.80-7.79 (d, J = 2.4 Hz, 1H), 7.78-7.75 (d, J = 8.4 Hz, 1H), 7.01 (s, 1H), 6.36 (bs, 1H), 5.42 (s, 1H), 4.75-4.69 (s, 1H), 4.40-4.37 (m, 1H), 3.15-3.14 (d, J = 5.2 Hz, 3H), 2.49-2.43 (m, 2H), 2 08-2.01 (m, 2H), 1.82-1.73 (m, 4H), 0.94-0.87 (m, 2H). |
| I-224 | (structure) | MS (ES): m/z 404.55 [M + H]⁺, LCMS purity: 100%, HPLC purity: 99.92%, $^1$H NMR (DMSO-$d_6$, 400 MHZ): 8.84-8.82 (d, J = 8 Hz, 1H), 8.80 (s, 1H), 8.46-8.41 (m, 2H), 8.35 (s, 1H), 8.24-8.23 (d, J = 8 Hz, 1H), 7.32-7.29 (m, 1H), 6.80 (s, 1H), 5.24-5.23 (t, J = 4 Hz, 1H), 4.58-4.56 (m, 1H), 3.13-3.12 (d, J = 4 Hz, 3H), 2.44-2.38 (m, 2H), 2.07-2.05 (t, J = 8 Hz, 2H), 1.61-1.59 (d, J = 4 Hz), 1.83-1.75 (m, 2H). |

TABLE 31-continued

| Compound # | Reagent | Chiral Separation Conditions and Characterization Data |
|---|---|---|
| I-151 | (pyridine with NH₂ and OCHF₂ substituents) | MS(ES): m/z 404.39 [M + H]⁺, LCMS purity: 100%, HPLC purity: 99.07%, ¹H NMR (DMSO-d₆, 400 MHZ): 9.18 (s, 1H), 8.45-8.43 (d, J = 6.8 Hz, 1H), 8.14 (s, 1H), 8.04-8.03 (d, J = 3.6 Hz, 1H), 7.99-7.98 (d, J = 4 Hz 1H), 7.90-7.88 (d, J = 8.4 Hz, 1H), 7.80 (s, 1H), 7.34-7.31 (m, 1H), 5.88 (s, 1H), 4.40-4.37 (m, 1H), 2.93-2.92 (d, J = 4.8 Hz, 3H), 2.20-2.19 (d, J = 4.8 Hz, 2H), 1.64 (s, 4H). |
| I-269 | (3-amino-1-(2-methoxyethyl)pyridin-2(1H)-one) | MS(ES): m/z 412.47 [M + H]⁺, LCMS purity: 100%, HPLC purity: 100%, ¹H NMR (DMSO-d₆, 400 MHZ): 8.93 (s, 1H), 8.29-8.27 (d, J = 6.4 Hz, 1H), 8.18 (s, 1H), 7.98-7.96 (d, J = 8.4 Hz, 2H), 7.36-7.35 (d, J = 5.6 Hz, 1H), 6.30-6.26 (t, J = 7.2 Hz, 2H), 4.49-4.45 (m, 1H), 4.20-4.18 (t, 2H), 3.67-3.65 (t, 2H), 3.27 (s, 3H), 2.91-2.90 (d, J = 4 Hz, 3H), 2.34-2.32 (m, 2H), 1.93-1.86 (m, 2H), 1.76-1.72 (m, 2H). |
| I-386 | (3-amino-1-(4-methyloxazol-2-yl)pyridin-2(1H)-one) | MS (ES): m/z 435.51 [M + H]⁺, LCMS purity: 100%, HPLC purity: 99.79%, ¹H NMR (DMSO-d₆, 400 MHZ): 9.09 (s, 1H), 8.37-8.36 (s, J = 6 Hz, 1H), 8.19 (s, 1H), 8.04-8.03 (d, J = 1.2 Hz, 1H), 7.99-7.98 (d, J = 4.8 Hz, 1H), 7.94-7.92 (d, J = 8 Hz, 1H), 7.48-7.46 (d, J = 5.6 Hz, 1H), 6.45-6.41 (t, J = 7.2 Hz, 1H), 6.21 (s, 1H), 4.49-4.43 (m, 1H), 2.91-2.90 (d, J = 4.8 Hz, 3H), 2.33-2.31 (d, J = 8.4 Hz, 2H), 2.19 (s, 3H), 1.93-1.89 (m, 2H), 1.74-1.68 (m, 2H). |
| I-122 | (3-amino-1-(5-(dimethylcarbamoyl)pyrazin-2-yl)pyridin-2(1H)-one) | MS (ES): m/z 503.54 [M + H]⁺, LCMS purity: 100%, HPLC purity: 100%, ¹H NMR (DMSO-d₆, 400 MHZ): 9.24 (s, 1H), 9.12 (s, 1H), 8.93(s, 1H), 8.43-8.42 (d, J = 7.2 Hz, 1H), 8.21 (s, 1H), 7.99-7.97 (d, J = 7.6 Hz, 2H), 7.70-7.69 (d, J = 6.4 Hz, 1H), 6.56-6.53 (t, J = 7.6 Hz, 1H), 6.27 (s, 1H), 4.52-4.46 (m, 1H), 3.09 (s, 3H), 3.06 (s, 3H), 2.93-2.92 (d, J = 4.8 Hz, 3H), 1.97-1.92 (m, 2H), 1.78-1.69 (m, 2H), 1.24 (bs, 2H). |
| I-163 | (3-amino-1-(5-morpholinopyridin-2-yl)pyridin-2(1H)-one)<br>97k | MS (ES): m/z 515.58 [M + H]⁺, LCMS purity: 98.41%, HPLC purity: 98.46%, ¹H NMR (DMSO-d₆, 400 MHZ): 9.00 (s, 1H), 8.37-8.35 (d, J = 7.2 Hz, 1H), 8.28 (s, 1H), 8.19 (s, 1H), 8.01-7.99 (d, J = 8.4 Hz, 1H), 7.94-7.93 (d, J = 4.8 Hz, 1H), 7.68-7.65 (d, J = 8.8 Hz, 1H), 7.59-7.53 (m, 2H), 6.43-6.39 (t, J = 7.2 Hz, 1H), 6.25 (s, 1H), 4.52-4.46 (m, 1H), 3.79 (s, 4H), 3.28 (s, 4H), 2.92-2.91 (d, J = 4.8 Hz, 3H), 2.34 (s, 2H), 2.00-1.92 (m, 2H), 1.77-1.69 (m, 2H). |

TABLE 31-continued

| Compound # | Reagent | Chiral Separation Conditions and Characterization Data |
|---|---|---|
| I-246 | 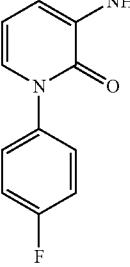 | MS (ES): m/z 448.25 [M + H]⁺, LCMS purity: 99.51%, HPLC purity: 99.54%, ¹H NMR (DMSO-d₆, 400 MHZ): 8.99 (s, 1H), 8.39-8.37 (d, J = 8 Hz, 1H), 8.19 (s, 1H), 7.99-7.97 (d, J = 8 Hz, 1H), 7.95-7.94 (d, J = 4 Hz, 1H), 7.59-7.57 (t, J = 8 Hz, 2H), 7.42-7.36 (m, 3H), 6.40-6.38 (t, J = 8 Hz, 1H), 6.25 (s, 1H), 4.50-4.46 (m, 1H), 2.90-2.89 (d, J = 4 Hz, 3H), 2.35-2.33 (m, 2H), 1.97-1.92 (m, 2H), 1.74-1.68 (m, 2H). |
| I-238 | 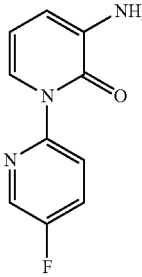 | MS (ES): m/z 449.47 [M + H]⁺, LCMS purity: 100%, HPLC purity: 99.73%, ¹H NMR (DMSO-d₆, 400 MHZ): 9.04 (s, 1H), 8.67-8.66 (d, J = 4 Hz, 1H), 8.39-8.37 (d, J = 8 Hz, 1H), 8.19 (s, 1H), 8.05-7.92 (m, 4H), 7.58-7.56 (d, J = 8 Hz, 1H), 6.46-6.44 (t, J = 8 Hz, 1H), 6.24 (s, 1H), 4.51-4.45 (m, 1H), 2.91-2.90 (d, J = 4 Hz, 3H), 2.35-2.31 (m, 2H), 1.98-1.89 (m, 2H), 1.76-1.69 (m, 2H). |
| I-141 | 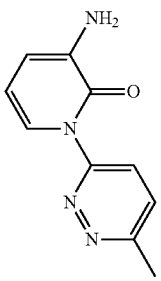
971 | MS (ES): m/z 446.49 [M + H]⁺, LCMS purity: 100%, HPLC purity: 98.93%, ¹H NMR (DMSO-d₆, 400 MHZ): 9.06 (s, 1H), 8.37 (s, 1H), 8.19 (s, 1H), 8.03-8.01 (d, J = 7.2 Hz, 2H), 7.81 (s, 1H), 7.61 (s, 1H), 6.49 (s, 1H), 6.25 (s, 1H), 5.76 (s, 1H), 4.50-4.48 (bs, 1H), 2.91 (s, 3H), 2.72 (s, 3H), 2.33 (bs, 2H), 1.96-1.92 (t, J = 8.4 Hz, 2H), 1.7 (bs, 2H). |
| I-158 | 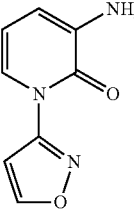 | MS (ES): m/z 421.43 [M + H]⁺, LCMS purity: 99.67%, HPLC purity: 98.82%, ¹H NMR (DMSO-d₆, 400 MHZ): 9.15-9.14 (m, 2H), 8.40-8.39 (d, J = 7.2 Hz, 1H), 8.20 (s, 1H), 7.99-7.94 (m, 2H), 7.66-7.65 (d, J = 6.8 Hz 1H), 7.22-7.21 (s, 1H), 6.51-6.48 (t, J = 7.2 Hz, 1H), 6.26 (s, 1H), 4.51-4.45 (m, 1H), 2.92-2.91 (d, J = 4.8 Hz, 3H), 1.95-1.90 (m, 3H), 1.76-1.68 (m, 3H). |
| I-290 | 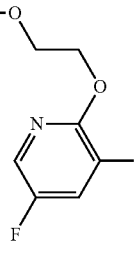 | MS (ES): m/z 430.38 [M + H]⁺, LCMS purity: 100%, HPLC purity: 99.51%, ¹H NMR (DMSO-d₆, 400 MHZ): 8.96 (bs, 1H), 8.44-8.42 (d, J = 8 Hz, 1H), 8.19 (s, 1H), 8.02 (bs, 1H), 7.88 (s, 1H), 7.87-7.86 (d, J = 4 Hz, 1H), 6.07 (s, 1H), 4.53-4.52 (t, J = 4 Hz, 2H), 4.48-4.52 (m, 1H), 3.75-3.74 (t, J = 4 Hz, 2H), 3.29 (s, 3H), 2.94 (s, 3H), 2.24-2.22 (m, 2H), 1.85-1.80 (m, 2H), 1.66-1.63 (m, 2H). |
| I-288 | 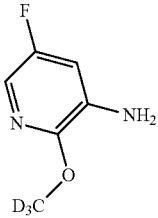 [SMILES: [2H]C([2H])([2H])Oc1ncc(F)cc1N] | MS (ES): m/z 389.41 [M + H]⁺, LCMS purity: 100%, HPLC purity: 100%, ¹H NMR (DMSO-d₆, 400 MHZ): 9.07 (s, 1H), 8.45-8.43 (d, J = 8 Hz, 1H), 8.18 (s, 1H), 8.00-7.99 (d, J = 4 Hz, 1H), 7.86 (s, 1H), 7.84 (s, 1H), 6.06 (s, 1H), 4.46-4.44 (m, 1H), 2.92-2.91 (d, J = 4 Hz, 3H), 2.23 (bs, 2H), 1.86-1.81 (m, 2H), 1.64 (m, 2H). |

TABLE 31-continued

| Compound # | Reagent | Chiral Separation Conditions and Characterization Data |
|---|---|---|
| I-216 | (3-amino-2-cyclopropoxypyridine) | MS (ES): m/z 394.28 [M + H]⁺, LCMS purity: 96.38%, HPLC purity: 95.05%, ¹H NMR (DMSO-d₆, 400 MHZ): 8.76 (s, 1H), 8.30-8.28 (d, J = 8 Hz, 1H), 8.12 (s, 1H), 7.97-7.90 (m, 3H), 7.07-7.04 (m, 1H), 5.85 (s, 1H), 4.40-4.34 (m, 2H), 2.92-2.91 (d, J = 4 Hz, 3H), 1.75-1.65 (m, 5H), 1.23 (s, 1H), 0.78-0.73 (m, 4H). |
| I-342 | (3-amino-1-(1,3-dimethyl-1H-pyrazol-5-yl)pyridin-2(1H)-one) | MS (ES): m/z 448.41 [M + H]⁺, LCMS purity: 99.53%, HPLC purity: 98.55%, ¹H NMR (DMSO-d₆, 400 MHZ): 9.06 (s, 1H), 8.52-8.42 (m, 1H), 8.20 (s, 1H), 7.98-7.94 (m, 2H), 7.29-7.28 (d, J = 6.16 Hz, 1H), 6.43-6.40 (t, J = 7.2 Hz, 1H), 6.27 (s, 2H), 4.54-4.45 (m, 1H), 3.56 (s, 3H), 3.56 (s, 3H), 2.91-2.90 (d, 3H), 2.36-2.34 (d, 2H), 1.99-1.89 (m, 2H), 1.74-1.69 (m, 2H), 1.56 (bs, 1H). |
| I-121 | 97n | MS(ES): m/z 528.4 [M + H]⁺, LCMS purity: 100%, HPLC purity: 99.30%, ¹H NMR (DMSO-d₆, 400 MHZ): 9.05 (s, 1H), 8.80 (s, 1H), 8.40-8.39 (d, J = 6.4 Hz, 1H), 8.20 (s, 2H), 8.00-7.96 (m, 3H), 7.68-7.66 (d, J = 6.8 Hz, 1H), 6.49-6.463 (t, J = 7.2 Hz, 1H), 6.26 (s, 1H), 4.52-4.46 (m, 1H), 3.53-3.51 (m, 4H), 2.93-2.92 (d, J = 4.4 Hz, 3H), 2.34-2.31 (m, 2H), 1.97-1.90 (m, 6H), 1.78-1.73 (m, 2H). |
| I-192 | (NH₂·HCl salt with piperidine-difluoroethyl) | MS (ES): m/z 501.53 [M + H]⁺, LCMS purity: 100%, HPLC purity: 100%, ¹H NMR (DMSO-d₆, 400 MHZ): 8.90 (s, 1H), 8.27-8.26 (d, J = 4 Hz, 1H), 8.17 (s, 1H), 7.95 (s, 1H), 7.93 (s, 1H), 7.50-7.49 (d, J = 4 Hz, 1H), 6.22-6.17 (m, 2H), 4.80 (s, 1H), 4.47-4.45 (d, J = 8 Hz, 1H), 3.08-3.05 (d, J = 2 Hz, 2H), 2.90-2.77 (m, 5H), 2.39-2.33 (m, 4H), 2.08 (s, 1H), 1.92 (m, 4H), 1.78-1.74 (m, 4H). |
| I-219 | (2-(2-methoxyethoxy)-3-aminopyridine) | MS (ES): m/z 412.46 [M + H]⁺, LCMS purity: 100%, HPLC purity: 99.77%, ¹H NMR (DMSO-d₆, 400 MHZ): 8.85 (s, 1H), 8.29-8.27 (d, J = 8 Hz, 1H), 8.12 (s, 1H), 7.98-7.96 (d, J = 8 Hz, 1H), 7.93-7.92 (m, 2H), 7.05-7.02 (m, 1H), 5.90 (s, 1H), 4.52-4.51 (t, J = 4 Hz, 2H), 4.42-4.36 (m, 1H), 3.71-3.70 (t, J = 4 Hz, 2H), 3.25 (s, 3H), 2.92 (s, 3H), 2.22-2.20 (m, 2H), 1.73-1.63 (m, 4H). |

TABLE 31-continued

| Compound # | Reagent | Chiral Separation Conditions and Characterization Data |
|---|---|---|
| I-193 | 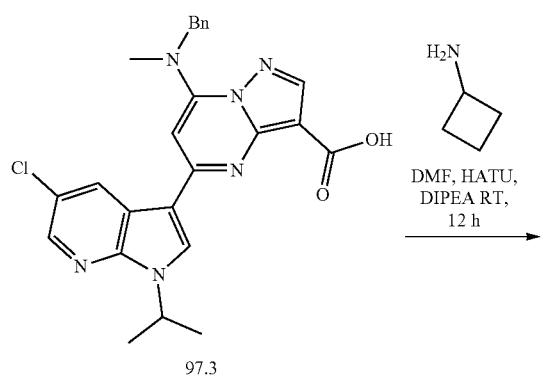 | MS (ES): m/z 449.30 [M + H]+, LCMS purity: 95.99%, HPLC purity: 99.30%, 1H NMR (DMSO-d6, 400 MHZ): 9.25 (s, 1H), 8.66-8.65 (d, J = 4 Hz, 1H), 8.53-8.51 (d, J = 8 Hz, 1H), 8.25 (s, 1H), 8.09-8.08 (t, J = 4 Hz, 2H), 7.94-7.92 (d, J = 8 Hz, 1H), 7.84-7.79 (m, 2H), 7.57-7.56 (t, J = 4 Hz, 1H), 6.38 (s, 1H), 4.57-4.52 (m, 1H), 2.92 (s, 3H), 2.34-2.32 (m, 2H), 2.04-1.99 (m, 2H), 1.71-1.69 (m, 2H). |
| I-160 | 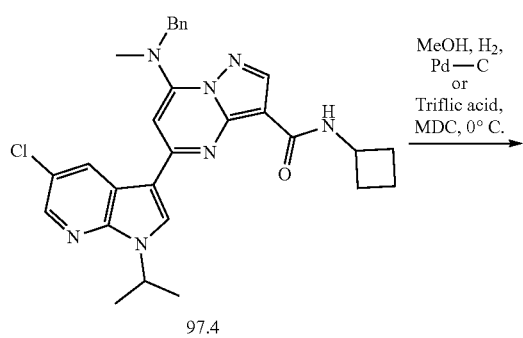 | MS(ES): m/z 435.46 [M + H]+, LCMS purity: 100%, HPLC purity: 99.77%, 1H NMR (DMSO-d6, 400 MHZ): 9.11 (s, 1H), 8.39-8.37 (d, J = 7.2 Hz, 1H), 8.20 (s, 1H), 7.98-7.94 (m, 2H), 7.63-7.61 (d, J = 6.4 Hz 1H), 6.90 (s, 1H), 6.49-6.45 (t, J = 7.2 Hz, 1H), 6.26 (s, 1H), 4.50-4.44 (m, 1H), 2.92-2.91 (d, J = 4.4 Hz, 3H), 2.34-2.32 (d, J = 7.6 Hz, 3H), 1.94-1.89 (m, 2H), 1.76-1.67 (m, 2H), 1.24 (bs, 2H). |

Synthesis of: 5-(5-chloro-1-isopropyl-1H-pyrrolo[2,3-b]pyridin-3-yl)-N-cyclobutyl-7-(methylamino)pyrazolo[1,5-a]pyrimidine-3-carboxamide (I-273)

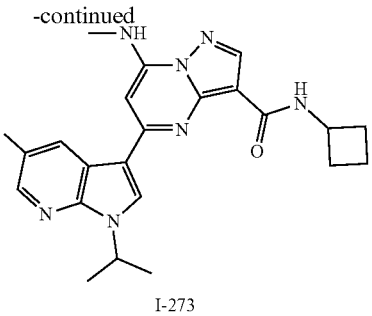

Synthesis of Compound 97.3.

Compound was synthesized as per Example 103 (I-272) to obtain 97.3.

Synthesis of Compound 97.4.

Compound was synthesized using general procedure of A to obtain 97.4 (0.075 g, 67.46%). MS (ES): m/z 529.26 [M+H]+.

Synthesis of Compound I-273:

Mixture of 97.4 (0.075 g, 0.142 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-273 (0.035 g, 56.27%), MS (ES): m/z 438.22 [M+H]+, LCMS purity: 96.04%, HPLC purity: 96.36%, 1H NMR (DMSO-d6, 400 MHZ): 8.88 (s, 1H), 8.786-8.781 (d, J=2 Hz, 1H), 8.43 (s, 1H), 8.37 (s, 1H), 8.29-8.28 (d, J=4 Hz, 1H), 8.23-8.21 (d, J=8 Hz, 1H), 6.80 (s, 1H), 5.19-5.16 (m, 1H), 4.62-4.56 (m, 1H), 3.12-3.11 (d, J=4 Hz, 3H), 2.36-2.34 (m, 2H), 2.11-2.07 (m, 2H), 1.75 (m, 2H), 1.60-1.58 (d, J=8 Hz, 6H).

Synthesis of N-cyclobutyl-5-((6'-methyl-2-oxo-2H-[1,2'-bipyridin]-3-yl)amino)-7-(methylamino)pyrazolo[1,5-a]pyrimidine-3-carboxamide (I-130)

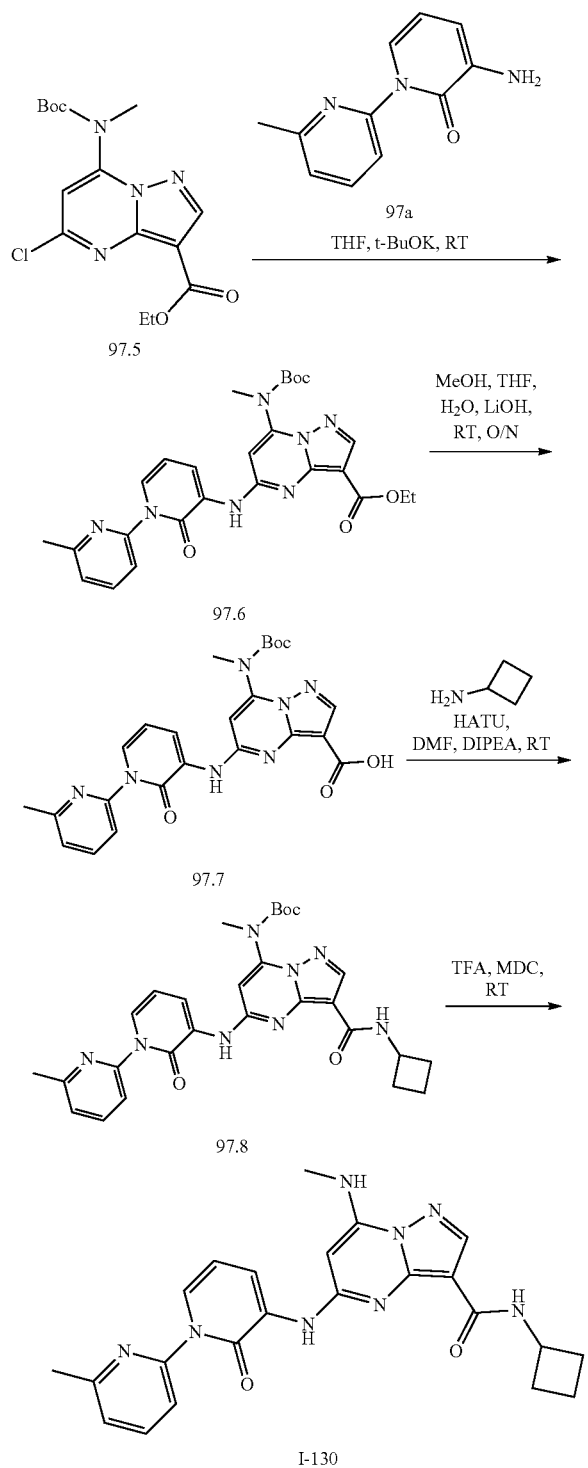

Synthesis of Compound 97.5.

Compound was synthesized using general procedure of core synthesis to obtain 97.5. (Yield: 62.21%). MS (ES): m/z 355.5 [M+H]+

Synthesis of Compound 97.6.

To a solution 97.5 (0.30 g, 0.84 mmol, 1.0 eq) and 97a (0.11 g, 0.92 mmol, 1.1 eq) in tetrahydrofuran (3 mL) was added, potassium tert.butoxide (1.7 mL, 1.78 mmol, 2.0 eq) at room temperature. The reaction mixture was stirred at room temperature. After completion of reaction, reaction mixture was transferred to ice cold water and product was extracted with ethylacetate. Organic layer was combined, dried over sodium sulphate and concentrated under reduced pressure to obtain crude material. This was further purified by column chromatography to obtain pure 97.6 (0.3 g, 70.56%). MS (ES): mz 520.56 [M+H][M+H]

Synthesis of Compound 97.7.

To a solution of 97.6 (0.31 g, 0.59 mmol, 1.0 eq), in tetrahydrofuran: methanol: water (5 mL, 1:1:1) was added lithium hydroxide (0.24 g, 5.90 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 50° C. Product was extracted with dichloromethane. Organic layer was combined, washed with brine solution, dried over sodium sulphate and concentrated under reduced pressure to obtain 97.7 (0.24 g, 81.84%). MS(ES): m/z 492.51 [M+H]+

Synthesis of Compound 97.8.

Compound was synthesized using general procedure A to obtain 97.8 (Yield: 30.08%). MS (ES): m/z 545.62 [M+H]+

Synthesis of Compound I-130.

Compound was synthesized using general procedure C to obtain I-130. (Yield: 41.35%). MS (ES): m/z 445.50 [M+H]+, LCMS purity: 98.78%, HPLC purity: 98.35%, 1H NMR (DMSO-$d_6$, 400 MHZ): 9.01 (s, 1H), 8.38-8.36 (d, J=6 Hz, 1H), 8.19 (s, 1H), 8.00-7.91 (m, 3H), 7.64-7.56 (m, 2H), 7.41-7.39 (d, J=7.6 Hz, 1H), 6.44-6.41 (t, J=7.6 Hz, 1H), 6.23 (s, 1H), 4.52-4.45 (m, 1H), 2.91-2.90 (d, J=4.8 Hz, 3H), 2.54-2.50 (m, 3H), 2.35-2.33 (d, J=8.4 Hz, 3H), 1.98-1.94 (m, 2H), 1.77-1.68 (m, 1H).

Characterization data for further compounds prepared by the above methods are presented in Table 32 below. Compounds in Table 32 were prepared by methods substantially similar to those described to prepare I-130, where 97a was replaced with the reagent as indicated in Table 32.

TABLE 32

| Compound # | Reagent | Chiral Separation Conditions and Characterization Data |
|---|---|---|
| I-149 | Cl, pyridine with NH2 and O-isopropyl substituents | MS (ES): m/z 430.91 [M + H]+, LCMS purity: 100%, HPLC purity: 98.70%, 1H NMR (DMSO-$d_6$, 400 MHZ): 8.77 (s, 1H), 8.37-8.37 (d, J = 2 Hz, 1H), 8.17 (s, 1H), 7.99-7.98 (d, J = 4.8 Hz, 1H), 7.93-7.93 (d, J = 2 Hz, 1H), 7.81-7.79 (d, J = 8.4 Hz, 1H), 5.97 (s, 1H), 5.35-5.29 (m, 1H), 4.42-4.36 (m, 1H), 2.94-2.93 (d, J = 4.8 Hz, 3H), 2.21-2.20 (m, 2H), 1.82-1.78 (m, 2H), 1.65-1.63 (m, 2H), 1.35-1.33 (d, J = 6 Hz, 6H). |

TABLE 32-continued

| Compound # | Reagent | Chiral Separation Conditions and Characterization Data |
|---|---|---|
| I-136 | 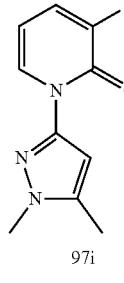 97i | MS (ES): m/z 448.50 [M + H]+, LCMS purity: 100%, HPLC purity: 99.89%, $^1$H NMR (DMSO-$d_6$, 400 MHZ): 9.02 (s, 1H), 8.31-8.30 (d, J = 7.2 Hz, 1H), 8.18 (s, 1H), 7.98-7.93 (m, 2H), 7.66-7.64 (m, 1H), 6.56 (s, 1H), 6.40-6.37 (t, J = 7.2 Hz, 1H), 6.24 (s, 1H), 3.77 (s, 3H), 3.17-3.16 (d, J = 5.2 Hz, 1H), 2.91-2.90 (d, J = 4.8 Hz, 3H), 2.33 (s, 3H), 2.01-1.99 (t, J = 6.8 Hz, 2H), 1.94-1.89 (m, 2H), 1.23 (s, 2H). |
| I-145 | 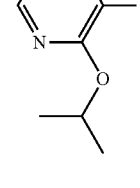 | MS (ES): m/z 396.47 [M + H]+, LCMS purity: 95.31%, HPLC purity: 96.51%, $^1$H NMR (DMSO-$d_6$, 400 MHZ): 8.69 (s, 1H), 8.28-8.28 (d, J = 1.6 Hz, 2H), 8.12 (s, 1H), 7.98-7.96 (d, J = 8.4 Hz 1H), 7.92-7.89 (m, 2H), 5.91 (s, 1H), 5.39-5.33 (m, 1H), 4.42-4.36 (m, 1H), 2.94-2.92 (d, J = 4.8 Hz, 3H), 2.20-2.21 (d, J = 4 Hz, 2H), 1.74-1.63 (m, 4H), 1.37-1.32 (m, 6H). |
| I-95 | 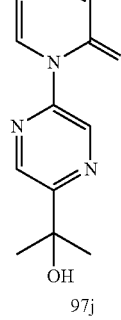 97j | MS (ES): m/z 490.53 [M + H]+, LCMS purity : 98.86%, HPLC purity: 98.42%, $^1$H NMR (DMSO-$d_6$, 400 MHZ): 9.10-9.08 (d, J = 8 Hz, 2H), 8.93 (s, 1H), 8.42 (s, 1H), 8.20 (s, 1H), 7.97 (s, 2H), 7.66-7.64 (d, J = 8 Hz, 1H), 6.50 (s, 1H), 6.27 (s, 1H), 5.64 (s, 1H), 4.50-4.48 (m, 1H), 2.92 (s, 3H), 2.34 (s, 2H), 1.94 (m, 2H), 1.76 (m, 2H), 1.55 (s, 6H). |
| I-94 | 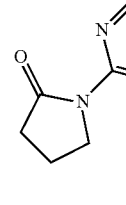 | MS (ES): m/z 421.52 [M + H]+, LCMS purity: 99.19%, HPLC purity: 99.43%, $^1$H NMR (DMSO-$d_6$, 400 MHZ): 9.86 (s, 1H), 8.20 (s, 1H), 8.13-8.11 (d, J = 8 Hz, 1H), 8.08-8.07 (d, J = 4 Hz, 1H), 7.94-7.92 (d, J = 8 Hz, 1H), 7.80-7.78 (t, J = 8 Hz, 1H), 7.42-7.40 (d, J = 8 Hz, 1H), 6.63 (s, 1H), 4.51-4.45 (m, 1H), 4.13-4.12 (t, J = 4 Hz, 2H), 2.98-2.97 (d, J = 4 Hz, 3H), 2.60 (s, 2H), 2.34-2.30 (m, 2H) 2.09 (s, 2H), 2.00-1.98 (d, J = 8 Hz, 2H), 1.76-1.67 (m, 2H). |
| I-139 | 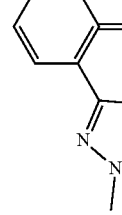 97m | MS (ES): m/z 434.48 [M + H]+, LCMS purity: 100%, HPLC purity: 99.89%, $^1$H NMR (DMSO-$d_6$, 400 MHZ): 9.05 (s, 1H), 8.34-8.32 (d, J = 6 Hz, 1H), 8.19 (s, 1H), 7.99-7.93 (m, 2H), 7.85-7.84 (d, J = 2 Hz, 1H), 7.70-7.70 (d, J = 1.2 Hz, 1H), 6.76-6.76 (d, J = 2 Hz, 1H), 6.43-6.39 (t, J = 7.2 Hz, 1H), 6.25 (s, 1H), 5.77 (s, 1H), 4.13-4.09 (m, 1H), 3.91 (s, 3H), 3.19-3.17 (d, J = 5.2 Hz, 1H), 2.92-2.91 (d, J = 4.8 Hz, 3H), 2.34-2.31 (m, 3H), 1.98-1.88 (m, 1H). |
| I-105 | 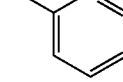 | Intermediate corresponding to 97.8 was first reacted with oxazolidin-2-one, DMEDA, K$_2$CO$_3$, and CuI in dioxane at 110° C. before BOC removal: MS (ES): m/z 423.29 [M + H]+, LCMS purity: 100%, HPLC purity: 97.98%, $^1$H NMR (DMSO-$d_6$, 400 MHZ): 9.97 (s, 1H), 8.22 (s, 1H), 8.15 (s, 2H), 7.83-7.81 (t, J = 8 Hz, 1H), 7.72-7.70 (d, J = 8 Hz, 1H), 7.41-7.40 (d, J = 4 Hz, 1H), 6.53 (s, 1H), 4.50-4.44 (m, 3H), 4.30-4.28 (t, J = 8 Hz, 2H), 2.96-2.95 (d, J = 4 Hz, 3H), 2.33-2.29 (m, 2H), 2.01-1.94 (m, 2H), 1.75-1.67 (m, 2H). |
| I-156 | 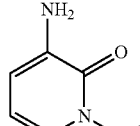 | MS (ES): m/z 489.55 [M + H]+, LCMS purity: 100%, HPLC purity: 100%, $^1$H NMR (DMSO-$d_6$, 400 MHZ): 8.51 (s, 1H), 7.89-7.87 (t, J = 7.6 Hz, 2H), 7.78-7.75 (m, 2H), 7.72-7.66 (m, 2H), 6.44-6.40 (t, J = 14.4 Hz, 1H), 4.42-4.38 (t, J = 16.4 Hz, 1H), 2.99 (s, 3H), 2.21 (m, 3H), 2.047-2.00 (m, 2H), 1.67 (s, 2H), 1.44 (s, 6H). |
| I-4 | 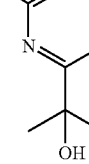 | MS (ES): m/z 368.52 [M + H]+, LCMS purity: 95% HPLC purity: 95.98% $^1$H NMR (DMSO-$d_6$, 400 MHZ): 8.96 (s, 1H), 8.33-8.32 (m, 1H), 8.13 (s, 1H), 7.99-7.91 (m, 3H), 7.06-7.03 (m, 1H), 5.91 (s, 1H), 4.44-4.38 (m, 1H), 3.97 (s, 3H), 2.93-2.91 (d, J = 4.8 Hz, 3H), 2.24-2.20 (m, 2H), 1.77-1.65 (m, 4H). |

Synthesis of Intermediate of 97a.

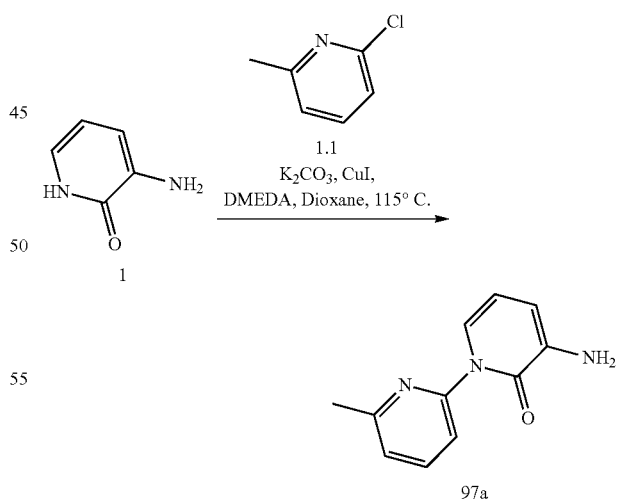

Synthesis of Compound 97a.

To a solution of 1. (2 g, 18.16 mmol, 1.0 eq) in 1,4-dioxane (10 mL), 1.1 (2.5 g, 19.97 mmol, 1.1 eq) was added. The reaction mixture was degassed for 10 min under argon atmosphere followed by addition of potassium carbonate (5.0 g, 36.32 mmol, 2.0 eq), N,N-dimethylethylenediamine (0.97 g, 5.44 mmol, 0.3 eq), and copper iodide (0.51 g, 2.72 mmol, 0.15 eq). The reaction mixture was heated at 115° C. for 48 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 97a (Yield: 41.04%). MS (ES): m/z 201.23 [M+H]

Synthesis of Intermediate of 97b.

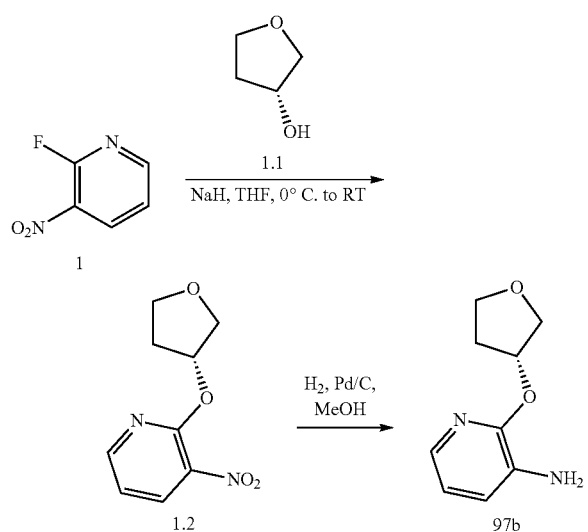

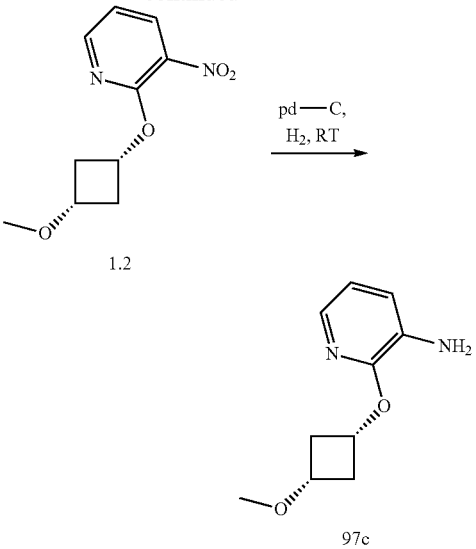

Synthesis of Compound 1.2.

To a cooled solution of 1 (1 g, 7.04 mmol, 1 eq) in tetrahydrofuran (10 mL) was added sodium hydride (0.570 mL, 14.08 mmol, 1.1 eq) followed by addition of 1.1 (0.930 g, 10.56 mmol, 1.5 eq) under nitrogen. The reaction was stirred at 0° C. for 30 min. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 15% ethyl acetate in hexane to obtain pure 1.2 (0.750 g, 50.70%), MS(ES): m/z 211.19 [M+H]$^+$.

Synthesis of Compound 97b.

To a solution of 1.2 (0.750 g, 3.57 mmol, 1.0 eq) in methanol (10 ml), palladium on charcoal (0.250 g) was added. Hydrogen was purged through reaction mixture for 3 h at room temperature. After completion of reaction, reaction mixture was filtered through celite-bed and washed with methanol. Filtrate was concentrated under reduced pressure to obtain pure 97b (0.600 g, 93.31%). MS (ES): m/z 181.21 [M+H]$^+$ Synthesis of Intermediate 97c.

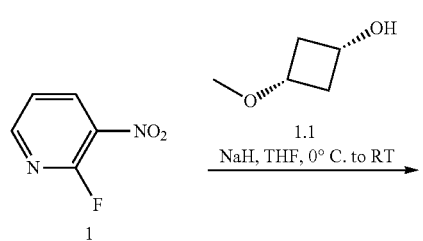

Synthesis of Compound 1.1.

Compound was synthesized as per Example 103 (I-111) to obtain 1.1.

Synthesis of Compound 1.2.

To a cooled solution of 1 (1 g, 7.04 mmol, 1 eq) in tetrahydrofuran (10 mL) was added sodium hydride (0.563 g, 14.08 mmol, 2 eq) followed by addition of 1.1 (0.790 g, 7.74 mmol, 1.1 eq) under nitrogen. The reaction was stirred at room temperature for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 9% ethyl acetate in hexane to obtain pure 1.2 (0.800 g, 50.70%), MS(ES): m/z 225.22 [M+H]$^+$.

Synthesis of Compound 97c.

To a solution of 1.2 (0800 g, 3.57 mmol, 1.0 eq) in methanol (10 ml), palladium on charcoal (0.250 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 0.9% methanol in dichloromethane to obtain pure 97c (0.500 g, 72.15%). MS (ES): m/z 195.23 [M+H]$^+$.

Synthesis of Intermediate 97d.

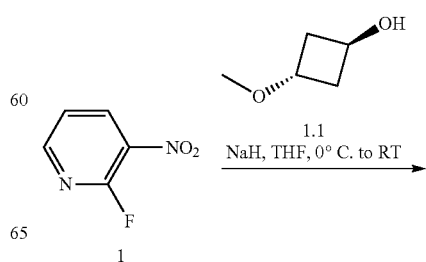

-continued

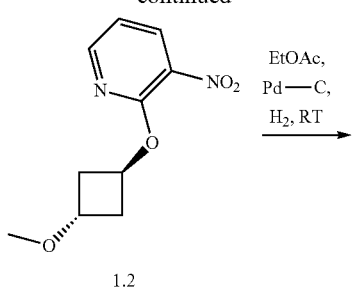

1.2

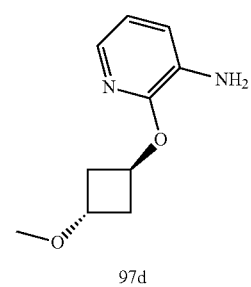

97d

Synthesis of Compound 1.1.

Compound was synthesized as per Example 103 (I-111) to obtain 1.1.

Synthesis of Compound 1.2.

To a cooled solution of 1.1 (0.711 g, 6.97 mmol, 1.1 eq) in tetrahydrofuran (7 mL) was added sodium hydride (0.278 g, 6.97 mmol, 1.1 eq) followed by addition of 1 (0.900 g, 6.33 mmol, 1 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 6% ethyl acetate in hexane to obtain pure 1.2 (0.800 g, 56.33%), MS(ES): m/z 225.22 [M+H]$^+$.

Synthesis of Compound 97d.

To a solution of 1.2 (0.800 g, 3.57 mmol, 1.0 eq) in ethyl acetate (6 ml), palladium on charcoal (0.100 g) was added. Hydrogen was purged through reaction mixture for 2-3 h at room temperature. After completion of reaction, reaction mixture was filtered through celite-bed and washed with methanol. Filtrate was concentrated under reduced pressure to obtain 97d (0.500 g, 72.15%). MS (ES): m/z 195.23 [M+H]$^+$ Synthesis of Intermediate 97e.

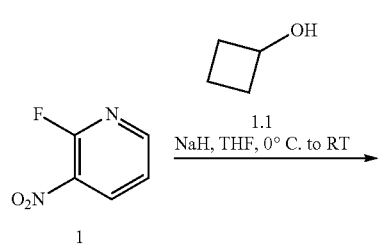

-continued

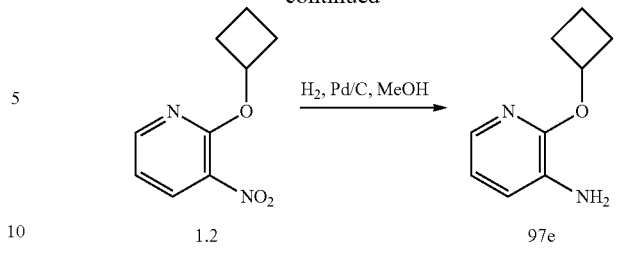

Synthesis of Compound 1.2.

To a cooled solution of 1 (1 g, 7.04 mmol, 1 eq) in tetrahydrofuran (10 mL) was added sodium hydride (0.310 g, 7.74 mmol, 1.1 eq) followed by addition of 1.1 (0.660 g, 9.15 mmol, 1.3 eq) under nitrogen. The reaction was stirred at room temperature for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 8% ethyl acetate in hexane to obtain pure 1.2 (0.900 g, 65.85%), MS(ES): m/z 195.19 [M+H]$^+$.

Synthesis of Compound 97e.

To a solution of 1.2 (0.900 g, 4.63 mmol, 1.0 eq) in methanol (10 ml), palladium on charcoal (0.250 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by trituration with pantane to obtain pure 97e (0.600 g, 78.84%). MS (ES): m/z 165.21 [M+H]$^+$.

Synthesis of Intermediate 97f.

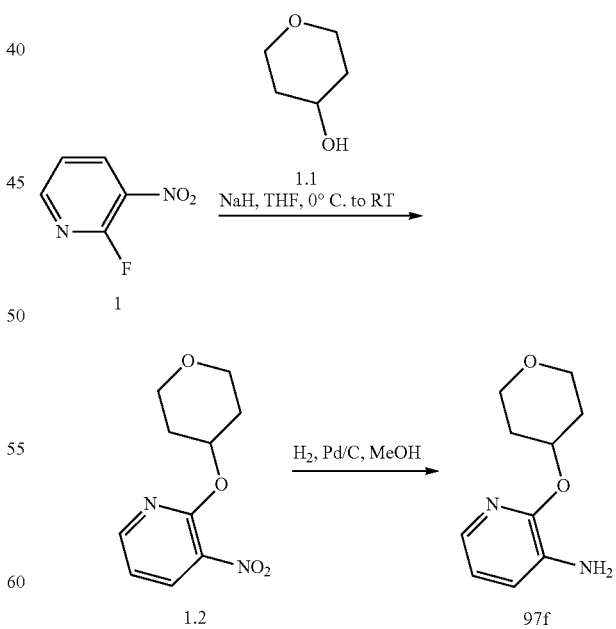

Synthesis of Compound 1.2.

To a cooled solution of 1 (1 g, 7.04 mmol, 1 eq) in tetrahydrofuran (10 mL) was added sodium hydride (0.570 mL, 14.08 mmol, 2 eq) followed by addition of 1.1 (0.934 g, 9.15 mmol, 1.3 eq) under nitrogen. The reaction was stirred at 0° C. for 30 min. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 15% ethyl acetate in hexane to obtain pure 1.2 (1 g, 63.37%), MS(ES): m/z 224.22 [M+H]$^+$.

Synthesis of Compound 97f.

To a solution of 1.2 (1 g, 4.46 mmol, 1.0 eq) in methanol (10 ml), palladium on charcoal (0.250 g) was added. Hydrogen was purged through reaction mixture for 3 h at room temperature. After completion of reaction, reaction mixture was filtered through celite-bed and washed with methanol. Filtrate was concentrated under reduced pressure to obtain pure 97f (0.800 g, 92.35%). MS (ES): m/z 195.23 [M+H]$^+$.

Synthesis of Intermediate 97g.

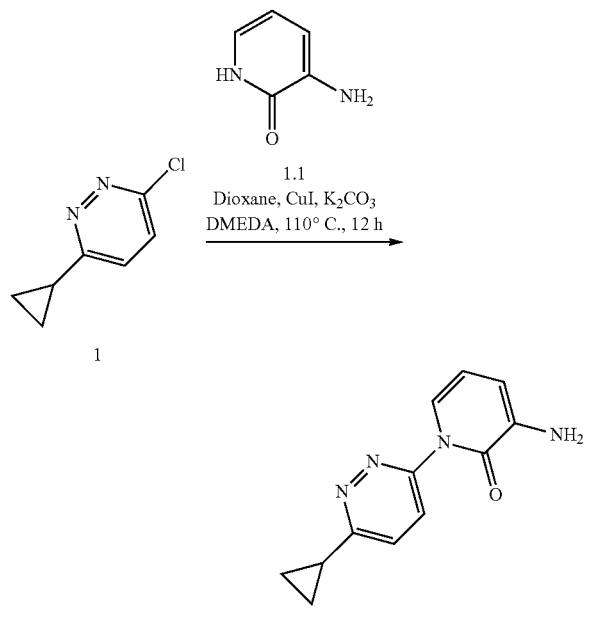

97g

Synthesis of Compound 97g.

To a solution of 1. (0.700 g, 4.53 mmol, 1.0 eq) and 1.1 (0.648 g, 5.89 mmol, 1.3 eq) in 1,4-dioxane (7 mL) was added potassium carbonate (1.25 g, 9.06 mmol, 2.0 eq) and degassed with argon for 15 min. Copper iodide (0.172 g, 0.906 mmol, 0.2 eq) and 1,2-dimethylethylenediamine (0.159 g, 1.81 mmol, 0.4 eq) was added and reaction mixture again degassed with argon for 5 min followed by heating at 110° C. for 12 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 4.1% methanol in dichloromethane to obtain pure 97 g (0.140 g, 13.55%). MS(ES): m/z 229.26 [M+H]$^+$.

Synthesis of Intermediate 97h.

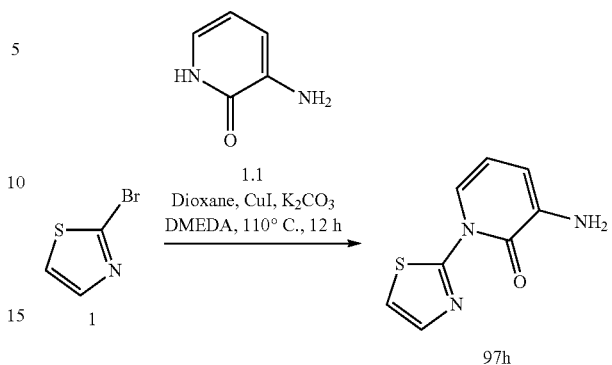

Synthesis of Compound 97h.

To a solution of 1. (1 g, 6.10 mmol, 1.0 eq) and 1.1 (0.805 g, 7.32 mmol, 1.2 eq) in 1,4-dioxane (10 mL) was added potassium carbonate (1.68 g, 12.20 mmol, 2.0 eq) and degassed with argon for 15 min. Copper iodide (0.348 g, 1.83 mmol, 0.3 eq) and 1,2-dimethylethylenediamine (0.161 g, 1.83 mmol, 0.3 eq) was added and reaction mixture again degassed with argon for 5 min followed by heating at 110° C. for 12 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.3% methanol in dichloromethane to obtain pure 97 h (0.900 g, 76.40%). MS(ES): m/z 194.22 [M+H]$^+$.

Synthesis of Intermediate 97i.

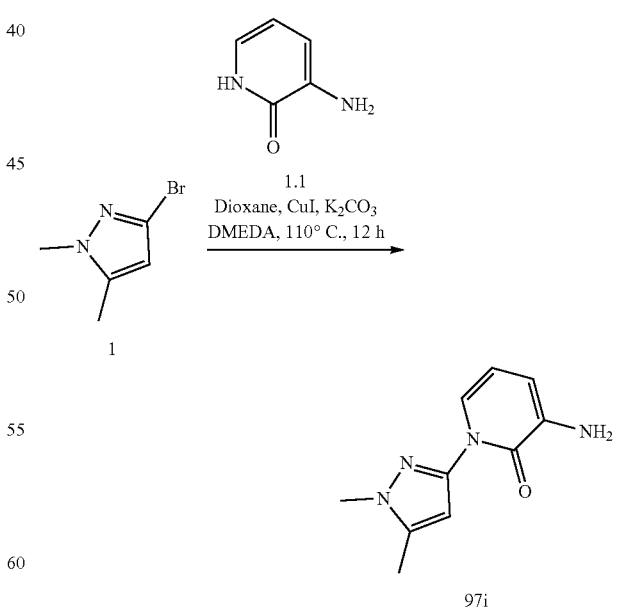

Synthesis of Compound 97i.

To a solution of 1. (1.5 g, 8.57 mmol, 1.0 eq) in 1,4-dioxane (10 mL), 1.1 (1.0 g, 9.42 mmol, 1.1 eq) was added. The reaction mixture was degassed for 10 min under argon atmosphere followed by addition of potassium carbonate (2.3 g, 17.14 mmol, 2.0 eq), N,N-dimethylethylenediamine (0.45 g, 2.57 mmol, 0.3 eq), and copper iodide (0.24 g, 1.28 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 1.2 (0.90 g, Yield: 51.42%). MS (ES): m/z 205.23 [M+H]$^+$.

Synthesis of Intermediate 97j.

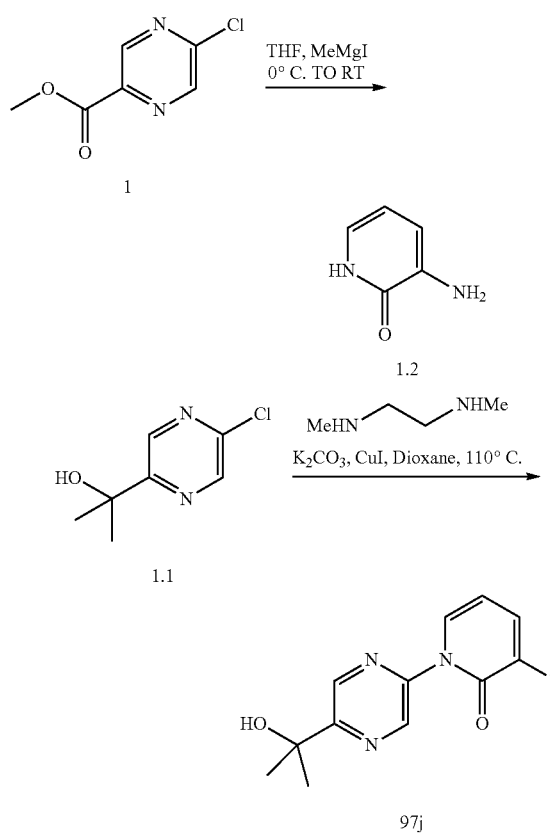

97j

Synthesis of Compound 1.1.

To a cooled solution of 1. (2.0 g, 11.59 mmol, 1.0 eq) in tetrahydrofuran (30 mL), was added methyl magnesium iodide (2.88 g, 17.39 mmol, 1.5 eq) under nitrogen at 0° C. The reaction was stirred at room temperature for 15 min. After completion of reaction, reaction mixture was transferred into 1N hydrochloric acid and extracted with ethyl acetate. Organic layer was washed with saturated sodium bicarbonate solution. Organic layer was combined, dried over sodium sulphate and concentrated under reduced pressure to obtain crude material. This was further purified by column chromatography and compound was eluted in 12% ethyl acetate in hexane to obtain pure 1.1 (1.4 g, 69.98%). MS (ES): m/z 173.61 [M+H]$^+$.

Synthesis of Compound 97j.

To a solution of 1.1 (1.4 g, 8.11 mmol, 1.0 eq) and 1.2 (0.803 g, 7.30 mmol, 0.9 eq) in 1,4-dioxane (20 mL) was added potassium carbonate (2.24 g, 16.22 mmol, 2.0 eq) and degassed with argon for 15 min. Copper iodide (0.308 g, 1.62 mmol, 0.2 eq) and 1,2-dimethylethylenediamine (0.286 g, 3.24 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 19% ethyl acetate in hexane to obtain pure 97j (0.600 g, 30.04%). MS(ES): m/z 247.27 [M+H]$^+$.

Synthesis of Intermediate 97k.

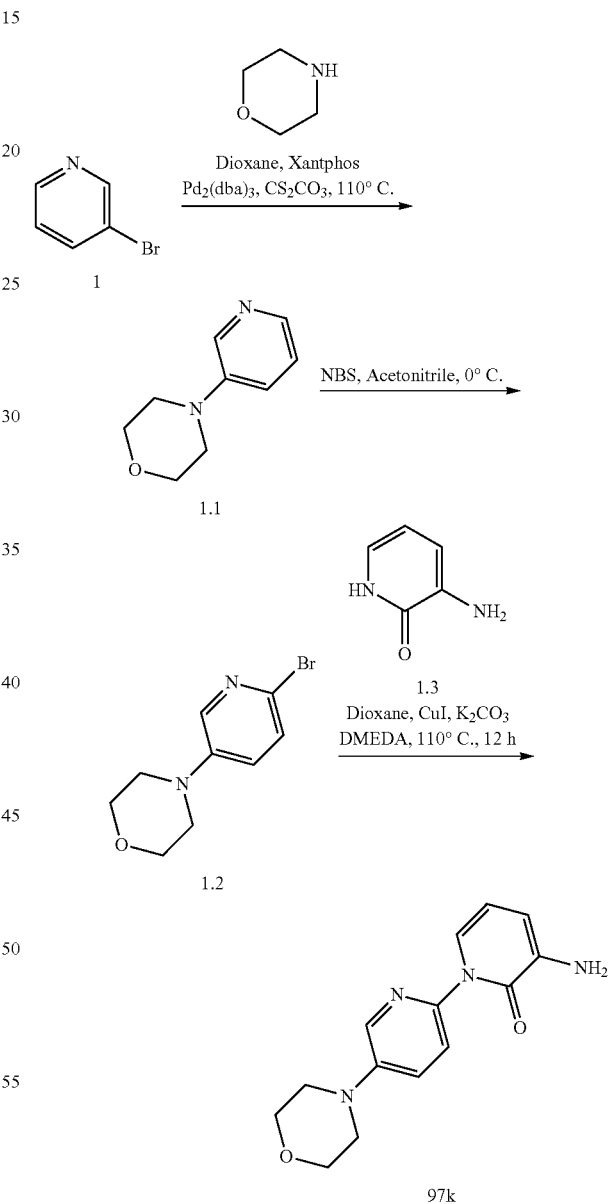

97k

Synthesis of Compound 1.1.

Compound was synthesized using general procedure B to obtain 1.1. (Yield: 96.22%). MS (ES): m/z 165.21 [M+H]$^+$ Synthesis of Compound 1.2.

To a solution of 1.1 (1 g, 6.09 mmol, 1.0 eq) in acetonitrile (30 mL), N-Bromosuccinimide (1.3 g, 7.30 mmol, 1.2 eq)

was added dropwise at 0° C. The reaction mixture was stirred at room temperature for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 15% ethylacetate in hexane to obtain 1.2. (0.41 g, Yield: 27.83%). MS (ES): m/z 244.10 [M+H]$^+$ Synthesis of Compound 97k.

To a solution of 1.2 (0.41 g, 1.69 mmol, 1.0 eq) in 1,4-dioxane (5 mL), 1.3 (0.20 g, 1.85 mmol, 1.1 eq) was added. The reaction mixture was degassed for 10 min under argon atmosphere followed by addition of potassium carbonate (0.23 g, 5.08 mmol, 2.0 eq), N,N-dimethylethylenediamine (0.07 g, 0.67 mmol, 0.4 eq), and copper iodide (0.06 g, 0.33 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 97k (0.15 g, Yield: 32.50%). MS (ES): m/z 273.31 [M+H]$^+$.

Synthesis of Intermediate 97l.

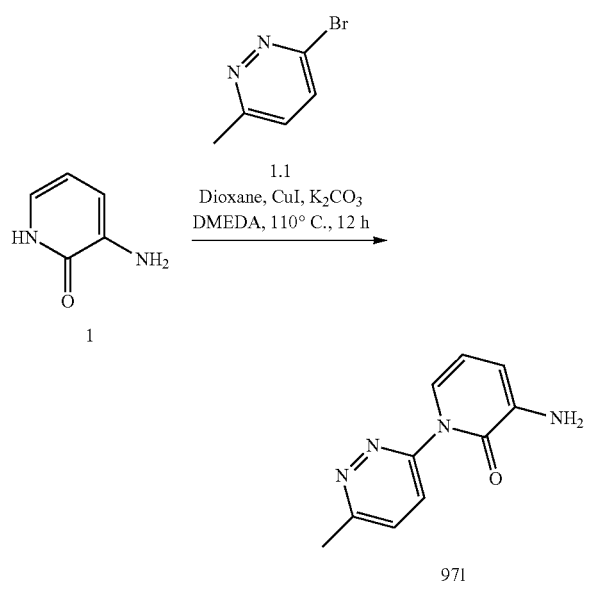

Synthesis of Compound 97l.

To a solution of 1. (1 g, 9.08 mmol, 1.0 eq) in 1,4-dioxane (10 mL), 1.1 (1.7 g, 9.98 mmol, 1.1 eq) was added. The reaction mixture was degassed for 10 min under argon atmosphere followed by addition of potassium carbonate (2.5 g, 18.16 mmol, 2.0 eq), N,N-dimethylethylenediamine (0.48 g, 2.72 mmol, 0.3 eq), and copper iodide (0.24 g, 1.28 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 97l (0.35 g, Yield: 19.06%). MS (ES): m/z 203.22 [M+H]$^+$ Synthesis of Intermediate 97m.

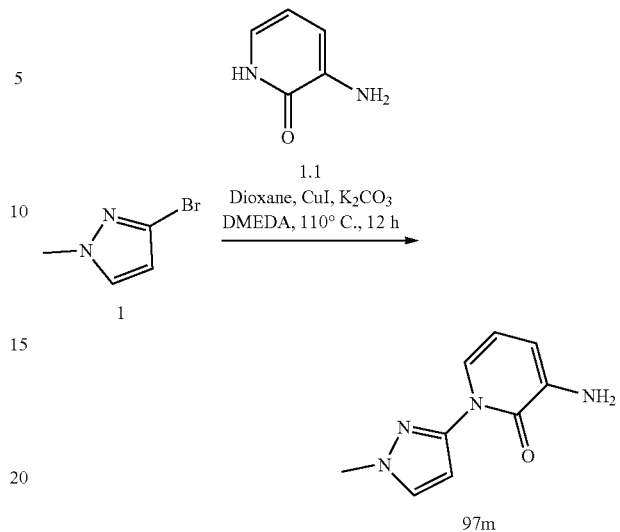

Synthesis of Compound 97m.

To a solution of 1. (2 g, 12.42 mmol, 1.0 eq) in 1,4-dioxane (10 mL), 1.1 (2.5 g, 13.66 mmol, 1.1 eq) was added. The reaction mixture was degassed for 10 min under argon atmosphere followed by addition of potassium carbonate (3.4 g, 24.84 mmol, 2.0 eq), N,N-dimethylethylenediamine (0.66 g, 3.72 mmol, 0.3 eq), and copper iodide (0.35 g, 1.86 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 97m (0.80 g, Yield: 33.86%). MS (ES): m/z 191.21 [M+H]$^+$.

Synthesis of Intermediate 97n.

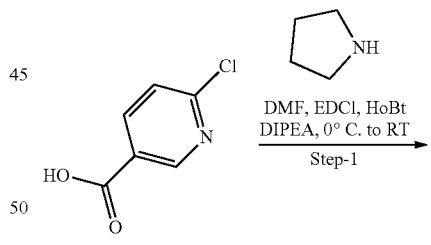

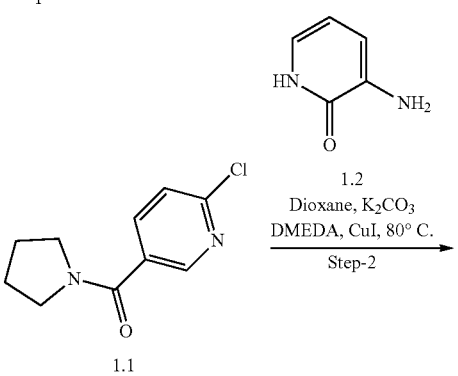

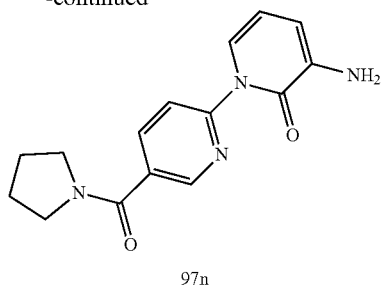

97n

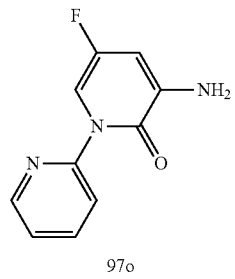

97o

Synthesis of Compound 1.1.

To a cooled solution of 1 (4.0 g, 25.47 mmol, 1.0 eq) and morpholine (3.32 g, 38.21 mmol, 1.5 eq) in N, N-dimethylformamide (40 mL) at 0° C. were added N-(3-Dimethylaminopropyl)-N'-ethylcarbodiimide hydrochloride (7.32 g, 38.21 mmol, 1.5 eq), 1-Hydroxybenzotriazole hydrate (4.12 g, 30.56 mmol, 1.2 eq) followed by N,N-Diisopropylethylamine (9.87 g, 76.41 mmol, 3.0 eq) and the reaction mixture was stirred at room temperature for 16 h. After completion of reaction, reaction mixture was transferred into water and extracted with ethyl acetate. Organic layer was combined, dried over sodium sulphate and concentrated under reduced pressure to obtain crude material. This was further purified by column chromatography and compound was eluted in 20% ethyl acetate in hexane to obtain pure 1.1 (2.5, 46.74%). MS(ES): m/z 211.06 [M+H]$^+$.

Synthesis of Compound 97n.

To a solution of 1.1 (1.0 g, 4.76 mmol, 1.2 eq) and 3-aminopyridin-2 (1H)-one (0.44 g, 3.96 mmol, 1.0 eq) in 1,4-dioxane was added potassium carbonate (1.36 g, 9.9 mmol, 2.5 q) and reaction mixture was degassed with Argon for 10 min. N,N'-Dimethylethylenediamine (0.14 g, 1.58 mmol, 0.4 eq) was added followed by addition of copper(I) iodide (015 g, 0.79 mmol, 0.2 q). The reaction mixture was heated to 120° C. for 4 h, after completion of reaction, reaction mixture was transferred into water and extracted with ethyl acetate. Organic layer was combined, washed with brine, dried over sodium sulphate and concentrated under reduced pressure to obtain crude. This was further purified by column chromatography and compound was eluted in 50% ethyl acetate in hexane to obtain 97n (0.5 g, 36.96%). MS(ES): m/z 285.13 [M+H]$^+$.

Synthesis of Intermediate 97o.

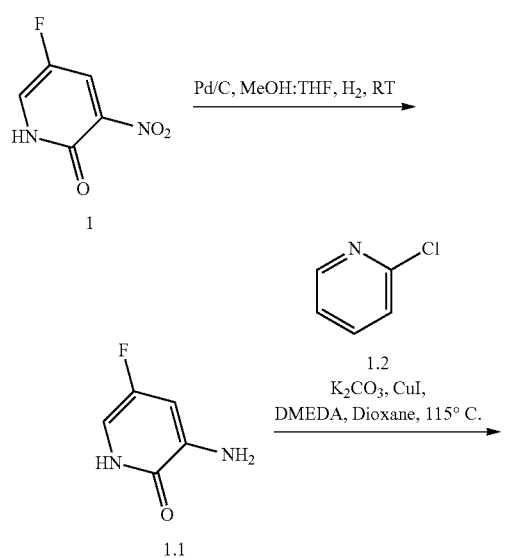

Synthesis of Compound 1.1.

To a solution of 1. (2.0 g, 12.65 mmol, 1.0 eq) in methanol (20 ml), palladium on charcoal (0.400 g) was added. Hydrogen was purged through reaction mixture for 2-3 h at room temperature. After completion of reaction, reaction mixture was filtered through celite-bed and washed with methanol. Filtrate was concentrated under reduced pressure to obtain 1.1 (1.32 g, 81.45%). MS (ES): m/z 129.11 [M+H]$^+$.

Synthesis of Compound 97o.

To a solution of 1.1 (0.500 g, 3.90 mmol, 1.0 eq) and 1.2 (0.487 g, 4.29 mmol, 1.1 eq) in 1,4-dioxane (5 mL) was added potassium carbonate (1.076 g, 7.80 mmol, 2.0 eq) and degassed with argon for 15 min. Copper iodide (0.148 g, 0.780 mmol, 0.2 eq) and 1,2-dimethylethylenediamine (0.137 g, 1.56 mmol, 0.4 eq) was added and reaction mixture again degassed with argon for 5 min followed by heating at 115° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.7% methanol in dichloromethane to obtain pure 97o (0.380 g, 47.45%). MS(ES): m/z 206.19 [M+H]$^+$.

Example 98: Synthesis of Compounds where $R^3$ is N-(oxetan-3-yl)carboxamide, $R^6$ is Hydrogen, and $R^7$ is Methylamine Synthesis of 5-((5-chloro-2-cyclobutoxypyridin-3-yl)amino)-7-(methylamino)-N-(oxetan-3-yl)pyrazolo[1,5-a]pyrimidine-3-carboxamide (I-93)

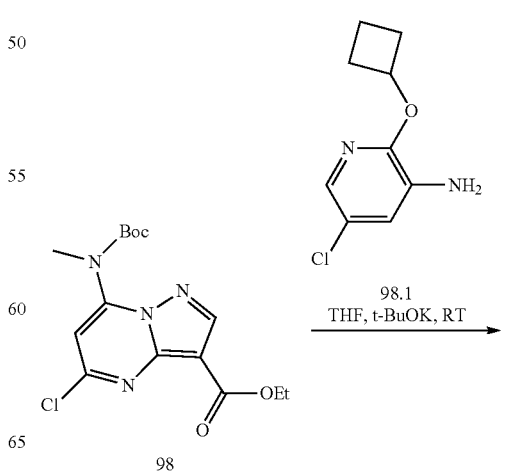

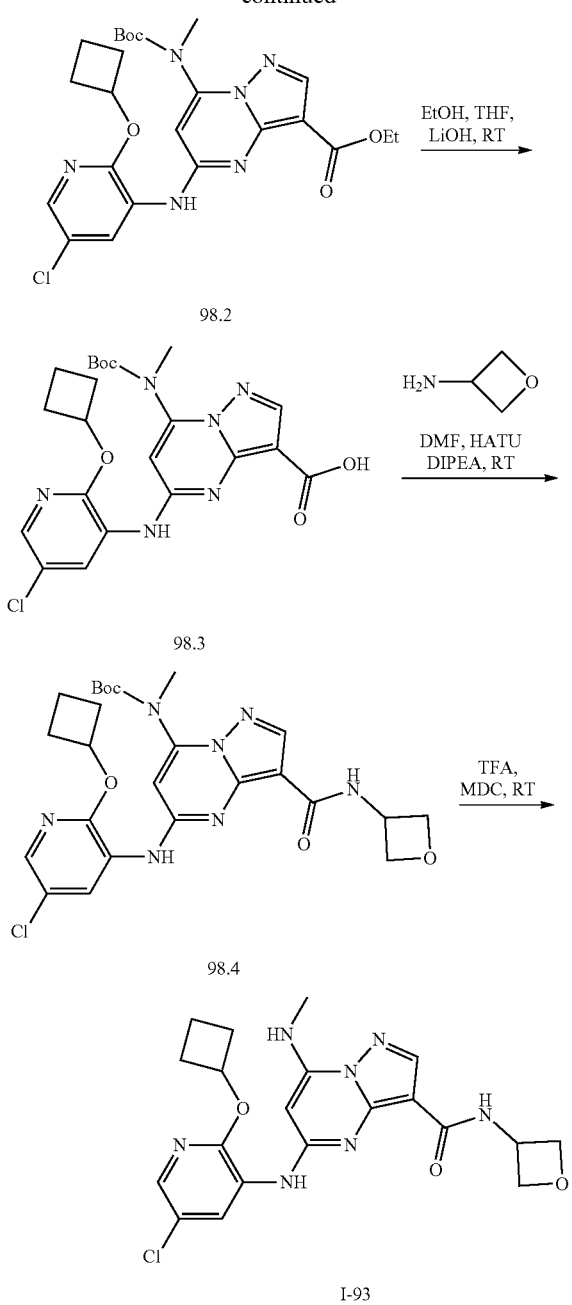

Synthesis of Compound 98.
Compound was synthesized using general procedure of core synthesis to obtain 98. (Yield: 62.21%). MS (ES): m/z 355.5 [M+H].

Synthesis of Compound 98.1.
Compound was synthesized according to intermediate 98a in the intermediates section.

Synthesis of Compound 98.2.
To a cooled solution of 98 (0.300 g, 0.847 mmol, 1.0 eq), and 98.1 (0.168 g, 0.847 mmol, 1 eq) in tetrahydrofuran (3 mL) at 0° C. was added potassium ter-butoxide (1.7 mL, 1.69 mmol, 2 eq). The reaction was stirred at room temperature for 16 h. After completion of reaction, reaction mixture was transferred into cooled ice water and product was extracted with ethyl acetate. Organic layer was combined and dried over sodium sulphate and concentrated under reduced pressure to obtain crude material. This was further purified by column chromatography and compound was eluted in 14% ethyl acetate in hexane to obtain pure 98.2. (0.260 g, 59.48%). MS (ES): m/z 517.98 [M+H]$^+$.

Synthesis of Compound 98.3.
To a solution of 98.2 (0.260 g, 0.502 mmol, 1.0 eq), in tetrahydrofuran: methanol: water (6 mL, 1:1:1) was added lithium hydroxide (0.210 g, 5.02 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.3% methanol in dichloromethane to obtain pure 98.3 (0.180 g, 73.20%). MS(ES): m/z 489.93 [M+H]$^+$.

Synthesis of Compound 98.4.
Compound was synthesized using general procedure A to obtain 98.4. (0.090 g, 44.94%). MS (ES): m/z 545.01 [M+H]$^+$.

Synthesis of Compound I-93. Compound was synthesized using general procedure C to obtain I-93 (0.040 g, 54.47%). MS (ES): m/z 444.35 [M+H]$^+$, LCMS purity: 100%, HPLC purity: 99.05%, $^1$H NMR (DMSO-d$_6$, 400 MHZ): 9.81 (s, 1H), 8.65 (s, 1H), 8.22 (s, 1H), 7.88-7.86 (d, J=8 Hz, 1H), 7.71-7.70 (d, J=4 Hz, 1H), 6.21 (s, 1H), 5.25-5.22 (m, 1H), 4.80-4.79 (m, 1H), 4.39 (s, 1H), 4.24-4.21 (m, 2H), 3.70-3.68 (m, 1H), 2.94-2.93 (d, J=4 Hz, 3H), 2.28-2.26 (t, J=8 Hz, 2H), 1.85-1.82 (m, 1H), 1.71-1.69 (m, 1H), 1.23 (s, 3H).

Characterization data for further compounds prepared by the above methods are presented in Table 33 below. Compounds in Table 33 were prepared by methods substantially similar to those described to prepare I-93, where 98.1 was replaced with the reagent as indicated in Table 33.

TABLE 33

| Compound # | Reagent | Chiral Separation Conditions and Characterization Data |
|---|---|---|
| I-87 | ![structure] | MS (ES): m/z 432.88 [M + H]$^+$, LCMS purity: 100%, HPLC purity: 98.83%, $^1$H NMR (MeOD, 400 MHZ): 9.62 (s, 1H), 8.69 (s, 1H), 8.41 (s, 1H), 8.03 (s, 1H), 7.78 (s, 1H), 6.28 (s, 1H), 5.36-5.32 (m, 1H), 5.05 (bs, 1H), 4.68 (bs, 1H), 4.38 (bs, 2H), 3.65 (bs, 1H), 3.55 (bs, 1H), 2.95-2.94 (d, J = 4.4 Hz, 3H), 1.40 (s, 6H). |

TABLE 33-continued

| Compound # | Reagent | Chiral Separation Conditions and Characterization Data |
|---|---|---|
| I-86 | 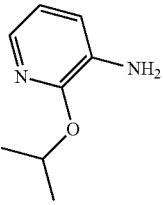 | MS (ES): m/z 398.44 [M + H]+, LCMS purity: 97.59%, HPLC purity: 96.72%, 1H NMR (DMSO-d6, 400 MHZ): 9.37-9.35 (d, J = 7.6 Hz, 1H), 8.34 (s, 1H), 8.20 (s, 1H), 7.78-7.73 (m, 2H), 6.92-6.89 (m, 1H), 6.10 (s, 1H), 5.41-5.38 (t, J = 6.4 Hz, 1H), 4.81 (s, 1H), 4.40-4.36 (m, 1H), 4.23-4.17 (m, 2H), 3.66-3.63 (m, 1H), 3.43-3.41 (m, 1H), 2.94-2.93 (d, J = 4.8 Hz, 3H), 1.40-1.39 (d, J = 6.4 Hz, 6H). |
| I-104 | 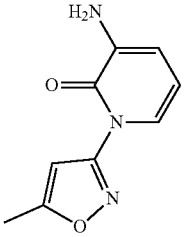 | MS (ES): m/z 437.39 [M + H]+, LCMS purity: 96.15%, HPLC purity: 100%, 1H NMR (DMSO-d6, 400 MHZ): 11.80 (s, 1H), 9.14-9.10 (m, 2H), 8.40 (s, 1H), 7.96-7.95 (d, J = 4 Hz, 1H), 7.55-7.53 (t, J = 8 Hz, 1H), 6.90 (s, 1H), 6.49-6.47 (t, J = 8 Hz, 1H), 6.38 (s, 1H), 4.47 (s, 1H), 4.48 (s, 1H) 4.39 (s, 1H), 3.65-3.63 (d, J = 8 Hz, 2H), 2.91-2.90 (d, J = 4 Hz, 3H), 2.67 (s, 3H). |
| I-109 | 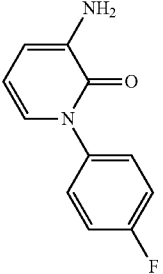 [SMILES: Nc1cccn(-c2ccc(F)cc2)c1=O] | MS (ES): m/z 448.30 [M − H]+, LCMS purity: 99.74%, HPLC purity: 98.59%, 1H NMR (DMSO-d6, 400 MHZ): 9.27-9.25 (d, J = 8 Hz, 1H), 8.87 (s, 1H), 8.20 (s, 1H), 7.75-7.74 (d, J = 4 Hz, 1H), 7.57-7.54 (m, 2H), 7.41-7.39 (d, J = 8 Hz, 2H), 7.25-7.24 (d, J = 4 Hz, 1H), 6.38-6.36 (t, J = 8 Hz, 1H), 6.25 (s, 1H), 4.82-4.81 (t, J = 4 Hz, 1H), 4.41-4.39 (t, J = 8 Hz, 1H), 4.26-4.18 (m, 2H), 3.66-3.64 (m, 1H), 3.46-3.42 (m, 1H), 2.89-2.88 (d, J = 4 Hz, 3H). |
| I-92 | 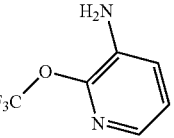 | MS (ES): m/z 424.42 [M + H]+, LCMS purity: 98.82%, HPLC purity: 100%, 1H NMR (DMSO-d6, 400 MHZ): 9.56-9.54 (d, J = 8 Hz, 1H), 9.07 (s, 1H), 8.27 (s, 1H), 7.95-7.94 (d, J = 4 Hz, 1H), 7.93-7.91 (d, J = 8 Hz, 1H), 7.38-7.35 (m, 1H), 6.08 (s, 1H), 4.88 (s, 1H), 4.44 (s, 1H), 4.26 (s, 2H), 3.64-3.62 (m, 1H), 3.45-3.44 (d, J = 4 Hz, 1H), 2.93-2.92 (d, J = 4 Hz, 3H). |
| I-83 | 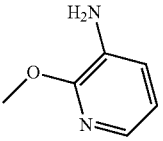 | MS (ES): m/z 370.39 [M + H]+, LCMS purity: 99.68%, HPLC purity: 100%, 1H NMR (DMSO-d6, 400 MHZ): 9.44-9.42 (d, J = 6.8 Hz, 1H), 8.68 (s, 1H), 8.18 (s, 1H), 7.75-7.74 (d, J = 4.8 Hz, 2H), 6.96-6.93 (m, 1H), 6.13 (s, 1H), 4.80-4.77 (t, J = 11.2 Hz, 1H), 4.39-4.35 (t, J = 8 Hz, 1H), 4.26-4.16 (m, 2H), 3.99 (s, 3H), 3.67-3.62 (m, 1H), 3.44-2.9 (m, 1H), 2.91-2.90 (d, J = 4.8 Hz, 3H). |
| I-88 | 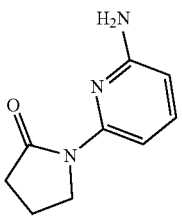 [SMILES: Nc1cccc(N2CCCC2=O)n1] | MS (ES): m/z 423.45 [M + H]+, LCMS purity: 100%, HPLC purity: 97.19%, 1H NMR (DMSO-d6, 400 MHZ): 9.87 (s, 1H), 8.22 (s, 1H), 8.02-8.00 (d, J = 8 Hz, 1H), 7.91-7.90 (d, J = 4 Hz, 2H), 7.69-7.68 (d, J = 5.6 Hz 2H), 6.87 (s, 1H), 4.86-4.80 (m, 1H), 4.22-4.11 (m, 4H), 3.64-3.61 (m, 1H), 3.42-3.35 (m, 1H), 2.97-2.96 (d, J = 4 Hz, 3H), 2.68-2.51 (m, 2H), 2.15-2.05 (m, 2H). |

Synthesis of 5-((1-(1-cyclopropyl-1H-pyrazol-3-yl)-2-oxo-1,2-dihydropyridin-3-yl)amino)-7-(methylamino)-N-(oxetan-3-yl)pyrazolo[1,5-a]pyrimidine-3-carboxamide (I-89)

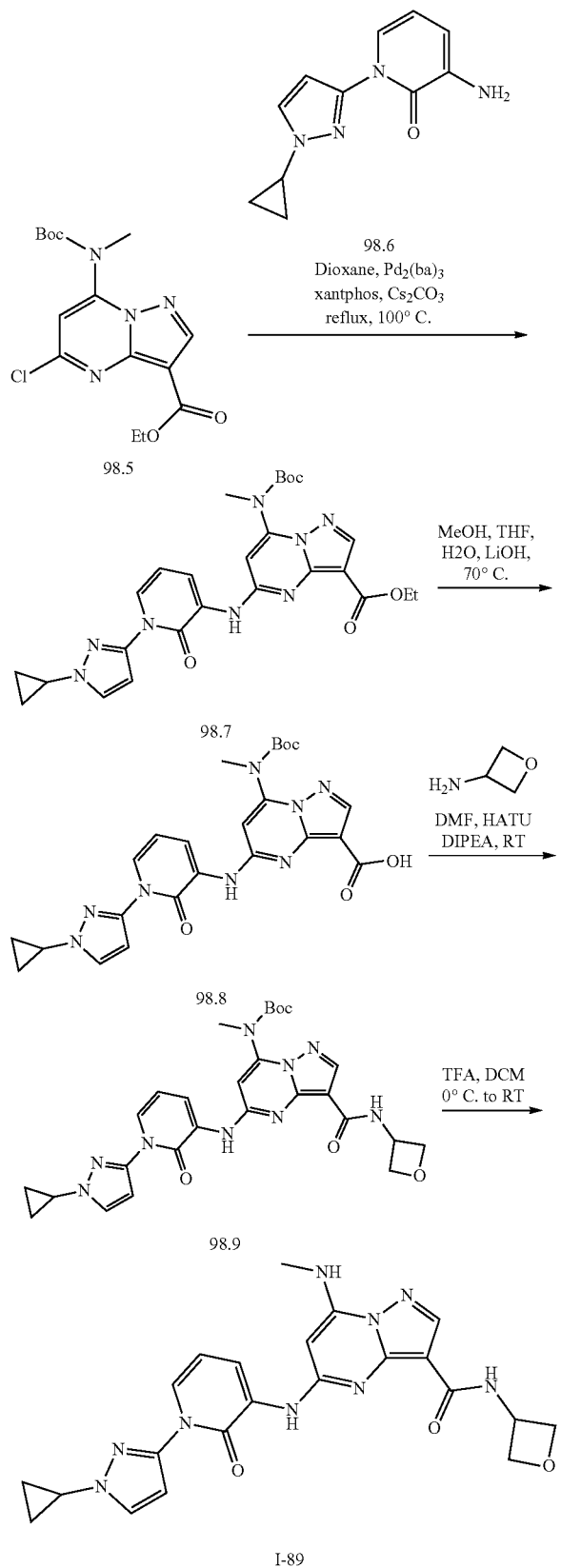

Synthesis of Compound 98.5.

Compound was synthesized using general procedure of core synthesis to obtain 98.5 (Yield: 62.21%). MS (ES): m/z 355.5 [M+H]$^+$.

Synthesis of Compound 98.6.

Compound was synthesized according to intermediate 98b in the intermediates section.

Synthesis of Compound 98.7.

Compound was synthesized using general procedure B to obtain 98.7 (0.270 g, 59.73%). MS (ES): m/z 535.58 [M+H]$^+$.

Synthesis of Compound 98.8.

To a solution of 98.7 (0.270 g, 0.505 mmol, 1.0 eq), in tetrahydrofuran: methanol: water (6 mL, 1:1:1) was added lithium hydroxide (0.212 g, 5.05 mmol, 10 eq). The reaction was stirred at 70° C. temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 98.8 (0.200 g, 78.18%). MS(ES): m/z 507.52 [M+H]$^+$.

Synthesis of Compound 98.9.

Compound was synthesized using general procedure A to obtain 98.9. (0.100 g, 45.10%). MS (ES): m/z 562.60 [M+H]$^+$.

Synthesis of Compound I-89. Compound was synthesized using general procedure C to obtain I-89 (0.035 g, 42.59%). MS (ES): m/z 462.56 [M+H]$^+$, LCMS purity: 100%, HPLC purity: 98.34%, $^1$H NMR (DMSO-d$_6$, 400 MHZ): 9.27-9.25 (d, J=8 Hz 1H), 8.26 (s, 1H), 8.20 (s, 1H), 7.93 (s, 1H), 7.77 (s, 1H), 7.62-7.61 (d, J=4 Hz, 1H), 6.78 (s, 1H), 6.39 (s, 1H), 6.28 (s, 1H), 4.82 (s, 1H), 4.39-4.37 (d, J=4 Hz, 1H), 4.27-4.20 (m, 2H), 3.79 (s, 1H), 3.65 (s, 1H), 2.90 (s, 3H), 1.25 (s, 1H), 1.12 (s, 2H), 1.02 (s, 2H).

Synthesis of Intermediate 98a.

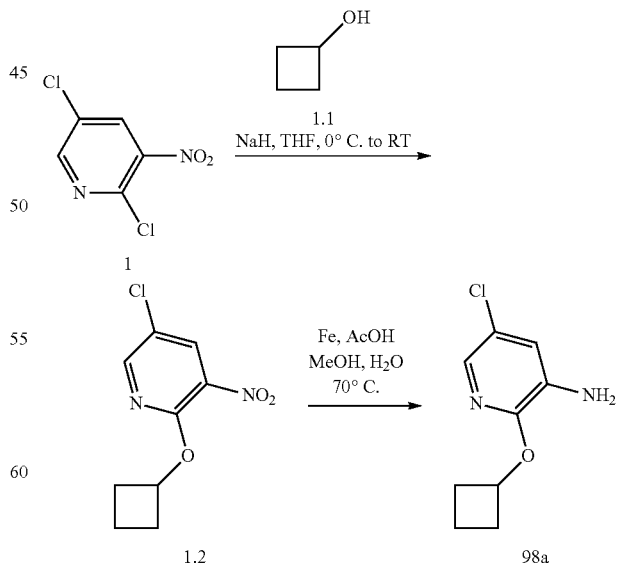

Synthesis of Compound 1.2.

To a cooled suspension of sodium hydride (0.250 g, 10.36 mmol, 1.0 eq) in tetrahydrofuran (20 mL) was added 1.1

(0.679 g, 9.42 mmol, 1.0 eq) drop wise. The reaction was stirred at 0° C. for 30 min. Compound 1 (2 g, 10.36 mmol, 1.1 eq) was added drop wise in reaction mixture and stirred at 0° C. for 30 min. Reaction mixture further stirred at room temperature for 16 h. After completion of reaction, reaction mixture was cooled to room temperature, transferred into ice-water and product was extracted with ethyl acetate. Organic layer was combined, washed with brine solution, dried over sodium sulphate and concentrated under reduced pressure to obtain crude material. This was further purified by column chromatography and compound was eluted in 8% ethyl acetate in hexane to obtain pure 1.2 (0.600 g, 27.85%), MS(ES): m/z 229.63 [M+H]$^+$.

Synthesis of Compound 98a.

To 1.2 (0.600 g, 2.64 mmol, 1.0 eq) added mixture of methanol:water (8 mL, 2:1) and acetic acid (1.58 g, 26.4 mmol, 10 eq). The reaction mixture was heated 60° C. then iron powder (1.18 g, 21.14 mmol, 8 eq) was added portion-wise. The reaction was stirred at 70° C. for 5 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 12% ethyl acetate in hexane to obtain pure 98a (0.400 g, 76.73%). MS(ES): m/z 199.65 [M+H]$^+$.

Synthesis of Intermediate 98b.

Synthesis of Compound 1.2.

To a solution of 1 (3 g, 20.41 mmol, 1 eq) and 1.1 (2.10 g, 24.49 mmol, 1.2 eq) in 1,2-dichloroethane (20 mL) was added sodium carbonate (2.57 g, 24.49 mmol, 1.2 eq), copper acetate (2.58 g, 14.28 mmol, 0.7 eq) and 2,2bipyridine (2.22 g, 14.28 mmol, 0.7 eq). Reaction mixture was degassed with oxygen followed by heating at 70° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 12% ethyl acetate in hexane to obtain pure 1.2 (2 g, 52.39%). MS(ES): m/z 188.04 [M+H]$^+$.

Synthesis of Compound 98b.

To a solution of 1.2 (2 g, 10.69 mmol, 1 eq) and 1.3 (1.06 g, 9.62 mmol, 0.9 eq) in 1,4-dioxane (20 mL) was added potassium carbonate (2.95 g, 21.38 mmol, 2.0 eq) and degassed with argon for 15 min. Copper iodide (0.304 g, 1.60 mmol, 0.15 eq) and 1,2-dimethylethylenediamine (0.281 g, 3.20 mmol, 0.3 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.9% methanol in dichloromethane to obtain pure 98b (1 g, 43.25%). MS(ES): m/z 217.24 [M+H]$^+$.

Example 99: Synthesis of Compounds where R$^3$ is N-(((1-(hydroxymethyl)cyclopropyl)methyl)carboxamide, R$^6$ is Hydrogen, and R$^7$ is Methylamine Synthesis of 5-((1-(2-fluorocyclopropyl)-2-oxo-1,2-dihydropyridin-3-yl)amino)-N-((1-(hydroxymethyl)cyclopropyl)methyl)-7-(methylamino)pyrazolo[1,5-a]pyrimidine-3-carboxamide (I-1061)

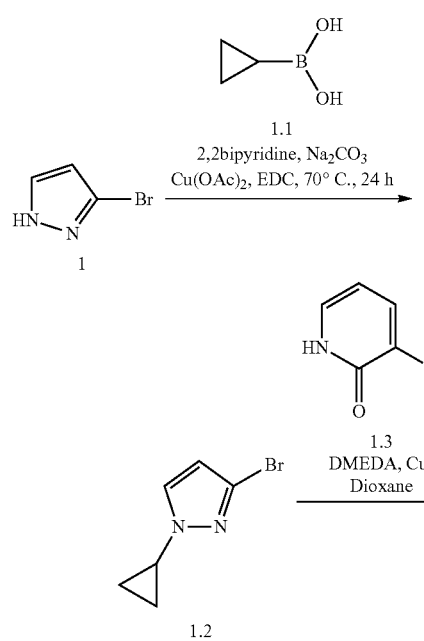

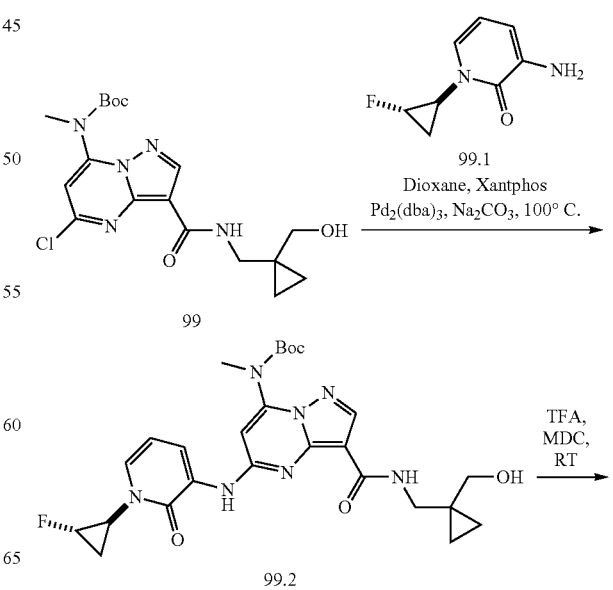

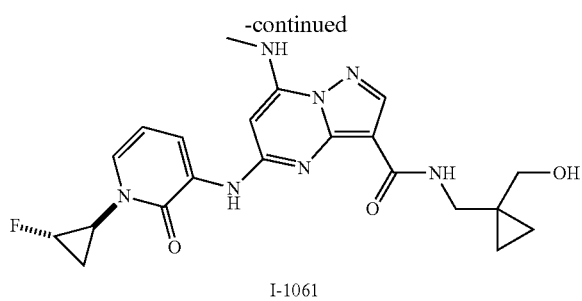

I-1061

Synthesis of Compound 99.
Compound was synthesized as per I-541 to obtain 99. (Yield: 45.44%). MS(ES): m/z 410.87 [M+H]+
Synthesis of Compound 99.1.
Compound was synthesized as per Example 101 (I-1060) to obtain 99.1. MS(ES): m/z 169.05 [M+H]+.
Synthesis of Compound 99.2.
Compound was synthesized using general procedure B to obtain 99.2 (0.150 g, 75.68%). MS(ES): m/z 541.58 [M+H]+.

Synthesis of Compound I-1061. Compound was synthesized using general procedure C to obtain I-1061 (0.025 g, 76.67%), MS (ES): m/z 442.45 [M+H]+, LCMS purity: 97.57%, HPLC purity: 96.05%, CHIRAL HPLC Purity: 100%, $^1$H NMR (DMSO-$d_6$, 400 MHZ): 8.91 (s, 1H), 8.22 (s, 1H), 8.20 (s, 1H), 7.93-7.92 (d, J=4.8 Hz, 1H), 7.80-7.77 (t, J=6 Hz, 1H), 7.16-7.15 (d, J=6.8 Hz, 1H), 6.37-6.33 (t, J=7.2 Hz, 1H), 6.24 (s, 1H), 4.64-4.61 (t, J=6 Hz, 1H), 3.35 (s, 3H), 3.30-3.28 (d, J=5.6 Hz, 2H), 2.91-2.90 (d, J=4.8 Hz, 3H), 1.56 (bs, 2H), 1.22 (bs, 3H), 0.43 (bs, 2H).

Synthesis of 5-((1-(((1S,2S)-2-fluorocyclopropyl)-2-oxo-1,2-dihydropyridin-3-yl)amino)-N-((1-(hydroxymethyl)cyclopropyl)methyl)-7-(methylamino)pyrazolo[1,5-a]pyrimidine-3-carboxamide (I-1121) and 5-((1-(((1R,2R)-2-fluorocyclopropyl)-2-oxo-1,2-dihydropyridin-3-yl)amino)-N-((1-(hydroxymethyl)cyclopropyl)methyl)-7-(methylamino)pyrazolo[1,5-a]pyrimidine-3-carboxamide (I-1122)

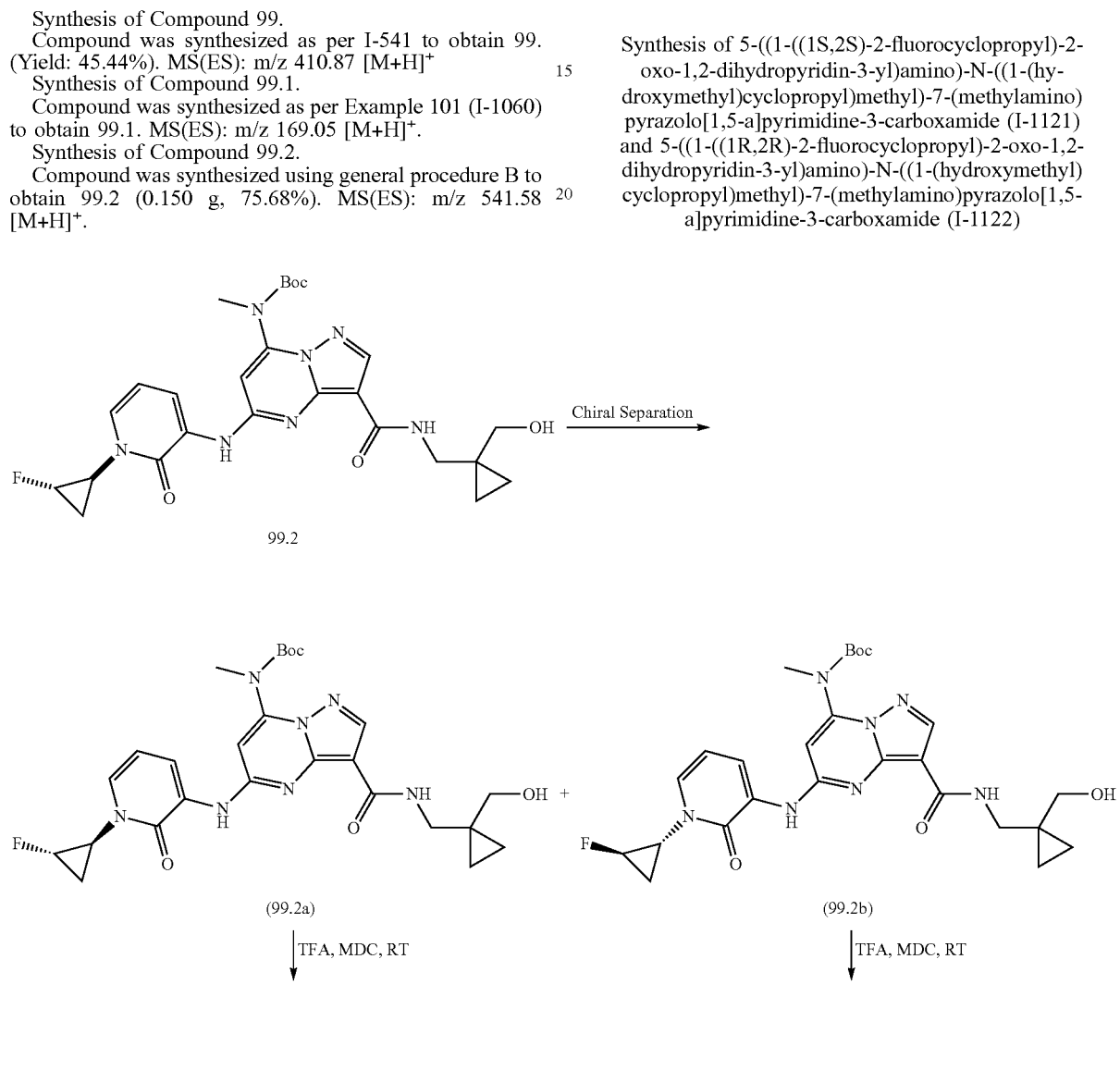

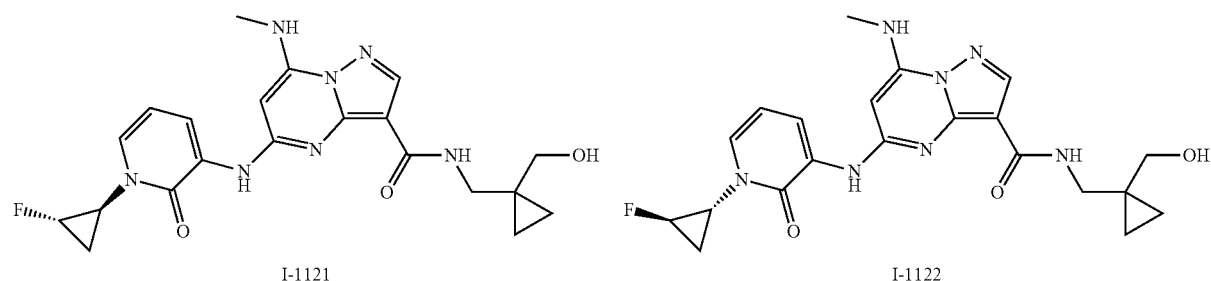

Synthesis of Compound 99.2a and 99.2b.

Isomers of 99.2 (0.110 g) were separated out using column (CHIRAL PAK AD-H 250×4.6 mm, 5 pM) and DEA in HEX_IPA-MEOH (50-50) as co-solvent with flow rate of 4 mL/min. to get pure fraction-1 (FR-a) and fraction-2 (FR-b). FR-a was concentrated under reduced pressure at 30° C. to afford pure 99.2a. (0.044 g). MS(ES): m/z 542.58 [M+H]$^+$. FR-b was concentrated under reduced pressure at 30° C. to afford pure 99.2b. (0.044 g). MS(ES): m/z 542.58 [M+H]$^+$.

Synthesis of Compound I-1121 and I-1122.

Compounds were synthesized using general procedure C to obtain 0.028 g: MS (ES): m/z 442.52 [M+H]$^+$, LCMS purity: 97.16%, HPLC purity: 97.14%, Chiral HPLC: 97.46%, $^1$H NMR (DMSO-d$_6$, 400 MHZ): 8.92 (s, 1H), 8.22-8.21 (m, 2H), 7.94-7.93 (d, J=4.8 Hz, 1H), 7.80-7.77 (m, 1H), 7.17-7.15 (d, J=6.8 Hz, 1H), 6.37-6.34 (t, J=7.2 Hz, 1H), 6.25 (s, 1H), 5.46-5.44 (d, J=7.2 Hz, 1H), 4.64-4.861 (m, 1H), 3.90-3.84 (m, 1H), 3.72-3.67 (m, 1H), 3.49-3.46 (m, 1H), 3.30-3.29 (d, J=5.6 Hz, 2H), 2.91-2.90 (d, J=4.4 Hz, 3H), 1.74-1.67 (m, 1H), 1.58-1.52 (m, 1H), 0.43-0.38 (m, 4H) and 0.029 g: MS (ES): m/z 442.52 [M+H]$^+$, LCMS purity: 97.60%, HPLC purity: 97.06%, Chiral HPLC: 98.04%, $^1$H NMR (DMSO-d$_6$, 400 MHZ): 8.92 (s, 1H), 8.22-8.21 (m, 2H), 7.94-7.93 (d, J=4.8 Hz, 1H), 7.80-7.77 (m, 1H), 7.17-7.15 (d, J=6.8 Hz, 1H), 6.37-6.34 (t, J=7.2 Hz, 1H), 6.25 (s, 1H), 5.46-5.44 (d, J=7.2 Hz, 1H), 4.64-4.861 (m, 1H), 3.90-3.84 (m, 1H), 3.72-3.67 (m, 1H), 3.49-3.46 (m, 1H), 3.30-3.29 (d, J=5.6 Hz, 2H), 2.91-2.90 (d, J=4.8 Hz, 3H), 1.76-1.67 (m, 1H), 1.56-1.49 (m, 1H), 0.43-0.38 (m, 4H).

Characterization data for further compounds prepared by the above methods are presented in Table 34 below. Compounds in Table 34 were prepared by methods substantially similar to those described to prepare I-1061, where 99.1 was replaced with the reagent as indicated in Table 34.

TABLE 34

| Compound # | Reagent | Chiral Separation Conditions and Characterization Data |
|---|---|---|
| I-1010 | NH$_2$•HCl | MS (ES): 496.47 [M + H]$^+$ LCMS purity: 98.69%, HPLC purity: 93.96%, $^1$H NMR (DMSO-d$_6$, 400 MHZ): 8.85 (s, 1H), 8.21 (s, 1H), 8.19 (s, 1H), 7.92-7.91 (d, J = 5.2 Hz, 1H), 7.83-7.80 (t, J = 6 Hz, 1H), 7.44-7.43 (d, J = 6.4 Hz, 1H), 6.43-6.40 (t, J = 7.2 Hz, 1H), 6.22 (s, 1H), 5.13 (bs, 1H), 4.64-4.61 (t, J = 5.6 Hz, 1H), 3.71 (bs, 1H), 3.58 (s, 1H), 3.41-3.40 (d, J = 6 Hz, 2H), 3.35 (s, 2H), 3.32-3.30 (d, J = 6 Hz, 2H), 3.28-3.26 (d, J = 8 Hz, 4H), 2.92-2.91 (d, J = 4.8 Hz, 3H), 2.02 (bs, 1H), 1.91-1.85 (m, 1H), 1.82 (bs, 1H), 1.75-1.65 (m, 4H), 1.41 (s, 1H). |
| I-1086 I-1087 | NH$_2$•HCl | Intermediate corresponding to 99.2 en route to I-1010 was separated into isomers before BOC removal: CHIRAL PAK AD-H (250 × 4.6 mm, 5 μM) and DEA in HEX_IPA-MEOH (50-50) at 4 mL/min. Product prepared from FR-a: MS (ES): m/z 496.61 [M + H]$^+$, LCMS purity: 100%, HPLC purity: 99.26%, Chiral HPLC: 100%, $^1$H NMR (DMSO-d$_6$, 400 MHZ): 8.85 (s, 1H), 8.21 (s, 1H), 8.19 (s, 1H), 7.92-7.91 (d, J = 5.2 Hz, 1H), 7.83-7.80 (t, J = 6.0 Hz, 1H), 7.44-7.43 (d, J = 6.0 Hz, 1H), 6.44-6.40 (t, J = 7.2 Hz, 1H), 6.23 (s, 1H), 5.13 (bs, 1H), 4.64-4.61 (t, J = 5.6 Hz, 1H), 3.71 (bs, 1H), 3.42-3.40 (d, J = 6.0 Hz, 2H), 3.32-3.31 (d, J = 5.6 Hz, 2H), 3.29 (s, 3H), 2.92-2.91 (d, J = 4.8 Hz, 3H), 2.05-2.03 (m, 1H), 1.91-1.85 (m, 2H), 1.82-1.65 (m, 4H), 1.44-1.638 (m, 1H), 0.45-0.39 (m, 4H). Product prepared from FR-b: MS (ES): m/z 496.61 [M + H]$^+$, LCMS purity: 98.93%, HPLC purity: 99.00%, Chiral HPLC: 98.65%, $^1$H NMR (DMSO-d$_6$, 400 MHZ): 8.85 (s, 1H), 8.21 (s, 1H), 8.19 (s, 1H), 7.92-7.91 (d, J = 4.8 Hz, 1H), 7.82-7.80 (t, J = 6.0 Hz, 1H), 7.44-7.43 (d, J = 6.0 Hz, 1H), 6.44-6.40 (t, J = 7.2 Hz, 1H), 6.23 (s, 1H), 5.13 (bs, 1H), 4.64-4.61 (t, J = 5.6 Hz, 1H), 3.71 (bs, 1H), 3.42-3.40 (d, J = 6.0 Hz, 2H), 3.32-3.31 (d, J = 5.6 Hz, 2H), 3.29 (s, 3H), 2.93-2.91 (d, J = 4.8 Hz, 3H), 2.06-2.02 (m, 1H), 1.91-1.85 (m, 2H), 1.82-1.65 (m, 4H), 1.44-1.638 (m, 1H), 0.45-0.39 (m, 4H). |

TABLE 34-continued

| Compound # | Reagent | Chiral Separation Conditions and Characterization Data |
|---|---|---|
| I-862 | 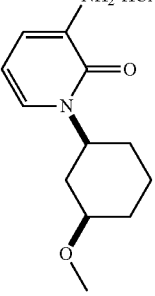 NH₂•HCl | MS (ES): m/z 496.71 [M + H]⁺, LCMS purity: 96.78%, HPLC purity: 97.10%, CHIRAL HPLC purity: 49.01%, 48.91%., ¹H NMR (DMSO-d₆, 400 MHZ): 8.83 (s, 1H), 8.21 (s, 1H), 8.20 (s, 1H) 7.92-7.80 (m, 2H), 7.48-7.46 (d, J = 8.0 Hz, 1H), 6.44-6.41 (m, 1H), 6.22 (s, 1H), 4.87-4.81 (m, 1H), 3.58 (s, 1H), 3.41-3.28 (m, 9H), 2.93-2.92 (d, J = 4.0 Hz, 3H), 2.19-2.16 (m, 1H), 2.07-2.04 (m, 1H), 1.88-1.85 (m, 1H), 1.74 (s, 1H), 1.65-1.56 (m, 2H), 1.43-1.40 (m, 1H), 1.17-1.14 (m, 1H), 0.45-0.40 (m, 3H). |
| I-928 I-929 | 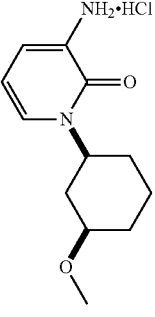 NH₂•HCl | Intermediate corresponding to 99.2 en route to I-862 was separated into isomers before BOC removal: CHIRAL PAK AD-H (250 × 4.6 mm, 5 μM) and DEA in HEX_IPA-MEOH (50-50) at 4 mL/min.<br>Product prepared from FR-a: MS (ES): m/z 496.62 [M + H]⁺, LCMS purity: 98.11%, HPLC purity: 95.26%, Chiral HPLC: 96.96%, ¹H NMR (DMSO-d₆, 400 MHz): 8.84 (s, 1H), 8.21-8.20 (m, 2H), 7.93-7.80 (m, 2H), 7.48-7.46 (d, J = 5.6 Hz, 1H), 6.44-6.41 (m, 1H), 6.23 (s, 1H), 4.87-4.81 (t, J = 4.0 Hz, 1H), 4.65-4.62 (m, 1H), 3.41-3.40 (d, J = 6.0 Hz, 2H), 3.32-3.31 (d, J = 5.6 Hz, 2H), 3.28 (s, 3H), 2.93-2.92 (d, J = 4.0 Hz, 3H), 2.19-2.16 (m, 1H), 2.07-2.04 (m, 1H), 1.88-1.85 (m, 1H), 1.74 (bs, 1H), 1.65-1.56 (m, 2H), 1.43-1.40 (m, 2H), 1.17-1.14 (m, 2H), 0.45-0.40 (m, 3H).<br>Product prepared from FR-b: MS (ES): m/z 496.82 [M + H]⁺, LCMS purity: 98.17%, HPLC purity: 96.19%, Chiral HPLC: 97.99%, ¹H NMR (DMSO-d₆, 400 MHz): 8.84 (s, 1H), 8.21-8.20 (m, 2H), 7.93-7.80 (m, 2H), 7.48-7.46 (d, J = 5.6 Hz, 1H), 6.44-6.41 (m, 1H), 6.23 (s, 1H), 4.87-4.81 (t, J = 4.0 Hz, 1H), 4.65-4.62 (m, 1H), 3.41-3.40 (d, J = 6.0 Hz, 2H), 3.32-3.31 (d, J = 5.6 Hz, 2H), 3.28 (s, 3H), 2.93-2.92 (d, J = 4.0 Hz, 3H), 2.19-2.16 (m, 1H), 2.07-2.04 (m, 1H), 1.88-1.85 (m, 1H), 1.74 (bs, 1H), 1.65-1.56 (m, 2H), 1.43-1.40 (m, 2H), 1.17-1.14 (m, 2H), 0.45-0.40 (m, 3H). |
| I-530 | 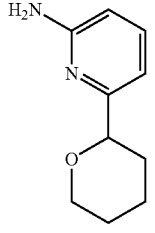 [SMILES: Nc1cccc(C2CCCCO2)n1] | MS (ES): m/z 452.51 [M + H]⁺ LCMS purity: 95.16%, HPLC purity: 98.99%, ¹H NMR (DMSO-d₆, 400 MHZ): 9.91 (s, 1H), 8.22 (s, 1H), 8.03-7.96 (m, 2H), 7.79-7.75 (t, J = 8 Hz, 1H), 7.60-7.58 (d, J = 8 Hz, 1H), 7.04-7.03 (d, J = 7.6 Hz, 2H), 6.68 (s, 1H), 4.64-4.61 (t, J = 11.6 Hz, 1H), 4.34-4.32 (d, J = 10.4 Hz, 1H), 4.07-4.00 (t, J = 11.2 Hz, 1H), 3.60-3.54 (m, 1H), 3.41-3.38 (d, J = 6 Hz, 2H), 3.30 (s, 2H), 2.95-2.94 (d, J = 4.4 Hz, 3H), 2.05-2.02 (m, 2H), 1.65-1.52 (m, 4H). 0.45-0.37 (m, 3H). |
| I-564 I-565 | 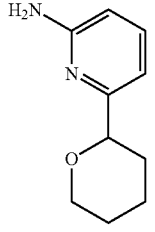 [SMILES: Nc1cccc(C2CCCCO2)n1] | I-530 was separated into isomers: CHIRAL PAK AD-H (250 × 4.6 mm, 5u) and 0.1% DEA in methanol and isopropyl alcohol at 4 mL/min.<br>FR-a: MS (ES): m/z 452.40 [M + H]⁺, LCMS purity: 98.95%, HPLC purity: 98.33%, CHIRAL HPLC purity: 96.48%. ¹H NMR (DMSO-d₆, 400 MHZ): 9.98 (s, 1H), 8.23 (s, 1H), 8.06-8.00 (m, 2H), 7.80-7.76 (t, J = 8 Hz, 1H), 7.61-7.59 (d, J = 8 Hz, 1H), 7.05-7.03 (d, J = 7.6 Hz, 1H), |

TABLE 34-continued

| Compound # | Reagent | Chiral Separation Conditions and Characterization Data |
|---|---|---|
| | | 6.73 (s, 1H), 4.71-4.68 (t, J = 6 Hz, 1H), 4.36-4.33 (d, J = 10.8 Hz, 1H), 4.08-4.05 (d, J = 11.6 Hz, 1H), 3.62-3.55 (m, 1H), 3.42-3.41 (d, J = 6 Hz, 2H), 3.32-3.31 (d, J = 5.6 Hz, 2H), 2.96-2.95 (d, J = 4.8 Hz, 3H), 2.06-2.03 (d, J = 13 Hz, 1H), 1.93-1.89 (d, J = 12.4 Hz, 1H), 1.67-1.63 (m, 4H), 0.46 (bs, 2H), 0.38 (bs, 2H). FR-b: MS (ES): m/z 452.40 [M + H]$^+$, LCMS purity: 99.08%, HPLC purity: 98.07%, CHIRAL HPLC purity: 97.68 $^1$H NMR (DMSO-d$_6$, 400 MHZ): 9.98 (s, 1H), 8.23 (s, 1H), 8.06-8.00 (m, 2H), 7.80-7.76 (t, J = 8 Hz, 1H), 7.61-7.59 (d, J = 9.4 Hz, 1H), 7.05-7.03 (d, J = 7.6 Hz, 1H), 6.73 (s, 1H), 4.71-4.68 (t, J = 4.8 Hz, 1H), 4.36-4.33 (d, J = 11.2 Hz, 1H), 4.08-4.05 (d, J = 12 Hz, 1H), 3.61-3.55 (m, 1H), 3.42-3.41 (d, J = 6 Hz, 2H), 3.32-3.31 (d, J = 5.6 Hz 2H), 2.96-2.95 (d, J = 4.8 Hz, 3H), 2.06-2.03 (d, J = 13.6 Hz, 1H), 1.93-1.89 (d, J = 13.2 Hz, 1H), 1.67-1.63 (m, 4H), 0.46 (bs, 2H), 0.38 (bs, 2H). |
| I-1047 | [structure: 3-amino-1-(2-methoxycyclohexyl)pyridin-2(1H)-one] | MS (ES): m/z 496.3 [M + H]$^+$, LCMS purity: 98.64%, HPLC purity: 97.42%, CHIRAL HPLC purity: 99.72%, $^1$H NMR (DMSO-d$_6$, 400 MHZ): 8.83 (s, 1H), 8.66-8.24 (s, 1H), 8.21 (s, 1H), 7.93-7.91 (d, J = 4.8 Hz, 1H), 7.85-7.82 (m, 1H), 7.36-7.35 (d, J = 6.8 Hz, 1H), 6.39-6.36 (t, J = 7.2 Hz, 1H), 6.21 (s, 1H), 4.91-4.87 (d, J = 13.2 Hz, 1H), 4.65-4.62 (d, J = 5.6 Hz, 1H), 3.58 (bs, 1H), 3.32-3.31 (d, J = 5.2 Hz, 1H), 3.12 (s, 3H), 2.92-2.91 (d, J = 4.8 Hz, 3H), 2.11 (bs, 2H), 1.86 (bs, 1H), 1.56 (bs, 2H), 1.47 (bs, 4H), 1.24 (bs, 2H), 0.39 (bs, 4H). |
| I-991 | [structure: 3-amino-1-(2-methoxycyclohexyl)pyridin-2(1H)-one] | MS (ES): m/z 496.32 [M + H]$^+$, LCMS purity: 100%, HPLC purity: 95.76%, CHIRAL HPLC: 100%, $^1$H NMR (DMSO-d$_6$, 400 MHZ): 8.82 (s, 1H), 8.22 (s, 1H), 8.20 (s, 1H), 7.92-7.91 (d, J = 4.4 Hz, 1H), 7.83-7.80 (t, J = 5.6 Hz, 1H), 7.35-7.33 (d, J = 7.2 Hz, 1H), 6.38-6.35 (t, J = 7.6 Hz, 1H), 6.20 (bs, 1H), 4.89 (bs, 1H), 4.64-4.61 (t, J = 6 Hz, 1H), 3.57 (bs, 1H), 3.35 (s, 2H), 3.30-3.29 (d, J = 5.6 Hz, 2H), 3.11 (s, 3H) 2.91-2.90 (d, J = 4.4 Hz, 3H), 2.09 (bs, 2H), 1.85 (bs, 1H), 1.57-1.54 (d, J = 10.8 Hz, 1H), 1.46 (bs, 4H), 0.43 (bs, 2H), 0.38 (bs, 2H). |
| I-846 | [structure: 3-amino-1-(1-(2-fluoroethyl)piperidin-4-yl)pyridin-2(1H)-one] | MS (ES): m/z 513.53 [M + H]$^+$, LCMS purity: 97.35%, HPLC purity: 95.13%, $^1$H NMR (DMSO-d$_6$, 400 MHZ): 8.84 (s, 1H), 8.21-8.20 (m, 2H), 7.92-7.91 (d, J = 5.2 Hz, 1H), 7.81-7.78 (t, J = 6.0 Hz, 1H), 7.46-7.45 (d, J = 6.0 Hz, 1H), 6.43-6.39 (m, 1H), 6.22 (s, 1H), 4.79 (s, 1H), 4.64-4.61 (m, 2H), 4.51 (s, 1H), 3.40-3.39 (d, J = 6.0 Hz, 3H), 3.31-3.30 (d, J = 5.6 Hz, 3H), 3.07-3.05 (m, 2H), 2.91-2.90 (d, J = 4.4 Hz, 3H), 2.25-2.20 (m, 2H), 1.95-1.93 (m, 2H), 1.78-1.77 (m, 2H), 0.44 (bs, 2H), 0.39 (bs, 2H). |

TABLE 34-continued

| Compound # | Reagent | Chiral Separation Conditions and Characterization Data |
|---|---|---|
| I-684 | 3-amino-1-(pyridin-2-yl)pyridin-2(1H)-one | MS (ES): m/z 461.5 [M + H]⁺ LCMS purity: 95.45%, HPLC purity: 98.89%, NMR (DMSO-d₆, 400 MHZ): 8.96 (s, 1H), 8.65-8.64 (d, J = 3.6 Hz, 1H), 8.34-8.32 (d, J = 6.8 Hz, 1H), 8.22 (s, 1H), 8.07-8.03 (t, J = 6.8 Hz, 1H), 7.95-7.94 (d, J = 4.8 Hz, 1H), 7.85-7.83 (d, J = 8 Hz, 2H), 7.57-7.52 (m, 2H), 6.55-6.51 (t, J = 7.2 Hz, 1H), 6.25 (s, 1H). 4.66-4.63 (t, J = 5.6 Hz, 1H), 3.43-3.41 (d, J = 6 Hz, 2H), 3.32 (s, 2H), 2.91-2.90 (d, J = 4.4 Hz, 3H), 0.46-0.40 (m, 4H). |
| I-749 | benzo[d]oxazol-4-amine | MS (ES): 408.37 [M + H]⁺ LCMS purity: 98.44%, HPLC purity: 98.24%, ¹H NMR (DMSO-d₆, 400 MHZ): 9.70 (s, 1H), 8.78 (s, 1H), 8.20 (s, 1H), 7.98 (bs, 2H), 7.49-7.47 (d, J = 6 Hz, 1H), 6.04 (s, 1H), 4.55 (bs, 1H), 3.36 (bs, 2H), 3.20-3.19 (d, J = 5.6 Hz, 2H), 2.94-2.93 (d, J = 4.4 Hz, 3H), 1.25 (s, 2H), 1.22 (s, 1H), 0.26 (bs, 3H). |
| I-545 | 3-amino-1-(4-methoxycyclohexyl)pyridin-2(1H)-one | MS (ES): m/z 496.58 [M + H]⁺ LCMS purity: 100%, HPLC purity: 97.96%, NMR (DMSO-d₆, 400 MHZ): 8.83 (s, 1H), 8.21 (s, 1H), 8.19 (s, 1H), 7.92-7.91 (d, J = 4.8 Hz, 1H), 7.82-7.79 (t, J = 6 Hz, 1H), 7.72-7.69 (m, 1H), 7.42-7.40 (d, J = 7.2 Hz, 1H), 6.43-6.40 (d, J = 7.2 Hz, 1H), 6.22 (s, 1H), 4.82-4.80 (d, J = 6 Hz, 1H), 4.67-4.61 (d, J = 6 Hz, 1H), 4.16-4.14 (t, J = 5.6 Hz, 1H), 3.41-3.39 (d, J = 6.4 Hz, 1H), 3.32-3.30 (d, J = 6 Hz, 2H), 3.28-3.21 (m, 1H), 2.92-2.91 (d, J = 4.8 Hz, 3H), 2.17-2.14 (d, J = 10.8 Hz, 2H), 1.83-1.81 (m, 4H), 1.38-1.11 (m, 4H), 0.90-0.89 (m, 2H), 0.44-0.39 (d, J = 3.6 Hz, 2H). |
| I-543 | 3-amino-1-(1-methylpiperidin-4-yl)pyridin-2(1H)-one | MS (ES): m/z 481.46 [M + H]⁺, LCMS purity: 96.30%, HPLC purity: 98.30%, ¹H NMR (DMSO-d₆, 400 MHZ): 8.61 (s, 1H), 8.21-8.19 (d, J = 7.2 Hz, 1H), 8.18 (s, 1H), 7.72 (bs, 1H), 7.57 (bs, 1H), 7.30-7.28 (d, J = 6.4 Hz, 1H), 7.11-7.09 (d, J = 8 Hz, 1H), 6.84-6.82 (d, J = 8 Hz, 1H), 6.45-6.42 (t, J = 7.2 Hz, 1H), 6.12 (s, 1H), 4.93 (bs, 2H), 3.44-3.42 (d, J = 6 Hz, 2H), 3.29 (s, 2H), 2.98-2.96 (d, J = 4.8 Hz, 3H), 1.96 (bs, 2H), 1.58 (s, 1H), 1.39 (s, 4H), 0.88-0.86 (d, J = 6.8 Hz, 2H), 0.46-0.43 (d, J = 12.4 Hz, 4H). |
| I-700 | (S)-3-amino-1-(tetrahydro-2H-pyran-3-yl)pyridin-2(1H)-one  B-ii | MS (ES): m/z 468.11 [M + H]⁺, LCMS purity: 97.07%, HPLC purity: 95.03%, CHIRAL HPLC purity: 96.70%, ¹H NMR (DMSO-d₆, 400 MHZ): 8.88 (s, 1H), 8.24-8.21 (d, J = 10 Hz, 2H), 7.93 (bs, 1H), 7.82-7.79 (t, J = 6 Hz, 1H), 7.51-7.49 (d, J = 6.4 Hz, 1H), 6.45-6.41 (t, J = 7.2 Hz, 1H), 6.24 (s, 1H), 4.91-4.86 (m, 1H), 4.64-4.61 (t, J = 5.6 Hz, 1H), 3.86-3.83 (m, 2H), 3.60 (s, 3H), 3.41-3.38 (m, 2H), 3.32-3.30 (d, J = 5.6 Hz, 2H), 2.92-2.91 (d, J = 4.8 Hz, 3H), 2.02 (s, 1H), 1.77 (bs, 2H), 0.44 (s, 4H). |

TABLE 34-continued

| Compound # | Reagent | Chiral Separation Conditions and Characterization Data |
|---|---|---|
| I-699 | B-i | MS (ES): m/z 468.32 [M + H]$^+$, LCMS purity: 95.12%, HPLC purity: 95.15%, CHIRAL HPLC purity: 97.17%, $^1$H NMR (DMSO-d$_6$, 400 MHZ): 8.88 (s, 1H), 8.24 (bs, 1H), 8.21 (s, 1H), 7.93-7.91 (d, J = 4.8 Hz, 1H), 7.82-7.79 (t, J = 6 Hz, 1H), 7.51-7.50 (d, J = 6.8 Hz, 1H), 6.45-6.38 (m, 1H), 6.24 (s, 1H), 4.91-4.86 (m, 1H), 4.64-4.61 (t, J = 6 Hz, 1H), 4.11-4.01 (m, 1H), 3.86-3.83 (m, 2H), 3.63 (s, 2H), 3.40-3.35 (m, 2H), 3.32-3.30 (d, J = 5.6 Hz, 2H), 2.92-2.91 (d, J = 4.8 Hz, 3H), 2.02 (s, 1H), 1.77 (bs, 2H), 0.44 (bs, 4H). |
| I-541 | | MS (ES): m/z 479.49 [M + H]$^+$, LCMS purity: 100%, HPLC purity: 99%, $^1$H NMR (DMSO-d$_6$, 400 MHZ): 8.99 (s, 1H), 8.52-8.51 (d, J = 4.4 Hz, 1H), 8.37-8.35 (d, J = 5.2 Hz, 1H), 8.23 (s, 1H), 8.09-8.04 (t, J = 8.8 Hz, 1H), 7.96-7.95 (d, J = 4.8 Hz, 1H), 7.84-7.81 (t, J = 6 Hz, 1H), 7.75-7.72 (m, 1H), 7.43-7.42 (m, 1H), 6.57-6.54 (t, J = 7.2 Hz, 1H), 6.24 (s, 1H), 3.43-3.41 (m, 3H), 3.83-3.33 (m, 3H), 2.91-2.90 (d, J = 4.8 Hz, 3H), 0.46-0.40 (m, 4H). |

Synthesis of N-((1-(hydroxymethyl)cyclopropyl)methyl)-7-(methylamino)-5-(1-(2-morpholinoethyl)-1H-pyrrolo[2,3-b]pyridin-3-yl)pyrazolo[1,5-a]pyrimidine-3-carboxamide (I-807)

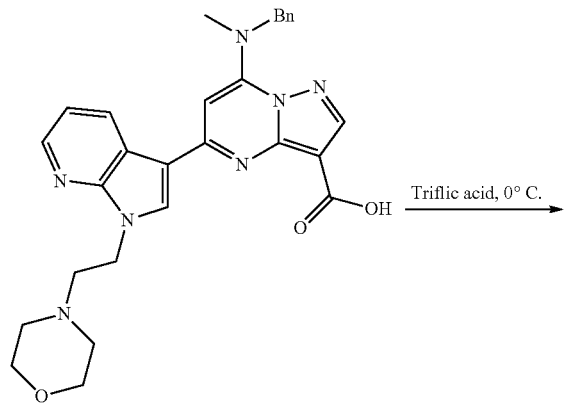

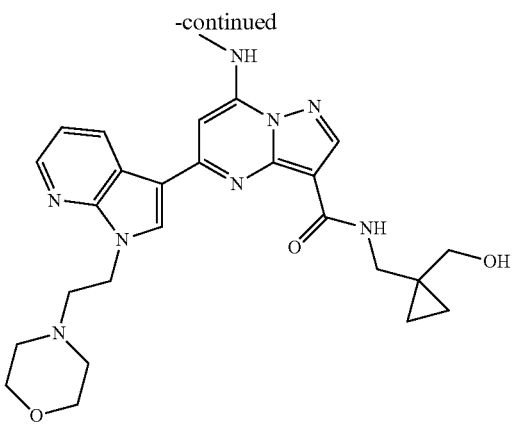

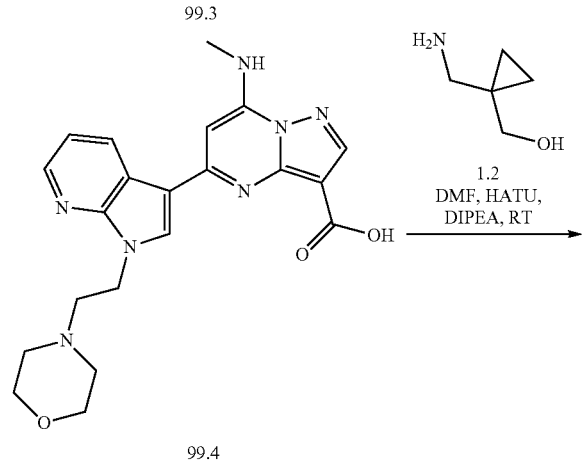

Synthesis of Compound 99.3.
Compound was synthesized as per I-582 to obtain 99.3 (Yield: 94.47%). MS (ES): m/z 512.44 [M+H]$^+$.

Synthesis of Compound 99.4.
Mixture of 99.3 (0.100 g, 0.1956 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with 10% MeOH: dichloromethane. Organic layer was combined, dried over sodium sulphate and concentrated under reduced pressure to obtain crude material. This was further purified by trituration with diethyl ether to a obtain 99.4 (0.070 g, 84.97%). MS (ES): m/z 422.19 [M+H]$^+$.

Synthesis of I-807. Compound was synthesized using general procedure of A to obtain I-807 (0.032 g, 38.18%). MS (ES): m/z 505.47 [M+H]$^+$, LCMS purity: 100%, HPLC purity: 99.85%, $^1$H NMR (DMSO-d$_6$, 400 MHZ): 8.70 (s, 2H), 8.38 (s, 2H), 8.31-8.30 (d, J=4 Hz, 2H), 7.35-7.33 (d, J=4 Hz, 1H), 6.67 (s, 1H), 4.71 (s, 1H), 7.30-7.27 (m, 1H), 4.51 (s, 2H), 3.55-3.48 (m, 6H), 3.39 (m, 1H), 3.12-3.11 (d, J=4 Hz, 3H), 2.83 (s, 2H), 2.52 (m, 4H), 0.53-0.47 (m, 4H).

Characterization data for further compounds prepared by the above methods are presented in Table 35 below. Compounds in Table 35 were prepared by methods substantially similar to those described to prepare I-807, where 99.3 was replaced with the reagent as indicated in Table 35.

TABLE 35

| Compound # | Reagent | Chiral Separation Conditions and Characterization Data |
|---|---|---|
| I-587 | ![structure] | MS (ES): m/z 434.52 [M + H]$^+$, LCMS purity: 95.88%, HPLC purity: 94.82%, $^1$H NMR (DMSO-d$_6$, 400 MHZ): 8.78 (s, 1H), 8.70-68 (d, J = 6.4 Hz, 1H), 8.38-38 (d, J = 3.6 Hz, 1H), 8.36 (s, 1H), 8.30-8.24 (m, 2H), 7.33-7.30 (m, 1H), 6.75 (s, 1H), 5.25-5.18 (m, 1H), 4.69-4.66 (t, J = 5.6 Hz, 1H), 3.48-3.47 (d, J = 5.6 Hz, 2H), 3.38-3.36 (t, J = 6 Hz, 3H), 3.17-3.16 (d, J = 5.2 Hz, 2H), 1.59-1.57 (d, J = 6.4 Hz, 6H), 0.51-0.41 (t, 4H). |

Synthesis of 5-((1-(2-cyclopropoxyethyl)-2-oxo-1,2-dihydropyridin-3-yl)amino)-N-((1-(hydroxymethyl)cyclopropyl)methyl)-7-(methylamino)pyrazolo[1,5-a]pyrimidine-3-carboxamide (I-577)

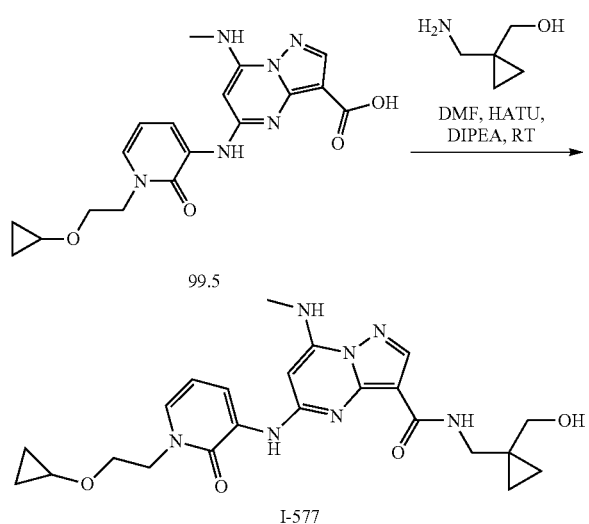

Synthesis of Compound 99.5

Compound was synthesized as per Example 109 (I-576). (0.3 g, 94.53%), MS (ES): m/z 385.5 [M+H]$^+$ Synthesis of Compound I-577.

Compound was synthesized using general procedure C to obtain I-577 (0.055 g, 44.22%). MS(ES): m/z 468.5 [M+H]$^+$. LCMS purity: 100%, HPLC purity: 99.75%, NMR (DMSO-d$_6$, 400 MHZ): 8.85 (s, 1H), 8.23 (s, 1H), 8.20 (s, 1H), 7.90-7.89 (d, J=4.4 Hz, 1H), 7.80 (s, 1H), 7.29-7.27 (d, J=6.8 Hz, 1H), 6.37-6.33 (t, J=6.8 Hz, 1H), 6.22 (s, 1H), 4.61 (s, 1H), 4.15 (s, 2H), 3.75 (s, 2H), 3.40-3.39 (d, J=5.6 Hz, 2H), 3.34-3.30 (d, J=13.6 Hz, 3H), 2.91-2.90 (d, J=4 Hz, 3H), 0.43-0.39 (m, 8H).

Characterization data for further compounds prepared by the above methods are presented in Table 36 below. Compounds in Table 36 were prepared by methods substantially similar to those described to prepare I-577, where 99.5 was replaced with the reagent as indicated in Table 36.

TABLE 36

| Compound # | Reagent | Chiral Separation Conditions and Characterization Data |
|---|---|---|
| I-426 | ![structure] | BOC was removed as a final step: MS(ES): m/z 424.4 [M + H]$^+$ LCMS purity: 99.41%, HPLC purity: 99.08%, $^1$H NMR (DMSO-d$_6$, 400 MHZ): 8.66 (bs, 1H), 8.28-8.26 (m, 1H), 8.16 (s, 1H), 7.92-7.90 (m, 2H), 7.82-7.79 (m, 1H), 7.10-7.07 (m, 1H), 5.88 (s, 1H), 4.57-4.54 (m, 1H), 4.35-4.33 (m, 1H), 3.30-3.29 (m, 2H), 3.21-3.20 (m, 2H), 2.92-2.91 (m, 3H), 0.81-0.74 (m, 4H), 0.31-0.29 (m, 4H). |
| I-425 | ![structure] | BOC was removed as a final step: MS(ES): m/z 398.07 [M + H]$^+$ LCMS purity: 99.41%, HPLC purity: 99.08%, $^1$H NMR (DMSO-d$_6$, 400 MHZ): 8.88 (bs, 1H), 8.29-8.28 (m, 1H), 8.16 (s, 1H), 7.92-7.81 (m, 3H), 7.08-7.05 (m, 1H), 5.93 (s, 1H), 4.57-4.54 (m, 1H), 3.96 (s, 3H), 3.31-3.29 (m, 2H), 3.21-3.20 (m, 2H), 2.91-2.90 (m, 3H), 0.31-0.29 (m, 4H). |

Example 100: Syntheses of compounds comprising N-(3-hydroxy-2-methylpropyl)aminocarbonyl at position 3 of the pyrazolo[1,5-a]pyrimidine 100.1. Synthesis of N-(3-hydroxy-2-methylpropyl)-5-((2-methoxypyridin-3-yl)amino)-7-(methylamino)pyrazolo[1,5-a]pyrimidine-3-carboxamide (I-434)

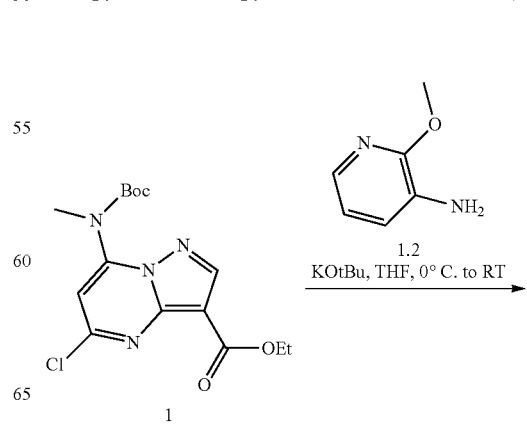

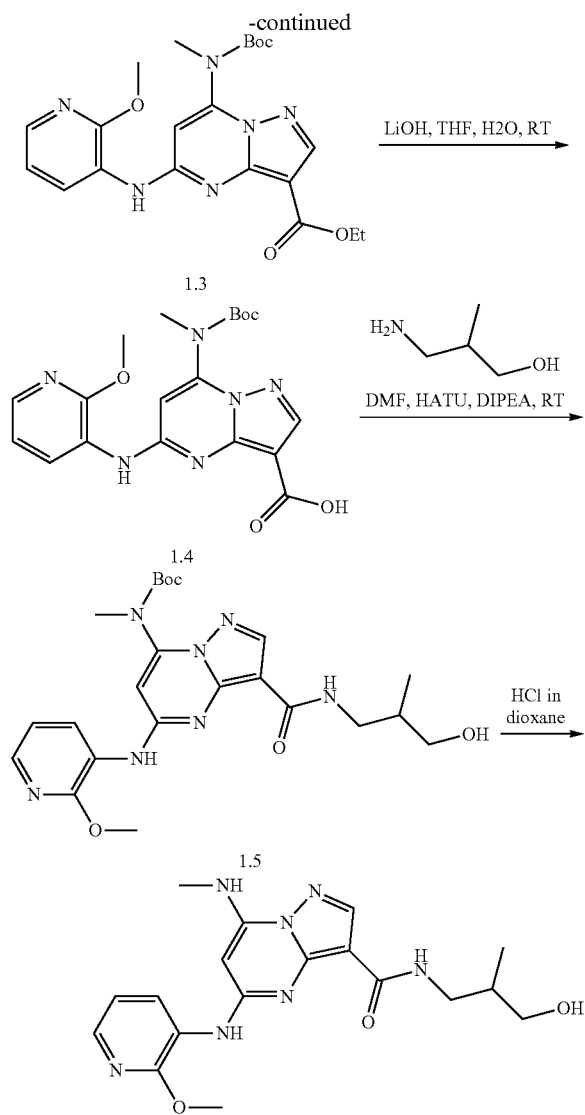

Synthesis of Compound 1.

Compound was synthesized using general procedure of core synthesis to obtain 1. (Yield: 62.21%). MS (ES): m/z 355.5 [M+H]+.

Synthesis of Compound 1.3.

To a cooled solution of 1. (0.500 g, 1.41 mmol, 1.0 eq), and 1.2 (0.174 g, 1.41 mmol, 1.0 eq) in tetrahydrofuran (10 mL) at 0° C. was added potassium ter-butoxide (2.8 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 1.3 (0.630 g, 96.22%). MS (ES): m/z 442.48 [M+H]+.

Synthesis of Compound 1.4.

To a solution of 1.3 (0.600 g, 1.36 mmol, 1.0 eq), in tetrahydrofuran: water (20 mL, 2:1) was added lithium hydroxide (0.312 g, 13.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 1.4 (0.400 g, 71.18%). MS(ES): m/z 415.42 [M+H]+.

Synthesis of Compound 1.5.

Compound was synthesized using general procedure A to obtain 1.5. (0.165 g, 70.42%), MS (ES): 486.24 [M+H]+

Synthesis of Compound I-434.

To 1.5. (0.165 g, 0.33 mmol, 1.0 eq) was added 4M hydrochloric acid in 1,4 Dioxane (3 mL) and stirred at room temperature for 4 h. After completion of reaction, reaction mixture was concentrated under reduced pressure; residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-434 (0.120 g, 91.62%). MS (ES): m/z 386.50 [M+H]+, LCMS purity: 99.04%, HPLC purity: 97.82%, CHIRAL HPLC purity: 49.95%, 50.04%, $^1$H NMR (DMSO-$d_6$, 400 MHZ): 8.90 (s, 1H), 8.28-8.26 (d, J=6.4 Hz, 1H), 7.92-7.88 (m, 2H), 7.83-7.80 (t, J=5.6 Hz, 1H), 7.07-7.00 (m, 1H), 5.92 (s, 1H), 4.56-4.53 (t, J=5.6 Hz, 1H), 3.95 (s, 3H), 3.22-3.19 (m, 4H), 3.15-3.08 (m, 1H), 2.91-2.90 (d, J=4.8 Hz, 3H), 1.69-1.65 (m, 1H), 0.78-0.76 (d, J=4.8 Hz, 3H).

Additional compounds prepared by substantially the same method, and their characterization data, are listed in the Table 37 below. The intermediate corresponding to 1.2 of the above scheme is also listed for each compound.

TABLE 37

| Compound | Intermediate | Characterization data |
|---|---|---|
| I-435 | ![structure] | MS (ES): m/z 412.45 [M + H]+ LCMS purity: 95.13%, HPLC purity: 91.09%, $^1$H NMR (DMSO-$d_6$, 400 MHZ): 8.69 (s, 1H), 8.28-8.26 (d, J = 6.8 Hz, 1H), 8.15 (s, 1H), 7.93-7.91 (m, 2H), 7.81-7.78 (m, 1H), 7.06-7.02 (m, 1H), 5.88 (s, 1H), 4.55 (bs, 1H), 4.35-4.32 (m, 1H), 3.25-3.24 (d, J = 4.8 Hz, 3H), 2.92-2.90 (d, J = 4.4 Hz, 3H), 1.69-1.64 (m, 1H), 1.27-1.23 (m, 1H), 0.89-0.76 (m, 7H). |

100.2. Synthesis of 5-((3'-fluoro-2-oxo-2H-[1,2'-bipyridin]-3-yl)amino)-N-(3-hydroxy-2-methylpropyl)-7-(methylamino)pyrazolo[1,5-a]pyrimidine-3-carboxamide (I-593)

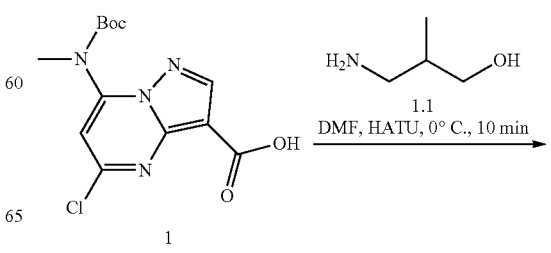

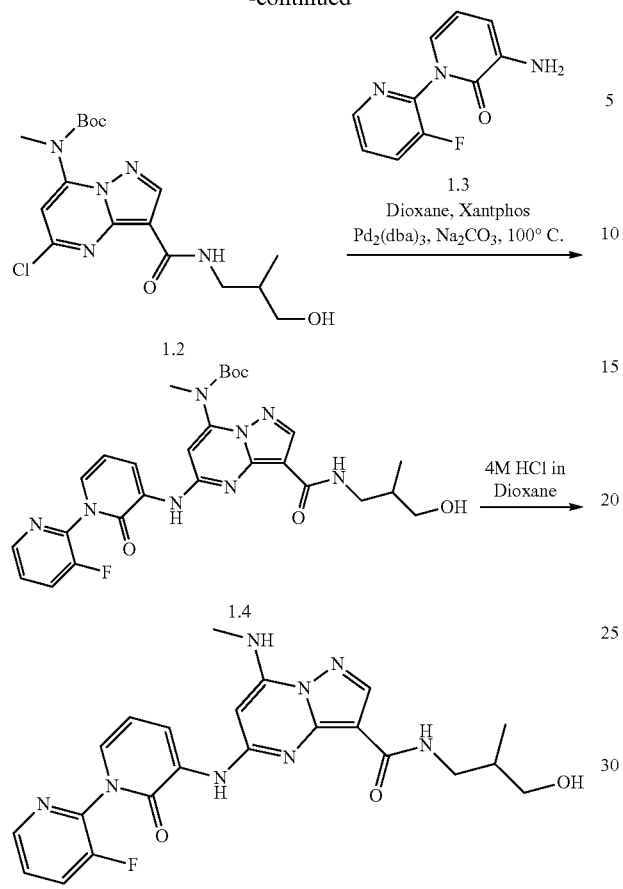

Synthesis of Compound 1.

Compound was synthesized using general procedure of core synthesis to obtain 1 (Yield: 71.67%).

Synthesis of Compound 1.2.

Compound was synthesized using general procedure A to obtain 1.2 (1.2 g, 49.27%). MS(ES): m/z 398.8 [M+H]$^+$.

Synthesis of Compound 1.4.

Compound was synthesized using general procedure B to obtain 1.4 (0.155 g, 60.47%). MS(ES): m/z 567.5 [M+H]$^+$.

Synthesis of Compound I-593:

Compound was synthesized using general procedure C to obtain I-593 (0.122 g, 95.60%), MS (ES): m/z 467.41 [M+H]$^+$, LCMS purity: 98.31%, HPLC purity: 96.37%, Chiral HPLC purity: 48.31%+49.96%, $^1$H NMR (DMSO-d$_6$, 400 MHZ): 9.03 (s, 1H), 8.53-8.52 (d, J=4.4 Hz, 1H), 8.37-8.35 (d, J=6.8, 1H), 8.23 (s, 1H), 8.10-8.06 (t, J=8.8 Hz 1H), 7.98-7.96 (d, J=4.4 Hz, 1H), 7.83-7.82 (m, 1H), 7.75-7.73 (m, 1H), 7.45-7.44 (d, J=6.8 Hz, 1H), 6.53-6.49 (t, J=7.2 Hz, 1H), 6.247 (s, 1H), 4.64-4.62 (t, J=5.2 Hz, 1H), 3.36 (s, 2H), 3.30-3.25 (m, 2H), 2.92-2.91 (d, J=4.4 Hz, 3H), 1.84-1.79 (m, 1H), 0.92-0.91 (m, 3H).

Additional compounds prepared by substantially the same method, and their characterization data, are listed in the Table 38 below. The intermediate corresponding to 1.3 of the above scheme is also listed for each compound.

TABLE 38

| Compound | Intermediate | Characterization data |
|---|---|---|
| I-613 | (structure) | MS (ES): m/z 484.31 [M + H]$^+$, LCMS purity: 100%, HPLC purity: 99.09%, $^1$H NMR (DMSO-d$_6$, 400 MHZ): 8.85 (s, 1H), 8.20 (s, 1H), 8.18 (s, 1H), 7.93-7.92 (d, J = 4.8 Hz, 1H), 7.80 (bs, 1H), 7.43-7.41 (d, J = 6.4 Hz, 1H), 6.37-6.34 (t, J = 7.2 Hz, 1H), 6.22 (s, 1H), 4.80 (bs, 1H), 4.63-4.60 (t, J = 5.6 Hz, 1H), 3.28 (s, 6H), 2.92-2.91 (d, J = 4.8 Hz, 3H), 2.14 (s, 3H), 1.81 (bs, 5H), 1.24 (s, 3H), 0.89-0.87 (d, J = 6.8 Hz, 3H). |
| I-633 | (structure) | MS(ES): m/z 452.61 [M + H]$^+$ LCMS purity: 97.71%, HPLC purity: 96.77%, Chiral HPLC purity: 49.60%, 46.7%, NMR (DMSO-d$_6$, 400 MHZ): 8.99 (s, 1H), 8.31 (s, 1H), 8.25-8.23 (d, J = 7.2 Hz, 1H), 8.21 (s, 1H), 7.95-7.94 (d, J = 3.6 Hz, 1H), 7.90 (s, 1H), 7.80 (s, 1H), 7.54-7.53 (d, J = 6.4 Hz, 1H), 6.45-6.41 (t, J = 6.8 Hz, 1H), 6.25 (s, 1H), 4.61 (s, 1H), 3.91 (s, 4H), 3.27-3.22 (m, 2H), 2.91-2.90 (d, J = 3.2 Hz, 3H), 1.79-1.78 (d, J = 5.6 Hz, 2H), 0.89-0.88 (d, J = 6.4 Hz, 3H). |
| I-649 | (structure) | MS (ES): m/z 456.52 [M + H]$^+$, LCMS purity: 100%, HPLC purity: 98.07%, Chiral HPLC purity: 98.07%, $^1$H NMR (DMSO-d$_6$, 400 MHZ): 8.87 (s, 1H), 8.22-8.21 (d, J = 4.0 Hz, 2H), 7.93-7.92 (d, J = 4.8 Hz, 1H), 7.82-7.79 (t, J = 6.0 Hz, 1H), 7.49-7.47 (d, J = 6.0 Hz, 1H), 6.39-6.36 (t, J = 7.2 Hz, 1H), 6.24 (s, 1H), 5.05 (m, 1H), 4.63-4.60 (m, 1H), 4.04-4.00 (dd, J = 3.2 Hz, 11.2 Hz, 2H), 3.58 (s, 2H), 3.55-3.49 (t, J = 11.2 Hz, 2H), 3.31-3.22 (m, 3H), 2.93-2.91 (d, J = 4.8 Hz, 3H), 2.00-1.94 (m, 2H), 1.81-1.75 (m, 2H), 0.90-0.88 (d, J = 6.8 Hz, 3H). |

TABLE 38-continued

| Compound | Intermediate | Characterization data |
|---|---|---|
| I-663 | | MS (ES): m/z 453.71 [M + H]⁺, LCMS purity: 100%, HPLC purity: 100%, CHIRAL HPLC purity: 50.25%, 48.78%, $^1$H NMR (DMSO-$d_6$, 400 MHZ): 9.04 (s, 1H), 8.31-8.30 (d, J = 7.2 Hz, 1H), 8.22 (s, 1H), 8.03 (s, 1H), 7.99-7.98 (d, J = 4.8 Hz, 1H), 7.79-7.76 (t, J = 5.6 Hz, 1H), 7.44-7.43 (d, J = 6 Hz, 1H), 6.48-6.45 (t, J = 7.2 Hz, 1H), 6.22 (s, 1H), 4.60 (bs, 1H), 3.31 (bs, 4H), 2.91-2.90 (d, J = 4.4 Hz, 3H), 2.19 (s, 3H), 1.80-1.75 (m, 1H), 0.88-0.87 (d, J = 6.8 Hz, 3H). |
| I-682 | | MS (ES): m/z 449.22 [M + H]⁺, LCMS purity: 99.46%, HPLC purity: 99.03%, CHIRAL HPLC purity: 49.46%, 49.85%, $^1$H NMR (DMSO-$d_6$, 400 MHZ): 9.99 (s, 1H), 8.66-8.65 (d, J = 3.6 Hz, 1H), 8.33-8.32 (d, J = 6 Hz, 1H), 8.23 (s, 1H), 8.08-8.04 (t, J = 6.4 Hz, 1H), 7.95 (bs, 1H), 7.86-7.82 (m, 2H), 7.59-7.54 (m, 2H), 6.50-6.47 (t, J = 7.2 Hz, 1H), 6.26 (s, 1H), 6.62 (bs, 2H), 3.35 (s, 1H), 3.30-3.23 (m, 2H), 2.92 (s, 3H), 1.84-1.79 (m, 1H), 0.92-0.91 (d, J = 6.8 Hz, 3H). |
| I-941 | | MS (ES): 466.76 [M + H]⁺, LCMS purity: 98.89%, HPLC purity: 98.32%, CHIRAL HPLC purity: 49.61%, 48.63%, $^1$H NMR (DMSO-$d_6$, 400 MHZ): 8.98 (s, 1H), 8.34-8.30 (d, J = 6 Hz, 1H), 8.22 (s, 1H), 7.97 (bs, 1H), 7.84-7.81 (t, J = 6 Hz, 1H), 7.61-7.58 (m, 2H), 7.51-7.47 (t, J = 9.2 Hz, 1H), 7.43-7.39 (t, J = 7.6 Hz, 1H), 7.36-7.34 (d, J = 5.6 Hz, 1H), 6.47-6.44 (t, J = 7.2 Hz, 1H), 6.24 (s, 1H), 4.65 (bs, 1H), 2.30-3.23 (m, 3H), 2.091 (s, 3H), 1.89-1.79 (m, 1H), 1.24 (s, 1H), 0.92-0.91 (d, J = 6.8 Hz, 3H). |
| I-944 | | MS (ES): m/z 454.71 [M + H]⁺, LCMS purity: 100%, HPLC purity: 98.76%, CHIRAL HPLC: 45.50%, 48.84%, $^1$H NMR (DMSO-$d_6$, 400 MHZ): 8.89 (bs, 1H), 8.21 (s, 1H), 8.16-8.14 (d, J = 7.2 Hz, 1H), 7.97 (bs, 1H), 7.83 (bs, 1H), 7.45-7.43 (d, J = 6.4 Hz, 1H), 6.36-6.33 (t, J = 7.2 Hz, 1H), 6.19 (s, 1H), 4.76 (bs, 1H), 3.28-3.20 (m, 3H), 2.91-2.90 (d, J = 4.4 Hz, 3H), 1.87-1.80 (m, 2H), 1.77 (bs, 4H), 1.47-1.44 (d, J = 12 Hz, 2H), 1.33 (s, 1H), 1.23-1.22 (d, J = 3.2 Hz, 3H), 0.88-0.86 (d, J = 6.8 Hz, 4H). |
| I-947 | | MS (ES): m/z 466.57 [M + H]⁺, LCMS purity: 99.25%, HPLC purity: 97.51%, CHIRAL HPLC: 50.53%, 48.27%, $^1$H NMR (DMSO-$d_6$, 400 MHZ): 8.96 (s, 1H), 8.32-8.30 (d, J = 7.2 Hz, 1H), 8.21 (s, 1H), 7.96-7.94 (d, J = 4.8 Hz, 1H), 7.83-7.80 (t, J = 5.6 Hz, 1H), 7.63-7.58 (m, 1H), 7.50-7.47 (d, J = 9.6 Hz, 1H), 7.37-7.36 (d, J = 4.4 Hz, 3H), 6.45-6.42 (t, J = 6.8 Hz, 1H), 6.25 (s, 1H), 4.64-4.62 (m, 1H), 3.29-3.24 (m, 2H), 2.91-2.90 (d, J = 4.4 Hz, 3H), 1.83-1.79 (m, 1H), 1.22 (bs, 2H), 0.91-0.90 (d, J = 6.4 Hz, 3H). |

1.3. Chiral separation of N-(3-hydroxy-2-methyl-propyl)-5-((2-methoxypyridin-3-yl)amino)-7-(methylamino)pyrazolo[1,5-a]pyrimidine-3-carboxamide (I-434)

-continued

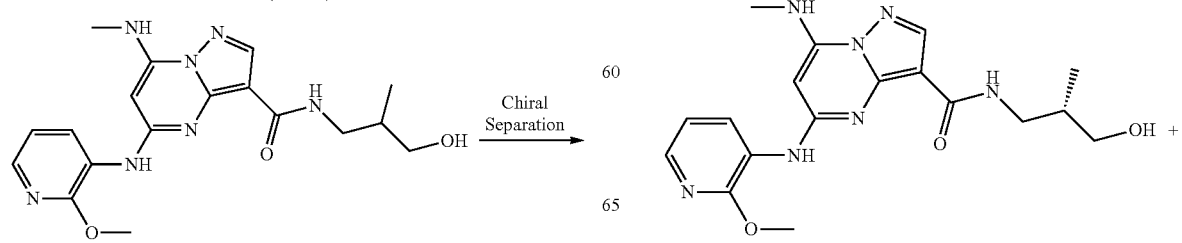

-continued

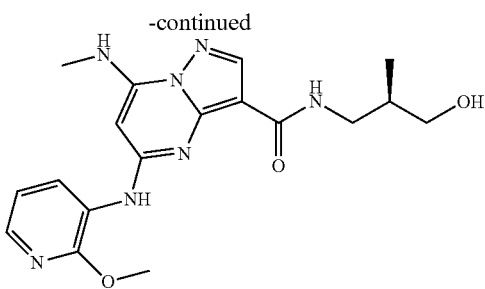

Isomers of I-434 (0.100 g), I-483 and I-484, were separated out using column (CHIRAL PAK AD-H 250×4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford one pure isomer (0.030 g). MS(ES): m/z 386.31 [M+H]+, LCMS purity: 100%, HPLC purity: 99.17%, CHIRAL HPLC purity: 100%, $^1$H NMR (DMSO-$d_6$, 400 MHZ): 8.92 (s, 1H), 8.29-8.27 (d, J=7.2 Hz, 1H), 8.16 (s, 1H), 7.94-7.88 (m, 2H), 7.84-7.81 (t, J=5.6 Hz, 1H), 7.04-7.01 (m, 1H), 5.93 (s, 1H), 4.58-4.55 (t, J=10.8 Hz, 1H), 3.96 (s, 3H), 3.29-3.24 (m, 3H), 3.15-3.10 (m, 1H), 2.92-2.91 (d, J=4.8 Hz, 3H), 1.70-1.65 (m, 1H), 0.78-0.77 (d, J=6.8 Hz, 3H).

FR-b was concentrated under reduced pressure at 30° C. to afford the other pure isomer (0.027 g). MS(ES): m/z 386.31 [M+H]+, LCMS purity: 98.88%, HPLC purity: 96.34%, CHIRAL HPLC purity: 95.05%, $^1$H NMR (DMSO-$d_6$, 400 MHZ): 8.91 (s, 1H), 8.28-8.26 (d, J=6 Hz, 1H), 8.15 (s, 1H), 8.00 (s, 2H), 7.83-7.80 (t, J=6 Hz, 1H), 7.04-7.00 (m, 1H), 5.92 (s, 1H), 4.55 (s, 1H), 3.95 (s, 3H), 3.25-3.23 (m, 3H), 3.15-3.08 (m, 1H), 2.91-2.90 (d, J=4.4 Hz, 3H), 1.69-1.64 (m, 1H), 0.78-0.77 (d, J=6.8 Hz, 3H).

Additional compounds prepared by substantially the same method, and their characterization data, are listed in the Table 39 below.

TABLE 39

| Compound | Isomers | Characterization data |
|---|---|---|
| I-682 | I-730<br>I-731 | FR-a: MS (ES): m/z 449.37 [M + H]+, LCMS purity: 99.82%, HPLC purity: 99.83%, CHIRAL HPLC purity: 100%, $^1$H NMR (DMSO-$d_6$, 400 MHZ): 9.01 (s, 1H), 8.66-8.65 (d, J = 4 Hz, 1H), 8.33-8.32 (d, J = 7.2 Hz, 1H), 8.23 (s, 1H), 8.08-8.05 (d, J = 6 Hz, 1H), 7.98-7.96 (d, J = 4.8 Hz, 1H), 7.86-7.82 (m, 2H), 7.59-7.54 (m, 2H), 6.50-6.47 (t, J = 7.6 Hz, 1H), 6.26 (s, 1H), 4.65-4.62 (t, J = 5.2 Hz, 1H), 3.92 (s, 1H), 3.30-3.23 (m, 2H), 2.93-2.91 (d, J = 4.8 Hz, 3H), 1.84-1.79 (m, 1H), 1.24 (s, 1H), 0.92-0.90 (d, J = 6.8 Hz, 3H).<br>FR-b: MS (ES): m/z 449.32 [M + H]+, LCMS purity: 99.66%, HPLC purity: 99.10%, CHIRAL HPLC purity: 99.60%, $^1$H NMR (DMSO-$d_6$, 400 MHZ): 9.01 (s, 1H), 8.66-8.65 (d, J = 4 Hz, 1H), 8.33-8.32 (d, J = 6.4 Hz, 1H), 8.23 (s, 1H), 8.08-8.05 (t, J = 8 Hz, 1H), 7.97 (bs, 1H), 7.86-7.83 (m, 2H), 7.59-7.54 (m, 2H), 6.50-6.47 (t, J = 7.2 Hz, 1H), 6.26 (s, 1H), 4.64 (bs, 1H), 3.92 (s, 1H) 3.30-3.23 (m, 2H), 2.92 (bs, 3H), 1.84-1.79 (m, 1H), 1.24 (s, 1H), 0.92-0.90 (d, J = 6.8 Hz, 3H). |
| I-663 | I-736<br>I-737 | FR-a: MS (ES): m/z 453.56 [M + H]+, LCMS purity: 97.90%, HPLC purity: 97.49%, CHIRAL HPLC purity: 97.41%, $^1$H NMR (DMSO-$d_6$, 400 MHZ): 8.81 (s, 1H), 8.67-8.65 (d, J = 6.4 Hz, 1H), 8.17 (s, 1H), 8.03-8.01 (d, J = 9.2 Hz, 1H), 7.90-7.89 (d, J = 4.8 Hz, 1H), 7.84-7.82 (m, 1H), 7.08-7.05 (m, 1H), 6.07 (s, 1H), 5.27 (bs, 1H), 4.56-4.49 (m, 1H), 4.30 (bs, 1H), 4.28 (s, 1H), 3.35 (bs, 1H), 2.92-2.91 (d, J = 4.8 Hz, 3H), 2.50 (s, 3H), 2.14-2.11 (m, 1H), 2.07-2.03 (m, 1H), 1.95-1.86 (m, 1H), 1.71-1.66 (m, 1H), 1.12-1.08 (m, 1H).<br>FR-b: MS (ES): m/z 453.51 [M + H]+, LCMS purity: 98.85%, HPLC purity: 98.85%, CHIRAL HPLC purity: 99.48%, $^1$H NMR (DMSO-$d_6$, 400 MHZ): 9.04 (s, 1H), 8.31-8.30 (d, J = 6.8 Hz, 1H), 8.22 (s, 1H), 8.03 (s, 1H), 7.99 (bs, 1H), 7.79-7.76 (t, J = 5.6 Hz, 1H), 7.44-7.43 (d, J = 6 Hz, 1H), 6.48-6.45 (t, J = 7.2 Hz, 1H), 6.22 (s, 1H), 4.60 (bs, 1H), 2.91 (s, 3H), 2.50 (s, 3H), 2.19 (s, 3H), 1.80-1.75 (m, 1H), 0.89-0.87 (d, J = 6.8 Hz, 4H). |
| I-613 | I-829<br>I-830 | FR-a: MS (ES): m/z 484.31 [M + H]+, LCMS purity: 100%, HPLC purity: 99.73%, CHIRAL HPLC purity: 99.65%, $^1$H NMR (DMSO-$d_6$, 400 MHZ): 8.85 (s, 1H), 8.20 (s, 1H), 8.18 (s, 1H), 7.93-7.92 (d, J = 4.4 Hz, 1H), 7.81-7.78 (t, J = 5.6 Hz, 1H), 7.43-7.41 (d, J = 6.4 Hz, 1H), 6.37-6.34 (t, J = 6.8 Hz, 1H), 6.22 (s, 1H), 4.80 (bs, 1H), 4.60 (bs, 1H), 3.28 (s, 5H), 2.92-2.91 (d, J = 4.8 Hz, 3H), 2.17-2.14 (d, J = 11.6 Hz, 2H), 1.80 (bs, 5H), 1.34-1.30 (m, 2H), 1.24 (s, 2H), 0.89-0.87 (d, J = 6.8 Hz, 4H).<br>FR-b: MS (ES): m/z 484.31 [M + H]+, LCMS purity: 99.35%, HPLC purity: 99.19%, CHIRAL HPLC purity: 100%, $^1$H NMR (DMSO-$d_6$, 400 MHZ): 8.85 (s, 1H), 8.20 (s, 1H), 8.18 (s, 1H), 7.93-7.92 (d, J = 4.8 Hz, 1H), 7.81-7.78 (t, J = 6 Hz, 1H), 7.43-7.41 (d, J = 6 Hz, 1H), 6.37-6.34 (t, J = 7.2 Hz, 1H), 6.22 (s, 1H), 4.80 (bs, 1H), 4.63-4.60 (t, J = 5.2 Hz, 1H), 3.28 (s, 5H), 2.92-2.91 (d, J = 4.8 Hz, 3H), 2.17-2.14 (d, J = 12 Hz, 2H), 1.81 (bs, 5H), 1.37-1.30 (m, 2H), 1.24 (s, 2H), 0.89-0.87 (d, J = 6.4 Hz, 4H). |
| I-947 | I-1033<br>I-1034 | FR-a: MS (ES): m/z 466.41 [M + H]+, LCMS purity: 100%, HPLC purity: 96.91%, CHIRAL HPLC purity: 96.69%, $^1$H NMR (DMSO-$d_6$, 400 MHZ): 8.96 (s, 1H), 8.31-8.30 (d, J = 4.0 Hz, 1H), 8.21 (s, 1H), 7.95-7.94 (d, J = 4.0 Hz, 1H), 7.83-7.80 (m, 1H), |

TABLE 39-continued

| Compound | Isomers | Characterization data |
|---|---|---|
| | | 7.61-7.58 (m, 1H), 7.49-7.47 (m, 1H), 7.37-7.36 (m, 3H), 6.45-6.42 (m, 1H), 6.25 (s, 1H), 4.64-4.61 (m, 1H), 3.34 (s, 3H), 3.27-3.24 (m, 2H), 2.91-2.90 (d, J = 4.0 Hz, 3H), 0.91-0.90 (d, J = 4.0 Hz, 3H). FR-b: MS (ES): m/z 466.62 [M + H]$^+$, LCMS purity: 100%, HPLC purity: 99.11%, CHIRAL HPLC purity: 99.63%, $^1$H NMR (DMSO-$d_6$, 400 MHZ): 8.96 (s, 1H), 8.31-8.30 (d, J = 4.0 Hz, 1H), 8.21 (s, 1H), 7.95 (s, 1H), 7.81 (s, 1H), 7.61-7.58 (m, 1H), 7.49-7.47 (m, 1H), 7.37-7.36 (m, 3H), 6.45-6.42 (m, 1H), 6.25 (s, 1H), 4.64-4.61 (m, 1H), 3.34 (s, 3H), 3.27-3.24 (m, 2H), 2.91-2.90 (d, J = 4.0 Hz, 3H), 0.91-0.90 (d, J = 4.0 Hz, 3H). |
| I-593 | I-868 I-869 | FR-a: MS (ES): m/z 467.32 [M + H]$^+$, LCMS purity: 97.79%, HPLC purity: 98.65%, CHIRAL HPLC purity: 100%, $^1$H NMR (DMSO-$d_6$, 400 MHZ): 9.03 (s, 1H), 8.53 (s, 1H), 8.36-8.35 (d, J = 4.0, 1H), 8.23 (s, 1H), 8.10-8.06 (t, J = 8.0 Hz 1H), 7.98 (s, 1H), 7.84 (s, 1H), 7.74 (s, 1H), 7.46-7.44 (d, J = 8.0 Hz, 1H), 6.51 (s, 1H), 6.24 (s, 1H), 4.65 (s, 1H), 3.51 (s, 2H), 3.39 (s, 2H), 2.92-2.91 (d, J = 4.0 Hz, 3H), 1.82-1.81 (m, 1H), 0.92-0.91 (m, 3H). FR-b: MS (ES): m/z 467.52 [M + H]$^+$, LCMS purity: 100%, HPLC purity: 99.12%, CHIRAL HPLC purity: 99.25%, $^1$H NMR (DMSO-$d_6$, 400 MHZ):- 9.03 (s, 1H), 8.52 (s, 1H), 8.36 (s, 1H), 8.23 (s, 1H), 8.07 (s, 1H), 7.97 (s, 1H), 7.83 (s, 1H), 7.74 (s, 1H), 7.44 (s, 1H), 6.51 (s, 1H), 6.24 (s, 1H), 4.64 (s, 1H), 3.38 (s, 4H), 2.92-2.91 (d, J = 4.0 Hz, 3H), 1.81 (s, 1H), 1.24-0.91 (m, 3H). |
| I-941 | I-1076 I-1077 | FR-a: MS (ES): m/z 466.27 [M + H]$^+$, LCMS purity: 99.01%, HPLC purity: 98.27%, CHIRAL HPLC purity: 99.52%, $^1$H NMR (DMSO-$d_6$, 400 MHZ): 8.98 (s, 1H), 8.33-8.32 (d, J = 6.0 Hz, 1H), 8.22 (s, 1H), 7.97-7.95 (d, J = 4.4 Hz, 1H), 7.83-7.81 (t, J = 5.6 Hz, 1H), 7.61-7.57 (m, 2H), 7.51-7.34 (m, 3H), 6.47-6.43 (m, 1H), 6.24 (s, 1H), 4.65-4.62 (m, 1H), 3.29-3.16 (m, 1H), 2.91-2.90 (d, J = 3.6 Hz, 3H), 2.67-2.57 (m, 2H), 1.83-1.78 (m, 1H), 1.05-0.99 (m, 1H), 0.91-0.90 (d, J = 6.8 Hz, 3H). FR-b: MS (ES): m/z 466.27 [M + H]$^+$, LCMS purity: 95.06%, HPLC purity: 95.85%, CHIRAL HPLC purity: 100%, $^1$H NMR (DMSO-$d_6$, 400 MHZ): 8.98 (s, 1H), 8.33-8.32 (d, J = 6.4 Hz, 1H), 8.22 (s, 1H), 7.97-7.96 (d, J = 4.0 Hz, 1H), 7.84-7.81 (m, 1H), 7.61-7.57 (m, 2H), 7.51-7.34 (m, 3H), 6.47-6.43 (t, J = 7.2 Hz, 1H), 6.24 (s, 1H), 4.65-4.62 (m, 1H), 3.29-3.24 (m, 1H), 2.91-2.90 (d, J = 4.0 Hz, 3H), 2.67-2.57 (m, 2H), 1.83-1.78 (m, 1H), 1.33-0.99 (m, 1H), 0.91-0.90 (d, J = 6.4 Hz, 3H). |
| I-649 (Chiral separation when methylamino at position 7 is protected by Boc, followed by removal of Boc) | I-1031 I-1032 | FR-a: MS (ES): m/z 456.36 [M + H]$^+$, LCMS purity: 97.86%, HPLC purity: 97.09%, Chiral HPLC: 97.33%, $^1$H NMR (DMSO-$d_6$, 400 MHZ): 8.88 (s, 1H), 8.21-8.20 (d, J = 3.6 Hz, 2H), 7.94-7.93 (d, J = 4.4 Hz, 1H), 7.82-7.79 (t, J = 5.6 Hz, 1H), 7.49-7.47 (d, J = 6.4 Hz, 1H), 6.39-6.36 (t, J = 6.8 Hz, 1H), 6.24 (s, 1H), 5.05-5.01 (m, 1H), 4.62 (s, 1H), 4.03-4.01 (d, J = 8.0 Hz, 3H), 3.52-3.46 (t, J = 13.2 Hz, 3H), 3.27-3.22 (m, 2H), 2.92-2.91 (d, J = 4.4 Hz, 3H), 2.02-1.94 (m, 2H), 1.81-1.75 (m, 3H), 0.89-0.88 (d, J = 6.4 Hz, 3H). FR-b: MS (ES): m/z 456.31 [M + H]$^+$, LCMS purity: 98.48%, HPLC purity: 97.12%, Chiral HPLC: 98.73%, $^1$H NMR (DMSO-$d_6$, 400 MHZ): 8.88 (s, 1H), 8.21 (s, 2H), 7.94-7.93 (d, J = 4.4 Hz, 1H), 7.80 (s, 1H), 7.49-7.47 (d, J = 6.4 Hz, 1H), 6.39-6.36 (t, J = 6.8 Hz, 1H), 6.24 (s, 1H), 5.05-5.01 (m, 1H), 4.62 (s, 1H), 4.03-4.01 (d, J = 8.0 Hz, 3H), 3.52-3.46 (t, J = 13.2 Hz, 3H), 3.25-3.22 (m, 2H), 2.92-2.91 (d, J = 4.4 Hz, 3H), 2.02-1.94 (m, 2H), 1.81-1.75 (m, 3H), 0.89-0.88 (d, J = 6.4 Hz, 3H). |
| I-944 (Chiral separation when methylamino at position 7 is protected by Boc, followed by removal of Boc) | I-1119 I-1120 | FR-a: MS (ES): m/z 454.32 [M + H]$^+$, LCMS purity: 100%, HPLC purity: 99.05%, Chiral HPLC: 98.46%, $^1$H NMR (DMSO-$d_6$, 400 MHZ): 8.95 (s, 1H), 8.21-8.18 (m, 2H), 7.92-7.91 (d, J = 4.8 Hz, 1H), 7.82-7.79 (t, J = 6.0 Hz, 1H), 7.44-7.43 (d, J = 6.0 Hz, 1H), 6.37-6.34 (t, J = 7.2 Hz, 1H), 6.22 (s, 1H), 4.84-4.78 (m, 1H), 3.87-3.84 (m, 1H), 3.25-3.21 (m, 4H), 2.93-2.91 (d, J = 4.8 Hz, 3H), 1.88-1.65 (m, 9H), 1.49-1.39 (m, 2H), 0.89-0.88 (m, 3H). FR-b: MS (ES): m/z 454.52 [M + H]$^+$, LCMS purity: 100%, HPLC purity: 99.48%, Chiral HPLC: 100%, $^1$H NMR (DMSO-$d_6$, 400 MHZ): 8.85 (s, 1H), 8.20-8.18 (m, 2H), 7.92-7.91 (d, J = 4.8 Hz, 1H), 7.82-7.79 (t, J = 6.0 Hz, 1H), 7.44-7.43 (d, J = 6.0 Hz, 1H), 6.37-6.34 (t, J = 7.2 Hz, 1H), 6.22 (s, 1H), 4.84-4.78 (m, 1H), 3.87-3.84 (m, 1H), 3.25-3.21 (m, 4H), 2.93-2.91 (d, J = 4.8 Hz, 3H), 1.88-1.65 (m, 9H), 1.49-1.39 (m, 2H), 0.89-0.88 (m, 3H). |
| I-633 | I-668 I-669 | FR-a: MS (ES): m/z 452.22 [M + H]$^+$, LCMS purity: 99.39%, HPLC purity: 99.46%, CHIRAL HPLC purity: 100%, $^1$H NMR (DMSO-$d_6$, 400 MHZ): 8.99 (s, 1H), 8.31 (s, 1H), 8.25-8.23 (d, J = 7.6 Hz, 1H), 8.21 (s, 1H), 7.95-7.93 (d, J = 4.8 Hz, 1H), 7.90 (s, 1H), 7.82-7.78 (t, J = 6.4 Hz, 1H), 7.54-7.53 (d, J = 6.8 Hz, 1H), 6.45-6.41 (t, J = 7.2 Hz, 1H) 6.25 (s, 1H), 4.62-4.60 (t, J = 5.2 Hz, |

TABLE 39-continued

| Compound | Isomers | Characterization data |
|---|---|---|
| | | 1H), 3.91 (s, 3H), 3.37-3.31 (m, 3H), 2.91-2.90 (d, J = 4.4 Hz, 3H), 1.81-1.76 (m, 1H), 1.23 (bs, 1H), 0.89-0.88 (d, J = 6.8 Hz, 3H).<br>FR-b: MS (ES): m/z 452.27 [M + H]$^+$, LCMS purity: 100%, HPLC purity: 96.86%, CHIRAL HPLC purity: 100%, $^1$H NMR (DMSO-d$_6$, 400 MHZ): 8.99 (s, 1H), 8.31 (s, 1H), 8.25-8.23 (d, J = 7.6 Hz, 1H), 8.20 (s, 1H), 7.94 (bs, 1H), 7.90 (s, 1H), 7.81-7.79 (t, J = 5.6 Hz, 1H), 7.54-7.53 (d, J = 7.2 Hz, 1H), 6.45-6.41 (t, J = 7.2 Hz, 1H) 6.25 (s, 1H), 4.62 (bs, 1H), 3.91 (s, 3H), 3.35-3.26 (m, 3H), 2.91-2.90 (d, J = 4.4 Hz, 3H), 1.81-1.76 (m, 1H), 1.23 (bs, 1H), 0.89-0.88 (d, J = 6.8 Hz, 3H). |

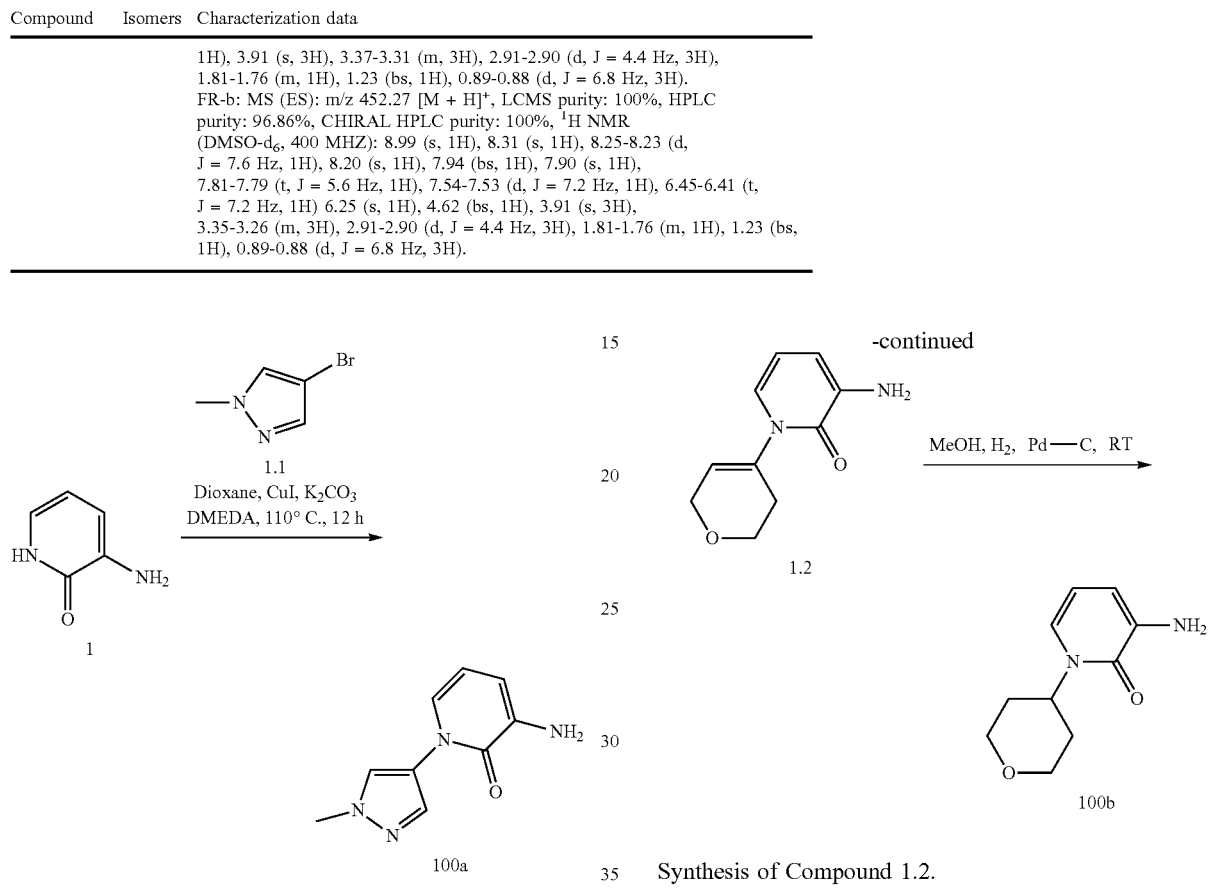

Synthesis of Compound 100a.

To a solution of 1. (1.0 g, 9.08 mmol, 1 eq) and 1.1 (1.7 g, 10.89 mmol, 1.2 eq) in 1,4-dioxane (10 mL) was added potassium carbonate (2.5 g, 18.16 mmol, 2.0 eq) and degassed with argon for 15 min. Copper iodide (0.345 g, 1.86 mmol, 0.2 eq) and 1,2-dimethylethylenediamine (0.319 g, 3.632 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 100a (0.6 g, 34.74%). MS(ES): m/z 191.20 [M+H]$^+$.

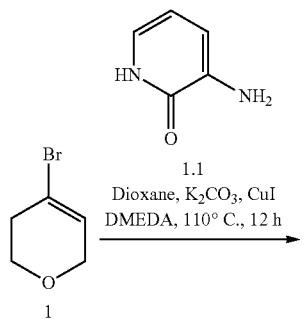

Synthesis of Compound 1.2.

To a solution of 1 (0.9 g, 8.18 mmol, 1.0 eq) in 1,4-dioxane (100 mL), 1.1 (2.0 g, 12.27 mmol, 1.5 eq) was added. The reaction mixture was degassed for 10 min under argon atmosphere followed by addition of potassium carbonate (2.26 g, 16.36 mmol, 2.0 eq), N,N-dimethylethylenediamine (0.287 g, 3.27 mmol, 0.4 eq), and copper iodide (0.31 g, 1.63 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 1.2 (1.2 g, Yield: 76.33%). MS (ES): m/z 193.22 [M+H]$^+$ Synthesis of Compound 100b.

To a solution of 1.2 (1.2 g, 6.24 mmol, 1.0 eq) in methanol (10 mL), palladium on charcoal (0.1 g) was added. Hydrogen was purged through reaction mixture for 24 h at room temperature. After completion of reaction, reaction mixture was filtered through celite-bed and washed with methanol. Filtrate was concentrated under reduced pressure to obtain 100b (0.96 g, 79.17%). MS(ES): m/z 195.23 [M+H]$^+$.

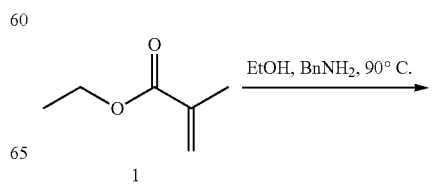

1483
-continued

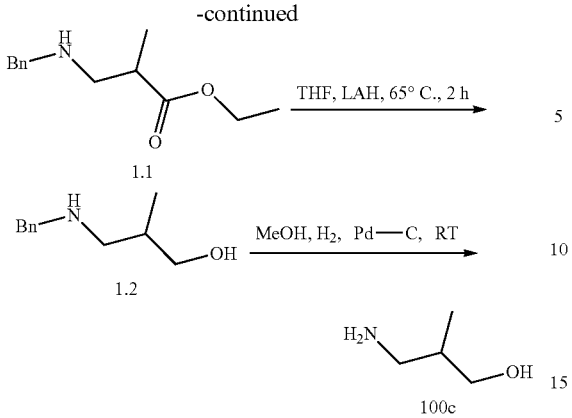

Synthesis of Compound 1.1.

To a solution of 1. (5 g, 43.85 mmol, 1.0 eq) in ethanol (10 mL), Benzyl amine (6.56 g, 61.39 mmol, 1.4 eq) was added. The reaction mixture was heated at 90° C. for 4 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.1. (2 g, 20.63%), MS (ES): m/z 222.14 [M+H]+

Synthesis of Compound 1.2.

To a solution of 1.1. (1.5 g, 6.78 mmol, 1.0 eq) in tetrahydrofuran (75 ml), Lithium aluminium hydride (1M in tetrahydrofuran) (20 mL, 20.34 mmol, 3.0 eq) was added dropwise at 0° C. The reaction mixture was heated at 65° C. for 2 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by 5% methanol in dichloromethane to obtain 1.2. (1.2 g, Yield: 98.76%). MS (ES): m/z 180.13 [M+H]+

Synthesis of Compound 100c.

To a solution of 1.2 (0.5 g, 2.78 mmol, 1.0 eq) in methanol (10 ml), palladium on charcoal (0.25 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 100c. (0.3 g, 96.53%). MS (ES): m/z 90.01 [M+H]+

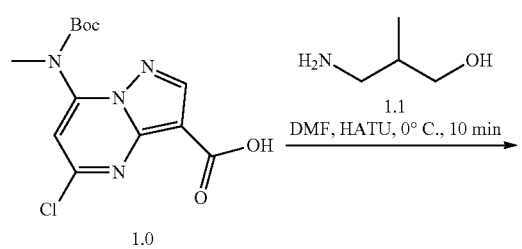

1484
-continued

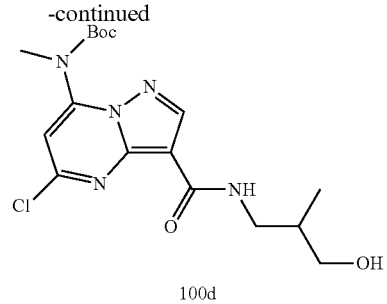

100d

Synthesis of Compound 1.0.

Compound was synthesized using general procedure of core synthesis to obtain 1.0 (Yield: 71.67%).

Synthesis of Compound 100d.

Compound was synthesized using general procedure A to obtain 100d (1.2 g, 49.27%). MS(ES): m/z 398.8 [M+H]+.

Example 101: Syntheses of compounds comprising N-(3-hydroxy-2,2-dimethylpropyl)aminocarbonyl at position 3 of the pyrazolo[1,5-a]pyrimidine 101.1. Synthesis of N-(3-hydroxy-2,2-dimethylpropyl)-7-(methylamino)-5-((2-oxo-2H-[1,2'-bipyridin]-3-yl)amino)pyrazolo[1,5-a]pyrimidine-3-carboxamide (I-683)

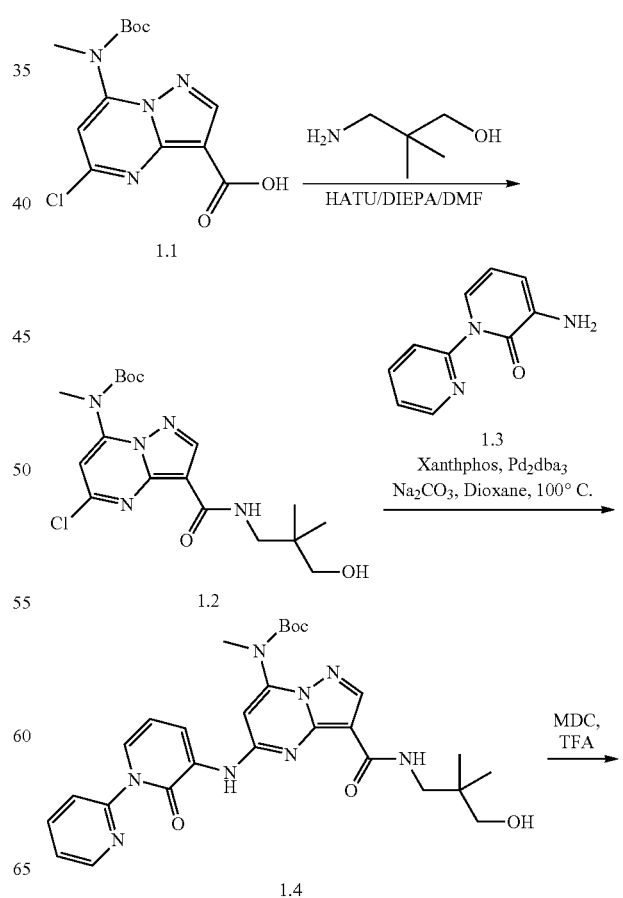

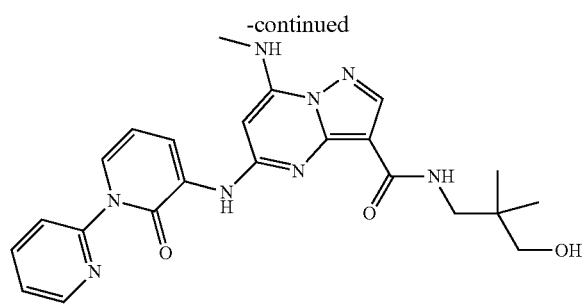

Synthesis of Compound 1.1.

Compound was synthesized using general procedure of core synthesis to obtain 1.1. 13.2 g, 71.67%). ¹H NMR (DMSO-d6, 400 MHZ): 12.63 (s, 1H), 8.63 (s, 1H), 7.55 (s, 1H), 3.31 (s, 3H), 1.29 (s, 9H).

Synthesis of Compound 1.2.

Compound was synthesized using general procedure A to obtain 1.2. (0.15 g, Yield: 59.80%). MS (ES): m/z 412.88 [M+H]⁺

Synthesis of Compound 1.4.

Compound was synthesized using general procedure B to obtain 1.4. (0.07 g, Yield: 51.25%). MS (ES): m/z 563.63 [M+H]⁺

Synthesis of Compound I-683. Compound was synthesized using general procedure C to obtain I-683 (0.041 g, 88.65%). MS(ES): m/z 463.50 [M+H]⁺ LCMS purity: 98.74%, HPLC purity: 98.50%, ¹H NMR (DMSO-d$_6$, 400 MHZ): 8.97 (s, 1H), 8.65-8.64 (d, J=3.6 Hz, 1H), 8.29-8.28 (d, J=6.4 Hz, 1H), 8.23 (s, 1H), 8.06-8.03 (t, J=7.2 Hz, 1H), 7.96 (bs, 1H), 7.87-7.83 (t, J=9.2 Hz, 2H), 7.57-7.53 (m, 2H), 6.50-6.46 (t, J=7.2 Hz, 1H), 6.25 (s, 1H), 4.71 (bs, 1H), 3.28-3.27 (d, J=6 Hz,2H), 3.12 (s, 2H), 2.91 (s, 3H), 0.84 (bs, 6H).

Additional compounds prepared by substantially the same method, and their characterization data, are listed in the Table 40 below. The intermediate corresponding to 1.3 of the scheme above is listed for each compound.

TABLE 40

| Compound | Intermediate | Characterization data |
|---|---|---|
| I-245 | (1-(4-fluorophenyl)-3-amino-2-oxopyridine structure) | MS (ES): m/z 480.26 [M + H]⁺, LCMS purity: 100%, HPLC purity: 99.70%, ¹H NMR (DMSO-d$_6$, 400 MHZ): 8.94 (s, 1H), 8.29-8.28 (d, J = 4 Hz, 1H), 8.24 (s, 1H), 7.97-7.96 (d, J = 4 Hz, 1H), 7.89-7.87 (t, J = 8 Hz, 1H), 7.57-7.54 (m, 2H), 7.42-7.40 (t, J = 8 Hz, 2H), 7.35-7.33 (d, J = 8 Hz, 1H), 6.46-6.44 (t, J = 8 Hz, 1H), 6.25 (s, 1H), 4.70-4.69 (t, J = 4 Hz, 1H), 3.29-3.27 (d, J = 8 Hz, 2H), 3.14-3.12 (d, J = 8 Hz, 2H), 2.92-2.91 (d, J = 4 Hz, 3H), 0.86 (s, 6H). |
| I-270 | (2-methoxy-5-methyl-3-aminopyridine structure) | MS(ES): m/z 414.48[M + H]⁺, LCMS purity: 95.06%, HPLC purity: 98.72%, ¹H NMR (DMSO-d$_6$, 400 MHZ): 8.85 (s, 1H), 8.17 (s, 1H), 8.01-7.92 (m, 3H), 7.72 (s, 1H), 5.86 (s, 1H), 4.59-4.56 (m, 1H), 3.90 (s, 3H), 3.18-3.13 (m, 2H), 2.98-2.90 (m, 5H), 2.27 (s, 3H), 0.61 (s, 6H). |
| I-283 | (2-methoxy-5-fluoro-3-aminopyridine structure) | MS (ES): m/z 418.45 [M + H]⁺, LCMS purity: 100%, HPLC purity: 98.74%, ¹H NMR (DMSO-d$_6$, 400 MHZ): 9.07 (s, 1H), 8.33-8.31 (d, J = 8 Hz, 1H), 8.22 (s, 1H), 8.03-8.02 (d, J = 4 Hz, 1H), 7.90-7.89 (t, J = 4 Hz, 1H), 7.83-7.82 (t, J = 4 Hz, 1H), 6.05 (s, 1H), 4.62-4.60 (t, J = 8 Hz, 1H), 3.96 (s, 3H), 3.17-3.16 (d, J = 4 Hz, 2H), 3.03-3.02 (d, J = 4 Hz, 2H), 2.93-2.91 (d, J = 8 Hz, 3H), 0.71 (s, 6H) |
| I-346 | (2-methoxy-3-aminopyridine structure) | MS (ES): m/z 400.46 [M + H]⁺, LCMS purity: 99.62%, HPLC purity: 99.44%, CHIRAL HPLC: 100%, ¹H NMR (DMSO-d$_6$, 400 MHZ): 8.89 (s, 1H), 8.24-8.22 (d, J = 6.8 Hz, 1H), 8.17 (s, 1H), 7.93-7.86 (m, 3H), 7.04-7.01 (m, 1H), 5.91 (s, 1H), 4.64-4.61 (m, 1H), 3.94 (s, 3H), 3.17-3.16 (d, J = 5.2 Hz, 2H), 3.14-3.12 (d, J = 6.4 Hz, 2H), 2.91-2.90 (d, J = 4.8 Hz, 3H), 0.70 (s, 6H). |
| I-347 | (2-OCD₃-3-aminopyridine structure) | MS (ES): m/z 403.47 [M + H]⁺, LCMS purity: 100%, HPLC purity: 99.74%, ¹H NMR (DMSO-d$_6$, 400 MHZ): 8.90 (s, 1H), 8.25-8.23 (d, J = 7.6 Hz, 1H), 8.18 (s, 1H), 7.94-7.87 (m, 3H), 7.05-7.01 (m, 1H), 5.92 (s, 1H), 4.65-4.61 (t, J = 6.0 Hz, 1H), 3.15-3.13 (d, J = 6.4 Hz, 2H), 3.03-3.02 (d, J = 6 Hz, 2H), 2.92-2.91 (d, J = 3 Hz, 3H), 0.71 (s, 6H). |

TABLE 40-continued

| Compound | Intermediate | Characterization data |
|---|---|---|
| I-350 | 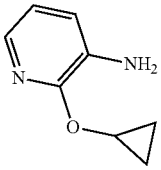 [SMILES: Nc1cccnc1OC1CC1] | MS (ES): m/z 426.49 [M + H]+, LCMS purity: 97.81%, HPLC purity: 96.78%, 1H NMR (DMSO-d6, 400 MHZ): 8.69 (s, 1H), 8.22-8.20 (d, J = 6.4 Hz, 1H), 8.17 (s, 1H), 7.93-7.92 (t, J = 4.8 Hz, 2H), 7.87-7.84 (t, J = 6.4 Hz, 1H), 7.06-7.03 (m, 1H), 5.86 (s, 1H), 4.63-4.60 (t, J = 12.4 Hz, 1H), 4.34-4.31 (m, 1H), 3.13-3.12 (d, J = 6.4 Hz, 2H), 3.02-3.01 (d, J = 6 Hz, 2H), 2.92-2.91 (d, J = 4.8 Hz, 3H), 0.85-0.73 (m, 10H). |
| I-355 | 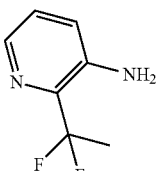 | MS (ES): m/z 434.39 [M + H]+, LCMS purity: 100%, HPLC purity: 100%, 1H NMR (DMSO-d6, 400 MHZ): 8.83 (s, 1H), 8.47-8.46 (d, J = 4.4 Hz, 1H), 8.14 (s, 1H), 8.12(s, 1H), 7.95(bs, 1H), 7.74-7.71 (t, J = 6.4 Hz, 1H), 7.62-7.59 (m, 1H), 5.85 (s, 1H), 4.53 (s, 1H), 2.96-2.89 (m, 6H), 2.06-1.96 (m, 4H), 0.50 (s, 6H). |
| I-509 | 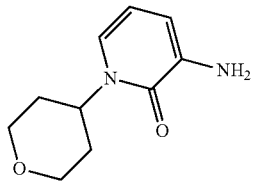 [SMILES: Nc1cccn(C2CCOCC2)c1=O] | MS (ES): m/z 470.56 [M + H]+, LCMS purity: 97.65%, HPLC purity: 96.50%, 1H NMR (DMSO-d6, 400 MHZ): 8.84 (s, 1H), 8.21 (s, 1H), 8.17-8.15 (d, J = 7.2 Hz, 1H), 7.92-7.91 (d, J = 4 Hz, 1H), 7.84 (bs, 1H), 7.46-7.45 (d, J = 6.4 Hz, 1H), 6.37 (bs, 1H), 6.22 (s, 1H), 5.03 (bs, 1H), 4.67 (bs, 1H), 4.01-3.99 (m, 2H), 3.53-3.48 (d, J = 11.2 Hz, 2H), 3.25-3.24 (d, J = 5.6 Hz, 3H), 3.10-3.09 (d, J = 5.2 Hz, 3H), 2.91-2.90 (d, , J = 3.6 Hz, 3H), 1.75 (bs, 2H), 0.82 (s, 6H). |
| I-510 | 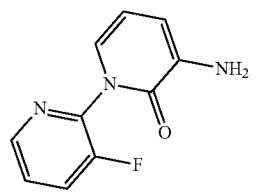 [SMILES: Nc1cccn(-c2ncccc2F)c1=O] | MS(ES): m/z 481.50 [M + H]+ LCMS purity: 95.17%, HPLC purity: 95.5%, NMR (DMSO-d6, 400 MHZ): 8.99 (s, 1H), 8.51-8.50 (d, J = 4.8 Hz, 1H), 8.32-8.30 (d, J = 7.6 Hz, 1H), 8.24 (s, 1H), 8.08-8.04 (t, J = 8.4 Hz, 1H), 7.97-7.96 (d, J = 4.4. Hz, 1H), 7.88-7.85 (t, J = 5.2 Hz, 1H), 7.74-7.70 (m, 1H), 7.43-7.42 (d, J = 6.8 Hz, 1H), 6.52 (t, J = 7.2 Hz, 1H). 6.23 (s, 1H), 4.70-4.67 (t, J = 6 Hz, 1H), 3.29-3.27 (d, J = 7.6 Hz, 2H), 3.13-3.11 (d, J = 6 Hz, 2H), 2.91-2.90 (d, J = 4.8 Hz, 3H), 0.84 (bs, 6H). |
| I-529 | 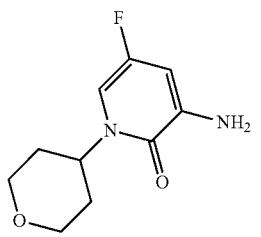 [SMILES: Nc1cc(F)cn(C2CCOCC2)c1=O] | MS (ES): m/z 488.31 [M + H]+, LCMS purity: 97.04%, HPLC purity: 94.24%, 1H NMR (DMSO-d6, 400 MHZ): 9.10 (s, 1H), 8.27 (s, 2H), 8.05-8.03 (d, J = 5.2 Hz, 1H), 7.89-7.087 (m, 1H), 7.66 (bs, 1H), 6.35 (s, 1H), 4.03-4.00 (d, J = 12 Hz, 3H), 3.58-3.51 (t, J = 12 Hz, 3H), 3.32 (s, 2H), 3.25-3.23 (d, J = 6.4 Hz, 2H), 3.10-3.09 (d, J = 5.6 Hz, 2H), 2.93-2.92(d, J = 4.4 Hz, 3H), 1.80-1.73 (m, 2H), 0.81 (s, 6H). |
| I-542 | 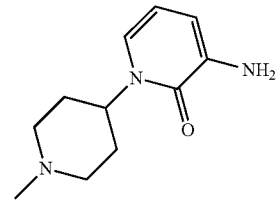 | MS (ES): m/z 483.41 [M + H]+, LCMS purity: 99.25%, HPLC purity: 96.86%, 1H NMR (DMSO-d6, 400 MHZ): 8.84 (s, 1H), 8.27-8.21 (s, 1H), 8.17-8.15 (d, J = 6.8 Hz, 1H), 7.93 (bs, 2H), 7.71 (bs, 1H), 7.41-7.42 (d, J = 4.8 Hz, 2H), 7.09 (bs, 1H), 6.83 (bs, 1H), 6.37-6.36 (d, J = 6.8 Hz, 1H), 6.22 (s, 1H), 4.76 (bs, 1H), 4.69-4.68 (d, J = 5.6 Hz, 1H), 4.13 (bs, 1H), 3.98 (bs, 1H), 3.50 (s, 1H), 3.25-3.24 (d, J = 6 Hz, 2H), 3.10-3.09 (d, J = 6 Hz, 2H), 2.91-2.90 (d, J = 4.4 Hz, 4H), 0.81(s, 9H). |

TABLE 40-continued

| Compound | Intermediate | Characterization data |
|---|---|---|
| I-544 | (3-amino-1-(4-methoxycyclohexyl)pyridin-2(1H)-one structure) | MS(ES): m/z 498.75 [M + H]$^+$ LCMS purity: 100%, HPLC purity: 98.82%, NMR (DMSO-d$_6$, 400 MHZ): 9.83 (s, 1H), 8.21 (s, 1H), 8.15-8.13 (d, J = 6.8 Hz, 1H), 7.92 (s, 1H), 7.84 (s, 1H), 7.40-7.39 (d, J = 6.4 Hz, 1H), 6.36-6.35 (d, J = 6 Hz, 1H), 6.21 (s, 1H), 4.78 (s, 1H), 4.67 (s, 1H), 3.34-3.23 (m, J = 10.8 Hz, 5H), 3.10-3.09 (d, J = 5.2 Hz, 2H), 2.91-2.90 (d, J = 3.6 Hz, 3H), 2.15-2.13(d, J = 9.2 Hz, 2H), 1.79(s, 4H). 1.3-1.23 (m, 3H), 0.81(s, 6H). |
| I-571 | (3-amino-1-(tetrahydropyran-3-yl)pyridin-2(1H)-one structure) | MS(ES): m/z 470.55 [M + H]$^+$ LCMS purity: 100%, HPLC purity: 98.82%, Chiral HPLC purity: 49.50%, 49.99%, NMR (DMSO-d$_6$, 400 MHZ): 8.91 (s, 1H), 8.23 (s, 1H), 8.17-8.15 (d, J = 7.2 Hz, 1H), 7.96 (s, 1H), 7.85 (s, 1H), 7.50-7.49 (d, J = 6.8 Hz, 1H), 6.38-6.35 (t, J = 7.2 Hz, 1H), 6.22 (s, 1H), 4.87 (s, 1H), 3.84-3.82 (d, J = 10 Hz, 2H), 3.59-3.3.43 (m, 4H), 3.25-3.24 (m, 2H), 3.10 (s, 2H), 2.91-2.90 (m, 3H), 2.06-1.1.95 (m, 1H), 1.76-1.72 (m, 1H), 1.27-1.17 (m, 1H), 0.86 (s, 6H). |
| I-579 | (6-amino-2-(tetrahydropyran-3-yl)pyridine structure) | MS (ES): m/z 454.40 [M + H]$^+$ LCMS purity: 96.55%, HPLC purity: 96.35%, CHIRAL HPLC purity: 100% MS (ES): m/z 454.55 [M + H]$^+$, $^1$H NMR (DMSO-d$_6$, 400 MHZ): 9.81 (s, 1H), 8.23 (s, 1H), 8.08-8.02 (m, 2H), 7.71-7.69 (t, J = 8.0 Hz, 1H), 7.51-7.49 (d, J = 8.0 Hz, 1H), 6.95-6.93(d, J = 8.0 Hz, 1H), 6.72 (s, 1H), 4.70 (s, 1H), 4.02-3.88 (m, 2H), 3.54-3.49 (t, J = 8.0 Hz, 1H), 3.24-3.23, (d, J = 4.0 Hz, 2H), 3.12-3.10, (d, J = 8.0 Hz, 2H), 2.98-2.88 (m, 4H), 2.01-1.85 (m, 2H), 1.67 (bs, 1H), 1.23 (bs, 1H), 1.19-1.11 (m, 1H) 0.83 (s, 6H). |
| I-580 | (6-amino-2-(tetrahydropyran-3-yl)pyridine structure, enantiomer) | MS (ES): m/z 454.40 [M + H]$^+$ LCMS purity: 100%, HPLC purity: 95.18%, CHIRAL HPLC purity: 97.62%, $^1$H NMR (DMSO-d$_6$, 400 MHZ): 9.81 (s, 1H) 8.23 (s, 1H), 8.08-8.02 (m, 2H), 7.71-7.69 (t, J = 8.0 Hz, 1H), 7.51-7.49 (d, J = 8.0 Hz, 1H), 6.95-6.93(d, J = 8.0 Hz, 1H), 6.72 (s, 1H), 4.70 (s, 1H), 4.02-3.88 (m, 2H), 3.54-3.49 (t, J = 8.0 Hz, 1H), 3.24-3.23 (d, J = 4.0 Hz, 2H), 3.12-3.10 (d, J = 8.0 Hz, 2H), 2.98-2.88 (m, 4H), 2.01-1.85 (m, 2H), 1.67 (bs, 1H), 1.23 (bs, 1H), 1.19-1.11 (m, 1H) 0.83 (s, 6H). |
| I-694 | (3-amino-5-chloro-1-(tetrahydropyran-4-yl)pyridin-2(1H)-one structure) | MS (ES): m/z 504.33 [M + H]$^+$, LCMS purity: 98.86%, HPLC purity: 97.86%, $^1$H NMR (DMSO-d$_6$, 400 MHZ): 9.09 (s, 1H), 8.27 (s, 1H), 8.24-8.23 (d, J = 2 Hz, 1H), 8.05-8.04 (d, J = 4.8 Hz, 1H), 7.94-7.91 (t, J = 6.4 Hz, 1H), 7.67 (bs, 1H), 6.33 (s, 1H), 4.97 (bs, 1H), 4.62 (bs, 1H), 4.02-3.99 (m, 2H), 3.53-3.47 (t, J = 11.2 Hz, 2H), 3.35 (s, 1H), 3.32-3.30 (d, J = 6.8 Hz , 1H), 3.09 (bs, 2H), 2.93-2.92 (d, J = 4.8 Hz, 3H), 2.07-1.99 (m, 2H), 1.76 (bs, 2H), 0.79 (s, 6H). |
| I-750 | (4-aminobenzoxazole structure) | MS (ES): 410.37 [M + H]$^+$ LCMS purity: 97.60%, HPLC purity: 94.90%, $^1$H NMR (DMSO-d$_6$, 400 MHZ): 9.70 (s, 1H), 8.76 (s, 1H), 8.19 (s, 1H), 7.98-7.89 (m, 3H), 7.48-7.43 (m, 2H), 6.01 (s, 1H), 4.62-4.61 (t, J = 6 Hz, 1H), 3.12-3.10 (d, J = 6.4 Hz, 2H), 2.99-2.98 (d, J = 6 Hz, 2H), 2.93-2.92 (d, J = 4.8 Hz, 3H), 0.64 (bs, 6H). |

TABLE 40-continued

| Compound | Intermediate | Characterization data |
|---|---|---|
| I-767 | 1.3 | MS (ES): m/z 477.6[M + H]⁺, LCMS purity: 100%, HPLC purity: 99.32, $^1$H NMR (DMSO-d$_6$, 400 MHZ): 9.96 (s, 1H), 8.57-8.56 (d, J = 2.4 Hz, 1H), 8.31-8.29 (d, J = 7.2 Hz, 1H), 8.23 (s, 1H), 7.97-7.95 (d, J = 4.8 Hz, 1H), 7.87-7.84 (m, 2H), 7.46-7.44 (d, J = 8 Hz, 1H), 7.38-7.37 (d, J = 5.6 Hz, 1H), 6.48-6.44 (t, 1H), 6.26 (s, 1H), 4.71-4.68 (t, 1H), 3.28-3.27 (d, J = 6.8 Hz, 2H), 3.13-3.12 (d, J = 6 Hz, 2H), 2.91-2.89 (d, J = 4.8 Hz, 3H), 2.56 (s, 3H), 0.85 (s, 6H). |
| I-847 | | MS (ES): m/z 515.48 [M + H]⁺, LCMS purity: 98.47%, HPLC purity: 97.46%, $^1$H NMR (DMSO-d$_6$, 400 MHZ): 8.86 (s, 1H), 8.23 (s, 1H), 8.18-8.16 (d, J = 6.0 Hz, 1H), 7.95-7.93 (d, J = 5.2 Hz, 1H), 7.87-7.84 (t, J = 6.4 Hz, 1H), 7.48-7.46 (d, J = 6.4 Hz, 1H), 6.38-6.35 (m, 1H), 6.23 (s, 1H), 4.83-4.77 (m, 1H), 4.71-4.53 (m, 2H), 4.51 (s, 1H), 3.27-3.25 (d, J = 6.0 Hz, 2H), 3.12-3.06 (m, 3H), 2.93-2.91 (d, J = 4.8 Hz, 3H), 2.73-2.66 (m, 2H), 2.26-2.20 (m, 2H), 2.02-1.90 (m, 3H), 1.78-1.76 (m, 2H), 0.83 (s, 6H). |
| I-850 | | MS (ES): m/z 477.42 [M + H]⁺, LCMS purity: 95.72%, HPLC purity: 97.48%, CHIRAL HPLC purity: 49.46%, 49.85%, $^1$H NMR (DMSO-d$_6$, 400 MHZ): 8.95 (s, 1H), 8.48-8.47 (d, J = 3.6 Hz, 1H), 8.34-8.32 (d, J = 5.6 Hz, 1H), 8.25 (s, 1H), 7.55-7.51 (m, 1H), 7.31-70.29 (m, 1H), 6.50-6.46 (t, J = 7.2 Hz, 1H), 6.25 (s, 1H), 3.51-3.50 (d, J = 4.4 Hz, 2H), 3.30-3.28 (d, J = 6.8 Hz, 2H), 3.13 (s, 2H), 2.92-2.91 (d, J = 4.4 Hz, 3H), 2.14 (s, 3H), 1.27 (s, 2H), 0.85 (s, 6H). |
| I-861 | | MS (ES): m/z 498.42 [M + H]⁺, LCMS purity: 97.91%, HPLC purity: 97.61%, CHIRAL HPLC purity: 46.12%, 51.19%. , $^1$H NMR (DMSO-d$_6$, 400 MHZ): 8.84 (s, 1H), 8.22 (s, 1H), 8.17-8.15 (d, J = 8.0 Hz, 1H), 7.95-7.84 (m, 2H), 7.47-7.45 (d, J = 8.0 Hz, 1H), 6.38-6.35 (m, 1H), 6.22 (s, 1H), 4.83-4.69 (m, 1H), 3.27-3.25 (m, 5H), 3.25 (s, 1H), 3.11 (s, 2H), 2.92-2.91 (d, J = 4.0 Hz, 3H), 2.17-2.15 (m, 1H), 2.06-2.03 (m, 2H), 1.87-1.84 (m, 1H), 1.72 (s, 1H), 1.63-1.55 (m, 2H), 1.42-1.35 (m, 1H), 1.19-1.14 (m, 1H), 0.82 (bs, 6H). |
| I-958 | | MS (ES): 498.42 [M + H]⁺ LCMS purity: 98.78%, HPLC purity: 98.04%, CHIRAL HPLC: 49.93%, 49.38%, $^1$H NMR (DMSO-d$_6$, 400 MHZ): 8.87 (s, 1H), 8.22 (s, 1H), 8.16-8.14 (d, J = 6 Hz, 1H), 7.94-7.93 (d, J = 4.8 Hz, 1H), 7.88-7.85 (t, J = 6.4 Hz, 1H), 7.44-7.43 (d, J = 6 Hz, 1H), 6.38-6.34 (t, J = 7.2 Hz, 1H), 6.22 (s, 1H), 3.71 (bs, 1H), 3.58 (s, 3H), 3.29 (s, 3H), 3.26-3.25 (d, J = 6.8 Hz, 2H), 3.11 (s, 2H), 2.92-2.91 (d, J = 4.8 Hz, 3H), 2.02 (bs, 2H), 1.36 (bs, 2H), 1.24 (bs, 3H), 0.83 (s, 6H). |
| I-990 | | MS (ES): m/z 498.57 [M + H]⁺, LCMS purity: 100%, HPLC purity: 100%, CHIRAL HPLC: 100%, $^1$H NMR (DMSO-d$_6$, 400 MHZ): 8.84 (s, 1H), 8.22 (s, 1H), 8.19-8.18 (d, J = 6.8 Hz, 1H), 7.94-7.93 (d, J = 4.4 Hz, 1H), 7.89 (s, 1H), 7.36-7.35 (d, J = 6.8 Hz, 1H), 6.35-6.31 (t, J = 6.8 Hz, 1H), 6.21 (s, 1H), 4.90-4.87 (d, J = 12.4 Hz, 1H), 4.69 (bs, 1H), 3.57 (bs, 1H), 3.26-3.25 (d, J = 5.6 Hz, 2H), 3.11 (bs, 5H), 2.93-2.92 (d, J = 3.6 Hz, 3H), 2.10 (bs, 2H), 1.86 (bs, 1H), 1.57-1.55 (d, J = 10 Hz, 1H), 1.47 (bs, 4H), 0.83 (bs, 6H). |

TABLE 40-continued

| Compound | Intermediate | Characterization data |
| --- | --- | --- |
| I-1046 | | MS (ES): m/z 498.60 [M + H]+, LCMS purity: 100%, HPLC purity: 100%, CHIRAL HPLC purity: 100%, 1H NMR (DMSO-d6, 400 MHZ): 8.84 (s, 1H), 8.22-8.18 (m, 2H), 7.94-7.89 (m, 2H), 7.36-7.35 (d, J = 6.8 Hz 1H), 6.35-6.33 (m, 1H), 6.21 (s, 1H), 4.90-4.87 (m, 1H), 4.69 (s, 1H), 3.57 (s, 1H), 3.26-3.25 (d, J = 6.4 Hz, 2H), 3.18 (bs, 5H), 2.93-2.92 (d, J = 4 Hz, 3H), 2.10 (bs, 2H), 1.86 (bs, 1H), 1.57 (bs, 1H), 1.47 (bs, 4H), 0.83 (s, 6H). |
| I-1060 | | MS (ES): m/z 444.45 [M + H]+, LCMS purity: 100%, HPLC purity: 99.84%, CHIRAL HPLC Purity: 100%, $^1$H NMR (DMSO-d$_6$, 400 MHZ): 8.92 (s, 1H), 8.22 (s, 1H), 8.17-8.16 (d, J = 7.2 Hz, 1H), 7.95-7.94 (d, J = 4.8 Hz, 1H), 7.84-7.80 (t, J = 6 Hz, 1H), 7.16-7.15 (d, J = 6.8 Hz, 1H), 6.32-6.28 (t, J = 7.2 Hz, 1H), 6.24 (s, 1H), 4.68 (bs, 1H), 3.89-3.81 (m, 1H), 3.25-3.24 (d, J = 5.6 Hz, 2H), 3.10-3.08 (d, J = 5.6 Hz, 2H), 2.91-2.90 (d, J = 4.8 Hz, 3H), 1.22 (bs, 3H), 0.81 (s, 6H). |

101.2. Synthesis of N-(3-hydroxy-2,2-dimethylpropyl)-5-(1-isopropyl-1H-pyrrolo[2,3-b]pyridin-3-yl)-7-(methylamino)pyrazolo[1,5-a]pyrimidine-3-carboxamide (I-588)

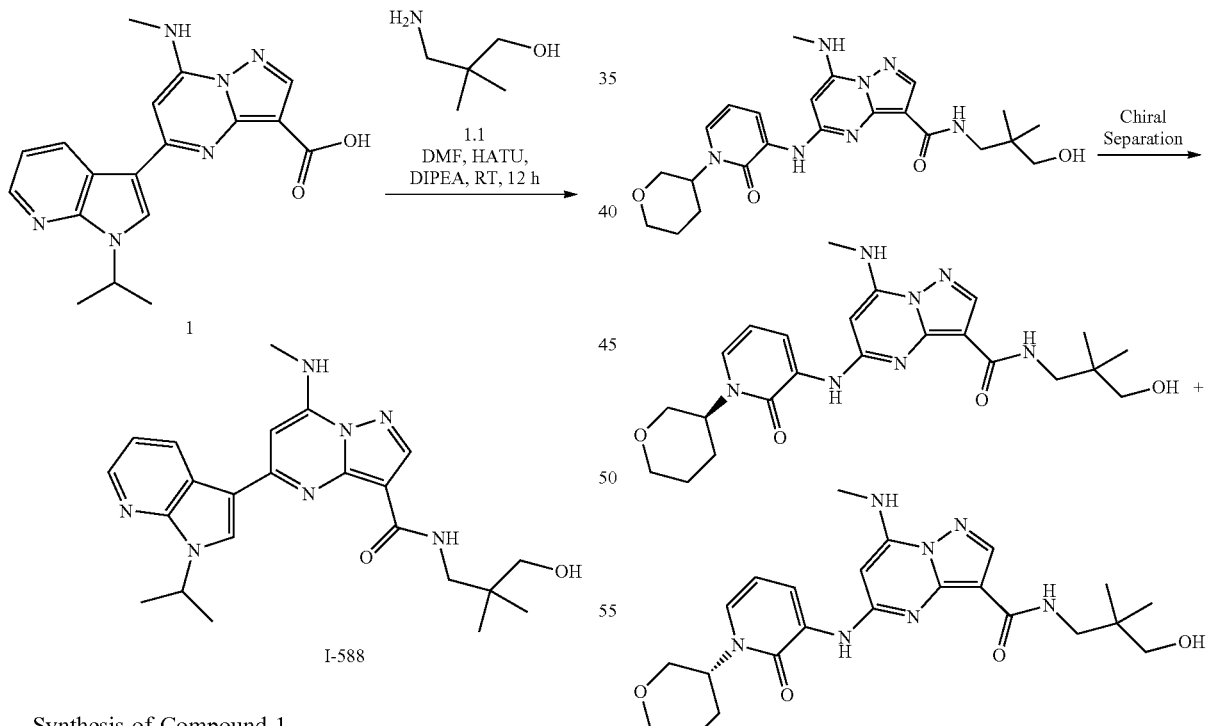

Synthesis of Compound 1.
Compound was synthesized as per experimental protocol of I-653 to obtain 1.

Synthesis of Compound I-588.
Compound was synthesized using general procedure A to obtain I-588. (Yield: 32.18%). MS (ES): m/z 436.53 [M+H]+, LCMS purity: 97.90%, HPLC purity: 97.86%, $^1$H NMR (DMSO-d$_6$, 400 MHZ): 8.76 (s, 1H), 8.67-8.65 (d, J=7.6 Hz, 1H), 8.37 (s, 1H), 8.27 (s, 1H), 7.32-7.31 (d, J=4.4 Hz, 1H), 7.20 (s, 1H), 6.75 (m, 2H), 5.21 (s, 1H), 4.73 (s, 1H), 3.18-3.12 (m, 4H), 2.67 (s, 3H), 1.58-1.57 (d, J=6.8 Hz, 6H), 0.88 (bs, 6H).

101.3. Chiral Separation of I-571

Synthesis of Compound I-598 & I-599.
Isomers of I-571 (0.120 g) were separated out using column (CHIRAL PAK AD-H 250×4.6 mm, 5 u) and 0.1% DEA in methanol and isopropyl alcohol as co-solvent with flow rate of 4 mL/min. to get pure fraction-1 (FR-a) and fraction-2 (FR-b). FR-a was concentrated under reduced pressure at 30° C. to afford one pure isomer (0.040 g). MS(ES): m/z 470.55 [M+H]⁺ LCMS purity: 98.45%, HPLC purity: 98.5%, Chiral HPLC purity: 99.08%, NMR (DMSO-d₆, 400 MHZ): 8.87 (s, 1H), 8.21 (s, 1H), 8.18-8.16 (d, J=6.8 Hz, 1H), 7.93-7.92 (d, J=4.8 Hz, 1H), 7.85-7.82 (t, J=6.4 Hz, 1H), 7.49-7.48 (d, J=6 Hz, 1H), 6.38-6.35 (t, J=7.2 Hz, 1H), 6.23 (s, 1H), 4.87-4.84 (d, J=10 Hz, 1H), 4.69-4.66 (t, J=6 Hz, 1H), 3.49-3.43 (m, 2H), 3.38-3.77 (m, 2H), 3.25-3.24 (d, J=6.8 Hz, 2H), 3.10-3.09 (d, J=6 Hz, 2H), 2.91-2.90 (d, J=4.4 Hz, 3H), 2.06-1.1.95 (m, 1H), 1.76-1.72 (m, 1H), 1.04-1.01 (m, 2H), 0.82 (bs, 6H).

FR-b was concentrated under reduced pressure at 30° C. to afford the other pure isomer (0.042 g). MS(ES): m/z 470.55 [M+H]⁺ LCMS purity: 100%, HPLC purity: 99.48%, Chiral HPLC purity: 99.39%, NMR (DMSO-d₆, 400 MHZ): 8.87 (s, 1H), 8.22 (s, 1H), 8.19-8.177 (d, J=6.8 Hz, 1H), 7.94-7.93 (d, J=4 Hz, 1H), 7.86-7.83 (t, J=6 Hz, 1H), 7.51-7.49 (d, J=6.8 Hz, 1H), 6.39-6.36 (t, J=7.2 Hz, 1H), 6.24 (s, 1H), 4.90-4.85 (t, J=10 Hz, 1H), 4.69 (s, 1H), 3.60-3.55 (t, J=10 Hz, 1H), 3.49-3.44 (t, J=10.4 Hz, 2H), 3.26-3.25 (d, J=6.4 Hz, 2H), 3.18 (s, 1H), 3.11-3.10 (d, J=5.2 Hz, 2H), 2.91-2.90 (d, J=4.4 Hz, 3H), 2.07-2.03 (m, 1H), 1.77-1.71 (m, 1H) 1.04-1.01 (m, 2H), 0.83 (bs, 6H).

Additional compounds prepared by substantially the same method, and their characterization data, are listed in the Table 41 below.

2.4. Synthesis of N-(3-hydroxy-2,2-dimethylpropyl)-7-(methylamino)-5-(1-(2-morpholinoethyl)-1H-pyrrolo[2,3-b]pyridin-3-yl)pyrazolo[1,5-a]pyrimidine-3-carboxamide (I-818)

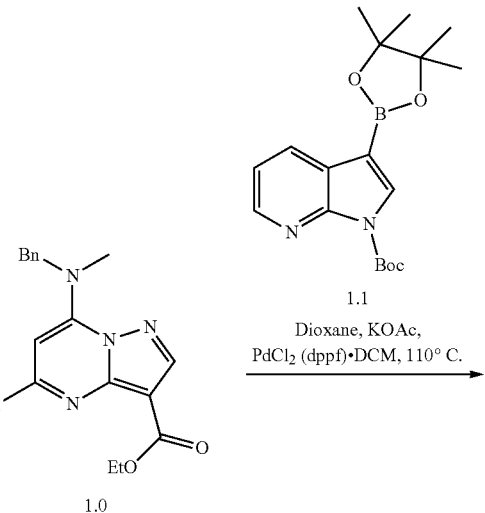

Dioxane, KOAc,
PdCl₂ (dppf)·DCM, 110° C.

TABLE 41

| Compound | Isomers | Characterization data |
| --- | --- | --- |
| I-861 (Chiral separation when methylamino at position 7 is protected by Boc, followed by removal of Boc) | I-950 I-951 | FR-a: MS (ES): m/z 498.57 [M + H]⁺, LCMS purity: 100%, HPLC purity: 98.51%, Chiral HPLC: 99.34%, ¹H NMR (DMSO-d₆, 400 MHZ): 8.85 (s, 1H), 8.25 (s, 1H), 8.17-8.15 (d, J = 8 Hz, 1H), 7.95-7.94 (d, J = 4.6 Hz, 1H), 7.87-7.86 (t, J = 6 Hz, 1H), 7.47-7.46 (d, J = 6 Hz, 1H), 6.39-6.37 (t, J = 7.6 Hz, 1H), 6.22 (s, 1H), 4.86-4.83 (t, J = 12 Hz, 1H), 4.69 (s, 1H), 3.27-3.25 (d, J = 8 Hz, 4H), 3.11 (s, 2H), 2.92-2.91 (d, J = 4.6 Hz, 3H), 2.17-2.15 (d, J = 8 Hz, 1H), 2.06-2.04 (d, J = 8 Hz, 1H), 1.86-1.84 (d, J = 8.6 Hz, 1H), 1.72 (s, 1H), 1.66-1.55 (m, 2H), 1.42-1.39 (t, J = 12.6 Hz, 2H), 1.24-1.11 (m, 2H), 0.82 (s, 6H). FR-b: MS (ES): m/z 498.42 [M + H]⁺, LCMS purity: 97.33%, HPLC purity: 98.61% Chiral HPLC: 100%, ¹H NMR (DMSO-d₆, 400 MHZ): 8.83 (s, 1H), 8.21 (s, 1H), 8.16-8.14 (d, J = 8 Hz, 1H), 7.93-7.92 (d, J = 4.6 Hz, 1H), 7.86-7.85 (t, J = 6 Hz, 1H), 7.83 (s, 1H), 7.46-7.44 (d, J = 6 Hz, 1H), 6.38-6.36 (t, J = 7.6 Hz, 1H), 6.21 (s, 1H), 4.85-4.82 (t, J = 12 Hz, 1H), 4.79 (s, 1H), 3.27-3.25 (d, J = 8 Hz, 4H), 3.10 (s, 2H), 2.91-2.90 (d, J = 4.6 Hz, 3H), 2.17-2.15 (d, J = 8 Hz, 1H), 2.05-2.03 (d, J = 8 Hz, 1H), 1.86-1.84 (d, J = 8.6 Hz, 1H), 1.72 (s, 1H), 1.66-1.55 (m, 2H), 1.41-1.38 (t, J = 12.6 Hz, 2H), 1.24-1.11 (m, 2H), 0.82 (s, 6H). |
| I-958 (Chiral separation when methylamino at position 7 is protected by Boc, followed by removal of Boc) | I-1027 I-1028 | FR-a: MS (ES): m/z 498.47 [M + H]⁺, LCMS purity: 100%, HPLC purity: 99.03%, Chiral HPLC: 100%, ¹H NMR (DMSO-d₆, 400 MHZ): 8.86 (s, 1H), 8.22 (s, 1H), 8.16-8.15 (d, J = 6.4 Hz, 1H), 7.94-7.93 (d, J = 4.8 Hz, 1H), 7.88-7.85 (m, 1H), 7.44-7.43 (d, J = 6.4 Hz, 1H), 6.38-6.35 (t, J = 7.2 Hz, 1H), 6.23 (s, 1H), 4.68 (s, 1H), 3.71 (bs, 1H), 3.58 (s, 1H), 3.32-3.25 (m, 5H), 3.11 (s, 2H), 2.93-2.91 (d, J = 4.8 Hz, 3H), 2.05-2.02 (m, 1H), 1.91-1.64 (m, 6H), 1.41-1.35 (m, 1H), 0.83 (s, 6H). FR-b: MS (ES): m/z 498.52 [M + H]⁺, LCMS purity: 100%, HPLC purity: 99.51%, Chiral HPLC: 99.42%, ¹H NMR (DMSO-d₆, 400 MHZ): 8.86 (s, 1H), 8.22 (s, 1H), 8.16-8.15 (d, J = 6.8 Hz, 1H), 7.94-7.93 (d, J = 4.8 Hz, 1H), 7.88-7.85 (m, 1H), 7.44-7.43 (d, J = 6.4 Hz, 1H), 6.38-6.35 (t, J = 7.2 Hz, 1H), 6.23 (s, 1H), 4.69 (s, 1H), 3.71 (bs, 1H), 3.58 (s, 1H), 3.30-3.25 (m, 5H), 3.12-3.11 (d, J = 5.2 Hz, 2H), 2.93-2.91 (d, J = 4.4 Hz, 3H), 2.05-2.02 (m, 1H), 1.91-1.64 (m, 6H), 1.41-1.35 (m, 1H), 0.83 (s, 6H). |

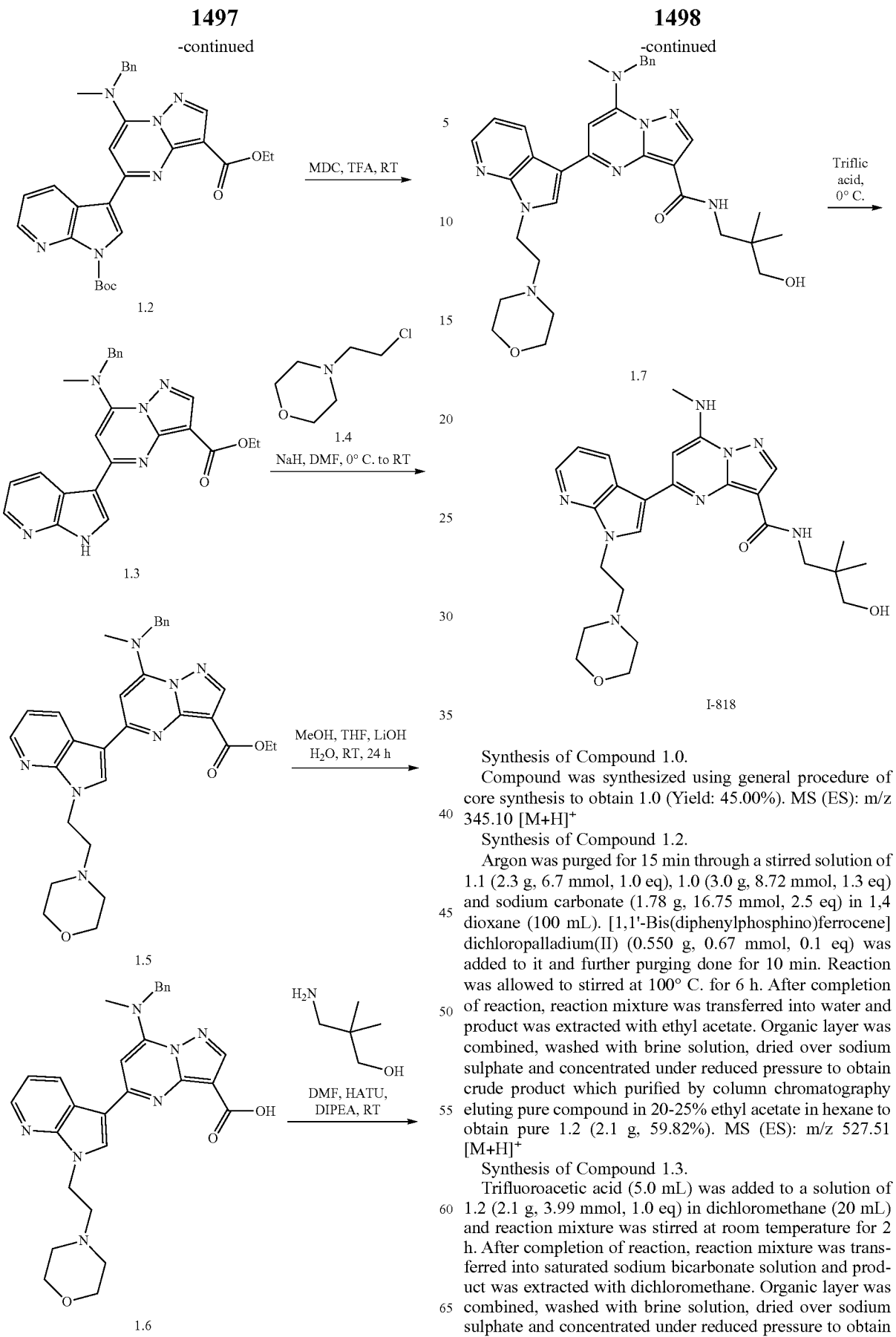

Synthesis of Compound 1.0.

Compound was synthesized using general procedure of core synthesis to obtain 1.0 (Yield: 45.00%). MS (ES): m/z 345.10 [M+H]$^+$ Synthesis of Compound 1.2.

Argon was purged for 15 min through a stirred solution of 1.1 (2.3 g, 6.7 mmol, 1.0 eq), 1.0 (3.0 g, 8.72 mmol, 1.3 eq) and sodium carbonate (1.78 g, 16.75 mmol, 2.5 eq) in 1,4 dioxane (100 mL). [1,1'-Bis(diphenylphosphino)ferrocene] dichloropalladium(II) (0.550 g, 0.67 mmol, 0.1 eq) was added to it and further purging done for 10 min. Reaction was allowed to stirred at 100° C. for 6 h. After completion of reaction, reaction mixture was transferred into water and product was extracted with ethyl acetate. Organic layer was combined, washed with brine solution, dried over sodium sulphate and concentrated under reduced pressure to obtain crude product which purified by column chromatography eluting pure compound in 20-25% ethyl acetate in hexane to obtain pure 1.2 (2.1 g, 59.82%). MS (ES): m/z 527.51 [M+H]$^+$ Synthesis of Compound 1.3.

Trifluoroacetic acid (5.0 mL) was added to a solution of 1.2 (2.1 g, 3.99 mmol, 1.0 eq) in dichloromethane (20 mL) and reaction mixture was stirred at room temperature for 2 h. After completion of reaction, reaction mixture was transferred into saturated sodium bicarbonate solution and product was extracted with dichloromethane. Organic layer was combined, washed with brine solution, dried over sodium sulphate and concentrated under reduced pressure to obtain 1.3. (1.69 g, 99.41%). MS (ES): m/z 427.51 [M+H]$^+$ Synthesis of Compound 1.5.

sodium hydride (0.225 g, 5.6 mmol, 4.0 eq) was added to a solution of 1.3 (0.600 g, 1.4 mmol, 1.0 eq) in N—N-Dimethylformamide (12 mL) at 0° C. portion wise. Reaction mixture was stirred at same temperature for 20 min, 1.4 (0.635 g, 4.22 mmol, 1.2 eq) was added and mixture was allowed to stir at room temperature for 6 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography eluting pure compound in 2-2.5% methanol in dichloromethane to obtain pure 1.5 (420 mg, 55.26%). MS (ES): m/z 540.51 [M+H]$^+$.

Synthesis of Compound 1.6.

To a solution of 1.5 (0.400 g, 0.744 mmol, 1.0 eq), in tetrahydrofuran: methanol: water (20 mL, 1:1:1) was added lithium hydroxide (0.315 g, 7.44 mmol, 10 eq). The reaction was stirred 60° C. for 6 h. After completion of reaction, reaction mixture was concentrated under reduced pressure to obtain residue. To this added water and acidified with 1N hydrochloric acid to adjust pH~6-6.5 at 10° C. Product was filtered and dried under vacuum to obtain pure 1.6 (0.360 g, 94.47%). MS(ES): m/z 512.2 [M+H]$^+$.

Synthesis of Compound 1.7.

Compound was synthesized using general procedure A to obtain 1.7. (0.065 g, 55.72%), MS (ES): 597.33 [M+H]$^+$ Synthesis of Compound I-818:

Mixture of 1.7 (0.065 g, 0.108 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with dichloromethane. Organic layer was combined, dried over sodium sulphate and concentrated under reduced pressure to obtain crude material. This was further purified by trituration with diethyl ether to a obtain I-818 (0.040 g, 72.49%), MS (ES): m/z 507.36 [M+H]—, LCMS purity: 96.81%, HPLC purity: 98.08%, $^1$H NMR (DMSO-d$_6$, 400 MHZ): 9.90 (bs, 1H), 8.74-8.69 (t, J=7.2 Hz, 2H), 8.45-8.42 (t, J=3.6 Hz, 2H), 8.35 (bs, 2H), 7.40 (bs, 1H), 6.64 (s, 1H), 4.77 (bs, 3H), 4.11 (bs, 1H), 3.77 (bs, 3H), 3.66 (bs, 3H), 3.37 (bs, 4H), 3.19 (s, 2H), 3.12-3.11 (d, J=4 Hz, 3H), 0.88 (s, 6H).

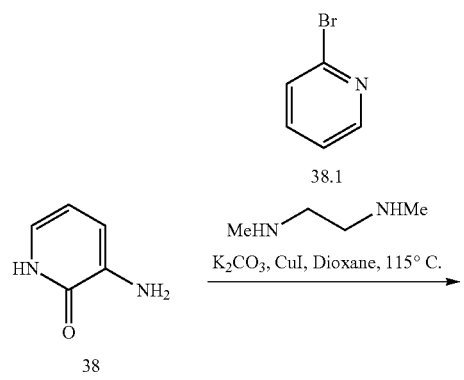

To a solution of 38 (2 g, 18.18 mmol, 1.0 eq) in 1,4-dioxane (40 mL), 38.1 (7.2 g, 45.45 mmol, 2.5 eq) was added. The reaction mixture was degassed for 10 min under argon atmosphere followed by addition of potassium carbonate (7.5 g, 54.54 mmol, 3.0 eq), N,N-dimethylethylenediamine (0.640 g, 7.27 mmol, 0.4 eq), and copper iodide (0.692 g, 3.636 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 101a (2 g, Yield: 58.82%). MS (ES): m/z 188.20 [M+H]$^+$ Synthesis of Compound 1.1.

To a cooled solution of 1 (1 g, 6.33 mmol, 1 eq) in hexane (10 mL) was added silver carbonate (3.50 g, 12.66 mmol, 2 eq) followed by addition of iodomethane (0.988 g, 6.96 mmol, 1.1 eq) under nitrogen. The reaction was stirred at 150° C. for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 8% ethyl acetate in hexane to obtain pure 1.1 (0.580 g, 53.27%), MS(ES): m/z 173.12 [M+H]$^+$.

Synthesis of Compound 101b.

To a solution of 1.1 (0.580 g, 3.37 mmol, 1.0 eq) in methanol (6 ml), palladium on charcoal (0.150 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 1.6% methanol in dichloromethane to obtain pure 101b (0.400 g, 83.51%). MS (ES): m/z 143.13 [M+H]⁺.

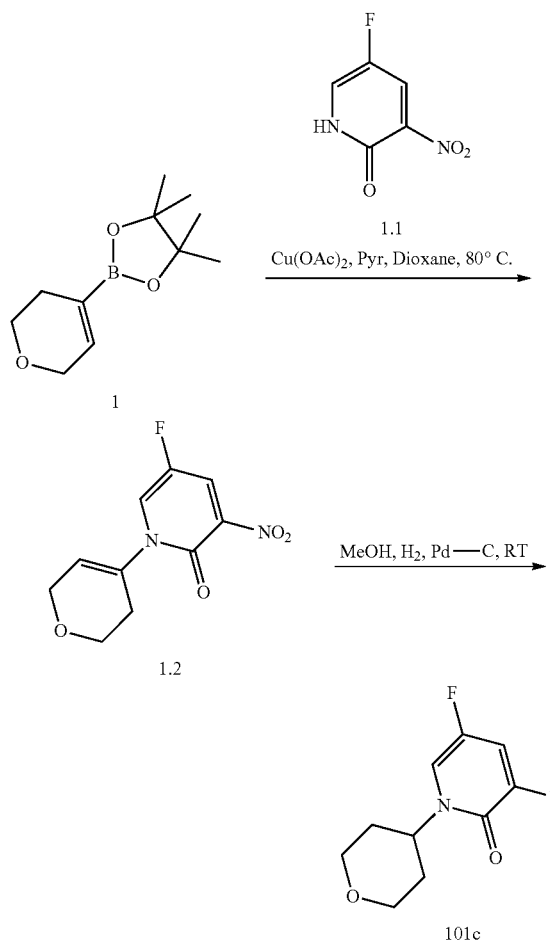

Synthesis of Compound 1.2.

To a solution of 1 (0.500 g, 2.38 mmol, 1.0 eq), in 1,4-dioxane (5 mL) were added copper acetate (0.432 g, 2.38 mmol, 1.0 eq), 1.1 (0.864 g, 5.47 mmol, 2.3 eq) and Pyridine (0.376 g, 4.76 mmol, 2.0 eq). Reaction mixture stirred at 80° C. for 16 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.2 (0.140 g, 24.49%). MS(ES): m/z 241.06 [M+H]⁺

Synthesis of Compound 101c.

To a solution of 1.2 (0.140 g, 0.58 mmol, 1.0 eq) in methanol (3 ml), palladium on charcoal (0.080 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 101c. (0.080 g, 64.67%). MS (ES): m/z 231.10 [M+H]⁺

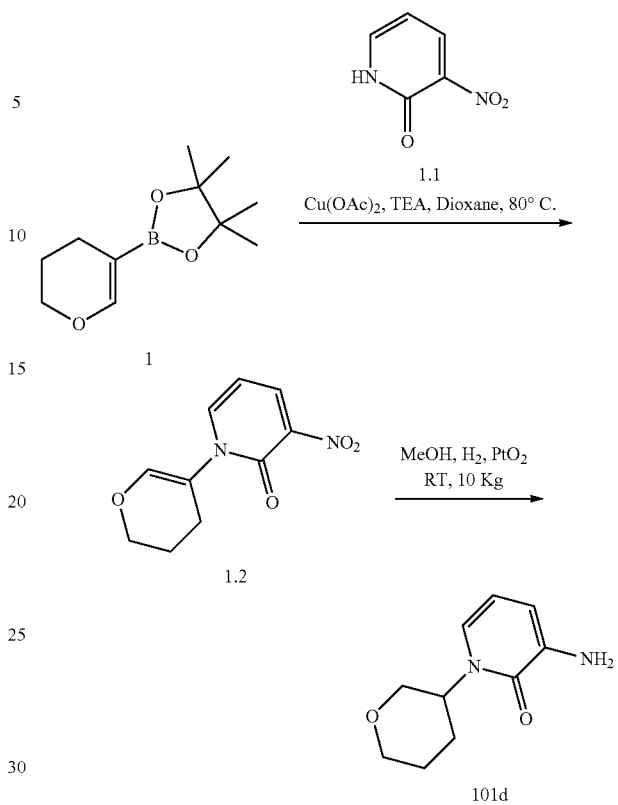

Synthesis of Compound 1.2:

To a solution of 1 (1.0 g, 4.76 mmol, 1.0 eq), in 1,4-dioxane (10 mL) were added copper acetate (0.8 g, 4.76 mmol, 1.0 eq), 1.1 (0.6 g, 11.81 mmol, 2.4 eq) and triethyl amine (1.3 mL, 9.52 mmol, 2.0 eq) was added to reaction mixture and stirred at 80° C. for 16 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.2 (0.360 g, 34.98%). MS(ES): m/z 222.20 [M+H]⁺

Synthesis of Compound 101d.

To a solution of 1.2 (0.36 g, 1.6 mmol, 1.0 eq) in methanol (15 mL), platinum dioxide (0.2 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 101d (0.8 g, 52.13%). MS (ES): m/z 194.23 [M+H]

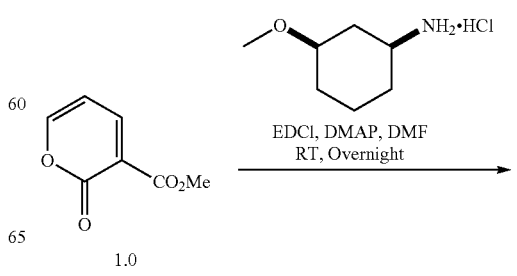

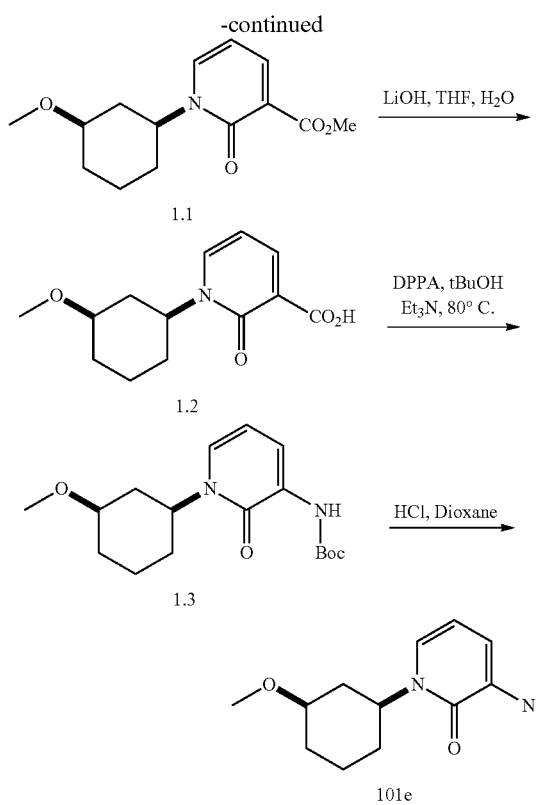

trated under reduced pressure to obtain crude material. This was further purified by combi flash using 1.0% MeOH in Dichloromethane as eluent to 1.3 (0.408 g, Yield: 63.60%). MS(ES): m/z 323.41 [M+H]$^+$.

Synthesis of Compound 101e.

To 1.3 (0.408 g, 1.27 mmol, 1.0 eq) was added 4M hydrochloric acid in 1,4-Dioxane (7 mL) and stirred at room temperature for 4 h. After completion of reaction, reaction mixture was concentrated under reduced pressure, residue was triturated with diethyl ether to obtain 101e (0.272 g, 96.69%). MS (ES): m/z 223.29 [M+H]$^+$

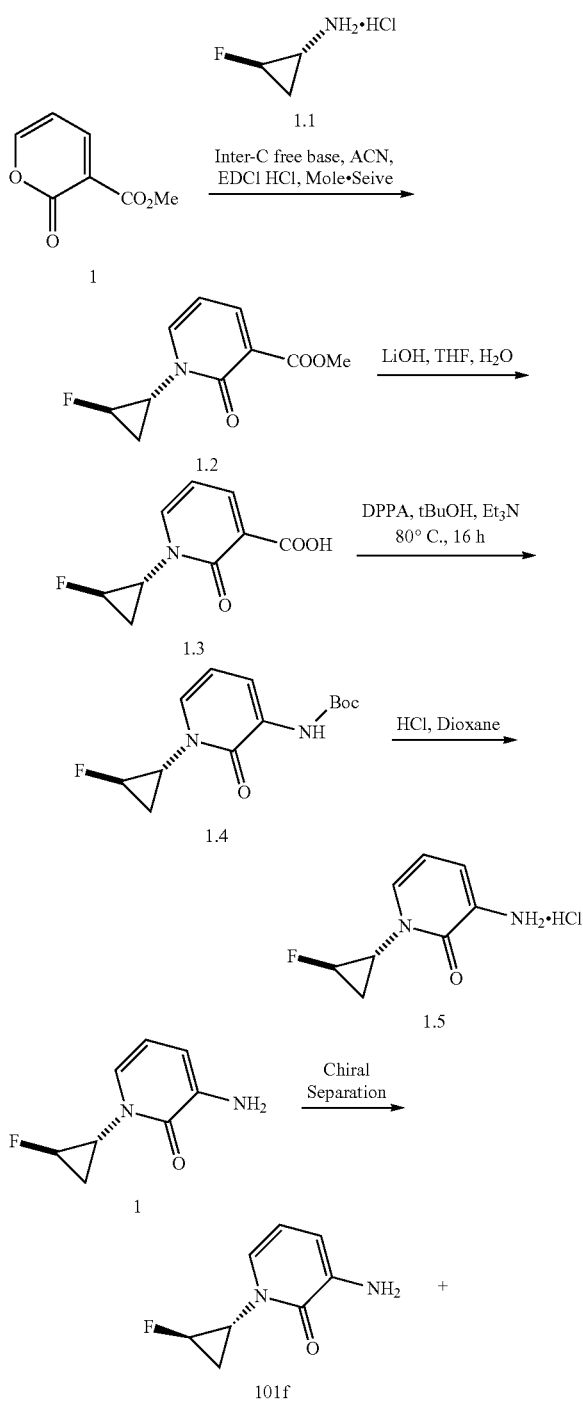

Synthesis of Compound 1.1.

To a solution of 1.0 (2.0 g, 12.98 mmol, 1.0 eq) in N,N-dimethylformamide (60 mL) was added cis-3-methoxycyclohexan-1-amine hydrochloride (2.15 g, 12.98 mmol, 1.0 eq). The reaction mixture was stirred at room temperature for 1 h followed by addition of N-Ethyl-N'-(3-dimethylaminopropyl) carbodiimide hydrochloride (3.23 g, 16.87 mmol, 1.3 eq) and 4-dimethylaminopryidine (0.396 g, 3.24 mmol, 0.25 eq). The reaction was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 30% ethyl acetate in hexane as eluent to 1.1 (1.70 g, Yield: 49.38%). MS(ES): m/z 266.31 [M+H]$^+$ Synthesis of Compound 1.2.

To a solution of 1.1 (0.800 g, 3.02 mmol, 1.0 eq), in tetrahydrofuran: methanol: water (20 mL, 1:1:1) was added lithium hydroxide (0.633 g, 15.1 mmol, 5.0 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.1 (0.500 g, Yield: 65.99%). MS(ES): m/z: 252.28 [M+H]$^+$.

Synthesis of Compound 1.3.

To a solution of 1.2 (0.500 g, 1.99 mmol, 1.0 eq) in Tert-Butyl alcohol was added di-phenylphosphorylazide (0.711 g, 2.58 mmol, 1.3 eq), triethylamine (0.342 g, 3.38 mmol, 1.7 eq). The reaction was stirred at 90° C. for 16 h. After completion of reaction, reaction mixture was concen-

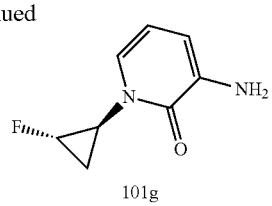

101g

Synthesis of compound 1.2.

To a cooled solution of 1 (0.5 g, 3.24 mmol, 1.0 eq), in Acetonitrile (10 mL) was added 1.1 (0.395 g, 3.56 mmol, 1.1 eq). The reaction mixture was stirred at 0° C. for 30 min and further stirred at room temperature for 15 min. N-Ethyl-N'-(3-dimethylaminopropyl)carbodiimide hydrochloride (0.652 g, 4.21 mmol, 1.3 eq) and Mole. Sieve were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.320 g, 46.71%). MS(ES): m/z 212.07 [M+H]$^+$.

Synthesis of Compound 1.3.

To a solution of 1.2 (0.320 g, 1.51 mmol, 1.0 eq), in tetrahydrofuran: water (8 mL, 2:1) was added lithium hydroxide (0.362 g, 15.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.265 g, 88.70%). MS(ES): m/z 198.05 [M+H]$^+$.

Synthesis of Compound 1.4.

To a solution of 1.3 (0.265 g, 1.34 mmol, 1.0 eq) in tert.butanol (6 mL) was added triethylamine (0.230 g, 2.27 mmol, 1.7 eq) and diphenyl phosphoryl azide (0.478 g, 1.74 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.160 g, 44.37%). MS(ES): m/z 269.13 [M+H]$^+$.

Synthesis of Compound 1.5.

A cooled solution of 1.4 (0.160 g, 0.59 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 1.5. (0.125 g, 98.33%). MS(ES): m/z 205.05 [M+HCl]$^+$.

Synthesis of Compound 101f and 101 g.

Isomers of 1 (0.420 g) were separated out using column (CHIRAL PAK AD-H 250×4.6 mm, 5 μM) and DEA in methanol as co-solvent with flow rate of 4 mL/min. to get pure fraction-1 and fraction-2 (FR-b). FR-a was evaporated under reduced pressure at 30° C. to afford pure 101f. (0.190 g). MS(ES): m/z 169.07 [M+H]$^+$. FR-b was evaporated under reduced pressure at 30° C. to afford pure 101 g. (0.180 g). MS(ES): m/z 169.07 [M+H]$^+$ Example 102: Syntheses of compounds comprising N-(-2-methoxycyclobutyl)aminocarbonyl at position 3 of the pyrazolo[1,5-a]pyrimidine 102.1. Synthesis of N-(-2-methoxycyclobutyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-814)

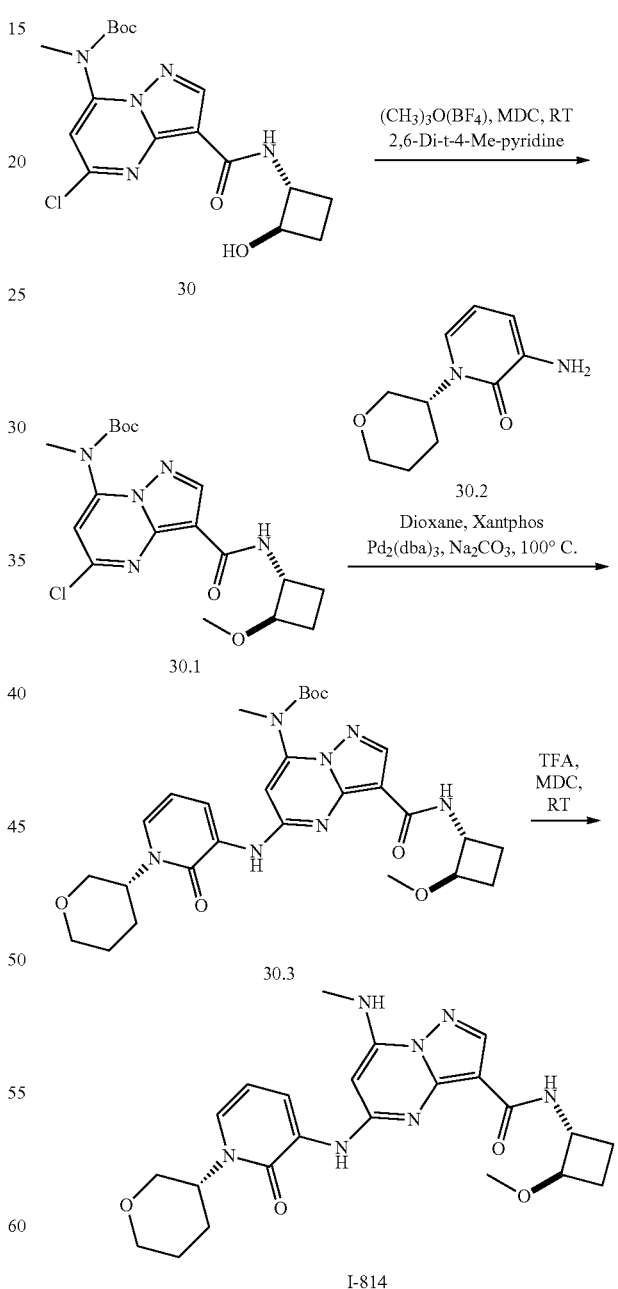

Synthesis of Compound 30.

Compound was synthesized as per experimental protocol of I-676 to obtain 30. (Yield: 52.83%), MS (ES): m/z 396.14 [M+H]$^+$ Synthesis of Compound 30.1.

To a solution of 30 (1.0 g, 2.52 mmol, 1 eq) in dichloromethane (20 mL), Triethyloxonium tetrafluoroborate (0.957 g, 5.04 mmol, 2.0 eq) and 2,6-Di-tert-butyl-4-methylpyridine (1.54 g, 7.56 mmol, 3.0 eq) was added. The reaction mixture was stirred at room temperature for 4 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 30.1. (0.600 g, Yield: 57.95%). MS (ES): m/z 410.16 [M+H]$^+$ Synthesis of Compound 30.3.

Compound was synthesized using general procedure B to obtain 30.3. (0.150 g, 86.65%), MS (ES): 568.28 [M+H]$^+$ Synthesis of Compound I-814:

Compound was synthesized using general procedure C to obtain I-814 (0.120 g, 97.13%), MS (ES): m/z 468.51 [M+H]$^+$, LCMS purity: 100%, HPLC purity: 96.92%, Chiral HPLC: 49.46%, 49.90%, $^1$H NMR (DMSO-d$_6$, 400 MHZ): 8.96 (s, 1H), 8.26-8.24 (d, J=7.2 Hz, 1H), 8.21 (s, 1H), 8.08-8.06 (d, J=8.8 Hz, 1H), 7.95-7.94 (d, J=4.4 Hz, 1H), 7.58-7.56 (t, J=7.2 Hz, 1H), 6.36-6.33 (t, J=6.8 Hz, 1H), 6.24 (s, 1H), 4.90 (bs, 1H), 4.35-4.30 (m, 1H), 3.86 (bs, 2H), 3.73-3.68 (m, 1H), 3.62-3.57 (t, J=10 Hz, 1H), 3.50-3.45 (t, J=10.4 Hz, 1H), 3.36 (s, 1H), 3.21 (bs, 2H), 2.92-2.91 (d, J=4.8 Hz, 3H), 1.78 (bs, 2H), 1.56-1.51 (m, 1H), 1.43-1.35 (m, 2H), 1.25 (bs, 2H), 1.12-1.09 (m, 1H).

Additional compounds prepared by substantially the same method, and their characterization data, are listed in the Table 42 below. The intermediate corresponding to 30.2 of the above scheme is listed for each compound.

TABLE 42

| Compound | Intermediate | Characterization data |
|---|---|---|
| I-815 | 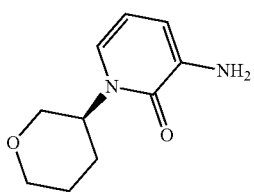 [SMILES: Nc1cccn([C@H]2CCCOC2)c1=O] | MS (ES): m/z 468.40 [M + H]$^+$, LCMS purity: 97.55%, HPLC purity: 97.19%, Chiral HPLC: 48.14%, 50.77%, , $^1$H NMR (DMSO-d$_6$, 400 MHZ): 8.96 (s, 1H), 8.26-8.24 (d, J = 6 Hz, 1H), 8.21 (s, 1H), 8.08-8.05 (d, J = 9.2 Hz, 1H), 7.95-7.94 (d, J = 4.8 Hz, 1H), 7.57-7.56 (d, J = 5.6 Hz, 1H), 6.36-6.32 (t, J = 7.2 Hz, 1H), 6.24 (s, 1H), 4.92-4.89 (m, 1H), 4.34-4.30 (t, J = 8.4 Hz, 1H), 3.87-3.83 (t, J = 7.6 Hz, 2H), 3.71-3.69 (d, J = 7.6 Hz, 1H), 3.61-3.56 (t, J = 10 Hz, 1H), 3.48 (bs, 1H), 3.21 (s, 3H), 2.92-2.91 (d, J = 4.8 Hz, 3H), 1.99 (bs, 1H), 1.78-1.72 (m, 3H), 1.56-1.51 (t, J = 9.6 Hz, 1H), 1.40-1.35 (t, J = 9.6 Hz, 2H), 1.25 (bs, 1H). |
| I-816 | 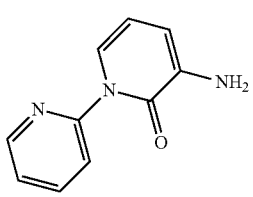 [SMILES: Nc1cccn(-c2ccccn2)c1=O] | MS (ES): m/z 461.40 [M + H]$^+$, LCMS purity: 98.84%, HPLC purity: 93.86%, Chiral HPLC: 47.78%, 51.75%, $^1$H NMR (DMSO-d$_6$, 400 MHZ): 9.06 (s, 1H), 8.66 (bs, 1H), 8.36-8.34 (d, J = 7.2 Hz, 1H), 8.22 (s, 1H), 8.12-8.07 (m, 1H), 8.05-8.04 (d, J = 1.6 Hz, 1H), 7.99-7.97 (d, J = 5.2 Hz, 1H), 7.88-7.86 (d, J = 8 Hz, 1H), 7.64-7.62 (d, J = 7.2 Hz, 1H), 7.57-7.54 (m, 1H), 6.47-6.44 (t, J = 7.2 Hz, 1H), 6.24 (s, 1H), 4.36-4.29 (m, 1H), 3.77-3.71 (m, 1H), 3.22 (s, 3H), 2.92-2.91 (d, J = 4.8 Hz, 3H), 2.18-2.06 (m, 2H), 1.56-1.49 (m, 1H), 1.46-1.39 (m, 1H). |
| I-817 | 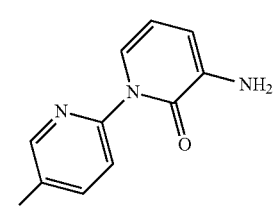 | MS (ES): m/z 479.37 [M + H]$^+$, LCMS purity: 100%, HPLC purity: 96.81%, Chiral HPLC: 48.65%, 48.75%, , $^1$H NMR (DMSO-d$_6$, 400 MHZ): 9.06 (s, 1H), 8.68-8.67 (d, J = 2.8 Hz, 1H), 8.36-8.34 (d, J = 6 Hz, 1H), 8.22 (s, 1H), 8.11-8.09 (d, J = 9.2 Hz, 1H), 8.06-8.03 (m, 1H), 8.02-7.93 (m, 1H), 7.60-7.59 (d, J = 5.6 Hz, 1H), 6.48-6.44 (t, J = 7.2 Hz, 1H), 6.25 (s, 1H), 4.35-4.31 (m, 1H), 3.76-3.71 (m, 1H), 3.22 (s, 3H), 3.18-3.17 (d, J = 5.2 Hz, 1H), 2.92-2.91 (d, J = 4.4 Hz, 3H), 2.17-2.05 (m, 2H), 1.56-1.51 (m, 1H), 1.43-1.38 (m, 1H). |

TABLE 42-continued

| Compound | Intermediate | Characterization data |
|---|---|---|
| I-843 | 3-amino-1-(6-methylpyridin-3-yl)pyridin-2(1H)-one derivative | MS (ES): m/z 475.36 [M + H]⁺, LCMS purity: 97.78%, HPLC purity: 97.44%, CHIRAL HPLC: 46.90%, 46.26%, ¹H NMR (DMSO-d₆, 400 MHZ): 9.04 (bs, 1H), 8.60 (bs, 1H), 8.38-8.36 (d, J = 7.6 Hz, 1H), 8.23 (s, 1H), 8.10-8.08 (d, J = 8.8 Hz, 1H), 7.97 (bs, 1H), 7.90-7.88 (d, J = 8 Hz, 1H), 7.48-7.43 (m, 2H), 6.44-6.41 (t, J = 6.8 Hz, 1H), 6.26 (s, 1H), 4.37-4.33 (t, J = 7.6 Hz, 1H), 3.76-3.74 (d, J = 7.6 Hz, 1H), 3.23 (s, 3H), 2.91 (bs, 3H), 2.58 (bs, 3H), 1.57-1.52 (t, J = 9.6 Hz, 2H), 1.45-1.40 (t, J = 9.2 Hz, 1H), 1.25 (bs, 1H). |
| I-863 | 3-amino-1-(3-fluoropyridin-2-yl)pyridin-2(1H)-one derivative | MS (ES): m/z 479.42 [M + H]⁺, LCMS purity: 100%, HPLC purity: 98.97%, Chiral HPLC: 49.85%, 49.96%, , ¹H NMR (DMSO-d₆, 400 MHZ): 9.08 (s, 1H), 8.53-8.52 (d, J = 4.4 Hz, 1H), 8.39-8.37 (d, J = 7.2 Hz, 1H), 8.23 (s, 1H), 8.11 (s, 1H), 8.09 (s, 1H), 7.98 (bs, 1H), 7.76-7.72 (m, 1H), 7.50-7.49 (d, J = 7.2 Hz, 1H), 6.50-6.47 (t, J = 6.8 Hz, 1H), 6.22 (s, 1H), 4.36-4.32 (t, J = 8 Hz, 1H), 3.78-3.72 (m, 1H), 3.23 (s, 3H), 2.92 (s, 2H), 2.18-2.06 (m, 2H), 1.59-1.49 (m, 1H), 1.42-1.37 (m, 1H), 1.25 (bs, 1H). |
| I-864 | 3-amino-1-(pyridin-3-yl)pyridin-2(1H)-one derivative | MS (ES): m/z 461.37 [M + H]⁺, LCMS purity: 98.07%, HPLC purity: 98.52%, Chiral HPLC: 49.65%, 49.73%, , ¹H NMR (DMSO-d₆, 400 MHZ): 9.05 (s, 1H), 8.77-8.76 (d, J = 2.4 Hz, 1H), 8.70-8.69 (d, J = 4 Hz, 1H), 8.39-8.38 (d, J = 6 Hz, 1H), 8.23 (s, 1H), 8.10-8.08 (d, J = 9.2 Hz, 1H), 8.05-8.03 (d, J = 8.4 Hz, 1H), 7.98-7.97 (d, J = 4.8 Hz, 1H), 7.66-7.62 (m, 1H), 7.48-7.46 (m, 1H), 6.46-6.43 (t, J = 6.8 Hz, 1H), 6.26 (s, 1H), 4.37-4.33 (t, J = 8 Hz, 1H), 3.79-3.73 (m, 1H), 3.23 (s, 3H), 2.92-2.91(d, J = 4.8 Hz, 3H), 1.25 (bs, 3H), 0.87 (bs, 1H). |
| I-865 | 3-amino-1-(2-methylpyridin-3-yl)pyridin-2(1H)-one derivative | MS (ES): m/z 475.31 [M + H]⁺, LCMS purity: 98.34%, HPLC purity: 95.92%, Chiral HPLC: 47.58%, 50.32%, , ¹H NMR (DMSO-d₆, 400 MHZ): 9.03 (s, 1H), 8.48-8.47 (d, J = 4 Hz, 1H), 8.40-8.38 (d, J = 7.6 Hz, 1H), 8.23 (s, 1H), 8.14-8.11 (m, 1H), 7.99-7.98 (d, J = 4.8 Hz, 1H), 7.96-7.94 (d, J = 7.6 Hz, 1H), 7.55-7.52 (m, 1H), 7.36-7.35 (d, J = 6 Hz, 1H), 6.46-6.43 (t, J = 6.8 Hz, 1H), 6.23 (s, 1H), 4.38-4.34 (t, J = 8.4 Hz, 2H), 3.78-3.73 (m, 1H), 3.23 (s, 3H), 2.92-2.91(d, J = 4.8 Hz, 3H), 2.15 (bs, 5H), 1.56-1.51 (m, 1H). |
| I-890 | 3-amino-1-(4-methyloxazol-2-yl)pyridin-2(1H)-one derivative | MS (ES): m/z 465.27 [M + H]⁺, LCMS purity: 96.44%, HPLC purity: 97.42%, CHIRAL HPLC 48.98%, 48.93%, ¹H NMR (DMSO-d₆, 400 MHZ): 9.11 (bs, 1H), 8.35-8.33 (d, J = 7.6 Hz, 1H), 8.23 (s, 1H), 8.06-8.05 (d, J = 6.4 Hz, 2H), 8.02 (s, 1H), 7.51-7.49 (d, J = 6 Hz, 1H), 6.47-6.43 (t, J = 7.2 Hz, 1H), 6.21 (s, 1H), 4.34-4.30 (t, J = 8 Hz, 1H), 3.74-3.69 (m, 1H), 3.21 (s, 3H), 2.92 (s, 3H), 2.20 (bs, 3H), 1.54-1.50 (t, J = 8.8 Hz, 1H), 1.41-1.36 (t, J = 10 Hz, 1H), 1.25 (bs, 1H), 1.12-1.09 (t, J = 7.2 Hz, 1H). |

TABLE 42-continued

| Compound | Intermediate | Characterization data |
|---|---|---|
| I-895 | (2-methyloxazol-5-yl pyridinone with NH2) | MS (ES): m/z 464.49 [M + H]+, LCMS purity: 100%, HPLC purity: 97.17%, CHIRAL HPLC: 49.18%, 49.24%, 1H NMR (DMSO-d6, 400 MHZ): 9.14 (s, 1H), 8.32-8.31 (d, J = 6 Hz, 1H), 8.23 (s, 1H), 8.07-8.05 (d, J = 8.8 Hz, 1H), 7.99 (bs, 1H), 7.89-7.57 (m, 1H), 7.41 (s, 1H), 6.51-6.47 (t, J = 7.2 Hz, 1H), 6.23 (s, 1H), 4.34-4.30 (t, J = 8.4 Hz, 1H), 3.74-3.68 (m, 1H), 3.21 (s, 3H), 2.93-2.91 (d, J = 4.8 Hz, 3H), 2.52 (s, 3H), 2.16-2.04 (m, 2H), 1.55-1.50 (t, J = 8.8 Hz, 1H), 1.42-1.25 (m, 1H). |
| I-917 | (N-isopropyl pyridinone with NH2) | MS (ES): m/z 426.70 [M + H]+, LCMS purity: 95.47%, HPLC purity: 95.39%, CHIRAL HPLC: 46%, 47%, 1H NMR (DMSO-d6, 400 MHZ): 9.94 (s, 1H), 8.24-8.21 (m, 2H), 8.09-8.07 (d, J = 5.2 Hz, 1H), 7.94-7.93 (d, J = 5.2 Hz, 1H), 7.50-7.48 (d, J = 6.8 Hz, 1H), 6.37-6.33 (t, J = 7.2 Hz, 1H), 6.23 (s, 1H), 5.21-5.18 (m, 1H), 4.35-4.31 (m, 1H), 3.74-3.70 (m, 1H), 3.21 (s, 3H), 2.92-2.91 (d, J = 4.8 Hz, 3H), 2.17-2.07 (m, 2H), 1.56-1.48 (m, 2H), 1.36 (s, 6H). |
| I-959 | (4-methoxy-4-methylcyclohexyl pyridinone with NH2) | MS (ES): m/z 510.41 [M + H]+, LCMS purity: 100%, HPLC purity: 99.11%, Chiral HPLC: 47.26%, 52.74%, 1H NMR (DMSO-d6, 400 MHZ): 8.92 (s, 1H), 8.23-8.22 (d, J = 7.2 Hz, 1H), 8.20 (s, 1H), 8.09-8.07 (d, J = 8.8 Hz, 1H), 7.95-7.93 (d, J = 4.8 Hz, 1H), 7.59-7.57 (d, J = 6.4 Hz, 1H), 6.33-6.30 (t, J = 7.2 Hz, 1H), 6.22 (s, 1H), 4.76 (bs, 1H), 4.34-4.30 (t, J = 8 Hz, 1H), 3.73-3.68 (m, 1H), 3.36 (s, 1H), 3.20 (s, 5H), 2.92-2.91 (d, J = 4.4 Hz, 3H), 2.14-2.05 (m, 2H), 1.94 (bs, 3H), 1.88 (bs, 2H), 1.60-1.51(m, 3H), 1.40-1.35 (t, J = 9.6 Hz, 1H), 1.24 (bs, 4H). |
| I-984 | (5-fluoropyridin-3-yl pyridinone with NH2) | MS (ES): m/z 479.52 [M + H]+, LCMS purity: 97.50%, HPLC purity: 95.14%, CHIRAL HPLC: 49.43%, 48.71%, 1H NMR (DMSO-d6, 400 MHZ): 9.08 (s, 1H), 8.76-8.75 (d, J = 2.4 Hz, 1H), 8.69 (bs, 1H), 8.39-8.38 (d, J = 6 Hz, 1H), 8.23 (s, 1H), 8.19-8.17 (d, J = 9.6 Hz, 1H), 8.09-8.07 (d, J = 9.2 Hz, 1H), 7.99-7.98 (d, J = 4.8 Hz, 1H), 7.51-7.50 (d, J = 5.6 Hz, 1H), 6.47-6.44 (t, J = 7.2 Hz, 1H), 6.27 (s, 1H), 4.39-4.30 (m, 1H), 3.78-3.72 (m, 1H), 3.17 (s, 3H), 2.92-2.91 (d, J = 4.8 Hz, 3H), 2.19-2.06 (m, 3H), 1.40-1.34 (m, 1H). |
| I-995 | (3-methoxycyclohexyl pyridinone with NH2) | MS (ES): 496.57 [M + H]+ LCMS purity: 100%, HPLC purity: 96.17%, CHIRAL HPLC: 50.13%, 49.38%, 1H NMR (DMSO-d6, 400 MHZ): 8.90 (s, 1H), 8.23 (s, 1H), 8.20 (s, 1H), 8.09-8.06 (d, J = 9.2 Hz, 1H), 7.94-7.93 (d, J = 4.8 Hz, 1H), 7.53-7.51 (d, J = 6.8 Hz, 1H), 6.35-6.31 (t, J = 7.2 Hz, 1H), 6.21 (s, 1H), 4.87-4.81 (t, J = 12.4 Hz, 1H), 4.34-4.30 (t, J = 8 Hz, 1H), 3.73-3.67 (m, 1H), 3.51 (s, 1H), 3.27 (s, 3H), 3.20 (bs, 3H), 2.92-2.91 (d, J = 4.8 Hz, 3H), 2.19-2.07 (m, 3H), 2.06 (s, 1H), 1.88-1.85 (d, J = 13.6 Hz, 1H), 1.74 (bs, 1H), 1.61-1.50 (m, 3H), 1.39-1.27 (m, 2H), 1.23 (bs, 1H). |

TABLE 42-continued

| Compound | Intermediate | Characterization data |
|---|---|---|
| I-996 | | MS (ES): 496.62 [M + H]+ LCMS purity: 100%, HPLC purity: 96.18%, CHIRAL HPLC: 49.00%, 48.72%, $^1$H NMR (DMSO-d$_6$, 400 MHZ): 8.91 (s, 1H), 8.22 (s, 1H), 8.19 (s, 1H), 8.08-8.05 (d, J = 9.2 Hz, 1H), 7.95-7.94 (d, J = 4.8 Hz, 1H), 7.52-7.50 (d, J = 6 Hz, 1H), 6.34-6.30 (t, J = 7.2 Hz, 1H), 6.21 (s, 1H), 4.86-4.80 (t, J = 12 Hz, 1H), 4.33-4.28 (t, J = 8 Hz, 1H), 3.71-3.66 (m, 1H), 3.50 (s, 1H), 3.26 (s, 3H), 3.19 (bs, 3H), 2.91-2.90 (d, J = 4.8 Hz, 3H), 2.18-2.04 (m, 3H), 1.87-1.83 (d, J = 3.2 Hz, 1H), 1.73 (bs, 1H), 1.67-1.57 (m, 3H), 1.38-1.29 (m, 2H), 1.23 (bs, 1H), 1.13 (bs, 1H). |
| I-1014 | | MS (ES): m/z 468.57 [M + H]+, LCMS purity: 100%, HPLC purity: 99.40%, CHIRAL HPLC purity: 48%, 51%, $^1$H NMR (DMSO-d$_6$, 400 MHZ): 8.97 (s, 1H), 8.29-8.28 (d, J = 5.6 Hz 1H), 8.21-8.20 (d, J = 6.8 Hz, 1H), 8.08-8.06 (d, J = 8.8 Hz, 1H), 7.97-7.94 (d, J = 4.8 Hz, 1H), 7.53-7.52 (d, J = 6.0 Hz 1H), 6.36-6.32 (t, J = 7.6 Hz 1H), 6.23 (s, 1H), 5.05 (m, 1H), 4.34-4.32 (m, 1H), 4.30-4.27 (m, 1H), 4.03-4.00 (m, 2H), 3.88-3.83(m, 1H), 3.72-3.69 (m, 1H), 3.21-3.20 (d, J = 2.8 Hz, 3H), 2.92-2.91 (d, J = 4.8 Hz 3H), 2.16 (m, 2H), 2.38-2.36 (d, J = 7.6 Hz, 2H), 1.78 (m, 2H), 1.56 (m, 1H), 1.25 (m, 1H). |
| I-1037 | | MS (ES): 496.61 [M + H]+ LCMS purity: 100%, HPLC purity: 98.19%, CHIRAL HPLC: 49.65, 49.73%, $^1$H NMR (DMSO-d$_6$, 400 MHZ): 8.89 (s, 1H), 8.24-8.22 (d, J = 7.2 Hz, 1H), 8.20 (s, 1H), 8.11-8.09 (d, J = 9.2 Hz, 1H), 7.93-7.92 (d, J = 4.8 Hz, 1H), 7.42-7.40 (d, J = 7.2 Hz, 1H), 6.32-6.28 (t, J = 7.2 Hz, 1H), 6.18 (s, 1H), 4.88 (bs, 1H), 4.34-4.30 (m, 1H), 3.71-3.66 (m, 2H), 3.16 (s, 4H), 3.11 (s, 3H), 2.92-2.91 (d, J = 4.8 Hz, 3H), 2.16-2.04 (m, 4H), 1.86 (bs, 1H), 1.39 (bs, 6H). |
| I-1049 | | MS (ES): 513.72 [M + H]+ LCMS purity: 100%, HPLC purity: 97.03%, CHIRAL HPLC: 49.13% 50.65%, $^1$H NMR (DMSO-d$_6$, 400 MHZ): 8.92 (s, 1H), 8.24-8.22 (d, J = 6.4 Hz, 1H), 8.20 (s, 1H), 8.07-8.05 (d, J = 9.2 Hz, 1H), 7.95-7.93 (d, J = 4.8 Hz, 1H), 7.53-7.51 (d, J = 6.8 Hz, 1H), 6.34-6.30 (t, J = 7.2 Hz, 1H), 6.22 (s, 1H), 4.83-4.77 (m, 1H), 4.64-4.62 (t, J = 4.8 Hz, 1H), 4.52-4.50 (t, J = 4.8 Hz, 1H), 4.36-4.28 (m, 1H), 3.73-3.67 (m, 1H), 3.42-3.36 (m, 2H), 3.20 (s, 3H), 3.08-3.05 (d, J = 11.2 Hz, 2H), 2.92-2.91 (d, J = 4.4 Hz, 3H), 2.74-2.71(t, J = 4.8 Hz, 1H), 2.67-2.65 (t, J = 4.8 Hz, 1H), 1.98-1.90 (m, 2H), 1.77 (bs, 2H), 1.58-1.48 (m, 1H), 1.42-1.32 (m, 1H), 1.24 (bs, 1H), 1.12 (bs, 1H). |
| I-1051 | | MS (ES): m/z 408.57 [M + H]+, LCMS purity: 96%, HPLC purity: 98.16%, CHIRAL HPLC: 50%, 49%, $^1$H NMR (DMSO-d$_6$, 400 MHZ): 9.79 (s, 1H), 8.82 (s, 1H), 8.18 (s, 1H), 8.15-8.13 (d, J = 9.2 Hz, 1H), 8.00-7.95 (m, 2H), 7.56-7.54 (d, J = 8 Hz, 1H), 7.47-7.43 (t, 1H), 6.00 (s, 1H), 4.24-4.20 (m, 1H), 3.45-3.39 (m, 1H), 3.13 (s, 3H), 2.95-2.94 (d, J = 4.4 Hz, 3H), 2.04-1.97 (m, 2H), 1.48-1.44 (m, 1H), 1.11-1.06 (m, 1H). |

TABLE 42-continued

| Compound | Intermediate | Characterization data |
|---|---|---|
| I-1052 | 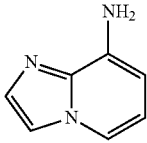 | MS (ES): 407.27 [M + H]+ LCMS purity: 97.11%, HPLC purity: 96.64%, CHIRAL HPLC purity: 49.32%, 50.67%, $^1$H NMR (DMSO-d$_6$, 400 MHZ): 9.62 (bs, 1H), 8.33-8.31 (d, J = 6.4 Hz, 1H), 8.22 (s, 1H), 8.19-8.17 (d, J = 8.8 Hz, 1H), 8.05 (bs, 1H), 8.02 (bs, 1H), 7.95-7.93 (d, J = 6.8 Hz, 1H), 7.63 (bs, 1H), 6.91 (bs, 1H), 6.27 (s, 1H), 4.32-4.29 (m, 1H), 3.64-3.62 (d, J = 7.2 Hz, 1H), 3.18 (s, 3H), 2.95-2.94 (d, J = 4 Hz, 3H), 2.09 (bs, 2H), 1.54-1.49 (t, J = 10.4 Hz, 2H). |
| I-1056 | 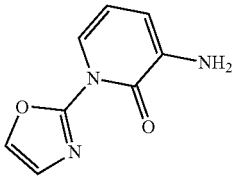 [SMILES: Nc1cccn(-c2ncco2)c1=O] | MS (ES): 451.30 [M + H]+ LCMS purity: 98.39%, HPLC purity: 99.04%, CHIRAL HPLC: 49.35%, 50.20%, $^1$H NMR (DMSO-d$_6$, 400 MHZ): 9.12 (s, 1H), 8.36 (s, 1H), 8.34 (s, 1H), 8.23 (s, 1H), 8.06-8.01 (m, 2H), 7.53 (bs, 1H), 7.50 (s, 1H), 6.49-6.45 (t, J = 7.2 Hz, 1H), 6.21 (s, 1H), 4.34-4.30 (m, 1H), 3.75-3.69 (m, 1H), 3.21 (s, 3H), 2.92-2.91 (d, J = 4.8 Hz, 3H), 2.16-2.04 (m, 2H), 1.24 (bs, 2H). |
| I-1059 | 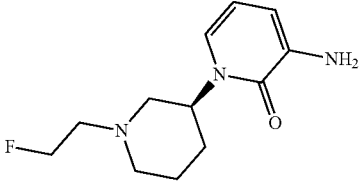 [SMILES: Nc1cccn([C@H]2CCCN(CCF)C2)c1=O] | MS (ES): m/z 513.57 [M + H]+, LCMS purity: 99.51%, HPLC purity: 50.04%, 49.13%, $^1$H NMR (DMSO-d$_6$, 400 MHZ): 8.94 (s, 1H), 8.25-8.23 (d, J = 6.8 Hz, 1H), 8.20 (s, 1H), 8.08-8.06 (d, J = 8.8 Hz, 1H), 7.94-7.93 (d, J = 4 Hz, 1H), 7.61-7.60 (d, J = 4.8 Hz, 1H), 7.09-7.08 (d, J = 5.6 Hz, 1H), 6.84-6.82 (d, J = 7.6 Hz, 1H), 6.32 (bs, 1H), 6.23 (bs, 1H), 4.95 (bs, 1H), 4.62 (bs, 1H), 4.50 (bs, 1H), 4.34-4.30 (t, J = 7.6 Hz, 1H), 3.97 (bs, 1H), 3.73-3.67 (m, 1H), 3.20 (s, 3H), 2.92-2.91 (d, J = 4.8 Hz, 3H), 2.86 (bs, 1H), 2.66 (bs, 1H), 2.36 (bs, 1H), 2.19-2.04 (m, 3H), 1.82 (bs, 2H), 1.56-1.51 (m, 3H). |
| I-1062 | 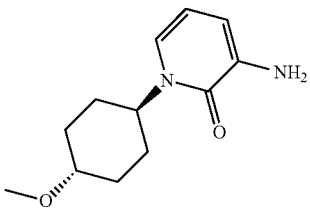 | MS (ES): 496.32 [M + H]+ LCMS purity: 100%, HPLC purity: 97.00%, CHIRAL HPLC purity: 49.86%, 49.01%, $^1$H NMR (DMSO-d$_6$, 400 MHZ): 8.90 (s, 1H), 8.22 (s, 1H), 8.19 (s, 1H), 8.07-8.05 (d, J = 8.8 Hz, 1H), 7.94-7.93 (d, J = 4.8 Hz, 1H), 7.46-7.45 (d, J = 6 Hz, 1H), 6.33-6.30 (t, J = 7.2 Hz, 1H), 6.21 (s, 1H), 4.80 (bs, 1H), 4.33-4.26 (m, 1H), 3.71-3.68 (t, J = 7.6 Hz, 2H), 3.27 (s, 3H), 3.19 (s, 3H), 3.17 (s, 1H), 2.91-2.90 (d, J = 4.8 Hz, 3H), 1.77 (bs, 5H), 1.54-1.47 (m, 2H), 1.33-1.26 (m, 2H), 1.23 (bs, 2H). |
| I-1063 | 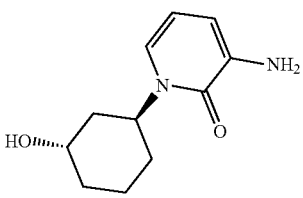 [SMILES: Nc1cccn([C@H]2CCC[C@H](O)C2)c1=O] | MS (ES): m/z 482.70 [M + H]+, LCMS purity: 100%, HPLC purity: 95.29%, CHIRAL HPLC: 49%, 50%, $^1$H NMR (DMSO-d$_6$, 400 MHZ): 8.90 (s, 1H), 8.21-8.20 (d, J = 3.6 Hz, 2H), 8.09-8.07 (d, J = 9.2 Hz, 1H), 7.94-7.93 (d, J = 4 Hz, 1H), 7.48-7.46 (d, J = 5.6 Hz, 1H), 6.33-6.29 (t, J = 7.2 Hz, 1H), 6.21 (s, 1H), 5.32-5.25 (m, 1H), 4.36-4.28 (m, 1H), 4.15 (s, 1H), 3.73-3.67 (m, 1H), 3.51 (bs, 1H), 3.20 (s, 3H), 2.92-2.91 (d, J = 4.8 Hz, 3H), 2.19-2.05 (m, 2H), 2.00-1.93 (m, 2H), 1.90-1.83 (m, 2H), 1.80-1.62 (m, 4H), 1.44 (bs, 2H). |

TABLE 42-continued

| Compound | Intermediate | Characterization data |
|---|---|---|
| I-1064 | (3-amino-1-((1S,3S)-3-hydroxycyclohexyl)pyridin-2(1H)-one structure) | MS (ES): m/z 482.70 [M + H]+, LCMS purity: 97.49%, HPLC purity: 96.41%, CHIRAL HPLC: 49%, 49%, 1H NMR (DMSO-d6, 400 MHZ): 8.90 (s, 1H), 8.21-8.20 (d, J = 3.6 Hz, 2H), 8.09-8.07 (d, J = 9.2 Hz, 1H), 7.94-7.93 (d, J = 4 Hz, 1H), 7.48-7.46 (d, J = 5.6 Hz, 1H), 6.33-6.29 (t, J = 7.2 Hz, 1H), 6.21 (s, 1H), 5.32-5.25 (m, 1H), 4.36-4.28 (m, 1H), 4.15 (s, 1H), 3.73-3.67 (m, 1H), 3.51 (bs, 1H), 3.20 (s, 3H), 2.92-2.91 (d, J = 4.8 Hz, 3H), 2.19-2.05 (m, 2H), 2.00-1.93 (m, 2H), 1.90-1.83 (m, 2H), 1.80-1.62 (m, 4H), 1.44 (bs, 2H). |
| I-1066 | (3-amino-1-(5-fluoro-1-methyl-1H-pyrazol-4-yl)pyridin-2(1H)-one structure) | MS (ES): m/z 482.41 [M + H]+, LCMS purity: 100%, HPLC purity: 98.56%, CHIRAL HPLC: 49.57%, 50.26%, 1H NMR (DMSO-d6, 400 MHZ): 9.05 (bs, 1H), 8.32-8.30 (d, J = 7.6 Hz, 1H), 8.21 (s, 1H), 8.07-8.05 (d, J = 9.2 Hz, 1H), 7.97-7.96 (d, J = 8.8 Hz, 1H), 7.76-7.75 (d, J = 2.4 Hz, 1H), 7.39-7.37 (d, J = 5.6 Hz, 1H), 6.41-6.37 (t, J = 7.2 Hz, 1H), 6.23 (s, 1H), 4.34-4.30 (m, 1H), 3.80 (m, 3H), 3.74-3.68 (m, 1H), 3.20 (s, 3H), 2.90-2.89 (d, J = 4.4 Hz, 3H), 1.54-1.47 (m, 2H), 1.23 (bs, 2H). |
| I-1088 | (3-amino-1-(3-oxabicyclo[3.1.0]hexan-6-yl)pyridin-2(1H)-one structure) | MS (ES): m/z 465.851 [M + H]+, LCMS purity: 99%, HPLC purity: 97%, CHIRAL HPLC purity: 50: 49%, 1H NMR (DMSO-d6, 400 MHZ): 8.97 (s, 1H), 8.23-8.20 (m, 2H), 8.07-8.05 (d, J = 8.8 Hz, 1H), 7.94-7.93 (d, J = 4.4 Hz, 1H), 7.34-7.33 (d, J = 6.0 Hz, 1H), 6.28-6.26 (m, 1H), 6.24-6.21 (m, 1H), 4.34-4.30 (m, 1H), 4.02-4.00 (m, 2H), 3.75-3.67 (m, 3H), 3.20 (s, 3H), 3.16 (s, 1H), 2.92-2.90 (d, J = 5.2 Hz, 3H), 2.29 (s, 2H), 2.16-2.00 (m, 2H), 1.55-1.51 (m, 1H), 1.42-1.32 (m, 1H). |
| I-1093 | (3-amino-1-((1S,2S)-2-hydroxycyclobutyl)pyridin-2(1H)-one structure) | MS(ES): m/z 454.46 [M + H]+ LCMS purity: 100%, HPLC purity: 97.28%, CHIRAL HPLC: 48.87%, 51.12%, 1H NMR (DMSO-d6, 400 MHZ): 8.95 (s, 1H), 8.25-8.23 (d, J = 7.2 Hz, 1H), 8.20 (s, 1H), 8.09-8.07 (d, J = 9.2 Hz, 1H), 7.94-7.93 (d, J = 5.2 Hz, 1H), 7.54-7.52 (d, J = 6.4 Hz, 1H), 6.37-6.34 (t, J = 6.8 Hz, 1H), 6.22 (s, 1H), 5.64-5.63 (d, J = 5.6 Hz, 1H), 4.98-4.91 (m, 1H), 4.35-4.28 (m, 2H), 3.74-3.68 (m, 1H), 3.58 (s, 1H), 3.21 (s, 3H), 2.91-2.90 (d, J = 4.8 Hz, 3H), 2.14-2.04 (m, 3H), 1.63 (bs, 2H), 1.24 (bs, 2H). |
| I-1094 | (3-amino-1-((1R,2R)-2-hydroxycyclobutyl)pyridin-2(1H)-one structure) | MS(ES): m/z 454.62 [M + H]+ LCMS purity: 100%, HPLC purity: 98.40%, CHIRAL HPLC: 48.93%, 51.06%, 1H NMR (DMSO-d6, 400 MHZ): 8.95 (s, 1H), 8.25-8.23 (d, J = 7.2 Hz, 1H), 8.20 (s, 1H), 8.09-8.07 (d, J = 9.2 Hz, 1H), 7.94-7.93 (d, J = 5.2 Hz, 1H), 7.54-7.52 (d, J = 6.4 Hz, 1H), 6.37-6.34 (t, J = 6.8 Hz, 1H), 6.22 (s, 1H), 5.64-5.63 (d, J = 5.6 Hz, 1H), 4.98-4.91 (m, 1H), 4.39-4.28 (m, 2H), 3.74-3.68 (m, 1H), 3.58 (s, 1H), 3.21 (s, 3H), 2.91-2.90 (d, J = 4.8 Hz, 3H), 1.69 (bs, 4H), 1.35-1.31 (m, 1H), 1.24 (bs, 2H). |

TABLE 42-continued

| Compound | Intermediate | Characterization data |
|---|---|---|
| I-1095 | (structure: 3-amino-1-[1-(2-fluoroethyl)piperidin-3-yl]pyridin-2(1H)-one derivative) | MS (ES): 513.62 [M + H]+ LCMS purity: 100%, HPLC purity: 99.19%, CHIRAL HPLC: 49.75% 50.24%, 1H NMR (DMSO-d6, 400 MHZ): 8.93 (s, 1H), 8.25-8.23 (d, J = 7.2 Hz, 1H), 8.20 (s, 1H), 8.08-8.05 (d, J = 9.2 Hz, 1H), 7.93-7.91(d, J = 4.8 Hz, 1H), 7.61-7.59 (d, J = 6.8 Hz, 1H), 6.34-6.30 (t, J = 7.2 Hz, 1H), 6.23 (s, 1H), 4.95 (bs, 1H), 4.63-4.61 (t, J = 4.8 Hz, 1H), 4.51-4.49 (t, J = 4.8 Hz, 1H), 4.37-4.28 (m, 1H), 3.73-3.68 (m, 1H), 3.21 (s, 3H), 2.96 (bs, 1H), 2.92-2.91 (d, J = 4.8 Hz, 3H), 2.83 (bs, 1H), 2.75-2.73 (t, J = 4.4 Hz, 1H), 2.68-2.65 (t, J = 4.8 Hz, 1H), 2.22-2.16 (t, J = 10.4 Hz, 1H), 2.14-2.00 (m, 3H), 1.77 (bs, 3H), 1.66 (bs, 1H), 1.42-1.38 (m, 1H), 1.35-1.24 (m, 1H). |
| I-1097 | (structure: 3-amino-1-(2-methoxycyclohexyl)pyridin-2(1H)-one) | MS (ES): m/z 496.67 [M + H]+, LCMS purity: 99.37%, HPLC purity: 99.05%, CHIRAL HPLC: 49.28%, 49.87%, 1H NMR (DMSO-d6, 400 MHz): 8.89 (s, 1H), 8.25-8.23 (d, J = 7.6 Hz, 1H), 8.20 (s, 1H), 8.11-8.09 (m, 1H), 7.39-7.92 (d, J = 5.2 Hz, 1H), 7.42-7.40 (d, J = 6.8 Hz, 1H), 6.32-6.29 (t, J = 7.2 Hz, 1H), 6.19 (s, 1H), 4.91-4.88 (d, J = 12.8 Hz, 1H), 4.36-4.28 (m, 1H), 3.71-3.68 (m, 1H), 3.58 (s, 1H), 3.20 (s, 3H), 3.13-3.12 (d, J = 3.2 Hz, 3H), 2.92-2.91 (d, J = 4.8 Hz, 3H), 2.16-2.07 (m, 4H), 1.86 (s, 1H), 1.59-1.24 (m, 7H). |
| I-1098 | (structure: 3-amino-1-(3-methoxycyclohexyl)pyridin-2(1H)-one) | MS (ES): 496.67 [M + H]+ LCMS purity: 100%, HPLC purity: 97.68%, CHIRAL HPLC: 49.20%, 49.11%, 1H NMR (DMSO-d6, 400 MHZ): 8.92 (s, 1H), 8.22 (s, 1H), 8.20 (s, 1H), 8.07-8.06 (d, J = 4.4 Hz, 1H), 7.93-7.92 (d, J = 4.8 Hz, 1H), 7.50-7.48 (d, J = 7.2 Hz, 1H), 6.34-6.31 (t, J = 6.8 Hz, 1H), 6.21 (s, 1H), 5.12 (bs, 1H), 4.34-4.30 (m, 1H), 3.71 (bs, 2H), 3.26 (s, 3H), 3.20 (s, 3H), 2.92-2.91 (d, J = 8.4 Hz, 3H), 2.14 (bs, 1H), 2.07-2.03 (m, 2H), 1.91-1.82 (m, 2H), 1.35 (bs, 3H), 1.24 (bs, 3H), 0.88-0.85 (m, 1H). |
| I-1099 | (structure: 3-amino-1-(4-methoxycyclohexyl)pyridin-2(1H)-one) | MS (ES): m/z 496.70 [M + H]+, LCMS purity: 99.72%, HPLC purity: 97.69%, CHIRAL HPLC: 49%, 50%, 1H NMR (DMSO-d6, 400 MHZ): 8.92 (s, 1H), 8.22-8.20 (d, J = 8.8 Hz, 2H), 8.09-8.06 (d, J = 9.2 Hz, 1H), 7.93-7.92 (d, J = 4.8 Hz, 1H), 7.49-7.84 (d, J = 6.0 Hz, 1H), 6.34-6.33 (t, J = 7.2 Hz, 1H), 6.21 (s, 1H), 5.13 (s, 1H), 4.45-4.30 (m, 1H), 3.71-3.67 (m, 1H), 3.21 (s, 3H), 3.29 (s, 3H), 2.20-2.20 (d, J = 1.2 Hz 3H), 2.16-2.03 (m, 3H), 1.78-1.65 (m, 4H), 1.58-1.48 (m, 3H), 1.40-1.31 (m, 3H). |
| I-1102 | (structure: 8-amino-[1,2,4]triazolo[4,3-a]pyridine) | MS (ES): m/z 408.57 [M + H]+, LCMS purity: 100%, HPLC purity: 98.54%, CHIRAL HPLC: 48.03%, 51.74%, 1H NMR (DMSO-d6, 400 MHZ): 9.89 (s, 1H), 8.72-8.70 (d, J = 6.8 Hz, 1H), 8.57 (s, 1H), 8.28-8.26 (d, J = 7.6 Hz, 1H), 8.22 (s, 1H), 8.06 (s, 1H), 8.03 (s, 1H), 7.20-7.17 (t, J = 7.2 Hz, 1H), 6.18 (s, 1H), 4.27-4.21 (m, 1H), 3.15 (s, 3H), 2.94-2.93 (d, J = 4.8 Hz, 3H), 2.09-2.02 (m, 2H), 1.55 (bs, 1H), 1.23 (bs, 2H). |

102.2. Synthesis of N-(2-methoxycyclobutyl)-7-(methylamino)-5-(1-(2-(4-methylpiperazin-1-yl)ethyl)-1H-pyrrolo[2,3-b]pyridin-3-yl)pyrazolo[1,5-a]pyrimidine-3-carboxamide (I-885)

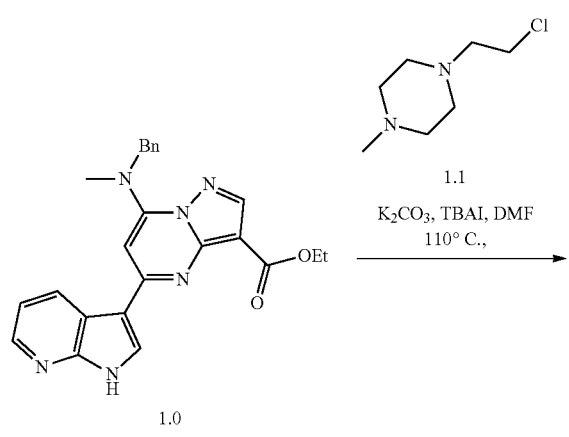

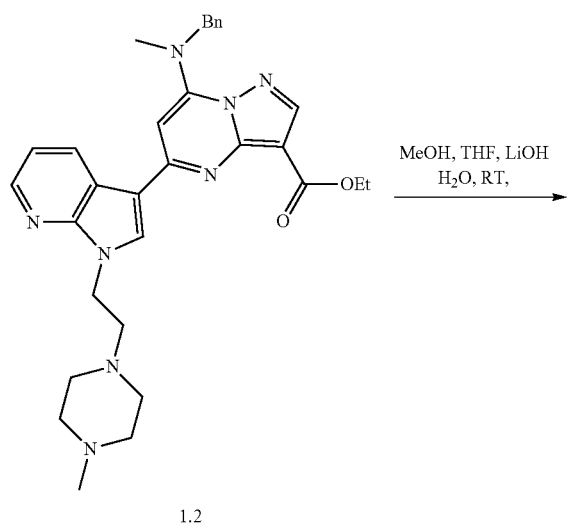

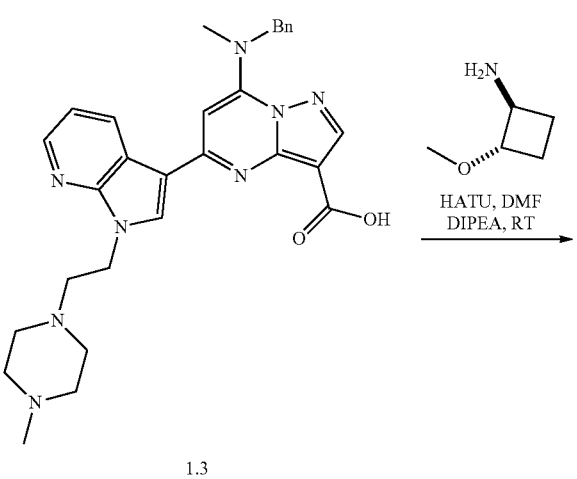

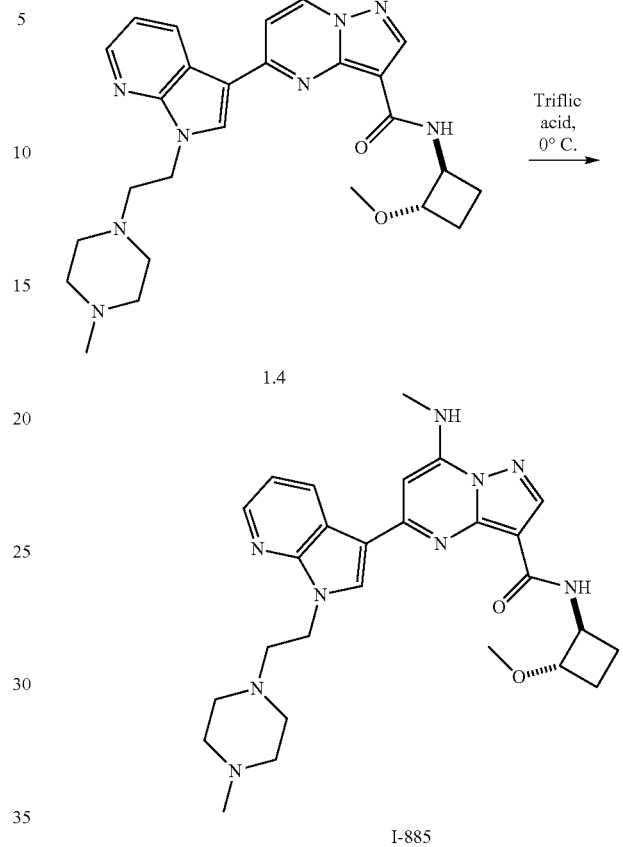

Synthesis of Compound 1.0.

Compound was synthesized as per experimental protocol Example 67 of I-653 to obtain 1.0 (0.500 g, Yield: 90.55%). MS (ES): m/z 427.48 [M+H]

Synthesis of Compound 1.2.

To a solution of 1.0 (0.500 g, 1.17 mmol, 1.0 eq) in N,N-Dimethyl formamide (5 mL) was added 1-(2-chloroethyl)-4-methylpiperazine (0.380 g, 2.34 mmol, 2.0 eq), Potassium carbonate (0.485 g, 3.57 mmol, 3.0 eq), followed by addition of Tetrabutylammonium iodide (0.043 g, 0.117 mmol, 0.1 eq). The reaction was stirred at 110° C. for 48 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 52% ethyl acetate in hexane to obtain pure 1.2 (0.184 g, Yield: 28.40%), MS(ES): m/z 553.68 [M+H]$^+$.

Synthesis of Compound 1.3:

To a solution of 1.2 (0.184 g, 0.332 mmol, 1.0 eq), in tetrahydrofuran: methanol: water (10 mL, 2:2:1) was added lithium hydroxide (0.069 g, 1.66 mmol, 5.0 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.120 g, Yield: 68.72%). MS(ES): m/z 525.63 [M+H]⁺.

Synthesis of Compound 1.4.

Compound was synthesized using general procedure A to obtain 1.4. (0.140 g, 75.53%), MS (ES): 608.34 [M+H]⁺

Synthesis of Compound I-885:

The compound 1.4 (0.140 g, 0.23 mmol, 1.0 eq) was dissolved in dichloromethane (5 mL). Triflic acid (1 mL) was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-885 (0.103 g, Yield: 86.38%). MS(ES): m/z 518.72 [M+H]⁺, LCMS purity: 99.18%, HPLC purity: 96.58%, CHIRAL HPLC: 49.57%, 47.97%, $^1$H NMR (DMSO-$d_6$, 400 MHZ): 8.77-8.76 (d, J=6.8 Hz, 1H), 8.69 (s, 1H), 8.53-8.51 (d, J=9.2 Hz, 1H), 8.42-8.41 (d, J=3.6 Hz, 1H), 8.38 (s, 1H), 8.29-8.28 (d, J=4.8 Hz, 1H), 7.33-7.30 (m, 1H), 6.69 (s, 1H), 4.52-4.48 (t, J=6.4 Hz, 2H), 4.41-4.37 (t, J=8 Hz, 1H), 3.88-3.82 (m, 1H), 3.25 (s, 3H), 3.12-3.10 (d, J=5.2 Hz, 3H), 2.85-2.82 (t, J=6.4 Hz, 2H), 1.34 (bs, 4H), 2.18 (s, 6H), 1.63-1.56 (m, 3H), 0.87-0.85 (m, 2H).

Additional compounds prepared by substantially the same method, and their characterization data, are listed in the Table 43 below. The intermediate corresponding to 1.1 of the above scheme is listed for each compound.

TABLE 43

| Compound | Intermediate | Characterization data |
|---|---|---|
| I-886 | 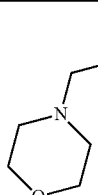 | MS (ES): m/z 505.27 [M + H]⁺, LCMS purity: 97.48%, HPLC purity: 96.18%, CHIRAL HPLC: 48.61%, 49.47%, $^1$H NMR (DMSO-$d_6$, 400 MHZ): 8.77-8.76 (d, J = 6.8 Hz, 1H), 8.71 (s, 1H), 8.53-8.51 (d, J = 8.8 Hz, 1H), 8.42-8.41 (d, J = 3.6 Hz, 1H), 8.38 (s, 1H), 8.30-8.29 (d, J = 4.8 Hz, 1H), 7.33-7.30 (m, 1H), 6.70 (s, 1H), 4.53-4.50 (t, J = 6.8 Hz, 2H), 4.43-4.39 (t, J = 7.6 Hz, 1H), 3.87-3.82 (m, 1H), 3.55 (bs, 4H), 3.24 (s, 3H), 3.11-3.10 (d, J = 4.8 Hz, 3H), 2.85-2.81 (t, J = 6.4 Hz, 2H), 1.60-1.50 (m, 3H), 1.24 (bs, 3H), 0.87-0.84 (m, 2H). |
| I-1065 | 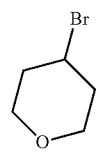 | MS (ES): m/z 476.67 [M + H]⁺, LCMS purity: 99.50%, HPLC purity: 97.91%, $^1$H NMR (DMSO-$d_6$, 400 MHZ): 8.90 (s, 1H), 8.80-8.78 (d, J = 7.2 Hz, 1H), 8.53-8.51 (d, J = 9.2 Hz, 1H), 8.43-8.42 (d, J = 3.6 Hz, 1H), 8.38 (s, 1H), 8.27-8.26 (d, J = 4.8 Hz, 1H), 7.35-7.32 (m, 1H), 6.83 (s, 1H), 4.43-4.39 (m, 1H), 4.10-4.08 (m, 2H), 3.85-3.81 (m, 1H), 3.66-3.61 (t, J = 11.6 Hz, 1H), 3.24 (s, 3H), 3.13-3.12 (d, J = 4.8 Hz, 3H), 2.23-2.14 (m, 4H), 2.03-2.00 (m, 3H), 1.60-1.50 (m, 3H). |

102.3. Synthesis of N-(2-methoxycyclobutyl)-7-(methylamino)-5-((2-(methylcarbamoyl)furan-3-yl)amino)pyrazolo[1,5-a]pyrimidine-3-carboxamide (I-1111)

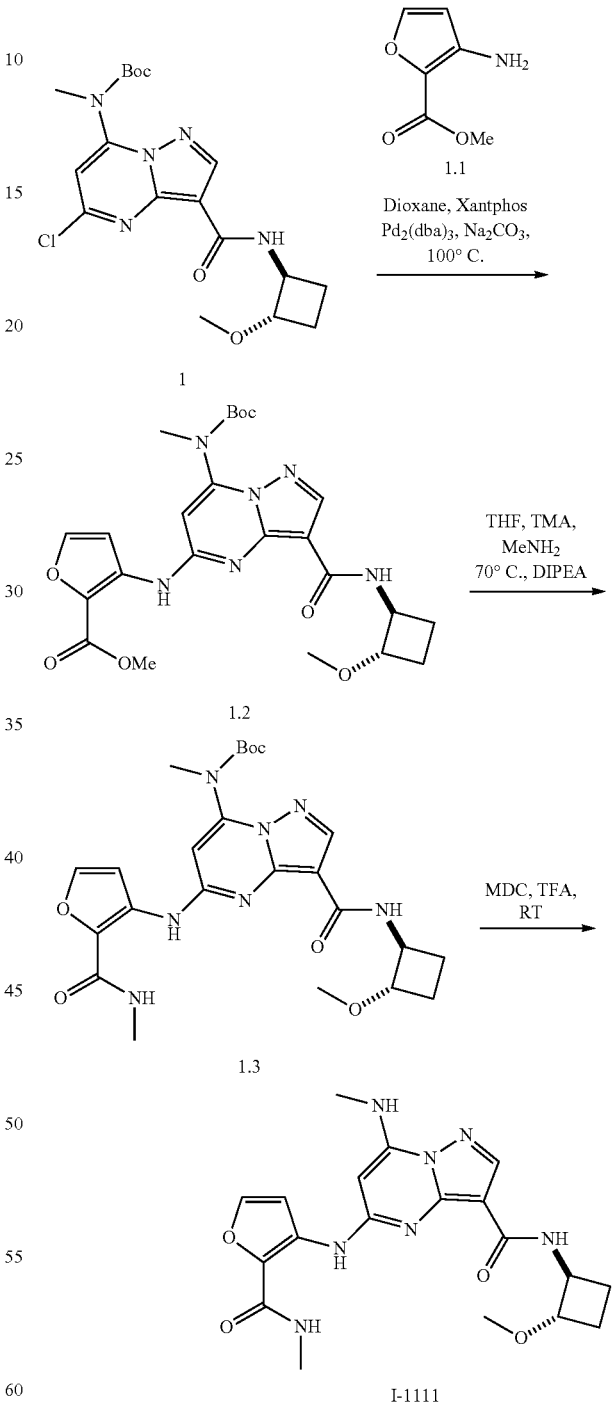

Synthesis of Compound 1.

Compound was synthesized as per experimental protocol Example 30 of I-814 to obtain 1. (Yield: 57.95%), MS (ES): m/z 410.16 [M+H]⁺

Synthesis of Compound 1.2.

Compound was synthesized using general procedure B to obtain 1.2. (0.190 g, Yield: 60.54%). MS (ES): m/z 515.22 [M+H]$^+$ Synthesis of Compound 1.3.

To a solution of 1.2 (0.190 g, 0.36 mmol, 1.0 eq) in tetrahydrofuran (3 mL) was added Trimethylamine (0.047 g, 0.81 mmol, 1.5 eq), Methylamine (0.025 g, 0.81 mmol, 1.5 eq) and N,N-Diisopropylethylamine (0.092 g, 0.72 mmol, 2 eq). The reaction was stirred at 70° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.3% methanol in dichloromethane to obtain pure 1.3. (0.150 g, 79.10%). MS(ES): m/z 514.24 [M+H]$^+$.

Synthesis of Compound I-1111:

Compound was synthesized using general procedure C to obtain I-1111 (0.120 g, 99.37%), MS (ES): m/z 414.25 [M+H]$^+$, LCMS purity: 100%, HPLC purity: 99.66%, CHIRAL HPLC: 49.93%, 49.84%, $^1$H NMR (DMSO-d$_6$, 400 MHZ): 9.36 (s, 1H), 8.28-8.27 (d, J=4.4 Hz, 1H), 8.21 (s, 1H), 8.12-8.09 (d, J=8.8 Hz, 1H), 8.01-8.00 (d, J=4.8 Hz, 1H), 7.93-7.92 (d, J=1.6 Hz, 1H), 7.40 (bs, 1H), 6.00 (bs, 1H), 4.33-4.29 (m, 1H), 3.74-3.68 (m, 1H), 3.21 (s, 3H), 2.94-2.93 (d, J=4.8 Hz, 3H), 2.79-2.78 (d, J=4.8 Hz, 3H), 2.12-2.05 (m, 2H), 1.55-1.45 (m, 1H), 1.24 (bs, 1H).

102.4. Chiral separation of N-(-2-methoxycyclobutyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-814)

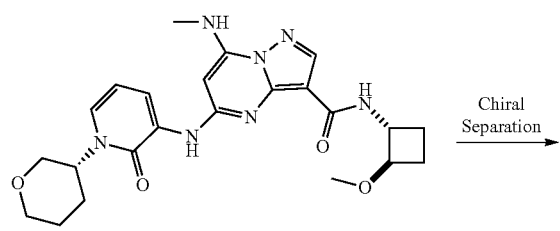

Chiral Separation →

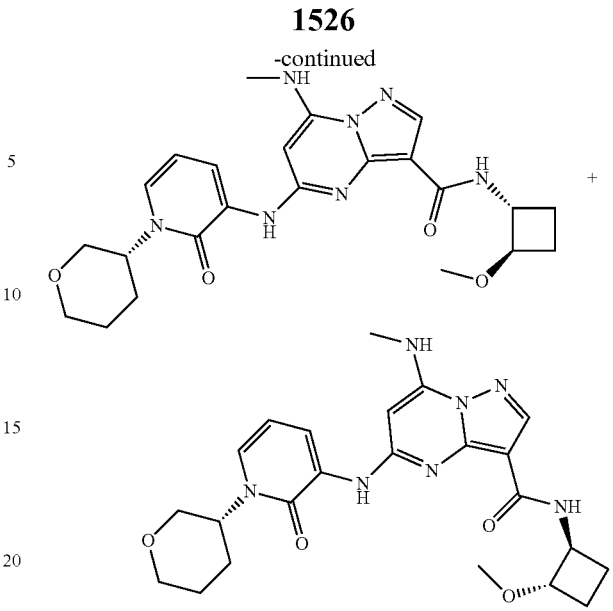

Isomers of I-814 (0.12 g), I-902 and I-903, were separated using column (CHIRAL PAK AD-H 250×4.6 mm, 5 u) 0.1% DEA in MEOH (70-30) to get pure fraction-1 (FR-a) and fraction-2 (FR-b). FR-a was concentrated under reduced pressure at 30° C. to afford pure FR-a (0.025 g). MS(ES): m/z 468.52 [M+H]$^+$, LCMS purity: 99.58%, HPLC purity: 99.24%, CHIRAL HPLC purity: 100%, $^1$H NMR (DMSO-d$_6$, 400 MHZ): 8.96 (s, 1H), 8.28-8.26 (d, J=5.6 Hz, 1H), 8.21 (s, 1H), 8.08-8.06 (d, J=9.2 Hz, 1H), 7.96-7.94 (d, J=4.8 Hz, 1H), 7.58-7.56 (d, J=6.8 Hz, 1H), 6.36-6.33 (t, J=7.2 Hz, 1H), 6.24 (s, 1H), 4.92-4.87 (m, 1H), 4.34-4.30 (m, 1H), 3.88-3.83 (m, 2H), 3.73-3.68 (m, 1H), 3.62-3.57 (m, 1H), 3.50-3.45 (t, J=8.8 Hz, 1H), 3.21 (s, 3H), 2.92-2.91 (d, J=4.8 Hz, 3H), 2.17-1.97 (m, 4H), 1.78-1.72 (m, 2H), 1.56-1.49 (m, 1H), 1.43-1.35 (m, 1H).

FR-b was concentrated under reduced pressure at 30° C. to afford pure FR-b (0.026 g). MS(ES): m/z 468.23 [M+H]$^+$, LCMS purity: 100%, HPLC purity: 99.27%, CHIRAL HPLC purity: 100%, $^1$H NMR (DMSO-d$_6$, 400 MHZ): 8.96 (s, 1H), 8.26-8.24 (d, J=6.8 Hz, 1H), 8.21 (s, 1H), 8.08-8.06 (d, J=7.6 Hz, 1H), 7.95-7.94 (d, J=5.2 Hz, 1H), 7.57-7.56 (d, J=6.4 Hz, 1H), 6.36-6.33 (t, J=7.2 Hz, 1H), 6.24 (s, 1H), 4.92-4.87 (m, 1H), 4.34-4.28 (m, 1H), 3.88-3.83 (m, 2H), 3.73-3.68 (m, 1H), 3.62-3.57 (m, 1H), 3.50-3.45 (t, J=8.8 Hz, 1H), 3.21 (s, 3H), 2.92-2.91 (d, J=4.8 Hz, 3H), 2.16-1.97 (m, 4H), 1.81-1.72 (m, 2H), 1.58-1.48 (m, 1H), 1.43-1.32 (m, 1H).

Additional compounds prepared by substantially the same method, and their characterization data, are listed in the Table 44 below.

TABLE 44

| Compound | Isomers | Characterization data |
|---|---|---|
| I-815 | I-876 I-877 | FR-a: MS (ES): m/z 468.37 [M + H]$^+$, LCMS purity: 100%, HPLC purity: 98.91%, CHIRAL HPLC purity: 98.87%, $^1$H NMR (DMSO-d$_6$, 400 MHZ): 8.96 (s, 1H), 8.26-8.24 (d, J = 7.2 Hz, 1H), 8.21 (s, 1H), 8.08-8.06 (d, J = 9.2 Hz, 1H), 7.95-7.94 (d, J = 4.8 Hz, 1H), 7.58-7.56 (d, J = 6.8 Hz, 1H), 7.39-7.31 (m, 1H), 6.36-6.33 (t, J = 7.2 Hz, 1H), 6.24 (s, 1H), 4.92-4.87 (m, 1H), 4.38-4.31 (m, 1H), 3.89-3.83 (m, 1H), 3.74-3.68 (m, 1H), 3.63-3.57 (m, 1H), 3.50-3.46 (m, 1H), 3.21 (s, 3H), 2.91 (s, 3H), 2.22-1.98 (m, 3H), 1.78-1.72 (m, 1H), 1.56-1.49 (m, 1H), 1.42-1.24 (m, 3H). FR-b: MS (ES): m/z 468.71 [M + H]$^+$, LCMS purity: 99.85%, HPLC purity: 99.04%, CHIRAL HPLC purity: 98.53%, $^1$H NMR (DMSO-d$_6$, 400 MHZ): 8.96 (s, 1H), 8.26-8.24 (d, J = 7.2 Hz, 1H), 8.21 (s, 1H), 8.08-8.06 (d, J = 9.2 Hz, 1H), 7.95-7.94 (d, J = 4.8 Hz, 1H), |

TABLE 44-continued

| Compound | Isomers | Characterization data |
| --- | --- | --- |
| | | 7.58-7.56 (d, J = 6.4 Hz, 1H), 7.39-7.30 (m, 1H), 6.36-6.33 (t, J = 7.2 Hz, 1H), 6.24 (s, 1H), 4.92-4.87 (m, 1H), 4.38-4.28 (m, 1H), 3.88-3.83 (m, 1H), 3.74-3.68 (m, 1H), 3.63-3.57 (m, 1H), 3.50-3.46 (m, 1H), 3.21 (s, 3H), 2.91 (s, 3H), 2.22-1.98 (m, 3H), 1.78-1.69 (m, 1H), 1.58-1.48 (m, 1H), 1.42-1.25 (m, 3H). |
| I-816 | I-908 I-909 | FR-a: MS (ES): m/z 461.42 [M + H]$^+$, LCMS purity: 99.70%, HPLC purity: 99.53%, CHIRAL HPLC purity: 100%, $^1$H NMR (DMSO-d$_6$, 400 MHZ): 9.05 (s, 1H), 8.27 (s, 1H), 8.37-8.35 (m, 2H), 8.23 (s, 1H), 8.12-8.05 (m, 1H), 7.97 (s, 1H), 7.88-7.87 (d, J = 8.0 Hz, 1H), 7.65-7.63 (d, J = 6.0 Hz, 1H), 7.58-7.56 (m, 1H), 6.48-6.45 (t, J = 6.8 Hz, 1H), 6.25 (s, 1H), 4.37-4.33 (m, 1H), 3.76-3.74 (d, J = 7.6 Hz, 1H), 3.23 (s, 3H), 2.93 (s, 3H), 2.82-2.79 (m, 2H), 2.16-2.08 (m, 2H). FR-b: MS (ES): m/z 461.57 [M + H]$^+$, LCMS purity: 95.64%, HPLC purity: 95.06%, CHIRAL HPLC purity: 98.21%, $^1$H NMR (DMSO-d$_6$, 400 MHZ): 8.66-8.65 (d, J = 3.6 Hz, 1H), 8.38 (s, 1H), 8.34-8.32 (d, J = 5.6 Hz, 1H), 8.22 (s, 1H), 8.15-8.12 (d, J = 9.2 Hz, 1H), 8.08-8.04 (t, J = 8.0 Hz, 1H), 7.85-7.83 (d, J = 8.0 Hz, 1H), 7.63-7.61 (d, J = 7.2 Hz, 1H), 7.57-7.54 (m, 1H), 6.48-6.45 (t, J = 7.2 Hz, 1H), 6.19 (s, 1H), 4.35-4.31 (m, 1H), 3.76-3.71 (m, 2H), 3.21 (s, 3H), 2.92 (s, 3H), 2.82-2.79 (m, 2H), 2.17-2.06 (m, 2H). |
| I-817 (Chiral separation when methylamino at position 7 is protected by Boc, followed by removal of Boc) | I-926 I-927 | FR-a: MS (ES): m/z 479.37 [M + H]$^+$, LCMS purity: 98.13%, HPLC purity: 98.03%, Chiral HPLC: 99.05%, $^1$H NMR (DMSO-d$_6$, 400 MHZ): 9.05 (s, 1H), 8.68 (s, 1H), 8.36-8.34 (d, J = 6.2 Hz, 1H), 8.23 (s, 1H), 8.11-8.09 (d, J = 8 Hz, 1H), 8.05-8.04 (t, J = 4.8 Hz, 1H), 7.97 (s, 1H), 7.61-7.59 (d, J = 8 Hz, 1H), 6.48-6.46 (d, J = 8 Hz, 1H), 6.24 (s, 1H), 4.36-4.34 (t, J = 8.5 Hz, 1H), 3.75-3.73 (d, J = 7.3 Hz, 1H), 3.22 (s, 3H), 2.92 (s, 3H), 2.1-2.06 (m, 2H), 1.56-1.54 (t, J = 8 Hz, 1H), 1.43-1.35 (m, 1H), 1.24 (bs, 1H). FR-b: MS (ES): m/z 479.41 [M + H]$^+$, LCMS purity: 100%, HPLC purity: 98.60 Chiral HPLC: 99.08%, $^1$H NMR (DMSO-d$_6$, 400 MHZ): 9.05 (s, 1H), 8.68-8.67 (d, J = 4.2 Hz, 1H), 8.36-8.34 (d, J = 6.2 Hz, 1H), 8.23 (s, 1H), 8.11-8.09 (d, J = 8 Hz, 1H), 8.05-8.04 (t, J = 4.8 Hz, 1H), 7.97 (s, 1H), 7.61-7.59 (d, J = 8 Hz, 1H), 6.48-6.46 (t, J = 8 Hz, 1H), 6.24 (s, 1H), 4.36-4.34 (t, J = 8.5 Hz, 1H), 3.75-3.73 (m, 1H), 3.22 (s, 3H), 2.92 (s, 3H), 2.1-2.06 (m, 2H), 1.56-1.54 (t, J = 8 Hz, 1H), 1.43-1.35 (m, 1H), 1.24 (bs, 1H). |
| I-843 (Chiral separation when methylamino at position 7 is protected by Boc, followed by removal of Boc) | I-973 I-974 | FR-a: MS (ES): m/z 475.66 [M + H]$^+$, LCMS purity: 100%, HPLC purity: 98.05%, CHIRAL HPLC purity: 99.89%, $^1$H NMR (DMSO-d$_6$, 400 MHZ): 8.35-8.32 (d, J = 8 Hz, 1H), 8.23 (s, 1H), 8.06-8.00 (m, 3H), 7.51-7.49 (m, 3H), 6.45-6.43 (t, J = 8 Hz, 1H), 6.21 (s, 1H), 4.32-4.30 (t, J = 8 Hz, 1H), 3.73-3.71 (d, J = 8 Hz, 3H), 3.21 (s, 3H), 2.93-2.91 (d, 3H), 2.20 (s, 2H), 2.14-2.05 (m, 1H), 1.52-1.50 (t, J = 8 Hz, 1H), 1.38-1.35 (t, J = 12 Hz, 1H), 1.27-1.25 (d, J = 8 Hz, 1H). FR-b: MS (ES): m/z 475.66 [M + H]$^+$, LCMS purity: 100%, HPLC purity: 99.17%, CHIRAL HPLC purity: 96.45%, $^1$H NMR (DMSO-d$_6$, 400 MHZ): 9.10 (s, 1H), 8.35-8.33 (d, J = 8 Hz, 1H), 8.23 (s, 1H), 8.06-8.00 (m, 3H), 7.51-7.49 (m, 3H), 6.45-6.43 (t, J = 8 Hz, 1H), 6.21 (s, 1H), 4.31-4.29 (t, J = 8 Hz, 1H), 3.72-3.70 (d, J = 8 Hz, 1H), 3.21 (s, 3H), 2.93-2.91 (d, J = 8 Hz, 3H), 2.20 (s, 2H), 2.14-2.05 (m, 1H), 1.52-1.50 (t, J = 8 Hz, 1H), 1.38-1.35 (t, J = 12 Hz, 1H), 1.27-1.25 (d, J = 8 Hz, 1H). |
| I-863 (Chiral separation when methylamino at position 7 is protected by Boc, followed by removal of Boc) | I-904 I-905 | FR-a: MS (ES): m/z 479.31 [M + H]$^+$, LCMS purity: 100%, HPLC purity: 98.30%, Chiral HPLC: 98.50 $^1$H NMR (DMSO-d$_6$, 400 MHZ): 9.08 (s, 1H), 8.53-8.52 (d, J = 4.6 Hz, 1H), 8.39-8.37 (d, J = 6.8 Hz, 1H), 8.23 (s, 1H), 8.11 (s, 1H), 8.09-8.06 (d, J = 12 Hz, 1H), 7.99-7.98 (d, J = 4 Hz, 1H), 7.76-7.72 (m, 1H), 7.50-7.49 (d, J = 4.2 Hz, 1H), 6.50-6.48 (t, J = 8 Hz, 1H), 6.22 (s, 1H), 4.36-4.34 (t, J = 8 Hz, 1H), 3.77-3.72 (m, 1H), 3.22 (s, 3H), 2.91-2.90 (d, J = 4 Hz, 3H), 2.18-2.06 (m, 1H), 1.56-1.46 (m, 1H), 1.44-1.37 (m, 1H), 1.25 (s, 1H). FR-b: MS (ES): m/z 479.31 [M + H]$^+$, LCMS purity: 97.33%, HPLC purity: 98.61% Chiral HPLC: 100%, $^1$H NMR (DMSO-d$_6$, 400 MHZ): 9.08 (s, 1H), 8.53-8.52 (d, J = 4.6 Hz, 1H), 8.39-8.37 (d, J = 6.8 Hz, 1H), 8.23 (s, 1H), 8.11 (s, 1H), 8.09-8.06 (d, J = 12 Hz, 1H), 7.99-7.98 (d, J = 4 Hz, 1H), 7.76-7.72 (m, 1H), 7.50-7.49 (d, J = 4.2 Hz, 1H), 6.50-6.48 (t, J = 8 Hz, 1H), 6.22 (s, 1H), 4.36-4.34 (t, J = 8 Hz, 1H), 3.77-3.72 (m, 1H), 3.22 (s, 3H), 2.92-2.91 (d, J = 4 Hz, 3H), 2.18-2.06 (m, 1H), 1.56-1.46 (m, 1H), 1.44-1.37 (m, 1H), 1.25 (s, 1H). |
| I-864 | I-922 I-923 | FR-a: MS (ES): m/z 461.62 [M + H]$^+$, LCMS purity: 100%, HPLC purity: 100%, CHIRAL HPLC purity: 99.19%, $^1$H NMR (DMSO-d$_6$, 400 MHZ): 9.04 (s, 1H), 8.77-8.76 (d, J = 2.0 Hz, 1H), 8.70-8.69 (d, J = 3.6 Hz, 1H), 8.40-8.38 (d, J = 7.6 Hz, 1H), 8.23 (s, 1H), 8.10-8.08 (d, J = 5.2 Hz, 1H), 8.04-8.02 (d, J = 8.4 Hz, 1H), 7.97-7.96 (d, J = 4.8 Hz, 1H), 7.66-7.62 (m, 1H), 7.48-7.47 (m, 1H), 6.46-6.43 (m, 1H), 6.26 (s, 1H), 4.39-4.31 (m, 1H), 3.79-3.73 (m, 1H), |

TABLE 44-continued

| Compound | Isomers | Characterization data |
|---|---|---|
| | | 3.24 (s, 3H), 2.92-2.91 (d, J = 4.4 Hz, 3H), 2.19-2.06 (m, 2H), 1.60-1.38 (m, 2H).<br>FR-b: MS (ES): m/z 461.47 [M + H]+, LCMS purity: 100%, HPLC purity: 96.91%, CHIRAL HPLC purity: 95.44%, $^1$H NMR (DMSO-$d_6$, 400 MHZ): 9.05 (s, 1H), 8.77 (s, 1H), 8.70-8.69 (d, J = 4.0 Hz, 1H), 8.39-8.37 (d, J = 6.8 Hz, 1H), 8.23 (s, 1H), 8.10-8.08 (d, J = 4.8 Hz, 1H), 8.04-8.02 (d, J = 8.0 Hz, 1H), 7.98-7.97 (d, J = 4.8 Hz, 1H), 7.65-7.62 (m, 1H), 7.48-7.47 (m, 1H), 6.46-6.43 (m, 1H), 6.26 (s, 1H), 4.37-4.31 (m, 1H), 3.78-3.73 (m, 1H), 3.23 (s, 3H), 2.92-2.91 (d, J = 4.4 Hz, 3H), 2.19-2.06 (m, 2H), 1.57-1.35 (m, 2H). |
| I-865 (Chiral separation when methylamino at position 7 is protected by Boc, followed by removal of Boc) | I-924 I-925 | FR-a: MS (ES): m/z 475.76 [M + H]+, LCMS purity: 98.44%, HPLC purity: 97.44%, Chiral HPLC: 99.82%, $^1$H NMR (DMSO-$d_6$, 400 MHZ): 9.02 (s, 1H), 8.48-8.47 (d, J = 4 Hz, 1H), 8.40-8.38 (d, J = 6.4 Hz, 1H), 8.23 (s, 1H), 8.13-8.10 (m, 1H), 7.99-7.94 (m, 1H), 7.55-7.52 (m, 1H), 7.37-7.35 (d, J = 6.8 Hz, 1H), 6.46-6.44 (t, J = 7 Hz, 1H), 6.23 (s, 1H), 4.36-4.30 (m, 1H), 3.78-3.73 (m, 2H), 3.23-3.22 (d, J = 4.6 Hz, 3H), 2.92-2.91 (d, J = 4.6 Hz, 3H), 2.1-2.06 (m, 2H), 1.56-1.54 (t, J = 8 Hz, 1H), 1.43-1.35 (m, 2H), 1.24 (s, 2H).<br>FR-b: MS (ES): m/z 475.71 [M + H]+, LCMS purity: 97.81%, HPLC purity: 97.42% Chiral HPLC: 99.15%, $^1$H NMR (DMSO-$d_6$, 400 MHZ): 9.02 (s, 1H), 8.48-8.47 (d, J = 4 Hz, 1H), 8.40-8.38 (d, J = 6.4 Hz, 1H), 8.23 (s, 1H), 8.13-8.10 (m, 1H), 7.99-7.94 (m, 1H), 7.55-7.52 (m, 1H), 7.37-7.35 (d, J = 6.8 Hz, 1H), 6.46-6.44 (t, J = 7 Hz, 1H), 6.23 (s, 1H), 4.36-4.30 (m, 1H), 3.78-3.73 (m, 2H), 3.23-3.22 (d, J = 4.6 Hz, 3H), 2.92-2.91 (d, J = 4.6 Hz, 3H), 2.1-2.06 (m, 2H), 1.56-1.54 (t, J = 8 Hz, 1H), 1.43-1.35 (m, 2H), 1.24 (s, 2H). |
| I-885 | I-952 I-953 | FR-a: MS (ES): m/z 518.99 [M + H]+, LCMS purity: 95.12%, HPLC purity: 96.78%, CHIRAL HPLC purity: 99.11%, $^1$H NMR (DMSO-$d_6$, 400 MHZ): 8.82-8.80 (m, 1H), 8.24 (s, 2H), 8.36 (s, 1H), 7.33-7.31 (m, 1H), 6.60 (s, 1H), 4.60-4.51 (m, 3H), 3.95-3.91 (m, 1H), 3.37 (s, 3H), 3.19 (s, 3H), 2.97-2.95 (m, 2H), 2.80-2.60 (m, 6H), 2.35 (s, 3H), 2.33-2.20 (m, 4H), 1.73-1.61 (m, 4H).<br>FR-b: MS (ES): m/z 518.62 [M + H]+, LCMS purity: 95.22%, HPLC purity: 96.64%, CHIRAL HPLC purity: 95.79%, $^1$H NMR (DMSO-$d_6$, 400 MHZ): 8.82-8.80 (m, 1H), 8.24 (s, 2H), 8.36 (s, 1H), 7.33-7.31 (m, 1H), 6.60 (s, 1H), 4.60-4.51 (m, 3H), 3.95-3.91 (m, 1H), 3.37 (s, 3H), 3.19 (s, 3H), 2.97-2.95 (m, 2H), 2.80-2.60 (m, 6H), 2.35 (s, 3H), 2.33-2.20 (m, 4H), 1.73-1.61 (m, 4H). |
| I-890 (Chiral separation when methylamino at position 7 is protected by Boc, followed by removal of Boc) | I-975 I-976 | FR-a: MS (ES): m/z 465.66 [M + H]+, LCMS purity: 100%, HPLC purity: 98.05%, CHIRAL HPLC purity: 99.89%, $^1$H NMR (DMSO-$d_6$, 400 MHZ): 8.34-8.33 (d, J = 8 Hz, 1H), 8.23 (s, 1H), 8.06-8.00 (m, 3H), 7.51-7.49 (m, 1H), 6.47-6.43 (t, J = 8 Hz, 1H), 6.21 (s, 1H), 4.33-4.29 (t, J = 8 Hz, 1H), 3.72-3.70 (d, J = 8 Hz, 1H), 3.21 (s, 3H), 2.92-2.91 (d, J = 4.8 Hz, 3H), 2.20 (s, 3H), 2.13-2.05 (m, 2H), 1.54-1.49 (t, J = 8 Hz, 1H), 1.40-1.35 (t, J = 12 Hz, 1H), 1.27-1.24 (d, J = 8 Hz, 1H).<br>FR-b: MS (ES): m/z 465.66 [M + H]+, LCMS purity: 100%, HPLC purity: 99.17%, CHIRAL HPLC purity: 96.45%, $^1$H NMR (DMSO-$d_6$, 400 MHZ): 9.10 (s, 1H), 8.34-8.33 (d, J = 8 Hz, 1H), 8.23 (s, 1H), 8.06-8.00 (m, 3H), 7.51-7.49 (m, 1H), 6.47-6.43 (t, J = 8 Hz, 1H), 6.21 (s, 1H), 4.33-4.29 (t, J = 8 Hz, 1H), 3.74-3.69 (m, 1H), 3.21 (s, 3H), 2.92-2.91 (d, J = 4.8 Hz, 3H), 2.20 (s, 3H), 2.16-2.00 (m, 3H), 1.27-1.25 (d, J = 8 Hz, 1H). |
| I-895 (Chiral separation when methylamino at position 7 is protected by Boc, followed by removal of Boc) | I-1074 I-1075 | FR-a: MS (ES): m/z 465.37 [M + H]+, LCMS purity: 95.71%, HPLC purity: 96.10%, Chiral HPLC: 100%, $^1$H NMR (DMSO-$d_6$, 400 MHZ): 9.14 (s, 1H), 8.32-8.31 (d, J = 7.2 Hz, 1H), 8.23 (s, 1H), 8.07-8.05 (d, J = 8.8 Hz, 1H), 8.00-7.99 (d, J = 0.8 Hz, 1H), 7.59-7.57 (d, J = 7.2 Hz, 1H), 7.41 (s, 1H), 6.51-6.47 (t, J = 7.2 Hz, 1H), 6.23 (s, 1H), 4.34-4.30 (t, J = 8.0 Hz, 1H), 3.74-3.68 (m, 1H), 3.21 (s, 3H), 2.93-2.91 (d, J = 4.8 Hz, 3H), 2.52 (s, 3H), 2.16-2.04 (m, 2H), 1.55-1.50 (m, 1H), 1.42-1.25 (m, 1H).<br>FR-b: MS (ES): m/z 465.42 [M + H]+, LCMS purity: 98.98%, HPLC purity: 95.32%, Chiral HPLC: 99.73%, $^1$H NMR (DMSO-$d_6$, 400 MHZ): 9.14 (s, 1H), 8.32-8.31 (d, J = 7.2 Hz, 1H), 8.22 (s, 1H), 8.06-8.04 (d, J = 9.2 Hz, 1H), 8.00-7.99 (d, J = 4.8 Hz, 1H), 7.59-7.57 (d, J = 6.8 Hz, 1H), 7.41 (s, 1H), 6.51-6.47 (t, J = 7.2 Hz, 1H), 6.22 (s, 1H), 4.35-4.26 (m, 1H), 3.72-3.67 (m, 1H), 3.20 (s, 3H), 2.91-2.90 (d, J = 4.8 Hz, 3H), 2.52 (s, 3H), 2.15-2.02 (m, 2H), 1.55-1.47 (t, J = 8.8 Hz, 1H), 1.42-1.25 (m, 1H). |
| I-917 | I-979 I-980 | FR-a: MS (ES): m/z 426.67 [M + H]+, LCMS purity: 100%, HPLC purity: 99.03%, CHIRAL HPLC purity: 100%, $^1$H NMR (DMSO-$d_6$, 400 MHZ): 8.94 (s, 1H), 8.24-8.21 (m, 2H), 8.09-8.07 (d, J = 8.8 Hz, 1H), 7.94-7.93 (d, J = 4.8 Hz, 1H), 7.50-7.48 (d, J = 6.8 Hz, 1H), 6.36-6.33 (t, J = 6.8 Hz, 1H), 6.23 (s, 1H), 5.22-5.16 (m, 1H), 4.37-4.28 (m, 1H), 3.73-3.68 (q, J = 7.6 Hz, 1H), 3.21 (s, 3H), 2.92-2.91 (d, J = 4.4 Hz, 3H), 2.17-2.04 (m, 2H), 1.59-1.47 (m, 1H), 1.40-1.36 (m, 7H).<br>FR-b: MS (ES): m/z 426.47 [M + H]+, LCMS purity: 97.99%, HPLC |

TABLE 44-continued

| Compound | Isomers | Characterization data |
| --- | --- | --- |
| | | purity: 97.52%, CHIRAL HPLC purity: 99.10%, $^1$H NMR (DMSO-$d_6$, 400 MHZ): 8.94 (s, 1H), 8.24-8.21 (m, 2H), 8.09-8.07 (d, J = 9.2 Hz, 1H), 7.94-7.93 (d, J = 4.8 Hz, 1H), 7.50-7.48 (d, J = 6.4 Hz, 1H), 6.36-6.33 (t, J = 6.8 Hz, 1H), 6.23 (s, 1H), 5.22-5.16 (m, 1H), 4.35-4.28 (m, 1H), 3.74-3.68 (m, 1H), 3.21 (s, 3H), 2.92-2.91 (d, J = 4.4 Hz, 3H), 2.17-2.04 (m, 2H), 1.56-1.49 (m, 1H), 1.40-1.36 (m, 7H). |
| I-959 (Chiral separation when methylamino at position 7 is protected by Boc, followed by removal of Boc) | I-1105 I-1106 | FR-a: MS (ES): m/z 510.37 [M + H]$^+$, LCMS purity: 98.33%, HPLC purity: 95.90%, Chiral HPLC: 97.91%, $^1$H NMR (DMSO-$d_6$, 400 MHZ): 8.92 (s, 1H), 8.23-8.22 (d, J = 7.2 Hz, 1H), 8.20 (s, 1H), 8.08-8.06 (d, J = 8.8 Hz, 1H), 7.95-7.94 (d, J = 4.8 Hz, 1H), 7.58-7.57 (d, J = 6.0 Hz, 1H), 6.32-6.29 (t, J = 7.2 Hz, 1H), 6.21 (s, 1H), 4.76 (bs, 1H), 4.33-4.29 (t, J = 8.0 Hz, 1H), 3.72-3.67 (m, 1H), 3.19 (s, 3H), 3.16 (s, 3H), 2.91-2.90 (d, J = 4.8 Hz, 3H), 2.14-2.04 (m, 2H), 1.94 (bs, 3H), 1.88 (bs, 2H), 1.60-1.51 (m, 3H), 1.40-1.35 (t, J = 9.6 Hz, 1H), 1.24 (bs, 4H).<br>FR-b: MS (ES): m/z 510.57 [M + H]$^+$, LCMS purity: 96.92%, HPLC purity: 95.82%, Chiral HPLC: 97.23%, $^1$H NMR (DMSO-$d_6$, 400 MHZ): 8.92 (s, 1H), 8.23-8.21 (d, J = 6.4 Hz, 1H), 8.20 (s, 1H), 8.08-8.06 (d, J = 8.8 Hz, 1H), 7.95-7.93 (d, J = 5.2 Hz, 1H), 7.58-7.57 (d, J = 6.0 Hz, 1H), 6.33-6.29 (t, J = 7.2 Hz, 1H), 6.21 (s, 1H), 4.76 (bs, 1H), 4.33-4.29 (t, J = 8.8 Hz, 1H), 3.73-3.67 (m, 1H), 3.19 (s, 3H), 3.16 (s, 3H), 2.91-2.90 (d, J = 4.8 Hz, 3H), 2.14-2.04 (m, 2H), 1.94 (bs, 3H), 1.88 (bs, 2H), 1.60-1.51 (m, 3H), 1.40-1.35 (t, J = 9.6 Hz, 1H), 1.24 (bs, 4H). |
| I-984 | I-1084 I-1085 | FR-a: MS (ES): m/z 479.37 [M + H]$^+$, LCMS purity: 95.50%, HPLC purity: 95.98%, CHIRAL HPLC purity: 99.31%, $^1$H NMR (DMSO-$d_6$, 400 MHZ): 9.08 (s, 1H), 8.76-8.75 (d, J = 2.4 Hz, 1H), 8.69 (s, 1H), 8.40-8.38 (d, J = 7.2 Hz, 1H), 8.24 (s, 1H), 8.19-8.17 (d, J = 5.6 Hz, 1H), 8.10-8.08 (d, J = 9.2 Hz, 1H), 7.99-7.98 (d, J = 4.8 Hz, 1H), 7.52-7.50 (d, J = 6.8 Hz, 1H), 6.47-6.44 (t, J = 6.8 Hz, 1H), 6.27 (s, 1H), 4.37-4.33 (t, J = 8.0 Hz, 1H), 3.78-3.72 (m, 1H), 3.23 (s, 3H), 2.92-2.91 (d, J = 4.4 Hz, 3H), 2.19-2.08 (m, 2H), 1.57-1.40 (m, 2H).<br>FR-b: MS (ES): m/z 479.37 [M + H]$^+$, LCMS purity: 99.53%, HPLC purity: 97.41%, CHIRAL HPLC purity: 95.64%, $^1$H NMR (DMSO-$d_6$, 400 MHZ): 9.07 (s, 1H), 8.75-8.74 (d, J = 2.4 Hz, 1H), 8.68 (s, 1H), 8.38-8.37 (d, J = 7.6 Hz, 1H), 8.22 (s, 1H), 8.18-8.16 (d, J = 9.6 Hz, 1H), 8.09-8.07 (d, J = 9.2 Hz, 1H), 7.99-7.98 (d, J = 4.4 Hz, 1H), 7.51-7.49 (d, J = 6.8 Hz, 1H), 6.46-6.43 (t, J = 7.2 Hz, 1H), 6.26 (s, 1H), 4.35-4.31 (t, J = 8.0 Hz, 1H), 3.75-3.73 (m, 1H), 3.22 (s, 3H), 2.91-2.90 (d, J = 4.8 Hz, 3H), 2.15-2.06 (m, 2H), 1.55-1.40 (m, 2H). |
| I-995 (Chiral separation when methylamino at position 7 is protected by Boc, followed by removal of Boc) | I-1082 I-1083 | FR-a: MS (ES): m/z 496.41 [M + H]$^+$, LCMS purity: 100%, HPLC purity: 99.20%, Chiral HPLC: 98.30%, $^1$H NMR (DMSO-$d_6$, 400 MHZ): 8.91 (s, 1H), 8.23-8.21 (m, 2H), 8.08-8.06 (d, J = 9.2 Hz, 1H), 7.94-7.93 (d, J = 4.8 Hz, 1H), 7.53-7.51 (d, J = 6.0 Hz, 1H), 6.35-6.31 (t, J = 7.2 Hz, 1H), 6.22 (s, 1H), 4.88-4.82 (t, J = 12.0 Hz, 1H), 4.36-4.28 (m, 1H), 3.73-3.67 (m, 1H), 3.28 (s, 3H), 3.21 (s, 3H), 2.92-2.91 (t, J = 4.8 Hz, 3H), 2.20-2.03 (m, 4H), 1.92-1.11 (m, 8H).<br>FR-b: MS (ES): m/z 496.26 [M + H]$^+$, LCMS purity: 100%, HPLC purity: 99.38%, Chiral HPLC: 100%, $^1$H NMR (DMSO-$d_6$, 400 MHZ): 8.91 (s, 1H), 8.23-8.21 (m, 2H), 8.08-8.06 (d, J = 9.2 Hz, 1H), 7.94-7.93 (d, J = 4.8 Hz, 1H), 7.53-7.51 (d, J = 6.0 Hz, 1H), 6.35-6.32 (t, J = 7.2 Hz, 1H), 6.22 (s, 1H), 4.85 (m, 1H), 4.34-4.30 (m, 1H), 3.73-3.67 (m, 1H), 3.28 (s, 3H), 3.20 (s, 3H), 2.93-2.91 (t, J = 4.8 Hz, 3H), 2.20-2.03 (m, 4H), 1.92-1.11 (m, 8H). |
| I-996 | I-1125 I-1126 | FR-a: MS (ES): m/z 496.67 [M + H]$^+$, LCMS purity: 96.87%, HPLC purity: 97.07%, Chiral HPLC: 97.00%, $^1$H NMR (DMSO-$d_6$, 400 MHZ): 8.90 (s, 1H), 8.22 (s, 1H), 8.21 (s, 1H), 8.08-8.06 (d, J = 9.2 Hz, 1H), 7.94-7.92 (d, J = 5.2 Hz, 1H), 7.53-7.51 (d, J = 6.4 Hz, 1H), 6.35-6.32 (t, J = 7.2 Hz, 1H), 6.21 (s, 1H), 4.88-4.82 (t, J = 12.0 Hz, 1H), 4.37-4.28 (m, 1H), 3.73-3.68 (m, 1H), 3.28 (s, 4H), 3.18 (s, 3H), 2.93-2.92 (d, J = 4.8 Hz, 3H), 2.18-2.04 (m, 3H), 1.87-1.83 (d, J = 3.2 Hz, 1H), 1.73 (bs, 1H), 1.67-1.57 (m, 3H), 1.38-1.29 (m, 2H), 1.23 (bs, 1H), 1.13 (bs, 1H).<br>FR-b: MS (ES): m/z 496.72 [M + H]$^+$, LCMS purity: 100%, HPLC purity: 96.88%, Chiral HPLC: 99.37%, $^1$H NMR (DMSO-$d_6$, 400 MHZ): 8.91 (s, 1H), 8.23 (s, 1H), 8.22 (s, 1H), 8.09-8.06 (d, J = 9.2 Hz, 1H), 7.94-7.93 (d, J = 4.8 Hz, 1H), 7.53-7.51 (d, J = 6.8 Hz, 1H), 6.35-6.32 (t, J = 7.2 Hz, 1H), 6.21 (s, 1H), 4.88-4.82 (t, J = 12.0 Hz, 1H), 4.36-4.28 (m, 1H), 3.797-3.68 (m, 1H), 3.28 (s, 4H), 3.18 (s, 3H), 2.93-2.92 (d, J = 4.8 Hz, 3H), 2.18-2.04 (m, 3H), 1.87-1.83 (d, J = 3.2 Hz, 1H), 1.73 (bs, 1H), 1.67-1.57 (m, 3H), 1.38-1.29 (m, 2H), 1.23 (bs, 1H), 1.13 (bs, 1H). |
| I-1037 | I-1127 I-1128 | FR-a: MS (ES): m/z 496.41 [M + H]$^+$, LCMS purity: 100%, HPLC purity: 99.50%, Chiral HPLC: 100%, $^1$H NMR (DMSO-$d_6$, 400 MHZ): 8.90 (s, 1H), 8.24-8.23 (d, J = 6.8 Hz, 1H), 8.20 (s, 1H), 8.12-8.09 (d, J = 8.8 Hz, 1H), 7.94-7.93 (d, J = 4.8 Hz, 1H), 7.42-7.41 (d, J = 6.4 Hz, 1H), 6.32-6.31 (m, 1H), 6.18 (s, 1H), 4.91 (bs, 1H), |

TABLE 44-continued

| Compound | Isomers | Characterization data |
|---|---|---|
| | | 4.34-4.30 (m, 1H), 3.72-3.66 (m, 2H), 3.13 (s, 4H), 3.12 (s, 3H), 2.92-2.91 (d, J = 4.4 Hz, 3H), 2.13-2.11 (m, 4H), 1.86 (bs, 1H), 1.39 (bs, 6H). |
| | | FR-b: MS (ES): m/z 496.32 [M + H]⁺, LCMS purity: 99.22%, HPLC purity: 98.48%, Chiral HPLC: 99.37%, ¹H NMR (DMSO-d₆, 400 MHZ): 8.90 (s, 1H), 8.24-8.22 (d, J = 6.8 Hz, 1H), 8.20 (s, 1H), 8.12-8.09 (d, J = 8.8 Hz, 1H), 7.93-7.92 (d, J = 4.8 Hz, 1H), 7.42-7.41 (d, J = 6.4 Hz, 1H), 6.32-6.29 (t, J = 7.2 Hz, 1H), 6.18 (s, 1H), 4.91 (bs, 1H), 4.34-4.30 (m, 1H), 3.70-3.68 (m, 2H), 3.19 (s, 4H), 3.12 (s, 3H), 2.92-2.91 (d, J = 4.0 Hz, 3H), 2.13-2.11 (m, 4H), 1.86 (bs, 1H), 1.39 (bs, 6H). |
| | I-1057 I-1058 (Chiral separation when methylamino at position 7 is protected by Boc, followed by removal of Boc) | FR-a: MS (ES): m/z 482.61 [M + H]⁺, LCMS purity: 100%, HPLC purity: 96.4%, Chiral HPLC purity: 97.9%, ¹H NMR (DMSO-d₆, 400 MHZ): 8.88 (s, 1H), 8.24-8.23 (d, J = 6.4 Hz, 1H), 8.20 (s, 1H), 8.10-8.08 (d, J = 9.2 Hz, 1H), 7.93-7.90 (m, 1H), 7.44-7.42 (m, 1H), 6.31-6.28 (t, J = 7.2 Hz, 1H), 6.20 (s, 1H), 4.92-4.90 (m, 1H), 4.85-4.81 (d, J = 12.8 Hz, 1H), 4.35-4.31 (m, 1H), 3.97 (bs, 1H), 3.75-3.68 (m, 1H), 3.51-3.46 (m, 1H), 3.21 (s, 3H), 2.93-2.91 (m, 3H), 2.21-2.06 (m, 3H), 1.91-1.77 (m, 2H), 1.65-1.45 (m, 3H), 1.56-1.42 (m, 2H), 1.42-1.35 (m, 1H). FR-b: MS (ES): m/z 482.61 [M + H]⁺, LCMS purity: 99.40%, HPLC purity: 97.90%, Chiral HPLC purity: 100%, ¹H NMR (DMSO-d₆, 400 MHZ): 8.88 (s, 1H), 8.24-8.23 (d, J = 6.4 Hz, 1H), 8.20 (s, 1H), 8.10-8.08 (d, J = 9.2 Hz, 1H), 7.93-7.90 (m, 1H), 7.44-7.42 (m, 1H), 6.31-6.28 (t, J = 7.2 Hz, 1H), 6.20 (s, 1H), 4.92-4.90 (m, 1H), 4.85-4.81 (d, J = 12.8 Hz, 1H), 4.35-4.31 (m, 1H), 3.97 (bs, 1H), 3.75-3.68 (m, 1H), 3.51-3.46 (m, 1H), 3.21 (s, 3H), 2.93-2.91 (m, 3H), 2.21-2.06 (m, 3H), 1.91-1.77 (m, 2H), 1.65-1.45 (m, 3H), 1.56-1.42 (m, 2H), 1.42-1.35 (m, 1H). |
| I-1049 | I-1117 I-1118 | FR-a: MS (ES): m/z 513.60 [M + H]⁺, LCMS purity: 100%, HPLC purity: 99.53%, CHIRAL HPLC purity: 100%, ¹H NMR (DMSO-d₆, 400 MHZ): 8.91 (s, 1H), 8.25-8.23 (d, J = 7.2 Hz, 1H), 8.21 (s, 1H), 8.07-8.05 (d, J = 9.2 Hz, 1H), 7.93-7.92 (d, J = 4.8 Hz, 1H), 7.53-7.51 (d, J = 6.0 Hz, 1H), 6.34-6.31 (t, J = 7.2 Hz, 1H), 6.22 (s, 1H), 4.83-4.78 (m, 1H), 4.64-4.62 (m, 1H), 4.53-4.50 (m, 1H), 4.34-4.30 (m, 1H), 3.7349633-3.41 (m, 1H), 3.21 (s, 3H), 3.08-3.06 (m, 2H), 2.92 (s, 3H), 2.75-2.65 (m, 2H), 2.35-2.22 (m, 2H), 2.17-1.94 (m, 4H), 1.80-1.78 (m, 2H), 1.59-1.47 (m, 2H). FR-b: MS (ES): m/z 513.60 [M + H]⁺, LCMS purity: 100%, HPLC purity: 98.29%, CHIRAL HPLC purity: 100%, ¹H NMR (DMSO-d₆, 400 MHZ): 8.91 (s, 1H), 8.25-8.23 (d, J = 7.2 Hz, 1H), 8.21 (s, 1H), 8.07-8.05 (d, J = 9.2 Hz, 1H), 7.93-7.92 (d, J = 4.8 Hz, 1H), 7.53-7.51 (d, J = 6.0 Hz, 1H), 6.34-6.31 (t, J = 7.2 Hz, 1H), 6.22 (s, 1H), 4.83-4.78 (m, 1H), 4.64-4.62 (m, 1H), 4.53-4.50 (m, 1H), 4.34-4.30 (m, 1H), 3.73-3.41 (m, 1H), 3.21 (s, 3H), 3.08-3.06 (m, 2H), 2.92 (s, 3H), 2.75-2.65 (m, 2H), 2.35-2.22 (m, 2H), 2.17-1.94 (m, 4H), 1.80-1.78 (m, 2H), 1.59-1.47 (m, 2H). |
| I-1051 | I-1115 | FR-a: MS (ES): m/z 408.25 [M + H]⁺, LCMS purity: 97.67%, HPLC purity: 96.58%, CHIRAL HPLC purity: 96.0%, ¹H NMR (DMSO-d₆, 400 MHZ): 9.78 (s, 1H), 8.81 (s, 1H), 8.18 (s, 1H), 8.15-8.13 (d, J = 9.2 Hz, 1H), 7.98-7.95 (m, 2H), 7.56-7.54 (d, J = 8 Hz, 1H), 7.47-7.43 (t, J = 8 Hz, 1H), 3.36 (bs, 2H), 3.13 (s, 3H), 2.95-2.94 (d, J = 4 Hz, 3H), 2.03-1.97 (m, 2H), 1.11-1.04 (m, 3H). |
| I-1053 | I-1131 | FR-a: MS (ES): m/z 452.22 [M + H]⁺, LCMS purity: 98.00%, HPLC purity: 96.58%, CHIRAL HPLC purity: 98.00%, ¹H NMR (DMSO-d₆, 400 MHZ): 8.91 (s, 1H), 8.56-8.53 (m, 1H), 8.44-8.39 (m, 2H), 8.30-8.29 (d, J = 4.8 Hz, 1H), 7.64-7.58 (m, 1H), 6.81 (s, 1H), 5.21-5.14 (m, 1H), 4.46-4.42 (m, 1H), 3.88-3.85 (m, 1H), 3.23 (s, 3H), 3.13-3.12 (d, J = 5.2 Hz, 3H), 2.19-2.17 (d, J = 8 Hz, 1H), 2.08-2.06 (d, J = 6.4 Hz, 1H), 1.59 (s, 6H), 1.24 (bs, 2H). |
| I-1064 (Chiral separation when methylamino at position 7 is protected by Boc, followed by removal of Boc) | I-1129 I-1130 | FR-a: MS (ES): m/z 482.62 [M + H]⁺, LCMS purity: 95.01%, HPLC purity: 95.09%, Chiral HPLC: 96.59%, ¹H NMR (DMSO-d₆, 400 MHZ): 8.90 (s, 1H), 8.22-8.20 (m, 2H), 8.09-8.07 (d, J = 8.8 Hz, 1H), 7.94-7.93 (d, J = 4.8 Hz, 1H), 7.48-7.47 (d, J = 6.4 Hz, 1H), 6.33-6.29 (t, J = 7.2 Hz, 1H), 6.22 (s, 1H), 5.32-5.26 (t, J = 12.0 Hz, 1H), 4.71 (bs, 1H), 4.36-4.27 (m, 1H), 4.15 (s, 1H), 3.73-3.67 (m, 1H), 3.58 (s, 3H), 2.93-2.91 (d, J = 4.8 Hz, 3H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). FR-b: MS (ES): m/z 482.62 [M + H]⁺, LCMS purity: 98.10%, HPLC purity: 97.06%, Chiral HPLC: 99.08%, ¹H NMR (DMSO-d₆, 400 MHZ): 8.90 (s, 1H), 8.22-8.20 (m, 2H), 8.09-8.07 (d, J = 8.8 Hz, 1H), 7.95-7.93 (d, J = 4.8 Hz, 1H), 7.48-7.47 (d, J = 7.2 Hz, 1H), 6.33-6.29 (t, J = 6.8 Hz, 1H), 6.22 (s, 1H), 5.32-5.26 (t, J = 12.0 Hz, 1H), 4.71 (bs, 1H), 4.36-4.27 (m, 1H), 4.15 (s, 1H), 3.73-3.67 (m, 1H), 3.58 (s, 3H), 2.93-2.91 (d, J = 4.8 Hz, 3H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). |

TABLE 44-continued

| Compound | Isomers | Characterization data |
|---|---|---|
| I-1088 | I-1100<br>I-1101 | FR-a: MS (ES): m/z 465.51 [M − H]$^+$, LCMS purity: 100%, HPLC purity: 99.74%, CHIRAL HPLC purity: 100%, $^1$H NMR (DMSO-d$_6$, 400 MHZ): 8.98 (s, 1H), 8.23-8.21 (m, 2H), 8.08-8.06 (d, J = 8.8 Hz, 1H), 7.95-7.94 (d, J = 3.6 Hz, 1H), 7.34-7.33 (d, J = 6.4 Hz, 1H), 6.28-6.24 (m, 1H), 6.21 (s, 1H), 4.34-4.30 (m, 1H), 4.02-3.99 (d, J = 8.4 2H), 3.75-3.73 (m, 2H), 3.68-3.67 (m, 1H), 3.20 (s, 3H), 3.16 (s, 1H), 2.91-2.90 (d, J = 3.6 Hz, 3H), 2.34 (s, 2H), 2.16-2.00 (m, 2H), 1.55-1.50 (m, 1H), 1.39-1.34 (m, 1H).<br>FR-b: MS (ES): m/z 465.51 [M − H]$^+$, LCMS purity: 100%, HPLC purity: 97.52%, CHIRAL HPLC purity: 99.63%, $^1$H NMR (DMSO-d$_6$, 400 MHZ): 8.98 (s, 1H), 8.22-8.19 (m, 2H), 8.07-8.05 (d, J = 9.2 Hz, 1H), 7.96-7.94 (m, 1H), 7.34-7.32 (m, 1H), 6.27-6.25 (m, 1H), 4.33-4.29 (m, 1H), 4.00-3.98 (m, 2H), 3.74-3.65 (m, 3H), 3.68-3.67 (m, 1H), 3.19-3.15 (m, 4H), 2.90-2.89 (d, J = 4.4, 3H), 2.33 (s, 2H), 2.15-1.99 (m, 2H), 1.54-1.49 (m, 1H), 1.40-1.33 (m, 1H). |

102.5. Synthesis of 5-(5-fluoro-1-isopropyl-1H-pyrrolo[2,3-b]pyridin-3-yl)-N-((1S,2S)-2-methoxy-cyclobutyl)-7-(methylamino)pyrazolo[1,5-a]pyrimidine-3-carboxamide (I-1053)

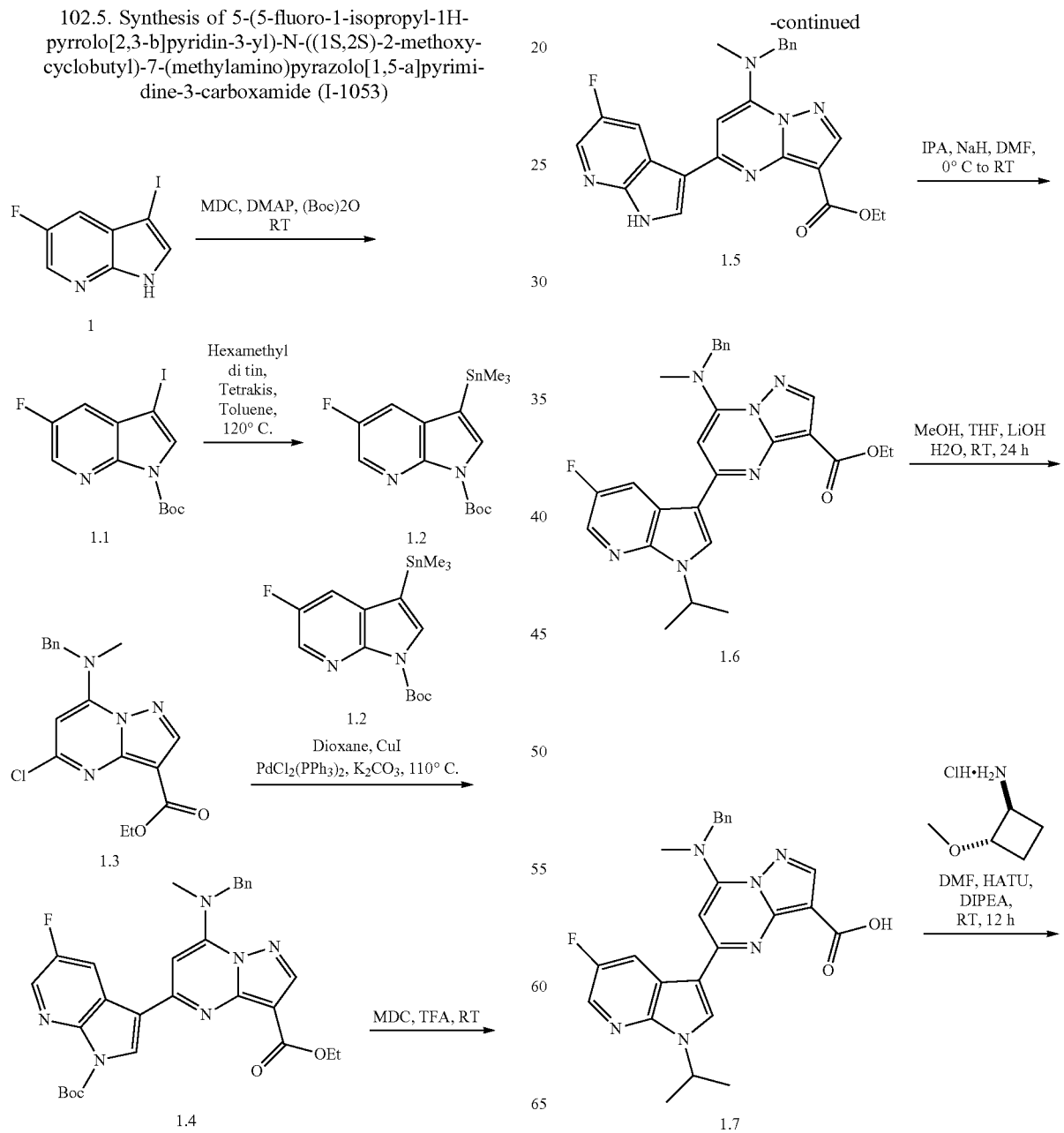

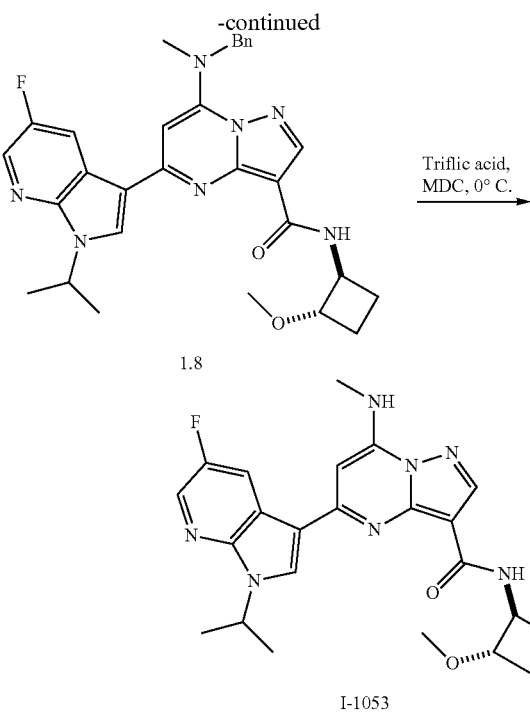

Synthesis of Compound 1.1.

To a solution of 1. (0.7 g, 2.67 mmol, 1 eq) in dichloromethane (7 mL), 4-Dimethylaminopyridine (0.015 g, 0.13 mmol, 0.05 eq) and Triethylamine (0.809 g, 8.01 mmol, 3 eq) was added. Di-tert-butyl dicarbonate (0.638 g, 2.93 mmol, 1.1 eq) was added at 0° C. The reaction mixture was stirred at room temperature for 1 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by column chromatography using 10% ethylacetate in hexane as eluant to obtain 1.1. (0.650 g, Yield: 67.19%). MS (ES): m/z 361.99 [M−H]+

Synthesis of Compound 1.2.

To a degassed solution of 1.1 (0.650 g, 1.79 mmol, 1.0 eq) and hexamethylditin (2.3 g, 7.16 mmol, 4.0 eq) in toluene (39 mL) was added tetrakis(triphenylphosphine)palladium (0) (0.196 g, 0.17 mmol, 0.1 eq) and the reaction mixture was heated at 120° C. for 2 h under $N_2$. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by column chromatography using 10% ethylacetate in hexane as eluant to obtain 1.2. (0.5 g, Yield: 69.81%). MS (ES): m/z 400.06 [M+H]+

Synthesis of Compound 1.3.

Compound was synthesized using general procedure of core synthesis to obtain 1.3. (Yield: 45%), MS(ES): m/z 345.10 [M+H]+.

Synthesis of Compound 1.4.

Argon was purged for 15 min through a stirring solution of 1.3 (3.5 g, 1.16 mmol, 1.0 eq), 1.2 (0.696 g, 1.74 mmol, 1.5 eq) and potassium carbonate (0.4 g, 2.9 mmol, 2.5 eq) in 1,4-dioxane (8 ml). Copper(I) iodide (0.043 g, 0.23 mmol, 0.2 eq) and Bis(triphenylphosphine)palladium(II) dichloride (0.077 mg, 0.11 mmol, 0.1 eq) was added to it and further purging done for 10 min. Reaction was allowed to stirred at 110° C. for 6 h. After completion of reaction, reaction mixture was poured over water and product was extracted with ethyl acetate. Organic layer was combined, washed with brine solution, dried over sodium sulphate and concentrated under reduced pressure to obtain 1.4. (0.4 g, 63.31%). MS (ES): m/z 545.23 [M+H]+

Synthesis of Compound 1.5.

Compound was synthesized using general procedure C to obtain 1.5. (0.310 g, 94.96%), MS (ES): 445.17 [M+H]+

Synthesis of Compound 1.6.

To a solution of 1.5 (0.310 g, 0.69 mmol, 1 eq) in Dimethylformamide (3 mL), Sodium hydride (0.033 g, 1.38 mmol, 2 eq) was added at 0° C. Isopropyl alcohol (0.053 mg, 0.89 mmol, 1.3 eq) was added to it and stirred at room temperature for 1 h. The reaction mixture was stirred at room temperature for 1 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 10% ethylacetate in hexane to obtain 1.6. (0.262 g, Yield: 77.21%). MS (ES): m/z 487.22 [M+H]+

Synthesis of Compound 1.7.

To a solution of 1.6 (0.262 g, 0.53 mmol, 1.0 eq), in methanol:tetrahydrofuran: water (5 mL, 2:2:1) was added lithium hydroxide (0.127 g, 5.3 mmol, 10 eq). The reaction was stirred at 60° C. for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.7. (0.2 g, 81.01%). MS(ES): m/z 459.19 [M+H]+

Synthesis of Compound 1.8:

Compound was synthesized as per general procedure A to obtain 1.8 (0.13, 55.05%). MS(ES): m/z 542.19 [M+H]+.

Synthesis of Compound I-1053:

Compound was synthesized using general procedure C to obtain I-1053 (0.021 g, 83.97%), MS (ES): m/z 452.21 [M+H]+, LCMS purity: 95.41%, HPLC purity: 95.89%, CHIRAL HPLC: 50.82%, 49.17%, $^1$H NMR (DMSO-$d_6$, 400 MHz): 8.91 (s, 1H), 8.56-8.53 (m, 1H), 8.44-8.39 (m, 2H), 8.30-8.29 (d, J=4.8 Hz, 1H), 7.64-7.58 (m, 1H), 6.81 (s, 1H), 5.21-5.14 (m, 1H), 4.46-4.42 (m, 1H), 3.88-3.85 (m, 1H), 3.23 (s, 3H), 3.13-3.12 (d, J=5.2 Hz, 3H), 2.19-2.17 (d, J=8 Hz, 1H), 2.08-2.06 (d, J=6.4 Hz, 1H), 1.59 (s, 6H), 1.24 (s, 2H).

102.6. Synthesis of 5-(1-cyclopropyl-1H-pyrrolo[2,3-b]pyridin-3-yl)-N-(2-methoxycyclobutyl)-7-(methylamino)pyrazolo[1,5-a]pyrimidine-3-carboxamide (I-1067)

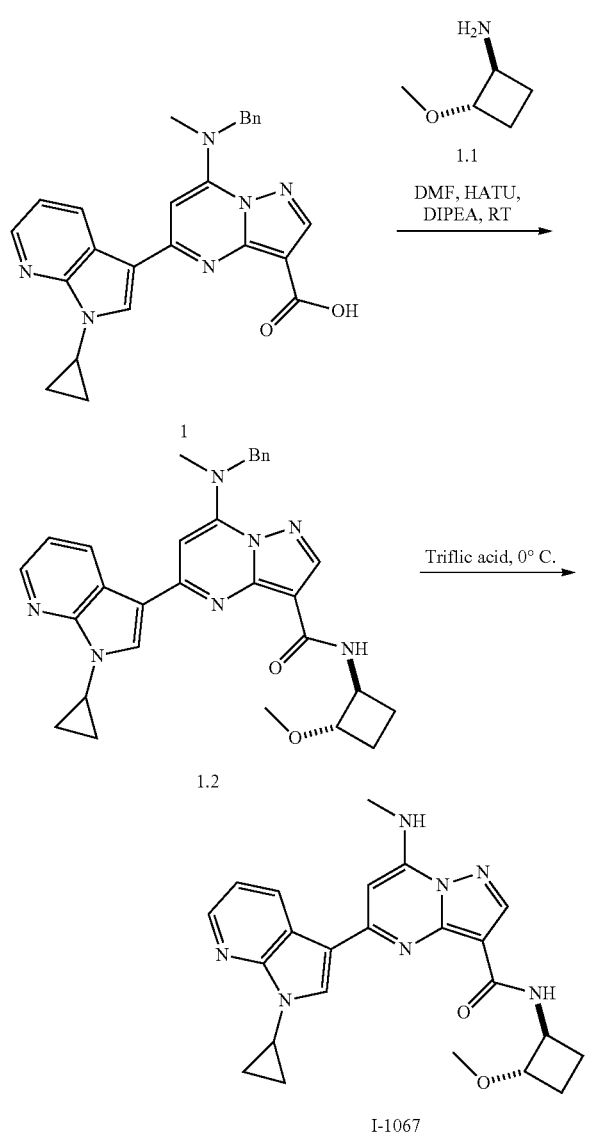

Synthesis of Compound 1.

Compound was synthesized as per experimental protocol Example 78 of I-960 to obtain 1. (Yield: 78.96%), MS (ES): m/z 439.18 [M+H]+

Synthesis of Compound 1.2.

Compound was synthesized using general procedure A to obtain 1.2. (0.145 g, 64.15%), MS (ES): 522.26 [M+H]+

Synthesis of Compound I-1067:

To a solution of 1.2 (0.145 g, 0.27 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1067 (0.100 g, 83.37%), MS (ES): m/z 432.37 [M+H]+, LCMS purity: 100%, HPLC purity: 95.35%, CHIRAL HPLC: 50.23%, 49.46%, $^1$H NMR (DMSO-d$_6$, 400 MHZ): 8.78-8.76 (d, J=6 Hz, 1H), 8.62 (s, 1H), 8.52-8.50 (d, J=8.8 Hz, 1H), 8.45-8.44 (d, J=4.4 Hz, 1H), 8.38 (s, 1H), 8.26-8.25 (d, J=4.8 Hz, 1H), 7.36-7.32 (m, 1H), 6.80 (s, 1H), 4.43-4.38 (m, 1H), 3.84-3.79 (m, 2H), 3.24 (s, 3H), 3.12-3.10 (d, J=4.8 Hz, 3H), 2.23-2.12 (m, 2H), 1.60-1.49 (m, 3H), 1.24 (bs, 3H).

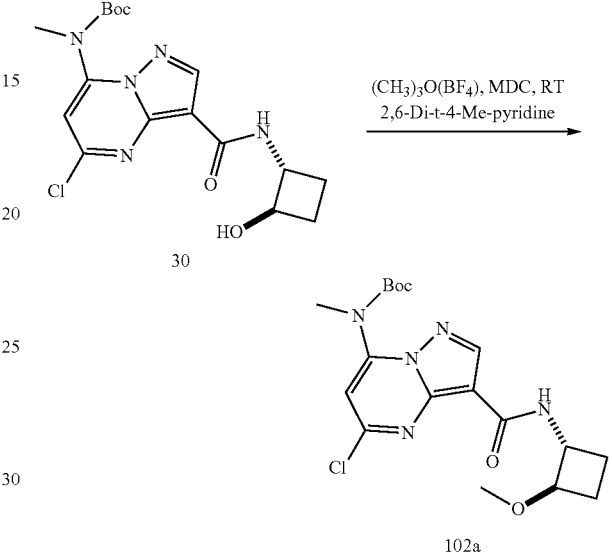

Synthesis of Compound 30.

Compound was synthesized as per experimental protocol of Example 29 of I-676 to obtain 30. (Yield: 52.83%), MS (ES): m/z 396.14 [M+H]+

Synthesis of Compound 102a.

To a solution of 30 (1.0 g, 2.52 mmol, 1 eq) in dichloromethane (20 mL), Triethyloxonium tetrafluoroborate (0.957 g, 5.04 mmol, 2.0 eq) and 2,6-Di-tert-butyl-4-methylpyridine (1.54 g, 7.56 mmol, 3.0 eq) was added. The reaction mixture was stirred at room temperature for 4 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 102a. (0.600 g, Yield: 57.95%). MS (ES): m/z 410.16 [M+H]+

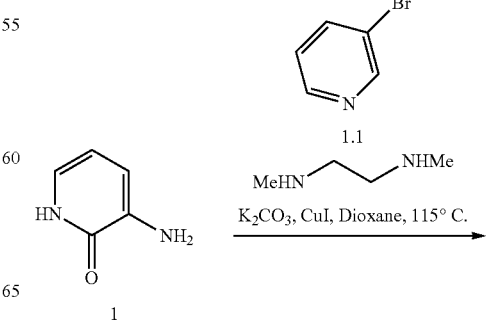

1541 -continued

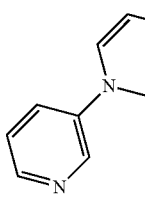
102b

Synthesis of Compound 102b.

To a solution of 1. (2.0 g, 18.16 mmol, 1 eq) and 1.1 (3.15 g, 19.97 mmol, 1.1 eq) in 1,4-dioxane (90 mL) was added potassium carbonate (5.0 g, 36.32 mmol, 2.0 eq) and degassed with argon for 15 min. Copper iodide (0.691 g, 3.63 mmol, 0.2 eq) and N1,N2-dimethylethane-1,2-diamine (0.639 g, 7.26 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 102b. (0.8 g, 23.53%). MS(ES): m/z 188.08 [M+H]$^+$.

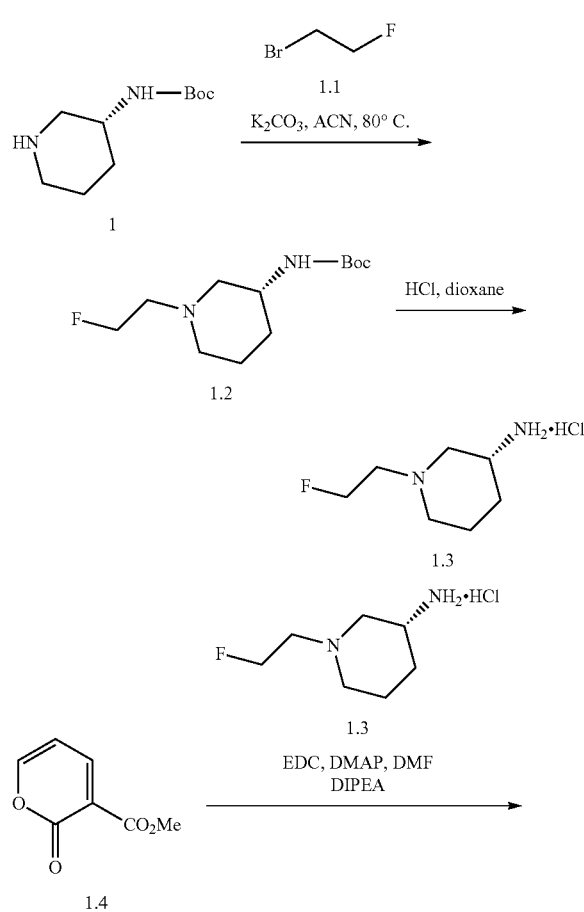

1542 -continued

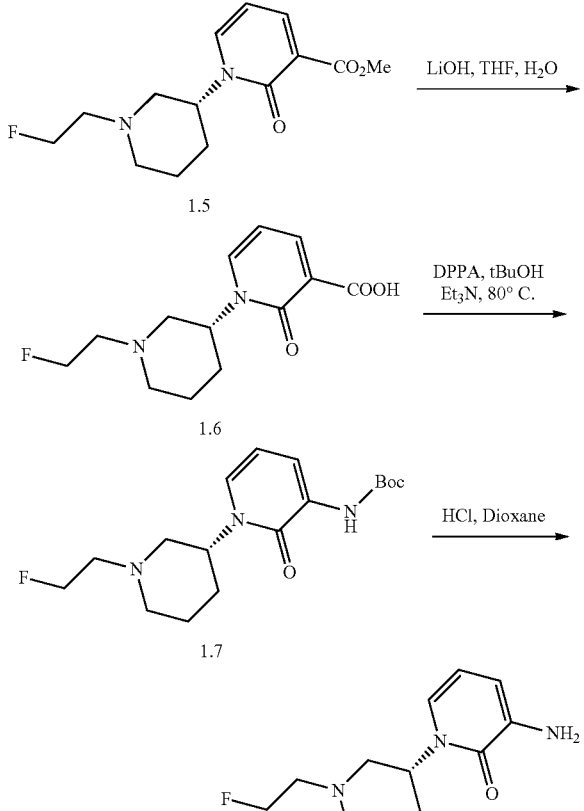

Synthesis of Compound 1.2.

To a cooled solution of 1 (2.0 g, 10.0 mmol, 1.0 eq), and 1.1 (1.5 g, 12.0 mmol, 1.2 eq) in Acetonitrile (60 mL) at 0° C. was added potassium carbonate (3.4 g, 25 mmol, 2.5 eq). The reaction was stirred at 80° C. for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 1.2. (1.7 g, 69.11%). MS (ES): m/z 247.18 [M+H]$^+$.

Synthesis of Compound 1.3.

A cooled solution of 1.2 (1.7 g, 6.90 mmol, 1 eq) in dioxane (35 mL) was added 4N hydrochloric acid in dioxane (70 mL) as a dropwise. The reaction mixture was stirred at room temperature for 2 h. After completion of reaction, reaction mixture was concentrated under reduced pressure to obtain pure 1.3. (1.5 g, 95.19%). MS(ES): m/z 183.10 [M+HCl]$^+$.

Synthesis of Compound 1.5.

To a cooled solution of 1.4 (1.5 g, 9.73 mmol, 1.0 eq), in N,N-dimethylformamide (18 mL) was added 1.3 (1.7 g, 9.73 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.9 g, 12.64 mmol, 1.3 eq), 4-Dimethylaminopyridine (0.236 g, 1.94 mmol, 0.2 eq) and N,N-Diisopropylethylamine (0.878 g, 6.81 mmol, 0.7 eq), was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.5. (0.710 g, 25.84%). MS(ES): m/z 283.14 [M+H]$^+$.

Synthesis of Compound 1.6.

To a solution of 1.5 (0.710 g, 2.51 mmol, 1.0 eq), in tetrahydrofuran: water (10 mL, 2:1) was added lithium hydroxide (0.602 g, 25.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.6. (0.455 g, 67.44%). MS(ES): m/z 269.13 [M+H]$^+$.

Synthesis of Compound 1.7.

To a solution of 1.6 (0.455 g, 1.69 mmol, 1.0 eq) in tert.butanol (8 mL) was added triethylamine (0.290 g, 2.87 mmol, 1.7 eq) and diphenyl phosphoryl azide (0.604 g, 2.19 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.7. (0.210 g, 36.48%). MS(ES): m/z 340.20[M+H]$^+$.

Synthesis of Compound 102c.

To 1.7 (0.210 g, 0.61 mmol, 1.0 eq) was added 4M hydrochloric acid in 1,4 Dioxane (8 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 102c. (0.160 g, Yield: 94.56%), MS (ES): m/z 240.15 [M+H]$^+$.

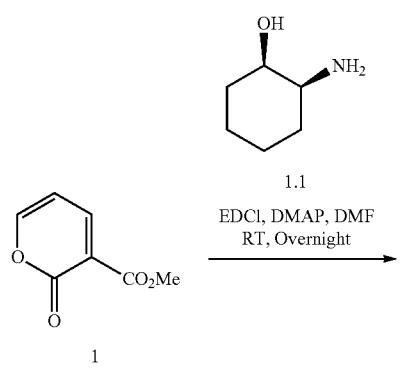

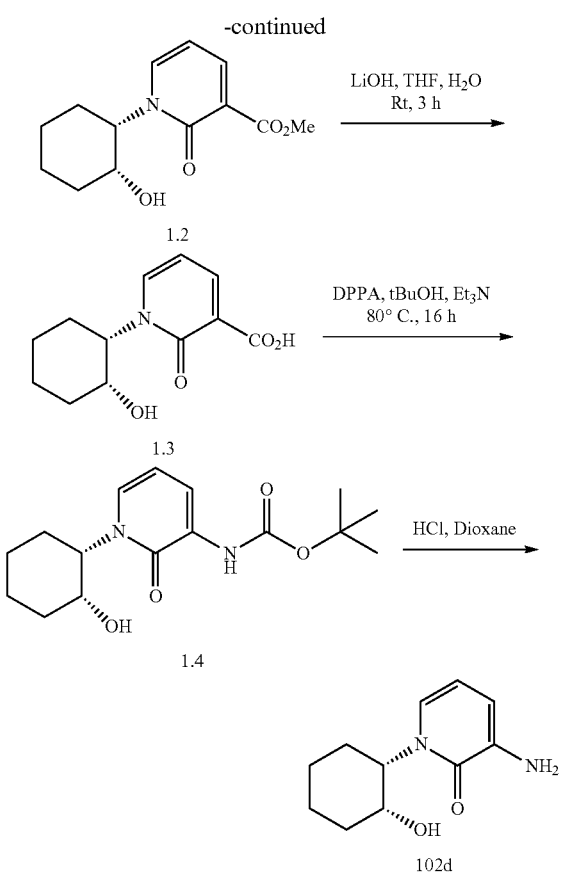

Synthesis of Compound 1.2.

To a stirred solution of 1.1 (5.0 g, 32.47 mmol, 1.0 eq) in N,N-dimethyl formamide (50 mL) was added 1 (5.0 g, 32.47 mmol, 1.0 eq) in one portion at 0° C. under Ar followed by diisopropyl ethyl amine (6.3 g, 48.71 mmol, 1.5 eq) and the reaction mixture was stirred at 0° C. for 3 h. 1-Ethyl-3-(3-dimethylaminopropyl)carbodiimide hydrochloride (8.1 g, 42.21 mmol, 1.3 eq) and 4-Dimethylaminopyridine (1.0 g, 8.11 mmol, 0.25 eq) were added under Ar and the reaction mixture was stirred at room temperature overnight. The reaction mixture was concentrated under reduced pressure and the residue was purified by column chromatography and compound was eluted in 1.9% methanol in dichloromethane to obtain pure 1.2 (4.3 g, 52.76%). MS(ES): m/z 252.42 [M+H]$^+$.

Synthesis of Compound 1.3.

To a stirred solution of 1.2 (1.5 g, 5.98 mmol, 1.0 eq) in tetrahydrofuran (45 mL) was added methanol (16.5 mL) and a solution of lithium hydroxide monohydrate (1.1 g, 25.71 mmol, 4.5 eq) in water (22 mL) and the reaction mixture was stirred at room temperature for 3 h. The reaction mixture was concentrated under vacuum and the residue was adjusted to pH 3 by slow addition of 1N hydrochloric acid at 0° C. The precipitate was collected by filtration and dried to obtain pure compound 1.3 (0.90 g, 48.06%). MS(ES): m/z 238.45 [M+H]$^+$.

Synthesis of Compound 1.4.

A stirred mixture of 1.3 (0.90 g, 3.80 mmol, 1.0 eq), tert butanol (11 mL), diphenyl phosphoryl azide (1.5 g, 5.32 mmol, 1.4 eq) and triethyl amine (540 mg, 5.32 mmol, 1.4 eq) was heated at 80° C. under $N_2$ for 18 h. The reaction mixture was evaporated under reduced pressure. The residue was dissolved in ethyl acetate and the organic solution was washed with water. The organic phase was dried over sodium sulfate and concentrated under reduced pressure to obtain crude product. This was purified by column chromatography and compound was eluted in 1% methanol in dichloromethane to obtain pure 1.4 (0.70 g, 59.82%). MS(ES): m/z 309.45 [M+H]⁺.

Synthesis of Compound 102d.

To a stirred solution of 1.4 (0.70 g, 2.27 mmol) in dichloromethane (10 mL) was added 4 M HCl in dioxane (5 mL) dropwise at 0° C. under N₂ and the reaction mixture was stirred at room temperature for 3 h. The reaction mixture was concentrated under reduced pressure and the solid residue was triturated with diethyl ether to obtain the hydrochloride salt of 102d (0.40 g, 72.11%). MS(ES): m/z 209.32 [M+H]⁺.

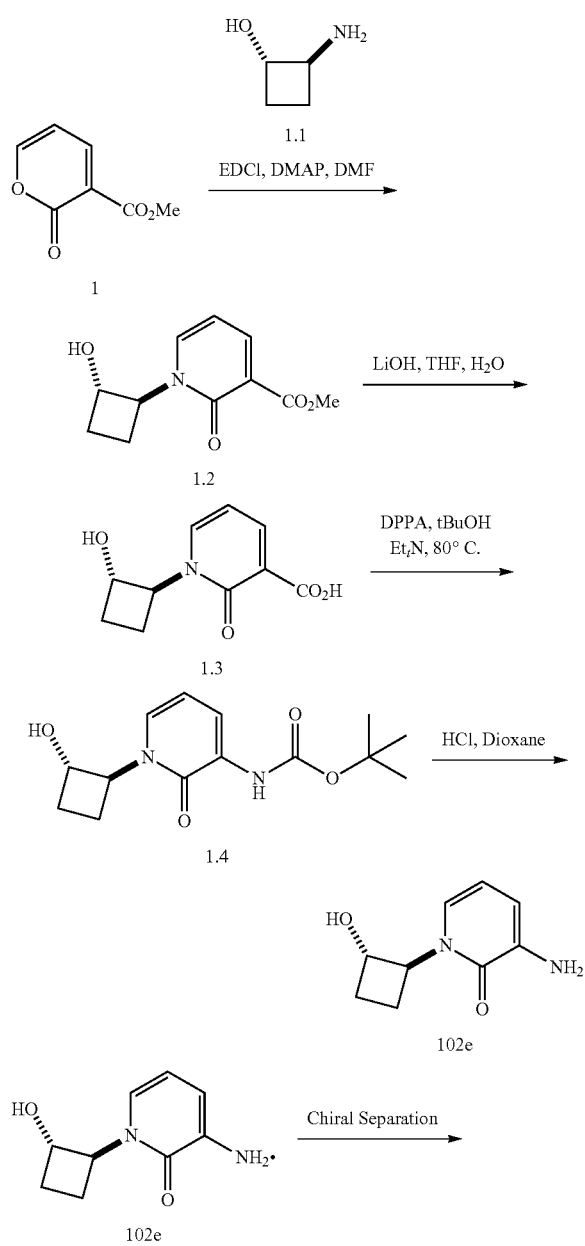

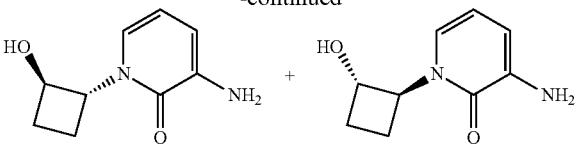

Synthesis of Compound 1.2.

To a cooled solution of 1. (1.0 g, 6.48 mmol, 1.0 eq), in N,N-dimethylformamide (12 mL) was added 1.1 (0.619 g, 7.12 mmol, 1.1 eq). The reaction mixture was stirred at 0° C. for 30 min and further stirred at room temperature for 15 min. N-Ethyl-N'-(3-dimethylaminopropyl)carbodiimide hydrochloride (1.3 g, 8.42 mmol, 1.3 eq) and 4-Dimethylaminopyridine (0.157 g, 1.29 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.8 g, 55.23%). MS(ES): m/z 224.09 [M+H]⁺.

Synthesis of Compound 1.3.

To a solution of 1.2 (0.8 g, 3.58 mmol, 1.0 eq), in tetrahydrofuran: water (12 mL, 2:1) was added lithium hydroxide (0.859 g, 35.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.7 g, 93.37%). MS(ES): m/z 210.07 [M+H]⁺.

Synthesis of Compound 1.4.

To a solution of 1.3. (0.7 g, 3.34 mmol, 1.0 eq) in tert.butanol (7 mL) was added triethylamine (0.572 g, 5.67 mmol, 1.7 eq) and diphenyl phosphoryl azide (1.19 g, 4.34 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.6 g, 63.97%). MS(ES): m/z 281.15 [M+H]⁺.

Synthesis of Compound 102e.

A cooled solution of 1.4 (0.6 g, 1.42 mmol, 1 eq) in dioxane (12 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 102e. (0.480 g, 99.82%). MS(ES): m/z 181.09 [M+HCl]⁺.

Isomers of 102e (0.48 g) were separated out using column (CHIRAL PAK AD-H 250×4.6 mm, 5 µM) and DEA in methanol as co-solvent with flow rate of 4 mL/min. to get pure fraction-1 and fraction-2 (FR-b). FR-a was evaporated under reduced pressure at 30° C. to afford pure FR-a (0.150 g). MS(ES): m/z 181.09 [M+H]⁺. FR-b was evaporated under reduced pressure at 30° C. to afford pure FR-b. (0.155 g). MS(ES): m/z 181.09 [M+H]

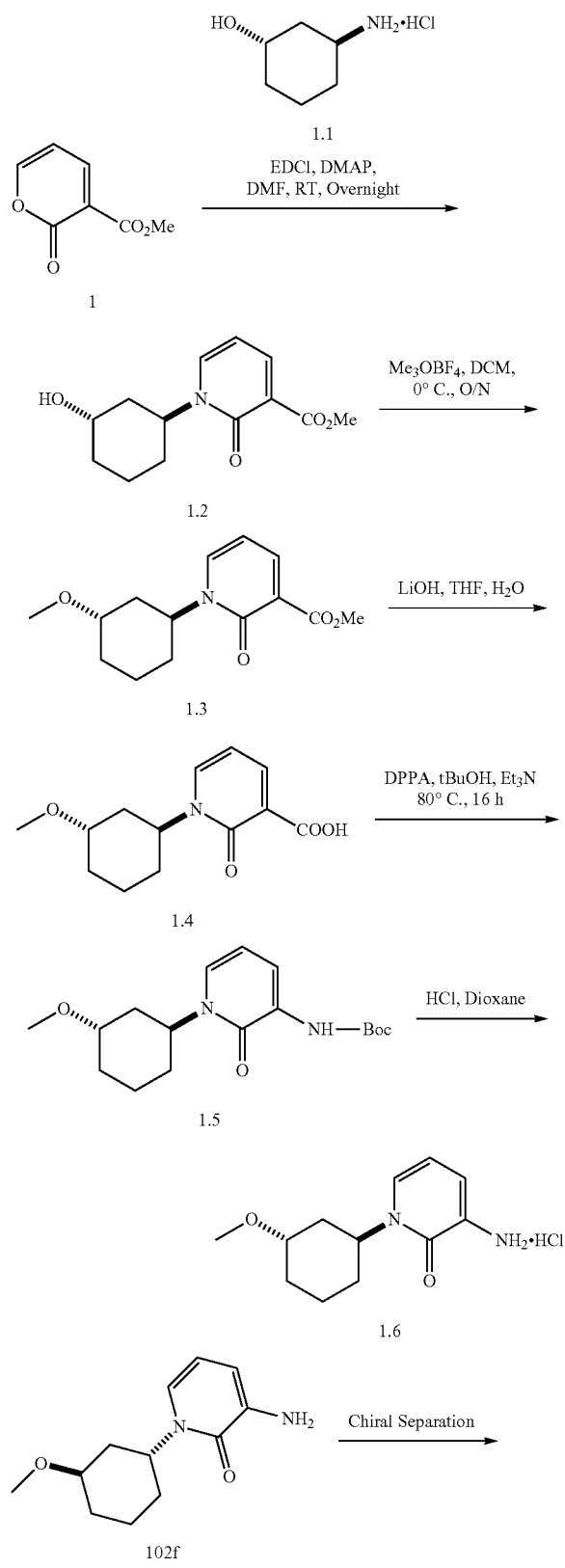

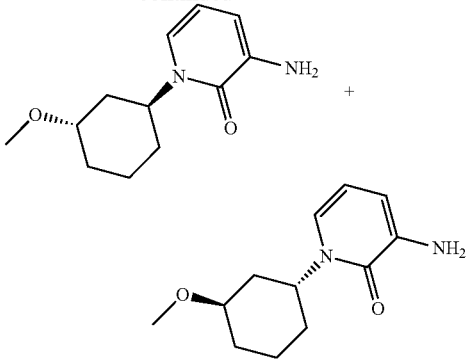

Synthesis of Compound 1.2.

To a cooled solution of 1 (1.0 g, 6.48 mmol, 1.0 eq), in N,N-dimethylformamide (15 mL) was added 1.1 (0.982 g, 6.48 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.30 g, 8.42 mmol, 1.3 eq) and 4-Dimethylaminopyridine (0.157 g, 1.29 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.4 g, 29.53%). MS(ES): m/z 252.12 [M+H]⁺.

Synthesis of Compound 1.3.

To a solution of 1.2 (0.4 g, 1.59 mmol, 1.0 eq), in dichloromethane (5 mL) was added Trimethyloxonium tetrafluoroborate (0.470 g, 3.18 mmol, 2.0 eq) at 0° C. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.3. (0.150 g, 35.52%). MS(ES): m/z 266.13 [M+H]⁺.

Synthesis of Compound 1.4.

To a solution of 1.3 (0.150 g, 0.56 mmol, 1.0 eq), in tetrahydrofuran: water (3 mL, 2:1) was added lithium hydroxide (0.134 g, 5.6 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.4. (0.123 g, 86.58%). MS(ES): m/z 252.12 [M+H]⁺.

Synthesis of Compound 1.5.

To a solution of 1.4 (0.123 g, 0.48 mmol, 1.0 eq) in tert.butanol (3 mL) was added triethylamine (0.081 g, 0.81 mmol, 1.7 eq) and diphenyl phosphoryl azide (0.171 g, 0.62 mmol, 1.3 eq) under nitrogen followed by heating at 80° C.

for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.5. (0.080 g, 50.69%). MS(ES): m/z 323.19 [M+H]+.

Synthesis of Compound 1.6.

A cooled solution of 1.5. (0.080 g, 0.24 mmol, 1 eq) in dioxane (2 mL) was added 4N hydrochloric acid in dioxane (5 mL) as a dropwise. The reaction mixture was stirred at room temperature for 2 h. After completion of reaction, reaction mixture was concentrated under reduced pressure to obtain pure 1.6. (0.060 g, 93.45%). MS(ES): m/z 259.12 [M+HCl]+.

Isomers of 102f (0.9 g) were separated out using column (CHIRAL PAK AD-H 250×4.6 mm, 5 μM) and DEA in methanol as co-solvent with flow rate of 4 mL/min. to get pure fraction-1 and fraction-2 (FR-b). FR-a was evaporated under reduced pressure at 30° C. to afford pure FR-a. (0.300 g). MS(ES): m/z 223.14 [M+H]+. FR-b was evaporated under reduced pressure at 30° C. to afford pure FR-b. (0.280 g). MS(ES): m/z 223.14 [M+H]+

Example 103: Synthesis of compounds comprising aminocarbonyl at position 3 of the pyrazolo[1,5-a]pyrimidine 103.1. Synthesis of 5-((3,5-dimethylphenyl)amino)-7-(methylamino)pyrazolo[1,5-a]pyrimidine-3-carboxamide (I-2)

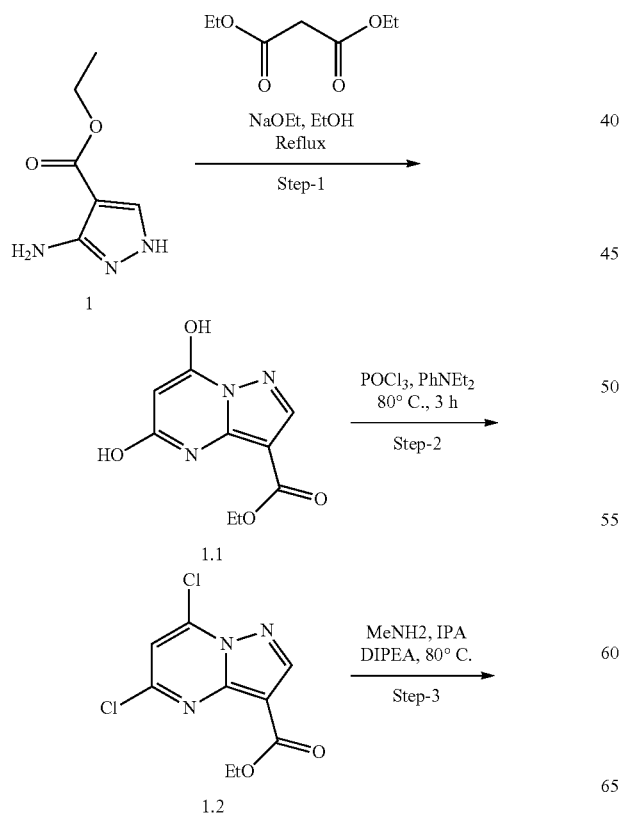

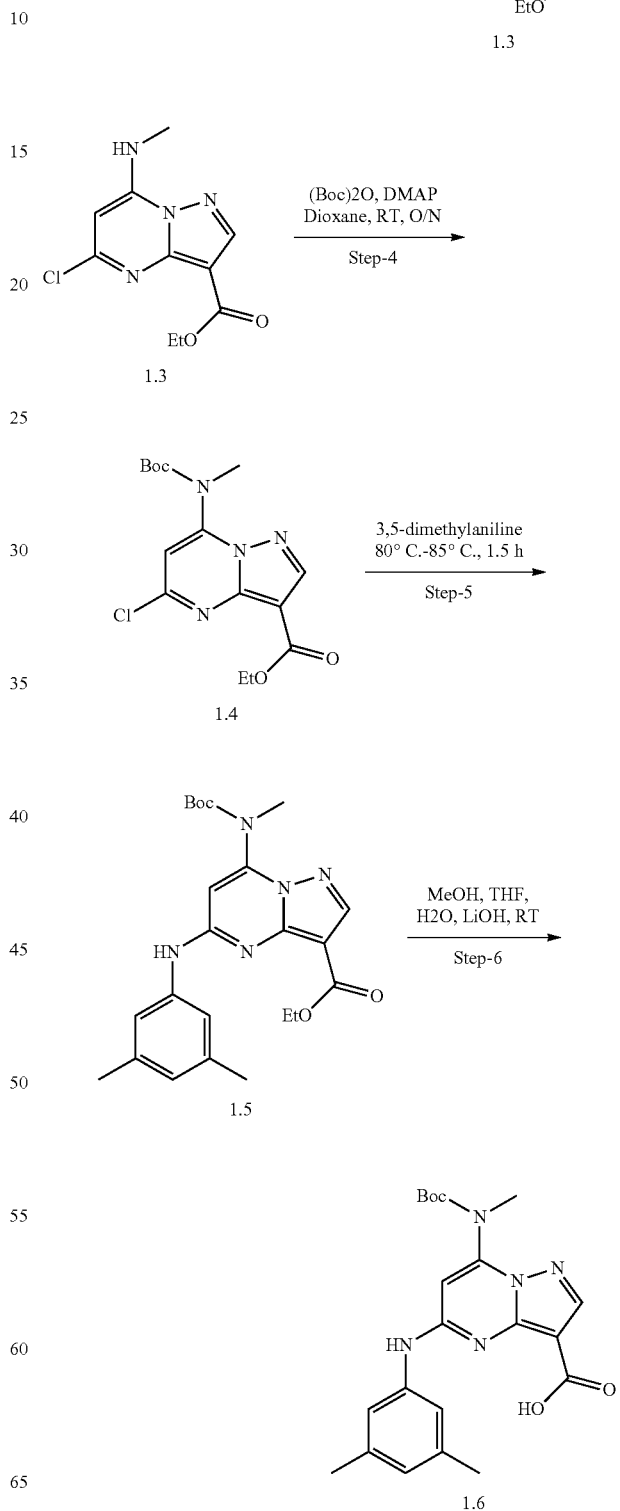

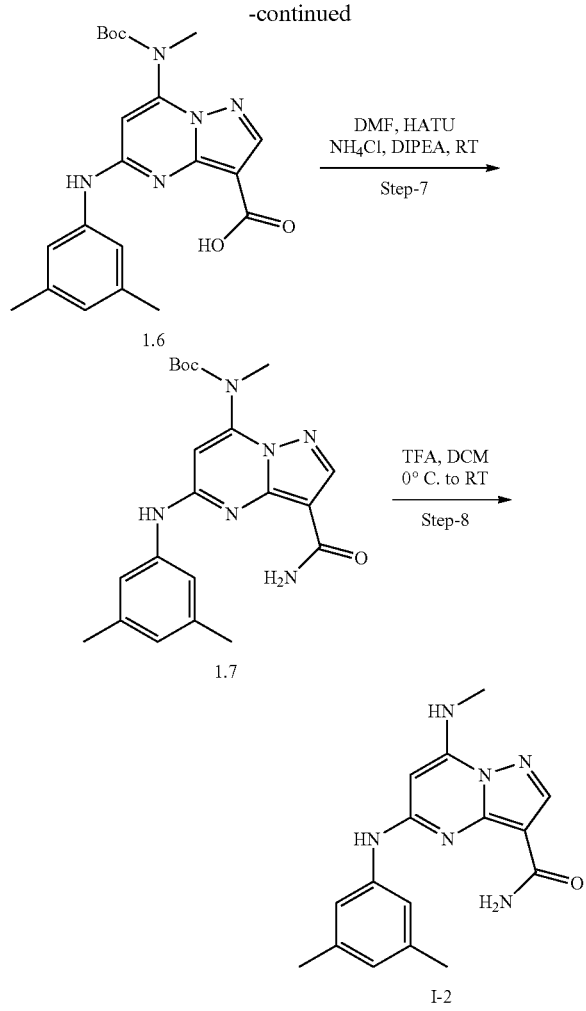

Synthesis of Compound 1.1.

To a solution of 1 (10 g, 64.45 mmol, 1.0 eq) in ethanol (300 mL) was added diethyl malonate (20.65 g, 128.9 mmol, 2.0 eq) followed by sodium ethoxide (74.97 g, 21% ethanol solution, 3.59 eq) was added dropwise. Reaction mixture was stirred with heating under reflux for 18 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure 1.1 (10 g, 69.52%). MS(ES): m/z 224.2 [M+H]$^+$.

Synthesis of Compound 1.2.

To a mixture of 1.1 (3 g, 13.44 mmol, 1.0 eq) in phosphorous oxychloride (8.7 mL) was added diethyl aniline (3.37 g, 22.56 mmol, 1.68 eq). Reaction mixture stirred at 80° C. for 3 h. After completion of reaction; reaction mixture was transferred into ice cold water, neutralized with saturated sodium bicarbonate solution and extracted with dichloromethane. Organic layer was combined, washed with brine solution, dried over sodium sulphate and concentrated under reduced pressure to pressure to obtain crude material. This was further purified by column chromatography and the compound was eluted in 15% ethyl acetate in hexane to obtain pure 1.2 (3.0 g, 85.82%). MS(ES): m/z 261 [M+H]$^+$.

Synthesis of Compound 1.3.

To a solution of 1.2 (3.0 g, 11.54 mmol, 1.0 eq) in isopropylalcohol (30 mL) was added diisopropylethylamine (4.2 mL, 23 mmol, 2.0 eq) at 0° C. followed by methylamine (6.9 mL, 13 mmol, 1.2 eq) and reaction mixture stirred at 80° C. for 16 h. After completion of reaction, reaction mixture was concentrated under reduced pressure to obtain residue. To this added water and extracted with dichloromethane Organic layer was combined, washed with brine solution, dried over sodium sulphate and concentrated under reduced pressure to pressure to obtain crude material. This was further purified by column chromatography and the compound was eluted in 40% ethyl acetate in hexane to obtain 1.3. (2.9 g, 95.12%). MS(ES): m/z 310[M+H]$^+$.

Synthesis of Compound 1.4.

To a solution of 1.3 (2.9 g, 11.39 mmol, 1.0 eq) in 1,4-dioxane (15 mL) was added N,N-dimethylaminopyridine (0.138 g, 1.139 mmol, 0.1 eq) followed by Di-tert-butyl dicarbonate (4.79 g, 22.78, 2.0 eq) and reaction mixture was stirred at room temperature for 16 h. After completion of reaction, reaction mixture was transferred in water product was extracted with dichloromethane. Organic layer was combined and dried over sodium sulphate and concentrated under reduced pressure to obtain crude material. This was further purified by column chromatography and the compound was eluted in 10% ethyl acetate in hexane to obtain 1.4. (2.9 g, 71.78%). MS(ES): m/z 355[M+H]$^+$.

Synthesis of Compound 1.5.

Mixture of 1.4 (1.0 g, 2.82 mmol, 1.0 eq) and 3,5-dimethylaniline (2 mL) was stirred at 80° C.–85° C. for 1.5 h. After completion of reaction, reaction mixture was transferred in water product was extracted with dichloromethane. Organic layer was combined and dried over sodium sulphate and concentrated under reduced pressure to obtain crude material. This was further purified by column chromatography and the compound was eluted in 20% ethyl acetate in hexane to obtain 1.5. (1.0 g, 80.72%). MS(ES): m/z 440.5 [M+H]$^+$.

Synthesis of Compound 1.6.

To a solution of 1.5 (1.0 g, 2.28 mmol, 1.0 eq), in tetrahydrofuran: methanol: water (15 mL, 1:1:1) was added lithium hydroxide (0.957 g, 22.8 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.6 (0.8 g, 85.45%). MS(ES): m/z 412 [M+H]$^+$.

Synthesis of Compound 1.7.

To a solution of 1.6 (0.150 g, 0.364 mmol, 1.0 eq), in N,N-dimethylformamide (3 mL) was added 1-[Bis(dimethylamino)methylene]-1H-1,2,3-triazolo[4,5-b]pyridinium 3-oxid hexafluorophosphate (0.276 g, 0.728 mmol, 2.0 eq) and stirred at room temperature for 20 min. To this added diisopropylethylamine (0.195 mL, 1.092 mmol, 3.0 eq) followed by addition of ammonium chloride (0.058 g, 1.092 mmol, 3.0 eq). The reaction mixture was stirred at room temperature for 1 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.7. (0.070 g, 46.78%). MS(ES): m/z 411.5 [M+H]$^+$.

Synthesis of Compound I-2.

The compound 1.7 (0.070 g, 0.170 mmol, 1.0 eq) was dissolved in dichloromethane (2 mL) and trifluoroacetic acid (0.1 mL) was added to the reaction mixture. The reaction was stirred at room temperature for 2 h. After completion of reaction, reaction mixture was poured in water, basified with saturated bicarbonate solution and product was extracted with ethyl acetate. Organic layer was combined and dried over sodium sulphate and concentrated under reduced pressure to obtain crude material. This was further purified by trituration with diethyl ether to obtain pure I-2 (0.025 g, 94.47%). MS(ES): m/z 311.54 [M+H]$^+$, LCMS purity: 98.61%, HPLC purity: 97.72%, $^1$H NMR (DMSO-d$_6$, 400 MHZ): 9.37 (s, 1H), 8.13 (s, 1H), 7.85-7.84 (d, J=4.8 Hz, 1H), 7.53 (s, 1H), 7.34 (s, 1H), 6.66 (s, 1H), 5.51 (s, 1H), 2.91 (s, 3H), 2.25 (s, 6H).

Additional compounds prepared by substantially the same method, and their characterization data, are listed in the Table 45 below. The intermediate corresponding to 3,5-dimethylaniline in step-5 of the above scheme is listed for each compound.

TABLE 45

| Compound | Intermediate | Characterization data |
|---|---|---|
| I-9 | (4-fluorophenyl-substituted aminopyridinone intermediate) | MS (ES): m/z 394.47 [M + H]$^+$, LCMS purity: 98.40%, HPLC purity: 98.08%, $^1$H NMR (DMSO-d$_6$, 400 MHZ): 8.93 (s, 1H), 8.28-8.27 (d, J = 7.2 Hz, 1H), 8.21 (s, 1H), 7.91 (m, 1H), 7.56 (t, 2H), 7.42-7.32 (m, 4H), 7.23 (s, 1H), 6.38-6.34 (t, J = 16 Hz, 1H), 6.21 (s, 1H), 2.92-2.91 (d, J = 4.4 Hz, 3H). |
| I-10 | (4-morpholinophenyl-substituted aminopyridinone intermediate) | MS (ES): m/z 461.66 [M + H]$^+$, LCMS purity: 94.48, HPLC purity: 96.5%, $^1$H NMR (DMSO-d$_6$, 400 MHZ): 9.68 (S, 1H), 8.79 (s, 1H), 8.41 (s, 1H), 7.99-7.97 (d, J = 6.8 Hz, 1H), 7.46-7.44 (d, J = 6.4 Hz, 1H), 7.36-7.34 (d, J = 8.4 Hz, 2H), 7.14-7.12 (d, J = 8 Hz, 2H), 6.42-6.38 (t, 1H), 5.97 (s, 1H), 3.78 (s, 4H), 3.23 (s, 4H), 3.00 (s, 3H). |
| I-11 | (1-methylpyrazol-4-amine intermediate) | MS (ES): m/z 287.47 [M + H]$^+$, LCMS purity: 98.32%, HPLC purity: 97.40%, $^1$H NMR (DMSO-d$_6$, 400 MHZ): 9.30 (s, 1H), 8.13 (s, 1H), 777 (s, 2H), 7.51 (s, 2H), 7.19 (s, 1H), 5.38 (s, 1H), 3.82 (s, 3H), 3.14 (m, 3H). |
| I-12 | (1-cyclohexyl-aminopyridinone intermediate) | MS (ES): m/z 382 [M + H]$^+$, LCMS purity: 94.78%, HPLC purity: 94.9%, $^1$H NMR (DMSO-d$_6$, 400 MHZ): 9.81 (bs, 1H), 8.971 (bs, 1H), 8.36 (s, 1H), 7.79 (d, 1H), 7.59-7.58 (d, J = 6.4 Hz, 1H), 6.38-6.34 (m, 1H), 5.85 (s, 1H), 4.76 (t, 1H), 2.98 (s, 3H), 1.85-1.77 (t, 4H), 1.65 (t, 2H), 1.42-1.39 (d, 2H), 1.21 (bs, 2H). |
| I-13 | (2,6-dimethylpyridin-4-amine intermediate) | MS (ES): m/z 312.53 [M + H]$^+$, LCMS purity: 99%, HPLC purity: 95.10%, $^1$H NMR (MeOD, 400 MHZ): 8.34 (s, 1H), 7.72 (s, 2H), 5.79 (s, 1H), 3.11 (s, 3H), 2.61 (s, 6H). |
| I-14 | (2-chloro-3-methylaniline intermediate) | MS (ES): m/z 331.45 [M + H]$^+$, LCMS purity: 99.63%, HPLC purity: 98.29%, $^1$H NMR (DMSO-d$_6$, 400 MHZ): 9.00 (s, 1H), 8.12 (s, 1H), 7.89-7.88 (d, J = 4.8 Hz, 1H), 7.65-7.64 (d, J = 7.6 Hz, 1H), 7.33 (s, 1H), 7.24-7.21 (t, 1H), 7.17-7.15 (d, J = 7.2 Hz, 1H), 7.03 (s, 1H), 5.73 (s, 1H), 2.92-2.91 (d, 3H), 2.39 (s, 3H). |
| I-15 | (1-(thiazol-2-yl)-aminopyridinone intermediate) | MS (ES): m/z 383.38 [M + H]$^+$, LCMS purity: 97.85%, HPLC purity: 98.95%, $^1$H NMR (DMSO-d$_6$, 400 MHZ): 9.29 (s, 1H), 8.50-8.48 (d, J = 7.2 Hz, 1H), 8.38-8.36 (d, J = 8 Hz, 1H), 8.22 (s, 1H), 7.98 (bs, 1H), 7.85 (bs, 1H), 7.73 (s, 1H), 7.30-7.23 (d, 2H), 6.65-6.63 (m, 1H), 6.29 (s, 1H), 2.93 (s, 2H), 1.24 (s, 1H). |

TABLE 45-continued

| Compound | Intermediate | Characterization data |
| --- | --- | --- |
| I-16 | 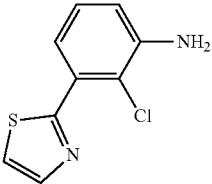 [SMILES: Nc1cccc(-c2nccs2)c1Cl] | MS (ES): m/z 400.57 [M + H]⁺, LCMS purity: 100%, HPLC purity: 97.25%, ¹H NMR (DMSO-d₆, 400 MHZ): 9.23 (s, 1H), 8.14 (s, 1H), 8.06-8.05 (d, J = 2.4 Hz, 1H), 7.99-7.90 (m, 4H), 7.49-7.45 (t, J = 7.6 Hz, 1H), 7.29 (s, 1H), 7.04 (s, 1H), 5.77 (s, 1H), 2.92 (s, 3H). |
| I-17 | 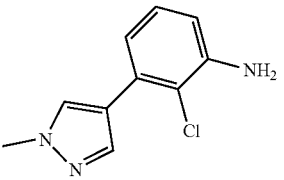 | MS (ES): m/z 397.84 [M + H]⁺, LCMS purity: 95.86%, HPLC purity: 99.15%, ¹H NMR (DMSO-d₆, 400 MHZ): 9.08 (s, 1H), 8.16-8.13 (d, J = 12.4 Hz, 2H), 7.91 (s, 1H), 7.82 (s, 1H), 7.68 (s, 1H), 7.34 (s, 3H), 7.06 (s, 1H), 5.75 (s, 1H), 3.88 (s, 3H), 2.90 (s, 3H). |
| I-18 | 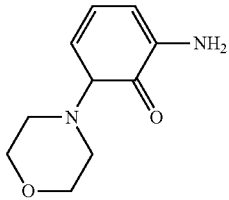 [SMILES: NC1=CC=CC(N2CCOCC2)C1=O] | MS (ES): m/z 402.57 [M + H]⁺, LCMS purity: 99.24%, HPLC purity: 97.96%, ¹H NMR (DMSO-d₆, 400 MHZ): 9.04 (s, 1H), 8.11 (s, 1H), 7.89-7.88 (d, J = 4.8 Hz, 1H), 7.48-7.46 (d, J = 8 Hz, 1H), 7.31-7.25 (m, 2H), 7.05 (s, 1H), 6.99-6.97 (d, J = 8 Hz, 1H), 5.72 (s, 1H), 3.76 (s, 4H), 2.98 (s, 3H), 2.91-2.90 (d, J = 4.4 Hz, 3H). |
| I-19 | 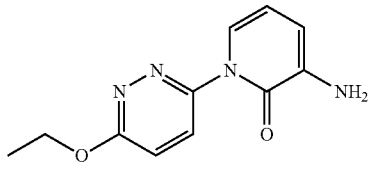 | MS (ES): m/z 422.65 [M + H]⁺, LCMS purity: 100%, HPLC purity: 98.65%, ¹H NMR (DMSO-d₆, 400 MHZ): 9.00 (s, 1H), 8.32-8.31 (d, J = 6.4 Hz, 1H), 8.20 (s, 1H), 8.04-8.01 (d, J = 9.6Hz, 1H), 7.93 (bs, 1H), 7.56 (bs, 1H), 7.45-7.43 (d, J = 9.2 Hz, 1H), 7.36 (s, 1H), 7.24 (s, 1H), 6.45 (s, 1H), 6.21 (s, 1H), 4.56-4.54 (d, J = 6.4 Hz, 1H), 2.90 (s, 2H), 1.42 (s, 2H), 1.23 (s, 3H). |
| I-20 | 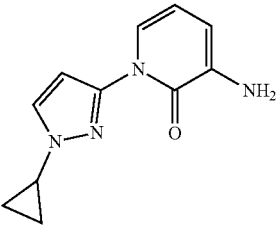 [SMILES: Nc1cccn(-c2ccn(C3CC3)n2)c1=O] | MS (ES): m/z 406.42 [M + H]⁺, LCMS purity: 100%, HPLC purity: 99.81%, ¹H NMR (DMSO-d₆, 400 MHZ): 9.00 (s, 1H), 8.26-8.24 (d, J = 6 Hz, 1H), 8.21 (s, 1H), 7.94-7.93 (s, 2H), 7.68-7.66 (d, J = 6.8 Hz, 1H), 7.33 (s, 1H), 7.24 (s, 1H), 6.76 (s, 1H), 6.40-6.36 (m, 1H), 6.24 (s, 1H), 3.81-3.78 (m, 1H), 2.92-2.91 (d, J = 2.4 Hz, 3H), 1.11 (bs, 2H), 1.02-1.01 (d, 2H). |
| I-24 | 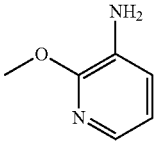 | MS (ES): m/z 314.39 [M + H]⁺, LCMS purity: 99.10%, HPLC purity: 98.71%, ¹H NMR (DMSO-d₆, 400 MHZ): 9.34 (m, 1H), 8.48 (m, 1H), 8.31 (s, 1H), 8.14-8.12 (d, J = 8 Hz, 1H), 8.00-7.99 (d, J = 4 Hz, 1H), 7.06-7.03 (m, 1H), 5.75 (s, 1H), 3.97 (s, 3H), 2.93 (s, 3H). |
| I-26 | 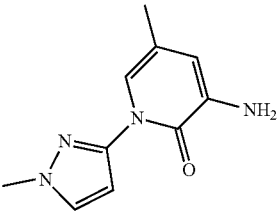 | MS(ES): m/z 394.23 [M + H]⁺, LCMS purity: 96.11%, HPLC purity: 99.85%, ¹H NMR (DMSO-d₆, 400 MHZ): 9.00 (s, 1H), 8.22-8.20 (d, J = 8 Hz, 2H), 7.93-7.92 (d, J = 4.4 Hz, 1H), 7.82 (s, 1H), 7.46 (s, 1H), 7.38 (s, 2H), 6.75 (s, 1H), 6.25 (s, 1H), 3.90 (s, 3H), 2.92-2.91 (d, J = 4 Hz, 3H), 2.138 (s, 3H). |
| I-27 | 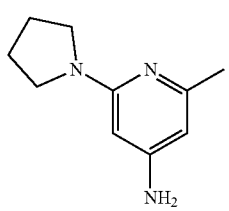 | MS (ES): m/z 367.47 [M + H]⁺, LCMS purity: 100%, HPLC purity: 97.97%, ¹H NMR (DMSO-d₆, 400 MHZ): 9.60 (s, 1H), 8.22 (s, 1H), 7.95 (s, 1H), 7.50-7.46 (d, J = 13.6 Hz, 2H), 6.70 (s, 1H), 6.50 (s, 1H), 5.62 (s, 1H), 3.345 (bs, 4H), 2.94-2.93 (d, J = 4.4 Hz, 3H), 2.27 (s, 3H), 1.95 (s, 4H). |

TABLE 45-continued

| Compound | Intermediate | Characterization data |
| --- | --- | --- |
| I-29 | | MS (ES): m/z 397.53 [M + H]+, LCMS purity: 95.90%, HPLC purity: 95.12%, CHIRAL HPLC purity: 98.13%, $^1$H NMR (DMSO-$d_6$, 400 MHZ): 11.69 (s, 1H), 9.66 (m, 1H), 8.23 (s, 1H), 8.04 (m, 1H), 7.47 (s, 1H), 7.38-7.33 (s, 1H), 6.56 (s, 1H), 5.67 (s, 1H), 4.09 (s, 1H), 3.51 (m, 4H), 3.28 (s, 3H), 2.94-2.93 (d, J = 4 Hz, 3H), 2.29 (s, 3H), 2.10-2.04 (m, 2H). |
| I-31 | | MS (ES): m/z 394.52 [M + H]+, LCMS purity: 100%, HPLC purity: 96.87%, $^1$H NMR (DMSO-$d_6$, 400 MHZ): 8.75 (s, 1H), 8.26-8.16 (m, 3H), 7.87 (s, 1H), 7.63 (s, 1H), 7.29 (s, 1H), 7.21 (bs, 2H), 6.18 (s, 1H), 3.92 (s, 3H), 2.98-2.97 (d, J = 4 Hz, 3H), 2.16 (s, 3H). |
| I-35 | | MS (ES): m/z 362.48 [M + H]+, LCMS purity: 97.17%, HPLC purity: 97.51%, $^1$H NMR (DMSO-$d_6$, 400 MHZ): 9.33 (s, 1H), 8.32 (S, 1H), 8.23-8.22 (d, J = 2.4 Hz, 1H), 7.69-7.68 (d, J = 4 Hz, 1H), 6.21 (s, 1H), 4.02-4.01 (d, J = 4 Hz, 2H), 2.94 (s, 3H), 1.29-1.23 (m, 3H). |
| I-37 | | MS (ES): m/z 435.57 [M + H]+, LCMS purity: 100%, HPLC purity: 97.07%, $^1$H NMR (DMSO-$d_6$, 400 MHZ): 8.99 (s, 1H), 8.30-8.28 (d, J = 8 Hz, 1H), 8.21 (s, 1H), 8.03-8.01 (t, J = 8 Hz, 1H), 7.93-7.92 (d, J = 4 Hz, 1H), 7.77-7.52 (d, J = 8 Hz, 1H), 7.71-7.69 (d, , J = 8 Hz, 1H), 7.60-7.58 (d, J = 8 Hz, 1H),7.36 (s, 1H), 7.24 (s, 1H), 6.45-6.43 (t, J = 8 Hz, 1H), 6.23 (s, 1H), 5.37 (s, 1H), 2.93-2.91 (d, J = 8 Hz, 3H), 1.54 (s, 6H). |
| I-40 | | MS (ES): m/z 389.43 [M + H]+, LCMS purity: 96.52%, HPLC purity: 97.86%, $^1$H NMR (DMSO-$d_6$, 400 MHZ): 9.03 (s, 1H), 8.63 (s, 1H), 8.29 (s, 1H), 8.22 (s, 1H), 8.04-8.03 (d, 4 Hz, 1H), 7.83-7.22 (d, J = 4 Hz, 1H), 7.34 (s, 1H), 7.20 (s, 1H), 6.04 (s, 1H), 5.45-5.43 (t, J = 8 Hz, 1H), 4.09-4.07 (t, J = 8 Hz, 2H), 3.91-3.90 (t, J = 4 Hz, 2H), 2.95-2.94 (d, J = 4 Hz, 3H). |
| I-48 | | MS (ES): m/z 395.38 [M + H]+, LCMS purity: 98.71%, HPLC purity: 96.61%, $^1$H NMR (DMSO-$d_6$, 400 MHZ): 9.47 (s, 1H), 8.64 (s, 1H), 8.35 (s, 1H), 8.13-8.11 (t, J = 8 Hz, 1H), 8.00 (s, 1H), 7.93 (s, 1H), 7.65-7.64 (d, , J = 4 Hz, 1H), 6.48-6.46 (t, J = 8 Hz, 1H), 6.07 (s, 1H), 2.98 (s, 3H). |
| I-60 | | MS (ES): m/z 383.54 [M + H]+, LCMS purity: 99.42%, HPLC purity: 98.74%, $^1$H NMR (DMSO-$d_6$, 400 MHZ): 8.26 (s, 1H), 8.11 (s, 1H), 7.45 (s, 1H), 7.35 (s, 1H), 7.18-7.09 (m, 2H), 6.52 (s, 1H), 5.67 (s, 1H), 5.02 (s, 1H), 4.43 (s, 1H), 3.51 (s, 3H), 2.94-2.93 (d, , J = 4 Hz, 3H), 2.33 (s, 3H), 2.05-1.96 (m, 2H). |

US 10,562,906 B2

TABLE 45-continued

| Compound | Intermediate | Characterization data |
| --- | --- | --- |
| I-61 | | MS (ES): m/z 397.53 [M + H]⁺, LCMS purity: 98.72%, HPLC purity: 96.54%, $^1$H NMR (DMSO-$d_6$, 400 MHZ): 9.63 (s, 1H), 8.23 (s, 1H), 8.03 (bs, 1H), 7.42 (s, 1H), 7.33 (s, 1H), 7.00 (bs, 1H), 6.65 (s, 1H), 5.62 (s, 1H), 4.94 (s, 1H), 4.12 (bs, 1H), 3.93-3.90 (m, 1H), 3.57-3.50 (m, 1H), 2.92-2.89 (m, 3H), 2.28 (s, 3H), 1.91 (bs, 1H), 1.72-1.68 (m, 1H), 1.53-1.40 (m, 2H), 1.29-1.23 (m, 2H). |
| I-69 | | MS (ES): m/z 395.37 [M + H]⁺, LCMS purity: 100%, HPLC purity: 99.53%, $^1$H NMR (DMSO-$d_6$, 400 MHZ): 9.62 (s, 1H), 8.31 (s, 1H), 8.16-8.15 (d, J = 4.8 Hz, 2H), 7.97-7.96 (d, J = 4 Hz, 1H), 7.70-7.64 (m, 2H), 7.40-7.36 (t, J = 8 Hz, 2H), 7.24 (s, 2H), 6.49 (s, 1H), 2.94 (s, 3H). |
| I-91 | | MS (ES): m/z 368.38 [M + H]⁺, LCMS purity: 99.9%, HPLC purity: 97.89%, $^1$H NMR (DMSO-$d_6$, 400 MHZ): 9.27 (s, 1H), 8.45-8.43 (d, J = 8 Hz, 1H), 8.17 (s, 1H), 8.07-8.25 (m, 1H), 8.03-8.02 (d, J = 4 Hz, 1H), 7.41-7.38 (m, 1H), 7.19 (s, 1H), 7.10 (s, 1H), 5.80 (s, 1H), 2.94-2.92 (d, J = 8 Hz, 3H). |

103.2. Synthesis of 5-(5,7-dimethyl-1H-indol-3-yl)-7-(methylamino)pyrazolo[1,5-a]pyrimidine-3-carboxamide (I-36)

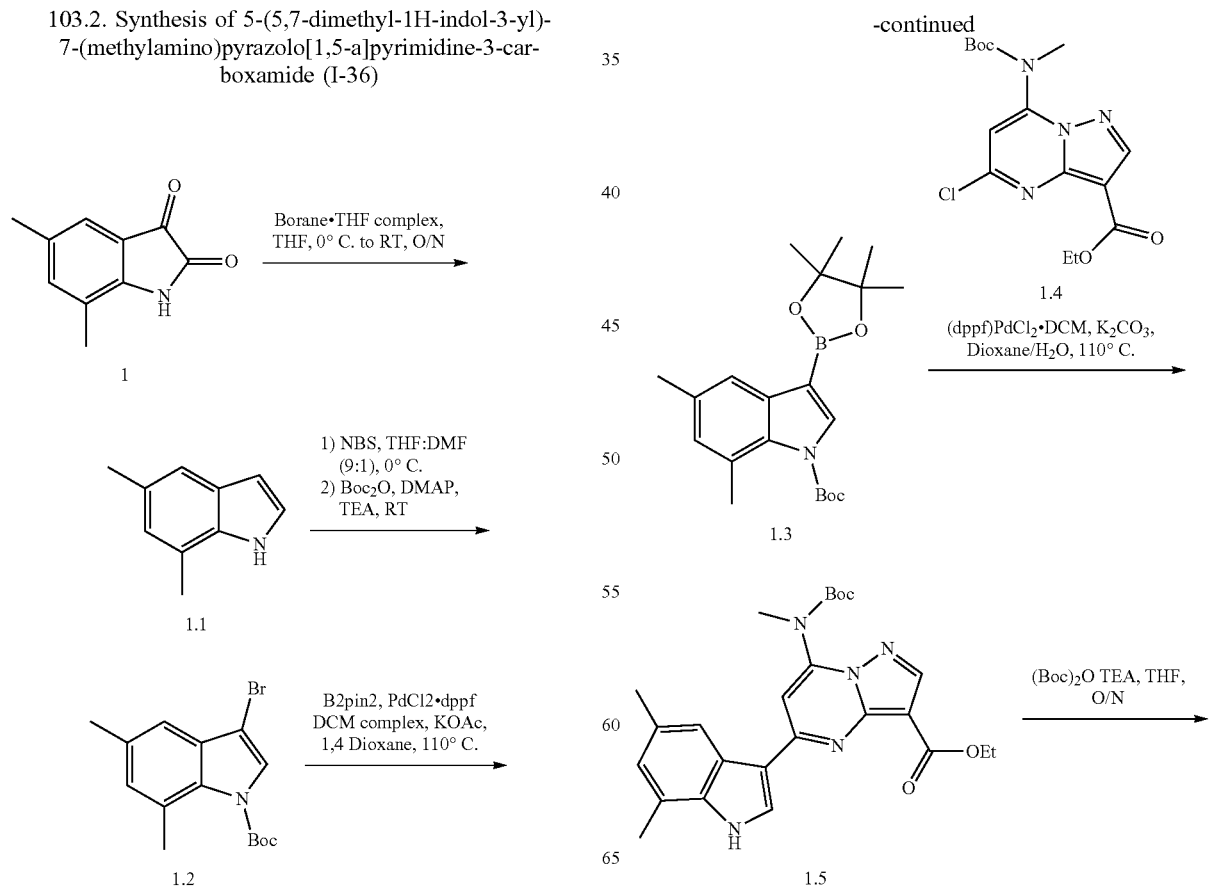

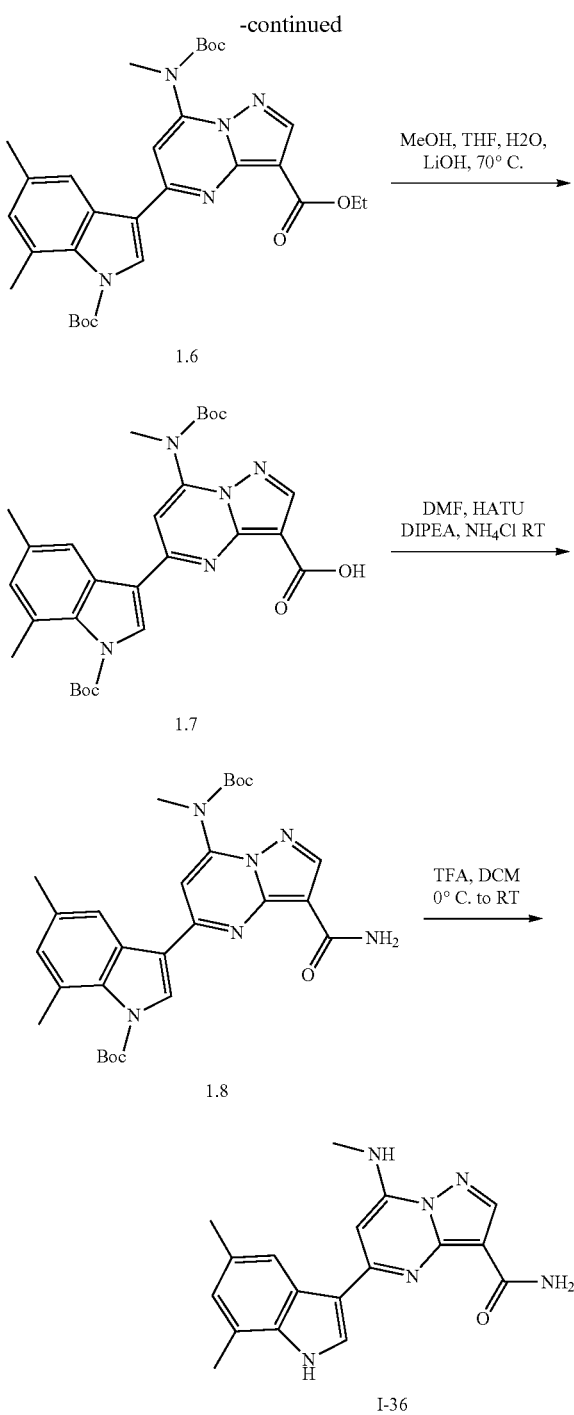

matography and compound was eluted in 30% ethyl acetate in hexane to obtain pure 1.1 (3.2 g, 39.61%). MS (ES): m/z 146.21 [M+H]+

Synthesis of Compound 1.2.

To a cooled solution of 1.1 (3.2 g, 22.04 mmol, 1.0 eq) in mixture of tetrahydrofuran:dimethylformamide (40 mL, 9:1), N-bromosuccinamide (3.92 g, 22.04 mmol, 1 eq) was added. Reaction mixture was stirred at 0° C. for 15 min followed by addition of triethylamine (7.79 g, 77.14 mmol, 3.5 eq), 4-Dimethylaminopyridine (15 mg), and Di-tert-butyl dicarbonate (13.75 g, 66.12 mmol, 3 eq) at same temperature. The reaction was stirred at room temperature for 30 min. After completion of reaction, reaction mixture transferred into ice cold water and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 1.2 (3.2 g, 44.79%). MS(ES): m/z 325.22 [M+H]+.

Synthesis of Compound 1.3.

To a solution of 1.2 (3.2 g, 9.87 mmol, 1.0 eq) in 1,4-dioxane (25 mL) was added bis(pinacolato)diboron (7.53 g, 29.61 mmol, 3 eq) and potassium acetate (2.90 g, 29.61 mmol, 3 eq). The reaction mixture was degassed for 10 min. under argon atmosphere, then 1,1'-Bis(diphenyl-phosphino)ferrocene]dichloropalladium(II)dichloride dichloromethane (0.241 g, 0.295 mmol, 0.03 eq) was added and again degassed for 5 min. The reaction was stirred at 110° C. for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 8% ethyl acetate in hexane to obtain pure 1.2 (1.2 g, 32.75%). MS(ES): m/z 372.28 [M+H]+.

Synthesis of Compound 1.4.

Compound was synthesized using general procedure of core synthesis to obtain 1.4 (Yield: 62.21%). MS (ES): m/z 355.5 [M+H]+

Synthesis of Compound 1.5.

To a solution of 1.4 (0.575 g, 1.62 mmol, 1.0 eq) in 1,4-dioxane (7 mL) and water (5 mL) was added 1.3 (1.2 g, 3.23 mmol, 2 eq), potassium carbonate (0.600 g, 4.86 mmol, 3 eq). The reaction mixture was degassed for 10 min. under argon atmosphere, then 1,1'-Bis(diphenylphosphino)ferrocene]dichloropalladium(II), dichloride dichloromethane (0.039 g, 0.0486 mmol, 0.03 eq) again degassed for 5 min. The reaction was stirred at 110° C. for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 21% ethyl acetate in hexane to obtain pure 1.5 (0.320 g, 42.72%). MS(ES): m/z 464.54 [M+H]+.

Synthesis of Compound 1.6.

To a cooled solution of 1.5 (0.320 g, 0.690 mmol, 1.0 eq) in tetrahydrofuran (2 mL) was added Triethylamine (0.243

Synthesis of Compound 1.1.

To a cooled solution of 1. (10.0 g, 57.08 mmol, 1.0 eq) in tetrahydrofuran (100 ml), borane tetrahydrofuran (114.0 mL, 114.16 mmol, 2.0 eq) was added dropwise at 0° C. temperature. The reaction was stirred at room temperature for 16 h. After completion of reaction, 5% hydrochloric acid was added. Reaction mixture was transferred into saturated sodium bicarbonate and product was extracted with ethyl acetate. Organic layer was combined and dried over sodium sulphate and concentrated under reduced pressure to obtain crude material. This was further purified by column chrog, 2.41 mmol, 3.5 eq). The reaction was stirred at 0° C. for 15 min. and Di-tert-butyl dicarbonate (0.430 g, 2.07 mmol, 3.0 eq) added dropwise at same temperature. The reaction was stirred at room temperature for 16 h. After completion of reaction, reaction mixture was extracted with ethyl acetate. Organic layer was combined, washed with brine solution, dried over sodium sulphate and concentrated under reduced pressure to obtain crude material. This was further purified by column chromatography and compound was eluted in 3% ethyl acetate in hexane to obtain pure 1.2 (0.200 g, 51.40%). MS(ES): m/z 564.66 [M+H]$^+$.

Synthesis of Compound 1.7.

To a solution of 1.5 (0.200 g, 0.354 mmol, 1.0 eq), in tetrahydrofuran: methanol: water (6 mL, 1:1:1) was added lithium hydroxide (0.148 g, 3.54 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.4% methanol in dichloromethane to obtain pure 1.7 (0.110 g, 57.88%). MS(ES): m/z 536.60 [M+H]$^+$.

Synthesis of Compound 1.8.

Compound was synthesized using general procedure A to obtain 1.8. (0.070 g, 63.75%). MS (ES): m/z 535.62 [M+H]$^+$ Synthesis of Compound I-36.

Compound was synthesized using general procedure C to obtain I-36 (0.030 g, 68.52%). MS (ES): m/z 335.27 [M+H]$^+$, LCMS purity: 100.0%, HPLC purity: 98.04%, $^1$H NMR (DMSO-d$_6$, 400 MHZ): 11.69 (s, 1H), 8.40 (s, 1H), 8.32 (s, 1H), 8.08-7.97 (m, 3H), 7.58 (s, 1H), 6.86 (s, 1H), 6.70 (s, 1H), 3.10-3.09 (d, J=4 Hz, 3H), 2.34 (s, 6H).

103.3. Synthesis of 5-((1-(isoxazol-3-yl)-2-oxo-1,2-dihydropyridin-3-yl)amino)-7-(methylamino)pyrazolo[1,5-a]pyrimidine-3-carboxamide (I-43)

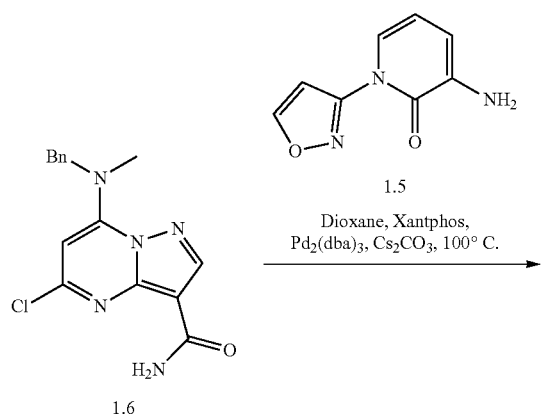

Synthesis of Compound 1.6.

Compound was synthesized using general procedure of core synthesis to obtain 1.6 (Yield: 45.0%). MS (ES): m/z 316.76 [M+H]$^+$ Synthesis of Compound 1.7.

Compound was synthesized using general procedure B synthesis to obtain 1.7 (0.055 g, 31.71%). MS (ES): m/z 457.47 [M+H]$^+$ Synthesis of Compound I-43.

Mixture of 1.7 (0.055 g, 0.120 mmol, 1.0 eq) and triflic acid (2 mL) was allowed to stir at 70'C for 1 h. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-43 (0.027 g, 61.17%). MS (ES): m/z 367.42 [M+H]$^+$, LCMS purity: 99.60%, HPLC purity: 98.59%, $^1$H NMR (DMSO-d$_6$, 400 MHZ): 9.13 (s, 1H), 9.07 (s, 1H), 8.31-8.30 (d, J=4 Hz, 1H), 8.21 (s, 1H), 7.95-7.94 (d, J=4 Hz, 1H), 7.60-7.59 (d, J=4 Hz, 1H), 7.30 (s, 1H), 7.20 (s, 2H), 6.47-6.45 (t, J=8 Hz, 1H), 6.24 (s, 1H), 2.92-2.90 (d, J=8 Hz, 3H).

Additional compounds prepared by substantially the same method, and their characterization data, are listed in the Table 46 below. The intermediate corresponding to 1.5 of the above scheme is listed for each compound.

TABLE 46

| Compound | Intermediate | Characterization data |
|---|---|---|
| I-45 | | MS (ES): m/z 474.35 [M + H]+, LCMS purity: 100%, HPLC purity: 100%, $^1$H NMR (DMSO-$d_6$, 400 MHZ): 8.99 (s, 1H), 8.78 (s, 1H), 8.30-8.29 (d, J = 4 Hz, 1H), 8.20 (s, 1H), 8.18-8.17 (d, J = 4 Hz, 1H), 7.96-7.92 (m, 2H), 7.62-7.61 (d, J = 4 Hz, 1H), 7.34 (s, 1H), 7.23 (s, 1H), 6.45-6.43 (t, J = 8 Hz, 1H), 6.22 (s, 1H), 3.52-3.48 (m, 4H), 2.92-2.91 (d, J = 4 Hz, 3H), 1.92-1.87 (m, 4H). |
| I-46 | | MS (ES): m/z 381.83 [M + H]+, LCMS purity: 100%, HPLC purity: 97.47%, $^1$H NMR (DMSO-$d_6$, 400 MHZ): 9.05 (s, 1H), 8.30-8.29 (d, J = 4 Hz, 1H), 8.21 (s, 1H), 7.95-7.94 (d, J = 4 Hz, 1H), 7.58-7.56 (d, J = 8 Hz 1H), 7.31 (s, 1H), 7.21 (s, 1H), 6.88 (s, 1H), 6.46-6.44 (t, J = 8 Hz, 1H), 6.24 (s, 1H), 2.92-2.91 (d, J = 4 Hz, 3H), 2.51 (s, 3H). |
| I-47 | | MS (ES): m/z 367.58 [M + H]+, LCMS purity: 95.11%, HPLC purity: 95.03%, $^1$H NMR (DMSO-$d_6$, 400 MHZ): 11.27 (s, 1H), 9.32 (s, 2H), 7.95-7.93 (d, J = 8 Hz, 1H), 7.89-7.87 (t, J = 8 Hz, 1H), 6.89-6.87 (d, J = 8 Hz, 1H), 6.49 (s, 1H), 4.22-4.20 (t, J = 8 Hz, 2H), 3.07-3.05 (d, J = 8 Hz, 3H), 2.61-2.59 (t, J = 8 Hz, 2H), 2.12-2.06 (m, 2H). |
| I-51 | | MS (ES): m/z 390.53 [M − H]+, LCMS purity: 98.35%, HPLC purity: 98.59%, $^1$H NMR (DMSO-$d_6$, 400 MHZ): 9.03 (s, 1H), 8.91-8.89 (d, J = 8 Hz, 1H), 8.30-8.28 (d, J = 8 Hz, 1H), 8.21 (s, 1H), 7.95-7.94 (d, J = 4 Hz 2H), 7.76-7.74 (d, J = 8 Hz, 1H), 7.32 (s, 1H), 7.22 (s, 1H), 6.48-6.46 (t, J = 8 Hz, 1H), 6.23 (s, 1H), 2.91-2.90 (d, J = 4 Hz, 3H), 2.71 (s, 3H). |
| I-53 | | MS (ES): m/z 449.51 [M + H]+, LCMS purity: 98.97%, HPLC purity: 97.25%, $^1$H NMR (DMSO-$d_6$, 400 MHZ): 9.21 (s, 1H), 9.06 (s, 1H), 8.91 (s, 1H), 8.33-8.31 (t, J = 8 Hz, 1H), 8.21 (s, 1H), 7.93 (s, 1H), 7.65-7.63 (d, J = 8 Hz, 1H), 7.33 (s, 1H), 7.24 (bs, 1H), 6.51-6.50 (t, J = 4 Hz, 1H), 6.24 (s, 1H), 3.08-3.05 (d, J = 12 Hz, 6H), 2.92-2.91 (d, J = 4 Hz, 3H). |
| I-54 | | MS (ES): m/z 381.43 [M + H]+, LCMS purity: 98.46%, HPLC purity: 95.00%, $^1$H NMR (DMSO-$d_6$, 400 MHZ): 9.93 (s, 1H), 8.21 (s, 2H), 8.05 (s, 1H), 7.44 (s, 1H), 7.39 (s, 1H), 7.25 (s, 1H), 5.69 (s, 1H), 4.00-3.98 (t, J = 8 Hz, 2H), 2.93-2.92 (d, J = 4 Hz, 3H), 2.60-2.58 (t, J = 8 Hz, 2H), 2.37 (s, 3H), 2.04-1.99 (m, 2H). |
| I-59 | | MS(ES): m/z 398.44 [M + H]+, LCMS purity: 98.03%, HPLC purity: 98.40%, $^1$H NMR (DMSO-$d_6$, 400 MHZ): 8.83 (s, 1H), 8.18 (s, 1H), 8.15-8.13 (d, J = 7.2 Hz, 1H), 7.89-7.88 (d, J = 5.2 Hz, 1H), 7.41-7.40 (d, J = 6 Hz, 1H), 7.32 (s, 1H), 7.20 (s, 1H), 6.30-6.26 (t, J = 7.2 Hz, 1H), 6.18 (s, 1H), 4.78-4.70 (m, 2H), 3.52-3.49 (m, 1H), 2.92-2.91 (d, J = 4.8 Hz, 3H), 1.98-1.95 (d, J = 10 Hz, 2H), 1.81-1.77 (m, 4H), 1.37-1.34 (m, 2H). |

TABLE 46-continued

| Compound | Intermediate | Characterization data |
|---|---|---|
| I-63 | | MS (ES): m/z 436.62 [M + H]+, LCMS purity: 95.42%, HPLC purity: 95.28%, $^1$H NMR (DMSO-d$_6$, 400 MHZ): 9.08 (s, 1H), 9.03 (s, 1H), 8.93 (s, 1H), 8.33-8.31 (d, J = 8 Hz, 1H), 8.22 (s, 1H), 7.95-7.94 (d, J = 4 Hz, 1H), 7.61-7.60 (d, J = 6.8 Hz, 1H), 7.35 (s, 1H), 7.24 (s, 1H), 6.49-6.45 (t, 1H), 6.24 (s, 1H), 5.65 (s, 1H), 2.93-2.92 (d, J = 4 Hz, 3H), 1.55 (s, 6H) |
| I-65 | | MS(ES): m/z 369.23 [M + H]+, LCMS purity: 95.59%, HPLC purity: 98.22%, $^1$H NMR (DMSO-d$_6$, 400 MHZ): 9.73 (s, 1H), 8.19 (s, 1H), 7.74-7.65 (m, 3H), 7.17-7.15 (d, J = 8 Hz, 1H), 6.82 (s, 1H), 4.49-4.47 (t, J = 8 Hz, 2H), 4.33-4.31 (t, J = 8.4 Hz, 2H), 3.01-3.00 (d, 2H). |
| I-67 | | MS (ES): m/z 447.46 [M + H]+, LCMS purity: 95.69%, HPLC purity: 95.11%, $^1$H NMR (DMSO-d$_6$, 400 MHZ): 8.84 (s, 1H), 8.18 (s, 1H), 8.15-8.13 (d, J = 1.6 Hz, 1H), 7.89-7.88 (d, J = 4.4 Hz, 1H), 7.46-7.44 (d, J = 6.4 Hz, 1H), 7.32 (s, 1H), 7.21 (s, 1H), 6.31-6.25 (t, J = 7.2 Hz, 1H), 6.18 (s, 1H), 4.78 (s, 1H), 3.07-3.05 (d, J = 11.6 Hz, 2H), 2.91-2.90 (d, J = 4.8 Hz, 3H), 2.81-2.76 (m, 2H), 1.93-1.915 (d, J = 8.8 Hz, 2H), 1.76-1.74 (d, 2H). |
| I-68 | | MS(ES): m/z 467.55 [M + H]+, LCMS purity: 95.69%, HPLC purity: 95.11%, $^1$H NMR (DMSO-d$_6$, 400 MHZ): 8.83 (s, 1H), 8.18-8.14 (t, J = 13.6 Hz, 2H), 7.88-7.87 (d, J = 4.8 Hz, 1H), 7.31-7.27 (t, J = 10.8 Hz, 2H), 7.21 (s, 1H), 6.35-6.31 (t, J = 14 Hz, 2H), 6.18 (s, 1H), 4.89 (s, 1H), 3.65 (s, 4H), 2.91-2.90 (d, J = 4.8 Hz, 3H), 2.40-2.33 (m, 4H), 2.15-2.09 (m, 3H), 1.98-1.89 (m, 2H), 1.53 (s, 4H). |
| I-71 | | MS (ES): m/z 404.52 [M + H]+, LCMS purity: 97.22%, HPLC purity: 96.42%, CHIRAL HPLC purity: (50.17%, 49.82%), $^1$H NMR (DMSO-d$_6$, 400 MHZ): 8.81 (s, 1H), 8.55-7.55 (d, J = 1.6 Hz, 1H), 8.21 (s, 1H), 8.00-7.99 (d, J = 4 Hz, 1H), 7.86-7.86 (d, J = 2 Hz, 1H), 7.31 (s, 1H), 7.21 (s, 1H), 6.01 (s, 1H), 5.53 (s, 1H), 3.97-3.88 (m, 3H), 3.78-3.73 (m, 1H), 2.95-2.94 (d, J = 4 Hz, 3H), 2.29-2.24 (m, 1H), 2.17-2.14 (m, 1H). |
| I-72 | | MS(ES): m/z 342.38 [M + H]+, LCMS purity: 95.80%, HPLC purity: 99.05%, $^1$H NMR (DMSO-d$_6$, 400 MHZ): 8.63 (s, 1H), 8.23-8.22 (d, J = 4 Hz, 1H), 8.15 (s, 1H), 7.90-7.86 (m, 2H), 7.33 (s, 1H), 7.12 (s, 1H), 6.94-6.91 (m, 1H), 5.89 (s, 1H), 5.38 (s, 1H), 2.94-2.92 (d, J = 4.8 Hz, 3H), 1.35-1.24 (m, 6H). |

TABLE 46-continued

| Compound | Intermediate | Characterization data |
| --- | --- | --- |
| I-73 | (6-methyl-4-amino-2-(1-methyl-1H-pyrazol-4-yl)pyridazin-3(2H)-one) | MS(ES): m/z 395.40 [M + H]⁺, LCMS purity: 96.98%, HPLC purity: 97.31%, ¹H NMR (DMSO-d₆, 400 MHZ): 9.63 (s, 1H), 8.34 (s, 1H), 8.29 (s, 1H), 8.12 (s, 2H), 7.97 (s, 1H), 7.25-7.27 (m, 1H), 7.42-7.47 (m, 1H), 6.47 (s, 1H), 3.91 (s, 3H), 2.94-2.92 (d, J = 4.4 Hz, 3H), 2.35-2.33 (d, J = 7.6 Hz, 3H). |
| I-75 | (5-methyl-3-amino-1-(1-methyl-1H-pyrazol-5-yl)pyridin-2(1H)-one) | MS(ES): m/z 394.41 [M + H]⁺, LCMS purity: 99.37%, HPLC purity: 98.66%, ¹H NMR (DMSO-d₆, 400 MHZ): 9.01 (s, 1H), 8.30-8.30 (d, J = 1.6 Hz, 1H), 8.30 (s, 1H), 7.94-7.93 (d, J = 4.8 Hz, 1H), 7.56-7.55 (d, J = 1.6 Hz, 1H), 7.46 (s, 1H), 7.37 (s, 1H), 7.05 (s, 1H), 6.45-6.45 (d, J = 2 Hz, 1H), 6.24 (s, 1H), 3.62 (s,3H), 2.90-2.89 (d, J = 4.8 Hz, 3H), 2.10 (s, 3H). |
| I-78 | (5-chloro-3-amino-2-isopropoxypyridine) | MS(ES): m/z 376.82 [M + H]⁺, LCMS purity: 100%, HPLC purity: 100%, ¹H NMR (DMSO-d₆, 400 MHZ): 8.75 (s, 1H), 8.52-8.52 (d, J = 2 Hz, 1H), 8.20 (s, 1H), 7.99-7.98 (d, J = 4.8 HZ, 1H), 7.85-7.85 (d, J = 2.4 Hz, 1H), 7.31 (s, 1H), 7.21 (s, 1H), 6.04 (s, 1H), 5.35-5.29 (m, 1H), 2.94 (s, 3H), 1.361-1.34 (d, J = 6 Hz, 6H) |
| I-80 | (5-chloro-3-amino-2-cyclobutoxypyridine) | MS(ES): m/z 388.83 [M + H]⁺, LCMS purity: 99.18%, HPLC purity: 98.86%, ¹H NMR (DMSO-d₆, 400 MHZ): 8.87 (s, 1H), 8.55-8.55 (d, J = 2.4 Hz, 1H), 8.21(s, 1H), 8.00-7.96 (d, J = 4.8 Hz, 1H), 7.83-7.82 (d, J = 2.4 Hz, 1H), 7.32 (s, 1H), 7.21 (s, 1H), 6.02 (s, 1H), 5.24-5.18 (m, 1H), 2.95-2.94 (d, J = 4.8 Hz, 3H), 2.56-2.51 (m, 2H), 2.43-2.34 (m, 2H), 1.83-1.81 (m, 1H), 1.69-1.66 (m, 1H). |
| I-84 | (5-chloro-3-amino-2-((tetrahydrofuran-3-yl)oxy)pyridine) | MS(ES): m/z 404.83 [M + H]⁺, LCMS purity: 99.14%, HPLC purity: 99.05%, Chiral HPLC purity: 98.91%, ¹H NMR (DMSO-d₆, 400 MHZ): 8.82 (s, 1H), 8.56 (s, 1H), 8.21 (s, 1H), 8.02-8.01 (d, J = 4.4 Hz, 1H), 7.87 (s, 1H), 7.32 (s, 1H), 7.21 (s, 1H), 6.01 (s, 1H), 5.54 (s, 1H), 3.98-3.89 (m, 3H), 3.79-3.73 (m, 1H), 2.95-2.94 (d, J = 4.8 Hz, 3H), 2.34-2.14 (m, 2H). |
| I-96 | (5-chloro-3-amino-2-((3-methoxycyclobutyl)oxy)pyridine) | MS (ES): m/z 418.44 [M + H]⁺, LCMS purity: 97.59%, HPLC purity: 96.28%, CHIRAL HPLC purity: 99.42%, ¹H NMR (DMSO-d₆, 400 MHZ): 8.88 (s, 1H), 8.57-8.56 (d, J = 4 Hz, 1H), 8.20 (s, 1H), 8.00 (s, 1H), 7.818-7.812 (d, J = 2.4 Hz, 1H), 7.32 (s, 1H), 7.19 (s, 1H), 6.03 (s, 1H), 4.91-4.90 (t, J = 4 Hz, 1H), 4.04-4.02 (d, J = 8 Hz, 1H), 3.68-3.66 (t, J = 8 Hz, 1H), 3.16 (s, 3H), 2.85-2.82 (m, 2H), 2.10-2.07 (m, 3H). |

TABLE 46-continued

| Compound | Intermediate | Characterization data |
|---|---|---|
| I-108 | | MS (ES): m/z 370.33 [M + H]+, LCMS purity: 97.34%, HPLC purity: 96.72%, $^1$H NMR (DMSO-$d_6$, 400 MHZ): 8.87 (s, 1H), 8.18 (s, 2H), 7.89 (s, 1H), 7.31-7.28 (t, J = 12 Hz, 2H), 7.21 (s, 1H), 6.32 (s, 1H), 6.20 (s, 1H), 5.51-5.50 (d, J = 4 Hz, 1H), 4.08-4.07 (d, J = 4 Hz, 2H), 3.89 (s, 2H), 3.78-3.76 (d, J = 8 Hz, 2H), 2.91 (s, 3H), 2.01 (m, 1H). |
| I-111 | | MS (ES): m/z 418.44 [M + H]+, LCMS purity: 96.05%, HPLC purity: 96.11%, $^1$H NMR (DMSO-$d_6$, 400 MHZ): 8.86 (s, 1H), 8.53 (s, 1H), 8.20 (s, 1H), 8.01-8.00 (d, J = 4 Hz, 1H), 7.83 (s, 1H), 7.31 (s, 1H), 7.19 (s, 1H), 6.01 (s, 1H), 5.32-5.30 (t, J = 8 Hz, 1H), 4.10-4.08 (t, J = 8 Hz, 1H), 3.17 (s, 3H), 2.95-2.93 (d, J = 8 Hz, 3H), 2.43-2.41 (t, J = 8 Hz, 4H). |
| I-112 | | MS (ES): m/z 421.52 [M + H]+, LCMS purity: 98.39%, HPLC purity: 95.48%, $^1$H NMR (DMSO-$d_6$, 400 MHZ): 9.91 (s, 1H), 8.24 (s, 1H), 8.10 (s, 1H), 7.51 (s, 1H), 7.26 (s, 1H), 7.14 (s, 1H), 7.03 (s, 1H), 5.61 (s, 1H), 3.38-3.34 (m, 4H), 2.94-2.93 (d, J = 4 Hz, 3H), 1.99-1.95 (m, 4H). |
| I-114 | | MS (ES): m/z 434.50 [M + H]+, LCMS purity: 99.28%, HPLC purity: 99.12%, $^1$H NMR (DMSO-$d_6$, 400 MHZ): 8.91 (s, 1H), 8.23-8.23 (d, J = 2 Hz, 1H), 8.20 (s, 1H), 7.92-7.91 (d, J = 4 Hz, 1H), 7.52 (s, 1H), 7.46 (s, 1H), 7.39 (s, 1H), 7.02 (s, 1H), 6.23 (s, 1H), 3.64-3.58 (s, 1H), 2.91-2.90 (d, J = 4 Hz, 3H), 2.23 (s, 3H), 2.09 (s, 3H), 1.09-1.02 (m, 4H) |
| I-152 | | MS(ES): m/z 350.30 [M + H]+, LCMS purity: 96.58%, HPLC purity: 98.99%, $^1$H NMR (DMSO-$d_6$, 400 MHZ): 9.12 (s, 1H), 8.39-8.37 (d, J = 8 Hz, 1H), 8.16 (s, 1H), 7.97-7.96 (d, J = 4.4 Hz, 2H), 7.77 (s, 1H), 7.24 (m, 2H), 7.01 (s, 1H), 5.88 (s, 1H), 2.93-2.91 (d, J = 4.4 Hz, 3H). |
| I-178 | | MS (ES): m/z 454.80 [M + H]+, LCMS purity: 97.28%, HPLC purity: 95.12%, $^1$H NMR (DMSO-$d_6$, 400 MHZ): 9.13 (s, 1H), 8.44 (s, 1H), 8.24 (s, 1H), 8.08 (s, 1H), 8.00 (bs, 1H), 7.47 (s, 1H), 7.17 (s, 1H), 6.33 (s, 1H), 3.69 (s, 3H), 2.91-2.89 (d, J = 4.8 Hz, 3H), 2.04 (s, 4H), 1.04 (bs, 1H). |

TABLE 46-continued

| Compound | Intermediate | Characterization data |
| --- | --- | --- |
| I-180 | (structure: 5-chloro-1-(1-cyclopropyl-5-methyl-1H-pyrazol-4-yl)-3-amino-pyridin-2(1H)-one) | MS (ES): m/z 454.37 [M − H]+, LCMS purity: 97.32%, HPLC purity: 96.77%, 1H NMR (DMSO-d6, 400 MHZ): 9.13 (s, 1H), 8.46 (s, 1H), 8.25 (s, 1H), 8.00 (s, 1H), 7.57 (s, 1H), 7.47 (s, 2H), 7.19 (s, 1H), 6.33 (s, 1H), 3.61 (bs, 1H), 2.92 (s, 3H), 2.25 (s, 3H), 1.08 (bs, 4H). |
| I-190 | (structure: 5-chloro-3-(tributylstannyl)-7-(tetrahydro-2H-pyran-4-yl)-1-Boc-indole) | MS (ES): m/z 425.40 [M + H]+, LCMS purity: 96.07%, HPLC purity: 96.61%, 1H NMR (DMSO-d6, 400 MHZ): 12.06 (s, 1H), 8.50-8.49 (d, J = 4 Hz, 1H), 8.34 (s, 1H), 8.23 (s, 1H), 8.16-8.15 (d, J = 4 Hz, 1H), 7.70 (s, 1H), 7.57 (s, 1H), 7.08 (s, 1H), 6.70 (s, 1H), 4.03-4.00 (d, J = 12 Hz, 2H), 3.59-3.53 (m, 2H), 3.10-3.08 (d, J = 8 Hz, 3H), 2.08 (s, 1H), 1.80 (bs, 4H). |
| I-195 | (structure: 3-amino-1-((S)-tetrahydrofuran-3-yl)pyridin-2(1H)-one) | MS (ES): m/z 370.18 [M + H]+, LCMS purity: 97.89%, HPLC purity: 97.27%, CHIRAL HPLC purity: 98.45%, 1H NMR (DMSO-d6, 400 MHZ): 10.01 (s, 1H), 9.15 (s, 1H), 8.48 (s, 1H), 7.71 (bs, 2H), 7.45 (bs, 2H), 6.36 (bs, 1H), 5.77 (s, 1H), 5.47 (s, 1H), 4.03 (s, 1H), 3.87 (s, 2H), 3.74 (s, 1H), 2.98 (s, 3H), 1.97 (s, 2H). |
| I-196 | (structure: 3-amino-1-((R)-tetrahydrofuran-3-yl)pyridin-2(1H)-one) | MS (ES): m/z 370.47 [M + H]+, LCMS purity : 97.60%, HPLC purity: 97.79%, CHIRAL HPLC purity: 99.40%, 1H NMR (DMSO-d6, 400 MHZ): 10.01 (s, 1H), 9.15 (s, 1H), 8.48 (s, 1H), 7.71 (bs, 2H), 7.45 (bs, 2H), 6.36 (bs, 1H), 5.77 (s, 1H), 5.47 (s, 1H), 4.03 (s, 1H), 3.87 (s, 2H), 3.74 (s, 1H), 2.98 (s, 3H), 1.97 (s, 2H). |

103.4. Synthesis of 5-(5-chloro-1-isopropyl-1H-pyrrolo[2,3-b]pyridin-3-yl)-7-(methylamino)pyrazolo[1,5-a]pyrimidine-3-carboxamide (I-272)

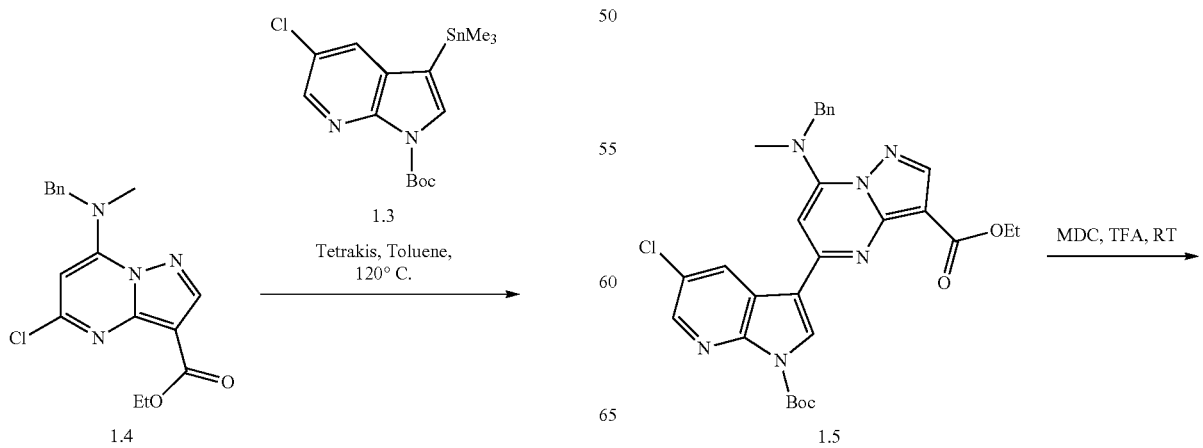

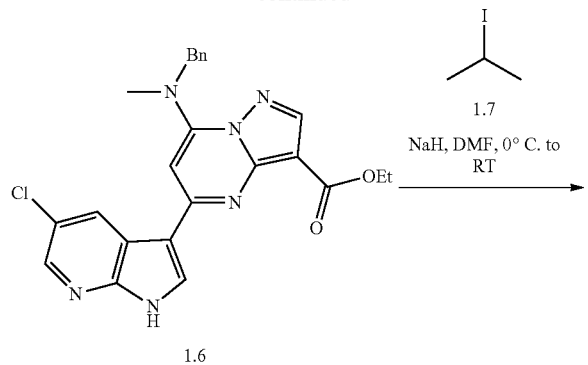
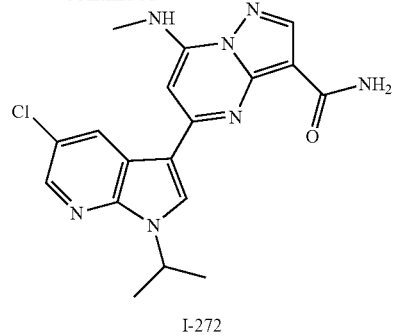

Synthesis of Compound 1.4.

Compound was synthesized using general procedure of core synthesis to obtain 1.4 (Yield: 45.00%). MS (ES): m/z 345.10 [M+H]$^+$ Synthesis of Compound 1.5.

To a solution of 1.4. (0.500 g, 1.45 mmol, 1.0 eq) in toluene (10 mL), palladium-tetrakis(triphenylphosphine) (0.161 g, 0.14 mmol, 0.1 eq) was added. The reaction mixture was degassed for 10 min. under argon atmosphere, then 1.3 (0.800 g, 2.10 mmol, 1.5 eq) was added and reaction was stirred at 120° C. for 1 h. After completion of reaction, reaction mixture was filtered through celite-bed and was with ethyl acetate. Filtrate was concentrated under reduced pressure to obtain pure 1.5 (0.400 g, 49.17%). MS (ES): m/z 562.64 [M+H]$^+$.

Synthesis of Compound 1.6.

Compound was synthesized using general procedure C to obtain pure 1.6 (0.320 g, 97.38%). MS(ES): m/z 461.92 [M+H]$^+$.

Synthesis of Compound 1.8.

To a cooled solution of 1.6 (0.320 g, 0.695 mmol, 1 eq) in dimethylformamide (4 mL) was added sodium hydride (0.041 g, 1.04 mmol, 1.5 eq) followed by addition of 1.7 (0.130 g, 0.764 mmol, 1.1 eq) under nitrogen atm. The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 5% ethyl acetate in hexane to obtain pure 1.8 (0.300 g, 85.51%), MS(ES): m/z 504.00 [M+H]$^+$.

Synthesis of Compound 1.9.

To a solution of 1.8 (0.300 g, 0.596 mmol, 1.0 eq), in tetrahydrofuran: methanol: water (6 mL, 1:1:1) was added lithium hydroxide (0.250 g, 5.96 mmol, 10 eq). The reaction was stirred at room temperature for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.4% methanol in dichloromethane to obtain pure 1.9 (0.220 g, 77.66%). MS(ES): m/z 475.95 [M+H]$^+$.

Synthesis of Compound 1.10.

Compound was synthesized using general procedure of A to obtain 1.10 (0.048 g, 48.10%). MS (ES): m/z 474.97 [M+H]$^+$

Synthesis of Compound I-272:

Mixture of 1.10 (0.048 g, 0.101 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-272 (0.025 g, 64.31%), MS (ES): m/z 384.39 [M+H]$^+$, LCMS purity: 95.18%, HPLC purity: 95.86%, $^1$H NMR (DMSO-d$_6$, 400 MHZ): 8.88 (s, 1H), 8.69 (s, 1H), 8.40-8.38 (d, J=8 Hz, 2H), 8.26-8.25 (d, J=4 Hz, 1H), 7.63 (s, 1H), 7.57 (s, 1H), 6.78 (s, 1H), 5.18-5.06 (m, 1H), 3.13-3.12 (d, J=4 Hz, 3H), 1.59-1.58 (d, J=4 Hz, 6H).

103.5: Synthesis of 5-((5-methyl-1-(1-methyl-1H-pyrazol-4-yl)-6-oxo-1,6-dihydropyridin-3-yl)amino)-7-(methylamino)pyrazolo[1,5-a]pyrimidine-3-carboxamide (I-287)

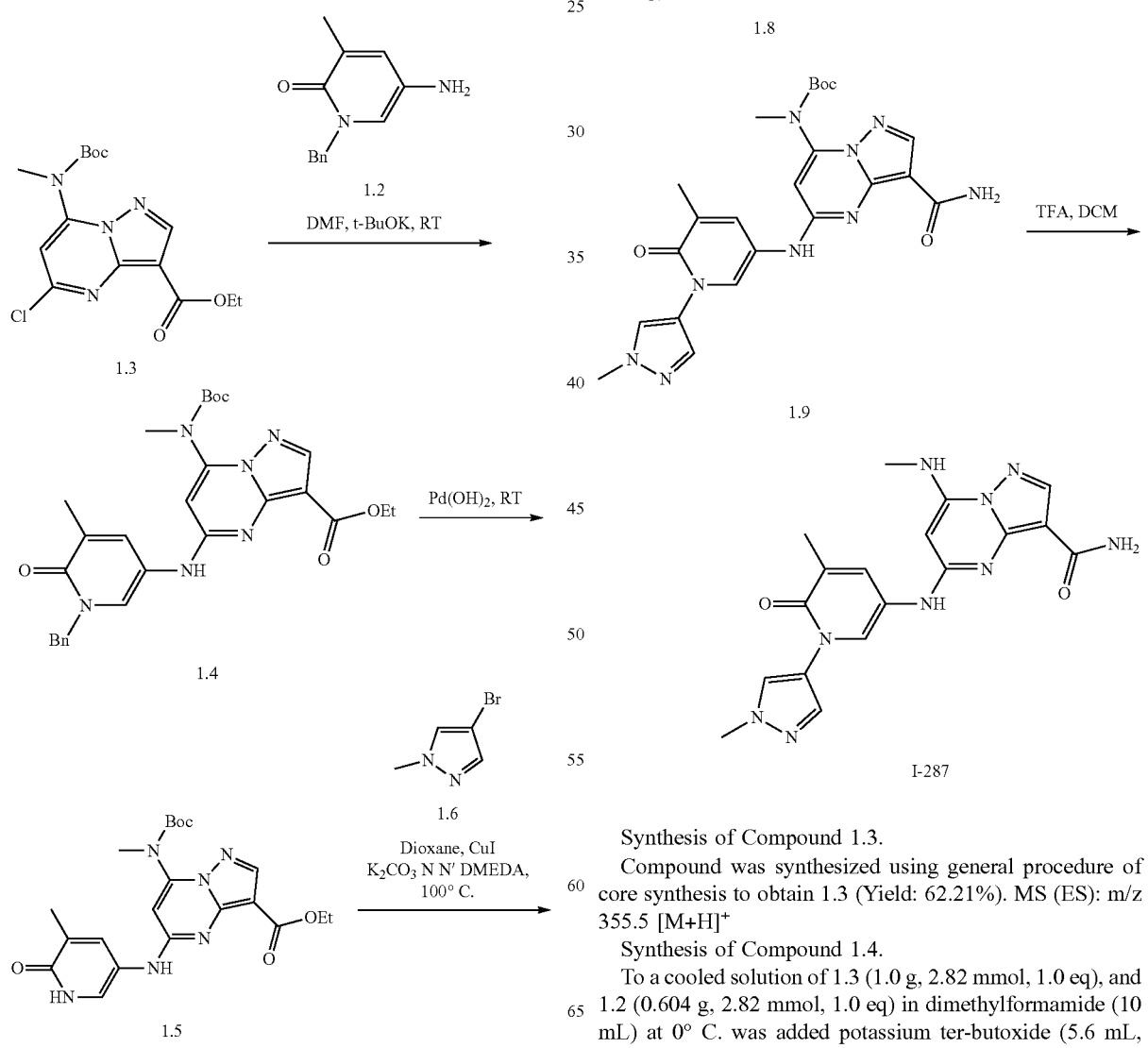

Synthesis of Compound 1.3.

Compound was synthesized using general procedure of core synthesis to obtain 1.3 (Yield: 62.21%). MS (ES): m/z 355.5 [M+H]$^+$

Synthesis of Compound 1.4.

To a cooled solution of 1.3 (1.0 g, 2.82 mmol, 1.0 eq), and 1.2 (0.604 g, 2.82 mmol, 1.0 eq) in dimethylformamide (10 mL) at 0° C. was added potassium ter-butoxide (5.6 mL, 5.64 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 1.4 (0.630 g, 41.97%). MS (ES): m/z 533.66 [M+H]$^+$.

Synthesis of Compound 1.5.

To a solution of 1.4 (0.630 g, 2.82 mmol, 1.0 eq) in methanol (7 mL) was added palladium hydroxide (0.300 g). The reaction was stirred at room temperature for 16 h. After completion of reaction, reaction mixture was filtered through celite-bed and washed with methanol. Filtrate was concentrated under reduced pressure to obtain crude material. This was further purified by column chromatography and compound was eluted in 2.0% methanol in dichloromethane to obtain pure 1.5 (0.240 g, 45.85%). MS (ES): m/z 443.48 [M+H]$^+$ Synthesis of Compound 1.7.

To a solution of 1.5 (0.240 g, 0.542 mmol, 1.0 eq) and 1.6 (0.174 g, 1.08 mmol, 2 eq) in 1,4-dioxane (3 mL) was added potassium carbonate (0.225 g, 1.62 mmol, 3.0 eq) and degassed with argon for 15 min. Copper iodide (0.021 g, 0.108 mmol, 0.2 eq) and 1,2-dimethylethylenediamine (0.019 g, 0.216 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.6% methanol in dichloromethane to obtain pure 1.7 (0.130 g, 45.86%). MS(ES): m/z 523.57 [M+H]$^+$.

Synthesis of Compound 1.8.

To a solution of 1.7 (0.095 g, 0.182 mmol, 1.0 eq), in tetrahydrofuran: methanol: water (2 mL, 2:1:1) was added lithium hydroxide (0.076 g, 1.82 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 1.8 (0.050 g, 55.62%). MS(ES): m/z 495.51 [M+H]$^+$.

Synthesis of Compound 1.9.

Compound was synthesized using general procedure A to obtain 1.9. (0.035 g, 70.14%). MS (ES): m/z 494.53 [M+H]$^+$ Synthesis of Compound I-287.

Compound was synthesized using general procedure C to obtain I-287 (0.020 g, 71.68%). MS (ES): m/z 394.17 [M+H]$^+$, LCMS purity: 97.13%, HPLC purity: 95.08%, $^1$H NMR (DMSO-d$_6$, 400 MHZ): 9.11 (s, 1H), 8.30 (s, 1H), 8.14 (s, 1H), 7.90 (s, 1H), 7.85 (s, 1H), 7.53 (s, 1H), 7.37 (s, 1H), 7.12-7.08 (m, 1H), 6.84 (m, 1H), 5.42-5.37 (m, 1H), 3.89 (s, 3H), 2.90 (bs, 3H), 2.09 (s, 3H).

103.6. Synthesis of 7-(methylamino)-5-(1-(2-morpholinoethyl)-1H-pyrrolo[2,3-b]pyridin-3-yl)pyrazolo[1,5-a]pyrimidine-3-carboxamide (I-796)

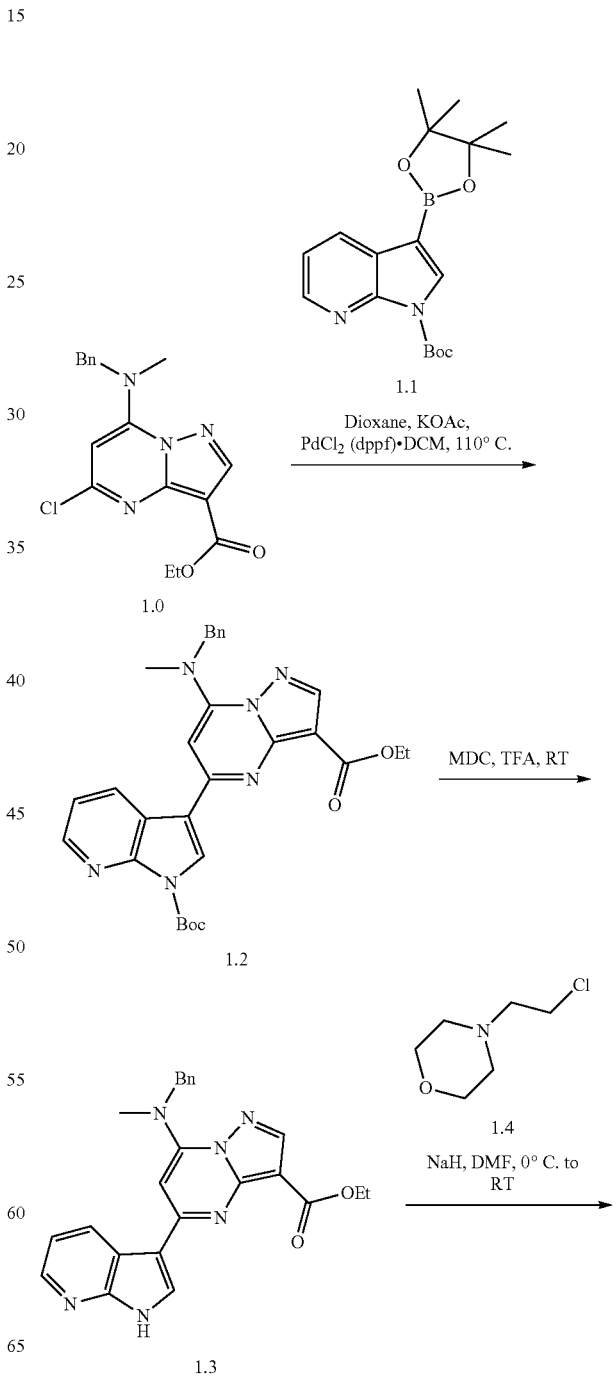

-continued

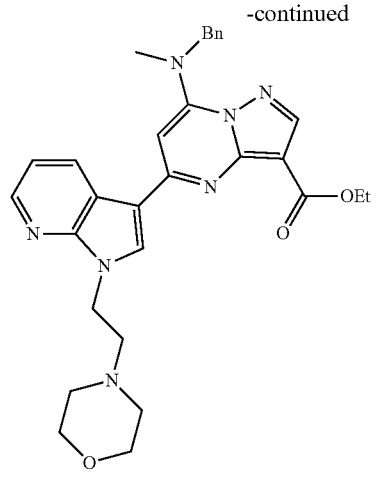

1.5

MeOH, THF, LiOH
H₂O, RT, 24 h
→

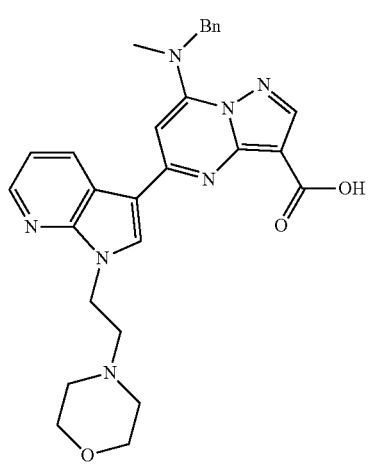

1.6

DMF, HATU, NH4Cl
DIPEA, RT
→

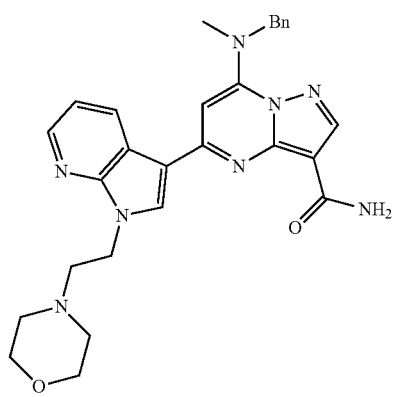

1.7

Triflic acid, 0° C.
→

-continued

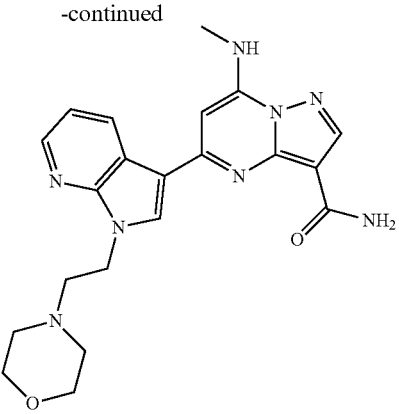

I-796

Synthesis of Compound 1.0.

Compound was synthesized using general procedure of core synthesis to obtain 1.0 (Yield: 45.00%). MS (ES): m/z 345.10 [M+H]⁺

Synthesis of Compound 1.2.

Argon was purged for 15 min through a stirred solution of 1.1 (2.3 g, 6.7 mmol, 1.0 eq), 1.0 (3.0 g, 8.72 mmol, 1.3 eq) and sodium carbonate (1.78 g, 16.75 mmol, 2.5 eq) in 1,4 dioxane (100 mL). [1,1'-Bis(diphenylphosphino)ferrocene]dichloropalladium(II) (0.550 g, 0.67 mmol, 0.1 eq) was added to it and further purging done for 10 min. Reaction was allowed to stirred at 100° C. for 6 h. After completion of reaction, reaction mixture was transferred into water and product was extracted with ethyl acetate. Organic layer was combined, washed with brine solution, dried over sodium sulphate and concentrated under reduced pressure to obtain crude product which purified by column chromatography eluting pure compound in 20-25% ethyl acetate in hexane to obtain pure 1.2 (2.1 g, 59.82%). MS (ES): m/z 527.51 [M+H]⁺

Synthesis of Compound 1.3.

Trifluoroacetic acid (5.0 mL) was added to a solution of 1.2 (2.1 g, 3.99 mmol, 1.0 eq) in dichloromethane (20 mL) and reaction mixture was stirred at room temperature for 2 h. After completion of reaction, reaction mixture was transferred into saturated sodium bicarbonate solution and product was extracted with dichloromethane. Organic layer was combined, washed with brine solution, dried over sodium sulphate and concentrated under reduced pressure to obtain 1.3. (1.69 g, 99.41%). MS (ES): m/z 427.51 [M+H]⁺

Synthesis of Compound 1.5.

sodium hydride (0.225 g, 5.6 mmol, 4.0 eq) was added to a solution of 1.3 (0.600 g, 1.4 mmol, 1.0 eq) in N—N-Dimethylformamide (12 mL) at 0° C. portion wise. Reaction mixture was stirred at same temperature for 20 min, 1.4 (0.635 g, 4.22 mmol, 1.2 eq) was added and mixture was allowed to stir at room temperature for 6 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography eluting pure compound in 2-2.5% methanol in dichloromethane to obtain pure 1.5 (420 mg, 55.26%). MS (ES): m/z 540.51 [M+H]⁺.

Synthesis of Compound 1.6.

To a solution of 1.5 (0.400 g, 0.744 mmol, 1.0 eq), in tetrahydrofuran: methanol: water (20 mL, 1:1:1) was added lithium hydroxide (0.315 g, 7.44 mmol, 10 eq). The reaction was stirred 60° C. for 6 h. After completion of reaction, reaction mixture was concentrated under reduced pressure to obtain residue. To this added water and acidified with 1N hydrochloric acid to adjust pH~6-6.5 at 10° C. Product was filtered and dried under vacuum to obtain pure 1.6 (0.360 g, 94.47%). MS(ES): m/z 512.2 [M+H]+.

Synthesis of Compound 1.7.

Compound was synthesized using general procedure of A to obtain 1.7 (0.070 g, 70.13%). MS (ES): m/z 511.25 [M+H]+

Synthesis of I-796.

Mixture of 1.7 (0.070 g, 0.1372 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with 10% MeOH: dichloromethane. Organic layer was combined, dried over sodium sulphate and concentrated under reduced pressure to obtain crude material. This was further purified by trituration with diethyl ether to a obtain I-796 (0.030 g, 52.04%), MS (ES): m/z 421.50 [M+H]+, LCMS purity: 100%, HPLC purity: 97.65%, $^1$H NMR (DMSO-$d_6$, 400 MHZ): 8.71 (s, 1H), 8.64-8.62 (d, J=8 Hz, 1H), 8.39-8.37 (t, J=4 Hz, 2H), 8.26 (s, 1H), 7.80 (s, 1H), 7.44 (s, 1H), 7.30-7.27 (m, 1H), 6.66 (s, 1H), 4.52-4.49 (t, J=4 Hz, 2H), 3.55 (s, 4H), 3.11 (s, 3H), 2.83-2.80 (t, 4 Hz, 2H), 2.52 (m, 4H).

Additional compounds prepared by substantially the same method, and their characterization data, are listed in the Table 47 below. The intermediate corresponding to 1.4 of the above scheme is listed for each compound.

TABLE 47

| Compound | Intermediate | Characterization data |
|---|---|---|
| I-797 | 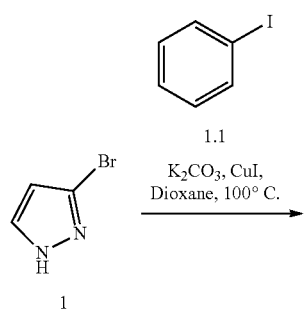 | MS (ES): m/z 419.32 [M + H]+, LCMS purity: 97.27%, HPLC purity: 97.28%, $^1$H NMR (DMSO-$d_6$, 400 MHZ): 8.70 (s, 1H), 8.64-8.62 (d, J = 7.6 Hz, 1H), 8.39-8.38 (d, J = 4 Hz, 1H), 8.36 (s, 1H), 8.26-8.25 (d, J = 4.4 Hz, 1H), 7.79 (bs, 1H), 7.42 (bs, 1H), 7.30-7.27 (m, 1H), 6.66 (s, 1H), 5.77 (s, 1H), 4.49 (bs, 2H), 3.12-3.10 (d, J = 4.8 Hz, 3H), 2.77 (bs, 2H), 2.51 (s, 2H), 1.48 (bs, 4H), 1.39 (bs, 2H), 1.24 (s, 1H). |

103.7. Synthesis of 7-(methylamino)-5-(1-phenyl-1H-pyrazol-3-yl)pyrazolo[1,5-a]pyrimidine-3-carboxamide (I-39)

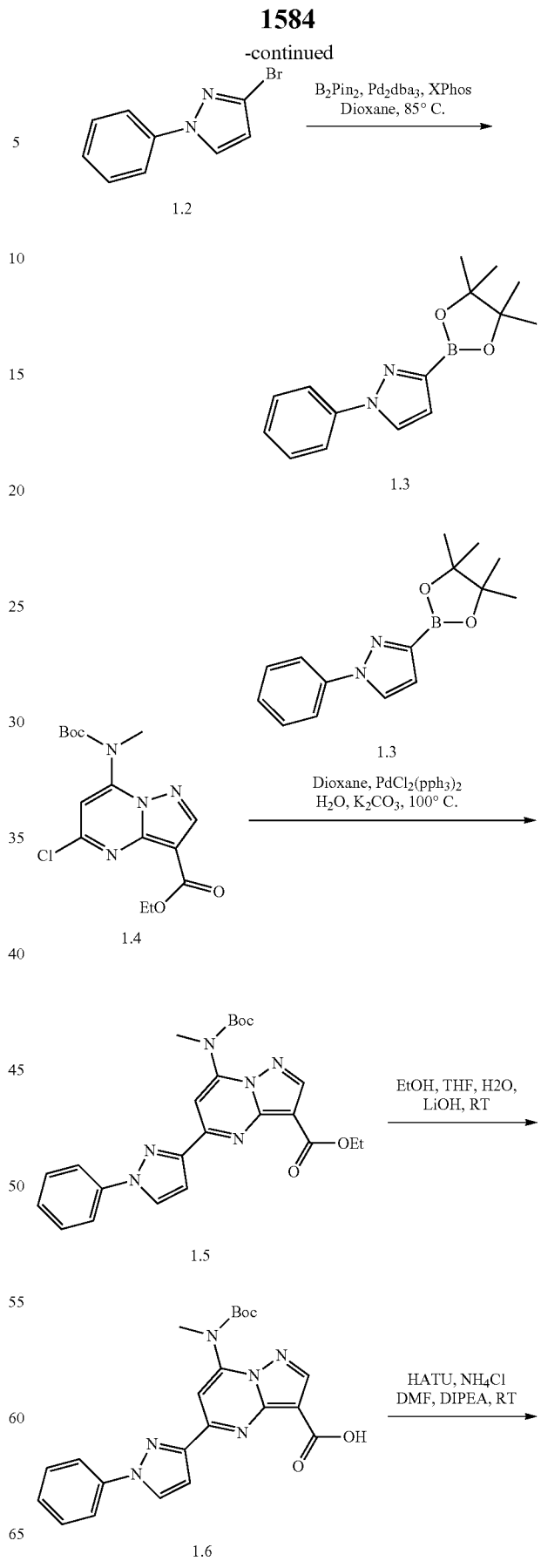

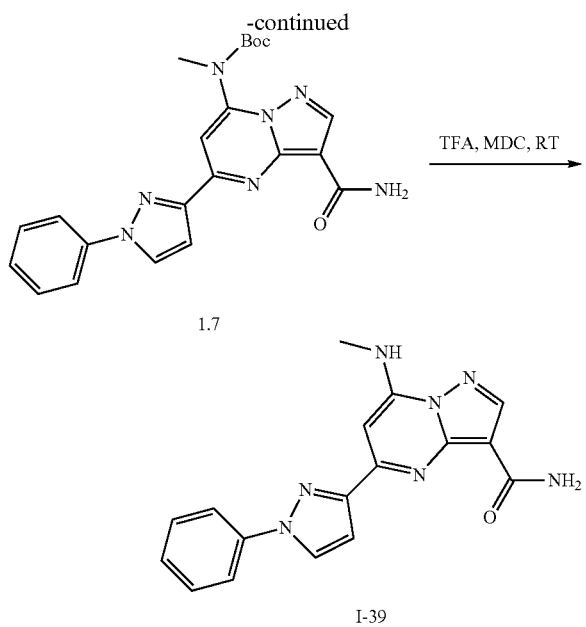

Synthesis of Compound 1.2.

To a solution of 1 (2 g, 13.61 mmol, 1.0 eq) and 1.1 (3.3 g, 16.33 mmol, 1.2 eq) in 1,4-dioxane (30 mL) was added potassium carbonate (4.2 g, 30.62 mmol, 2.25 eq) and degassed with argon for 15 min. Copper iodide (0.258 g, 1.36 mmol, 0.1 eq) and 1,2-diaminocyclohexane (0.386 g, 2.72 mmol, 0.2 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 7% ethyl acetate in hexane to obtain pure 1.2 (1.8 g, 29.30%). MS(ES): m/z 224.07[M+H]$^+$.

Synthesis of Compound 1.3.

To a solution of 1.2 (1.8 g, 8.07 mmol, 1.0 eq) in 1,4-dioxane (18 mL) was added bis(pinacolato)diboron (4.1 g, 16.14 mmol, 2 eq) and potassium acetate (2.38 g, 24.21 mmol, 3 eq). The reaction mixture was degassed for 10 min. under argon atmosphere, then 2-dicyclohexylphosphino-2',4',6'-triisopropylbiphenyl (0.010 g, 0.160 mmol, 0.02 eq) and tris(dibenzylideneacetone)dipalladium(0) (0.073 g, 0.080 mmol, 0.01 eq) added, again degassed for 5 min. The reaction mixture was stirred at 85° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 27% ethyl acetate in hexane to obtain pure 1.2 (1 g, 45.88%). MS(ES): m/z 271.14 [M+H]$^+$.

Synthesis of Compound 1.4.

Compound was synthesized using general procedure of core synthesis to obtain 1.4 (Yield: 62.21%). MS (ES): m/z 355.5 [M+H]$^+$ Synthesis of Compound 1.5.

To a solution of 1.4 (0.500 g, 1.41 mmol, 1.0 eq) in 1,4-dioxane (12 mL) and water (3 mL) was added 1.3 (0.46 g, 1.69 mmol, 1.20 eq), potassium carbonate (0.600 g, 4.23 mmol, 3 eq). The reaction mixture was degassed for 10 min. under argon atmosphere, then dichlorobis(triphenylphosphine)palladium(II) (0.098 g, 0.141 mmol, 0.1 eq) again degassed for 5 min. The reaction was stirred at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 23% ethyl acetate in hexane to obtain pure 1.5 (0.300 g, 46.03%). MS(ES): m/z 463.51 [M+H]$^+$.

Synthesis of Compound 1.6.

To a solution of 1.5 (0.300 g, 0.648 mmol, 1.0 eq), in tetrahydrofuran: methanol: water (6 mL, 1:1:1) was added lithium hydroxide (0.272 g, 6.48 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.4% methanol in dichloromethane to obtain pure 1.6 (0.200 g, 70.97%). MS(ES): m/z 435.46 [M+H]$^+$.

Synthesis of Compound 1.7.

Compound was synthesized using general procedure A to obtain 1.7. (0.085 g, 42.60%). MS (ES): m/z 434.47 [M+H]$^+$ Synthesis of Compound I-39.

Compound was synthesized using general procedure C to obtain I-39 (0.030 g, 45.89%). MS (ES): m/z 334.17 [M+H]$^+$, LCMS purity: 95.83%, HPLC purity: 100%, $^1$H NMR (DMSO-d$_6$, 400 MHZ): 8.70 (d, J=2.4 Hz, 1H), 8.49-8.47 (d, J=8 Hz, 1H), 8.42 (s, 1H), 8.03-8.01 (d, J=8 Hz, 1H), 7.80 (s, 2H), 7.60-7.58 (t, J=8 Hz, 2H), 7.42-7.34 (m, 3H), 6.90 (s, 1H), 3.13-3.11 (d, J=8 Hz, 3H).

Additional compounds prepared by substantially the same method, and their characterization data, are listed in the Table 48 below. The intermediate corresponding to 1 of the above scheme is listed for each compound.

TABLE 48

| Compound | Intermediate | Characterization data |
|---|---|---|
| I-44 | 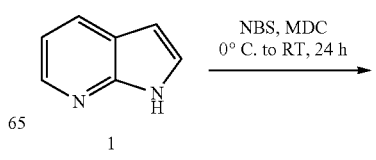 | MS (ES): m/z 334.45 [M + H]$^+$, LCMS purity: 98.48%, HPLC purity: 96.89%, $^1$H NMR (DMSO-d$_6$, 400 MHZ): 9.40 (s, 1H), 8.55 (s, 1H), 8.36-8.34 (d, J = 8 Hz, 2H), 7.97-7.95 (d, J = 8 Hz, 2H), 7.80 (s, 1H), 7.59-7.57 (t, J = 8 Hz, 2H), 7.40-7.39 (t, , J = 4 Hz, 1H), 7.25 (s, 1H), 6.73 (s, 1H), 3.10-3.09 (d, J = 4 Hz, 3H). |

103.8. Synthesis of 5-(1-isopropyl-1H-pyrrolo[2,3-b]pyridin-3-yl)-7-(methylamino)pyrazolo[1,5-a]pyrimidine-3-carboxamide (I-222)

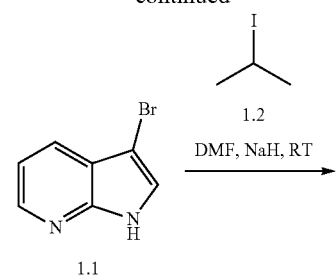

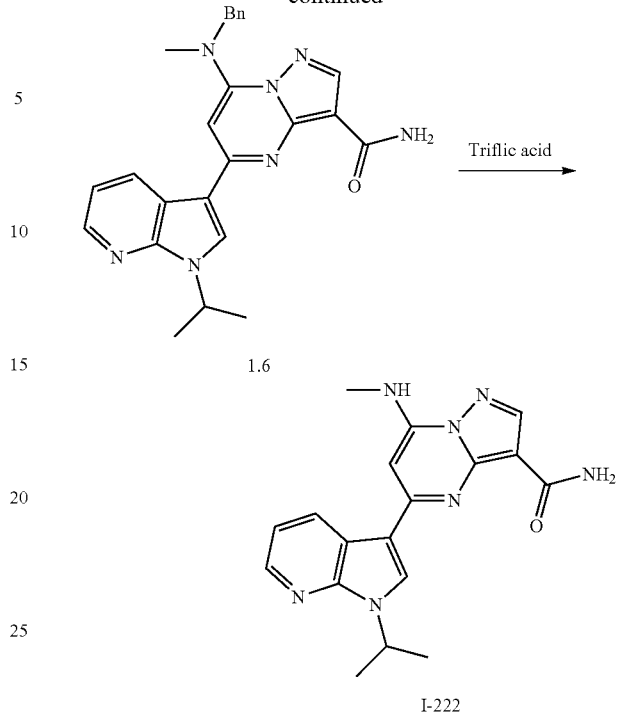

Synthesis of Compound 1.1.

To a cooled solution of 1 (1 g, 8.46 mmol, 1.0 eq) in dichloromethane (20 mL), N-bromosuccinamide (1.65 g, 9.30 mmol, 1.1 eq) was added. The reaction mixture was stirred at room temperature for 16 h. After completion of reaction, reaction mixture transferred into ice cold water and product was extracted with ethyl acetate. Organic layer was combined, washed with brine solution, dried over sodium sulphate and concentrated under reduced pressure to obtain crude material. This was further purified by column chromatography and compound was eluted in 9% ethyl acetate in hexane to obtain pure 1.1 (1.4 g, 83.94%). MS(ES): m/z 198.04 [M+H]$^+$.

Synthesis of Compound 1.3.

To a cooled solution of 1.1 (1.4 g, 7.11 mmol, 1 eq) in tetrahydrofuran (12 mL) was added sodium hydride (0.446 g, 11.16 mmol, 1.5 eq) followed by addition of 1.2 (1.45 g, 8.53 mmol, 1.2 eq) under nitrogen. The reaction was stirred at room temperature for 16 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 7% ethyl acetate in hexane to obtain pure 1.3 (1.2 g, 70.63%), MS(ES): m/z 240.12 [M+H]$^+$.

Synthesis of Compound 1.4.

To a solution of 1.3 (1.2 g, 5.02 mmol, 1.0 eq) in dimethylformamide (15 mL) was added bis(pinacolato)diboron (3.81 g, 15.06 mmol, 3 eq), potassium acetate (1.23 g, 12.5 mmol, 2.5 eq). The reaction mixture was degassed for 10 min. under argon atmosphere, then [1,1'-Bis(diphenylphosphino)ferrocene]dichloropalladium(II) (0.409 g, 0.502 mmol, 0.1 eq) was added and again degassed for 5 min. The reaction was stirred at 60° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 10% ethyl acetate in hexane as eluant to obtain pure 1.4 (0.800 g, 55.70%). MS(ES): m/z 287.18 [M+H]+.

Synthesis of Compound 1.5.

Compound was synthesized using general procedure of core synthesis to obtain 1.5 (Yield: 62.0%). MS (ES): m/z 316.76 [M+H]+

Synthesis of Compound 1.6.

To a solution of 1.5 (0.100 g, 0.317 mmol, 1.0 eq) in dimethylformamide (5 mL) was added 1.4 (0.228 g, 0.793 mmol, 2.5 eq), sodium carbonate (0.084 g, 0.793 mmol, 2.5 eq) and [1,1'-Bis(diphenylphosphino)ferrocene]dichloropalladium(II) (0.026 g, 0.031 mmol, 0.1 eq), degassed for 10 min and stirred at 90° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 16% ethyl acetate in hexane as eluant to obtain pure 1.6 (0.050 g, 35.92%). MS(ES): m/z 440.52 [M+H]+.

Synthesis of Compound I-222.

Mixture of 1.6 (0.050 g, 0.113 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-222 (0.035 g, 88.06%). MS (ES): m/z: 350.27 [M+H]+, LCMS purity: 100%, HPLC purity: 99.65%, $^1$H NMR (DMSO-$d_6$, 400 MHZ): 8.79 (s, 1H), 9.06 (s, 1H), 8.65-8.63 (d, J=8 Hz, 1H), 8.38-8.35 (d, J=12 Hz, 1H), 8.21 (s, 1H), 7.78 (s, 1H), 7.40 (s, 1H), 7.27 (s, 1H), 6.77 (s, 1H), 5.20 (m, 1H), 3.12 (s, 3H), 1.89-1.57 (d, J=8 Hz, 6H).

Additional compounds prepared by substantially the same method, and their characterization data, are listed in the Table 49 below. The intermediate corresponding to 1 of the above scheme is listed for each compound.

TABLE 49

| Compound | Intermediate | Characterization data |
|---|---|---|
| I-255 | ![5-methyl-7-azaindole] | MS (ES): m/z: 364.44 [M + H]+, LCMS purity: 99.24%, HPLC purity: 96.28%, $^1$H NMR (DMSO-$d_6$, 400 MHZ): 8.74 (s, 1H), 8.45 (s, 1H), 8.33 (s, 1H), 8.22 (s, 1H), 8.18-8.17 (d, J = 4 Hz, 1H), 7.84 (bs, 1H), 7.55 (s, 1H), 6.75 (s, 1H), 5.16-5.13 (s, 1H), 3.11-3.10 (d, J = 4 Hz, 3H), 2.45 (s, 3H), 1.57-1.55 (d, J = 8 Hz, 6H). |

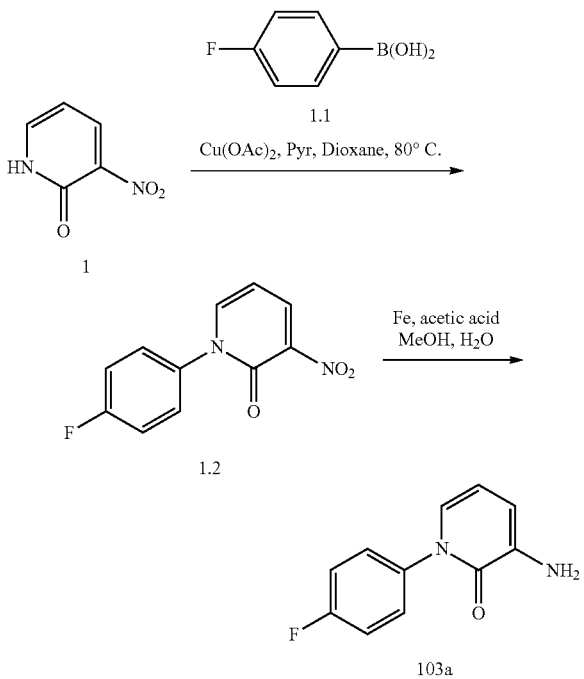

Synthesis of Compound 1.2.

To a solution of 1 (0.8 g, 5.71 mmol, 1.0 eq) and 1.1 (1.58 g, 11.42 mmol, 2.0 eq) in 1,4-dioxane (35 mL), copper acetate (1.5 g, 8.57 mmol, 1.5 eq), pyridine (3.8 mL) was added. The reaction mixture was heated at 80° c. for 40 h. After completion of reaction, reaction mixture was transferred into cold ice water and product was extracted with ethyl acetate. Organic layer was combined, washed with 1N hydrochloric acid, dried over sodium sulphate and concentrated under reduced pressure to obtain crude material. This was further purified by column chromatography using 20% ethyl acetate in hexane as eluant to obtain pure 1.2 (1 g, 23.94%). MS(ES): m/z 235 [M+H]+.

Synthesis of Compound 103a.

To a mixture of 1.2 (0.1 g, 0.427 mmol, 1.0 eq) and iron (0.11 g, 2.13 mmol, 5.0 eq) in methanol (0.8 mL), water (0.2 mL) was added acetic acid (0.3 mL, 6.41 mmol, 15 eq). The reaction mixture was heated at 60° C. for 1 h. After completion of reaction, reaction mixture was filtered, diluted with water and product was extracted with ethyl acetate. Organic layer was combined, washed with brine solution, dried over sodium sulphate and concentrated under reduced pressure to obtain crude material. This was further purified by column chromatography using 30% ethyl acetate in hexane as eluant to obtain pure 103a (0.4 g, 57.34%). MS(ES): m/z 205 [M+H]+.

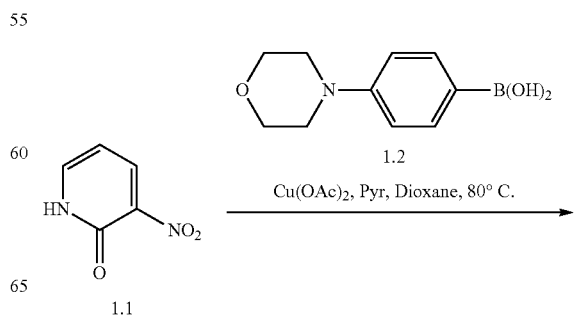

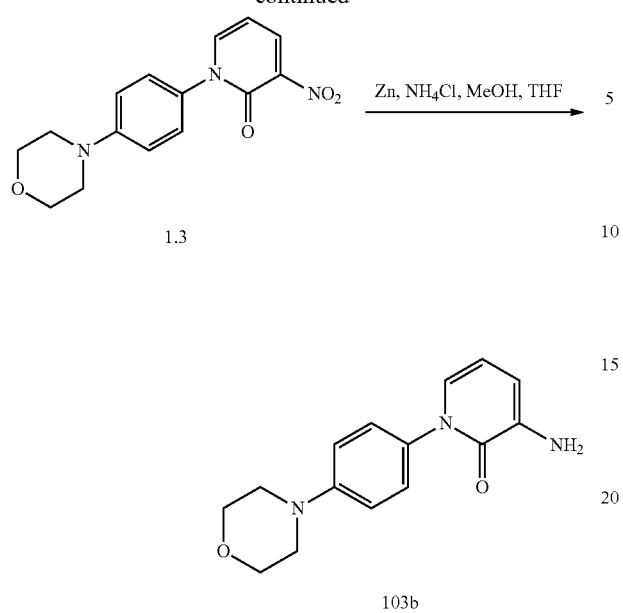

Synthesis of Compound 1.3.

To a solution of 1 (1 g, 7.14 mmol, 1.0 eq) and 1.2 (2.9 g, 14.28 mmol, 2.0 eq) in 1,4-dioxane (60 mL), copper acetate (1.9 g, 10.71 mmol, 1.5 eq) and pyridine (5.0 mL) was added. The reaction mixture was heated at 80° C. for 40 h. After completion of reaction, reaction mixture was transferred into ice cold water and product was extracted with ethyl acetate. Organic layer was combined, washed with 1N hydrochloric acid, dried over sodium sulphate and concentrated under reduced pressure to obtain crude material. This was further purified by column chromatography using 30% ethyl acetate in hexane as eluant to obtain pure 1.3 (1 g, 21.39%). MS(ES): m/z 302 [M+H]$^+$.

Synthesis of Compound 103b.

To a solution of 1.3 (0.40 g, 1.53 mmol, 1.0 eq) in tetrahydrofuran: methanol (5 mL, 1:1) was added zinc (0.99 g, 15.3 mmol, 10 eq), and ammonium chloride (0.81 g, 15.3 mmol, 10 eq). Reaction mixture was heated at 60° C. for 6 h. After completion of reaction, reaction mixture was filtered, filtrate was concentrated under reduced pressure to obtain 103b (0.21 g, 50.70%). MS(ES): m/z 272 [M+H]$^+$.

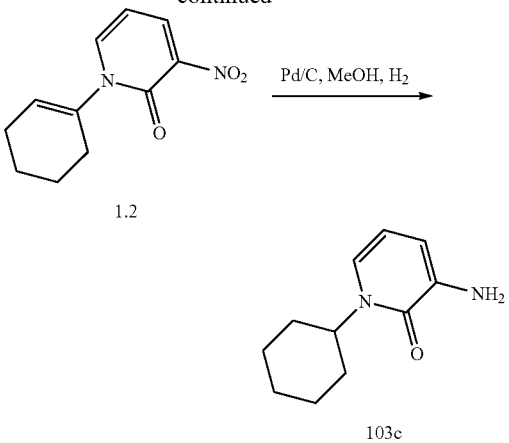

Synthesis of Compound 1.2.

To a solution of 1 (1 g, 7.14 mmol, 1.0 eq) in acetonitrile: ethanol (1.3 ml 2:1) added 2-(cyclohex-1-en-1-yl)-4,4,5,5-tetramethyl-1,3,2-dioxaborolane (0.29 g, 14.2 mmol, 2.0 eq) and copper acetate (1.2 g, 7.14 mmol, 1.0 eq) followed by triethylamine (0.86 g, 8.56 mmol, 1.2 eq). The reaction mixture was heated at 80° C. for 24 h. After completion of reaction, reaction mixture was filtered through celite and concentrated under reduced pressure to obtain crude material. This was further purified by combi flash using 15% ethyl acetate in hexane as eluant to obtain pure 1.2 (0.570 g, 36.26%). MS(ES): m/z 221.

Synthesis of Compound 103c.

To a solution of 1.2 (0.57 g, 4.07 mmol, 1.0 eq) in methanol (5 mL), palladium on charcoal (0.100 g) was added. Hydrogen was purged through reaction mixture for 24 h at room temperature. After completion of reaction, reaction mixture was filtered through celite-bed and washed with methanol. Filtrate was concentrated under reduced pressure to obtain 103c (0.150 g, 16.74%). MS(ES): m/z 193 [M+H]$^+$.

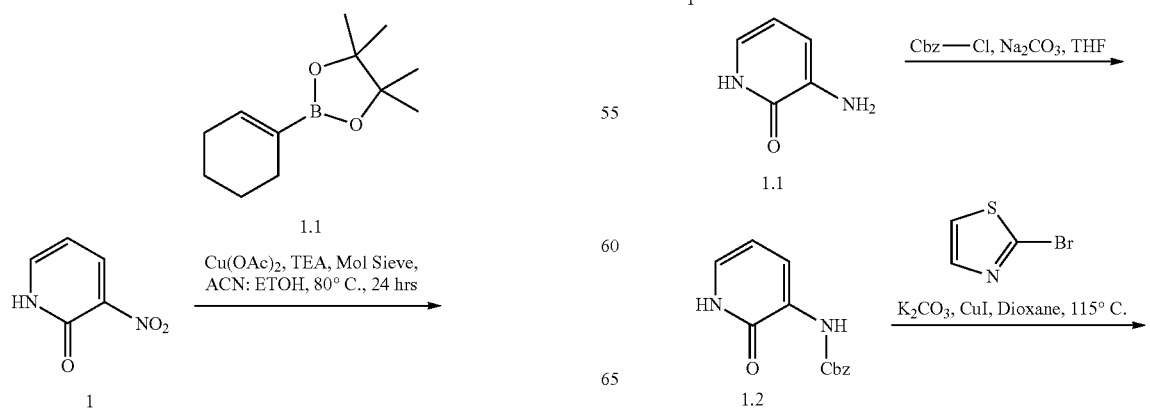

-continued

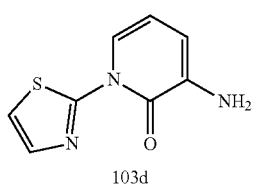
1.3

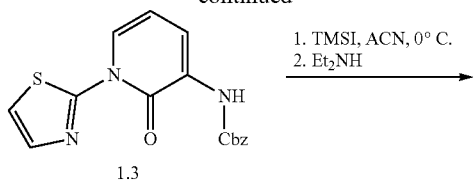

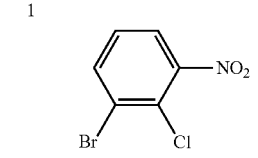
103d

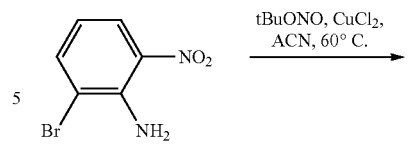
1

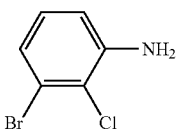
1.1

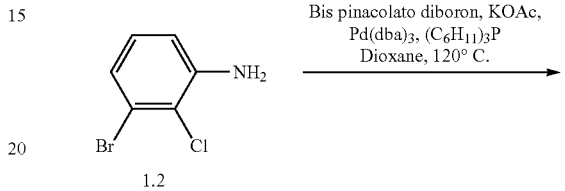

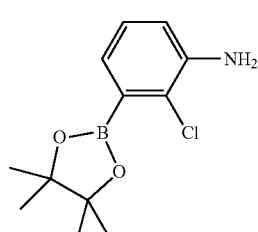
1.2

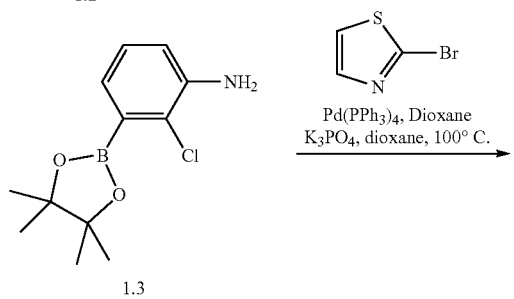
1.3

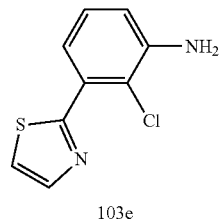
103e

Synthesis of Compound 1.1.

To a solution of 1 (5 g, 35.6 mmol, 1.0 eq) in methanol (50 mL), palladium on charcoal (2.0 g) was added. Hydrogen was purged through reaction mixture for 24 h at room temperature. After completion of reaction, reaction mixture was filtered through celite-bed and washed with methanol. Filtrate was concentrated under reduced pressure to obtain 1.1 (3.2 g, 81.43%). MS(ES): m/z 111.12 [M+H]$^+$ Synthesis of Compound 1.2.

To a solution of 1.1 (3.2 g, 29.06 mmol, 1.0 eq) in tetrahydrofuran (65 ml), sodium carbonate (6.1 g, 58.1 mmol, 2.0 eq) and benzyl chloroformate (6.2 g, 36.3 mmol, 1.2 eq) was added at 0° C. The reaction mixture was stirred for 16 h at room temperature. After completion of reaction, reaction mixture was transferred into saturated bicarbonate solution and product was extracted with ethyl acetate. Organic layer was combined, dried over sodium sulphate and concentrated under reduced pressure to obtain crude material. This was further purified by column chromatography using 15% ethyl acetate in hexane as eluant to obtain pure 1.2 (2.1 g, 29.59%). MS(ES): m/z 245 [M+H]$^+$.

Synthesis of Compound 1.3.

To a solution of 1.2 (2.1 g, 8.60 mmol, 1.0 eq) in 1,4-dioxane (10 mL), 2-bromothiazole (2.1 g, 12.9 mmol, 1.5 eq) copper iodide (0.16 g, 0.86 mmol, 0.1 eq) was added. The reaction mixture was heated at 115° C. for 16 h. After completion of reaction, reaction mixture was transferred into ice cold water and product was extracted with ethyl acetate. Organic layer was combined, dried over sodium sulphate and concentrated under reduced pressure to obtain crude material. This was further purified by column chromatography using 10% ethyl acetate in hexane as eluant to obtain pure 1.3 (1.8 g, 63.95%). MS(ES): m/z 328 [M+H]$^+$.

Synthesis of Compound 103d.

To a solution of 1.3 (1.8 g, 7.37 mmol, 1.0 eq) in acetonitrile (1 mL), trimethylsilyl iodide (5.8 g, 29.4 mmol, 4.0 eq), was added. The reaction mixture was stirred for 18 h at room temperature. Diethylamine (0.1 mL) was added to reaction and stirred for 20 min. After completion of reaction, reaction mixture was transferred into ice cold water and product was extracted with ethyl acetate. Organic layer was combined, dried over sodium sulphate and concentrated under reduced pressure to obtain crude material. This was further purified by column chromatography using 20% ethyl acetate in hexane as eluant to obtain pure 103d (0.60 g, 56.47%). MS(ES): m/z 194 [M+H]$^+$.

Synthesis of Compound 1.1.

To a solution of 1 (5 g, 23.04 mmol, 1.0 eq), in acetonitrile (50 mL), copper chloride (3.7 g, 27.64 mmol, 1.2 eq) and tert-butyl nitrite was added. The reaction mixture was heated at 60° C. for 12 h. After completion of reaction, reaction mixture was, transferred to ice cold water and product was extracted with ethyl acetate. Organic layer was combined, dried over sodium sulphate and concentrated under reduced pressure to obtain crude material. This was further purified by column chromatography using 100% hexane as eluant to obtain pure 1.1 (3.8 g, 69.76%). MS (ES): m/z 237.45 [M+H]$^+$ Synthesis of Compound 1.2.

To a solution of 1.1 (3.8 g, 16.07 mmol, 1.0 eq), in ethanol (30 mL), iron powder (4.4 g, 80.35 mmol, 5.0 eq) and acetic acid (5.7 mL) was added. The reaction mixture was stirred at room temperature for 2 h. After completion of reaction, reaction mixture was, transferred into sodium bicarbonate solution and product was extracted with ethyl acetate. Organic layer was combined, dried over sodium sulphate and concentrated under reduced pressure to obtain crude material. This was further purified by column chromatography using 12% ethylacetate in hexane as eluant to obtain pure 1.2 (3.0 g, 90.14%). MS (ES): m/z 207.47 [M+H]$^+$ Synthesis of Compound 1.3.

To a solution of 1.2. (3 g, 14.53 mmol, 1.0 eq) in 1,4-dioxane (80 mL), Bispinacolatodiborane (4.4 g, 17.43 mmol, 1.2 eq) and tris(dibenzylideneacetone)dipalladium(0) (0.39 g, 0.43 mmol, 0.03 eq), Tricyclohexylphosphine (0.28 g, 1.0 mmol, 0.07 eq), potassium acetate (2.1 g, 21.79 mmol, 1.5 eq) was added. The reaction mixture was degassed for 15 min. under argon atmosphere. The reaction mixture was heated at 120° C. for 2 h. After completion of reaction, reaction mixture was, transferred ice cold water and product was extracted with ethyl acetate. Organic layer was combined, dried over sodium sulphate and concentrated under reduced pressure to obtain crude material. This was further purified by column chromatography using 10% ethyl acetate in hexane as eluant to obtain pure 1.3. (2.8 g, 76.01%). MS (ES): m/z 254.53[M+H]$^+$ Synthesis of Compound 103e.

To a solution of 1.3. (2.8 g, 11.04 mmol, 1.0 eq), in 1,4-dioxane (25 mL), 2-bromothiazole (1.8 g, 11.04 mmol, 1.0 eq) Palladium-tetrakis(triphenylphosphine) (2.5 g, 2.20 mmol, 0.2 eq) and potassium phosphate tribasic (4.6 g, 22.08 mmol, 2.0 eq) was added. The reaction mixture was degassed for 15 min. under argon atmosphere. The reaction mixture was heated at 100° C. for 1 h. After completion of reaction, reaction mixture was, transferred ice cold water and product was extracted with ethyl acetate. Organic layer was combined, dried over sodium sulphate and concentrated under reduced pressure to obtain crude material. This was further purified by column chromatography using 12% ethyl acetate in hexane as eluant to obtain pure 103e. (0.50 g, 21.49%). MS (ES): m/z 211.68[M+H]$^+$

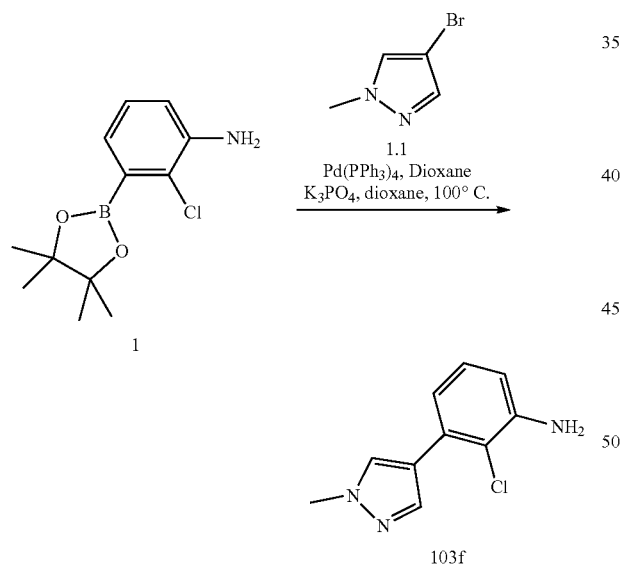

Synthesis of Compound 1.

Compound was synthesized as per experimental protocol of 102e.

Synthesis of Compound 103f.

To a solution of 1. (2.0 g, 7.89 mmol, 1.0 eq) in 1,4-dioxane (25 mL), 1.1 (1.2 g, 7.89 mmol, 1.0 eq) Palladium-tetrakis(triphenylphosphine) (1.8 g, 1.57 mmol, 0.2 eq) and potassium phosphate tribasic (3.3 g, 15.78 mmol, 2.0 eq) was added. The reaction mixture was degassed for 15 min. under argon atmosphere and heated at 100° C. for 1 h. After completion of reaction, reaction mixture was, transferred into ice cold water and product was extracted with ethyl acetate. Organic layer was combined, dried over sodium sulphate and concentrated under reduced pressure to obtain crude material. This was further purified by column chromatography using 12% ethyl acetate in hexane as eluant to obtain pure 103f. (0.53 g, 32.35%). MS (ES): m/z 208.66 [M+H]$^+$

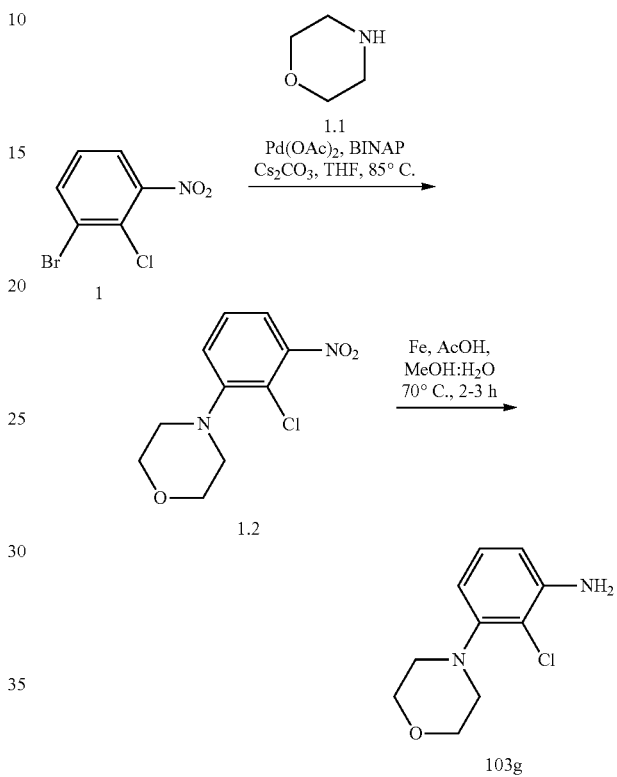

Synthesis of Compound 1.2.

To a solution of 1 (2.0 g, 8.46 mmol, 1.0 eq) in tetrahydrofuran (3 mL) was added palladium acetate (0.189 g, 0.846 mmol, 0.1 eq) and cesium carbonate (4.11 g, 12.69 mmol, 1.5 eq). The reaction mixture was degassed for 10 min under argon atmosphere followed by addition of 1.1 (2.20 g, 25.38 mmol, 3 eq) and again degassed for 5 min. The reaction was stirred at 85° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 1.2 (1.1 g, 49.50%). MS(ES): m/z 243.60 [M+H]$^+$.

Synthesis of Compound 103g.

To 1.2 (1.1 g, 4.43 mmol, 1.0 eq) added mixture of methanol:water (10 mL, 2:1) and acetic acid (2.7 g, 44.3 mmol, 10 eq). The reaction mixture was heated 70° C. then iron powder (2.48 g, 44.3 mmol, 10 eq) was added portionwise. The reaction was stirred at 70° C. for 3 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 30% ethyl acetate in hexane to obtain pure 103 g (0.60 g, 62.23%). MS(ES): m/z 213.68 [M+H]⁺.

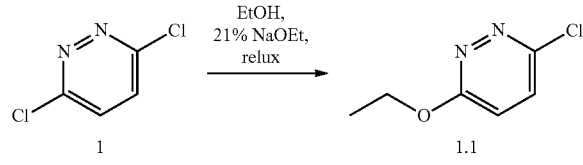

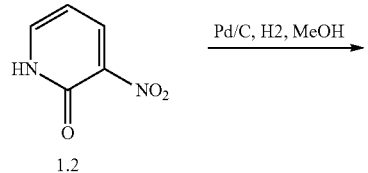

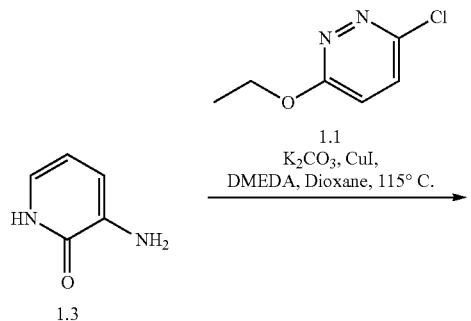

Synthesis of Compound 1.1.

To a solution of 1 (4 g, 26.8 mmol, 1.0 eq), in ethanol (10.4 mL) sodium ethoxide (21%) (8.6 mL, 26.8 mmol, 1.0 eq) was added in 0° C. The reaction mixture was stirred at room temperature for 3 h. After completion of reaction, reaction mixture was, transferred to ice cold water. Organic layer was combined, dried over sodium sulphate and concentrated under reduced pressure to obtain crude material. This was further purified by column chromatography to obtain pure 1.1 (3.2 g, 75.15%). MS(ES): m/z 159 [M+H]⁺

Synthesis of Compound 1.3.

To a solution of 1.2 (15 g, 107.07 mmol, 1.0 eq) in methanol (100 mL), palladium on charcoal (1.5 g) was added. Hydrogen was purged through reaction mixture for 24 h at room temperature. After completion of reaction, reaction mixture was filtered through celite-bed and washed with methanol. Filtrate was concentrated under reduced pressure to obtain 1.3 (1 g, 93.30%). MS(ES): m/z 111 [M+H]⁺.

Synthesis of Compound 103h.

To a solution of 1.3 (11 g, 99.89 mmol, 1.0 eq), in 1,4-dioxane (100 mL) was added 1.1 (17 g, 1.9.8 mmol, 1.1 eq), potassium carbonate (27 g, 199.78 mmol, 2.0 eq) and 1,2-dimethylethylenediamine (35.1 g, 39.95 mmol, 0.4 eq). The reaction mixture was heated at 115° C. temperature for 16 h. After completion of reaction, reaction mixture was, transferred to ice cold water and product was extracted with ethyl acetate. Organic layer was combined, dried over sodium sulphate and concentrated under reduced pressure to obtain crude material. This was further purified by column chromatography using 15% ethyl acetate in hexane as eluant to obtain pure 103 h (0.50 g, 2.16%). MS(ES): m/z 233 [M+H]⁺

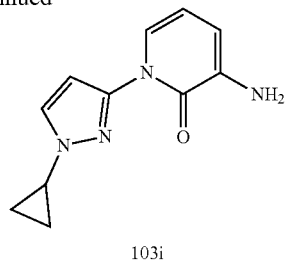

Synthesis of Compound 1.1.

To a solution of 1 (5 g, 44.22 mmol, 1.0 eq), 1,2-dichloroethane (100 mL), 2,2bipyridine (6.8 g, 44.22 mmol, 1.0 eq), sodium carbonate (9.3 g, 88.44 mmol, 2.0 eq) and copper acetate (8 g, 44.22 mmol, 1.0 eq) was added. The reaction mixture was heated at 70° C. for 16 h. After completion of reaction, reaction mixture was filtered through celite and concentrated under reduced pressure to obtain crude material. This was further purified by combi flash using 20% ethyl acetate in hexane as eluant to obtain pure 1.1 (3 g, 44.30%). MS(ES): m/z 154.14 [M+H]$^+$ Synthesis of Compound 1.2.

To a solution of 1.1 (3 g, 19.59 mmol, 1.0 eq) in methanol (60 mL), palladium on charcoal (0.85 g) was added. Hydrogen was purged through reaction mixture for 16 h at room temperature. After completion of reaction, reaction mixture was filtered through celite-bed and washed with methanol. Filtrate was concentrated under reduced pressure to obtain 1.2 (1.8 g, 74.16%). MS(ES): m/z 124.16 [M+H]$^+$ Synthesis of Compound 1.4.

To a solution of 1.3 (1 g, 8.12 mmol, 1.0 eq) in N,N-dimethylformamide (10 mL), methyl 2-oxo-2H-pyran-3-carboxylate (1.2 g, 8.12 mmol, 1.0 eq), was added at 0° C. The reaction mixture was stirred at same temperature for 3 h. 1-ethyl-3-(3-dimethylaminopropylcarbodiimide (2.0 g, 10.55 mol, 1.3 eq) and 4-dimethylaminopridine (0.19 g, 1.62 mmol, 0.2 eq) was added. The reaction was stirred at room temperature for 16 h. After completion of reaction, reaction mixture was, transferred into ice cold water. Organic layer was combined, dried over sodium sulphate and under reduced pressure to obtain 1.4 (0.60 g, 28.50%). MS(ES): m/z 260.27 [M+H]$^+$ Synthesis of Compound 1.5.

To a solution of 1.4 (0.60 g, 2.31 mmol, 1.0 eq), in tetrahydrofuran: methanol: water (5 mL, 1:1:1) was added lithium hydroxide (0.97 g, 23.1 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.5 (0.50 g, 1137.22%). MS(ES): m/z 246.24 [M+H]$^+$.

Synthesis of Compound 1.6.

To a solution of 1.5 (0.50 g, 26.32 mmol, 1.0 eq), diphenyl phosphoryl azide (9.4 g, 34.21 mmol, 1.3 eq), trimethylamine (0.2 mL), in tertiary butanol (0.5 mL) was added. The reaction mixture was heated at 75° C. for 48 h. After completion of reaction, Organic layer was combined, washed with brine solution, dried over sodium sulphate and concentrated under reduced pressure to obtain 1.6 (0.35 g, 4.20%). MS(ES): m/z 317.36 [M+H]$^+$.

Synthesis of Compound 103i

To a solution of 1.6 (0.35 g, 0.94 mmol, 1.0 eq), potassium hydroxide (0.10 g, 1.88 mmol, 2.0 eq) was added in ethylene glycol (4 mL). The reaction mixture was heated at 100° C. for 16 h. After completion of reaction, Organic layer was combined, washed with brine solution, dried over sodium sulphate and concentrated under reduced pressure to obtain crude material. This was further purified by combi flash using 5% methanol in dichloromethane as eluant to 103i (0.16 g, 78.03%). MS(ES): m/z 217.24 [M+H]$^+$.

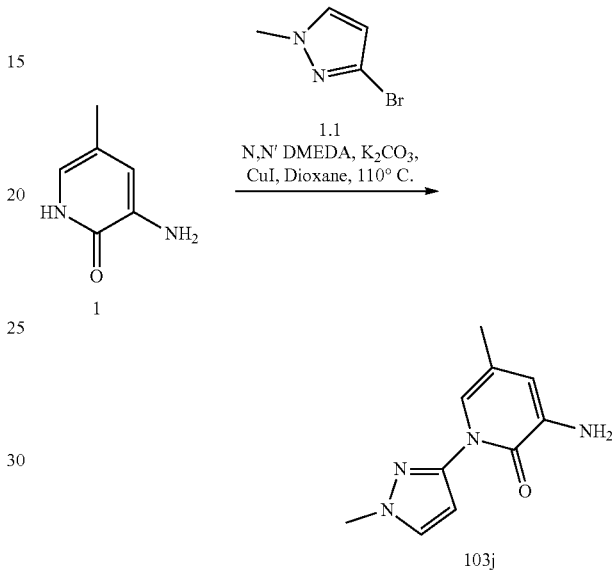

Synthesis of Compound 103j.

To a solution of 1 (1 g, 8.06 mmol, 1.0 eq) and 1.1 (1.56 g, 9.67 mmol, 1.2 eq) in 1,4-dioxane (25 mL) was added potassium carbonate (4.82 g, 20.15 mmol, 2.5 eq) and degassed with argon for 15 min. Copper iodide (0.154 g, 0.806 mmol, 0.1 eq) and 1,2-dimethylethylenediamine (0.141 g, 1.612 mmol, 0.2 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 30% ethyl acetate in hexane to obtain pure 103j (0.800 g, 48.63%). MS(ES): m/z 205.23[M+H]$^+$.

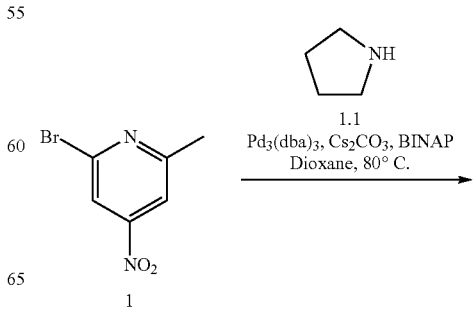

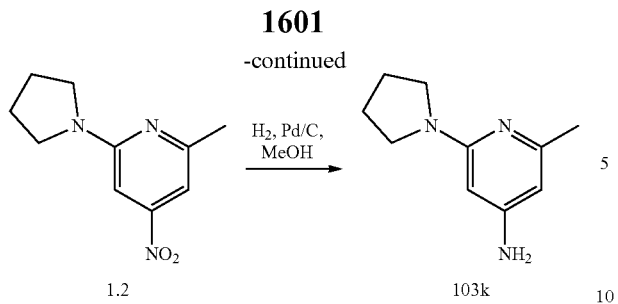

Synthesis of Compound 1.2.

To a solution of 1 (1 g, 4.61 mmol, 1.0 eq) in 1,4-dioxane (5 mL) was added tris(dibenzylideneacetone)dipalladium (0.420 g, 0.461 mmol, 0.1 eq) and cesium carbonate (4.5 g, 13.83 mmol, 3.00 eq) and (2,2'-bis(diphenylphosphino)-1,1'-binaphthyl) (0.575 g, 0.922 mmol, 0.2 eq). The reaction mixture was degassed for 10 min. under argon atmosphere, then 1.1 (0.430 g, 5.99 mmol, 1.3 eq), degassed for 5 min. The reaction was stirred at 100° C. for 30 min. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 1.2 (0.500 g, 52.36%). MS(ES): m/z 207.23[M+H]$^+$.

Synthesis of Compound 103k.

To a solution of 1.2 (0.500 g, 2.41 mmol, 1.0 eq) in methanol (7 ml), palladium on charcoal (0.200 g) was added. Hydrogen was purged through reaction mixture for 2-3 h at room temperature. After completion of reaction, reaction mixture was filtered through celite-bed and washed with methanol. Filtrate was concentrated under reduced pressure to obtain 103k (0.400 g, 93.53%). MS (ES): m/z 178.25 [M+H]$^+$.

Synthesis of Compound 1.2.

To a solution of 1 (1 g, 4.61 mmol, 1.0 eq) in 1,4-dioxane (20 mL) was added tris(dibenzylideneacetone)dipalladium (0.422 g, 0.462 mmol, 0.1 eq) and cesium carbonate (4.51 g, 13.86 mmol, 3.0 eq) and (2,2'-bis(diphenylphosphino)-1,1'-binaphthyl) (0.573 g, 0.924 mmol, 0.2 eq). The reaction mixture was degassed for 10 min under argon atmosphere and added 1.1 (0.955 g, 6.91 mmol, 1.5 eq), again degassed for 5 min. The reaction mixture was stirred at 80° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 1.2 (0.430 g, 39.33%). MS(ES): m/z 238.26[M+H]$^+$.

Synthesis of Compound 103l.

To a solution of 1.2 (0.430 g, 1.81 mmol, 1.0 eq) in methanol (10 ml), palladium on charcoal (0.100 g) was added. Hydrogen was purged through reaction mixture for 2-3 h at room temperature. After completion of reaction, reaction mixture was filtered through celite-bed and washed with methanol. Filtrate was concentrated under reduced pressure to obtain 103l (0.380 g, 95.83%). MS (ES): m/z 208.28 [M+H]$^+$

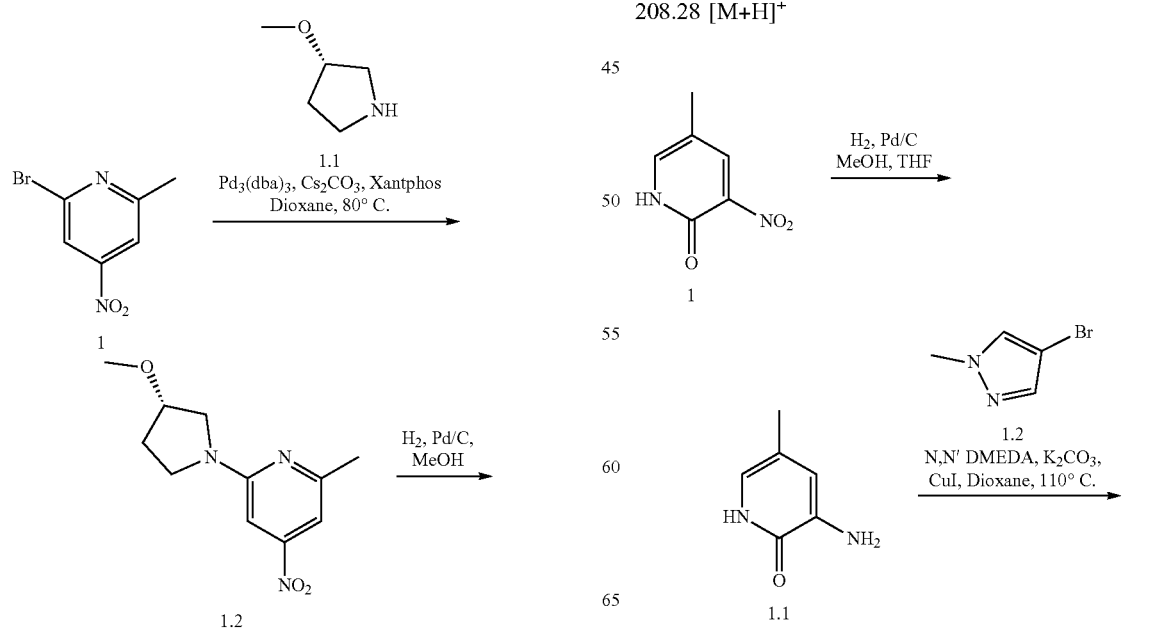

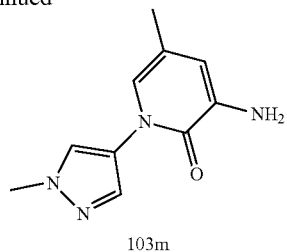

103m

Synthesis of Compound 1.1.

To a solution of 1. (4.0 g, 1.81 mmol, 1.0 eq) in methanol (60 ml), palladium on charcoal (2.0 g) was added. Hydrogen was purged through reaction mixture for 2-3 h at room temperature. After completion of reaction, reaction mixture was filtered through celite-bed and washed with methanol. Filtrate was concentrated under reduced pressure to obtain 1.1 (3.0 g, 93.11%). MS (ES): m/z 125.14 [M+H]$^+$.

Synthesis of Compound 103m.

To a solution of 1.1 (1 g, 8.06 mmol, 1.0 eq) and 1.2 (1.56 g, 9.67 mmol, 1.2 eq) in 1,4-dioxane (20 mL) was added potassium carbonate (2.22 g, 16.12 mmol, 2.0 eq) and degassed with argon for 15 min. Copper iodide (0.306 g, 1.612 mmol, 0.2 eq) and 1,2-dimethylethylenediamine (0.283 g, 3.22 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.8% methanol in dichloromethane to obtain pure 103m (0.800 g, 48.63%). MS(ES): m/z 205.23 [M+H]$^+$.

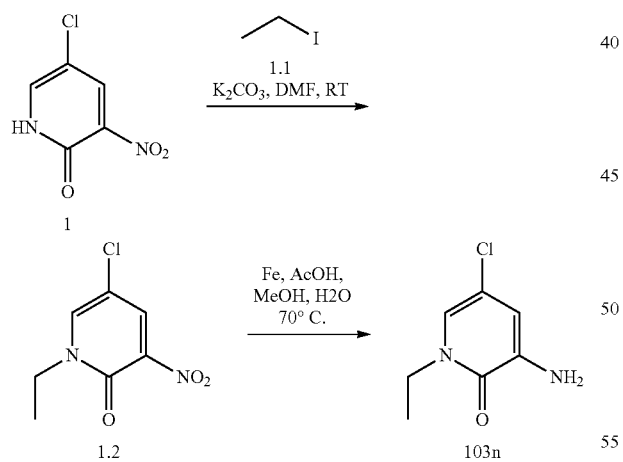

Synthesis of Compound 1.1.

To a solution of 1. (2.0 g, 11.46 mmol, 1.0 eq) in dimethylformamide (40 ml), potassium carbonate (4.47 g, 28.65 mmol, 2.5 eq) was added. Ethyl iodide (2.17 g, 17.19 mmol, 1.5 eq) was added dropwise at room temperature. The reaction was stirred at room temperature for 16 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 1.1 (1.2 g, 51.69%). MS (ES): m/z 203.59 [M+H]$^+$ Synthesis of Compound 103n.

To 1.2 (1.2 g, 5.92 mmol, 1.0 eq) added mixture of methanol:water (9 mL, 2:1) and acetic acid (3.55 g, 59.2 mmol, 10 eq). The reaction mixture was heated 60° C. then iron powder (1.65 g, 29.6 mmol, 5 eq) was added portionwise. The reaction was stirred at 70° C. for 5 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 23% ethyl acetate in hexane to obtain pure 103n (0.700 g, 68.47%). MS(ES): m/z 173.61 [M+H]$^+$.

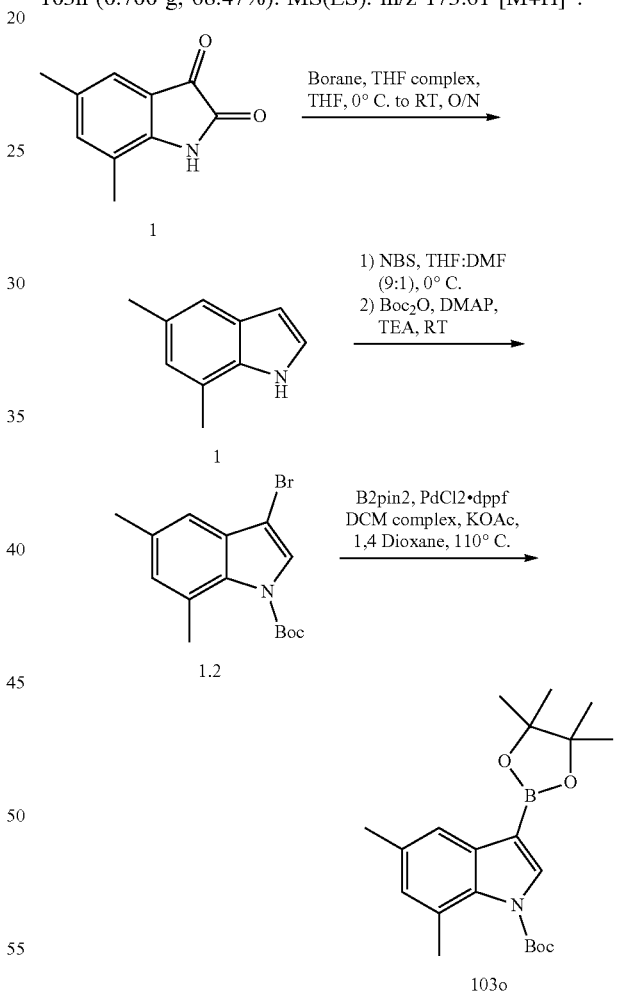

Synthesis of Compound 1.1.

To a cooled solution of 1. (10.0 g, 57.08 mmol, 1.0 eq) in tetrahydrofuran (100 ml), borane tetrahydrofuran (114.0 mL, 114.16 mmol, 2.0 eq) was added dropwise at 0° C. temperature. The reaction was stirred at room temperature for 16 h. After completion of reaction, 5% hydrochloric acid was added. Reaction mixture was transferred into saturated sodium bicarbonate and product was extracted with ethyl acetate. Organic layer was combined and dried over sodium sulphate and concentrated under reduced pressure to obtain crude material. This was further purified by column chromatography and compound was eluted in 30% ethyl acetate in hexane to obtain pure 1.1 (3.2 g, 39.61%). MS (ES): m/z 146.21 [M+H]$^+$ Synthesis of Compound 1.2.

To a cooled solution of 1.1 (3.2 g, 22.04 mmol, 1.0 eq) in mixture of tetrahydrofuran:dimethylformamide (40 mL, 9:1), N-bromosuccinamide (3.92 g, 22.04 mmol, 1 eq) was added. Reaction mixture was stirred at 0° C. for 15 min followed by addition of triethylamine (7.79 g, 77.14 mmol, 3.5 eq), 4-Dimethylaminopyridine (15 mg), and Di-tert-butyl dicarbonate (13.75 g, 66.12 mmol, 3 eq) at same temperature. The reaction was stirred at room temperature for 30 min. After completion of reaction, reaction mixture transferred into ice cold water and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 1.2 (3.2 g, 44.79%). MS(ES): m/z 325.22 [M+H]$^+$.

Synthesis of Compound 103o.

To a solution of 1.2 (3.2 g, 9.87 mmol, 1.0 eq) in 1,4-dioxane (25 mL) was added bis(pinacolato)diboron (7.53 g, 29.61 mmol, 3 eq) and potassium acetate (2.90 g, 29.61 mmol, 3 eq). The reaction mixture was degassed for 10 min. under argon atmosphere, then 1,1'-Bis(diphenylphosphino)ferrocene]dichloropalladium(II)dichloride dichloromethane (0.241 g, 0.295 mmol, 0.03 eq) was added and again degassed for 5 min. The reaction was stirred at 110° C. for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 8% ethyl acetate in hexane to obtain pure 103o (1.2 g, 32.75%). MS(ES): m/z 372.28 [M+H]$^+$.

Synthesis of Compound 1.1.

To a cooled solution of 1. (3.0 g, 13.89 mmol, 1.0 eq) in diethylether (100 mL), was added methyl magnesium iodide (2.0 g, 20.83 mmol, 1.5 eq) with under nitrogen. The reaction was stirred at room temperature for 5 min. After completion of reaction, reaction mixture was quenched with 1N hydrochloric acid and extracted with ethyl acetate. Organic layer was wash with bicarbonate solution and combined and dried over sodium sulphate and concentrated under reduced pressure to obtain crude material. This was further purified by column chromatography and compound was eluted in 12% ethyl acetate in hexane to obtain pure 1.1 (2.8 g, 93.31%). MS (ES): m/z 217.05 [M+H]$^+$.

Synthesis of Compound 103p.

To a solution of 1. (2.8 g, 12.96 mmol, 1.0 eq) and 1.2 (1.28 g, 11.66 mmol, 0.9 eq) in 1,4-dioxane (20 mL) was added potassium carbonate (3.57 g, 25.92 mmol, 2.0 eq) and degassed with argon for 15 min. Copper iodide (0.492 g, 2.59 mmol, 0.2 eq) and 1,2-dimethylethylenediamine (0.456 g, 5.18 mmol, 0.4 eq) was added and reaction mixture again degassed with argon for 5 min followed by heating at 115° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 19% ethyl acetate in hexane to obtain pure 103p (1.6 g, 50.34%). MS(ES): m/z 246.48 [M+H]$^+$.

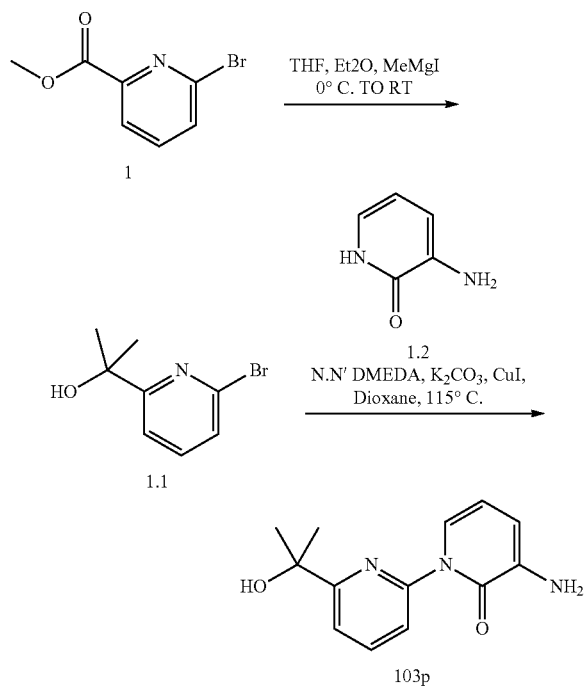

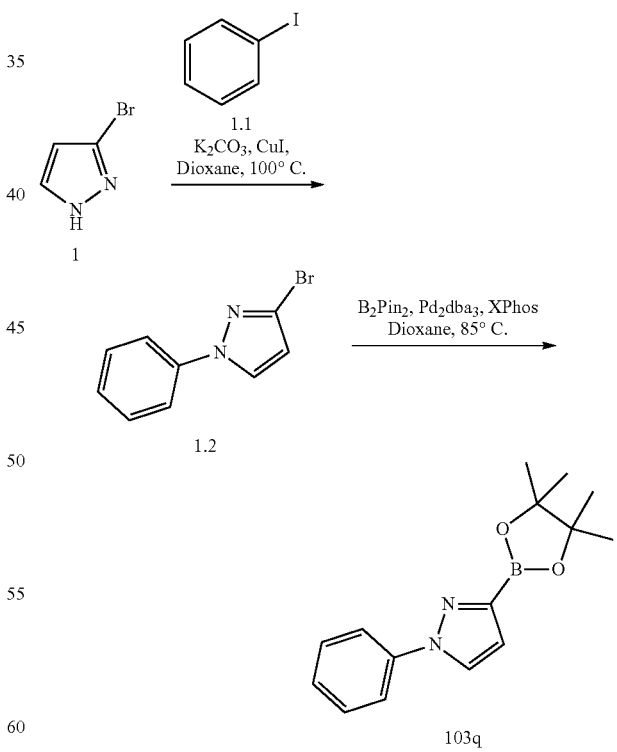

Synthesis of Compound 1.2.

To a solution of 1 (2 g, 13.61 mmol, 1.0 eq) and 1.1 (3.3 g, 16.33 mmol, 1.2 eq) in 1,4-dioxane (30 mL) was added potassium carbonate (4.2 g, 30.62 mmol, 2.25 eq) and degassed with argon for 15 min. Copper iodide (0.258 g, 1.36 mmol, 0.1 eq) and 1,2-diaminocyclohexane (0.386 g, 2.72 mmol, 0.2 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 7% ethyl acetate in hexane to obtain pure 1.2 (1.8 g, 29.30%). MS(ES): m/z 224.07[M+H]$^+$.

Synthesis of Compound 103q.

To a solution of 1.2 (1.8 g, 8.07 mmol, 1.0 eq) in 1,4-dioxane (18 mL) was added bis(pinacolato)diboron (4.1 g, 16.14 mmol, 2 eq) and potassium acetate (2.38 g, 24.21 mmol, 3 eq). The reaction mixture was degassed for 10 min. under argon atmosphere, then 2-dicyclohexylphosphino-2', 4',6'-triisopropylbiphenyl (0.010 g, 0.160 mmol, 0.02 eq) and tris(dibenzylideneacetone)dipalladium(0) (0.073 g, 0.080 mmol, 0.01 eq) added, again degassed for 5 min. The reaction mixture was stirred at 85° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 27% ethyl acetate in hexane to obtain pure 103q (1 g, 45.88%). MS(ES): m/z 271.14 [M+H]$^+$.

reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 9% ethyl acetate in hexane to obtain pure 1.1 (0.450 g, 23.82%). MS (ES): m/z 330.74 [M+H]$^+$ Synthesis of Compound 103r.

To 1.2 (0.450 g, 1.36 mmol, 1.0 eq) added mixture of methanol:water (4 mL, 2:1) and acetic acid (0.816 g, 13.6 mmol, 10 eq). The reaction mixture was heated 65° C. then iron powder (0.380 g, 6.8 mmol, 5 eq) was added portionwise. The reaction was stirred at 65° C. for 5 h. After completion of reaction, reaction mixture was cooled to room temperature and filtered. Filtrate was neutralised with saturated sodium bicarbonate and product was extracted with ethyl acetate. Organic layer was combined, washed with brine solution, dried over sodium sulphate and concentrated under reduced pressure to obtain crude material. This was further purified by column chromatography and compound was eluted in 16% ethyl acetate in hexane to obtain pure 103r (0.300 g, 73.33%). MS(ES): m/z 300.76 [M+H]$^+$.

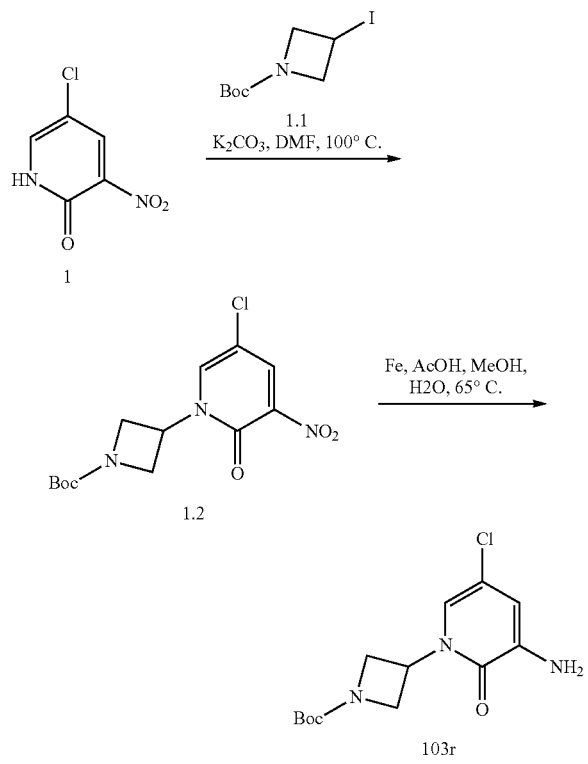

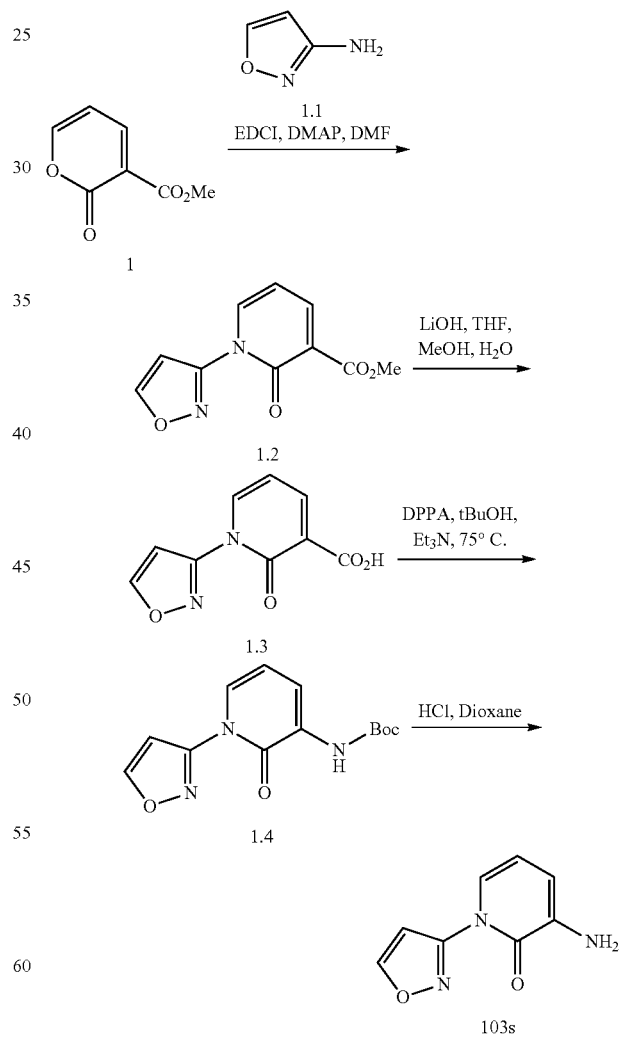

Synthesis of Compound 1.1.

To a solution of 1. (1.0 g, 5.73 mmol, 1.0 eq) in dimethylformamide (10 ml), potassium carbonate (1.98 g, 14.35 mmol, 2.5 eq) was added. 1.1 (2.43 g, 8.59 mmol, 1.5 eq) was added dropwise at room temperature. The reaction was stirred at room temperature for 16 h. After completion of Synthesis of Compound 1.2.

To a cooled solution of 1 (2 g, 12.98 mmol, 1.0 eq), in N,N-dimethylformamide (20 mL) was added 1.1 (1.09 g, 12.98 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.61 g, 16.87 mmol, 1.3 eq) and 4-Dimethylaminopyridine (0.395 g, 3.24 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (1.0 g, 35%). MS(ES): m/z 221.18 [M+H]$^+$.

Synthesis of Compound 1.3.

To a solution of 1.2 (1 g, 4.54 mmol, 1.0 eq), in tetrahydrofuran: methanol: water (40 mL, 2:1:1) was added lithium hydroxide (0.953 g, 22.7 mmol, 5 eq). The reaction was stirred at room temperature for 1 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.675 g, 72.09%). MS(ES): m/z 207.16 [M+H]$^+$.

Synthesis of Compound 1.4.

To a solution of 1.3 (0.675 g, 3.27 mmol, 1 eq) in tert.butanol (8 mL) was added triethylamine (0.561 g, 5.56 mmol, 1.7 eq) and diphenyl phosphoryl azide (1.16 g, 4.25 mmol, 1.3 eq) under nitrogen followed by heating at 75° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 15% ethyl acetate in hexane to obtain pure 1.4 (0.480 g, 52.87%). MS(ES): m/z 278.28 [M+H]$^+$.

Synthesis of Compound 103s.

A solution of 1.4 (0.480 g, 1.73 mmol, 1 eq) in hydrochloric acid in dioxane (6 mL) was stirred at room temperature for 16 h. After completion of reaction, reaction mixture was concentrated under reduced pressure to obtain pure 103s (0.250 g, 81.52%). MS(ES): m/z 178.16 [M+H]$^+$.

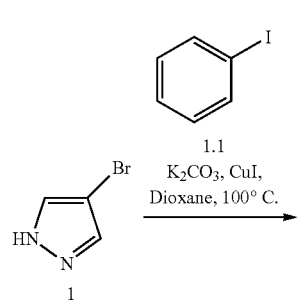

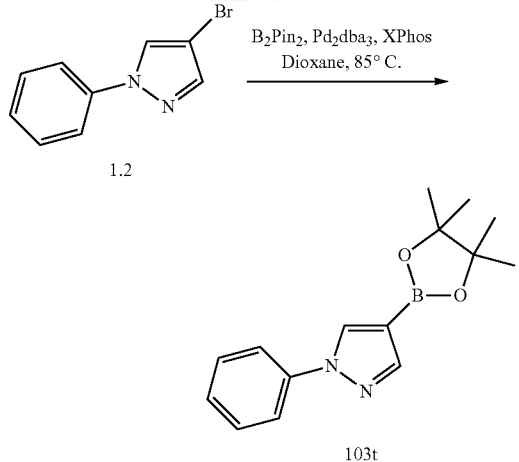

Synthesis of Compound 1.1.

To a solution of 1 (5 g, 34.02 mmol, 1.0 eq) and 1.1 (8.33 g, 40.42 mmol, 1.2 eq) in 1,4-dioxane (40 mL) was added potassium carbonate (10.56 g, 76.54 mmol, 2.25 eq) and degassed with argon for 15 min. Copper iodide (0.646 g, 3.40 mmol, 0.1 eq) and 1,2-diaminocyclohexane (0.589 g, 6.80 mmol, 0.2 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 7% ethyl acetate in hexane to obtain pure 1.2 (3.2 g, 42.17%). MS(ES): m/z 224.07[M+H]$^+$.

Synthesis of Compound 103t.

To a solution of 1.2 (2.7 g, 8.07 mmol, 1.0 eq) in 1,4-dioxane (30 mL) was added bis(pinacolato)diboron (3.7 g, 16.14 mmol, 1.2 eq), potassium acetate (2.38 g, 24.21 mmol, 2 eq). The reaction mixture was degassed for 10 min. under argon atmosphere, then 2-dicyclohexylphosphino-2', 4',6'-triisopropylbiphenyl (0.116 g, 0.160 mmol, 0.02 eq) tris(dibenzylideneacetone)dipalladium(0) (0.110 g, 0.080 mmol, 0.01 eq) again degassed for 5 min. The reaction was stirred at 85° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 27% ethyl acetate in hexane to obtain pure 103t (1.2 g, 36.70%). MS(ES): m/z 271.14 [M+H]$^+$.

-continued

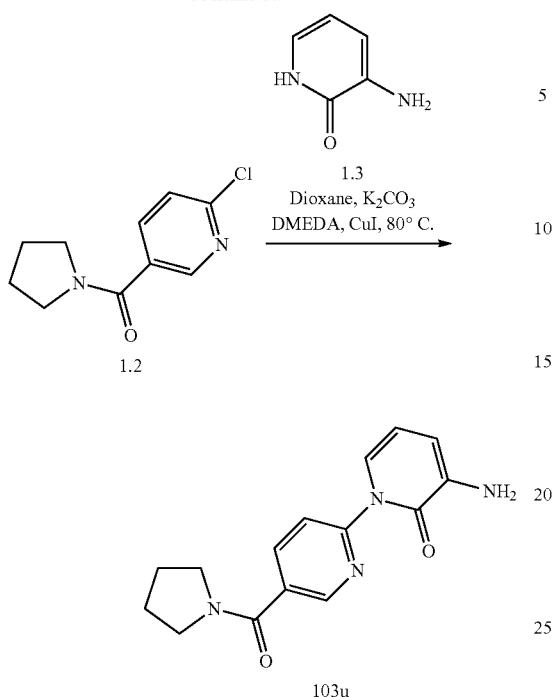

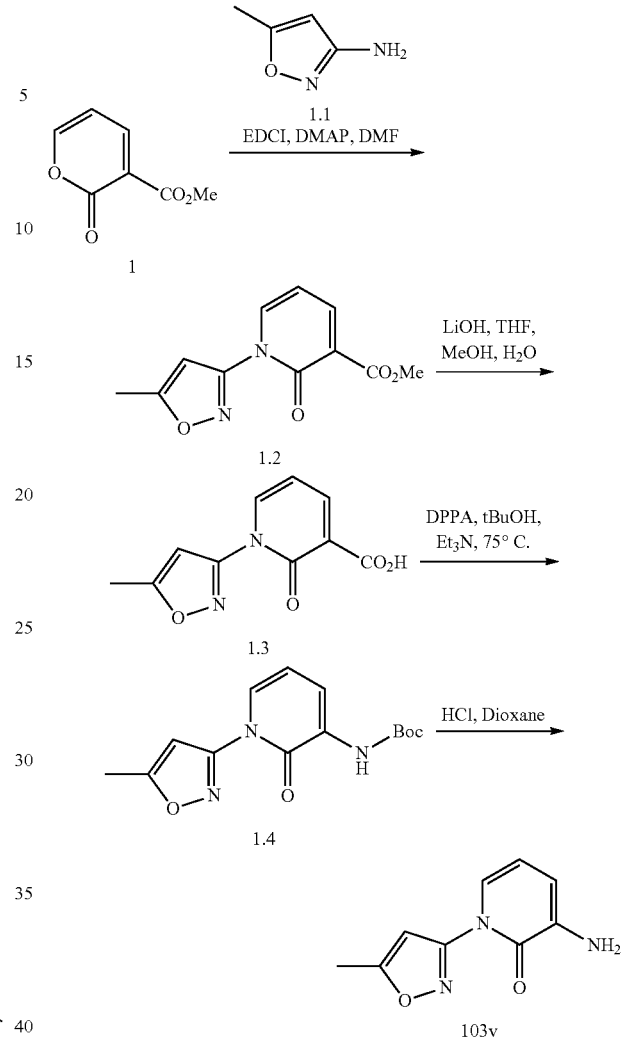

Synthesis of Compound 1.2.

To a cooled solution of 1 (4 g, 25.39 mmol, 1.0 eq), in N,N-dimethylformamide (40 mL) was added 1-hydroxybenzotriazole (4.11 g, 30.47 mmol, 1.2 eq), diisopropylethylamine (5.25 mL, 101.56 mmol, 4.0 eq) and N-Ethyl-N'-(3-dimethylaminopropyl)carbodiimide hydrochloride (8.28 g, 43.16 mmol, 1.7 eq) was added. The reaction mixture was stirred at 0° C. temperature for 15 min. Further added 1.1 (2.17 g, 30.47 mmol, 1.2 eq) and reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 8% ethyl acetate in hexane to obtain 1.2 (2.5 g, 46.74%). MS(ES): m/z 211.66 [M+H]$^+$.

Synthesis of Compound 103u.

To a solution of 1.2 (1 g, 4.75 mmol, 1 eq) and 1.3 (0.627 g, 5.70 mmol, 1.2 eq) in 1,4-dioxane (10 mL) was added potassium carbonate (1.31 g, 9.5 mmol, 2.0 eq) and degassed with argon for 15 min. Copper iodide (0.190 g, 0.95 mmol, 0.2 eq) and 1,2-dimethylethylenediamine (0.167 g, 1.9 mmol, 0.4 eq) was added and reaction mixture again degassed with argon for 5 min followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 103 u (0.500 g, 37.05%). MS(ES): m/z 285.32 [M+H]$^+$.

Synthesis of Compound 1.2.

To a cooled solution of 1 (3 g, 19.47 mmol, 1.0 eq), in N,N-dimethylformamide (30 mL) was added 1.1 (1.92 g, 19.47 mmol, 1 eq). The reaction mixture was stirred at 0° C. temperature for 3 h and further stirred at room temperature for 15 min. N-Ethyl-N'-(3-dimethylaminopropyl)carbodiimide hydrochloride (3.92 g, 25.31 mmol, 1.3 eq) and 4-Dimethylaminopyridine (0.594 g, 4.86 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (1.7 g, 37.29%). MS(ES): m/z 235.21 [M+H]$^+$.

Synthesis of Compound 1.3.

To a solution of 1.2 (1.7 g, 7.26 mmol, 1.0 eq), in tetrahydrofuran: methanol: water (68 mL, 2:1:1) was added lithium hydroxide (1.52 g, 36.3 mmol, 5 eq). The reaction was stirred at room temperature for 1 h. After completion of reaction, reaction mixture was concentrated under reduced pressure to obtain residue. To this added water and acidified with 1N hydrochloric acid to adjust pH~6-6.5 at 10° C.

Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (1.3 g, 81.34%). MS(ES): m/z 221.18 [M+H]+.

Synthesis of Compound 1.4.

To a solution of 1.3 (1.3 g, 5.90 mmol, 1 eq) in tert.butanol (20 mL) was added triethylamine (1.01 g, 10.03 mmol, 1.7 eq) and diphenyl phosphoryl azide (2.10 g, 7.67 mmol, 1.3 eq) under nitrogen followed by heating at 75° C. for 48 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 15% ethyl acetate in hexane to obtain pure 1.4 (0.400 g, 23.26%). MS(ES): m/z 292.31 [M+H]+.

Synthesis of Compound 103v.

A solution of 1.4 (0.400 g, 1.37 mmol, 1 eq) in hydrochloric acid in dioxane (5 mL) was stirred at room temperature for 16 h. After completion of reaction, reaction mixture was concentrated under reduced pressure to obtain pure 103v (0.250 g, 95.23%). MS(ES): m/z 292.19 [M+H]+.

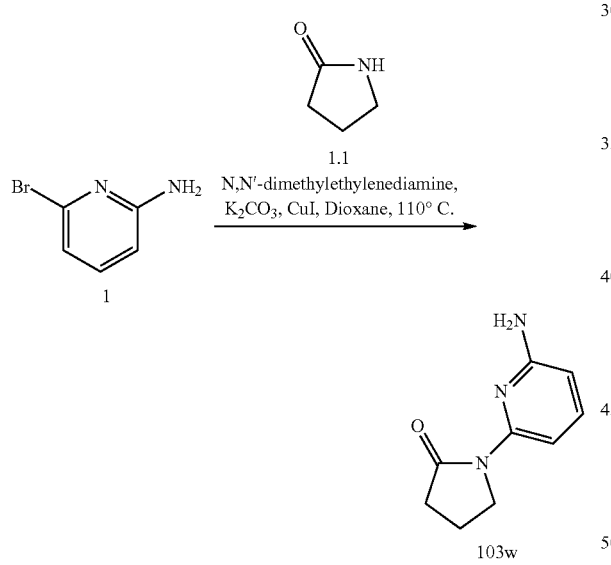

Synthesis of Compound 103w.

To a solution of 1 (0.500 g, 2.89 mmol, 1 eq) and 1.1 (0.295 g, 3.47 mmol, 1.2 eq) in 1,4-dioxane (5 mL) was added potassium carbonate (0.797 g, 5.78 mmol, 2.0 eq) and degassed with argon for 15 min. Copper iodide (0.109 g, 0.578 mmol, 0.2 eq) and 1,2-dimethylethylenediamine (0.101 g, 1.15 mmol, 0.4 eq) was added and reaction mixture again degassed with argon for 5 min followed by heating at 110° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 103 w (0.320 g, 62.49%). MS(ES): m/z 178.2 [M+H]+.

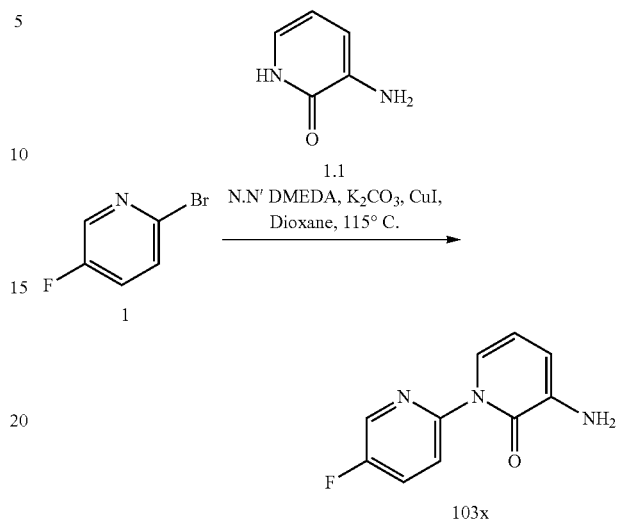

Synthesis of Compound 103x.

To a solution of 1. (1 g, 5.68 mmol, 1.0 eq) and 1.1 (1.25 g, 11.36 mmol, 2 eq) in 1,4-dioxane (20 mL) was added potassium carbonate (1.56 g, 11.36 mmol, 2.0 eq) and degassed with argon for 15 min. Copper iodide (0.324 g, 1.70 mmol, 0.3 eq) and 1,2-dimethylethylenediamine (0.150 g, 1.70 mmol, 0.3 eq) was added and reaction mixture again degassed with argon for 5 min followed by heating at 115° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.4% methanol in dichloromethane to obtain pure 103x (0.800 g, 68.61%). MS(ES): m/z 206.19 [M+H]+.

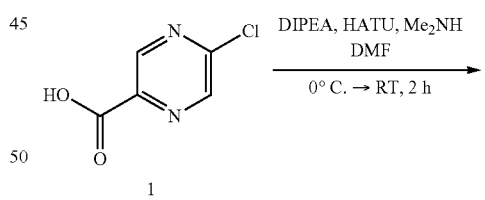

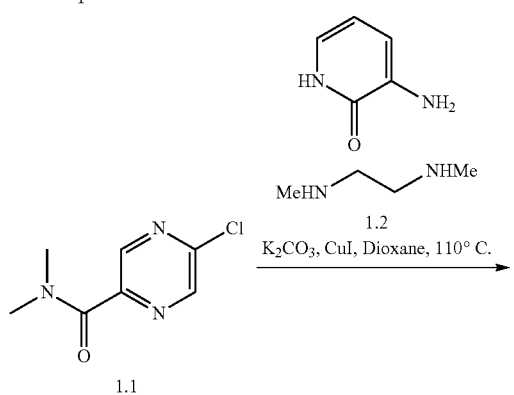

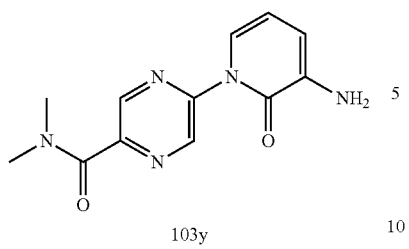
103y

Synthesis of Compound 1.1.

To a cooled solution of 1 (3 g, 18.92 mmol, 1.0 eq), in N,N-dimethylformamide (30 mL) was added 1-[Bis(dimethylamino)methylene]-1H-1,2,3-triazolo[4,5-b]pyridinium 3-oxid hexafluorophosphate (8.65 g, 22.70 mmol, 1.2 eq) and stirred at room temperature for 20 min. Reaction mixture again cooled diisopropylethylamine (7.32 mL, 56.76 mmol, 3.0 eq) was added followed by addition of dimethylamine (0.851 g, 18.92 mmol, 1.0 eq). The reaction mixture was stirred at room temperature for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 0.9% methanol in dichloromethane to obtain 1.1 (2.5 g, 71.18%). MS(ES): m/z 186.61 [M+H]$^+$.

Synthesis of Compound 103y.

To a solution of 1.1 (3 g, 13.47 mmol, 1.2 eq) and 1.2 (0.989 g, 11.22 mmol, 1.0 eq) in 1,4-dioxane (30 mL) was added potassium carbonate (3.71 g, 26.94 mmol, 2.0 eq) and degassed with argon for 15 min. Copper iodide (0.371 g, 2.69 mmol, 0.2 eq) and 1,2-dimethylethylenediamine (0.474 g, 5.38 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.5% methanol in dichloromethane to obtain pure 103y (1.2 g, 41.24%). MS(ES): m/z 260.27 [M+H]$^+$.

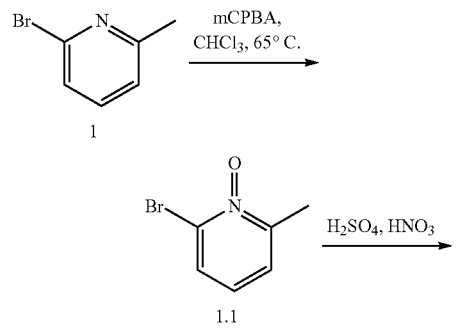

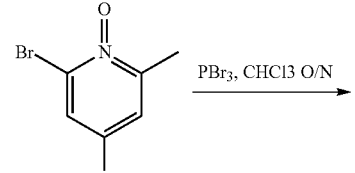

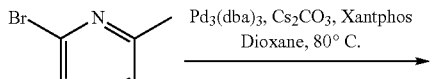

Synthesis of Compound 1.1.

To a cooled solution of 1 (10 g, 58.13 mmol, 1.0 eq), in dichloromethane (100 mL) was added meta-Chloroperoxybenzoic acid (20 g, 116.26 mmol, 2 eq). The reaction mixture was stirred at room temperature for 3 h. After completion of reaction, reaction mixture was filtrated, filtrate was wash with 1N sodium hydroxide. Organic layer was combined, dried over sodium sulphate and concentrated under reduced pressure to obtain crude material. This was further purified by column chromatography and the compound was eluted in 27% ethyl acetate in hexane to obtain 1.1 (8 g, 73.19%). MS(ES): m/z 189.02 [M+H]$^+$.

Synthesis of Compound 1.2.

To a cooled 1.1 (8 g, 42.55 mmol, 1.0 eq) was added sulfuric acid (11.33 mL, 212.77 mmol, 5 eq) and nitric acid (8.96 mL, 202.11 mmol, 4.75 eq). The reaction mixture was stirred at room temperature for 15 min. Further reaction mixture was heated 80° C. for 16 h. After completion of reaction, reaction mixture was transferred into ice cold water, product was precipitated out. Product was filtrated and dried well to obtain pure 1.2 (5 g, 50.43%). MS(ES): m/z 234.02 [M+H]$^+$.

Synthesis of Compound 1.3.

To a solution of 1.2 (5 g, 21.46 mmol, 1.0 eq) in chloroform (50 mL) was added phosphorus tribromide (7.6 mL, 64.38 mmol, 3 eq). The reaction mixture was heated 60° C. for 16 h. After completion of reaction, reaction mixture was transferred into ice cold 2N sodium hydroxide and product was extracted with dichloromethane. Organic layer was combined, washed with brine solution, dried over sodium sulphate and concentrated under reduced pressure to obtain pure 1.3 (3.2 g, 68.72%). MS(ES): m/z 218.02 [M+H]$^+$.

Synthesis of Compound 1.5.

Compound was synthesized using general procedure B to obtain 1.5 (1.2 g, 58.86%). MS (ES): m/z 222.22 [M+H]+

Synthesis of Compound 103z.

To a solution of 1.5 (1.2 g, 1.81 mmol, 1.0 eq) in methanol (17 ml), palladium on charcoal (0.300 g) was added. Hydrogen was purged through reaction mixture for 16 h at room temperature. After completion of reaction, reaction mixture was filtered through celite-bed and washed with methanol. Filtrate was concentrated under reduced pressure to obtain 103z (0.550 g, 53.02%). MS (ES): m/z 192.03 [M+H]+

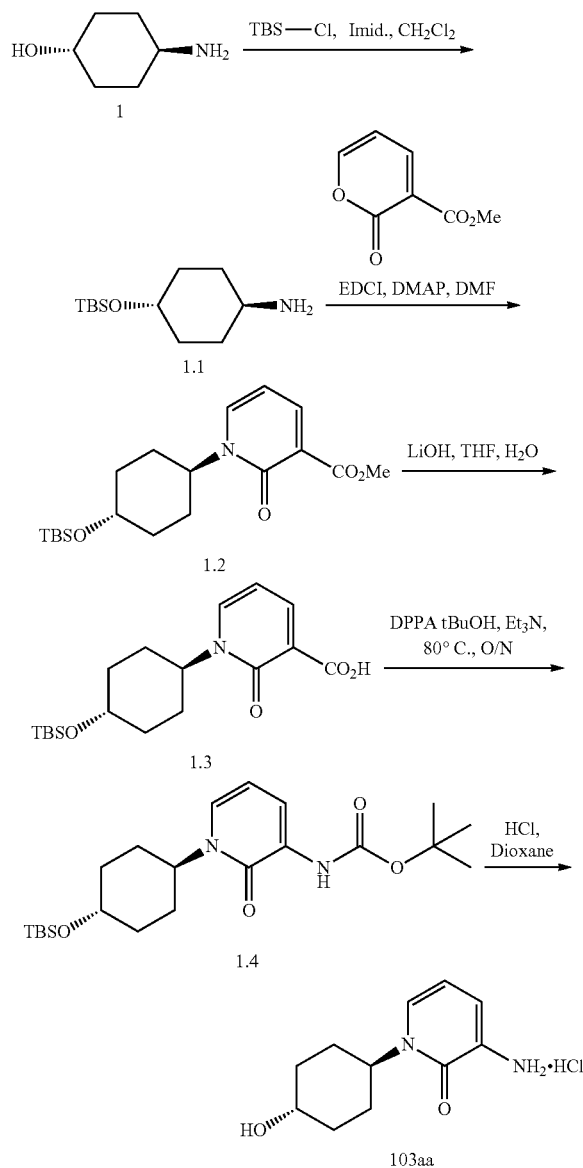

Synthesis of Compound 1.1.

To a solution of 1 (10 g, 86.82 mmol, 1.0 eq) in dichloromethane (200 mL) was added imidazole (29.5 g, 434.1 mmol, 5.0 eq) and tert-butyldimethylsilyl chloride (19.6 g, 130.23 mmol, 1.5 eq). The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% methanol in dichloromethane as eluant to obtain pure 1.1 (7.2 g, 36.14%). MS(ES): m/z 230.44 [M+H]+

Synthesis of Compound 1.2.

To a solution of 1.1 (7.2 g, 31.38 mmol, 1.0 eq) in dimethylformamide (40 mL) was added methyl 2-oxo-2H-pyran-3-carboxylate (4.8 g, 31.38 mmol, 1.0 eq). The reaction mixture was stirred at room temperature for 7 h followed by addition of 1-ethyl-3-(3-dimethylaminopropylcarbodiimide (6.5 g, 34.51 mol, 1.1 eq) and 4-dimethylaminopridine (0.95 g, 7.84 mmol, 0.25 eq). The reaction was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 30% ethylacetate in hexane as eluant to 1.2 (2.7 g, 23.54%). MS(ES): m/z 366.55 [M+H]+

Synthesis of Compound 1.3.

To a solution of 1.2 (2.7 g, 7.39 mmol, 1.0 eq), in tetrahydrofuran: methanol: water (5 mL, 1:1:1) was added lithium hydroxide (3.1 g, 73.9 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.3 (2.2 g, 84.73%). MS(ES): m/z 352.52 [M+H]+.

Synthesis of Compound 1.4.

To a solution of 1.3 (2.2 g, 6.26 mmol, 1.0 eq) tert-butanol (35 mL) was added diphenylphosphorylazide (2.7 g, 10.01 mmol, 1.6 eq), trimethylamine (1.5 mL). The reaction mixture was heated at 75° C. for 18 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% ethyl acetate in hexane as eluant to 1.4 (1.27 g, 48.01%). MS(ES): m/z 423.64 [M+H]+.

Synthesis of Compound 103aa.

To a solution of 1.4 (1.27 g, 3.00 mmol, 1.0 eq) in dry dichloromethane (10 mL) was added 4M hydrochloric acid in dioxane (5 mL) was at 0° C. The reaction mixture was stirred at room temperature for 16 h. Reaction mixture was concentrated under reduced pressure to obtain crude material. This was further purified by trituration with diethyl ether to obtain 103aa (0.50 g, 69.35%). MS(ES): m/z 245.72 [M+H]+.

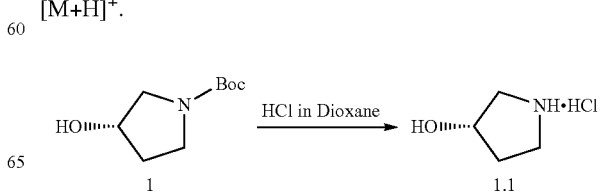

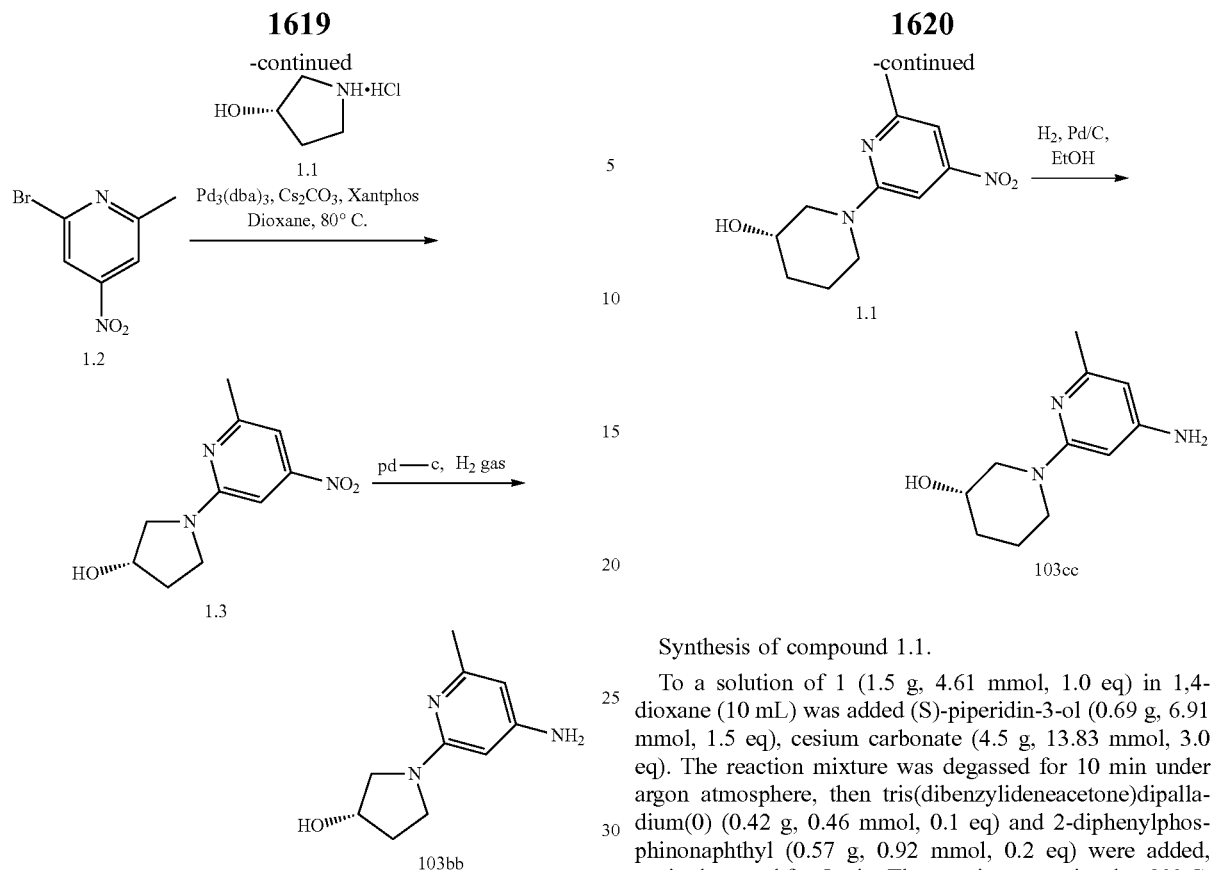

Synthesis of Compound 1.1.

To 1 (2 g, 26.8 mmol, 1.0 eq) added hydrochloric acid in 1,4-dioxane (2 mL). The reaction mixture was stirred at room temperature for 1 h. After completion of reaction, reaction mixture was concentrated under reduced pressure to obtain residue which was stirred with diethyl ether and filtered to obtain pure 1.1 (1.2 g, 85.97%). MS(ES): m/z 88.12 [M+H]⁺

Synthesis of Compound 1.3.

Compound was synthesized using general procedure B to obtain 1.3 (0.700, 56.71%). MS (ES): m/z 224.23 [M+H]⁺

Synthesis of Compound 103bb.

To a solution of 1.3 (0.700 g, 3.14 mmol, 1.0 eq) in methanol (15 mL), palladium on charcoal (0.200 g) was added. Hydrogen was purged through reaction mixture for 24 h at room temperature. After completion of reaction, reaction mixture was filtered through celite-bed and washed with methanol. Filtrate was concentrated under reduced pressure to obtain 103bb (0.380 g, 62.71%). MS(ES): m/z 194.25 [M+H]⁺

Synthesis of compound 1.1.

To a solution of 1 (1.5 g, 4.61 mmol, 1.0 eq) in 1,4-dioxane (10 mL) was added (S)-piperidin-3-ol (0.69 g, 6.91 mmol, 1.5 eq), cesium carbonate (4.5 g, 13.83 mmol, 3.0 eq). The reaction mixture was degassed for 10 min under argon atmosphere, then tris(dibenzylideneacetone)dipalladium(0) (0.42 g, 0.46 mmol, 0.1 eq) and 2-diphenylphosphinonaphthyl (0.57 g, 0.92 mmol, 0.2 eq) were added, again degassed for 5 min. The reaction was stirred at 80° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluent to obtain pure 1.1 (0.93 g, 85.07%). MS(ES): m/z 238.26 [M+H]⁺

Synthesis of Compound 103cc.

To a solution of 1.1 (0.93 g, 3.92 mmol, 1.0 eq) in methanol (10 mL), palladium on charcoal (0.20 g) was added. Hydrogen was purged through reaction mixture for 24 h at room temperature. After completion of reaction, reaction mixture was filtered through celite-bed and washed with methanol. Filtrate was concentrated under reduced pressure to obtain 103cc (0.62 g, 76.31%). MS(ES): m/z 208.02 [M+H]⁺

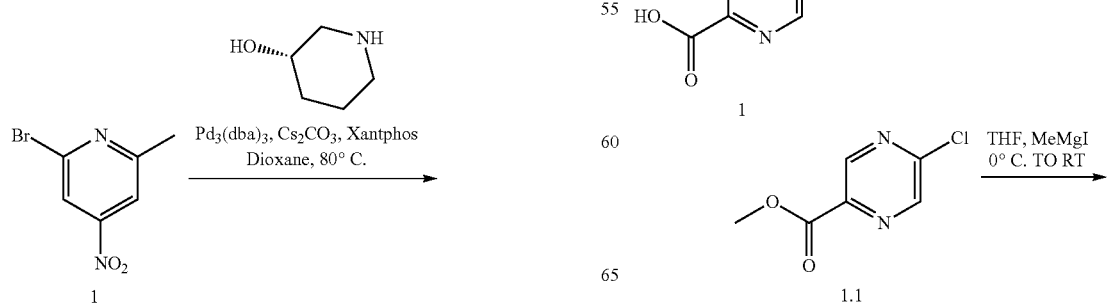

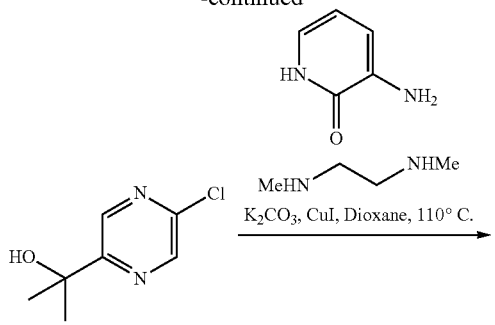
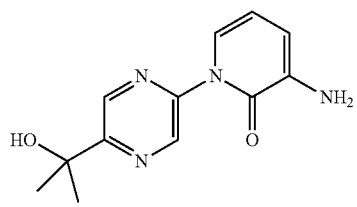 [SMILES: CC(C)(O)c1cnc(-n2cccc(N)c2=O)cn1]
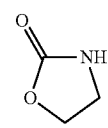
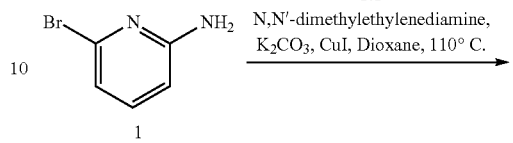
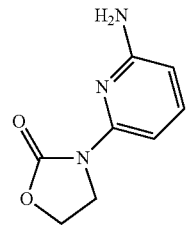

Synthesis of Compound 1.1.

To a solution of 1 (2 g, 12.62 mmol, 1.0 eq) in methanol (14 mL) was added and trimethylsilane diazomethane (2.8 g, 25.24 mmol, 2.0 eq) and diethyl ether (14 mL). The reaction mixture was stirred at room temperature for 2 h. After completion of reaction, reaction mixture concentrated under reduced pressure to obtain residue. This was further purified by trituration with hexane to obtain pure 1.1 (1.5 g, 73.50%). MS(ES): m/z 173.57 [M+H]$^+$ Synthesis of Compound 1.2.

To a solution of 1.1 (1.6 g, 9.27 mmol, 1.0 eq) in tetrahydrofuran (4 mL) was added and methyl magnesium iodide (2.12 mL) at −10° C. The reaction mixture was stirred at 0° C. for 1 h. After completion of reaction, reaction mixture was transferred into dilute hydrochloric acid and product was extracted with ethyl acetate. Organic layer was combined, washed with brine solution, dried over sodium sulphate and concentrated under reduced pressure to obtain crude material. This was further purified by column chromatography by using 10% ethyl acetate in hexane as eluant to 1.2 (0.60 g, 26.28%). MS(ES): m/z 173.5 [M+H]$^+$ Synthesis of Compound 103dd.

To a solution of 1.2. (0.56 g, 3.24 mmol, 1.0 eq) in 1,4-dioxane (9 mL), potassium carbonate (0.89 g, 6.48 mmol, 2.0 eq), copper iodide (0.18 g, 0.97 mmol, 0.3 eq), 3-aminopyridin-2(1H)-one (0.71 g, 6.348 mmol, 2.0 eq) and N1,N2-dimethylethane-1,2-diamine (0.08 g, 0.97 mmol, 0.3 eq) was added. The reaction mixture was heated at 110° C. for 2 h. Reaction mixture was transferred into ice cold water and product was extracted by ethyl acetate. Organic layer was combined, washed with brine solution, dried over sodium sulphate and concentrated under reduced pressure to obtain crude material. This was further purified by column chromatography by using 2% methanol in dichloromethane as eluant to obtain 103dd (0.28 g, 35.05%). MS(ES): m/z 247.27 [M+H]$^+$ Synthesis of Compound 103ee.

To a solution of 1 (1 g, 5.78 mmol, 1.0 eq) and 1.1 (0.75 g, 8.67 mmol, 1.5 eq) in 1,4-dioxane (10 mL) was added potassium carbonate (1.5 g, 11.56 mmol, 2.0 eq). The reaction mixture was degassed for 10 min under argon atmosphere, copper iodide (0.10 g, 0.57 mmol, 0.1 eq) and N,N-dimethylethylenediamine (0.10 g, 1.15 mmol, 0.2 eq) were added. The reaction mixture was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 70% ethylacetate in hexane as eluant to obtain pure 103ee (0.75 g, 72.42%). MS(ES): m/z 180.18 [M+H]$^+$.

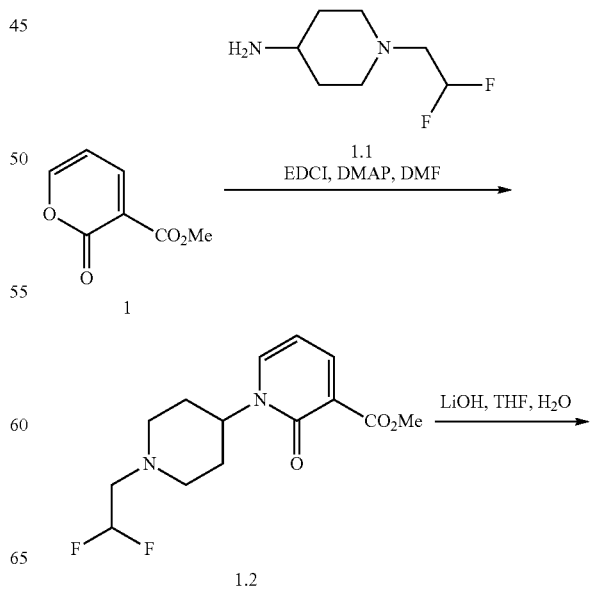

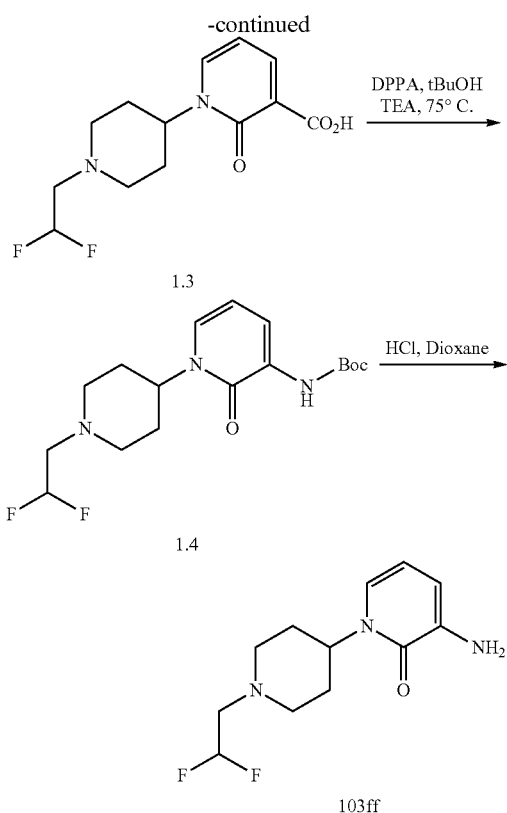

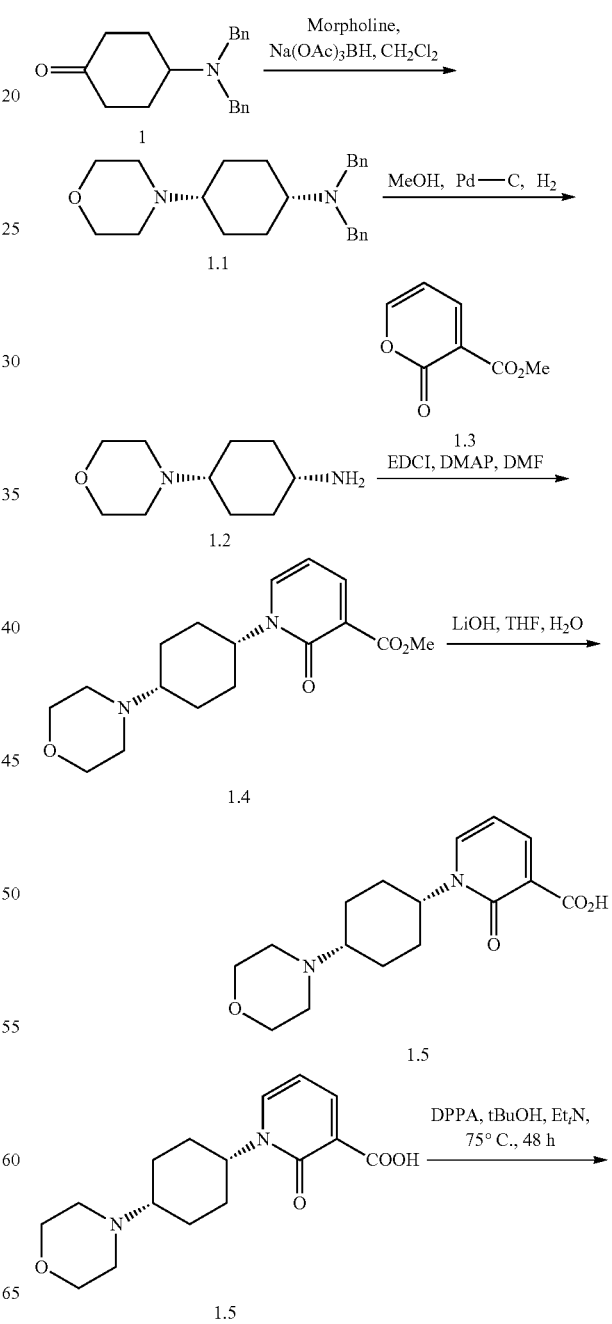

ice cold water and product was extracted with ethylacetate. Organic layer was combined, washed with brine solution, dried over sodium sulphate and concentrated under reduced pressure to obtain crude material. This was further purified by combi flash using 5% ethyl acetate in hexane as eluant to 1.4 (0.21 g, 48.06%). MS(ES): m/z 357.40 [M+H]⁺.

Synthesis of Compound 103ff.

To 1.4 (0.21 g, 0.58 mmol, 1.0 eq) added hydrochloric acid in 1,4-dioxane (2 mL). The reaction mixture was stirred at room temperature for 1 h. After completion of reaction, reaction mixture was concentrated under reduced pressure to obtain residue which was stirred with diethyl ether and filtered to obtain pure 103ff (0.11 g, 63.73%). MS (ES): m/z 294.74 [M+H]⁺.

Synthesis of Compound 1.2.

To a solution of 1 (1.40 g, 9.08 mmol, 1.0 eq) in dimethylformamide (10 mL) was added 1.1 (1.49 g, 9.08, 1.0 eq). The reaction mixture was stirred at room temperature for 1 h followed by addition of N-Ethyl-N'-(3-dimethylaminopropyl) carbodiimidehydrochloride (2.6 g, 13.62 mol, 1.5 eq) and 4-dimethylaminopryidine (0.27 g, 2.27 mmol, 0.25 eq). The reaction was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 30% ethylacetate in hexane as eluant to 1.2 (0.62 g, 22.73%). MS(ES): m/z 301.31 [M+H]⁺

Synthesis of Compound 1.3.

To a solution of 1.2 (0.62 g, 2.06 mmol, 1.0 eq), in tetrahydrofuran: methanol: water (5 mL, 1:1:1) was added lithium hydroxide (0.86 g, 20.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.3 (0.35 g, 59.22%). MS(ES): m/z: 287.28 [M+H]⁺.

Synthesis of Compound 1.4.

To a solution of 1.3 (0.35 g, 1.22 mmol, 1.0 eq) in tert-butanol (3 mL) was added diphenylphosphorylazide (0.53 g, 1.95 mmol, 1.6 eq), trimethylamine (2.5 mL). The reaction mixture was heated at 75° C. for 18 h. After completion of reaction, reaction mixture was transferred into

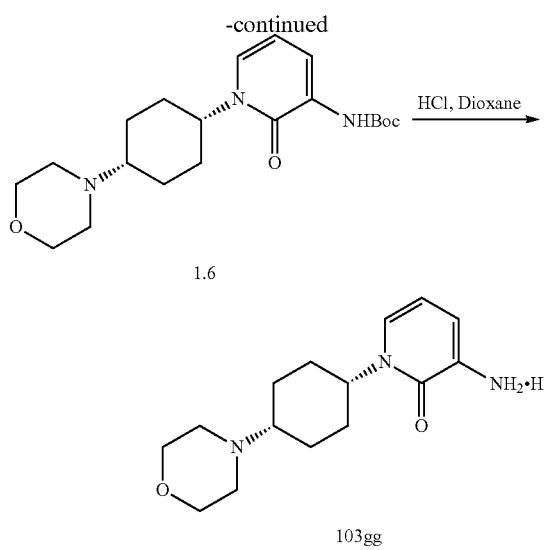

Synthesis of Compound 1.1.

To a solution of 1 (10 g, 34.08 mmol, 1.0 eq) in dichloromethane (250 mL) was added morpholine (4.4 g, 51.12 mmol, 1.5 eq) and Sodium triacetoxyhydroborate (10.8 g, 51.12 mmol, 1.5 eq). The reaction mixture was stirred at room temperature for 18 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 20% ethylacetate in hexane as eluant to 1.1 (6.5 g, 52.32%). MS(ES): m/z 365.53 [M+H]+

Synthesis of Compound 1.2.

To a solution of 1.1 (6.5 g, 17.83 mmol, 1.0 eq) in methanol (60 mL), palladium on charcoal (0.5 g) was added. Hydrogen was purged through reaction mixture for 24 h at room temperature. After completion of reaction, reaction mixture was filtered through celite-bed and washed with methanol. Filtrate was concentrated under reduced pressure to obtain 1.2 (2.7 g, 82.17%). MS(ES): m/z 185.28 [M+H]+

Synthesis of Compound 1.4.

To a solution of 1.2 (2.7 g, 14.65 mmol, 1.0 eq) in N,N-dimethylformamide (25 mL) was added 1.3 (2.2 g, 14.65 mmol, 1.0 eq). The reaction mixture was stirred at room temperature for 1 h followed by addition of N-Ethyl-N'-(3-dimethylaminopropyl) carbodiimidehydrochloride (3.6 g, 19.04 mol, 1.3 eq) and 4-dimethylaminopryidine (0.44 g, 3.66 mmol, 0.25 eq). The reaction was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 30% ethyl acetate in hexane as eluant to 1.4 (1.2 g, 25.56%). MS(ES): m/z 321.39 [M+H]+.

Synthesis of Compound 1.5.

To a solution of 1.4 (1.2 g, 3.75 mmol, 1.0 eq), in tetrahydrofuran: methanol: water (5 mL, 1:1:1) was added lithium hydroxide (1.5 g, 37.5 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 1.5 (0.81 g, 70.59%). MS(ES): m/z: 307.36 [M+H]+.

Synthesis of Compound 1.6.

To a solution of 1.5 (0.81 g, 2.64 mmol, 1.0 eq) in tert-butanol (10 mL) was added diphenylphosphorylazide (1.2 g, 4.48 mmol, 1.7 eq), trimethylamine (0.26 g, 2.64 mmol, 1.7 eq). The reaction mixture was heated at 75° C. for 48 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% ethyl acetate in hexane as eluant to 1.6 (0.41 g, 41.08%). MS(ES): m/z 378.49 [M+H]+.

Synthesis of Compound 103gg.

To a solution of 1.6 (0.41 g, 1.09 mmol, 1.0 eq) in dry dichloromethane (4 mL) was added 4M hydrochloric acid in dioxane (8 mL) at 0° C. The reaction mixture was stirred at room temperature for 16 h. After completion of reaction, reaction mixture was concentrated under reduced pressure to obtain crude material. This was further purified by trituration with diethylether to obtain 103 gg (0.14 g, 41.07%). MS(ES): m/z 314.83 [M+H]+.

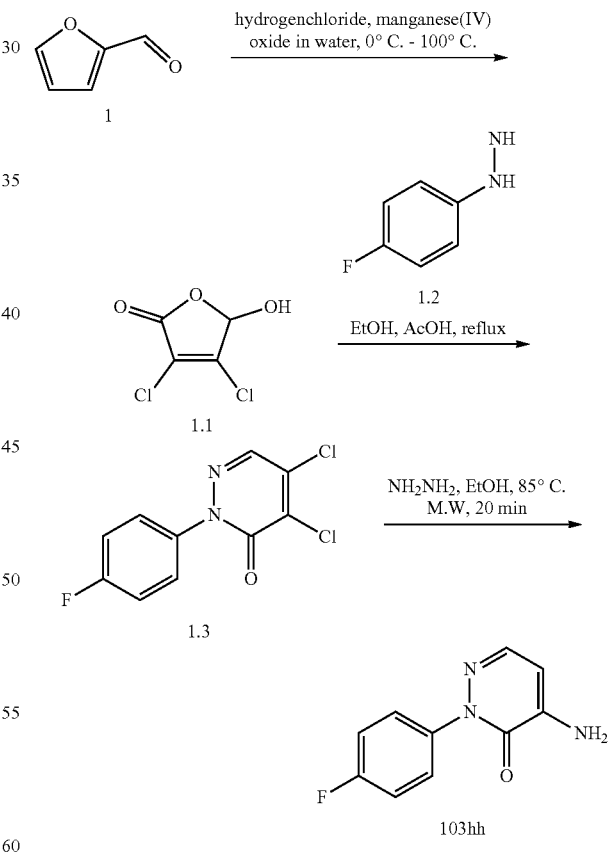

Synthesis of Compound 1.1.

To a cooled solution of manganese dioxide (3.2 g, 374.65 mmol, 3.6 eq) in Hydrochloric acid (200 mL) at 0° C. was added 1 (10 g, 104.07 mmol, 1.0 eq). The reaction mixture was stirred at 60° C. for 30 min. Again manganese dioxide (1.8 g, 208.14 mmol, 2.0 eq) was added. The reaction mixture was heated at 100° C. After completion of reaction, reaction mixture was cooled to room temperature, and residue was dissolved in ether and concentrated under reduced pressure to obtain 1.1 (5 g, 28.43%). MS(ES): m/z 169.96 [M+H]⁺.

Synthesis of Compound 1.3.

To a solution of 1.1 (5 g, 29.59 mmol, 1.0 eq) and 1.2 (3.7 g, 29.59 mmol, 1.0 eq) in ethanol (80 mL) was added acetic acid (8 mL). The reaction mixture was stirred at 100° C. for 5 h. After completion of reaction, reaction mixture was concentrated under reduced pressure to obtain residue. To this added water and solid filtered out, dried well to obtain 1.3 (2.6 g, 33.91%). MS(ES): m/z 260.06 [M+H]⁺.

Synthesis of Compound 103hh.

To a solution of 1.3 (2.6 g, 10.04 mmol, 1.0 eq) in ethanol (10 mL), hydrazine hydrate (1.9 g, 100.4 mmol, 10 eq) was added. The reaction mixture was stirred at 85° C. for 20 min in microwave. After completion of reaction, reaction mixture was concentrated under reduced pressure to obtain crude material. This was further purified by combi flash using 5% methanol in dichloromethane as eluant to obtain pure 103hh (0.50 g, 24.28%). MS(ES): m/z 206.19 [M+H]⁺.

extracted with ethyl acetate. Organic layer was combined and dried over sodium sulphate and concentrated under reduced pressure to obtain crude material. This was further purified by column chromatography and compound was eluted in 13% ethyl acetate in hexane to obtain pure 1.2 (0.350 g, 27.61%), MS(ES): m/z 245.63 [M+H]⁺.

Synthesis of Compound 103ii.

To a solution of 1.2 (0.350 g, 1.43 mmol, 1.0 eq) in acetic acid (20 ml), palladium on charcoal (0.160 g) was added. Hydrogen was purged through reaction mixture for 16 h at room temperature. After completion of reaction, reaction mixture was filtered through celite-bed and washed with methanol. Filtrate was concentrated under reduced pressure to obtain crude material. This was further purified by column chromatography and compound was eluted in 17% ethyl acetate in hexane to obtain pure 103ii (0.165 g, 53.73%). MS (ES): m/z 215.05 [M+H]⁺.

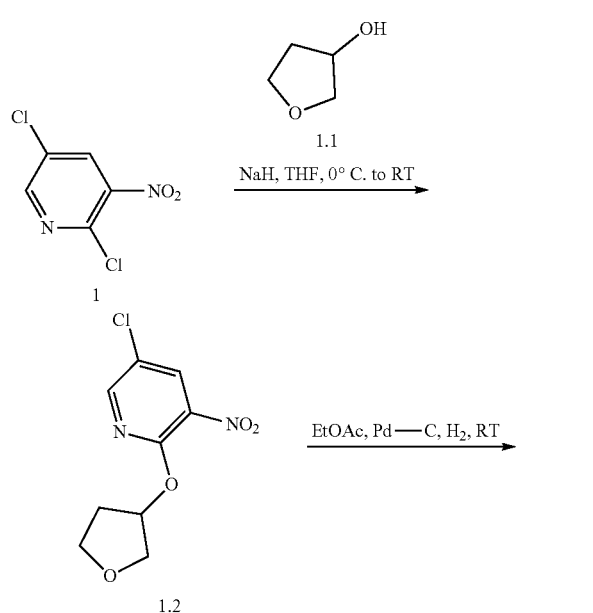

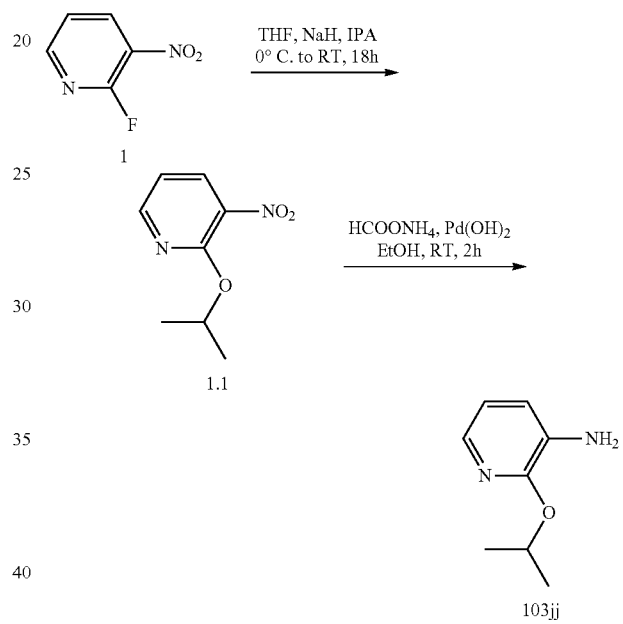

Synthesis of Compound 1.2.

To a cooled solution of 1 (1 g, 5.18 mmol, 1.0 eq) in tetrahydrofuran (20 mL) was added sodium hydride (0.311 g, 7.77 mmol, 1.5 eq) followed by addition of 1.1 (0.502 g, 5.70 mmol, 1.1 eq) under nitrogen. The reaction was stirred at 0° C. for 1 h. After completion of reaction, reaction mixture was transferred into ice cold water and product was Synthesis of Compound 1.1.

To a cooled suspension of sodium hydride (0.35 g, 14.78 mmol, 1.05 eq) in tetrahydrofuran (20 mL), isopropanol (2.1 g, 14.78 mmol, 1.05 eq) was added at 0° C. The reaction mixture was stirred at 0° C. for 30 min. followed by addition of 1 (2 g, 14.08 mmol, 1.0 eq). Again reaction mixture was stirred at 0° C. for 30 min and at room temperature for 18 h. After completion of reaction, reaction mixture was cooled to room temperature, transferred into ice-water and product was extracted with ethyl acetate. Organic layer was combined, washed with brine solution, dried over sodium sulphate and concentrated under reduced pressure to obtain crude material. This was further purified by combi flash using 70% ethylacetate in hexane as eluant to obtain pure 1.1 (1.3 g, 50.70%). MS(ES): m/z 182.18 [M+H]⁺.

Synthesis of Compound 103jj.

To a solution of 1.1 (1.3 g, 7.14 mmol, 1.0 eq) in ethanol (60 mL) was added ammonia formate (2.2 g, 35.7 mmol, 5.0 eq) and palladium hydroxide (0.20 g). The reaction mixture was stirred at 90° C. for 2 h. After completion of reaction, reaction mixture was filtered through celite-bed and washed with methanol. Filtrate was concentrated under reduced pressure to obtain 103jj (1.05 g, 96.68%). MS(ES): m/z 153.20 [M+H]⁺

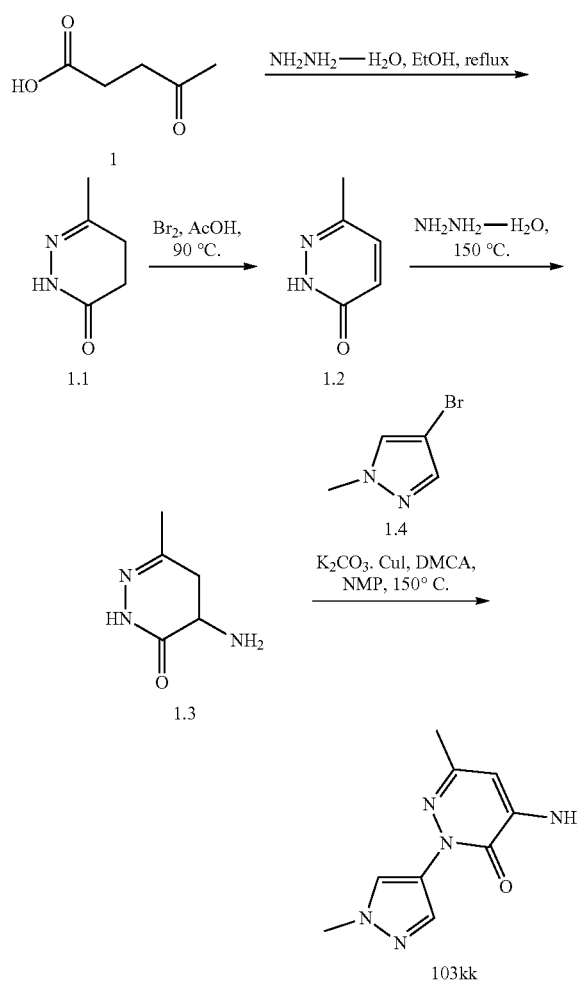

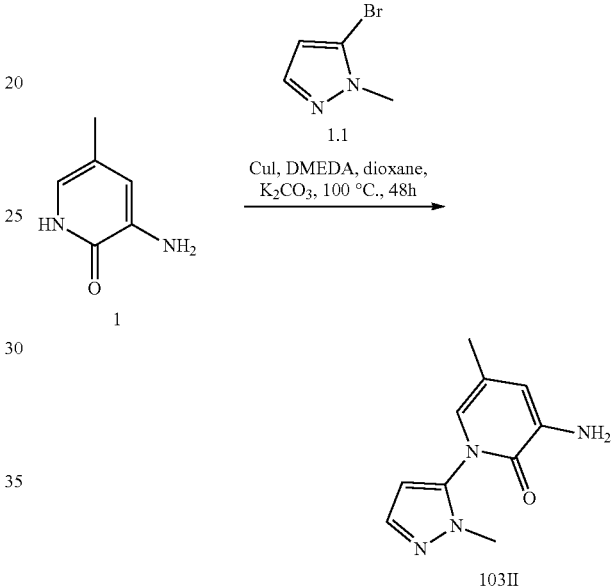

Synthesis of Compound 103kk.

To a solution of 1.3 (0.60 g, 4.79 mmol, 1.0 eq) in N-methyl-2-pyrolidone (20 mL) was added 1.4 (0.92 g, 5.74 mmol, 1.2 eq), dimethyl acetamide (0.34 g, 2.39 mmol, 0.5 eq), copper iodide (0.91 g, 4.79 mmol, 1.0 eq) and potassium carbonate (1.3 g, 9.58 mmol, 2.0 eq). The reaction mixture was heated at 150° C. for 2 h. After completion of reaction, reaction mixture was transferred into ice cold water and Product was extracted with ethylacetate. Organic layer was combined, washed with brine solution, dried over sodium sulphate and concentrated under reduced pressure to obtain crude material. This was further purified by column chromatography by using 2% methanol in dichloromethane as eluant to 103kk (0.50 g, 50.81%). MS(ES): m/z 206.22 [M+H]+

Synthesis of Compound 1.1.

To a solution of 1 (5 g, 0.43 mmol, 1.0 eq) in ethanol (30 mL), Hydrazine hydrate (25.8 g, 0.51 mmol, 1.2 eq) was added. The reaction mixture was refluxed for 3 h. After completion of reaction, reaction mixture was concentrated under reduced pressure to obtain 1.1 (4.5 g, 93.20%). MS(ES): m/z 113.13 [M+H]+

Synthesis of Compound 1.2.

To a solution of 1.1 (4.5 g, 40.13 mmol, 1.0 eq) in acetic acid (40 mL), bromine (4.8 g, 60.19 mmol, 1.5 eq) was added dropwise at 0° C. The reaction mixture was heated at 90° C. for 16 h. After completion of reaction, reaction mixture was concentrated under reduced pressure, transferred into saturated bicarbonate solution, filtered and washed with water. Filtrate was concentrated under reduced pressure to obtain 1.2 (2.5 g, 56.57%). MS(ES): m/z 111.12 [M+H]+.

Synthesis of Compound 1.3.

To a solution of 1.2 (2.5 g, 22.70 mmol, 1.0 eq) in Hydrazine hydrate (2.6 g, 52.21 mmol, 2.3 eq) was added. The reaction mixture was heated at 150° C. for 16 h. After completion of reaction, reaction mixture was concentrated under reduced pressure to obtain crude material. This was further purified by column chromatography using 5% methanol in dichloromethane as eluant to 1.3 (0.60 g, 21.12%). MS(ES): m/z 125.13 [M+H]+.

Synthesis of Compound 103ll.

To a solution of 1. (2 g, 16.11 mmol, 1.0 eq) in 1,4-dioxane (10 mL), 1.1 (3.1 g, 19.33 mmol, 1.2 eq) was added. The reaction mixture was degassed for 10 min under argon atmosphere followed by addition of potassium carbonate (4.4 g, 32.22 mmol, 2.0 eq), N,N-dimethylethylenediamine (0.42 g, 4.83 mmol, 0.3 eq), and copper iodide (0.45 g, 2.41 mmol, 0.15 eq). The reaction mixture was heated at 100° C. for 48 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 103ll (Yield: 3.95%). MS (ES): m/z 205.23 [M+H]+

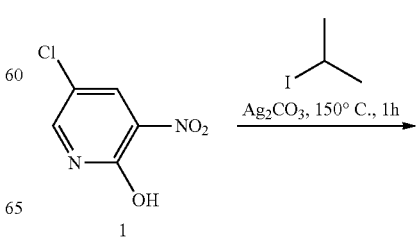

1631

-continued

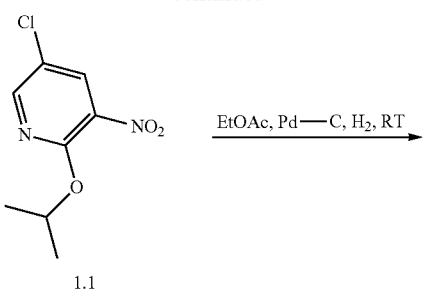

1.1

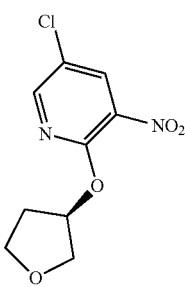 [SMILES: Nc1cc(Cl)cnc1O[C@@H]1CCOC1]

1.2

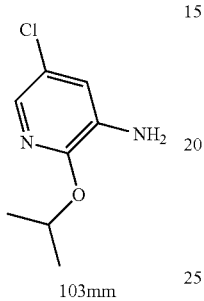

103mm

1632

-continued

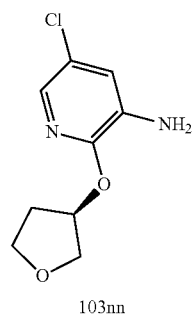

103nn

Synthesis of Compound 1.1.

To 1. (1.5 g, 8.59 mmol, 1.0 eq), silver carbonate (2.8 g, 10.30 mmol, 1.2 eq) and 2-iodopropane (1.7 mL, 17.78 mmol, 2.0 eq) was added dropwise. The reaction mixture was stirred at 150° C. for 1 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 2% ethyl acetate in hexane to obtain pure 1.1 (1.1 g, 59.09%). MS(ES): m/z 217.62 [M+H]⁺

Synthesis of Compound 103 mm.

To a solution of 1.1 (1.1 g, 5.08 mmol, 1.0 eq) in ethyl acetate (10 mL), palladium on charcoal (0.10 g) was added. Hydrogen was purged through reaction mixture for 24 h at room temperature. After completion of reaction, reaction mixture was filtered through celite-bed and washed with methanol. Filtrate was concentrated under reduced pressure to obtain 103 mm (0.70 g, 73.86%). MS(ES): m/z 187.64 [M+H]⁺.

Synthesis of Compound 1.2.

To a suspension of sodium hydride (0.55 g, 23.32 mmol, 1.5 eq) in tetrahydrofuran (20 mL) at 0° C. was added 1.1 (1.5 g, 17.10 mmol, 1.1 eq). The reaction mixture was stirred at 0° C. for 30 min followed by addition of 1 (3 g, 15.55 mmol, 1.0 eq) at same temperature. Again reaction mixture was stirred at 0° C. for 30 min and at room temperature for 12 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 20% ethyl acetate in hexane as eluant to obtain pure 1.2 (0.75 g, 19.72%). MS(ES): m/z 245.66 [M+H]⁺.

Synthesis of Compound 103nn.

To a solution of 1.2 (0.75 g, 3.07 mmol, 1.0 eq) in ethyl acetate (10 mL), palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 103nn (0.50 g, 75.98%). MS(ES): m/z 215.65 [M+H]⁺.

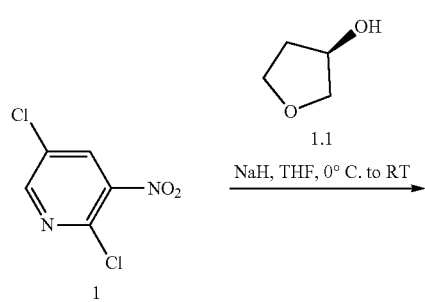

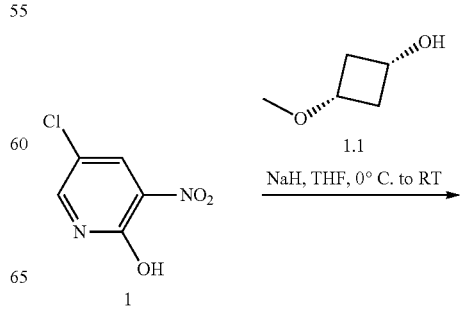

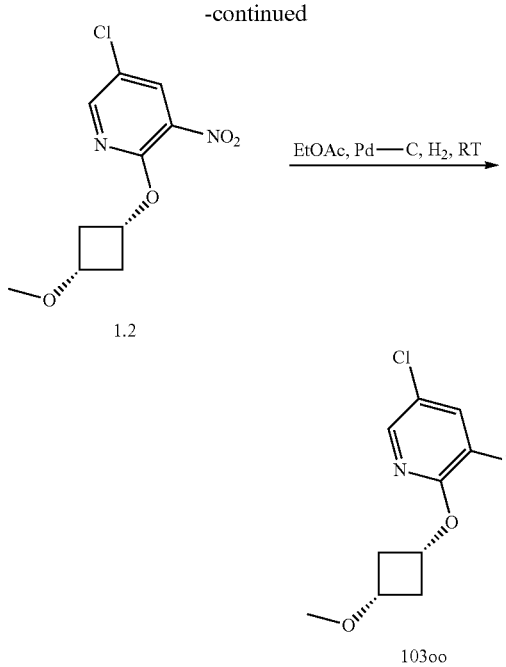

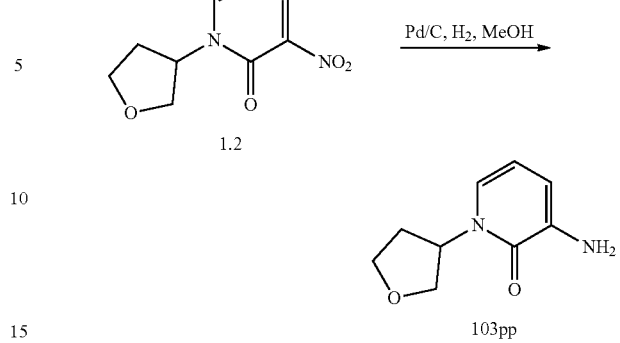

Synthesis of Compound 1.1.

Compound was synthesized as per experimental protocol of 103qq. to obtain 1.1.

Synthesis of Compound 1.2.

To a cooled solution of 1.1 (0.407 g, 3.99 mmol, 1.1 eq) in tetrahydrofuran (7 mL) was added sodium hydride (0.159 g, 3.99 mmol, 1.1 eq) followed by addition of 1 (0.700 g, 3.63 mmol, 1 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 6% ethyl acetate in hexane to obtain pure 1.2 (0.550 g, 58.62%), MS(ES): m/z 259.66 [M+H]$^+$.

Synthesis of Compound 103oo.

To a solution of 1.2 (0.550 g, 2.13 mmol, 1.0 eq) in ethyl acetate (6 ml), palladium on charcoal (0.200 g) was added. Hydrogen was purged through reaction mixture for 2-3 h at room temperature. After completion of reaction, reaction mixture was filtered through celite-bed and washed with methanol. Filtrate was concentrated under reduced pressure to obtain 103oo (0.432 g, 88.84%). MS (ES): m/z 229.68 [M+H]$^+$.

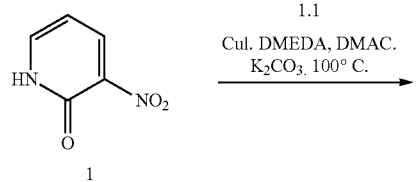

Synthesis of Compound 1.2.

To a solution of 1 (1 g, 7.14 mmol, 1.0 eq) and 1.1 (1.29 g, 8.57 mmol, 1.2 eq) in 1,4-dioxane (10 mL) was added potassium carbonate (1.97 g, 14.28 mmol, 2.0 eq) and degassed with argon for 15 min. Copper iodide (0.269 g, 1.42 mmol, 0.2 eq) and 1,2-dimethylethylenediamine (0.251 g, 2.85 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 0.4% methanol in dichloromethane to obtain pure 1.2 (0.650 g, 43.32%). MS(ES): m/z 211.19 [M+H]$^+$.

Synthesis of Compound 103pp.

To a solution of 1.2 (0.650 g, 3.09 mmol, 1.0 eq) in methanol (7 ml), palladium on charcoal (0.100 g) was added. Hydrogen was purged through reaction mixture for 2-3 h at room temperature. After completion of reaction, reaction mixture was filtered through celite-bed and washed with methanol. Filtrate was concentrated under reduced pressure to obtain 103pp (0.407 g, 73.03%). MS (ES): m/z 181.21 [M+H]$^+$.

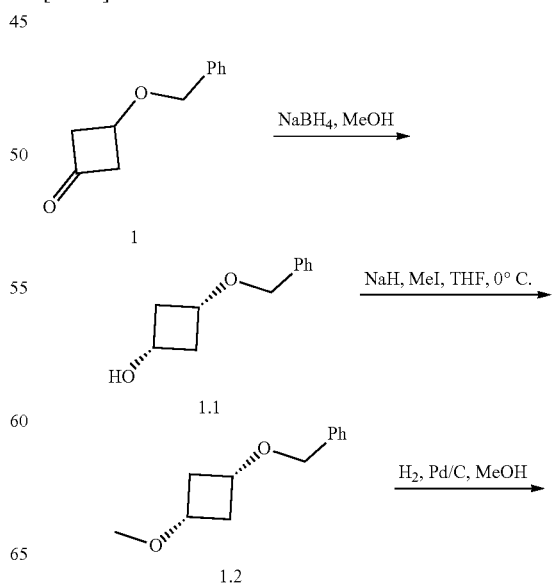

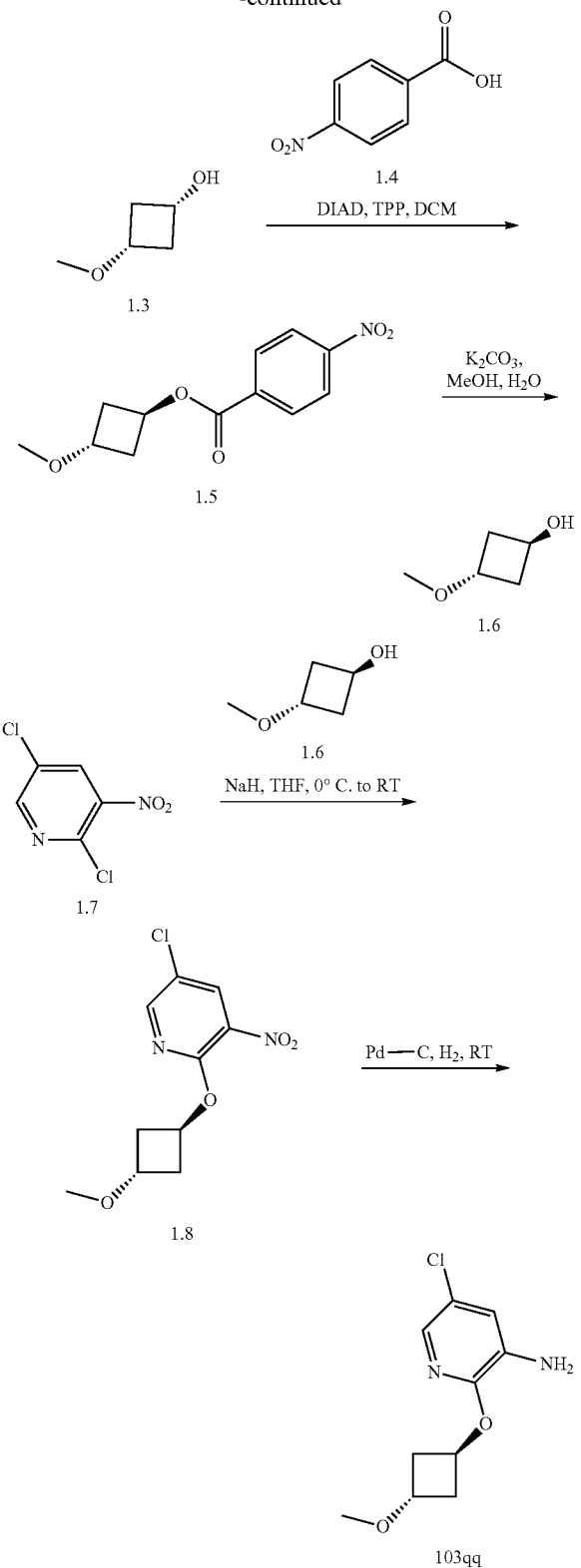

Synthesis of Compound 1.1.

To a cooled solution of 1 (5.0 g, 28.3 mmol, 1.0 eq) in methanol (50 mL) at 0° C. was added sodium borohydride (1.6 mL, 42.5 mmol, 1.5 eq). The reaction was stirred at room temperature for 1 h. After completion of reaction, reaction mixture was transferred into ice cooled water and product was extracted with ethyl acetate. Organic layer was combined and dried over sodium sulphate and concentrated under reduced pressure to obtain pure 1.2. (3.5 g, 69.21%). MS (ES): m/z 179.23 [M+H]$^+$ Synthesis of Compound 1.2.

To a cooled solution of 1.1 (3.5 g, 19.64 mmol, 1.0 eq) in tetrahydrofuran (35 mL) was added sodium hydride (1.18 g, 29.46 mmol, 1.5 eq) followed by methyl iodide (1.84 mL, 29.46 mmol, 1.5 eq). The reaction was stirred at room temperature for 2 h. After completion of reaction, reaction mixture was transferred into ice cooled water and product was extracted with ethyl acetate. Organic layer was combined and dried over sodium sulphate and concentrated under reduced pressure to obtain crude 1.2 (3.1 g, 82.11%), MS(ES): m/z 193.26 [M+H]$^+$.

Synthesis of Compound 1.3.

To a solution of 1.2 (3.1 g, 16.12 mmol, 1.0 eq) in methanol (30 ml), palladium on charcoal (1.5 g) was added. Hydrogen was purged through reaction mixture for 2-3 h at room temperature. After completion of reaction, reaction mixture was filtered through celite-bed and washed with methanol. Filtrate was concentrated under reduced pressure to obtain 1.3 (1.6 g, 97.16%). MS (ES): m/z 103.13 [M+H]$^+$ Synthesis of Compound 1.5.

To a solution of 1.3 (0.700 g, 6.85 mmol, 1 eq) in dichloromethane (16 mL) was added 1.4 (1.15 g, 6.85 mmol, 1 eq) and triphenylphosphine (2.15 g, 8.22 mmol, 1.2 eq). Diisopropyl azodicarboxylate (1.66 g, 8.22 mmol, 0.15 eq) was added dropwise at 0° C. The reaction was stirred at room temperature for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 15% ethyl acetate in hexane to obtain pure 1.5 (0.480 g, 27.88%). MS(ES): m/z 252.24 [M+H]$^+$.

Synthesis of Compound 1.6.

To a solution of 1.5 (0.480 g, 1.91 mmol, 1 eq) in methanol (5 mL) was added potassium carbonate (0.527 g, 3.82 mmol, 2 eq) and water (1 mL). The reaction was stirred at room temperature for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain 1.6 (0.190 g, 97.37%). MS(ES): m/z 103.13 [M+H]$^+$.

Synthesis of Compound 1.8.

To a cooled solution of 1.6 (0.166 g, 1.63 mmol, 1.05 eq) in tetrahydrofuran (3 mL) was added sodium hydride (0.042 g, 1.63 mmol, 1.05 eq) followed by 1.7 (0.300 g, 1.55 mmol, 1 eq). The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 6% ethyl acetate in hexane to obtain pure 1.8 (0.180 g, 44.77%), MS(ES): m/z 259.66 [M+H]$^+$.

Synthesis of Compound 103qq.

To a solution of 1.8 (0.180 g, 0.695 mmol, 1.0 eq) in methanol (3 ml), palladium on charcoal (0.150 g) was added. Hydrogen was purged through reaction mixture for 2-3 h at room temperature. After completion of reaction, reaction mixture was filtered through celite-bed and washed with methanol. Filtrate was concentrated under reduced pressure to obtain 103qq (0.100 g, 62.84%). MS (ES): m/z 229.68 [M+H]+.

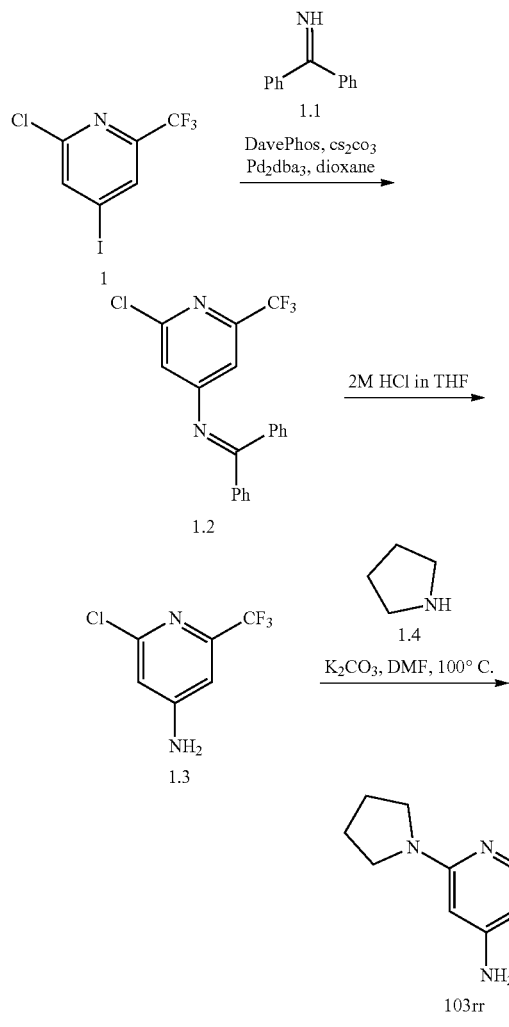

Synthesis of Compound 1.2.

To a solution of 1 (5 g, 16.26 mmol, 1.0 eq) in 1,4-dioxane (50 mL) was added 1.1 (3.29 g, 17.89 mmol, 1.1 eq), cesium carbonate (13.21 g, 40.65 mmol, 2.5 eq). The reaction mixture was degassed for 10 min. under argon atmosphere, then tris(dibenzylideneacetone)dipalladium(0) (0.744 g, 0.813 mmol, 0.05 eq) and 2-Dicyclohexylphosphino-2'-(N,N-dimethylamino)biphenyl (0.480 g, 1.22 mmol, 0.075 eq) were added, again degassed for 5 min. The reaction was stirred at 100° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 6% ethyl acetate in hexane as eluant to obtain pure 1.2 (2.8 g, 47.72%). MS(ES): m/z 361.76. [M+H]+.

Synthesis of Compound 1.3.

To a cooled solution of 1.2 (2.8 g, 7.76 mmol, 1 eq) in tetrahydrofuran (28 mL) was added 2M hydrochloric acid (2.8 mL) drop wise. The reaction was stirred at room temperature for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 14% ethyl acetate in hexane to obtain pure 1.3 (1.4 g, 91.77%). MS(ES): m/z 197.56 [M+H]+.

Synthesis of Compound 103rr.

To a solution of 1.3 (1.4 g, 7.12 mmol, 1 eq) and 1.4 (0.760 g, 13.47 mmol, 1.5 eq) in dimethylformamide (14 mL) was added potassium carbonate (2.45 g, 17.8 mmol, 2.5 eq). The reaction was stirred at room temperature for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 12% ethyl acetate in hexane to obtain pure 103rr (0.720 g, 43.72%). MS(ES): m/z 232.22 [M+H]+.

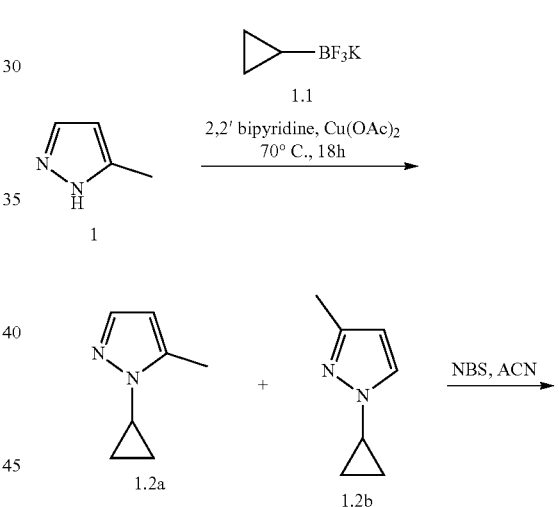

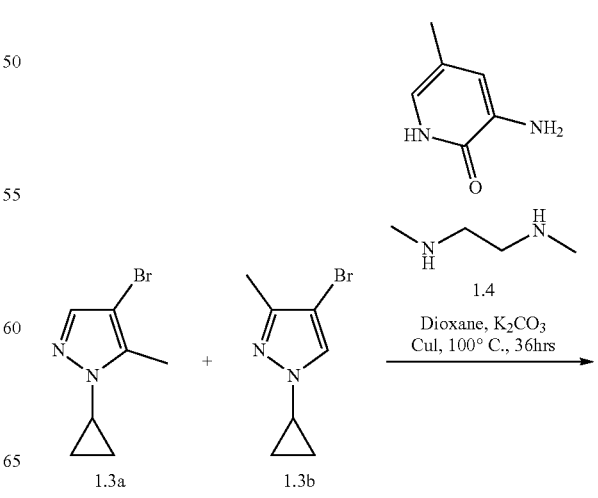

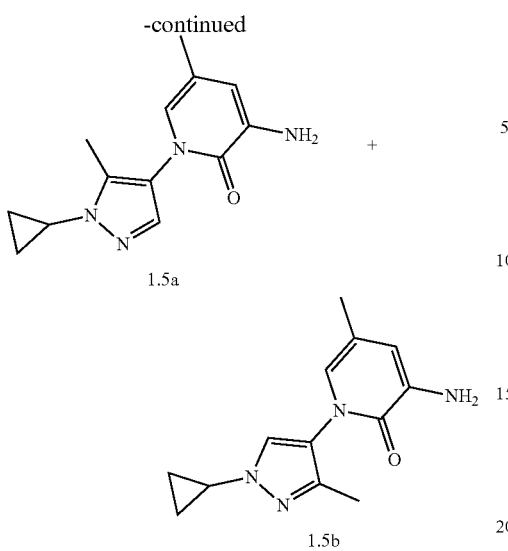

1.5a 1.5b

Synthesis of Compound 1.2a and 1.2b.

To a solution of 1 (15 g, 182.69 mmol, 1 eq) and 1.1 (54.07 g, 365.38 mmol, 2 eq) in 1,2-dichloroethane (150 mL) was added sodium carbonate (50.422 g, 365.38 mmol, 2 eq), copper acetate (33.25 g, 182.69 mmol, 1 eq) and 2,2-bipyridine (28.499 g, 182.69 mmol, 1 eq). Reaction mixture was degassed with oxygen followed by heating at 70° C. for 18 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 12% ethyl acetate in hexane to obtain (1.2a+1.2b) (9.2 g, 41.22%). MS(ES): m/z 123.17 [M+H]$^+$.

Synthesis of Compound 1.3a and 1.3b.

To a cooled solution of (1.2a+1.2b) (9.2 g, 75.30 mmol, 1.0 eq), in acetonitrile (92 mL) was added N-Bromosuccinimide (14.717 g, 82.83 mmol, 1.1 eq). The reaction was stirred at 0° C. for 30 min After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 10% ethyl acetate in hexane to obtain 1.3a+1.3b (6 g, 39.63%). MS(ES): m/z 202.07 [M+H]$^+$.

Synthesis of Compound 103ss and 103tt.

To a solution of (1.3a+1.3b) (2 g, 9.95 mmol, 1.0 eq) and 1.4 (2.47 g, 19.89 mmol, 2 eq) in 1,4-dioxane (20 mL) was added potassium carbonate (2.74 g, 19.89 mmol, 2.0 eq) and degassed with argon for 15 min. Copper iodide (0.566 g, 2.98 mmol, 0.3 eq) and 1,2-dimethylethylenediamine (0.263 g, 2.98 mmol, 0.3 eq) was added and reaction mixture again degassed with argon for 5 min followed by heating at 100° C. for 36 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 103ss (0.155 g, 6.38%). MS(ES): m/z 245.30 [M+H]$^+$ and 103tt (0.163 g, 6.71%). MS(ES): m/z 245.30 [M+H]$^+$.

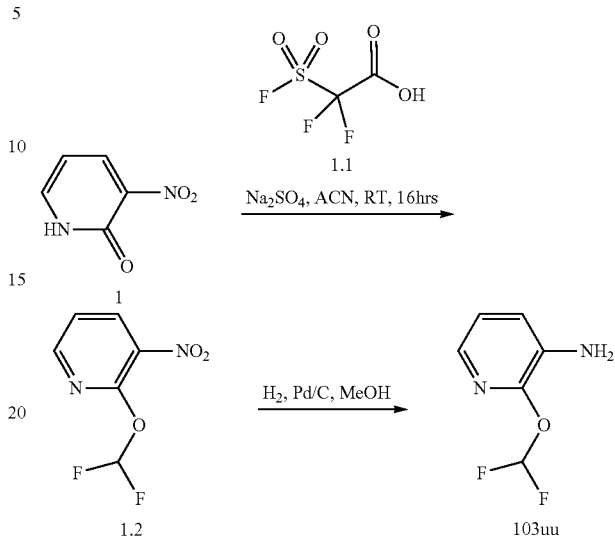

Synthesis of Compound 1.2.

To a solution of 1 (2 g, 14.28 mmol, 1.0 eq) in Acetonitrile (20 mL), 2,2-difluoro-2-(fluorosulfonyl)acetic acid (3.0 g, 17.13 mmol, 1.2 eq) was added at 0° C. The reaction mixture was stirred at room temperature for 16 h. After completion of reaction, reaction mixture transferred into water and product was extracted with ethyl acetate. Organic layer was combined, washed with brine solution, dried over sodium sulphate and concentrated under reduced pressure to obtain crude material. This was further purified by combi flash using 20% ethyl acetate in hexane as eluant to obtain pure 1.2 (0.80 g, 29.48%). MS(ES): m/z 191.11 [M+H]$^+$ Synthesis of Compound 103uu.

To a solution of 1.2 (0.80 g, 4.21 mmol, 1.0 eq) in methanol (5 mL) palladium on charcoal (0.10 g) was added. Hydrogen was purged through reaction mixture for 2 h at room temperature. After completion of reaction, reaction mixture was filtered through celite-bed and washed with methanol. Filtrate was concentrated under reduced pressure to obtain 103uu (0.60 g, 89.04%). MS(ES): m/z 161.12 [M+H]$^+$.

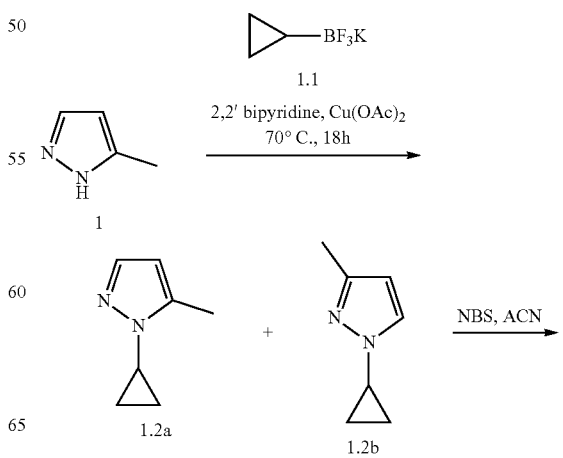

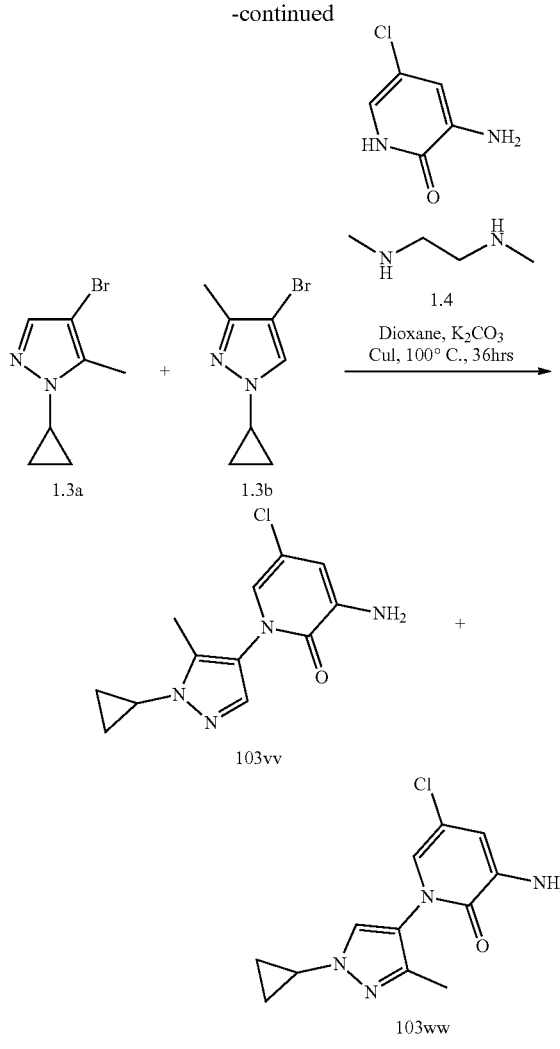

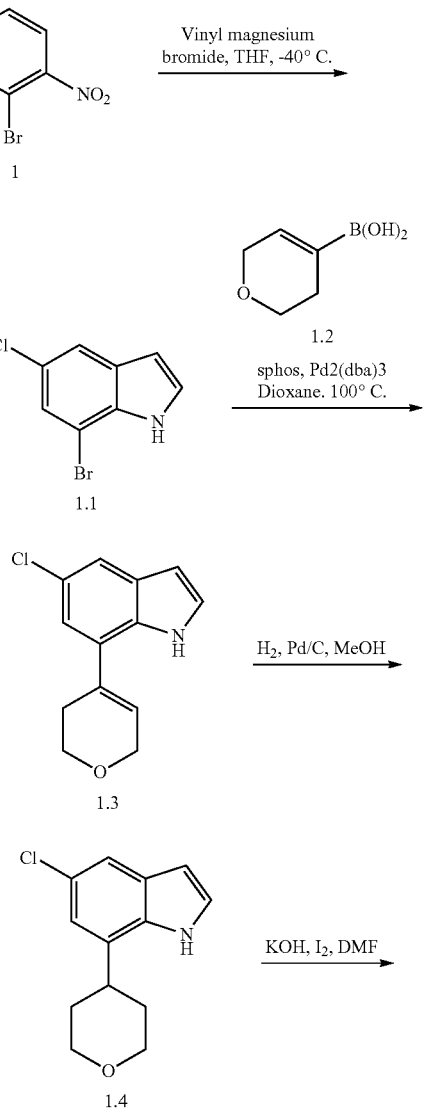

purified by column chromatography and compound was eluted in 10% ethyl acetate in hexane to obtain 1.3a+1.3b (6 g, 39.63%). MS(ES): m/z 202.07 [M+H]⁺.

Synthesis of Compound 103vv and 103ww.

To a solution of (1.3a+1.3b) (3 g, 14.92 mmol, 1.0 eq) and 1.4 (2.63 g, 29.84 mmol, 2 eq) in 1,4-dioxane (20 mL) was added potassium carbonate (4.12 g, 29.84 mmol, 2.0 eq) and degassed with argon for 15 min. Copper iodide (0.850 g, 4.47 mmol, 0.3 eq) and 1,2-dimethylethylenediamine (0.393 g, 4.47 mmol, 0.3 eq) was added and reaction mixture again degassed with argon for 5 min followed by heating at 100° C. for 36 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1% methanol in dichloromethane to obtain pure 103vv (0.200 g, 6.38%). MS(ES): m/z 265.71 [M+H]⁺ and 103ww (0.120 g, 3.04%). MS(ES): m/z 265.71 [M+H]⁺.

Synthesis of Compound 1.2a and 1.2b.

To a solution of 1 (15 g, 182.69 mmol, 1 eq) and 1.1 (54.07 g, 365.38 mmol, 2 eq) in 1,2-dichloroethane (150 mL) was added sodium carbonate (50.422 g, 365.38 mmol, 2 eq), copper acetate (33.25 g, 182.69 mmol, 1 eq) and 2,2-bipyridine (28.499 g, 182.69 mmol, 1 eq). Reaction mixture was degassed with oxygen followed by heating at 70° C. for 18 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 12% ethyl acetate in hexane to obtain (1.2a+1.2b) (9.2 g, 41.22%). MS(ES): m/z 123.17 [M+H]⁺.

Synthesis of Compound 1.3a and 1.3b.

To a cooled solution of (1.2a+1.2b) (9.2 g, 75.30 mmol, 1.0 eq), in acetonitrile (92 mL) was added N-Bromosuccinimide (14.717 g, 82.83 mmol, 1.1 eq). The reaction was stirred at 0° C. for 30 min After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further -continued

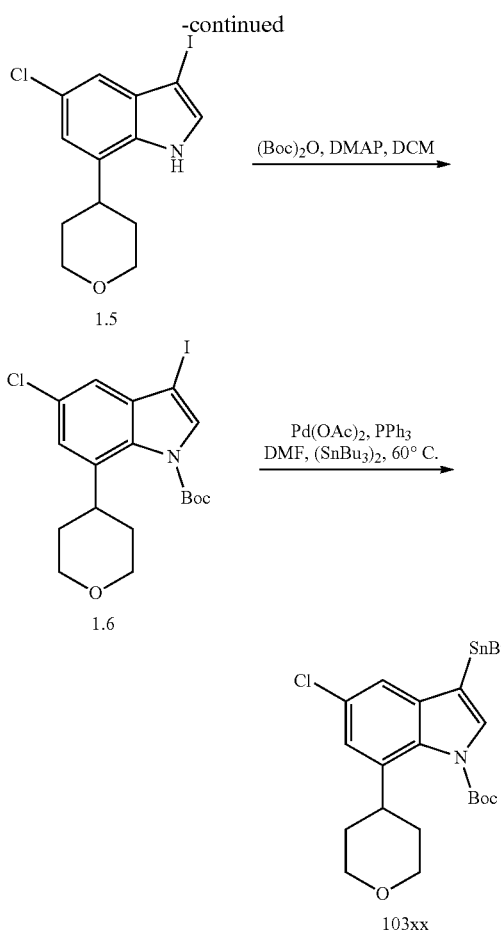

Synthesis of Compound 1.1.

To solution of 1 (10 g, 42.49 mmol, 1.0 eq) in tetrahydrofuran (100 mL) was added vinyl magnesium bromide (16.69 g, 127.47 mmol, 3.0 eq) dropwise at −40° C. under nitrogen. The reaction mixture was stirred at −40° C. for 1 h. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 6% ethyl acetate in hexane to obtain pure 1.1 (2.5 g, 25.65%). MS (ES): m/z 231.49 [M+H]$^+$ Synthesis of Compound 1.3.

To a solution of 1.1 (2.5 g, 10.85 mmol, 1.0 eq) in 1,4-dioxane (30 mL) was added 1.2 (1.46 g, 11.39 mmol, 1.05 eq) and cesium carbonate (7.05 g, 21.7 mmol, 2 eq). The reaction mixture was degassed for 10 min. under argon atmosphere, then 2-dicyclohexylphosphino-2',6'-dimethoxybiphenyl (0.178 g, 0.434 mmol, 0.04 eq) and tris(dibenzylideneacetone)dipalladium(0) (0.397 g, 0.434 mmol, 0.04 eq) added, again degassed for 5 min. The reaction mixture was stirred at 100° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 11% ethyl acetate in hexane to obtain pure 1.3 (1.6 g, 63.12%). MS(ES): m/z 234.70 [M+H]$^+$.

Synthesis of Compound 1.4.

To a solution of 1.3. (1.6 g, 6.86 mmol, 1.0 eq) in methanol (20 ml) and tetrahydrofuran (3 mL), palladium on charcoal (0.250 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by combi flash using as eluant in 20% ethyl acetate in hexane to obtain pure 1.4 (1.2 g, 74.36%). MS (ES): m/z 236.71 [M+H]$^+$.

Synthesis of Compound 1.5.

To a solution of 1.4 (1.2 g, 5.09 mmol, 1.0 eq) in dimethylformamide (7 mL) was added potassium hydroxide (1.08 g, 20.36 mmol, 4 eq) and solution of iodine (1.29 g, 5.09 mmol, 1 eq) in dimethylformamide (5 mL). The reaction was stirred at room temperature for 1 h. After completion of reaction, reaction mixture transferred into ice cold water, solid was generated, filtrated, dried under reduced pressure to obtain pure 1.5 (1.1 g, 59.75%). MS(ES): m/z 362.61 [M+H]$^+$.

Synthesis of Compound 1.6.

To a solution of 1.5 (1.1 g, 3.04 mmol, 1.0 eq) in dichloromethane (15 mL), was added 4-Dimethylaminopyridine (0.037 g, 0.303 mmol, 0.1 eq) and Di-tert-butyl dicarbonate (0.80 g, 3.65 mmol, 1.2 eq) at same temperature. The reaction was stirred at room temperature for 5 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using as eluant in 6% ethyl acetate in hexane to obtain pure 1.6 (1 g, 71.20%). MS(ES): m/z 462.72 [M+H]$^+$.

Synthesis of Compound 103xx.

To a solution of 1.6 (0.600 g, 1.30 mmol, 1.0 eq) in dimethylformamide (15 mL), was added tributyltin hydride (0.580 g, 1.36 mmol, 1.05 eq), palladium acetate (0.015 g, 0.065 mmol, 0.05 eq) and triphenylphosphine (0.003 g, 0.01 mmol, 0.008 eq). The reaction mixture was degassed for 10 min. under argon atmosphere, then reaction was stirred at 60° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude 103xx (0.860 g). MS(ES): m/z 626.23 [M+H]$^+$.[crude was directly use for next step].

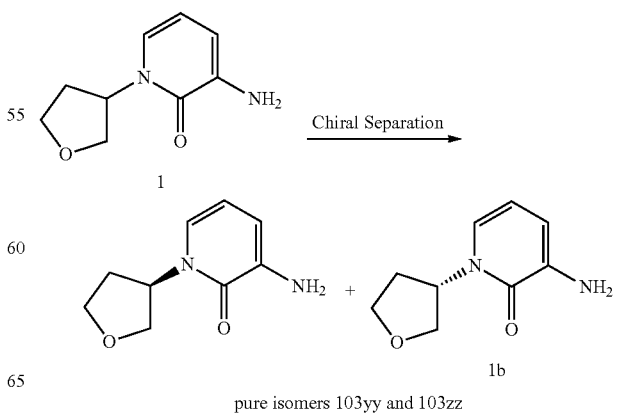

pure isomers 103yy and 103zz

Synthesis of Compound 1.

Compound was synthesized as per experimental protocol of 103pp. to obtain 1.

Synthesis of Compound 103yy and 103zz.

Isomers of 1 (0.407 g) were separated out using column (CHIRAL PAK IG 250×4.6 mm, 5 μM) and 0.1% Diethylamine in methanol as co-solvent with flow rate of 4 mL/min. to get pure fraction-1 and fraction-2 (FR-b). FR-a was evaporated under reduced pressure at 30° C. to afford pure FR-a. (0.121 g). MS(ES): m/z 181.09 [M+H]$^+$, LCMS purity: 99%, CHIRAL HPLC purity: 97%. FR-b was evaporated under reduced pressure at 30° C. to afford pure FR-b. (0.112 g). MS(ES): m/z 181.09 [M+H]$^+$, LCMS purity: 98%, CHIRAL HPLC purity: 96%.

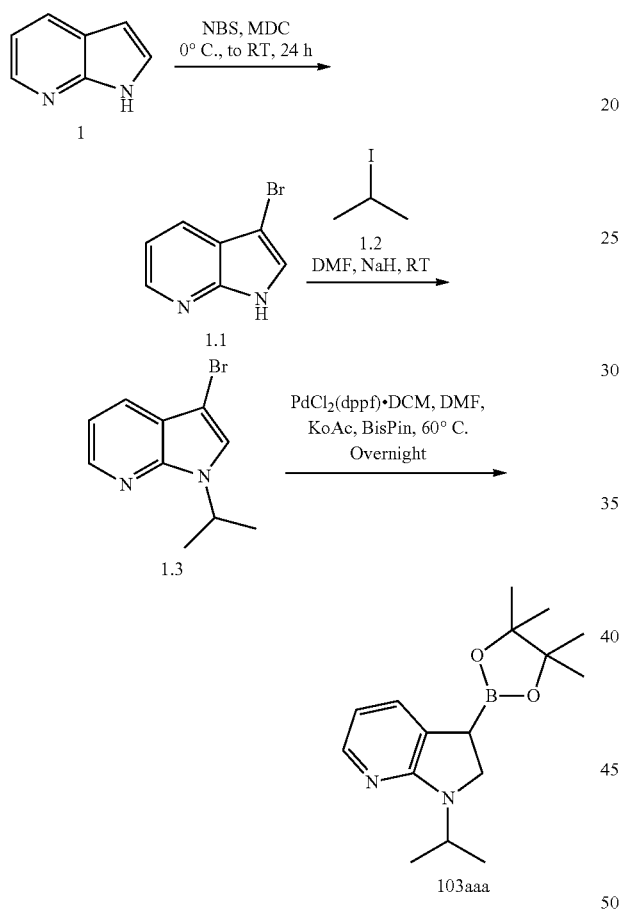

Synthesis of Compound 1.1.

To a cooled solution of 1 (1 g, 8.46 mmol, 1.0 eq) in dichloromethane (20 mL), N-bromosuccinamide (1.65 g, 9.30 mmol, 1.1 eq) was added. The reaction mixture was stirred at room temperature for 16 h. After completion of reaction, reaction mixture transferred into ice cold water and product was extracted with ethyl acetate. Organic layer was combined, washed with brine solution, dried over sodium sulphate and concentrated under reduced pressure to obtain crude material. This was further purified by column chromatography and compound was eluted in 9% ethyl acetate in hexane to obtain pure 1.1 (1.4 g, 83.94%). MS(ES): m/z 198.04 [M+H]$^+$.

Synthesis of Compound 1.3.

To a cooled solution of 1.1 (1.4 g, 7.11 mmol, 1 eq) in tetrahydrofuran (12 mL) was added sodium hydride (0.446 g, 11.16 mmol, 1.5 eq) followed by addition of 1.2 (1.45 g, 8.53 mmol, 1.2 eq) under nitrogen. The reaction was stirred at room temperature for 16 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 7% ethyl acetate in hexane to obtain pure 1.3 (1.2 g, 70.63%), MS(ES): m/z 240.12 [M+H]$^+$.

Synthesis of Compound 103aaa.

To a solution of 1.3 (1.2 g, 5.02 mmol, 1.0 eq) in dimethylformamide (15 mL) was added bis(pinacolato)diboron (3.81 g, 15.06 mmol, 3 eq), potassium acetate (1.23 g, 12.5 mmol, 2.5 eq). The reaction mixture was degassed for 10 min. under argon atmosphere, then [1,1'-Bis(diphenylphosphino)ferrocene]dichloropalladium(II) (0.409 g, 0.502 mmol, 0.1 eq) was added and again degassed for 5 min. The reaction was stirred at 60° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 10% ethyl acetate in hexane as eluant to obtain pure 103aaa (0.800 g, 55.70%). MS(ES): m/z 287.18 [M+H]$^+$.

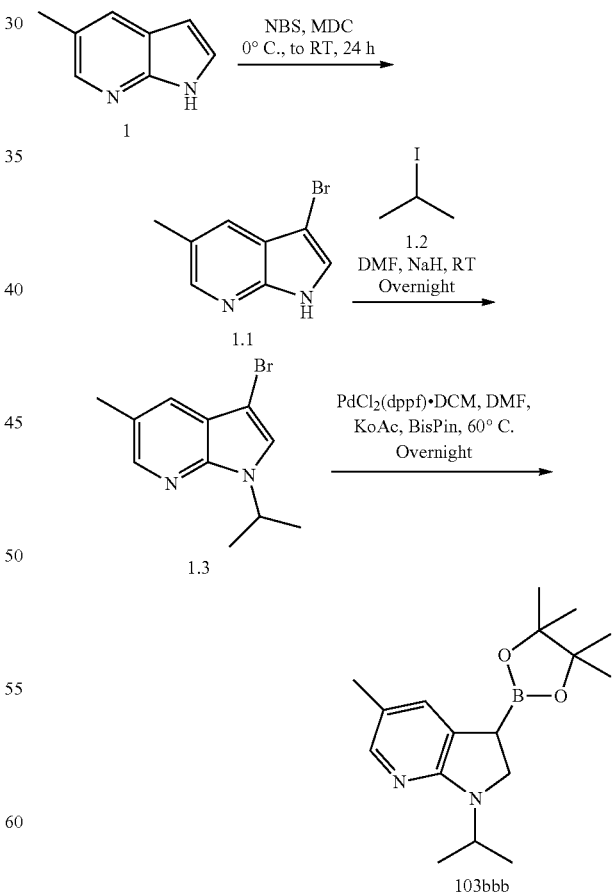

Synthesis of Compound 1.1.

To a cooled solution of 1 (3 g, 22.70 mmol, 1.0 eq) in dichloromethane (50 mL), N-bromosuccinamide (4.44 g, 24.97 mmol, 1.1 eq) was added. The reaction mixture was stirred at room temperature for 16 h. After completion of reaction, reaction mixture transferred into ice cold water and product was extracted with ethyl acetate. Organic layer was combined, washed with brine solution, dried over sodium sulphate and concentrated under reduced pressure to obtain crude material. This was further purified by column chromatography and compound was eluted in 9% ethyl acetate in hexane to obtain pure 1.1 (1.5 g, 31.31%). MS(ES): m/z 212.06 [M+H]⁺.

Synthesis of Compound 1.3.

To a cooled solution of 1.1 (1.5 g, 7.14 mmol, 1 eq) in dimethylformamide (15 mL) was added sodium hydride (0.188 g, 7.85 mmol, 1.1 eq) followed by addition of 1.2 (1.33 g, 7.85 mmol, 1.1 eq) under nitrogen. The reaction was stirred at room temperature for 16 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 7% ethyl acetate in hexane to obtain pure 1.3 (1.1 g, 61.14%), MS(ES): m/z 254.14 [M+H]⁺.

Synthesis of Compound 103bbb.

To a solution of 1.3 (1.1 g, 4.35 mmol, 1.0 eq) in dimethylformamide (12 mL) was added bis(pinacolato)diboron (3.30 g, 13.05 mmol, 3 eq), potassium acetate (1.06 g, 10.87 mmol, 2.5 eq). The reaction mixture was degassed for 10 min. under argon atmosphere, then [1,1'-Bis(diphenylphosphino)ferrocene]dichloropalladium(II) (0.355 g, 0.435 mmol, 0.1 eq) was added and again degassed for 5 min. The reaction was stirred at 60° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 11% ethyl acetate in hexane as eluant to obtain pure 103bbb (0.800 g, 61.33%). MS(ES): m/z 301.21 [M+H]⁺.

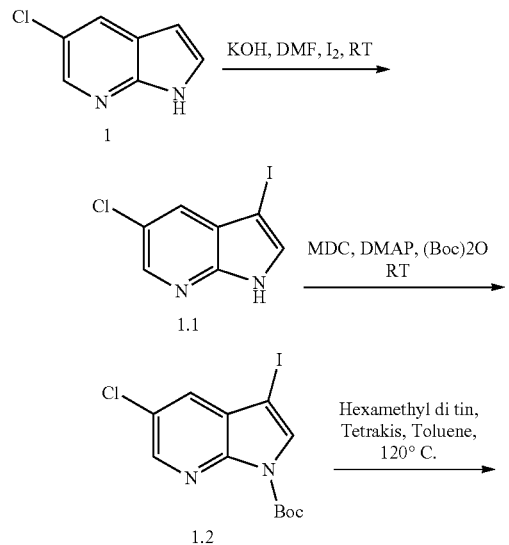

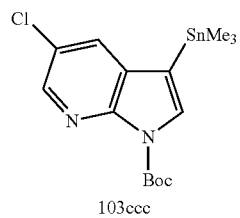

Synthesis of Compound 1.1.

To cooled solution of 1 (5 g, 32.77 mmol, 1.0 eq) in dimethylformamide (50 mL) was added potassium hydroxide (7.34 g, 131.08 mmol, 4.0 eq). The reaction mixture was stirred at 0° C. for 10 min, iodine (8.32 g, 32.77 mmol, 1.0 eq) was added and reaction mixture was stirred at 0° C. for 30 min. After completion of reaction, reaction mixture was transferred into cold ice water. Precipitated solid filtered, dried well to obtain pure 1.1 (4.3 g, 47.12%). MS (ES): m/z 279.48 [M+H]⁺

Synthesis of Compound 1.2.

To a solution of 1.1 (4.3 g, 15.44 mmol, 1.0 eq) in dichloromethane (43 mL), was added 4-Dimethylaminopyridine (0.188 g, 1.54 mmol, 0.1 eq) and Di-tert-butyl dicarbonate (3.70 g, 16.98 mmol, 1.1 eq) at same temperature. The reaction was stirred at room temperature for 3 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude 1.2 (4 g, 68.42%). MS(ES): m/z 379.59 [M+H]⁺. [crude was directly use for next step].

Synthesis of Compound 103ccc.

To a solution of 1.2. (4 g, 10.57 mmol, 1.0 eq) in toluene (40 mL), palladium-tetrakis(triphenylphosphine) (1.22 g, 1.06 mmol, 0.1 eq) was added. The reaction mixture was degassed for 10 min. under argon atmosphere, then hexamethyl ditin (5.18 g, 15.85 mmol, 1.5 eq) was added and reaction was stirred at 120° C. for 1 h. After completion of reaction, reaction mixture was filtered through celite-bed. Filtrate was concentrated under reduced pressure to obtain crude material. This was further purified by combi flash using as eluant in 0.2% ethyl acetate in hexane to obtain pure 103ccc (1.5 g, 34.17%). MS (ES): m/z 416.51 [M+H]⁺.

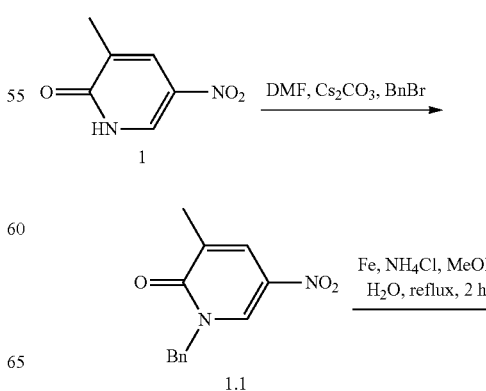

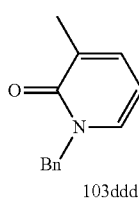

103ddd

Synthesis of Compound 1.1.

To a solution of 1. (5.0 g, 32.44 mmol, 1.0 eq) in dimethylformamide (50 mL), was added benzyl bromide (31.823 g, 97.32 mmol, 1.5 eq) and cesium carbonate (8.32 g, 48.66 mmol, 1.5 eq). The reaction was stirred at 90° C. for 2 h. After completion of reaction, reaction mixture was transferred in cold ice water and extracted with ethyl acetate. Organic layer was wash with brine solution and combined and dried over sodium sulphate and concentrated under reduced pressure to obtain crude material. This was further purified by column chromatography and compound was eluted in 12% ethyl acetate in hexane to obtain pure 1.1 (3.2 g, 40.38%). MS (ES): m/z 245.25 [M+H]$^+$ Synthesis of Compound 103ddd.

To a solution of 1.1 (3.2 g, 13.10 mmol, 1.0 eq) in methanol:water (39 mL, 10:2), was added ammonium chloride (1.40 g, 26.2 mmol, 2 eq) and iron powder (3.67 g, 65.5 mmol, 5 eq) was added at 0° C. The reaction was stirred at 90° C. for 2 h. After completion of reaction, reaction mixture was transferred in cold ice water and extracted with ethyl acetate. Organic layer was wash with brine solution and combined and dried over sodium sulphate and concentrated under reduced pressure to obtain crude material. This was further purified by column chromatography and compound was eluted in 1.8% methanol in dichloromethane to obtain pure 103ddd (1.65 g, 58.78%). MS (ES): m/z 215.27 [M+H]$^+$.

Example 104: Syntheses of Compounds Comprising N-((1R,5S,6r)-3-oxabicyclo[3.1.0]hexan-6-yl) aminocarbonyl at position 3 of the pyrazolo[1,5-a]pyrimidine 104.1. Synthesis of N-((1R,5S,6r)-3-oxabicyclo [3.1.0]hexan-6-yl)-5-((2-methoxypyridin-3-yl) amino)-7-(methylamino)pyrazolo[1,5-a]pyrimidine-3-carboxamide(I-445)

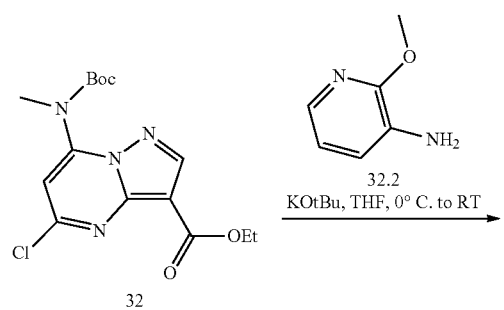

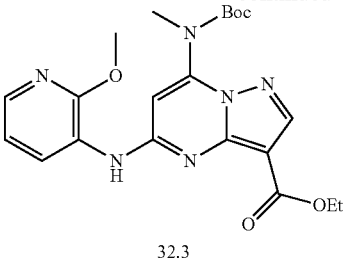

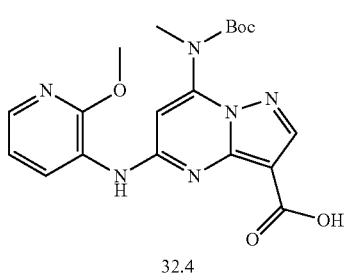

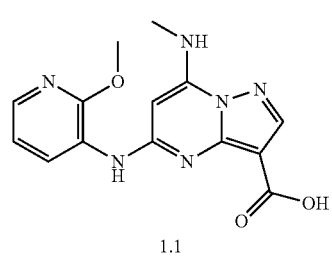

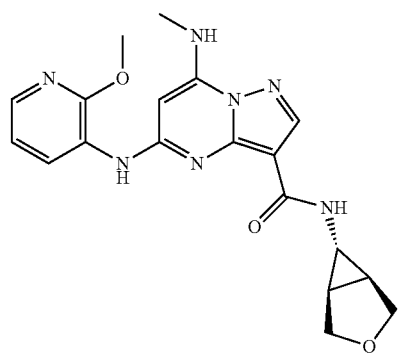

I-445

Synthesis of Compound 32.

Compound was synthesized using general procedure of core synthesis to obtain 32. (Yield: 62.21%). MS (ES): m/z 355.5 [M+H]$^+$ Synthesis of Compound 32.3.

To a cooled solution of 32. (0.500 g, 1.41 mmol, 1.0 eq), and 32.2 (0.174 g, 1.41 mmol, 1.0 eq) in tetrahydrofuran (10 mL) at 0° C. was added potassium ter-butoxide (2.8 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 32.3 (0.630 g, 96.22%). MS (ES): m/z 442.48 [M+H]+

Synthesis of Compound 32.4.

To a solution of 32.3 (0.600 g, 1.36 mmol, 1.0 eq), in tetrahydrofuran: water (20 mL, 2:1) was added lithium hydroxide (0.312 g, 13.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 32.4 (0.400 g, 71.18%). MS(ES): m/z 415.42 [M+H]+.

Synthesis of Compound 1.1.

To 32.4 (0.400 g, 0.96 mmol, 1.0 eq) was added 4M hydrochloric acid in 1,4 Dioxane (2 mL, 4M) at 0° C. and reaction was stirred at room temperature for 4 h. After completion of reaction, reaction mixture was concentrated under reduced pressure, residue was triturated with diethyl ether to obtain 1.1 (0.3 g, 98.89%), MS (ES): m/z 315.11 [M+H]+

Synthesis of Compound I-445:

Compound was synthesized using general procedure A to obtain I-445 (0.043 g, 42.72%), MS (ES): m/z 396.17 [M+H]+, LCMS purity: 95.52%, HPLC purity: 99.60%, Chiral HPLC purity: 99.66%, $^1$H NMR (DMSO-$d_6$, 400 MHZ): 8.96 (s, 1H), 8.23-8.21 (d, J=8 Hz 1H), 8.15 (s, 1H), 7.95-7.91 (q, J=4 Hz, 2H), 7.85 (d, J=3.6 Hz, 1H), 7.07-7.04 (m, 1H), 5.88 (s, 1H), 3.96 (s, 3H), 3.89-3.88 (d, J=4 Hz, 1H), 3.65-3.63 (d, J=8 Hz, 2H), 2.94-2.97 (m, 3H), 1.68 (s, 2H), 1.24 (s, 2H).

Additional compounds prepared by substantially the same method, and their characterization data, are listed in the Table 50 below. The intermediate corresponding to 32.2 of the above scheme is listed for each compound.

TABLE 50

| Compound | Intermediate | Characterization data |
|---|---|---|
| I-446 | (pyridine with O-cyclopropyl and NH2 substituents) | MS (ES): m/z 422.50 [M + H]+, LCMS purity: 99.52%, HPLC purity: 99.65%, Chiral HPLC purity: 100%, $^1$H NMR (DMSO-$d_6$, 400 MHZ): 8.7 (s, 1H), 8.21-8.19 (d, J = 8 Hz, 1H), 8.14 (s, 1H), 7.97-7.91 (q, J = 4 Hz, 8 Hz, 2H), 7.82-7.81 (d, J = 4 Hz, 1H), 7.08-7.05 (m, 1H), 5.82 (s, 1H), 4.35-4.32 (m, 1H), 3.87-3.85 (d, J = 8 Hz, 2H), 3.64-3.62 (d, J = 8 Hz, 2H), 2.91-2.90 (d, J = 4 Hz, 4H), 1.66 (s, 2H), 0.80-0.69 (m, 4H). |
| I-447 | (pyridine with O-CD3 and NH2 substituents) | MS (ES): m/z 399.22 [M + H]+, LCMS purity: 95.52%, HPLC purity: 97.48%, Chiral HPLC purity: 97.74%, $^1$H NMR (DMSO-$d_6$, 400 MHZ): 8.96 (s, 1H), 8.23-8.21 (d, J = 8 Hz 1H), 8.15 (s, 1H), 7.95-7.91 (q, J = 4 Hz, 8 Hz, 2H), 7.86-7.85 (d, J = 4 Hz, 1H), 7.07-7.04 (m, 1H), 5.88 (s, 1H), 3.88-3.86 (d, J = 8 Hz, 2H), 3.65-3.63 (d, J = 8 Hz, 2H), 2.91-2.90 (d, J = 4 Hz, 3H), 1.68 (s, 2H), 1.24 (bs, 1H). |
| I-650 | (pyridinone with tetrahydropyran and NH2 substituents) | MS (ES): m/z 466.51 [M + H]+, LCMS purity: 100%, HPLC purity: 98.52%, $^1$H NMR (DMSO-$d_6$, 400 MHZ): 8.93 (s, 1H), 8.19-8.16 (m, 1H), 7.94-7.93 (d, J = 4.4 Hz, 1H), 7.85-7.84 (d, J = 3.6 Hz, 1H), 7.56-7.54 (d, J = 5.2 Hz, 1H), 6.38-6.34 (t, J = 7.2 Hz, 1H), 6.21 (s, 1H), 4.91-4.88 (m, 1H), 3.93-3.83 (m, 4H), 3.69-3.67 (d, J = 8.0 Hz, 2H), 3.61-3.56 (t, J = 10.0 Hz, 1H), 3.50-3.45 (t, J = 8.8 Hz, 1H), 2.91-2.90 (d, J = 4.8 Hz, 3H), 2.62 (s, 2H), 2.08-1.98 (m, 2H), 1.78-1.71 (m, 2H), 1.33-1.24 (m, 2H). |
| I-651 | (pyridinone with tetrahydropyran and NH2 substituents) | MS (ES): m/z 466.51 [M + H]+, LCMS purity: 100%, HPLC purity: 98.64%, $^1$H NMR (DMSO-$d_6$, 400 MHZ): 8.93 (s, 1H), 8.19-8.16 (m, 1H), 7.94-7.93 (d, J = 4.4 Hz, 1H), 7.86-7.85 (d, J = 3.6 Hz, 1H), 7.56-7.55 (d, J = 5.2 Hz, 1H), 6.38-6.34 (t, J = 7.2 Hz, 1H), 6.21 (s, 1H), 4.89 (s, 1H), 3.92-3.90 (d, J = 8.0 Hz, 2H), 3.85 (s, 2H), 3.69-3.67 (d, J = 8.4 Hz, 2H), 3.59 (s, 1H), 3.47 (s, 2H), 2.91-2.90 (d, J = 4.8 Hz, 3H), 2.61 (s, 1H), 1.97 (m, 2H), 2.00-198 (m, 1H), 1.84 (s, 2H), 1.79 (m, 1H). |

104.2. Synthesis of N-((1R,5S,6r)-3-oxabicyclo[3.1.0]hexan-6-yl)-5-((5-chloro-2-oxo-1-(tetrahydro-2H-pyran-3-yl)-1,2-dihydropyridin-3-yl)amino)-7-(methylamino)pyrazol[1,5-a]pyrimidine-3-carboxamide (I-741)

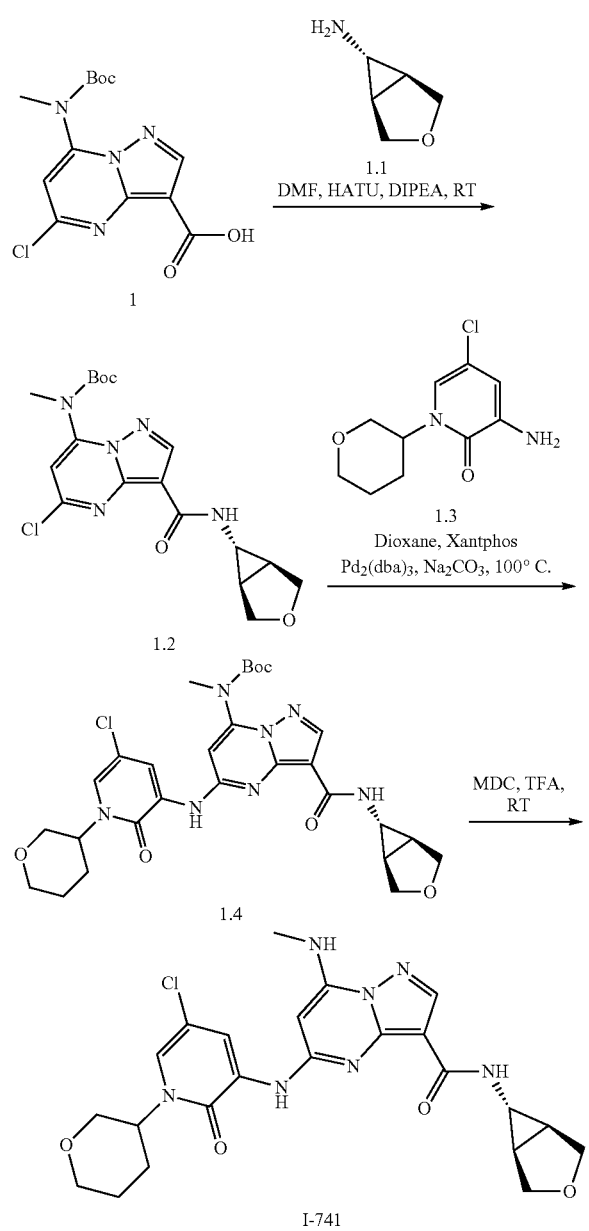

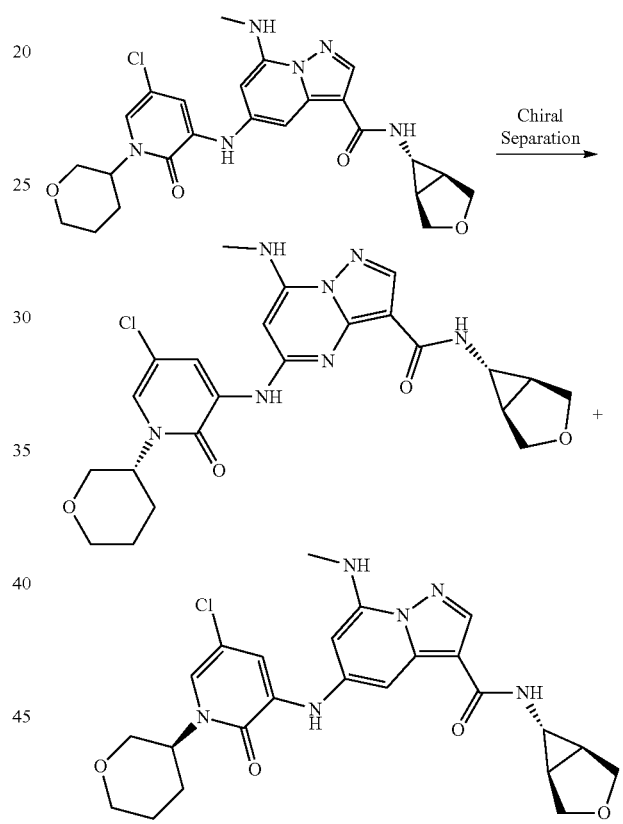

Synthesis of Compound 1.

Compound was synthesized using general procedure of core synthesis to obtain 1. (Yield: 71.67%). MS (ES): m/z 327.08 [M+H]+

Synthesis of Compound 1.2.

Compound was synthesized using general procedure A to obtain 1.2. (0.160 g, 42.73%), MS (ES): 408.14 [M+H]+

Synthesis of Compound 1.3.

Compound was synthesized as per experimental protocol of I-711 to obtain 1.3. (Yield: 67.65%), MS (ES): m/z 229.07 [M+H]+.

Synthesis of Compound 1.4.

Compound was synthesized using general procedure B to obtain 1.4. (0.120 g, 50.98%), MS (ES): 601.22 [M+H]+

Synthesis of Compound I-741:

Compound was synthesized using general procedure C to obtain I-741 (0.075 g, 75.02%), MS (ES): 500.47 [M+H]+ LCMS purity: 95.14%, HPLC purity: 96.06%, CHIRAL HPLC: 47.41% 47.09%, $^1$H NMR (DMSO-$d_6$, 400 MHZ): 8.27 (bs, 1H), 8.23 (s, 1H), 8.02-8.01 (d, J=5.2 Hz, 1H), 7.72 (bs, 1H), 7.64 (bs, 1H), 6.33 (s, 1H), 4.86 (bs, 1H), 3.90-3.88 (d, J=8.4 Hz, 2H), 3.83 (bs, 2H), 3.67-3.65 (d, J=6.8 Hz, 2H), 3.51-3.46 (t, J=10.4 Hz, 1H), 3.18-3.17 (d, J=5.2 Hz, 1H), 2.91-2.90 (d, J=4.4 Hz, 2H), 1.91 (s, 3H), 1.76 (bs, 3H), 1.24 (bs, 3H).

104.3. Chiral Separation of Compound I-741

Synthesis of compounds I-799 and I-800.

Isomers of I-741 (0.075 g) were separated out using column CHIRALPAK IB (250 mm*4.6 mm, 5 u) in 0.1% DEA in HEXANE IPA:Methanol (50:50) as co-solvent with flow rate of 4 mL/min. to get pure fraction-1 (FR-a) and fraction-2 (FR-b).

FR-a was concentrated under reduced pressure at 30° C. to afford pure FR-a (0.021 g). MS(ES): m/z 500.46 [M+H]+, LCMS purity: 96.58%, HPLC purity: 96.29%, CHIRAL HPLC purity: 99.04%, $^1$H NMR (DMSO-$d_6$, 400 MHZ): 9.06 (s, 1H), 8.26-8.27 (d, J=4 Hz, 1H), 8.23 (s, 1H), 8.02-8.01 (d, J=4 Hz, 1H), 7.72-7.71 (d, J=4 Hz, 1H), 7.64-7.63 (d, J=3.2 Hz, 1H), 6.32 (s, 1H), 4.88-4.84 (t, J=8 Hz, 1H), 3.90-3.81 (m, 4H), 3.67-3.63 (t, J=16 Hz, 3H), 3.52-3.46 (t, J=12 Hz, 1H), 2.91-2.90 (d, J=4 Hz, 3H), 2.13-2.08 (m, 1H), 1.97-1.91 (m, 3H), 1.77-1.70 (m, 2H), 1.24 (bs, 1H).

FR-b was concentrated under reduced pressure at 30° C. to afford pure FR-b (0.021 g). MS(ES): m/z 500.26 [M+H]⁺, LCMS purity: 100%, HPLC purity: 99.31%, CHIRAL HPLC purity: 98.02%, ¹H NMR (DMSO-d₆, 400 MHZ): 9.06 (s, 1H), 8.26-8.27 (d, J=4 Hz, 1H), 8.23 (s, 1H), 8.02-8.01 (d, J=4 Hz, 1H), 7.72-7.71 (d, J=4 Hz, 1H), 7.64-7.63 (d, J=3.2 Hz, 1H), 6.32 (s, 1H), 4.88-4.84 (t, J=8 Hz, 1H), 3.90-3.81 (m, 4H), 3.67-3.63 (t, J=16 Hz, 3H), 3.52-3.46 (t, J=12 Hz, 1H), 2.91-2.90 (d, J=4 Hz, 3H), 2.13-2.08 (m, 1H), 1.97-1.91 (m, 3H), 1.77-1.70 (m, 2H), 1.24 (bs, 1H).

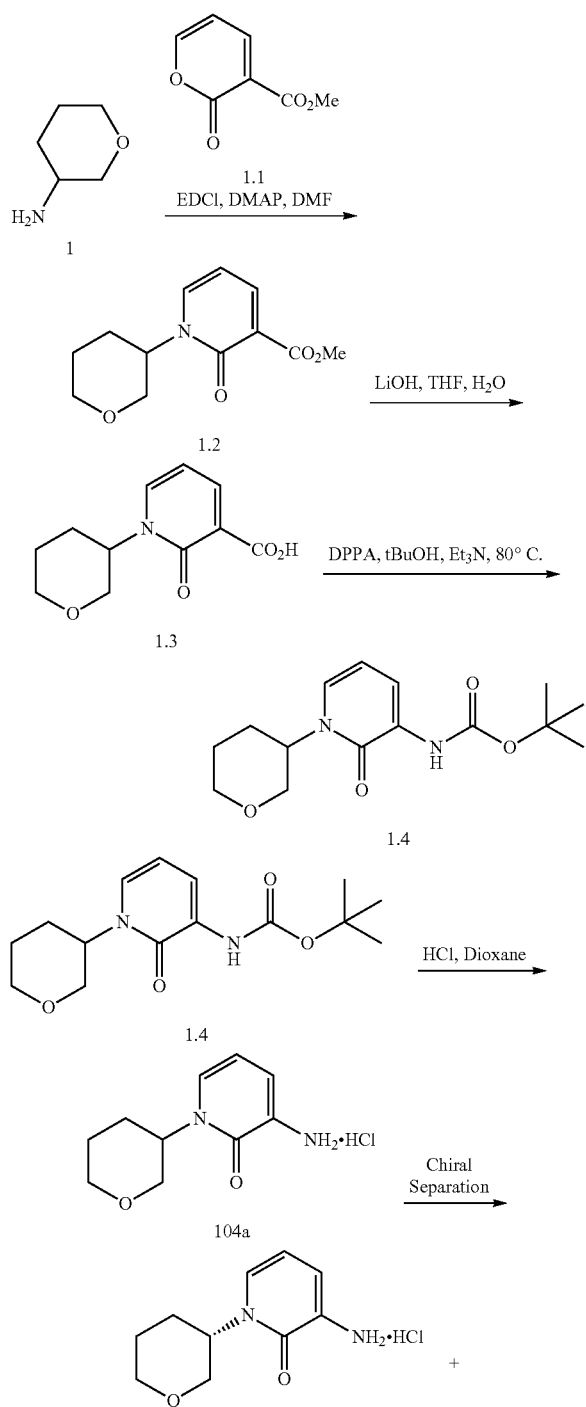

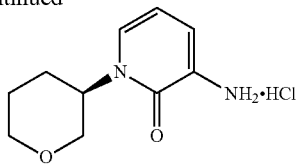

Synthesis of Compound 1.2.

To a cooled solution of 1 (0.65 g, 6.49 mmol, 1.0 eq), in N,N-dimethylformamide (10 mL) was added 1.1 (1.0 g, 6.49 mmol, 1.0 eq). The reaction mixture was stirred at 0° C. for 6 h and further stirred at room temperature for 15 min. N-Ethyl-N'-(3-dimethylaminopropyl)carbodiimide hydrochloride (1.65 g, 8.43 mmol, 1.3 eq) and 4-Dimethylaminopyridine (0.2 g, 1.62 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.2 (0.6 g, 39.35%). MS(ES): m/z 238.26 [M+H]⁺.

Synthesis of Compound 1.3.

To a solution of 1.2 (0.6 g, 2.53 mmol, 1.0 eq), in tetrahydrofuran: methanol: water (10 mL, 2:2:1) was added lithium hydroxide (1.06 g, 25.3 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.5 g, 88.57%). MS(ES): m/z 224.23 [M+H]⁺.

Synthesis of Compound 1.4.

To a solution of 1.3 (0.70 g, 3.14 mmol, 1.0 eq) in tert.butanol (8 mL) was added triethylamine (0.54 g, 5.33 mmol, 1.7 eq) and diphenyl phosphoryl azide (1.12 g, 5.33 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.6 g, 65.00%). MS(ES): m/z 295.35 [M+H]⁺.

Synthesis of Compound 104a.

A cooled solution of 1.4 (0.6 g, 2.04 mmol, 1 eq) in dioxane (2 mL) was added 4N hydrochloric acid in dioxane (3 mL) as a dropwise. The reaction mixture was stirred at room temperature for 2 h. After completion of reaction, reaction mixture was concentrated under reduced pressure to obtain pure 104a (0.4 g, 85.06%). MS(ES): m/z 231.11 [M+H]⁺.

Synthesis of Compound 104b and 104c.

Isomers of 104a (0.4 g) were separated out using column (CHIRAL PAK IB 250 mm*4.6 mm, 5 u) in 0.1% Diethyl amine in methanol as co-solvent with flow rate of 4 mL/min.

to get pure fraction-1 and fraction-2. Fraction-1 was concentrated under reduced pressure at 30° C. to afford pure Fraction-1 (0.15 g). MS (ES): m/z 195.11 [M+H]⁺, LCMS purity: 100%, HPLC purity: 99.84% CHIRAL HPLC: 98%, Fraction-2 was concentrated under reduced pressure at 30° C. to afford pure Fraction-2 (0.14 g). MS (ES): m/z 195.11 [M+H]⁺, LCMS purity: 100%, HPLC purity: 99.90%, CHIRAL HPLC: 99%.

Example 105: Synthesis of Compounds Comprising N-(3-hydroxycyclopentyl)aminocarbonyl at Position 3 of the pyrazolo[1,5-a]pyrimidine 105.1. Synthesis of 5-((2-cyclopropoxypyridin-3-yl) amino)-N-(3-hydroxycyclopentyl)-7-(methylamino) pyrazolo[1,5-a]pyrimidine-3-carboxamide (I-461)

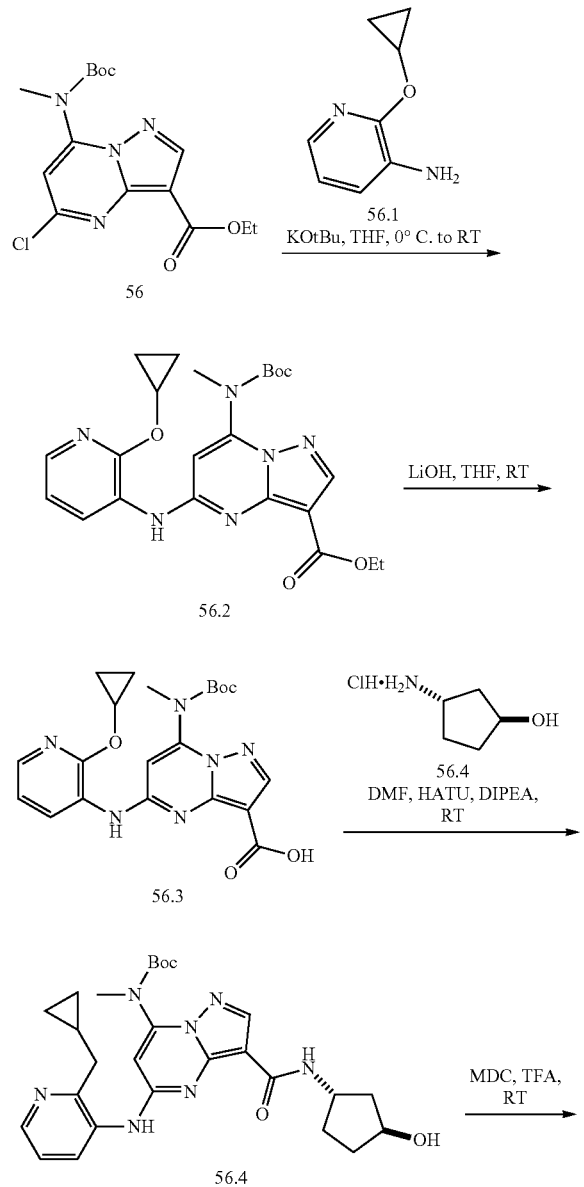

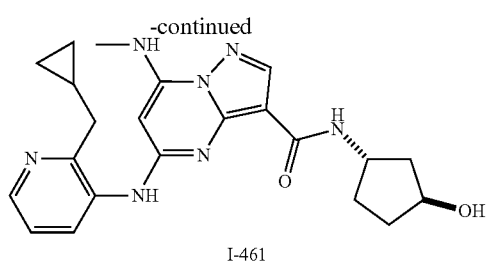

I-461

Synthesis of Compound 56.

Compound was synthesized using general procedure of core synthesis to obtain 56. (Yield: 62.21%). MS (ES): m/z 355.5 [M+H]⁺

Synthesis of Compound 56.1.

Compound was synthesized as per experimental protocol of Example 55 of I-215 to obtain 56.1

Synthesis of Compound 56.2.

To a cooled solution of 56. (3.0 g, 8.46 mmol, 1.0 eq), and 56.1 (1.27 g, 8.46 mmol, 1.0 eq) in tetrahydrofuran (30 mL) at 0° C. was added potassium ter-butoxide (16.9 mL, 16.92 mmol, 2.0 eq). The reaction was stirred at room temperature for 1 h. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 56.2 (2.45 g, 61.84%). MS (ES): m/z 469.5 [M+H]⁺.

Synthesis of Compound 56.3.

To a solution of 56.2 (2.4 g, 5.12 mmol, 1.0 eq), in tetrahydrofuran: water (80 mL, 2:1) was added lithium hydroxide (2.150 g, 51.2 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 56.3 (1.8 g, 79.78%). MS(ES): m/z 441.5 [M+H]⁺.

Synthesis of Compound I-461.

Compound was synthesized using general procedure C to obtain I-461 (0.150 g, 97.60%), MS (ES): m/z 424.22 [M+H]⁺, LCMS purity: 100%, HPLC purity: 99.01%, Chiral HPLC purity: 50.06%+49.93%, ¹H NMR (DMSO-d₆, 400 MHZ): 8.72 (s, 1H), 8.21-8.19 (d, J=8 Hz, 1H), 8.13 (s, 1H), 7.95-7.90 (m, 2H), 7.64-7.62 (d, J=8 Hz, 1H), 7.00-6.97 (m, 1H), 5.83 (s, 1H), 4.56-4.55 (s, 1H), 4.40-4.32 (m, 2H), 4.14 (bs, 1H), 2.91 (s, 3H), 2.06-2.03 (m, 1H), 1.89-1.88 (m, 2H), 1.46-1.44 (bs, 1H), 1.38-1.31 (m, 1H), 1.23-1.14 (m, 1H), 0.79-0.76 (m, 4H).

Additional compounds prepared by substantially the same method, and their characterization data, are listed in the Table 51 below. The intermediate corresponding to of the 56.1 above scheme is listed for each compound.

TABLE 51

| Compound | Intermediate | Characterization data |
|---|---|---|
| I-462 | 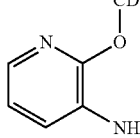 | MS (ES): m/z 401.22 [M + H]+, LCMS purity: 100%, HPLC purity: 99.66%, CHIRAL HPLC: (50.04%, 49.95%) $^1$H NMR (DMSO-$d_6$, 400 MHZ): 9.92 (s, 1H), 8.23-8.21 (d, J = 6.4 Hz, 1H), 8.14 (s, 1H), 7.92-7.91 (d, J = 3.2 Hz, 2H), 7.66-7.64 (d, J = 8 Hz, 1H), 6.98-6.95 (m, 1H), 5.89 (d, 1H), 4.57-4.56 (d, J = 4 Hz, 1H), 4.42-4.36 (m, 1H), 4.05 (s, 1H), 2.92-2.90 (m, 3H), 2.74 (s, 1H), 2.10-2.03 (m, 1H), 1.89-1.81 (m, 2H), 1.40-1.34 (m, 2H). |
| I-467 | 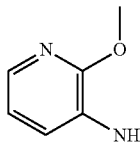 | MS (ES): m/z 398.22 [M + H]+, LCMS purity: 100%, HPLC purity: 100%, CHIRAL HPLC: 49.73%, 50.26%, $^1$H NMR (DMSO-$d_6$, 400 MHZ): 8.92 (s, 1H), 8.23-8.21 (d, J = 6.8 Hz, 1H), 8.14 (s, 1H), 7.92-7.90 (m, 2H), 7.66-7.64 (d, J = 8 Hz, 1H), 6.98-6.95 (m, 1H), 5.89 (s, 1H), 4.57-4.56 (d, J = 3.6 Hz, 1H), 4.42-4.36 (m, 1H), 4.15 (bs, 1H), 3.95 (s, 3H), 2.92-2.90 (d, J = 4.8 Hz, 3H), 2.08-2.03 (m, 1H), 1.89-1.82 (m, 2H), 1.56 (bs, 1H), 1.45 (bs, 1H), 1.36-1.33 (m, 1H). |

105.2. Chiral Separation of I-461

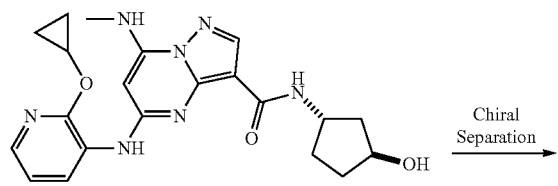

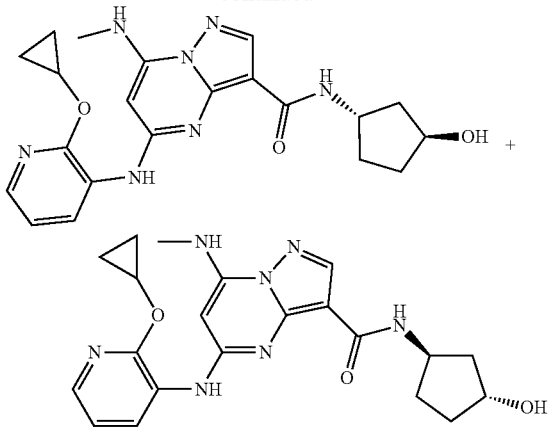

Synthesis of compounds I-489 and I-490.

Isomers of I-461 (0.120 g) were separated out using column (CHIRALPAK AD-H (250 mm*4.6 mm, 5 u)) in 0.1% DEA in MEOH as co-solvent (25%) with flow rate of 3 mL/min. to get pure fraction-1 (FR-a) and fraction-2 (FR-b). FR-a was concentrated under reduced pressure at 30° C. to afford pure FR-a (0.040 g). MS(ES): m/z 424.38 [M+H]+, LCMS purity: 99.33%, HPLC purity: 98.88%, CHIRAL HPLC purity: 100%, $^1$H NMR (DMSO-$d_6$, 400 MHZ): 8.73 (s, 1H), 8.21-8.20 (d, J=6.4 Hz, 1H), 8.14 (s, 1H), 7.96-7.95 (d, J=3.6 Hz, 1H), 7.92-7.90 (d, J=4.8 Hz, 2H), 7.64-7.63 (d, J=7.6 Hz, 1H), 7.01-6.98 (m, 1H), 5.85 (s, 1H), 4.57-4.56 (d, J=3.6 Hz, 1H), 4.41-4.35 (m, 1H), 4.16 (bs, 1H), 2.92-2.91 (d, J=4.8 Hz, 3H), 2.08-2.01 (m, 1H), 1.89-1.80 (m, 2H), 1.47-1.45 (bs, 1H), 1.39-1.32 (m, 1H), 1.24-1.13 (m, 1H), 0.80-0.69 (m, 4H).

FR-b was concentrated under reduced pressure at 30° C. to afford pure FR-b (0.045 g). MS(ES): m/z 424.33 [M+H]+, LCMS purity: 98.33%, HPLC purity: 99.03%, CHIRAL HPLC purity: 97.83%, $^1$H NMR (DMSO-$d_6$, 400 MHZ): 8.73 (s, 1H), 8.21-8.20 (d, J=6.4 Hz, 1H), 8.14 (s, 1H), 7.96-7.95 (d, J=3.6 Hz, 2H), 7.92-7.90 (d, J=4.8 Hz, 1H), 7.64-7.63 (d, J=7.6 Hz, 1H), 7.01-6.98 (m, 1H), 5.85 (s, 1H), 4.57-4.56 (d, J=3.6 Hz, 1H), 4.42-4.33 (m, 1H), 4.16 (bs, 1H), 2.92-2.91 (d, J=4.8 Hz, 3H), 2.07-2.03 (m, 1H), 1.89-1.81 (m, 2H), 1.47-1.45 (bs, 1H), 1.39-1.32 (m, 1H), 1.21-1.13 (m, 1H), 0.80-0.69 (m, 4H).

Additional compounds prepared by substantially the same method, and their characterization data, are listed in the Table 52 below.

TABLE 52

| Compound | Isomers | Characterization data |
|---|---|---|
| I-467 | I-487<br>I-488 | FR-a: MS (ES): m/z 398.22 [M + H]+, LCMS purity: 100%, HPLC purity: 99.51%, CHIRAL HPLC purity: 100%, $^1$H NMR (DMSO-$d_6$, 400 MHZ): 8.91 (s, 1H), 8.22-8.20 (d, J = 7.6 Hz, 1H), 8.13 (s, 1H), 7.92-7.90 (m, 2H), 7.65-7.63 (d, J = 7.6 Hz, 1H), 6.98-6.94 (m, 1H), 5.88 (s, 1H), 4.56 (bs, 1H), 4.41-4.36 (m, 1H), 4.15 (bs, 1H), 3.94 (s, 3H), 2.90 (bs, 3H), 2.07-2.02 (m, 2H), 1.88-1.81 (m, 2H), 1.39-1.32 (m, 1H), 1.21-1.15 (m, 1H).<br>FR-b: MS (ES): m/z 398.17 [M + H]+, LCMS purity: 100%, HPLC purity: 99.36%, CHIRAL HPLC purity: 96.63%, $^1$H NMR (DMSO-$d_6$, 400 MHZ): 8.92 (s, 1H), 8.23-8.21 (d, J = 7.2 Hz, 1H), 8.14 (s, 1H), 7.92-7.91 (d, J = 4 Hz, 2H), 7.66-7.64 (d, J = 8 Hz, 1H), 6.98-6.95 (m, 1H), 5.89 (s, 1H), |

TABLE 52-continued

| Compound | Isomers | Characterization data |
|---|---|---|
| | | 4.57-4.56 (d, J = 3.2 Hz, 1H), 4.42-4.36 (m, 1H), 4.15 (bs, 1H), 3.95 (s, 3H), 3.18-3.17 (d, J = 4.4 Hz, 1H), 2.92-2.90 (bs, 3H), 2.69-2.67 (d, J = 6.8 Hz, 1H), 2.09-2.01 (m, 2H), 1.40-1.33 (m, 1H), 1.21-1.15 (m, 1H). |
| I-462 | I-500 I-501 | FR-a: MS (ES): m/z 401.22 [M + H]$^+$, LCMS purity: 100%, HPLC purity: 100%, CHIRAL HPLC purity: 100%, $^1$H NMR (DMSO-d$_6$, 400 MHZ): 8.89 (s, 1H), 8.22-8.20 (m, 1H), 8.13 (s, 1H), 7.92-7.87 (m, 2H), 7.65-7.63 (d, J = 9.6 Hz, 1H), 6.97-6.94 (m, 1H), 5.88 (s, 1H), 4.55-4.54 (d, J = 3.6 Hz, 1H), 4.42-4.36 (m, 1H), 4.15 (bs, 1H), 2.91-2.90 (d, J = 4.4 Hz, 3H), 2.07-2.02 (m, 1H), 1.88-1.84 (m, 2H), 1.46-1.44 (m, 1H), 1.39-1.32 (m, 1H), 1.23-1.14 (m, 1H). FR-b: MS (ES): m/z 401.27 [M + H]$^+$, LCMS purity: 100%, HPLC purity: 99.64%, CHIRAL HPLC purity: 96.13%, $^1$H NMR (DMSO-d$_6$, 400 MHZ): 8.90 (s, 1H), 8.23-8.21 (d, J = 6.8 Hz, 1H), 8.14 (s, 1H), 7.93-7.88 (m, 2H), 7.66-7.64 (d, J = 7.6 Hz, 1H), 6.98-6.95 (m, 1H), 5.89 (s, 1H), 4.55 (bs, 1H), 4.42-4.37 (m, 1H), 4.16 (bs, 1H), 2.92-2.91 (d, J = 4.8 Hz, 3H), 2.10-2.07 (m, 1H), 1.89-1.81 (m, 2H), 1.40-1.33 (m, 1H), 1.19-1.16 (m, 2H). |
| I-701 | I-728 I-729 | FR-a: MS (ES): m/z 468.46 [M + H]$^+$, LCMS purity: 100%, HPLC purity: 99.38%, CHIRAL HPLC purity: 100%, $^1$H NMR (DMSO-d$_6$, 400 MHZ): 8.87 (s, 1H), 8.30-8.28 (d, J = 7.2 Hz, 1H), 8.18 (s, 1H), 7.90-7.89 (d, J = 4.8 Hz 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.90-4.85 (m, 1H), 4.75-4.74 (d, J = 3.2 Hz, 1H), 4.30-4.24 (m, 1H), 4.16 (bs, 1H), 3.85-3.82 (m, 2H), 3.60-3.55 (t, J = 10 Hz, 1H), 2.90-2.89 (d, J = 4.4 Hz, 3H), 2.28-2.21 (m, 1H), 1.66-1.60 (m, 5H), 1.44-1.38 (m, 1H), 1.23 (bs, 2H), 1.04-1.03 (d, J = 6 Hz, 1H), 0.87-0.83 (m, 1H). FR-b: MS (ES): m/z 468.48 [M + H]$^+$, LCMS purity: 100%, HPLC purity: 99.44%, CHIRAL HPLC purity: 98.38%, $^1$H NMR (DMSO-d$_6$, 400 MHZ): 8.87 (s, 1H), 8.30-8.28 (d, J = 7.2 Hz, 1H), 8.18 (s, 1H), 7.90-7.89 (d, J = 4.4 Hz 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.90-4.85 (m, 1H), 4.75-4.74 (d, J = 3.2 Hz, 1H), 4.30-4.24 (m, 1H), 4.16 (bs, 1H), 3.85-3.82 (m, 2H), 3.60-3.55 (t, J = 10 Hz, 1H), 2.90-2.89 (d, J = 4.4 Hz, 3H), 2.28-2.21 (m, 1H), 1.66-1.62 (m, 5H), 1.44-1.38 (m, 1H), 1.23 (bs, 2H), 1.04-1.03 (d, J = 6 Hz, 1H), 0.87-0.83 (m, 1H). |
| I-702 | I-738 I-739 | FR-a: MS (ES): m/z 468.66 [M + H]$^+$, LCMS purity: 95.03%, HPLC purity: 99.90%, CHIRAL HPLC purity: 99.00%, $^1$H NMR (DMSO-d$_6$, 400 MHZ): 8.87 (s, 1H), 8.30-8.28 (d, J = 7.2 Hz, 1H), 8.18 (s, 1H), 7.89 (bs, 1H), 7.68-7.66 (d, J = 8 Hz, 1H), 7.50-7.48 (d, J = 6.8 Hz, 1H), 6.49-6.46 (t, J = 6.8 Hz, 1H), 6.26 (s, 1H), 4.88 (bs, 1H), 4.74 (bs, 1H), 4.28-4.26 (d, J = 6.8 Hz, 1H), 4.16 (bs, 1H), 3.82 (bs, 2H), 3.60-3.55 (t, J = 10.4 Hz, 1H), 2.90-2.89 (d, J = 3.6 Hz, 3H), 2.26-2.23 (m, 2H), 1.64 (bs, 6H), 1.24 (bs, 1H), 1.18-1.14 (t, J = 7.2 Hz, 1H), 0.85 (bs, 1H). FR-b: MS (ES): m/z 468.66 [M + H]$^+$, LCMS purity: 100%, HPLC purity: 98.75%, CHIRAL HPLC purity: 98%, $^1$H NMR (DMSO-d$_6$, 400 MHZ): 8.87 (s, 1H), 8.30-8.29 (d, J = 6.4 Hz, 1H), 8.18 (s, 1H), 7.90-7.89 (d, J = 4.8 Hz, 1H), 7.68-7.66 (d, J = 7.6 Hz, 1H), 7.50-7.48 (d, J = 6.4 Hz, 1H), 6.49-6.46 (t, J = 7.2 Hz, 1H), 6.26 (s, 1H), 4.88 (bs, 1H), 4.75-4.74 (d, J = 2.8 Hz, 1H), 4.28-4.26 (d, J = 7.6 Hz, 1H), 4.16 (bs, 1H), 3.82 (bs, 2H), |

TABLE 52-continued

| Compound | Isomers | Characterization data |
|---|---|---|
| | | 3.60-3.55 (t, J = 10.4 Hz, 1H), 2.90-2.89 (d, J = 4.8 Hz, 3H), 2.26-2.23 (m, 2H), 1.60 (bs, 6H), 1.24 (bs, 1H), 1.18-1.14 (t, J = 7.2 Hz, 1H), 0.85 (bs, 1H). |

105.3. Synthesis of N-(3-hydroxycyclopentyl)-7-(methylamino)-5-((2-oxo-1-((R)-tetrahydro-2H-pyran-3-yl)-1,2-dihydropyridin-3-yl)amino)pyrazolo[1,5-a]pyrimidine-3-carboxamide (I-701)

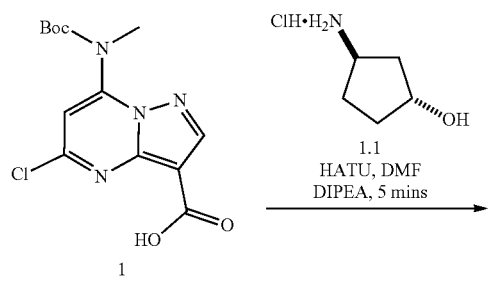

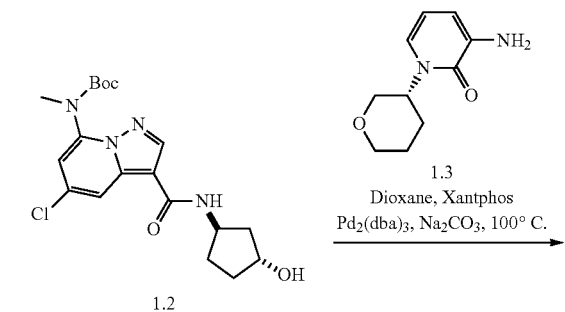

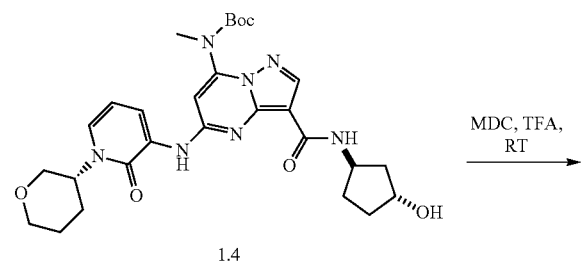

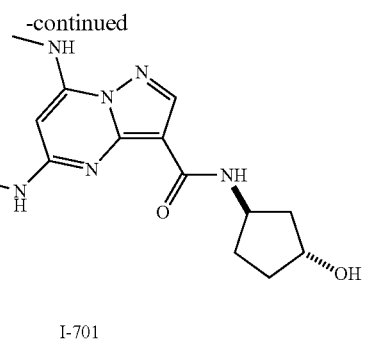

I-701

Synthesis of Compound 1.

Compound was synthesized using general procedure of core synthesis to obtain 1. (Yield: 71.67%). MS (ES): m/z 327.08 [M+H]$^+$ Synthesis of Compound 1.2.

Compound was synthesized using general procedure A to obtain 1.2. (0.6 g, 59.79%), MS (ES): m/z 410.1 [M+H]$^+$ Synthesis of Compound 1.3.

Compound was synthesized according to the experimental protocols provided for the intermediates. MS (ES): m/z 195.11 [M+H]$^+$ Synthesis of Compound 1.4.

Compound was synthesized using general procedure B to obtain 1.4. (0.140 g, 67.39%), MS (ES): m/z 568.28 [M+H]$^+$ Synthesis of Compound I-701:

To 1.4 (0.140 g, 0.24 mmol, 1.0 eq) was added 4M hydrochloric acid in 1,4 Dioxane (3 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-701 (0.110 g, 95.40%). MS (ES): m/z 468.32 [M+H]$^+$, LCMS purity: 97.78%, HPLC purity: 97.41%, CHIRAL HPLC purity: 49.80%, 50.19%, $^1$H NMR (DMSO-d$_6$, 400 MHZ): 8.87 (s, 1H), 8.30-8.28 (d, J=6.8 Hz, 1H), 8.18 (s, 1H), 7.90-7.89 (d, J=4.8 Hz, 1H), 7.68-7.66 (d, J=8 Hz, 1H), 7.50-7.48 (d, J=6.8 Hz, 1H), 6.49-6.46 (t, J=7.2 Hz, 1H), 6.26 (s, 1H), 4.90-4.85 (m, 1H), 4.74-4.74 (d, J=3.2 Hz, 1H), 4.30-4.24 (m, 1H), 4.16 (bs, 1H), 3.85-3.82 (m, 2H), 3.60-3.55 (t, J=10.4 Hz, 1H), 2.90-2.89 (d, J=4.4 Hz, 3H), 2.28-2.21 (m, 1H), 1.96 (s, 4H), 1.76-1.62 (m, 5H), 1.19-1.16 (d, J=7.2 Hz, 1H).

Additional compounds prepared by substantially the same method, and their characterization data, are listed in the Table 53 below. The intermediate corresponding to of the 1.3 above scheme is listed for each compound.

TABLE 53

| Compound | Intermediate | Characterization data |
|---|---|---|
| I-702 | 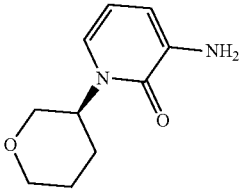 [SMILES: Nc1cccn([C@H]2CCCOC2)c1=O] | MS (ES): m/z 468.32 [M + H]+, LCMS purity: 99.39%, HPLC purity: 99.24%, CHIRAL HPLC: 50.85%, 49.14%, 1H NMR (DMSO-d6, 400 MHZ): 8.87 (s, 1H), 8.30-8.28 (d, J = 6.8 Hz, 1H), 8.18 (s, 1H), 7.90-7.89 (d, J = 4.8 Hz, 1H), 7.68-7.66 (d, J = 8 Hz, 1H), 7.50-7.48 (d, J = 6.8 Hz, 1H), 6.49-6.46 (t, J = 7.2 Hz, 1H), 6.26 (s, 1H), 4.88 (bs, 1H), 4.30-4.24 (m, 1H), 4.16 (bs, 1H), 3.60 (s, 3H), 3.41-3.36 (m, 4H), 2.90-2.89 (d, J = 4.8 Hz, 3H), 1.72-1.64 (m, 6H), 1.11-1.07 (t, J = 6.8 Hz, 2H). |

Example 106: Synthesis of compound comprising N-(3-hydroxycyclohexyl)aminocarbonyl at position 3 of the pyrazolo[1,5-a]pyrimidine 106.1. Synthesis of N-(3-hydroxycyclohexyl)-5-((2-methoxypyridin-3-yl)amino)-7-(methylamino)pyrazolo[1,5-a]pyrimidine-3-carboxamide (I-459)

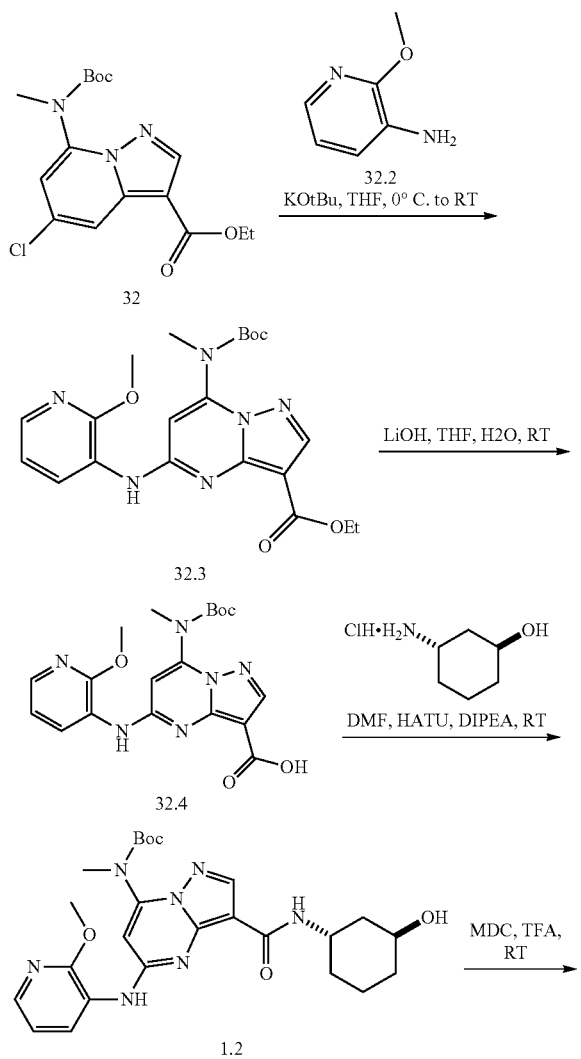

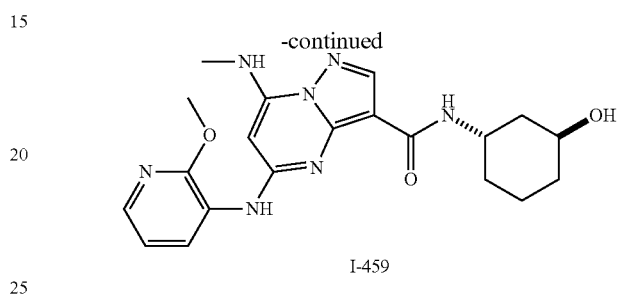

Synthesis of Compound 32.

Compound was synthesized using general procedure of core synthesis to obtain 32. (Yield: 62.21%). MS (ES): m/z 355.5 [M+H]+

Synthesis of Compound 32.3.

To a cooled solution of 32. (0.500 g, 1.41 mmol, 1.0 eq), and 32.2 (0.174 g, 1.41 mmol, 1.0 eq) in tetrahydrofuran (10 mL) at 0° C. was added potassium ter-butoxide (2.8 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 32.3 (0.630 g, 96.22%). MS (ES): m/z 442.48 [M+H]+.

Synthesis of Compound 32.4.

To a solution of 32.3 (0.600 g, 1.36 mmol, 1.0 eq), in tetrahydrofuran: water (20 mL, 2:1) was added lithium hydroxide (0.312 g, 13.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 32.4 (0.400 g, 71.18%). MS(ES): m/z 415.42 [M+H]+.

Synthesis of Compound 1.2.

Compound was synthesized using general procedure A to obtain 1.2. (0.210 g, Yield: 56.70%). MS (ES): m/z 512.58 [M+H]+.

Synthesis of Compound I-459:

Compound was synthesized using general procedure C to obtain I-459 (0.154 g, Yield: 91.18%). MS (ES): m/z 412.17 [M+H]+, LCMS purity: 97.51%, HPLC purity: 95.08%, Chiral HPLC: 50.01% and 48.68%. 1H NMR (DMSO-d6, 400 MHZ): 8.91 (s, 1H), 8.24-8.23 (d, J=4.0 Hz, 1H), 8.14 (s, 1H), 7.92-7.91 (m, 2H), 7.59-7.57 (d, J=8.0 Hz, 1H), 7.01-6.98 (m, 1H), 5.90 (s, 1H), 4.15-4.11 (m, 1H), 3.90 (bs, 4H), 2.92-2.90 (d, J=8.0 Hz, 3H), 1.76-1.52 (m, 4H), 1.55-1.52 (m, 1H), 1.39-1.36 (m, 2H), 1.08-1.00 (m, 2H).

Additional compounds prepared by substantially the same method, and their characterization data, are listed in the Table 54 below. The intermediate corresponding to 32.2 of the above scheme is listed for each compound.

TABLE 54

| Compound | Intermediate | Characterization Data |
|---|---|---|
| I-460 | ![intermediate structure with CD3, N, O, NH2] | MS (ES): m/z 415.33 [M + H]+, LCMS purity: 98.87%, HPLC purity: 98.20%, CHIRAL HPLC: 49.57% + 48.61%, $^1$H NMR (DMSO-$d_6$, 400 MHZ): 8.89 (s, 1H), 8.23-8.21 (d, J = 7.6 Hz, 1H), 8.14-8.13 (m, 1H), 7.91-7.90 (m, 2H), 7.58-7.56 (m, 1H), 7.00-6.97 (m, 1H), 5.90 (s, 1H), 4.48 (s, 1H), 4.15 (s, 1H), 3.90 (s, 1H), 2.90 (s, 3H), 1.75 (s, 2H), 1.66-1.63 (m, 2H), 1.38-1.36 (m, 2H), 1.28-1.22 (m, 1H), 1.05-1.02 (m, 1H). |

7.2. Chiral Separation of Compound I-459

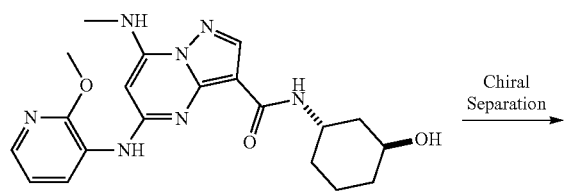

Chiral Separation →

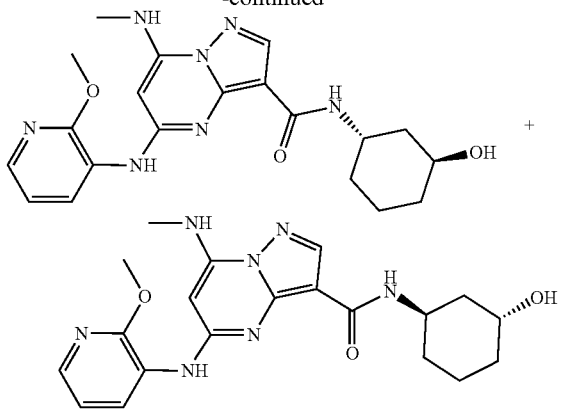

Synthesis of I-496 and I-497.

Isomers of I-459 (0.154 g) were separated out using column (CHIRALPAK AD-H (250 mm*4.6 mm, 5 u)) in 0.1% DEA in MeOH with flow rate of 4 mL/min. to get pure fraction-1 (FR-a) and fraction-2 (FR-b).

FR-a was concentrated under reduced pressure at 30° C. to afford pure FR-a (0.034 g). MS(ES): m/z 412.30 [M+H]+, LCMS purity: 99.45%, HPLC purity: 99.04%, CHIRAL HPLC purity: 99.83%, $^1$H NMR (DMSO-$d_6$, 400 MHZ: 8.89 (s, 1H), 8.24-8.22 (d, J 8.0 Hz, 1H), 8.14 (s, 1H), 7.92-7.90 (m, 2H), 7.58-7.55 (d, J=12 Hz, 1H), 7.00-6.91 (m, 1H), 5.90 (s, 1H), 4.15-4.13 (m, 1H), 3.95 (s, 1H), 3.90-3.88 (m, 4H), 2.91-2.90 (d, J=4.0 Hz, 3H), 1.76-1.52 (m, 4H), 1.38-1.00 (m, 4H).

FR-b was concentrated under reduced pressure at 30° C. to afford pure FR-b (0.032 g). MS(ES): m/z 412.22 [M+H]+, LCMS purity: 98.58%, HPLC purity: 97.29%, CHIRAL HPLC purity: 99.37%, $^1$H NMR (DMSO-$d_6$, 400 MHZ): 8.89 (s, 1H), 8.23-8.22 (d, J=4.0 Hz, 1H), 8.14 (s, 1H), 7.92-7.91 (m, 2H), 7.58-7.55 (d, J=12 Hz, 1H), 7.00-6.97 (m, 1H), 5.90 (s, 1H) 4.47 (s, 1H), 4.15-4.13 (m, 1H), 4.00-3.90 (m, 4H), 2.91-2.90 (d, J 8.0 Hz, 3H), 1.75-1.51 (m, 4H), 1.38-1.23 (m, 4H).

Additional compounds prepared by substantially the same method, and their characterization data, are listed in the Table 55 below.

TABLE 55

| Compound | Isomers | Characterization Data |
|---|---|---|
| I-460 | I-498<br>I-499 | FR-a: MS (ES): m/z 414.48 [M + H]+, LCMS purity: 99.52%, HPLC purity: 98.48%, CHIRAL HPLC: 100% $^1$H NMR (DMSO-$d_6$, 400 MHZ): 8.88 (s, 1H), 8.23-8.21 (dd, J = 6.4 Hz, 7.6 Hz, 1H), 8.13 (s, 1H), 7.97-7.87 (m, 2H), 7.57-7.55 (m, 1H), 7.00-6.97 (m, 1H), 5.90 (s, 1H), 4.47-4.46 (m, 1H), 4.15-4.13 (m, 1H), 3.90 (s, 1H), 2.91-2.90 (d, J = 4.8, 3H), 1.75-1.66 (m, 2H), 1.63-1.60 (m, 1H), 1.54-1.52 (m, 1H), 1.38-1.36 (m, 2H), 1.28-1.23 (m, 1H), 1.09-1.00 (m, 1H).<br>FR-b: MS (ES): m/z 414.48 [M + H]+, LCMS purity: 100%, HPLC purity: 99.01%, CHIRAL HPLC: 99.52% $^1$H NMR (DMSO-$d_6$, 400 MHZ): 8.88 (s, 1H), 8.23-8.21 (dd, J = 6.0 Hz, 7.6 Hz, 1H), 8.13 (s, 1H), 7.92-7.88 (m, 2H), 7.57-7.55 (d, J = 8.4, 1H), 7.00-6.97 (m, 1H), 5.90 (s, 1H), 4.47-4.46 (m, 1H), 4.14-4.10 (m, 1H), 3.90 (s, 1H), 2.91-2.90 (d, J = 4.8, 3H), 1.75-1.66 (m, 2H), 1.67-1.63 (m, 1H), 1.54-1.52 (m, 1H), 1.38-1.36 (m, 2H), 1.28-1.23 (m, 1H), 1.08-1.00 (m, 1H). |

TABLE 55-continued

| Compound | Isomers | Characterization Data |
|---|---|---|
| I-703 | I-734<br>I-735 | FR-a: MS (ES): m/z 482.31 [M + H]+, LCMS purity: 100%, HPLC purity: 99.66%, CHIRAL HPLC purity: 100%, $^1$H NMR (DMSO-$d_6$, 400 MHZ): 8.89 (s, 1H), 8.21 (s, 1H), 8.19 (s, 1H), 7.92-7.91 (d, J = 4.8 Hz, 1H), 7.54-7.52 (d, J = 7.6 Hz, 2H), 6.31-6.27 (t, J = 7.2 Hz, 1H), 6.24 (s, 1H), 5.77 (s, 1H), 4.91-4.86 (m, 1H), 4.55 (bs, 1H), 4.24-4.21 (m, 1H), 3.98 (bs, 1H), 3.86-3.82 (m, 2H), 3.61-3.56 (t, J = 10.4 Hz, 1H), 3.49-3.44 (t, J = 8.8 Hz, 1H), 2.91-2.90 (d, J = 4.4 Hz, 3H), 2.08 (bs, 1H), 1.77-1.72 (m, 4H), 1.49-1.40 (m, 4H), 1.24-1.19 (m, 2H). FR-b: MS (ES): m/z 482.56 [M + H]+, LCMS purity: 97.79%, HPLC purity: 96.00%, CHIRAL HPLC purity: 100%, $^1$H NMR (DMSO-$d_6$, 400 MHZ): 8.89 (s, 1H), 8.20 (s, 1H), 8.18 (s, 1H), 7.91-7.90 (d, J = 4.8 Hz, 1H), 7.53-7.51 (d, J = 7.6 Hz, 2H), 6.30-6.26 (t, J = 7.2 Hz, 1H), 6.23 (s, 1H), 5.76 (s, 1H), 4.87 (bs, 1H), 4.54 (bs, 1H), 4.20 (bs, 1H), 3.97 (bs, 1H), 3.84 (bs, 2H), 3.59-3.54 (t, J = 9.2 Hz, 1H), 3.48-3.43 (t, J = 8.4 Hz, 1H), 2.90-2.89 (d, J = 4.4 Hz, 3H), 2.06 (bs, 1H), 1.76-1.71 (m, 4H), 1.48-1.38 (m, 4H), 1.23-1.18 (m, 2H). |
| I-704 | I-780<br>I-781 | FR-a: MS (ES): m/z 482.62 [M + H]+, LCMS purity: 97.97%, HPLC purity: 98.34%, CHIRAL HPLC purity: 100%, $^1$H NMR (DMSO-$d_6$, 400 MHZ): 8.90 (s, 1H), 8.21 (s, 1H), 8.19 (s, 1H), 7.92-7.91 (d, J = 4.8 Hz, 1H), 7.54-7.52 (d, J = 8 Hz, 2H), 6.31-6.27 (t, J = 7.2 Hz, 1H), 6.24 (s, 1H), 4.91-4.86 (m, 1H), 4.55 (bs, 1H), 4.23-4.21 (m, 1H), 3.99 (bs, 1H), 3.86-3.82 (t, J = 7.6 Hz, 2H), 3.60-3.55 (t, J = 10.4 Hz, 1H), 3.49-3.44 (t, J = 8.4 Hz, 1H), 2.91-2.90 (d, J = 4.8 Hz, 3H), 1.88 (bs, 3H), 1.77-1.72 (m, 4H), 1.48-1.40 (m, 3H), 1.24-1.19 (m, 2H). FR-b: MS (ES): m/z 482.62 [M + H]+, LCMS purity: 99.37%, HPLC purity: 96.94%, CHIRAL HPLC purity: 100%, $^1$H NMR (DMSO-$d_6$, 400 MHZ): 8.90 (s, 1H), 8.21 (s, 1H), 8.19 (s, 1H), 7.92-7.91 (d, J = 4.4 Hz, 1H), 7.54-7.53 (d, J = 7.6 Hz, 2H), 6.31-6.27 (t, J = 7.2 Hz, 1H), 6.24 (s, 1H), 4.88 (bs, 1H), 4.55 (bs, 1H), 4.23 (bs, 1H), 3.99 (bs, 1H), 3.85 (bs, 2H), 3.60-3.55 (t, J = 10 Hz, 1H), 3.49-3.44 (t, J = 10.4 Hz, 1H), 2.91-2.90 (d, J = 4 Hz, 3H), 1.88 (bs, 3H), 1.77-1.72 (m, 4H), 1.49-1.40 (m, 3H), 1.12-1.08 (t, J = 6.8 Hz, 2H). |
| I-919 | I-1078<br>I-1079 | FR-a: MS (ES): m/z 440.37 [M + H]+, LCMS purity: 96.64%, HPLC purity: 97.41%, CHIRAL HPLC purity: 100%, $^1$H NMR (DMSO-$d_6$, 400 MHZ): 8.88 (s, 1H), 8.19-8.18 (m, 2H), 7.91-7.90 (d, J = 4.8 Hz, 1H), 7.56-7.54 (d, J = 8.4 Hz, 1H), 7.47-7.45 (d, J = 6.8 Hz, 1H), 6.31-6.28 (t, J = 7.2 Hz, 1H), 6.24 (s, 1H), 5.21-5.15 (m, 1H), 4.57-4.56 (d, J = 3.2 Hz, 1H), 4.24-4.22 (m, 1H), 3.99 (s, 1H), 2.92-2.91 (d, J = 4.8 Hz, 3H), 1.92-1.88 (m, 2H), 1.75-1.69 (m, 1H), 1.60-1.57 (m, 1H), 1.50-1.46 (m, 2H), 1.37-1.35 (d, J = 4.2 Hz, 6H), 1.25-1.17 (m, 2H). FR-b: MS (ES): m/z 440.37 [M + H]+, LCMS purity: 96.81%, HPLC purity: 98.24%, CHIRAL HPLC purity: 95.57%, $^1$H NMR (DMSO-$d_6$, 400 MHZ): 8.88 (s, 1H), 8.19-8.18 (m, 2H), 7.91-7.90 (d, J = 4.8 Hz, 1H), 7.56-7.54 (d, J = 8.4 Hz, 1H), 7.47-7.45 (d, J = 6.8 Hz, 1H), 6.31-6.28 (t, J = 7.2 Hz, 1H), 6.24 (s, 1H), 5.21-5.15 (m, 1H), 4.57-4.56 (d, J = 3.2 Hz, 1H), 4.24-4.22 (m, 1H), 3.99 (s, 1H), 2.92-2.91 (d, J = 4.8 Hz, 3H), 1.92-1.88 (m, 2H), 1.75-1.69 (m, 1H), |

TABLE 55-continued

| Compound | Isomers | Characterization Data |
|---|---|---|
| | | 1.60-1.57 (m, 1H), 1.50-1.46 (m, 2H), 1.37-1.35 (d, J = 4.2 Hz, 6H), 1.25-1.17 (m, 2H). |

106.3. Synthesis of 5-N-(3-hydroxycyclohexyl)-5-((1-isopropyl-2-oxo-1,2-dihydropyridin-3-yl)amino)-7-(methylamino)pyrazolo[1,5-a]pyrimidine-3-carboxamide (I-919)

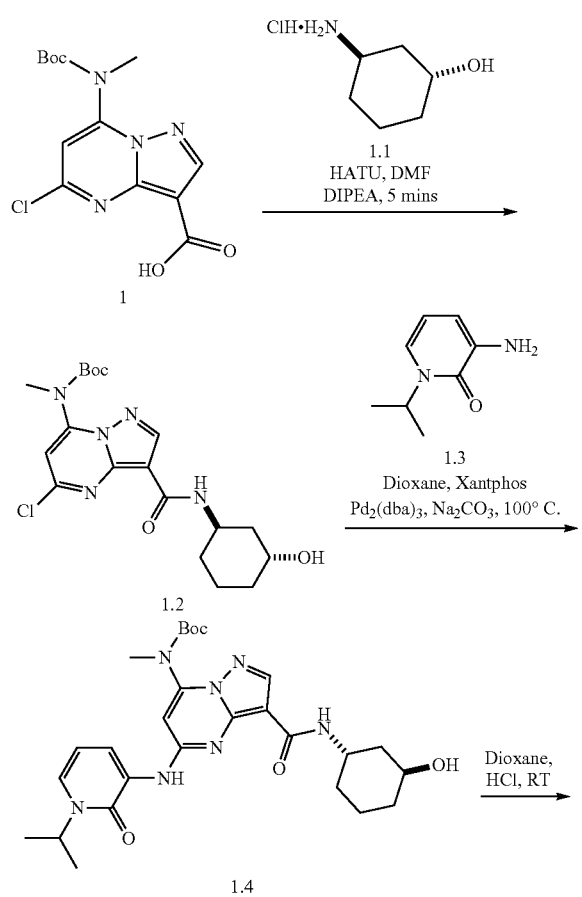

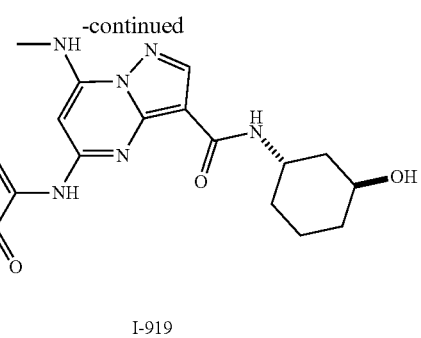

I-919

Synthesis of Compound 1.

Compound was synthesized using general procedure of core synthesis to obtain 1. (Yield: 71.67%). MS (ES): m/z 327.08 [M+H]$^+$ Synthesis of Compound 1.2.

Compound was synthesized using general procedure A to obtain 1.2. (0.3 g, 46.25%), MS (ES): 424.17 [M+H]$^+$ Synthesis of Compound 1.4.

Compound was synthesized using general procedure B to obtain 1.4. (0.125 g, 65.46%), MS (ES): m/z 539.64 [M+H]$^+$ Synthesis of Compound I-919:

Compound was synthesized using general procedure C to obtain I-919 (0.100 g, 98.22%). MS (ES): m/z 440.23 [M+H]$^+$, LCMS purity: 95.01%, HPLC purity: 98.24%, CHIRAL HPLC purity: 46.35%, 50.58%,1H NMR (DMSO-d6, 400 MHZ): 8.96 (bs, 1H), 8.21 (s, 1H), 8.15-8.14 (d, J=6.8 Hz, 1H), 7.99 (bs, 1H), 7.59-7.57 (d, J=7.6 Hz 1H), 7.47-7.46 (d, J=6.81H), 6.31-6.27 (t, J=14.4 Hz, 1H), 6.19 (s, 1H), 5.20-5.13 (m, 1H), 4.22 (s, 1H), 3.98 (s, 1H), 2.91-2.90 (d, J=3.2 Hz, 3H), 1.89-1.86 (d, J=11.2 Hz, 2H), 1.59-1.56 (m, 2H), 1.45 (m, 3H), 1.40-1.35 (d, J=18 Hz, 6H), 1.22-1.15 (m, 2H).

Additional compounds prepared by substantially the same method, and their characterization data, are listed in the Table 56 below. The intermediate corresponding to 1.3 of the above scheme is listed for each compound.

TABLE 56

| Compound | Intermediate | Characterization Data |
|---|---|---|
| I-703 | ![intermediate structure with tetrahydropyran, pyridinone, NH2] | MS (ES): m/z 482.52 [M + H]$^+$, LCMS purity: 100%, HPLC purity: 98.44%, CHIRAL HPLC: 48.94%, 49.35%, $^1$H NMR (DMSO-d$_6$, 400 MHZ): 8.91 (s, 1H), 8.21 (s, 1H), 8.19 (s, 1H), 7.93-7.92 (d, J = 4.8 Hz, 1H), 7.55-7.53 (d, J = 8 Hz, 2H), 6.31-6.27 (t, J = 6.8 Hz, 1H), 6.24 (s, 1H), 5.78 (s, 1H), 4.91-4.86 (m, 1H), 4.56 (bs, 1H), 4.23-4.21 (m, 1H), 3.98 (bs, 1H), 3.86-3.82 (t, J = 5.2 Hz, 2H), 3.60-3.55 (t, J = 9.6 Hz, 1H), 3.18 (s, 1H), 2.91-2.90 (d, J = 6.8 Hz, 3H), 2.69 (bs, 1H), 2.10-2.03 (m, 1H), 1.77-1.72 (m, 3H), 1.49-1.48 (d, J = 4.4 Hz, 3H), 1.24-1.19 (m, 2H), 1.09 (s, 1H). |

TABLE 56-continued

| Compound | Intermediate | Characterization Data |
|---|---|---|
| I-704 | | MS (ES): m/z 482.31 [M + H]⁺, LCMS purity: 100%, HPLC purity: 96.83%, CHIRAL HPLC: 52.32%, 47.67%, ¹H NMR (DMSO-d₆, 400 MHZ): 8.90 (s, 1H), 8.21 (s, 1H), 8.19 (s, 1H), 7.92-7.91 (d, J = 4.8 Hz, 1H), 7.54-7.52 (d, J = 8 Hz, 2H), 6.31-6.27 (t, J = 7.2 Hz, 1H), 6.24 (s, 1H), 4.88 (bs, 1H), 4.55-4.54 (d, J = 2.8 Hz, 1H), 4.24-4.21 (m, 1H), 3.99 (bs, 1H), 3.85 (bs, 2H), 3.60-3.55 (t, J = 9.6 Hz, 1H), 3.49-6.44 (t, J = 8 Hz, 1H), 2.91-2.90 (d, J = 4.4 Hz, 3H), 1.88 (bs, 2H), 1.77-1.71 (m, 4H), 1.40-1.37 (d, J = 12.4 Hz, 4H), 1.24-1.19 (m, 2H). |

Example 107. Synthesis of compound comprising N-(2-hydroxycyclobutyl)aminocarbonyl at position 3 of the pyrazolo[1,5-a]pyrimidine 107.1. Synthesis of N-((1R,2R)-2-hydroxycyclobutyl)-5-((2-methoxypyridin-3-yl)amino)-7-(methylamino)pyrazolo[1,5-a]pyrimidine-3-carboxamide (I-363)

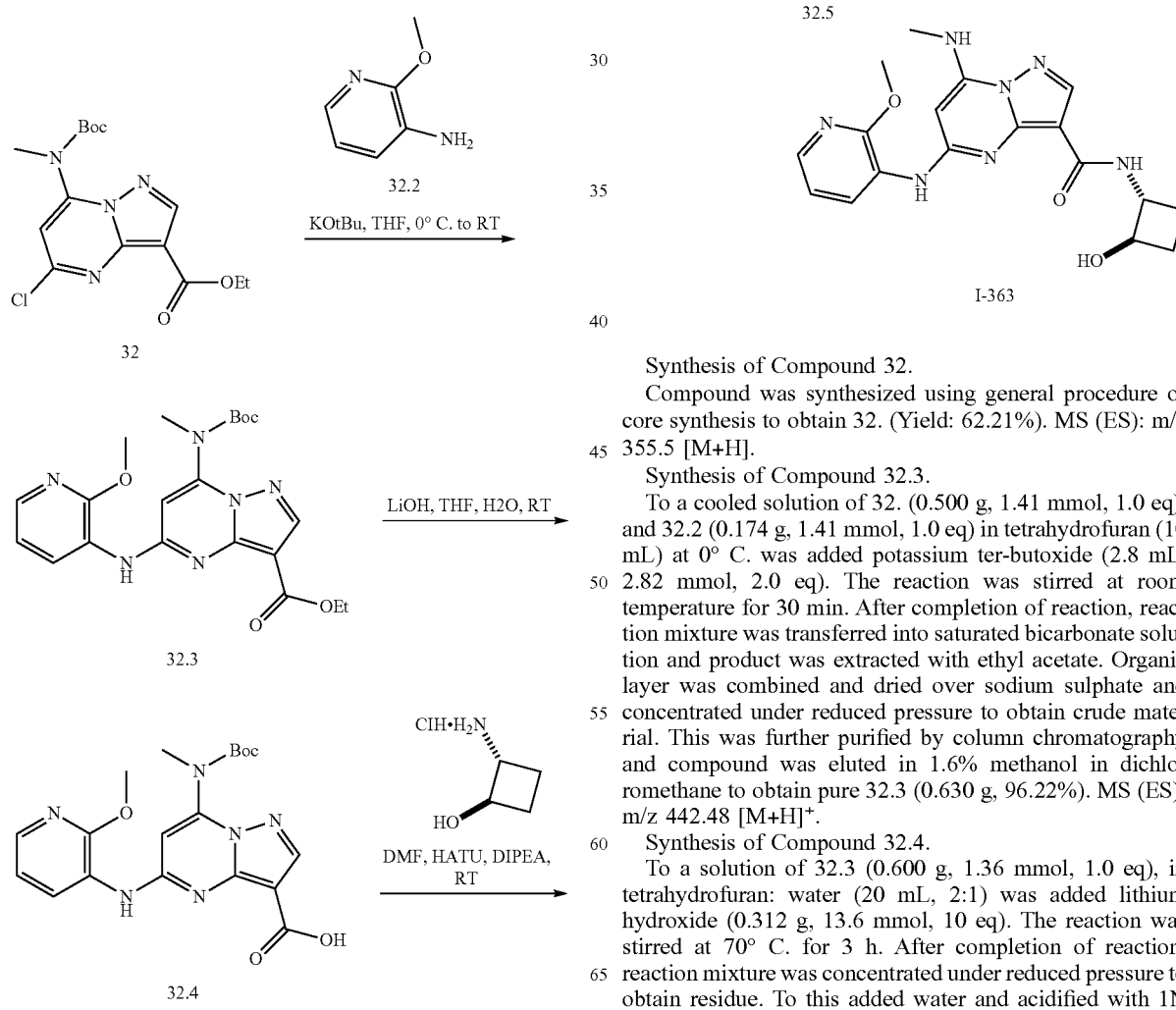

Synthesis of Compound 32.

Compound was synthesized using general procedure of core synthesis to obtain 32. (Yield: 62.21%). MS (ES): m/z 355.5 [M+H].

Synthesis of Compound 32.3.

To a cooled solution of 32. (0.500 g, 1.41 mmol, 1.0 eq), and 32.2 (0.174 g, 1.41 mmol, 1.0 eq) in tetrahydrofuran (10 mL) at 0° C. was added potassium ter-butoxide (2.8 mL, 2.82 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 32.3 (0.630 g, 96.22%). MS (ES): m/z 442.48 [M+H]⁺.

Synthesis of Compound 32.4.

To a solution of 32.3 (0.600 g, 1.36 mmol, 1.0 eq), in tetrahydrofuran: water (20 mL, 2:1) was added lithium hydroxide (0.312 g, 13.6 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 32.4 (0.400 g, 71.18%). MS(ES): m/z 415.42 [M+H]⁺.

Synthesis of Compound 32.5.

Compound was synthesized using general procedure A to obtain 32.5. (0.160 g, 768.57%). MS (ES): m/z 484.53 [M+H]⁺

Synthesis of Compound I-363.

Compound was synthesized using general procedure C to obtain I-363 (0.105 g, 82.76%). MS (ES): m/z 384.41 [M+H]⁺, LCMS purity: 99.67%, HPLC purity: 98.98%, Chiral HPLC purity: 49.64%+49.66%, ¹H NMR (DMSO-d₆, 400 MHZ): 8.97 (s, 1H), 8.30-8.28 (d, J=7.2 Hz, 1H), 8.15 (s, 1H), 8.05-8.02 (d, J=9.2 Hz, 1H), 7.94 (s, 2H), 7.05-7.02 (m, 1H), 5.92 (s, 1H), 5.36-5.34 (d, 1 J=7.2 Hz, 1H), 4.20-4.15 (t, J=8 Hz, 1H), 3.90 (s, 3H), 3.68-3.62 (m, 1H), 2.92-2.91 (d, J=4.4 Hz, 1H), 2.02-1.90 (m, 2H), 1.48-1.33 (m, 1H), 1.24 (bs, 1H), 1.13-1.03 (m, 2H).

Additional compounds prepared by substantially the same method, and their characterization data, are listed in the Table 57 below. The intermediate corresponding to of the 32.2 above scheme is listed for each compound.

TABLE 57

| Compound | Intermediate | Characterization Data |
|---|---|---|
| I-366 | 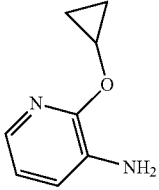 [SMILES: Nc1cccnc1OC1CC1] | MS (ES): m/z 410.45 [M + H]⁺, LCMS purity: 100%, HPLC purity: 99.41%, Chiral HPLC purity: 49.33% + 49.52%, ¹H NMR (DMSO-d₆, 400 MHZ): 8.76 (s, 1H), 8.29-8.27 (d, J = 6.4 Hz, 1H), 8.19 (s, 1H), 8.01-7.92 (m, 3H), 7.07-7.04 (m, 1H), 5.87 (s, 1H), 5.34-5.32 (d, J = 7.2 Hz, 1H), 4.37-4.34 (m, 1H), 4.21-4.41 (m, 1H), 3.72-3.57 (m, 1H), 2.92-2.91 (d, J = 4.8 Hz, 2H), 2.01-1.90 (m, 2H), 1.56-1.34 (m, 1H), 1.33 (s, 1H), 1.10-1.05 (m, 1H), 1.03-0.74 (m, 4H). |
| I-373 | 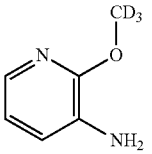 | MS (ES): m/z 387.45 [M + H]⁺, LCMS purity: 100%, HPLC purity: 100%, CHIRAL HPLC purity: 49.35%, 50.64%, ¹H NMR (DMSO-d₆, 400 MHZ): 8.97 (s, 1H), 8.30-8.28 (d, J = 6.4 Hz, 1H), 8.15 (s, 1H), 8.05-8.02 (d, J = 9.2 Hz, 1H), 7.93 (bs, 2H), 7.05-7.02 (m, 1H), 5.92 (s, 1H), 5.36-5.34 (d, J = 7.2 Hz, 1H) 4.20-4.15 (t, J = 8.4 Hz, 1H), 3.68-3.64 (t, J = 7.6 Hz, 1H), 2.92-2.91 (d, J = 4.8 Hz, 3H), 2.02-1.90 (m, 3H), 1.13-1.06 (m, 1H). |
| I-472 | 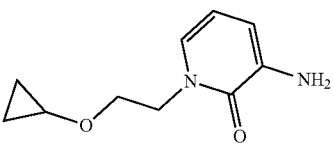 [SMILES: Nc1cccn(CCOC2CC2)c1=O] | MS (ES): m/z 454.47 [M + H]⁺, LCMS purity: 96.20%, HPLC purity: 95.86%, CHIRAL HPLC purity: 48.09%, 47.56% ¹H NMR (DMSO-d₆, 400 MHZ): 8.95 (s, 1H), 8.26-8.24 (d, J = 7.2 Hz, 1H), 8.19 (s, 1H), 8.04-8.02 (d, J = 8.8 Hz, 1H), 7.94-7.93 (s, J = 4.8 Hz, 1H), 7.35-7.33 (d, J = 6.8 Hz, 1H), 6.31-6.28 (t, J = 7.2 Hz, 1H), 6.23 (s, 1H), 5.45-5.43(d, J = 7.2 Hz, 1H), 4.25-4.16 (m, 3H), 3.87-3.83 (t, J = 8 Hz, 1H), 3.77-3.75 (t, J = 5.2 Hz, 2H), 2.91-2.90 (d, J = 4.4 Hz, 3H), 2.06-1.99 (m, 2H), 1.51-1.46 (t, J = 9.6 Hz, 2H), 1.26-1.19 (m, 2H), 0.40 (bs, 3H). |
| I-602 | 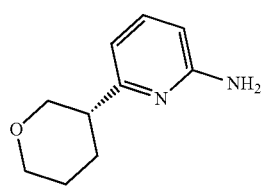 [SMILES: Nc1cccc([C@@H]2CCCOC2)n1] | MS(ES): m/z 438.6 [M + H]⁺ LCMS purity: 100%, HPLC purity: 97.69%, NMR (DMSO-d₆, 400 MHZ): 9.90 (s, 1H), 8.21-8.076 (m, 3H), 7.72-7.68 (d, J = 7.6 Hz, 1H), 7.56 (s, 1H), 6.97-6.96 (d, J = 7.6 Hz, 1H), 6.69 (s, 1H), 5.41 (d, J = 7.2 Hz, 1H), 4.24-4.20 (t, J = 8.4 Hz, 1H), 4.02-3.88 (m, 4H), 4.55-4.50 (d, J = 10.8 Hz, 1H), 2.97-42.89 (m, J = 10.8 Hz, 4H), 2.01-1.89 (m, 4H), 1.67 (s, 2H), 1.50-1.45 (d, J = 9.2 Hz 1H), 1.31-1.24 (m, 1H). |
| I-603 | 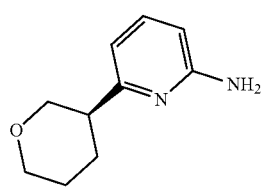 [SMILES: Nc1cccc([C@H]2CCCOC2)n1] | MS(ES): m/z 438.6 [M + H]⁺ LCMS purity: 98.99%, HPLC purity: 97.46%, NMR (DMSO-d₆, 400 MHZ): 9.90 (s, 1H), 8.21 (s, 1H), 8.162-140 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.41-5.39 (d, J = 7.2 Hz, 1H), 4.24-4.20 (m, 1H), 4.02-3.88 (m, 3H), 3.55-3.50 (t, |

TABLE 57-continued

| Compound | Intermediate | Characterization Data |
|---|---|---|
| | | J = 10.8 Hz, 1H), 2.97-2.96 (m, 1H), 2.89 (s, 3H), 2.03-1.89 (m, 4H), 1.67 (bs, 2H), 1.50-1.45 (m, 1H), 1.31-1.24 (m, 2H). |

107.2. Chiral Separation of I-363

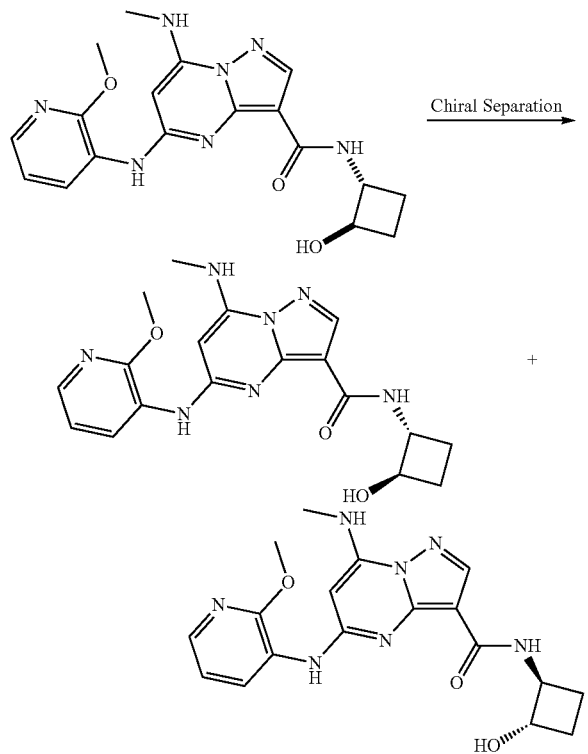

Synthesis of Compound I-395 & I-396.

Isomers of I-363 (0.105 g) were separated out using column (CHIRAL PAK AD-H 250×4.6 mm, 5 u) 0.1% DEA_HEX_IPA-ACN(70-30)_GRD-07 to get pure fraction-1 (FR-a) and fraction-2 (FR-b). FR-a was concentrated under reduced pressure at 30° C. to afford pure FR-a (0.025 g). MS(ES): m/z 384.45 [M+H]$^+$, LCMS purity: 100%, HPLC purity: 100%, CHIRAL HPLC purity: 99.78%, $^1$H NMR (DMSO-d$_6$, 400 MHZ): 8.98 (s, 1H), 8.30-8.28 (d, J=7.6 Hz, 1H), 8.15 (s, 1H), 8.04-8.02 (d, J 8.8 Hz, 1H), 7.94-7.94 (d, J=3.6 Hz, 2H), 7.05-7.02 (m, 1H), 5.92 (s, 1H), 5.36-5.34 (d, J=6.8 Hz, 1H), 4.20-4.15 (t, J=8.4 Hz, 1H), 3.97 (s, 3H), 3.68-3.64 (t, J=7.2 Hz, 1H), 2.92-2.91 (d, J=4.8 Hz, 3H), 2.02-1.91 (m, 2H), 1.48-1.38 (m, 1H), 1.13-1.03 (m, 1H).

FR-b was concentrated under reduced pressure at 30° C. to afford pure FR-b (0.025 g). MS(ES): m/z 384.45 [M+H]$^+$, LCMS purity: 100%, HPLC purity: 99.67%, CHIRAL HPLC purity: 98.79%, $^1$H NMR (DMSO-d$_6$, 400 MHZ): 8.97 (s, 1H), 8.30-8.28 (d, J=7.6 Hz, 1H), 8.15 (s, 1H), 8.04-8.02 (d, J=9.2 Hz, 1H), 7.94-7.94 (d, J=3.2 Hz, 2H), 7.05-7.02 (m, 1H), 5.92 (s, 1H), 5.35 (s, 1H), 4.22-4.13 (m, 1H) 3.97 (s, 3H), 3.67-3.65 (d, J=7.2 Hz, 1H), 2.92 (s, 3H), 2.02-1.90 (m, 2H), 1.48-1.38 (m, 1H), 1.13-1.04 (m, 1H).

Additional compounds prepared by substantially the same method, and their characterization data, are listed in the Table 58 below.

TABLE 58

| Compound | Isomers | Characterization Data |
|---|---|---|
| I-366 | I-397<br>I-398 | FR-a: MS (ES): m/z 410.32 [M + H]$^+$,<br>LCMS purity: 100%, HPLC purity: 98.57%,<br>CHIRAL HPLC purity: 99.66%, $^1$H NMR<br>(DMSO-d$_6$, 400 MHZ): 8.77 (bs, 1H),<br>8.30-8.28 (d, J = 6.8 Hz, 1H), 8.15 (s, 1H), 8.02 (s, 1H),<br>8.00 (s, 1H) 7.08-7.04 (m, 1H), 5.88 (s, 1H),<br>5.35 (bs, 1H), 4.36 (bs, 1H), 4.22-4.13 (m, 1H),<br>3.69-3.63 (m, 1H), 2.92 (s, 3H), 2.02-1.90 (m,<br>2H), 1.48-1.40 (m, 1H), 1.24 (s, 1H),<br>1.14-1.04 (m, 1H), 0.86 (bs, 4H).<br>FR-b: MS (ES): m/z 410.50 [M + H]$^+$,<br>LCMS purity: 100%, HPLC purity: 99.69%,<br>CHIRAL HPLC purity: 98.36%, $^1$H NMR<br>(DMSO-d$_6$, 400 MHZ): 8.77 (bs, 1H),<br>8.29-8.27 (d, J = 8 Hz, 1H), 8.15 (s, 1H), 7.99 (s, 1H),<br>7.93 (s, 1H), 7.07-7.04 (m, 1H), 5.87 (s, 1H),<br>5.38 (bs, 1H), 4.36 (bs, 1H), 4.21-4.12 (m, 1H),<br>3.68-3.64 (m, 1H), 2.91 (s, 3H), 2.01-1.89 (m,<br>2H), 1.47-1.40 (m, 1H), 1.23 (s, 1H),<br>1.10-1.03 (m, 1H), 0.81 (bs, 4H). |
| I-373 | I-410<br>I-411 | FR-a: MS (ES): m/z 385.51 [M − H]$^+$,<br>LCMS purity: 100%, HPLC purity: 100%,<br>CHIRAL HPLC purity: 100%, $^1$H NMR<br>(DMSO-d$_6$, 400 MHZ): 8.97 (s, 1H),<br>8.30-8.28 (d, J = 7.6 Hz, 1H), 8.15 (s, 1H), 8.04-8.02 (d, |

TABLE 58-continued

| Compound | Isomers | Characterization Data |
|---|---|---|
| | | J = 9.2 Hz, 1H), 7.94-7.92 (m, 2H), 7.05-7.02 (m, 1H), 5.92 (s, 1H), 5.35-5.33 (d, J = 7.2 Hz, 1H), 3.68-3.64 (t, J = 7.6 Hz, 1H), 2.92-2.91 (d, J = 4.8 Hz, 3H), 2.02-1.91 (m, 3H), 1.45-1.41 (t, J = 9.6 Hz, 1H), 1.11-1.06 (m, 1H). FR-b: MS (ES): m/z 385.34 [M − H]$^+$, LCMS purity: 100%, HPLC purity: 100%, CHIRAL HPLC purity: 99.27%, $^1$H NMR (DMSO-d$_6$, 400 MHZ): 8.97 (s, 1H), 8.30-8.28 (d, J = 7.6 Hz, 1H), 8.15 (s, 1H), 8.04-8.02 (d, J = 8.8 Hz, 1H), 7.94-7.92 (t, J = 4.4 Hz, 2H), 7.05-7.02 (m, 1H), 5.92 (s, 1H), 5.35-5.33 (d, J = 7.2 Hz, 1H), 3.68-3.64 (m, 1H), 2.92-2.91 (d, J = 4.4 Hz, 3H), 2.00-1.91 (m, 3H), 1.45-1.40 (t, J = 9.6 Hz, 1H) 1.11-1.06 (m, 1H). |
| I-472 | I-513 I-514 | FR-a: MS (ES): m/z 454.50 [M + H]$^+$. LCMS purity: 95.95%, HPLC purity: 96.49%, Chiral HPLC purity: 100%, NMR (DMSO-d$_6$, 400 MHZ): 8.93 (s, 1H), 8.25-8.23 (d, J = 6 Hz, 1H), 8.19 (s, 1H), 8.03-8.01 (d, J = 8.8 Hz, 1H), 7.92 (s, 1H), 7.34-7.32 (d, J = 6.8 Hz, 1H), 6.30-6.27 (t, J = 7.2 Hz, 1H), 6.22 (s, 1H), 5.43 (s, 1H), 4.24-4.15 (m, 4H), 3.85-3.83 (d, J = 6 Hz, 1H), 3.77-3.74 (t, J = 5.2 Hz, 2H), 2.90-2.90 (d, J = 2.8 Hz, 3H), 2.12-1.98 (m, 2H), 1.53-1.43 (m, 1H), 1.29-1.14 (m, 3H), 0.41-0.40 (m, 2H). FR-b: MS (ES): m/z 454.50 [M + H]$^+$ LCMS purity: 100%, HPLC purity: 99.72%, Chiral HPLC purity: 98.37%, NMR (DMSO-d$_6$, 400 MHZ): 8.93 (s, 1H), 8.25-8.23 (d, J = 7.2 Hz, 1H), 8.19 (s, 1H), 8.03-8.01 (d, J = 8.8 Hz, 1H), 7.92-7.91 (d, J = 4.8 Hz, 1H), 7.34-7.32 (d, J = 6.8 Hz, 1H), 6.30-6.27 (t, J = 7.2 Hz, 1H), 6.22 (s, 1H), 5.43-5.42 (d, J = 7.2 Hz, 1H), 4.24-4.15 (m, 4H), 3.86-3.80 (m, 1H), 3.77-3.74 (t, J = 5.2 Hz, 2H), 2.91-2.89 (d, J = 4.8 Hz, 3H), 2.12-1.98 (m, 2H), 1.53-1.43 (m, 1H), 1.23-1.15 (m, 3H), 0.41-0.40 (m, 2H). |
| I-528 | I-596 I-597 | FR-a: MS (ES): m/z 454.50 [M + H]$^+$, LCMS purity: 100%, HPLC purity: 100% CHIRAL HPLC: 100%, $^1$H NMR (DMSO-d$_6$, 400 MHZ): 8.92 (s, 1H), 8.26-8.24 (d, J = 6.8 Hz, 1H), 8.20 (s, 1H), 8.03-8.01 (d, J = 8.4 Hz, 1H), 7.94-7.92 (d, J = 4.8 Hz, 1H), 7.52-7.50 (d, J = 6 Hz, 1H), 6.38-6.34 (t, J = 7.2 Hz, 1H), 6.24 (s, 1H), 5.45-5.44 (d, J = 7.2 Hz, 1H), 5.08-5.02 (m, 1H), 4.24-4.20 (t, J = 7.6 Hz, 1H), 4.03-4.00 (m, 2H), 3.87-3.83 (t, J = 7.6 Hz, 1H), 3.55-3.50 (t, J = 12 Hz, 2H), 2.92-2.91 (d, J = 4.4 Hz, 3H), 2.04-2.1.94 (m, 2H), 1.78-1.76 (d, J = 10.4 Hz, 2H), 1.56-1.47 (m, 2H), 1.25-1.16 (m, 2H). FR-b: MS (ES): m/z 454.50 [M + H]$^+$, LCMS purity: 100%, HPLC purity: 100% CHIRAL HPLC: 99.58%, $^1$H NMR (DMSO-d$_6$, 400 MHZ): 8.92 (s, 1H), 8.26-8.24 (d, J = 6.4 Hz, 1H), 8.20 (s, 1H), 8.03-8.01 (d, J = 9.2 Hz, 1H), 7.94-7.93 (d, J = 4.8 Hz, 1H), 7.52-7.51 (d, J = 5.6 Hz, 1H), 6.38-6.34 (t, J = 7.2 Hz, 1H), 6.25 (s, 1H), 4.24-4.20 (t, J = 8.8 Hz, 1H), 4.03-4.01 (m, 2H), 3.87-3.83 (t, J = 7.2 Hz, 1H), 3.55-3.50 (t, J = 11 Hz, 2H), 2.92-2.91 (d, J = 4.8 Hz, 3H), 2.04-2.1.97 (m, 4H), 1.78-1.75 (d, J = 12.4.4 Hz, 2H), 1.54-1.47 (m, 2H), 1.30-1.11 (m, 2H) |
| I-540 | I-635 I-636 | FR-a: MS (ES): m/z 482.82 [M + H]$^+$. LCMS purity: 100%, HPLC purity: 99.77%, Chiral HPLC purity: 100%, NMR (DMSO-d$_6$, 400 MHZ): 8.89 (s, 1H), 8.23-8.21 (d, J = 7.2 Hz, 1H), 8.18 (s, 1H), 8.02-8.01 (d, J = 8.8 Hz, 1H), 7.93-7.92 (d, J = 4.8 Hz, 1H), 7.45-7.43 (d, J = 8.8 Hz, 1H), 6.35-6.31 (t, J = 7.2 Hz, 1H), 6.22 (s, 1H), 5.45-5.44 (d, J = 6.8 Hz, 1H), 4.23-4.19 (t, J = 8.4 Hz, 1H), 3.85-3.82 (t, J = 7.2 Hz, 1H), 3.27 (s, 3H), 3.23-3.22 (m, 1H), 2.91-2.90 (d, J = 4.8 Hz, 3H), 2.16-2.13 (d, J = 10.8 Hz, 2H), 2.03-2.01 (d, J = 7.2 Hz, 2H), 1.81-1.77 (m, 4H), 1.50-1.46 (t, J = 8.8 Hz, 2H), 1.34-1.18 (m, 4H). FR-b: MS (ES): m/z 482.82 [M + H]$^+$. |

TABLE 58-continued

| Compound | Isomers | Characterization Data |
|---|---|---|
| | | LCMS purity: 100%, HPLC purity: 100%, Chiral HPLC purity: 97.89%, NMR (DMSO-$d_6$, 400 MHZ): 8.90 (s, 1H), 8.24-8.22 (d, J = 7.2 Hz, 1H), 8.20 (s, 1H), 8.03-8.01 (d, J = 8.8 Hz, 1H), 7.94-7.93 (d, J = 4.8 Hz, 1H), 7.46-7.44 (d, J = 6.8 Hz, 1H), 6.36-6.32 (t, J = 7.2 Hz, 1H), 6.23 (s, 1H), 5.46-5.44 (d, J = 7.2 Hz, 1H), 4.24-4.20 (t, J = 8.4 Hz, 1H), 3.87-3.83 (t, J = 7.2 Hz, 1H), 3.28 (s, 3H), 3.25-3.21 (m, 1H), 2.92-2.91 (d, J = 4.4 Hz, 3H), 2.17-2.14 (d, J = 11.2 Hz, 2H), 2.06-2.02 (d, J = 8 Hz, 2H), 1.81-1.76 (m, 4H), 1.52-1.47 (t, J = 9.6 Hz, 2H), 1.35-1.19 (m, 4H). |
| I-586 | I-639 I-640 | FR-a: MS (ES): m/z 420.33 [M + H]$^{+\cdot}$ LCMS purity: 96.79%, HPLC purity: 95.24%, Chiral HPLC purity: 95.68%, NMR (DMSO-$d_6$, 400 MHZ): 9.00-8.82 (s, 1H), 8.79-8.77 (d, J = 6.8 Hz, 1H), 8.52-8.50 (d, J = 8.8 Hz, 1H), 8.42-8.41 (d, J = 4.4 Hz, 1H), 8.37 (s, 1H), 8.27 (s, 1H), 7.30-7.27 (m, 1H), 6.81 (s, 1H), 5.53-5.52 (bs, J = 12.4 Hz, 1H), 5.22-5.21 (m, 1H), 4.33-4.27 (m, 1H), 4.02-00 (m, 1H), 3.13-3.12 (d, J = 4 Hz, 3H), 2.82-2.80 (m, 2H), 2.11-2.09 (m, 2H), 1.60-1.59 (d, 6H). FR-b: MS (ES): m/z 420.33 [M + H]$^{+\cdot}$ LCMS purity: 99.51%, HPLC purity: 97.19%, Chiral HPLC purity: 98.03%, NMR (DMSO-$d_6$, 400 MHZ): 8.82 (s, 1H), 8.79-8.77 (d, J = 7.6 Hz, 1H), 8.52-8.50 (d, J = 8.8 Hz, 1H), 8.42-8.41 (d, J = 3.6 Hz, 1H), 8.37 (s, 1H), 8.27-8.25 (d, J = 4.8 Hz, 1H), 7.34-7.231 (m, 1H), 6.81 (s, 1H), 5.51-5.49 (d, J = 7.2 Hz, 1H), 5.24-5.19 (m, 1H), 4.33-4.29 (m, 1H), 4.03-3.99 (m, 1H), 3.13-3.12 (d, J = 4.4 Hz, 3H), 2.82-2.80 (m, 2H), 2.11-2.09 (m, 2H), 1.60-1.59 (d, 6H). |
| I-603 | I-664 I-665 | FR-a: MS (ES): m/z 438.50 [M + H]$^+$, LCMS purity: 100%, HPLC purity: 100%, CHIRAL HPLC purity: 100%, $^1$H NMR (DMSO-$d_6$, 400 MHZ): 9.90 (s, 1H), 8.21-8.08 (m, 3H), 7.70 (m, 1H), 7.56 (m, 1H), 6.97-6.96 (d, J = 6.8 Hz, 1H), 6.69 (s, 1H), 5.41-5.39 (d, J = 6.8 Hz, 1H), 4.22 (s, 1H), 4.00-3.88 (m, 3H), 3.55-3.50 (t, J = 10.4 Hz, 1H), 2.97 (s, 4H), 2.01-1.91 (m, 4H), 1.67 (s, 2H), 1.50-1.214 (t, J = 9.2 Hz, 1H). 1.31-1.23 (m, 2H). FR-b: MS (ES): m/z 438.50 [M + H]$^+$, LCMS purity: 100%, HPLC purity: 98.84%, CHIRAL HPLC purity: 96.69%, $^1$H NMR (DMSO-$d_6$, 400 MHZ): 9.90 (s, 1H), 8.21 (s, 1H), 8.16-8.13 (d, J = 8.8 Hz, 1H), 8.08-8.07 (d, J = 4.4 Hz, 1H), 7.72-7.68 (t, J = 7.6 Hz, 1H), 7.57 (s, 1H), 6.98-6.96 (d, J = 7.6 Hz, 1H), 6.69 (s, 1H), 5.41-5.39 (d, J = 7.6 Hz, 1H), 4.24-4.20 (m, 1H), 4.02-3.88 (m, 3H), 3.55-3.50 (t, J = 10.8 Hz, 1H), 2.97-2.89 (m, 4H), 2.01-1.89 (m, 4H), 1.67 (s, 2H), 1.50-1.45 (t, J = 9.2 Hz, 1H), 1.34-1.11 (m, 2H). |
| I-602 | I-666 I-667 | FR-a: MS (ES): m/z 438.50 [M + H]$^+$, LCMS purity: 100%, HPLC purity: 100%, CHIRAL HPLC purity: 100%, $^1$H NMR (DMSO-$d_6$, 400 MHZ): 9.91 (s, 1H), 8.21 (s, 1H), 8.16-14 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.42-5.40 (d, J = 7.2 Hz, 1H), 4.26-4.18 (m, 1H), 4.02-3.88 (m, 3H), 3.55-3.50 (t, J = 10.8 Hz, 1H), 2.97-2.89 (m, 4H), 2.06-1.86 (m, 4H), 1.69-1.67 (m, 2H), 1.52-1.34 (m, 3H). FR-b: MS (ES): m/z 438.50 [M + H]$^+$, LCMS purity: 100%, HPLC purity: 100%, CHIRAL HPLC purity: 99%, $^1$H NMR (DMSO-$d_6$, 400 MHZ): 9.91 (s, 1H), 8.21 (s, 1H), 8.16-14 (d, J = 8.8 Hz, 1H), 8.08-07 (d, J = 4.8 Hz, 1H), 7.72-7.68 (t, J = 8 Hz, 1H), 7.57-7.55 (d, J = 7.2 Hz, 1H), 6.97-6.96 (d, J = 7.6 Hz, 1H), 6.69 (s, 1H), 5.42-5.40 (d, J = 7.2 Hz, 1H), 4.26-4.18 (m, 1H), 4.02-3.88 (m, 3H), |

TABLE 58-continued

| Compound | Isomers | Characterization Data |
| --- | --- | --- |
| | | 3.55-3.50 (t, J = 10.8 Hz, 1H), 2.97-2.89 (m, 4H), 2.06-1.86 (m, 4H), 1.69-1.67 (m, 2H), 1.52-1.34 (m, 3H) |
| I-697 | I-724<br>I-725 | FR-a: MS (ES): m/z 454.66 [M + H]+·<br>LCMS purity: 100%, HPLC purity: 97.82%,<br>Chiral HPLC purity: 97.82%, NMR (DMSO-$d_6$, 400 MHZ): 8.95 (s, 1H), 8.25-8.23 (d, J = 6.4 Hz, 1H), 8.19 (s, 1H), 8.02-7.99 (d, J = 8.8 Hz, 1H), 7.94-7.92 (d, J = 4.8 Hz, 1H), 7.54-7.53 (d, J = 6.4 Hz, 1H), 6.36-6.32 (t, J = 7.2 Hz, 1H), 6.24 (s, 1H), 5.45 (s, 1H), 4.91-4.86 (m, 1H), 4.23-4.19 (t, J = 8.4 Hz, 1H), 3.84 (s, 3H), 3.59-3.54 (t, J = 10 Hz, 1H), 3.48-3.43 (t, J = 11.2 Hz, 1H), 3.17-3.16 (J = 4 Hz, 1H), 2.91-2.89 (d, J = 4.4 Hz, 3H), 2.05-2.03 (m, 5H), 1.77-1.71 (m, 2H).<br>FR-b: MS (ES): m/z 454.66 [M + H]+·<br>LCMS purity: 100%, HPLC purity: 98.63%,<br>Chiral HPLC purity: 97.82%, NMR (DMSO-$d_6$, 400 MHZ): 8.95 (s, 1H), 8.25-8.23 (d, J = 6.4 Hz, 1H), 8.19 (s, 1H), 8.02-7.99 (d, J = 8.8 Hz, 1H), 7.94-7.92 (d, J = 4.8 Hz, 1H), 7.54-7.53 (d, J = 6 Hz, 1H), 6.36-6.33 (t, J = 7.2 Hz, 1H), 6.24 (s, 1H), 5.45-43 (d, J = 7.6 Hz, 1H), 4.91-4.86 (m, 1H), 4.23-4.19 (t, J = 8 Hz, 1H), 3.86-3.82 (t, J = 8 Hz, 3H), 3.60-3.55 (t, J = 10.4 Hz, 1H), 3.48-3.43 (t, J = 11.2 Hz, 1H), 3.17-3.16 (d, J = 5.2 Hz, 1H), 2.91-2.89 (d, J = 4.8 Hz, 3H), 2.04-2.03 (m, 5H), 1.77-1.71 (m, 2H) |
| I-698 | I-726<br>I-727 | FR-a: MS (ES): m/z 454.5 [M + H]+, LCMS purity: 95.02%, HPLC purity: 95.43%, CHIRAL HPLC purity: 100%, $^1$H NMR (DMSO-$d_6$, 400 MHZ): 8.94 (s, 1H), 8.25-8.23 (d, J = 6.4 Hz, 1H), 8.19 (s, 1H), 7.99 (bs, 1H), 7.93-7.92 (d, J = 4.8 Hz, 1H), 7.54-7.53 (d, J = 6 Hz, 1H), 6.36-6.33 (t, J = 7.2 Hz, 1H), 6.24 (s, 1H), 5.45-5.43 (d, J = 7.2 Hz, 1H), 4.91-4.86 (m, 1H), 4.23-4.19 (m, 1H), 3.84-3.82 (m, 3H), 3.60-3.55 (t, J = 10.4 Hz, 1H), 3.48-3.43 (t, J = 11.2 Hz, 1H), 2.91-2.89 (d, J = 4.4 Hz, 3H), 2.04-2.02 (d, J = 6 Hz, 5H), 1.51-1.46 (m, 1H), 1.23-1.18 (m, 2H).<br>FR-b: MS (ES): m/z 454.4 [M + H]+, LCMS purity: 98.96%, HPLC purity: 100%, CHIRAL HPLC purity: 100%, $^1$H NMR (DMSO-$d_6$, 400 MHZ): 8.94 (s, 1H), 8.25-8.23 (d, J = 7.2 Hz, 1H), 8.19 (s, 1H), 7.99 (bs, 1H), 7.93-7.92 (d, J = 4.4 Hz, 1H), 7.54-7.53 (d, J = 6 Hz, 1H), 6.36-6.32 (t, J = 7.2 Hz, 1H), 6.24 (s, 1H), 5.45-5.43 (d, J = 7.2 Hz, 1H), 4.91-4.86 (m, 1H), 4.23-4.19 (m, 1H), 3.86-3.82 (m, 3H), 3.60-3.54 (t, J = 10 Hz, 1H), 3.48-3.43 (t, J = 8.4 Hz, 1H), 2.91-2.89 (d, J = 4.4 Hz, 3H), 2.04-2.03 (d, J = 6 Hz, 5H), 1.51-1.46 (m, 1H), 1.23-1.19 (m, 2H). |
| I-658 | I-768<br>I-769 | FR-a: MS (ES): m/z 451.22 [M + H]+, LCMS purity: 98.60%, HPLC purity: 100%, CHIRAL HPLC purity: 100%, $^1$H NMR (DMSO-$d_6$, 400 MHZ): 8.98 (s, 1H), 8.65-8.63 (d, J = 7.2 Hz, 1H), 8.24 (s, 1H), 8.04-7.95 (m, 3H), 7.42-7.41 (d, J = 6.4 Hz, 1H), 6.54-6.50 (t, J = 7.2 Hz, 1H), 6.31 (s, 1H), 5.47-46 (d, J = 3.2 Hz, 1H), 4.60-4.55 (m, 1H), 4.37 (s, 1H), 3.19-17 (d, J = 5.2 Hz, 1H), 2.93-2.92 (d, J = 4.8 Hz, 3H), 2.20 (s, 2H), 2.13-1.94 (m, 2H), 1.76 (s, 2H).<br>FR-b: MS (ES): m/z 451.22 [M + H]+, LCMS purity: 98.32%, HPLC purity: 98.53%, CHIRAL HPLC purity: 98.38%, $^1$H NMR (DMSO-$d_6$, 400 MHZ): 8.98 (s, 1H), 8.65-8.63 (d, J = 7.2 Hz, 1H), 8.23 (s, 1H), 8.04 (s, 1H), 8.02 (s, 1H), 7.95 (s, 1H), 7.42-7.49 (d, J = 6.8 Hz, 1H), 6.54-6.50 (t, J = 7.2 Hz, 1H), 6.31 (s, 1H), 4.60-4.56 (t, J = 7.2 Hz, 1H), 4.37 (s, 1H), 2.93-2.92 (s, 3H), 2.20 (s, 4H), 2.13-1.94 (m, 2H), 1.79-1.76 (d, J = 9.6 Hz, 2H). |

TABLE 58-continued

| Compound | Isomers | Characterization Data |
|---|---|---|
| I-675 | I-776<br>I-777 | FR-a: MS (ES): m/z 465.32 [M + H]$^+$,<br>LCMS purity: 100%, HPLC purity: 99.0%<br>CHIRAL HPLC: 97.%, $^1$H NMR (DMSO-d$_6$,<br>400 MHZ): 9.08 (s, 1H), 8.52-8.51 (d, J = 4.0 Hz,<br>1H), 8.39-8.38 (d, J = 4.0 Hz, 1H), 8.21 (s, 1H),<br>8.10-8.02 (m, 2H), 7.98-7.97 (d, J = 4.0 Hz, 1H),<br>7.75-7.71 (m, 1H), 7.48-7.46 (m, 1H),<br>6.51-6.47 (t, J = 7.2 Hz 1H), 6.23 (s, 1H), 5.48-5.46 (d,<br>J = 8.0 Hz, 1H), 4.27-4.19 (m, 1H),<br>3.93-3.85, (m, 1H), 2.91-2.89, (d, J = 8.0 Hz, 3H),<br>2.08-2.00 (m, 2H), 1.54-1.44 (m, 1H), 1.31-1.21 (m,<br>1H)<br>FR-b: MS (ES): m/z 465.32 [M + H]$^+$,<br>LCMS purity: 100%, HPLC purity: 99.05%<br>CHIRAL HPLC: 98.04%, $^1$H NMR (DMSO-<br>d$_6$, 400 MHZ): 9.08 (s, 1H), 8.52-8.51 (d,<br>J = 4.0 Hz, 1H), 8.39-8.38 (d, J = 4.0 Hz, 1H),<br>8.21 (s, 1H), 8.10-8.02 (m, 2H), 7.98-7.97 (d,<br>J = 4.0 Hz, 1H), 7.75-7.71 (m, 1H), 7.48-7.46 (m,<br>1H), 6.51-6.47 (t, J = 7.2 Hz, 1H), 6.23 (s, 1H),<br>5.48-5.46 (d, J = 8.0 Hz, 1H), 4.27-4.21 (m, 1H),<br>3.91-3.87, (m, 1H), 2.91-2.89, (d, J = 8.0 Hz,<br>3H), 2.06-2.02 (m, 2H), 1.54-1.47 (m, 1H),<br>1.31-1.21 (m, 1H). |
| I-712 | I-825<br>I-826 | FR-a: MS (ES): m/z 488.37 [M + H]$^+$,<br>LCMS purity: 98.62%, HPLC purity: 97.36%,<br>CHIRAL HPLC purity: 96.69%, $^1$H NMR<br>(DMSO-d$_6$, 400 MHZ): 9.03 (s, 1H), 8.26 (s,<br>1H), 8.22-8.21 (d, J = 4 Hz, 1H) 8.03-8.02 (d,<br>J = 8 Hz, 1H), 7.73-7.68 (m, 2H), 6.34 (s, 1H),<br>5.37-5.35 (d, J = 8 Hz, 1H), 5.04-5.01 (t,<br>J = 12 Hz, 1H), 4.31-4.29 (t, J = 8 Hz, 1H),<br>4.02-3.98 (m, 3H), 2.93-2.92 (d, J = 4.2 Hz, 3H),<br>2.06-1.96 (m, 5H), 1.78-1.75 (d, J = 11.8 Hz, 2H),<br>1.49-1.35 (m, 3H).<br>FR-b: MS (ES): m/z 488.42 [M + H]$^+$,<br>LCMS purity: 100%, HPLC purity: 96.94%,<br>CHIRAL HPLC purity: 99.43%, $^1$H NMR<br>(DMSO-d$_6$, 400 MHZ): 9.03 (s, 1H), 8.26 (s,<br>1H), 8.22-8.21 (d, J = 4 Hz, 1H), 8.03 (s, 1H),<br>7.73-7.68 (m, 2H), 6.34 (s, 1H), 5.37 (s, 1H),<br>5.04-5.01 (t, J = 12 Hz, 1H), 4.31-4.29 (t,<br>J = 8 Hz, 1H), 4.03-4.01 (d, J = 8 Hz, 3H), 2.92 (s,<br>3H), 2.06-1.96 (m, 5H), 1.78-1.75 (d,<br>J = 11.8 Hz, 2H), 1.49-1.35 (m, 3H). |
| I-792 | I-835<br>I-836 | FR-a: MS (ES): m/z 491.57 [M + H]$^+$,<br>LCMS purity: 100%, HPLC purity: 99.58%,<br>CHIRAL HPLC purity: 99.38%, $^1$H NMR<br>(DMSO-d$_6$, 400 MHZ): 8.77-8.75 (d, J = 7.6 Hz,<br>1H), 8.71 (s, 1H), 8.51-8.49 (d, J = 8.4 Hz, 1H),<br>8.41-8.40 (d, J = 3.6 Hz, 1H), 8.37 (s, 1H),<br>8.30-8.28 (d, J = 4.4 Hz, 1H), 7.33-7.30 (m, 1H),<br>6.70 (s, 1H), 5.52-5.50 (d, J = 6.4 Hz, 1H),<br>4.52-4.49 (t, J = 6.4 Hz, 2H), 4.33-4.29 (m, 1H),<br>4.03-4.00 (m, 1H), 3.55 (bs, 4H), 3.11-3.10 (d, J = 3.6 Hz,<br>3H), 2.84-2.81 (t, J = 6.4 Hz, 2H), 2.52 (bs, 4H),<br>2.11-2.09 (d, J = 6 Hz, 2H), 1.56-1.52 (m, 1H),<br>1.37-1.32 (m, 1H).<br>FR-b: MS (ES): m/z 491.41 [M + H]$^+$,<br>LCMS purity: 100%, HPLC purity: 99.22%,<br>CHIRAL HPLC purity: 100%, $^1$H NMR<br>(DMSO-d$_6$, 400 MHZ): ): 8.77-8.75 (d, J = 8 Hz,<br>1H), 8.72 (s, 1H), 8.51-8.49 (d, J = 8.4 Hz, 1H),<br>8.42-8.41 (d, J = 4.4 Hz, 1H), 8.37 (s, 1H),<br>8.30-8.29 (d, J = 4.4 Hz, 1H), 7.34-7.30 (m, 1H),<br>6.70 (s, 1H), 5.52-5.50 (d, J = 6.8 Hz, 1H),<br>4.53-4.49 (t, J = 6.4 Hz, 2H), 4.33-4.29 (m, 1H),<br>4.03-4.00 (m, 1H), 3.55 (bs, 4H), 3.11-3.10 (d, J = 4.4 Hz,<br>3H), 2.84-2.81 (t, J = 6.8 Hz, 2H), 2.52 (bs, 4H),<br>2.11-2.09 (d, J = 6 Hz, 2H), 1.56-1.52 (m, 1H),<br>1.37-1.32 (m, 1H). |
| I-794 | I-837<br>I-838 | FR-a: MS (ES): m/z 489.26 [M + H]$^+$,<br>LCMS purity: 100%, HPLC purity: 99.49%,<br>CHIRAL HPLC purity: 99.92%, $^1$H NMR<br>(DMSO-d$_6$, 400 MHZ): 8.77-8.76 (d, J = 6.8 Hz,<br>1H), 8.71 (s, 1H), 8.51-8.49 (d, J = 8.4 Hz, 1H),<br>8.42-8.41 (d, J = 4.0 Hz, 1H), 8.38 (s, 1H),<br>8.29-8.28 (d, J = 4.8 Hz, 1H), 7.34-7.31 (m, 1H), |

TABLE 58-continued

| Compound | Isomers | Characterization Data |
|---|---|---|
| | | 6.70 (s, 1H), 5.51-5.49 (d, J = 7.2 Hz, 1H), 4.49 (s, 1H), 4.35-4.27 (m, 1H), 4.06-3.98 (m, 1H), 3.11-3.10 (d, J = 4.8 Hz, 3H), 2.78 (s, 1H), 2.11-2.09 (d, J = 7.2 Hz, 2H), 1.59-1.48 (m, 5H), 1.38-1.24 (m, 6H), 1.08-1.04 (m, 1H), 0.89-0.85 (m, 2H). FR-b: MS (ES): m/z 489.47 [M + H]$^+$, LCMS purity: 100%, HPLC purity: 99.52%, CHIRAL HPLC purity: 98.93%, $^1$H NMR (DMSO-d$_6$, 400 MHZ): 8.77-8.75 (d, J = 7.2 Hz, 1H), 8.71 (s, 1H), 8.51-8.49 (d, J = 8.4 Hz, 1H), 8.42-8.41 (d, J = 4.0 Hz, 1H), 8.38 (s, 1H), 8.29-8.28 (d, J = 4.8 Hz, 1H), 7.34-7.31 (m, 1H), 6.70 (s, 1H), 5.52-5.50 (d, J = 7.2 Hz, 1H), 4.51 (s, 1H), 4.35-4.27 (m, 1H), 4.06-3.98 (m, 1H), 3.11-3.10 (d, J = 4.8 Hz, 3H), 2.74 (s, 1H), 2.11-2.09 (d, J = 7.2 Hz, 2H), 1.59-1.48 (m, 5H), 1.38-1.24 (m, 6H), 1.08-1.04 (m, 1H), 0.89-0.85 (m, 2H) |
| I-756 (Chiral separation when methylamino at position 7 is protected by Boc, followed by removal of Boc) | I-857 | FR-a: MS (ES): m/z 394.35 [M + H]$^+$, LCMS purity: 98.05%, HPLC purity: 96.13%, Chiral HPLC: 98.13%, $^1$H NMR (DMSO-d$_6$, 400 MHZ): 9.78 (s, 1H), 8.80 (s, 1H), 8.18 (s, 1H), 8.12-8.10 (d, J = 9.2 Hz, 1H), 8.05-8.03 (d, J = 8 Hz, 1H), 7.99 (bs, 1H), 7.53-7.51 (d, J = 8 Hz, 1H), 7.46-7.42 (m, 1H), 6.05 (s, 1H), 4.22-4.14 (m, 1H), 3.18 (s, 1H), 2.94-2.94 (d, J = 3.2 Hz, 3H), 2.01-1.91 (m, 2H), 1.56 (bs, 1H), 1.24 (s, 1H), 1.08-1.01 (m, 1H). |
| I-845 (Chiral separation when methylamino at position 7 is protected by Boc, followed by removal of Boc) | I-898 I-899 | FR-a: MS (ES): m/z 499.42 [M + H]$^+$, LCMS purity: 100%, HPLC purity: 99.45%, Chiral HPLC: 100%, $^1$H NMR (DMSO-d$_6$, 400 MHZ): 8.28 (s, 1H), 8.54-8.52 (d, J = 8 Hz, 1H), 8.21 (s, 1H), 8.05-8.03 (d, J = 8 Hz, 1H), 7.90-7.89 (d, J = 4.6 Hz, 1H), 7.46-7.44 (d, J = 8 Hz, 1H), 6.42-6.40 (t, J = 8.2 Hz, 1H), 6.27 (s, 1H), 5.78 (s, 1H), 5.42-5.40 (d, J = 8 Hz, 1H), 4.84-4.81 (t, J = 12.8 Hz, 1H), 4.63-4.50 (m, 3H), 4.36 (s, 1H), 3.09-3.06 (d, J = 12.6 Hz, 2H), 2.92-2.91 (d, J = 4.6 Hz, 3H), 2.73-2.61 (m, 2H), 2.26-2.24 (t, J = 8.2 Hz, 3H), 2.16-1.93 (m, 4H), 1.79-1.77 (m, 2H). FR-b: MS (ES): m/z 499.42 [M + H]$^+$, LCMS purity: 100%, HPLC purity: 98.88% Chiral HPLC: 100%, $^1$H NMR (DMSO-d$_6$, 400 MHZ): 8.28 (s, 1H), 8.54-8.52 (d, J = 8 Hz, 1H), 8.21 (s, 1H), 8.05-8.03 (d, J = 8 Hz, 1H), 7.90-7.89 (d, J = 4.6 Hz, 1H), 7.46-7.44 (d, J = 8 Hz, 1H), 6.42-6.40 (t, J = 8.2 Hz, 1H), 6.27 (s, 1H), 5.78 (s, 1H), 5.42-5.40 (d, J = 8 Hz, 1H), 4.84-4.81 (t, J = 12.8 Hz, 1H), 4.63-4.50 (m, 3H), 4.36 (s, 1H), 3.09-3.06 (d, J = 12.6 Hz, 2H), 2.92-2.91 (d, J = 4.6 Hz, 3H), 2.73-2.61 (m, 2H), 2.26-2.24 (t, J = 8.2 Hz, 3H), 2.16-1.93 (m, 4H), 1.79-1.77 (m, 2H). |
| I-852 | I-920 I-921 | FR-a: MS (ES): m/z 504.82 [M + H]$^+$, LCMS purity: 100%, HPLC purity: 99.19%, CHIRAL HPLC purity: 97.72%, $^1$H NMR (DMSO-d$_6$, 400 MHZ): 8.77-8.75 (d, J = 6.8 Hz, 1H), 8.71 (s, 1H), 8.51-8.49 (d, J = 8.8 Hz, 1H), 8.42-8.41 (d, J = 3.6 Hz, 1H), 8.38 (s, 1H), 8.29-8.28 (d, J = 4.8 Hz, 1H), 7.34-7.31 (m, 1H), 6.69 (s, 1H), 5.51-5.49 (d, J = 7.2 Hz, 1H), 4.51-4.48 (t, J = 6.8 Hz, 2H), 4.33-4.29 (m, 1H), 4.04-4.00 (m, 1H), 3.12-3.10 (d, J = 4.8 Hz, 3H), 2.84-2.81 (t, J = 6.8 Hz, 2H), 2.34-2.29 (m, 4H), 2.13-2.10 (m, 6H), 1.57-1.52 (m, 2H), 1.38-1.28 (m, 3H). FR-b: MS (ES): m/z 504.67 [M + H]$^+$, LCMS purity: 98.13%, HPLC purity: 97.28%, CHIRAL HPLC purity: 97.21%, $^1$H NMR (DMSO-d$_6$, 400 MHZ): 8.77-8.76 (d, J = 6.8 Hz, 1H), 8.71 (s, 1H), 8.51-8.49 (d, J = 8.8 Hz, 1H), 8.42-8.41 (d, J = 3.6 Hz, 1H), 8.38 (s, 1H), 8.29-8.28 (d, J = 4.8 Hz, 1H), 7.34-7.31 (m, 1H), 6.70 (s, 1H), 5.51-5.49 (d, J = 7.2 Hz, 1H), 4.51-4.48 (t, J = 6.8 Hz, 2H), 4.34-4.29 (m, 1H), |

TABLE 58-continued

| Compound | Isomers | Characterization Data |
|---|---|---|
| | | 4.04-4.01 (m, 1H), 3.12-3.10 (d, J = 4.8 Hz, 3H), 2.84-2.81 (t, J = 6.8 Hz, 2H), 2.35-2.31 (m, 4H), 2.14-2.10 (m, 6H), 1.59-1.50 (m, 2H), 1.44-1.31 (m, 3H). |
| | I-930 I-931 (Chiral separation when methylamino at position 7 is protected by Boc, followed by removal of Boc) | FR-a: MS (ES): m/z 501.52 [M + H]$^+$, LCMS purity: 95.11%, HPLC purity: 95.45%, Chiral HPLC: 97.89%, $^1$H NMR (DMSO-d$_6$, 400 MHZ): 9.02 (s, 1H), 8.26 (s, 1H), 8.21-8.20 (d, J = 2.4 Hz, 1H), 8.03-8.02 (d, J = 4.8 Hz, 1H), 7.72-7.70 (d, J = 8.8 Hz, 1H), 7.64 (s, 1H), 6.33 (s, 1H), 5.37-5.36 (d, J = 7.2 Hz, 1H), 4.73 (s, 1H), 4.31-4.27 (m, 1H), 4.02-3.98 (m, 1H), 3.58 (s, 2H), 2.93-2.92 (d, J = 4.8 Hz, 3H), 2.34 (s, 3H), 2.09-1.96 (m, 6H), 1.77-1.74 (m, 2H), 1.49-1.35 (s, 2H). FR-b: MS (ES): m/z 501.52 [M + H]$^+$, LCMS purity: 96.49%, HPLC purity: 95.94%, Chiral HPLC: 98.76%, $^1$H NMR (DMSO-d$_6$, 400 MHz): 97.89%, $^1$H NMR (DMSO-d$_6$, 400 MHz): 9.02 (s, 1H), 8.26 (s, 1H), 8.21-8.20 (d, J = 2.4 Hz, 1H), 8.03-8.02 (d, J = 4.8 Hz, 1H), 7.73-7.71 (d, J = 8.8 Hz, 1H), 7.65 (s, 1H), 6.34 (s, 1H), 5.38-5.36 (d, J = 7.2 Hz, 1H), 4.73 (s, 1H), 4.34-4.27 (m, 1H), 4.02-3.96 (m, 1H), 3.58 (s, 2H), 2.93-2.92 (d, J = 4.8 Hz, 3H), 2.23 (s, 3H), 2.09-1.96 (m, 6H), 1.77-1.74 (m, 2H), 1.49-1.35 (s, 2H). |
| I-705 (Chiral separation when methylamino at position 7 is protected by Boc, followed by removal of Boc) | I-971 I-972 | FR-a: MS (ES): m/z 447.46 [M + H]$^+$, LCMS purity: 100%, HPLC purity: 95.36%, Chiral HPLC: 97.98%, $^1$H NMR (DMSO-d$_6$, 400 MHZ): 9.06 (s, 1H), 8.67-8.66 (d, J = 4.2 Hz, 1H), 8.37-8.35 (d, J = 6 Hz, 1H), 8.22 (s, 1H), 8.09-8.06 (m, 2H), 7.98-7.97 (d, J = 4.2 Hz, 1H), 7.87-7.85 (d, J = 8 Hz, 1H), 7.62-7.60 (m, 1H), 7.57-7.54 (m, 1H), 6.49-6.47 (t, J = 8 Hz, 1H) 6.26 (s, 1H), 5.48-5.46 (d, J = 6 Hz, 1H), 4.26-4.24 (t, J = 8 Hz, 1H), 3.91-3.89 (t, J = 7.9 Hz, 1H), 2.92-2.91 (d, J = 4.5 Hz, 3H), 2.10-2.01 (m, 2H), 1.52-1.50 (t, J = 7.8 Hz, 1H), 1.31-1.24 (m, 1H) FR-b: MS (ES): m/z 447.21 [M + H]$^+$, LCMS purity: 100%, HPLC purity: 95%, Chiral HPLC: 95.14%, $^1$H NMR (DMSO-d$_6$, 400 MHZ): 9.06 (s, 1H), 8.67-8.66 (d, J = 4.2 Hz, 1H), 8.37-8.35 (d, J = 6 Hz, 1H), 8.22 (s, 1H), 8.09-8.06 (m, 2H), 7.98-7.97 (d, J = 4.2 Hz, 1H), 7.87-7.85 (d, J = 8 Hz, 1H), 7.62-7.60 (m, 1H), 7.57-7.54 (m, 1H), 6.49-6.47 (t, J = 8 Hz, 1H) 6.26 (s, 1H), 5.48-5.46 (d, J = 6 Hz, 1H), 4.26-4.24 (t, J = 8 Hz, 1H), 3.91-3.89 (t, J = 7.9 Hz, 1H), 2.92-2.91 (d, J = 4.5 Hz, 3H), 2.10-2.01 (m, 2H), 1.52-1.50 (t, J = 7.8 Hz, 1H), 1.31-1.24 (m, 1H) |
| I-918 (Chiral separation when methylamino at position 7 is protected by Boc, followed by removal of Boc) | I-981 I-982 | FR-a: MS (ES): m/z 412.42 [M + H]$^+$, LCMS purity: 98.47%, HPLC purity: 98.30%, Chiral HPLC: 97.30%, $^1$H NMR (DMSO-d$_6$, 400 MHZ): 8.93 (s, 1H), 8.25-8.23 (d, J = 8 Hz, 1H), 8.20 (s, 1H), 8.04-8.02 (d, J = 8.8 Hz, 1H), 7.93-7.92 (d, J = 4.8 Hz, 1H), 7.48-7.46 (d, J = 8.3 Hz, 1H), 6.36-6.34 (t, J = 8.6 Hz, 1H), 6.24 (s, 1H), 5.21-5.16 (m, 1H), 4.25-4.19 (m, 1H), 3.85-3.83 (t, J = 7.8 Hz, 1H), 3.58 (s, 1H), 2.92-2.91 (d, J = 4 Hz, 3H), 2.07-2.05 (d, J = 8 Hz, 1H), 1.56-1.52 (m, 1H), 1.50-1.45 (m, 2H), 1.38-1.36 (d, J = 8 Hz, 6H). FR-b: MS (ES): m/z 412.57 [M + H]$^+$, LCMS purity: 9, 6.57%, HPLC purity: 99.53%, Chiral HPLC: 98.80%, $^1$H NMR (DMSO-d$_6$, 400 MHZ): 8.94 (s, 1H), 8.25-8.24 (d, J = 4.8 Hz, 1H), 8.20 (s, 1H), 8.04-8.02 (d, J = 8.8 Hz, 1H), 7.93-7.92 (d, J = 4.8 Hz, 1H), 7.48-7.46 (t, J = 8.3 Hz, 1H), 6.38-6.37 (t, J = 4 Hz, 1H), 6.24 (s, 1H), 5.21-5.16 (m, 1H), 4.27-4.19 (m, 1H), 3.85-3.83 (t, J = 7.8 Hz, 1H), 3.58 (s, 1H), 2.92-2.91 (d, J = 4 Hz, 3H), 2.07-2.05 (d, J = 8 Hz, H), 1.50-1.45 (m, 2H), 1.38-1.36 (d, J = 8 Hz, 6H). |

TABLE 58-continued

| Compound | Isomers | Characterization Data |
|---|---|---|
| I-943 (Chiral separation when methylamino at position 7 is protected by Boc, followed by removal of Boc) | I-1002<br>I-1003 | FR-a: MS (ES): m/z 452.51 [M + H]$^+$,<br>LCMS purity: 97.43%, HPLC purity: 96.74%,<br>Chiral HPLC: 98.30%, $^1$H NMR (DMSO-d$_6$,<br>400 MHZ): 8.95 (s, 1H), 8.22 (s, 1H), 8.21 (s,<br>1H), 8.06-8.04 (d, J = 8.4 Hz, 1H), 7.98 (s, 1H),<br>7.49-7.48 (d, J = 6.8 Hz, 1H), 6.37-6.33 (t,<br>J = 7.2 Hz, 1H), 6.22 (s, 1H), 4.84-4.78 (m, 1H),<br>4.25-4.21 (m, 1H), 3.75-3.68 (m, 1H),<br>3.52-3.47 (m, 1H), 2.93-2.92 (d, J = 4.4 Hz, 3H),<br>2.03-2.01 (d, J = 8 Hz, 2H), 1.87-1.78 (m, 3H),<br>1.70-1.67 (m, 2H), 1.52-1.42 (m, 3H), 1.25-1.21 (m,<br>4H).<br>FR-b: MS (ES): m/z 452.51 [M + H]$^+$,<br>LCMS purity: 96.44%, HPLC purity: 95%,<br>Chiral HPLC: 99.05%, $^1$H NMR (DMSO-d$_6$,<br>400 MHZ): 8.94 (s, 1H), 8.22 (s, 1H), 8.21 (s,<br>1H), 8.06-8.04 (d, J = 8.4 Hz, 1H), 7.98 (s, 1H),<br>7.49-7.48 (d, J = 6.8 Hz, 1H), 6.37-6.33 (t,<br>J = 6.8 Hz, 1H), 6.22 (s, 1H), 4.84-4.78 (m, 1H),<br>4.25-4.18 (m, 1H), 3.75-3.68 (m, 1H),<br>3.52-3.47 (m, 1H), 2.93-2.92 (d, J = 4.4 Hz, 3H),<br>2.04-2.02 (d, J = 8 Hz, 2H), 1.87-1.78 (m, 3H),<br>1.70-1.67 (m, 2H), 1.52-1.42 (m, 3H), 1.25-1.21 (m,<br>4H). |
| I-946 | I-1023<br>I-1024 | FR-a: MS (ES): m/z 464.31 [M + H]$^+$,<br>LCMS purity: 99.57%, HPLC purity: 99.14%,<br>CHIRAL HPLC purity: 95.01%, $^1$H NMR<br>(DMSO-d$_6$, 400 MHZ): 9.04 (s, 1H),<br>8.36-8.38 (d, J = 8 Hz, 1H), 8.22 (s, 1H), 8.04-8.06 (d,<br>J = 8 Hz, 1H), 7.99-7.98 (m, 1H), 7.60-7.65 (m,<br>1H), 7.50-7.52 (d, J = 8 Hz, 1H), 7.36-7.42 (m,<br>3H), 6.43-6.45 (t, J = 8 Hz, 1H), 6.27 (s, 1H),<br>5.48-5.50 (d, J = 8 Hz, 1H), 4.20-4.27 (m, 1H),<br>3.88-3.92 (m, 1H), 2.91-2.92 (d, J = 4 Hz, 3H),<br>2.02-2.08 (m, 2H), 1.48-1.54 (m, 2H).<br>FR-b: MS (ES): m/z 464.31 [M + H]$^+$,<br>LCMS purity: 99.41%, HPLC purity: 99.57%,<br>CHIRAL HPLC purity: 95.01%, $^1$H NMR<br>(DMSO-d$_6$, 400 MHZ): 9.04 (s, 1H),<br>8.36-8.38 (d, J = 7.2 Hz, 1H), 8.22 (s, 1H), 8.04-8.06 (d,<br>J = 8 Hz, 1H), 7.99-7.98 (m, 1H), 7.60-7.65 (m,<br>1H), 7.50-7.52 (d, J = 8 Hz, 1H), 7.36-7.42 (m,<br>3H), 6.43-6.45 (t, J = 8 Hz, 1H), 6.27 (s, 1H),<br>5.48-5.50 (d, J = 8 Hz, 1H), 4.20-4.28 (m, 1H),<br>3.86-3.92 (m, 1H), 2.90-2.92 (d, J = 8 Hz, 3H),<br>2.02-2.08 (m, 2H), 1.48-1.54 (m, 2H). |
| I-940 (Chiral separation when methylamino at position 7 is protected by Boc, followed by removal of Boc) | I-1038<br>I-1039 | FR-a: MS (ES): m/z 464.67 [M + H]$^+$,<br>LCMS purity: 99.07%, HPLC purity: 96.25%,<br>Chiral HPLC: 100%, $^1$H NMR (DMSO-d$_6$,<br>400 MHZ): 9.04-9.02 (d, J = 6.4 Hz, 1H),<br>8.38-8.35 (t, J = 6.8 Hz, 1H), 8.21 (s, 1H),<br>8.04-8.02 (d, J = 8.8 Hz, 1H), 7.98-7.97 (d, J = 4.8 Hz, 1H),<br>7.64-7.35 (m, 4H), 6.45-6.40 (m, 1H),<br>6.26-6.25 (d, J = 6.0 Hz, 1H), 5.49-5.47 (d, J = 7.2 Hz,<br>1H), 4.28-4.21 (m, 1H), 3.91-3.87 (t, J = 8.0 Hz,<br>1H), 3.57 (s, 2H), 2.91-2.90 (d, J = 4.4 Hz, 3H),<br>2.07-2.01 (m, 2H), 1.33-1.23 (m, 2H).<br>FR-b: MS (ES): m/z 464.47 [M + H]$^+$,<br>LCMS purity: 97.025%, HPLC purity:<br>98.08%, Chiral HPLC: 100%, $^1$H NMR<br>(DMSO-d$_6$, 400 MHZ): 9.04 (s, 1H), 8.36 (s,<br>1H), 8.21 (s, 1H), 8.04-8.02 (m, 2H),<br>7.60-7.39 (m, 4H), 6.43 (s, 1H), 6.26 (s, 1H), 5.47 (bs,<br>1H), 4.23 (bs, 1H), 3.89 (bs, 1H), 3.57 (bs, 2H),<br>2.90 (bs, 3H), 2.05 (bs, 2H), 1.33-1.23 (m, 2H). |
| I-994 (Chiral separation when methylamino at position 7 is protected by Boc, followed by removal of Boc) | I-1054<br>I-1055 | FR-a: MS (ES): m/z 482.56 [M + H]$^+$,<br>LCMS purity: 100%, HPLC purity: 99.24%,<br>Chiral HPLC: 99.48%, $^1$H NMR (DMSO-d$_6$,<br>400 MHZ): 8.91 (s, 1H), 8.25-8.23 (d, J = 6.8 Hz,<br>1H), 8.20 (s, 1H), 8.04-8.01 (d, J = 8.8 Hz, 1H),<br>7.95-7.93 (d, J = 4.8 Hz, 1H), 7.52-7.50 (d,<br>J = 6.4 Hz, 1H), 6.37-6.33 (t, J = 7.2 Hz, 1H),<br>6.24 (s, 1H), 5.46-5.45 (d, J = 5.6 Hz, 1H),<br>4.88-4.82 (t, J = 12.4 Hz, 1H), 4.28-4.21 (m, 1H), 3.85 (s,<br>1H), 3.28 (s, 3H), 2.92-2.91 (d, J = 4.8 Hz, 3H),<br>2.20-2.17 (m, 2H), 2.07-1.92 (m, 3H),<br>1.68-1.43 (m, 4H), 1.40-1.20 (m, 3H).<br>FR-b: MS (ES): m/z 582.51 [M + H]$^+$, |

TABLE 58-continued

| Compound | Isomers | Characterization Data |
| --- | --- | --- |
| | | LCMS purity: 100%, HPLC purity: 96.40%, Chiral HPLC: 95.67%, $^1$H NMR (DMSO-d$_6$, 400 MHZ): 8.91 (s, 1H), 8.25-8.23 (d, J = 6.8 Hz, 1H), 8.20 (s, 1H), 8.04-8.01 (d, J = 8.8 Hz, 1H), 7.95-7.93 (d, J = 4.8 Hz, 1H), 7.52-7.50 (d, J = 6.4 Hz, 1H), 6.37-6.33 (t, J = 7.2 Hz, 1H), 6.24 (s, 1H), 5.46-5.45 (d, J = 5.6 Hz, 1H), 4.88-4.82 (t, J = 12.4 Hz, 1H), 4.28-4.21 (m, 1H), 3.85 (s, 1H), 3.28 (s, 3H), 2.92-2.91 (d, J = 4.8 Hz, 3H), 2.20-2.17 (m, 2H), 2.07-1.92 (m, 3H), 1.68-1.43 (m, 4H), 1.40-1.20 (m, 3H). |
| I-676 (Chiral separation when methylamino at position 7 is protected by Boc, followed by removal of Boc) | I-1070 I-1071 | FR-a: MS (ES): m/z 467.42 [M + H]$^+$, LCMS purity: 100%, HPLC purity: 99.83%, Chiral HPLC: 98.86%, $^1$H NMR (DMSO-d$_6$, 400 MHZ): 9.23 (s, 1H), 8.68-8.66 (d, J = 6.8 Hz, 1H), 8.43-8.41 (d, J = 7.2 Hz, 1H), 8.24 (s, 1H), 8.06-8.04 (d, J = 8.8 Hz, 1H), 7.98-7.97 (d, J = 4.8 Hz, 1H), 7.54 (s, 1H), 6.73-6.69 (t, J = 7.2 Hz, 1H), 6.38 (s, 1H), 5.78 (bs, 1H), 4.60-4.57 (t, J = 6.0 Hz, 1H), 4.38 (s, 1H), 3.35-3.33 (m, 1H), 2.94-2.93 (d, J = 4.8 Hz, 3H), 2.20-1.95 (m, 3H), 1.79 (s, 1H), 1.56 (s, 1H), 1.35-1.24 (m, 1H). FR-b: MS (ES): m/z 467.47 [M + H]$^+$, LCMS purity: 98.83%, HPLC purity: 97.74%, Chiral HPLC: 100%, $^1$H NMR (DMSO-d$_6$, 400 MHZ): 9.22 (s, 1H), 8.68-8.66 (d, J = 7.2 Hz, 1H), 8.43-8.41 (d, J = 6.4 Hz, 1H), 8.24 (s, 1H), 8.06-8.04 (d, J = 8.8 Hz, 1H), 7.98-7.97 (d, J = 5.2 Hz, 1H), 7.54 (s, 1H), 6.73-6.69 (t, J = 7.2 Hz, 1H), 6.38 (s, 1H), 5.48-5.47 (d, J = 3.6 Hz, 1H), 4.60-4.57 (t, J = 6.0 Hz, 1H), 4.39 (s, 1H), 3.35-3.33 (m, 1H), 2.94-2.93 (d, J = 4.8 Hz, 3H), 2.20-1.95 (m, 3H), 1.79 (s, 1H), 1.56 (s, 1H), 1.35-1.24 (m, 1H). |
| I-962 (Chiral separation when methylamino at position 7 is protected by Boc, followed by removal of Boc) | I-1107 I-1108 | FR-a: MS (ES): m/z 496.57 [M + H]$^+$, LCMS purity: 95.08%, HPLC purity: 95.02%, Chiral HPLC: 95.53%, $^1$H NMR (DMSO-d$_6$, 400 MHZ): 8.92 (s, 1H), 8.23-8.22 (d, J = 6.4 Hz, 1H), 8.19 (s, 1H), 8.04-8.02 (d, J = 8.8 Hz, 1H), 7.95-7.93 (d, J = 4.8 Hz, 1H), 7.57-7.55 (d, J = 6.4 Hz, 1H), 6.34-6.31 (t, J = 7.2 Hz, 1H), 6.22 (s, 1H), 5.49 (s, 1H), 4.76 (bs, 1H), 4.24-4.19 (m, 1H), 3.85-3.83 (m, 1H), 3.16 (s, 3H), 2.91-2.90 (d, J = 4.4 Hz, 3H), 2.06-2.00 (m, 2H), 1.80 (bs, 6H), 1.60-1.50 (m, 3H), 1.24 (bs, 4H). FR-b: MS (ES): m/z 496.57 [M + H]$^+$, LCMS purity: 95.71%, HPLC purity: 95.11%, Chiral HPLC: 98.80%, $^1$H NMR (DMSO-d$_6$, 400 MHZ): 8.92 (s, 1H), 8.23-8.22 (d, J = 7.2 Hz, 1H), 8.19 (s, 1H), 8.04-8.02 (d, J = 8.8 Hz, 1H), 7.94-7.93 (d, J = 4.4 Hz, 1H), 7.57-7.55 (d, J = 6.4 Hz, 1H), 6.35-6.31 (t, J = 7.2 Hz, 1H), 6.23 (s, 1H), 5.48 (bs, 1H), 4.76 (bs, 1H), 4.24-4.19 (m, 1H), 3.85-3.83 (m, 1H), 3.16 (s, 3H), 2.91-2.90 (d, J = 4.0 Hz, 3H), 2.06-2.00 (m, 2H), 1.80 (bs, 6H), 1.60-1.50 (m, 3H), 1.24 (bs, 4H). |
| I-752 (Chiral separation when methylamino at position 7 is protected by Boc, followed by removal of Boc) | I-1123 I-1124 | FR-a: MS (ES): m/z 482.67 [M + H]$^+$, LCMS purity: 100%, HPLC purity: 98.85%, Chiral HPLC: 100%, $^1$H NMR (DMSO-d$_6$, 400 MHZ): 8.91 (s, 1H), 8.25-8.23 (d, J = 7.2 Hz, 1H), 8.20 (s, 1H), 8.03-8.01 (d, J = 8.8 Hz, 1H), 7.94-7.93 (d, J = 4.8 Hz, 1H), 7.52-7.51 (d, J = 6.4 Hz, 1H), 6.37-6.33 (t, J = 7.2 Hz, 1H), 6.23 (s, 1H), 5.46-5.44 (d, J = 7.2 Hz, 1H), 4.88-4.82 (m, 1H), 4.25-4.21 (m, 1H), 3.87-3.84 (m, 1H), 3.28 (s, 3H), 2.93-2.91 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). FR-b: MS (ES): m/z 482.41 [M + H]$^+$, LCMS purity: 100%, HPLC purity: 98.87%, Chiral HPLC: 97.65%, $^1$H NMR (DMSO-d$_6$, |

TABLE 58-continued
| Compound | Isomers | Characterization Data |
|---|---|---|
| | | 400 MHZ): 8.91 (s, 1H), 8.23-8.22 (d, J = 6.4 Hz, 1H), 8.20 (s, 1H), 8.03-8.01 (d, J = 8.8 Hz, 1H), 7.94-7.93 (d, J = 5.2 Hz, 1H), 7.51-7.50 (d, J = 6.4 Hz, 1H), 6.36-6.33 (t, J = 6.8 Hz, 1H), 6.22 (s, 1H), 5.46 (bs, 1H), 4.87-4.81 (m, 1H), 4.24-4.20 (m, 1H), 3.85-3.83 (m, 1H), 3.27 (s, 3H), 2.92-2.90 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). |
107.3. Synthesis of N-((1R,2R)-2-hydroxycyclobutyl)-5-(1-isopropyl-1H-pyrrolo[2,3-b]pyridin-3-yl)-7-(methylamino)pyrazolo[1,5-a]pyrimidine-3-carboxamide I-586
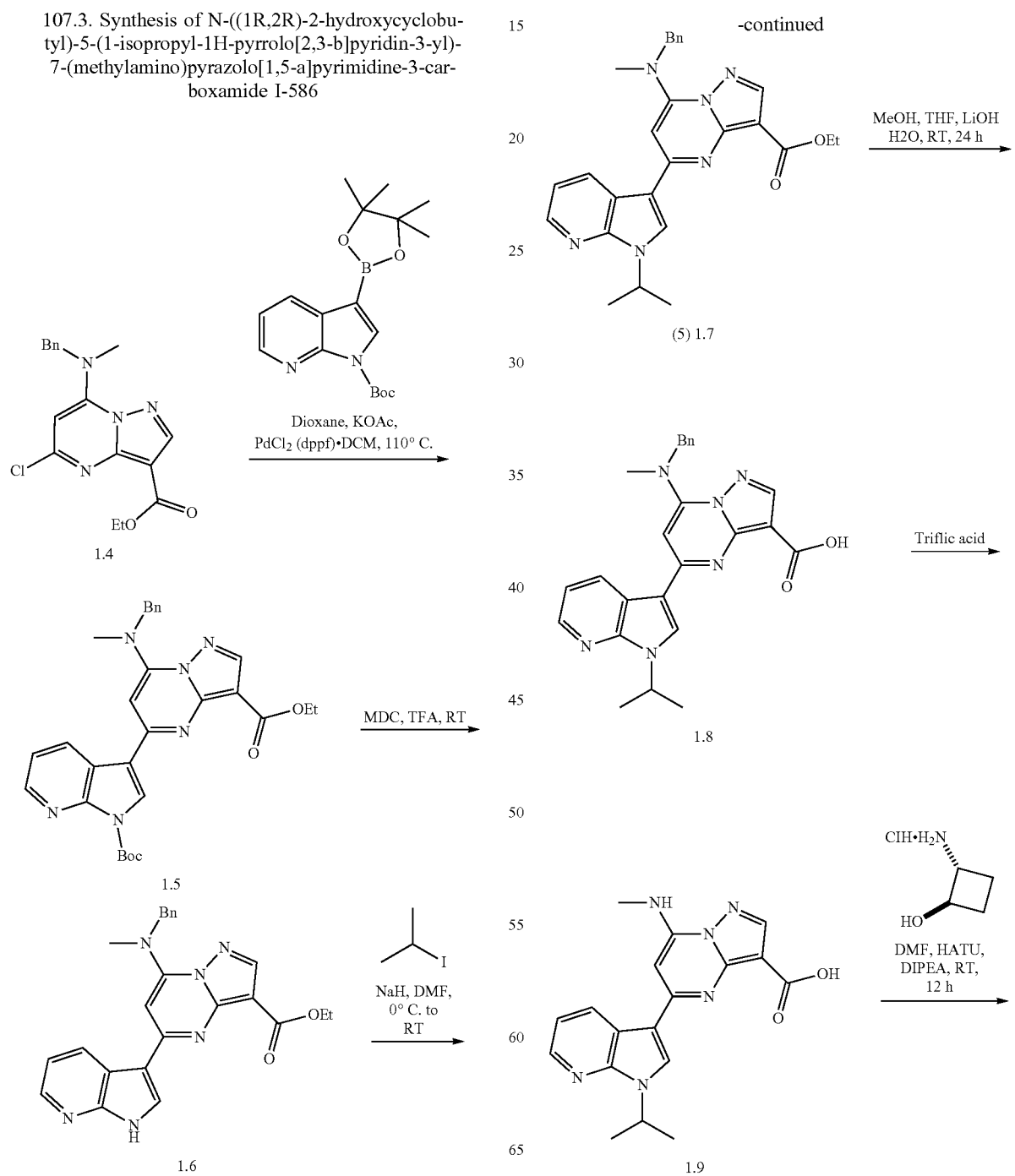

-continued

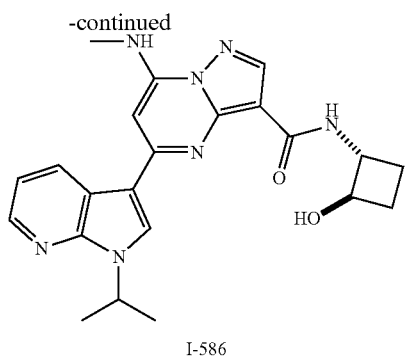

I-586

Synthesis of Compound 1.4

Compound was synthesized using general procedure of core synthesis to obtain 1.4 (26 g, 62.21%). MS(ES): m/z 355 [M+H]$^+$.

Synthesis of Compound 1.5

To a solution of 1.4 (0.1 g, 0.290 mmol, 1.0 eq), in dioxane (5 mL) were added tert-butyl 3-(4,4,5,5-tetramethyl-1,3,2-dioxaborolan-2-yl)-1H-pyrrolo[2,3-b]pyridine-1-carboxylate (0.129 g, 0.377, 1.3 eq) and sodium carbonate (0.076 g, 0.725 mmol 2.5 eq). The reaction mixture was degassed for 10 min. under argon atmosphere, then [1,1'-Bis(diphenylphosphino)ferrocene]dichloropalladium (II), complex with dichloromethane (0) (0.028 g, 0.029 mmol 0.1 eq) was added, again degassed for 5 min. The reaction was stirred at 100° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using eluted in 25% ethyl acetate in hexane to obtain pure 1.5 (0.083 g, 54.35%). MS(ES): m/z 527 [M+H]$^+$.

Synthesis of Compound 1.6

Compound was synthesized using general procedure C to obtain 1.6 (0.220 g, 9055%). MS(ES): m/z 427 [M+H]$^+$.

Synthesis of Compound 1.7

To a cooled solution of 1.6 (1 g, 2.34 mmol, 1.0 eq) in tetrahydrofuran (10 mL) was added sodium hydride (0.200 g, 4.68 mmol, 2 eq) and stirred for 20 min. followed by addition of 2-Iodopropane (1.3 g, 3.52 mmol, 1.5 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 52% ethyl acetate in hexane to obtain pure 1.7 (0.85 g, 77.37%), MS(ES): m/z 469.60 [M+H]$^+$.

Synthesis of Compound 1.8

To a solution of 1.7 (0.3 g, 0.95 mmol, 1.0 eq), in tetrahydrofuran: methanol: water (10 mL, 2:2:1) was added lithium hydroxide (0.396 g, 9.58 mmol, 5 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.8 (0.25 g, 83.64%). MS(ES): m/z 441.51 [M+H]$^+$.

Synthesis of Compound 1.9

The compound 1.8 (0.2 g, 0.45 mmol, 1.0 eq) was dissolved in dichloromethane (2 mL). Triflic acid was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 1.9 (0.12 g, 75.40%). MS(ES): m/z 351.38 [M+H]$^+$ Synthesis of Compound I-586.

Compound was synthesized using general procedure A to obtain I-586. (Yield: 64.89%). MS (ES): m/z 420.49 [M+H]$^+$, LCMS purity: 96.49%, HPLC purity: 96.15%, Chiral HPLC: 50.03%, 49.97%, $^1$H NMR (DMSO-d$_6$, 400 MHZ): 8.81 (s, 1H), 8.79-8.77 (d, J=8.0 Hz, 1H), 8.52-8.50 (d, J=8.4 Hz, 1H), 8.42-8.41 (d, J=4.4 Hz, 1H), 8.37 (s, 1H), 8.26-8.24 (d, J=5.2 Hz, 1H), 7.34-7.31 (m, 1H), 6.81 (s, 1H), 5.50-5.48 (d, J=7.2 Hz, 1H), 5.24-5.21 (m, 1H), 4.33-4.29 (t, J=8.8 Hz, 1H), 4.03-3.99 (d, J=8.0 Hz, 1H), 3.13-3.12 (d, J=4.8 Hz, 3H), 2.11-2.09 (d, J=5.2 Hz, 2H), 1.60-1.59 (d, J=6.4 Hz, 6H), 1.37-1.32 (t, J=9.2 Hz, 1H), 1.25 (bs, 1H).

107.4. Synthesis of N-((1R,2R)-2-hydroxycyclobutyl)-7-(methylamino)-5-((1-(4-methyloxazol-2-yl)-2-oxo-1,2-dihydropyridin-3-yl)amino)pyrazolo[1,5-a]pyrimidine-3-carboxamide: I-658

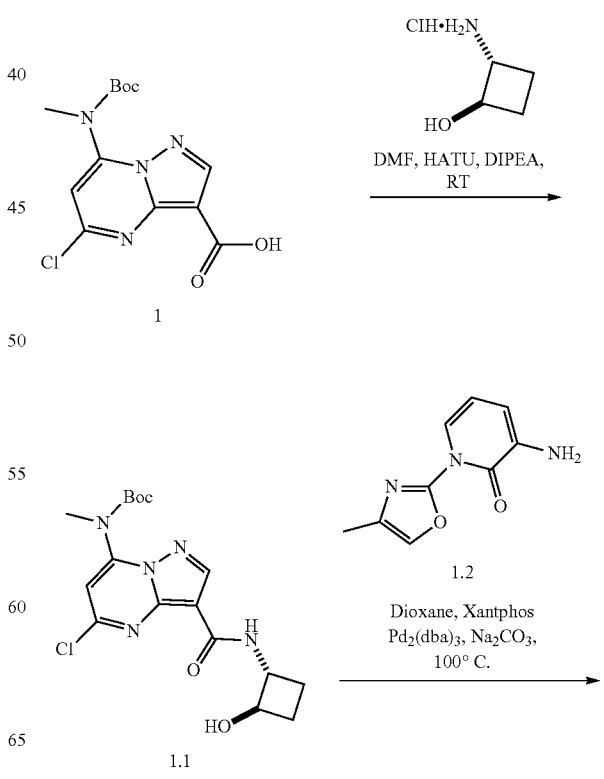

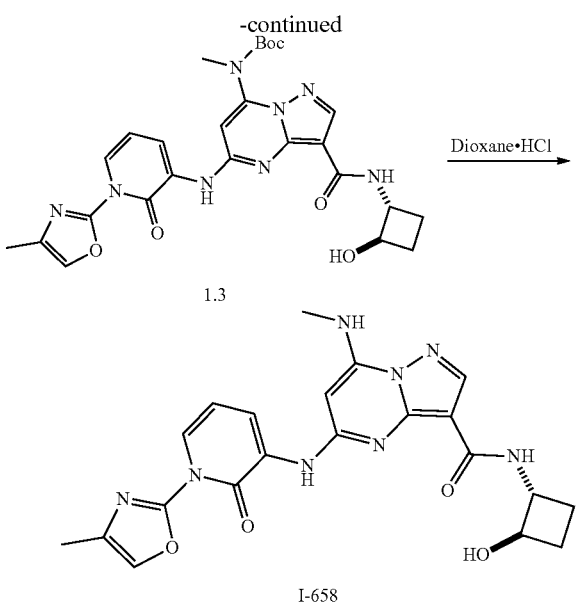

Synthesis of Compound 1:
Compound was synthesized as per experimental protocol of core synthesis to obtain 1.

Synthesis of Compound 1.1:
Compound was synthesized using general procedure A to obtain 1.1. (0.2 g, 50.51%) MS(ES): m/z 396.84 [M+H]⁺

Synthesis of Compound 1.2:
Compound was synthesized according to the experimental protocols of the intermediates.

Synthesis of Compound 1.3.
Compound was synthesized using general procedure B to obtain 1.1. (0.128 g, 65.73%) MS(ES): m/z 551.83 [M+H]

Synthesis of Compound I-658:
The compound 1.3 (0.128 g, 0.233 mmol, 1.0 eq) was dissolved in dichloromethane (2 mL) and 4M HCl in dioxane (0.2 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure: I-658: (0.09 g, 94%). MS(ES): m/z 451.83 [M+H]⁺ LCMS purity: 100%, HPLC purity: 95.78%, Chiral HPLC purity: 49.79%, 49.91%, NMR (DMSO-d₆, 400 MHZ): 9.98 (s, 1H), 8.63-8.61 (t, J=6 Hz, 1H), 8.23 (s, 1H), 8.03-7.96 (m, 3H), 7.41-7.39 (m, 1H), 6.53-6.49 (t, J=7.6 Hz, 1H), 6.30 (s, 1H), 5.47 (s, 1H), 4.60-4.55 (m, 1H), 4.36 (s, 1H), 3.57 (s, 3H), 2.91 (s, 3H), 2.19-2.17 (d, J=0.8 Hz, 2H), 2.02-1.93 (m, 2H).

Additional compounds prepared by substantially the same method, and their characterization data, are listed in the Table 59 below. The intermediate corresponding to of the 1.2 above scheme is listed for each compound.

TABLE 59

| Compound | Intermediate | Characterization data |
|---|---|---|
| I-675 | (pyridine-pyridone with F, NH₂) | MS (ES): m/z 465.35 [M + H]⁺, LCMS purity: 98.06%, HPLC purity: 94.39%, Chiral HPLC purity: 49.33% + 47.90%, ¹H NMR (DMSO-d₆, 400 MHZ): 9.08 (s, 1H), 8.52-8.51 (d, J = 4.4 Hz, 1H), 8.39-8.38 (d, J = 5.6, 1H), 8.21 (s, 1H), 8.10-8.02 (m, 2H), 7.98-7.97 (d, J = 5.2 Hz, 1H), 7.75-7.71 (m, 1H), 7.47-7.46 (d, J = 5.6, 1H), 6.51-6.47 (m, 1H), 6.23 (s, 1H), 5.47-5.45 (d, J = 7.6 Hz, 1H), 4.25-4.21 (m, 1H), 3.91-3.87 (m, 1H), 2.91-2.89 (d, J = 4.8 Hz, 3H), 2.04-2.02 (m, 2H), 1.51-1.41 (m, 1H), 1.28-1.25 (m, 1H). |
| I-676 | (thiazole-pyridone, NH₂) | MS (ES): m/z 467.22 [M + H]⁺, LCMS purity: 100%, HPLC purity: 95.88%, CHIRAL HPLC: 47.58%, 46.55%, ¹H NMR (DMSO-d₆, 400 MHZ): 9.34 (s, 1H), 8.47-8.46 (d, J = 6.4 Hz, 1H), 8.39-8.37 (d, J = 7.2 Hz, 1H), 8.23 (s, 1H), 8.02-8.00 (d, J = 8.8 Hz, 2H), 7.54 (s, 1H), 6.68-6.64 (t, J = 7.2 Hz, 1H), 6.29 (s, 1H), 5.78 (bs, 1H), 4.25-4.20 (t, J = 8.4 Hz, 2H), 3.87-3.85 (d, J = 8 Hz, 1H), 2.93 (bs, 3H), 2.07-2.01 (m, 2H), 1.52-1.47 (d, J = 9.2 Hz, 2H), 1.25-1.20 (m, 2H). |
| I-697 | (tetrahydropyran-pyridone, NH₂) | MS (ES): m/z 454.40 [M + H]⁺, LCMS purity: 100%, HPLC purity: 97.56%, CHIRAL HPLC: 50.29%, 49.70%, ¹H NMR (DMSO-d₆, 400 MHZ): 8.94 (s, 1H), 8.25-8.23 (d, J = 6 Hz, 1H), 8.19 (s, 1H), 7.99 (s, 1H), 7.93-7.92 (d, J = 5.2 Hz, 1H), 7.54-7.52 (d, J = 6.8 Hz, 1H), 6.36-6.33 (t, J = 6.8 Hz, 1H), 6.24 (s, 1H), 5.45-5.43 (d, J = 7.2 Hz, 1H), 4.91-4.86 (m, 1H), 4.23-4.19 (t, J = 8.8 Hz, 1H), 3.82 (bs, 3H), 3.55 (s, 2H), 2.91-2.90 (d, J = 4.8 Hz, 3H), 1.99 (s, 6H), 1.55 (bs, 1H), 1.51-1.44 (m, 1H). |

TABLE 59-continued

| Compound | Intermediate | Characterization data |
|---|---|---|
| I-698 | | MS (ES): m/z 454.45 [M + H]+, LCMS purity: 100%, HPLC purity: 95.44%, CHIRAL HPLC: 50.39%, 48.75%, 1H NMR (DMSO-d6, 400 MHZ): 8.94 (s, 1H), 8.25-8.23 (d, J = 6 Hz, 1H), 8.19 (s, 1H), 7.99 (bs, 1H), 7.93-7.92 (d, J = 4.8 Hz, 1H), 7.54-7.53 (d, J = 6 Hz, 1H), 6.36-6.32 (t, J = 7.2 Hz, 1H), 6.24 (s, 1H), 5.45-5.43 (d, J = 7.2 Hz, 1H), 4.91-4.86 (m, 1H), 4.13-4.09 (m, 1H), 3.86-3.82 (t, J = 7.6 Hz, 3H), 3.60-3.55 (t, J = 10.4 Hz, 1H), 3.48-3.44 (t, J = 9.2 Hz, 1H), 2.91-2.89 (d, J = 4.8 Hz, 3H), 1.77 (bs, 3H), 1.51-1.43 (m, 2H), 1.23-1.16 (m, 3H). |
| I-705 | | MS (ES): m/z 447.46 [M + H]+, LCMS purity: 97.43%, HPLC purity: 97.25%, 1H NMR (DMSO-d6, 400 MHZ): 9.06 (s, 1H), 8.67-8.66 (d, J = 4.0 Hz, 1H), 8.37-8.35 (d, J = 8.0 Hz, 1H), 8.22 (s, 1H), 8.07-8.05 (d, J = 8.0 Hz, 2H), 7.98 (s, 1H), 7.87-7.85 (d, J = 8.0 Hz, 1H), 7.62-7.54 (m, 2H), 6.49-6.45 (t, J = 8.0 Hz, 1H), 6.26 (s, 1H), 4.26-4.22 (m, 1H), 3.89 (s, 1H), 2.92 (s, 3H), 2.07-2.00 (m, 2H), 1.55-1.48 (m, 1H), 1.28-1.24 (m, 1H), 1.20-1.17 (m, 1H) |
| I-712 | | MS (ES): m/z 488.26 [M + H]+, LCMS purity: 94.81%, HPLC purity: 97.96%, CHIRAL HPLC: 43.67%, 46.70%, 1H NMR (DMSO-d6, 400 MHZ): 9.03 (s, 1H), 8.26 (s, 1H), 8.22-8.21 (d, J = 6 Hz, 1H), 8.03-8.02 (d, J = 4.8 Hz, 1H), 7.73-7.69 (m, 2H), 6.34 (s, 1H), 5.01 (m, 1H), 4.31-4.27 (m, 1H), 4.01-4.00 (d, J = 4 Hz, 2H), 3.53-3.48 (t, J = 11.6 Hz, 2H), 2.93-2.91 (d, J = 4.8 Hz, 3H), 2.06-1.96 (t, 5H), 1.78-1.75 (d, J = 12 Hz, 2H), 1.49-1.37 (m, 3H). |
| I-756 | | MS (ES): m/z 394.4 [M + H]+, LCMS purity: 98.95%, HPLC purity: 98.42%, Chiral HPLC: 44.46%, 51.41%, 1H NMR (DMSO-d6, 400 MHZ): 9.78 (s, 1H), 8.80 (s, 1H), 8.18 (s, 1H), 8.12-8.10 (d, J = 9.2 Hz, 1H), 8.05-8.03 (d, J = 8 Hz, 1H), 7.99-7.98 (d, J = 4.8 Hz, 1H), 7.53-7.51 (d, J = 8 Hz, 1H), 7.47-7.42 (m, 1H), 6.05 (s, 1H), 5.36-5.35 (d, J = 7.6 Hz, 1H), 4.20-4.16 (t, J = 4.8 Hz, 1H), 3.67-3.63 (t, J = 8 Hz, 1H), 2.95-2.94 (d, J = 4.4 Hz, 3H), 2.02-1.91 (m, 2H), 1.46-1.41 (t, J = 8.8 Hz, 1H), 1.24 (bs, 1H). |
| I-845 | | MS (ES): m/z 499.42 [M + H]+, LCMS purity: 98.36%, HPLC purity: 97.61%, 1H NMR (DMSO-d6, 400 MHZ): 8.94 (s, 1H), 8.28-8.26 (d, J = 6.8 Hz, 1H), 8..20 (s, 1H), 7.99 (bs, 1H), 7.96-7.95 (d, J = 4.4 Hz, 1H), 7.27 (bs, 1H), 6.44 (bs, 1H), 6.25 (s, 1H), 5.45 (bs, 1H), 5.10 (bs, 1H), 4.97 (bs, 1H), 4.85 (bs, 1H), 4.24-4.20 (t, J = 8.4 Hz, 1H), 3.84 (bs, 1H), 3.68-3.66 (d, J = 8.8 Hz, 2H), 3.57 (bs, 1H), 3.49 (bs, 1H), 2.91-2.90 (t, J = 4.4 Hz, 3H), 2.33 (bs, 2H), 2.10-1.99 (m, 4H), 1.51-1.44 (m, 1H), 1.23-1.16 (m, 3H). |
| I-918 | | MS (ES): m/z 412.20 [M + H]+, LCMS purity: 96.64%, HPLC purity: 96.03%, CHIRAL HPLC purity: 48.49%, 50.57%, 1H NMR (DMSO-d6, 400 MHZ): 8.94 (s, 1H), 8.23-8.19 (m, 2H), 8.04-8.80 (d, J = 8.8 Hz, 2H), 7.48-7.46 (d, J = 6.8 Hz, 1H), 6.37-6.33 (m, 1H), 5.19-5.16 (m, 1H), 4.24-4.20 (m, 1H), 3.85-3.81 (m, 1H), 3.64 (s, 3H), 2.90 (s, 3H), 2.03-2.01 (d, |

TABLE 59-continued

| Compound | Intermediate | Characterization data |
|---|---|---|
| | | J = 7.2 Hz, 2H), 1.36-1.34 (d, J = 6.8 Hz, 6H), 1.29-1.19 (m, 1H). |
| I-940 | 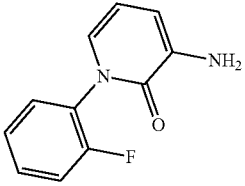 [SMILES: Nc1cccn(-c2ccccc2F)c1=O] | MS (ES): m/z 464.71 [M + H]+, LCMS purity: 96.38%, HPLC purity: 96.25%, CHIRAL HPLC purity: 50.25%, 49.74%, 1H NMR (DMSO-d6, 400 MHZ): 9.07 (bs, 1H), 8.40-8.38 (d, J = 7.2 Hz, 1H), 8.23 (s, 1H), 8.06-8.03 (d, J = 8.8 Hz, 1H), 7.98-7.97 (d, J = 4.8 Hz, 1H), 7.61-7.59 (d, J = 7.6 Hz, 2H), 7.52-7.48 (t, J = 9.2 Hz, 1H), 7.44-7.38 (m, 2H), 6.47-6.43 (t, J = 7.2 Hz, 1H), 6.26 (s, 1H), 5.49-5.47 (d, J = 7.2 Hz, 1H), 4.27-4.23 (m, 1H), 3.58 (s, 3H), 2.92-2.91 (d, J = 4.4 Hz, 3H), 2.09-2.02 (m, 2H). |
| I-943 | 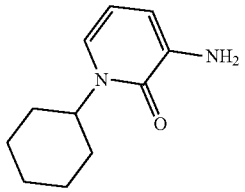 [SMILES: Nc1cccn(C2CCCCC2)c1=O] | MS (ES): m/z 452.76 [M + H]+, LCMS purity: 95.56%, HPLC purity: 94.86%, CHIRAL HPLC: 49.03%, 50.86%, 1H NMR (DMSO-d6, 400 MHZ): 8.89 (s, 1H), 8.22-8.21 (d, J = 6.8 Hz, 1H), 8.18 (s, 1H), 8.02-8.00 (d, J = 8.4 Hz, 1H), 7.92-7.91 (d, J = 4.8 Hz, 1H), 7.47-7.46 (d, J = 6.8 Hz, 1H), 6.35-6.31 (t, J = 7.2 Hz, 1H), 6.22 (s, 1H), 4.80 (bs, 1H), 4.23-4.19 (m, 1H), 3.57 (s, 1H), 2.91-2.90 (d, J = 4.4 Hz, 3H), 2.03-2.01 (d, J = 8 Hz, 2H), 1.87-1.78 (m, 4H), 1.70-1.67 (m, 3H), 1.57-1.42 (m, 3H), 1.23 (bs, 3H). |
| I-946 | 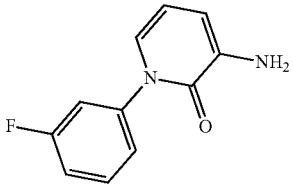 [SMILES: Nc1cccn(-c2cccc(F)c2)c1=O] | MS (ES): m/z 464.71 [M + H]+, LCMS purity: 97.18%, HPLC purity: 95.98%, CHIRAL HPLC: 49.08%, 50.92%, 1H NMR (DMSO-d6, 400 MHZ): 9.02 (bs, 1H), 8.37-8.35 (d, J = 6.4 Hz, 1H), 8.22 (s, 1H), 8.06-8.03 (d, J = 8.8 Hz, 1H), 7.65-7.59 (m, 1H), 7.52-7.50 (d, J = 10 Hz, 1H), 7.42-7.36 (m, 3H), 6.45-6.41 (t, J = 7.2 Hz, 1H), 6.26 (s, 1H), 4.28-4.20 (m, 1H), 3.93-3.87 (m, 1H), 2.91 (s, 3H), 2.08-2.00 (m, 2H), 1.51-1.46 (t, J = 10 Hz, 1H), 1.26 (bs, 3H). |
| I-962 | 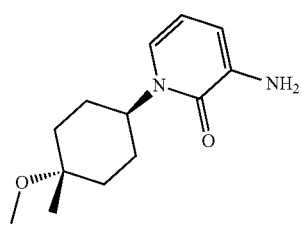 | MS (ES): m/z 496.57 [M + H]+, LCMS purity: 100%, HPLC purity: 95.47%, Chiral HPLC: 50.49%, 49.51%, 1H NMR (DMSO-d6, 400 MHZ): 8.92 (s, 1H), 8.24-8.22 (d, J = 6.8 Hz, 1H), 8.20 (s, 1H), 8.04-8.02 (d, J = 8.8 Hz, 1H), 7.94-7.93 (d, J = 4.8 Hz, 1H), 7.57-7.55 (d, J = 6.8 Hz, 1H), 6.35-6.31 (t, J = 6.8 Hz, 1H), 6.23 (s, 1H), 5.46-45.44 (d, J = 7.2 Hz, 1H), 4.76 (bs, 1H), 4.27-4.18 (m, 1H), 3.89-31 (m, 1H), 3.17 (s, 3H), 2.92-2.91 (d, J = 4.8 Hz, 3H), 2.06-2.00 (m, 2H), 1.80 (bs, 6H), 1.60-1.50 (m, 3H), 1.24 (bs, 4H). |
| I-993 | 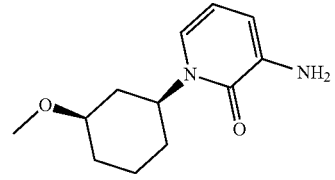 | MS (ES): m/z 482.52 [M + H]+, LCMS purity: 100%, HPLC purity: 99.00%, CHIRAL HPLC purity: 49.7%, 50.3%, 1H NMR (DMSO-d6, 400 MHZ): 8.91 (s, 1H), 8.24-8.22 (d, J = 7.2 Hz, 1H), 8.20 (s, 1H), 8.03-8.01 (d, J = 8.8 Hz, 1H), 7.95-7.93 (d, J = 5.2 Hz, 1H), 7.51-7.50 (d, J = 6.4 Hz, 1H), 6.36-6.33 (t, J = 6.8 Hz, 1H), 6.23 (s, 1H), 5.46 (bs, 1H), 4.81 (bs, 1H), 4.24-4.20 (m, 1H), 3.85 (bs, 1H), 3.28 (s, 3H), 2.92-2.91 (d, J = 4.8 Hz, 3H), 2.17 (bs, 1H), 2.04-2.00 (m, 3H), 1.85 (bs, 1H), 1.74 (bs, 1H), 1.64-1.58 (m, 2H), 1.49-1.39 (m, 2H), 1.20-1.11 (m, 3H). |

TABLE 59-continued

| Compound | Intermediate | Characterization data |
|---|---|---|
| I-994 | (structure: 3-amino-1-(3-methoxycyclohexyl)pyridin-2(1H)-one) | MS (ES): 482.57 [M + H]$^+$ LCMS purity: 98.07%, HPLC purity: 97.72%, CHIRAL HPLC: 50.73%, 48.17%, $^1$H NMR (DMSO-d$_6$, 400 MHZ): 8.91 (s, 1H), 8.24-8.22 (d, J = 6.8 Hz, 1H), 8.20 (s, 1H), 8.03-8.01 (d, J = 8.4 Hz, 1H), 7.94-7.93 (d, J = 4.8 Hz, 1H), 7.51-7.50 (d, J = 6.4 Hz, 1H), 6.36-6.33 (t, J = 7.2 Hz, 1H), 6.23 (s, 1H), 5.45 (bs, 1H), 4.87-4.81 (t, J = 12.4 Hz, 1H), 4.26-4.18 (m, 1H), 3.86-3.84 (d, J = 7.2 Hz, 1H), 3.28 (s, 3H), 2.92-2.91 (d, J = 4.8 Hz, 3H), 2.17 (bs, 1H), 2.06-2.00 (m, 3H), 1.88-1.85 (d, J = 13.2 Hz, 1H), 1.75 (bs, 1H), 1.61-1.56 (m, 2H), 1.49-1.39 (m, 2H), 1.30-1.20 (m, 3H). |
| I-1091 | (structure: 3-amino-1-(2-fluorocyclopropyl)pyridin-2(1H)-one) | MS (ES): m/z 428.32 [M + H]$^+$, LCMS purity: 100%, HPLC purity: 98%, CHIRAL HPLC, 49%:49%, $^1$H NMR (DMSO-d$_6$, 400 MHZ): 8.99 (s, 1H), 8.23-8.19 (d, J = 6.8 Hz, 2H), 8.01-7.99 (s, 1H), 7.95-7.94 (d, J = 4.8 Hz, 1H), 7.21-7.19 (d, J = 7.6, 1H), 6.29-6.24 (d, J = 7.2 Hz, 2H), 5.08-4.93 (s, 1H), 4.23-4.21 (m, 1H), 3.90-3.82 (d, J = 6 Hz, 2H), 2.91-2.90 (d, J = 4.8 Hz, 3H), 2.04-1.98 (m, 2H), 1.76-1.71 (m, 1H), 1.58-1.45 (m, 3H), 1.33 (s, 1H). |
| I-1092 | (structure: 3-amino-1-(2-fluorocyclopropyl)pyridin-2(1H)-one, other enantiomer) | MS (ES): m/z 428.40 [M + H]$^+$, LCMS purity: 95.27%, HPLC purity: 96.10%, CHIRAL HPLC Purity: 100%, $^1$H NMR (DMSO-d$_6$, 400 MHZ): 8.99 (s, 1H), 8.25-8.23 (d, J = 7.2 Hz, 1H), 8.20 (s, 1H), 8.02-8.00 (d, J = 8.8 Hz, 1H), 7.95-7.93 (d, J = 4.8 Hz, 1H), 7.22-7.20 (d, J = 7.2 Hz, 1H), 7.09-7.07 (d, J = 7.6 Hz, 1H), 6.84-6.82 (d, J = 8.4 Hz, 1H), 6.30-6.27 (t, J = 7.2 Hz, 1H), 6.25 (s, 1H), 4.24-4.18 (m, 1H), 2.92-2.91 (d, J = 4.8 Hz, 3H), 2.06-1.99 (m, 2H), 1.56 (bs, 3H), 1.24 (bs, 3H). |

107.5. Synthesis of N-(2-hydroxycyclobutyl)-7-(methylamino)-5-(1-(2-morpholinoethyl)-1H-pyrrolo[2,3-b]pyridin-3-yl)pyrazolo[1,5-a]pyrimidine-3-carboxamide (I-792)

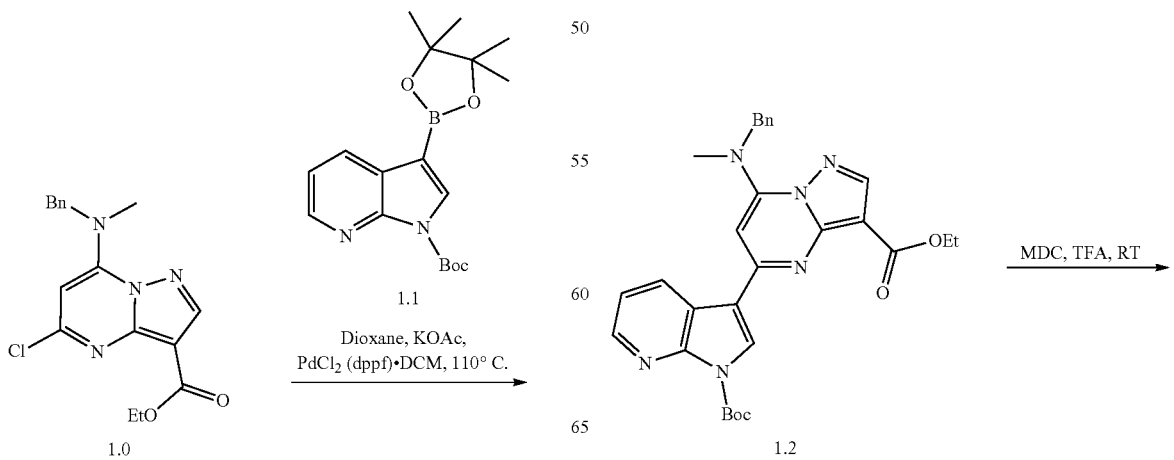

1707
-continued

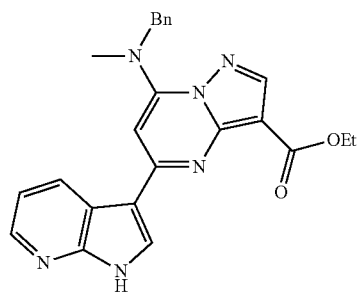

1.3

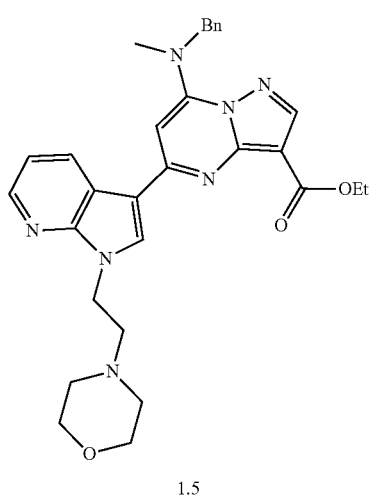

1.5

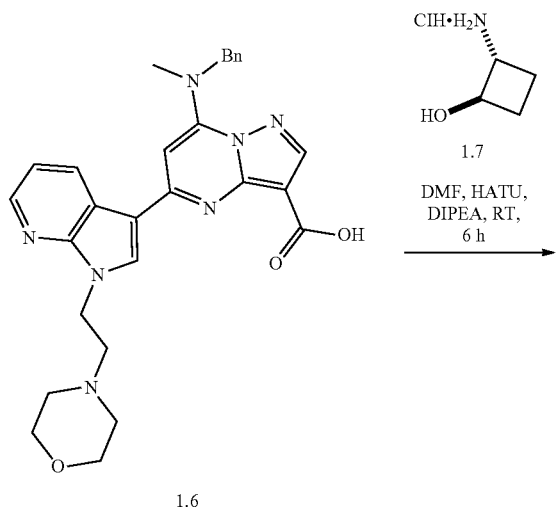

1.6

1708
-continued

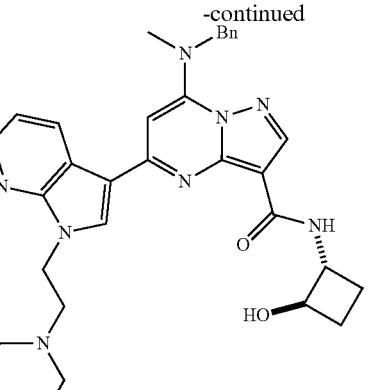

1.8

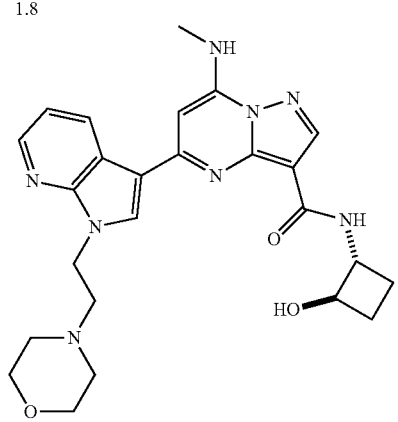

I-792

Synthesis of Compound 1.0.

Compound was synthesized using general procedure of core synthesis to obtain 1.0 (Yield: 45.00%). MS (ES): m/z 345.10 [M+H]+

Synthesis of Compound 1.2.

Argon was purged for 15 min through a stirred solution of 1.1 (2.3 g, 6.7 mmol, 1.0 eq), 1.0 (3.0 g, 8.72 mmol, 1.3 eq) and sodium carbonate (1.78 g, 16.75 mmol, 2.5 eq) in 1,4 dioxane (100 mL). [1,1'-Bis(diphenylphosphino)ferrocene]dichloropalladium(II) (0.550 g, 0.67 mmol, 0.1 eq) was added to it and further purging done for 10 min. Reaction was allowed to stirred at 100° C. for 6 h. After completion of reaction, reaction mixture was transferred into water and product was extracted with ethyl acetate. Organic layer was combined, washed with brine solution, dried over sodium sulphate and concentrated under reduced pressure to obtain crude product which purified by column chromatography eluting pure compound in 20-25% ethyl acetate in hexane to obtain pure 1.2 (2.1 g, 59.82%). MS (ES): m/z 527.51 [M+H]+

Synthesis of Compound 1.3.

Trifluoroacetic acid (5.0 mL) was added to a solution of 1.2 (2.1 g, 3.99 mmol, 1.0 eq) in dichloromethane (20 mL) and reaction mixture was stirred at room temperature for 2 h. After completion of reaction, reaction mixture was transferred into saturated sodium bicarbonate solution and product was extracted with dichloromethane. Organic layer was combined, washed with brine solution, dried over sodium sulphate and concentrated under reduced pressure to obtain 1.3. (1.69 g, 99.41%). MS (ES): m/z 427.51 [M+H]+

Synthesis of Compound 1.5.

sodium hydride (0.225 g, 5.6 mmol, 4.0 eq) was added to a solution of 1.3 (0.600 g, 1.4 mmol, 1.0 eq) in N—N-

Dimethylformamide (12 mL) at 0° C. portion wise. Reaction mixture was stirred at same temperature for 20 min, 1.4 (0.635 g, 4.22 mmol, 1.2 eq) was added and mixture was allowed to stir at room temperature for 6 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography eluting pure compound in 2-2.5% methanol in dichloromethane to obtain pure 1.5 (420 mg, 55.26%). MS (ES): m/z 540.51 [M+H]+.

Synthesis of Compound 1.6.

To a solution of 1.5 (0.400 g, 0.744 mmol, 1.0 eq), in tetrahydrofuran: methanol: water (20 mL, 1:1:1) was added lithium hydroxide (0.315 g, 7.44 mmol, 10 eq). The reaction was stirred 60° C. for 6 h. After completion of reaction, reaction mixture was concentrated under reduced pressure to obtain residue. To this added water and acidified with 1N hydrochloric acid to adjust pH~6-6.5 at 10° C. Product was filtered and dried under vacuum to obtain pure 1.6 (0.360 g, 94.47%). MS(ES): m/z 512.2 [M+H]+.

Synthesis of Compound 1.8.

Compound was synthesized using general procedure A to obtain 1.8. (0.170 g, 74.88%), MS (ES): 581.29 [M+H]+

Synthesis of Compound I-792:

Mixture of 1.8 (0.170 g, 0.292 mmol, 1.0 eq) in 1.0 ml dichloromethane was cooled to 0° C. and triflic acid (1 mL) was added to it and mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-792 (0.110 g, 76.59%), MS (ES): m/z 491.57 [M+H]+, LCMS purity: 100%, HPLC purity: 97.71%, Chiral HPLC: 47.82%, 46.59%, $^1$H NMR (DMSO-d$_6$, 400 MHZ): 8.77-8.76 (d, J=6.8 Hz, 1H), 8.71 (s, 1H), 8.51-8.49 (d, J=8.4 Hz, 1H), 8.41-8.41 (d, J=3.6 Hz, 1H), 8.37 (s, 1H), 8.28 (bs, 1H), 7.34-7.30 (m, 1H), 6.70 (m, 1H), 5.51 (bs, 1H), 4.53-4.49 (t, J=6.8 Hz, 2H), 4.33-4.27 (m, 1H), 4.03-4.01 (d, J=8 Hz, 1H), 3.55 (bs, 4H), 3.13-3.11 (s, 3H), 2.85-2.81 (t, J=6.4 Hz, 3H), 2.11-2.09 (d, J=6.8 Hz, 3H), 1.59-1.49 (m, 2H), 1.40-1.30 (m, 1H), 1.12-1.08 (t, J=7.2 Hz, 1H).

Additional compounds prepared by substantially the same method, and their characterization data, are listed in the Table 60 below. The intermediate corresponding to of the 1.4 above scheme is listed for each compound.

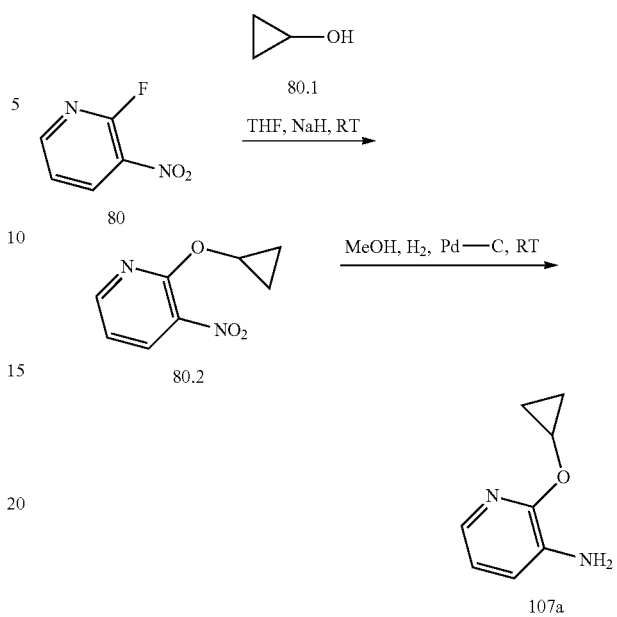

Synthesis of Compound 80.2.

To a cooled solution of 80 (1 g, 7.04 mmol, 1.0 eq) in tetrahydrofuran (10 mL) was added sodium hydride (0.323 g, 14.08 mmol, 2.0 eq) followed by addition of cyclo propanol (0.530 g, 9.15 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 3-4% ethyl acetate in hexane to obtain pure 80.2 (0.900 g, 70.98%), MS(ES): m/z 181.16 [M+H]+.

Synthesis of Compound 107a.

To a solution of 80.2 (0.900 g, 5.00 mmol, 1.0 eq) in methanol (10 mL), palladium on charcoal (0.4 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 107a (0.600 g, 79.98%). MS (ES): m/z 151.18 [M+H]+.

TABLE 60

| Compound | Intermediate | Characterization data |
|---|---|---|
| I-794 | Cl-piperidinylethyl | MS (ES): m/z 489.57 [M + H]+, LCMS purity: 100%, HPLC purity: 99.76%, Chiral HPLC: 49.65%, 50.20%, $^1$H NMR (DMSO-d$_6$, 400 MHZ): 8.76-8.74 (d, J = 7.6 Hz, 1H), 8.69 (s, 1H), 8.50-8.48 (d, J = 8.8 Hz, 1H), 8.41-8.40 (d, J = 4 Hz, 1H), 8.36 (s, 1H), 8.28-8.27 (d, J = 4.4 Hz, 1H), 7.32-7.29 (m, 1H), 6.69 (s, 1H), 4.30-4.26 (t, J = 8.4 Hz, 1H), 4.03-3.97 (m, 1H), 3.75 (bs, 2H), 3.10-3.09 (d, J = 4.4 Hz, 3H), 2.77 (bs, 2H), 2.45 (bs, 4H), 2.10-2.08 (d, J = 6.8 Hz, 2H), 1.47 (bs, 4H), 1.36-1.27 (m, 3H), 0.87-0.84 (t, J = 6 Hz, 2H). |

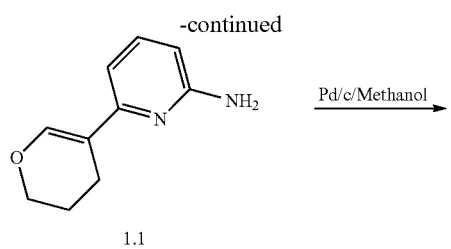

1.1

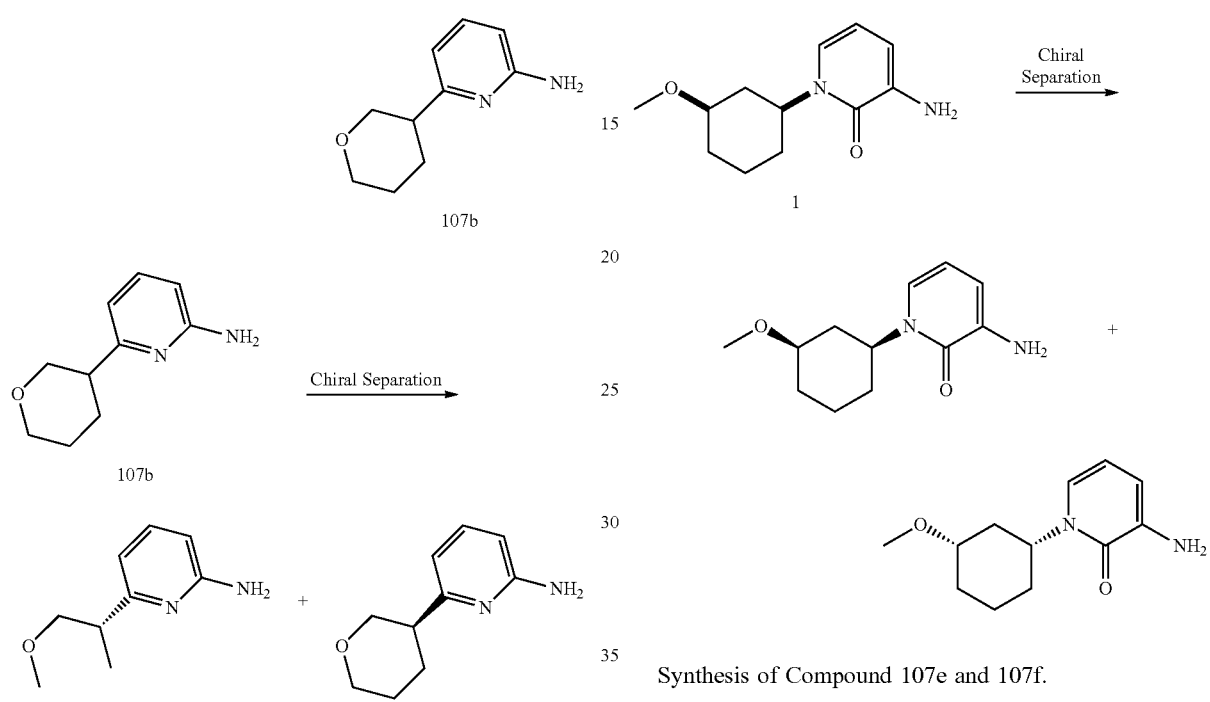

Synthesis of Compound 1.1:

To a solution of 1 (2 g, 9.09 mmol, 1.0 eq), in N,N-dimethylformamide (18 mL) and water (1.6 mL) were added sodium carbonate (4.2 g, 40.297 mmol, 4.5 eq) and 2-(3,4-dihydro-2H-pyran-5-yl)-4,4,5,5-tetramethyl-1,3,2-dioxaborolane (2.49 g, 11.81 mmol, 1.3 eq) at room temperature. The reaction mixture was degassed with argon for 15 min. Then Tetrakis(triphenylphosphine)palladium(0) (1.06 g, 0.909 mmol, 0.1 eq) was added to reaction mixture and stirred at 80° C. for 7 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.1 (1.32 g, 82.40%). MS(ES): m/z 177.23 [M+H]+

Synthesis of Compound 107b:

To a solution of 1.1 (1.3 g, 7.45 mmol, 1.0 eq) in methanol (15 mL), palladium on charcoal (0.511 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 107b (0.8 g, 52.13%). MS (ES): m/z 179.2 [M+H]+

Synthesis of Compound 107c and 107d.

Isomers of 107b (0.8 g) were separated out using column (CHIRAL PAK AD-H 250×4.6 mm, 5 μM) and 0.360% Diethylamine in methanol as co-solvent with flow rate of 4 mL/min. to get pure 107c fraction-1 and 107d fraction-2 (FR-b). FR-a was evaporated under reduced pressure at 30° C. to afford pure 107c. (0.36 g). MS(ES): m/z 179.2 [M+H]+, LCMS purity: 100%, CHIRAL HPLC purity: 100%. FR-b was evaporated under reduced pressure at 30° C. to afford pure 107d. (0.36 g). MS(ES): m/z 179.2 [M+H]+, LCMS purity: 98%, CHIRAL HPLC purity: 100%.

Synthesis of Compound 107e and 107f.

Isomers of 1 (0.855 g) were separated out using column (CHIRAL PAK AD-H 250×4.6 mm, 5M) and DEA in methanol as co-solvent with flow rate of 4 mL/min. to get pure 1a. fraction-1 and 1b. fraction-2 (FR-b). FR-a was evaporated under reduced pressure at 30° C. to afford pure 107e (0.233 g). MS(ES): m/z 223.14 [M+H]+. FR-b was evaporated under reduced pressure at 30° C. to afford pure 107f. (0.246 g). MS(ES): m/z 223.14 [M+H]+.

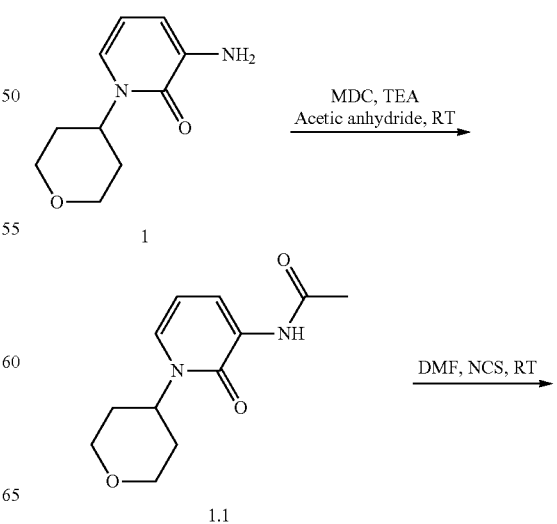

1.1

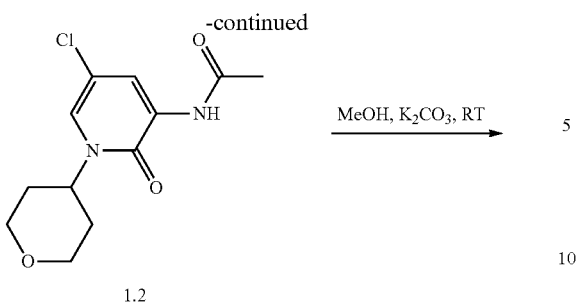

1.2

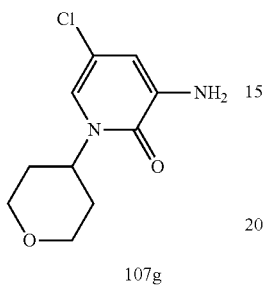

107g

Synthesis of Compound 1.

Compound was synthesized according to the experimental protocols of the intermediates. (Yield: 36.13%). MS (ES): m/z 195.23 [M+H]+

Synthesis of Compound 1.1.

To a solution of 1 (2.0 g, 10.30 mmol, 1.0 eq), in dichloromethane (45 mL) was added triethylamine (2.28 g, 22.66 mmol, 2.2 eq) and Acetic anhydride (1.15 g, 11.33 mmol, 1.1 eq) at room temperature. The reaction mixture was stirred at room temperature for 16 h. After completion of reaction, reaction mixture was transferred into water and product was extracted with dichloro methane. Organic layer was combined and dried over sodium sulphate and concentrated under reduced pressure to obtain 1.1. (1.8 g, 73.99%), MS(ES): m/z 237.12 [M+H]+.

Synthesis of Compound 1.2.

To a stirred solution of 1.1. (1.8 g, 7.59 mmol, 1.0 eq) in dimethyl formamide (18 mL) was added N-Chlorosuccinimide (2.01 g, 15.18 mmol, 2.0 eq) at room temperature. The reaction mixture was stirred for 16 h at room temperature. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 5% methanol in dichloromethane to obtain pure 1.2. (1.1 g, 53.34%). MS(ES): m/z 271.08 [M+2H]+.

Synthesis of Compound 107g.

To a solution of 1.2. (1.1 g, 4.07 mmol, 1.0 eq) in methanol (50 mL), potassium carbonate (5.61 g, 40.07 mmol, 10 eq) was added at room temperature The reaction mixture was stirred for 16 h at room temperature. After completion of reaction, reaction mixture was filtered and washed with methanol. Filtrate was concentrated under reduced pressure to obtain crude material. This was further purified by column chromatography and compound was eluted in 5% methanol in dichloromethane to obtain pure 107 g. (0.4 g, 43.05%). MS (ES): m/z 229.07 [M+H]+.

Example 108: Synthesis of Compounds Comprising N-((1R,2S)-2-fluorocyclopropyl)aminocarbonyl at Position 3 of the pyrazolo[1,5-a]pyrimidine 108.1. Synthesis of 5-((1-(1-cyclopropyl-1H-pyrazol-3-yl)-2-oxo-1,2-dihydropyridin-3-yl)amino)-N-((1R,2S)-2-fluorocyclopropyl)-7-(methylamino)pyrazolo[1,5-a]pyrimidine-3-carboxamide (I-106)

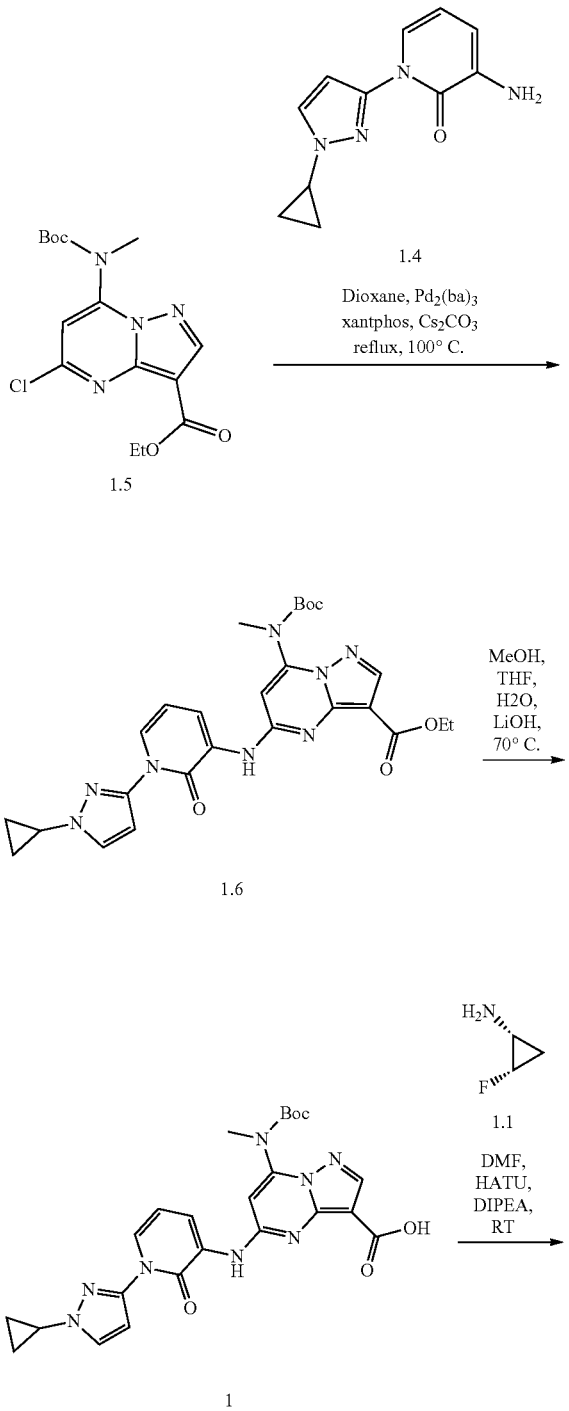

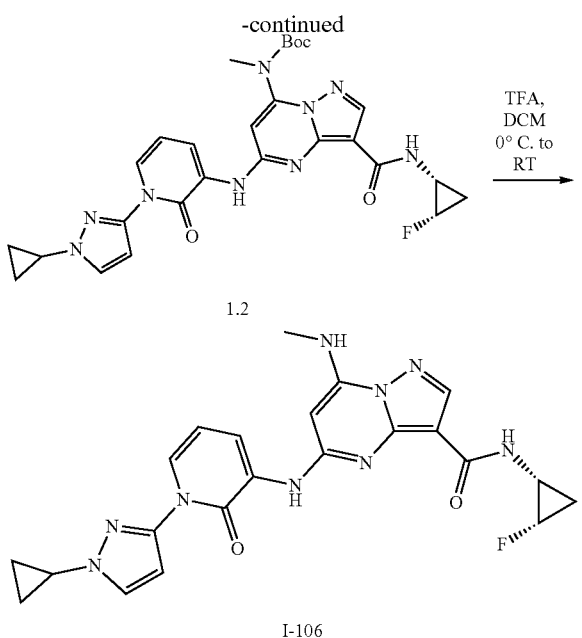

Synthesis of Compound 1.5.

Compound was synthesized using general procedure of core synthesis to obtain 1.5 (Yield: 62.21%). MS (ES): m/z 355.5 [M+H]⁺.

Synthesis of Compound 1.6.

Compound was synthesized using general procedure B to obtain 1.6 (0.270 g, 59.73%). MS (ES): m/z 535.58 [M+H]⁺.

Synthesis of Compound 1.

To a solution of 1.6 (0.270 g, 0.505 mmol, 1.0 eq), in tetrahydrofuran: methanol: water (6 mL, 1:1:1) was added lithium hydroxide (0.212 g, 5.05 mmol, 10 eq). The reaction was stirred at 70° C. temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1 (0.200 g, 78.18%). MS(ES): m/z 507.52 [M+H]⁺.

Synthesis of Compound 1.2.

Compound was synthesized using general procedure A to obtain 1.2. (0.050 g, 74.89%). MS (ES): m/z 564.59 [M+H]⁺

Synthesis of Compound I-106:

Compound was synthesized using general procedure C to obtain I-106 (0.035 g, 85.12%), MS (ES): m/z 464.40 [M+H]⁺, LCMS purity: 95.40%, HPLC purity: 96.16%, CHIRAL HPLC purity: 98.48%, ¹H NMR (DMSO-d₆, 400 MHZ): 9.00 (s, 1H), 8.25 (S, 1H), 8.20-8.18 (d, J=8 Hz, 1H), 7.96-7.93 (m, 2H), 7.81-7.80 (d, J=4 Hz, 1H), 7.66-7.65 (d, J=4 Hz, 1H), 6.74 (s, 1H), 6.37-6.36 (t, J=4 Hz, 1H), 6.26 (s, 1H), 4.81 (s, 1H), 3.79 (s, 1H), 3.00 (s, 1H), 2.91-2.90 (d, J=4 Hz, 3H), 1.23 (s, 2H), 1.09-1.07 (d, J=8 Hz, 2H), 1.01-1.00 (d, J=4 Hz, 2H).

Additional compounds prepared by substantially the same method, and their characterization data, are listed in the Table 61 below. The intermediate corresponding to 1.4 of the above scheme is listed for each compound.

TABLE 61

| Compound | Intermediate | Characterization Data |
|---|---|---|
| I-110 | | MS (ES): m/z 372.48 [M + H]⁺, LCMS purity: 100%, HPLC purity: 99.90%, ¹H NMR (DMSO-d₆, 400 MHZ): 8.90 (s, 1H), 8.23-8.21 (d, J = 8 Hz, 1H), 8.19 (s, 1H), 7.93-7.88 (m, 2H), 7.82-7.81 (d, J = 4 Hz, 1H), 6.99-6.96 (m, 1H), 5.93 (s, 1H), 4.87-4.86 (d, J = 4 Hz, 1H), 3.95 (s, 3H), 2.91-2.90 (d, J = 4 Hz, 4H), 1.14-1.07 (m, 1H), 0.75-0.69 (m, 1H). |
| I-115 | | MS (ES): m/z 453.36 [M + H]⁺, LCMS purity: 96.39%, HPLC purity: 99.66%, CHIRAL HPLC purity: 99.50%, ¹H NMR (DMSO-d₆, 400 MHZ): 8.99 (s, 1H), 8.67-8.66 (d, J = 4 Hz, 1H), 8.32-8.31 (d, J = 4 Hz, 1H), 8.26 (s, 1H), 8.05-7.92 (m, 3H), 7.84-7.83 (d, J = 4 Hz, 1H), 7.55-7.53 (d, J = 8 Hz, 1H), 6.42-6.41 (t, J = 4 Hz, 1H), 6.27 (s, 1H), 4.99-4.81 (m, 1H), 3.03-3.00 (m, 1H), 2.92-2.91 (d, J = 4 Hz, 3H), 1.30-1.20 (m, 1H), 0.95-0.86 (m, 1H). |
| I-117 | | MS (ES): m/z 480.35 [M + H]⁺, LCMS purity: 100%, HPLC purity: 98.72%, ¹H NMR (DMSO-d₆, 400 MHZ): 9.00 (s, 1H), 8.29-8.26 (m, 2H), 8.04-8.02 (d, J = 8 Hz, 1H), 7.97-7.96 (d, J = 4 Hz, 1H), 7.83-7.82 (d, J = 4 Hz, 1H), 7.57-7.56 (d, J = 4 Hz, 1H), 7.46-7.43 (d, J = 12 Hz, 1H), 6.45-6.43 (t, J = 8 Hz, 1H), 6.26 (s, 1H), 5.05-4.82 (m, 1H), 4.58-4.52 (m, 2H), 3.03-2.99 (m, 1H), 2.91-2.90 (d, J = 4 Hz, 3H), 1.44-1.42 (t, J = 8 Hz, 3H), 0.87-0.85 (m, 2H). |

TABLE 61-continued

| Compound | Intermediate | Characterization Data |
|---|---|---|
| I-123 | | MS (ES): m/z 493.52 [M + H]+, LCMS purity: 100%, HPLC purity: 99.70%, CHIRAL HPLC: 100%, $^1$H NMR (DMSO-$d_6$, 400 MHZ): 8.99 (s, 1H), 8.26-8.24 (d, J = 8.8 Hz, 2H), 8.03-7.95 (m, 2H), 7.85-7.84 (d, J = 6 Hz, 2H), 7.77-7.71 (m, 2H), 7.60-7.59 (d, J = 6 Hz, 1H), 6.44-6.40 (t, J = 14.4 Hz, 1H), 6.27 (s, 1H), 5.37 (s, 1H), 4.83-4.82 (m, 1H), 3.01-2.99 (m, 1H), 2.92-2.91 (m, 3H), 1.49 (s, 6H), 1.30-1.20 (m, 1H). |
| I-131 | | MS (ES): m/z 449.46 [M + H]+, LCMS purity: 99.25%, HPLC purity: 94.78%, $^1$H NMR (DMSO-$d_6$, 400 MHZ): 8.97 (s, 1H), 8.25-8.22 (m, 2H), 7.94-7.90 (m, 2H), 7.84-7.83 (d, J = 4.4 Hz, 1H), 7.62-7.60 (d, J = 8 Hz, 1H), 7.54-7.53(d, J = 1.6 Hz, 1H), 7.40-7.73 (m, 1H), 6.40-6.36 (m, 1H), 6.25 (s, 1H), 5.00-4.98 (m, 1H), 4.82-4.81 (s, 1H), 3.00-2.99 (m, 1H), 2.90 (s, 3H), 2.54-2.46 (m, 3H), 2.01-1.99 (d, J = 7.2 Hz, 1H). |
| I-132 | | MS (ES): m/z 452.44 [M + H]+, LCMS purity: 96.73%, HPLC purity: 95.73%, CHIRAL HPLC: 99.63%, $^1$H NMR (DMSO-$d_6$, 400 MHZ): 8.94 (s, 1H), 8.25-8.23 (d, J = 10 Hz, 2H), 7.95 (s, 1H), 7.83-7.82 (d, J = 4 Hz, 1H), 7.55-7.54 (d, J = 5.2 Hz, 2H), 7.41-7.39 (m, 2H), 7.34-7.32 (d, J = 6.8 Hz, 1H), 6.36-6.32 (t, J = 14 Hz, 1H), 6.25 (s, 1H), 4.99 (s, 1H), 4.82 (s, 1H), 3.01 (s, 1H), 2.90-2.89 (d, J = 4.4 Hz, 3H), 1.27-1.24 (m, 1H). |
| I-134 | | MS (ES): m/z 452.44 [M + H]+, LCMS purity: 100%, HPLC purity: 99.54%, $^1$H NMR (DMSO-$d_6$, 400 MHZ): 9.62 (s, 1H), 8.35 (s, 1H), 8.20-8.19 (d, J = 4.8 Hz, 1H), 8.09-8.08 (d, J = 4.8 Hz, 1H), 7.92-7.91 (d, J = 4 Hz, 1H), 7.75-7.91 (m, 3H), 7.40-7.35 (m, 2H), 6.51(s, 1H), 4.87-4.86 (m, 1H), 3.02-3.00 (m, 1H), 2.92 (s, 3H), 1.34-0.99 (m, 2H). |
| I-135 | | MS (ES): m/z 519.55 [M + H]+, LCMS purity: 95.01%, HPLC purity: 99.80%, CHIRAL HPLC: 98.54%, $^1$H NMR (DMSO-$d_6$, 400 MHZ): 8.91 (s, 1H), 8.25-8.21 (m, 2H), 7.94-7.93 (d, J = 4.8 Hz, 1H), 7.85-7.84 (d, J = 4.4 Hz, 1H), 7.34-7.28 (m, 3H), 7.08-7.06 (d, J = 8.8 Hz, 2H), 6.34-6.30 (t, J = 14 Hz, 1H), 6.25 (s, 1H), 4.98-4.82 (m, 1H), 3.77 (s, 4H), 3.20 (s, 4H), 3.03-3.01 (m, 1H), 2.92-2.90 (d, J = 4.4 Hz, 3H), 1.28-1.23 (m, 1H), 0.94 (m, 1H). |
| I-137 | | MS (ES): m/z 452.47 [M + H]+, LCMS purity: 100%, HPLC purity: 99.58%, CHIRAL HPLC: 100%, $^1$H NMR (DMSO-$d_6$, 400 MHZ): 8.96 (s, 1H), 8.25 (s, 1H), 8.18-8.17 (d, J = 6.4 Hz, 1H), 7.96-7.94 (d, J = 4.8 Hz, 1H), 7.81-7.80 (d, J = 4.4 Hz, 1H), 7.62-7.62 (d, J = 1.6 Hz, 1H), 6.55 (s, 1H), 6.35-6.32 (t, J = 7.2 Hz, 1H), 6.26 (s, 1H), 4.97 (m, 1H), 3.77 (s, 3H), 3.02-2.97 (m, 1H), 2.91-2.90 (d, J = 4 Hz, 3H), 2.32 (s, 3H), 1.26-1.18 (m, 2H). |
| I-140 | | MS (ES): m/z 438.44 [M + H]+, LCMS purity: 97.80%, HPLC purity: 97.95%, CHIRAL HPLC: 95.62%, $^1$H NMR (DMSO-$d_6$, 400 MHZ): 9.00 (s, 1H), 8.25 (s, 1H), 8.20-8.18 (d, J = 6.8 Hz, 1H), 7.96-7.95 (d, J = 4.8 Hz, 1H), 7.83-7.80 (m, 2H), 7.65-7.64 (d, J = 6.8 Hz, 1H), 6.74 (s, 1H), 6.37-6.34 (t, J = 7.2 Hz, 1H), 6.27 (s, 1H), 4.97-4.81 (m, 1H), 3.90 (s, 3H), 3.17-3.16 (d, J = 5.2 Hz, 1H), 2.91-2.90 (d, J = 2.8 Hz, 3H), 1.98-1.94 (m, 1H), 0.92-0.86 (m, 1H). |

TABLE 61-continued

| Compound | Intermediate | Characterization Data |
|---|---|---|
| I-147 | (pyridine with O-isopropyl and NH2) | MS (ES): m/z 400.43 [M + H]+, LCMS purity: 99.32%, HPLC purity: 99.34%, CHIRAL HPLC: 99.82%, $^1$H NMR (DMSO-$d_6$, 400 MHZ): 8.63 (s, 1H), 8.19-8.17 (d, J = 6.4 Hz, 2H), 7.93-7.82 (m, 3H), 6.94-6.91 (m, 1H), 5.94 (s, 1H), 5.37-5.31 (m, 1H), 4.87-4.69 (m, 1H), 2.94-2.87 (m, 4H), 1.34-1.32 (m, 6H), 1.17-1.07 (m, 1H), 0.72-0.73 (m, 1H). |
| I-148 | (chloro-pyridine with O-isopropyl and NH2) | MS (ES): m/z 434.87 [M + H]+, LCMS purity: 96.91%, HPLC purity: 95.45%, CHIRAL HPLC: 94.42%, $^1$H NMR (DMSO-$d_6$, 400 MHZ): 8.75 (s, 1H), 8.33-8.33 (d, J = 2.4 Hz, 1H), 8.22 (s, 1H), 8.02-8.00 (d, J = 5.2 Hz, 1H), 7.88-7.88 (d, J = 2 Hz, 1H), 7.81-7.80 (d, J = 4 Hz, 1H), 5.99 (s, 1H), 5.33-5.27 (m, 1H), 4.82-4.65 (m, 1H), 2.94-2.93 (d, J = 4.8 Hz, 3H), 2.85-2.81 (m, 1H), 1.33-1.23 (m, 6H), 1.18-1.09 (m, 2H). |

108.2. Synthesis of N-((1R,2S)-2-fluorocyclopropyl)-7-(methylamino)-5-((1-(2-methylpyrimidin-4-yl)-2-oxo-1,2-dihydropyridin-3-yl)amino)pyrazolo[1,5-a]pyrimidine-3-carboxamide (I-124)

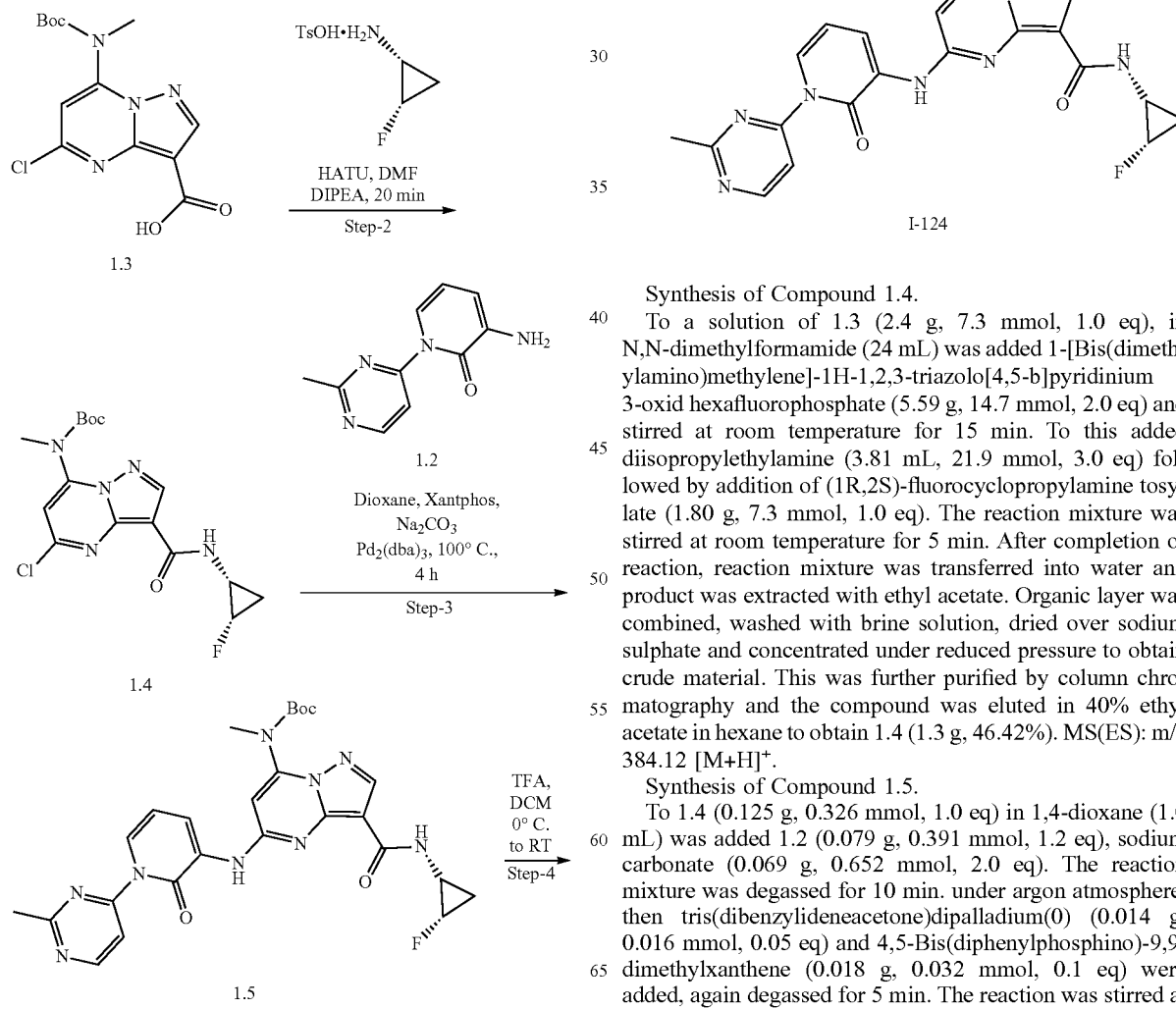

Synthesis of Compound 1.4.

To a solution of 1.3 (2.4 g, 7.3 mmol, 1.0 eq), in N,N-dimethylformamide (24 mL) was added 1-[Bis(dimethylamino)methylene]-1H-1,2,3-triazolo[4,5-b]pyridinium 3-oxid hexafluorophosphate (5.59 g, 14.7 mmol, 2.0 eq) and stirred at room temperature for 15 min. To this added diisopropylethylamine (3.81 mL, 21.9 mmol, 3.0 eq) followed by addition of (1R,2S)-fluorocyclopropylamine tosylate (1.80 g, 7.3 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.4 (1.3 g, 46.42%). MS(ES): m/z 384.12 [M+H]+.

Synthesis of Compound 1.5.

To 1.4 (0.125 g, 0.326 mmol, 1.0 eq) in 1,4-dioxane (1.0 mL) was added 1.2 (0.079 g, 0.391 mmol, 1.2 eq), sodium carbonate (0.069 g, 0.652 mmol, 2.0 eq). The reaction mixture was degassed for 10 min. under argon atmosphere, then tris(dibenzylideneacetone)dipalladium(0) (0.014 g, 0.016 mmol, 0.05 eq) and 4,5-Bis(diphenylphosphino)-9,9-dimethylxanthene (0.018 g, 0.032 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 1.5 (0.070 g, 39.10%). MS(ES): m/z 550.22 [M+H]$^+$.

Synthesis of Compound I-124.

The compound 1.5 (0.070 g, 0.129 mmol, 1.0 eq) was dissolved in dichloromethane (2 mL) and trifluoroacetic acid (0.1 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure I-124 (0.040 g, 70.17%). MS(ES): m/z 450.37 [M+H]$^+$, LCMS purity: 100%, HPLC purity: 97.26%, $^1$H NMR (DMSO-d$_6$, 400 MHz): 9.04 (s, 1H), 8.92-8.91 (d, J=5.2 Hz, 1H), 8.26 (s, 1H), 8.24 (s, 1H), 7.98-7.94 (m, 2H), 7.83-7.82 (d, J=4.4 Hz, 1H), 7.77-7.75 (d, J=6.8 Hz, 1H), 6.47-6.44 (t, J=7.2 Hz, 1H), 6.28 (s, 1H), 4.98-4.82 (d, 1H), 3.00 (brs, 1H), 2.92-2.91 (d, J=4.4 Hz, 3H), 2.77-2.68 (m, 3H), 1.27-1.22 (t, J=10.4 Hz, 2H).

Additional compounds prepared by substantially the same method, and their characterization data, are listed in the Table 62 below. The intermediate corresponding to 1.2 of the above scheme is listed for each compound.

TABLE 62

| Compound | Intermediate | Characterization Data |
|---|---|---|
| I-126 | | MS (ES): m/z 507.50 [M + H]$^+$, LCMS purity: 100%, HPLC purity: 100%, CHIRAL HPLC: 100%, $^1$H NMR (DMSO-d$_6$, 400 MHZ): 9.23 (s, 1H), 9.07 (s, 1H), 8.93 (s, 1H), 8.30-8.27 (t, J = 11.6 Hz, 2H), 7.99-7.98 (d, J = 4.8 Hz, 1H), 7.83-7.82 (d, J = 4.4 Hz 1H), 7.68-7.65 (d, J = 6.4 Hz, 1H), 6.51-6.48 (t, J = 14.4 Hz, 1H), 6.29 (s, 1H), 4.99-4.83 (m, 1H), 3.09-3.06 (d, J = 11.2 Hz, 6H), 2.93-2.92 (d, J = 4.8 Hz, 3H), 1.24 (m, 2H), 0.949-0.867 (m, 1H). |
| I-128 | | MS (ES): m/z 532.55 [M + H]$^+$, LCMS purity: 99.21%, HPLC purity: 98.32%, CHIRAL HPLC: 100%, $^1$H NMR (DMSO-d$_6$, 400 MHZ): 8.73 (s, 1H), 8.50 (s, 1H), 8.12-8.10 (d, J = 8.4 Hz, 1H), 7.95-7.93 (d, J = 8.4 Hz, 1H), 7.90-7.88 (d, J = 6.8 Hz, 1H), 7.79-7.78 (d, J = 6.4 Hz, 1H), 6.48-6.44 (t, J = 7.2 Hz, 1H), 4.81 (s, 1H), 4.64 (s, 1H), 3.50-3.44 (d, J = 6 Hz, 4H), 3.00 (s, 3H), 2.86 (s, 1H), 2.00 (s, 3H), 1.84 (bs, 4H), 1.19-0.99 (m, 2H). |
| I-142 | | MS (ES): m/z 518.53 [M + H]$^+$, LCMS purity: 99.73%, HPLC purity: 98.41%, $^1$H NMR (DMSO-d$_6$, 400 MHZ): 8.99 (s, 1H), 8.85 (s, 1H), 8.26 (s, 3H), 7.97 (s, 2H), 7.83 (s, 1H), 7.63 (s, 1H), 6.42 (s, 1H), 6.26 (s, 1H), 4.98-4.82 (m, 1H), 4.42 (s, 2H), 4.11 (s, 2H), 2.91 (s, 3H), 2.30 (bs, 2H), 1.23 (bs, 2H), 0.86 (bs, 1H). |
| I-144 | | MS (ES): m/z 453.40 [M + H]$^+$, LCMS purity: 100%, HPLC purity: 99.68%, Chiral HPLC: 99.34%, $^1$H NMR (DMSO-d$_6$, 400 MHZ): 9.02 (s, 1H), 8.52-8.51 (d, J = 4.4 Hz, 1H), 8.30-8.27 (m, 2H), 8.09-8.05 (t, J = 8.8 Hz, 1H), 7.99-7.98 (d, J = 4.8 Hz, 1H), 7.84-7.83 (d, J = 4.4 Hz, 1H), 7.75-7.71 (m, 1H), 7.44-7.43 (d, J = 5.6 Hz, 1H), 6.45-6.41 (t, J = 7.2 Hz, 1H), 6.25 (s, 1H), 5.01-4.83 (m, 1H), 3.03-3.00 (m, 1H), 2.91-2.90 (d, J = 4.8 Hz, 3H), 1.28-1.22 (m, 1H), 0.96-0.87 (m, 1H). |

TABLE 62-continued

| Compound | Intermediate | Characterization Data |
| --- | --- | --- |
| I-153 | | MS(ES): m/z 408.24 [M + H]⁺, LCMS purity: 96.65%, HPLC purity: 95.53%, CHIRAL HPLC purity: 97.78%, $^1$H NMR (DMSO-d$_6$, 400 MHZ): 8.35-8.33 (d, J = 8 Hz, 1H), 8.20 (s, 1H), 7.97-7.96 (t, J = 4 Hz, 2H), 7.78-7.76 (d, J = 8 Hz, 2H), 7.58 (s, 1H), 7.26-7.23 (m, 1H), 5.90 (s, 1H), 4.84-4.68 (m, 1H), 2.92 (s, 3H), 2.89-2.88 (m, 1H), 1.16-1.07 (m, 1H), 0.69-0.62 (m, 1H). |
| I-161 | | MS(ES): m/z 439.42 [M + H]⁺, LCMS purity: 100%, HPLC purity: 100%, CHIRAL HPLC: 99.29%, $^1$H NMR (DMSO-d$_6$, 400 MHZ): 9.06 (s, 1H), 8.26-8.24 (m, 2H), 8.00-7.98 (d, J = 4.8 Hz, 1H), 7.80-7.94 (d, J = 4.8 Hz, 1H), 7.59-7.57(d, J = 6.8 Hz 1H), 6.88 (s, 1H), 6.44-6.41 (t, J = 7.2 Hz, 1H), 6.28 (s, 1H), 4.98-4.81 (m, 1H), 3.00-2.98 (m, 1H), 2.92-2.91 (d, J = 4.8 Hz, 3H), 2.36 (s, 3H), 1.28-1.21 (m, 1H), 0.94-0.92 (m, 1H). |
| I-164 | | MS(ES): m/z 484.89 [M + H]⁺, LCMS purity: 96.69%, HPLC purity: 97.35%, CHIRAL HPLC purity: 96.44%, $^1$H NMR (DMSO-d$_6$, 400 MHZ): 9.19 (s, 1H), 8.40-8.39 (d, J = 2 Hz, 1H), 8.30 (s, 1H), 8.08-8.06 (d, J = 8.8 Hz, 2H) 7.86-7.82 (m, 3H), 6.35 (s, 1H), 4.93-4.77 (m, 1H), 2.96-2.91 (m, 4H), 2.73 (s, 3H), 1.24-1.18 (m, 2H). |
| I-165 | | MS(ES): m/z 476.49 [M + H]⁺, LCMS purity: 100%, HPLC purity: 99.57%, $^1$H NMR, CHIRAL HPLC: 100% (DMSO-d$_6$, 400 MHZ): 9.00 (s, 1H), 8.29-8.26 (d, J = 12 Hz, 2H), 8.01-7.97 (m, 2H), 7.83-7.75 (m, 2H), 7.60-7.59 (d, J = 6 Hz 1H), 6.45-6.41 (t, J = 14 Hz, 1H), 6.26 (s, 1H), 4.98-4.82 (m, 1H), 3.00 (s, 1H), 2.91-2.90 (d, J = 4 Hz, 3H), 2.37 (s, 1H), 1.27-1.14 (m, 5H), 0.93 (bs, 1H). |
| I-166 | | MS (ES): m/z 456.61 [M + H]⁺, LCMS purity: 100%, HPLC purity: 95.65%, CHIRAL HPLC purity: 97.80%, $^1$H NMR (DMSO-d$_6$, 400 MHZ): 8.84 (s, 1H), 8.24 (s, 1H), 8.12-8.10 (d, J = 8 Hz, 1H), 7.93-7.92 (d, J = 4 Hz, 1H), 7.81-7.80 (d, J = 4 Hz, 1H), 7.42-7.40 (d, J = 8 Hz, 1H), 6.28-6.27 (t, J = 4 Hz, 1H), 6.23 (s, 1H), 4.98-4.77 (m, 2H), 3.52 (m, 1H), 2.99-2.95 (m, 1H), 2.92-2.91 (d, J = 4 Hz, 3H), 1.98-1.95 (m, 2H), 1.81-1.77 (m, 4H), 1.37-1.34 (m, 3H), 1.28-1.18 (m, 1H), 0.90-0.83 (m, 1H). |
| I-170 | | MS (ES): m/z 412.61 [M + H]⁺, LCMS purity: 95.43%, HPLC purity: 95.36%, CHIRAL HPLC purity: 96.11%, $^1$H NMR (DMSO-d$_6$, 400 MHZ): 8.74 (s, 1H), 8.23-8.21 (d, J = 8 Hz, 1H), 8.20 (s, 1H), 7.95-7.93 (d, J = 8 Hz, 1H), 7.85-7.83 (t, J = 8 Hz, 2H), 6.97-6.93 (m, 1H), 5.96 (s, 1H), 5.26-5.24 (t, J = 8 Hz, 1H), 4.87-4.70 (m, 1H), 2.94-2.93 (d, J = 4 Hz, 3H), 2.90 (m, 1H), 1.86-1.78 (m, 2H), 1.72-1.63 (m, 2H), 1.24-1.23 (m, 2H), 0.89-0.86 (m, 1H), 0.78-0.64 (m, 1H). |

TABLE 62-continued

| Compound | Intermediate | Characterization Data |
|---|---|---|
| I-174 | (tetrahydropyran-4-yloxy connected to 3-aminopyridin-2-yl) | MS (ES): m/z 442.52 [M + H]+, LCMS purity: 96.11%, HPLC purity: 95.20%, $^1$H NMR (DMSO-d$_6$, 400 MHZ): 8.67 (s, 1H), 8.19 (s, 1H), 8.18-8.16 (d, J = 8 Hz, 1H), 7.92-7.90 (t, J = 8 Hz, 2H), 7.82-7.80 (d, J = 8 Hz, 1H), 6.98-6.97 (t, J = 4 Hz, 1H), 5.92 (s, 1H), 5.31-5.27 (m, 1H), 4.84-4.67 (m, 1H), 3.88-3.84 (m, 2H), 3.51-3.45 (m, 2H), 2.95-2.94 (d, J = 4 Hz, 3H), 2.89-2.87 (m, 1H), 2.00 (bs, 2H), 1.74-1.67 (m, 2H), 1.17-1.08 (m, 1H), 0.65-0.63 (m, 1H). |
| I-177 | (D$_3$C-O-pyridine with NH$_2$) | MS (ES): m/z 375.23 [M + H]+, LCMS purity: 100%, HPLC purity: 99.36%, CHIRAL HPLC purity: 100%, $^1$H NMR (DMSO-d$_6$, 400 MHZ): 8.90 (s, 1H), 8.23-8.21 (d, J = 8 Hz, 1H), 8.19 (s, 1H), 7.93-7.92 (d, J = 4 Hz, 1H), 7.89-7.88 (d, J = 4 Hz, 1H), 7.83-7.81 (d, J = 4 Hz, 1H), 6.99-6.98 (t, J = 4 Hz, 1H), 5.93 (s, 1H), 4.87-4.69 (m, 1H), 2.91-2.90 (d, J = 4 Hz, 4H), 1.23-1.10 (m, 1H), 0.77-0.68 (m, 1H). |
| I-186 | (trans-methoxycyclobutyl-O-pyridine-NH$_2$) | MS (ES): m/z 442.52 [M + H]+, LCMS purity: 100%, HPLC purity: 96.31%, CHIRAL HPLC purity: 99.10%, $^1$H NMR (DMSO-d$_6$, 400 MHZ): 8.76 (s, 1H), 8.25-8.23 (d, J = 8 Hz, 1H), 8.21 (s, 1H), 7.95-7.94 (d, J = 4 Hz, 1H), 7.85-7.81 (m, 2H), 6.98-6.95 (m, 1H), 5.96 (s, 1H), 4.95-4.73 (m, 2H), 3.68-3.66 (t, J = 8 Hz, 1H), 3.16 (s, 3H), 2.95-2.93 (d, J = 8 Hz, 3H), 2.87-2.82 (m, 2H), 2.08-2.02 (m, 2H), 1.24 (bs, 1H), 1.18-1.13 (m, 1H), 0.77-0.68 (m, 1H). |
| I-189 | (cis-methoxycyclobutyl-O-pyridine-NH$_2$) | MS (ES): m/z 442.51 [M + H]+, LCMS purity: 95.30%, HPLC purity: 96.30%, CHIRAL HPLC purity: 98.75%, $^1$H NMR (DMSO-d$_6$, 400 MHZ): 8.75 (s, 1H), 8.22-8.20 (m, 1H), 7.95-7.94 (d, J = 4 Hz, 1H), 7.87-7.86 (d, J = 4 Hz, 1H), 7.83-7.82 (d, J = 4 Hz, 1H), 6.98-6.95 (m, 1H), 5.93 (s, 1H), 5.35-5.34 (t, J = 4 Hz, 1H), 4.87 (s, 1H), 4.70 (s, 1H), 4.06-4.05 (t, J = 4 Hz, 1H), 3.16 (s, 3H), 2.95-2.90 (m, 4H), 2.41-2.39 (m, 4H), 1.17-1.12 (m, 1H), 0.72-0.68 (m, 1H). |
| I-194 | (5-fluoro-3-amino-N-(pyridin-2-yl)pyridin-2(1H)-one) | MS (ES): m/z 453.51 [M + H]+, LCMS purity: 98.77%, HPLC purity: 97.95%, CHIRAL HPLC purity: 99.00%, $^1$H NMR (DMSO-d$_6$, 400 MHZ): 9.21 (s, 1H), 8.65-8.64 (d, J = 4 Hz, 1H), 8.38-8.36 (d, J = 4 Hz, 1H), 8.30 (s, 1H), 8.08-8.06 (t, J = 8 Hz, 2H), 7.92-7.90 (d, J = 8 Hz, 1H), 7.78-7.74 (m, 2H), 7.56-7.54 (t, J = 8 Hz, 1H), 6.57 (s, 1H), 4.91-4.74 (m, 1H), 2.96 (m, 1H), 2.91 (s, 3H), 1.23-1.14 (m, 1H), 1.00-0.93 (m, 1H). |
| I-198 | (5-fluoro-3-amino-N-(6-methylpyridazin-3-yl)pyridin-2(1H)-one) | MS (ES): m/z 468.52 [M + H]+, LCMS purity: 100%, HPLC purity: 99.11%, $^1$H NMR (DMSO-d$_6$, 400 MHZ): 9.24 (s, 1H), 8.44-8.41 (m, 1H), 8.31 (s, 1H), 8.11-8.09 (d, J = 8 Hz, 2H), 7.86-7.78 (m, 3H), 6.38 (s, 1H), 4.91-4.75 (m, 1H), 2.97 (m, 1H), 2.92 (s, 3H), 2.68 (s, 3H), 1.25-1.17 (m, 2H). |

TABLE 62-continued

| Compound | Intermediate | Characterization Data |
| --- | --- | --- |
| I-200 | | MS (ES): m/z 432.46 [M + H]⁺, LCMS purity: 97.64%, HPLC purity: 96.26%, Chiral HPLC purity: 99.26%, ¹H NMR (DMSO-d₆, 400 MHZ): 8.86 (s, 1H), 8.23 (s, 1H), 8.15-8.13 (d, J = 8 Hz, 1H), 7.92-7.91 (d, J = 4 Hz, 1H), 7.83 (s, 1H), 7.29-7.27 (d, J = 8 Hz, 1H), 6.24-6.22 (d, J = 8 Hz, 2H), 4.81-4.79 (d, J = 8 Hz, 1H), 4.78 (s, 1H), 4.59 (m, 1H), 4.30-4.27 (d, J = 12 Hz, 1H), 3.83-3.70 (m, 2H), 2.92 (s, 1H), 2.90-2.89 (d, J = 4 Hz, 3H), 1.35-1.31 (m, 2H), 0.71-0.69 (m, 2H). |
| I-211 | | MS (ES): m/z 418.29 [M + H]⁺, LCMS purity: 98.43%, HPLC purity: 97.98%, CHIRAL HPLC purity: 100%, ¹H NMR (DMSO-d₆, 400 MHZ): 8.72 (s, 1H), 8.29-8.25 (m, 2H), 8.03-8.02 (d, J = 4 Hz, 1H), 7.81-7.78 (m, 2H), 6.08 (s, 1H), 5.32-5.30 (d, J = 8 Hz, 1H), 4.85-4.67 (m, 1H), 2.96-2.94 (d, J = 8 Hz, 3H), 2.92 (m, 1H), 1.37-1.35 (d, J = 8 Hz, 6H), 1.16-1.10 (m, 1H), 0.87-0.81 (m, 1H), 0.75 (bs, 1H). |
| I-214 | | MS (ES): m/z 414.49 [M + H]⁺, LCMS purity: 99.55%, HPLC purity: 95.84%, CHIRAL HPLC purity: 97.37%, ¹H NMR (DMSO-d₆, 400 MHZ): 8.58 (s, 1H), 8.17 (s, 1H), 7.96 (s, 1H), 7.90-7.88 (m, 2H), 7.71 (s, 1H), 5.85 (s, 1H), 5.29-5.28 (t, J = 4 Hz, 1H), 4.80-4.64 (m, 1H), 2.92-2.91 (d, J = 4 Hz, 3H), 2.81-2.80 (m, 1H), 2.33 (s, 3H), 1.299-1.293 (d, J = 2.4 Hz, 6H), 1.14-1.06 (m, 1H), 0.61-0.55 (m, 1H). |
| I-217 | | MS (ES): m/z 398.17 [M + H]⁺, LCMS purity: 100%, HPLC purity: 99.03%, CHIRAL HPLC purity: 100%, ¹H NMR (DMSO-d₆, 400 MHZ): 8.70 (s, 1H), 8.24-8.22 (d, J = 8 Hz, 1H), 8.20 (s, 1H), 7.95-7.92 (m, 2H), 7.82-7.81 (d, J = 4 Hz, 1H), 7.02-6.99 (m, 1H), 5.90 (s, 1H), 4.89-4.69 (m, 1H), 4.35-4.32 (m, 1H), 2.92-2.91 (d, J = 4 Hz, 3H), 1.23-1.21 (m, 1H), 0.79-0.71 (m, 6H). |
| I-220 | | MS (ES): m/z 416.41 [M + H]⁺, LCMS purity: 100%, HPLC purity: 98.84%, CHIRAL HPLC purity: 100%, ¹H NMR (DMSO-d₆, 400 MHZ): 8.80 (s, 1H), 8.20 (s, 1H), 8.19 (s, 1H), 7.93 (bs, 1H), 7.88-7.87 (d, J = 4 Hz, 1H), 7.83-7.81 (d, J = 8 Hz, 1H), 6.99-6.96 (m, 1H), 5.93 (s, 1H), 4.85-4.69 (m, 1H), 4.51-4.50 (t, J = 4 Hz, 2H), 3.71-3.70 (t, J = 4 Hz, 2H), 3.26 (s, 3H), 2.92 (s, 3H), 2.89 (m, 1H), 1.16-1.11 (m, 1H), 0.72-0.66 (m, 1H). |
| I-227 | | MS (ES): m/z 440.41 [M + H]⁺, LCMS purity: 100%, HPLC purity: 98.78%, CHIRAL HPLC purity: 100%, ¹H NMR (DMSO-d₆, 400 MHZ): 8.62 (s, 1H), 8.19 (s, 1H), 8.17-8.15 (d, J = 8 Hz, 1H), 7.92-7.91 (d, J = 4 Hz, 1H), 7.89-7.88 (d, J = 4 Hz, 1H), 7.83-7.82 (d, J = 4 Hz, 1H), 6.95-6.92 (m, 1H), 5.92 (s, 1H), 5.12-5.07 (m, 1H), 4.86-4.69 (m, 1H), 2.95-2.93 (d, J = 8 Hz, 3H), 2.90-2.86 (m, 1H), 1.75-1.73 (m, 2H), 1.55-1.47 (m, 2H), 1.37-1.32 (m, 2H), 1.27-1.21 (m, 2H), 1.16-1.11 (m, 2H), 0.89-0.85 (m, 1H), 0.73-0.72 (m, 1H) |

TABLE 62-continued

| Compound | Intermediate | Characterization Data |
|---|---|---|
| I-229 | (oxetan-3-yloxy)pyridin-3-amine structure | MS (ES): m/z 427.51 [M + H]⁺, LCMS purity: 99.26%, HPLC purity: 98.99%, CHIRAL HPLC purity: 100%, ¹H NMR (DMSO-d₆, 400 MHZ): 9.90 (s, 1H), 8.26 (s, 1H), 8.11 (s, 1H), 8.00-7.99 (d, J = 4 Hz, 1H), 7.79-7.77 (t, J = 8 Hz, 1H), 7.69-7.67 (d, J = 8 Hz, 1H), 7.34-7.32 (d, J = 8 Hz, 1H), 6.59 (s, 1H), 4.93-4.76 (m, 1H), 4.50-4.48 (t, J = 8 Hz, 2H), 4.29-4.27 (t, J = 8 Hz, 2H), 2.96 (s, 4H), 1.24-1.20 (m, 1H), 1.04-0.98 (m, 1H). |
| I-230 | 1-(1-(2,2-difluoroethyl)piperidin-4-yl)-3-amino-pyridin-2(1H)-one structure | MS (ES): m/z 505.53 [M + H]⁺, LCMS purity: 100%, HPLC purity: 100%, CHIRAL HPLC purity: 100%, ¹H NMR (DMSO-d₆, 400 MHZ): 8.68 (s, 1H), 8.19 (s, 1H), 8.13-8.11 (d, J = 8 Hz, 1H), 7.93 (s, 1H), 7.90-7.89 (d, J = 4 Hz, 1H), 7.82-7.81 (d, J = 4 Hz, 1H), 6.96-6.94 (t, J = 8 Hz, 1H), 6.23-6.09 (m, 1H), 5.88 (s, 1H), 5.08 (s, 1H), 4.83-4.67 (m, 1H), 2.93 (s, 3H), 2.87-2.86 (m, 1H), 2.76 (m, 2H), 2.70-2.61 (m, 2H), 2.40-2.34 (m, 2H), 1.95 (bs, 2H), 1.73-1.72 (m, 2H), 1.16-1.06 (m, 1H), 0.66-0.59 (m, 1H) |
| I-235 | 3-amino-5-methyl-1-(1-methyl-1H-pyrazol-4-yl)pyridin-2(1H)-one structure | MS (ES): m/z 452.51 [M + H]⁺, LCMS purity: 99.51%, HPLC purity: 99.68%, CHIRAL HPLC purity: 100%, ¹H NMR (DMSO-d₆, 400 MHZ): 8.91 (s, 1H), 8.31 (s, 1H), 8.24 (s, 1H), 8.08-8.07 (d, J = 4 Hz, 1H), 7.96-7.94 (d, J = 8 Hz, 1H), 7.91 (s, 1H), 7.86-7.85 (d, J = 4 Hz, 1H), 7.37 (s, 1H), 6.23 (s, 1H), 4.93-4.76 (m, 1H), 3.90 (s, 3H), 2.91-2.90 (d, J = 4 Hz, 3H), 2.87-2.85 (m, 1H), 2.17 (s, 3H), 1.22-1.16 (m, 1H), 0.94-0.85 (m, 1H) |
| I-236 | 3-(6-aminopyridin-2-yl)oxazolidin-2-one structure | MS (ES): m/z 427.51 [M + H]⁺, LCMS purity: 99.26%, HPLC purity: 98.99%, CHIRAL HPLC purity: 100%, ¹H NMR (DMSO-d₆, 400 MHZ): 9.90 (s, 1H), 8.26 (s, 1H), 8.11 (s, 1H), 8.00-7.99 (d, J = 4 Hz, 1H), 7.79-7.77 (t, J = 8 Hz, 1H), 7.69-7.67 (d, J = 8 Hz, 1H), 7.34-7.32 (d, J = 8 Hz, 1H), 6.59 (s, 1H), 4.93-4.76 (m, 1H), 4.50-4.48 (t, J = 8 Hz, 2H), 4.29-4.27 (t, J = 8 Hz, 2H), 2.96 (s, 4H), 1.24-1.20 (m, 1H), 1.04-0.98 (m, 1H) |
| I-239 | 2-((4-hydroxycyclohexyl)oxy)pyridin-3-amine structure | MS (ES): m/z 456.27 [M + H]⁺, LCMS purity: 97.02%, HPLC purity: 95.00%, CHIRAL HPLC purity: 99.36%, ¹H NMR (DMSO-d₆, 400 MHZ): 8.62 (s, 1H), 8.18 (s, 1H), 8.16-8.14 (d, J = 8 Hz, 1H), 7.93-7.92 (d, J = 4 Hz, 1H), 7.88-7.87 (d, J = 4 Hz, 1H), 7.82-7.81 (d, J = 4 Hz, 1H), 6.94-6.91 (m, 1H), 5.90 (s, 1H), 5.05-5.00 (m, 1H), 4.85-4.68 (m, 1H), 4.60-4.59 (d, J = 4 Hz, 1H), 3.49-3.46 (m, 1H), 2.93-2.92 (d, J = 4 Hz, 3H), 2.88-2.85 (m, 1H), 2.03-1.99 (m, 2H), 1.86-1.83 (m, 2H), 1.52-1.46 (m, 2H), 1.34-1.26 (m, 2H), 1.19-1.08 (m, 1H), 0.72-0.68 (m, 1H) |
| I-243 | 3-amino-1-(thiazol-2-yl)pyridin-2(1H)-one structure | MS (ES): m/z 441.17 [M + H]⁺, LCMS purity: 99.53%, HPLC purity: 98.41%, ¹H NMR (DMSO-d₆, 400 MHZ): 9.30 (s, 1H), 8.51-8.49 (d, J = 8 Hz, 1H), 8.31-8.29 (d, J = 8 Hz, 1H), 8.27 (s, 1H), 8.02 (s, 1H), 7.85-7.84 (d, J = 4 Hz, 1H), 7.80-7.79 (d, J = 4 Hz, 1H), 7.73-7.72 (d, J = 4 Hz, 1H), 6.63-6.61 (d, J = 8 Hz, 1H), 6.32 (s, 1H), 4.99-4.88 (m, 1H), 3.01 (bs 1H), 2.92 (s, 3H), 1.27-1.21 (m, 1H), 0.97-0.78 (m, 1H). |

TABLE 62-continued

| Compound | Intermediate | Characterization Data |
|---|---|---|
| I-244 | (structure: 6-amino-pyridin-2-yl pyrrolidin-2-one) | MS (ES): m/z 425.29 [M + H]⁺, LCMS purity: 98.98%, HPLC purity: 99.47%, ¹H NMR (DMSO-d₆, 400 MHZ): 9.91 (s, 1H), 8.27 (s, 1H), 8.15 (s, 1H), 8.03 (s, 1H), 7.91-7.89 (d, J = 8 Hz, 1H), 7.76-7.74 (t, J = 8 Hz, 1H), 7.28-7.26 (d, J = 8 Hz, 1H), 6.67 (s, 1H), 4.91-4.75 (m, 1H), 4.12-4.11 (t, J = 4 Hz, 2H), 2.97-2.96 (d, J = 4 Hz, 3H), 2.93-2.89 (m, 1H), 2.61-2.59 (t, J = 8 Hz, 2H), 2.08-2.07 (t, J = 4 Hz, 2H), 1.26-1.17 (m, 1H), 0.99-0.85 (m, 1H) |
| I-249 | (structure: trans-methoxycyclohexyloxy-aminopyridine) | MS (ES): m/z 470.46 [M + H]⁺, LCMS purity: 97.93%, HPLC purity: 97.67%, CHIRAL HPLC purity: 97.67%, ¹H NMR (DMSO-d₆, 400 MHZ): 8.64 (s, 1H), 8.18 (s, 1H), 8.15-8.13 (d, J = 8 Hz, 1H), 7.92-7.91 (d, J = 4 Hz, 1H), 7.89-7.88 (d, J = 4 Hz, 1H), 7.82-7.81 (d, J = 4 Hz, 1H), 6.95-6.92 (m, 1H), 5.89 (s, 1H), 5.09-5.07 (t, J = 4 Hz, 1H), 4.84-4.67 (m, 1H), 3.29 (s, 3H), 3.23-3.20 (m, 1H), 2.93-2.92 (d, J = 4 Hz, 3H), 2.89-2.85 (m, 1H), 1.99-1.97 (m, 4H), 1.54-1.51 (m, 2H), 1.34-1.28 (m, 2H), 1.17-1.67 (m, 1H), 0.69-0.68 (m, 1H) |
| I-250 | (structure: methylpyrazolyl-aminopyridinone) | MS (ES): m/z 452.17 [M + H]⁺, LCMS purity: 100%, HPLC purity: 99.86%, CHIRAL HPLC purity: 100%, ¹H NMR (DMSO-d₆, 400 MHZ): 8.94 (s, 1H), 8.25 (s, 1H), 8.11-8.10 (d, J = 4 Hz, 1H), 7.97 (bs, 1H), 7.88-7.87 (d, J = 4 Hz, 1H), 7.838-7.833 (d, J = 2 Hz, 1H), 7.49 (s, 1H), 6.76-6.75 (d, J = 4 Hz, 1H), 6.24 (s, 1H), 4.95-4.75 (m, 1H), 3.90 (s, 3H), 2.91 (s, 3H), 2.88-2.87 (m, 1H), 2.18 (s, 3H), 1.25-1.15 (m, 1H), 0.95-0.87 (m, 1H) |
| I-259 | (structure: 5-methyl-3-amino-2-(OCD₃)pyridine) | MS (ES): m/z 389.45 [M + H]⁺, LCMS purity: 98.93%, HPLC purity: 97.80%, ¹H NMR (DMSO-d₆, 400 MHZ): 8.84 (s, 1H), 8.18 (s, 1H), 8.01 (s, 1H), 7.92-7.91 (d, J = 4 Hz, 1H), 7.88-7.87 (d, J = 4 Hz, 1H), 7.74 (s, 1H), 5.86 (s, 1H), 4.82-4.65 (m, 1H), 2.91-2.90 (d, J = 4 Hz, 3H), 2.84-2.81 (m, 1H), 2.27 (s, 3H), 1.15-1.06 (m, 1H), 0.64-0.58 (m, 1H). |
| I-262 | (structure: 5-methylthiazol-2-yl aminopyridinone) | MS (ES): m/z 455.4 [M + H]⁺, LCMS purity: 100%, HPLC purity: 98.42%, ¹H NMR (DMSO-d₆, 400 MHZ): 9.26 (s, 1H), 8.43-8.41 (d, J = 8 Hz, 1H), 8.29 (s, 1H), 8.27 (s, 1H), 8.02-8.01 (d, J = 4 Hz, 1H), 7.80-7.78 (d, J = 8 Hz, 1H), 7.53 (s, 1H), 6.60-6.58 (t, J = 8 Hz, 1H), 6.31 (s, 1H), 4.99-4.82 (m, 1H), 3.00 (s, 1H), 2.93-2.91 (d, J = 8 Hz, 3H), 2.48 (s, 3H), 1.26-1.21 (m, 1H), 0.92-0.86 (m, 1H). |
| I-265 | (structure: 5-methoxypyridin-2-yl aminopyridinone) | MS (ES): m/z 465.46 [M + H]⁺, LCMS purity: 99.46%, HPLC purity: 97.69%, CHIRAL HPLC: 97.69%, ¹H NMR (DMSO-d₆, 400 MHZ): 8.97 (s, 1H), 8.32-8.32 (d, J = 2.8 Hz, 1H), 8.26-8.23 (m, J = 3.6 Hz, 2H), 7.96-7.95 (d, J = 4.4 Hz, 1H), 7.85-7.83 (d, J = 4.4 Hz, 1H), 7.77-7.75 (d, J = 8.8 Hz, 1H), 7.66-7.63 (m, 1H), 7.51-7.49 (d, J = 7.2 Hz, 1H), 6.40-6.36 (t, J = 7.2 Hz, 1H), 6.26 (s, 1H), 4.99-4.83 (m, 1H), 3.98 (m, 3H), 2.92-2.91 (d, J = 4.8 Hz, 3H), 1.28-1.22 (m, 2H), 0.93-0.81 (m, 1H). |
| I-268 | (structure: 2-methoxyethyl aminopyridinone) | MS (ES): m/z 416.43 [M + H]⁺, LCMS purity: 100%, HPLC purity: 98.86%, CHIRAL HPLC: 100%, ¹H NMR (DMSO-d₆, 400 MHZ): 8.87 (s, 1H), 8.23 (s, 1H), 8.14-8.12 (d, J = 7.2 Hz, 1H), 7.92-7.91 (d, J = 4 Hz, 1H), 7.81-7.80 (d, J = 4.4 Hz, 1H), 7.32-7.30 (d, J = 6.8 Hz, 1H), 6.24-6.21 (t, J = 7.2 Hz, 2H), |

TABLE 62-continued

| Compound | Intermediate | Characterization Data |
|---|---|---|
| | | 4.98-4.78 (m, 1H), 4.18-4.16 (t, 2H), 3.65-3.63 (t, 2H), 3.25 (s, 3H), 2.99-2.98 (m, 1H), 2.90-2.89 (d, J = 3.6 Hz, 3H), 1.33-1.18 (m, 2H). |
| I-275 | 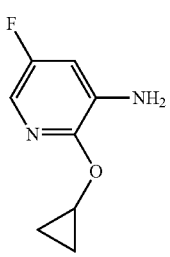 | [0001] MS (ES): m/z 416.17 [M + H]+, LCMS purity: 97.89%, HPLC purity: 98.01%, CHIRAL HPLC purity: 96.18%, $^1$H NMR (CDCL$_3$-d$_6$, 400 MHZ): 8.43 (s, 1H), 8.39-8.37 (d, J = 8 Hz, 1H), 7.88 (s, 1H), 7.78-7.77 (d, J = 4 Hz, 1H), 6.98 (s, 1H), 6.34-6.33 (d, J = 4 Hz, 1H), 5.42 (s, 1H), 4.88-4.71 (m, 1H), 4.38-4.37 (d, J = 4 Hz, 1H), 3.15-3.13 (d, J = 8 Hz, 3H), 3.11-3.09 (m, 1H), 1.32-1.22 (m, 1H), 1.15-1.09 (m, 1H), 0.93-0.87 (m, 4H). |
| I-279 | 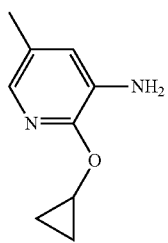 | MS (ES): m/z 412.22 [M + H]+, LCMS purity: 98.95%, HPLC purity: 96.96%, Chiral HPLC purity: 99.16%, $^1$H NMR (DMSO-d$_6$, 400 MHZ): 8.65 (s, 1H), 8.19 (s, 1H), 8.01 (s, 1H), 7.93-7.92 (d, J = 4 Hz, 1H), 7.87-7.86 (d, J = 4 Hz, 1H), 7.76 (s, 1H), 5.82 (s, 1H), 4.84-4.64 (m, 1H), 4.30-4.27 (m, 1H), 2.92-2.90 (d, J = 8 Hz, 3H), 2.84-2.80 (m, 1H), 2.27 (s, 3H), 1.15-1.06 (m, 1H), 0.78-0.71 (m, 4H), 0.66-0.64 (m, 1H). |
| I-280 | 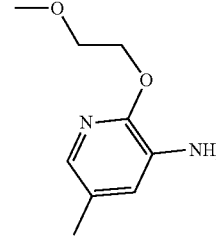 | MS (ES): m/z 430.22 [M + H]+, LCMS purity: 100%, HPLC purity: 99.01%, CHIRAL HPLC purity: 96.99%, $^1$H NMR (DMSO-d$_6$, 400 MHZ): 8.74 (s, 1H), 8.17 (s, 1H), 7.97 (s, 1H), 7.91-7.90 (d, J = 4 Hz, 1H), 7.88-7.87 (d, J = 4 Hz, 1H), 7.72 (s, 1H), 5.84 (s, 1H), 4.80-4.63 (m, 1H), 4.43-4.42 (d, J = 4 Hz, 2H), 3.67-3.66 (t, J = 4 Hz, 2H), 3.23 (s, 3H), 2.92-2.90 (d, J = 8 Hz, 3H), 2.83-2.80 (m, 1H), 2.25 (s, 3H), 1.11-1.06 (m, 1H), 0.60-0.54 (m, 1H). |
| I-285 | 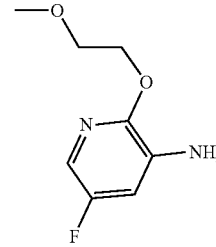 | MS (ES): m/z 434.17 [M + H]+, LCMS purity: 98.96%, HPLC purity: 98.74%, CHIRAL HPLC purity: 99.35%, $^1$H NMR (DMSO-d$_6$, 400 MHZ): 8.91 (s, 1H), 8.30-8.28 (d, J = 8 Hz, 1H), 8.24 (s, 1H), 8.03-8.02 (d, J = 4 Hz, 1H), 7.818-7.811 (d, J = 2.8 Hz, 1H), 7.79-7.78 (d, J = 4 Hz, 1H), 6.06 (s, 1H), 4.83-4.65 (m, 1H), 4.50-4.49 (t, J = 4 Hz, 2H), 3.73-3.72 (t, J = 4 Hz, 2H), 3.28 (s, 3H), 2.94-2.92 (d, J = 8 Hz, 4H), 1.17-1.07 (m, 1H), 0.81-0.74 (m, 1H) |
| I-289 | 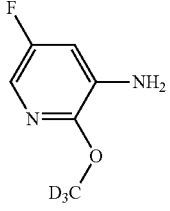 | MS (ES): m/z 393.17 [M + H]+, LCMS purity: 98.97%, HPLC purity: 99.12%, CHIRAL HPLC purity: 100%, $^1$H NMR (DMSO-d$_6$, 400 MHZ): 9.05 (s, 1H), 8.19 (s, 1H), 8.32-8.30 (d, J = 8 Hz, 1H), 8.25 (s, 1H), 8.04-8.03 (d, J = 4 Hz, 1H), 7.83-7.82 (d, J = 4 Hz, 1H), 7.79-7.78 (d, J = 4 Hz, 1H), 6.07 (s, 1H), 4.85-4.69 (m, 1H), 2.93-2.91 (d, J = 8 Hz, 4H), 1.18-1.09 (m, 1H), 0.83-0.77 (m, 1H). |
| I-292 | 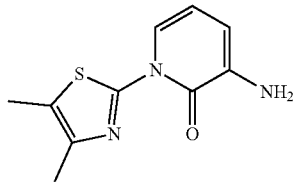 | MS (ES): m/z 469.46 [M + H]+, LCMS purity: 98.68%, HPLC purity: 99.35%, CHIRAL HPLC purity: 97.17%, $^1$H NMR (DMSO-d$_6$, 400 MHZ): 9.24 (s, 1H), 8.40-8.39 (d, J = 4 Hz, 1H), 8.27 (s, 1H), 8.25 (s, 1H), 8.01-8.00 (d, J = 4 Hz, 1H), 7.79-7.78 (d, J = 4 Hz, 1H), 6.58-6.57 (t, J = 4 Hz, 1H), 6.30 (s, 1H), 4.99-4.82 (m, 1H), 3.00 (m, 1H), 2.92-2.91 (d, J = 4 Hz, 3H), 2.37 (s, 3H), 2.32 (s, 3H), 1.26-1.21 (m, 1H), 0.92-0.86 (m, 1H). |

TABLE 62-continued

| Compound | Intermediate | Characterization Data |
|---|---|---|
| I-296 | | MS (ES): m/z 438.22 [M + H]+, LCMS purity: 100%, HPLC purity: 99.70%, CHIRAL HPLC purity: 100%, 1H NMR (DMSO-d6, 400 MHZ): 8.98 (s, 1H), 8.30 (s, 1H), 8.25 (s, 1H), 8.18-8.17 (d, J = 4 Hz, 1H), 7.96-7.95 (d, J = 4 Hz, 1H), 7.89 (s, 1H), 7.82-7.81 (d, J = 4 Hz, 1H), 7.53-7.51 (d, J = 8 Hz, 1H), 6.36-6.35 (t, J = 4 Hz, 1H), 6.26 (s, 1H), 4.99-4.80 (m, 1H), 3.91 (s, 3H), 3.01-2.98 (m, 1H), 2.91-2.90 (d, J = 4 Hz, 3H), 1.28-1.19 (m, 1H), 0.94-0.86 (m, 1H). |
| I-300 | | MS (ES): m/z 406.40 [M + H]+, LCMS purity: 99.74%, HPLC purity: 99.40%, CHIRAL HPLC purity: 100%, 1H NMR (DMSO-d6, 400 MHZ): 8.81 (s, 1H), 8.49-8.48 (d, J = 4 Hz, 1H), 8.16 (s, 1H), 8.13 (s, 1H), 7.98-7.97 (d, J = 4 Hz, 1H), 7.68-7.67 (d, J = 4 Hz, 1H), 7.60-7.57 (m, 1H), 5.88 (s, 1H), 4.75-4.57 (m, 1H), 2.94-2.93 (d, J = 4 Hz, 3H), 2.78 (m, 1H), 2.07-1.98 (m, 3H), 1.03-1.01 (m, 1H), 0.42-0.35 (m, 1H) |
| I-302 | | MS (ES): m/z 449.46 [M + H]+, LCMS purity: 99.13%, HPLC purity: 98.93%, CHIRAL HPLC: 99.49% 1H NMR (DMSO-d6, 400 MHZ): 8.96 (s, 1H), 8.53-8.52 (d, J = 4.4 Hz, 2H), 8.25 (s, 2H), 7.96 (s, 1H), 7.83 (s, 2H), 7.39-7.38 (d, J = 6.4 Hz, 1H), 6.37 (s, 1H), 6.25 (s, 1H), 4.99-4.82 (m, 1H), 3.00 (s, 1H), 2.90 (s, 3H), 2.40 (s, 3H), 1.24 (m, 2H). |
| I-304 | | MS (ES): m/z 525.60 [M + H]+, LCMS purity: 100%, HPLC purity: 100%, 1H NMR (DMSO-d6, 400 MHZ): 8.85 (s, 1H), 8.23 (s, 1H), 8.13-8.11 (d, J = 7.2 Hz, 1H), 7.92-7.91 (m, 1H), 7.81-7.80 (d, J = 4.4 Hz, 1H), 7.29-7.28 (d, J = 6.4 Hz, 1H), 6.34-6.31 (t, J = 7.2 Hz, 1H), 6.23 (s, 1H), 4.89-4.79 (m, 2H), 4.04-4.02 (m, 1H), 3.66 (s, 4H), 2.91-2.90 (d, J = 4.4 Hz, 4H), 2.34 (s, 4H), 2.15-2.09 (m, 3H), 1.99 (s, 1H), 1.93-1.90 (d, J = 11.6 Hz, 2H), 1.52 (s, 4H). |
| I-305 | | MS (ES): m/z 440.46 [M + H]+, LCMS purity: 97.21%, HPLC purity: 96.97%, Chiral HPLC purity: 98.97%, 1H NMR (DMSO-d6, 400 MHZ): 8.84 (s, 1H), 8.11-8.10 (d, J = 4 Hz, 1H), 7.93-7.92 (d, J = 4 Hz, 1H), 7.81-7.79 (d, J = 8 Hz, 1H), 7.43-7.41 (d, J = 8 Hz, 1H), 6.29-6.27 (t, J = 8 Hz, 1H), 6.22 (s, 1H), 4.97-4.76 (m, 2H), 3.00-2.96 (m, 1H), 2.91-2.90 (d, J = 4 Hz, 3H), 1.87-1.77 (m, 4H), 1.71-1.63 (m, 3H), 1.48-1.38 (m, 2H), 1.27-1.18 (m, 2H), 0.89-0.83 (m, 1H). |
| I-307 | | MS (ES): m/z 400.43 [M + H]+, LCMS purity: 99.54%, HPLC purity: 98.45%, CHIRAL HPLC: 100% 1H NMR (DMSO-d6, 400 MHZ): 9.79 (s, 1H), 8.37-8.35 (d, J = 7.6 Hz, 1H), 8.25-8.24 (d, J = 3.6 Hz, 2H), 8.033 (s, 1H), 7.83 (s, 1H), 7.34 (s, 1H), 5.66 (s, 1H), 4.88-4.72 (m, 1H), 2.96-2.95 (d, J = 4.4 Hz, 3H), 2.89 (s, 1H), 1.59 (s, 6H), 1.19-1.10 (m, 2H), 0.74-0.69 (m, 1H). |
| I-308 | | MS (ES): m/z 547.58 [M + H]+, LCMS purity: 98.97%, HPLC purity: 97.35%, CHIRAL HPLC purity: 100%, 1H NMR (DMSO-d6, 400 MHZ): 8.94 (s, 1H), 8.26-8.23 (m, 2H), 7.96 (m, 1H), 7.84 (m, 1H), 7.42 (s, 3H), 7.33-7.31 (d, J = 8 Hz, 1H), 6.35 (m, 1H), 6.26 (s, 1H), 5.00-4.83 (m, 1H), 4.15-4.13 (d, J = 8 Hz, 1H), 3.63 (m, 3H), 3.51 (s, 1H), 3.18-3.17 (d, J = 4 Hz, 3H), 3.01 (bs, 2H), 2.90 (m, 3H), 1.24 (bs, 4H), 0.94-0.86 (m, 2H). |

TABLE 62-continued

| Compound | Intermediate | Characterization Data |
|---|---|---|
| I-309 | | MS (ES): m/z 472.88 [M + H]+, LCMS purity: 100%, HPLC purity: 99.72%, 1H NMR (DMSO-d6, 400 MHZ): 9.17(s, 1H), 8.29 (s, 2H), 8.05-8.04 (d, J = 4.4 Hz, 1H), 7.85-7.78 (m, 3H), 6.77 (s, 1H), 6.33 (s, 1H), 4.92-4.76 (m, 1H), 3.91 (s, 3H), 2.92-2.88 (m, 4H), 1.23-1.17 (m, 1H), 1.02-0.96 (m, 1H). |
| I-312 | | MS (ES): m/z 471.88 [M + H]+, LCMS purity: 100%, HPLC purity: 99.70%, 1H NMR (DMSO-d6, 400 MHZ): 9.15 (s, 1H), 8.35 (s, 1H), 8.29 (s, 2H), 8.06-8.05 (d, J = 4.8 Hz, 1H), 7.96 (s, 1H), 7.80-7.79 (d, J = 3.2 Hz, 2H), 6.34 (s, 1H), 4.92-4.92 (m, 1H), 3.36 (s, 3H), 2.91 (s, 3H), 2.87 (s, 1H), 1.25-1.19 (m, 1H), 1.17-0.96 (bs, 1H). |
| I-315 | | MS (ES): m/z 486.26 [M + H]+, LCMS purity: 98.66%, HPLC purity: 98.40%, 1H NMR (DMSO-d6, 400 MHZ): 9.14(s, 1H), 8.28-8.27 (d, J = 3.6 Hz, 2H), 8.05-8.04 (d, J = 4.8 Hz, 1H), 7.79-7.78 (d, J = 2.8 Hz, 1H), 7.75-7.74 (d, J = 2.4 Hz, 1H), 6.59 (s, 1H), 6.33 (s, 1H), 4.90-4.75 (m, 1H), 3.77 (s, 3H), 2.91-2.87 (m, 4H), 2.32 (s, 3H), 1.22-1.14 (m, 1H), 1.01-0.95 (m, 1H) |
| I-317 | | MS (ES): m/z 484.3 [M + H]+, LCMS purity: 100%, HPLC purity: 97.84%, CHIRAL HPLC: 100% 1H NMR (DMSO-d6, 400 MHZ): 9.23 (s, 1H), 8.90-8.92 (d, J = 5.6 Hz, 1H), 8.35-8.34 (d, J = 2.4 Hz, 2H), 8.08 (s, 1H), 7.98-7.96 (d, J = 5.6 Hz, 2H), 7.81-7.80 (d, J = 3.2 Hz, 1H), 6.35 (s, 1H), 4.93-4.74 (m, 1H), 2.92 (s, 4H), 2.73 (s, 3H), 1.25-1.15 (m, 1H), 1.04-0.98 (m, 1H). |
| I-319 | | MS (ES): m/z 541.48 [M + H]+, LCMS purity: 100%, HPLC purity: 100%, CHIRAL HPLC purity: 100%, 1H NMR (DMSO-d6, 400 MHZ): 9.22 (s, 2H), 8.92 (s, 1H), 8.38 (s, 1H), 8.29 (s, 1H), 8.06 (bs, 1H), 7.81 (s, 2H), 6.35 (s, 1H), 4.92-4.75 (m, 1H), 3.08-3.04 (d, 6H), 2.91 (s, 4H), 1.22-1.15 (m, 1H), 1.02-0.96 (m, 1H). |
| I-323 | | MS (ES): m/z 489.93 [M + H]+, LCMS purity: 98.65%, HPLC purity: 97.42%, 1H NMR, CHIRAL HPLC: 100%, (CDCl3, 400 MHZ): 8.49 (s, 1H), 8.42 (s, 1H), 7.83 (s, 1H), 7.66 (s, 1H), 7.30 (s, 1H), 4.88-4.72 (m, 1H), 3.27(s, 3H), 2.90-2.85 (m, 1H), 2.65 (s, 3H), 1.39-1.29 (m, 2H), 1.21-1.15 (m, 1H). |

TABLE 62-continued

| Compound | Intermediate | Characterization Data |
|---|---|---|
| I-326 | (5-chloro-1-(1-cyclopropyl-5-methyl-1H-pyrazol-4-yl)pyridin-2(1H)-one with NH₂ substituent) | MS (ES): m/z 512.28 [M + H]⁺, LCMS purity: 99.19%, HPLC purity: 97.66%, CHIRAL HPLC purity: 100%, ¹H NMR (DMSO-d₆, 400 MHZ): 9.08 (s, 1H), 8.31-8.31 (d, J = 2 Hz, 1H), 8.29 (s, 1H), 8.05-8.04 (d, J = 4 Hz, 1H), 7.80-7.79 (d, J = 4 Hz, 1H), 7.57 (s, 1H), 7.49-7.48 (d, J = 4 Hz, 1H), 6.33 (s, 1H), 4.92-4.76 (m, 1H), 3.61-3.61 (m, 1H), 2.91-2.90 (d, J = 4 Hz, 3H), 2.88 (m, 1H), 2.25 (m, 3H), 1.24-1.18 (m, 2H), 1.09-0.97 (m, 4H). |
| I-330 | (1-(tetrahydro-2H-pyran-4-yl)-3-aminopyridin-2(1H)-one derivative) | MS (ES): m/z 442.16 [M + H]⁺, LCMS purity: 99.56%, HPLC purity: 97.37%, CHIRAL HPLC purity: 95.84%, ¹H NMR (DMSO-d₆, 400 MHZ): 8.86 (s, 1H), 8.23 (s, 1H), 8.13-8.12 (d, J = 4 Hz, 1H), 7.93-7.92 (d, J = 4 Hz, 1H), 7.80-7.79 (d, J = 4 Hz, 1H), 7.47-7.45 (d, J = 8 Hz, 1H), 6.30-6.029 (t, J = 4 Hz, 1H), 6.23 (s, 1H), 5.06-4.08 (m, 2H), 4.00-3.99 (d, J = 4 Hz, 2H), 3.54-3.51 (t, J = 12 Hz, 2H), 2.99 (m, 1H), 2.91-2.90 (d, J = 4 Hz, 3H), 2.06-1.99 (m, 2H), 1.76-1.73 (m, 2H), 1.28-1.20 (m, 1H), 0.90-0.83 (m, 1H). |
| I-332 | (5-chloro-1-(1-cyclopropyl-1H-pyrazol-3-yl)-3-aminopyridin-2(1H)-one derivative) | MS (ES): m/z 498.16 [M + H]⁺, LCMS purity: 99.39%, HPLC purity: 96.04%, ¹H NMR (DMSO-d₆, 400 MHZ): 9.18 (s, 1H), 8.28 (s, 2H), 8.05-8.04 (d, J = 4 Hz, 1H), 7.95-7.95 (d, J = 2 Hz, 1H), 7.79 (s, 2H), 6.76-6.76 (d, J = 2 Hz, 1H), 6.33 (s, 1H), 4.91-4.74 (m, 1H), 3.81-3.78 (m, 1H), 2.91-2.90 (d, J = 4 Hz, 3H), 2.87 (m, 1H), 1.23-1.17 (m, 1H), 1.14-1.11 (m, 2H), 1.01-0.95 (m, 3H). |
| I-334 | (5-chloro-1-(6-cyclopropylpyridazin-3-yl)-3-aminopyridin-2(1H)-one derivative) | MS (ES): m/z 510.16 [M + H]⁺, LCMS purity: 99.52%, HPLC purity: 100%, CHIRAL HPLC purity: 100%, ¹H NMR (DMSO-d₆, 400 MHZ): 9.17 (s, 1H), 8.385-8.380 (d, J = 2 Hz, 1H), 8.29 (s, 1H), 8.07-8.05 (d, J = 8 Hz, 1H), 8.02-8.00 (d, J = 8 Hz, 1H), 7.81-7.77 (m, 3H), 6.33 (s, 1H), 4.92-4.75 (m, 1H), 2.91-2.90 (d, J = 4 Hz, 3H), 2.88 (m, 1H), 2.41-2.34 (m, 1H), 1.25-1.13 (m, 5H), 1.0-0.96 (m, 1H). |
| I-335 | (1-(1-methyl-1H-pyrazol-5-yl)-3-aminopyridin-2(1H)-one derivative) | MS (ES): m/z 438.34 [M + H]⁺, LCMS purity: 100%, HPLC purity: 99.79%, CHIRAL HPLC purity: 100%, ¹H NMR (DMSO-d₆, 400 MHZ): 9.02 (s, 1H), 8.30-8.29 (d, J = 4 Hz, 1H), 8.27 (s, 1H), 8.00-7.99 (d, J = 4 Hz, 1H), 7.82-7.81 (d, J = 4 Hz, 1H), 7.55-7.55 (d, J = 2 Hz, 1H), 7.28-7.26 (d, J = 8 Hz, 1H), 6.49-6.49 (d, J = 2 Hz, 1H), 6.41-6.39 (t, J = 8 Hz, 1H), 6.28 (s, 1H), 5.01-4.81 (m, 1H), 3.64 (s, 3H), 3.03-2.99 (m, 1H), 2.91-2.90 (d, J = 4 Hz, 3H), 1.30-1.20 (m, 1H), 0.97-0.86 (m, 1H). |
| I-341 | (1-(1,3-dimethyl-1H-pyrazol-5-yl)-3-aminopyridin-2(1H)-one derivative) | MS (ES): m/z 452.36 [M + H]⁺, LCMS purity: 99.42%, HPLC purity: 100%, CHIRAL HPLC purity: 100%, ¹H NMR (DMSO-d₆, 400 MHZ): 9.01 (s, 1H), 8.29 (s, 1H), 8.27 (s, 1H), 7.99 (s, 1H), 7.81-7.80 (d, J = 4.4 Hz, 1H), 6.39-6.35 (t, J = 7.2 Hz, 1H), 6.28-6.26 (d, J = 7.6 Hz, 1H), 4.99-4.83 (m, 1H), 3.54 (s, 3H), 3.00-2.98 (m, 1H), 2.90 (s, 3H), 2.21 (s, 3H), 1.26-1.18 (m, 2H), 0.90-0.86 (m, 2H). |

TABLE 62-continued

| Compound | Intermediate | Characterization Data |
|---|---|---|
| I-344 | | MS (ES): m/z 470.52 [M + H]+, LCMS purity: 100%, HPLC purity: 97.44%, CHIRAL HPLC: 98.56%, $^1$H NMR (DMSO-$d_6$, 400 MHZ): 8.84 (s, 1H), 8.23 (s, 1H), 8.12-8.10 (d, J = 7.2 Hz, 1H), 7.93-7.92 (d, J = 4.8 Hz, 1H), 7.80-7.79 (d, J = 4.4 Hz, 1H), 7.41-7.39 (d, J = 6 Hz, 1H), 6.29-6.22 (m, 2H), 5.06 (s, 1H), 3.27 (s, 3H), 3.00-2.96 (m, 1H), 2.91-2.90 (d, J = 4.8 Hz, 3H), 2.16-2.09 (m, 2H), 1.80-1.70 (m, 3H), 1.34-1.23 (m, 3H), 1.83 (m, 3H), 0.89-0.81 (m, 1H) |
| I-349 | | MS(ES): m/z 455.2 [M + H]+, LCMS purity: 100%, HPLC purity: 99.68%, chiral HPLC: 96.85%, $^1$H NMR (DMSO-$d_6$, 400 MHZ): 8.85 (s, 1H), 8.23 (s, 1H), 8.13-8.11 (d, J = 7.2 Hz, 1H), 7.93-7.91 (d, J = 4.8 Hz, 1H), 7.80-7.79 (d, J = 4.4 Hz, 1H), 7.43-7.42 (d, J = 6.8 Hz, 1H), 6.29-6.22 (m, 1H), 4.79-4.72 (m, 2H), 2.98-2.97 (m, 2H), 2.91-2.90 (m, 4H), 2.22 (s, 3H), 2.09-2.03 (m, 2H), 1.97-1.89 (m, 2H), 1.75-1.73 (m, 2H), 1.25-1.20 (m, 1H), 0.89-0.83 (m, 1H). |
| I-357 | | MS (ES): m/z 470.4 [M + H]+, LCMS purity: 99.51%, HPLC purity: 99.33%, $^1$H NMR (DMSO-$d_6$, 400 MHZ): 8.85 (s, 1H), 8.12-8.11 (d, J = 6.8 Hz, 1H), 7.93 (s, 1H), 7.80 (s, 1H), 7.34-7.32 (d, J = 6.4 Hz, 1H), 6.29-6.22 (m, 2H), 4.96 (bs, 1H), 4.82 (bs, 2H), 2.99 (s, 1H), 2.91 (s, 3H), 2.06-2.03 (d, J = 12.4 Hz, 2H), 1.92-1.86 (m, 2H), 1.61-1.58 (d, J = 9.6 Hz, 4H), 1.23 (bs, 4H), 0.90-0.841 (m, 1H). |
| I-360 | | MS (ES): m/z 484.57 [M + H]+, LCMS purity: 100%, HPLC purity: 99.03%, Chiral HPLC purity: 99.01%, $^1$H NMR (DMSO-$d_6$, 400 MHZ): 8.86 (s, 1H), 8.24 (s, 1H), 8.13-8.11(d, J = 7.2 Hz, 1H), 7.94-7.93 (d, J = 1.6 Hz, 1H), 7.81-7.80 (d, J = 4.4 Hz, 1H), 7.34-7.33 (d, J = 4 Hz, 1H), 6.31-6.27 (t, J = 7.2 Hz, 1H), 6.24 (s, 1H), 4.81-4.79 (m, 1H), 3.15 (s, 3H), 2.99 (s, 1H), 2.92-2.91 (d, J = 4.4 Hz, 3H), 1.94-1.82 (m, 4H), 1.59-1.47 (m, 4H), 1.33-1.24 (m, 1H), 1.22 (s, 3H), 0.90-0.84 (m, 2H). |
| I-362 | | MS (ES): m/z 484.31 [M + H]+, LCMS purity: 95.90%, HPLC purity: 97.81%, Chiral HPLC purity: 97.27%, $^1$H NMR (DMSO-$d_6$, 400 MHZ): 8.86 (s, 1H), 8.24 (s, 1H), 8.13-8.11 (d, J = 6.8 Hz, 1H), 7.94-7.93 (d, J = 4.8 Hz, 1H), 7.82-7.80 (d, J = 4.4 Hz, 1H), 7.52-7.51 (d, J = 6.8 Hz, 1H), 6.29-6.23 (m, 2H), 4.97-4.96 (m, 1H), 4.81-4.72 (m, 1H), 3.16 (s, 3H), 3.00-2.98 (d, J = 7.2 Hz, 1H), 2.91-2.90 (d, J = 4.8 Hz, 3H), 1.93-1.74 (m, 6H), 1.60-1.57 (m, 2H), 1.30-1.10 (m, 4H), 0.92-0.83 (m, 1H) |
| I-365 | | MS (ES): m/z 456.32 [M + H]+, LCMS purity: 100%, HPLC purity: 98.38%, Chiral HPLC purity: 49.82% + 50.17%, $^1$H NMR (DMSO-$d_6$, 400 MHZ): 8.86 (s, 1H), 8.24 (s, 1H), 8.14-8.12 (d, J = 7.2 Hz, 1H), 7.94-7.92 (d, J = 4.8 Hz, 1H), 7.82-7.81 (d, J = 4.4 Hz, 1H), 7.28-7.27 (d, J = 6.8 Hz, 1H), 6.23-6.19 (t, J = 6.8 Hz, 2H), 5.77 (s, 1H), 4.97 (s, 1H), 4.80 (s, 1H), 4.14-4.11 (d, J = 13.2 Hz, 1H), 3.92-3.85 (m, 2H), 3.67-3.64 (d, J = 10 Hz, 1H), 3.35-3.26 (m, 1H), 2.98 (bs, 1H), 2.91-2.90 (d, J = 4.8 Hz, 2H), 1.80 (bs, 1H), 1.62-1.59 (d, J = 12.4 Hz, 1H), 1.46 (bs, 2H), 1.28-1.21 |(m, 2H), 0.90-0.84 (m, 1H) |

TABLE 62-continued

| Compound | Intermediate | Characterization Data |
|---|---|---|
| I-369 | | MS (ES): m/z 439.51 [M + H]⁺, LCMS purity: 100%, HPLC purity: 99.79%, Chiral HPLC purity: 100%, $^1$H NMR (DMSO-d$_6$, 400 MHZ): 9.03 (s, 1H), 8.26-8.23 (d, J = 9.6 Hz, 1H), 8.03-7.99 (t, J = 9.6 Hz, 2H), 7.79-7.78 (d, J = 4.4 Hz, 1H), 7.44-7.42 (d, J = 6.8 Hz, 1H), 6.40-6.36 (t, J = 7.2 Hz, 1H), 6.24 (s, 1H), 4.97 (s, 1H), 4.81 (bs, 1H), 2.99 (s, 1H), 2.91-2.90 (d, J = 4.4 Hz, 3H), 2.19 (s, 3H), 1.27-1.80 (m, 1H), 0.92 (bs, 1H). |
| I-370 | | MS (ES): m/z 470.52 [M + H]⁺, LCMS purity: 100%, HPLC purity: 99.01%, Chiral HPLC purity: 99.82%, $^1$H NMR (DMSO-d$_6$, 400 MHZ): 8.85 (s, 1H), 8.24 (s, 1H), 8.13-8.11 (d, J = 7.2 Hz, 1H), 7.94-7.93 (d, J = 4.8 Hz, 1H), 7.81-7.80 (d, J = 4.8 Hz, 1H), 7.39-7.38 (d, J = 6.4 Hz, 1H), 6.32-6.30 (t, J = 6.8 Hz, 1H), 6.23 (s, 1H), 4.97 (bs, 1H), 4.81-4.75 (m, 1H), 4.31 (s, 1H), 3.01-2.99 (bs, 1H), 2.91-2.90 (d, J = 4.4 Hz, 3H), 2.05-1.19 (m, 2H), 1.70-1.67 (d, J = 12.8 Hz, 2H), 1.56-1.50 (m, 4H), 1.28-1.17 (m, 4H), 0.86 (bs, 1H). |
| I-372 | | MS (ES): m/z 470.30 [M + H]⁺, LCMS purity: 100%, HPLC purity: 96.54%, Chiral HPLC purity: 100%, $^1$H NMR (DMSO-d$_6$, 400 MHZ): 8.86 (s, 1H), 8.24 (s, 1H), 8.12-8.11 (d, J = 4 Hz, 1H), 7.94-7.93 (d, J = 4 Hz, 1H), 7.81-7.80 (d, J = 4 Hz, 1H), 7.50-7.48 (d, J = 8 Hz, 1H), 6.28-6.23 (m, 2H), 4.81-4.73 (m, 2H), 4.48 (s, 1H), 2.98 (s, 1H), 2.91-2.90 (d, J = 4 Hz, 3H), 1.89-1.80 (m, 2H), 1.61-1.56 (m, 6H), 1.27 (s, 3H), 0.90-0.84 (m, 2H). |
| I-379 | | MS (ES): m/z 456.43 [M + H]⁺, LCMS purity: 99.14%, HPLC purity: 98.47%, $^1$H NMR (DMSO-d$_6$, 400 MHZ): 9.22 (s, 1H), 8.32-8.29 (m, 2H), 8.06-8.05 (d, J = 4.8 Hz, 1H), 7.85-7.84 (d, J = 2.0 Hz, 1H), 7.77-7.74 (m, 2H), 6.82-6.81 (d, J = 2.4 Hz, 1H), 6.37 (s, 1H), 4.90-4.73 (m, 1H), 3.90 (s, 3H), 2.98-2.94 (m, 1H), 2.92-2.91 (d, J = 4.8 Hz, 3H), 1.23-1.15 (m, 1H), 1.00-0.93 (m, 1H). |
| I-383 | | MS (ES): m/z 411.37 [M + H]⁺, LCMS purity: 98.70%, HPLC purity: 95.76%, $^1$H NMR (DMSO-d$_6$, 400 MHZ): 8.19 (s, 1H), 8.08 (s, 1H), 7.96 (s, 1H), 7.45-7.41 (t, J = 8 Hz, 1H), 7.09 (s, 1H), 6.57 (s, 1H), 6.05-6.03 (d, J = 8 Hz 1H), 3.54-3.43 (m, 4H), 3.16 (s, 3H) 2.83-2.82 (d, J = 3.6 Hz, 1H), 1.95 (s, 4H), 0.77-0.76 (d, J = 5.6 Hz, 2H), 0.58 (bs, 2H) |
| I-385 | | MS (ES): m/z 470.22 [M + H]⁺, LCMS purity: 97.14%, HPLC purity: 98.06%, $^1$H NMR (DMSO-d$_6$, 400 MHZ): 9.21 (s, , 1H), 8.32-8.31 (d, J = 3.2 Hz, 2H), 8.07-8.06 (d, J = 4.8 Hz, 1H), 7.76-7.73 (m, 2H), 6.64 (s, 1H), 6.37 (s, 1H), 5.77 (s, 1H), 4.90-4.74 (m, 1H), 3.78 (s, 3H), 2.92-2.91 (d, J = 4.8 Hz, 4H) 2.33 (s, 3H), 1.21-1.16 (m, 1H). |

TABLE 62-continued

| Compound | Intermediate | Characterization Data |
| --- | --- | --- |
| I-389 | | MS(ES): m/z 531.55 [M + H]⁺ LCMS purity: 98.45%, HPLC purity: 95.30%, Chiral HPLC purity: 98.47%, NMR (DMSO-d$_6$, 400 MHZ): 8.91 (s, 1H), 8.25-8.22 (m, 2H), 7.96-95 (d, J = 4.8 Hz, 1H), 7.83-7.82 (d, J = 4.4 Hz, 1H), 7.42-7.31 (m, 6H), 6.35-6.31 (t, J = 7.2 Hz, 1H), 6.25 (s, 1H), 3.82 (s, 1H), 3.10 (bs, 1H), 3.01 (bs, 1H), 2.91-2.89 (d, J = 4.8 Hz, 3H), 2.67 (s, 2H), 2.45-2.43 (d, J = 9.6 Hz, 4H), 1.90-1.75 (m, 2H), 1.47-1.22 (m, 2H), 0.87-0.84 (m, 2H). |
| I-405 | | MS (ES): m/z 452.61 [M + H]⁺, LCMS purity: 100%, HPLC purity: 99.72%, CHIRAL HPLC: 100% ¹H NMR (DMSO-d$_6$, 400 MHZ): 8.94 (s, 1H), 8.26-8.24 (d, J = 8 Hz, 2H), 7.96-7.82 (m, 1H), 7.63 (s, 1H), 7.24-7.22 (d, J = 6.8 Hz, 1H), 6.33-6.28 (m, 1H), 4.99 (s, 1H), 4.83 (s, 1H), 3.84(s, 3H), 2.91-2.90 (d, J = 4.8 Hz, 3H), 1.88 (s, 3H), 1.30-1.18 (m, 3H), 0.87 (bs, 1H) |
| I-407 | | MS (ES): m/z 522.62 [M + H]⁺. LCMS purity: 100%, HPLC purity: 99.28%, ¹H NMR (DMSO-d$_6$, 400 MHZ): 9.00 (s, 1H), 8.34 (s, 1H), 8.25(s, 1H), 8.18-8.16 (d, J = 8.0 Hz, 1H), 7.96-7.93 (m, 2H), 7.82-7.81 (d, J = 4.0 Hz, 1H), 7.55-7.53 (d, J = 8.0 Hz, 1H), 6.36-6.33 (t, 1H), 6.25 (s, 1H), 4.97-4.82 (d, J = 4.0 Hz, 1H), 4.0-4.06 (d, J = 8 Hz, 2H), 3.85-3.83 (d, J = 8.0 Hz, 2H), 3.29-3.23 (t, 2H), 2.99 (s, 1H), 2.91-2.90 (d, J = 4.0 Hz, 3H), 2.08 (bs, 1H), 1.45-1.42 (m, 2H), 1.30-1.21 (m, 3H), 0.92-0.85 (m, 1H) |
| I-416 | | MS (ES): m/z 470.31 [M + H]⁺, LCMS purity: 99.36%, HPLC purity: 98.80%, CHIRAL HPLC purity: 99.36%, ¹H NMR (DMSO-d$_6$, 400 MHZ): 8.83-8.82 (d, J = 4.8 Hz, 1H), 8.55 (s, 1H), 7.98-7.97 (d, = 4 Hz, 1H), 7.81-7.78 (t, J = 10 Hz, 1H), 7.65 (s, 2H), 7.44 (s, 1H), 6.97(s, 1H), 4.96-4.80 (m, 1H), 3.77(s, 3H), 3.04-3.03 (d, J = 4.8 Hz, 4H), 1.97 (s, 3H), 0.88 (s, 2H). |
| I-442 | | MS(ES): m/z 456.22 [M + H]⁺ LCMS purity: 100%, HPLC purity: 99.63%, Chiral HPLC purity: 50.15%, 49.85%, NMR (DMSO-d$_6$, 400 MHZ): 8.90 (s, 1H), 8.23 (s, 1H), 8.14-8.12 (d, J = 6.8 Hz, 1H), 7.93-7.92 (d, J = 4.8 Hz, 1H), 7.80-7.79 (d, J = 4.4 Hz, 1H), 7.40-7.38 (d, J = 6.4 Hz, 1H), 6.31-6.27 (d, J = 7.2 Hz, 1H), 6.24 (s, 1H), 5.01-4.97 (d, J = 6 Hz, 1H), 4.81 (s, 1H), 4.07-4.05 (d, J = 6 Hz, 1H), 3.18 (s, 3H), 2.99 (s, 1H), 2.90-2.89 (d, J = 9.2 Hz, 3H), 1.85-1.1.56 (m, 4H), 2.24-1.20 (m, 2H), 0.90-0.84 (m, 2H) |
| I-454 | | MS (ES): m/z 442.22 [M + H]⁺, LCMS purity: 96.94%, HPLC purity: 100%, CHIRAL HPLC: 100%, ¹H NMR (DMSO-d$_6$, 400 MHZ): 8.89 (s, 1H), 8.23 (s, 1H), 8.15-8.13 (d, J = 7.2 Hz, 1H), 7.94-7.92 (d, J = 4.8 Hz, 1H), 7.82-7.81 (d, J = 4.4 Hz, 1H), 7.30-7.28 (d, J = 6.8 Hz, 1H), 6.25-6.21 (m, 2H), 4.90-4.75 (m, 1H), 4.16-4.14 (t, J = 5.2 Hz, 2H), 3.75-3.73 (t, J = 4.8 Hz, 2H), 2.98-2.89 (m, 4H), 1.24-1.22 (m, 2H), 0.77 (bs, 1H), 0.39 (bs, 4H). |

| Compound | Intermediate | Characterization Data |
|---|---|---|
| I-474 | (tetrahydropyran-2-yl substituted 3-amino-pyridin-2(1H)-one structure) | MS (ES): m/z 442.34 [M + H]+, LCMS purity: 100%, HPLC purity: 99.62%, Chiral HPLC: 100%, $^1$H NMR (DMSO-$d_6$, 400 MHZ): 8.90 (s, 1H), 8.24 (s, 1H), 8.15-8.13 (d, J = 7.2 Hz, 1H), 7.95-7.93 (d, J = 4.8 Hz, 1H), 7.81-7.80 (d, J = 4.8 Hz, 1H), 7.51-7.48 (d, J = 6.4 Hz, 1H), 6.31-6.28 (t, J = 7.2 Hz, 1H), 6.25 (s, 1H), 4.99-4.79 (m, 2H), 3.85-3.83 (m, 2H), 3.60-3.54 (t, J = 10.0 Hz, 1H), 3.49-3.44 (m, 1H), 3.33-3.29 (t, J = 7.2 Hz, 1H), 3.00-2.97 (m, 1H), 2.91-2.90 (d, J = 4.8 Hz, 3H), 2.18-1.89 (m, 2H), 1.73-1.71 (m, 1H), 1.26-1.15 (m, 1H), 0.92-0.84 (m, 1H) |
| I-475 | (tetrahydropyran-2-yl enantiomer structure) | MS (ES): m/z 442.34 [M + H]+, LCMS purity: 99.68%, HPLC purity: 98.54%, Chiral HPLC: 100%, $^1$H NMR (DMSO-$d_6$, 400 MHZ): 8.90 (s, 1H), 8.24 (s, 1H), 8.15-8.13 (d, J = 7.2 Hz, 1H), 7.95-7.94 (d, J = 4.8 Hz, 1H), 7.81-7.80 (d, J = 4.8 Hz, 1H), 7.51-7.49 (d, J = 6.4 Hz, 1H), 6.31-6.27 (t, J = 7.2 Hz, 1H), 6.25 (s, 1H), 4.98-4.80 (m, 2H), 3.85-3.83 (m, 2H), 3.60-3.54 (t, J = 10.0 Hz, 1H), 3.49-3.44 (m, 1H), 3.33-3.29 (t, J = 7.2 Hz, 1H), 3.00-2.97 (m, 1H), 2.91-2.90 (d, J = 4.8 Hz, 3H), 2.18-1.89 (m, 2H), 1.73-1.71 (m, 1H), 1.28-1.21 (m, 1H), 0.92-0.82 (m, 1H). |
| I-505 | (1,4,5-trimethylpyrazol-3-yl substituted 3-amino-pyridin-2(1H)-one structure) | MS (ES): m/z 466.49 [M + H]+, LCMS purity: 100%, HPLC purity: 100%, Chiral HPLC: 99.54%, $^1$H NMR (DMSO-$d_6$, 400 MHZ): 8.93 (s, 1H), 8.26 (s, 2H), 7.96-7.83 (m, 2H), 7.20 (s, 1H), 6.29 (s, 2H), 4.99-4.83 (m, 1H), 3.76 (s, 3H), 3.01 (s, 1H), 2.91 (s, 3H), 2.25 (s, 3H), 1.81 (s, 3H), 1.25 (s, 1H), 0.94-0.88 (m, 1H) |
| I-506 | (1-methylpiperidin-3-yl substituted 3-amino-pyridin-2(1H)-one structure) | MS (ES): m/z 455.3 [M + H]+, LCMS purity: 99.25%, HPLC purity: 98.72%, CHIRAL HPLC purity: 50.07%, 48.97%, $^1$H NMR (DMSO-$d_6$, 400 MHZ): 8.88 (s, 1H), 8.24 (s, 1H), 8.14-8.12 (d, J = 6.8 Hz, 1H), 7.95-7.93 (d, J = 4.8 Hz, 1H), 7.81-7.80 (d, J = 4.4 Hz, 1H), 7.55-7.54 (d, J = 6.4 Hz, 1H), 6.29-6.26 (m, 1H), 4.96 (bs, 1H), 2.98 (bs, 1H), 2.91-2.90 (d, J = 4.8 Hz, 2H), 2.79 (bs, 1H), 2.68 (bs, 3H), 2.32 (s, 4H), 1.79-1.72 (m, 3H), 1.28-1.29 (m, 3H), 0.90-0.84 (m, 2H). |
| I-507 | (2-methoxycyclopentyl substituted 3-amino-pyridin-2(1H)-one structure) | MS(ES): m/z 456.5 [M + H]+, LCMS purity: 98.39%, HPLC purity: 98.44%, Chiral HPLC purity: 50.24%, 49.75%, NMR (DMSO-$d_6$, 400 MHZ): 8.86 (s, 1H), 8.23 (s, 1H), 8.15-8.13 (d, J = 7.2 Hz, 1H), 7.92-7.91 (d, J = 4.8 Hz, 1H), 7.82-7.81 (d, J = 4.4 Hz, 1H), 7.37-7.35 (d, J = 6.8 Hz, 1H), 6.25-6.22 (t, J = 7.2 Hz, 2H), 5.09-5.03 (m, 1H), 3.89 (s, 1H) 3.02 (s, 3H), 2.91-2.89 (d, J = 4.8 Hz, 3H), 3.00-2.91 (m, 1H), 1.96-1.82 (m, 3H), 1.65-1.63 (d, J = 8.8 Hz, 2H), 1.26-1.20 (m, 2H), 0.81-0.78 (m, 2H). |
| I-521 | (5-fluoro-1-(tetrahydropyran-3-yl)-3-amino-pyridin-2(1H)-one structure) | MS (ES): m/z 460.35[M + H]+, LCMS purity: 99.07%, HPLC purity: 98.51%, CHIRAL HPLC: 49.63%, 48.07%, $^1$H NMR (DMSO-$d_6$, 400 MHZ): 9.09 (s, 1H), 8.27 (s, 1H), 8.25-8.24 (d, J = 2.4 Hz, 1H), 8.03-8.01 (d, J = 4.8 Hz, 1H), 7.73-7.72 (d, J = 4 Hz, 1H), 7.66-7.64 (m, 1H), 6.35 (s, 1H), 4.88 (s, 1H), 4.72 (bs, 1H), 3.83-3.81 (m, 2H), 3.61-3.56 (t, J = 10 Hz, 1H), 3.47-3.43 (t, J = 8.4 Hz, 1H), 2.91-2.90 (d, J = 4.8 Hz, 3H), 2.11-2.05 (m, 1H), 1.95 (bs, |

TABLE 62-continued

| Compound | Intermediate | Characterization Data |
|---|---|---|
| | | 1H), 1.76-1.69 (m, 2H), 1.20-1.09 (m, 1H), 0.90-0.86 (m, 2H). |
| I-522 | *[structure: 6-aminopyridine with tetrahydropyran]* | MS(ES): m/z 426.47 [M + H]⁺ LCMS purity: 95.29%, HPLC purity: 98.80%, Chiral HPLC purity: 48.18%, 48.5%, NMR (DMSO-d$_6$, 400 MHZ): 9.88 (s, 1H), 8.25 (s, 1H), 8.09-8.08 (d, J = 4.8 Hz, 1H), 7.99-7.98 (d, J = 4 Hz, 1H), 7.69-7.65 (t, J = 7.6 Hz, 1H), 7.50-7.48 (d, J = 8 Hz, 1H), 6.96-6.94 (d, J = 7.6 Hz, 1H), 6.73 (s, 1H), 4.93-4.76 (m, 1H), 4.03-4.00 (d, J = 8.8 Hz, 1H), 3.91-3.89 (m, 1H), 3.56-3.50 (t, J = 10.8 Hz, 1H), 2.92-2.91 (d, J = 3.6 Hz, 3H), 2.89 (bs, 2H), 1.93-1.89 (m, 2H), 1.70-1.69 (m, 2H), 1.29-1.28 (m, 3H). |
| I-526 | *[structure: dimethylthiazoline-pyridinone-amine]* | MS (ES): m/z 471.46 [M + H]⁺, LCMS purity: 100%, HPLC purity: 100%, CHIRAL HPLC: 97.89%, ¹H NMR (DMSO-d$_6$, 400 MHZ): 8.30 (s, 1H), 8.20-8.18 (d, J = 3.6 Hz, 1H), 7.99-7.97(d, J = 4.8 Hz, 1H), 7.92-7.91 (d, J = 6.4 Hz, 1H), 7.76-7.75 (d, J = 4.4 Hz, 1H), 6.42-6.39 (t, J = 7.2 Hz, 1H), 6.26 (s, 1H), 4.96 (bs, 1H), 4.80-4.78 (m, 1H), 3.23 (s, 2H), 2.99-2.96 (m, 1H), 2.90-2.89 (d, J = 4.8 Hz, 3H), 1.37 (s, 6H), 1.26-1.17 (m, 2H). |
| I-532 | *[structure: dioxino-pyridine amine]* | MS (ES): m/z 399.39 [M + H]⁺, LCMS purity: 100%, HPLC purity: 100%, CHIRAL HPLC: 100%, ¹H NMR (DMSO-d$_6$, 400 MHZ): 9.80 (s, 1H), 8.21 (s, 1H), 7.97-7.91 (m, 2H), 7.38-7.24(m, 2H), 6.11 (s, 1H), 4.93-4.77 (m, 1H), 4.42 (s, 2H), 4.23 (s, 2H), 2.93-2.89 (d, J = 4.4 Hz, 3H), 1.24-1.17 (m, 1H), 0.94-0.87 (m, 1H). |
| I-553 | *[structure: pyrrolidinyl-7-azaindole]* | MS (ES): m/z 435.27 [M + H]⁺, LCMS purity: 100%, HPLC purity: 98.94%, CHIRAL HPLC: 99.14%, ¹H NMR (DMSO-d$_6$, 400 MHZ): 8.78-8.76 (d, J = 8 Hz, 1H), 8.47-8.46 (d, J = 4.8 Hz, 1H), 8.44-8.42(m, 2H), 7.89-7.88 (d, J = 4.8 Hz, 1H), 7.58 (s, 1H), 7.28-7.24 (m, 1H), 6.44 (s, 1H), 4.99-4.81 (m, 1H), 3.50 (bs, 4H), 3.12-3.11 (d, J = 4.8 Hz, 3H), 1.96 (bs, 5H), 1.28-1.21 (m, 1H), 1.11-1.07 (t, J = 7.2 Hz, 1H). |
| I-555 | *[structure: morpholinyl-7-azaindole]* | MS (ES): m/z 451.30 [M + H]⁺, LCMS purity: 100%, HPLC purity: 98.81%, CHIRAL HPLC: 98.96%, ¹H NMR (DMSO-d$_6$, 400 MHZ): 8.80-8.78 (d, J = 8.4 Hz, 1H), 8.53-8.52 (d, J = 4.8 Hz, 1H), 8.45-8.44 (m, 2H), 7.89-7.87 (d, J = 4.8 Hz, 1H), 7.82 (s, 1H), 7.30-7.27 (s, 1H), 6.50 (s, 1H), 4.84-4.80 (m, 1H), 3.86 (bs, 4H), 3.40 (bs, 4H), 3.13-3.12 (d, J = 4.8 Hz, 3H), 3.04-3.01 (m, 1H), 1.28-1.18 (m, 2H). |
| I-570 | *[structure: fluoroethyl-piperidinyl-pyridinone-amine]* | MS (ES): m/z 487.31 [M + H]⁺, LCMS purity: 100%, HPLC purity: 99.75%, ¹H NMR (DMSO-d$_6$, 400 MHZ): 8.86 (s, 1H), 8.24 (s, 1H), 8.14-8.12 (d, J = 7.2 Hz, 1H), 7.94-7.93 (d, J = 4.8 Hz, 1H), 7.81-7.80 (d, J = 4.8 Hz, 1H), 7.48-7.46 (d, J = 6.8 Hz, 1H), 6.30-6.26 (t, J = 7.2 Hz, 1H), 6.24 (s, 1H), 4.83-4.77 (m, 1H), 4.64-4.62 (t, J = 4.8 Hz, 1H), 4.52-4.50 (t, J = 4.8 Hz, 1H), 3.08-3.05 (d, J = 11.2 Hz, 3H), 2.92-2.91 (d, J = 4.8 Hz, 3H), 2.74-2.72 (t, J = 4.8 Hz, 2H), 2.26-2.20 (t, J = 11.6 Hz, 2H), 1.96-1.95 (d, J = 2.8 Hz, 2H), 1.79 (bs, 2H), 1.29-1.21 (m, 2H), 0.93-0.86 (bs, 1H). |

TABLE 62-continued

| Compound | Intermediate | Characterization Data |
| --- | --- | --- |
| I-575 | (1-methylpiperazin-4-yl substituted 1H-pyrrolo[3,2-b]pyridine) | MS (ES): m/z 464.52 [M + H]⁺, LCMS purity: 100%, HPLC purity: 95.11%, ¹H NMR (DMSO-d₆, 400 MHZ): 8.82-8.80 (d, J = 8.4 Hz, 1H), 8.55-8.52 (m, 1H), 8.47-8.45 (m, 2H), 7.90-7.89 (d, J = 4.4 Hz, 1H), 7.81 (s, 1H), 7.31-7.28 (dd, J = 4.8 Hz, 8.4 Hz, 1H), 6.51 (s, 1H), 4.99-4.83 (m, 1H), 3.37 (s, 4H), 3.14-3.13 (d, J = 4.4 Hz, 3H), 3.08-3.02 (m, 1H), 2.61 (s, 4H), 2.30 (s, 3H), 1.35-1.19 (m, 2H). |
| I-590 | (6-morpholinopyridin-2-amine) | MS (ES): m/z 427.51 [M + H]⁺, LCMS purity: 100%, HPLC purity: 98.01%, CHIRAL HPLC Purity: 100%, ¹H NMR (DMSO-d₆, 400 MHZ): 9.93 (s, 1H), 8.32 (bs, 2H), 7.56 (bs, 1H), 6.81 (bs, 1H), 6.50 (bs, 2H), 4.90-4.74 (m, 1H), 3.74 (m, 4H), 3.49 (m, 4H), 2.94 (bs, 4H), 1.22-1.20 (m, 3H). |
| I-592 | (benzoxazol-4-amine) | MS (ES): m/z 382.37 [M + H]⁺, LCMS purity: 97.72%, HPLC purity: 98.39%, ¹H NMR (DMSO-d₆, 400 MHZ): 9.74 (s, 1H), 8.78 (s, 1H), 8.23 (s, 1H), 7.98-7.90 (m, 3H), 7.49-7.42 (d, J = 6.4 Hz, 1H), 7.42-7.38 (t, J = 8 Hz, 1H), 6.06 (s, 1H), 4.87-4.70 (m, 1H), 2.94-2.88 (m, 4H), 0.70-0.64 (m, 2H). |
| I-607 | (3-amino-1-(3-fluoro-1-methyl-1H-pyrazol-4-yl)pyridin-2(1H)-one) | MS (ES): m/z 456.51 [M + H]⁺, LCMS purity: 100%, HPLC purity: 99.28%, Chiral HPLC purity: 99%, ¹H NMR (DMSO-d₆, 400 MHZ): 9.00(s, 1H), 8.26 (s, 1H), 8.22-8.21 (d, J = 6.8 Hz, 1H), 8.13 (s, 1H), 7.98-7.97 (d, J = 4.8 Hz, 1H), 7.82-7.81 (d, J = 4.4 Hz, 1H), 7.34-7.33 (d, J = 5.6 Hz, 1H), 6.36-6.32 (t, J = 14.4 Hz, 1H), 6.26 (s, 1H), 4.99-4.84 (m, 1H), 3.82 (s, 3H), 3.02-2.91 (m, 4H), 2.29-2.14 (m, 2H) |
| I-619 | (6-(2-oxa-6-azaspiro[3.3]heptan-6-yl)pyridin-2-amine) | MS(ES): m/z 439.5 [M + H]⁺ LCMS purity: 95.62%, HPLC purity: 95.93%, NMR (DMSO-d₆, 400 MHZ): 9.64 (s, 1H), 8.24 (s, 1H), 8.04-8.023 (m, 2H), 7.49-7.45 (t, J = 8 Hz, 1H), 6.91-6.89 (d, J = 8 Hz, 2H), 6.71 (s, 1H), 6.04-6.02 (d, J = 8 Hz, 1H), 4.48-4.45 (t, J = 7.2 Hz, 2H), 4.91 (s, 1H), 4.25-4.22 (d, J = 9.6 Hz, 2H), 4.07-4.05 (d, J = 8.8 Hz, 2H), 3.02-2.82 (m, 5H), 1.25-1.19 (m, 2H). |
| I-624 | (3-amino-4-fluoro-1-(thiazol-2-yl)pyridin-2(1H)-one) | MS (ES): m/z 459.41 [M + H]⁺, LCMS purity: 100%, HPLC purity: 99.60%, Chiral HPLC purity: 98.96%, ¹H NMR (DMSO-d₆, 400 MHZ): 9.05 (s, 1H), 8.88-8.83 (t, J = 7.2 Hz, 1H), 8.17 (s, 1H), 7.98-7.97 (m, 1H), 7.85-7.82 (m, 2H), 7.70-7.69 (m, 1H), 6.87-6.82 (t, J = 7.6 Hz, 1H), 5.70 (s, 1H), 4.67-4.51(bs, 1H), 2.94 (s, 3H), 2.79-2.75 (m, 1H), 1.00-0.92 (m, 1H), 0.48-0.41 (m, 1H). |
| I-626 | (3-amino-5-fluoro-1-(1-methylpiperidin-4-yl)pyridin-2(1H)-one) | MS (ES): m/z 473.36 [M + H]⁺, LCMS purity: 99.37%, HPLC purity: 98.43%, ¹H NMR (DMSO-d₆, 400 MHZ): 9.07 (s, 1H), 8.29 (s, 1H), 8.22-8.21 (d, J = 2.8 Hz, 1H), 8.03 (bs, 1H), 7.75-7.74 (d, J = 4.4 Hz, 1H), 7.62-7.60 (m, 1H), 6.35 (s, 1H), 4.89 (bs, 1H), 4.79-4.73 (m, 1H), 2.92 (s, 5H), 2.23 (s, 3H), 2.09-2.06 (d, J = 11.6 Hz, 2H), 2.02-1.93 (m, 2H), 1.75-1.67 (m, 2H), 1.24-1.19 (m, 1H), 1.14-1.10 (t, J = 12.4 Hz, 1H), 0.97 (bs, 1H). |
| I-632 | (2,3-dihydrofuro[3,2-b]pyridin-5-amine) | MS (ES): m/z 384.26 [M + H]⁺, LCMS purity: 100%, HPLC purity: 100%, ¹H NMR (DMSO-d₆, 400 MHZ): 9.83 (s, 1H), 8.22 (s, 1H), 7.95 (bs, 2H), 7.58-7.56 (d, J = 8.4 Hz, 1H), 7.15-7.13 (d, J = 8.8 Hz, 1H), 6.03 (bs, |

TABLE 62-continued

| Compound | Intermediate | Characterization Data |
|---|---|---|
| | | 1H), 4.78-4.76 (m, 1H), 4.66-4.62 (t, J = 8.8 Hz, 2H), 3.28-3.24 (t, J = 8.8 Hz, 2H), 3.19-3.17 (d, J = 5.2 Hz, 1H), 2.92-2.90 (d, J = 4.8 Hz, 4H), 1.27-1.17 (m, 1H) |
| I-656 | | MS(ES): m/z 481.64 [M + H]+· LCMS purity: 97.82%, HPLC purity: 100%, NMR (DMSO-d$_6$, 400 MHZ): 9.57 (s, 1H), 8.23 (s, 1H), 8.04-8.03 (d, J = 3.6 Hz, 2H), 7.49-7.45 (t, J = 7.6 Hz, 1H), 6.86-6.84 (d, J = 7.6 Hz, 1H), 6.61 (s, 1H), 6.47-6.45 (d, J = 8.4 Hz, 1H), 4.92 (s, 1H), 4.76 (s, 1H), 3.78-3.71 (m, 4H), 3.53-3.47 (m, 2H), 3.42-3.35 (m, 1H), 2.94-2.93 (d, J = 4.4 Hz, 3H), 1.94-1.87 (m, 2H), 1.73-1.69 (t, J = 7.6 Hz, 2H), 1.61-1.59 (m, 3H), 1.23-1.07 (m, 2H). |
| I-660 | | MS (ES): m/z 382.34 [M + H]+, LCMS purity: 100%, HPLC purity: 100%, $^1$H NMR (DMSO-d$_6$, 400 MHZ): 9.83 (s, 1H), 8.66-8.64 (d, J = 6.8 Hz, 1H), 8.55 (s, 1H), 8.28 (s, 1H), 8.25-8.23 (d, J = 7.6 Hz, 1H), 8.07-8.06 (d, J = 4.8 Hz, 1H), 7.84-7.83 (d, J = 4.4 Hz, 1H), 7.14-7.11 (t, J = 7.2 Hz, 1H), 6.26 (s, 1H), 4.95-4.94 (m, 1H), 4.78 (bs, 1H), 2.95-2.94 (d, J = 4.4 Hz, 3H), 1.23-1.16 (m, 1H), 0.84 (bs, 1H) |
| I-673 | | MS (ES): m/z 483.47 [M + H]+, LCMS purity: 97.45%, HPLC purity: 97.20%, CHIRAL HPLC: 97.12% $^1$H NMR (DMSO-d$_6$, 400 MHZ): 8.99 (s, 1H), 8.27-8.22 (m, 3H), 7.98-7.96 (d, J = 4.8 Hz, 1H), 7.83-7.77 (m, 2H), 7.37-7.35 (d, J = 6.8 Hz, 1H), 6.41-6.37 (t, J = 7.2 Hz, 1H), 6.24 (s, 1H), 4.98-4.80 (m, 1H), 3.95 (s, 3H), 3.17-3.16 (d, J = 5.2 Hz, 1H), 3.02-2.99 (m, 1H), 2.90-2.89 (d, J = 4.8 Hz, 3H), 1.29-1.23 (m, 1H). |
| I-681 | | MS (ES): m/z 435.46 [M + H]+, LCMS purity: 100%, HPLC purity: 97.99%, Chiral HPLC purity: 100%, $^1$H NMR (DMSO-d$_6$, 400 MHZ): 9.00 (s, 1H), 8.66-8.65 (d, J = 3.6 Hz, 1H), 8.27 (s, 1H), 8.25 (s, 1H), 8.08-8.04 (t, J = 6.8 Hz 1H), 7.98-7.97 (d, J = 4.8 Hz, 1H), 7.86 (s, 1H), 7.84 (s, 1H), 7.58-7.54 (m, 2H), 6.43-6.39 (t, 1H), 6.27 (s, 1H), 5.00-4.83 (m, 1H), 3.03-3.00 (m, 1H), 2.92-2.91 (d, J = 4.8 Hz, 1H), 1.28-1.20 (m, 2H), 0.97-0.88 (m, 2H) |
| I-693 | | MS (ES): m/z 476.36 [M + H]+, LCMS purity: 100%, HPLC purity: 99.03%, CHIRAL HPLC: (50.14%, 49.85%) $^1$H NMR (DMSO-d$_6$, 400 MHZ): 9.04 (s, 1H), 8.26 (s, 1H), 8.22-8.22 (d, J = 2 Hz, 1H), 8.02-8.01 (d, J = 4.8 Hz, 1H), 7.75 (bs, 1H), 7.69-7.68 (d, J = 2 Hz, 1H), 6.32 (s, 1H), 4.89-4.82 (m, 2H), 4.74 (bs, 1H), 3.82 (bs, 2H), 3.66-3.62 (t, J = 10 Hz, 1H), 3.50-3.45 (t, J = 8.8 Hz, 1H), 3.17-3.16 (d, J = 5.2 Hz, 1H), 2.91-2.90 (d, J = 4.8 Hz, 3H), 2.86 (bs, 1H), 1.75 (bs, 2H), 1.23-1.16 (m, 2H). |
| I-709 | | MS (ES): m/z 439.44 [M + H]+, LCMS purity: 95.07%, HPLC purity: 93.57%, CHIRAL HPLC: 99.72%, $^1$H NMR (DMSO-d$_6$, 400 MHZ): 9.60 (s, 1H), 8.24 (s, 1H), 8.04-8.03 (d, J = 4 Hz, 2H), 7.55-7.51 (t, J = 8 Hz, 1H), 6.94-6.92 (d, J = 6.8 Hz, 1H), 6.70 (bs, 1H), 6.34-6.32 (d, J = 7.6 Hz, 1H), 5.27-5.25 (d, J = 6.8 Hz, 2H), 4.92 (bs, 1H), 4.76 (bs, 1H), 4.66-4.64 (d, J = 7.2 Hz, 2H), 3.87-3.83 (t, J = 6.8 Hz, 2H), 2.94-2.94 (d, J = 3.2 Hz, 3H), 2.58 (s, 3H), 1.25-1.20 (m, 1H). |

TABLE 62-continued

| Compound | Intermediate | Characterization Data |
| --- | --- | --- |
| I-716 | (3-amino-1-(oxazol-2-yl)pyridin-2(1H)-one structure) | MS (ES): m/z 425.33 [M + H]⁺, LCMS purity: 96.67%, HPLC purity: 96.60%, ¹H NMR (DMSO-d₆, 400 MHZ): 9.06 (s, 1H), 8.34 (s, 1H), 8.26 (s, 1H), 8.24 (s, 1H), 7.80-7.79 (d, J = 4.4 Hz, 1H), 7.49 (s, 1H), 7.46-7.44 (d, J = 8.4 Hz, 1H), 6.42-6.38 (d, J = 7.2 Hz, 1H), 6.24 (s, 1H), 5.98 (bs, 1H), 5.24 (bs, 1H), 2.98 (bs, 1H), 2.90 (s, 3H), 0.92-0.86 (m, 2H) |
| I-718 | (3-amino-1-(2-methyloxazol-5-yl)pyridin-2(1H)-one structure) | MS (ES): m/z 439.39 [M + H]⁺, LCMS purity: 99.39%, HPLC purity: 98.59%, CHIRAL HPLC: 99.31%, ¹H NMR (DMSO-d₆, 400 MHZ): 9.08 (s, 1H), 8.27 (s, 1H), 8.23-8.21 (d, J = 7.2 Hz, 1H), 8.01-8.00 (d, J = 4.8 Hz, 1H), 7.80-7.79 (d, J = 4.4 Hz, 1H), 7.53-7.51 (d, J = 6.8 Hz, 1H), 7.40 (s, 1H), 6.45-6.41 (t, J = 7.2 Hz, 1H), 6.27 (s, 1H), 4.99-4.82 (m, 1H), 2.92-2.91 (d, J = 4.4 Hz, 3H), 2.50 (s, 3H), 1.28-1.19 (m, 1H), 0.87 (bs, 2H) |
| I-719 | (3-amino-1-(5-fluoro-1-methyl-1H-pyrazol-4-yl)pyridin-2(1H)-one structure) | MS (ES): m/z 456.4 [M + H]⁺, LCMS purity: 100%, HPLC purity: 99.48%, Chiral HPLC purity: 96.10%, ¹H NMR (DMSO-d₆, 400 MHZ): 9.98 (s, 1H), 8.25-8.20 (m, 2H), 7.97-7.95 (d, J = 4.8 Hz, 1H), 7.81-7.80 (d, J = 4.8 Hz, 1H), 7.75-7.74 (d, J = 2 Hz, 1H), 7.34-7.32 (d, J = 5.6 Hz, 1H), 6.36-6.33 (t, J = 7.2 Hz, 1H), 6.25 (s, 1H), 4.99-4.79 (m, 1H), 3.80 (s, 3H), 3.01-2.97 (m, 1H), 2.90-2.89 (d, J = 4.8 Hz, 3H), 1.28-1.18 (m, 1H), 0.93-0.87 (m, 1H). |
| I-748 | (3-amino-1-(pyridin-3-yl)pyridin-2(1H)-one structure) | MS(ES): m/z 435.51 [M + H]⁺ LCMS purity: 100%, HPLC purity: 98.54%, CHIRAL HPLC: 99.81% ¹H NMR (DMSO-d₆, 400 MHZ): 8.98 (s, 1H), 8.74 (s, 1H), 8.68-8.67 (d, J = 4.0 Hz, 1H), 8.26 (s, 2H), 8.02-8.00 (d, J = 8.0 Hz, 1H), 7.97-7.96 (d, J = 4.0 Hz, 1H), 7.84-7.82 (d, J = 8.0 Hz, 1H), 7.64-7.60 (m, 1H), 7.42-7.41 (d, J = 4.0 Hz, 1H), 6.40-6.37 (m, 1H), 6.26 (s, 1H), 4.99-4.81 (m, 1H), 3.02-2.99 (m, 1H), 2.90-2.89 (d, J = 4.0 Hz, 3H), 1.30-1.20 (m, 1H), 0.96-0.88 (m, 1H). |
| I-759 | (3-amino-5-chloro-1-(1-methylpiperidin-3-yl)pyridin-2(1H)-one structure) | MS (ES): 491.5 [M + H]⁺ LCMS purity: 97.01%, HPLC purity: 96.33%, CHIRAL HPLC: 46.36% 47.39%, ¹H NMR (DMSO-d₆, 400 MHZ): 9.03 (s, 1H), 8.26 (s, 1H), 8.22-8.21 (d, J = 2 Hz, 1H), 8.02-8.01 (d, J = 4.8 Hz, 1H), 7.77-7.75 (d, J = 5.6 Hz, 2H), 6.31 (s, 1H), 4.90 (bs, 2H), 4.72 (bs, 1H), 3.32 (s, 1H), 2.91-2.90 (d, J = 4.8 Hz, 3H), 2.22 (bs, 3H), 2.08 (s, 2H), 1.77 (bs, 4H), 1.62 (bs, 2H), 1.23-1.16 (m, 1H) |
| I-762 | (3-amino-1-(oxazol-5-yl)pyridin-2(1H)-one structure) | MS (ES): m/z 425.25 [M + H]⁺, LCMS purity: 99.55%, HPLC purity: 98.61%, CHIRAL HPLC: 99.21%, ¹H NMR (DMSO-d₆, 400 MHZ): 9.10 (s, 1H), 8.51 (s, 1H), 8.26 (s, 1H), 8.24-8.22 (d, J = 7.2 Hz, 1H), 7.99 (bs, 1H), 7.79-7.78 (d, J = 4.4 Hz, 1H), 7.57 (bs, 2H), 6.46-6.43 (t, J = 7.2 Hz, 1H), 6.27 (s, 1H), 4.97 (bs, 1H), 4.81 (bs, 1H), 2.91-2.90 (d, J = 4.4 Hz, 3H), 1.27-1.18 (m, 2H). |
| I-766 | (3-amino-1-(6-methylpyridin-3-yl)pyridin-2(1H)-one structure) | MS (ES): m/z 449.44 [M + H]⁺, LCMS purity: 99.03%, HPLC purity: 98.80%, CHIRAL HPLC: 99.66%, ¹H NMR (DMSO-d₆, 400 MHZ): 8.97 (s, 1H), 8.58-8.57 (d, J = 2.4 Hz, 1H), 8.25 (s, 1H), 8.24 (s, 1H), 7.96-7.95 (d, J = 4.8 Hz, 1H), 7.88-7.87 (d, J = 2.4 Hz, 1H), 7.86-7.82 (m, 1H), 7.46-7.44 (d, J = 8 Hz, 1H), 7.39-7.37 (d, J = 6.8 Hz, 1H), 6.39-6.35 (t, J = 7.2 Hz, 1H), 6.26 (s, 1H), 4.98 (bs, 1H), 4.82 (bs, 1H), 2.99 (bs, 1H), 2.90- |

TABLE 62-continued

| Compound | Intermediate | Characterization Data |
|---|---|---|
| | | 2.89 (d, J = 4.8 Hz, 3H), 2.564.98 (s, 3H), 1.29-1.22 (m, 1H). |
| I-789 | (5-chloro-3-amino-1-(1-methylpiperidin-4-yl)pyridin-2(1H)-one structure) | MS(ES): m/z 489.61 [M + H]+, LCMS purity: 98.80%, HPLC purity: 99.48%, Chiral HPLC purity: 97.96%, 49.55%, NMR (DMSO-d6, 400 MHZ): 9.02 (s, 1H), 8.27 (s, 1H), 8.22 (d, J = 4 Hz, 1H), 8.03-8.02 (d, J = 4.8 Hz, 1H), 7.77 (s, 1H), 7.60-60 (d, J = 2.4 Hz, 1H), 6.32 (s, 1H), 4.91 (s, 1H), 2.92-2.91 (d, J = 4.4 Hz, 3H), 2.86 (bs, 1H), 2.22 (d, 3H), 2.09-1.99 (m, 3H), 1.76-1.73 (d, J = 10 Hz, 2H), 1.24 (s, 2H), 1.20-1.17 (m, 1H), 1.00 (bs, 1H), 0.94 (bs, 1H), 0.86 (s, 1H). |
| I-790 | (3-amino-1-(4-methyloxazol-5-yl)pyridin-2(1H)-one structure) | MS (ES): m/z 439.39[M + H]+, LCMS purity: 96.88%, HPLC purity: 95.89%, CHIRAL HPLC: 94.97%, 1H NMR (DMSO-d6, 400 MHZ): 9.03 (s, 1H), 8.44 (s, 1H), 8.27-8.25 (d, J = 6.4 Hz, 2H), 8.01-8.00 (d, J = 4.8 Hz, 1H), 7.81-7.80 (d, J = 4.4 Hz, 1H), 7.36-7.35 (d, J = 5.6 Hz, 1H), 6.41-6.37 (t, J = 7.2 Hz, 1H), 6.26 (s, 1H), 4.99 (bs, 1H), 4.82 (bs, 1H), 3.02 (s, 1H), 2.91-2.90 (d, J = 4.8 Hz, 3H), 2.06 (s, 3H), 1.27-1.22 (m, 1H). |
| I-795 | (3-amino-1-(3-methoxycyclohexyl)pyridin-2(1H)-one structure) | MS (ES): m/z 470.51 [M + H]+, LCMS purity: 100%, HPLC purity: 98.67%, Chiral HPLC: 56.99%, 40.12%, 1H NMR (DMSO-d6, 400 MHZ): 8.86 (s, 1H), 8.25 (s, 1H), 8.13-8.12 (d, J = 7.2 Hz, 1H), 7.95-7.94 (d, J = 4.8 Hz, 1H), 8.82-7.81 (d, J = 4.4 Hz, 1H), 7.48-7.46 (d, J = 6.8 Hz, 1H), 6.31-6.27 (t, , J = 7.2 Hz, 1H), 6.24 (s, 1H), 4.83-4.82 (m, 2H), 3.31 (s, 3H), 3.01-2.98 (m, 1H), 2.92-2.91 (d, J = 4.8 Hz, 3H), 2.19-2.16 (d, J = 10.8 Hz, 1H), 2.07-2.08 (m, 1H), 1.74 (bs, 1H), 1.64-1.58 (t, J = 12 Hz, 2H), 1.21 (bs, 4H), 0.91-0.84 (m, 2H). |
| I-811 | (3-amino-1-(3-oxabicyclo[3.1.0]hexan-6-yl)pyridin-2(1H)-one structure) | MS (ES): m/z 440.29 [M + H]+, LCMS purity: 100%, HPLC purity: 95.44%, CHIRAL HPLC purity: 98.94, 1H NMR (DMSO-d6, 400 MHZ): 8.92 (s, 1H), 8.24 (s, 1H), 8.12-8.11 (d, J = 4.0 Hz, 1H), 7.95-7.93 (d, J = 8.0 Hz, 1H), 7.80-7.79 (d, J = 4.0 Hz, 1H), 7.29-7.27 (d, J = 8.0 Hz, 1H), 6.22 (s, 2H), 4.97-4.81 (m, 1H), 4.01-3.99 (d, J = 8.0 Hz, 2H), 3.75-3.73 (d, J = 8.0 Hz, 2H), 3.14 (s, 1H), 2.99 (s, 1H), 2.91-2.90 (d, J = 4.0 Hz, 3H), 2.28 (s, 2H), 1.26-1.17 (m, 1H), 0.90 (bs, 1H) |
| I-813 | (3-amino-1-(2-methylpyridin-3-yl)pyridin-2(1H)-one structure) | MS (ES): m/z 449.41 [M + H]+, LCMS purity: 100%, HPLC purity: 98.81%, CHIRAL HPLC: 99.17%, 1H NMR (DMSO-d6, 400 MHZ): 8.96 (s, 1H), 8.48-8.47 (d, J = 4 Hz, 1H), 8.31-8.29 (d, J = 7.2 Hz, 1H), 8.27 (s, 1H), 7.98-7.93 (m, 2H), 7.85-7.84 (d, J = 4 Hz, 1H), 7.54-7.51 (m, 1H), 7.31-7.29 (d, J = 6.4 Hz, 1H), 6.41-6.38 (t, J = 6.8 Hz, 1H), 6.26 (s, 1H), 5.00 (bs, 1H), 4.83 (bs, 1H), 3.02 (bs, 1H), 2.91-2.90 (d, J = 4.4 Hz, 3H), 2.15 (s, 3H), 1.31-1.21 (m, 1H). |
| I-849 | (3-amino-1-(1-(2-fluoroethyl)piperidin-3-yl)pyridin-2(1H)-one structure) | MS (ES): 487.52 [M + H]+ LCMS purity: 97.62%, HPLC purity: 98.67%, CHIRAL HPLC: 52.66% 46.18%, 1H NMR (DMSO-d6, 400 MHZ): 8.89 (s, 1H), 8.24 (s, 1H), 8.14-8.13 (d, J = 7.2 Hz, 1H), 7.94-7.93 (d, J = 4.8 Hz, 1H), 7.81-7.80 (d, J = 4.4 Hz, 1H), 7.56-7.55 (d, J = 6.8 Hz, 1H), 6.29-6.28 (d, J = 6.8 Hz, 1H), 6.25 (s, 1H), 4.95 (bs, 1H), 4.81 (bs, 1H), 4.63-4.61 (t, J = 4.8 Hz, 1H), 4.51-4.50 (d, J = 4.4 Hz, 1H), 2.92-2.91 (d, J = 4.8 Hz, 3H), 2.86 (bs, 3H), 2.74-2.72 (t, J = 4.8 Hz, 1H), 2.67-2.65 (t, J = 5.2 Hz, 1H), 2.38 (bs, 1H), |

| Compound | Intermediate | Characterization Data |
|---|---|---|
| | | 2.21-2.16 (t, J = 10.4 Hz, 1H), 1.80 (bs, 2H), 1.77 (bs, 1H), 1.65 (bs, 1H), 1.28-1.19 (m, 1H), 0.84 (bs, 1H). |
| I-860 | 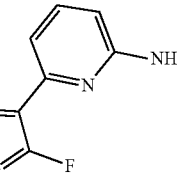 | MS (ES): m/z 440.27 [M + H]+, LCMS purity: 100%, HPLC purity: 99.46%, CHIRAL HPLC: 100%, 1H NMR (DMSO-d6, 400 MHZ): 9.94 (bs, 1H), 8.29 (bs, 1H), 8.22 (bs, 1H), 8.04 (bs, 1H), 7.79-7.75 (t, J = 7.2 Hz, 1H), 7.43 (bs, 1H), 7.21-7.19 (d, J = 7.2 Hz, 1H), 6.75 (bs, 1H), 4.93 (bs, 1H), 4.77 (bs, 1H), 3.82 (s, 3H), 2.93-2.92 (d, J = 4.4 Hz, 3H), 1.24 (bs, 2H), 1.07 (bs, 1H). |
| I-882 | 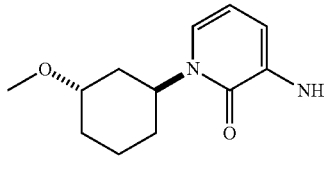 | MS (ES): m/z 470.52 [M + H]+, LCMS purity: 99.13%, HPLC purity: 98.51%, 1H NMR (DMSO-d6, 400 MHZ): 8.87 (s, 1H), 8.24 -s, 1H), 8.12-8.11 (d, J = 6.4 Hz, 1H), 7.94-7.93 (d, J = 4.8 Hz, 1H), 7.82-7.81 (d, J = 4.4 Hz, 1H), 7.44-7.43 (d, J = 5.6 Hz, 1H), 6.30-6.27 (t, J = 7.2 Hz, 1H), 6.24 (s, 1H), 5.12 (bs, 1H), 4.99-4.96 (m, 1H), 4.83-4.79 (m, 1H), 3.71 (bs, 1H), 3.26 (bs, 3H), 3.01-2.97 (m, 1H), 2.92-2.91(d, J = 4.8 Hz, 3H), 2.06 (s, 1H), 1.35 (bs, 2H), 1.24-1.17 (m, 4H), 0.93-0.80 (m, 2H). |
| I-889 | 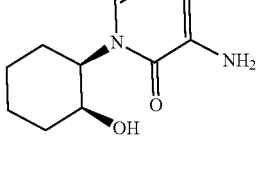 | MS (ES): m/z 456.52 [M + H]+, LCMS purity: 100%, HPLC purity: 99.75%, CHIRAL HPLC: 100%, 1H NMR (DMSO-d6, 400 MHZ): 8.84 (s, 1H), 8.24 (s, 1H), 8.14-8.12 (d, J = 6.8 Hz, 1H), 7.93-7.92 (d, J = 5.2 Hz, 1H), 7.84-7.83 (d, J = 4.4 Hz, 1H), 7.39-7.37 (d, J = 6 Hz, 1H), 6.26-6.23 (t, J = 7.2 Hz, 1H), 6.21 (s, 1H), 4.92-4.91 (d, J = 4.8 Hz, 1H), 4.80 (bs, 2H), 3.95 (bs, 1H), 3.47 (s, 3H), 2.97 (bs, 1H), 2.92-2.91 (d, J = 4.8 Hz, 3H), 2.10 (s, 1H), 1.87-1.85 (d, J = 10.8 Hz, 1H), 1.80-1.77 (d, J = 9.2 Hz, 1H), 1.62 (bs, 2H), 1.29-1.20 (m, 1H), 0.91 (bs, 1H). |
| I-892 | 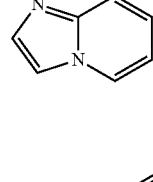 | MS (ES): m/z 381.47 [M + H]+, LCMS purity: 100%, HPLC purity: 98.11%, CHIRAL HPLC: 99.26%, 1H NMR (DMSO-d6, 400 MHZ): 9.54 (s, 1H), 8.27-8.25 (d, J = 6 Hz, 2H), 8.01 (bs, 2H), 7.93-7.92 (d, J = 4.8 Hz, 1H), 7.90-7.88 (d, J = 7.6 Hz, 1H), 7.60 (s, 1H), 7.86-6.83 (t, J = 7.2 Hz, 1H), 6.33 (s, 1H), 4.97 (bs, 1H), 4.81 (bs, 1H), 2.95-2.93 (d, J = 4.8 Hz, 3H), 1.27-1.19 (m, 2H). |
| I-912 | 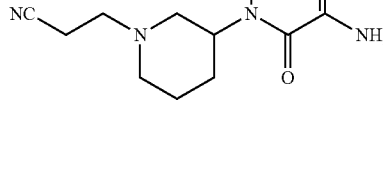 | MS(ES): m/z 494.82 [M + H]+, LCMS purity: 97.25%, HPLC purity: 97.39%, Chiral HPLC purity: 46.80%: 50.72%, 1H NMR (DMSO-d6, 400 MHZ): 8.70-8.69 (d, J = 4.0 Hz, 1H), 8.22-8.18 (m, 2H), 7.94-7.83 (m, 3H), 6.98-6.95 (m, 1H), 5.90-5.89 (m, 1H), 5.14 (s, 1H), 4.86-4.70 (m, 1H), 3.07 (s, 1H), 2.94-2.93 (d, J = 4.0 Hz, 3H) 2.89 (s, 1H), 2.75-2.72 (s, 1H), 2.69-2.63 (m, 4H), 2.24-2.23 (m, 1H), 2.10-2.02 (m, 2H), 1.74 (s, 1H), 1.51-1.46 (m, 2H) 1.18-1.12 (m, 1H) 0.72-0.66 (m, 1H). |
| I-915 | 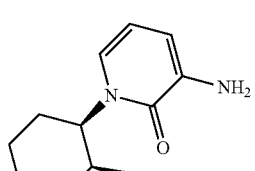 | MS (ES): m/z 470.55 [M + H]+, LCMS purity: 99.32%, HPLC purity: 97.77%, 1H NMR (DMSO-d6, 400 MHZ): 8.84 (s, 1H), 8.24 (s, 1H), 8.15-8.14 (d, J = 6.8 Hz, 1H), 7.94-7.92 (d, J = 4.8 Hz, 1H), 7.83-7.82 (d, J = 4.4 Hz, 1H), 7.37-7.35 (d, J = 6.0 Hz, 1H), 6.27-6.22 (m, 2H), 4.98-4.79 (m, 2H), 3.58 (s, 1H), 3.12 (s, 3H), 3.01-2.97 (m, 1H), 2.92-2.91 (d, J = 4.8 Hz 3H), 2.10 (s, 2H), 1.85 (bs, 2H), 1.58-1.55 (m, 2H), 1.24-1.21 (t, J = 10.8 Hz, 2H), 0.92-0.84 (m, 2H). |

TABLE 62-continued

| Compound | Intermediate | Characterization Data |
|---|---|---|
| I-916 | | MS (ES): m/z 428.76 [M + H]+, LCMS purity: 97%, HPLC purity: 96%, CHIRAL HPLC: 48%, 52%, $^1$H NMR (DMSO-$d_6$, 400 MHZ): 8.89 (s, 1H), 8.24 (s, 1H), 8.15-8.13 (d, J = 7.2 Hz, 1H), 7.94-7.93 (d, J = 6.4 Hz, 1H), 7.82-7.81(bs, 1H), 7.49-7.47 (d, J = 6.4 Hz, 1H), 6.33-6.31 (t, J = 6.8 Hz, 1H), 6.24 (s, 1H), 5.63-5.62 (d, J = 6.8 Hz, 1H), 4.97-4.82 (m, 2H), 4.37 (bs, 1H), 3.00 (bs, 1H), 2.91-2.90 (d, J = 4.4 Hz, 3H), 2.14-2.12 (d, J = 7.2 Hz, 2H), 1.63(bs, 2H) 1.24-1.21 (d, J = 11.6 Hz, 2H). |
| I-934 | | MS (ES): m/z 473.57 [M + H]+, LCMS purity: 100%, HPLC purity: 96.88%, Chiral HPLC: 100%, $^1$H NMR (DMSO-$d_6$, 400 MHZ): 8.88 (bs, 1H), 8.25 (s, 1H), 8.14-8.12 (d, J = 7.2 Hz, 1H), 7.94-7.93 (d, J = 4.8 Hz, 1H), 7.83-7.82 (d, J = 4.4 Hz, 1H), 7.61-7.59 (d, J = 6.8 Hz, 1H), 5.48 (s, 1H), 4.97-4.79 (m, 1H), 4.67-4.65 (m, 1H), 4.56-4.53 (m, 1H), 3.14 (s, 1H), 2.99-2.97 (m, 2H), 2.92-2.91 (d, J = 4.8 Hz, 3H), 2.84-2.69 (m, 3H), 2.39-2.35 (m, 2H), 1.78 (s, 1H), 1.29-1.17 (m, 2H), 0.92-0.83 (m, 2H). |
| I-935 | | MS (ES): m/z 473.57 [M + H]+, LCMS purity: 100%, HPLC purity: 96.82%, Chiral HPLC: 100%, $^1$H NMR (DMSO-$d_6$, 400 MHZ): 8.89 (bs, 1H), 8.25 (s, 1H), 8.13-8.12 (d, J = 6.8 Hz, 1H), 7.95-7.94 (d, J = 4.8 Hz, 1H), 7.83-7.82 (d, J = 4.4 Hz, 1H), 7.61-7.59 (d, J = 6.8 Hz, 1H), 5.48 (s, 1H), 4.97-4.79 (m, 1H), 4.67-4.65 (m, 1H), 4.56-4.53 (m, 1H), 3.14 (s, 1H), 2.99-2.97 (m, 2H), 2.92-2.91 (d, J = 4.8 Hz, 3H), 2.84-2.69 (m, 3H), 2.39-2.35 (m, 2H), 1.78 (s, 1H), 1.29-1.17 (m, 2H), 0.92-0.83 (m, 2H). |
| I-938 | | MS (ES): 453.61 [M + H]+, LCMS purity: 100%, HPLC purity: 99.81%, CHIRAL HPLC purity: 100%, $^1$H NMR (DMSO-$d_6$, 400 MHZ): 9.01 (bs, 1H), 8.27 (bs, 1H), 8.24 (bs, 1H), 8.01 (bs, 1H), 7.81 (bs, 1H), 7.33-7.31 (d, J = 6 Hz, 1H), 6.39-6.36 (t, J = 6.8 Hz, 1H), 6.25 (bs, 1H), 4.99 (bs, 1H), 4.83 (bs, 1H), 3.00 (bs, 1H), 2.91-2.90 (d, J = 3.6 Hz, 3H), 2.43 (s, 3H), 2.00 (s, 3H), 1.25-1.21 (m, 1H). |
| I-965 | | MS (ES): m/z 442.31 [M + H]+, LCMS purity: 98.62%, HPLC purity: 95.22%, CHIRAL HPLC: 95.00%, $^1$H NMR (DMSO-$d_6$, 400 MHZ): 8.87 (s, 1H), 8.26 (s, 1H), 8.15-8.13 (d, J = 7.2 Hz, 1H), 7.93-7.92 (d, J = 4.8 Hz, 1H), 7.85-7.81 (d, J = 4.4 Hz, 1H), 7.41-7.39 (d, J = 6.0 Hz, 1H), 6.25-6.22 (m, 2H), 4.97-4.92 (m, 1H), 4.88 (bs, 1H), 4.21 (s, 1H), 2.91-2.85 (m, 4H), 2.15-1.88 (m, 4H), 1.71-1.61 (m, 2H), 0.82-0.77 (m, 2H), 0.53-0.52 (m, 1H). |
| I-966 | | MS (ES): m/z 442.52 [M + H]+, LCMS purity: 98.58%, HPLC purity: 98.29%, CHIRAL HPLC: 100%, $^1$H NMR (DMSO-$d_6$, 400 MHZ): 8.86 (s, 1H), 8.24 (s, 1H), 8.15-8.13 (d, J = 7.2 Hz, 1H), 7.92 (s, 1H), 7.85-7.84 (d, J = 4.4 Hz, 1H), 7.42-7.40 (d, J = 7.2 Hz, 1H), 6.25-6.22 (m, 2H), 4.97-4.96 (m, 1H), 4.82 (bs, 1H), 4.21 (s, 1H), 3.01 (s, 1H), 2.92 (s, 3H), 2.15-1.88 (m, 4H), 1.71-1.61 (m, 2H), 0.82-0.77 (m, 2H), 0.53-0.52 (m, 1H). |

TABLE 62-continued

| Compound | Intermediate | Characterization Data |
|---|---|---|
| I-968 | | MS (ES): m/z 453.37 [M + H]+, LCMS purity: 100%, HPLC purity: 100%, $^1$H NMR (DMSO-$d_6$, 400 MHZ): 9.07 (bs, 1H), 8.75-8.75 (d, J = 2.4 Hz, 1H), 8.68 (s, 1H), 8.28 (s, 1H), 8.27 (s, 1H), 8.16-8.15 (d, J = 2 Hz, 1H), 7.99-7.98 (d, J = 4.8 Hz, 1H), 7.84-7.83 (d, J = 4.4 Hz, 1H), 7.47-7.45 (d, J = 5.2 Hz, 1H), 6.43-6.39 (t, J = 7.2 Hz, 1H), 6.28 (s, 1H), 5.02-4.98 (m, 1H), 4.86-4.82 (m, 1H), 2.91-2.90 (d, J = 4.4 Hz, 3H), 0.94-0.89 (m, 2H). |
| I-983 | | MS (ES): 456.57 [M + H]+ LCMS purity: 100%, HPLC purity: 98.19%, CHIRAL HPLC: 49.12, 50.87%, $^1$H NMR (DMSO-$d_6$, 400 MHZ): 8.85 (s, 1H), 8.24 (s, 1H), 8.12-8.10 (d, J = 7.2 Hz, 1H), 7.94-7.93 (d, J = 4.8 Hz, 1H), 7.82-7.81 (d, J = 4.4 Hz, 1H), 7.42-7.41 (d, J = 6 Hz, 1H), 6.27-6.25 (d, J = 7.2 Hz, 1H), 6.24 (s, 1H), 5.28 (bs, 1H), 4.97 (bs, 1H), 4.83-4.79 (m, 1H), 4.14 (s, 1H), 2.98 (bs, 1H), 2.92-2.91 (d, J = 4.8 Hz, 3H), 1.93-1.86 (m, 2H), 1.83-1.76 (m, 2H), 1.61 (bs, 4H), 1.28-1.19 (m, 2H). |
| I-986 | | MS (ES): m/z 480.52 [M + H]+, LCMS purity: 97.89%, HPLC purity: 99.02%, CHIRAL HPLC purity: 98.81%, $^1$H NMR (DMSO-$d_6$, 400 MHZ): 8.89 (s, 1H), 8.25 (s, 1H), 8.14-8.12 (d, J = 7.6 Hz, 1H), 7.95-7.94 (d, J = 4.0 Hz, 1H), 7.82-7.81 (d, J = 4.4 Hz, 1H), 7.65-7.63 (d, J = 7.2 Hz 1H), 6.31-6.25 (m, 2H), 5.49 (bs, 1H), 4.97-4.82 (m, 1H), 3.13 (m, 1H), 3.02-3.00 (m, 2H), 2.92 (bs, 3H), 2.72 (m, 1H), 2.40-2.36 (m, 1H), 1.80 (bs, 2H), 2.16-2.00 (m, 2H), 1.27-1.11 (m, 2H), 1.12-1.10 (m, 2H). |
| I-987 | | MS (ES): m/z 480.57 [M + H]+, LCMS purity: 98.43%, HPLC purity: 98.01%, CHIRAL HPLC Purity: 100%, $^1$H NMR (DMSO-$d_6$, 400 MHZ): 8.88 (s, 1H), 8.24 (s, 1H), 8.13-8.12 (d, J = 6.4, 1H), 7.94-7.93 (m, 1H), 7.81-7.93 (m, 1H), 7.64-7.63 (m, 1H), 6.31-6.25 (m, 2H), 5.50 (bs, 1H), 4.99-4.79 (bs, 1H), 3.42-3.35 (m, 1H) 3.15-3.11 (m, 1H) 3.02-2.99 (m, 2H) 2.92-2.90 (m, 3H), 2.77-2.75 (m, 2H) 2.72-2.70 (m, 2H) 2.52-2.34 (m, 1H) 1.81-1.76 (m, 1H) 1.35-1.24 (m, 2H), 1.21-1.19 (m, 1H). |
| I-988 | | MS(ES): m/z 456.52 [M + H]+, LCMS purity: 100%, HPLC purity: 99.70%, Chiral HPLC purity: 100%, $^1$H NMR (DMSO-$d_6$, 400 MHZ): 8.84 (s, 1H), 8.24 (s, 1H), 8.15-8.12 (d, J = 7.6 Hz, 1H), 7.93 (bs, 1H), 7.85-7.83 (m, 1H), 7.39-7.37 (d, J = 6.8 Hz, 1H), 6.27-6.22 (m, 2H), 5.00-4.97 (m, 1H), 4.84-4.81 (m, 1H), 3.95 (bs, 1H), 2.99 (bs, 1H), 2.91 (s, 3H), 2.21-2.13 (m, 1H), 1.92-1.85 (m, 1H), 1.84-1.75 (m, 1H), 1.70-1.55 (m, 2H), 1.55-1.39 (m, 3H), 1.31-1.16 (m, 1H), 0.95-0.85 (m, 2H). |
| I-997 | | MS (ES): m/z 442.66 [M + H]+, LCMS purity: 100%, HPLC purity: 97.85%, CHIRAL HPLC purity: 52.46%, 46.53%, $^1$H NMR (DMSO-$d_6$, 400 MHZ): 8.91 (s, 1H), 8.24 (s, 1H), 8.15-8.14 (d, J = 7.2 Hz, 1H), 7.95-7.94 (d, J = 4.4 Hz, 1H), 7.82-7.80 (d, J = 4.4 Hz, 1H), 7.56-7.55 (d, J = 6.4 Hz, 1H), 6.34-6.30 (t, J = 6.8 Hz, 1H), 6.25 (s, 1H), 5.20-5.14 (m, 1H), 4.98 (bs, 1H), 4.26-4.20 (m, 1H), 3.16 (s, 3H), 2.91-2.90 (d, J = 3.6 Hz, 3H), 2.20-2.14 (m, 2H), 1.89-1.84 (t, J = 10.4 Hz, 1H), 1.66-1.61 (t, J = 9.6 Hz, 1H), 1.24 (bs, 3H). |

TABLE 62-continued

| Compound | Intermediate | Characterization Data |
|---|---|---|
| I-1045 | | MS(ES): m/z 470.57 [M + H]⁺, LCMS purity: 100%, HPLC purity: 99.51%, Chiral HPLC purity: 99.87%, ¹H NMR (DMSO-d₆, 400 MHZ): 8.84 (s, 1H), 8.24 (s, 1H), 8.15-8.13 (d, J = 7.2 Hz, 1H), 7.94-7.92 (d, J = 4.8 Hz, 1H), 7.84-7.82 (m, 1H), 7.37-7.35 (d, J = 6.0 Hz, 1H), 6.28-6.24 (t, J = 7.2 Hz, 1H), 6.21 (s, 1H), 4.97-4.79 (m, 2H), 3.57 (bs, 1H), 3.12 (s, 3H), 3.01-2.97 (m, 1H), 2.92-2.91 (d, J = 4.4 Hz, 3H), 2.18-2.05 (m, 2H), 1.92-1.85 (m, 1H), 1.61-1.40 (m, 5H), 1.31-1.18 (m, 1H), 0.96-0.83 (m, 1H). |
| I-1110 | | MS (ES): m/z 428.42 [M + H]⁺, LCMS purity: 100%, HPLC purity: 99.73%, CHIRAL HPLC: 49.14%, 50.86%, ¹H NMR (DMSO-d₆, 400 MHZ): 8.84 (s, 1H), 8.24 (s, 1H), 8.15-8.13 (d, J = 7.2 Hz, 1H), 7.91-7.90 (d, J = 4.8 Hz, 1H), 7.85-7.83 (t, J = 5.2 Hz, 1H), 7.45-7.44 (d, J = 6.4 Hz, 1H), 6.27-6.23 (t, J = 7.2 Hz, 2H), 5.19-5.15 (m, 2H), 4.99 (bs, 1H), 4.96 (bs, 1H), 4.52 (bs, 1H), 3.18 (bs, 1H), 3.18 (bs, 1H), 2.92-2.90 (d, J = 4.8 Hz, 3H), 2.76-2.67 (m, 1H), 1.75-1.70 (t, J = 10.8 Hz, 1H), 1.30-1.20 (m, 1H), 0.94(bs, 1H). |

108.3. Synthesis of N-((1R,2S)-2-fluorocyclopropyl)-5-(1-isopropyl-1H-pyrrolo[2,3-b]pyridin-3-yl)-7-(methylamino)pyrazolo[1,5-a]pyrimidine-3-carboxamide (I-225)

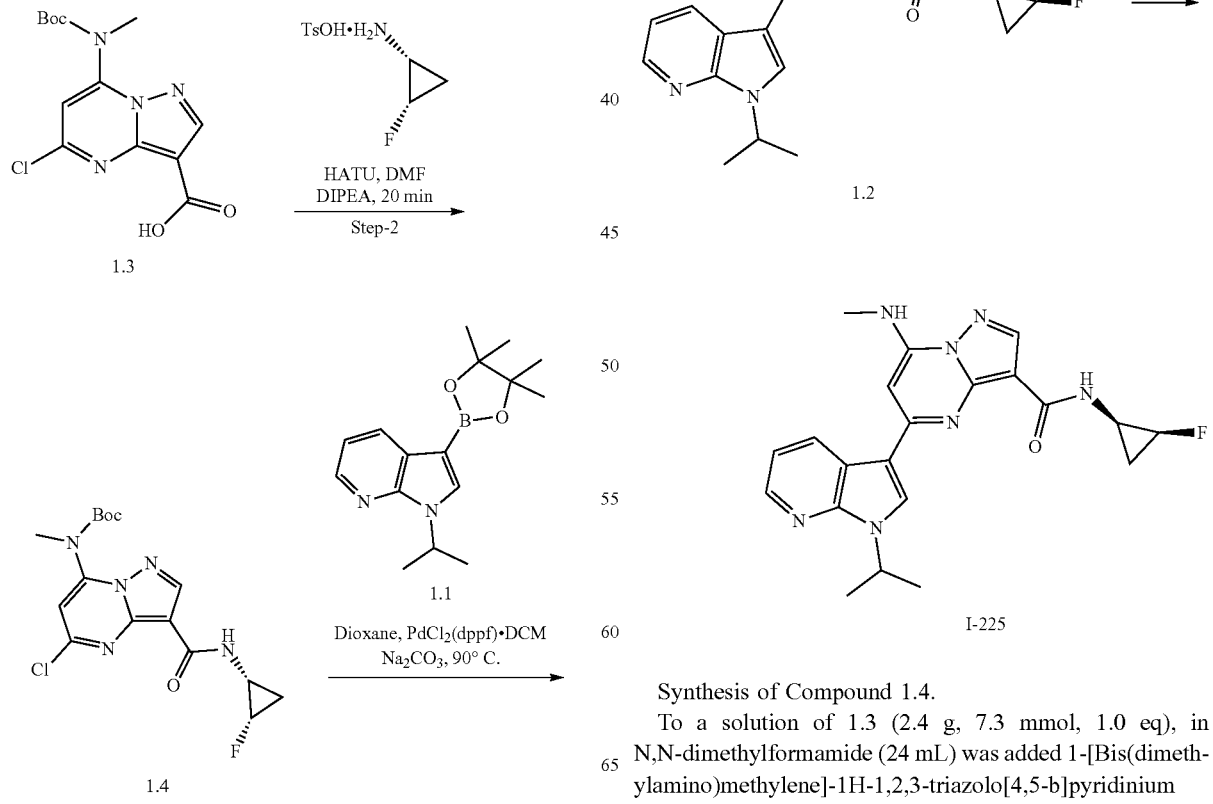

Synthesis of Compound 1.4.

To a solution of 1.3 (2.4 g, 7.3 mmol, 1.0 eq), in N,N-dimethylformamide (24 mL) was added 1-[Bis(dimethylamino)methylene]-1H-1,2,3-triazolo[4,5-b]pyridinium 3-oxid hexafluorophosphate (5.59 g, 14.7 mmol, 2.0 eq) and stirred at room temperature for 15 min. To this added diisopropylethylamine (3.81 mL, 21.9 mmol, 3.0 eq) followed by addition of (1R,2S)-fluorocyclopropylamine tosylate (1.80 g, 7.3 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain 1.4 (1.3 g, 46.42%). MS(ES): m/z 384.12 [M+H]$^+$.

Synthesis of Compound 1.2.

To a solution of 1 (0.100 g, 0.261 mmol, 1.0 eq) in dimethylformamide (5 mL) was added 1.1 (0.187 g, 0.652 mmol, 2.5 eq), sodium carbonate (0.069 g, 0.652 mmol, 2.5 eq) and [1,1'-Bis(diphenylphosphino)ferrocene]dichloropalladium(II) (0.021 g, 0.026 mmol, 0.1 eq), degassed for 10 min and stirred at 90° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 15% ethyl acetate in hexane as eluant to obtain pure 1.5 (0.054 g, 40.83%). MS(ES): m/z 508.57 [M+H]$^+$.

Synthesis of Compound I-225:

Compound was synthesized using general procedure C to obtain I-225 (0.035 g, 80.74%), MS (ES): m/z 408.54 [M+H]$^+$, LCMS purity: 100%, HPLC purity: 99.03%, CHIRAL HPLC purity: 100%, $^1$H NMR (DMSO-d$_6$, 400 MHZ): 8.73 (s, 1H), 8.68-8.66 (d, J=8 Hz, 1H), 8.41 (s, 1H), 8.40-8.39 (d, J=4 Hz, 1H), 8.36-8.35 (d, J=4 Hz, 1H), 8.27 (s, 1H), 7.28-7.25 (m, 1H), 6.77 (s, 1H), 5.23-5.18 (m, 1H), 5.05-4.89 (m, 1H), 3.13 (s, 3H), 3.10-3.09 (m, 1H), 1.59-1.57 (d, J=8 Hz, 6H), 1.34-1.27 (m, 1H), 1.11-1.04 (m, 1H).

Additional compounds prepared by substantially the same method, and their characterization data, are listed in the Table 63 below. The intermediate corresponding to 1.1 of the above scheme is listed for each compound.

108.4. Synthesis of 5-(5-chloro-1-isopropyl-1H-pyrrolo[2,3-b]pyridin-3-yl)-N-((1R,2S)-2-fluorocyclopropyl)-7-(methylamino)pyrazolo[1,5-a]pyrimidine-3-carboxamide (I-254)

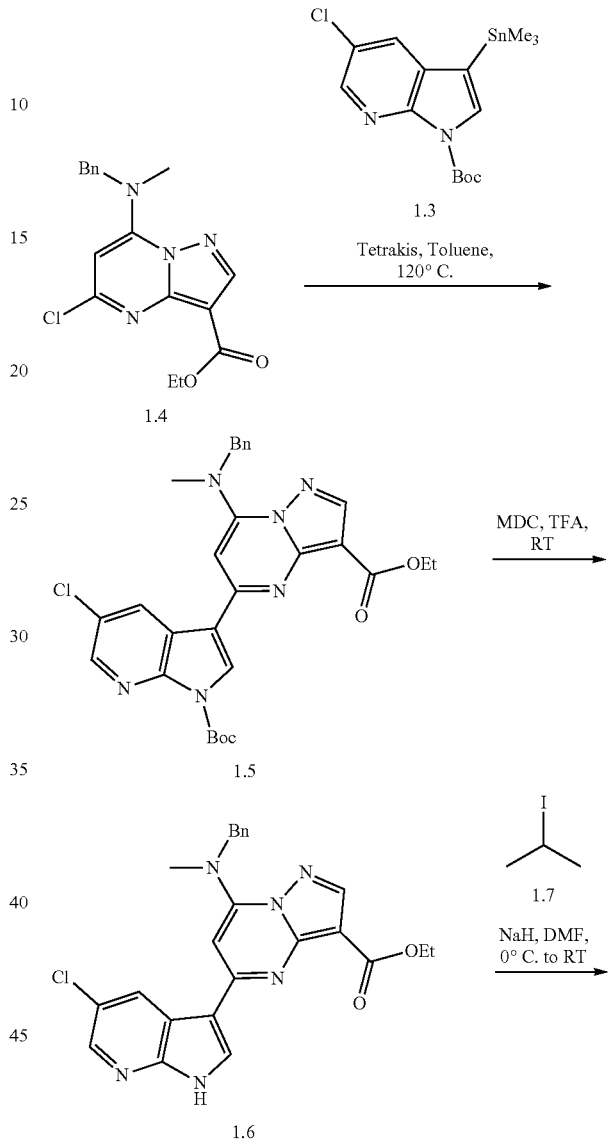

TABLE 63

| Compound | Intermediate | Characterization Data |
|---|---|---|
| I-257 | (5-methyl-1H-pyrrolo[2,3-b]pyridin-3-yl boronic acid pinacol ester structure) | MS (ES): m/z 422.50 [M + H]$^+$, LCMS purity: 100%, HPLC purity: 99.30%, CHIRAL HPLC purity: 100%, $^1$H NMR (DMSO-d$_6$, 400 MHZ): 8.62 (s, 1H), 8.42 (s, 1H), 8.39-8.37 (d, J = 8 Hz, 2H), 8.24-8.22 (d, J = 8 Hz, 2H), 6.72 (s, 1H), 5.18-5.11 (m, 1H), 5.03-4.84 (m, 1H), 3.11 (s, 3H), 3.06-3.03 (m, 1H), 2.47 (s, 3H), 1.56-1.55 (d, J = 4 Hz, 6H), 1.31-1.24 (m, 1H), 1.01-0.94 (m, 1H). |

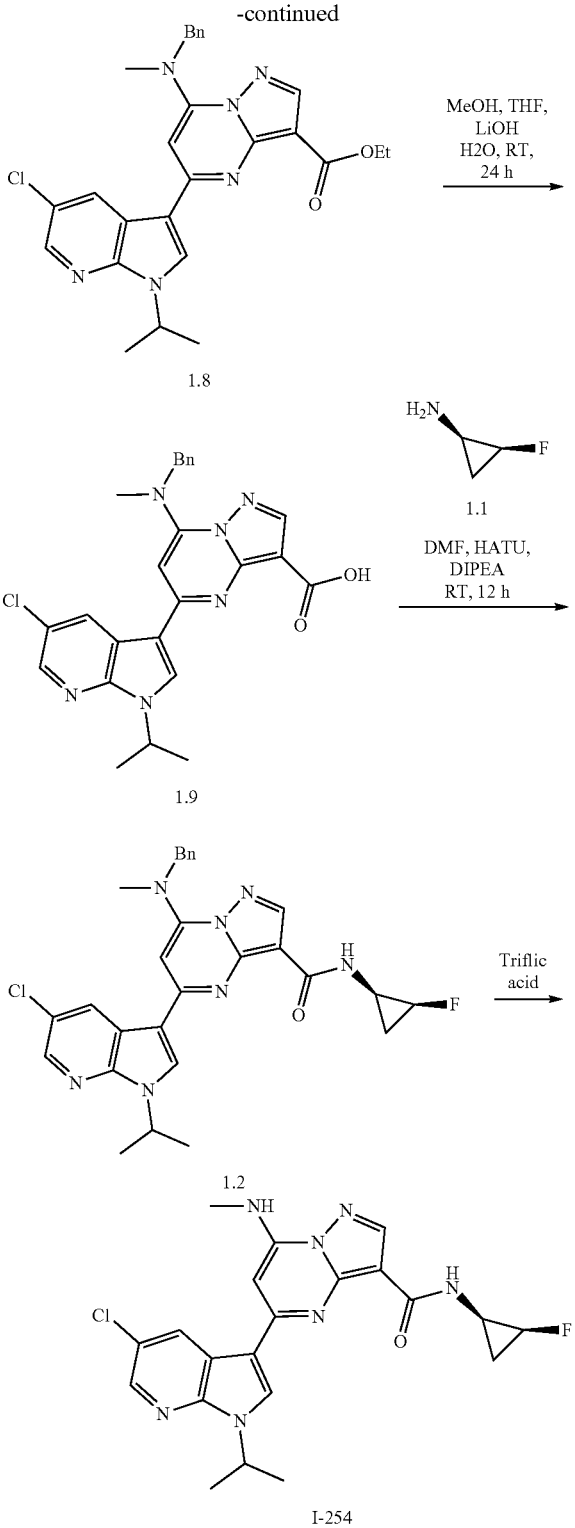

Synthesis of Compound 1.4.

Compound was synthesized using general procedure of core synthesis to obtain 1.4 (Yield: 45.00%). MS (ES): m/z 345.10 [M+H]+

Synthesis of Compound 1.5.

To a solution of 1.4. (0.500 g, 1.45 mmol, 1.0 eq) in toluene (10 mL), palladium-tetrakis(triphenylphosphine) (0.161 g, 0.14 mmol, 0.1 eq) was added. The reaction mixture was degassed for 10 min. under argon atmosphere, then 1.3 (0.800 g, 2.10 mmol, 1.5 eq) was added and reaction was stirred at 120° C. for 1 h. After completion of reaction, reaction mixture was filtered through celite-bed and was with ethyl acetate. Filtrate was concentrated under reduced pressure to obtain pure 1.5 (0.400 g, 49.17%). MS (ES): m/z 562.64 [M+H]+.

Synthesis of Compound 1.6.

Compound was synthesized using general procedure C to obtain pure 1.6 (0.320 g, 97.38%). MS(ES): m/z 461.92 [M+H]+.

Synthesis of Compound 1.8.

To a cooled solution of 1.6 (0.320 g, 0.695 mmol, 1 eq) in dimethylformamide (4 mL) was added sodium hydride (0.041 g, 1.04 mmol, 1.5 eq) followed by addition of 1.7 (0.130 g, 0.764 mmol, 1.1 eq) under nitrogen atm. The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 5% ethyl acetate in hexane to obtain pure 1.8 (0.300 g, 85.51%), MS(ES): m/z 504.00 [M+H]+.

Synthesis of Compound 1.9.

To a solution of 1.8 (0.300 g, 0.596 mmol, 1.0 eq), in tetrahydrofuran: methanol: water (6 mL, 1:1:1) was added lithium hydroxide (0.250 g, 5.96 mmol, 10 eq). The reaction was stirred at room temperature for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 1.4% methanol in dichloromethane to obtain pure 1.9 (0.220 g, 77.66%). MS(ES): m/z 475.95 [M+H]+.

Synthesis of Compound 1.2.

Compound was synthesized using general procedure of A to obtain 1.2 (0.063 g, 56.24%). MS (ES): m/z 533.02 [M+H]+

Synthesis of Compound I-254:

Mixture of 1.2 (0.063 g, 0.122 mmol, 1.0 eq) and triflic acid (1 mL) was allowed to stir at room temperature for 30 min. After completion of reaction, reaction mixture was transferred into saturated bicarbonate solution and product was extracted with dichloromethane. Organic layer was combined, dried over sodium sulphate and concentrated under reduced pressure to obtain crude material. This was further purified by trituration with diethyl ether to a obtain I-254 (0.025 g, 47.78%), MS (ES): m/z 442.46 [M+H]+, LCMS purity: 100%, HPLC purity: 96.90%, $^1$H NMR (DMSO-$d_6$, 400 MHZ): 8.81 (s, 1H), 8.63 (s, 1H), 8.40-8.39 (d, J=4 Hz, 2H), 8.31-8.30 (d, J=4 Hz, 1H), 8.27-8.26 (d, J=4 Hz, 1H), 6.76 (s, 1H), 5.18-5.11 (m, 1H), 4.99-4.82 (m, 1H), 3.12-3.10 (d, J=8 Hz, 3H), 3.02 (m, 1H), 1.57-1.55 (d, J=8 Hz, 6H), 1.30-1.25 (m, 1H), 1.05-0.99 (m, 1H).

108.5. Synthesis of N-((1R,2S)-2-fluorocyclopropyl)-7-(methylamino)-5-((2-oxo-1-(1,4-dioxaspiro 14.51 decan-8-yl)-1,2-dihydropyridin-3-yl)amino)pyrazolo[1,5-a]pyrimidine-3-carboxamide(I-415)

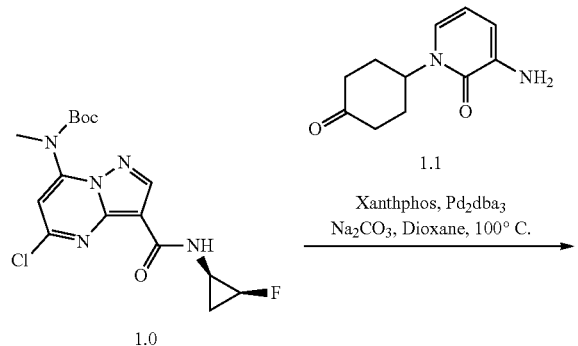
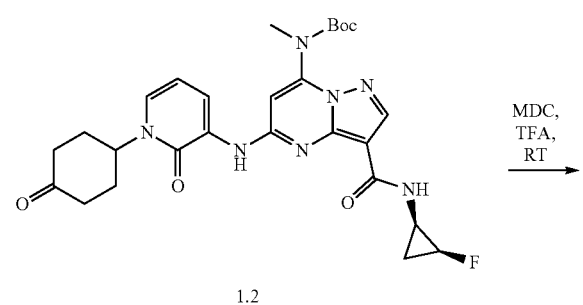
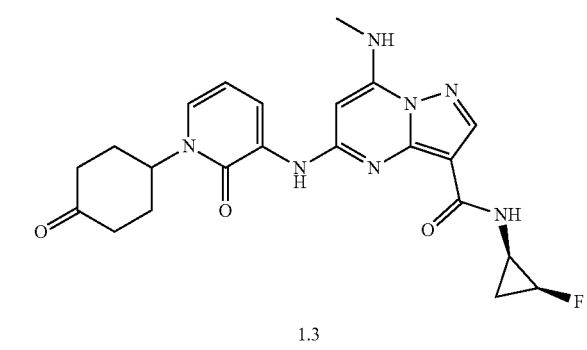
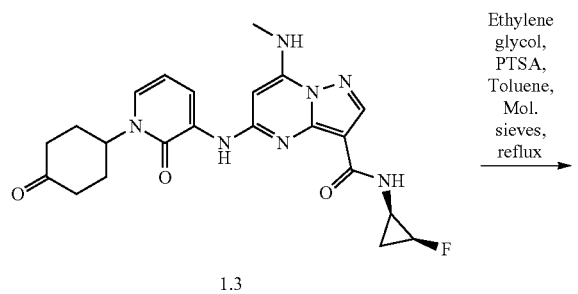
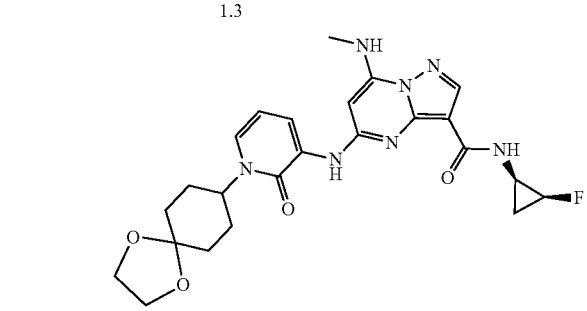

Synthesis of Compound 1.0:—
Compound was synthesized as per experimental protocol Example 19 of I-144.

Synthesis of Compound 1.1:—
Compound was synthesized according to the experimental protocols of the intermediates.

Synthesis of Compound 1.2:—
Compound was synthesized using general procedure of B synthesis to obtain 1.2 (Yield: 55.46%). MS (ES): m/z 554.24 [M+H]$^+$ Synthesis of Compound 1.3:—
Compound was synthesized using general procedure of C synthesis to obtain 1.3 (Yield: 97.66%). MS (ES): m/z 454.48 [M+H]$^+$ Synthesis of Compound I-415:—
To a solution of 1.3 (0.080 g, 0.17 mmol, 1.0 eq) in toluene was added ethylene glycol (0.021 g, 0.34 mmol, 2.0 eq), p-Toluene sulfonic acid (0.043 g, 0.25 mmol, 1.5 eq), followed by addition of molecular sieve (0.016 g). The reaction was stirred at 110° C. for 16 h. After completion of reaction, reaction mixture was concentrated under reduced pressure to obtain crude material. This was further purified by Preparative HPLC to obtain I-415 (0.050 g, Yield: 56.97%), MS (ES): m/z 498.26 [M+H]$^+$, LCMS purity: 100%, HPLC purity: 99.90%, CHIRAL HPLC: 100%, $^1$H NMR (DMSO-d$_6$, 400 MHZ): 8.86 (s, 1H), 8.24 (s, 1H), 8.13-8.11 (d, J=7.2 Hz, 1H), 7.95-7.93 (d, J=4.8 Hz, 1H), 7.80-7.79 (d, J=4.8 Hz, 1H), 7.37-7.36 (d, J=6.8 Hz, 1H), 6.29-6.25 (t, J=7.2 Hz, 1H), 6.23 (s, 1H), 4.99-4.82 (m, 2H), 3.95-3.89 (m, 4H), 2.92-2.90 (d, J=4.8 Hz, 4H), 1.89-1.70 (m, 8H), 1.28-1.18 (m, 2H), 0.91-0.82 (m, 2H).

108.6. Chiral Separation of I-365

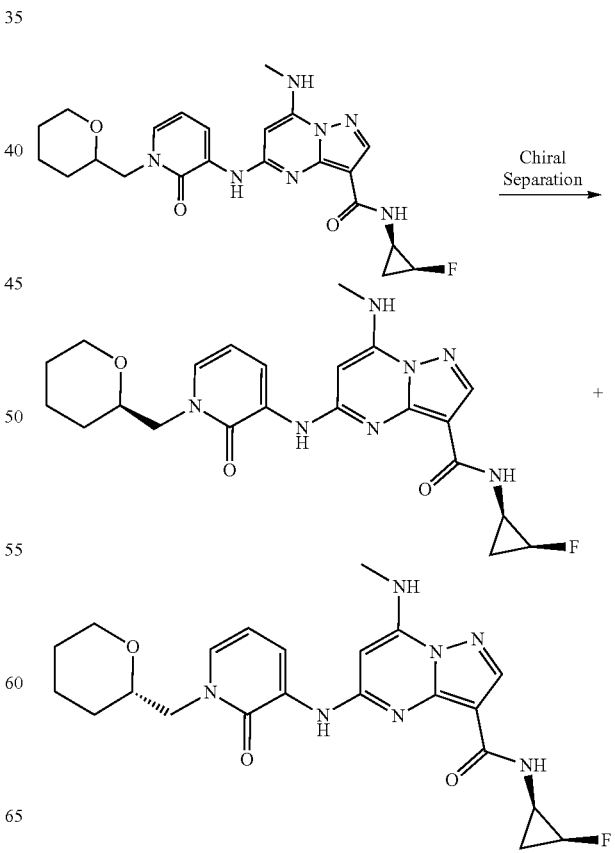

Synthesis of Compound I-427 & I-428.

Isomers of I-365 (0.09 g) were separated out using column (CHIRAL PAK AD-H 250×4.6 mm, 5 μM) in DEA as co-solvent with flow rate of 4 mL/min. to get pure fraction-1 (FR-a) and fraction-2 (FR-b). FR-a was concentrated under reduced pressure at 30° C. to afford pure FR-a (0.04 g). MS(ES): m/z 456.1 [M+H]$^+$, LCMS purity: 100%, HPLC purity: 100%, Chiral HPLC purity: 98.83%, $^1$H NMR (DMSO-d$_6$, 400 MHZ): 8.85 (s, 1H), 8.23 (s, 1H), 8.13-8.11 (d, J=7.2 Hz, 1H), 7.93-7.92 (d, J=4.8 Hz, 1H), 7.81-7.80 (d, J=4.4 Hz, 1H), 7.27-7.25 (d, J=6.8 Hz, 1H), 6.22-6.19 (t, J=6.8 Hz, 2H), 5.77 (s, 1H), 4.97-4.78 (m, 1H), 4.14-4.10 (d, J=13.2 Hz, 1H), 3.91-3.84 (m, 2H), 3.67-3.61 (m, 1H), 3.35-3.26 (m, 1H), 2.97-2.89 (m, 4H), 1.79 (bs, 1H), 1.61-1.58 (d, J=12.4 Hz, 1H), 1.46 (bs, 3H), 1.28-1.18 (m, 2H), 0.91-0.83 (m, 1H).

FR-b was concentrated under reduced pressure at 30° C. to afford pure FR-b (0.040 g). MS(ES): m/z 456.32 [M+H]$^+$, LCMS purity: 100%, HPLC purity: 99.43%, Chiral HPLC purity: 95.91%, $^1$H NMR (DMSO-d$_6$, 400 MHZ): 8.85 (s, 1H), 8.23 (s, 1H), 8.13-8.11 (d, J=7.2 Hz, 1H), 7.93-7.92 (d, J=4.8 Hz, 1H), 7.82-7.81 (d, J=4.4 Hz, 1H), 7.27-7.26 (d, J=6.8 Hz, 1H), 6.22-6.19 (t, J=6.8 Hz, 2H), 5.77 (s, 1H), 4.96-4.79 (m, 1H), 4.14-4.10 (d, J=13.2 Hz, 1H), 3.91-3.84 (m, 2H), 3.66-3.64 (m, 1H), 3.35-3.24 (m, 1H), 2.97-2.89 (m, 4H), 1.79 (bs, 1H), 1.61-1.58 (d, J=12.4 Hz, 1H), 1.45 (bs, 3H), 1.27-1.20 (m, 2H), 0.90-0.83 (m, 1H).

Additional compounds prepared by substantially the same method, and their characterization data, are listed in the Table 64 below.

TABLE 64

| Compound | Isomers | Characterization Data |
|---|---|---|
| I-450 | I-485<br>I-486 | FR-a: MS(ES): m/z 456.22 [M + H]$^+$, LCMS purity: 100%, HPLC purity: 99.75%, CHIRAL HPLC purity: 100%, $^1$H NMR (DMSO-d$_6$, 400 MHZ): 8.91 (s, 1H), 8.23 (s, 1H), 8.13 (bs, 1H), 7.93 (s, 1H), 7.80 (s, 1H), 7.39 (bs, 1H), 6.28(s, 1H), 6.24 (s, 1H), 4.99 (bs, 1H), 4.06 (s, 1H), 3.18 (s, 3H), 2.98 (bs, 1H), 2.89 (s, 2H), 2.11 (bs, 2H), 1.84-1.67 (m, 4H), 1.12-1.06 (m, 2H), 0.89-0.84 (m, 2H).<br>FR-b: MS(ES): m/z 456.22 [M + H]$^+$, LCMS purity: 100%, HPLC purity: 100%, CHIRAL HPLC purity: 99.81%, $^1$H NMR (DMSO-d$_6$, 400 MHZ): 8.91 (s, 1H), 8.23 (s, 1H), 8.13 (bs, 1H), 7.93 (s, 1H), 7.80 (s, 1H), 7.39 (s, 1H), 6.29 (s, 1H), 6.24 (s, 1H), 4.99 (bs, 1H), 4.06 (s, 1H), 3.18 (s, 3H), 2.98 (bs, 2.89 (s, 3H), 2.11 (bs, 2H), 1.84-1.67 (m, 4H), 1.04 (bs, 2H), 0.90-0.85 (m, 2H). |
| I-452 | I-517<br>I-518 | FR-a: MS(ES): m/z 437.45 [M + H]$^+$, LCMS purity: 100%, HPLC purity: 100% CHIRAL HPLC: 100%, $^1$H NMR (DMSO-d$_6$, 400 MHZ): 8.75-8.73 (d, J = 6.8 Hz, 1H), 8.69 (s, 1H), 8.58 (s. 1H), 8.50 (s, 1H), 8.16 (s, 1H), 7.40 (s, 1H), 6.88 (s, 1H), 5.79 (s, 1H), 5.04-4.88 (m, 1H), 4.21 (s, 2H), 4.08-3.97 (m, 2H), 3.12-3.06 (m, 4H), 1.29-1.23 (m, 2H), 1.01-0.95 (m, 2H)<br>FR-b: MS(ES): m/z 437.45 [M + H]$^+$, LCMS purity : 100%, HPLC purity: 99.61% CHIRAL HPLC: 98.04%, $^1$H NMR (DMSO-d$_6$, 400 MHZ): 8.74-8.72 (d, J = 7.6 Hz, 1H), 8.69-8.68 (d, J = 3.2 Hz, 1H), 8.58-8.56 (d, J = 4.8 Hz, 1H), 8.50 (s, 1H), 8.16-8.15 (d, J = 4.0 Hz, 1H), 7.41-7.38 (m, 2H), 6.87 (s, 1H), 5.79 (s, 1H), 5.04-4.87 (m, 1H), 4.23-4.19 (m, 2H), 4.09-4.06 (m, 1H), 4.01-3.96 (m, 1H), 3.12-3.11 (d, J = 4.8 Hz, 3H), 1.33-1.23 (m, 2H), 1.01-0.95 (m, 2H). |
| I-506 | I-535<br>I-536 | FDR-a: MS (ES): m/z 455.40 [M + H]$^+$, LCMS purity: 100%, HPLC purity: 99.13% CHIRAL HPLC: 99.51%, $^1$H NMR (DMSO-d$_6$, 400 MHZ): 8.86 (s, 1H), 8.23 (s, 1H), 8.13-8.11 (d, J = 6.8 Hz, 1H), 7.92-7.91 (d, 7 = 4.4 Hz, 1H), 7.80-7.79 (d, J = 4.4 Hz, 1H), 7.54-7.53 (d, J = 6.8 Hz, 1H), 6.28-6.23 (m, J = 7.2 Hz, 2H), 4.96-4.94 (t, J = 5.6 Hz, 1H), 3.00-2.96 (t, 1H), 2.91-2.90 (d, J = 4.4 Hz, 3H), 2.79-2.78 (d, J = 7.6 Hz, 2H), 2.70-2.67 (d, J = 10.8 Hz, 2H), 2.21-2.19 (m, 2H), 2.04-1.98 (m, 1H), 1.77-1.61 (m, 3H), 1.27-1.09 (m, 2H), 0.89-0.83 (m, 2H).<br>FR-b: MS(ES): m/z 455.40 [M + H]$^+$, LCMS purity: 100%, HPLC purity : 98.54% CHIRAL HPLC: 96.96%, $^1$H NMR (DMSO-d$_6$, 400 MHZ): 8.87 (s, 1H), 8.24 (s, 1H), 8.14-8.12 (d, J = 7.2 Hz, 1H), 7.93-7.92 (d, J = 4.8 Hz, 1H), 7.81-7.80 (d, J = 4.8 Hz, 1H), 7.55-7.54 (d, J = 6.4 Hz, 1H), 6.29-6.24 (m, 2H), 4.96-4.94 (t, J = 5.6 Hz, 1H), 3.00-2.97 (t, J = 8 Hz 1H), 2.92-2.91 (d, J = 4.4 Hz, 3H), 2.81-2.79 (d, J = 7.6 Hz, 1H), 2.73-2.71 (d, J = 7.2 Hz, 1H), 2.21-2.19 (m, 2H), 2.05-2.00 (m, J = 10.4 Hz, 2H), 1.79-1.62 (m, J = 6 Hz, 4H), 1.28-1.05 (m, 2H), 0.92-0.82 (m, 2H) |

TABLE 64-continued

| Compound | Isomers | Characterization Data |
| --- | --- | --- |
| I-507 | I-537<br>I-538 | FR-a: MS(ES): m/z 456.50 [M + H]⁺, LCMS purity: 99.59%, HPLC purity: 99.67%, Chiral HPLC purity: 100%, NMR (DMSO-$d_6$, 400 MHZ): 8.86 (s, 1H), 8.23 (s, 1H), 8.14-8.13 (d, J = 6.8 Hz, 1H), 7.92-7.90 (d, J = 4.8 Hz, 1H), 7.82-7.81 (d, J = 4.4 Hz, 1H), 7.37-7.35 (d, J = 7.2 Hz, 1H), 6.25-6.22 (t, J = 7.2 Hz, 2H), 5.09-5.03 (m, 1H), 3.89 (s, 1H) 3.02 (s, 3H), 3.00-2.91 (m, 1H), 2.91-2.90 (d, J = 4.8 Hz, 3H), 1.96-1.82 (m, 3H), 1.65-1.63 (d, J = 8 Hz, 2H), 1.25-1.18 (m, 2H), 0.89-0.83 (m, 2H).<br>FR-b: MS(ES): m/z 456.50 [M + H]⁺ LCMS purity: 99.04%, HPLC purity: 99.19%, Chiral HPLC purity: 99.062%, NMR (DMSO-$d_6$, 400 MHZ): 8.86 (s, 1H), 8.23 (s, 1H), 8.15-8 13 (d, J = 7.2 Hz, 1H), 7.92-7.90 (d, J = 4.8 Hz, 1H), 7.82-7.81 (d, J = 4.8 Hz, 1H), 7.37-7.35 (d, J = 6 Hz, 1H), 6.25-6.22 (t, J = 7.2 Hz, 2H), 5.07-5.03 (m, 1H), 3.89 (s, 1H) 3.03 (s, 3H), 3.00-2.91 (m, 1H), 2.91-2.90 (d, J = 4.8 Hz, 3H), 1.98-1.82 (m, 3H), 1.65-1.63 (d, J = 8.4 Hz, 2H), 1.28-1.18 (m, 2H), 0.92-0.89 (m, 2H). |
| I-521 | I-558<br>I-559 | FR-a: MS(ES): m/z 460.22 [M + H]⁺, LCMS purity: 99.05%, HPLC purity: 98.61%, CHIRAL HPLC purity: 96.12%. ¹H NMR (DMSO-$d_6$, 400 MHZ): 9.11 (s, 1H), 8.29 (s, 1H), 8.24-8.23 (d, J = 2.8 Hz, 1H), 8.04-8.03 (d, J = 4.8 Hz, 1H), 7.74-7.73 (d, J = 4.4 Hz, 1H), 7.68-7.66 (m, 1H), 6.36 (s, 1H), 4.90-4.86 (m, 2H), 4.74-4.71 (bs, 1H) 3.84-3.79 (m, 2H), 3.62-3.57 (t, J = 10 Hz, 1H), 3.46-3.44 (t, J = 2.4 Hz, 1H), 2.92-2.91 (d, J = 4.8 Hz, 3H), 2.09-2.06 (m, 1H), 1.96 (bs, 1H), 1.25-1.15 (m, 1H), 1.06-1.04 (d, J = 6 Hz, 3H).<br>FR-b: MS(ES): m/z 460.27 [M + H]⁺, LCMS purity: 100%, HPLC purity: 100%, CHIRAL HPLC purity: 100%, ¹H NMR (DMSO-$d_6$, 400 MHZ): 9.11 (s, 1H), 8.29 (s, 1H), 8.24-8.23 (d, J = 2.8 Hz, 1H), 8.04-8.03 (d, J = 4.8 Hz, 1H), 7.74-7.73 (d, J = 4.4 Hz, 1H), 7.68-7.66 (m, 1H), 6.36 (s, 1H), 4.89-4.86 (m, 1H), 4.74-4.72 (bs, 1H) 3.84-3.82 (m, 2H), 3.62-3.57 (t, J = 10 Hz, 1H), 3.49-3.44 (t, J = 11.2 Hz, 1H), 2.92-2.91 (d, J = 4.8 Hz, 3H), 2.09-2.06 (m, 1H), 1.96 (bs, 1H), 1.25-1.15 (m, 1H), 1.06-1.04 (d, J = 6 Hz, 3H). |
| I-522 | I-562<br>I-563 | FR-a: MS(ES): m/z 426.32 [M + H]⁺, LCMS purity: 98.71%, HPLC purity: 99.84%, CHIRAL HPLC purity: 100%, ¹H NMR (DMSO-$d_6$, 400 MHZ): 9.88 (s, 1H), 8.25 (s, 1H), 8.09 (s, 1H), 7.98 (s, 1H), 7.69-7.65 (d, J = 7.6 Hz, 1H), 7.50 (s, 1H), 6.96-6.94 (d, J = 7.2 Hz, 1H), 6.73 (s, 1H), 4.93-4.77 (m, 1H), 4.03-01 (d, J = 9.2 Hz, 1H), 3.92-3.89 (d, J = 10 Hz, 1H), 3.55-3.50 (t, J = 10.4 Hz, 1H), 2.98-2.94 (m, 3H), 1.92 (bs, 2H), 1.68 (bs, 2H), 1.35-1.24 (m, 2H). 1.23-0.86 (m, 3H).<br>FR-b: MS(ES): m/z 426.32 [M + H]⁺, LCMS purity: 97.18%, HPLC purity: 96.86%, CHIRAL HPLC purity: 97.96%, ¹H NMR (DMSO-$d_6$, 400 MHZ): 9.88 (s, 1H), 8.26 (s, 1H), 8.09-08 (d, J = 4 Hz, 1H), 7.91 (s, 1H), 7.69-7.65 (t, J = 7.6 Hz, 1H), 7.50-7.48 (d, J = 7.6 Hz, 1H), 6.96-6.95 (d, J = 7.2 Hz, 1H), 6.73 (s, 1H), 4.93-4.77 (m, 1H), 4.03-01 (d, J = 9.6 Hz, 1H), 3.92-3.89 (d, J = 10.4 Hz, 1H), 3.56-3.51 (t, J = 10.8 Hz, 1H), 2.99-2.93 (m, 3H), 1.92 (bs, 2H), 1.68 (bs, 2H), 1.35-1.24 (m, 2H), 1.23-0.87 (m, 3H). |
| I-693 | I-772<br>I-773 | FR-a: MS(ES): m/z 476.47 [M + H]⁺, LCMS purity: 100%, HPLC purity: 98.75%, CHIRAL HPLC purity: 100%, ¹H NMR (DMSO-$d_6$, 400 MHZ): 9.06 (s, 1H), 8.28 (s, 1H), 8.24-8.23 (d J = 4 Hz, 2H), 8.04-8.03 (d, J = 4 Hz , 1H), 7.77-7.76 (d, J = 4 Hz, 1H), 7.70 (d, J = 2.4 Hz, 1H), 6.33 (s, 1H), 4.91-4.75 (m, 1H), 3.85-3.80 (t, J = 6.4 Hz, 2H), 3.68-3.63 (m, 1H), 3.51-3.47 (t, J = 12 Hz, 1H), 2.92-2.91 (d, J = 4 Hz, 3H), 2.88-2.86 (m, 1H), 2.13-2.10 (m, 1H), 1.96 (s, 1H), 1.76-1 70 (m, 2H), 1.25-0.95 (m, 2H).<br>FR-b: MS(ES): m/z 476.57 [M + H]⁺, LCMS purity: 99.50%, HPLC purity: 100%, CHIRAL HPLC purity: 98.25%, ¹H NMR (DMSO-$d_6$, 400 MHZ): 9.06 (s, 1H), 8.28 (s, 1H), 8.24-8.23 (d J = 4 Hz, 2H), 8.04-8.03 (d, J = 4 Hz, 1H), 7.77-7.76 (d, |

TABLE 64-continued

| Compound | Isomers | Characterization Data |
| --- | --- | --- |
| | | J = 4 Hz, 1H), 7.70 (d, J = 2.4 Hz, 1H), 6.33 (s, 1H), 4.91-4.75 (m, 1H), 3.85-3.80 (t, J = 6.4 Hz, 2H), 3.68-3.63 (m, 1H), 3.51-3.47 (t, J = 12 Hz, 1H), 2.92-2.91 (d, 3H), 2.88-2.86 (m, 1H), 2.13-2.10 (m, 1H), 1.96 (s, 1H), 1.76-1.70 (m, 2H), 1.25-0.95 (m, 2H). |
| I-795 (Chiral separation when methylamino at position 7 is protected by Boc, followed by removal of Boc) | I-839 I-840 | FR-a: MS (ES): m/z 470.51 [M + H]+, LCMS purity: 100%, HPLC purity: 99.10%, Chiral HPLC: 98.68 $^1$H NMR (DMSO-d$_6$, 400 MHZ): 8.86 (s, 1H), 8.25 (s, 1H), 8.13-8.12 (d, J = 4 Hz, 1H), 7.95-7.94 (d, J = 4 Hz, 1H), 7.82-7.81 (d, J = 4 Hz, 1H), 6.31-6.29 (t, J = 8.4 Hz, 1H), 6.24 (s, 1H), 4.86-4.80 (m, 2H), 3.33-3.31 (d, = 8.2 Hz, 1H), 3.28-3.26 (d, J = 8.4 Hz, 3H), 3.01-2.98 (m, 1H), 2.93-2.92 (d, J = 4 Hz, 3H), 2.19-2.17 (d, J = 8 Hz, 1H), 2.06-2.04 (d, J = 8 Hz, 1H), 188-1 85 (d, J = 12.6 Hz, 1H), 1.77-1.74 (d, J = 13 Hz, 1H), 1.67-1.55 (m, 1H), 1.46-1.35 (m, 2H), 1.29-1.10 (m, 4H)<br>FR-b: MS(ES): m/z 470.50 [M + H]+, LCMS purity: 100%, HPLC purity: 100% Chiral HPLC: 96.04%, $^1$H NMR (DMSO-d$_6$, 400 MHZ): 8.86 (s, 1H), 8.25 (s, 1H), 8.13-8.12 (d, J = 4 Hz, 1H), 7.95-7.94 (d, J = 4 Hz, 1H), 7.82-7.81 (d, J = 4 Hz, 1H), 6.31-6.29 (t, J = 8.4 Hz, 1H), 6.24 (s, 1H), 4.86-4.80 (m, 2H), 3.33-3.31 (d, = 8.2 Hz, 1H), 3.28-3.26 (d, J = 8.4 Hz, 3H), 3.01-2.98 (m, 1H), 2.93-2.92 (d, J = 4 Hz, 3H), 2.19-2.17(d, J = 8 Hz, 1H), 2.06-2.04 (d, J = 8 Hz, 1H), 1.88-1.85 (d, J = 12.6 Hz, 1H), 1.77-1.74 (d, J = 13 Hz, 1H), 1.67-1.55 (m, 1H), 1.46-1.35 (m, 2H), 1.29-1.10 (m, 4H) |
| I-759 | I-853 I-854 | FR-a: MS(ES): m/z 489.42 [M + H]+, LCMS purity: 100%, HPLC purity: 97.39%, CHIRAL HPLC purity: 99.65%, $^1$H NMR (DMSO-d$_6$, 400 MHZ): 9.04 (s, 1H), 8.27 (s, 1H), 8.23-8.22 (d, J = 2 Hz, 1H), 8.03-8.02 (d, J = 4.8 Hz. 1H), 7.77 (bs, 2H), 6.32 (bs, 1H), 4.90 (bs, 1H), 4.74 (bs, 1H), 2.92-2.91 (d, J = 4.8 Hz, 4H), 2.23 (s, 5H), 2.10 (s, 4H), 1.63 (bs, 2H), 1.24-1.18 (m, 2H).<br>FR-b: MS(ES): m/z 489.42 [M + H]+, LCMS purity: 100%, HPLC purity: 99.38%, CHIRAL HPLC purity: 100%, $^1$H NMR (DMSO-d$_6$, 400 MHZ): 9.03 (s, 1H), 8.27 (s, 1H), 8.22 (s, 2H), 8.03-8.02 (d, J = 4.8 Hz, 1H), 7.79-7.77 (t, J = 5.6 Hz, 2H), 6.32 (s, 1H), 4.91 (bs, 2H), 4.75 (bs, 1H), 2.92-2.91 (d, J = 4.4 Hz, 4H), 2.77-2.76 (d, J = 7.2 Hz, 1H), 2.63 (bs, 2H), 2.30 (s, 1H), 2.23 (s, 3H), 2.12-2.10 (d, J = 8 Hz, 1H), 1.63 (bs, 1H), 1.24-1.14 (m, 2H). |
| I-849 | I-900 I-901 | FR-a: MS(ES): m/z 487.71 [M + H]+, LCMS purity: 100%, HPLC purity: 99.01%, CHIRAL HPLC purity: 99.47%, $^1$H NMR (DMSO-d$_6$, 400 MHZ): 8.89 (s, 1H), 8.24 (s, 1H), 8.15-8.13 (d, J = 7.2 Hz, 1H), 7.95-7.93 (d, J = 5.2 Hz, 1H), 7.82-7.81 (d, J = 4.4 Hz, 1H), 7.57-7.55 (d, J = 6.4 Hz, 1H), 6.29-6.25 (m, 2H), 4.97-4.94 (m, 1H), 4.83-4.81 (m, 1H), 4.63-4.61 (t, J = 4.8 Hz, 1H), 4.52-4.49 (t, J = 4.8 Hz, 1H), 3.00-2.84 (m, 6H), 2.75-2.72 (t, J = 4.8 Hz, 1H), 2.68-2.65 (t, J = 4.8 Hz, 1H), 2.38-2.33 (m, 1H), 2.22-2.16 (t, J = 6.8 Hz, 1H), 1.81-1.74 (m, 2H), 1.65 (s, 1H), 1.26-1.19 (m, 1H), 0.92-0.89 (m, 2H).<br>FR-b: MS(ES): m/z 487.36 [M + H]+, LCMS purity: 100%, HPLC purity: 99%, CHIRAL HPLC purity: 98.32%, $^1$H NMR (DMSO-d$_6$, 400 MHZ): 8.89 (s, 1H), 8.24 (s, 1H), 8.15-8.13 (d, J = 7.2 Hz, 1H), 7.95-7.93 (d, J = 5.2 Hz, 1H), 7.82-7.80 (d, J = 4.4 Hz, 1H), 7.57-7.55 (d, J = 6.4 Hz, 1H), 6.30-6.25 (m, 2H), 4.96-4.95 (m, 1H), 4.81-4.80 (m, 1H), 4.63-4.61 (t, J = 4.8 Hz, 1H), 4.51-4.49 (t, J = 4.8 Hz, 1H), 3.01-2.83 (m, 6H), 2.75-2.72 (t, J = 4.8 Hz, 1H), 2.68-2.65 (t, J = 4.8 Hz, 1H), 2.38-2.33 (m, 1H), 2.22-2.16 (t, J = 6.8 Hz, 1H), 1.81-1.77 (m, 2H), 1.66 (s, 1H), 1.29-1.19 (m, 1H), 0.92-0.86 (m, 2H). |
| I-916 | I-998 I-999 | FR-a: MS(ES): m/z 428.47 [M + H]+, LCMS purity: 99.47%, HPLC purity: 98.57%, CHIRAL HPLC purity: 100%, $^1$H NMR (DMSO-d$_6$, 400 MHZ): 8.90 (s, 1H), 8.24 (s, 1H), 8.15-8 13 (d, J = 8 Hz, 1H), 7.95-7.94 (d, J = 4 Hz, 1H), 7.83-7.82 (d, J = 4 Hz, 1H), 7.49-7.47 (d, J = 8 Hz, 1H), 6.33-6.31 (t, J = 8Hz, 1H), 6.25 (s, 1H), 4.97-4.90 (m, 2H), 4.39- |

TABLE 64-continued

| Compound | Isomers | Characterization Data |
|---|---|---|
| | | 4.37 (t, J = 8 Hz, 1H), 2.99 (s, 1H), 2.92-2.90 (d, J = 8 Hz, 3H), 2.14-2.12 (d, J = 8 Hz, 2H), 1.62 (s, 2H), 1.35-1.24 (m, 3H).<br>FR-b: MS(ES): m/z 428.47 [M + H]$^+$, LCMS purity: 99.15%, HPLC purity: 98.39%, CHIRAL HPLC purity: 98.04%, $^1$H NMR (DMSO-d$_6$, 400 MHZ): 8.90(s, 1H), 8.24 (s, 1H), 8.14-8.13 (d, J = 4 Hz, 1H), 7.93 (s, 1H), 7.81 (s, 1H), 7.46 (s, 1H), 6.30 (s, 1H), 6.24 (s, 1H), 4.94-4.92 (m, J = 8 Hz, 2H), 4.36 (s, 1H), 2.99 (s, 1H), 2.90 (s, 3H), 2.13-2.11 (d, J = 8 Hz, 2H), 1.62 (s, 2H), 1.35-1.24 (m, 3H). |
| I-997 | I-1021<br>I-1022 | FR-a: MS(ES): m/z 442.31 [M + H]$^+$, LCMS purity: 100%, HPLC purity: 98.77%, CHIRAL HPLC purity: 100%, $^1$H NMR (DMS0-d$_6$, 400 MHZ): 8.91 (s, 1H), 8.24 (s, 1H), 8.16-8.14 (d, J = 8 Hz, 1H), 7.95-7.94 (d, J = 4 Hz, 1H), 7.80-7.78 (d, J = 8 Hz, 1H), 7.57-7.55 (d, J = 8 Hz, 1H), 6.34-6.32 (t, J = 8 Hz, 1H), 6.26 (s, 1H), 5.20-5.14 (m, 1H), 4.99-484 (m, 1H), 4.27-4.21 (m, 1H), 3.19-3.17 (d, J = 8 Hz, 3H), 3.02-2.98 (m, 1H), 2.92-2.90 (d, J = 8 Hz, 3H), 2.21-2.14 (m, 2H), 1.84-1.82 (t, J = 8 Hz, 1H), 1.30-1.18 (m, 1H), 1.17-1.15 (d, J = 8 Hz, 1H), 0.94-0.88 (m, 1H).<br>FR-b: MS(ES): m/z 442.31 [M + H]$^+$, LCMS purity: 100%, HPLC purity: 98.91%, CHIRAL HPLC purity: 98.29%, $^1$H NMR (DMSO-d$_6$, 400 MHZ): 8.91 (s, 1H), 8.24 (s, 1H), 8.16-8.14 (d, J = 8 Hz, 1H), 7.95-7.94 (d, J = 4 Hz, 1H), 7.80-7.78 (d, J = 8 Hz, 1H), 7.57-7.55 (d, J = 8 Hz, 1H), 6.34-6.32 (t, J = 8 Hz, 1H), 6.26 (s, 1H), 5.19-5.14 (m, 1H), 4.99-4.82 (m, 1H), 4.27-4.21 (m, 1H), 3.19-3.17 (d, J = 8 Hz, 3H), 3.02-2.98 (m, 1H), 2.92-2.90 (d, J = 8 Hz, 3H), 2.21-2.14 (m, 2H), 1.84-1.82 (t, J = 8 Hz, 1H), 1.30-1.18 (m, 1H), 1.17-1.15 (d, J = 8 Hz, 1H), 0.94-0.88 (m, 1H). |
| I-983 (Chiral separation when methylamino at position 7 is protected by Boc, followed by removal of Boc) | I-1029<br>I-1030 | FR-a: MS(ES): m/z 456.52 [M + H]$^+$, LCMS purity: 100%, HPLC purity: 97.18%, Chiral HPLC: 100%, $^1$H NMR (DMSO-d$_6$, 400 MHZ): 8.84 (s, 1H), 8.24 (s, 1H), 8.12-8.10 (d, J = 6.8 Hz, 1H), 7.93-7.92 (d, J = 4.4 Hz, 1H), 7.82-7.81 (d, J = 4.8 Hz, 1H), 7.42-7.41 (d, J = 6.0 Hz, 1H), 6.28-6.24 (m, 2H), 5.31-5.25 (m, 1H), 4.98-4.81 (m, 1H), 4.69-4.68 (s, 1H), 4.15 (s, 1H), 3.01-2.98 (m, 1H), 2.93-2.91 (d, J = 4.8 Hz, 3H), 1.70-1.47 (m, 2H), 1.30-1.21 (m, 4H), 0.95-0.85 (m, 4H).<br>FR-b: MS (ES): m/z 456.57 [M + H]$^+$, LCMS purity : 96.82%, HPLC purity : 97.61%, Chiral HPLC: 95.75%, $^1$H NMR (DMSO-d$_6$, 400 MHZ): 8.84 (s, 1H), 8.24 (s, 1H), 8.12-8.10 (d, J = 6.8 Hz, 1H), 7.93-7.92 (d, J = 4.4 Hz, 1H), 7.82-7.81 (d, J = 4.8 Hz, 1H), 7.42-7.41 (d, J = 6.0 Hz, 1H), 6.28-6.24 (m, 2H), 5.31-5.25 (m, 1H), 4.98-4.81 (m, 1H), 4.69-4.68 (s, 1H), 4.15 (s, 1H), 3.01-2.98 (m, 1H), 2.93-2.91 (d, J = 4.8 Hz, 3H), 1.70-1.47 (m, 2H), 1.30-1.21 (m, 4H), 0.95-0.85 (m, 4H). |
| I-912 | I-1040<br>I-1041 | FR-a: MS(ES): m/z 494.72 [M + H]$^+$, LCMS purity: 99.07%, HPLC purity: 98.06%, CHIRAL HPLC purity: 100%, $^1$H NMR (DMSO-d$_6$, 400 MHZ): 8.70-8.69 (d, J = 4.0 Hz, 1H), 8.22-8.18 (m, 2H), 7.94-7.83 (m, 3H), 6.98-6.95 (m, 1H), 5.90-5.89 (m, 1H), 5.14 (s, 1H), 4.86-4.70 (m, 1H), 3.07 (s, 1H), 2.94-2.93 (d, J = 4.0 Hz, 3H) 2.89 (s, 1H), 2.75-2.72 (s, 1H), 2.69-2.63 (m, 4H), 2.24-2.23 (m, 1H), 2.10-2.02 (m, 2H), 1.74 (s, 1H), 1.51-1 46 (m, 2H) 1.18-1.12 (m, 1H) 0.72-0.66 (m, 1H)<br>FR-b: MS(ES): m/z 494.56 [M + H]$^+$, LCMS purity: 100%, HPLC purity: 99.14%, CHIRAL HPLC purity: 99.19%, $^1$H NMR (DMSO-d$_6$, 400 MHZ): 8.70-8 69 (d, J = 4.0 Hz, 1H), 8.22-8.18 (m, 2H), 7.94-7.83 (m, 3H), 6.98-6.95 (m, 1H), 5.90-5.89 (m, 1H), 5.14 (s, 1H), 4.86-4.70 (m, 1H), 3.07 (s, 1H), 2.94-2.93 (d, J = 4.0 Hz, 3H) 2.89 (s, 1H), 2.75-2.72 (s, 1H), 2.69-2.63 (m, 4H), 2.24-2.23 (m, 1H), 2.10-2.02 (m, 2H), 1.74 (s, 1H), 1.51-1.46 (m, 2H) 1.18-1.12 (m, 1H) 0.72-0.66 (m, 1H). |

TABLE 64-continued

| Compound | Isomers | Characterization Data |
|---|---|---|
| I-882 (Chiral separation when methylamino at position 7 is protected by Boc, followed by removal, of Boc) | I-1042<br>I-1043 | FR-a: MS(ES): m/z 470.37 [M + H]+, LCMS purity: 100%, HPLC purity : 97.44%, Chiral HPLC: 98.52%, $^1$H NMR (DMSO-d$_6$, 400 MHZ): 8.87 (s, 1H), 8.24 (s, 1H), 8.13-8.11 (d, J = 7.2 Hz, 1H), 7.94-7.92 (d, J = 4.8 Hz, 1H), 7.82-7.81 (d, J = 4.4 Hz, 1H), 7.44-7.43 (d, J = 6.0 Hz, 1H), 6.30-6.27 (t, J = 7.2 Hz, 1H), 6.24 (s, 1H), 5.12 (s, 1H), 4.99-4.79 (m, 1H), 3.71 (s, 1H), 3.29 (s, 3H), 3.01-2.98 (m, 1H), 2.92-2.91 (d, J = 4.8 Hz, 3H), 2.06-2.02 (m, 1H), 1.91-1.65 (m, 6H), 1 41-1.33 (m, 1H), 0.92-0.83 (m, 2H).<br>FR-b: MS (ES): m/z 470.37 [M + H]+, LCMS purity: 100%, HPLC purity: 98.02%, Chiral HPLC: 100%, $^1$H NMR (DMSO-d$_6$, 400 MHZ): 8.87 (s, 1H), 8.24 (s, 1H), 8.13-8.11 (d, J = 6.8 Hz, 1H), 7.94-7.92 (d, J = 4.8 Hz, 1H), 7.82-7.81 (d, J = 4.4 Hz, 1H), 7.44-7.43 (d, J = 6.0 Hz, 1H), 6.30-6.27 (t, J = 7.2 Hz, 1H), 6.24 (s, 1H), 5.12 (s, 1H), 4.99-4.79 (m, 1H), 3.71 (s, 1H), 3.29 (s, 3H), 3.01-2.98 (m, 1H), 2.92-2.91 (d, J = 4.8 Hz, 3H), 2.06-2.02 (m, 1H), 1.91-1.65 (m, 6H), 1 41-1.33 (m, 1H), 0.92-0.82 (m, 2H). |

108.7. Synthesis of N-((1R,2S)-2-fluorocyclopropyl)-7-(methylamino)-5-(1-(tetrahydro-2H-pyran-4-yl)-1H-pyrazolo[3,4-b]pyridin-3-yl)pyrazolo[1,5-a]pyrimidine-3-carboxamide (I-450)

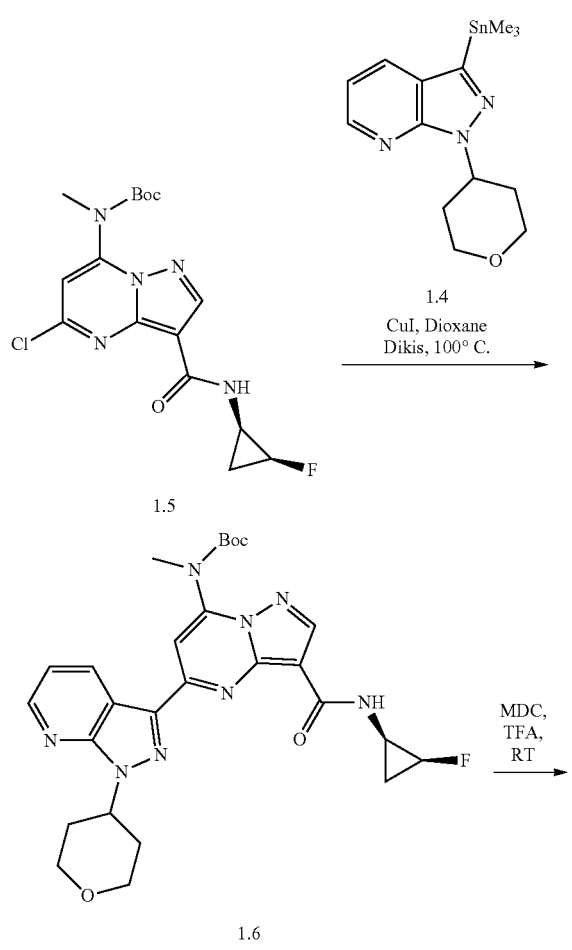

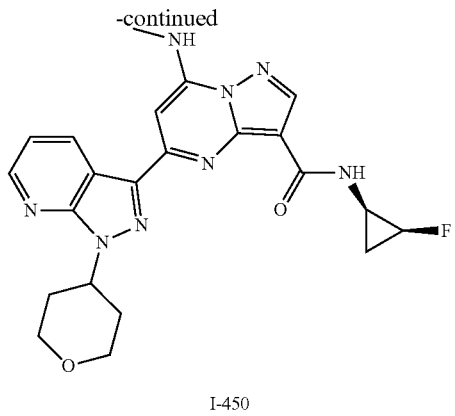

Synthesis of Compound 1.5.

Compound was synthesized as per experimental protocol Example 19 of I-144 to obtain 1.5 (Yield: 51.08%). MS (ES): m/z 384.81 [M+H]+

Synthesis of Compound 1.6.

To a degassed solution of 1.4 (0.240 g, 0.587 mmol, 1.5 eq) and 1.5 (0.150 g, 0.391 mmol, 1.0 eq) in 1,4-dioxane (6.0 mL) was added Bis(triphenylphosphine)palladium(II) dichloride (0.027 g, 0.039 mmol, 0.1 eq) and cuprous iodide (0.008 g, 0.039 mmol, 0.1 eq) and the reaction mixture was stirred at 100° C. for 5 h. After completion of reaction, reaction mixture was cooled to room temperature and filtered. The filtrate was concentrated under reduced pressure to obtain crude material. This was further purified by combi flash using 75% ethyl acetate in hexane as eluant to obtain pure 1.6 (0.140 g, 43.34%). MS(ES): m/z 551.25 [M+H]+.

Synthesis of Compound I-450.

Compound was synthesized using general procedure C to obtain to obtain pure I-450 (0.060 g, 52.44%). MS (ES): m/z 451.35 [M+H]+, LCMS purity: 99.84%, HPLC purity: 99.46%, Chiral HPLC purity: 100%, $^1$H NMR (DMSO-d$_6$, 400 MHZ): 9.03-9.00 (m, 1H), 8.94 (bs, 1H), 8.64 (s, 1H), 7.89-7.85 (m, 1H), 7.63 (bs, 1H), 7.04 (s, 1H), 5.41-5.38 (m, 1H), 4.93-4.77 (m, 1H), 4.47-4.44 (m, 2H), 4.39-4.34 (m, 1H), 3.93-3.86 (t, J=12.0 Hz, 2H), 3.57 (s, 3H), 2.97 (bs, 1H), 2.65-2.62 (m, 1H), 2.27-2.16 (m, 2H), 1.43-1.37 (m, 1H), 1.30-1.21 (m, 1H).

Additional compounds prepared by substantially the same method, and their characterization data, are listed in the Table 65 below. The intermediate corresponding to 1.4 of the above scheme is listed for each compound.

TABLE 65

| Compound | Intermediate | Characterization Data |
| --- | --- | --- |
| I-451 | 3-(SnMe₃)-1-isopropyl-1H-pyrazolo[3,4-b]pyridine | MS (ES): m/z 409.45 [M + H]⁺, LCMS purity: 100%, HPLC purity: 99.86%, Chiral HPLC purity: 100%, $^1$H NMR (DMSO-$d_6$, 400 MHZ): 8.73-8.70 (d, J = 7.6 Hz, 1H), 8.66-8.65 (m, 1H), 8.56 (bs, 1H), 8.49 (s, 1H), 8.18-8.17 (m, 1H), 7.38-7.35 (m, 1H), 6.88 (s, 1H), 5.38-5.31 (m, 1H), 5.04-4.88 (m, 1H), 3.11 (s, 3H), 2.08 (s, 1H), 1.63-1.61 (d, J = 6.8 Hz, 6H), 1.31-1.25 (m, 1H), 1.01-0.94 (m, 1H). |
| I-452 | 3-(SnMe₃)-1-(tetrahydrofuran-3-yl)-1H-pyrazolo[3,4-b]pyridine | MS (ES): m z 437.45 [M + H]⁺, LCMS purity: 100%, HPLC purity: 99.18%, Chiral HPLC: 50.05: 49.95%, $^1$H NMR (DMSO-$d_6$, 400 MHZ): 8.74-8.72 (d, J = 8.0 Hz, 1H), 8.69-8.68 (d, J = 3.2 Hz, 1H), 8.59-8.58 (d, J = 4.4 Hz, 1H), 8.50 (s, 1H), 8.16-8.15 (d, J = 3.6 Hz, 1H), 7.4-7.38 (m, 2H), 6.87 (s, 1H), 5.79-5.77 (d, J = 6.4 Hz, 1H), 5.04-4.88 (m, 1H), 4.23-4.19 (m, 2H), 4.09-4.07 (m, 1H), 4.00-3.95 (m, 1H), 3.12-3.11 (d, J = 4.0 Hz, 3H), 3.06 (s, 1H), 1.33-1.23 (s, 1H), 1.01-0.95 (s, 1H). |
| I-456 | 3-(SnMe₃)-1-(2-morpholinoethyl)-1H-pyrazolo[3,4-b]pyridine | MS (ES): mz 480.22 [M + H]⁺, LCMS purity: 100 %, HPLC purity: 100%, Chiral HPLC purity 99%, $^1$H NMR (DMSO-$d_6$, 400 MHZ): 9.88 (bs, 1H) 8.81-8.79 (d, J = 8.0 Hz, 1H), 8.73-8.67 (m, 2H), 8.55 (s, 1H), 8.17-8.16 (d, J = 4.4 Hz, 1H), 7.48-7.45 (m, 1H), 6.89 (s, 1H), 5.06-5.03 (m, 3H), 4.92-4.88 (m, 1H), 4.02-3.7 (m, 5H), 3.27 (bs, 2H), 3.12-3.08 (m, 4H), 1.35-1.25 (m, 2H), 0.97-0.95 (m, 1H). |
| I-458 | 3-(SnMe₃)-1-(2-piperidinoethyl)-1H-pyrazolo[3,4-b]pyridine | MS (ES): mz 478.22 [M + H]⁺, LCMS purity: 100%, HRLC purity: 100%, Chiral HPLC purity 100%, $^1$H NMR (DMSO-$d_6$, 400 MHZ): 8.73-8.71 (d, J = 8.0 Hz, 1H), 8.68-8.67 (d, J = 3.6 Hz, 1H), 8.58-8.57 (m, 1H), 8.54 (s, 1H), 8.50 (s, 1H), 8.16-8.15 (d, J = 4.0 Hz, 1H), 7.39-7.36 (m, 1H), 6.86 (s, 1H), 5.06-4.90 (m, 1H), 4.4 (bs, 2H), 3.12-3.09 (m, 3H), 3.08 (bs, 1H), 2.88 (bs, 2H), 2.33 (bs, 1H), 1.55-1.29 (m, 4H), 1.27-1.22 (m, 4H), 0.95-0.94 (m, 2H). |

TABLE 65-continued
| Compound | Intermediate | Characterization Data |
|---|---|---|
| I-480 | (structure shown) | MS (ES): m/z 493.3 [M + H]+, LCMS purity: 100%, HPLC purity: 99.18%, ¹H NMR (DMSO-d₆, 400 MHZ): 8.74 (s, 1H), 8.68 (bs, 1H), 8.59-8.57 (d, J = 4.8 Hz, 1H), 8.52 (s, 1H), 8.17 (bs, 1H), 7.39-7.36 (m, 1H), 6.88 (bs, 2H), 5.05-4.89 (m, 1H), 4.72 (bs, 2H), 3.12-3.11 (d, J = 4.8 Hz, 4H), 2.91-2.88 (t, J = 6.4 Hz, 2H), 2.25 (bs, 4H), 2.11 (b, 4H), 1.34-1.25 (m, 2H), 1.03 (bs, 1H), 0.97 (bs, 1H). |
108.8. Synthesis of 5-(1-butyl-1H-pyrrolo[2,3-b]pyridin-3-yl)-N-((1R,2S)-2-fluorocyclopropyl)-7-(methylamino)pyrazolo[1,5-a]pyrimidine-3-carboxamide (I-478)
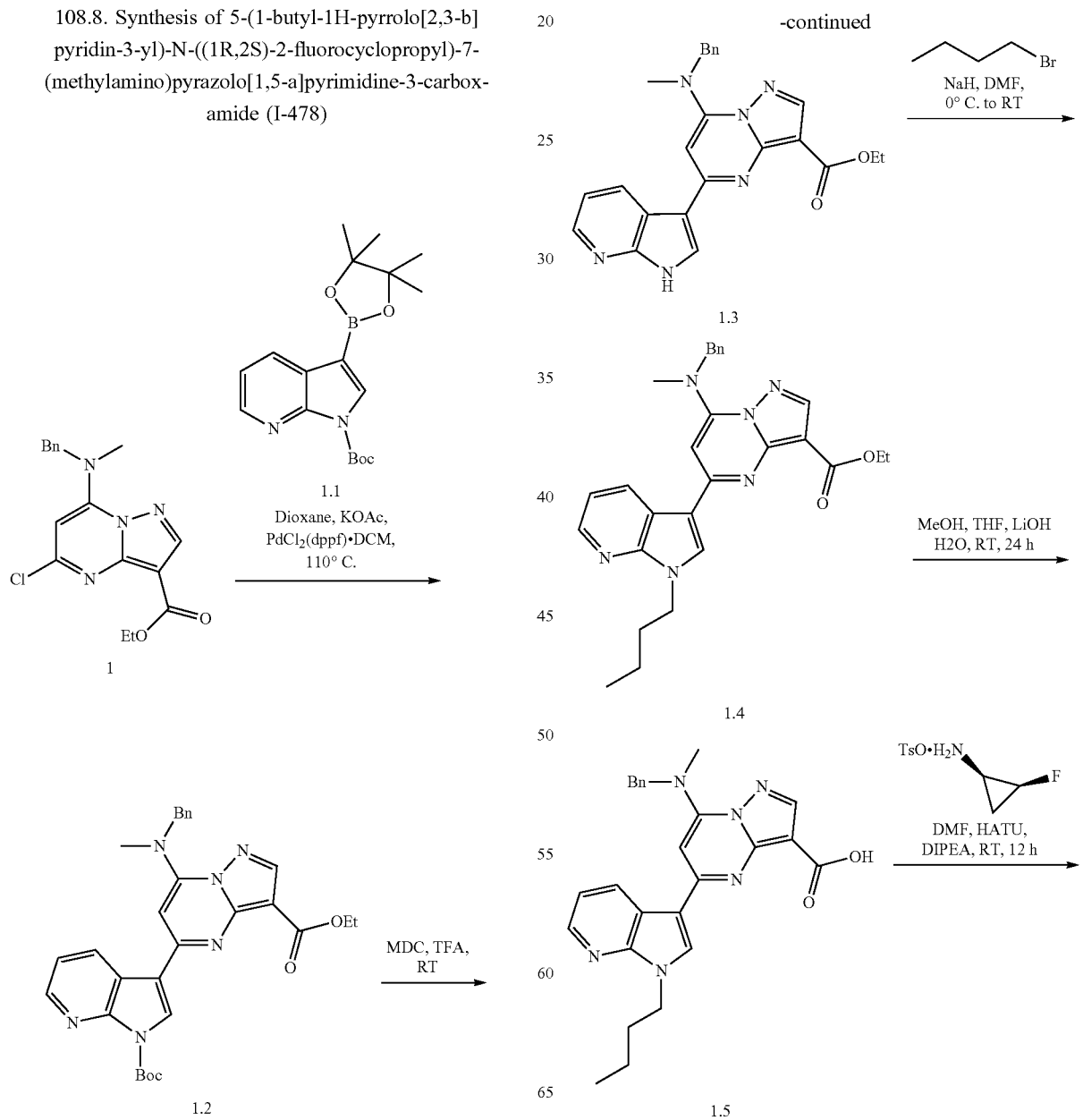

-continued

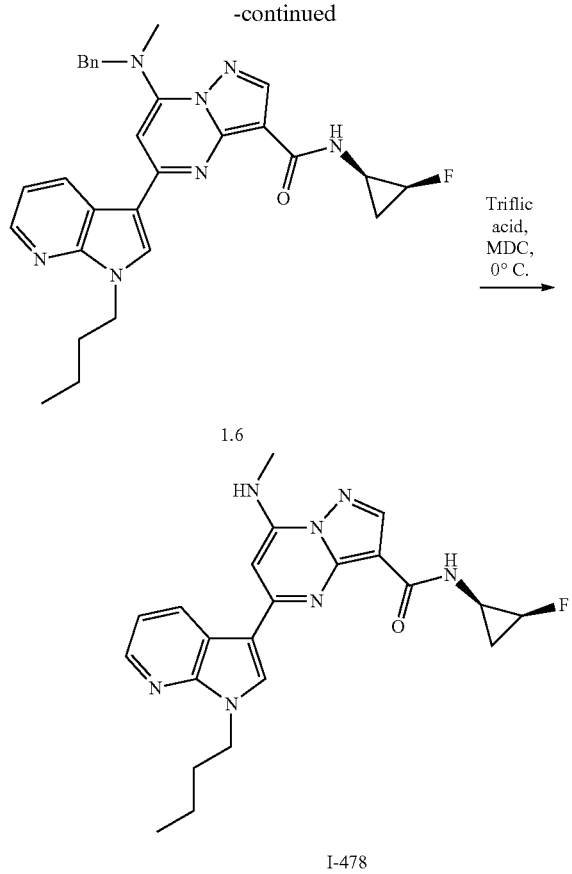

1.6

I-478

Synthesis of Compound 1.

Compound was synthesized using general procedure of core synthesis to obtain 1. (Yield: 45%), MS (ES): m/z 345.10 [M+H]+

Synthesis of Compound 1.2.

Argon was purged for 15 min through a stirring solution of 1 (1.0 g, 2.90 mmol, 1.0 eq), 1.1 (1.29 g, 3.77 mmol, 1.3 eq) and Potassium acetate (0.711 g, 7.25 mmol, 2.5 eq) in 1,4 dioxane(45 ml) [1,1'-Bis(diphenylphosphino) ferrocene]dichloropalladium(II) (0.212 mg, 0.29 mmol, 0.1 eq) was added to it and further purging done for 10 min. Reaction was allowed to stirred at 100° C. for 6 h. After completion of reaction, reaction mixture was poured over water and product was extracted with ethyl acetate. Organic layer was combined, washed with brine solution, dried over sodium sulphate and concentrated under reduced pressure to obtain crude product which purified by column chromatography on silica gel eluting pure compound in 20-25% ethyl acetate in hexane to obtain pure 1.2. (0.8 g, 52.29%). MS (ES): m/z 527.24 [M+H]+

Synthesis of Compound 1.3.

Compound was synthesized using general procedure C to obtain 1.3. (0.610 g, 94.15%). MS (ES): m/z 427.18 [M+H]+.

Synthesis of Compound 1.4.

sodium hydride (60% in mineral oil) (0.134 mg, 5.6 mmol, 4.0 eq) was added a solution of 1.3 (600 mg, 1.40 mmol, 1.0 eq) in N—N-Dimethylformamide (12 mL) at 0° C. portion wise and stirred at same temperature for 20 min. N-butyl bromide (0.230 mg, 1.68 mmol, 1.2 eq) was added and mixture was allowed to stir at room temperature for 6 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography using silica gel (230-400 mesh) eluting pure compound in 2-2.5% methanol in dichloromethane to obtain pure 1.4. (520 mg, 75.33%). MS (ES): m/z 483.25 [M+H]+

Synthesis of Compound 1.5.

To a solution of 1.4 (0.520 g, 1.07 mmol, 1.0 eq), in tetrahydrofuran: methanol: water (25 mL, 1:1:1) was added lithium hydroxide (0.256 mg, 10.7 mmol, 10 eq). The reaction was stirred 60° C. for 6 h. After completion of reaction, reaction mixture was concentrated under reduced pressure to obtain residue. To this added water and acidified with IN hydrochloric acid to adjust pH~6-6.5 at 10° C. Product was filtered and dried under vacuum to obtain pure 1.5. (0.450 mg, 91.88%). MS(ES): m/z 455.22 [M+H]+.

Synthesis of Compound 1.6.

Compound was synthesized using general procedure A to obtain 1.6. (0.100 g, 59.23%), MS (ES): 512.2 [M+H]+

Synthesis of Compound I-478.

Mixture of 1.6 (0.1 g, 0.19 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-478 (0.035 g, 42.48%), MS (ES): m/z 422.33 [M+H]+, LCMS purity: 99.35%, HPLC purity: 100%, 1H NMR (DMSO-d6, 400 MHZ): 8.67 (s, 2H), 8.41 (s, 1H), 8.34-8.33 (d, J=4.4 Hz, 1H), 8.29-8.28 (d, J=4.8 Hz, 1H), 7.28-7.25 (m, 1H), 7.07 (bs, 2H), 6.72 (s, 1H), 5.06-4.86 (m, 1H), 4.39-4.35 (t, J=6.8 Hz, 2H), 3.79 (bs, 1H), 3.11-3.05 (m, 3H), 1.93-1.86 (m, 2H), 1.37-1.29 (m, 3H), 1.04-0.94 (m, 3H).

Additional compounds prepared by substantially the same method, and their characterization data, are listed in the Table 66 below. The intermediate corresponding to n-butyl bromide (the step from 1.3 to 1.4) of the above scheme is listed for each compound.

TABLE 66

| Compound | Intermediate | Characterization Data |
|---|---|---|
| I-583 | Cl-CH2CH2-N(morpholine) | MS (ES): m/z 479.39 [M + H]+, LCMS purity: 95.78%, HPLC purity: 96.98%, Chiral HPLC: 100%, 1H NMR (DMSO-d6, 400 MHZ): 8.66-8.62 (m, 2H), 8.41-8.36 (m, 2H), 8.30-8.29 (m, 2H), 7.28-7.23 (m, 1H), 6.66 (s, 1H), 5.05-4.85 (m, 1H), 4.50-4.46 (t, J = 12.8 Hz, 2H), 3.53 (s, 4H), 3.16-3.04 (m, 4H), 2.82-2.79 (t, J = 12.8, 2H), 2.43-2.37 (m, 4H), 1.31-1.24 (m, 1H), 1.03-0.92 (m, 1H). |
| I-585 | Cl-CH2CH2-N(piperidine) | MS (ES): m/z 477.39 [M + H]+, LCMS purity: 100%, HPLC purity: 100%, Chiral HPLC purity: 99%, 1H NMR (DMSO-d6, 400 MHZ): 8.64-8.62 (d, J = 8.0 Hz, 1H), 8.55 (s, 1H), 8.47 (bs, 1H), 8.38-8.37 (d, J = 4.0 Hz, 1H), 8.32 (bs, 1H), 7.27-7.24 (m, 1H), 6.55 (bs, 1H), 5.03-4 87 (m, 1H), 4.84-4.45 (t, J = 13.2 Hz, 2H), 3.09 (s, 4H), 2.78-2.69 (t, J = 13.2, 2H), 2.53-2.44 (m, 4H), 1.49-1.45 (m, 4H), 1.42-1.21 (m, 4H), 1.01-0.86 (m, 1H). |

TABLE 66-continued

| Compound | Intermediate | Characterization Data |
|---|---|---|
| I-617 | Cl (structure) | MS (ES): m/z 492.57 [M + H]$^+$, LCMS purity: 100%, HPLC purity: 98.19%, CHIRAL HPLC: 100%, $^1$H NMR (DMSO-d$_6$, 400 MHZ): 8.64 (s, 2H), 8.41-8.34 (m, 4H), 7.26 (bs, 1H), 6.67 (bs, 1H), 5.04 (bs, 1H), 4.88 (bs 1H), 4.47 (bs, 2H), 3.11 (bs, 4H), 2.80 (bs, 3H), 2.29 (bs, 4H), 2.13 (s, 4H), 1.29 (bs, 2H), 1.10-0.97 (m, 1H) |

108.9. Synthesis of N-((1R,2S)-2-fluorocyclopropyl)-7-(methylamino)-5-((2-oxo-1-(2-oxaspiro[3.3] heptan-6-yl)-1,2-dihydropyridin-3-yl)amino)pyrazolo[1,5-a]pyrimidine-3-carboxamide(I-551)

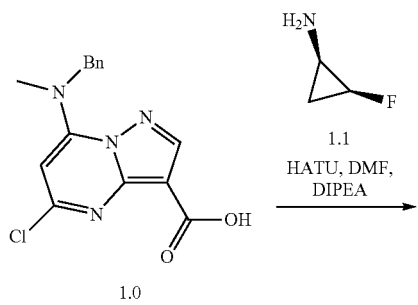

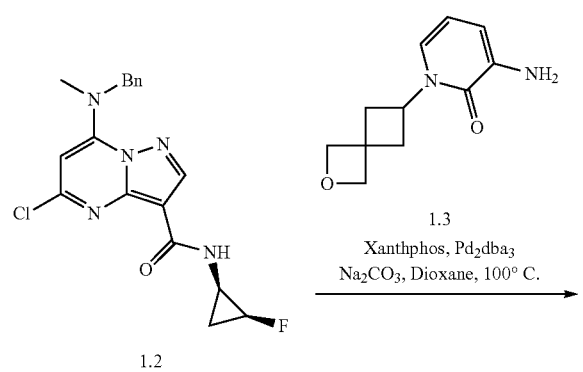

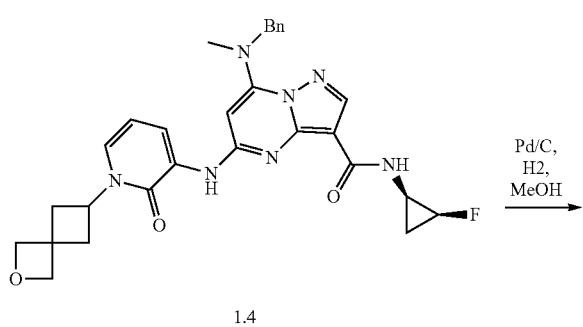

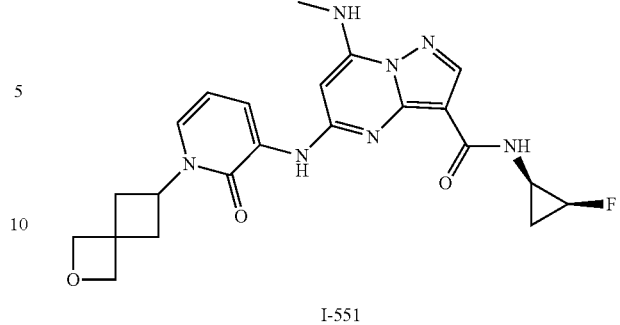

I-551

Synthesis of Compound 1.0.

Compound was synthesized using general procedure of core synthesis to obtain 1.0. (Yield: 60.5%), MS (ES): m/z 317.75 [M+H]$^+$.

Synthesis of Compound 1.2

Compound was synthesized using general procedure A to obtain 1.2 (74.14%), MS (ES): m/z 374.1 [M+H]$^+$ Synthesis of Compound 1.4.

Compound was synthesized using general procedure B to obtain 1.4. (0.045 g, 28.88%), MS (ES): m/z 544.60 [M+H]$^+$ Synthesis of Compound I-551:—

To a solution of 1.4 (0.045 g, 0.077 mmol, 1.0 eq) in Methanol (5.0 mL), palladium on charcoal (0.050 g) was added. Hydrogen was purged through reaction mixture for 2 h at room temperature. After completion of reaction, reaction mixture was filtered through celite-bed and washed with Ethanol. Filtrate was concentrated under reduced pressure to obtain crude which was triturated with diethyl ether to obtain I-551 (0.025 g, Yield: 71.35%). MS(ES): m/z 454.35 [M+H]$^+$. LCMS purity: 97.05%, HPLC purity: 95.04%, CHIRAL HPLC: 98.62% $^1$H NMR (DMSO-d$_6$, 400 MHZ): 8.86 (s, 1H), 8.23 (s, 1H), 8.12-8.10 (d, J=8.0 Hz, 1H), 7.93-7.92 (d, J=4.0 Hz, 1H), 7.81-7.79 (d, J=8.0 Hz, 1H), 7.42-7.41 (d, J=4.0 Hz, 1H), 6.29-6.25 (t, J=8.0 Hz, 1H), 6.20 (s, 1H), 4.95-4.91 (m, 1H), 4.80 (s, 1H), 4.71 (s, 1H), 4.55 (s, 2H), 2.98 (s, 1H), 2.90-2.89 (d, J=4.0 Hz, 3H), 2.76-2.67 (m, 3H), 1.27-1.19 (m, 2H), 0.89-0.87 (m, 2H).

Additional compounds prepared by substantially the same method, and their characterization data, are listed in the Table 67 below. The intermediate corresponding to 1.3 of the above scheme is listed for each compound.

TABLE 67

| Compound | Intermediate | Characterization Data |
|---|---|---|
| I-757 | 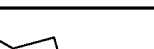 | MS (ES): m/z 413.43 [M + H]+ LCMS purity: 100%, HPLC purity: 98.00%, CHIRAL HPLC: 100%, ¹H NMR (DMSO-d₆, 400 MHZ): 9.64-9.62 (d, J = 7.2 Hz, 1H), 8.24 (s, 1H), 8.05-8.04 (d, J = 3.6 Hz, 2H), 7.48-7.44 (t, J = 7.6 Hz, 1H), 6.83-6.77 (m, 1H), 6.01-5.98 (m, 1H), 5.70-5.68 (d, J = 6.4 Hz, 1H), 4.91 (bs, 1H), 4.75 (bs, 1H), 4.59 (bs, 1H), 4.23-4.19 (t, J = 7.6 Hz, 2H), 3.75-3.72 (m, 2H), 2.96-2.95 (m, 3H), 1.61-1.55 (m, 1H), 1.34-1.30 (m, 1H), 0.95-0.91 (t, J = 7.2 Hz, 1H). |

108.10. Synthesis of -((1-(1-(2-cyanoethyl)piperidin-4-yl)-2-oxo-1,2-dihydropyridin-3-yl)amino)-N-((1R,2S)-2-fluorocyclopropyl)-7-(methylamino)pyrazolo[1,5-a]pyrimidine-3-carboxamide (I-628)

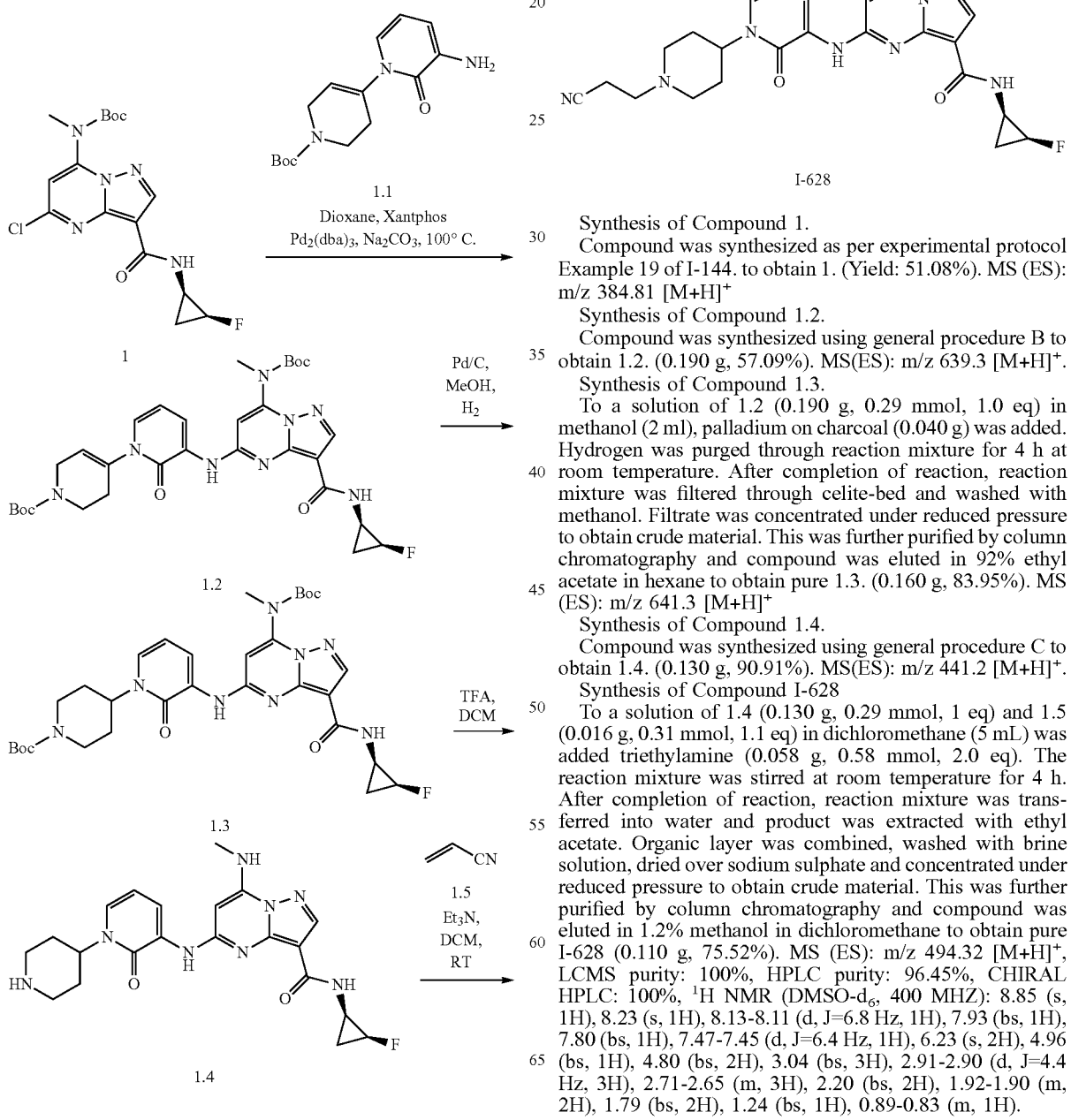

Synthesis of Compound 1.

Compound was synthesized as per experimental protocol Example 19 of I-144. to obtain 1. (Yield: 51.08%). MS (ES): m/z 384.81 [M+H]⁺

Synthesis of Compound 1.2.

Compound was synthesized using general procedure B to obtain 1.2. (0.190 g, 57.09%). MS(ES): m/z 639.3 [M+H]⁺.

Synthesis of Compound 1.3.

To a solution of 1.2 (0.190 g, 0.29 mmol, 1.0 eq) in methanol (2 ml), palladium on charcoal (0.040 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 92% ethyl acetate in hexane to obtain pure 1.3. (0.160 g, 83.95%). MS (ES): m/z 641.3 [M+H]⁺

Synthesis of Compound 1.4.

Compound was synthesized using general procedure C to obtain 1.4. (0.130 g, 90.91%). MS(ES): m/z 441.2 [M+H]⁺.

Synthesis of Compound I-628

To a solution of 1.4 (0.130 g, 0.29 mmol, 1 eq) and 1.5 (0.016 g, 0.31 mmol, 1.1 eq) in dichloromethane (5 mL) was added triethylamine (0.058 g, 0.58 mmol, 2.0 eq). The reaction mixture was stirred at room temperature for 4 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure I-628 (0.110 g, 75.52%). MS (ES): m/z 494.32 [M+H]⁺, LCMS purity: 100%, HPLC purity: 96.45%, CHIRAL HPLC: 100%, ¹H NMR (DMSO-d₆, 400 MHZ): 8.85 (s, 1H), 8.23 (s, 1H), 8.13-8.11 (d, J=6.8 Hz, 1H), 7.93 (bs, 1H), 7.80 (bs, 1H), 7.47-7.45 (d, J=6.4 Hz, 1H), 6.23 (s, 2H), 4.96 (bs, 1H), 4.80 (bs, 2H), 3.04 (bs, 3H), 2.91-2.90 (d, J=4.4 Hz, 3H), 2.71-2.65 (m, 3H), 2.20 (bs, 2H), 1.92-1.90 (m, 2H), 1.79 (bs, 2H), 1.24 (bs, 1H), 0.89-0.83 (m, 1H).

9.11. Synthesis of N-((1R,2S)-2-fluorocyclopropyl)-7-(methylamino)-5-((2-(methylcarbamoyl)furan-3-yl)amino)pyrazolo[1,5-a]pyrimidine-3-carboxamide (I-888)

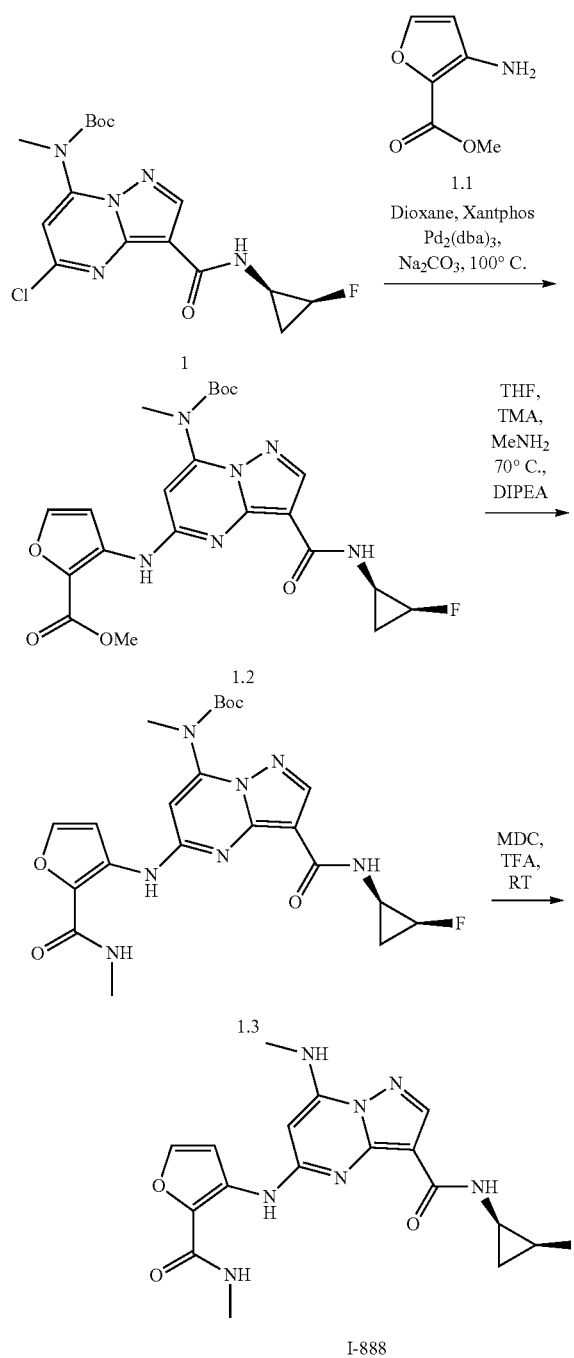

Synthesis of Compound 1.

Compound was synthesized as per experimental protocol Example 19 of I-144. to obtain 1. (Yield: 51.08%). MS (ES): m/z 384.81 [M+H]+

Synthesis of Compound 1.2.

Compound was synthesized using general procedure B to obtain 1.2. (0.150 g, 58.93%), MS (ES): 489.19 [M+H]+

Synthesis of Compound 1.3.

To a cooled solution of 1 (0.150 g, 0.30 mmol, 1.0 eq) in tetrahydrofuran (12 mL) was added Methylamine (0.018 g, 0.6 mmol, 2.0 eq) followed by Trimethylaluminium (0.064 g, 0.9 mmol, 3.0 eq) and N,N-Diisopropylethylamine (0.096 g, 0.75 mmol, 2.5 eq). The reaction mixture was stirred at 70° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.3. (0.095 g, 63.46%). MS(ES): m/z 488.20 [M+H]+.

Synthesis of Compound I-888:

Compound was synthesized using general procedure C to obtain I-888 (0.060 g, 79.48%), MS (ES): m/z 388.89 [M+H]+, LCMS purity: 100%, HPLC purity: 98.58%, CHIRAL HPLC: 100%,1H NMR (DMSO-$d_6$, 400 MHZ): 9.38 (s, 1H), 8.27 (s, 1H), 8.25 (s, 1H), 8.03-8.01 (d, J=4.8 Hz, 1H), 7.85-7.84 (d, J=4.4 Hz, 1H), 7.81-7.80 (d, J=1.6 Hz, 1H), 7.30 (bs, 1H), 5.99 (s, 1H), 4.78-4.75 (m, 1H), 2.94-2.93 (d, J=4.8 Hz, 4H), 2.79-2.78 (d, J=4.4 Hz, 3H), 1.24 (s, 1H), 1.22-1.16 (m, 1H).

Additional compounds prepared by substantially the same method, and their characterization data, are listed in the Table 68 below. The intermediate corresponding to 1.1 of the above scheme is listed for each compound.

TABLE 68

| Compound | Intermediate | Characterization Data |
|---|---|---|
| I-914 | 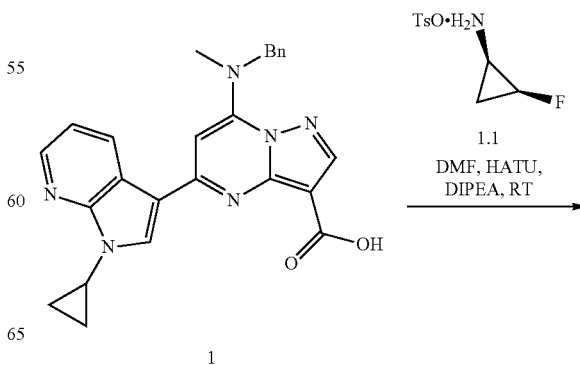 (shown as small structure) | MS (ES): m/z 405.65 [M + H]+, LCMS purity: 100%, HPLC purity: 98.42%, CHIRAL HPLC: 98.55%, 1H NMR (DMSO-$d_6$, 400 MHZ): 10.38 (s, 1H), 9.27 (s, 1H), 9.00-8.99 (d, J = 4.4 Hz, 1H), 8.29 (s, 1H), 8.04 (s, 1H), 7.78-7.77 (d, J = 4.4 Hz, 1H), 5.91 (s, 1H), 4.99-4.83 (m, 1H), 2.97 (s, 3H), 2.85 (s, 3H), 1.24 (s, 2H), 0.76-0.53 (m, 1H). |

108.12. Synthesis of 5-(1-cyclopropyl-1H-pyrrolo[2,3-b]pyridin-3-yl)-N-((1R,2S)-2-fluorocyclopropyl)-7-(methylamino)pyrazolo[1,5-a]pyrimidine-3-carboxamide(I-961)

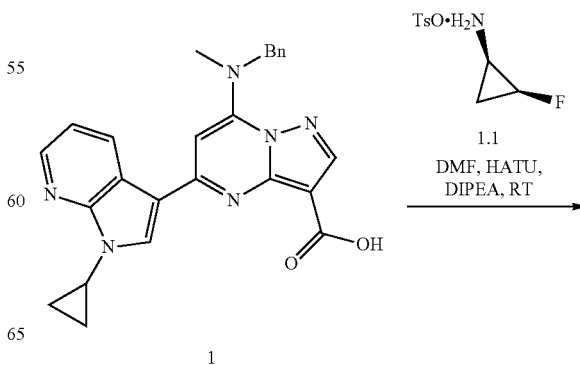

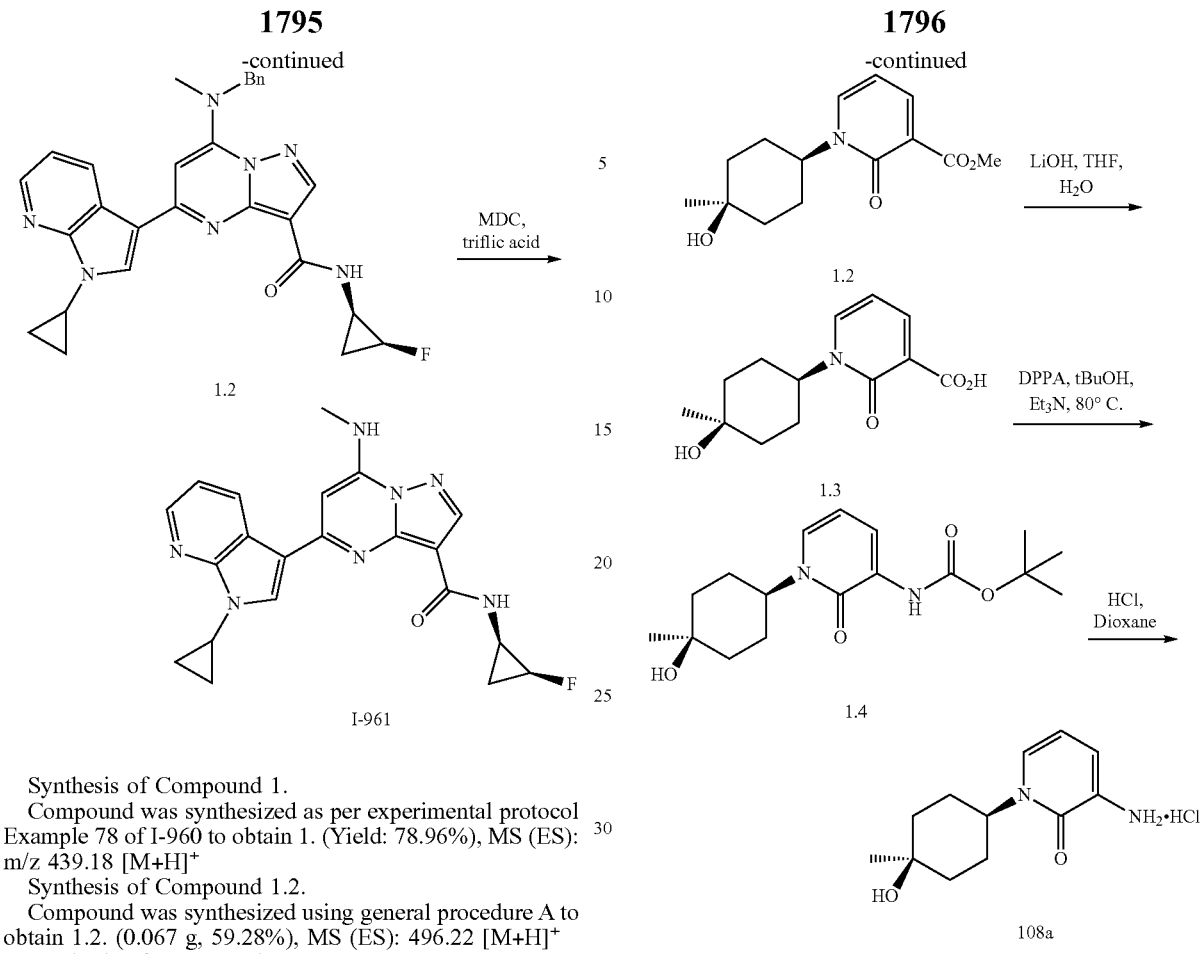

Synthesis of Compound 1.

Compound was synthesized as per experimental protocol Example 78 of I-960 to obtain 1. (Yield: 78.96%), MS (ES): m/z 439.18 [M+H]$^+$ Synthesis of Compound 1.2.

Compound was synthesized using general procedure A to obtain 1.2. (0.067 g, 59.28%), MS (ES): 496.22 [M+H]$^+$ Synthesis of Compound I-961:

Mixture of 1.2 (0.067 g, 0.13 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-961 (0.035 g, 63.85%), MS (ES): m/z 406.20 [M+H]$^+$, LCMS purity: 100%, HPLC purity: 97.84%, CHIRAL HPLC: 100%, $^1$H NMR (DMSO-$d_6$, 400 MHZ): 8.67-8.65 (d, J=7.6 Hz, 1H), 8.56 (s, 1H), 8.42-8.42 (d, J=1.2 Hz, 1H), 8.41 (s, 1H), 8.33-8.32 (d, J=4.4 Hz, 1H), 8.28-8.27 (d, J=4.8 Hz, 1H), 7.30-7.27 (m, 1H), 6.77 (s, 1H), 5.06-5.04 (m, 1H), 4.90-4.86 (m, 1H), 3.82-3.76 (m, 1H), 3.12-3.11 (d, J=4.8 Hz, 3H), 1.34-1.25 (m, 2H), 1.17-1.16 (d, J=5.6 Hz, 4H).

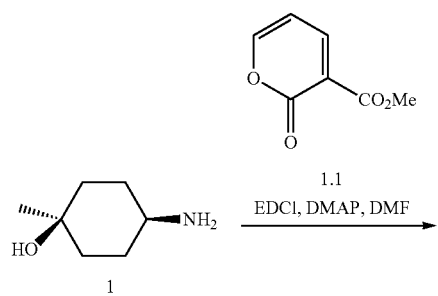

Synthesis of Compound 1.2.

To a cooled solution of 1 (1.2 g, 9.29 mmol, 1.0 eq), in N,N-dimethylformamide (10 mL) was added 1.1 (1.43 g, 9.29 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.87 g, 12.07 mmol, 1.3 eq) and 4-Dimethylaminopyridine (0.843 g, 2.32 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (0.260 g, 10.55%). MS(ES): m/z 266.31 [M+H]$^+$.

Synthesis of Compound 1.3.

To a solution of 1.2 (0.260 g, 0.98 mmol, 1.0 eq), in tetrahydrofuran: water (10 mL, 2:1) was added lithium hydroxide (0.412 g, 9.81 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.190 g, 77.16%). MS(ES): m/z 252.28 [M+H]⁺.

Synthesis of Compound 1.4.

To a solution of 1.3 (0.190 g, 0.75 mmol, 1.0 eq) in tert.butanol (5 mL) was added triethylamine (0.128 g, 1.27 mmol, 1.7 eq) and diphenyl phosphoryl azide (0.268 g, 0.975 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.067 g, 27.48%). MS(ES): m/z 323.41 [M+H]⁺.

Synthesis of Compound 108a.

A cooled solution of 1.4 (0.067 g, 0.207 mmol, 1 eq) in dioxane (3 mL) was added 4N hydrochloric acid in dioxane (4 mL) as a dropwise. The reaction mixture was stirred at room temperature for 2 h. After completion of reaction, reaction mixture was concentrated under reduced pressure to obtain pure 108a (0.037 g, 80.10%). MS(ES): m/z 223.29 [M−HCl]⁺.

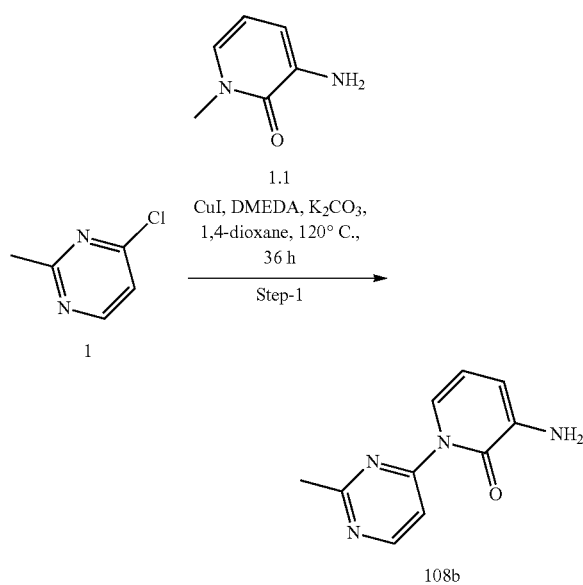

Synthesis of Compound 108b.

To a solution of 1 (0.5 g, 3.90 mmol, 1.0 eq) and 1.1 0.58 g, 4.68 mmol, 1.2 eq) in 1,4-dioxane was added potassium carbonate (1.34 g, 9.75 mmol, 2.5 eq) and reaction mixture was degassed with Argon for 10 min. To this N,N'-Dimethylethylenediamine (0.14 g, 1.56 mmol, 0.4 eq) was added followed by addition of copper(I) iodide (015 g, 0.79 mmol, 0.2 q). The reaction mixture was heated to 120° C. for 36 h. After completion of reaction, reaction mixture was transferred into water and extracted with ethyl acetate. Organic layer combined, washed with brine, dried over sodium sulphate and concentrated under reduced pressure to obtain crude material.

(Eight Similar Batches were Taken and Crude Material was Combined).

This was further purified by column chromatography and compound was eluted in 50% ethyl acetate in hexane to obtain 108b (0.3 g, 4.76%). MS(ES): m/z 203.09 [M+H]⁺.

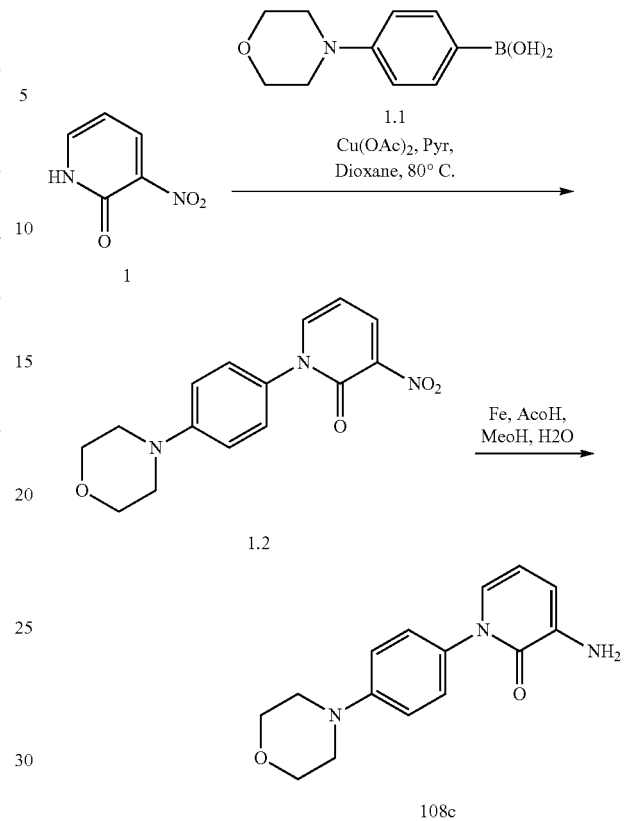

Synthesis of Compound 1.2.

To a solution of 1. (2 g, 14.28 mmol, 1.0 eq) in 1,4-dioxane (50 mL), 1.1 (4.4 g, 21.42 mmol, 1.5 eq) was added followed by Copper acetate (3.8 g, 21.42 mmol, 1.5 eq) and pyridine (10 mL). The reaction mixture was degassed for 30 min under oxygen atmosphere and heated at 80° C. for 16 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 100% ethylacetate to obtain 1.2 (1.5 g, Yield: 34.87%). MS (ES): m/z 302.30 [M+H]⁺.

Synthesis of Compound 108c.

To a solution of 1.2. (1.5 g, 4.98 mmol, 1.0 eq) in methanol: water (1:1) was added. Then iron powder (1.3 g, 24.9 mmol, 5.0 eq) and acetic acid (2 mL) was added. The reaction mixture was heated at 60° C. for 15 min. After completion of reaction, reaction mixture was filtered through celite pad and washed with ethylacetate and product was extracted with ethylacetate. Organic layer was combined, washed with brine solution, dried over sodium sulphate and concentrated under reduced pressure to obtain crude material. This was further purified by 5% methanol in dichloromethane to obtain 108c (1. g, Yield: 74.03%). MS (ES): m/z 272.32 [M+H]⁺.

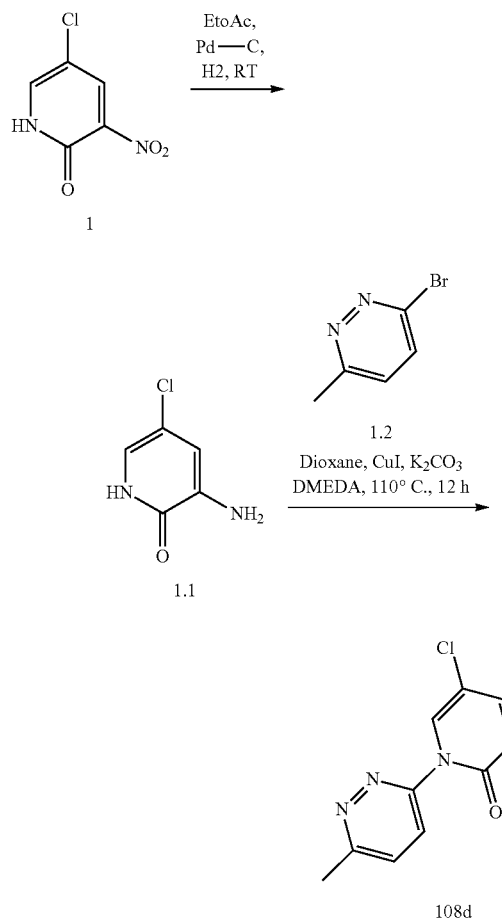

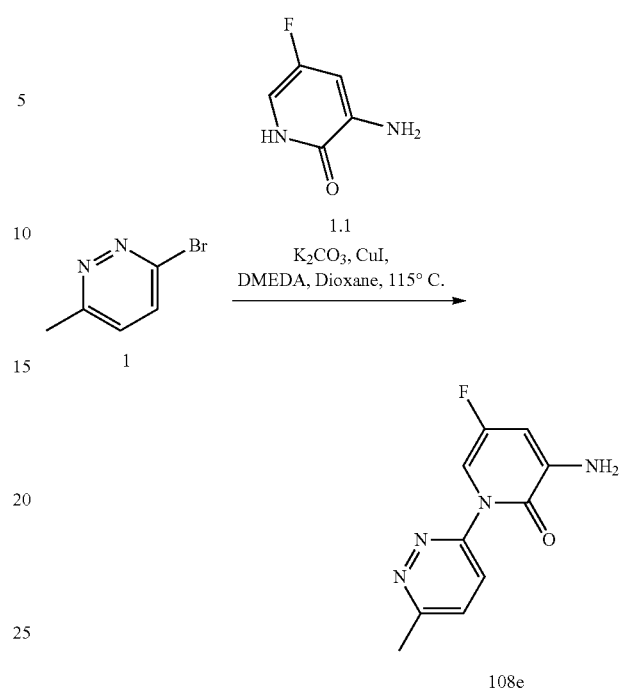

Synthesis of Compound 108e.

To a solution of 1 (1 g, 5.78 mmol, 1.0 eq) and 1.1 (0.814 g, 6.36 mmol, 1.1 eq) in 1,4-dioxane (10 mL) was added potassium carbonate (1.59 g, 11.56 mmol, 2.0 eq) and degassed with argon for 15 min. Copper iodide (0.218 g, 1.15 mmol, 0.2 eq) and 1,2-dimethylethylenediamine (0.202 g, 2.30 mmol, 0.4 eq) was added and reaction mixture again degassed with argon for 5 min followed by heating at 115° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1% methanol in dichloromethane to obtain pure 108e (0.480 g, 37.71%). MS(ES): m/z 221.21 [M+H]$^+$.

Synthesis of Compound 1.1.

To a solution of 1. (5 g, 28.65 mmol, 1.0 eq) in ethyl acetate (45 mL), palladium on charcoal (1 g) was added. Hydrogen was purged through reaction mixture for 2 h at room temperature. After completion of reaction, reaction mixture was filtered through celite-bed and washed with methanol. Filtrate was concentrated under reduced pressure to obtain 1.1 (1.2 g, 28.98%). MS(ES): m/z 145.56 [M+H]$^+$ Synthesis of Compound 108d.

To a solution of 1.1. (0.40 g, 2.77 mmol, 1.0 eq) in 1,4-dioxane (4 mL), 1.2 (0.57 g, 3.32 mmol, 1.2 eq) was added. The reaction mixture was degassed for 10 min under argon atmosphere followed by addition of potassium carbonate (0.76 g, 5.54 mmol, 2.0 eq), N,N-dimethylethylenediamine (0.09 g, 0.83 mmol, 0.3 eq), and copper iodide (0.07 g, 0.41 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108d (Yield: 48.87%). MS (ES): m/z 236.66 [M+H]

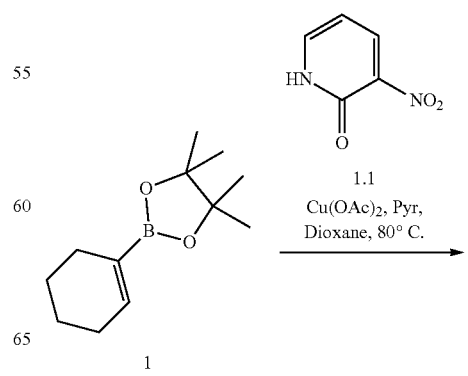

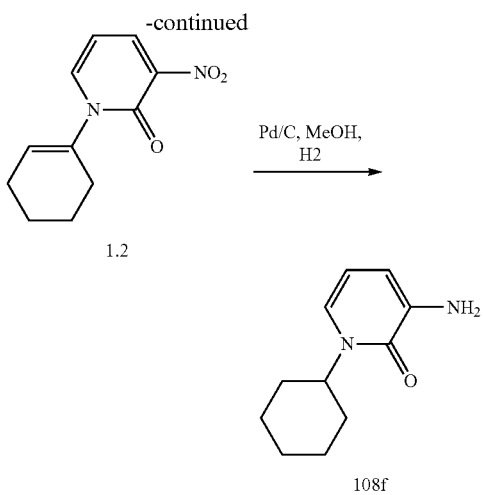

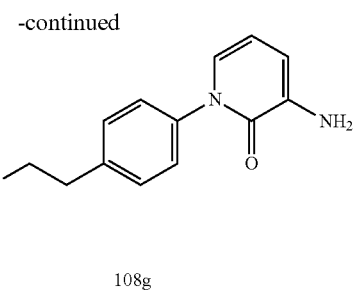

Synthesis of Compound 1.2.

To a solution of 1 (0.250 g, 1.78 mmol, 1.0 eq) and 1.1 (0.419 g, 1.78 mmol, 1.0 eq) in acetonitrile:ethanol (2:1, 15 mL) was added copper acetate (0.324 g, 1.78 mmol, 1.0 eq) and triethylamine (0.5 mL, 3.56 mmol, 2.0 eq) under nitrogen. The reaction was stirred at 80° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 0.7% methanol in dichloromethane to obtain pure 1.2 (0.162 g, 27.56%), MS(ES): m/z 330.36 [M+H]+.

Synthesis of Compound 108g.

To a solution of 1.2 (0.162 g, 0.491 mmol, 1.0 eq) in methanol (3 ml), palladium on charcoal (0.040 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 2.1% methanol in dichloromethane to obtain pure 108 g (0.072 g, 48.90%). MS (ES): m/z 300.37 [M+H]+.

Synthesis of Compound 1.2.

To a solution of 1 (0.500 g, 2.4 mmol, 1.0 eq) in 1,4-dioxane (5 mL), 1.1 (0.673 g, 4.81 mmol, 2.0 eq) copper acetate (0.655 g, 3.6 mmol, 1.5 eq) and pyridine (2.5 mL) was added. The reaction mixture was stirred at 80° C. for 1 h. After completion of reaction, reaction mixture was, filtered through celite and product was washed with methanol. Organic layer was combined, dried over sodium sulphate and concentrated under reduced pressure to obtain crude material. This was further purified by column chromatography using 25% ethyl acetate in hexane as eluant to obtain pure to obtain pure 1.2 (0.260 g, 49.14%). MS(ES): m/z 221.23 [M+H]+

Synthesis of Compound 108f.

To a solution of 1.2 (0.260 g, 0.85 mmol, 1.0 eq) in methanol (4 mL), palladium on charcoal (0.05 g) was added. Hydrogen was purged through reaction mixture for 4 h at room temperature. After completion of reaction, reaction mixture was filtered through celite-bed and washed with methanol. Filtrate was concentrated under reduced pressure to obtain 108f (0.220 g, 96.92%). MS(ES): m/z 193.26 [M+H]+.

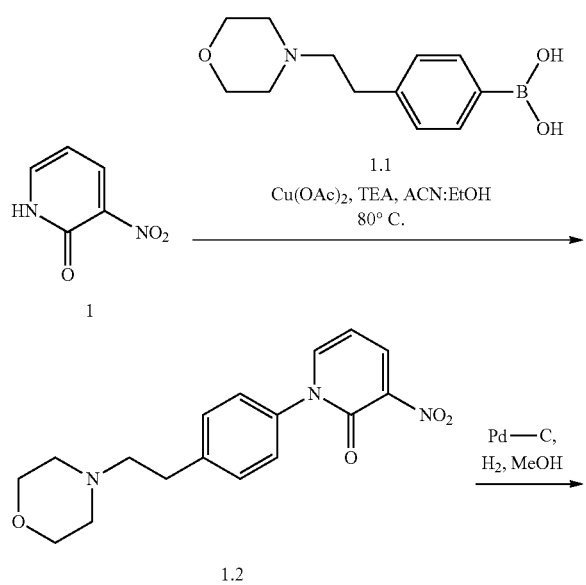

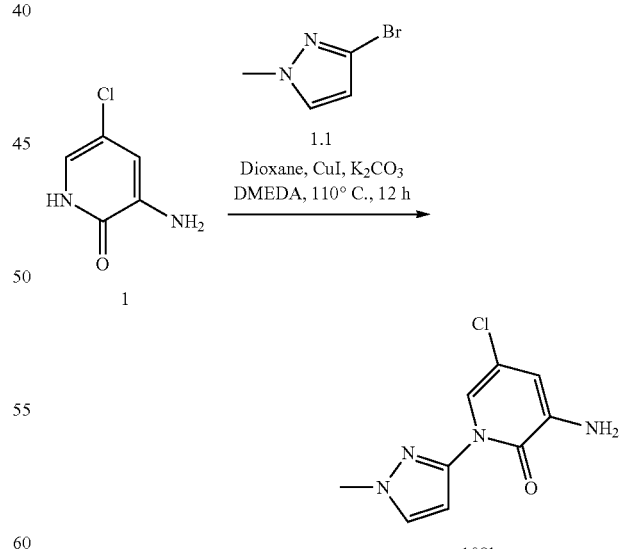

Synthesis of Compound 108h.

To a solution of 1 (1 g, 6.92 mmol, 1.0 eq) in 1,4-dioxane (100 mL), 1.1 (1.6 g, 10.38 mmol, 1.5 eq) was added. The reaction mixture was degassed for 10 min under argon atmosphere followed by addition of potassium carbonate (1.9 g, 13.84 mmol, 2.0 eq), N,N-dimethylethylenediamine (0.24 g, 2.76 mmol, 0.4 eq), and copper iodide (0.26 g, 1.38 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108 h (0.40 g, Yield: 25.74%). MS (ES): m/z 225.65 [M+H]+

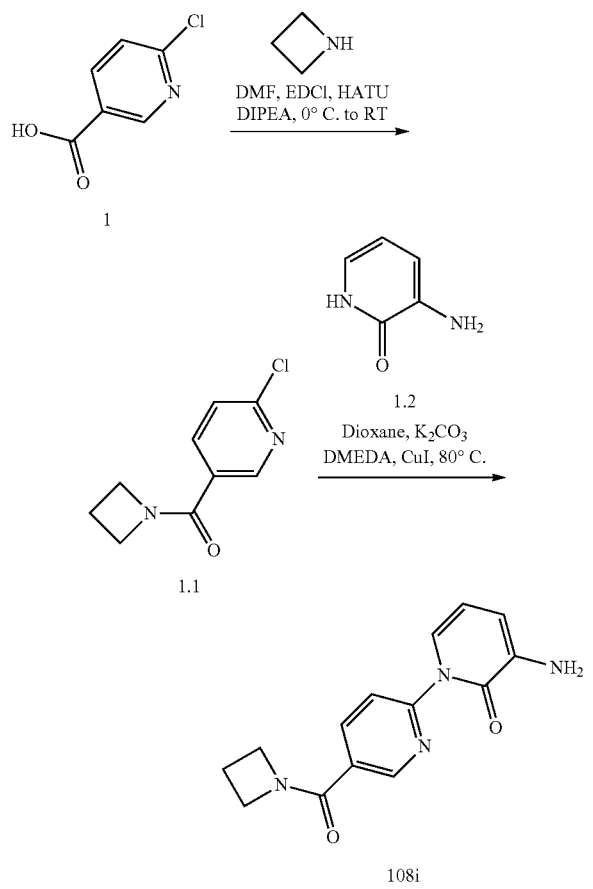

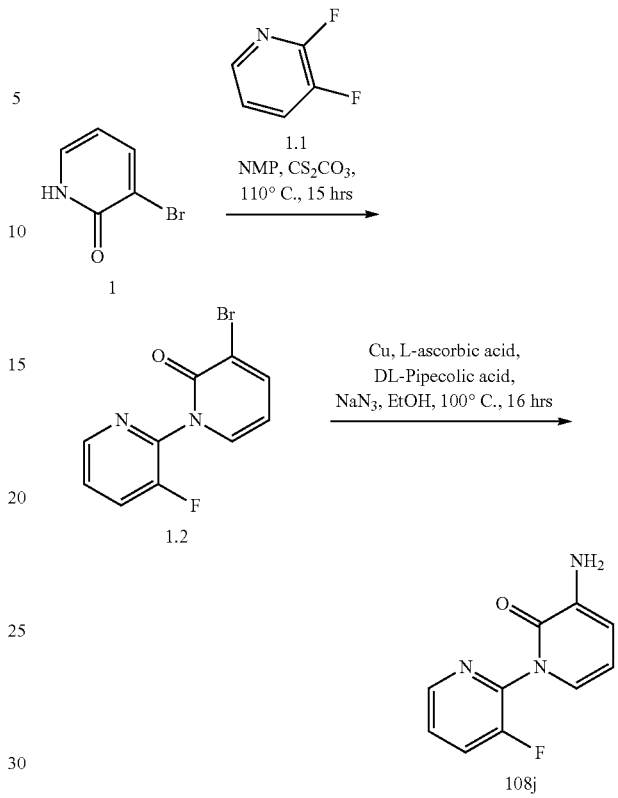

Synthesis of Compound 1.1.

Compound was synthesized using general procedure A to obtain 1.1. (Yield: 60.09%). MS (ES): m/z 197.63 [M+H]+

Synthesis of Compound 108i.

To a solution of 1.1 (0.50 g, 2.54 mmol, 1.0 eq) in 1,4-dioxane (5 mL), 1.2 (0.27 g, 2.54 mmol, 1.1 eq) was added. The reaction mixture was degassed for 10 min under argon atmosphere followed by addition of potassium carbonate (0.70 g, 5.08 mmol, 2.0 eq), N,N-dimethylethylenediamine (0.08 g, 1.0 mmol, 0.4 eq), and copper iodide (0.09 g, 0.50 mmol, 0.2 eq). The reaction mixture was heated at 80° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108i (0.26 g, Yield: 37.83%). MS (ES): m/z 271.29 [M+H]+.

Synthesis of Compound 1.2.

To a solution of 1 (10 g, 57.47 mmol, 1.0 eq) in 1-methylpyrrolidin-2-one (240 mL), 1.1 (7.34 g, 63.79 mmol, 1.1 eq) was added followed by addition of cesium carbonate (46.81 g, 143.67 mmol, 2.5 eq). The reaction mixture was heated at 110° C. for 15 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified column chromatography using 50% ethyl acetate in hexane as eluant to obtain 1.2 (2.6 g, 16.81%). MS (ES): m/z 269.04 [M]+

Synthesis of Compound 108j.

To a solution of 1.2 (2.6 g, 9.66 mmol, 1.0 eq) in ethanol (26 mL) was added copper powder (0.073 g, 1.15 mmol, 0.12 eq), L-ascorbic acid (0.34 g, 1.93 mmol, 0.2 eq), DL-Pipecolic acid (0.37 g, 2.89 mmol, 0.3 eq) and sodium azide (2.26 g, 34.77 mmol, 3.6 eq). The reaction mixture was heated at 100° C. for 16 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified column chromatography using 55-60% ethyl acetate in hexane as eluant to obtain 108j (1.6 g, 80.70%). MS (ES): m/z 206.29 [M+H]+.

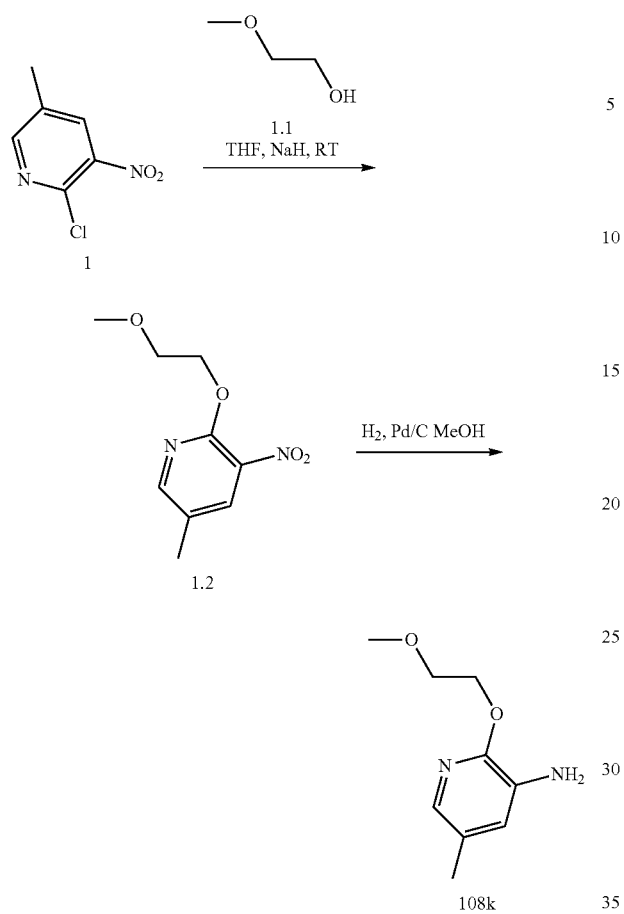
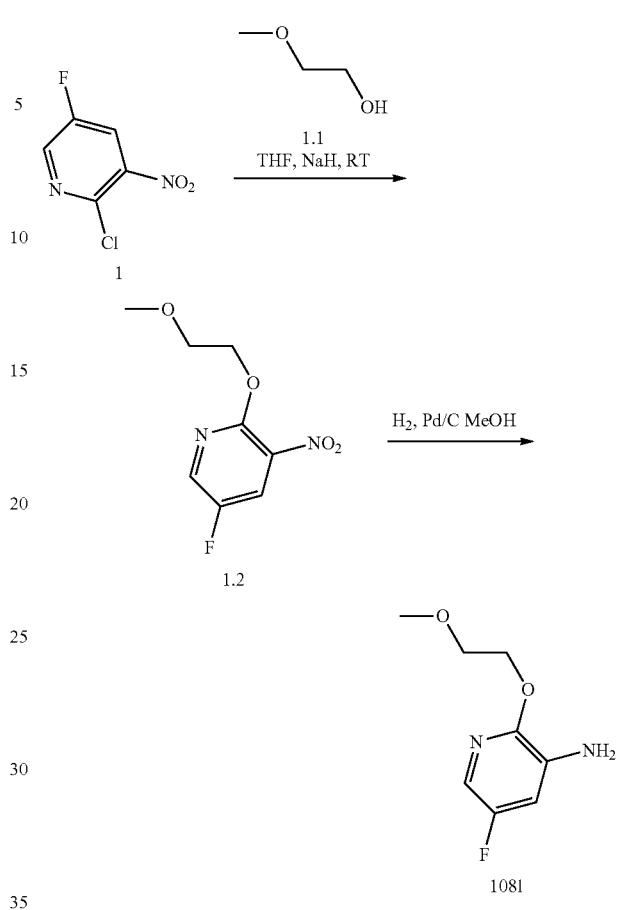

Synthesis of Compound 1.2.

To a cooled solution of 1 (1 g, 5.79 mmol, 1 eq) in tetrahydrofuran (10 mL) was added sodium hydride (0.166 g, 11.58 mmol, 2 eq) followed by addition of 1.1 (0.573 g, 7.53 mmol, 1.3 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 14% ethyl acetate in hexane to obtain pure 1.2 (0.550 g, 44.73%), MS(ES): m/z 213.21 [M+H]$^+$.

Synthesis of Compound 108k.

To a solution of 1.2 (0.550 g, 2.59 mmol, 1.0 eq) in methanol (6 ml), palladium on charcoal (0.130 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by column chromatography and compound was eluted in 1.6% methanol in dichloromethane to obtain pure 1.3 (0.420 g, 88.93%). MS (ES): m/z 183.22 [M+H]$^+$.

Synthesis of Compound 1.2.

To a cooled solution of 1 (1 g, 5.66 mmol, 1.2 eq) in tetrahydrofuran (20 mL) was added sodium hydride (0.102 g, 7.08 mmol, 1.5 eq) followed by addition of 1.1 (0.360 g, 4.72 mmol, 1 eq) under nitrogen. The reaction was stirred at 0° C. for 1 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 8% ethyl acetate in hexane to obtain pure 1.2 (0.370 g, 36.26%), MS(ES): m/z 217.17[M+H]$^+$.

Synthesis of Compound 108l.

To a solution of 1.2 (0.370 g, 1.71 mmol, 1.0 eq) in methanol (5 ml), palladium on charcoal (0.120 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 28% ethyl acetate in hexane to obtain pure 108l (0.180 g, 56.48%). MS (ES): m/z 187.19 [M+H]$^+$.

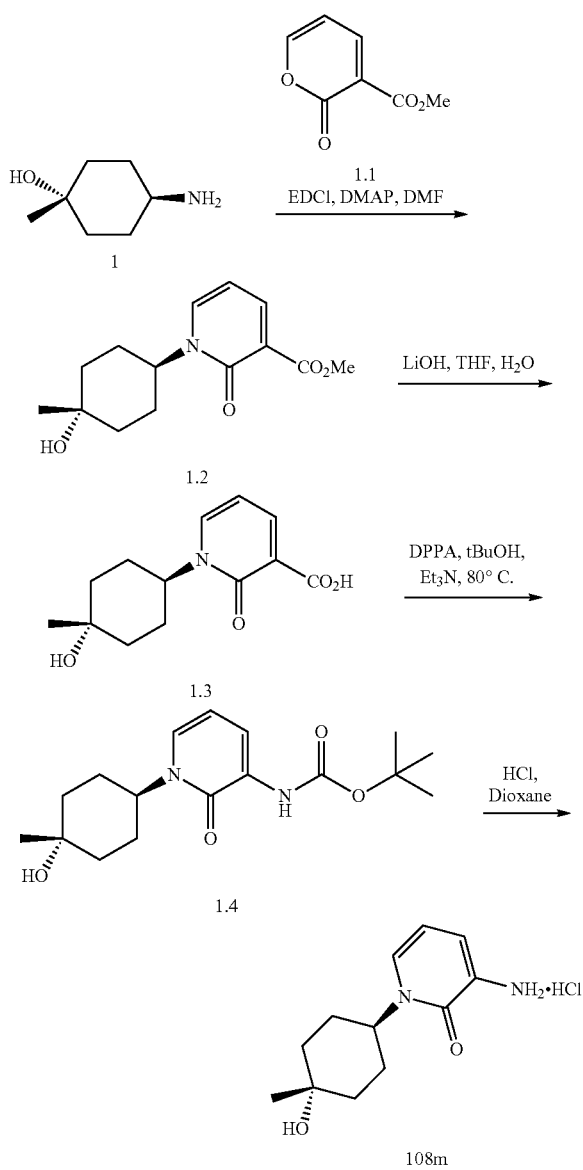

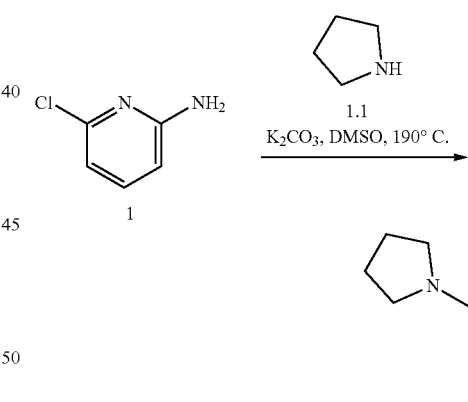

hydroxide (0.272 g, 6.48 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.150 g, 92.08%). MS(ES): m/z 252.12 [M+H]$^+$.

Synthesis of Compound 1.4.

To a solution of 1.3 (0.150 g, 0.596 mmol, 1.0 eq) in tert.butanol (5 mL) was added triethylamine (0.102 g, 1.01 mmol, 1.7 eq) and diphenyl phosphoryl azide (0.212 g, 0.778 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.100 g, 51.96%). MS(ES): m/z 323.41 [M+H]$^+$.

Synthesis of Compound 108m.

A cooled solution of 1.4 (0.100 g, 0.310 mmol, 1 eq) in dioxane (5 mL) was added 4N hydrochloric acid in dioxane (4 mL) as a dropwise. The reaction mixture was stirred at room temperature for 2 h. After completion of reaction, reaction mixture was concentrated under reduced pressure to obtain pure 108m (0.070 g, 87.22%). MS(ES): m/z 223.41 [M−HCl]$^+$.

Synthesis of Compound 1.2.

To a cooled solution of 1 (0.900 g, 6.97 mmol, 1.0 eq), in N,N-dimethylformamide (8 mL) was added 1.1 (1.07 g, 6.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.140 g, 9.06 mmol, 1.3 eq) and 4-Dimethylaminopyridine (0.479 g, 1.74 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2 (0.172 g, 9.31%). MS(ES): m/z 266.31 [M+H]$^+$.

Synthesis of Compound 1.3.

To a solution of 1.2 (0.172 g, 0.648 mmol, 1.0 eq), in tetrahydrofuran: water (10 mL, 2:1) was added lithium Synthesis of Compound 108n.

To a solution of 1 (1 g, 7.77 mmol, 1.0 eq) in dimethyl sulphoxide (10 mL), 1.1 (1.65 g, 23.31 mmol, 3.0 eq) was added. The reaction mixture was degassed for 10 min under argon atmosphere followed by addition of potassium carbonate (3.21 g, 23.31 mmol, 3.0 eq). The reaction mixture was heated at 190° C. for 10 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108n (0.400 g, Yield: 31.50%). MS (ES): m/z 164.11 [M+H]$^+$

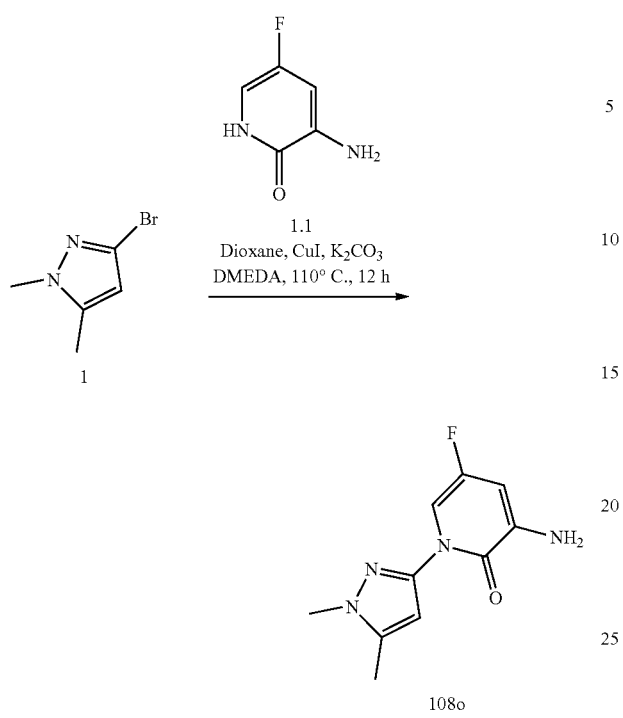

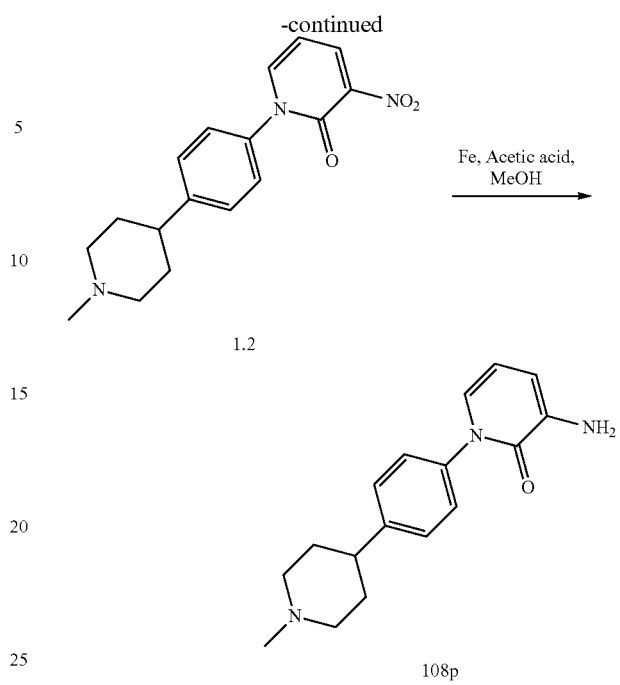

Synthesis of Compound 108o.

To a solution of 1 (1 g, 5.71 mmol, 1.0 eq) in 1,4-dioxane (100 mL), 1.1 (1.8 g, 8.57 mmol, 1.5 eq) was added. The reaction mixture was degassed for 10 min under argon atmosphere followed by addition of potassium carbonate (1.57 g, 11.42 mmol, 2.0 eq), N,N-dimethylethylenediamine (0.20 g, 2.28 mmol, 0.4 eq), and copper iodide (0.216 g, 1.14 mmol, 0.2 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108o (0.550 g, Yield: 43.32%). MS (ES): m/z 223.10 [M+H]+

Synthesis of Compound 1.2:

To a solution of 1 (0.5 g, 1.66 mmol, 1.0 eq), in ethanol: acetonitrile (50 mL) was added copper acetate (0.301 g, 1.66 mmol, 1.0 eq), 1.1 (0.23 g, 1.66 mmol, 1.0 eq) and triethyl amine (0.46 mL, 3.32 mmol, 2.0 eq) and stirred at 90° C. for 16 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.2 (0.210 g, 40.38%). MS(ES): m/z 314.38 [M+H]+

Synthesis of Compound 108p:

To a solution of 1.2 (0.210 g, 0.67 mmol, 1.0 eq) in methanol and acetic acid (10 mL), iron (0.184 g, 3.35 mmol, 5.0 eq) was added. Reaction mixture was stirred for 5 h at room temperature. After completion of reaction, reaction mixture was filtered through celite-bed and washed with methanol. Filtrate was concentrated under reduced pressure to obtain crude material and basified with saturated bicarbonate solution. Product was extracted with ethyl acetate. Organic layer was combined and dried over sodium sulphate and concentrated under reduced pressure to obtain crude material. This was further purified by trituration with diethyl ether to obtain pure 108p (0.110 g, 57.92%). MS (ES): m/z 284.38 [M+H].

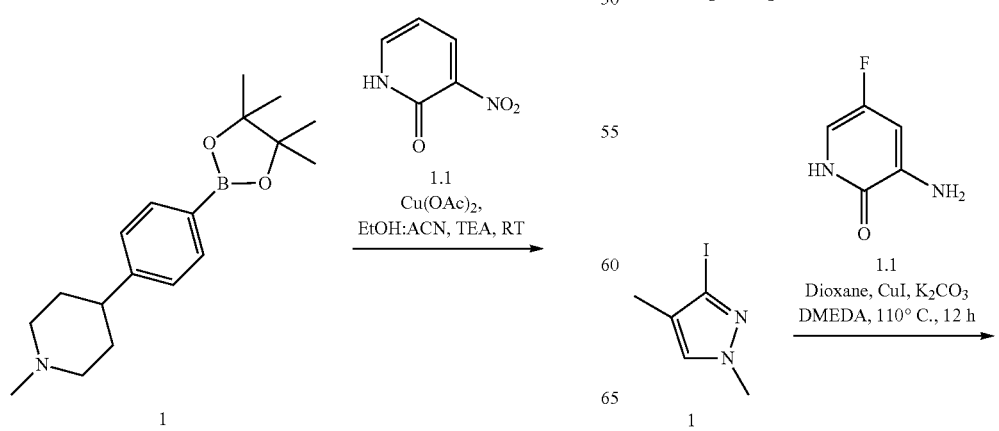

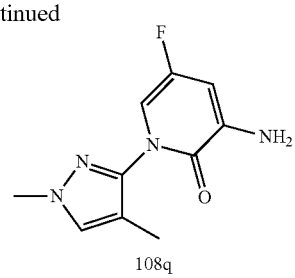

108q

Synthesis of Compound 108q.

To a solution of 1 (0.8 g, 3.60 mmol, 1 eq) in 1,4-dioxane (40 mL), 1.1 (0.599 g, 4.68 mmol, 1.3 eq) was added. The reaction mixture was degassed for 10 min under argon atmosphere followed by addition of potassium carbonate (1.24 g, 9.0 mmol, 2.5 eq), N,N-dimethylethylenediamine (0.079 g, 0.9 mmol, 0.25 eq), and copper iodide (0.102 g, 0.54 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108q (0.045 g, Yield: 5.62%). MS (ES): m/z 223.10 [M+H]+

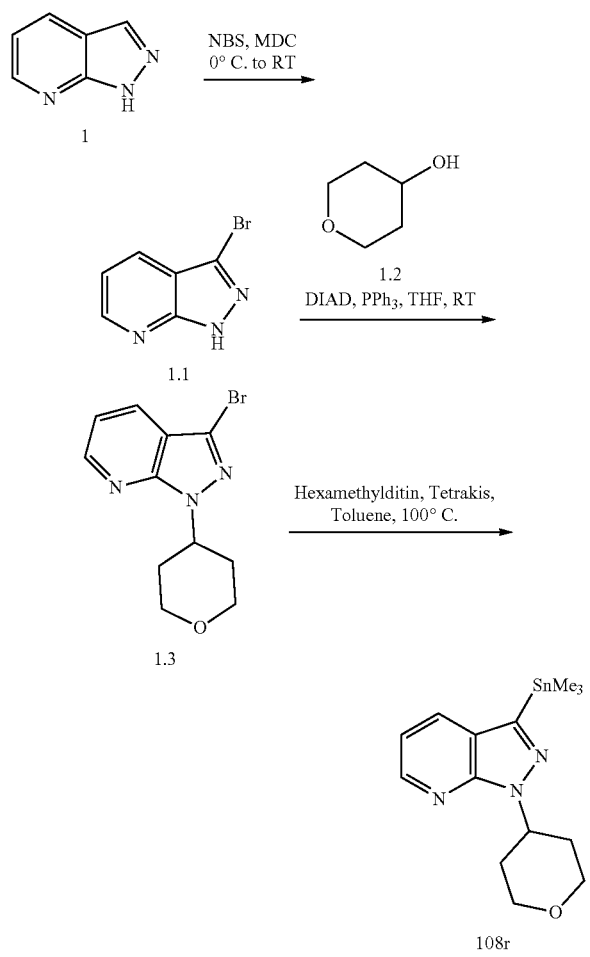

Synthesis of Compound 1.1.

To a stirred solution of 1 (3.0 g, 25.21 mmol, 1.0 eq) in dimethyl formamide (30 mL) was added N-bromosuccinimide (4.7 g, 26.47 mmol, 1.05 eq) at 10° C. under $N_2$ portionwise. Reaction mixture was stirred for 30 min. After completion of reaction, reaction mixture was transferred into ice cold water and the precipitated solid was collected by filtration, dried well to obtain 1.1 (3.23 g, 66%). MS(ES): m/z 198.96 [M+2H]+.

Synthesis of Compound 1.3.

To a stirred solution of 1.1 (3.0 g, 15.15 mmol, 1.0 eq), 1.2 (3.1 g, 30.30 mmol, 2.0 eq) and triphenyl phosphine (7.9 g, 30.30 mmol, 2.0 eq) in dry tetrahydrofuran (75 mL) was added diisipropyl azodicarboxylate (6.1 g, 30.30 mmol, 2.0 eq) at 0° C. under Ar dropwise over 20 min. The reaction mixture was stirred at room temperature for 16 h. The reaction mixture was concentrated under reduced pressure to obtain the crude material. The residue was further purified by column chromatography and compound was eluted in 24% ethyl acetate in hexane to obtain pure 1.3 (3.0 g, 70.25%). MS(ES): m/z 283.21 [M+H]+.

Synthesis of Compound 108r.

To a degassed solution of 1.3 (1.0 g, 3.54 mmol, 1.0 eq) and hexamethyl ditin (4.6 g, 14.18 mmol, 4.0 eq) in toluene (60 mL) was added tetrakis(triphenylphosphine)palladium (0) (0.410 g, 0.35 mmol, 0.1 eq) and the reaction mixture was heated at 100° C. for 2 h under $N_2$. Reaction mixture was cooled to room temperature purified by column chromaography using 6.0% ethyl acetate in hexane to obtain pure 108r (0.840 g, 64.61%). MS(ES): m/z 368.25 [M+H]+.

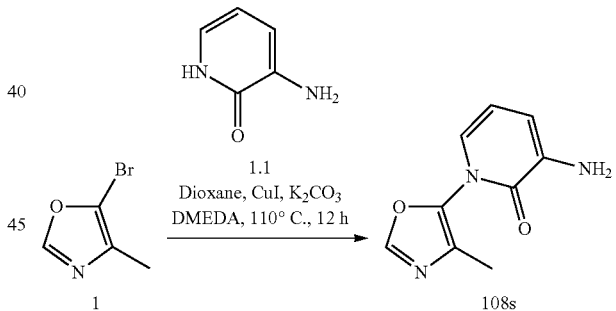

Synthesis of Compound 108s.

To a solution of 1 (0.8 g, 4.93 mmol, 1 eq) in 1,4-dioxane (45 mL), 1.1 (0.650 g, 5.91 mmol, 1.2 eq) was added. The reaction mixture was degassed for 10 min under argon atmosphere followed by addition of potassium carbonate (1.70 g, 12.32 mmol, 2.5 eq), N,N-dimethylethylenediamine (0.108 g, 1.23 mmol, 0.25 eq), and copper iodide (0.139 g, 0.73 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 108s. (0.37 g, Yield: 39.19%). MS (ES): m/z 192.07 [M+H]+

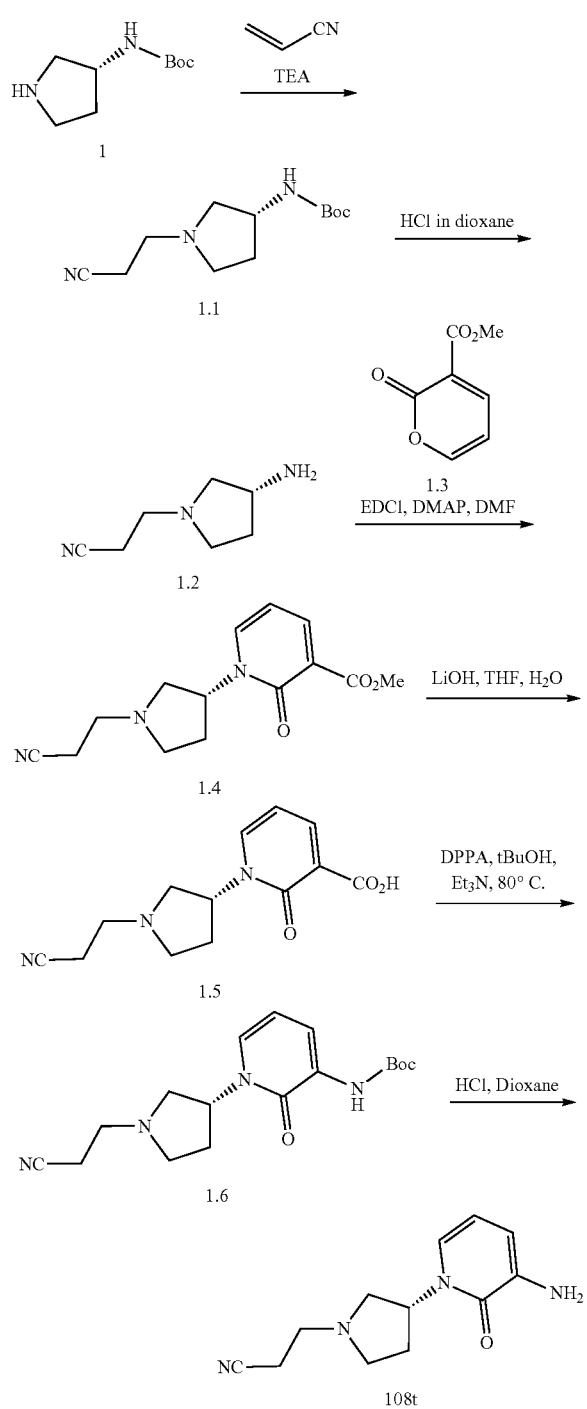

Synthesis of Compound 1.1.

To a solution of 1 (5 g, 26.88 mmol, 1.0 eq) in ethanol (50 ml) were added acrylonitrile (7.1 g, 134.4 mmol, 5.0 eq) and triethyl amine (8.1 g, 80.64 mmol, 3.0 eq) and stirred at 80° C. for 2 h. After completion of reaction, reaction mixture was transferred into water and product was extracted with ethyl acetate. Organic layer was combined and dried over sodium sulphate and concentrated under reduced pressure to obtain 1.1. (4.6 g, 71.60%). MS(ES): m/z 240.17 [M+H]

Synthesis of Compound 1.2.

A cooled solution of 1.1 (4.6 g, 19.24 mmol, 1 eq) in dioxane (35 mL) was added 4N hydrochloric acid in dioxane (60 mL) as a dropwise. The reaction mixture was stirred at room temperature for 2 h. After completion of reaction, reaction mixture was concentrated under reduced pressure to obtain pure 1.2. (4.6 g, 97.17%). MS(ES): m/z 140.11 [M+HCl]$^+$ Synthesis of Compound 1.4.

To a cooled solution of 1.2 (4.6 g, 33.09 mmol, 1.0 eq), in N,N-dimethylformamide (45 mL) was added 1.3 (5.0 g, 33.09 mmol, 1.0 eq). The reaction mixture was stirred at 0° C. for 30 min and further stirred at room temperature for 15 min. N-Ethyl-N'-(3-dimethylaminopropyl)carbodiimide hydrochloride (6.6 g, 43.09 mmol, 1.3 eq), 4-Dimethylaminopyridine (0.807 g, 6.61 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.4. (0.945 g, 10.39%). MS(ES): m/z 276.1[M+H]$^+$ Synthesis of Compound 1.5.

To a solution of 1.4 (0.945 g, 3.43 mmol, 1.0 eq), in tetrahydrofuran: water (14 mL, 2:1) was added lithium hydroxide (0.823 g, 34.3 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.5. (0.650 g, 72.48%). MS(ES): m/z 262.11 [M+H]$^+$ Synthesis of Compound 1.6.

To a solution of 1.5 (0.650 g, 2.48 mmol, 1.0 eq) in tert.butanol (12 mL) was added triethylamine (0.425 g, 4.21 mmol, 1.7 eq) and diphenyl phosphoryl azide (0.886 g, 3.22 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.6. (0.3 g, 36.28%). MS(ES): m/z 333.19 [M+H]$^+$ Synthesis of Compound 108t.

To 1.6 (0.3 g, 0.90 mmol, 1.0 eq) was added 4M hydrochloric acid in 1,4 Dioxane (12 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 108t. (0.180 g, Yield: 85.86%), MS (ES): m/z 233.13 [M+H].

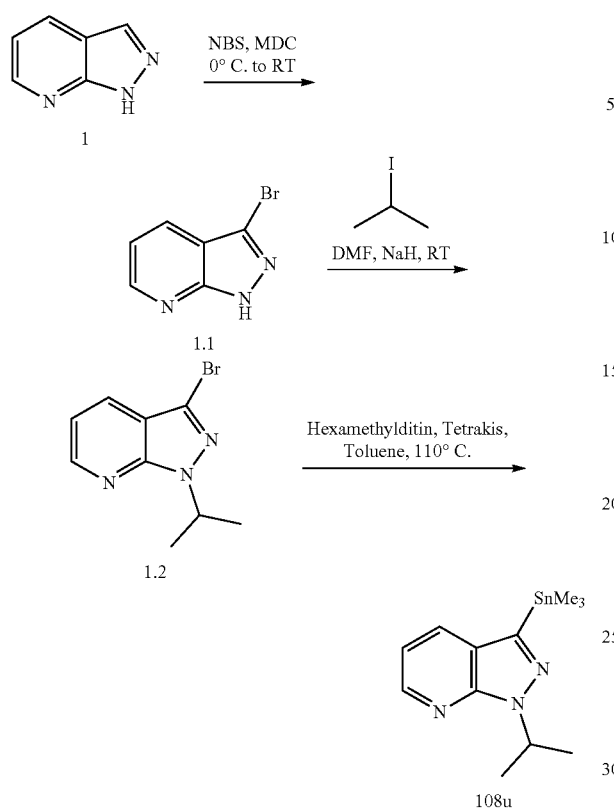

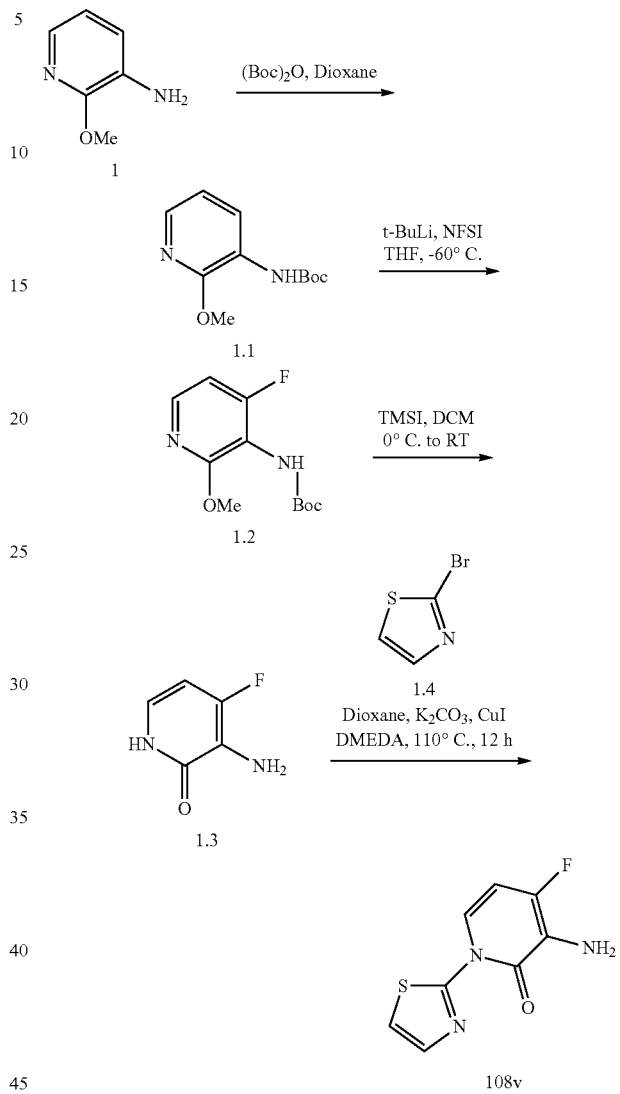

using 5.0% ethyl acetate in hexane as eluant to obtain pure 108 u (0.260 g, 99.05%). MS(ES): m/z 325.44 [M+H]$^+$.

Synthesis of Compound 1.1.

To a stirred solution of 1 (3.0 g, 25.21 mmol, 1.0 eq) in dimethyl formamide (30 mL) was added N-bromo succinimide (4.7 g, 26.47 mmol, 1.05 eq) at 10° C. under N$_2$ portionwise. Reaction mixture was stirred for 30 min. After completion of reaction, reaction mixture was transferred into ice cold water and the precipitated solid was collected by filtration, dried well to obtain 1.1 (3.23 g, 66.00%). MS(ES): m/z 198.96 [M+2H]$^+$.

Synthesis of Compound 1.2.

To a stirred suspension of sodium hydride (0.796 g, 19.89 mmol, 1.3 eq, 60% dispersion) in N,N-dimethyl formamide (10 mL) was added a solution of 1.1 (3.0 g, 15.30 mmol, 1.0 eq) in N,N-dimethyl formamide (15 mL) dropwise at 0° C. under N$_2$. The mixture was stirred for 20 mins under the same conditions and a solution of isopropyl iodide (3.1 g, 18.36 mmol, 1.2 eq) in N,N-dimethyl formamide (5 mL) was added dropwise. The reaction mixture was stirred at room temperature for 14 h. After completion of reaction, reaction mixture was transferred into ice cold water and the product was extracted with ethyl acetate. Organic layer was combined, washed with brine, dried over sodium sulfate and concentrated under reduced pressure to obtain crude material. This was further purified by column chromaography using 30% ethyl acetate in hexane as eluant to obtain pure 1.2 (2.46 g, 67.5%). MS(ES): m/z 240.41 [M+H]$^+$.

Synthesis of Compound 108u.

To a degassed solution of 1.2 (0.200 g, 0.83 mmol, 1.0 eq) and hexamethyl ditin (1.05 g, 3.33 mmol, 4.0 eq) in toluene (10 mL) was added Tetrakis(triphenylphosphine)palladium (0) (0.097 g, 0.08 mmol, 0.1 eq) and the reaction mixture was heated at 100° C. for 1 h under N$_2$. The RM was cooled to room temperature purified by column chromaography Synthesis of Compound 1.1.

To a stirred solution of 1 (10.0 g, 80.64 mmol, 1.0 eq) in 1,4-dioxane (100 mL) was added di-tert-butyl carbonate (1.595 g, 11.56 mmol, 1.2 eq) at room temperature under N$_2$ and the reaction mixture heated at 100° C. for 14 h. The reaction mixture was transferred into cold water and product was extracted with ethyl acetate. The combined organic phase was dried over sodium sulphate and concentrated under reduced pressure to obtain crude material. This was further purified by column chromatography and compound was eluted in 1% ethyl acetate in hexane to obtain pure 1.1 (12.0 g, 66.66%). MS(ES): m/z 225.44 [M+H]$^+$.

Synthesis of Compound 1.2.

To a stirred solution of 1.1 (10.0 g, 44.64 mmol, 1.0 eq) in dry tetrahydrofuran (200 mL) was added ter-butyl lithium (105 mL, 1.7 M in pentane, 178.57 mmol, 4.0 eq) at −70° C. under argon dropwise over 20 mins. The reaction mixture was allowed to warm to −25° C. over 40 mins, stirred for 10 mins and recooled to −70° C. A solution of N-fluorobenzenesulfonamide (15.0 g, 47.61 mmol, 1.06 eq) in dry tetrahydrofuran (50 mL) was added dropwise over 5 mins and the mixture was allowed to warm to −20° C. over 40 mins. The reaction was quenched by slow addition of cold water and the product was extracted with ethyl acetate. The combined organic phase was dried over sodium sulphate and concentrated under reduced pressure to obtain crude material. This was further purified by column chromatography and compound was eluted in 4% ethyl acetate in hexane to obtain pure 1.2 (5.2 g, 48.06%). MS(ES): m/z 243.425 [M+H]⁺.

Synthesis of Compound 1.3.

To a stirred solution of 1.2 (5.0 g, 20.66 mmol, 1.0 eq) in dichloromethane (50 mL) was added a solution of trimethyl silyl iodide (4.6 g, 22.72 mmol, 1.1 eq) in dichloromethane (20 mL) dropwise at 0° C. under $N_2$ and the reaction mixture was stirred at room temperature for 4 h. The reaction mixture was evaporated under reduced pressure. The residue was dissolved in dichloromethane and some wet crystals of sodium thiosulfate were added. The mixture was stirred until the brown colour disappeared. The mixture was filtered and the solid residue was washed with 30% ethyl acetate in hexane, dried well to obtain 1.3 (1.0 g, 34.42%). ¹H NMR (DMSO-d₆, 400 MHZ): 11.56 (brs, 1H), 6.76-6.72 (t, J=7.2 Hz, 1H), 6.24-6.20 (t, J=7.6 Hz, 1H), 4.76 (s, 2H).

Synthesis of Compound 108v.

To a degassed solution of 1.3 (0.650 g, 5.08 mmol, 1.0 eq) and 1.4 (1.33 g, 7.62 mmol, 1.5 eq) in dimethylformamide (16 mL) was added potassium orthophosphate (2.15 g, 10.15 mmol, 2.0 eq), cuprous iodide (0.193 g, 1.02 mmol, 0.2 eq) and N, N'-dimethylethylene diamine (0.180 g, 2.03 mmol, 0.4 eq) and the reaction mixture was heated at 90° C. for 4 h under $N_2$. Reaction mixture was cooled to room temperature filtered and the filtrate was concentrated under reduced pressure to obtain residue which was further purified by column chromatography and compound was eluted in 8.5% ethyl acetate in hexane to obtain pure 108v (0.100 g, 9.35%). ¹H NMR (DMSO-d₆, 400 MHZ): 8.20-8.15 (t, J=7.2 Hz, 1H), 7.80-7.78 (d, J=3.6 Hz, 1H), 7.67-7.60 (d, J=3.6 Hz, 1H), 6.72-6.67 (t, J=8.4 Hz, 1H), 5.41 (s, 2H).

(0.048 g, 0.544 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 108 w (0.033 g, 11.64%). MS(ES): m/z 202.2 [M+H]⁺.

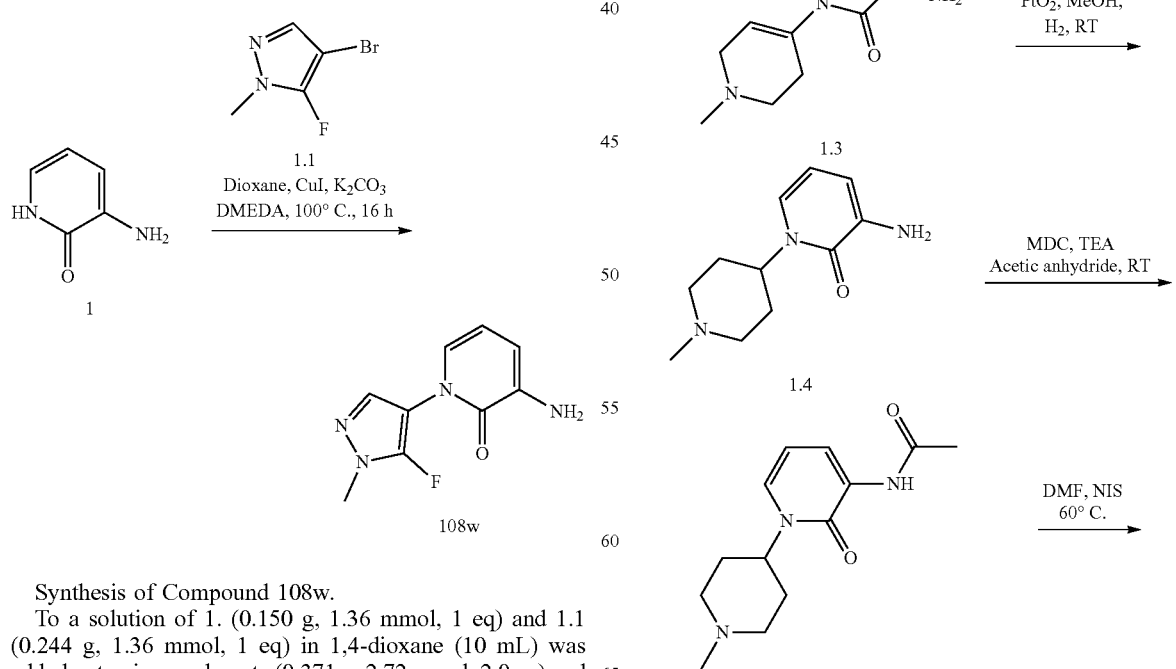

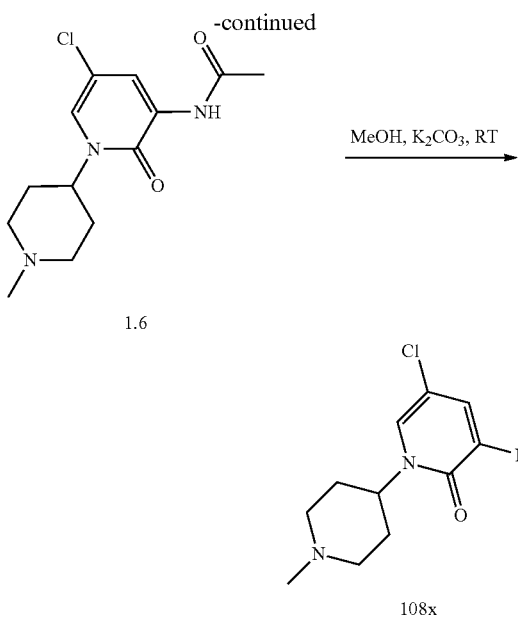

Synthesis of Compound 1.2:

To a solution of 1. (10 g, 71.42 mmol, 1.0 eq), in 1,4-dioxane (100 mL) were added copper acetate (12.96 g, 71.42 mmol, 1.0 eq), 1.1 (15.92 g, 71.42 mmol, 1.0 eq) and triethyl amine (20 mL, 142 mmol, 2.0 eq) and stirred at 80° C. for 16 h. After completion of reaction, reaction mixture was transferred into water and product was extracted with ethyl acetate. Organic layer was combined and dried over sodium sulphate and concentrated under reduced pressure to obtain crude material. This was further purified by trituration with diethyl ether to obtain pure 1.2 (9 g, 53.60%). MS(ES): m/z 236.24 [M+H]$^+$ Synthesis of Compound 1.3:

To a solution of 1.2 (9 g, 38.13 mmol, 1.0 eq) in acetic acid (90 mL), iron (10.6 g, 190.1 mmol, 5 eq) was added. Reaction mixture was stirred for 5 h at room temperature. After completion of reaction, reaction mixture was filtered through celite-bed and washed with methanol. Filtrate was concentrated under reduced pressure to obtain crude material and basified with saturated bicarbonate solution. Product was extracted with ethyl acetate. Organic layer was combined and dried over sodium sulphate and concentrated under reduced pressure to obtain crude material. This was further purified by trituration with diethyl ether to obtain pure 1.3 (6 g, 76.40%). MS (ES): m/z 206.38 [M+H].$^+$ Synthesis of Compound 1.4:

To a solution of 1.3 (6 g, 29.12 mmol, 1.0 eq) in methanol (15 mL), palladium on charcoal (0.6 g) was added. Hydrogen was purged through reaction mixture for 5 h at room temperature. After completion of reaction, reaction mixture was filtered through celite-bed and washed with methanol. Filtrate was concentrated under reduced pressure to obtain crude material. This was further purified by trituration with n-pentane to obtain pure 1.4 (5 g, 82.52%). MS (ES): m/z 208 [M+H]$^+$ Synthesis of Compound 1.5:

To a solution of 1.4 (5 g, 24.15 mmol, 1.0 eq) in dichloromethane (25 mL), was added triethyl amine (4.8 g, 48.30 mmol, 2.0 eq) and acetic anhydride (12.25 g, 120 mmol, 5.0 eq) at 0° C. The reaction mixture was stirred at room temperature for 3 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.5 (5.5 g, Yield: 91.45%). MS (ES): m/z 250.5 [M+H]$^+$ Synthesis of Compound 1.6:

To a solution of 1.5 (5.5 g, 22.08 mmol, 1.0 eq) in dichloromethane (50 mL), was added N-Iodo-succinimide (5.9 g, 26.50 mmol, 1.2. eq) at 0° C. The reaction mixture was stirred at room temperature for 16 h. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 3% methanol in dichloromethane to obtain 1.6 (1.8 g, Yield: 28.75%). MS (ES): m/z 284.5 [M+H]$^+$ Synthesis of Compound 108x:

To a solution of 1.6 (1.8 g, 6.3 mmol, 1.0 eq) in methanol (15 mL), potassium carbonate (1.75 g, 12.7 mmol, 2 eq.) was added. Reaction mixture was stirred for overnight at room temperature. After completion of reaction, reaction mixture was filtered through celite-bed and washed with methanol. Filtrate was concentrated under reduced pressure to obtain crude material. This was further purified by trituration with n-pentane to obtain pure 108x (0.8 g, 50.17%). MS (ES): m/z 242.5 [M+H]$^+$

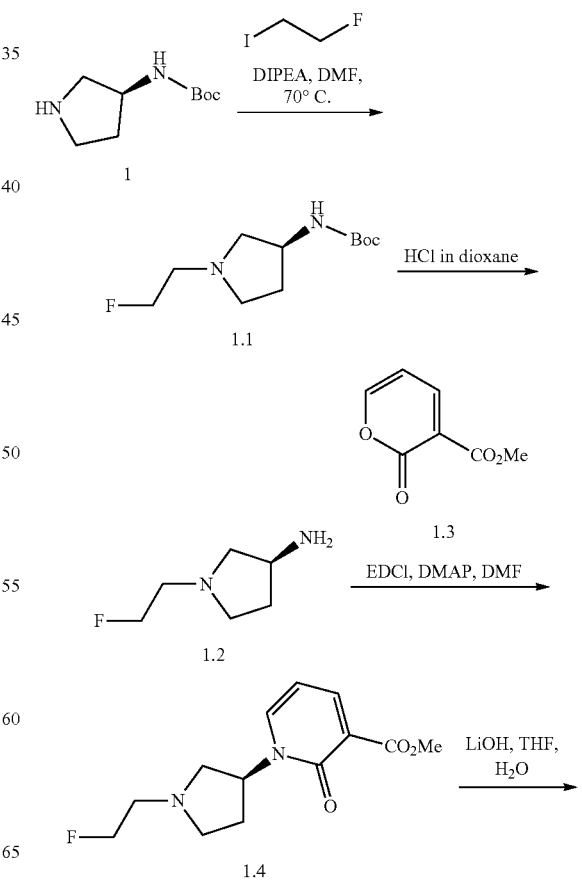

1821

-continued

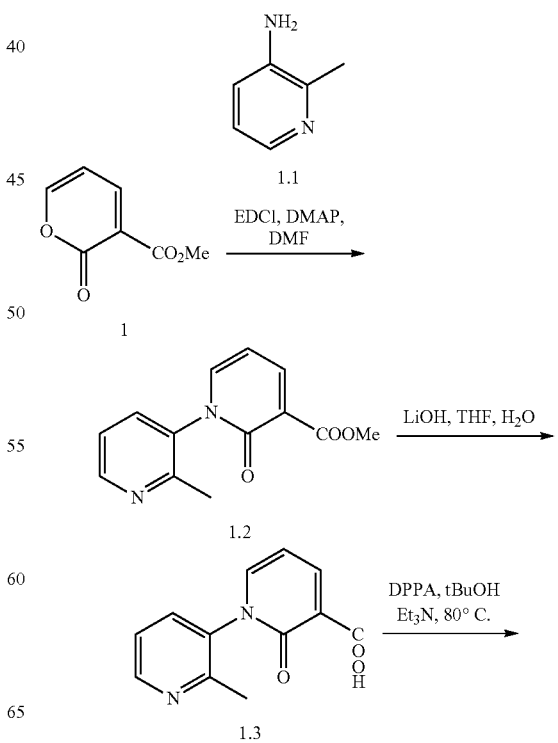

Synthesis of Compound 1.1.

To a solution of 1 (2.0 g, 10.74 mmol, 1 eq) and 1-fluoro-2-iodoethane (2.24 g, 12.89 mmol, 1.2 eq) in N,N-dimethylformamide (20 mL) was added N,N-Diisopropyl-ethylamine (4.164 g, 32.22 mmol, 3.0 eq) and degassed with argon for 15 min followed by heating at 70° C. for 6 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 1.1 (1.7 g, 68.15%). MS(ES): m/z 233.30 [M+H]$^+$.

Synthesis of Compound 1.2.

To 1.1 (1.2 g, 7.32 mmol, 1.0 eq) was added 4M hydrochloric acid in 1,4 Dioxane (25 mL) and stirred at room temperature for 4 h. After completion of reaction, reaction mixture was concentrated under reduced pressure, residue was triturated with diethyl ether to obtain 1.2. (0.9 g, 93.04%). MS (ES): m/z 133.18 [M+H]$^+$ Synthesis of Compound 1.4.

To a cooled solution of 1.2 (0.9 g, 6.81 mmol, 1.0 eq), in N,N-dimethylformamide (10 mL) was added 1.3 (1.05 g, 6.81 mmol, 1.0 eq). The reaction mixture was stirred at 0° C. for 6 h and further stirred at room temperature for 15 min. N-Ethyl-N'-(3-dimethylaminopropyl)carbodiimide hydrochloride (1.44 g, 7.57 mmol, 1.3 eq) and 4-Dimethylamin-opyridine (0.141 g, 1.16 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 1.4. (0.37 g, 20.25%). MS(ES): m/z 269.29 [M+H]$^+$.

Synthesis of Compound 1.5.

To a solution of 1.4 (0.370 g, 1.38 mmol, 1.0 eq), in tetrahydrofuran: water (6 mL, 2:1) was added lithium hydroxide (0.288 g, 12.0 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.5. (0.31 g, 88.42%). MS(ES): m/z 255.26 [M+H]$^+$.

Synthesis of Compound 1.6.

To a solution of 1.5 (0.310 g, 1.22 mmol, 1.0 eq) in tert.butanol (6 mL) was added triethylamine (0.210 g, 2.074 mmol, 1.7 eq) and diphenyl phosphoryl azide (0.436 g, 1.586 mmol, 1.3 eq) under nitrogen followed by heating at 85° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 1.6. (0.210 g, 52.93%). MS(ES): m/z 326.38 [M+H]$^+$.

Synthesis of Compound 108y.

To 1.6 (0.210 g, 0.645 mmol, 1.0 eq) was added 4M hydrochloric acid in 1,4 Dioxane (5 mL) and stirred at room temperature for 4 h. After completion of reaction, reaction mixture was concentrated under reduced pressure, residue was triturated with diethyl ether to obtain 108y (0.10 g, 68.78%). MS (ES): m/z 226.27 [M+H]$^+$

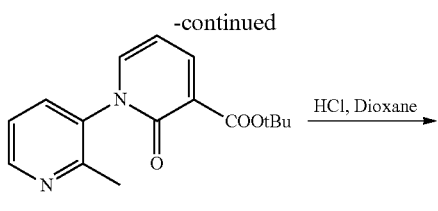

1.4

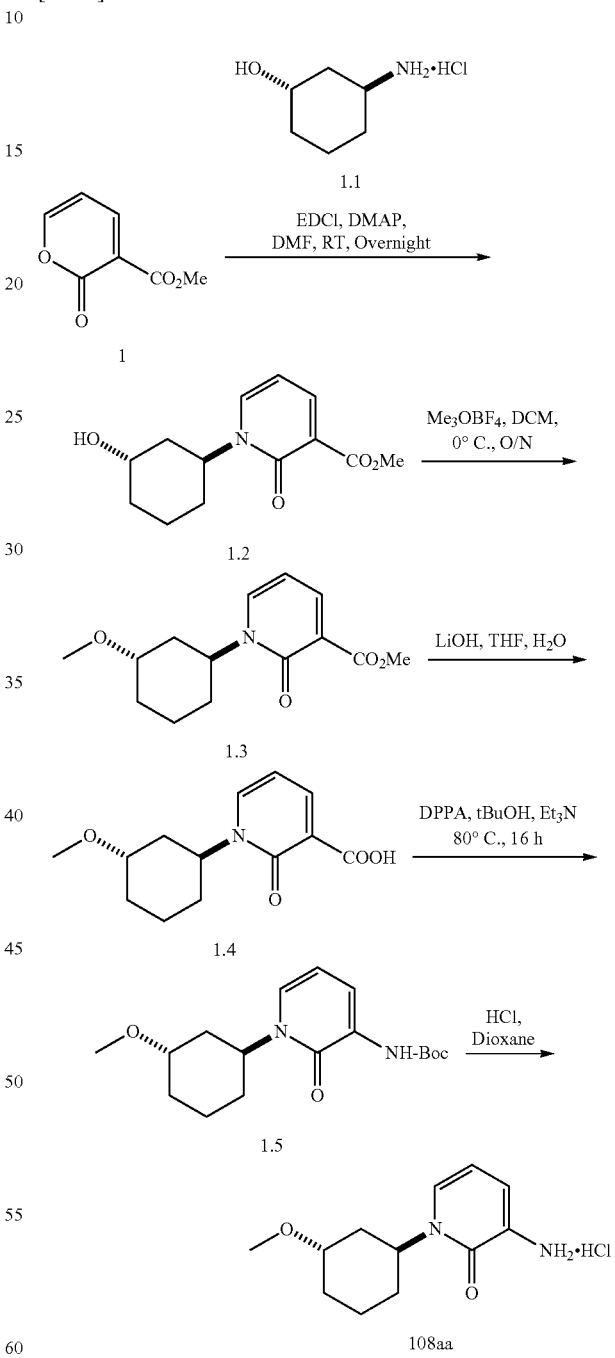

Synthesis of Compound 108z.

A cooled solution of 1.4 (1.1 g, 3.84 mmol, 1 eq) in dioxane (10 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 108z. (0.760 g, 98.31%). MS(ES): m/z 202.09 [M+H]$^+$ Synthesis of Compound 1.2.

To a cooled solution of 1 (2.0 g, 12.97 mmol, 1.0 eq), in N,N-dimethylformamide (55 mL) was added 1.1 (1.40 g, 12.97 mmol, 1.0 eq). The reaction mixture was stirred at 0° C. for 6 h and further stirred at room temperature for 15 min. N-Ethyl-N'-(3-dimethylaminopropyl)carbodiimide hydrochloride (2.61 g, 16.86 mmol, 1.3 eq) and 4-Dimethylaminopyridine (0.316 g, 2.59 mmol, 0.2 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 49% ethyl acetate in hexane to obtain 1.2. (1.9 g, 59.94%). MS(ES): m/z 245.09 [M+H]$^+$.

Synthesis of Compound 1.3.

To a solution of 1.2 (1.9 g, 7.77 mmol, 1.0 eq), in tetrahydrofuran: methanol: water (90 mL, 2:2:1) was added lithium hydroxide (0.745 g, 31.08 mmol, 4.0 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 1.3. (1.5 g, 83.76%). MS(ES): m/z 231.07 [M+H]$^+$.

Synthesis of Compound 1.4.

To a solution of 1.3. (1.5 g, 6.51 mmol, 1.0 eq) in tert.butanol (30 mL) was added triethylamine (1.1 g, 11.06 mmol, 1.7 eq) and diphenyl phosphoryl azide (2.32 g, 8.46 mmol, 1.3 eq) under nitrogen followed by heating at 80° C. for 24 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 40% ethyl acetate in hexane to obtain pure 1.4. (1.1 g, 98.96%). MS(ES): m/z 287.14 [M+H]$^+$.

Synthesis of Compound 1.2.

To a cooled solution of 1 (1.0 g, 6.48 mmol, 1.0 eq), in N,N-dimethylformamide (15 mL) was added 1.1 (0.982 g, 6.48 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.30 g, 8.42 mmol, 1.3 eq) and 4-Dimethylaminopyridine (0.157 g, 1.29 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.4 g, 29.53%). MS(ES): m/z 252.12 [M+H]$^+$.

Synthesis of Compound 1.3.

To a solution of 1.2 (0.4 g, 1.59 mmol, 1.0 eq), in dichloromethane (5 mL) was added Trimethyloxonium tetrafluoroborate (0.470 g, 3.18 mmol, 2.0 eq) at 0° C. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 1.3. (0.150 g, 35.52%). MS(ES): m/z 266.13 [M+H]$^+$.

Synthesis of Compound 1.4.

To a solution of 1.3 (0.150 g, 0.56 mmol, 1.0 eq), in tetrahydrofuran: water (3 mL, 2:1) was added lithium hydroxide (0.134 g, 5.6 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.4. (0.123 g, 86.58%). MS(ES): m/z 252.12 [M+H]$^+$.

Synthesis of Compound 1.5.

To a solution of 1.4 (0.123 g, 0.48 mmol, 1.0 eq) in tert.butanol (3 mL) was added triethylamine (0.081 g, 0.81 mmol, 1.7 eq) and diphenyl phosphoryl azide (0.171 g, 0.62 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.5. (0.080 g, 50.69%). MS(ES): m/z 323.19 [M+H]$^+$.

Synthesis of Compound 108aa.

A cooled solution of 1.5. (0.080 g, 0.24 mmol, 1 eq) in dioxane (2 mL) was added 4N hydrochloric acid in dioxane (5 mL) as a dropwise. The reaction mixture was stirred at room temperature for 2 h. After completion of reaction, reaction mixture was concentrated under reduced pressure to obtain pure 108aa. (0.060 g, 93.45%). MS(ES): m/z 259.12 [M+HCl]$^+$.

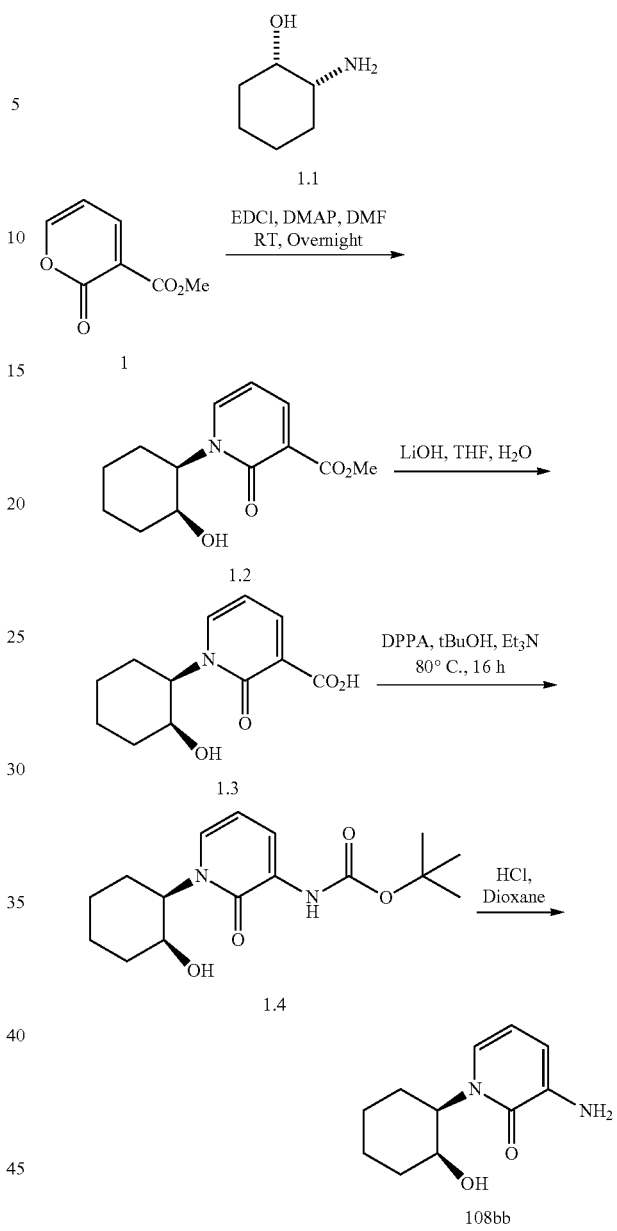

Synthesis of Compound 1.2.

To a cooled solution of 1 (0.154 g, 0.99 mmol, 1.0 eq), in N,N-dimethylformamide (5 mL) was added 1.1 (0.114 g, 0.99 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.198 g, 1.28 mmol, 1.3 eq) and 4-Dimethylaminopyridine (0.023 g, 0.19 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.7 g, 53.67%). MS(ES): m/z 252.12 [M+H]$^+$.

Synthesis of Compound 1.3.

To a solution of 1.2 (0.4 g, 1.59 mmol, 1.0 eq), in tetrahydrofuran: water (4 mL, 2:1) was added lithium hydroxide (0.360 g, 15 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.3 g, 79.43%). MS(ES): m/z 238.10 $[M+H]^+$.

Synthesis of Compound 1.4.

To a solution of 1.3 (0.3 g, 1.26 mmol, 1.0 eq) in tert.butanol (9 mL) was added triethylamine (0.216 g, 2.14 mmol, 1.7 eq) and diphenyl phosphoryl azide (0.448 g, 1.63 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.160 g, 41.03%). MS(ES): m/z 309.18 $[M+H]^+$.

Synthesis of Compound 108bb.

A cooled solution of 1.4 (0.160 g, 0.51 mmol, 1 eq) in dioxane (4 mL) was added 4N hydrochloric acid in dioxane (8 mL) as a dropwise. The reaction mixture was stirred at room temperature for 2 h. After completion of reaction, reaction mixture was concentrated under reduced pressure to obtain pure 108bb. (0.1 g, 92.55%). MS(ES): m/z 209.12 $[M+HCl]^+$.

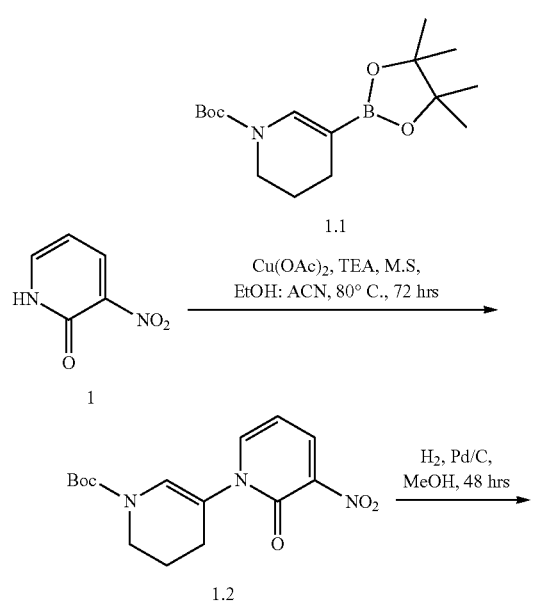

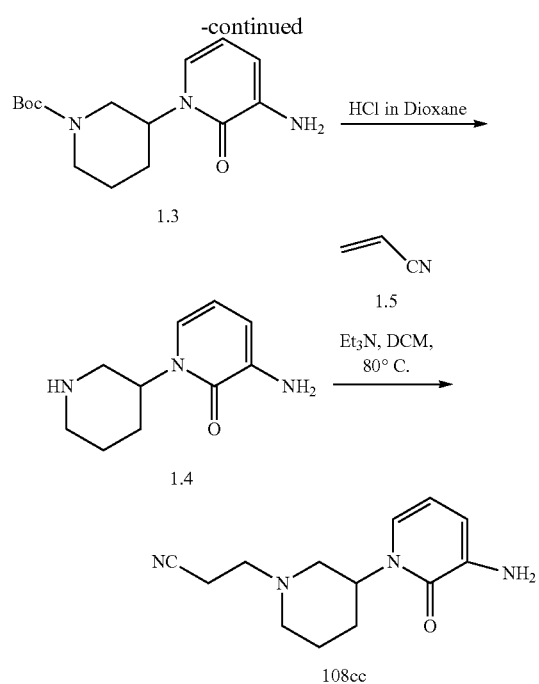

Synthesis of Compound 1.2.

To a stirred solution of 1 (1.2 g, 8.09 mmol, 1.0 eq) and 1.1 (2.5 g, 8.09 mmol, 1.0 eq) in a mixture of acetonitrile (20 mL) and ethanol (4 mL) was added copper (II) acetate (1.3 g, 8.09 mmol, 1.0 eq), triethyl amine (1.63 g, 16.18 mmol, 2.0 eq) and powdered molecular sieves (0.500 g, 4A) and the reaction mixture was stirred at 80° C. for 72 h. The reaction mixture was filtered, water was added to the filtrate and extracted with ethyl acetate. The combined organic extract was dried over sodium sulfate and concentrated under reduced pressure to get the crude product. This was purified by column chromatography and compound was eluted in 10% ethyl acetate in hexane to obtain pure 1.2 (0.700 g, 26.92%). MS(ES): m/z 3222.42 $[M+H]^+$.

Synthesis of Compound 1.3.

A stirred mixture of 1.2 (0.400 g, 1.24 mmol, 1.0 eq) and palladium on carbon (0.200 g, 10% w/w, 50% moisture) in methanol was hydrogenated under 1 atmosphere pressure of hydrogen at room temperature for 1 h. The reaction mixture was filtered through celite and the filtrate was concentrated under reduced pressure to get the crude product. This was purified by column chromatography and compound was eluted in 25% ethyl acetate in hexane to obtain pure 1.3 (0.300 g, 82.19%). MS(ES): m/z 294.34 $[M+H]^+$.

Synthesis of Compound 1.4.

To a stirred solution of 1.3 (0.300 g, 1.02 mmol) in dichloromethane (3 mL) was added 4 M HCl in dioxane (3 mL) dropwise at 0° C. under $N_2$ and the reaction mixture was stirred at room temperature for 3 h. The reaction mixture was concentrated under reduced pressure and the solid residue was triturated with pentane to obtain the hydrochloride salt of 1.4 (0.230 g, 97.95%). MS(ES): m/z 194.44 $[M+H]^+$.

Synthesis of Compound 108cc.

To a stirred mixture of 1.4 (0.180 g, 0.93 mmol, 1.0 eq) in ethanol (3 mL) was added 1.5 (0.180 g, 0.93 mmol, 5.0 eq) followed by triethyl amine (0.190 g, 1.87 mmol, 2.0 eq) and the reaction mixture was heated at 80° C. for 5 h. The reaction mixture was concentrated under reduced pressure and the residue was purified by column chromatography and compound was eluted in 1.9% methanol in dichloromethane to obtain pure 108cc (0.090 g, 39.21%). MS(ES): m/z 247.34 [M+H]+.

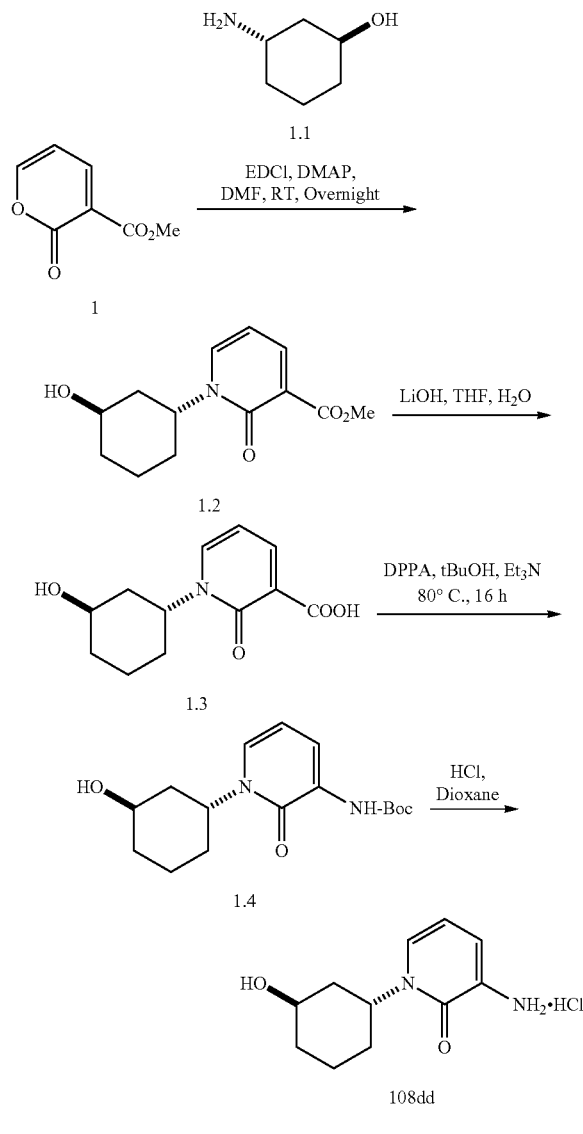

Synthesis of Compound 1.2.

To a cooled solution of 1. (1.3 g, 8.43 mmol, 1.0 eq), in N,N-dimethylformamide (20 mL) was added 1.1 (0.969 g, 8.43 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.69 g, 10.95 mmol, 1.3 eq) and 4-Dimethylaminopyridine (0.204 g, 1.68 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.9 g, 42.46%). MS(ES): m/z 252.12 [M+H]+.

Synthesis of Compound 1.3.

To a solution of 1.2 (0.9 g, 3.58 mmol, 1.0 eq), in tetrahydrofuran: water (12 mL, 2:1) was added lithium hydroxide (0.859 g, 35.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.710 g, 83.55%). MS(ES): m/z 238.10 [M+H]+.

Synthesis of Compound 1.4.

To a solution of 1.3 (0.710 g, 2.99 mmol, 1.0 eq) in tert.butanol (15 mL) was added triethylamine (0.513 g, 5.08 mmol, 1.7 eq) and diphenyl phosphoryl azide (1.0 g, 3.88 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.4 g, 43.34%). MS(ES): m/z 309.18[M+H]+.

Synthesis of Compound 108dd.

To a cooled solution of 1.4 (0.4 g, 1.29 mmol, 1 eq) in dioxane (6 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 108dd. (0.320 g, 97.66%). MS(ES): m/z 245.10 [M+HCl]+.

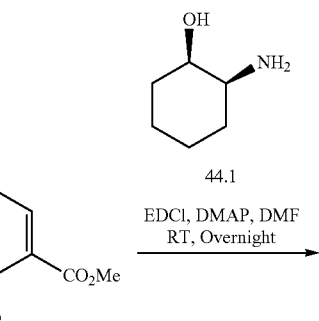

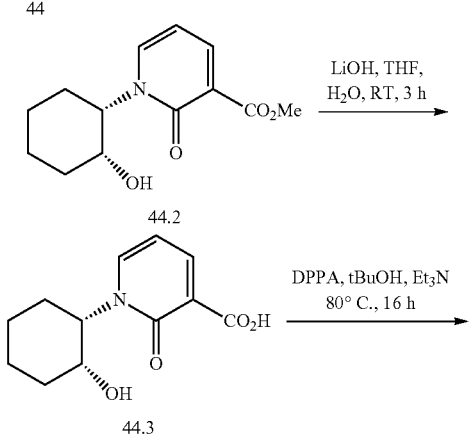

-continued

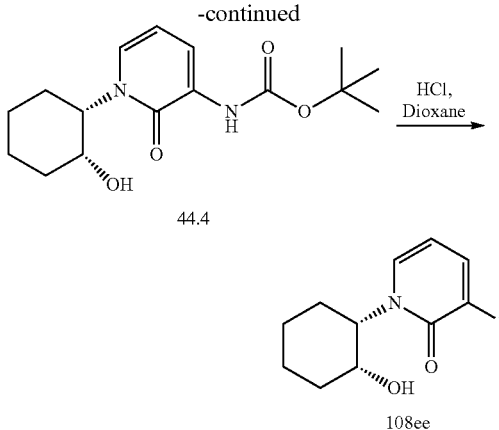

44.4

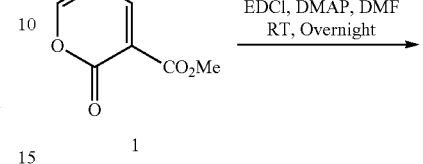

108ee

Synthesis of Compound 44.2.

To a stirred solution of 44.1 (5.0 g, 32.47 mmol, 1.0 eq) in N,N-dimethyl formamide (50 mL) was added 44 (5.0 g, 32.47 mmol, 1.0 eq) in one portion at 0° C. under Ar followed by diisopropyl ethyl amine (6.3 g, 48.71 mmol, 1.5 eq) and the reaction mixture was stirred at 0° C. for 3 h. 1-Ethyl-3-(3-dimethylaminopropyl)carbodiimide hydrochloride (8.1 g, 42.21 mmol, 1.3 eq) and then 4-Dimethylaminopyridine (1.0 g, 8.11 mmol, 0.25 eq) were added under argon and the reaction mixture was stirred at room temperature overnight. The reaction mixture was concentrated under reduced pressure to obtain residue which was purified by column chromatography and compound was eluted in 1.9% methanol in dichloromethane to obtain pure 44.2 (4.3 g, 52.76%). MS(ES): m/z 252.42 [M+H]$^+$.

Synthesis of Compound 44.3.

To a stirred solution of 44.2 (1.5 g, 5.98 mmol, 1.0 eq) in tetrahydrofuran (45 mL) was added methanol (16.5 mL) and a solution of lithium hydroxide monohydrate (1.1 g, 25.71 mmol, 4.5 eq) in water (22 mL) and the reaction mixture was stirred at room temperature for 3 h. The reaction mixture was concentrated under vacuum and the residue was adjusted to pH 3 by slow addition of 1N hydrochloric acid at 0° C. The precipitate was collected by filtration and dried to obtain pure compound 44.3 (0.90 g, 48.06%). MS(ES): m/z 238.45 [M+H]$^+$.

Synthesis of Compound 44.4.

A stirred mixture of 44.3 (0.90 g, 3.80 mmol, 1.0 eq), tert butanol (11 mL), diphenyl phosphoryl azide (1.5 g, 5.32 mmol, 1.4 eq) and triethyl amine (540 mg, 5.32 mmol, 1.4 eq) was heated at 80° C. under N$_2$ for 18 h. The reaction mixture was evaporated under reduced pressure. The residue was dissolved in ethyl acetate and the organic solution was washed with water. The organic phase was dried over sodium sulfate and concentrated under reduced pressure to obtain the crude. This was further purified by column chromatography and compound was eluted in 1% methanol in dichloromethane to obtain pure 44.4 (0.70 g, 59.82%). MS(ES): m/z 309.45 [M+H]$^+$.

Synthesis of Compound 108ee.

To a stirred solution of 44.4 (0.70 g, 2.27 mmol) in dichloromethane (10 mL) was added 4 M HCl in dioxane (5 mL) dropwise at 0° C. under N$_2$ and the reaction mixture was stirred at room temperature for 3 h. Reaction mixture concentrated under reduced pressure to obtain residue which was triturated with diethyl ether to obtain 108ee (0.40 g, 72.11%). MS(ES): m/z 209.32 [M+H]$^+$.

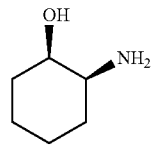

1.1

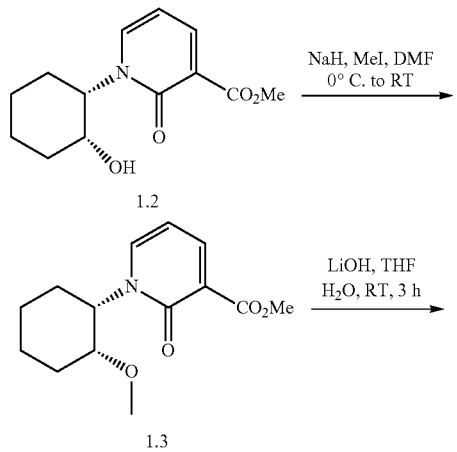

1.2

1.3

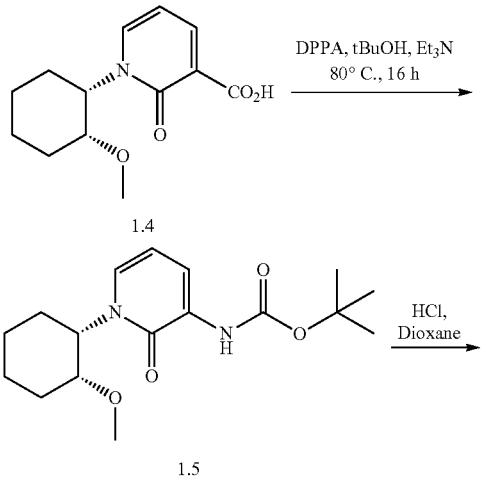

1.4

1.5

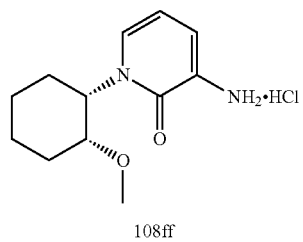

108ff

Synthesis of Compound 1.2.

To a stirred solution of 1.1 (5.0 g, 32.47 mmol, 1.0 eq) in N,N-dimethyl formamide (50 mL) was added 1 (5.0 g, 32.47 mmol, 1.0 eq) in one portion at 0° C. under Ar followed by diisopropyl ethyl amine (6.3 g, 48.71 mmol, 1.5 eq) and the reaction mixture was stirred at 0° C. for 3 h. 1-Ethyl-3-(3-dimethylaminopropyl)carbodiimide hydrochloride (8.1 g, 42.21 mmol, 1.3 eq) and 4-Dimethylaminopyridine (1.0 g, 8.11 mmol, 0.25 eq) were added under Ar and the reaction mixture was stirred at room temperature overnight. The reaction mixture was concentrated under reduced pressure and the residue was purified by column chromatography and compound was eluted in 1.9% methanol in dichloromethane to obtain pure 1.2 (4.3 g, 52.76%). MS(ES): m/z 252.42 [M+H]$^+$.

Synthesis of Compound 1.3.

To a stirred solution of 1.2 (4.0 g, 15.94 mmol, 1.0 eq) in dimethylformamide (40 mL) was added sodium hydride (1.3 g, 31.88 mmol, 2.0 eq, 60% dispersion) in small portions over 10 minutes under N$_2$ at 0° C. After stirring at room temperature for 15 minutes the reaction mixture was recooled to 0° C. and methyl iodide (2.9 g, 20.72 mmol, 1.3 eq) was added dropwise slowly over 10 minutes. The reaction mixture was stirred at room temperature for 2 h and then quenched with ice-water and extracted with ethyl acetate. The combined organic extract was washed with brine dried over sodium sulphate and concentrated under reduced pressure to get the crude product. This was purified by column chromatography and compound was eluted in 30% ethyl acetate in hexane to obtain pure 1.3 (2.30 g, 54.50%). MS(ES): m/z 266.34 [M+H]$^+$.

Synthesis of Compound 1.4.

To a stirred solution of 1.3 (2.30 g, 8.68 mmol, 1.0 eq) in tetrahydrofuran (70 mL) was added methanol (24.5 mL) and a solution of lithium hydroxide monohydrate (1.5 g, 34.72 mmol, 4.0 eq) in water (35 mL) and the reaction mixture was stirred at room temperature for 3 h. The reaction mixture was concentrated under reduced pressure and the residue was adjusted to pH 3 by slow addition of 1N HCl at 0° C. The precipitate was collected by filtration and dried to obtain pure compound 1.4 (1.9 g, 87.55%). MS(ES): m/z 252.45 [M+H]$^+$.

Synthesis of Compound 1.5.

A stirred mixture of 1.4 (1.90 g, 7.57 mmol, 1.0 eq), tert butanol (20 mL), diphenyl phosphoryl azide (2.9 g, 10.60 mmol, 1.4 eq) and triethyl amine (1.07 g, 10.60 mmol, 1.4 eq) was heated at 80° C. under N$_2$ for 18 h. The reaction mixture was evaporated under reduced pressure. The residue was dissolved in ethyl acetate and the organic solution was washed with water. The organic phase was dried over sodium sulfate and concentrated under reduced pressure to get the crude product. This was purified by column chromatography and compound was eluted in 1% methanol in dichloromethane to obtain pure 1.5 (1.8 g, 74.07%). MS(ES): m/z 323.34 [M+H]$^+$.

Synthesis of Compound 108ff.

To a stirred solution of 1.5 (1.8 g, 5.59 mmol) in dichloromethane (18 mL) was added 4 M HCl in dioxane (15 mL) dropwise at 0° C. under N$_2$ and the reaction mixture was stirred at room temperature for 3 h. Reaction mixture concentrated under reduced pressure and the solid residue was triturated with diethyl ether to obtain the hydrochloride salt of 108ff (1.20 g, 82.75%). MS(ES): m/z 223.64 [M+H]$^+$.

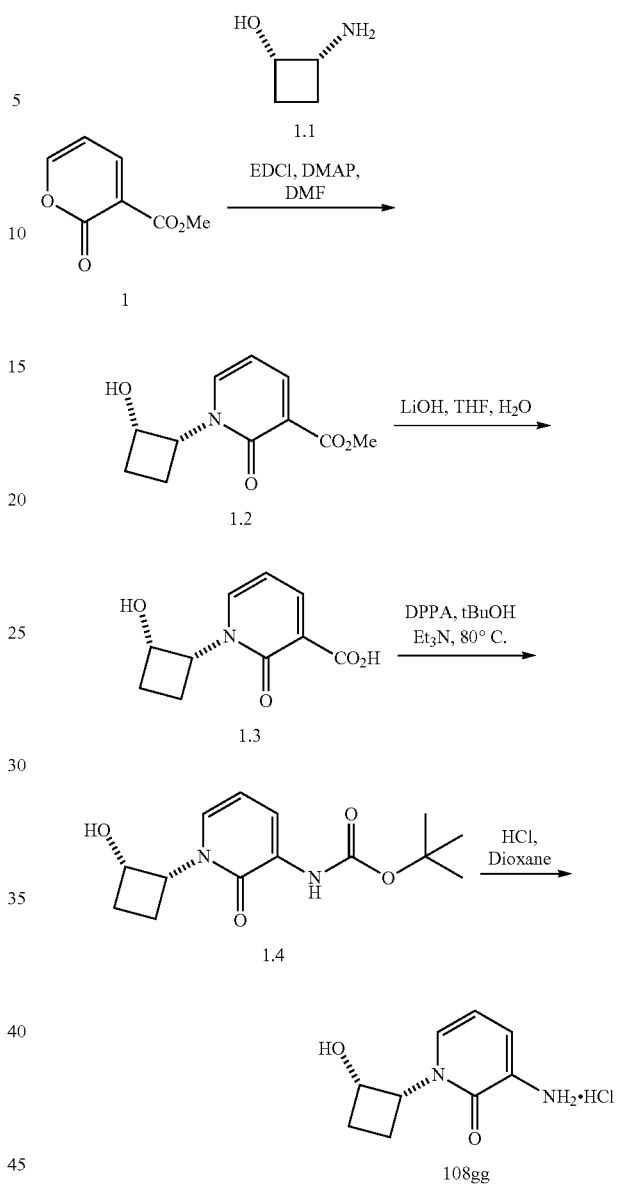

Synthesis of Compound 1.2.

To a cooled solution of 1 (2.0 g, 12.97 mmol, 1.0 eq), in N,N-dimethylformamide (25 mL) was added 1.1 (1.12 g, 12.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.6 g, 16.86 mmol, 1.3 eq) and 4-Dimethylaminopyridine (0.315 g, 2.59 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (1.3 g, 44.88%). MS(ES): m/z 224.09 [M+H]$^+$.

Synthesis of Compound 1.3.

To a solution of 1.2 (1.3 g, 5.82 mmol, 1.0 eq), in tetrahydrofuran: water (26 mL, 2:1) was added lithium hydroxide (1.3 g, 58.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3. (0.9 g, 73.87%). MS(ES): m/z 210.07 [M+H]+.

Synthesis of Compound 1.4.

To a solution of 1.3 (0.9 g, 4.30 mmol, 1.0 eq) in tert.butanol (12 mL) was added triethylamine (0.738 g, 7.31 mmol, 1.7 eq) and diphenyl phosphoryl azide (1.5 g, 5.59 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.8 g, Yield: 66.34%). MS(ES): m/z 281.15 [M+H]+.

Synthesis of Compound 108gg.

A cooled solution of 1.4 (0.8 g, 2.85 mmol, 1 eq) in dioxane (14 mL) was added 4N hydrochloric acid in dioxane (25 mL) as a dropwise. The reaction mixture was stirred at room temperature for 2 h. After completion of reaction, reaction mixture was concentrated under reduced pressure to obtain pure 108gg. (0.650 g, 97.05%). MS(ES): m/z 217.07 [M+HCl]+.

Example 109: Synthesis of compounds comprising N-(2-oxaspiro[3.3]heptan-6-yl)aminocarbonyl at position 3 of pyrazolo[1,5-a]pyrimidine

109.1. Synthesis of 5-((1-(2-cyclopropoxyethyl)-2-oxo-1,2-dihydropyridin-3-yl)amino)-7-(methylamino)-N-(2-oxaspiro[3.3]heptan-6-yl)pyrazolo[1,5-a]pyrimidine-3-carboxamide: (I-576)

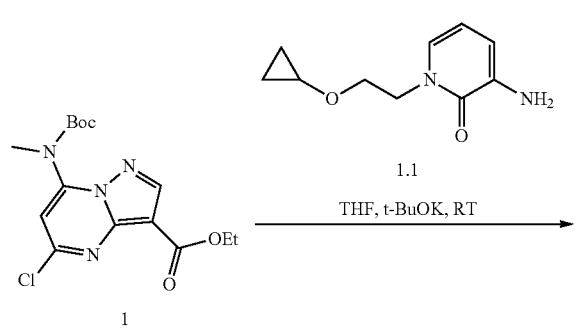

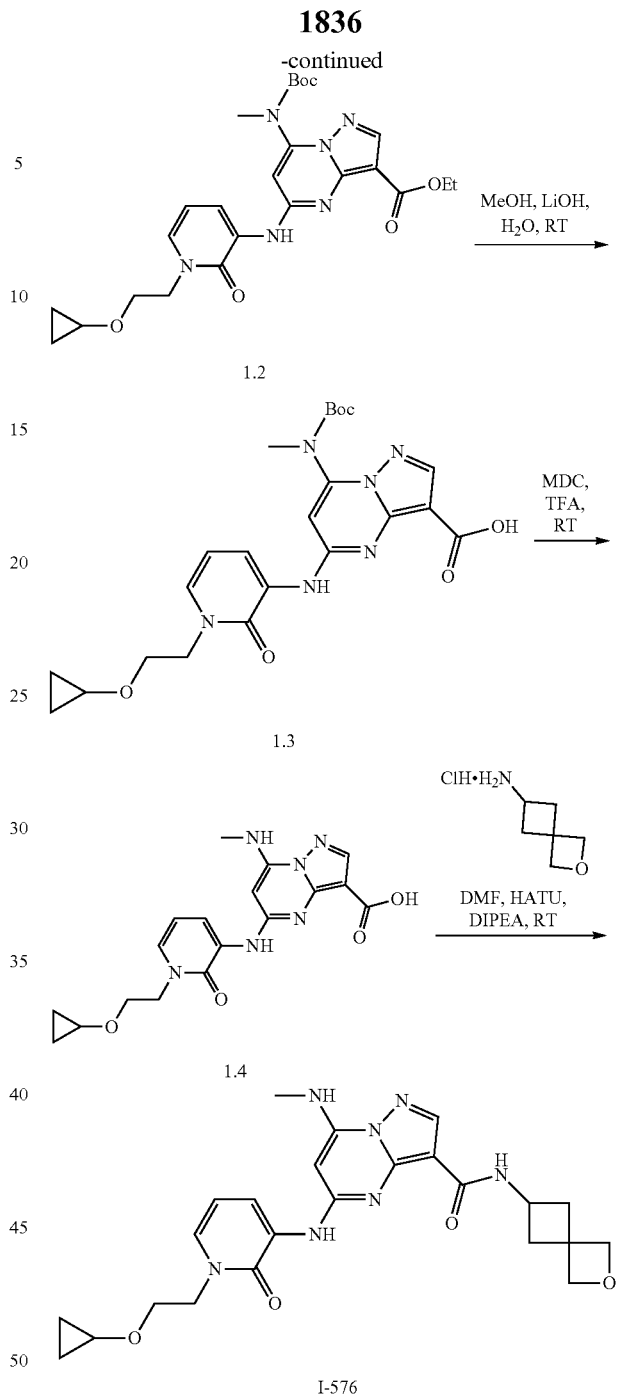

Synthesis of Compound 1.

Compound was synthesized using general procedure of core synthesis to obtain 1. (Yield: 62.21%). MS (ES): m/z 355.5 [M+H]+.

Synthesis of Compound 1.2.

To a cooled solution of 1. (0.6 g, 1.69 mmol, 1.0 eq), and 1.1 (0.329 g, 1.69 mmol, 1.0 eq) in tetrahydrofuran (10 mL) at 0° C. was added potassium tert-butoxide (3.38 mL, 3.38 mmol, 2.0 eq). The reaction was stirred at room temperature for 30 min. After completion of reaction, reaction mixture was transferred into saturated bicarbonate solution and product was extracted with ethyl acetate. Organic layer was combined and dried over sodium sulphate and concentrated under reduced pressure to obtain crude material. This was further purified by column chromatography and compound was eluted in 1.6% methanol in dichloromethane to obtain pure 1.2 (0.550 g, 63.45%). MS (ES): m/z 513.57 [M+H]⁺.

Synthesis of Compound 1.3.

To a solution of 1.2 (0.550 g, 1.07 mmol, 1.0 eq), in tetrahydrofuran: water (20 mL, 2:1) was added lithium hydroxide (0.44 g, 10.7 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by trituration with hexane to obtain pure 1.3 (0.400 g, 76.94%). MS(ES): m/z 485.5 [M+H]⁺.

Synthesis of Compound 1.4.

Compound was synthesized using general procedure C to obtain 1.4 (0.3 g, 94.53%), MS (ES): m/z 385.5 [M+H]⁺

Synthesis of Compound I-576.

Compound was synthesized using general procedure A to obtain I-576: (0.05 g, 32.06%). MS(ES): m/z 480.54 [M+H]⁺ LCMS purity: 100%, HPLC purity: 100%, NMR (DMSO-d₆, 400 MHZ): 8.91 (s, 1H), 8.20-8.16 (m, 2H), 7.90-7.89 (d, J=6 Hz, 2H), 7.34-7.33 (d, J=6.4 Hz, 1H), 6.23-6.18 (m, 2H), 4.66 (s, 2H), 4.52 (s, 2H), 4.29-4.23 (m, 1H), 4.1 (s, 2H), 3.75 (s, 2H), 2.90-2.89 (d, J=3.6 Hz, 3H), 2.65-2.63 (d, J=8 Hz, 3H), 2.08-2.03 (t, J=9.6 Hz, 2H), 0.40 (bs, 4H).

Additional compounds prepared by substantially the same method, and their characterization data, are listed in the Table 69 below. The intermediate corresponding to 1.1 of the above scheme is also listed for each compound.

109.2. Synthesis of 5-(1-isopropyl-1H-pyrrolo[2,3-b]pyridin-3-yl)-7-(methylamino)-N-(2-oxaspiro[3.3]heptan-6-yl)pyrazolo[1,5-a]pyrimidine-3-carboxamide: (1-629)

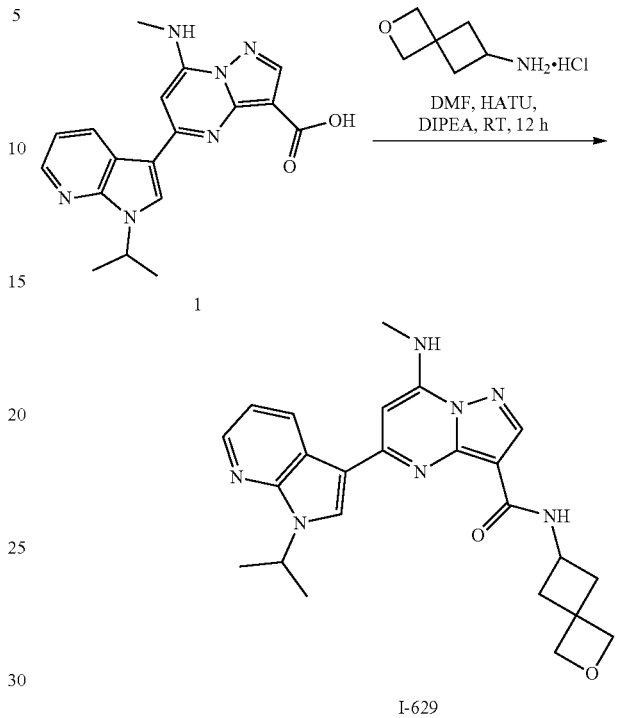

Synthesis of Compound 1

Compound was synthesized as per experimental protocol Example 67 of I-653. (0.12 g, 75.40%). MS(ES): m/z 351.38 [M+H]⁺

Synthesis of Compound I-629.

Compound was synthesized using general procedure A to obtain I-629: (0.035 g, 32.38%). MS(ES): m/z 446.5

TABLE 69

| Compound | Intermediate | Characterization Data |
|---|---|---|
| I-417 | 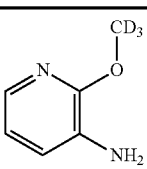 | MS (ES): m/z 413.23 [M + H]⁺, LCMS purity: 99.07%, HPLC purity: 98.17%, ¹H NMR (DMSO-d₆, 400 MHZ): 8.97 (s, 1H), 8.23-8.21 (d, J = 4 Hz, 1H), 8.13 (s, 1H), 7.95-7.89 (m, 3H), 7.00-6.97 (m, 1H), 5.87 (s, 1H), 4.64 (s, 2H), 4.51 (s, 2H) 4.24-4.18 (m, 1H), 2.92-2.90 (d, J = 4.8 Hz, 3H), 2.51 (bs, 2H), 1.89-1.84 (m, 1H), 1.28-1.25 (m, 1H). |
| I-433 | 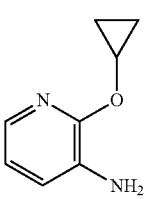 | MS (ES): m/z 436.32 [M + H]⁺, LCMS purity: 100%, HPLC purity: 98.66%, ¹H NMR (DMSO-d₆, 400 MHZ): 8.78 (s, 1H), 8.22-8.20 (d, J = 6.8 Hz, 1H), 8.13 (s, 1H), 7.98-7.87 (m, 3H), 7.03-7.00 (m, 1H), 5.82 (m, 1H), 4.63 (s, 2H), 4.51 (s, 2H), 4.35 (bs, 1H), 4.23-4.17 (m, 1H), 2.92-2.91 (d, J = 4.4 Hz, 3H), 2.51 (bs, 2H), 1.86-1.83 (t, J = 2.8 Hz, 2H), 0.78-0.71 (m, 4H). |
| I-495 | 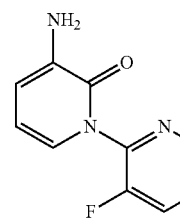 | MS (ES): m/z 491.41 [M + H]⁺, LCMS purity: 95.54%, HPLC purity: 96.35%, ¹H NMR (DMSO-d₆, 400 MHZ): 9.05 (s, 1H), 8.52-8.51 (d, J = 4.4 Hz, 1H), 8.34-8.33 (d, J = 1.6 Hz, 1H), 8.19 (s, 1H), 8.09-8.05 (m, 1H), 7.96-7.89 (m, 2H), 7.75-7.71 (m, 1H), 7.50-7.48 (m, 1H), 6.44-6.41 (t, J = 14.4 Hz, 1H), 6.19 (bs, 1H), 4.66 (s, 2H), 4.51 (s, 2H), 4.27-4.24 (m, 1H), 2.89 (s, 3H), 2.70-2.65 (m, 2H), 2.14-2.08 (m, 2H). |

[M+H]⁺. LCMS purity: 100%, HPLC purity: 96.75%, NMR (DMSO-d₆, 400 MHZ): 8.80 (s, 1H), 8.76-8.74 (d, J=7.6 Hz, 1H), 8.43 (s, 1H), 8.37-35 (d, J=8 Hz, 2H), 8.26 (s, 1H), 7.27 (s, 1H), 6.79 (s, 1H), 5.22 (bs, 1H), 4.71 (s, 2H), 4.55 (s, 2H), 4.38-4.34 (m, 1H), 3.13-3.12 (d, J=4 Hz, 3H), 2.74 (s, 2H), 2.23-2.21 (d, J=8.8 Hz, 2H), 1.60-1.59 (d, J=6.4 Hz, 6H).

Example 110: N-hydroxy-5-((2-methoxypyridin-3-yl)amino)-7-(methylamino)pyrazolo[1,5-a]pyrimidine-3-carboxamide (I-710)

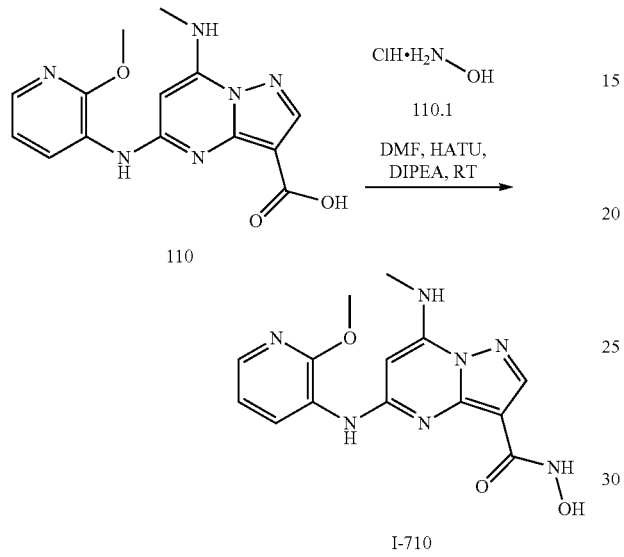

Synthesis of Compound 1.0
Compound was synthesized as per experimental protocol of Example 32 to obtain 1.0 (Yield: 71.18%), MS (ES): m/z 315.42 [M+H]⁺

Synthesis of Compound I-710.
Compound was synthesized using general procedure A to obtain I-710 (0.04 g, 27.8%). MS (ES): m/z 330.2 [M+H]⁺, LCMS purity: 97.99%, HPLC purity: 95.28%, ¹H NMR (DMSO-d₆, 400 MHZ): 8.90 (bs, 1H), 8.40 (bs, 1H), 8.15 (s, 1H), 7.87 (s, 2H), 7.01-6.98 (m, 1H), 5.81 (s, 1H), 3.96 (s, 4H), 2.89 (s, 4H).

Example 111: 5-((3'-fluoro-2-oxo-2H-[1,2'-bipyridin]-3-yl)amino)-7-(methylamino)pyrazolo[1,5-a]pyrimidine-3-carboxylic acid (I-893)

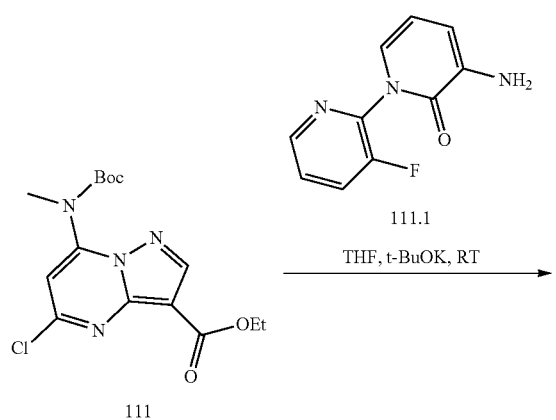

Synthesis of Compound 111.
Compound was synthesized using general procedure of core synthesis to obtain 111. (Yield: 62.21%). MS (ES): m/z 355.5 [M+H]⁺.

Synthesis of Compound 111.1.
Compound was synthesized as per experimental protocol of Example 19 to obtain 111.1. (Yield: 80.70%). MS (ES): m/z 206.29 [M+H]⁺

Synthesis of Compound 111.2.
To a cooled solution of 111 (0.2 g, 0.56 mmol, 1.0 eq), and 111.1 (0.114 g, 0.56 mmol, 1.0 eq) in tetrahydrofuran (4 mL) at 0° C. was added potassium ter-butoxide (1M in tetrahydrofuran) (1.1 mL, 1.12 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 111.2. (0.136 g, 45.91%). MS (ES): m/z 526.22 [M+H]⁺.

Synthesis of Compound 111.3.
To a solution of 111.2 (0.136 g, 0.25 mmol, 1.0 eq), in tetrahydrofuran: methanol: water (4 mL, 2:2:1) was added lithium hydroxide (0.025 g, 2.5 mmol, 10 eq). The reaction was stirred at RT for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 111.3. (0.096 g, 74.87%). MS(ES): m/z 496.17 [M+H]

Synthesis of Compound I-893:

Compound was synthesized using general procedure C to obtain I-893 (0.056 g, 73.11%), MS (ES): m/z 396.27 [M+H]+, LCMS purity: 95.20%, HPLC purity: 92.78%, $^1$H NMR (DMSO-d$_6$, 400 MHZ): 11.89 (bs, 1H), 9.20-9.19 (d, J=6.8 Hz, 1H), 8.99 (bs, 1H), 8.51 (bs, 1H), 8.25 (bs, 1H), 8.06 (bs, 1H), 7.85 (bs, 1H), 7.73 (bs, 1H), 7.35-7.34 (t, J=6 Hz, 1H), 6.41 (bs, 1H), 6.31 (bs, 1H), 2.89 (bs, 3H).

Example 112: Synthesis of compounds comprising (2-methoxycyclopropyl)aminocarbonyl at position 3 of the pyrazolo[1,5-a]pyrimidine 112.1. Synthesis of N-(2-methoxycyclopropyl)-7-(methylamino)-5-((2-oxo-1-((S)-tetrahydro-2H-pyran-3-yl)-1,2-dihydropyridin-3-yl)amino)pyrazolo[1,5-a]pyrimidine-3-carboxamide (I-1415)

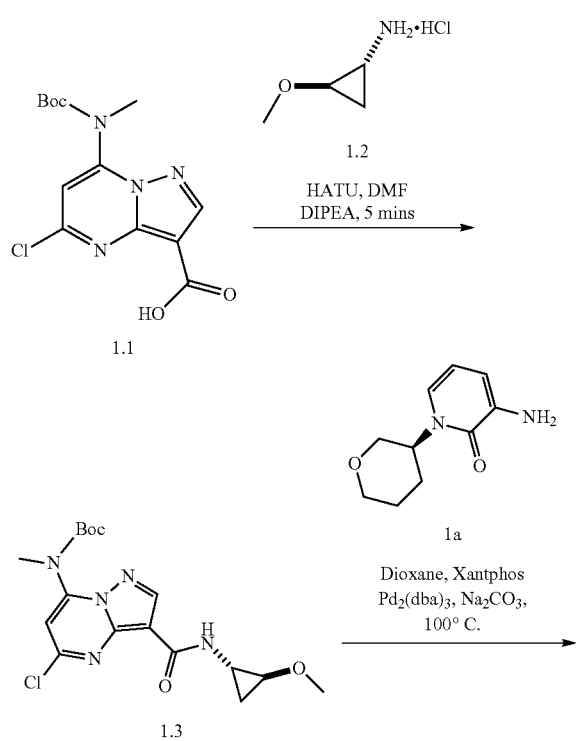

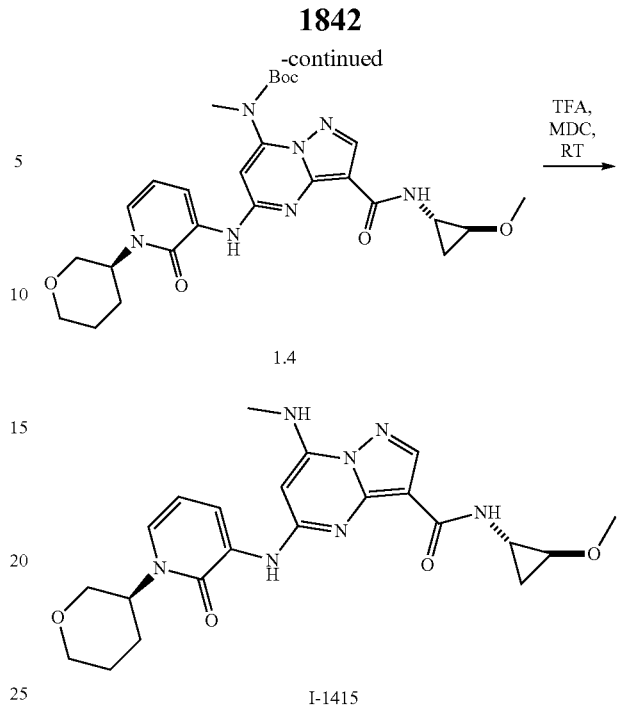

Synthesis of Compound 1.1.

Compound was synthesized using general procedure of core synthesis to obtain 1.1. (Yield: 71.67%). MS (ES): m/z 327.08 [M+H]+

Synthesis of Compound 1.3.

Compound was synthesized using general procedure A to obtain 1.3. (0.640 g, 52.83%), MS (ES): 396.14 [M+H]+

Synthesis of Compound 1.4.

Compound was synthesized using general procedure B to obtain 1.4. (0.140 g, 77.00%), MS (ES): 554.27 [M+H]+

Synthesis of Compound I-1415:

Compound was synthesized using general procedure C to obtain I-1415 (0.028 g, 85.45%), MS (ES): 454.57 [M+H]+ LCMS purity: 98.79%, HPLC purity: 98.58%, CHIRAL HPLC purity: 48.78%, 50.56%, $^1$H NMR (DMSO-d$_6$, 400 MHZ): 8.87 (s, 1H), 8.22 (s, 1H), 8.17-8.16 (d, J=7.2 Hz, 1H), 7.93-7.92 (d, J=4.8 Hz, 1H), 7.67-7.66 (d, J=4 Hz, 1H), 7.51-7.49 (d, J=6.8 Hz, 1H), 6.31-6.28 (t, J=7.2 Hz, 1H), 6.24 (s, 1H), 4.90-4.85 (m, 1H), 3.82 (bs, 2H), 3.75-3.70 (t, J=8.4 Hz, 1H), 3.30 (s, 2H), 3.17-3.16 (d, J=5.2 Hz, 3H), 3.09-3.03 (m, 1H), 2.90-2.89 (d, J=4.8 Hz, 3H), 2.06-1.96 (m, 2H), 1.76-1.70 (m, 2H), 1.23 (bs, 2H).

Additional compounds prepared by substantially the same method, and their characterization data, are listed in the table below. The intermediate corresponding to 1a of the above scheme is also listed for each compound.

| Compound | Intermediate | Characterization data |
|---|---|---|
| I-1413 | ![structure with pyridine, N-pyridinone, NH2, F] | MS (ES): 465.47 [M + H]+ LCMS purity: 95.34%, HPLC purity: 95.02%, CHIRAL HPLC purity: 50.27%, 48.68%, $^1$H NMR (DMSO-d$_6$, 400 MHZ): 9.00 (s, 1H), 8.53-8.52 (d, J = 4 Hz, 1H), 8.33-8.31 (d, J = 7.2 Hz, 1H), 8.26 (s, 1H), 8.10-8.05 (t, J = 9.2 Hz, 1H), 7.98-7.97 (d, J = 4.4 Hz, 1H), 7.76-7.70 (m, 2H), 7.44-7.43 (d, J = 6.8 Hz, 1H), 6.46-6.43 (t, J = 7.2 Hz, 1H), 6.26 (s, 1H), 4.39-4.38 (d, J = 4 Hz, 1H), 3.82-3.76 (m, 1H), 3.29 (s, 3H), 3.12-3.09 (m, 1H), 2.91-2.90 (d, J = 4.8 Hz, 3H), 0.56 (bs, 1H). |

112.2. Chiral Separation

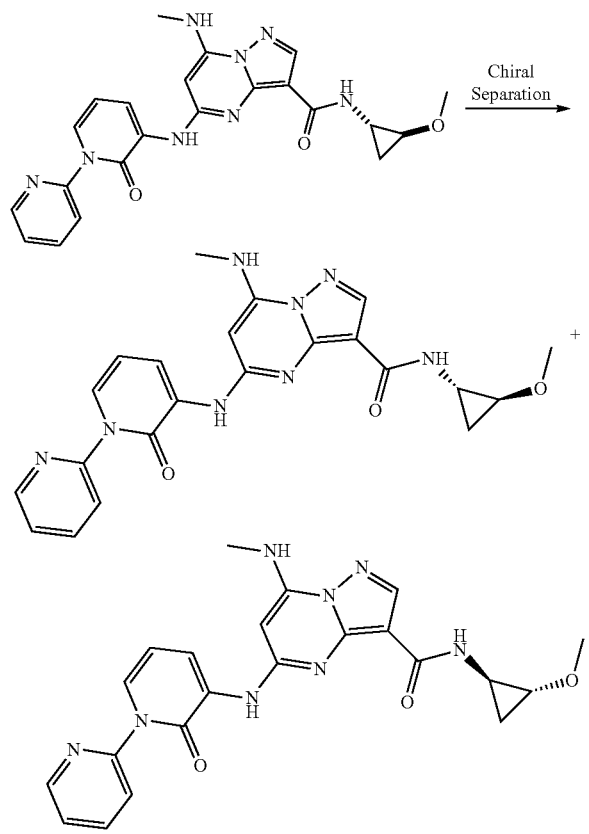

Chiral Separation

Synthesis of compound I-1286 & I-1287.

Isomers of I-1412 (0.12 g) were separated out using column (CHIRAL PAK AD-H 250×4.6 mm, 5 u) 0.1% DEA_MEOH (70-30) to get pure fraction-1 (FR-a) and fraction-2 (FR-b). FR-a was concentrated under reduced pressure at 30° C. to afford pure FR-a (0.035 g). MS(ES): m/z 447.61 [M+H]$^+$, LCMS purity: 100%, HPLC purity: 98.11%, CHIRAL HPLC purity: 99.01%, $^1$H NMR (DMSO-$d_6$, 400 MHZ): 8.98 (s, 1H), 8.67-8.66 (d, J=4.0 Hz, 1H), 8.31-8.29 (d, J=7.6 Hz, 1H), 8.26 (s, 1H), 8.08-8.05 (m, 1H), 7.97-7.96 (d, J=4.4 Hz, 1H), 7.87-7.85 (d, J=7.6 Hz, 1H), 7.73-7.71 (d, J=6.4 Hz, 1H), 7.59-7.54 (m, 2H), 6.45-6.41 (m, 1H), 6.27 (s, 1H), 3.29 (s, 4H), 3.12-3.11 (m, 1H), 2.92-2.91 (d, J=4.4 Hz, 3H), 1.09-1.04 (m, 1H), 0.57-0.56 (m, 1H).

FR-b was concentrated under reduced pressure at 30° C. to afford pure FR-b (0.035 g). MS(ES): m/z 447.56 [M+H]$^+$, LCMS purity: 100%, HPLC purity: 98.11%, CHIRAL HPLC purity: 99.43%, $^1$H NMR (DMSO-$d_6$, 400 MHZ): 8.98 (s, 1H), 8.67-8.66 (d, J=4.0 Hz, 1H), 8.31-8.29 (d, J=7.2 Hz, 1H), 8.26 (s, 1H), 8.08-8.05 (m, 1H), 7.97-7.96 (d, J=4.4 Hz, 1H), 7.87-7.85 (d, J=7.6 Hz, 1H), 7.73-7.71 (d, J=6.4 Hz, 1H), 7.59-7.54 (m, 2H), 6.45-6.41 (m, 1H), 6.28 (s, 1H), 3.29 (s, 4H), 3.19-3.11 (m, 1H), 2.92-2.91 (d, J=4.0 Hz, 3H), 1.09-1.07 (m, 1H), 0.57-0.56 (m, 1H).

Additional compounds prepared by substantially the same method, and their characterization data, are listed in the table below.

| Compound | Isomers | Characterization data |
|---|---|---|
| I-1413 (Chiral separation when the methylamino at position 7 is protected by Boc, followed by removal of Boc) | I-1311 I-1312 | FR-a: MS (ES): m/z 465.46 [M + H]$^+$, LCMS purity: 95.70%, HPLC purity: 95.40%, Chiral HPLC: 100%, $^1$H NMR (DMSO-$d_6$, 400 MHZ): 9.00 (s, 1H), 8.53-8.52 (d, J = 8.2 Hz, 1H), 8.33-8.31 (d, J = 8.4 Hz, 1H), 8.26 (s, 1H), 8.10-8.08 (t, J = 8.2 Hz, 1H), 7.98-7.97 (d, J = 4 Hz, 1H), 7.76-7.75 (t, J = 4 Hz, 1H), 7.72-7.70 (d, J = 7.8 Hz, 1H), 7.45-7.43 (d, J = 8 Hz, 1H), 6.47-6.45 (t, J = 7.8 Hz, 1H), 6.26 (s, 1H), 4.38-4.37 (d, J = 4 Hz, 1H), 3.80-3.76 (m, 1H), 3.29 (s, 3H), 3.12-3.09 (m, 1H), 2.91-2.90 (d, J = 4 Hz, 3H), 0.58-0.57 (t, J = 3.6 Hz, 1H). FR-b: MS (ES): m/z 464.46 [M + H]$^+$, LCMS purity: 95.09%, HPLC purity: 95.55% Chiral HPLC: 98.41%, $^1$H NMR (DMSO-$d_6$, 400 MHZ): 9.00 (s, 1H), 8.53-8.52 (d, J = 8.2 Hz, 1H), 8.33-8.31 (d, J = 8.4 Hz, 1H), 8.26 (s, 1H), 8.10-8.08 (t, J = 8.2 Hz, 1H), 7.98-7.97 (d, J = 4 Hz, 1H), 7.76-7.75 (t, J = 4 Hz, 1H), 7.72-7.70 (d, J = 7.8 Hz, 1H), 7.45-7.43 (d, J = 8 Hz, 1H), 6.47-6.45 (t, J = 7.8 Hz, 1H), 6.26 (s, 1H), 4.38-4.37 (d, J = 4 Hz, 1H), 3.80-3.76 (m, 1H), 3.12-3.09 (m, 1H), 2.91-2.90 (d, J = 4 Hz, 3H), 3.29 (s, 3H), 0.58-0.57 (t, J = 3.6 Hz, 1H). |
| I-1414 (Chiral separation when the methylamino at position 7 is protected by Boc, followed by removal of Boc) | I-1269 I-1270 | FR-a: MS (ES): 454.82 [M + H]$^+$ LCMS purity: 100%, HPLC purity: 100%, CHIRAL HPLC: 98.93%, $^1$H NMR (DMSO-$d_6$, 400 MHZ): 8.87 (s, 1H), 8.22 (s, 1H), 8.17-8.15 (d, J = 6.8 Hz, 1H), 7.93-7.91 (d, J = 4.8 Hz, 1H), 7.67-7.66 (d, J = 6 Hz, 1H), 7.50-7.49 (d, J = 6.8 Hz, 1H), 6.31-6.28 (t, J = 7.2 Hz, 1H), 6.24 (s, 1H), 4.87 (bs, 1H), 3.82 (bs, 2H), 3.58-3.53 (t, J = 10 Hz, 1H), 3.35 (s, 2H), 3.17 (s, 3H), 3.06 (bs, 1H), 2.90-2.89 (d, J = 4.8 Hz, 3H), 1.96 (bs, 1H), 1.76 (bs, 2H), 1.23 (bs, 1H), 1.06-1.04 (d, J = 7.2 Hz, 1H), 0.51 (bs, 1H). FR-b: MS (ES): 454.82 [M + H]$^+$ LCMS purity: 100%, HPLC purity: 100%, CHIRAL HPLC: 95.77%, $^1$H NMR (DMSO-$d_6$, 400 MHZ): 8.87 (s, 1H), 8.22 (s, 1H), 8.17-8.15 (d, J = 6.8 Hz, 1H), 7.93-7.91 (d, J = 4.8 Hz, 1H), 7.67-7.66 (d, J = 6 Hz, 1H), 7.50-7.49 (d, J = 6.8 Hz, 1H), 6.31-6.28 (t, J = 7.2 Hz, 1H), 6.24 (s, 1H), 4.87 (bs, 1H), 3.82 (bs, 2H), 3.59-3.54 (t, J = 10 Hz, 1H), 3.35 (s, 2H), 3.24 (s, 3H), 3.06 (bs, 1H), 2.90-2.89 (d, J = 4.8 Hz, 3H), 1.96 (bs, 1H), 1.76 (bs, 2H), 1.23 (bs, 1H), 1.06-1.04 (d, J = 7.2 Hz, 1H), 0.52 (bs, 1H). |

Example 113: Synthesis of compounds comprising N-(2-hydroxy-2-methylcyclohexyl)aminocarbonyl at position 3 of the pyrazolo[1,5-a]pyrimidine 113.1. Synthesis of I-1318

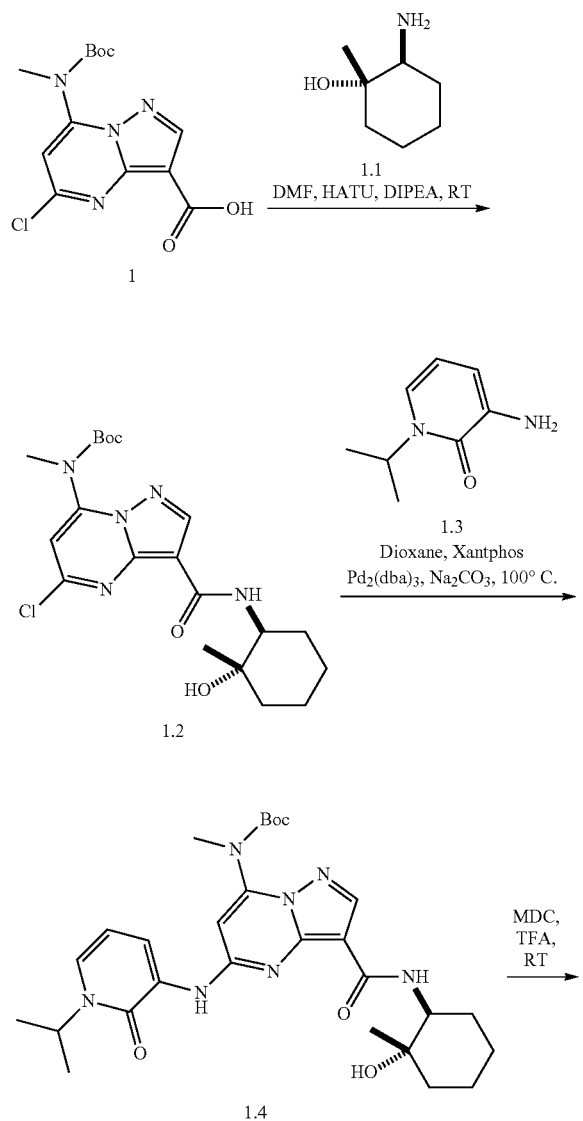

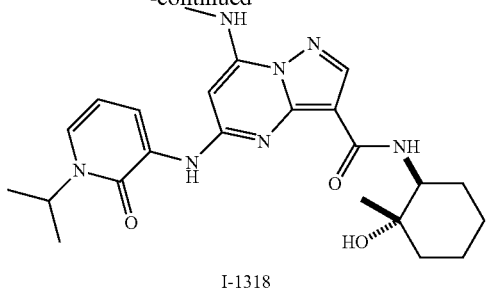

I-1318

Synthesis of Compound 1.

Compound was synthesized using general procedure of core synthesis to obtain 1. MS (ES): m/z 327.08 [M+H]$^+$ Synthesis of Compound 1.2.

Compound was synthesized using general procedure A to obtain 1.2. (0.055 g, 41.05%), MS (ES): 438.19 [M+H]

Synthesis of Compound 1.3.

Compound was synthesized as per experimental protocol of the intermediates to obtain 1.3. (Yield: 82.29%), MS (ES): m/z 153.10 [M+H]

Synthesis of Compound 1.4.

Compound was synthesized using general procedure B to obtain 1.4. (0.130 g, 68.55%), MS (ES): 554.30 [M+H]$^+$ Synthesis of Compound I-1318:

Compound was synthesized using general procedure C to obtain I-1318 (0.021 g, 85.45%), MS (ES): 454.41 [M+H]$^+$ LCMS purity: 100%, HPLC purity: 100%, CHIRAL HPLC: 48.38%, 51.62%, $^1$H NMR (DMSO-d$_6$, 400 MHZ): 8.82 (s, 1H), 8.21 (s, 1H), 8.15-8.14 (d, J=6 Hz, 1H), 7.93-7.91 (d, J=4.8 Hz, 1H), 7.56-7.54 (d, J=8.4 Hz, 1H), 7.44-7.42 (d, J=5.6 Hz, 1H), 6.31-6.27 (t, J=6.8 Hz, 1H), 6.21 (s, 1H), 5.19-5.13 (m, 1H), 4.76 (m, 1H), 3.92 (bs, 1H), 2.91-2.90 (d, J=4.4 Hz, 3H), 1.88 (bs, 1H), 1.61 (bs, 3H), 1.58 (bs, 1H), 1.44 (bs, 1H), 1.35-1.33 (d, J=6.8 Hz, 6H), 1.23 (s, 2H), 1.01 (s, 3H).

Additional compounds prepared by substantially the same method, and their characterization data, are listed in the table below. The intermediate corresponding to 1.3 of the above scheme is also listed for each compound.

| Compound | Intermediate | Characterization data |
|---|---|---|
| I-1315 | (structure: 1-(tetrahydropyran-4-yl)-3-amino-2-oxo-pyridine) | MS (ES): 496.82 [M + H]$^+$ LCMS purity: 97.27%, HPLC purity: 98.85%, CHIRAL HPLC: 47.73%, 49.72%, $^1$H NMR (DMSO-d$_6$, 400 MHZ): 8.81 (s, 1H), 8.22-8.21 (d, J = 2.8 Hz, 1H), 8.17-8.15 (d, J = 6.4 Hz, 1H), 7.94-7.92 (d, J = 5.2 Hz, 1H), 7.55-7.53 (d, J = 8 Hz, 1H), 7.47-7.46 (d, J = 6 Hz, 1H), 6.31-6.27 (t, J = 7.2 Hz, 1H), 6.21 (s, 1H), 4.99 (bs, 1H), 4.75 (s, 1H), 4.25 (s, 1H), 3.99 (bs, 2H), 3.92 (bs, 1H), 3.86-3.84 (t, J = 5.2 Hz, 1H), 3.53-3.48 (t, J = 11.6 Hz, 2H), 2.91-2.90 (d, J = 4.8 Hz, 3H), 1.61 (bs, 4H), 1.41 (bs, 2H), 1.33 (bs, 2H), 1.22 (bs, 2H), 1.03 (s, 3H). |

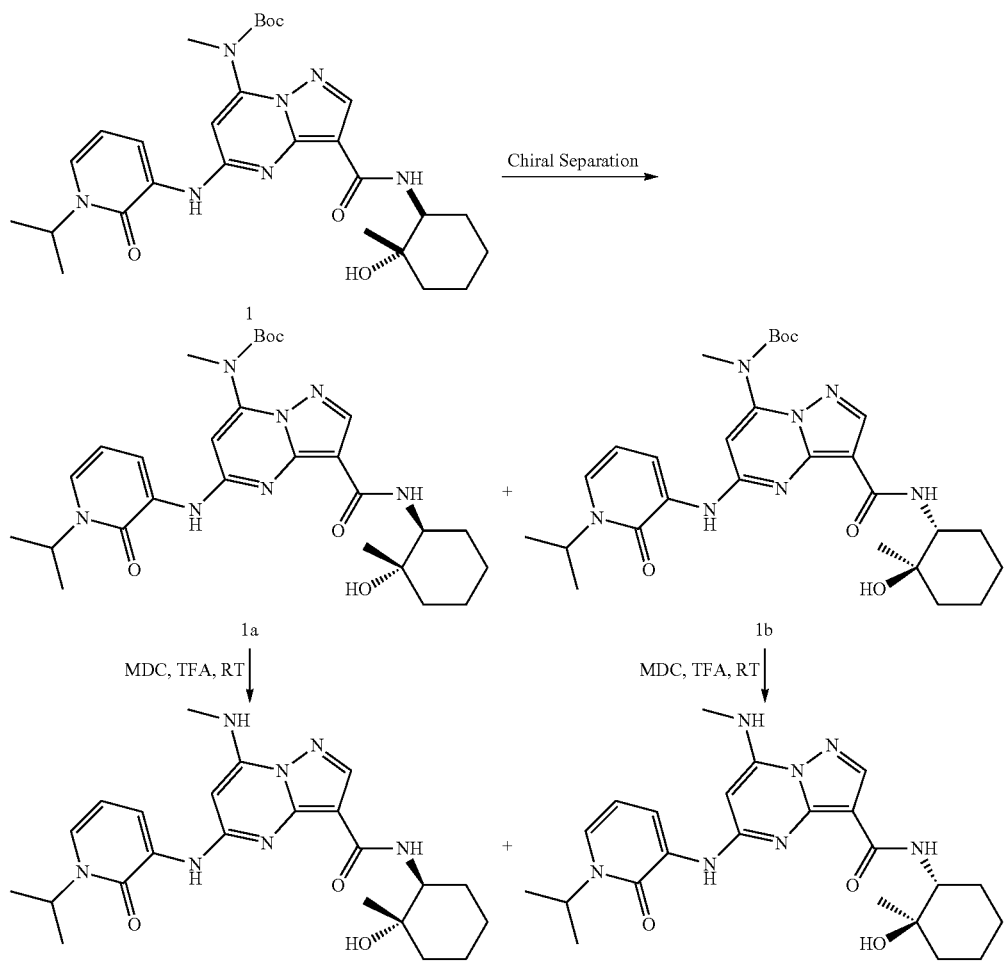

Synthesis of Compound 1.

Compound was synthesized as per experimental protocol of I-1318 to obtain 1. (Yield: 66.66%). MS (ES): m/z 554.58 [M+H]$^+$.

Synthesis of compound 1a and 1b.

Isomers of 1 (0.110 g) were separated out using column CHIRALCEL OX-H (250 mm*4.6 mm, 5 u) and 0.1% DEA_HEX_IPA-CAN (70-30) as co-solvent with flow rate of 4 mL/min. to get pure fraction-1 (FR-a) and fraction-2 (FR-b). FR-a was concentrated under reduced pressure at 30° C. to afford pure 1a (0.040 g). MS(ES): 554.58 [M+H]$^+$. FR-b was concentrated under reduced pressure at 30° C. to afford pure 1b (0.042 g). MS(ES): m/z 554.58 [M+H]$^+$.

Synthesis of Compound I-1276 and I-1277:

Compound was synthesized using general procedure C to obtain FR-a (0.021 g) MS (ES): m/z 454.42 [M+H]$^+$, LCMS purity: 98.09%, HPLC purity: 99.22%, Chiral HPLC: 98.66%, $^1$H NMR (DMSO-d$_6$, 400 MHZ): 8.83 (s, 1H), 8.22 (s, 1H), 8.17-8.15 (d, J=7.2 Hz, 1H), 7.93-7.92 (d, J=4.8 Hz, 1H), 7.57-7.55 (d, J=8.2 Hz, 1H), 7.45-7.43 (d, J=7.2 Hz, 1H), 6.32-6.30 (d, J=7.2 Hz, 1H), 6.22 (s, 1H), 5.20-5.16 (m, 1H), 4.77 (s, 1H), 3.93 (s, 1H), 2.92-2.91 (d, J=4 Hz, 3H), 1.89 (s, 1H), 1.62-1.60 (d, J=8 Hz, 3H), 1.45-1.42 (d, J=10.8 Hz, 1H), 1.36-1.34 (d, J=7.8 Hz, 9H), 1.02 (s, 3H).

And FR-b (0.024 g) MS (ES): m/z 454.42 [M+H]$^+$, LCMS purity: 100%, HPLC purity: 100% Chiral HPLC: 99.75%, $^1$H NMR (DMSO-d$_6$, 400 MHZ): 8.83 (s, 1H), 8.22 (s, 1H), 8.17-8.15 (d, J=7.2 Hz, 1H), 7.93-7.92 (d, J=4.8 Hz, 1H), 7.57-7.55 (d, J=8.2 Hz, 1H), 7.45-7.43 (d, J=7.2 Hz, 1H), 6.32-6.30 (d, J=7.2 Hz, 1H), 6.22 (s, 1H), 5.20-5.16 (m, 1H), 4.77 (s, 1H), 3.93 (s, 1H), 2.92-2.91 (d, J=4 Hz, 3H), 1.89 (s, 1H), 1.62-1.60 (d, J=8 Hz, 3H), 1.45-1.42 (d, J=10.8 Hz, 1H), 1.36-1.34 (d, J=7.8 Hz, 9H), 1.02 (s, 3H).

Example 114: Synthesis of compounds comprising N-(2-ethoxycyclobutyl)aminocarbonyl at position 3 of the pyrazolo[1,5-a]pyrimidine 114.1. Synthesis of I-1294

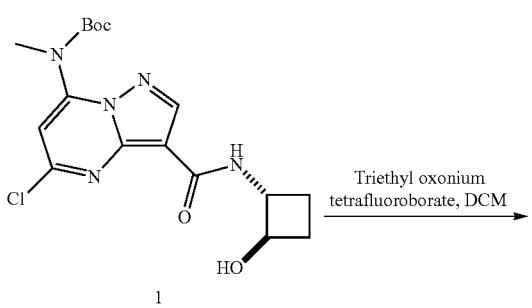

-continued

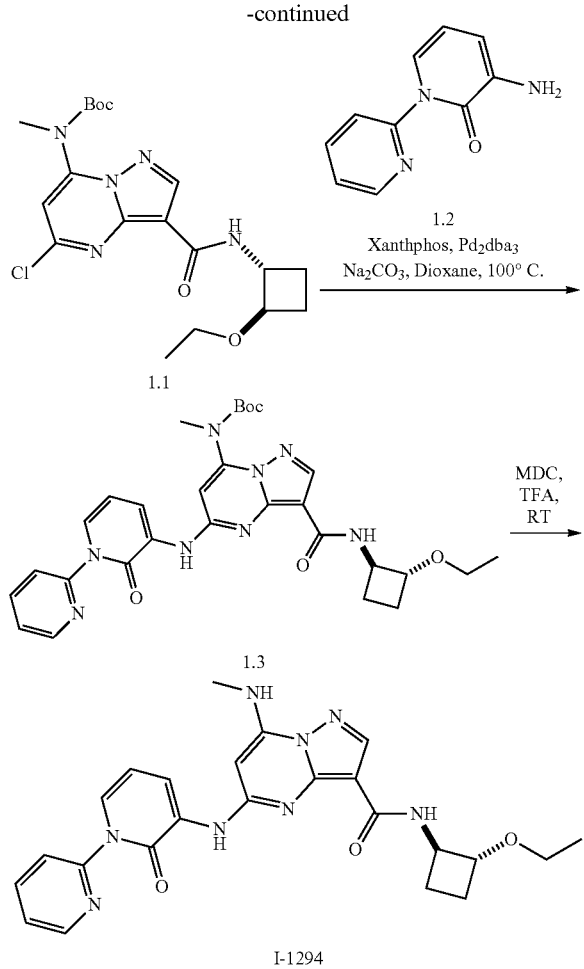

Synthesis of Compound 1.

Compound was synthesized as per experimental protocol of I-705 to obtain 1. (Yield: 45.44%), MS (ES): m/z 396.84 [M+H]+

Synthesis of Compound 1.1.

To a cooled solution of 1. (0.135 g, 0.34 mmol, 1.0 eq), in dichloromethane (3 mL) was added Trimethyloxonium tetrafluoroborate (0.1 g, 0.68 mmol, 2.0 eq). The reaction mixture was stirred at room temperature for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.5% methanol in dichloromethane to obtain 1.1. (0.045 g, 31.13%). MS(ES): m/z 424.17 [M+H]+

Synthesis of Compound 1.2.

Compound was synthesized as per experimental protocol of the intermediates to obtain 1.2. (Yield: 58.82%), MS (ES): m/z 188.20 [M+H]+

Synthesis of Compound 1.3.

Compound was synthesized using general procedure B to obtain 1.3. (0.125 g, 73.77%), MS (ES): 575.27 [M+H]+

Synthesis of Compound I-1294:

Compound was synthesized using general procedure C to obtain I-1294 (0.020 g, 80.73%), MS (ES): 475.57 [M+H]+ LCMS purity: 95.42%, HPLC purity: 95.00%, $^1$H NMR (DMSO-$d_6$, 400 MHZ): 9.06 (s, 1H), 8.67-8.65 (d, J=4.4 Hz, 1H), 8.35-8.33 (d, J=7.6 Hz, 1H), 8.22 (s, 1H), 8.12-8.05 (m, 2H), 7.98-7.97 (d, J=5.2 Hz, 1H), 7.87-7.85 (d, J=8 Hz, 1H), 7.64-7.62 (d, J=7.2 Hz, 1H), 7.57-7.54 (m, 1H), 6.47-6.43 (t, J=7.2 Hz, 1H), 6.22 (s, 1H), 4.36-4.30 (m, 1H), 3.83-3.78 (m, 1H), 2.54-3.47 (m, 2H), 2.92-2.91 (d, J=4.8 Hz, 3H), 2.17-2.06 (m, 2H), 1.56-1.49 (m, 2H), 1.09-1.06 (t, J=6.8 Hz, 3H).

114.2. Chiral Separation

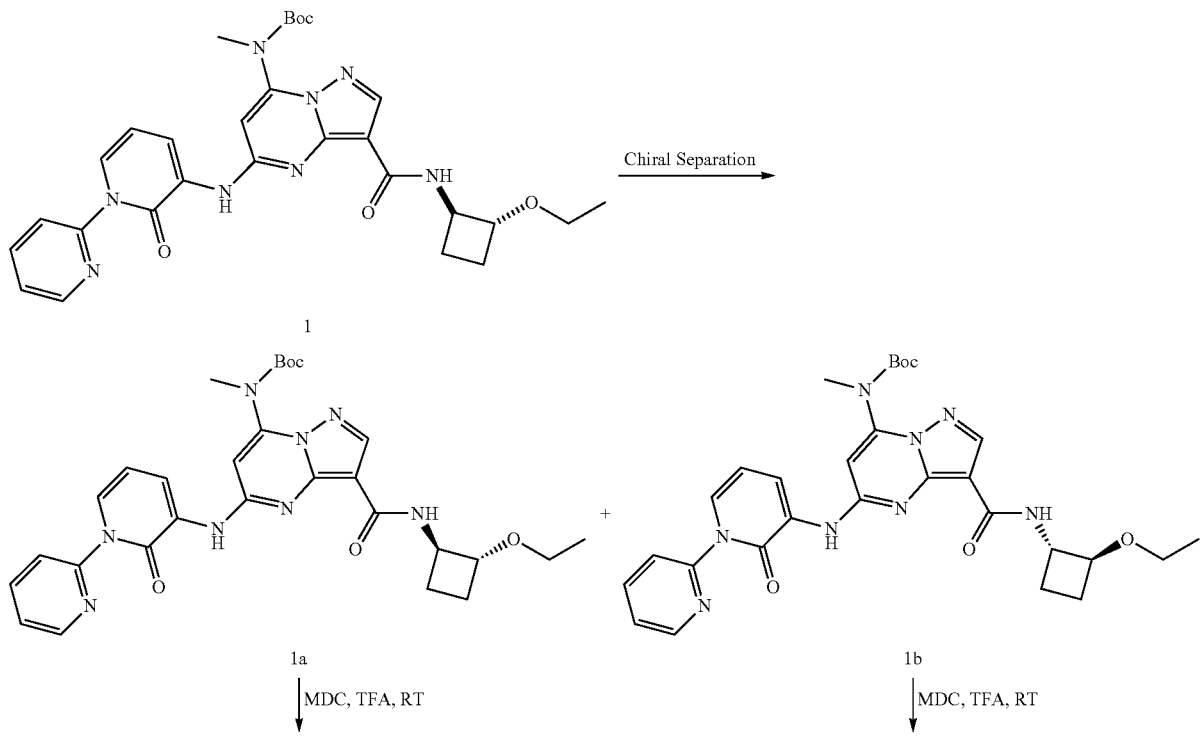

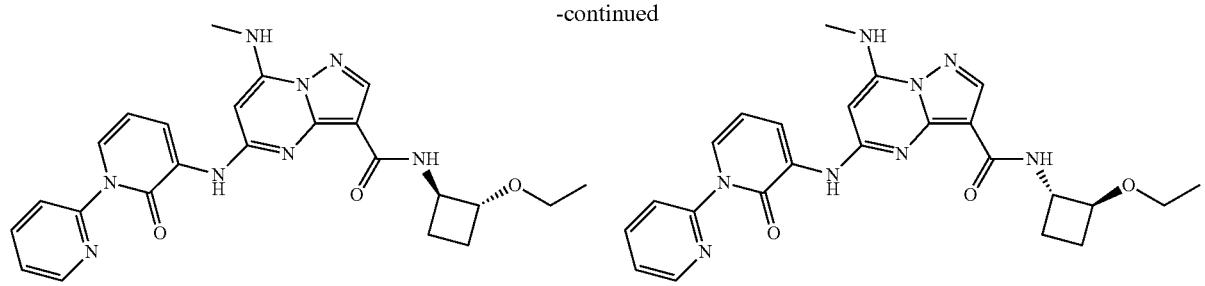

-continued

Synthesis of Compound 1.
Compound was synthesized as per experimental protocol of I-1294 to obtain 1. (Yield: 73.77%), MS (ES): 575.27 [M+H]$^+$ Synthesis of compound 1a and 1b.
Isomers of 1 (0.1 g) were separated out using column CHIRALPAK OX-H (250 mm*4.6 mm, 5 u) and DEA_HEX_IPA-ACN (70-30)_as co-solvent with flow rate of 4 mL/min. to get pure fraction-1 (FR-a) and fraction-2 (FR-b). FR-a was concentrated under reduced pressure at 30° C. to afford pure 1a. (0.038 g). MS(ES): m/z 575.27 [M+H]$^+$. FR-b was concentrated under reduced pressure at 30° C. to afford pure 1b. (0.037 g). MS(ES): m/z 575.27 [M+H]$^+$.

Synthesis of Compound I-1231 and I-1232:
Compound was synthesized using general procedure C to obtain FR-a (0.024 g, Yield: 76.48%), MS (ES): 475.61 [M+H]$^+$ LCMS purity: 100%, HPLC purity: 99.28%, CHIRAL HPLC: 100%, $^1$H NMR (DMSO-$d_6$, 400 MHZ): 9.04 (s, 1H), 8.65-8.64 (d, J=3.6 Hz, 1H), 8.34-8.32 (d, J=6 Hz, 1H), 8.21 (s, 1H), 8.11-8.04 (m, 2H), 7.97-7.95 (d, J=4.8 Hz, 1H), 7.86-7.84 (d, J=8 Hz, 1H), 7.63-7.61 (d, J=5.6 Hz, 1H), 7.56-7.53 (m, 1H), 6.46-6.42 (t, J=7.2 Hz, 1H), 6.23 (s, 1H), 4.35-4.31 (t, J=7.6 Hz, 1H), 3.82-3.77 (m, 1H), 3.51-3.46 (m, 2H), 2.91-2.90 (d, J=4.8 Hz, 3H), 2.16-2.05 (m, 2H), 1.55-1.48 (m, 1H), 1.40-1.34 (m, 1H), 1.08-1.05 (t, J=6.8 Hz, 3H).

And FR-b (0.037 g, Yield: 78.55%), MS (ES): 475.66 [M+H]$^+$ LCMS purity: 100%, HPLC purity: 99.00%, CHIRAL HPLC: 98.91%, $^1$H NMR (DMSO-$d_6$, 400 MHZ): 9.05 (s, 1H), 8.65-8.64 (d, J=3.6 Hz, 1H), 8.34-8.32 (d, J=6 Hz, 1H), 8.21 (s, 1H), 8.11-8.04 (m, 2H), 7.98-7.97 (d, J=4.8 Hz, 1H), 7.86-7.84 (d, J=8 Hz, 1H), 7.63-7.61 (d, J=5.6 Hz, 1H), 7.56-7.53 (m, 1H), 6.46-6.42 (t, J=7.2 Hz, 1H), 6.23 (s, 1H), 4.35-4.31 (t, J=7.6 Hz, 1H), 3.82-3.76 (m, 1H), 3.51-3.46 (m, 2H), 2.91-2.90 (d, J=4.8 Hz, 3H), 2.13-2.07 (m, 2H), 1.55-1.48 (m, 1H), 1.40-1.34 (m, 1H), 1.08-1.05 (t, J=6.8 Hz, 3H).

Example 115: Synthesis of compounds comprising N-(2-hydroxy-2-methylcyclopentyl)aminocarbonyl at position 3 of the pyrazolo[1,5-a]pyrimidine 115.1. Synthesis of I-1336

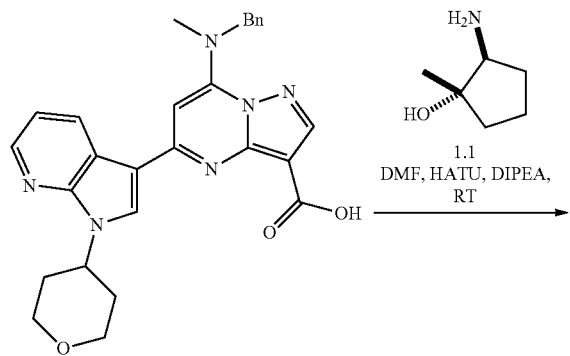

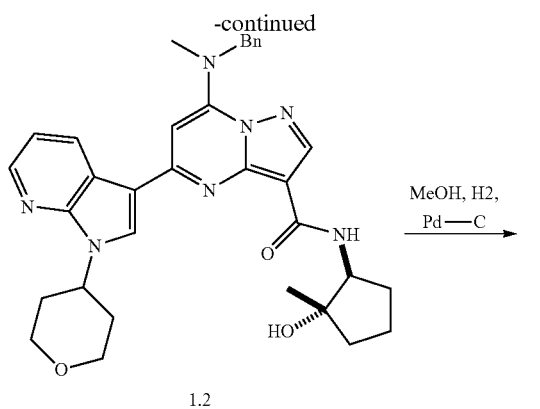

-continued

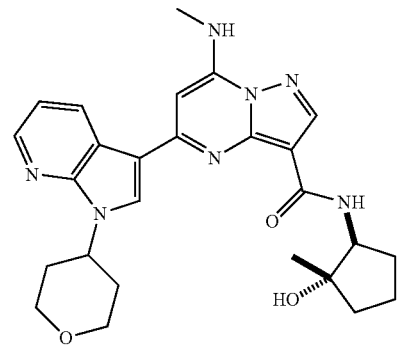

I-1336

Synthesis of Compound 1.
Compound was synthesized as per experimental protocol of I-1048 to obtain 1. (Yield: 98.76%), MS (ES): m/z 483.21 [M+H]$^+$ Synthesis of Compound 1.2.
Compound was synthesized using general procedure A to obtain 1.2. (0.150 g, 62.43%), MS (ES): 580.30 [M+H]$^+$ Synthesis of Compound I-1336: To a solution of 1.2 (0.040 g, 0.069 mmol, 1.0 eq) in methanol (1 ml), palladium on charcoal (0.020 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure I-1336 (0.025 g, Yield: 74.01%). MS (ES):

m/z 490.52 [M+H]⁺ LCMS purity: 100%, HPLC purity: 99.27%, CHIRAL HPLC: 49.97%, 50.02%, ¹H NMR (DMSO-d₆, 400 MHZ): 8.80 (s, 1H), 8.71-8.69 (d, J=8 Hz, 1H), 8.40 (s, 2H), 7.29-7.28 (d, J=4.8 Hz, 1H), 8.02-8.00 (d, J=8 Hz, 1H), 7.29-7.25 (m, 1H), 6.79 (s, 1H), 5.10-5.07 (m, 1H), 4.92 (bs, 1H), 4.31-4.26 (m, 1H), 4.09-4.07 (d, J=8 Hz, 1H), 3.65-3.60 (t, J=10.8 Hz, 2H), 3.13-3.12 (d, J=4.8 Hz, 3H), 1.77 (bs, 2H), 1.68 (bs, 2H), 1.64-1.58 (m, 1H), 1.24 (bs, 6H), 1.03 (bs, 3H).

Additional compounds prepared by substantially the same method, and their characterization data, are listed in the table below. The intermediate corresponding to 1 of the above scheme is also listed for each compound.

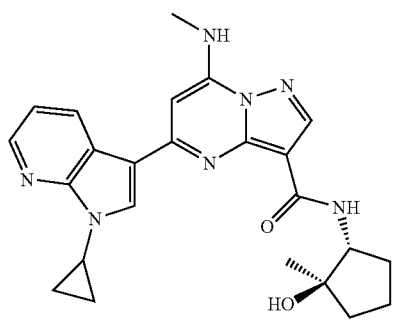

| Compound | Intermediate | Characterization data |
|---|---|---|
| I-1335 | (structure shown) synthesized as per experimental protocol of I-960 | MS (ES): m/z 446.62 [M + H]⁺ LCMS purity: 98.26%, HPLC purity: 97.48%, CHIRAL HPLC: 48.16%, 48.80%, ¹H NMR (DMSO-d₆, 400 MHZ): 8.67-8.65 (d, J = 7.6 Hz, 1H), 8.52 (s, 1H), 8.41-8.41 (d, J = 3.2 Hz, 1H), 8.38 (s, 1H), 8.28-8.27 (d, J = 5.2 Hz, 1H), 7.99 (bs, 1H), 7.28-7.25 (m, 1H), 6.74 (s, 1H), 4.90 (s, 1H), 3.79-3.76 (m, 1H), 3.11-3.10 (d, J = 4.8 Hz, 3H), 1.55 (bs, 4H), 1.23 (bs, 4H), 1.16-1.15 (d, J = 5.6 Hz, 3H), 1.11 (s, 3H). |

115.2. Chiral Separation

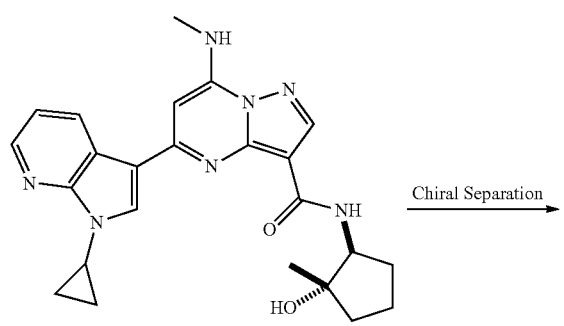

Synthesis of Compound I-1280 & I-1281.

Isomers of I-1335 (0.110 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure FR-a (0.028 g). MS(ES): m/z 446.76 [M+H]⁺, LCMS purity: 98.05%, HPLC purity: 97.26%, CHIRAL HPLC purity: 100%, ¹H NMR (DMSO-d₆, 400 MHZ): 8.68-8.66 (d, J=7.6 Hz, 1H), 8.52 (s, 1H), 8.43-8.42 (d, J=4 Hz, 1H), 8.39 (s, 1H), 8.29-8.27 (d, J 5.2 Hz, 1H), 8.02-8.00 (d, J 7.6 Hz, 1H), 7.29-7.26 (m, 1H), 6.75 (s, 1H), 4.91 (s, 1H), 4.31-4.25 (m, 1H), 3.80-3.77 (m, 1H), 3.12-3.11 (d, J=4.8 Hz, 3H), 2.95-2.89 (m, 1H), 1.24 (bs, 4H), 1.17-1.16 (d, J=5.2 Hz, 4H), 1.12 (s, 3H), 1.06-1.04 (d, J=6.4 Hz, 1H).

FR-b was concentrated under reduced pressure at 30° C. to afford pure FR-b (0.030 g). MS(ES): m/z 446.76 [M+H]⁺, LCMS purity: 100%, HPLC purity: 99.39%, CHIRAL HPLC purity: 98.83%, ¹H NMR (DMSO-d₆, 400 MHZ): 8.68-8.66 (d, J=7.6 Hz, 1H), 8.52 (s, 1H), 8.43-8.42 (d, J=4 Hz, 1H), 8.39 (s, 1H), 8.29-8.27 (d, J=5.2 Hz, 1H), 8.02-8.00 (d, J=7.6 Hz, 1H), 7.29-7.26 (m, 1H), 6.75 (s, 1H), 4.31-4.25 (m, 1H), 3.81-3.76 (m, 1H), 3.12-3.11 (d, J=4.8 Hz, 3H), 1.76 (bs, 3H), 1.59-1.54 (m, 2H), 1.24 (bs, 2H), 1.17-1.16 (d, J=5.2 Hz, 4H), 1.05-1.04 (d, J=6 Hz, 3H).

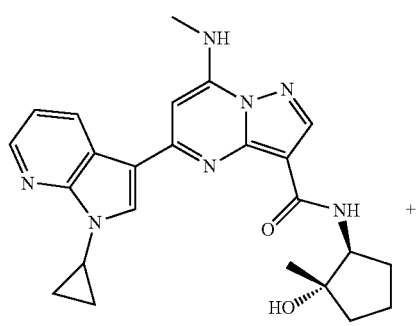

Additional compounds prepared by substantially the same method, and their characterization data, are listed in the table below.

| Compound | Isomers | Characterization data |
|---|---|---|
| I-1316 | I-1238<br>I-1239 | FR-a: MS(ES): m/z 421.72 [M + H]⁺, LCMS purity: 99.64%, HPLC purity: 99.37%, CHIRAL HPLC purity: 100%, ¹H NMR (DMSO-d₆, 400 MHZ): 9.51 (s, 1H), 8.27-8.26 (d, J = 6.4 Hz, 1H), 8.24 (s, 1H), 7.99 (bs, 2H), 7.85-7.84 (d, J = 7.2 Hz, 1H), 7.65-7.63 (d, J = 7.6 Hz, 1H), 7.59 (s, 1H), 6.84-6.80 (t, J = 7.2 Hz, 1H), 6.28 (s, 1H), 4.21-4.12 (m, 1H), 3.18-3.17 (d, J = 4.8 Hz, 1H), 2.94-2.93 (d, J = 4.4 Hz, 3H), 2.16 (bs, 1H), 1.66 (bs, 3H), 1.55 (bs, 1H), 1.42-1.37 (m, 1H), 1.00 (s, 3H).<br>FR-b : MS(ES): m/z 421.72 [M + H]⁺, LCMS purity: 100%, HPLC purity: 100%, CHIRAL HPLC purity: 99.24%, ¹H NMR (DMSO-d₆, 400 MHZ): 9.51 (s, 1H), 8.26-8.25 (d, J = 6.4 Hz, 1H), 8.23 (s, 1H), 8.01 (bs, 2H), 7.85-7.83 (d, J = 7.2 Hz, 1H), 7.64-7.62 (d, J = 7.6 Hz, 1H), 7.59 (s, 1H), 6.83-6.79 (t, J = 7.2 Hz, 1H), 6.27 (s, 1H), 4.88 (s, 1H), 4.18-4.14 (m, 1H), 3.17-3.16 (d, J = 4.8 Hz, 1H), 2.93-2.92 (d, J = 4.4 Hz, 3H), 2.16 (bs, 1H), 1.68 (bs, 3H), 1.37-1.36 (m, 1H), 0.99 (s, 3H). |
| I-1317 | I-1240<br>I-1241 | FR-a: MS(ES): m/z 440.67 [M + H]⁺, LCMS purity: 97.85%, HPLC purity: 97.59%, CHIRAL HPLC purity: 99.06%, ¹H NMR (DMSO-d₆, 400 MHZ): 8.86 (s, 1H), 8.22 (s, 1H), 8.14-8.12 (d, J = 6.4 Hz, 1H), 7.93-7.92 (d, J = 4.8 Hz, 1H), 7.56-7.54 (d, J = 7.6 Hz, 1H), 7.45-7.43 (d, J = 6.4 Hz, 1H), 6.28-6.25 (t, J = 7.2 Hz, 1H), 6.23 (s, 1H), 5.20-5.14 (m, 1H), 4.94 (s, 1H), 4.23-4.12 (m, 1H), 2.92-2.91 (d, J = 4.8 Hz, 3H), 2.24-2.17 (m, 1H), 1.73-1.65 (m, 2H), 1.63 (bs, 2H), 1.46-1.41 (m, 1H), 1.36-1.34 (d, J = 6.8 Hz, 6H), 1.06 (s, 3H).<br>FR-b: MS(ES): m/z 440.67 [M + H]⁺, LCMS purity: 96.43%, HPLC purity: 99.15%, CHIRAL HPLC purity: 97.84%, ¹H NMR (DMSO-d₆, 400 MHZ): 8.86 (s, 1H), 8.22 (s, 1H), 8.14-8.12 (d, J = 6.4 Hz, 1H), 7.93-7.92 (d, J = 4.8 Hz, 1H), 7.56-7.54 (d, J = 7.6 Hz, 1H), 7.45-7.44 (d, J = 6.4 Hz, 1H), 6.28-6.25 (t, J = 7.2 Hz, 1H), 6.23 (s, 1H), 5.20-5.14 (m, 1H), 4.94 (s, 1H), 4.22-4.17 (m, 1H), 2.92-2.91 (d, J = 4.8 Hz, 3H), 2.22-2.20 (m, 1H), 1.73-1.65 (m, 2H), 1.63 (bs, 2H), 1.46-1.41 (m, 1H), 1.36-1.34 (d, J = 6.8 Hz, 6H), 1.06 (s, 3H). |
| I-1336 | I-1221<br>I-1222 | FR-a: MS(ES): m/z 490.57 [M + H]⁺, LCMS purity: 100%, HPLC purity: 98.06%, CHIRAL HPLC purity: 100%, ¹H NMR (DMSO-d₆, 400 MHZ): 8.79 (s, 1H), 8.71-8.69 (d, J = 6.4 Hz, 1H), 8.39 (s, 2H), 8.28 (bs, 1H), 8.02-8.00 (d, J = 8 Hz, 1H), 7.29-7.25 (m, 1H), 6.79 (s, 1H), 5.13-5.07 (m, 1H), 4.92 (s, 1H), 4.31-4.26 (m, 1H), 4.09-4.07 (d, J = 7.6 Hz, 2H), 3.65-3.60 (t, J = 12 Hz, 2H), 3.12 (s, 3H), 2.22-2.18 (m, 1H), 1.77 (bs, 3H), 1.64-1.58 (m, 3H), 1.24 (bs, 2H), 1.13 (s, 4H).<br>FR-b: MS(ES): m/z 490.97 [M + H]⁺, LCMS purity: 98.84%, HPLC purity: 98.75%, CHIRAL HPLC purity: 99.18%, ¹H NMR (DMSO-d₆, 400 MHZ): 8.79 (s, 1H), 8.71-8.69 (d, J = 6.4 Hz, 1H), 8.39 (s, 2H), 8.28-8.27 (d, J = 4.8 Hz, 1H), 8.02-8.00 (d, J = 8 Hz, 1H), 7.29-7.25 (m, 1H), 6.79 (s, 1H), 5.13-5.07 (m, 1H), 4.92 (s, 1H), 4.31-4.26 (m, 1H), 4.10-4.07 (d, J = 7.6 Hz, 2H), 3.65-3.60 (t, J = 12 Hz, 2H), 3.13-3.12 (d, J = 4.8 Hz, 3H), 2.22-2.18 (m, 1H), 1.77 (bs, 3H), 1.64-1.58 (m, 3H), 1.24 (bs, 2H), 1.13 (s, 4H). |

115.3. Synthesis of N-(2-hydroxy-2-methylcyclopentyl)-7-(methylamino)-5-((2-oxo-1-(tetrahydro-2H-pyran-4-yl)-1,2-dihydropyridin-3-yl)amino)pyrazolo[1,5-a]pyrimidine-3-carboxamide (I-1254)

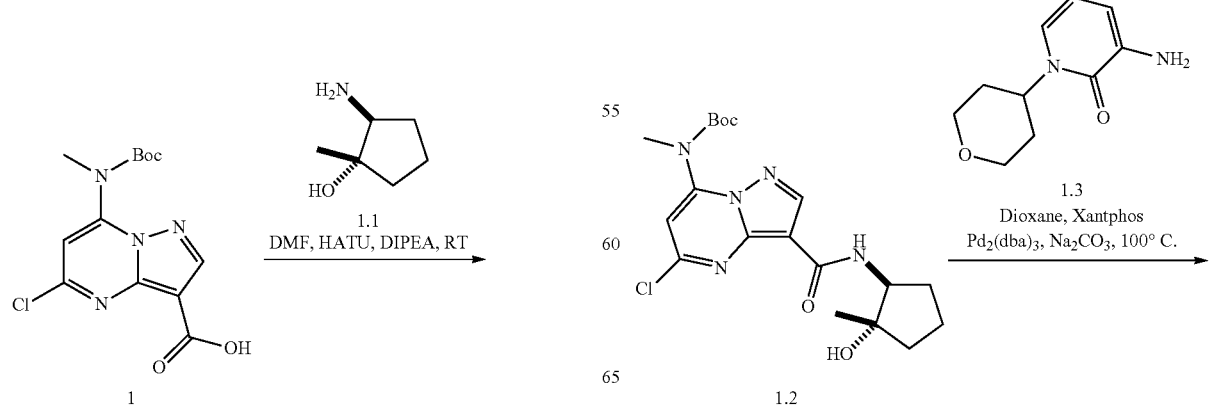

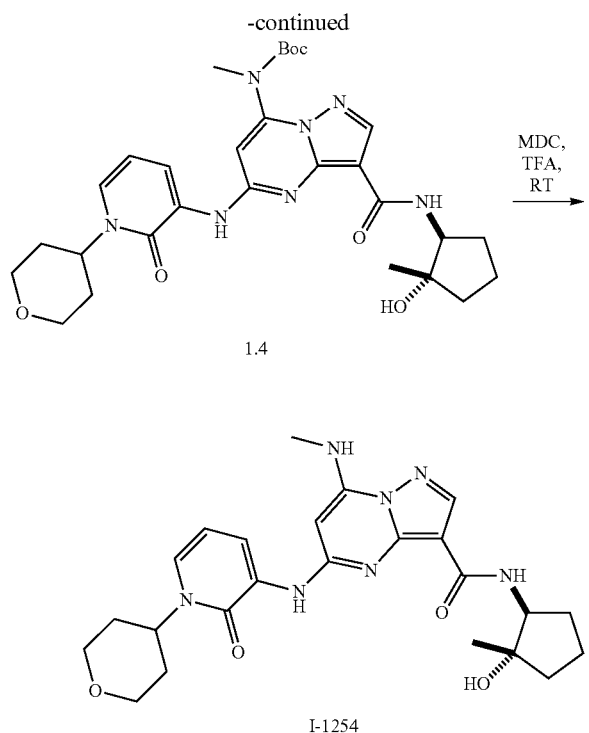

1.4

I-1254

Synthesis of Compound 1.

Compound was synthesized using general procedure of core synthesis to obtain 1. MS (ES): m/z 327.08 [M+H]+

Synthesis of Compound 1.2.

Compound was synthesized using general procedure A to obtain 1.2. (0.410 g, 98.80%), MS (ES): 424.17 [M+H]+

Synthesis of Compound 1.3.

Compound was synthesized as per experimental protocol of the intermediates to obtain 1.3. (Yield: 36.13%), MS (ES): m/z 195.23 [M+H]+

Synthesis of Compound 1.4.

Compound was synthesized using general procedure B to obtain 1.4. (0.172 g, 83.56%), MS (ES): 582.30 [M+H]+

Synthesis of Compound I-1254:

Compound was synthesized using general procedure C to obtain I-1254 (0.023 g, 69.45%), MS (ES): m/z 482.77 [M+H]+, LCMS purity: 100%, HPLC purity: 99.24%, CHIRAL HPLC: 47.25%, 48.62%, $^1$H NMR (DMSO-d$_6$, 400 MHZ): 8.84 (s, 1H), 8.22 (s, 1H), 8.14-8.13 (d, J=6 Hz, 1H), 7.94-7.93 (d, J=4.8 Hz, 1H), 7.54-7.52 (d, J=8 Hz, 1H), 7.48-7.47 (d, J=6.4 Hz, 1H), 6.27-6.23 (t, J=7.2 Hz, 1H), 6.22 (s, 1H), 5.05-4.99 (m, 1H), 4.93 (s, 1H), 4.21-4.15 (m, 1H), 4.02-3.99 (m, 2H), 3.53-3.48 (t, J=11.2 Hz, 2H), 2.91-2.90 (d, J=4.8 Hz, 3H), 2.18 (bs, 1H), 1.97-1.94 (d, J=11.2 Hz, 2H), 1.67 (bs, 3H), 1.60 (bs, 3H), 1.44-1.39 (m, 1H), 1.05 (s, 3H).

Example 116: Synthesis of N-(3-methoxycyclopentyl)-7-(methylamino)-5-((2-oxo-1-(tetrahydro-2H-pyran-4-yl)-1,2-dihydropyridin-3-yl)amino)pyrazolo[1,5-a]pyrimidine-3-carboxamide (I-1334)

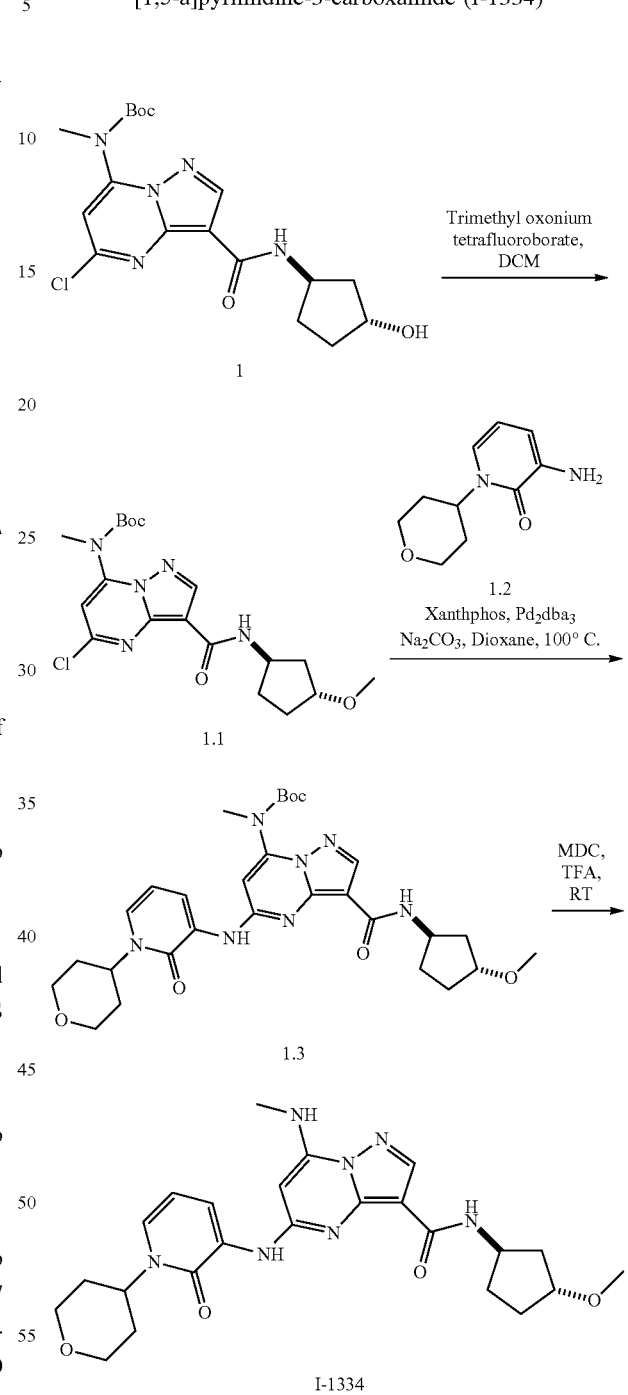

I-1334

Synthesis of Compound 1.

Compound was synthesized as per experimental protocol of I-701 to obtain 1. (Yield: 59.79%), MS (ES): m/z 410.1 [M+H]+.

Synthesis of Compound 1.1.

To a cooled solution of 1. (0.3 g, 0.73 mmol, 1.0 eq), in dichloromethane (5 mL) was added Trimethyloxonium tetrafluoroborate (0.216 g, 1.46 mmol, 2.0 eq). The reaction mixture was stirred at room temperature for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.5% methanol in dichloromethane to obtain 1.1. (0.155 g, 49.96%). MS(ES): m/z 424.17 [M+H]

Synthesis of Compound 1.2.

Compound was synthesized as per experimental protocol of the intermediates to obtain 1.2. (Yield: 36.13%), MS (ES): m/z 195.23 [M+H]

Synthesis of Compound 1.3.

Compound was synthesized using general procedure B to obtain 1.3. (0.138 g, 67.05%), MS (ES): 582.30 [M+H]

Synthesis of Compound I-1334: Compound was synthesized using general procedure C to obtain I-1334 (0.028 g, 89.00%), MS (ES): 482.41 [M+H]$^+$ LCMS purity: 100%, HPLC purity: 98.29%, $^1$H NMR (DMSO-d$_6$, 400 MHZ): 8.87 (s, 1H), 8.23-8.22 (d, J=5.6 Hz, 1H), 7.92-791 (d, J=4.8 Hz, 1H), 7.66-7.64 (d, J=7.6 Hz, 1H), 7.49-7.48 (d, J=6.4 Hz, 1H), 6.29-6.25 (t, J=6.8 Hz, 1H), 6.21 (s, 1H), 4.35-4.29 (m, 1H), 4.25 (bs, 1H), 4.11 (bs, 2H), 3.86 (bs, 1H), 3.54-3.48 (t, J=11.6 Hz, 2H), 3.18 (s, 3H), 2.90-2.89 (d, J=4 Hz, 3H), 2.11 (bs, 2H), 1.97-1.95 (d, J=10 Hz, 2H), 1.76-1.74 (d, J=8.8 Hz, 2H), 1.33 (s, 1H), 1.23 (bs, 4H).

Example 117: Synthesis of Compounds Comprising N-(3-methoxycyclohexyl)aminocarbonyl at Position 3 of the pyrazolo[1,5-a]pyrimidine (I-1297)

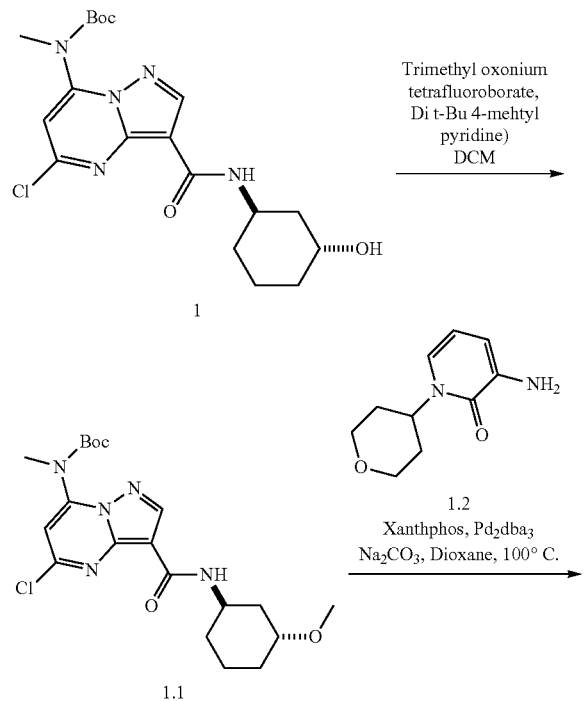

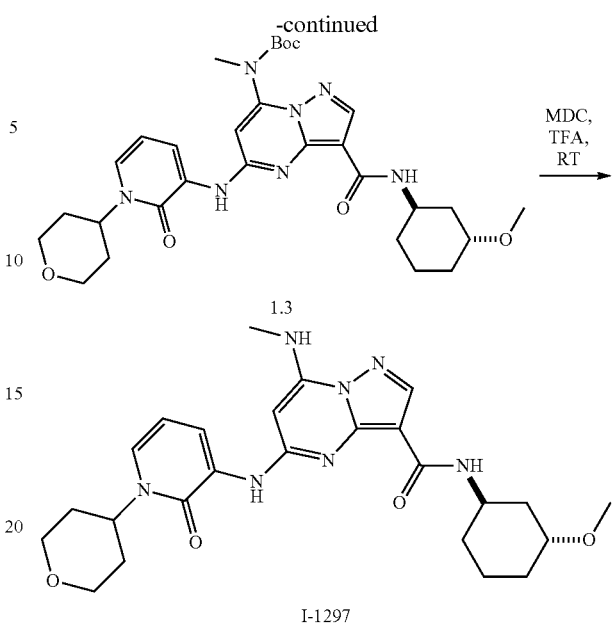

Synthesis of Compound 1.

Compound was synthesized as per experimental protocol of I-703 to obtain 1. (Yield: 46.25%), MS (ES): m/z 424.17 [M+H]$^+$ Synthesis of Compound 1.1.

To a solution of 1 (0.590 g, 1.39 mmol, 1.0 eq), in dichloromethane (6 mL) was added Trimethyloxonium tetrafluoroborate (0.411 g, 2.78 mmol, 2.0 eq) and Di t-Bu 4-methyl pyridine (0.854 g, 4.17 mmol, 3.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 2.5% methanol in dichloromethane to obtain pure 1.1. (0.360 g, 59.06%). MS (ES): m/z 438.19 [M+H]$^+$ Synthesis of Compound 1.2.

Compound was synthesized as per experimental protocol of the intermediates to obtain 1.2. (Yield: 36.13%), MS (ES): m/z 195.23 [M+H]$^+$ Synthesis of Compound 1.3.

Compound was synthesized using general procedure B to obtain 1.3. (0.160 g, Yield: 78.42%). MS (ES): m/z 596.32 [M+H]$^+$ Synthesis of Compound I-1297:

Compound was synthesized using general procedure C to obtain I-1297. (Yield: 0.024 g, 72.12%). MS (ES): m/z 496.67 [M+H]$^+$, LCMS purity: 95.04%, HPLC purity: 95.55%, $^1$H NMR (DMSO-d$_6$, 400 MHZ): 8.88 (s, 1H), 8.21 (s, 1H), 8.19 (s, 1H), 7.93-7.91 (d, J=4.8 Hz, 1H), 7.58-7.56 (d, J=8 Hz, 1H), 7.50-7.48 (d, J=6.4 Hz, 1H), 6.32-6.29 (t, J=6.8 Hz, 1H), 6.23 (s, 1H), 4.03-4.00 (d, J=12 Hz, 2H), 3.58-3.49 (m, 3H), 3.25 (s, 3H), 2.92-2.91 (d, J=4.8 Hz, 3H), 2.14 (bs, 1H), 2.00-1.93 (m, 4H), 1.78 (bs, 3H), 1.54 (bs, 2H), 1.39-1.36 (d, J=11.2 Hz, 2H), 1.20 (bs, 2H).

Additional compounds prepared by substantially the same method, and their characterization data, are listed in the table below. The intermediate corresponding to 1.2 of the above scheme is also listed for each compound.

| Compound | Intermediate | Characterization data |
|---|---|---|
| I-1289 | 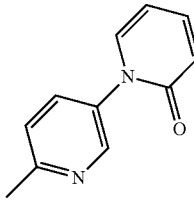 | MS (ES): m/z 503.58 [M + H]+, LCMS purity: 100%, HPLC purity: 100%, CHIRAL HPLC purity: 50:49%, $^1$H NMR (DMSO-$d_6$, 400 MHZ): 8.98 (s, 1H), 8.58 (s, 1H), 8.20 (s, 1H), 7.88-7.86 (d, J = 7.6 Hz, 2H), 7.58 (s, 1H), 7.47-7.45 (d, J = 7.2 Hz, 2H), 6.38 (s, 1H), 6.25 (s, 1H), 4.11 (s, 1H), 3.59 (s, 1H), 3.25 (s, 3H), 2.89 (s, 3H), 2.56 (s, 3H), 2.16-2.14 (d, J = 10.4 Hz, 1H), 1.93 (s, 1H) 1.78 (s, 1H) 1.61-1.55 (m, 2H), 1.38-1.23 (m, 4H). |
| I-1288 | 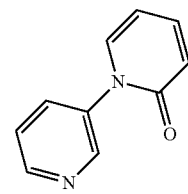 | MS (ES): m/z 489.67 [M + H]+, LCMS purity: 95.42%, HPLC purity: 96.56%, CHIRAL HPLC purity: 48:48%, $^1$H NMR (DMSO-$d_6$, 400 MHZ): 9.00 (s, 1H), 8.76-8.75 (d, J = 2.4 Hz, 1H), 8.70-8.69 (d, J = 4.8 Hz, 1H), 8.35-8.33 (d, J = 7.2 Hz, 1H), 8.22 (s, 1H), 8.04-8.02 (d, J = 8.4 Hz, 1H), 7.96-7.95 (d, J = 4.8 Hz, 1H), 7.65-7.56 (m, 2H), 7.46-7.44 (d, J = 6.8 Hz, 1H), 6.43-6.39 (t, J = 7.2 Hz, 1H), 6.27 (s, 1H), 4.12-4.10 (m, 1H), 3.61 (s, 1H), 3.27 (s, 3H), 2.92-2.91 (d, J = 4.8 Hz, 3H), 2.18-2.15 (m, 1H), 1.96-1.94 (m, 1H), 1.82-1.79 (m, 1H), 1.65-1.53 (m, 2H), 1.43-1.30 (m, 2H), 1.26-1.24 (m, 1H). |
| I-1253 | 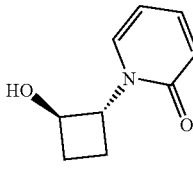 | MS (ES): m/z 482.82 [M + H]+, LCMS purity: 99.35%, HPLC purity: 99.25%, CHIRAL HPLC: 48.51%, 50.98%, $^1$H NMR (DMSO-$d_6$, 400 MHZ): 8.90 (s, 1H), 8.21 (s, 1H), 8.19 (s, 1H), 7.93-7.91 (d, J = 4.8 Hz, 1H), 7.60-7.58 (d, J = 8 Hz, 1H), 7.52-7.50 (d, J = 6.8 Hz, 1H), 6.34-6.31 (t, J = 7.2 Hz, 1H), 6.23 (s, 1H), 5.64-5.62 (d, J = 6.8 Hz, 1H), 4.95-4.93 (d, J = 8.4 Hz, 1H), 4.39-4.35 (m, 1H), 4.08 (bs, 1H), 3.59 (bs, 1H), 3.25 (s, 3H), 2.92-2.90 (d, J = 4.8 Hz, 3H), 2.15-2.13 (d, J = 7.2 Hz, 3H), 1.78 (bs, 1H), 1.63 (bs, 3H), 1.58 (bs, 3H), 0.90-0.86 (t, J = 7.2 Hz, 2H). |
| I-1252 | 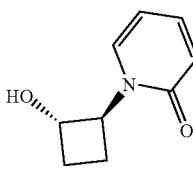 | MS (ES): m/z 482.41 [M + H]+, LCMS purity: 98.09%, HPLC purity: 98.11%, CHIRAL HPLC: 41.28%, 49.65%, $^1$H NMR (DMSO-$d_6$, 400 MHZ): 8.89 (s, 1H), 8.20 (s, 1H), 8.18 (s, 1H), 7.91-7.90 (d, J = 4.8 Hz, 1H), 7.59-7.57 (d, J = 8.4 Hz, 1H), 7.50.7.49 (d, J = 6.8 Hz, 1H), 7.39 (bs, 2H), 6.33-6.29 (t, J = 7.2 Hz, 1H), 6.22 (s, 1H), 5.62 (bs, 1H), 4.93-4.91 (d, J = 8.4 Hz, 1H), 4.36 (bs, 1H), 4.07 (bs, 1H), 3.57 (bs, 1H), 3.24 (s, 3H), 2.90-2.89 (d, J = 4.8 Hz, 3H), 2.13-2.11 (d, J = 7.2 Hz, 3H), 1.77 (bs, 3H), 1.59 (bs, 3H), 0.85 (bs, 1H). |

Example 118: Synthesis of Compounds Comprising N-(3-hydroxycyclopentyl)aminocarbonyl at Position 3 of the pyrazolo[1,5-a]pyrimidine

118.1. Synthesis of Compound I-1358

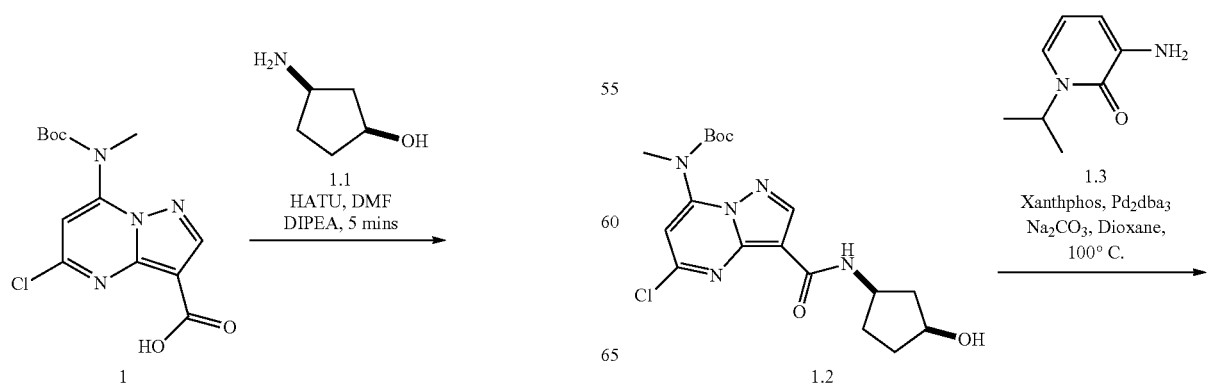

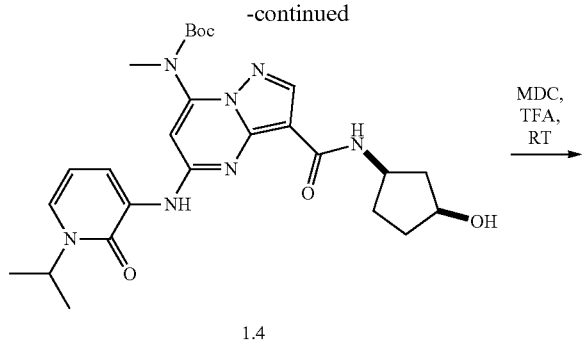

Synthesis of Compound 1.

Compound was synthesized using general procedure of core synthesis to obtain 1. (Yield: 71.67%). MS (ES): 327.7 [M+H]⁺.

Synthesis of Compound 1.2.

Compound was synthesized using general procedure A to obtain 1.2. (0.3 g, 47.83%), MS (ES): 410.87 [M+H]+.

Synthesis of Compound 1.3.

Compound was synthesized as per experimental procedure of the intermediates to obtain 1.3 (84%). MS (ES): m/z 153.2 [M+H]+.

Synthesis of Compound 1.4.

Compound was synthesized using general procedure B synthesis to obtain 1.4 (Yield: 015 g, 62.64%). MS (ES): m/z 590.7 [M+H]+.

Synthesis of Compound I-1358:

Compound was synthesized using general procedure C to obtain I-1358 (0.025 g, 75.28%), MS (ES): m/z 426.29 [M+H]+, LCMS purity: 100%, HPLC purity: 99.51%, CHIRAL HPLC: 51.63%, 48.36%, ¹H NMR (DMSO-d₆, 400 MHz): 8.87 (s, 1H), 8.29-8.28 (d, J 6 Hz, 1H), 8.19 (s, 1H), 7.90-7.89 (d, J=4.8 Hz, 1H), 7.71-7.69 (d, J=8 Hz, 1H), 7.44-7.43 (d, J=6 Hz, 1H), 6.51-6.48 (m, 1H), 6.26 (s, 1H), 5.22-5.15 (m, 1H), 4.76 (s, 1H), 4.31-4.27 (m, 1H), 4.18 (s, 1H) 3.36 (s, 1H), 2.91 (s, 3H), 2.30-2.22 (m, 1H), 2.02-2.01 (m, 1H), 1.71-1.62 (m, 3H), 1.45-1.24 (m, 6H).

Additional compounds prepared by substantially the same method, and their characterization data, are listed in the table below. The intermediate corresponding to 1.3 of the above scheme is also listed for each compound.

| Compound | Intermediate | Characterization data |
|---|---|---|
| I-1357 | ![structure] | MS (ES): m/z 468.53 [M + H]+, LCMS purity: 100%, HPLC purity: 98.54%, CHIRAL HPLC: 49.57%, 49.94%, ¹H NMR (DMSO-d₆, 400 MHz): 8.85 (s, 1H), 8.31-8.29 (d, J = 6.8 Hz, 1H), 8.19 (s, 1H), 7.91 (s, 1H), 7.70-7.68 (d, J = 4.2 Hz, 1H), 7.47-7.46 (d, J = 6.8 Hz, 1H), 6.49 (s, 1H), 6.26 (s, 1H), 5.04 (s, 1H), 4.75 (s, 1H), 4.27 (s, 2H), 4.18 (bs, 1H), 4.03-4.01 (d, J = 9.2 Hz, 1H), 3.86 (s, 1H), 3.58-3.49 (m, 2H), 2.91 (s, 3H), 2.34-2.25 (m, 2H), 2.01-1.97 (m, 3H), 1.77-1.67 (m, 2H), 1.42 (bs, 1H), 1.24 (bs, 1H). |

118.2. Chiral Separation

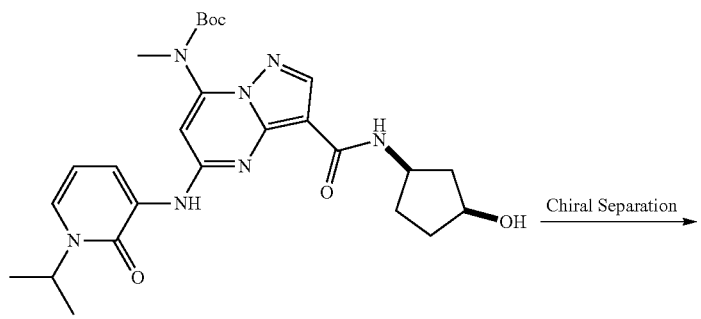

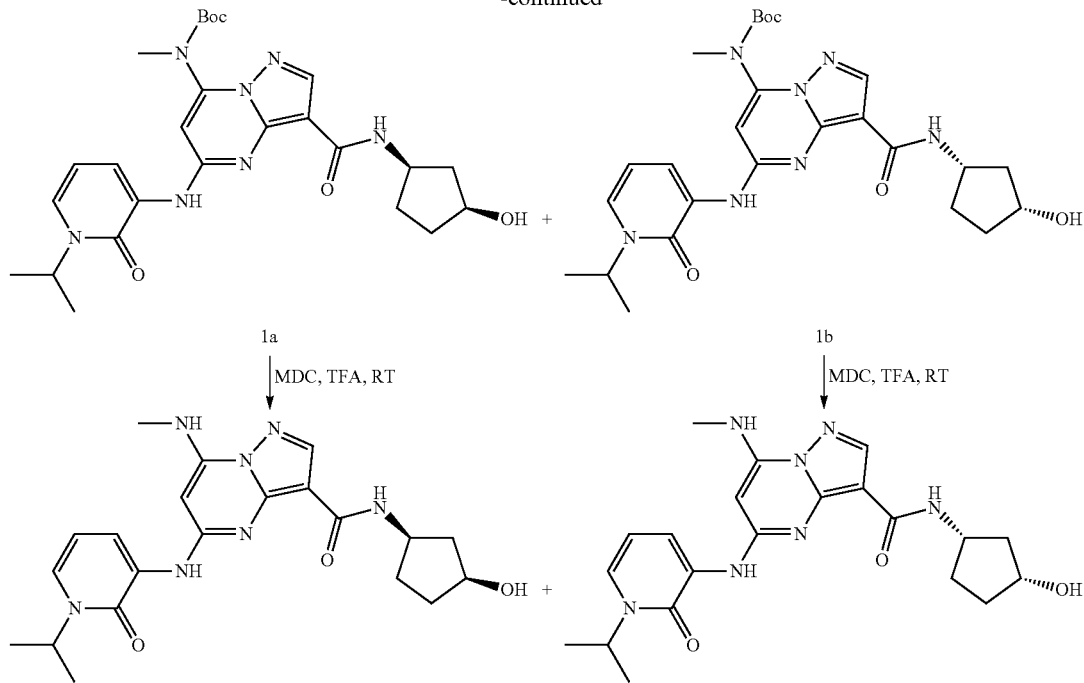

Synthesis of Compound 1.

Compound was synthesized as per experimental protocol of I-1358 to obtain 1. (Yield: 62.64%), MS (ES): 590.7 [M+H]+

Synthesis of compound 1a and 1b.

Isomers of 1 (0.1 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 1a. (0.040 g). MS(ES): m/z 526.27 [M+H]+. FR-b was concentrated under reduced pressure at 30° C. to afford pure 1b. (0.040 g). MS(ES): m/z 526.27 [M+H]+.

Synthesis of Compound I-1265 and I-1266:

Compound was synthesized using general procedure C to obtain FR-a (0.029 g, 89.56%). MS (ES): m/z 426.82 [M+H]+, LCMS purity: 98.96%, HPLC purity: 100%, Chiral HPLC: 100%, $^1$H NMR (DMSO-$d_6$, 400 MHZ): 8.86 (s, 1H), 8.28-8.27 (d, J=6.8 Hz, 1H), 8.18 (s, 1H), 7.90-7.89 (d, J=4.8 Hz, 1H), 7.70-7.68 (d, J=7.6 Hz, 1H), 7.43-7.42 (d, J=6.8 Hz, 1H), 6.50-6.47 (t, J=7.2 Hz, 1H), 6.25 (s, 1H), 5.19-5.16 (t, J=6.8 Hz, 1H), 4.30-4.24 (m, 1H), 4.16 (bs, 1H), 3.57 (s, 1H), 2.90-2.89 (d, J=4.8 Hz, 3H), 1.72-1.66 (m, 3H), 1.36-1.34 (d, J=6.8 Hz, 6H), 1.23 (bs, 2H), 1.11-1.07 (t, J=7.2 Hz, 1H).

And FR-b (0.029 g, 89.56%). MS (ES): m/z 426.82 [M+H]+, LCMS purity: 100%, HPLC purity: 100%, Chiral HPLC: 95.39%, $^1$H NMR (DMSO-$d_6$, 400 MHZ): 8.86 (s, 1H), 8.28-8.27 (d, J=6.8 Hz, 1H), 8.18 (s, 1H), 7.90-7.89 (d, J=4.8 Hz, 1H), 7.70-7.68 (d, J=7.6 Hz, 1H), 7.43-7.42 (d, J=6.8 Hz, 1H), 6.50-6.47 (t, J=7.2 Hz, 1H), 6.25 (s, 1H), 5.19-5.16 (t, J=6.8 Hz, 1H), 4.30-4.26 (m, 1H), 4.16 (bs, 1H), 3.57 (s, 1H), 2.90-2.89 (d, J=4.8 Hz, 3H), 1.66 (bs, 3H), 1.36-1.34 (d, J=6.8 Hz, 6H), 1.23 (bs, 2H), 1.11-1.07 (t, J=7.2 Hz, 1H).

Additional compounds prepared by substantially the same method, and their characterization data, are listed in the table below.

| Compound | Isomers | Characterization data |
|---|---|---|
| I-1357 | I-1263<br>I-1264 | FR-a: MS (ES): m/z 468.82 [M + H]+, LCMS purity: 100%, HPLC purity: 99.29%, CHIRAL HPLC: 96.63%, $^1$H NMR (DMSO-$d_6$, 400 MHZ): 8.85 (s, 1H), 8.30-8.28 (d, J = 7.2 Hz, 1H), 8.18 (s, 1H), 7.91-7.89 (d, J = 4.8 Hz, 1H), 7.69-7.67 (d, J = 7.6 Hz, 1H), 7.47-7.45 (d, J = 7.2 Hz, 1H), 6.49-6.46 (t, J = 7.2 Hz, 1H), 6.25 (s, 1H), 5.04 (bs, 1H), 4.75-4.74 (d, J = 3.2 Hz, 1H), 4.28-4.26 (d, J = 7.6 Hz, 1H), 4.17 (bs, 1H), 4.02-4.00 (d, J = 7.6 Hz, 2H), 3.57 (bs, 2H), 3.54-3.48 (d, J = 6.8 Hz, 1H), 2.91-2.90 (d, J = 4.8 Hz, 3H), 2.02-1.96 (m, 3H), 1.66 (bs, 1H), 1.23 (bs, 5H).<br>FR-b: MS (ES): m/z 468.82 [M + H]+, LCMS purity: 100%, HPLC purity: 97.00%, CHIRAL HPLC: 95.63%, $^1$H NMR (DMSO-$d_6$, 400 MHZ): 8.85 (s, 1H), 8.30-8.28 (d, J = 7.2 Hz, 1H), 8.18 (s, 1H), 7.91-7.89 (d, J = 4.8 Hz, 1H), 7.69-7.67 (d, J = 7.6 Hz, 1H), 7.46-7.45 (d, J = 7.2 Hz, 1H), 6.49-6.46 (t, J = 7.2 Hz, 1H), 6.25 (s, 1H), 5.04 (bs, 1H), 4.75-4.74 (d, J = 3.2 Hz, 1H), 4.30-4.26 (m, 1H), 4.16 (bs, 1H), 4.02-4.00 (d, J = 7.6 Hz, 2H), 3.57 (bs, 1H), 3.54-3.48 (d, J = 6.8 Hz, 2H), 2.91- |

| Compound | Isomers | Characterization data |
|---|---|---|
| | | 2.90 (d, J = 4.8 Hz, 3H), 2.01-1.93 (m, 3H), 1.66 (bs, 1H), 1.23 (bs, 5H). |

Example 119: Synthesis of Compounds Comprising N-(3-hydroxy-3-methylcyclohexyl)aminocarbonyl at Position 3 of the pyrazolo[1,5-a]pyrimidine 119.1. Synthesis of I-1337

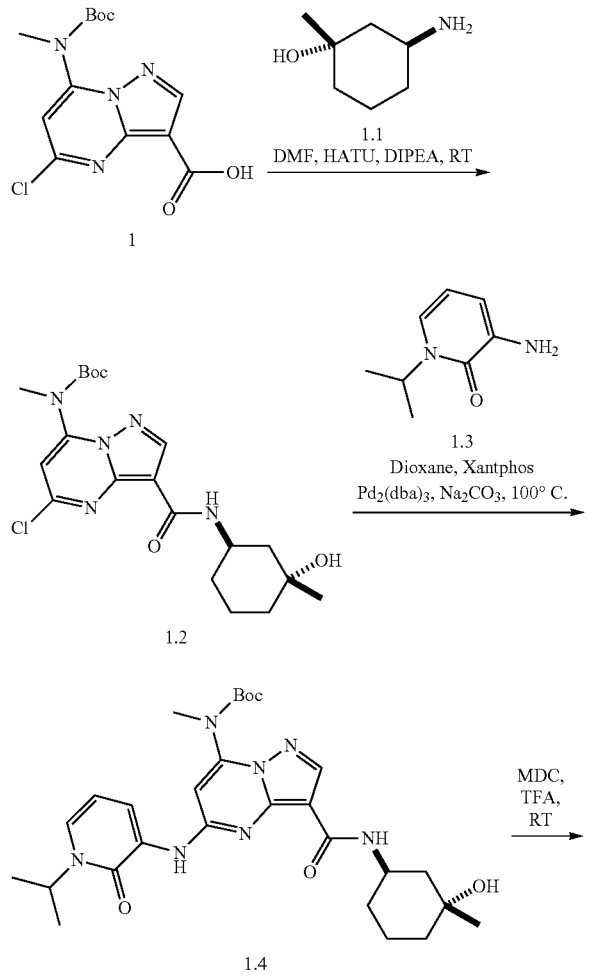

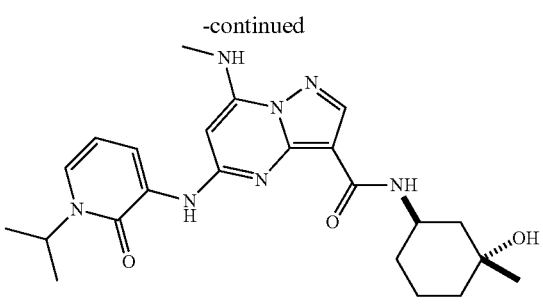

I-1337

Synthesis of Compound 1.

Compound was synthesized using general procedure of core synthesis to obtain 1. MS (ES): m/z 327.08 [M+H]⁺

Synthesis of Compound 1.2.

Compound was synthesized using general procedure A to obtain 1.2. (0.160 g, 95.50%), MS (ES): 438.19 [M+H]

Synthesis of Compound 1.3.

Compound was synthesized as per experimental protocol of the intermediates to obtain 1.3. (Yield: 82.29%), MS (ES): m/z 153.10 [M+H]

Synthesis of Compound 1.4.

Compound was synthesized using general procedure B to obtain 1.4. (0.140 g, 73.82%), MS (ES): 554.30 [M+H]⁺

Synthesis of Compound I-1337:

Compound was synthesized using general procedure C to obtain I-1337 (0.025 g, 76.30%), MS (ES): 454.77 [M+H]⁺ LCMS purity: 100%, HPLC purity: 99.23%, CHIRAL HPLC: 49.44%, 50.55%, ¹H NMR (DMSO-d₆, 400 MHZ): 8.90 (s, 1H), 8.19 (s, 1H), 8.17 (s, 1H), 7.91 (bs, 1H), 7.57-7.55 (d, J=8.8 Hz, 1H), 7.50-7.48 (d, J=6.8 Hz, 1H), 6.28-6.27 (t, J=6.8 Hz, 1H), 6.24 (s, 1H), 5.20-5.17 (m, 1H), 4.26 (s, 1H), 4.16 (bs, 1H), 2.92-2.91 (d, J=4.8 Hz, 3H), 2.52 (s, 3H), 2.06-1.97 (m, 1H), 1.89-1.86 (d, J=13.2 Hz, 1H), 1.74 (bs, 1H), 1.54 (bs, 2H), 1.37-1.35 (d, J=6.8 Hz, 6H), 1.22 (bs, 3H).

119.2. Chiral Separation

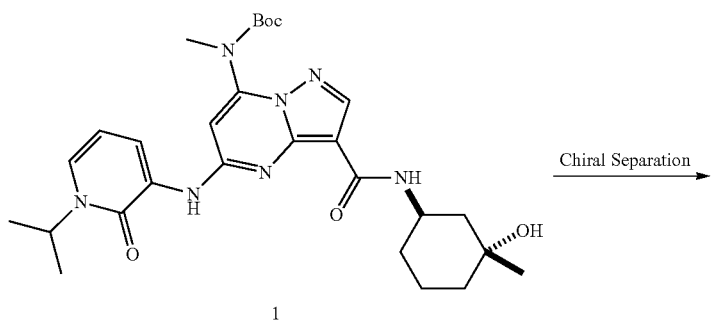

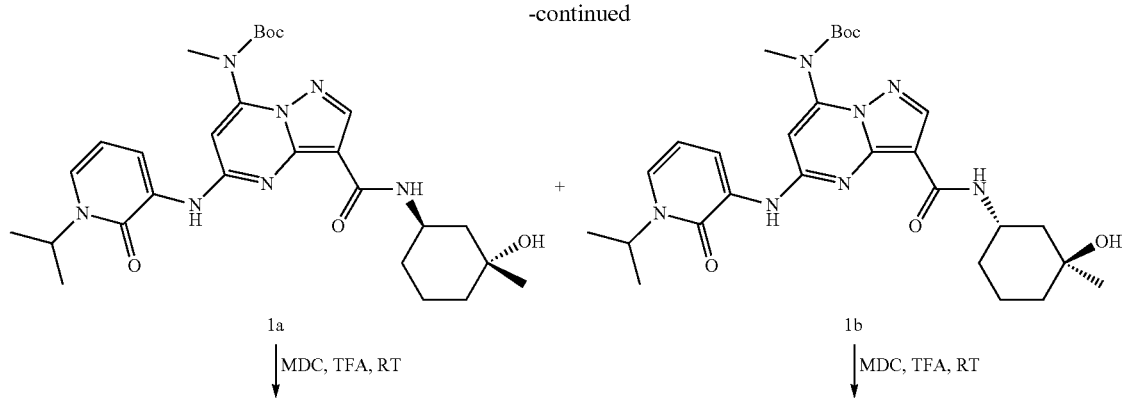

1a            1b

MDC, TFA, RT      MDC, TFA, RT

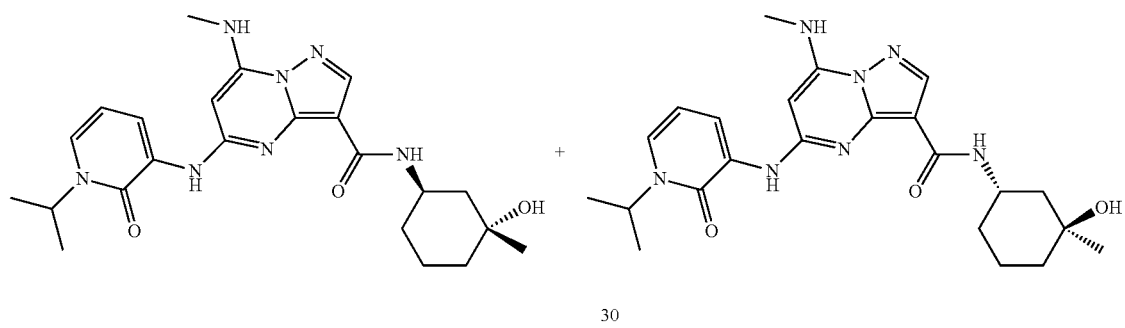

Synthesis of Compound 1.

Compound was synthesized as per experimental protocol of I-1337 to obtain 1. (Yield: 73.82%), MS (ES): 554.30 [M+H]$^+$ Synthesis of compound 1a and 1b.

Isomers of 1 (0.1 g) were separated out using column CHIRALPAK AD-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 1a. (0.040 g). MS(ES): m/z 554.30 [M+H]$^+$. FR-b was concentrated under reduced pressure at 30° C. to afford pure 1b. (0.040 g). MS(ES): m/z 554.30 [M+H]$^+$.

Synthesis of Compound I-1242 and I-1243:

Compound was synthesized using general procedure C to obtain FR-a (0.029 g, 88.50%), MS (ES): 454.66 [M+H]$^+$ LCMS purity: 100%, HPLC purity: 98.93%, CHIRAL HPLC: 100%, $^1$H NMR (DMSO-d$_6$, 400 MHZ): 8.90 (s, 1H), 8.19 (s, 1H), 8.17 (s, 1H), 7.92-7.90 (d, J=4.8 Hz, 1H), 7.57-7.55 (d, J=8.8 Hz, 1H), 7.50-7.48 (d, J=6.8 Hz, 1H), 6.28-6.27 (t, J=6.8 Hz, 1H), 6.24 (s, 1H), 5.22-5.15 (m, 1H), 4.26 (s, 1H), 4.16 (bs, 1H), 2.92-2.91 (d, J=4.8 Hz, 3H), 2.52 (s, 3H), 1.54 (bs, 2H), 1.37-1.35 (d, J=6.4 Hz, 6H), 1.24 (bs, 2H), 1.18 (s, 4H).

And FR-b (0.029 g, 88.50%), MS (ES): 454.77 [M+H]$^+$ LCMS purity: 100%, HPLC purity: 98.88%, CHIRAL HPLC: 100%, $^1$H NMR (DMSO-d$_6$, 400 MHZ): 8.88 (s, 1H), 8.18 (s, 1H), 8.16 (s, 1H), 7.90-7.89 (d, J=4.8 Hz, 1H), 7.57-7.53 (d, J=8.8 Hz, 1H), 7.48-7.47 (d, J=6.8 Hz, 1H), 6.27-6.23 (t, J=6.8 Hz, 1H), 6.22 (s, 1H), 5.19-5.15 (m, 1H), 4.24 (s, 1H), 4.15 (bs, 1H), 2.90-2.89 (d, J=4.8 Hz, 3H), 2.50 (s, 3H), 1.56 (bs, 2H), 1.35-1.34 (d, J=6.4 Hz, 6H), 1.23 (bs, 2H), 1.16 (s, 4H).

Example 120: Synthesis of N-(3-methoxy-3-methyl-cyclohexyl)-7-(methylamino)-5-((2-oxo-1-(tetra-hydro-2H-pyran-4-yl)-1,2-dihydropyridin-3-yl)amino)pyrazolo[1,5-a]pyrimidine-3-carboxamide (I-1274)

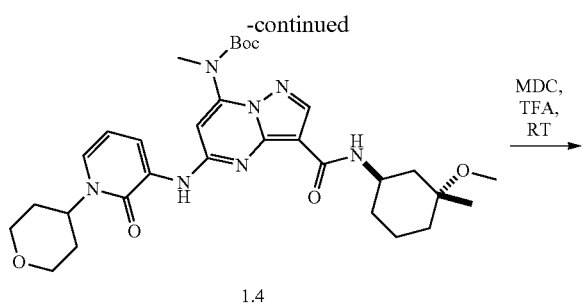

1.4

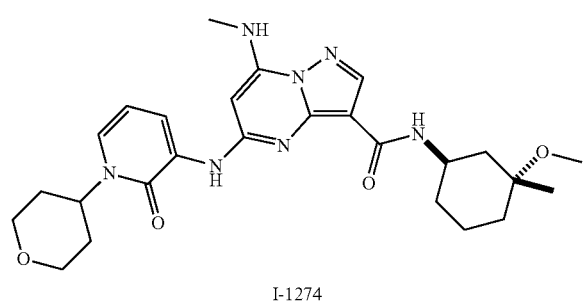

I-1274

Synthesis of Compound 1.

Compound was synthesized using general procedure of core synthesis to obtain 1. MS (ES): m/z 327.08 [M+H]⁺

Synthesis of Compound 1.2.

Compound was synthesized using general procedure A to obtain 1.2. (0.510 g, Yield: 55.86%), MS (ES): 452.20 [M+H]⁺

Synthesis of Compound 1.3.

Compound was synthesized as per experimental protocol of the intermediates to obtain 1.3. (Yield: 36.13%), MS (ES): m/z 195.23 [M+H]⁺

Synthesis of Compound 1.4.

Compound was synthesized using general procedure B to obtain 1.4. (0.120 g, Yield: 77.35%), MS (ES): 610.33 [M+H]⁺

Synthesis of Compound I-1274:

Compound was synthesized using general procedure C to obtain I-1274 (0.020 g, 79.76%), MS (ES): m/z 510.92 [M+H]⁺, LCMS purity: 100%, HPLC purity: 98.58%, Chiral HPLC purity: 47.20%, 49.45%, ¹H NMR (DMSO-d₆, 400 MHZ): 8.88 (s, 1H), 8.19 (s, 1H), 8.17 (s, 1H), 7.92-7.91 (d, J=4.8 Hz, 1H), 7.57-7.55 (d, J=8.4 Hz, 1H), 7.51-7.50 (d, J 6 Hz, 1H), 6.29-6.26 (t, J=7.2 Hz, 1H), 6.22 (s, 1H), 5.06 (bs, 1H), 4.01-3.99 (m, 3H), 3.54-3.48 (t, J=11.2 Hz, 2H), 3.13 (s, 3H), 2.91-2.89 (d, J=4.8 Hz, 3H), 1.55 (bs, 2H), 1.23 (bs, 6H), 1.14 (s, 5H), 0.85-0.79 (m, 2H).

Additional compounds prepared by substantially the same method, and their characterization data, are listed in the table below. The intermediate corresponding to 1.3 of the above scheme is also listed for each compound

| Compound | Intermediate | Characterization data |
|---|---|---|
| I-1237 | ![structure] | MS (ES): m/z 510.51 [M + H]⁺, LCMS purity: 100%, HPLC purity: 99.08%, CHIRAL HPLC: 50.16%, 49.83%, ¹H NMR (DMSO-d₆, 400 MHZ): 8.91 (s, 1H), 8.20 (s, 1H), 8.17 (s, 1H), 7.92-7.91 (d, J = 4.8 Hz, 1H), 7.56-7.54 (d, J = 7.2 Hz, 2H), 6.29-6.25 (t, J = 7.2 Hz, 1H), 6.23 (s, 1H), 3.98 (bs, 2H), 3.84 (bs, 2H), 3.59-3.54 (d, J = 9.2 Hz, 1H), 3.48-3.42 (t, J = 10.8 Hz, 1H), 3.13 (s, 3H), 2.90-2.89 (d, J = 4.8 Hz, 3H), 2.07 (s, 1H), 1.96 (bs, 2H), 1.55 (bs, 3H), 1.23 (bs, 3H), 1.11 (s, 6H). |
| I-1236 | ![structure] | MS (ES): m/z 510.82 [M + H]⁺, LCMS purity: 98.57%, HPLC purity: 96.75%, CHIRAL HPLC: 48.80%, 48.38%, ¹H NMR (DMSO-d₆, 400 MHZ): 8.90 (s, 1H), 8.20 (s, 1H), 8.17 (s, 1H), 7.91-7.90 (d, J = 4.8 Hz, 1H), 7.56-7.54 (d, J = 7.2 Hz, 2H), 6.29-6.25 (t, J = 7.2 Hz, 1H), 6.23 (s, 1H), 4.88 (bs, 1H), 3.99 (bs, 1H), 3.84 (bs, 2H), 3.59-3.55 (t, J = 9.6 Hz, 1H), 3.49-3.43 (t, J = 10.8 Hz, 1H), 3.13 (s, 3H), 2.90-2.89 (d, J = 4.8 Hz, 3H), 1.96 (bs, 2H), 1.55 (bs, 3H), 1.23 (bs, 4H), 1.14 (s, 6H). |
| I-1235 | ![structure] | MS (ES): m/z 468.87 [M + H]⁺, LCMS purity: 100%, HPLC purity: 99.37%, CHIRAL HPLC: 49.17%, 50.33%, ¹H NMR (DMSO-d₆, 400 MHZ): 8.90 (s, 1H), 8.18 (s, 2H), 7.91-7.90 (d, J = 4.4 Hz, 1H), 7.58-7.56 (d, J = 7.2 Hz, 1H), 7.49-7.47 (d, J = 6 Hz, 1H), 6.31-6.27 (t, J = 7.2 Hz, 1H), 6.23 (s, 1H), 5.20-5.17 (m, 1H), 4.02 (bs, 1H), 3.14 (s, 3H), 2.91-2.90 (d, J = 4.8 Hz, 3H), 1.77 (bs, 1H), 1.56 (bs, 3H), 1.37-1.35 (d, J = 6.8 Hz, 6H), 1.24 (bs, 3H), 1.12 (bs, 4H). |

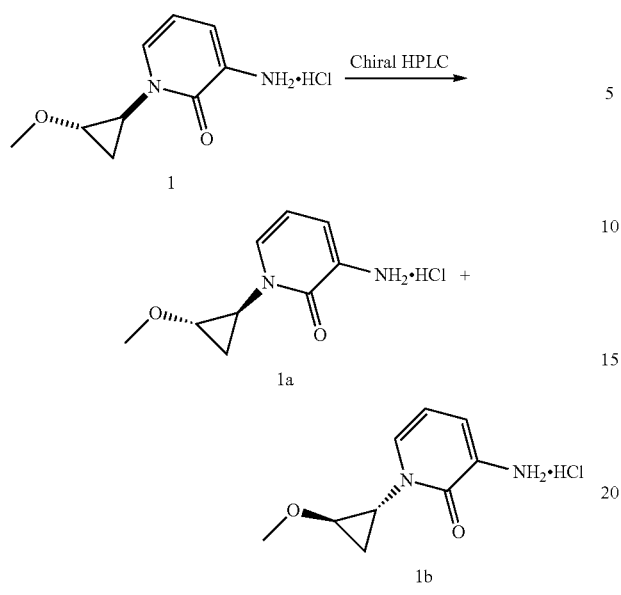

Synthesis of Compound 1.

Compound was synthesized as per experimental protocol of the intermediates to obtain 1. (Yield: 94.88%), MS (ES): m/z 217.07 [M+H]$^+$ Synthesis of compound 1a and 1b.

Isomers of 1 (0.105 g) were separated out using column CHIRALPAK AD-H (250 mm*4.6 mm, 5 u) and 0.1% DEA in IPA:MEOH (50:50) as co-solvent with flow rate of 4 mL/min. to get pure fraction-1 (FR-a) and fraction-2 (FR-b). FR-a was concentrated under reduced pressure at 30° C. to afford pure 1a. (0.205 g). MS(ES): m/z 217.07 [M+H]$^+$. FR-b was concentrated under reduced pressure at 30° C. to afford pure 1b. (0.210 g). MS(ES): m/z 217.07 [M+H]$^+$ While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound selected from the group consisting of:

I-1

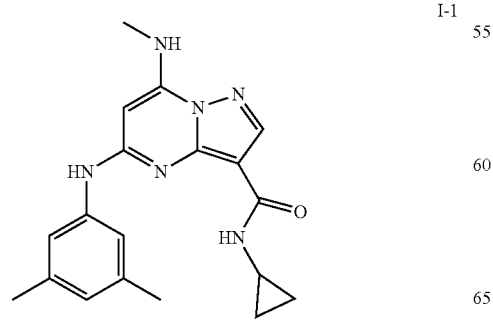

I-2

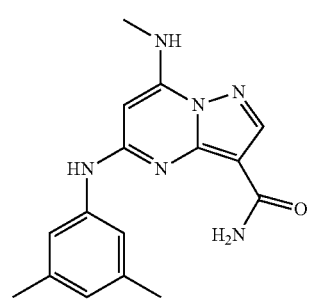

I-3

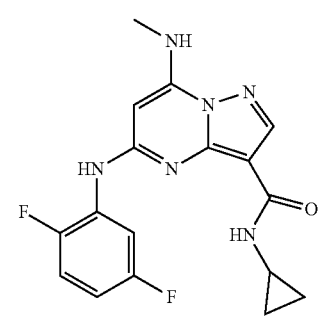

I-5

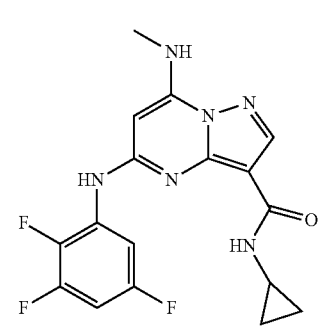

I-6

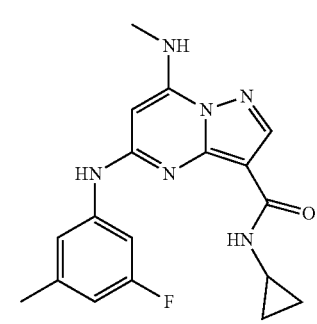

I-14

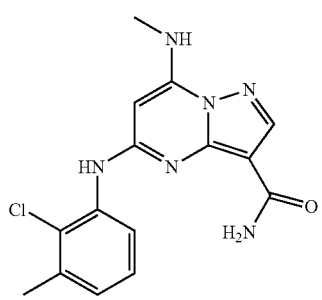

I-16
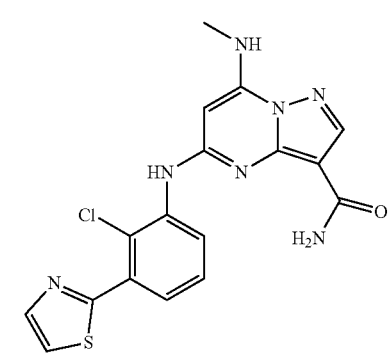
I-17
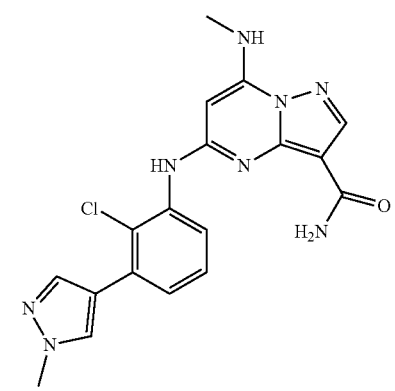
I-36
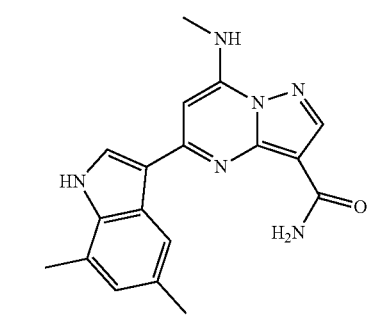
I-190
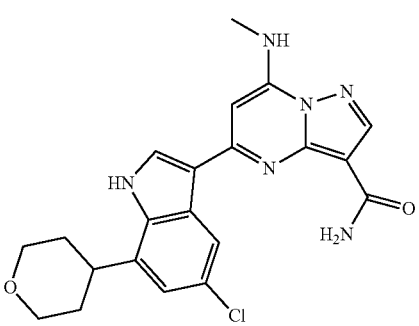
I-222
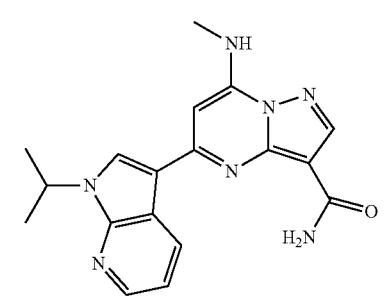
I-223
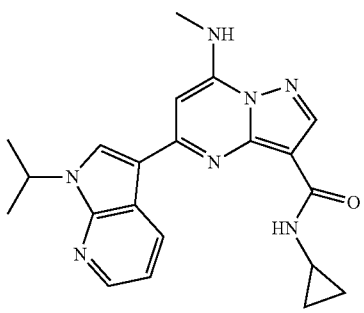
I-224
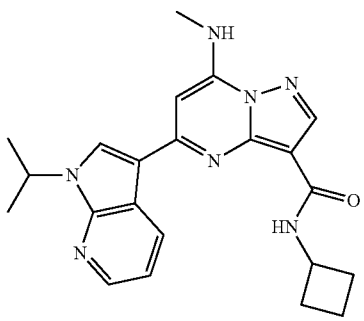
I-225
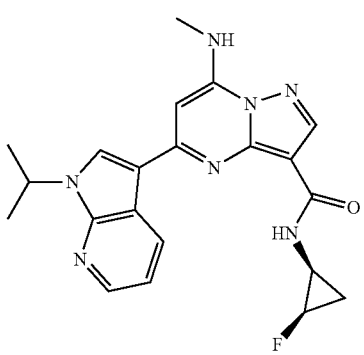
I-255
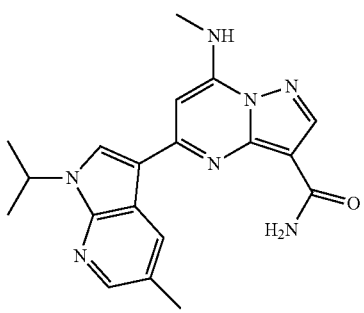
I-272
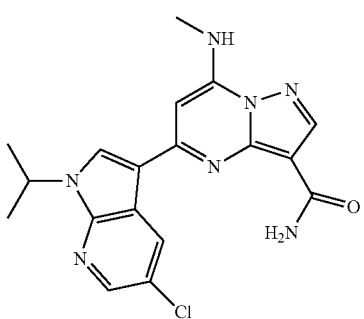

I-578
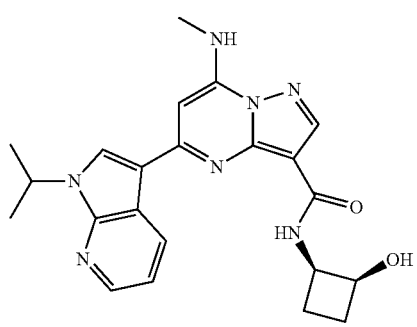
I-592
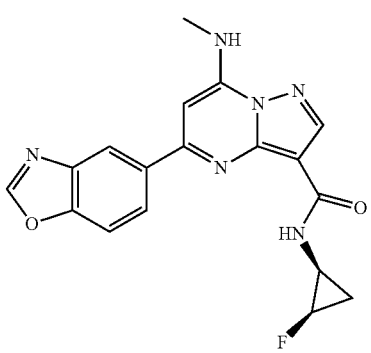
I-585
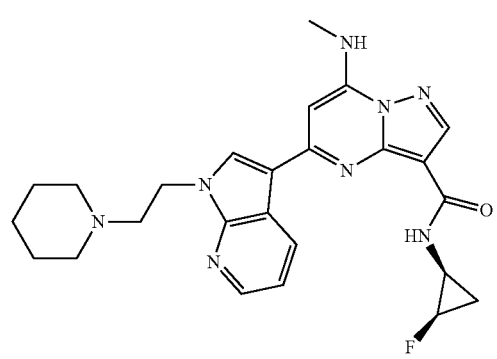
I-630
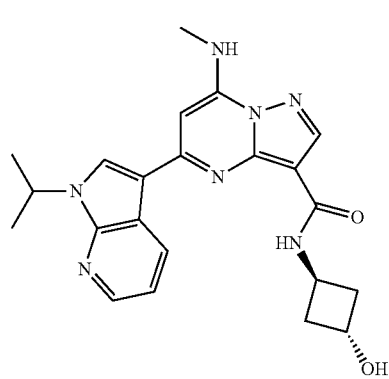
I-586
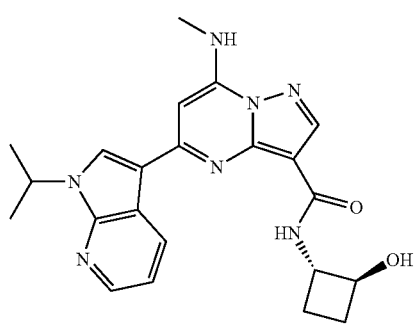
I-637
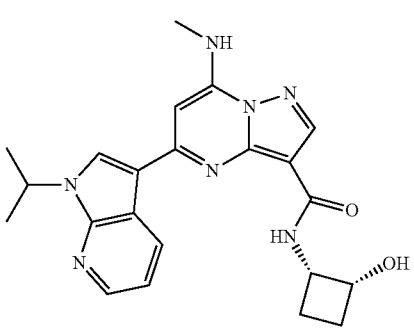
I-591
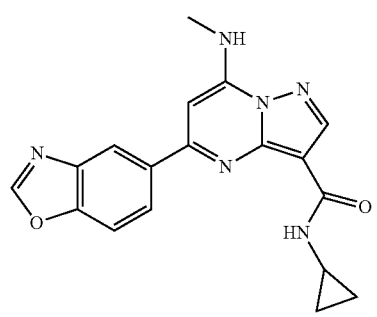
I-639
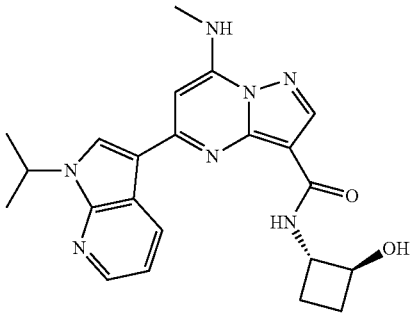

1879
-continued
I-640
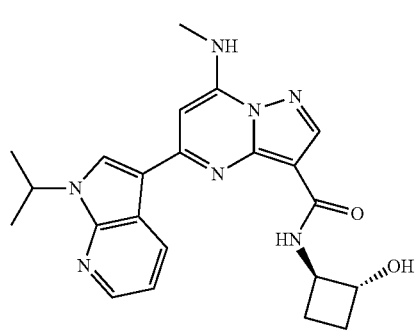
I-661
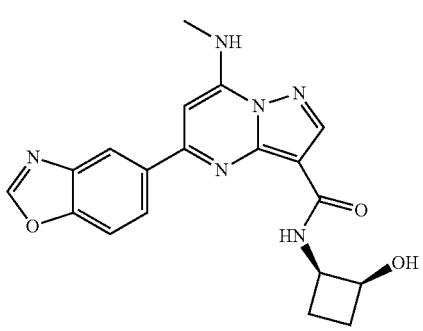
I-750
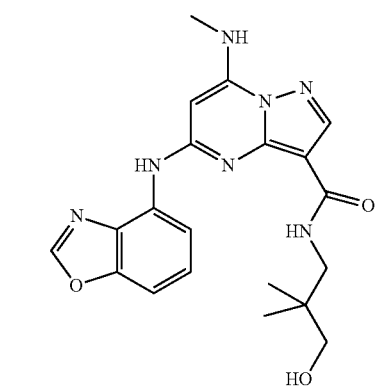
I-756
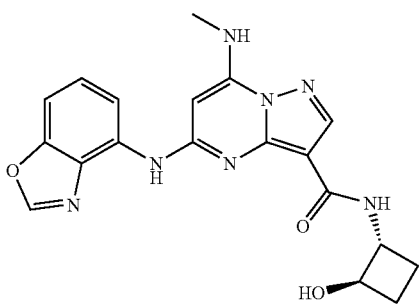
I-770
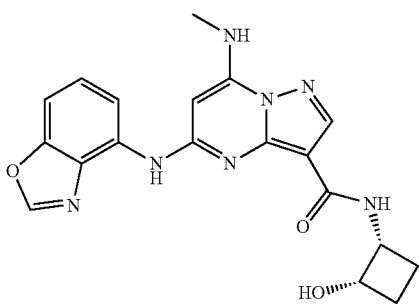
1880
-continued
I-834
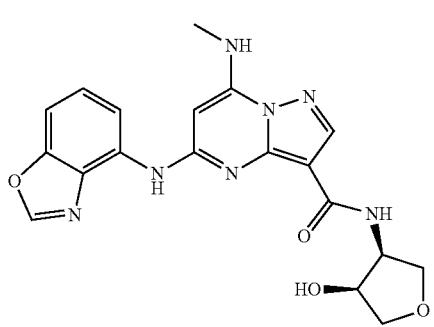
I-837
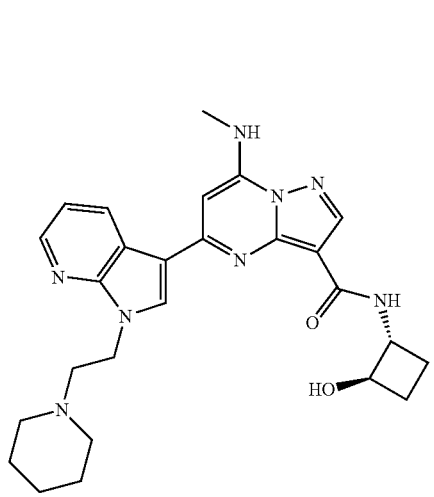
I-842
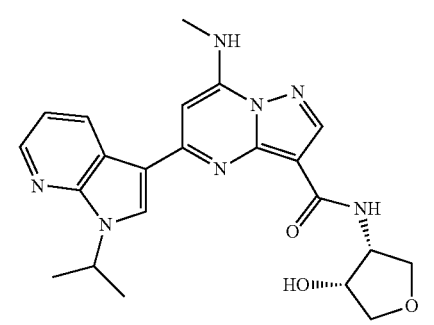
I-857
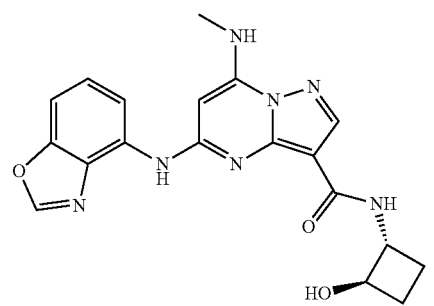

I-886 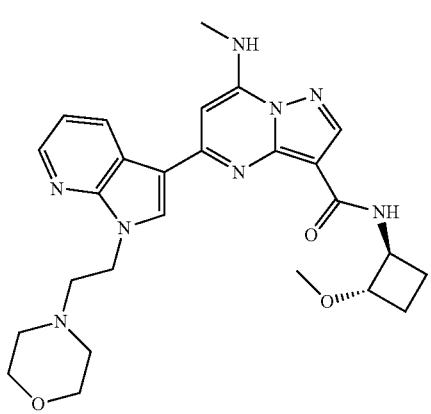
I-914 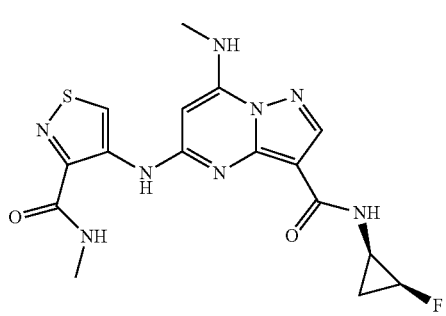
I-887 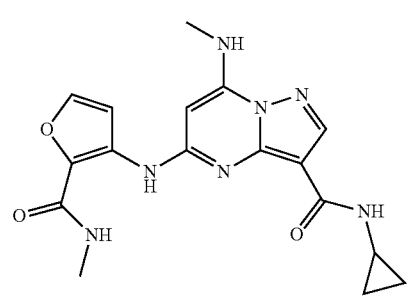
I-960 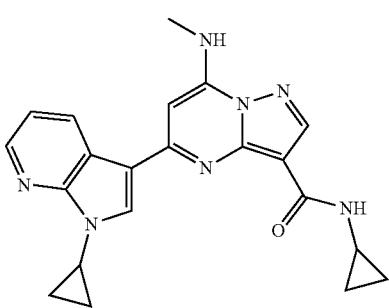
I-888 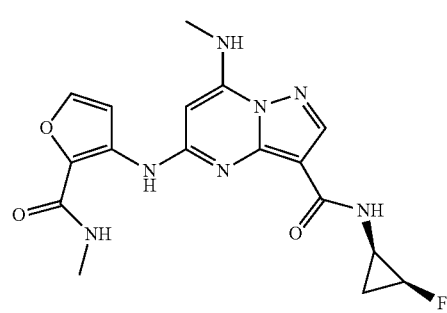
I-961 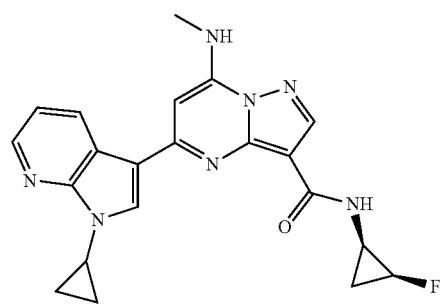
I-891 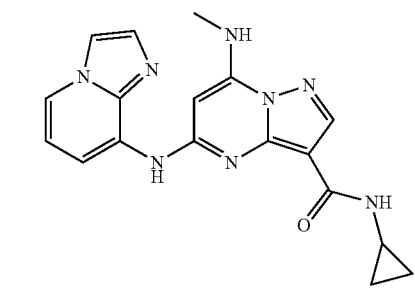
I-992 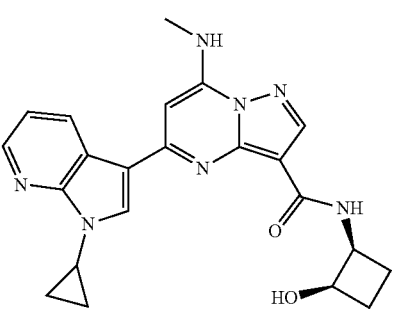
I-892 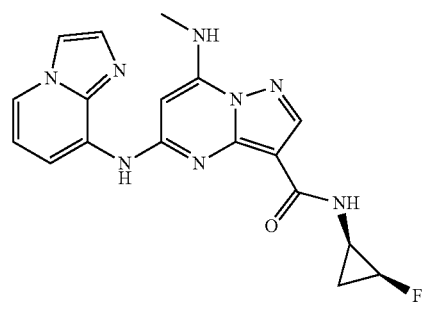
I-1051 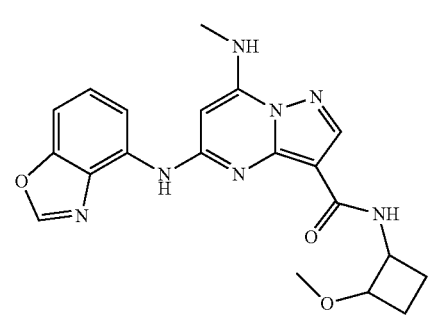

1883
-continued
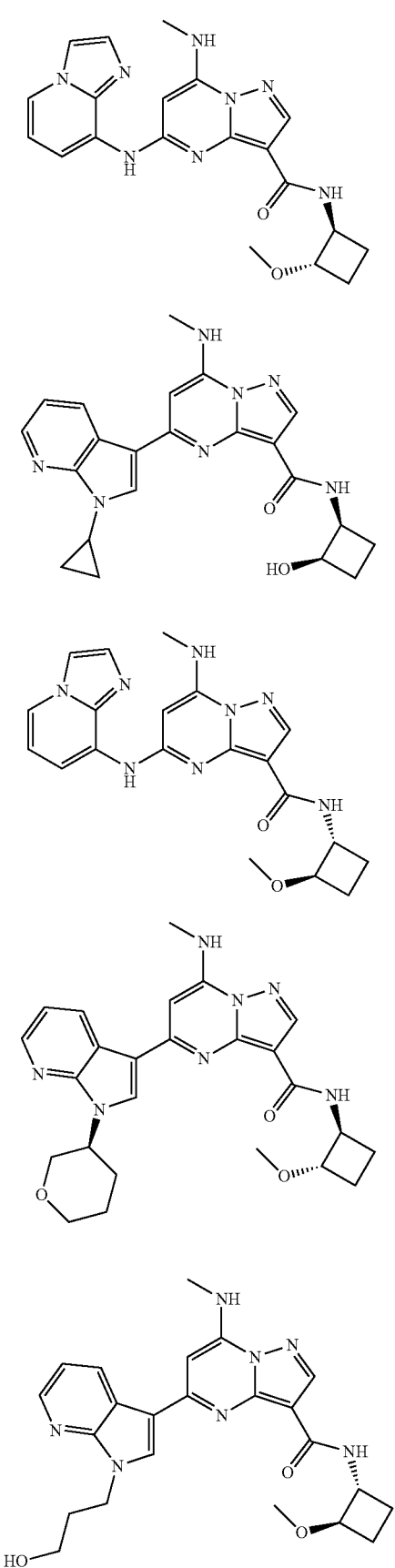
I-1052
I-1080
I-1133
I-1283
I-1299
1884
-continued
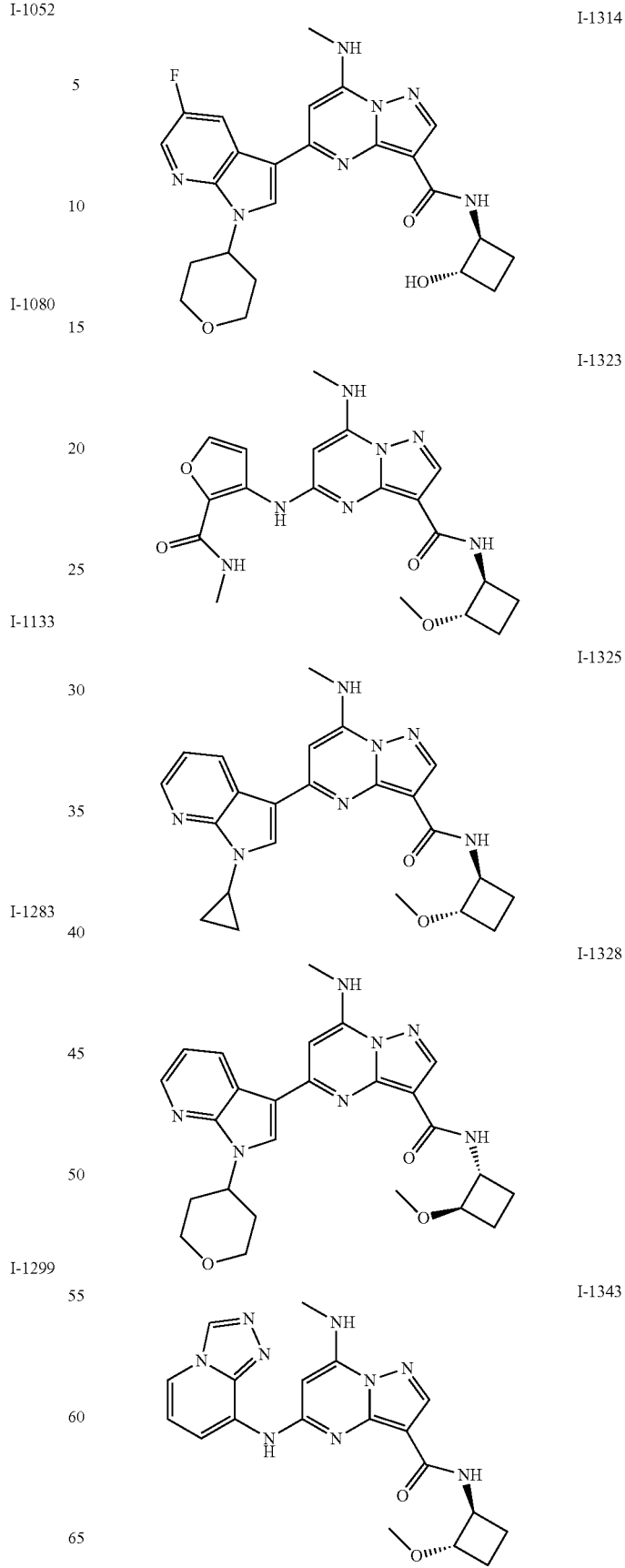
I-1314
I-1323
I-1325
I-1328
I-1343

1885
-continued
I-1362
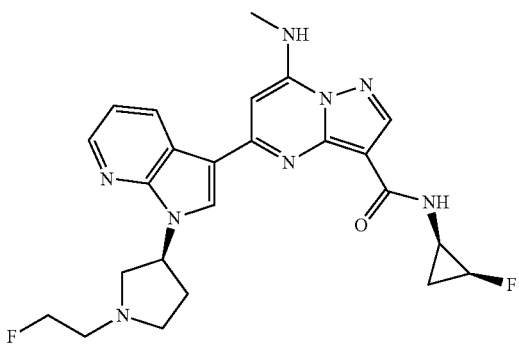
I-1364
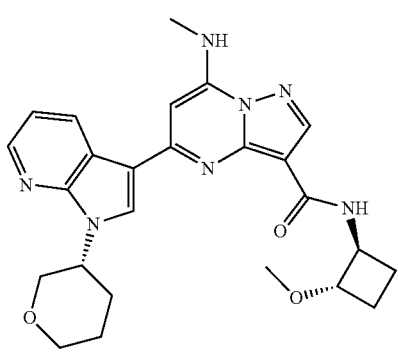
I-1365
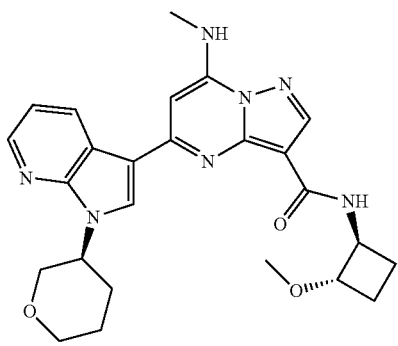
I-1366
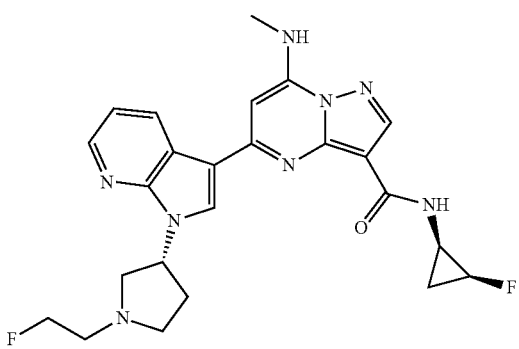
1886
-continued
I-1387
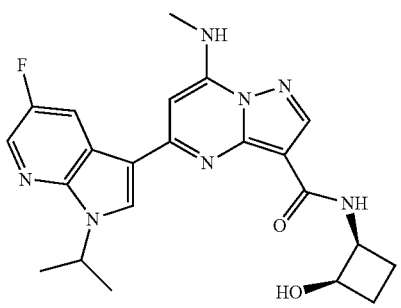
and
I-1388
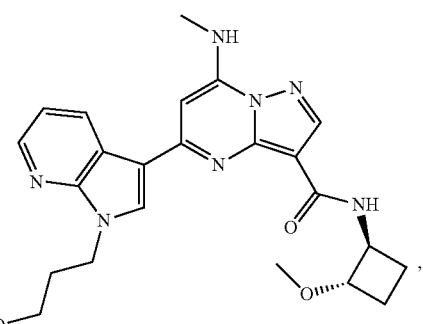
or a pharmaceutically acceptable salt thereof.
2. The compound of claim 1, wherein said compound is selected from the group consisting of:
I-1
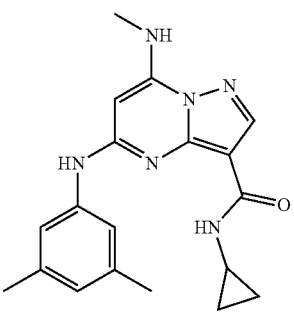
I-2
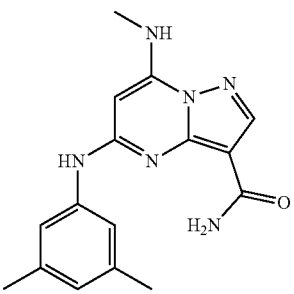

-continued
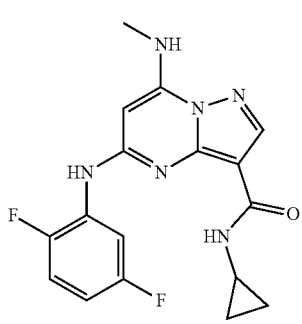
I-3
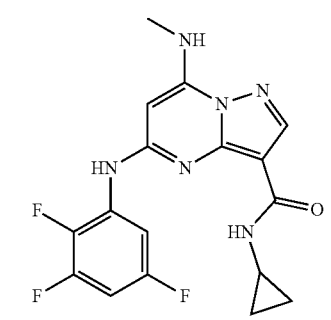
I-5
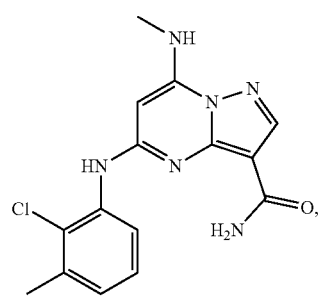 and
I-6
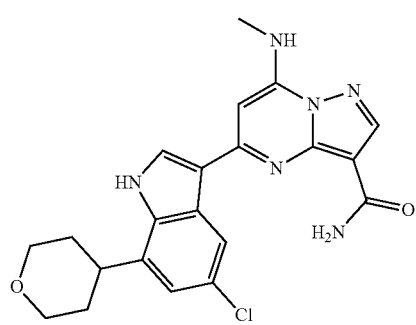
I-14
or a pharmaceutically acceptable salt thereof.
3. The compound of claim 1, wherein said compound is selected from the group conisting of:
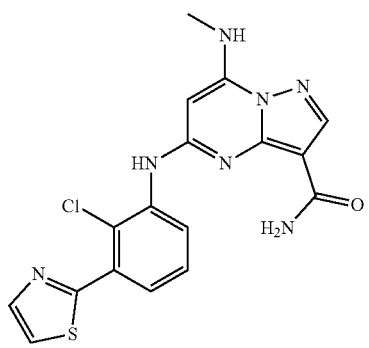
I-16
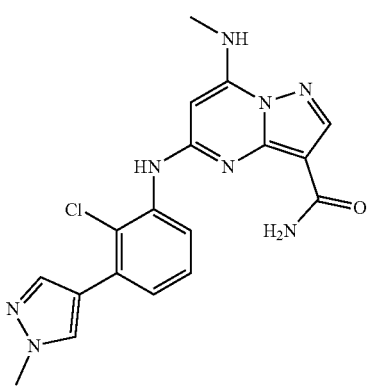
I-17
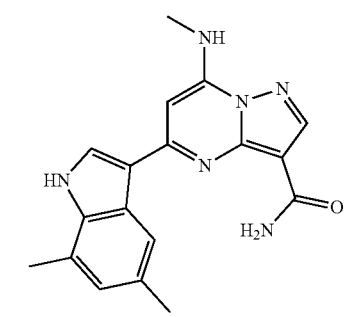
I-36
I-190

I-222
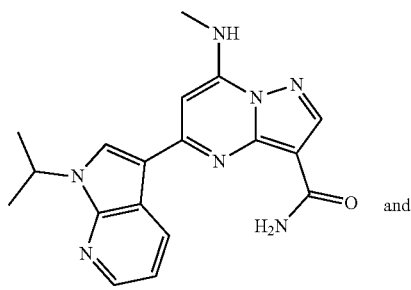 and
I-223
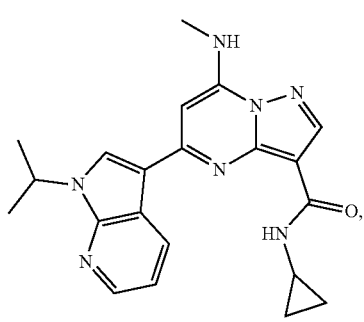
or a pharmaceutically acceptable salt thereof.
4. The compound of claim 1, wherein said compound is selected from the group consisting of:
I-224
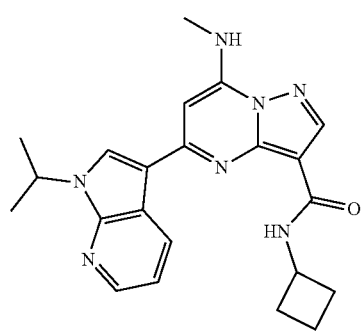
I-225
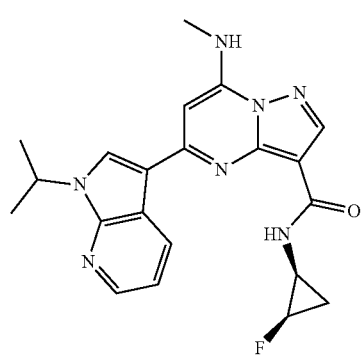
I-255
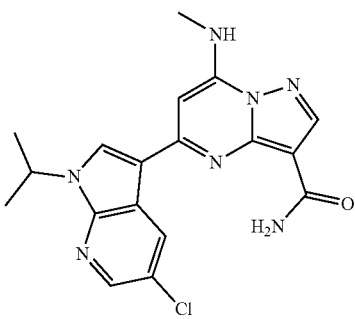
I-272
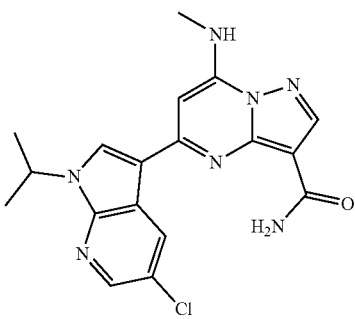
I-578
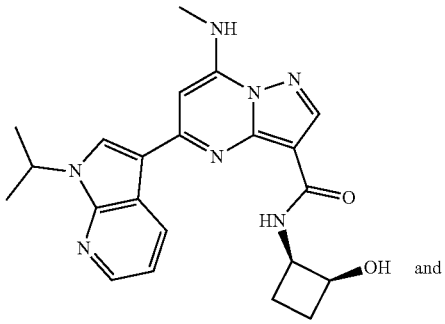
I-585
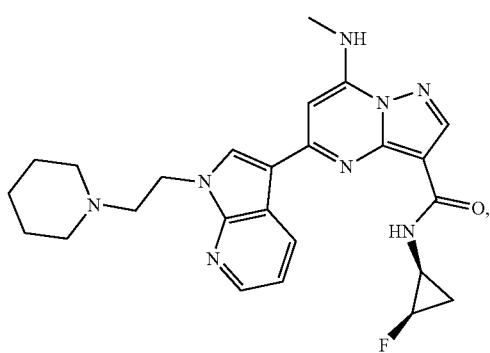
or a pharmaceutically acceptable salt thereof.
5. The compound of claim 1, wherein said compound is selected from the group consisting of:

I-586
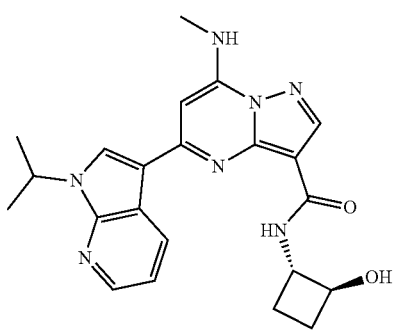
I-591
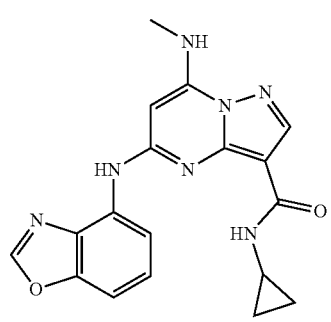
I-592
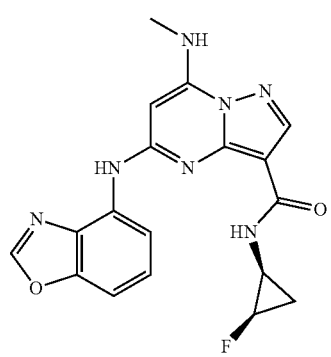
I-630
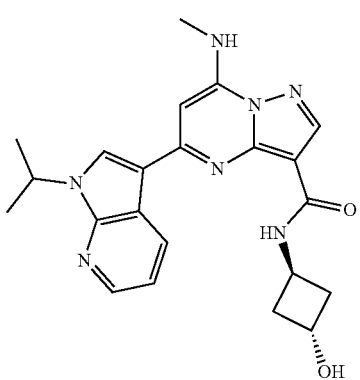
-continued
I-637
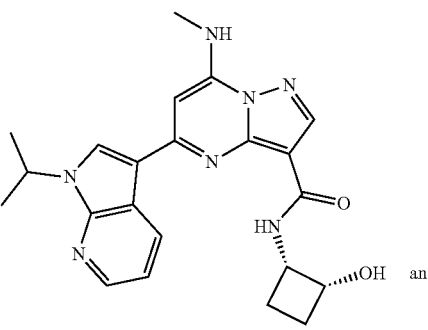
and
I-639
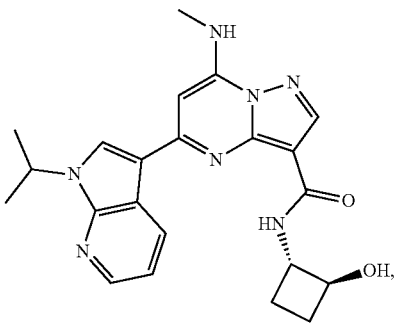
or a pharmaceutically acceptable salt thereof.
6. The compound of claim 1, wherein said compound is selected from the group consisting of:
I-640
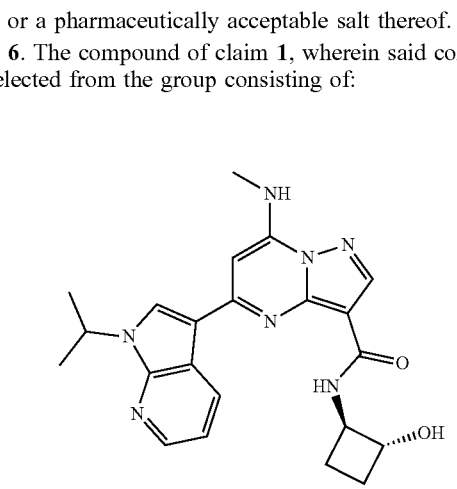
I-661
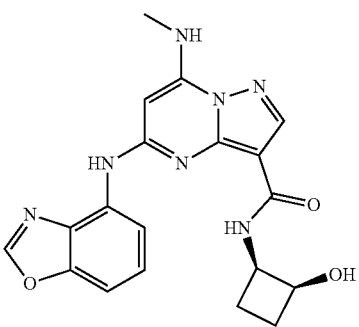

I-750
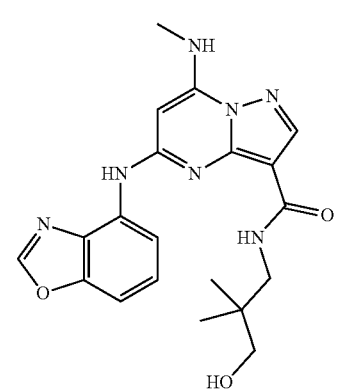
I-756
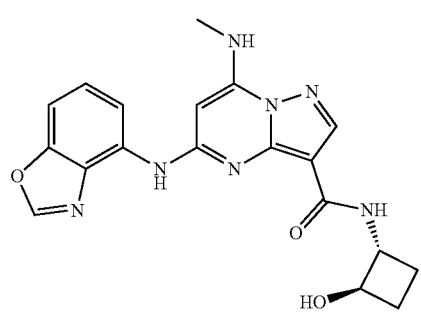
I-770
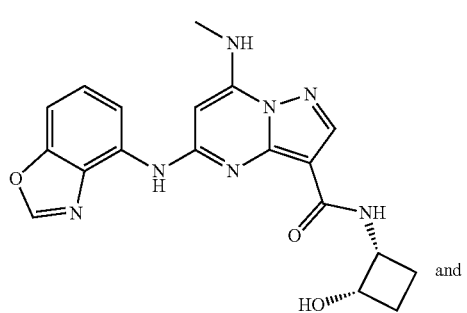
and
I-834
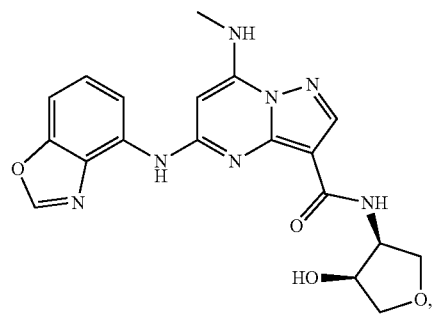
or a pharmaceutically acceptable salt thereof.
7. The compound of claim 1, wherein said compound is selected from the group consisting of:
I-837
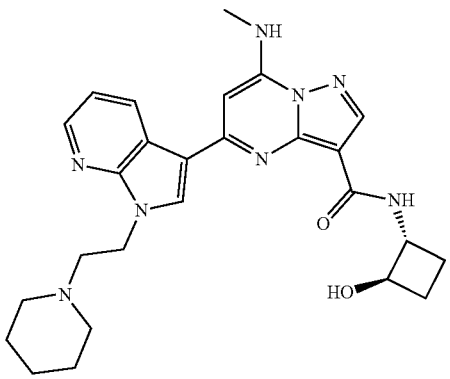
I-842
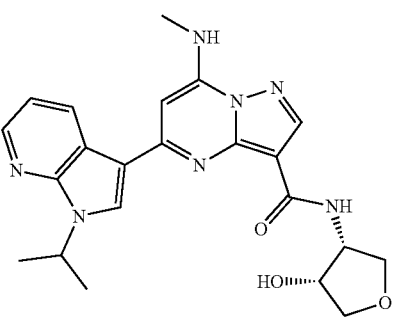
I-857
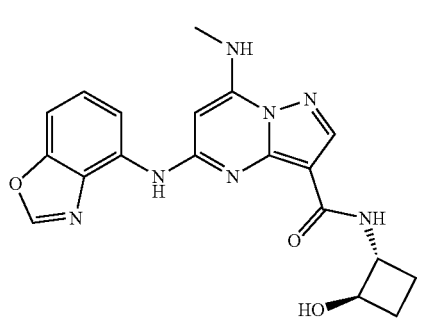
I-886
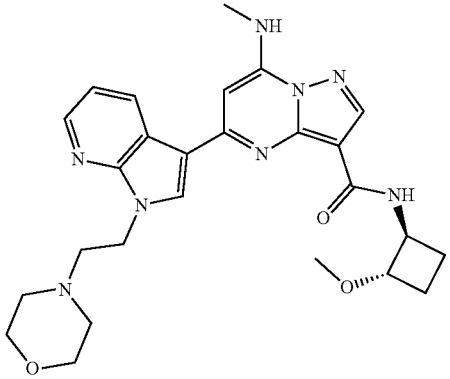

I-887
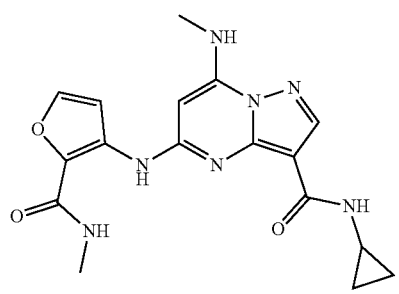
and
I-888
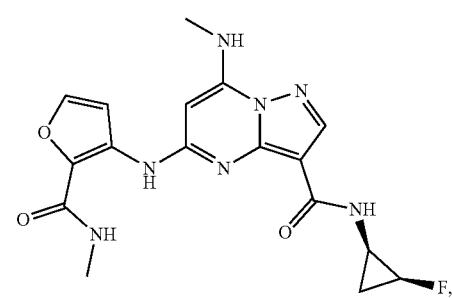
or a pharmaceutically acceptable salt thereof.
8. The compound of claim 1, wherein said compound is selected from the group consisting of:
I-891
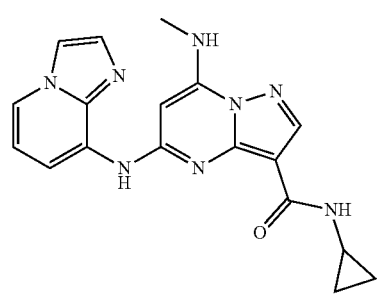
I-892
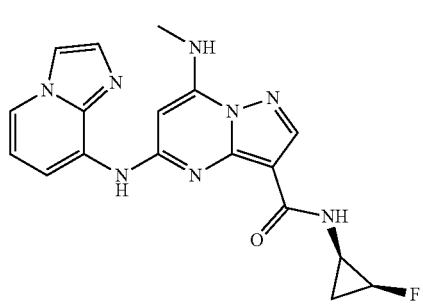
I-914
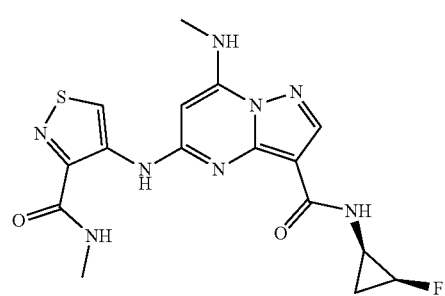
I-960
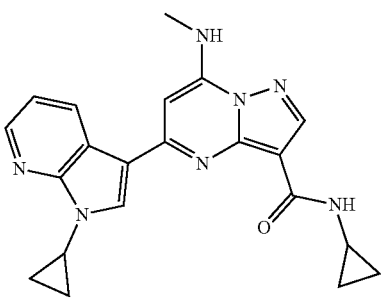
I-961
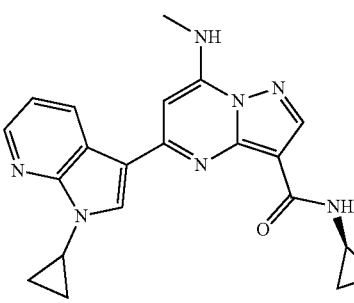
and
I-992
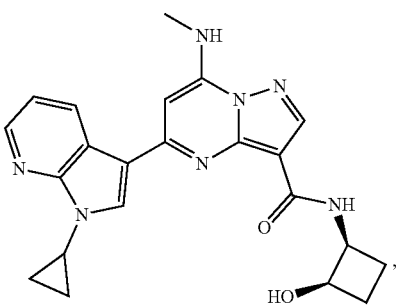
or a pharmaceutically acceptable salt thereof.
9. The compound of claim 1, wherein said compound is selected from the group consisting of:
I-1051
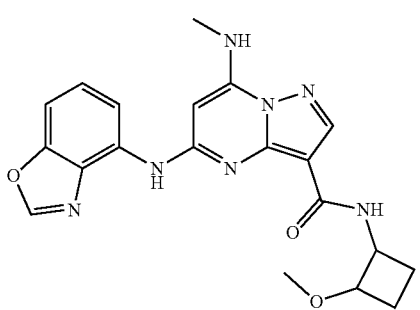

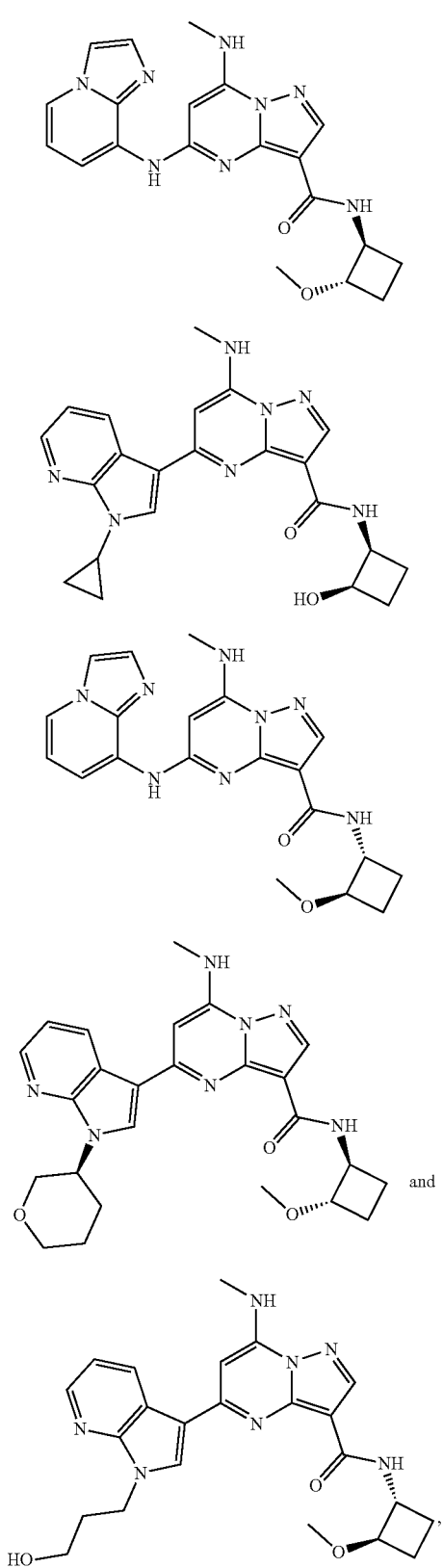
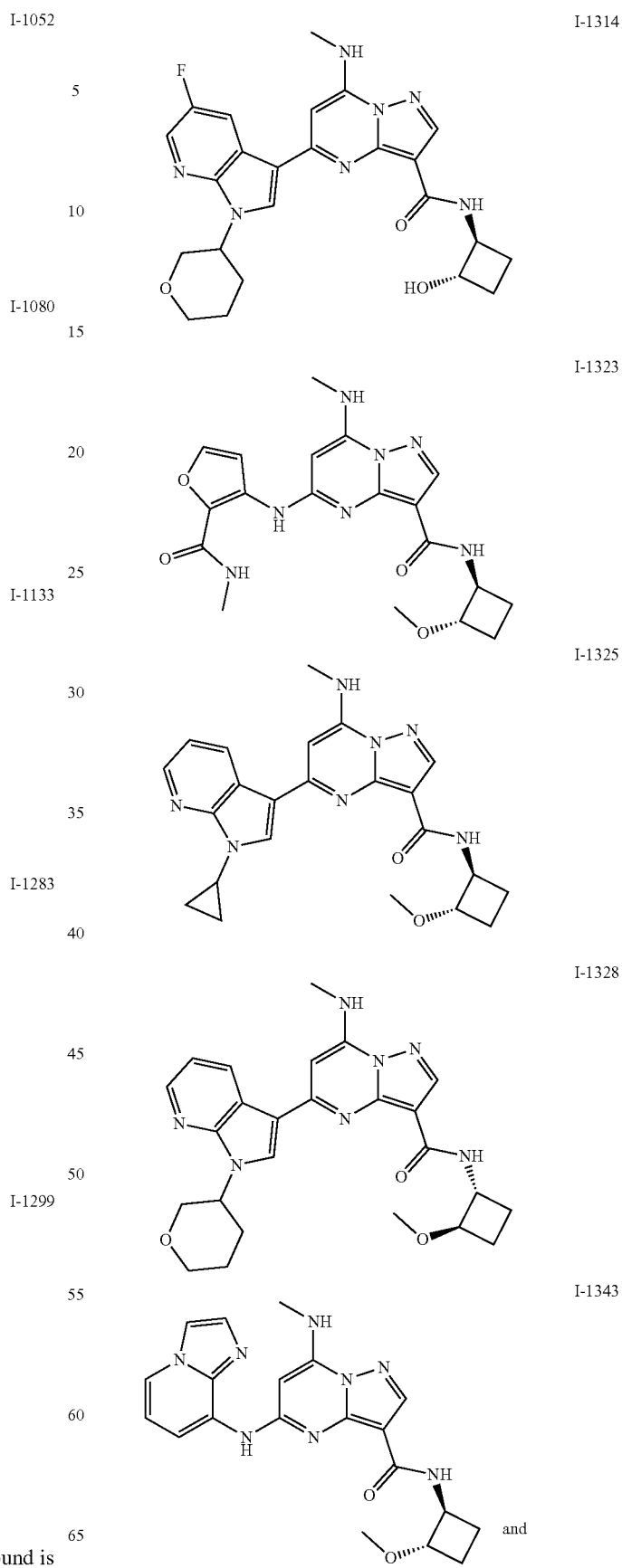
or a pharmaceutically acceptable salt thereof.
10. The compound of claim 1, wherein said compound is selected from the group consisting of:

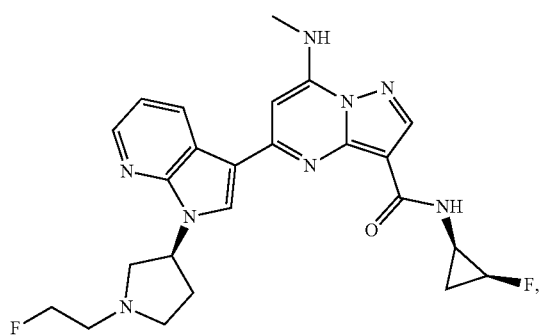

or a pharmaceutically acceptable salt thereof.

11. The compound of claim 1, wherein said compound is selected from the group consisting of:

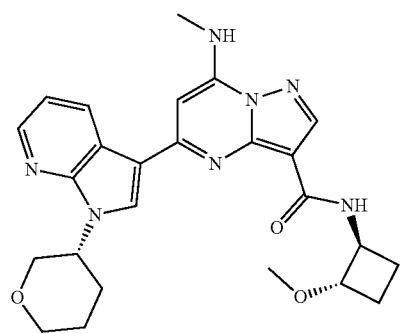

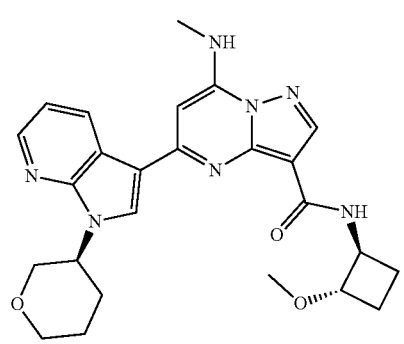

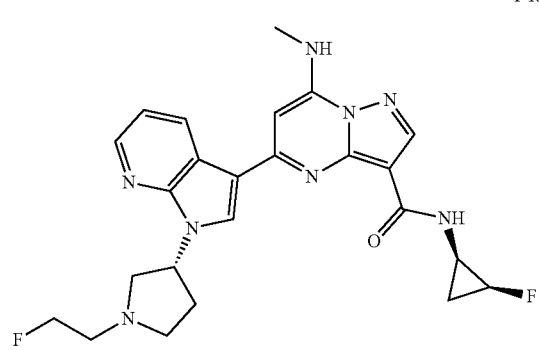

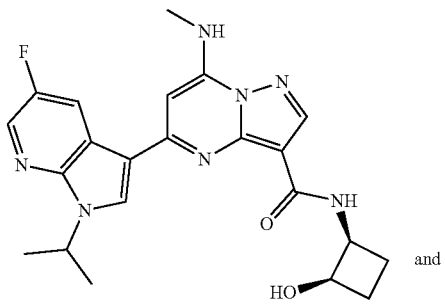

or a pharmaceutically acceptable salt thereof.

12. A pharmaceutical composition comprising a compound according to claim 1, or a pharmaceutically acceptable salt thereof, and a pharmaceutically acceptable carrier, adjuvant, or vehicle.

13. A compound of the formula:

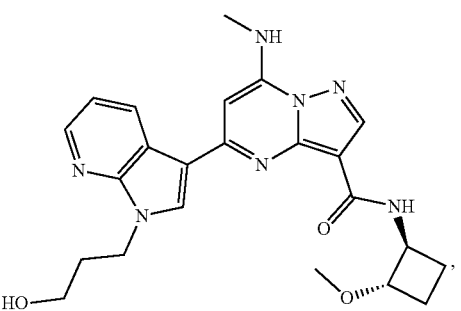

or a pharmaceutically acceptable salt thereof.

14. A pharmaceutical composition comprising a compound of the formula:

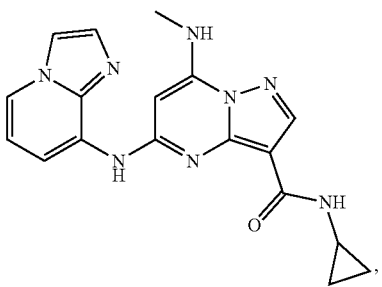

or a pharmaceutically acceptable salt thereof, and a pharmaceutically acceptable carrier, adjuvant, or vehicle.

15. A compound of the formula:

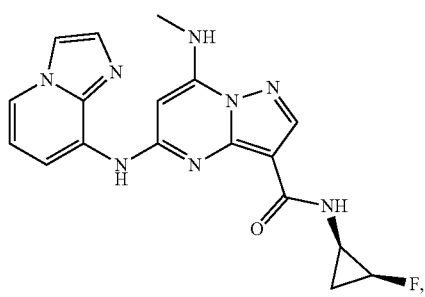

I-892 or a pharmaceutically acceptable salt thereof.

16. A pharmaceutical composition comprising a compound of the formula:

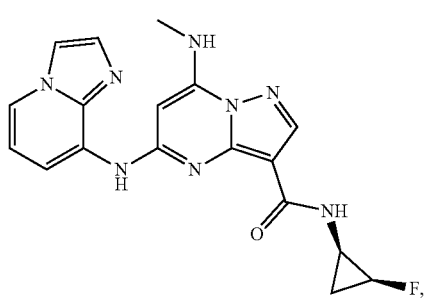

I-892 or a pharmaceutically acceptable salt thereof, and a pharmaceutically acceptable carrier, adjuvant, or vehicle.

17. A compound of the formula:

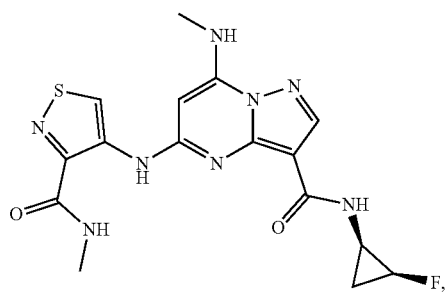

I-914 or a pharmaceutically acceptable salt thereof.

18. A pharmaceutical composition comprising a compound of the formula:

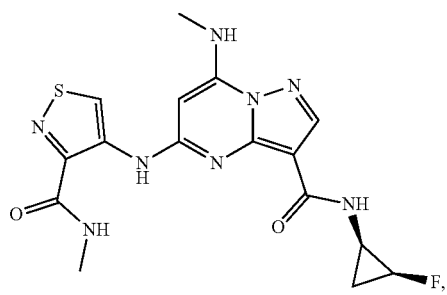

I-914 or a pharmaceutically acceptable salt thereof, and a pharmaceutically acceptable carrier, adjuvant, or vehicle.

19. A compound of the formula:

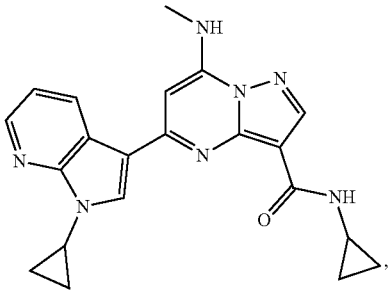

I-960 or a pharmaceutically acceptable salt thereof.

20. A pharmaceutical composition comprising a compound of the formula:

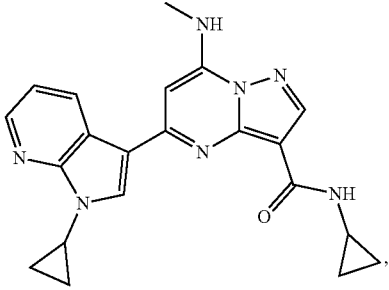

I-960 or a pharmaceutically acceptable salt thereof, and a pharmaceutically acceptable carrier, adjuvant, or vehicle.

21. A compound of the formula:

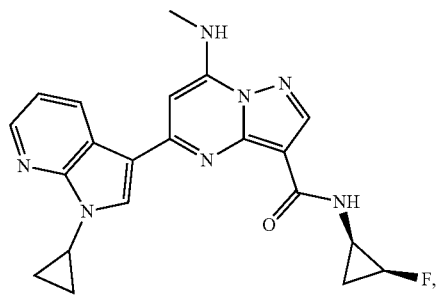

I-961 or a pharmaceutically acceptable salt thereof.

22. A pharmaceutical composition comprising a compound of the formula:

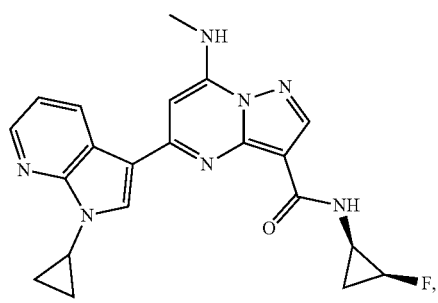

I-961 or a pharmaceutically acceptable salt thereof, and a pharmaceutically acceptable carrier, adjuvant, or vehicle.

23. A compound of the formula:

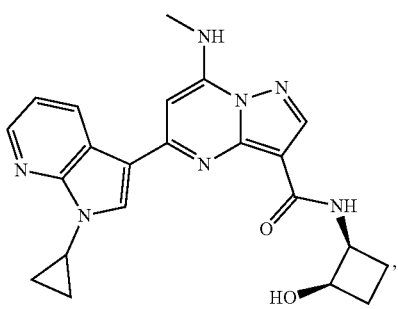

I-992 or a pharmaceutically acceptable salt thereof.

24. A pharmaceutical composition comprising a compound of the formula:

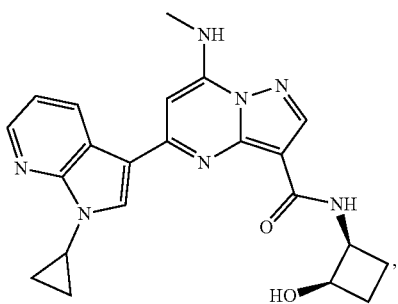

I-992 or a pharmaceutically acceptable salt thereof, and a pharmaceutically acceptable carrier, adjuvant, or vehicle.

25. A compound of the formula:

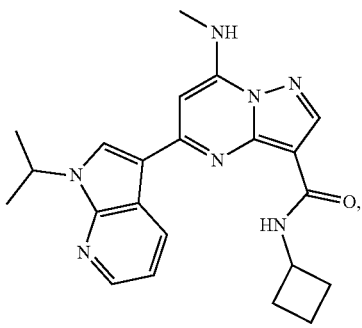

I-224 or a pharmaceutically acceptable salt thereof.

26. A pharmaceutical composition comprising a compound of the formula:

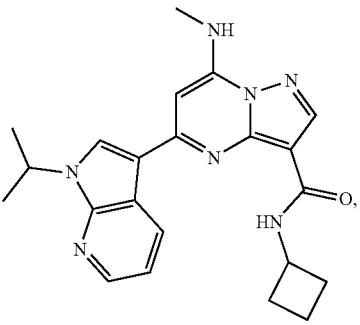

I-224 or a pharmaceutically acceptable salt thereof, and a pharmaceutically acceptable carrier, adjuvant, or vehicle.

27. A compound of the formula:

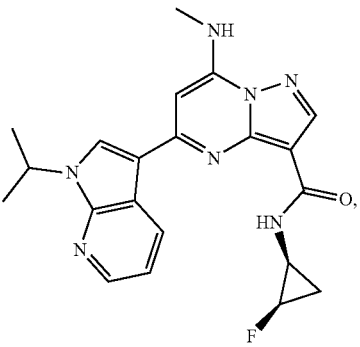

I-225 or a pharmaceutically acceptable salt thereof.

28. A pharmaceutical composition comprising a compound of the formula:

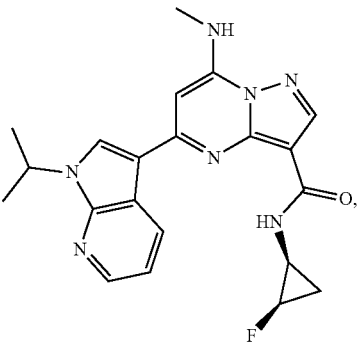

I-225 or a pharmaceutically acceptable salt thereof, and a pharmaceutically acceptable carrier, adjuvant, or vehicle.

* * * * *